(12) United States Patent
Cho et al.

(10) Patent No.: US 11,780,856 B2
(45) Date of Patent: Oct. 10, 2023

(54) COMPOUND AND ORGANIC LIGHT-EMITTING DEVICE COMPRISING SAME

(71) Applicant: LG CHEM, LTD., Seoul (KR)

(72) Inventors: Hye Min Cho, Daejeon (KR); Sujeong Geum, Daejeon (KR); Seonwoo Kim, Daejeon (KR); Wanpyo Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/427,865

(22) PCT Filed: Nov. 27, 2020

(86) PCT No.: PCT/KR2020/017076
§ 371 (c)(1),
(2) Date: Aug. 2, 2021

(87) PCT Pub. No.: WO2021/107681
PCT Pub. Date: Jun. 3, 2021

(65) Prior Publication Data
US 2023/0075017 A1  Mar. 9, 2023

(30) Foreign Application Priority Data

Nov. 29, 2019 (KR) .................. 10-2019-0156840
May 20, 2020 (KR) .................. 10-2020-0060591

(51) Int. Cl.
*C07F 5/02* (2006.01)
*C09K 11/06* (2006.01)
(Continued)

(52) U.S. Cl.
CPC ............ *H01L 51/008* (2013.01); *C07F 5/027* (2013.01); *C09K 11/06* (2013.01);
(Continued)

(58) Field of Classification Search
CPC ..... C07F 5/027; H01L 51/008; H01L 51/0059
See application file for complete search history.

(56) References Cited

U.S. PATENT DOCUMENTS

2004/0251816 A1  12/2004 Leo et al.
2018/0301629 A1  10/2018 Hatakeyama et al.
(Continued)

FOREIGN PATENT DOCUMENTS

CN  106467553 A  3/2017
CN  110943176 A  3/2020
(Continued)

OTHER PUBLICATIONS

Computer-generated English-language translation of WO-2020218079-A1 (Partial).*

(Continued)

*Primary Examiner* — Vu A Nguyen
(74) *Attorney, Agent, or Firm* — DENTONS US LLP

(57) ABSTRACT

A compound of Chemical Formula 1 and an organic light emitting device including the same, the compound used as a material of an organic material layer of the organic light emitting device and providing high color purity and enhanced lifetime properties of the organic light emitting device.

(Continued)

[Chemical Formula 1]

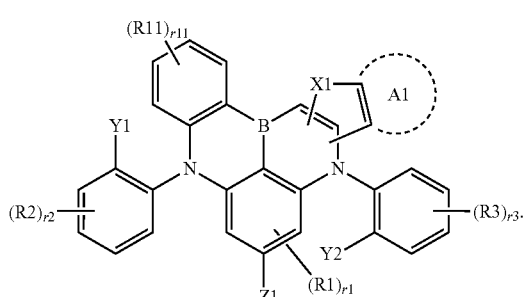

16 Claims, 7 Drawing Sheets

(51) Int. Cl.
*H01L 51/00* (2006.01)
*H01L 51/50* (2006.01)

(52) U.S. Cl.
CPC .... *C09K 2211/188* (2013.01); *H01L 51/5012* (2013.01); *H01L 2251/5384* (2013.01)

(56) References Cited

U.S. PATENT DOCUMENTS

| | | |
|---|---|---|
| 2019/0058124 A1 | 2/2019 | Hatakeyama et al. |
| 2019/0165279 A1 | 5/2019 | Fujita |
| 2019/0207112 A1 | 7/2019 | Hatakeyama et al. |
| 2019/0280209 A1 | 9/2019 | Fujita |
| 2019/0341571 A1 | 11/2019 | Liaptsis |
| 2020/0024263 A1 | 1/2020 | Ito et al. |
| 2020/0058885 A1 | 2/2020 | Hong et al. |
| 2020/0098991 A1 | 3/2020 | Kim et al. |
| 2020/0144513 A1 | 5/2020 | Hatakeyama et al. |
| 2020/0144514 A1 | 5/2020 | Hatakeyama et al. |
| 2020/0144515 A1 | 5/2020 | Hatakeyama et al. |
| 2020/0172558 A1 | 6/2020 | Joo et al. |
| 2020/0176679 A1 | 6/2020 | Jeong et al. |
| 2020/0227639 A1 | 7/2020 | Yamatani |
| 2020/0403165 A1 | 12/2020 | Park et al. |
| 2021/0005825 A1 | 1/2021 | Tasaki et al. |
| 2021/0184121 A1 | 6/2021 | Suh et al. |
| 2022/0089617 A1 | 3/2022 | Kim et al. |
| 2022/0263027 A1 | 8/2022 | Kim et al. |
| 2022/0271226 A1 | 8/2022 | Heo et al. |

FOREIGN PATENT DOCUMENTS

| | | |
|---|---|---|
| CN | 111253421 A | 6/2020 |
| CN | 113227066 A | 8/2021 |
| CN | 113348171 A | 9/2021 |
| CN | 113366002 A | 9/2021 |
| CN | 113454092 A | 9/2021 |
| CN | 113454093 A | 9/2021 |
| CN | 113795497 A | 12/2021 |
| CN | 113812015 A | 12/2021 |
| CN | 113841262 A | 12/2021 |
| CN | 113906580 A | 1/2022 |
| CN | 113924665 A | 1/2022 |
| CN | 114026147 A | 2/2022 |
| EP | 3565018 A1 | 6/2019 |
| EP | 3792989 A1 | 3/2021 |
| EP | 3 907 228 A1 | 10/2021 |
| EP | 3915979 A1 | 12/2021 |
| EP | 3 960 744 A1 | 2/2022 |
| EP | 4001284 A1 | 5/2022 |
| JP | 2010215759 A | 9/2010 |
| KR | 2017-0127593 A | 11/2017 |
| KR | 1876763 B1 | 7/2018 |
| KR | 10-2018-0098121 A | 9/2018 |
| KR | 2018-0122298 A | 11/2018 |
| KR | 2018-0134850 A | 12/2018 |
| KR | 2019-0062177 A | 6/2019 |
| KR | 2019-0101900 A | 9/2019 |
| KR | 2019-0126791 A | 11/2019 |
| KR | 2019-0127529 A | 11/2019 |
| KR | 2020-0066208 A | 6/2020 |
| KR | 2020-0087906 A | 7/2020 |
| KR | 2020-0125583 A | 11/2020 |
| KR | 2020-0145674 A | 12/2020 |
| KR | 2021-0010389 A | 1/2021 |
| KR | 2021-0027179 A | 3/2021 |
| KR | 10-2430998 B1 | 8/2022 |
| WO | 2003-012890 A2 | 2/2003 |
| WO | 2015-102118 A1 | 7/2015 |
| WO | 2017-188111 A1 | 11/2017 |
| WO | 2018-186374 A1 | 10/2018 |
| WO | 2020054676 A1 | 3/2020 |
| WO | WO-2020218079 A1 * | 10/2020 ............... C07F 5/02 |
| WO | 2020-231214 A1 | 11/2020 |
| WO | 2021010770 A1 | 1/2021 |

OTHER PUBLICATIONS

STN Registry RN2377144-83-5, Oct. 15, 2019 (2 Pgs).
Santoro et al., "Effective Method for the Computation of Optical Spectra of Large Molecules at Finite Temperature Including the Duschinsky and Herzberg-Teller Effect: The QX Band of Porphyrin as a Case Study", The Journal of Chemical Physics 128, 224311 (2008).
Kondo et al., "Narrowband Deep-Blue Organic Light-Emitting Diode Featuring an Organoboron-Based Emitter", Nature Photonics vol. 13, 678-682 (2019).

* cited by examiner

COMPOUND AND ORGANIC LIGHT-EMITTING DEVICE COMPRISING SAME

CROSS-REFERENCE TO RELATED APPLICATIONS

This application is a National Phase entry pursuant to 35 U.S.C § 371 of International Application No. PCT/KR2020/017076 filed on Nov. 27, 2020, and claims priority to and the benefits of Korean Patent Application No. 10-2019-0156840, filed on Nov. 29, 2019, and Korean Patent Application No. 10-2020-0060591, filed on May 20, 2020, the disclosures of which are incorporated herein by reference in their entireties.

FIELD OF DISCLOSURE

The present specification relates to a compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required. In a blue organic light emitting device among these, high color purity and long lifetime properties are essential, however, there are lack of technologies to obtain these both due to instability caused by high energy of a blue material. Recently, a thermally active delayed fluorescent material having a core structure including boron has been newly developed and received attention for high efficiency and color purity, however, the material has a disadvantage of short lifetime due to high triplet energy and low inverse interphase transition rate.

Accordingly, development of a blue organic light emitting body capable of obtaining both high color purity and long lifetime properties has been required.

SUMMARY

The present specification is directed to providing a compound, and an organic light emitting device including the same.

One embodiment of the present specification provides a compound represented by the following Chemical Formula 1.

[Chemical Formula 1]

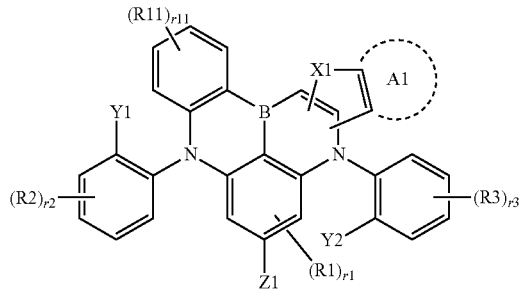

in Chemical Formula 1,

X1 is O or S,

A1 is a substituted or unsubstituted aromatic hydrocarbon ring; a substituted or unsubstituted aliphatic hydrocarbon ring; or a substituted or unsubstituted fused ring of aromatic hydrocarbon ring and aliphatic hydrocarbon ring, at least one of Y1 and Y2 is deuterium; a cyano group; a halogen group; a substituted or unsubstituted alkyl group; a substituted or unsubstituted silyl group; a substituted or unsubstituted alkenyl group; a substituted or unsubstituted aryl group; a substituted or unsubstituted fused ring group of aromatic hydrocarbon ring and aliphatic hydrocarbon ring; or a substituted or unsubstituted heterocyclic group, or adjacent groups of Y1 and Y2 bond to each other to form a substituted or unsubstituted ring, and the remainder is hydrogen, Z1 is hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, R1 to R3 and R11 are the same as or different from each other, and each independently hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, or adjacent groups among R1 to R3 and R11 bond to each other to form a substituted or unsubstituted hydrocarbon ring, r1 is 1 or 2, when r1 is 2, the two R1 s in the parentheses are the same as or different from each other, r2, r3 and r11 are each an integer of 1 to 4, when r2 is 2 or greater, the two or more R2 s in the parentheses are the same as or different from each other, when r3 is 2 or greater, the two or more R3 s in the parentheses are the same as or different from each other, when r11 is 2 or greater, the two or more R11 s in the parentheses are the same as or different from each other, and Chemical Formula 1 includes at least one fused aliphatic hydrocarbon ring substituted with a substituted or unsubstituted alkyl group.

Another embodiment of the present specification provides an organic light emitting device including a first electrode; a second electrode provided opposite to the first electrode; and an organic material layer including one or more layers provided between the first electrode and the second electrode, wherein one or more layers of the organic material layer include the compound.

ADVANTAGEOUS EFFECTS

A compound according to one embodiment of the present specification can be used as a material of an organic material layer of an organic light emitting device, and by using the same, high color purity and/or enhancement in lifetime properties can be obtained in the organic light emitting device.

DESCRIPTION OF REFERENCE NUMERAL

Figure 1:
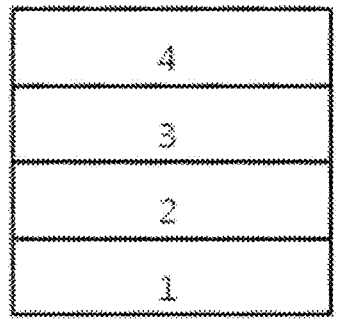
FIG. 1 and FIG. 2 each illustrates an organic light emitting device according to one embodiment of the present specification.

1: Substrate
2: First Electrode
3: Light Emitting Layer
4: Second Electrode
5: Hole Injection Layer
6: Hole Transfer Layer
7: Electron Blocking Layer
8: First Electron Transfer Layer
9: Second Electron Transfer Layer
10: Electron Injection Layer

DETAILED DESCRIPTIONS

Hereinafter, the present specification will be described in more detail.

An organic light emitting device using an existing boron-based compound has more favorable efficiency compared to an organic light emitting device using a pyrene-based compound, but has a disadvantage of short lifetime. However, the compound represented by Chemical Formula 1 includes S or O, which lowers first triplet excitation energy of Chemical Formula 1, and thereby increases a difference between first singlet excitation energy and the first triplet excitation energy. Accordingly, triplet quenching is suppressed, and an organic light emitting device including the same has an increased device efficiency in a host-dopant system.

In addition, Chemical Formula 1 has a left-right asymmetric structure, and has a substituent in which at least one of Y1 and Y2 is not hydrogen, and therefore, has excellent thermal stability due to a lower sublimation temperature compared to an existing boron-based compound considering the molecular weight, and is also suited for deposition when manufacturing an organic light emitting device. Chemical Formula 1 includes at least one aliphatic hydrocarbon ring substituted with a substituted or unsubstituted alkyl group and thereby has 1) high oxidation stability, and a lifetime of an organic light emitting device including the same increases, and with the structural properties, 2) molecular planarity is minimized, and 3) molecular volume increases, and efficiency of the organic light emitting device including the same increases by minimizing concentration quenching.

Particularly, an organic light emitting device using the compound of Chemical Formula 1 having a substituent in which at least one of Y1 and Y2 is not hydrogen as a dopant of a light emitting layer has a minimized intermolecular interaction between a host and the dopant, and as a result, an organic light emitting device with high efficiency and long lifetime may be obtained.

Throughout the specification of the present application, a term "combination thereof" included in a Markush-type expression means a mixture or a combination of one or more selected from the group consisting of constituents described in the Markush-type expression, and means including one or more selected from the group consisting of the constituents.

Examples of substituents in the present specification are described below, however, the substituents are not limited thereto.

In the present specification,

means a linking site.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one or more substituents selected from the group consisting of deuterium; a halogen group; a cyano group; an alkyl group; a cycloalkyl group; an alkoxy group; an aryloxy group; an alkylthioxy group; an arylthioxy group; an alkenyl group; a haloalkyl group; a haloalkoxy group; an arylalkyl group; a silyl group; a boron group; an amine group; an aryl group; a fused ring group of aromatic hydrocarbon ring and aliphatic hydrocarbon ring; and a heterocyclic group, or being substituted with a substituent linking two or more substituents among the substituents illustrated above, or having no substituents.

In the present specification, linking two or more substituents refers to linking hydrogen of any one substituent to another substituent. For example, linking two substituents may include a phenyl group and a naphthyl group being linked to become a substituent of

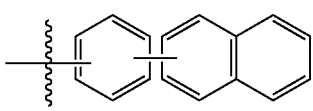

or

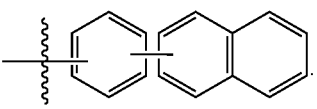

In addition, linking three substituents includes not only continuously linking (substituent 1)-(substituent 2)-(substituent 3), but also linking (substituent 2) and (substituent 3) to (substituent 1). For example, a phenyl group, a naphthyl group and an isopropyl group may be linked to become a substituent of or

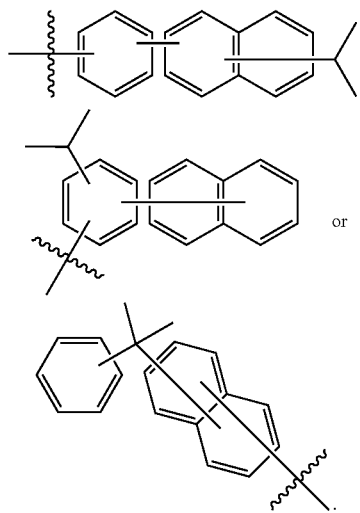

The same rule described above applies to cases of linking four or more substituents.

In the present specification, examples of the halogen group may include fluorine, chlorine, bromine or iodine.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methyl-pentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, an adamantyl group, a bicyclo[2.2.1]octyl group, a norbornyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the haloalkyl group means, in the definition of the alkyl group, hydrogen of the alkyl group being substituted with at least one halogen group.

In the present specification, the haloalkoxy group means, in the definition of the alkoxy group, hydrogen of the alkoxy group being substituted with at least one halogen group.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracene group, a phenanthrene group, a triphenylene group, a pyrene group, a phenalene group, a perylene group, a chrysene group, a fluorene group and the like, but are not limited thereto.

In the present specification, the fluorene group may be substituted, and adjacent groups may bond to each other to form a ring.

When the fluorene group is substituted, [SJS1]

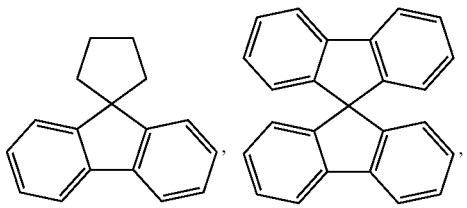

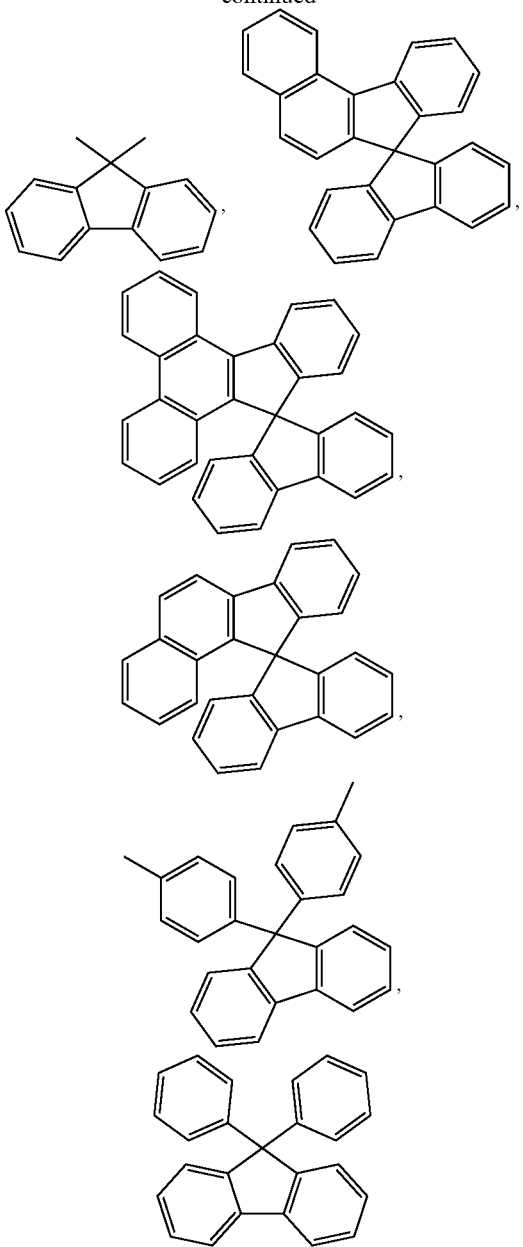

and the like may be included, however, the structure is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

For example, in Chemical Formula 1, R2 and Y1, two or more R2 s, R3 and Y2, two or more R3 s, Z1 and R1, two or more R1 s, and two or more R11 s are "adjacent groups".

In the present specification, the arylalkyl group means the alkyl group being substituted with an aryl group, and the examples of the aryl group and the alkyl group described above may be applied to the aryl group and the alkyl group of the arylalkyl group.

In the present specification, the aryloxy group means, in the definition of the alkoxy group, the alkyl group of the alkoxy group being substituted with an aryl group. Examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, but are not limited thereto.

In the present specification, the alkyl group of the alkylthioxy group is the same as the examples of the alkyl group described above. Specific examples of the alkylthioxy group may include a methylthioxy group, an ethylthioxy group, a tert-butylthioxy group, a hexylthioxy group, an octylthioxy group and the like, but are not limited thereto.

In the present specification, the aryl group in the arylthioxy group is the same as the examples of the aryl group described above. Specific examples of the arylthioxy group may include a phenylthioxy group, a 2-methylphenylthioxy group, a 4-tert-butylphenylthioxy group and the like, but are not limited thereto.

In the present specification, the heterocyclic group is a group including one or more atoms that are not carbon, that is, heteroatoms, and specifically, the heteroatom may include one or more atoms selected from the group consisting of O, N, Se, S and the like, and includes an aromatic heterocyclic group or an aliphatic heterocyclic group. The aromatic heterocyclic group may be represented by a heteroaryl group. The number of carbon atoms of the heterocyclic group is not particularly limited, but is preferably from 2 to 30, and the heterocyclic group may be monocyclic or polycyclic. Examples of the heterocyclic group may include a thiophene group, a furan group, a pyrrole group, an imidazole group, a thiazole group, an oxazole group, an oxadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthridine group, a phenanthroline group, an isoxazole group, a thiadiazole group, a dibenzofuran group, dibenzosilole group, a phenoxanthine group, a phenoxazine group, a phenothiazine group, a dihydroindenocarbazole group, a spirofluorenexanthene group, a spirofluorenethioxanthene group, a tetrahydronaphthothiophene group, a tetrahydronaphthofuran group, a tetrahydrobenzothiophene group, a tetrahydrobenzofuran group and the like, but are not limited thereto.

In the present specification, the silyl group may be an alkylsilyl group, an arylsilyl group, an alkylarylsilyl group, a heteroarylsilyl group or the like. As the alkyl group in the alkylsilyl group, the examples of the alkyl group described above may be applied, and as the aryl group in the arylsilyl group, the examples of the aryl group described above may be applied. As the alkyl group and the aryl group in the alkylarylsilyl group, the examples of the alkyl group and the aryl group may be applied, and as the heteroaryl group in the heteroarylsilyl group, the examples of the heterocyclic group may be applied.

In the present specification, the boron group may be —$BR_{100}R_{101}$. $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heterocyclic group having 2 to 30 carbon atoms. Specific examples of the boron group may include a trimethylboron group, a triethylboron group, a t-butyldimethylboron group, a triphenylboron group, a phenylboron group and the like, but are not limited thereto.

In the present specification, the amine group may be selected from the group consisting of —$NH_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, the N-alkylarylamine group means an amine group in which N of the amine group is substituted with an alkyl group and an aryl group. The alkyl group and the aryl group in the N-alkylarylamine group are the same as the examples of the alkyl group and the aryl group described above.

In the present specification, the N-arylheteroarylamine group means an amine group in which N of the amine group is substituted with an aryl group and a heteroaryl group. The aryl group and the heteroaryl group in the N-arylheteroarylamine group are the same as the examples of the aryl group and the heterocyclic group described above.

In the present specification, the N-alkylheteroarylamine group means an amine group in which N of the amine group is substituted with an alkyl group and a heteroaryl group. The alkyl group and the heteroaryl group in the N-alkylheteroarylamine group are the same as the examples of the alkyl group and the heterocyclic group described above.

In the present specification, examples of the alkylamine group include a substituted or unsubstituted monoalkylamine group, or a substituted or unsubstituted dialkylamine group. The alkyl group in the alkylamine group may be a linear or branched alkyl group. The alkylamine group including two or more alkyl groups may include linear alkyl groups, branched alkyl groups, or both linear alkyl groups and branched alkyl groups. For example, the alkyl group in the alkylamine group may be selected from among the examples of the alkyl group described above.

In the present specification, examples of the heteroarylamine group include a substituted or unsubstituted monoheteroarylamine group, or a substituted or unsubstituted diheteroarylamine group. The heteroarylamine group including two or more heteroaryl groups may include monocyclic heteroaryl groups, polycyclic heteroaryl groups, or both monocyclic heteroaryl groups and polycyclic heteroaryl groups. For example, the heteroaryl group in the heteroarylamine group may be selected from among the examples of the heterocyclic group described above.

In the present specification, the hydrocarbon ring group may be an aromatic hydrocarbon ring group, an aliphatic hydrocarbon ring group, or a fused ring group of aromatic hydrocarbon ring and aliphatic hydrocarbon ring, and may be selected from among the examples of the cycloalkyl group, the aryl group, and combination thereof. Examples of the hydrocarbon ring group may include a phenyl group, a cyclohexyl group, an adamantyl group, a bicyclo[2.2.1]heptyl group, a bicyclo[2.2.1]octyl group, a tetrahydronaphthalene group, a tetrahydroanthracene group, a 1,2,3,4-tetrahydro-1,4-methanonaphthalene group, a 1,2,3,4-tetrahydro-1,4-ethanonaphthalene group and the like, but are not limited thereto.

In the present specification, the meaning of "adjacent" in the "adjacent groups bond to each other to form a ring" is the same as described above, and the "ring" means a substituted or unsubstituted hydrocarbon ring; or a substituted or unsubstituted heteroring.

In the present specification, the hydrocarbon ring may be an aromatic hydrocarbon ring, an aliphatic hydrocarbon ring, or a fused ring of aromatic hydrocarbon ring and aliphatic hydrocarbon ring, and may be selected from among the examples of the cycloalkyl group, the aryl group and combinations thereof except for those that are not monovalent. Examples of the hydrocarbon ring may include benzene, cyclohexane, adamantane, bicyclo[2.2.1]heptane, bicyclo[2.2.1]octane, tetrahydronaphthalene, tetrahydroanthracene, 1,2,3,4-tetrahydro-1,4-methanonaphthalene, 1,2,3,4-tetrahydro-1,4-ethanonaphthalene and the like, but are not limited thereto.

In the present specification, the heteroring includes one or more atoms that are not carbon, that is, heteroatoms, and specifically, the heteroatom may include one or more atoms selected from the group consisting of O, N, Se, S and the like. The heteroring may be monocyclic or polycyclic, may be aromatic, aliphatic, or a fused ring of aromatic and aliphatic, and the aromatic heteroring may be selected from among the examples of the heteroaryl group of the heterocyclic group except for those that are not monovalent.

In the present specification, the aliphatic heteroring means an aliphatic ring including one or more of heteroatoms. Examples of the aliphatic heteroring may include oxirane, tetrahydrofuran, 1,4-dioxane, pyrrolidine, piperidine, morpholine, oxepane, azokane, thiokane, tetrahydronaphthothiophene, tetrahydronaphthofuran, tetrahydrobenzothiophene, tetrahydrobenzofuran and the like, but are not limited thereto.

Unless defined otherwise in the present specification, all technological and scientific terms used in the present specification have the same meanings as terms commonly understood by those skilled in the art. Although methods and materials similar or equivalent to those described in the present specification may be used in carrying out or experimenting embodiments of the present disclosure, suitable methods and materials are described later. All publications, patent applications, patents and other reference documents mentioned in the present specification are incorporated by reference in the present specification as a whole, and when conflicting, the present specification including definitions has priority unless specific passage is mentioned. Furthermore, materials, methods and examples are for illustrative purposes only, and not to limit the present specification.

According to one embodiment of the present specification, Chemical Formula 1 is represented by the following Chemical Formula 2 or 3.

[Chemical Formula 2]

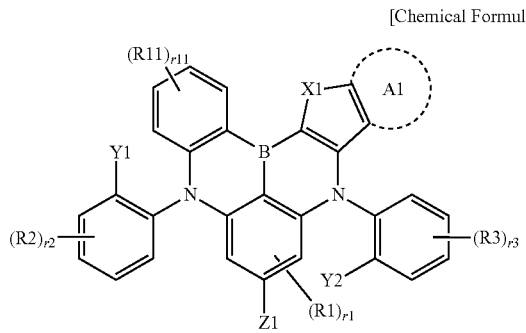

[Chemical Formula 3]

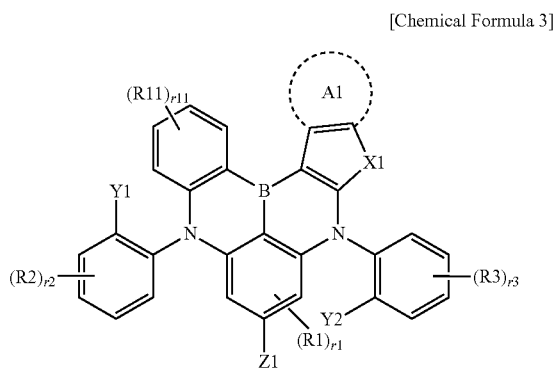

In Chemical Formulae 2 and 3,

X1, A1, Y1, Y2, Z1, R1 to R3, R11, r1 to r3 and r11 have the same definitions as in Chemical Formula 1.

According to one embodiment of the present specification, X1 is O.

According to one embodiment of the present specification, X1 is S.

According to one embodiment of the present specification, Chemical Formula 1 is represented by the following Chemical Formula 1-1 or 1-2.

[Chemical Formula 1-1]

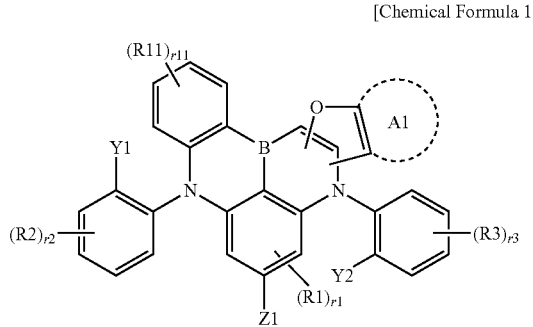

[Chemical Formula 1-2]

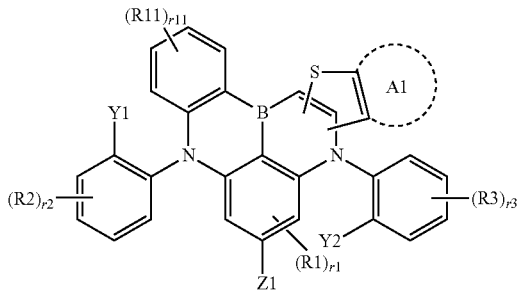

In Chemical Formulae 1-1 and 1-2,

A1, Y1, Y2, Z1, R1 to R3, R11, r1 to r3 and r11 have the same definitions as in Chemical Formula 1.

According to one embodiment of the present specification, Chemical Formula 1 is represented by any one of the following Chemical Formulae 4 to 7.

[Chemical Formula 4]

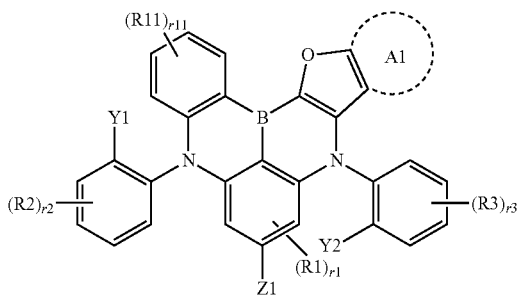

[Chemical Formula 5]

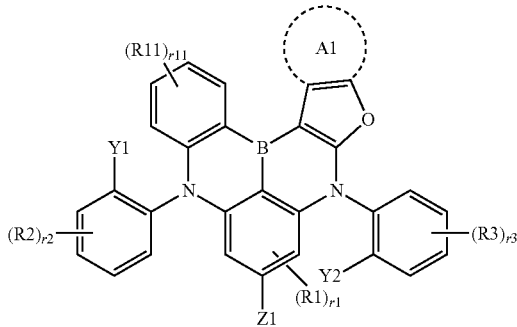

[Chemical Formula 6]

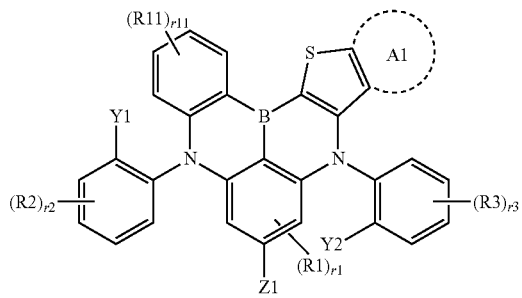

[Chemical Formula 1-4]

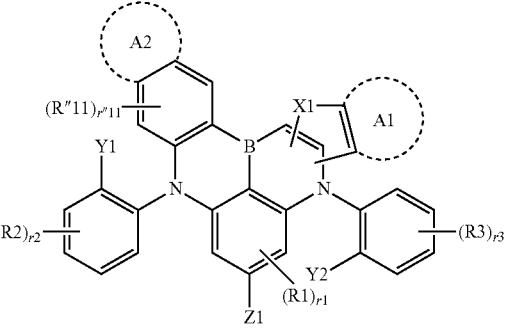

[Chemical Formula 1-5]

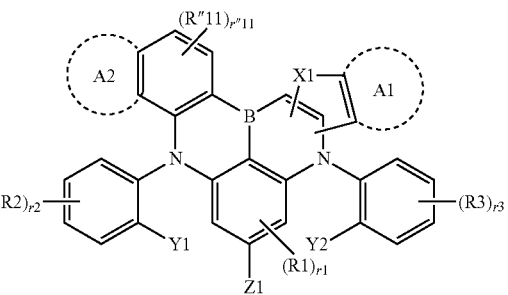

[Chemical Formula 7]

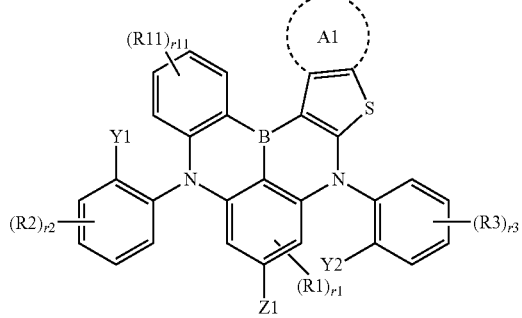

In Chemical Formulae 4 to 7,

A1, Y1, Y2, Z1, R1 to R3, R11, r1 to r3 and r11 have the same definitions as in Chemical Formula 1.

According to one embodiment of the present specification, Chemical Formula 1 is represented by any one of the following Chemical Formulae 1-3 to 1-5.

[Chemical Formula 1-3]

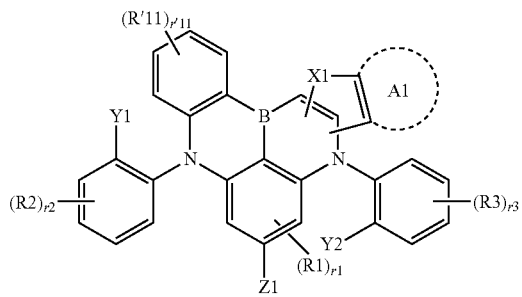

In Chemical Formulae 1-3 to 1-5,

X1, A1, Y1, Y2, Z1, R1 to R3, and r1 to r3 have the same definitions as in Chemical Formula 1, A2 is a substituted or unsubstituted aliphatic hydrocarbon ring, R'11 and R"11 are the same as or different from each other, and each independently hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, r'11 is an integer of 1 to 4, and when r'11 is 2 or greater, the two or more R'11 s in the parentheses are the same as or different from each other, and r"11 is 1 or 2, and when r"11 is 2, the two R"11 s in the parentheses are the same as or different from each other.

According to one embodiment of the present specification, Chemical Formula 1 includes one fused aliphatic hydrocarbon ring substituted with a substituted or unsubstituted alkyl group.

According to one embodiment of the present specification, Chemical Formula 1 includes two fused aliphatic hydrocarbon rings substituted with a substituted or unsubstituted alkyl group.

According to one embodiment of the present specification, Chemical Formula 1 includes three fused aliphatic hydrocarbon rings substituted with a substituted or unsubstituted alkyl group.

According to one embodiment of the present specification, Chemical Formula 1 includes four fused aliphatic hydrocarbon rings substituted with a substituted or unsubstituted alkyl group.

According to one embodiment of the present specification, Chemical Formula 1 includes at least one monocyclic or polycyclic fused aliphatic hydrocarbon ring having 3 to 30 carbon atoms substituted with a substituted or unsubstituted linear or branched alkyl group having 1 to 30 carbon atoms.

According to one embodiment of the present specification, Chemical Formula 1 includes at least one monocyclic or polycyclic fused aliphatic hydrocarbon ring having 3 to 20 carbon atoms substituted with a substituted or unsubstituted linear or branched alkyl group having 1 to 20 carbon atoms.

According to one embodiment of the present specification, Chemical Formula 1 includes at least one monocyclic or polycyclic fused aliphatic hydrocarbon ring having 3 to 10 carbon atoms substituted with a substituted or unsubstituted linear or branched alkyl group having 1 to 10 carbon atoms.

According to one embodiment of the present specification, Chemical Formula 1 includes at least one monocyclic or polycyclic fused aliphatic hydrocarbon ring having 3 to 30 carbon atoms substituted with a linear or branched alkyl group having 1 to 30 carbon atoms unsubstituted or substituted with deuterium.

According to one embodiment of the present specification, Chemical Formula 1 includes at least one monocyclic or polycyclic fused aliphatic hydrocarbon ring having 3 to 20 carbon atoms substituted with a linear or branched alkyl group having 1 to 20 carbon atoms unsubstituted or substituted with deuterium.

According to one embodiment of the present specification, Chemical Formula 1 includes at least one monocyclic or polycyclic fused aliphatic hydrocarbon ring having 3 to 10 carbon atoms substituted with a linear or branched alkyl group having 1 to 10 carbon atoms unsubstituted or substituted with deuterium.

According to one embodiment of the present specification, Chemical Formula 1 includes at least one monocyclic fused aliphatic hydrocarbon ring having 3 to 10 carbon atoms substituted with a linear or branched alkyl group having 1 to 30 carbon atoms unsubstituted or substituted with deuterium.

According to one embodiment of the present specification, Chemical Formula 1 includes at least one monocyclic or polycyclic fused aliphatic hydrocarbon ring having 3 to 30 carbon atoms unsubstituted or substituted with one or more selected from the group consisting of a linear or branched alkyl group having 1 to 30 carbon atoms unsubstituted or substituted with deuterium, and deuterium.

According to one embodiment of the present specification, Chemical Formula 1 includes at least one monocyclic or polycyclic fused aliphatic hydrocarbon ring having 3 to 20 carbon atoms unsubstituted or substituted with one or more selected from the group consisting of a linear or branched alkyl group having 1 to 20 carbon atoms unsubstituted or substituted with deuterium, and deuterium.

According to one embodiment of the present specification, Chemical Formula 1 includes at least one monocyclic or polycyclic fused aliphatic hydrocarbon ring having 3 to 10 carbon atoms unsubstituted or substituted with one or more selected from the group consisting of a linear or branched alkyl group having 1 to 10 carbon atoms unsubstituted or substituted with deuterium, and deuterium.

According to one embodiment of the present specification, Chemical Formula 1 includes one or more selected from the group consisting of a fused cyclohexane ring substituted with one or more selected from the group consisting of a methyl group substituted with deuterium, a methyl group and deuterium; a fused bicyclo[2.2.1]heptane ring substituted with a methyl group; and a fused bicyclo[2.2.1]octane ring substituted with a methyl group.

According to one embodiment of the present specification, Chemical Formula 1 includes one or more selected from the group consisting of a fused tetramethylcyclohexane ring; tetradeuteriumtetramethylcyclohexane; a fused tetratrideuteriummethylcyclohexane ring; a fused dimethylbicyclo[2.2.1]heptane ring; and a fused dimethylbicyclo[2.2.1]octane ring.

According to one embodiment of the present specification, Chemical Formula 1 includes at least one of a fused cyclohexane ring substituted with one or more selected from the group consisting of deuterium, a methyl group, and a methyl group substituted with deuterium; a fused bicyclo[2.2.1]heptane ring substituted with a methyl group; or a fused bicyclo[2.2.1]octane ring substituted with a methyl group.

According to one embodiment of the present specification, Chemical Formula 1 includes at least one of a fused tetramethylcyclohexane ring; tetradeuteriumtetramethylcyclohexane; a fused tetratrideuteriummethylcyclohexane ring; a fused bicyclo[2.2.1]heptane ring substituted with a methyl group; or a fused bicyclo[2.2.1]octane ring substituted with a methyl group.

According to one embodiment of the present specification, Chemical Formula 1 includes at least one fused cyclohexane ring substituted with a methyl group.

According to one embodiment of the present specification, Chemical Formula 1 includes at least one fused cyclohexane ring substituted with a methyl group substituted with deuterium.

According to one embodiment of the present specification, Chemical Formula 1 includes at least one fused cyclohexane ring substituted with a methyl group and deuterium.

According to one embodiment of the present specification, Chemical Formula 1 includes at least one fused bicyclo[2.2.1]heptane ring substituted with a methyl group.

According to one embodiment of the present specification, Chemical Formula 1 includes at least one fused bicyclo[2.2.1]octane ring substituted with a methyl group.

According to one embodiment of the present specification, Chemical Formula 1 includes at least one tetramethylcyclohexane.

According to one embodiment of the present specification, Chemical Formula 1 includes at least one tetramethylcyclohexane substituted with deuterium.

According to one embodiment of the present specification, Chemical Formula 1 includes at least one tetradeuteriumtetramethylcyclohexane.

According to one embodiment of the present specification, Chemical Formula 1 includes at least one fused tetratrideuteriummethylcyclohexane ring.

According to one embodiment of the present specification, Chemical Formula 1 includes at least one fused tetratrideuteriummethylcyclohexane ring substituted with deuterium.

According to one embodiment of the present specification, Chemical Formula 1 includes at least one fused dimethylbicyclo[2.2.1]heptane ring.

According to one embodiment of the present specification, Chemical Formula 1 includes at least one fused dimethylbicyclo[2.2.1]octane ring.

According to one embodiment of the present specification, Chemical Formula 1 includes at least one of the following structures.

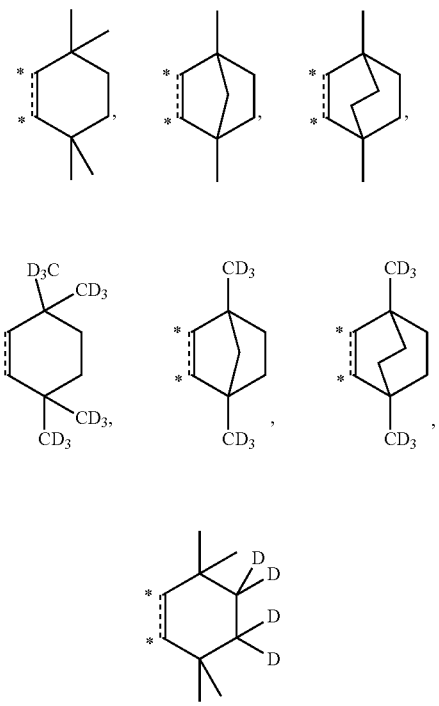

In the structures,

means a site bonding to adjacent ring in Chemical Formula 1, and in the structure, hydrogen at a position substitutable with deuterium may be substituted with deuterium.

According to one embodiment of the present specification, the meaning of "including at least one substituted or unsubstituted fused aliphatic hydrocarbon ring" is a substituted or unsubstituted aliphatic hydrocarbon ring being fused to at least one of fusible positions of Chemical Formula 1.

According to one embodiment of the present specification, the substituted or unsubstituted fused aliphatic hydrocarbon ring is included in at least one of Z1, A1, R11, R1 to R3, Y1 and Y2 of Chemical Formula 1.

In the present specification, including at least one substituted or unsubstituted fused aliphatic hydrocarbon ring in Chemical Formula 1 will be described using examples as follows, however, the structure is not limited thereto.

For example, 1) case of including a substituted or unsubstituted fused aliphatic hydrocarbon ring in R2 of Chemical Formula 1

When adjacent R2 s of Chemical Formula 1 bond to each other to form

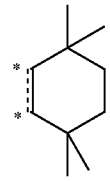

as the substituted or unsubstituted fused aliphatic hydrocarbon ring, adjacent R2 s may be represented as bonding to each other to form cyclohexane substituted with a methyl group, and may be represented by the following structure, however, the structure is not limited thereto.

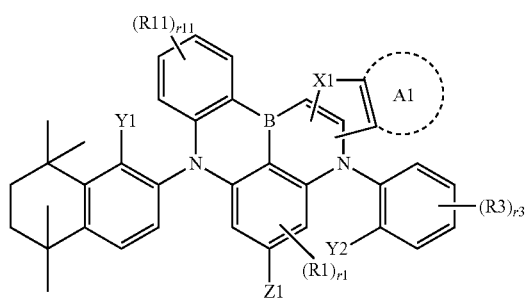

2) case of including a substituted or unsubstituted fused aliphatic hydrocarbon ring in A1 of Chemical Formula 1

When A1 of Chemical Formula 1 is benzene and includes

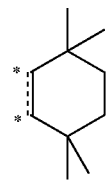

as the substituted or unsubstituted fused aliphatic hydrocarbon ring, A1 may be represented as tetrahydronaphthalene substituted with a methyl group, and may be represented by the following structure, however, Chemical Formula 1 is not limited to the following structure.

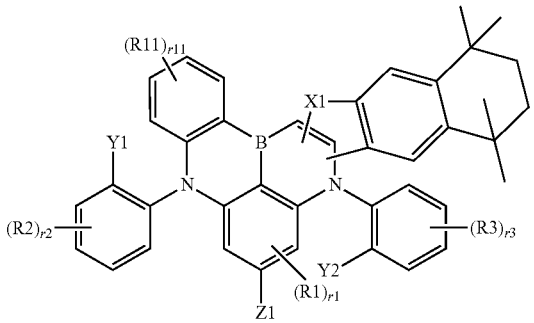

According to one embodiment of the present specification, A1 is a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms, R11 is hydrogen; a substituted or unsubstituted linear or branched alkyl group having 1 to 30 carbon atoms; a substituted or unsubstituted amine group; or a substituted or unsubstituted monocyclic or polycyclic heterocyclic group having 2 to 30 carbon atoms, or adjacent groups of R11 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms, at least one of Y1 and Y2 is deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic group having 2 to 30 carbon atoms, or bonds to adjacent groups to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms, and the remainder is hydrogen, Z1 is hydrogen; deuterium; a halogen group; a cyano group; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted linear or branched alkylsilyl group having 1 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms, and R2 and R3 are the same as or different from each other, and each independently hydrogen; deuterium; a halogen group; a cyano group; a substituted or unsubstituted linear or branched alkyl group having 1 to 30 carbon atoms; a substituted or unsubstituted linear or branched alkylsilyl group having 1 to 30 carbon atoms; a substituted or unsubstituted monocyclic or polycyclic arylsilyl group having 6 to 30 carbon atoms; a substituted or unsubstituted amine group; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic aryl group having 6 to 30 carbon atoms, or adjacent groups of R2 and R3 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, A1 is a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms.

According to one embodiment of the present specification, A1 is a substituted or unsubstituted monocyclic or polycyclic aromatic hydrocarbon ring having 6 to 20 carbon atoms; a substituted or unsubstituted monocyclic or polycyclic aliphatic hydrocarbon ring having 3 to 20 carbon atoms; or a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms.

According to one embodiment of the present specification, A1 is substituted or unsubstituted tetrahydronaphthalene; substituted or unsubstituted benzene; substituted or unsubstituted cyclohexane; substituted or unsubstituted methanonaphthalene; or substituted or unsubstituted ethanonaphthalene.

In A1, the "substituted or unsubstituted" means being substituted with one or more selected from the group consisting of deuterium; a halogen group; a cyano group; a linear or branched alkyl group having 1 to 30 carbon atoms unsubstituted or substituted with one or more selected from the group consisting of deuterium, and a monocyclic or polycyclic aryl group having 6 to 30 carbon atoms; a monocyclic or polycyclic cycloalkyl group having 3 to 30 carbon atoms; a monocyclic or polycyclic aryl group having 6 to 30 carbon atoms unsubstituted or substituted with a linear or branched alkyl group having 1 to 30 carbon atoms; a monocyclic or polycyclic heteroaryl group having 2 to 30 carbon atoms; and combinations thereof, or being unsubstituted.

In A1, the "substituted or unsubstituted" means being substituted with one or more selected from the group consisting of deuterium; F; a cyano group; a methyl group; a trideuteriumnethyl group ($CD_3$); an isopropyl group; a tert-butyl group; an adamantyl group; a cumyl group; a cumyl group substituted with deuterium; a phenyl group; a phenyl group substituted with a methyl group; a phenyl group substituted with a tert-butyl group; and combinations thereof, or being unsubstituted.

According to one embodiment of the present specification, A1 is tetrahydronaphthalene; benzene; cyclohexane; methanonaphthalene; or ethanonaphthalene, and the substituent is substituted with one or more selected from the group consisting of deuterium; F; a cyano group; a methyl group; a trideuteriumnethyl group ($CD_3$); an isopropyl group; a tert-butyl group; an adamantyl group; a cumyl group; a cumyl group substituted with deuterium; a phenyl group; a phenyl group substituted with a methyl group; a phenyl group substituted with a tert-butyl group; and combinations thereof, or is unsubstituted.

According to one embodiment of the present specification, R11 is hydrogen; a substituted or unsubstituted linear or branched alkyl group having 1 to 30 carbon atoms; a substituted or unsubstituted amine group; or a substituted or unsubstituted monocyclic or polycyclic heterocyclic group having 2 to 30 carbon atoms, or adjacent groups of R11 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, R11 is hydrogen; a substituted or unsubstituted linear or branched alkyl group having 1 to 20 carbon atoms; a substituted or unsubstituted amine group; or a substituted or unsubstituted monocyclic or polycyclic heterocyclic group having 2 to 20 carbon atoms, or adjacent groups of R11 bond to each other to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroring having 2 to 20 carbon atoms.

According to one embodiment of the present specification, R11 is hydrogen; a substituted or unsubstituted methyl group; a substituted or unsubstituted isopropyl group; a substituted or unsubstituted tert-butyl group; a substituted or unsubstituted phenyl group; a substituted or unsubstituted biphenyl group; a substituted or unsubstituted diphenylamine group; a substituted or unsubstituted ditetrahydronaphthylamine group; a substituted or unsubstituted carbazole group; or a substituted or unsubstituted hexahydrocarbazole group, or adjacent groups of R11 bond to each other to form substituted or unsubstituted cyclohexane; substituted or unsubstituted bicyclo[2.2.1]heptane; substituted or unsubstituted bicyclo[2.2.1]octane; substituted or unsubstituted indene; substituted or unsubstituted benzosilole; substituted or unsubstituted benzofuran; substituted or unsubstituted cyclopentanaphthalene; substituted or unsubstituted benzothiophene; or substituted or unsubstituted chromene.

In R11, the "substituted or unsubstituted" means being substituted with one or more selected from the group consisting of deuterium; a linear or branched alkyl group having 1 to 30 carbon atoms unsubstituted or substituted with one or more selected from the group consisting of deuterium, and a monocyclic or polycyclic aryl group having 6 to 30 carbon atoms; a monocyclic or polycyclic aryl group having 6 to 30 carbon atoms; and combinations thereof, or being unsubstituted.

In R11, the "substituted or unsubstituted" means being substituted with one or more selected from the group consisting of deuterium; a methyl group; a trideuteriummethyl group ($CD_3$); an isopropyl group; a tert-butyl group; a cumyl group; a cumyl group substituted with deuterium; a phenyl group; and combinations thereof, or being unsubstituted.

According to one embodiment of the present specification, R11 is hydrogen; a methyl group; an isopropyl group; a tert-butyl group; a phenyl group; a biphenyl group; a diphenylamine group; a ditetrahydronaphthylamine group; a carbazole group; or a hexahydrocarbazole group, or adjacent groups of R11 bond to each other to form cyclohexane; bicyclo[2.2.1]heptane; bicyclo[2.2.1]octane; indene; benzosilole; benzofuran; cyclopentanaphthalene; benzothiophene; or chromene, and the substituent is substituted with one or more selected from the group consisting of deuterium; a methyl group; a trideuteriummethyl group ($CD_3$); an isopropyl group; a tert-butyl group; a cumyl group; a cumyl group substituted with deuterium; a phenyl group; and combinations thereof, or is unsubstituted.

According to one embodiment of the present specification, r11 is 1.

According to one embodiment of the present specification, r11 is 2.

According to one embodiment of the present specification, when r11 is 1, R11 is hydrogen; a substituted or unsubstituted linear or branched alkyl group having 1 to 30 carbon atoms; a substituted or unsubstituted amine group; or a substituted or unsubstituted monocyclic or polycyclic heterocyclic group having 2 to 30 carbon atoms.

According to one embodiment of the present specification, when r11 is 1, R11 is hydrogen; a substituted or unsubstituted linear or branched alkyl group having 1 to 20 carbon atoms; a substituted or unsubstituted amine group; or a substituted or unsubstituted monocyclic or polycyclic heterocyclic group having 2 to 20 carbon atoms.

According to one embodiment of the present specification, when r11 is 1, R11 is hydrogen; a methyl group; an isopropyl group; a tert-butyl group; a phenyl group; a biphenyl group; a diphenylamine group; a ditetrahydronaphthylamine group; a carbazole group; or a hexahydrocarbazole group, and the substituent is substituted with one or more selected from the group consisting of deuterium; a methyl group; a trideuteriumnethyl group ($CD_3$); an isopropyl group; a tert-butyl group; a cumyl group; a cumyl group substituted with deuterium; a phenyl group; and combinations thereof, or is unsubstituted.

According to one embodiment of the present specification, when r11 is 2, adjacent R11 s bond to each other to form cyclohexane; bicyclo[2.2.1]heptane; bicyclo[2.2.1]octane; indene; benzosilole; benzofuran; cyclopentanaphthalene; benzothiophene; or chromene, each of which is unsubstituted or substituted with one or more selected from the group consisting of deuterium; a methyl group; a trideuteriumnethyl group ($CD_3$); an isopropyl group; a tert-butyl group; a cumyl group; a cumyl group substituted with deuterium; a phenyl group; and combinations thereof.

According to one embodiment of the present specification, r'11 is 1.

According to one embodiment of the present specification, R'11 is hydrogen; a substituted or unsubstituted linear or branched alkyl group having 1 to 20 carbon atoms; a substituted or unsubstituted amine group; or a substituted or unsubstituted monocyclic or polycyclic heterocyclic group having 2 to 20 carbon atoms.

According to one embodiment of the present specification, R'11 is hydrogen; a substituted or unsubstituted linear or branched alkyl group having 1 to 20 carbon atoms; a substituted or unsubstituted amine group; or a substituted or unsubstituted monocyclic or polycyclic heterocyclic group having 2 to 20 carbon atoms.

According to one embodiment of the present specification, R'11 is hydrogen; a methyl group; an isopropyl group;

a tert-butyl group; a phenyl group; a biphenyl group; a diphenylamine group; a ditetrahydronaphthylamine group; a carbazole group; or a hexahydrocarbazole group, and the substituent is substituted with one or more selected from the group consisting of deuterium; a methyl group; a trideuteriumnethyl group ($CD_3$); an isopropyl group; a tert-butyl group; a cumyl group; a cumyl group substituted with deuterium; a phenyl group; and combinations thereof, or is unsubstituted.

According to one embodiment of the present specification, A2 is a substituted or unsubstituted monocyclic or polycyclic aliphatic hydrocarbon ring having 3 to 30 carbon atoms.

According to one embodiment of the present specification, A2 is a substituted or unsubstituted monocyclic or polycyclic aliphatic hydrocarbon ring having 3 to 20 carbon atoms.

According to one embodiment of the present specification, A2 is cyclohexane; bicyclo[2.2.1]heptane; or bicyclo[2.2.1]octane, and the substituent is substituted with one or more selected from the group consisting of deuterium; a methyl group; a trideuteriumnethyl group ($CD_3$); an isopropyl group; a tert-butyl group; a cumyl group; a cumyl group substituted with deuterium; a phenyl group; and combinations thereof, or is unsubstituted.

According to one embodiment of the present specification, r"11 is 1.

According to one embodiment of the present specification, R"11 is hydrogen.

According to one embodiment of the present specification, at least one of Y1 and Y2 is deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic group having 2 to 30 carbon atoms, or bonds to adjacent groups to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterering having 2 to 30 carbon atoms, and the remainder is hydrogen.

According to one embodiment of the present specification, at least one of Y1 and Y2 is deuterium; a cyano group; a halogen group; a substituted or unsubstituted linear or branched alkyl group having 1 to 20 carbon atoms; a substituted or unsubstituted linear or branched alkylsilyl group having 1 to 20 carbon atoms; a substituted or unsubstituted linear or branched alkenyl group having 2 to 20 carbon atoms; a substituted or unsubstituted monocyclic or polycyclic aryl group having 6 to 20 carbon atoms; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heterocyclic group having 2 to 20 carbon atoms, or bonds to adjacent groups to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heterering having 2 to 20 carbon atoms, and the remainder is hydrogen.

According to one embodiment of the present specification, at least one of Y1 and Y2 is deuterium; a cyano group; F; a substituted or unsubstituted methyl group; a substituted or unsubstituted tert-butyl group; a substituted or unsubstituted trimethylsilyl group; a substituted or unsubstituted vinyl group; a substituted or unsubstituted phenyl group; a substituted or unsubstituted biphenyl group; a substituted or unsubstituted naphthyl group; or a substituted or unsubstituted phenanthrene group, or bonds to adjacent groups to form substituted or unsubstituted indene; substituted or unsubstituted benzofuran; substituted or unsubstituted benzothiophene; substituted or unsubstituted cyclopentanaphthalene; substituted or unsubstituted naphthofuran; substituted or unsubstituted tetrahydronaphthalene; substituted or unsubstituted benzosilole; substituted or unsubstituted benzene; substituted or unsubstituted naphthalene; or substituted or unsubstituted cyclohexane, and the remainder is hydrogen.

In Y1 and Y2, the "substituted or unsubstituted" means being substituted with one or more selected from the group consisting of deuterium; a halogen group; a cyano group; a linear or branched alkyl group having 1 to 30 carbon atoms unsubstituted or substituted with one or more selected from the group consisting of deuterium, a halogen group, and a monocyclic or polycyclic aryl group having 6 to 30 carbon atoms; a linear or branched alkylsilyl group having 1 to 30 carbon atoms; a monocyclic or polycyclic aryl group having 6 to carbon atoms; and combinations thereof, or being unsubstituted.

In Y1 and Y2, the "substituted or unsubstituted" means being substituted with one or more selected from the group consisting of deuterium; F; a cyano group; a methyl group; a trideuteriumnethyl group ($CD_3$); an isopropyl group; a tert-butyl group; a cumyl group; a cumyl group substituted with deuterium; a trifluoromethyl group ($CF_3$); a trimethylsilyl group; a phenyl group; and combinations thereof, or being unsubstituted.

According to one embodiment of the present specification, at least one of Y1 and Y2 is deuterium; a cyano group; F; a methyl group; a tert-butyl group; a trimethylsilyl group; a vinyl group; a phenyl group; a biphenyl group; a naphthyl group; or a phenanthrene group, or bonds to adjacent groups to form indene; benzofuran; benzothiophene; cyclopentanaphthalene; naphthofuran; tetrahydronaphthalene; benzosilole; benzene; naphthalene; or cyclohexane, and the remainder is hydrogen, and the substituent is substituted with one or more selected from the group consisting of deuterium; F; a cyano group; a methyl group; a trideuteriumnethyl group ($CD_3$); an isopropyl group; a tert-butyl group; a cumyl group; a cumyl group substituted with deuterium; a trifluoromethyl group ($CF_3$); a trimethylsilyl group; a phenyl group; and combinations thereof, or is unsubstituted.

According to one embodiment of the present specification, Y2 is hydrogen.

According to one embodiment of the present specification, Y1 is deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic group having 2 to 30 carbon atoms, or bonds to R2 to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, Y1 is deuterium; a cyano group; a halogen group; a substituted or unsubstituted linear or branched alkyl group having 1 to 20 carbon atoms; a substituted or unsubstituted linear or branched alkylsilyl group having 1 to 20 carbon atoms; a substituted or unsubstituted linear or branched alkenyl group having 2 to 20 carbon atoms; a substituted or unsubstituted monocyclic or polycyclic aryl group having 6 to 20 carbon atoms; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heterocyclic group having 2 to 20 carbon atoms, or bonds to R2 to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroring having 2 to 20 carbon atoms.

According to one embodiment of the present specification, Y1 is deuterium; a cyano group; F; a methyl group; a tert-butyl group; a trimethylsilyl group; a vinyl group; a phenyl group; a biphenyl group; a naphthyl group; or a phenanthrene group, or bonds to R2 to form indene; benzofuran; benzothiophene; cyclopentanaphthalene; naphthofuran; tetrahydronaphthalene; benzosilole; benzene; naphthalene; or cyclohexane, and the substituent is substituted with one or more selected from the group consisting of deuterium; F; a cyano group; a methyl group; a trideuteriumnethyl group ($CD_3$); an isopropyl group; a tert-butyl group; a cumyl group; a cumyl group substituted with deuterium; a trifluoromethyl group ($CF_3$); a trimethylsilyl group; a phenyl group; and combinations thereof, or is unsubstituted.

According to one embodiment of the present specification, Y1 is hydrogen.

According to one embodiment of the present specification, Y2 is deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic group having 2 to 30 carbon atoms, or bonds to R3 to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, Y2 is deuterium; a cyano group; a halogen group; a substituted or unsubstituted linear or branched alkyl group having 1 to 20 carbon atoms; a substituted or unsubstituted linear or branched alkylsilyl group having 1 to 20 carbon atoms; a substituted or unsubstituted linear or branched alkenyl group having 2 to 20 carbon atoms; a substituted or unsubstituted monocyclic or polycyclic aryl group having 6 to 20 carbon atoms; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heterocyclic group having 2 to 20 carbon atoms, or bonds to R3 to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroring having 2 to 20 carbon atoms.

According to one embodiment of the present specification, Y2 is deuterium; a cyano group; F; a methyl group; a tert-butyl group; a trimethylsilyl group; a vinyl group; a phenyl group; a biphenyl group; a naphthyl group; or a phenanthrene group, or bonds to R3 to form indene; benzofuran; benzothiophene; cyclopentanaphthalene; naphthofuran; tetrahydronaphthalene; benzosilole; benzene; naphthalene; or cyclohexane, and the substituent is substituted with one or more selected from the group consisting of deuterium; F; a cyano group; a methyl group; a trideuteriumnethyl group ($CD_3$); an isopropyl group; a tert-butyl group; a cumyl group; a cumyl group substituted with deuterium; a trifluoromethyl group ($CF_3$); a trimethylsilyl group; a phenyl group; and combinations thereof, or is unsubstituted.

According to one embodiment of the present specification, Y1 and Y2 are the same as or different from each other, and each independently deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic group having 2 to 30 carbon atoms, or any one or more of Y1 and R2, and Y2 and R3 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, Y1 and Y2 are the same as or different from each other, and each independently deuterium; a cyano group; a halogen group; a substituted or unsubstituted linear or branched alkyl group having 1 to 20 carbon atoms; a substituted or unsubstituted linear or branched alkylsilyl group having 1 to 20 carbon atoms; a substituted or unsubstituted linear or branched alkenyl group having 2 to 20 carbon atoms; a substituted or unsubstituted monocyclic or polycyclic aryl group having 6 to 20 carbon atoms; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heterocyclic group having 2 to 20 carbon atoms, or any one or more of Y1 and R2, and Y2 and R3 bond to each other to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroring having 2 to 20 carbon atoms.

According to one embodiment of the present specification, Y1 and Y2 are the same as or different from each other, and each independently deuterium; a cyano group; F; a methyl group; a tert-butyl group; a trimethylsilyl group; a vinyl group; a phenyl group; a biphenyl group; a naphthyl group; or a phenanthrene group, or any one or more of Y1 and R2, and Y2 and R3 bond to each other to form indene; benzofuran; benzothiophene; cyclopentanaphthalene; naphthofuran; tetrahydronaphthalene; benzosilole; benzene; naphthalene; or cyclohexane, and the substituent is substituted with one or more selected from the group consisting of deuterium; F; a cyano group; a methyl group; a trideuteriumnethyl group (CD$_3$); an isopropyl group; a tert-butyl group; a cumyl group; a cumyl group substituted with deuterium; a trifluoromethyl group (CF$_3$); a trimethylsilyl group; a phenyl group; and combinations thereof, or is unsubstituted.

According to one embodiment of the present specification, Z1 is hydrogen; deuterium; a halogen group; a cyano group; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted linear or branched alkylsilyl group having 1 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms.

According to one embodiment of the present specification, Z1 is hydrogen; deuterium; a halogen group; a cyano group; a substituted or unsubstituted linear or branched alkyl group having 1 to 20 carbon atoms; a substituted or unsubstituted monocyclic or polycyclic cycloalkyl group having 3 to 20 carbon atoms; a substituted or unsubstituted amine group; a substituted or unsubstituted linear or branched alkylsilyl group having 1 to 20 carbon atoms; a substituted or unsubstituted monocyclic or polycyclic aryl group having 6 to 20 carbon atoms; or a substituted or unsubstituted monocyclic or polycyclic heterocyclic group having 2 to 20 carbon atoms.

According to one embodiment of the present specification, Z1 is hydrogen; deuterium; F; a cyano group; a substituted or unsubstituted methyl group; a substituted or unsubstituted ethyl group; a substituted or unsubstituted isopropyl group; a substituted or unsubstituted n-butyl group; a substituted or unsubstituted tert-butyl group; a substituted or unsubstituted cyclohexyl group; a substituted or unsubstituted adamantyl group; a substituted or unsubstituted trimethylsilyl group; a substituted or unsubstituted diphenylamine group; a substituted or unsubstituted phenylbiphenylamine group; a substituted or unsubstituted phenylnaphthylamine group; a substituted or unsubstituted dibiphenylamine group; a substituted or unsubstituted ditetrahydronaphthylamine group; a substituted or unsubstituted phenyltetrahydronaphthylamine group; a substituted or unsubstituted N-phenyldibenzofuranamine group; a substituted or unsubstituted N-phenyldibenzothiophenamine group; a substituted or unsubstituted phenyl group; a substituted or unsubstituted biphenyl group; a substituted or unsubstituted naphthyl group; a substituted or unsubstituted dihydroacridine group; a substituted or unsubstituted hexahydrocarbazole group; a substituted or unsubstituted dihydrobenzoazasiline group; or a substituted or unsubstituted decahydrocarbazole group.

In Z1, the "substituted or unsubstituted" means being substituted with one or more selected from the group consisting of deuterium; a halogen group; a cyano group; a linear or branched alkyl group having 1 to 30 carbon atoms unsubstituted or substituted with one or more selected from the group consisting of deuterium, a halogen group, and a monocyclic or polycyclic aryl group having 6 to 30 carbon atoms; a linear or branched alkylsilyl group having 1 to 30 carbon atoms; a substituted or unsubstituted monocyclic or polycyclic arylamine group having 6 to 30 carbon atoms; a monocyclic or polycyclic aryl group having 6 to 30 carbon atoms; and combinations thereof, or being unsubstituted.

In Z1, the "substituted or unsubstituted" means being substituted with one or more selected from the group consisting of deuterium; F; a cyano group; a methyl group; a trideuteriumnethyl group (CD$_3$); an isopropyl group; a tert-butyl group; a trimethylsilyl group; a tert-butyldimethylsilyl group; a diphenylamine group; a phenyl group; and combinations thereof, or being unsubstituted.

According to one embodiment of the present specification, Z1 is hydrogen; deuterium; F; a cyano group; a methyl group; an ethyl group; an isopropyl group; an n-butyl group; a tert-butyl group; a cyclohexyl group; an adamantyl group;

a trimethylsilyl group; a diphenylamine group; a phenylbiphenylamine group; a phenylnaphthylamine group; a diphenylamine group; a ditetrahydronaphthylamine group; a phenyltetrahydronaphthylamine group; an N-phenyldibenzofuranamine group; an N-phenyldibenzothiophenamine group; a phenyl group; a biphenyl group; a naphthyl group; a dihydroacridine group; a hexahydrocarbazole group; a dihydrobenzoazasiline group; or a decahydrocarbazole group, and the substituent is substituted with one or more selected from the group consisting of deuterium; F; a cyano group; a methyl group; a trideuteriumnethyl group ($CD_3$); an isopropyl group; a tert-butyl group; a trimethylsilyl group; a tert-butyldimethylsilyl group; a diphenylamine group; a phenyl group; and combinations thereof, or is unsubstituted.

According to one embodiment of the present specification, r1 is 1.

According to one embodiment of the present specification, R1 is hydrogen.

According to one embodiment of the present specification, r2 is 1.

According to one embodiment of the present specification, r2 is 2.

According to one embodiment of the present specification, r3 is 1.

According to one embodiment of the present specification, r3 is 2.

According to one embodiment of the present specification, R2 and R3 are the same as or different from each other, and each independently hydrogen; deuterium; a halogen group; a cyano group; a substituted or unsubstituted linear or branched alkyl group having 1 to 30 carbon atoms; a substituted or unsubstituted linear or branched alkylsilyl group having 1 to 30 carbon atoms; a substituted or unsubstituted monocyclic or polycyclic arylsilyl group having 6 to 30 carbon atoms; a substituted or unsubstituted amine group; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic aryl group having 6 to 30 carbon atoms, or adjacent groups of R2 and R3 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

According to one embodiment of the present specification, R2 and R3 are the same as or different from each other, and each independently hydrogen; deuterium; a halogen group; a cyano group; a substituted or unsubstituted linear or branched alkyl group having 1 to 20 carbon atoms; a substituted or unsubstituted linear or branched alkylsilyl group having 1 to 20 carbon atoms; a substituted or unsubstituted monocyclic or polycyclic arylsilyl group having 6 to 20 carbon atoms; a substituted or unsubstituted amine group; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic aryl group having 6 to 20 carbon atoms, or adjacent groups of R2 and R3 bond to each other to form a substituted or unsubstituted monocyclic or polycyclic aliphatic hydrocarbon ring having 3 to 20 carbon atoms; a substituted or unsubstituted monocyclic or polycyclic aromatic hydrocarbon ring having 6 to 20 carbon atoms; a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroring having 2 to 20 carbon atoms.

According to one embodiment of the present specification, R2 and R3 are the same as or different from each other, and each independently hydrogen; deuterium; F; a cyano group; a substituted or unsubstituted methyl group; a substituted or unsubstituted isopropyl group; a substituted or unsubstituted tert-butyl group; a substituted or unsubstituted diphenylamine group; a substituted or unsubstituted trimethylsilyl group; a substituted or unsubstituted triphenylsilyl group; a substituted or unsubstituted tetrahydronaphthyl group; or a substituted or unsubstituted phenyl group, or adjacent groups of R2 and R3 bond to each other to form substituted or unsubstituted indene; substituted or unsubstituted benzofuran; substituted or unsubstituted benzothiophene; substituted or unsubstituted cyclopentanaphthalene; substituted or unsubstituted naphthofuran; substituted or unsubstituted tetrahydronaphthalene; substituted or unsubstituted benzosilole; substituted or unsubstituted benzene; substituted or unsubstituted naphthalene; or substituted or unsubstituted cyclohexane.

In R2 and R3, the "substituted or unsubstituted" means being substituted with one or more selected from the group consisting of deuterium; a halogen group; a cyano group; a linear or branched alkyl group having 1 to 30 carbon atoms; a linear or branched alkylsilyl group having 1 to 30 carbon atoms; a monocyclic or polycyclic arylsilyl group having 6 to 30 carbon atoms; a monocyclic or polycyclic arylamine group having 6 to 30 carbon atoms; a monocyclic or polycyclic aryl group having 6 to 30 carbon atoms; and combinations thereof, or being unsubstituted.

In R2 and R3, the "substituted or unsubstituted" means being substituted with one or more selected from the group consisting of deuterium; F; a cyano group; a methyl group; a tert-butyl group; a trimethylsilyl group; a triphenylsilyl group; a phenyl group; and combinations thereof, or being unsubstituted.

According to one embodiment of the present specification, R2 and R3 are the same as or different from each other, and each independently hydrogen; deuterium; F; a cyano group; a methyl group; an isopropyl group; a tert-butyl group; a diphenylamine group; a trimethylsilyl group; a triphenylsilyl group; a tetrahydronaphthyl group; or a phenyl group, or adjacent groups of R2 and R3 bond to each other to form indene; benzofuran; benzothiophene; cyclopentanaphthalene; naphthofuran; tetrahydronaphthalene; benzosilole; benzene; naphthalene; or cyclohexane, and the substituent is substituted with one or more selected from the group consisting of deuterium; F; a cyano group; a methyl group; a tert-butyl group; a trimethylsilyl group; a triphenylsilyl group; a phenyl group; and combinations thereof, or is unsubstituted.

As for the "adjacent group" in R2, Y1 may be the adjacent group when r2 is 1, and Y1 or R2 may be the adjacent group when r2 is 2 or greater.

As for the "adjacent group" in R3, Y2 may be the adjacent group when r3 is 1, and Y2 or R3 may be the adjacent group when r3 is 2 or greater.

In the present specification, the cumyl group means
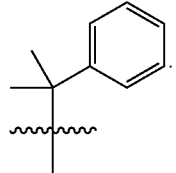 [SMILES: *C(C)(C)c1ccccc1]
According to one embodiment of the present specification, Chemical Formula 1 is any one selected from among the following compounds.
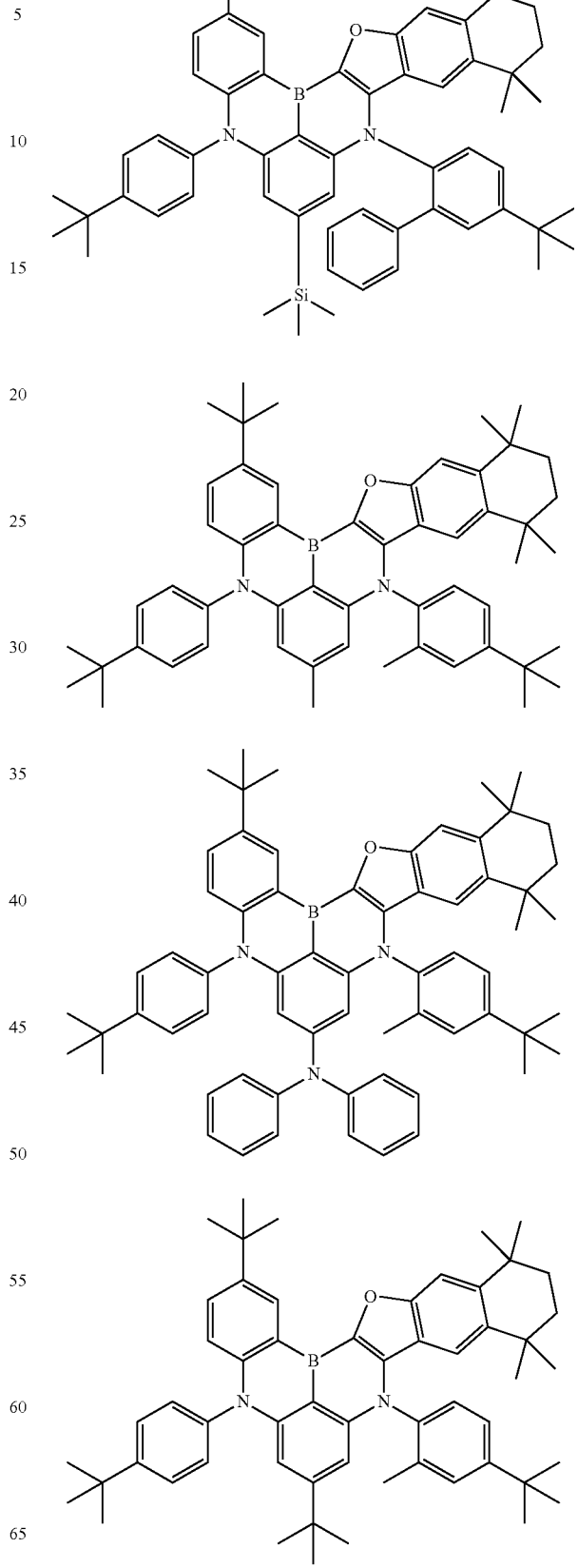

33
-continued
34
-continued
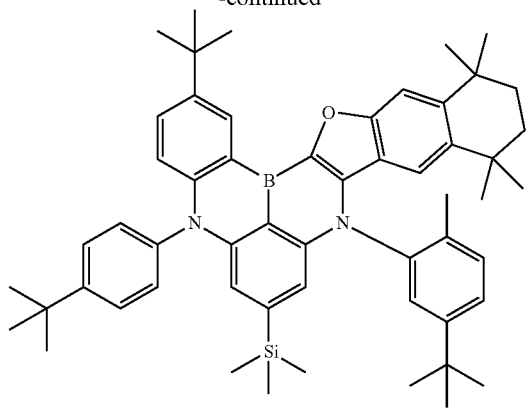
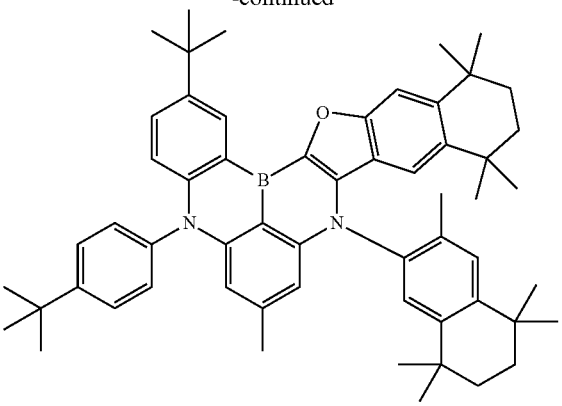
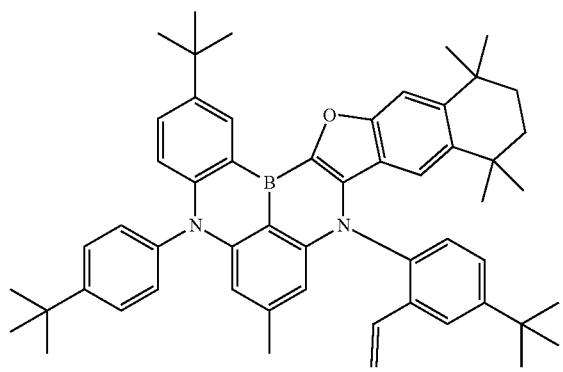
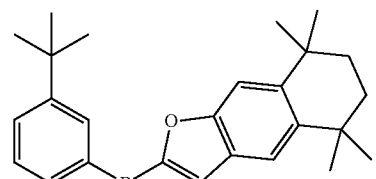
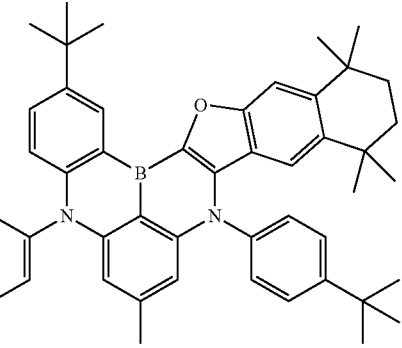
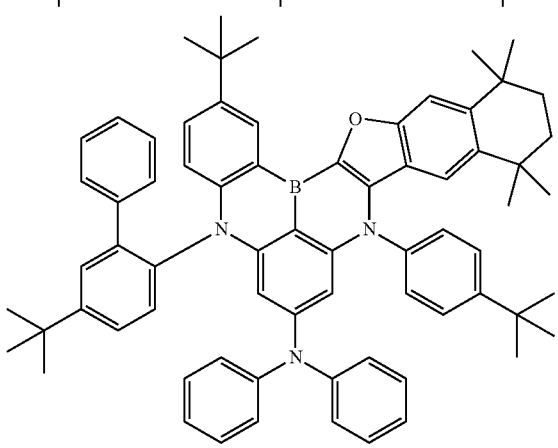

35
-continued
36
-continued
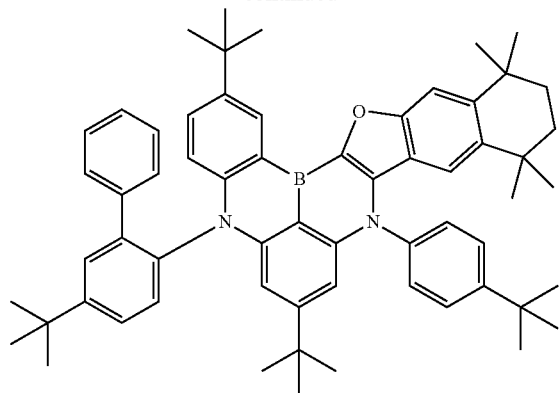
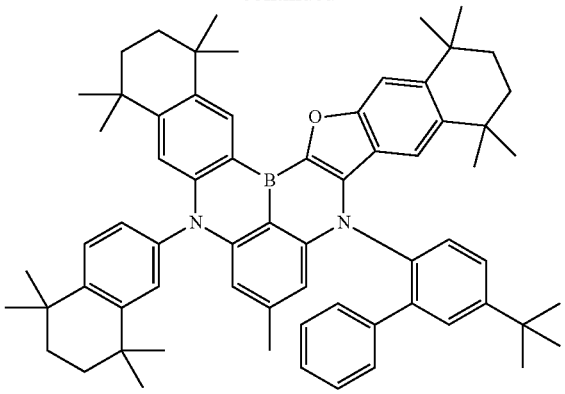

| 37 | 38 |
|---|---|
| -continued | -continued |
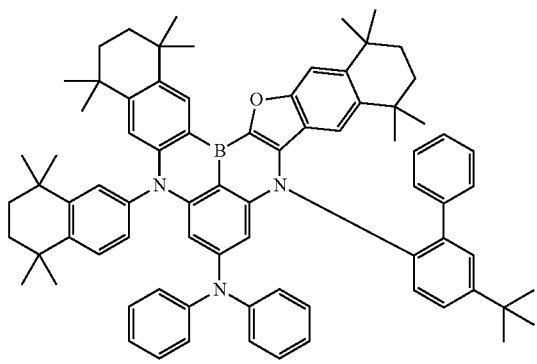
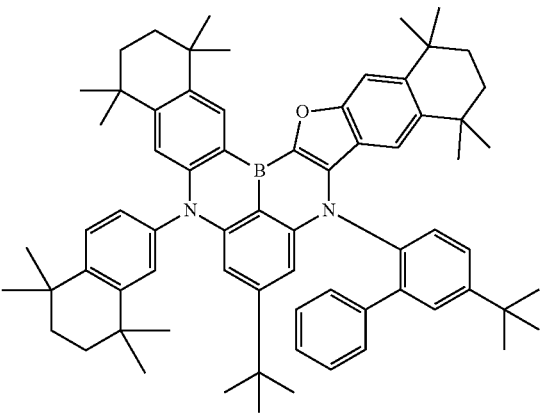
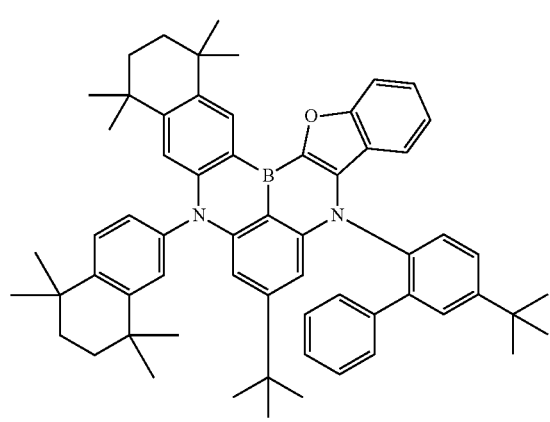
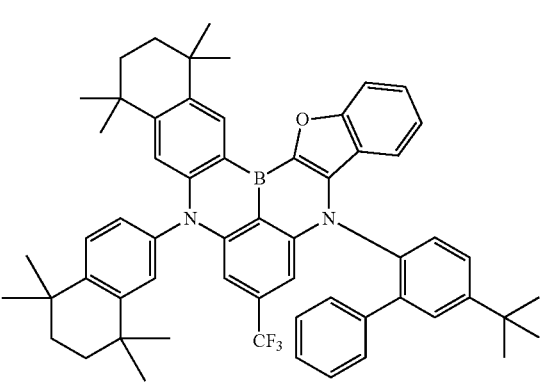
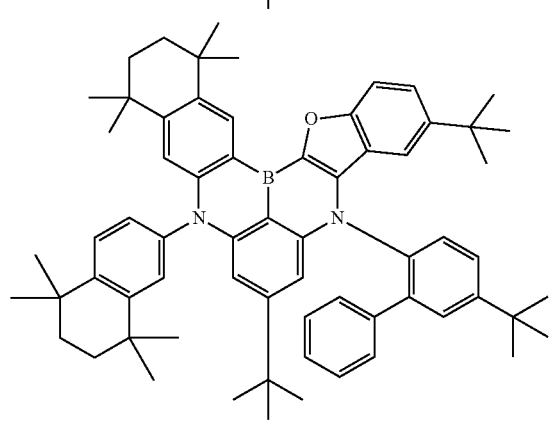
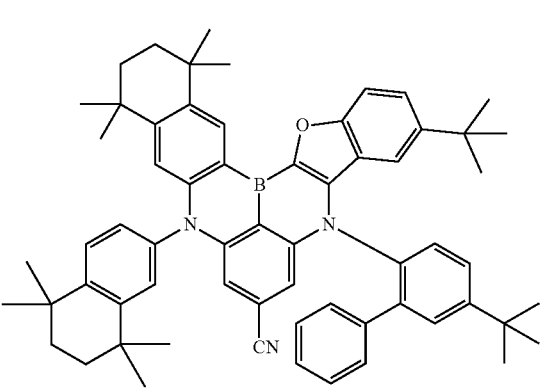

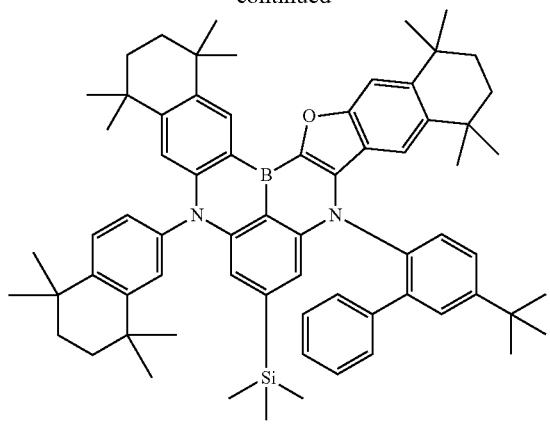
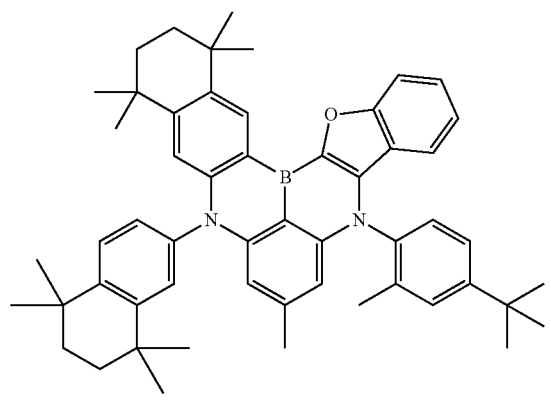
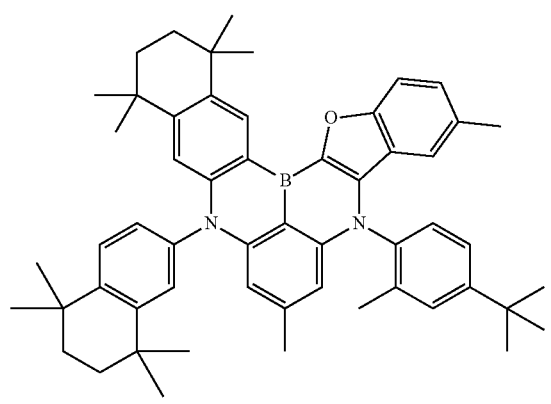
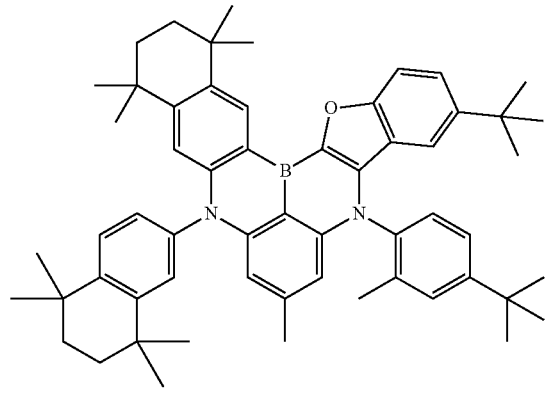
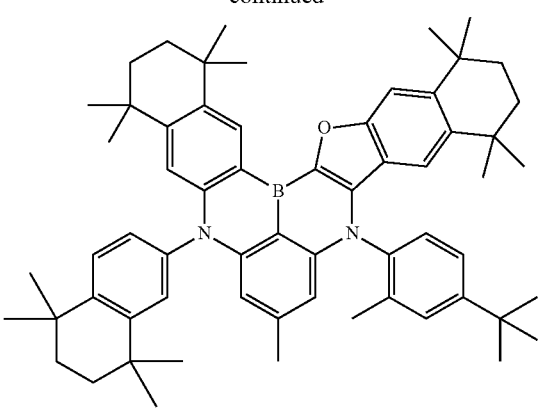

41
-continued
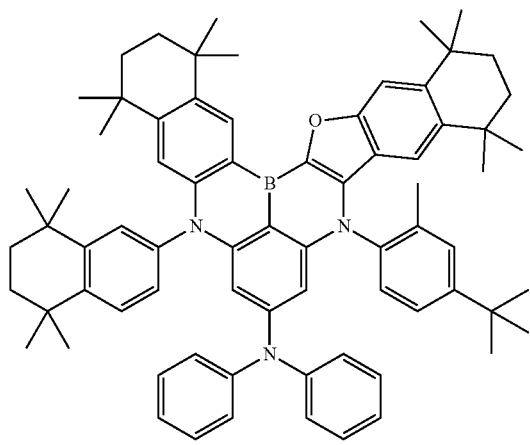
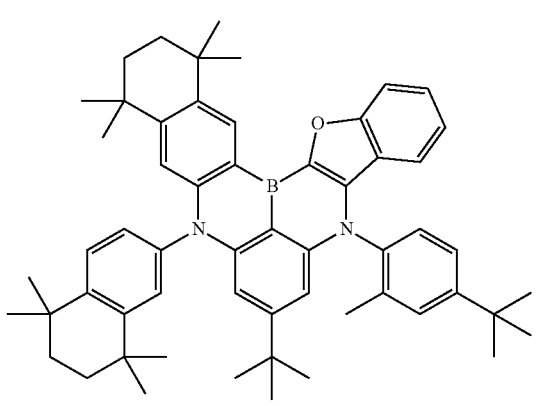
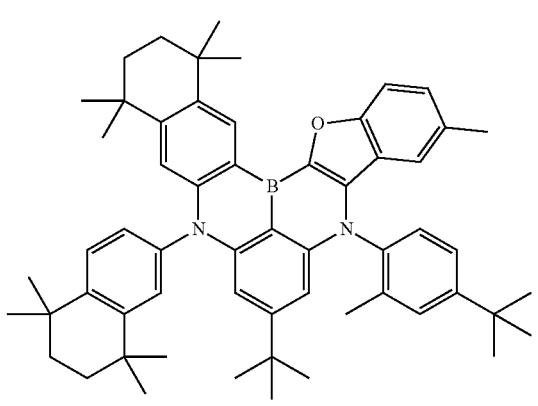
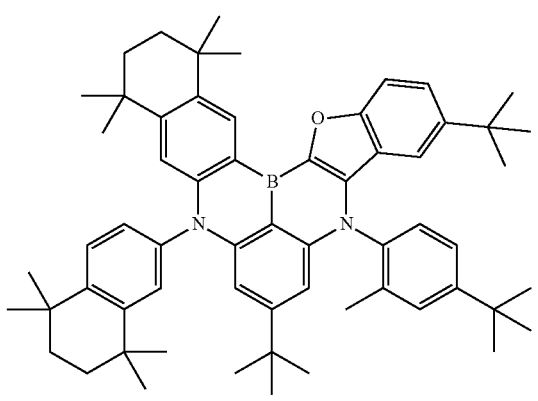
42
-continued
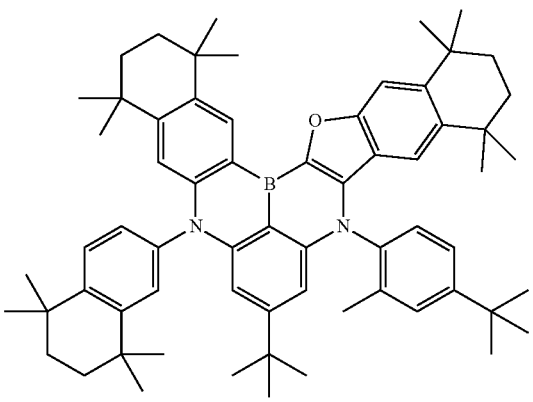
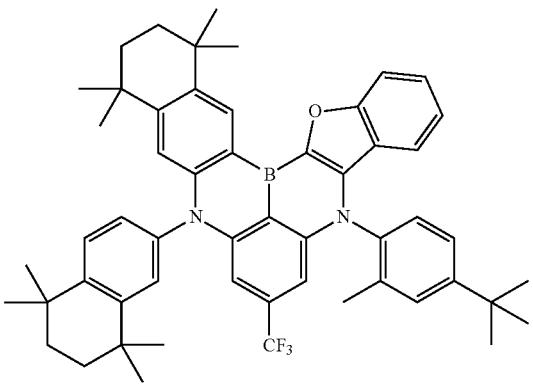
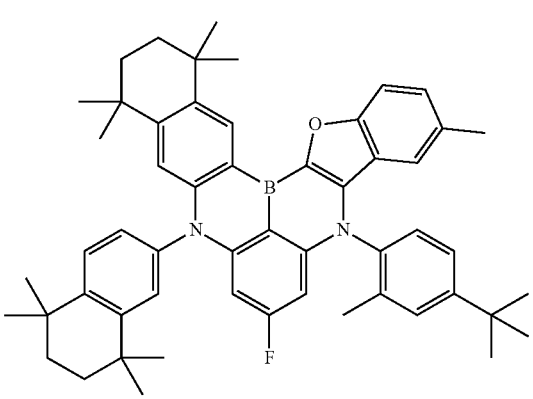
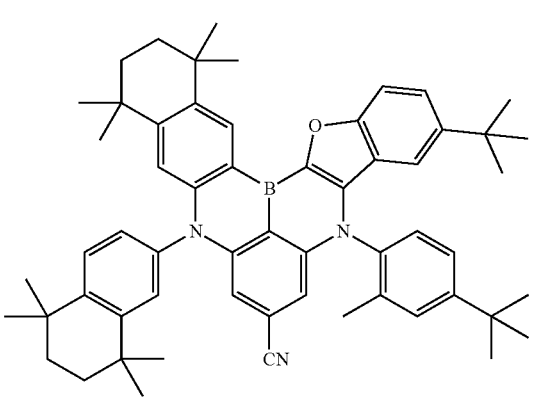

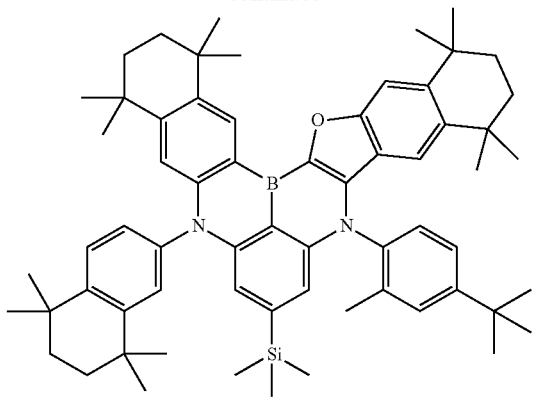
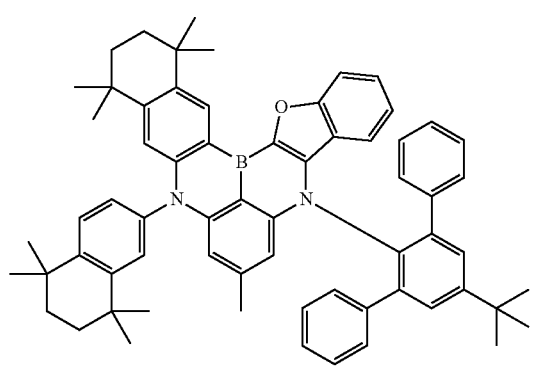
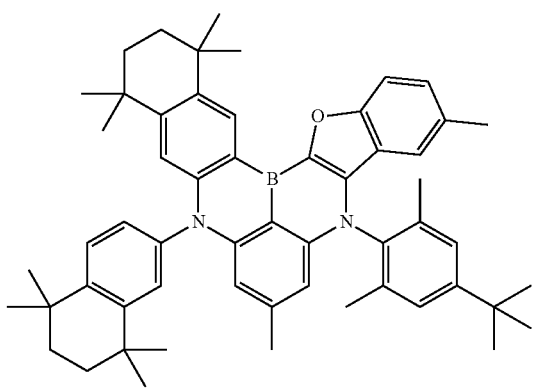
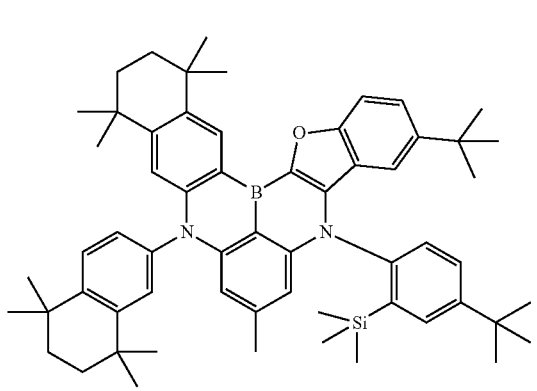
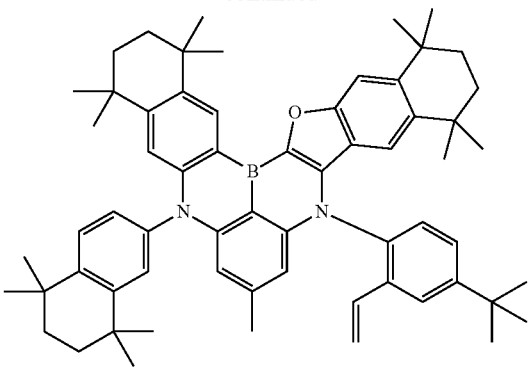
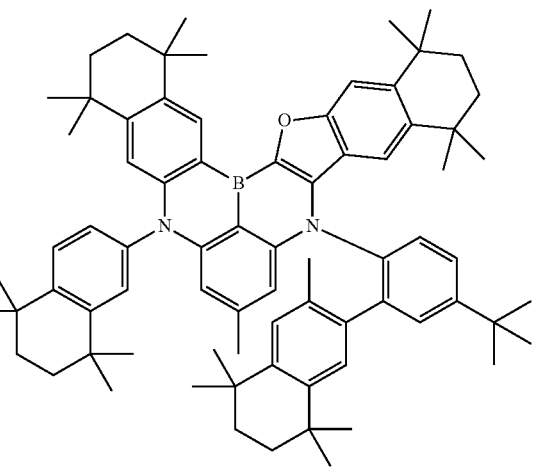
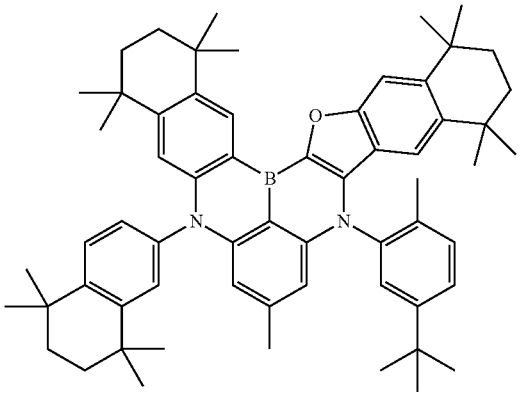
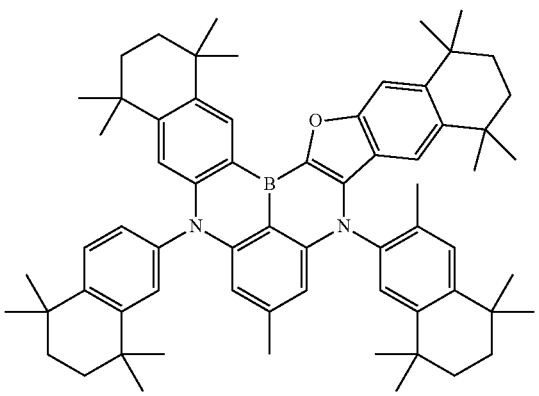

45
-continued
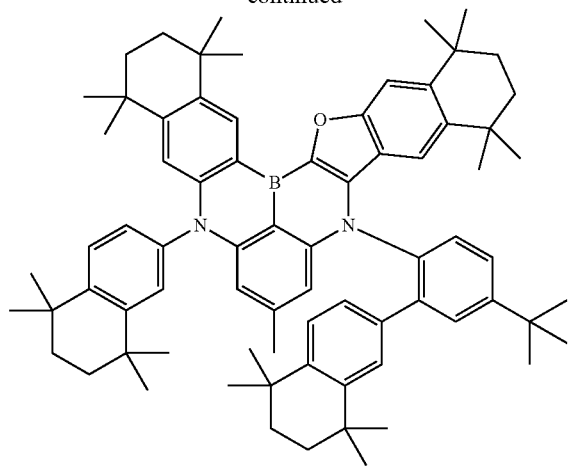
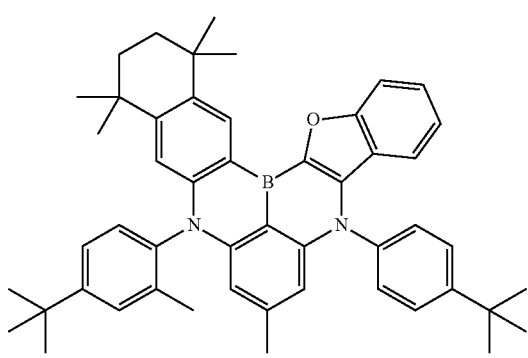
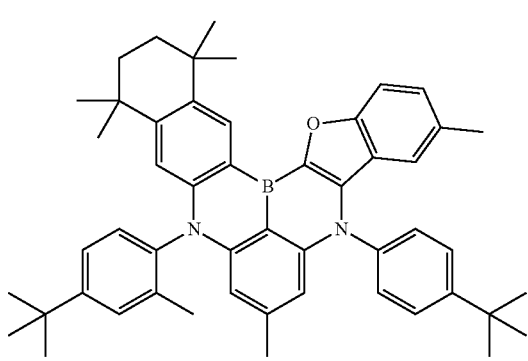
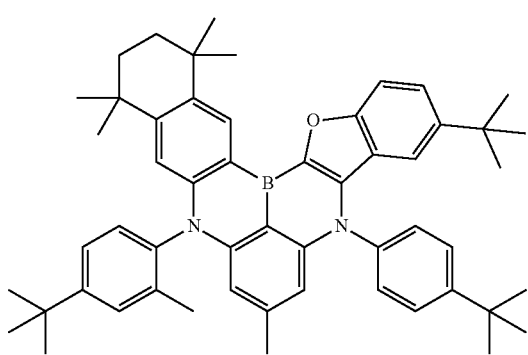
46
-continued
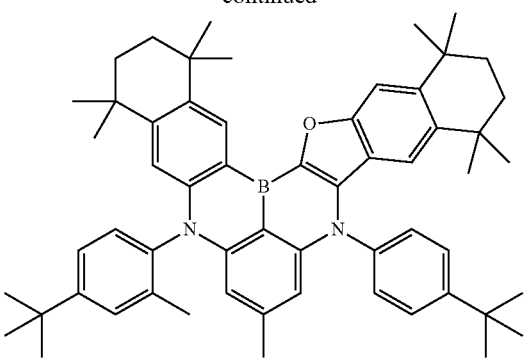
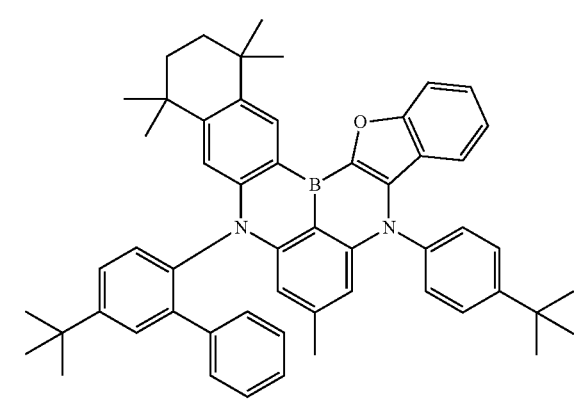
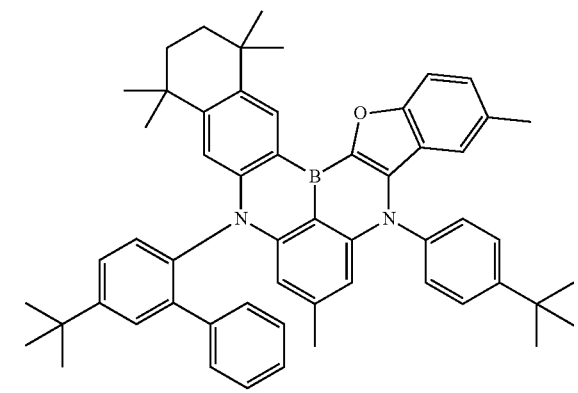
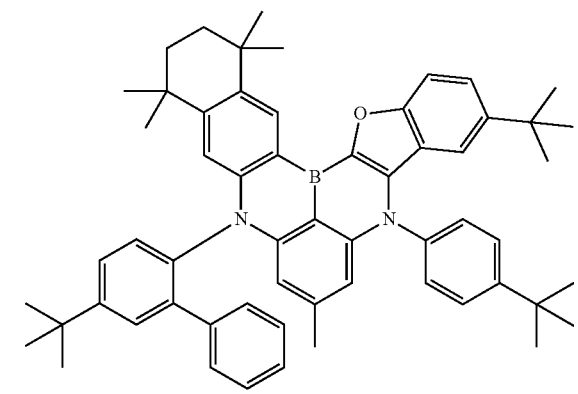

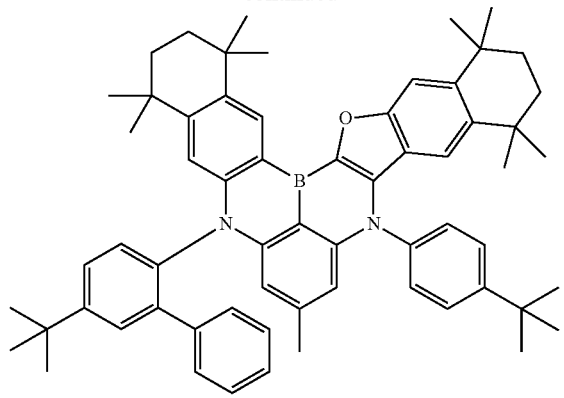
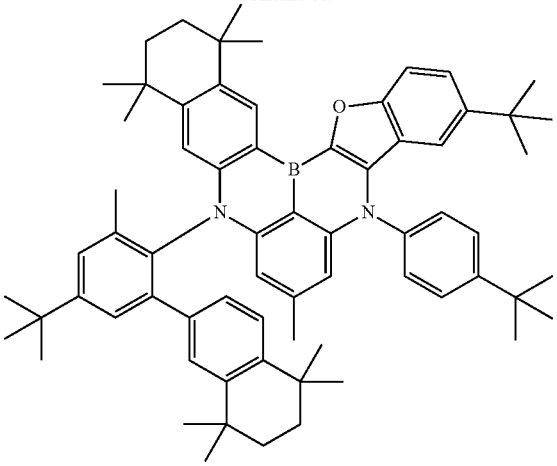
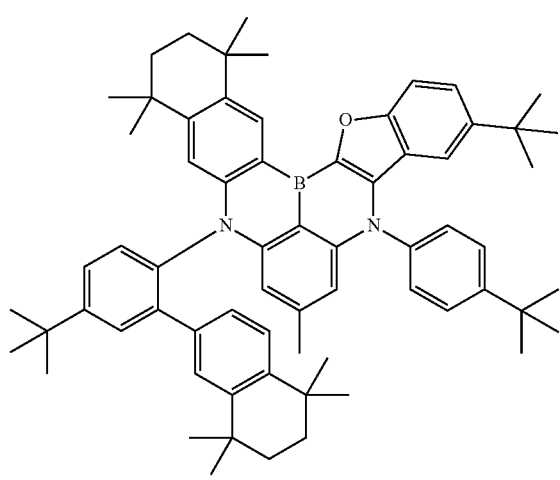
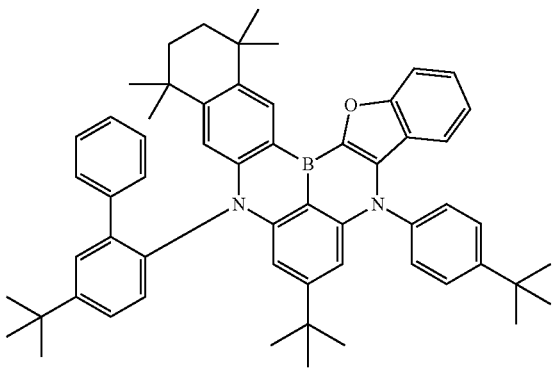
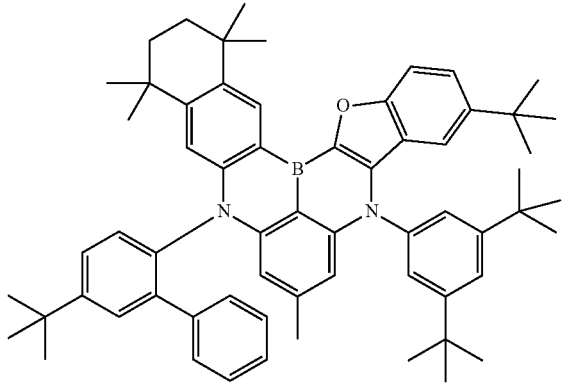
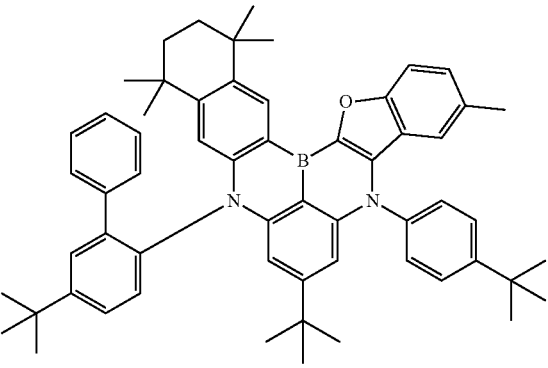
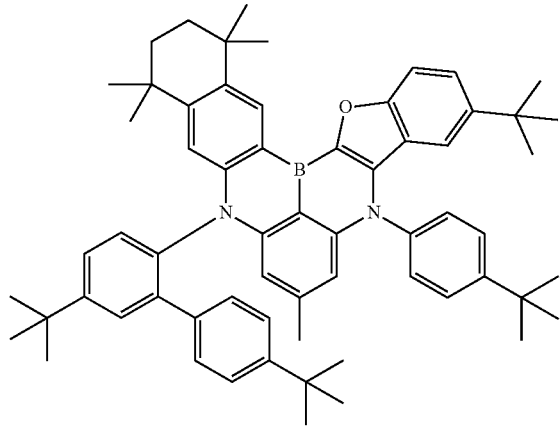
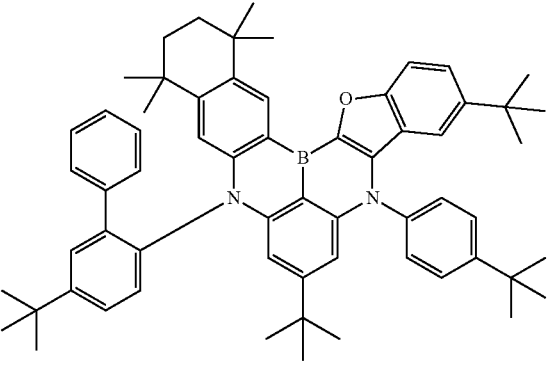

| 49 -continued | 50 -continued |
|---|---|
| 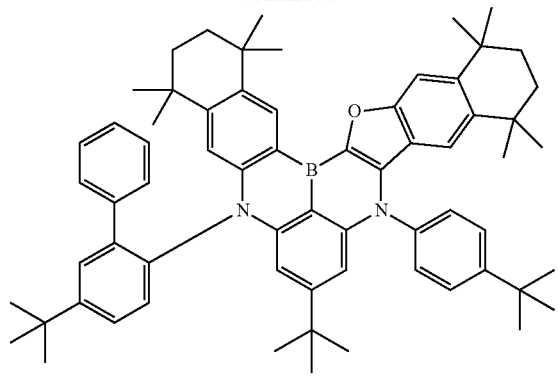 | 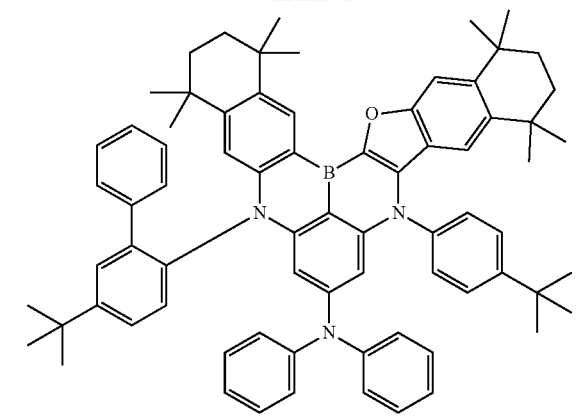 |
| 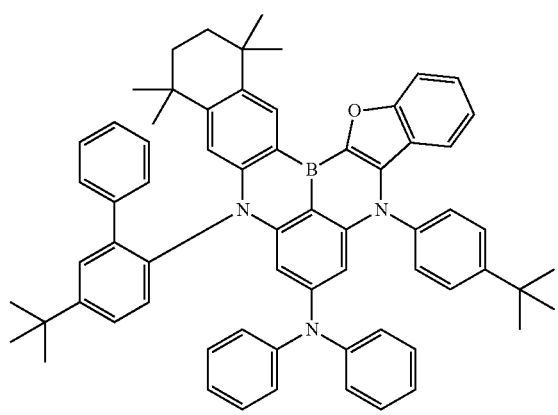 | 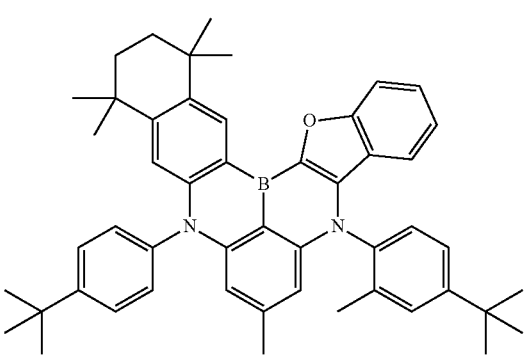 |
| 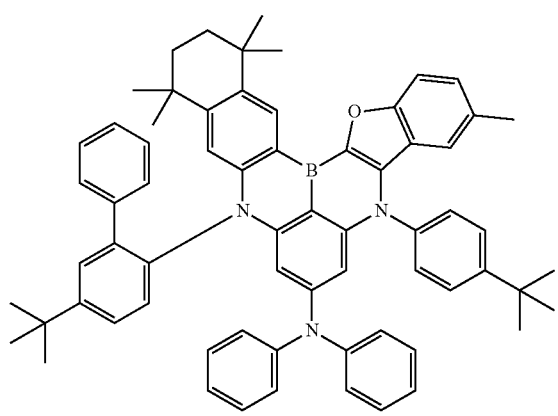 | 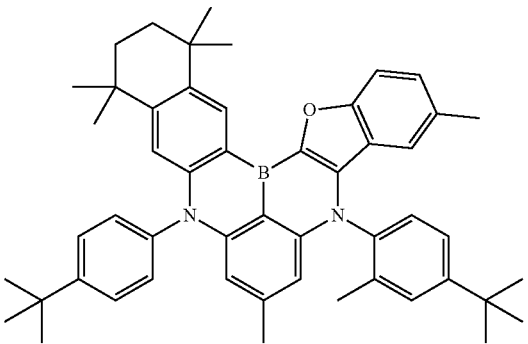 |
| 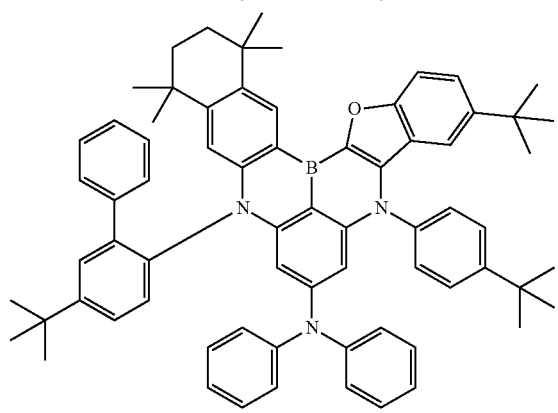 | 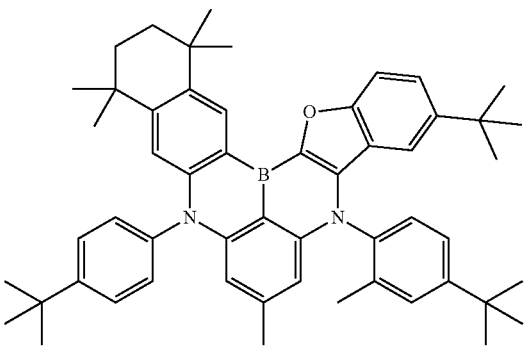 |

51
-continued
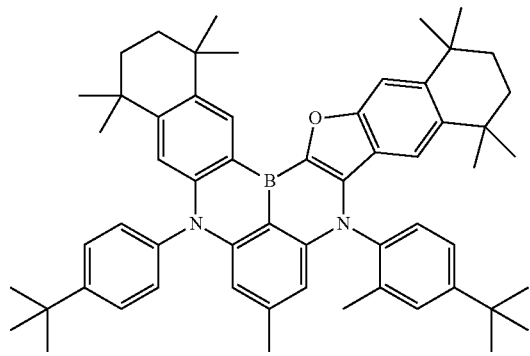
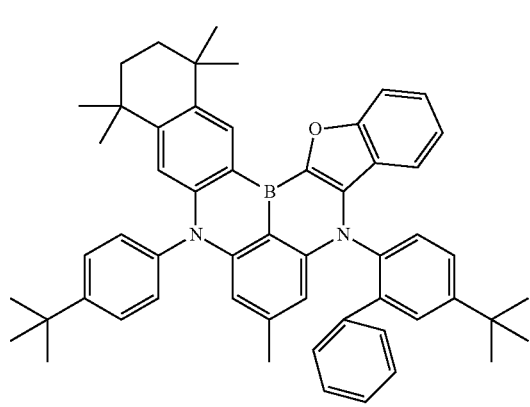
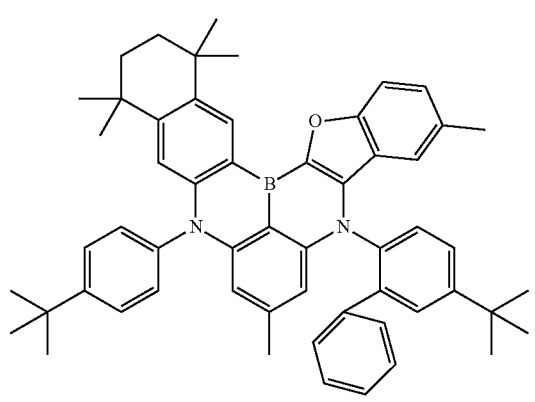
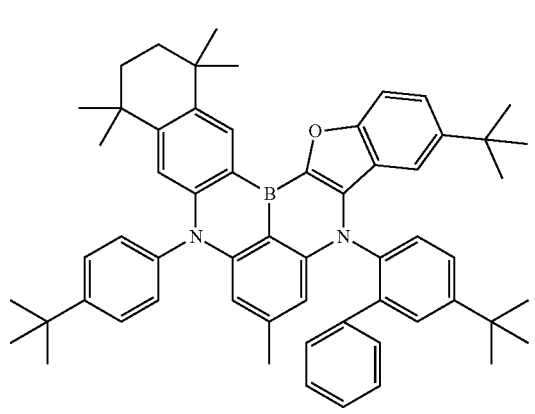
52
-continued
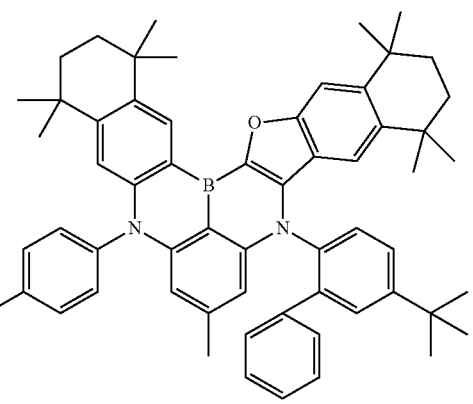
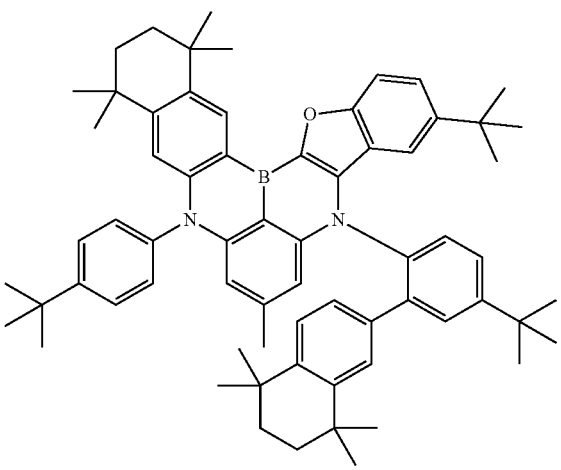
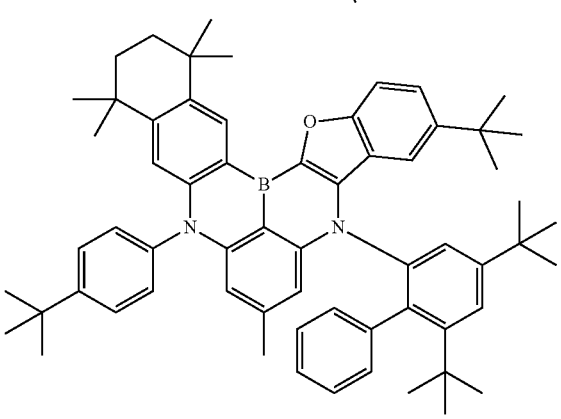
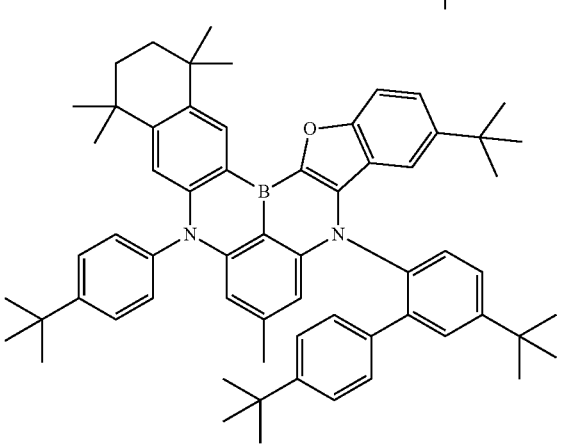

53
-continued
54
-continued
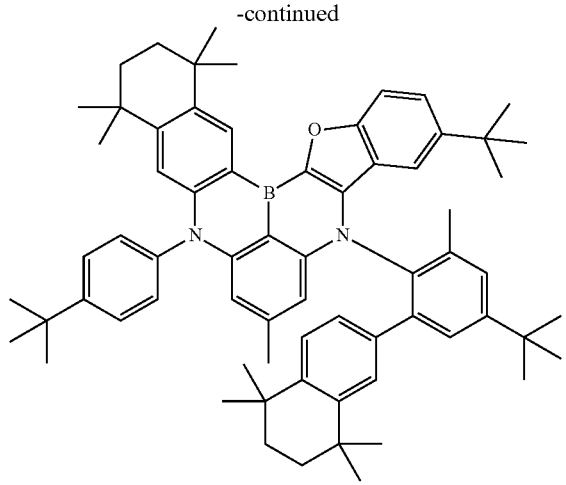
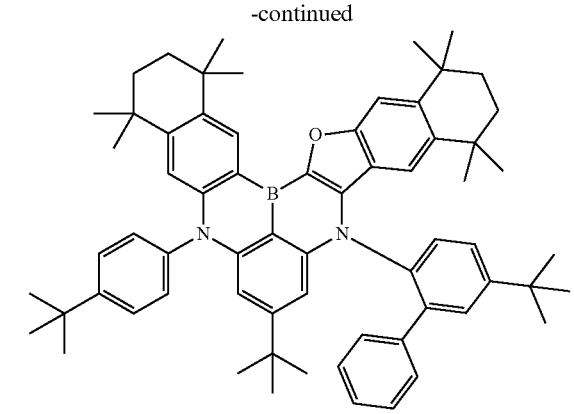
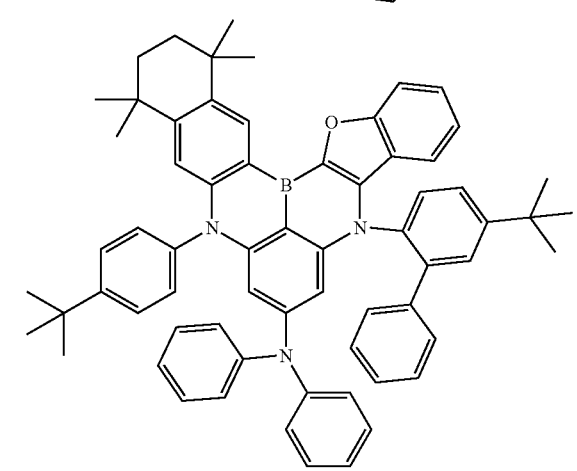
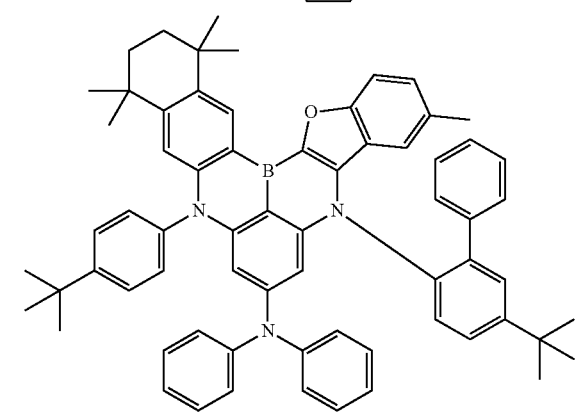
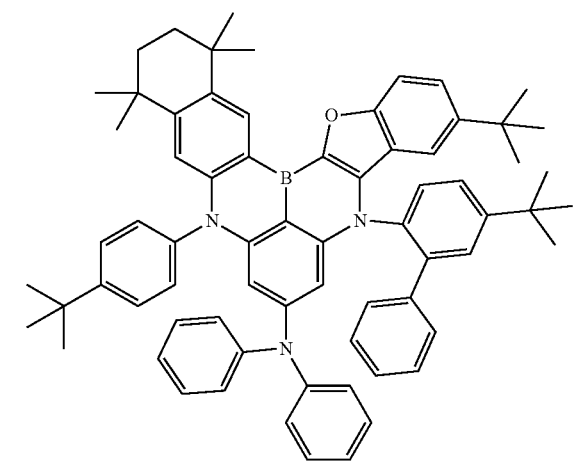

55
-continued
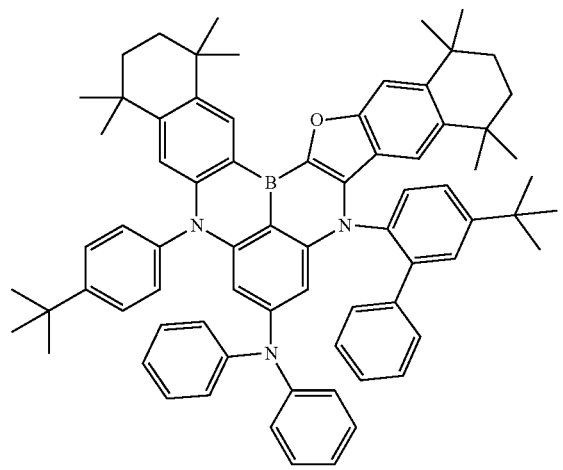
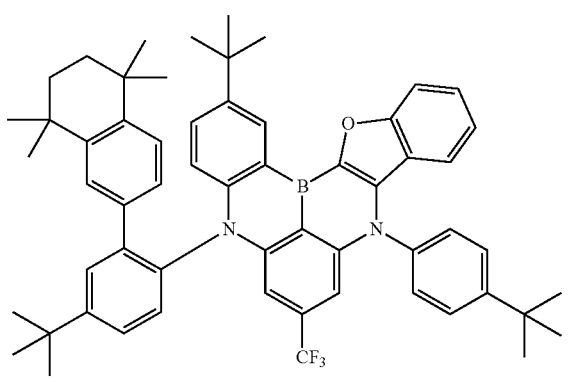
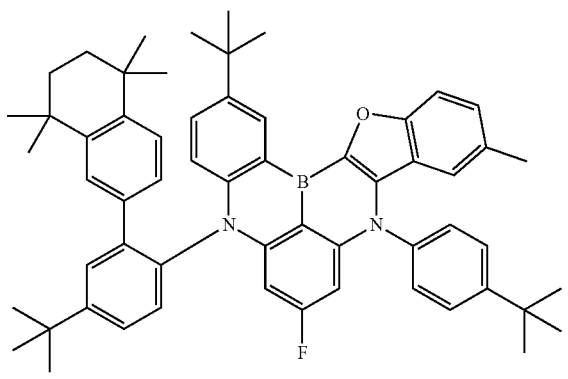
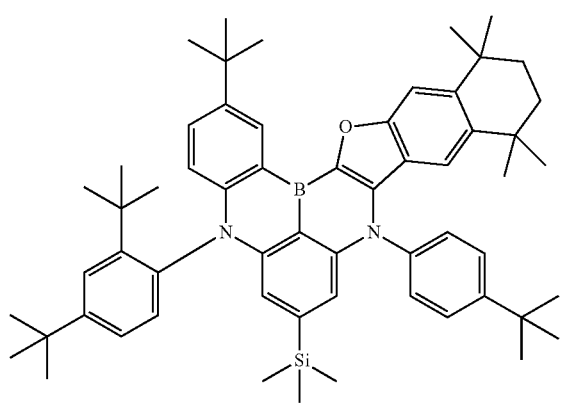
56
-continued
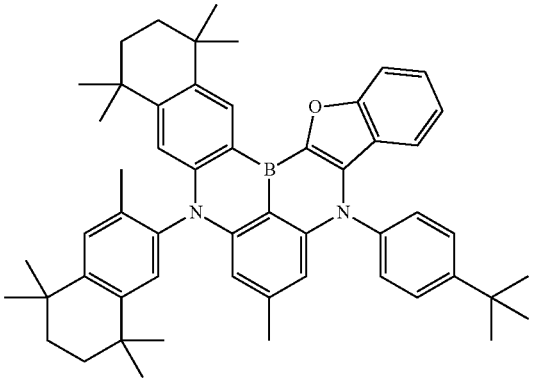
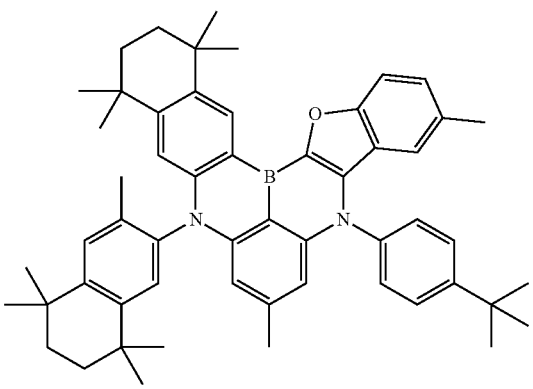
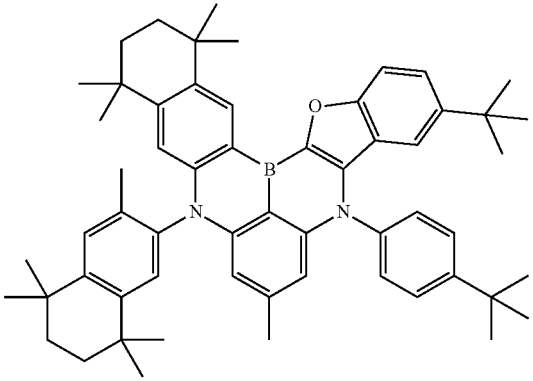
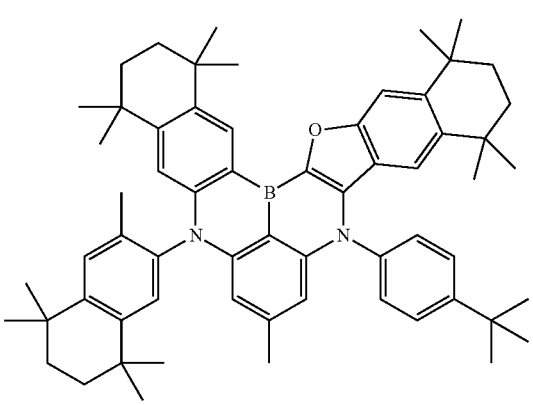

57
-continued
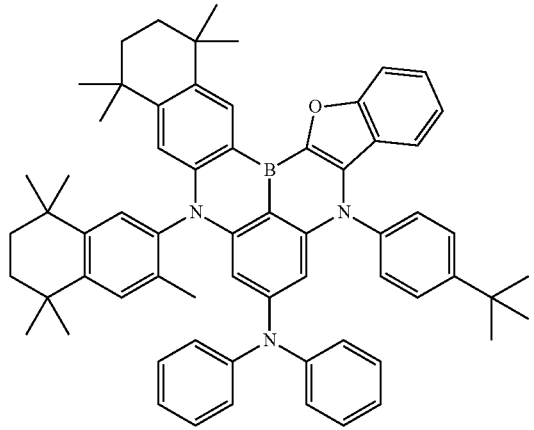
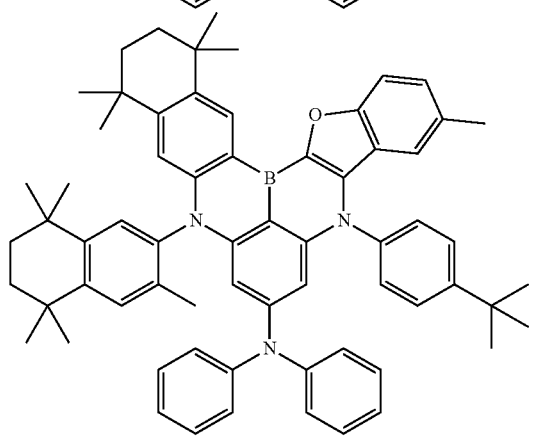
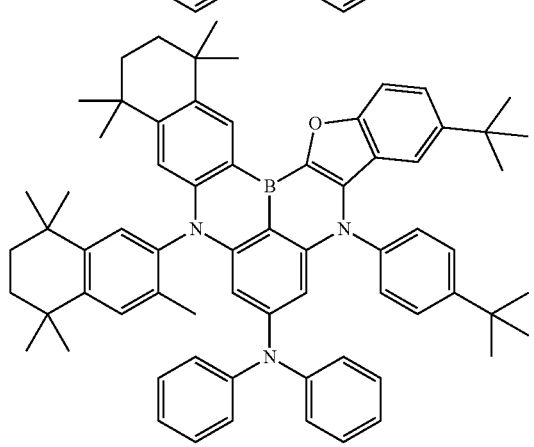
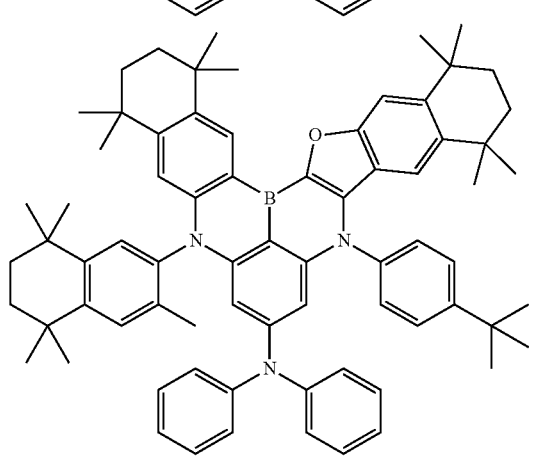
58
-continued
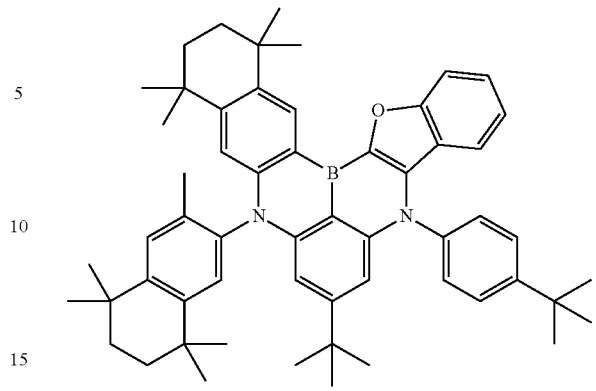
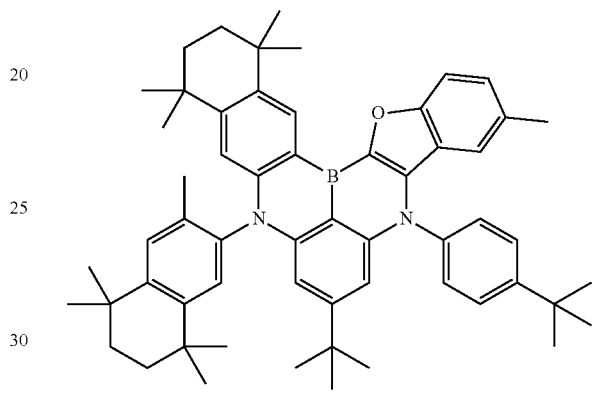

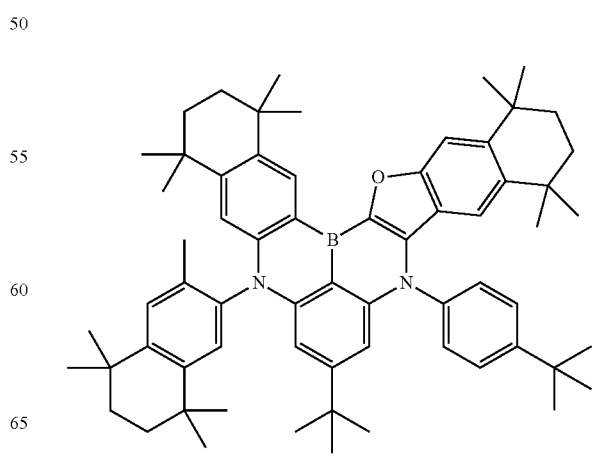

59
-continued
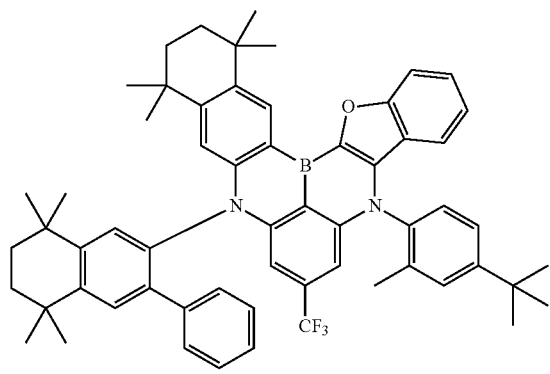
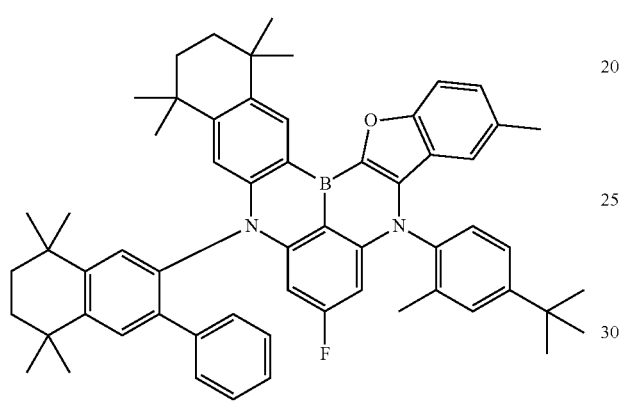
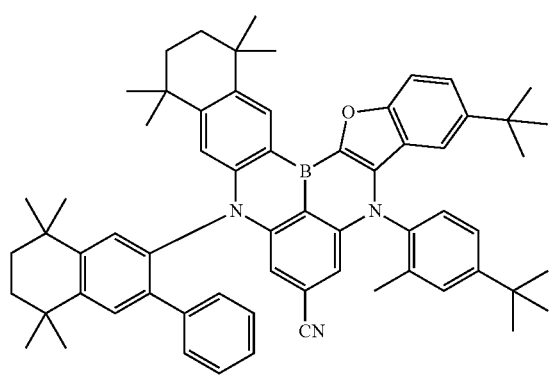
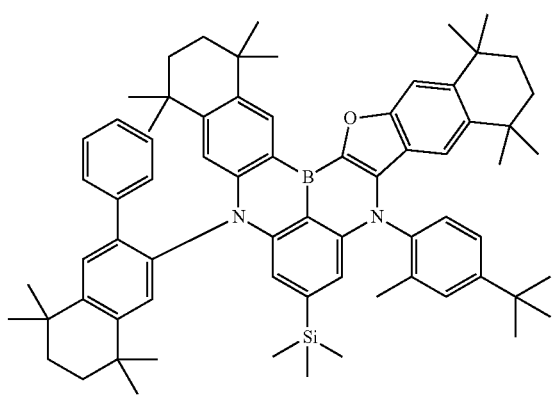
60
-continued
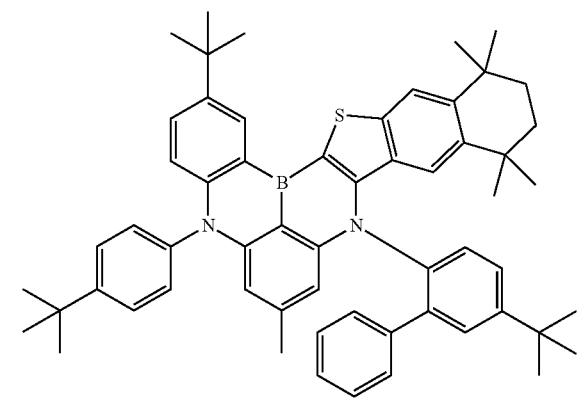
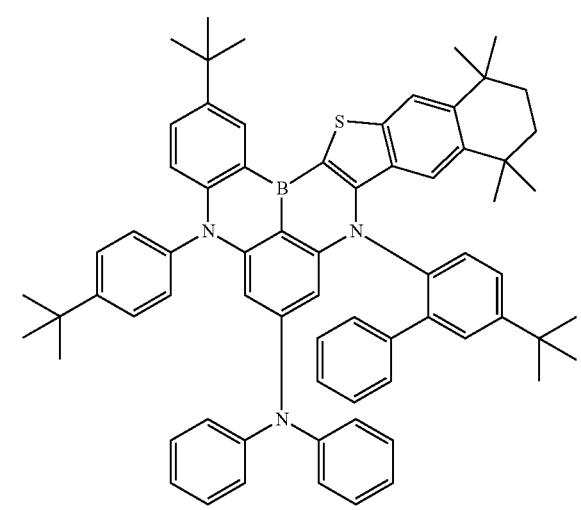
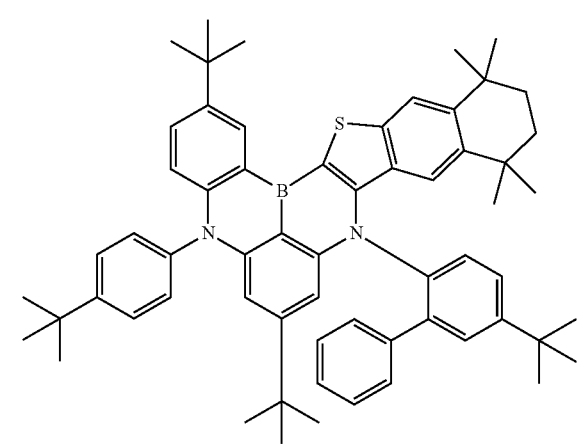

61
-continued
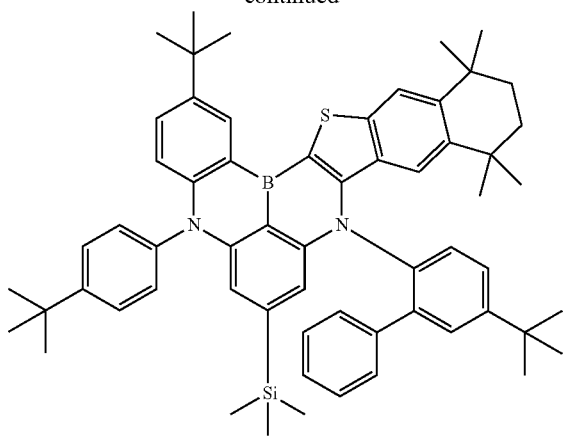
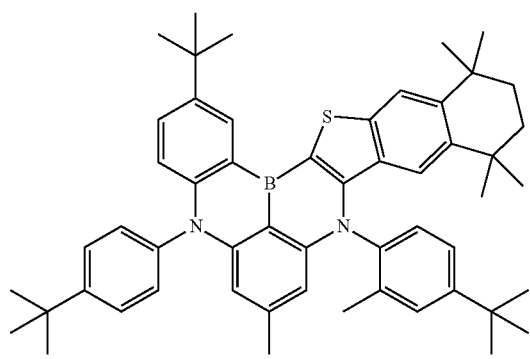
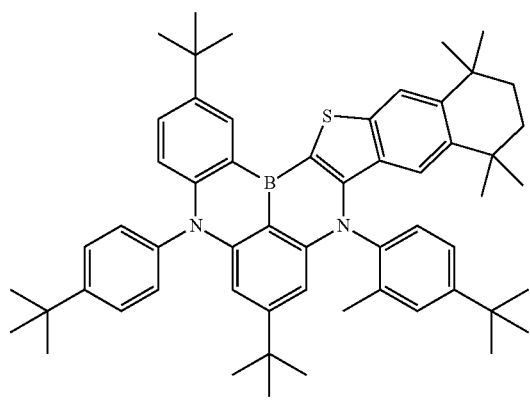
62
-continued
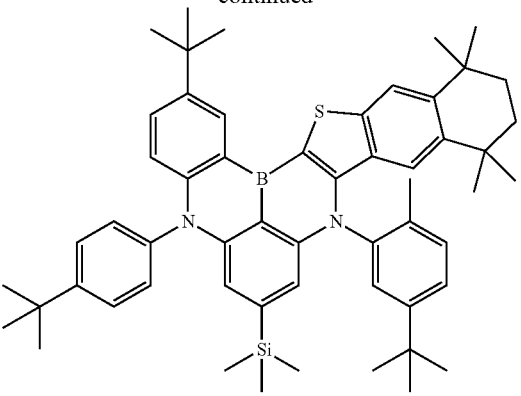
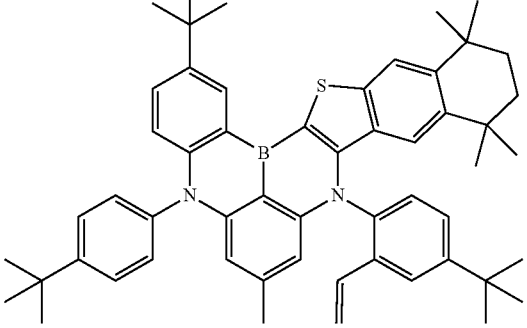
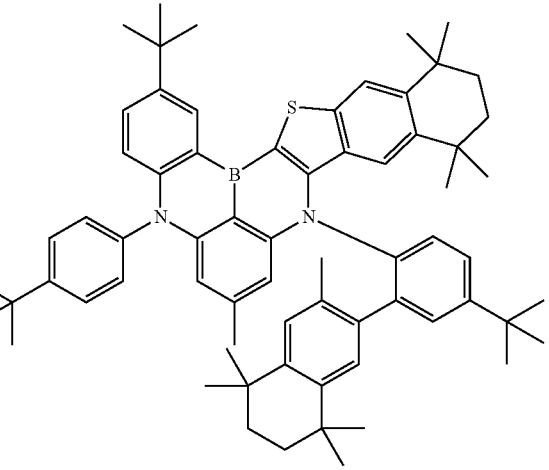
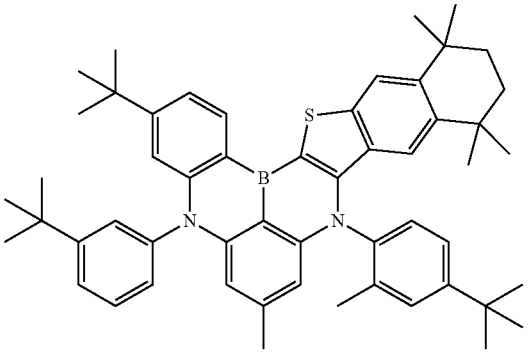

63
-continued
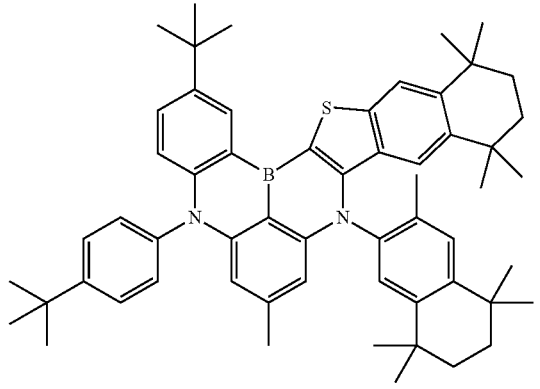
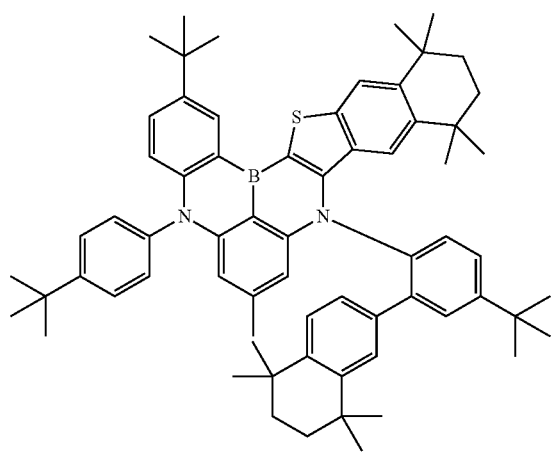 [SMILES: Cc1cc2c3c(c1)N(c1ccc(C(C)(C)C)cc1-c1ccc4c(c1)C(C)(C)CCC4(C)C)c1c(sc4cc5c(cc14)C(C)(C)CCC5(C)C)B3c1cc(C(C)(C)C)ccc1N2c1ccc(C(C)(C)C)cc1]
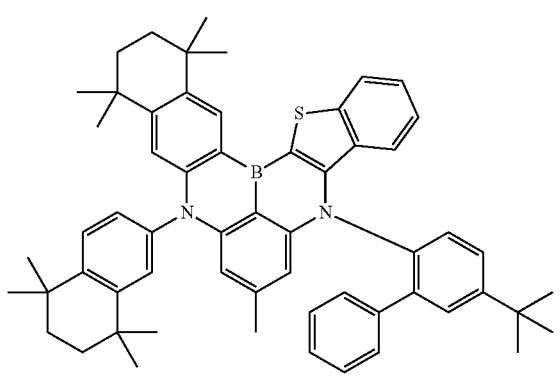
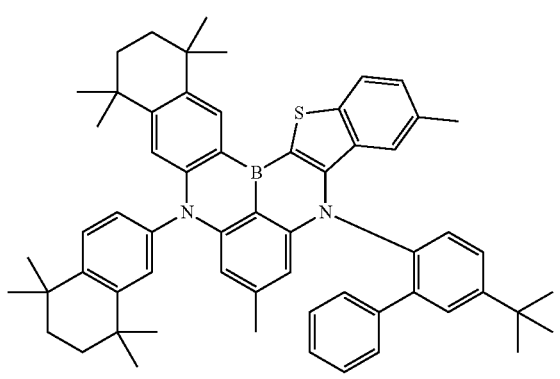
64
-continued
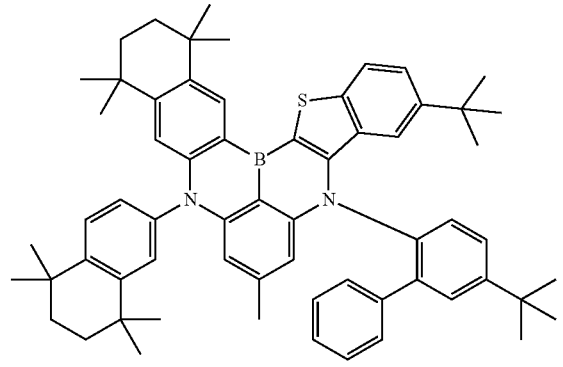
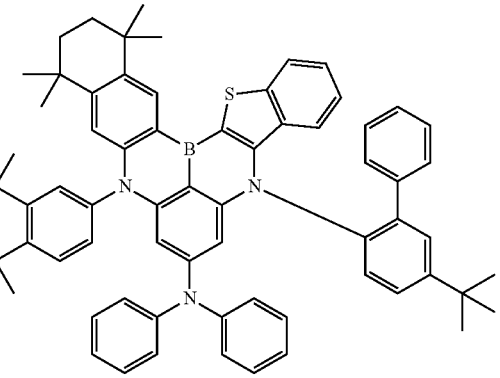
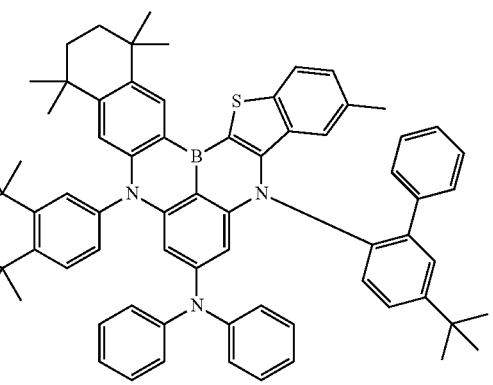

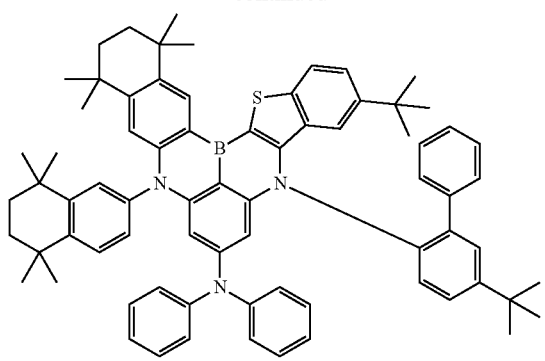
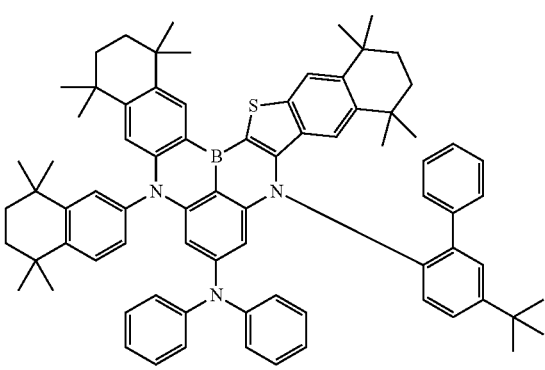
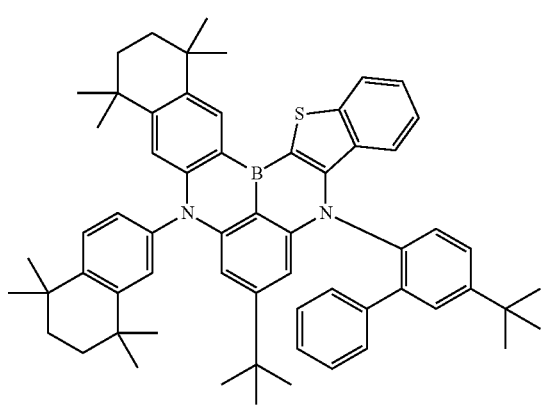
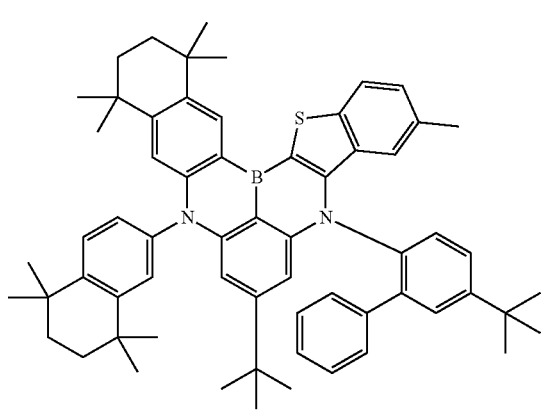
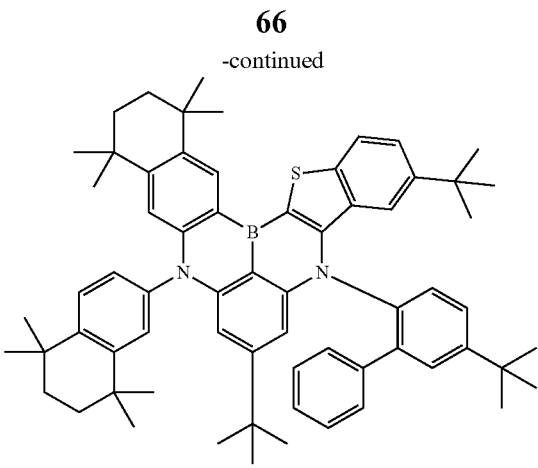
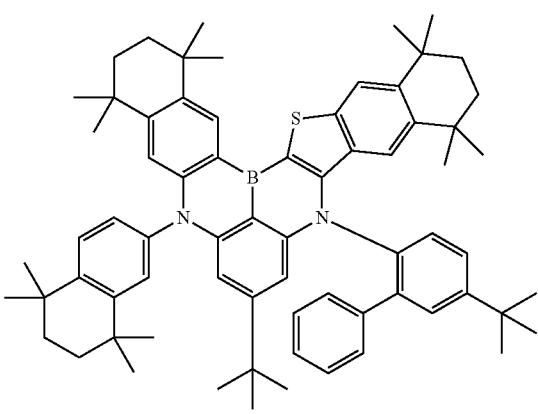
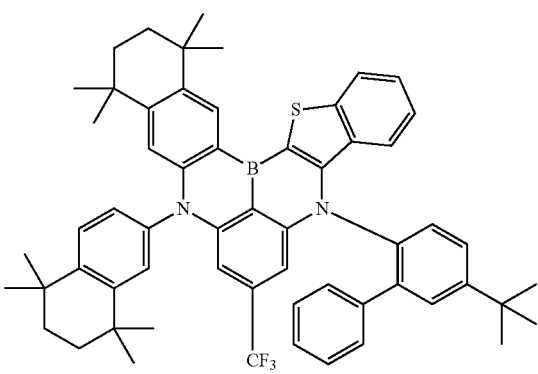
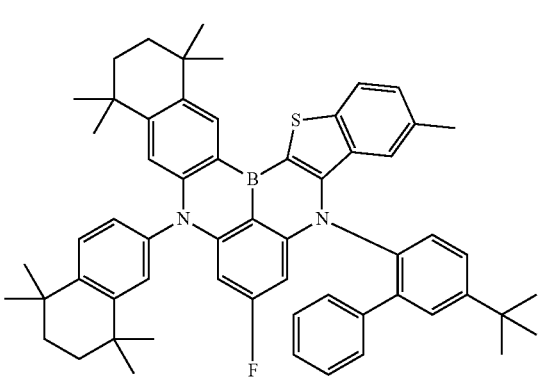

-continued

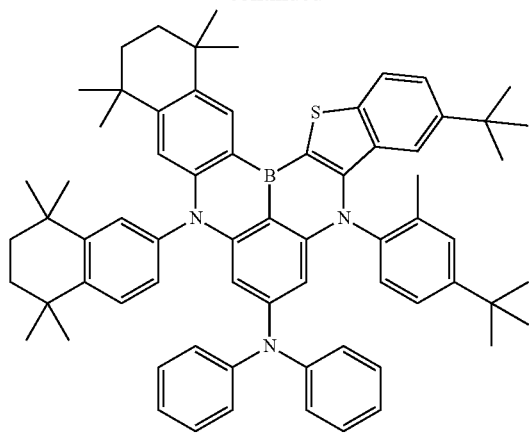
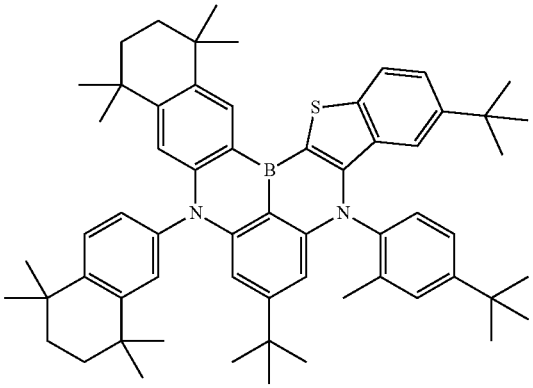
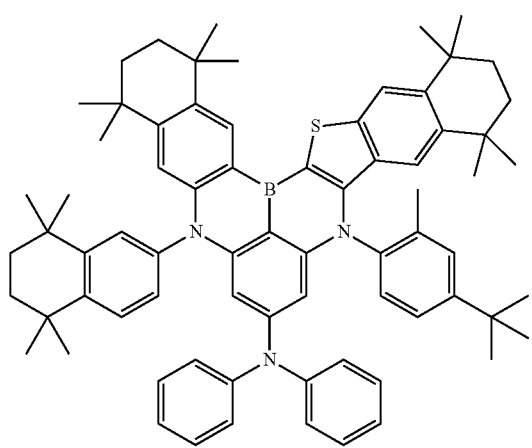
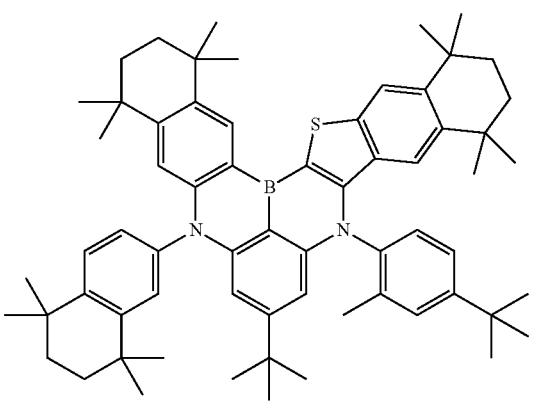
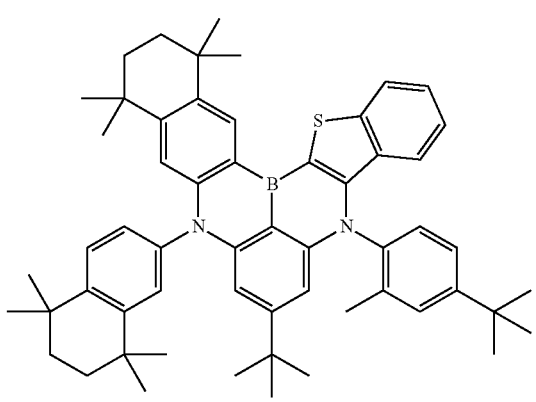
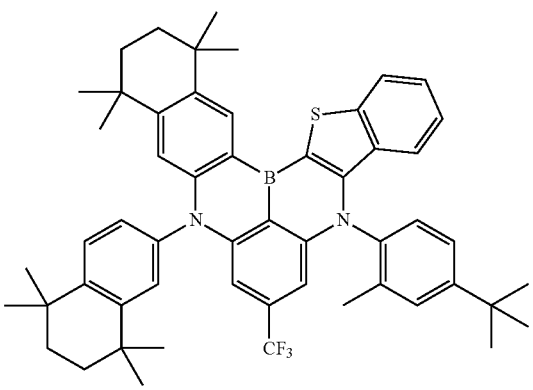
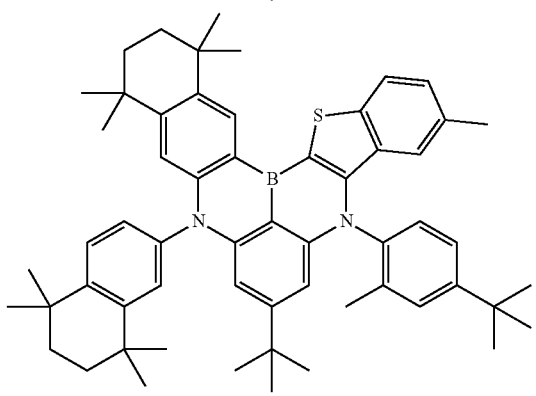
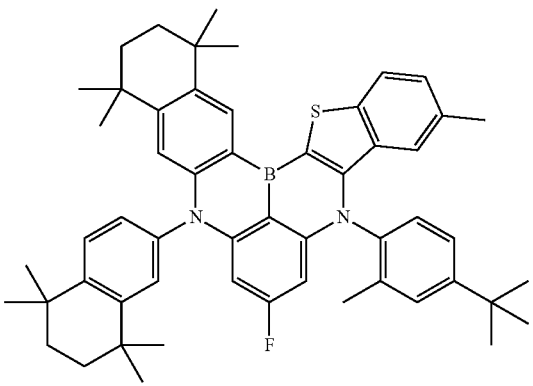

-continued
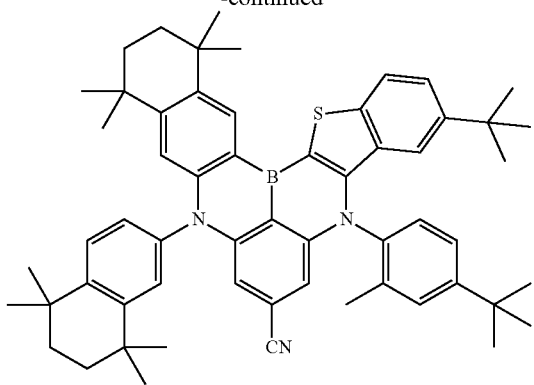
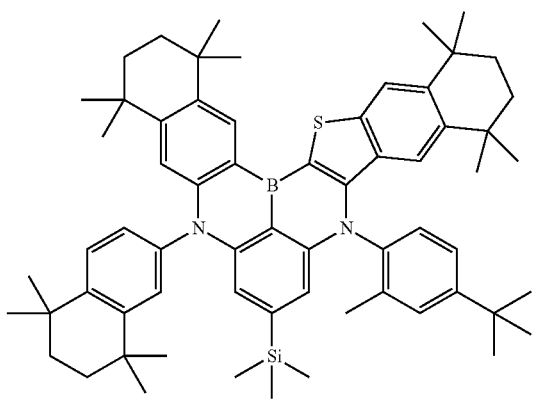
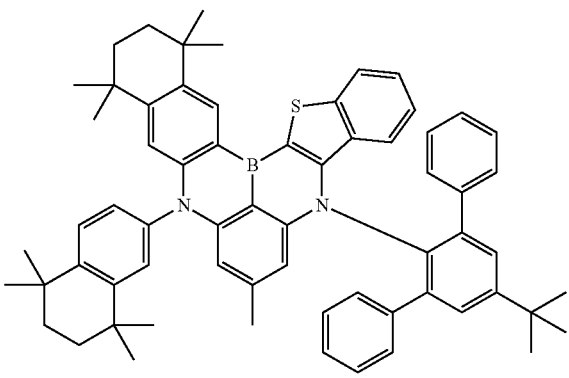
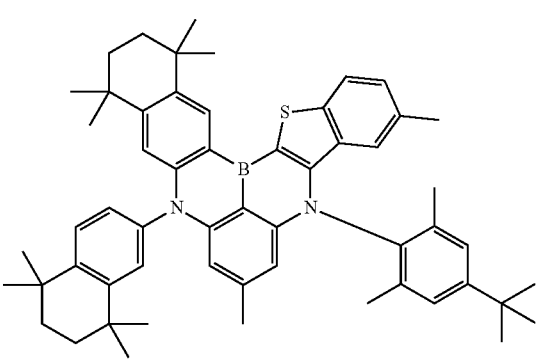
-continued
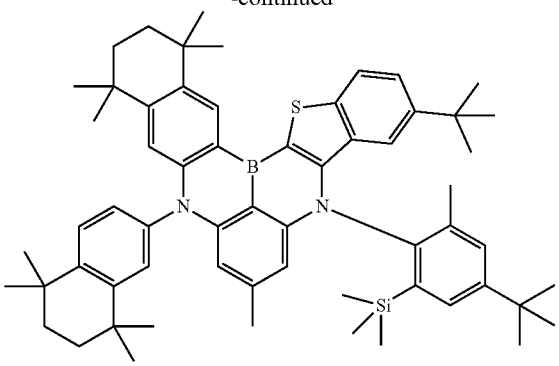
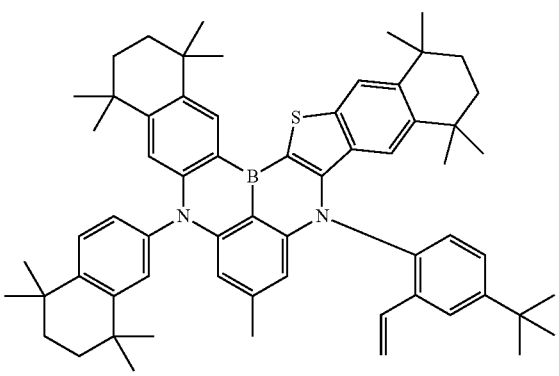
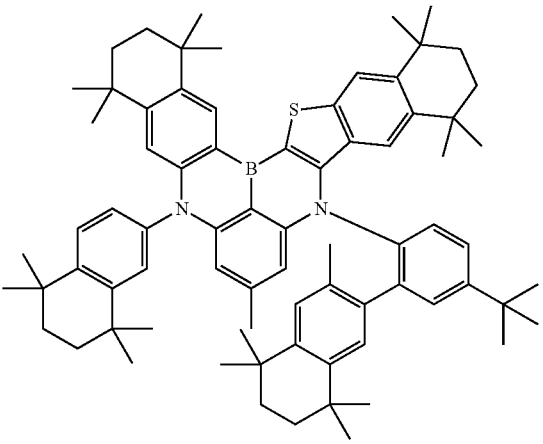
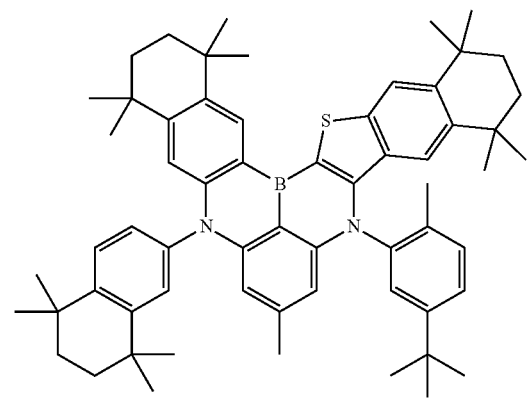

73
-continued
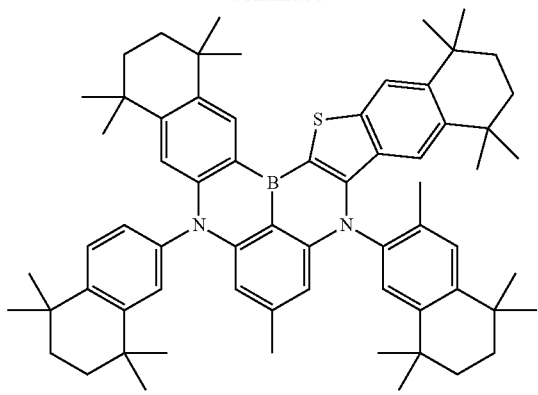
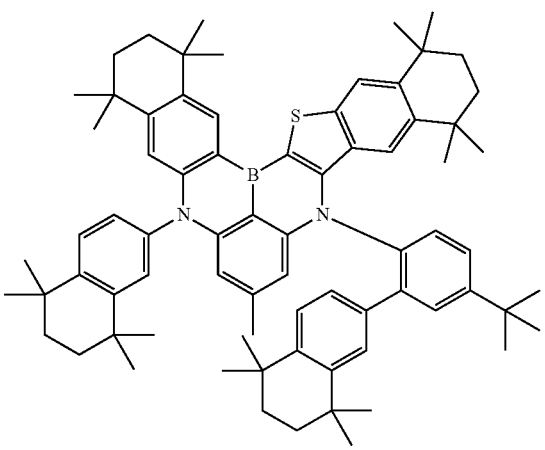
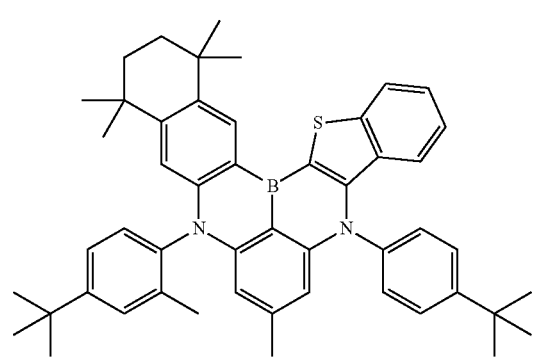
74
-continued
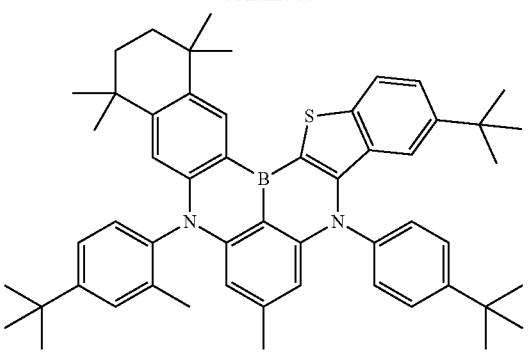
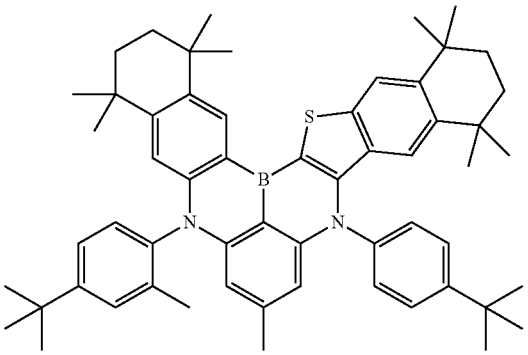
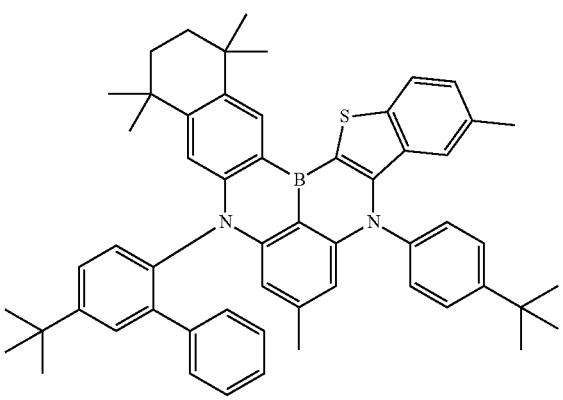

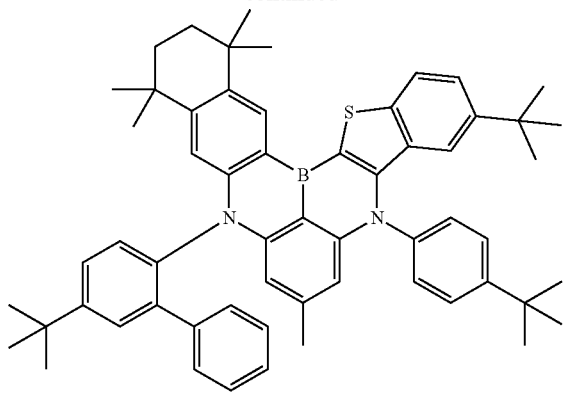
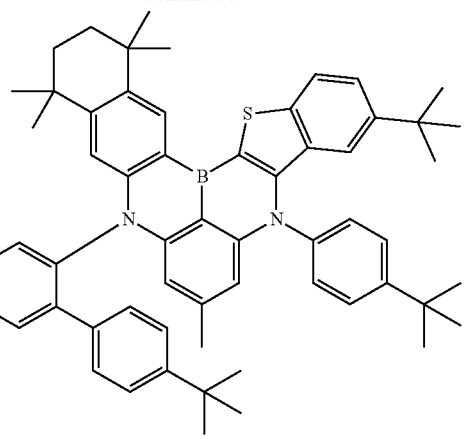
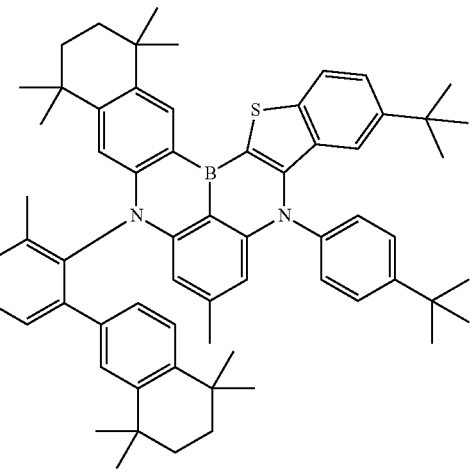
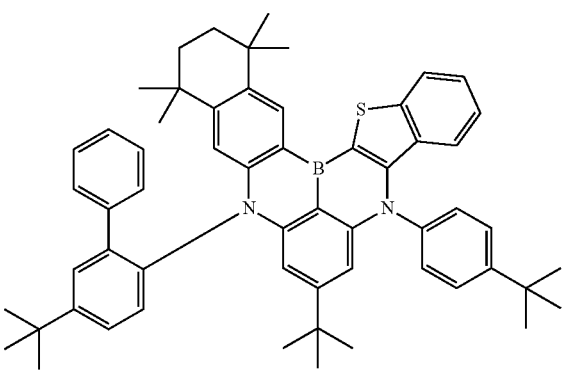
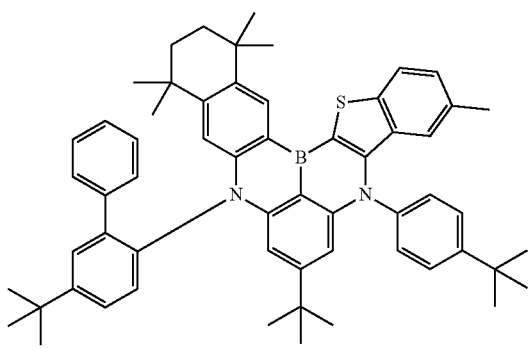

77
-continued
78
-continued
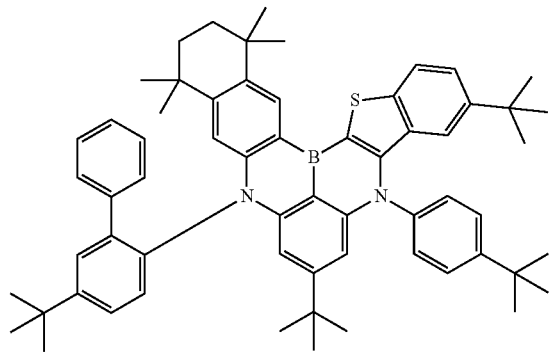
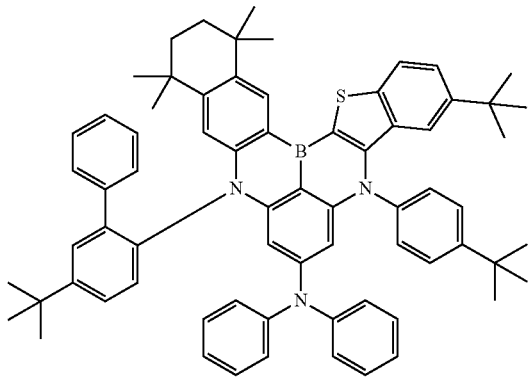
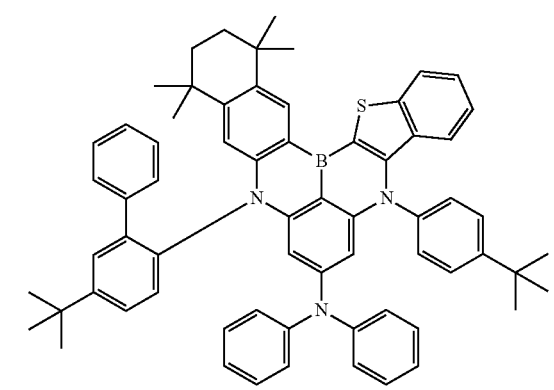
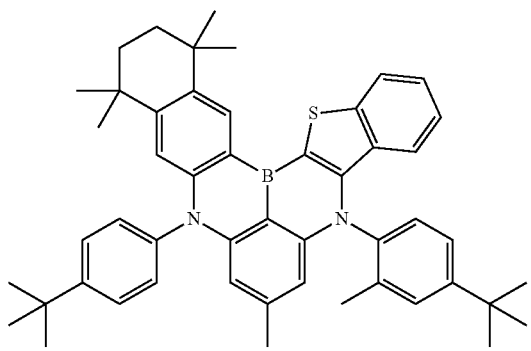
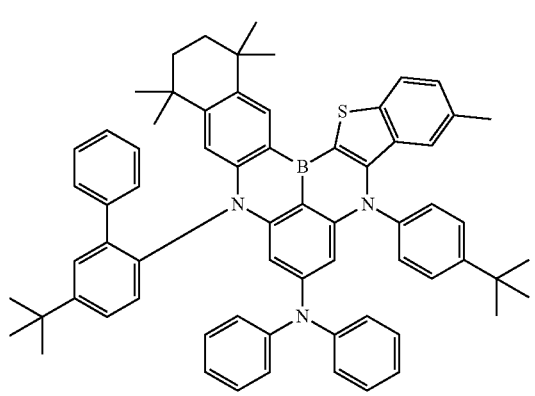
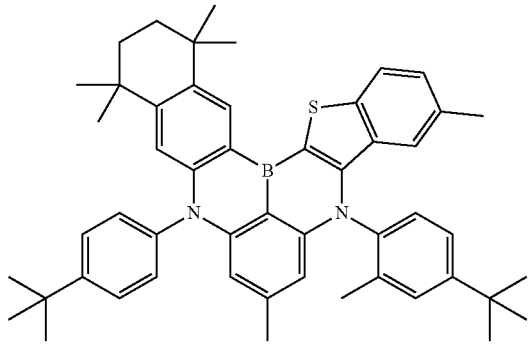

-continued
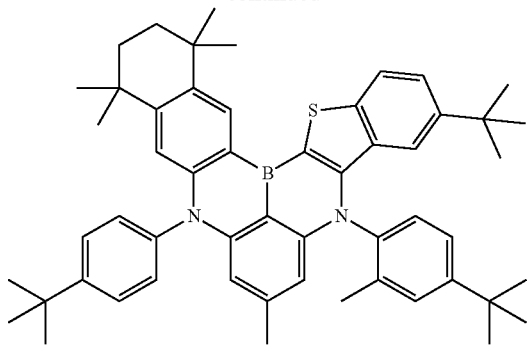
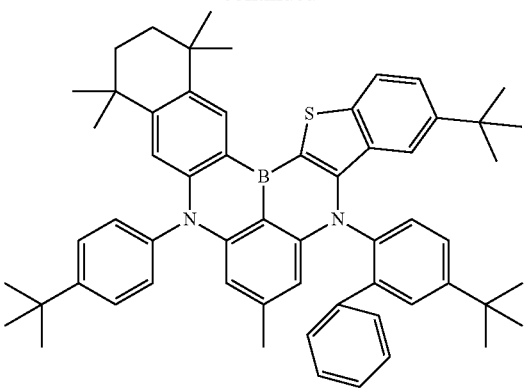
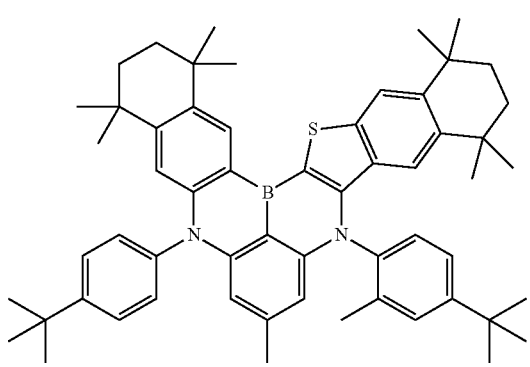
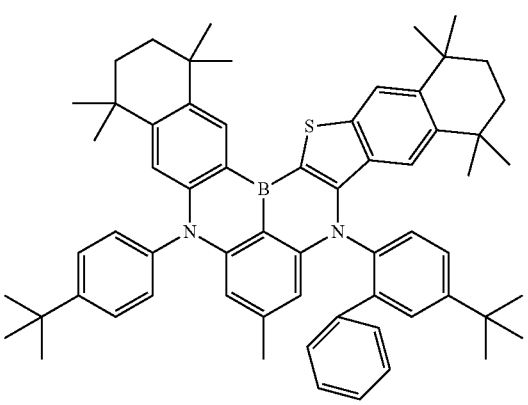
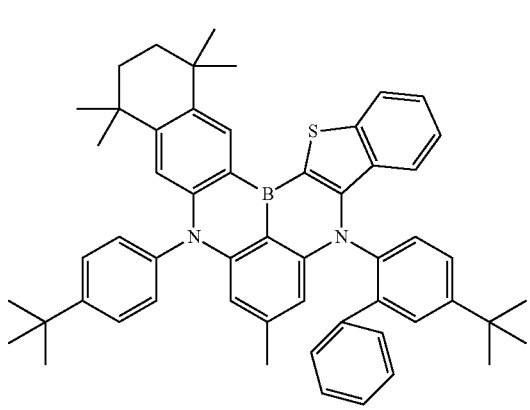
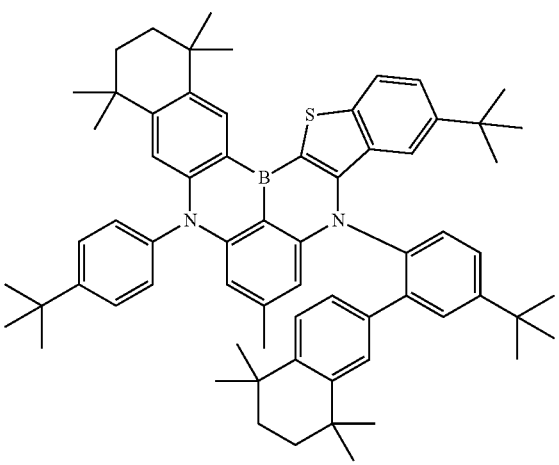
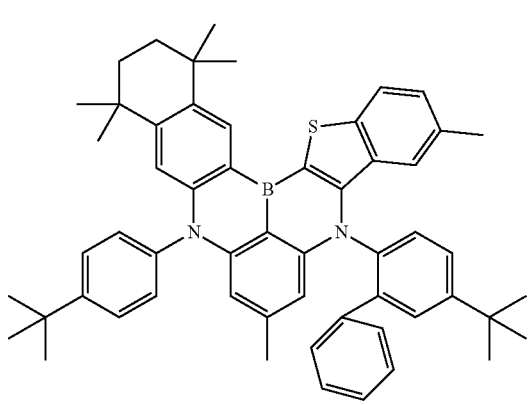
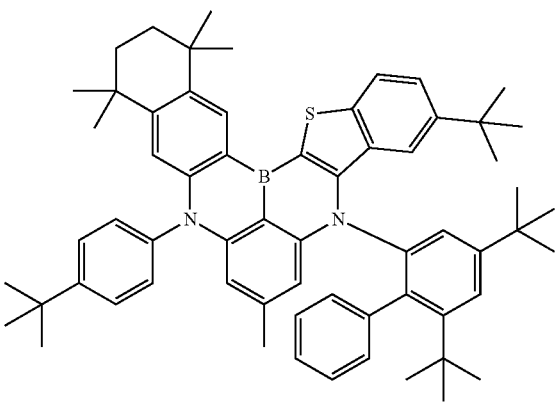

81
-continued
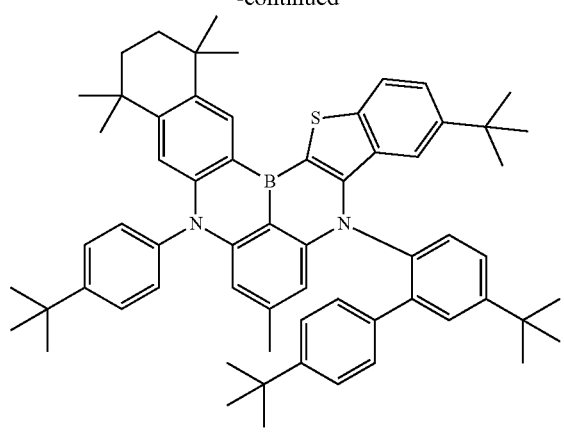
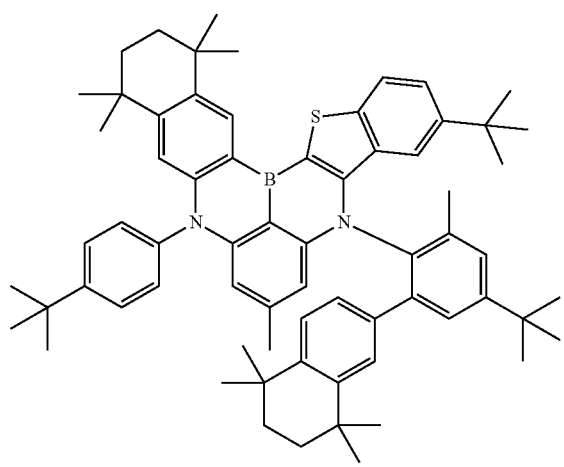
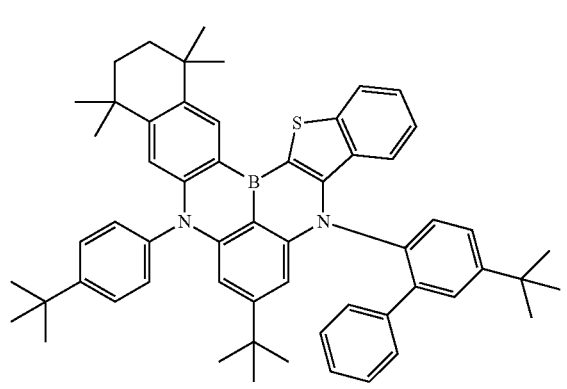
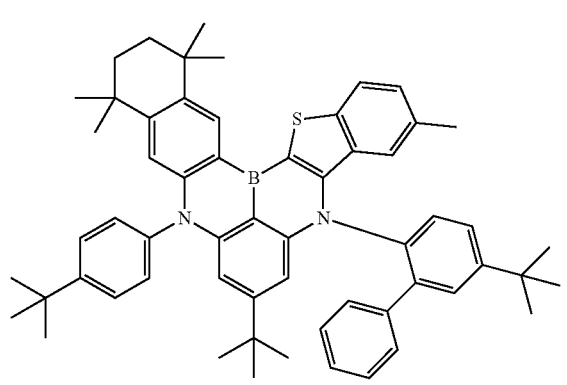
82
-continued
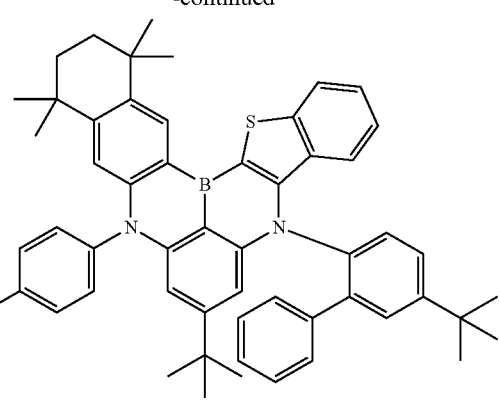
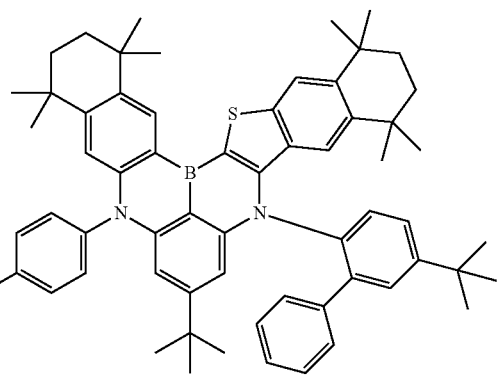
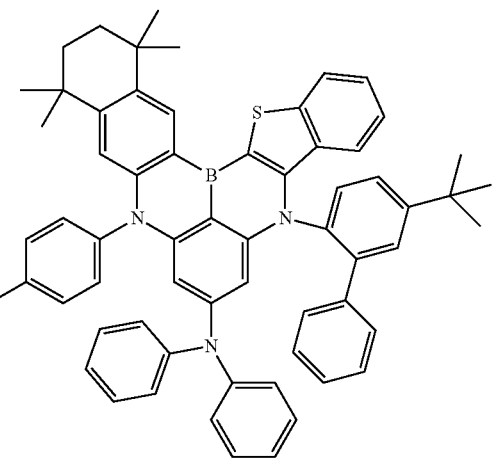
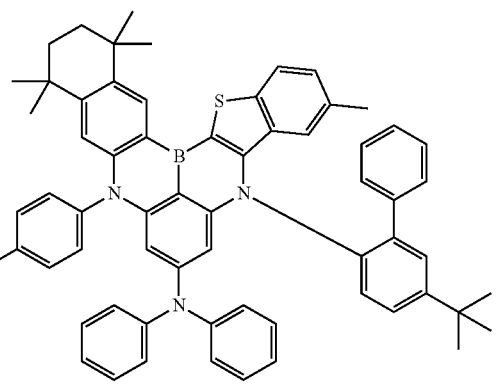

83
-continued
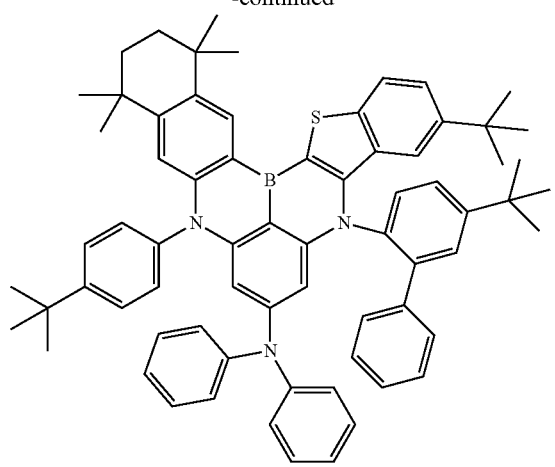
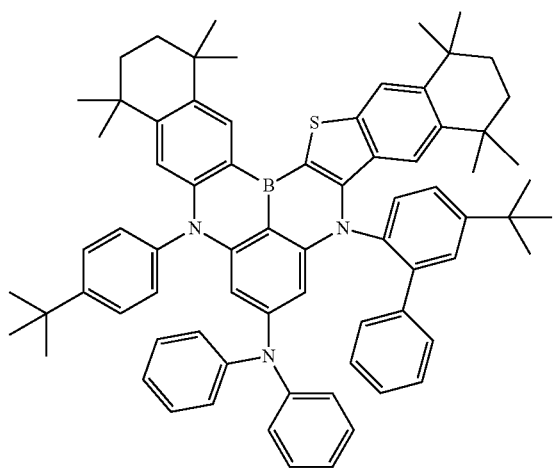
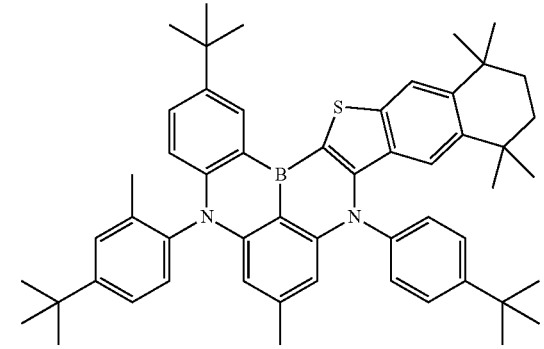
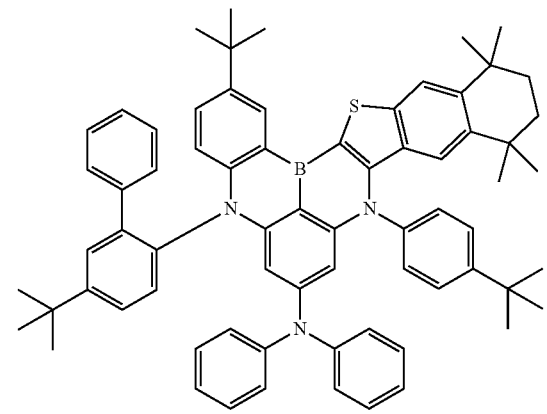
84
-continued
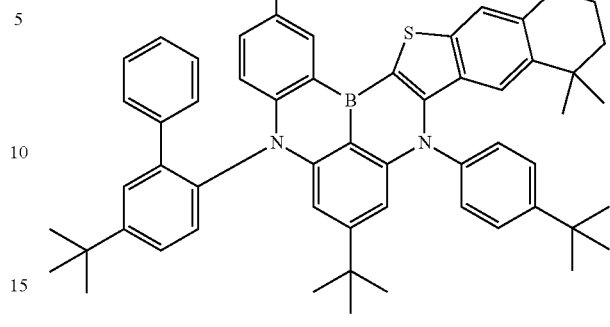
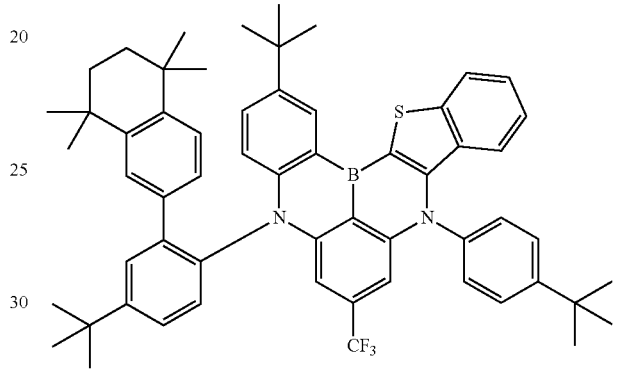
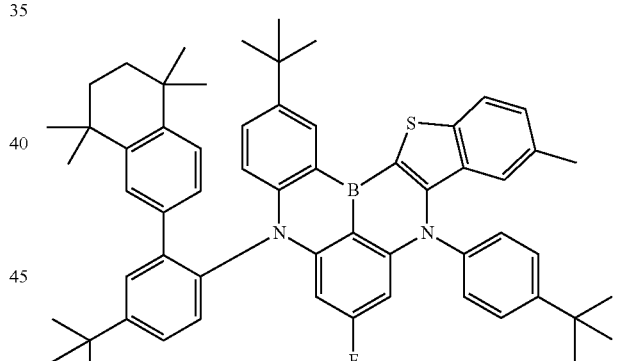
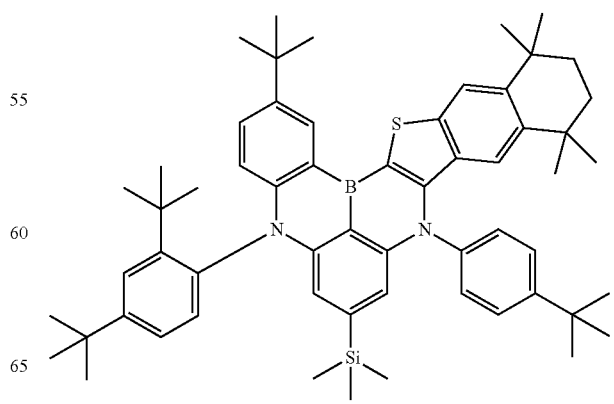

85
-continued
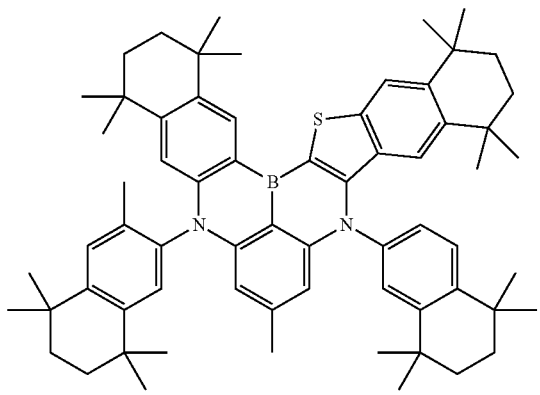
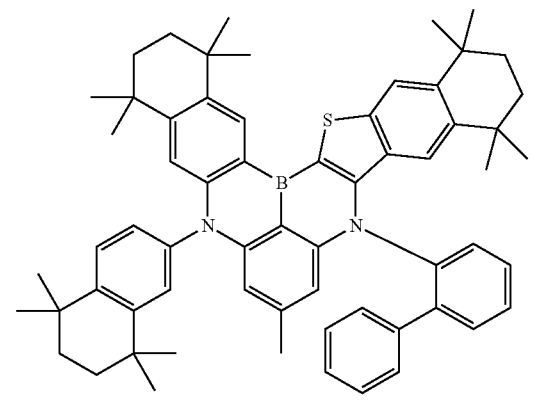
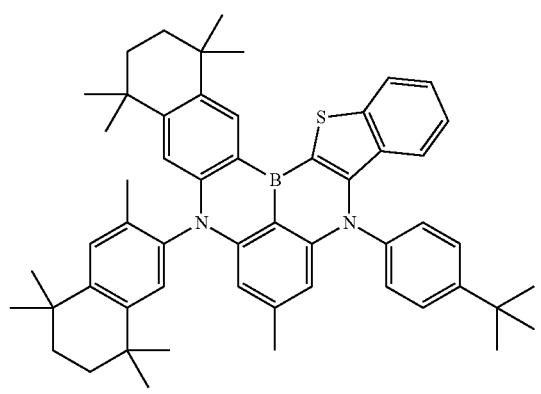
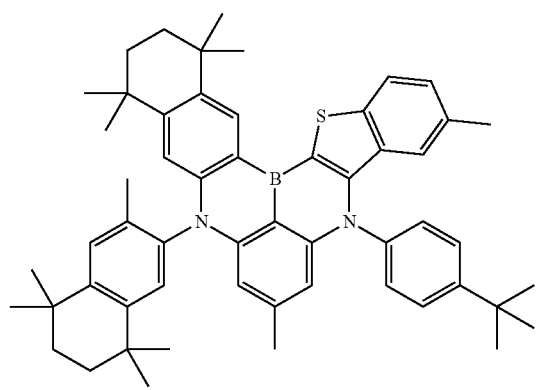
86
-continued
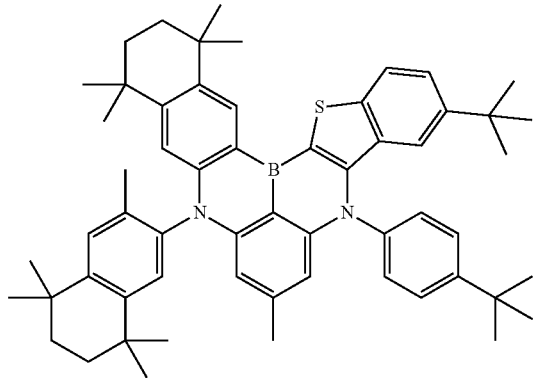
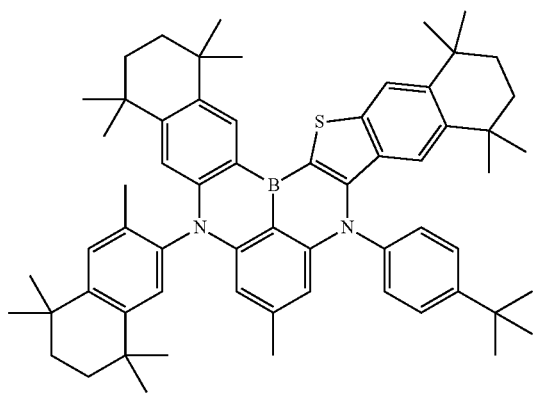
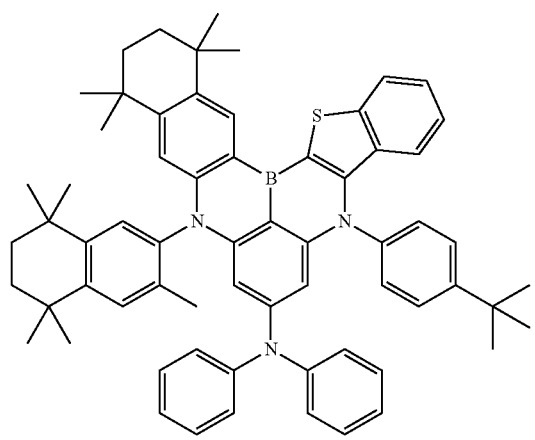
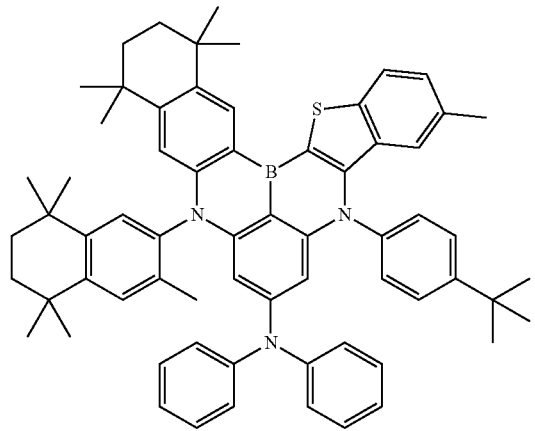

87
-continued
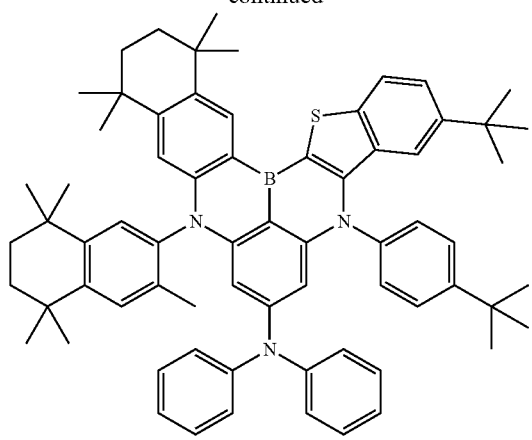
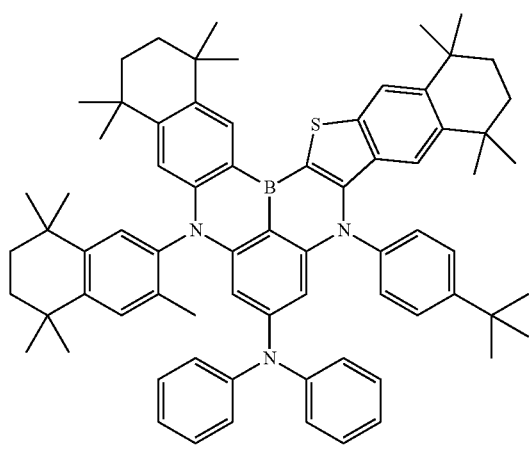
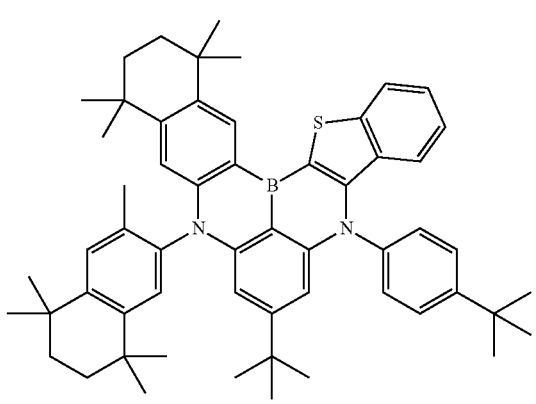
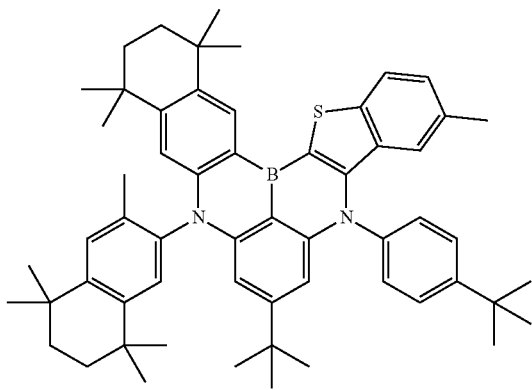
88
-continued
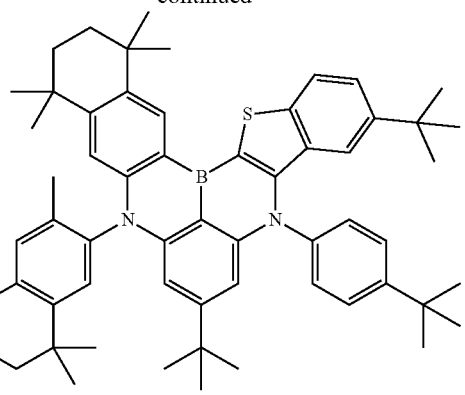
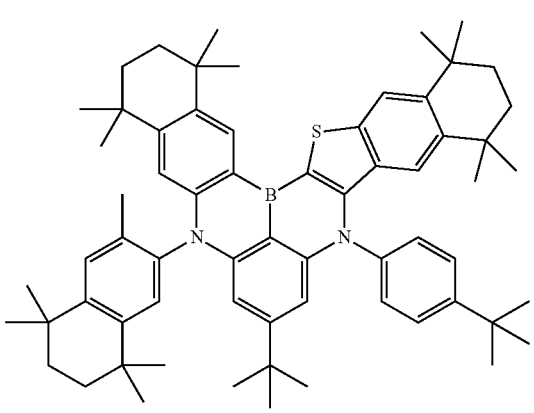
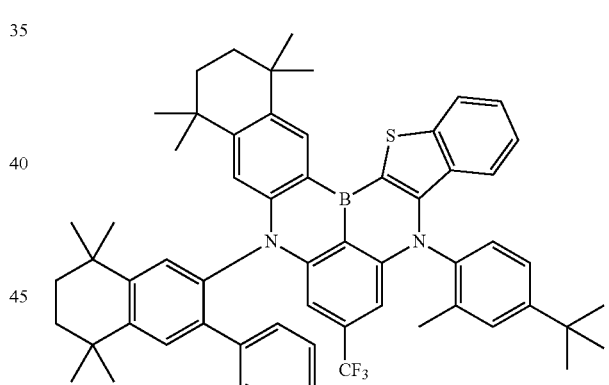
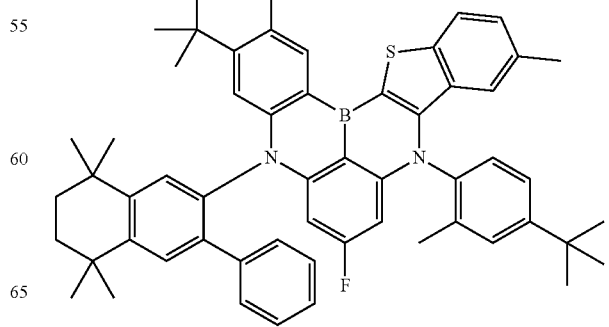

89
-continued
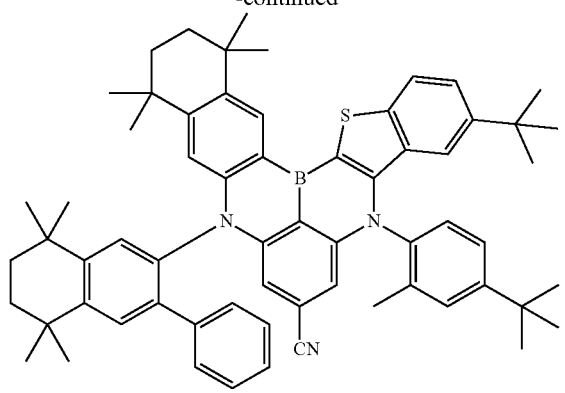
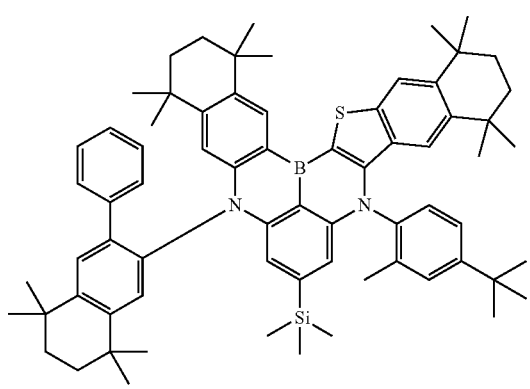
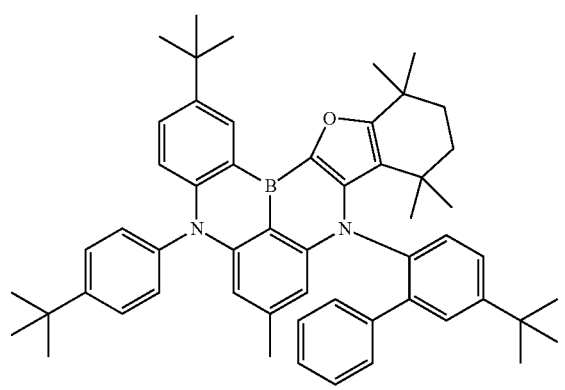
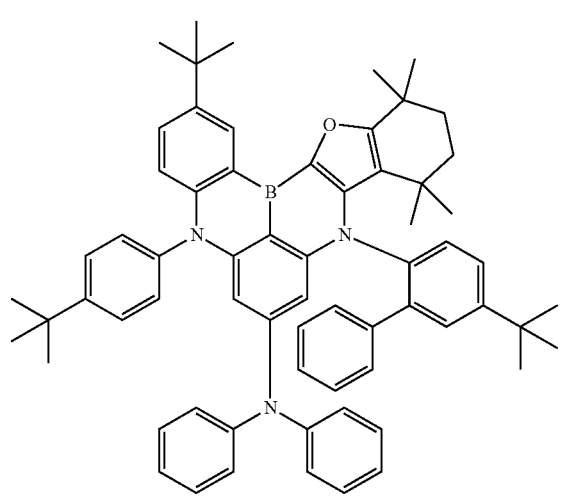
90
-continued
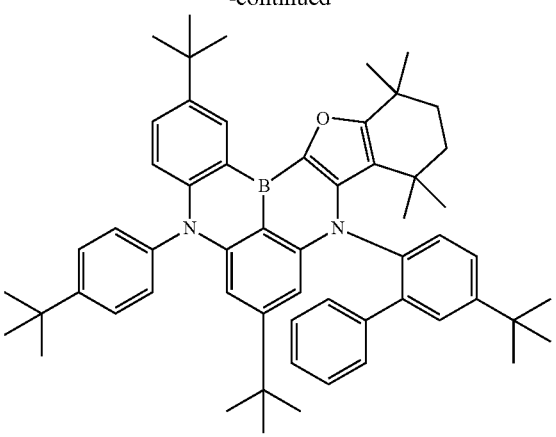
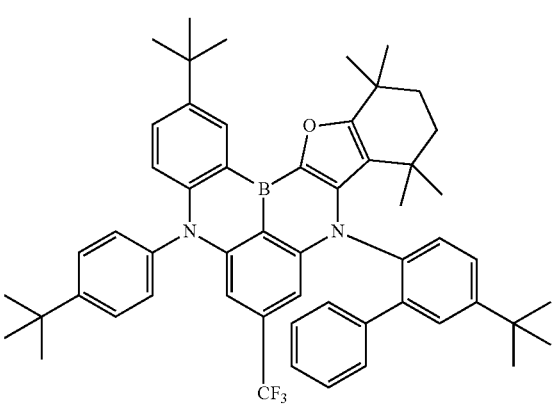
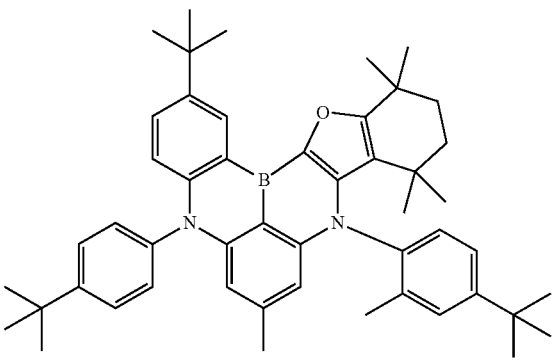
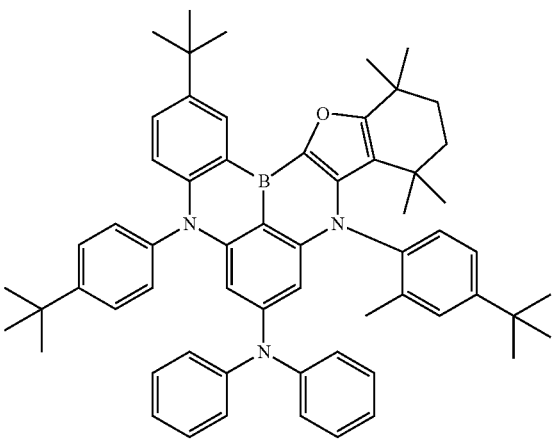

91
-continued
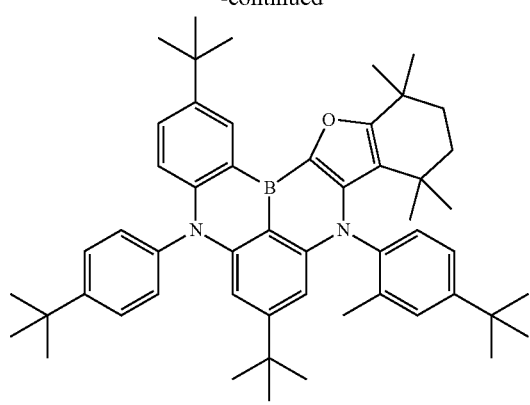
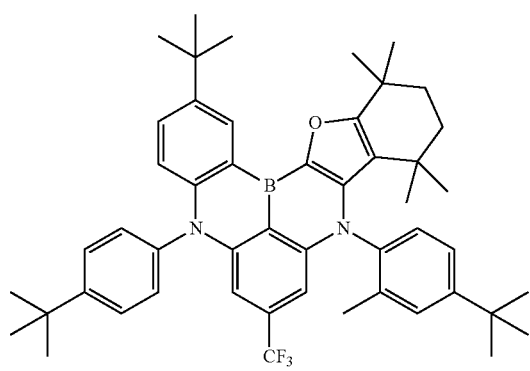
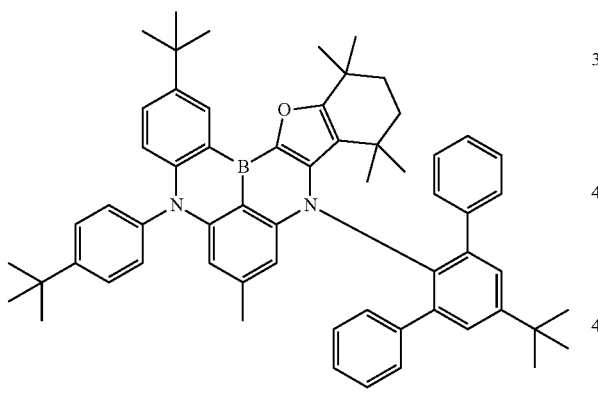
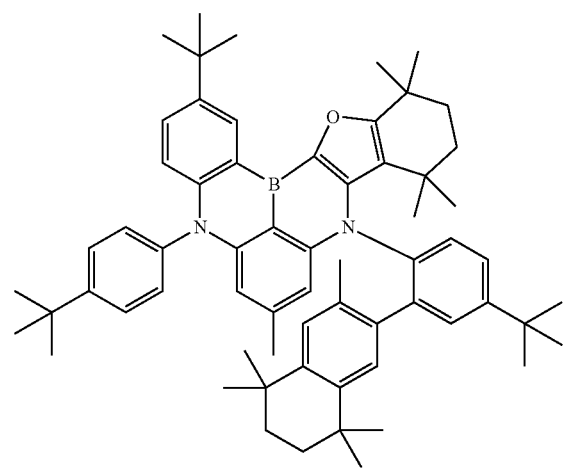
92
-continued
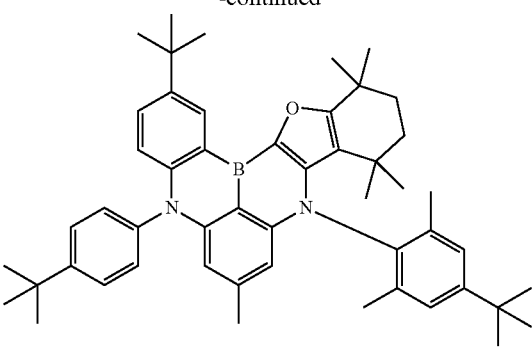
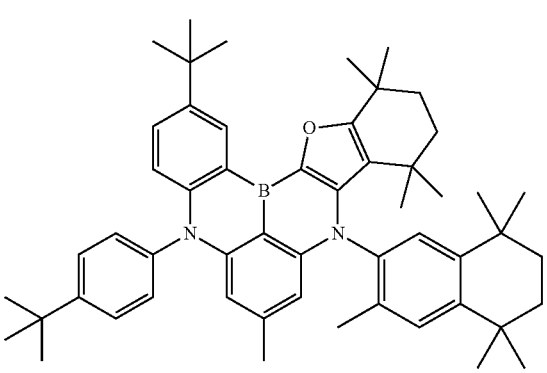
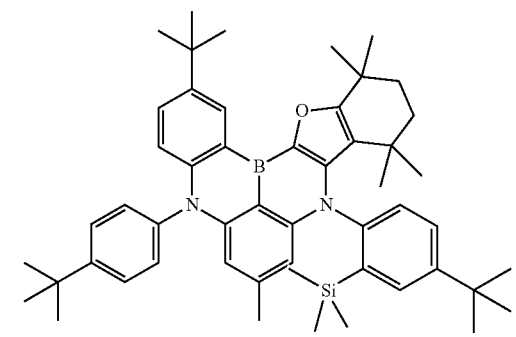
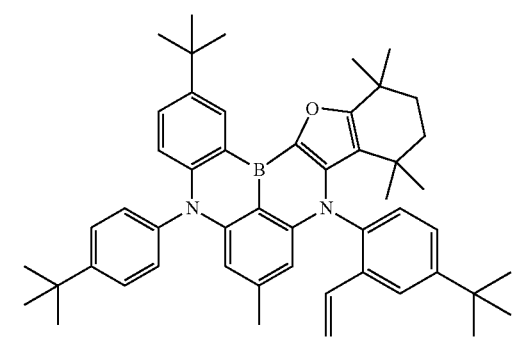

93
-continued
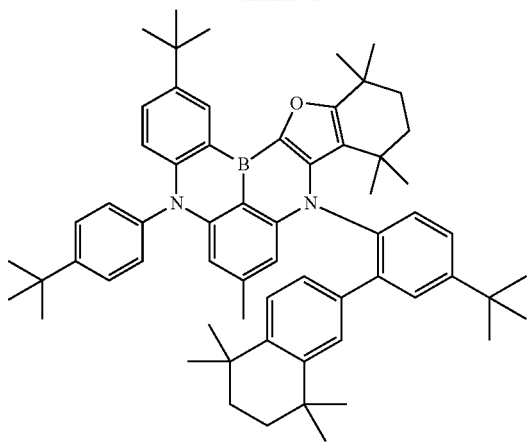
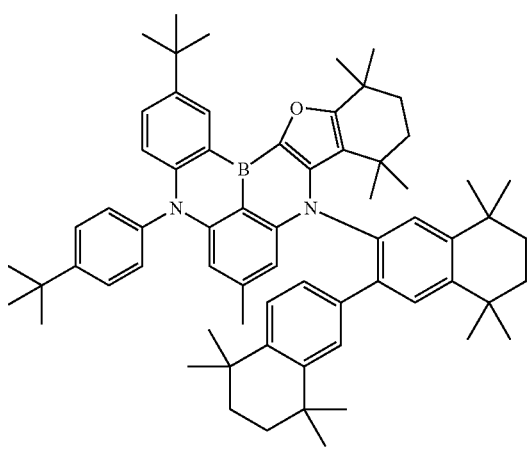
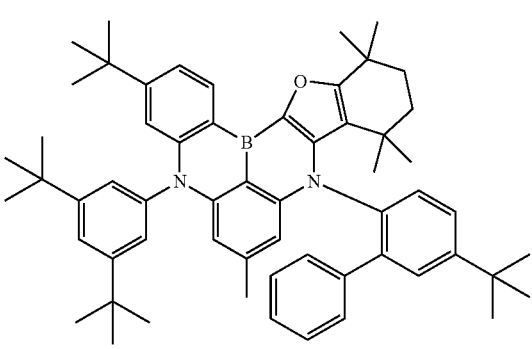
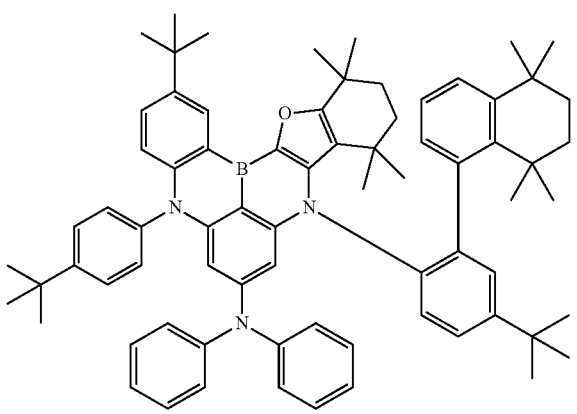
94
-continued
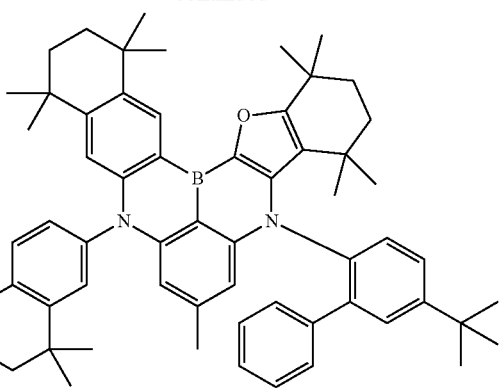
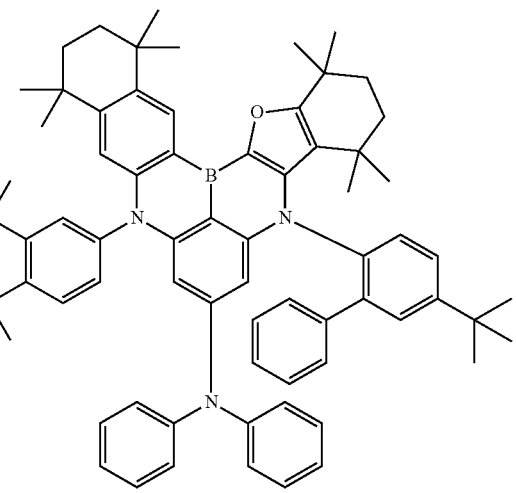
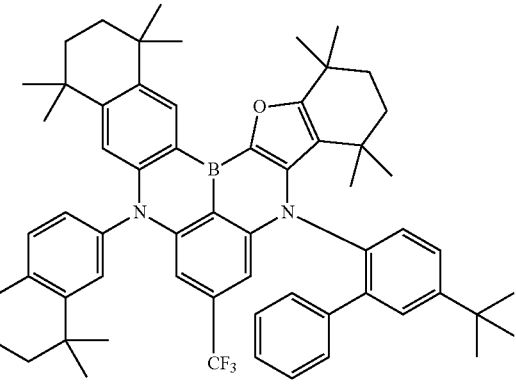

95
-continued
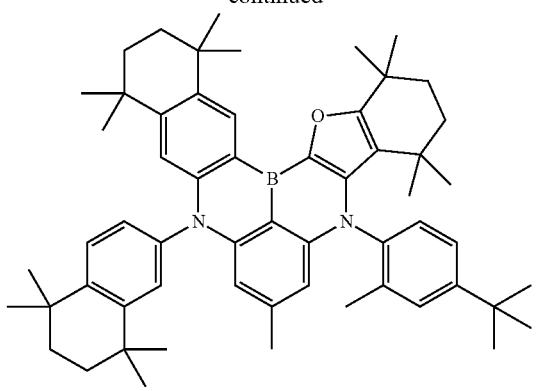
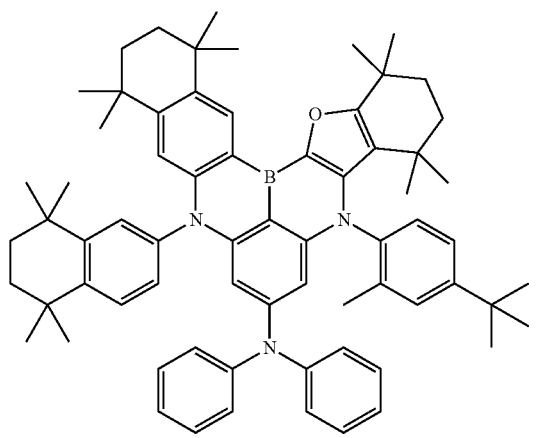
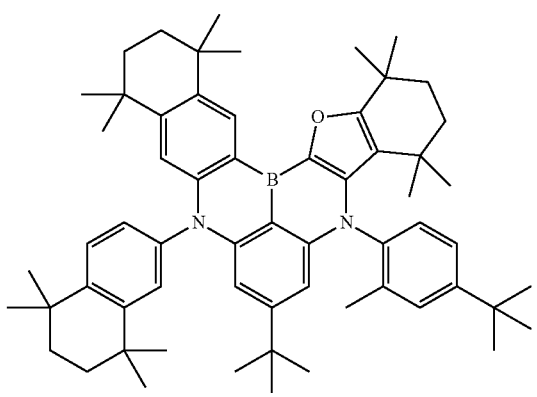
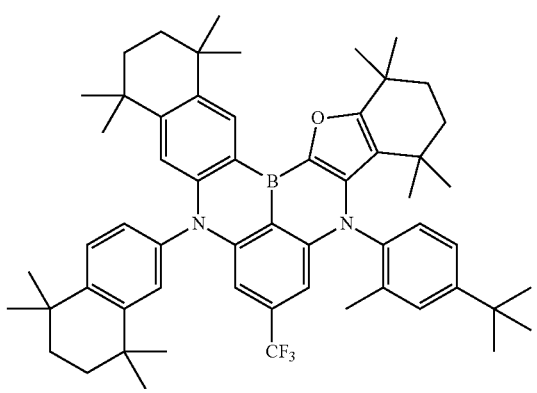
96
-continued
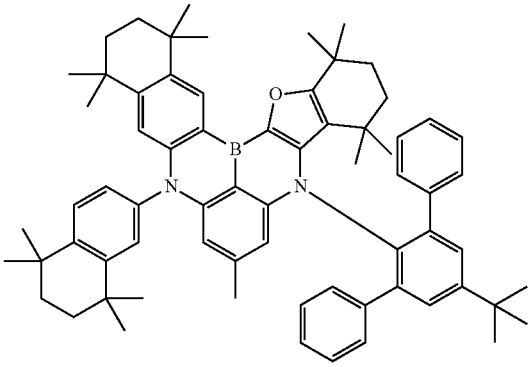
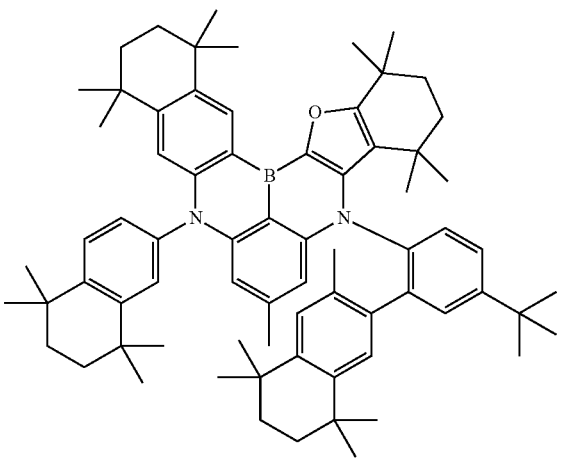
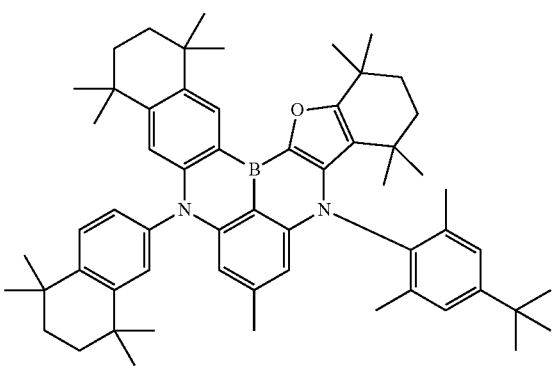
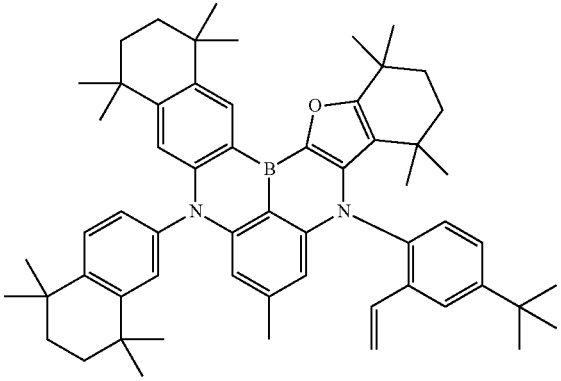

97
-continued
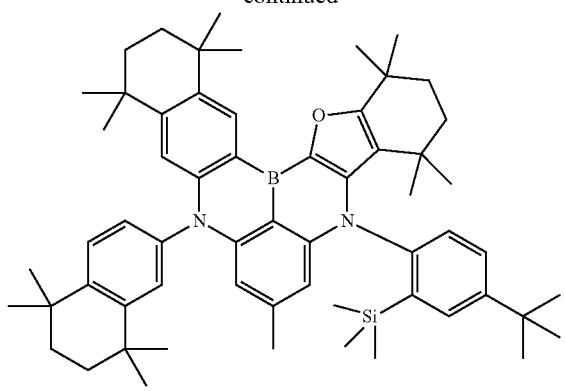
98
-continued
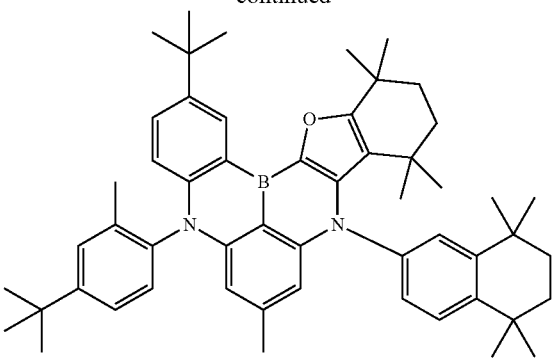
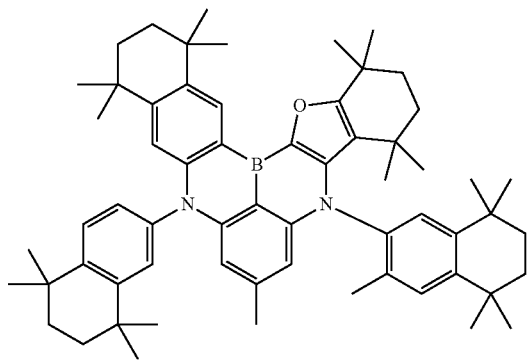
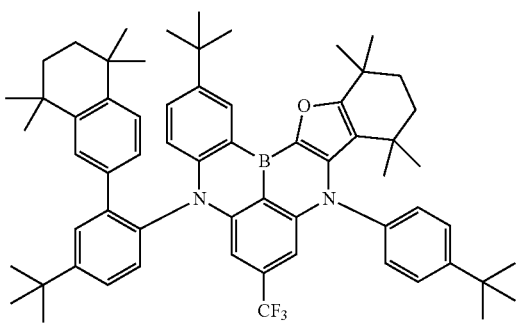
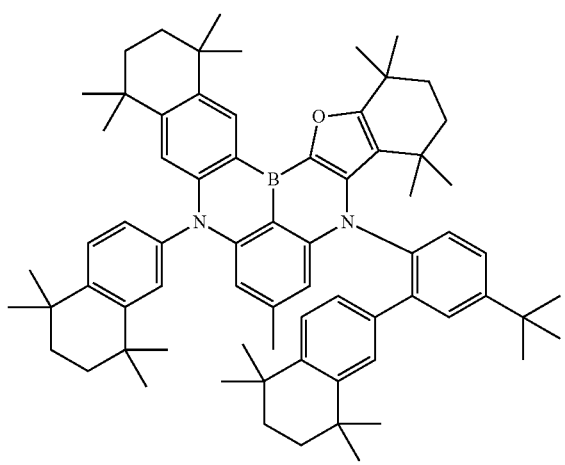
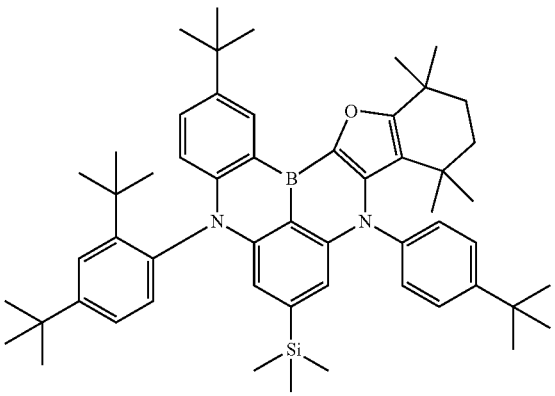
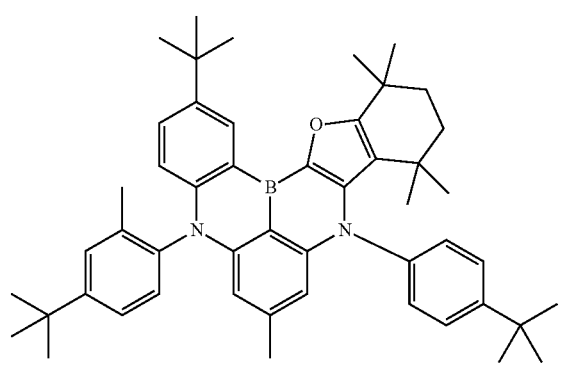
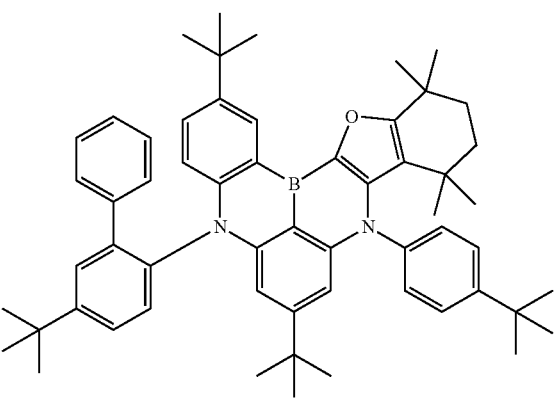

99
-continued
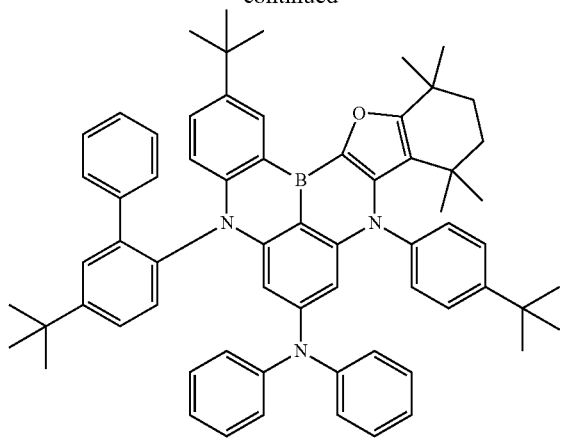
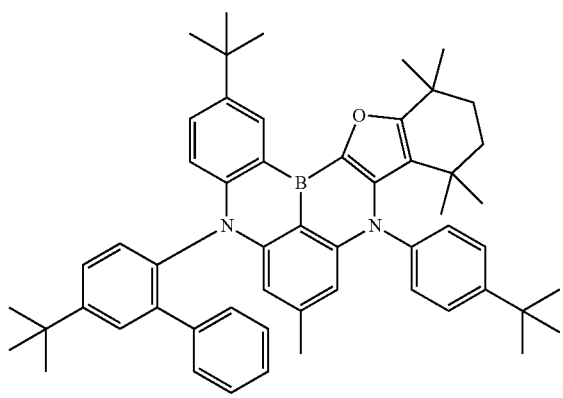
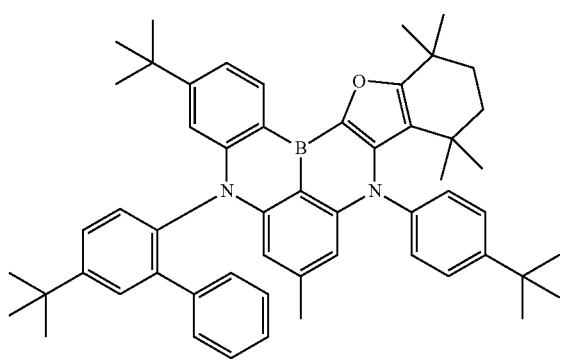
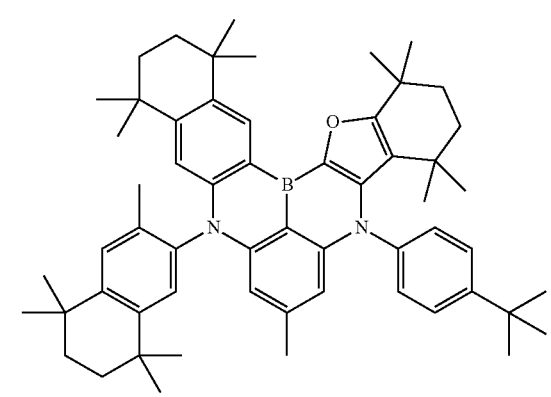
100
-continued
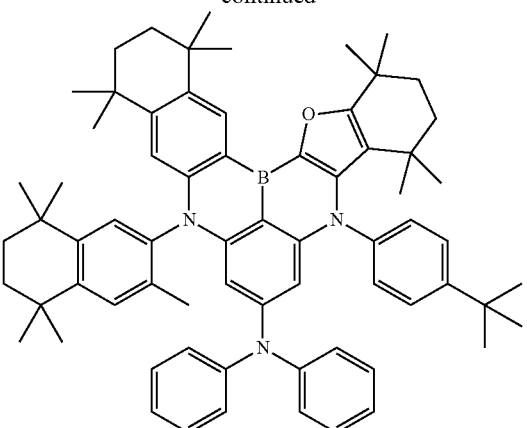
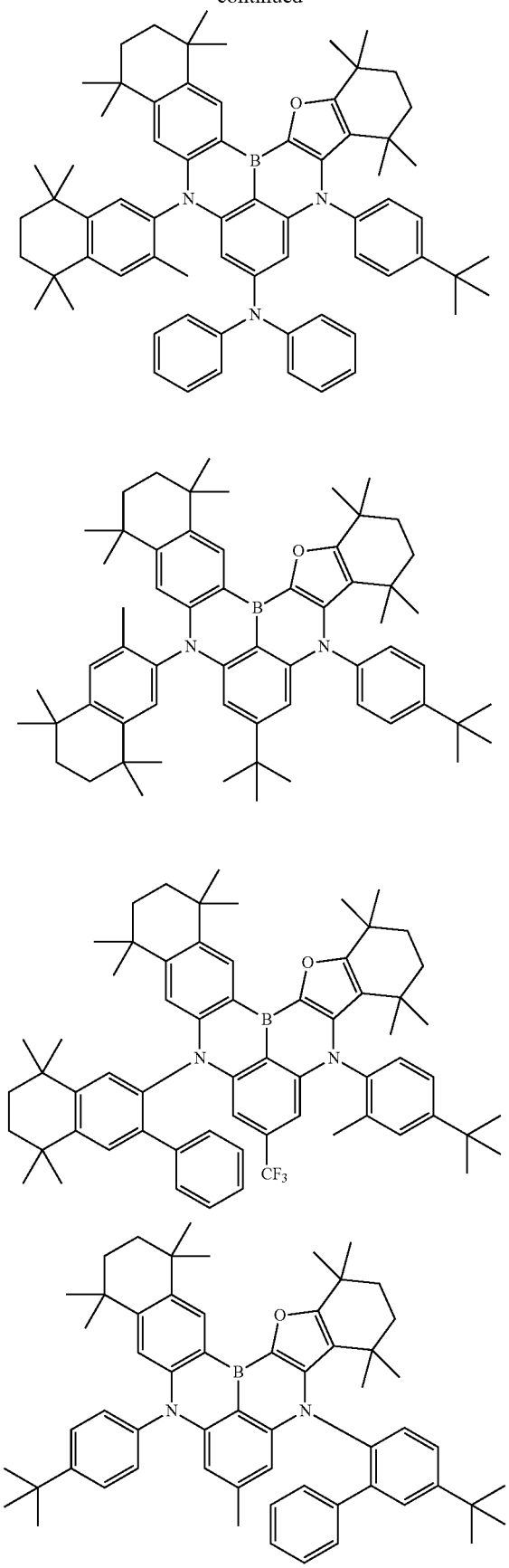

101
-continued
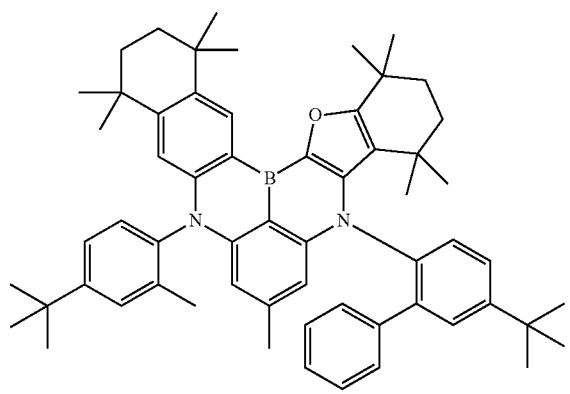
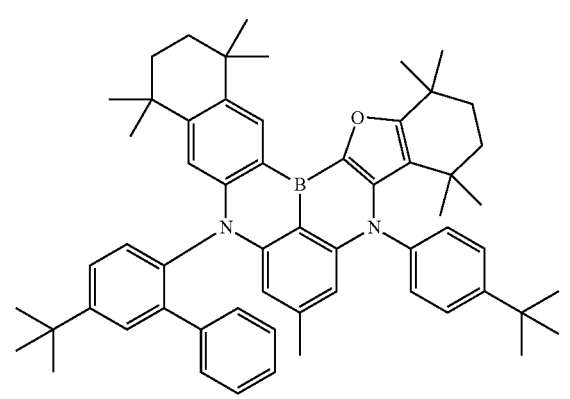
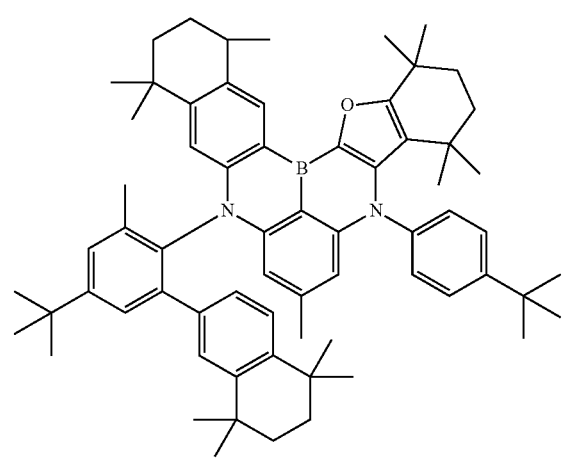
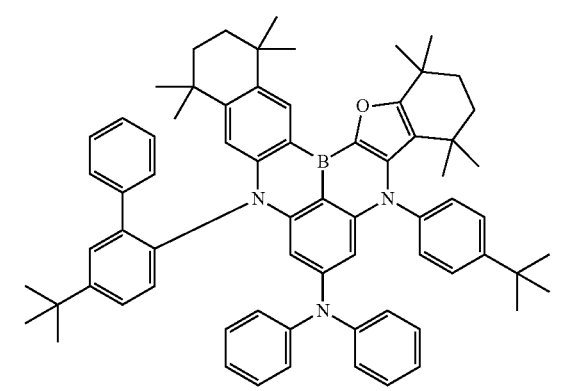
102
-continued
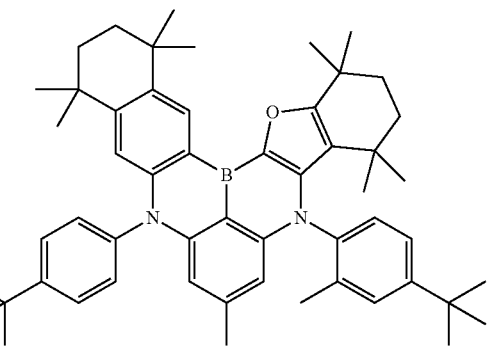
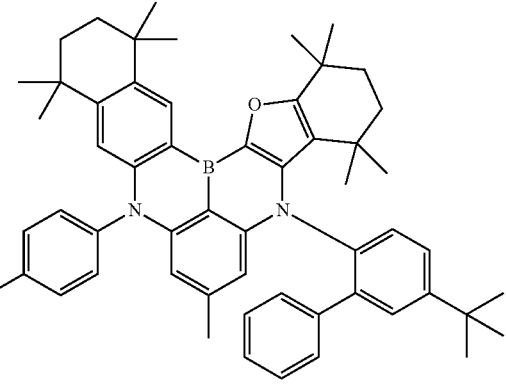
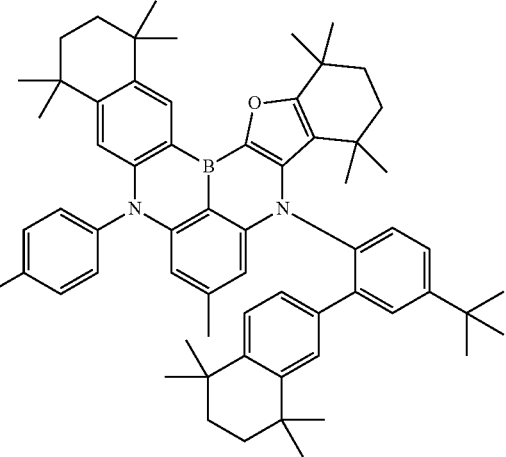
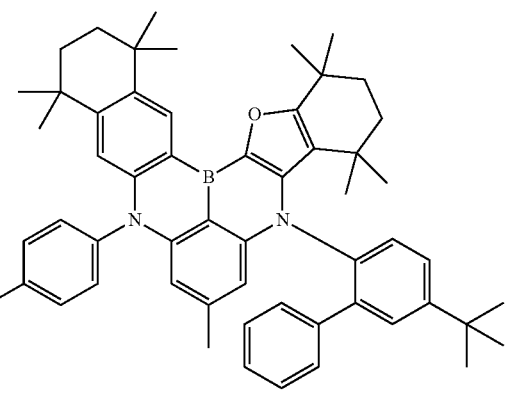

103
-continued
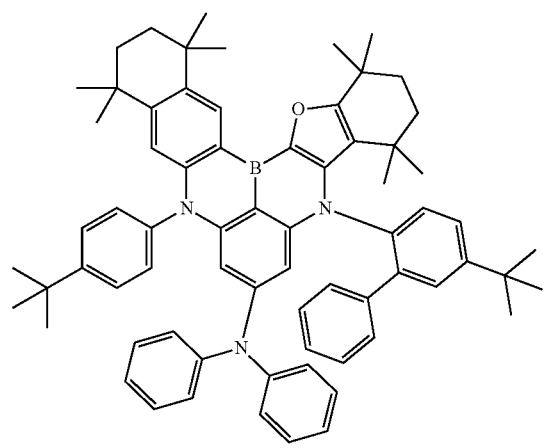
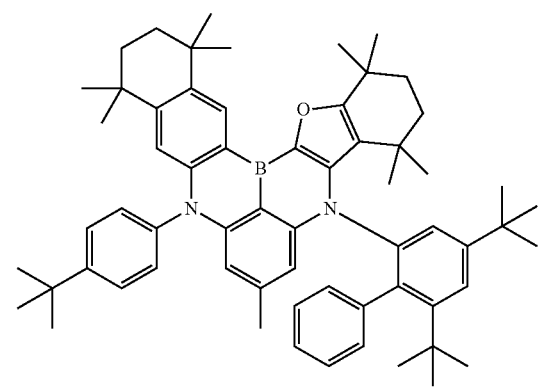
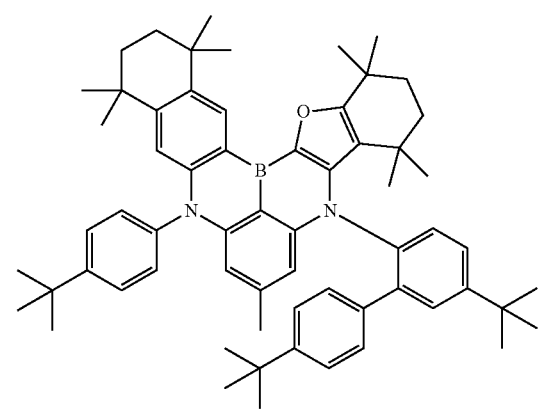
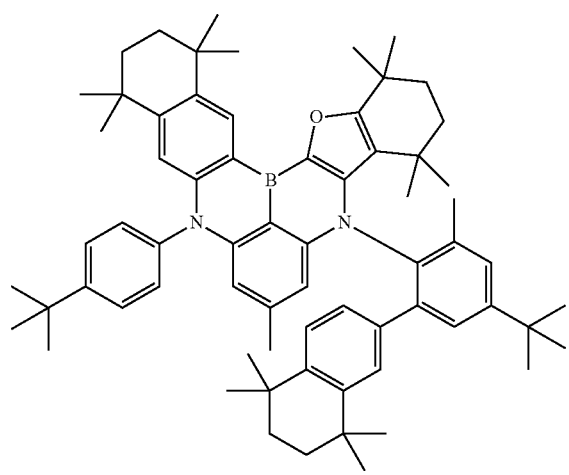 [SMILES: Cc1cc2c3c(c1)N(c1c(C)cc(C(C)(C)C)cc1-c1ccc4c(c1)C(C)(C)CCC4(C)C)c1c(oc4c1C(C)(C)CCC4(C)C)B3c1cc3c(cc1N2c1ccc(C(C)(C)C)cc1)C(C)(C)CCC3(C)C]
104
-continued
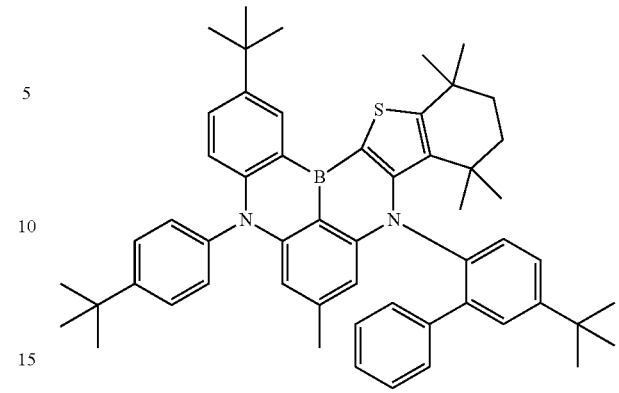
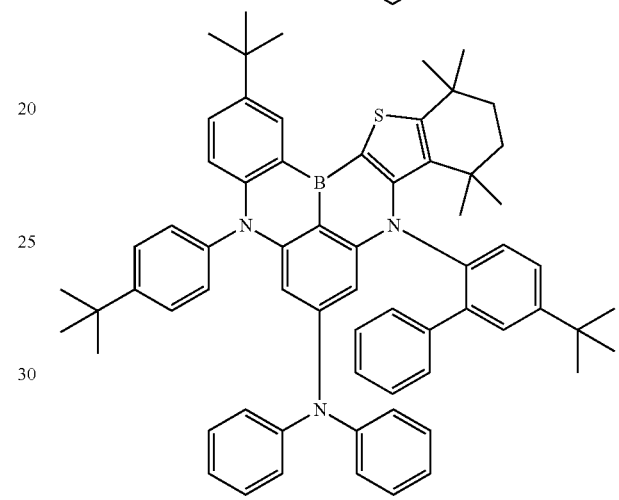
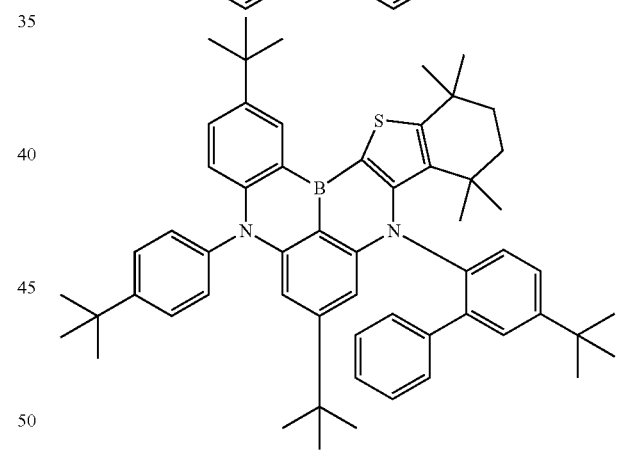
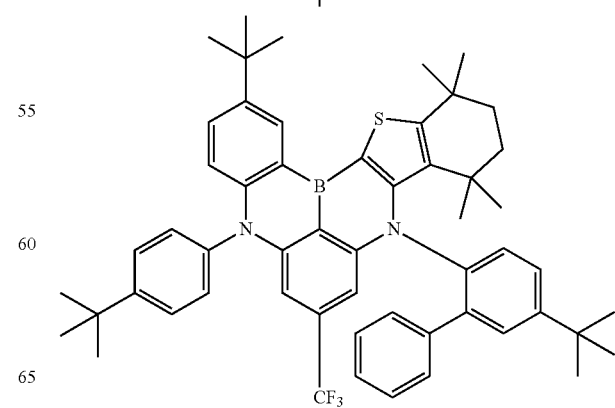

105
-continued
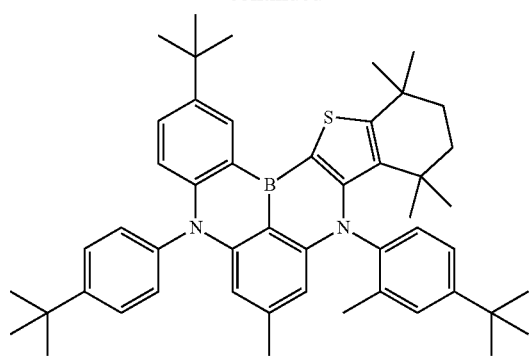
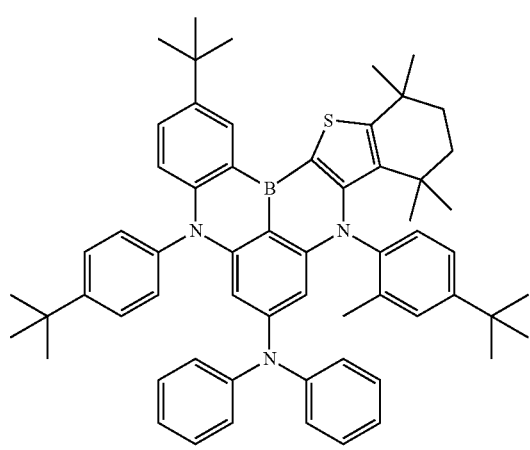
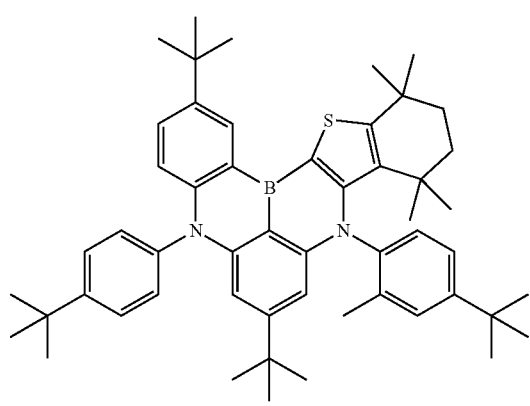
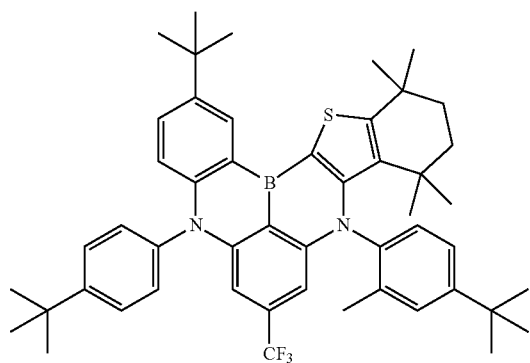
106
-continued
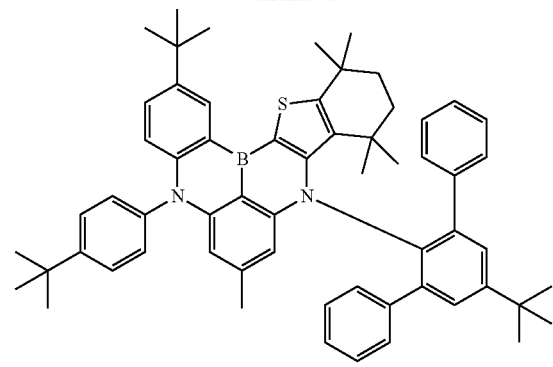
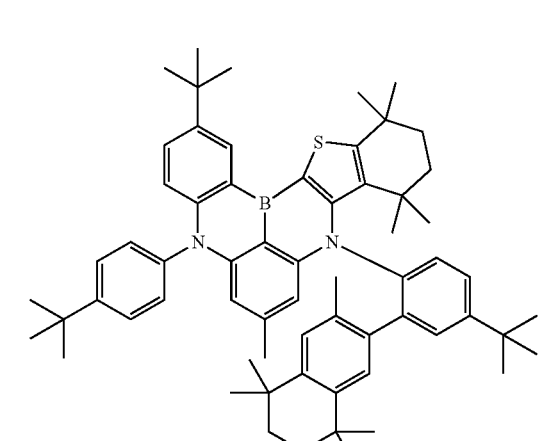
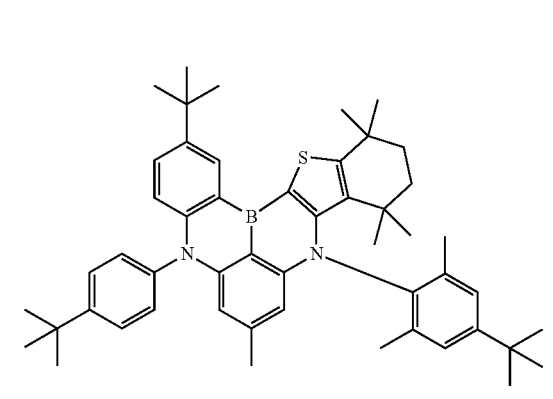
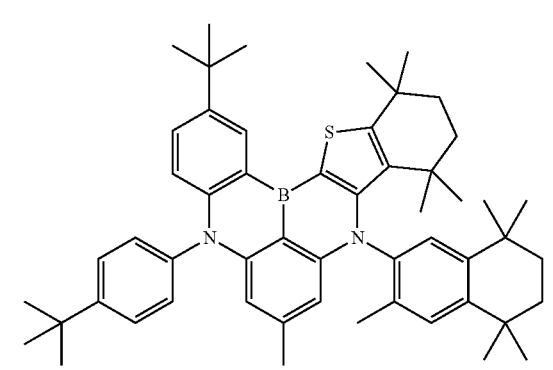

107
-continued
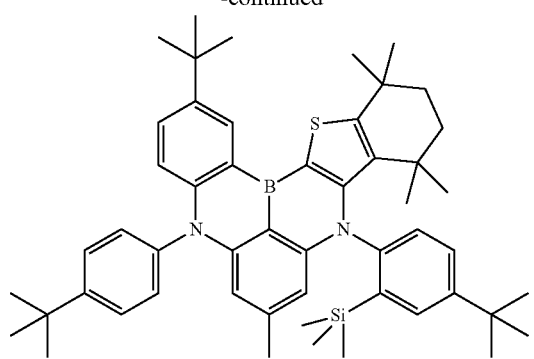
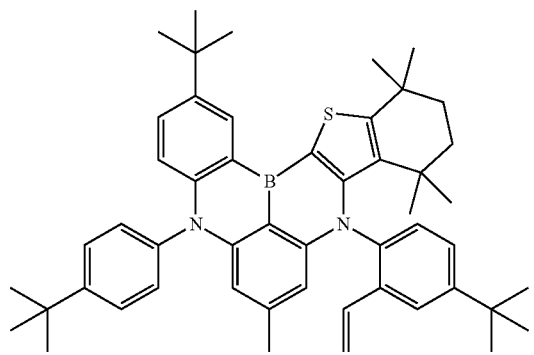
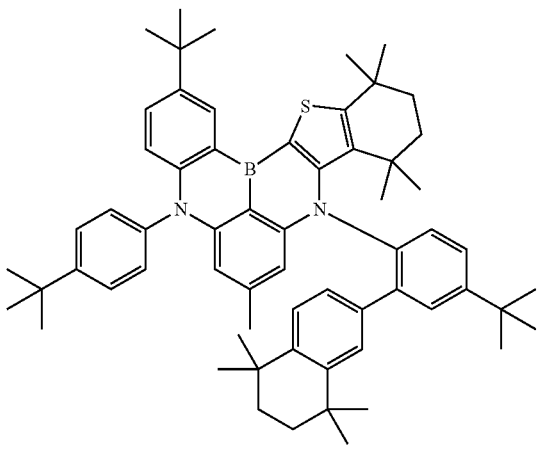
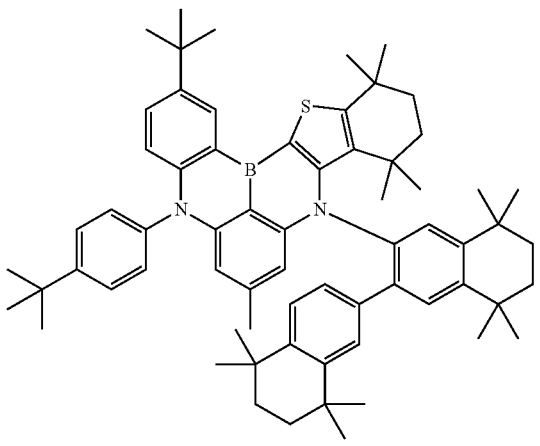
108
-continued
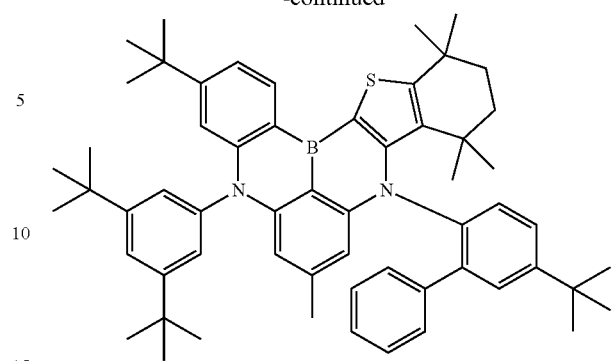
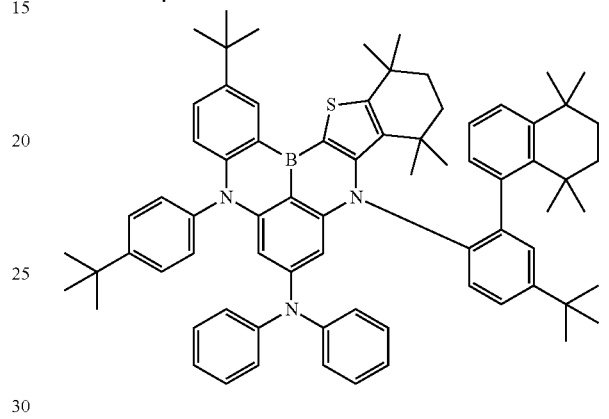
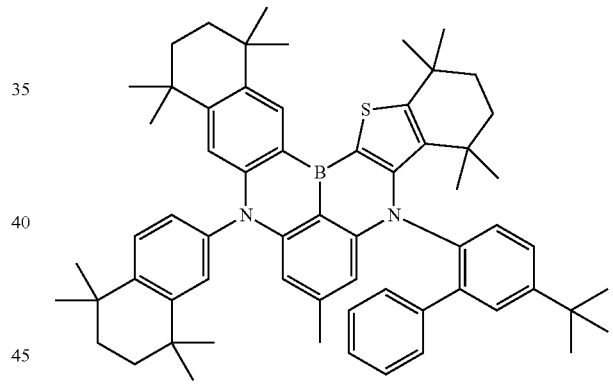
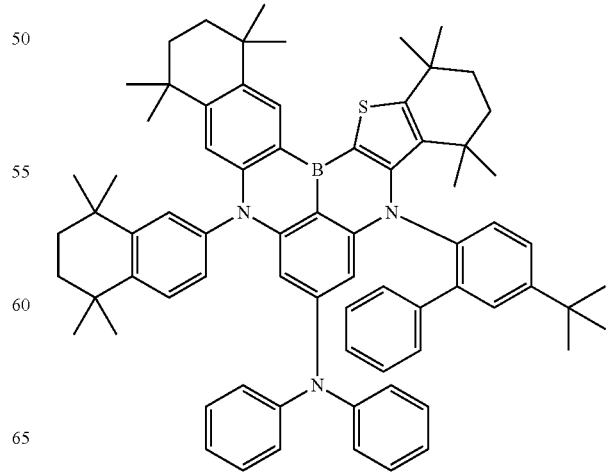

109
-continued
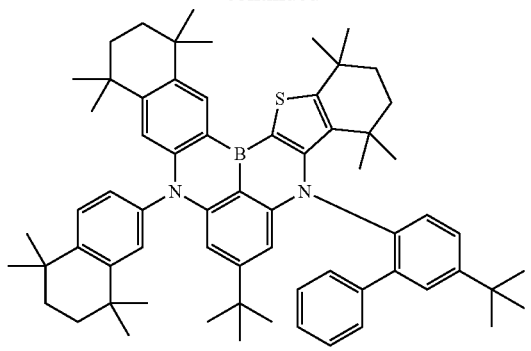
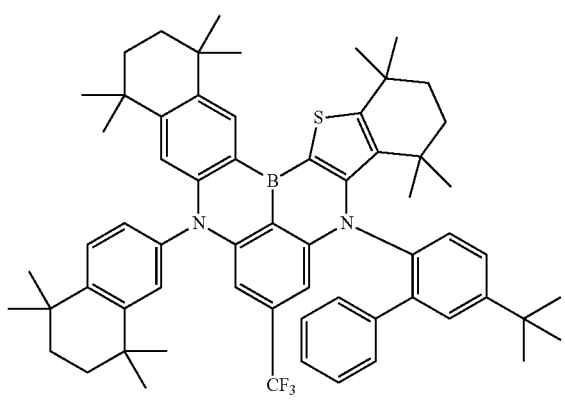
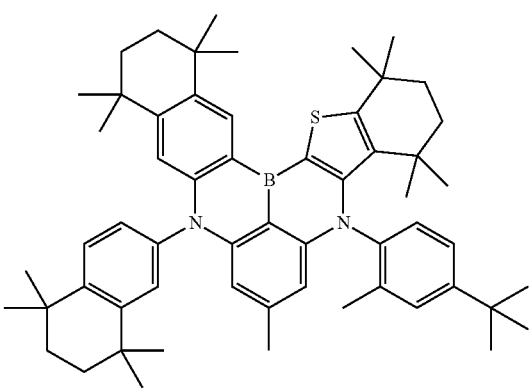
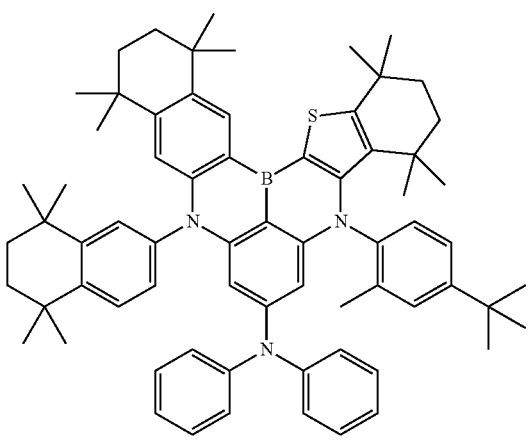
110
-continued
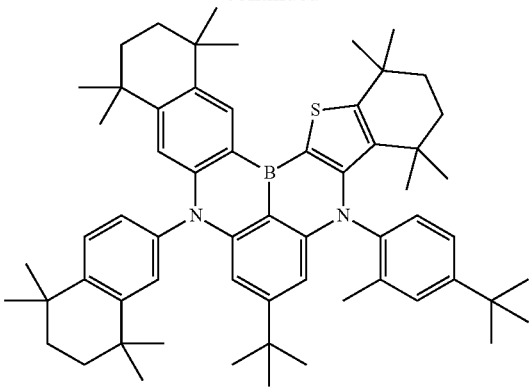
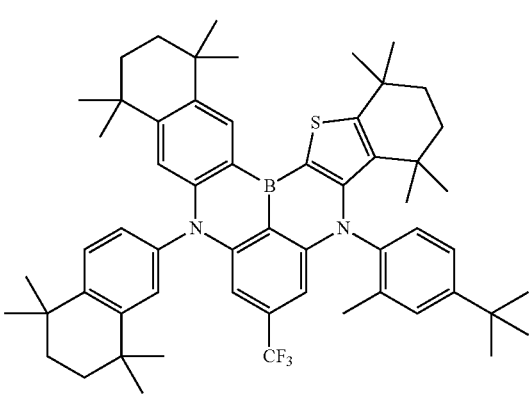
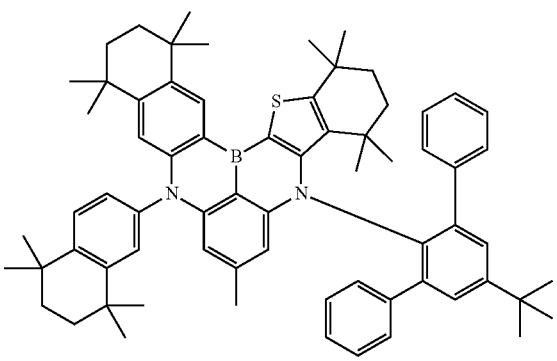
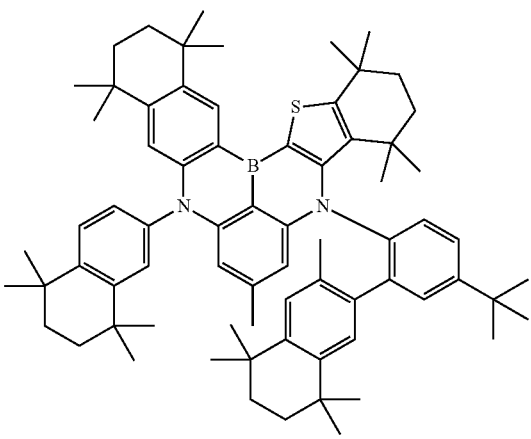

111
-continued
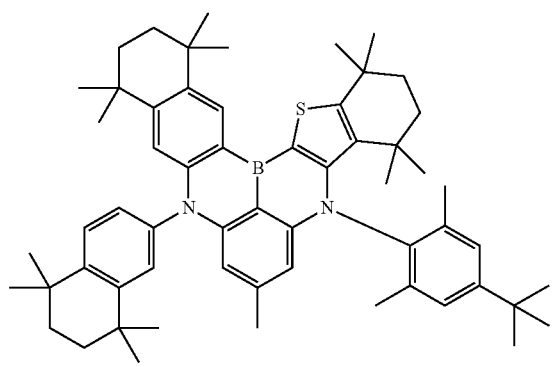
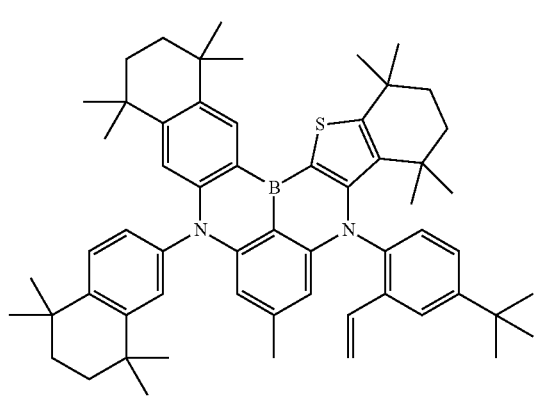
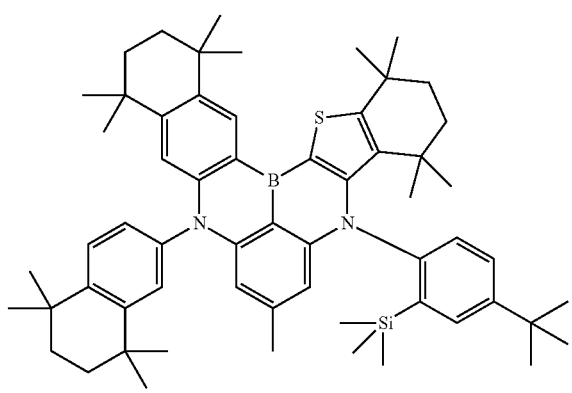
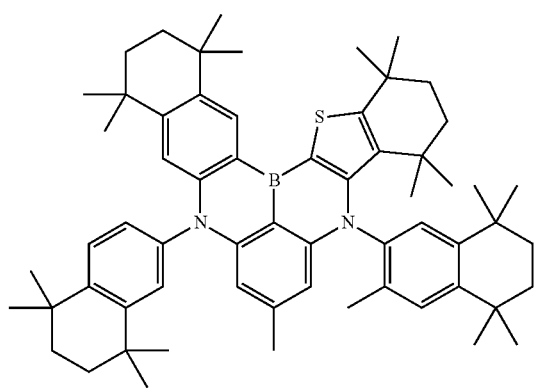
112
-continued
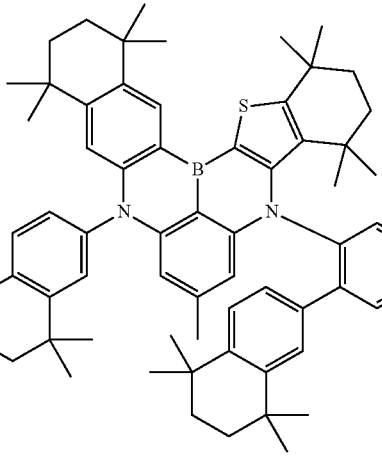
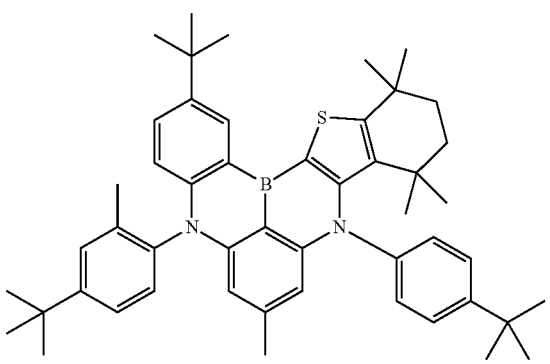
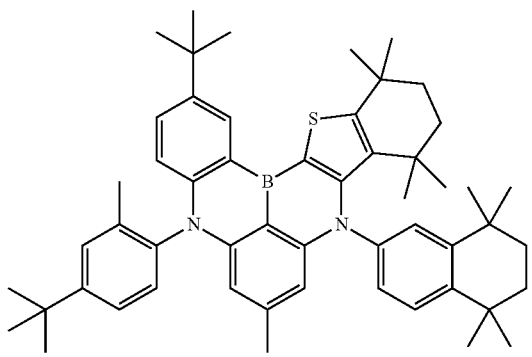
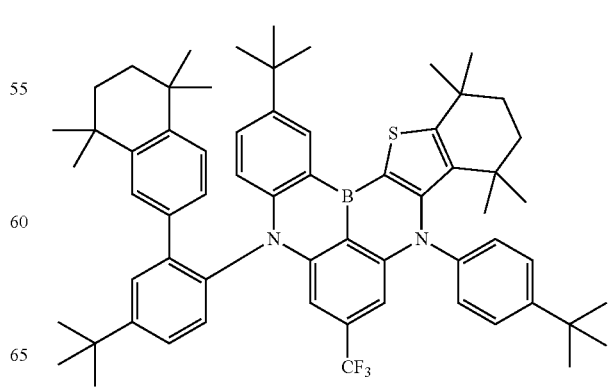

113
-continued
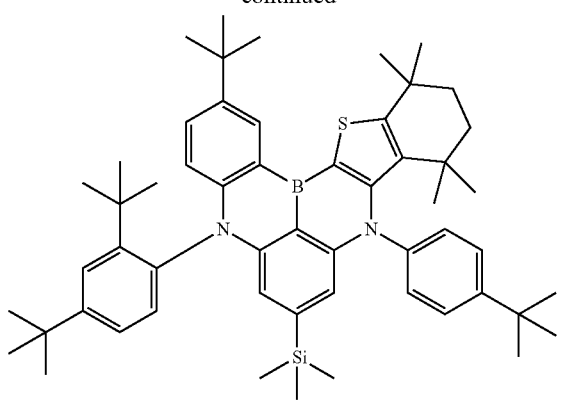
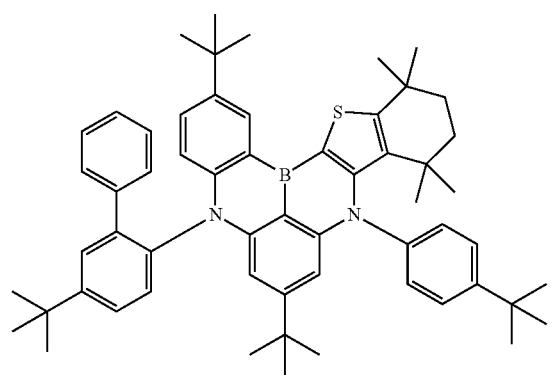
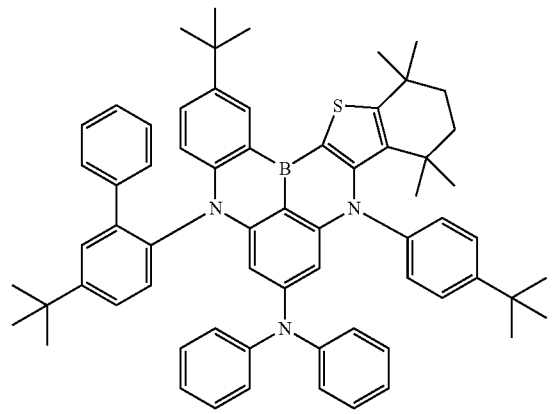
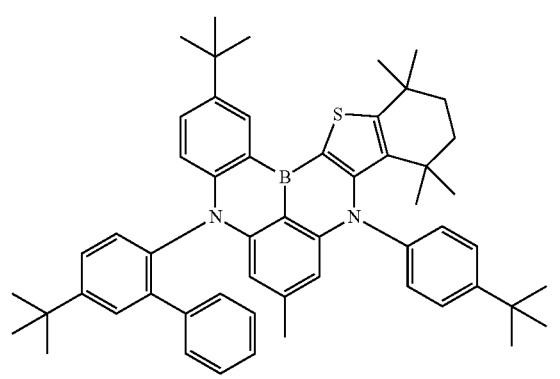
114
-continued
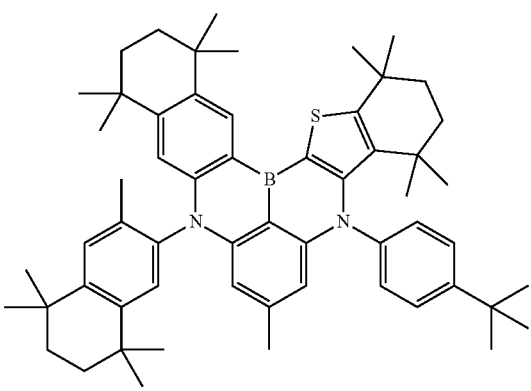
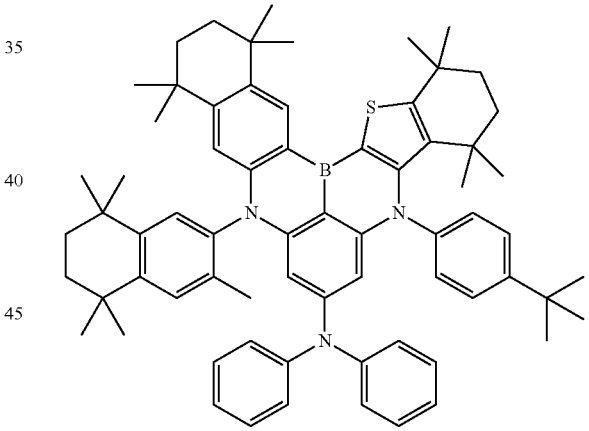
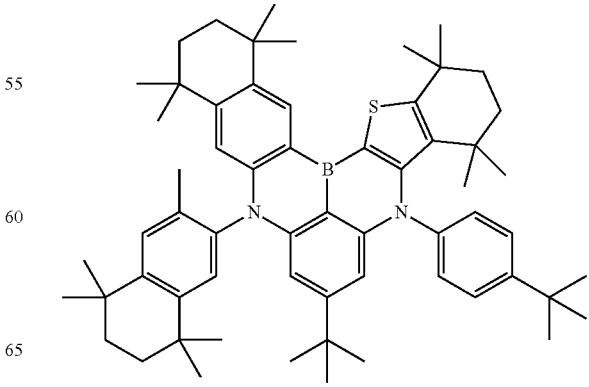

115
-continued
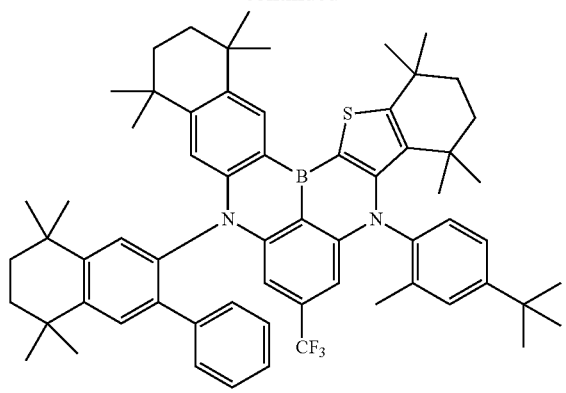
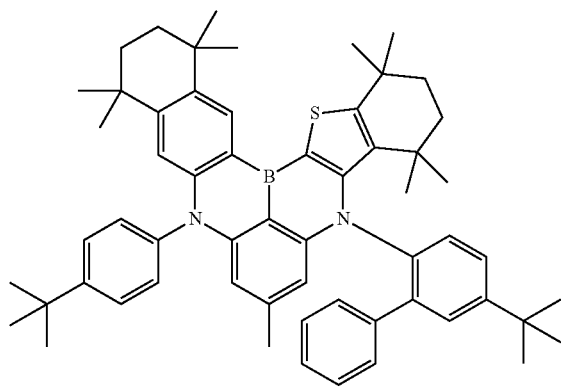
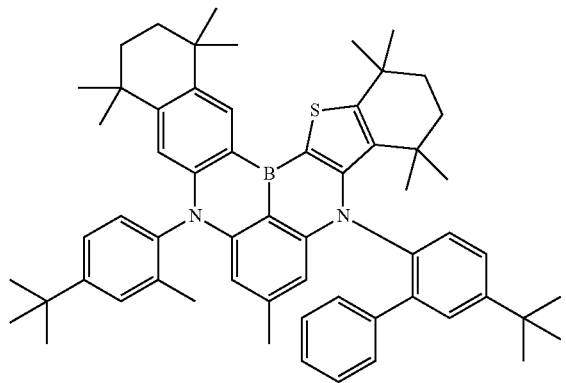
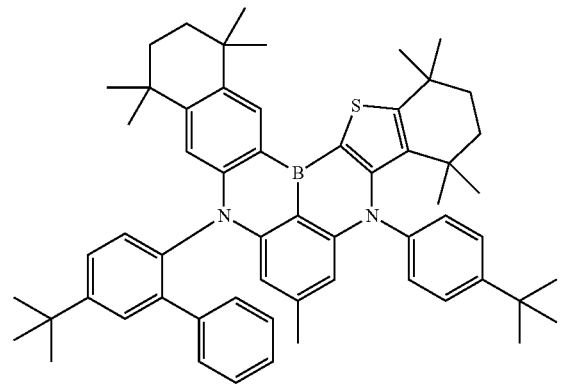
116
-continued
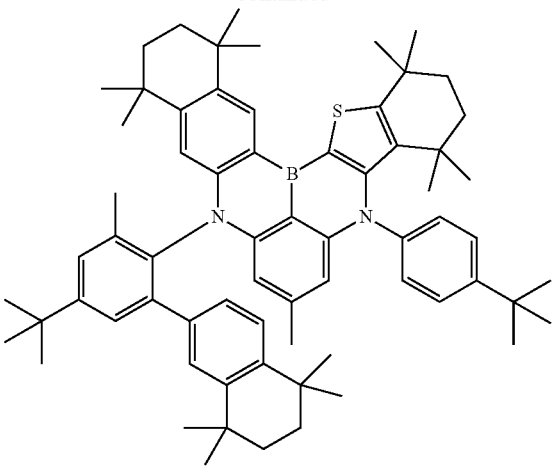
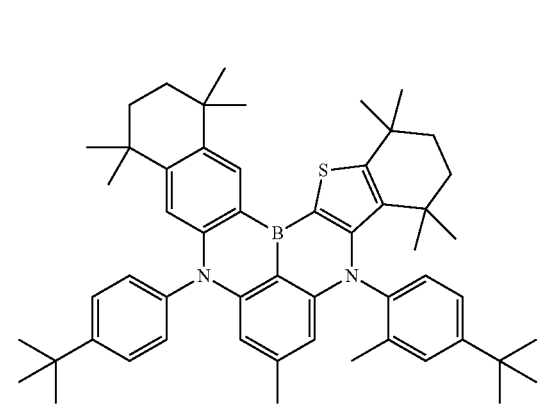
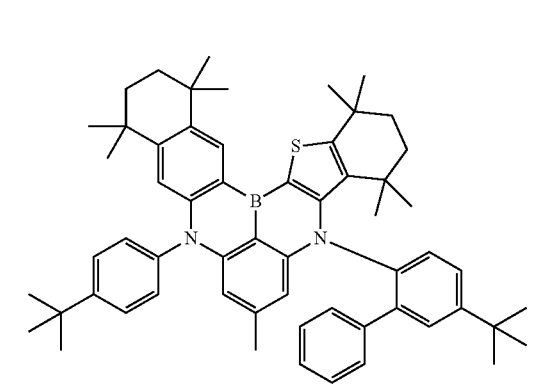

117
-continued
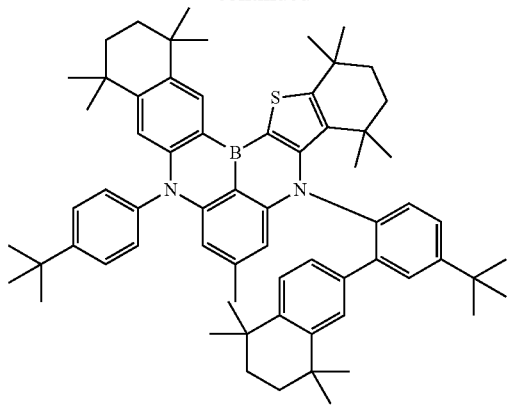 [SMILES: Cc1cc2c3c(c1)N(c1c(C)cc(C(C)(C)C)cc1-c1ccc4c(c1)C(C)(C)CCC4(C)C)c1c(sc4c1C(C)(C)CCC4(C)C)B3c1cc3c(cc1N2c1ccc(C(C)(C)C)cc1)C(C)(C)CCC3(C)C]
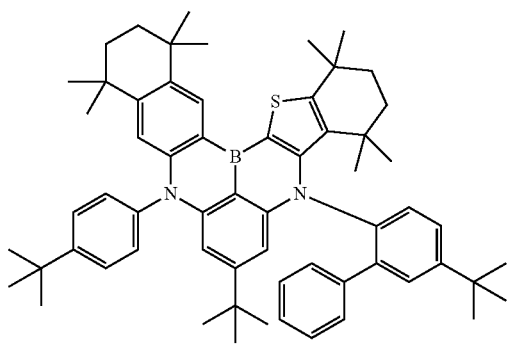
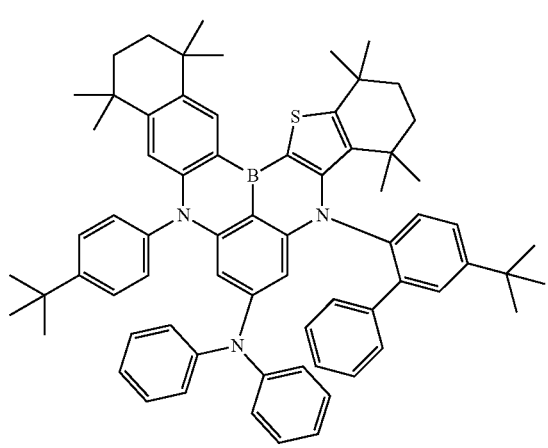
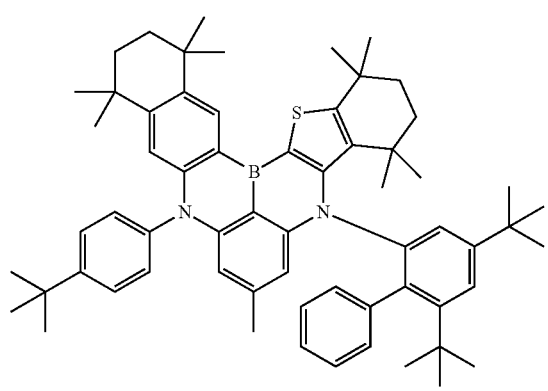
118
-continued
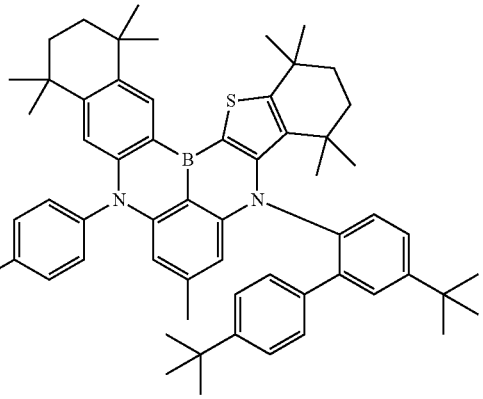
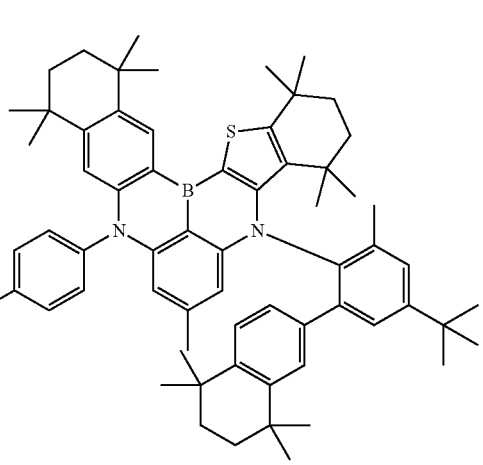
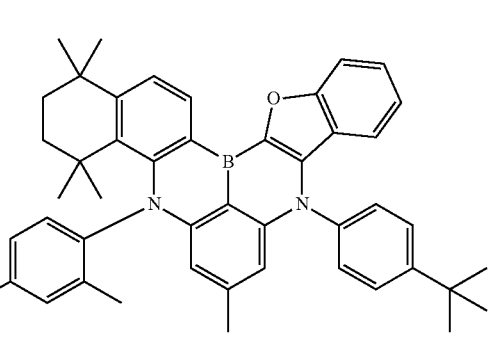
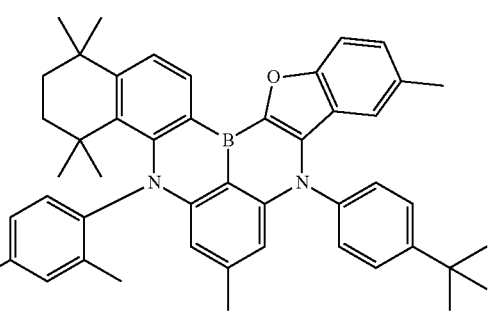

119
-continued
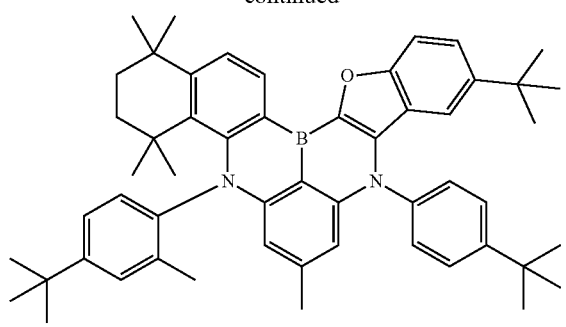
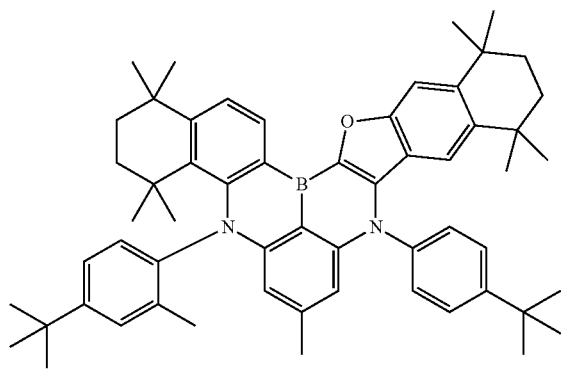
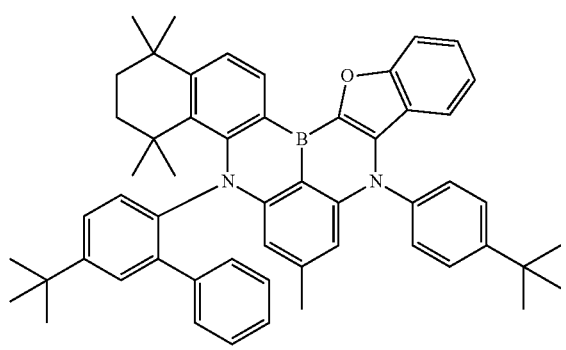
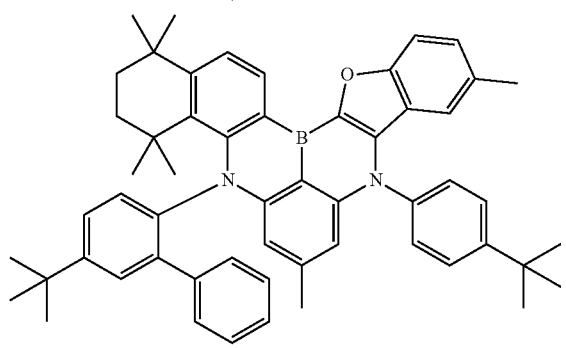
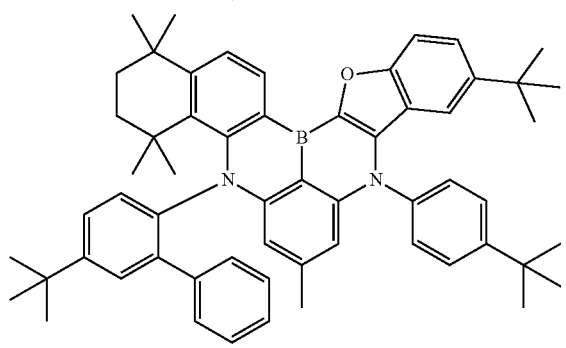
120
-continued
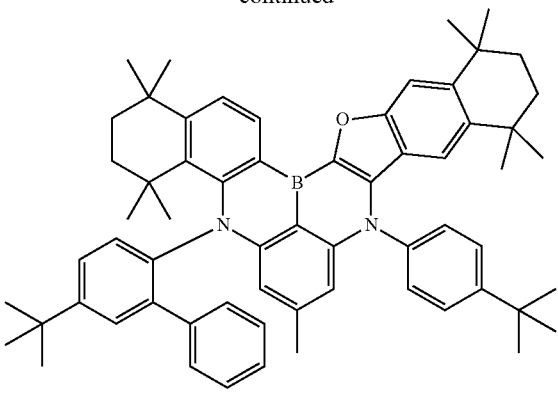
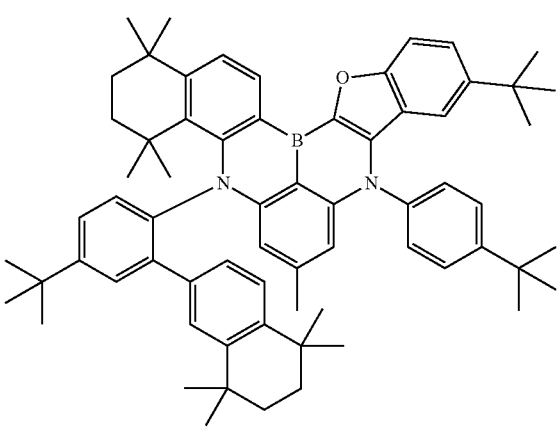
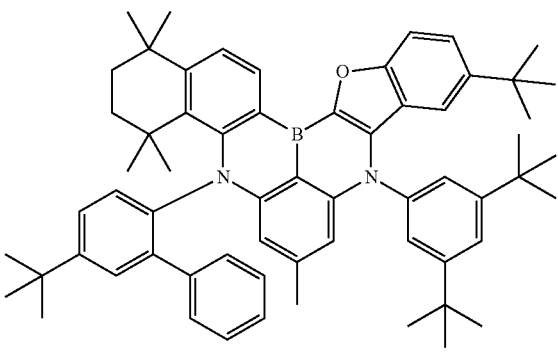
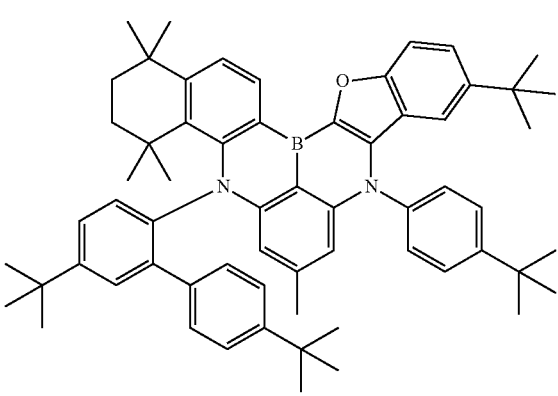

121
-continued
122
-continued
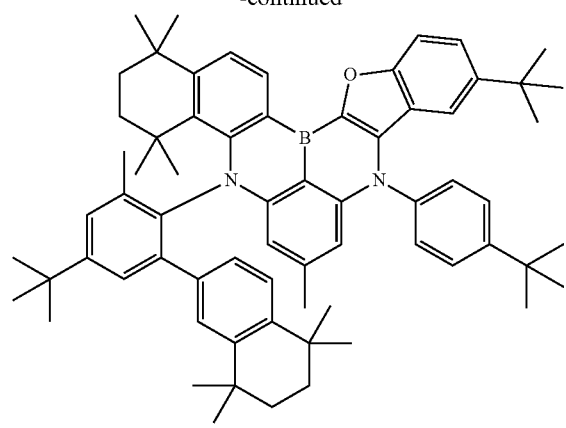
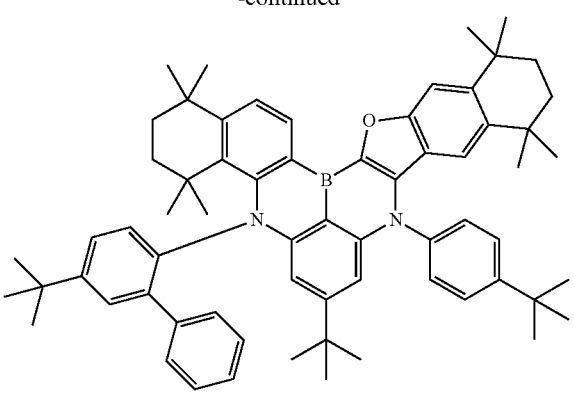

123
-continued
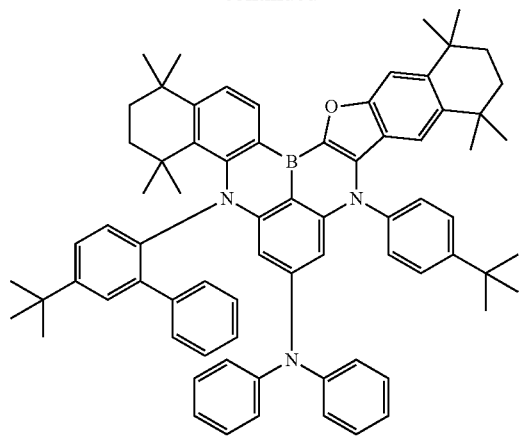
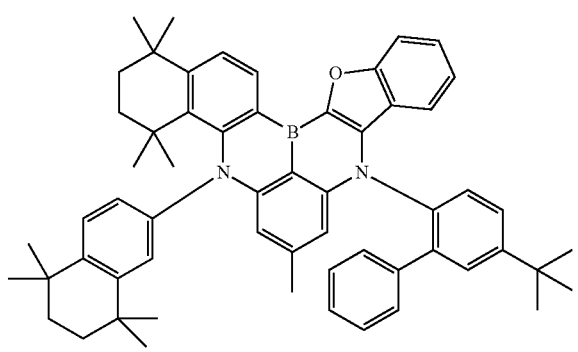
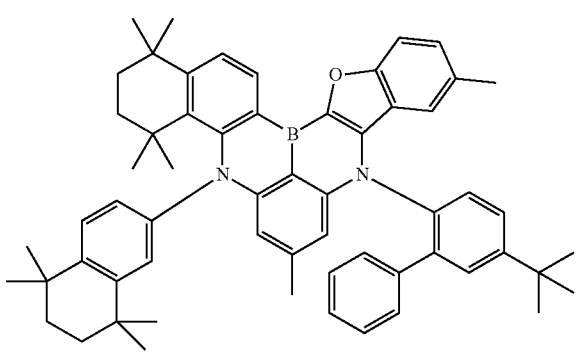
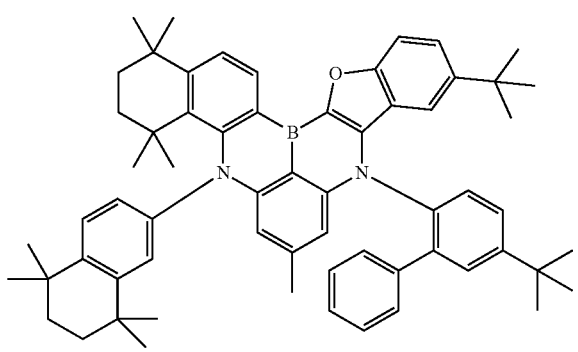
124
-continued
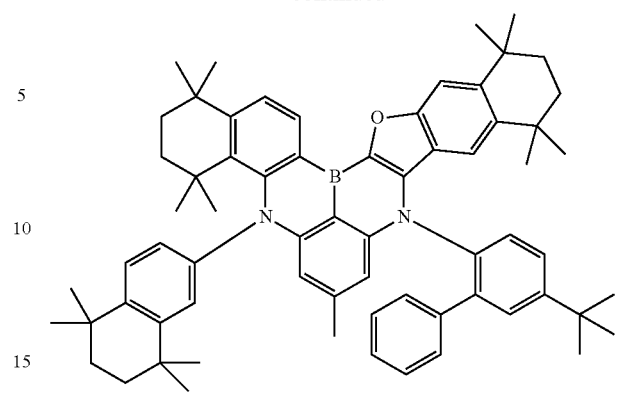
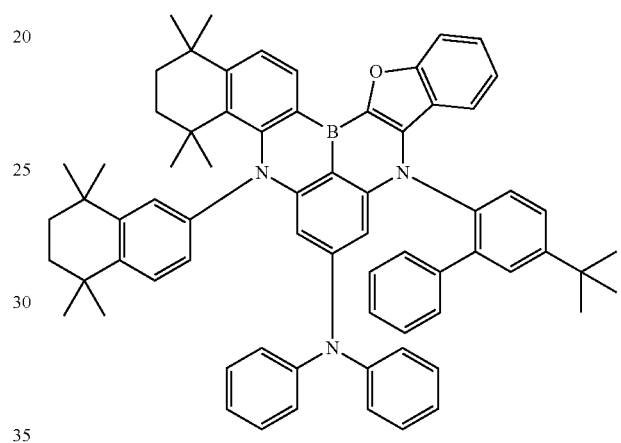
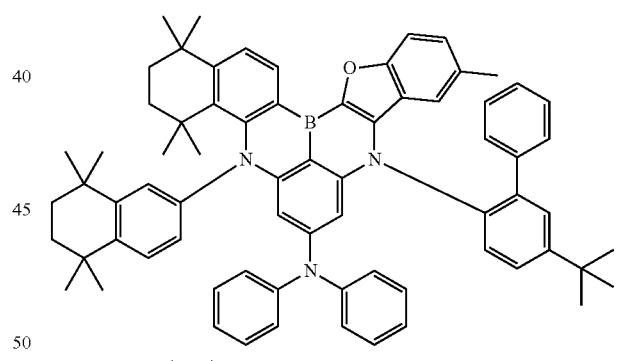
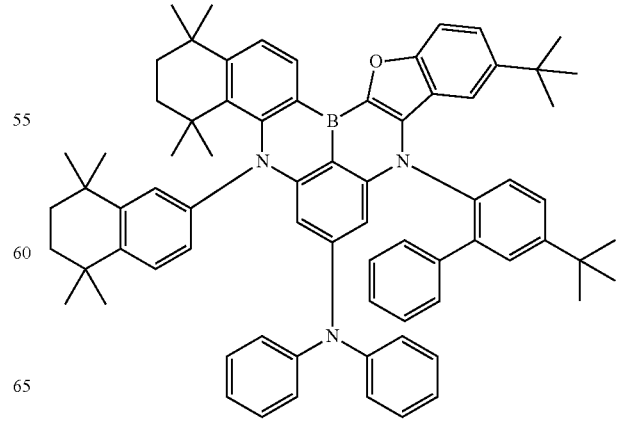

125
-continued
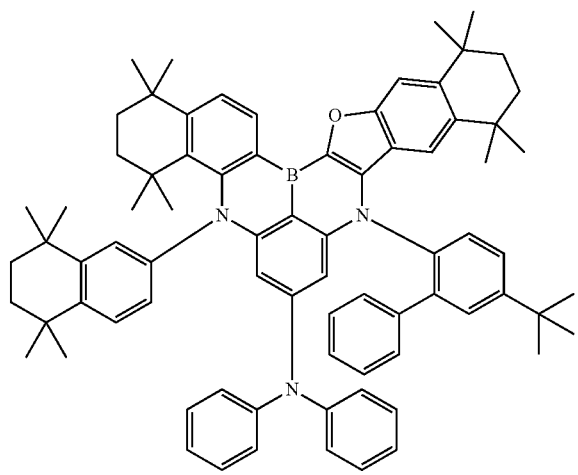
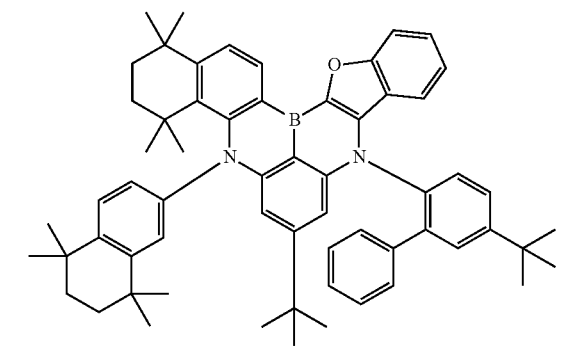

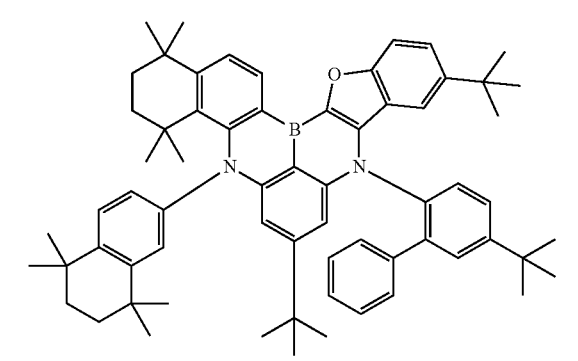
126
-continued
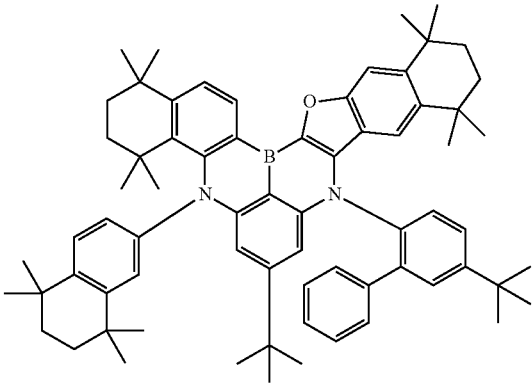
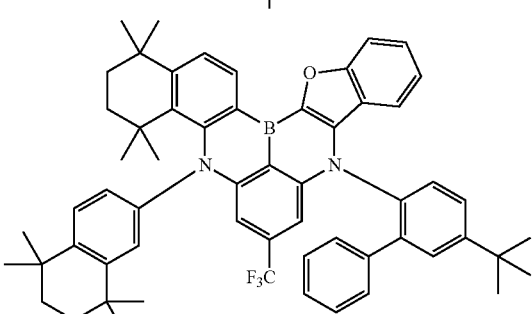
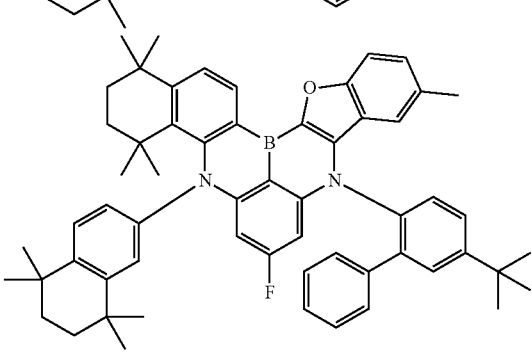
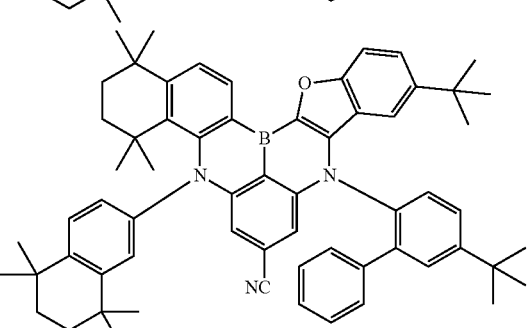
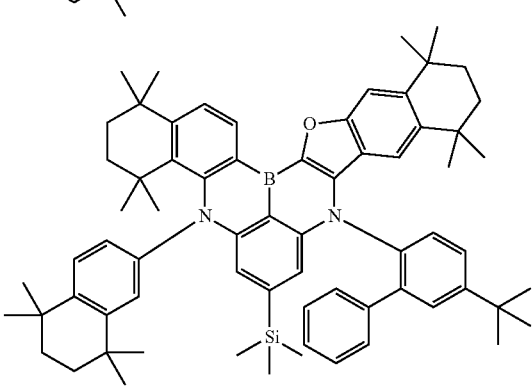

127
-continued
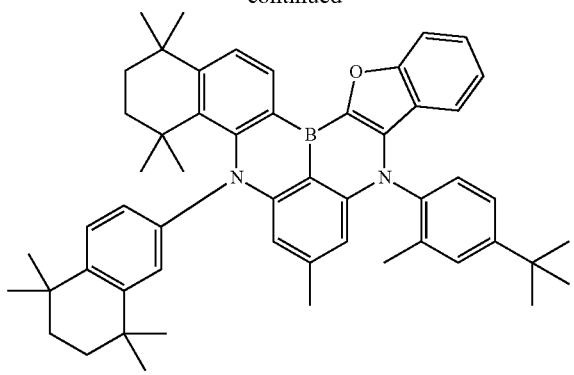
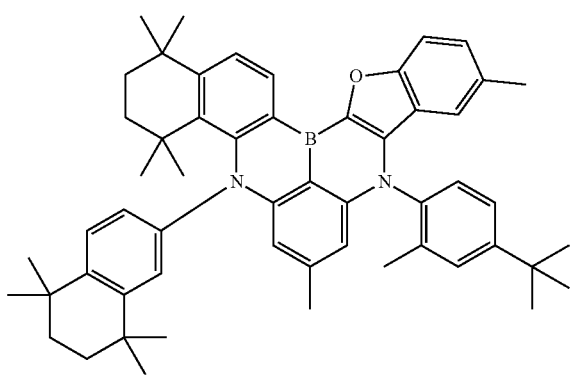
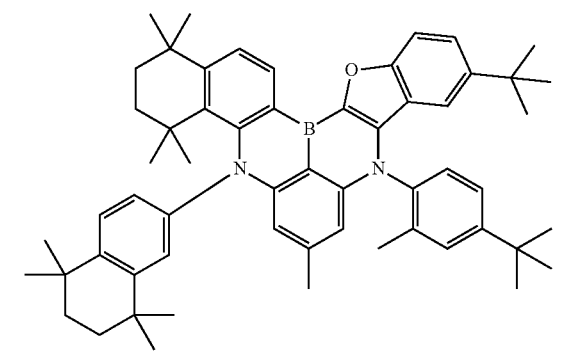
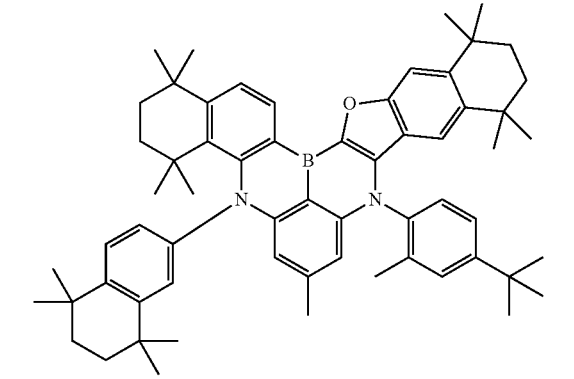
128
-continued
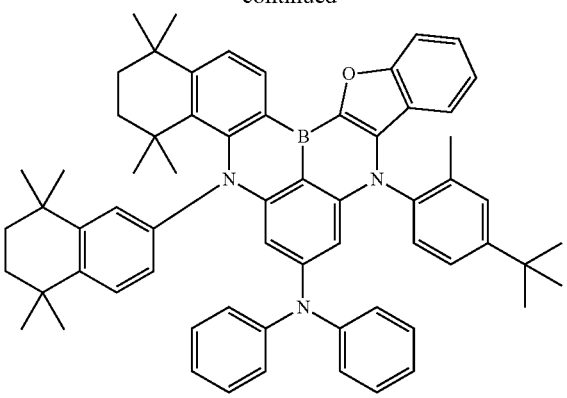
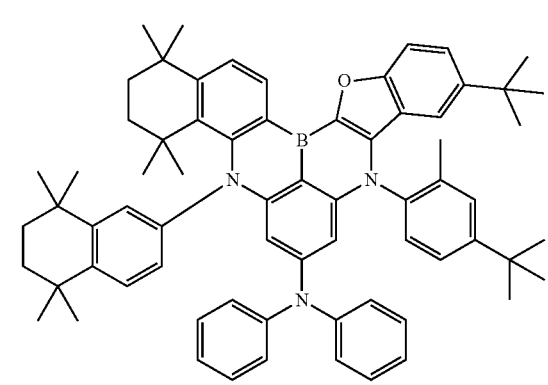
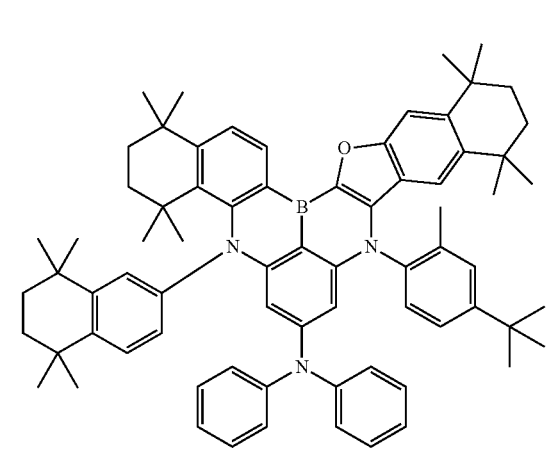

| 129 -continued | 130 -continued |
|---|---|
| 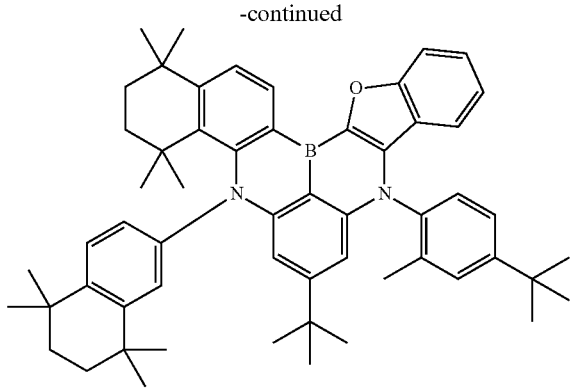 | 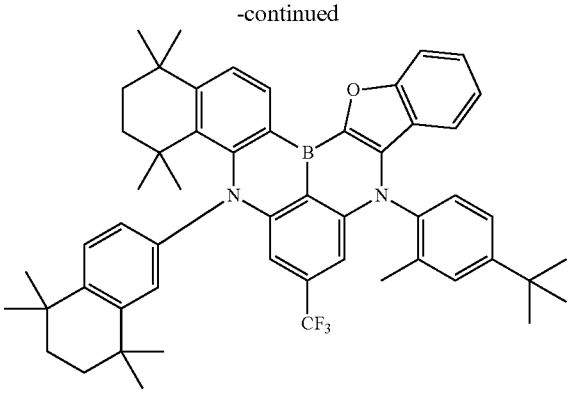 |
| 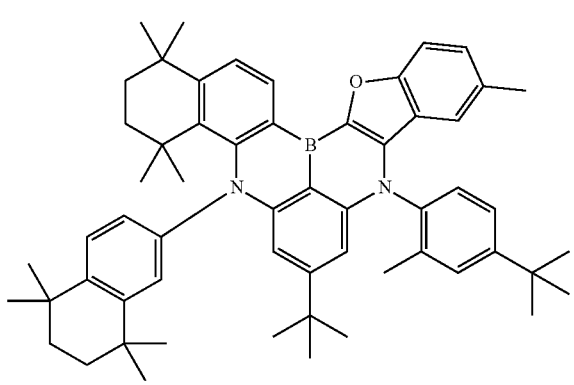 | 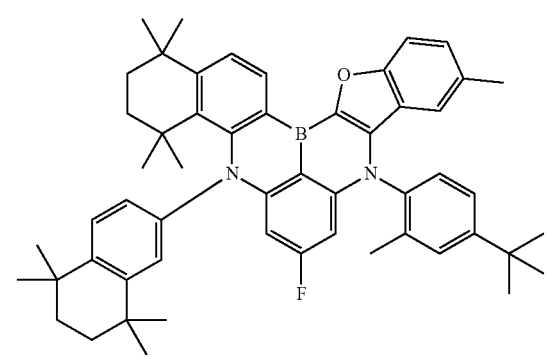 |
| 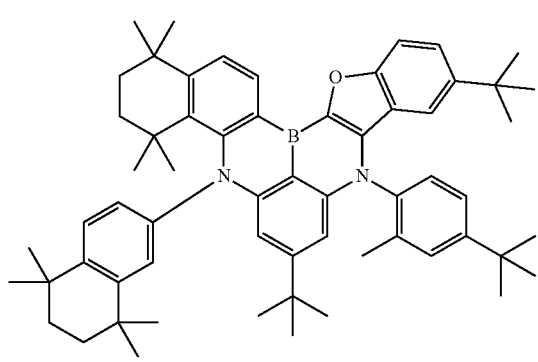 | 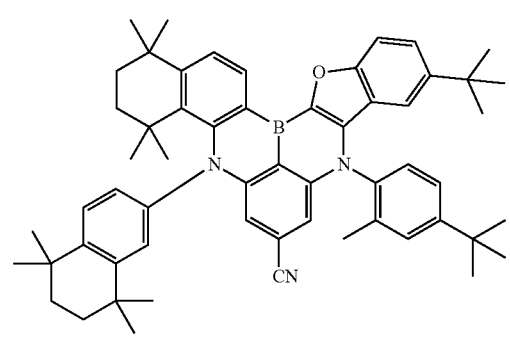 |
| 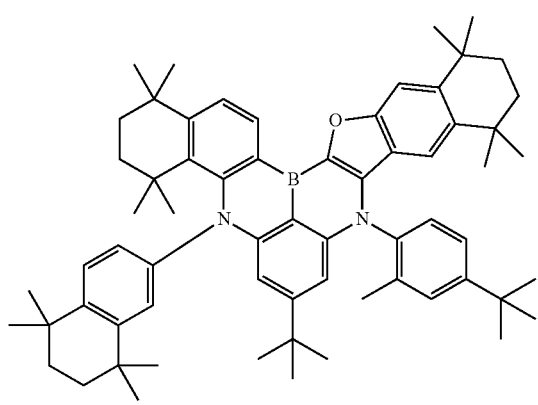 | 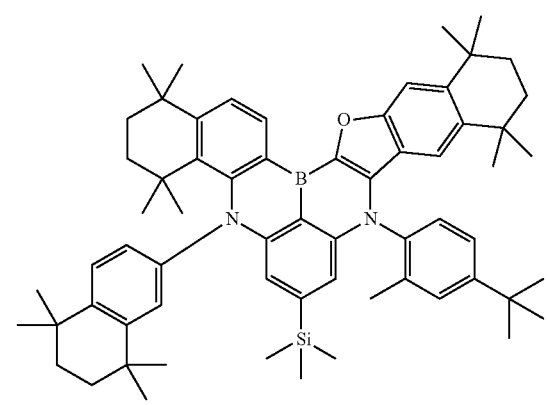 |

131
-continued
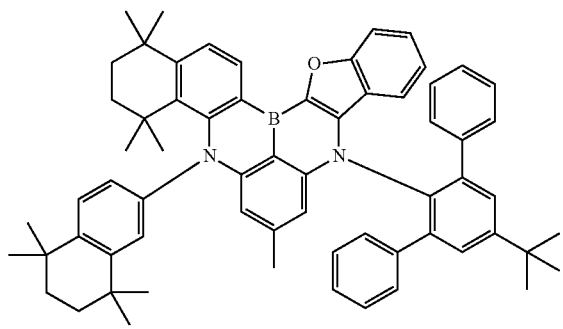
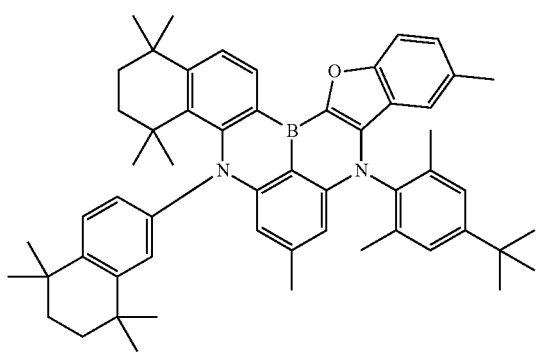
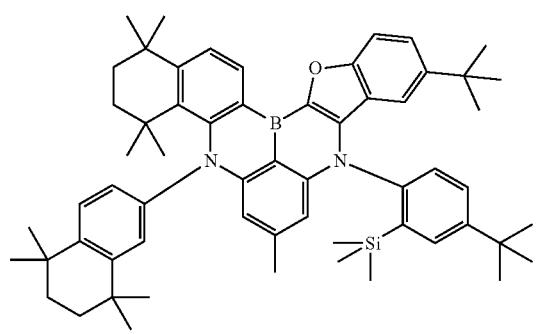
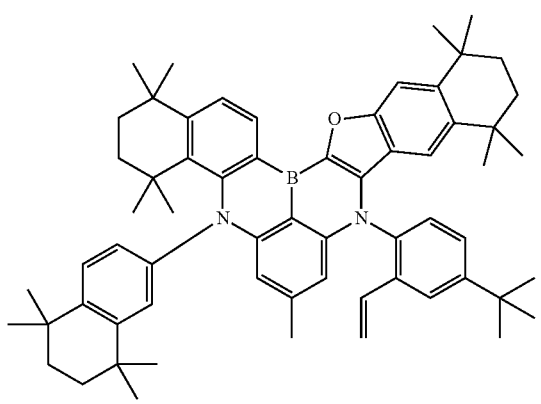
132
-continued
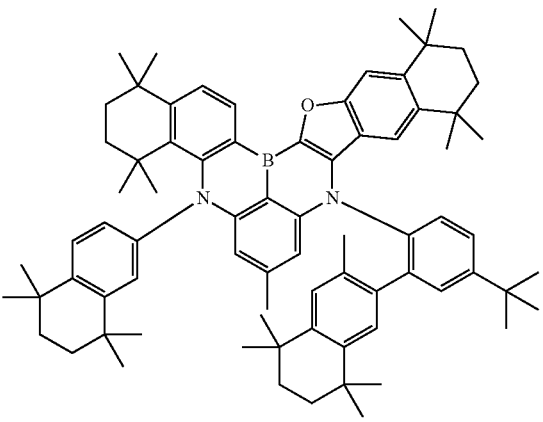
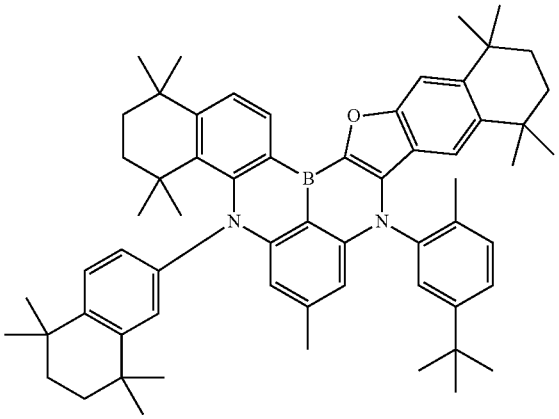
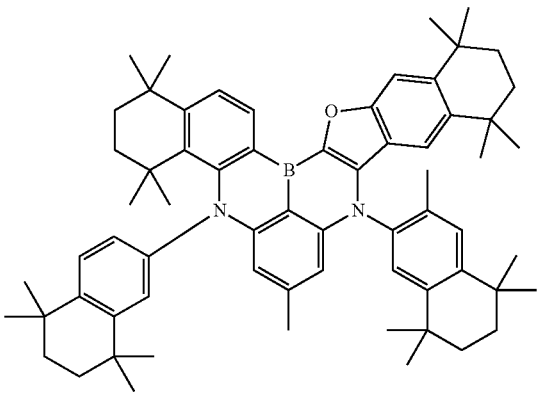
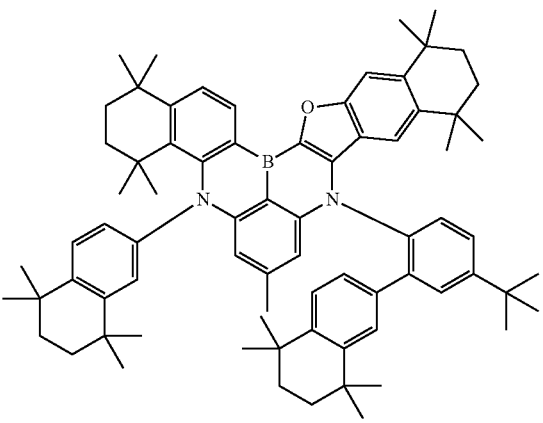

133
-continued
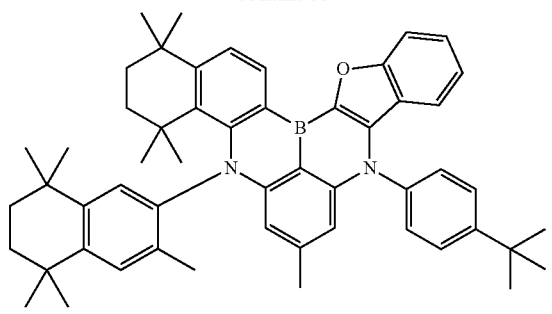
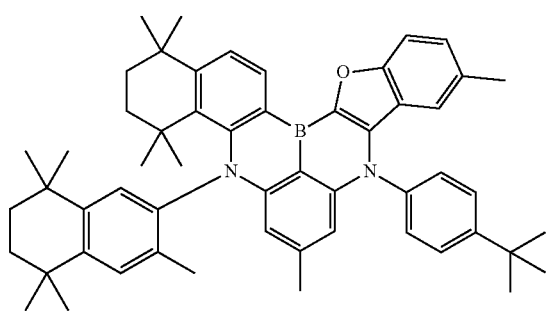
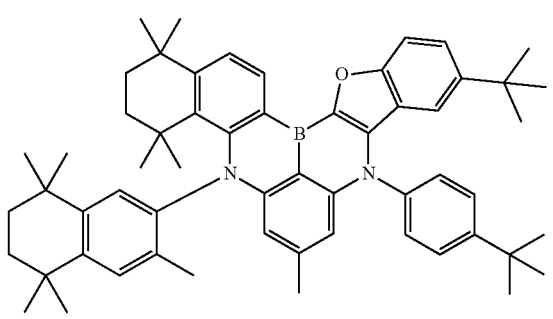
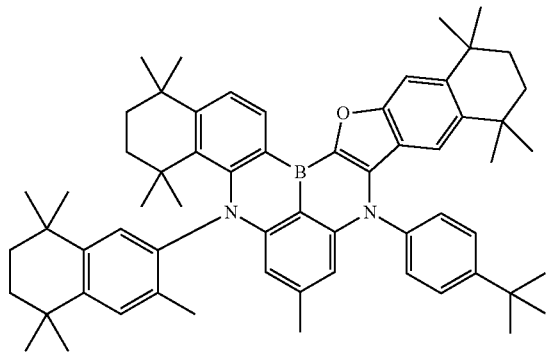
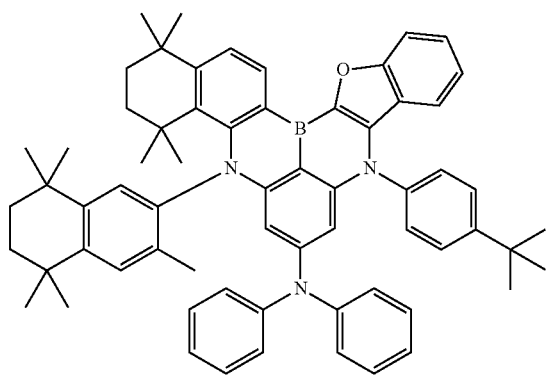
134
-continued
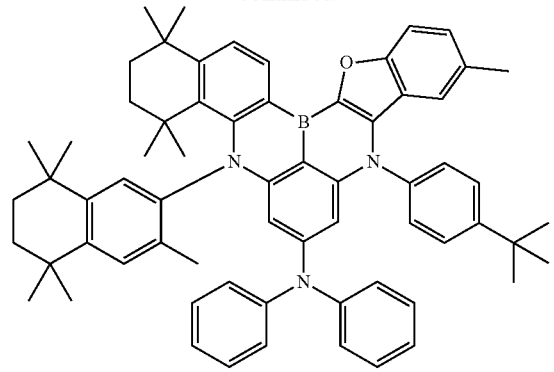
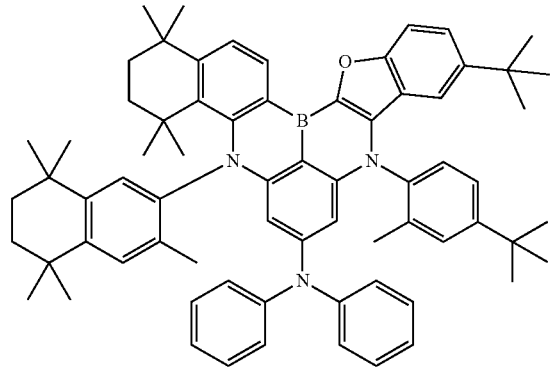
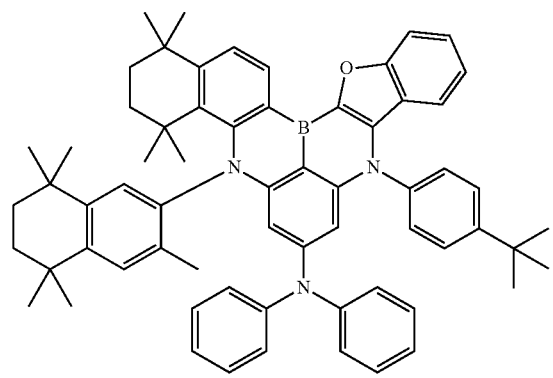
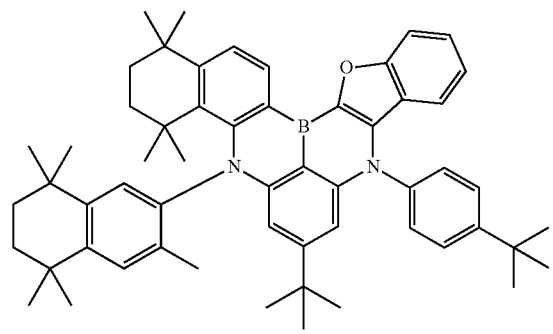

135
-continued
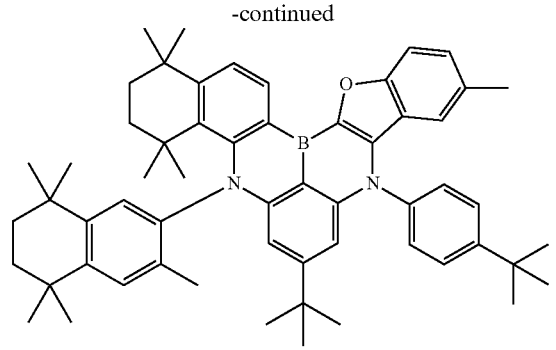
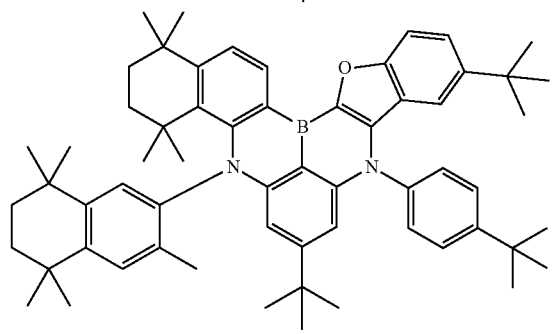
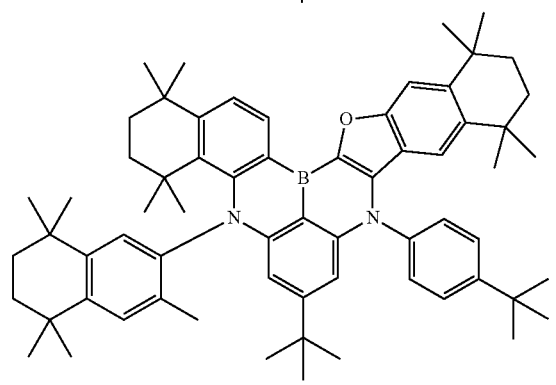
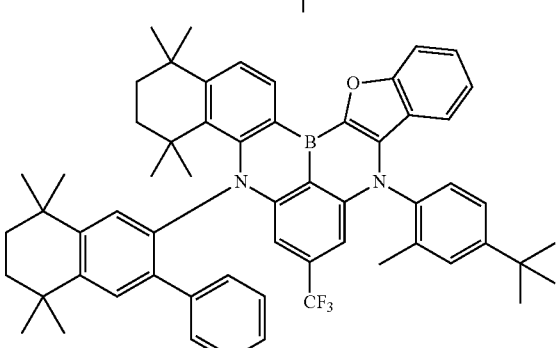
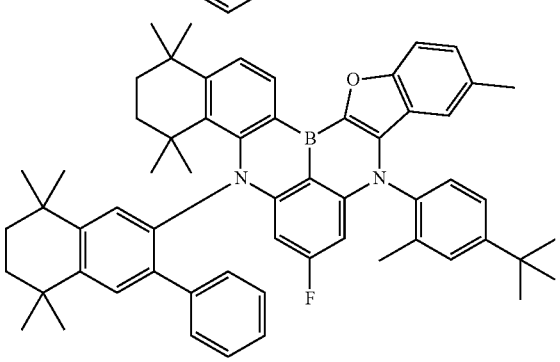
136
-continued
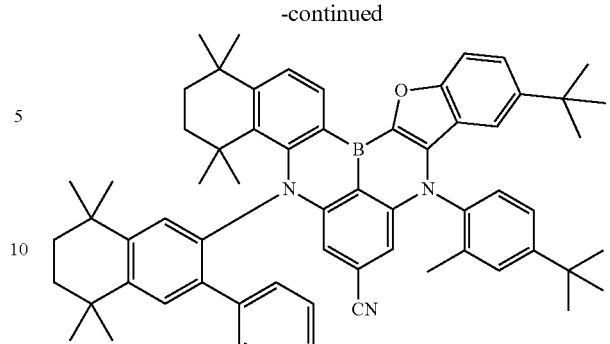
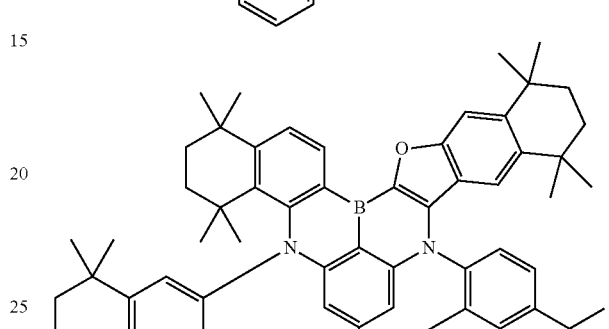
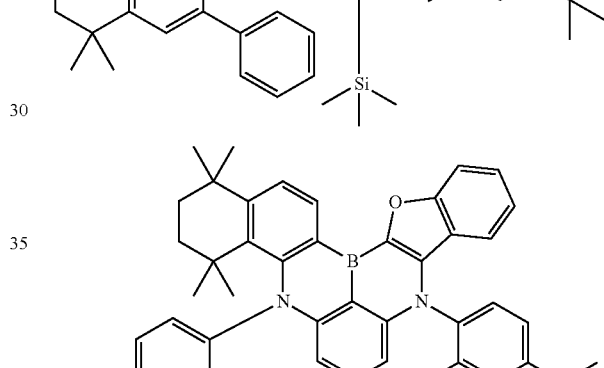
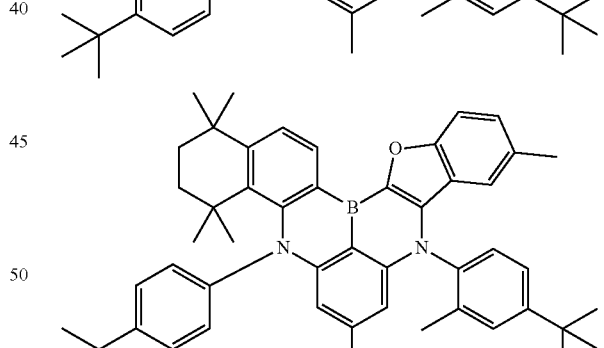
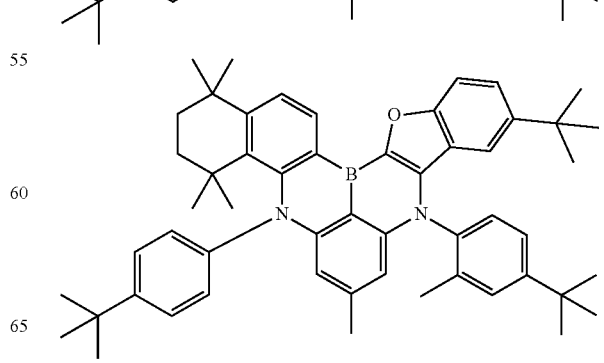

137
-continued
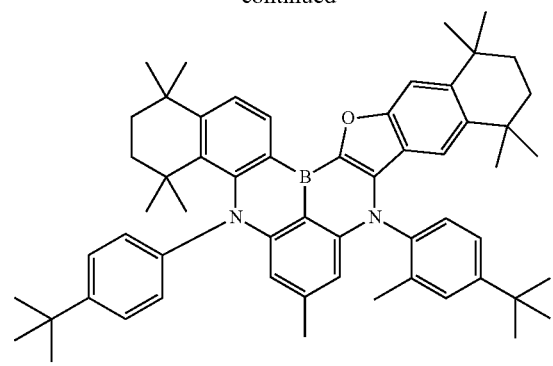
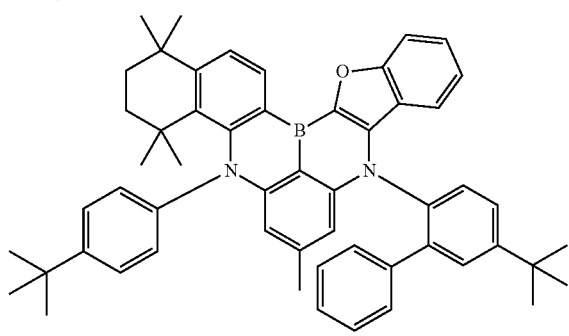
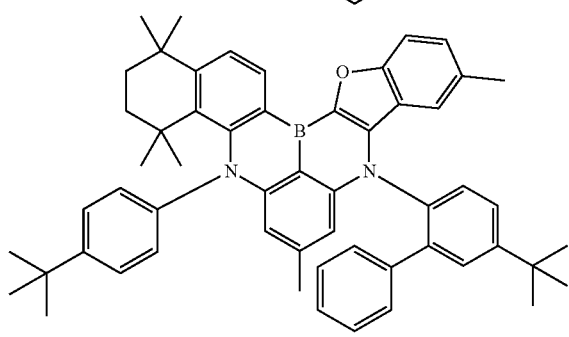
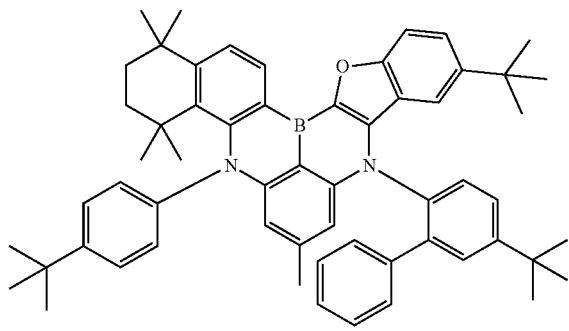
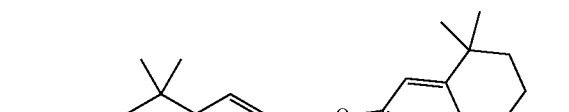
138
-continued
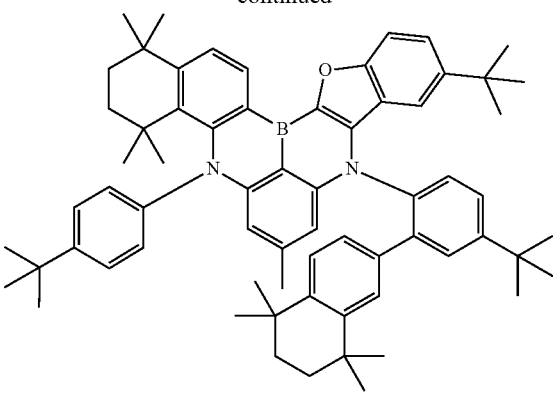
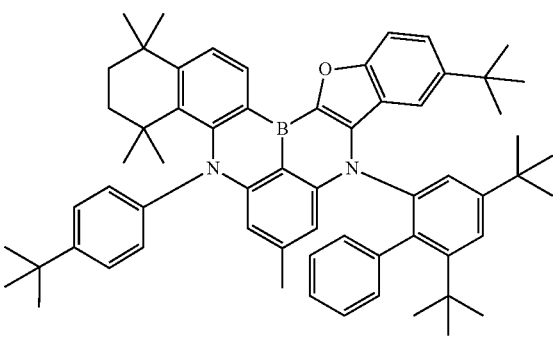
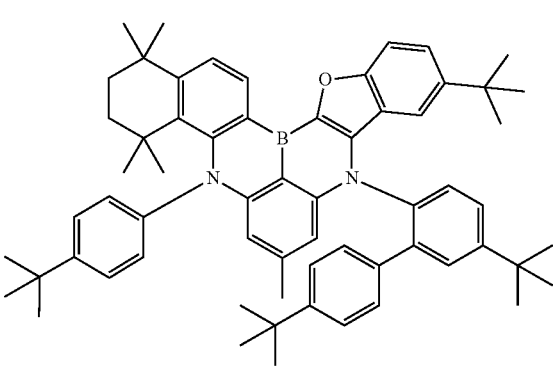
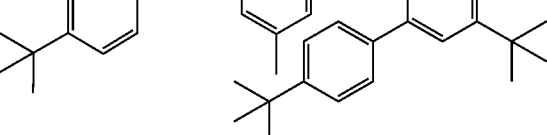
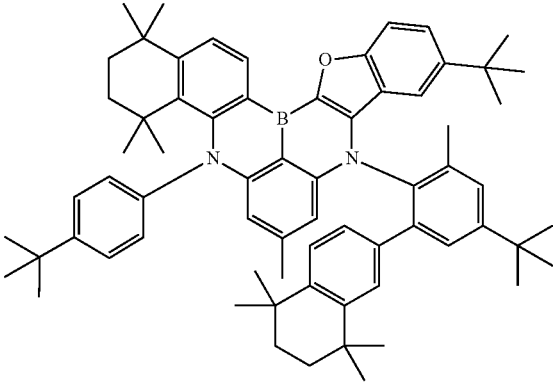

139
-continued
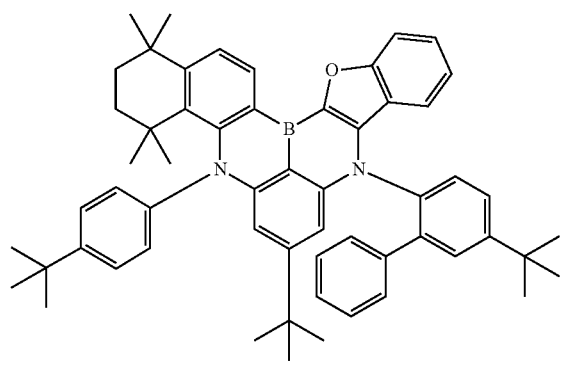
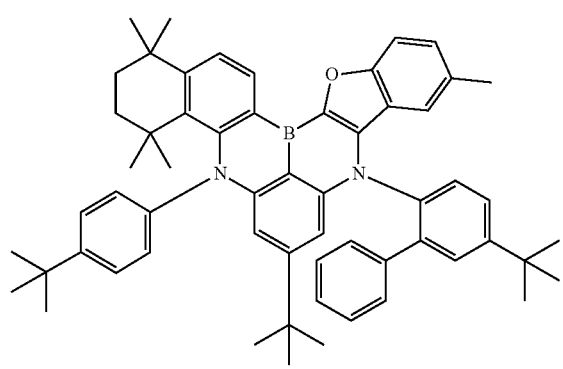
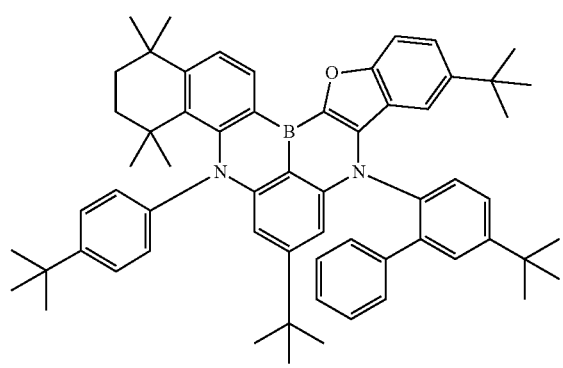
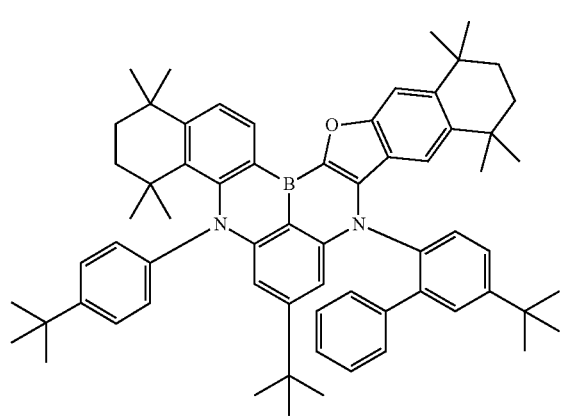
140
-continued
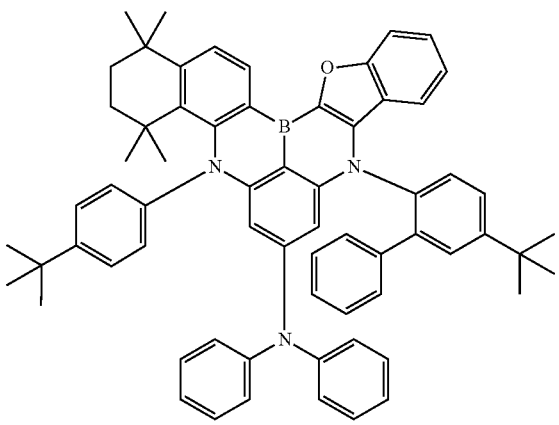
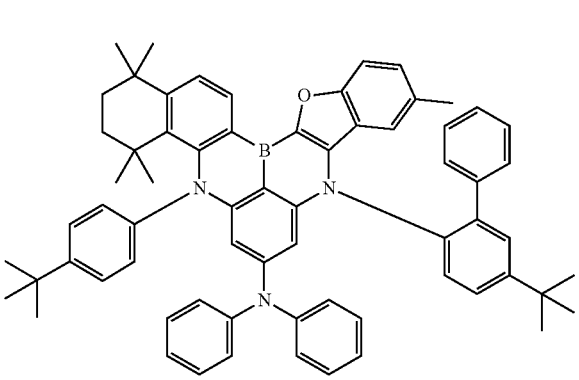
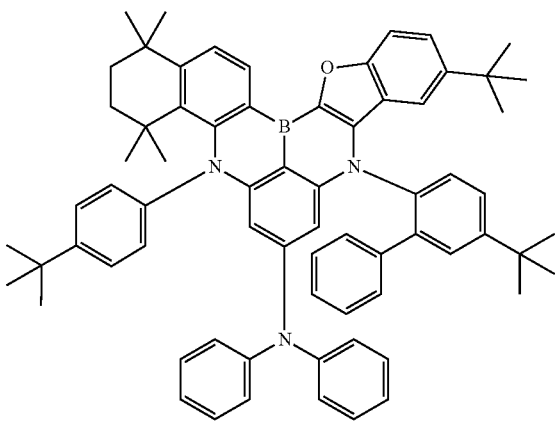
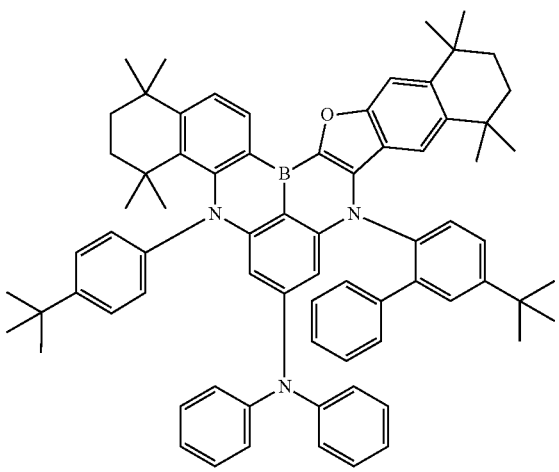

-continued
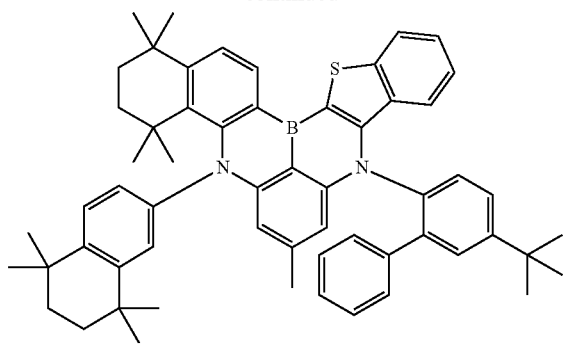
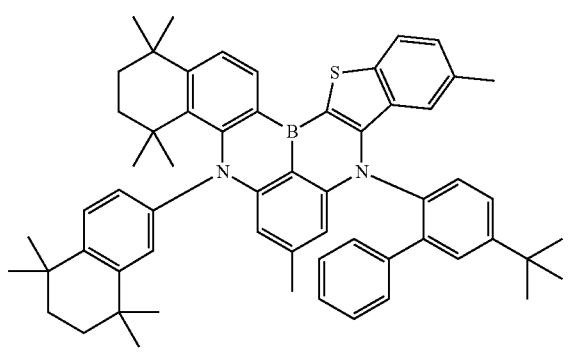
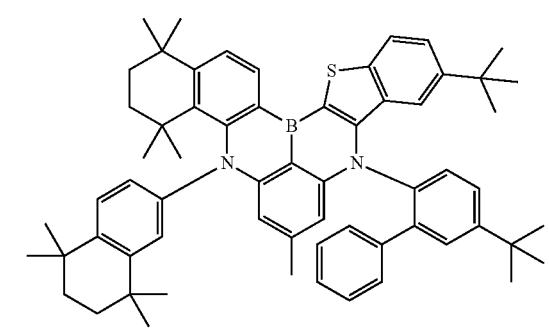
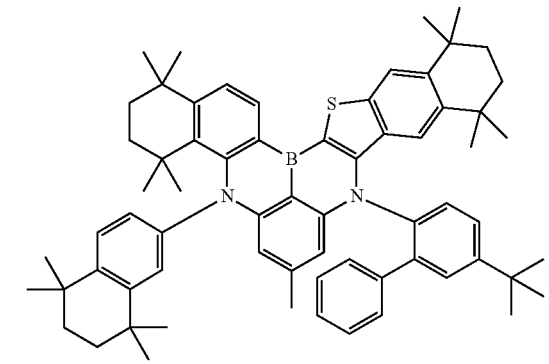
-continued
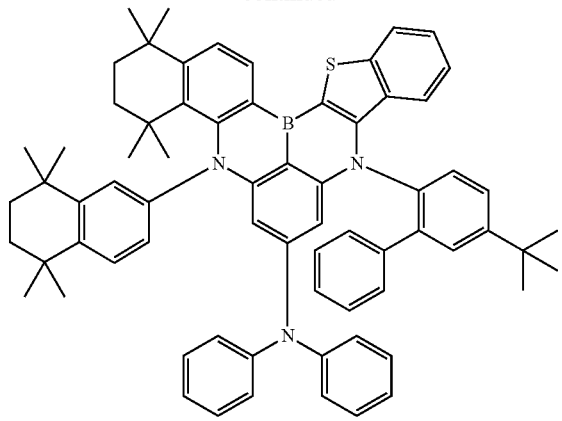
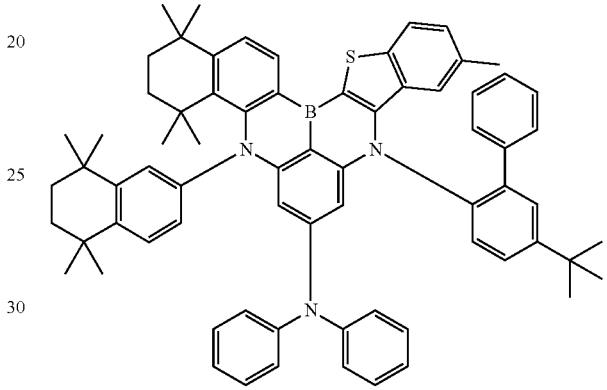
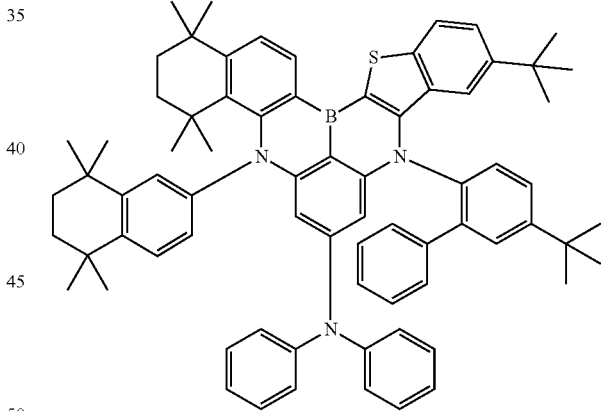
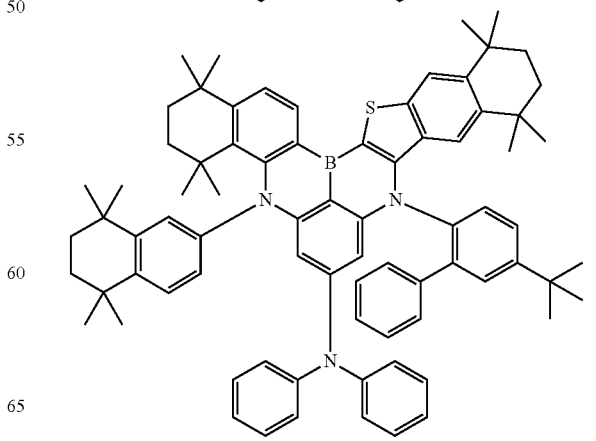

143
-continued
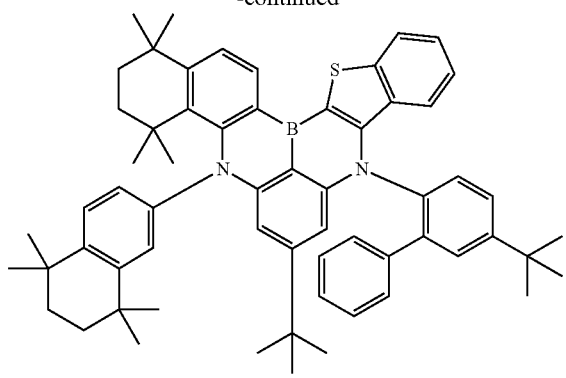
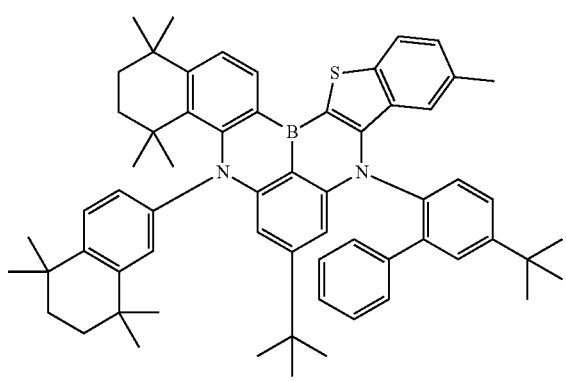
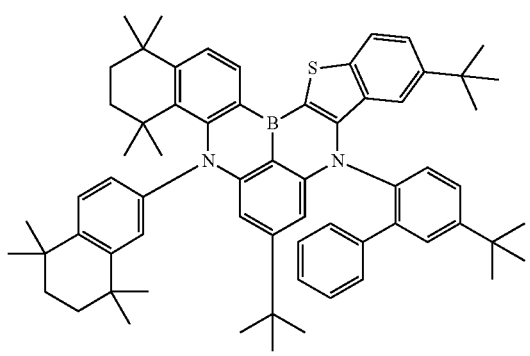
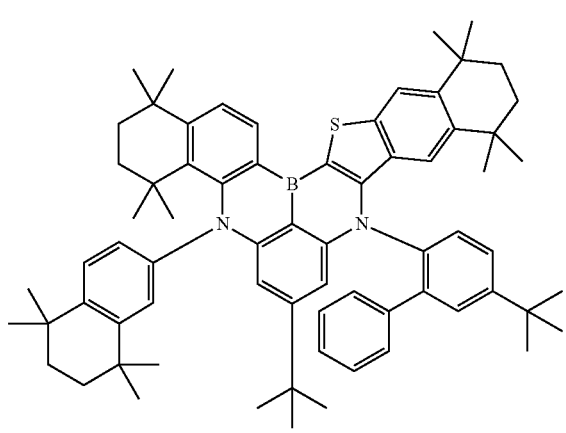
144
-continued
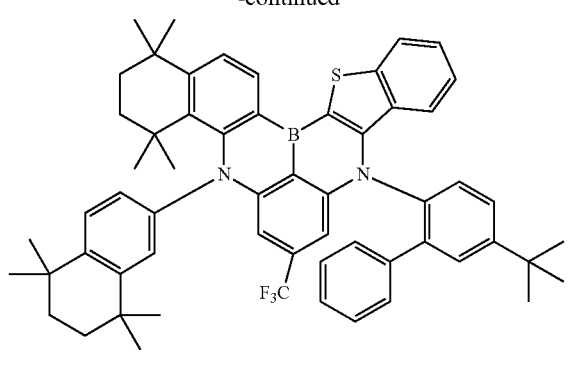
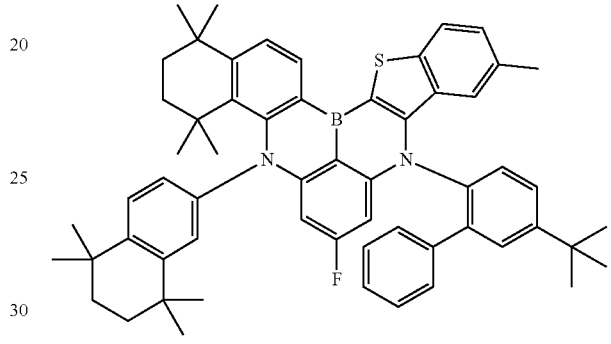
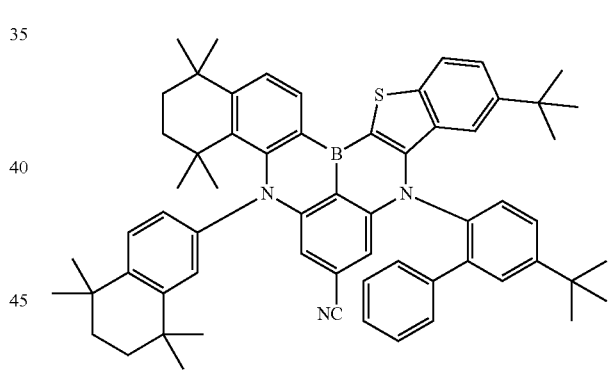
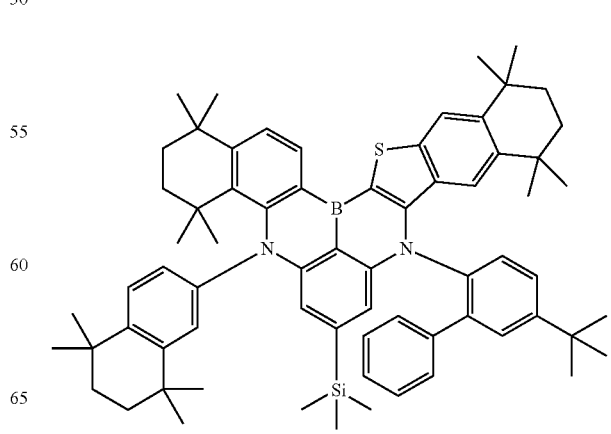

145
-continued
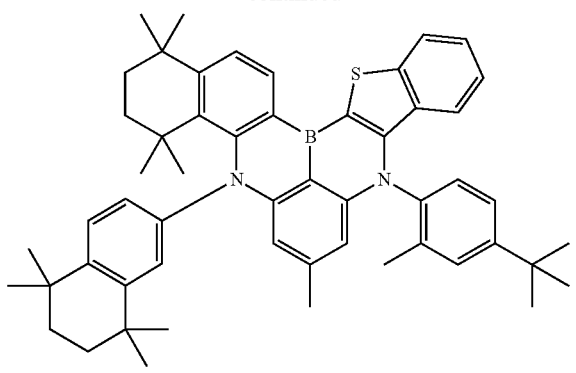
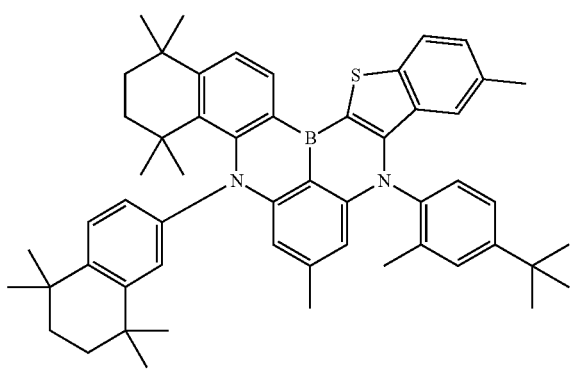
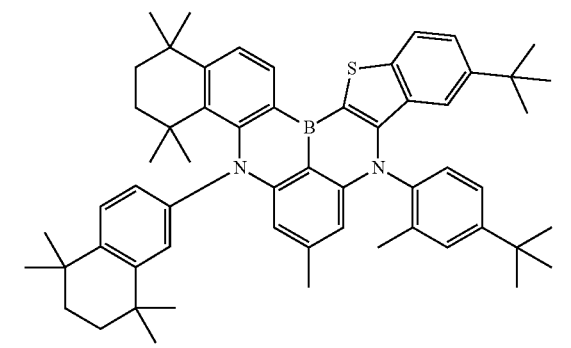
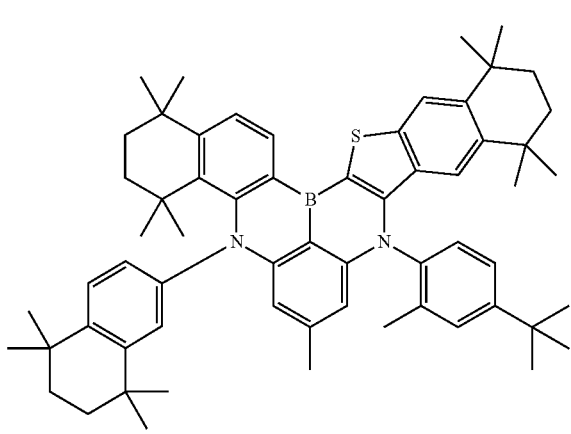
146
-continued
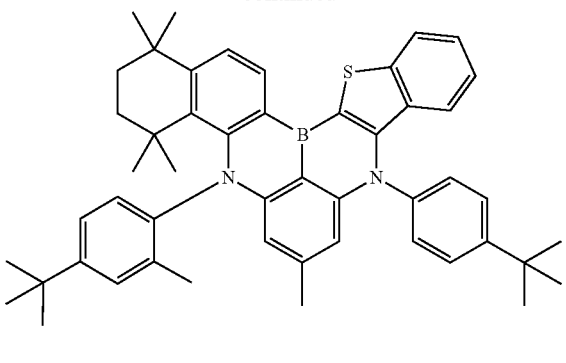
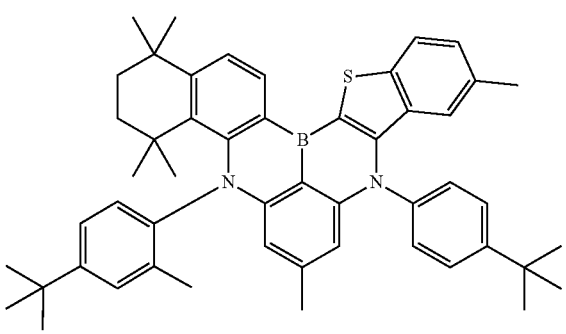
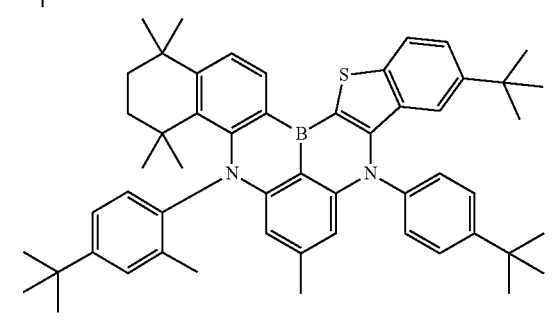
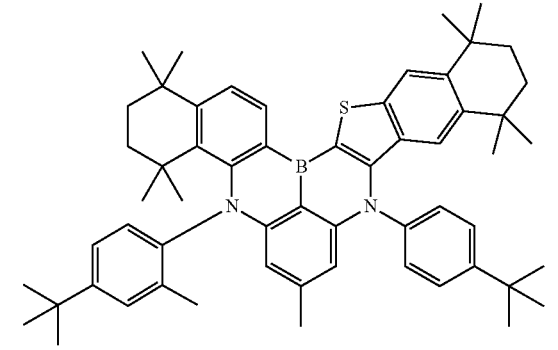
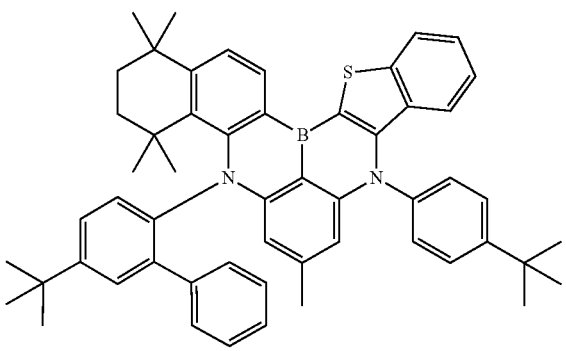

147
-continued
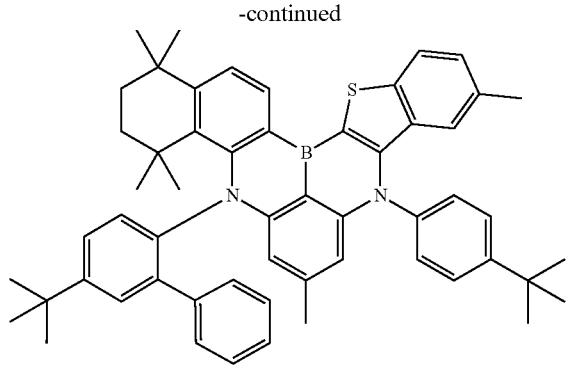
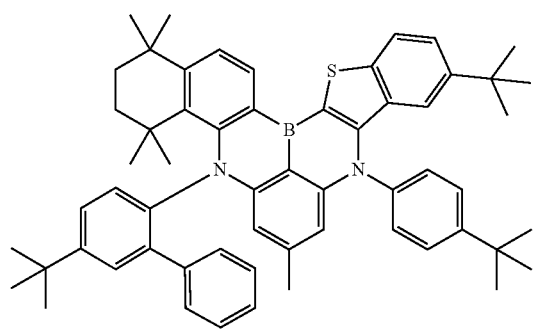
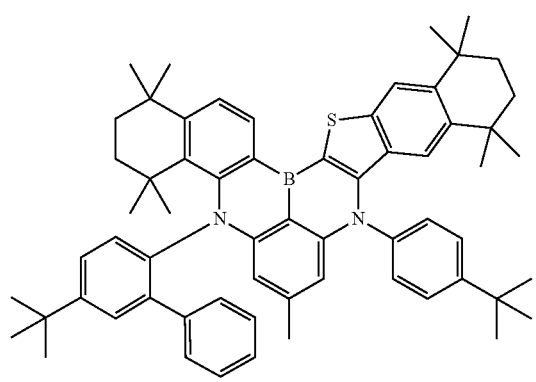
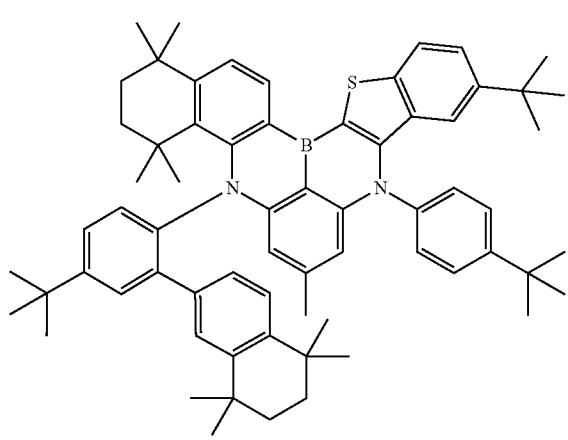
148
-continued
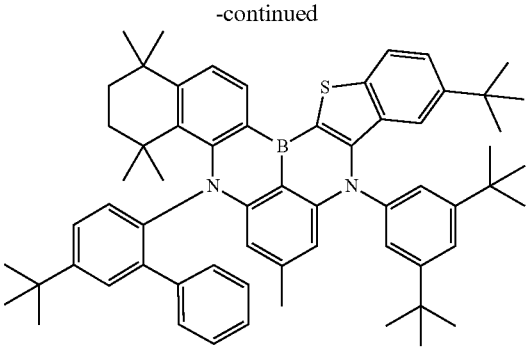
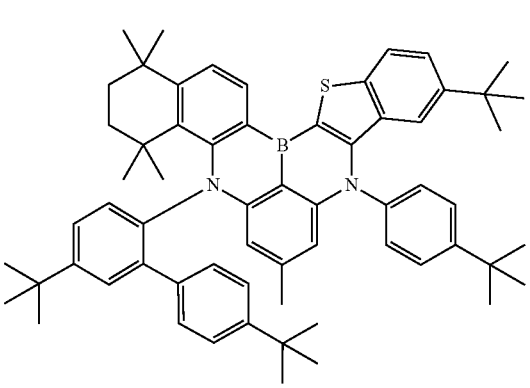
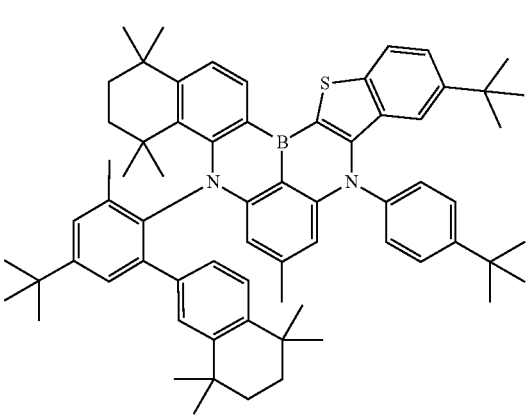
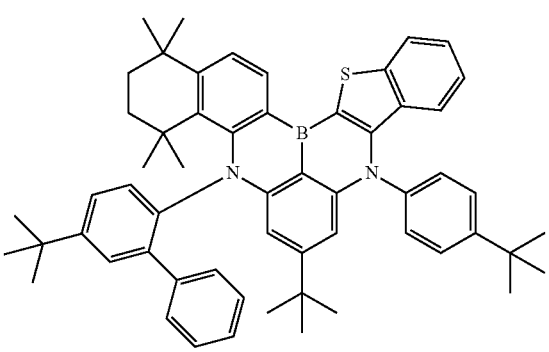

149
-continued
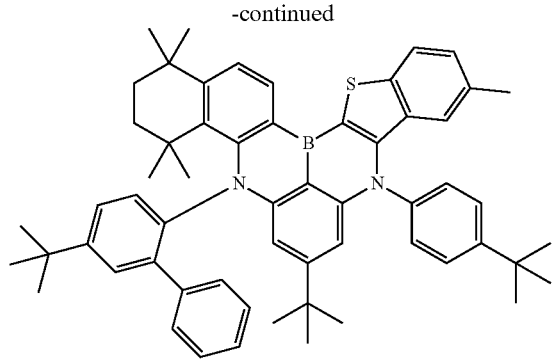
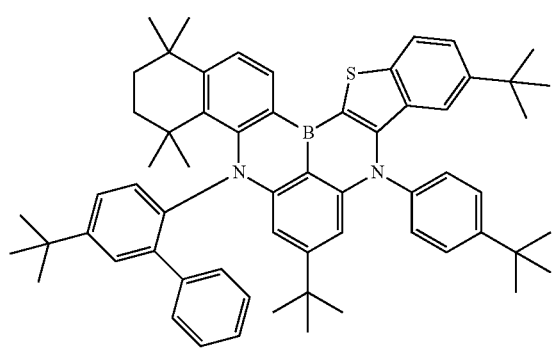
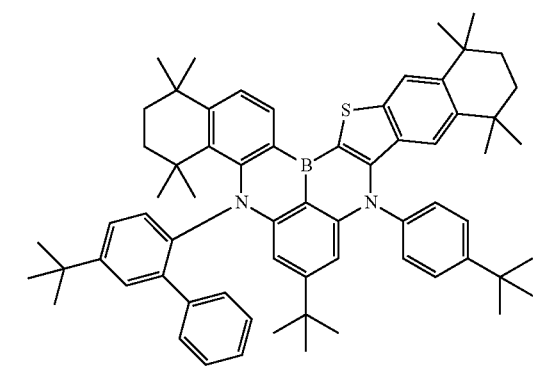
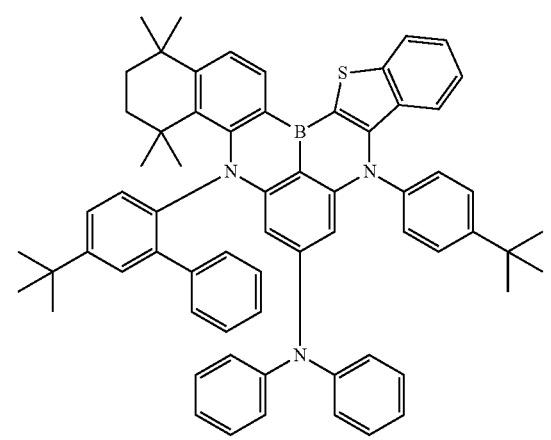
150
-continued
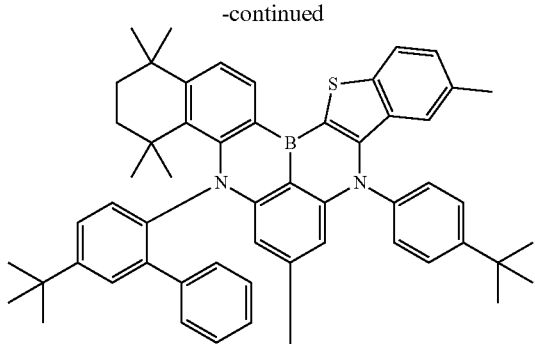
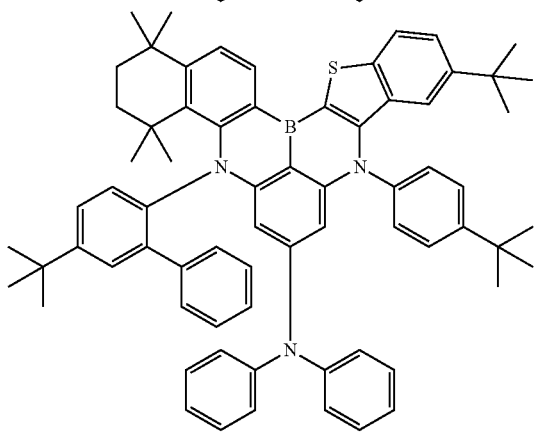
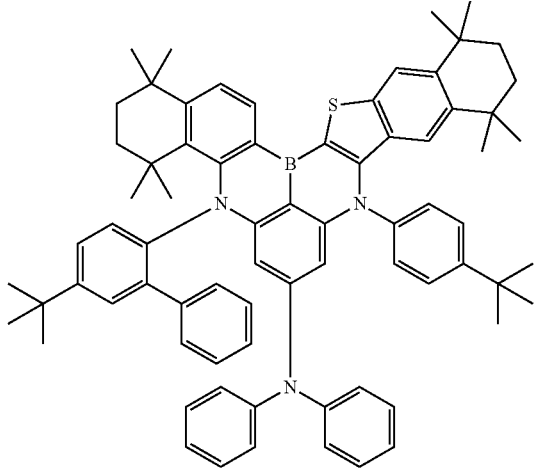
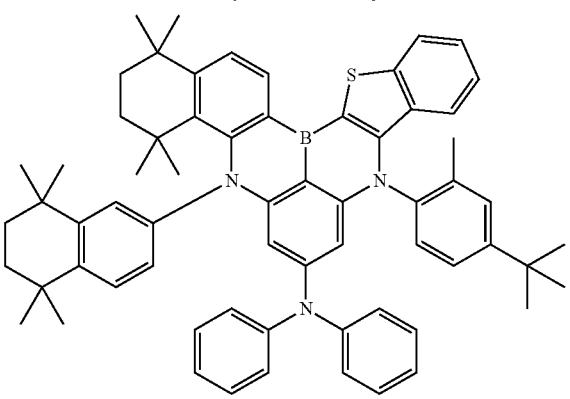

151
-continued
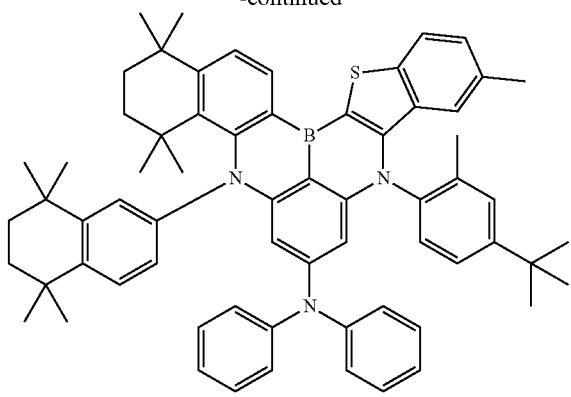
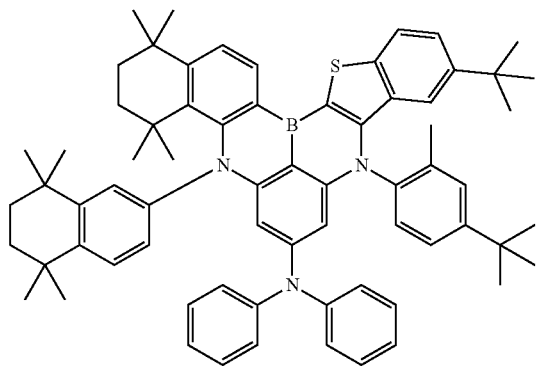
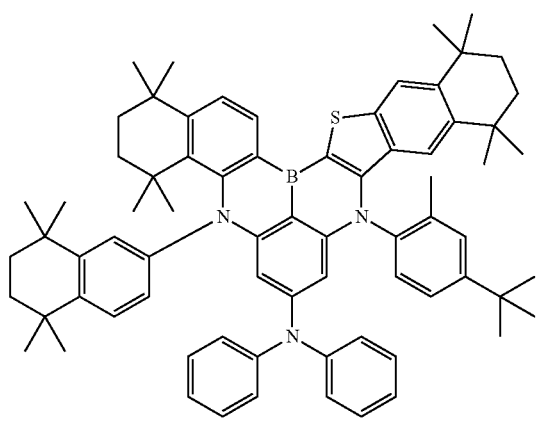
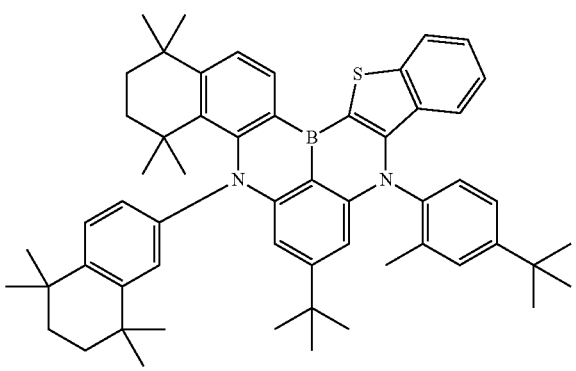
152
-continued
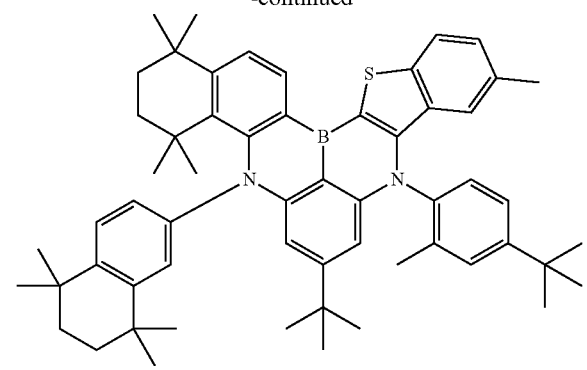
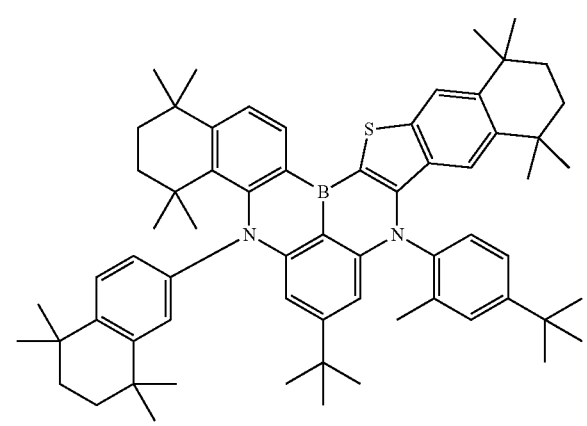
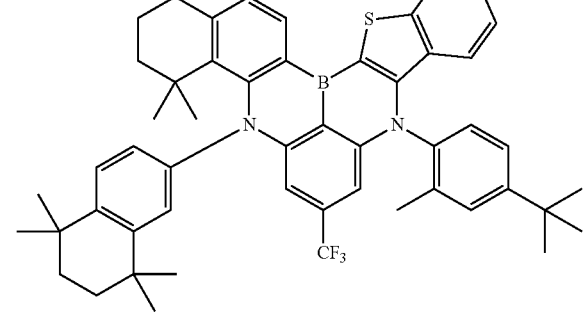

153
-continued
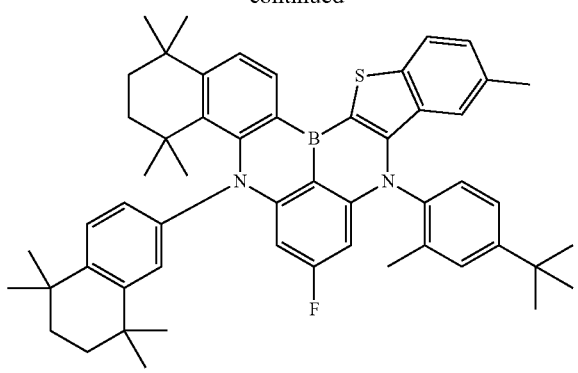
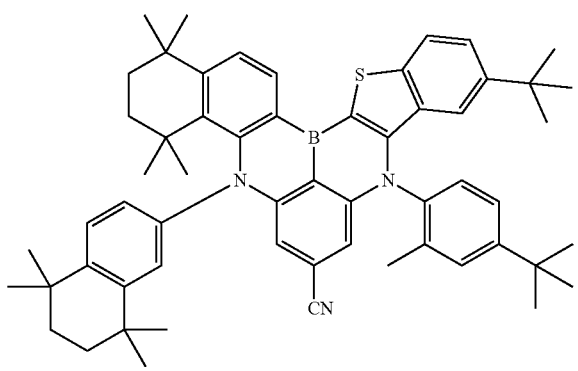
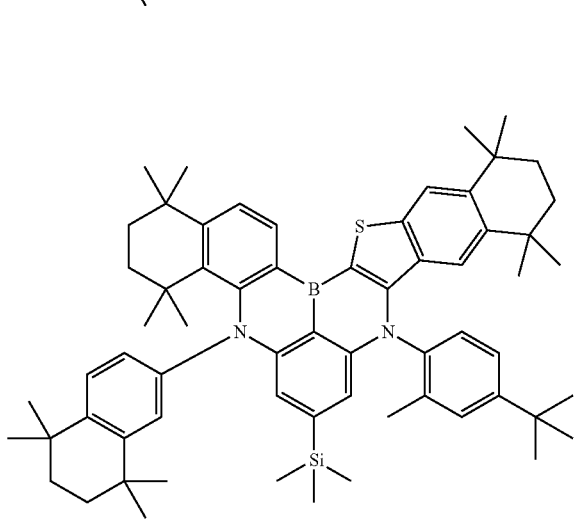
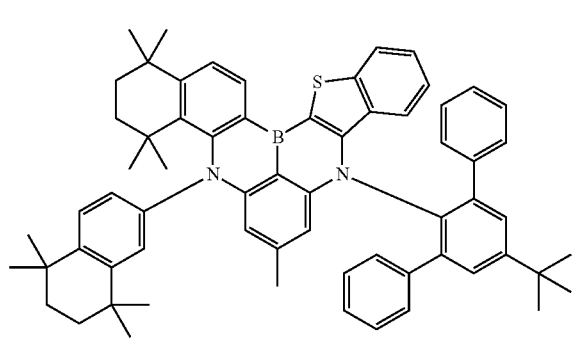
154
-continued
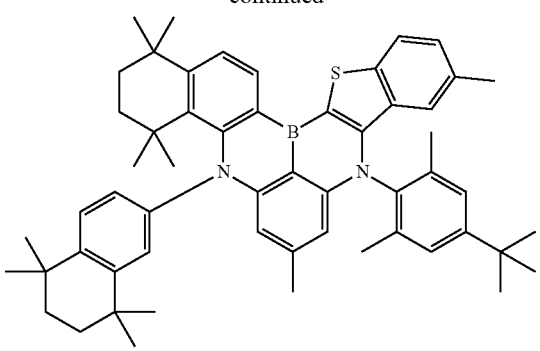
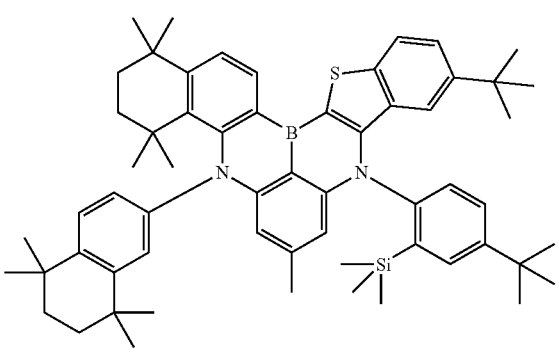
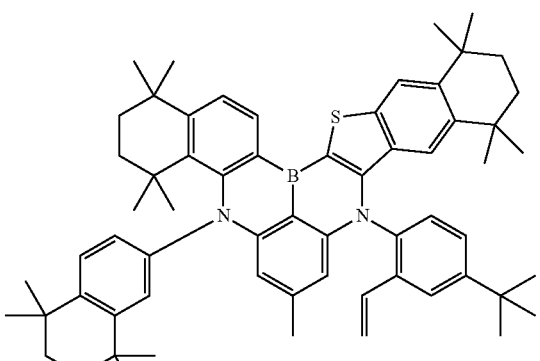
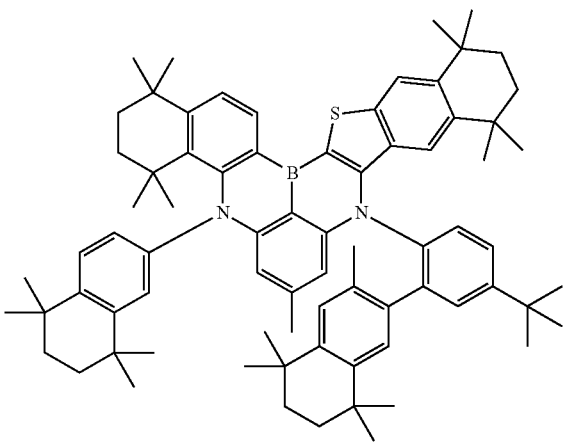

155
-continued
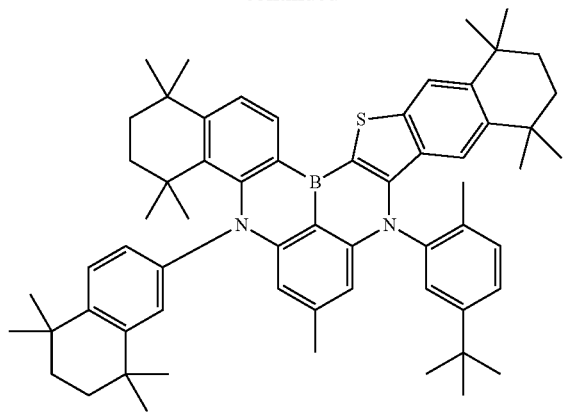
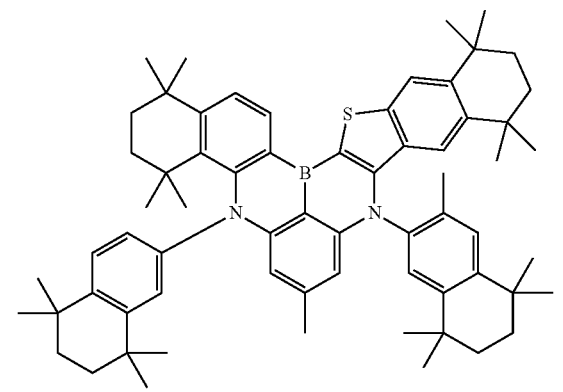
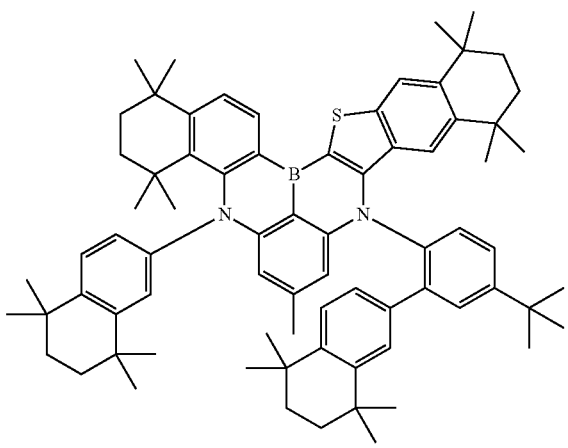
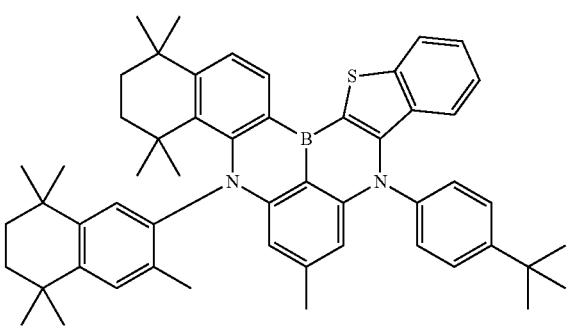
156
-continued
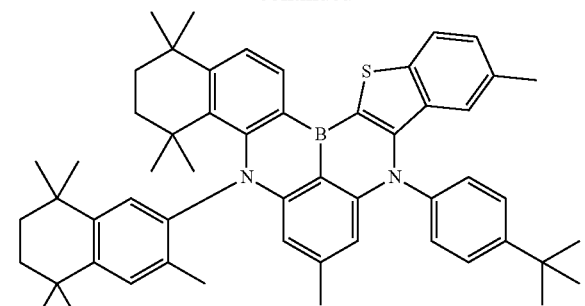
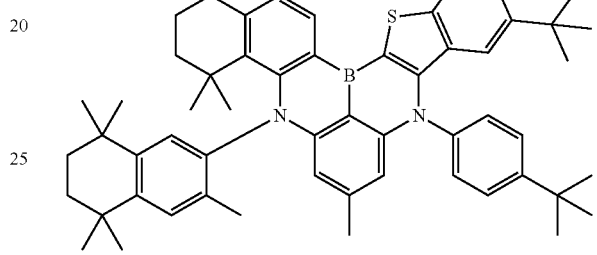
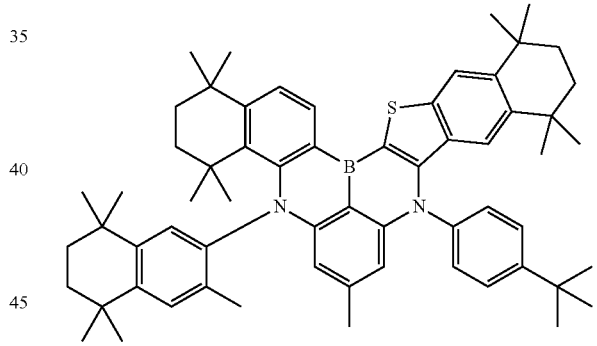
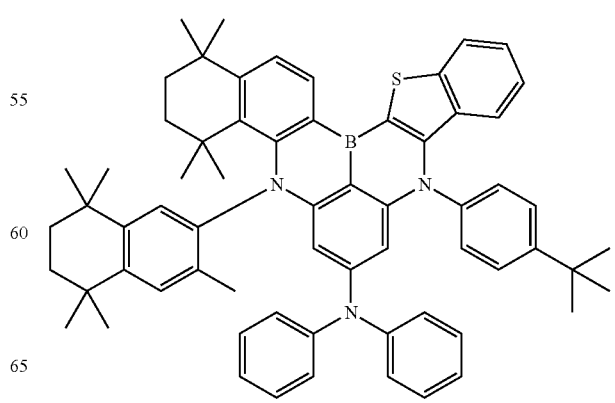

157
-continued
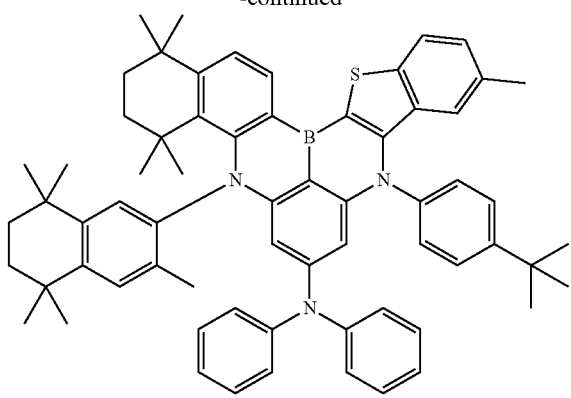
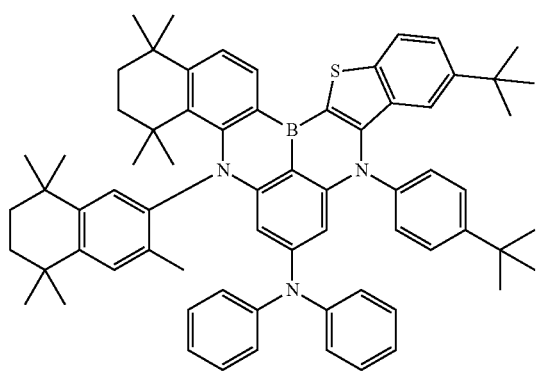
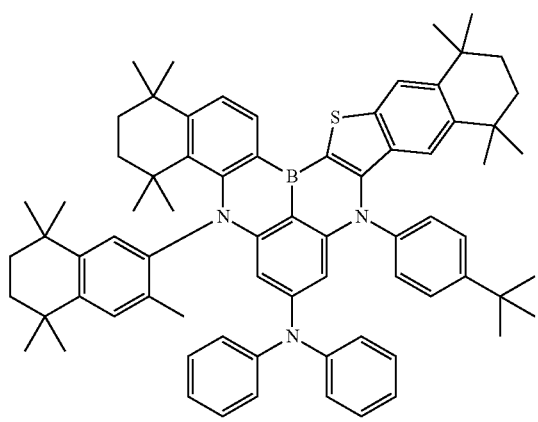
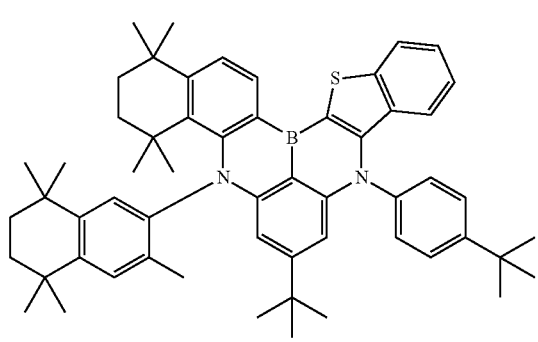
158
-continued
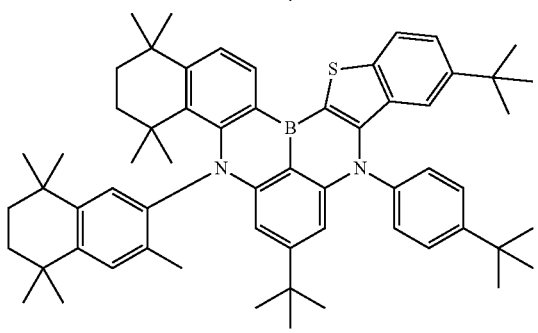
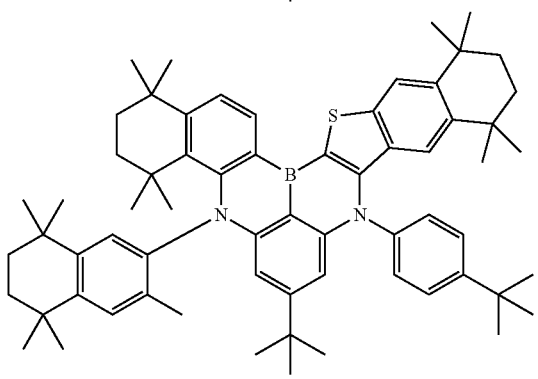
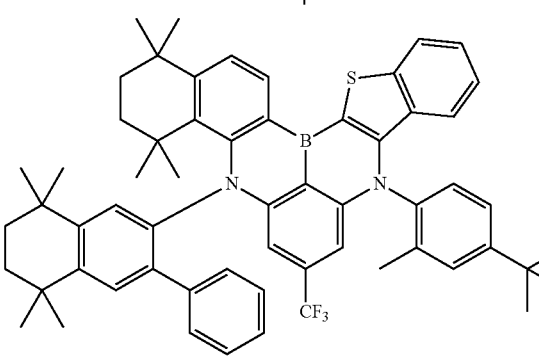
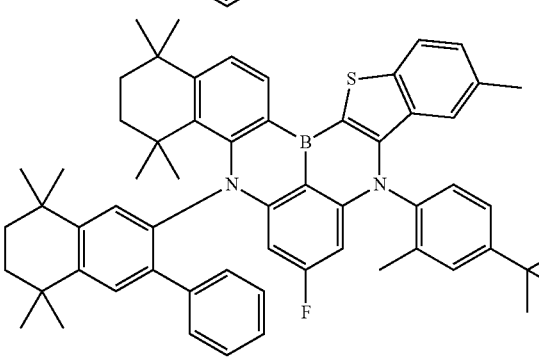

159
-continued
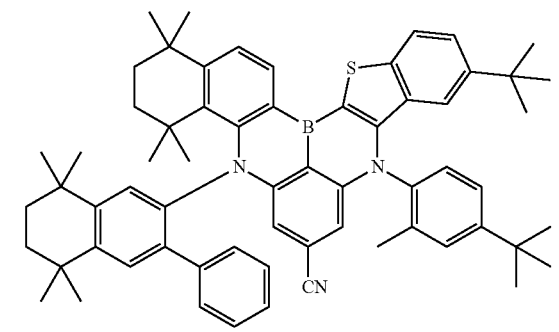
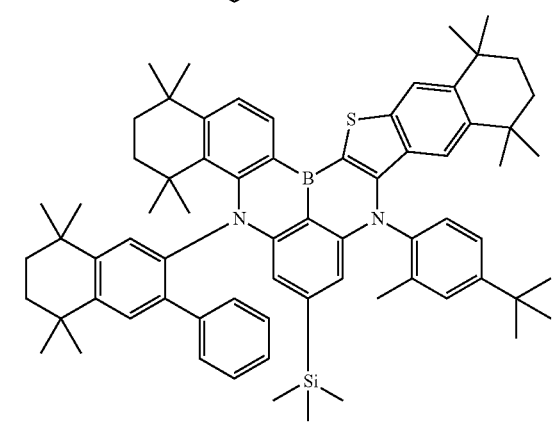
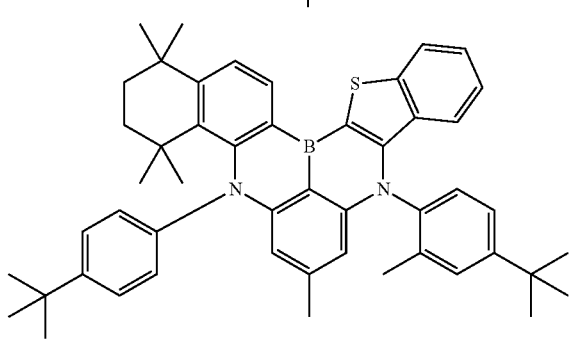
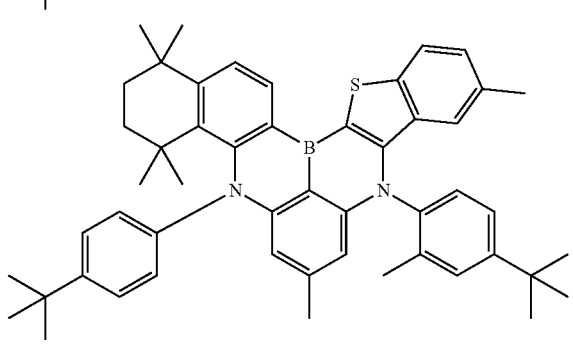
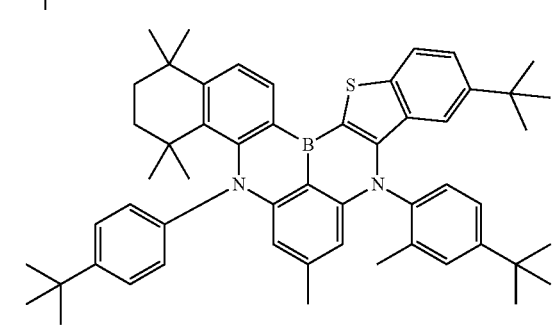
160
-continued
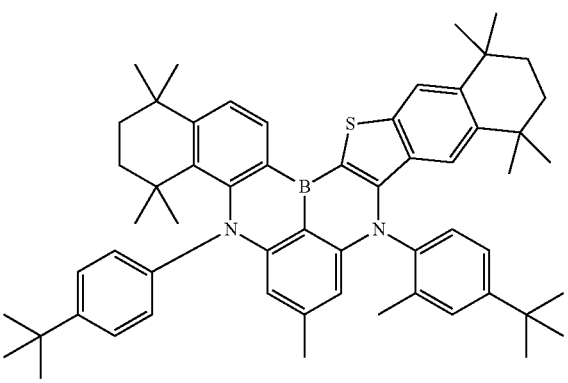
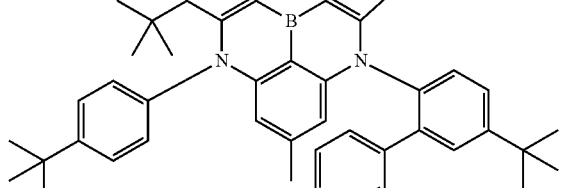
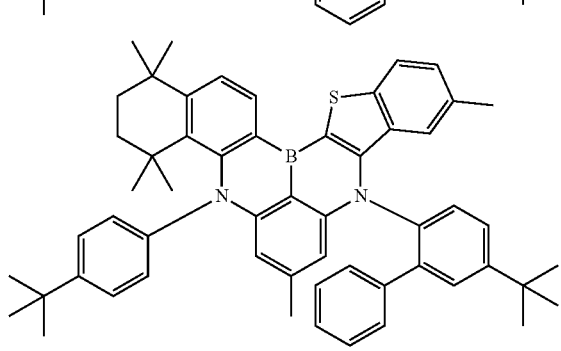
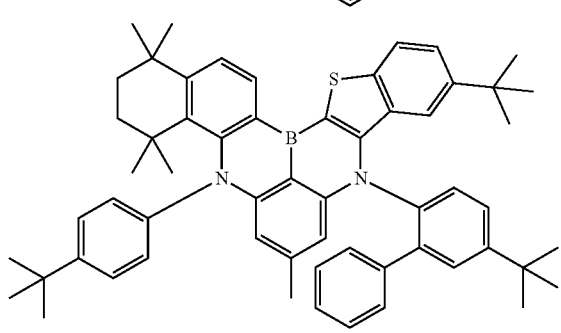
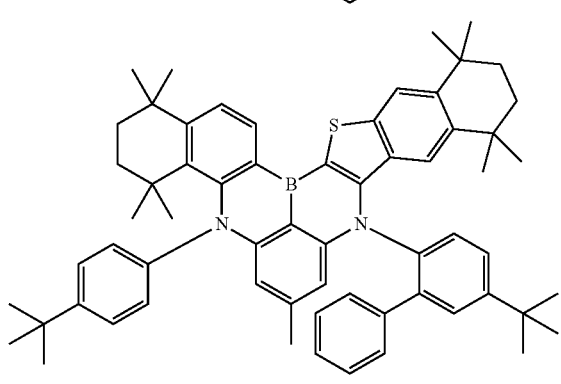

161
-continued
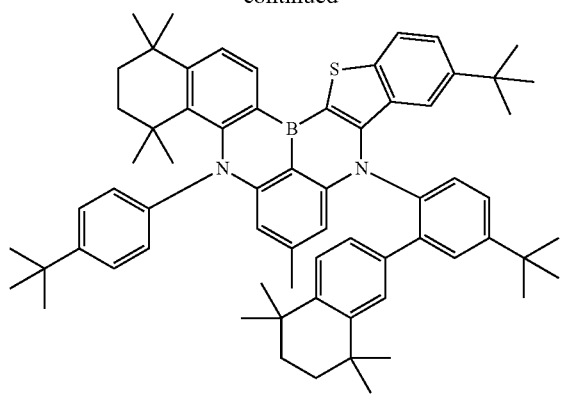
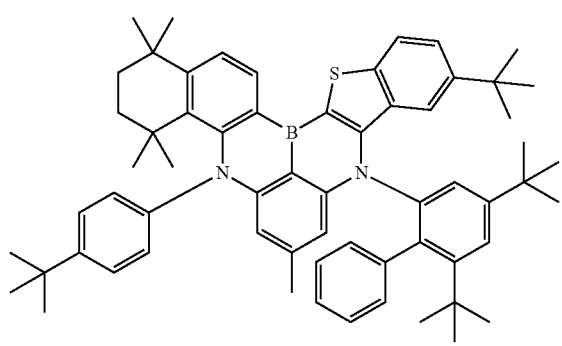
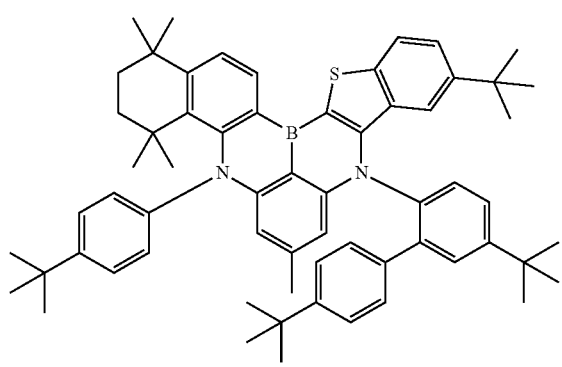
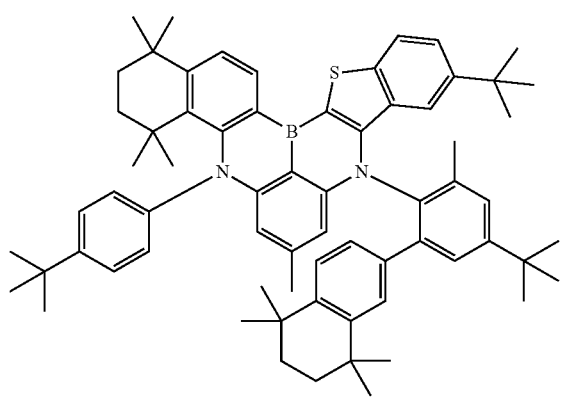
162
-continued
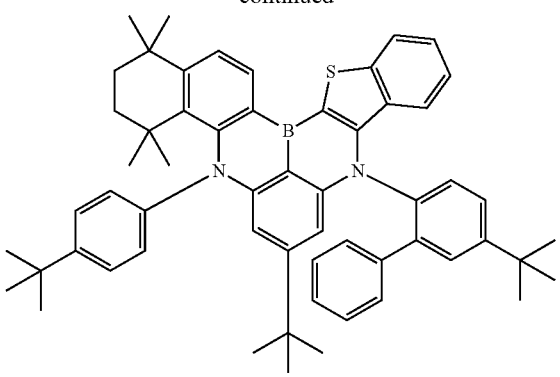
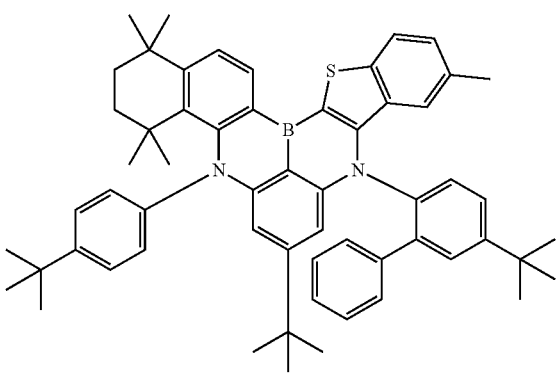
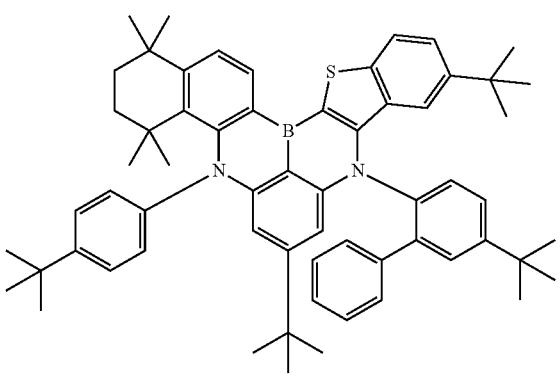
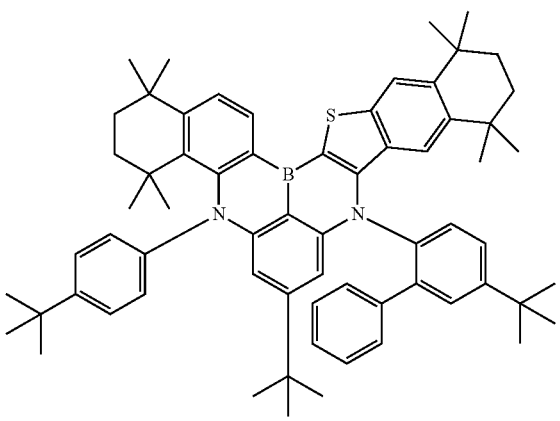

163
-continued
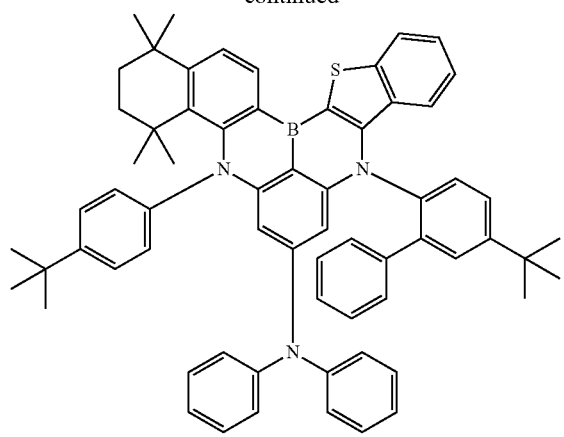
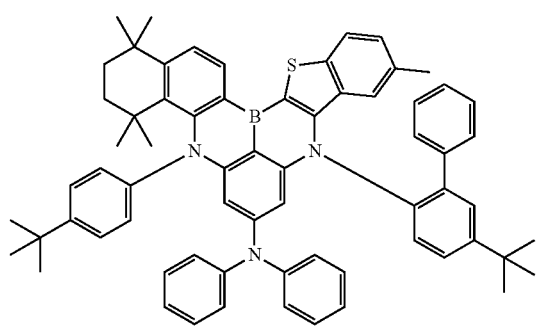
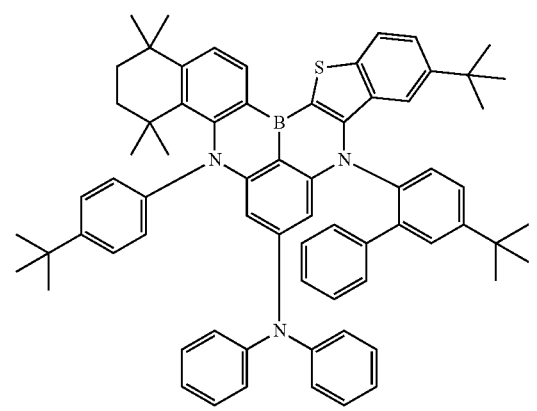
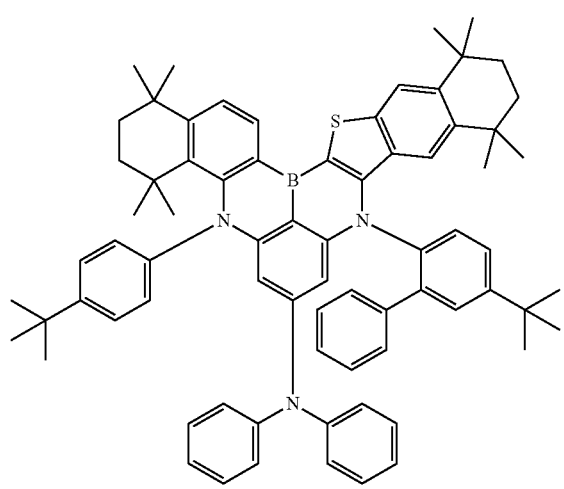
164
-continued
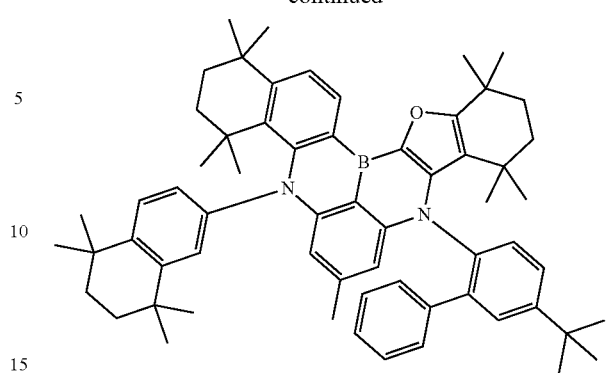
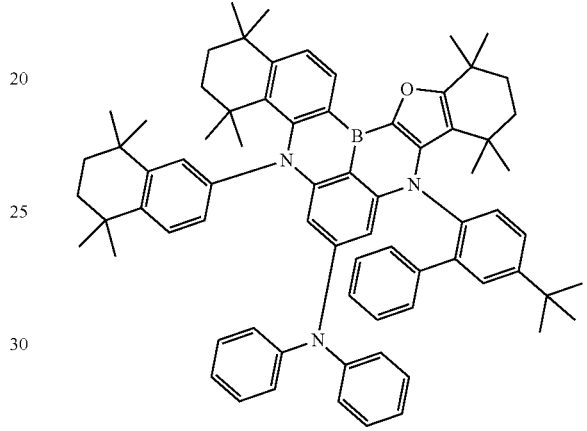
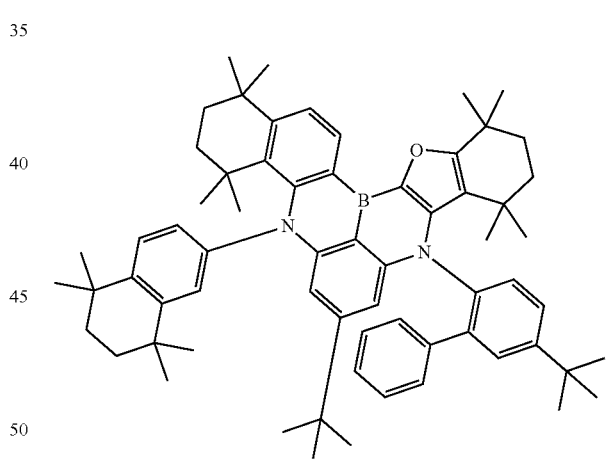
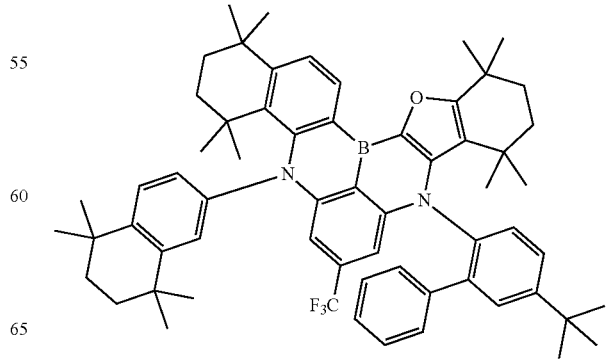

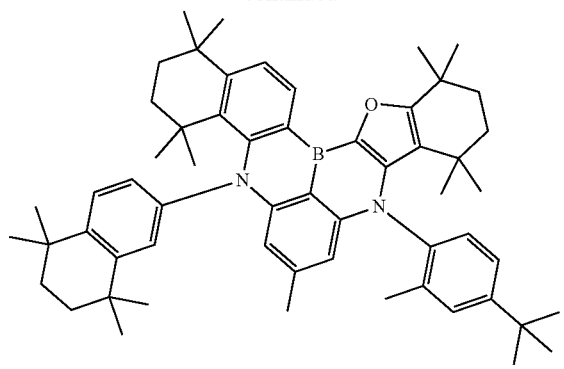
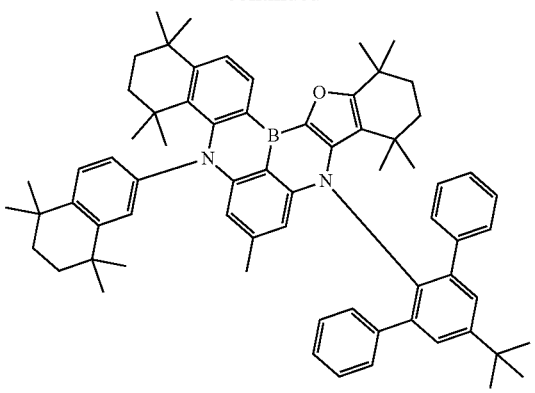
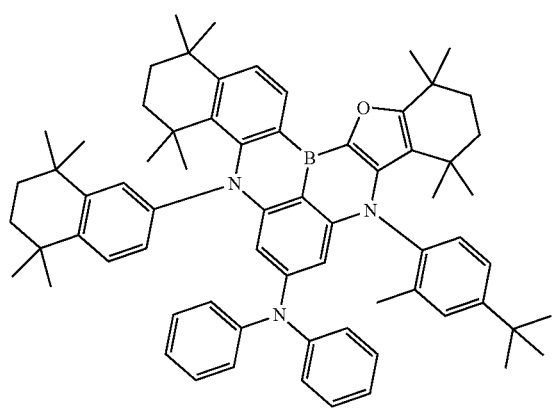
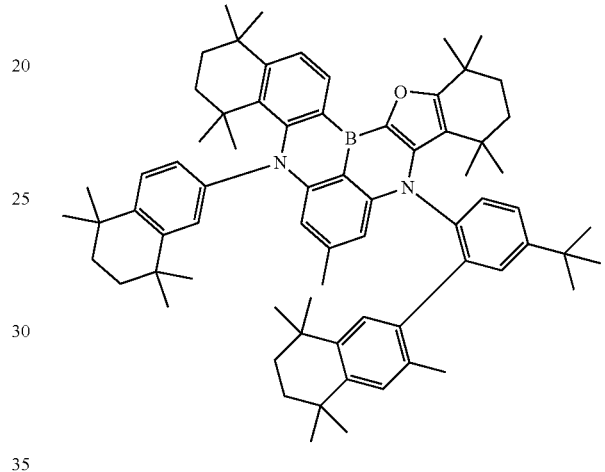
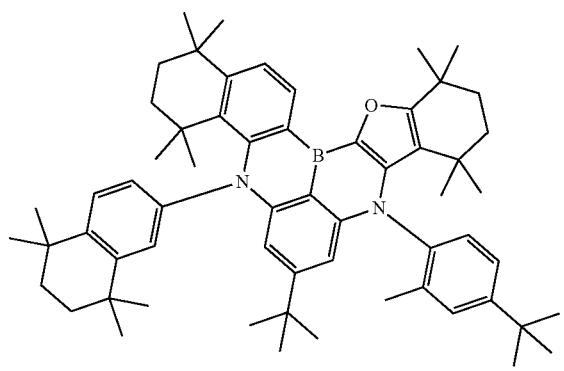
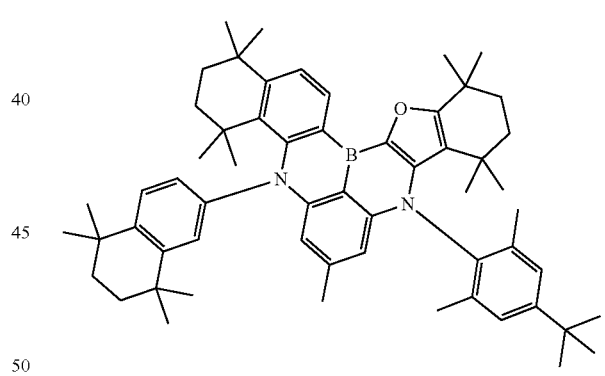
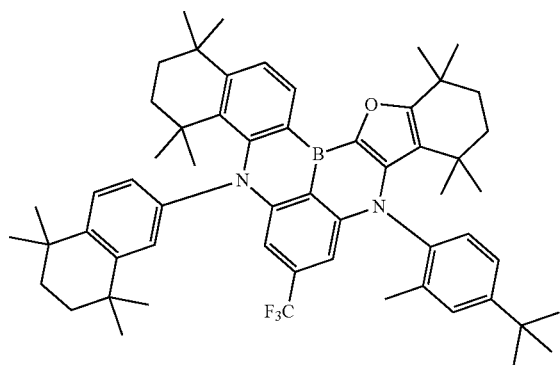
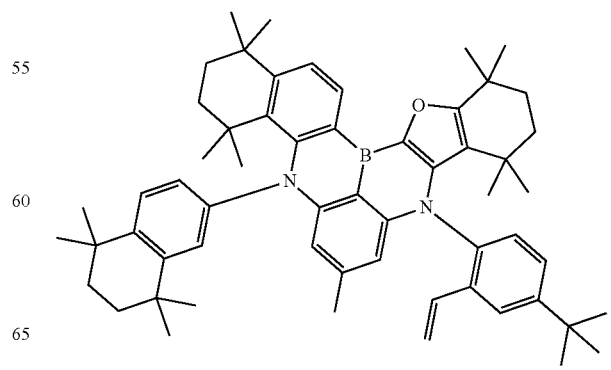

167
-continued
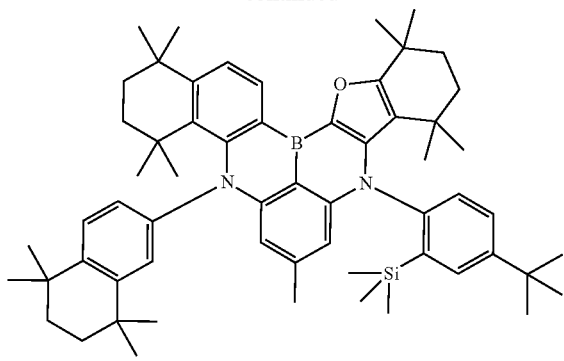
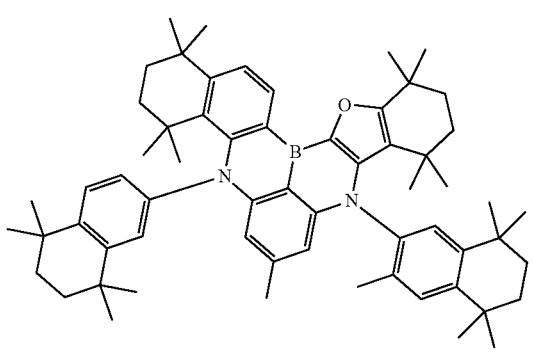
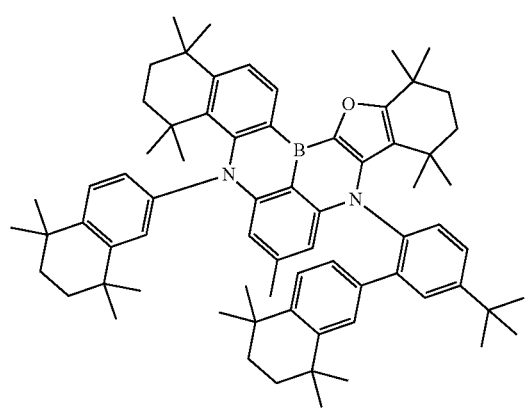
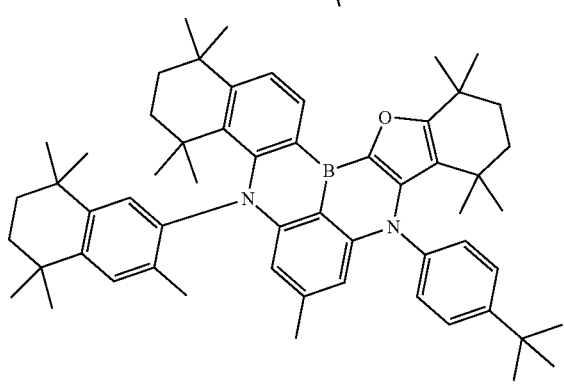
168
-continued
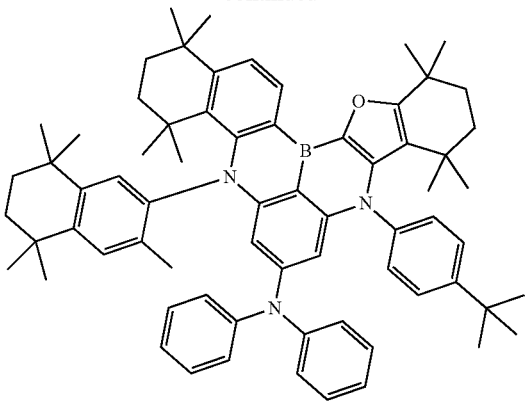
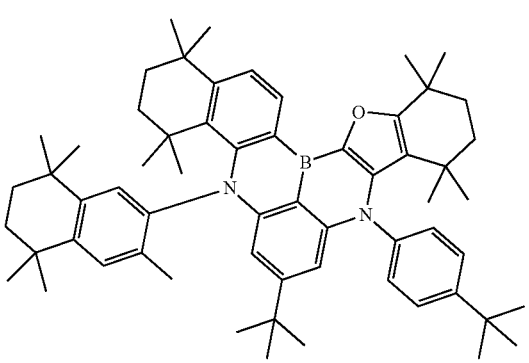
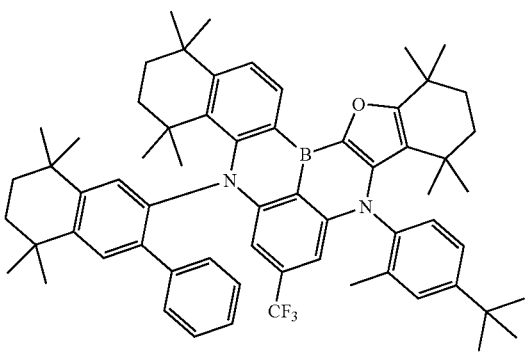
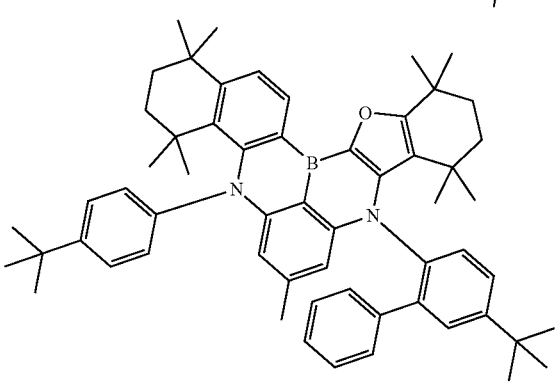

169
-continued
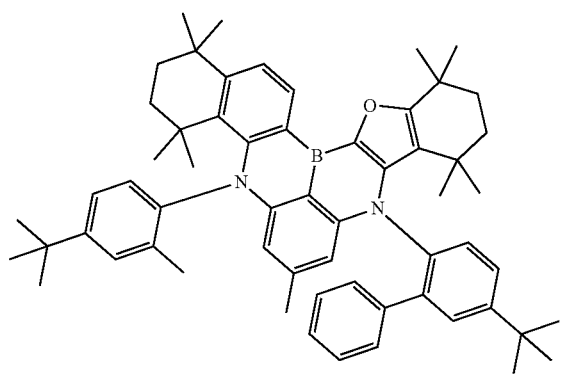
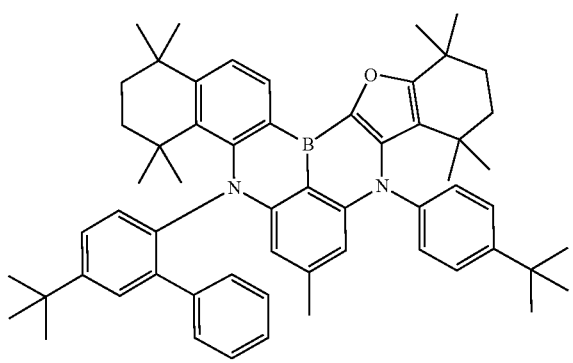
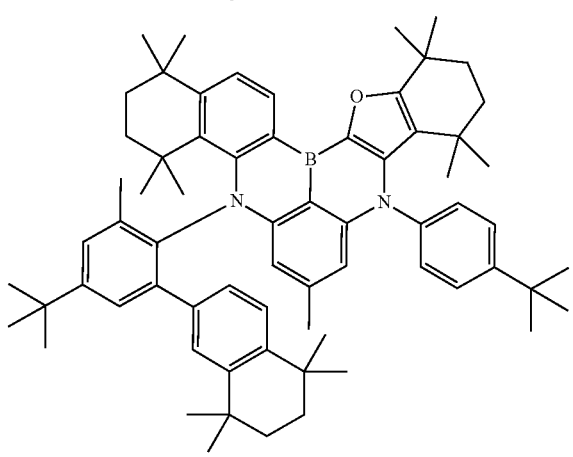
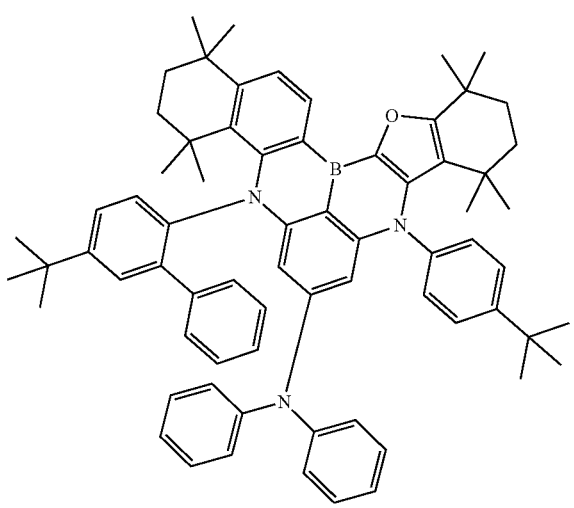
170
-continued
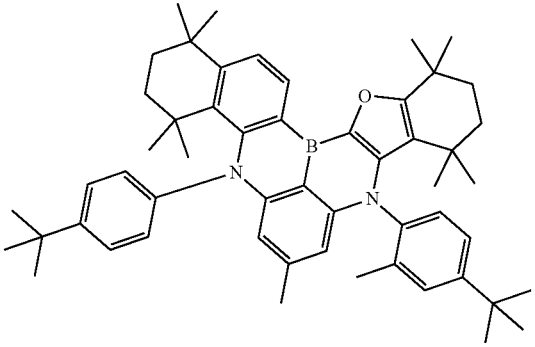
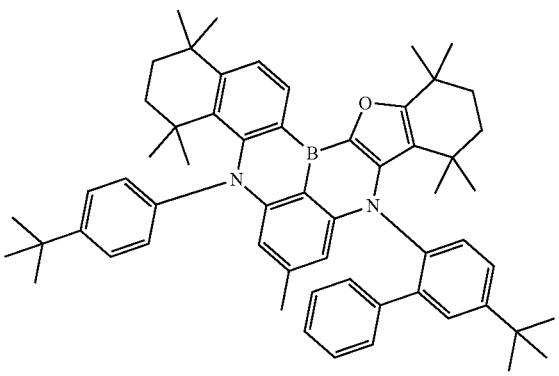
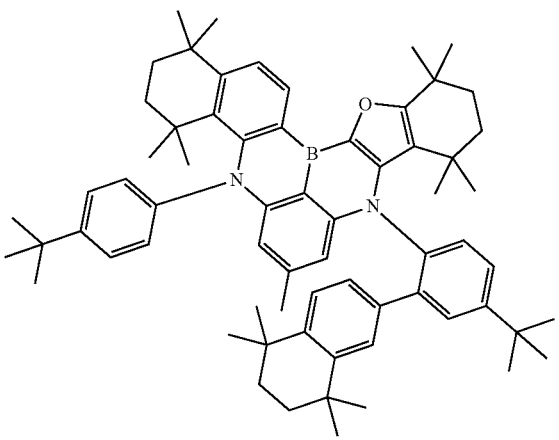
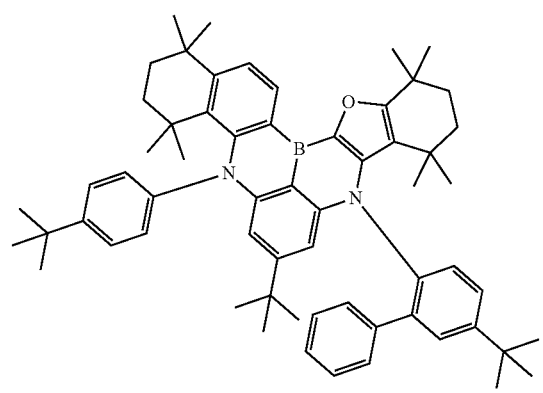

171
-continued
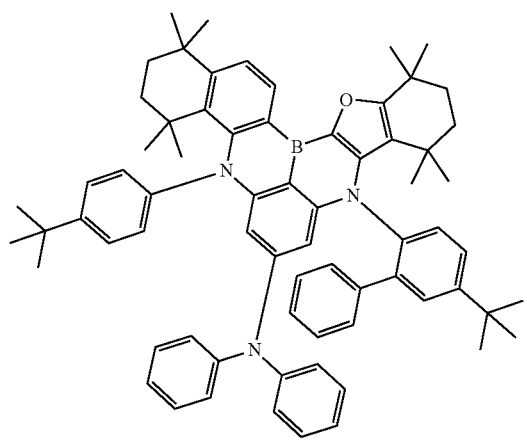
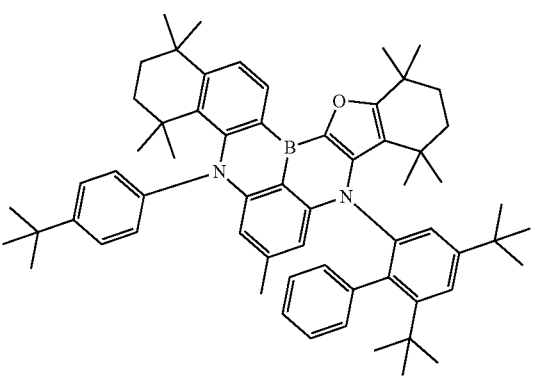
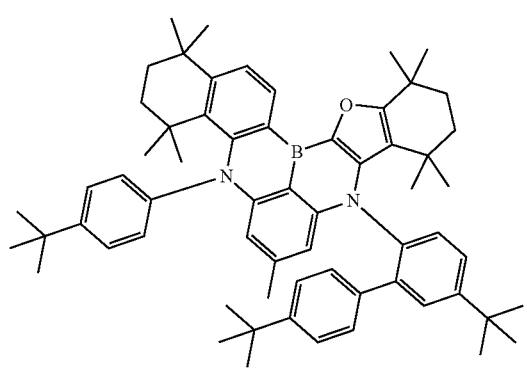
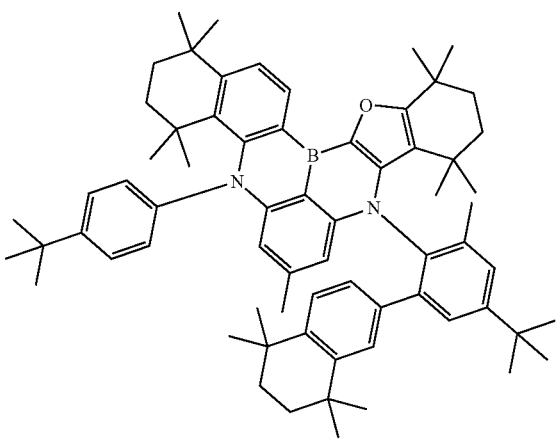 [SMILES: Cc1cc2c3c(c1)N(c1c(C)cc(C(C)(C)C)cc1-c1ccc4c(c1)C(C)(C)CCC4(C)C)c1c(oc4c1C(C)(C)CCC4(C)C)B3c1ccc3c(c1N2c1ccc(C(C)(C)C)cc1)C(C)(C)CCC3(C)C]
172
-continued
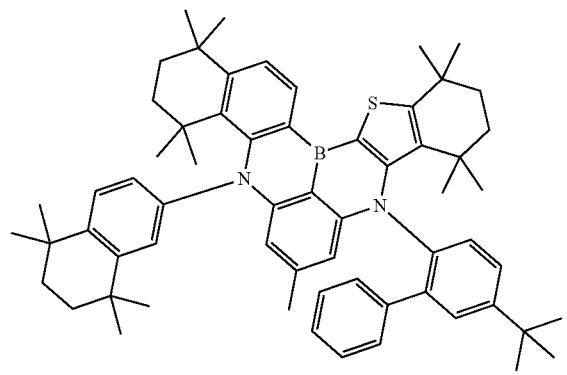
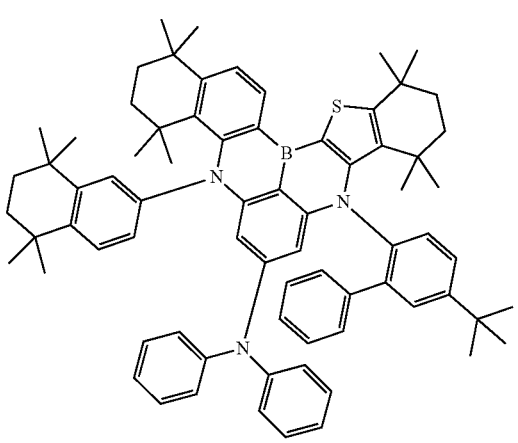
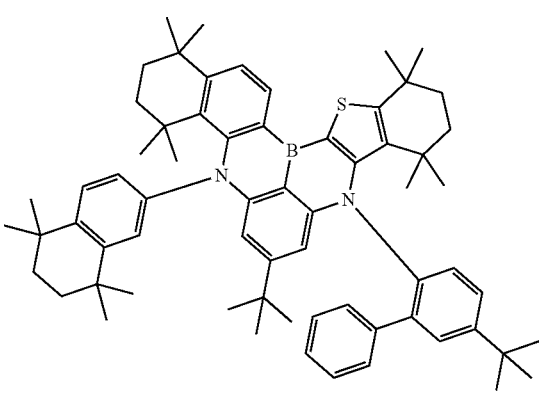
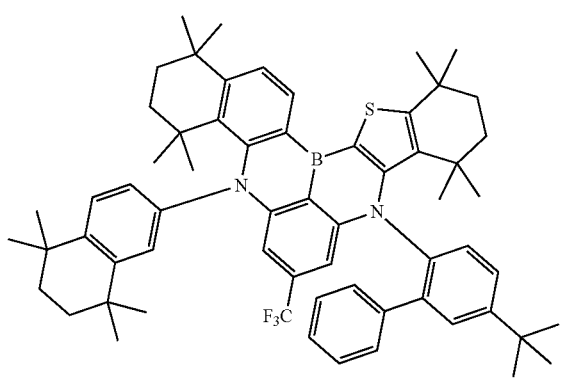

173
-continued
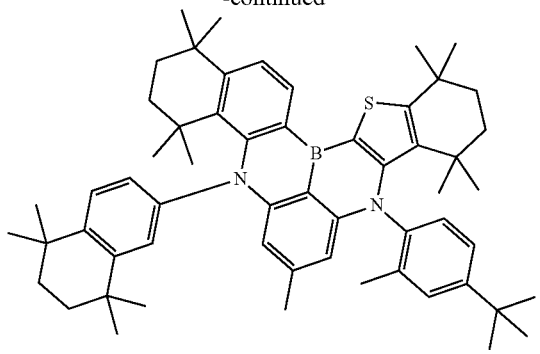
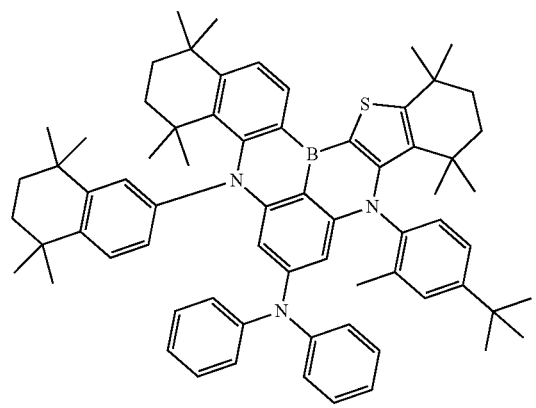
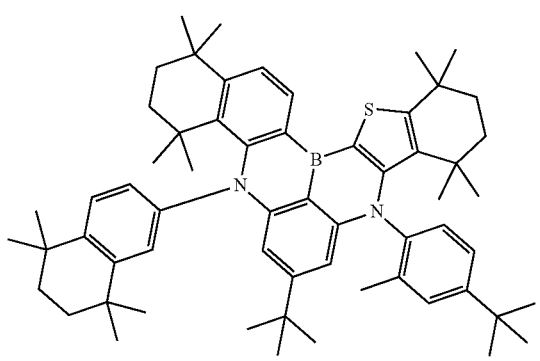
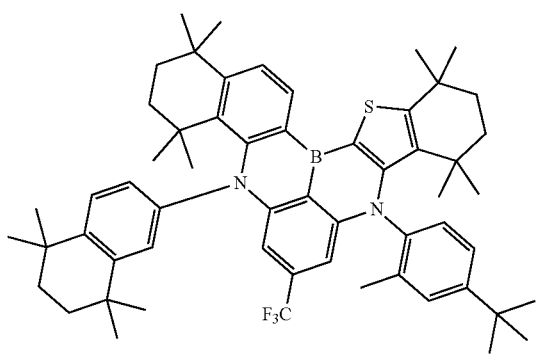
174
-continued
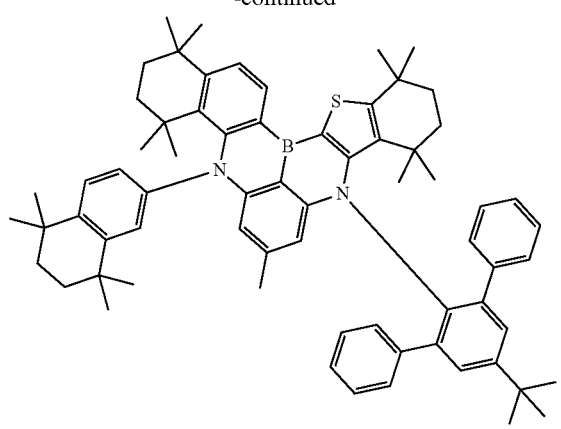
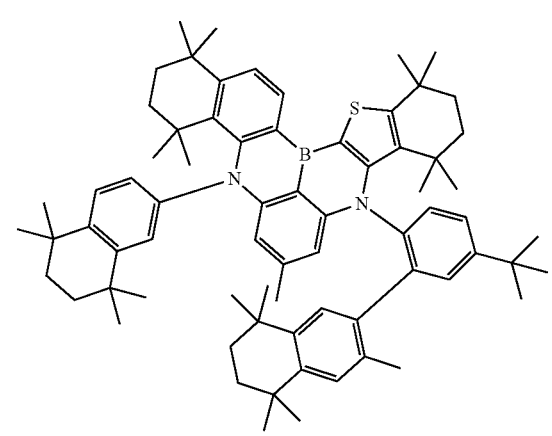
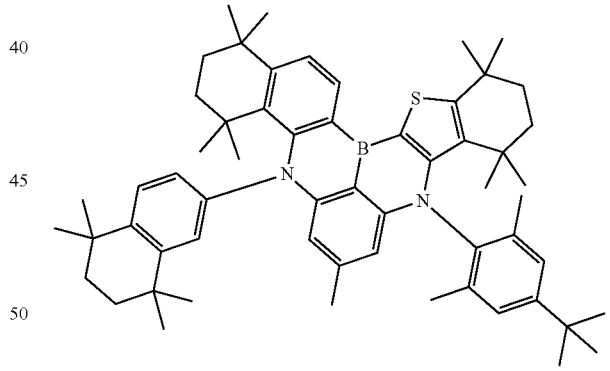
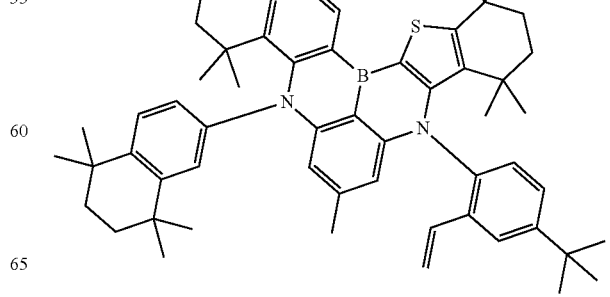

175
-continued
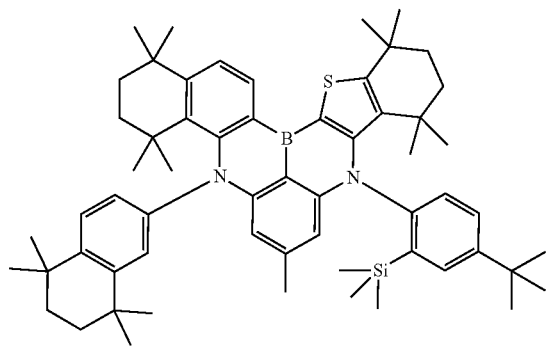
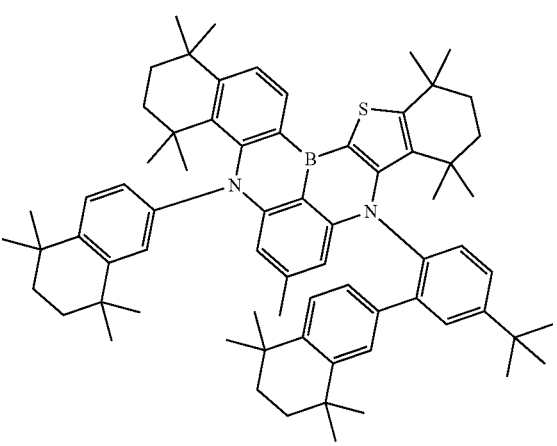
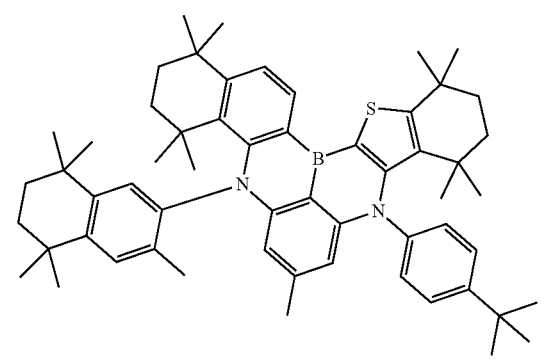
176
-continued
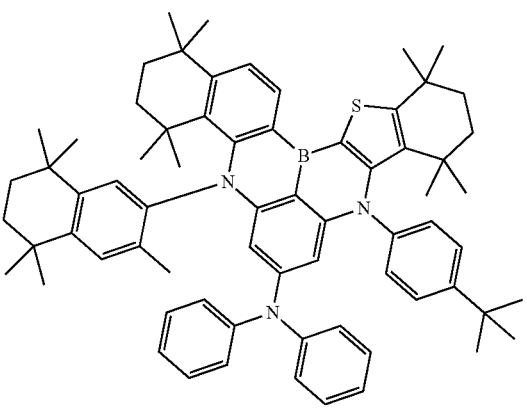
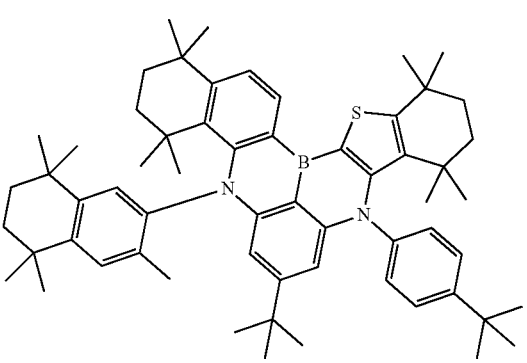
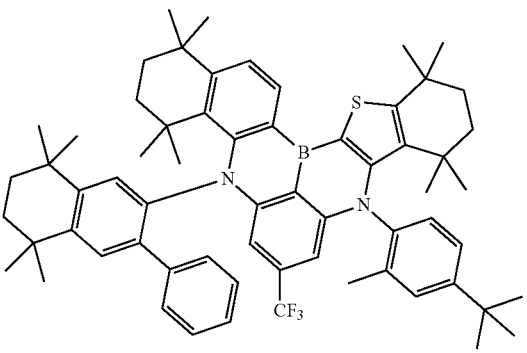
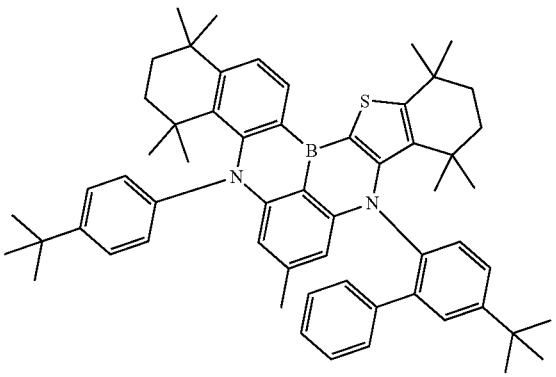

177
-continued
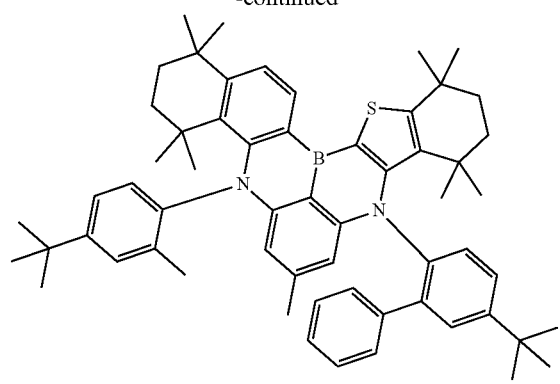
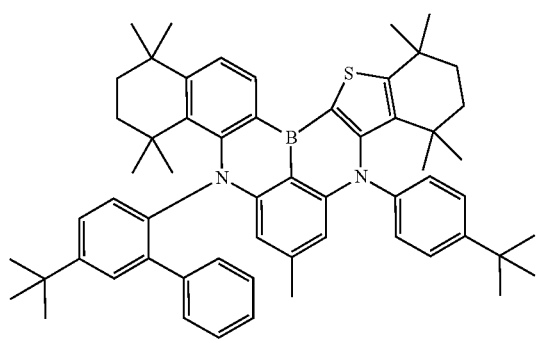
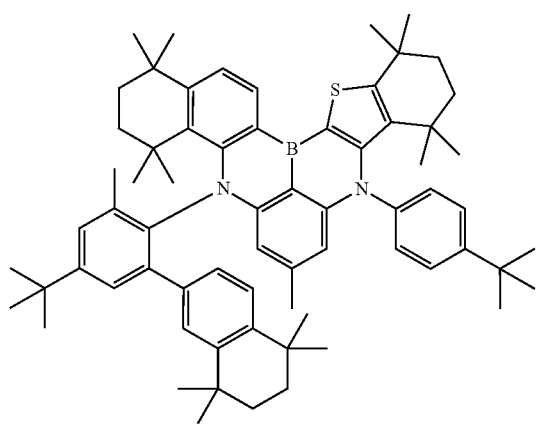
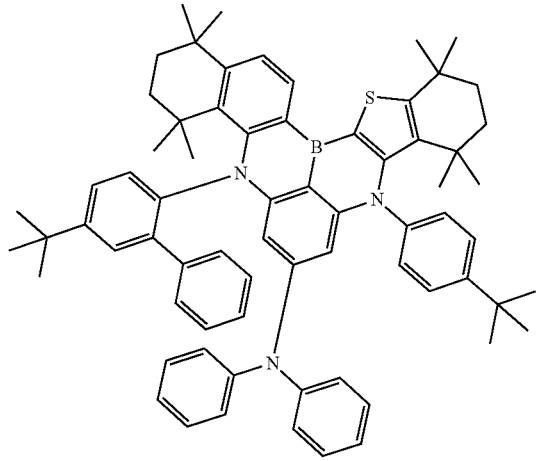
178
-continued
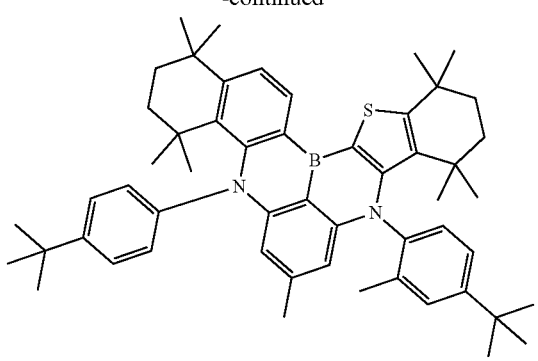
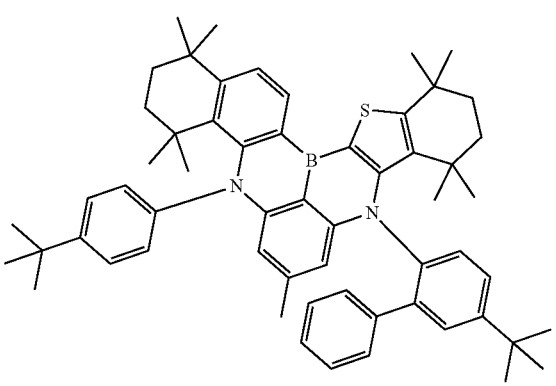
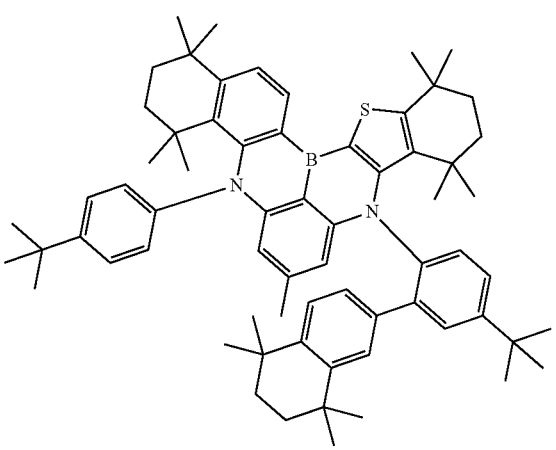
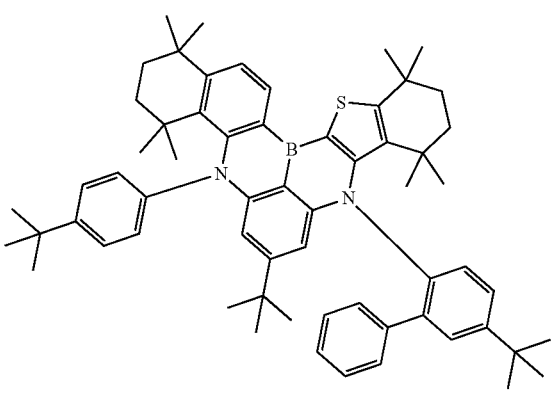

| 179 -continued | 180 -continued |
|---|---|
| 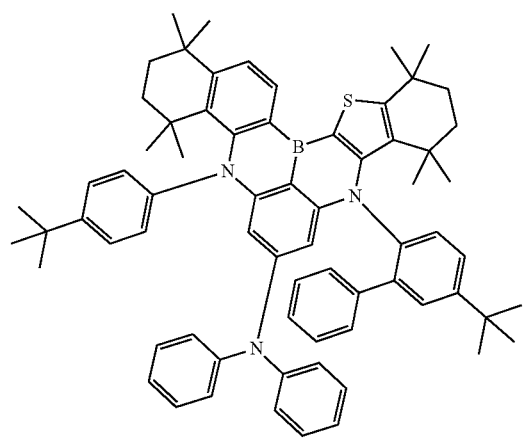 | 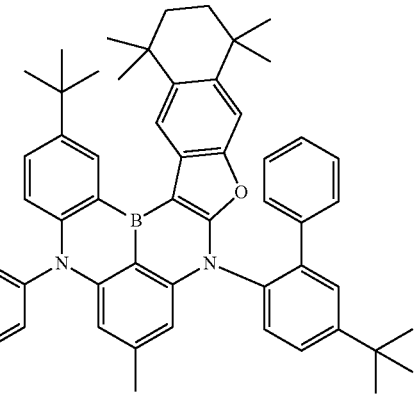 |
| 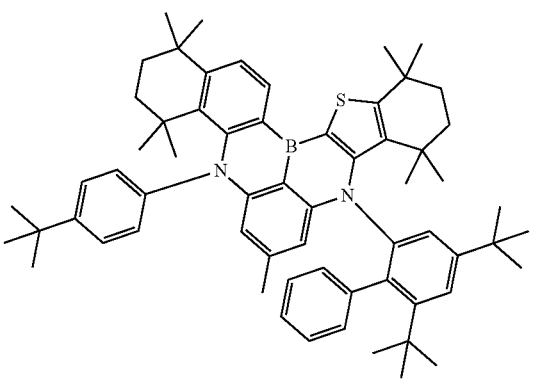 | 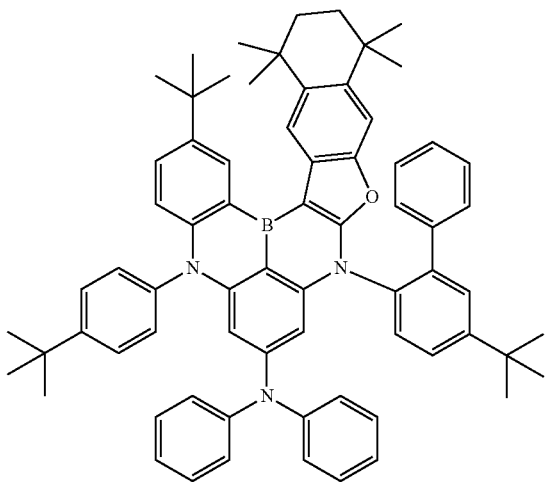 |
| 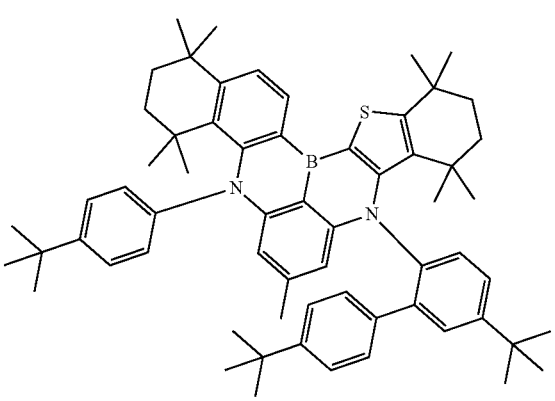 | |
| 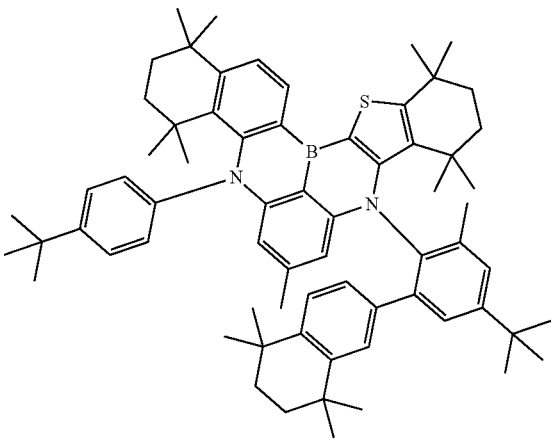 [SMILES: Cc1cc2c3c(c1)N(c1c(C)cc(C(C)(C)C)cc1-c1ccc4c(c1)C(C)(C)CCC4(C)C)c1c(sc4c1C(C)(C)CCC4(C)C)B3c1ccc3c(c1N2c1ccc(C(C)(C)C)cc1)C(C)(C)CCC3(C)C] | 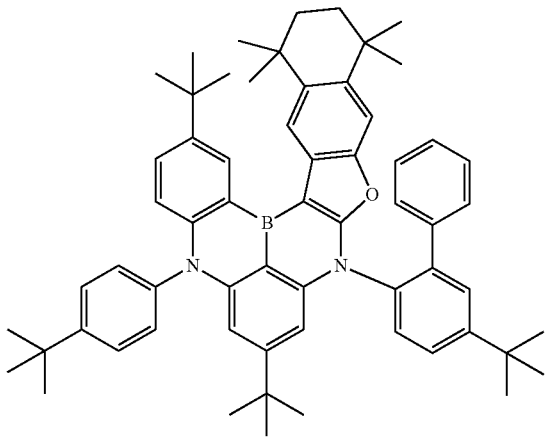 |

181
-continued
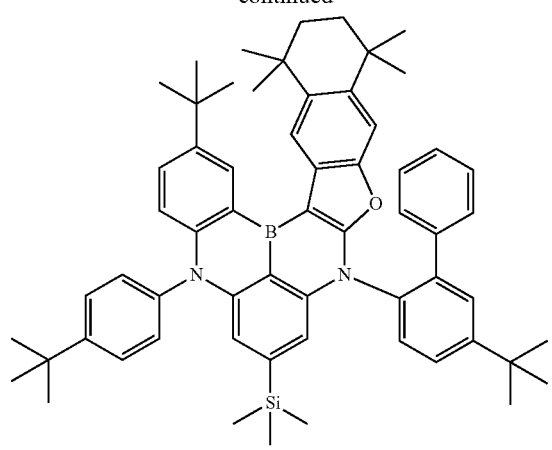
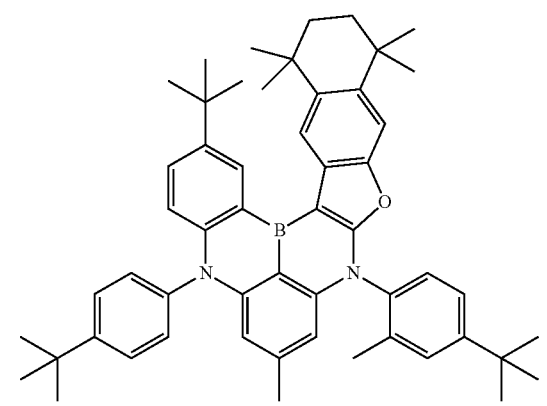
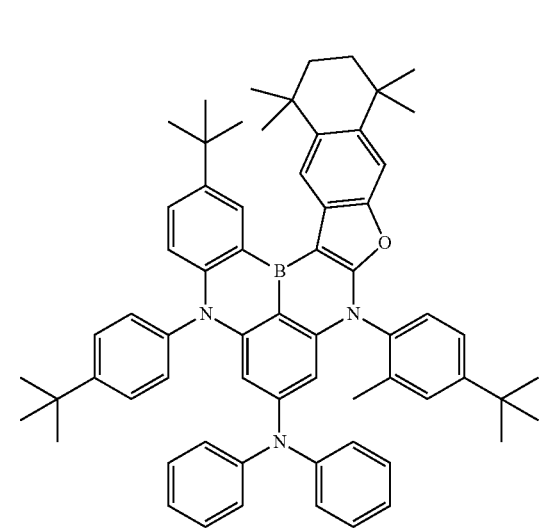
182
-continued
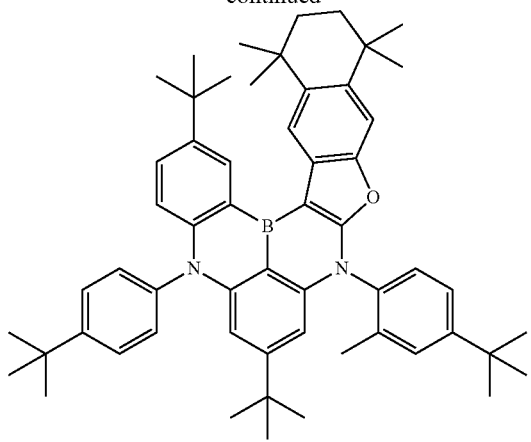
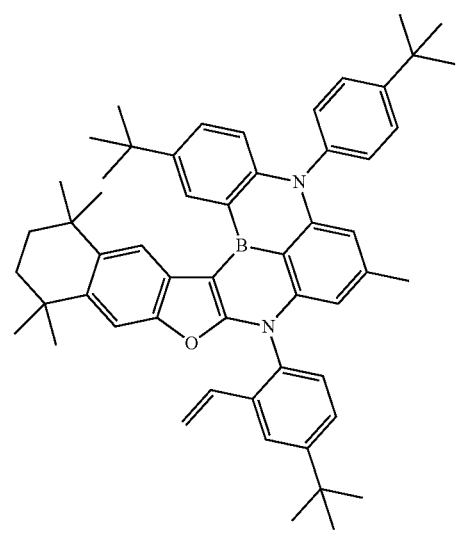

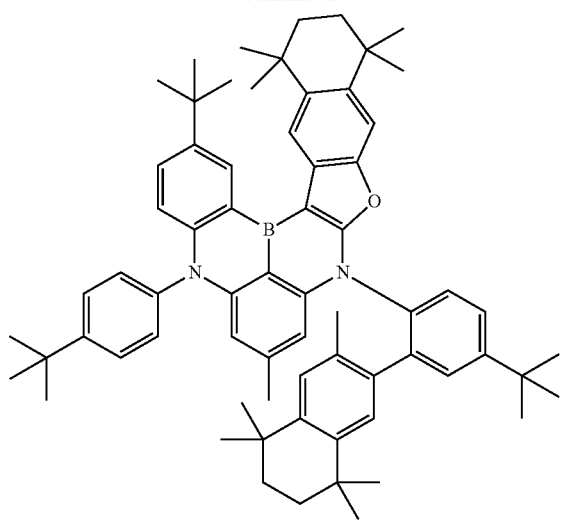
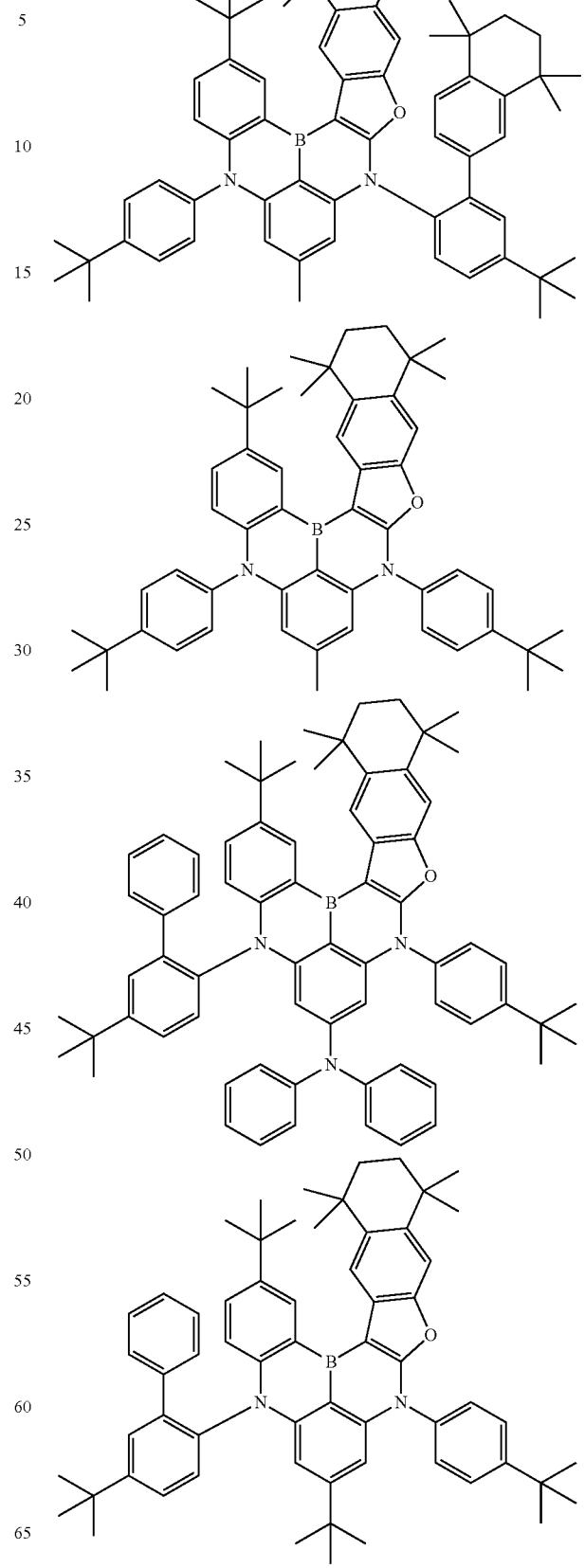

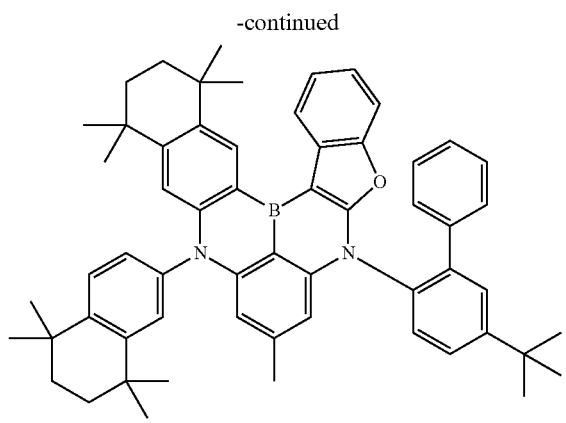
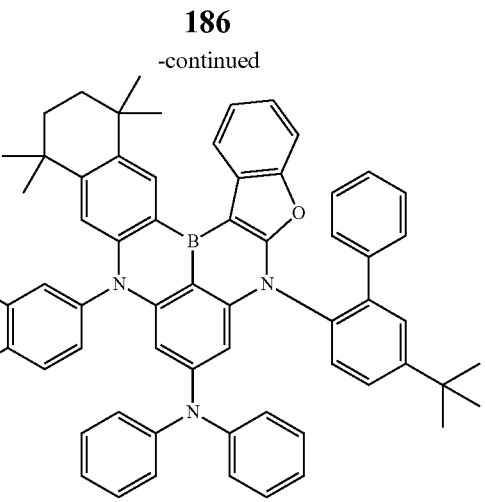
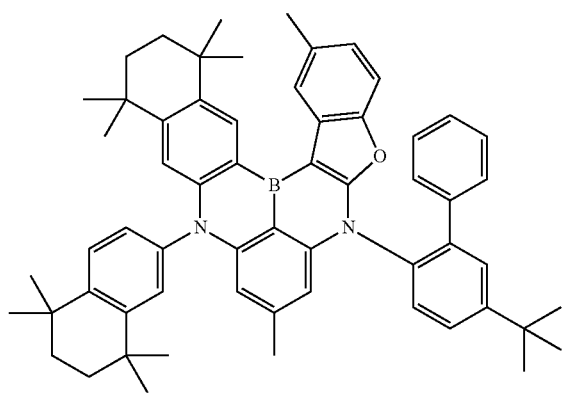
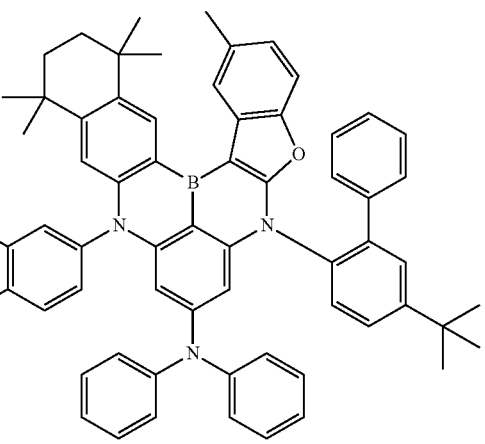
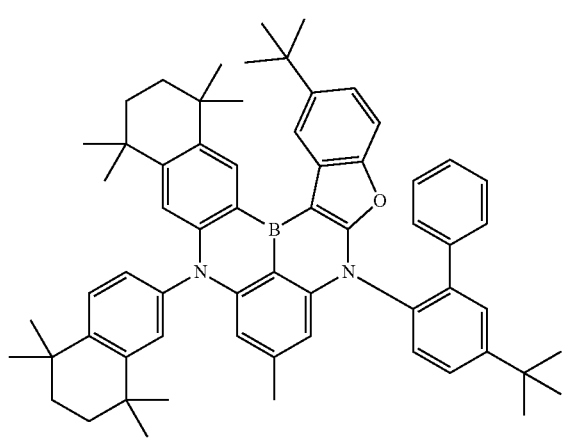
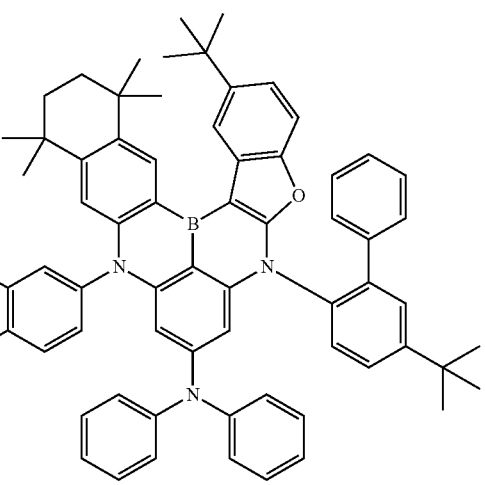

187
-continued
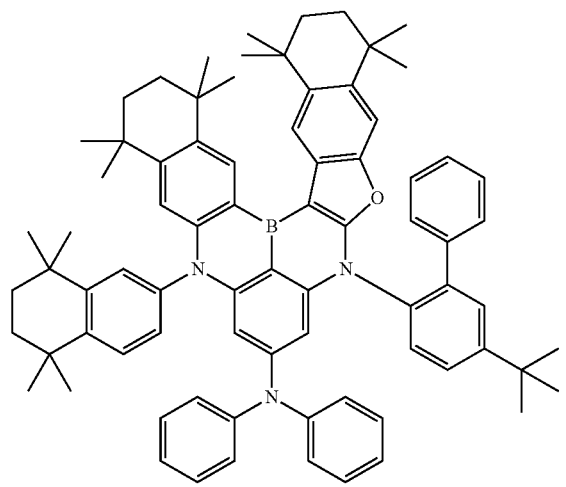
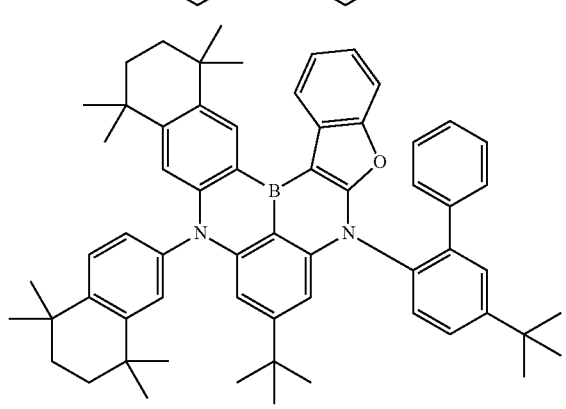
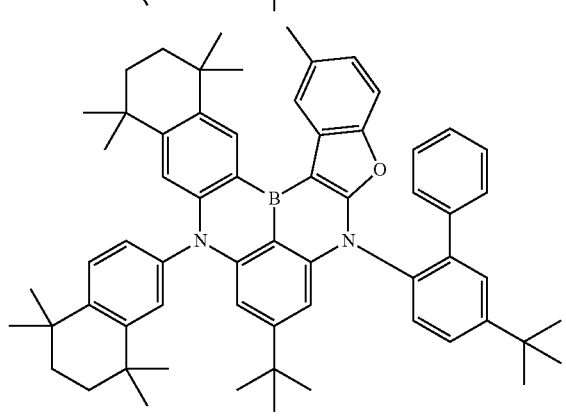
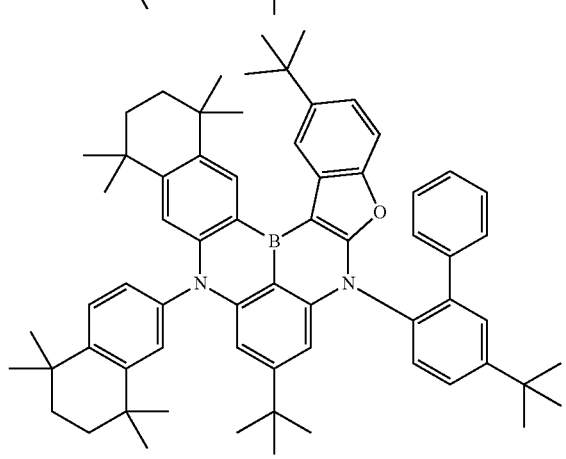
188
-continued
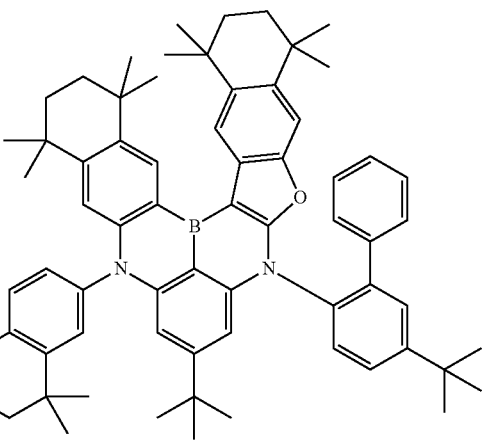
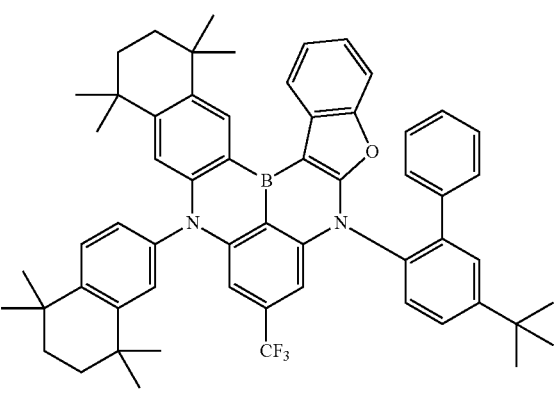
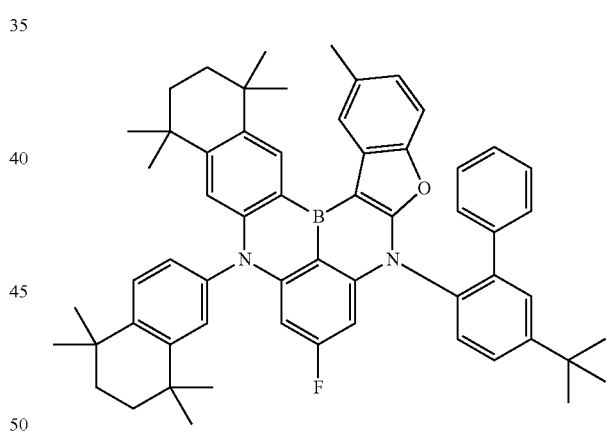
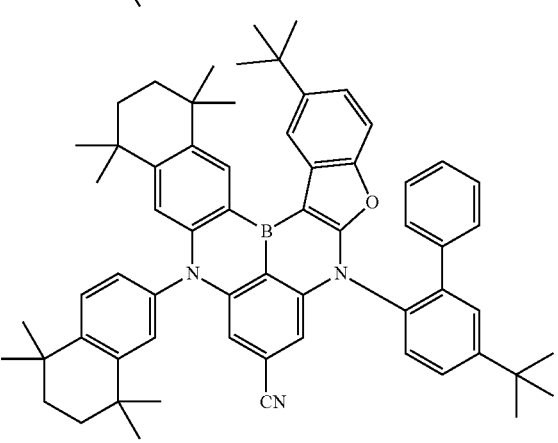

| 189 -continued | 190 -continued |
|---|---|
| 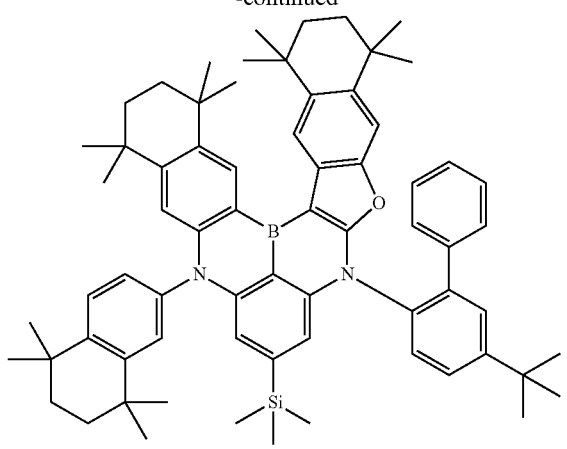 | 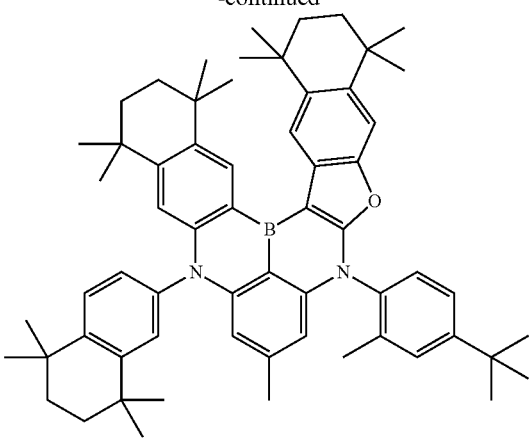 |
| 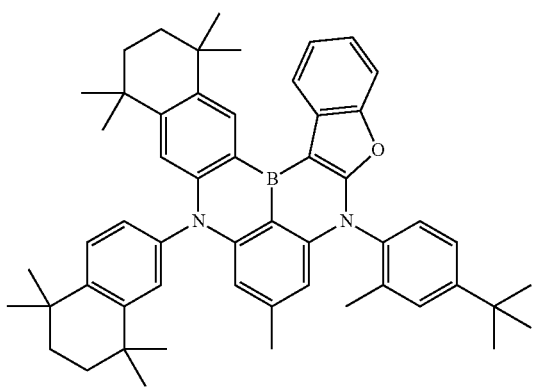 | 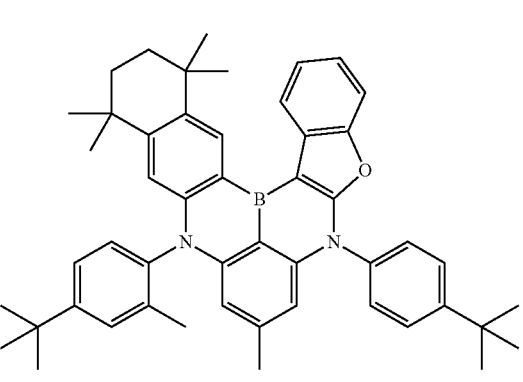 |
| 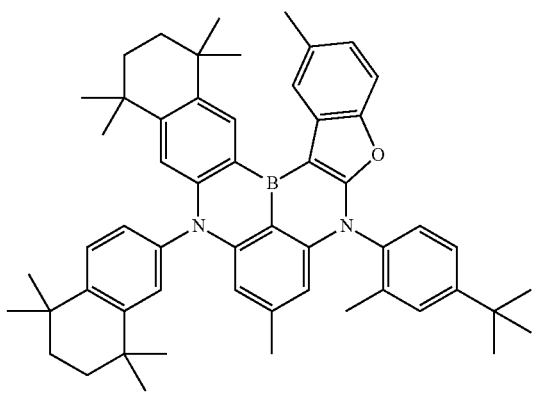 | 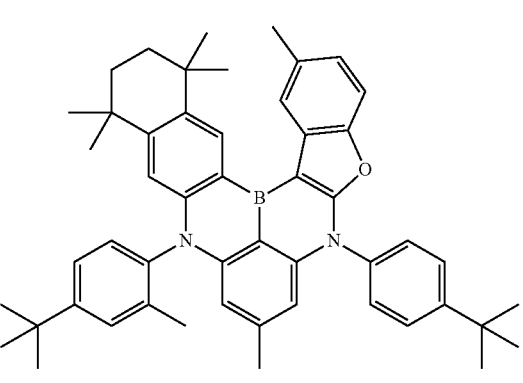 |
| 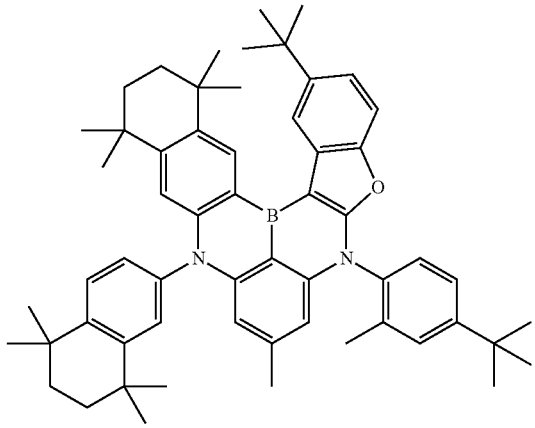 | 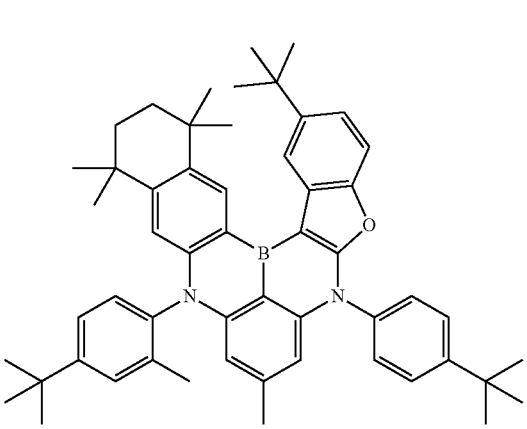 |

| 191 -continued | 192 -continued |
|---|---|
| 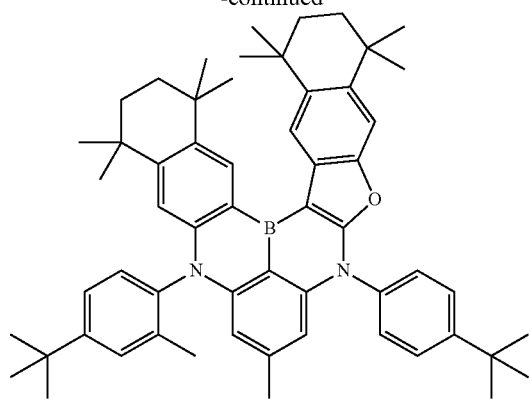 | 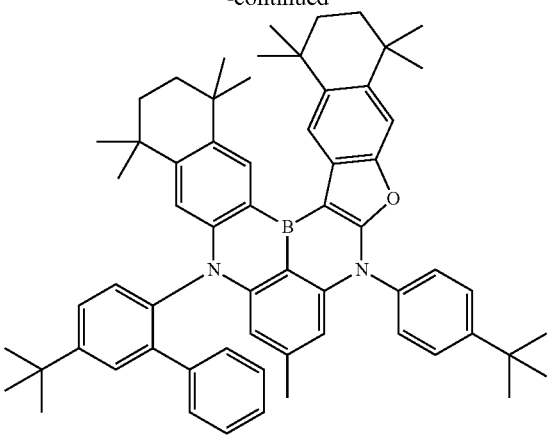 |
| 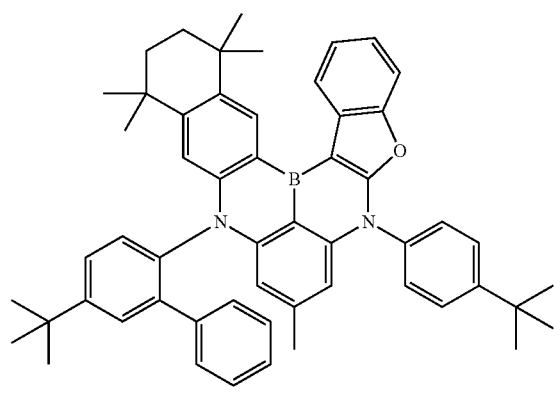 | |
| 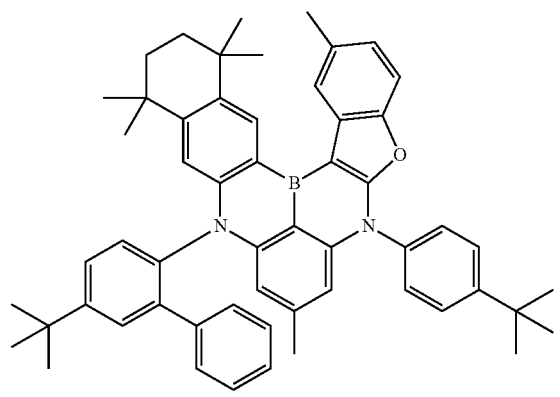 | 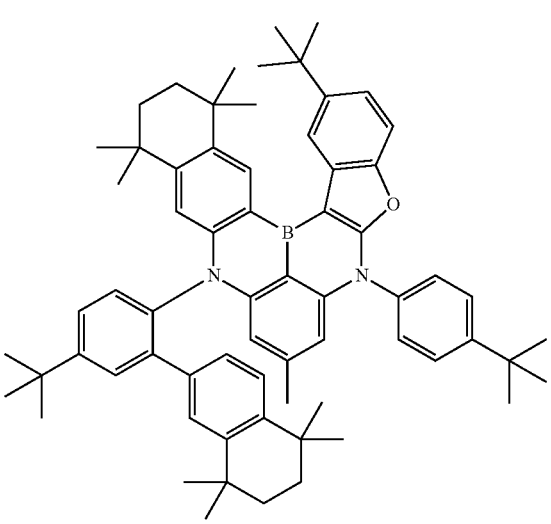 |
| 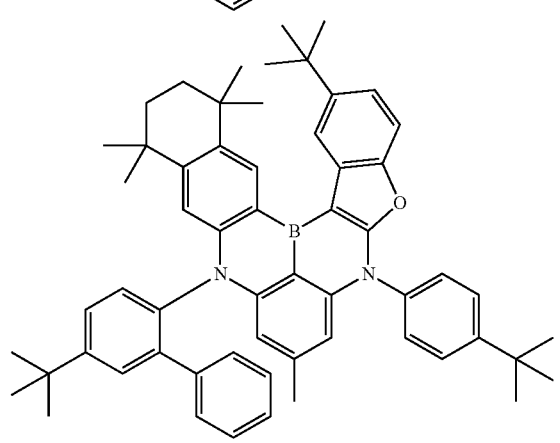 | 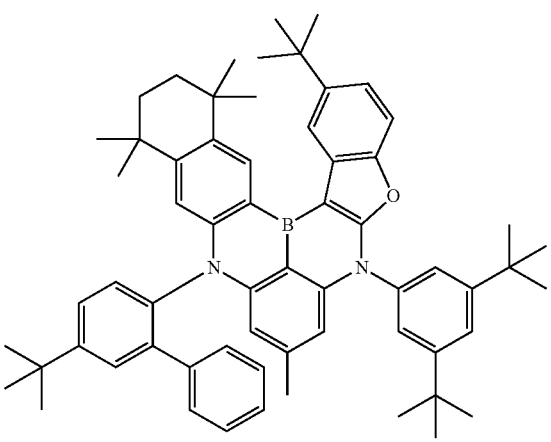 |

193
-continued
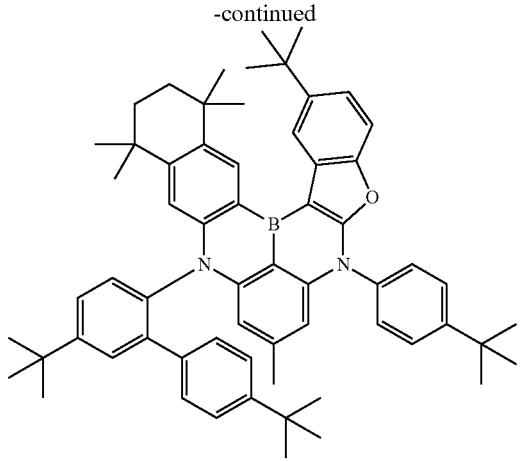
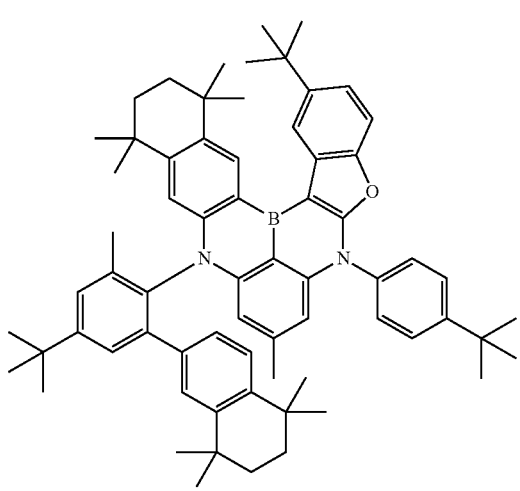
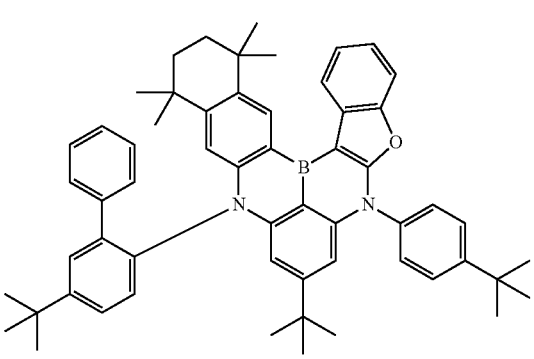
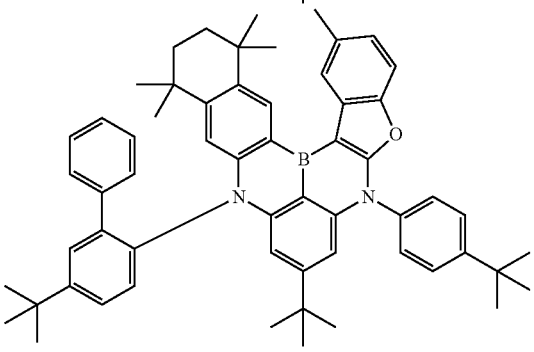
194
-continued
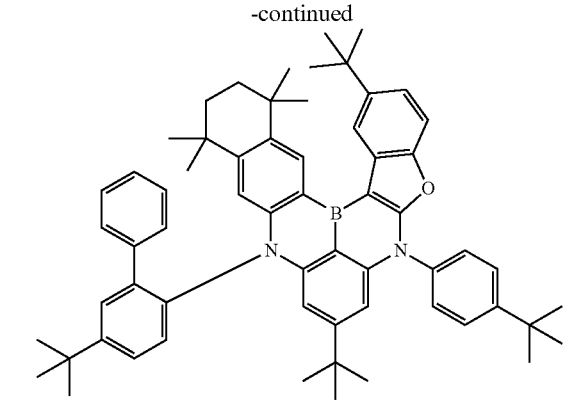
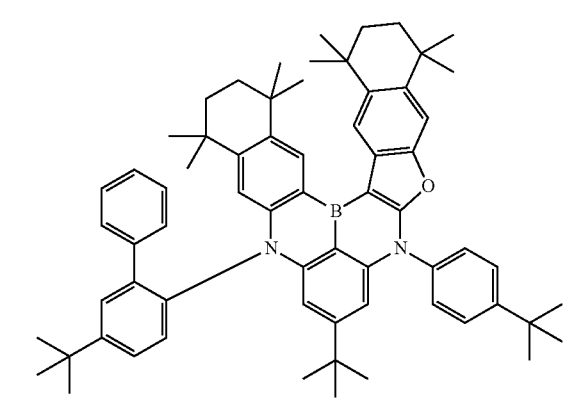
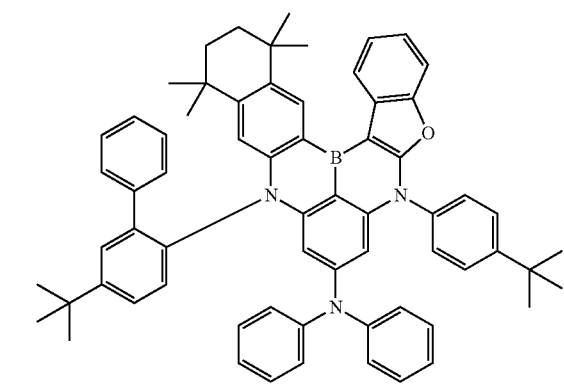
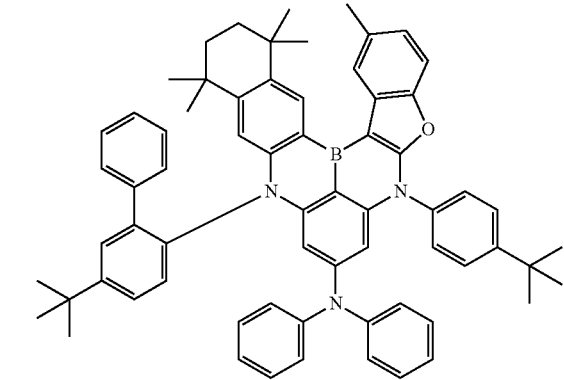

195
-continued
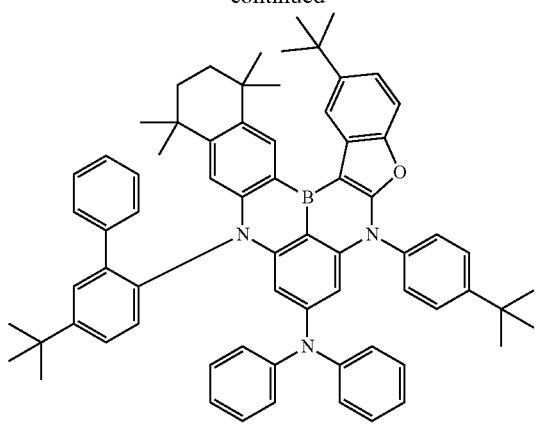
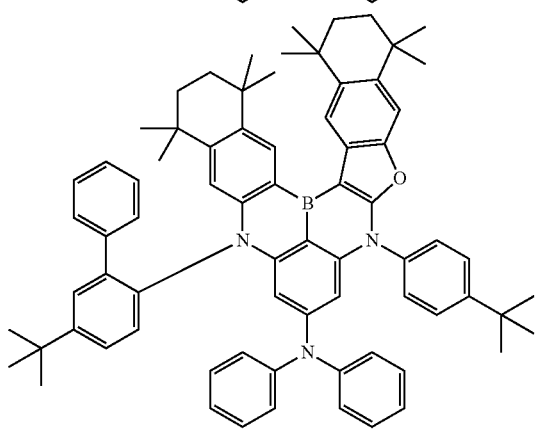
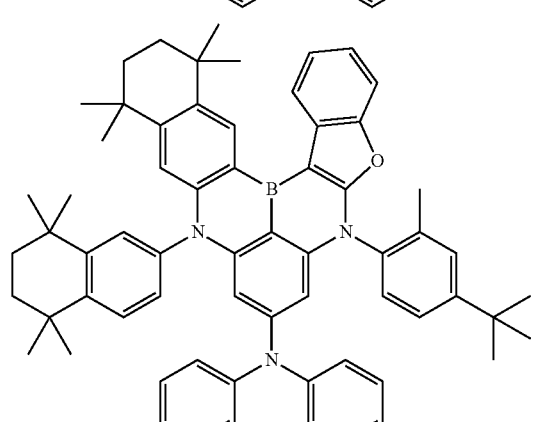
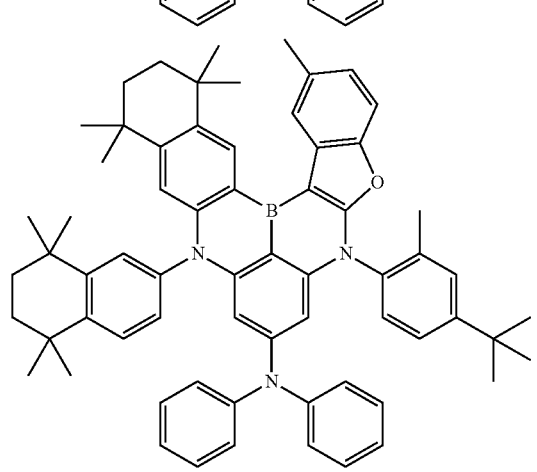
196
-continued
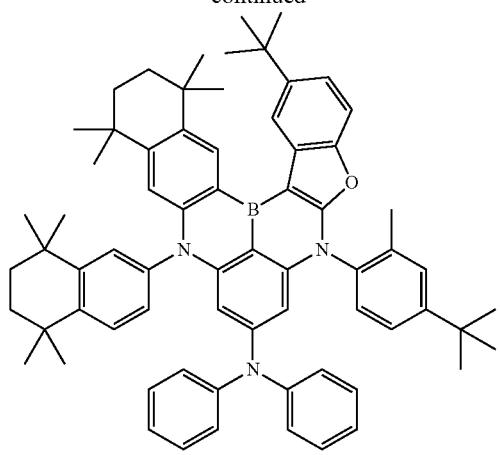
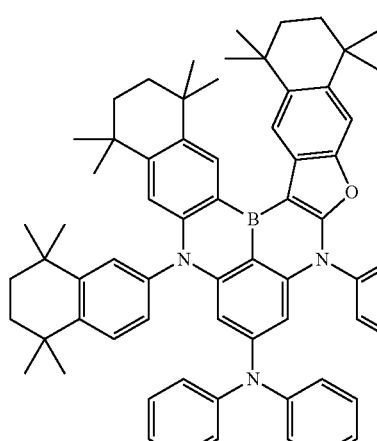
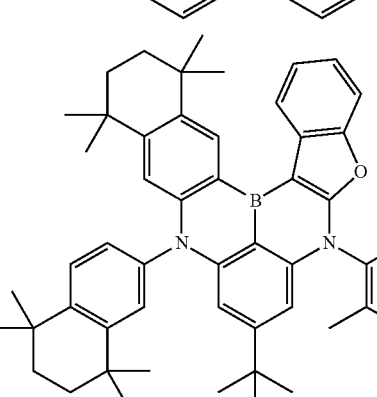
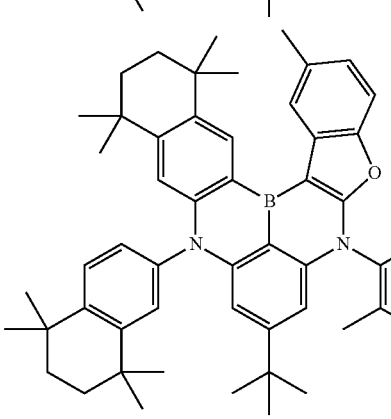

197
-continued
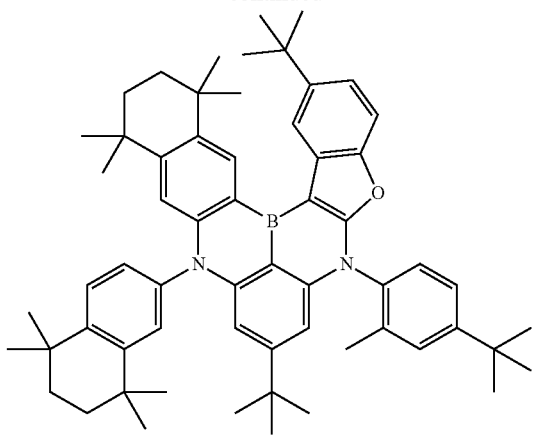
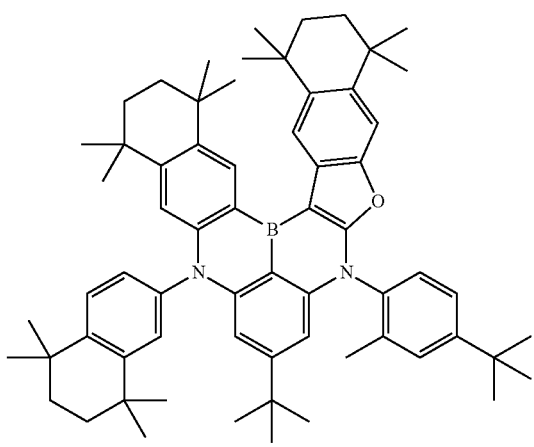
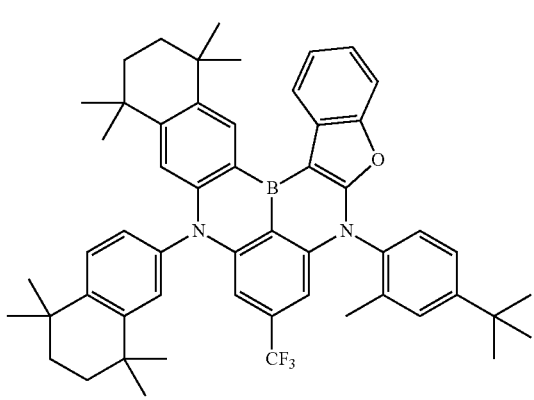
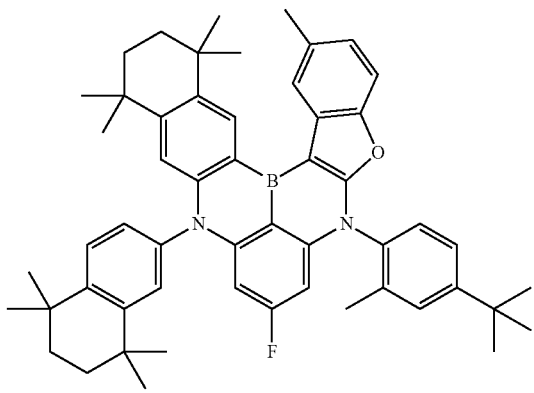
198
-continued
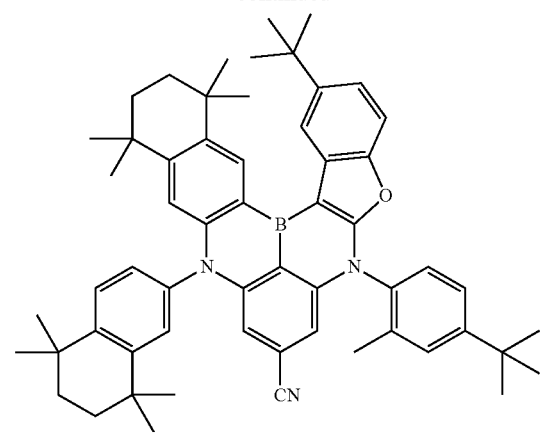
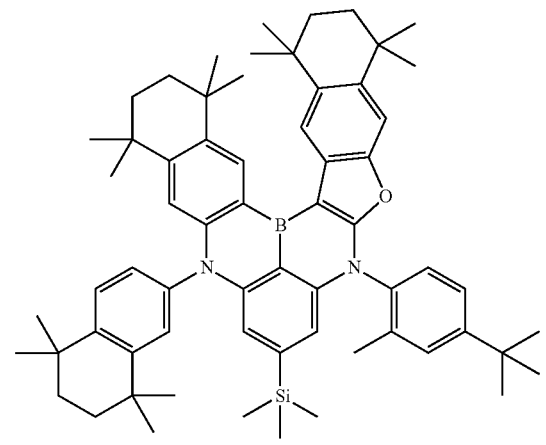
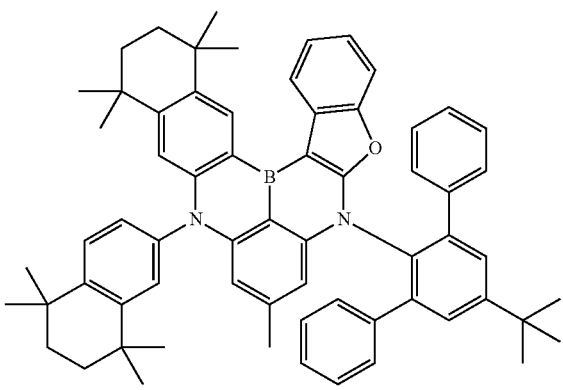
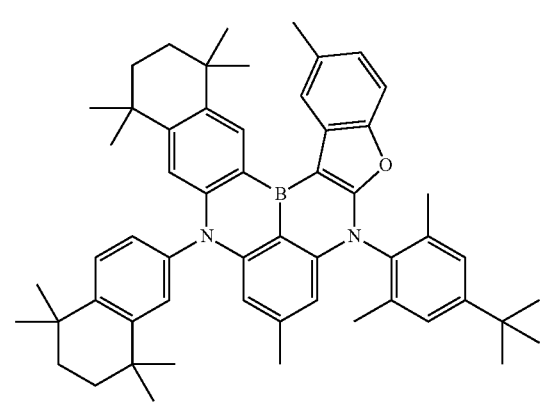

199
-continued
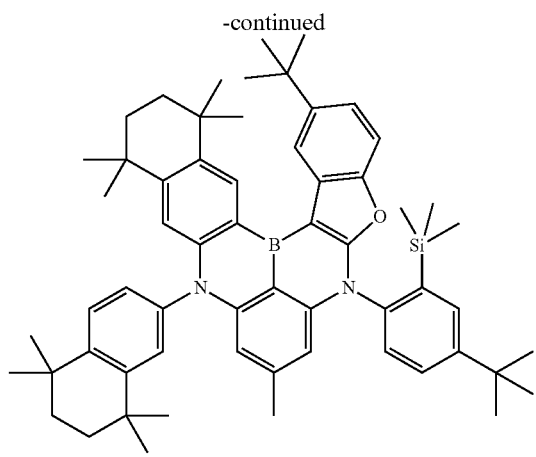
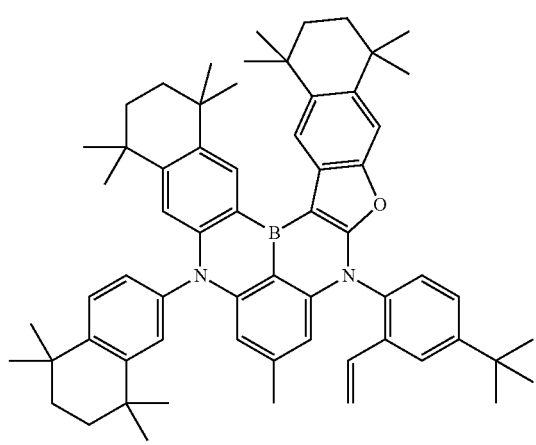
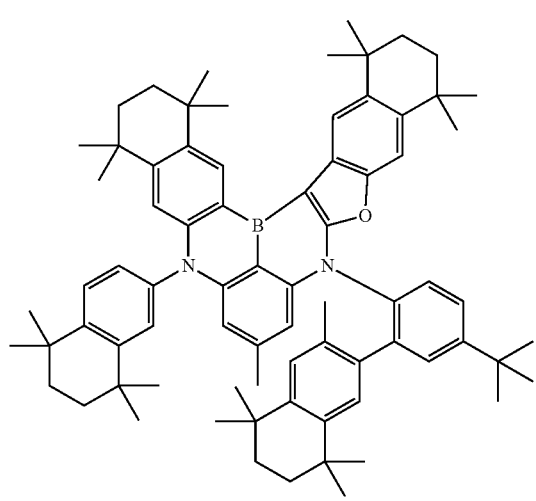
200
-continued
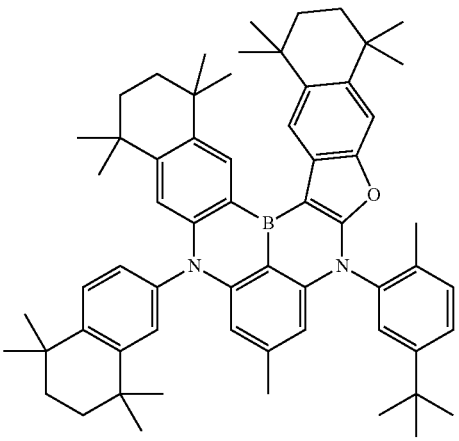
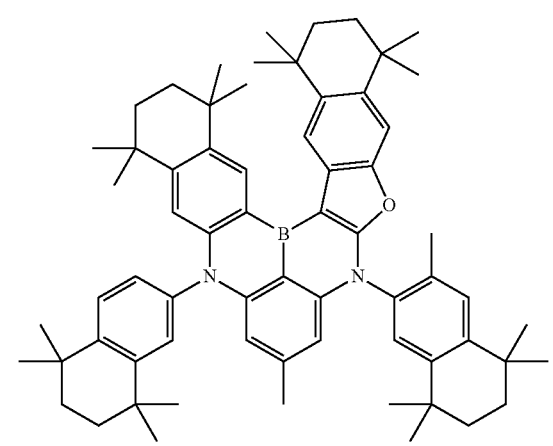
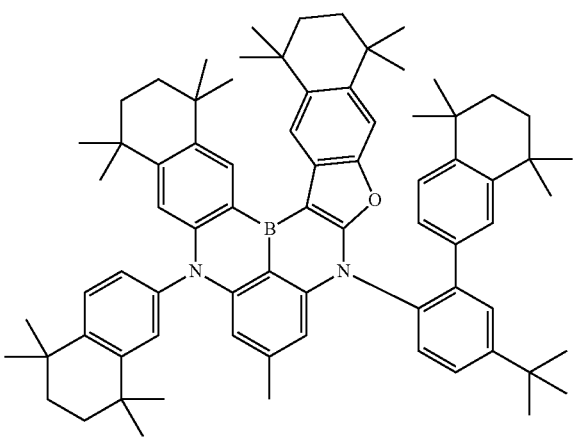
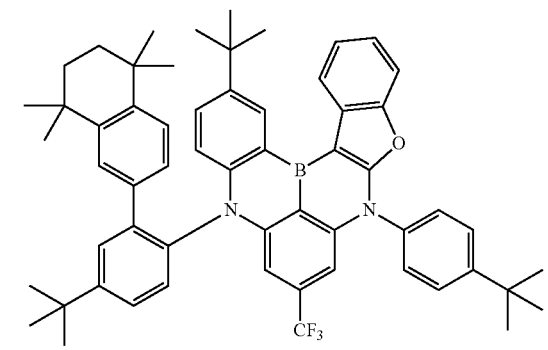

201
-continued
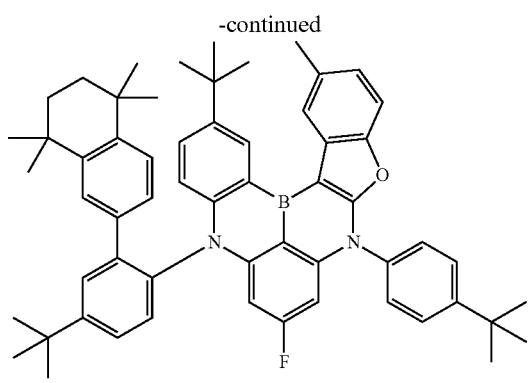
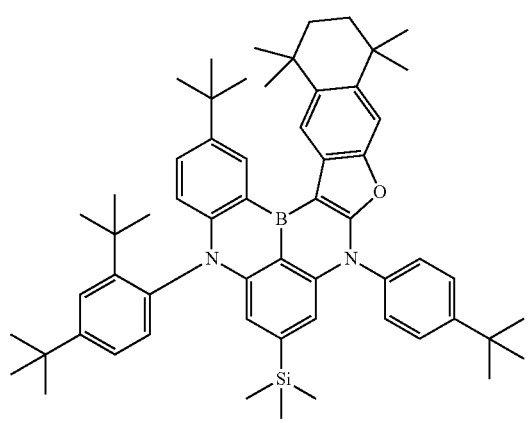
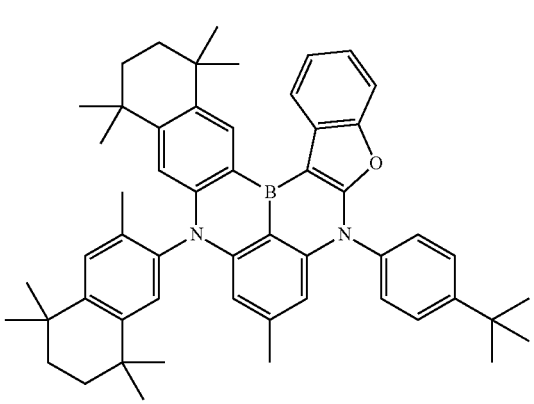
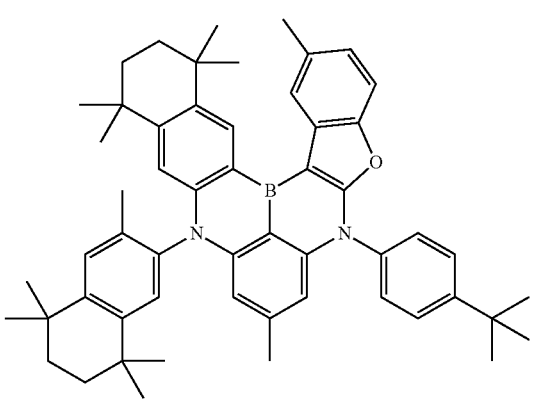
202
-continued
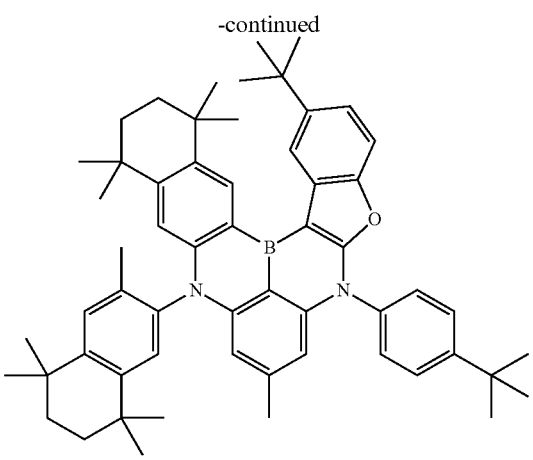
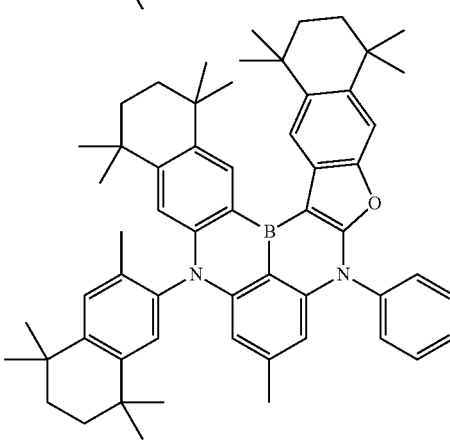
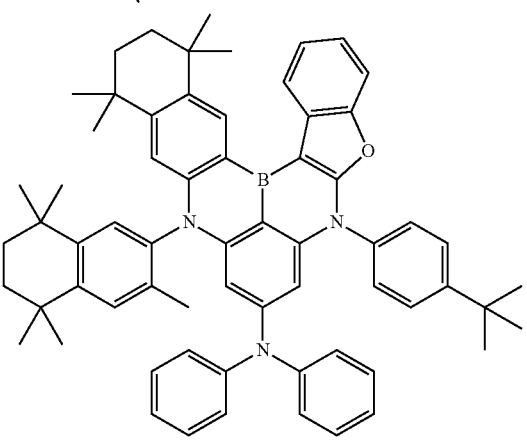
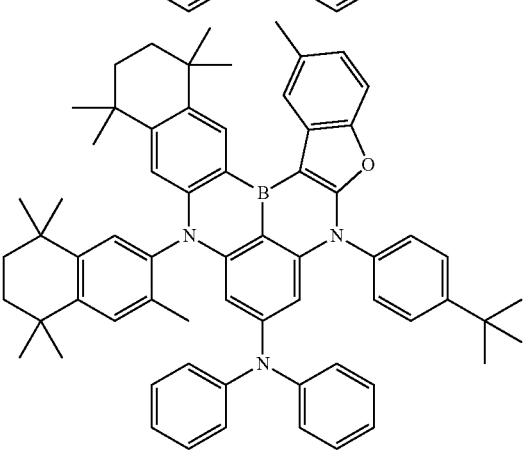

-continued
| 203 | 204 |
|---|---|
| 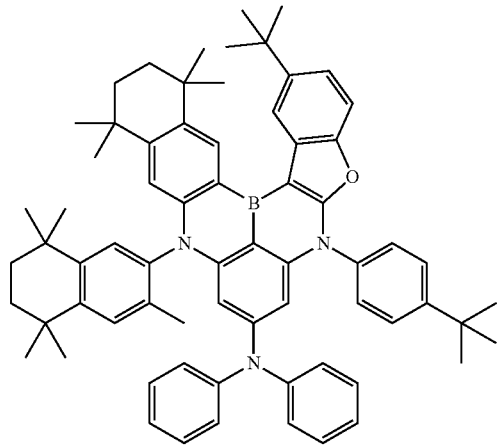 | 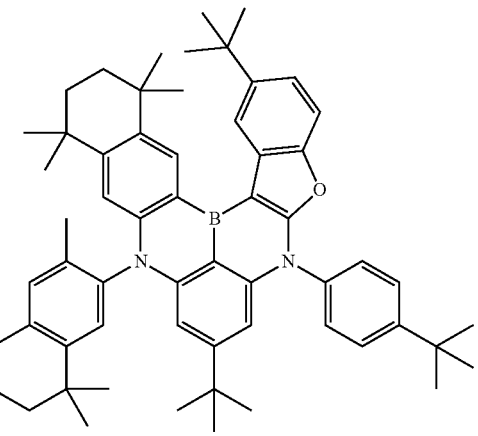 |
| 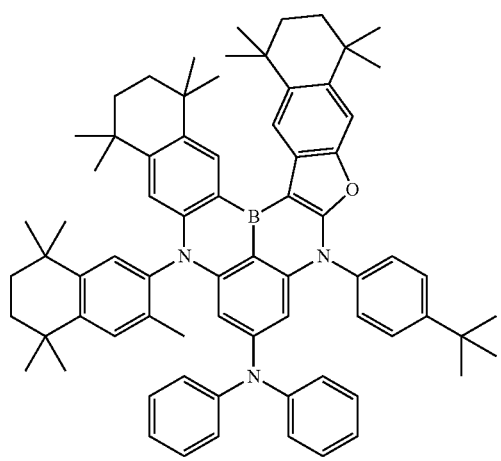 | 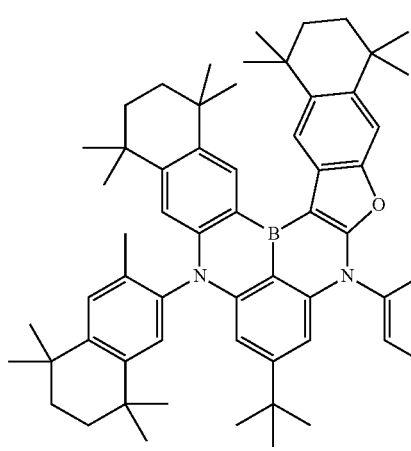 |
| 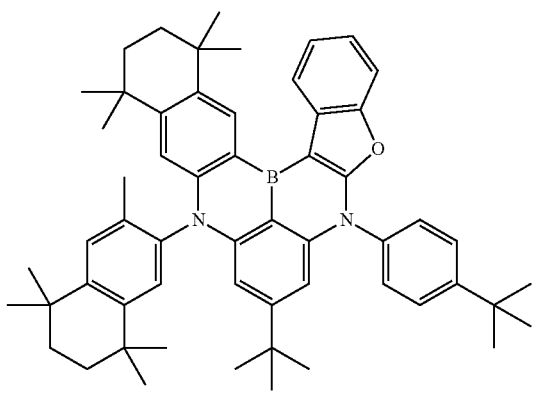 | 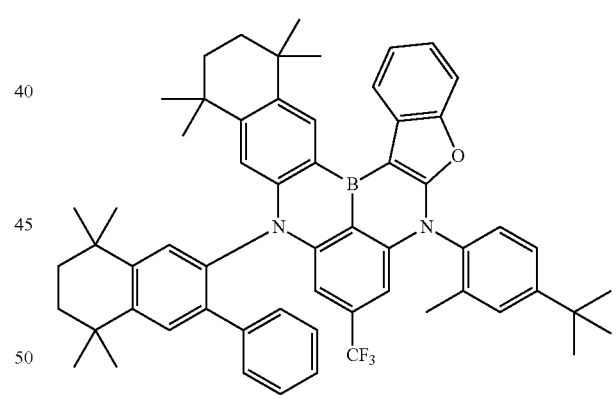 |
| 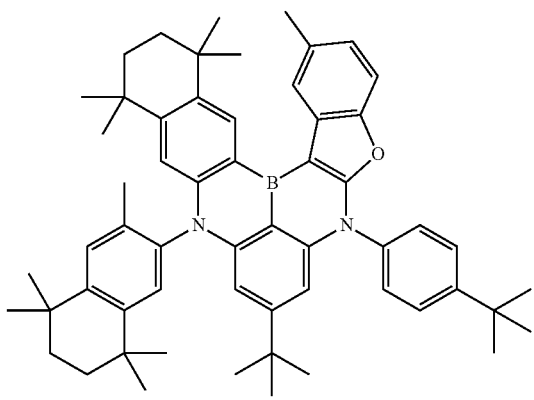 | 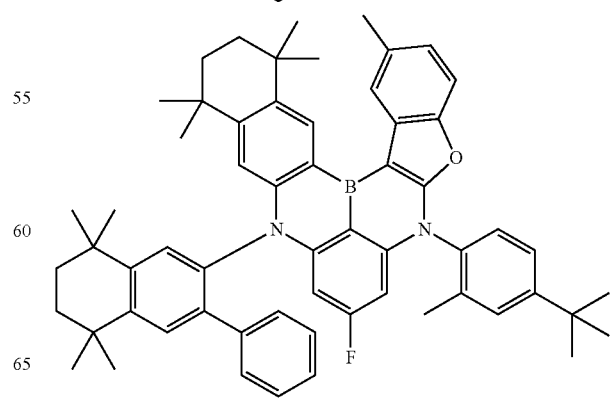 |

-continued
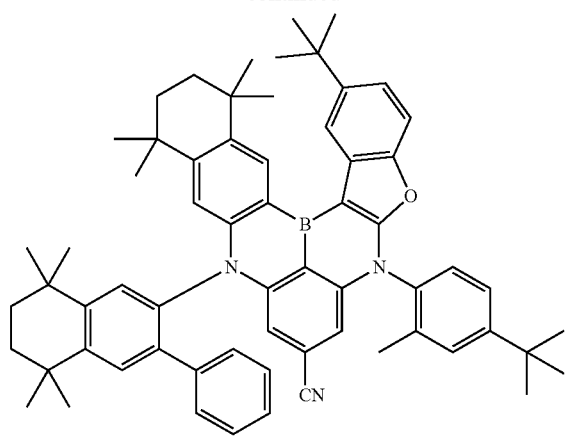

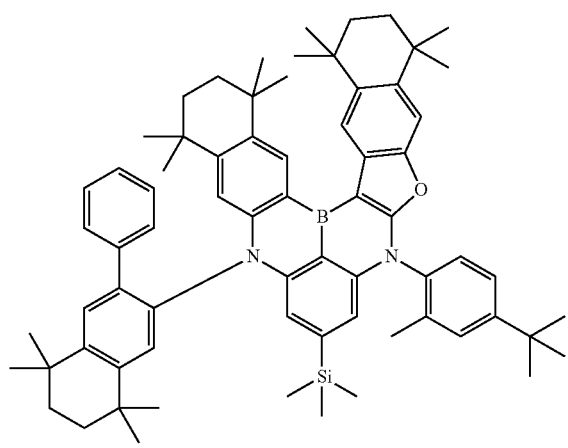
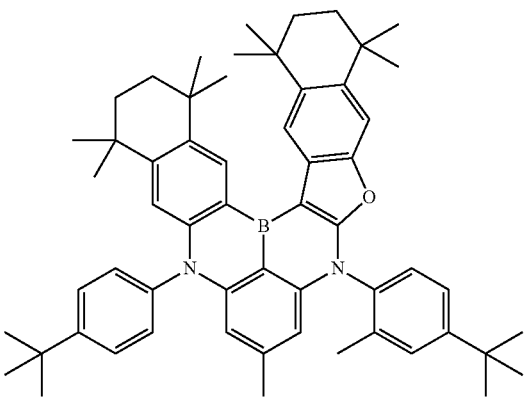
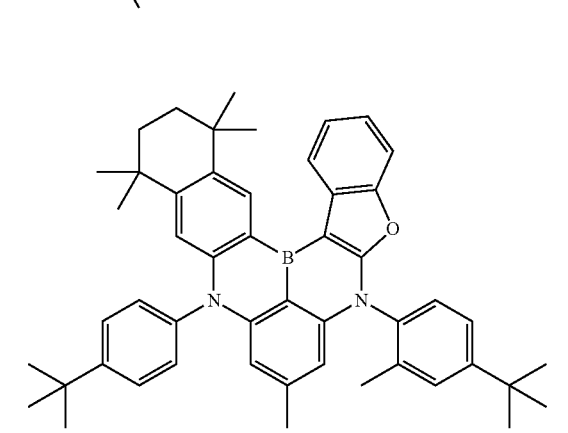
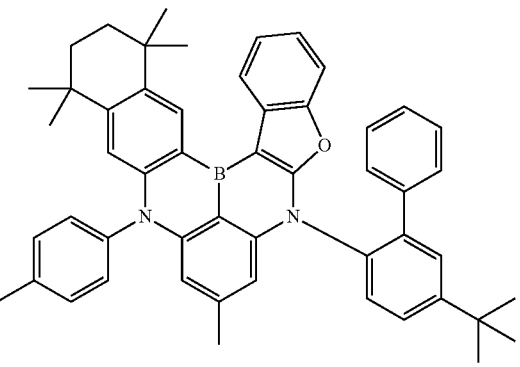
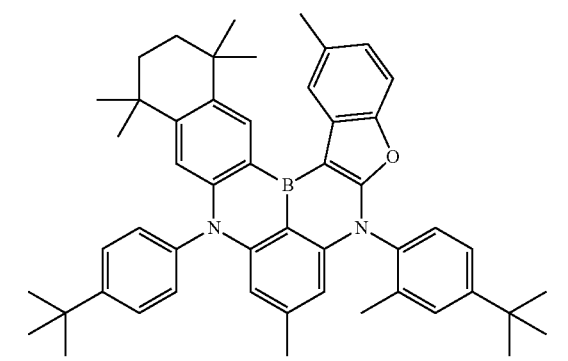
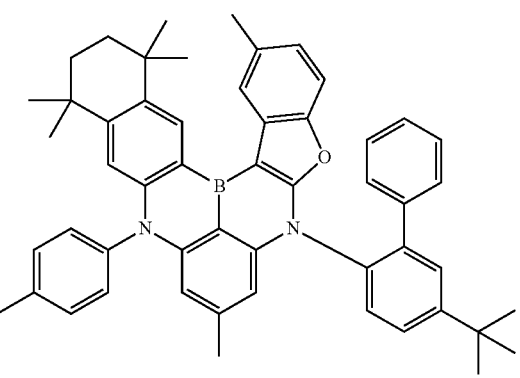

207
-continued
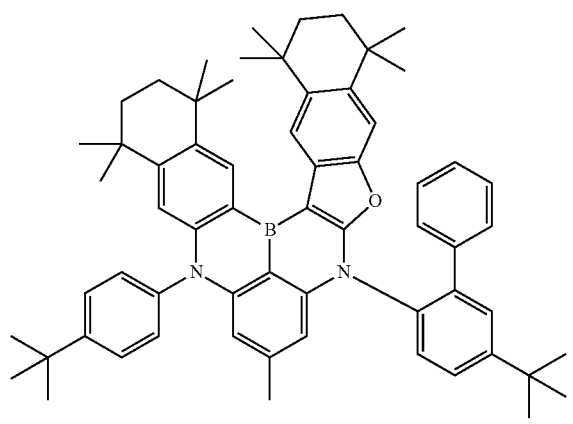
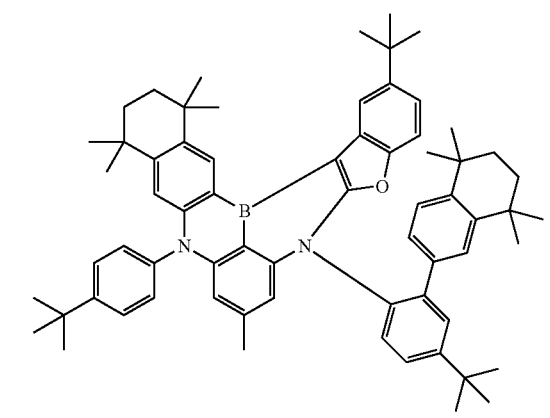
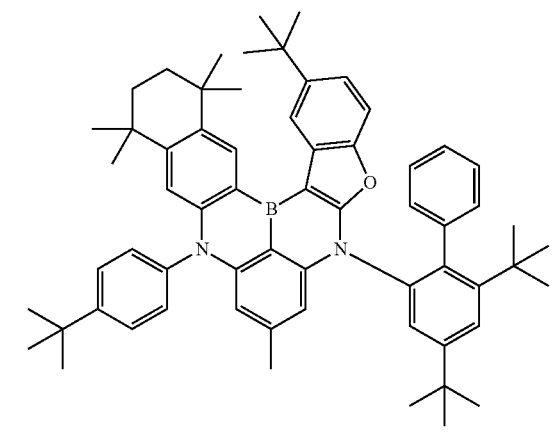
208
-continued
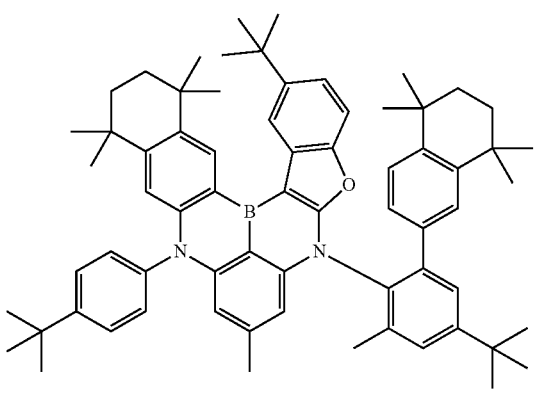
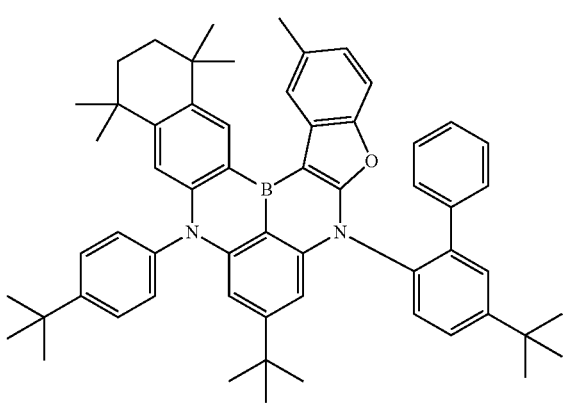

209
-continued
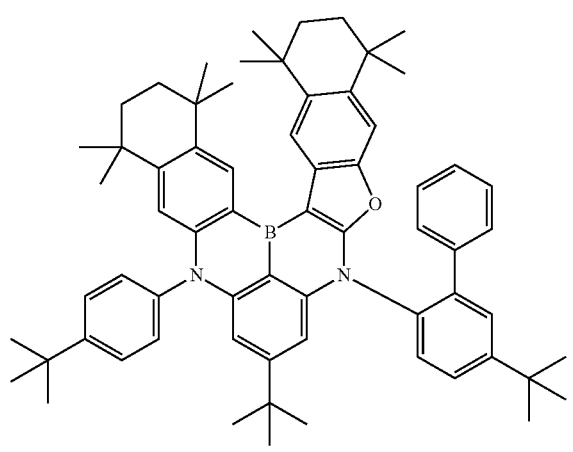
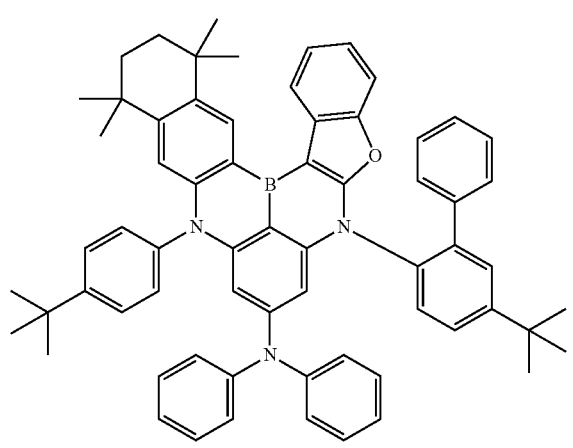
210
-continued
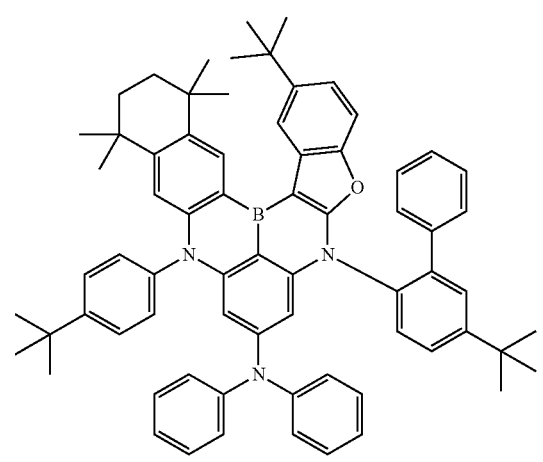
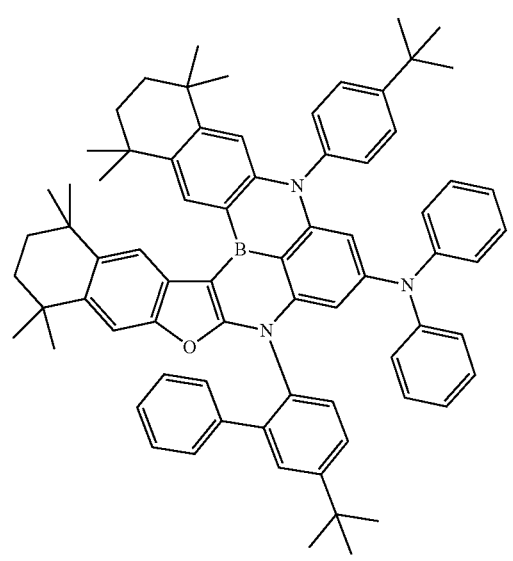

211
-continued
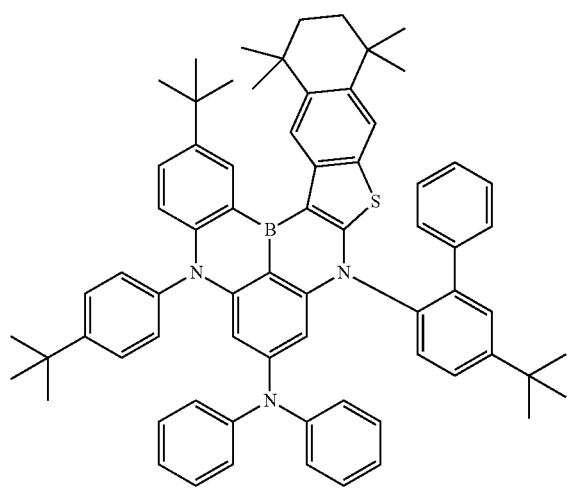
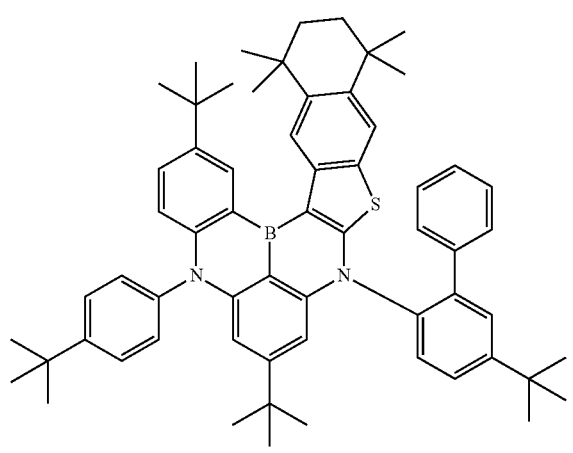
212
-continued
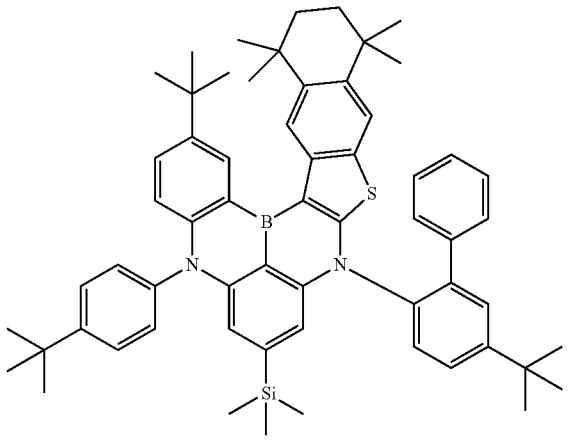
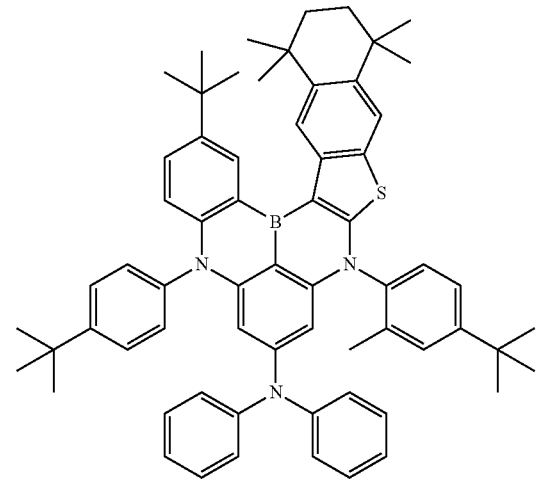

213
-continued
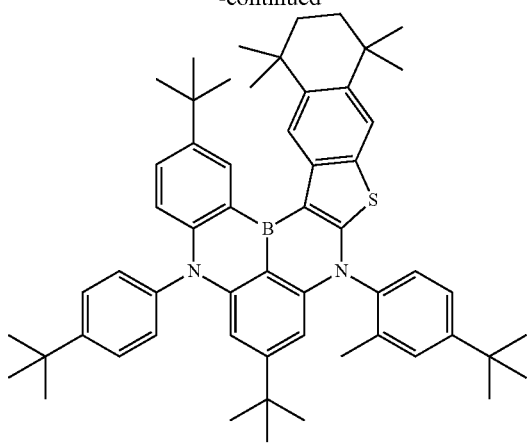
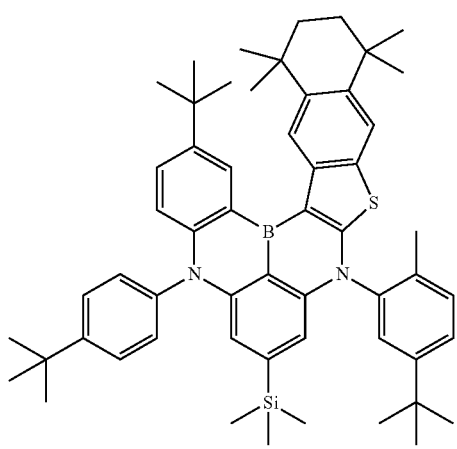
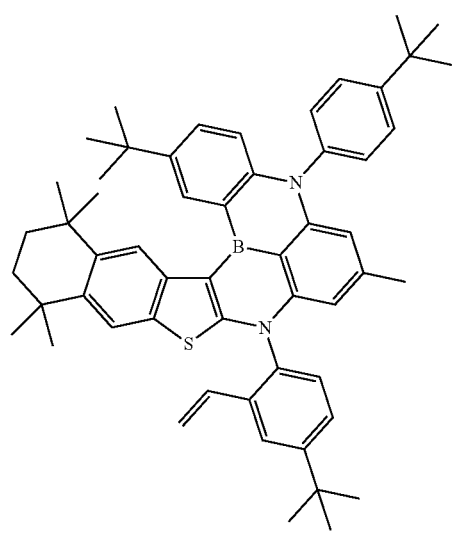
214
-continued
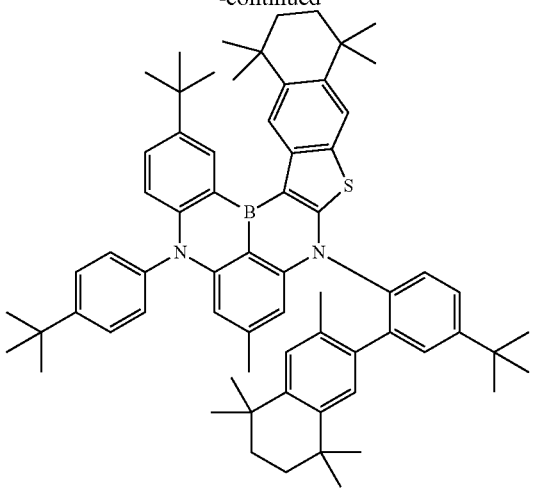
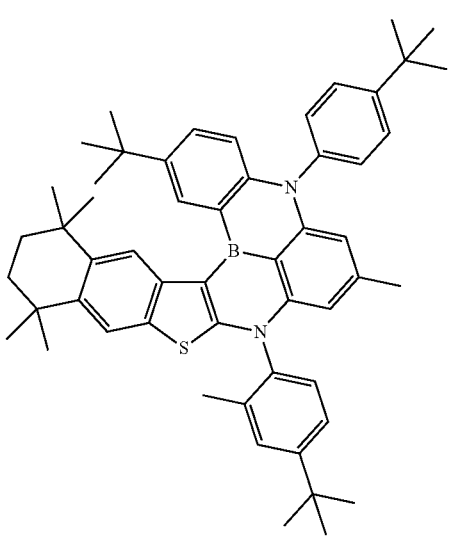
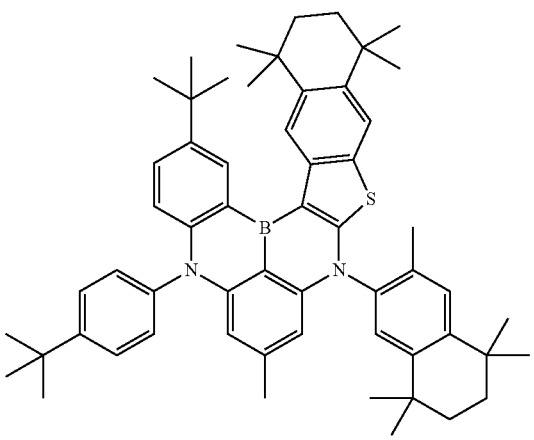

215
-continued
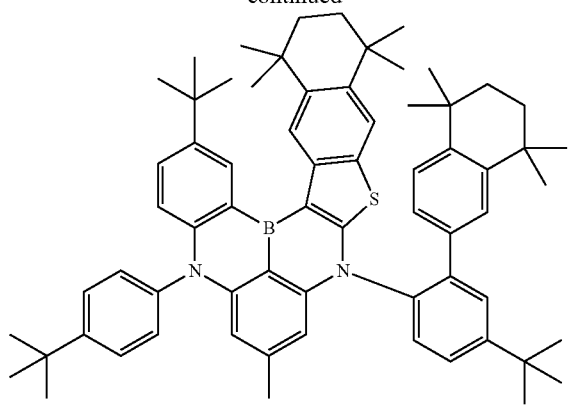
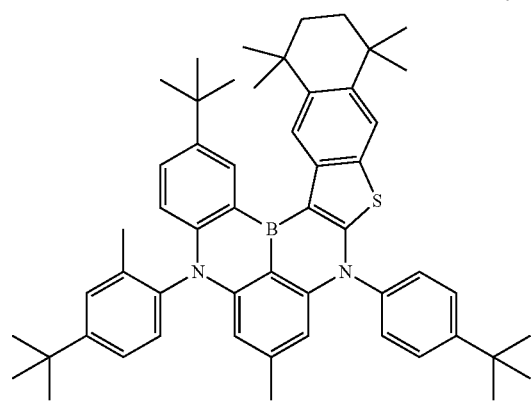
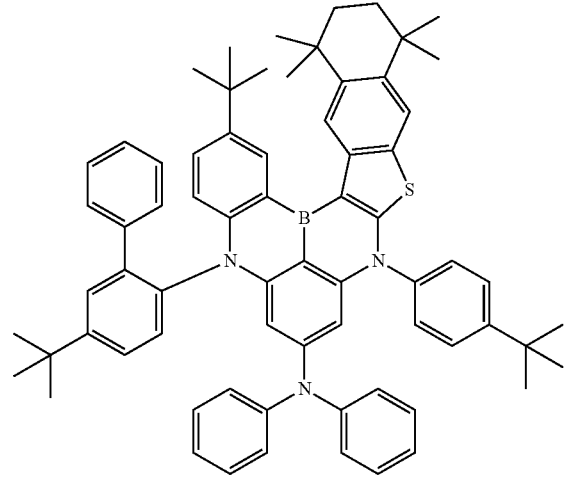
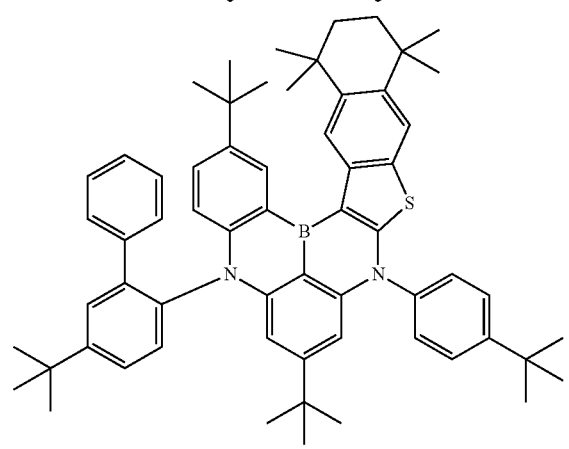
216
-continued
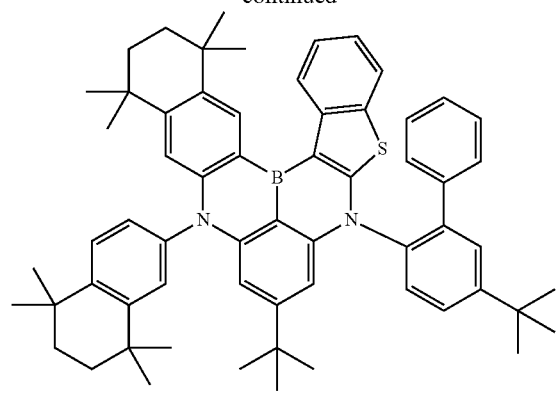
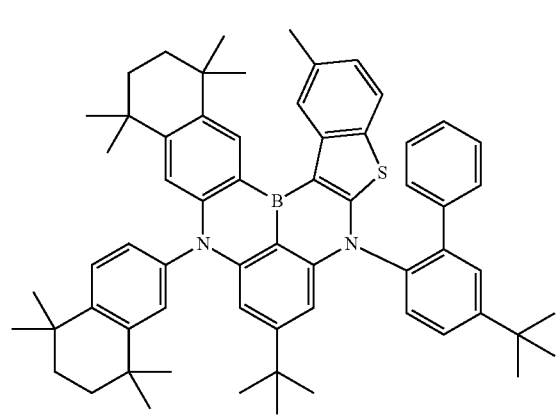
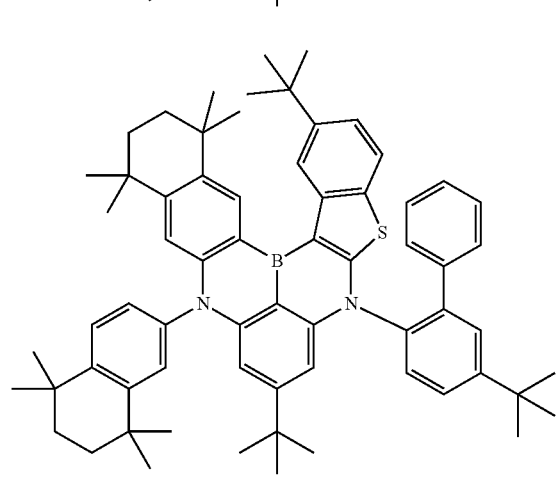
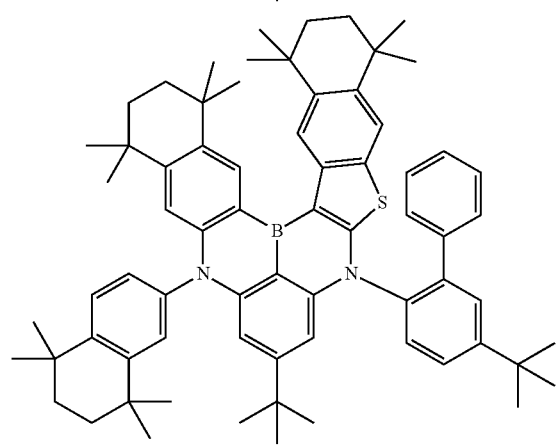

217
-continued
218
-continued
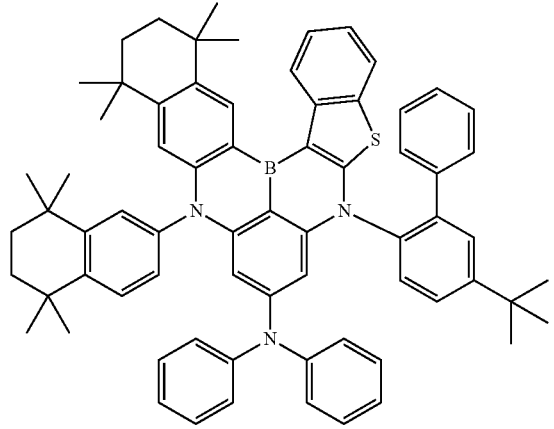
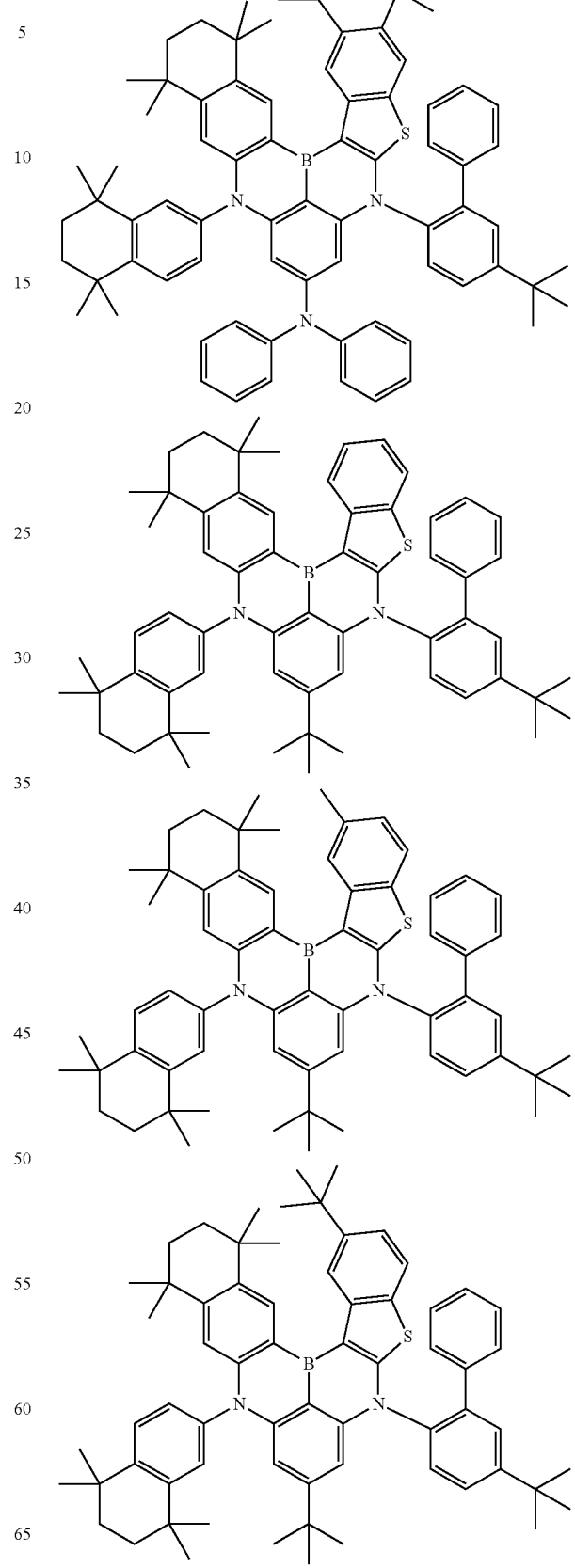

219
-continued
220
-continued
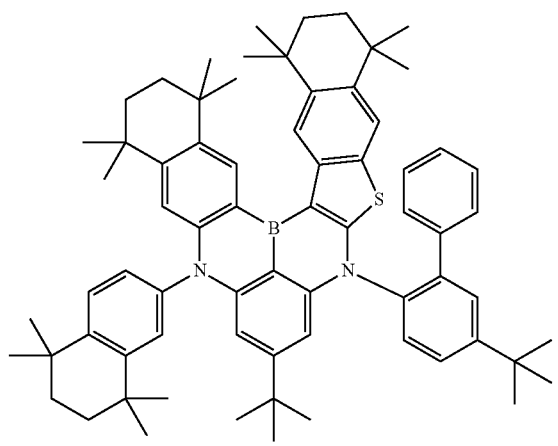
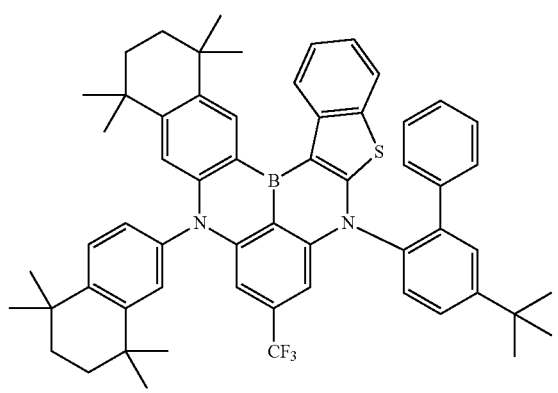
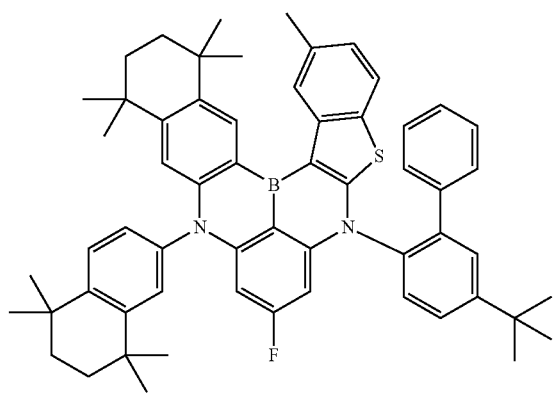
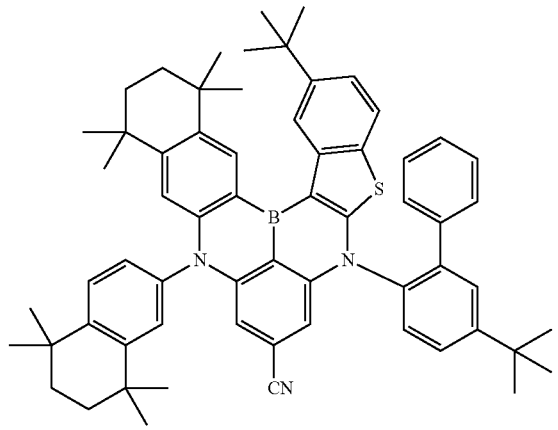
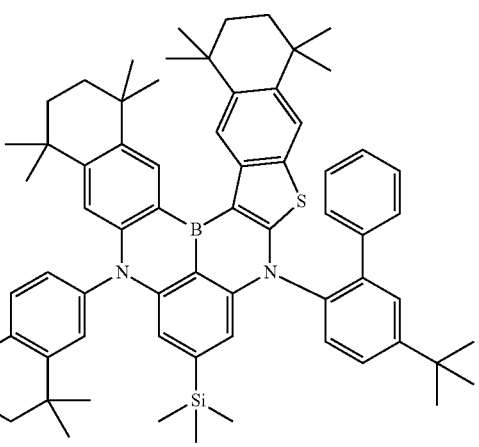
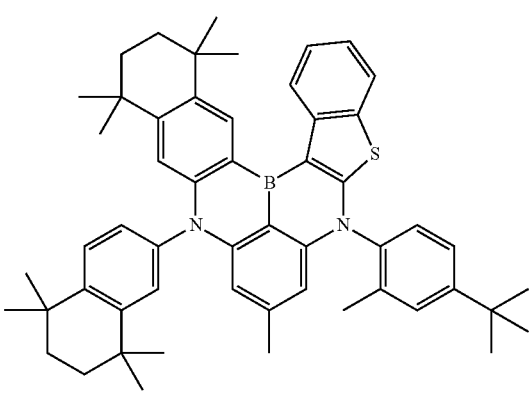
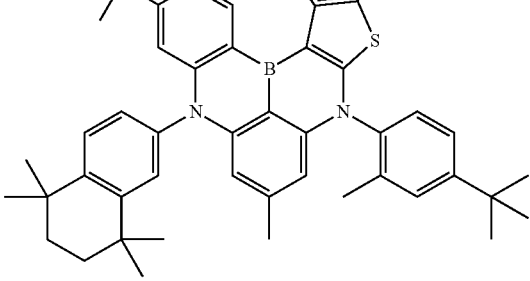

221
-continued
222
-continued
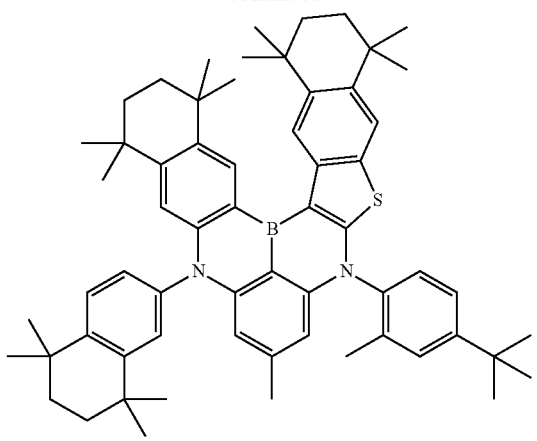
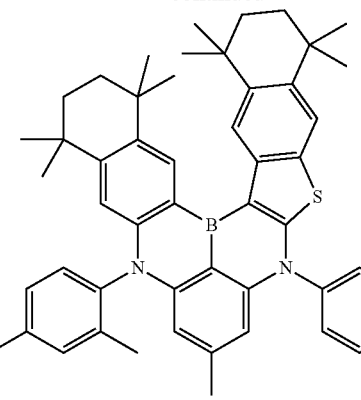
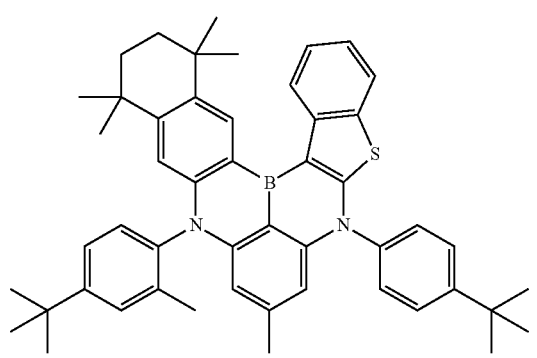
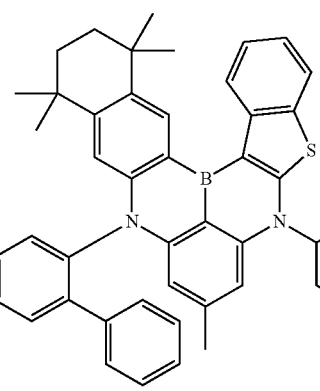
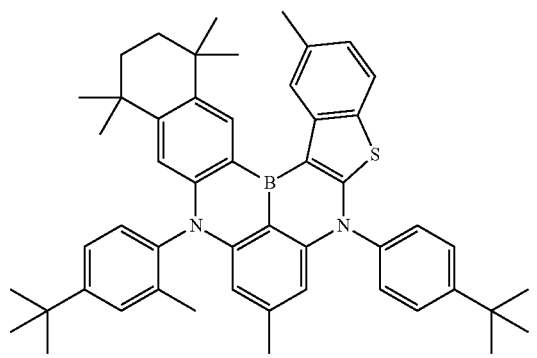
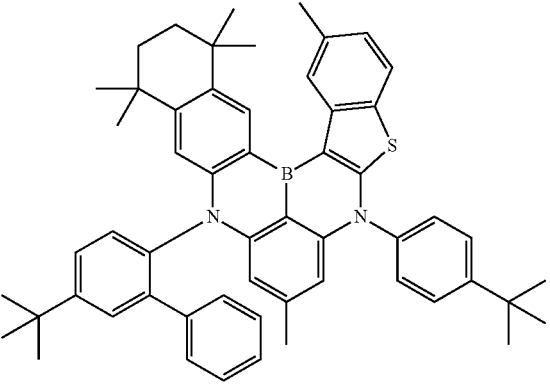
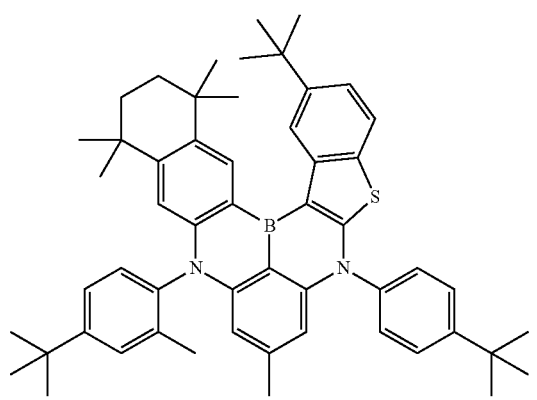
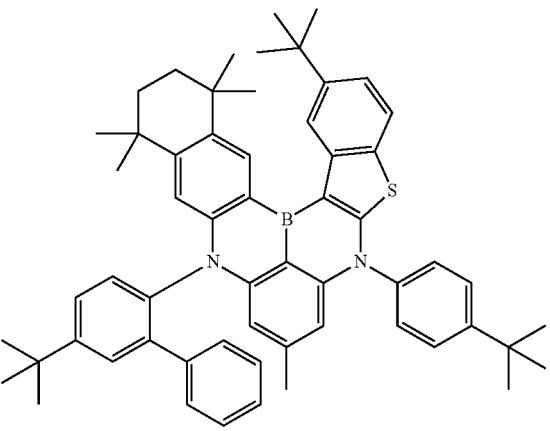

223
224
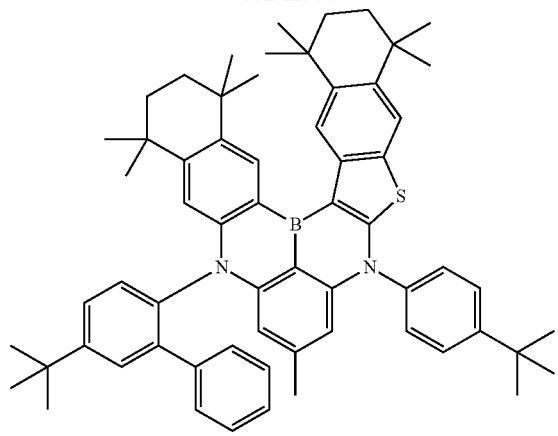
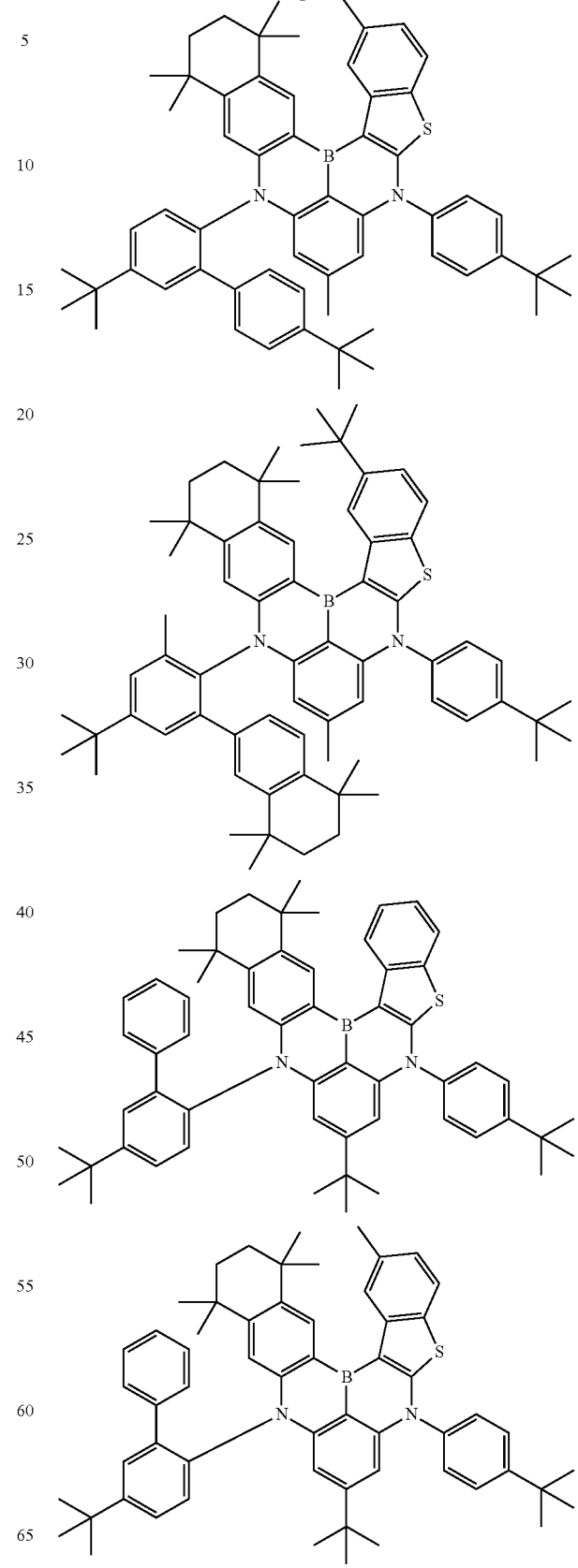

225
-continued
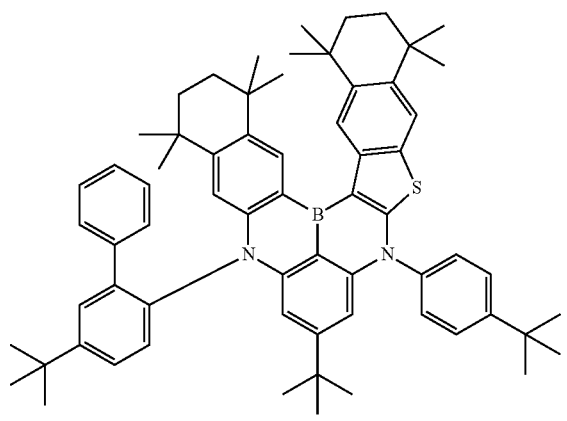
226
-continued
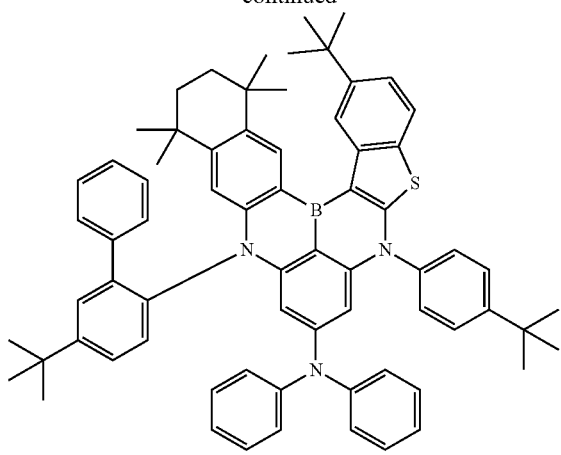
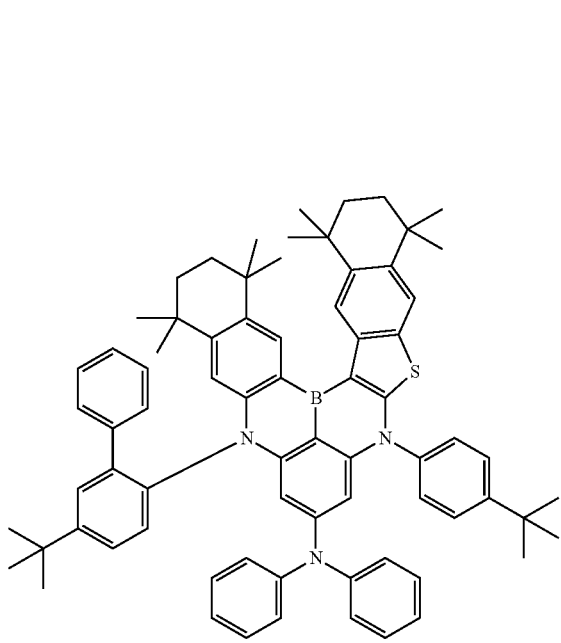
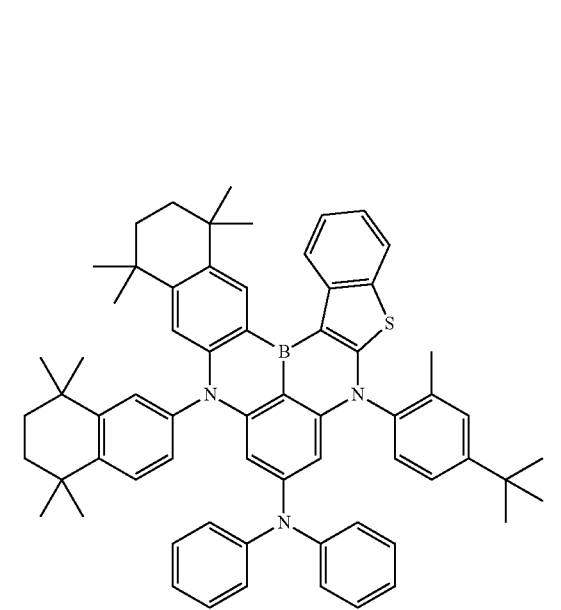

227
-continued
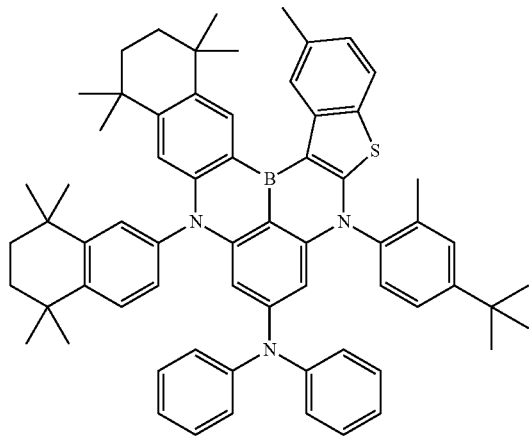
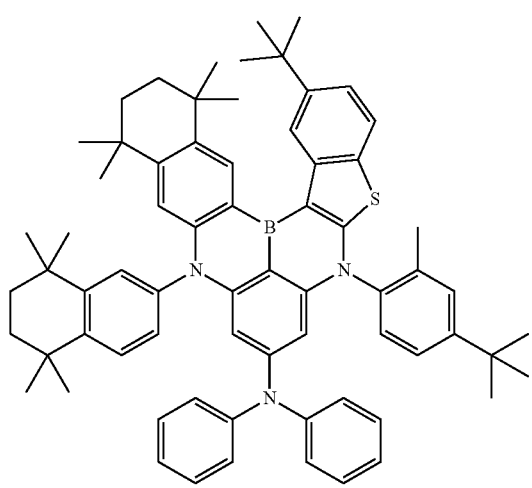
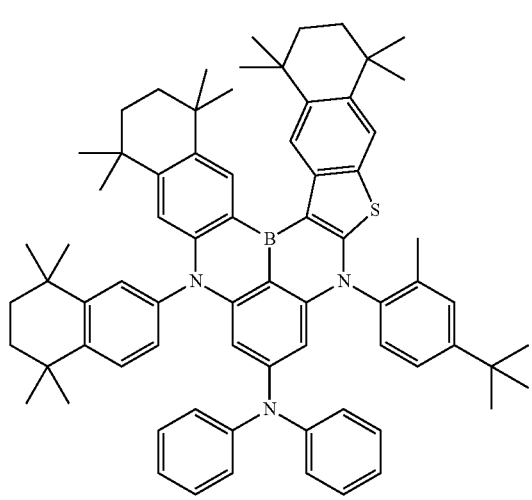
228
-continued
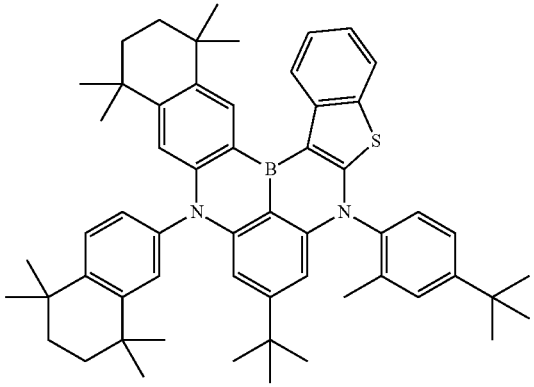
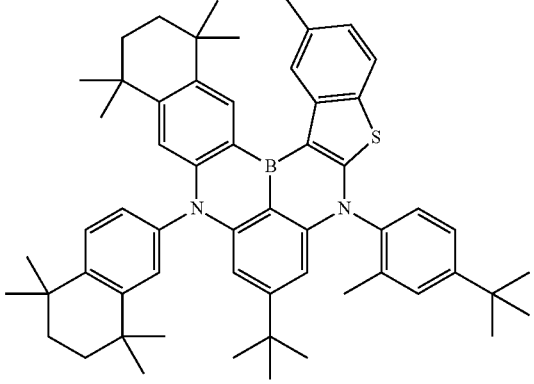
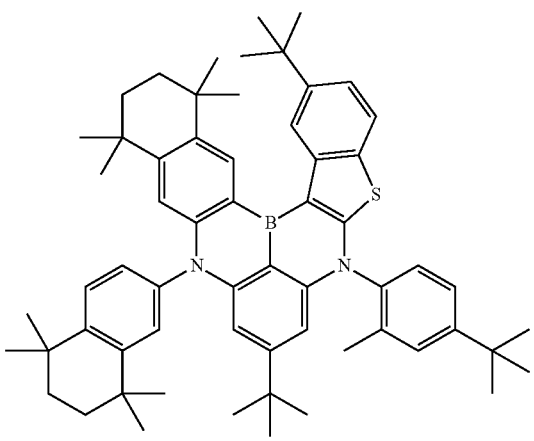
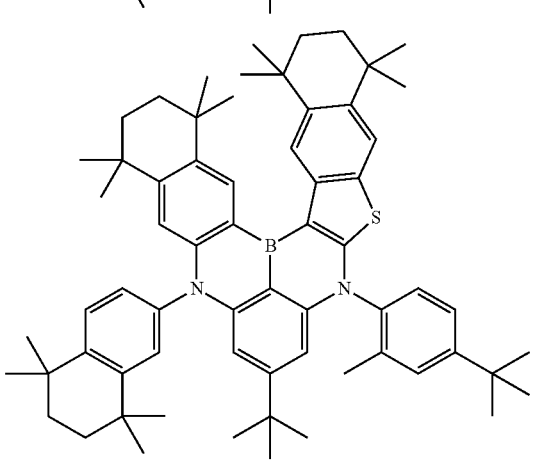

229
-continued
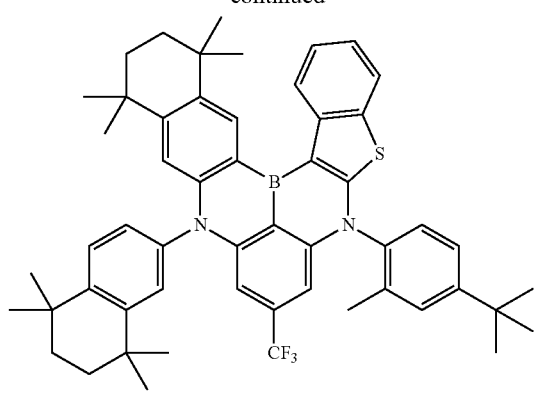
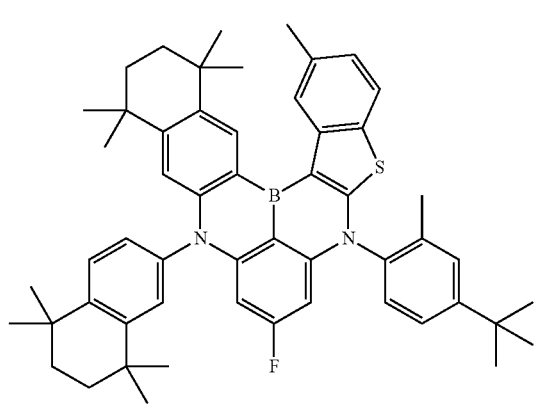
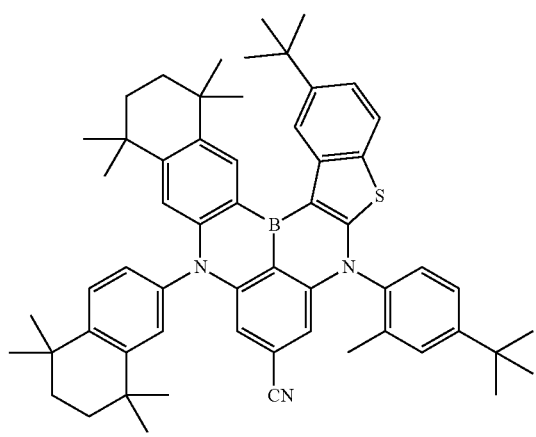
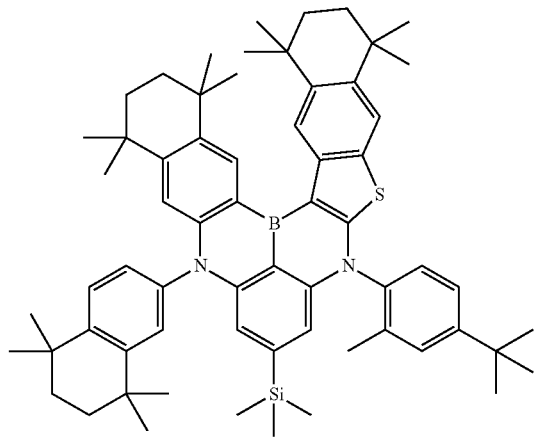
230
-continued
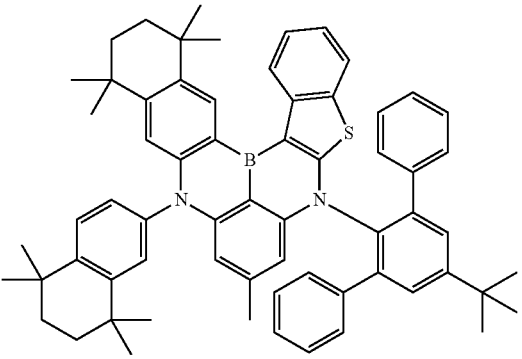
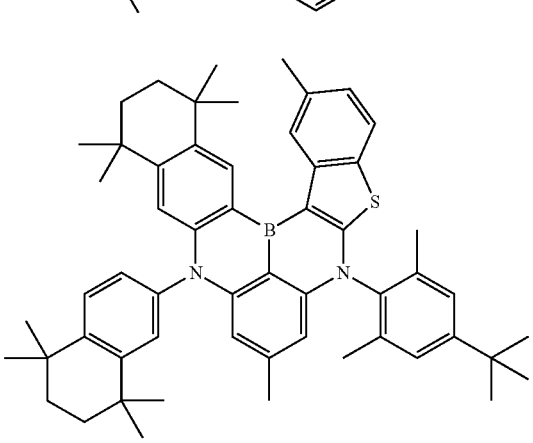
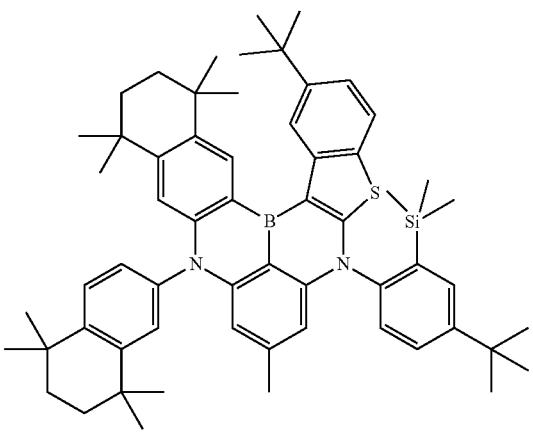
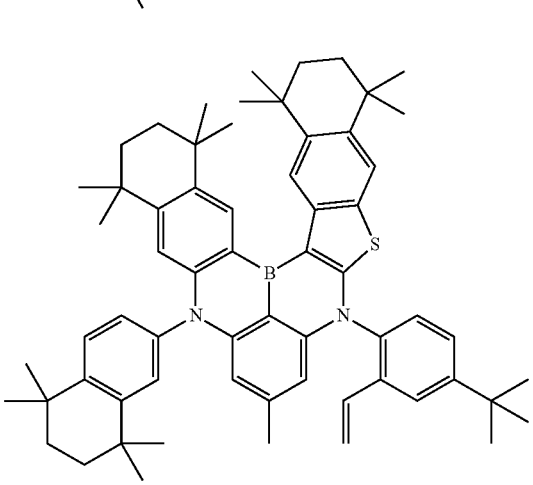

231
-continued
232
-continued
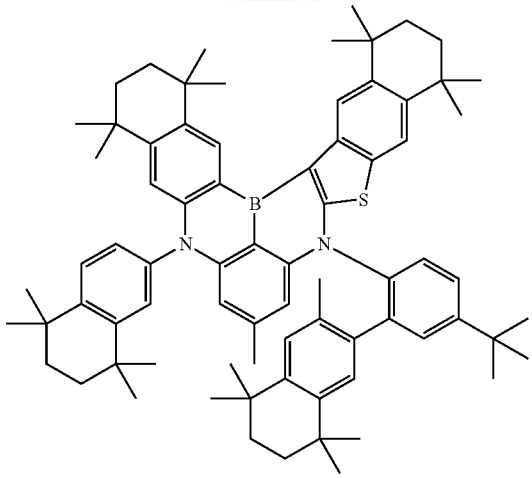
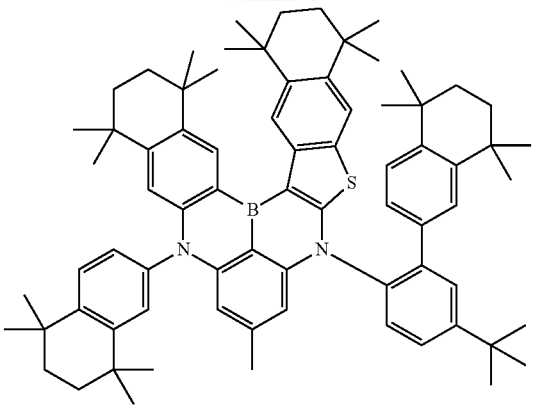
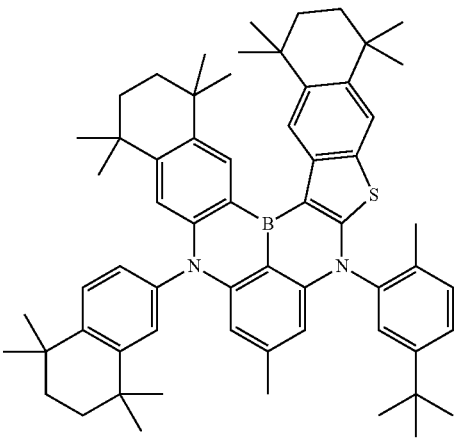
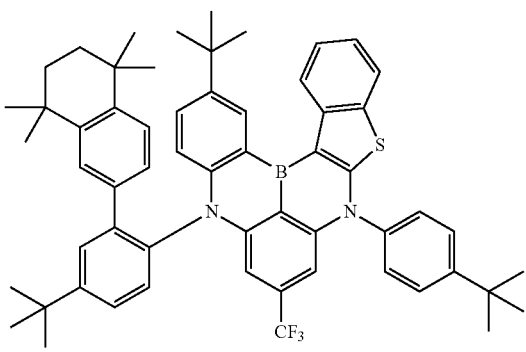
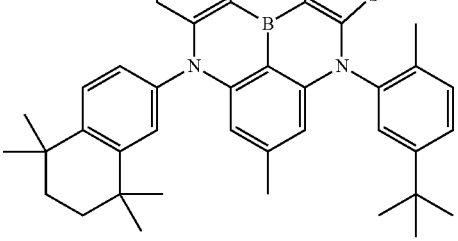
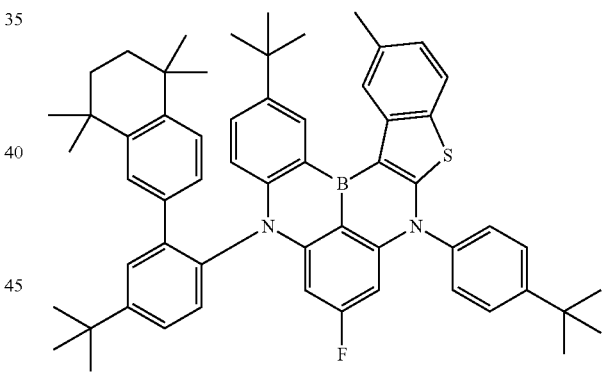
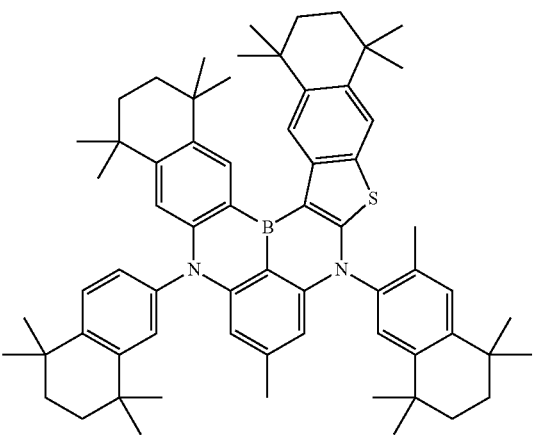
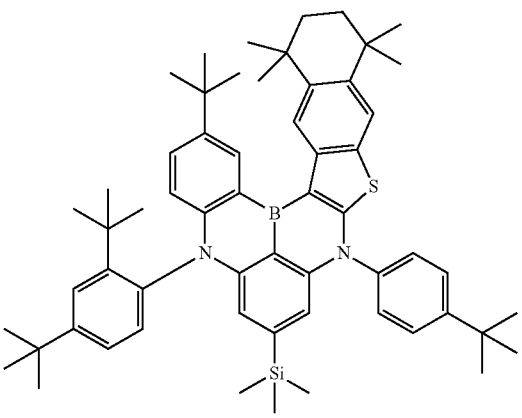

233
-continued
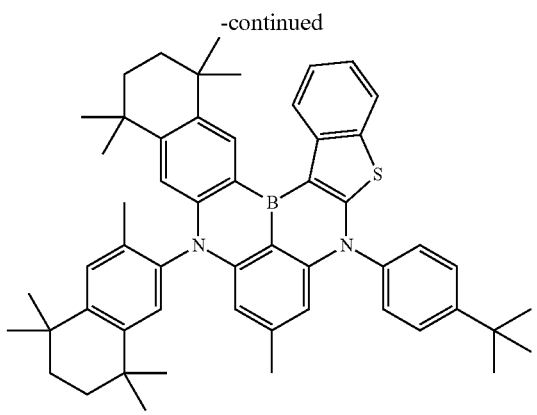
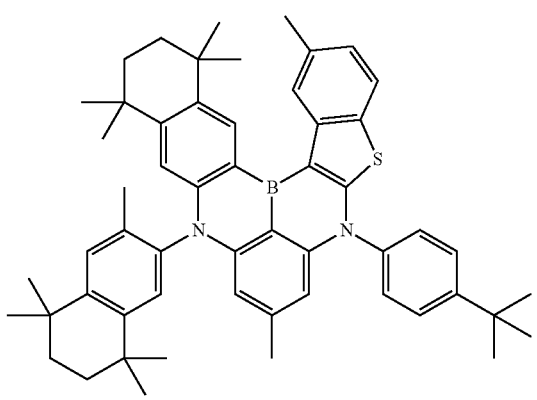
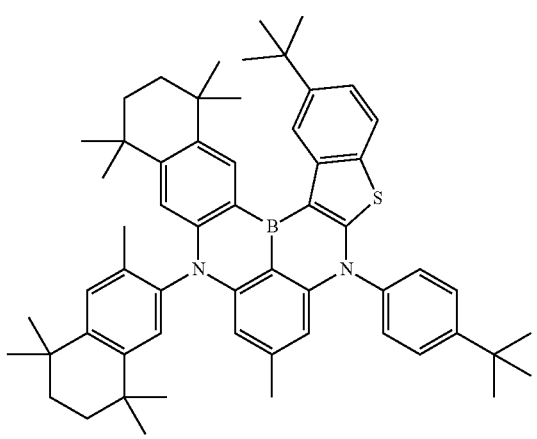
234
-continued
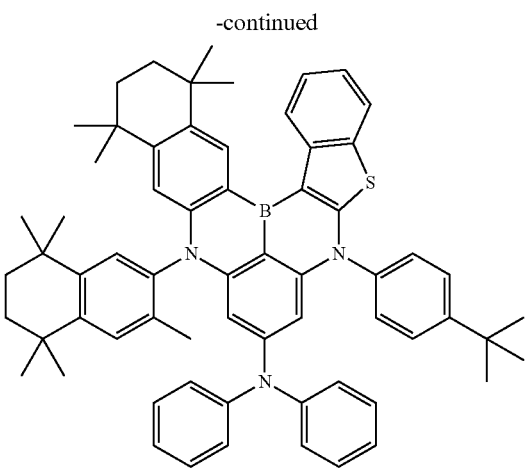
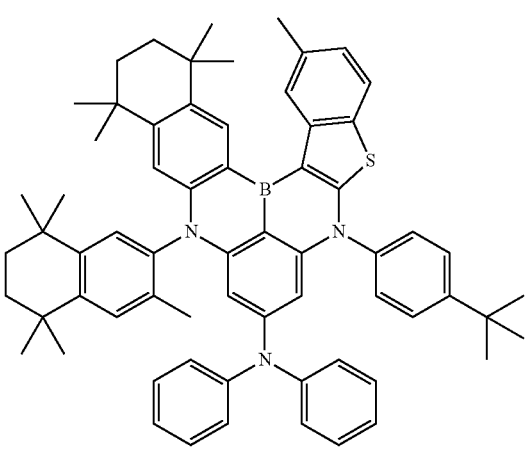
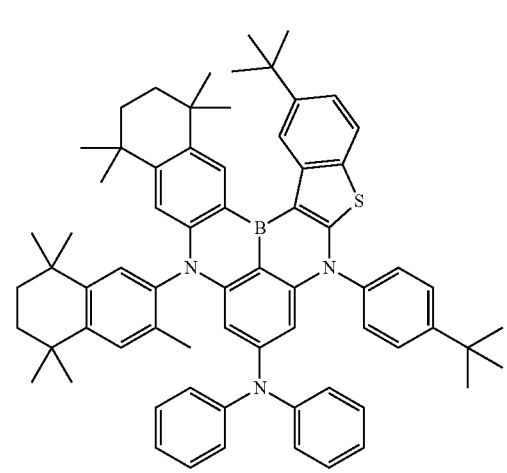

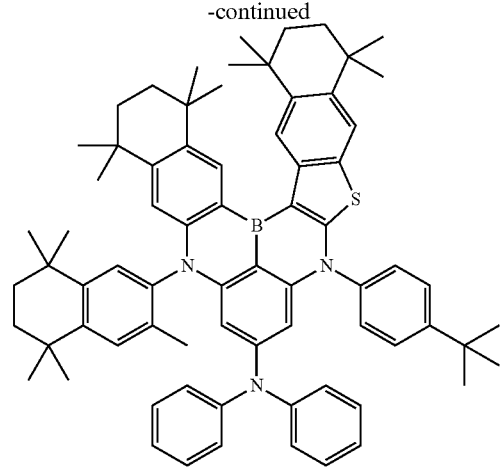
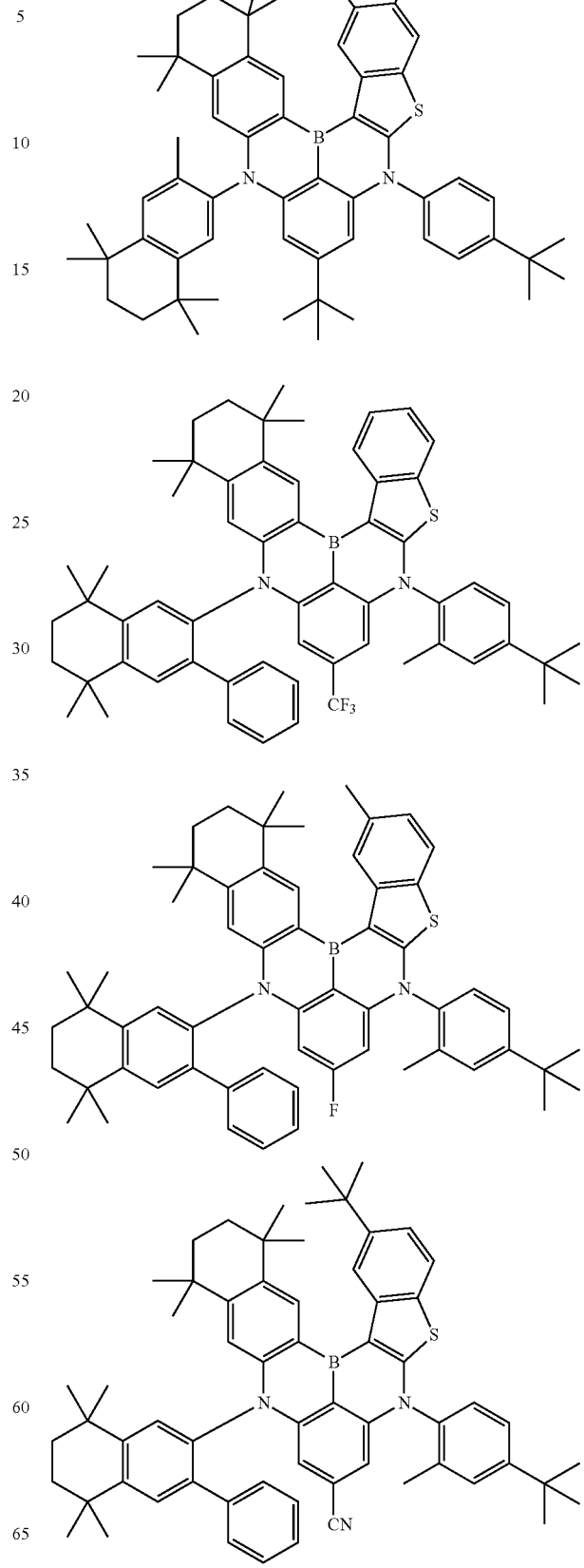

237
-continued
238
-continued
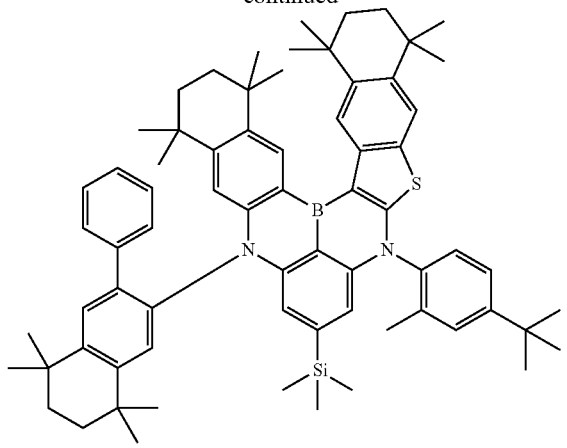
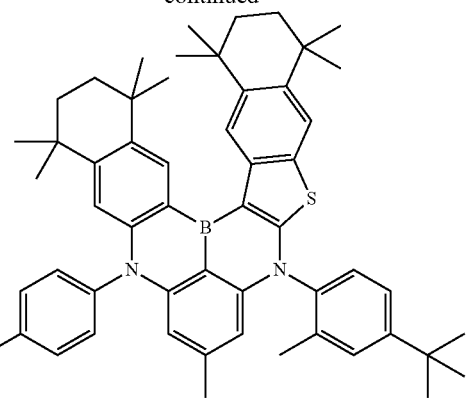
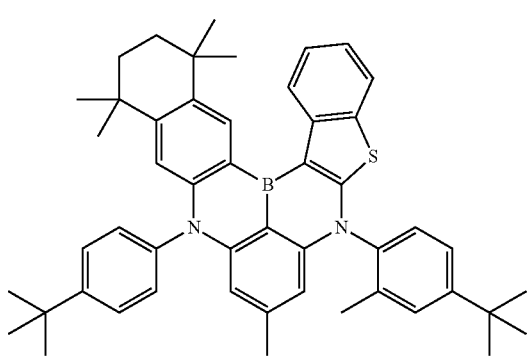
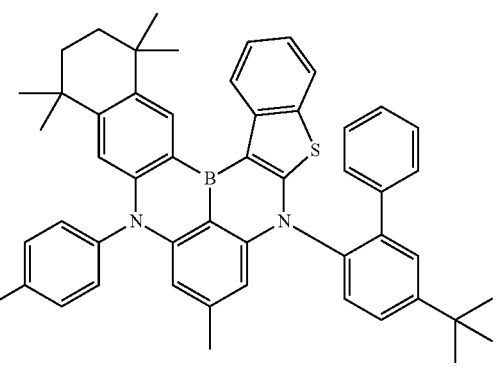
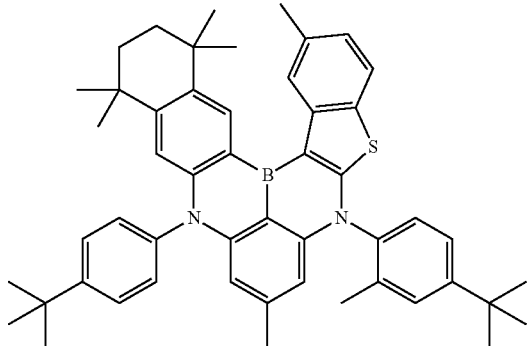
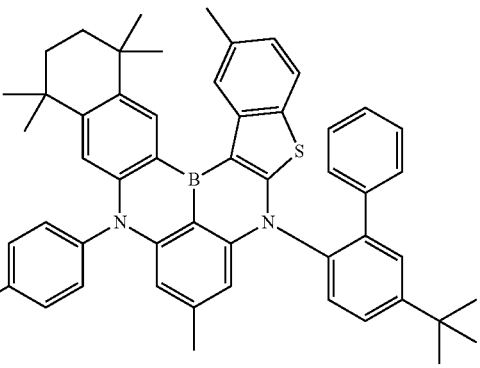
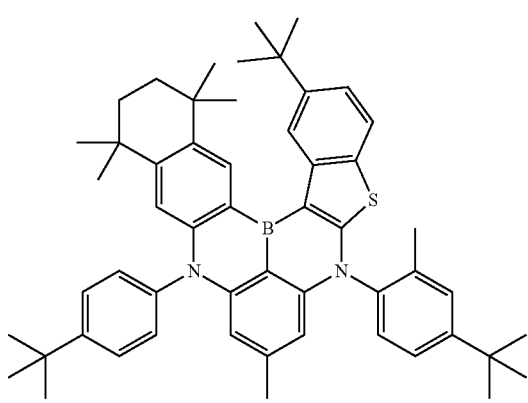
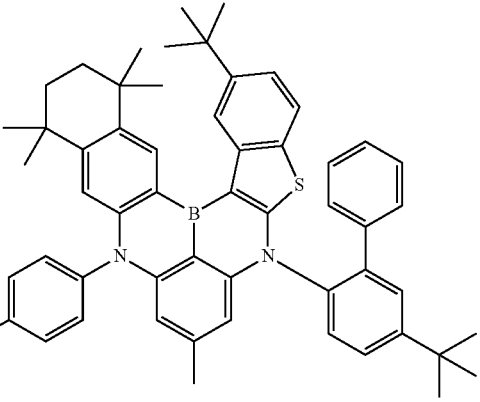

239
-continued
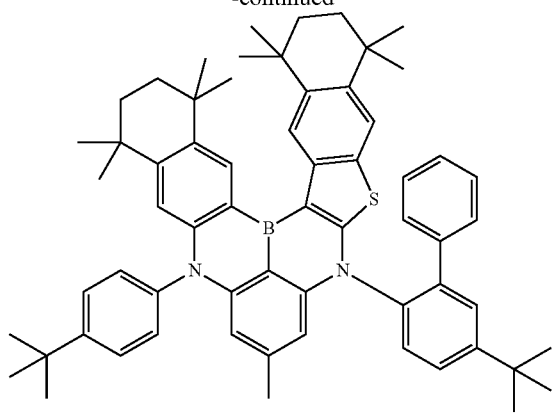
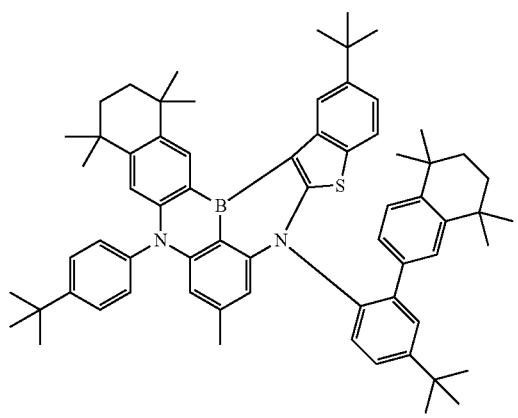
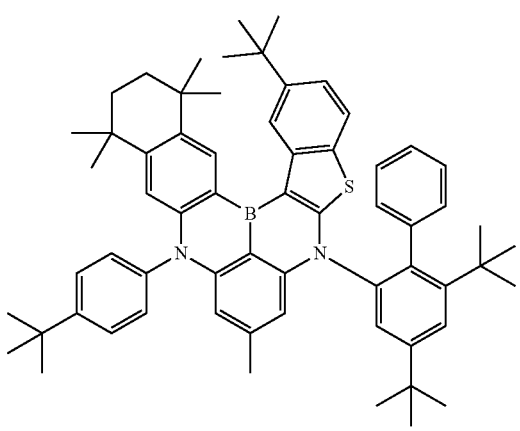
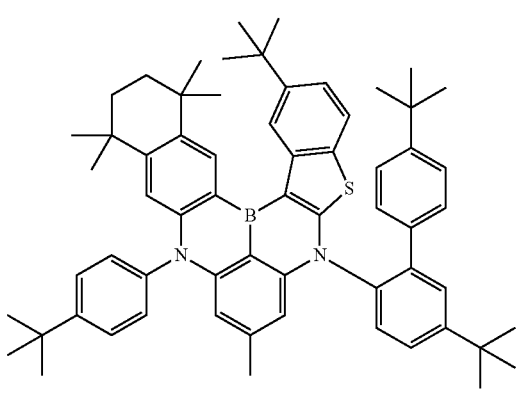
240
-continued
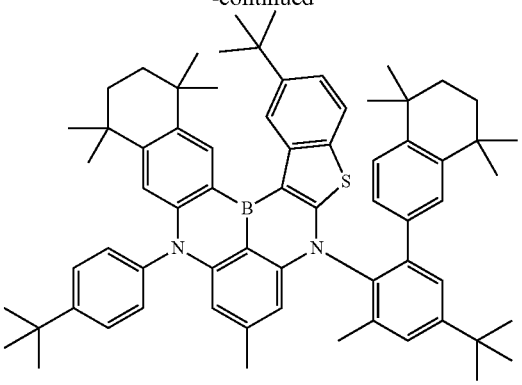
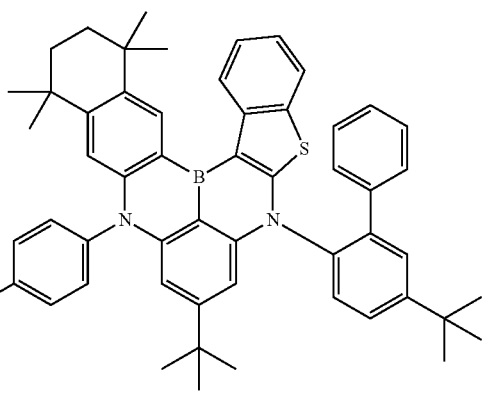
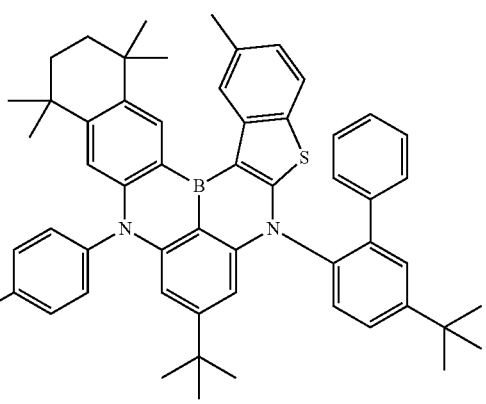
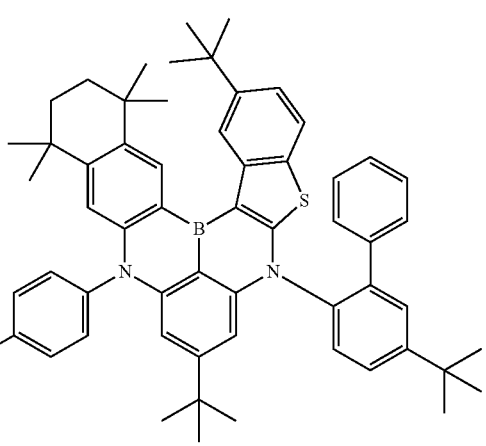

-continued
241
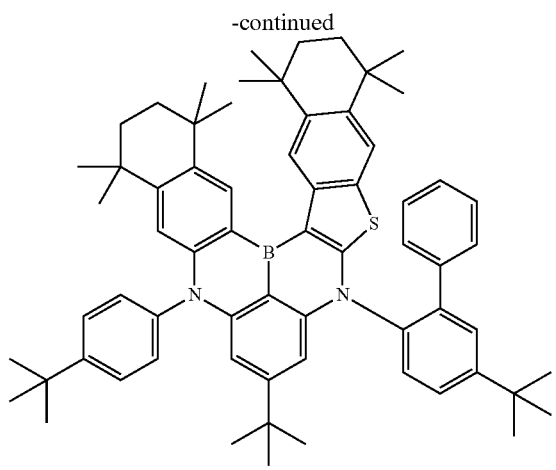
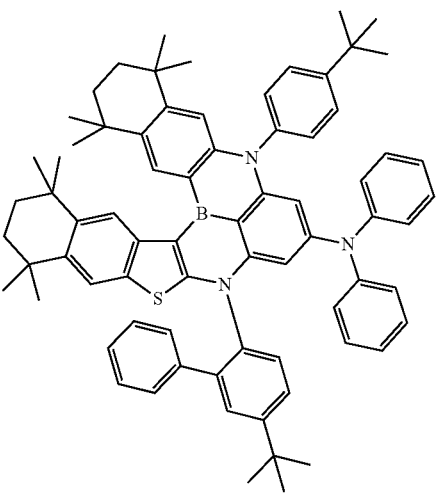
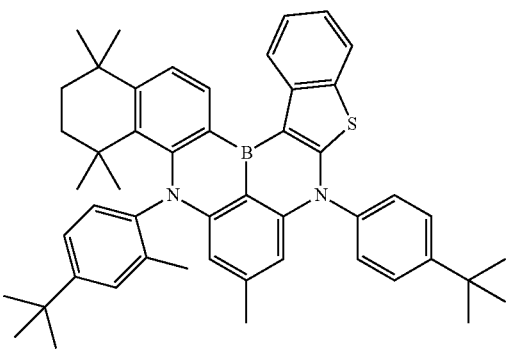
242
-continued
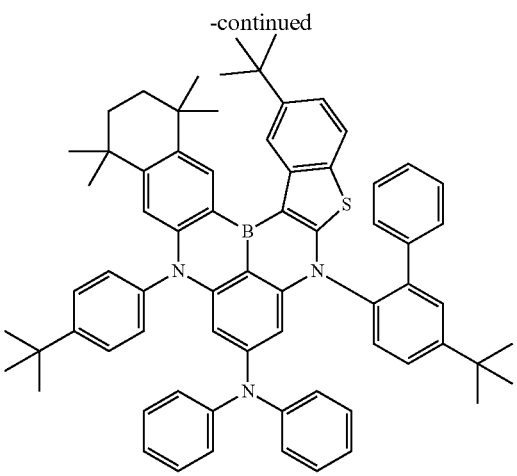
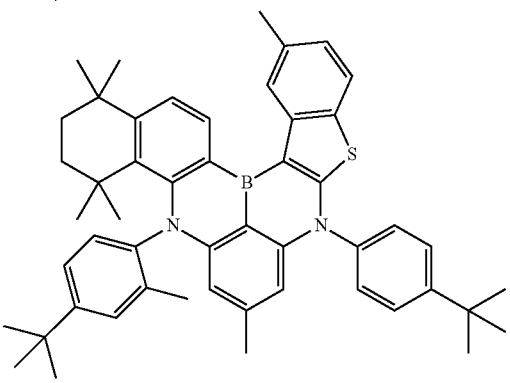

243
-continued
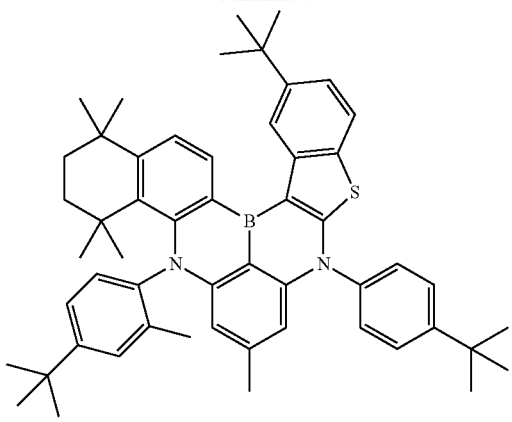
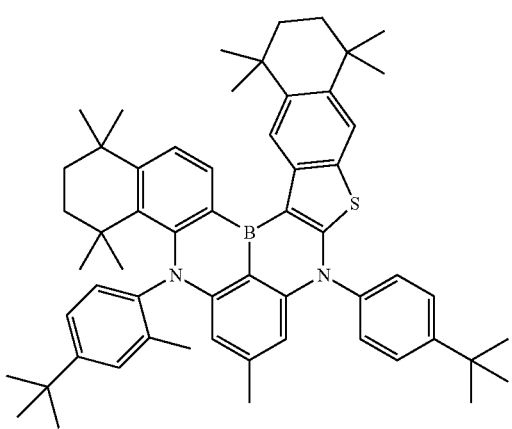
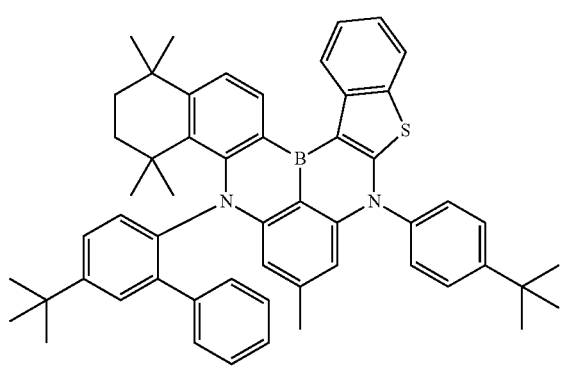
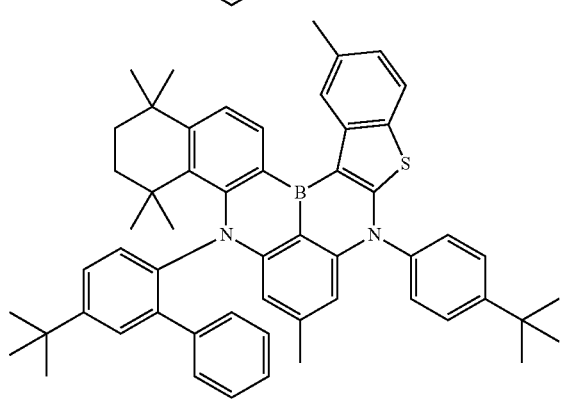
244
-continued
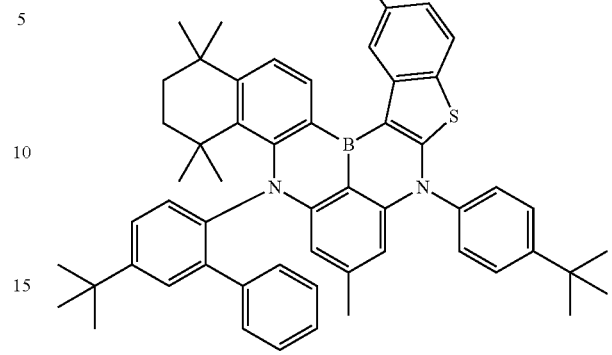
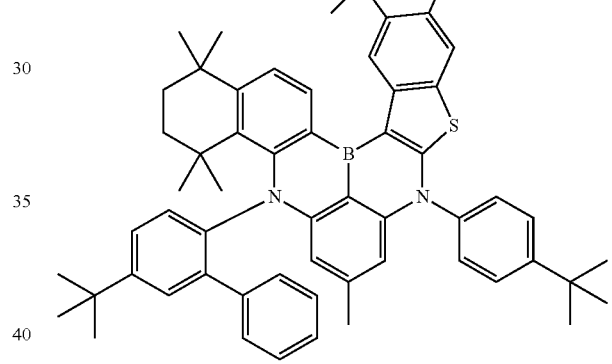
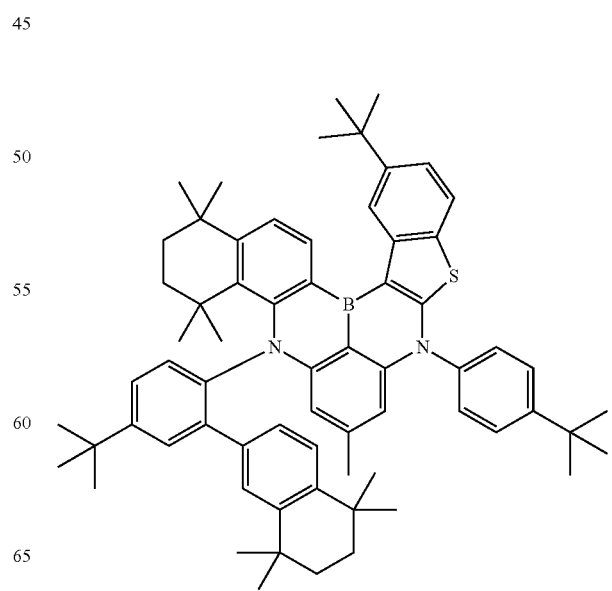

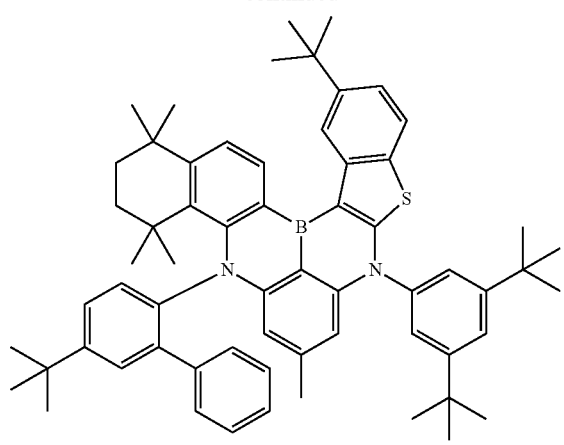
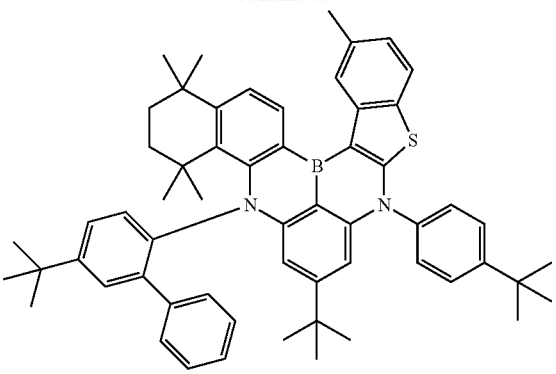
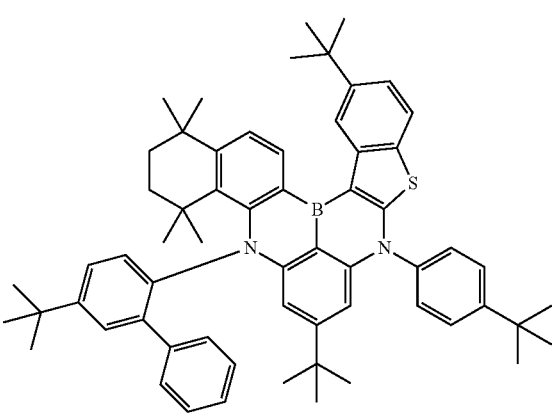
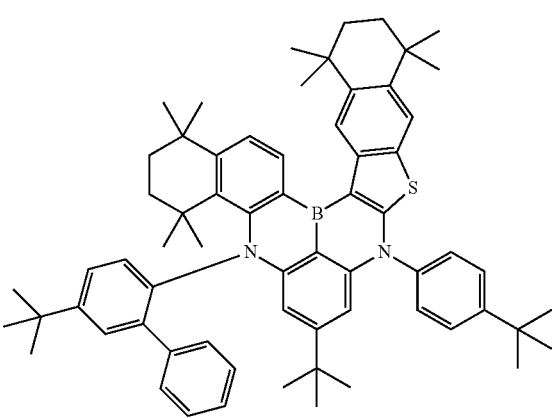
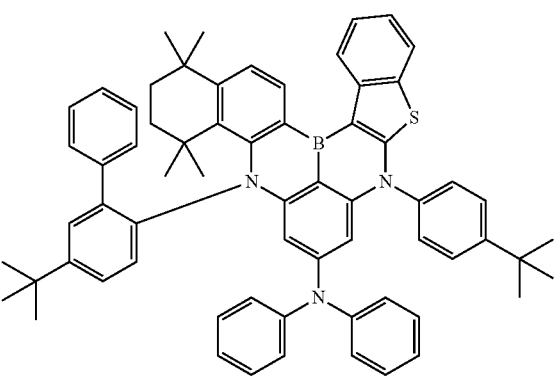

247
-continued
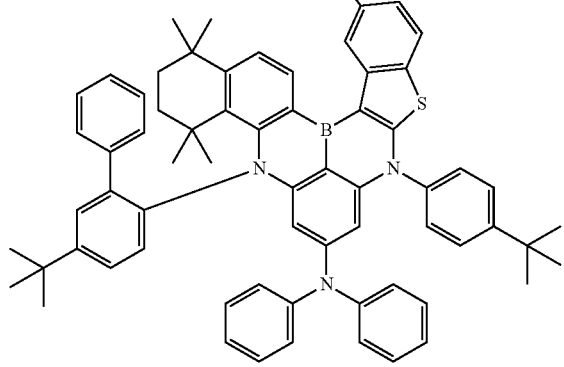
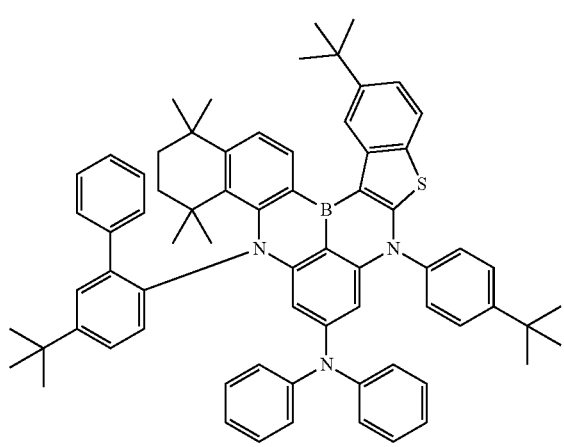
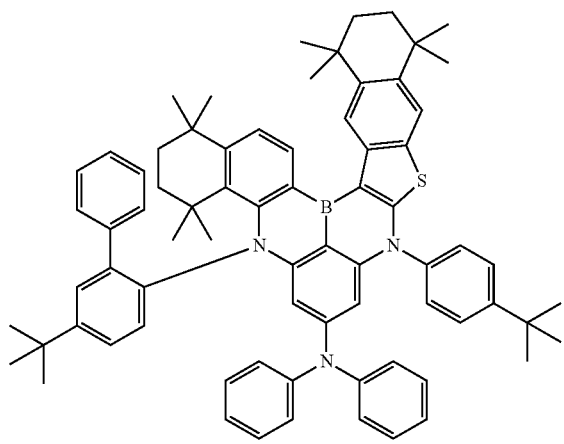
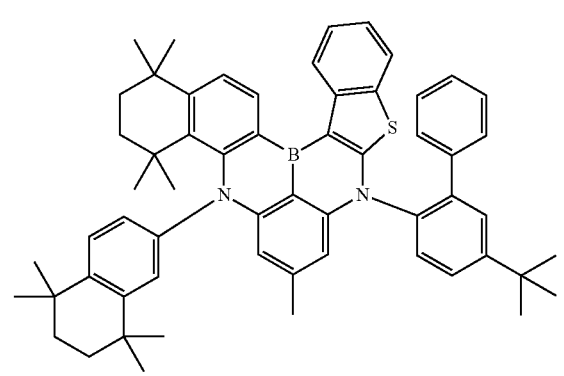
248
-continued
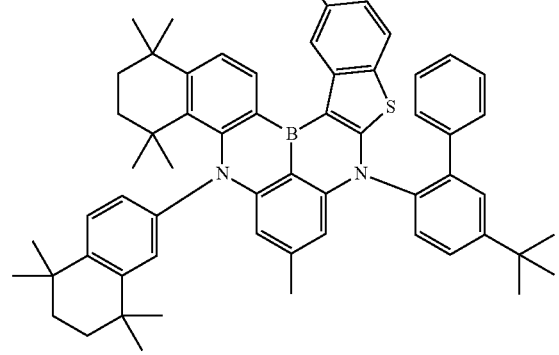
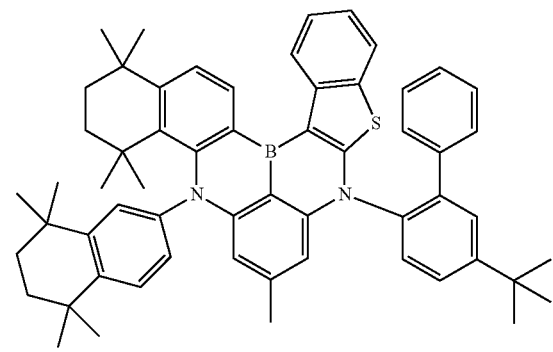
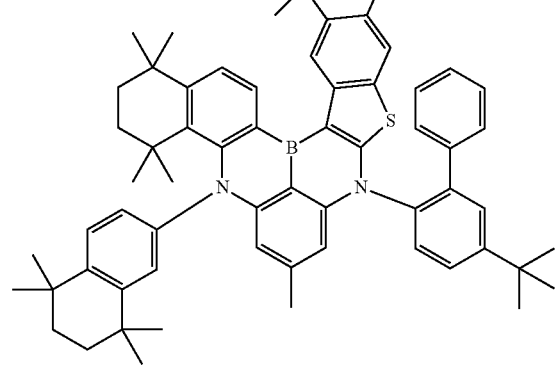
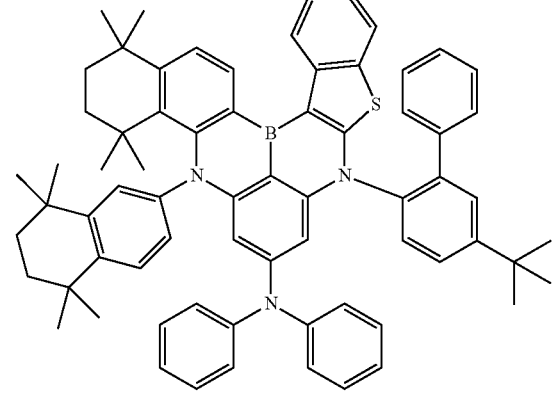

249 -continued
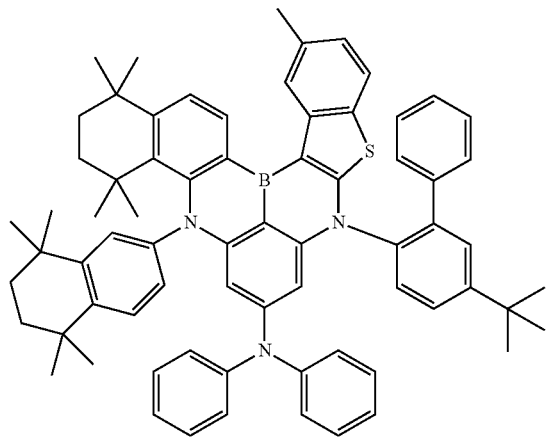
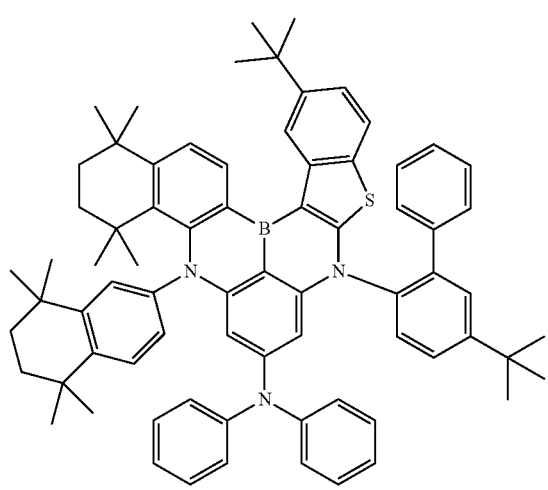
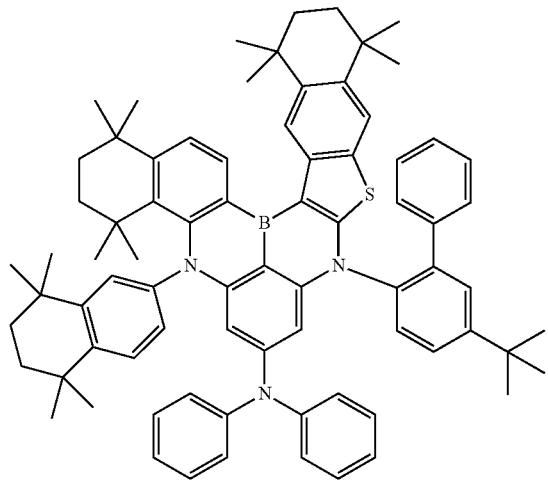
250 -continued
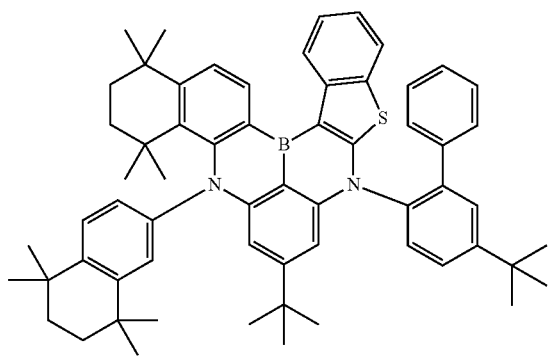
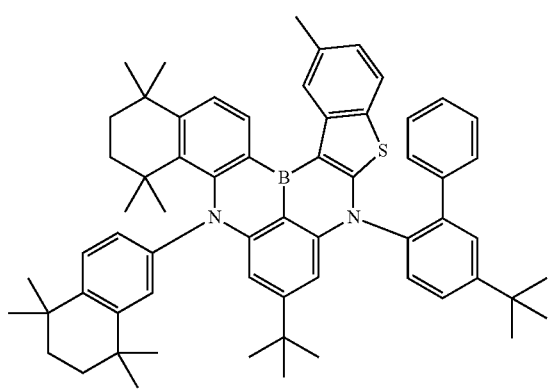
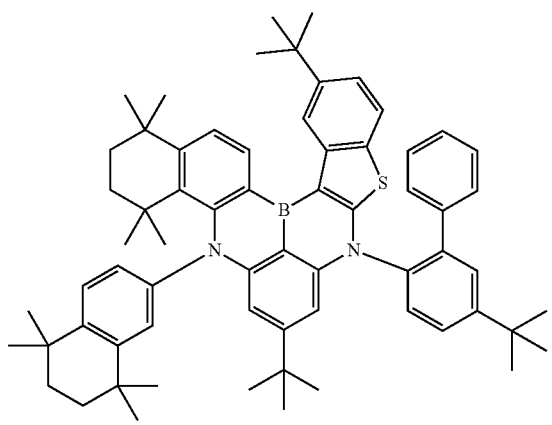
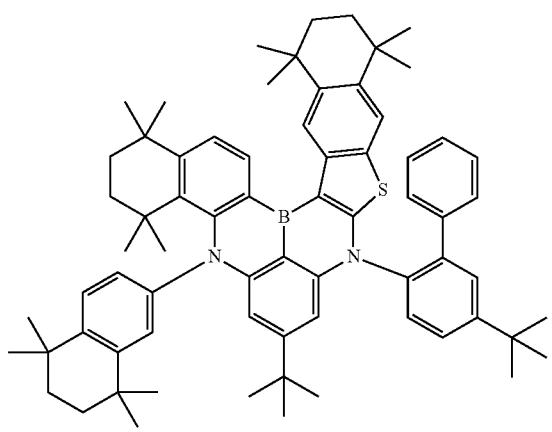

| 251 -continued | 252 -continued |
|---|---|
| 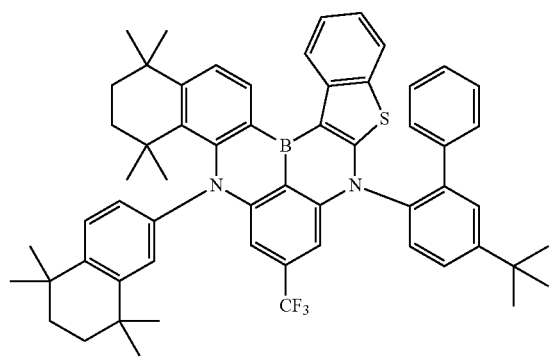 | 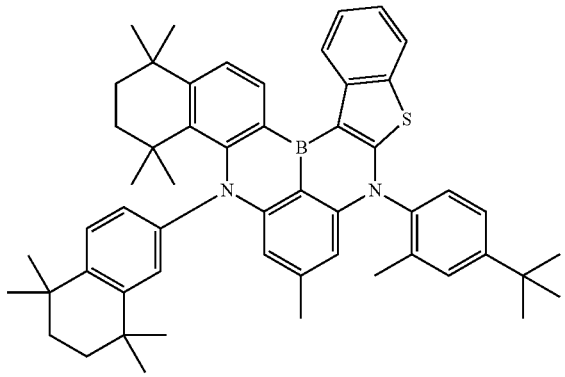 |
| 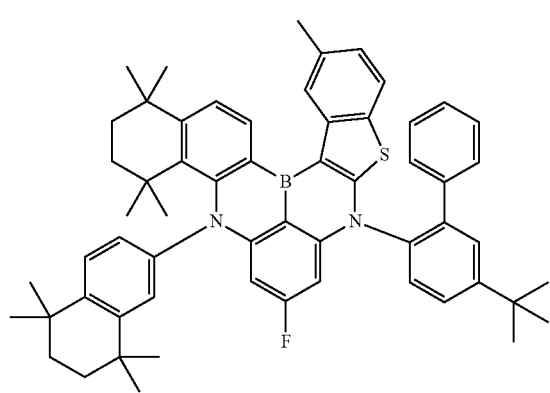 | 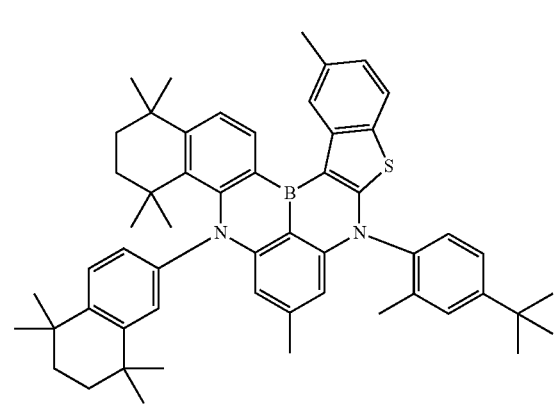 |
| 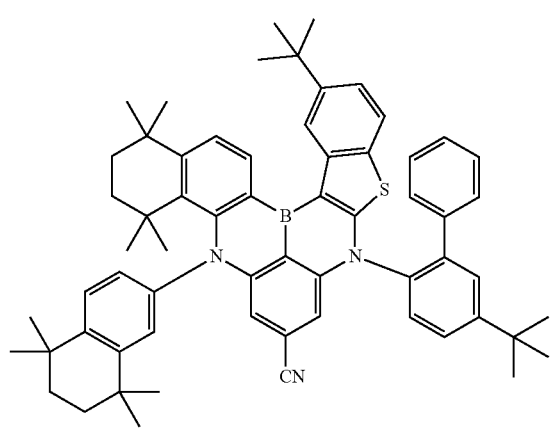 | 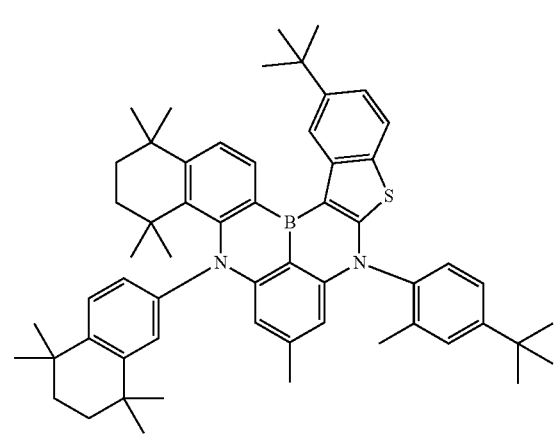 |
| 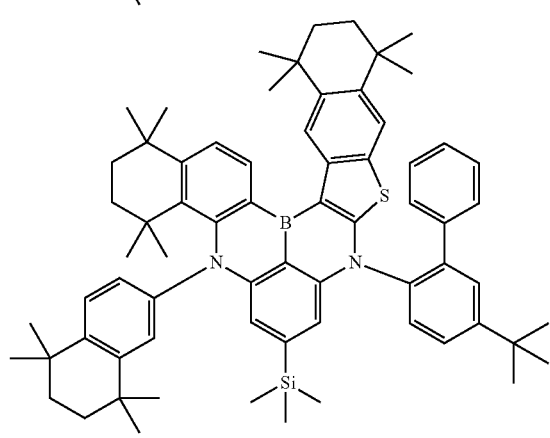 | 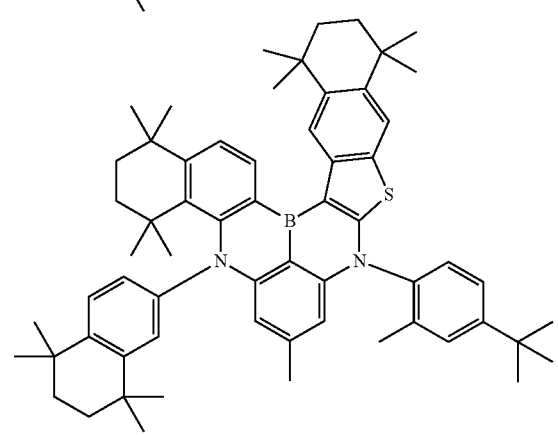 |

253
-continued
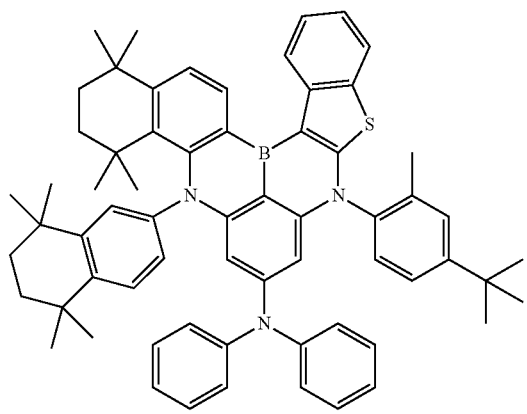
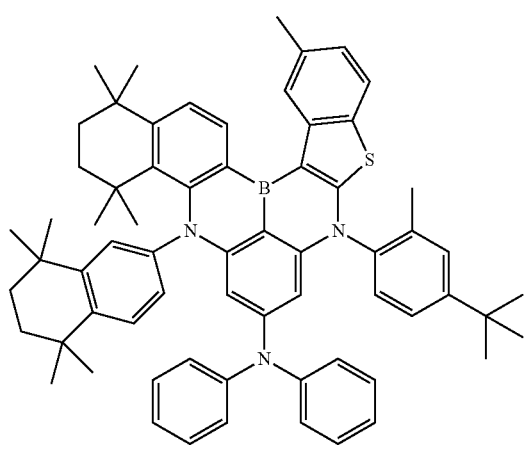
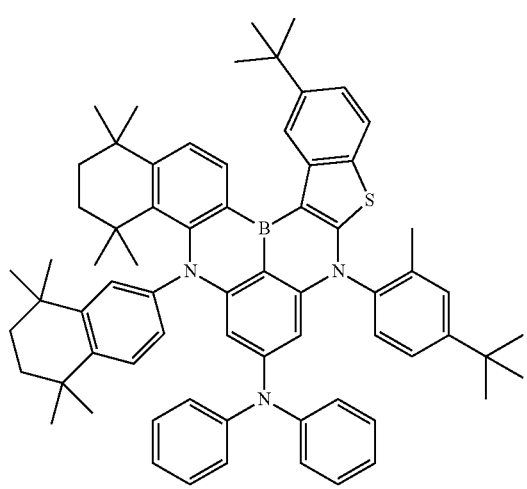
254
-continued
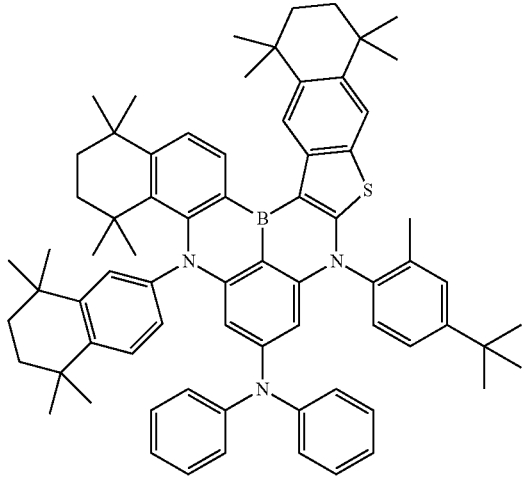
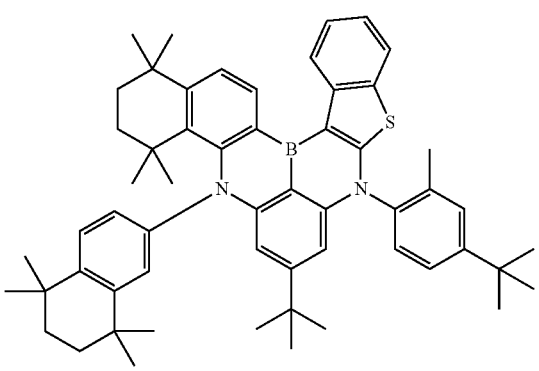
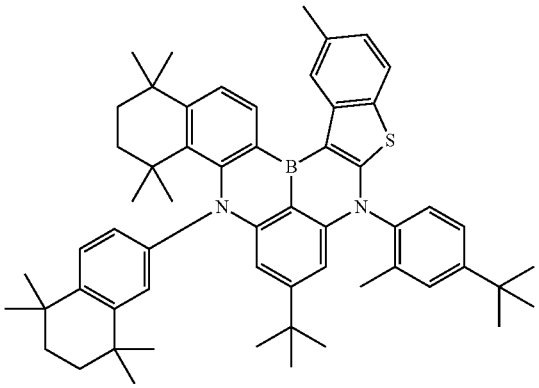
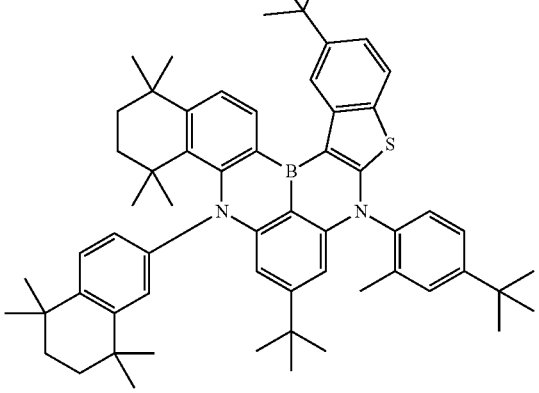

255
-continued
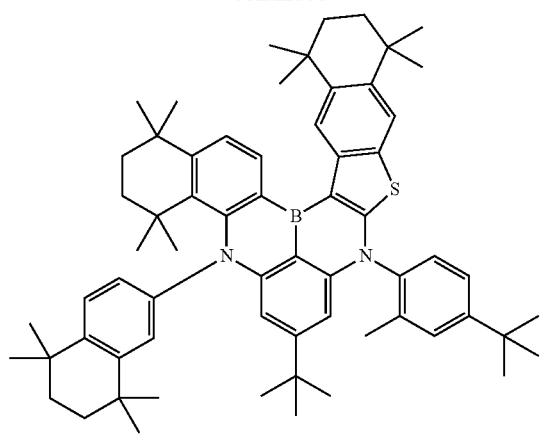
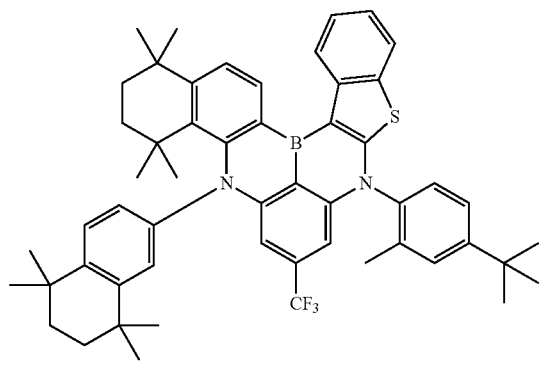
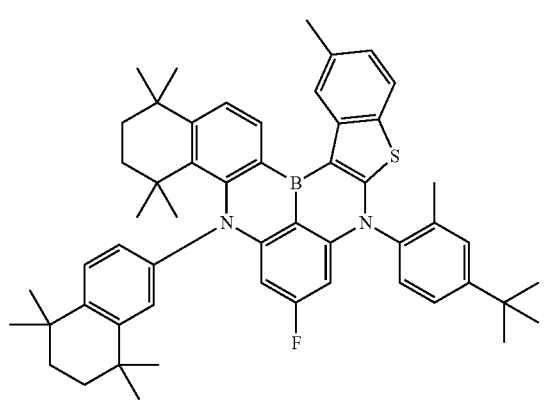
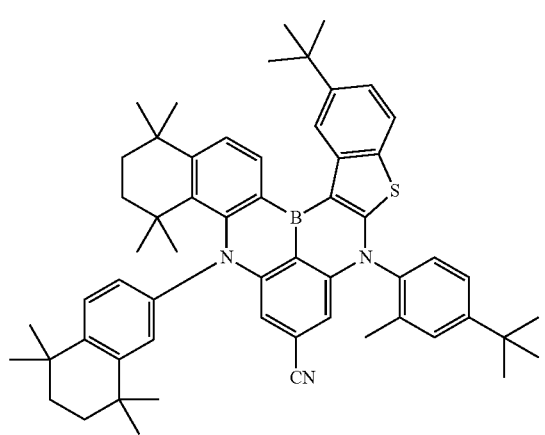
256
-continued
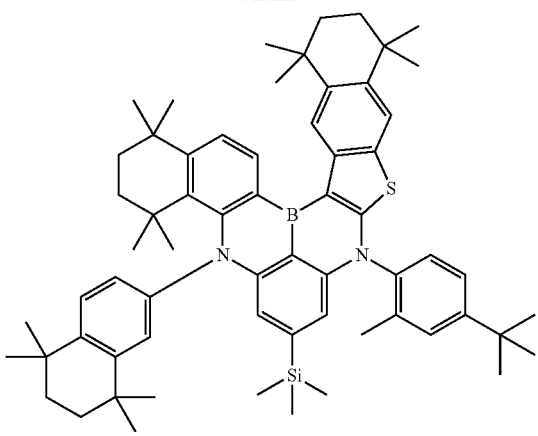
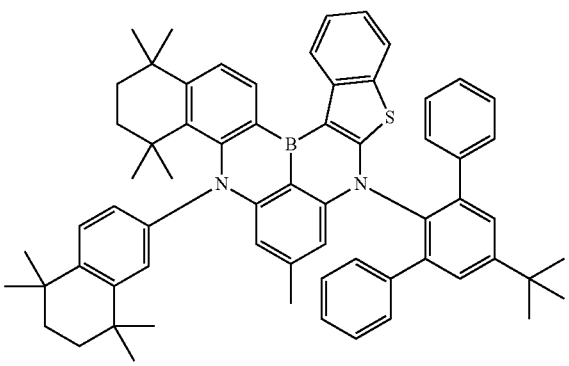
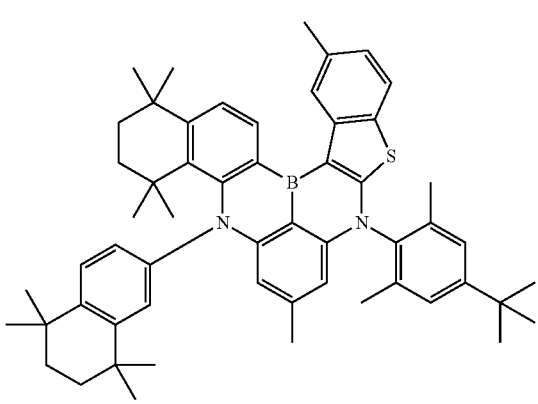
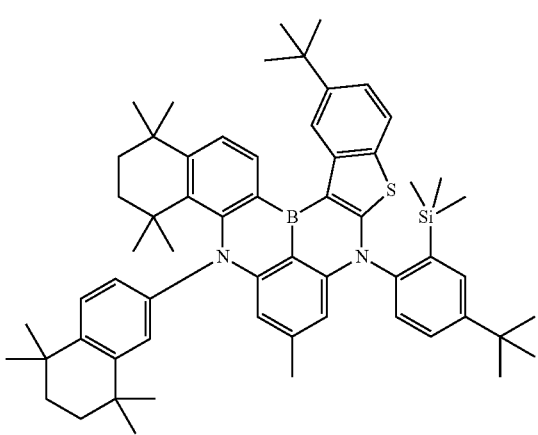

257
-continued
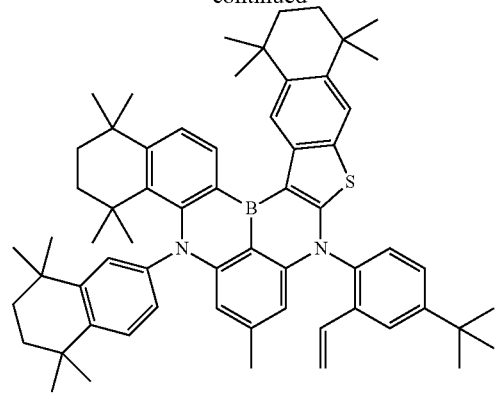
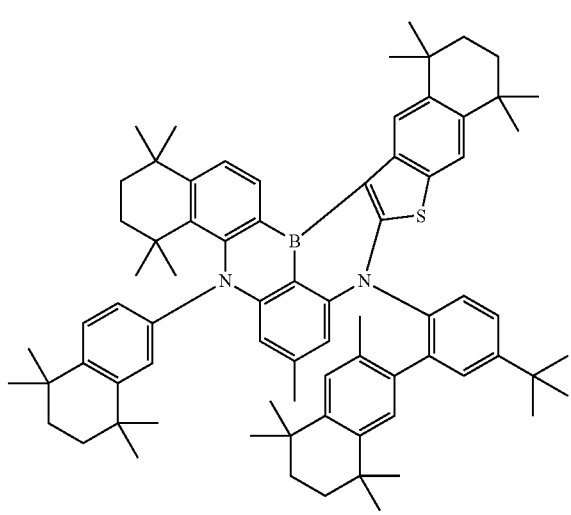
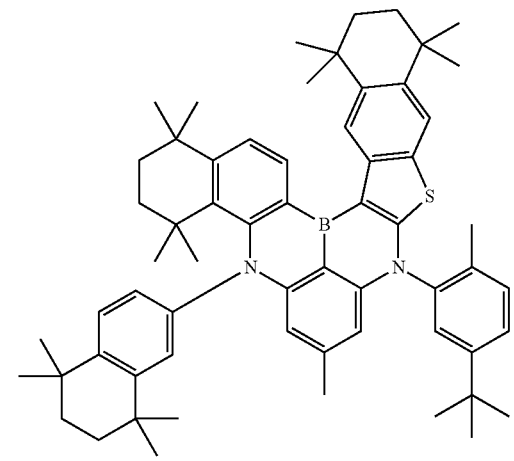
258
-continued
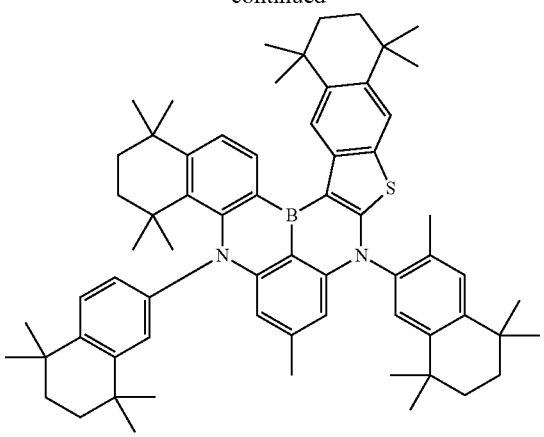
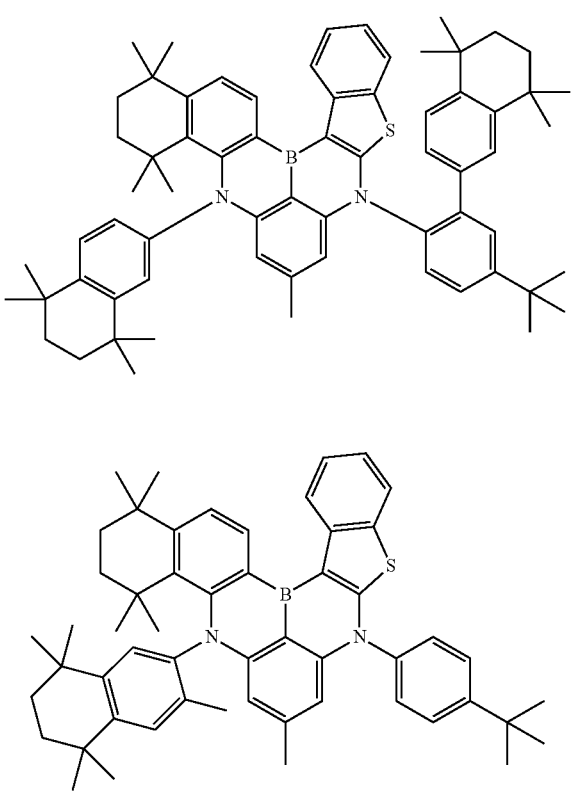
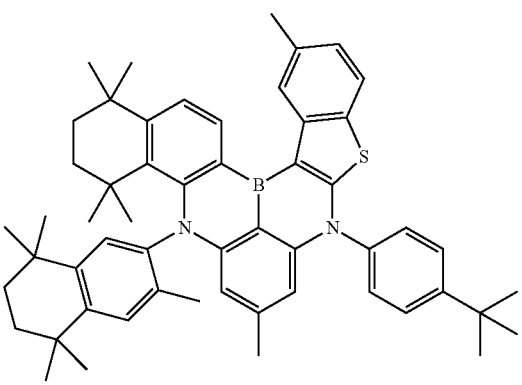

259
-continued
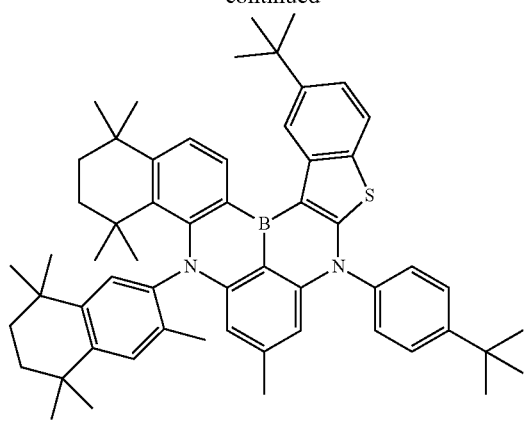
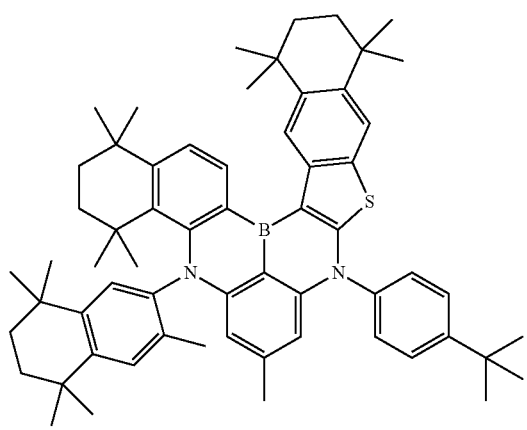
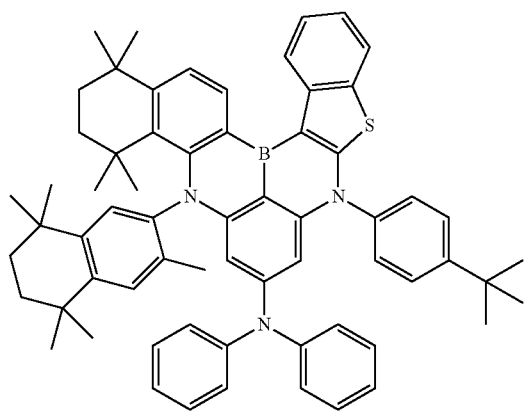
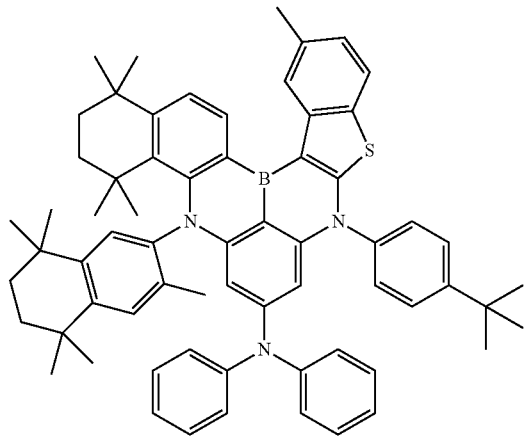
260
-continued
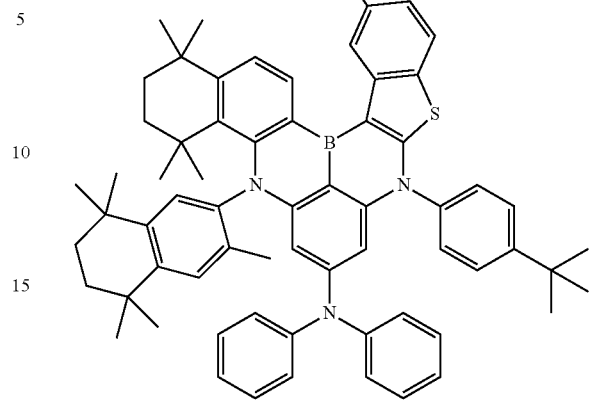
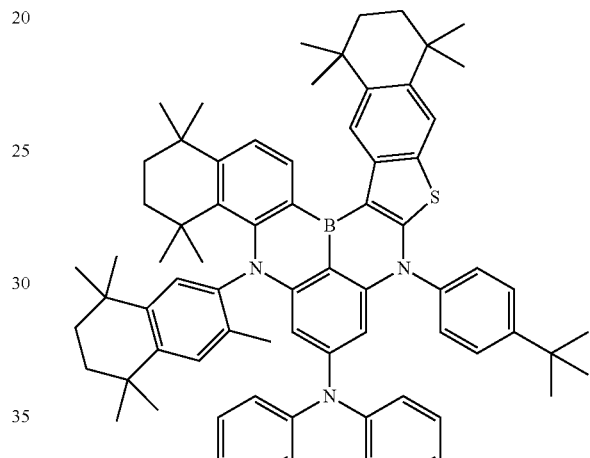
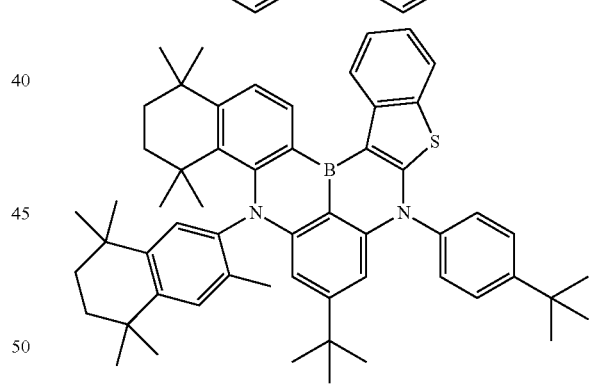
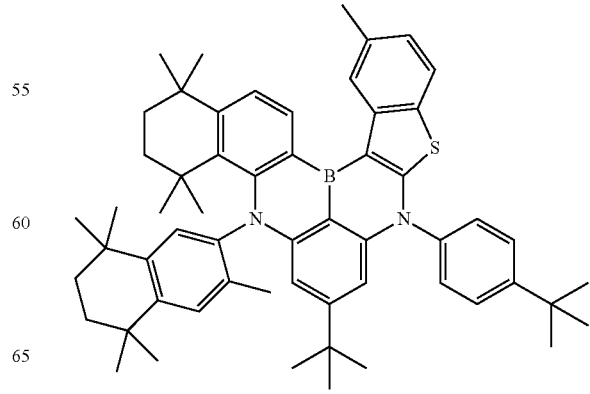

-continued
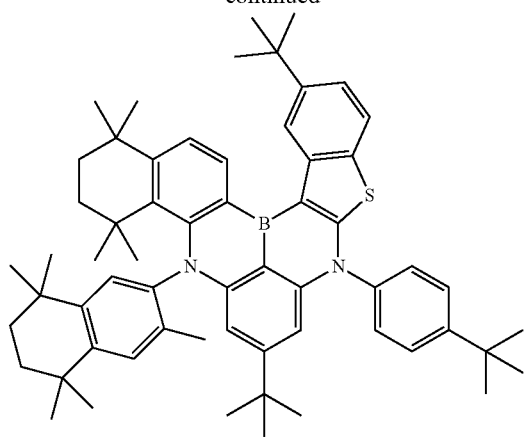 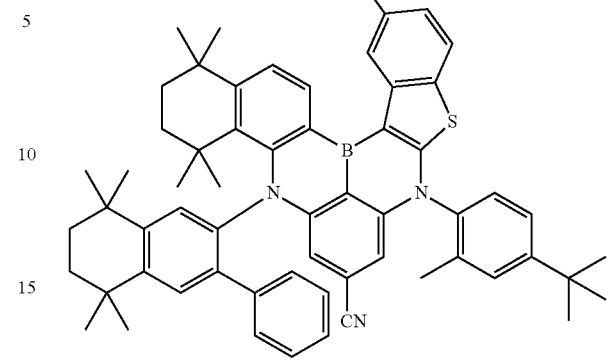
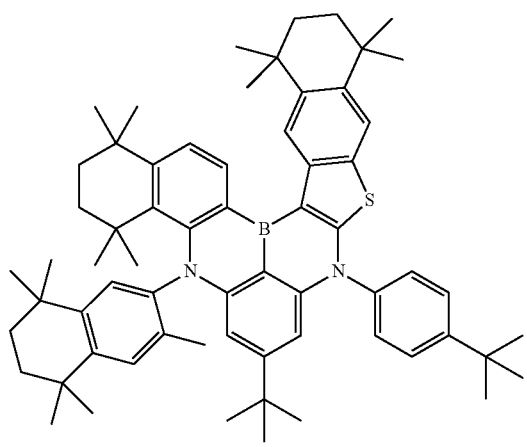 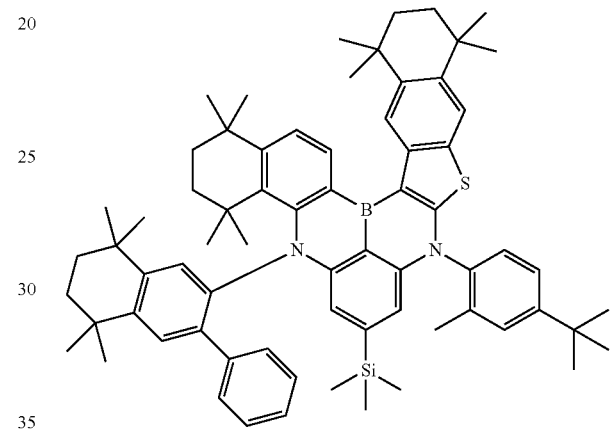
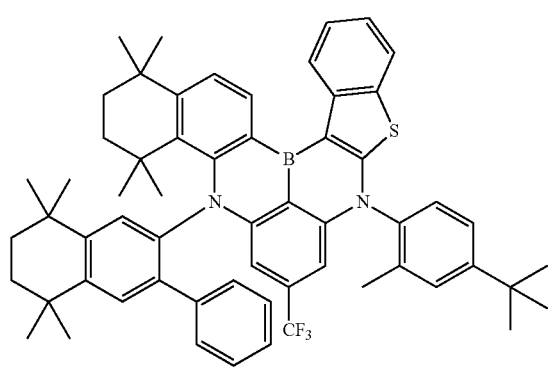 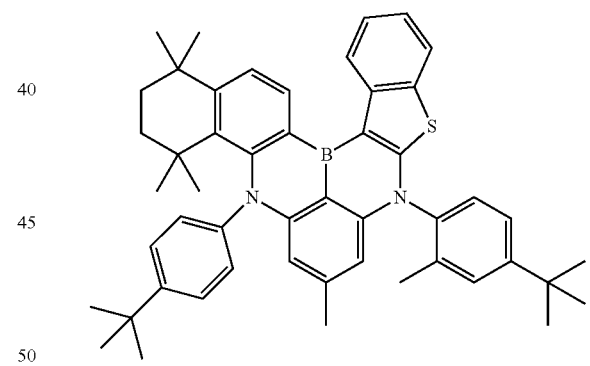
 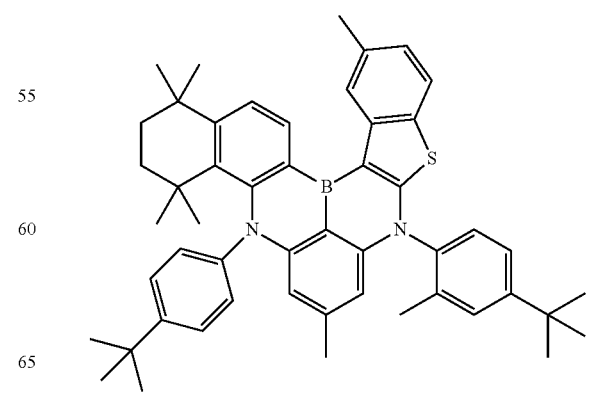

263
-continued
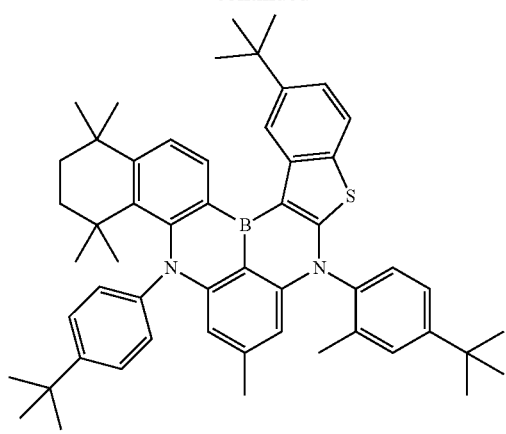
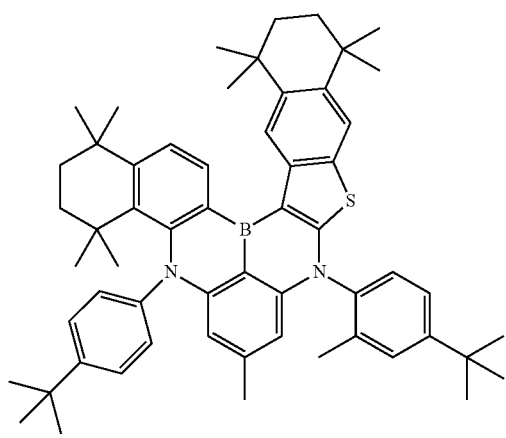
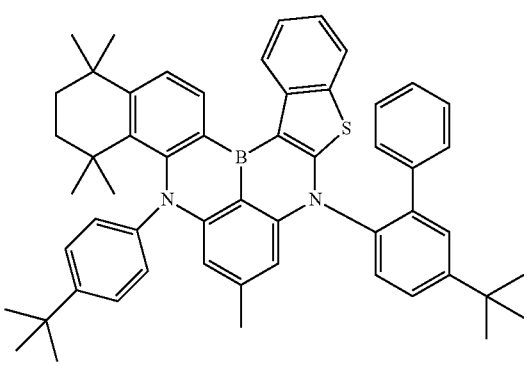
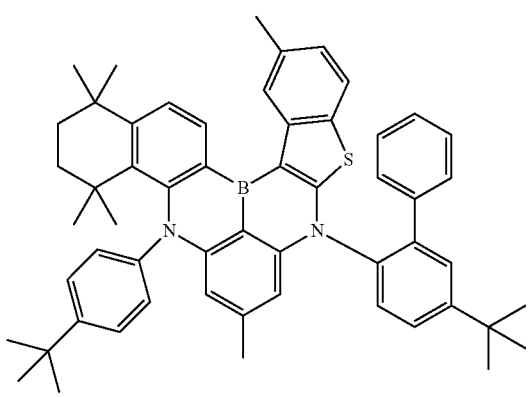
264
-continued
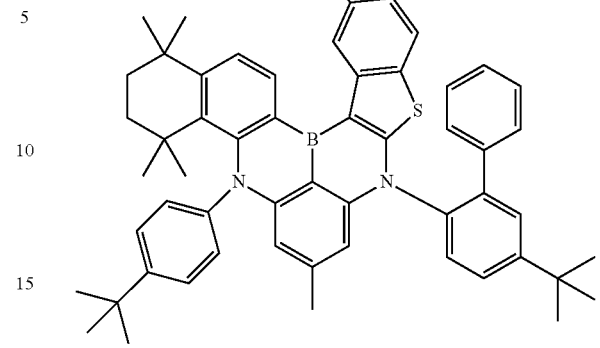
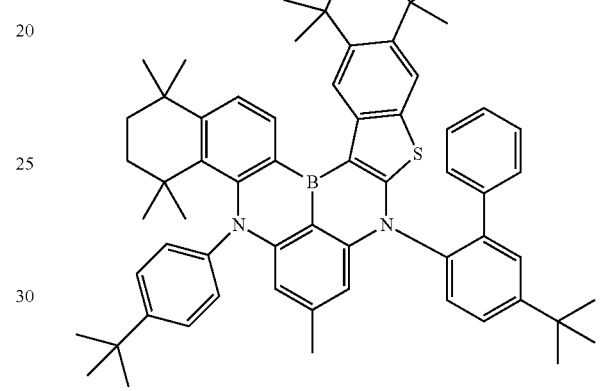
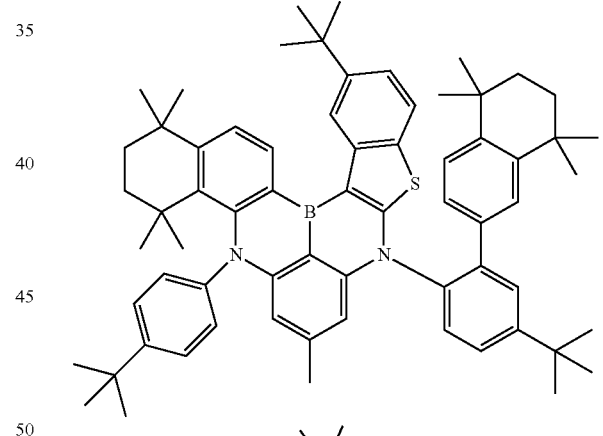
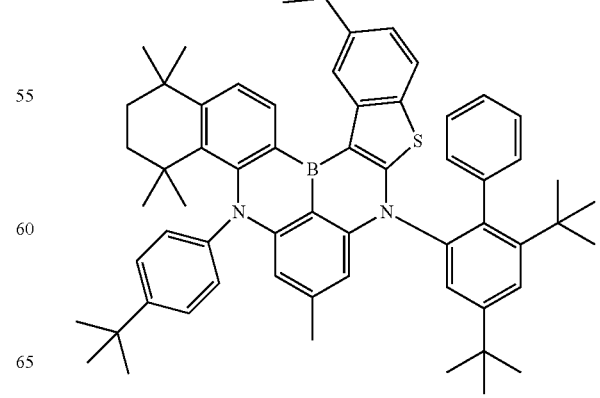

265
-continued
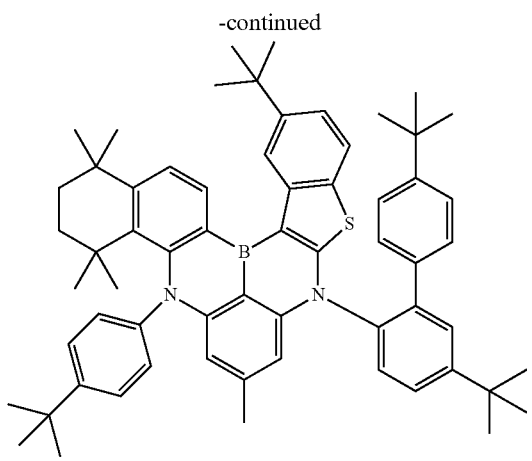
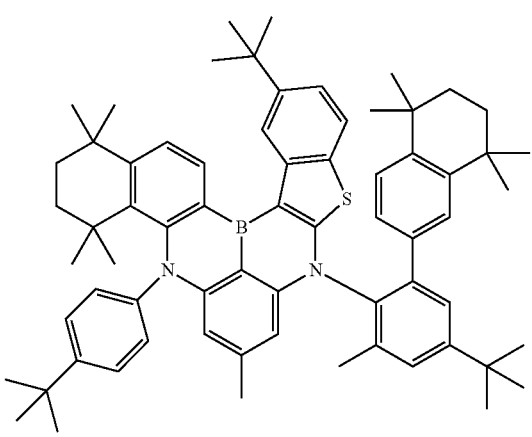
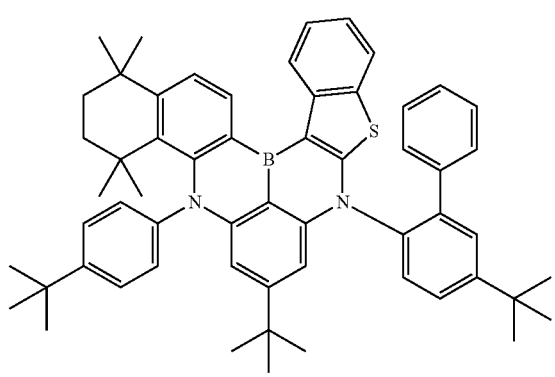
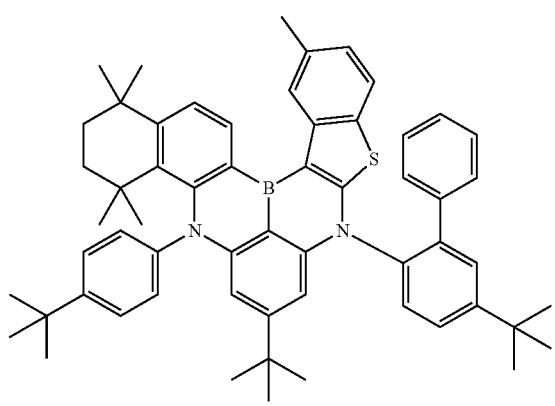
266
-continued
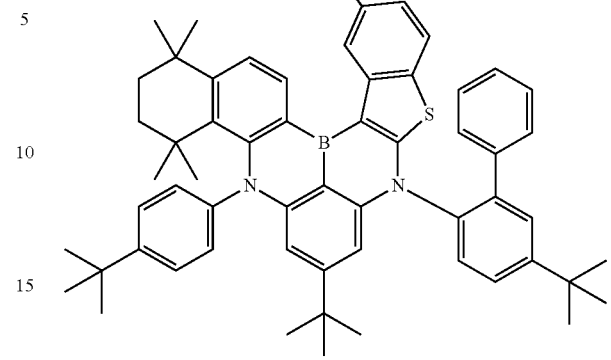
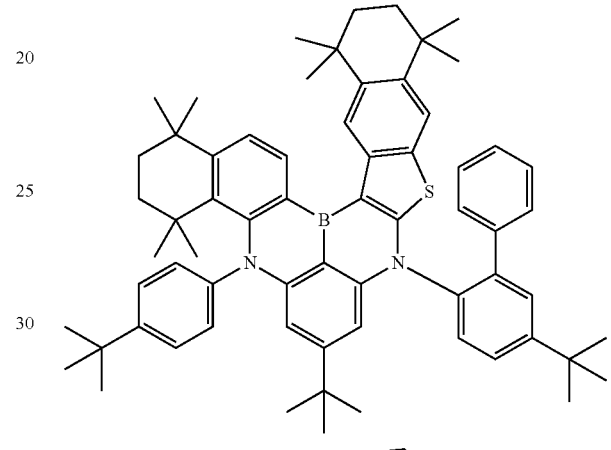
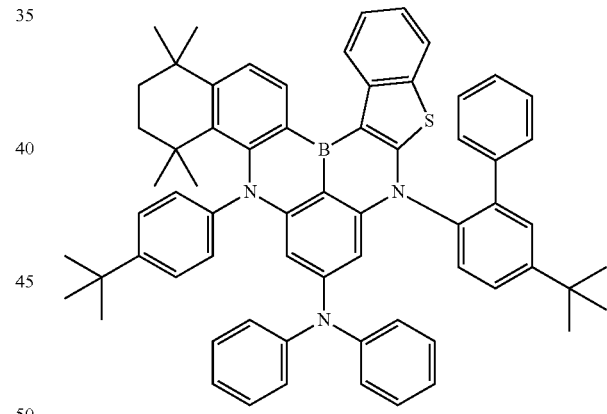
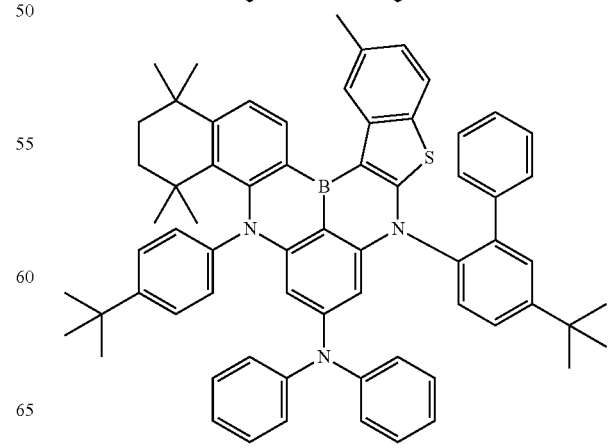

267
-continued
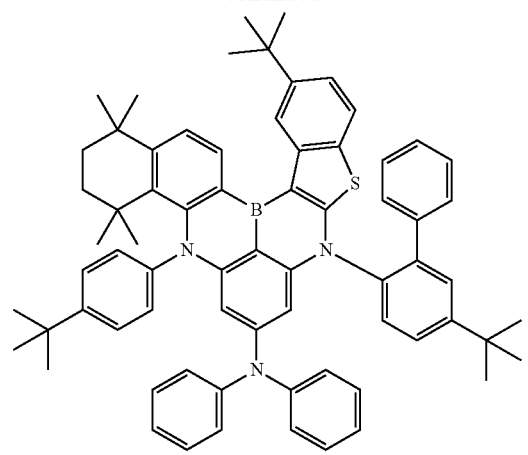
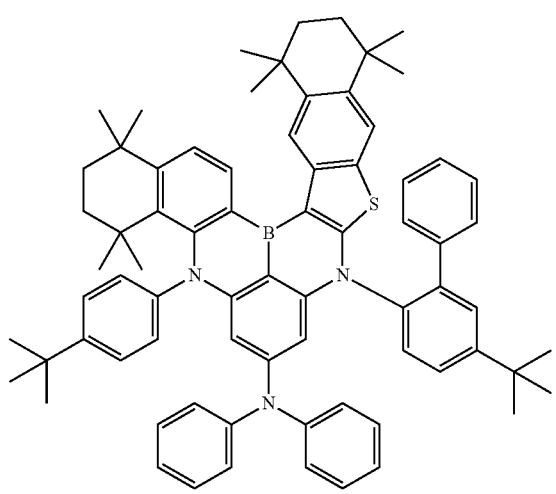
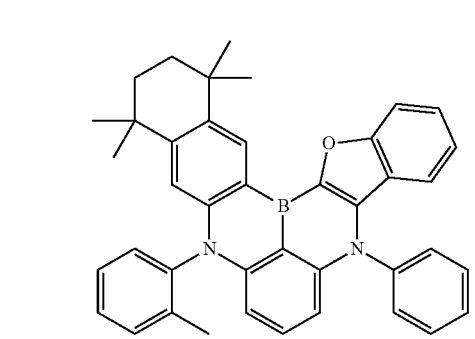
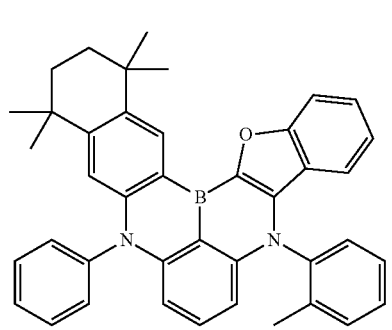
268
-continued
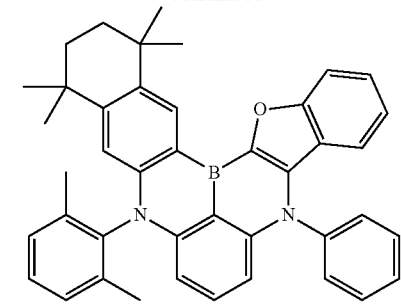
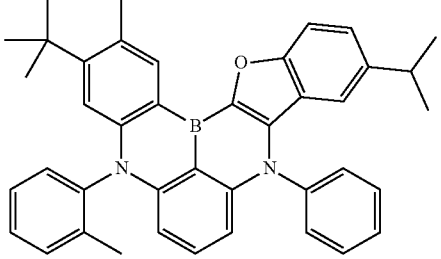
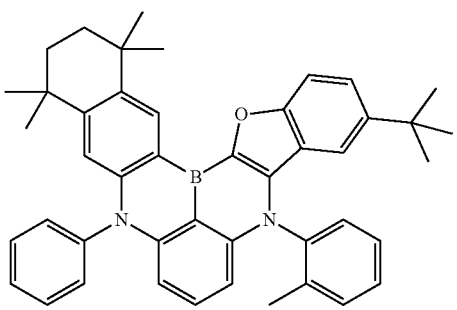
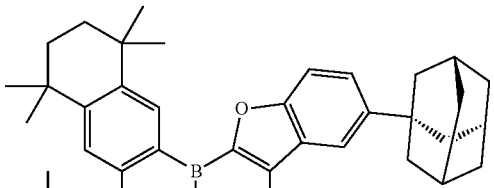
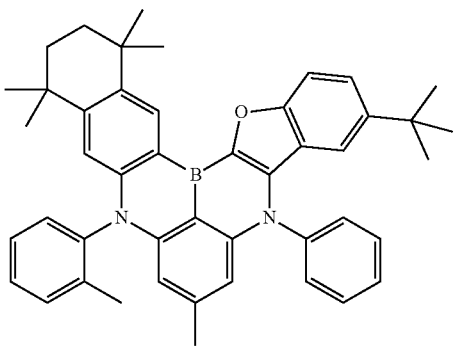

269
-continued
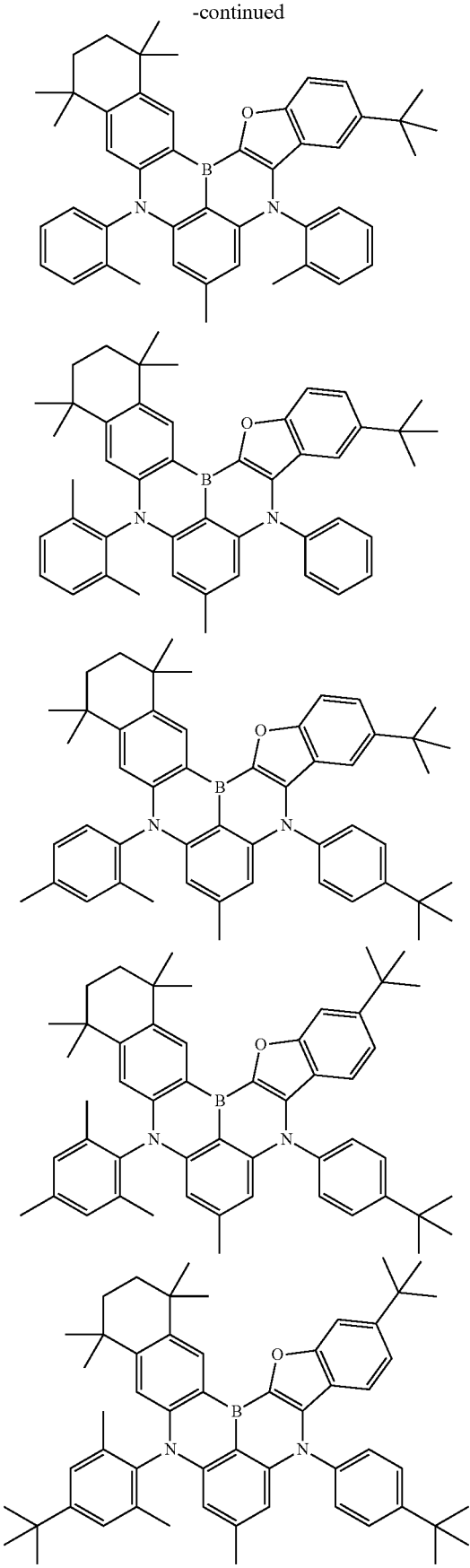
270
-continued
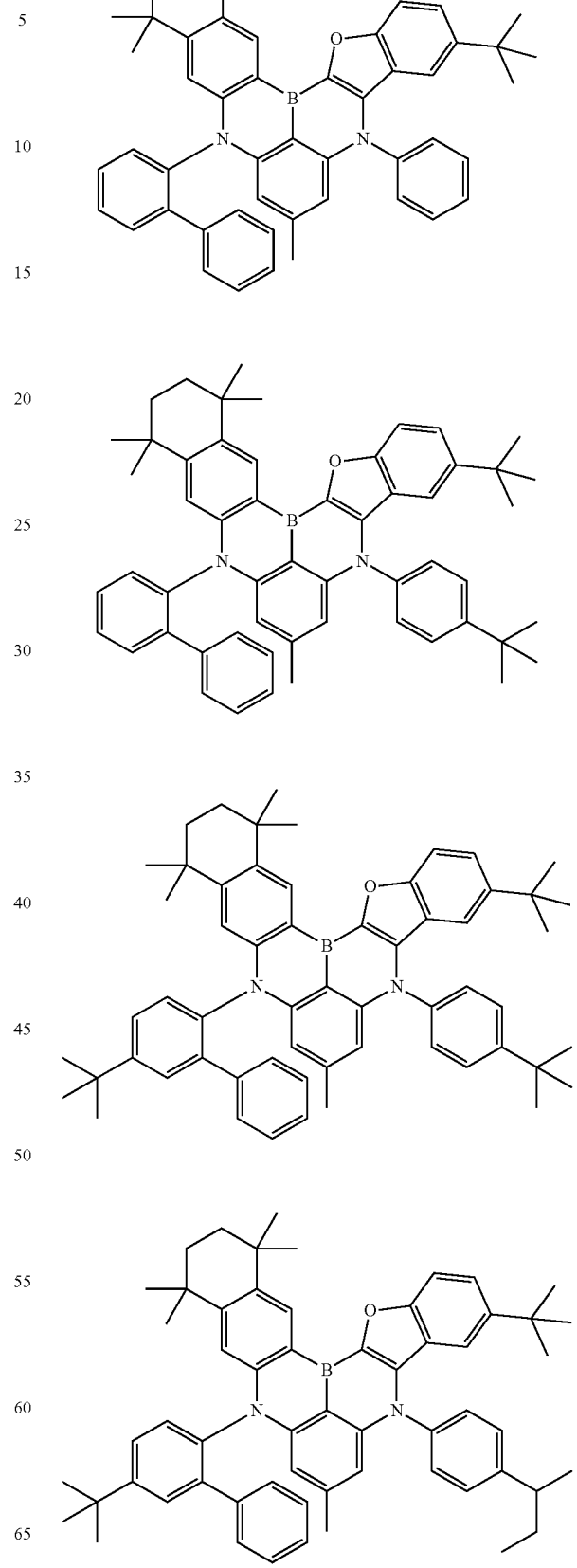

271
-continued
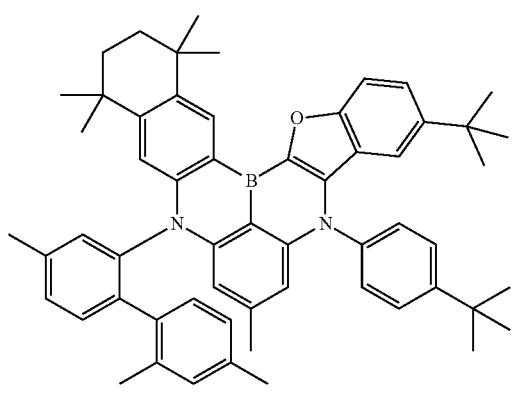
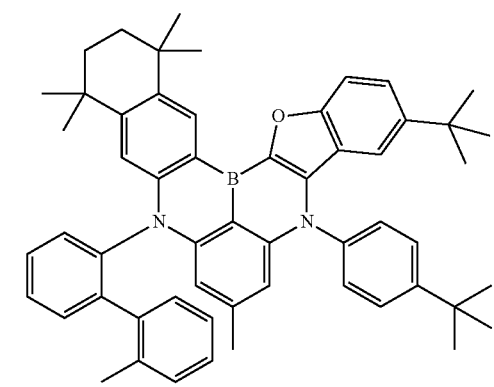
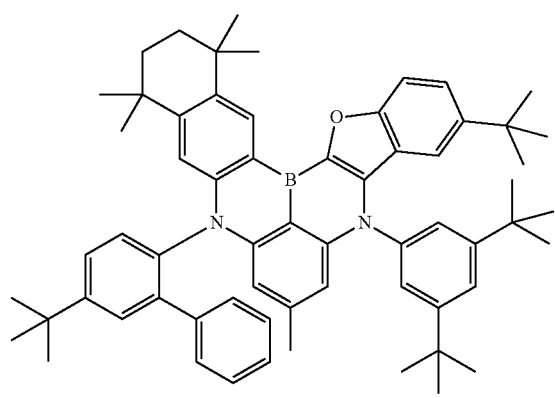
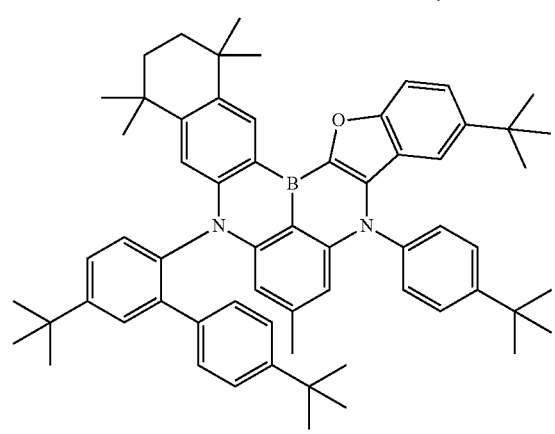
272
-continued
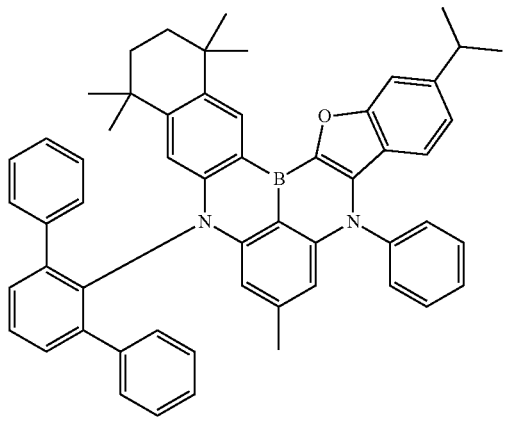
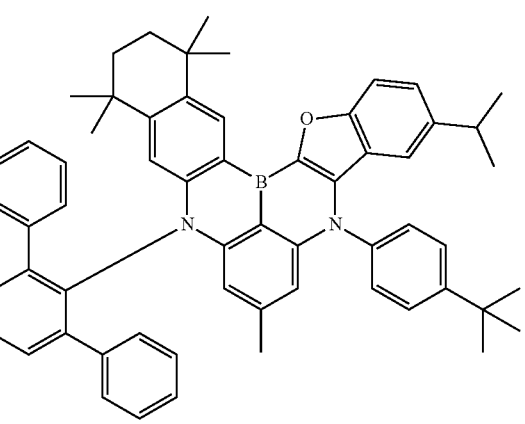
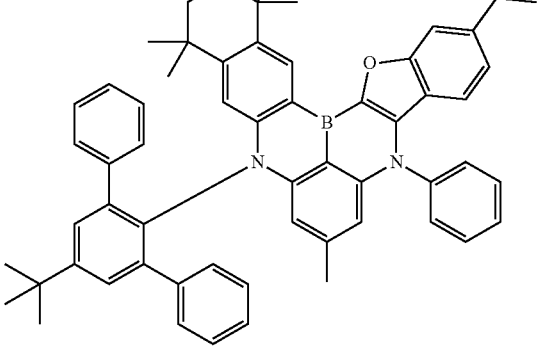
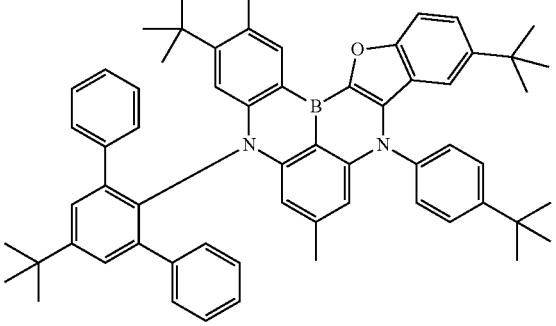

273
-continued
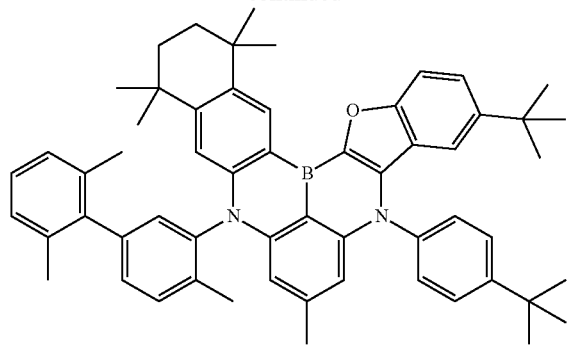
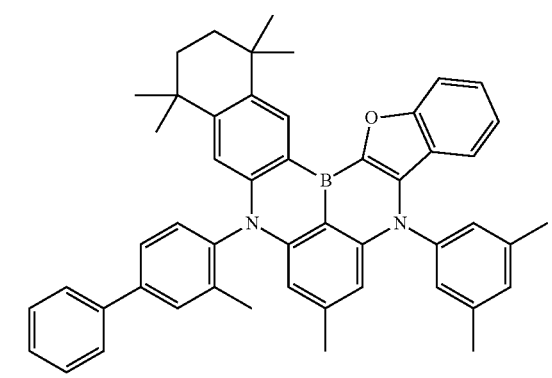
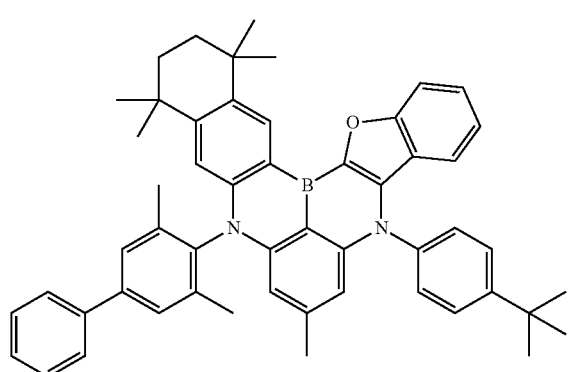
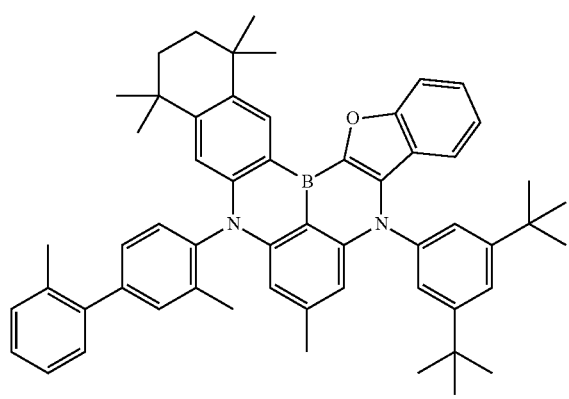
274
-continued
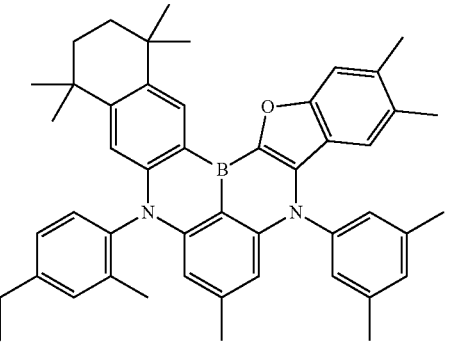
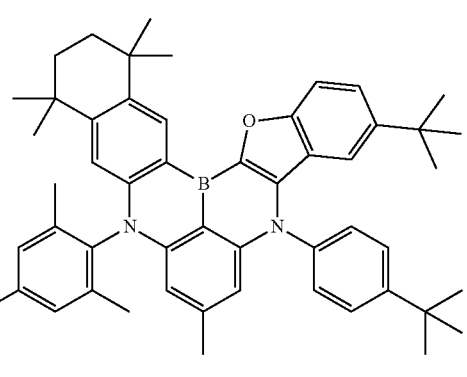
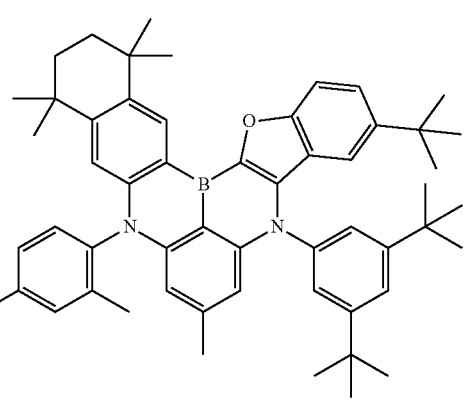
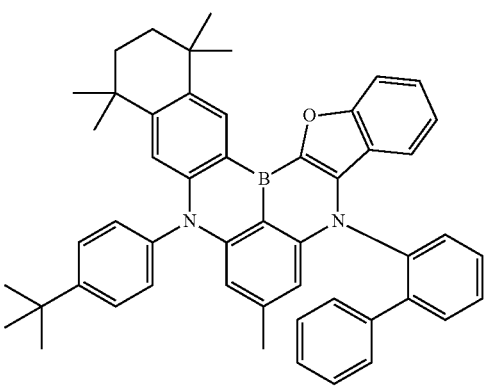

275
-continued
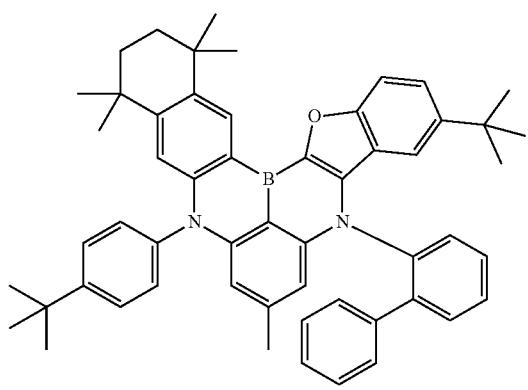
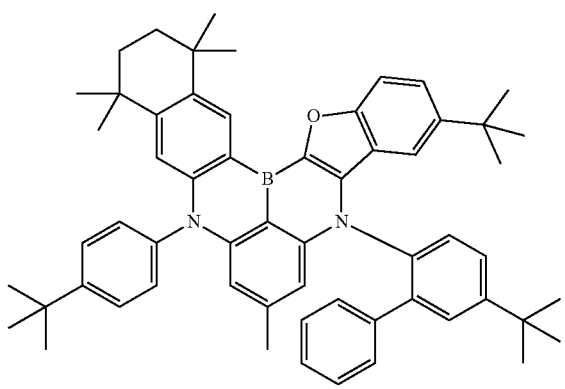
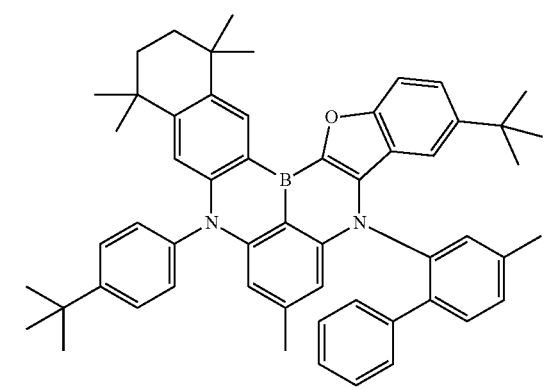
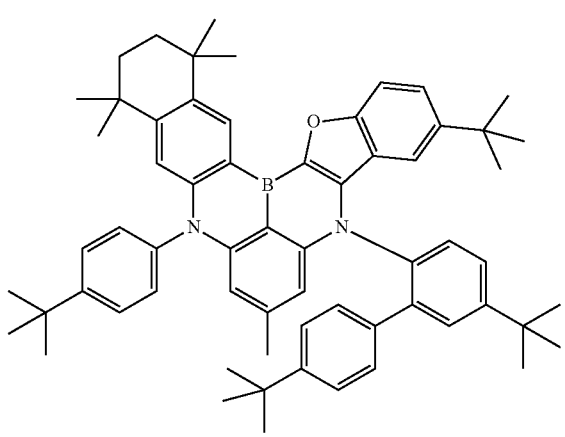
276
-continued
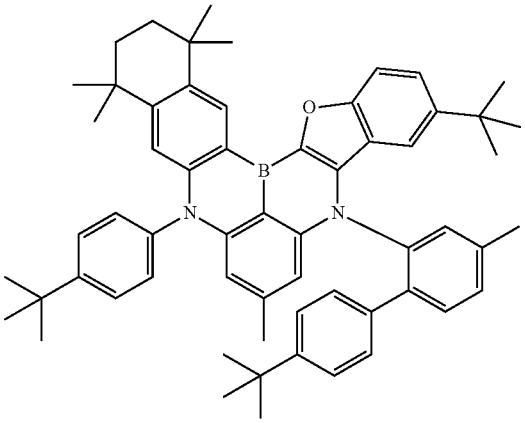
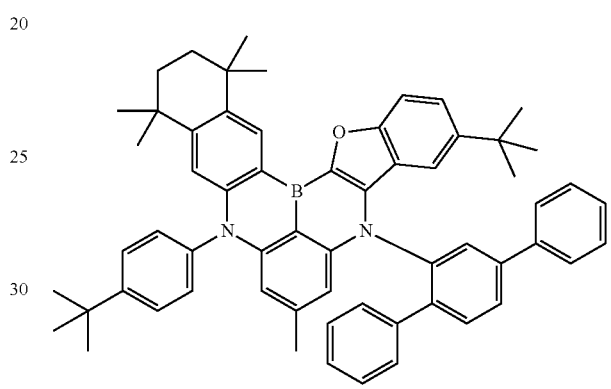

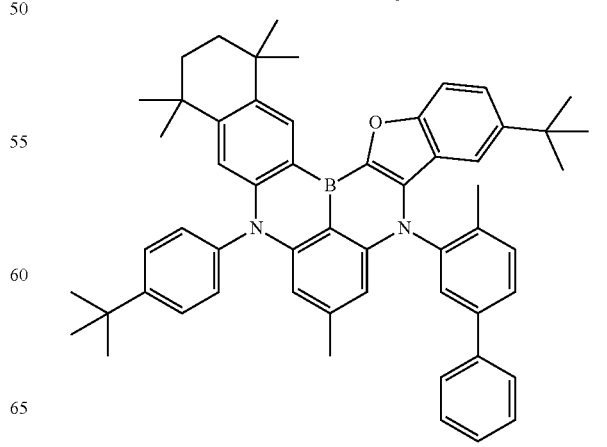

277
-continued
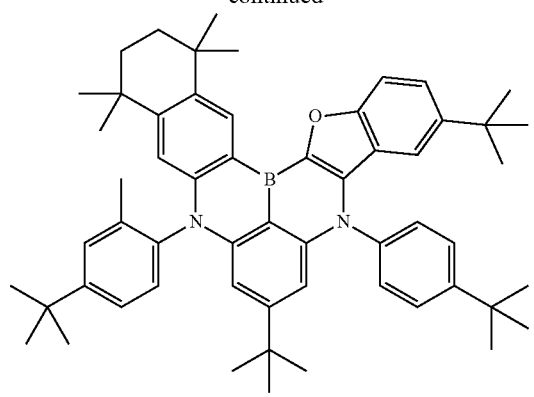
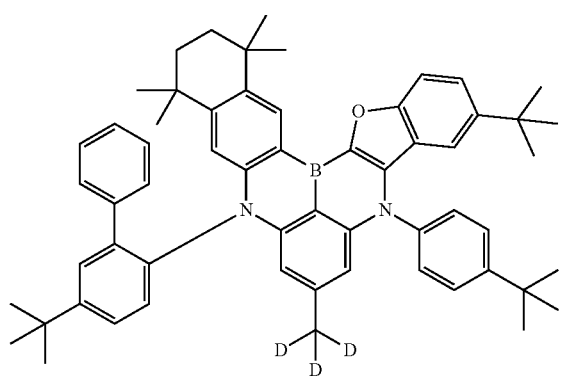
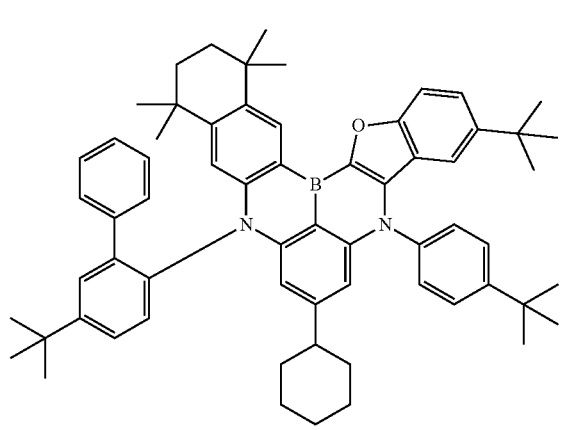
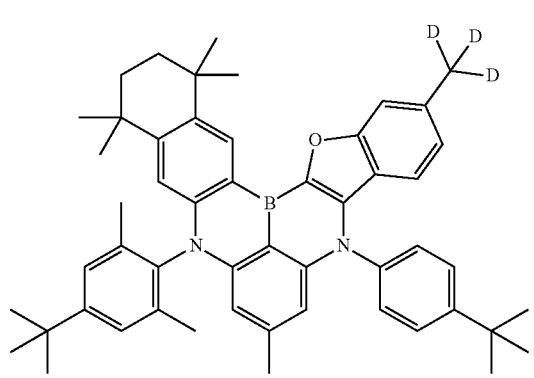
278
-continued
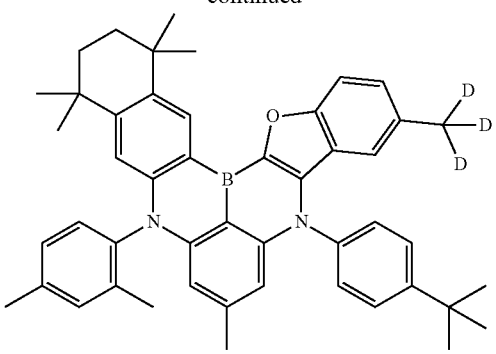
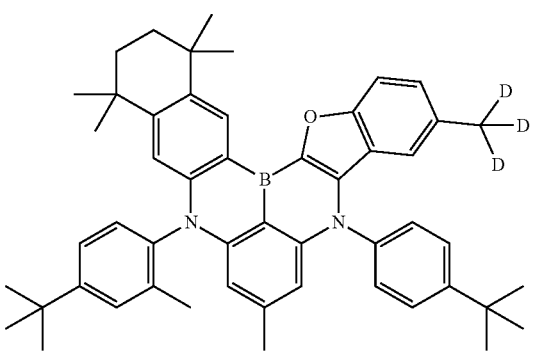
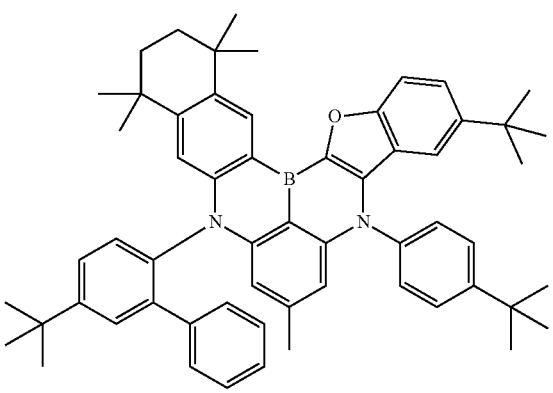
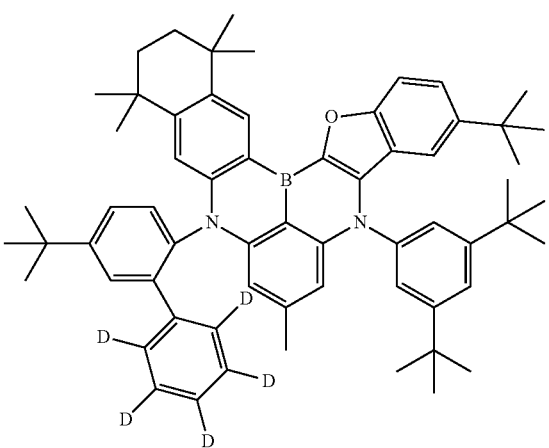

279
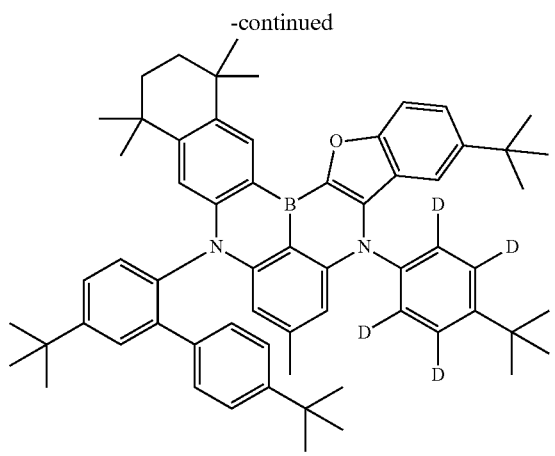
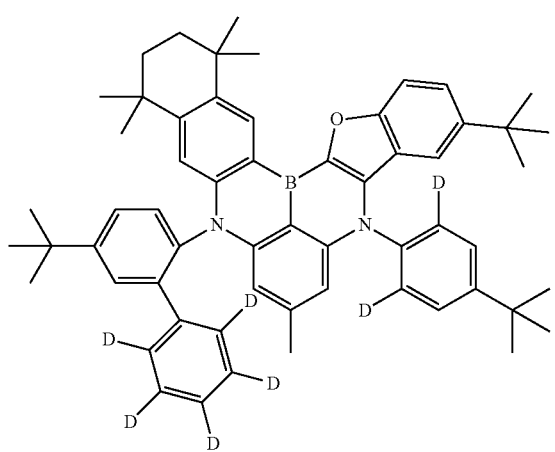
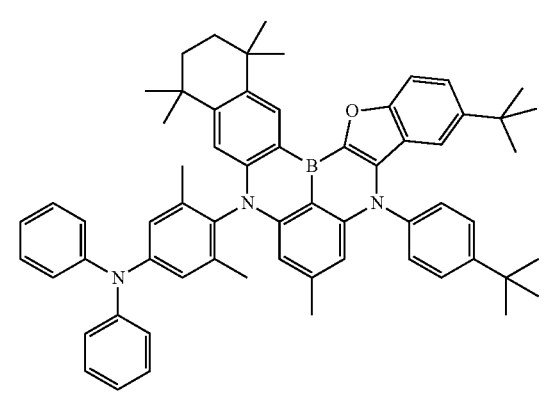
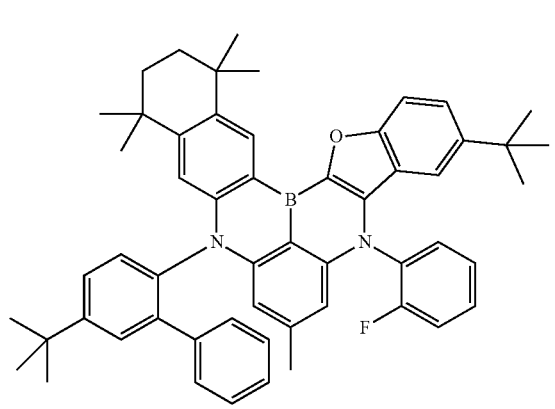
280
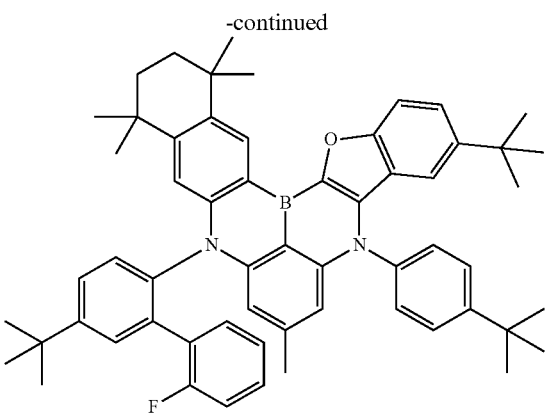
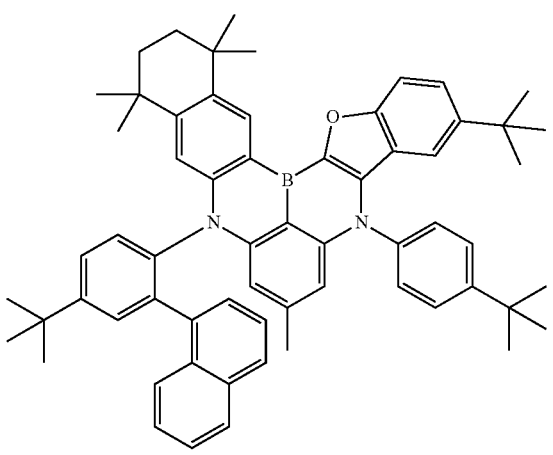
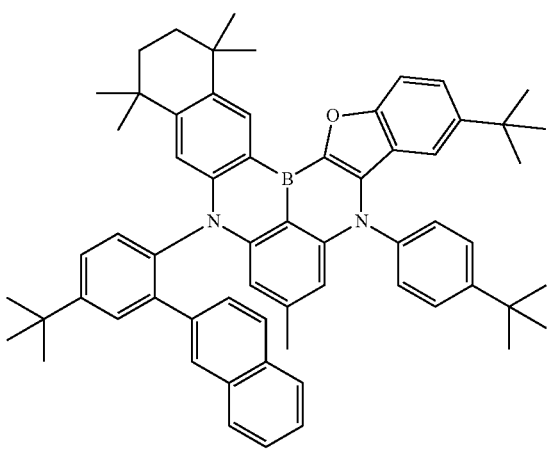
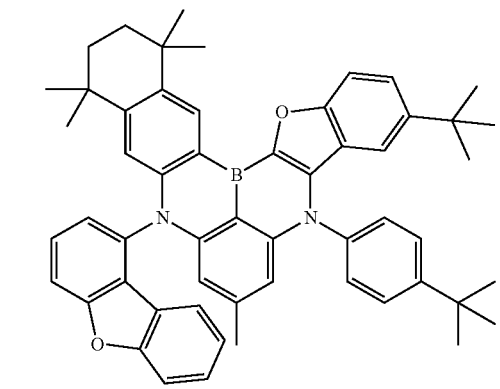

-continued
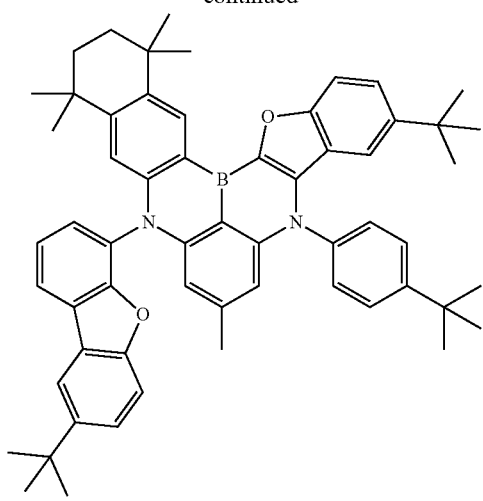
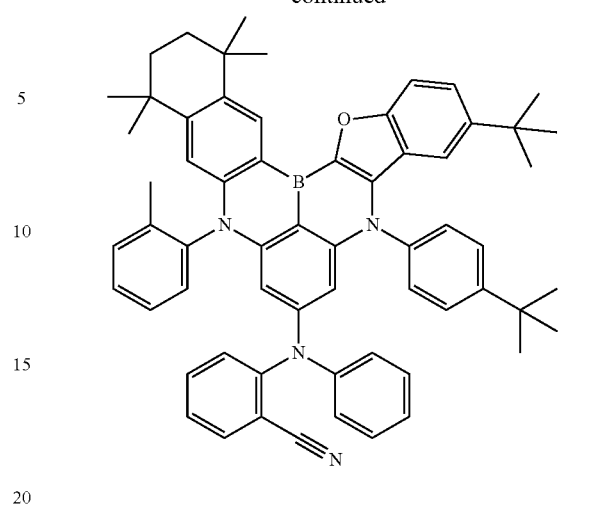
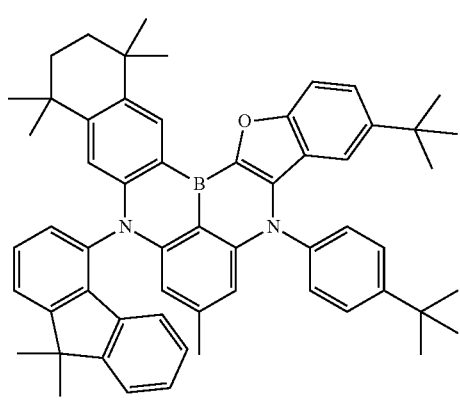
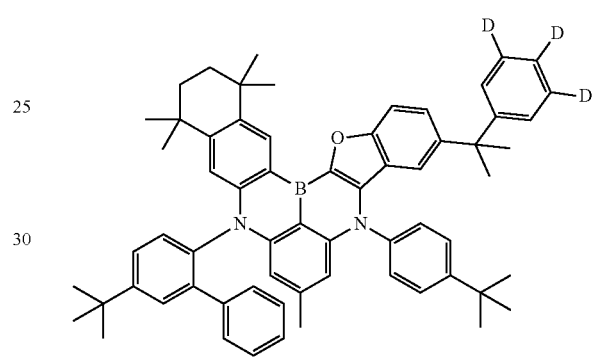
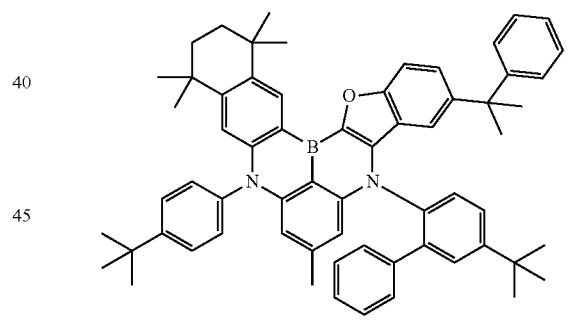
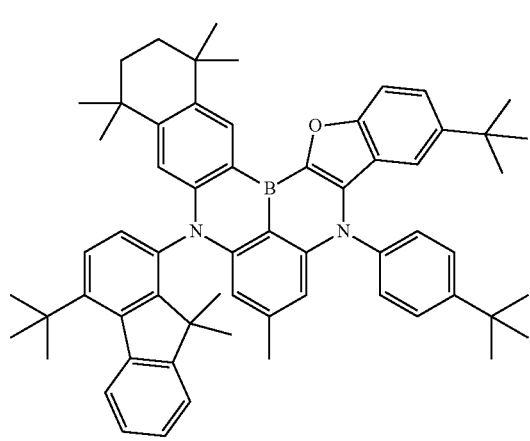
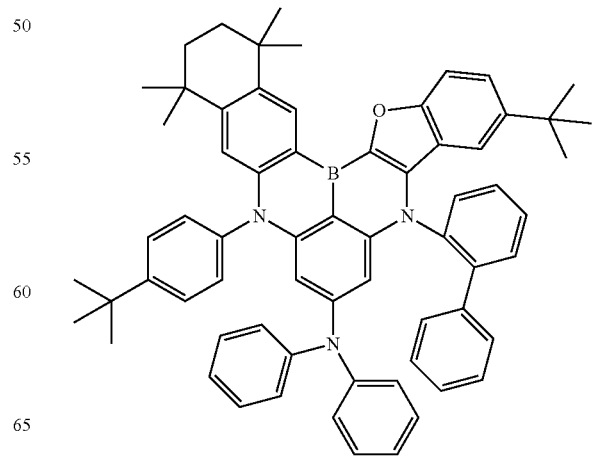

283
-continued
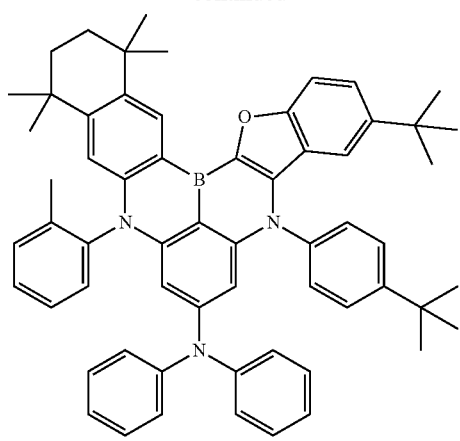
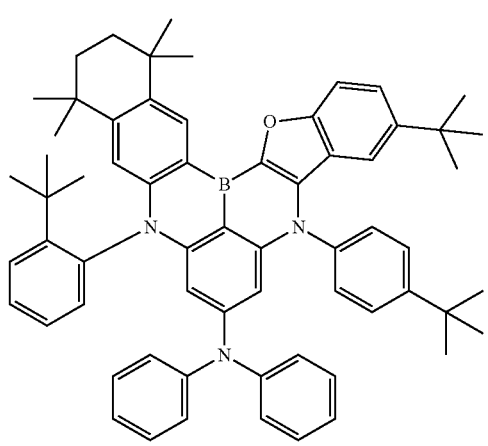
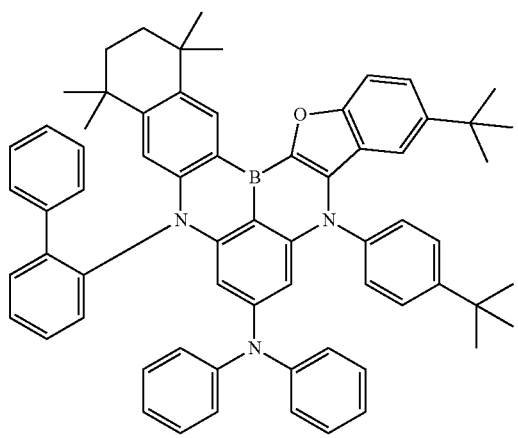
284
-continued
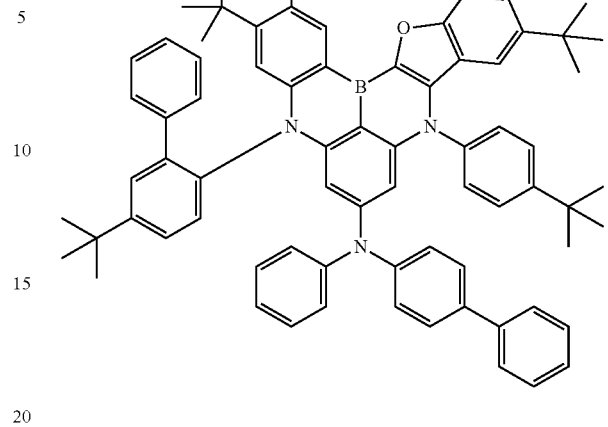
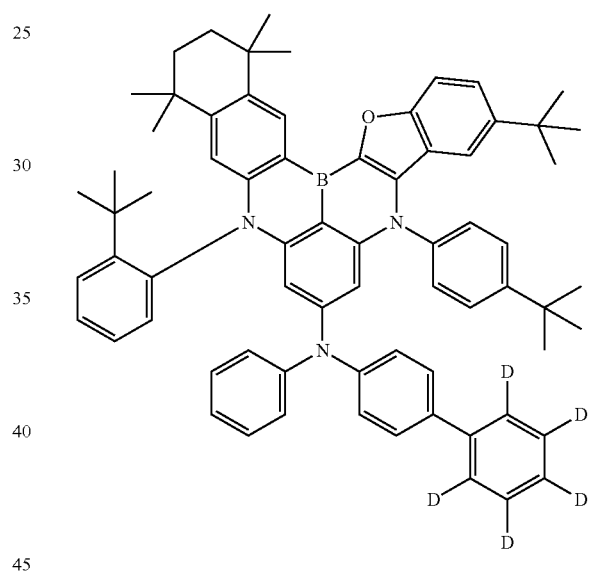
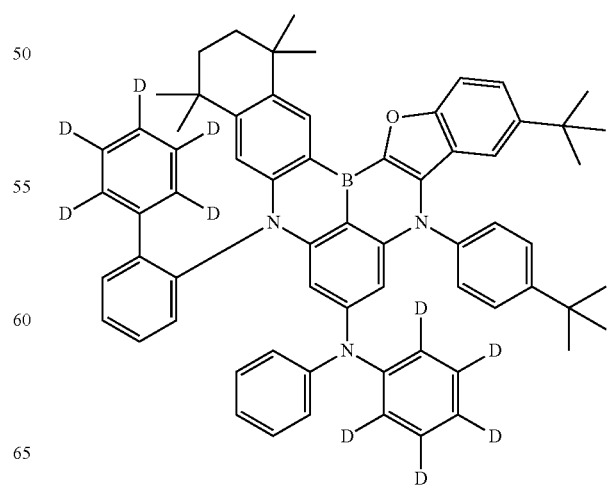

285
-continued
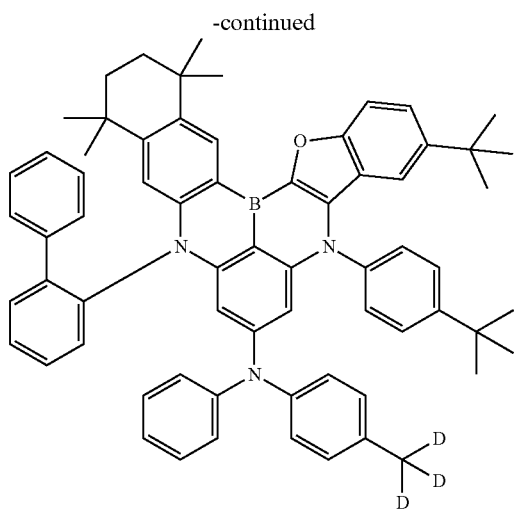
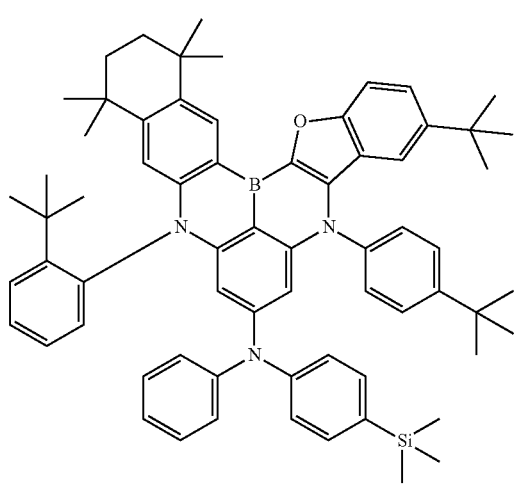
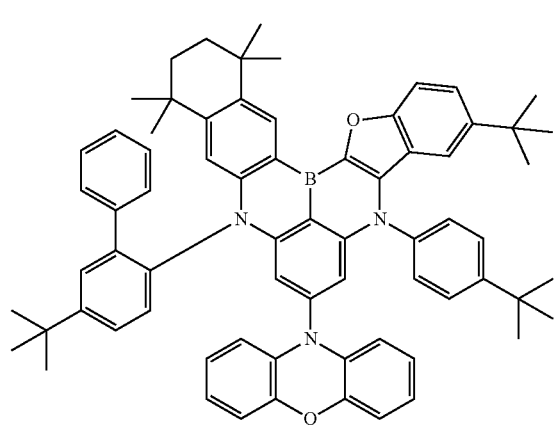
286
-continued
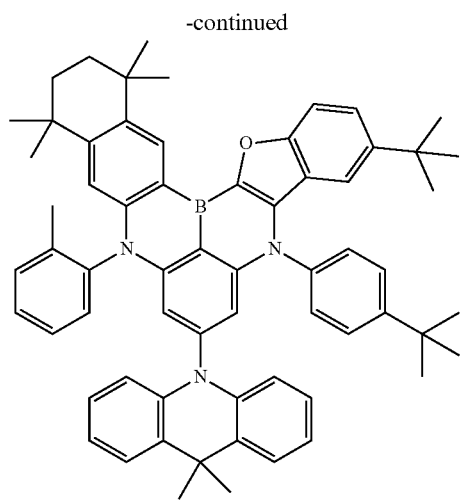
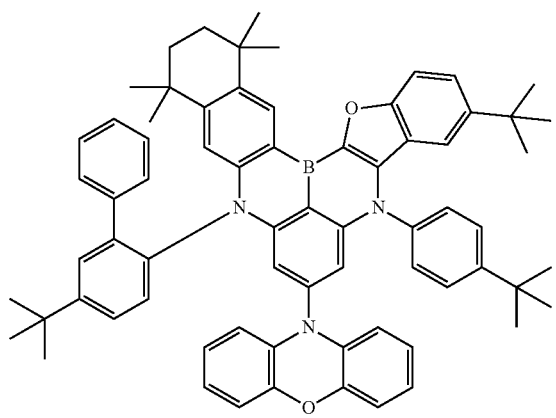
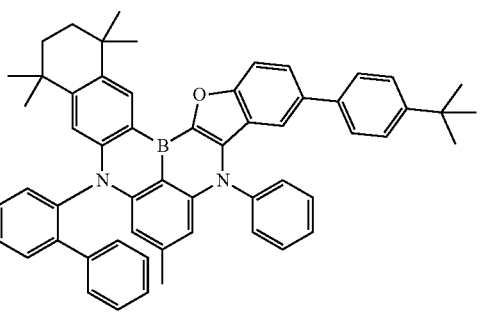

287
-continued
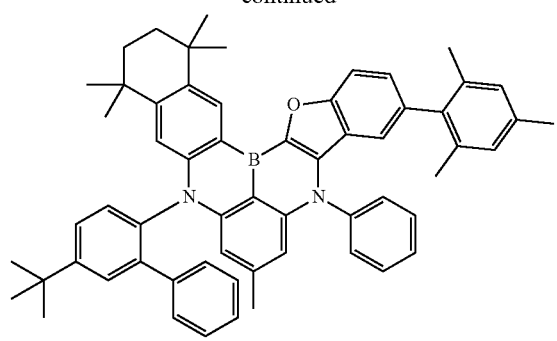
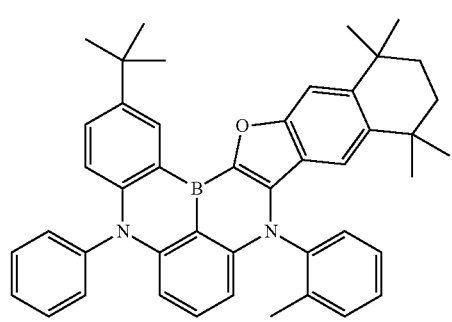
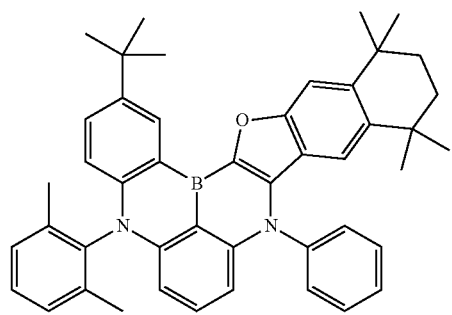
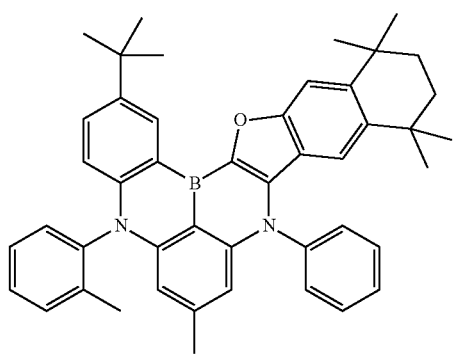
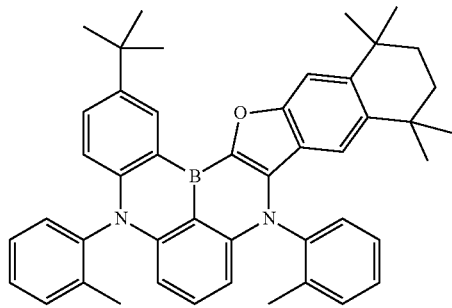
288
-continued
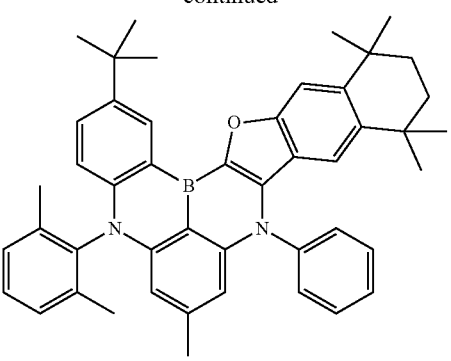
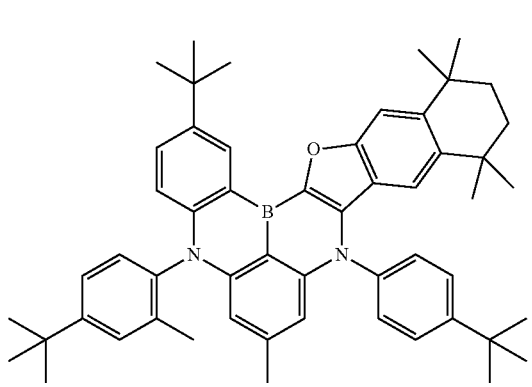
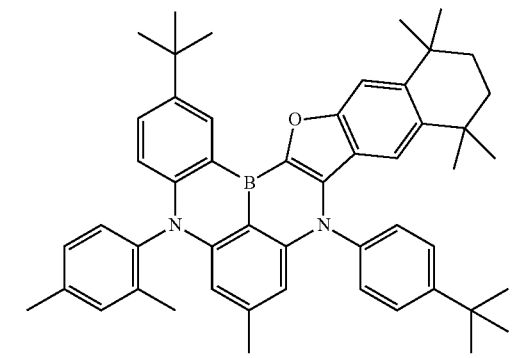
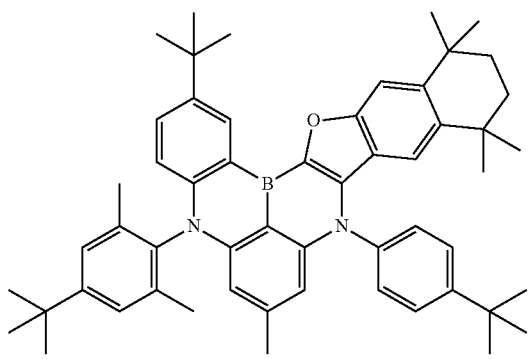

289
-continued
290
-continued
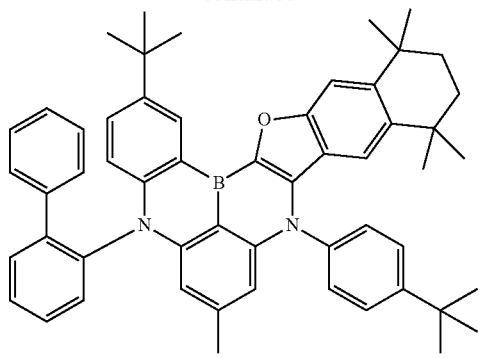
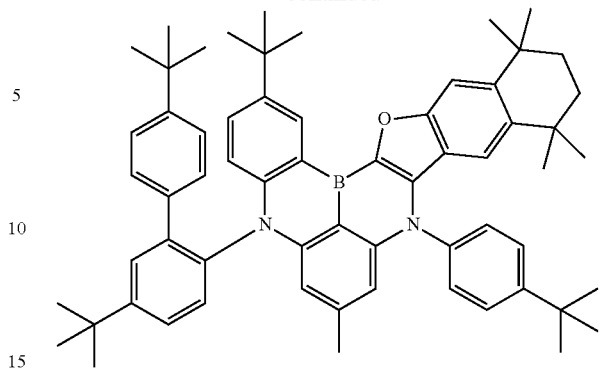
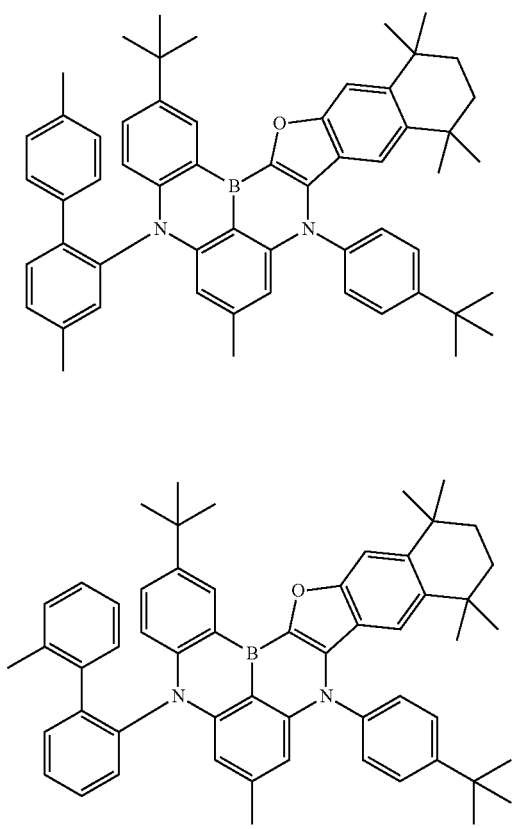
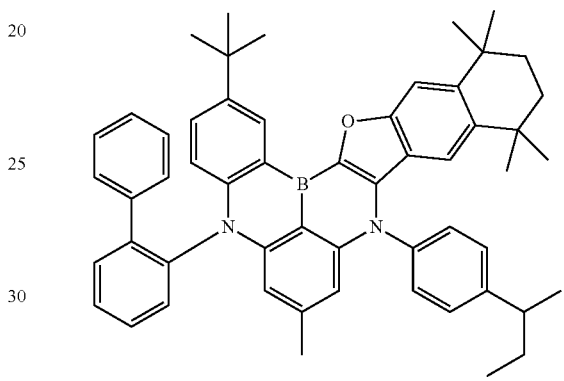
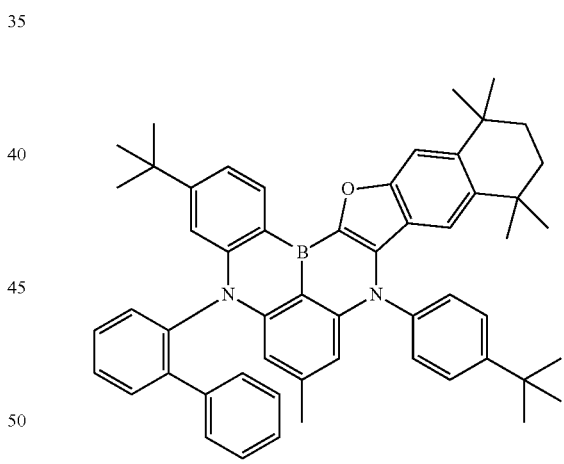
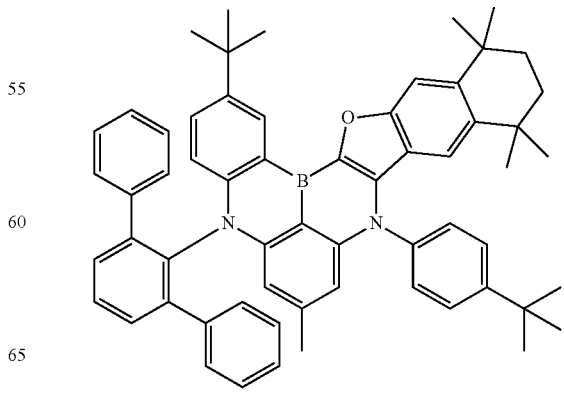

291
-continued
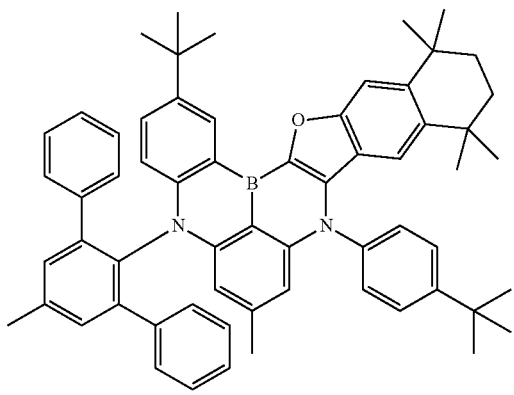
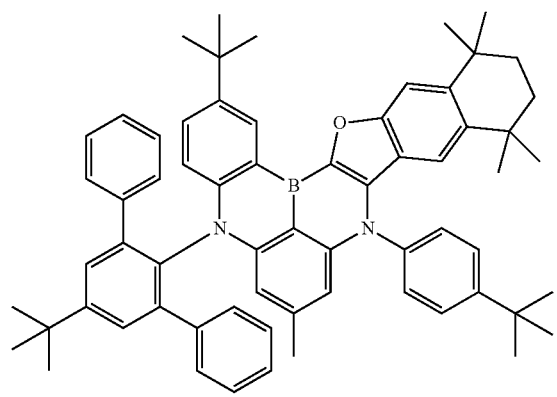
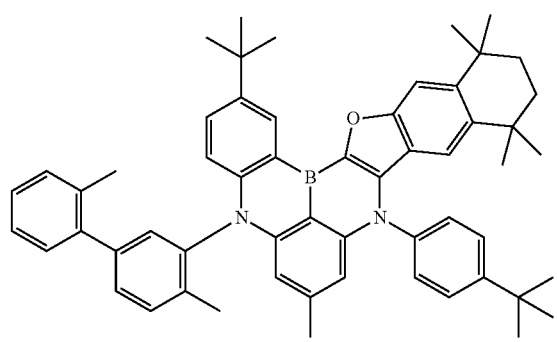
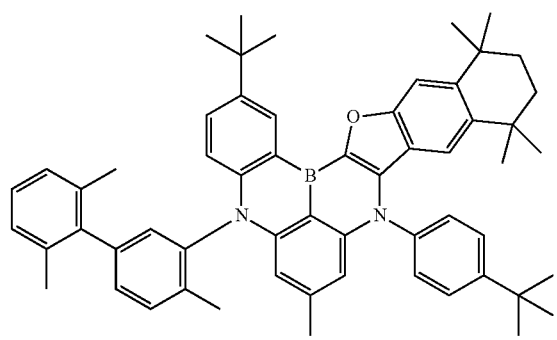
292
-continued
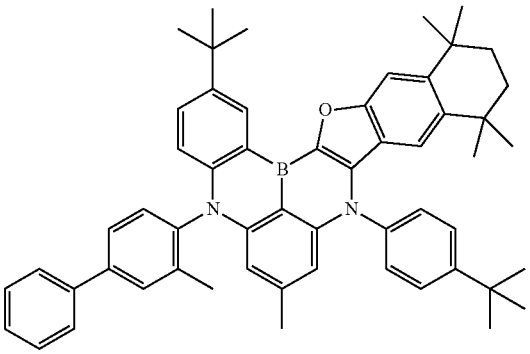
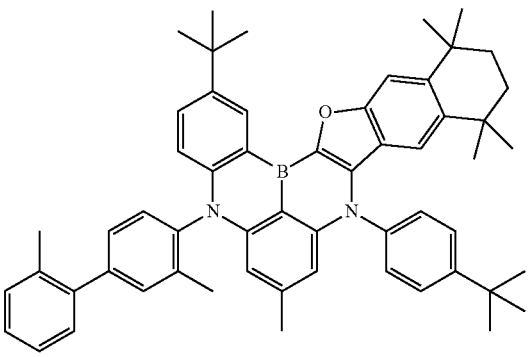
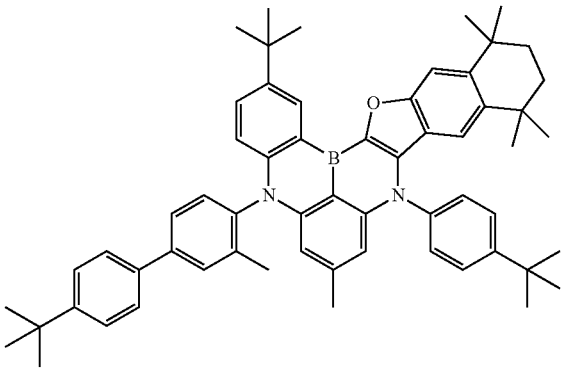
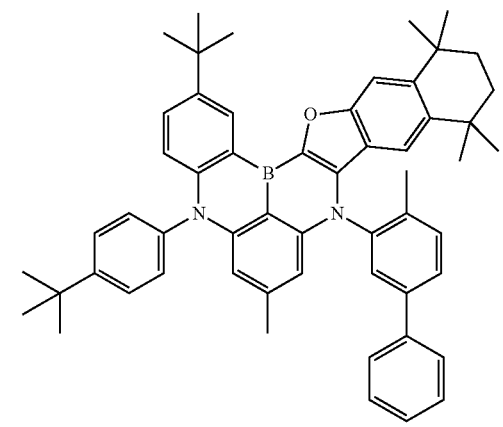

293
-continued
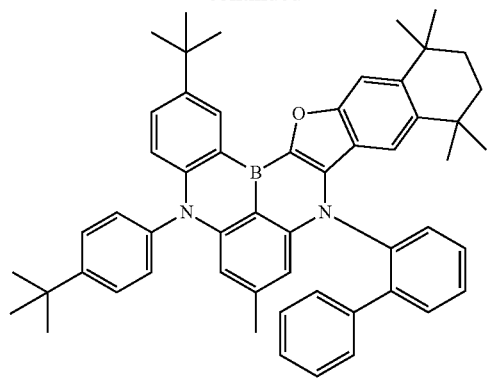
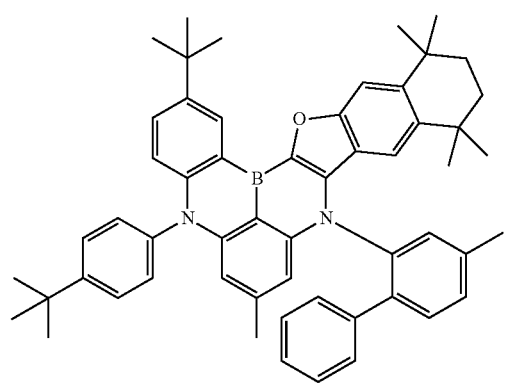
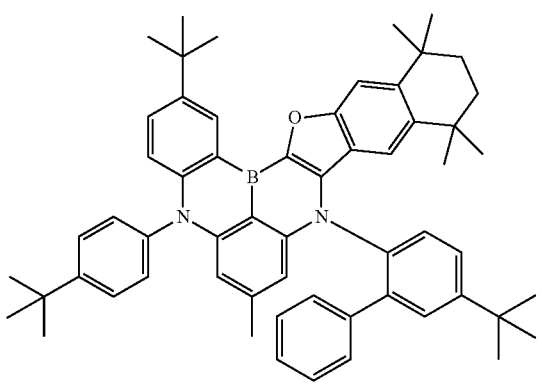
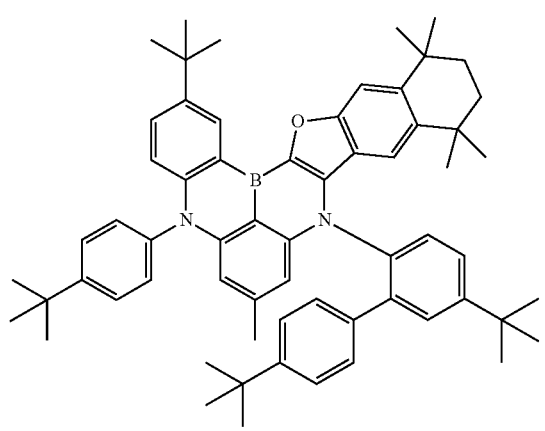
294
-continued
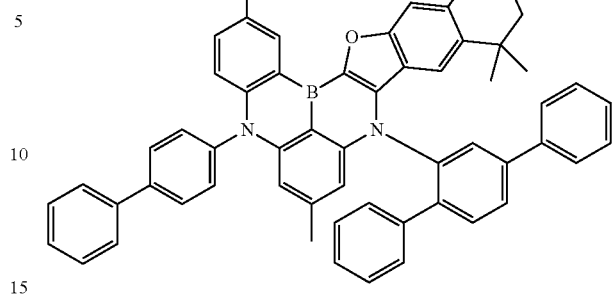
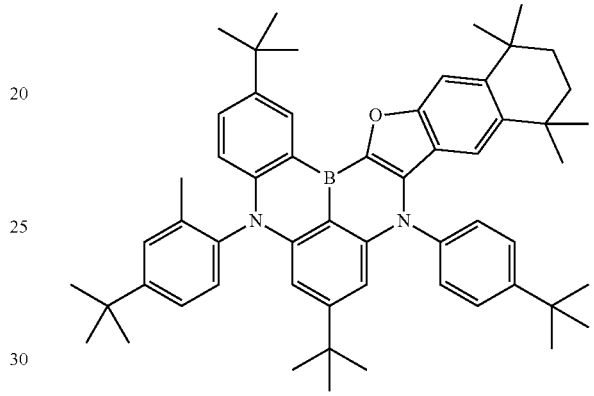
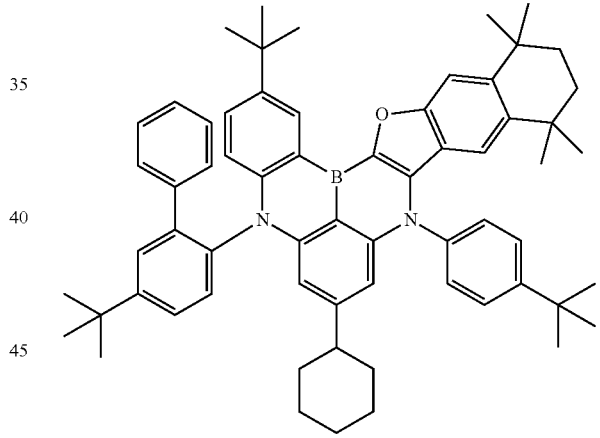
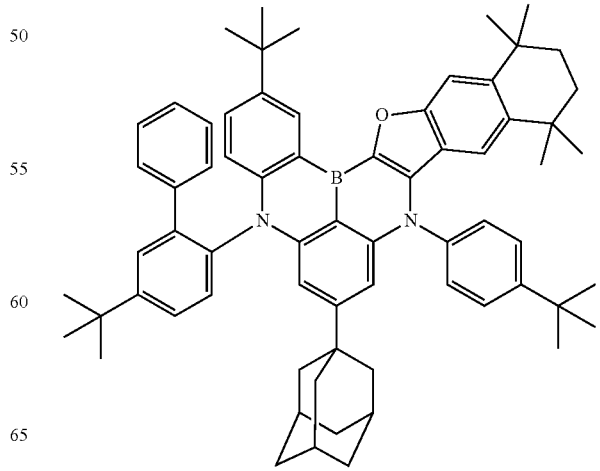

295
-continued
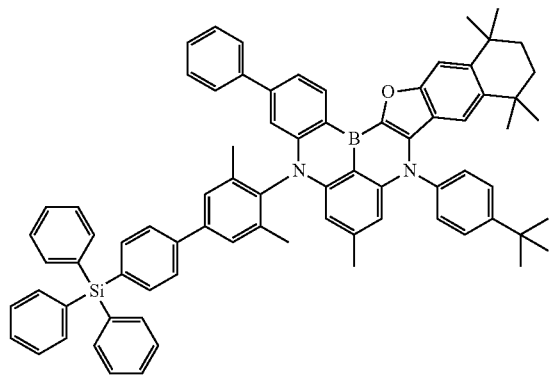
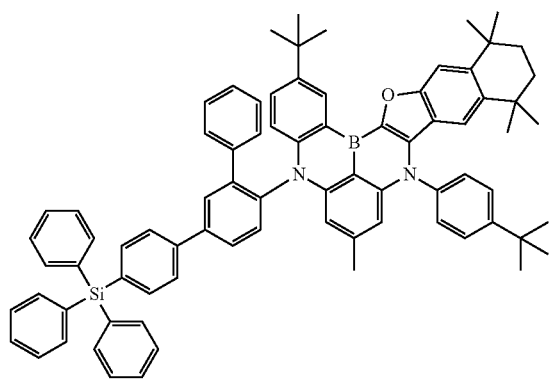
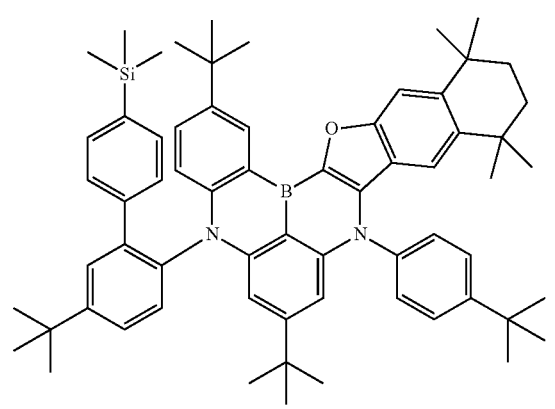
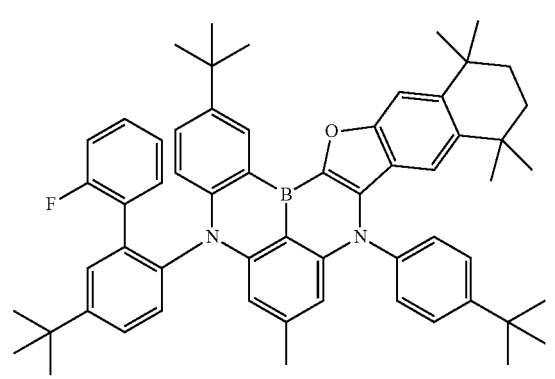
296
-continued
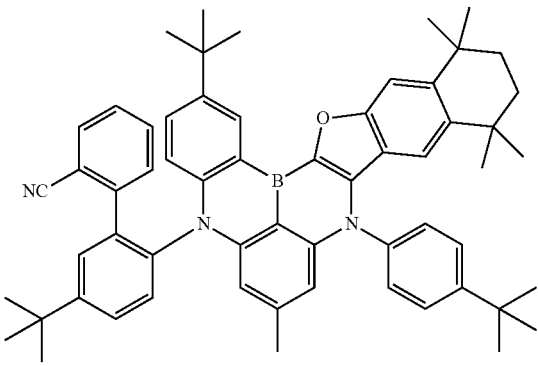
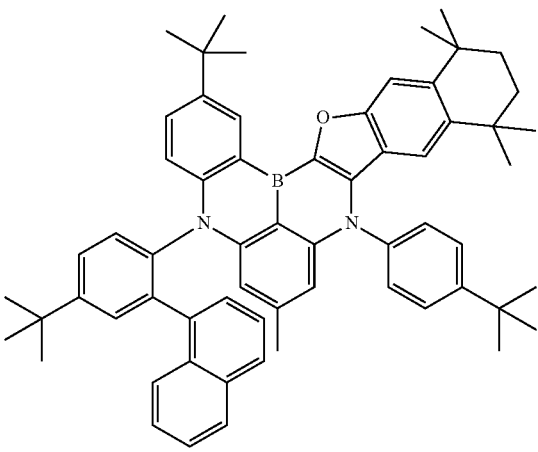
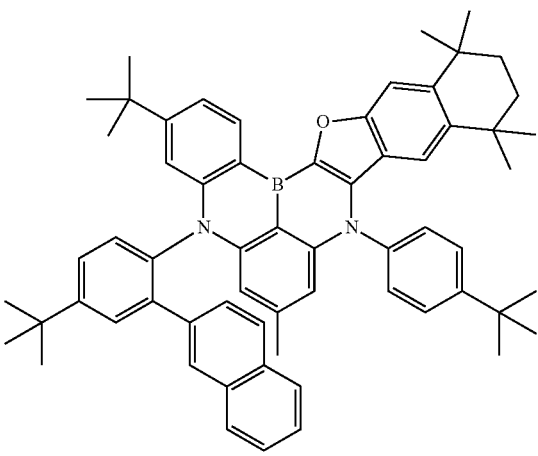
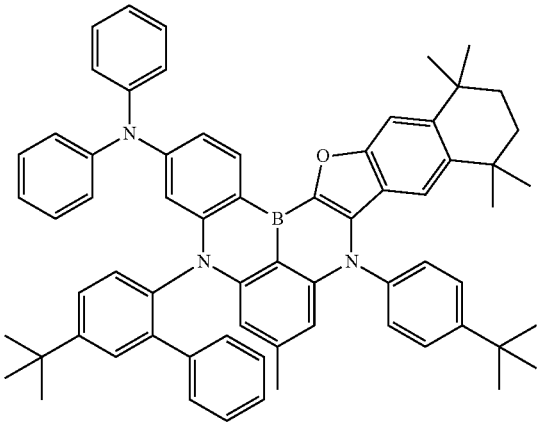

297
-continued
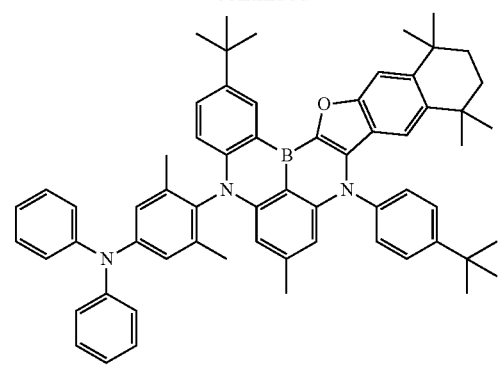
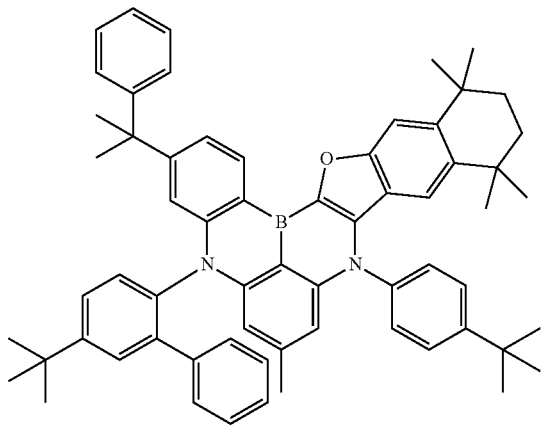
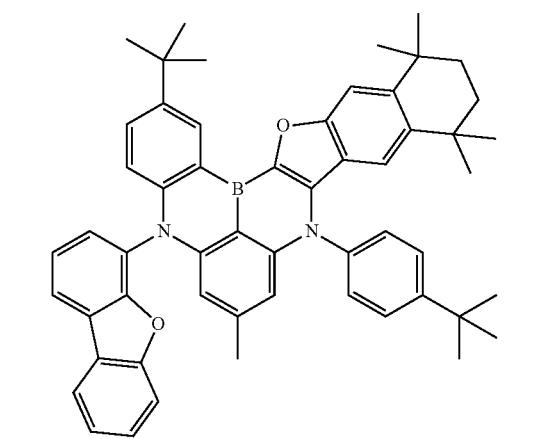
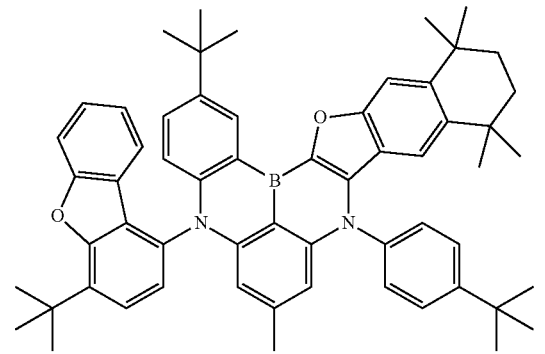
298
-continued
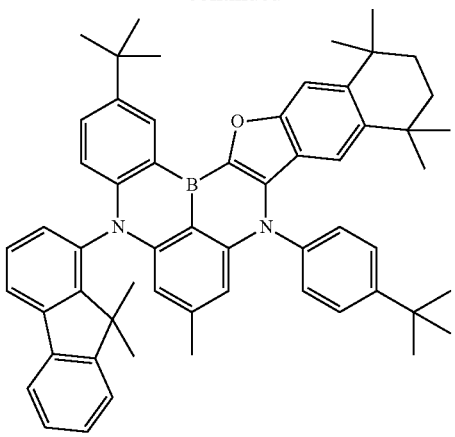
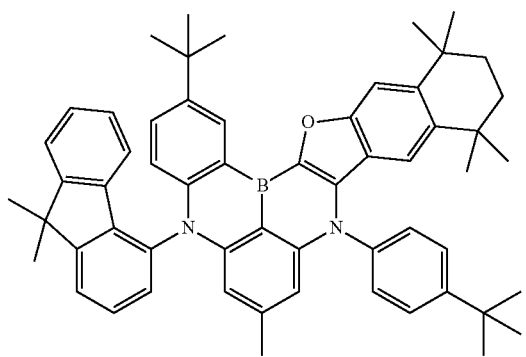
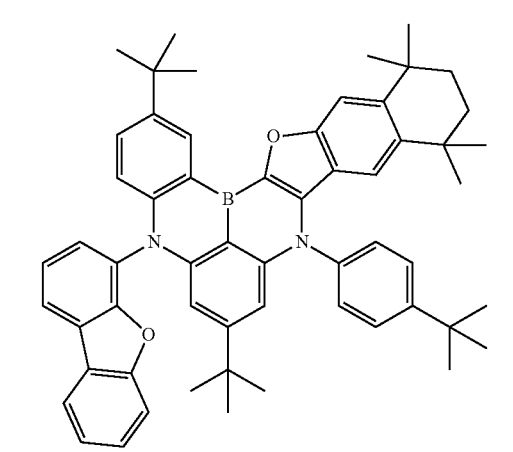
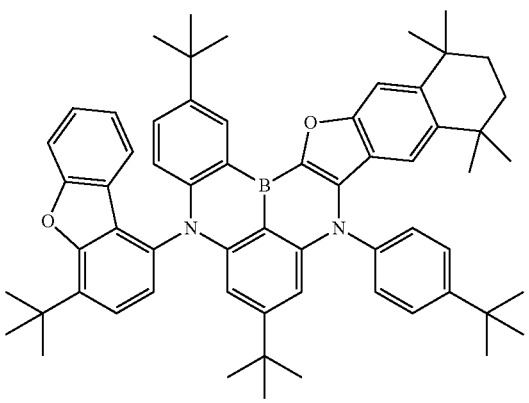

299
-continued
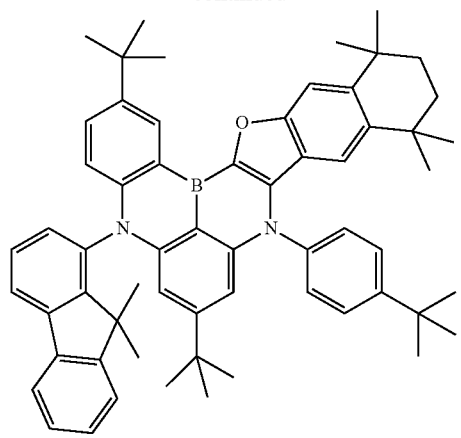
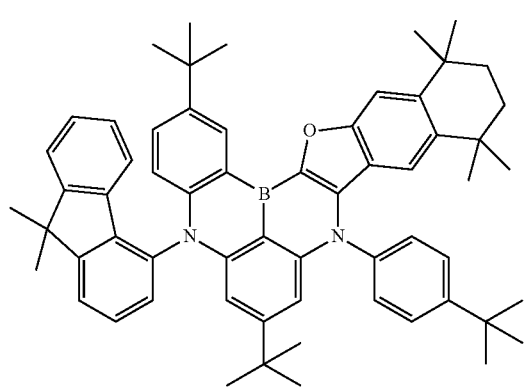
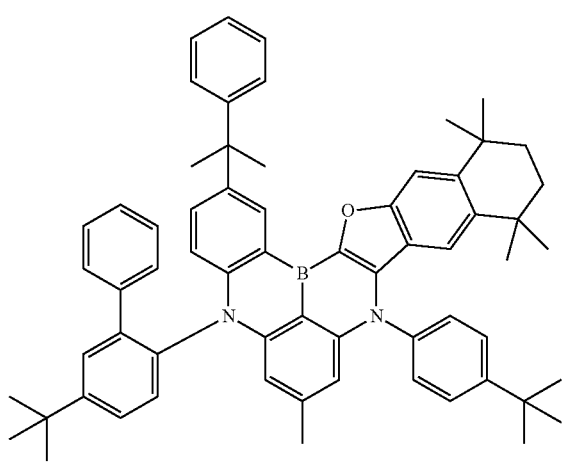
300
-continued
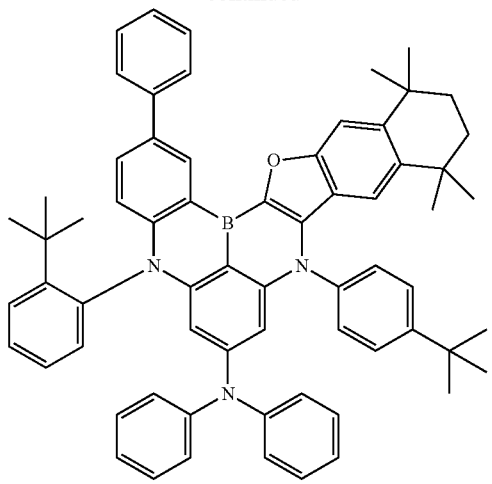
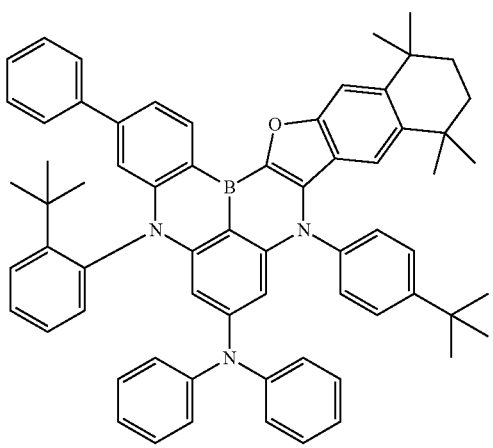
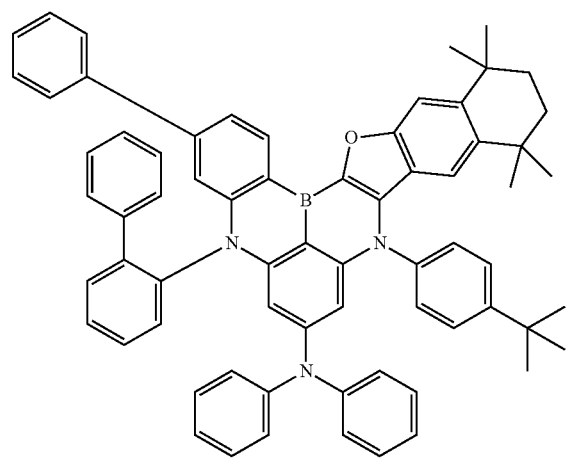

301
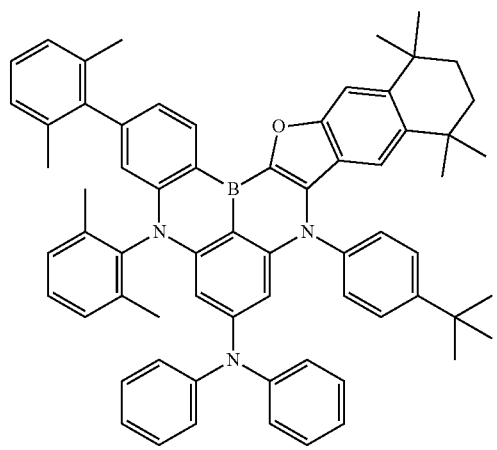
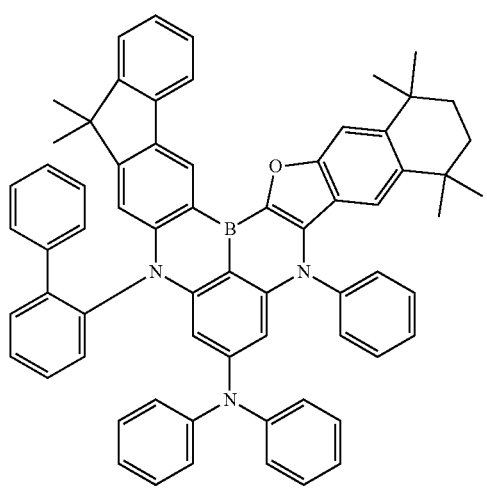
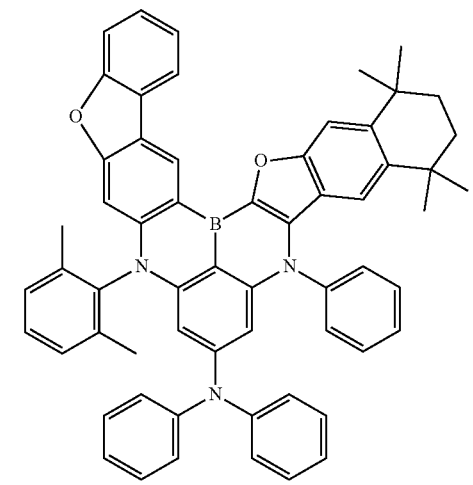
302
-continued
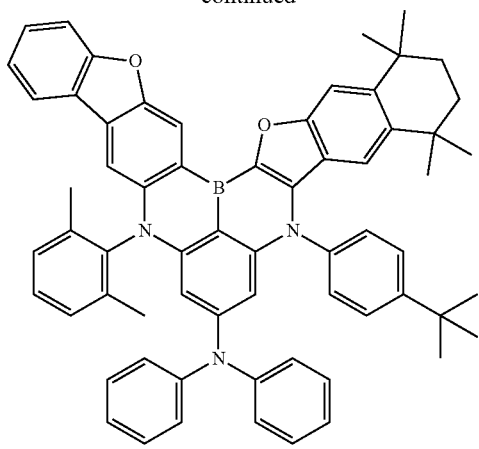
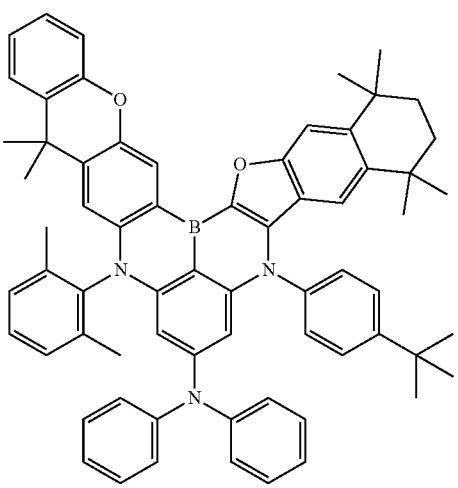
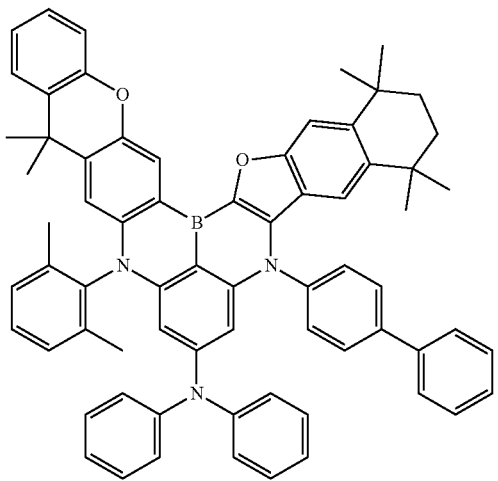

303
-continued
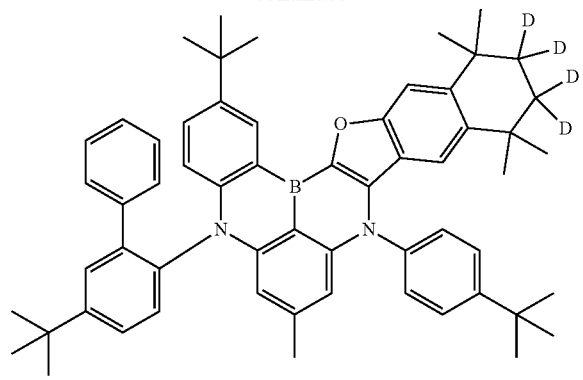
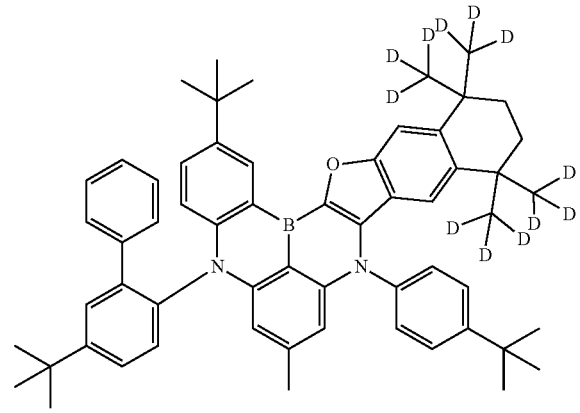
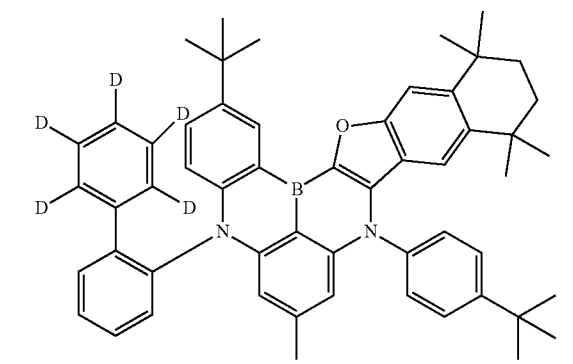
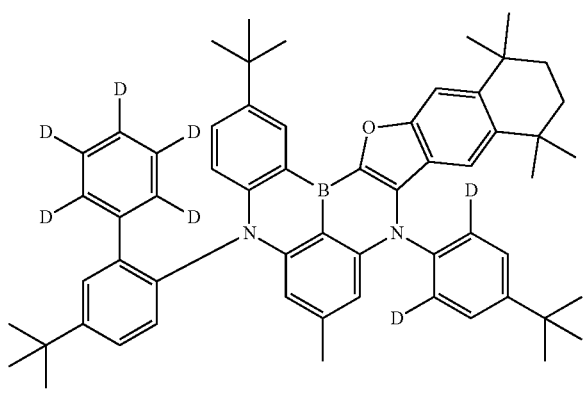
304
-continued
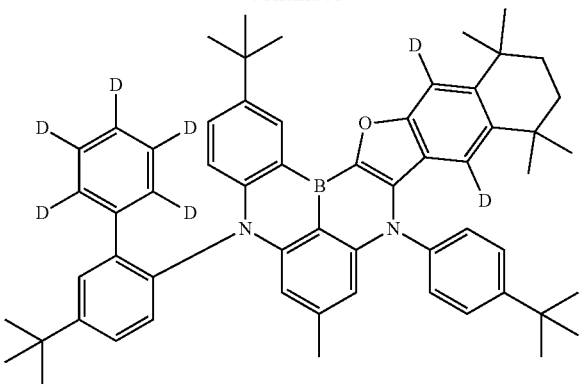
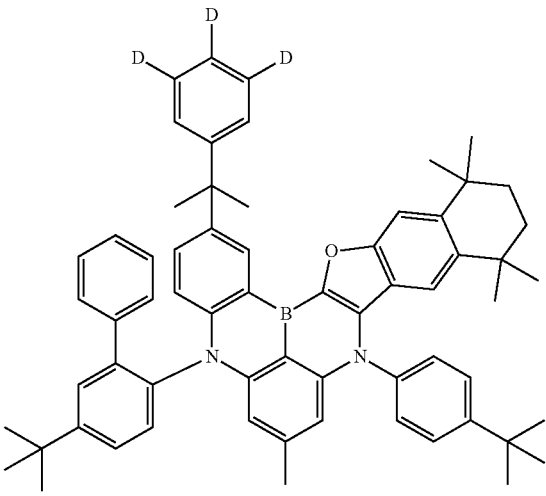

305
306
-continued
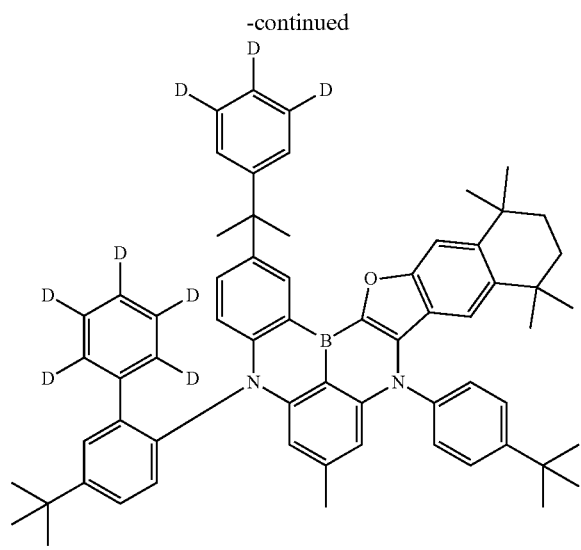
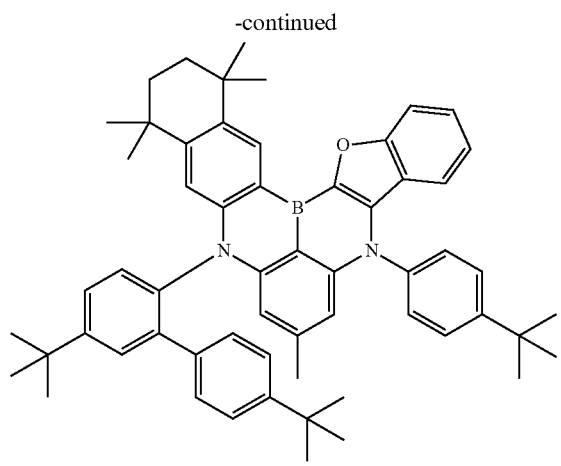

| 307 -continued | 308 -continued |
|---|---|
| 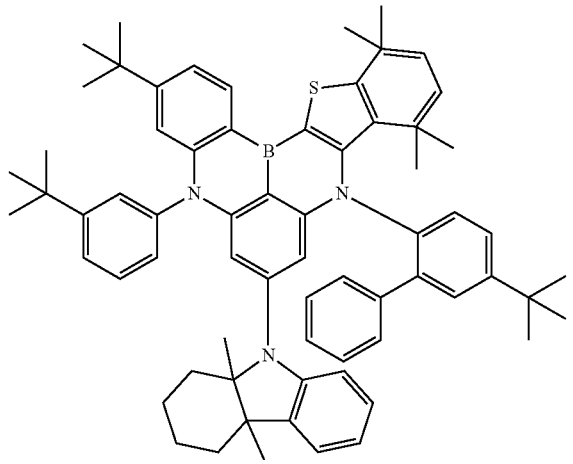 | 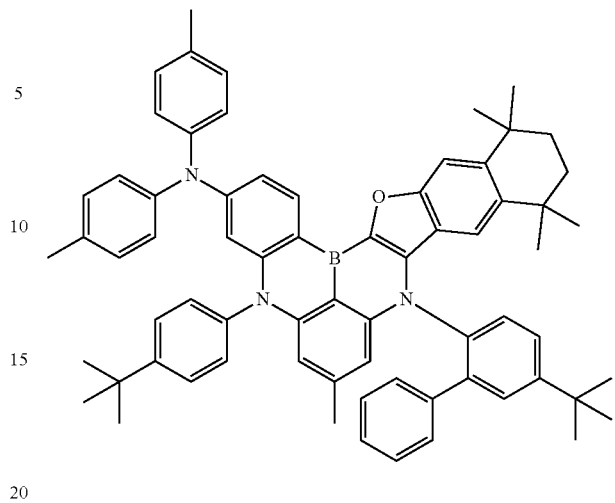 |
| 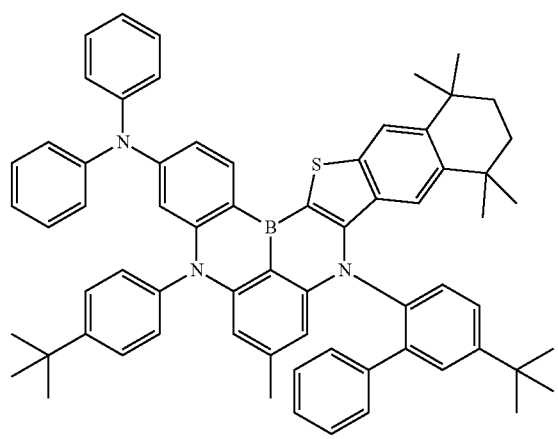 | 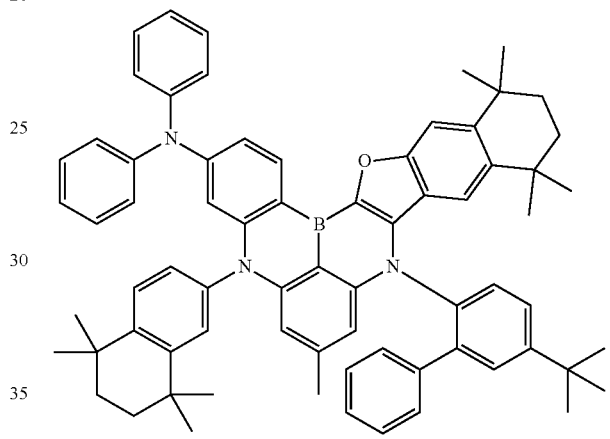 |
| | 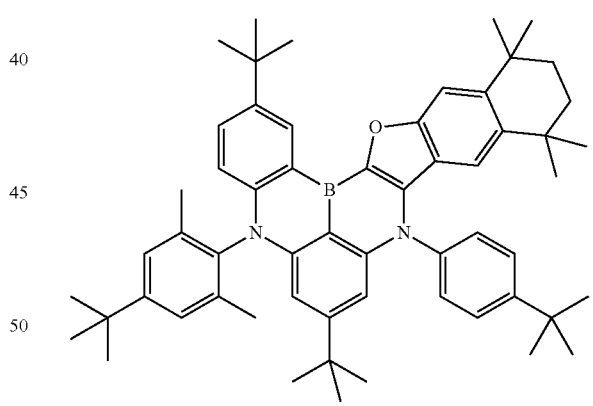 |
| 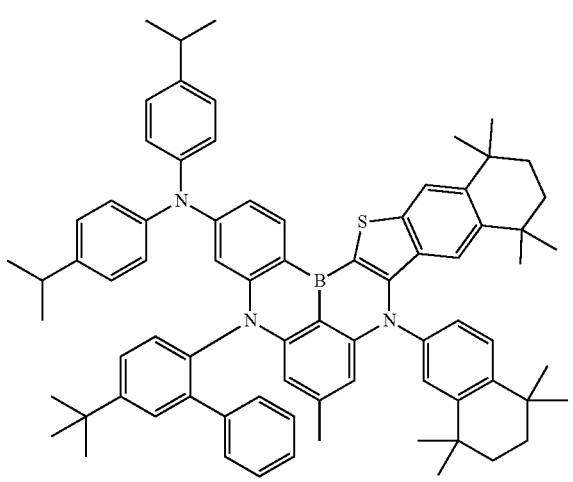 | 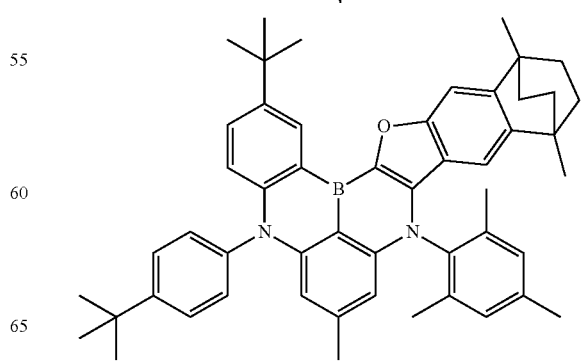 |

| 309 -continued | 310 -continued |
|---|---|
| 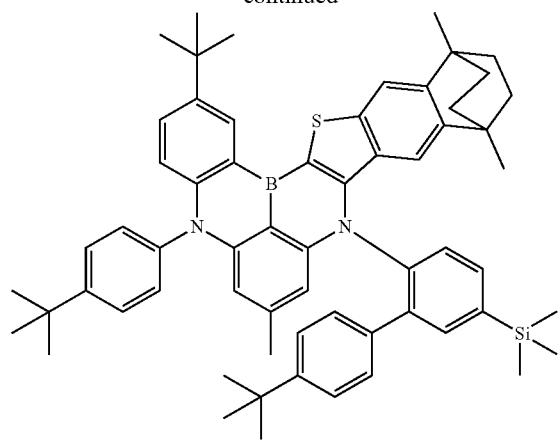 | 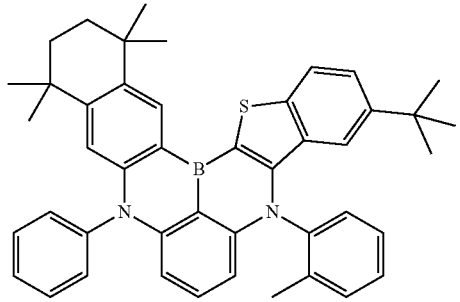 |
| 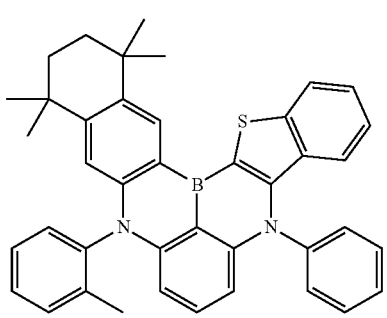 | 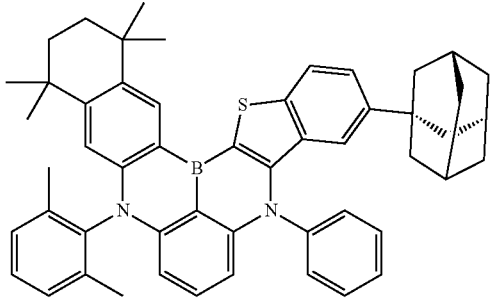 |
| 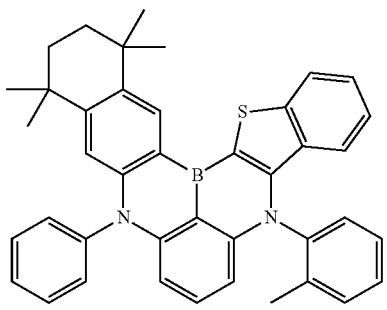 | 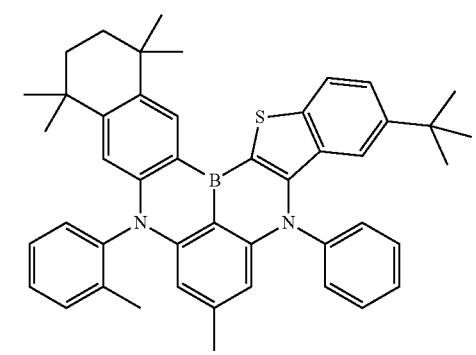 |
| 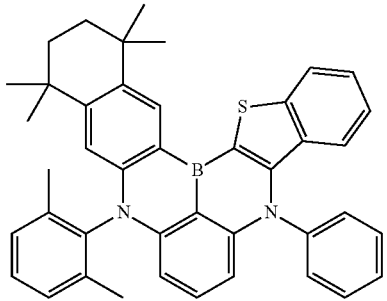 | 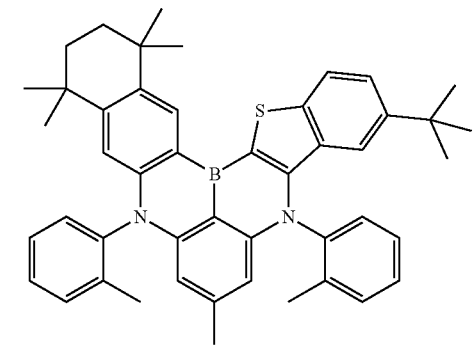 |
| 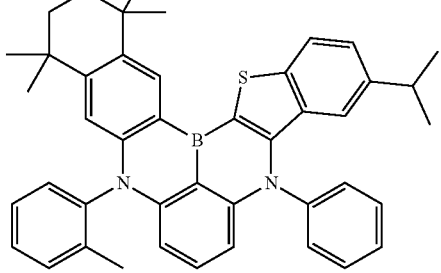 | 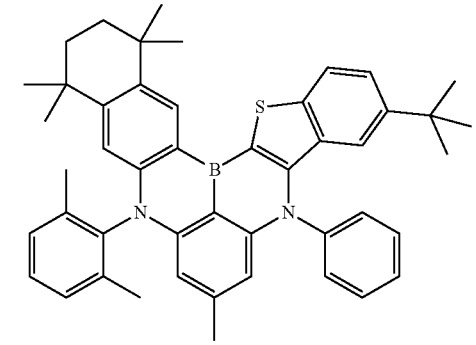 |

311
-continued
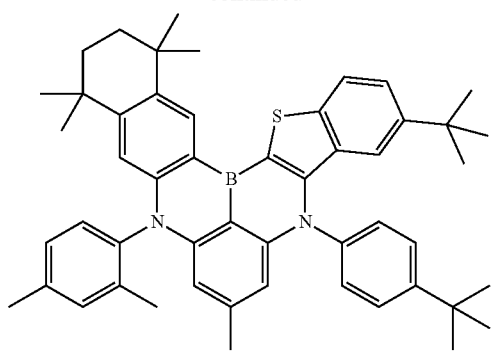
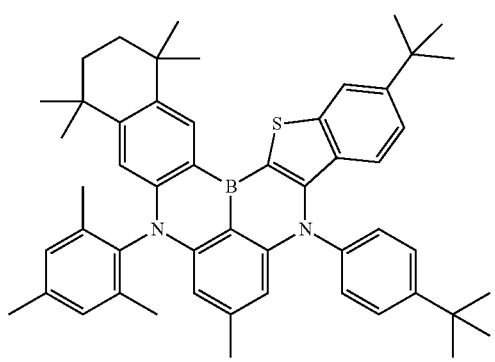
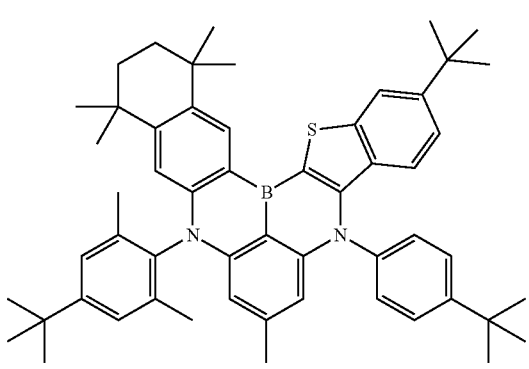
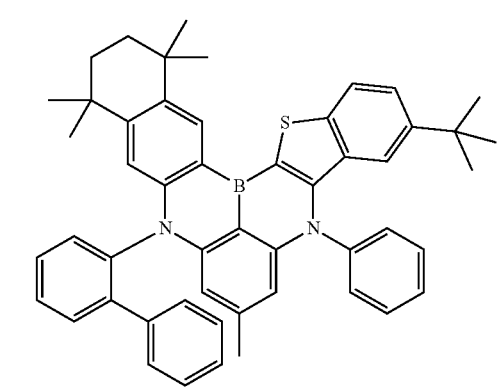
312
-continued
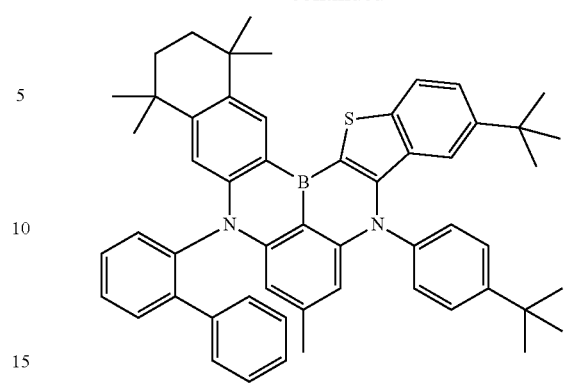
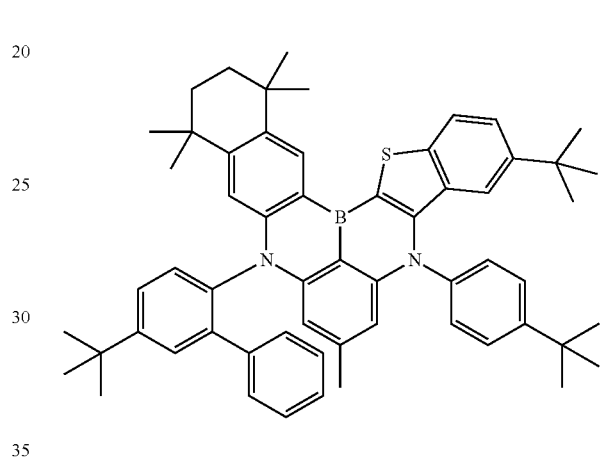
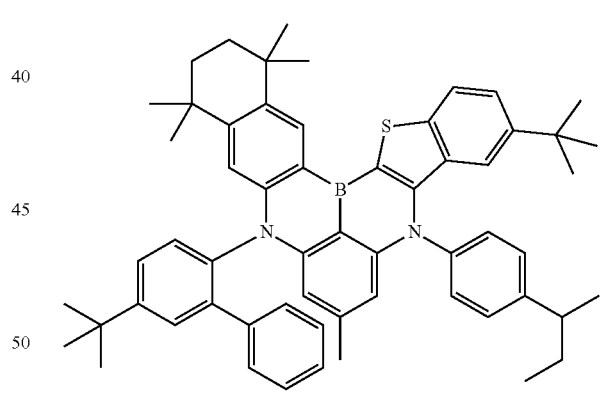
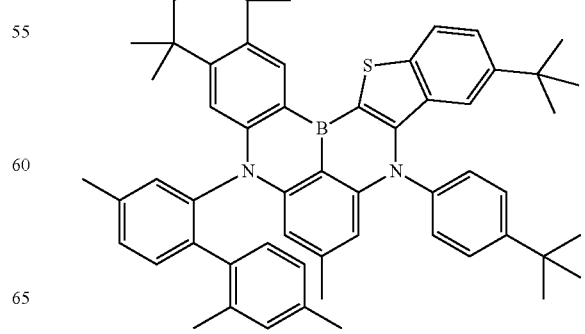

-continued
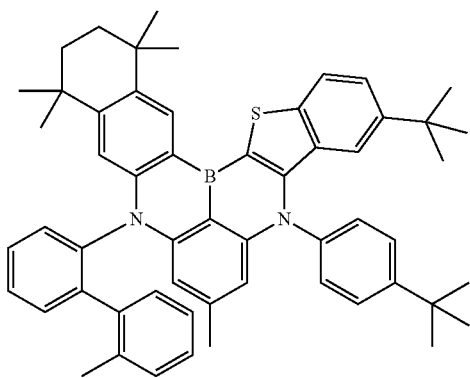
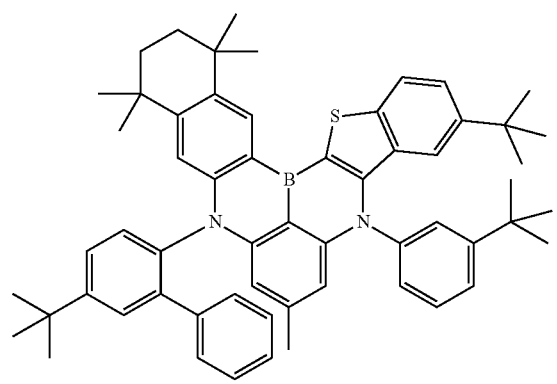
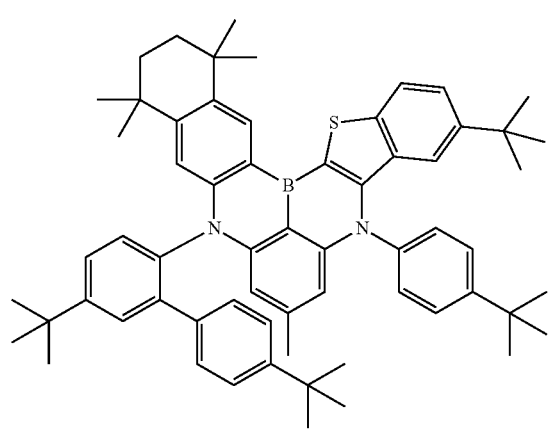
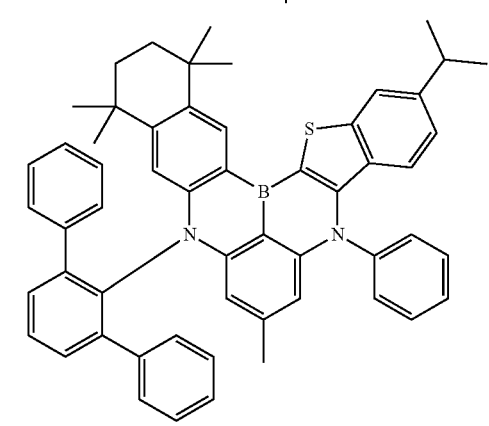
-continued
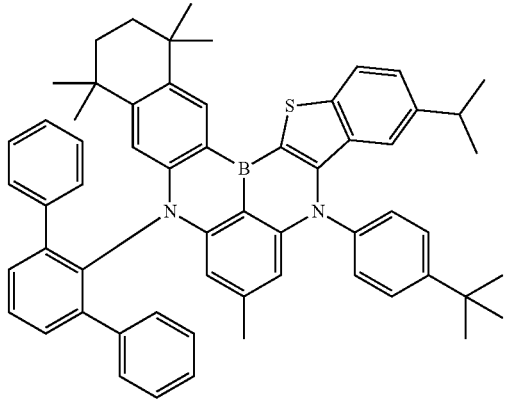
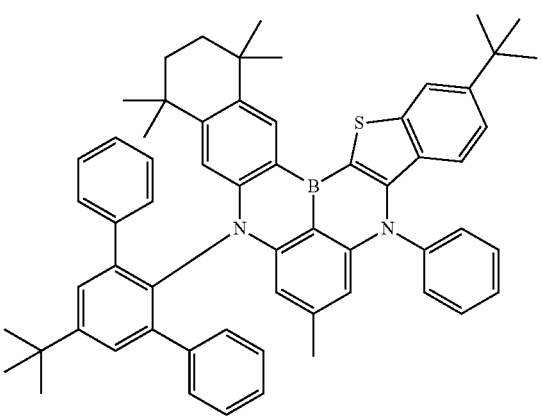
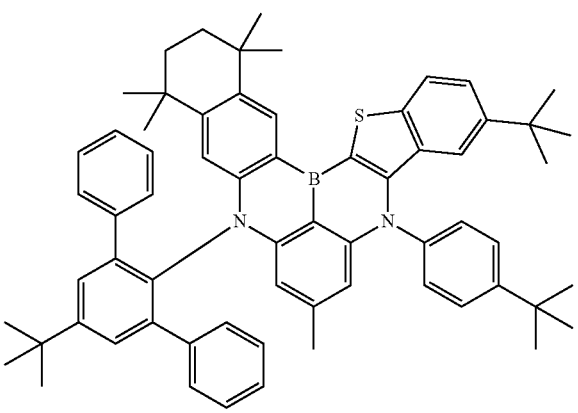
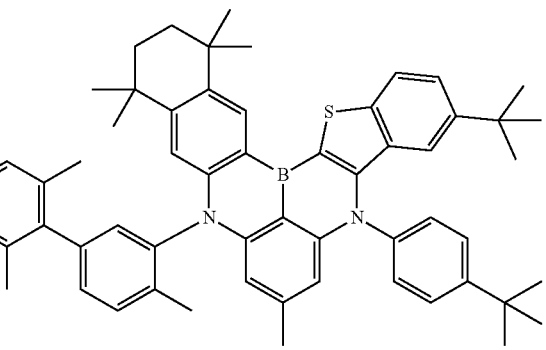

315
-continued
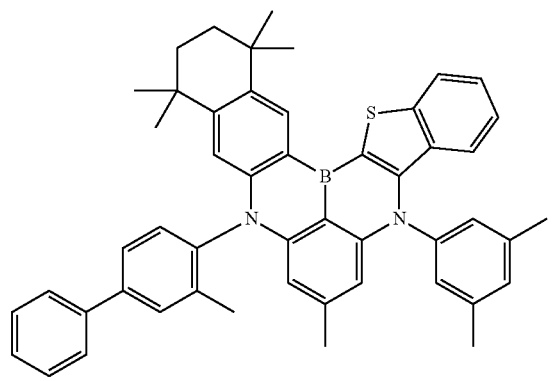
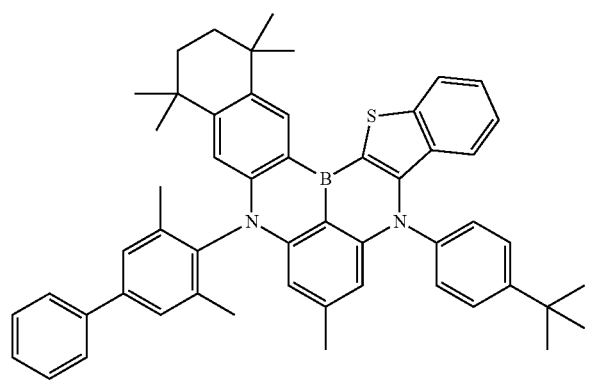
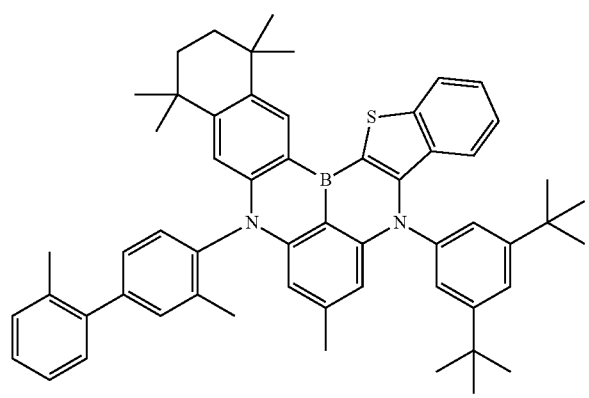
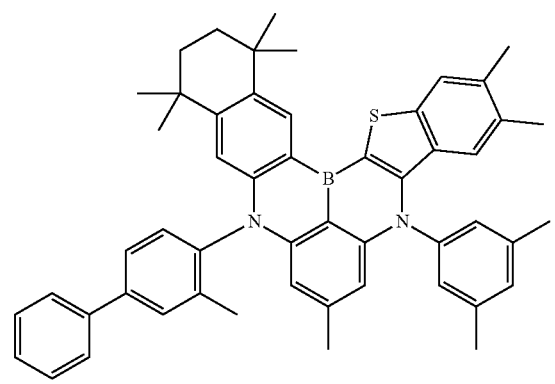
316
-continued
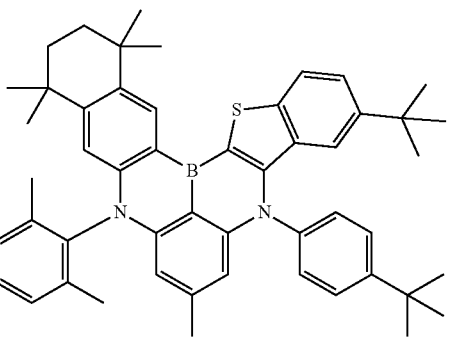
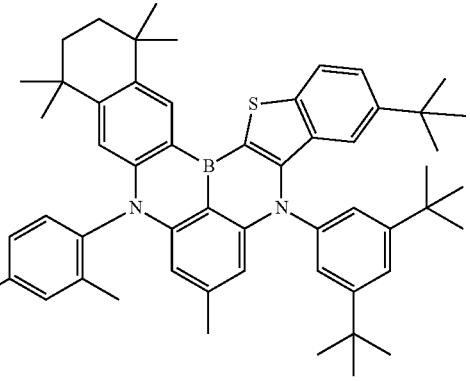
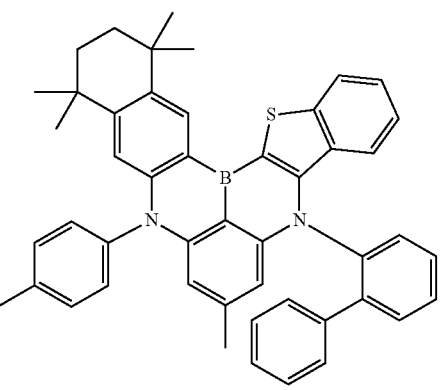
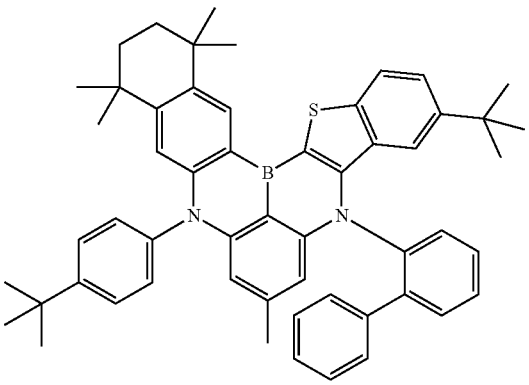

317
-continued
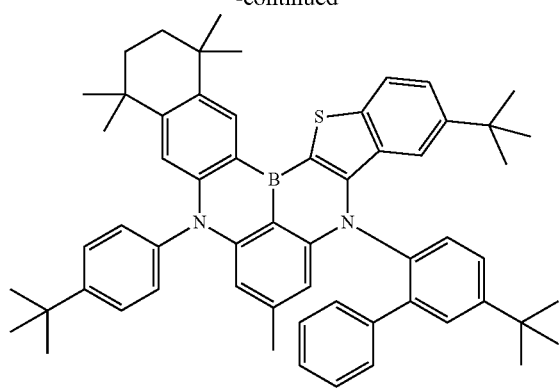
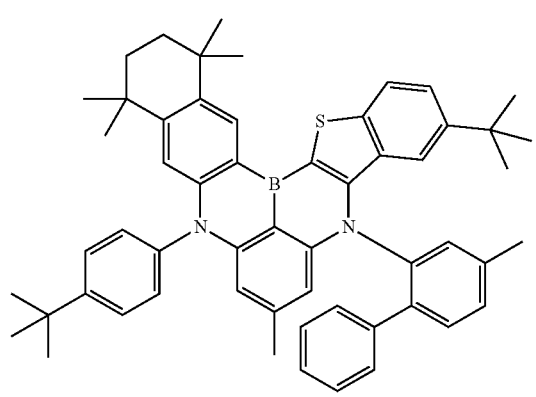
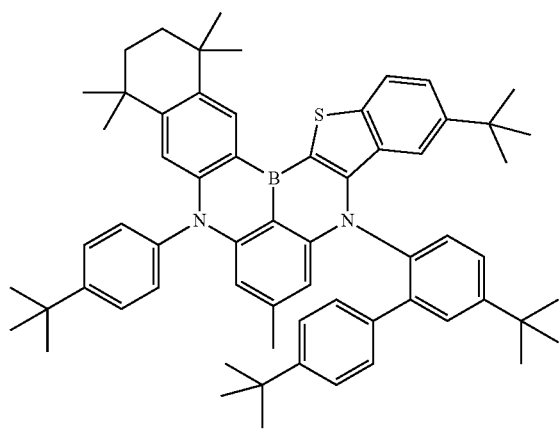
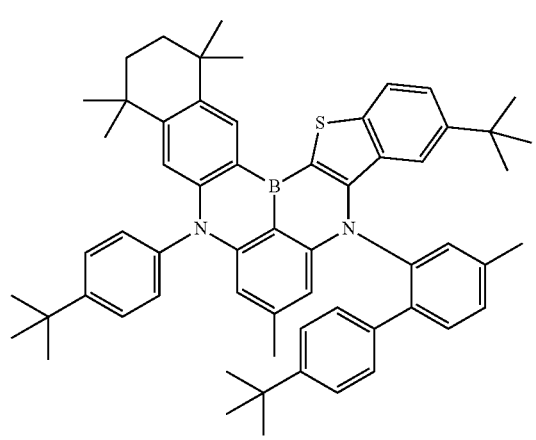
318
-continued
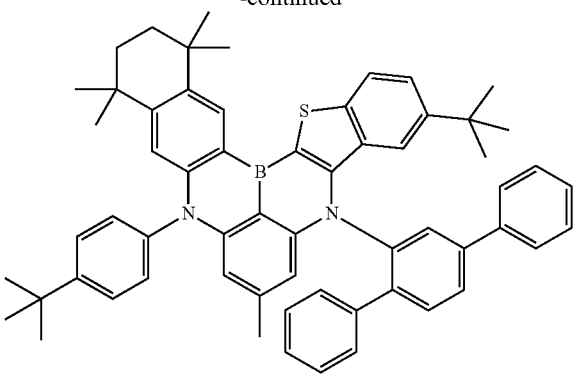
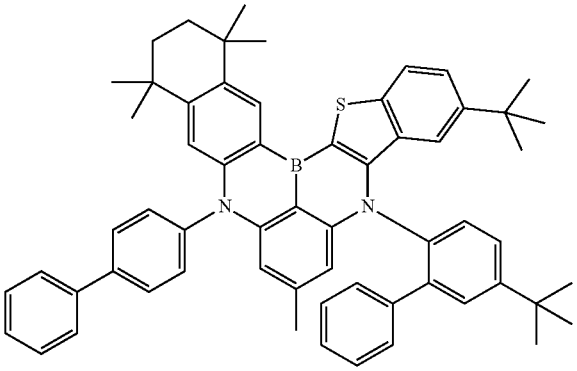
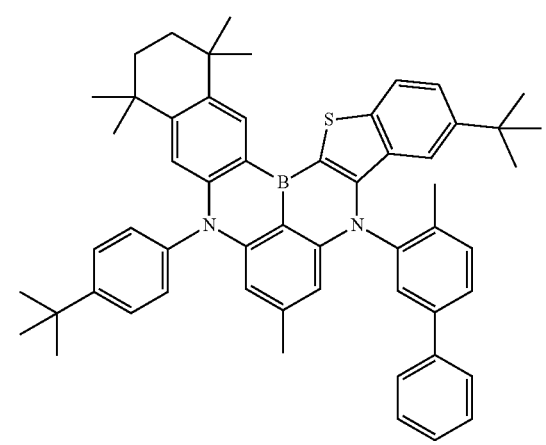
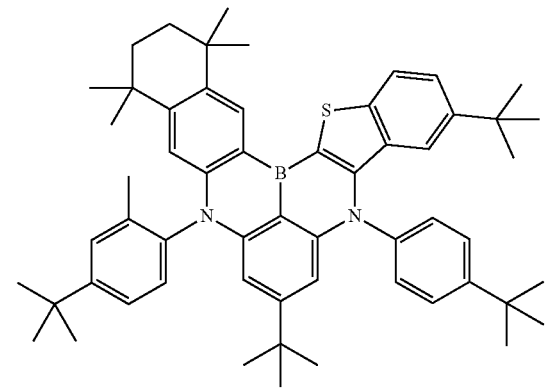

319
-continued
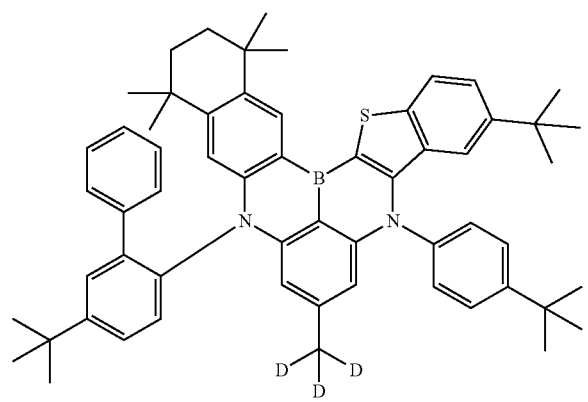
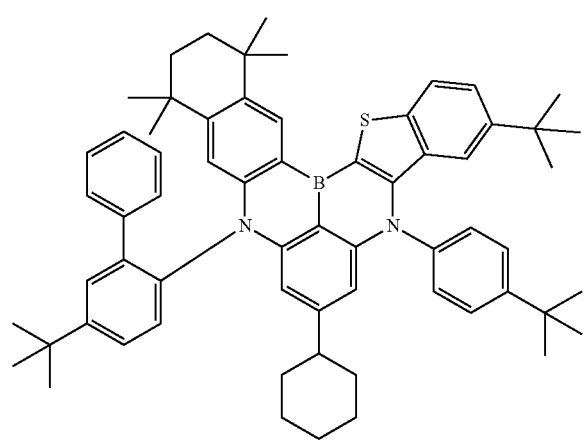
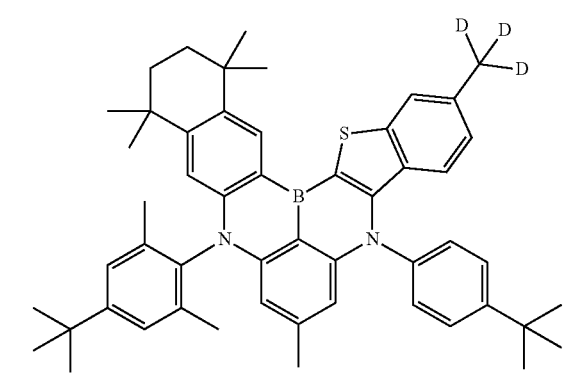
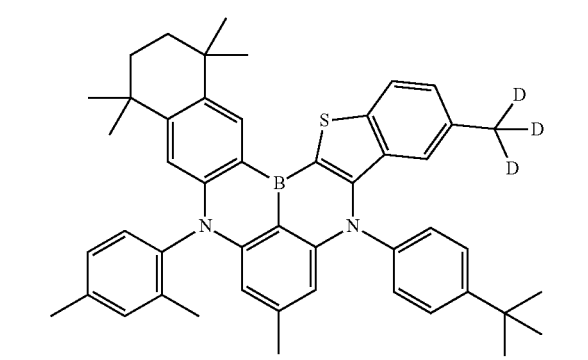
320
-continued
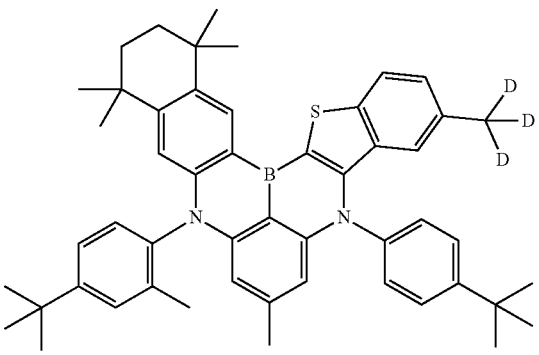
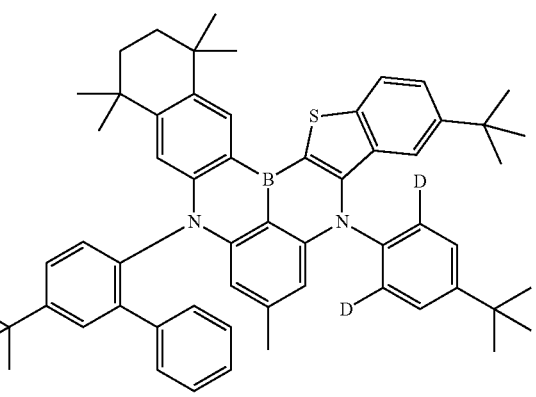
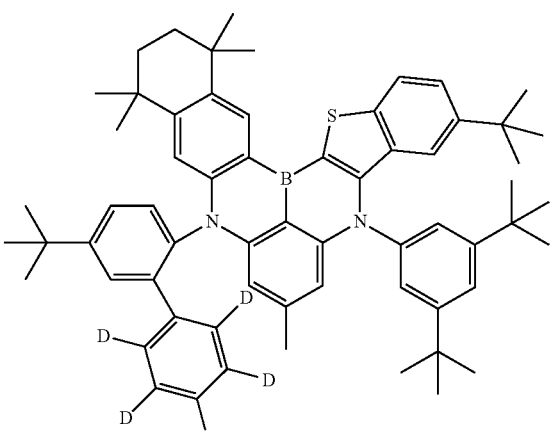
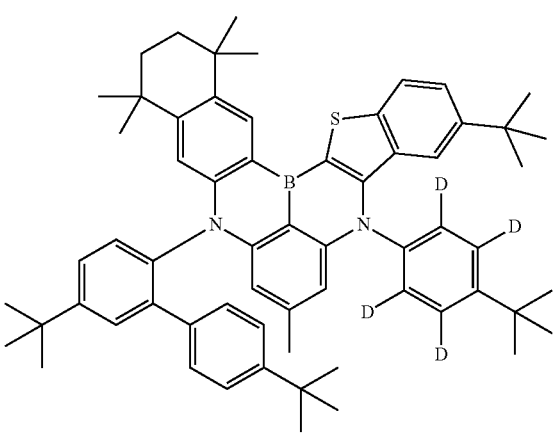

321
-continued
322
-continued
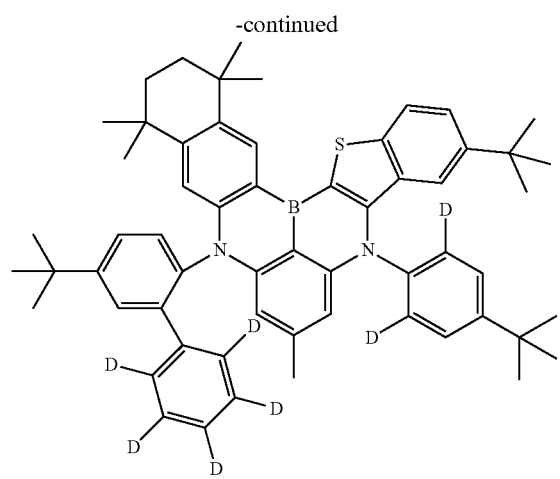
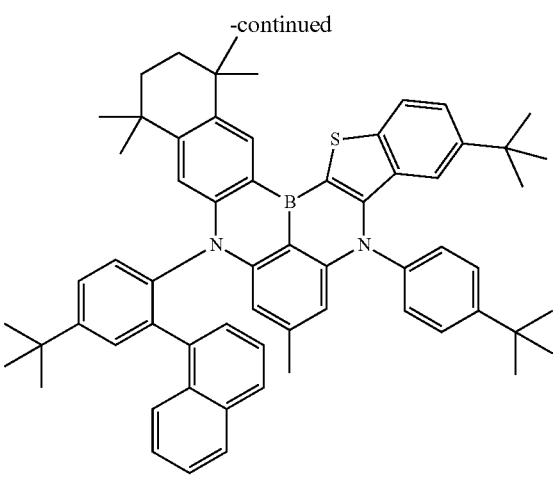

323
-continued
324
-continued
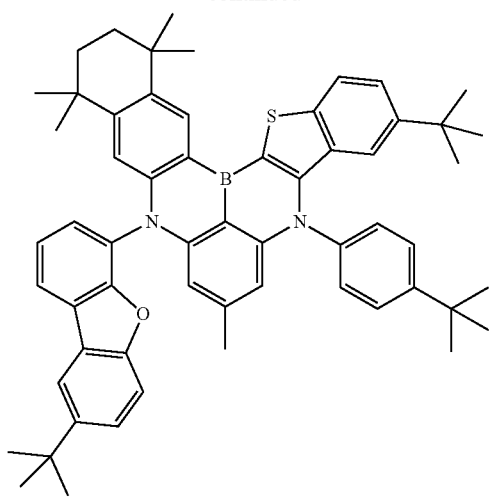
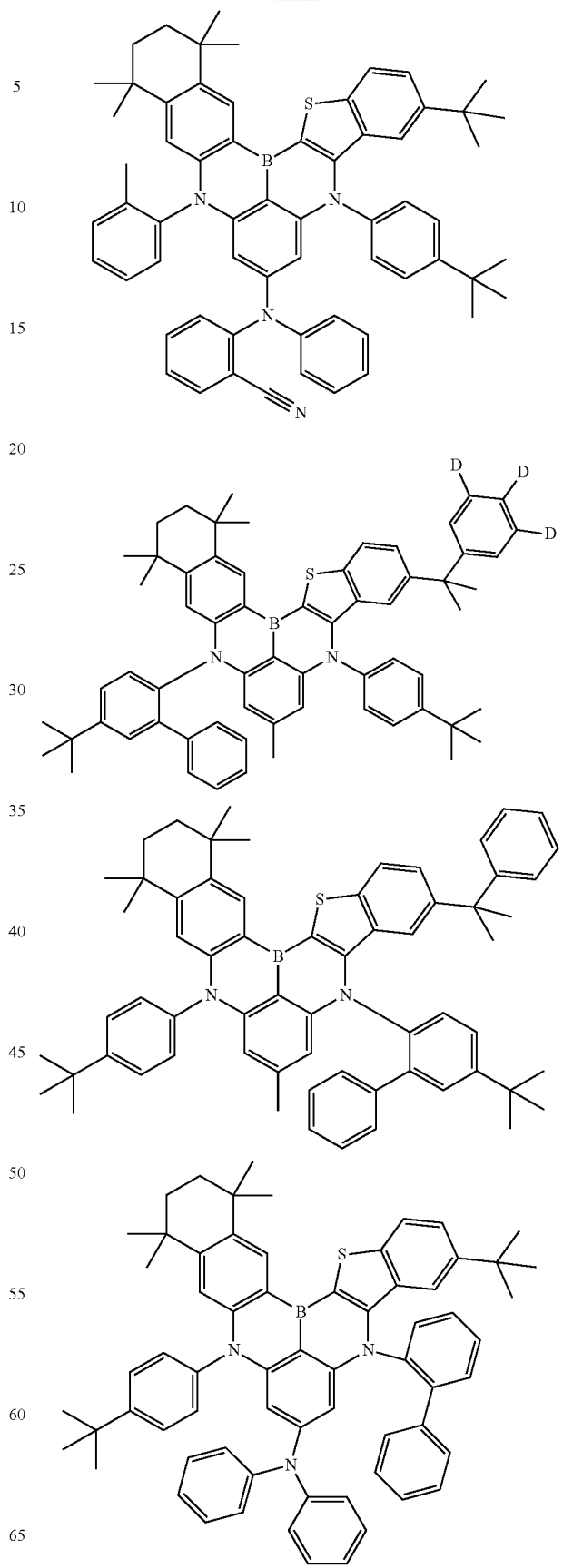

325
-continued
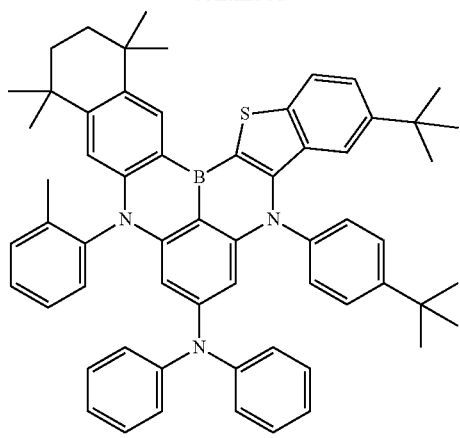
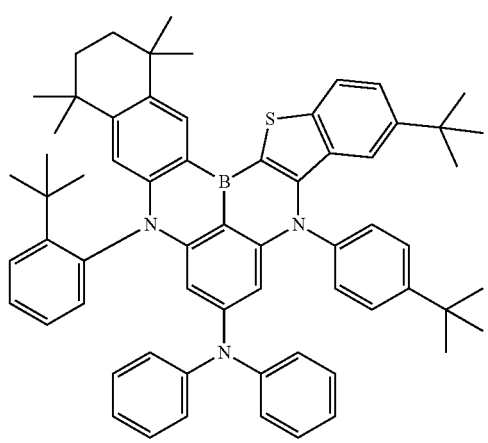
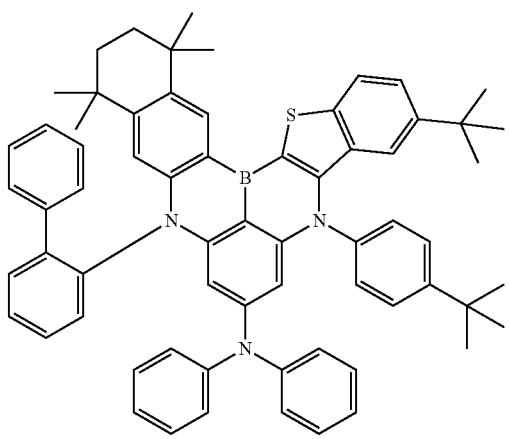
326
-continued
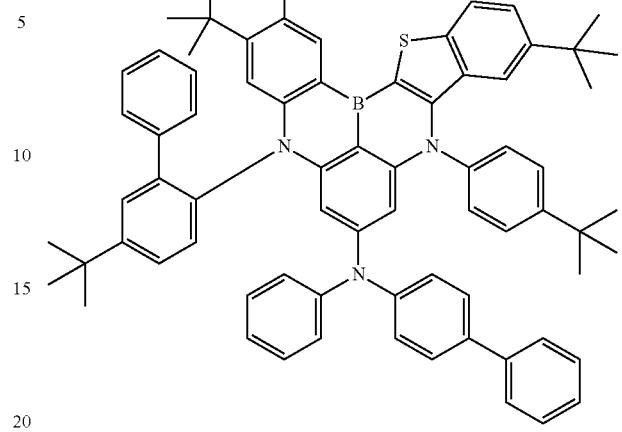
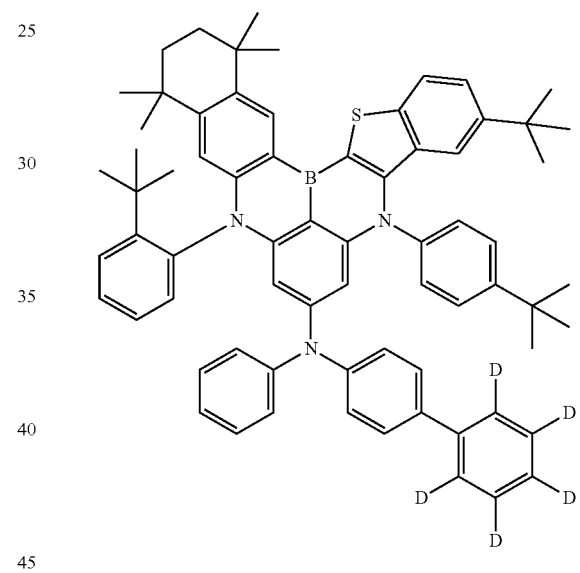
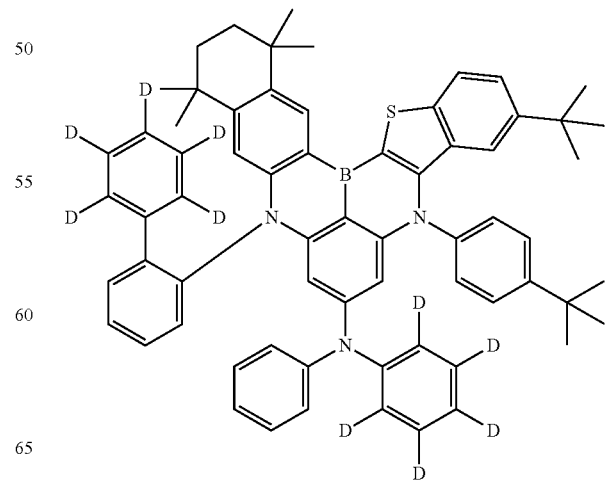

| 327 -continued | 328 -continued |
|---|---|
| 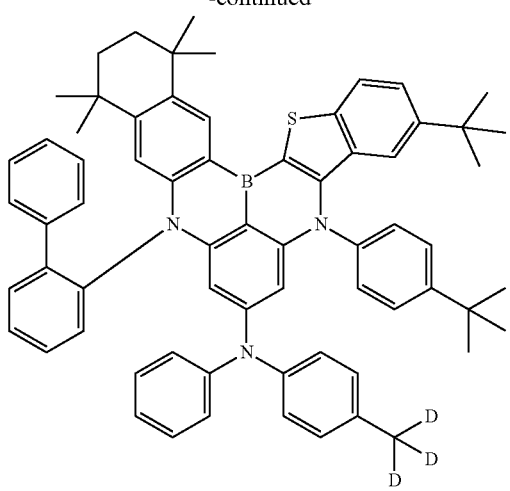 | 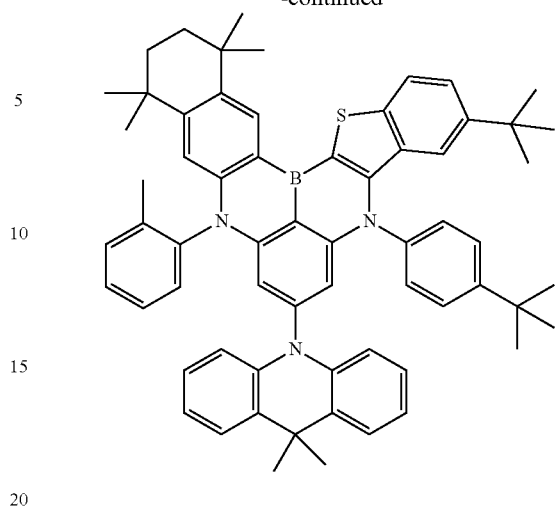 |
| 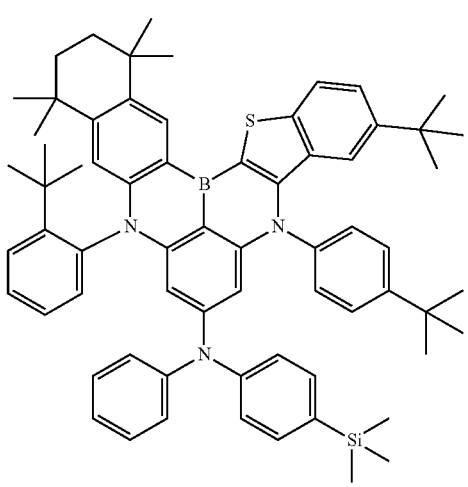 | 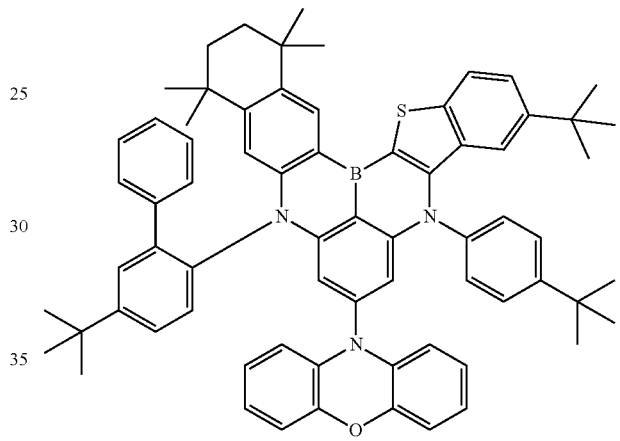 |
| 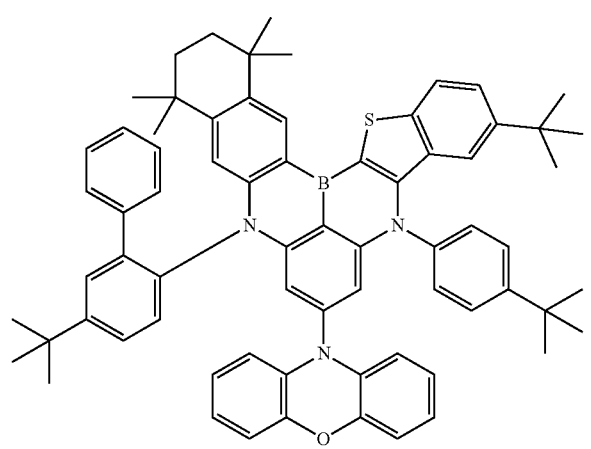 | 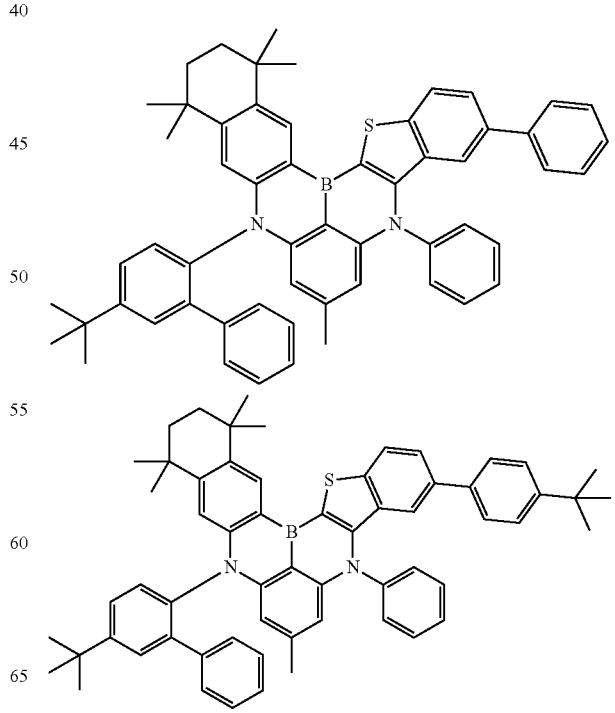 |

329
-continued
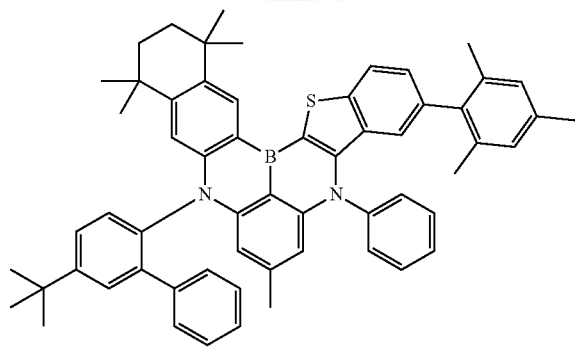
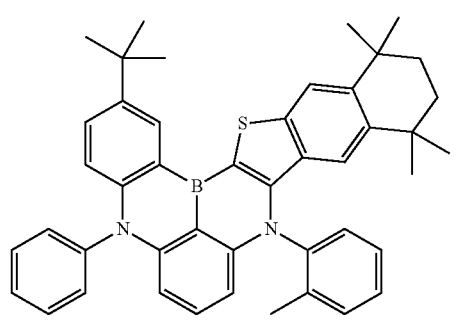
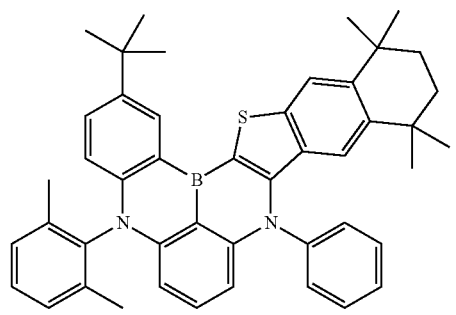
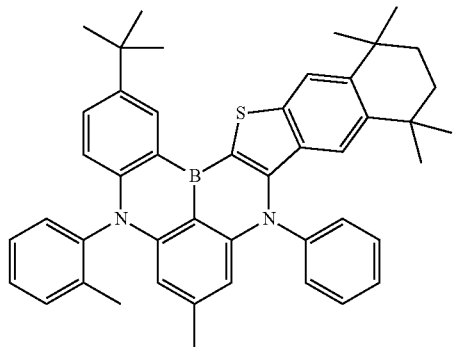
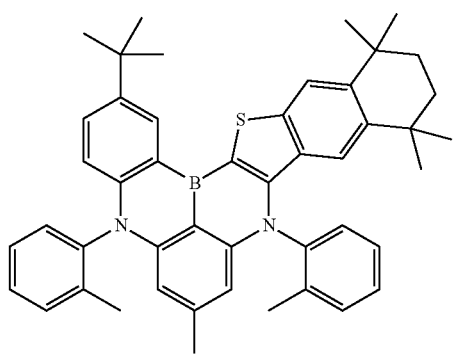
330
-continued
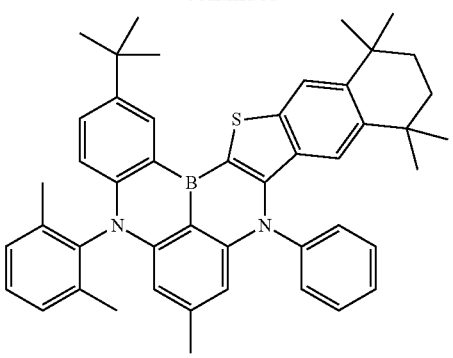
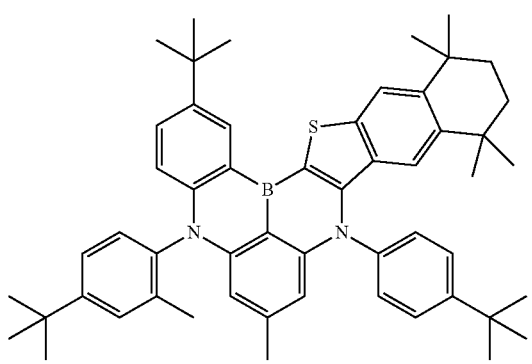

331
-continued
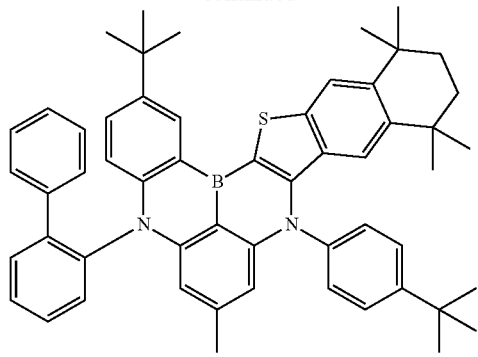
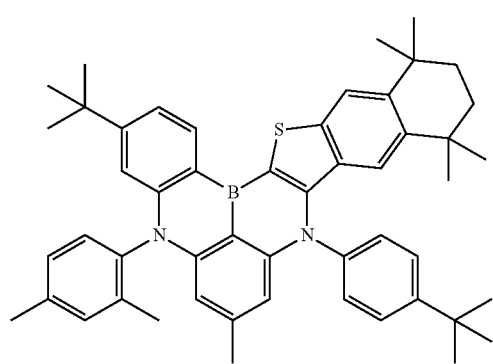
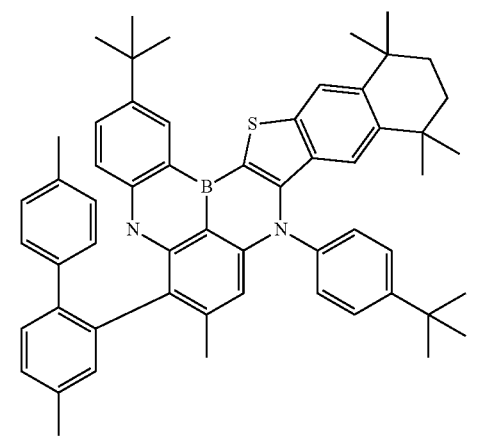
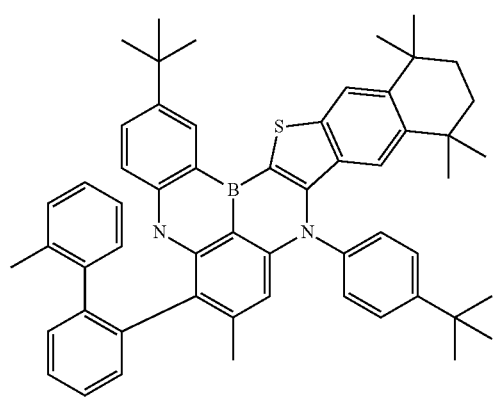
332
-continued
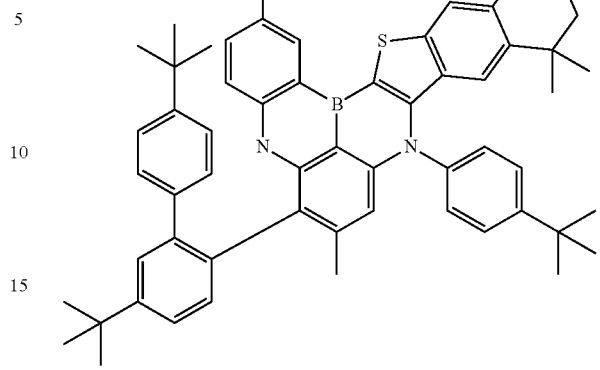
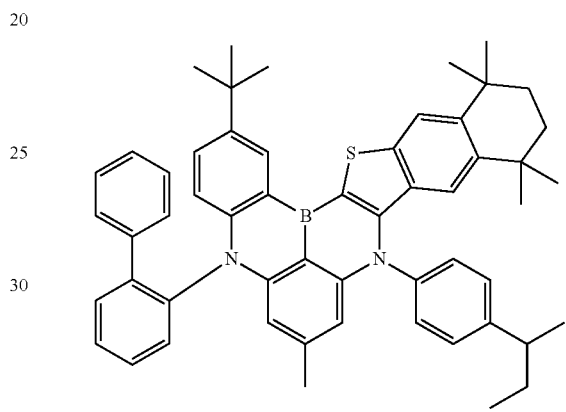
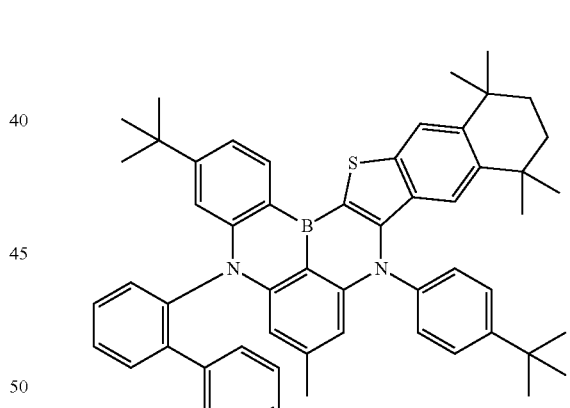
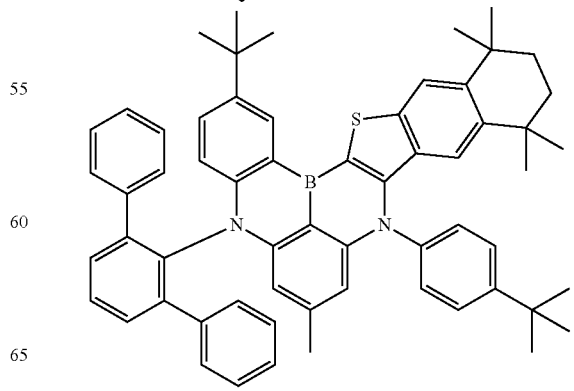

333
-continued
334
-continued
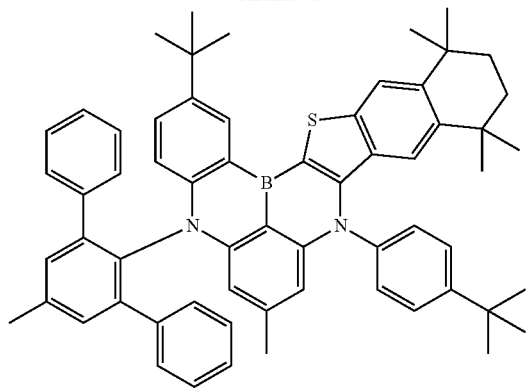
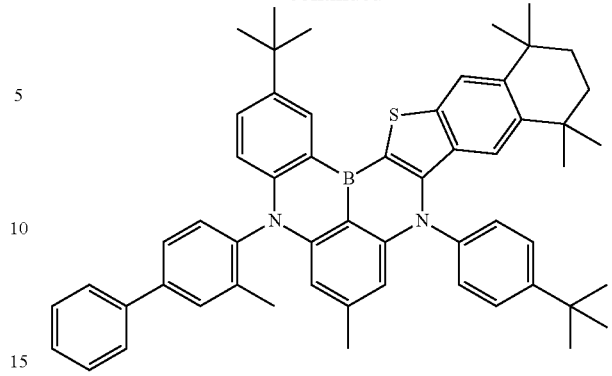
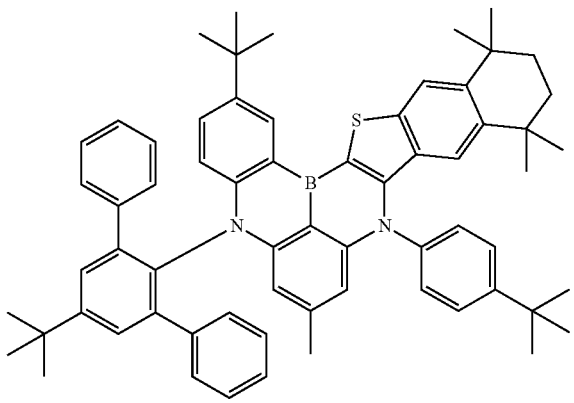
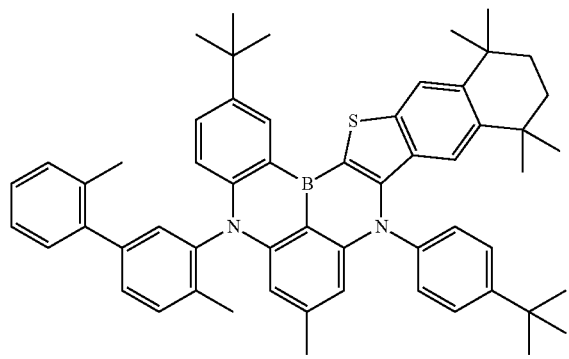
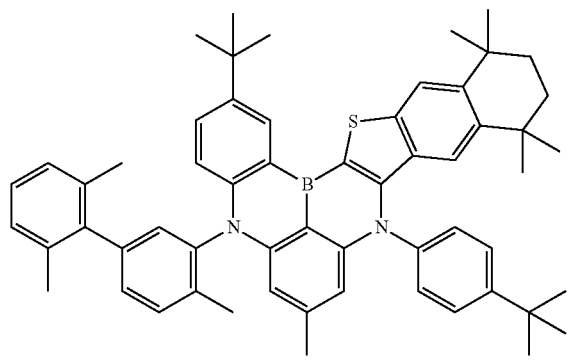

| 335 -continued | 336 -continued |
|---|---|
| 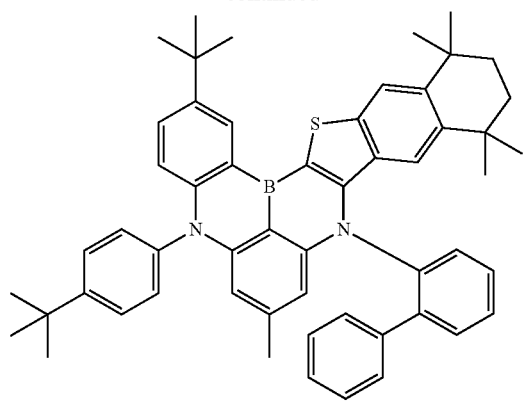 | 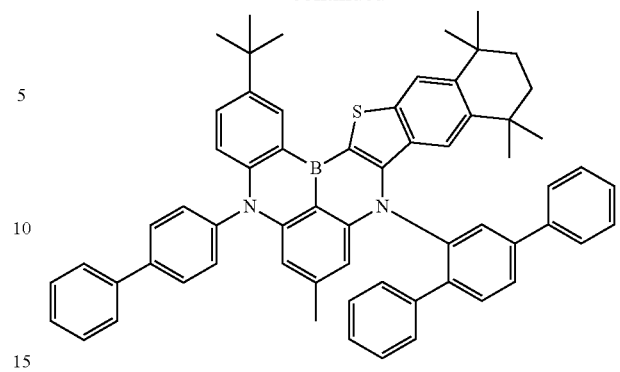 |
| 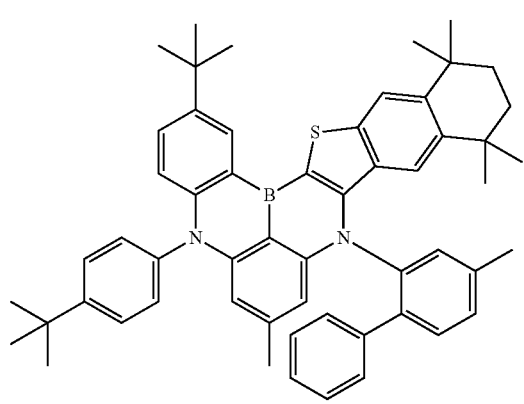 | 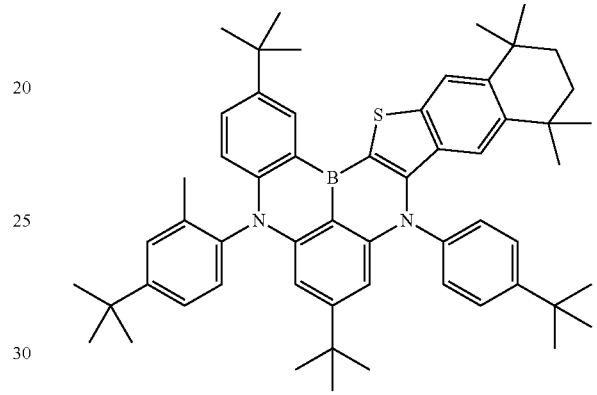 |
| 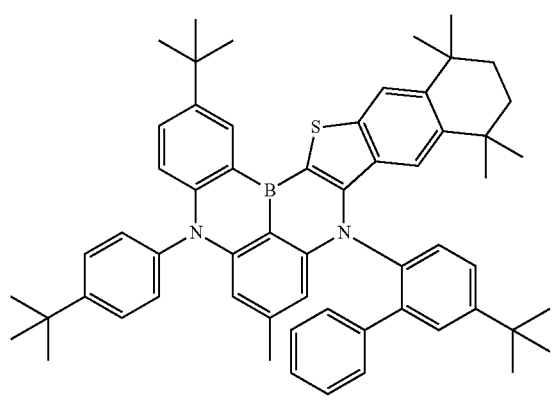 | 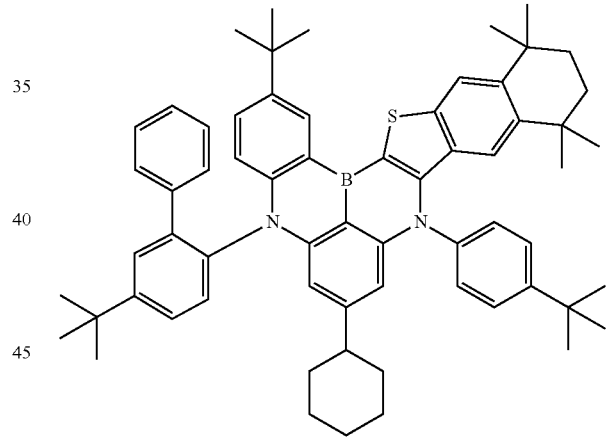 |
| 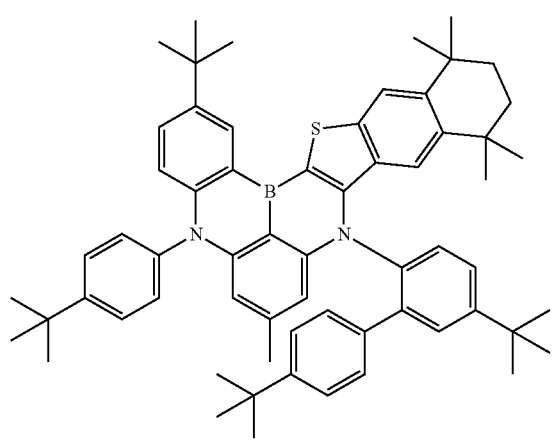 | 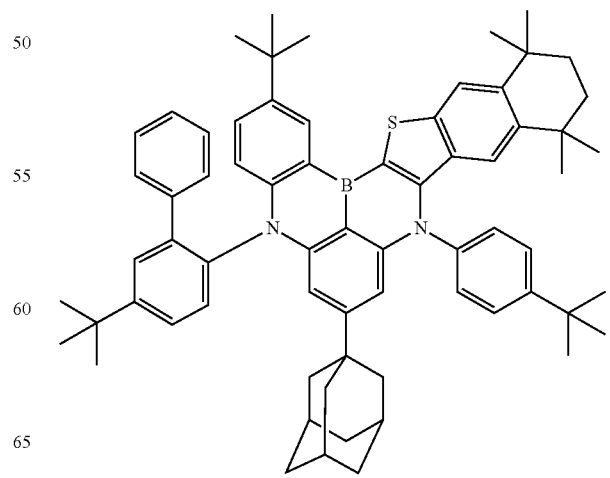 |

337
-continued
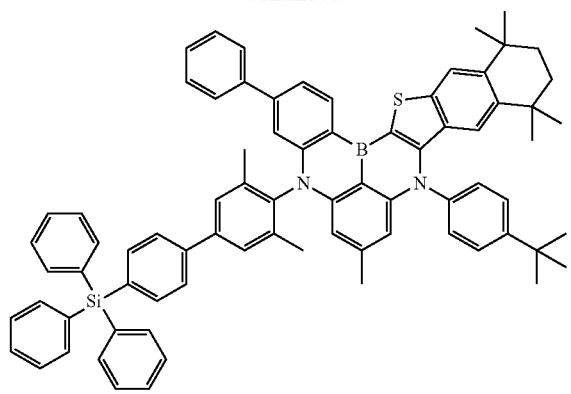
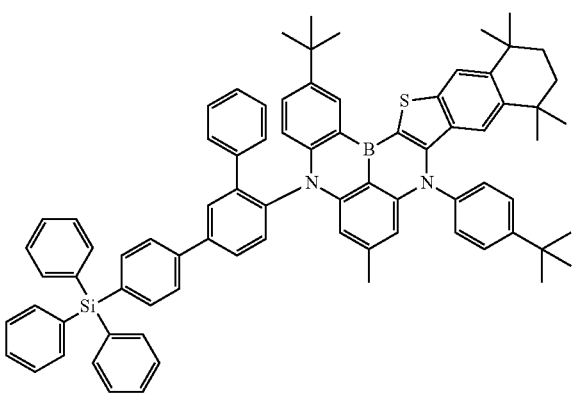
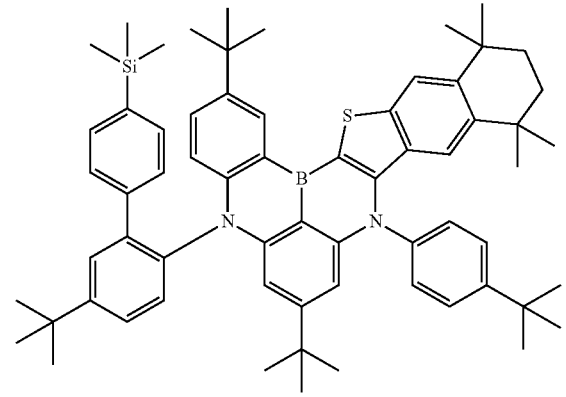
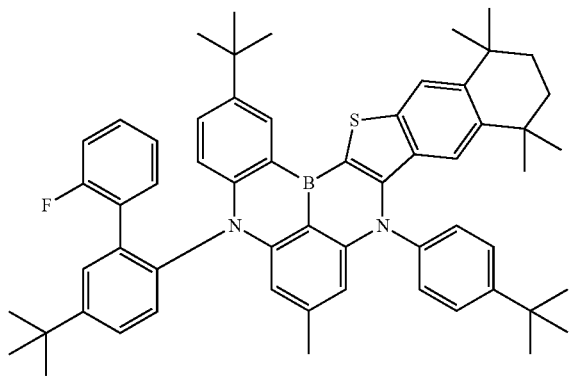
338
-continued
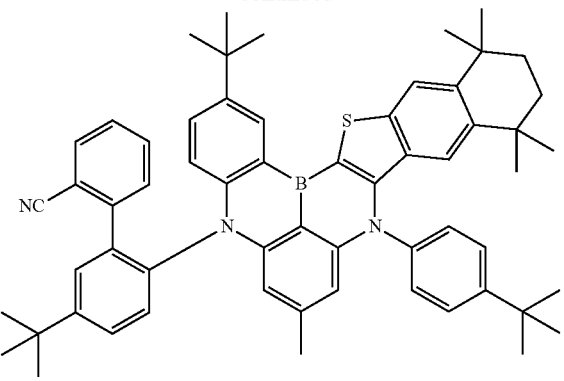
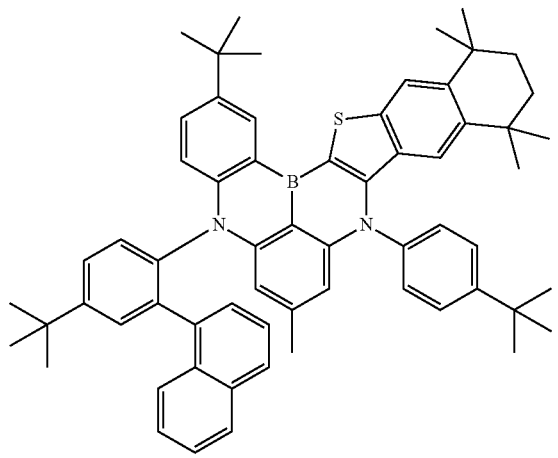
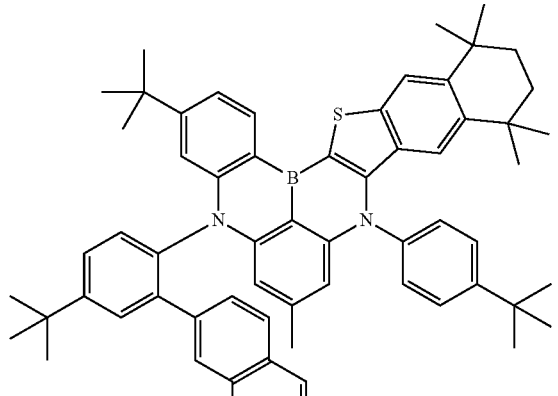
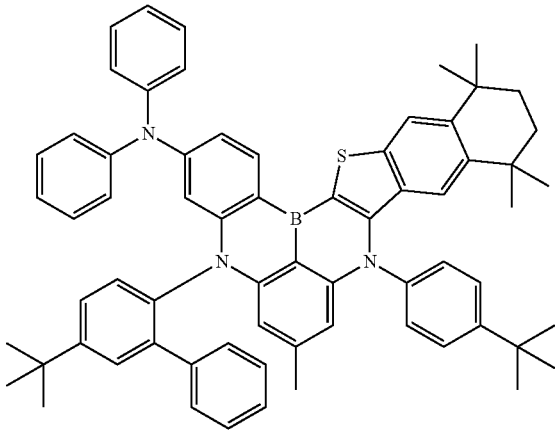

339
-continued
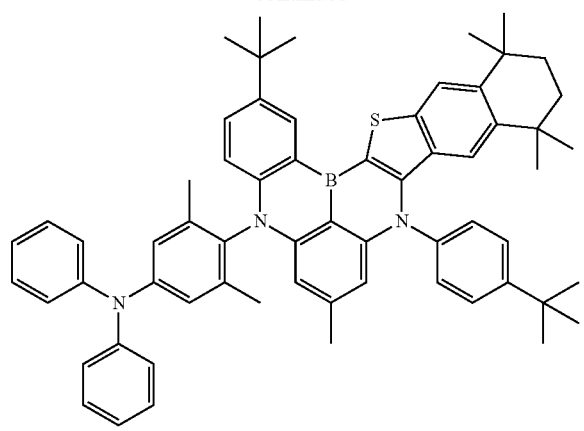
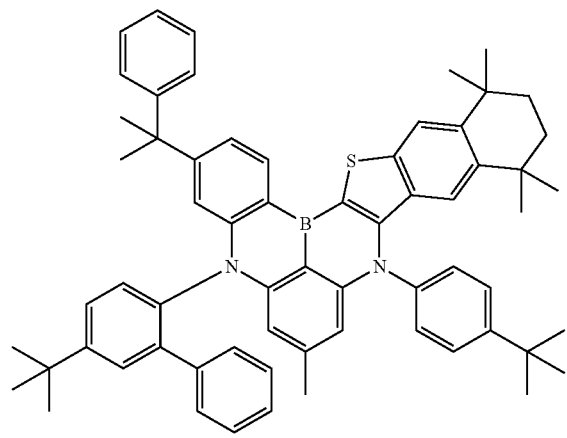
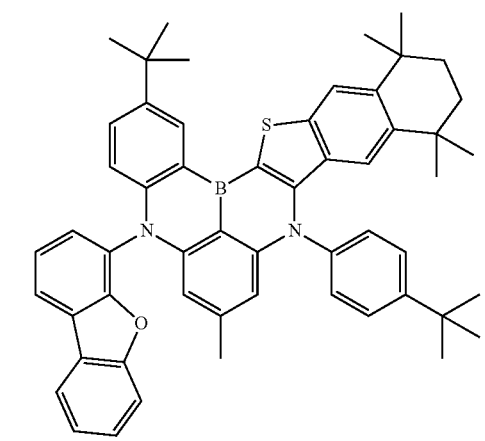
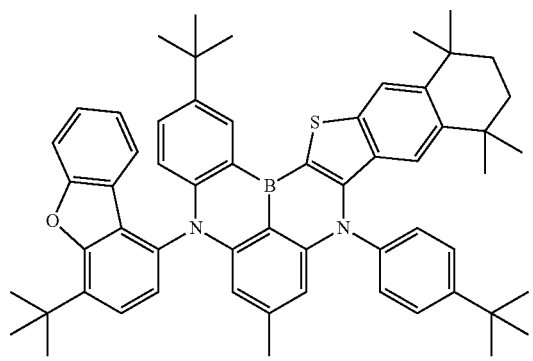
340
-continued
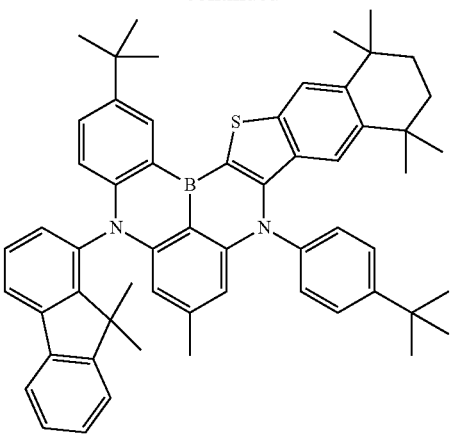
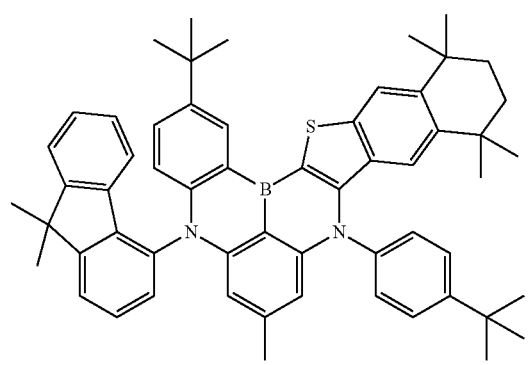
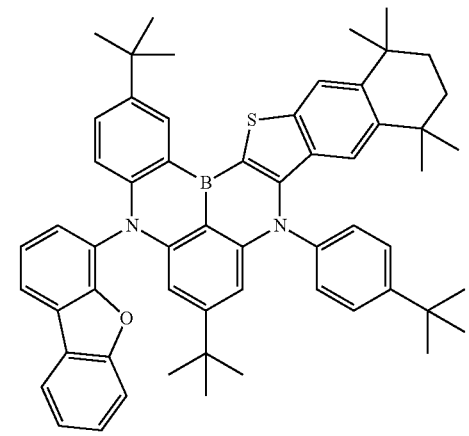
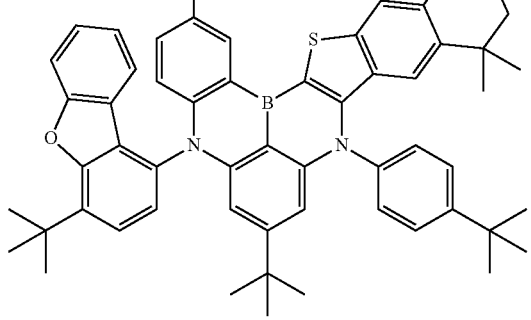

341
-continued
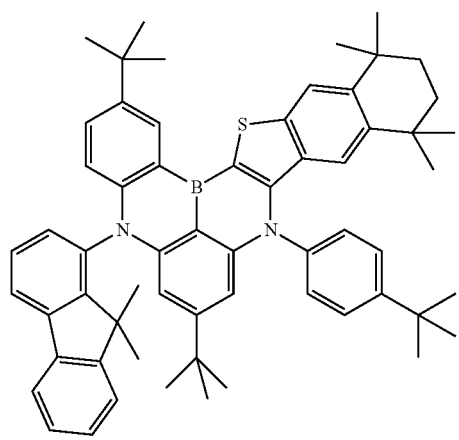
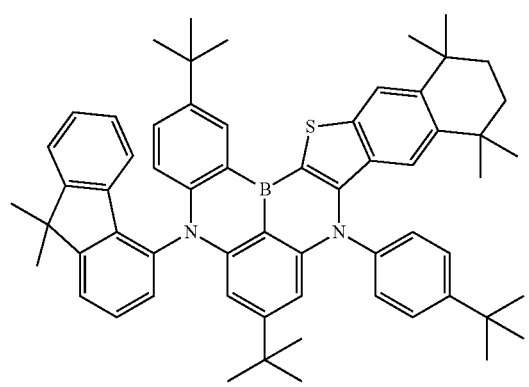
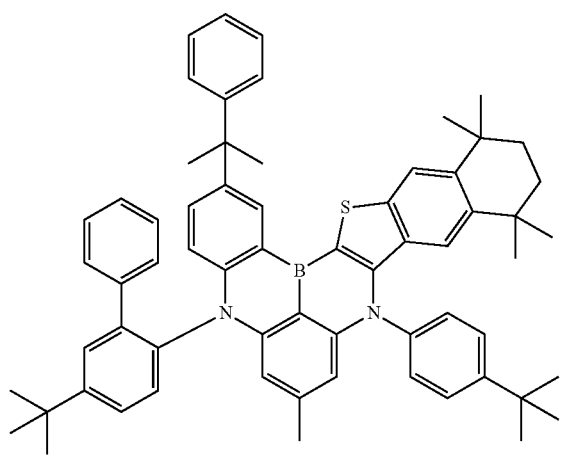
342
-continued
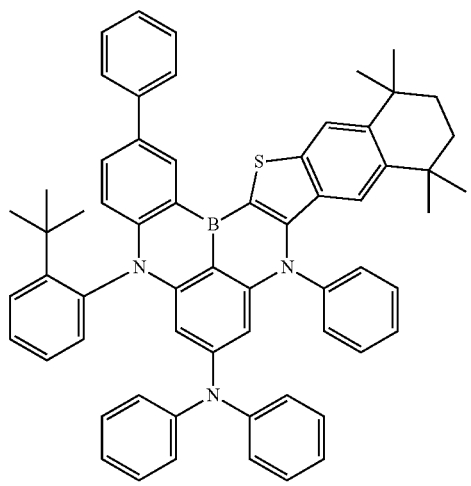
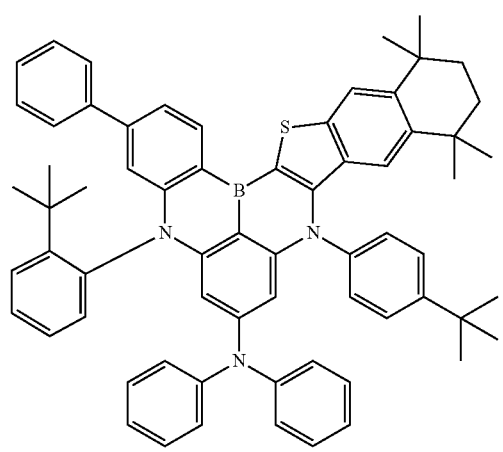
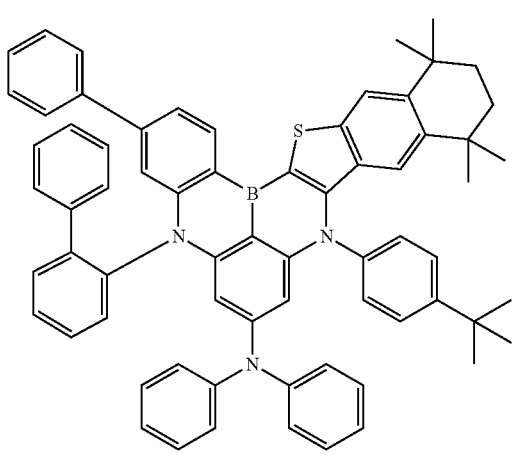

343
-continued
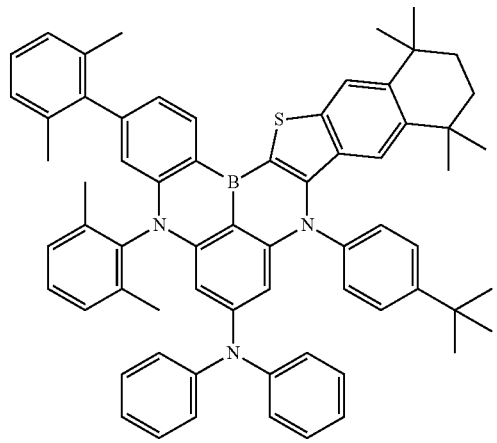
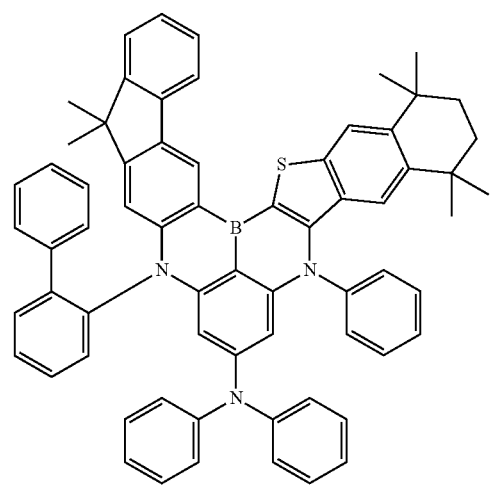
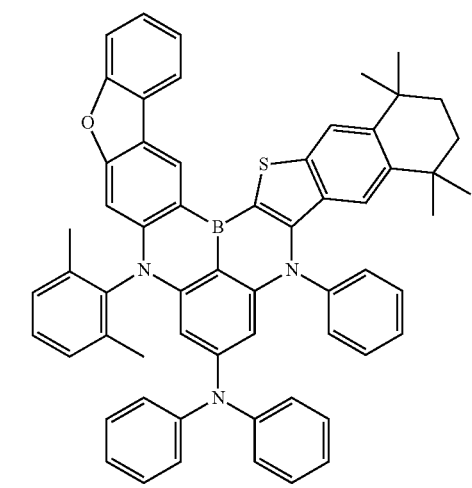
344
-continued
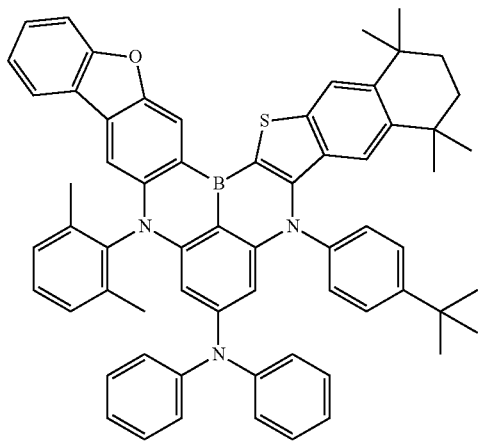
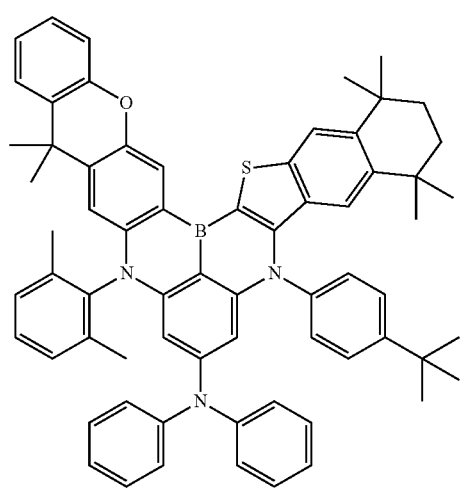
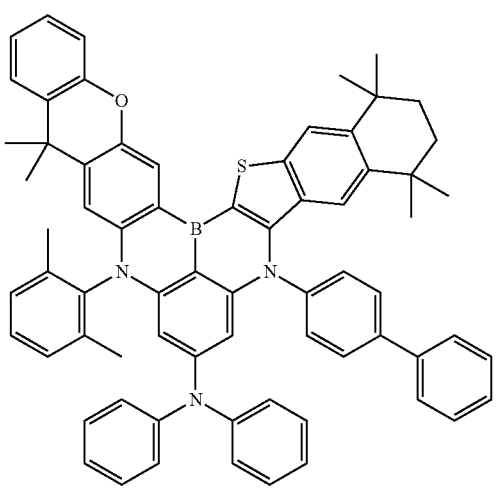

345
-continued
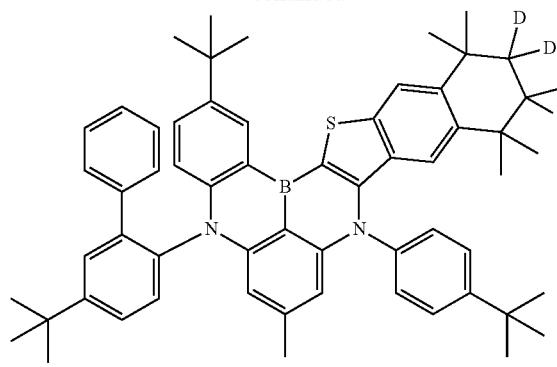
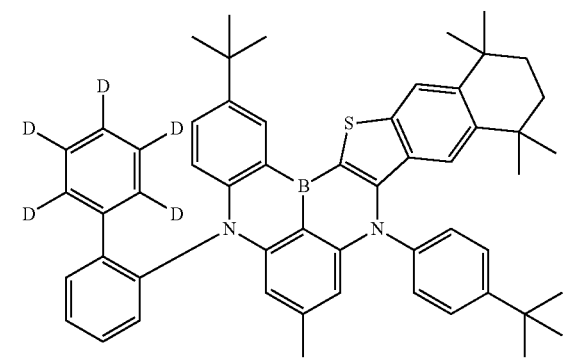
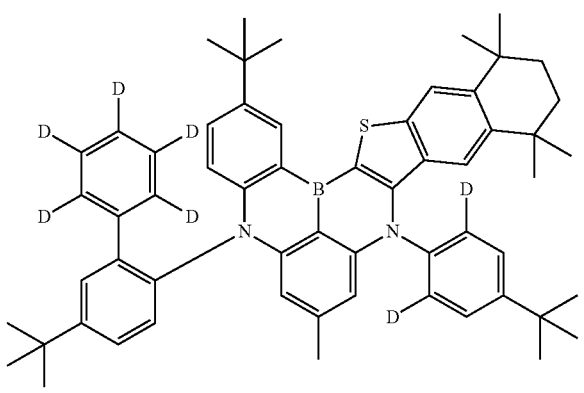
346
-continued
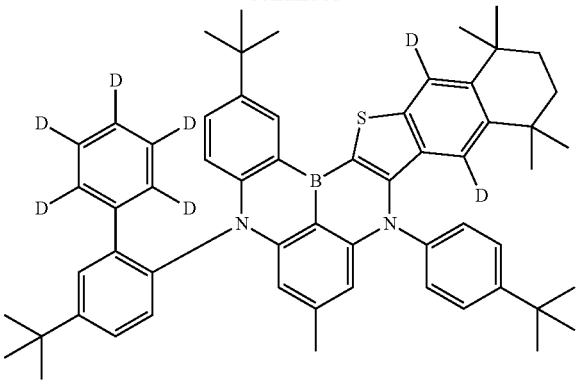
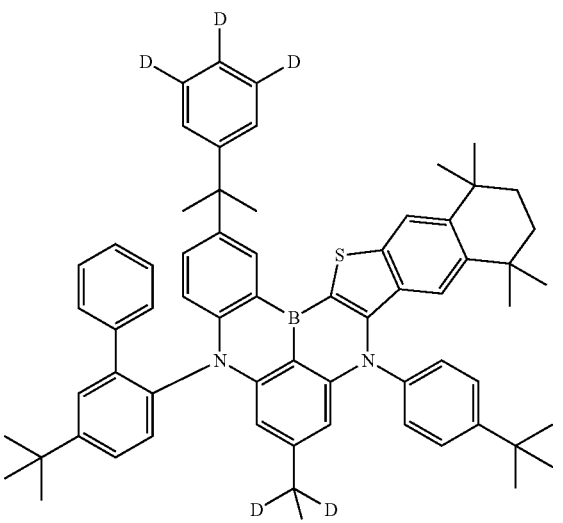

347
-continued
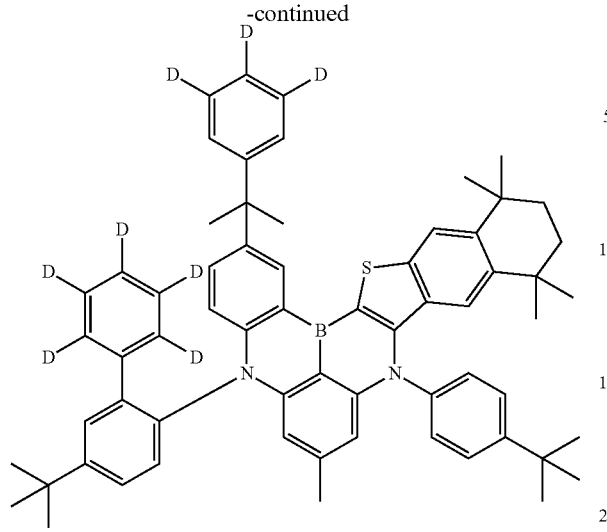
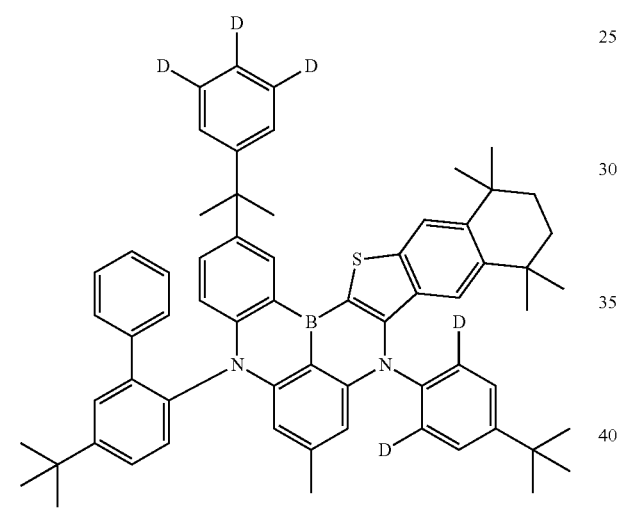
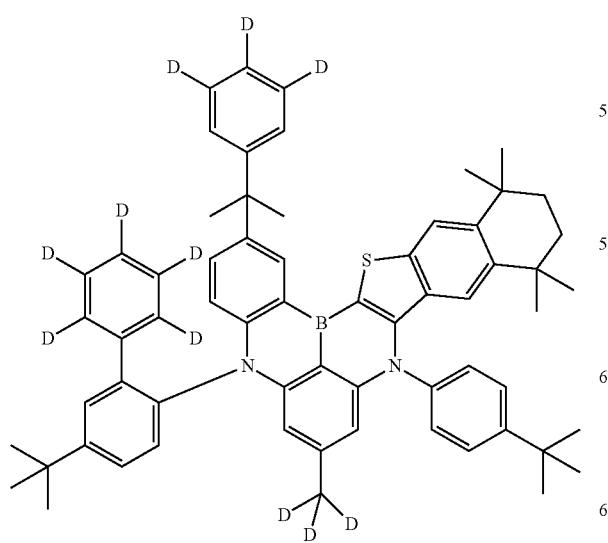
348
-continued
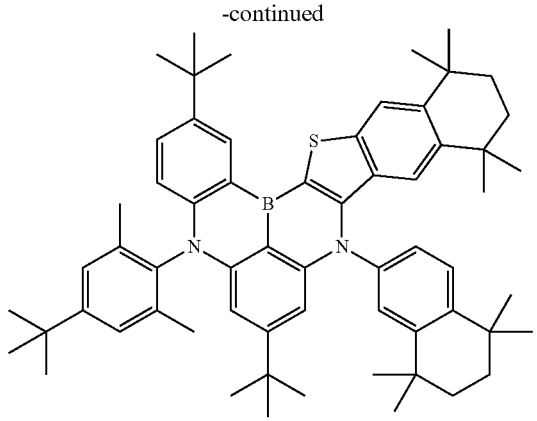
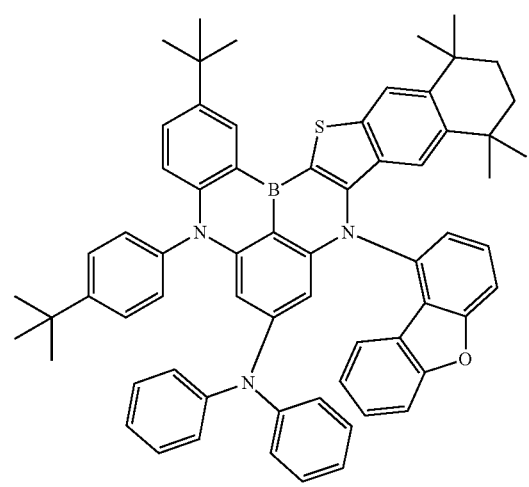
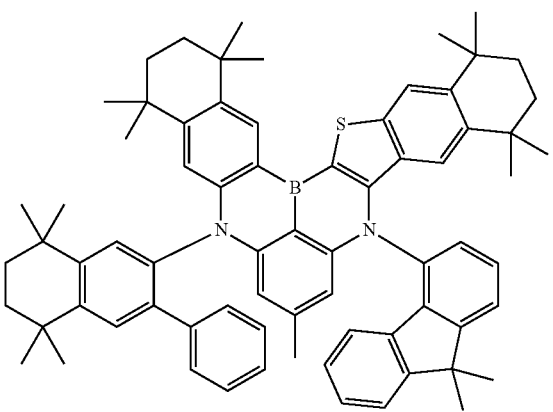

349
-continued
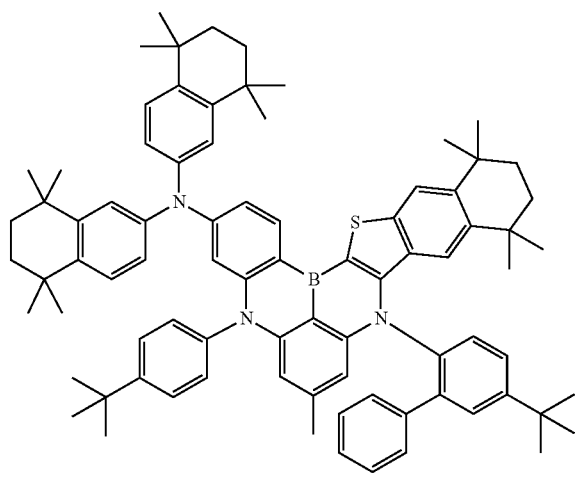
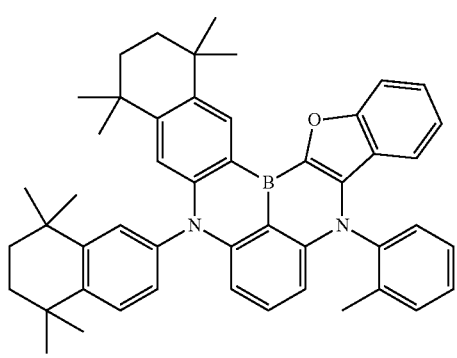
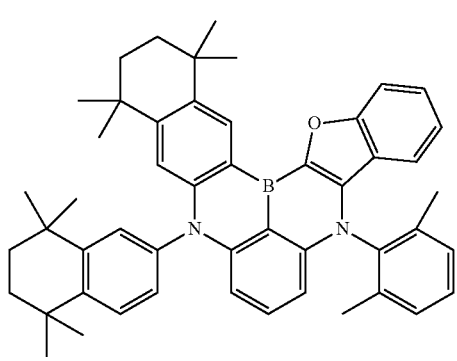
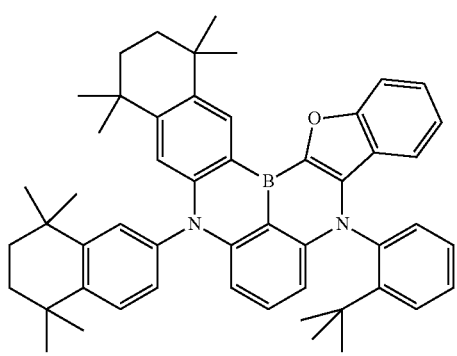
350
-continued
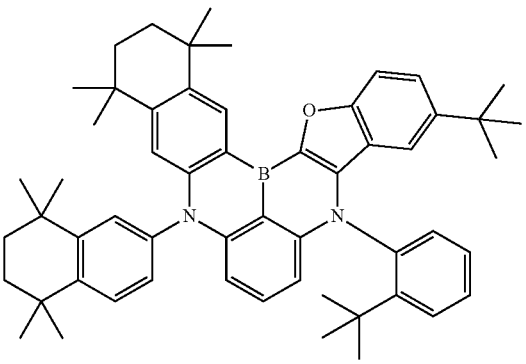
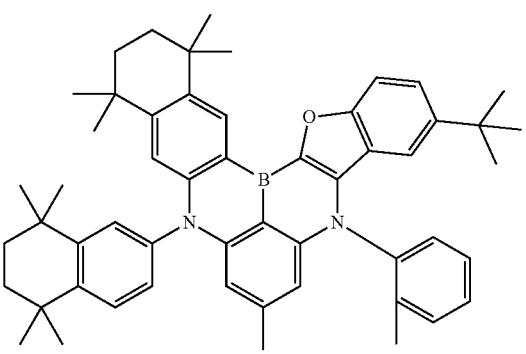
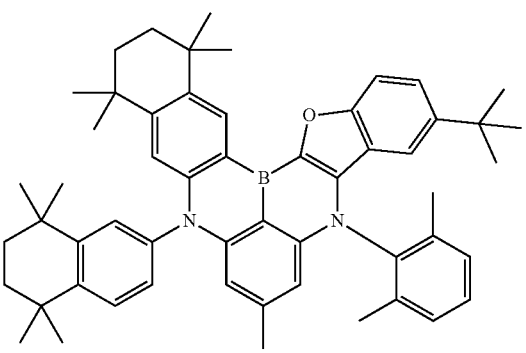
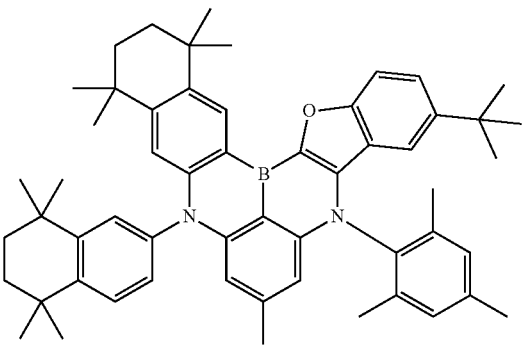

351
-continued
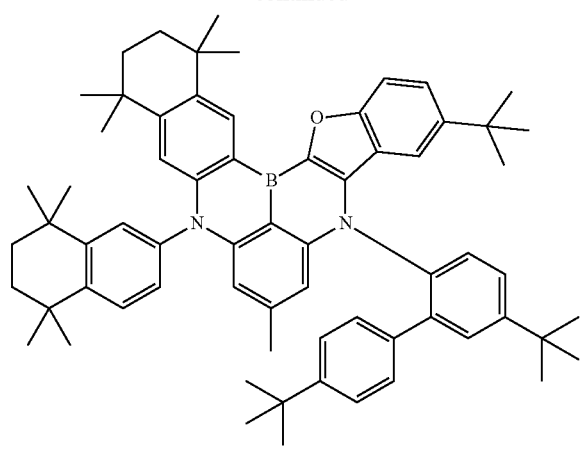
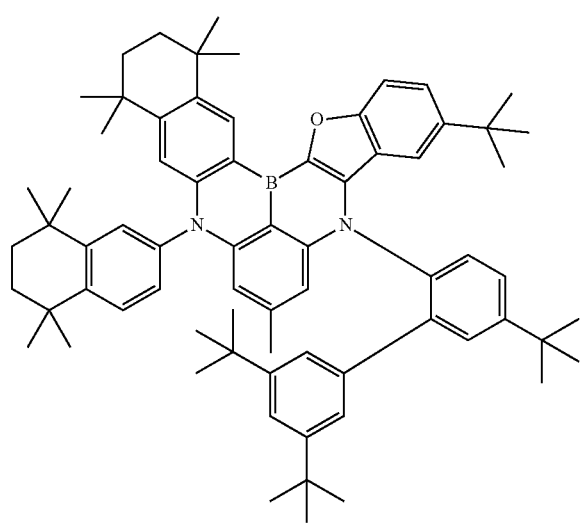
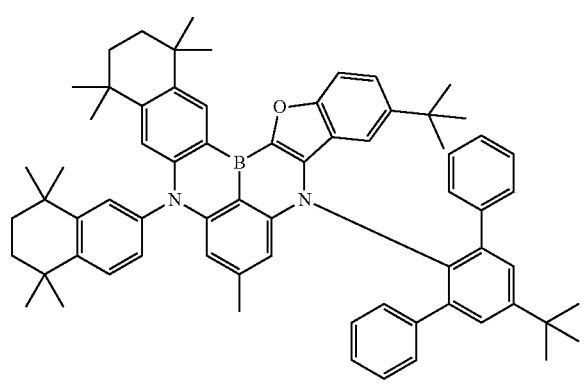
352
-continued
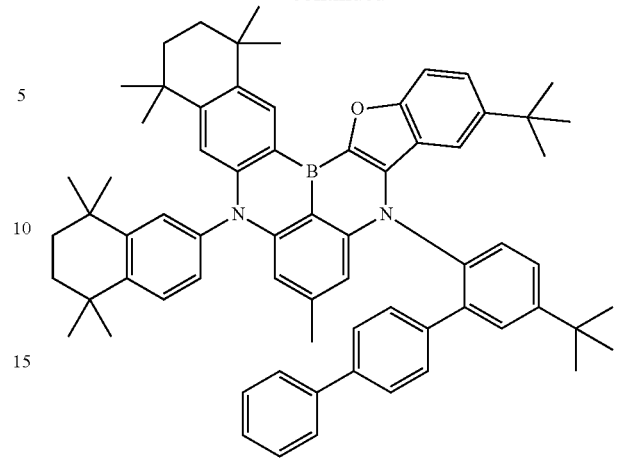
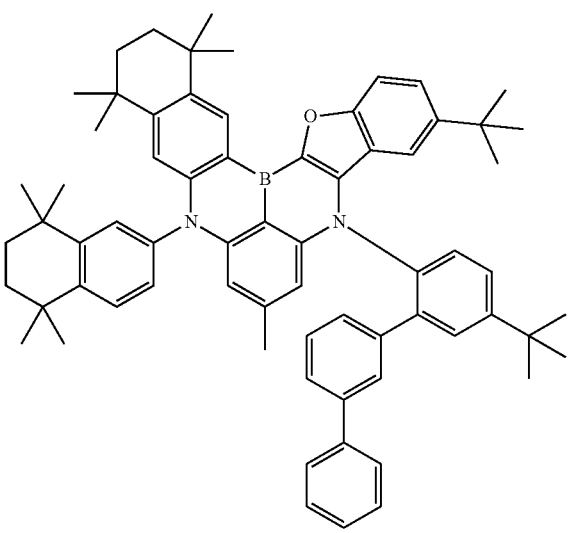
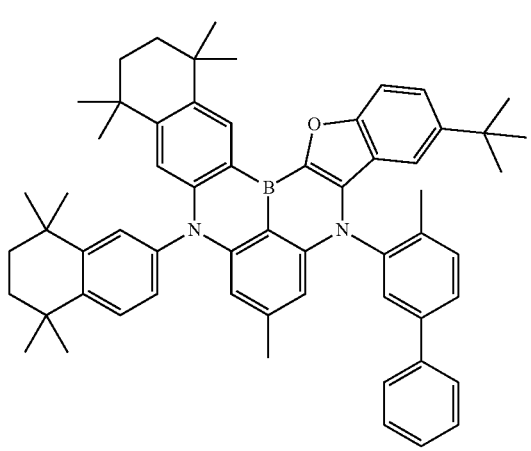

353
-continued
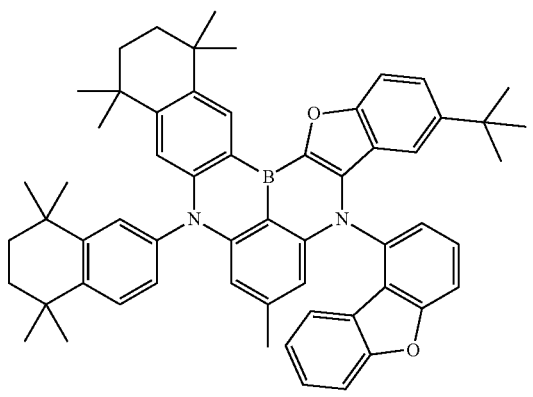
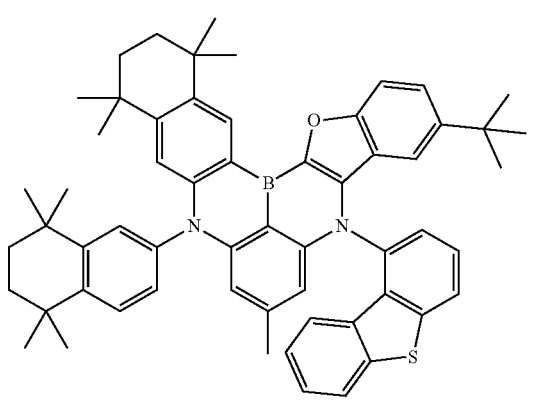
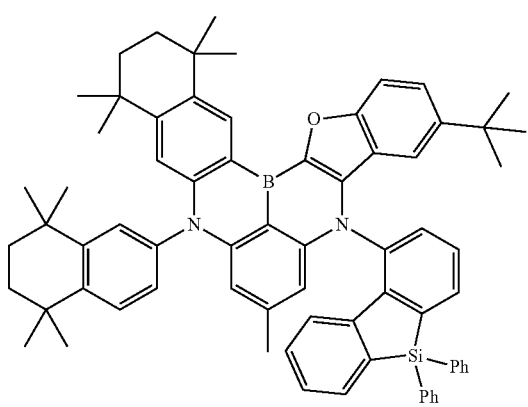
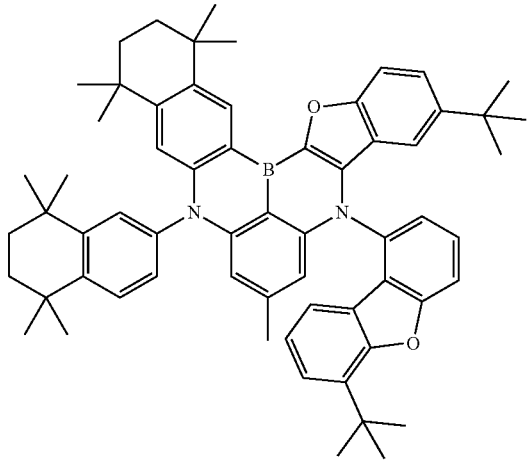
354
-continued
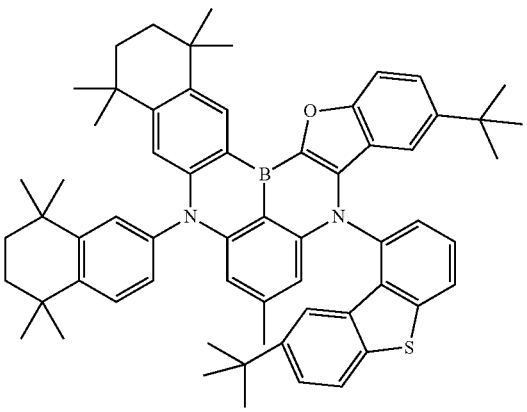
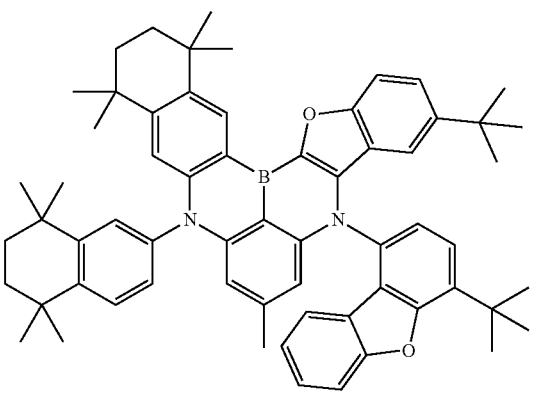
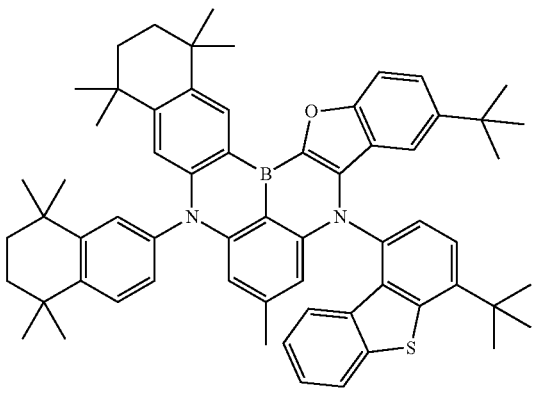
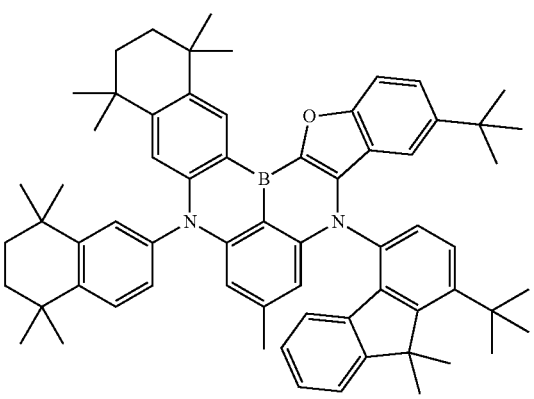

355
-continued
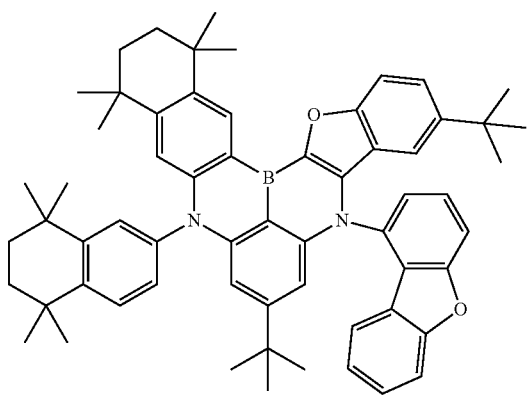
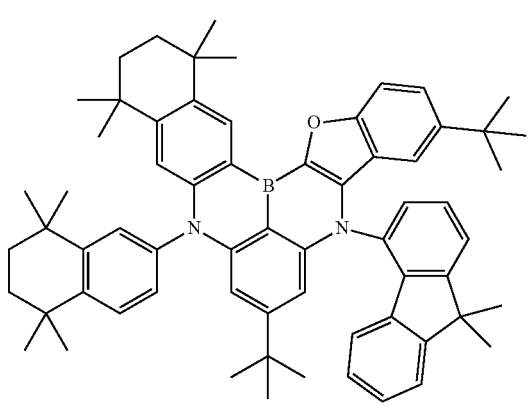
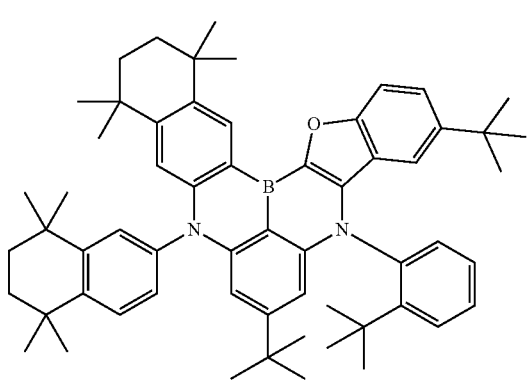
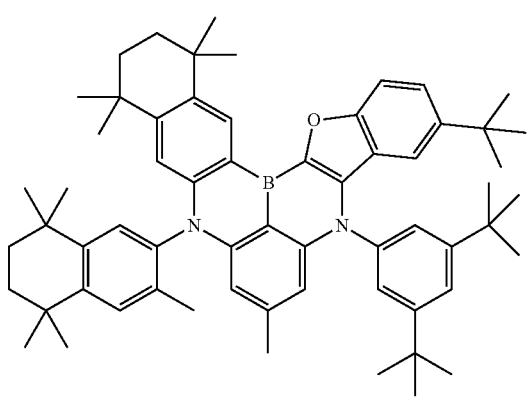
356
-continued
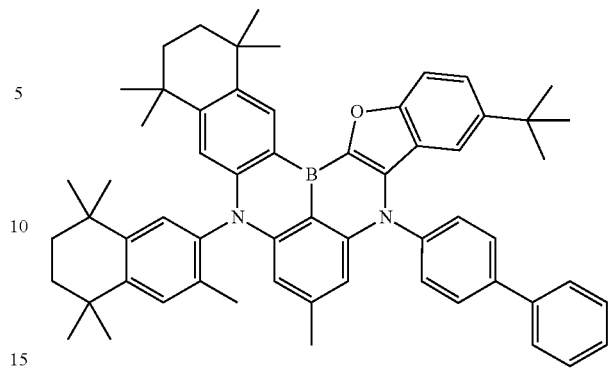
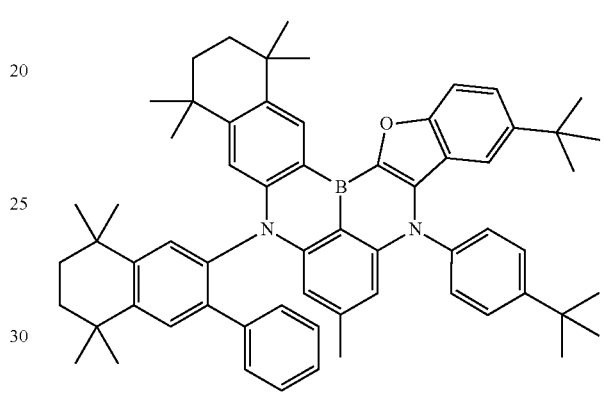
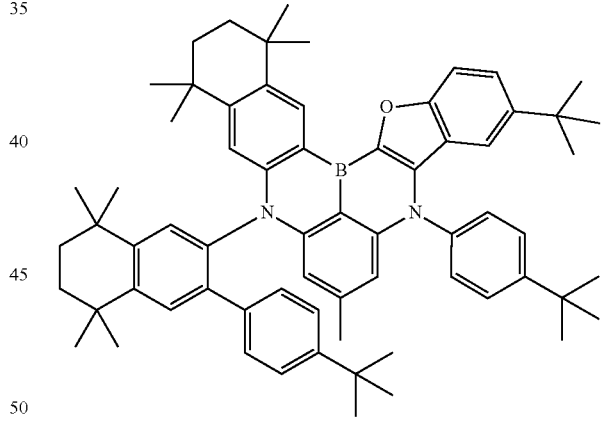
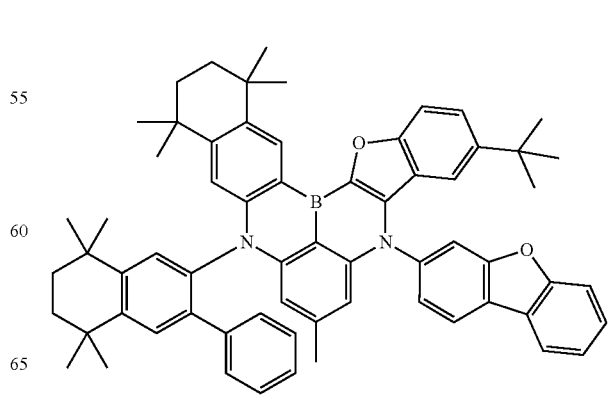

357
-continued
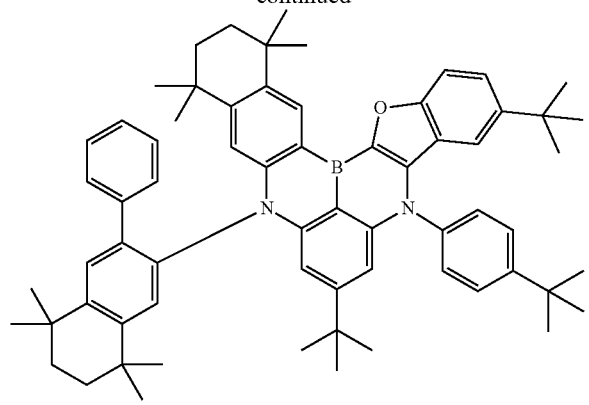
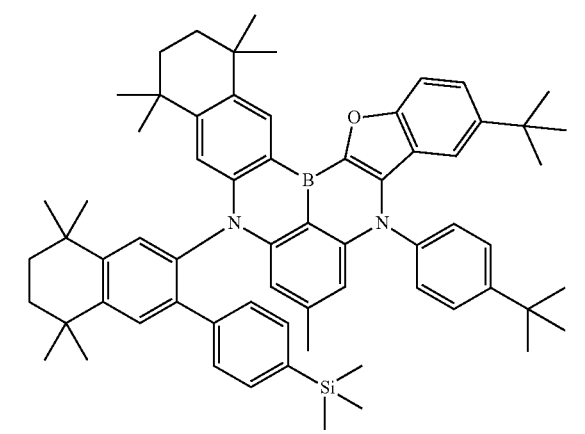
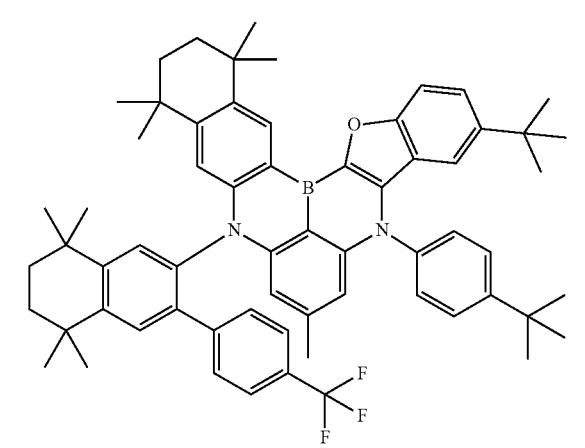
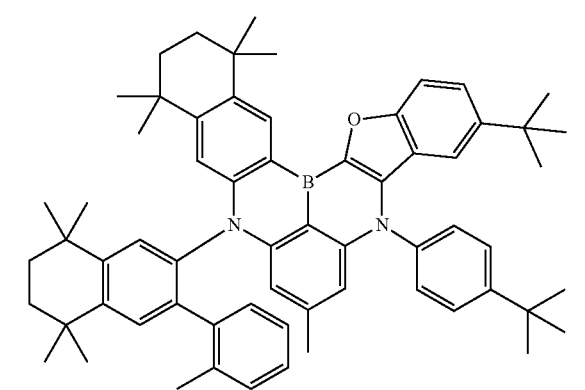
358
-continued
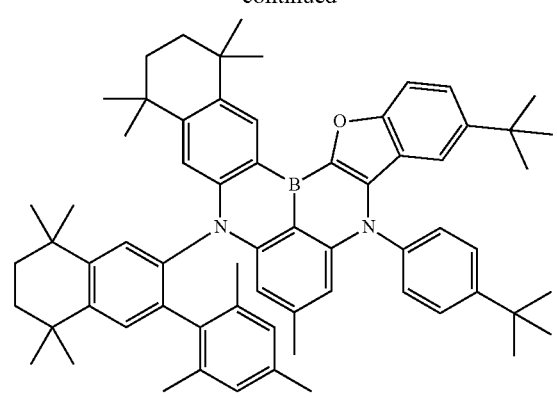
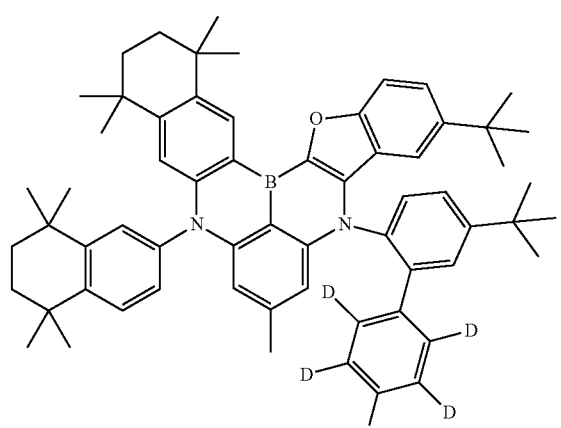
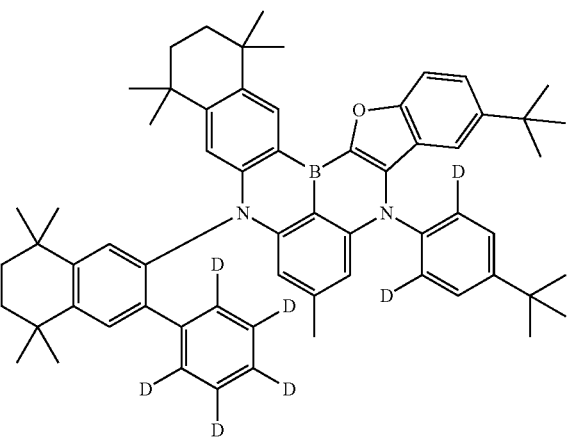
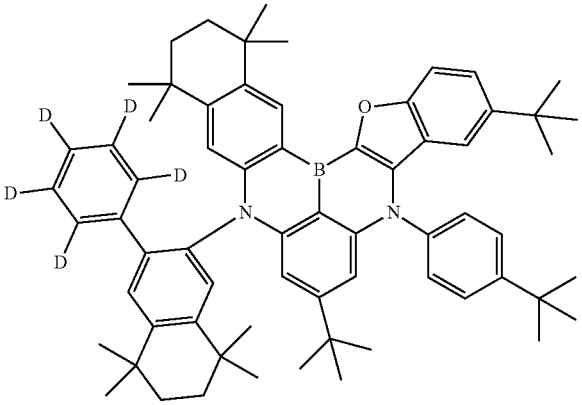

359
-continued
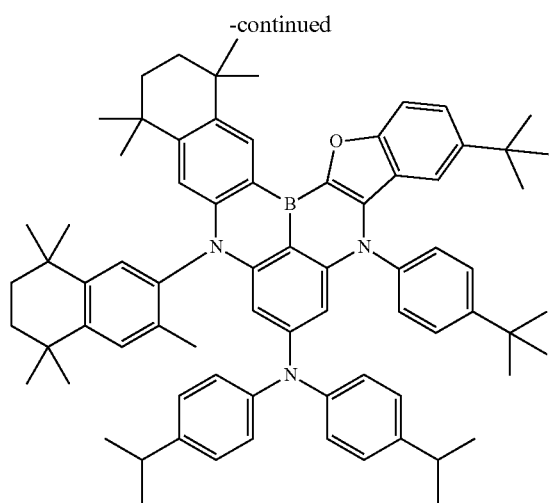
360
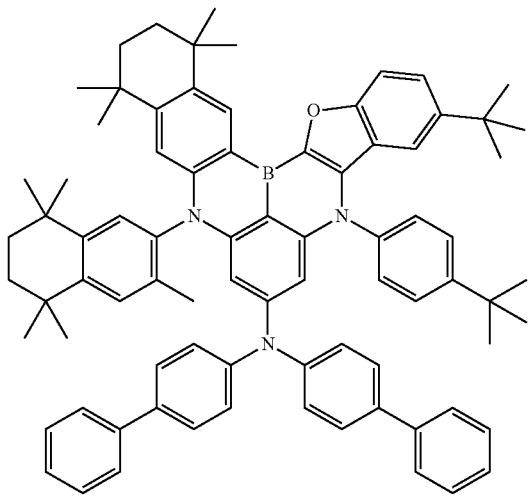
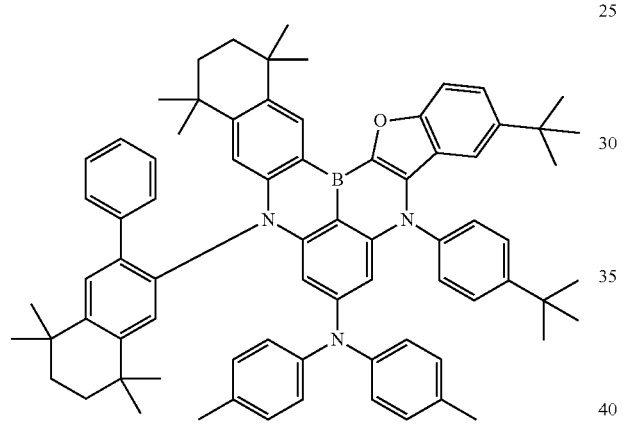
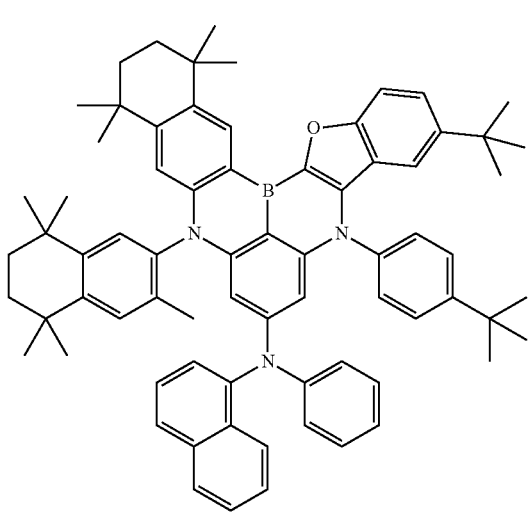
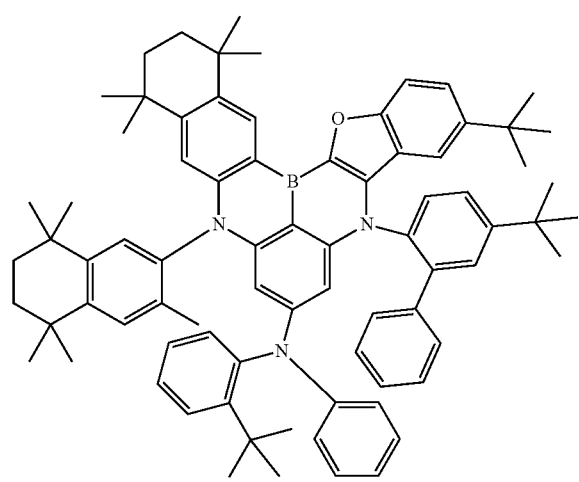 [SMILES: Cc1cc2c(cc1N1c3cc4c(cc3B3c5oc6ccc(C(C)(C)C)cc6c5N(c5ccc(C(C)(C)C)cc5-c5ccccc5)c5cc(N(c6ccccc6)c6ccccc6C(C)(C)C)cc1c53)C(C)(C)CCC4(C)C)C(C)(C)CCC2(C)C]
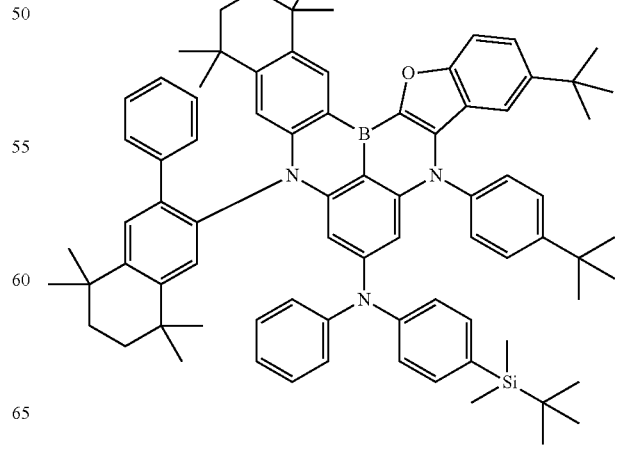

361
-continued
362
-continued
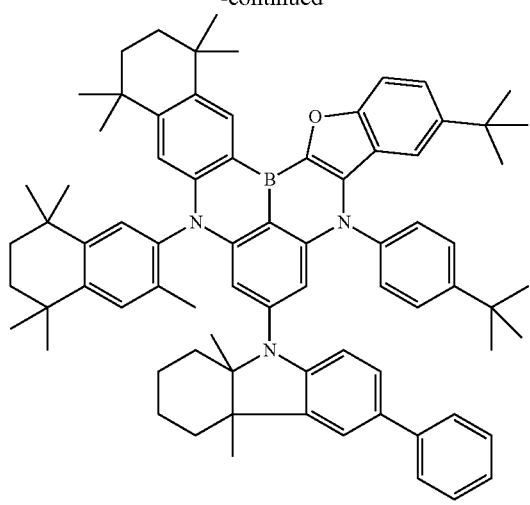
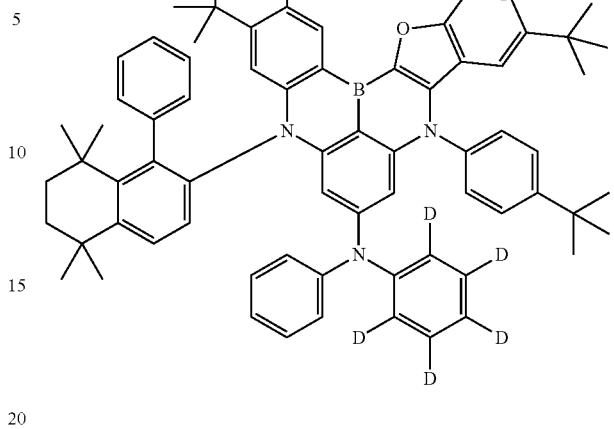
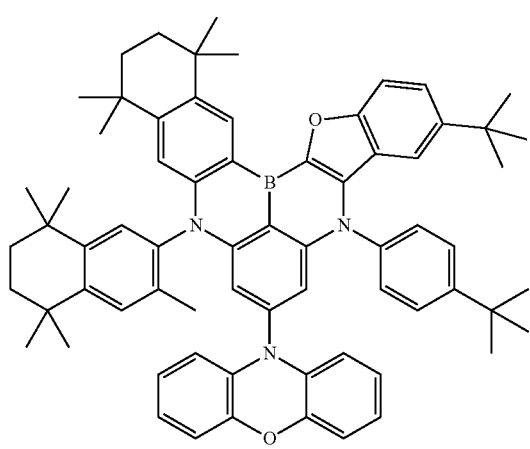
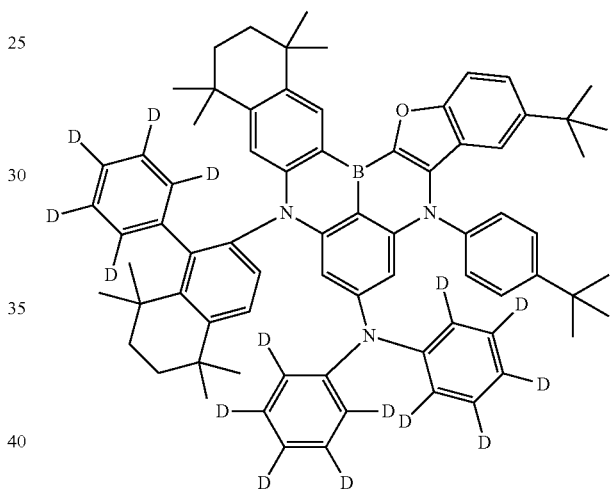
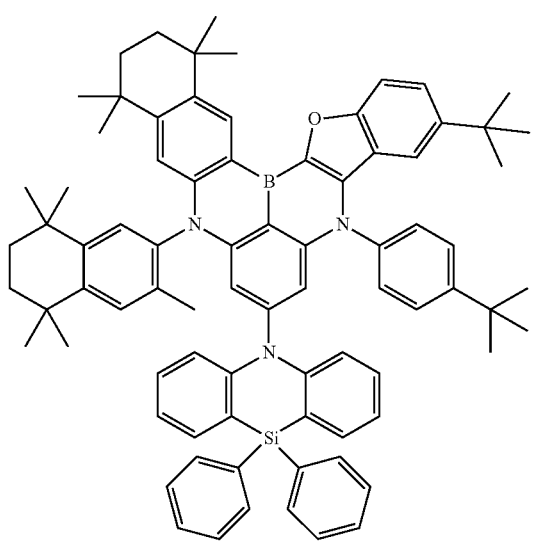
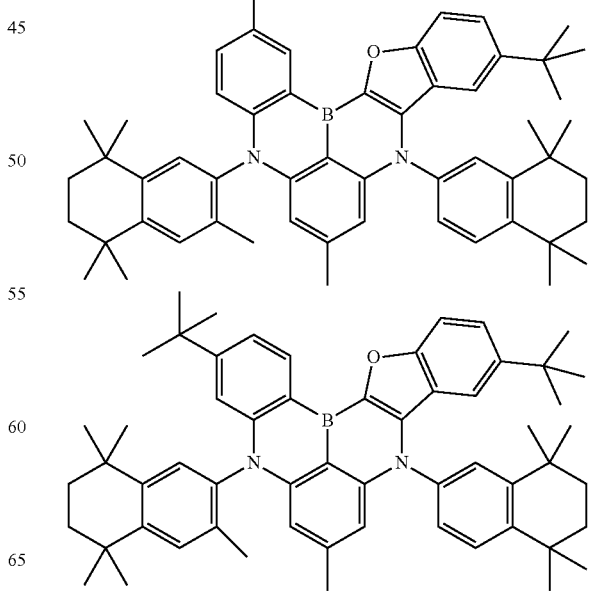

363
-continued
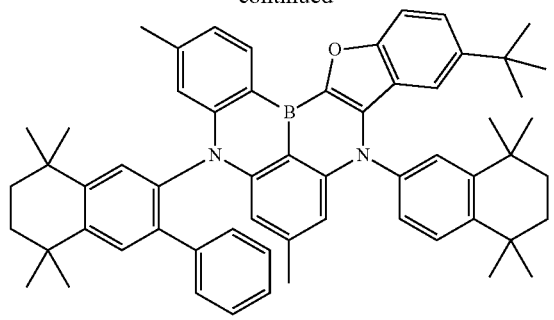
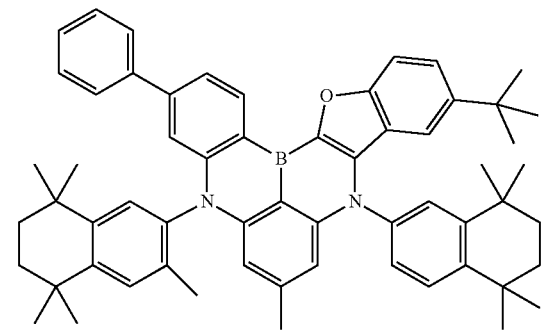
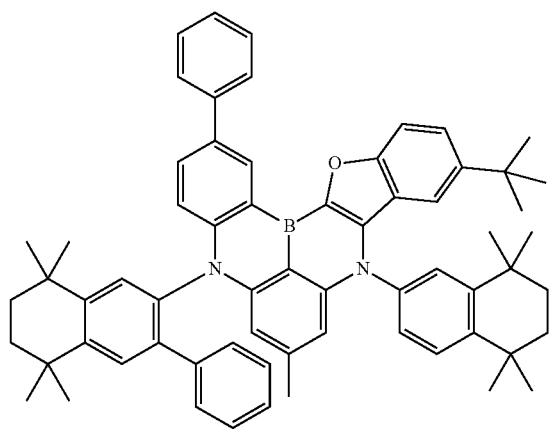
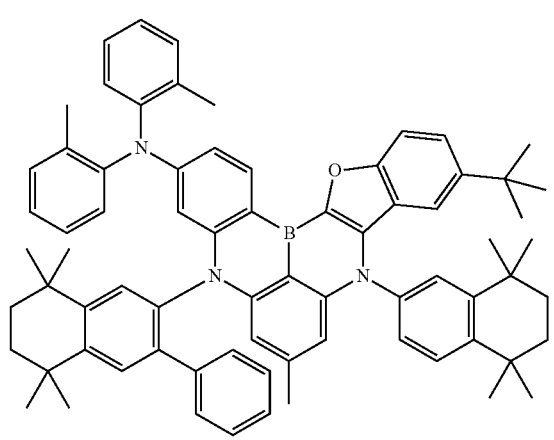
364
-continued
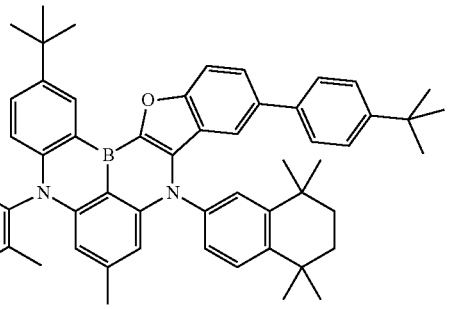
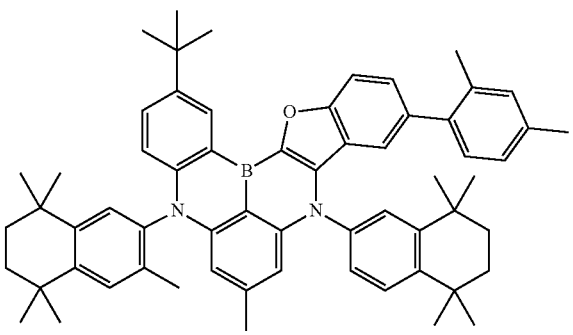
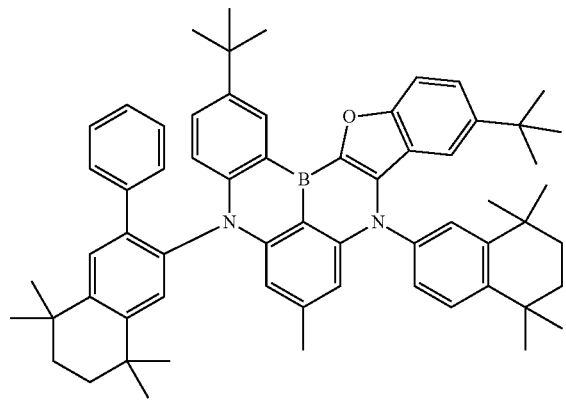
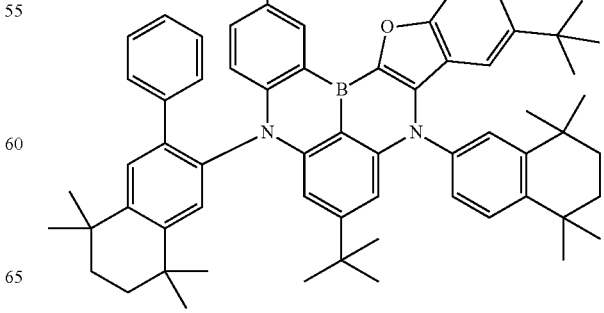

365
-continued
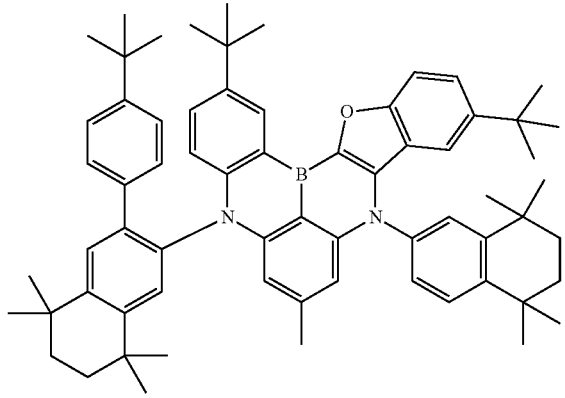
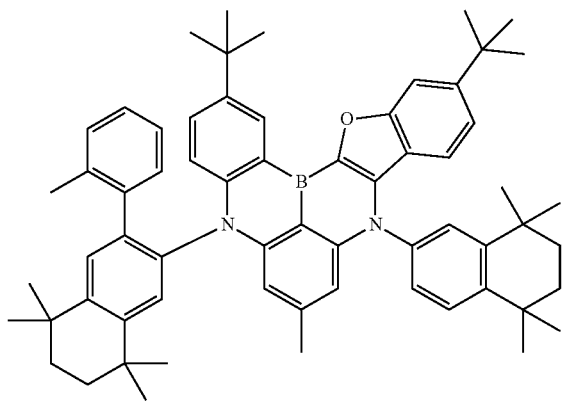
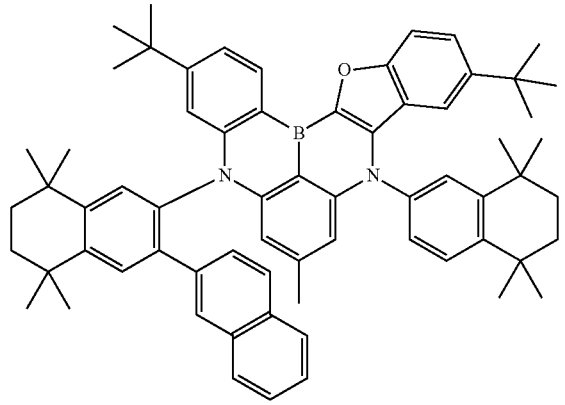
366
-continued
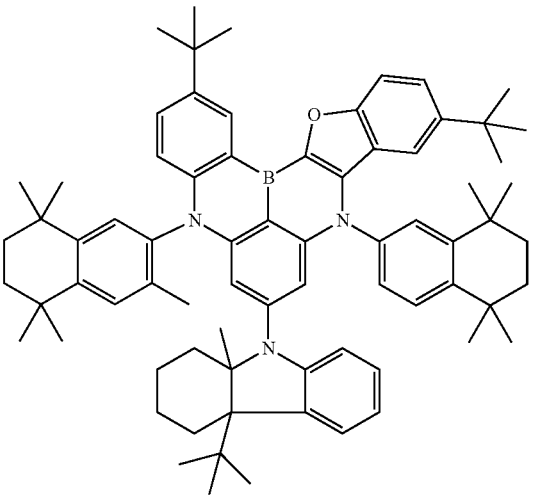
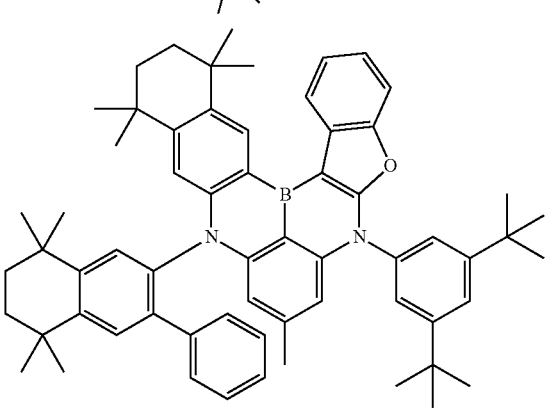
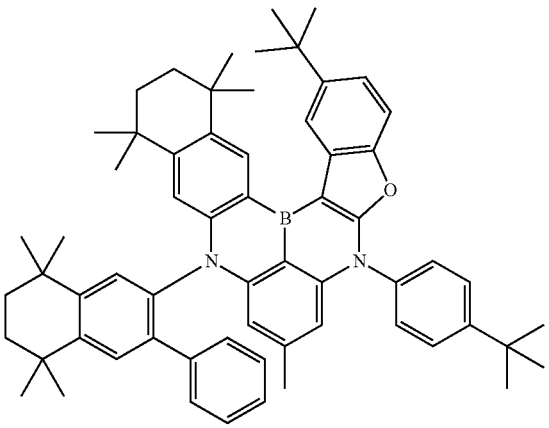
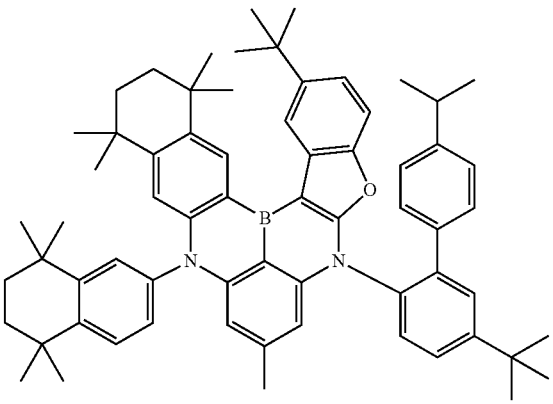

367
-continued
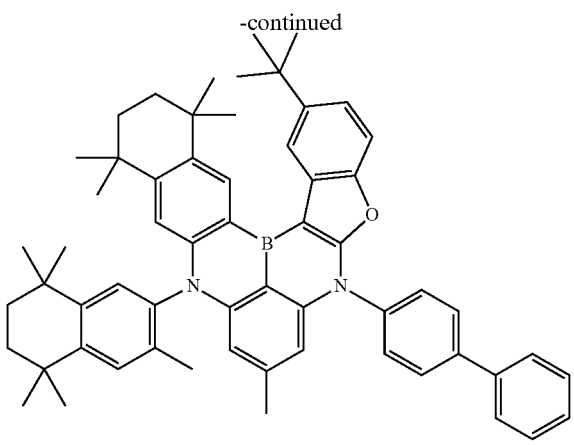
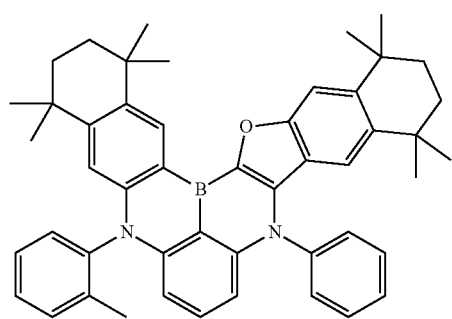
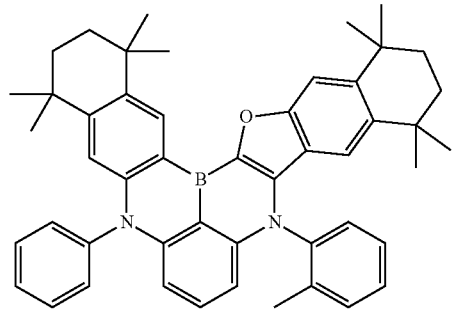
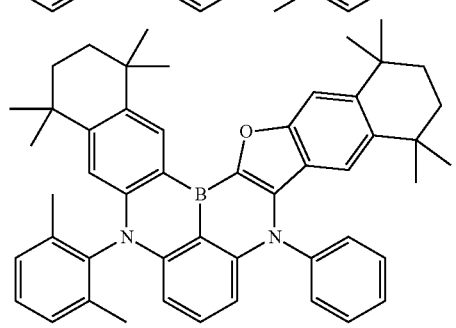
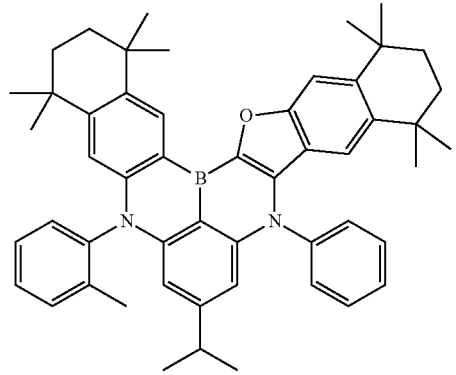
368
-continued
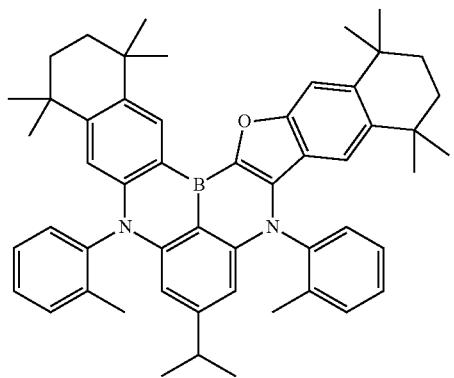
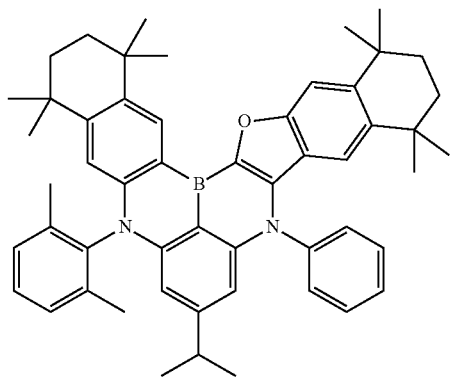
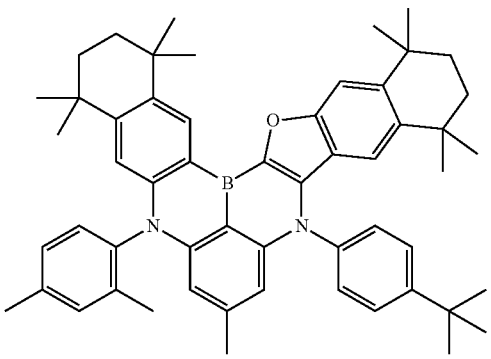
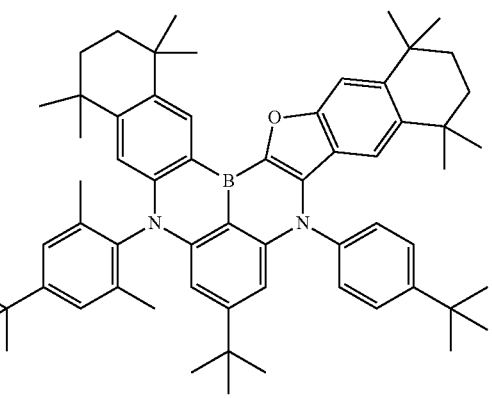

369
-continued
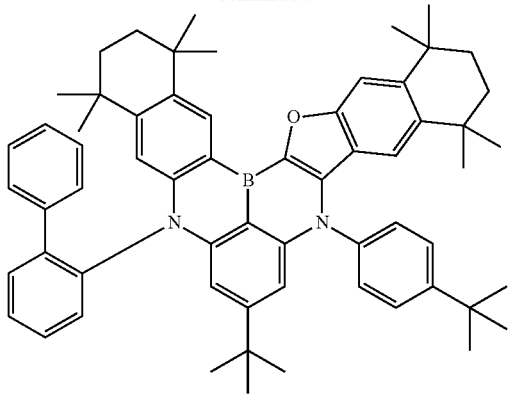
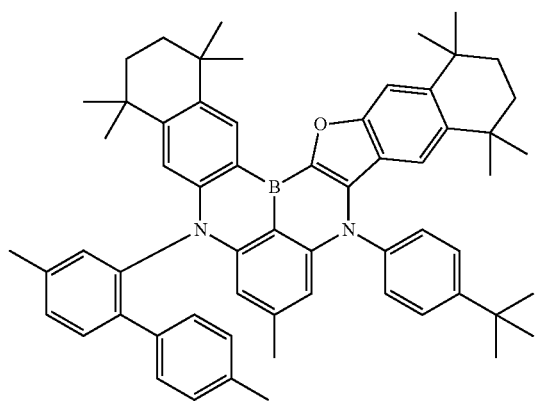
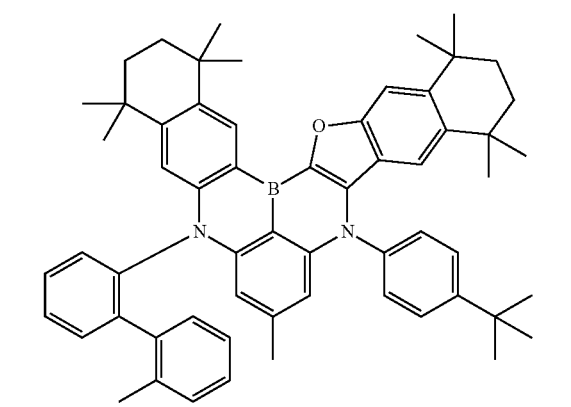
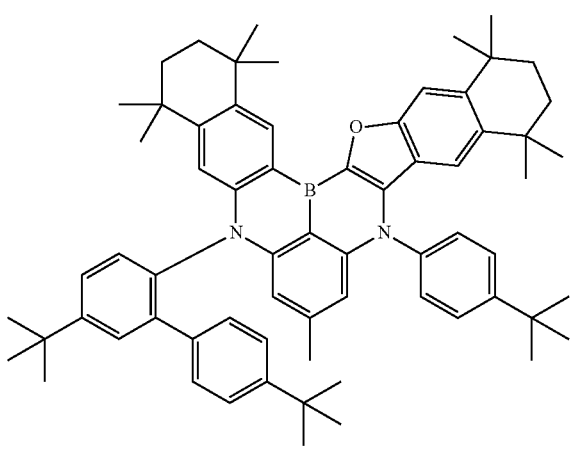
370
-continued
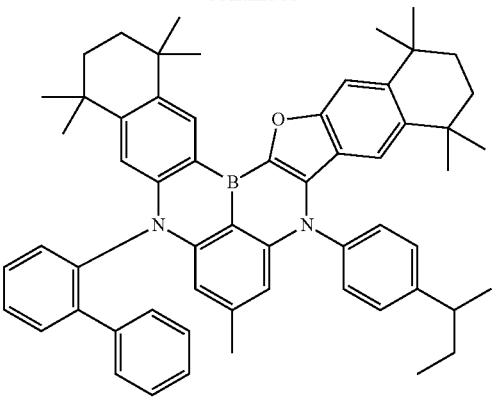
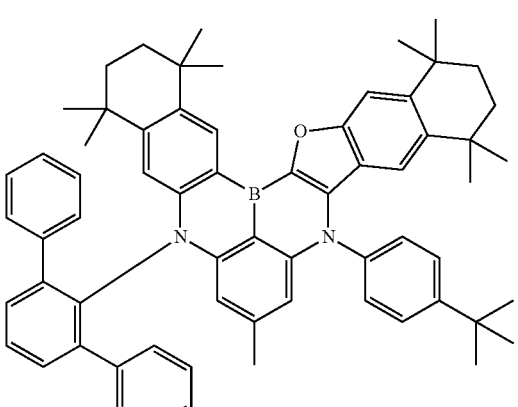
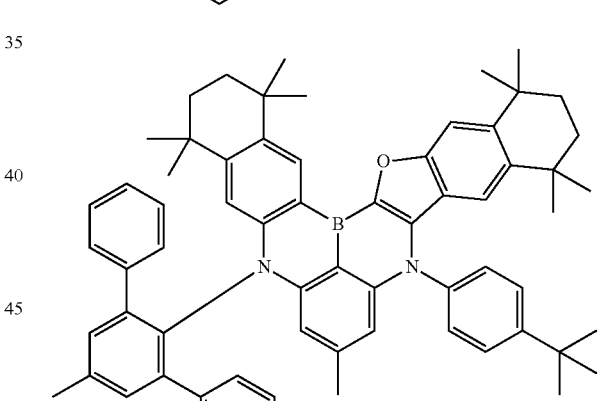

371
-continued
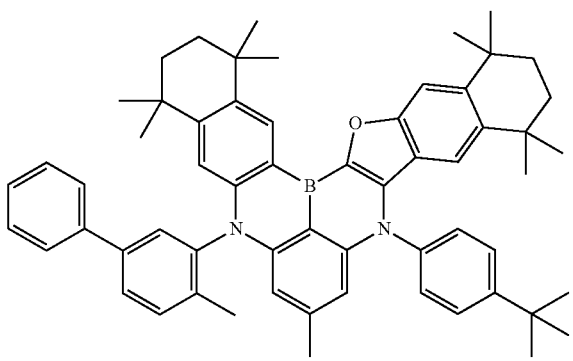
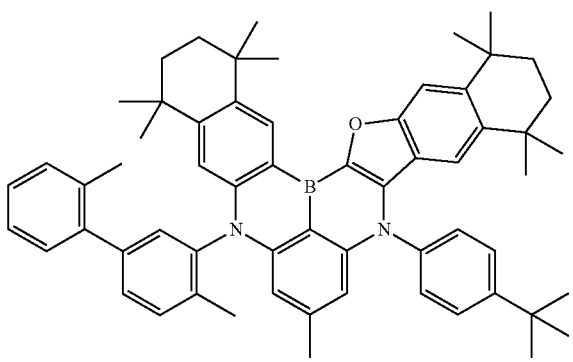
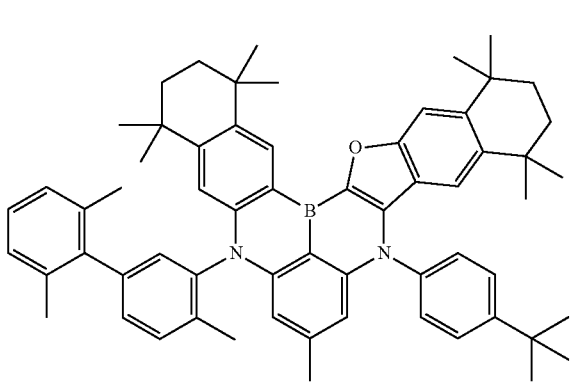
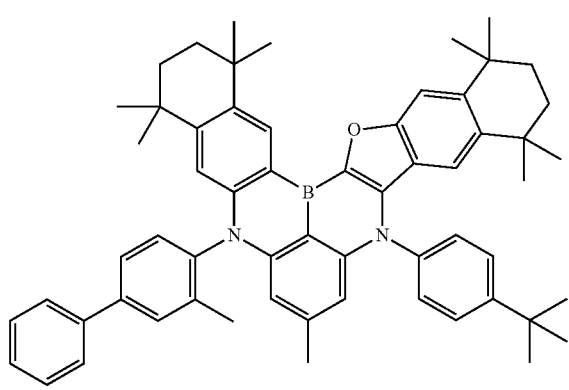
372
-continued
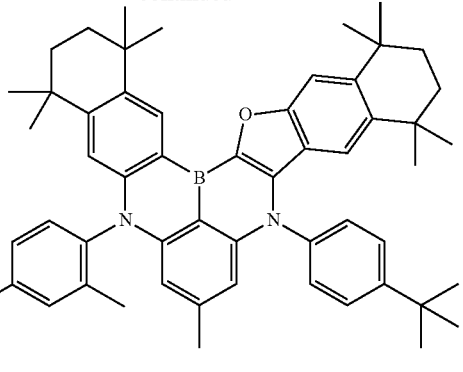
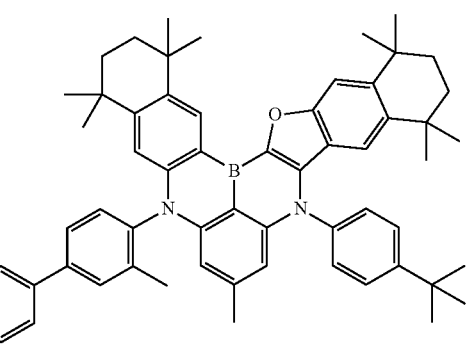
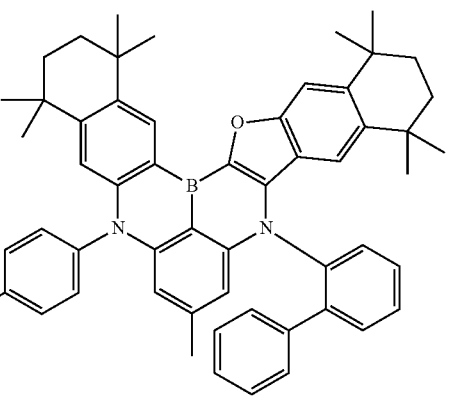
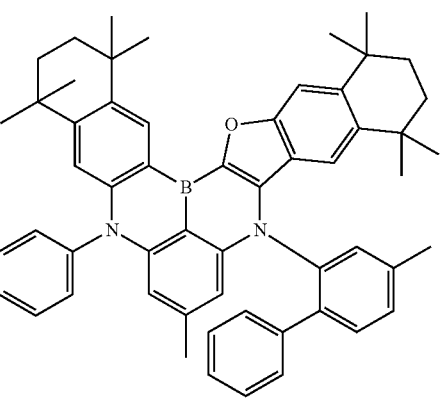

373
-continued
374
-continued
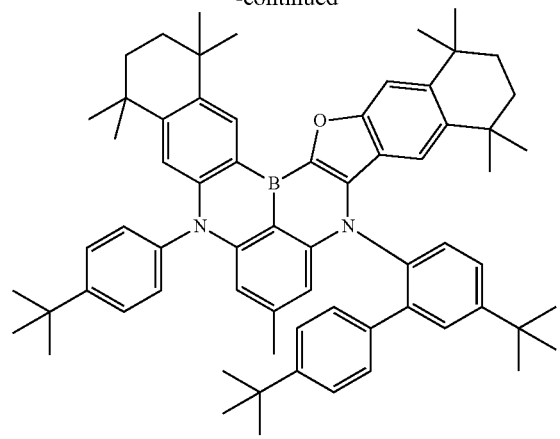
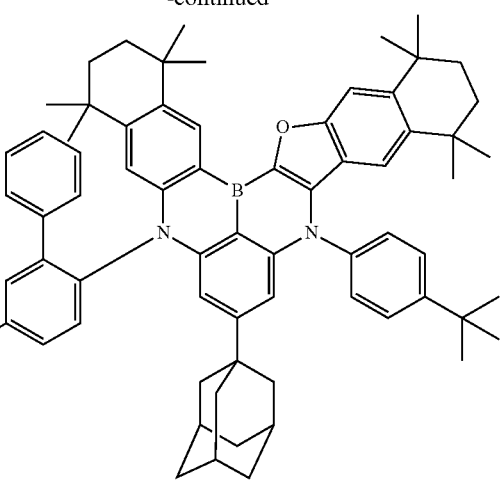
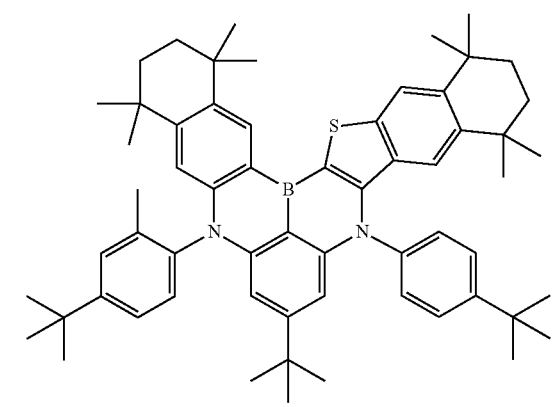
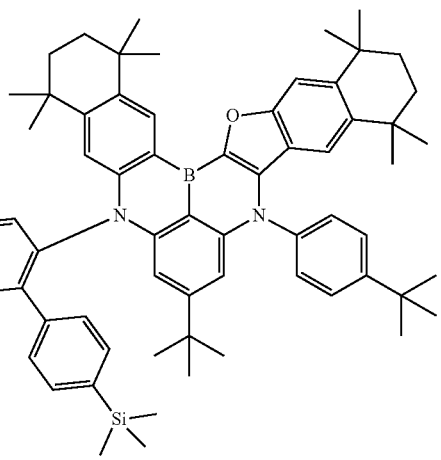
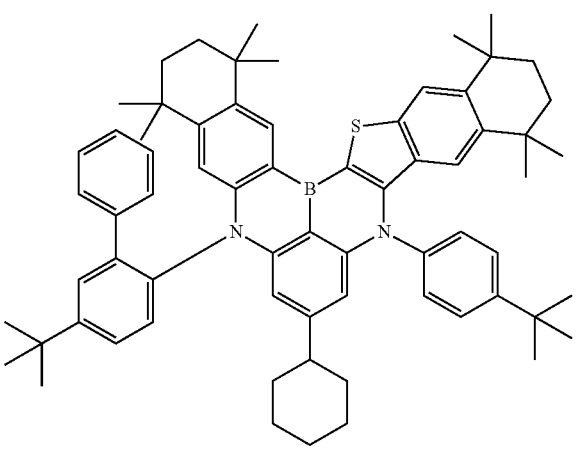
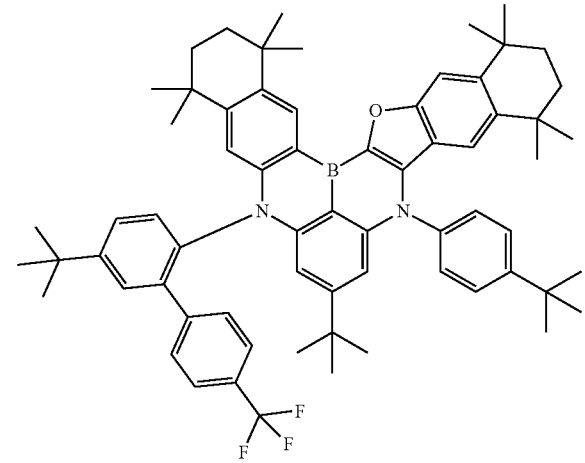

375
-continued
376
-continued
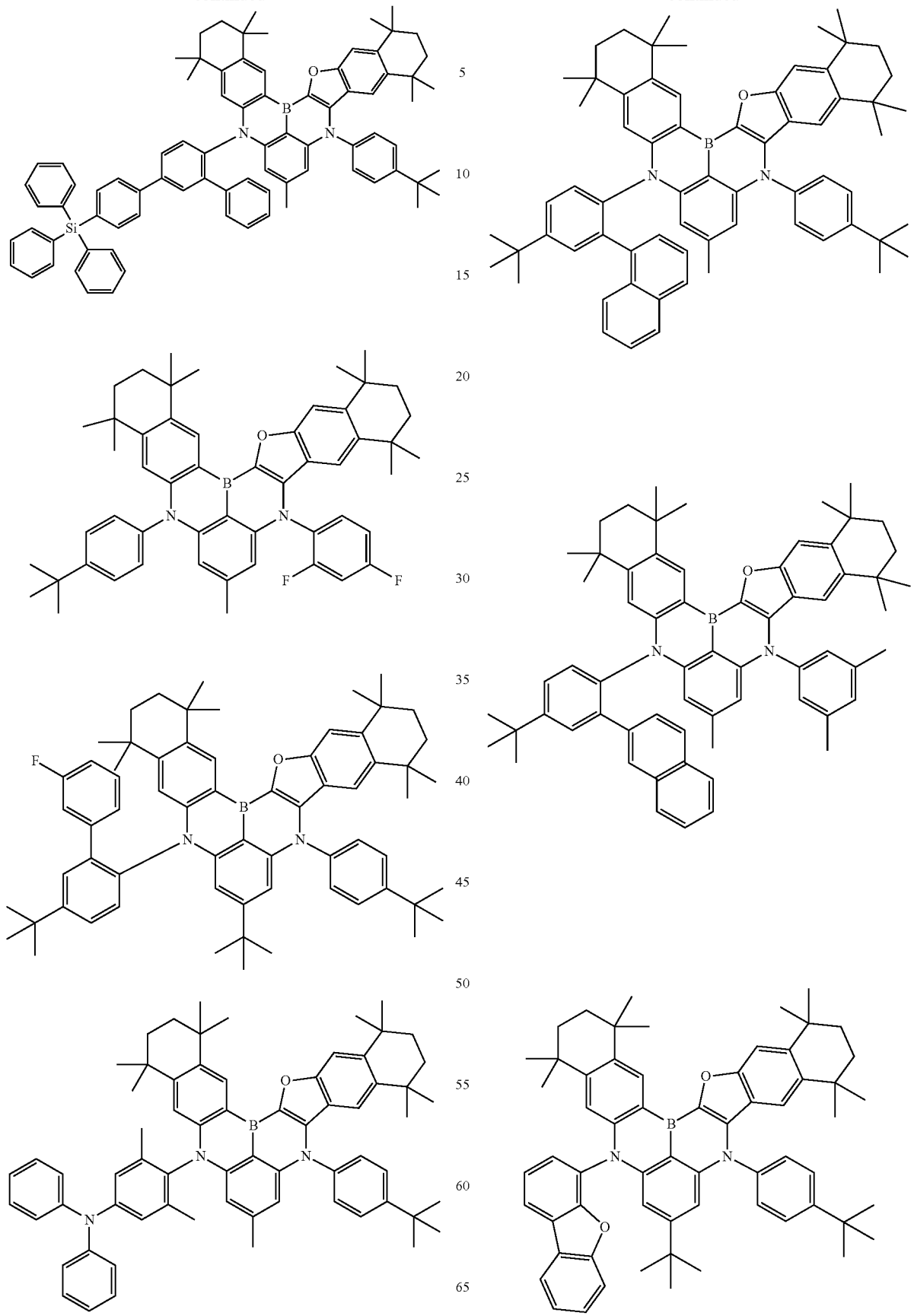

377
-continued
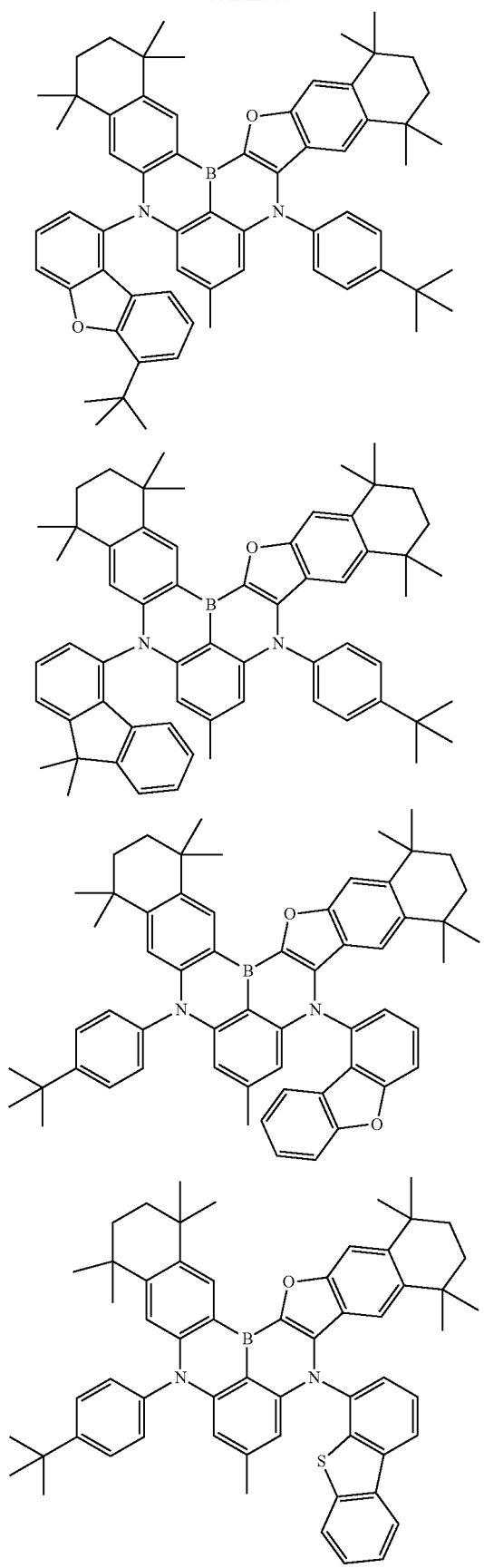
378
-continued
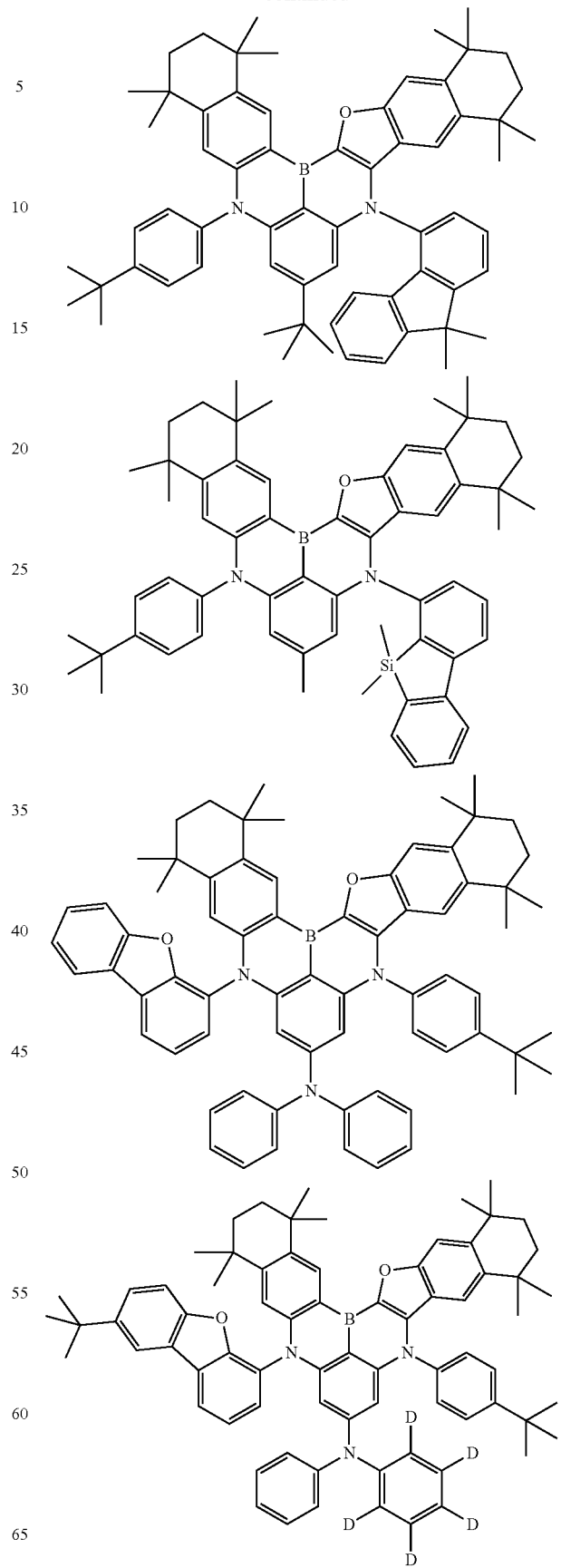

379
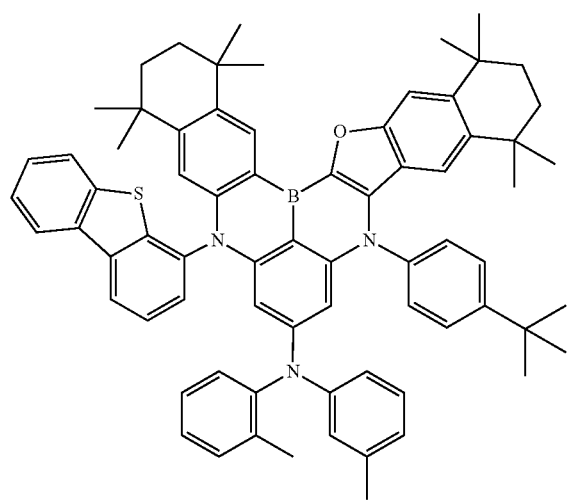
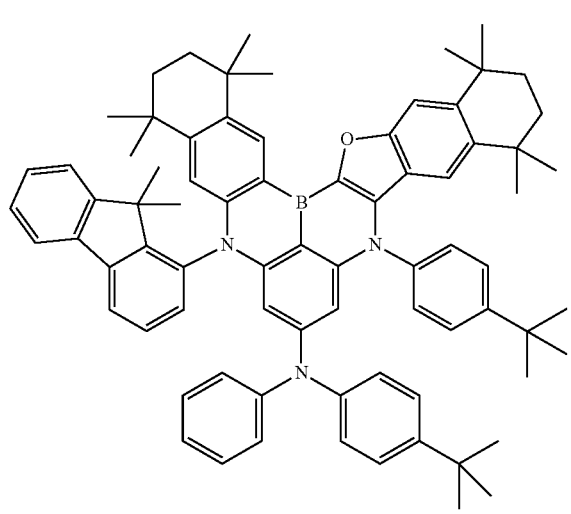
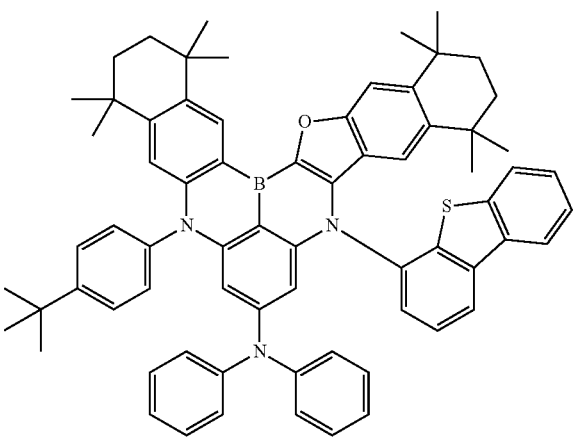 [SMILES: CC(C)(C)c1ccc(N2c3cc4c(cc3B3c5oc6cc7c(cc6c5N(c5cccc6c5sc5ccccc56)c5cc(N(c6ccccc6)c6ccccc6)cc2c53)C(C)(C)CCC7(C)C)C(C)(C)CCC4(C)C)cc1]
380
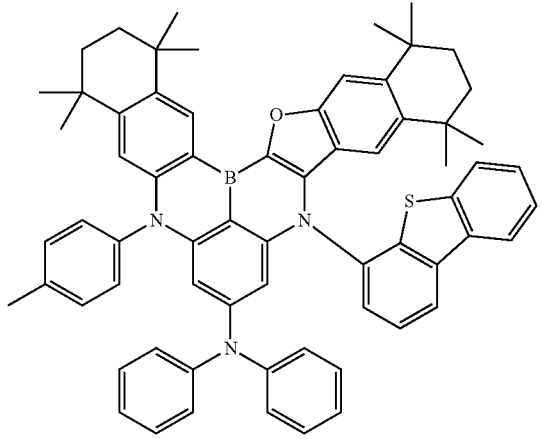
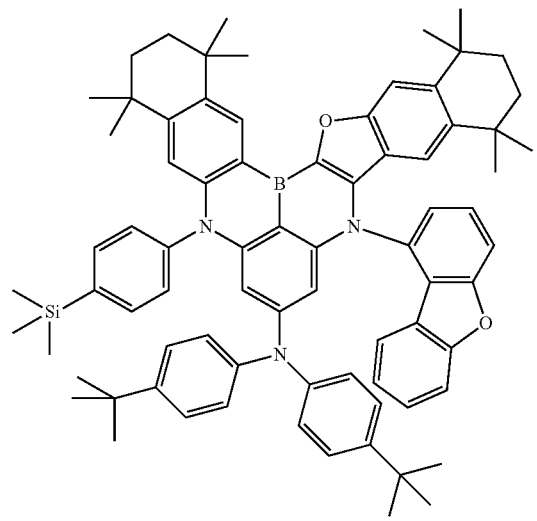
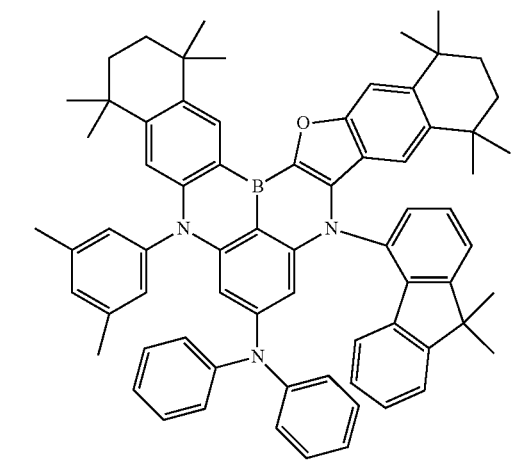

| 381 -continued | 382 -continued |
|---|---|
| 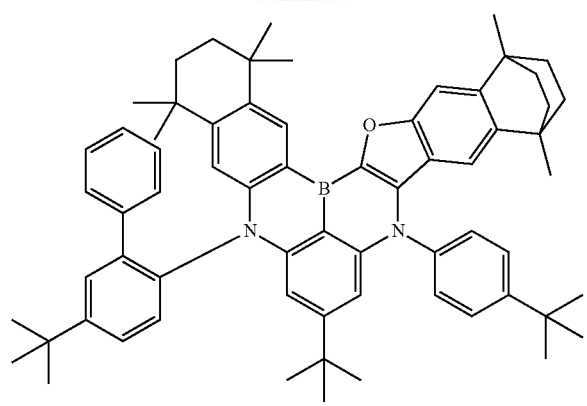 | 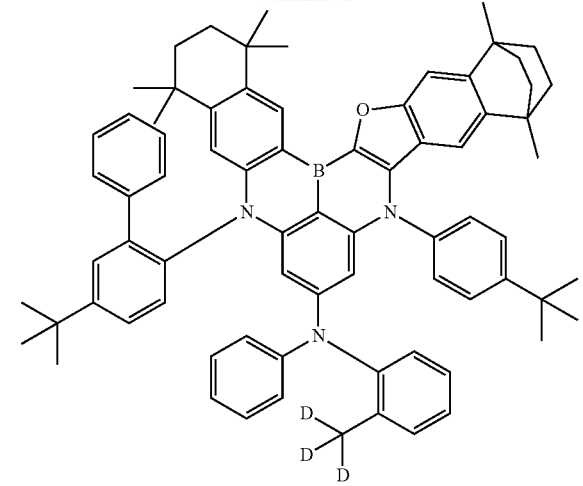 |
| 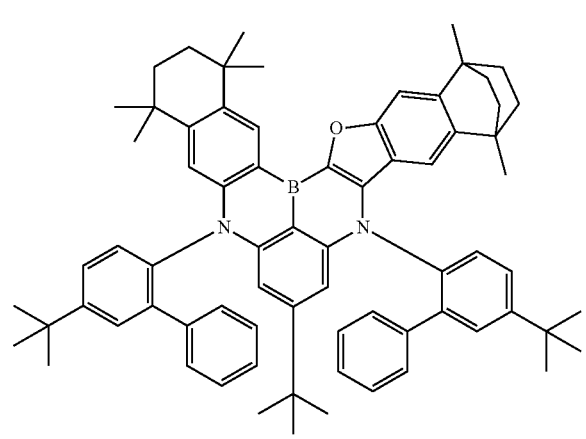 | 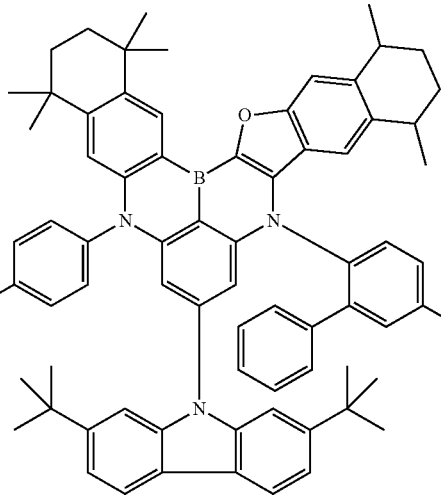 |
| 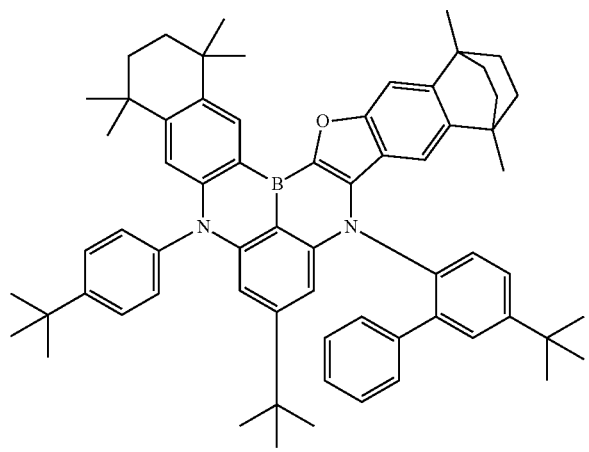 | 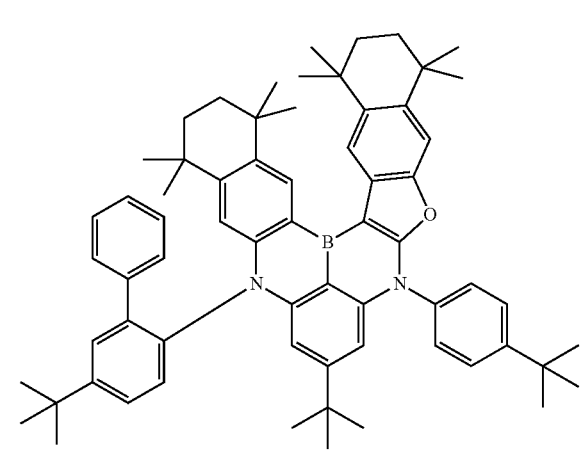 |

383
-continued
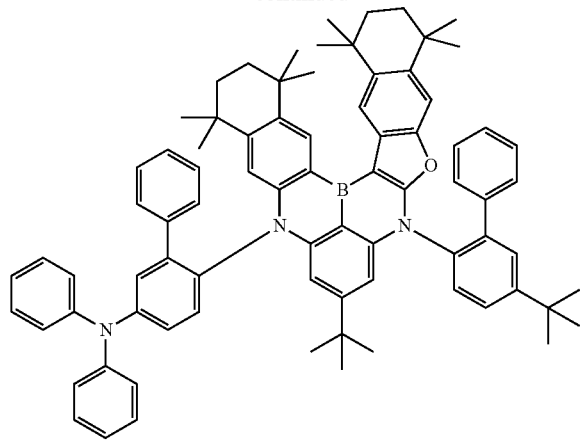
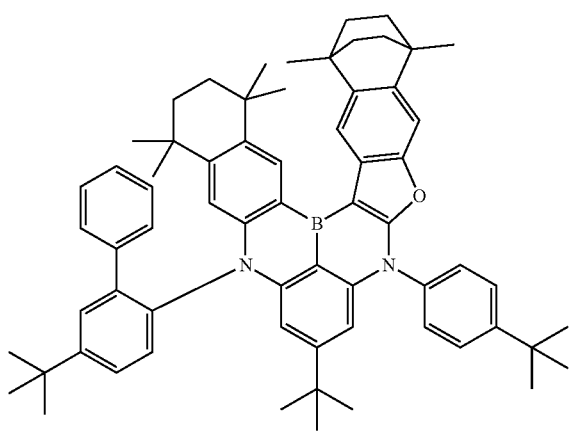
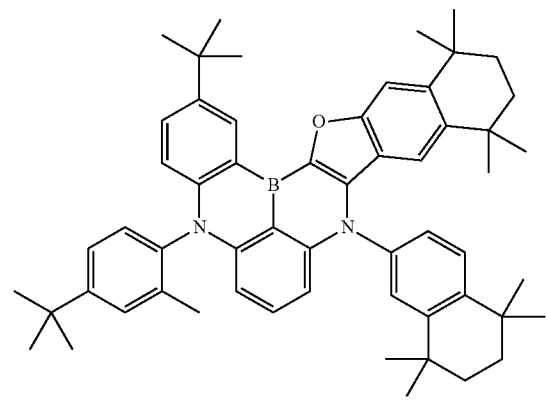
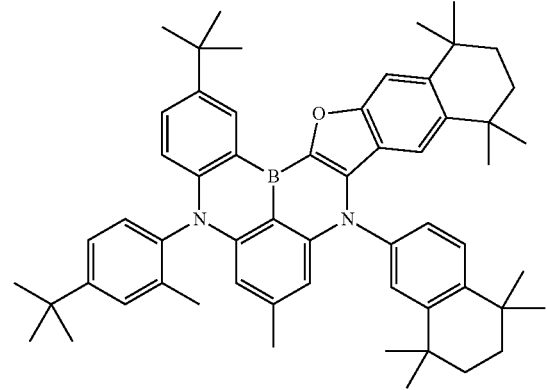
384
-continued
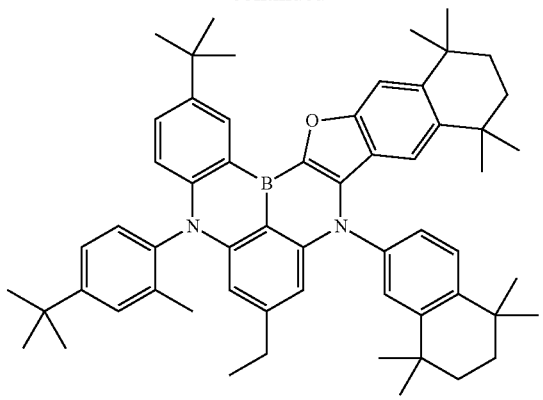
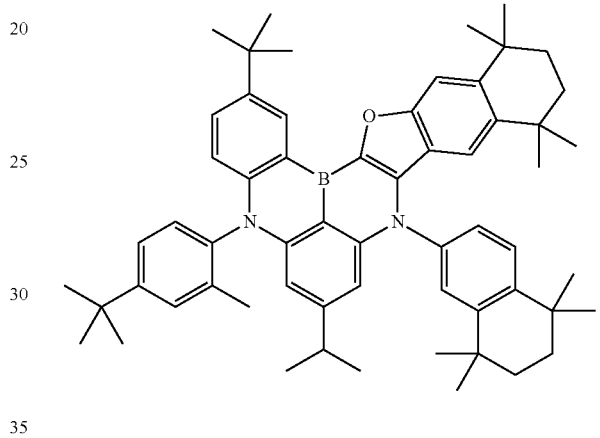
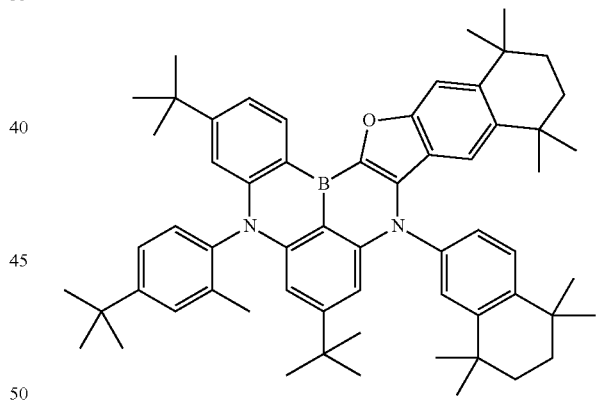
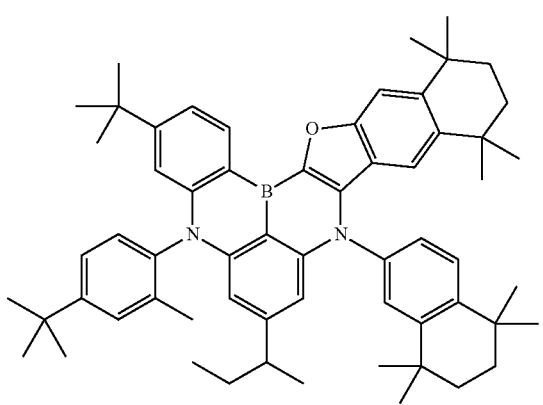

385
-continued
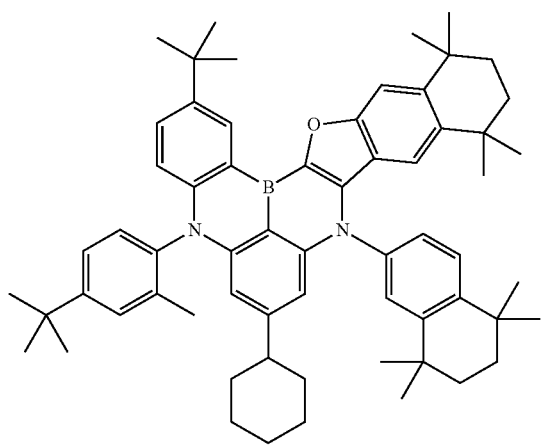
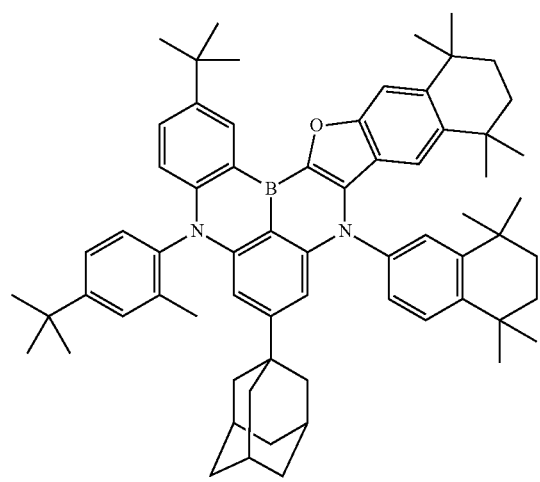
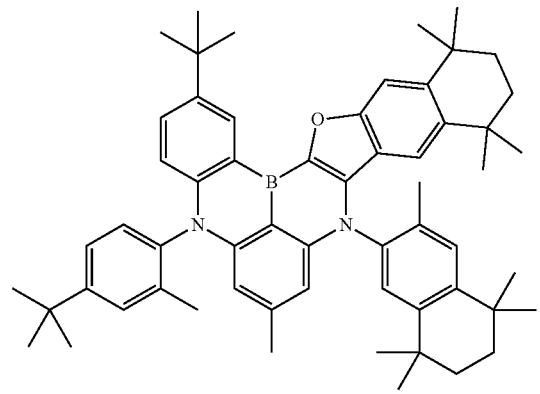
386
-continued
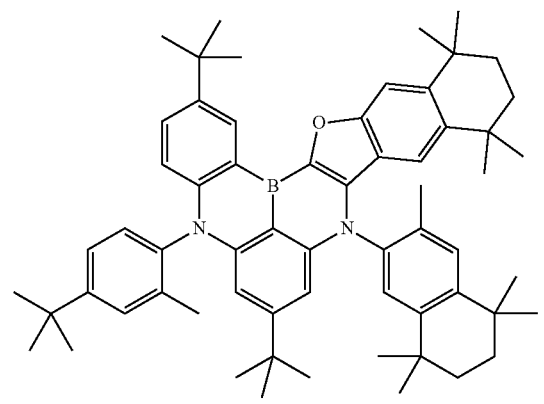
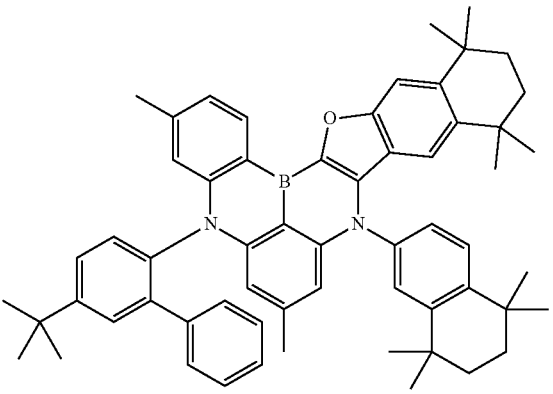

387
-continued
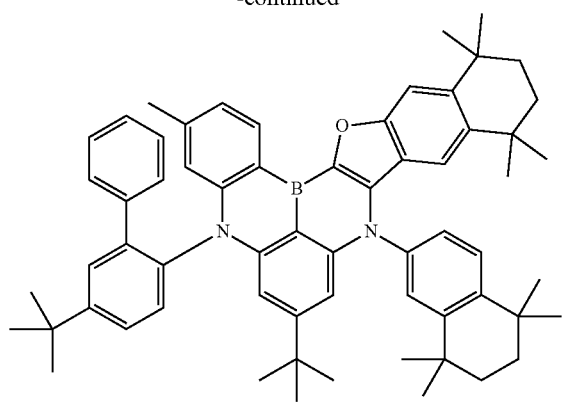
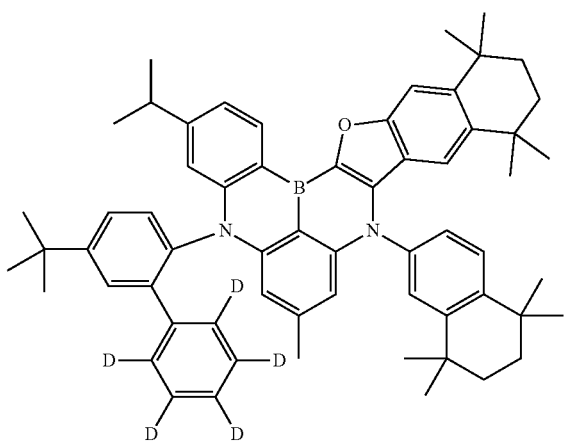
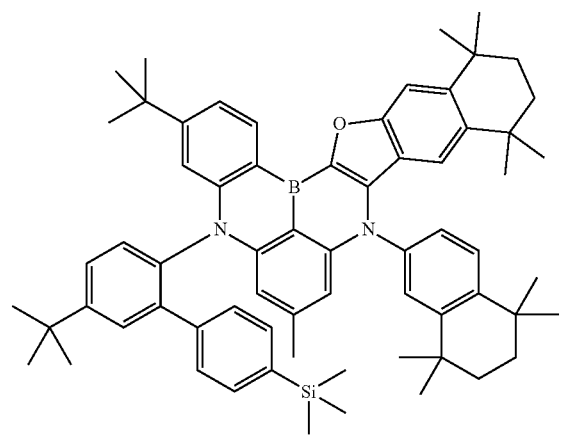
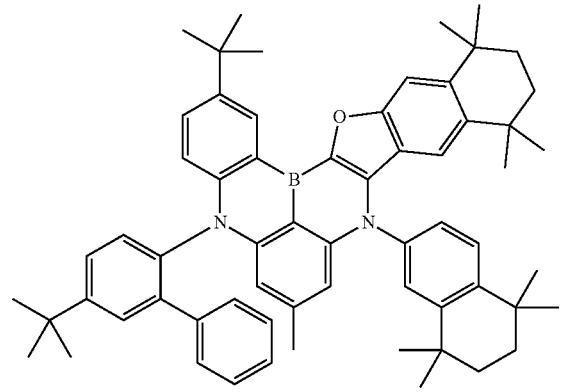
388
-continued
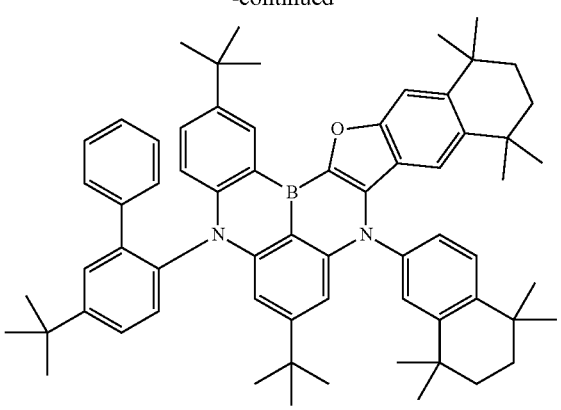
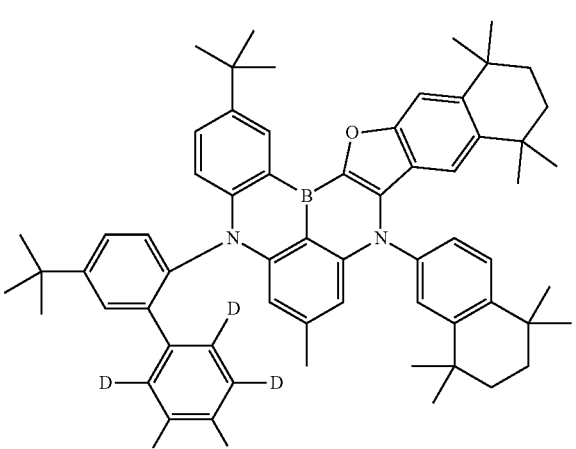
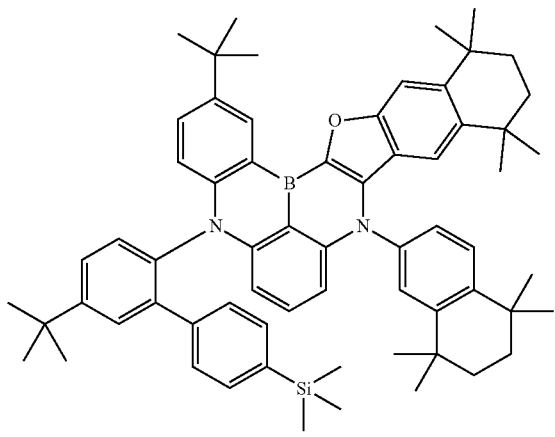
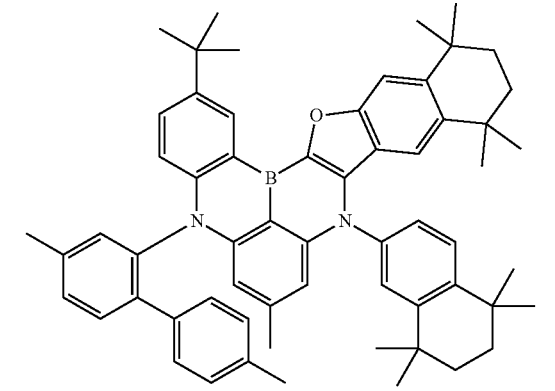

389
-continued
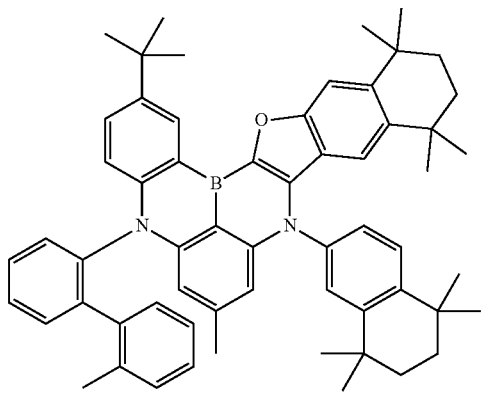
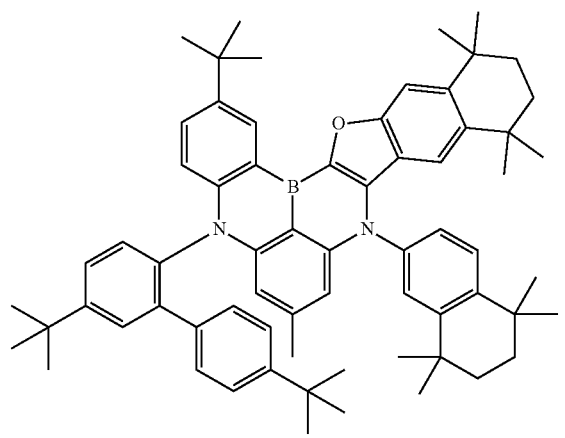
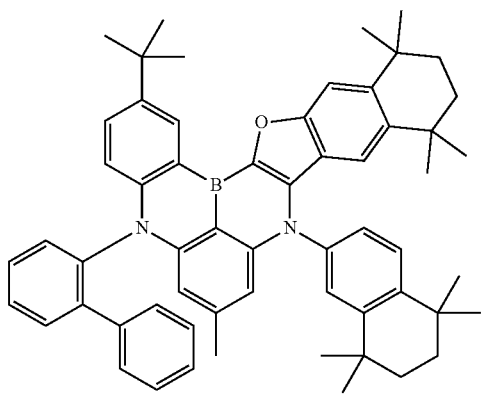
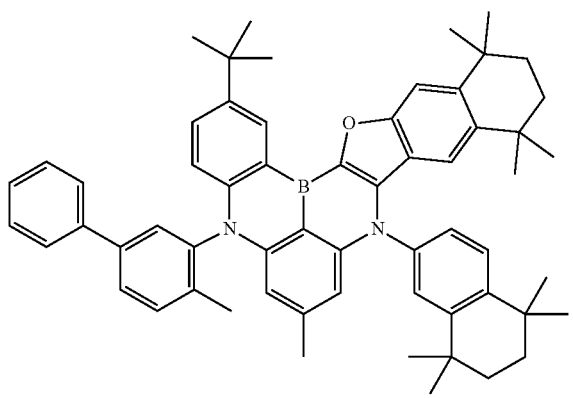
390
-continued
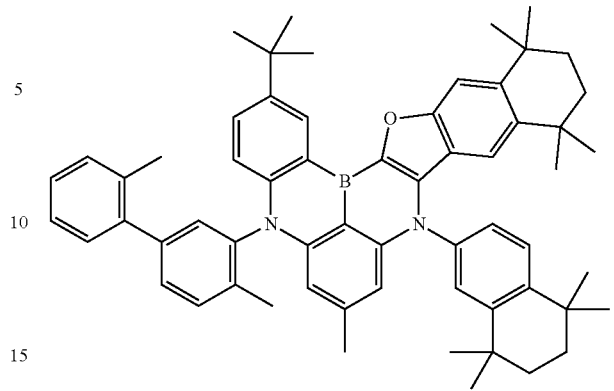

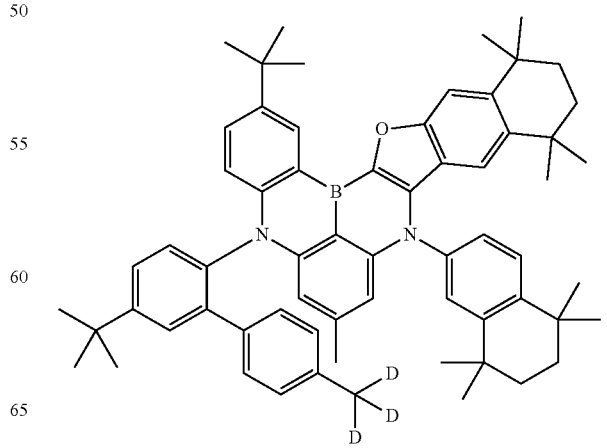

391
-continued
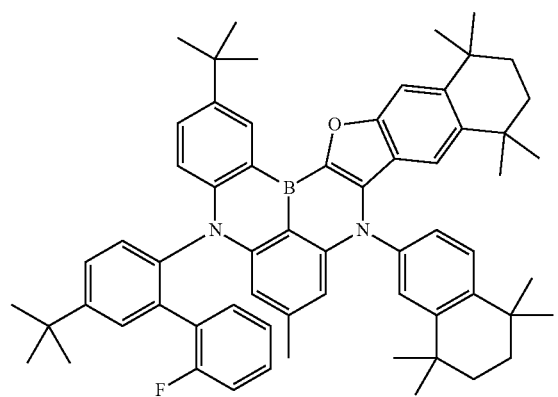
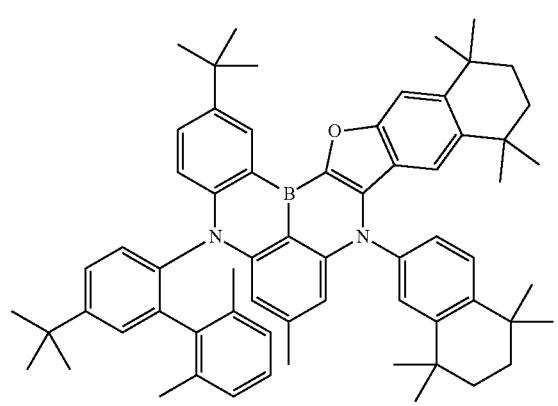
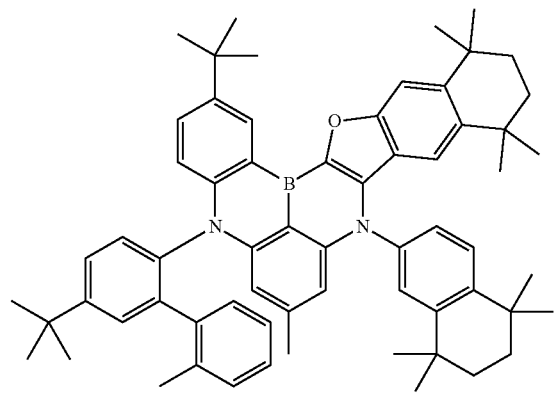
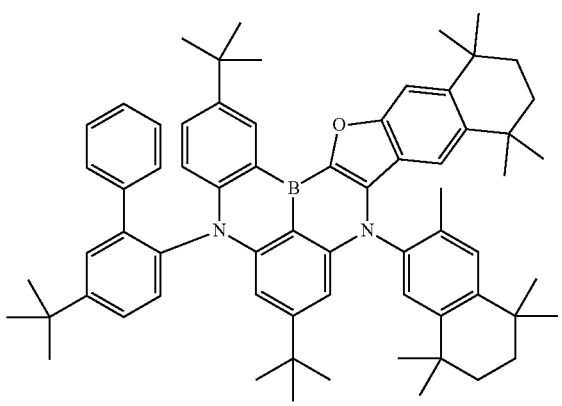
392
-continued
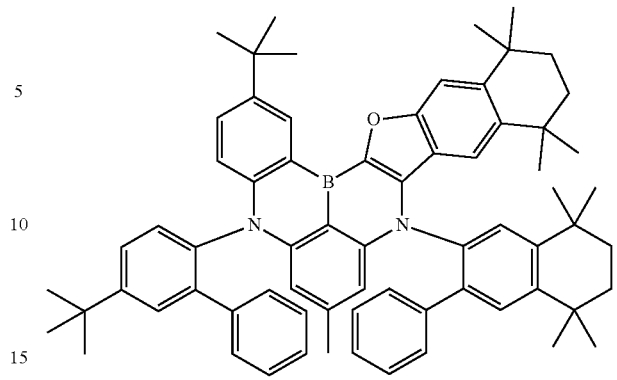
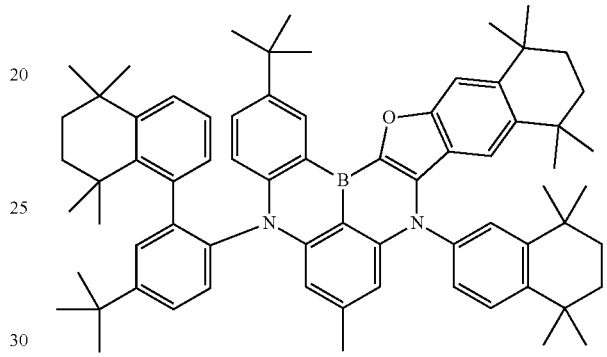
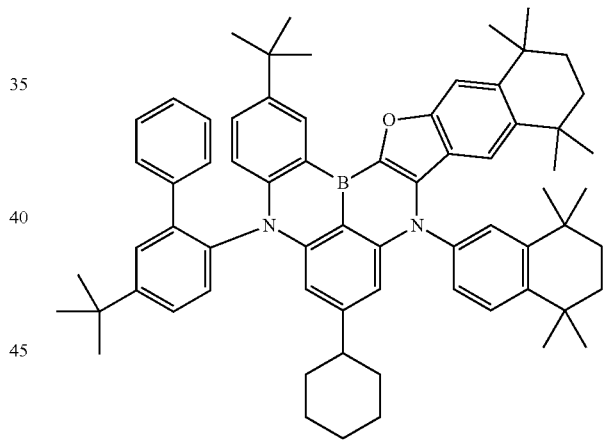
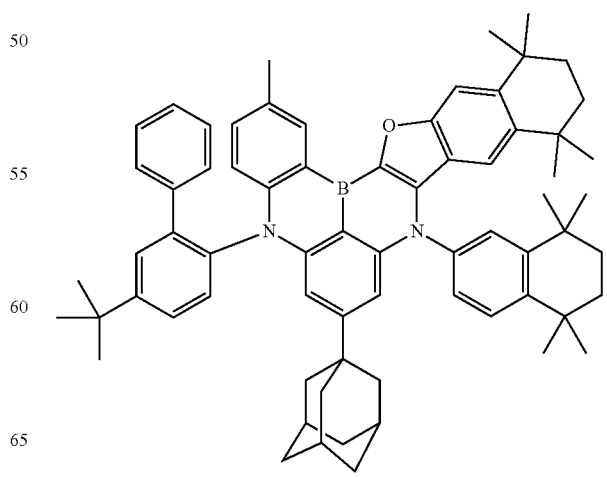

393
-continued
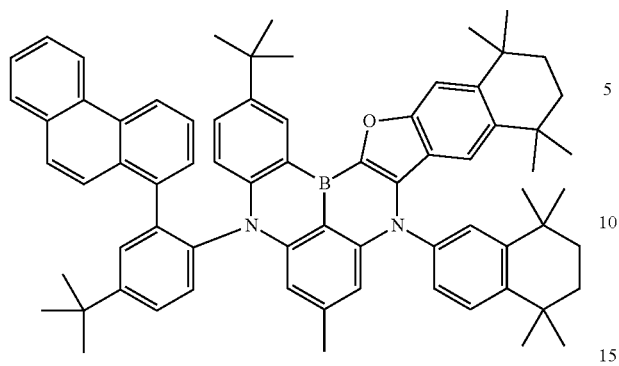
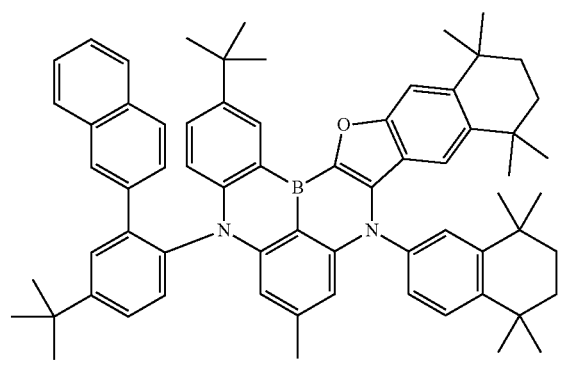
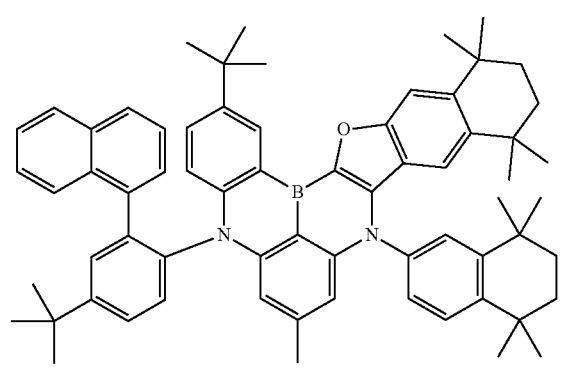
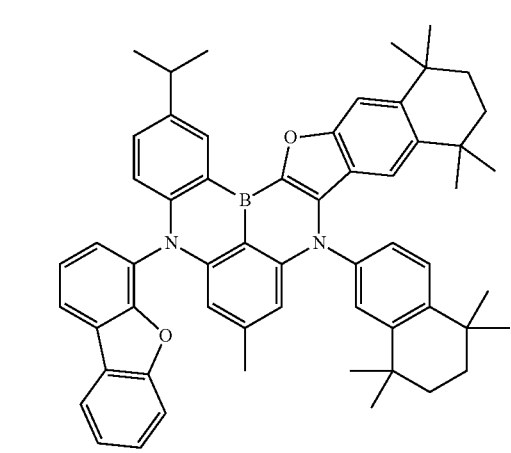
394
-continued
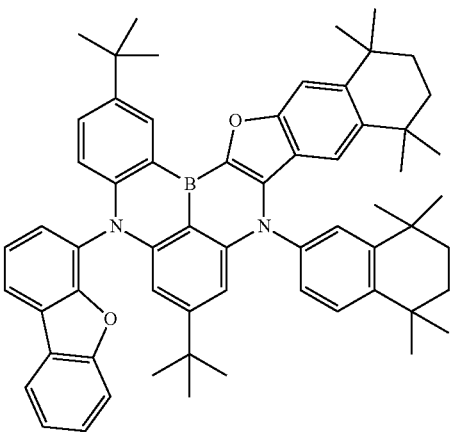
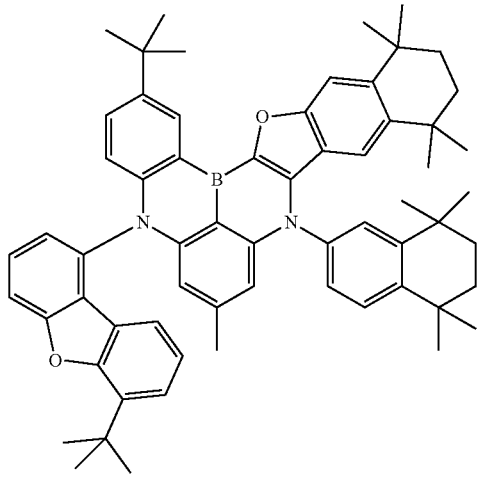
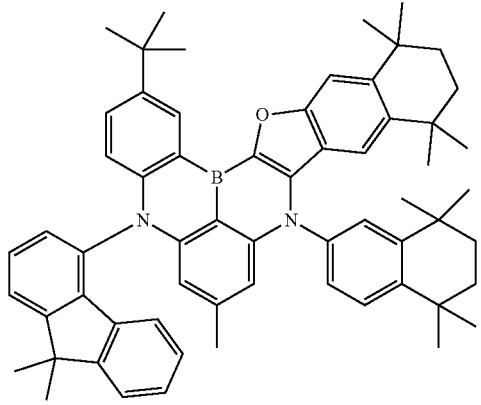
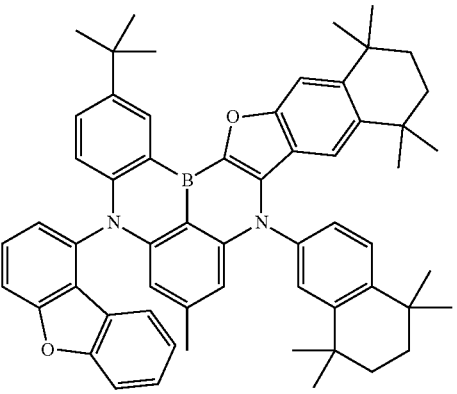

395
-continued
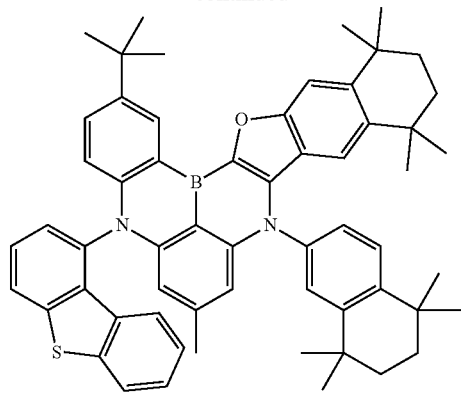
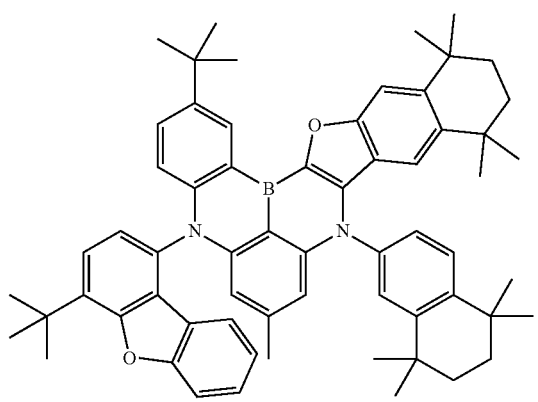
396
-continued
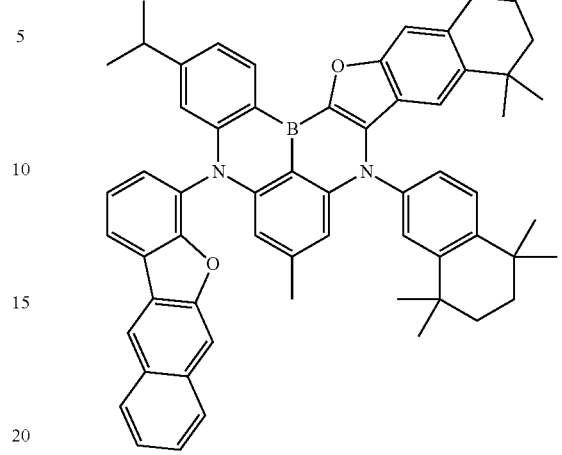
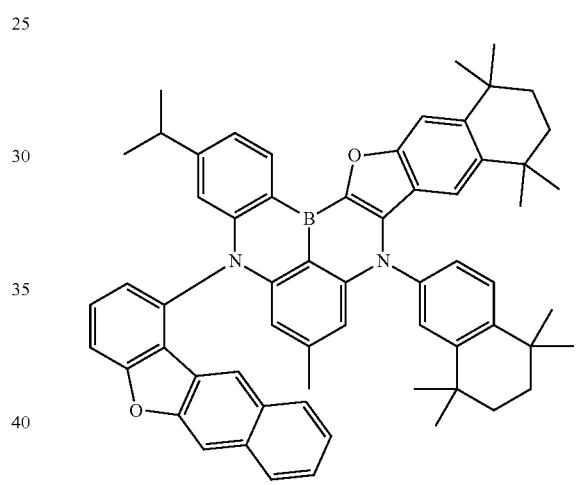
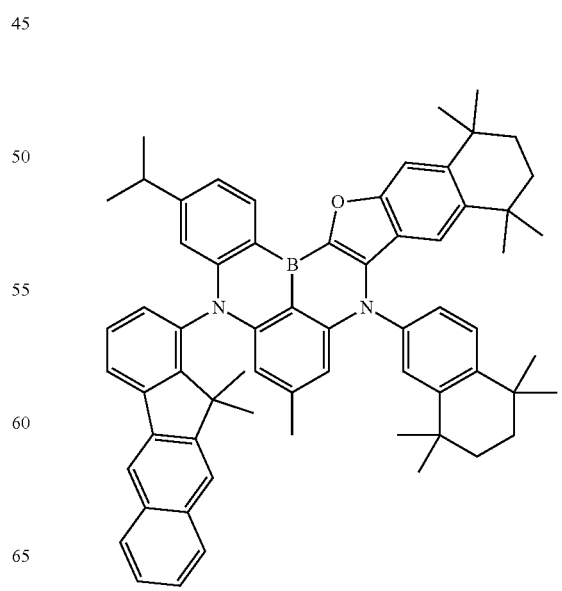

397
-continued
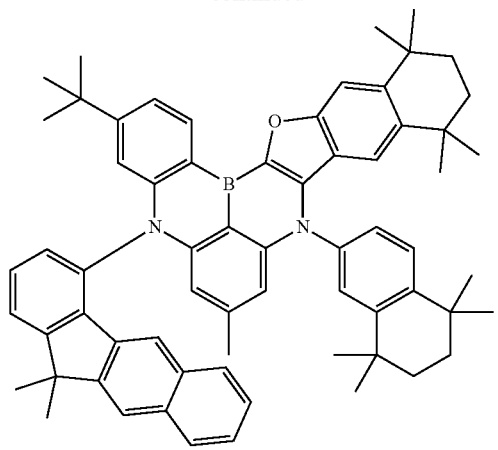
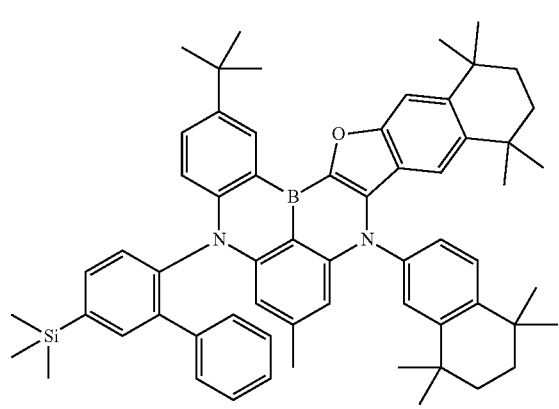
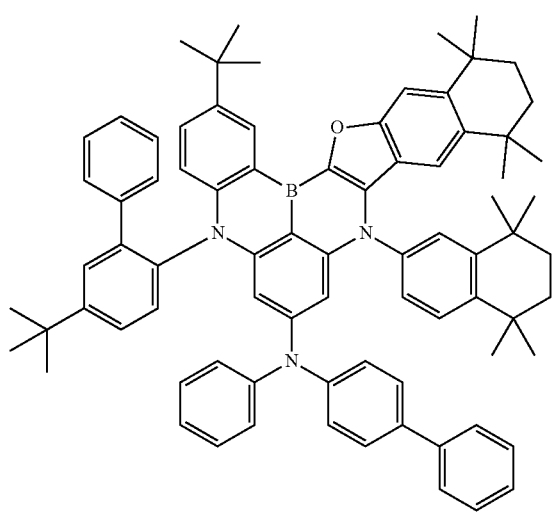
398
-continued
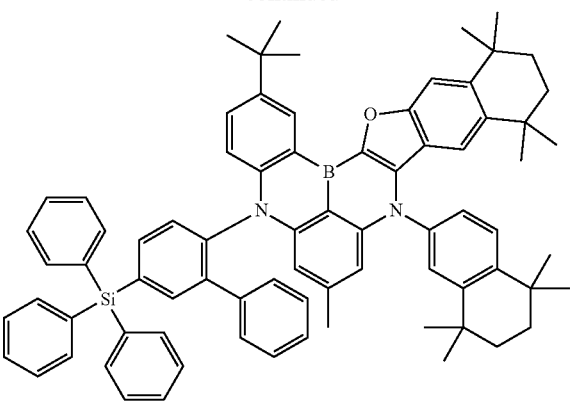
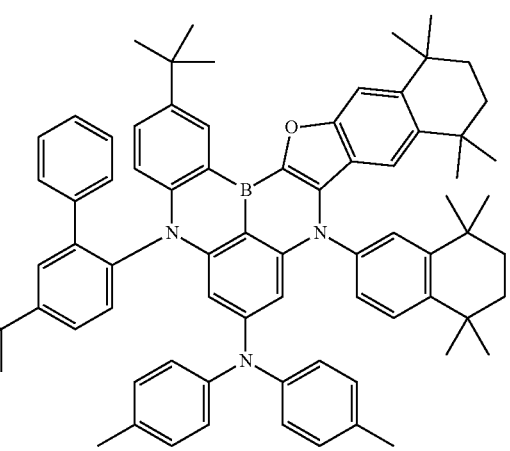
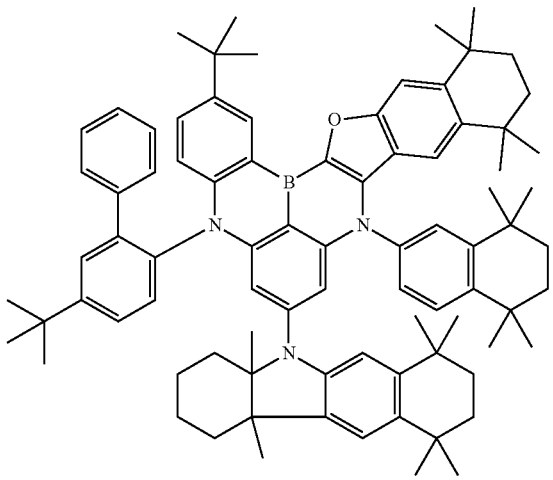

399
-continued
400
-continued
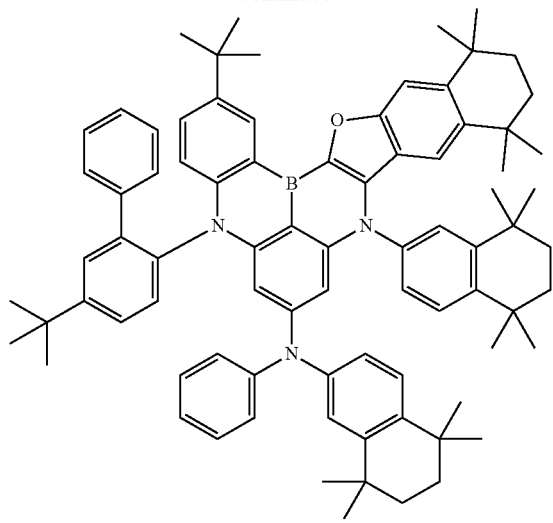
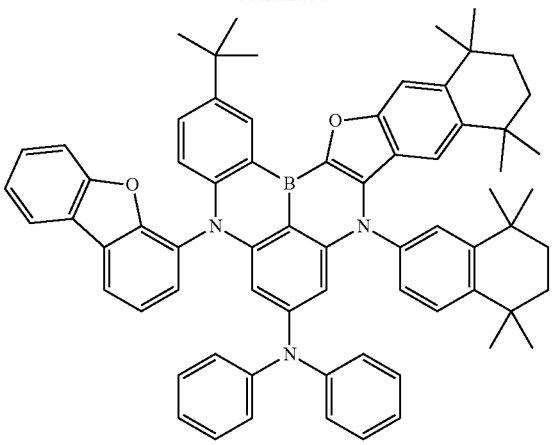
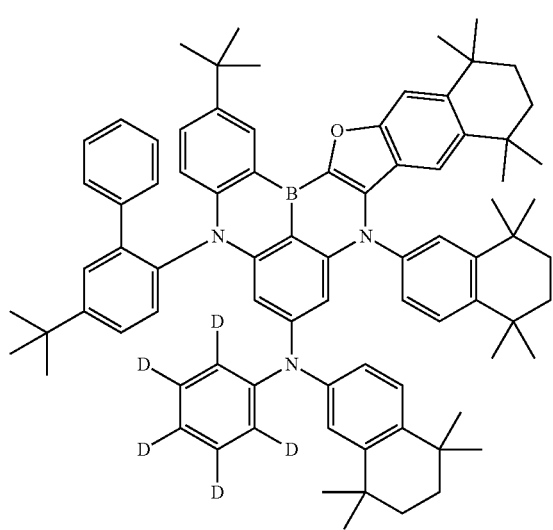
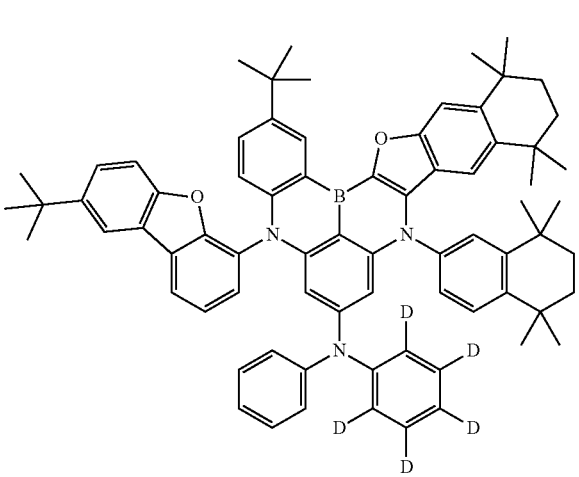
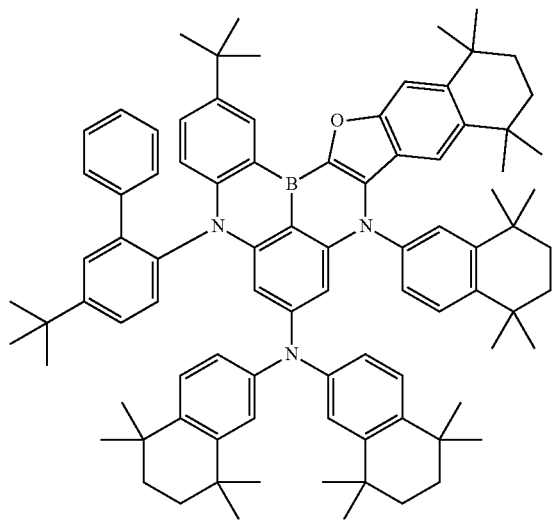
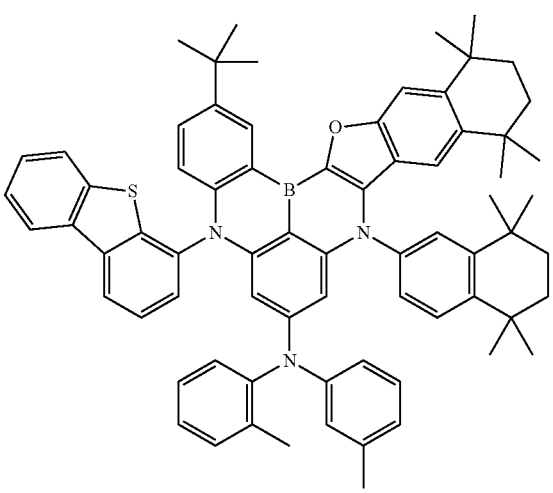

401
-continued
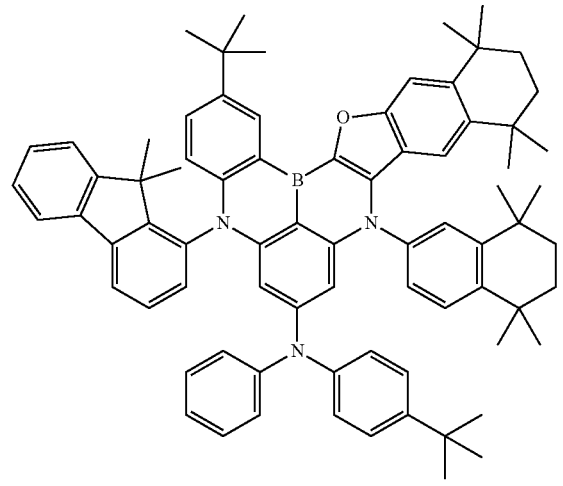
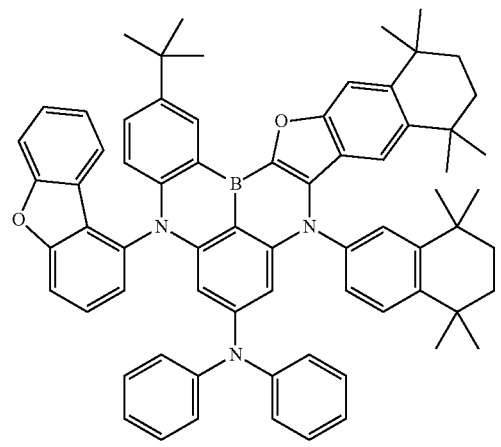
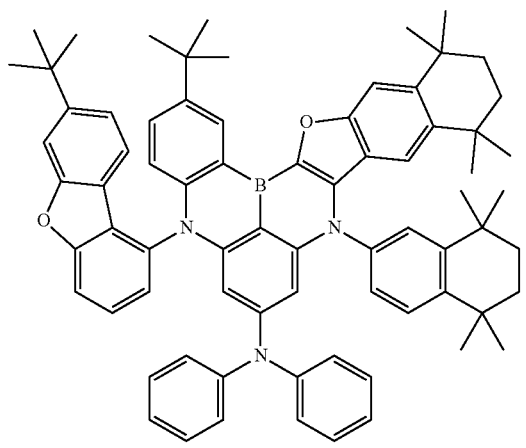
402
-continued
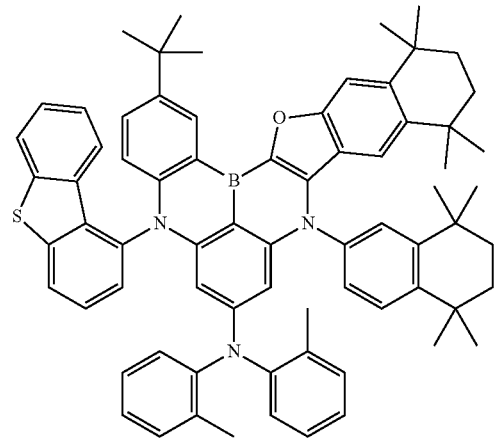
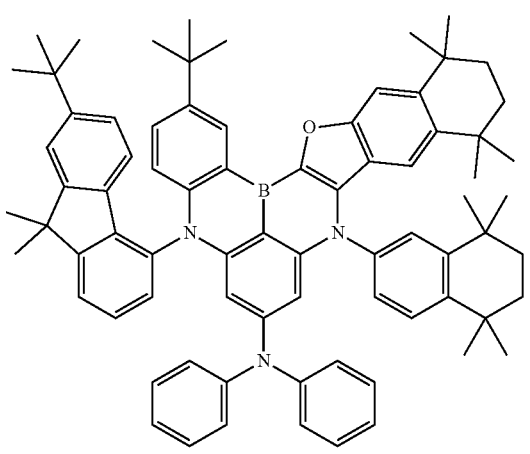
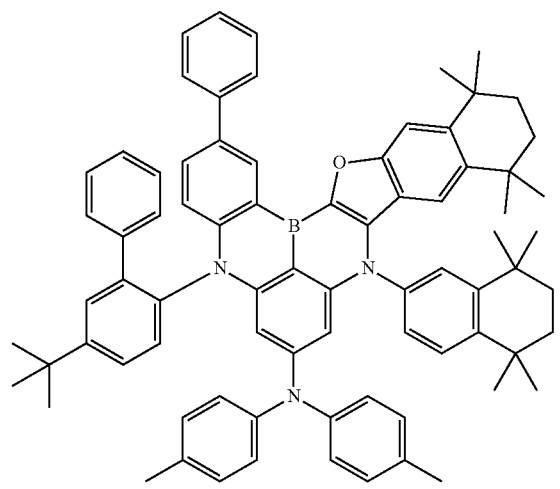

403
-continued
404
-continued
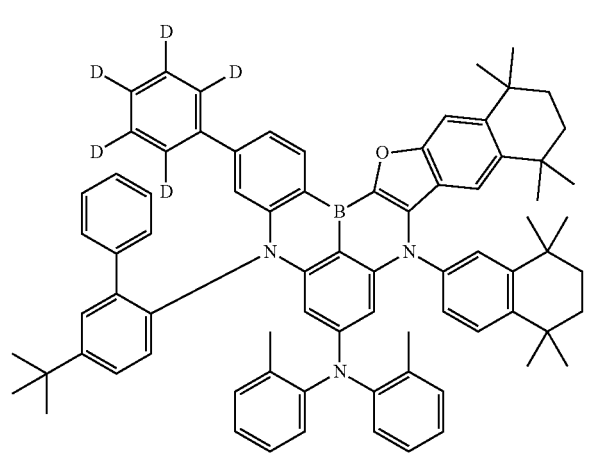
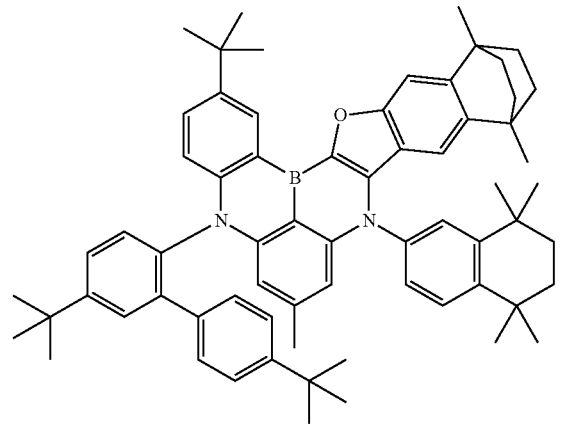

405
-continued
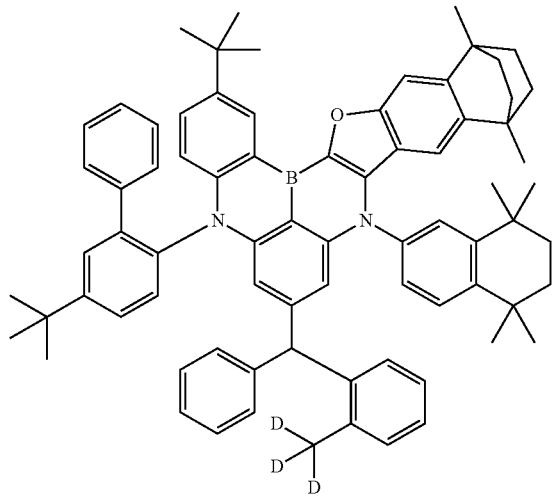
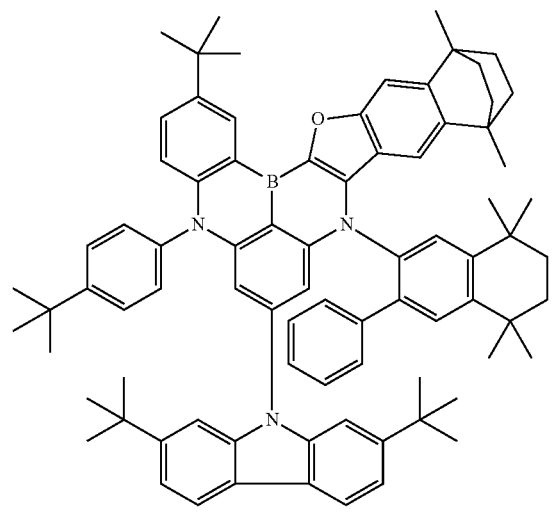
406
-continued
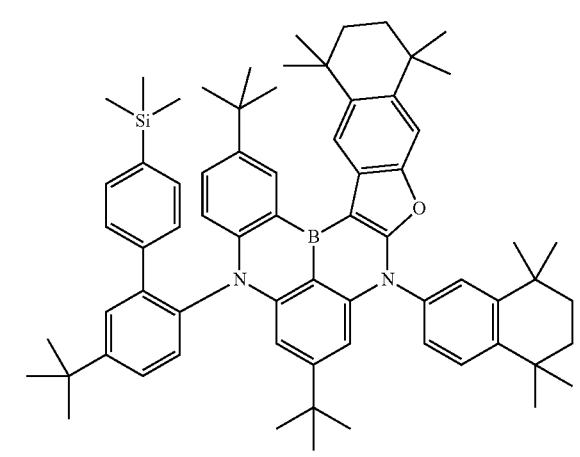
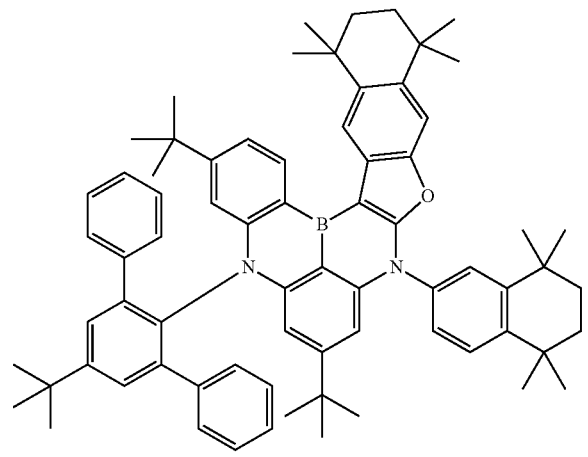
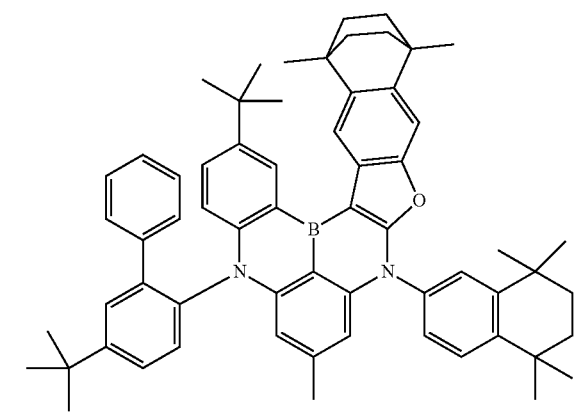

407
-continued
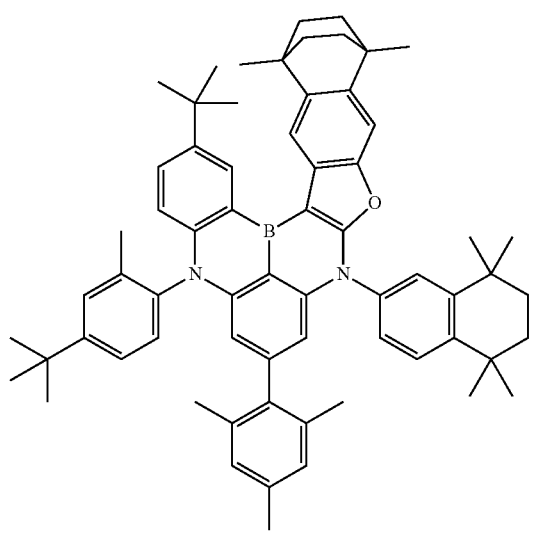
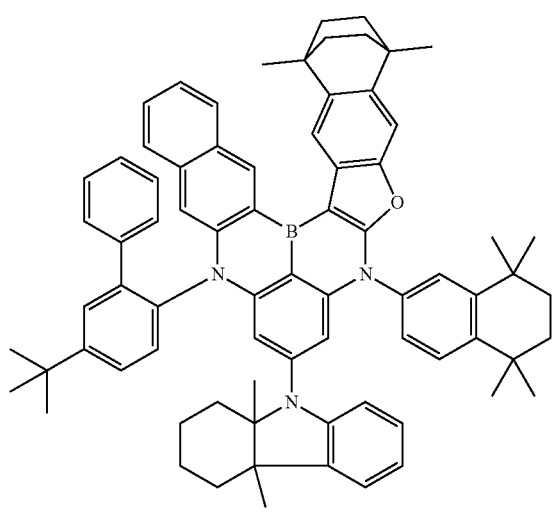
408
-continued

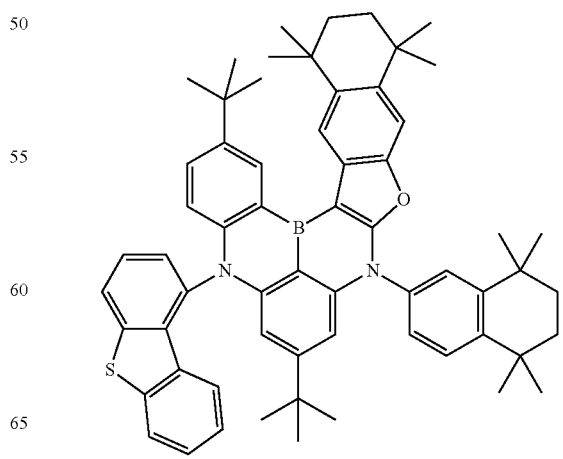

409
-continued
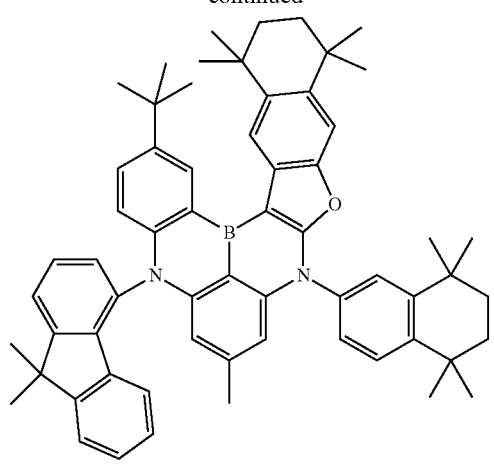
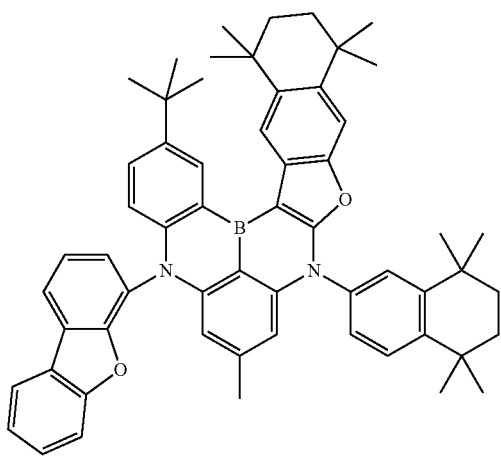
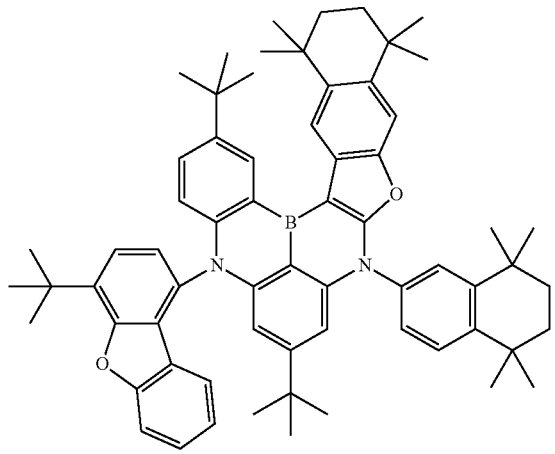
410
-continued
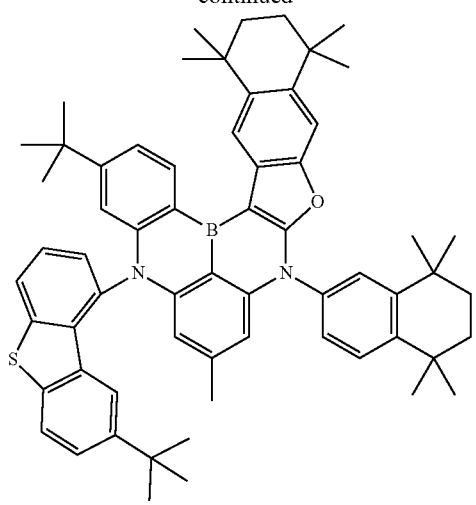
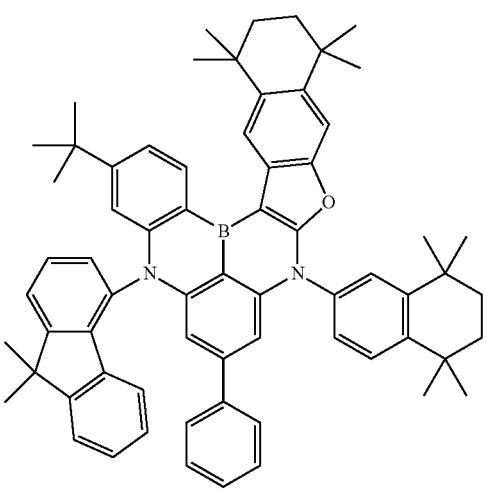
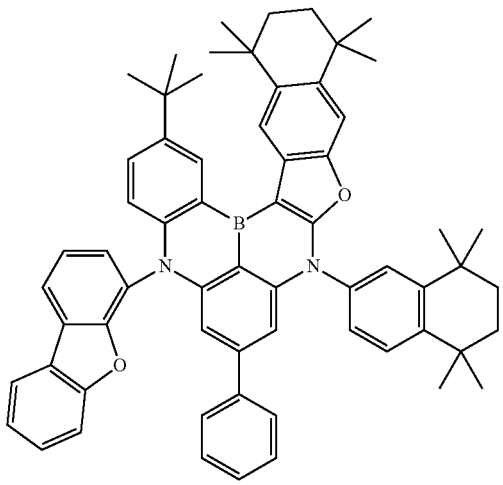

411
-continued
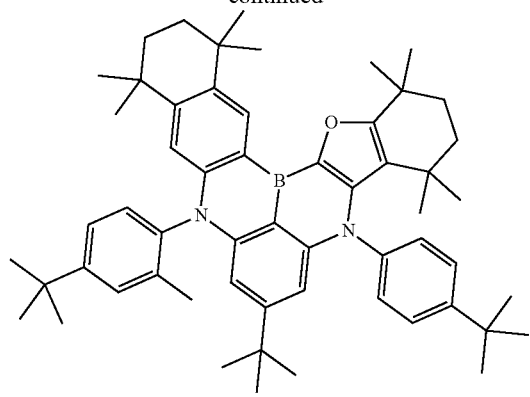
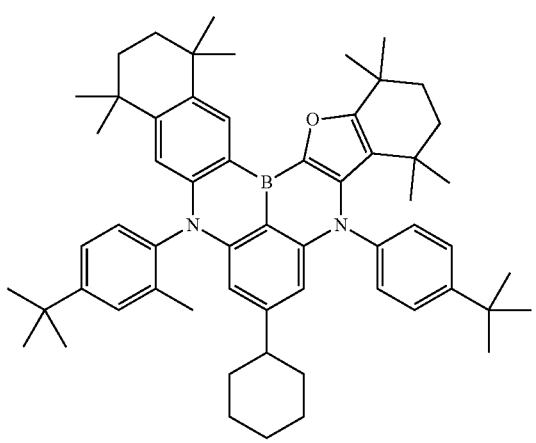
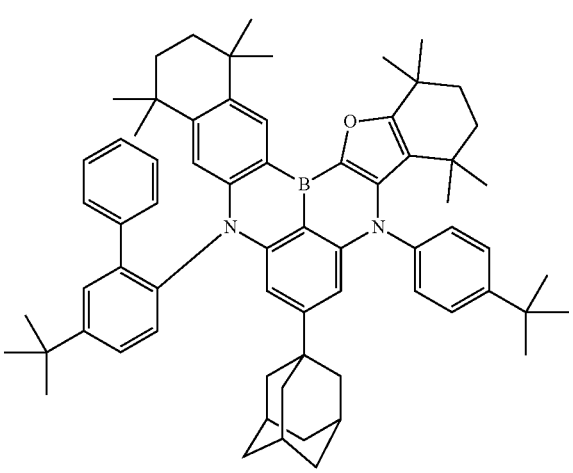
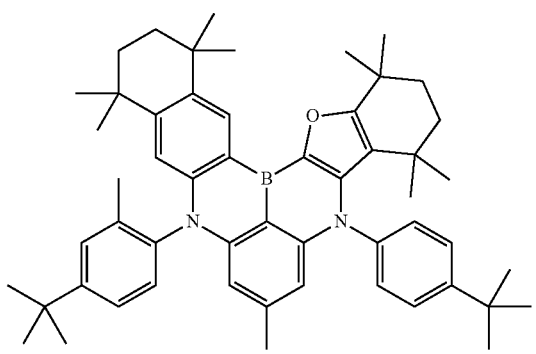
412
-continued
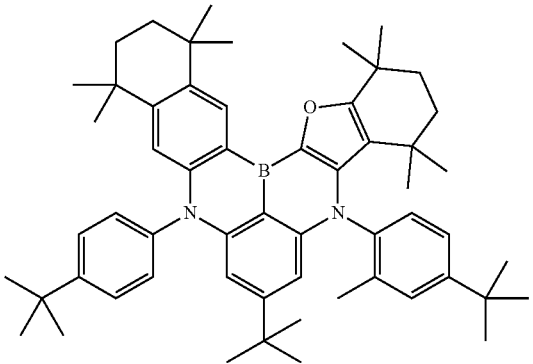
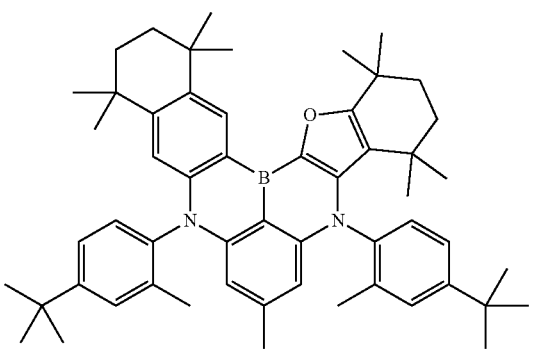
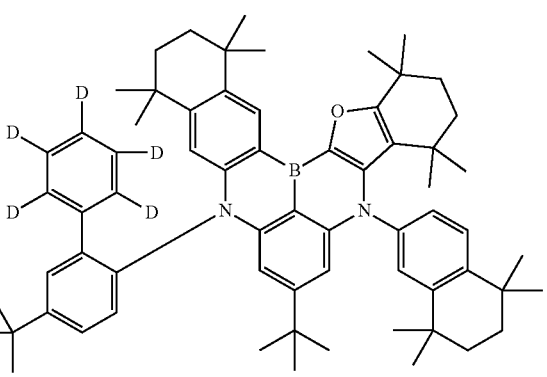
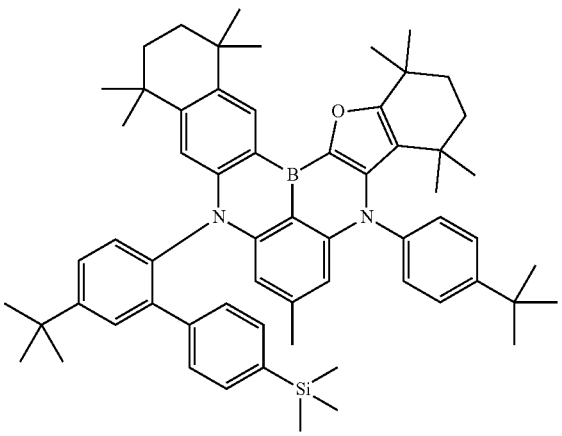

413
-continued
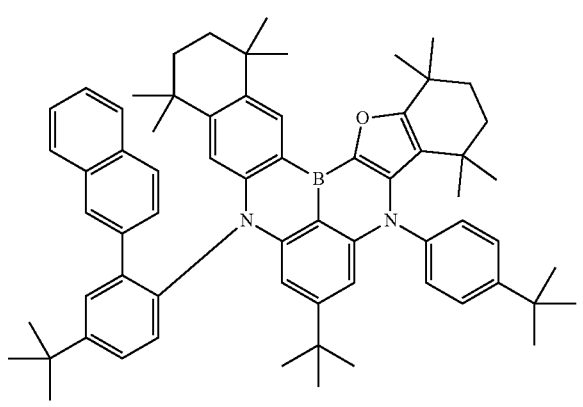
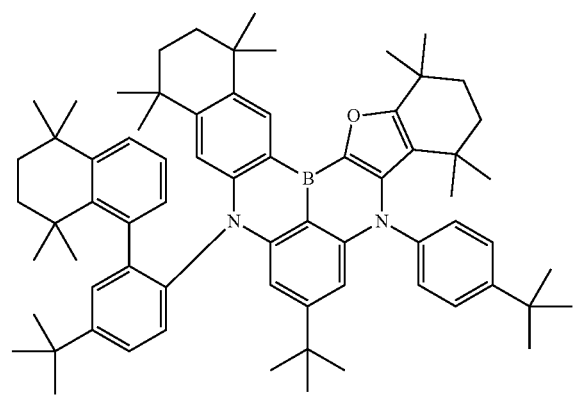
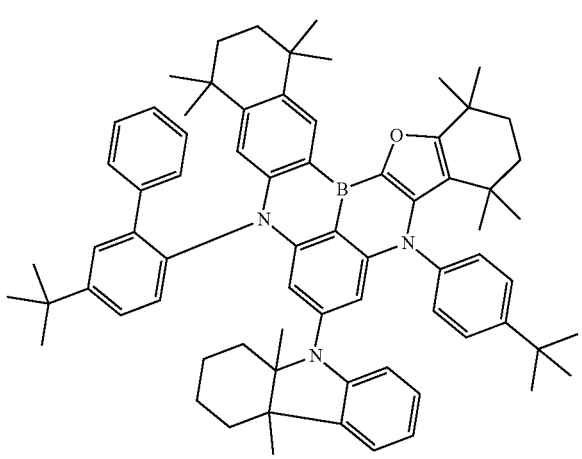
414
-continued
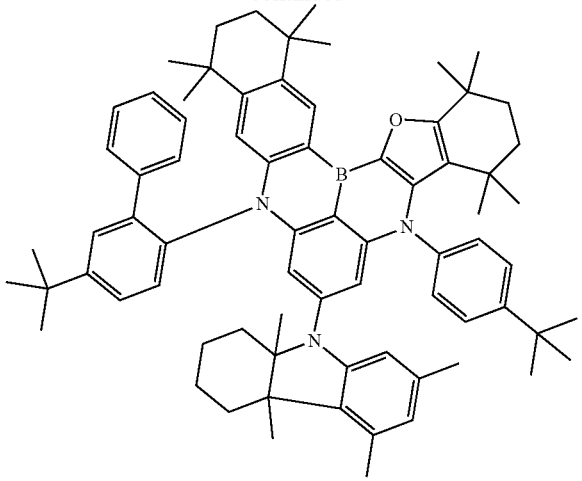
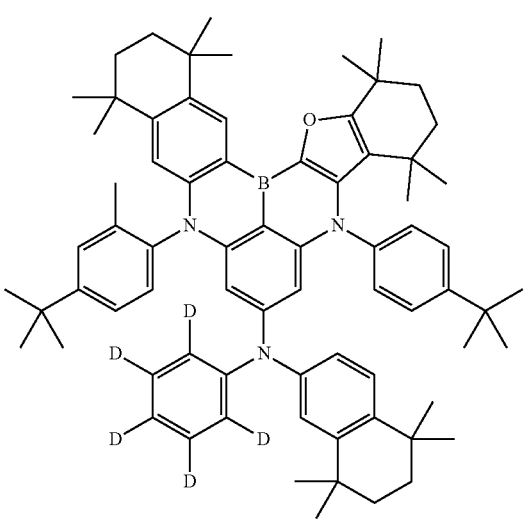
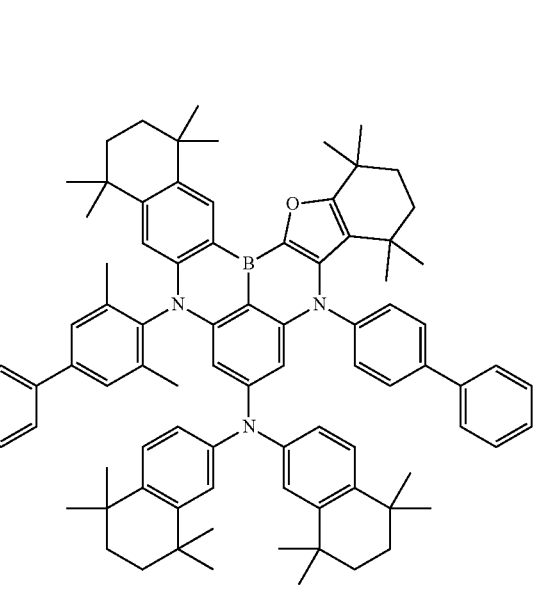

415
-continued
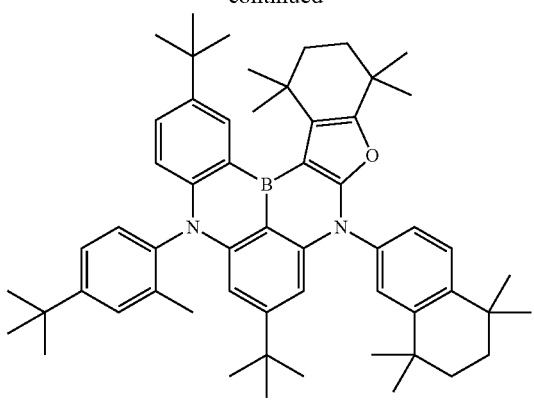
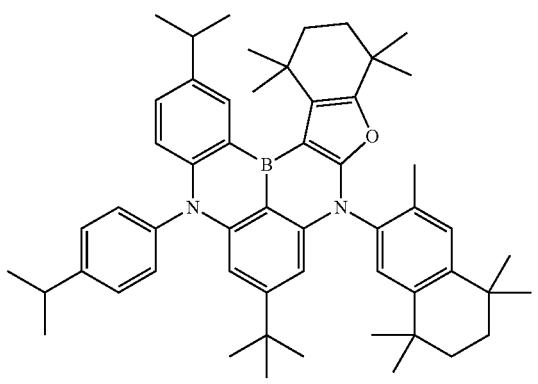
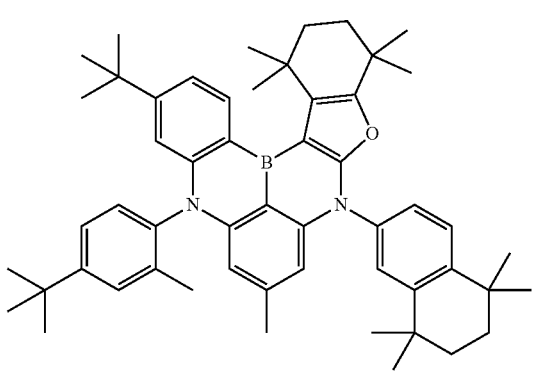
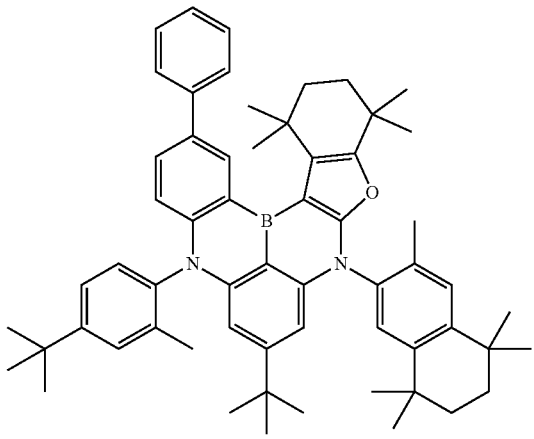
416
-continued
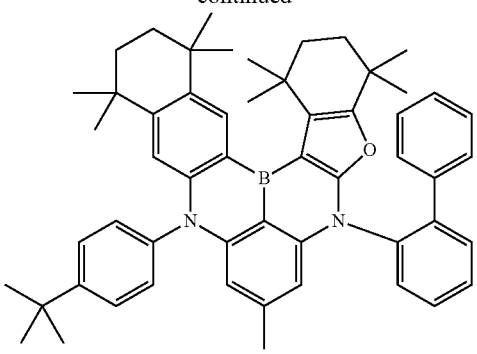
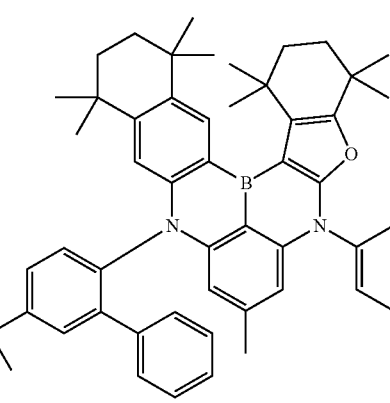
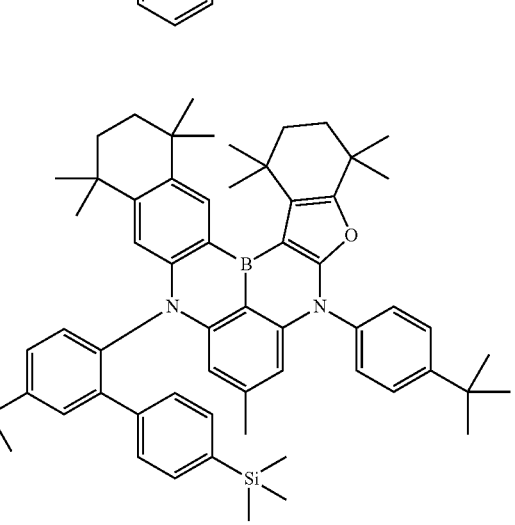
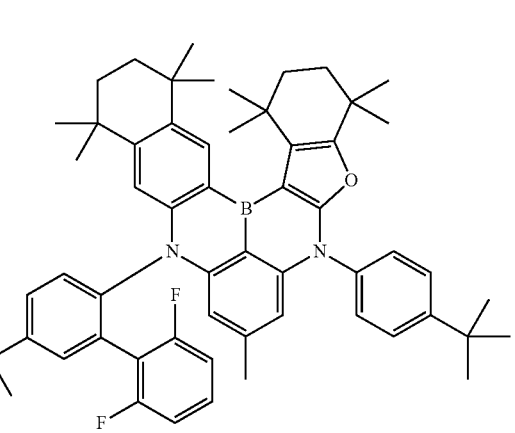

417
-continued
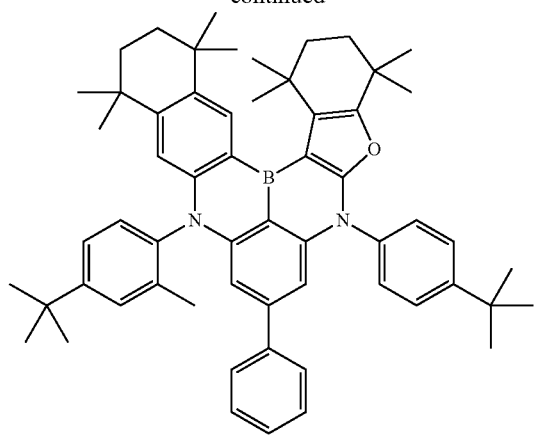
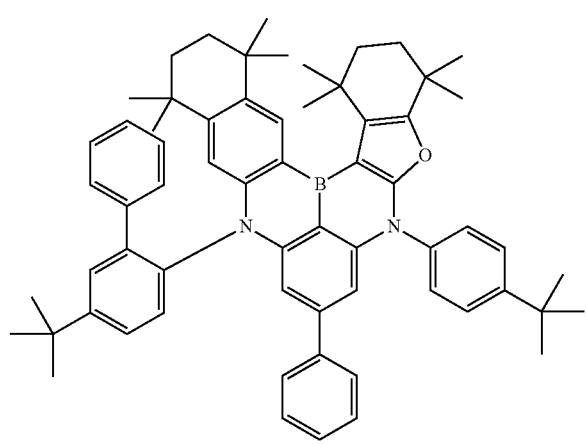
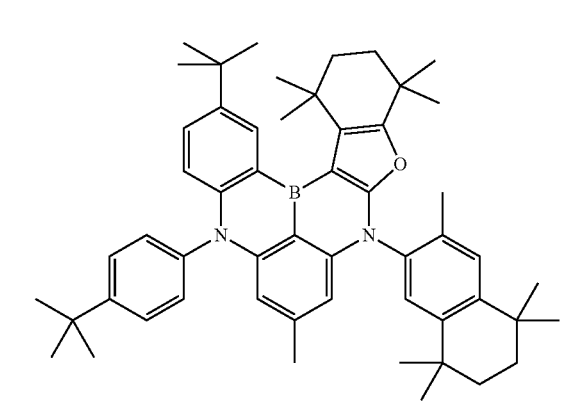
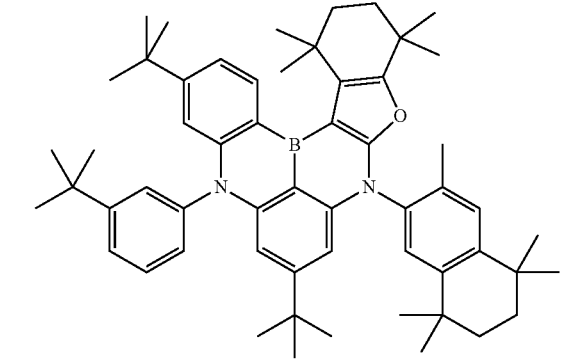
418
-continued
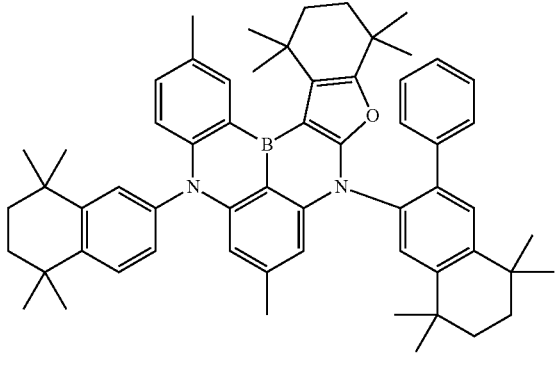
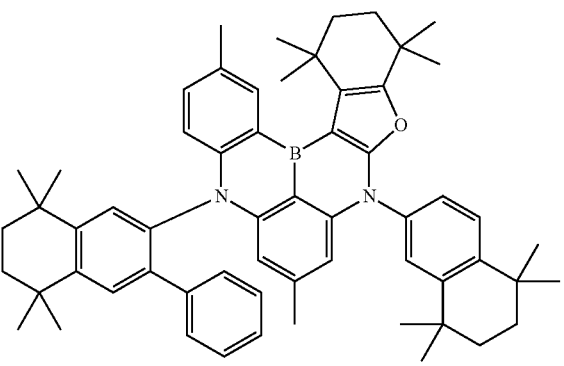
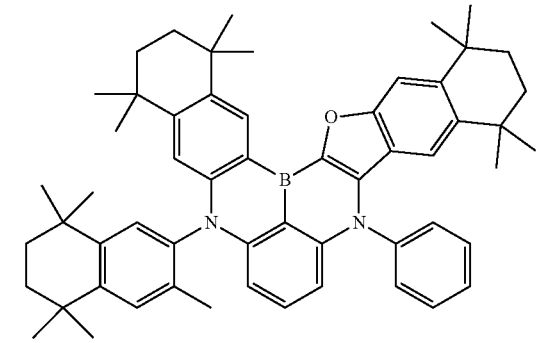
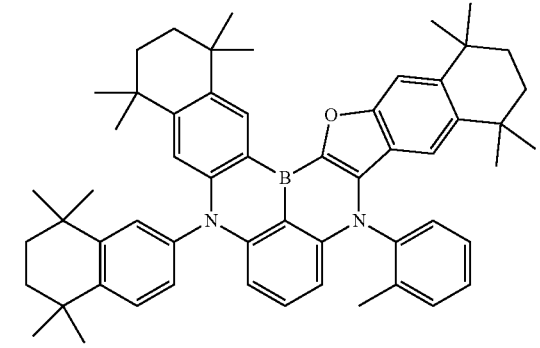

419
-continued
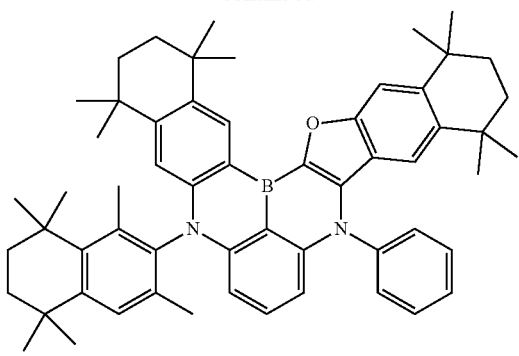
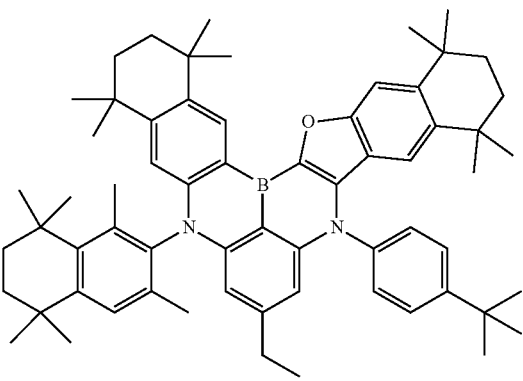
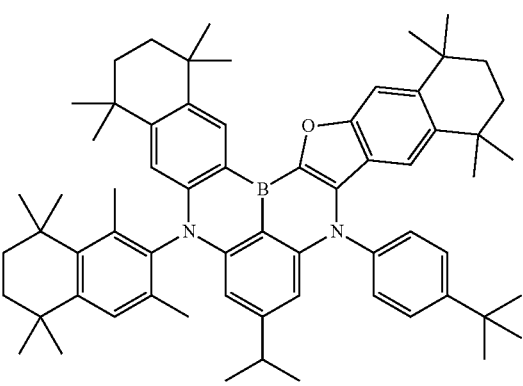
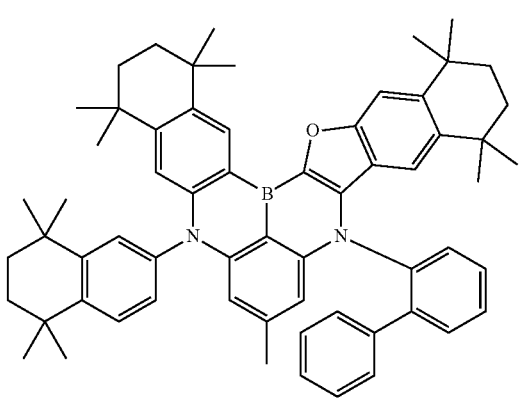
420
-continued
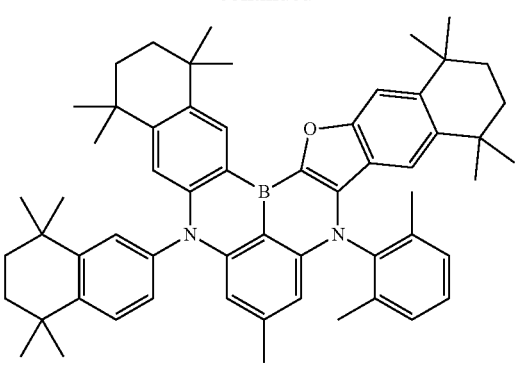
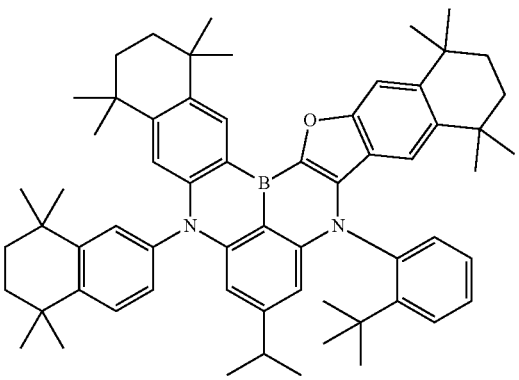
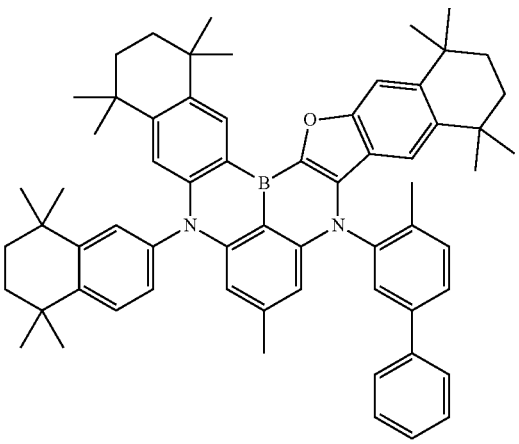
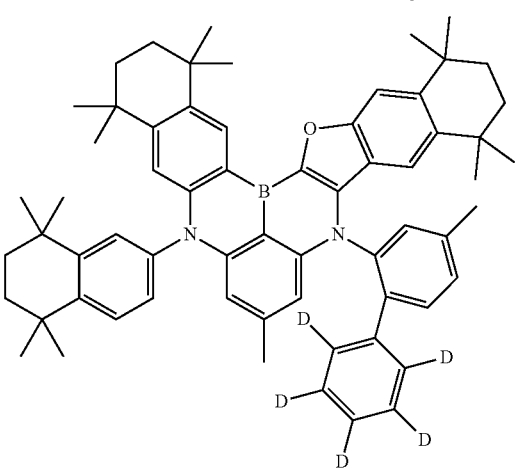

421
-continued
422
-continued
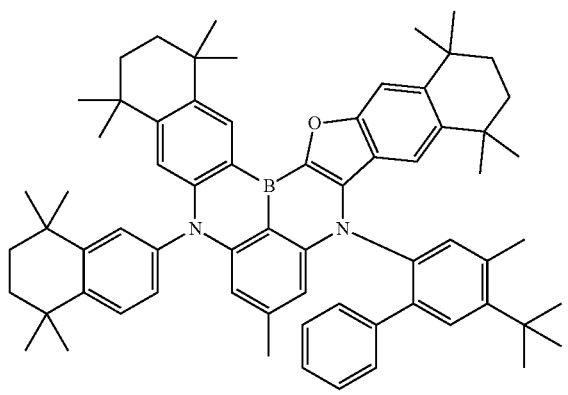
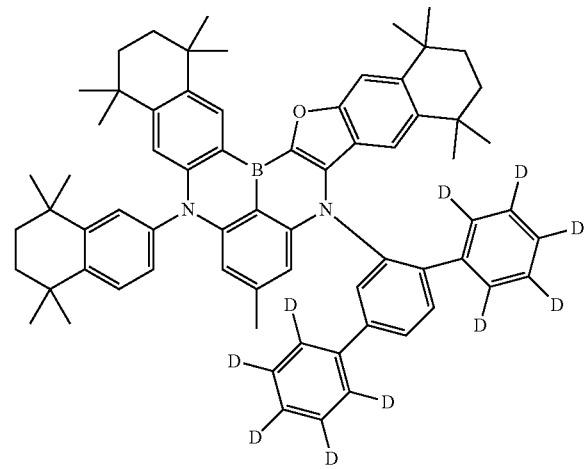
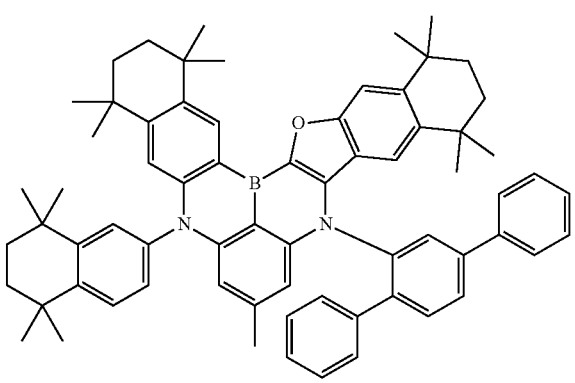
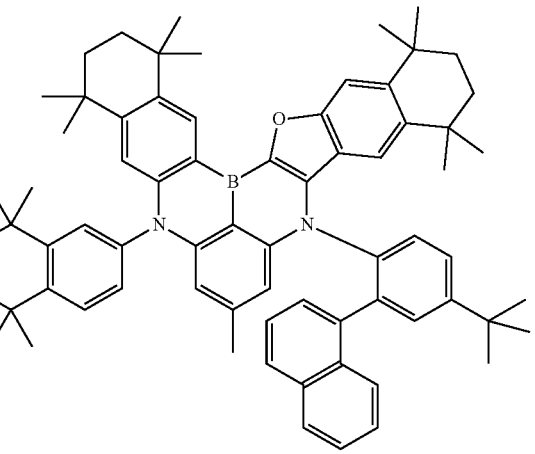
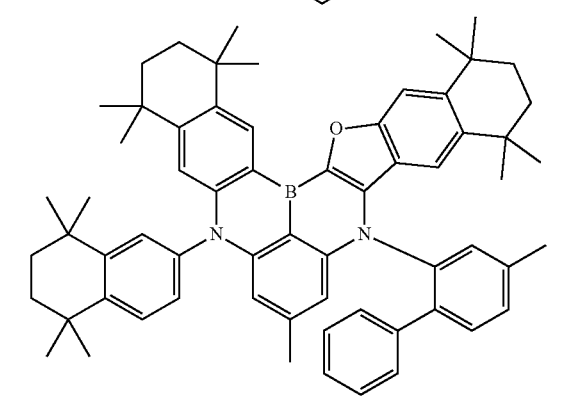
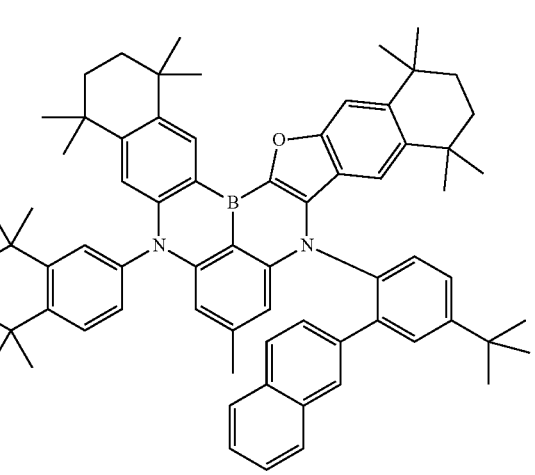

423
-continued
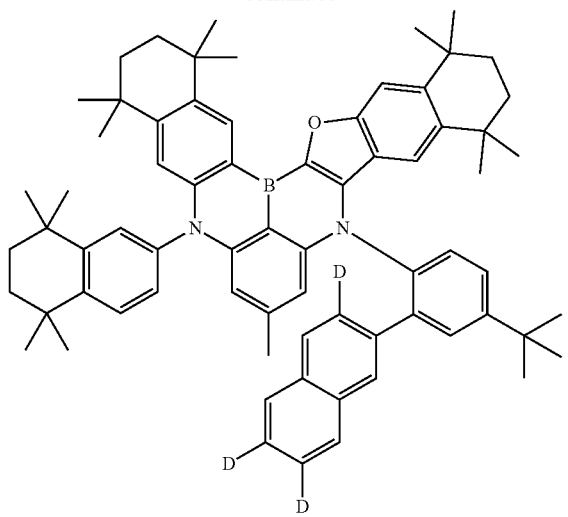
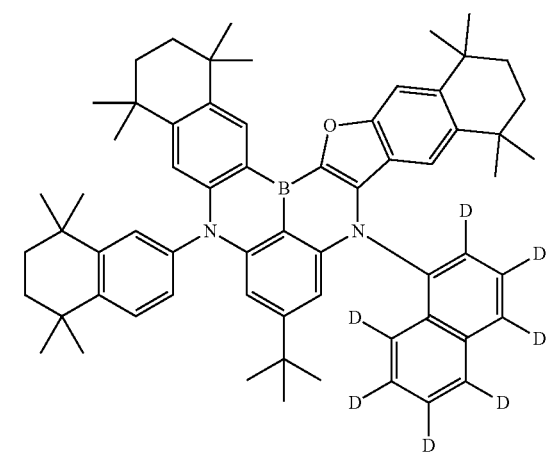
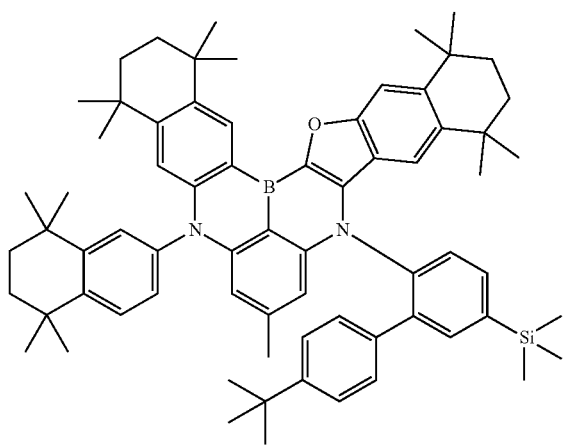
424
-continued
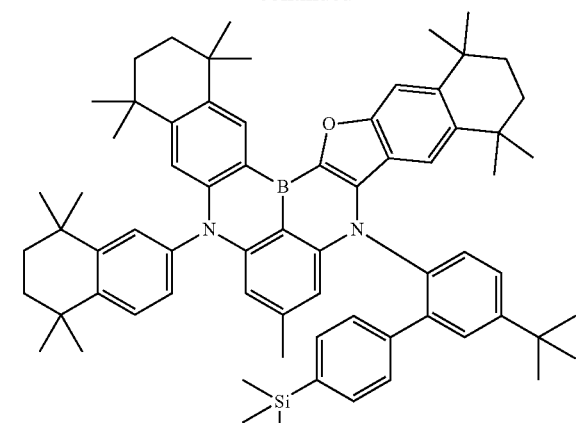
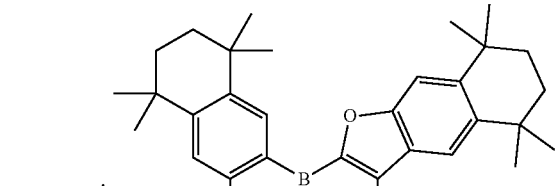
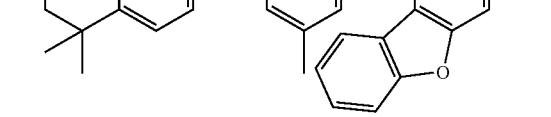
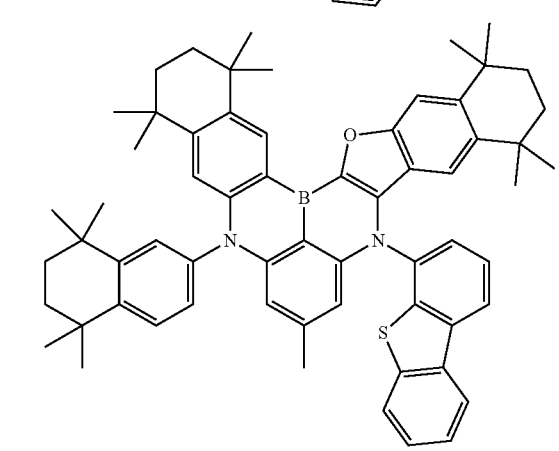
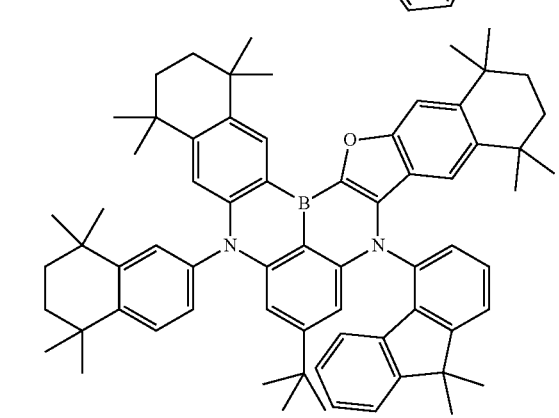

425
-continued
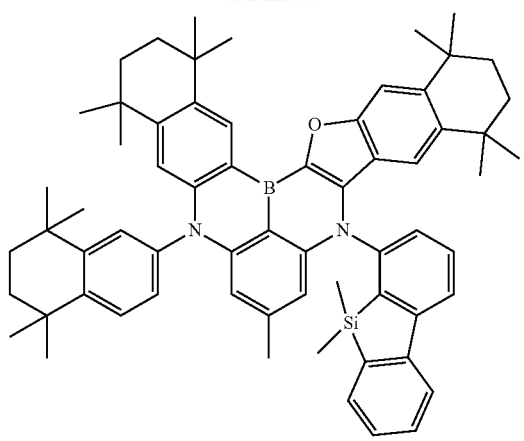
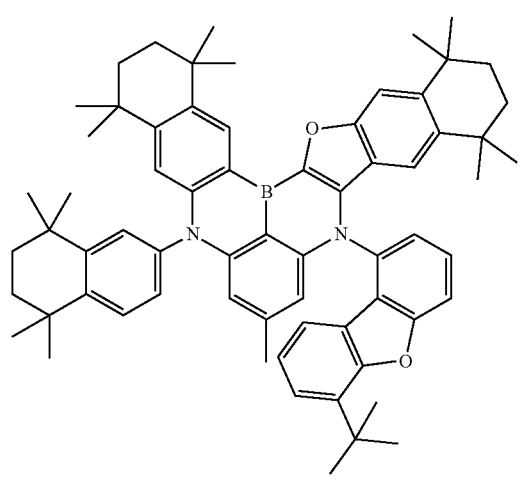
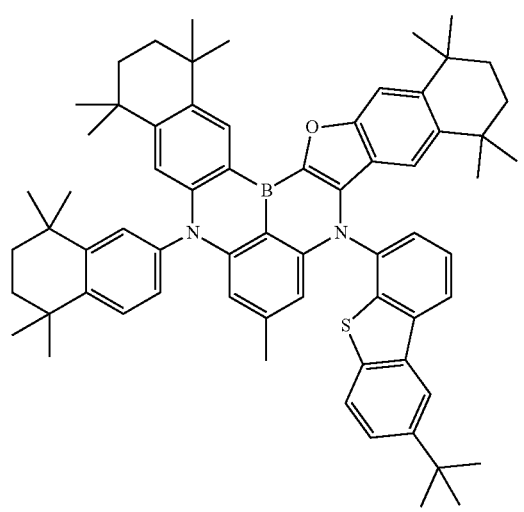
426
-continued
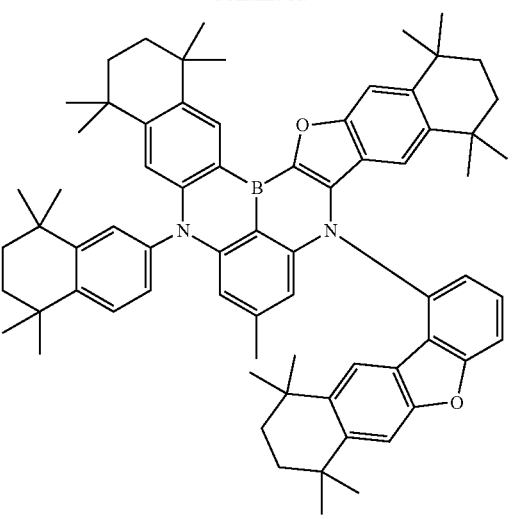
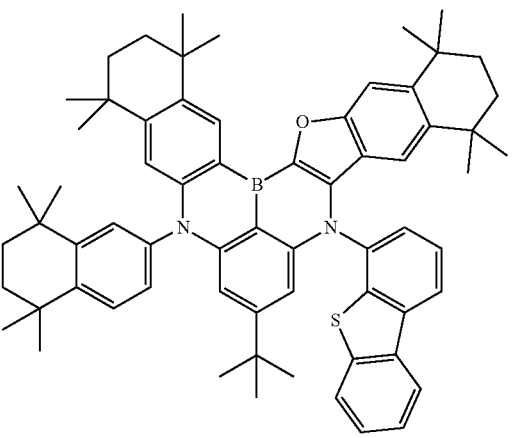
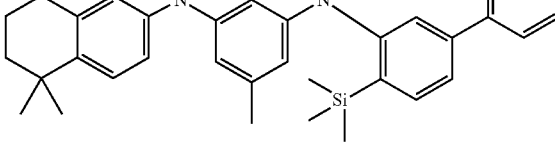
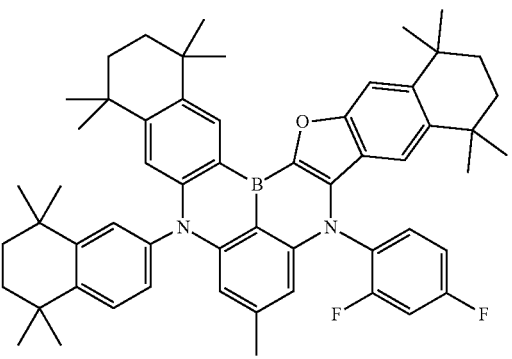

427
-continued
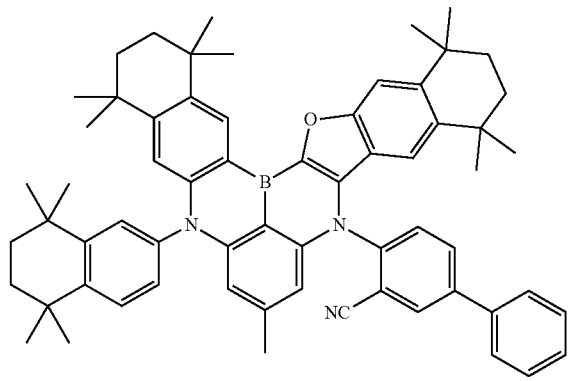
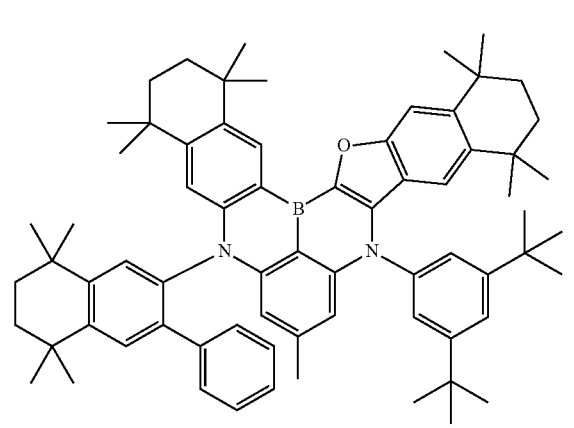
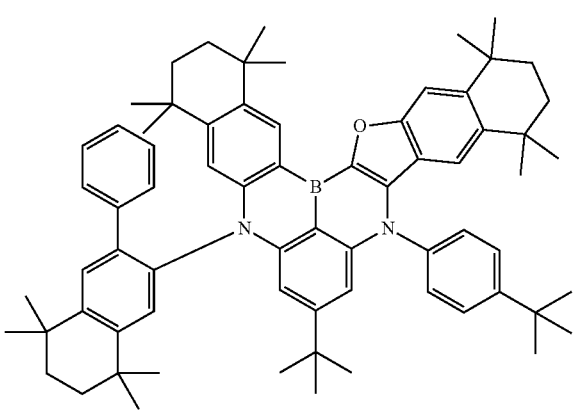
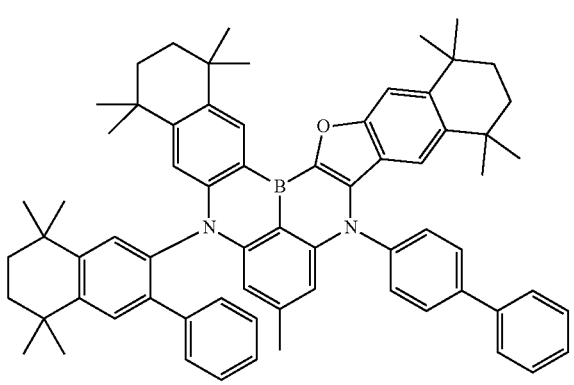
428
-continued
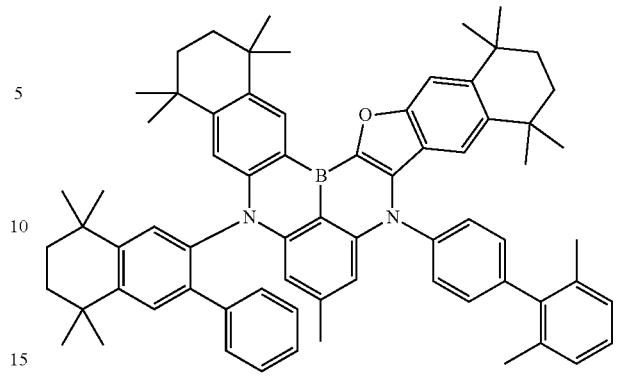
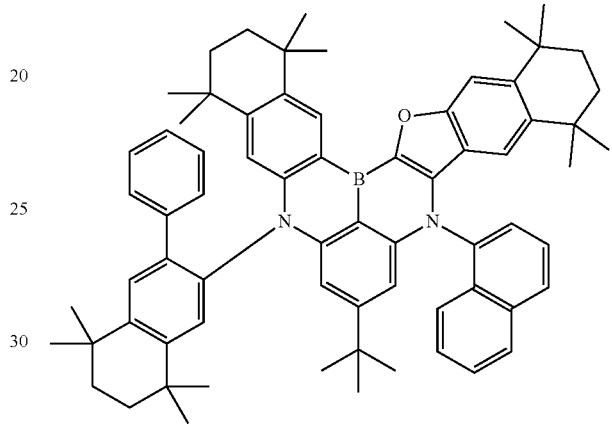
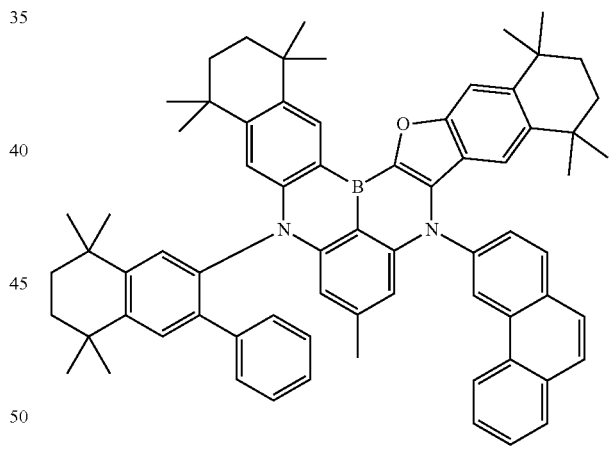
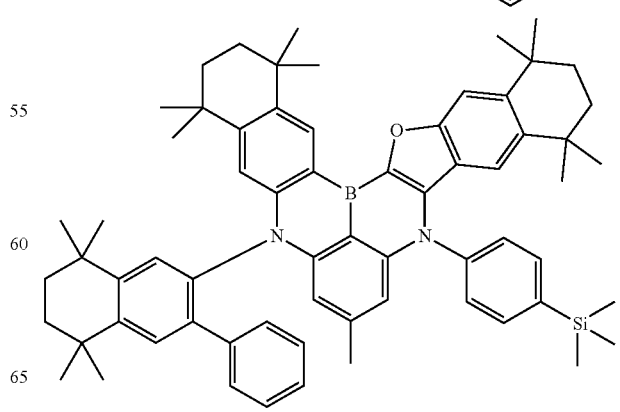

429
-continued
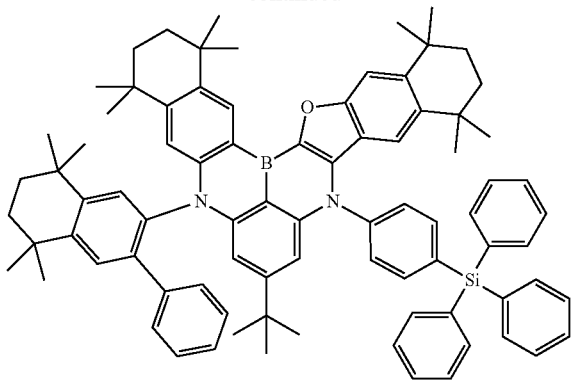
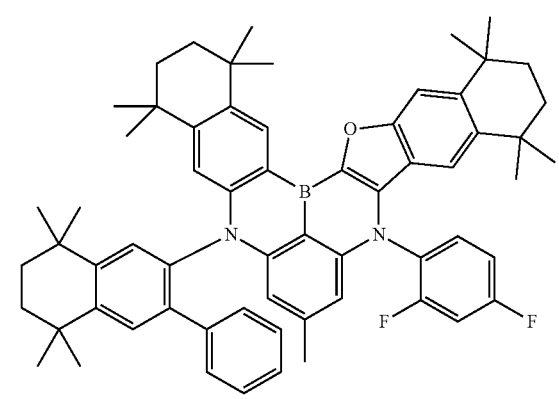
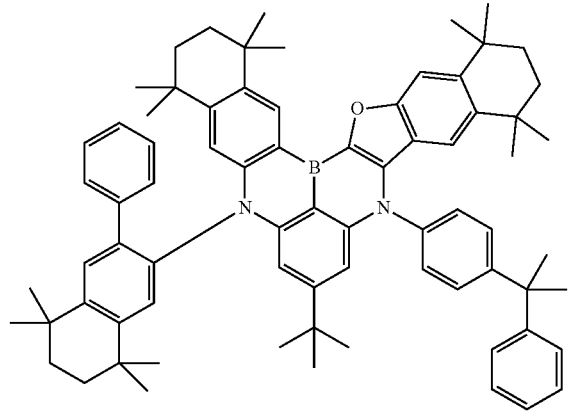
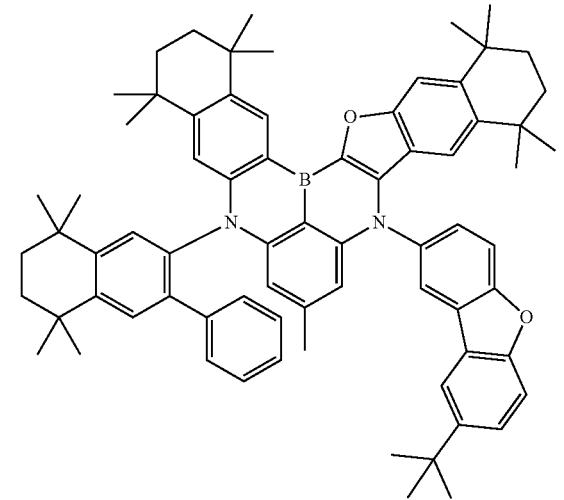
430
-continued
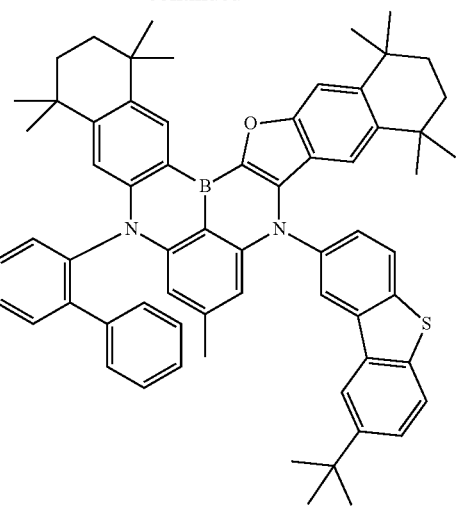
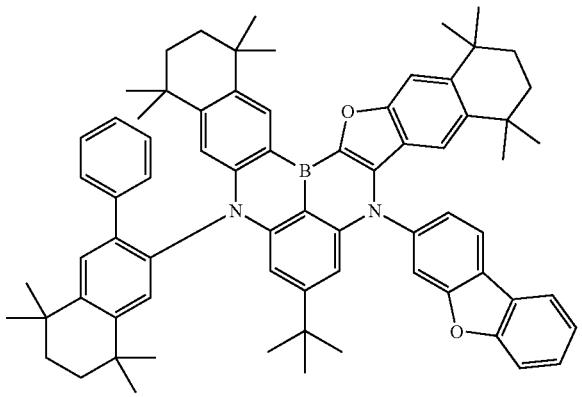
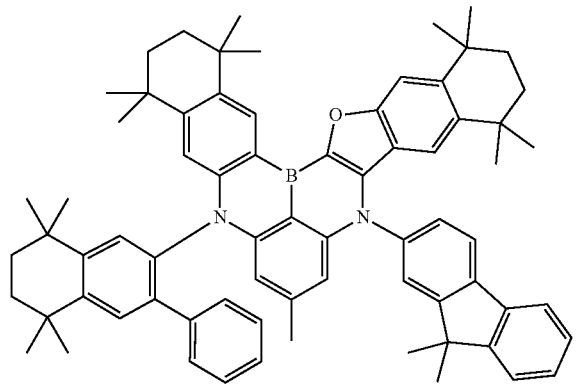
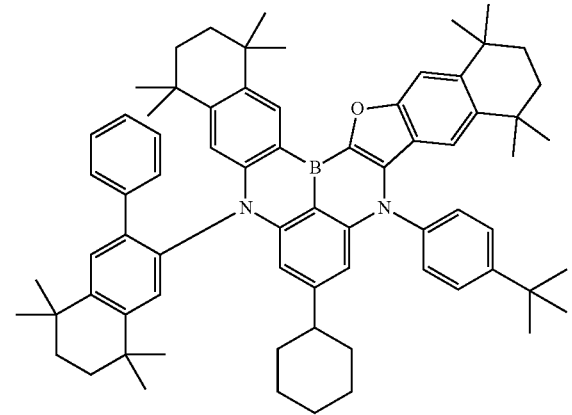

431
-continued
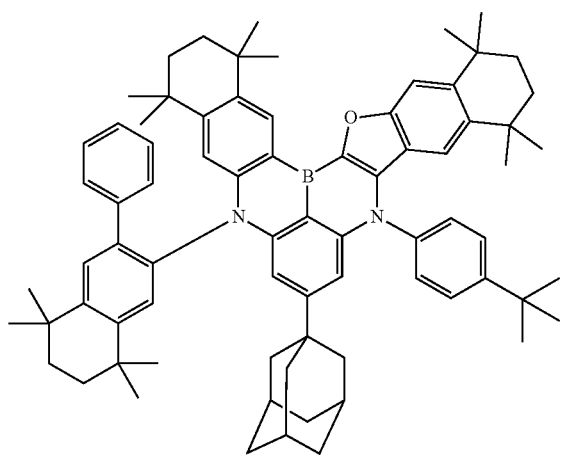
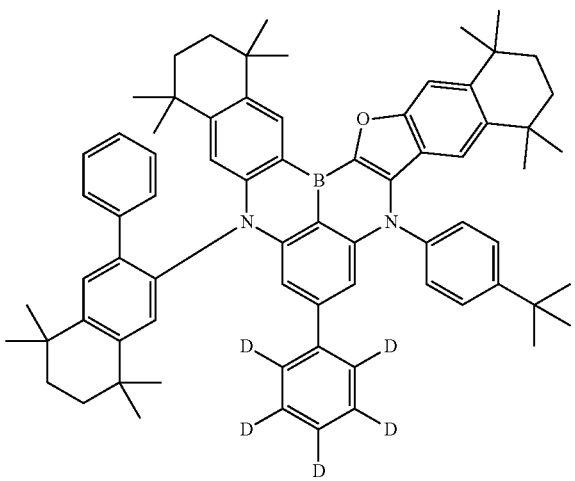
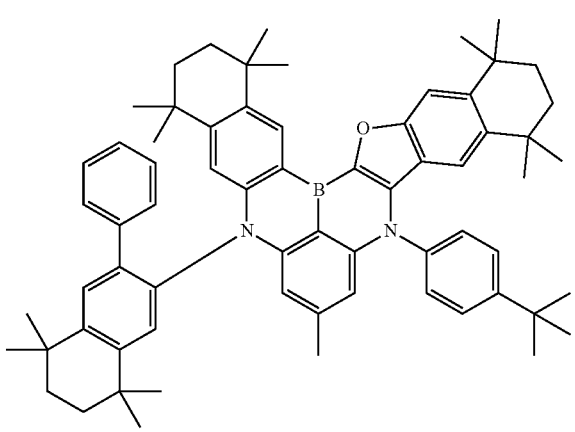
432
-continued
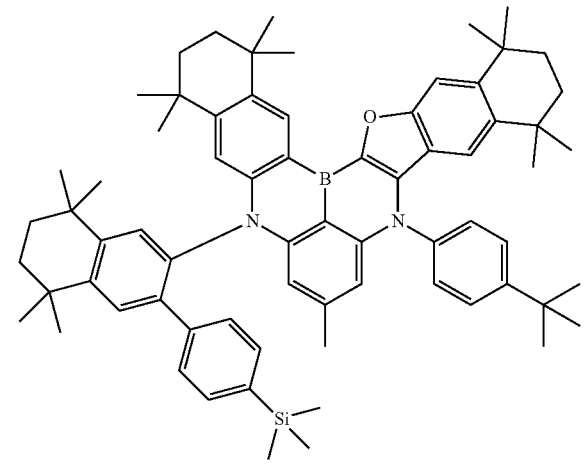
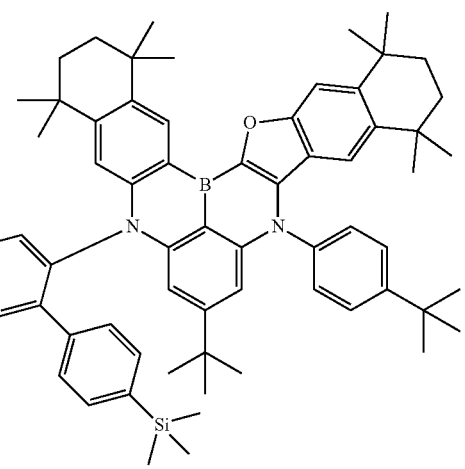
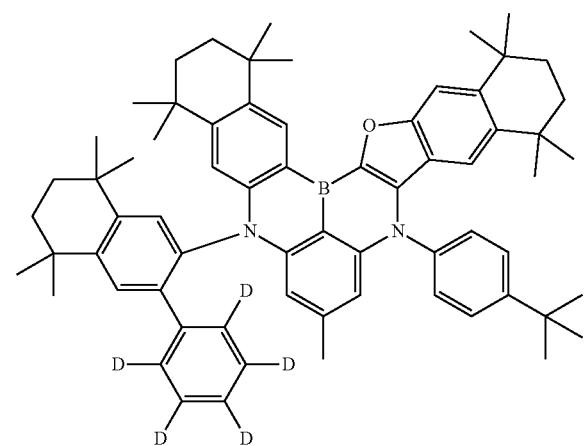

433
-continued
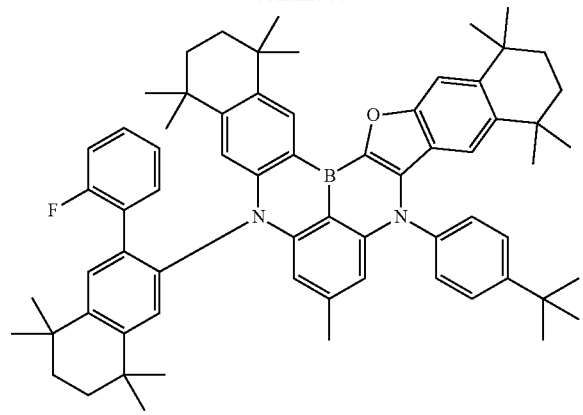
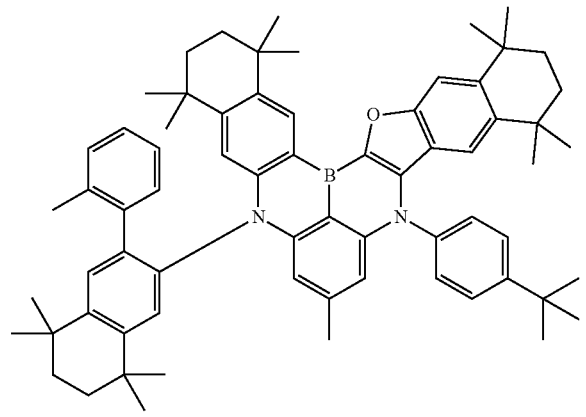
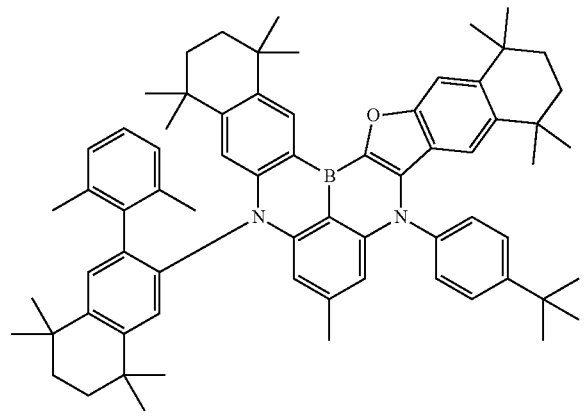
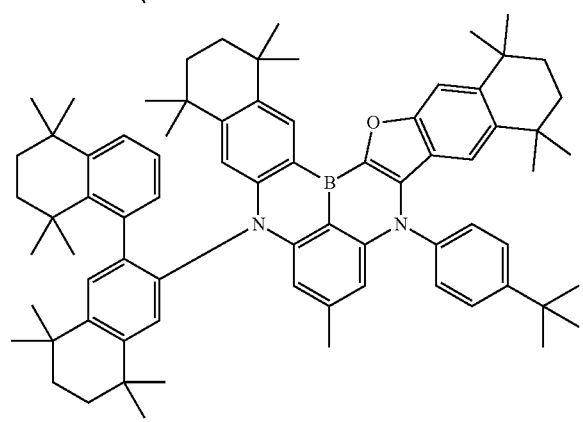
434
-continued
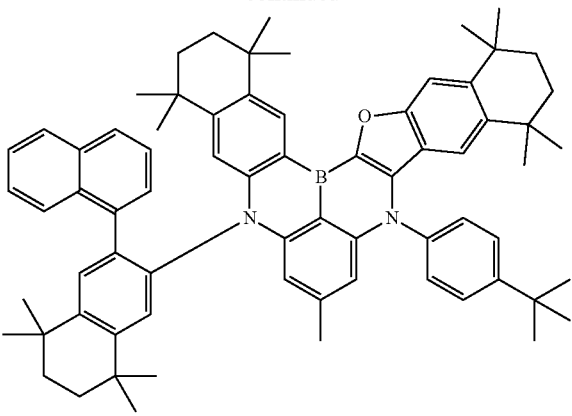
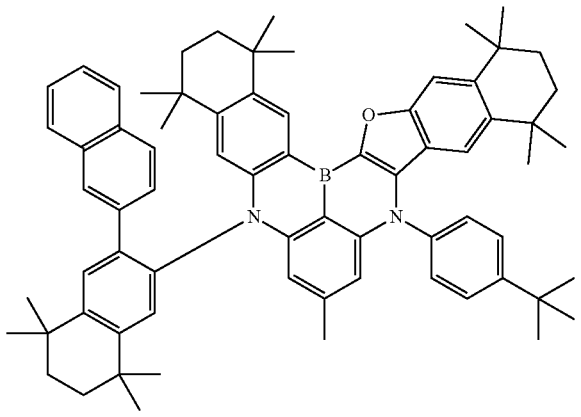
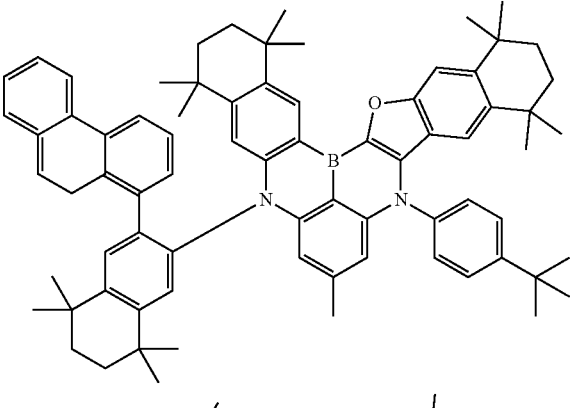
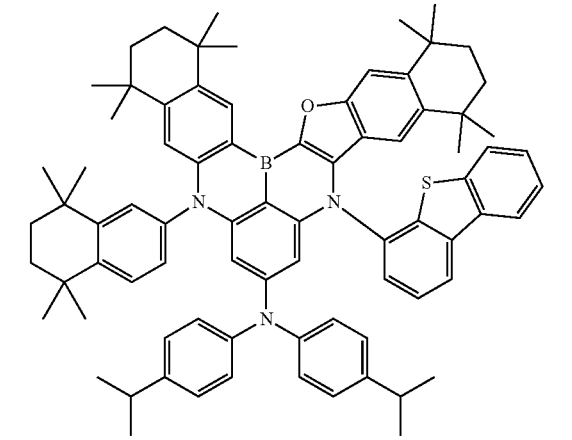

435
-continued
436
-continued
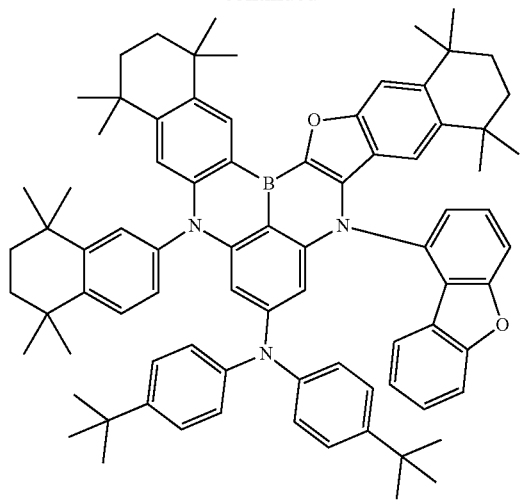
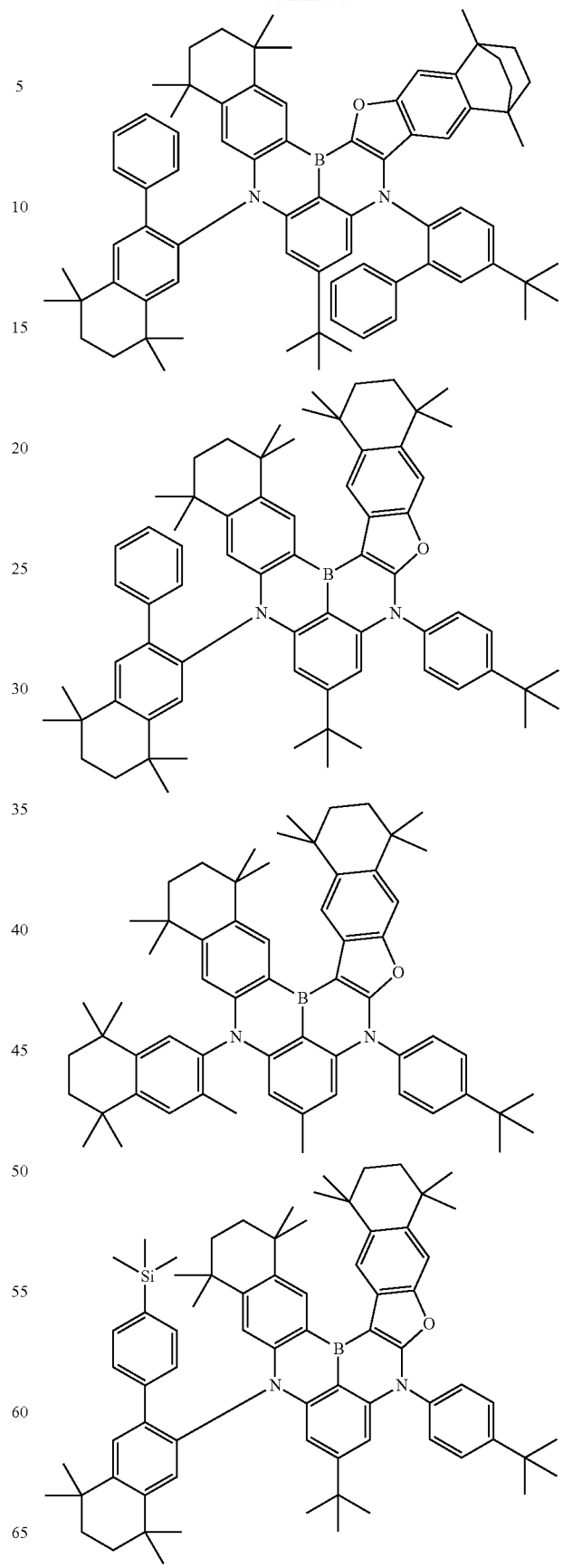

437
-continued
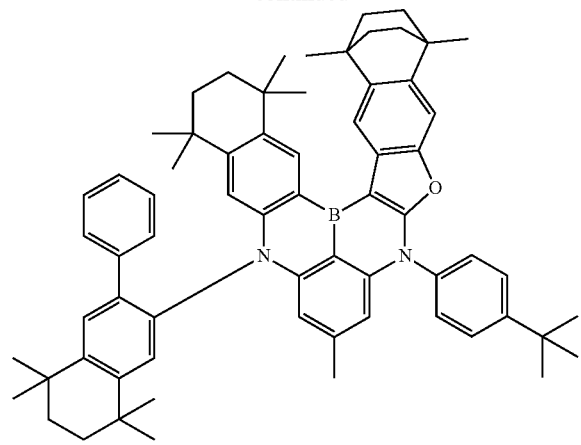
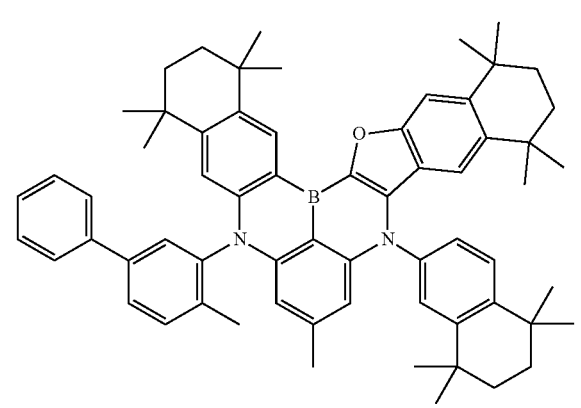
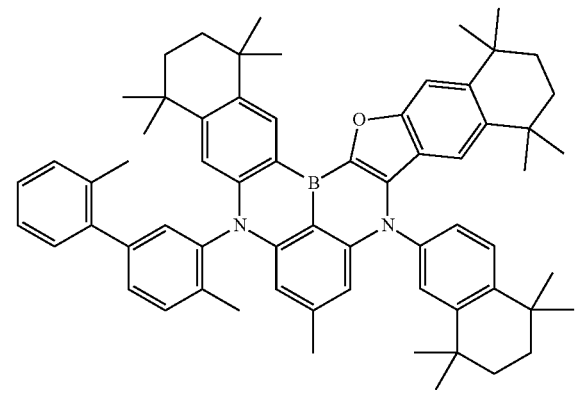
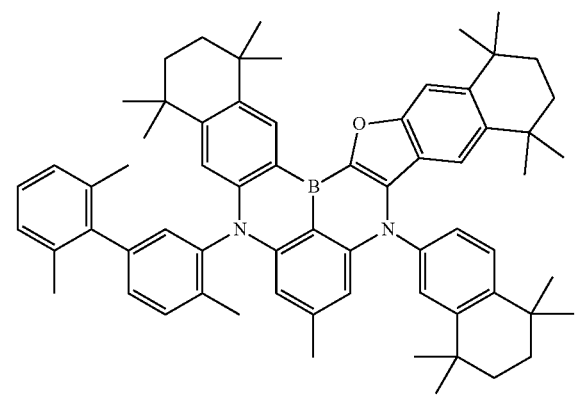
438
-continued
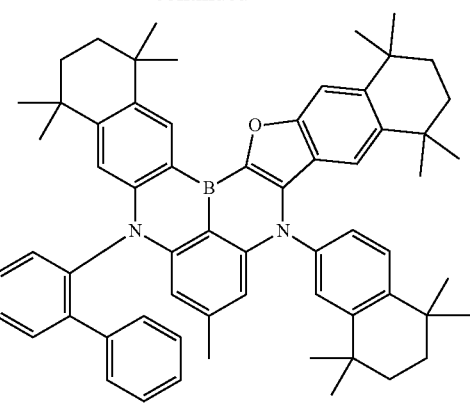

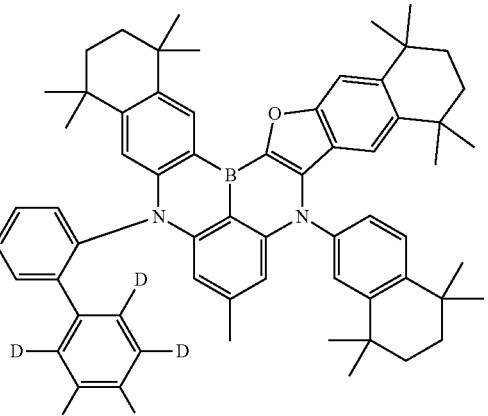
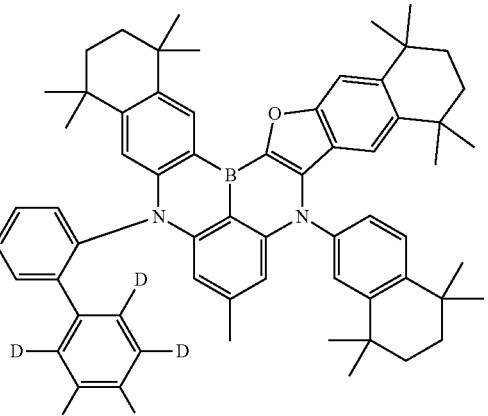

| 439 -continued | 440 -continued |
|---|---|
| 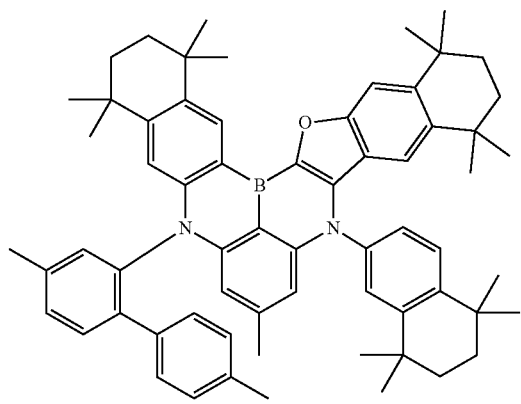 | 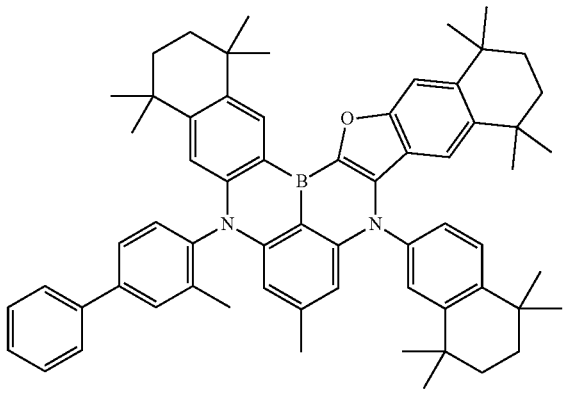 |
| 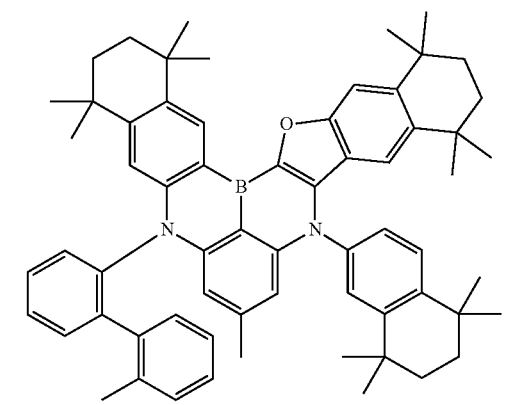 | 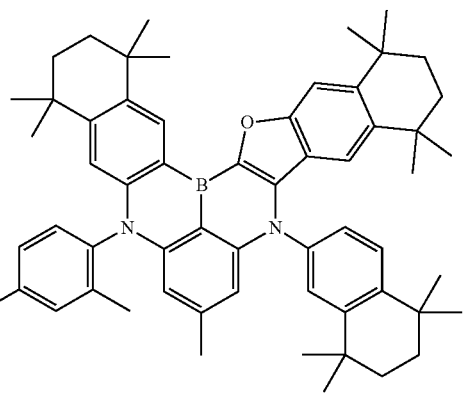 |
| 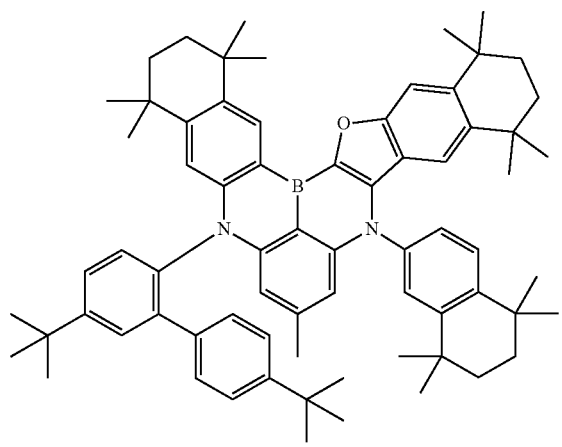 | 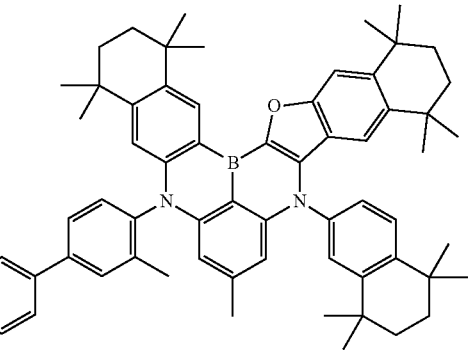 |
| 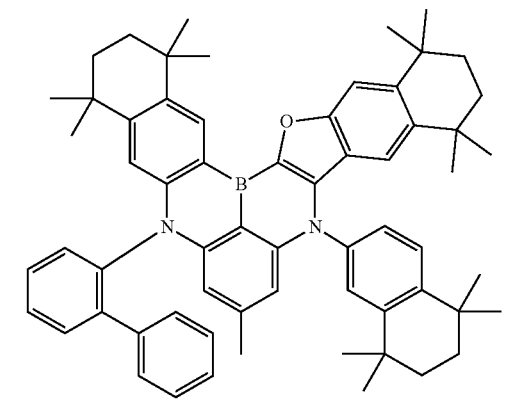 | 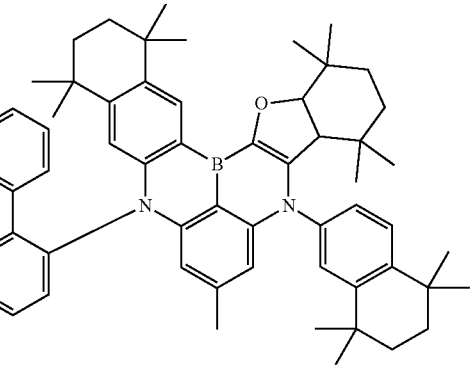 |

441
-continued
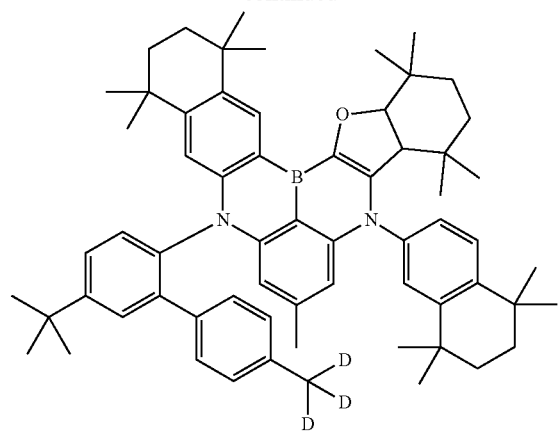

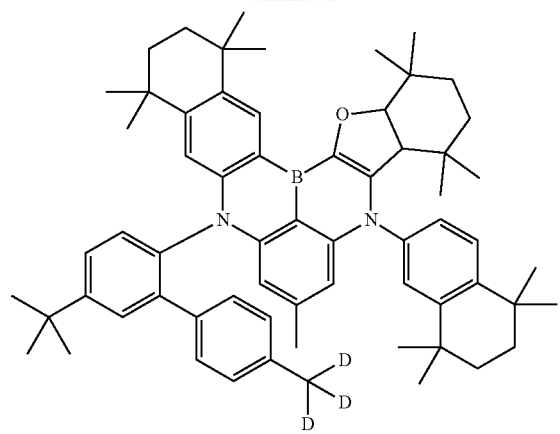
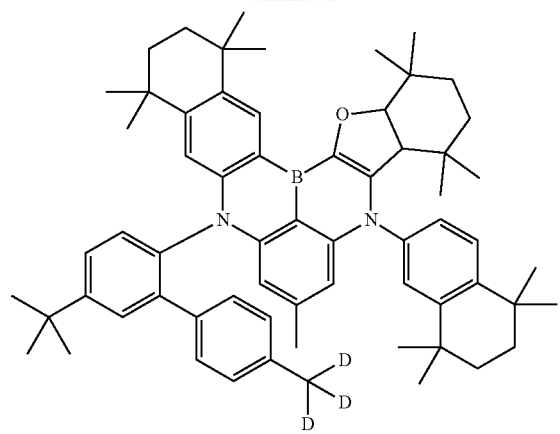
442
-continued
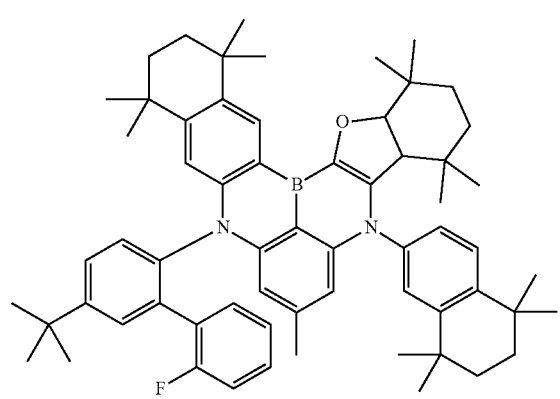
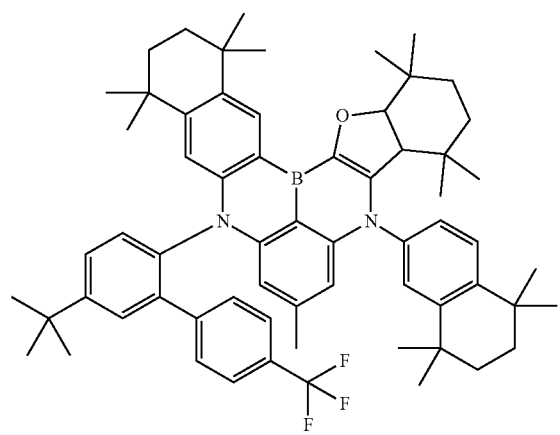
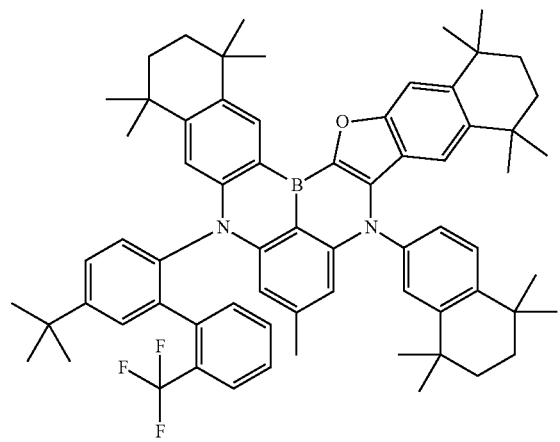

443
-continued
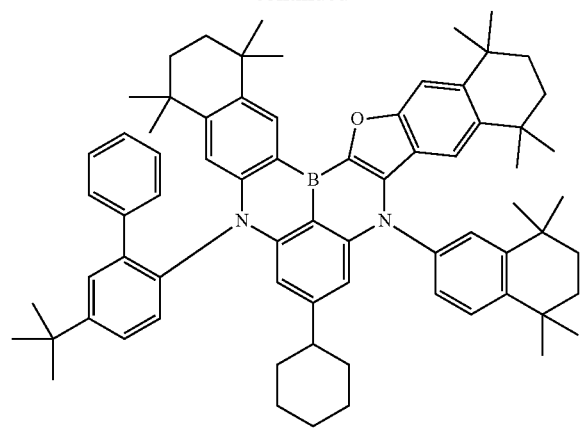
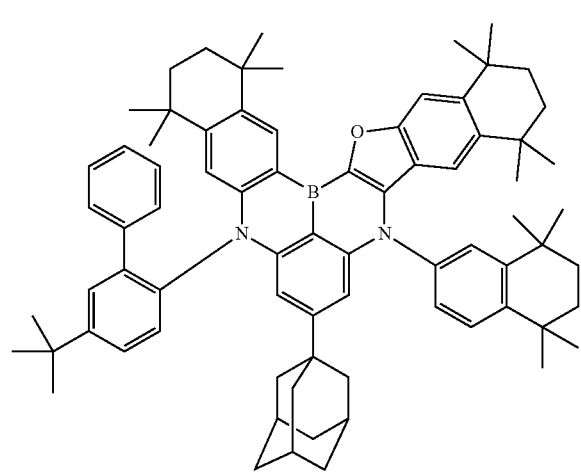
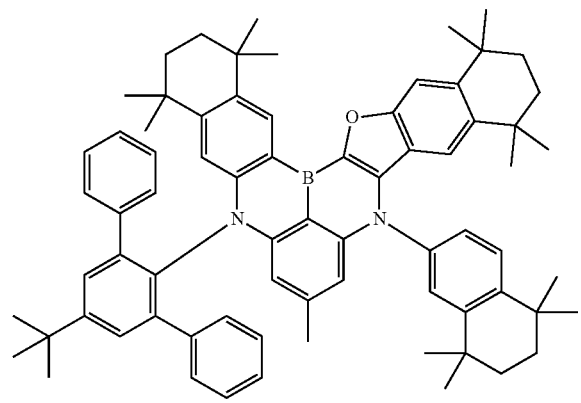
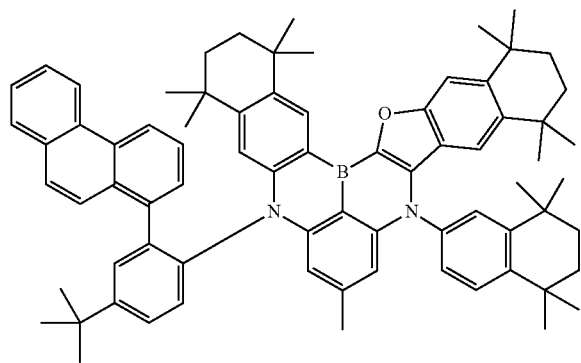
444
-continued
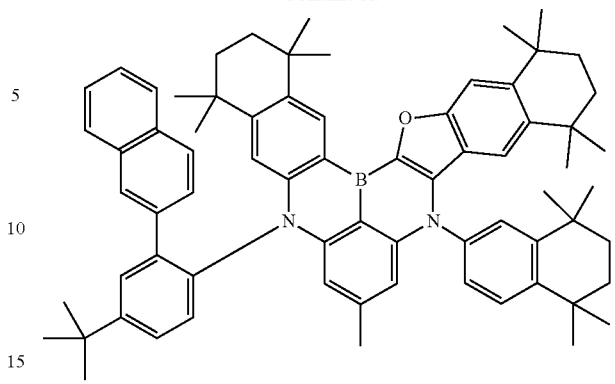
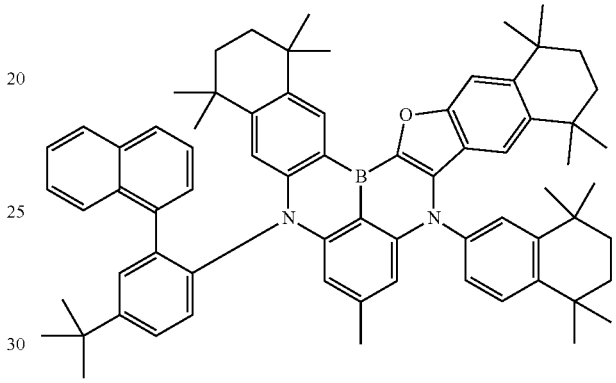
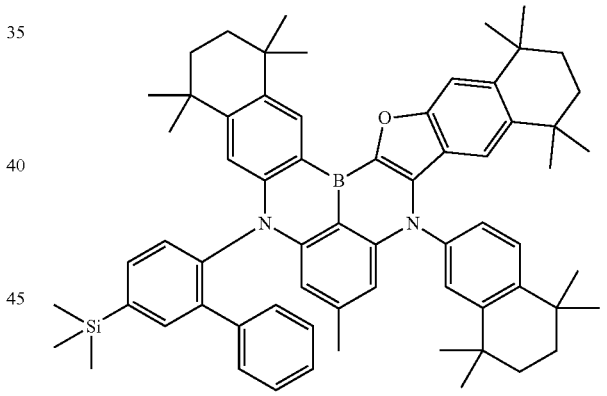
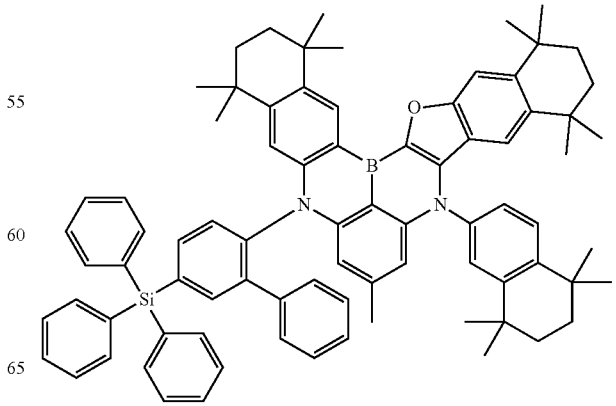

445
-continued
446
-continued
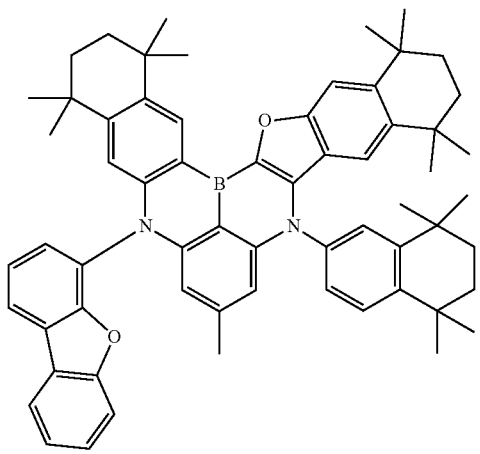
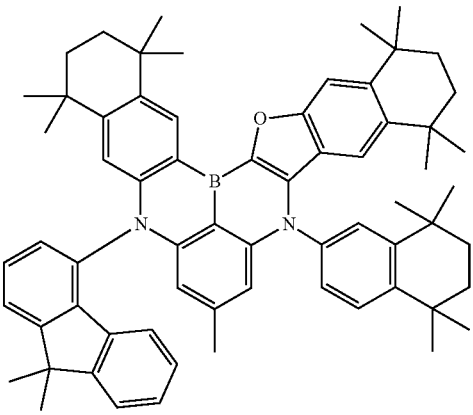
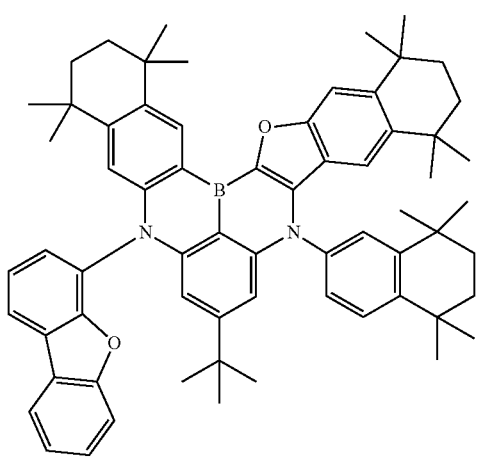
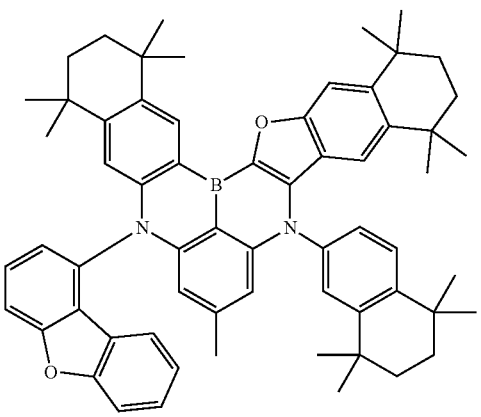
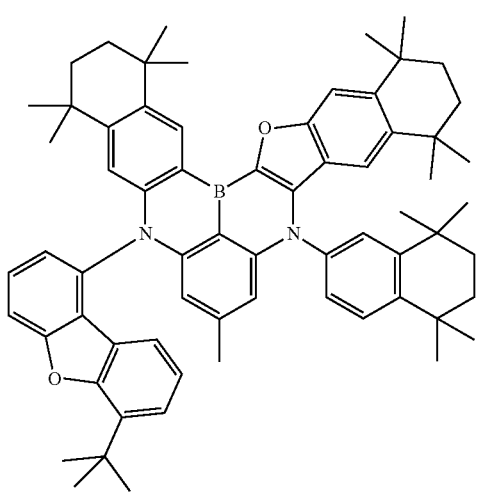
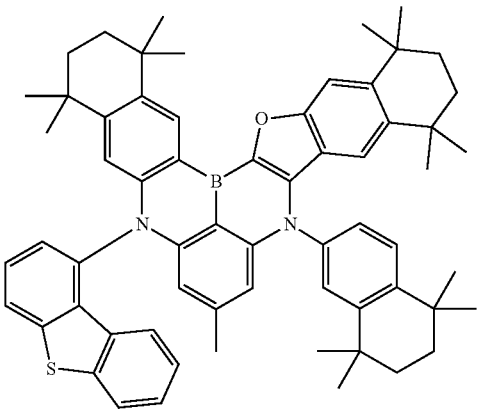
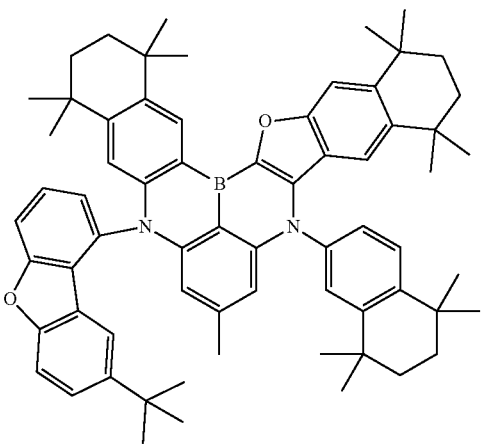

447
-continued
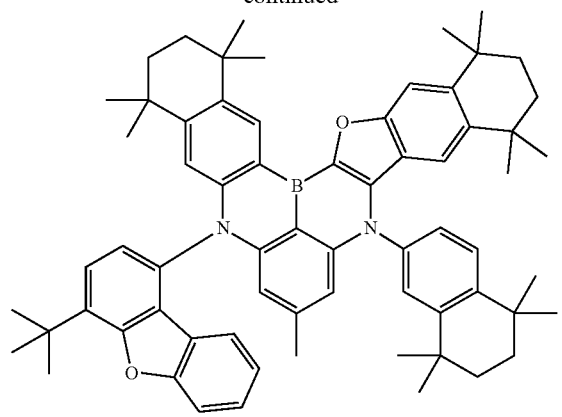
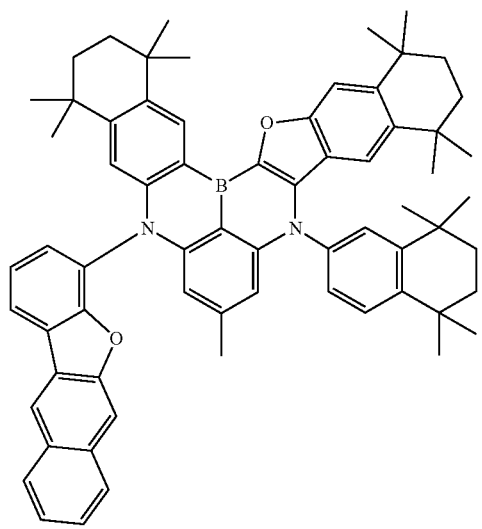
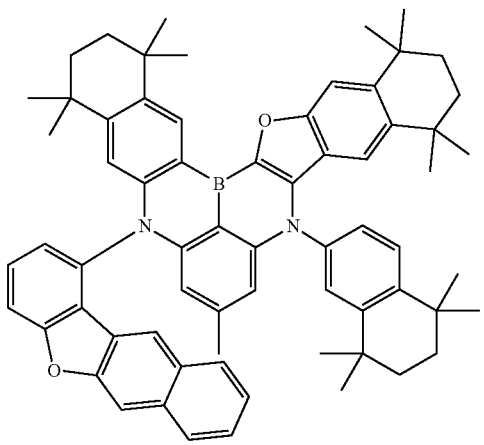
448
-continued
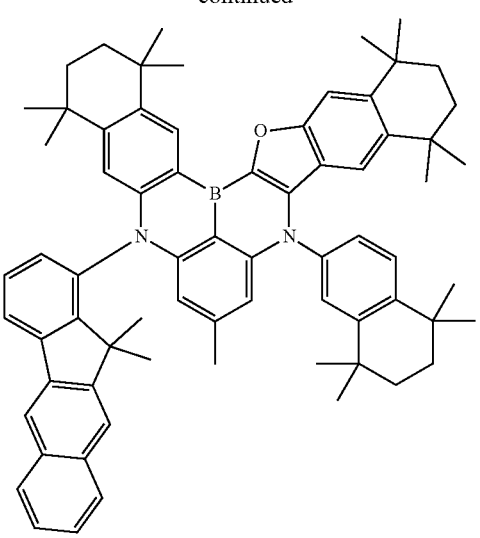
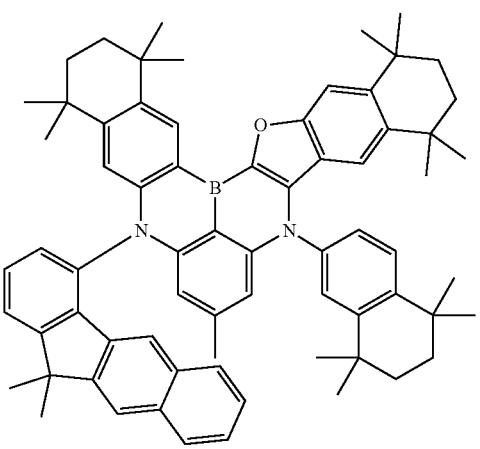
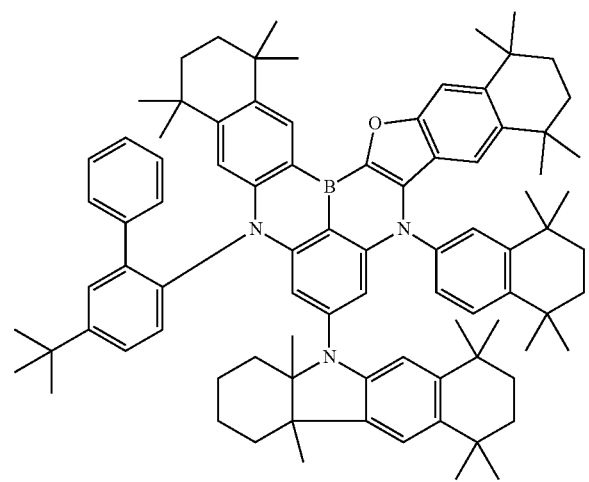

449
-continued
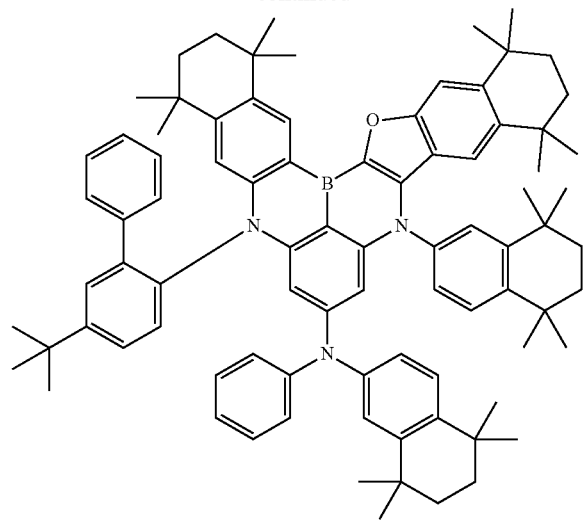
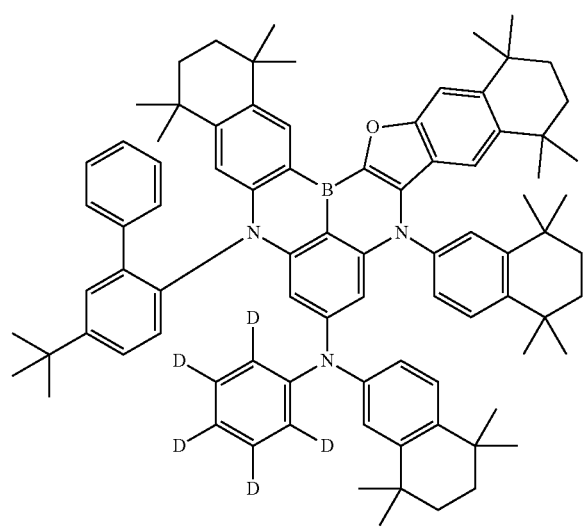
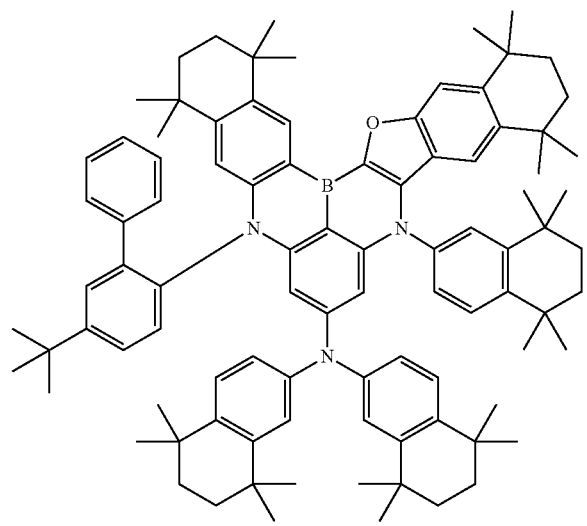
450
-continued
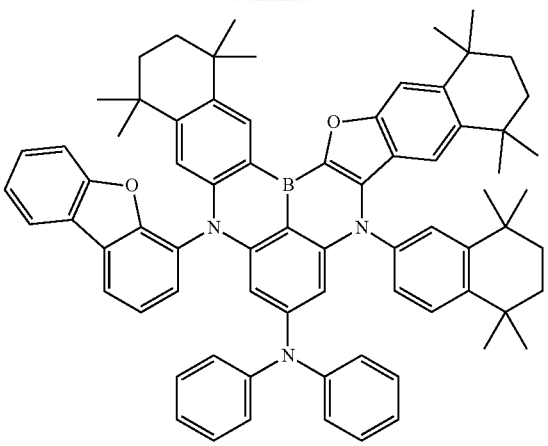
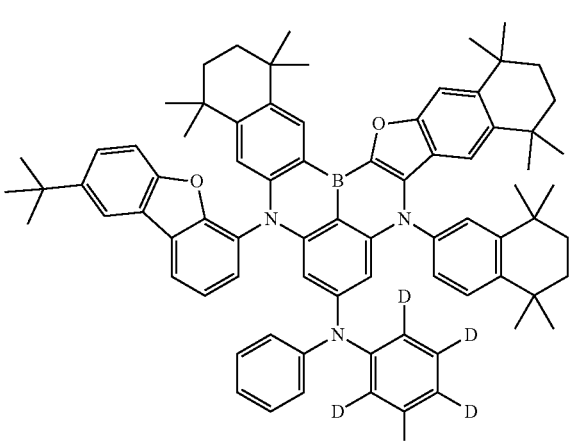
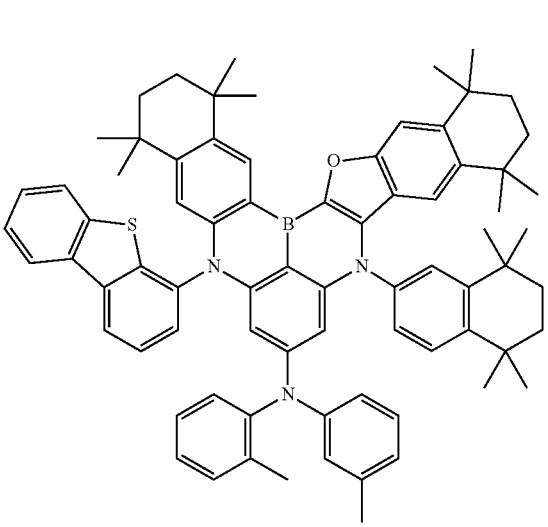

451
-continued
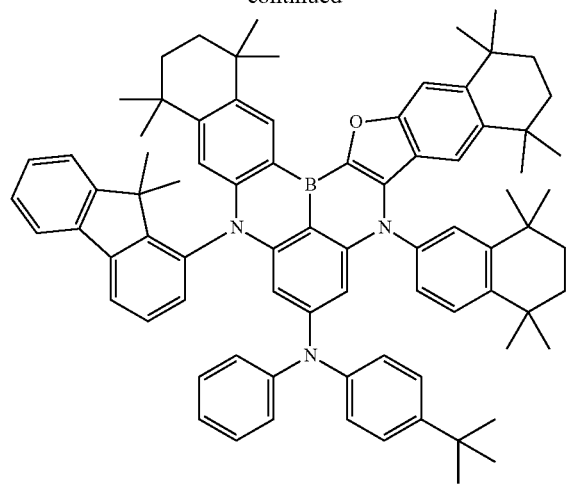
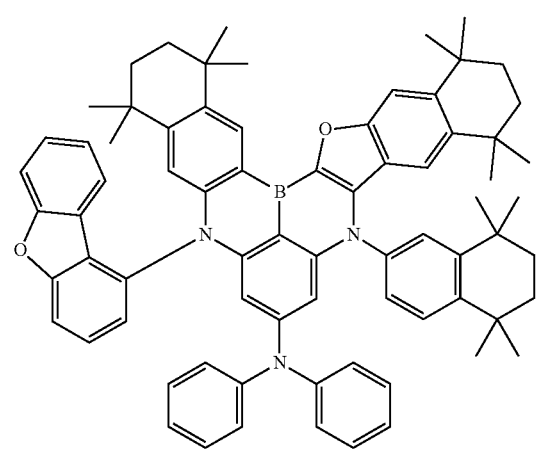
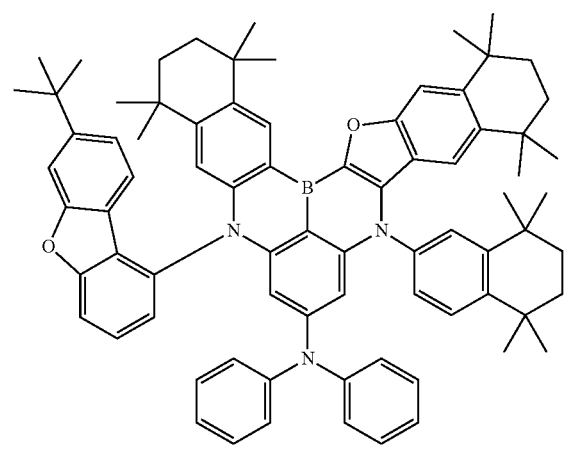
452
-continued
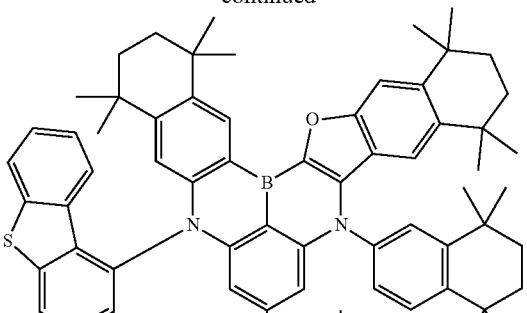
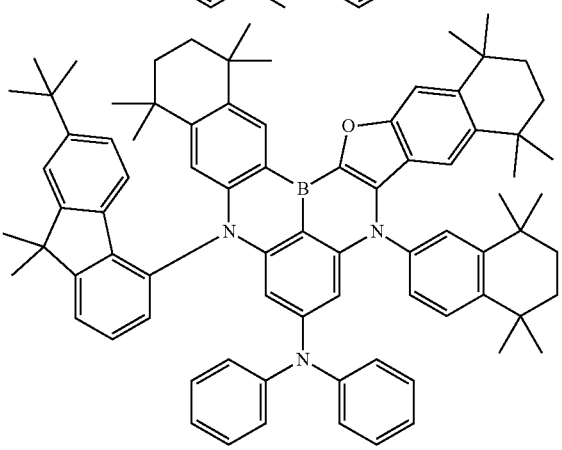
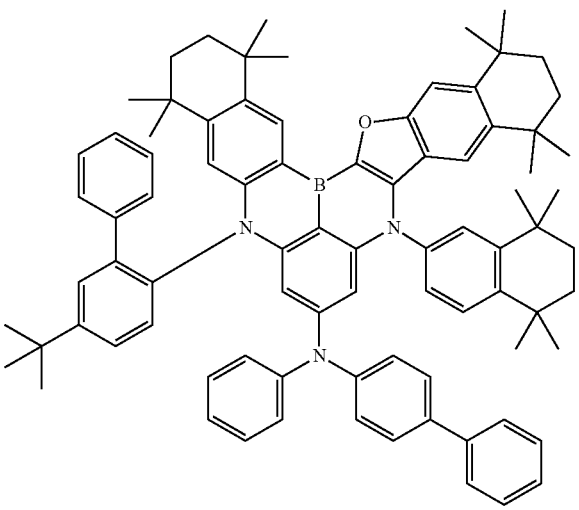
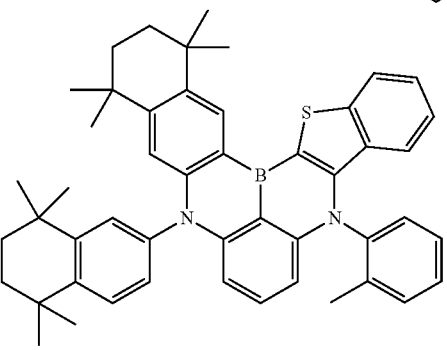

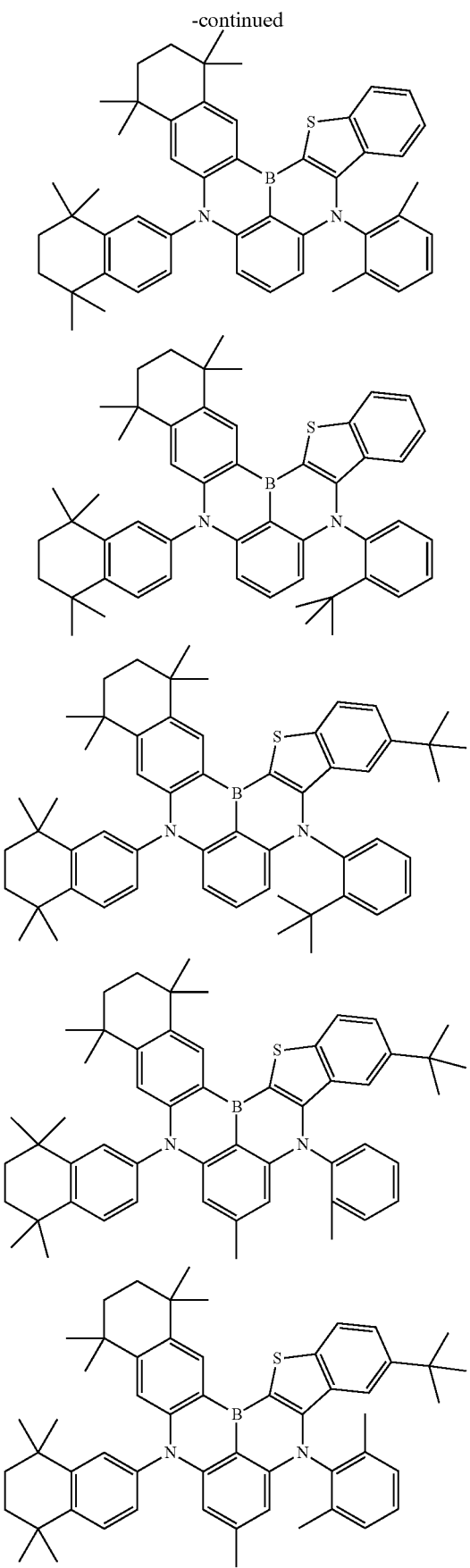

455
-continued
456
-continued
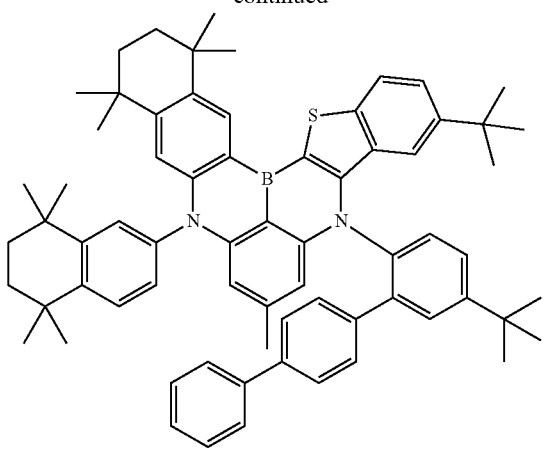
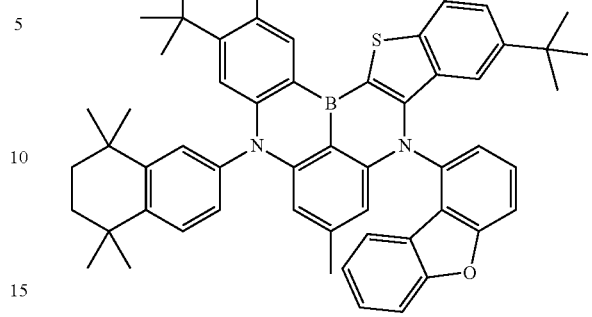
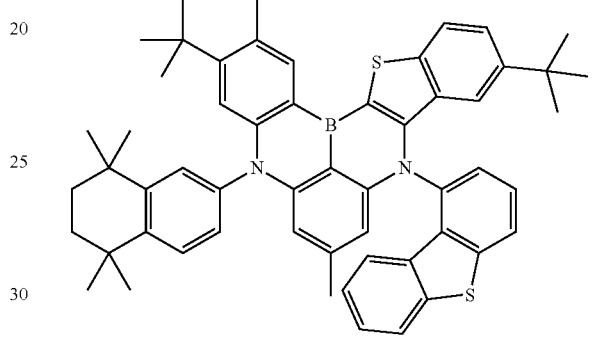
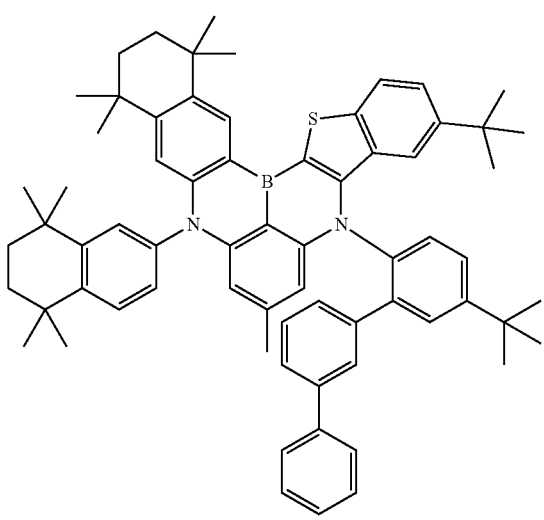
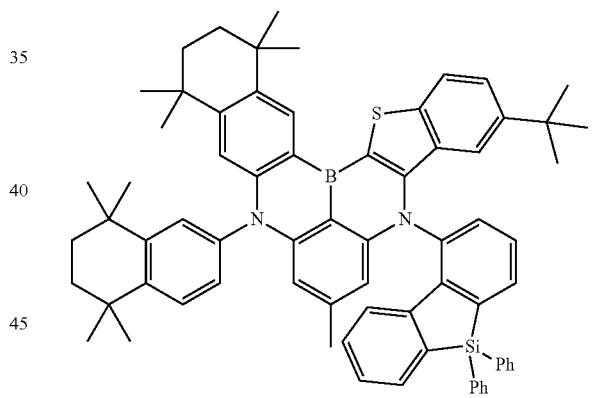
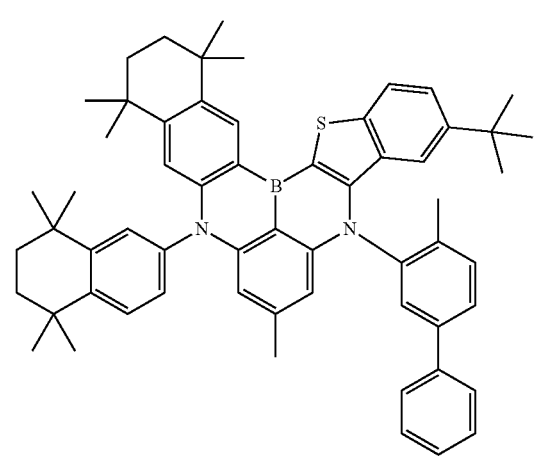
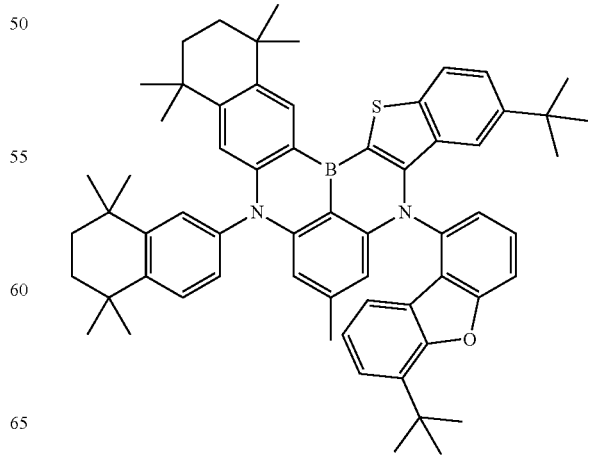

| 457 -continued | 458 -continued |
|---|---|
| 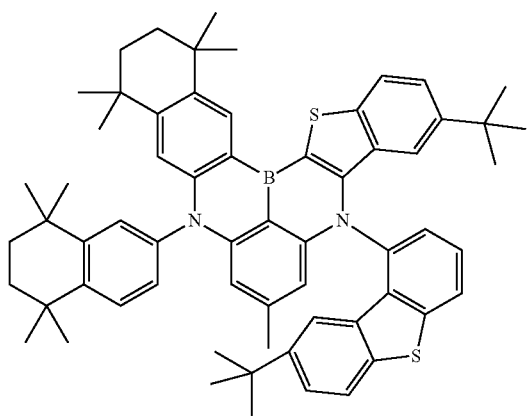 | 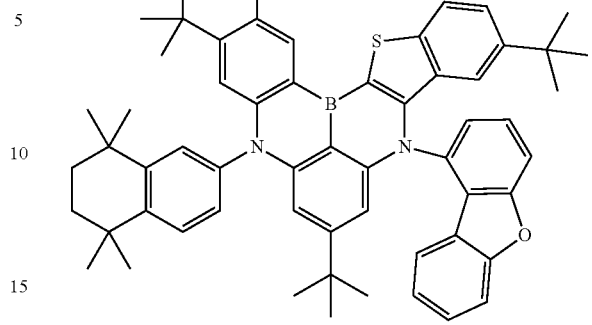 |
| 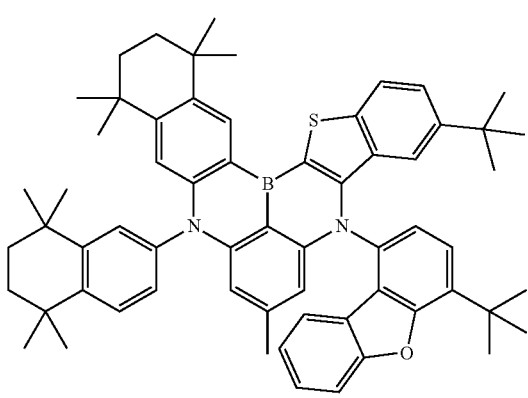 | 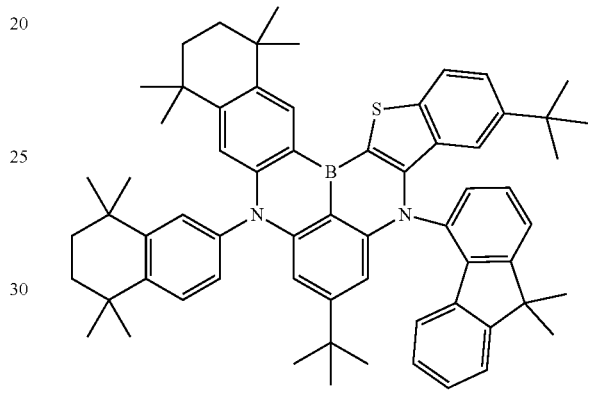 |
| 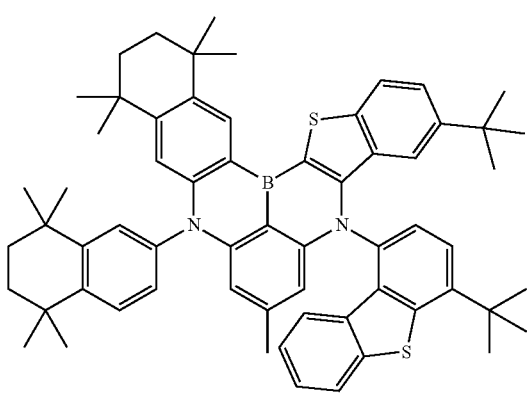 | 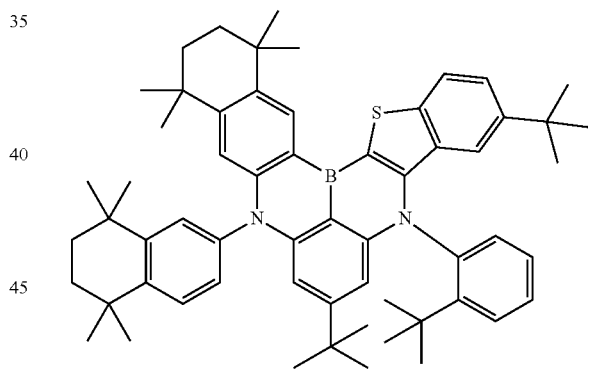 |
| 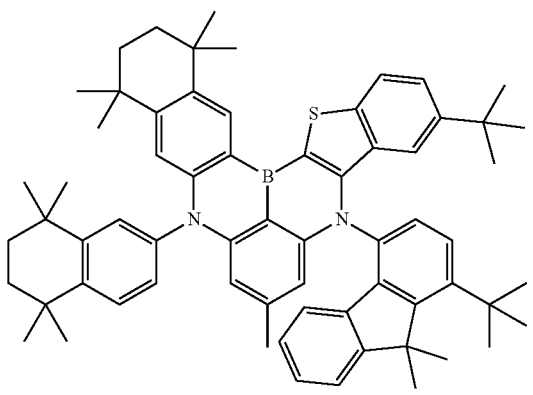 | 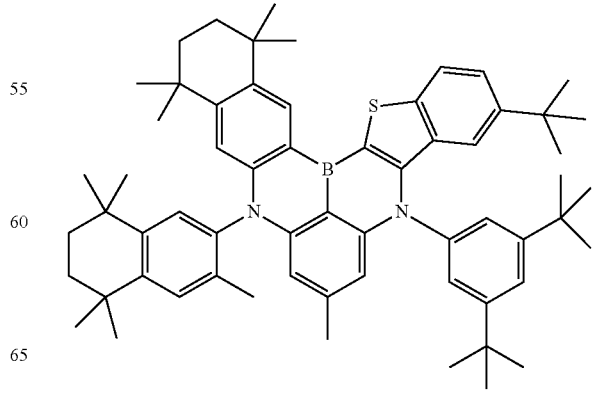 |

459
-continued
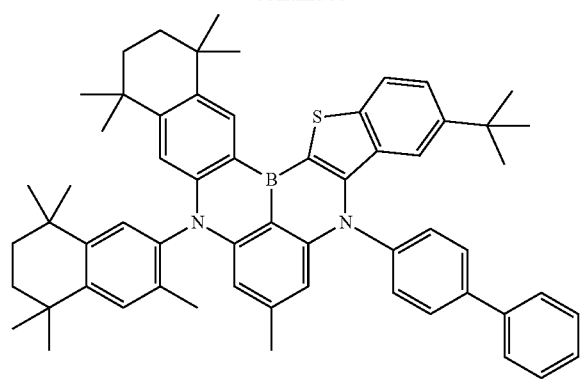
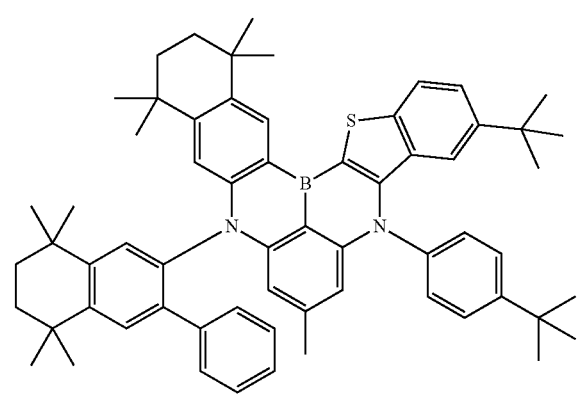
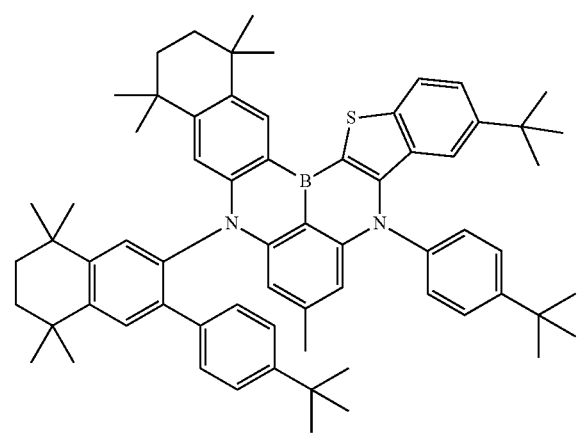
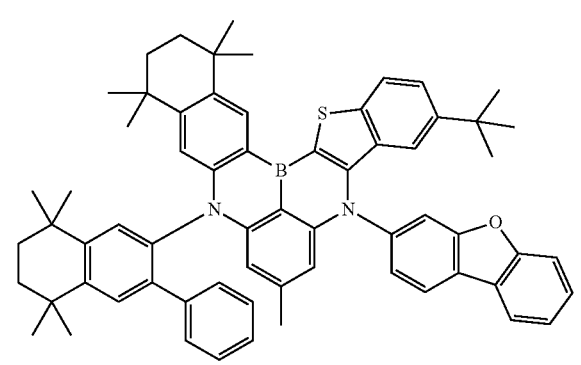
460
-continued
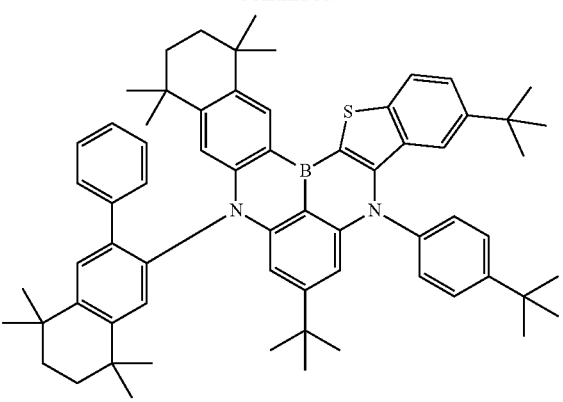
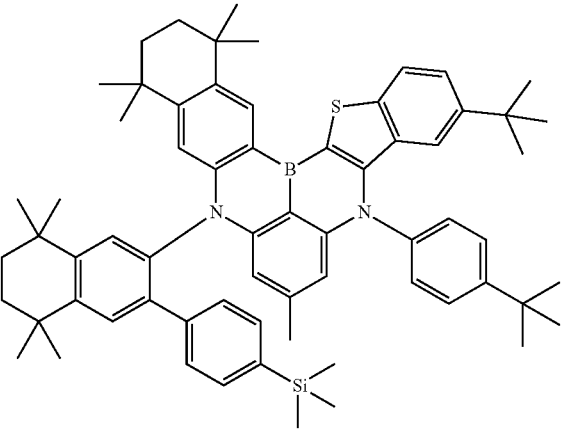
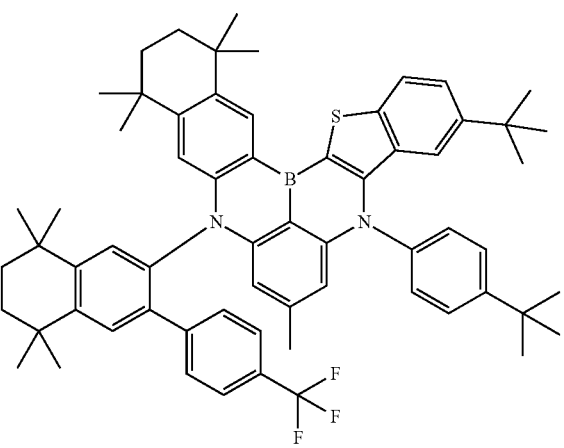
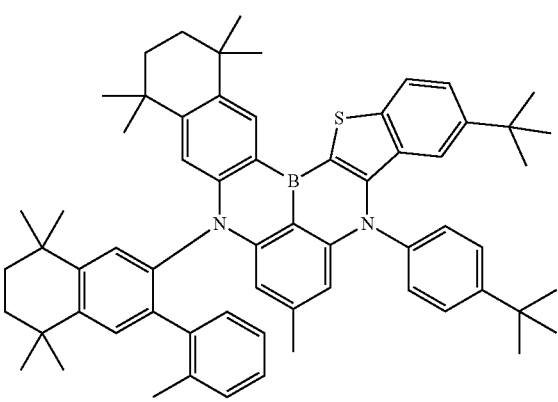

461
-continued
462
-continued
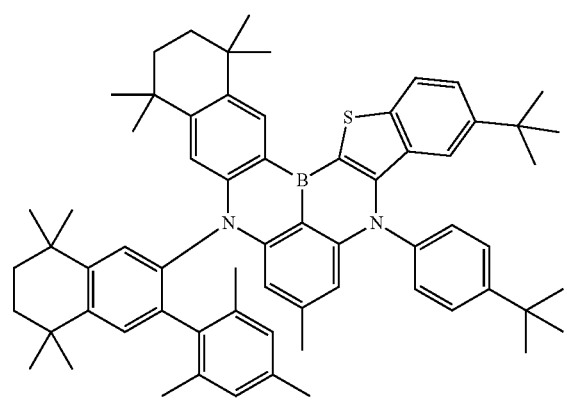
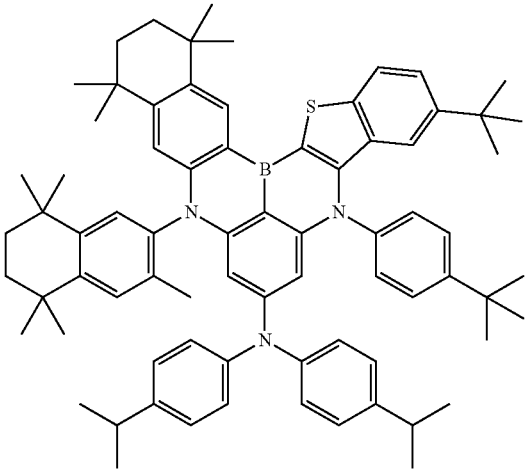
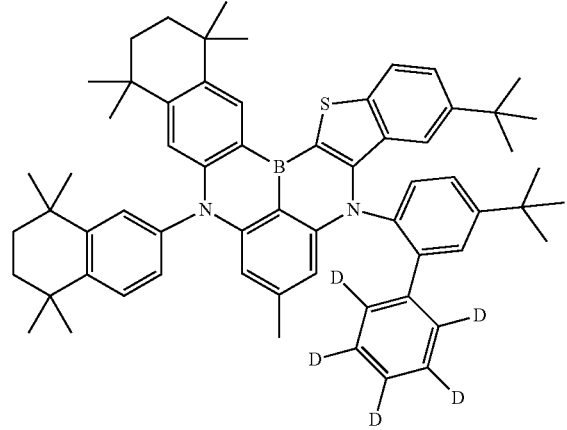
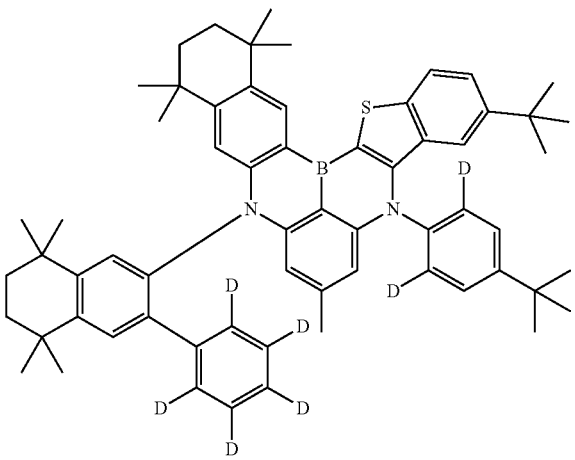
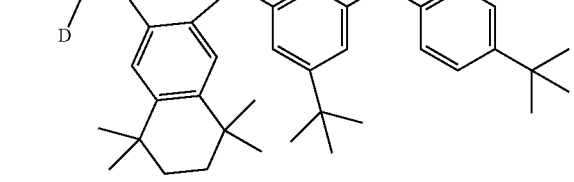

463
-continued
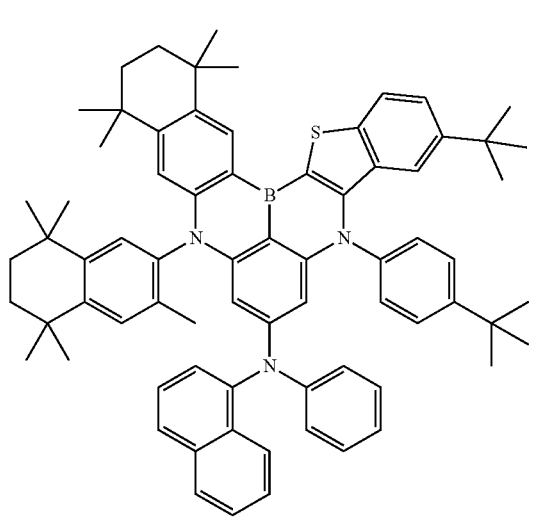
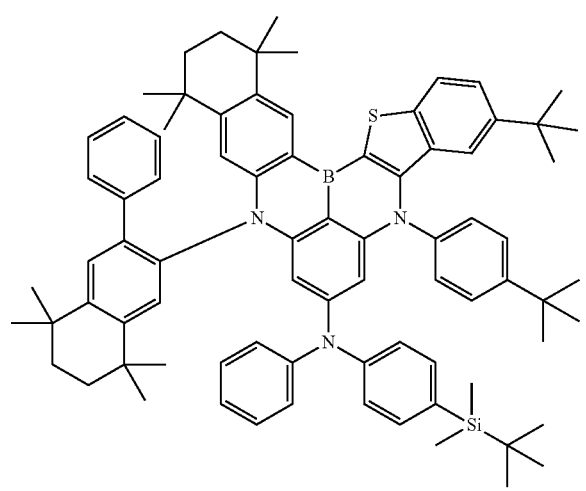
464
-continued

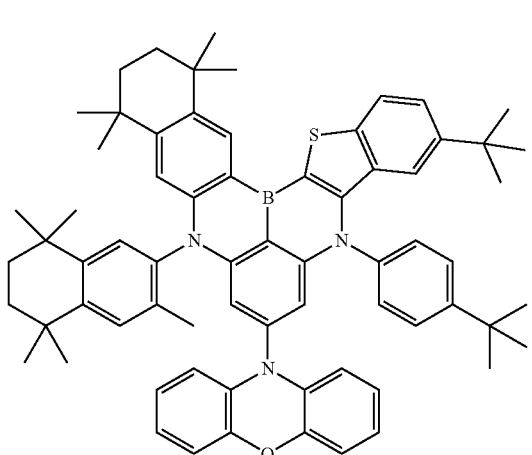
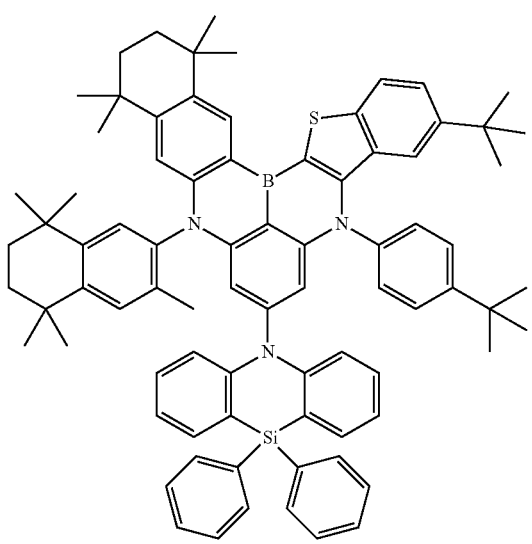

465
-continued
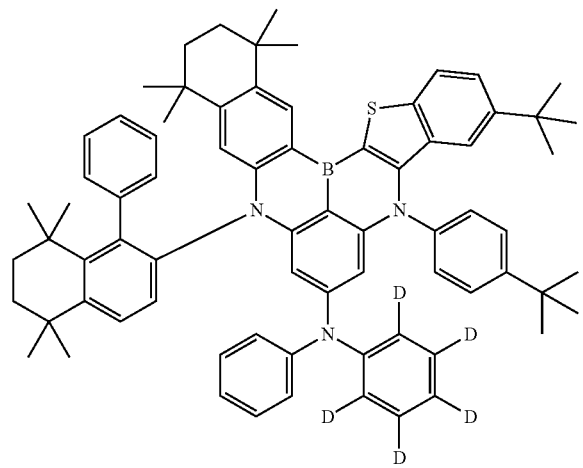
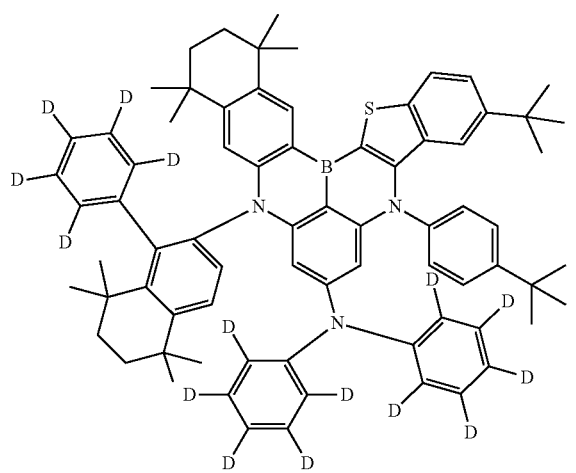
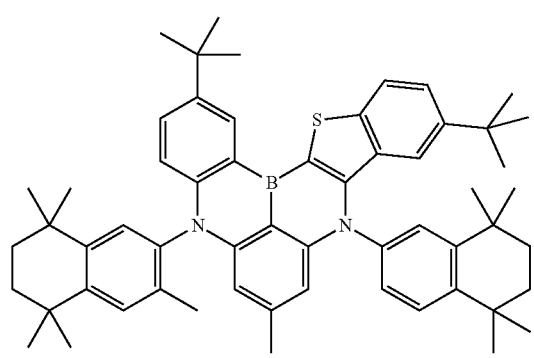
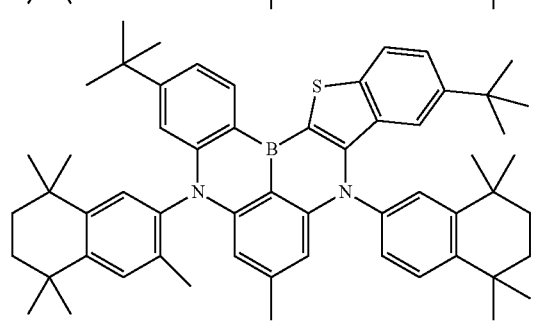
466
-continued
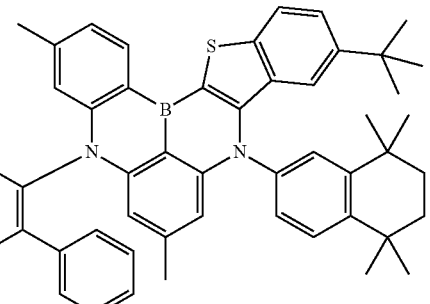
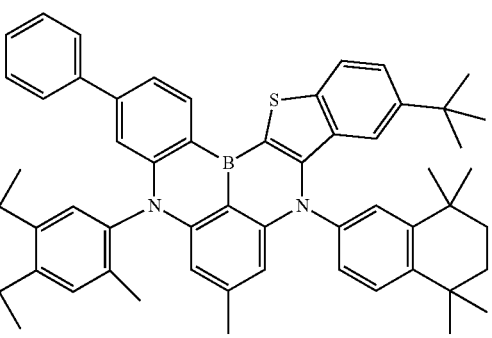
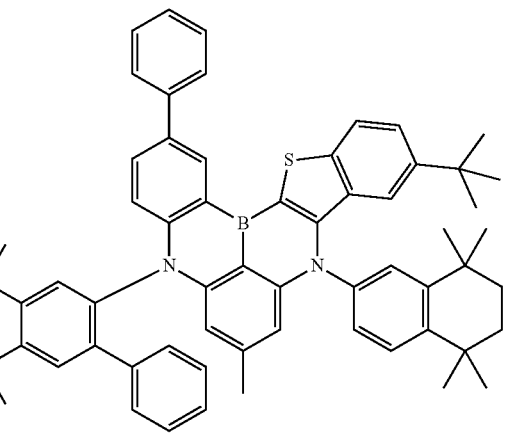
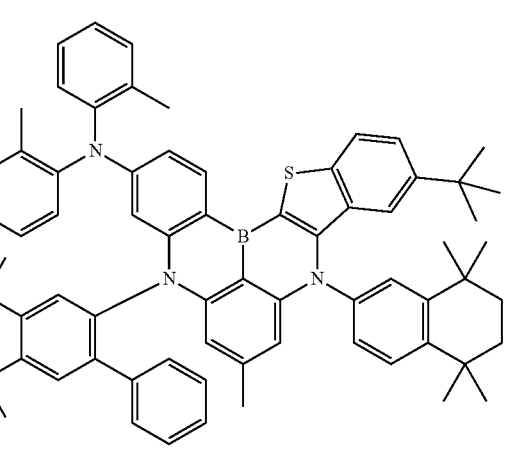

467
-continued

468
-continued

469
-continued
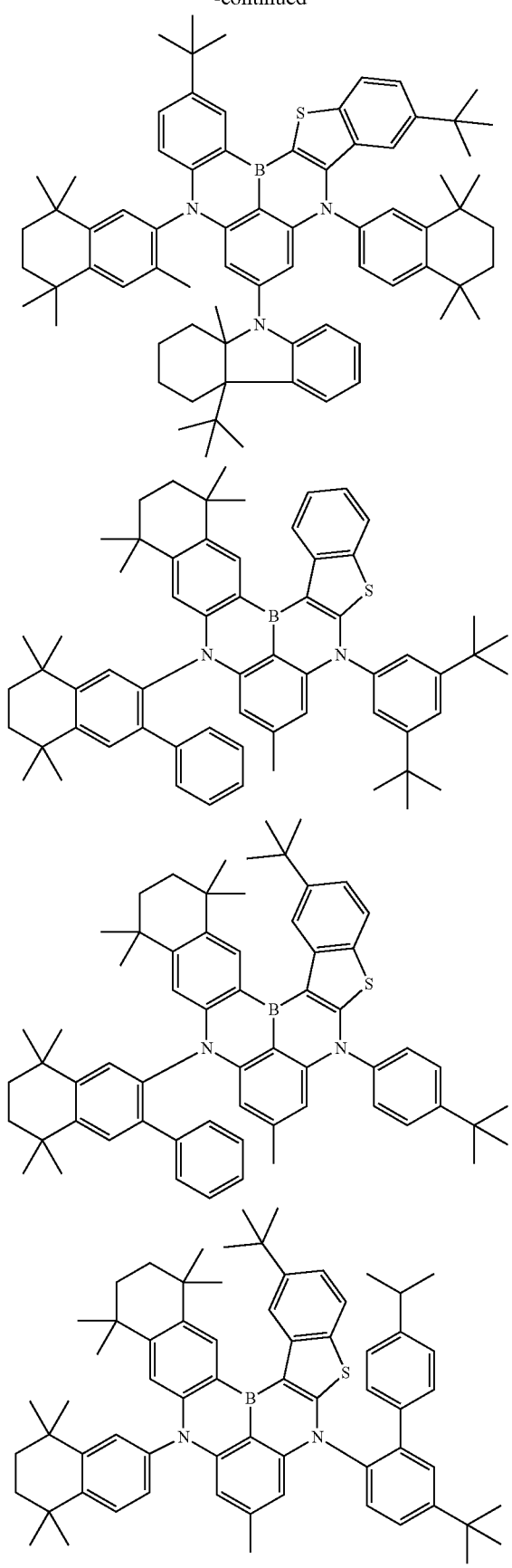
470
-continued
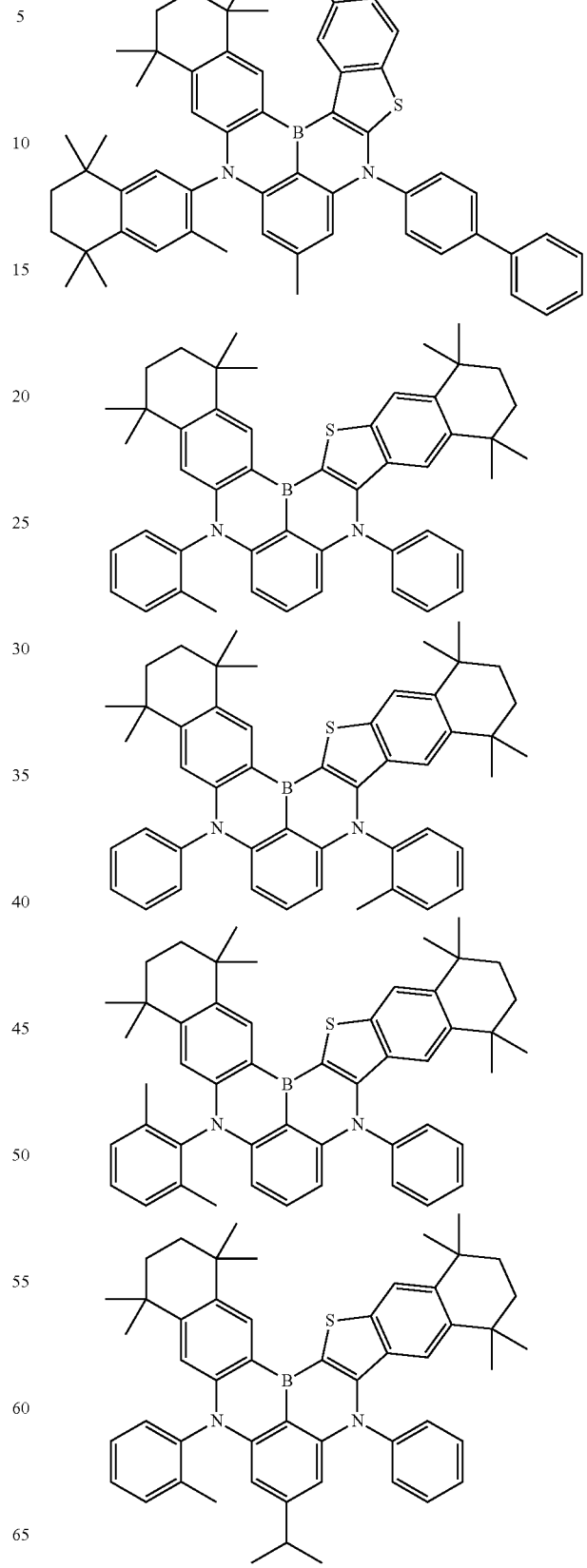

| 471 -continued | 472 -continued |
|---|---|
| 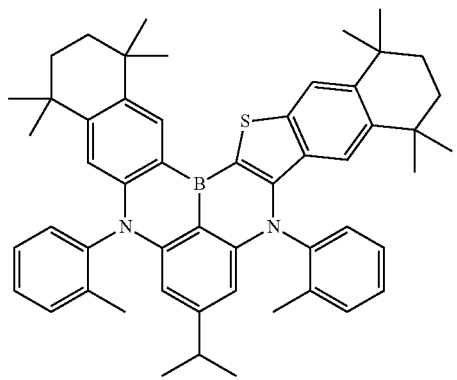 | 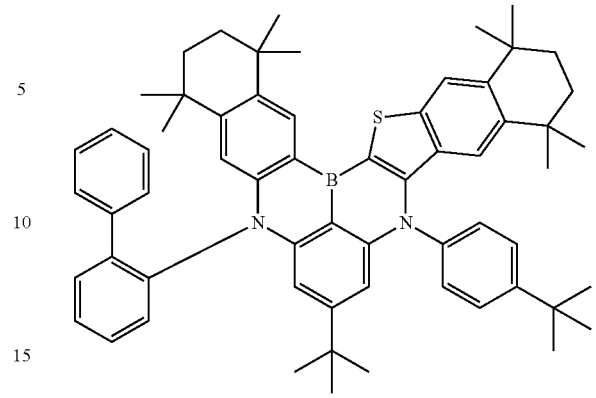 |
| 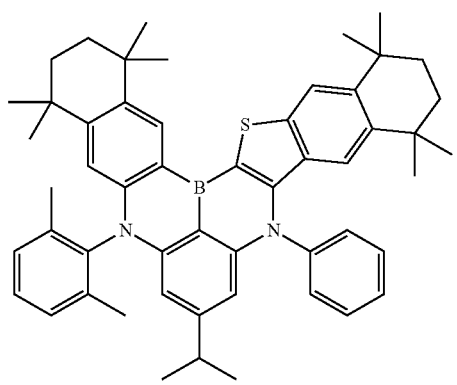 | 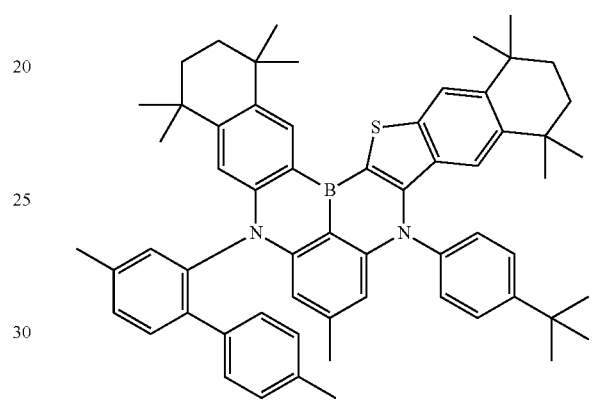 |
| 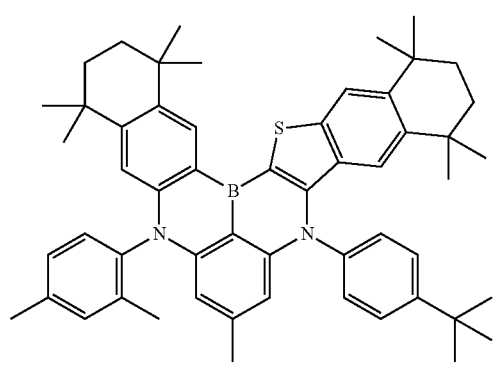 | 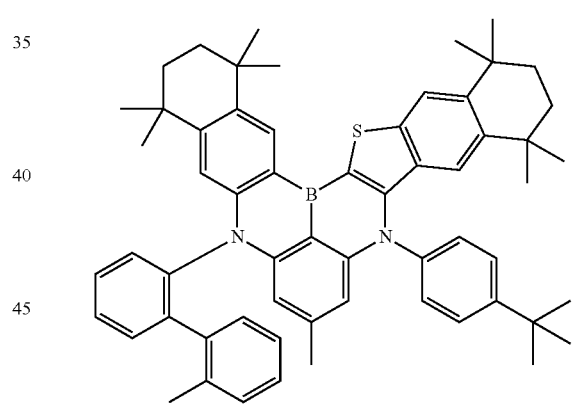 |
| 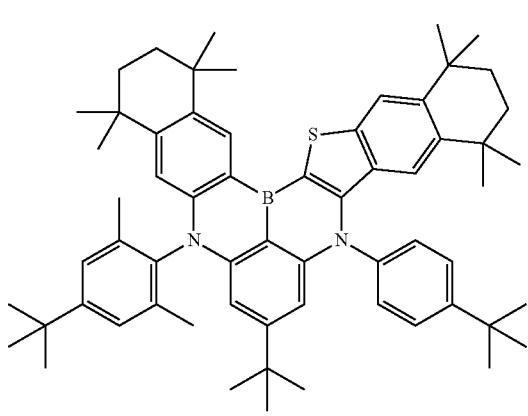 | 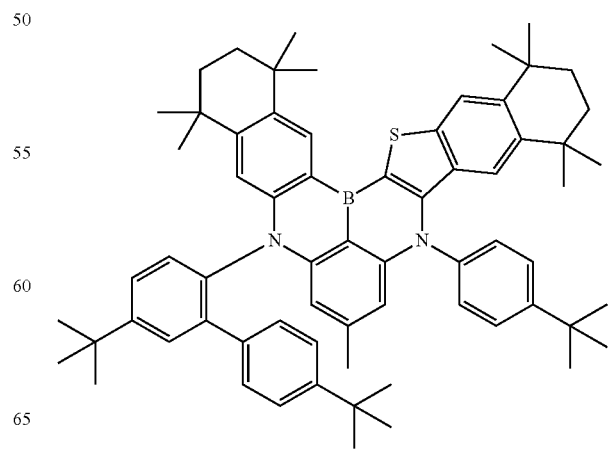 |

473
-continued
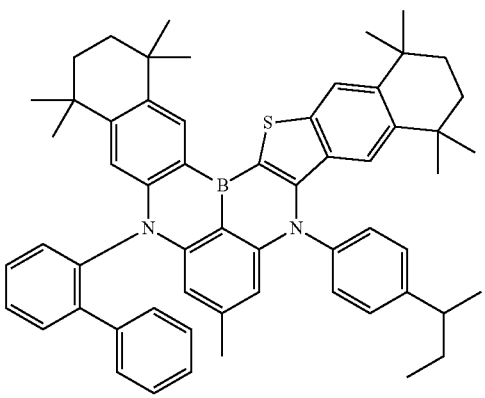
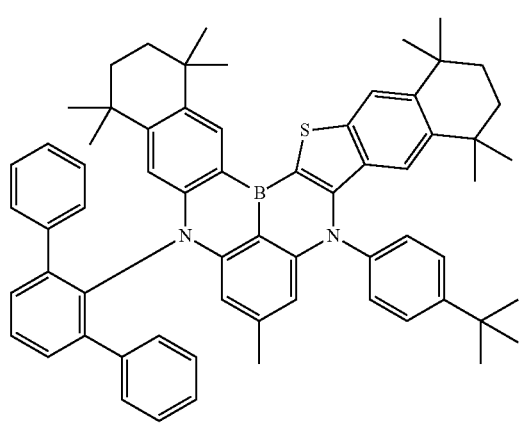
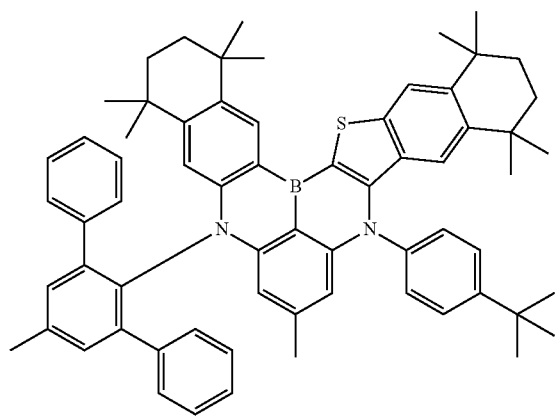
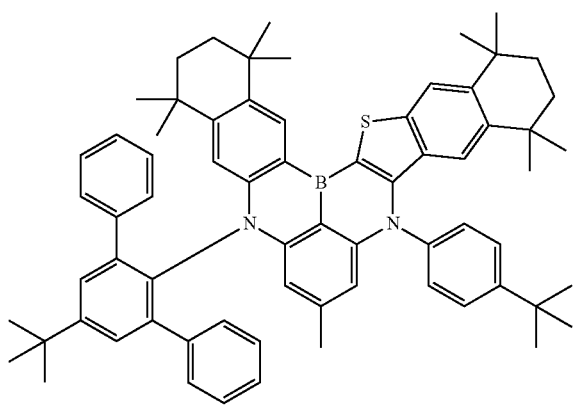
474
-continued
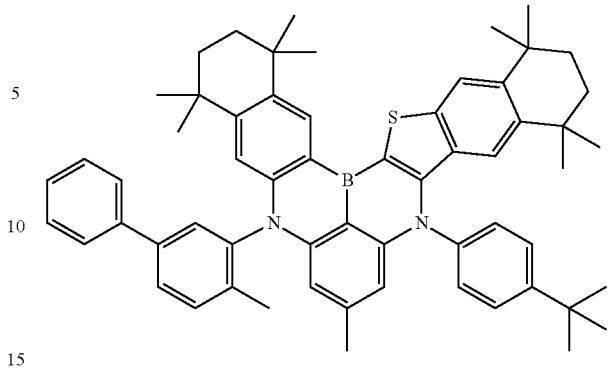
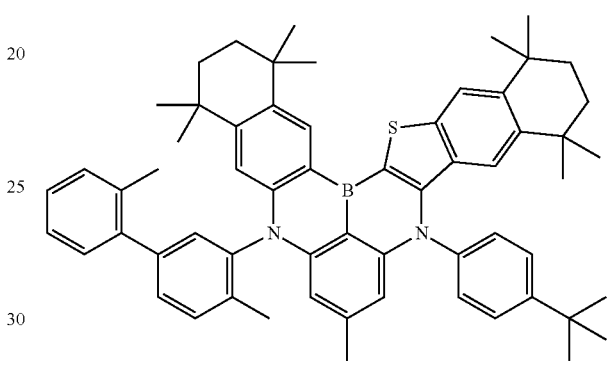
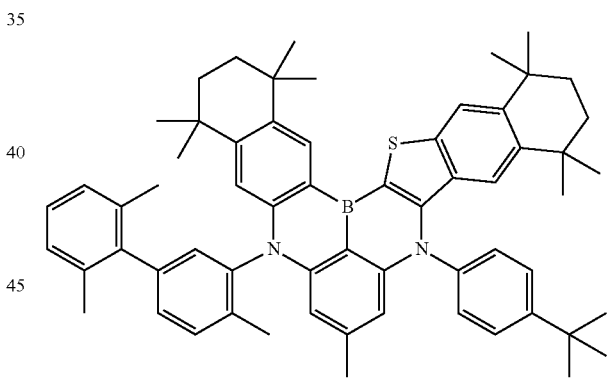
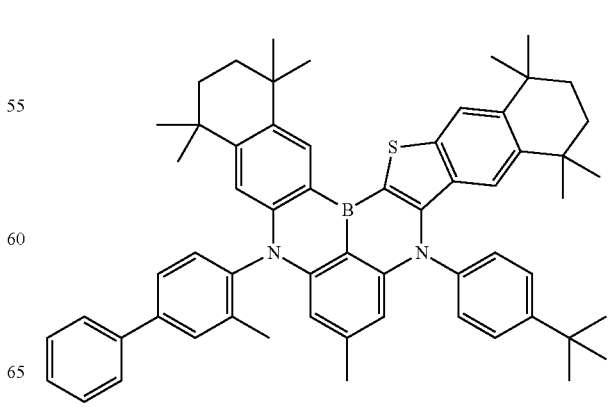

475
-continued
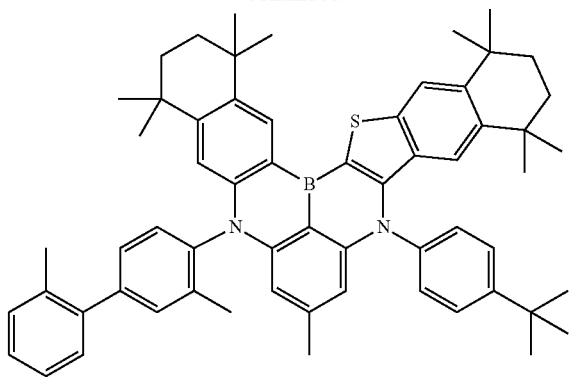
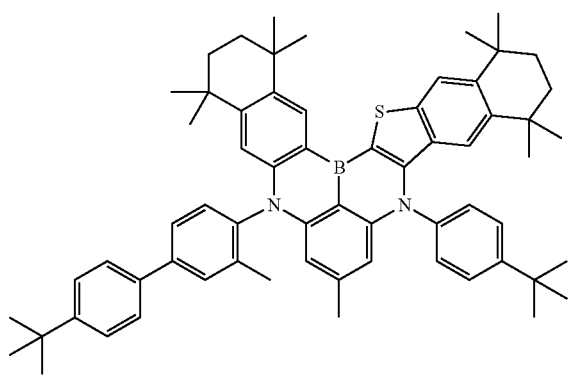
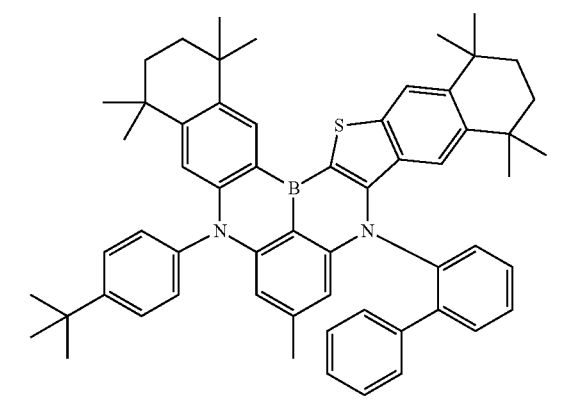
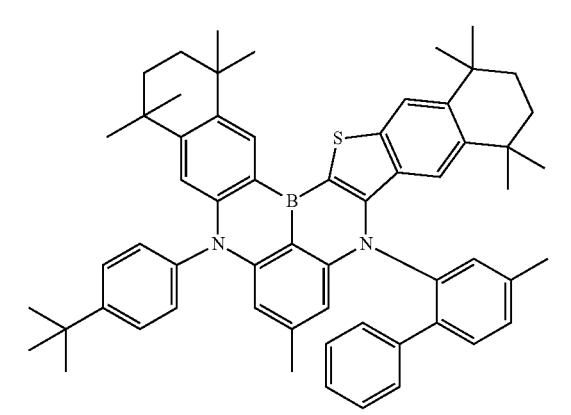
476
-continued
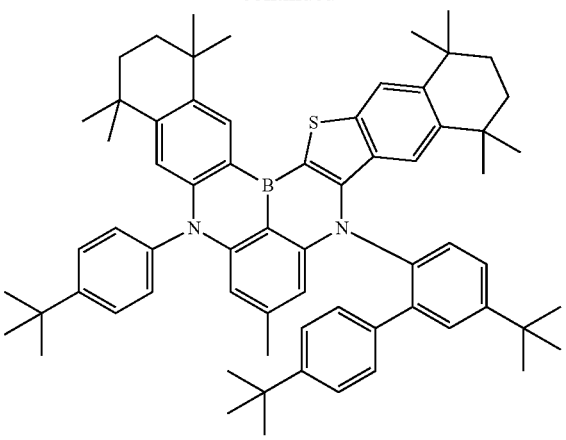
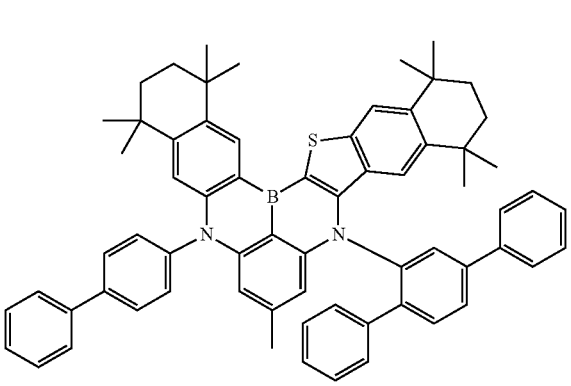
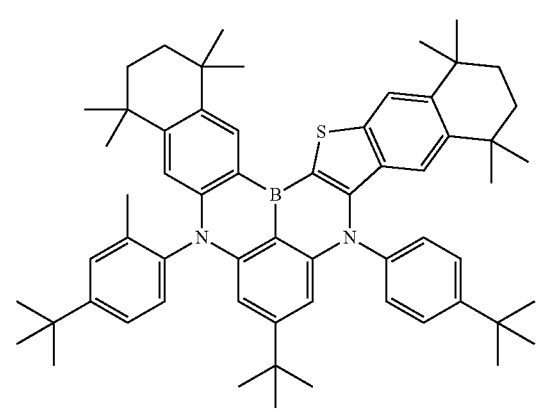
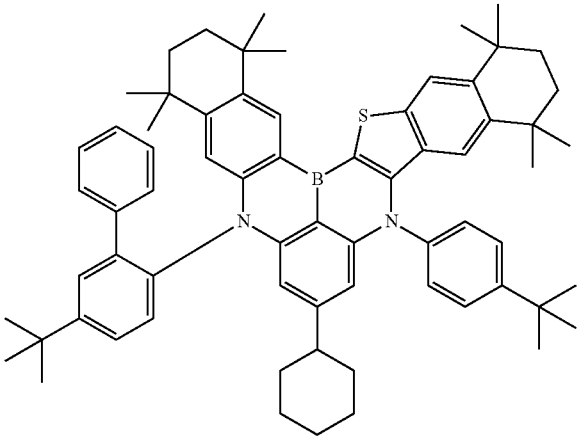

477
-continued
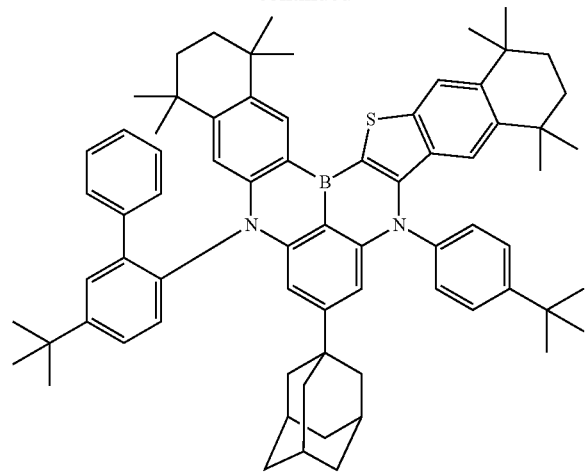
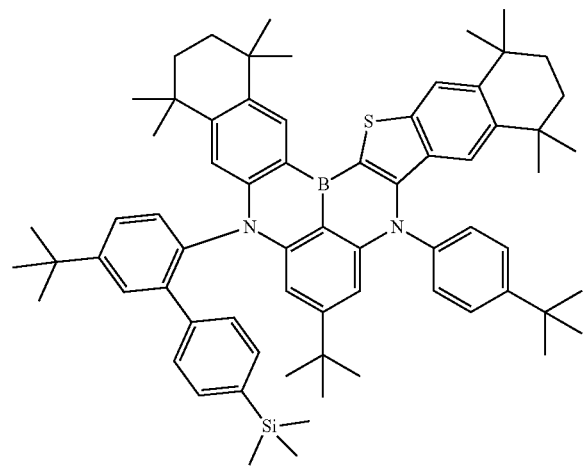
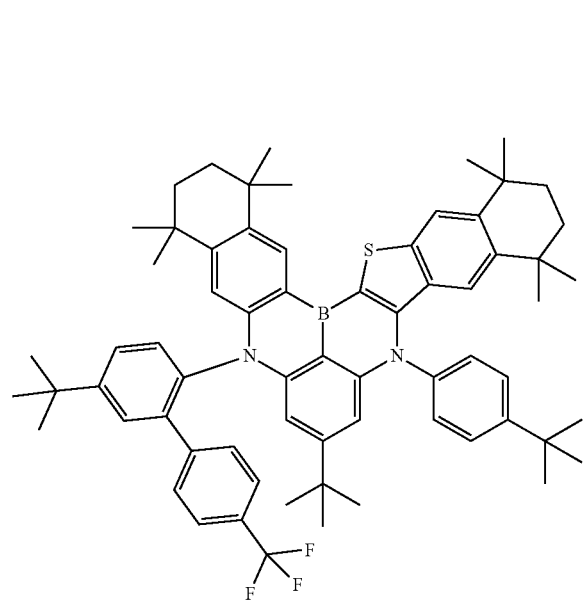
478
-continued
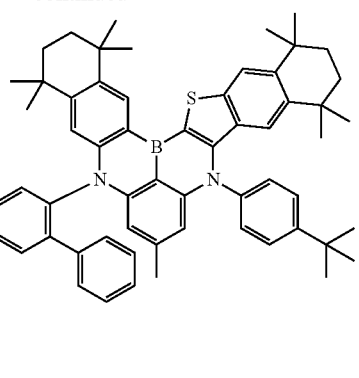
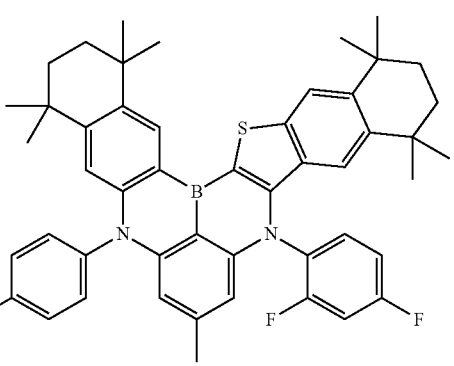
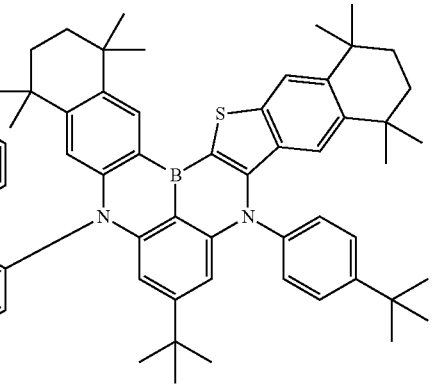
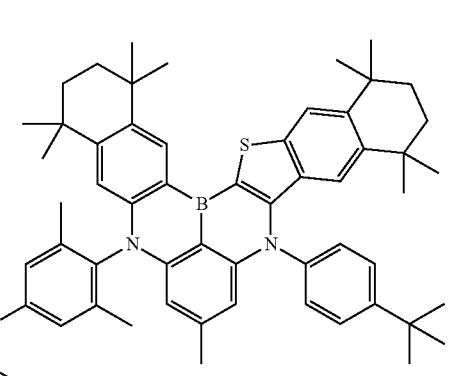

479
-continued
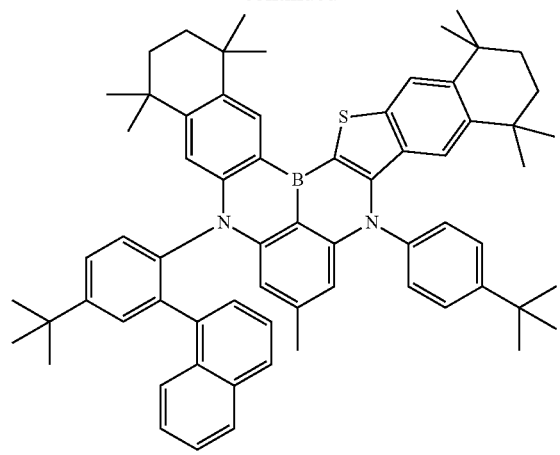
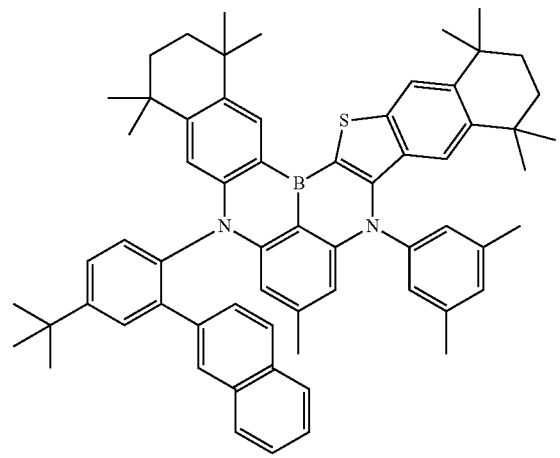
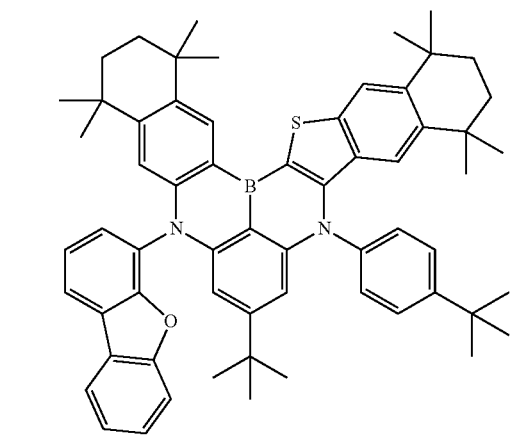
480
-continued
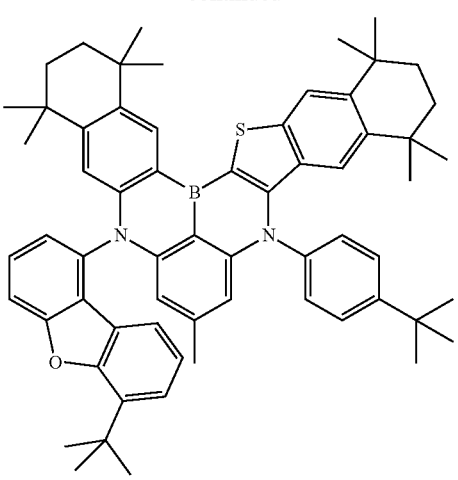
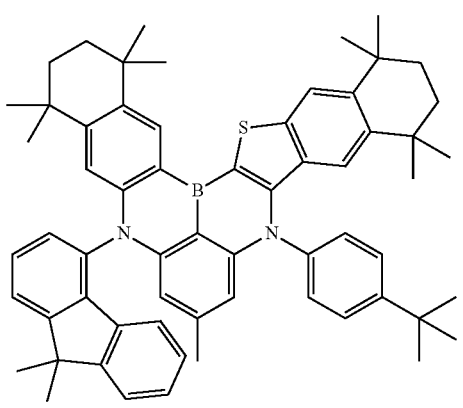
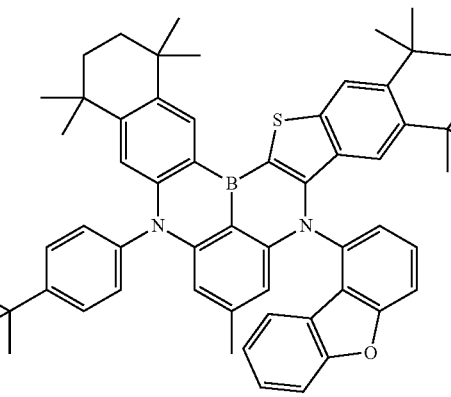
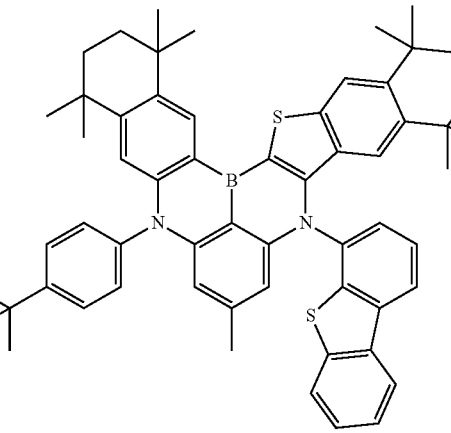

481
-continued
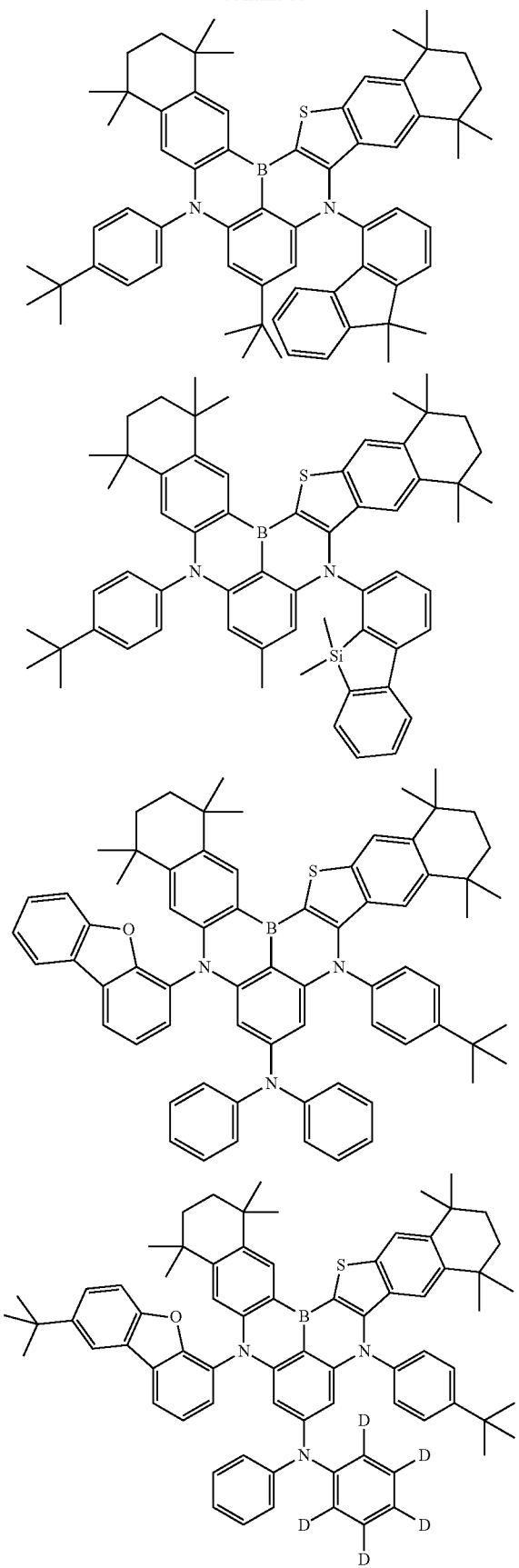
482
-continued
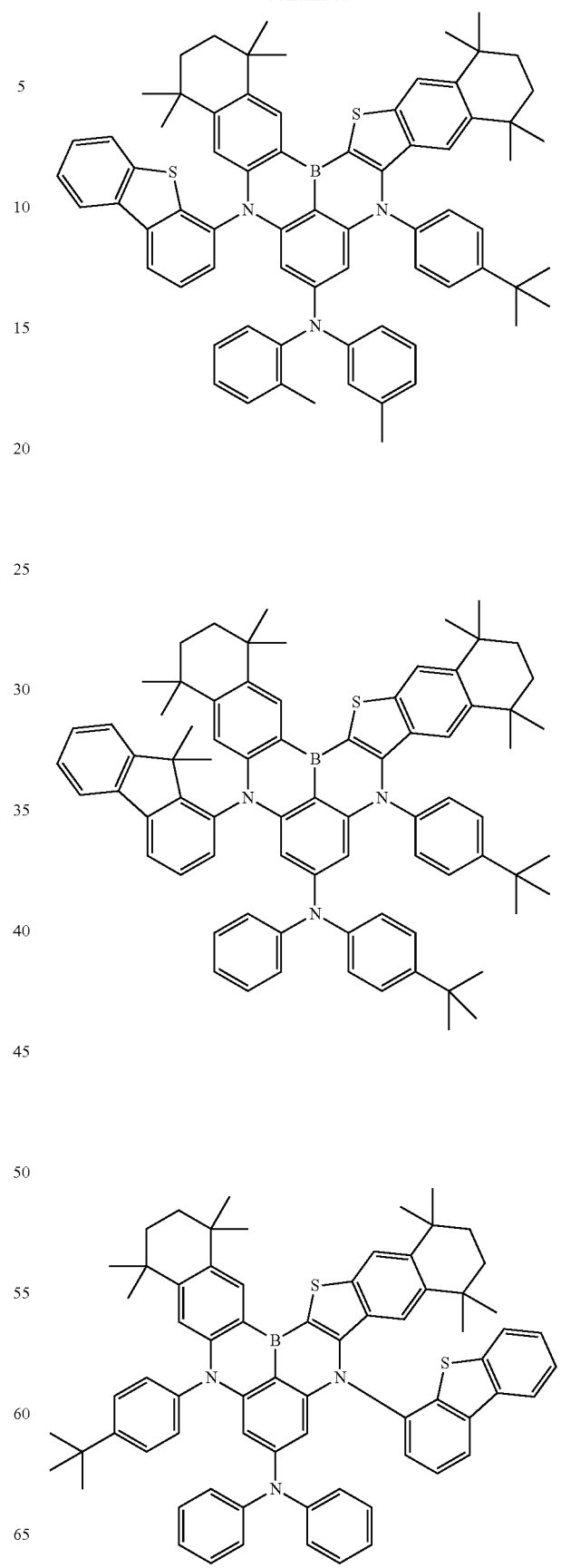

483
-continued
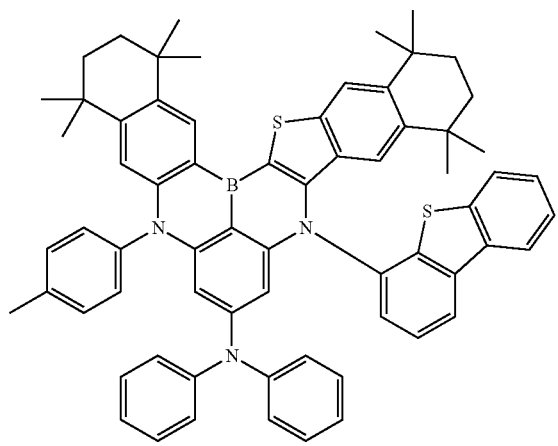
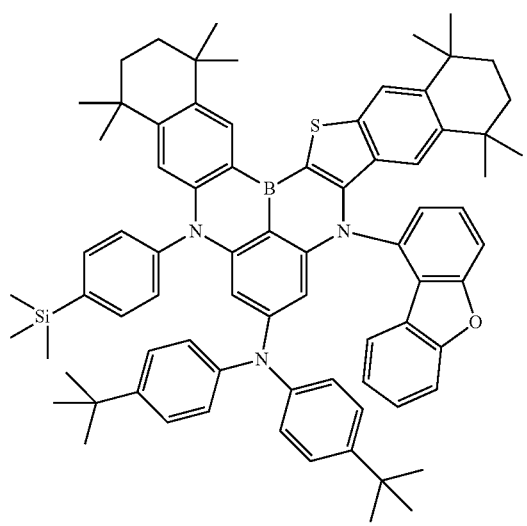
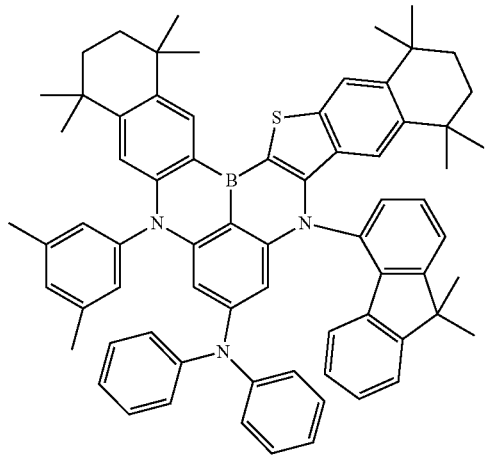
484
-continued
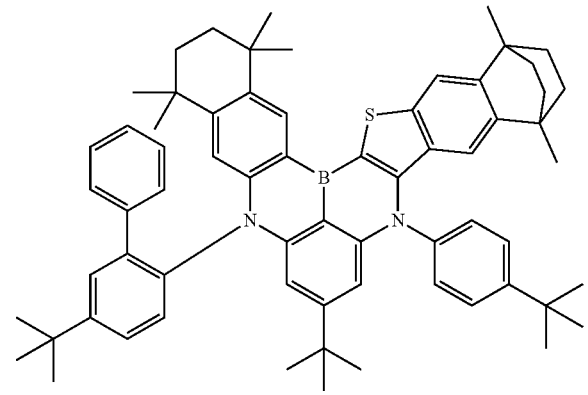
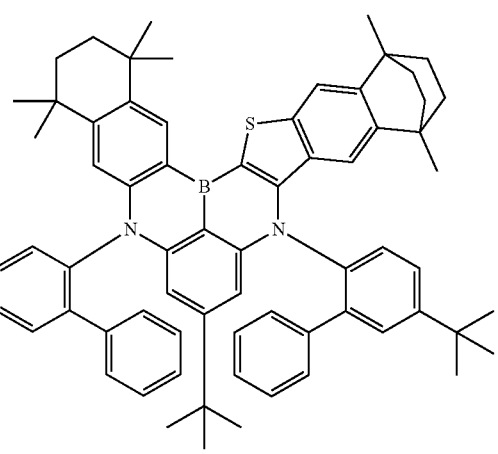
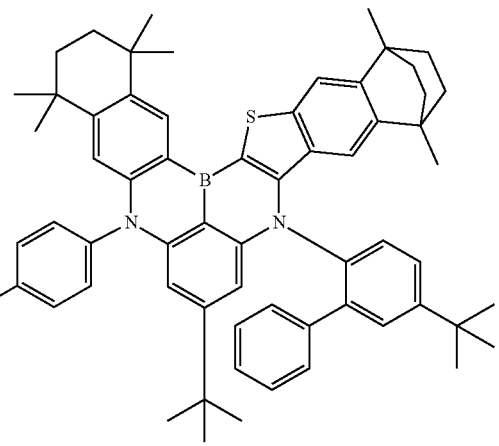

485
-continued
486
-continued
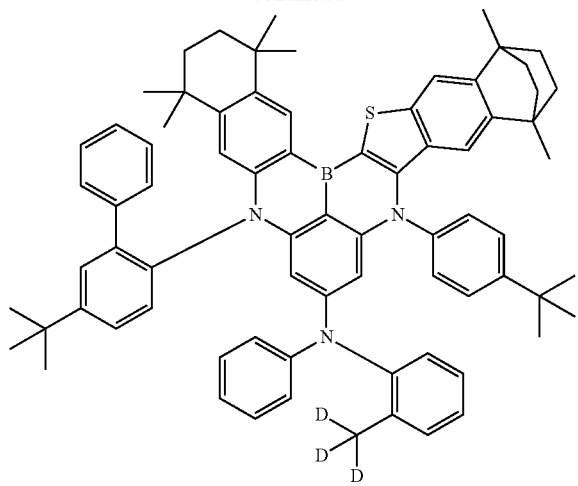
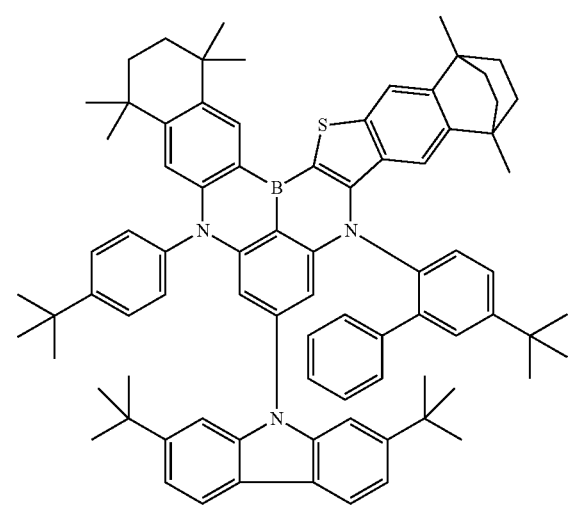
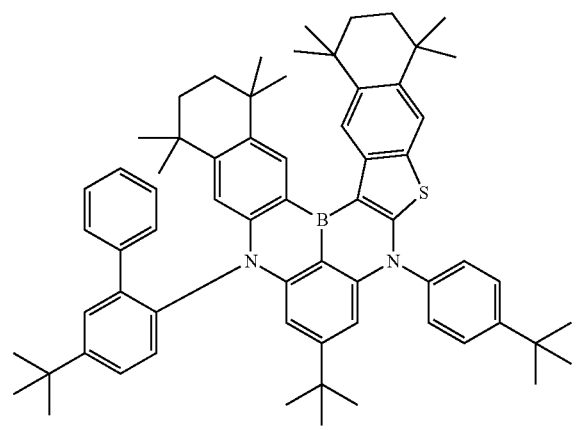
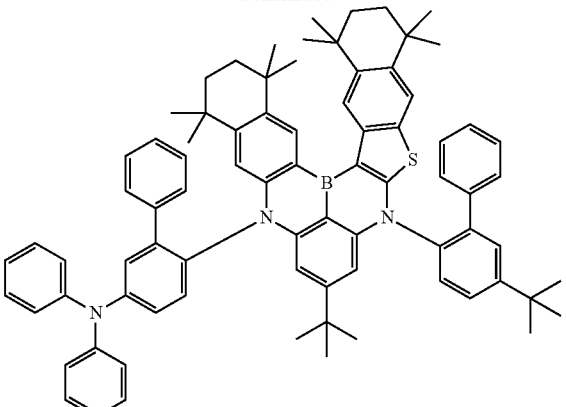
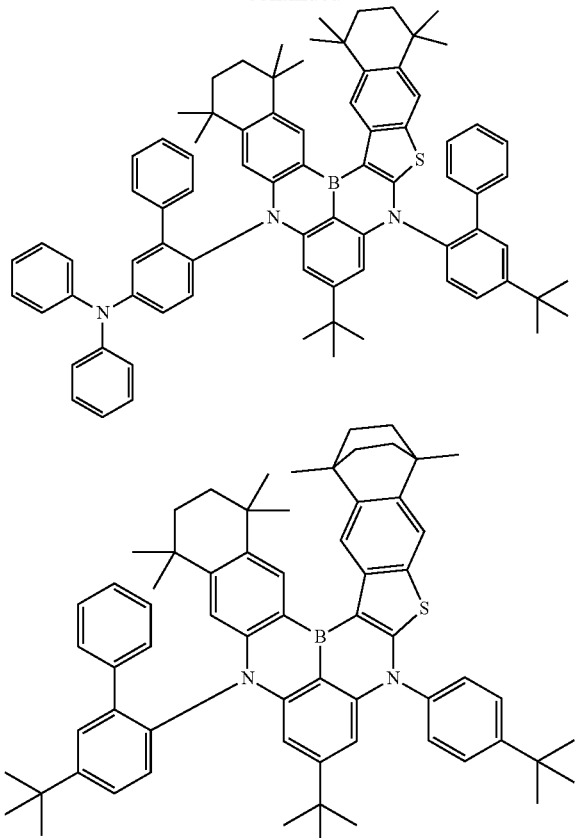
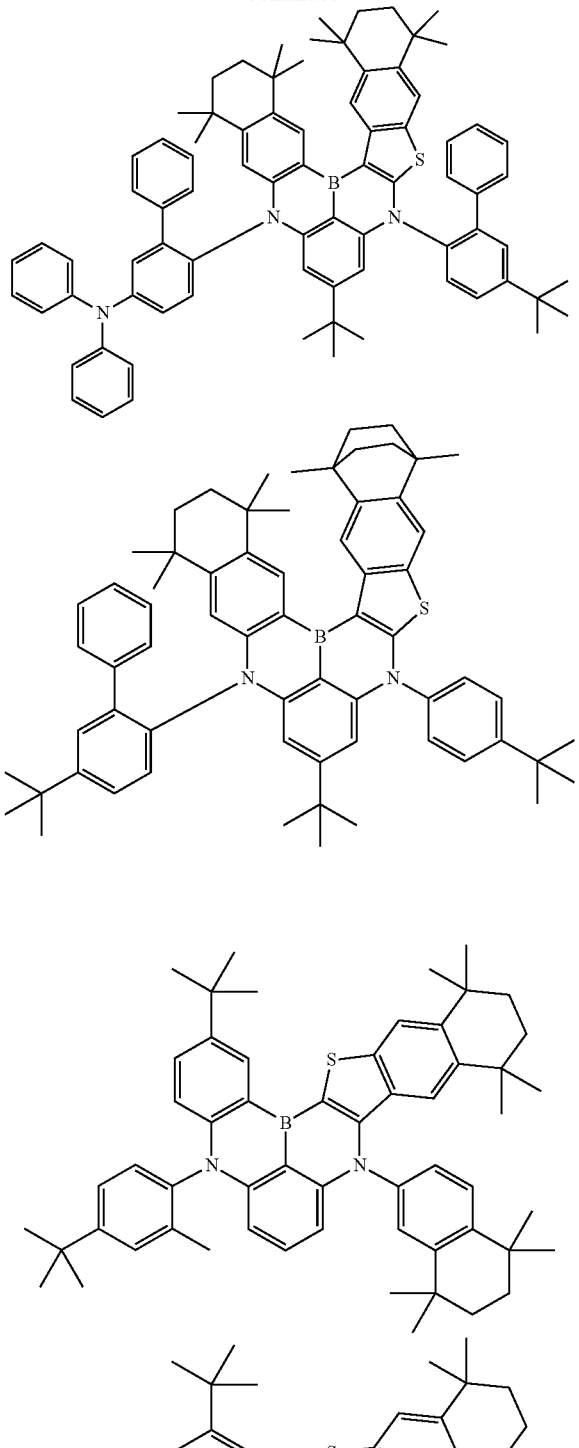

| 487 -continued | 488 -continued |
|---|---|
| 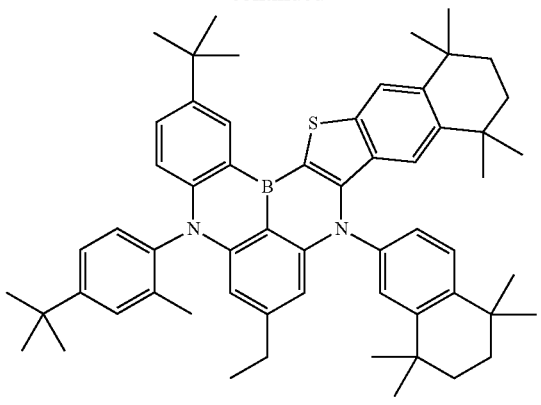 | 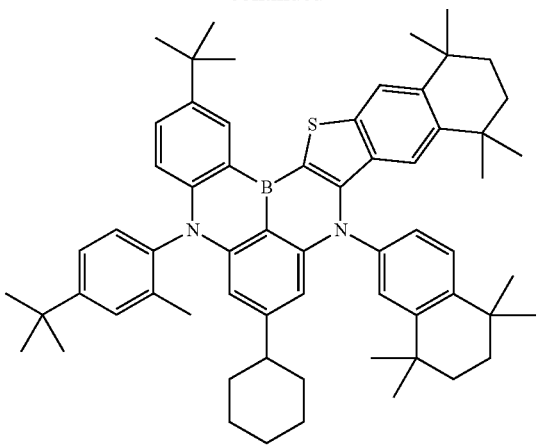 |
| 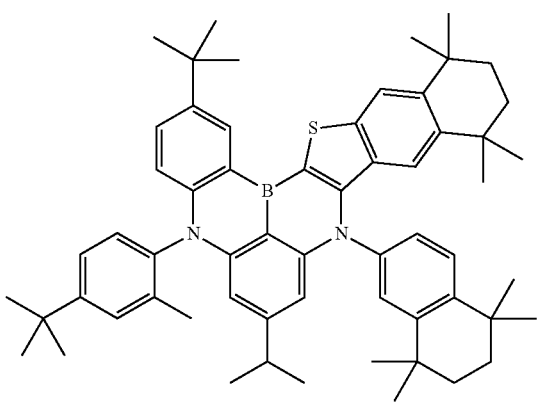 | 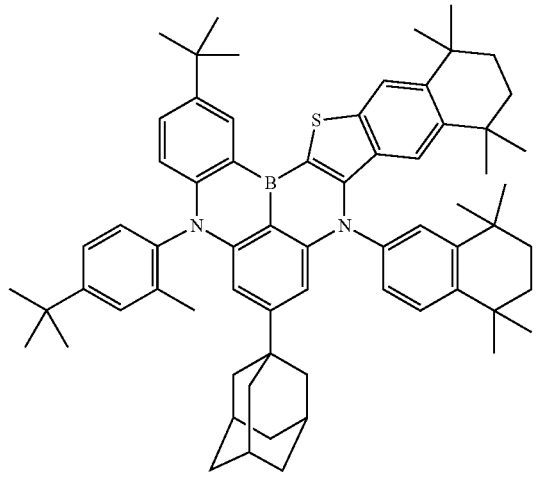 |
| 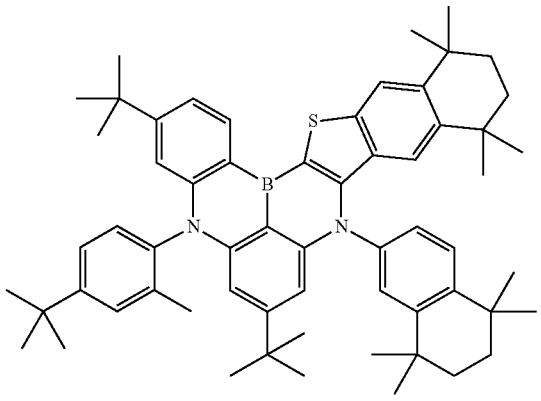 | 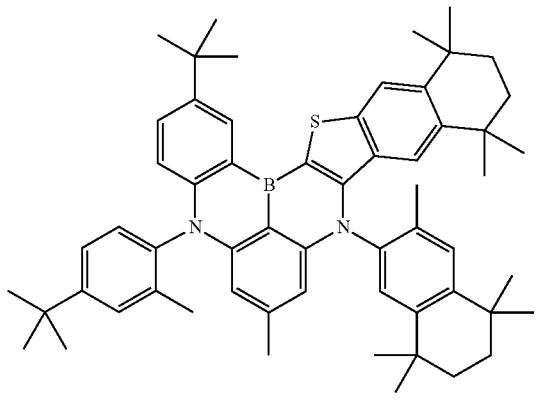 |
| 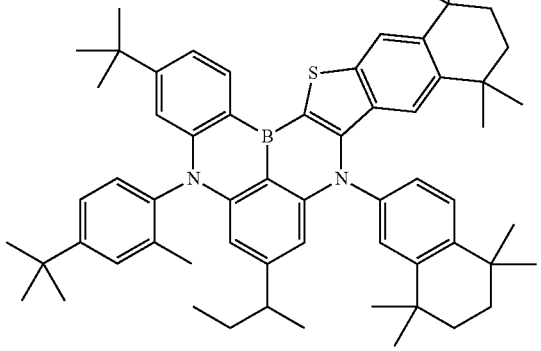 | 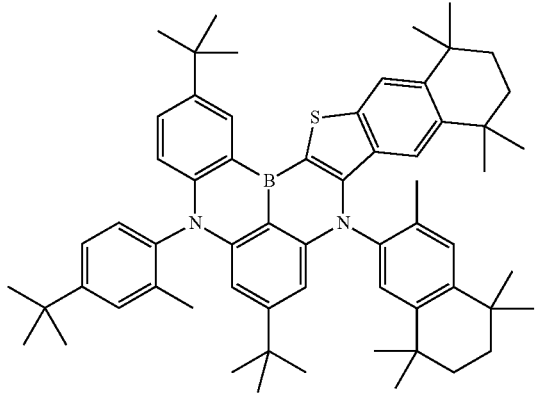 |

489
-continued
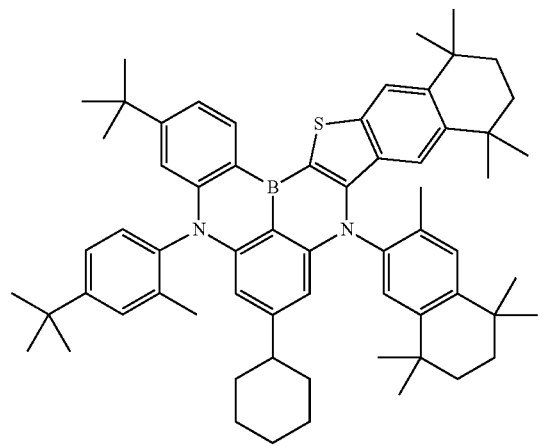
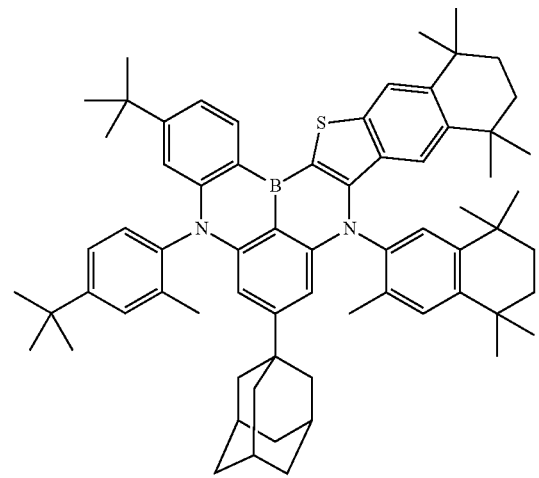
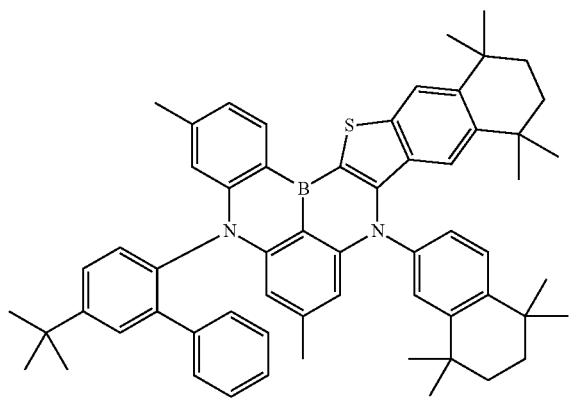
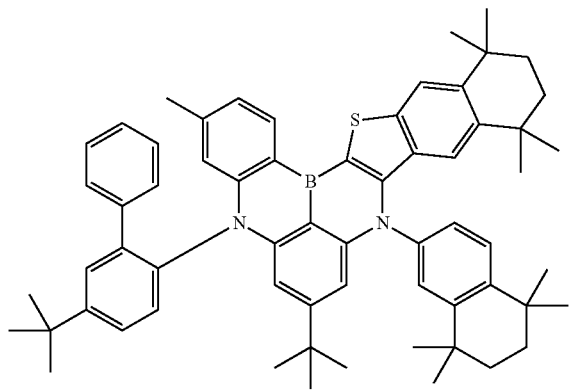
490
-continued
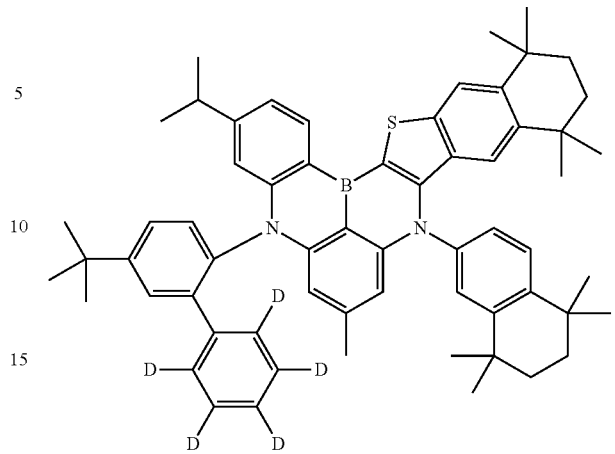
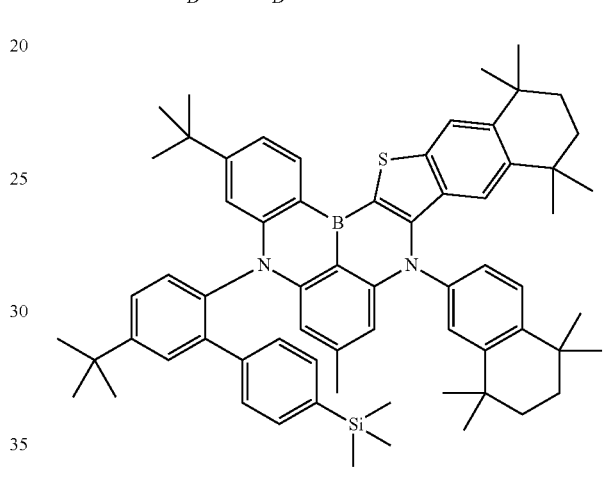
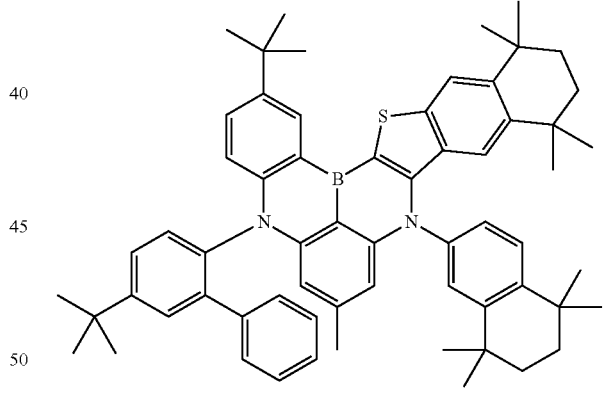
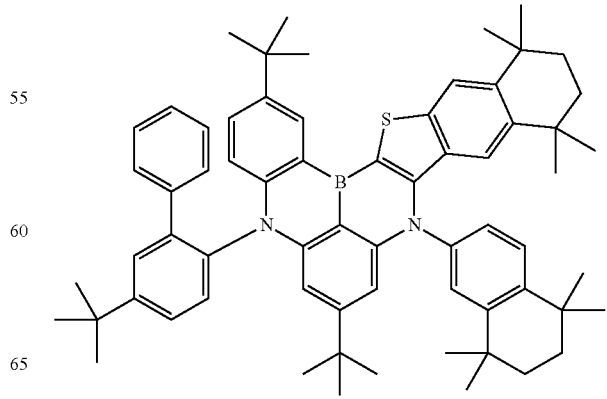

491
-continued
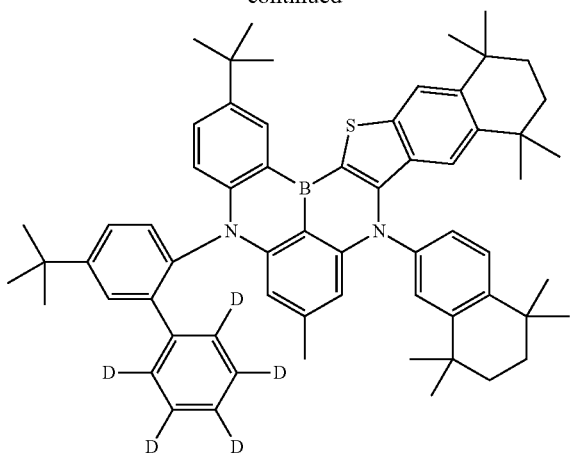
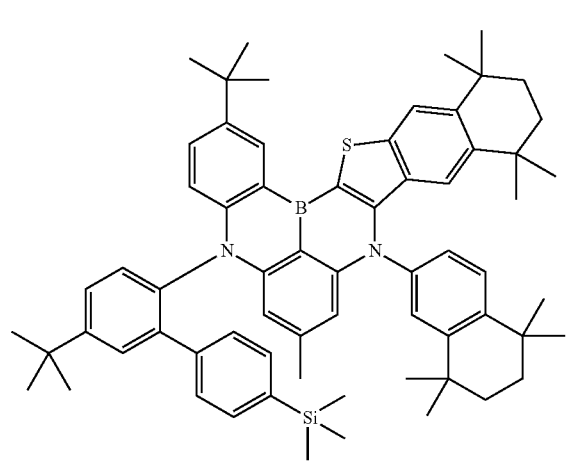
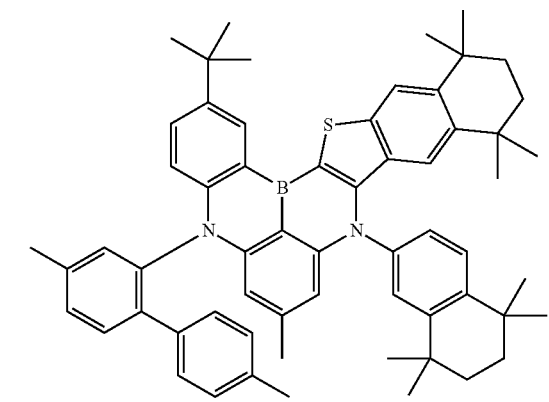
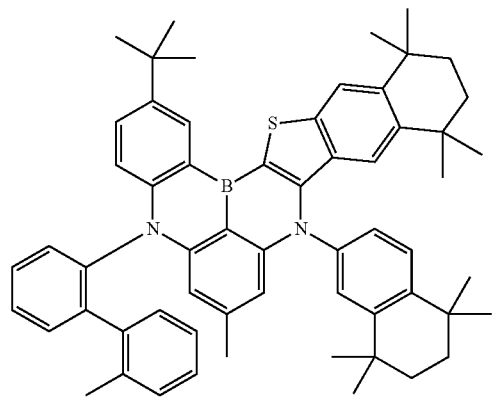
492
-continued
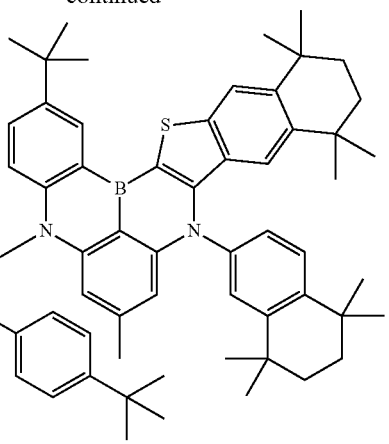
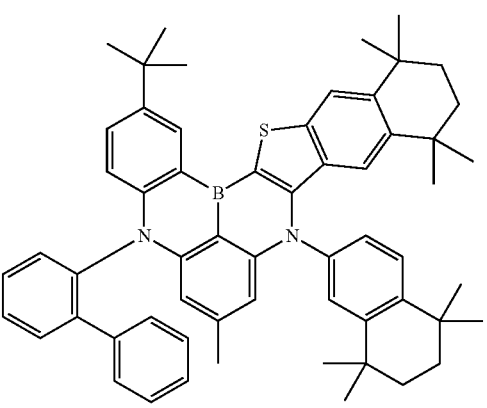
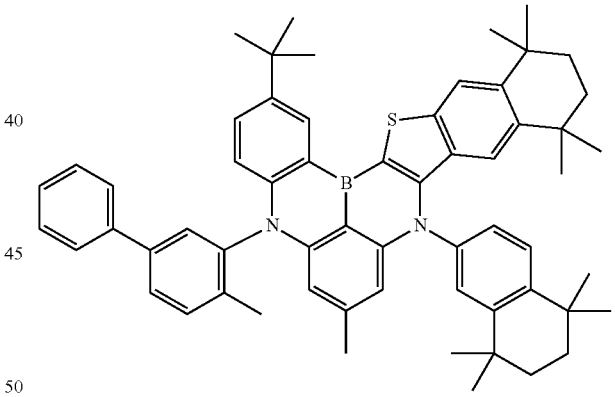
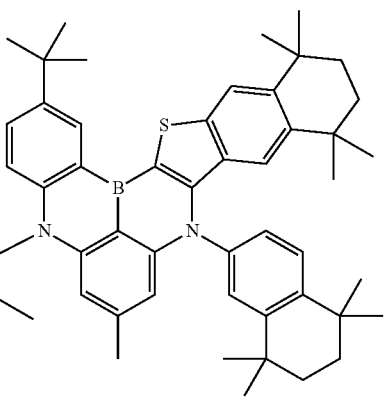

493
-continued
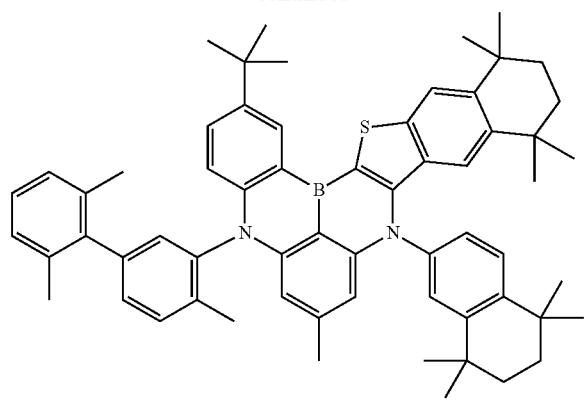
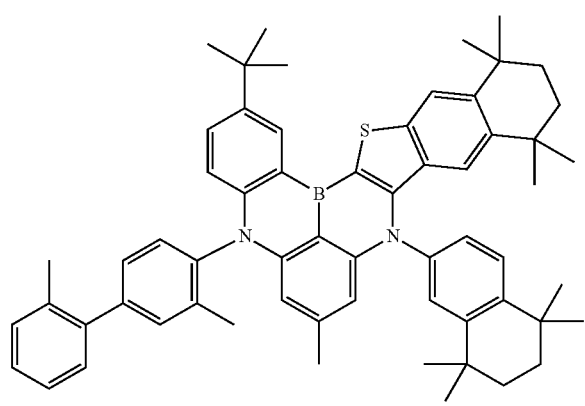
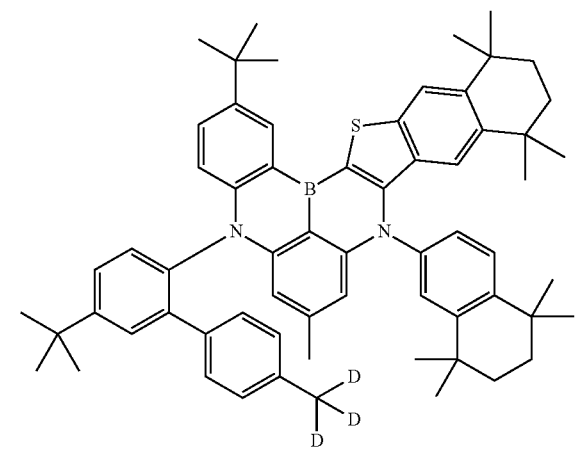
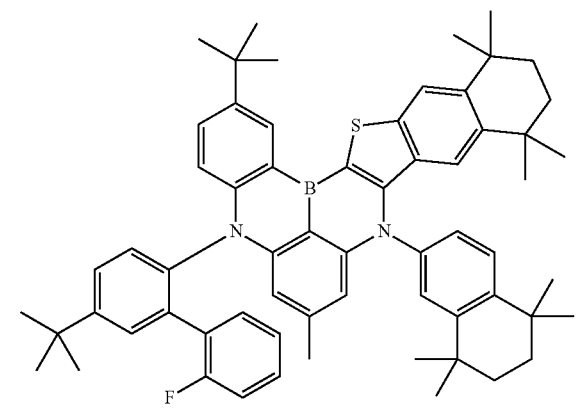
494
-continued
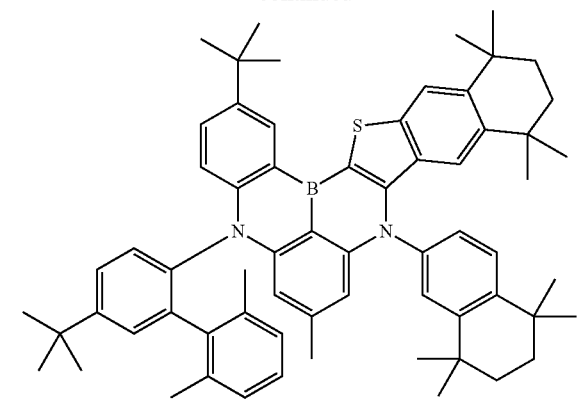
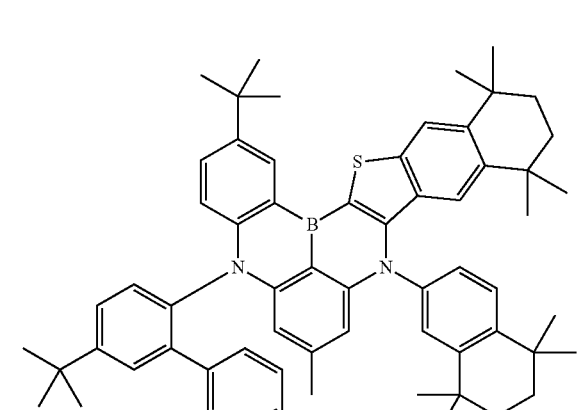

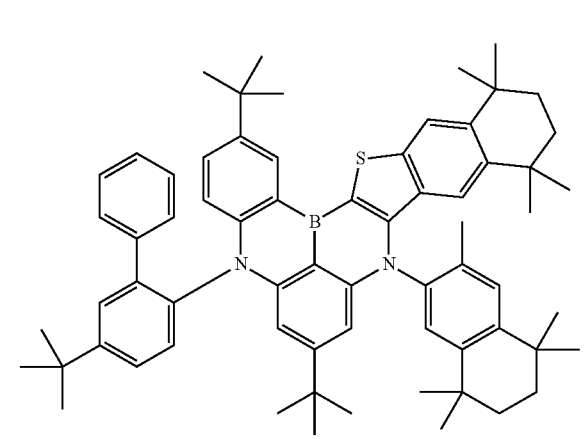

495
-continued
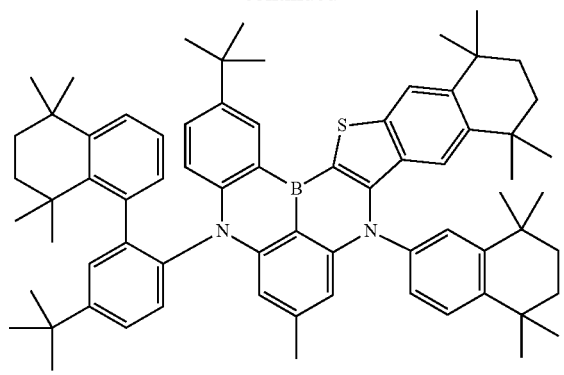
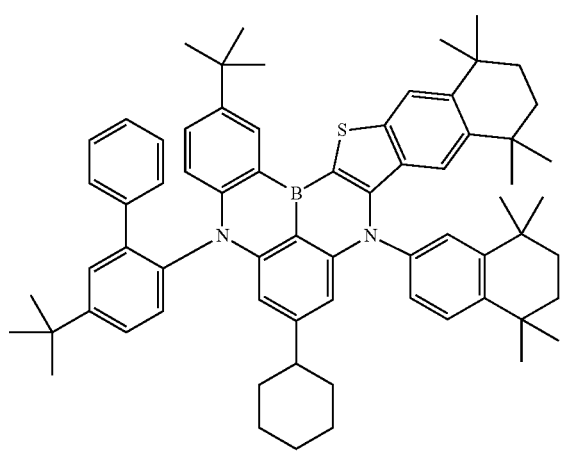
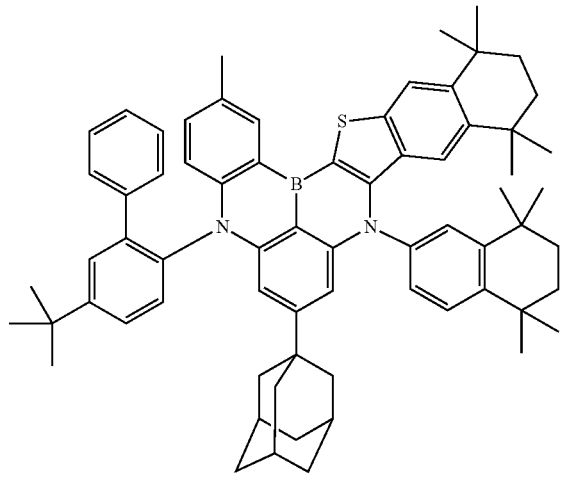
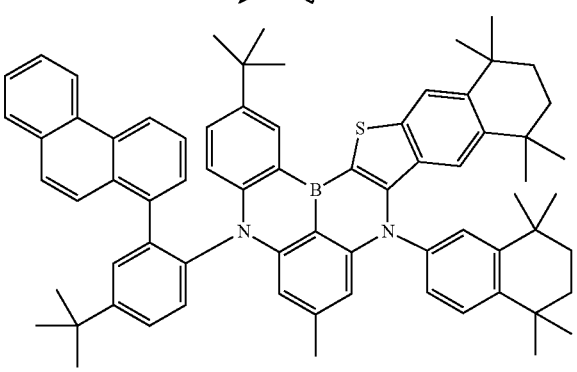
496
-continued
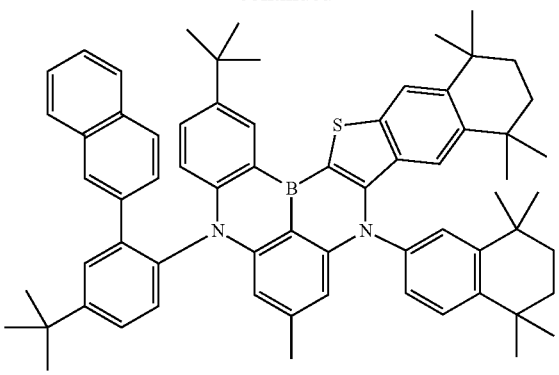
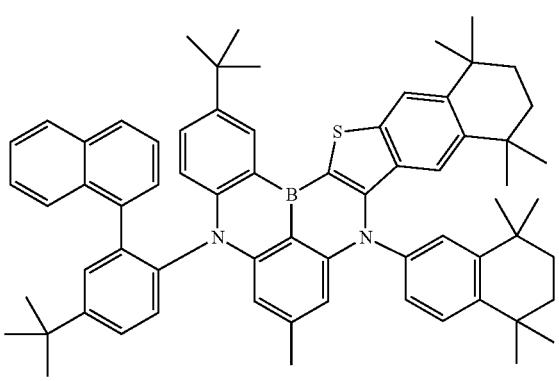
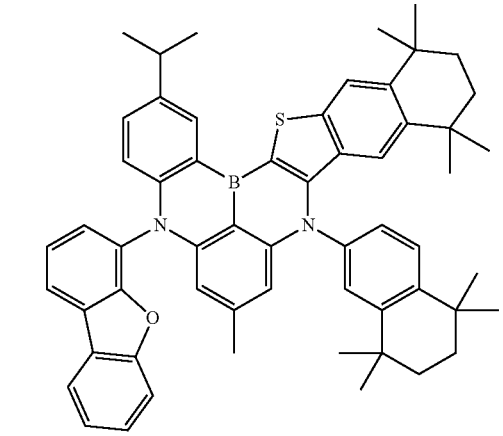
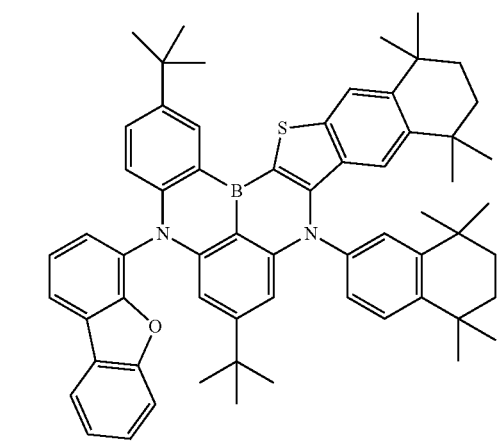

497
-continued
498
-continued
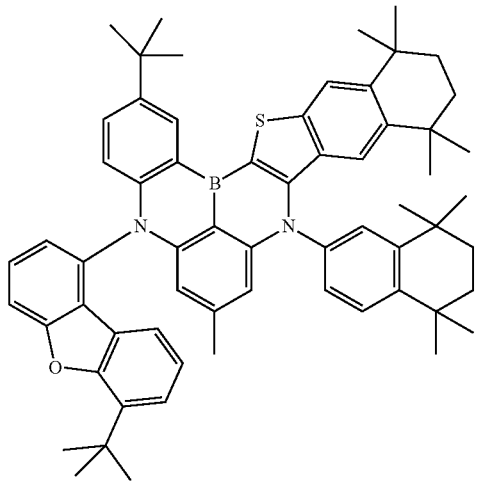
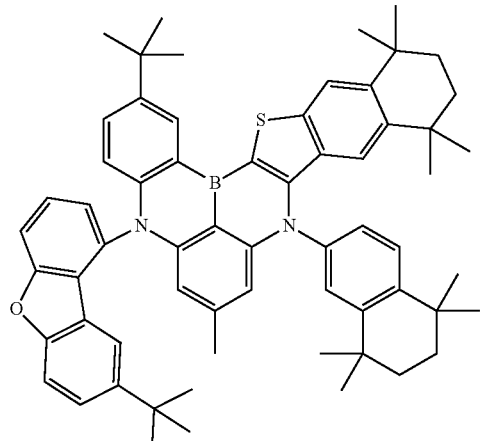
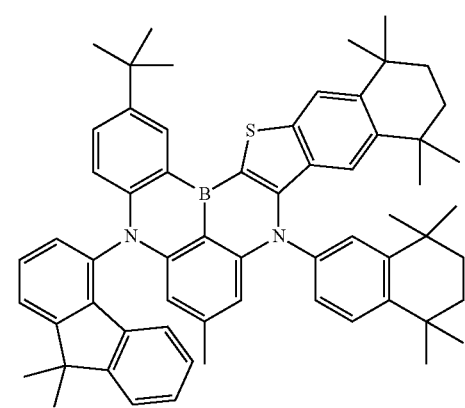
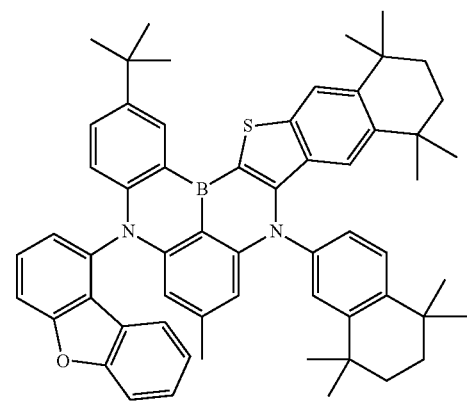
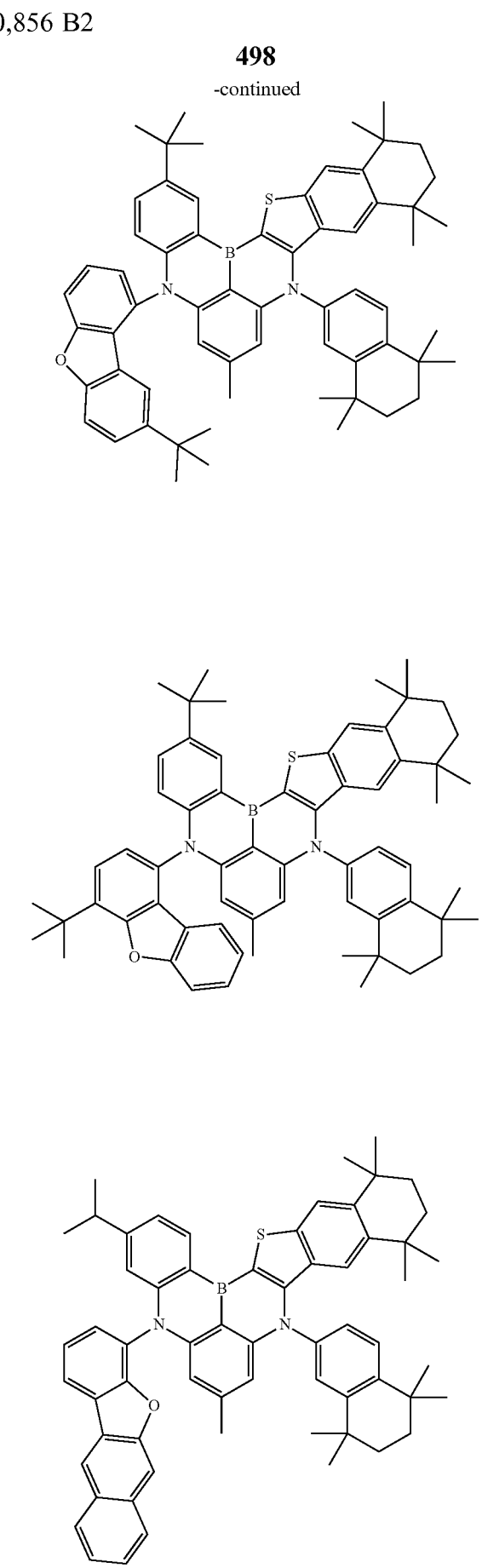

499
-continued
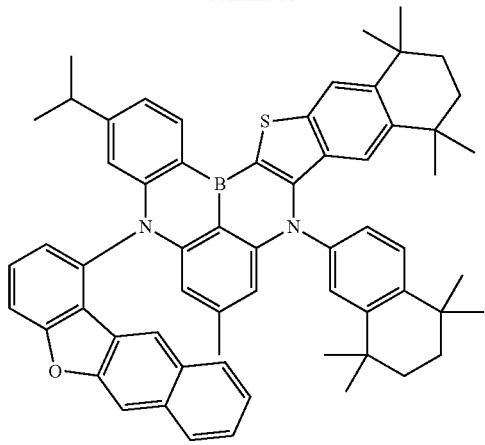
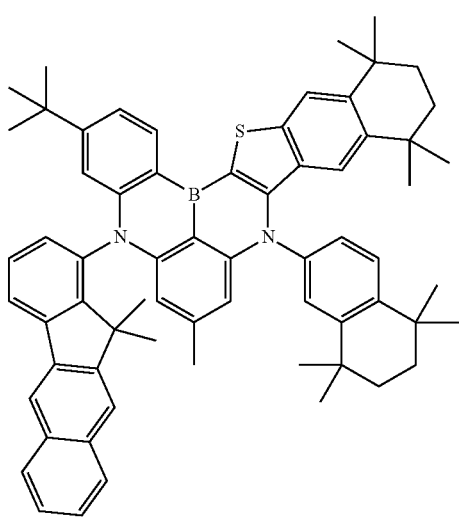
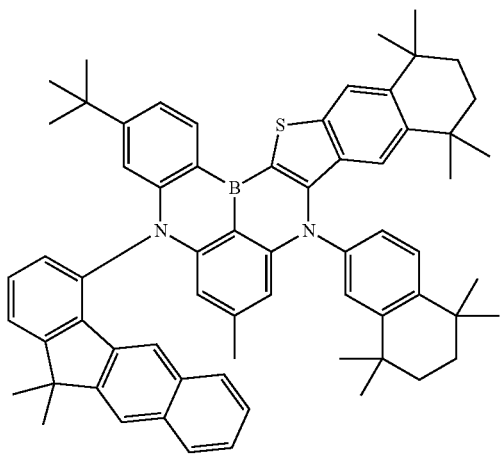
500
-continued
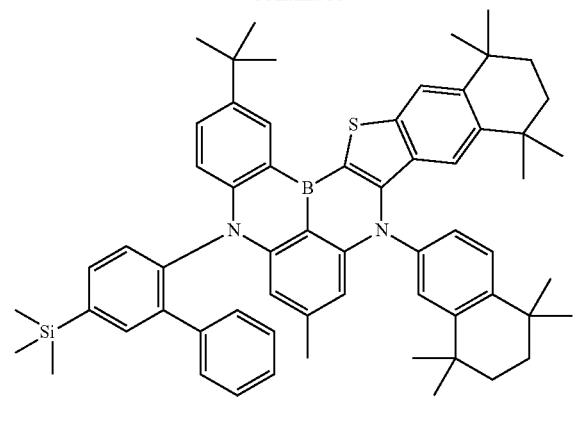
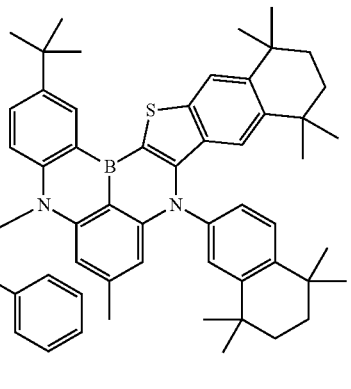

| 501 -continued | 502 -continued |
|---|---|
| 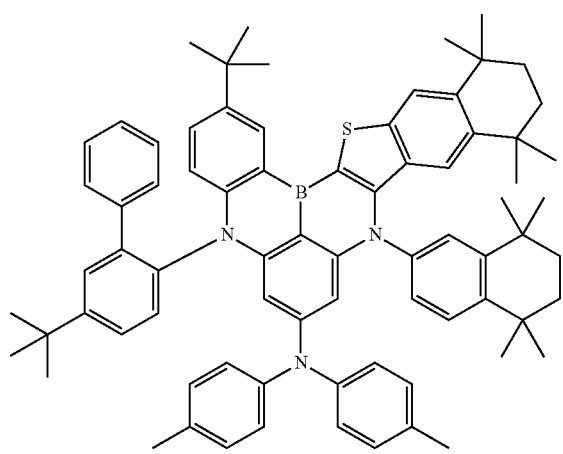 | 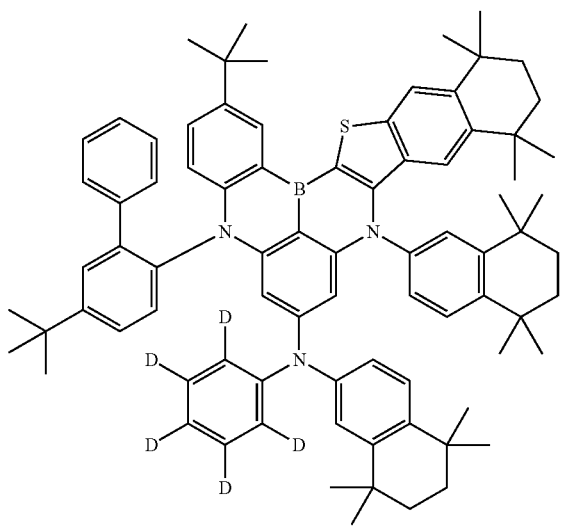 |
| 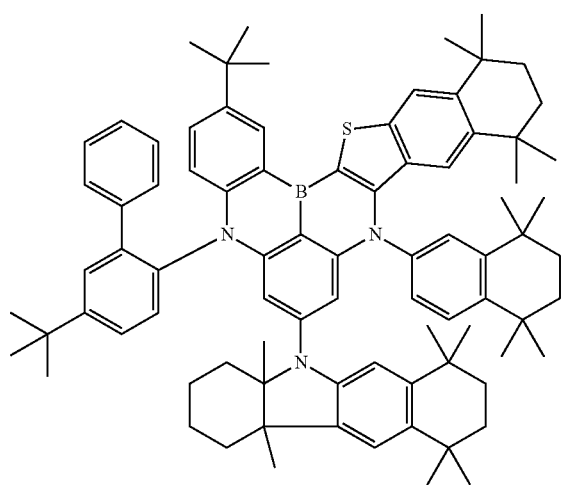 | |
| 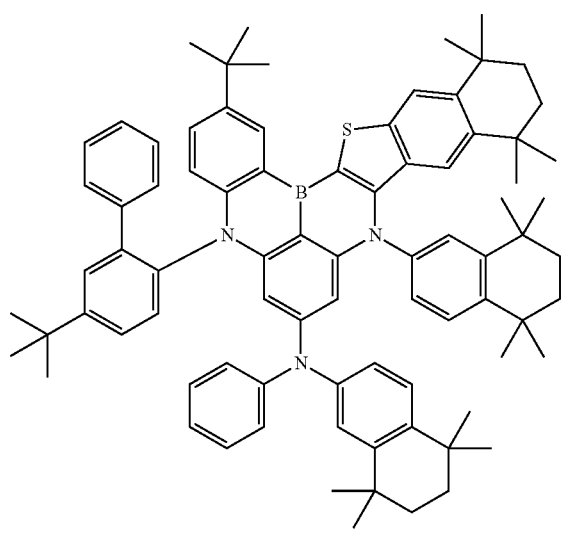 | 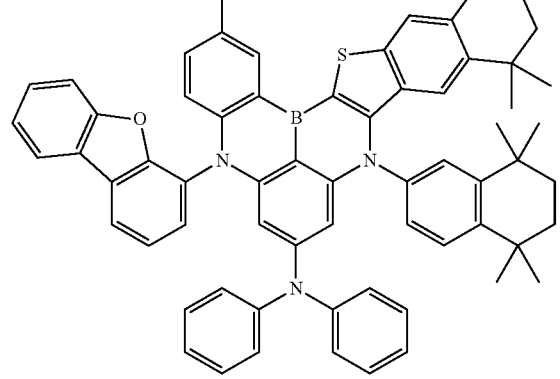 |

503
-continued
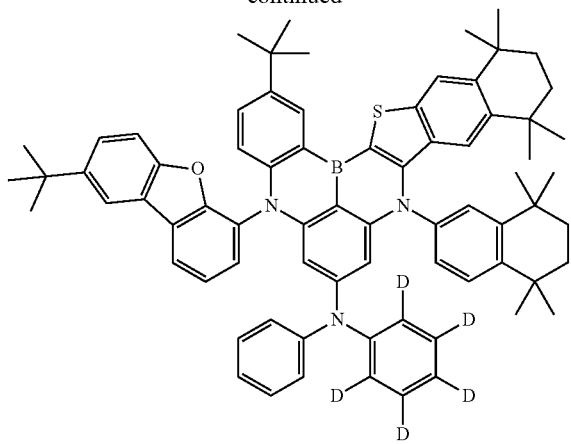
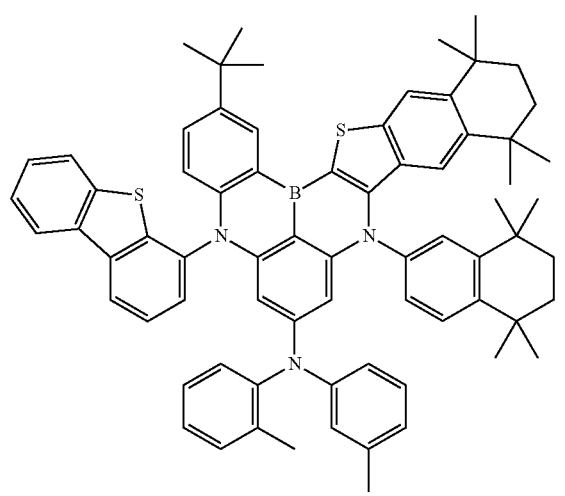
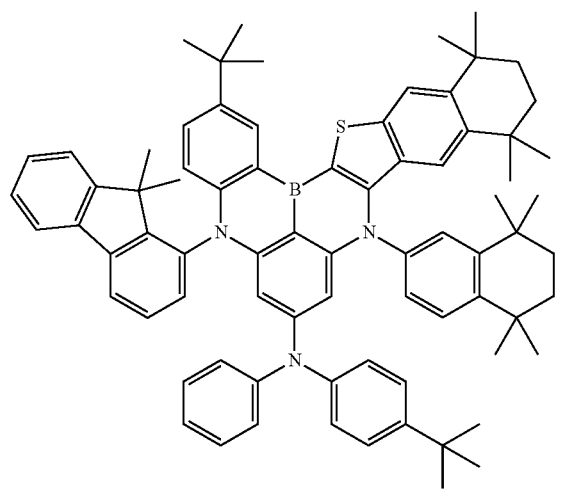
504
-continued
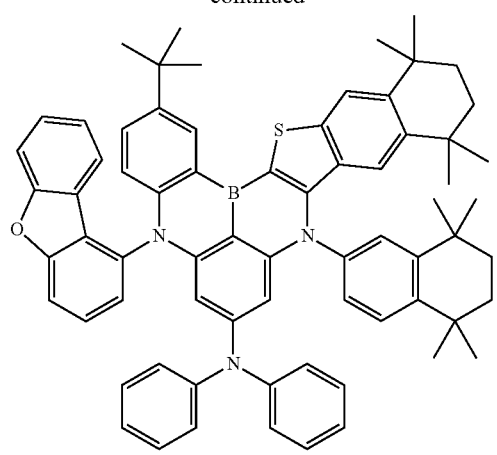
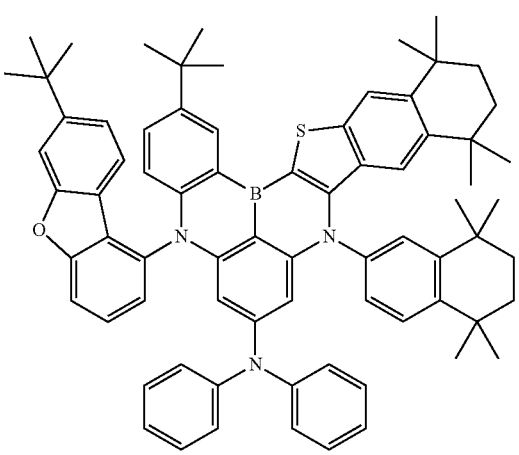
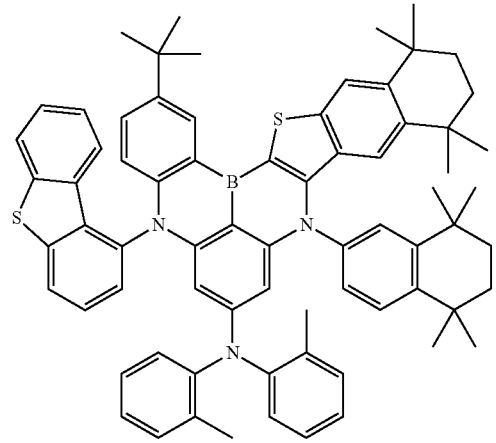

505
-continued
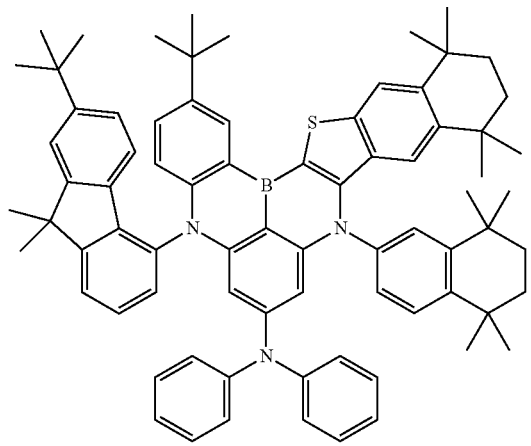
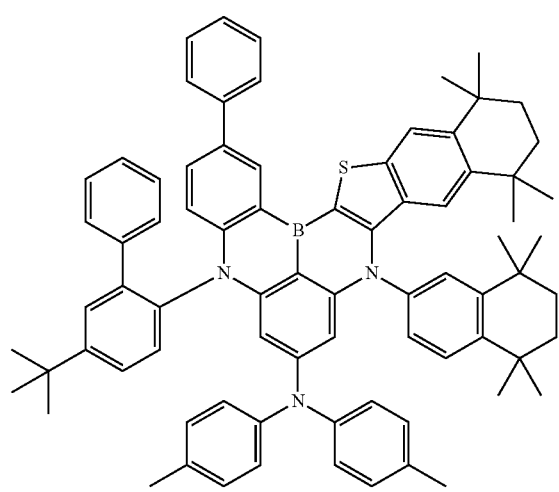
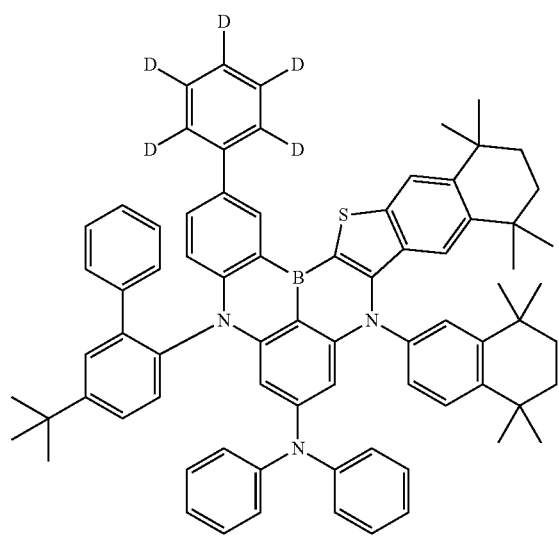
506
-continued
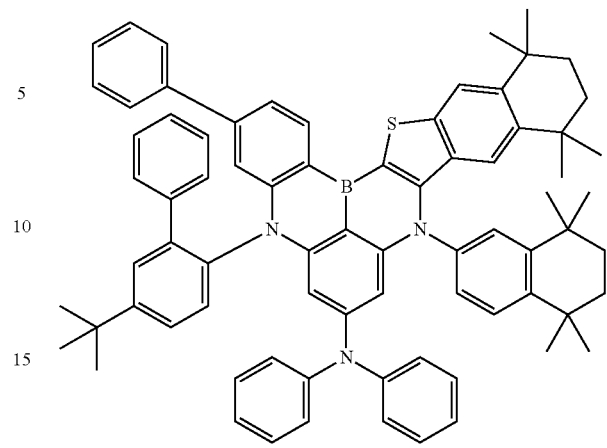
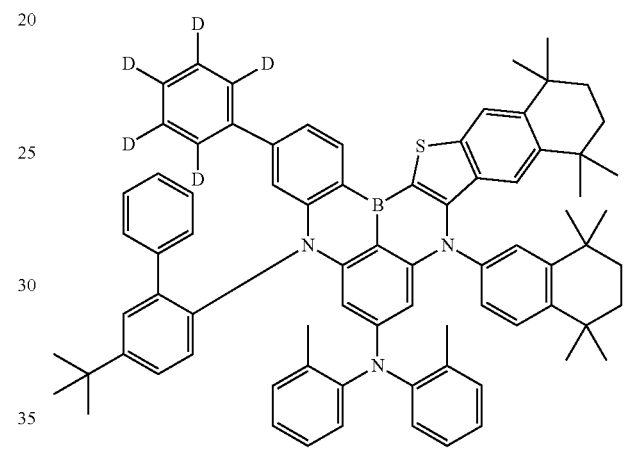
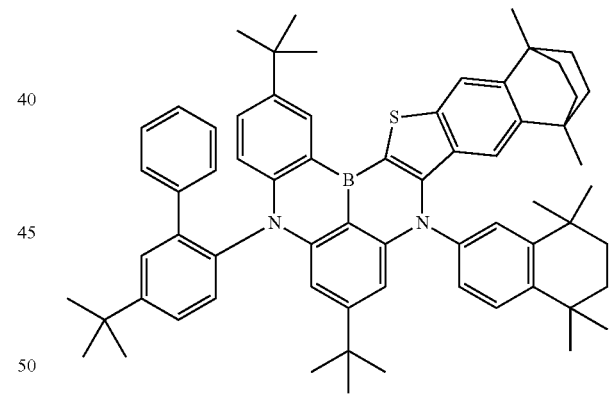
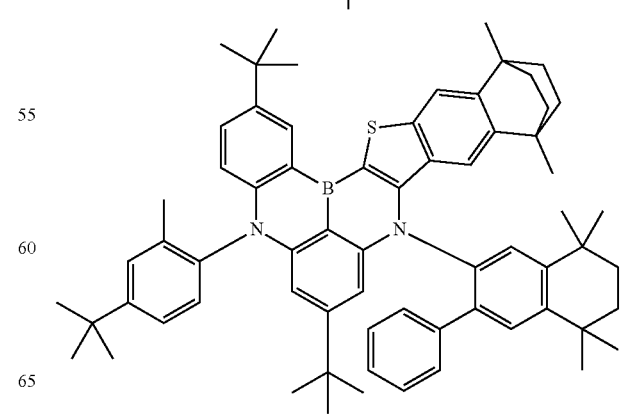

507
-continued
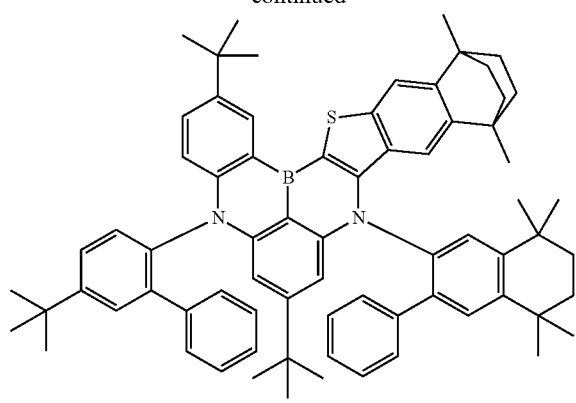
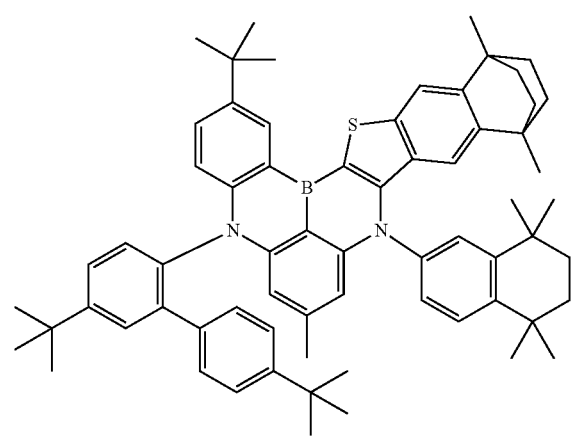
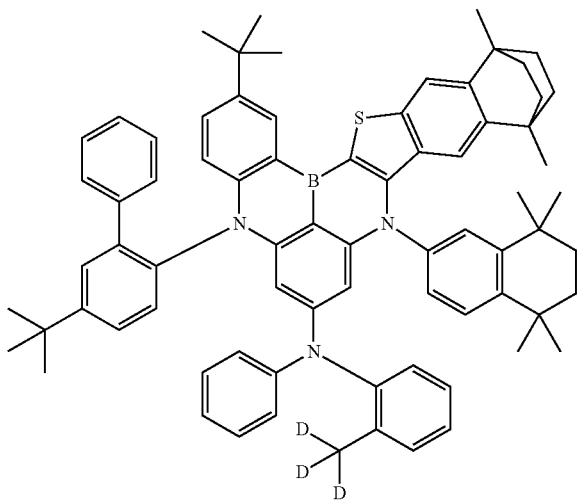
508
-continued
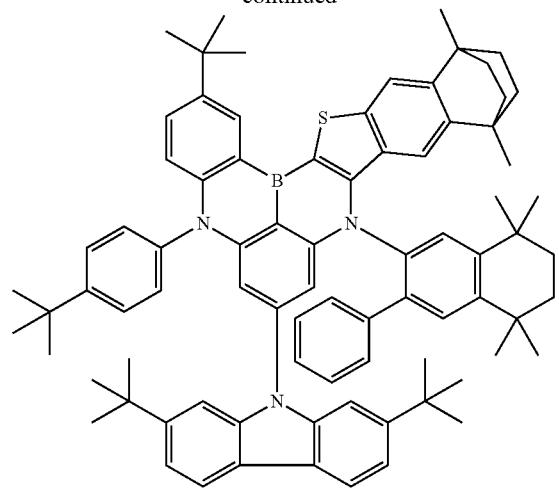
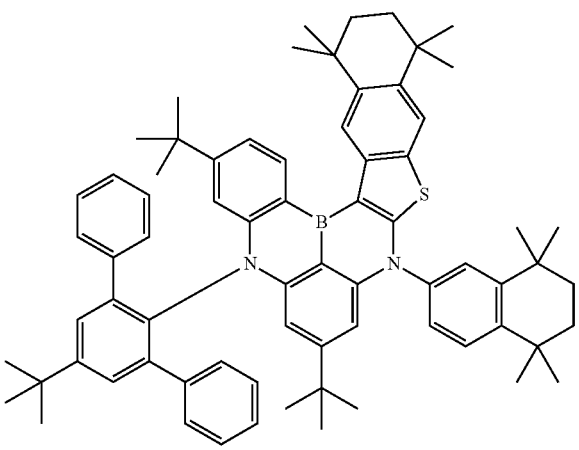
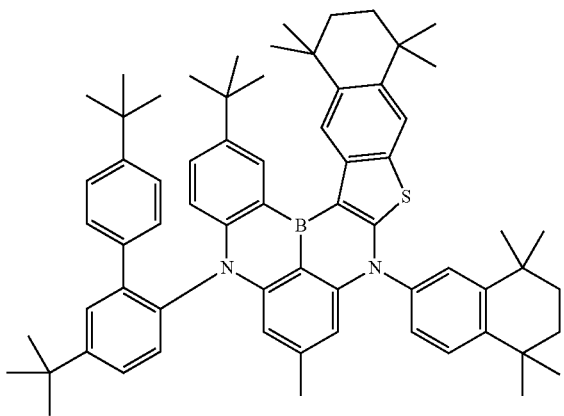

509
-continued
510
-continued
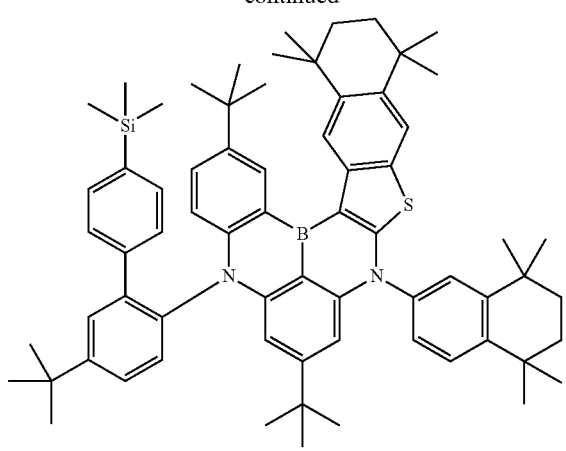
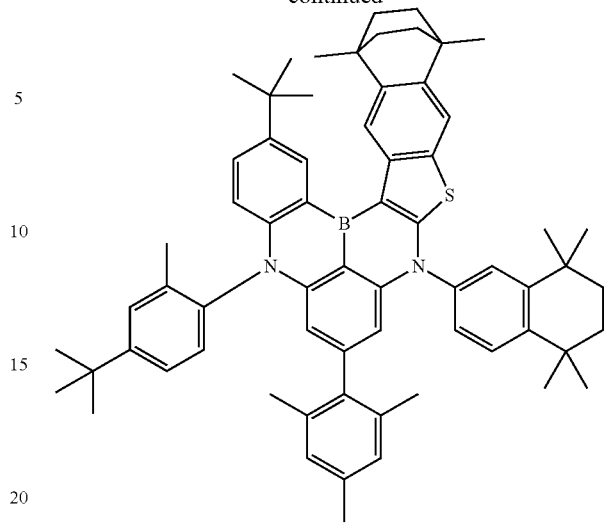
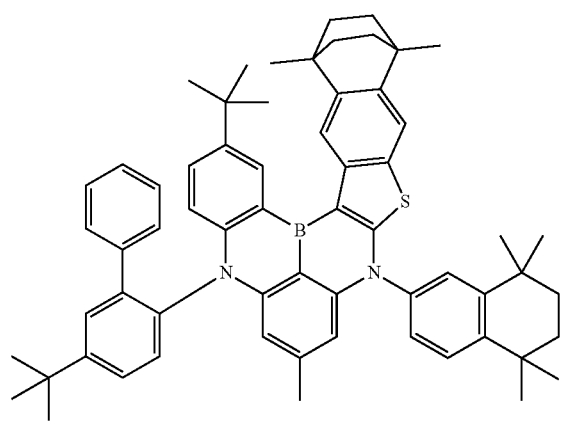
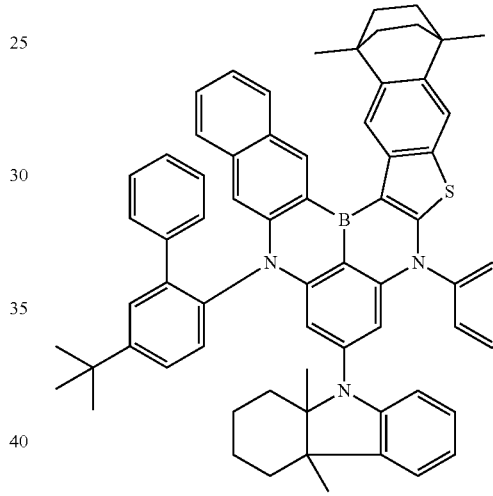
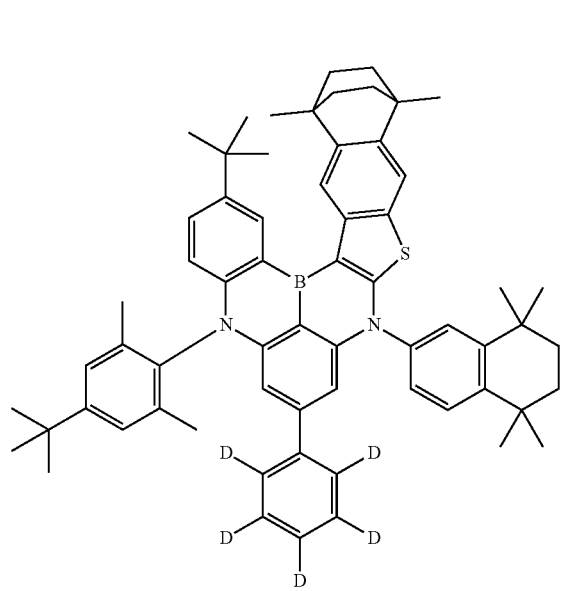
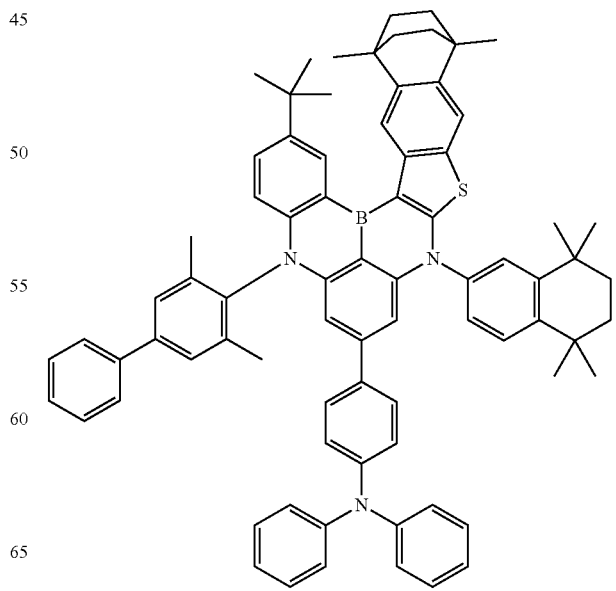

| 511 | 512 |
|---|---|
| -continued | -continued |
| 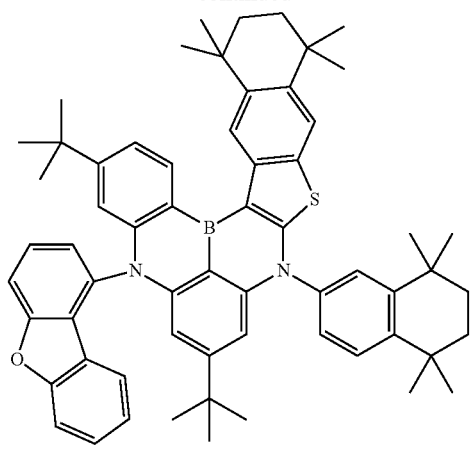 | 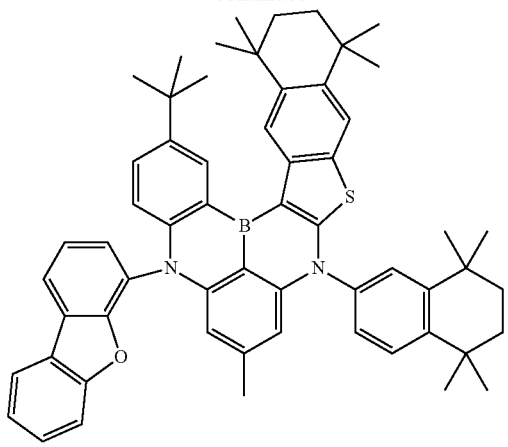 |
| 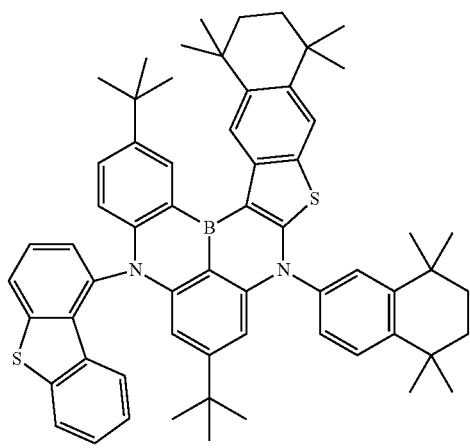 | 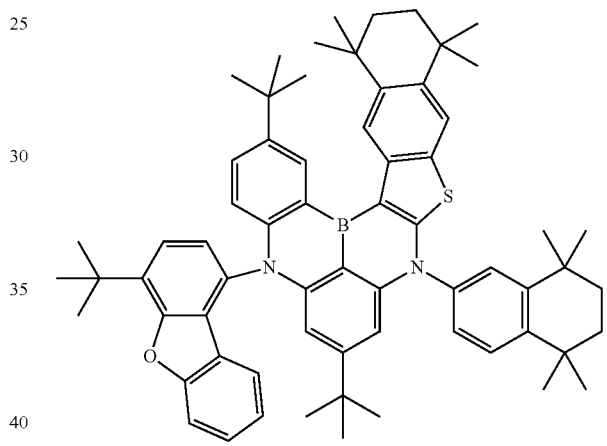 |
| 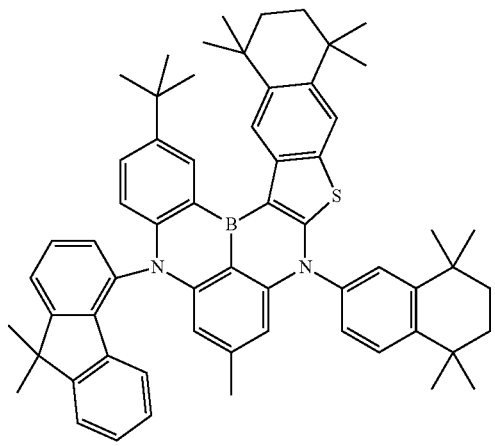 | 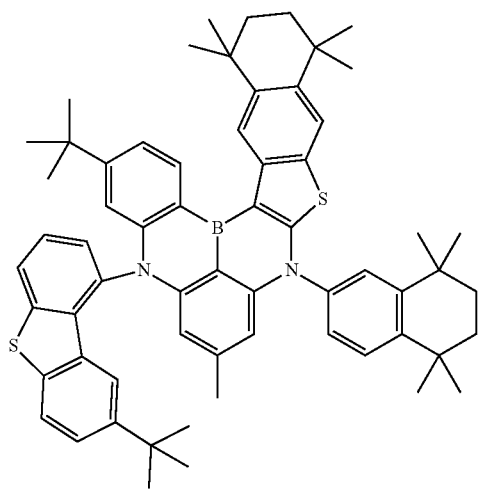 |

513
-continued
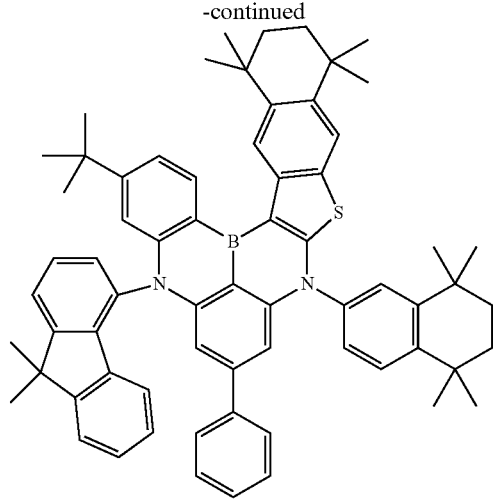
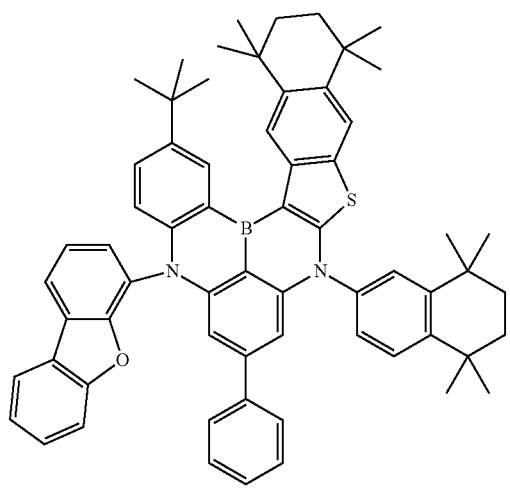
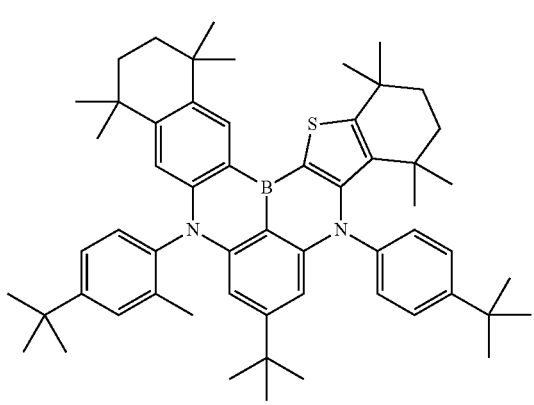
514
-continued
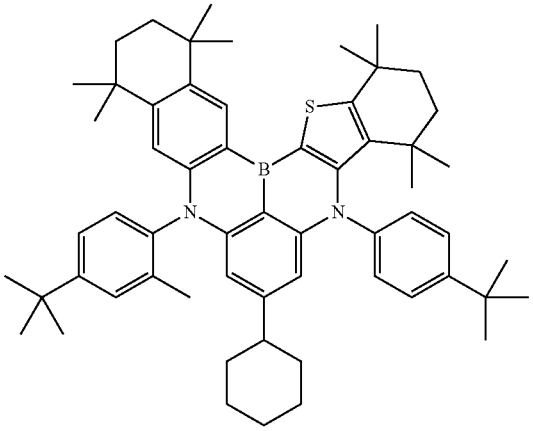
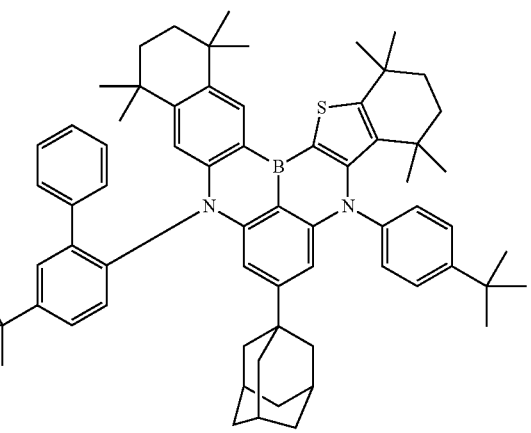
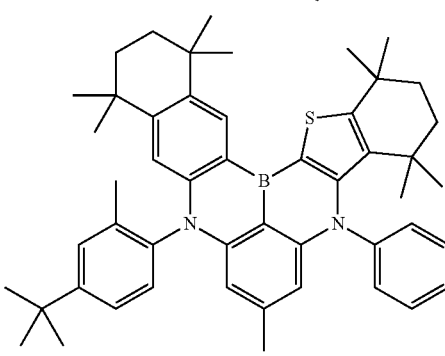
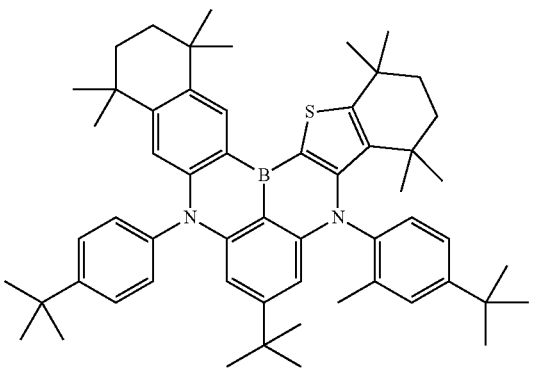

515
-continued
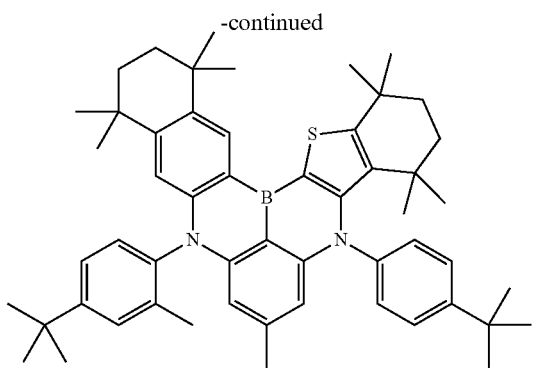
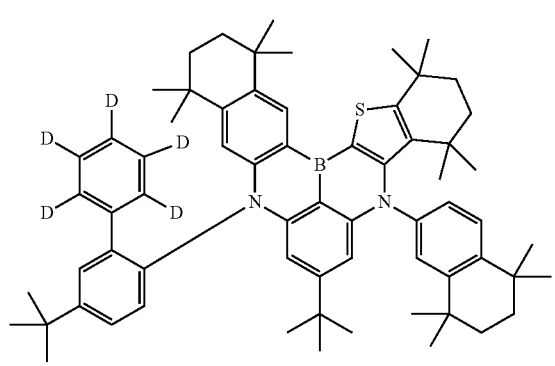
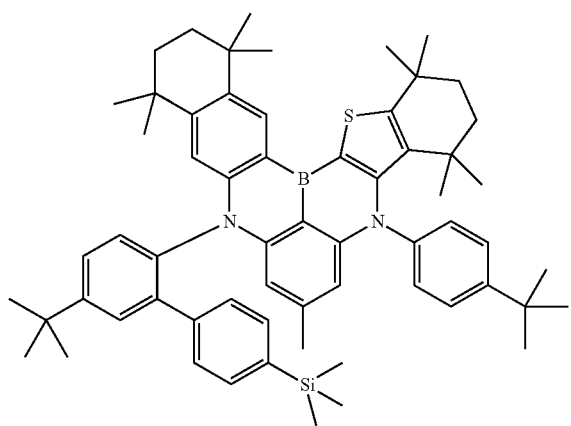
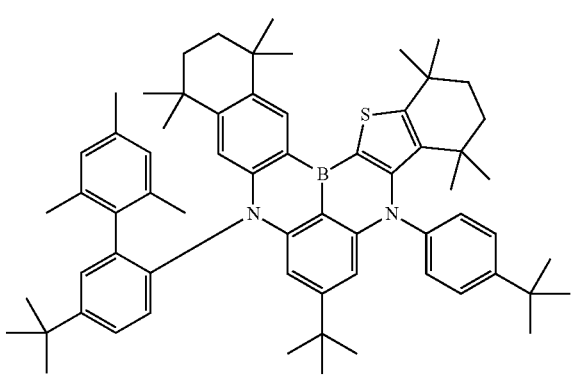
516
-continued
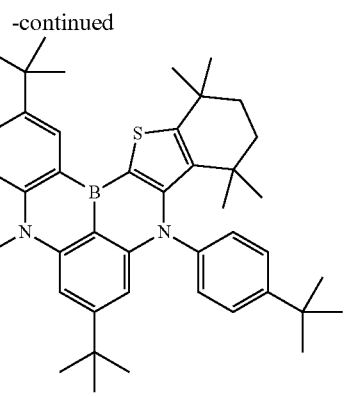
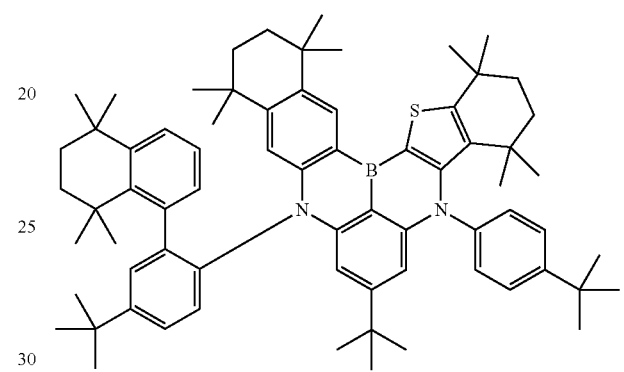
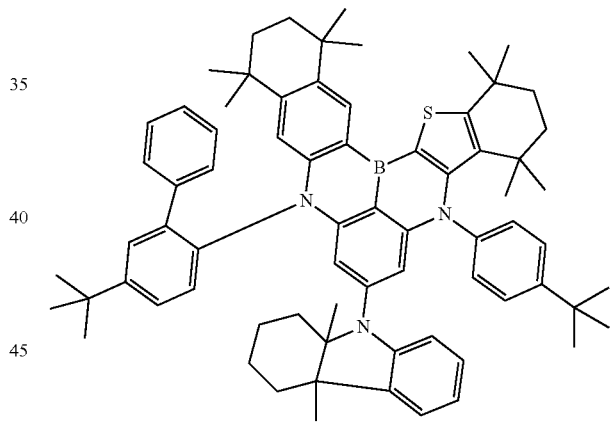
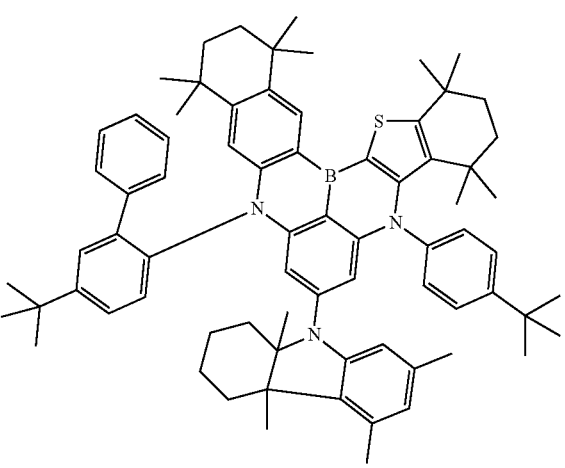

517
-continued
518
-continued
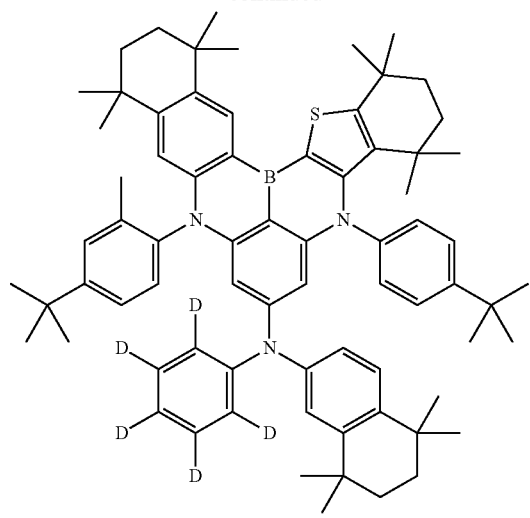
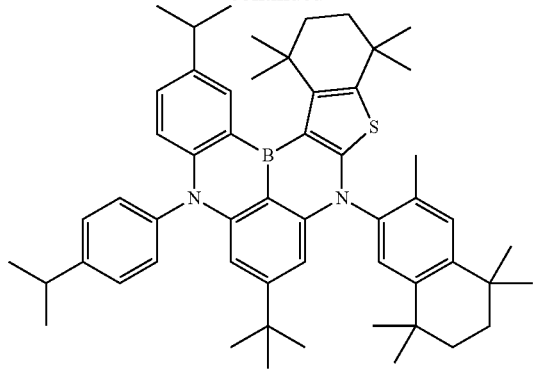
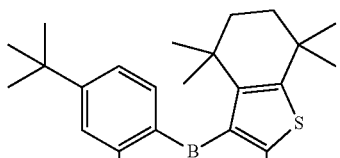
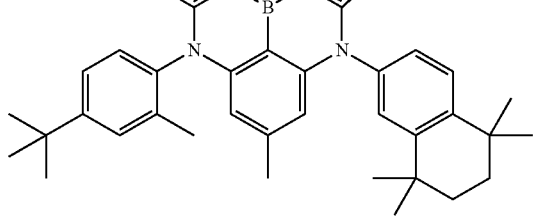
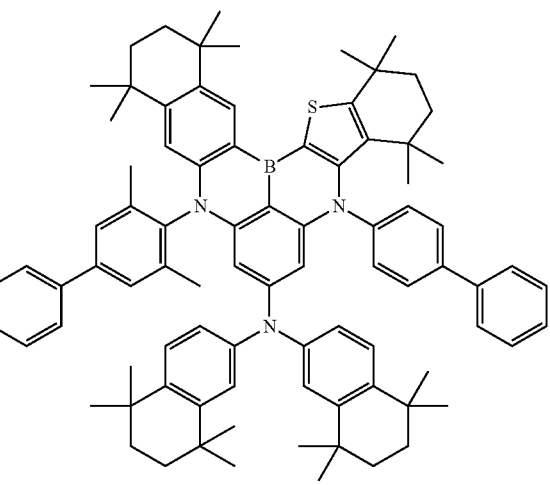
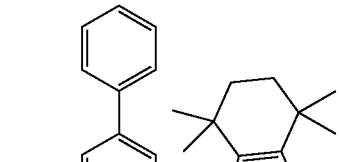
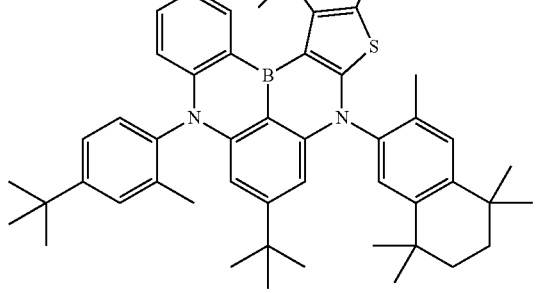
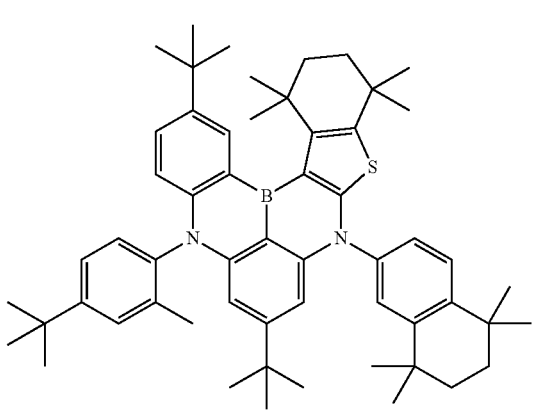
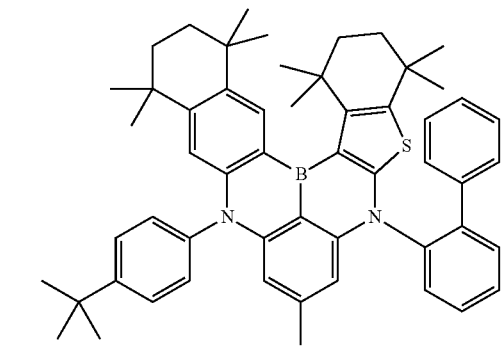

| 519 -continued | 520 -continued |
|---|---|
| 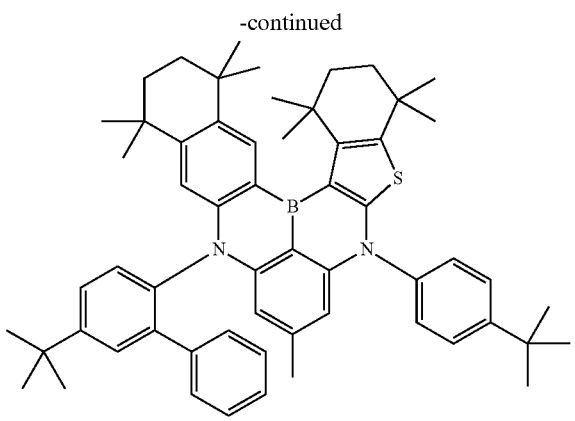 | 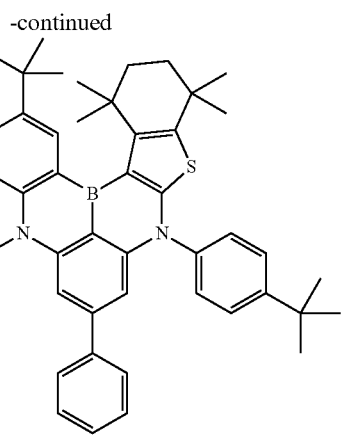 |
| 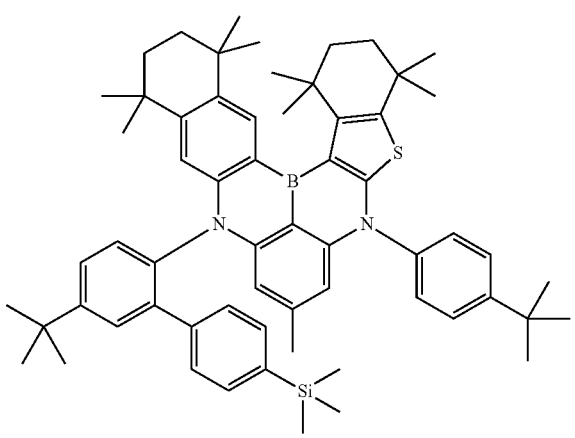 | |
| 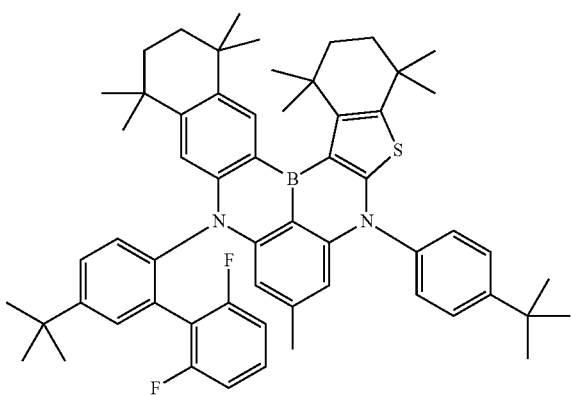 | 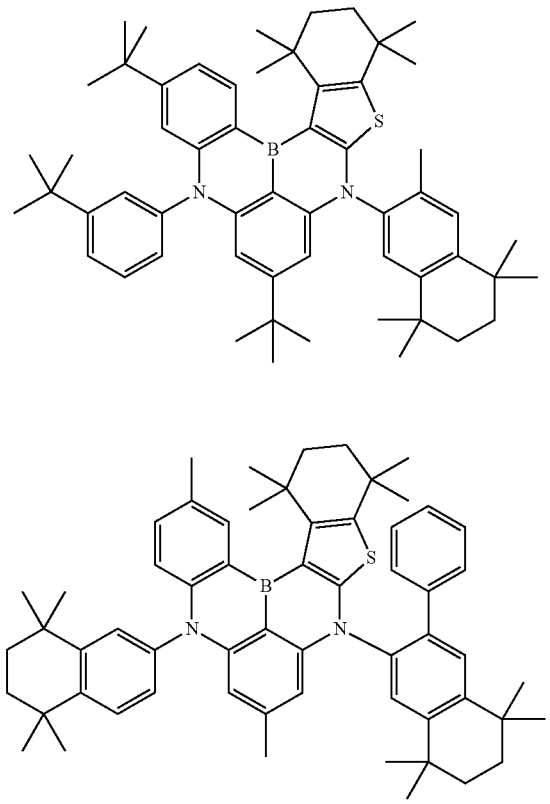 |
| 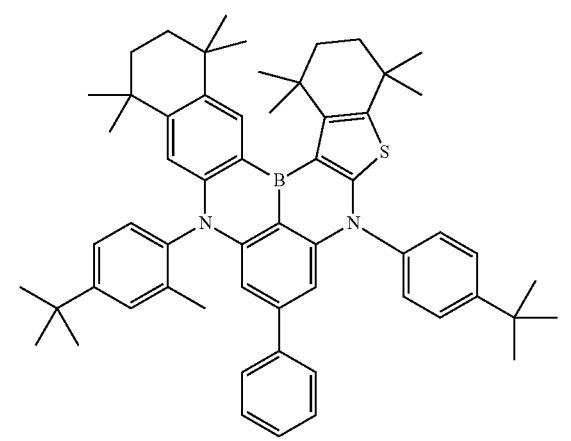 | |

521
-continued
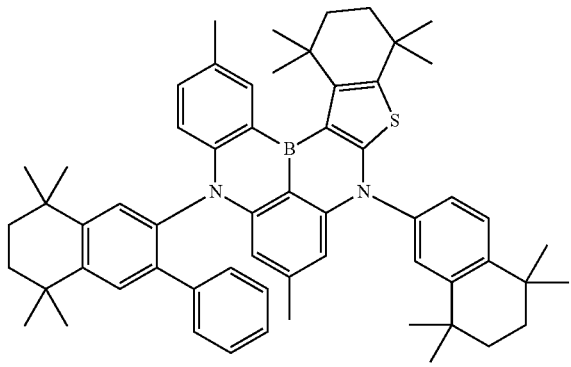
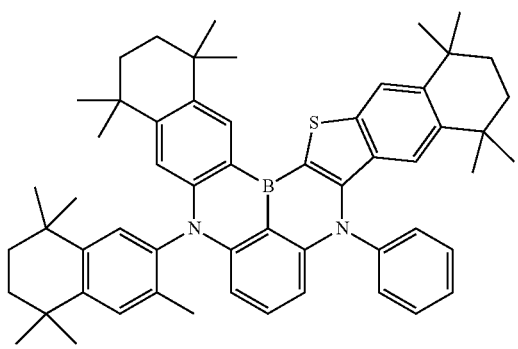
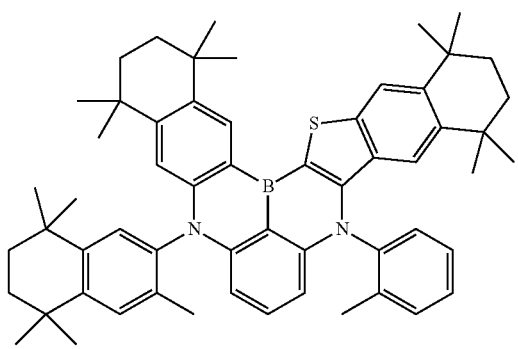
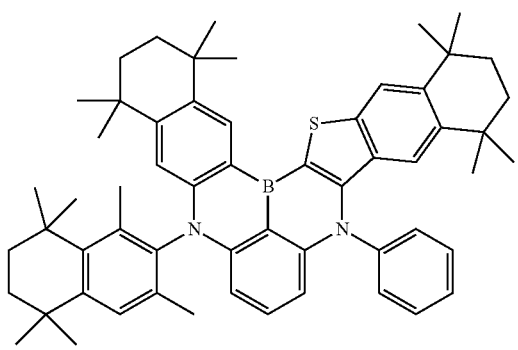
522
-continued
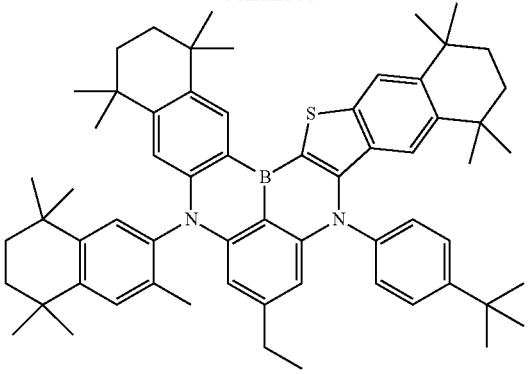
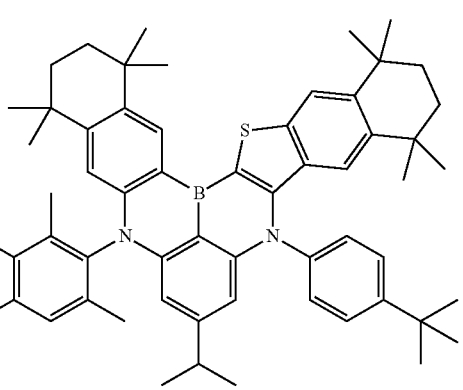
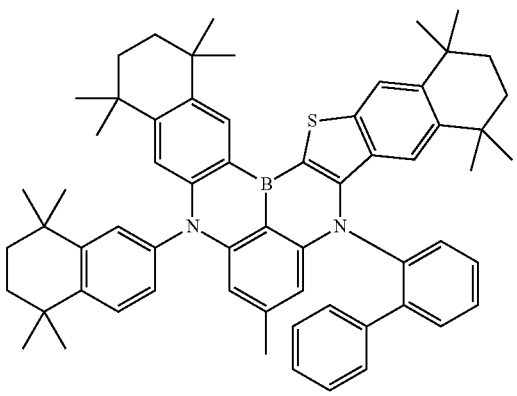
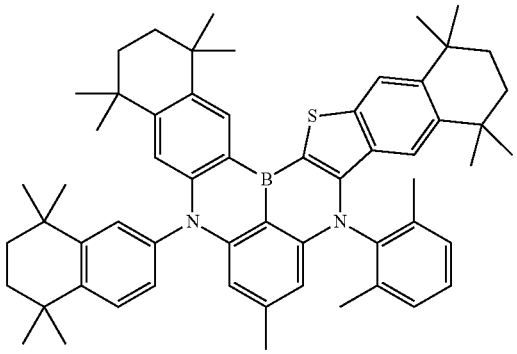

523
-continued
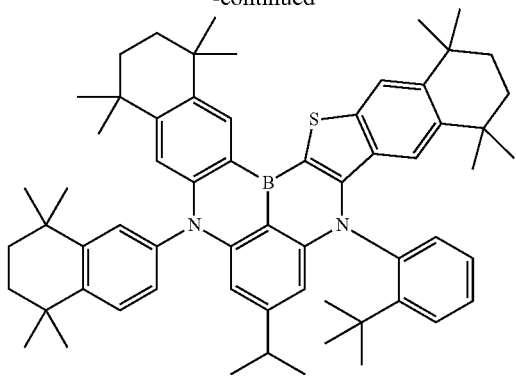
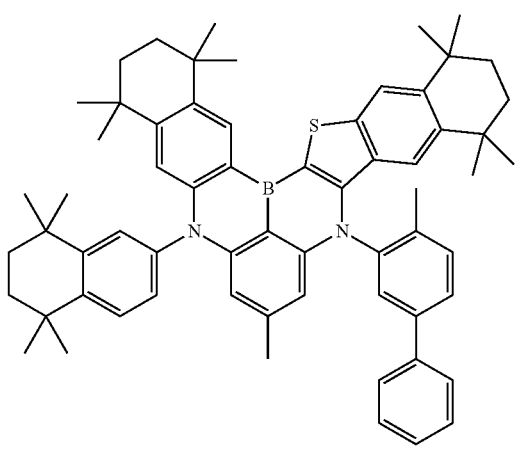
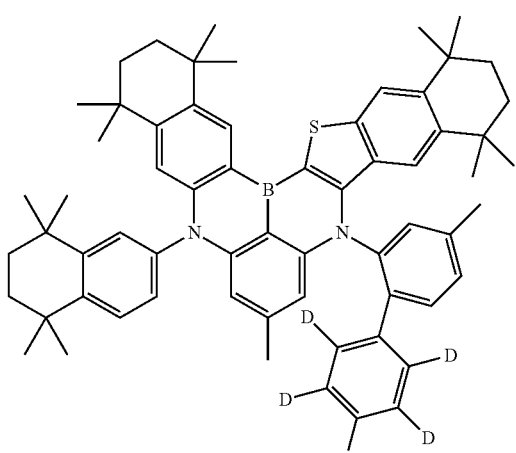
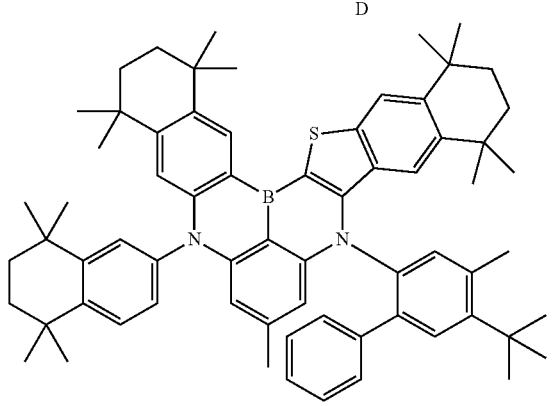
524
-continued
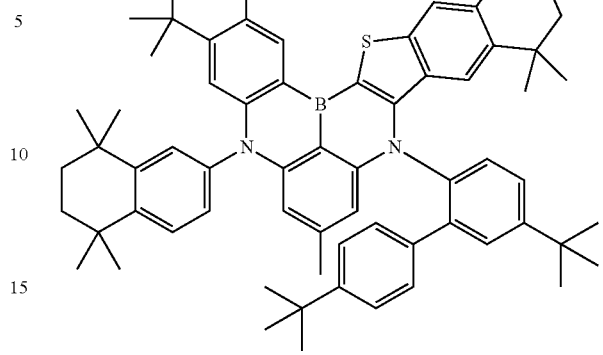
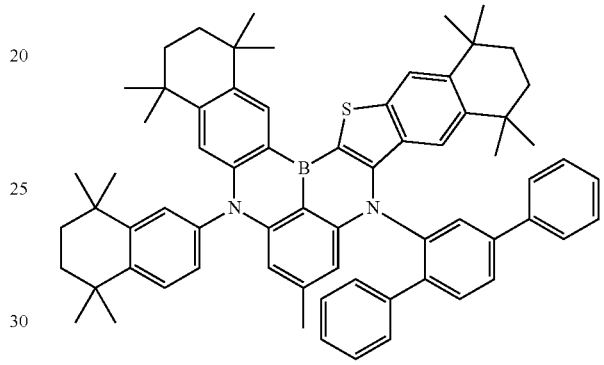
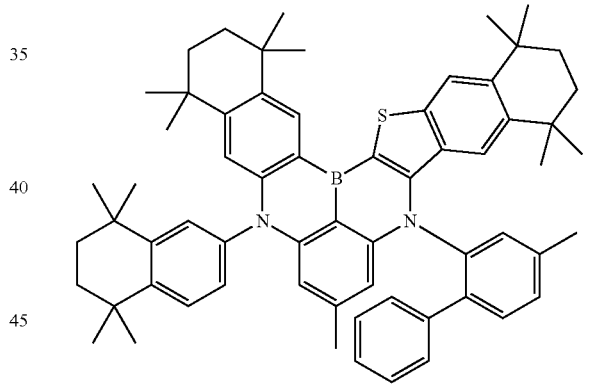
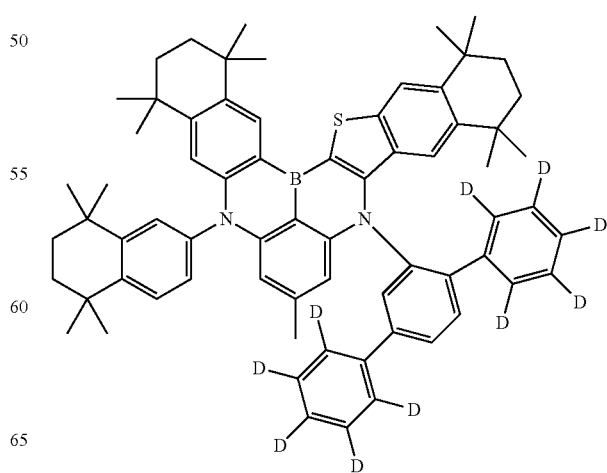

525
-continued
526
-continued
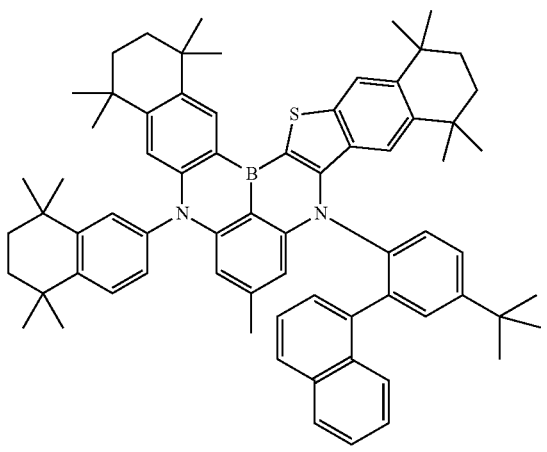
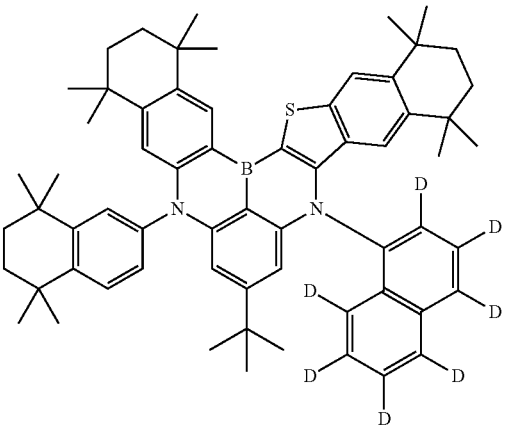
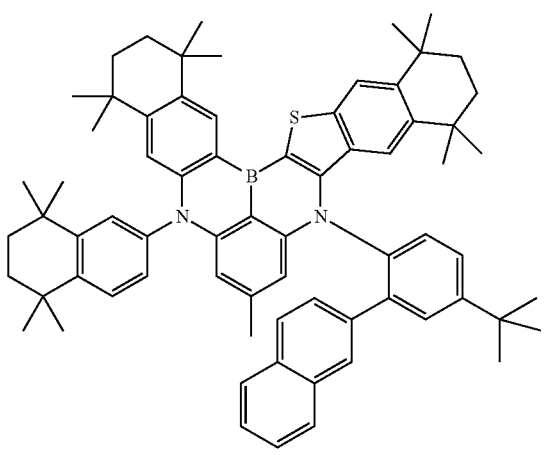
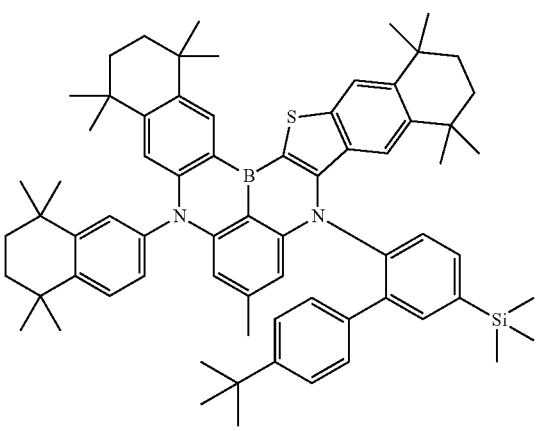
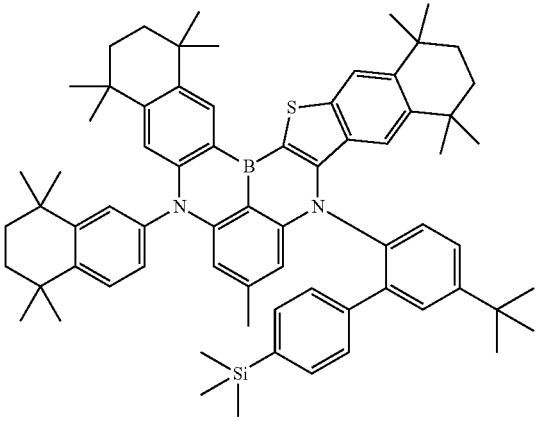
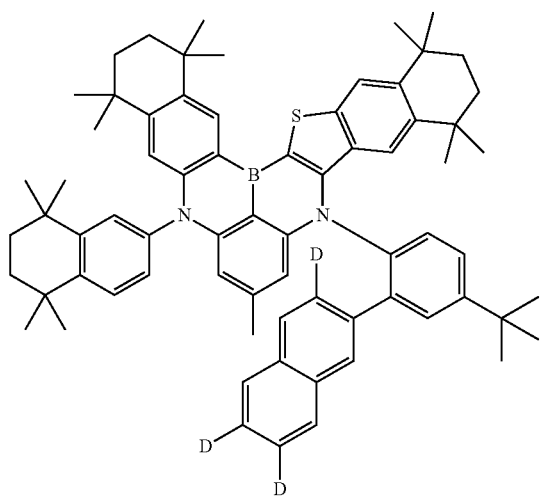
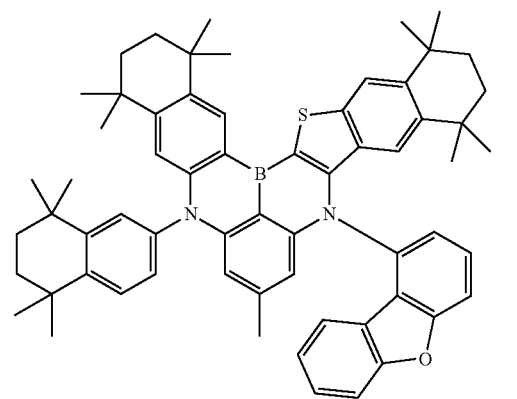

527
-continued
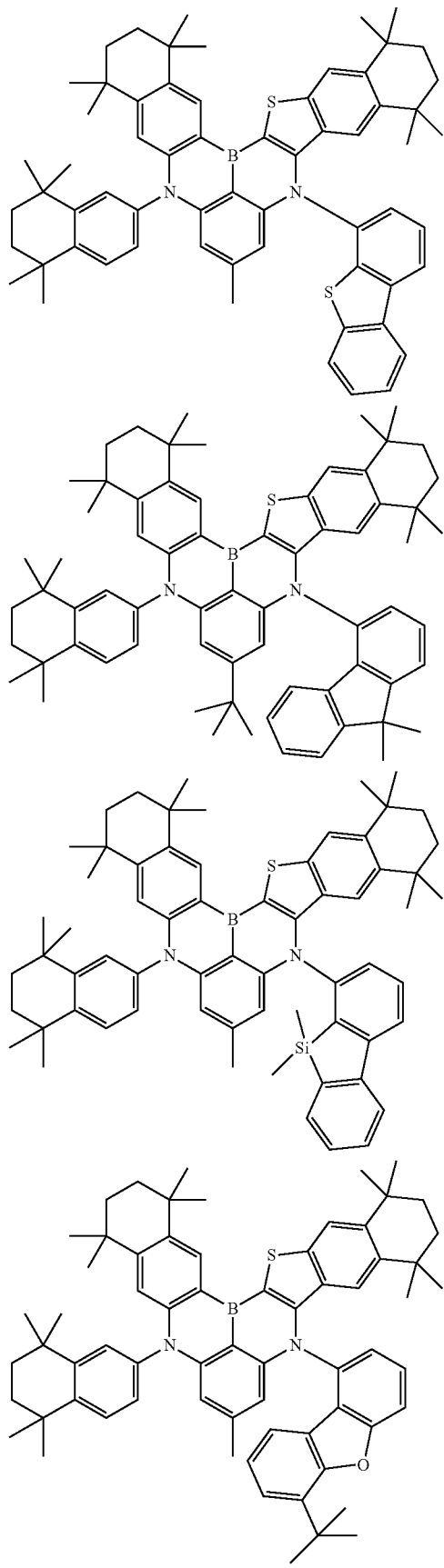
528
-continued
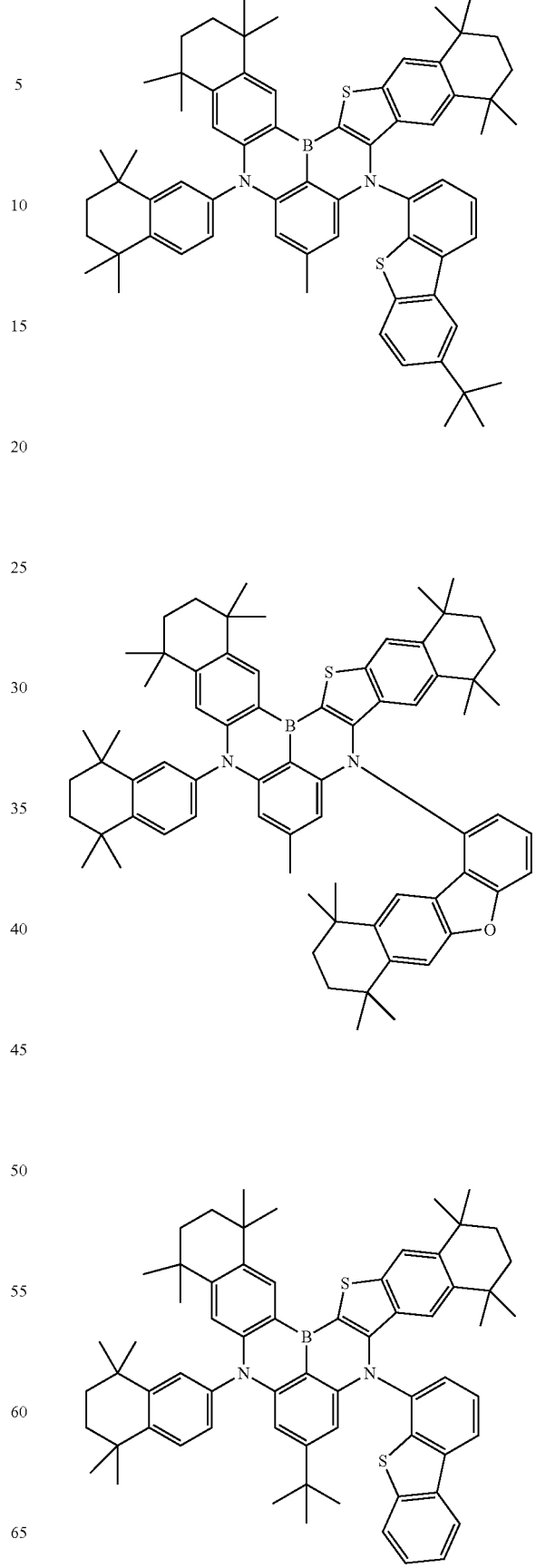

529
-continued
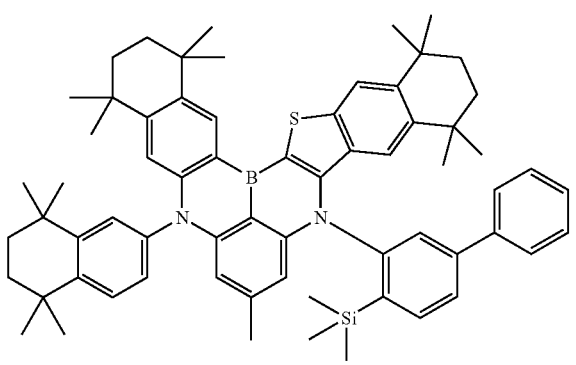
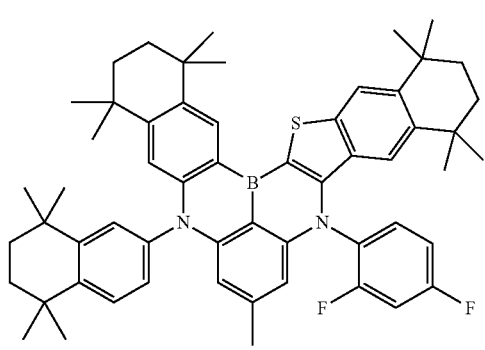
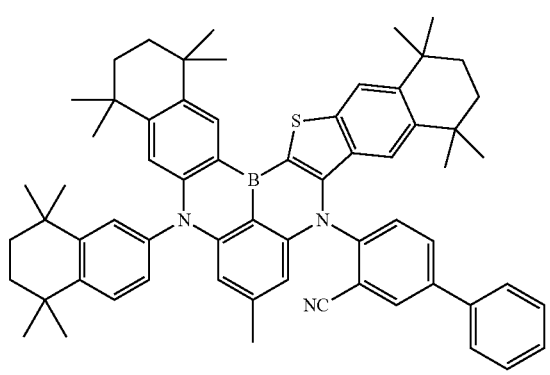
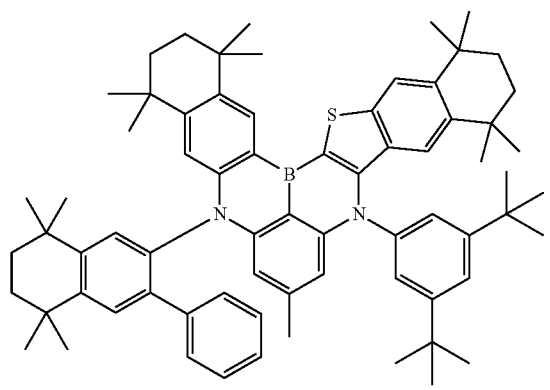
530
-continued
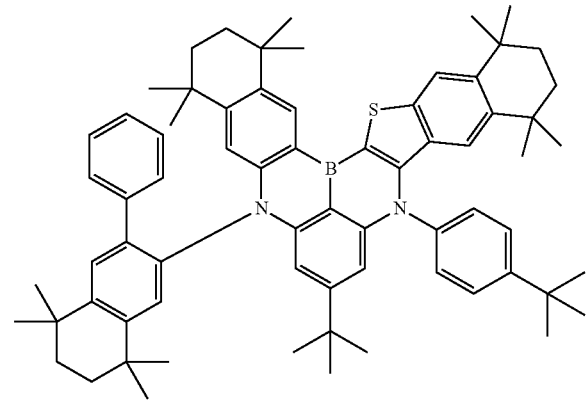
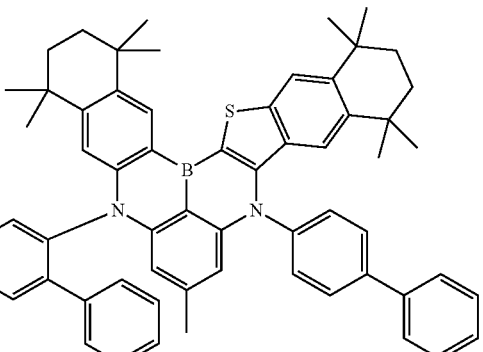
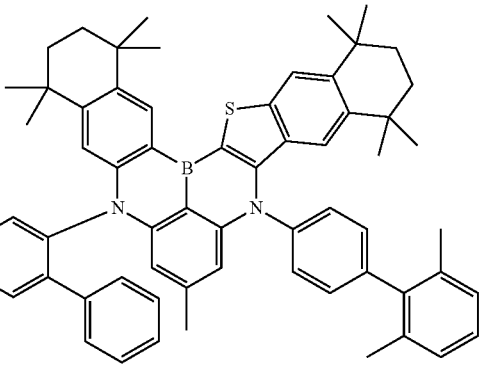
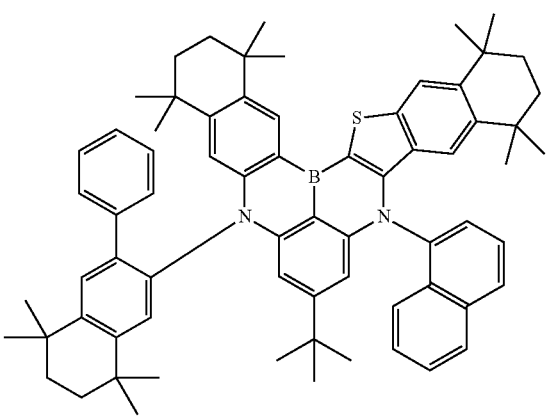

531
-continued
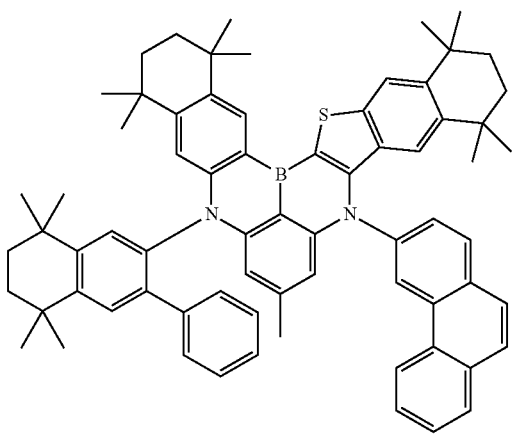
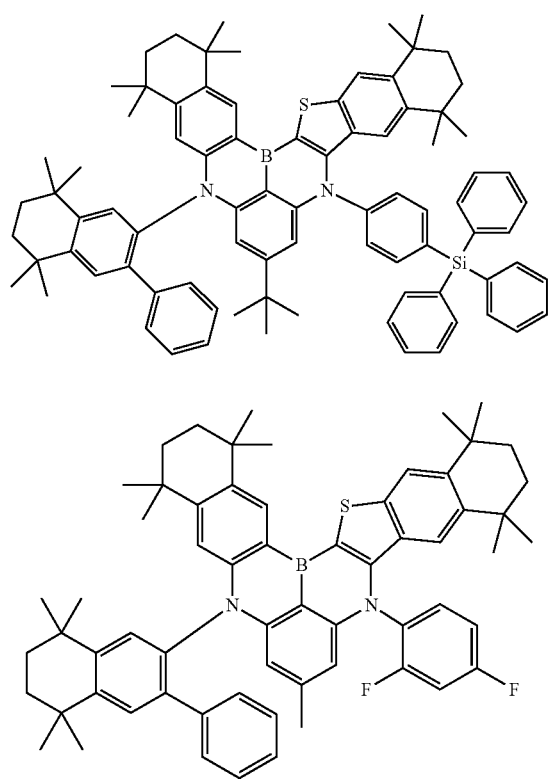
532
-continued
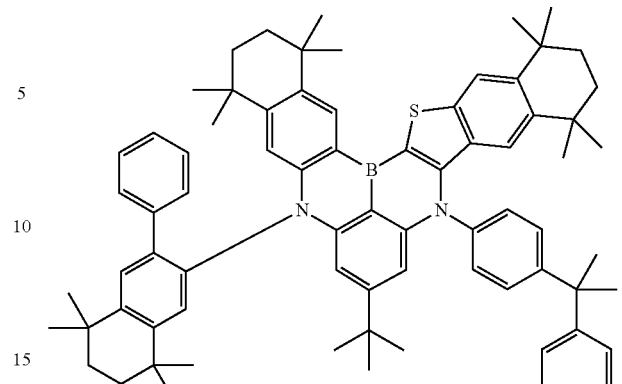
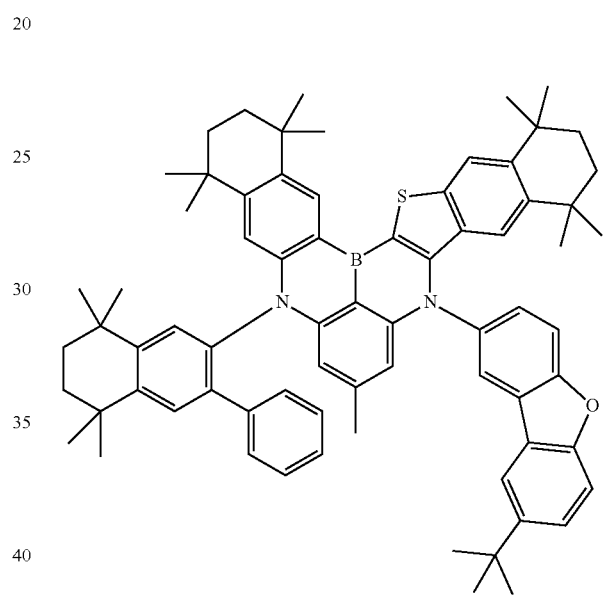
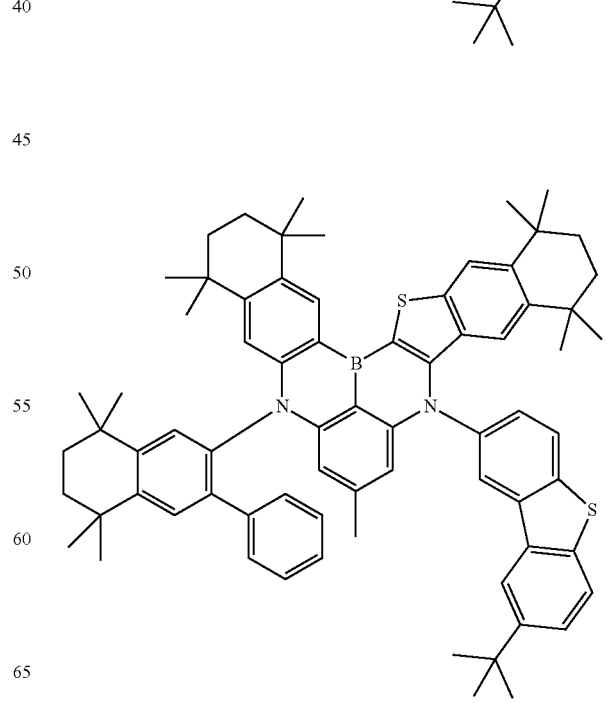

533
-continued
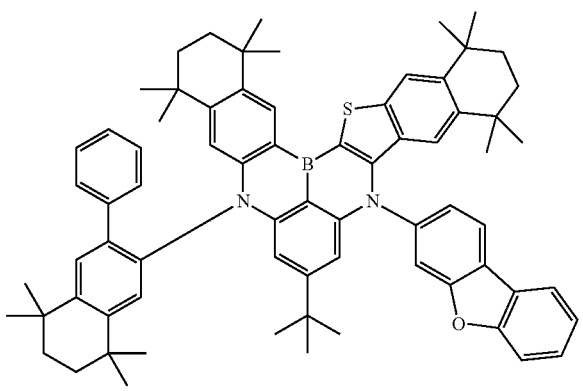
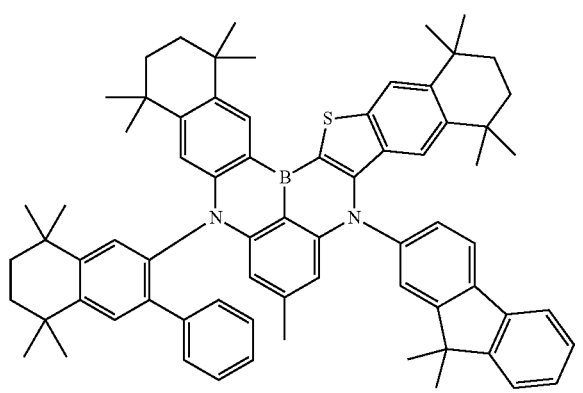
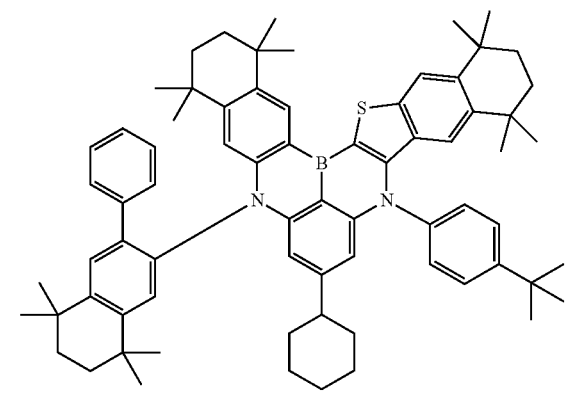
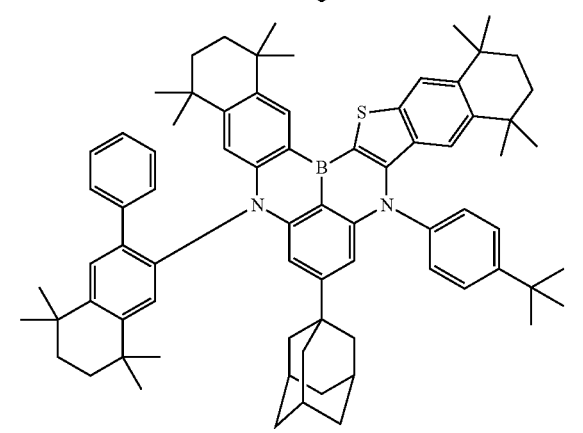
534
-continued
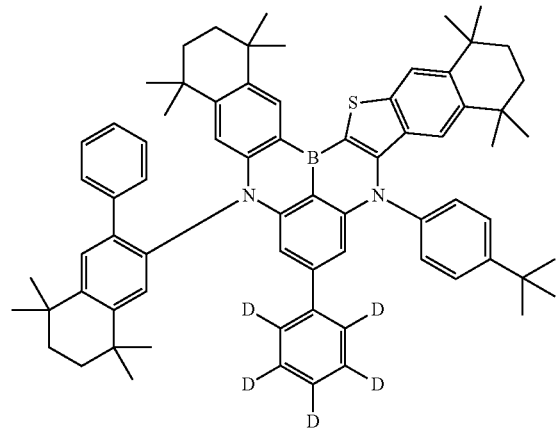
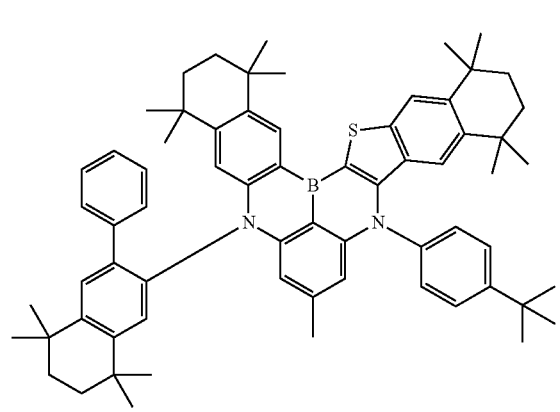
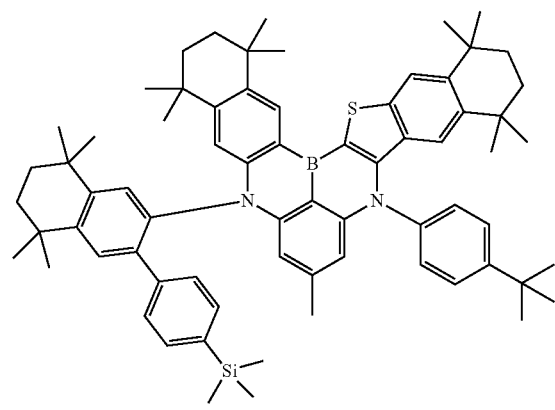
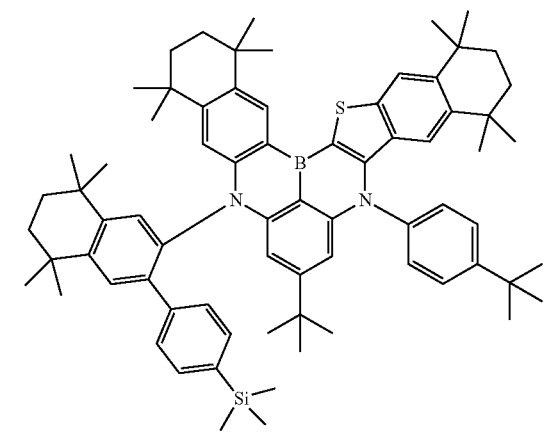

535 -continued
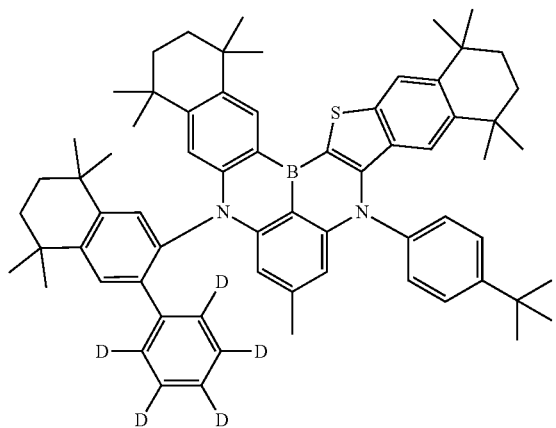
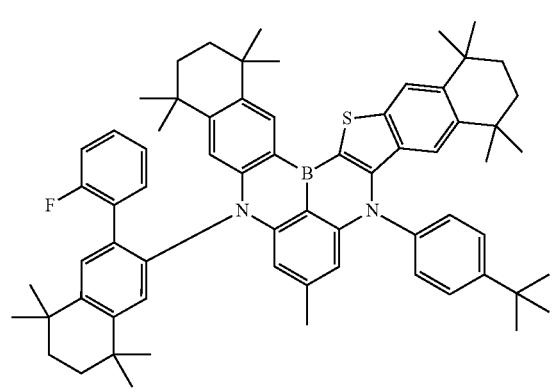
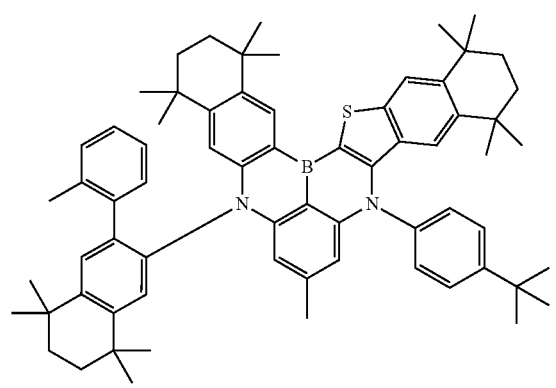
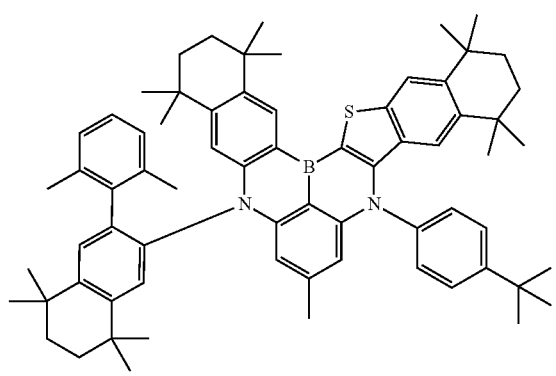
536 -continued
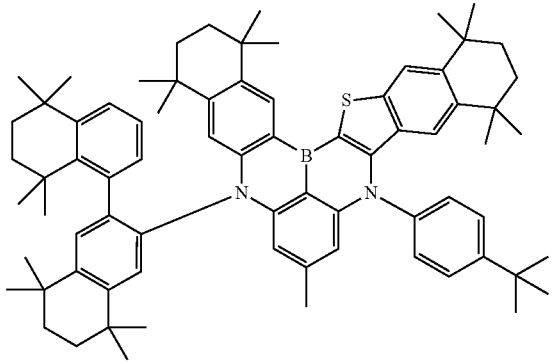
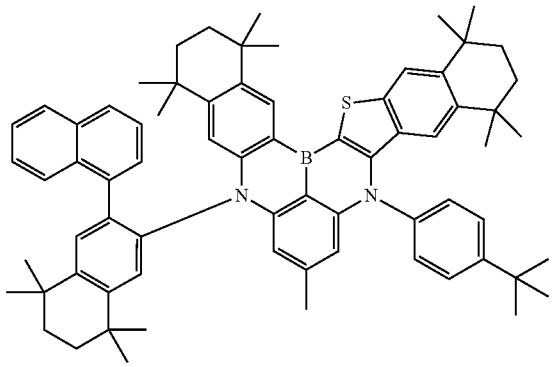
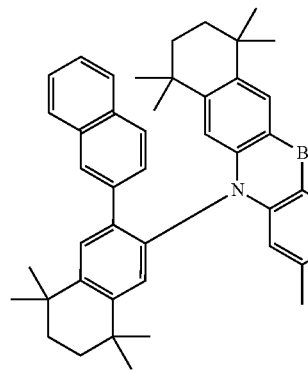
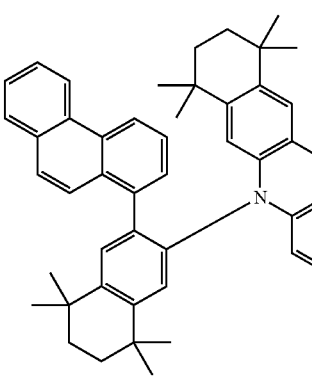

537
-continued
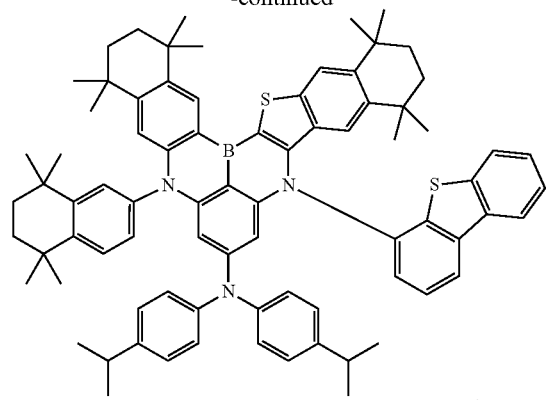
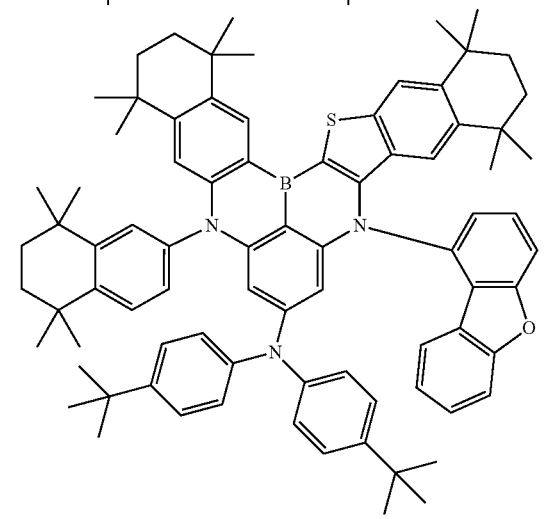
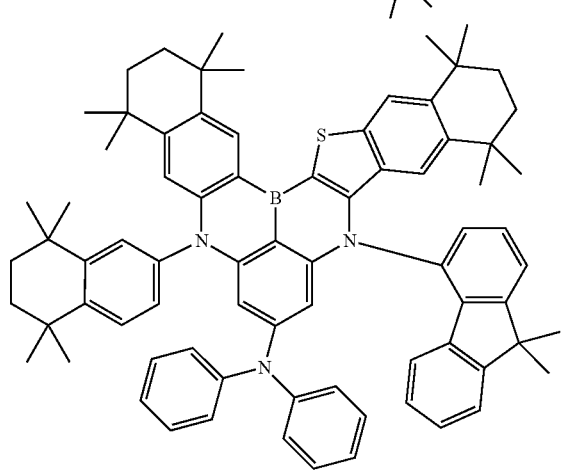
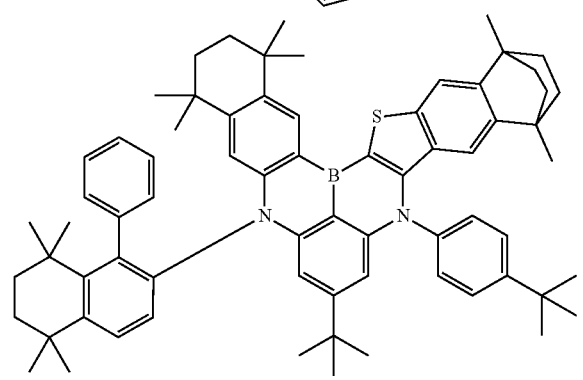
538
-continued
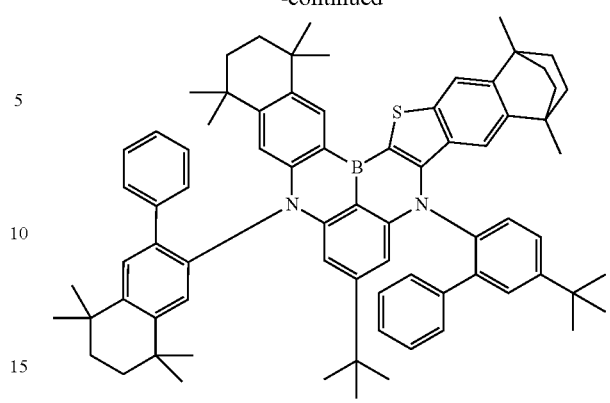
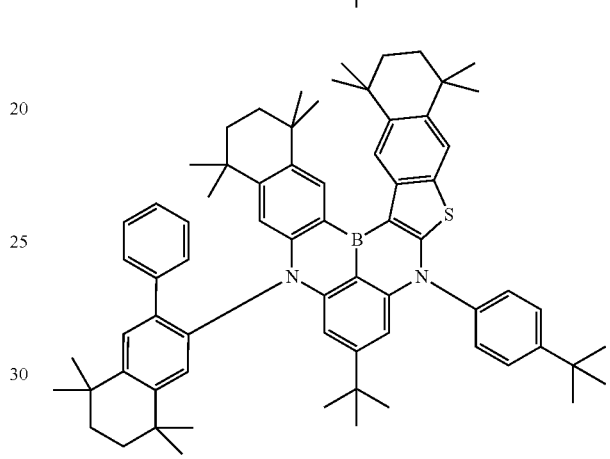
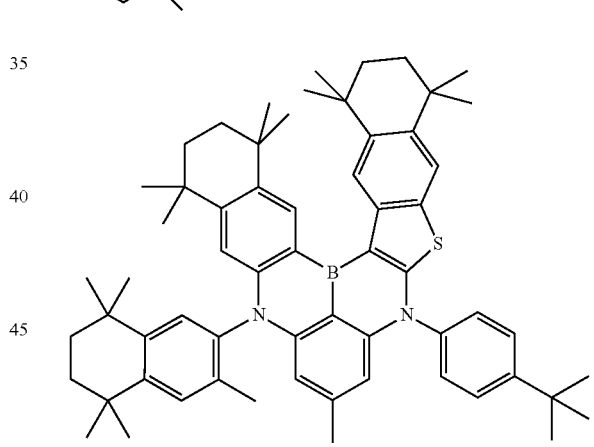
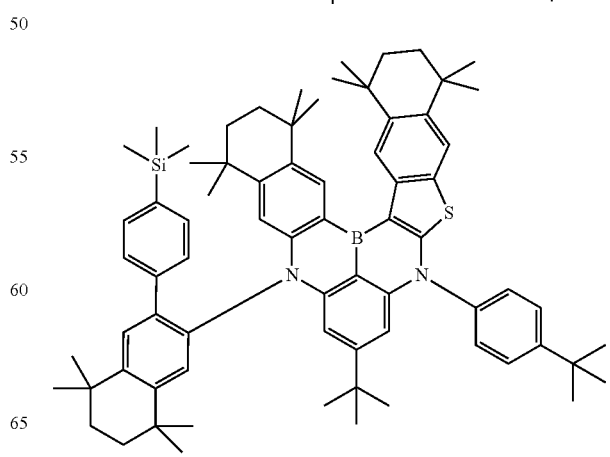

539
-continued
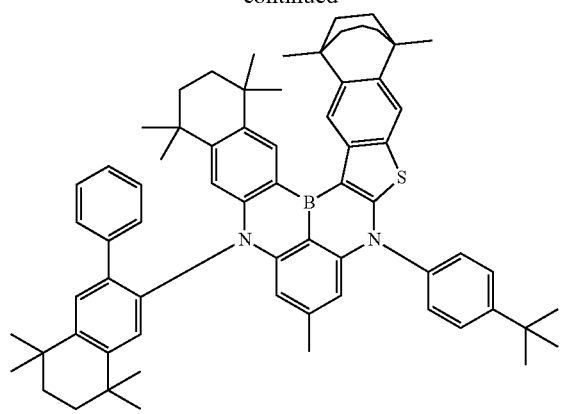
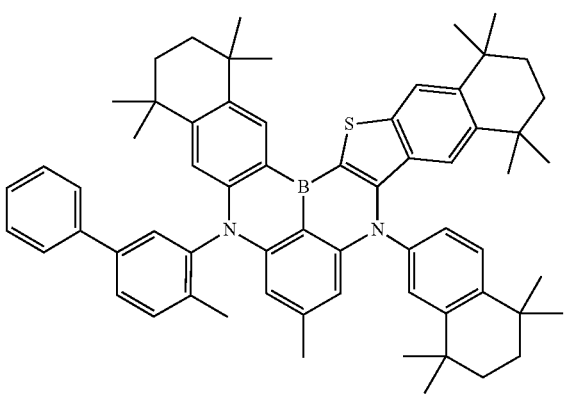
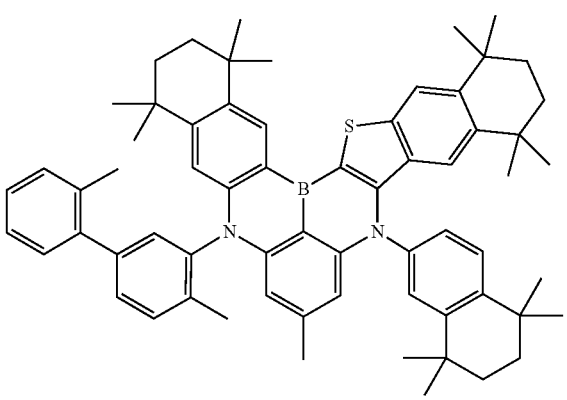
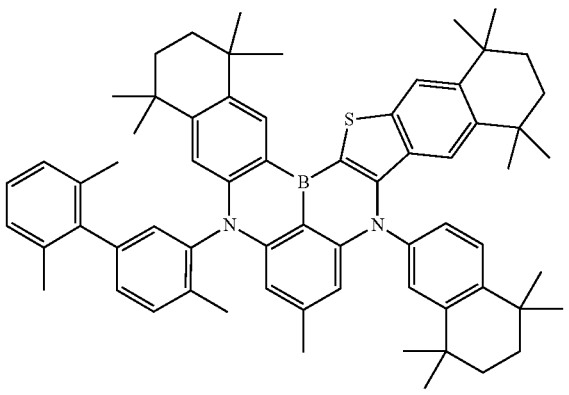
540
-continued
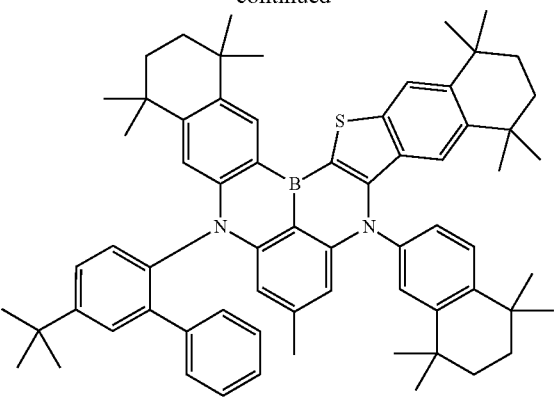
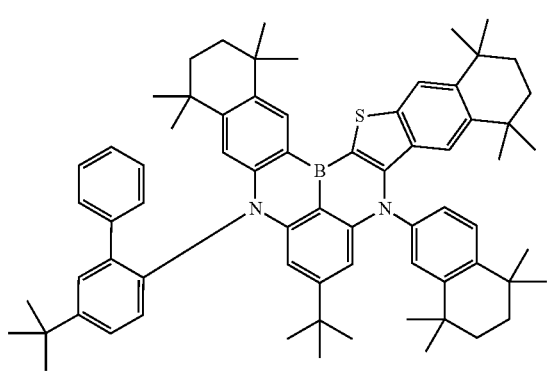
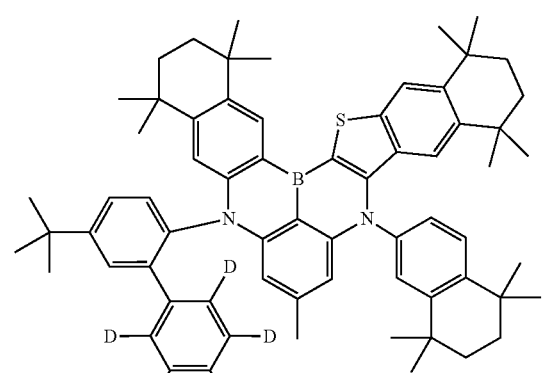
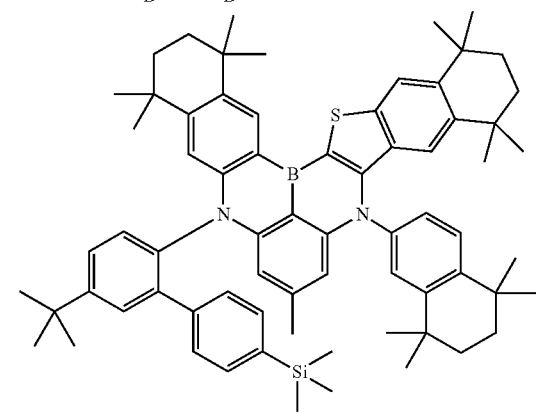

541
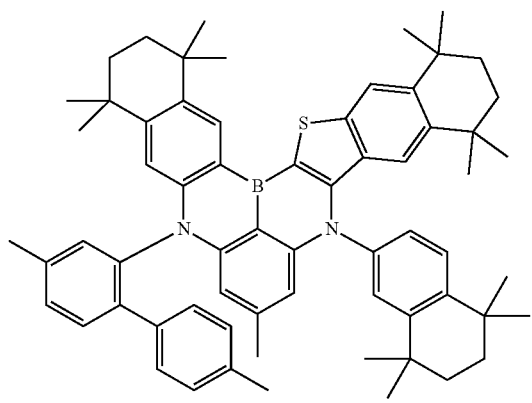
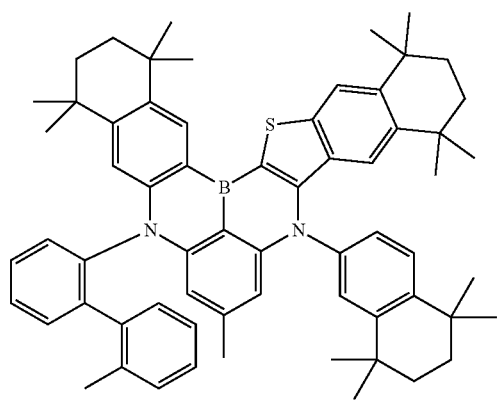
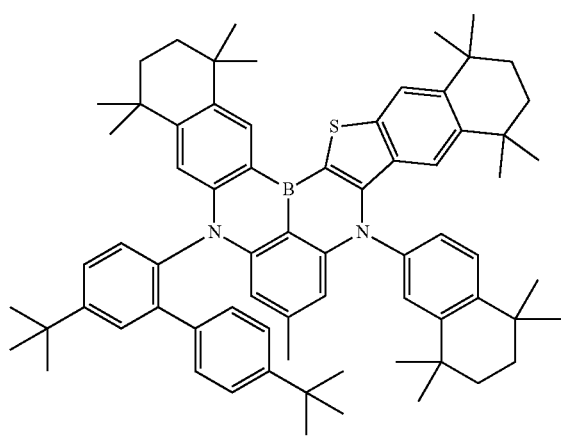
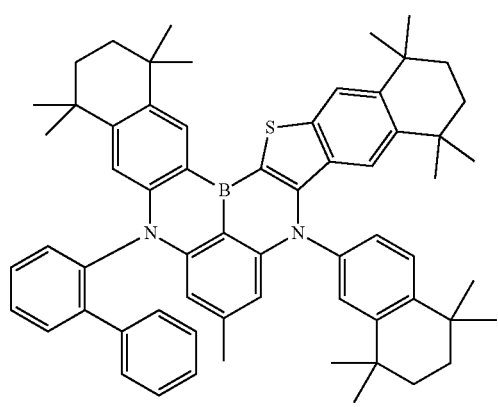
542
-continued
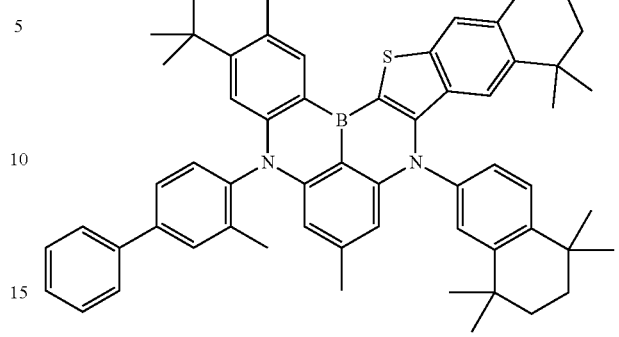
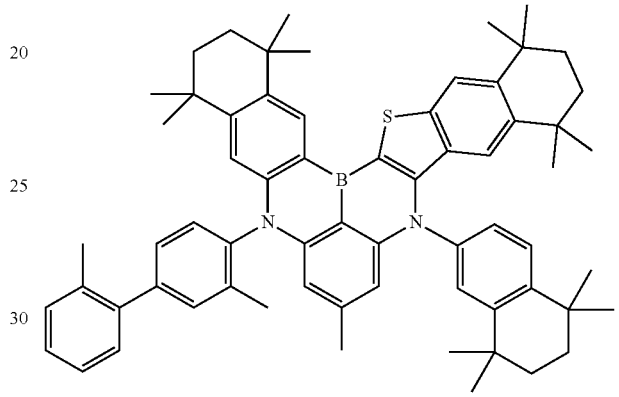
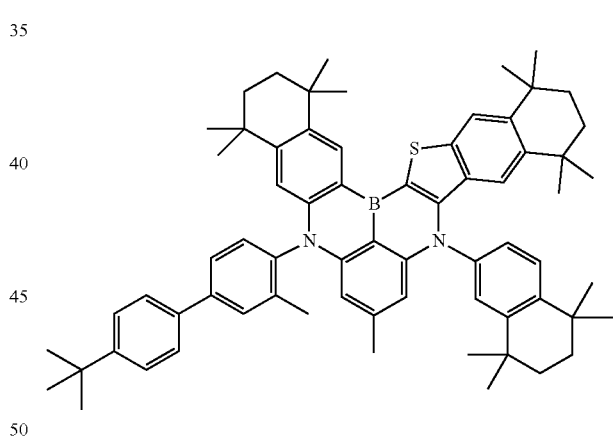
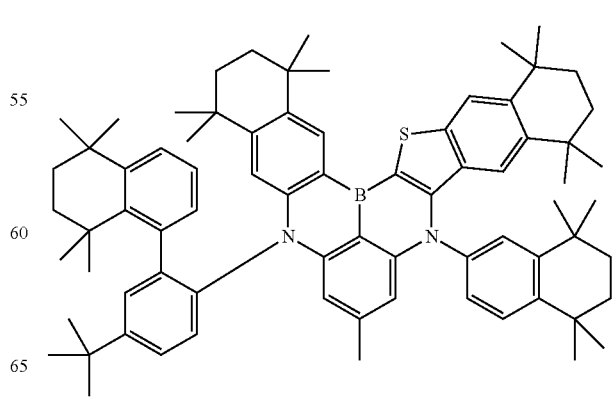

543
-continued
544
-continued
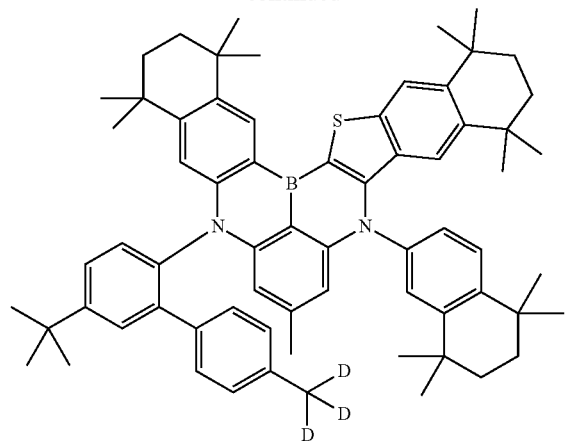
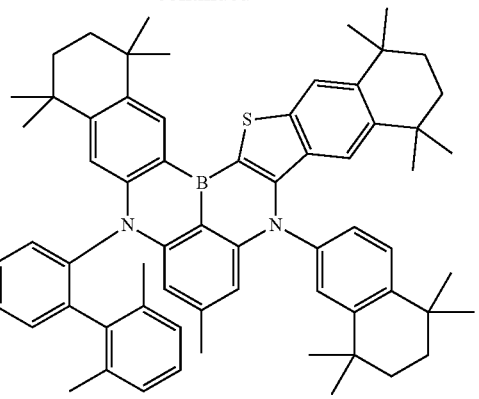
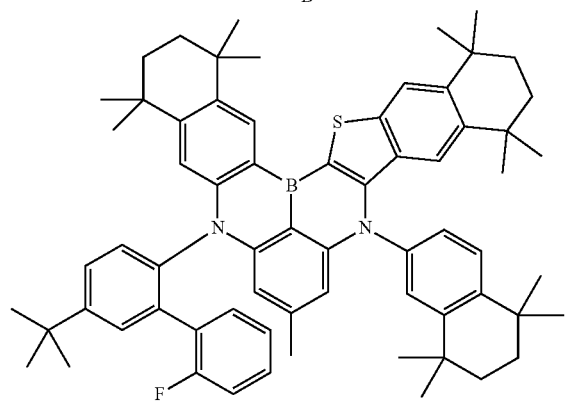
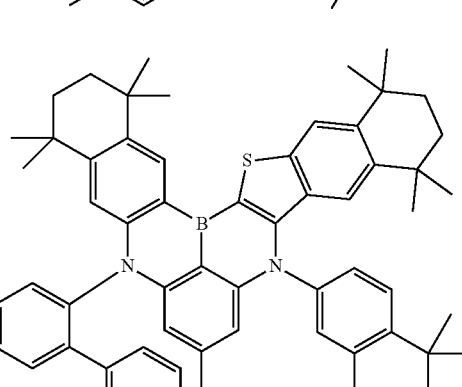
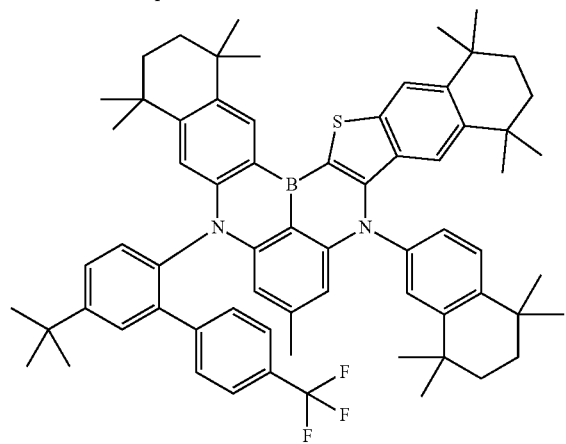
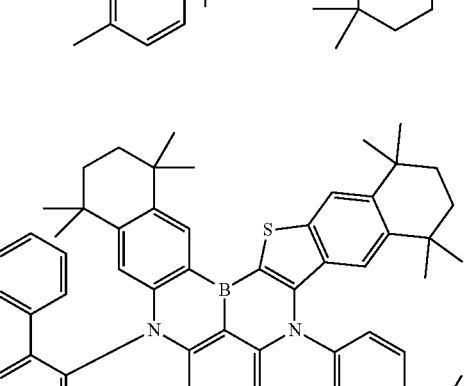
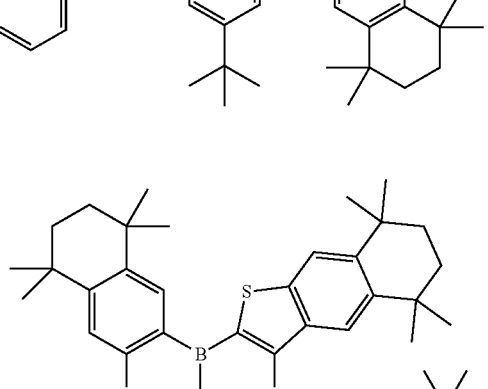
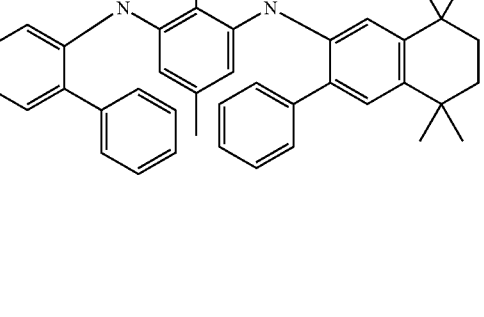

545
-continued
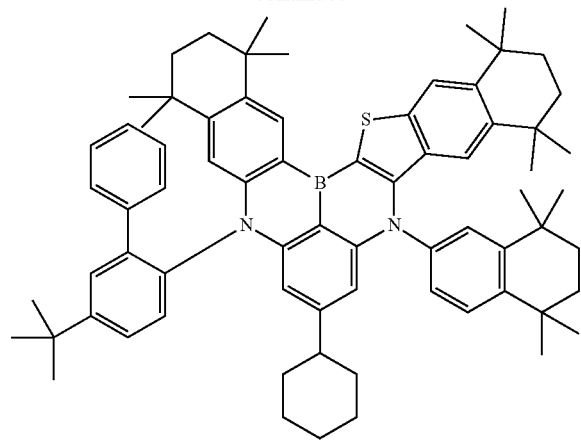
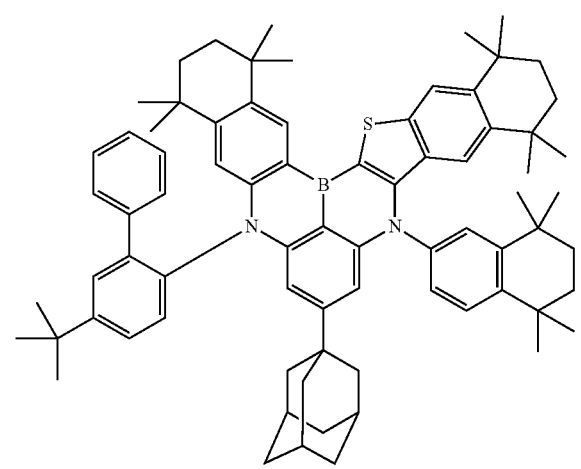
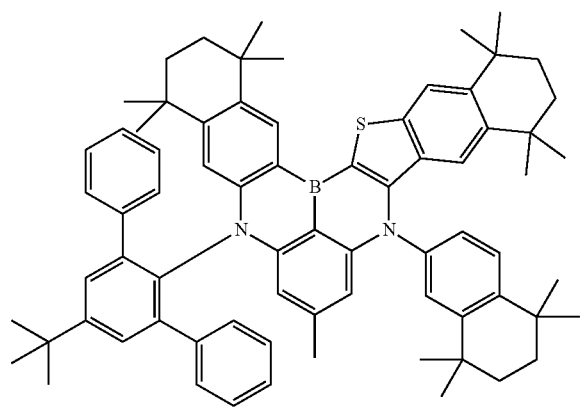
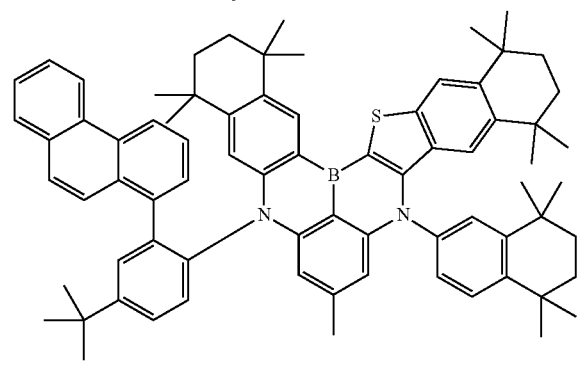
546
-continued
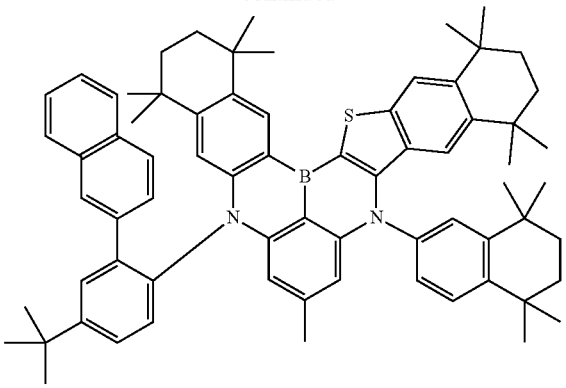
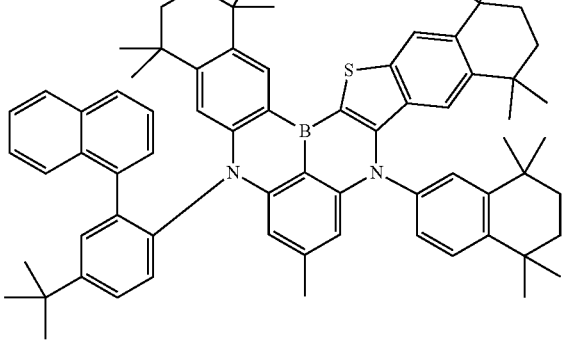
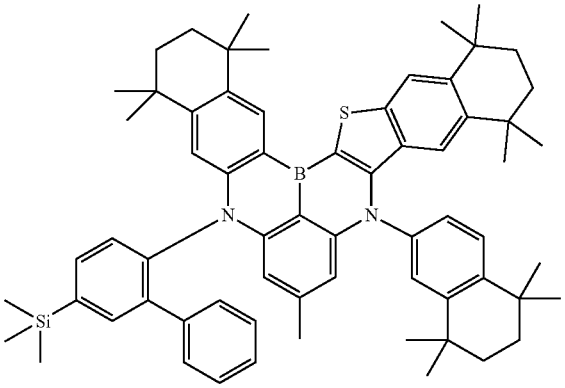
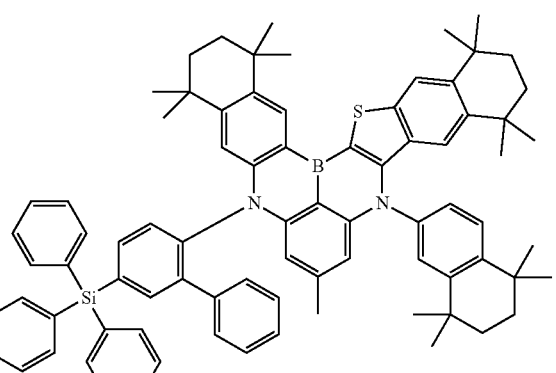

547
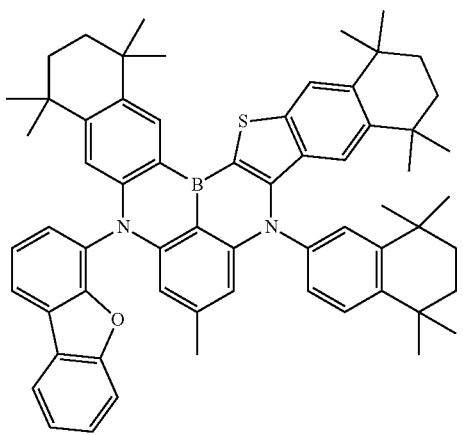
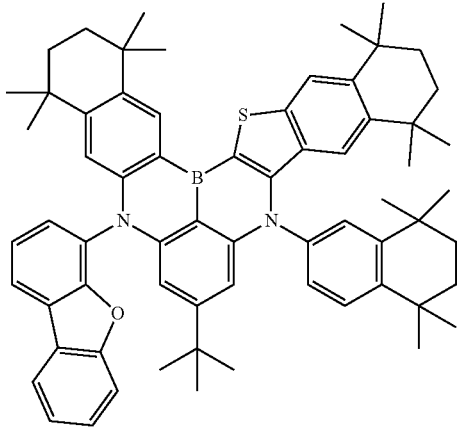
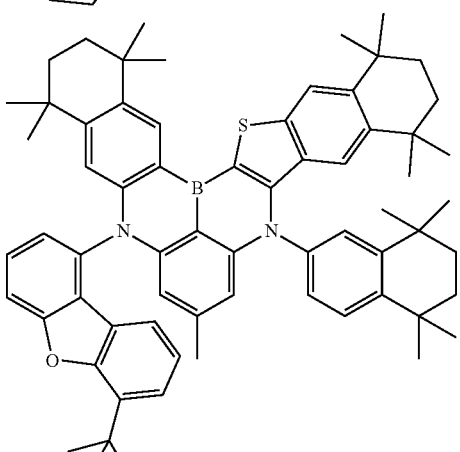
548
-continued
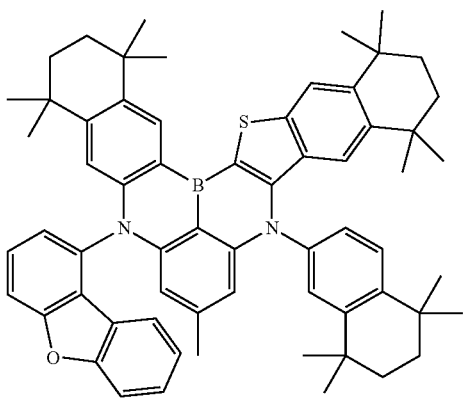
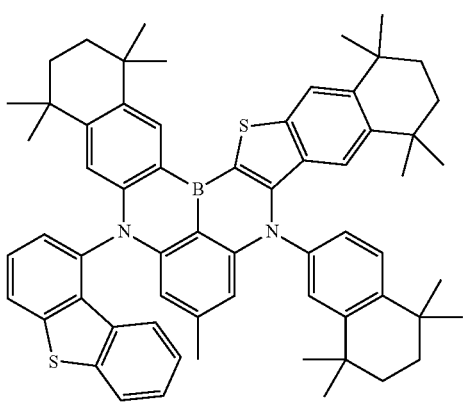
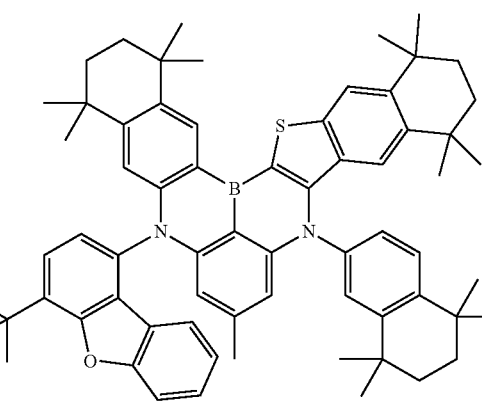

549
-continued
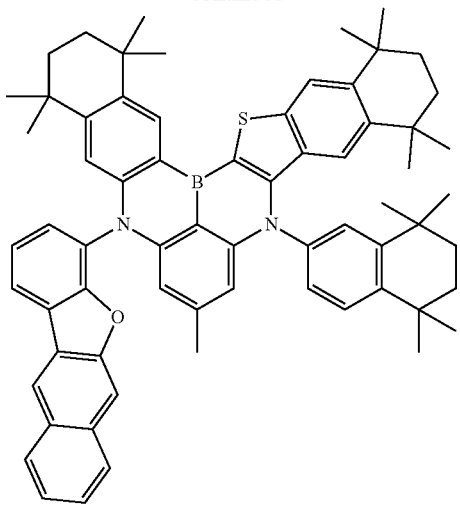
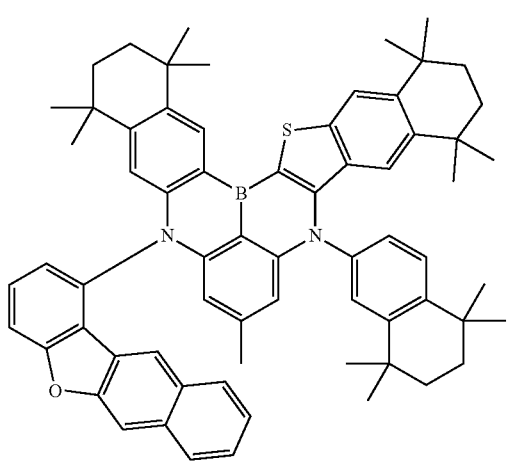
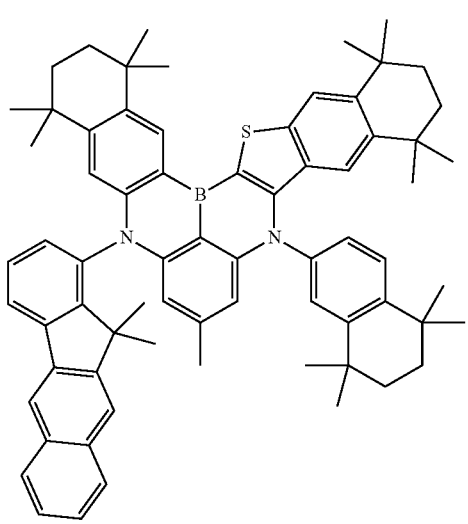
550
-continued
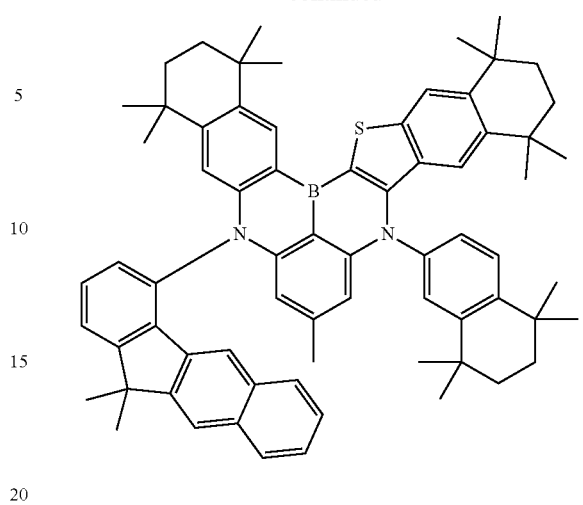
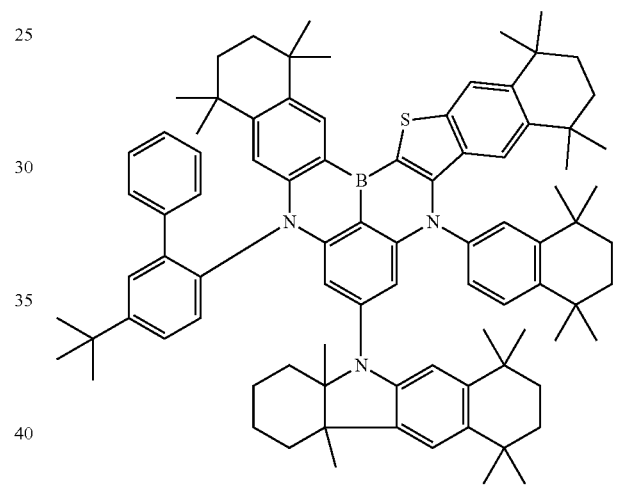
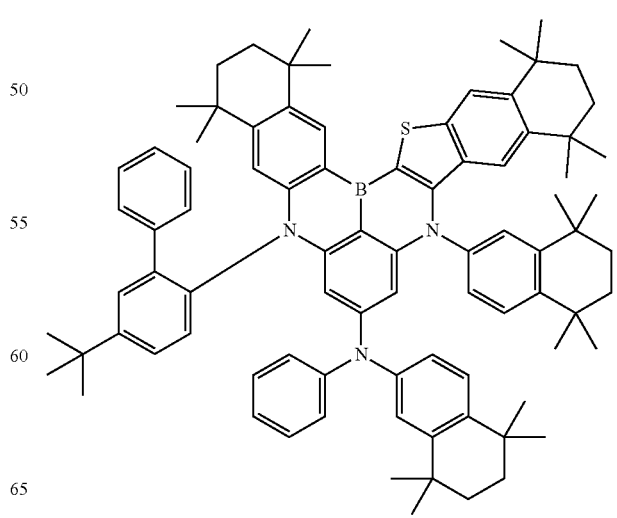

551
-continued
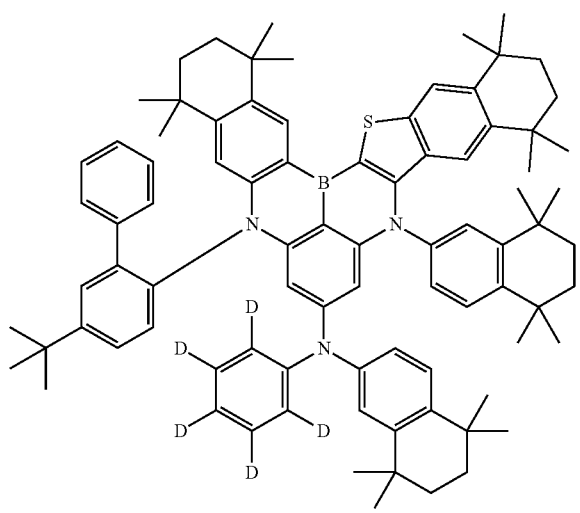
552
-continued
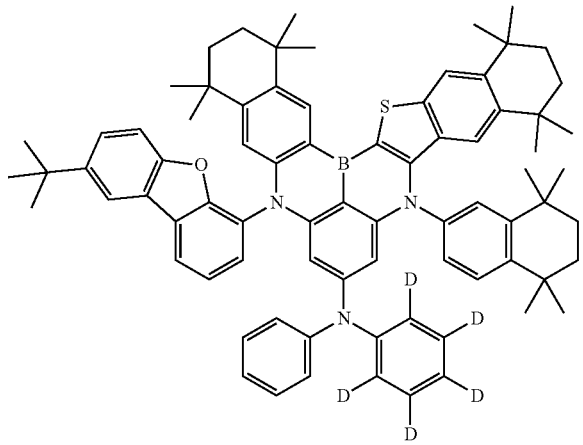
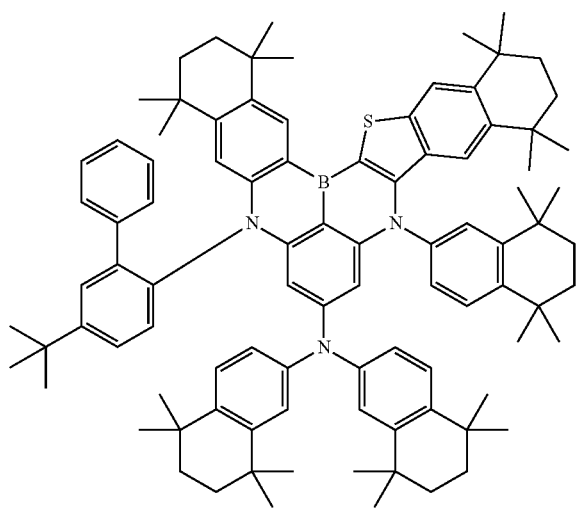
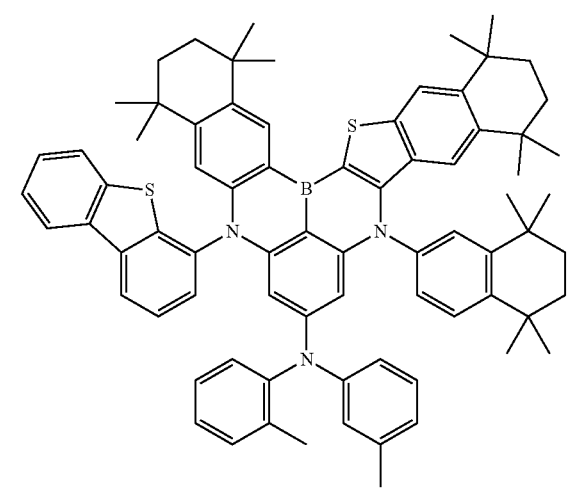
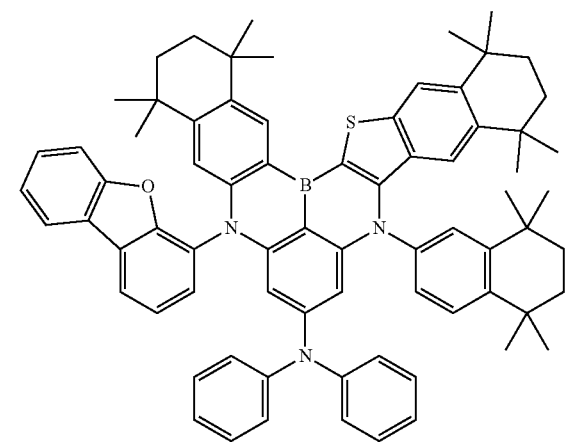
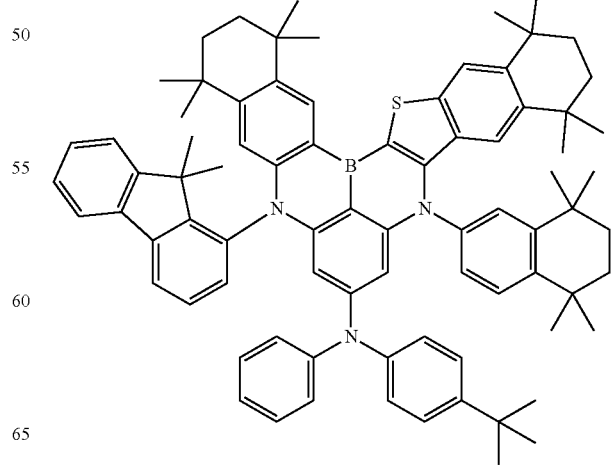

553
-continued
554
-continued
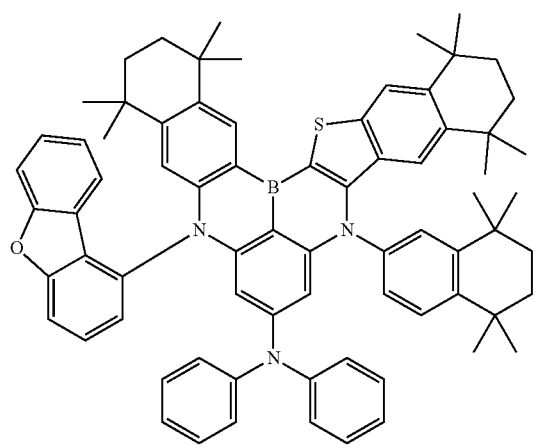
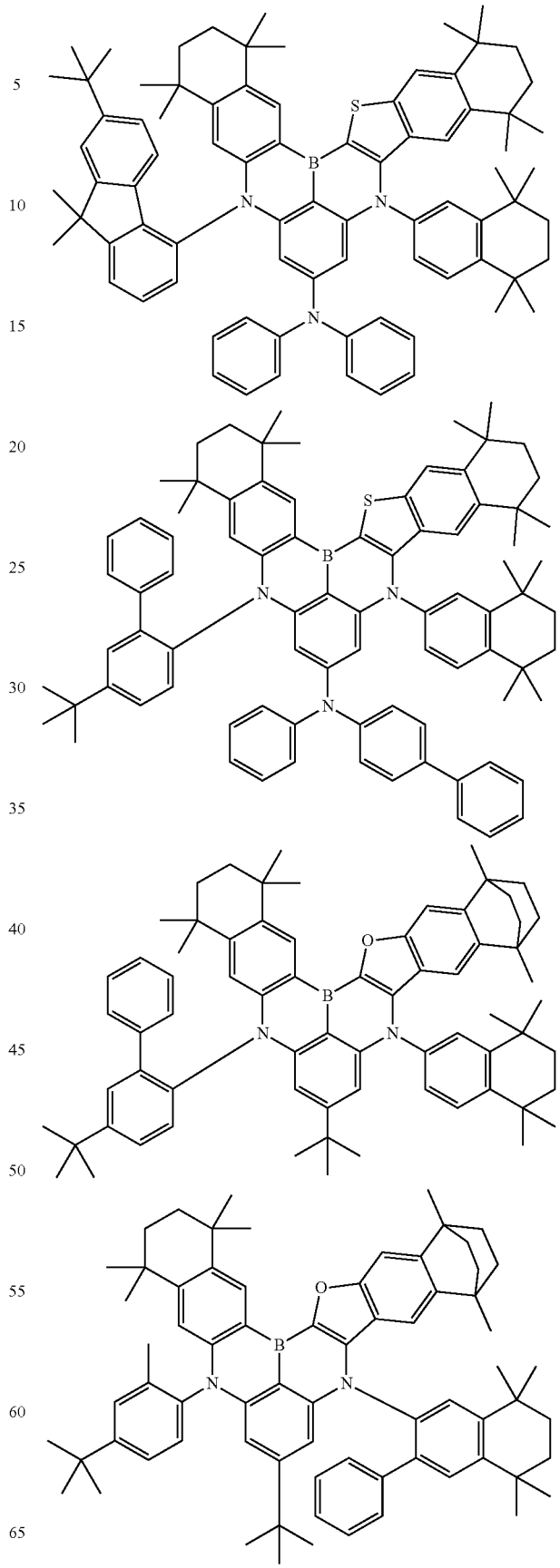

555
-continued
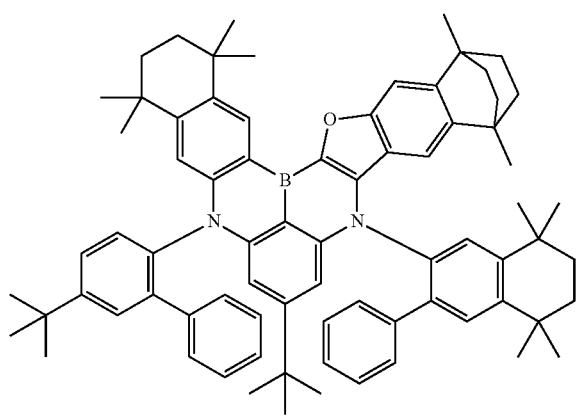
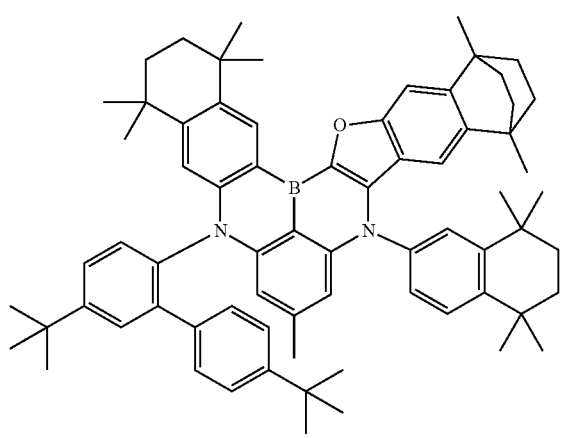
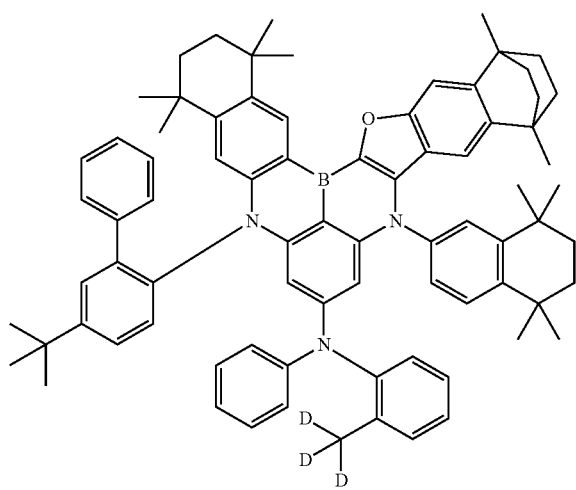
556
-continued
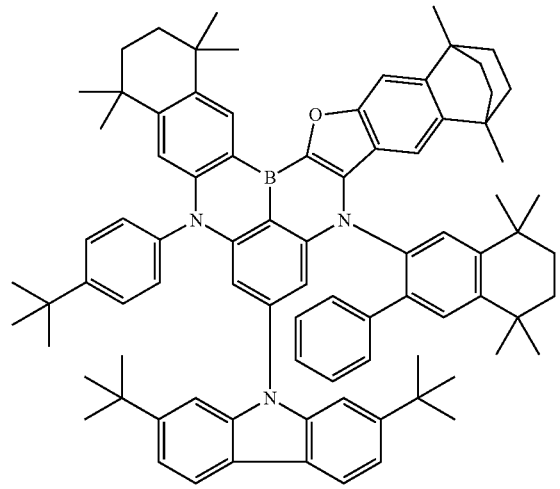
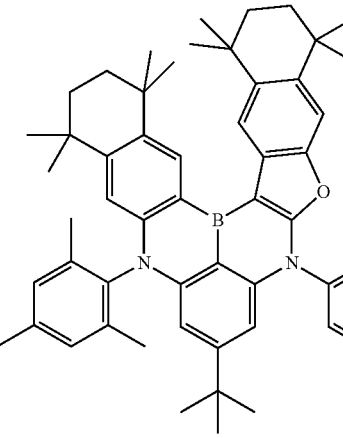
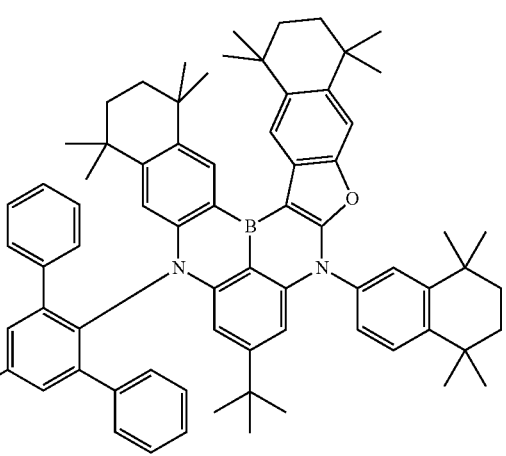

557
-continued
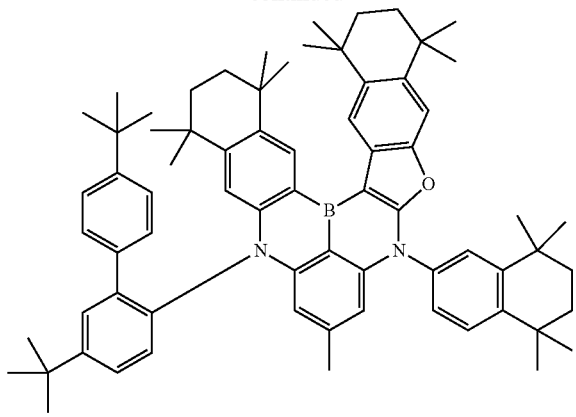
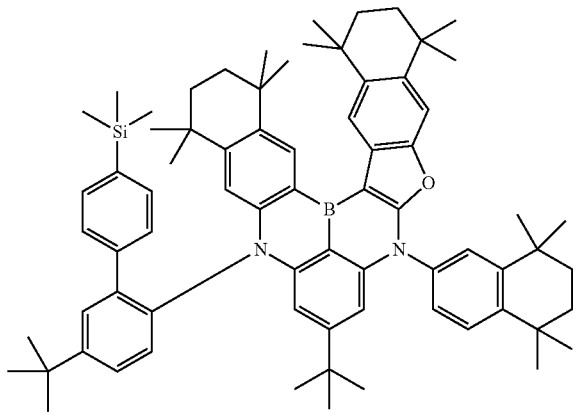
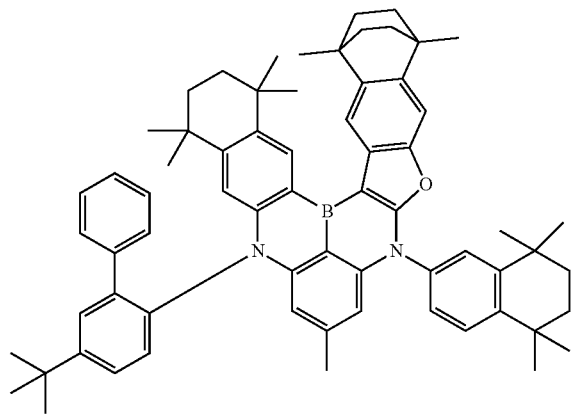
558
-continued
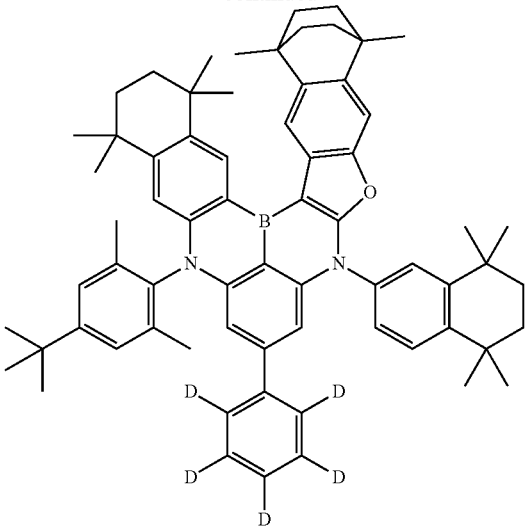
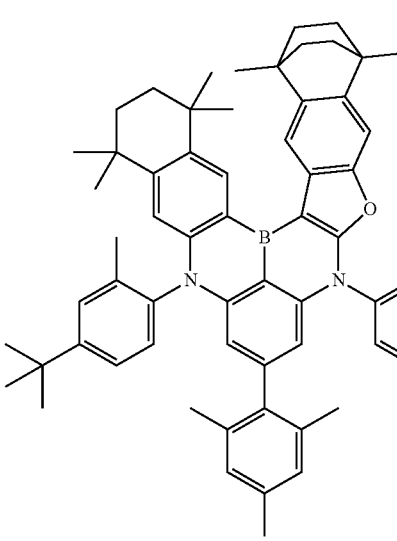
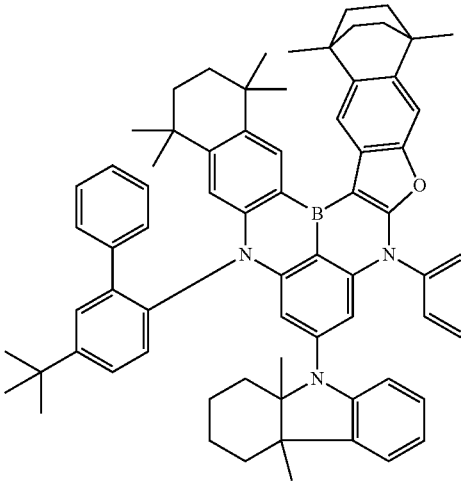

559
-continued
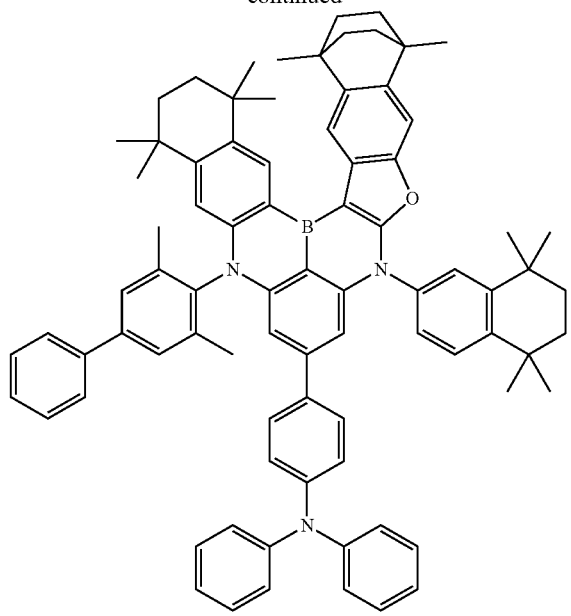
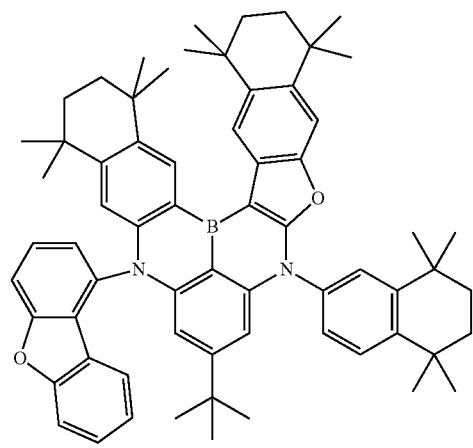
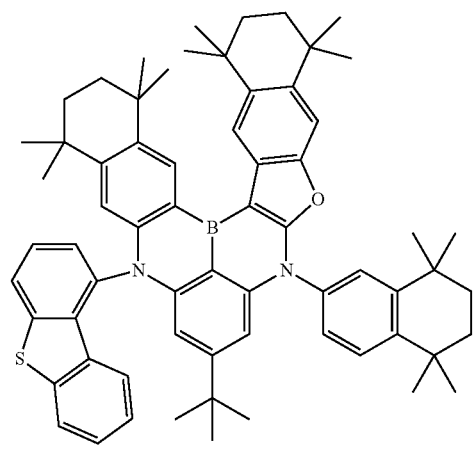
560
-continued
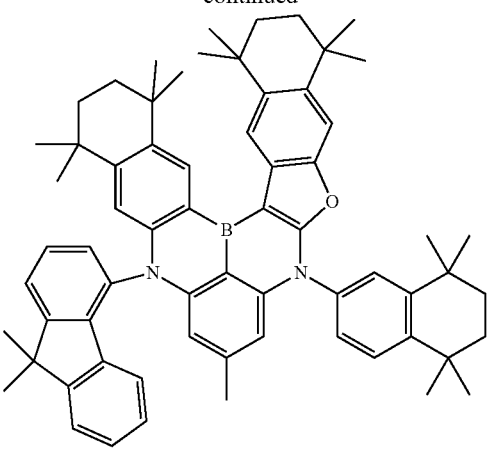
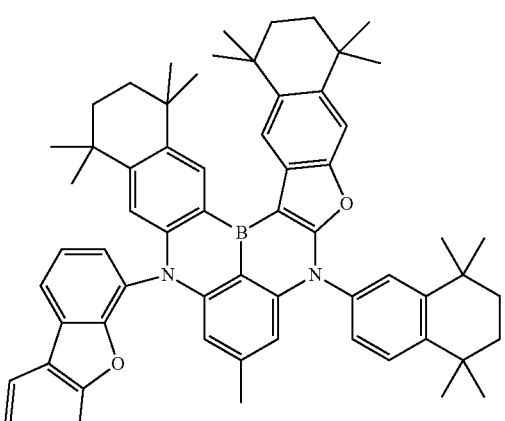
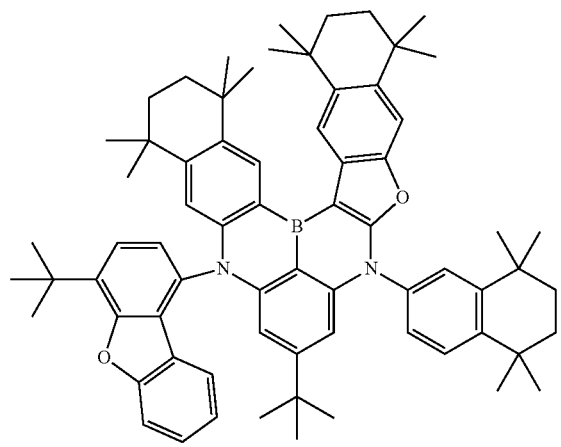

561
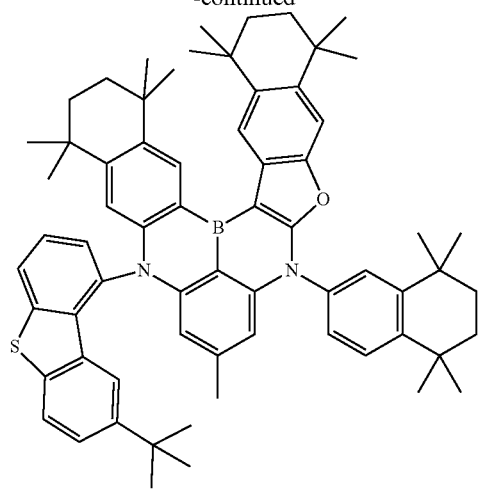
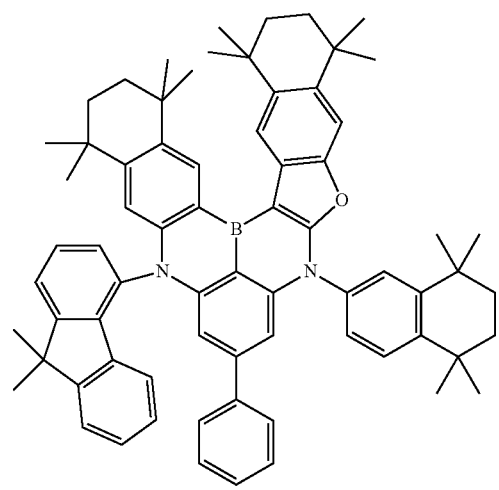
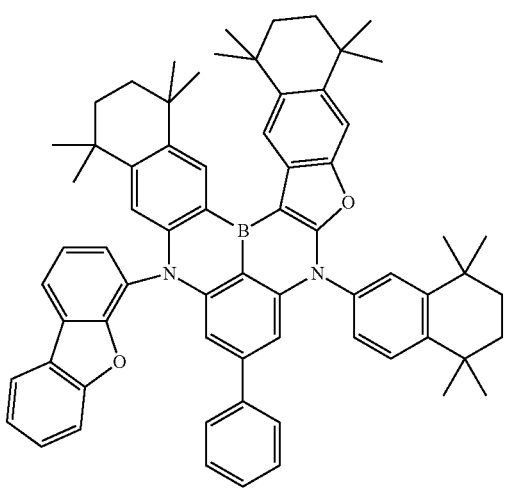 [SMILES: CC1(C)CCC(C)(C)c2cc(N3c4cc(-c5ccccc5)cc5c4B(c4cc6c(cc4N5c4cccc5c4oc4ccccc45)C(C)(C)CCC6(C)C)c4c3oc3cc5c(cc43)C(C)(C)CCC5(C)C)ccc21]
562
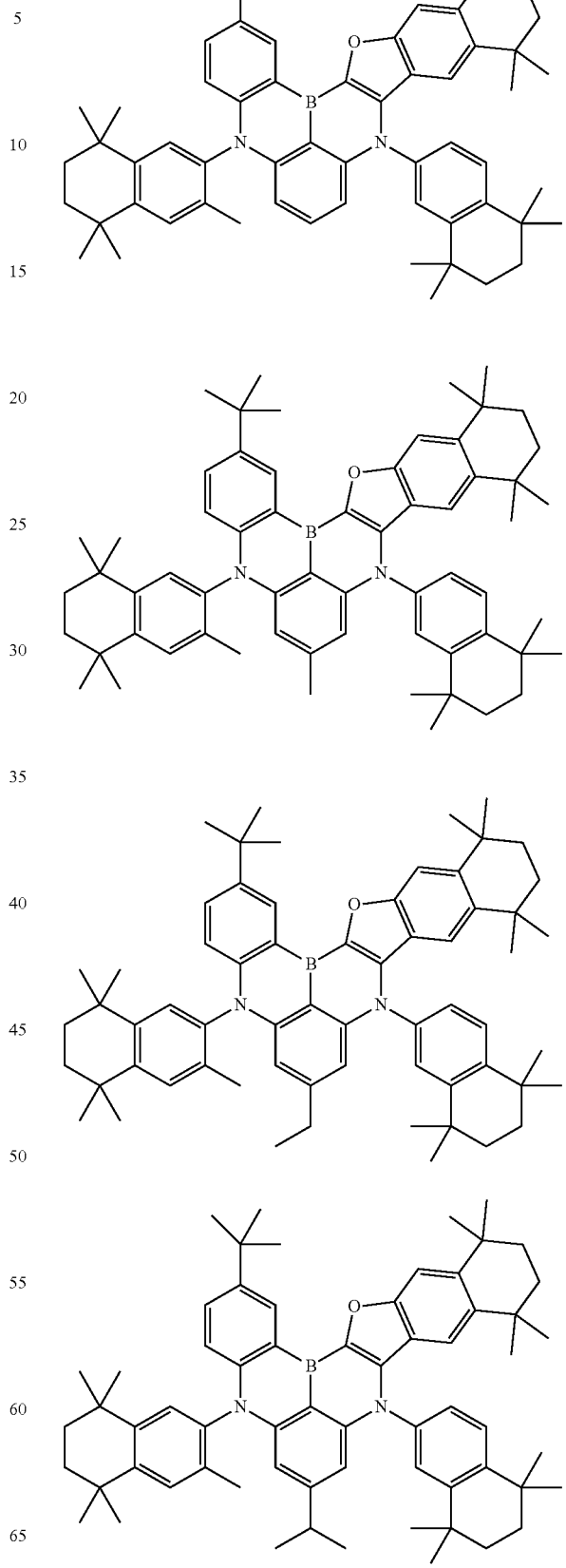

563
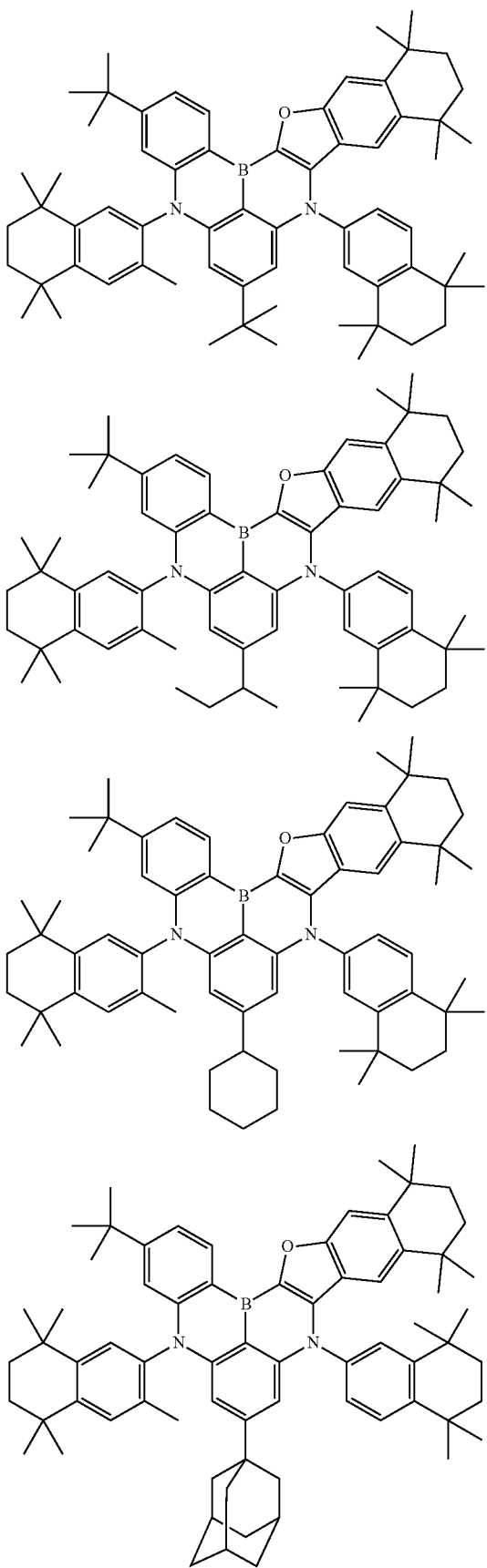
564
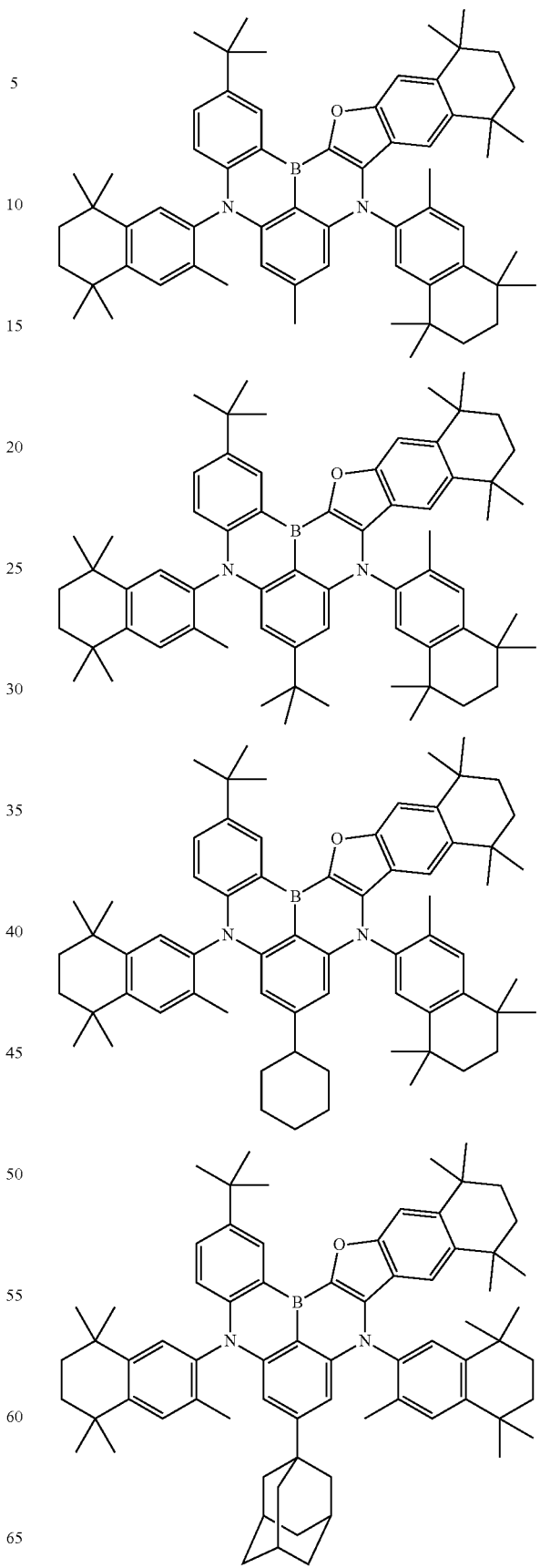

565
-continued
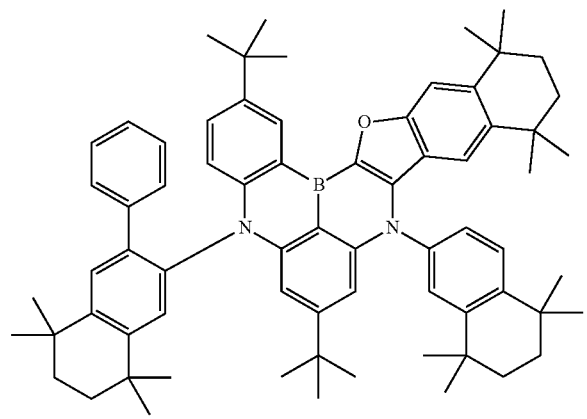
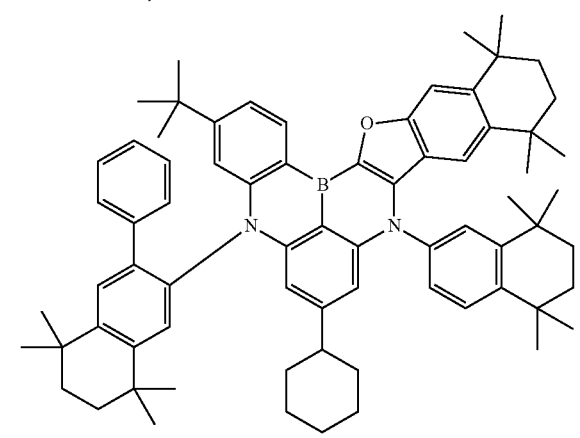
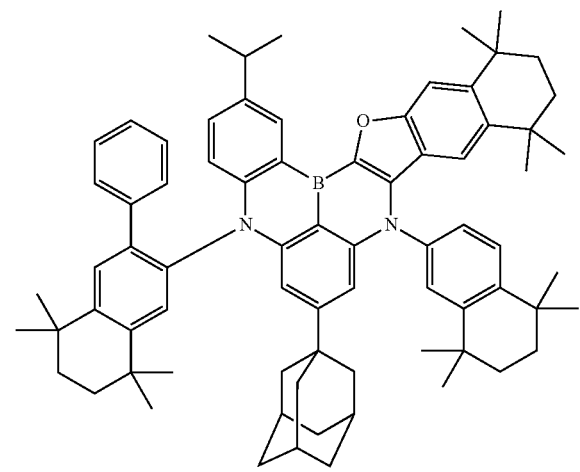
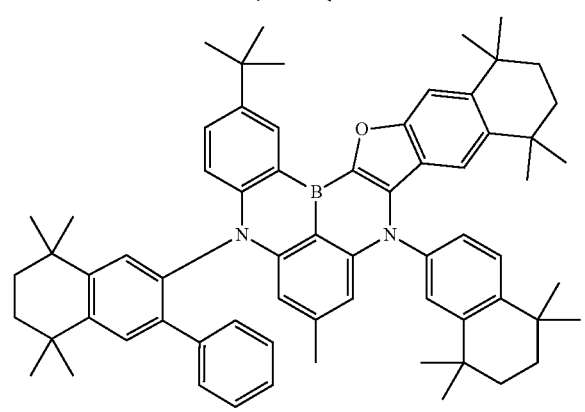
566
-continued
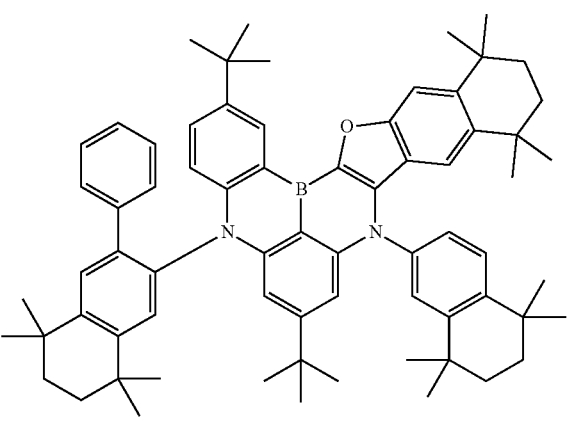
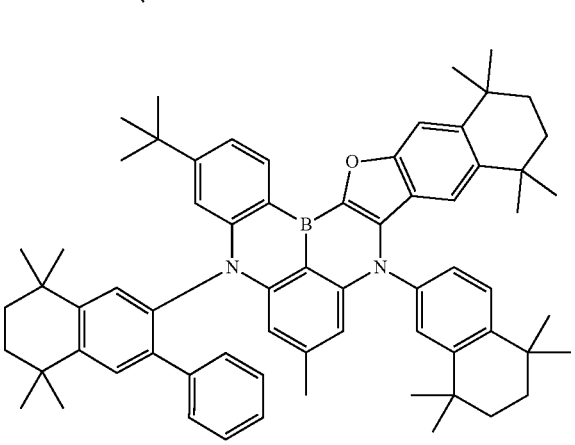
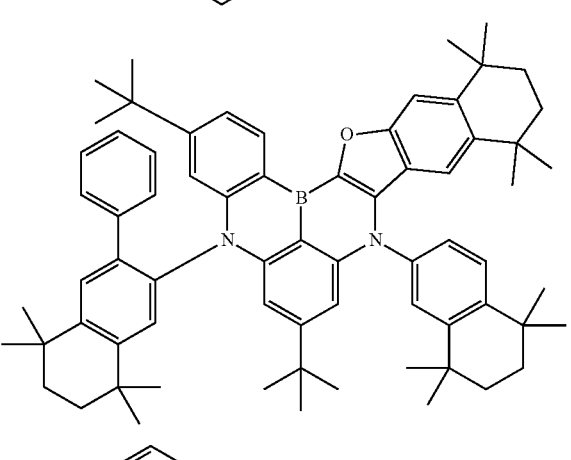
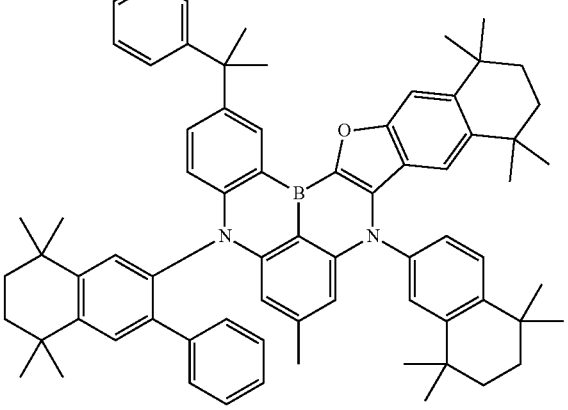

567
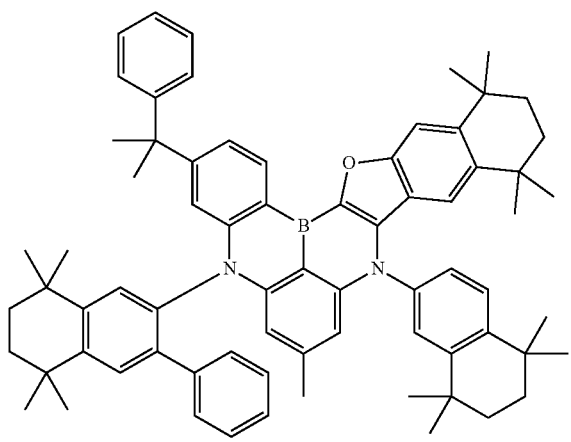
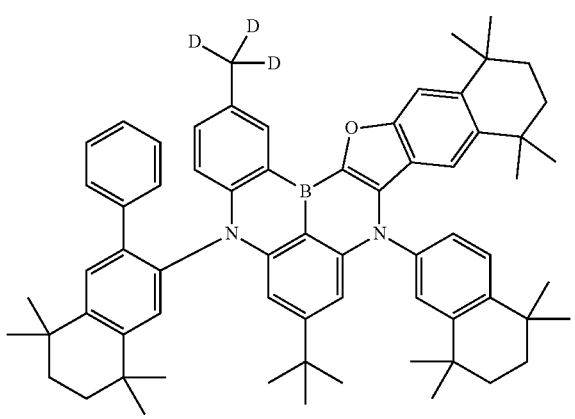
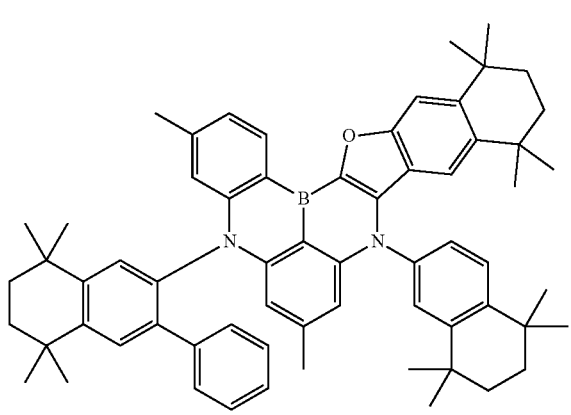
568
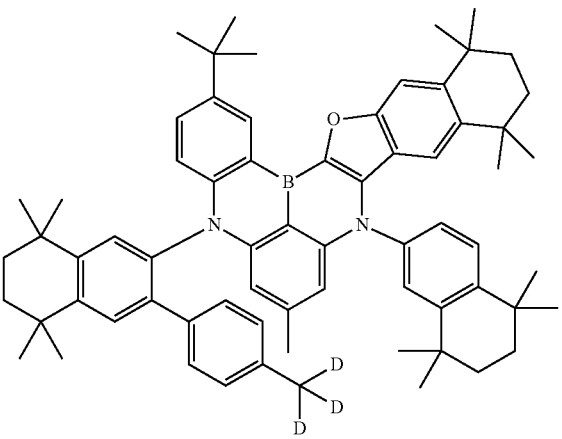
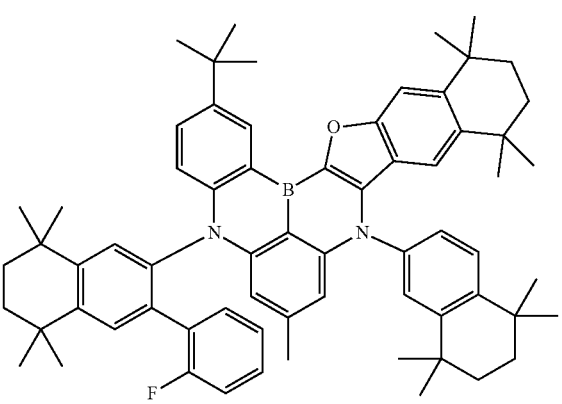
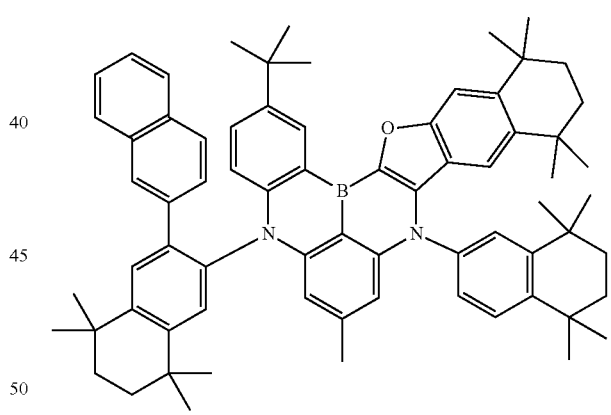
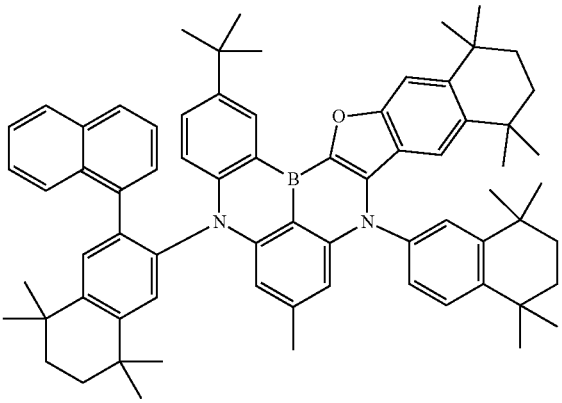

569
-continued
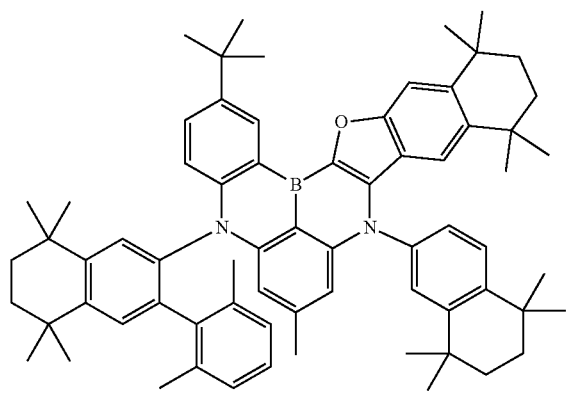
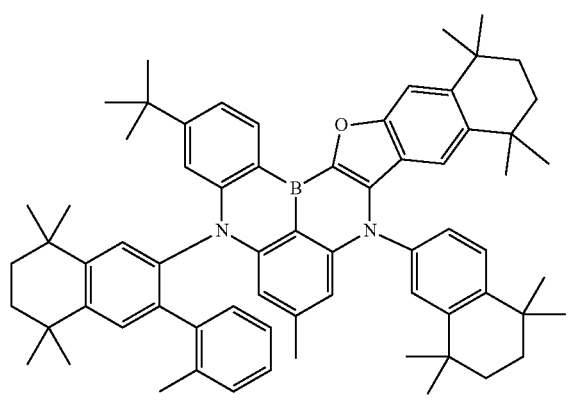
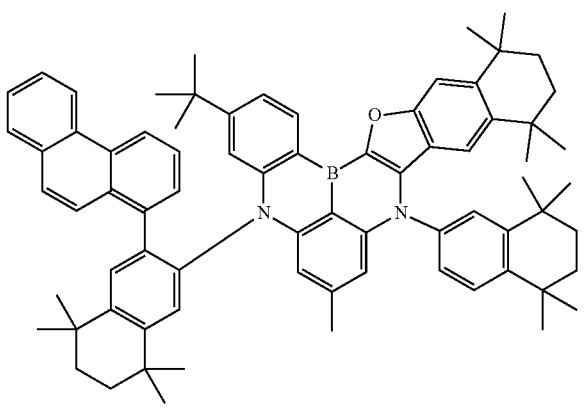
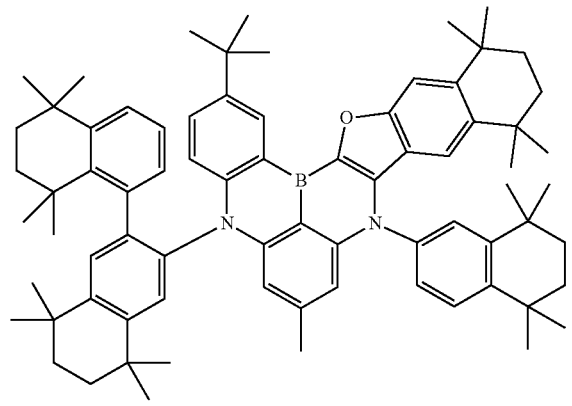
570
-continued
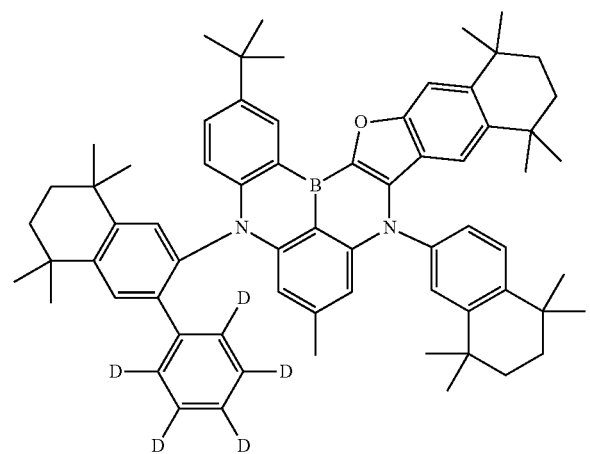
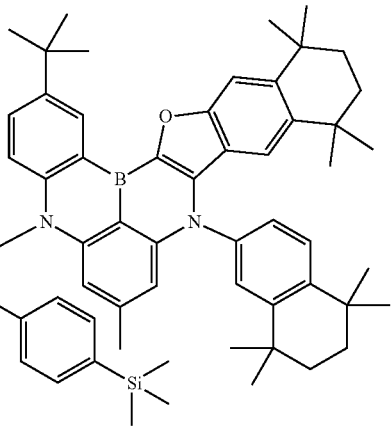
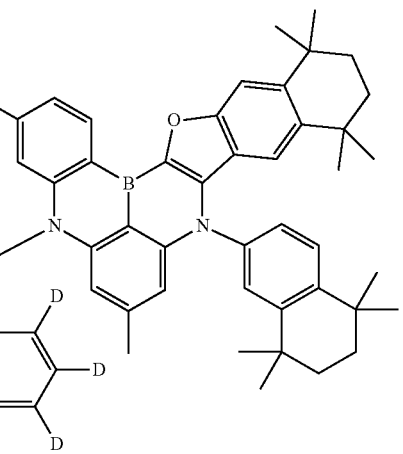

571
-continued
572
-continued
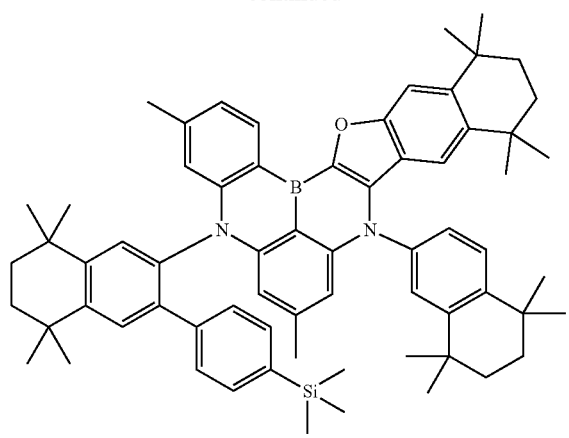
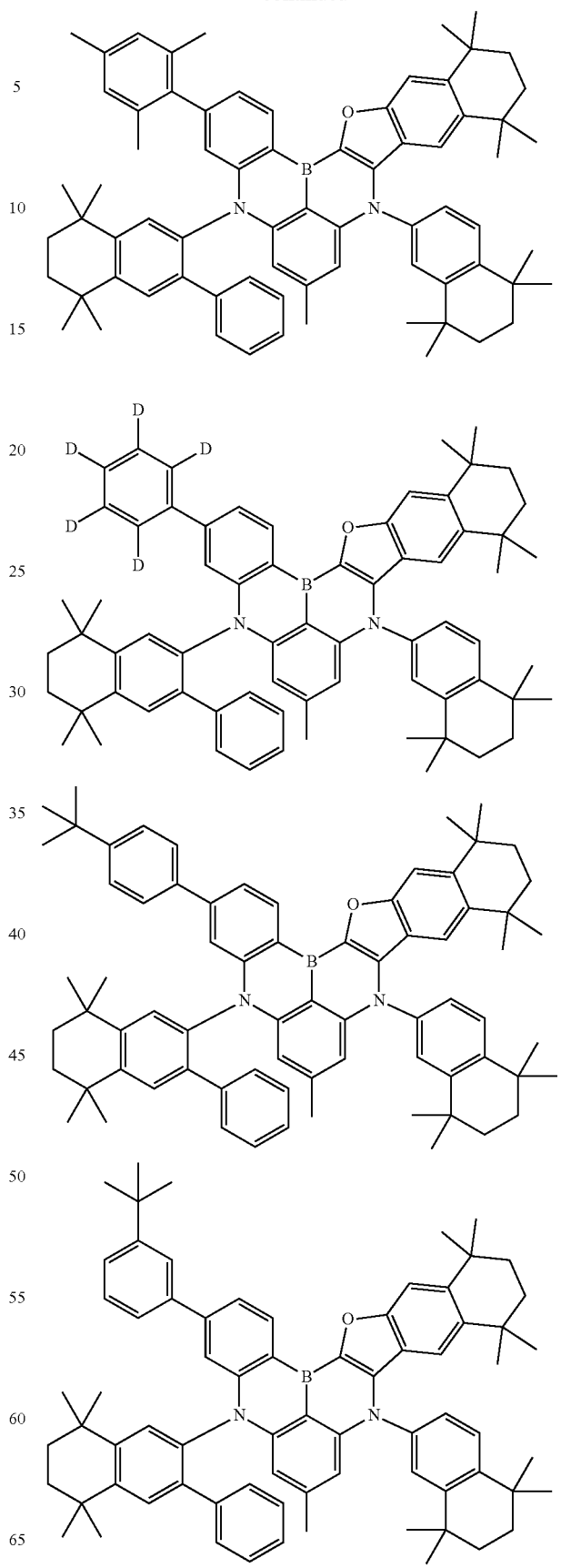

573
-continued
574
-continued
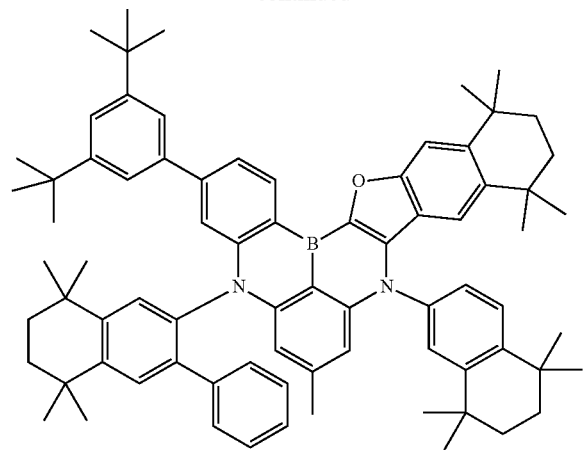
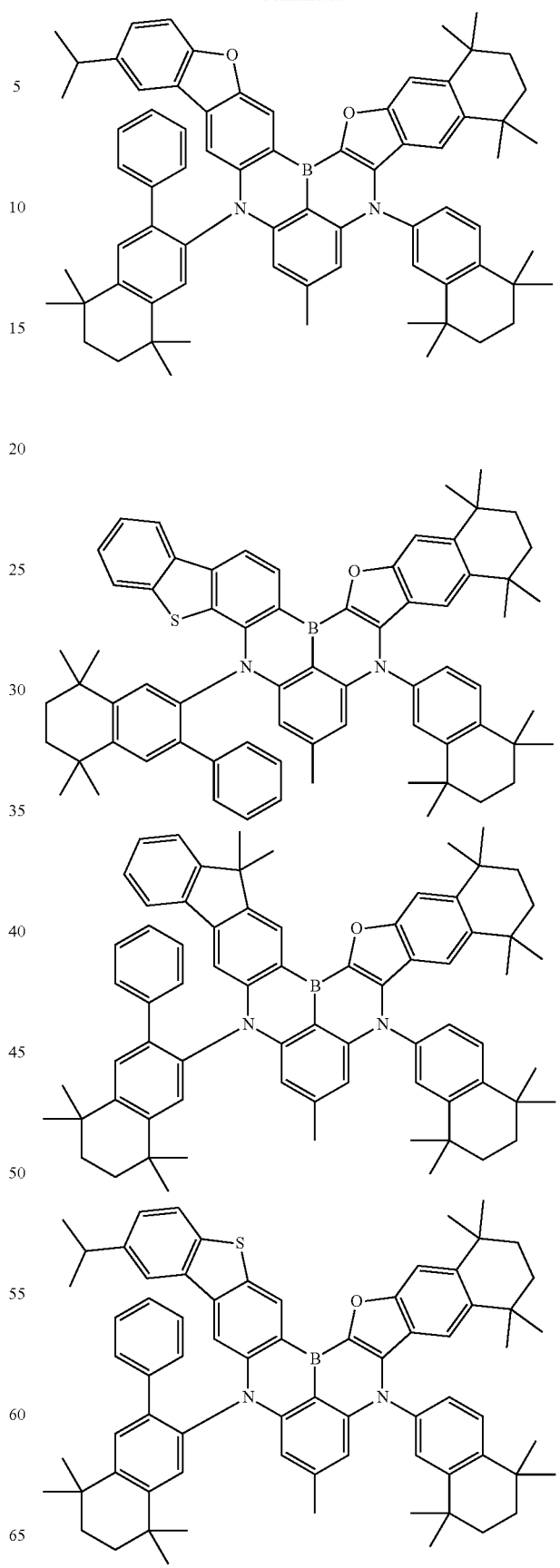

575
-continued
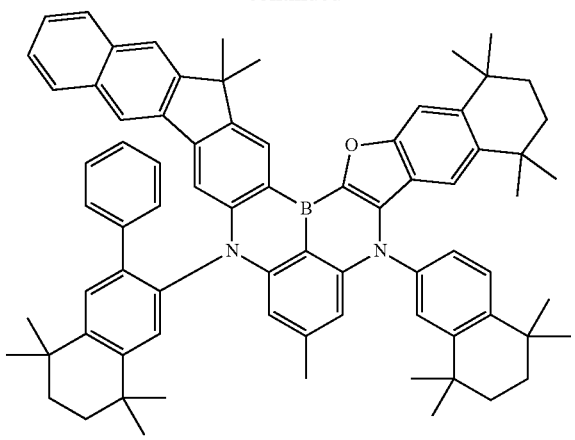
576
-continued
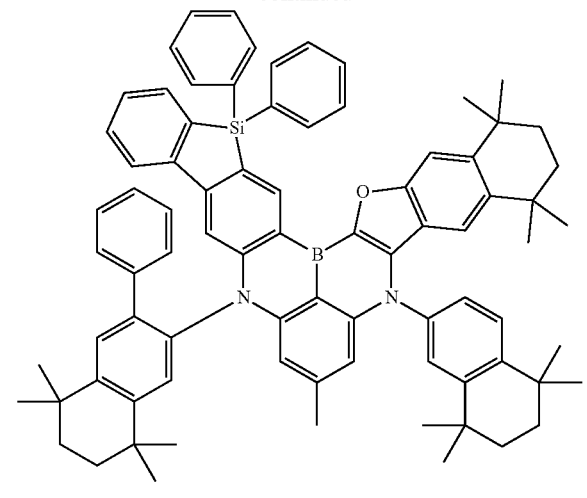
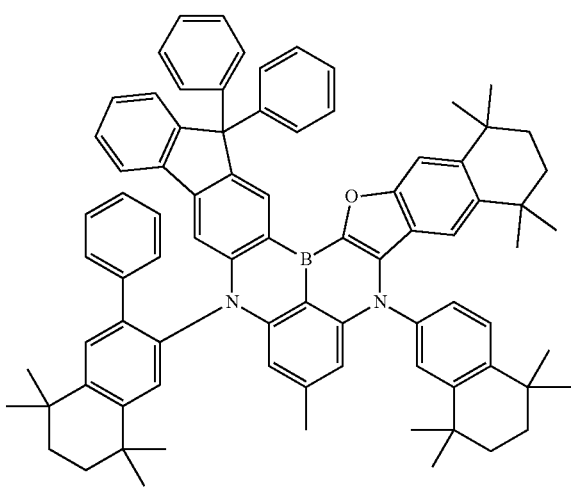
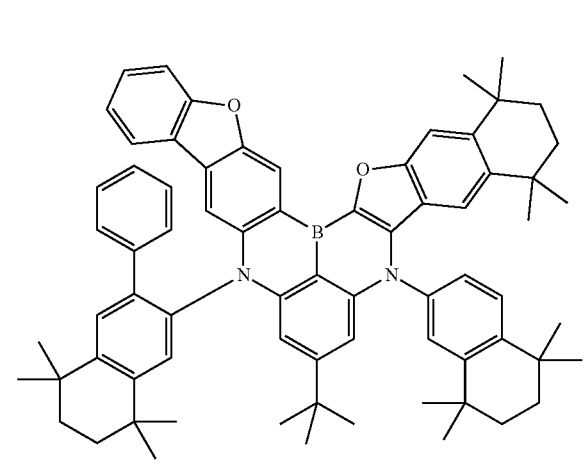
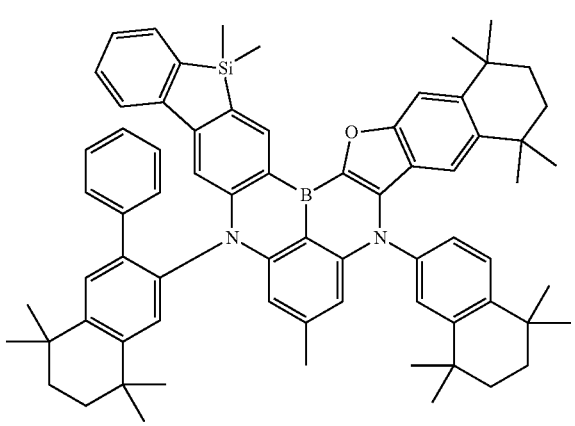
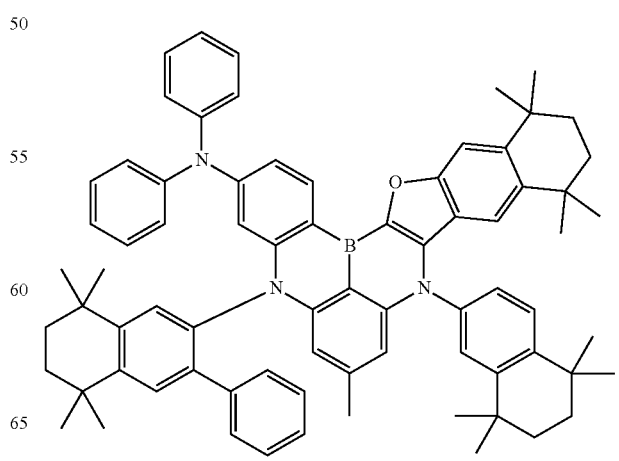

577
-continued
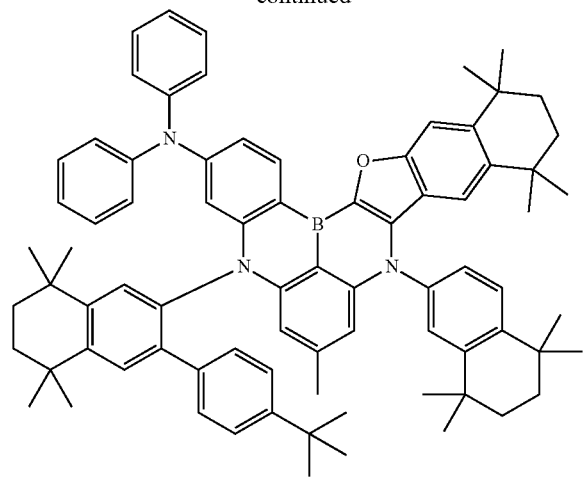
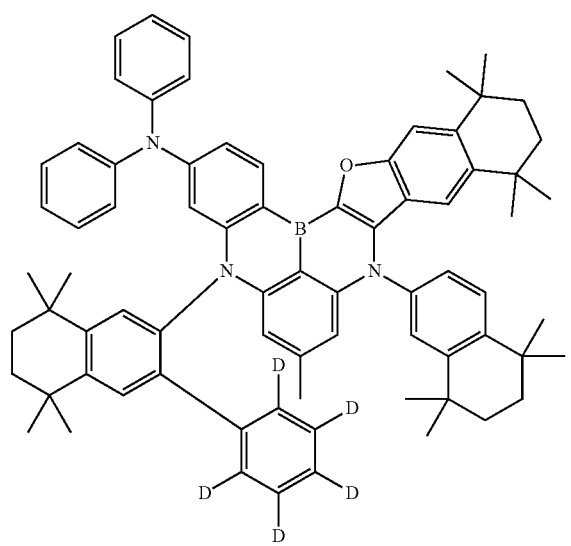
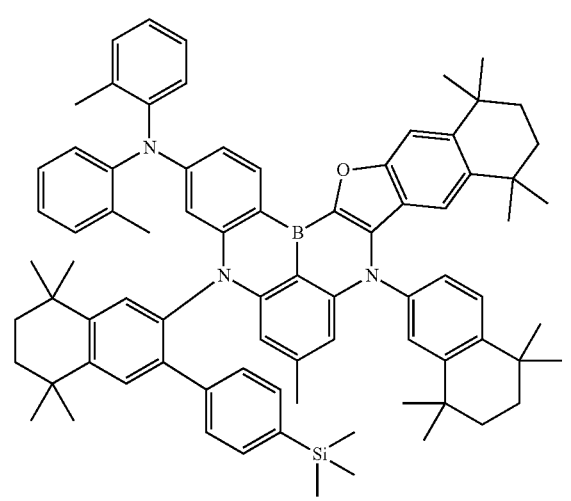
578
-continued
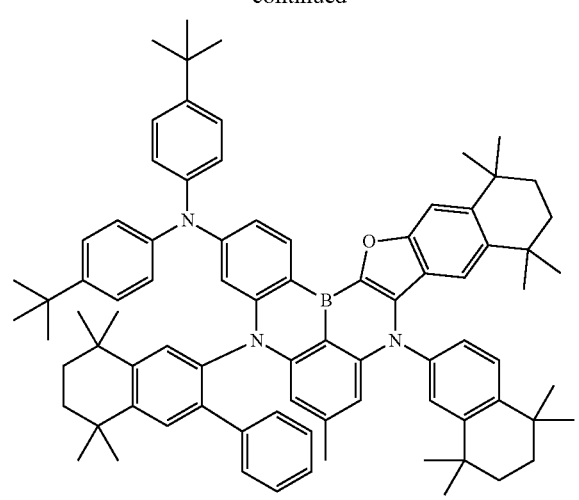
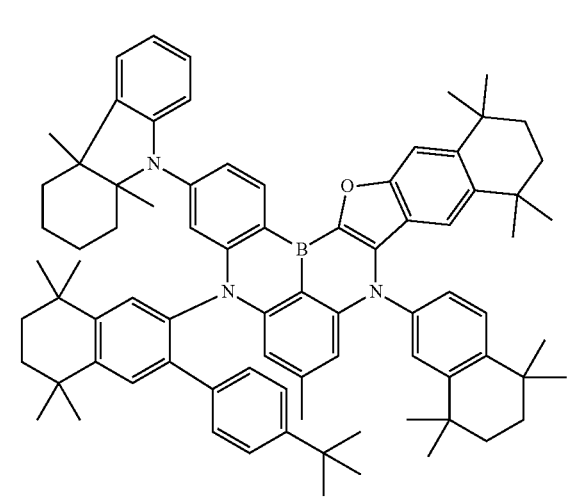
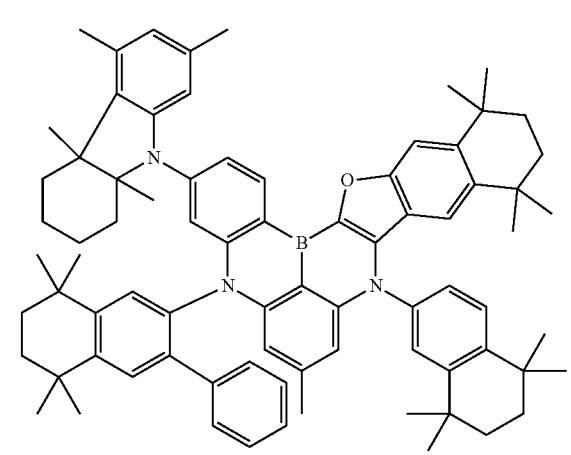

579
-continued
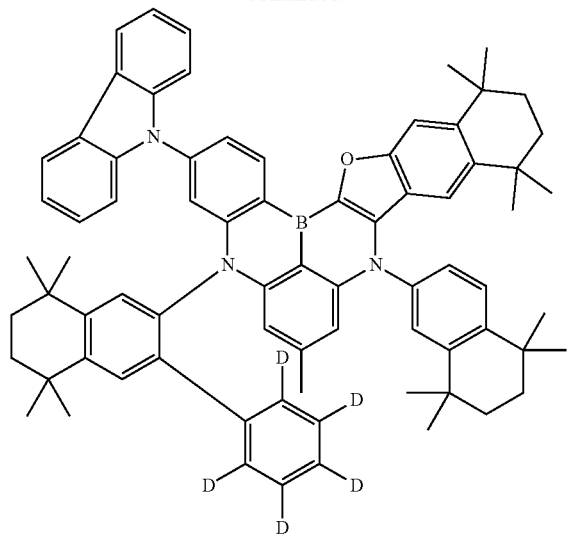
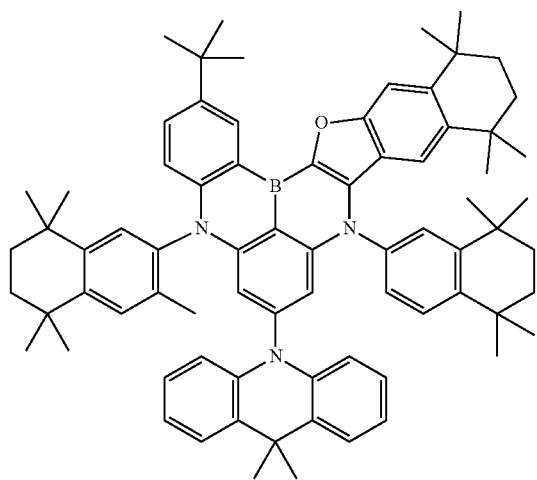
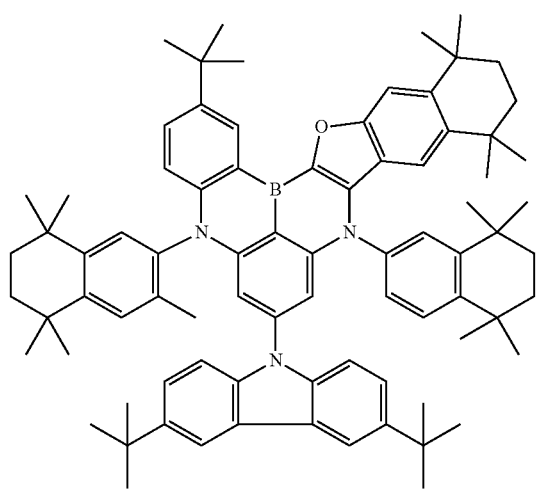
580
-continued
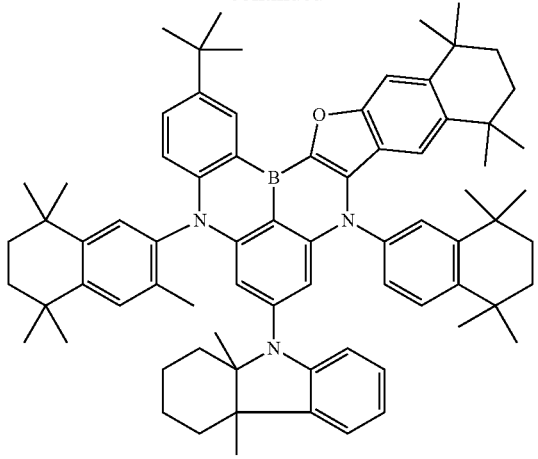
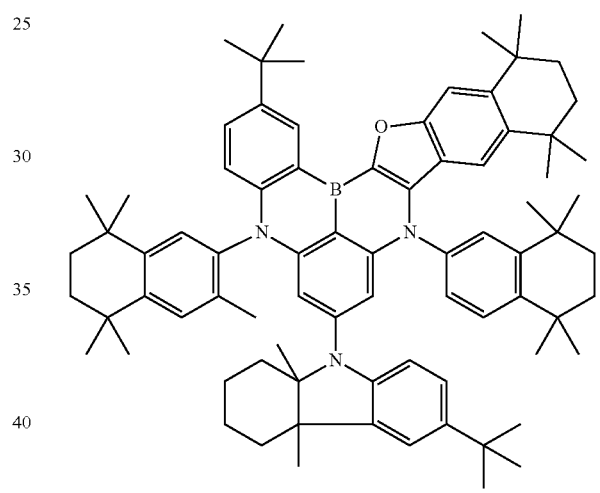
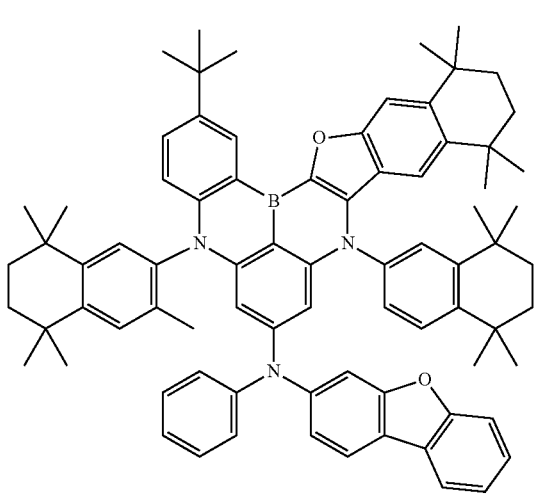

581
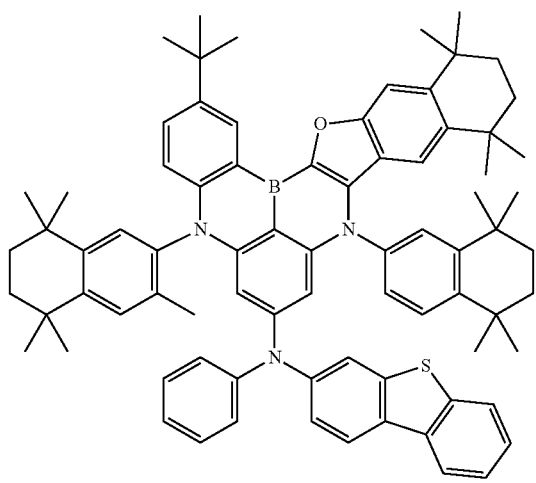
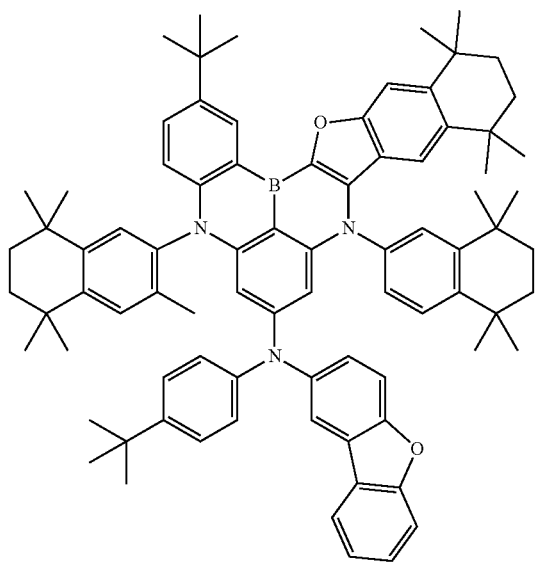
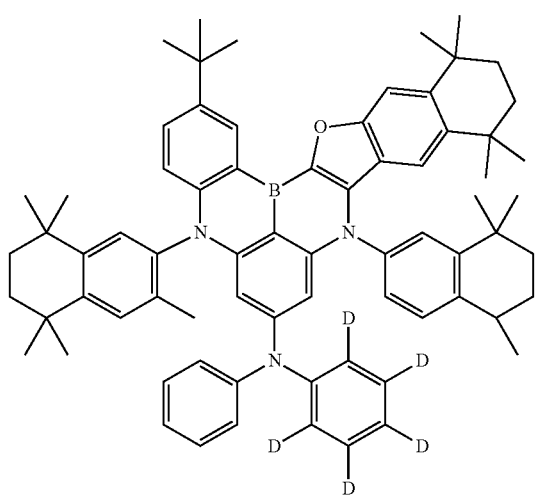
582
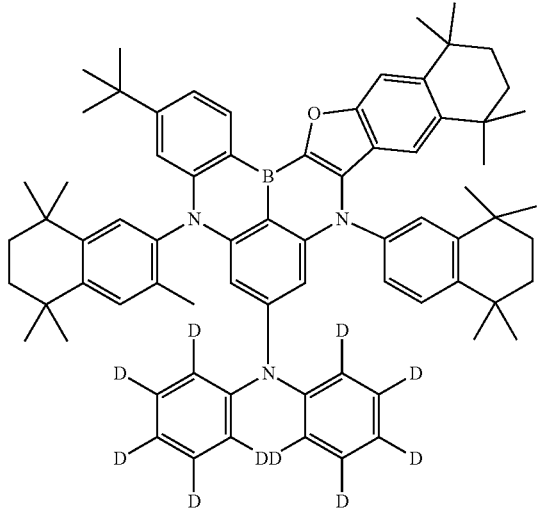
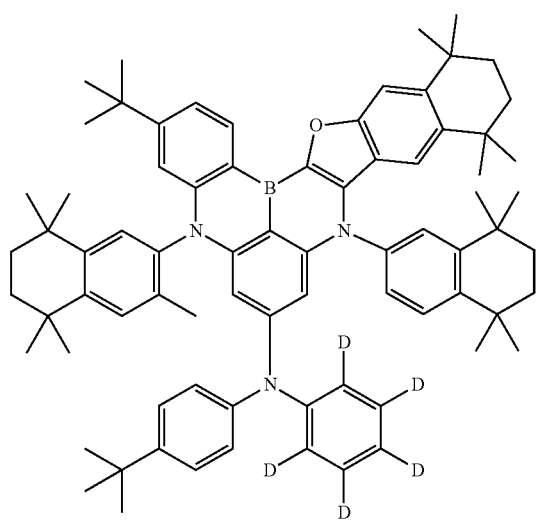
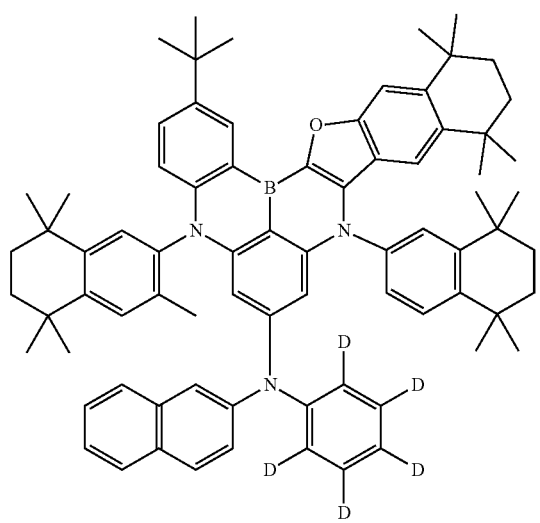

583
-continued
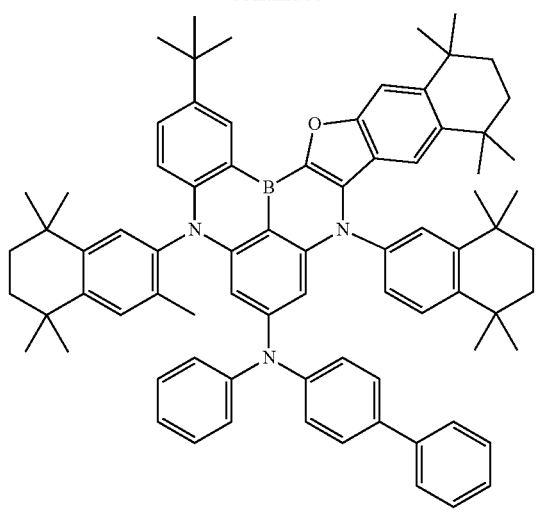
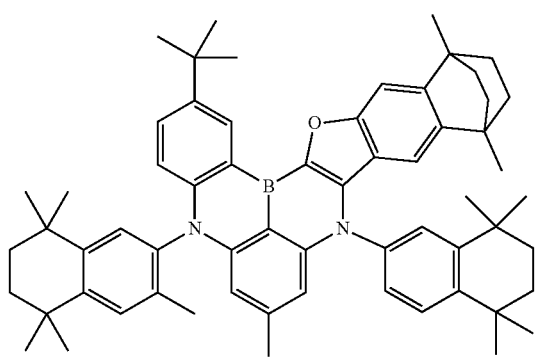
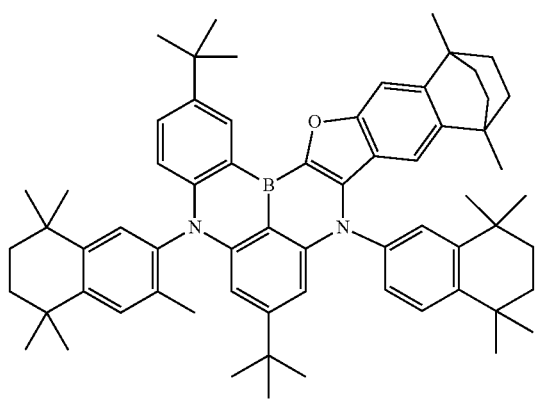
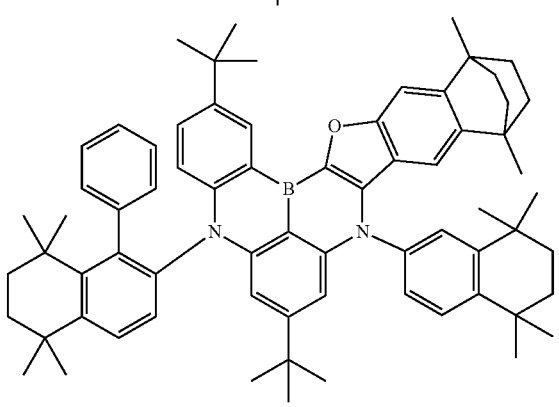
584
-continued
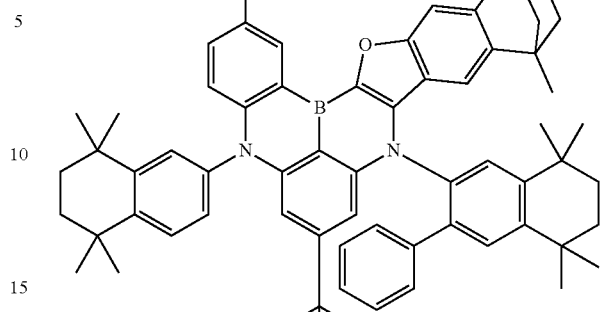
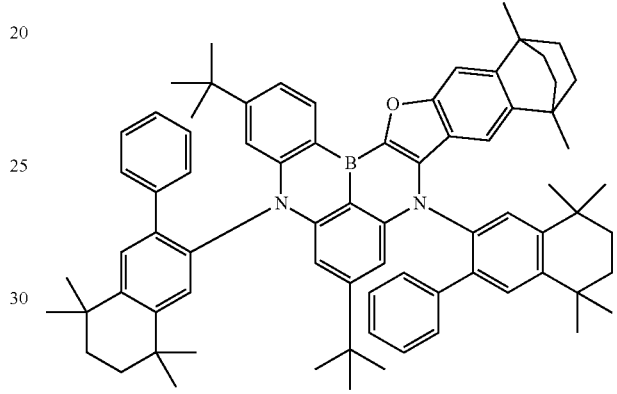
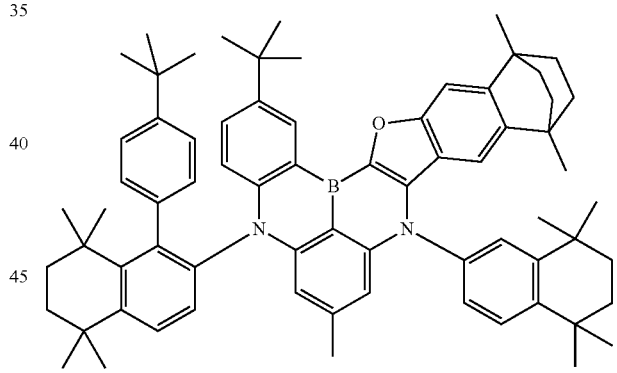
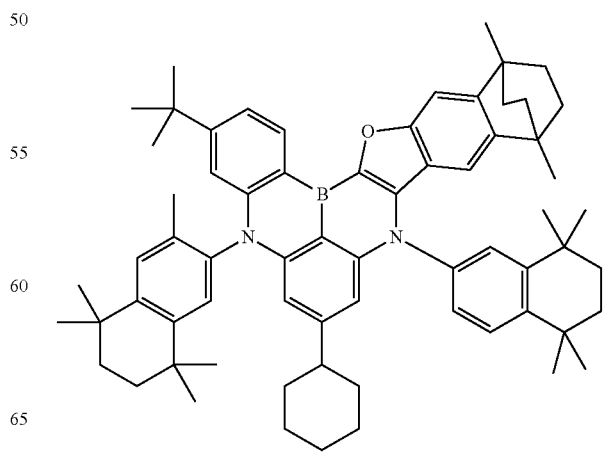

585
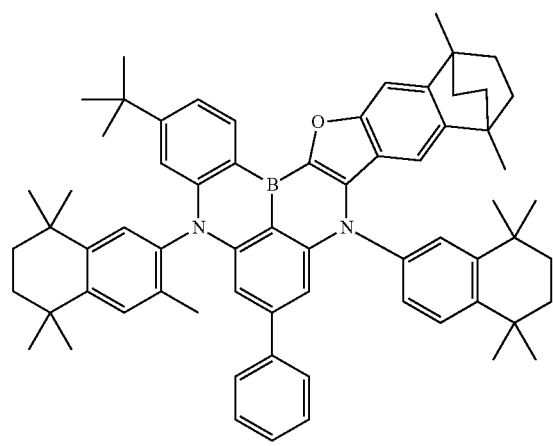
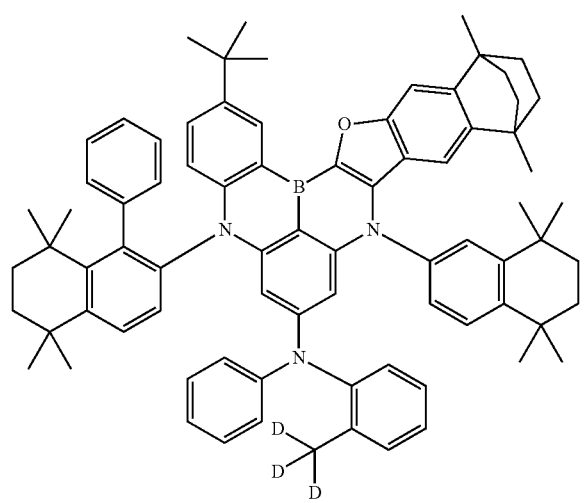
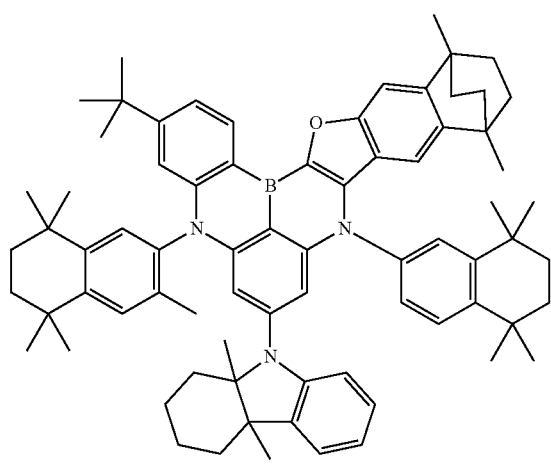
586
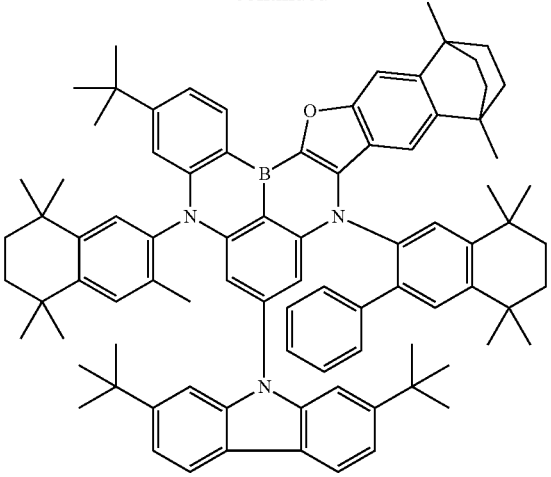
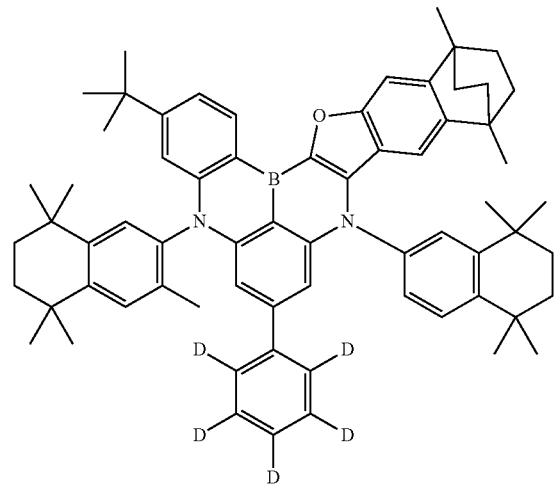
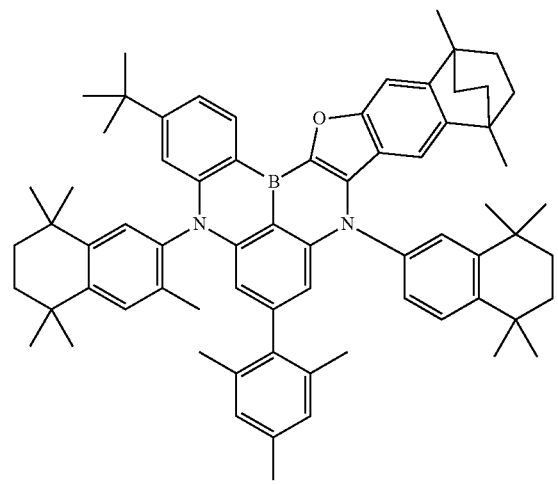

587
-continued
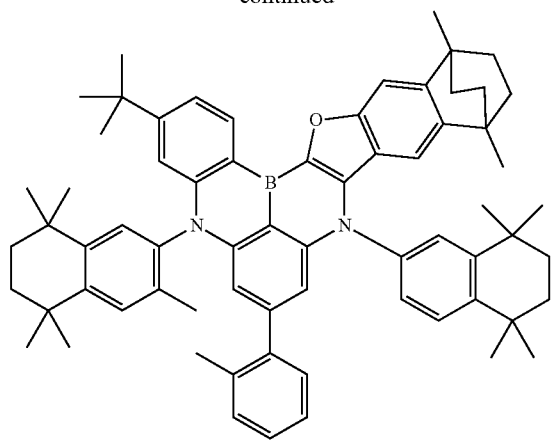
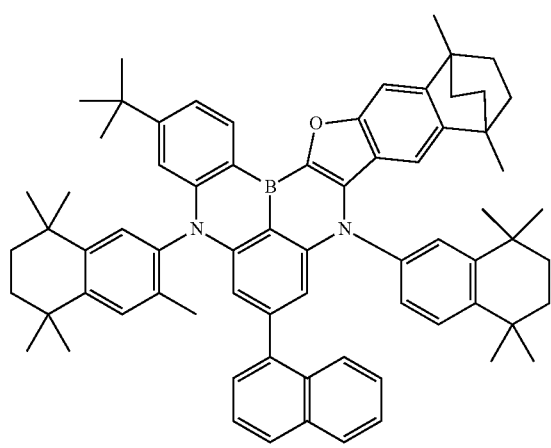
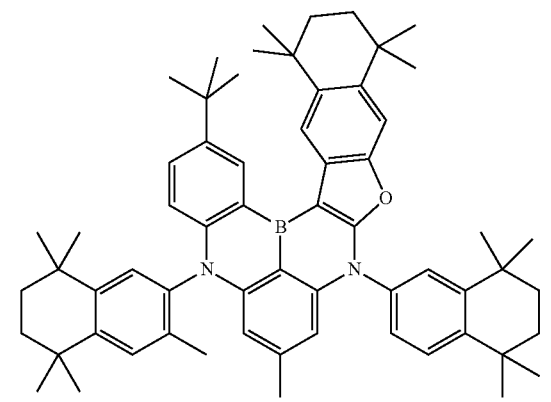
588
-continued
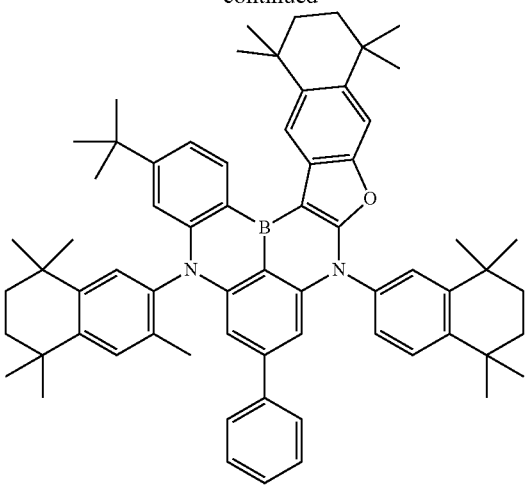
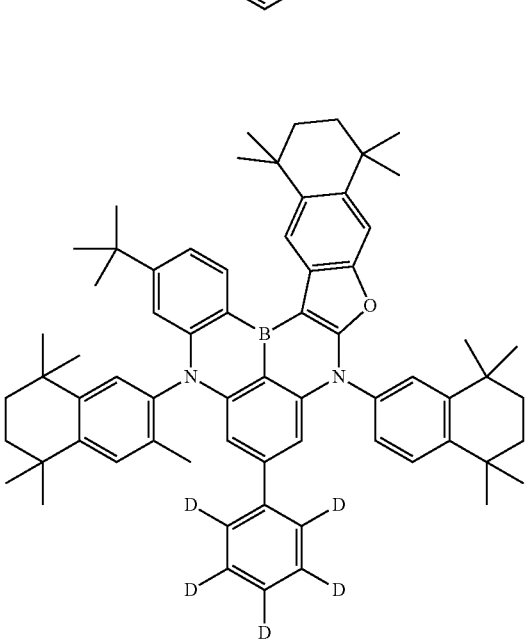
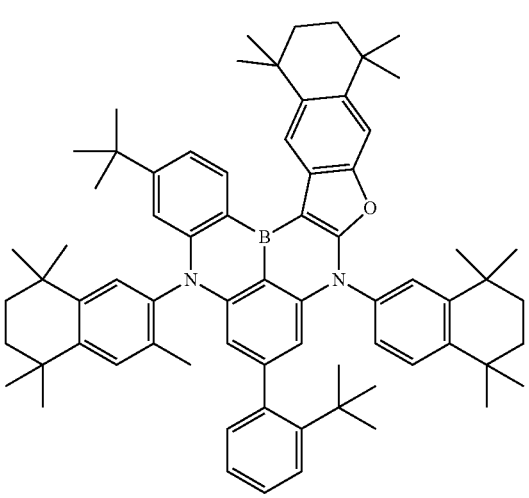

589
-continued
590
-continued
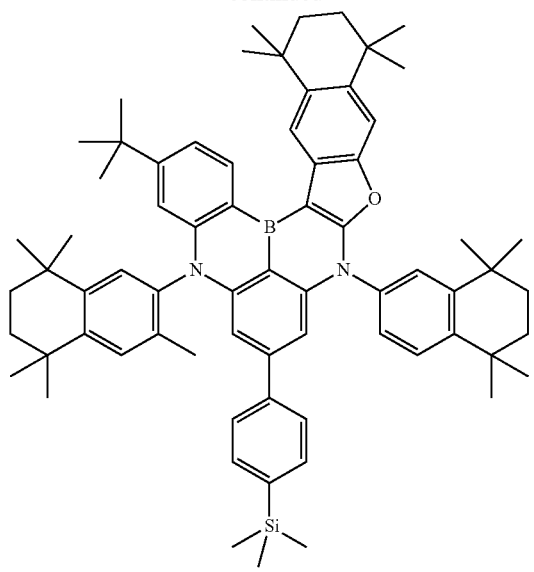
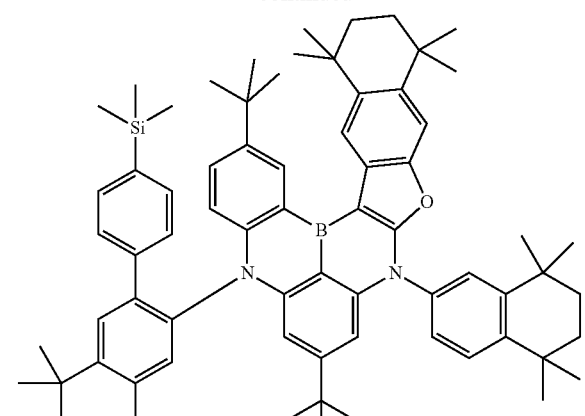
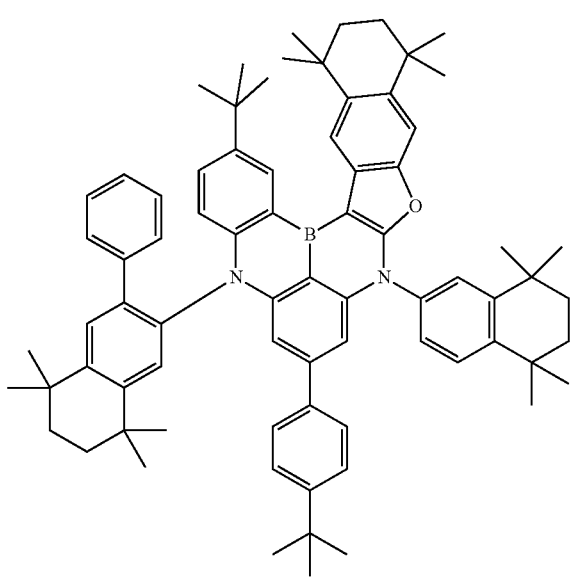
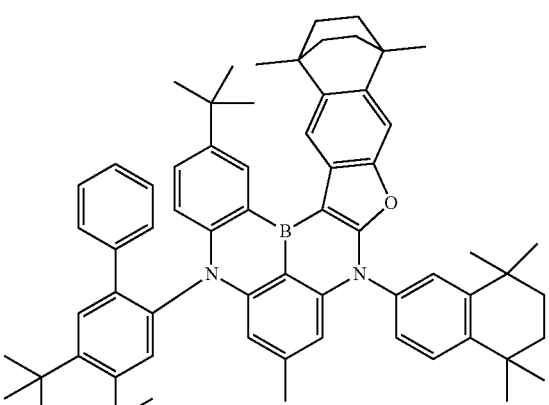
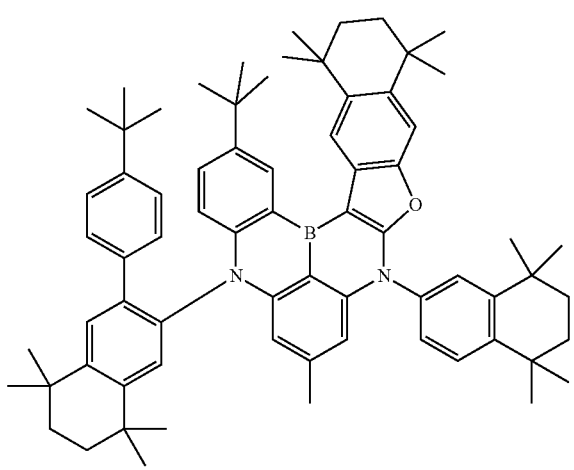
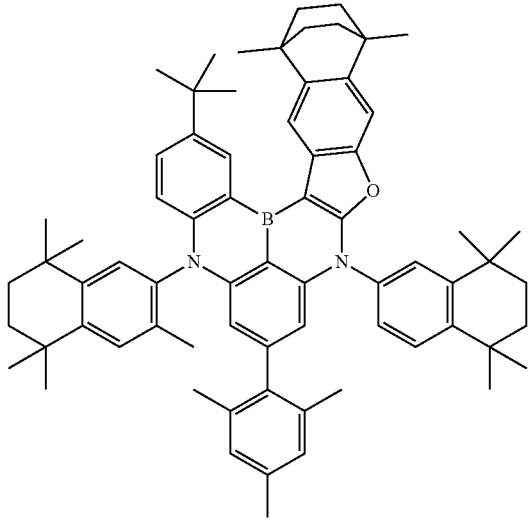

591
-continued
592
-continued
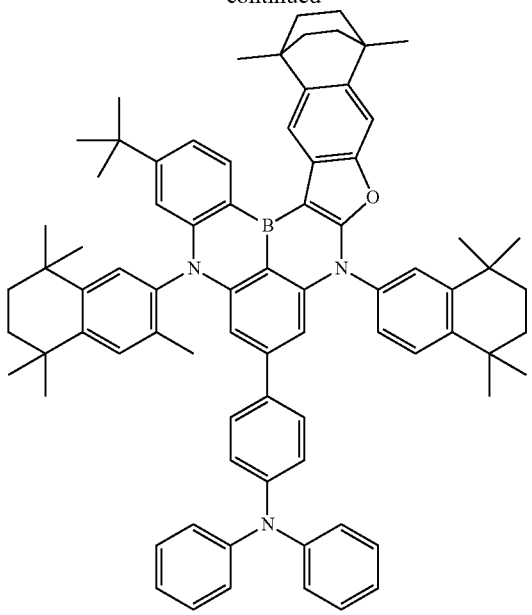
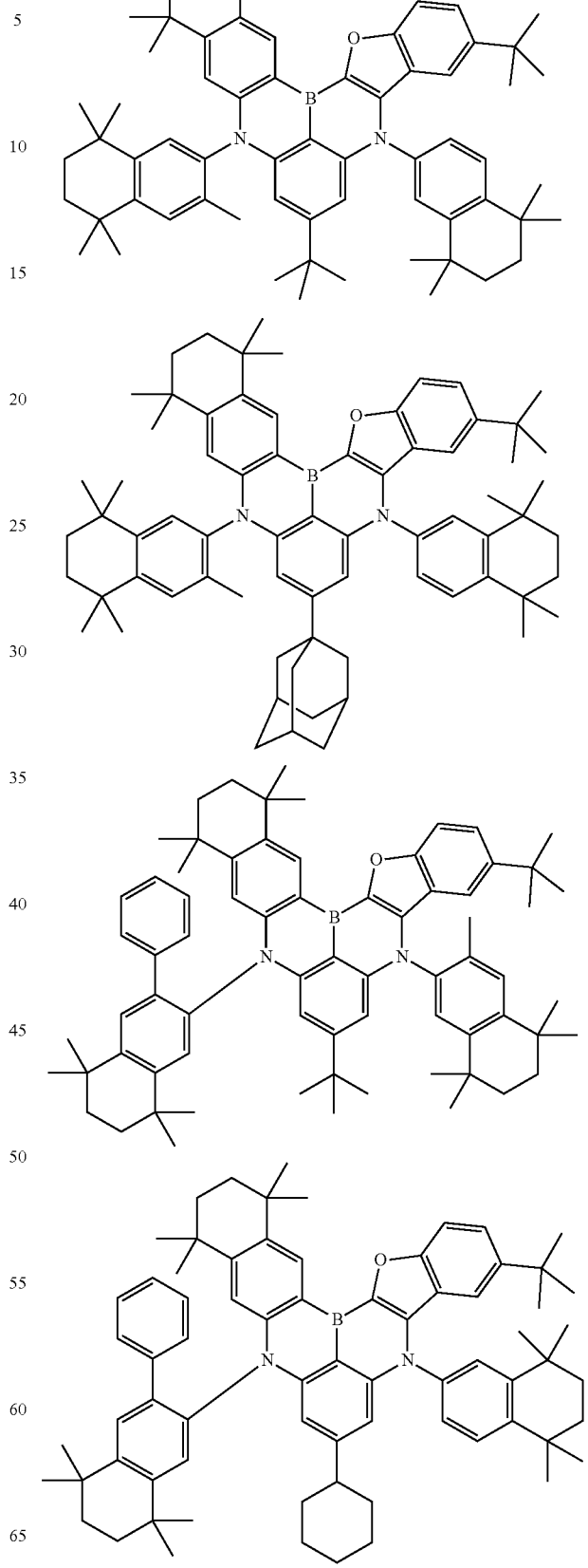

593
-continued
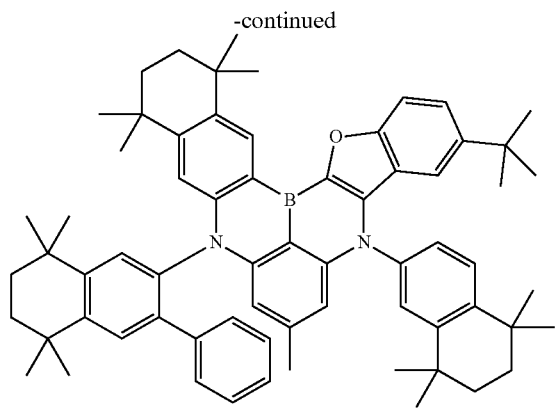
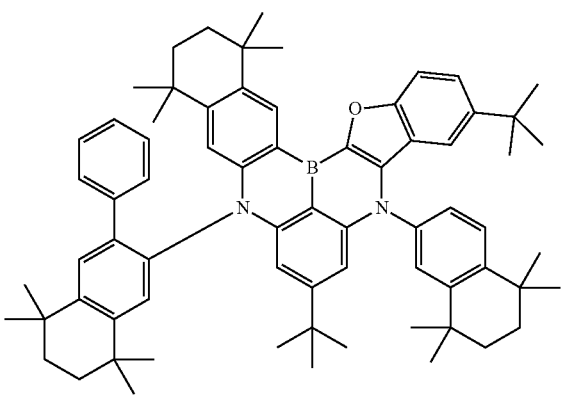
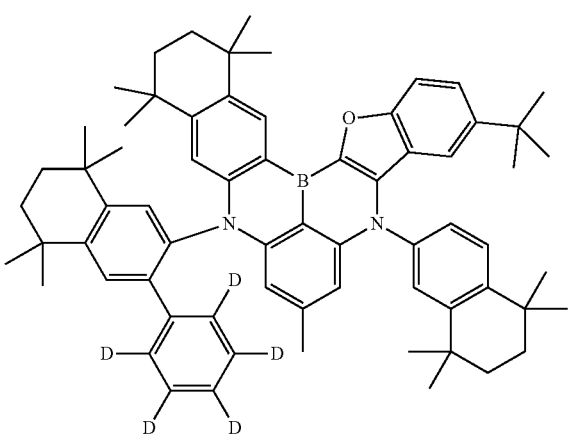
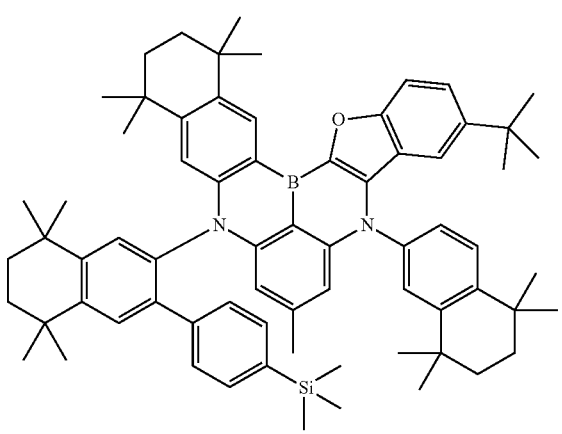
594
-continued
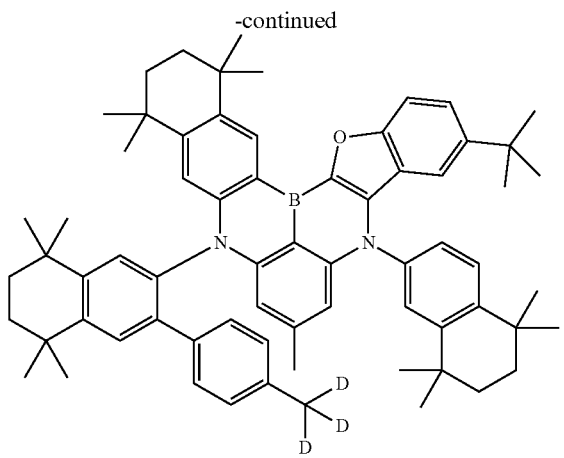
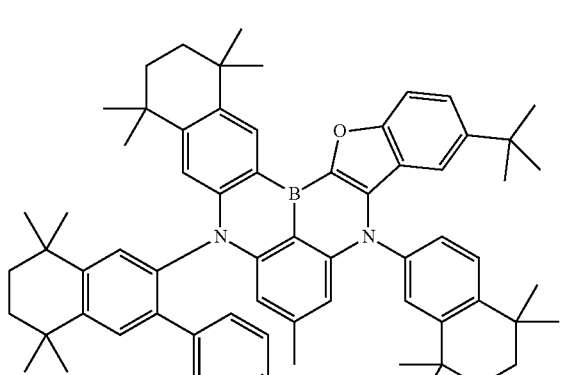
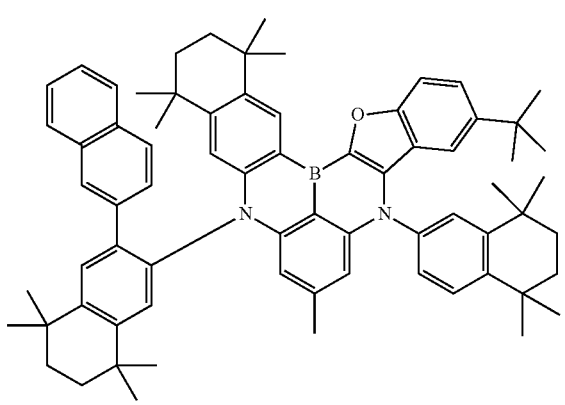
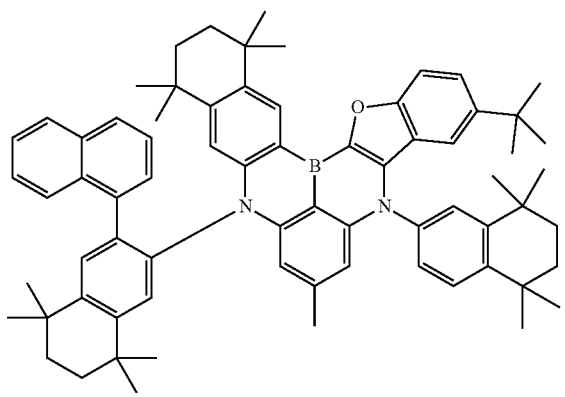

595
-continued
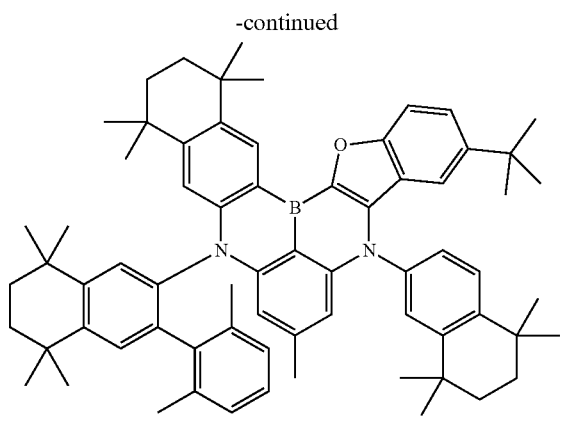
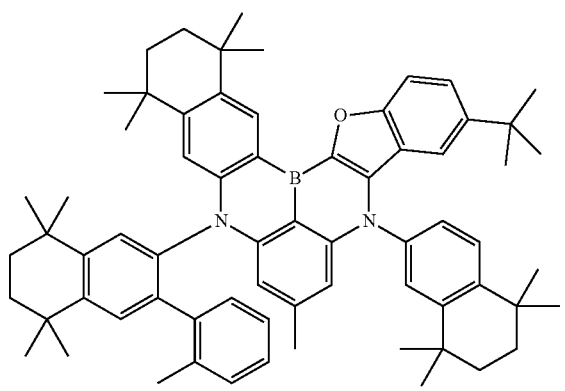
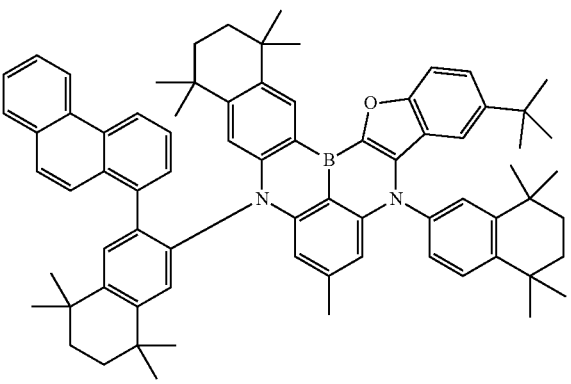
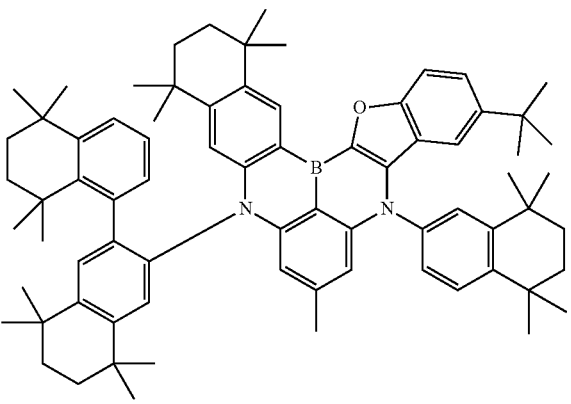
596
-continued
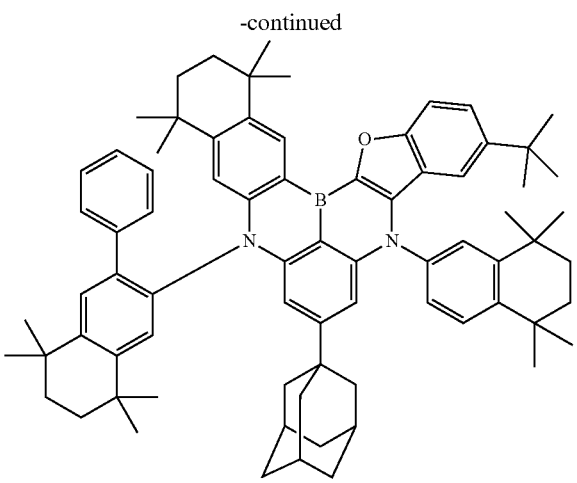
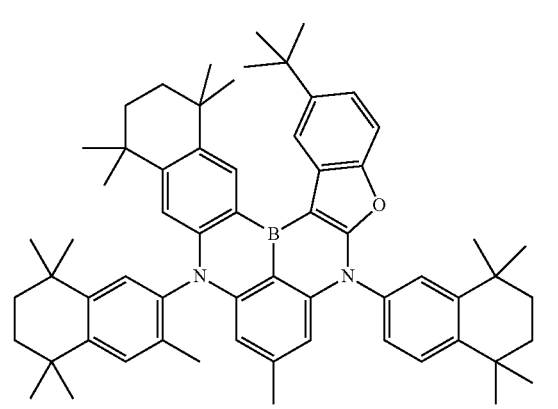
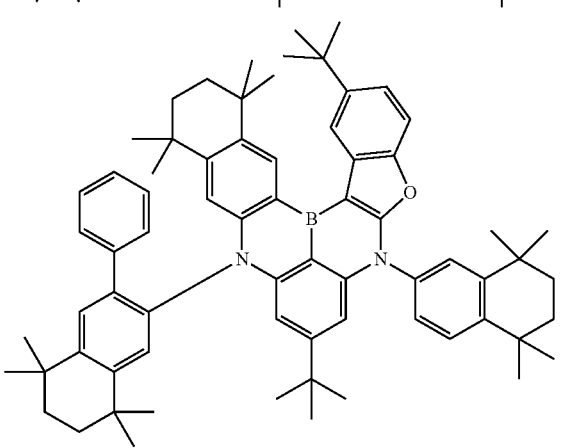
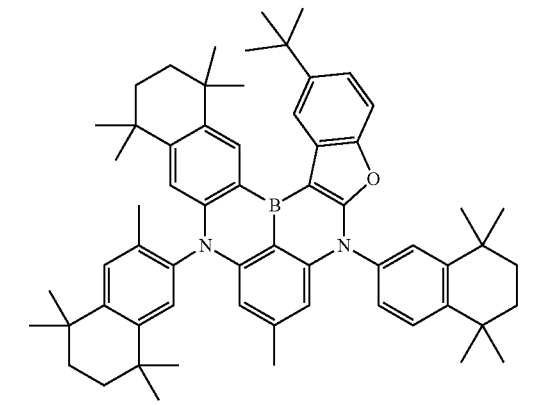

597
-continued
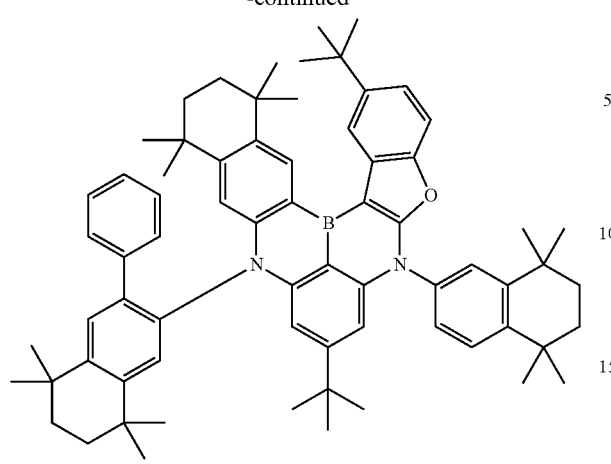
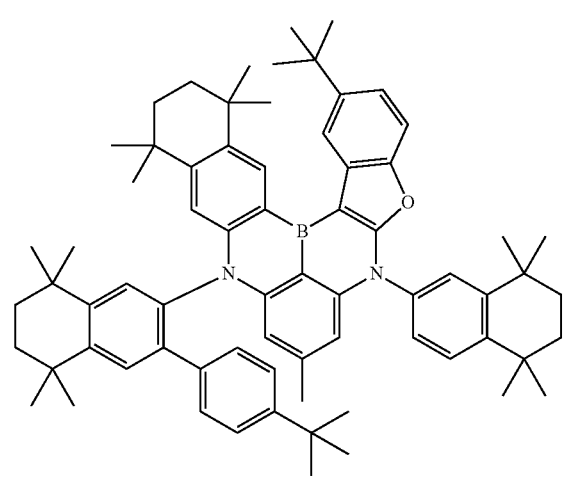
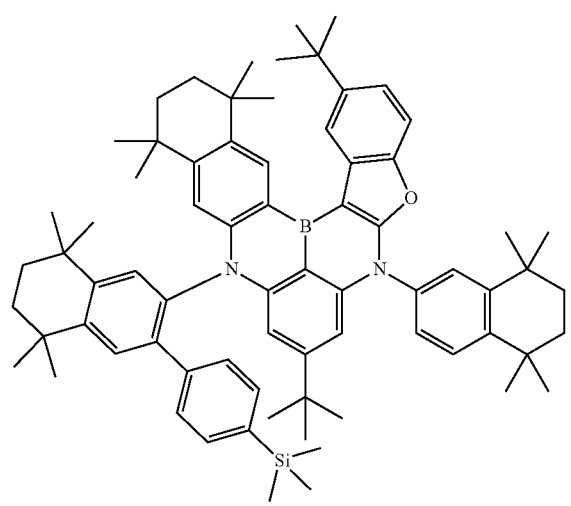
598
-continued
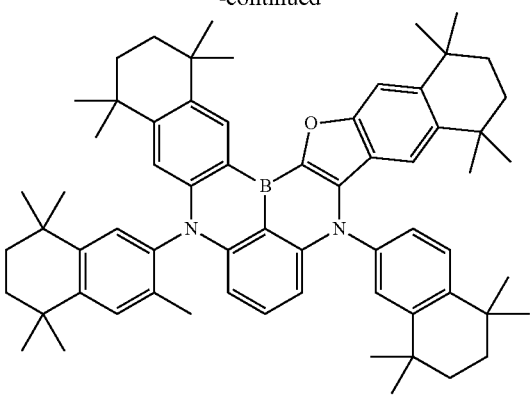
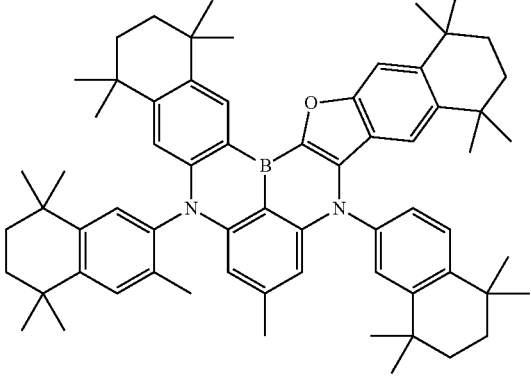
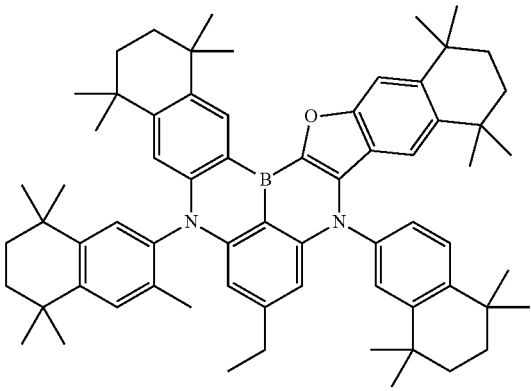
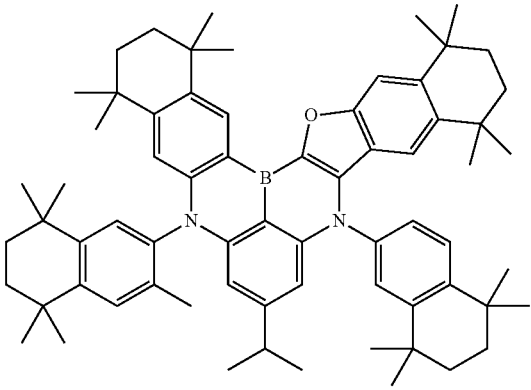

| 599 | 600 |
|---|---|
| 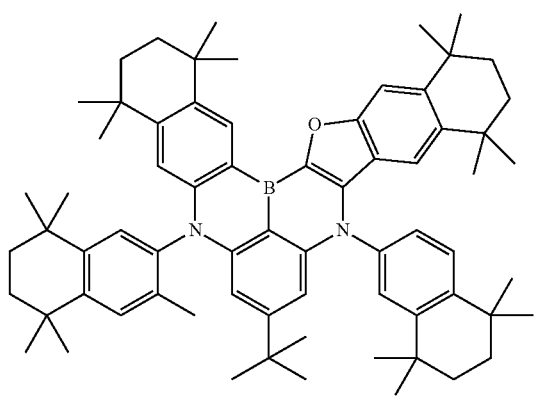 | 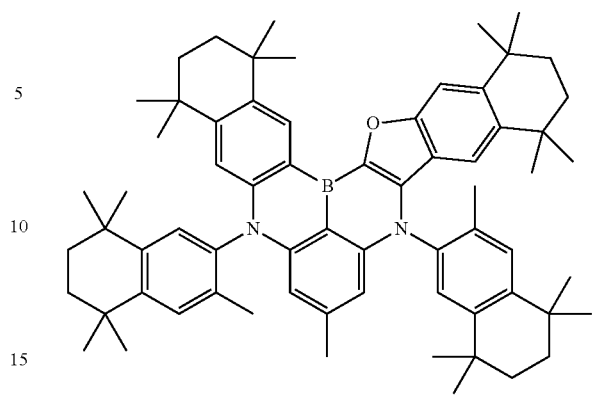 |
| 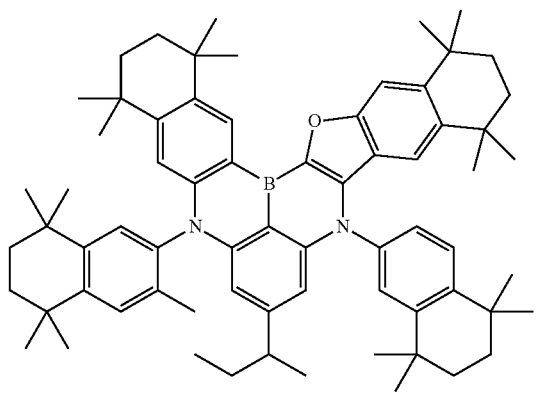 | 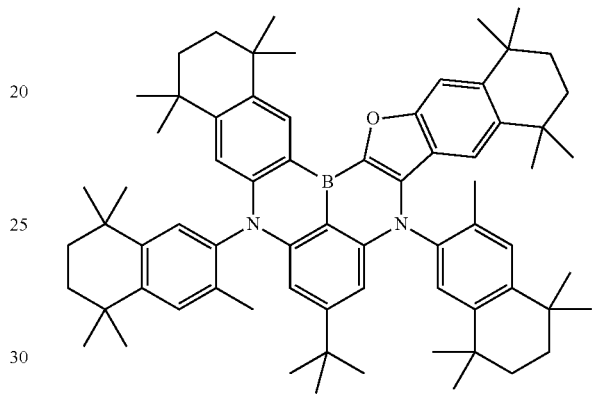 |
| 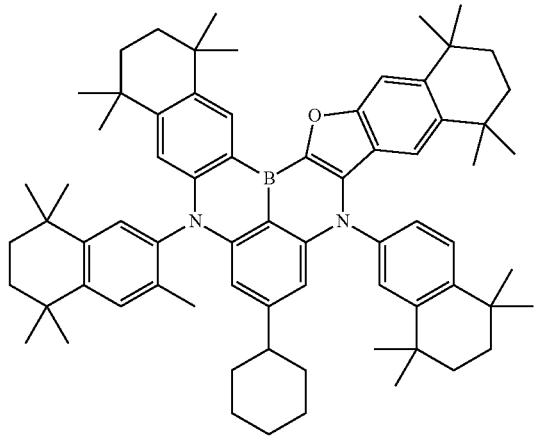 | 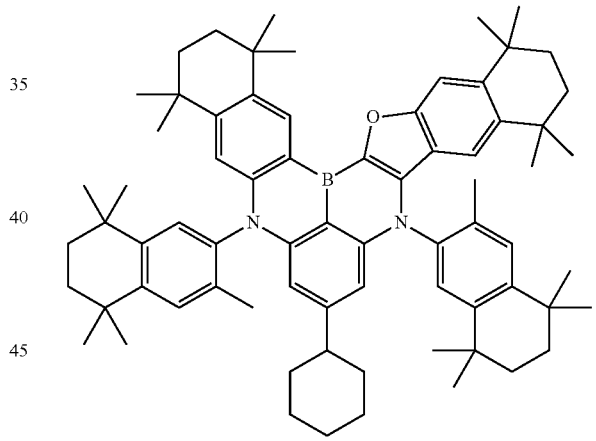 |
| 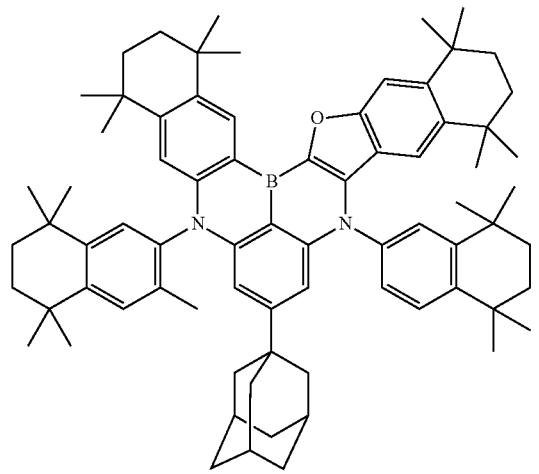 | 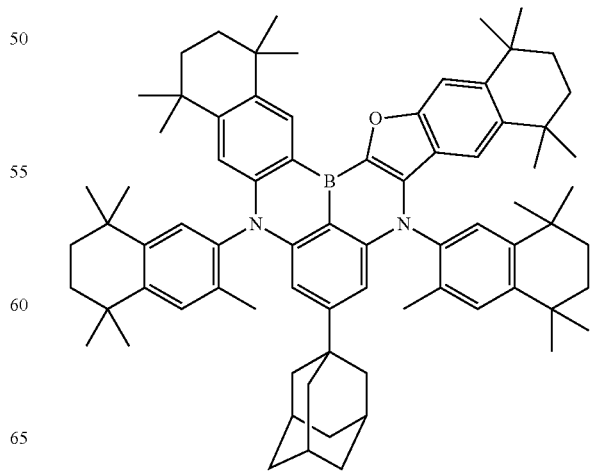 |

601
-continued
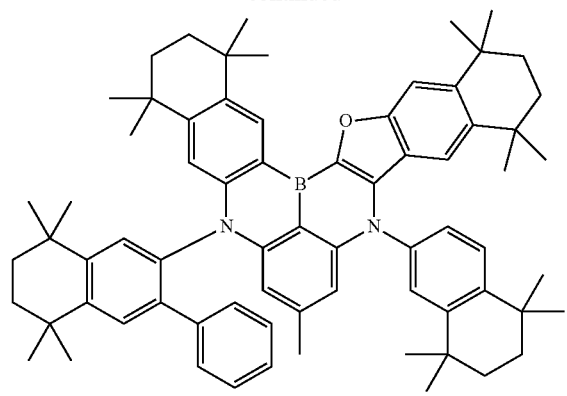
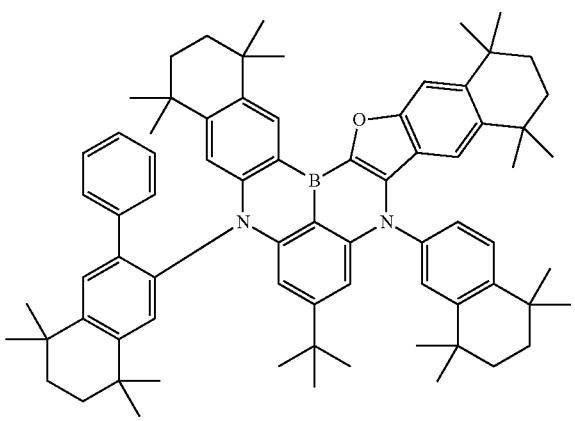
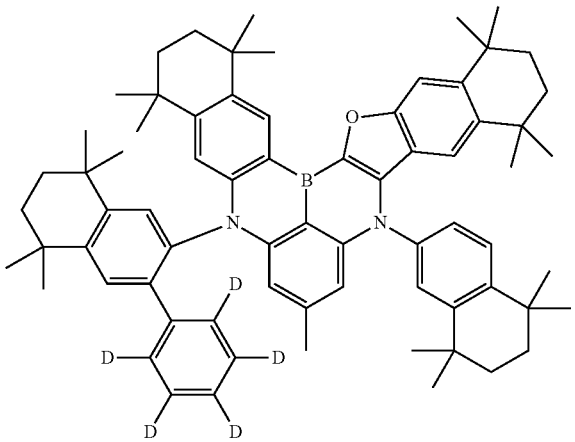
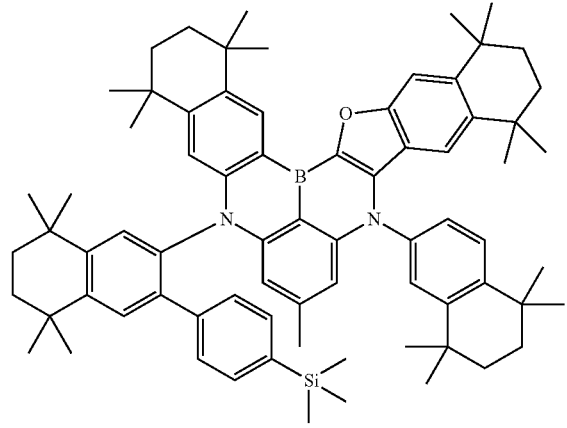
602
-continued
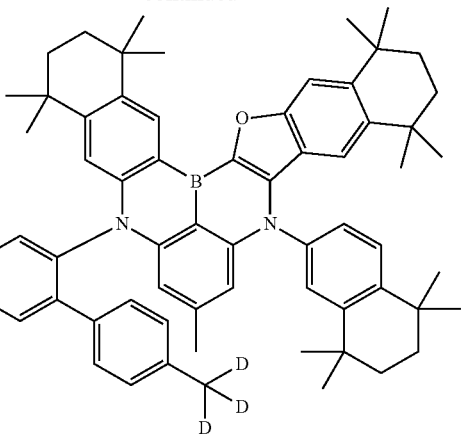
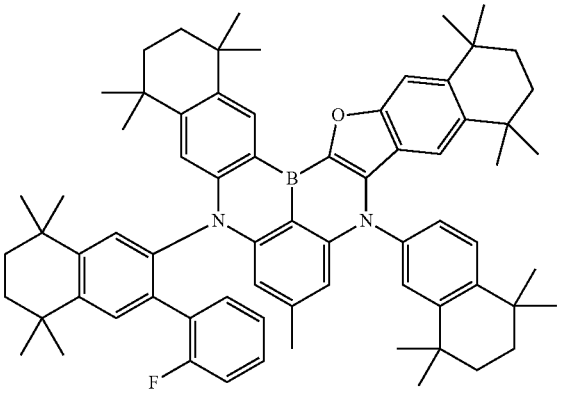
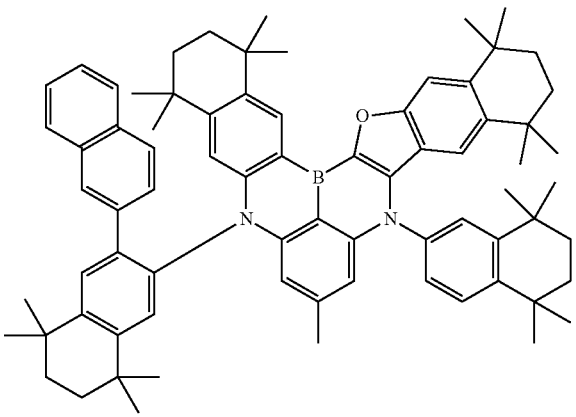
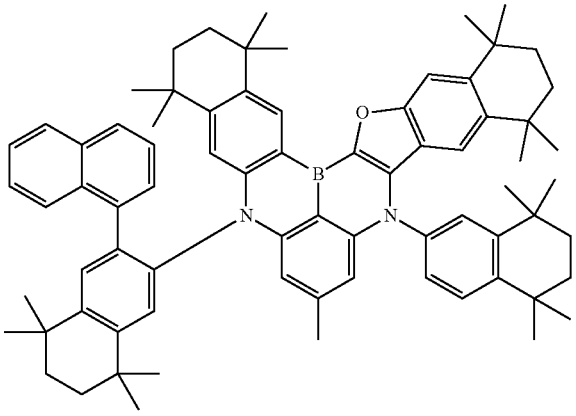

603
-continued
604
-continued
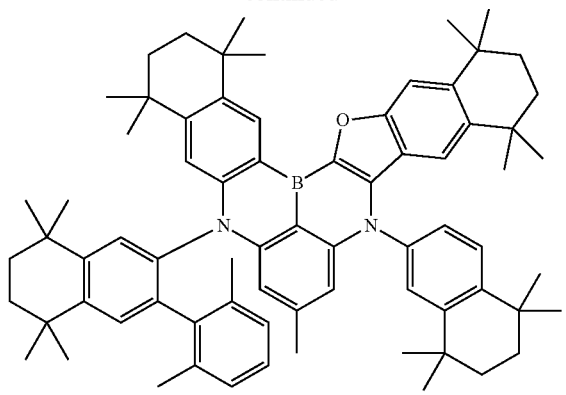
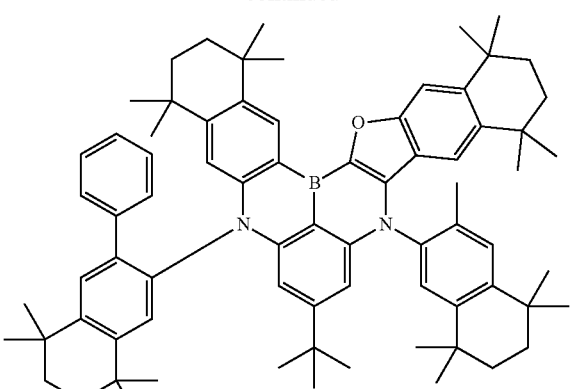

605
-continued
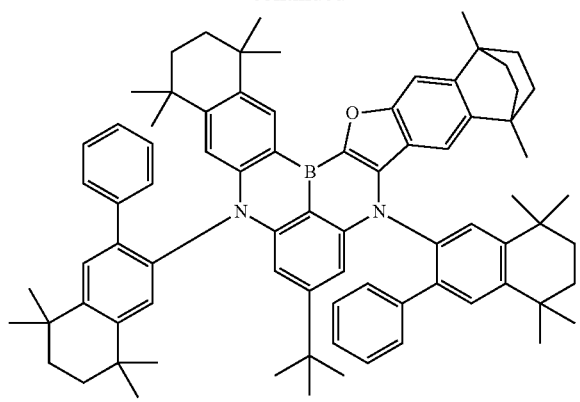
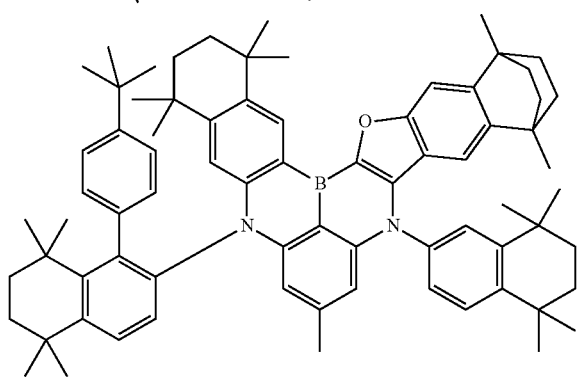
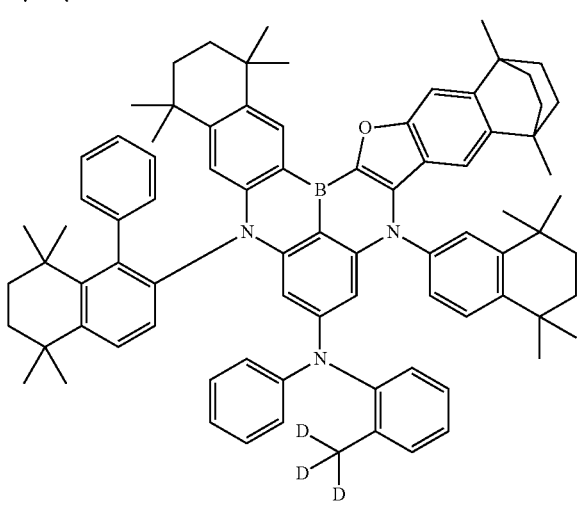
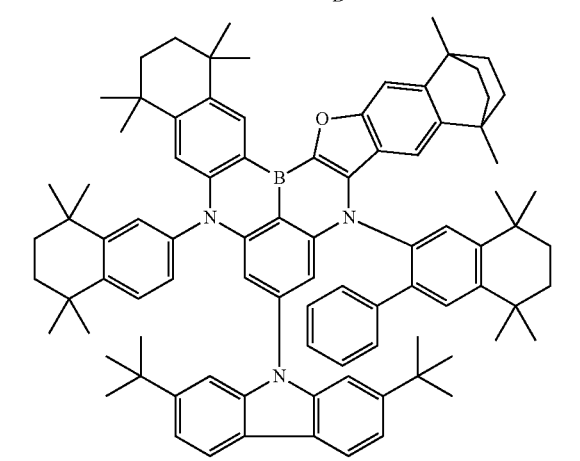
606
-continued
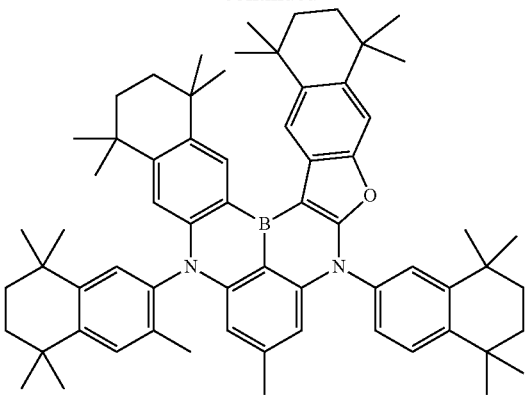
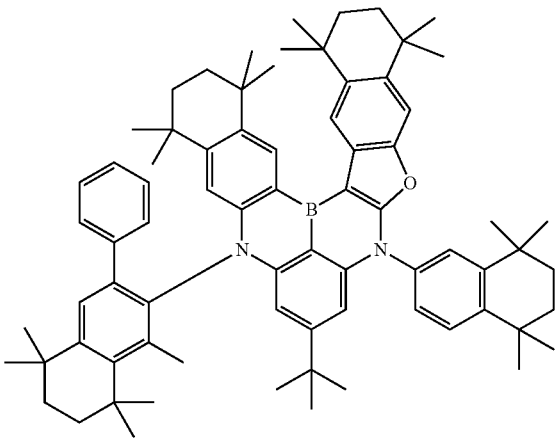
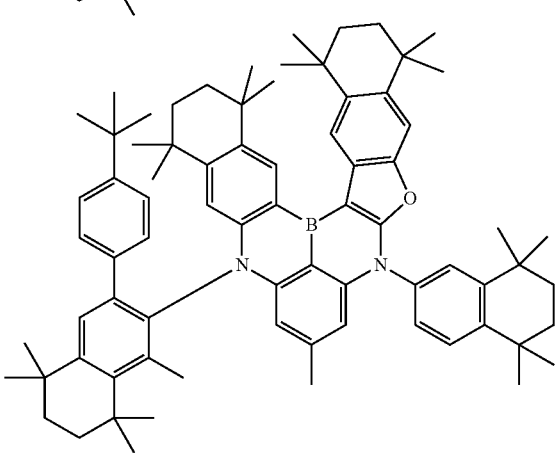
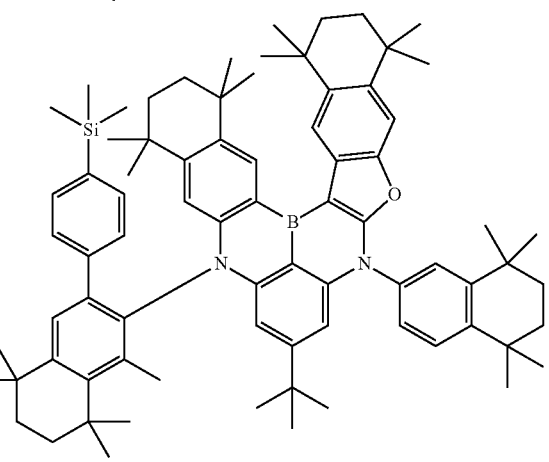

607
-continued
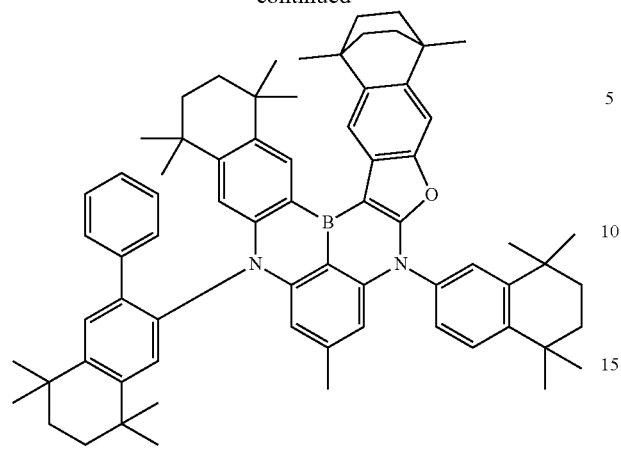
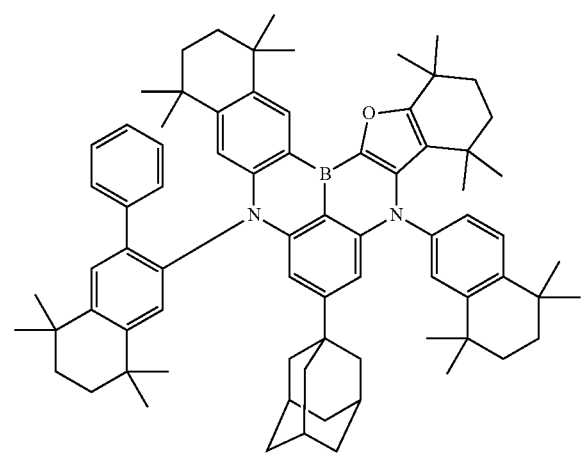
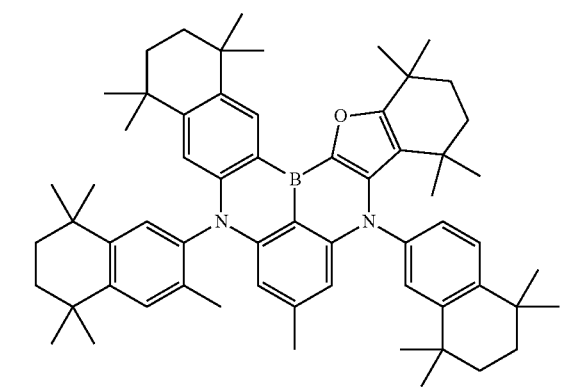
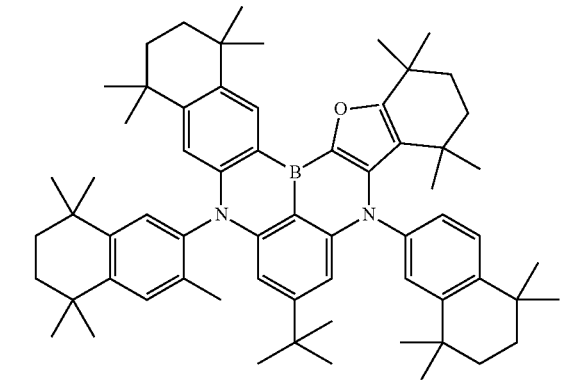
608
-continued
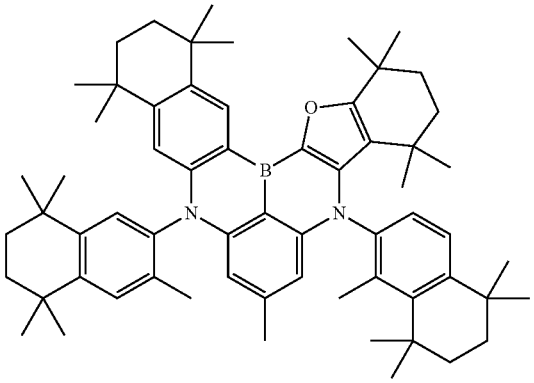
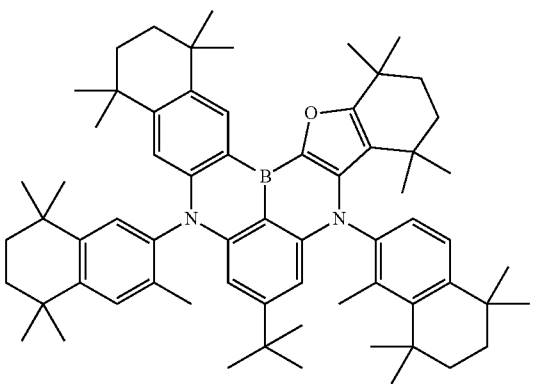
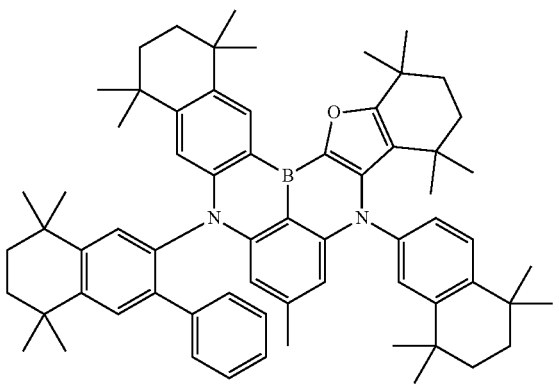
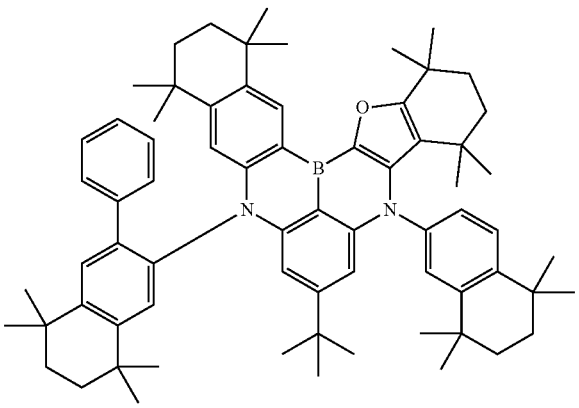

609
-continued
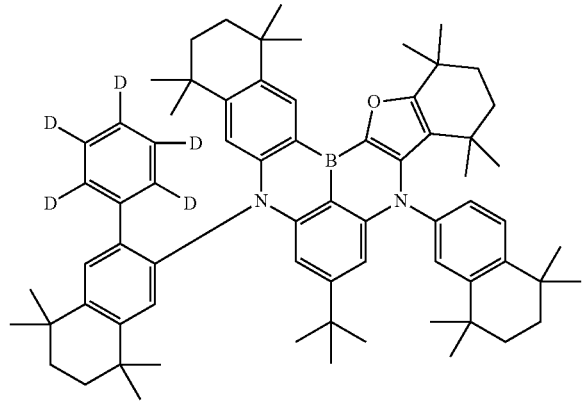
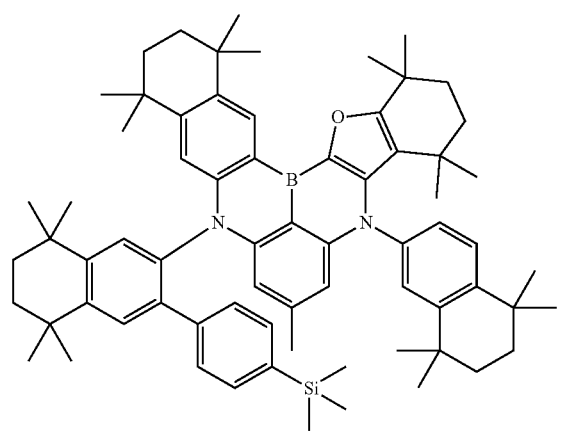
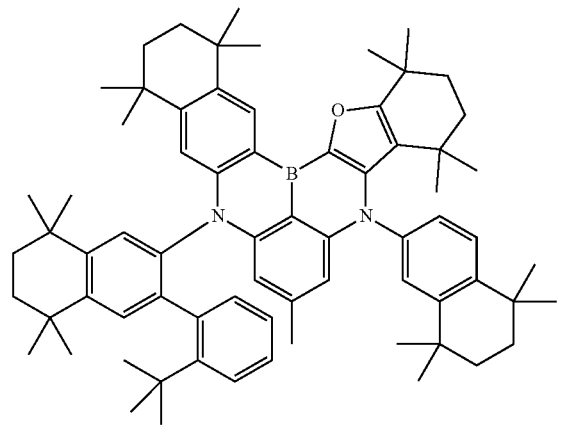
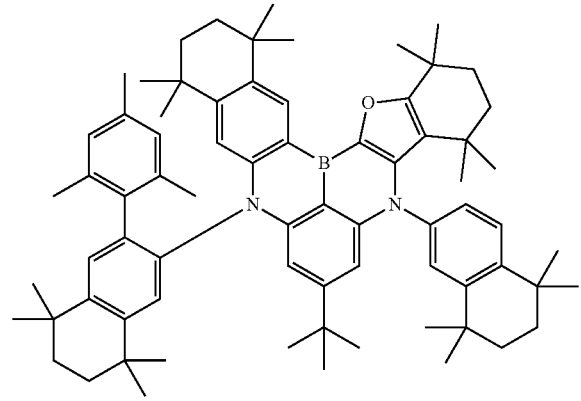
610
-continued
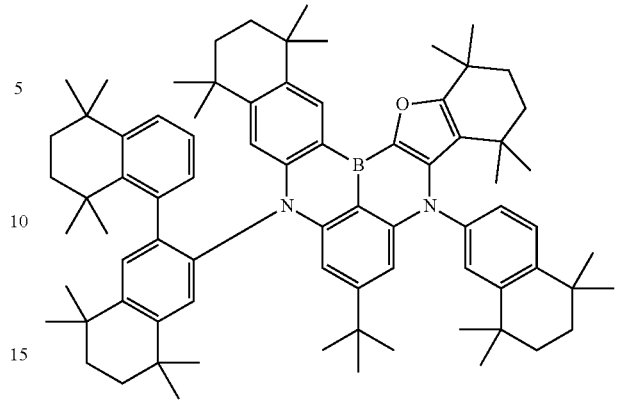
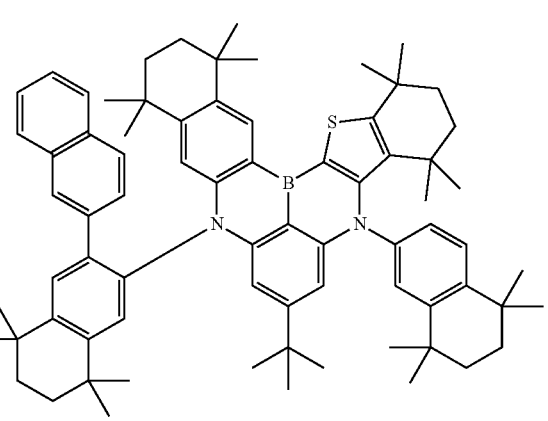
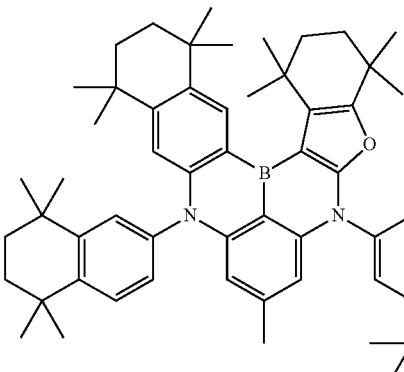
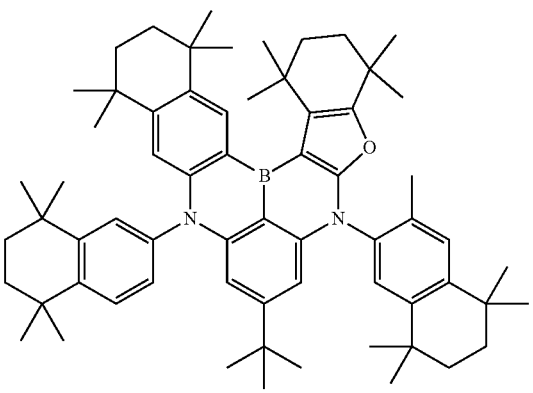

611
-continued
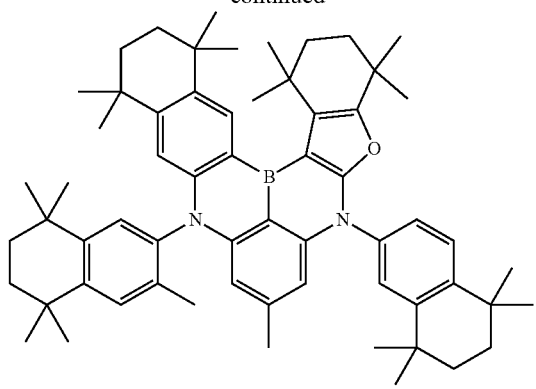
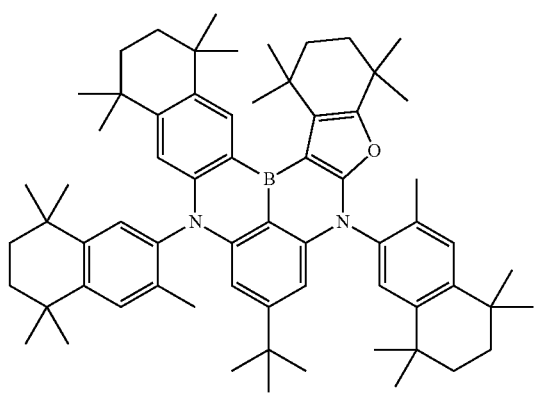
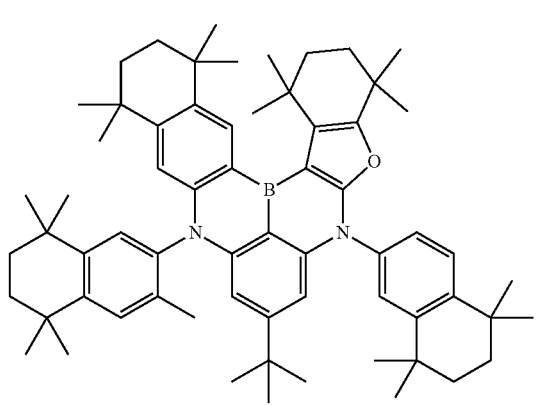
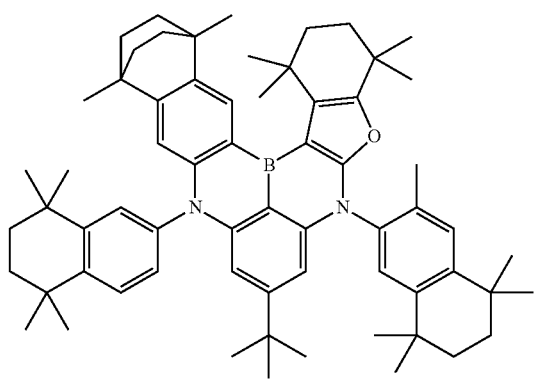
612
-continued
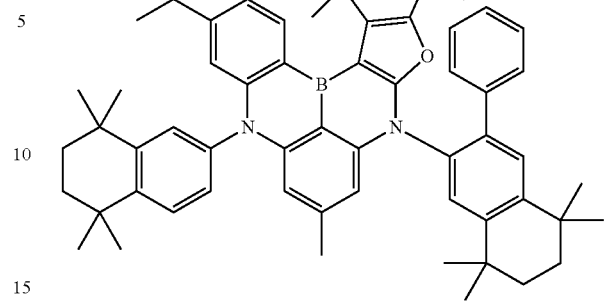
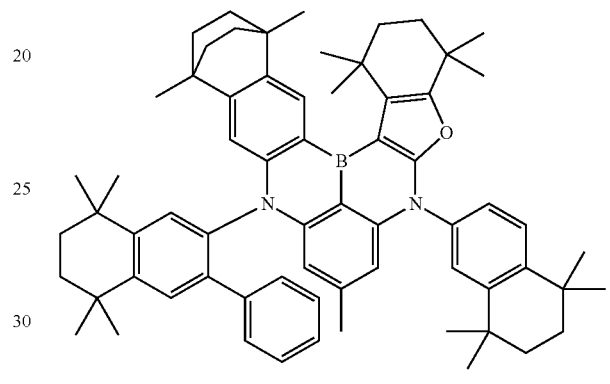
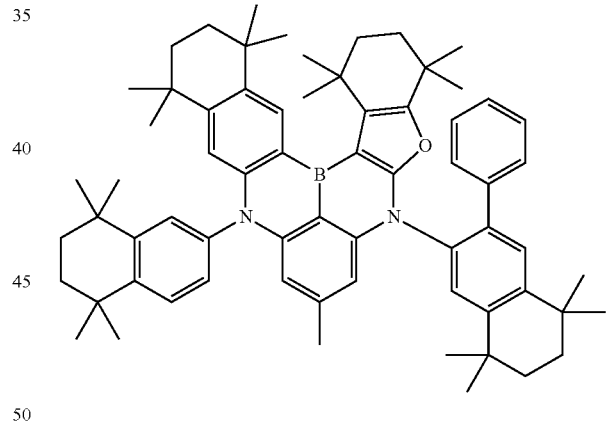
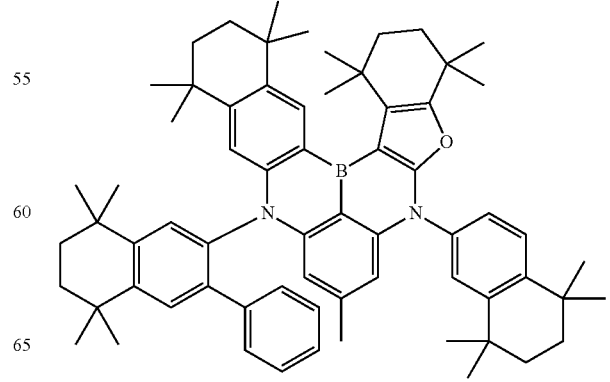

613
-continued
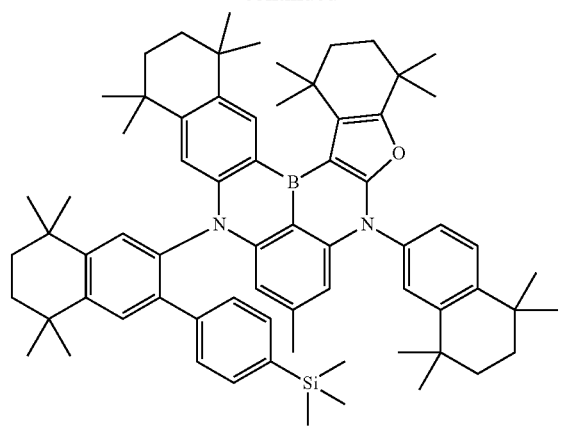
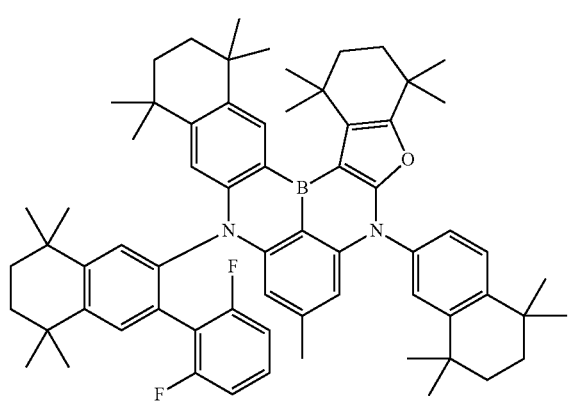
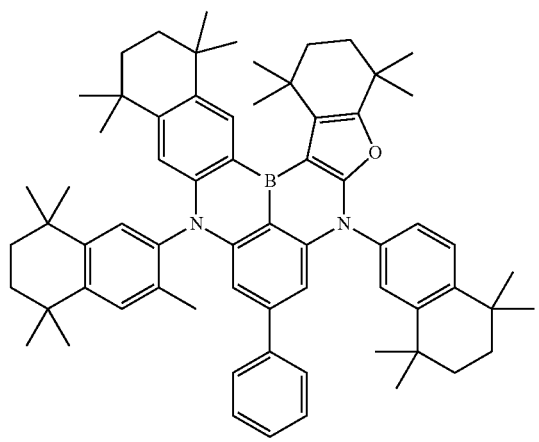
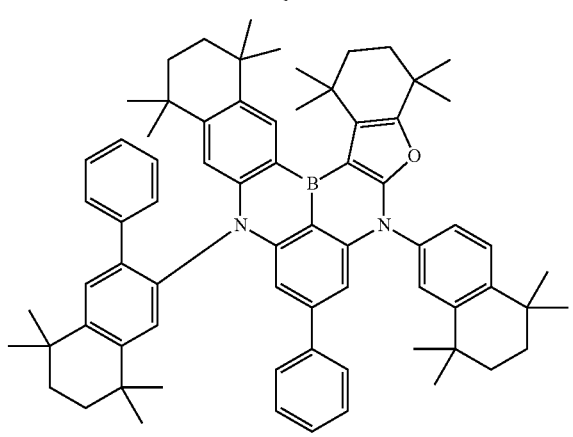
614
-continued
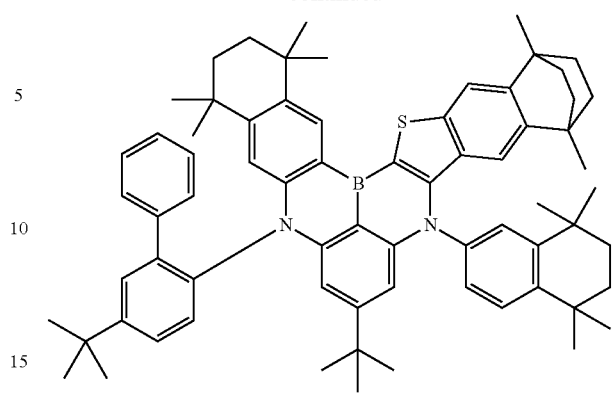
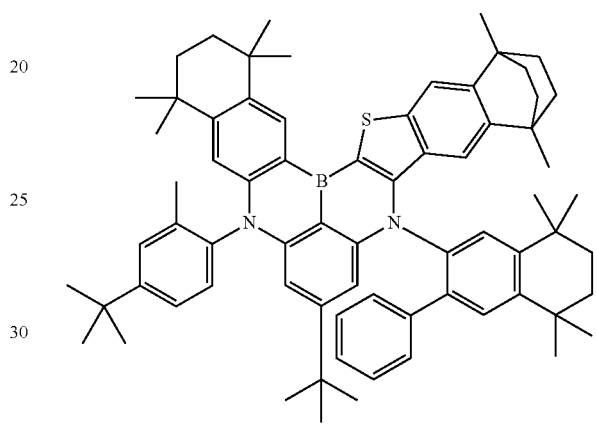
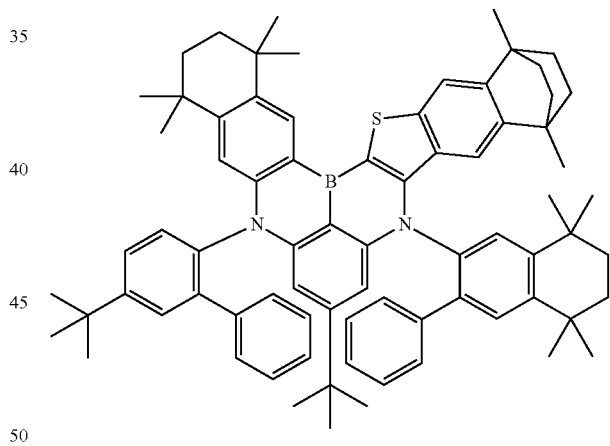
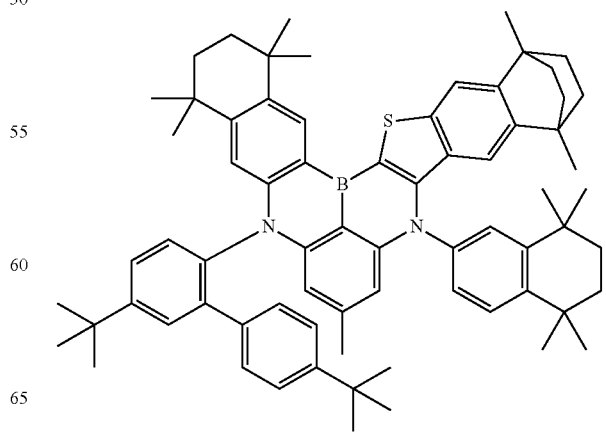

615
-continued
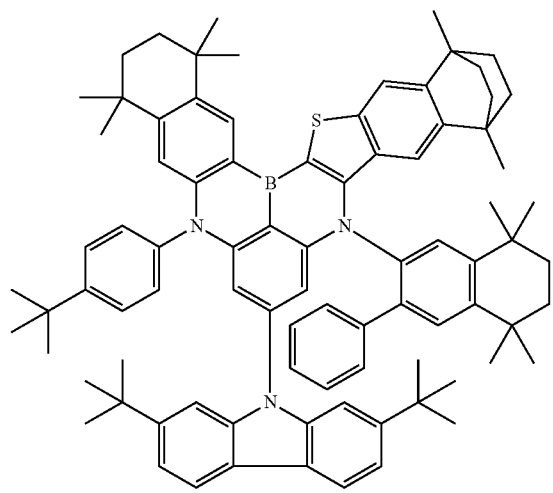
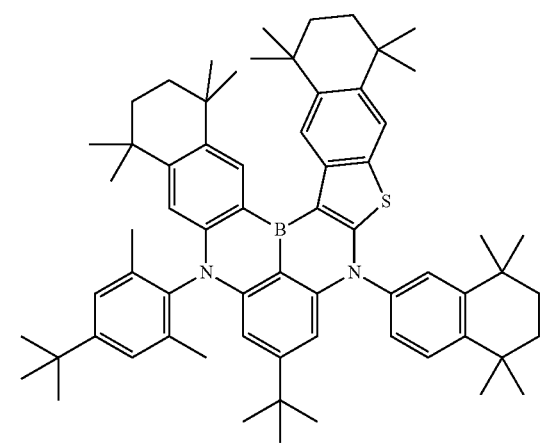
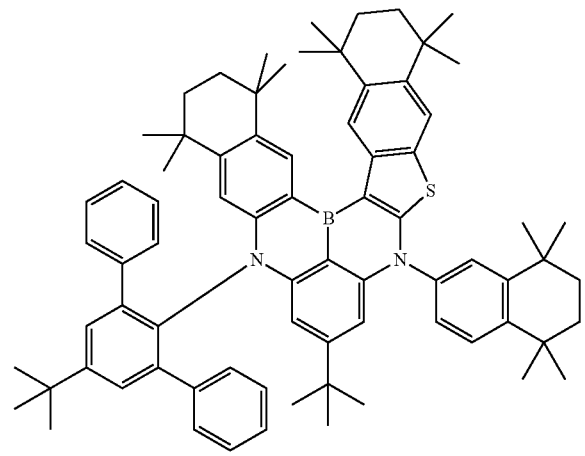
616
-continued
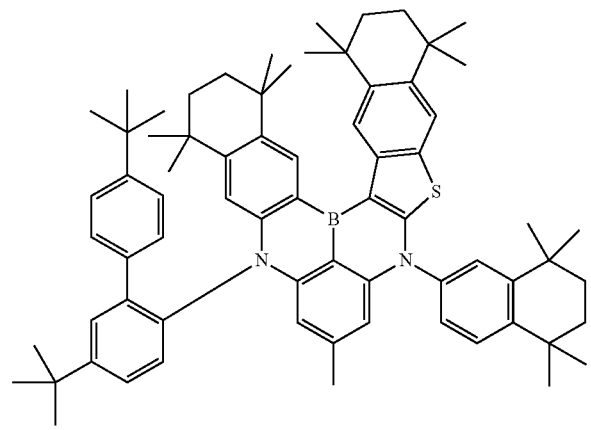
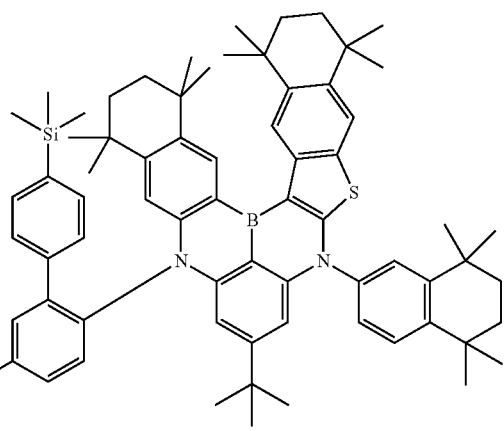
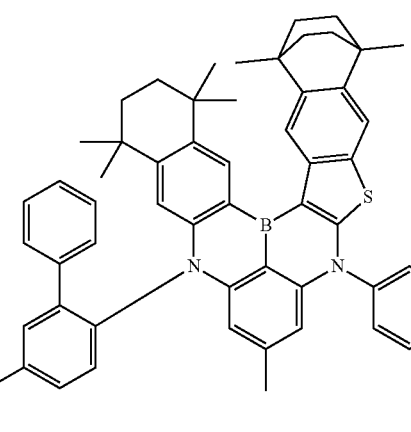

617
-continued
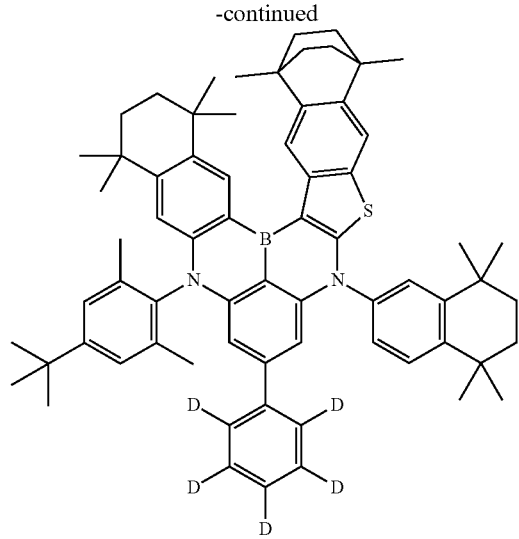
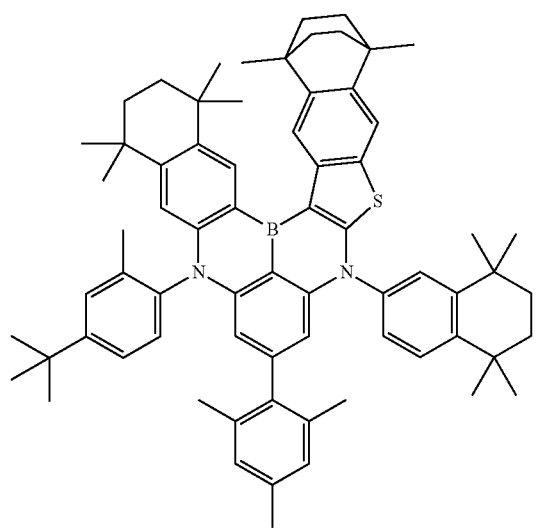
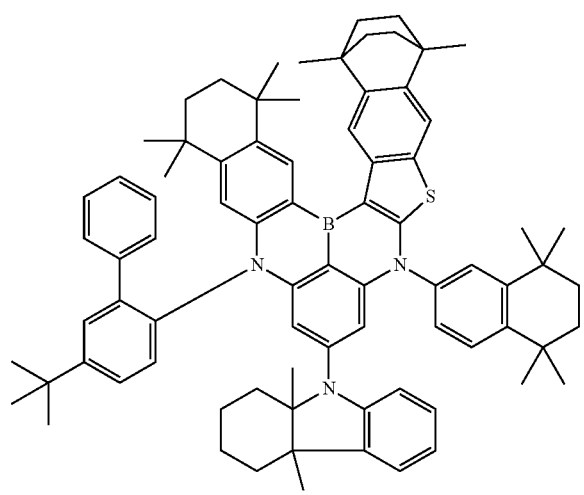
618
-continued
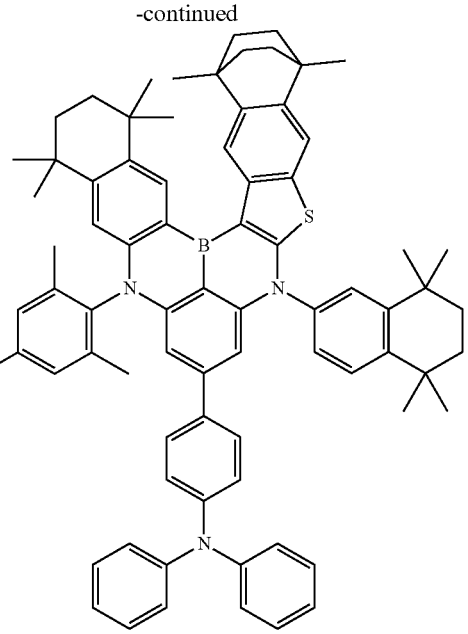
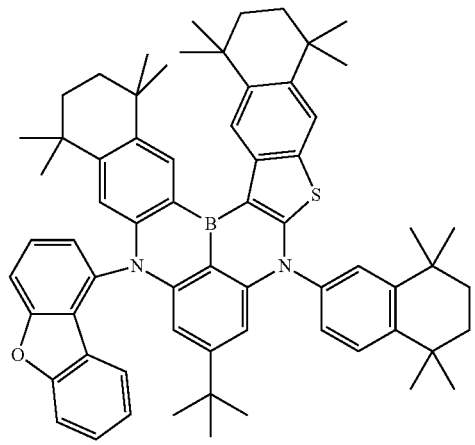
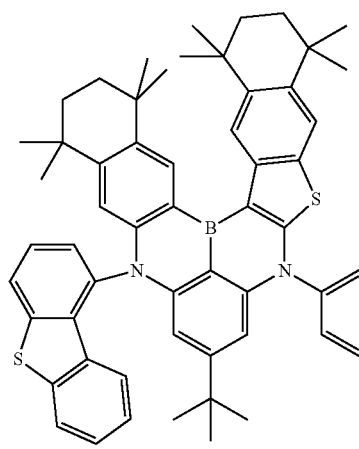

619
-continued
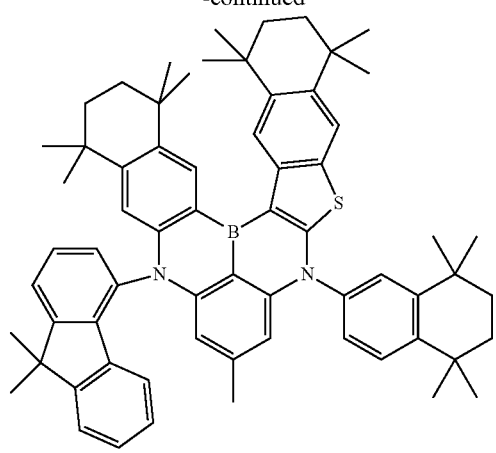
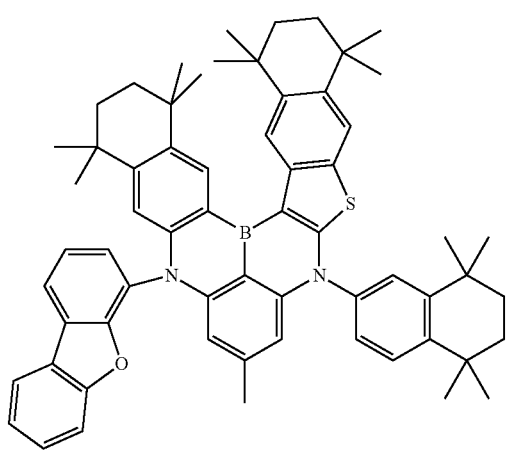
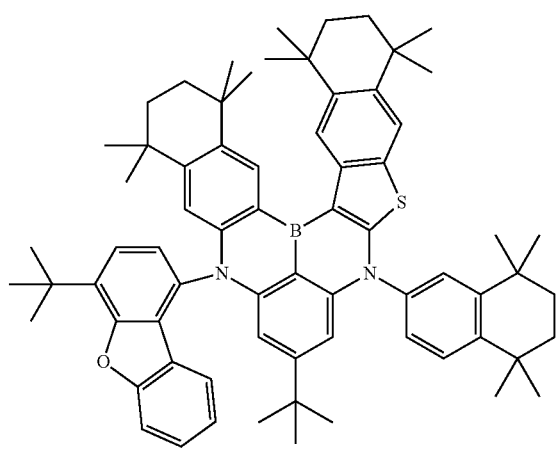
620
-continued
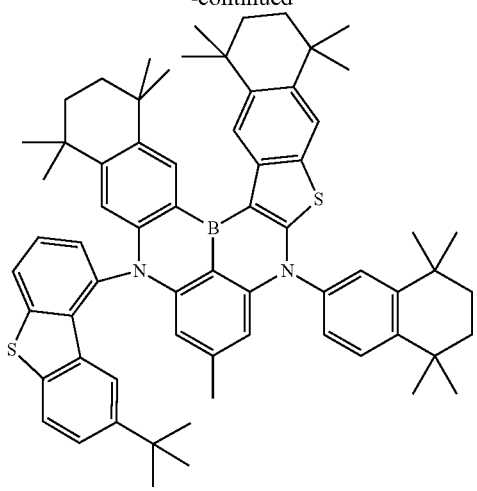
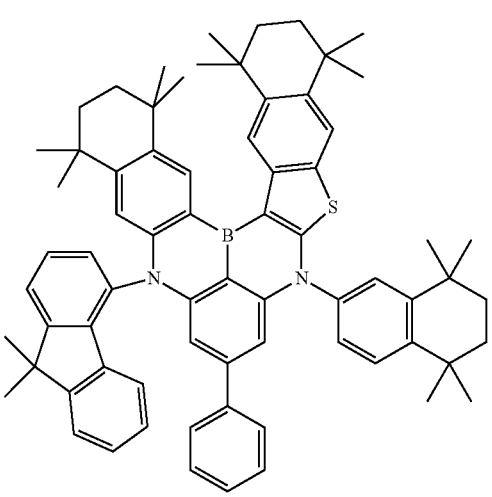
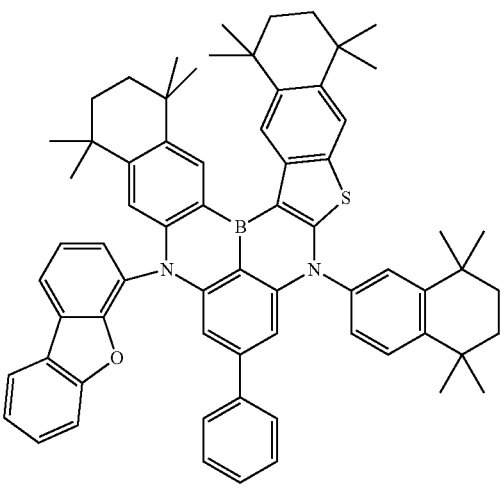

621
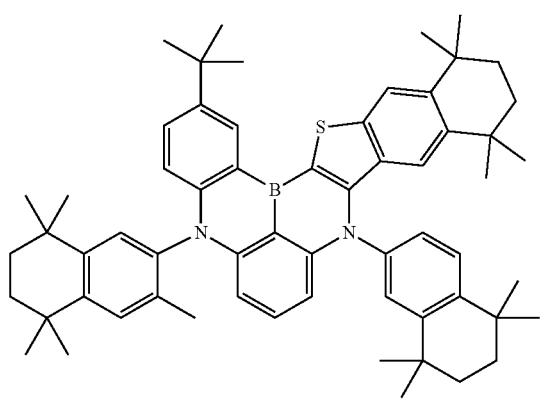
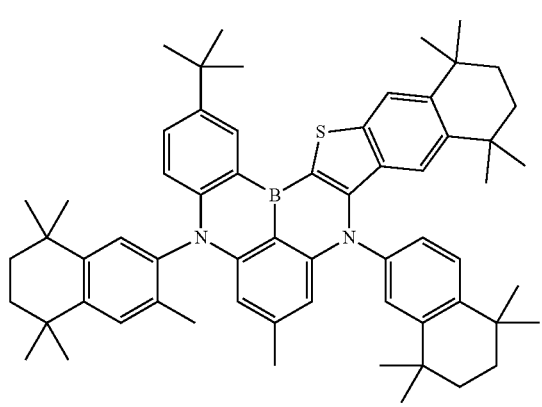
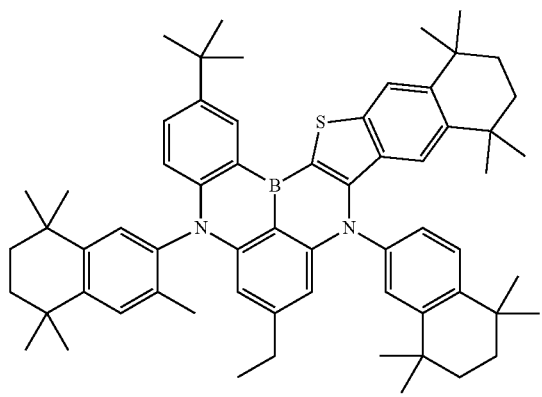
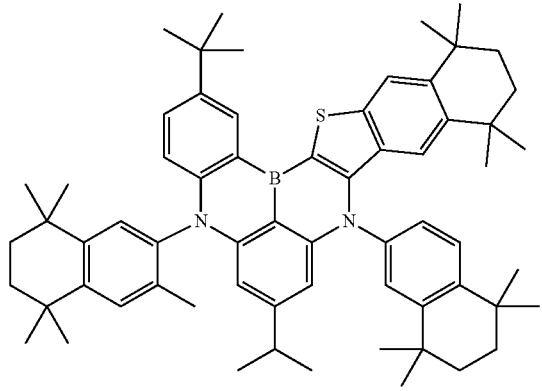
622
-continued
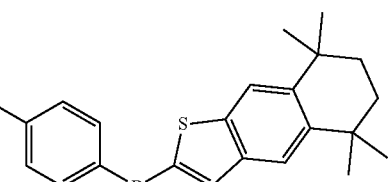
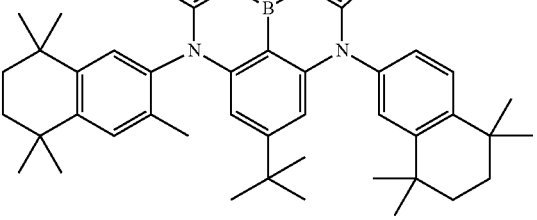
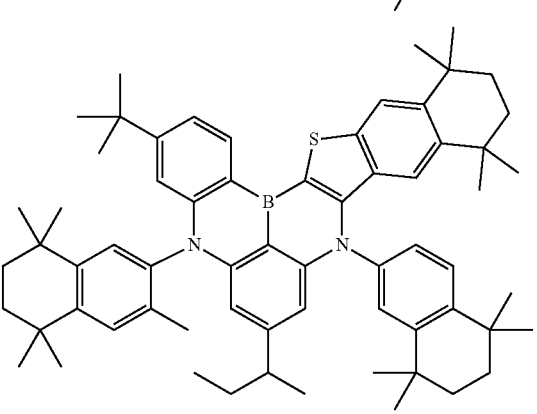
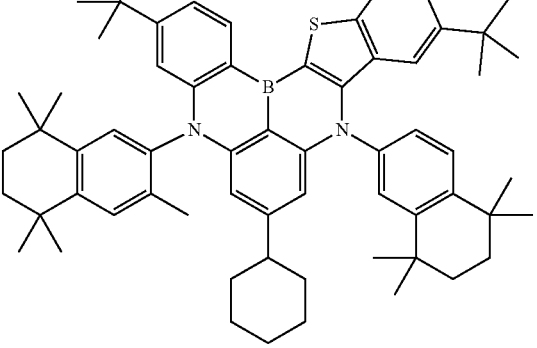
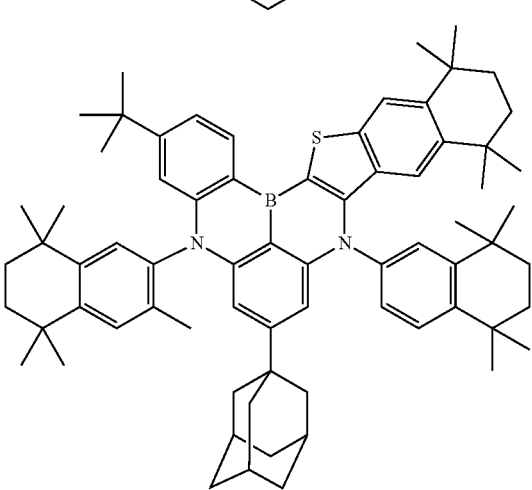

623
-continued
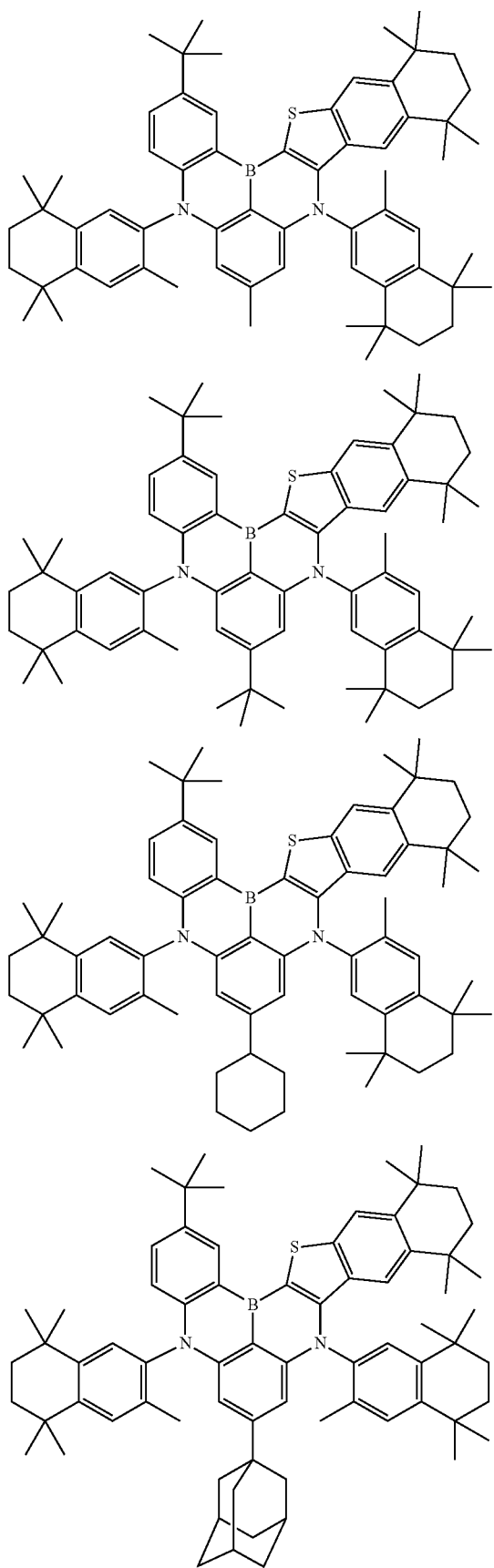
624
-continued
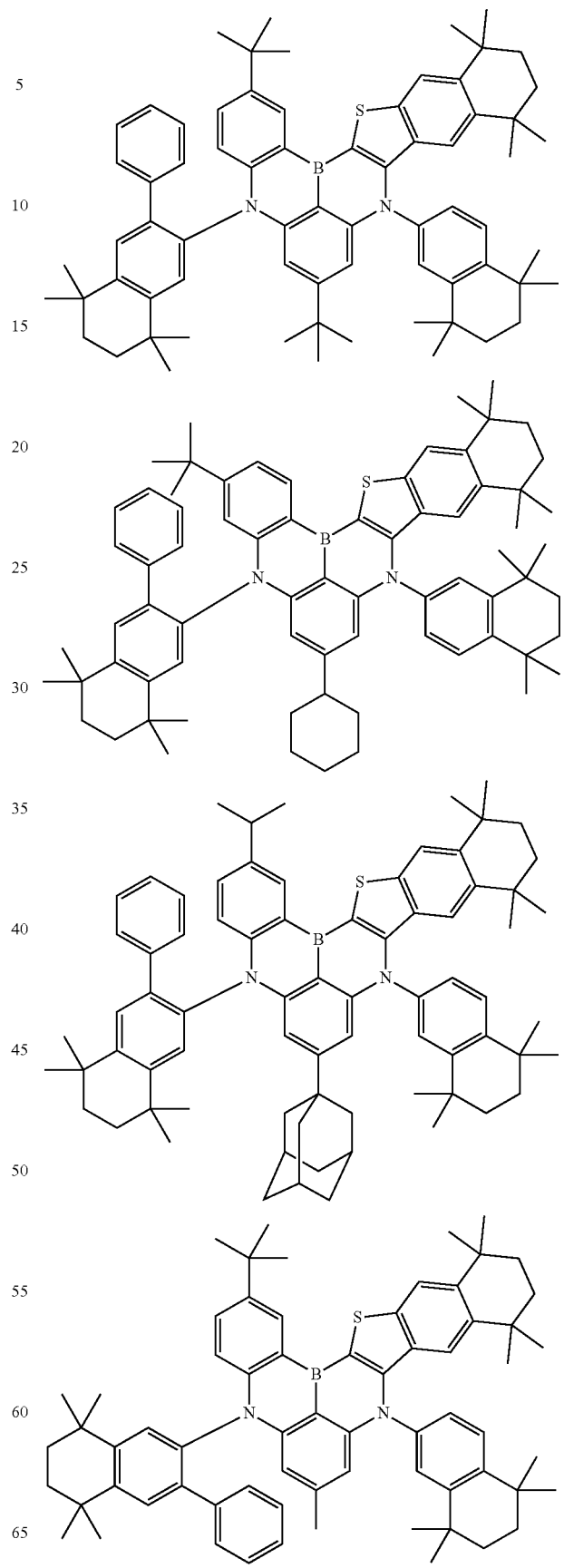

625
-continued
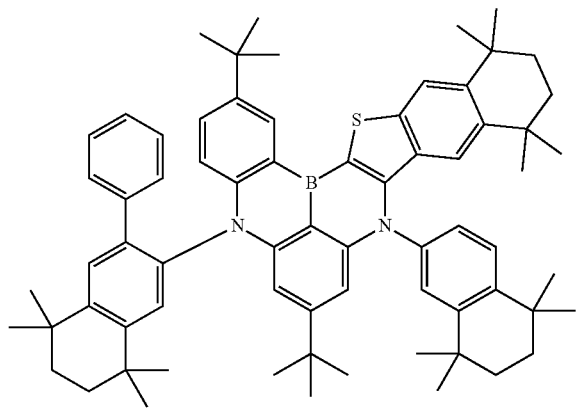
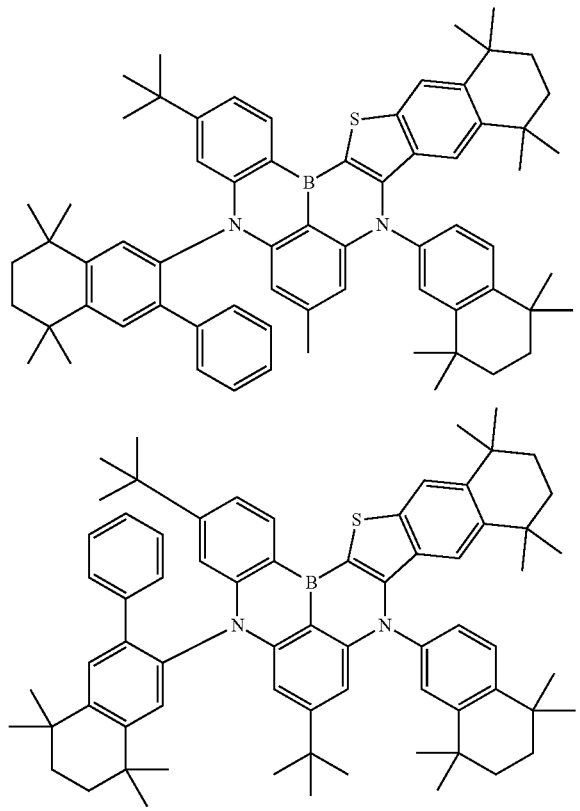
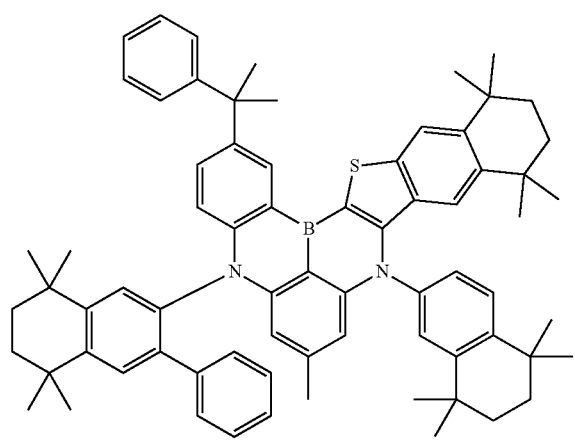
626
-continued
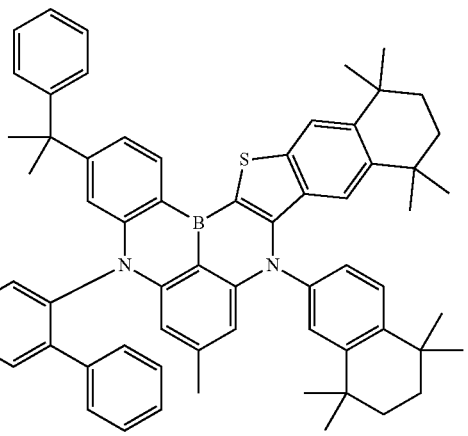
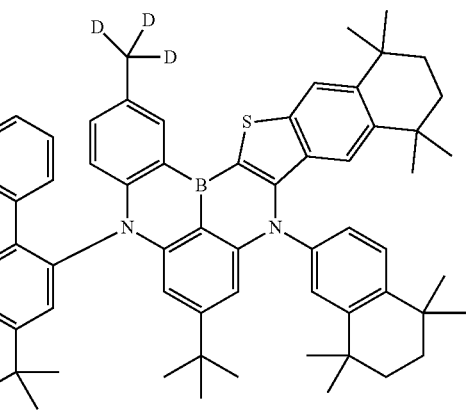
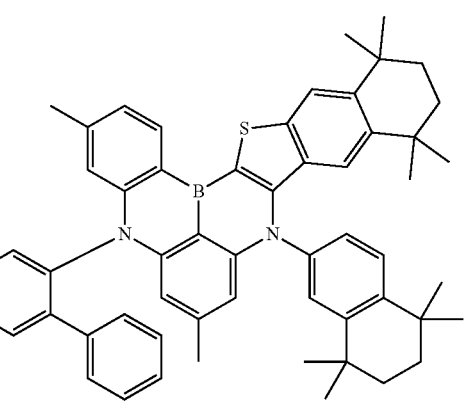

627
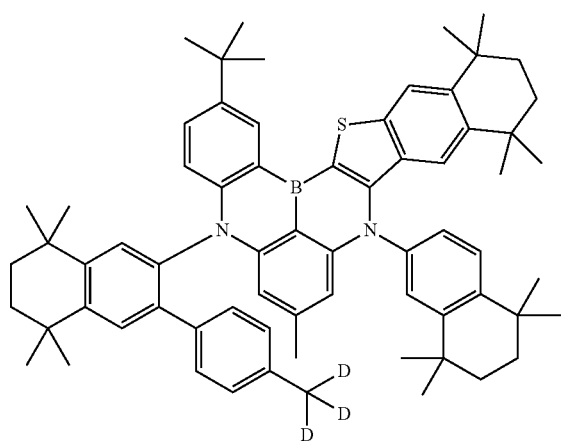
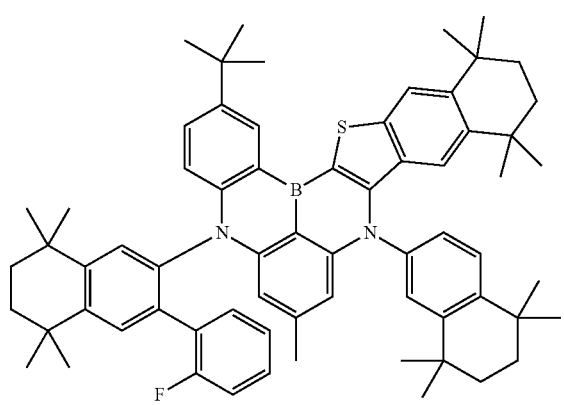
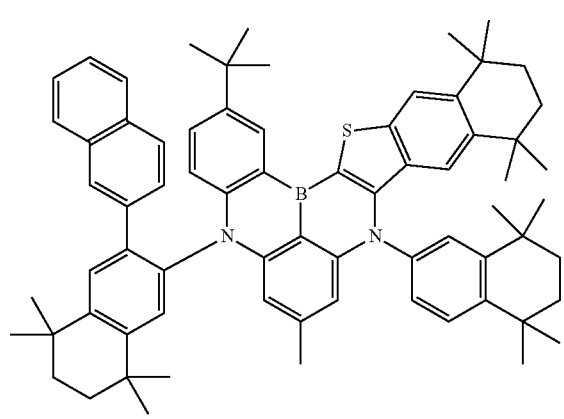
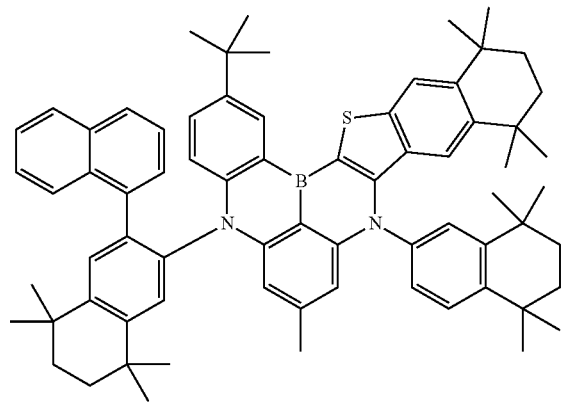
628
-continued
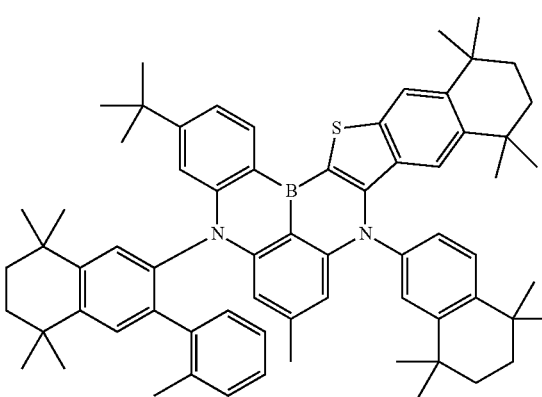
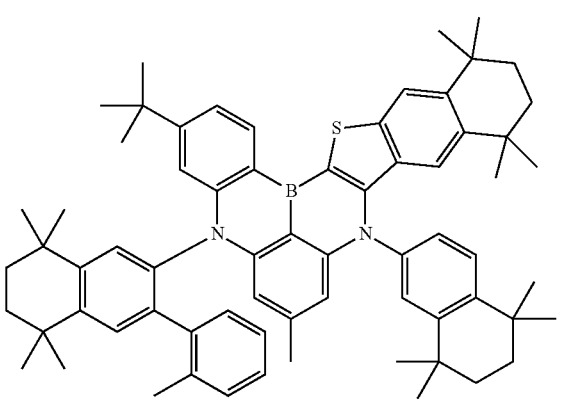
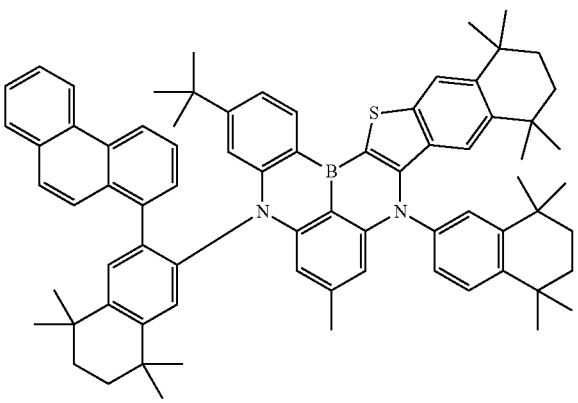
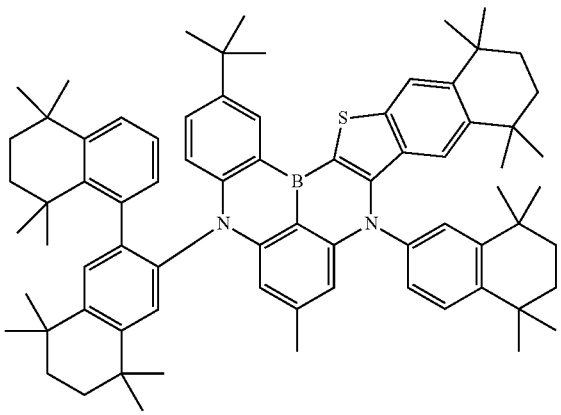

629
-continued
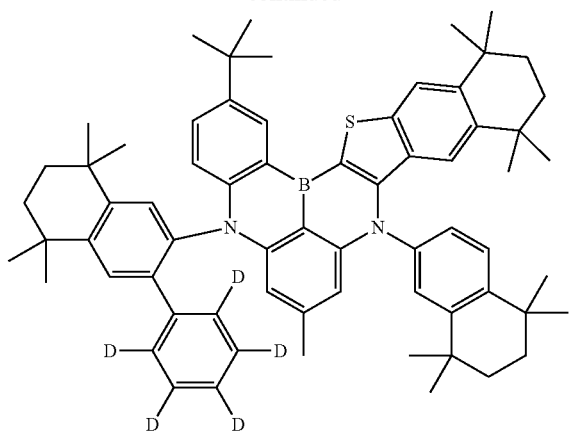
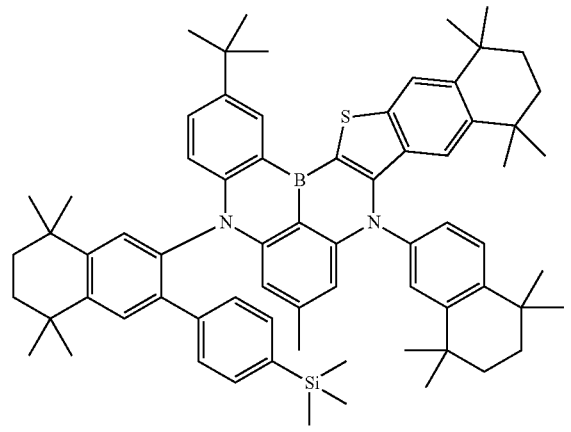
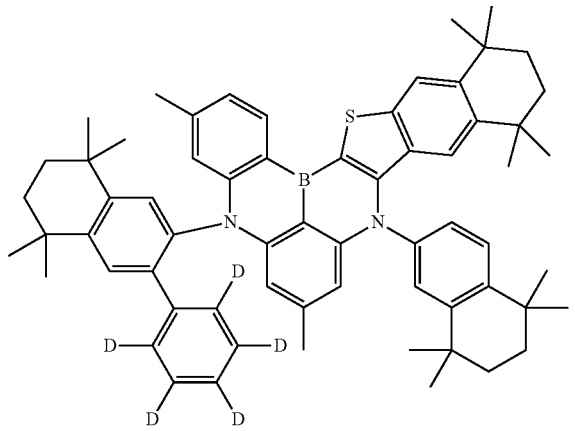
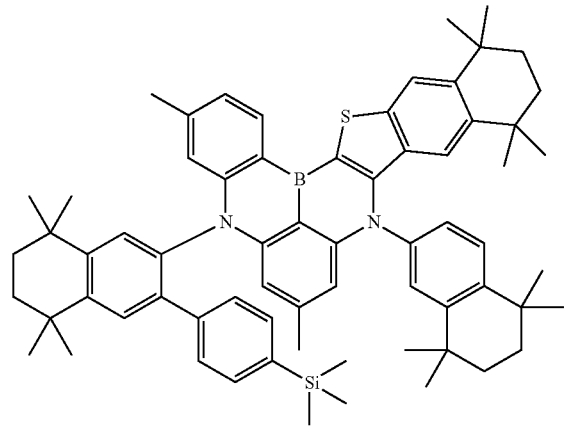
630
-continued
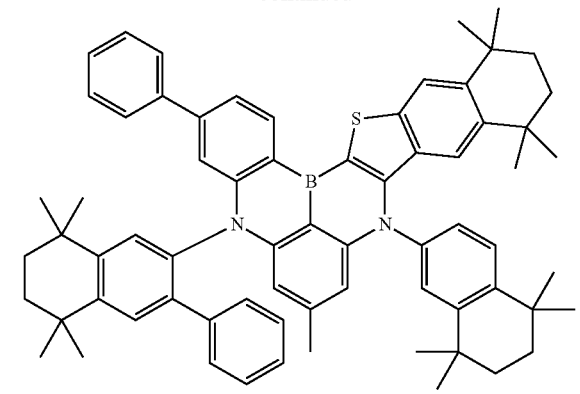
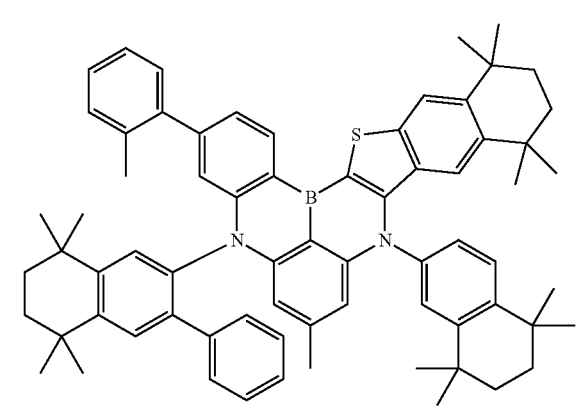
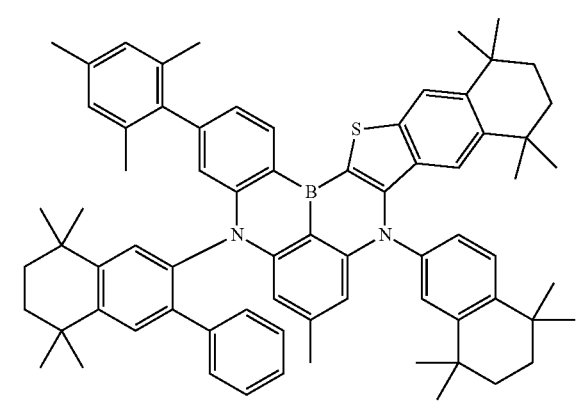

631
-continued
632
-continued
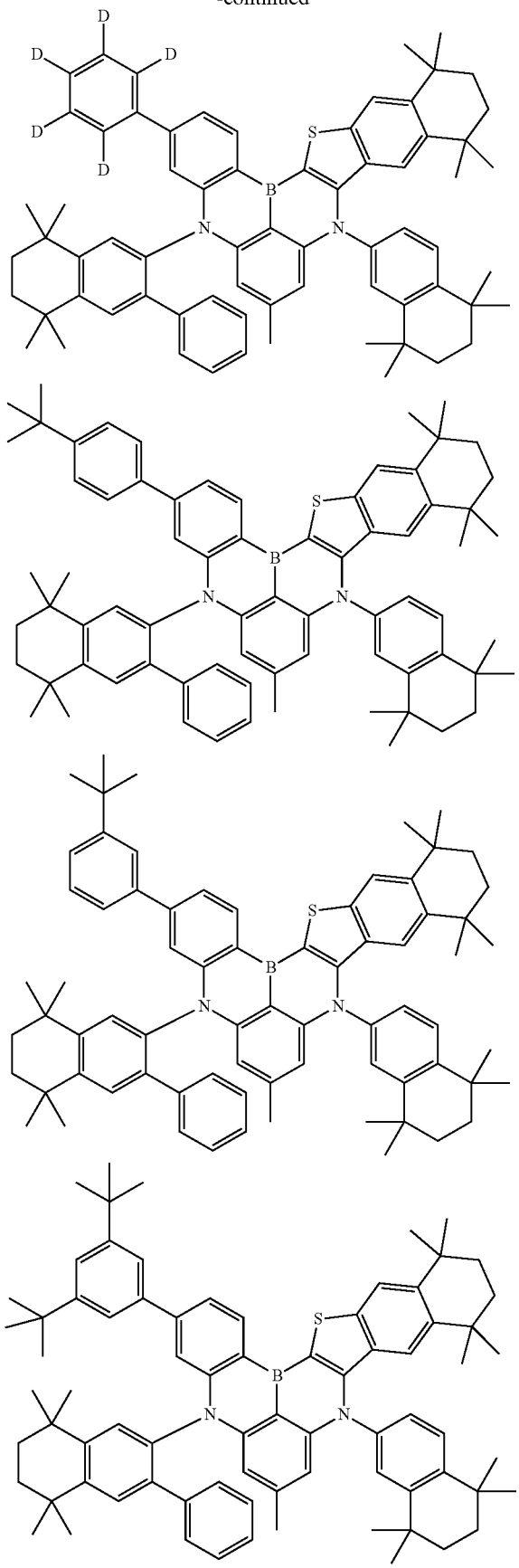
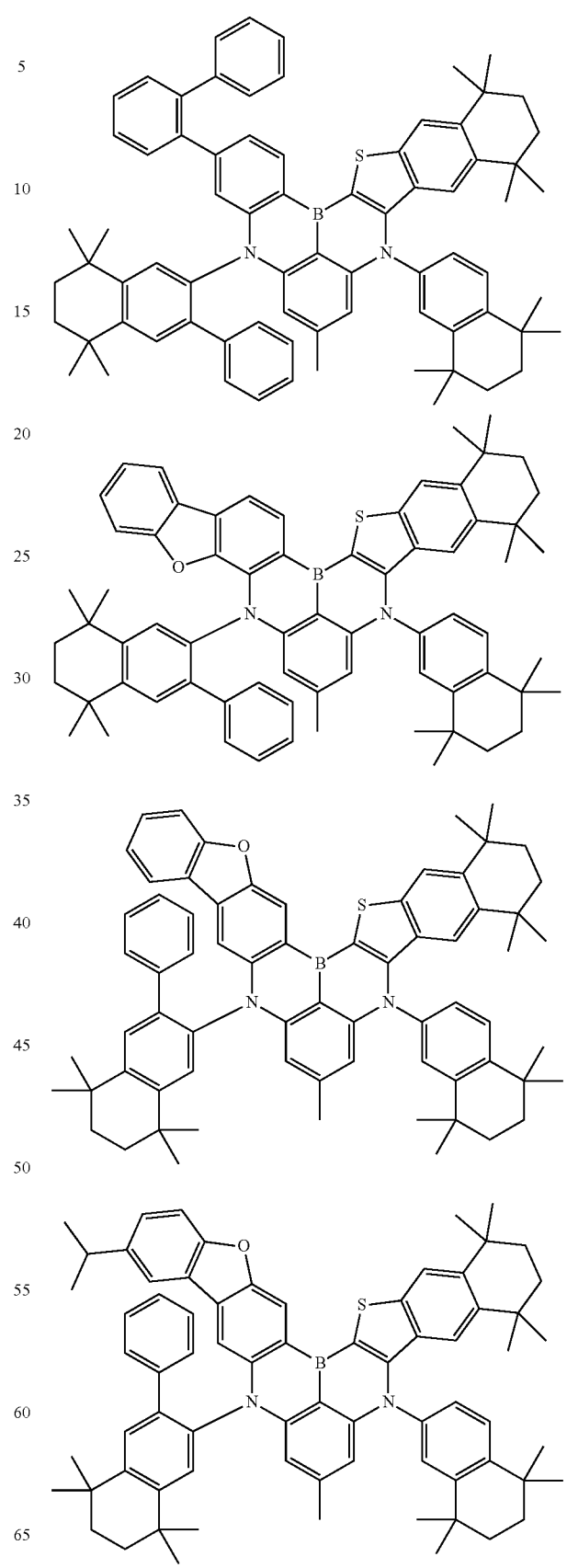

633
-continued
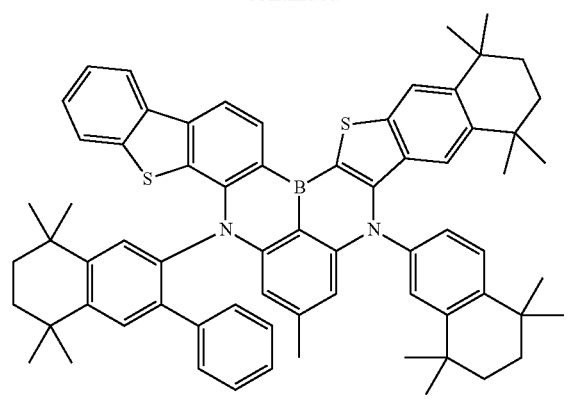
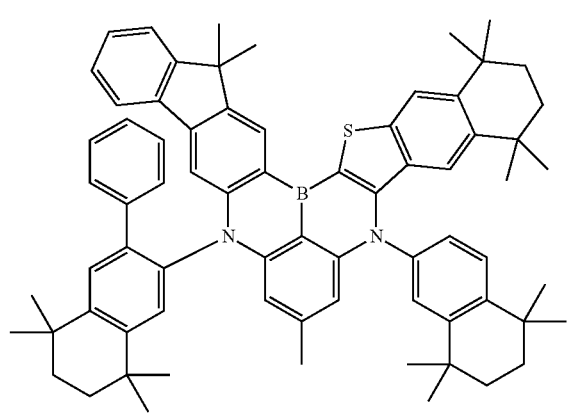
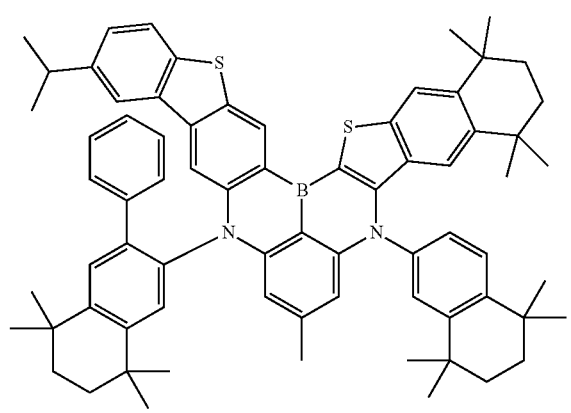
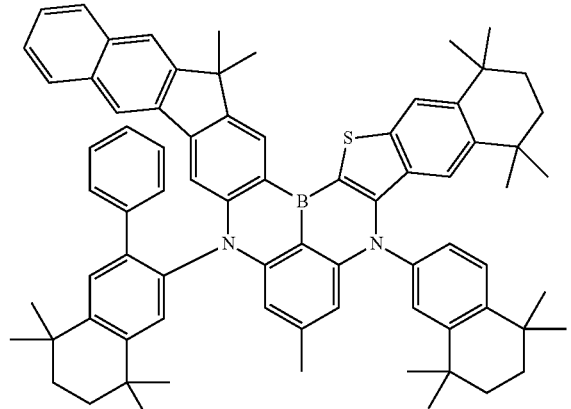
634
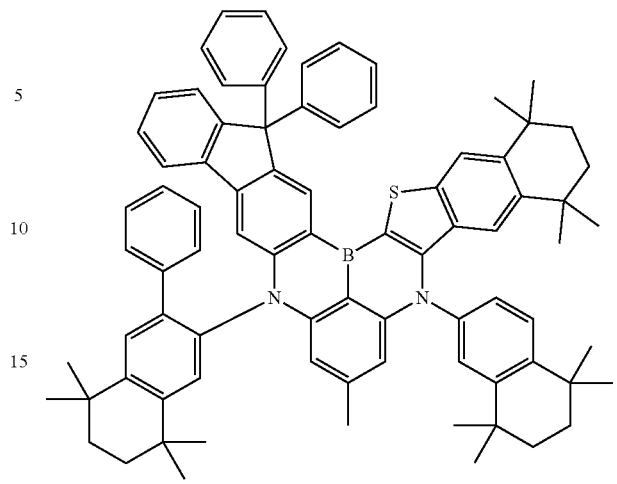
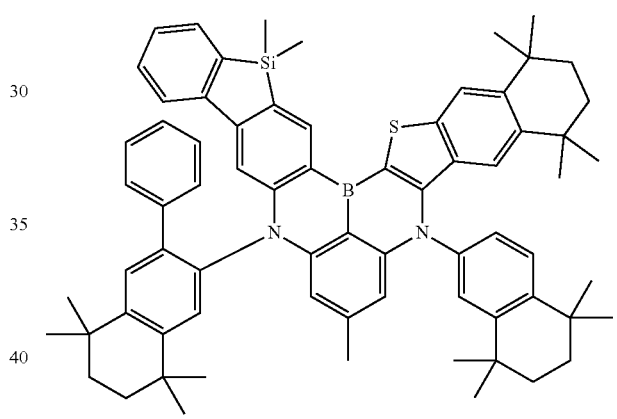
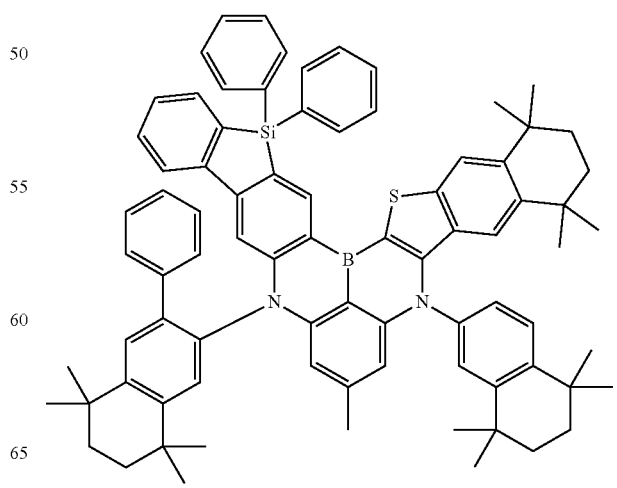

635
-continued
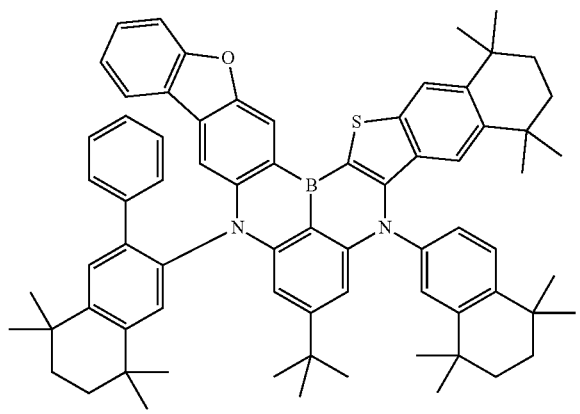
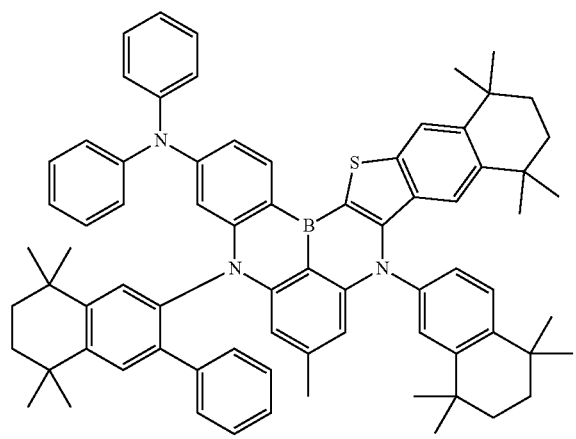
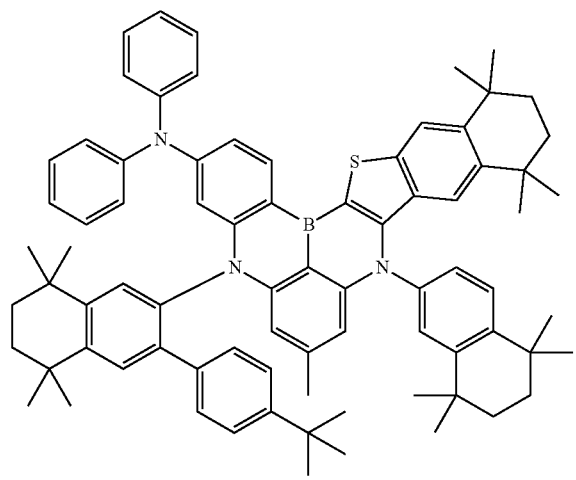
636
-continued
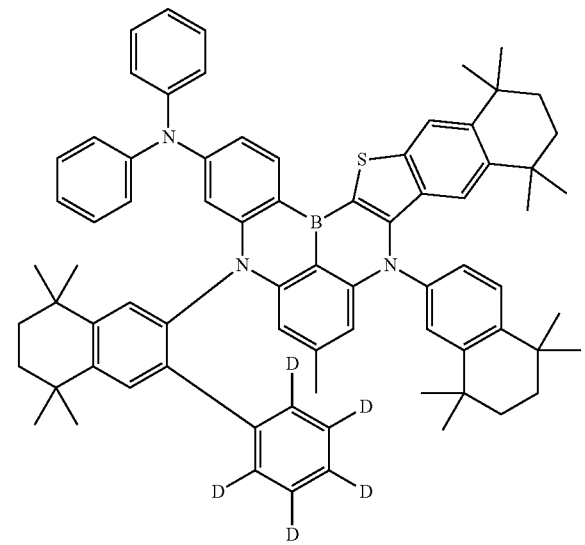
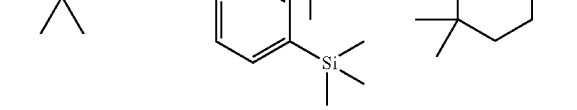
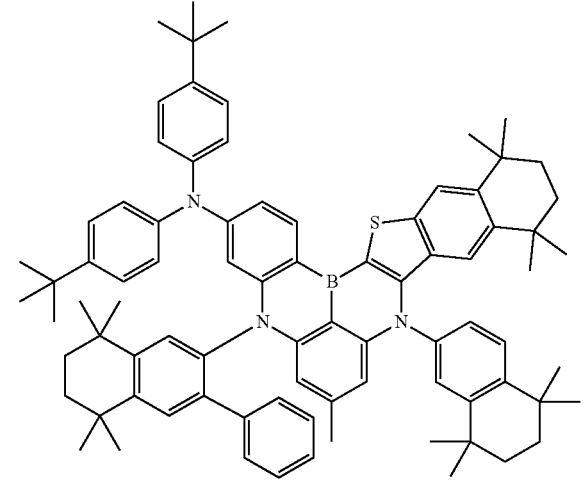

637
-continued
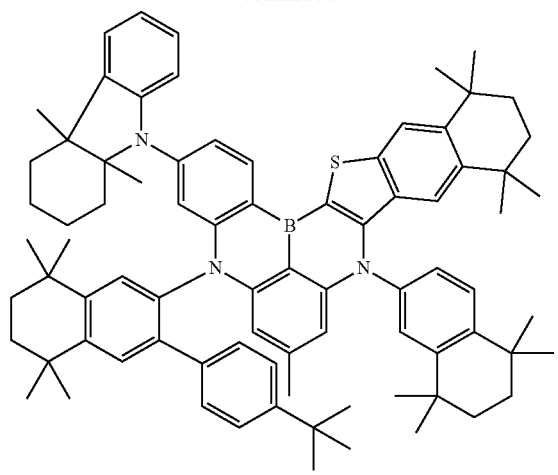
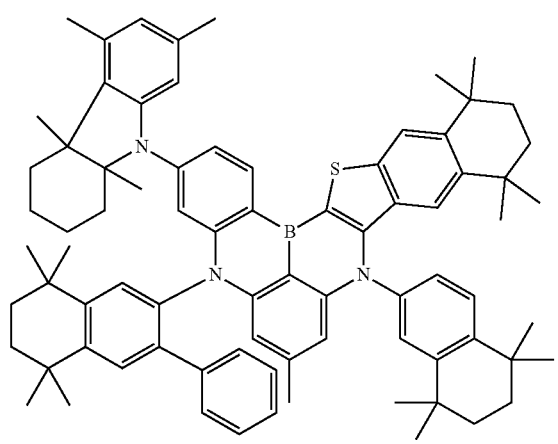
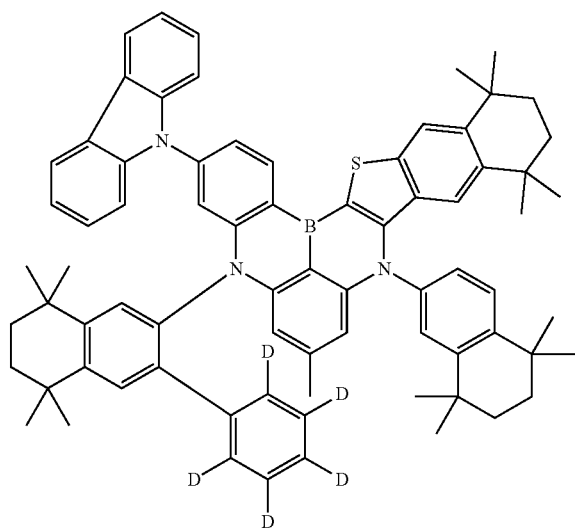
638
-continued
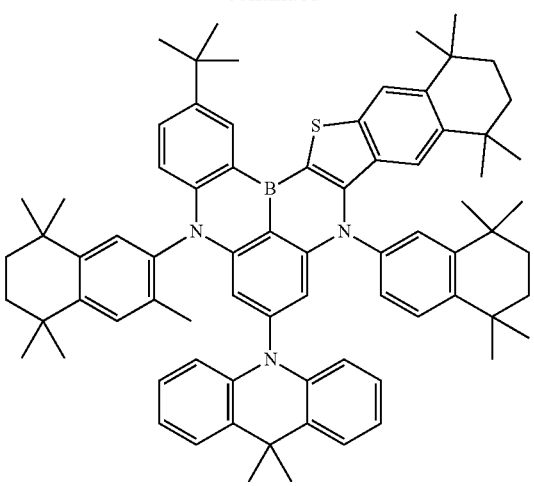
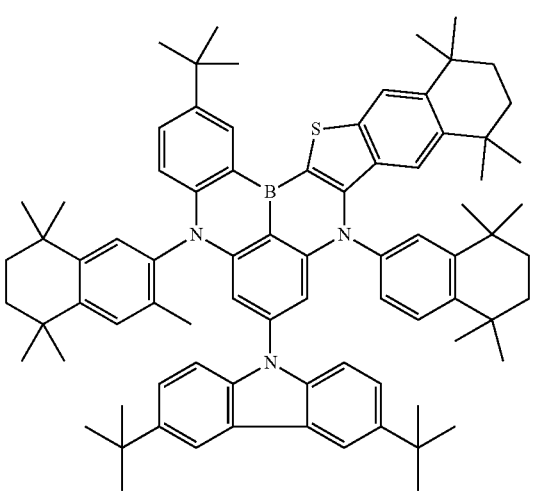
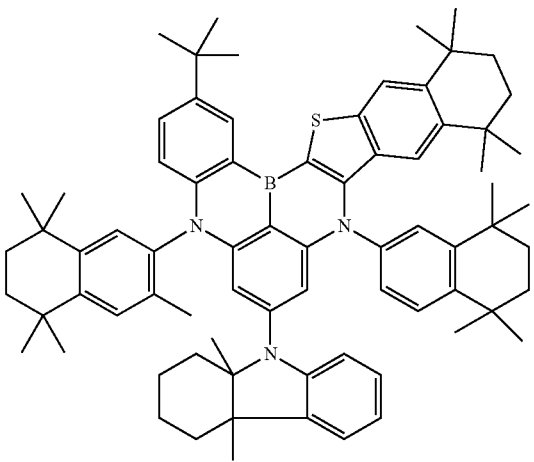

639
-continued
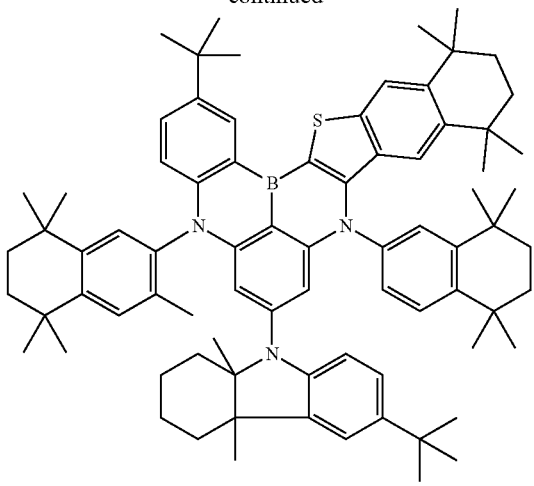
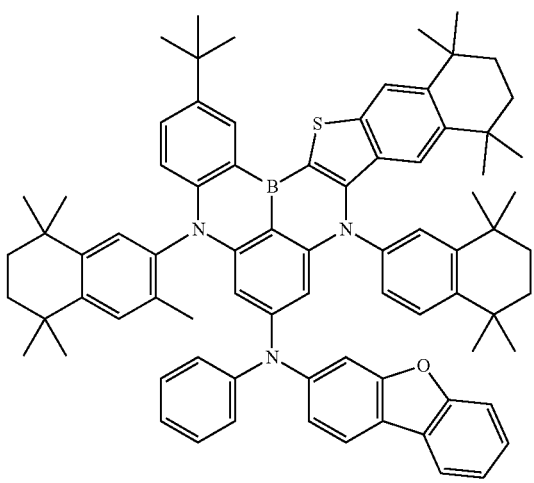
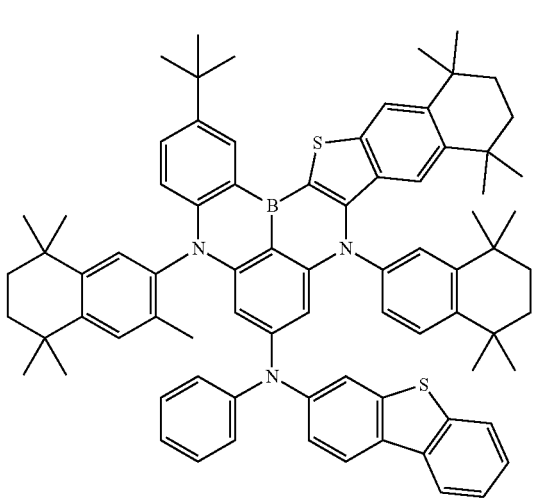
640
-continued
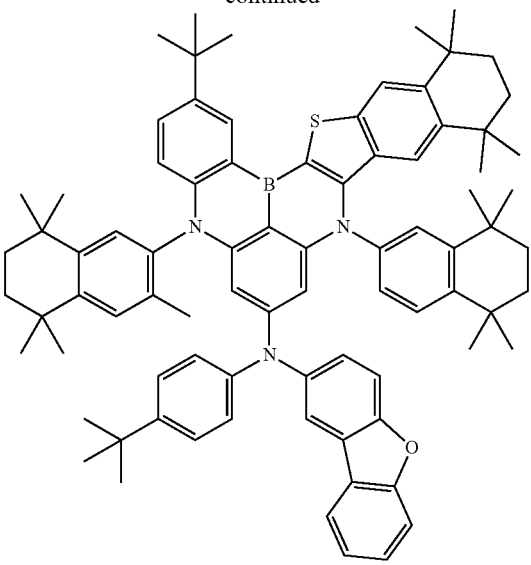
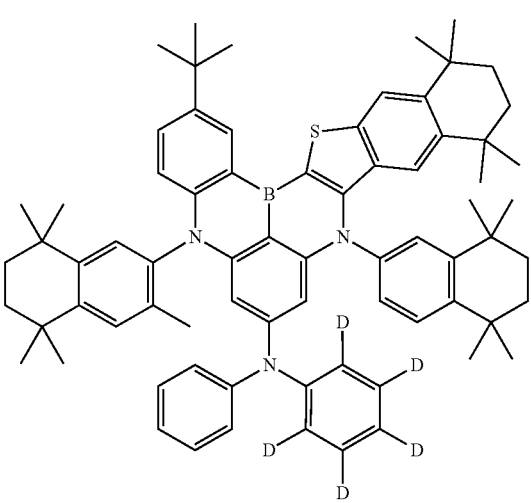
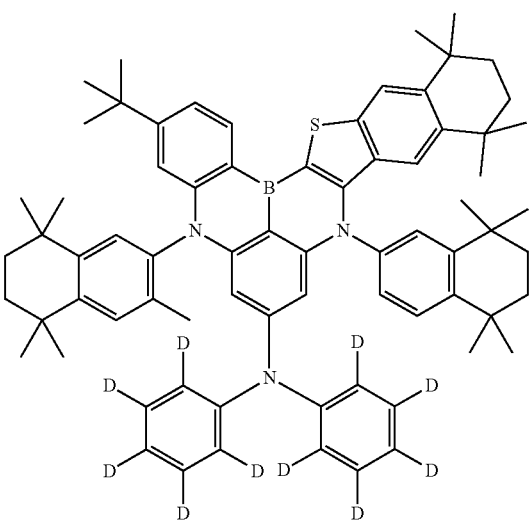

641
-continued
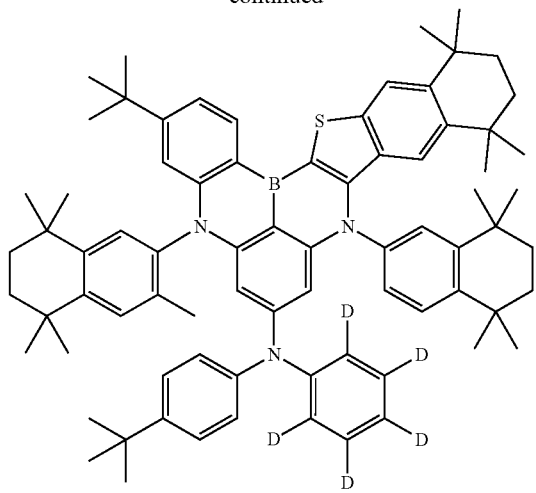
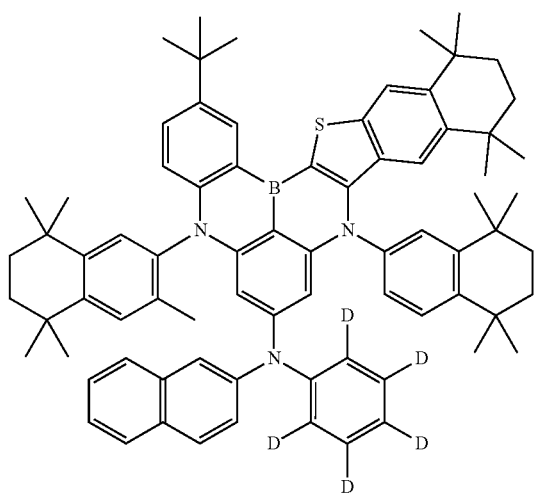
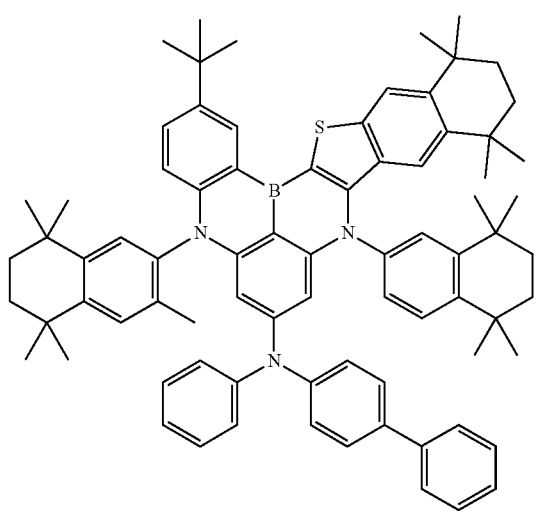
642
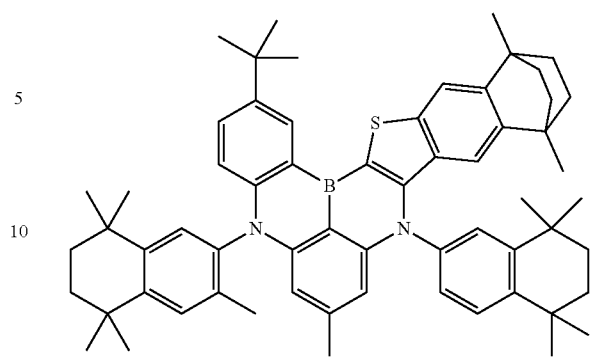
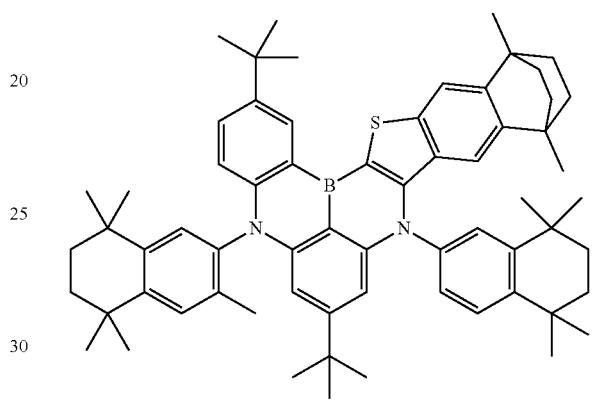
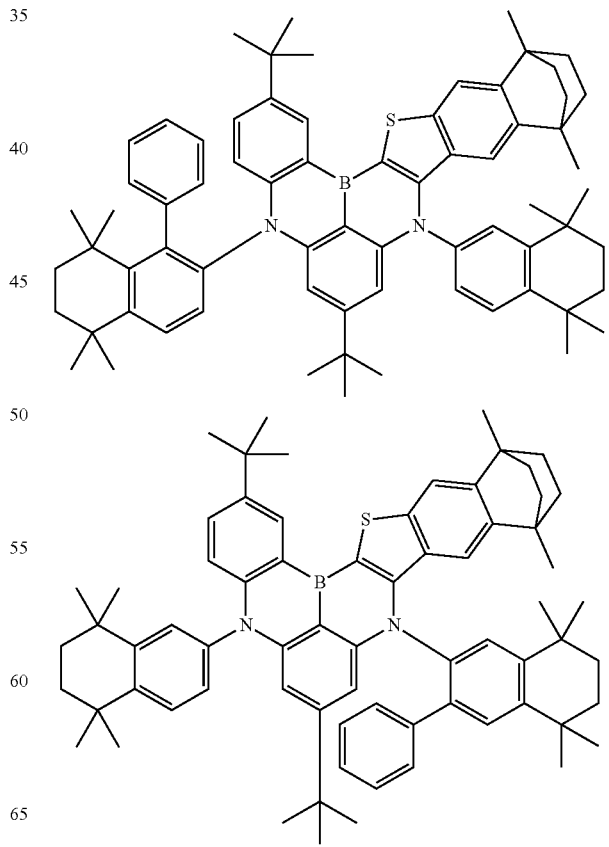

643
-continued
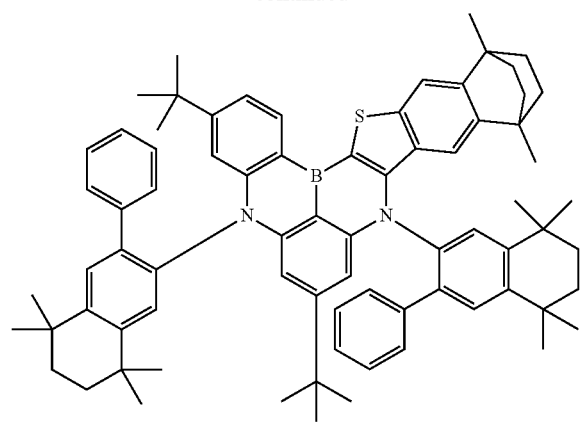
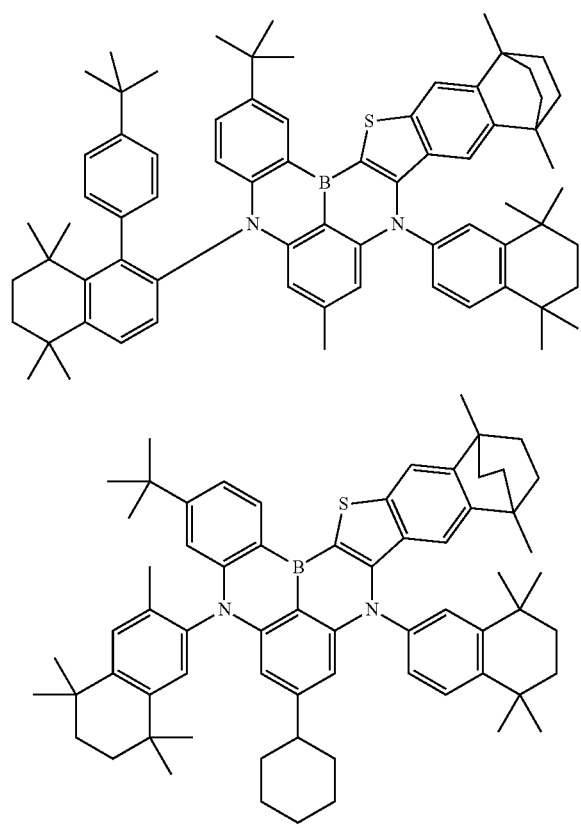
644
-continued
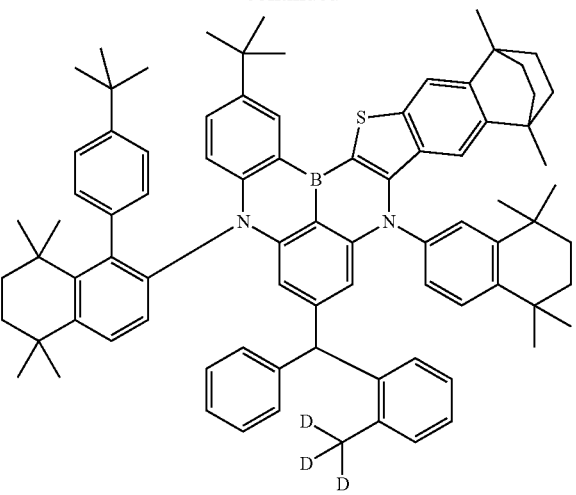
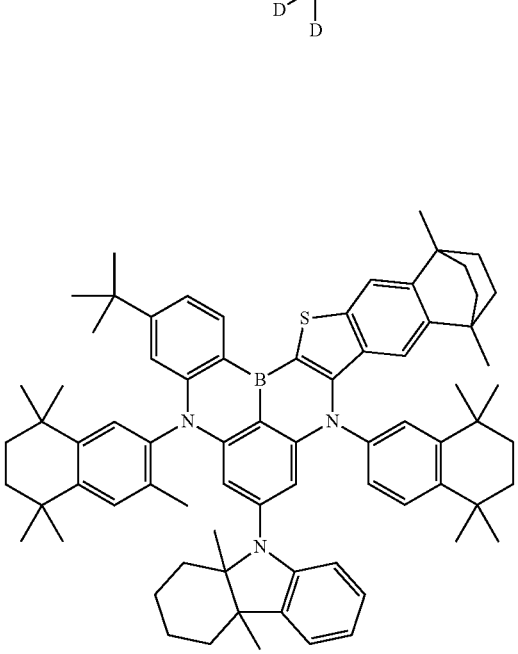
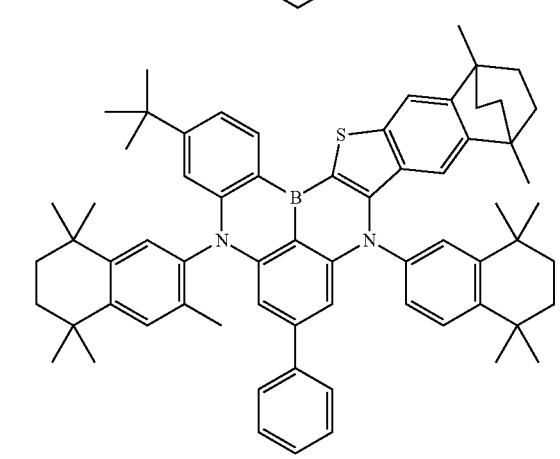
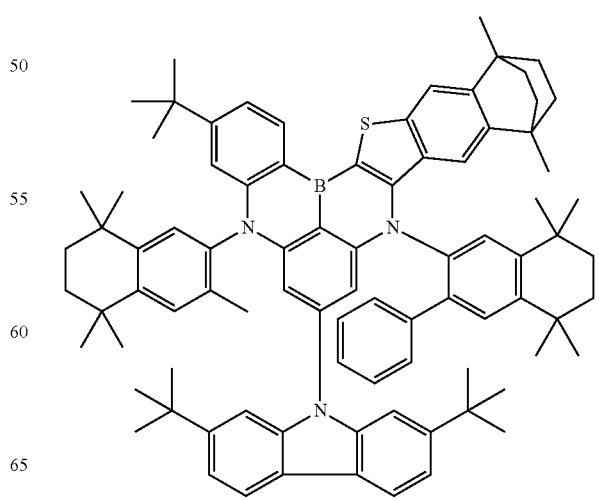

645
-continued
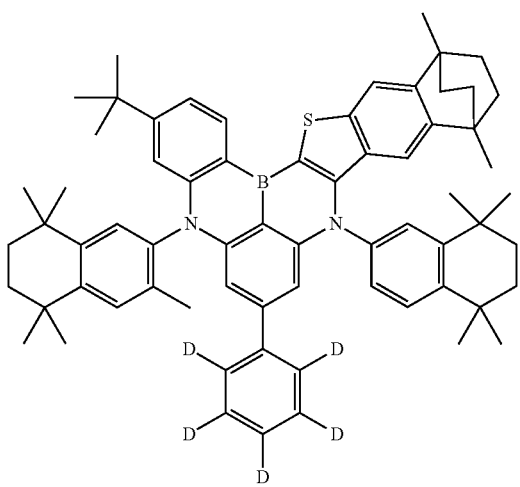
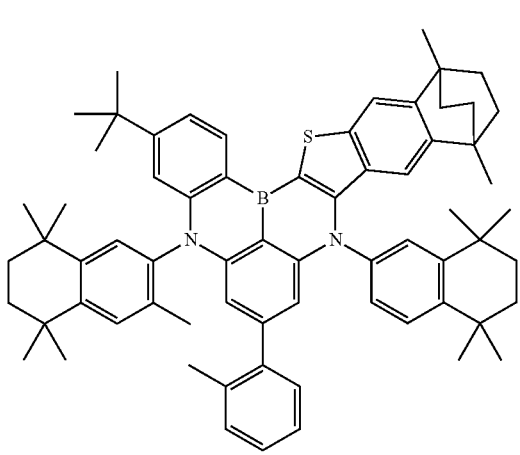
646
-continued
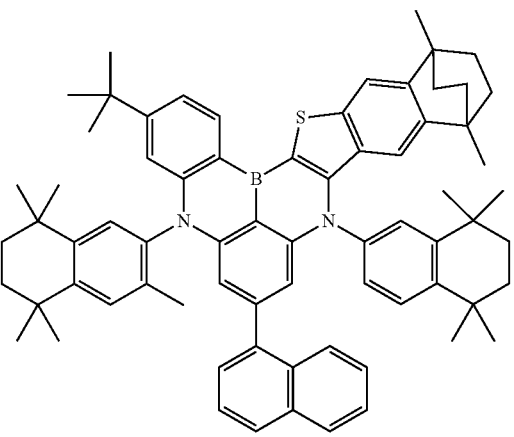
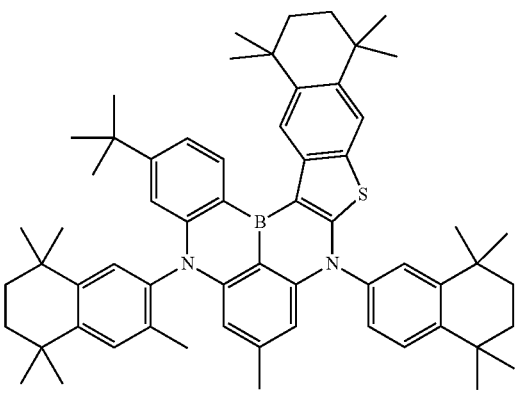

647
-continued
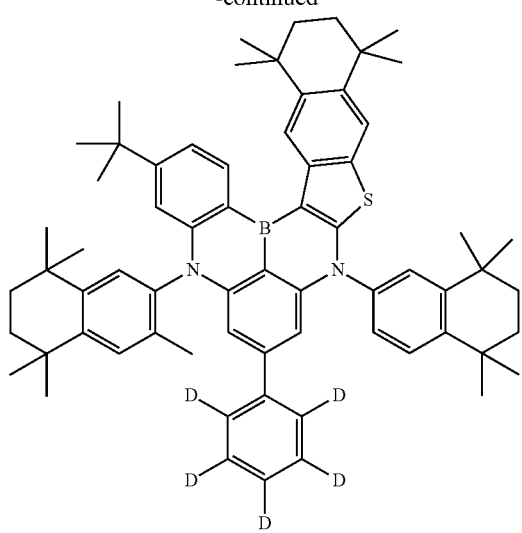
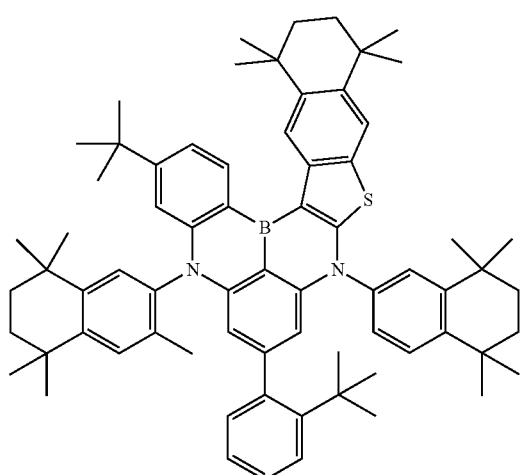
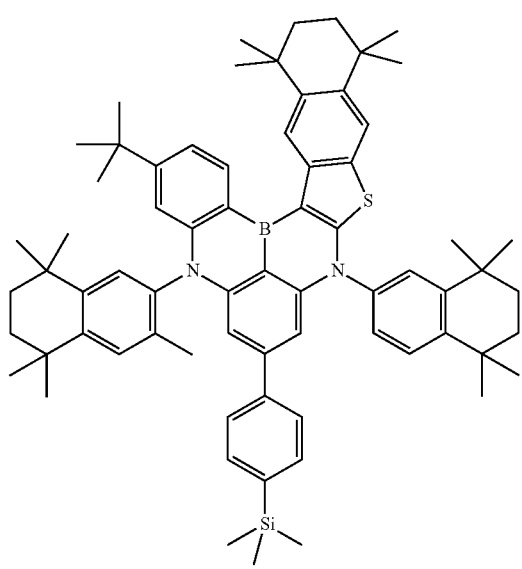
648
-continued
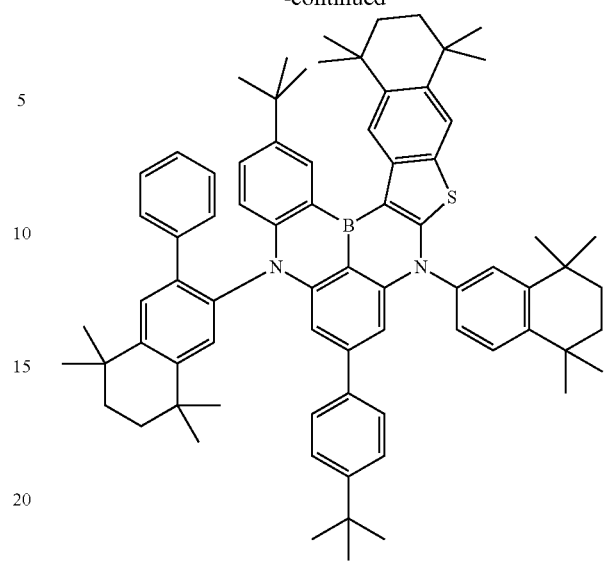
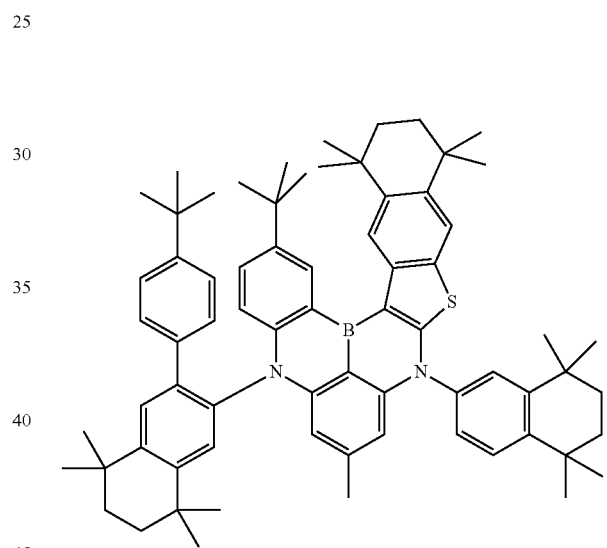
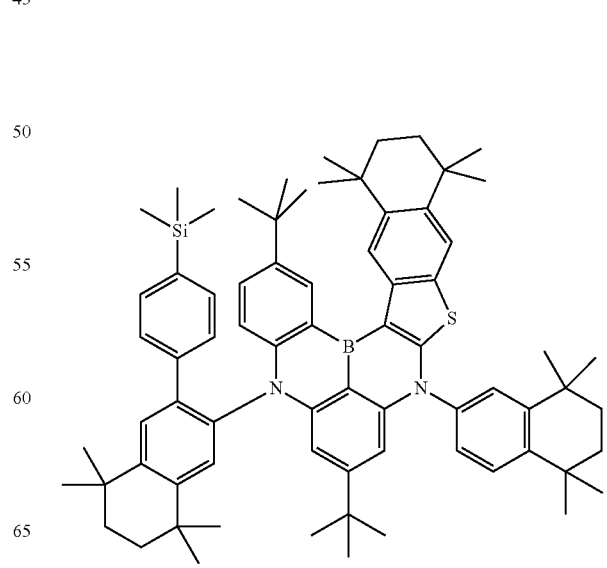

649
-continued
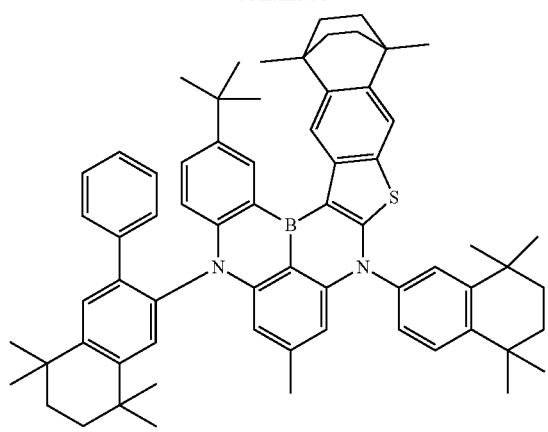
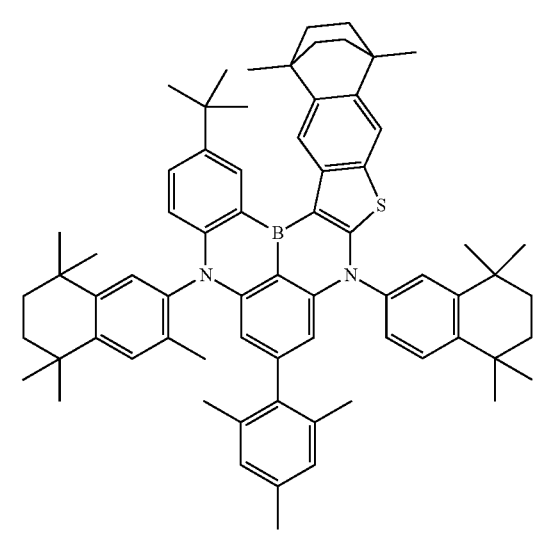
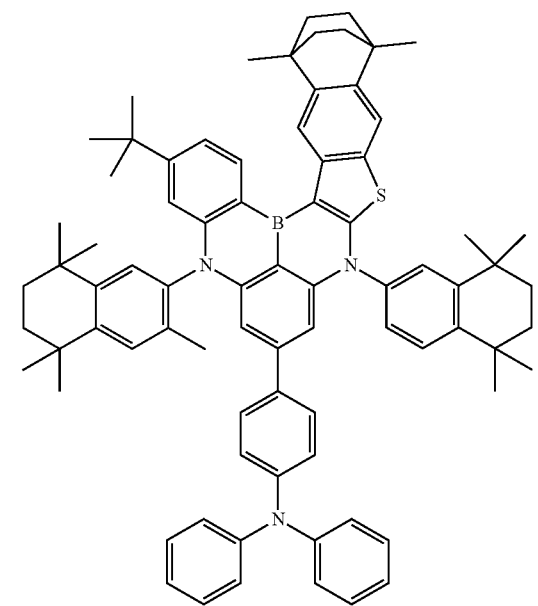
650
-continued
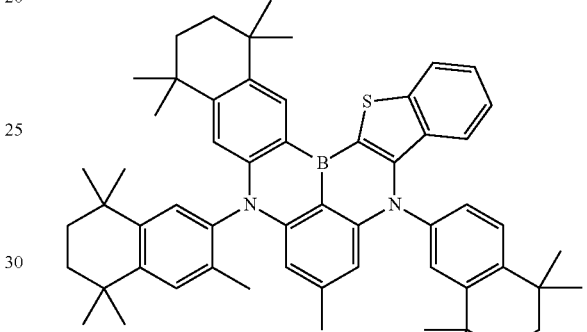
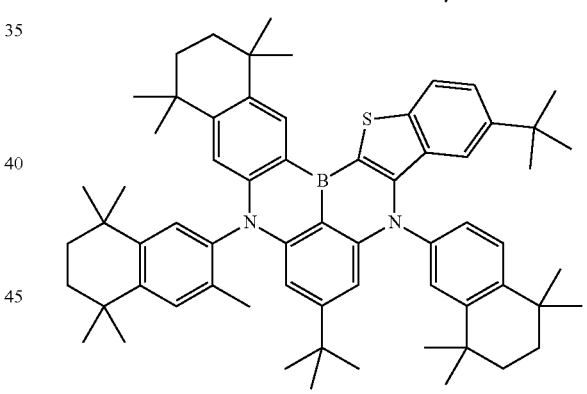
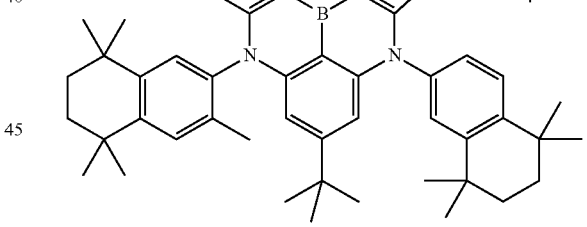
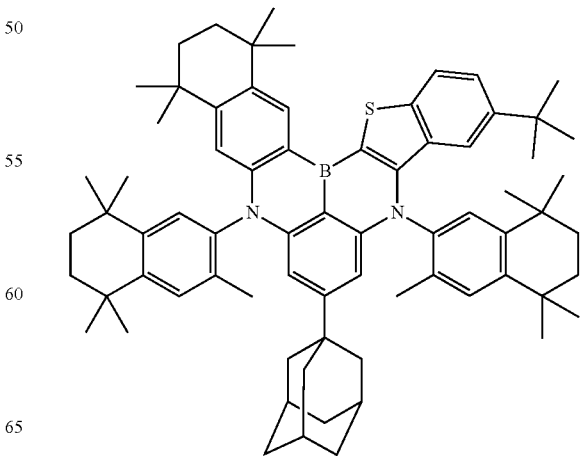

651
-continued
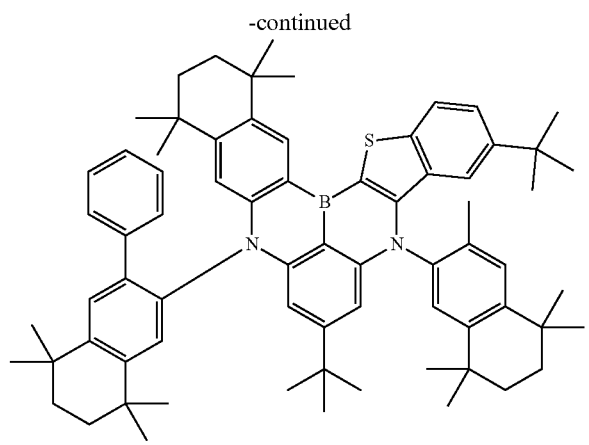
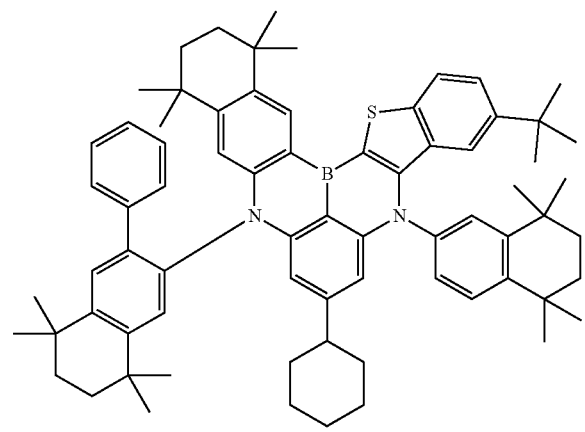
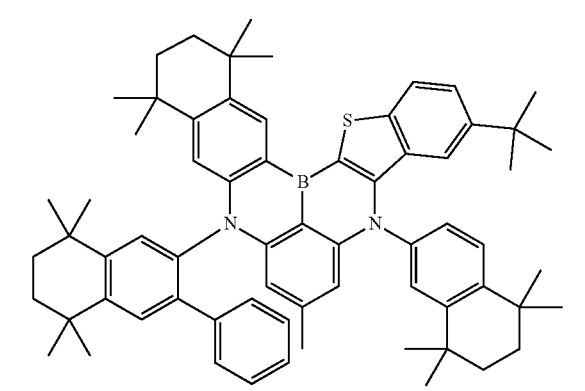
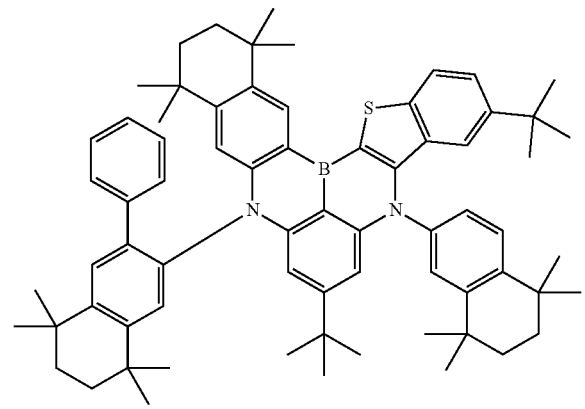
652
-continued
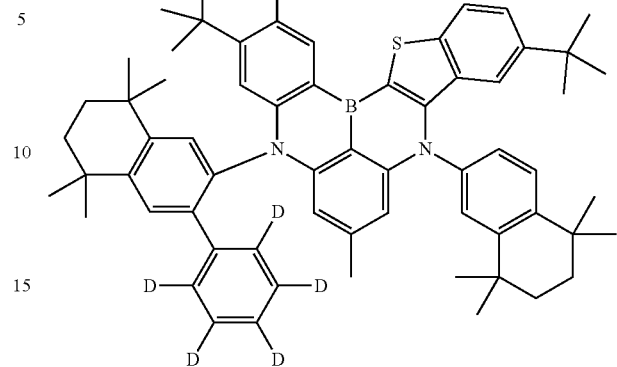
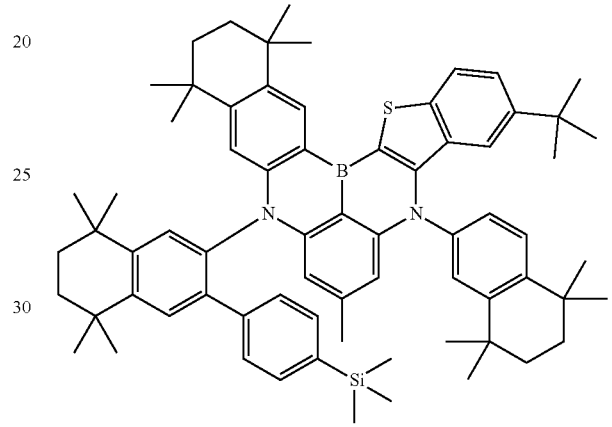
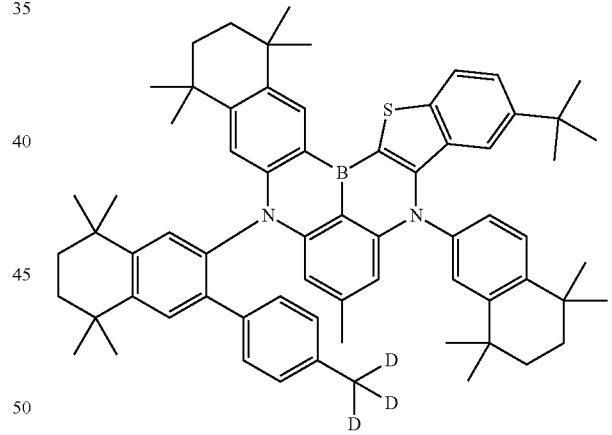
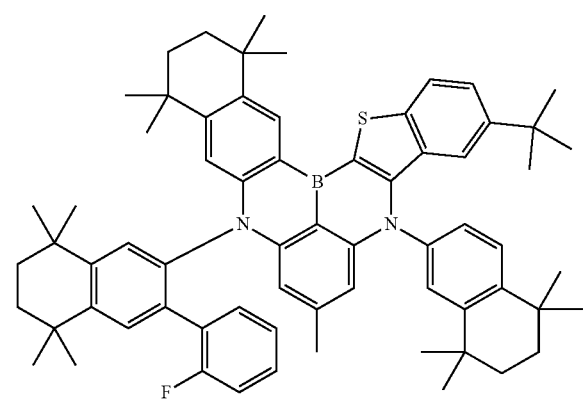

653
-continued
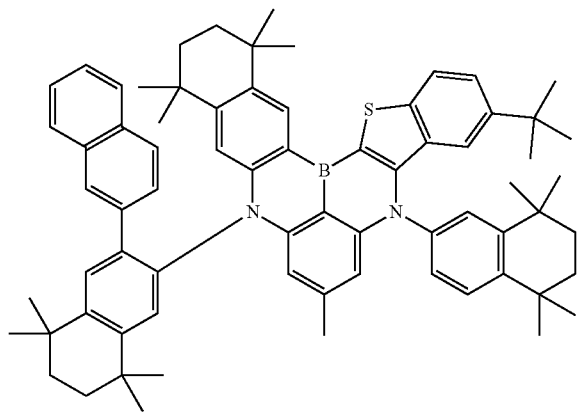
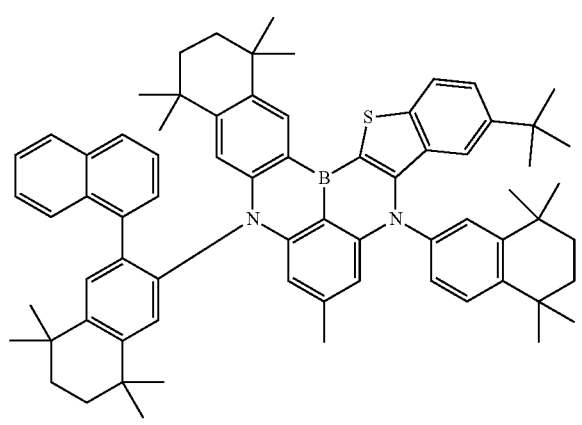
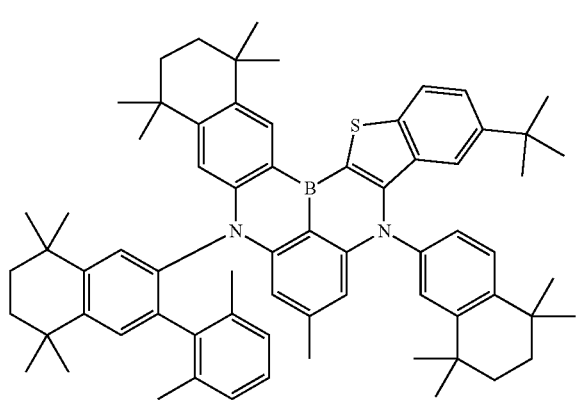
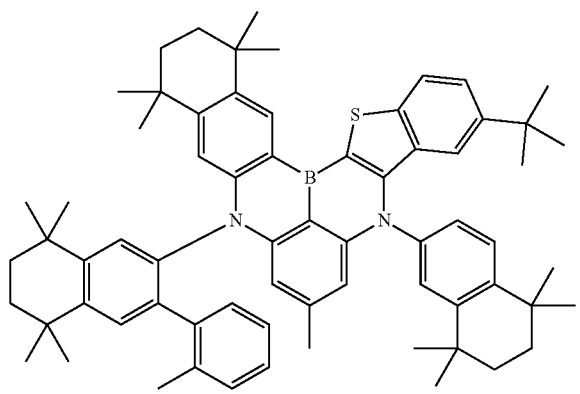
654
-continued
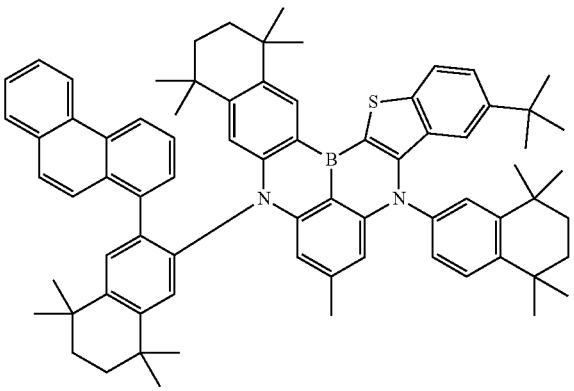
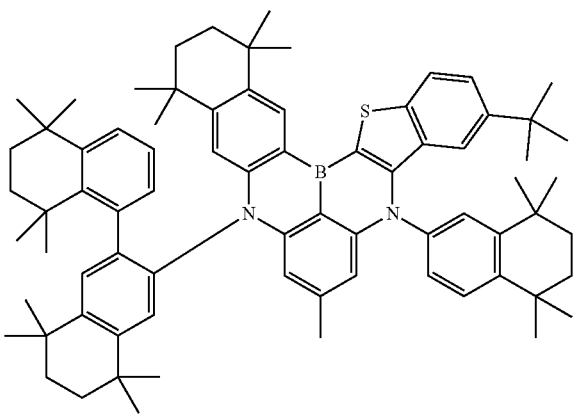
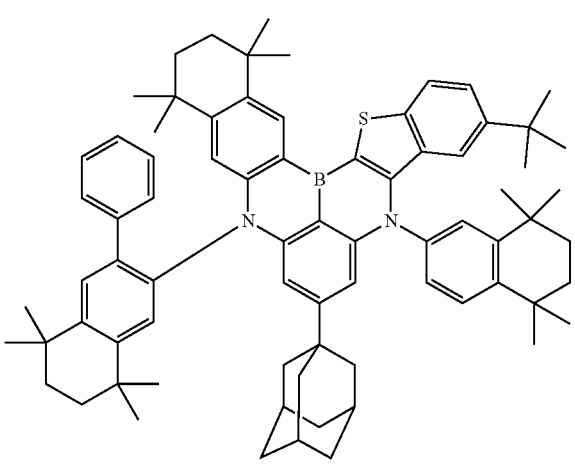
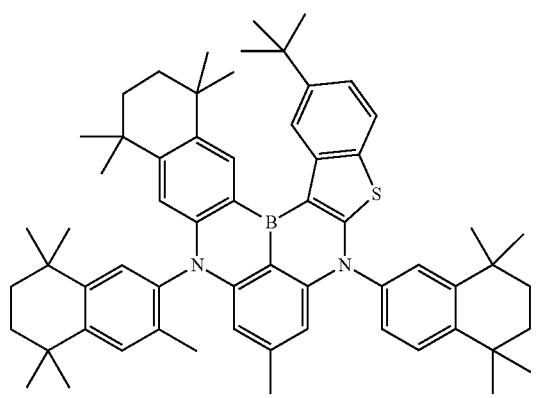

655
-continued
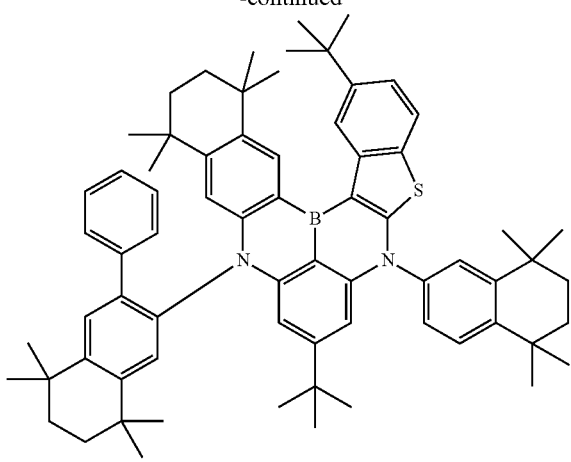
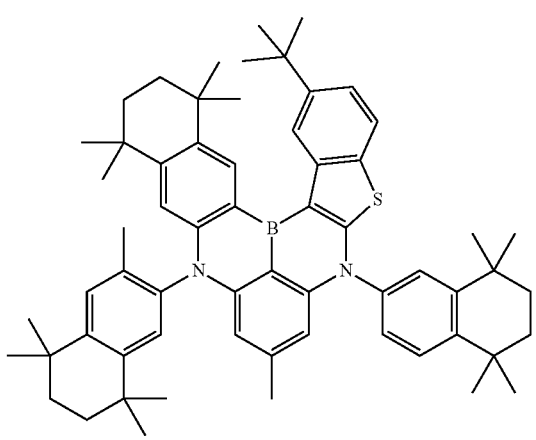
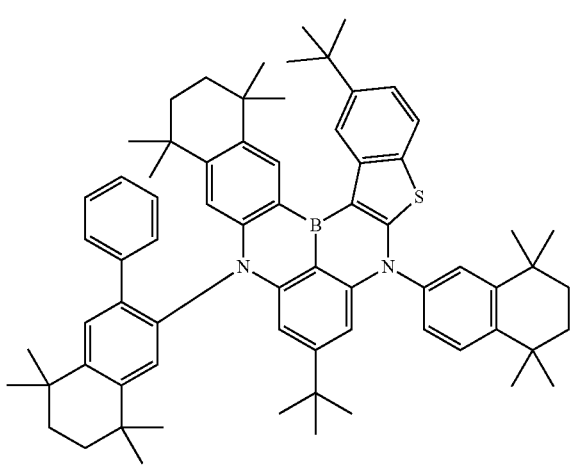
656
-continued
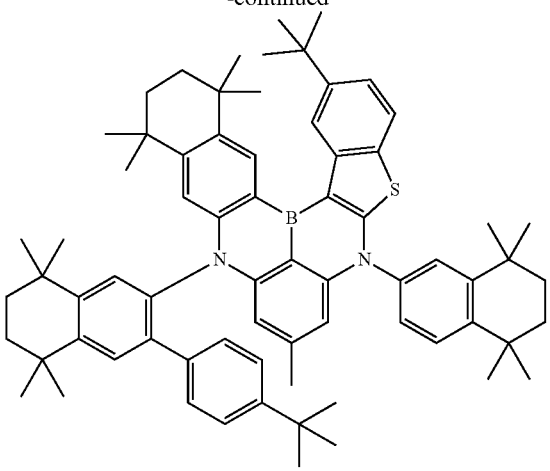
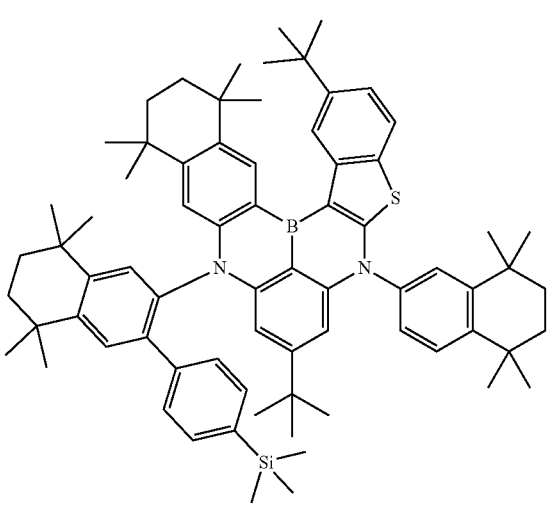
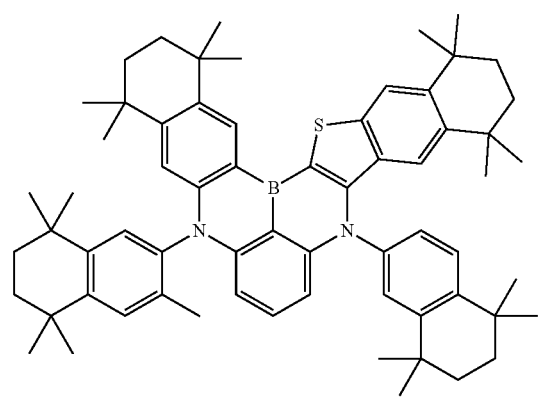

657
-continued
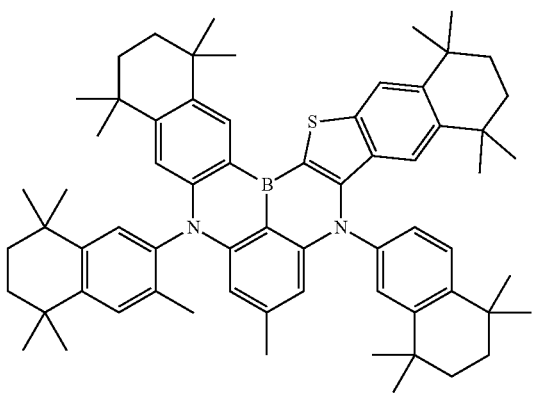
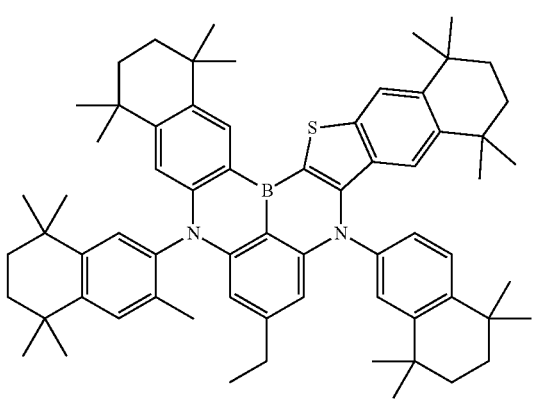
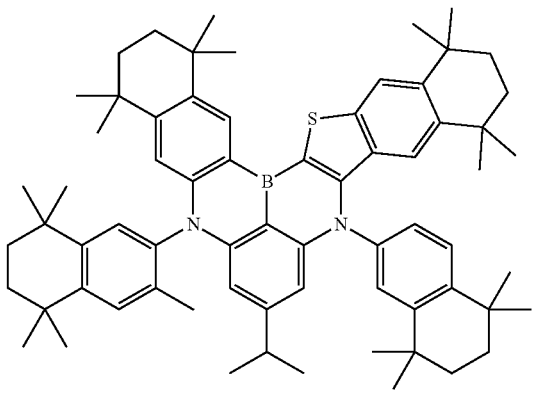
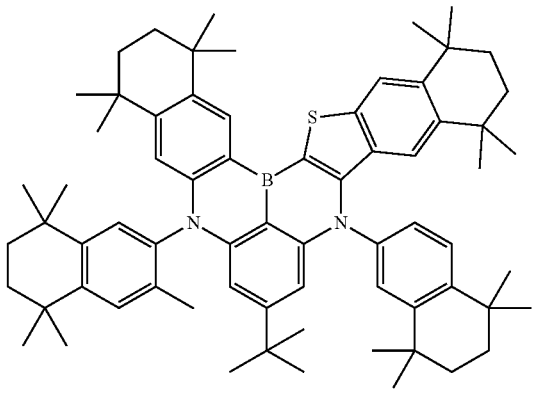
658
-continued
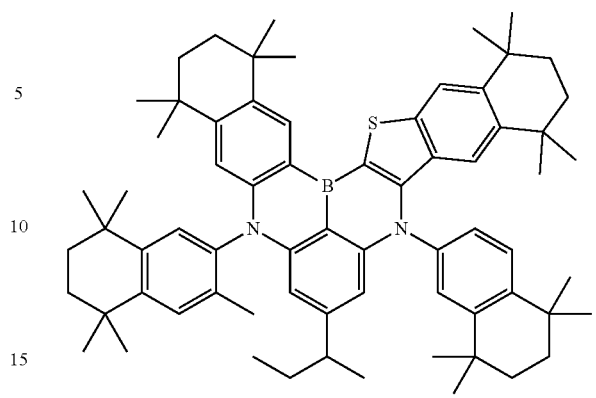
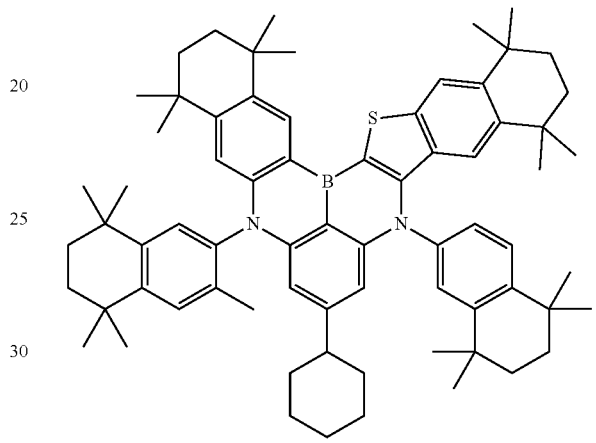
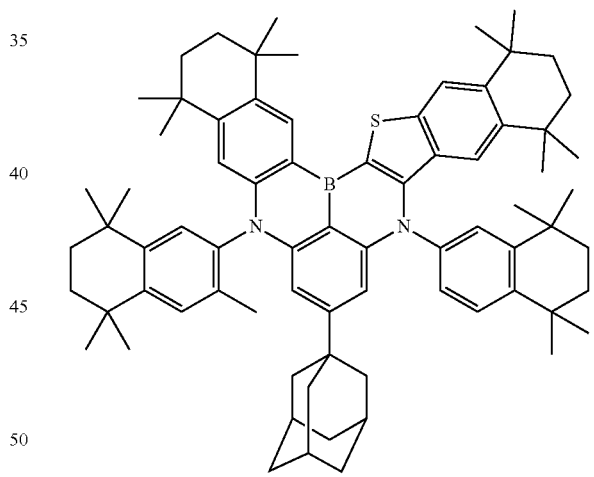
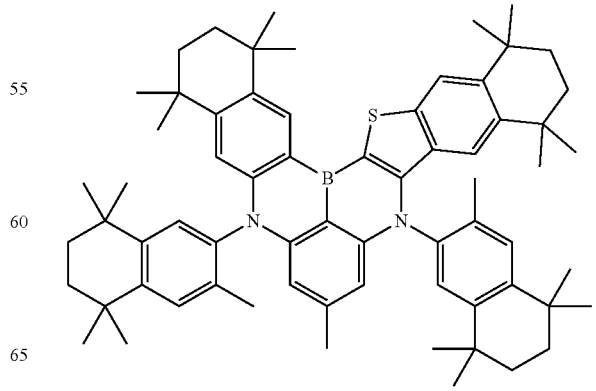

659
-continued
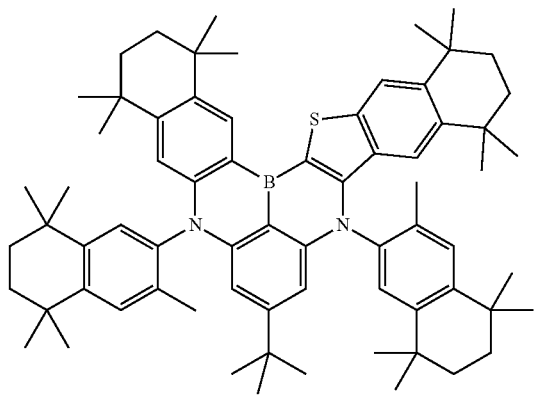
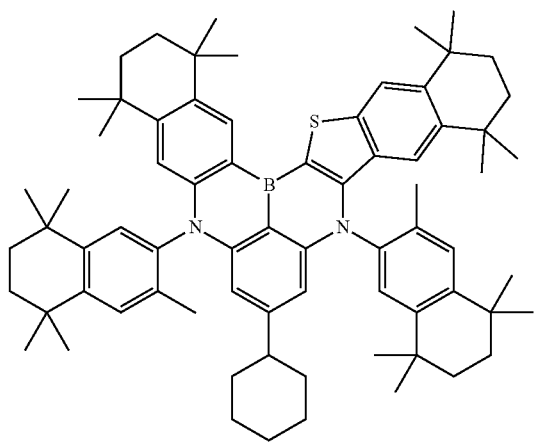
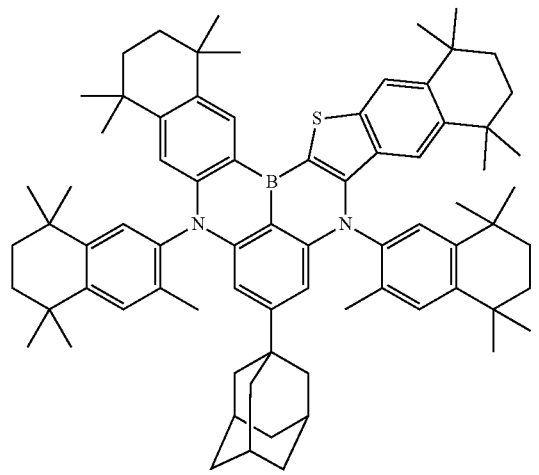
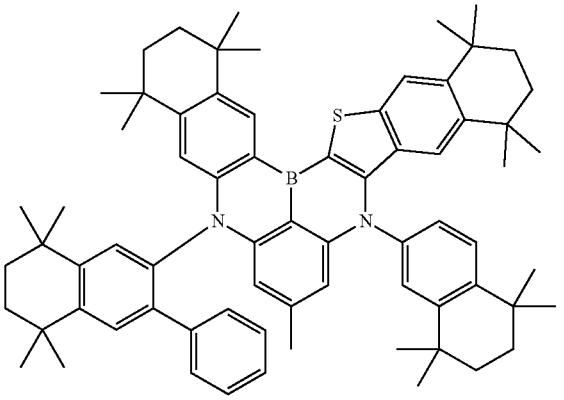
660
-continued
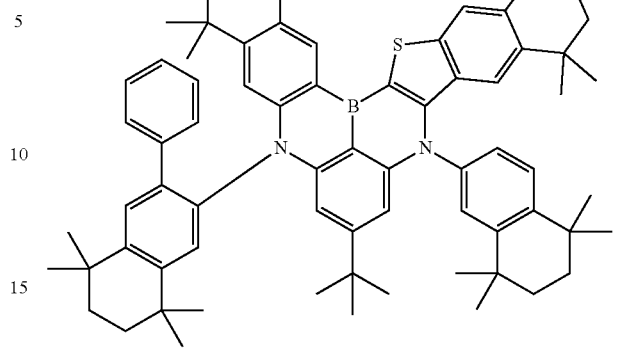
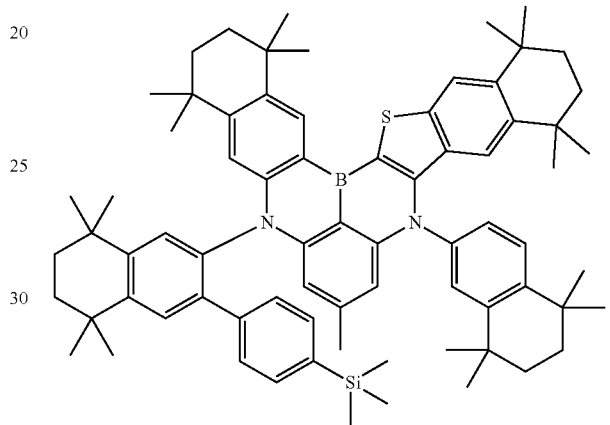
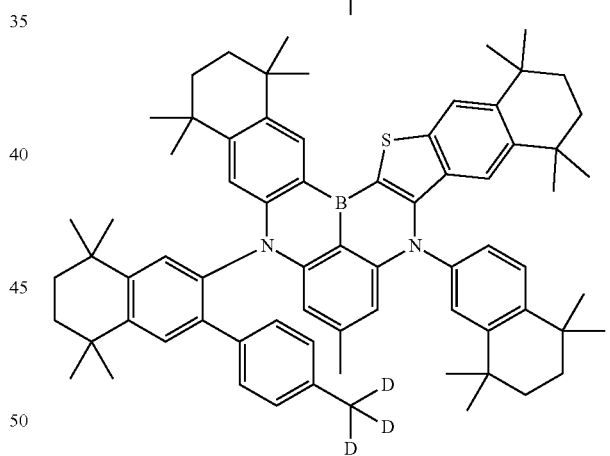
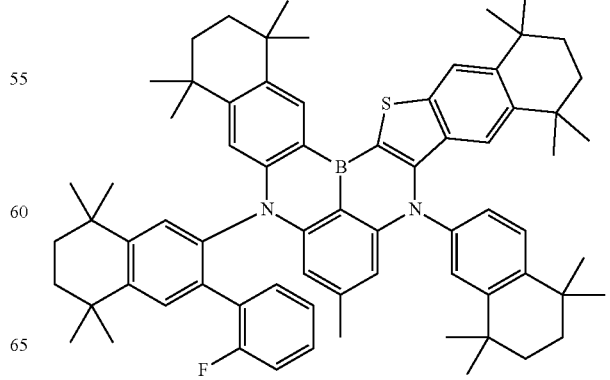

661
-continued
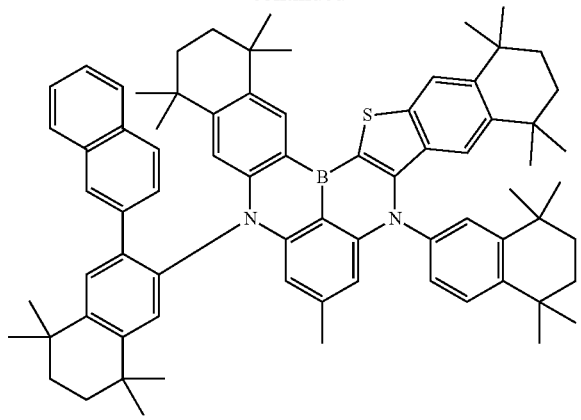
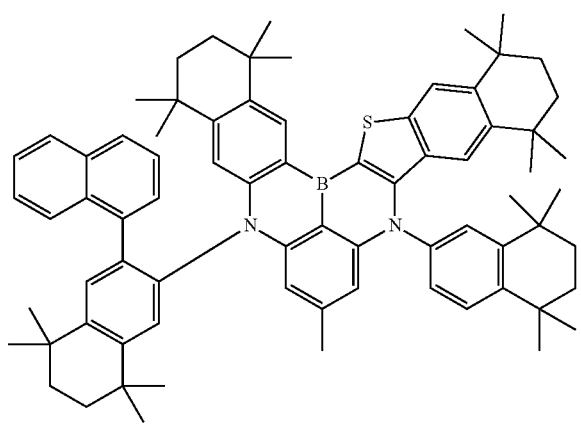
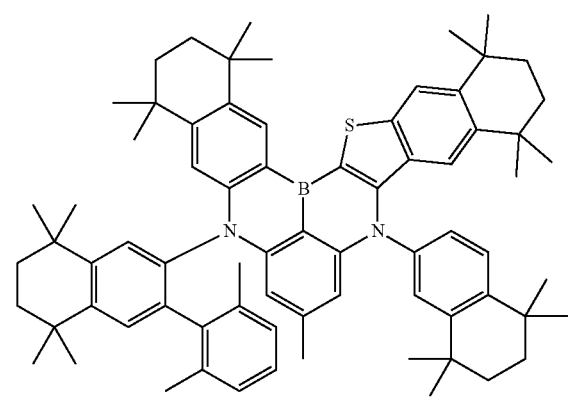
662
-continued
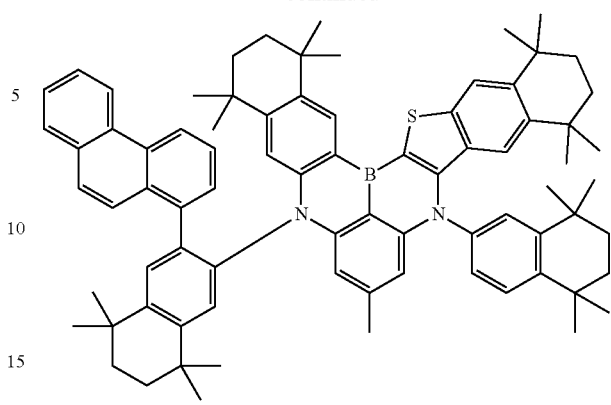
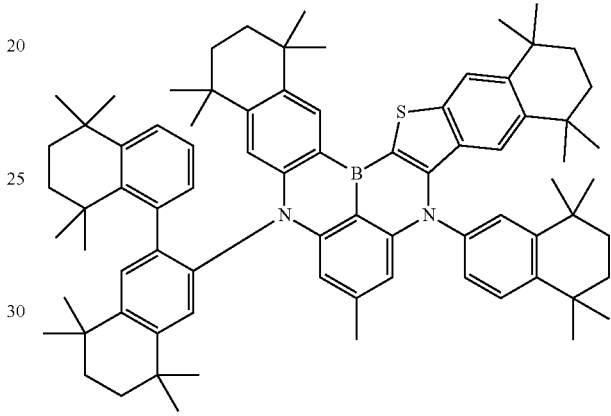
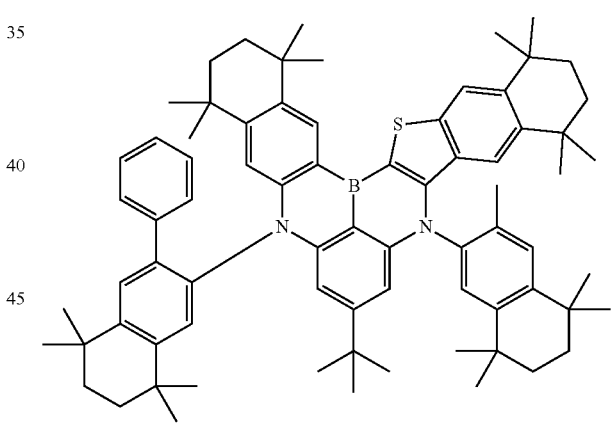
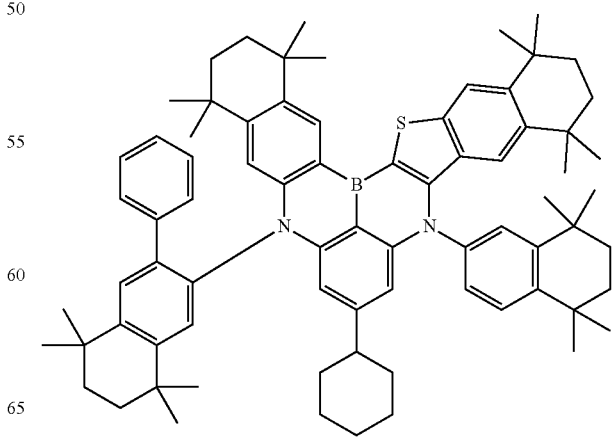

663
-continued
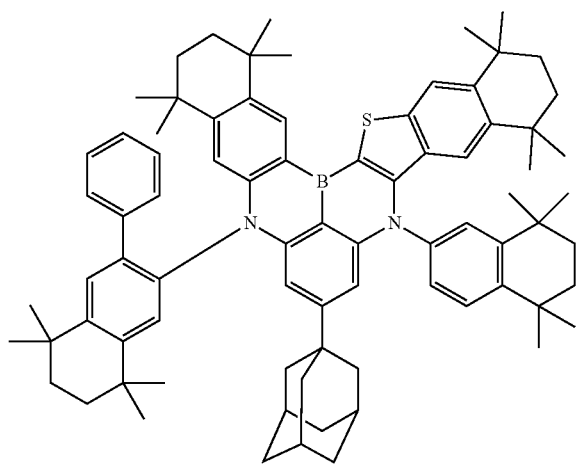
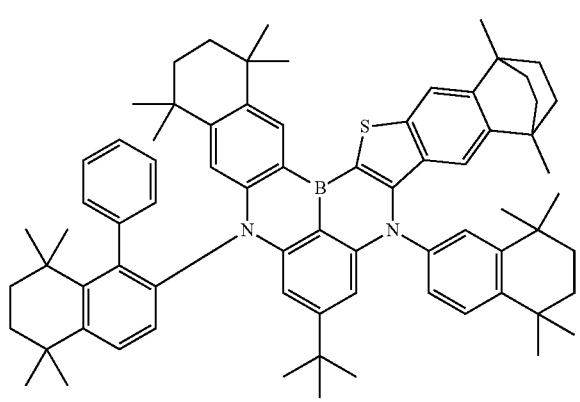
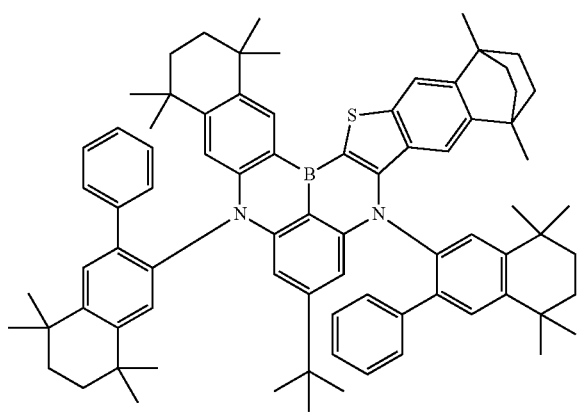
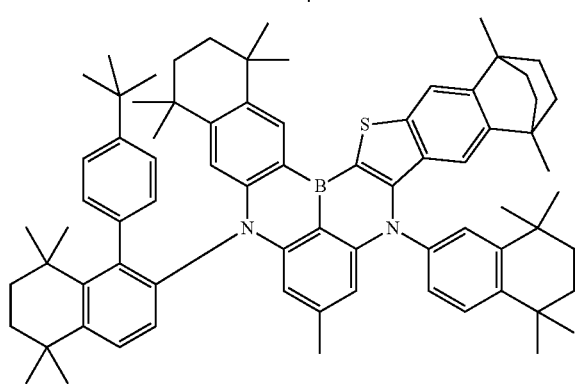
664
-continued
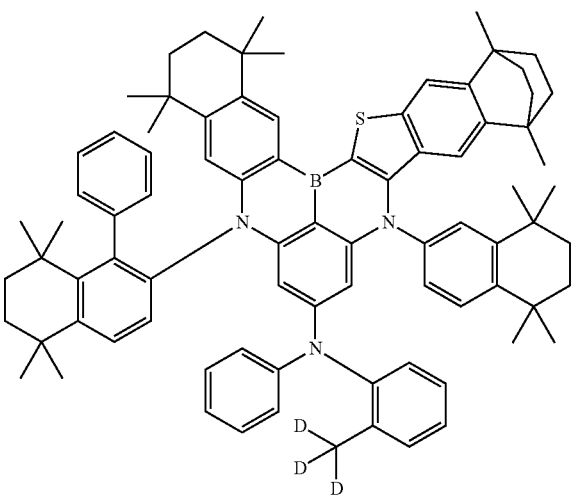 [SMILES: [2H]C([2H])([2H])c1ccccc1N(c1ccccc1)c1cc2c3c(c1)N(c1ccc4c(c1)C(C)(C)CCC4(C)C)c1c(oc4cc5c(cc14)C1(C)CCC5(C)CC1)B3c1cc3c(cc1N2c1ccc2c(c1-c1ccccc1)C(C)(C)CCC2(C)C)C(C)(C)CCC3(C)C]
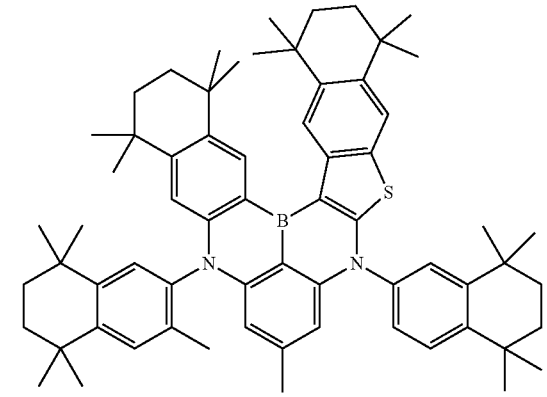

665
-continued
666
-continued
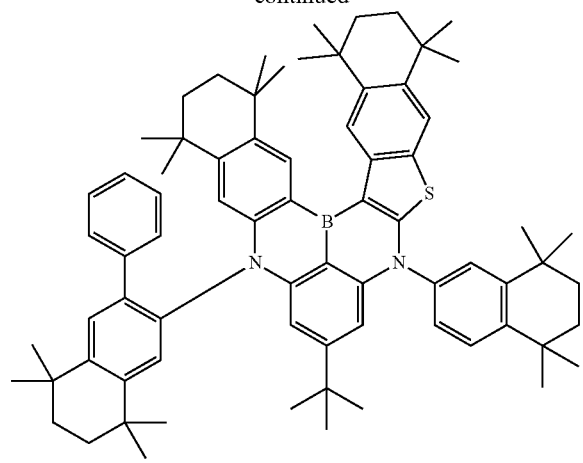
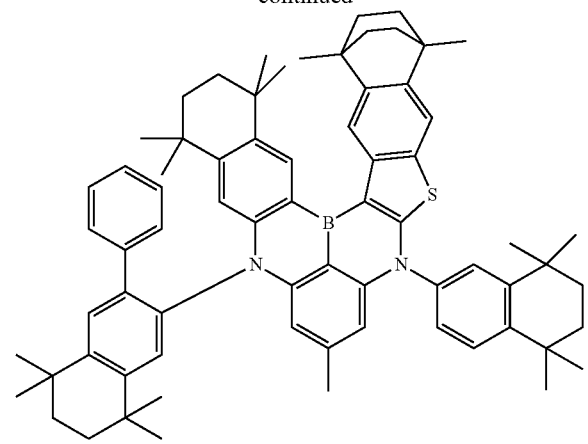
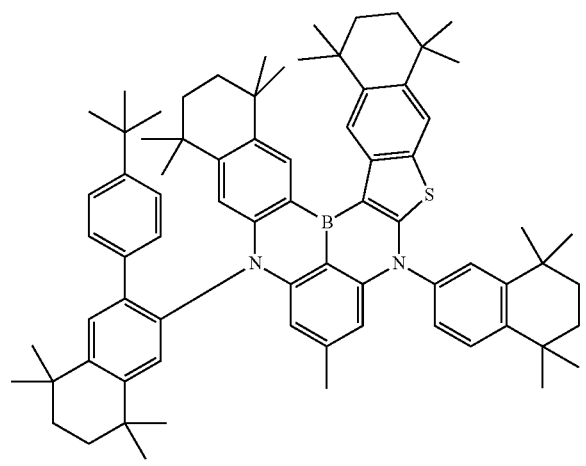
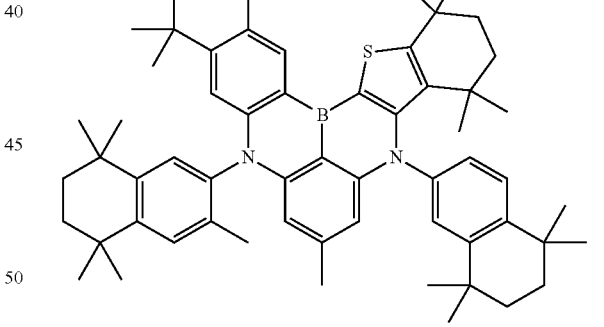
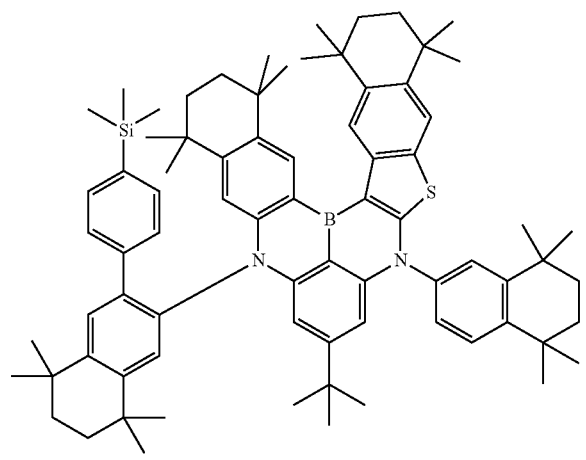
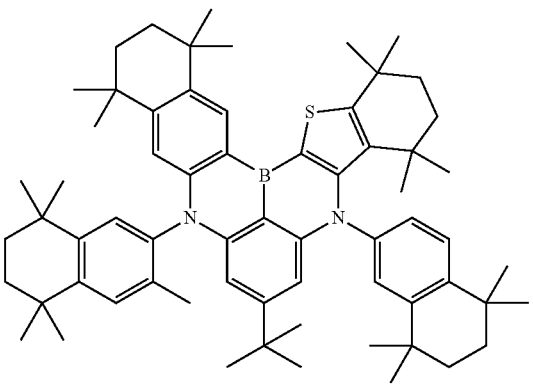

667
-continued
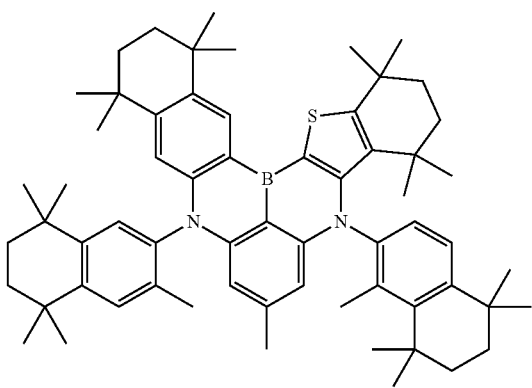
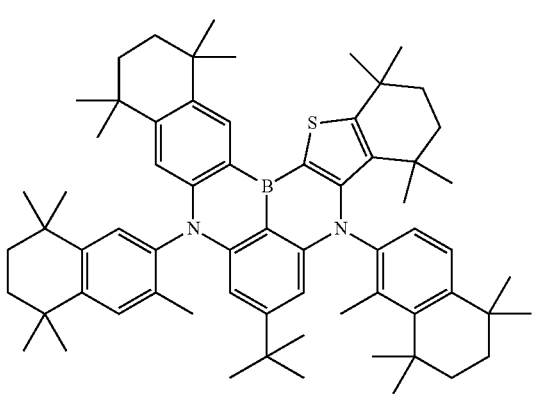
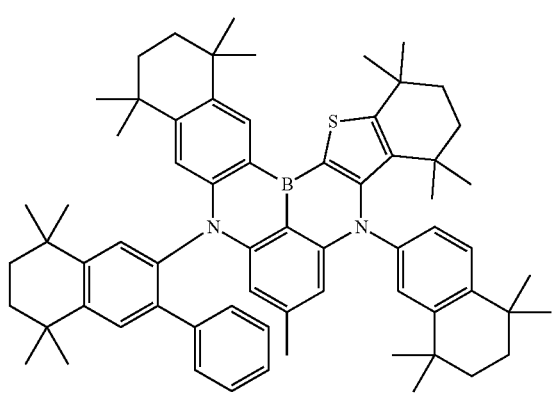
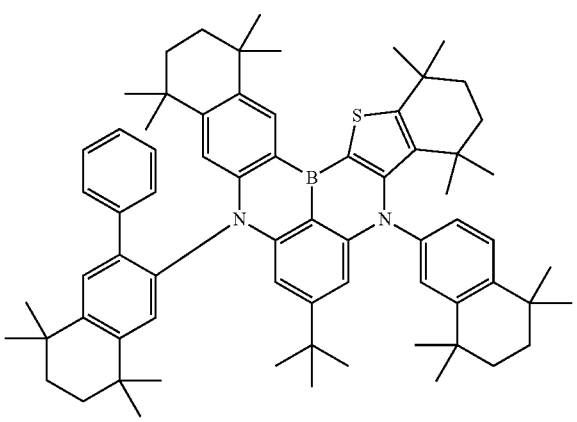
668
-continued
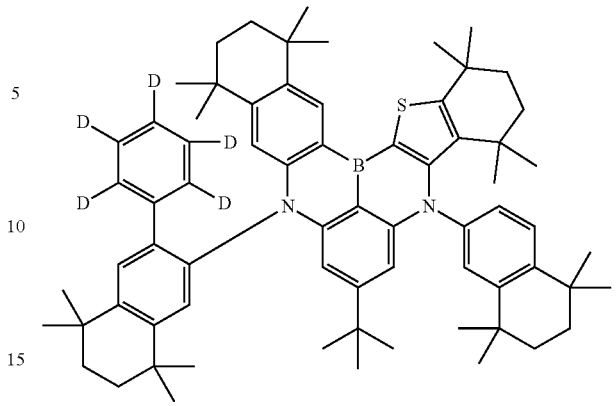
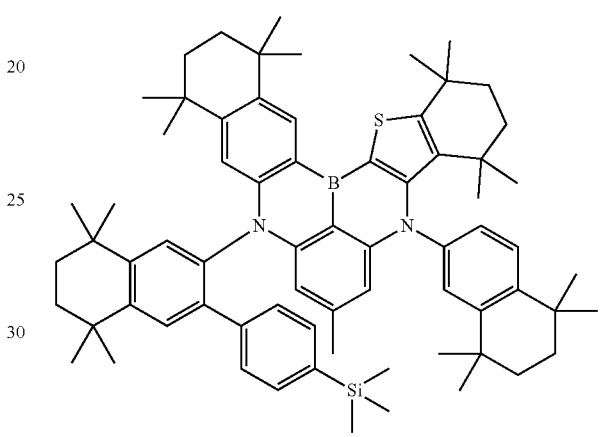
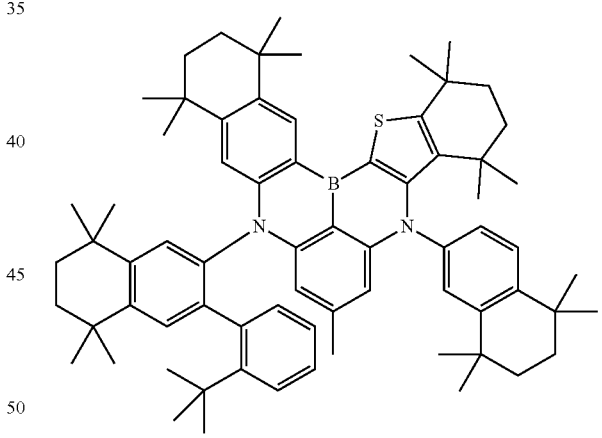
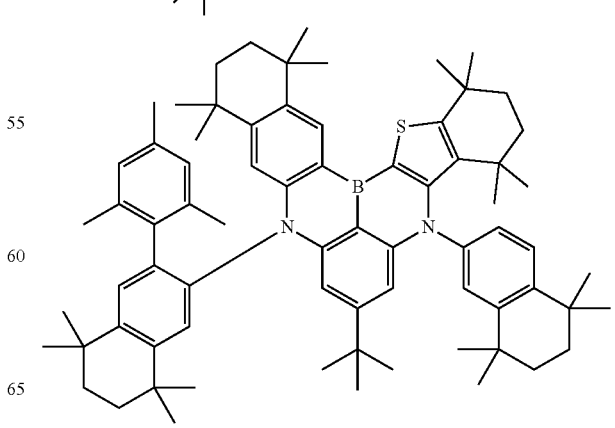

669
-continued
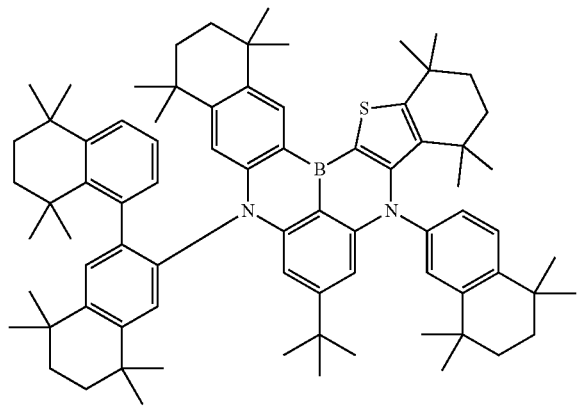
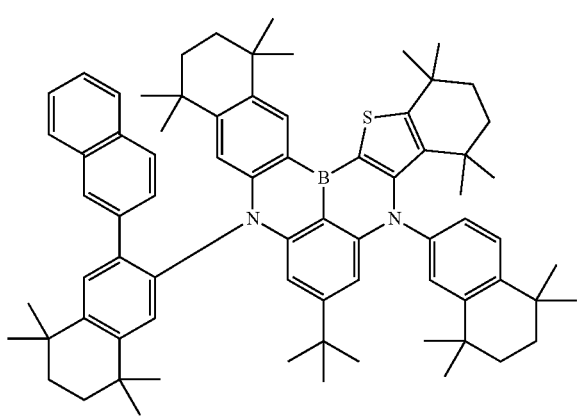
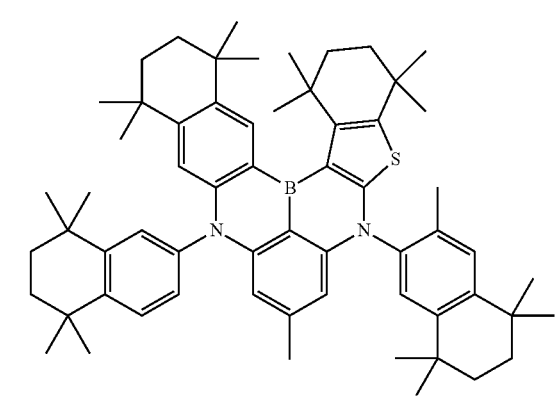
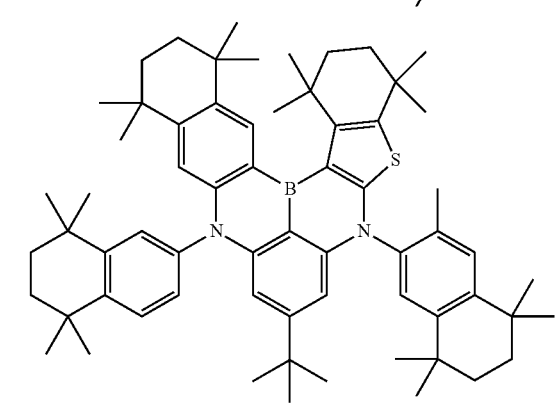
670
-continued
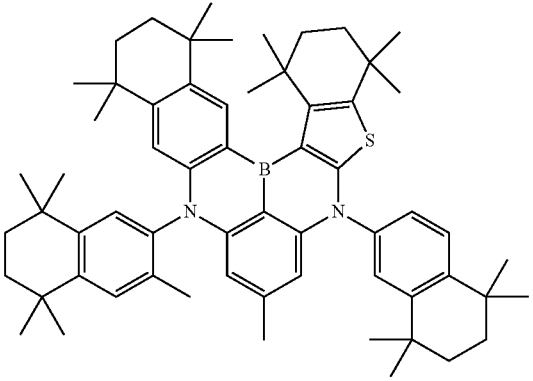
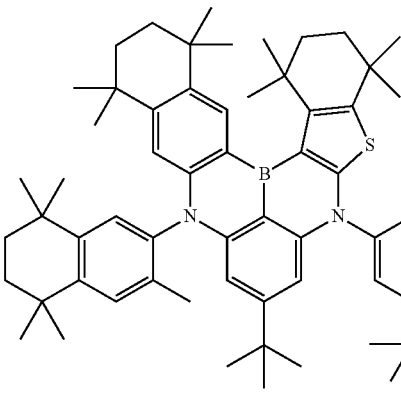
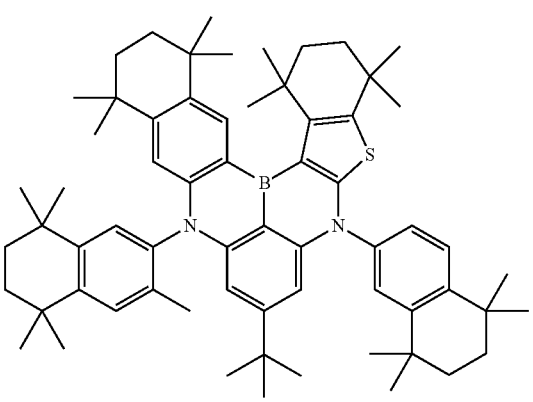
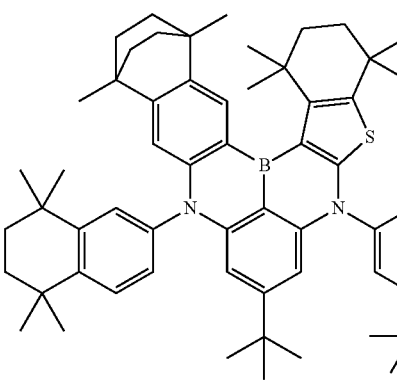

671
-continued
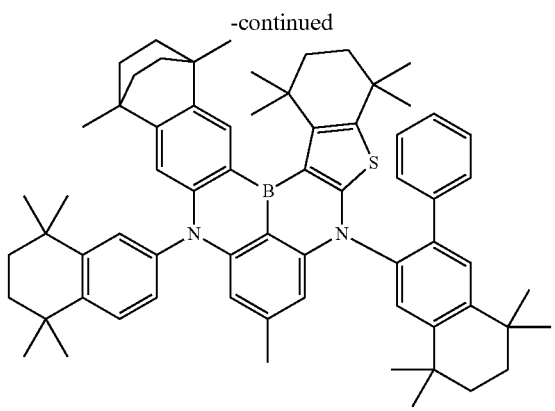
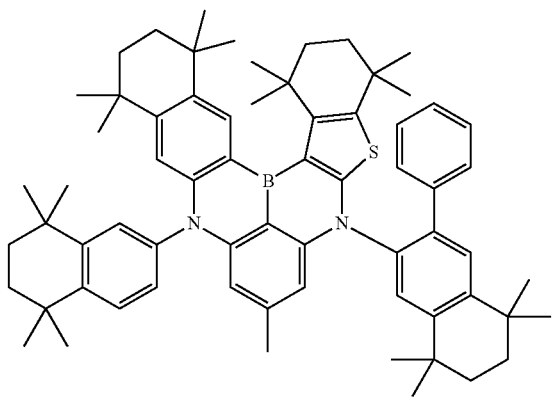
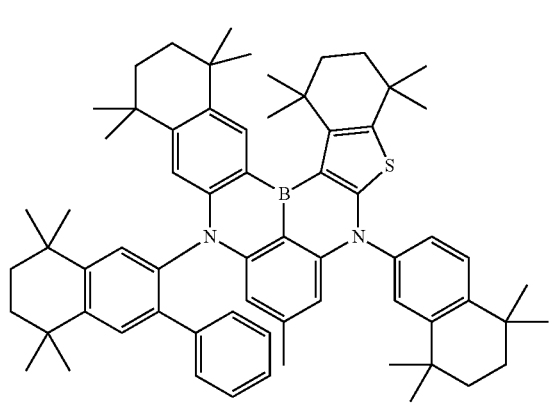
672
-continued
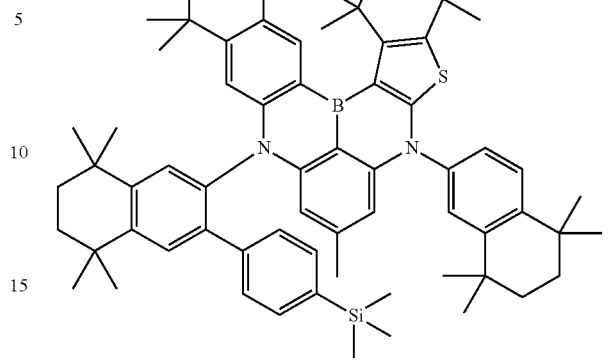
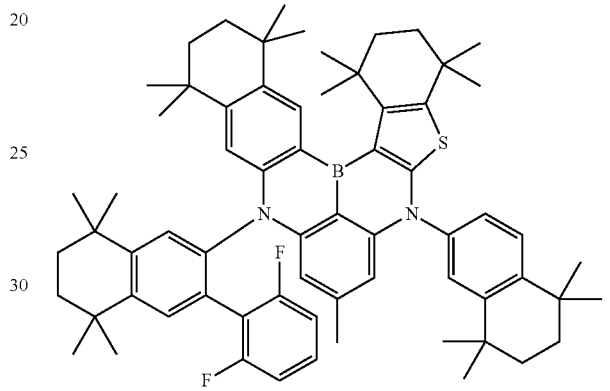
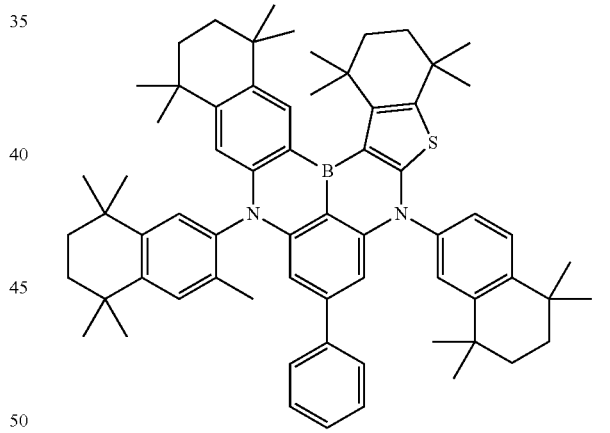
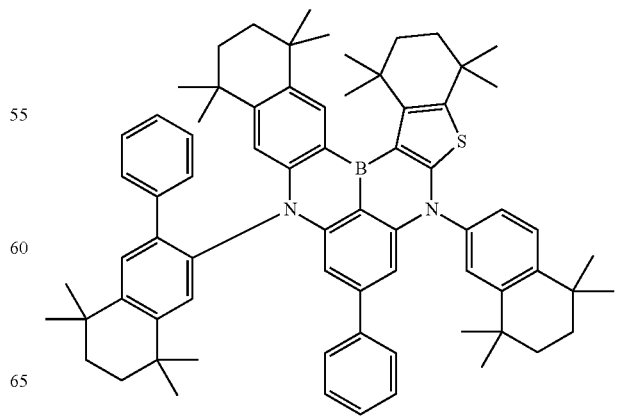

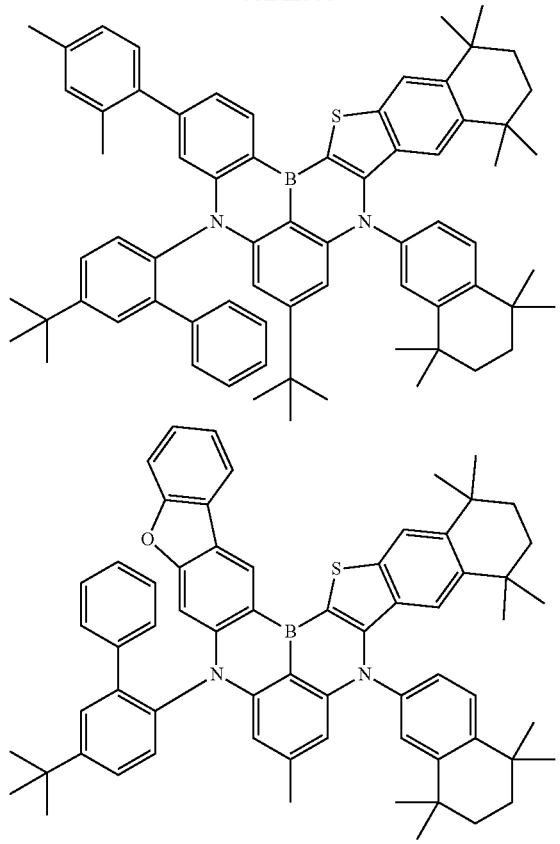

In the above-listed compounds, Ph is a phenyl group, and D is deuterium.

One embodiment of the present specification provides an organic light emitting device including the compound described above.

In the present specification, a description of a certain member being placed "on" another member includes not only a case of the one member being in contact with the another member but a case of still another member being present between the two members.

In the present specification, a description of a certain part "including" certain constituents means capable of further including other constituents, and does not exclude other constituents unless particularly stated on the contrary.

In the present specification, the "layer" has a meaning compatible with a 'film' mainly used in the art, and means coating covering a target area. The size of the "layer" is not limited, and each "layer" may have the same or a different size. According to one embodiment, the size of the "layer" may be the same as the whole device, may correspond to the size of a specific functional area, or may be as small as a single sub-pixel.

In the present specification, a meaning of a specific A material being included in a B layer includes both i) one or more of A materials being included in one B layer, and ii) a B layer being formed in one or more layers, and an A material being included in one or more of the B layers that is a multilayer.

In the present specification, a meaning of a specific A material being included in a C layer or a D layer includes both i) being included in one or more layers of one or more C layers, ii) being included in one or more layers of one or more D layers, or iii) being included in each of one or more C layers and one or more D layers.

In the present specification, "deuteration", "substituted with deuterium" or "deuterated" means hydrogen at a substitutable position of a compound being substituted with deuterium.

In the present specification, "X % substituted with deuterium", "X % deuterated", "degree of deuteration of X %", or "deuterium substitution rate of X %" means, in the corresponding structure, X % of hydrogens at substitutable positions being substituted with deuterium. For example, when the corresponding structure is dibenzofuran, the dibenzofuran being "substituted with deuterium by 25%", the dibenzofuran being "25% deuterated", the dibenzofuran having a "degree of deuteration of 25%", or the dibenzofuran having a "deuterium substitution rate of 25%" means two of eight hydrogens at substitutable positions of the dibenzofuran being substituted with deuterium.

In the present specification, the degree of deuteration may be identified using known methods such as nuclear magnetic resonance spectroscopy ($^1$H NMR), TLC/MS (thin-layer chromatography/mass spectrometry) or MALDI-TOF MS (matrix assisted laser desorption/ionization time-of-flight mass spectrometry).

One embodiment of the present specification provides an organic light emitting device including a first electrode; a second electrode provided opposite to the first electrode; and an organic material layer including one or more layers provided between the first electrode and the second electrode, wherein one or more layers of the organic material layer include the compound represented by Chemical Formula 1.

The organic material layer of the organic light emitting device of the present specification may be formed in a single layer structure, but may also be formed in a multilayer structure in which two or more layers are laminated. For example, the organic light emitting device of the present specification may have a structure including a hole injection layer, a hole transfer layer, a light emitting layer, an electron transfer layer, an electron injection layer, an electron blocking layer, a hole blocking layer and the like. However, the structure of the organic light emitting device is not limited thereto, and may include a smaller number of organic layers.

In one embodiment of the present specification, the organic material layer includes a light emitting layer, and the light emitting layer includes the compound represented by Chemical Formula 1.

In one embodiment of the present specification, the organic material layer includes a light emitting layer, and the light emitting layer includes the compound represented by Chemical Formula 1 as a dopant of the light emitting layer.

In one embodiment of the present specification, the organic material layer includes a light emitting layer, and the light emitting layer includes the compound represented by Chemical Formula 1 as a blue fluorescent dopant of the light emitting layer.

In one embodiment of the present specification, the organic light emitting device further includes one, two or more layers selected from the group consisting of a hole injection layer, a hole transfer layer, a light emitting layer, an electron transfer layer, an electron injection layer, a hole blocking layer and an electron blocking layer.

In one embodiment of the present specification, the light emitting layer further includes a host compound.

In one embodiment of the present specification, the light emitting layer further includes a host compound, and in the host compound, at least one hydrogen at a substitutable position is substituted with deuterium.

In one embodiment of the present specification, when the host compound is substituted with deuterium, the host compound is substituted with deuterium by 30% or more. In another embodiment, the host compound is substituted with deuterium by 40% or more. In another embodiment, the host compound is substituted with deuterium by 60% or more. In another embodiment, the host compound is substituted with deuterium by 80% or more. In another embodiment, the host compound is substituted with deuterium by 100%.

In one embodiment of the present specification, the light emitting layer further includes a compound represented by the following Chemical Formula H.

[Chemical Formula H]

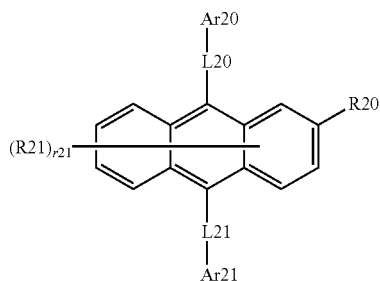

In Chemical Formula H,

L20 and L21 are the same as or different from each other, and each independently a direct bond; a substituted or unsubstituted arylene group; or a substituted or unsubstituted heteroarylene group, Ar20 and Ar21 are the same as or different from each other, and each independently hydrogen; deuterium; a substituted or unsubstituted aryl group; or a substituted or unsubstituted heterocyclic group, R20 and R21 are the same as or different from each other, and each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group, and r21 is an integer of 1 to 7, and when r21 is 2 or greater, the two or more R21 s in the parentheses are the same as or different from each other.

In one embodiment of the present specification, L20 and L21 are the same as or different from each other, and each independently a direct bond; a phenylene group unsubstituted or substituted with deuterium; a biphenylylene group unsubstituted or substituted with deuterium; a naphthylene group unsubstituted or substituted with deuterium; a divalent dibenzofuran group; or a divalent dibenzothiophene group.

In one embodiment of the present specification, Ar20 and Ar21 are the same as or different from each other, and each independently a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, Ar20 and Ar21 are the same as or different from each other, and each independently a substituted or unsubstituted monocyclic or polycyclic aryl group having 6 to 20 carbon atoms; or a substituted or unsubstituted monocyclic or polycyclic heterocyclic group having 2 to 20 carbon atoms.

In one embodiment of the present specification, Ar20 and Ar21 are the same as or different from each other, and each independently a substituted or unsubstituted monocyclic to tetracyclic aryl group having 6 to 20 carbon atoms; or a substituted or unsubstituted monocyclic to tetracyclic heterocyclic group having 2 to 20 carbon atoms.

In one embodiment of the present specification, Ar20 and Ar21 are the same as or different from each other, and each independently a substituted or unsubstituted phenyl group; a substituted or unsubstituted biphenyl group; a substituted or unsubstituted terphenyl group; a substituted or unsubstituted naphthyl group; a substituted or unsubstituted anthracene group; a substituted or unsubstituted phenanthrene group; a substituted or unsubstituted phenalene group; a substituted or unsubstituted fluorene group; a substituted or unsubstituted benzofluorene group; a substituted or unsubstituted furan group; a substituted or unsubstituted thiophene group; a substituted or unsubstituted dibenzofuran group; a substituted or unsubstituted naphthobenzofuran group; a substituted or unsubstituted dibenzothiophene group; or a substituted or unsubstituted naphthobenzothiophene group.

In one embodiment of the present specification, Ar20 and Ar21 are the same as or different from each other, and each independently a phenyl group unsubstituted or substituted with deuterium, or a monocyclic or polycyclic aryl group having 6 to 20 carbon atoms; a biphenyl group unsubstituted or substituted with deuterium, or a monocyclic or polycyclic aryl group having 6 to 20 carbon atoms; a naphthyl group unsubstituted or substituted with a monocyclic or polycyclic aryl group having 6 to 20 carbon atoms; a dibenzofuran group unsubstituted or substituted with a monocyclic or polycyclic aryl group having 6 to 20 carbon atoms; a naphthobenzofuran group unsubstituted or substituted with a monocyclic or polycyclic aryl group having 6 to 20 carbon atoms; a dibenzothiophene group unsubstituted or substituted with a monocyclic or polycyclic aryl group having 6 to 20 carbon atoms; or a naphthobenzothiophene group unsubstituted or substituted with a monocyclic or polycyclic aryl group having 6 to 20 carbon atoms.

In one embodiment of the present specification, Ar20 and Ar21 are the same as or different from each other, and each independently a phenyl group unsubstituted or substituted with deuterium; a biphenyl group unsubstituted or substituted with deuterium; a terphenyl group; a naphthyl group unsubstituted or substituted with deuterium; a phenanthrene group; a dibenzofuran group; a naphthobenzofuran group; a dibenzothiophene group; or a naphthobenzothiophene group.

In one embodiment of the present specification, Ar20 is a substituted or unsubstituted heterocyclic group, and Ar21 is a substituted or unsubstituted aryl group.

In one embodiment of the present specification, R20 is hydrogen; deuterium; a halogen group; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; deuterium; fluorine; a substituted or unsubstituted linear or branched alkyl group having 1 to 10 carbon atoms; a substituted or unsubstituted monocyclic or polycyclic cycloalkyl group having 3 to 10 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; a substituted or unsubstituted monocyclic or polycyclic aryl group having 6 to 20 carbon atoms; or a substituted or unsubstituted monocyclic or polycyclic heterocyclic group having 2 to 20 carbon atoms.

In one embodiment of the present specification, R20 is hydrogen; a substituted or unsubstituted monocyclic to tetracyclic aryl group having 6 to 20 carbon atoms; or a substituted or unsubstituted monocyclic to tetracyclic heterocyclic group having 2 to 20 carbon atoms.

In one embodiment of the present specification, R20 is hydrogen; a substituted or unsubstituted phenyl group; a substituted or unsubstituted biphenyl group; a substituted or unsubstituted terphenyl group; a substituted or unsubstituted naphthyl group; a substituted or unsubstituted anthracene group; a substituted or unsubstituted phenanthrene group; a substituted or unsubstituted phenalene group; a substituted or unsubstituted fluorene group; a substituted or unsubstituted benzofluorene group; a substituted or unsubstituted furan group; a substituted or unsubstituted thiophene group; a substituted or unsubstituted dibenzofuran group; a substituted or unsubstituted naphthobenzofuran group; a substituted or unsubstituted dibenzothiophene group; or a substituted or unsubstituted naphthobenzothiophene group.

In one embodiment of the present specification, R20 is hydrogen; deuterium; a phenyl group unsubstituted or substituted with deuterium, or a monocyclic or polycyclic aryl group having 6 to 20 carbon atoms; a biphenyl group unsubstituted or substituted with a monocyclic or polycyclic aryl group having 6 to 20 carbon atoms; a naphthyl group unsubstituted or substituted with deuterium, or a monocyclic or polycyclic aryl group having 6 to 20 carbon atoms; a dibenzofuran group unsubstituted or substituted with a monocyclic or polycyclic aryl group having 6 to 20 carbon atoms; a naphthobenzofuran group unsubstituted or substituted with a monocyclic or polycyclic aryl group having 6 to 20 carbon atoms; a dibenzothiophene group unsubstituted or substituted with a monocyclic or polycyclic aryl group having 6 to 20 carbon atoms; or a naphthobenzothiophene group unsubstituted or substituted with a monocyclic or polycyclic aryl group having 6 to 20 carbon atoms.

In one embodiment of the present specification, R20 is hydrogen; deuterium; a phenyl group unsubstituted or substituted with deuterium, a phenyl group or a naphthyl group; a biphenyl group; a naphthyl group unsubstituted or substituted with deuterium, a phenyl group or a naphthyl group; a dibenzofuran group; a naphthobenzofuran group; a dibenzothiophene group; or a naphthobenzothiophene group.

According to one embodiment of the present specification, R21 is hydrogen.

According to one embodiment of the present specification, R21 is deuterium.

In one embodiment of the present specification, when the compound represented by Chemical Formula H is substituted with deuterium, hydrogen at a substitutable position may be substituted with deuterium by 30% or more. In another embodiment, hydrogen at a substitutable position is substituted with deuterium by 40% or more in the structure of Chemical Formula H. In another embodiment, hydrogen at a substitutable position is substituted with deuterium by 60% or more in the structure of Chemical Formula H.

In another embodiment, hydrogen at a substitutable position is substituted with deuterium by 80% or more in the structure of Chemical Formula H. In another embodiment, hydrogen at a substitutable position is substituted with deuterium by 100% in the structure of Chemical Formula H.

In one embodiment of the present specification, the compound represented by Chemical Formula H is any one selected from among the following compounds.

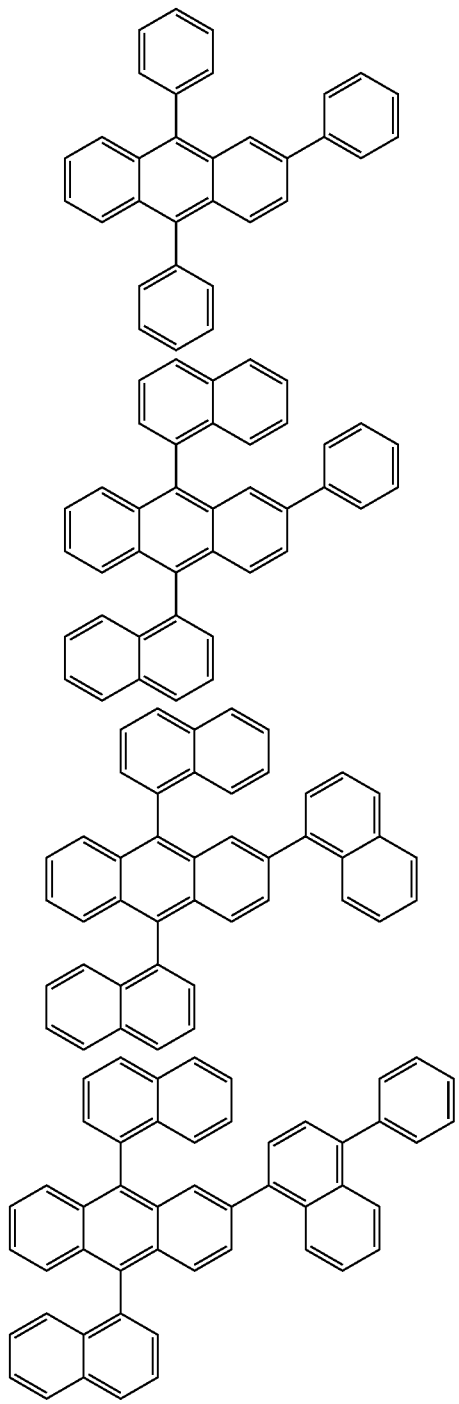

679
-continued
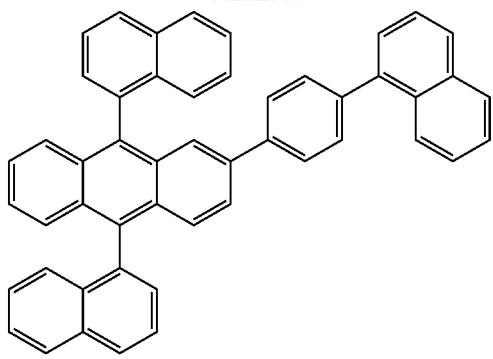
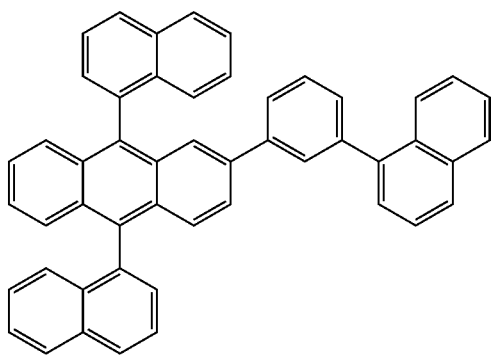
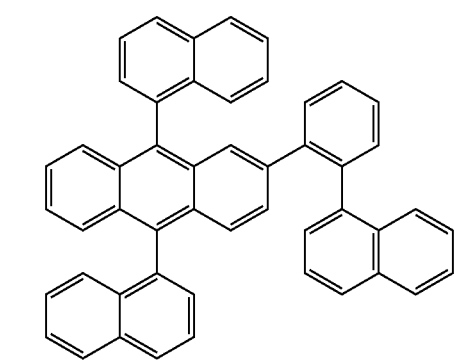
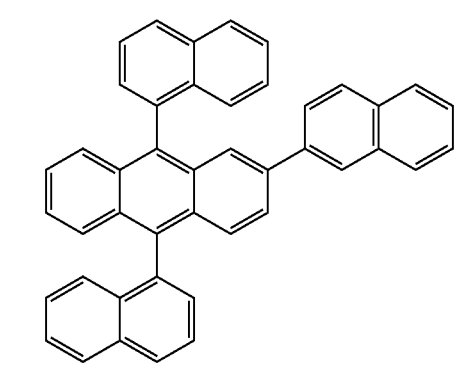
680
-continued
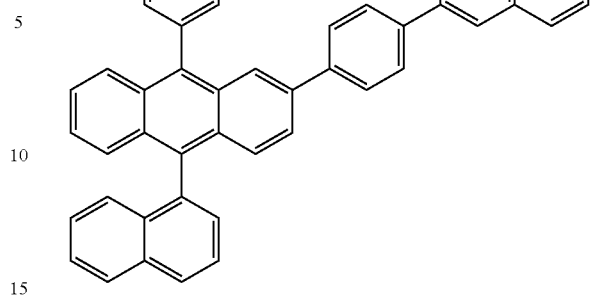
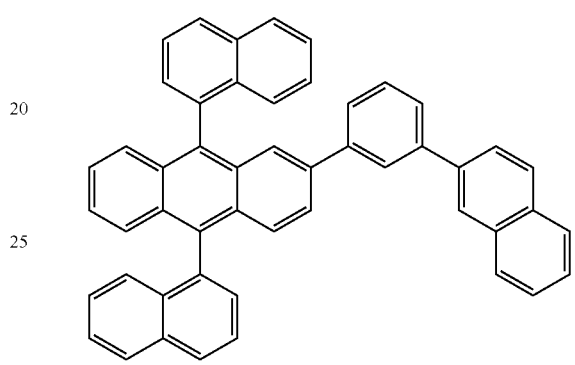
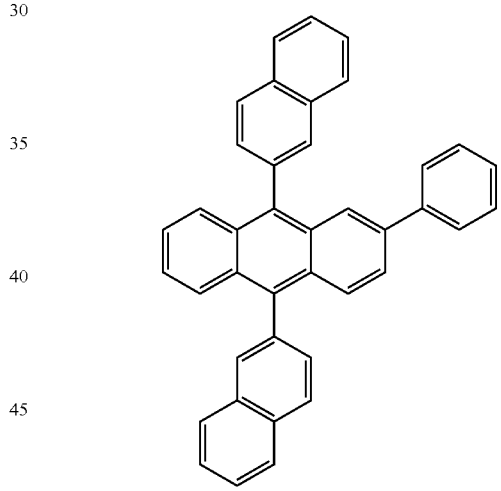
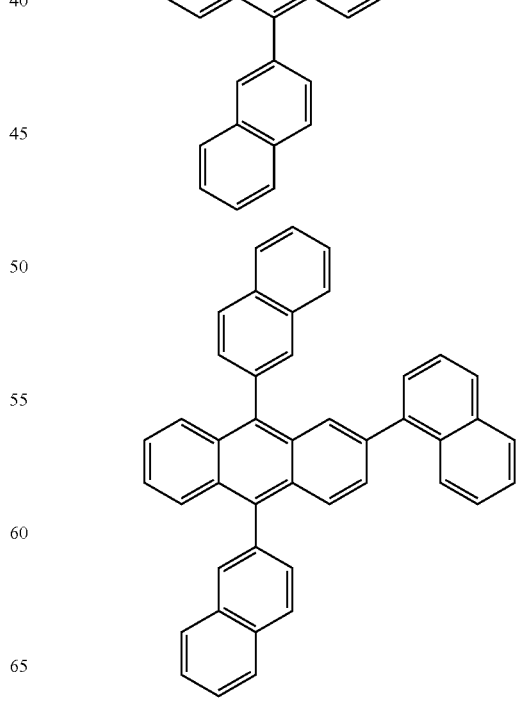

681
-continued
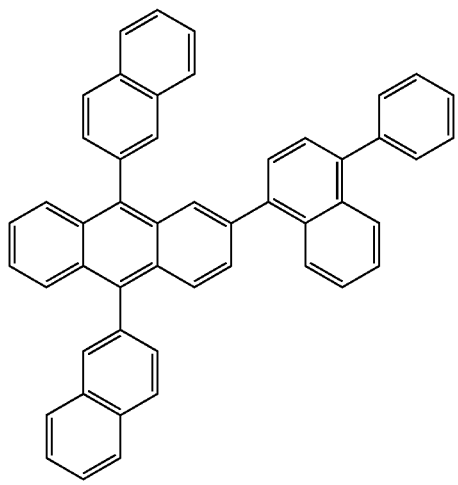
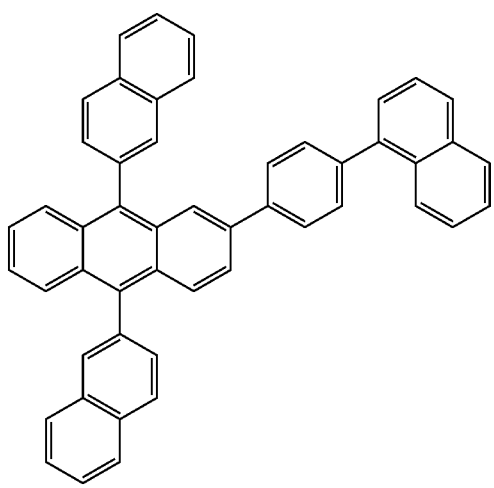
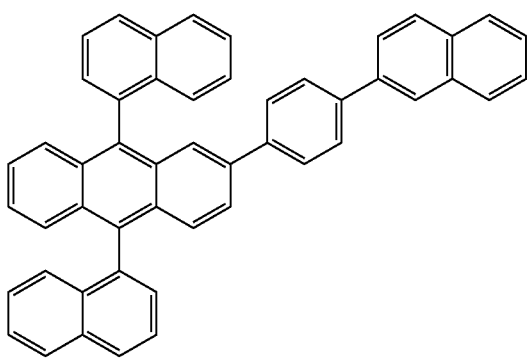
682
-continued
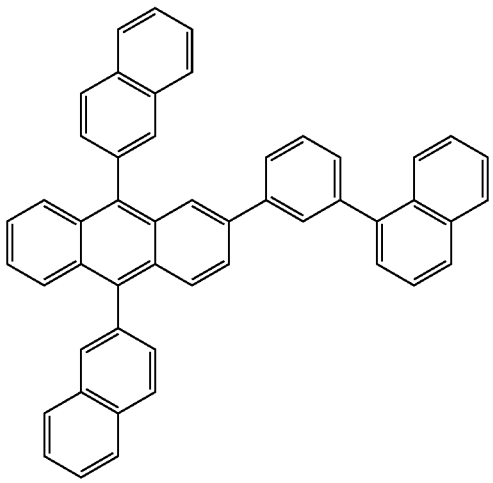
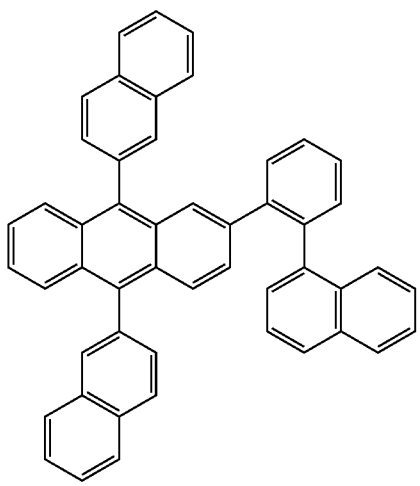
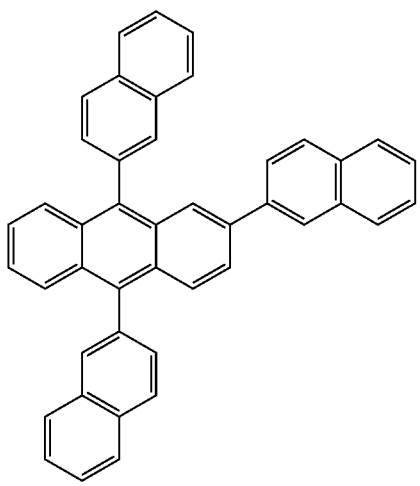

683
-continued
684
-continued
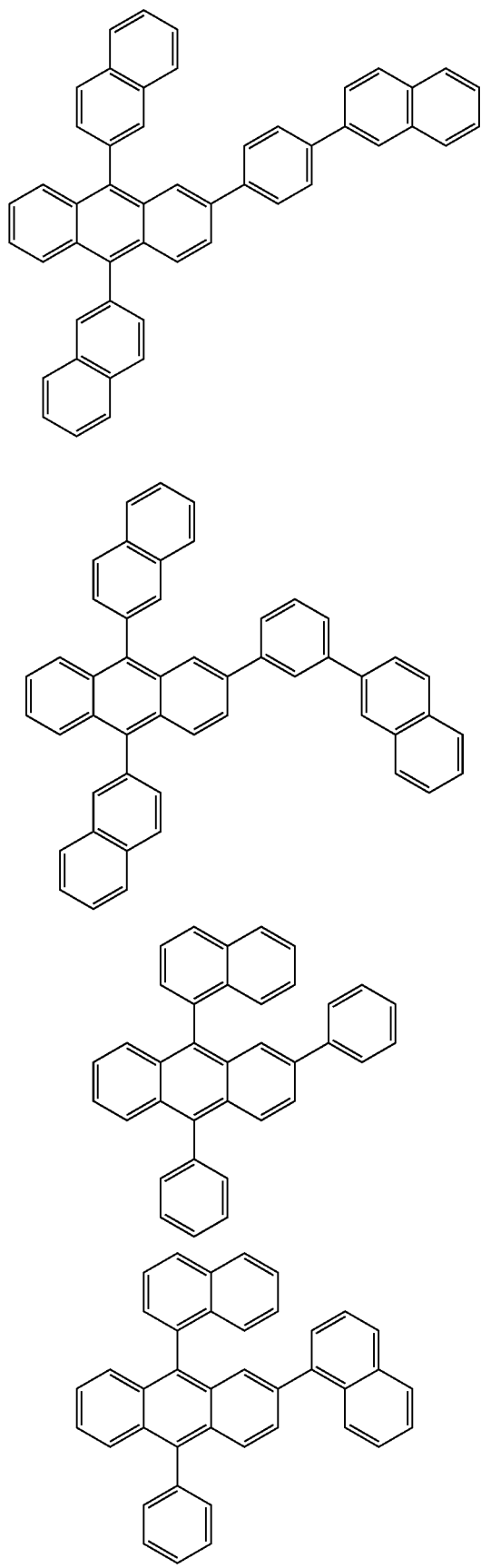
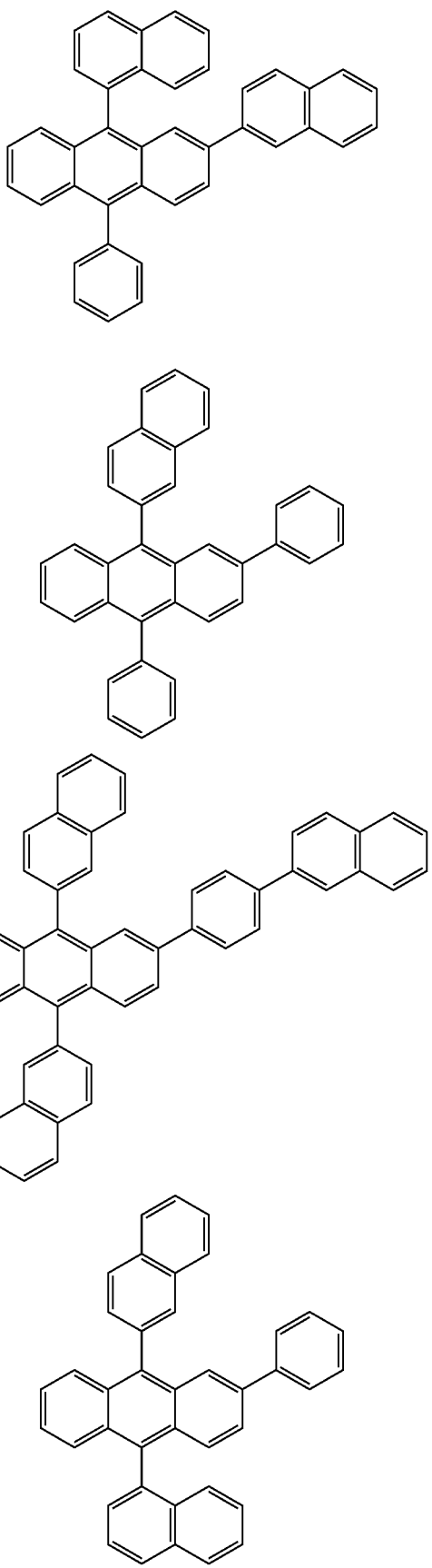

-continued
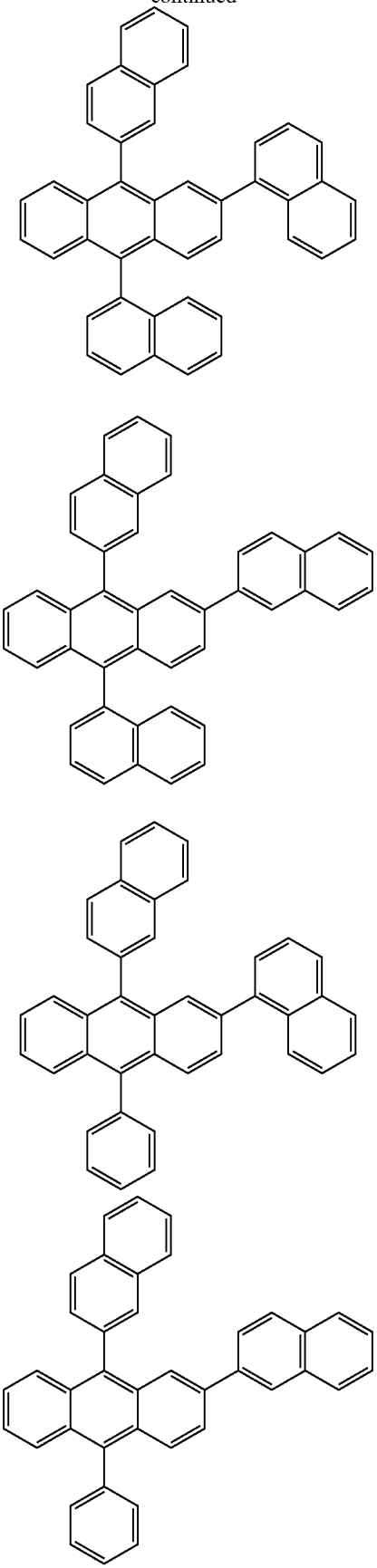
-continued
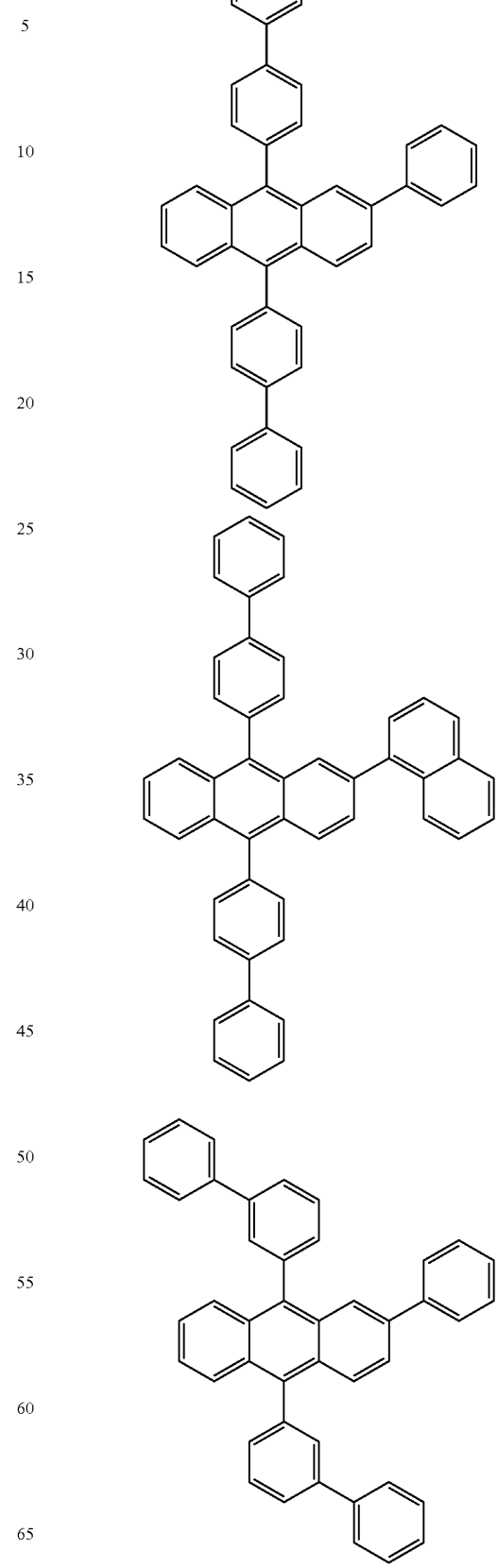

687
-continued
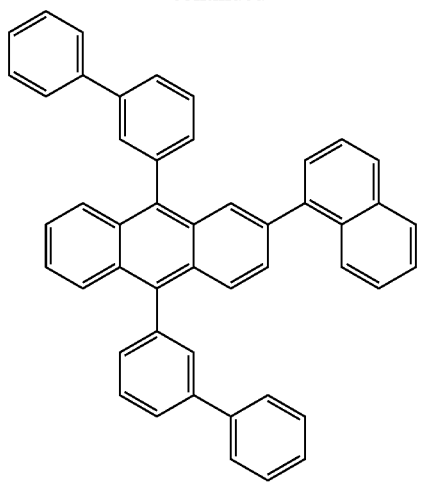
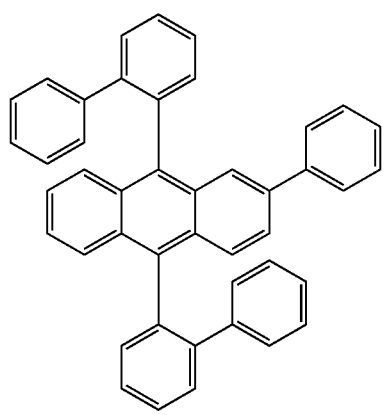
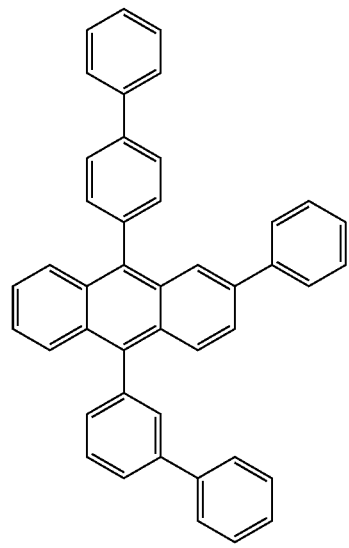
688
-continued
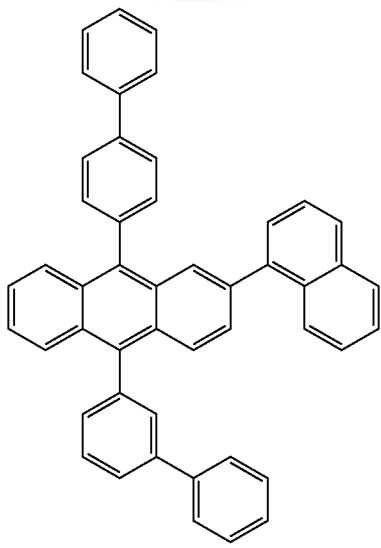
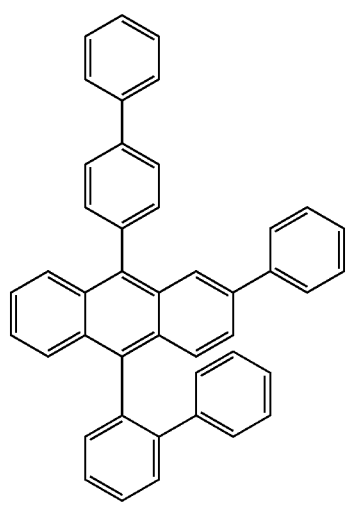
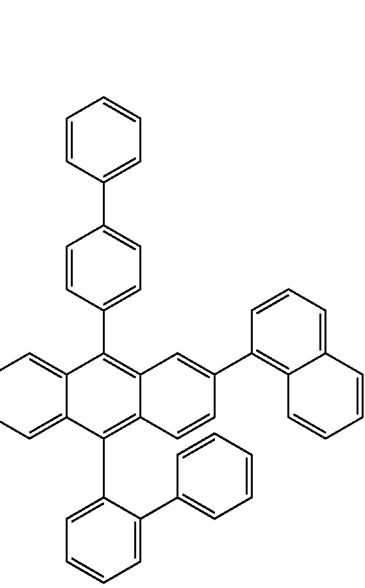

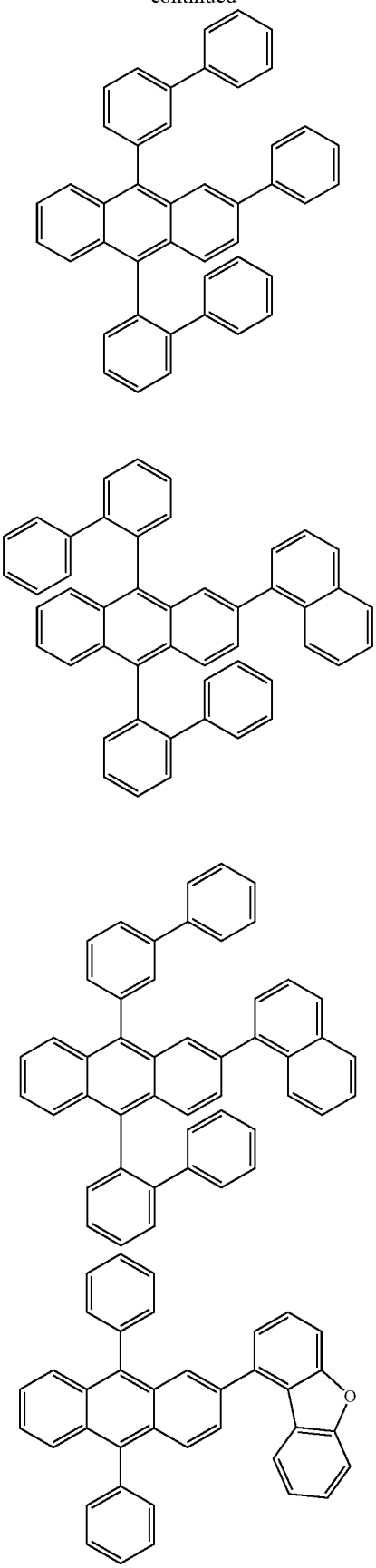
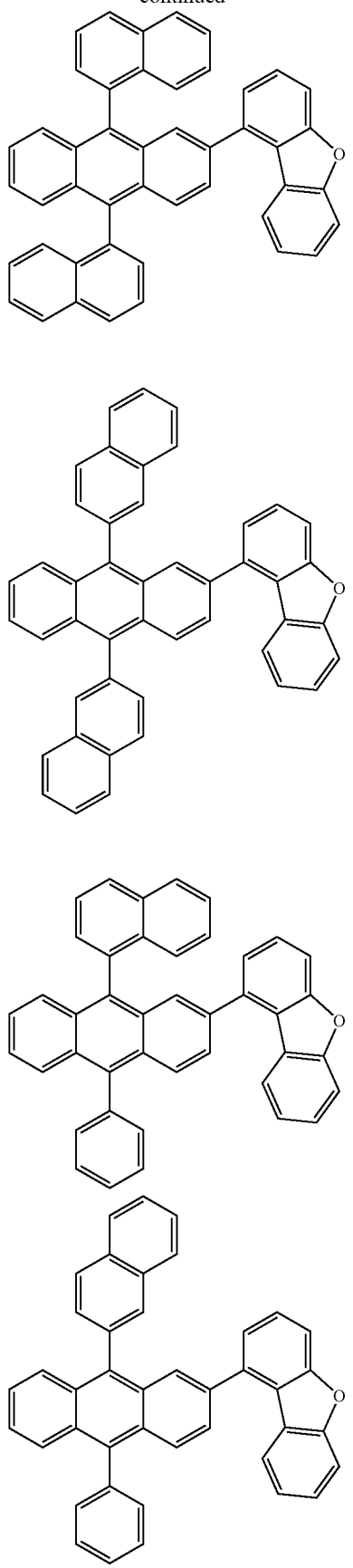

691
-continued
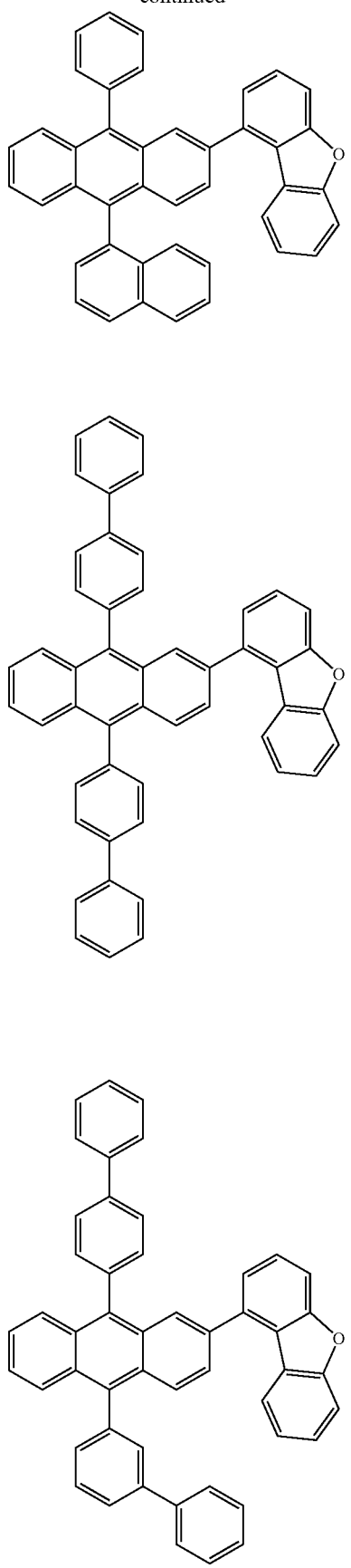
692
-continued
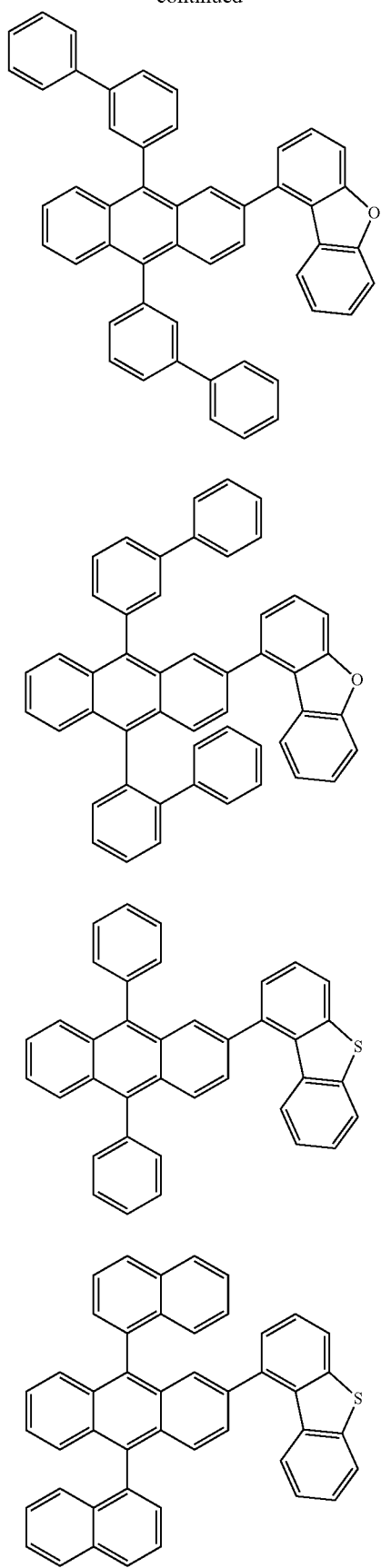

| 693 -continued | 694 -continued |
|---|---|
| 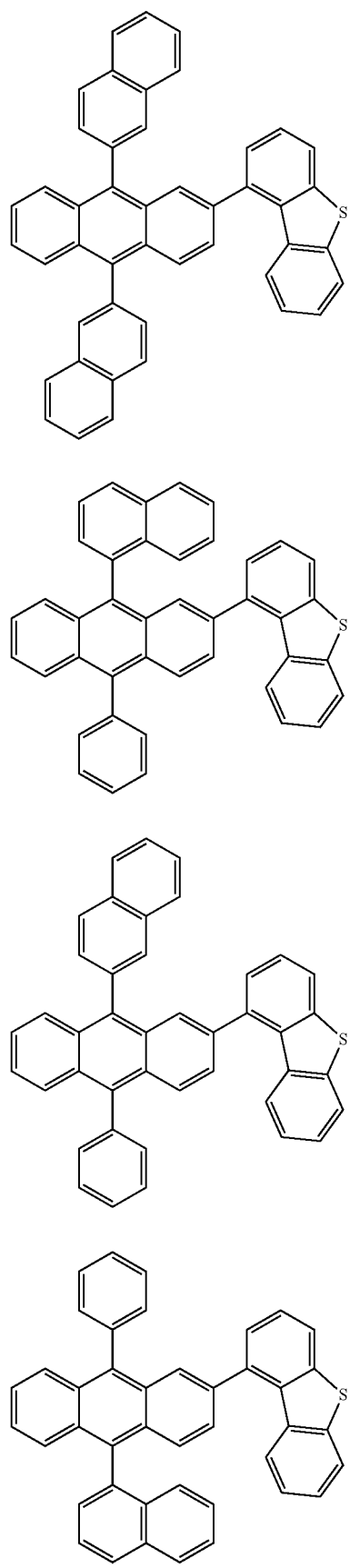 | 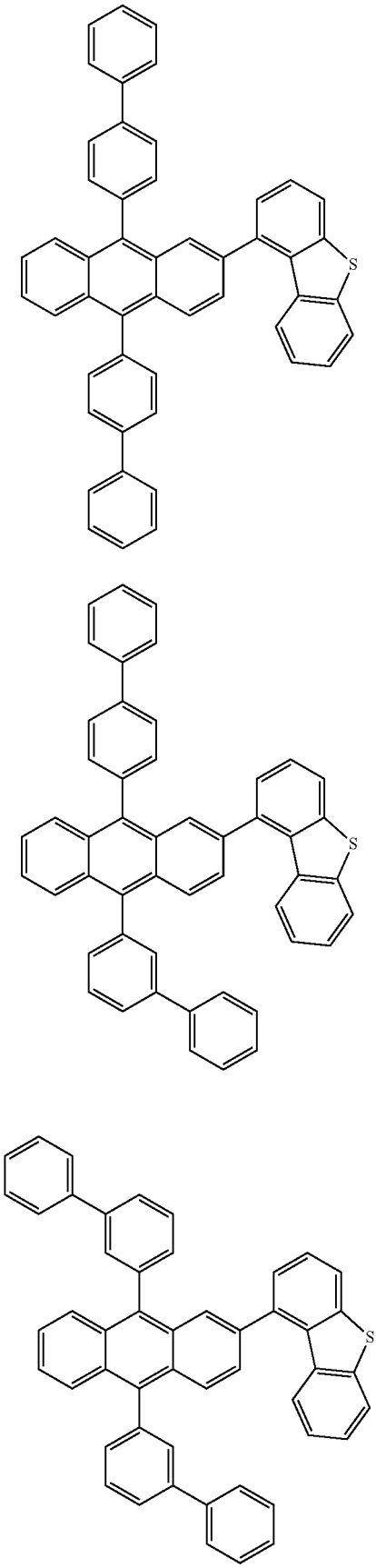 |

695
-continued
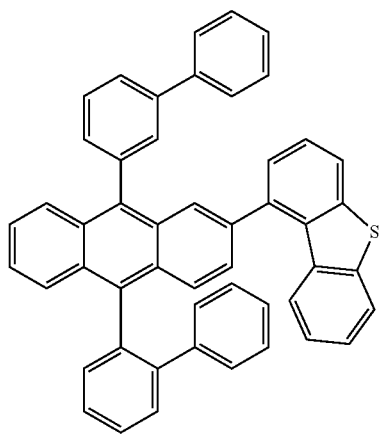
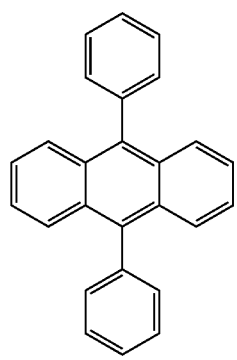
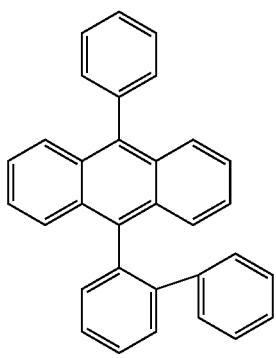
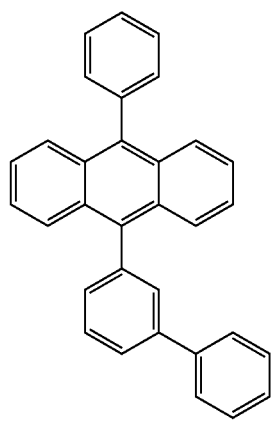
696
-continued
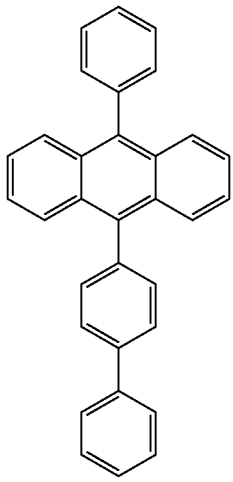
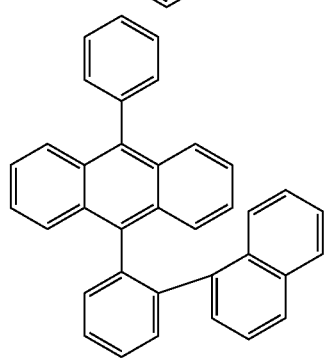
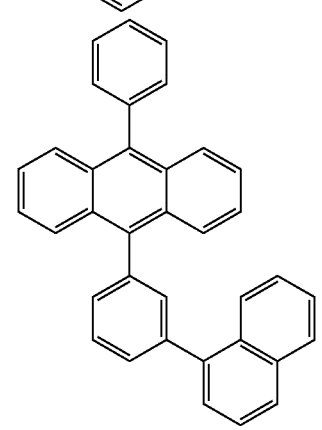
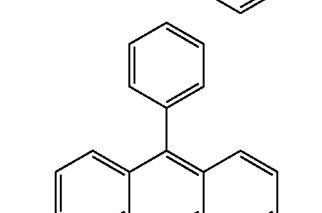
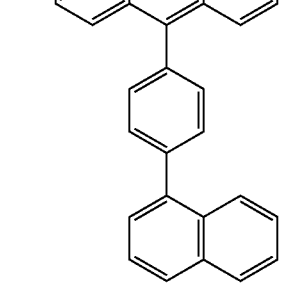

697
-continued
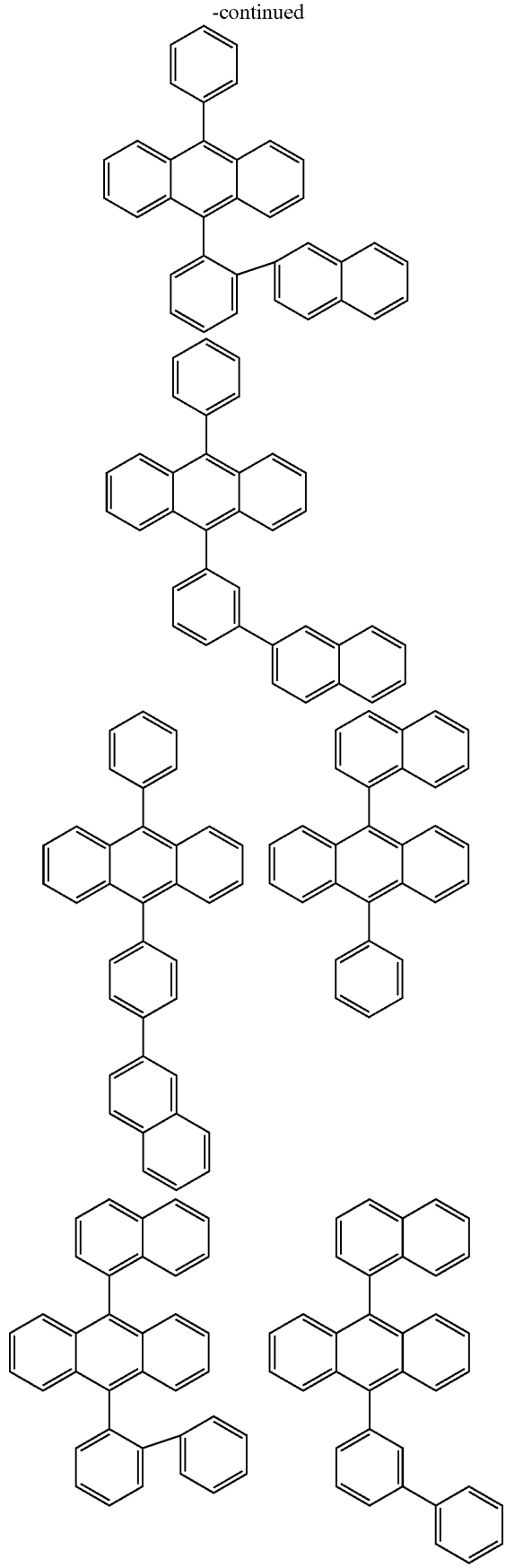
698
-continued
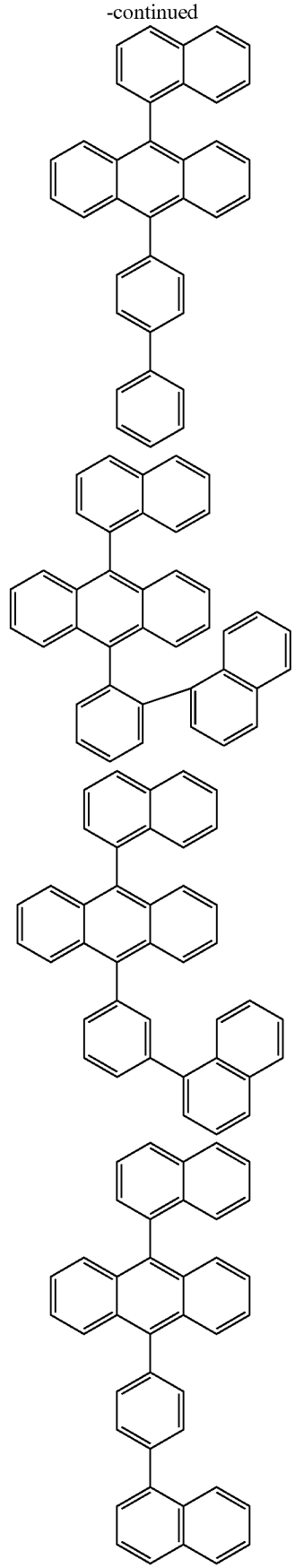

699
-continued
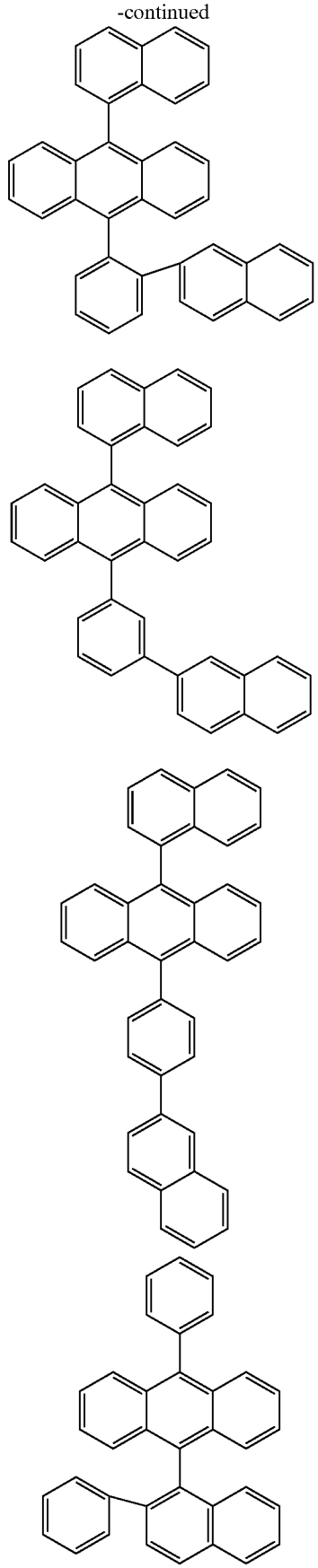
700
-continued
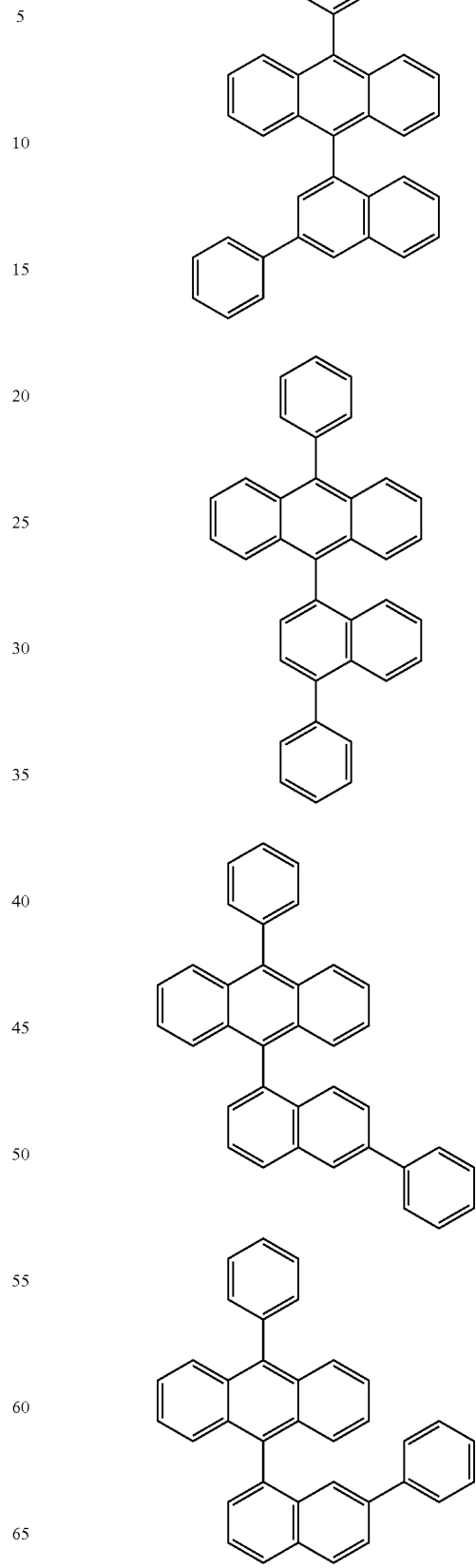

701
-continued

702
-continued
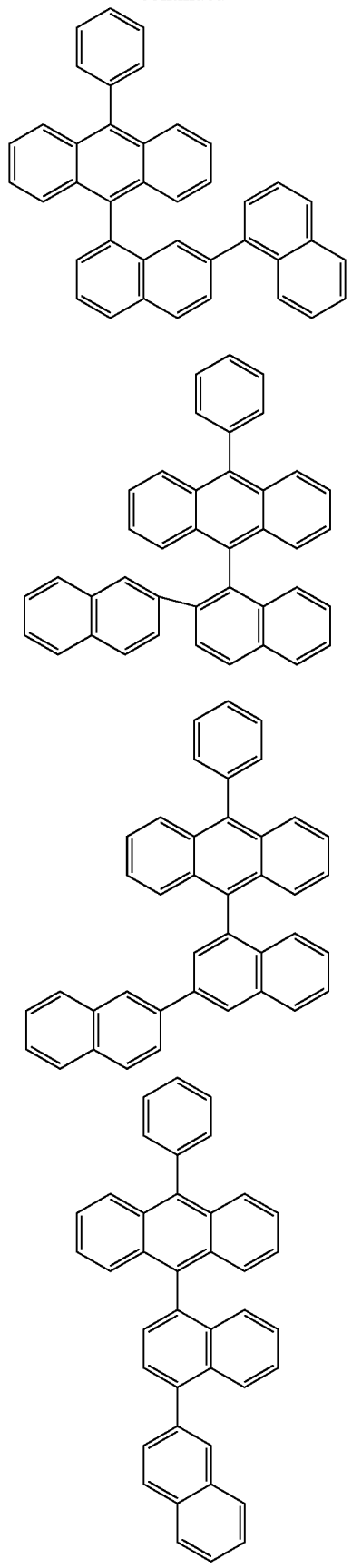

703
-continued
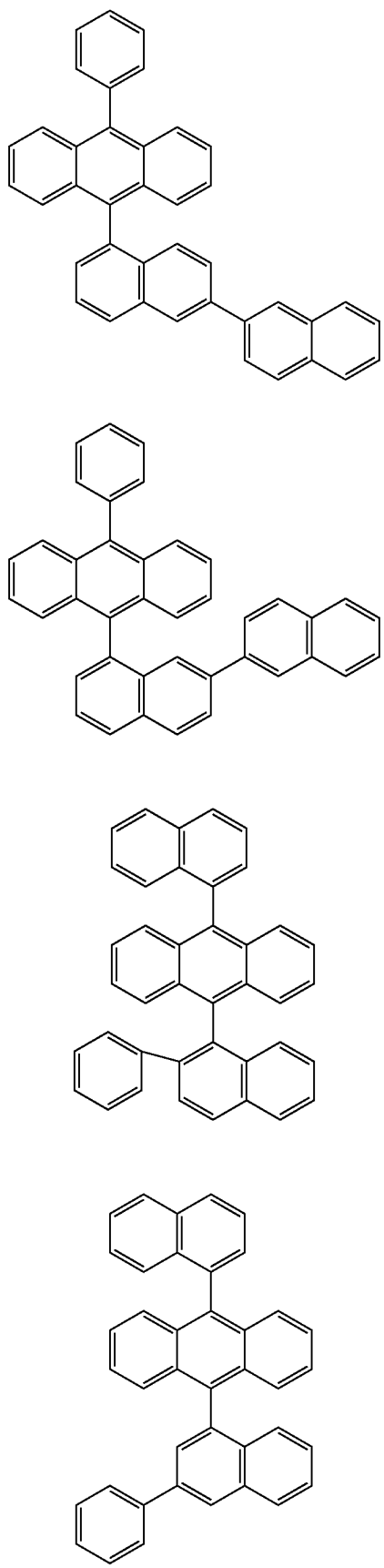
704
-continued
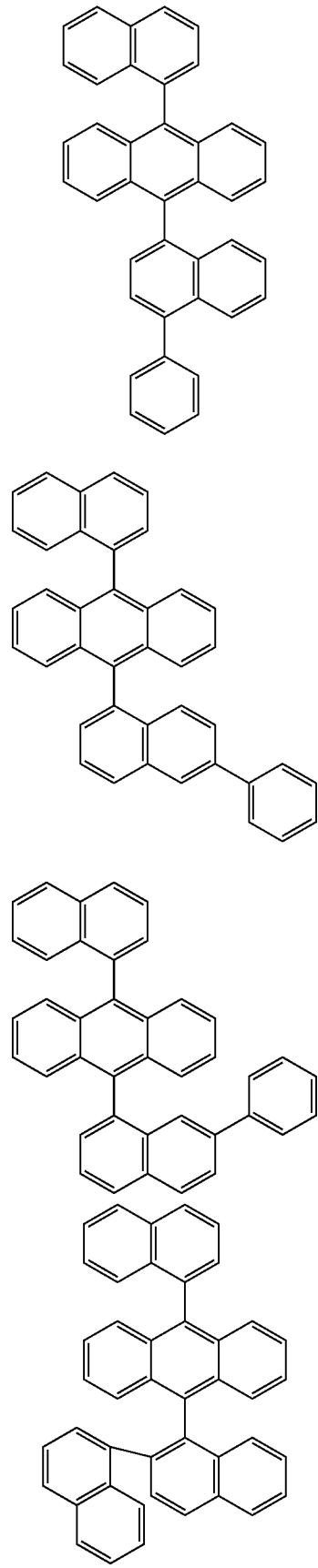

705
-continued
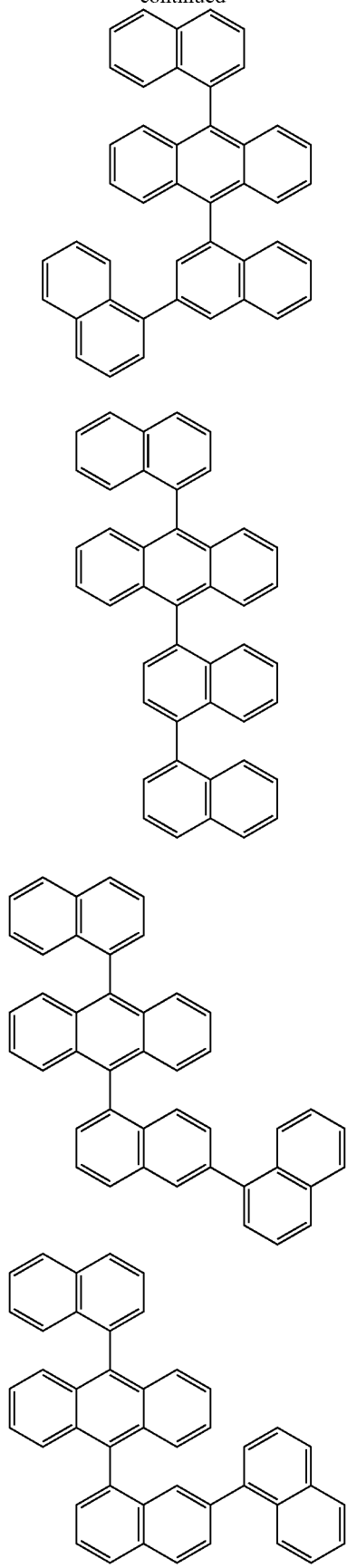
706
-continued
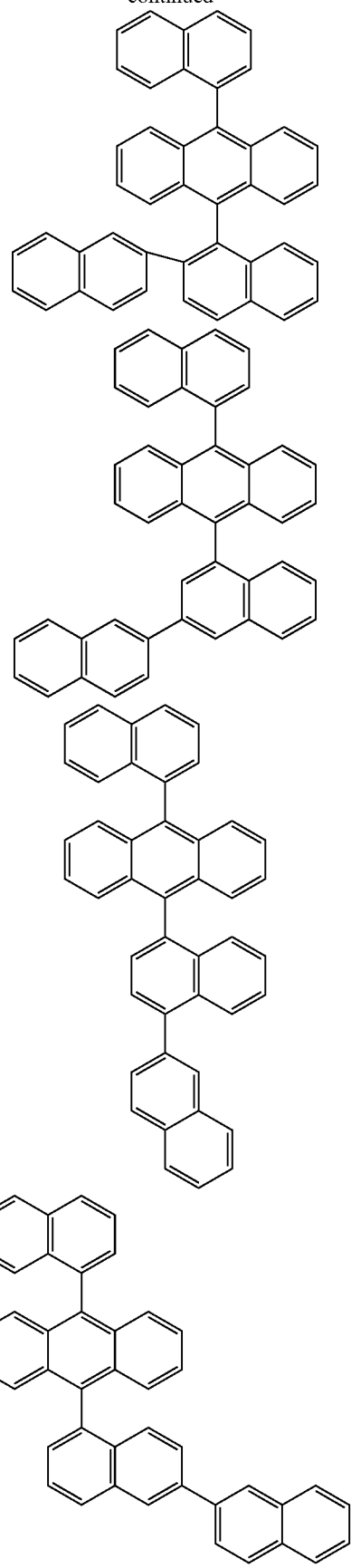

707
-continued
708
-continued
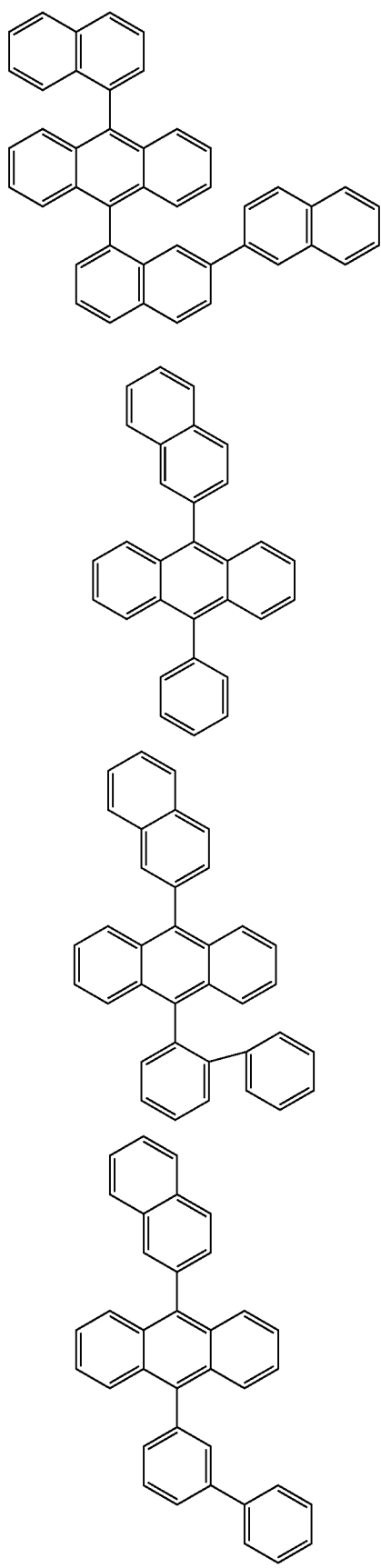
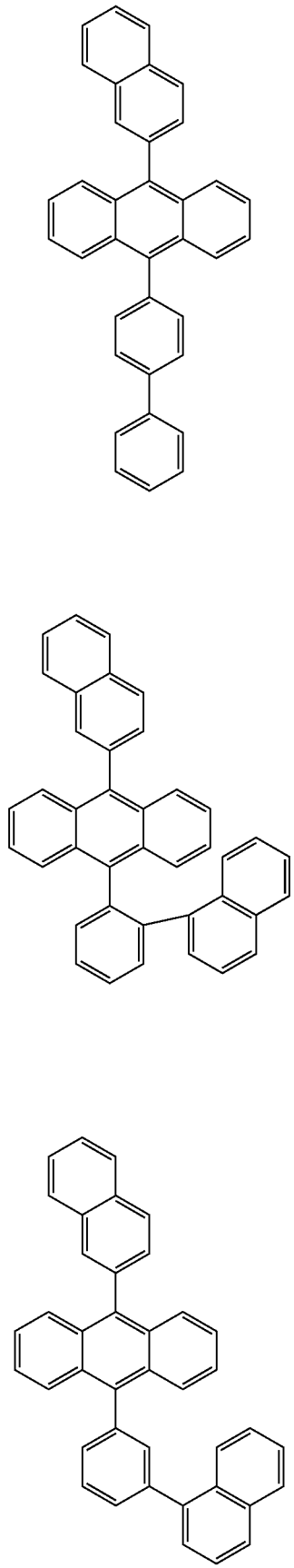

709
-continued
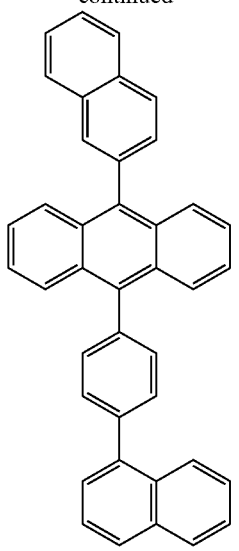
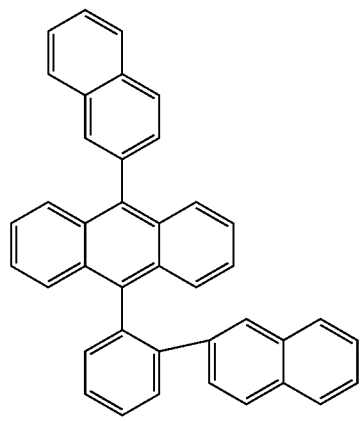
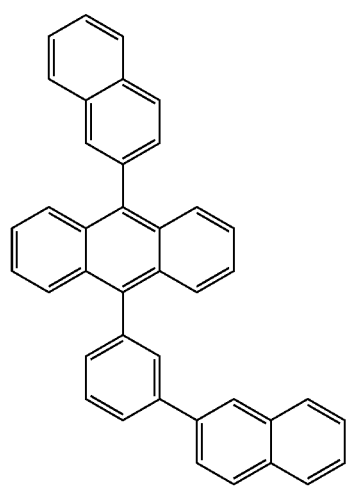
710
-continued
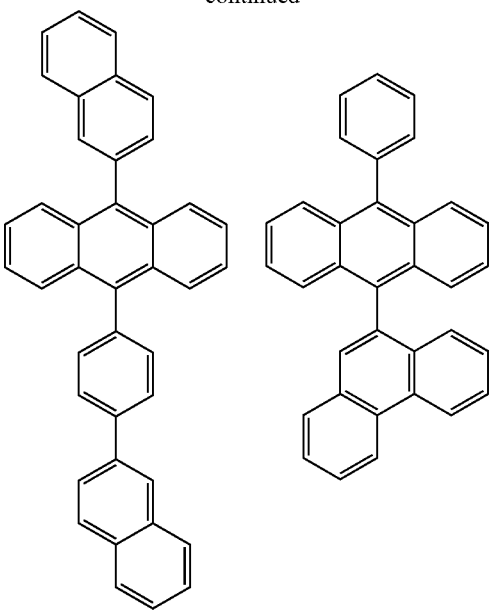
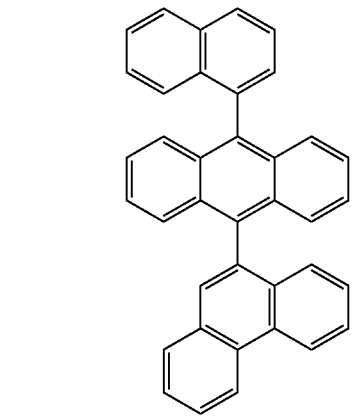
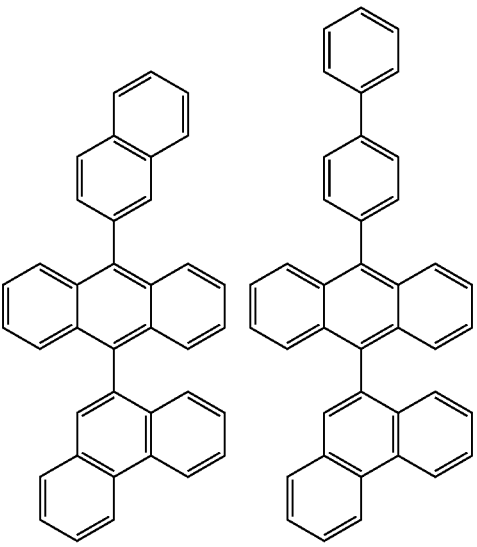

711
-continued
712
-continued
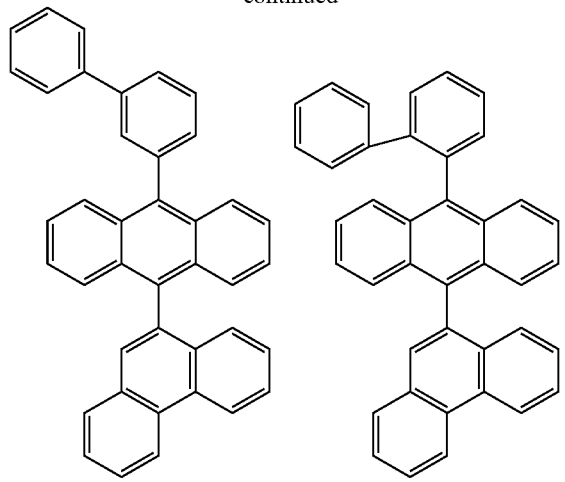
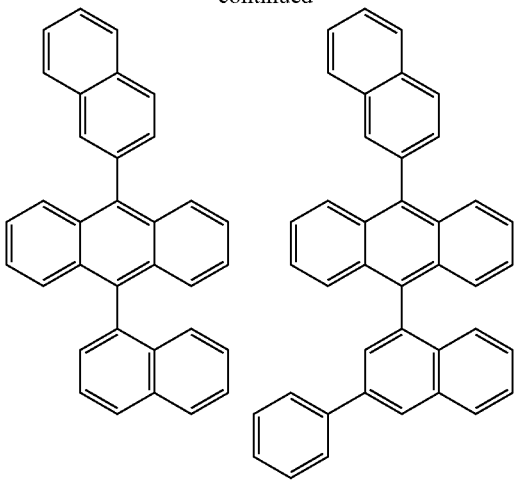
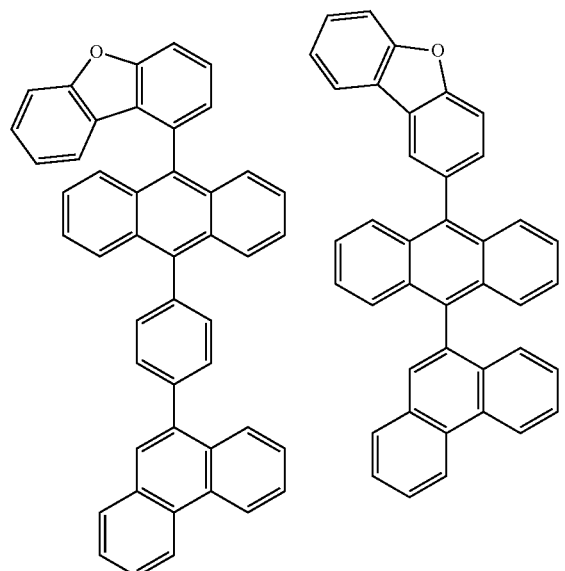
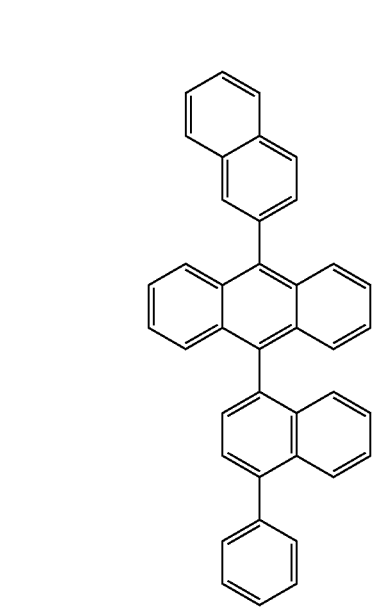
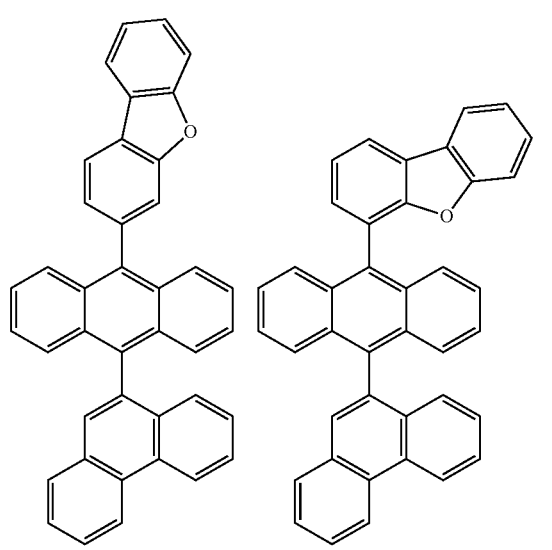
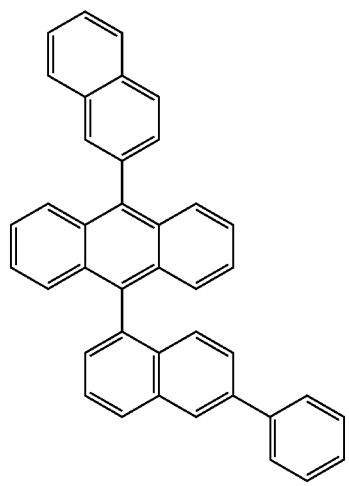

713
-continued
714
-continued
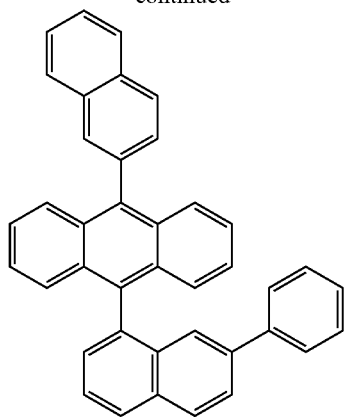
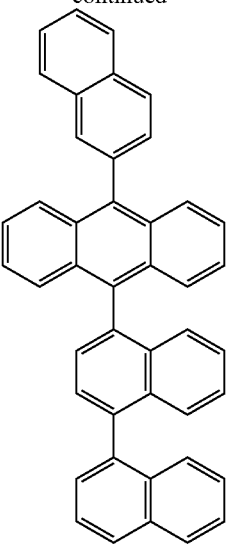
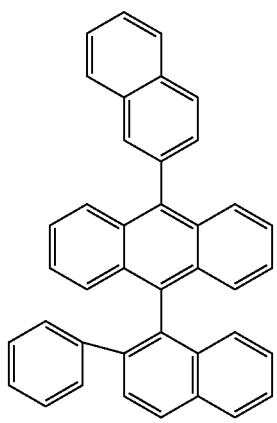
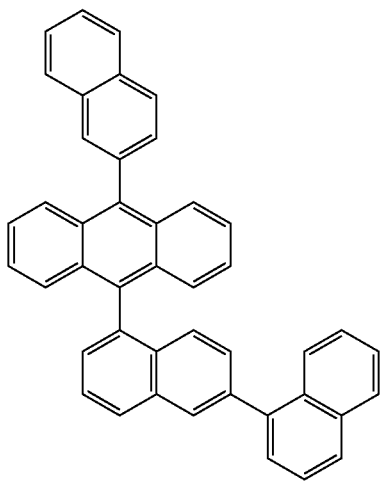
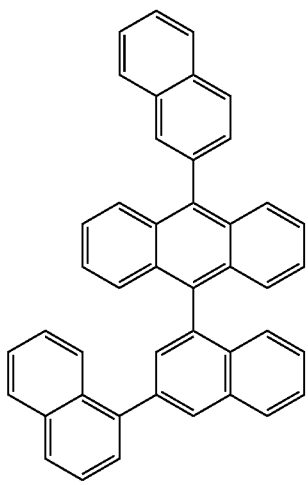
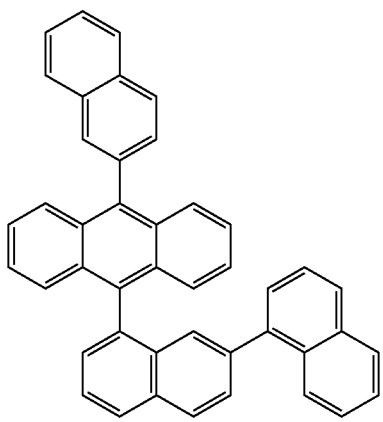

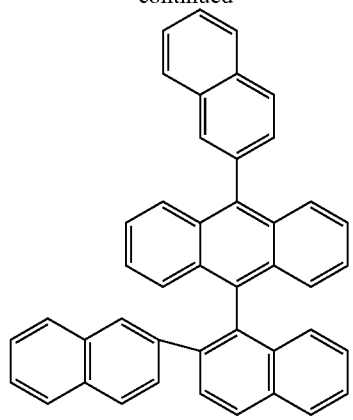
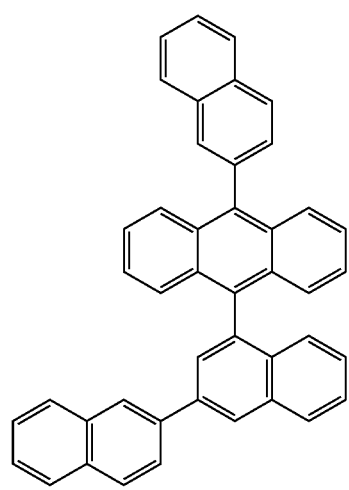
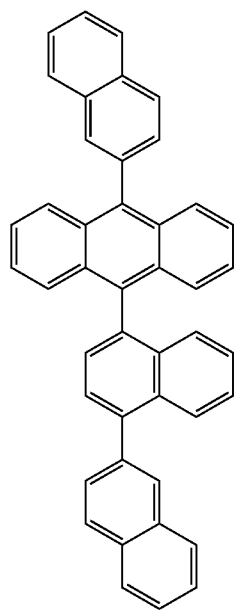
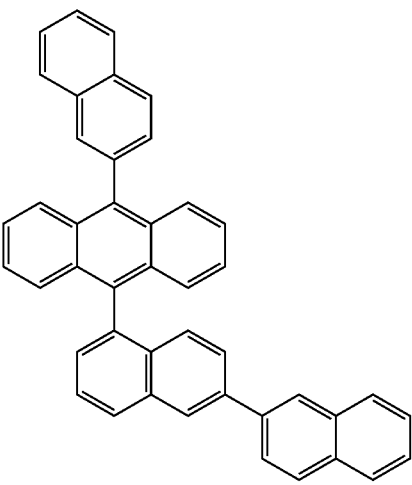
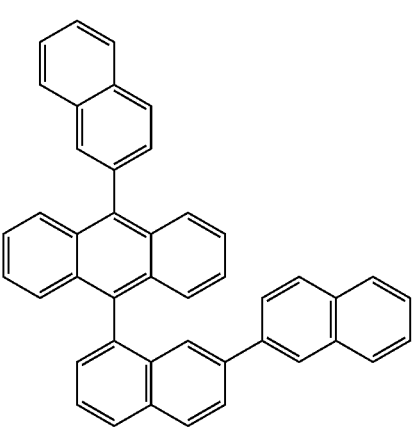
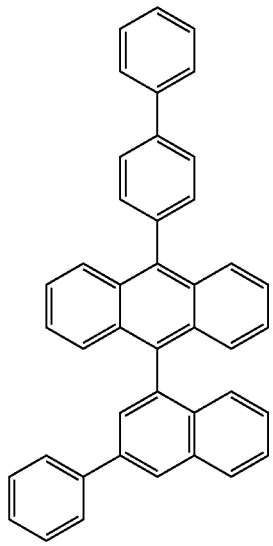

717
-continued
718
-continued
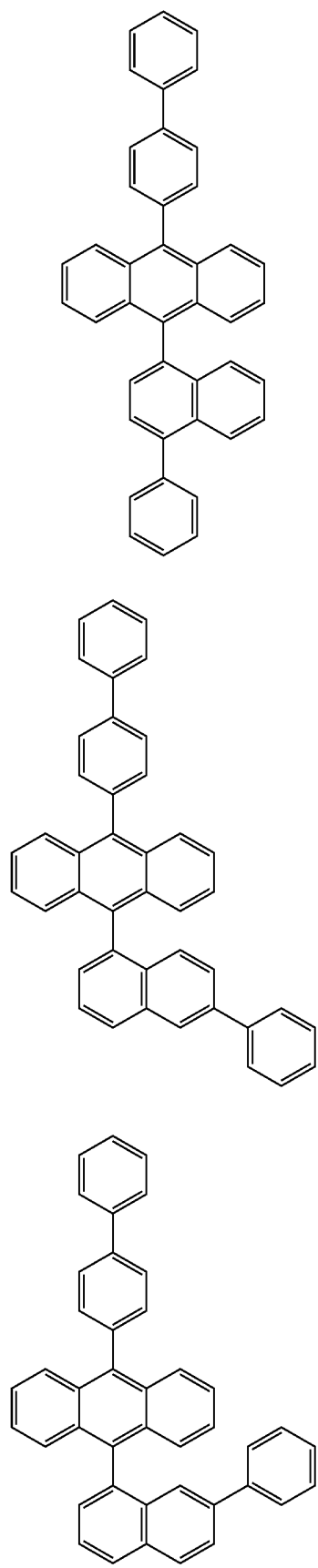
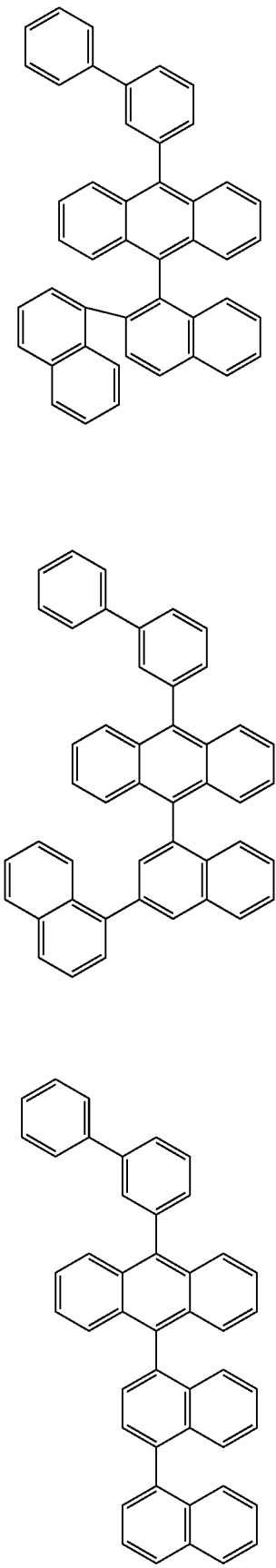

719
-continued
720
-continued
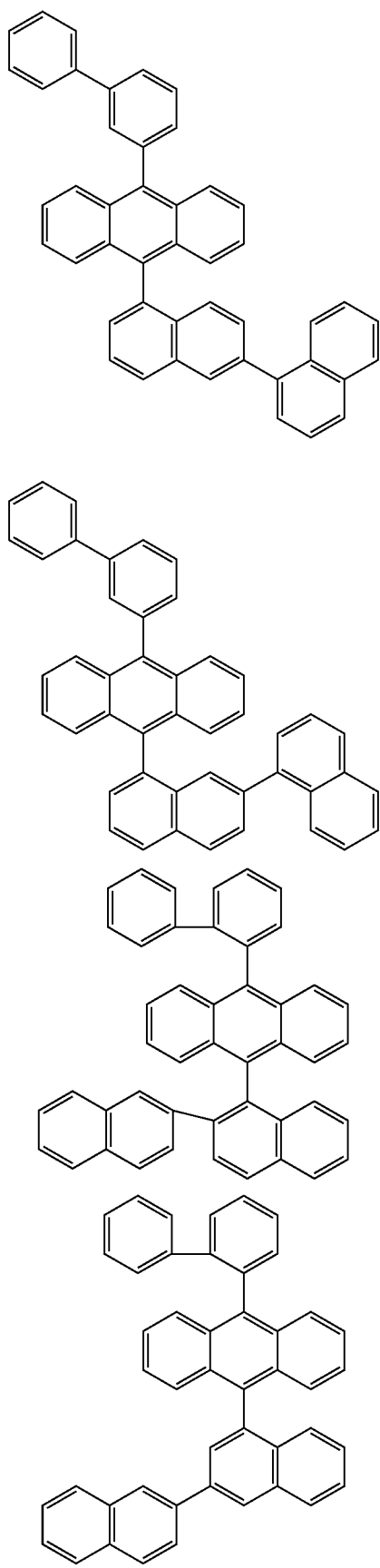
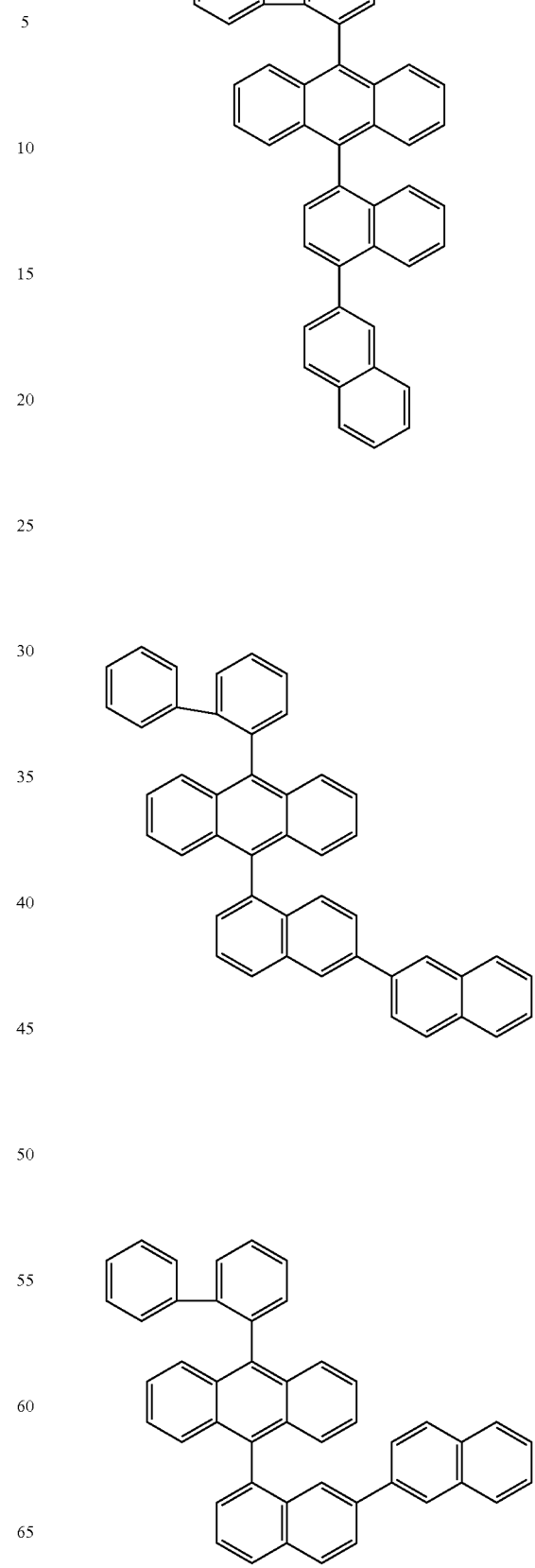

721
-continued
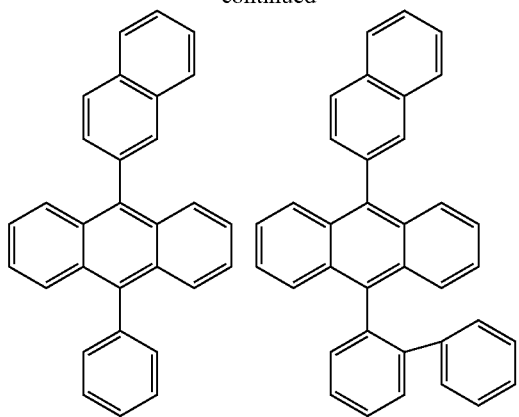
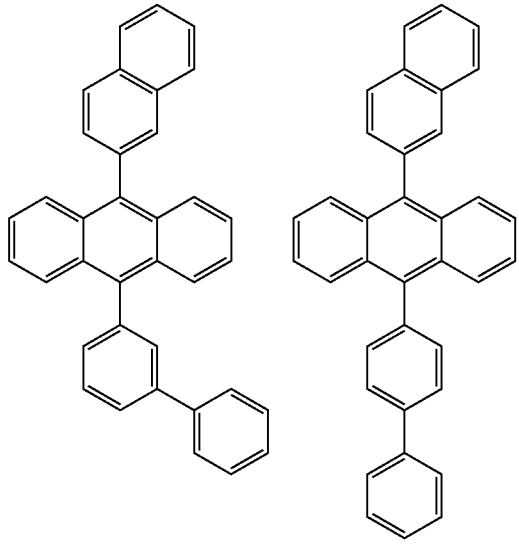
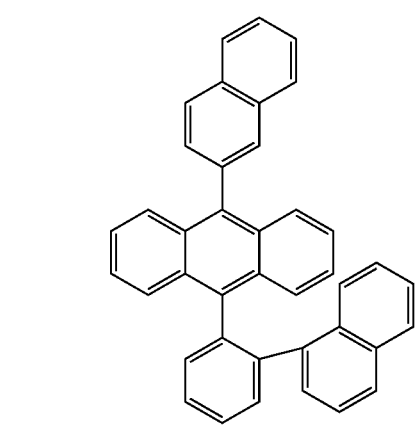
722
-continued
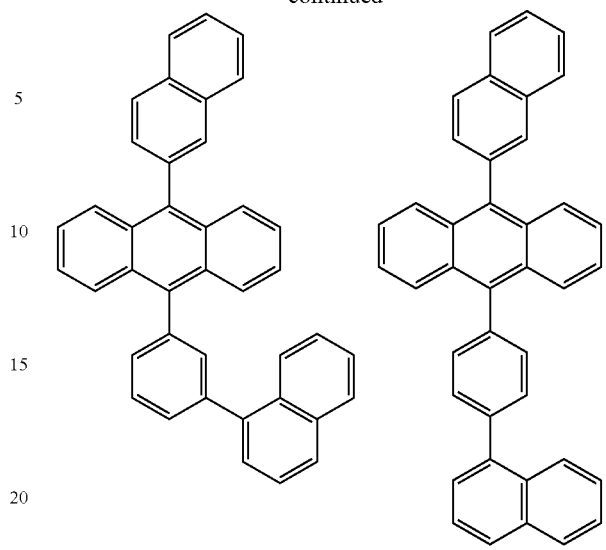
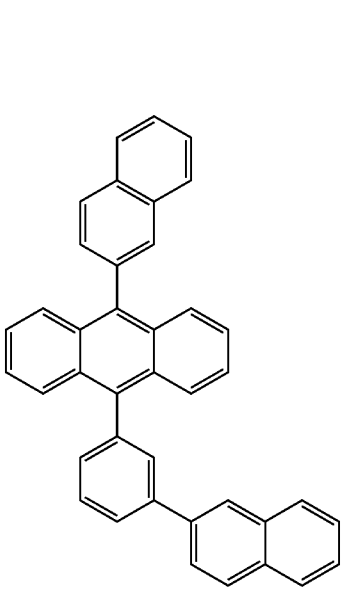

723
-continued
724
-continued
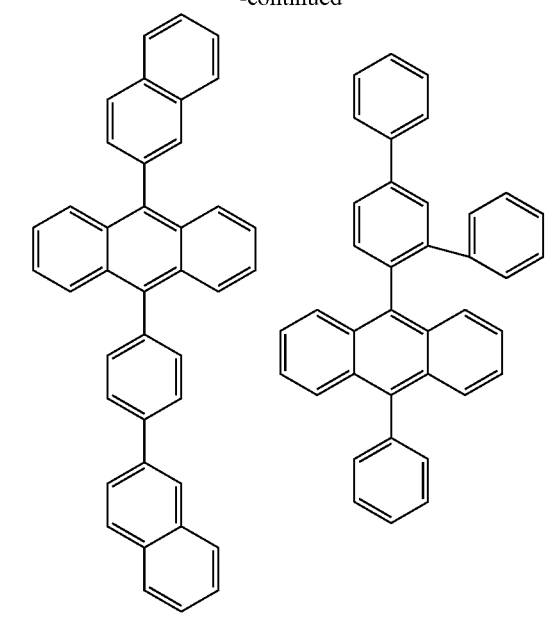
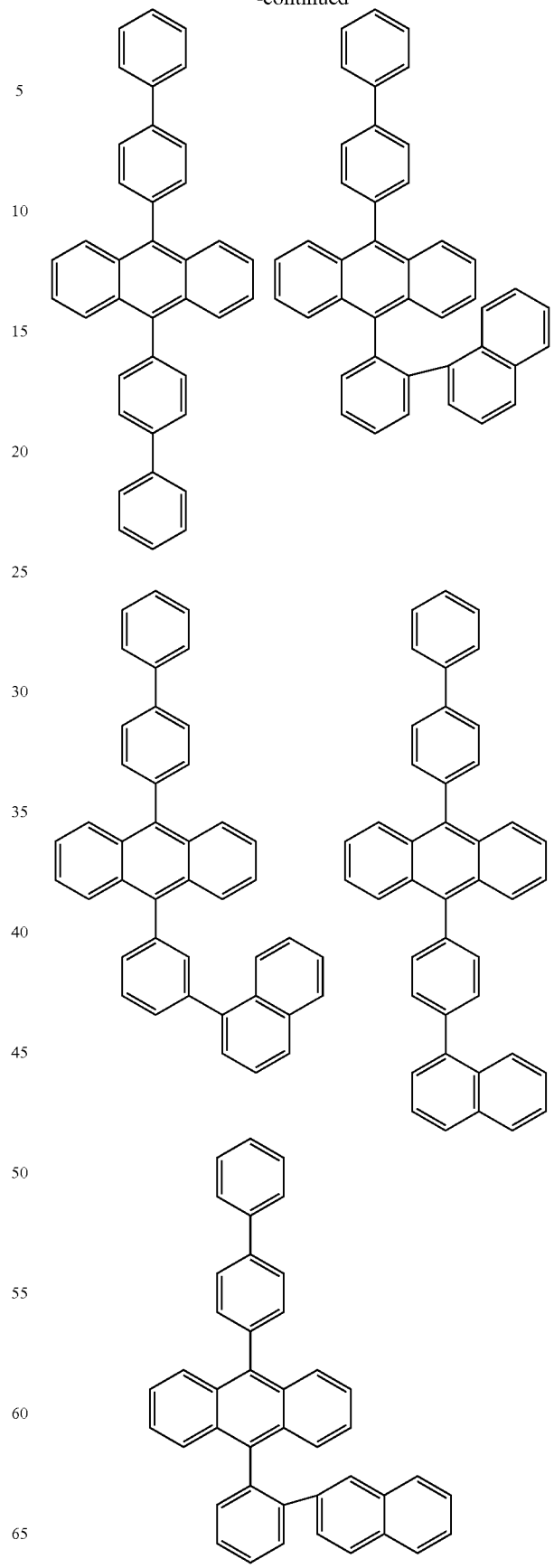

725
-continued
726
-continued
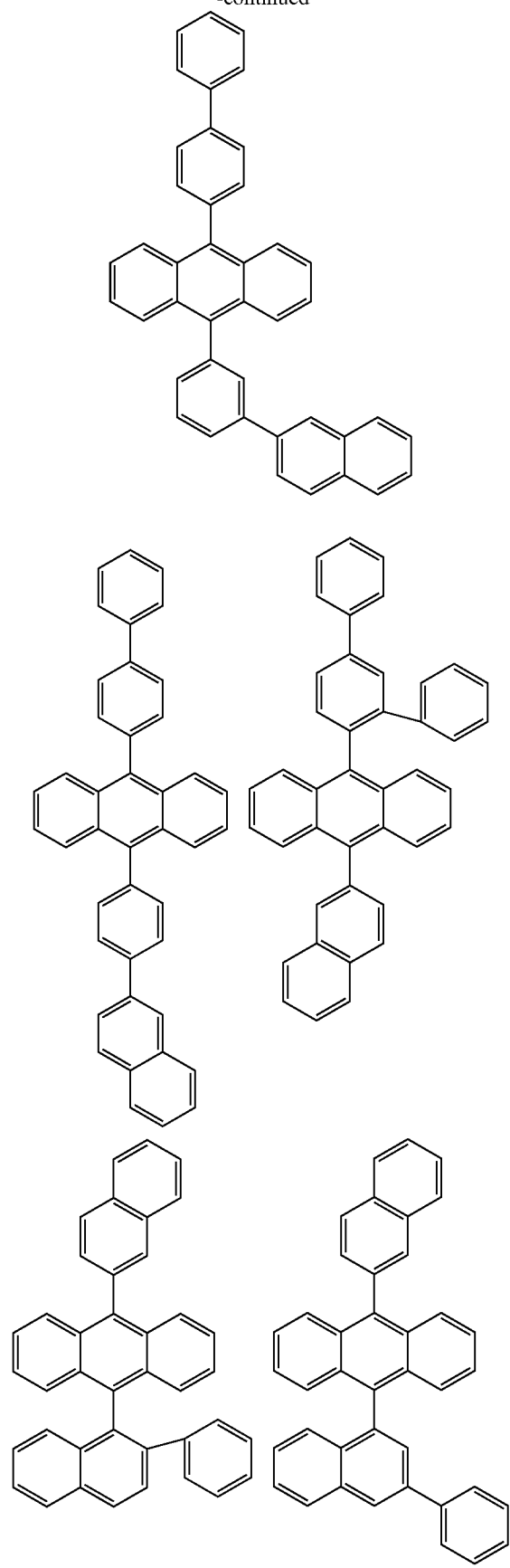
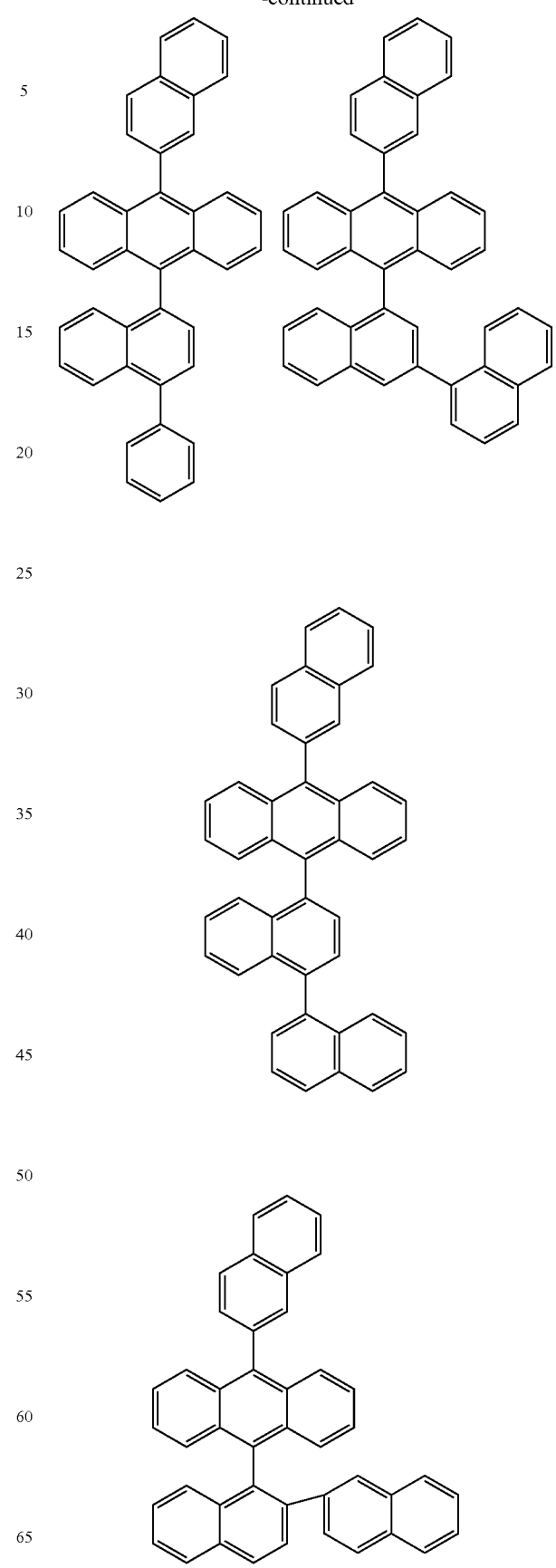

727
-continued
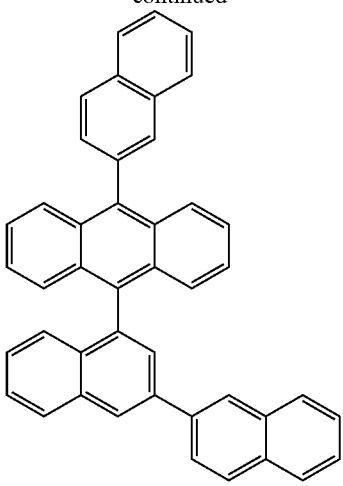
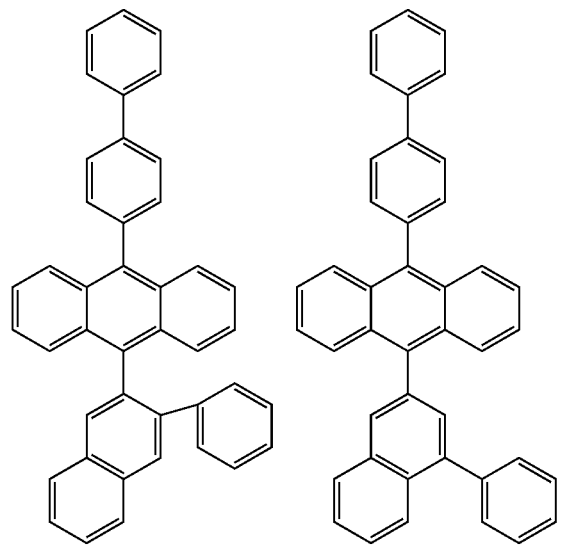
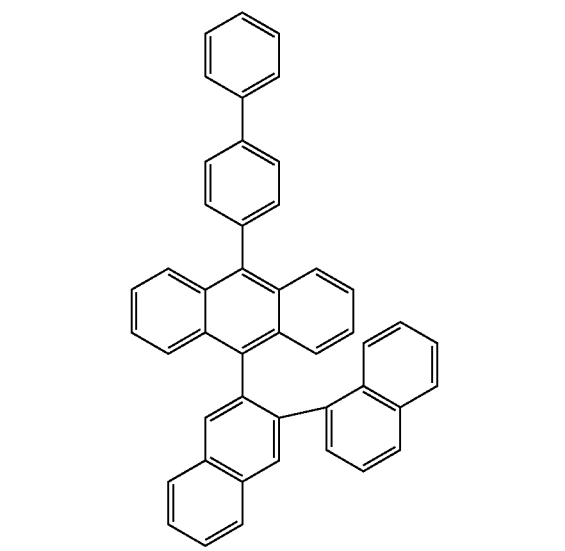
728
-continued
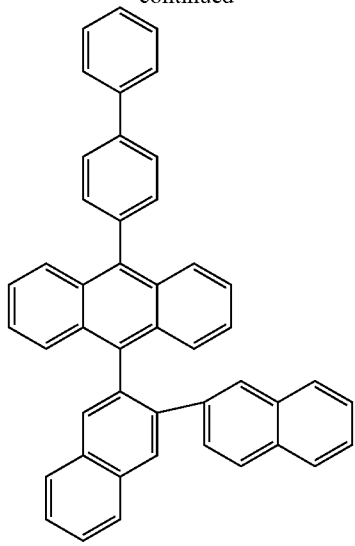
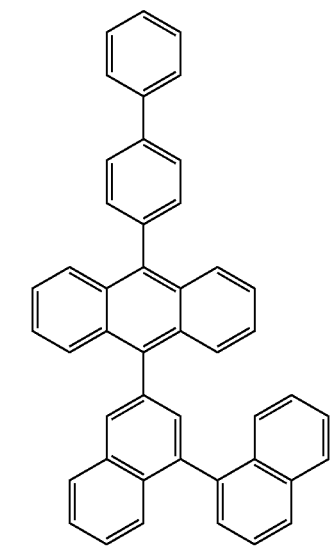
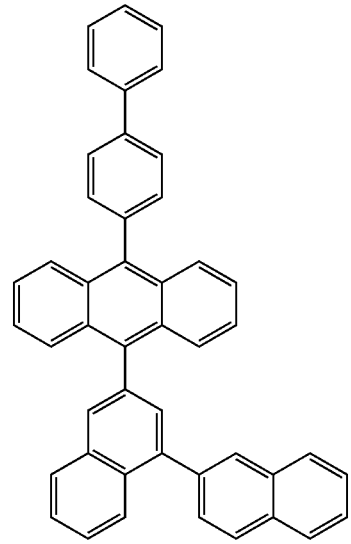

729
-continued
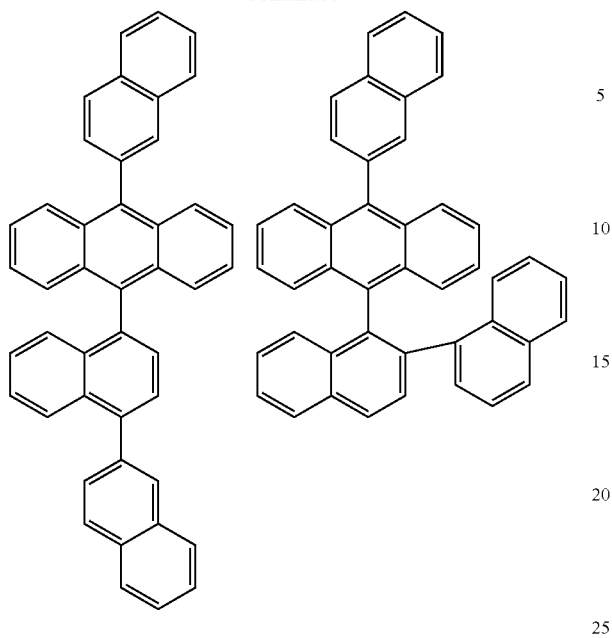
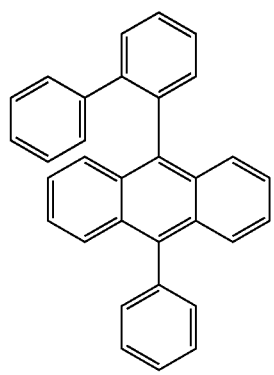
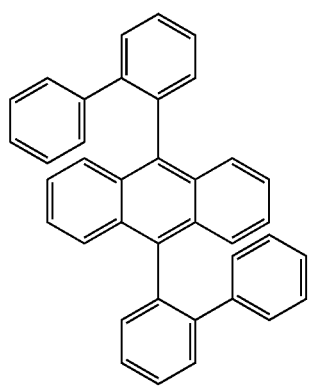
730
-continued
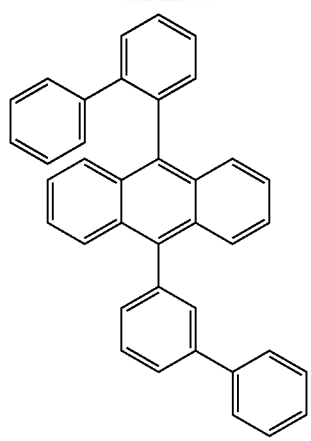
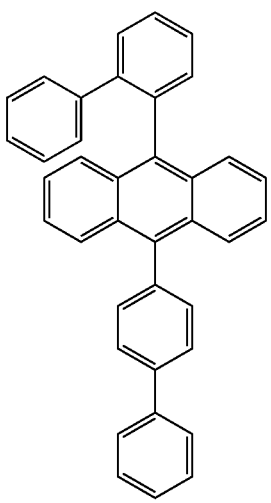
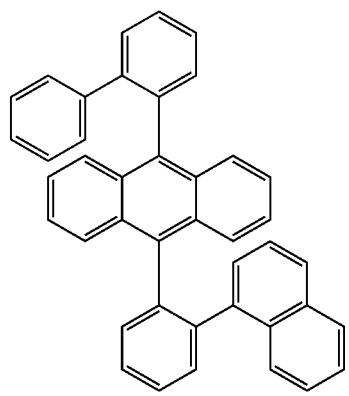

731
-continued
732
-continued
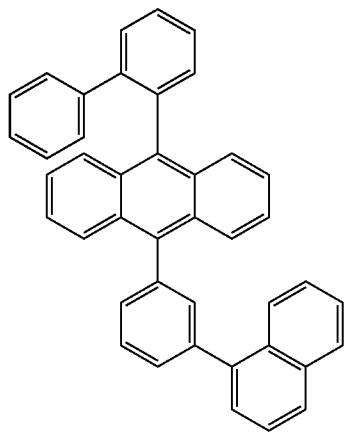
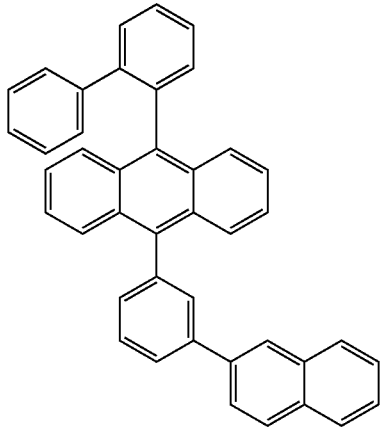
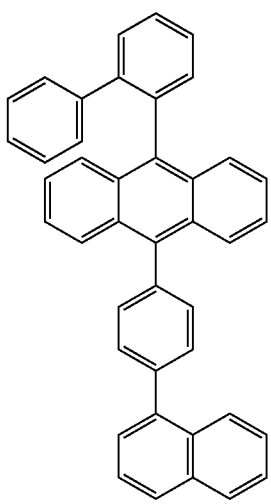
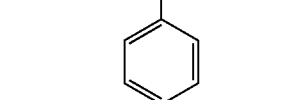
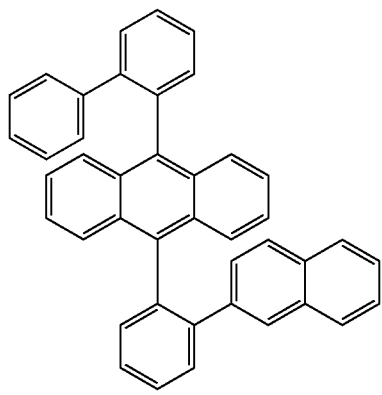

733
-continued
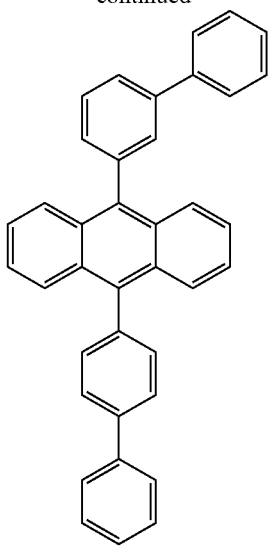
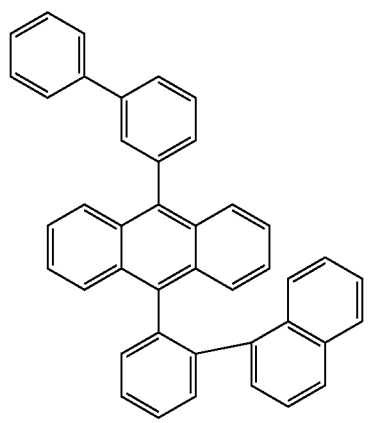
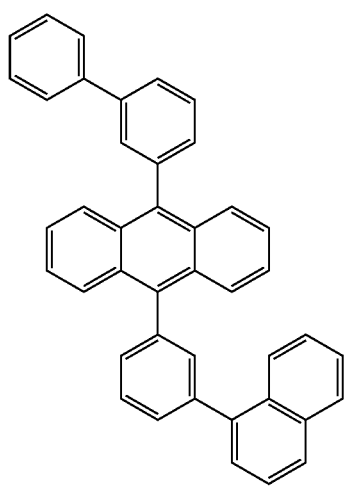
734
-continued
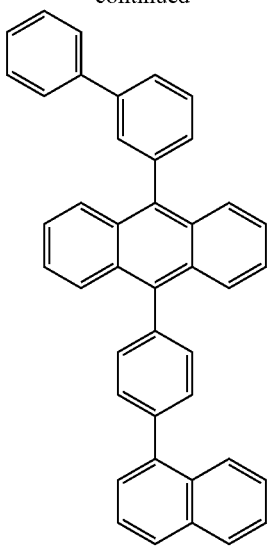
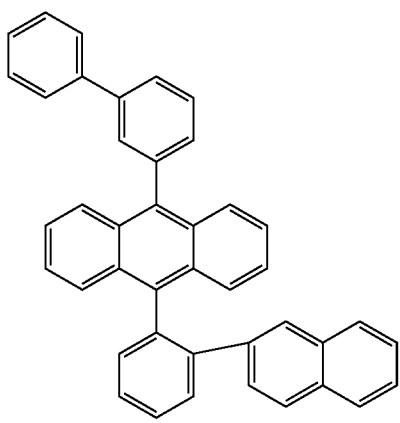
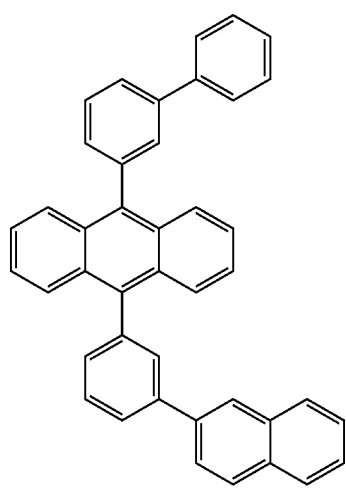

735
-continued
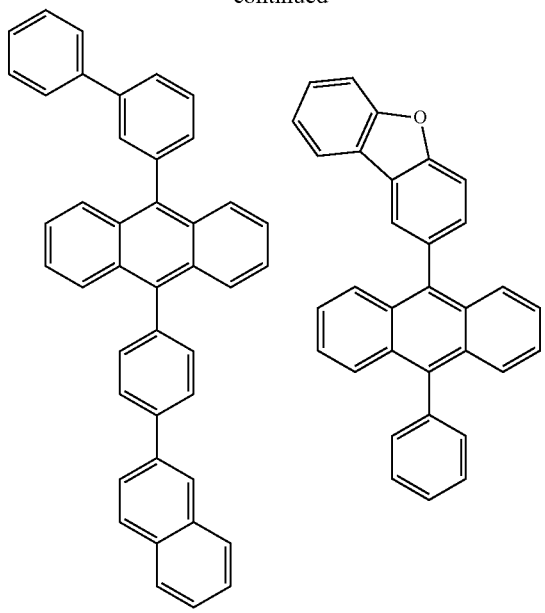
736
-continued
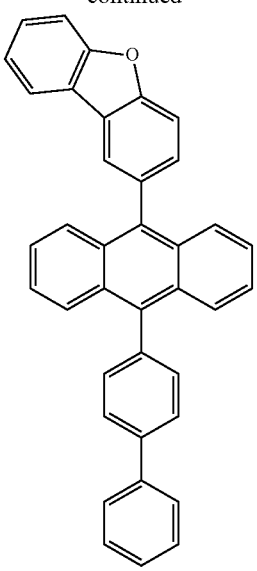
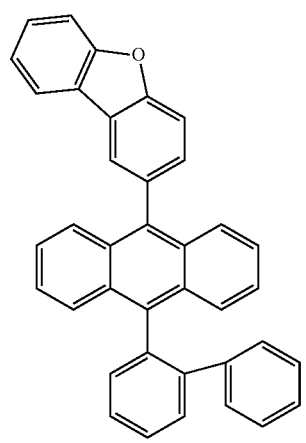
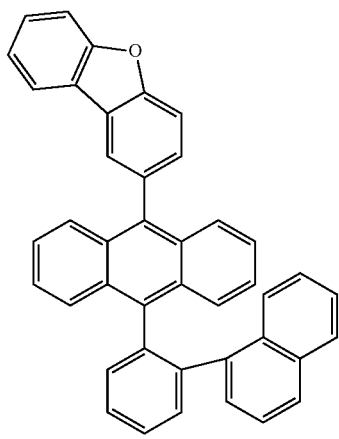
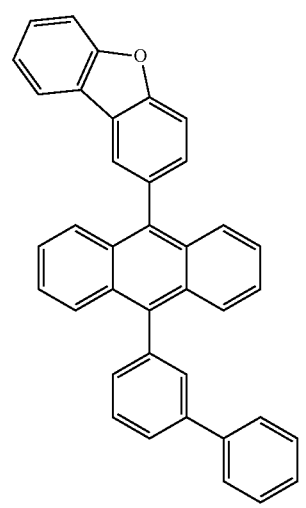
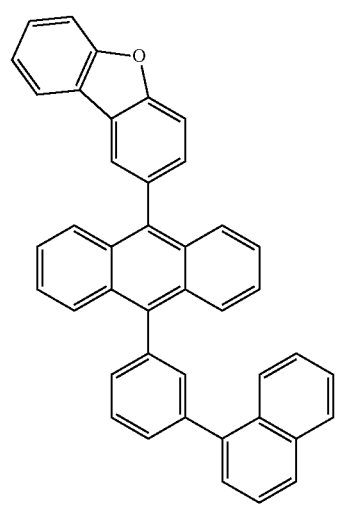

737
-continued
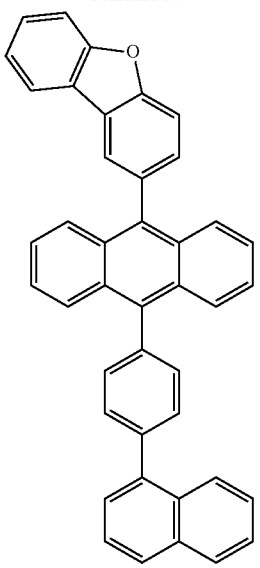
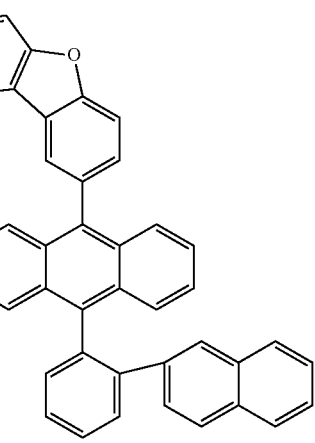
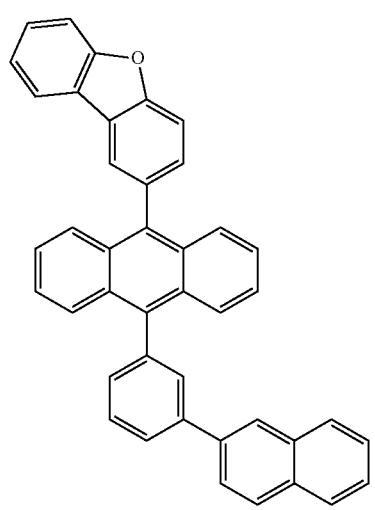
738
-continued
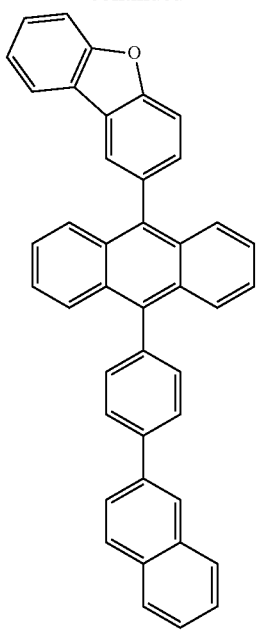
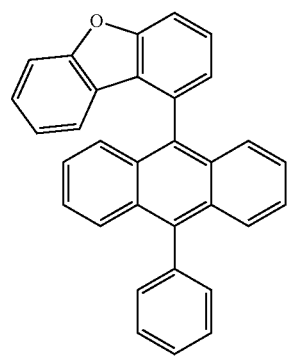
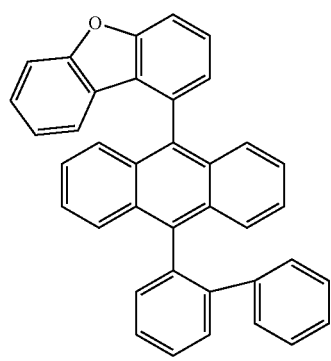

739
-continued
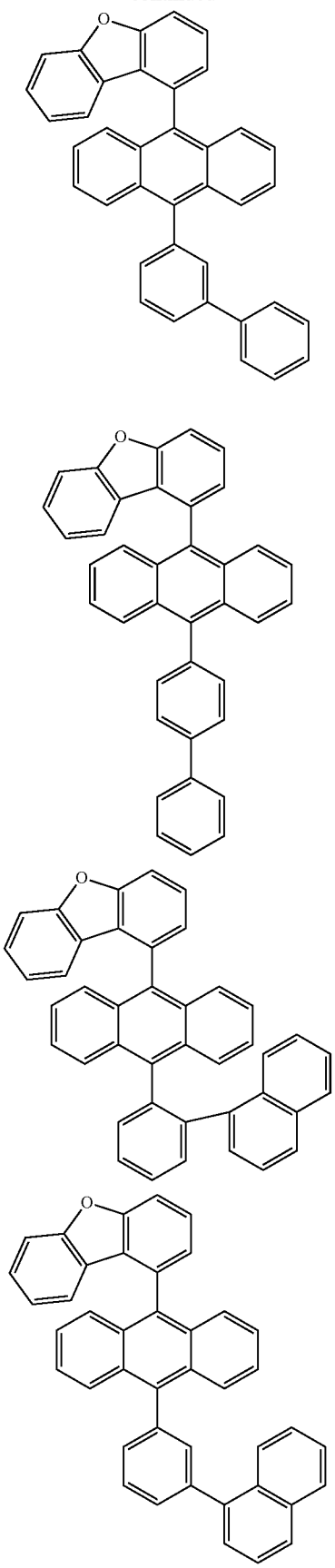
740
-continued
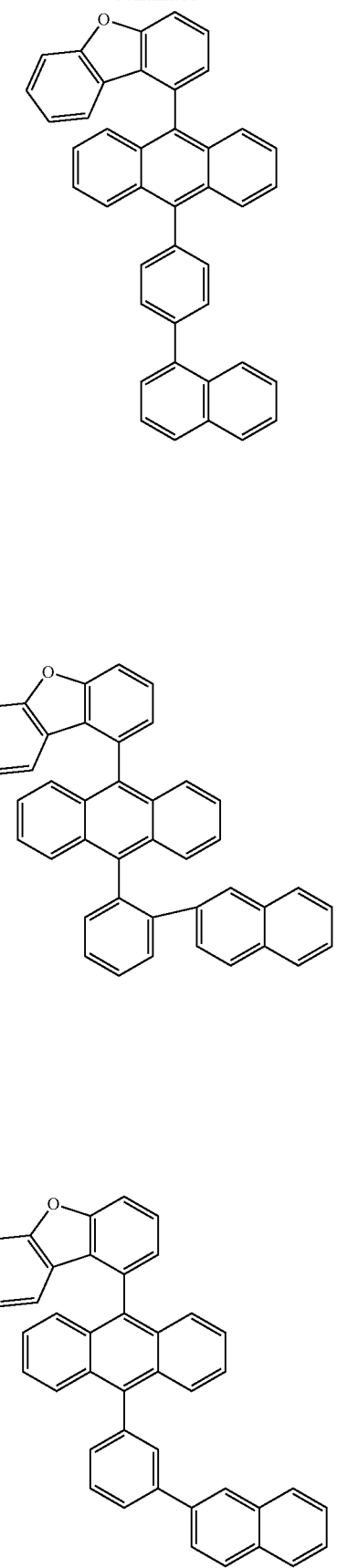

741
-continued
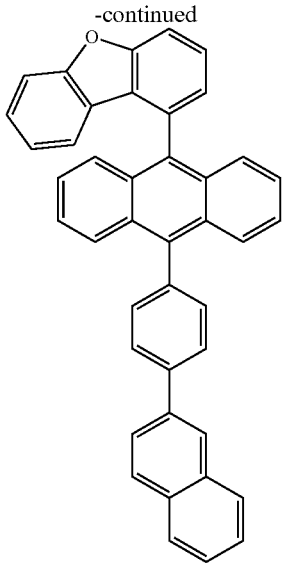
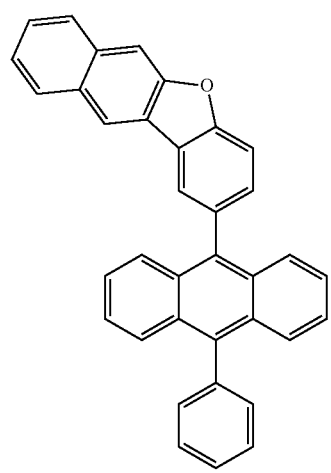
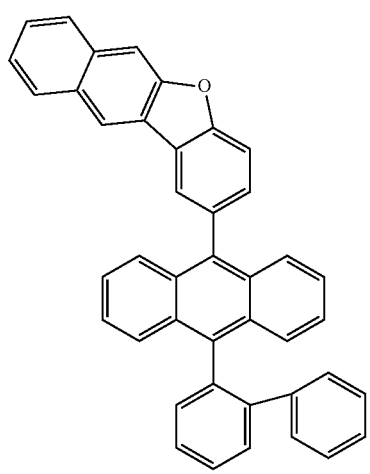
742
-continued
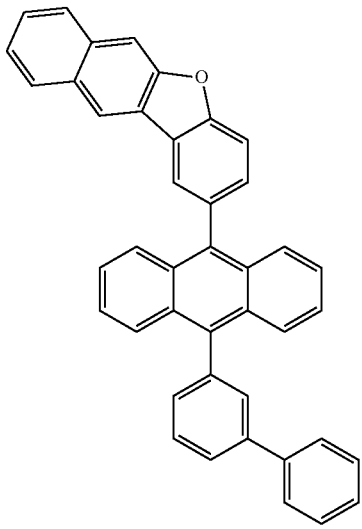
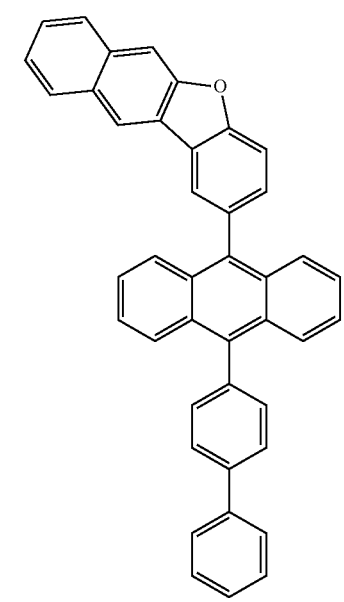
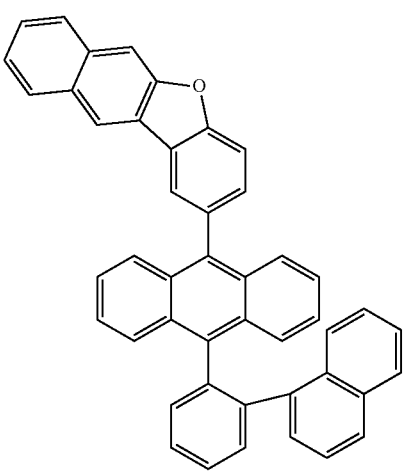

743
-continued
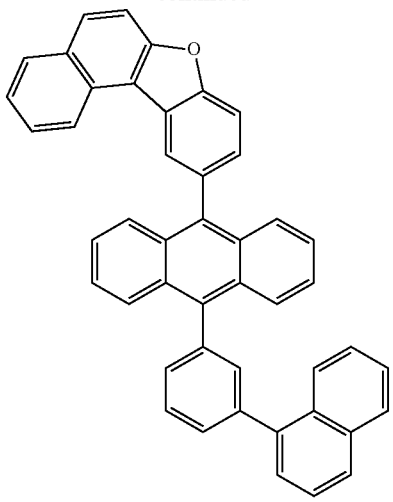
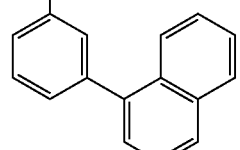
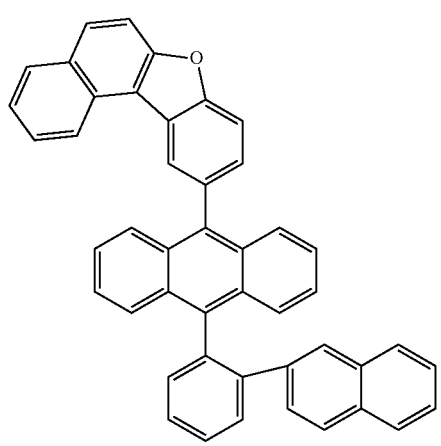
744
-continued
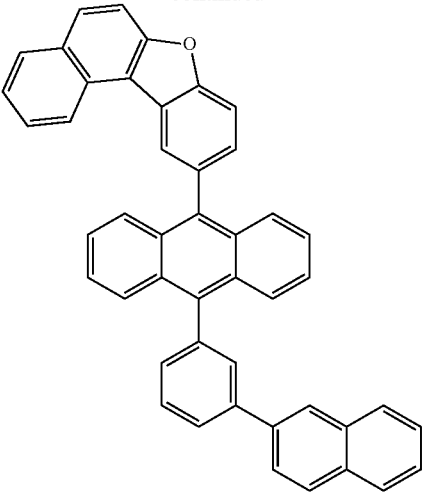
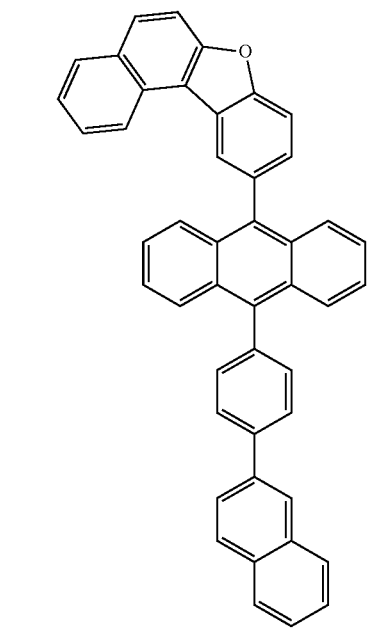
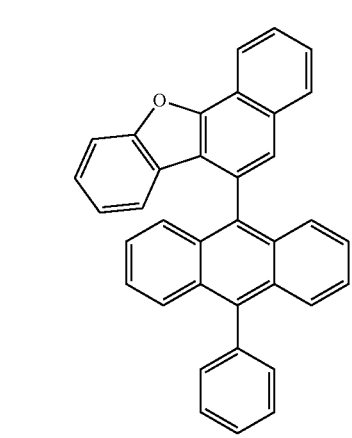

745
-continued
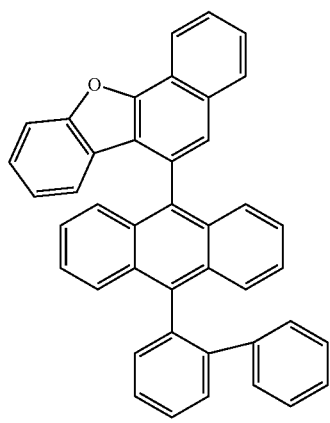
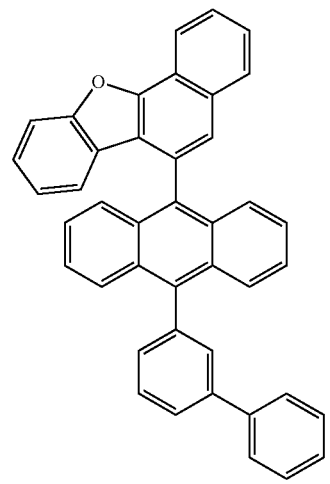
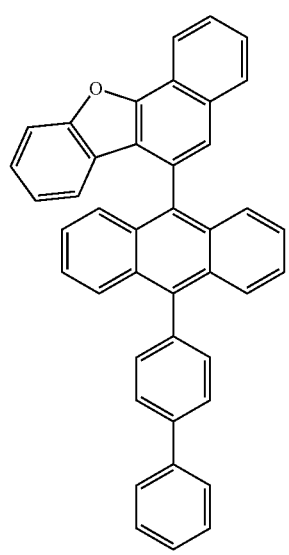
746
-continued
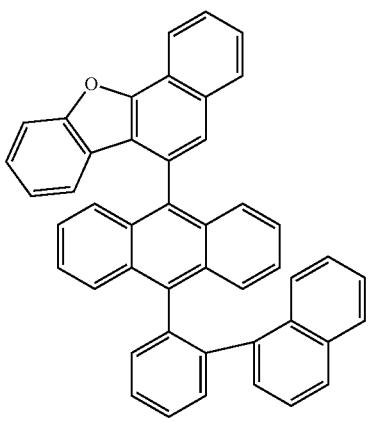
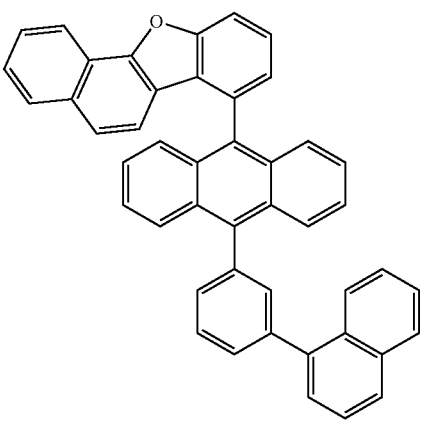
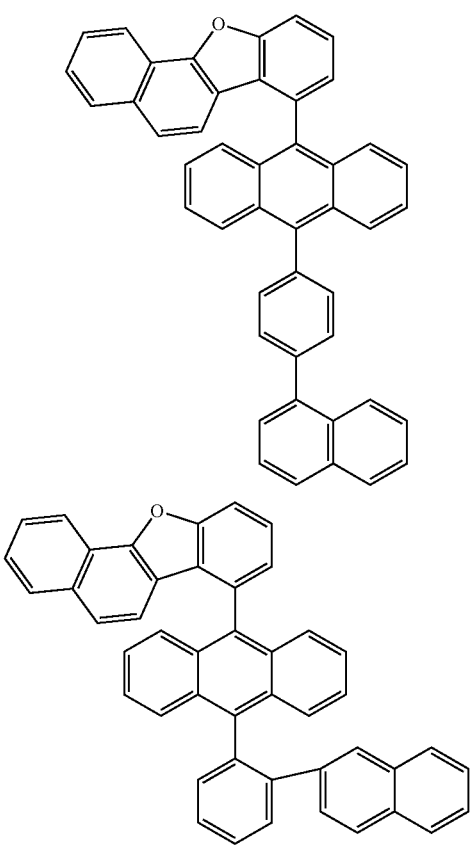

747
-continued
748
-continued
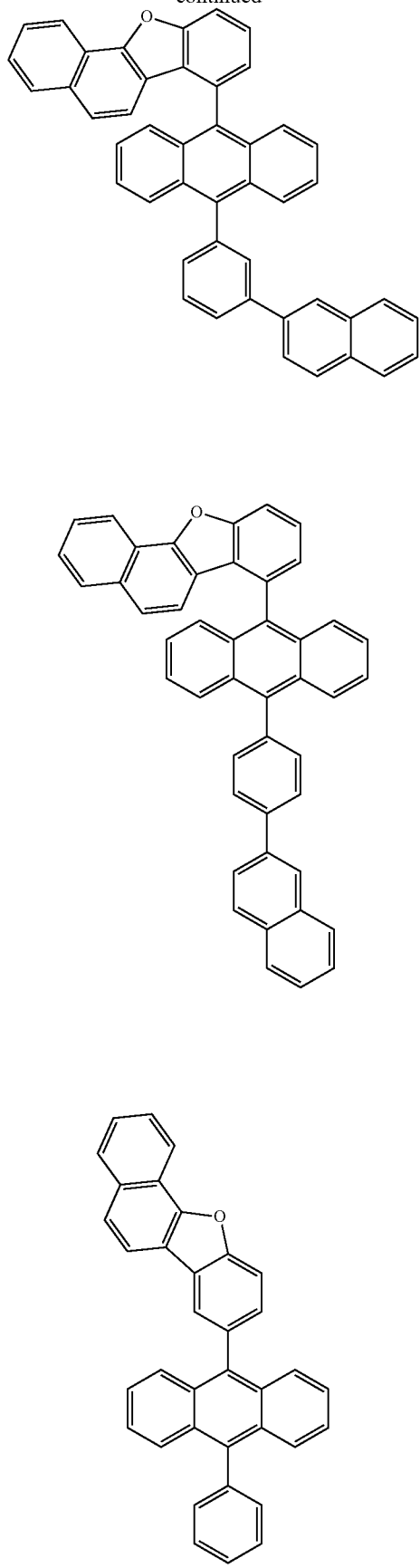
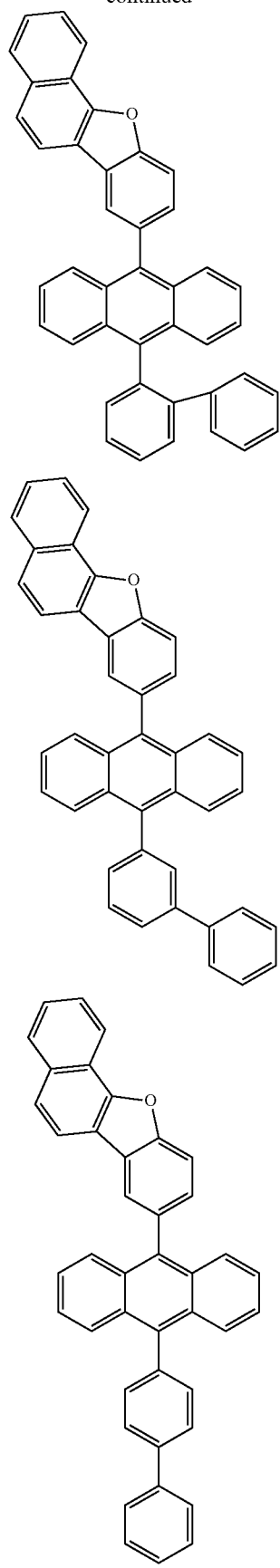

749
-continued
750
-continued
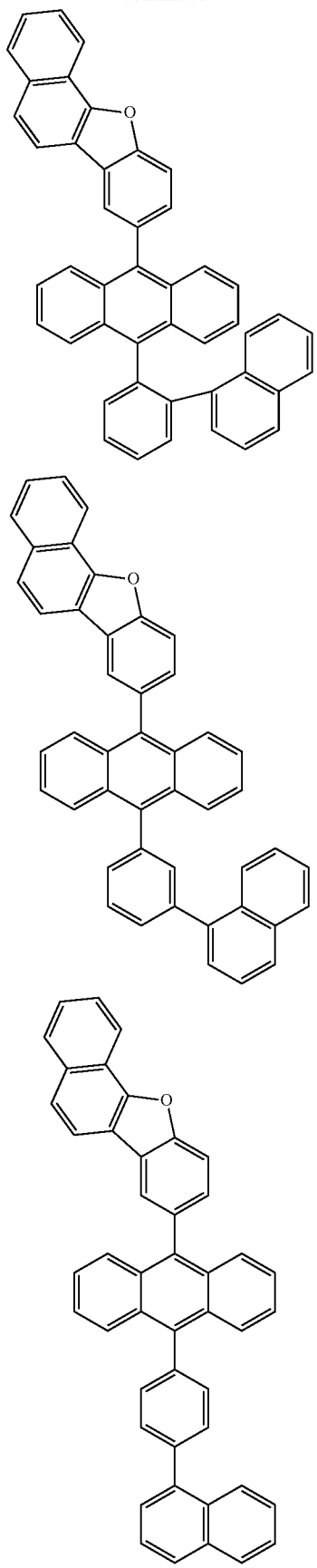
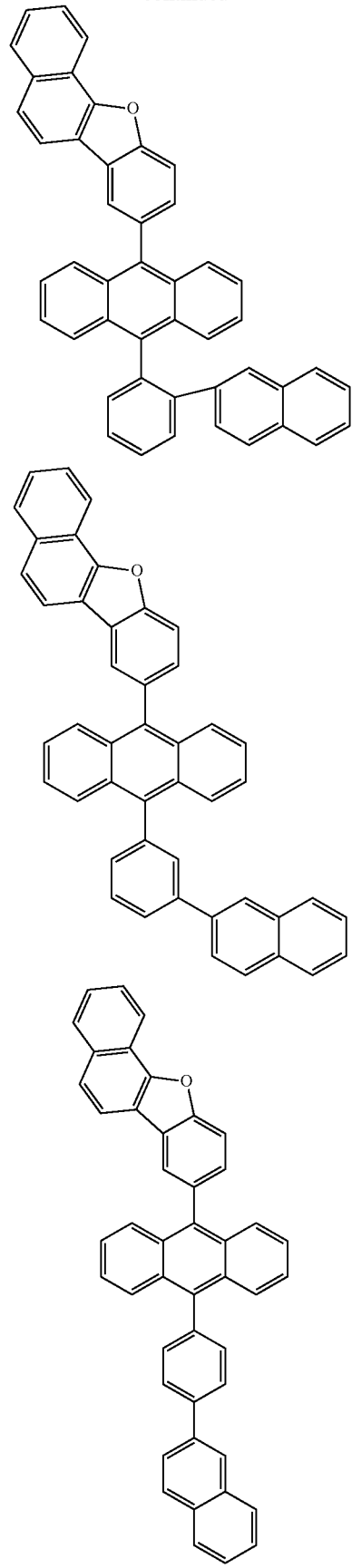

751
-continued
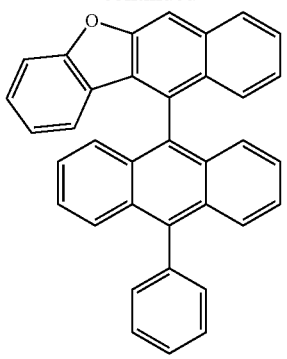
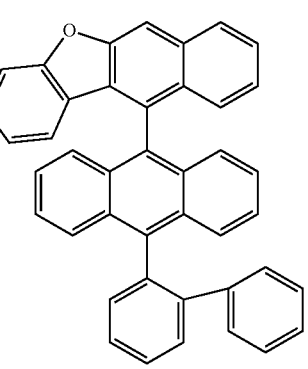
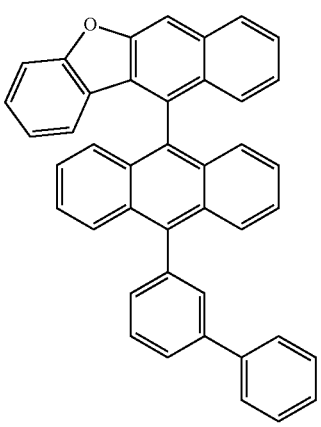
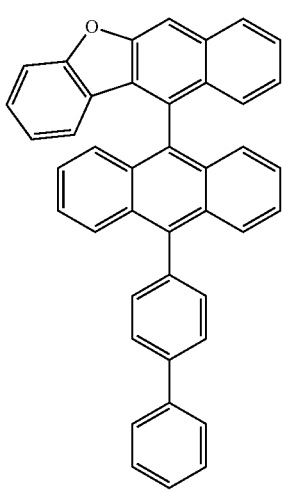
752
-continued
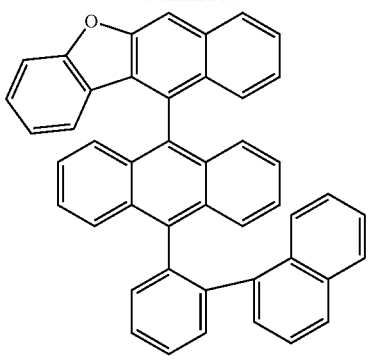
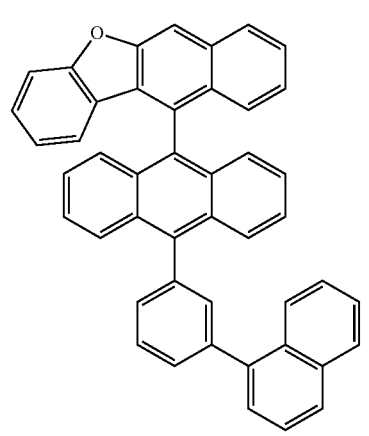
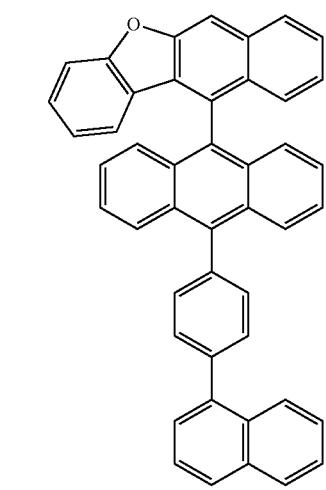
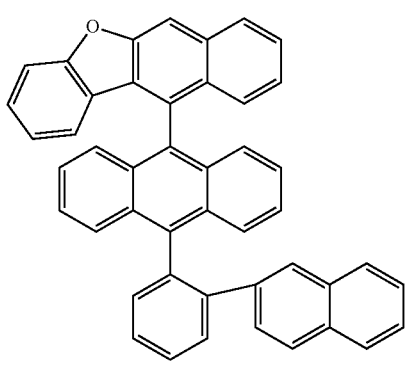

753
-continued
754
-continued
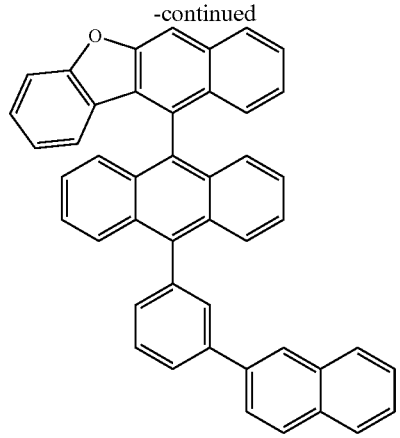
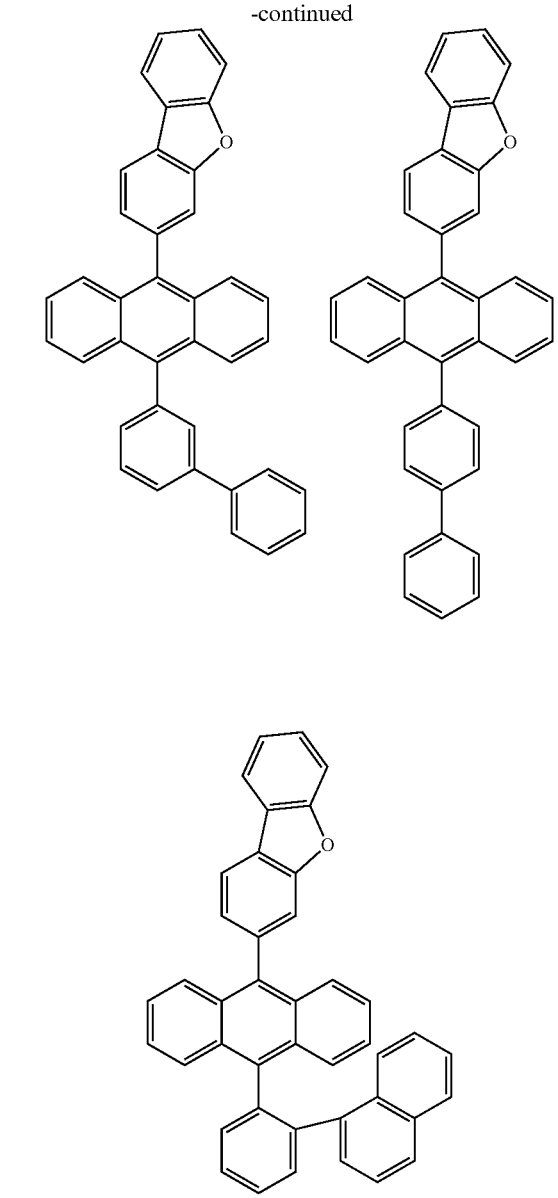
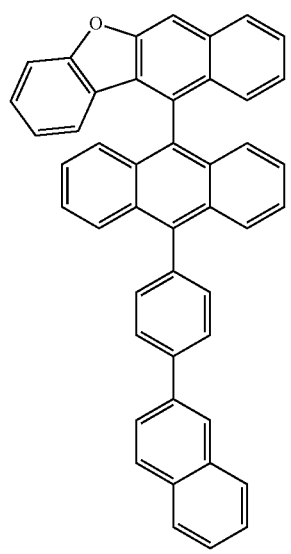
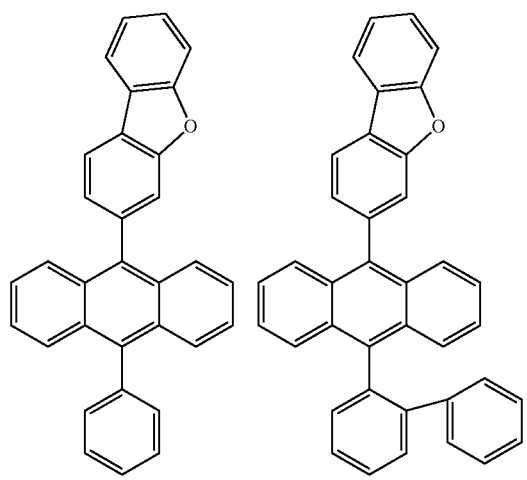

755
-continued
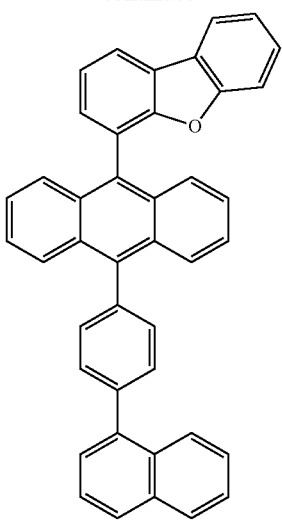
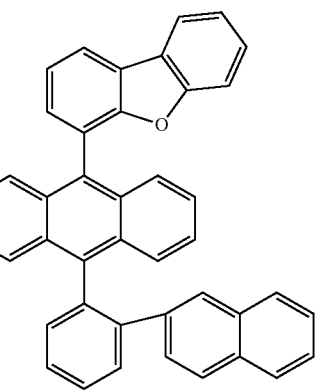
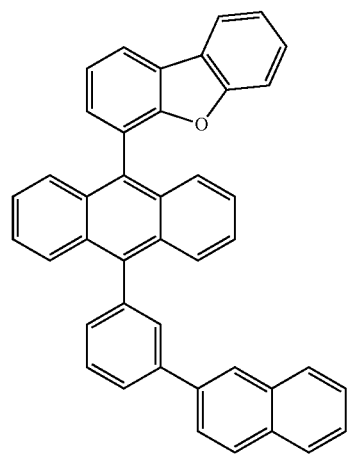
756
-continued
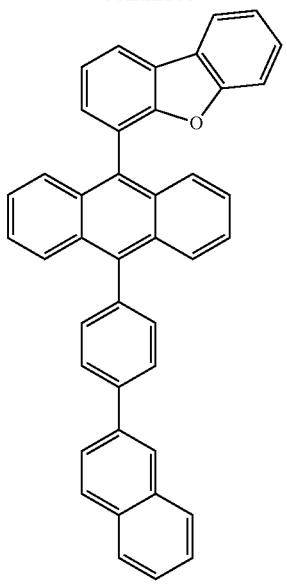
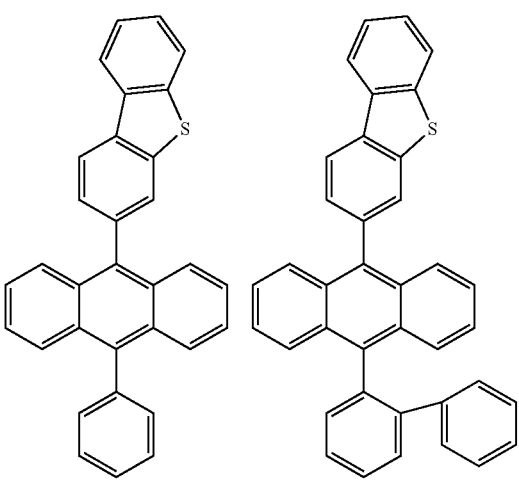
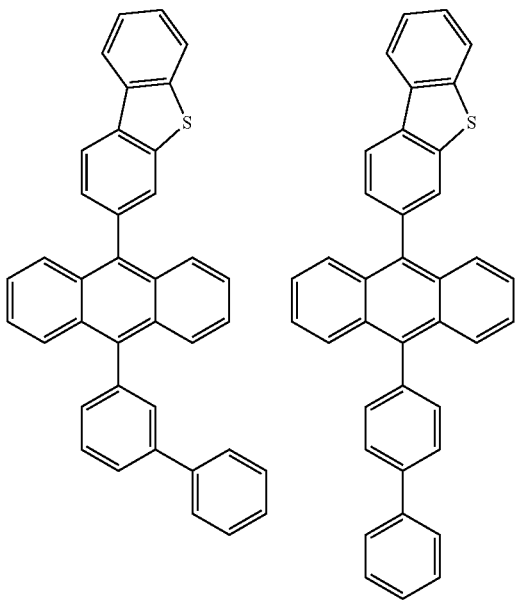

757
-continued
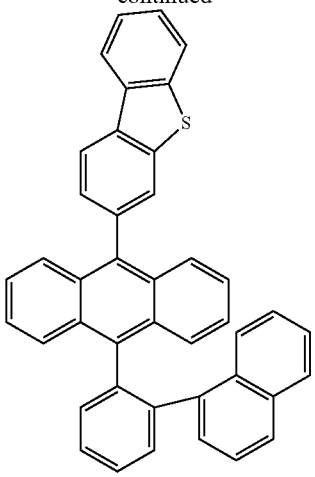
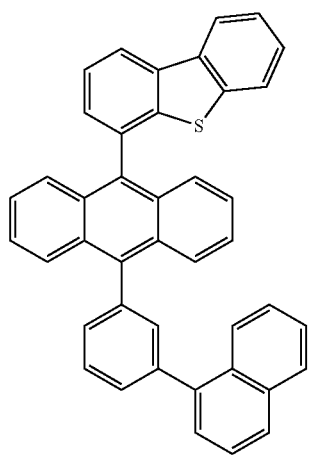
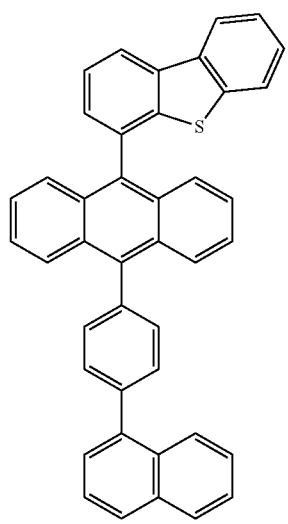
758
-continued
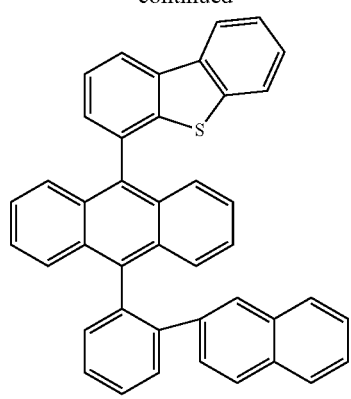
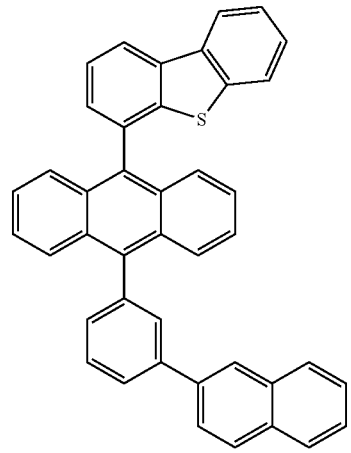
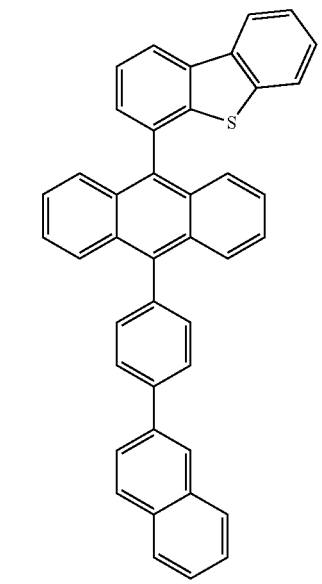

759
-continued
760
-continued
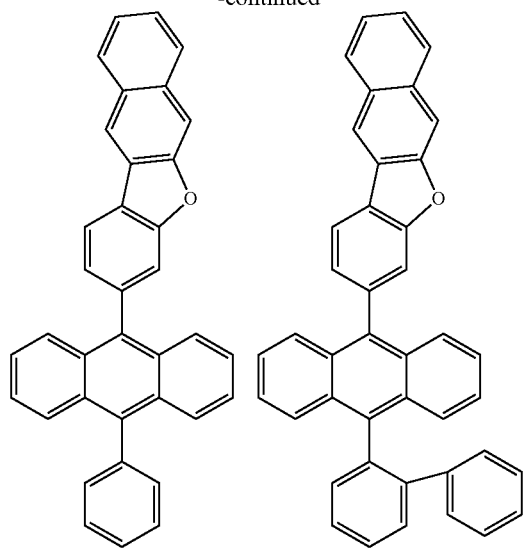
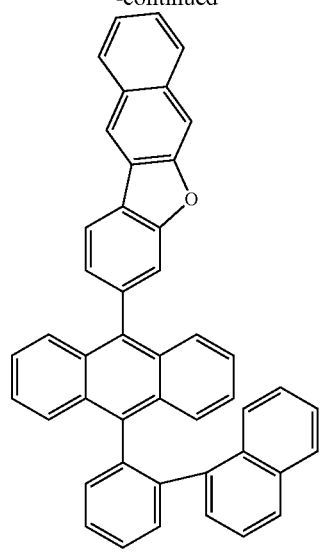

761
-continued
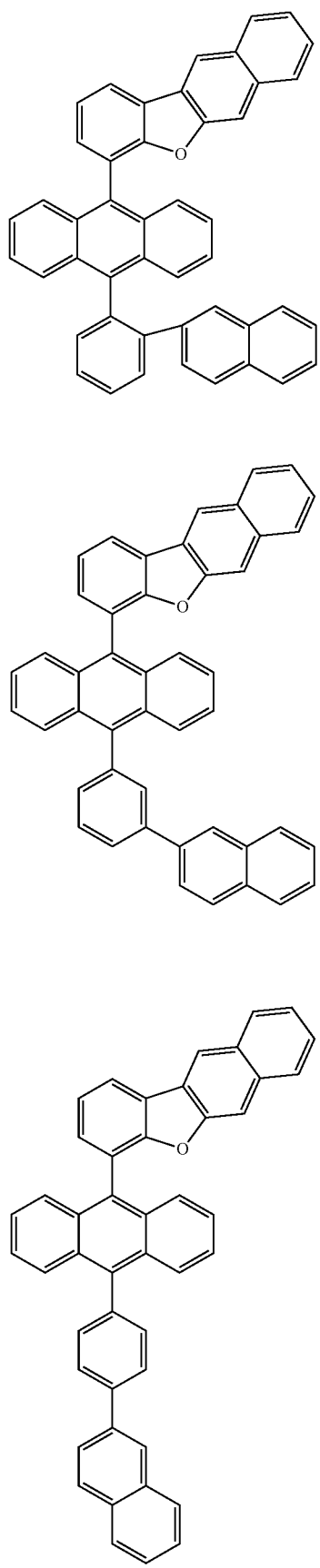
762
-continued
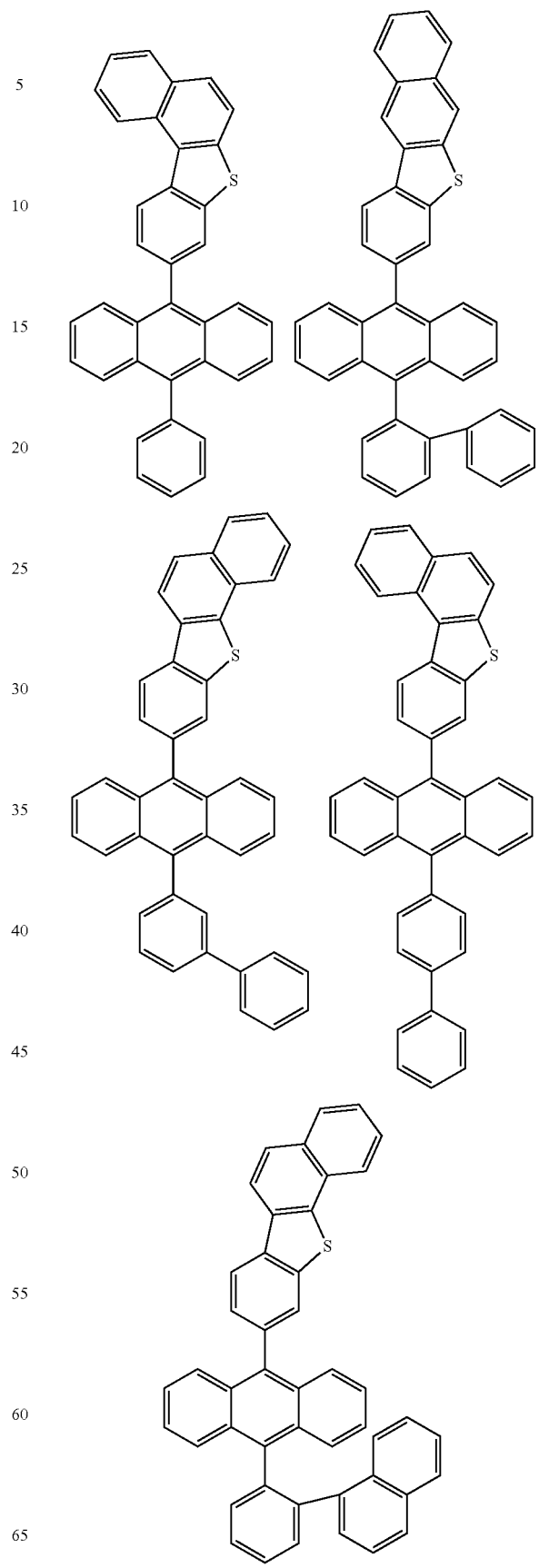

763
-continued
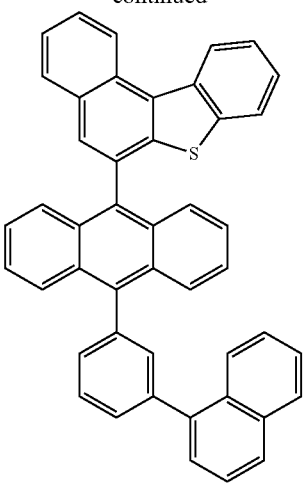
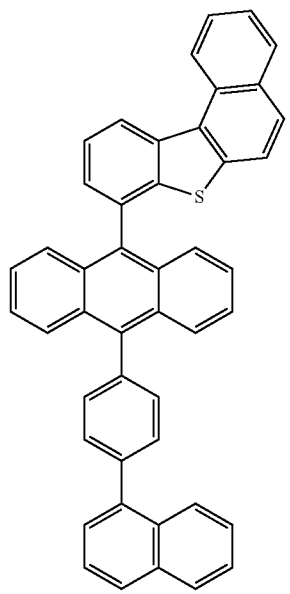
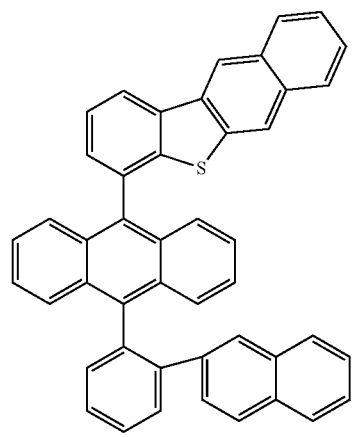
764
-continued
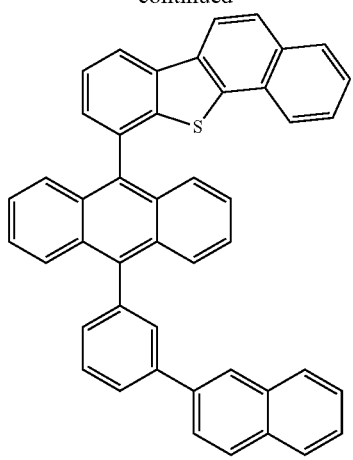
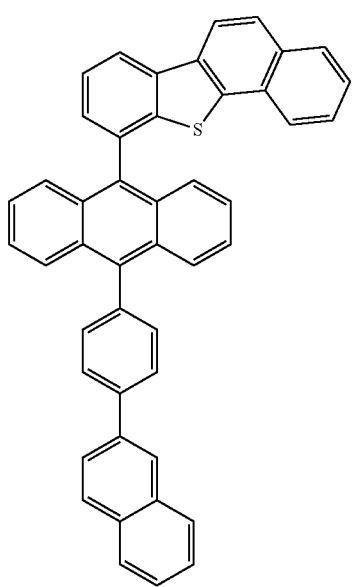
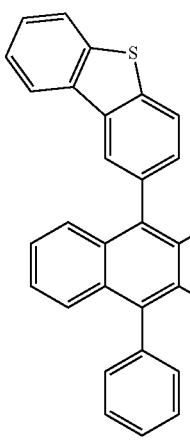 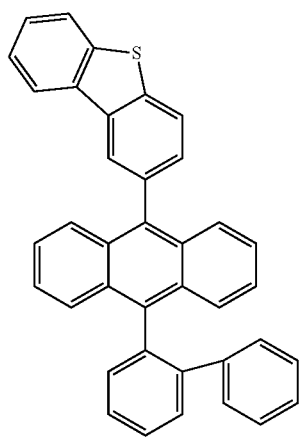

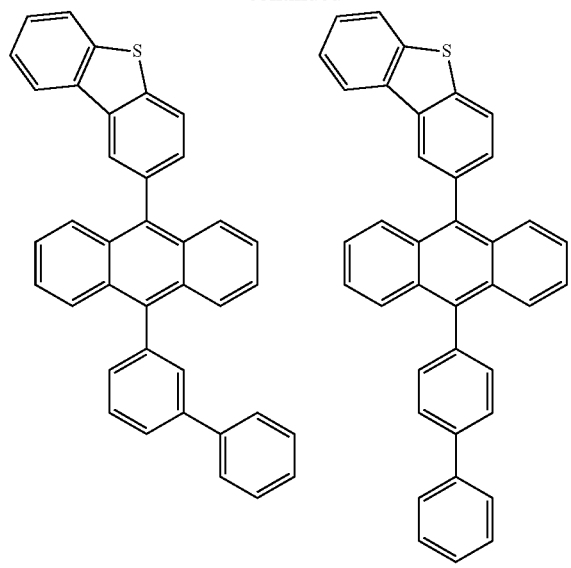
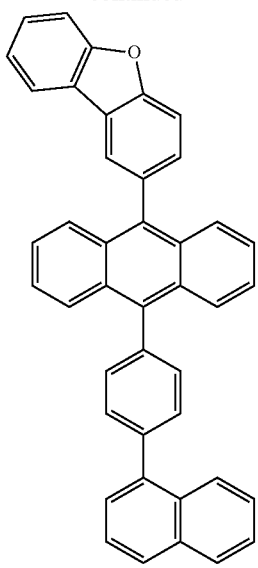
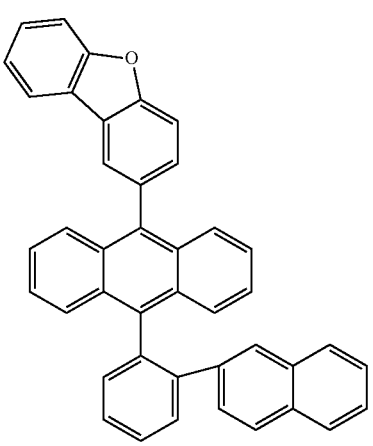
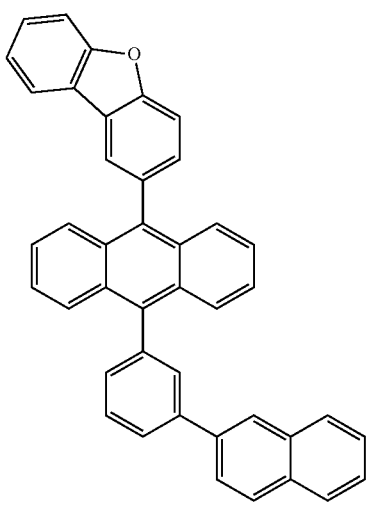

767
-continued
768
-continued
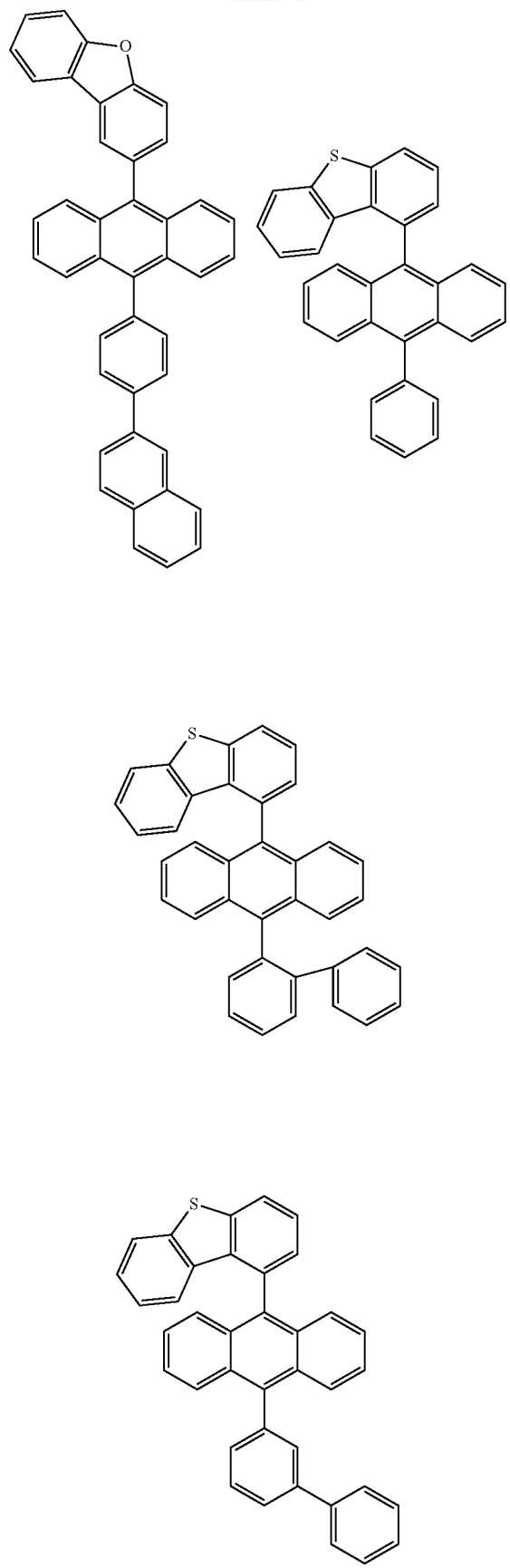
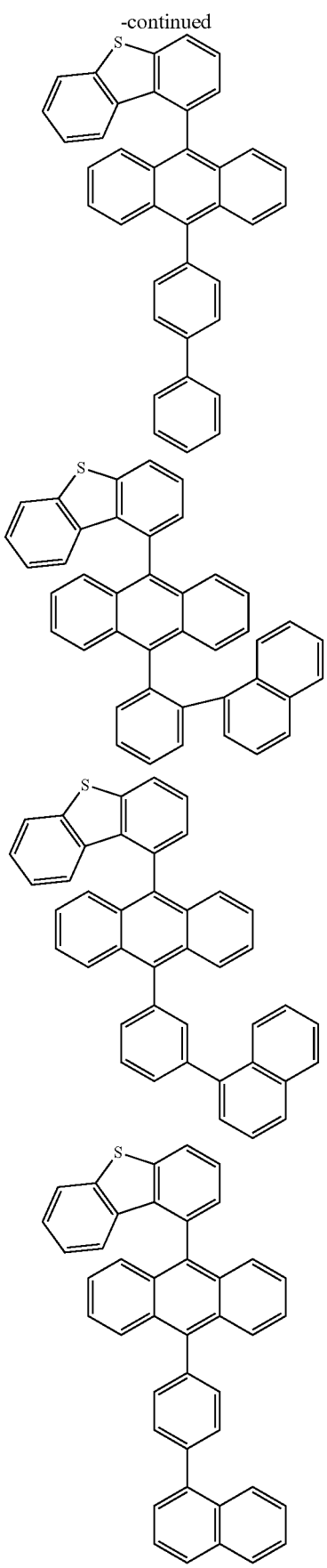

769
-continued
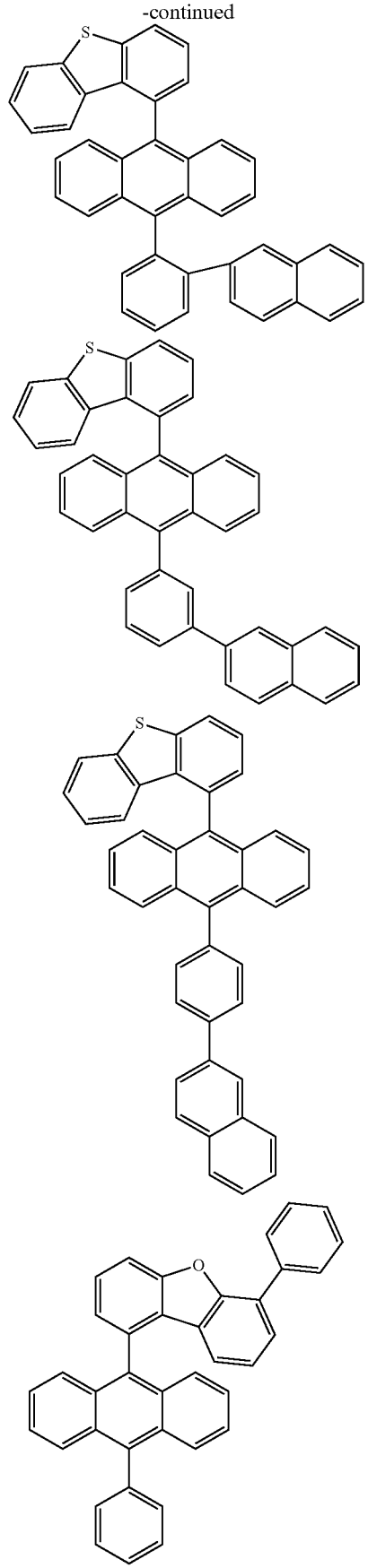
770
-continued
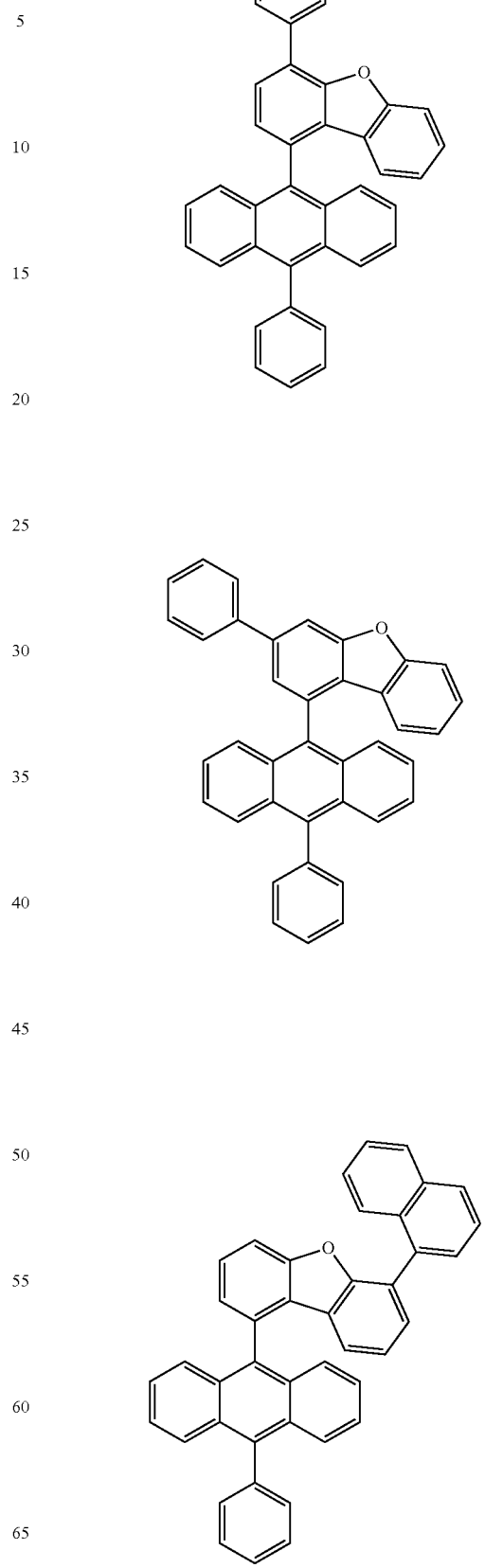

771
-continued
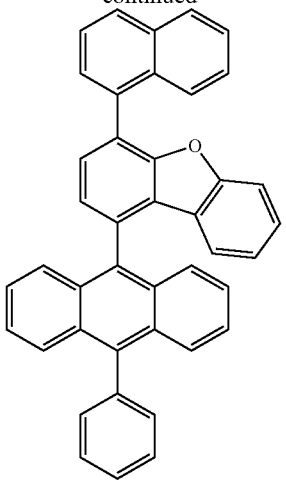
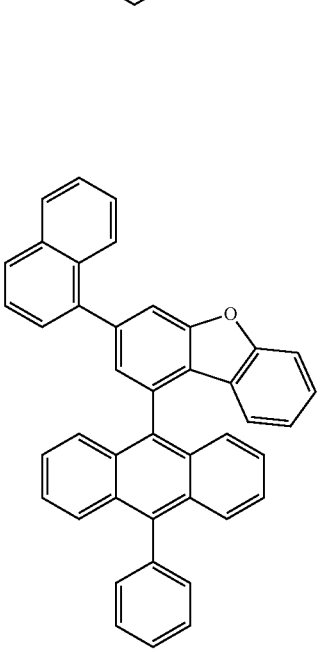
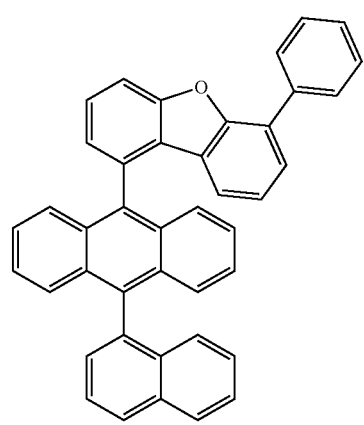
772
-continued
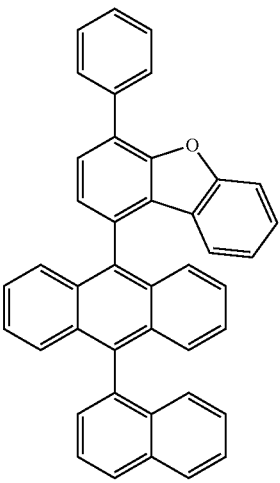
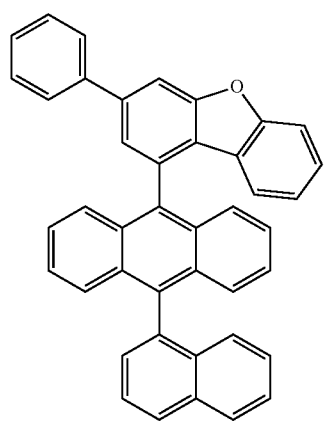
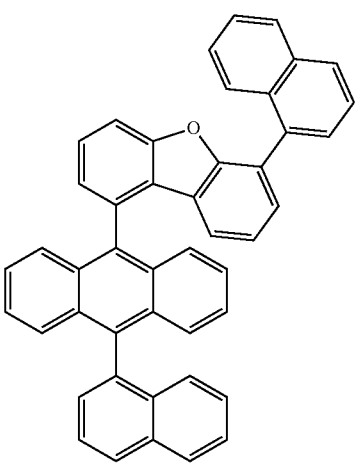

773
-continued
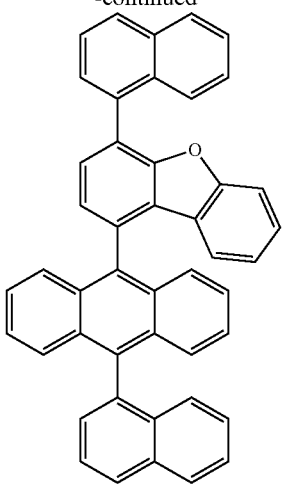
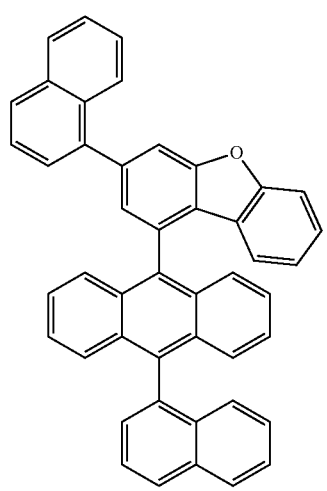
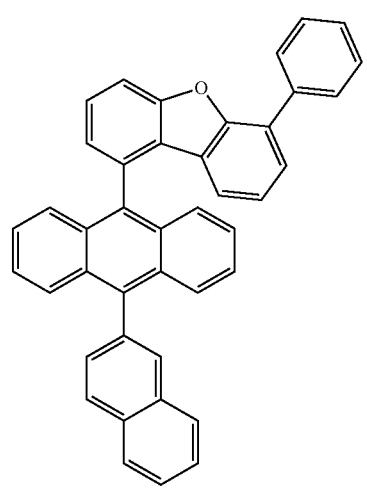
774
-continued
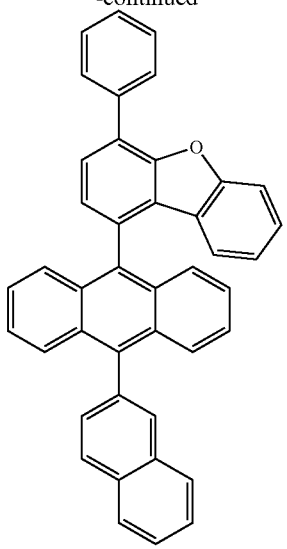
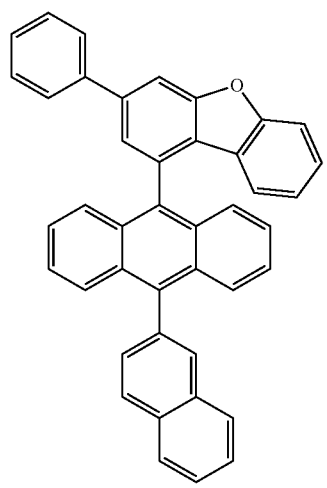
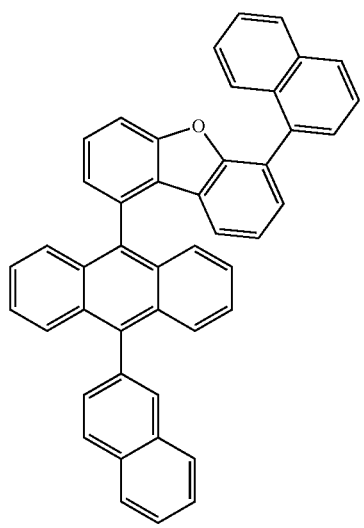

775
-continued
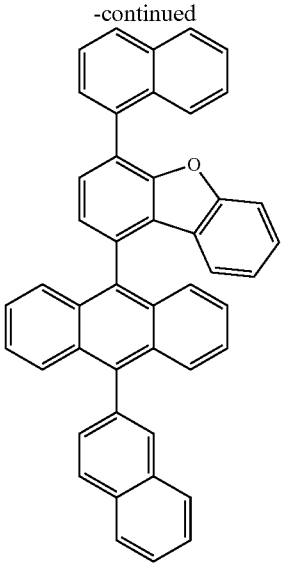
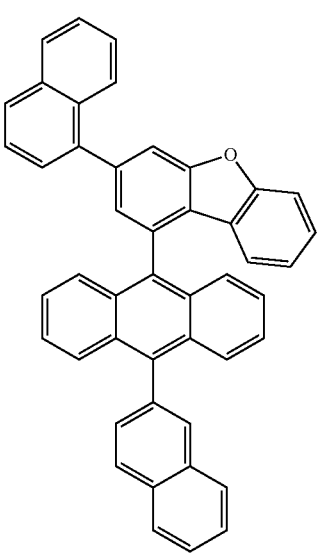
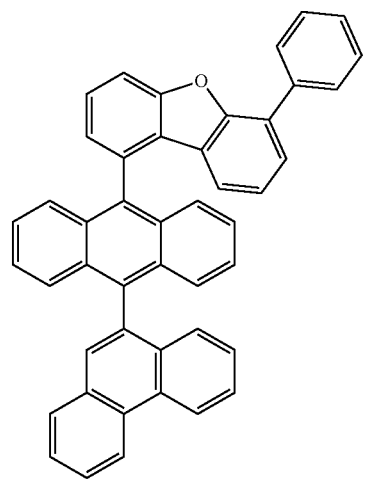
776
-continued
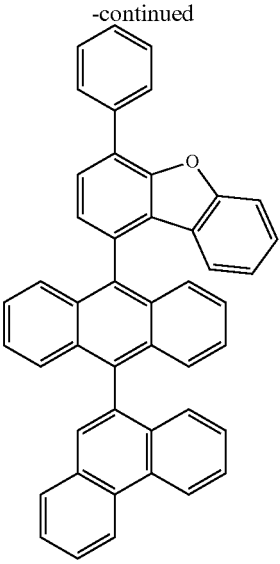
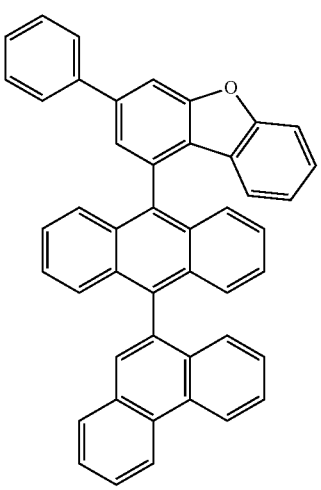
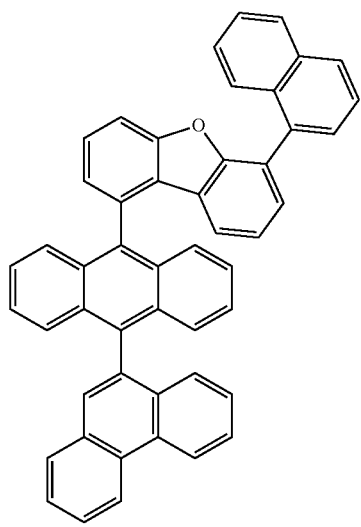

777
-continued
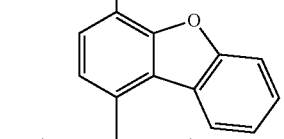
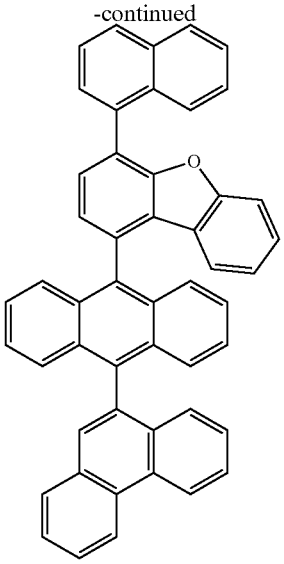
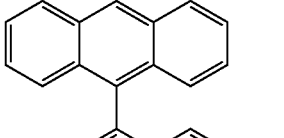
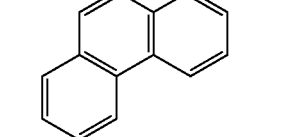
778
-continued
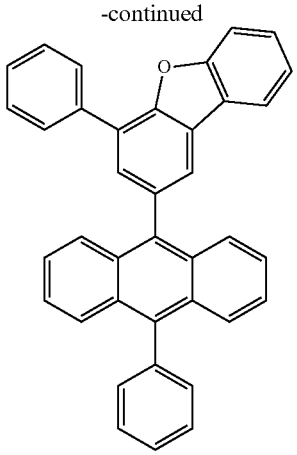
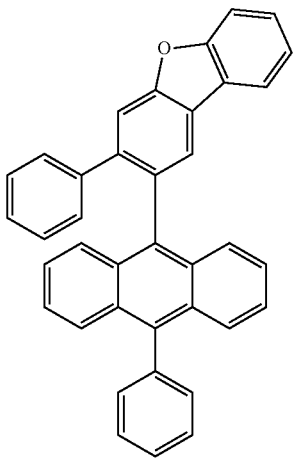
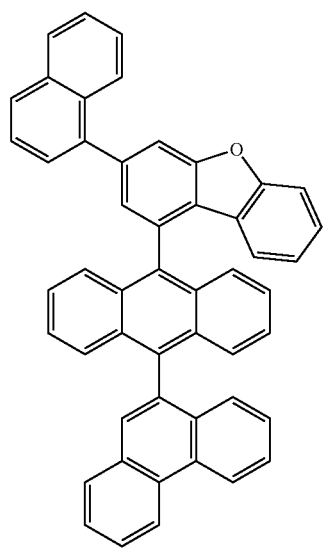
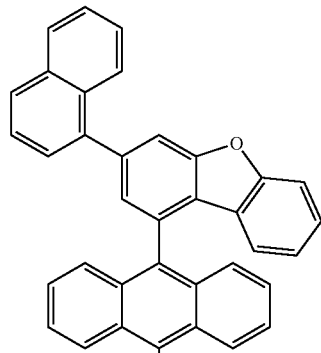
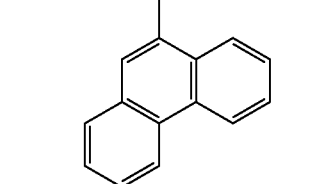
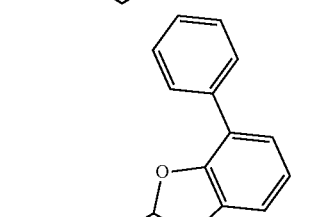
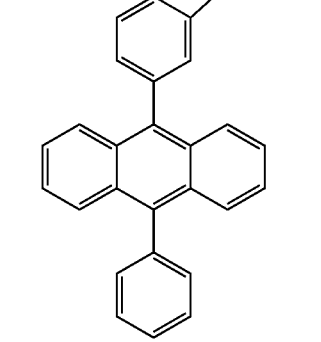
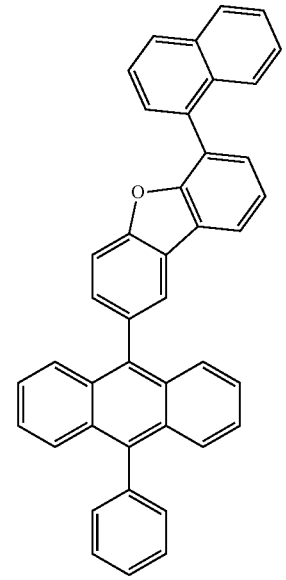

779
-continued
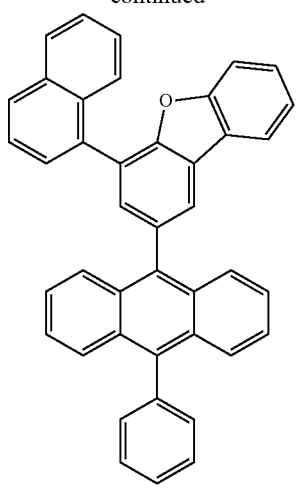
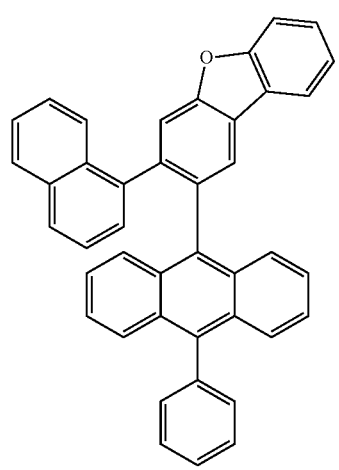
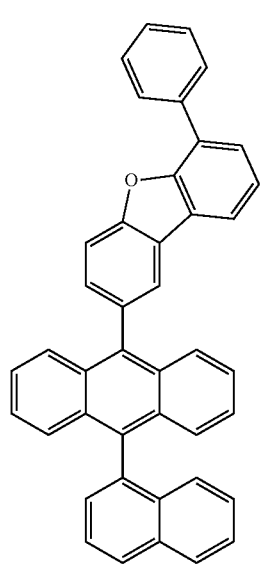
780
-continued
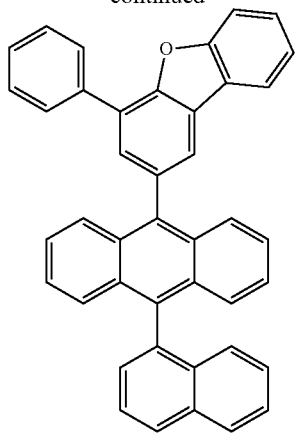
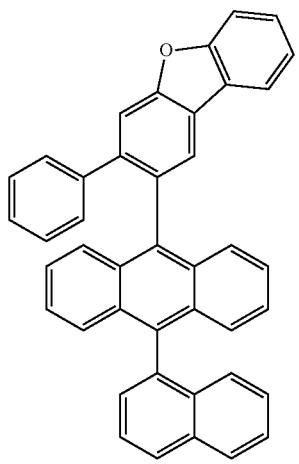
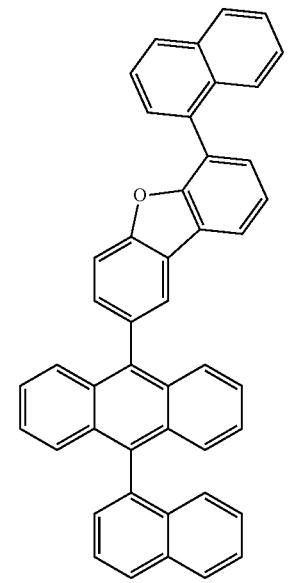

781
-continued
782
-continued
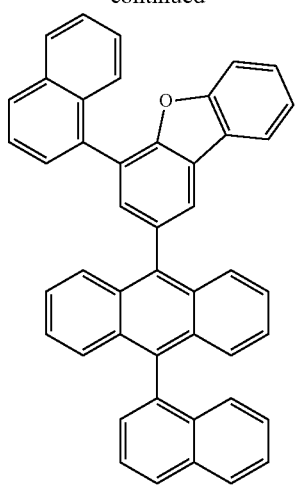
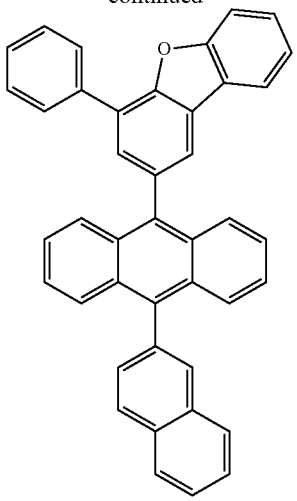

783
-continued
784
-continued
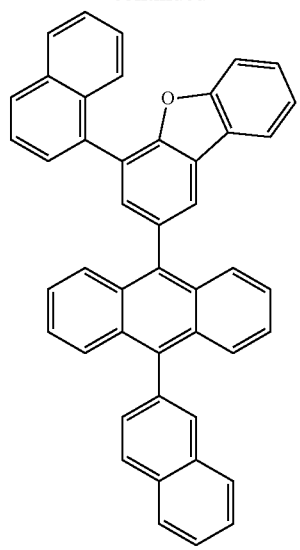
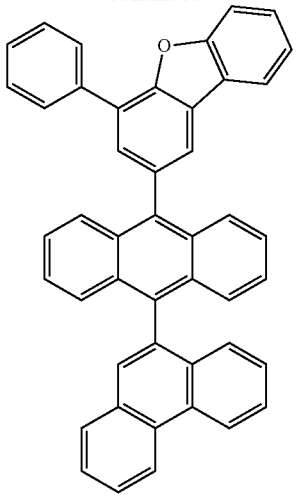

785
-continued
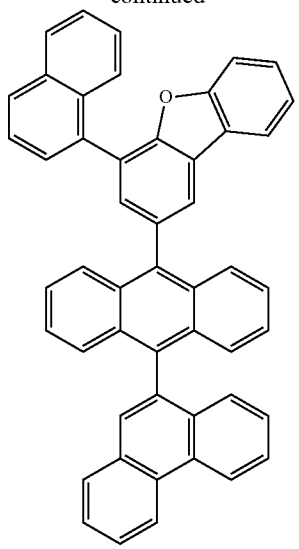
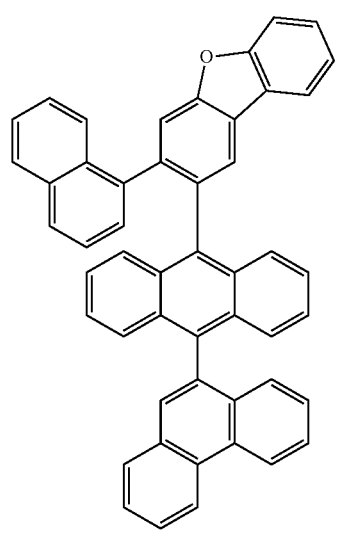
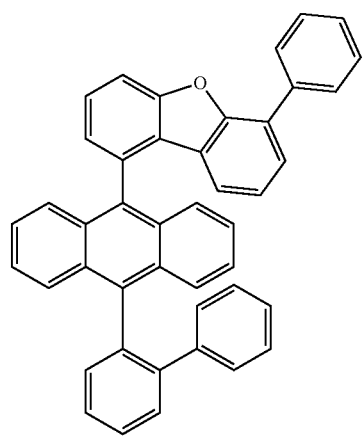
786
-continued
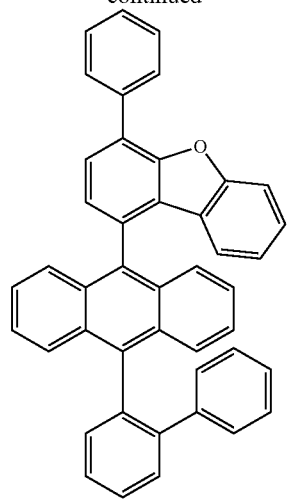
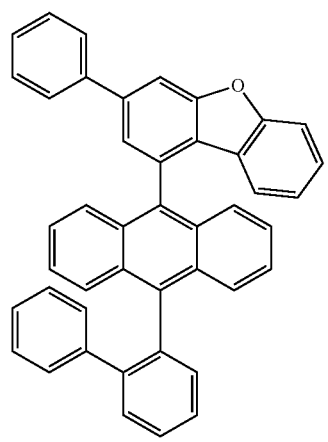
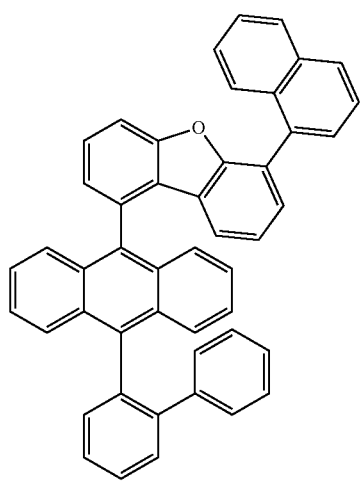

787
-continued
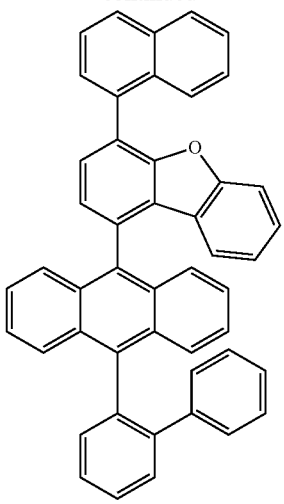
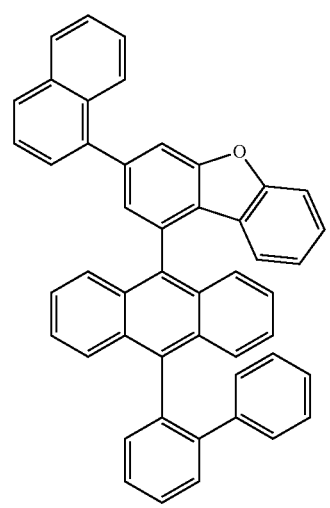
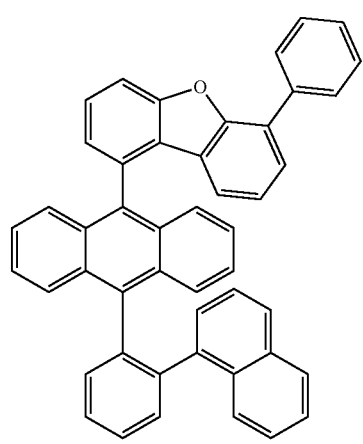
788
-continued
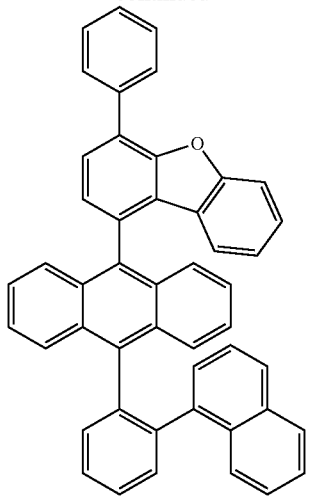
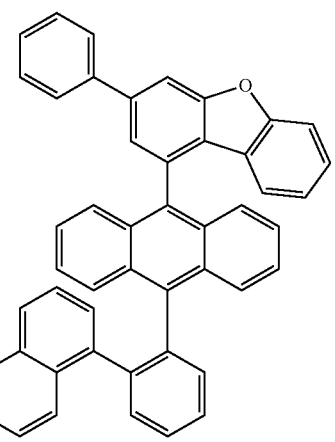
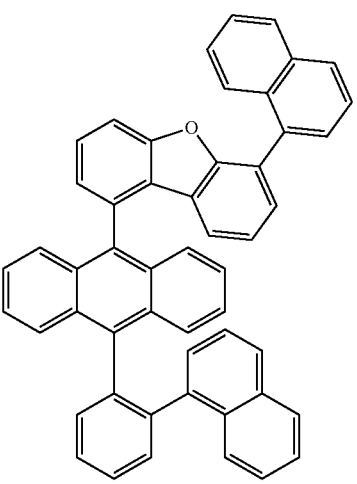

789
-continued
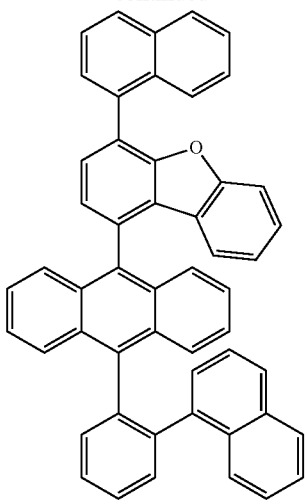
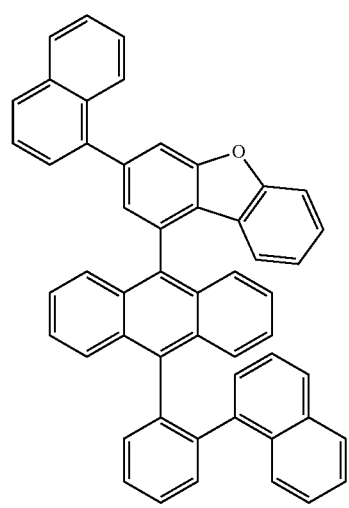
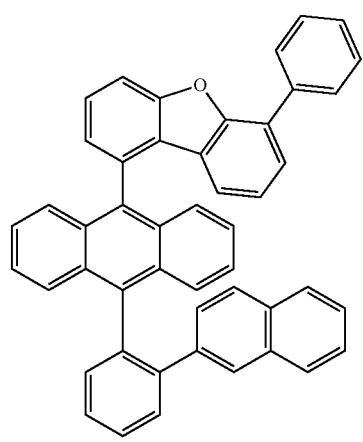
790
-continued
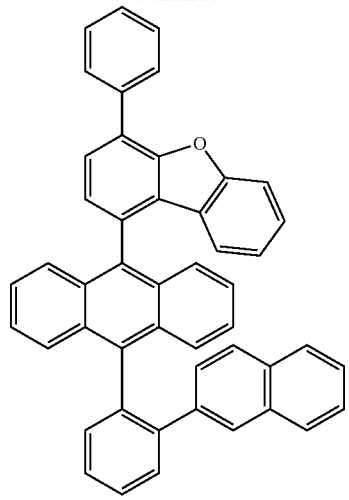
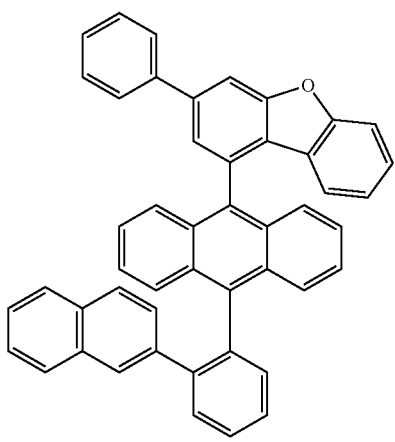
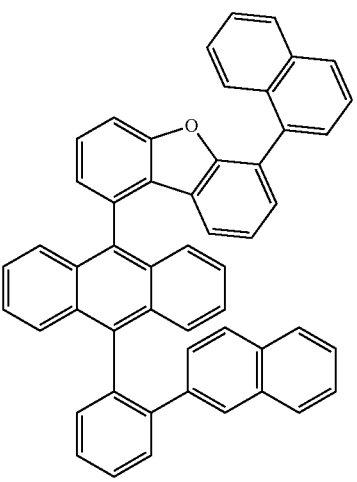

791
-continued
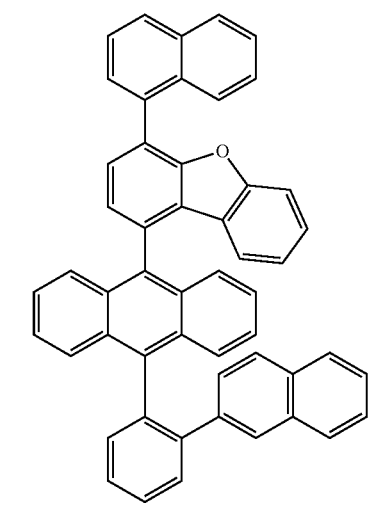
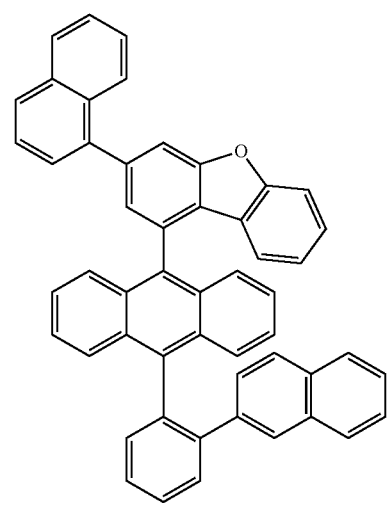
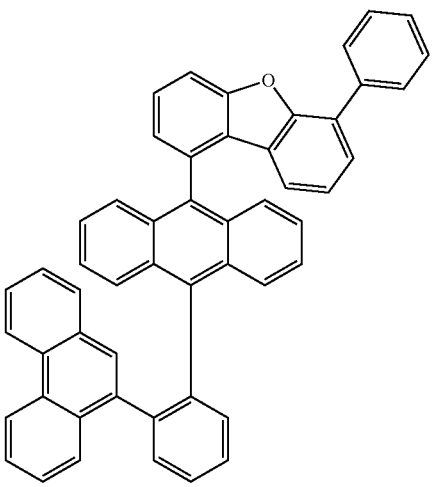
792
-continued
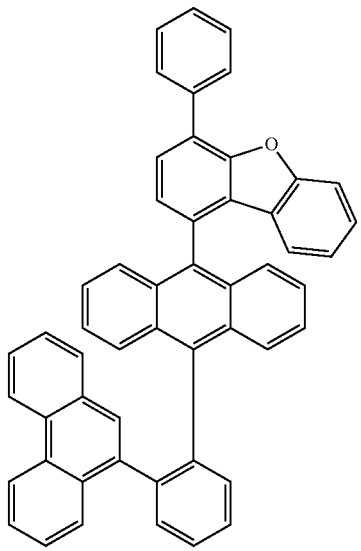
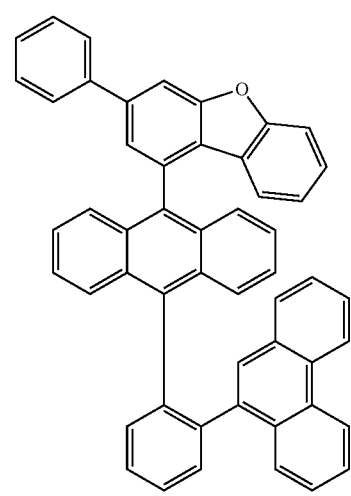
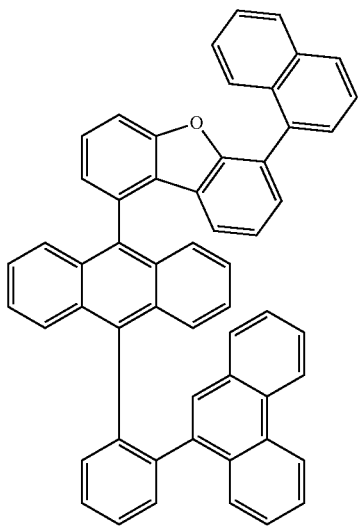

793
-continued
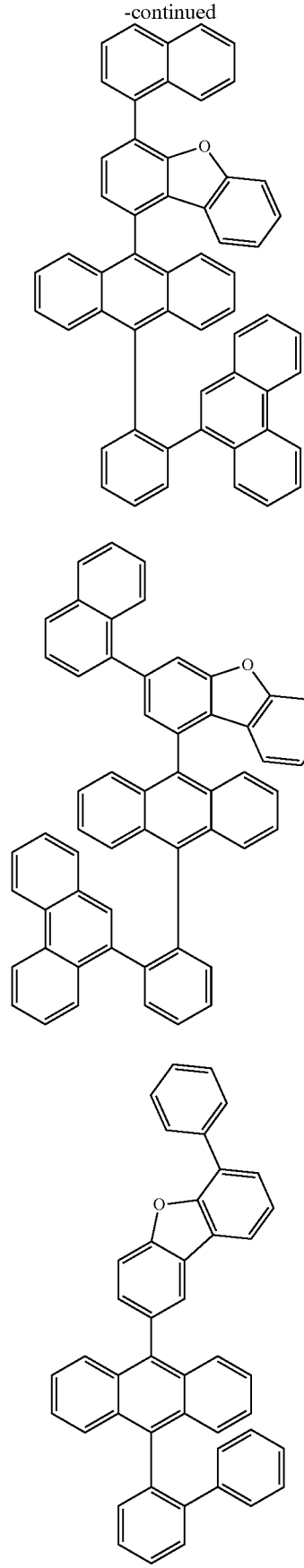
794
-continued
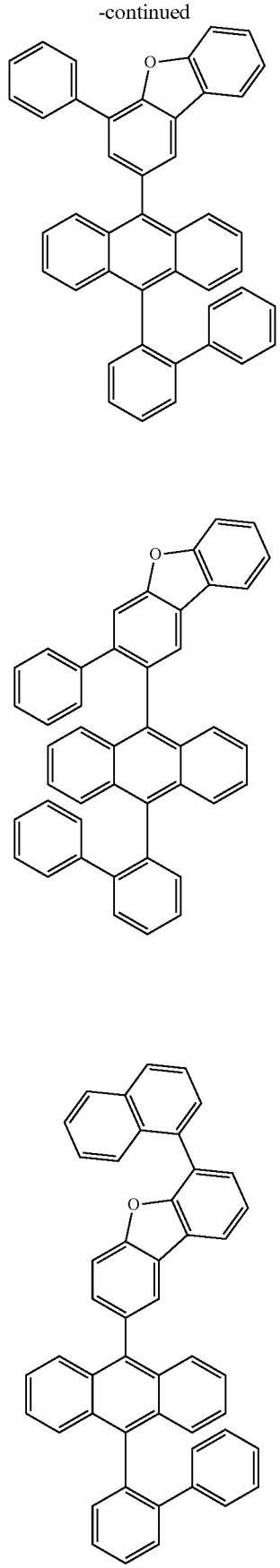

795
-continued
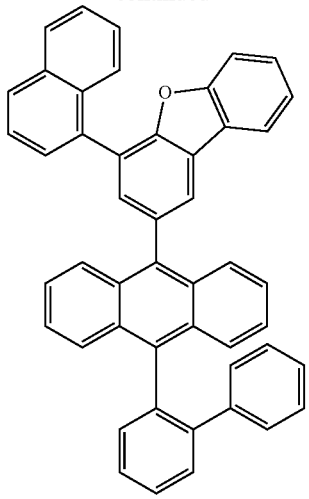
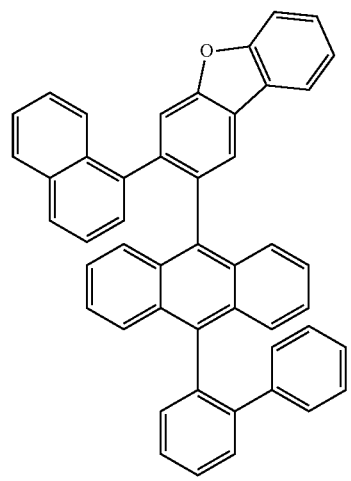
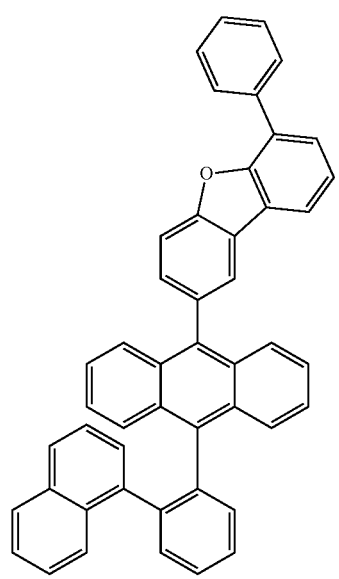
796
-continued
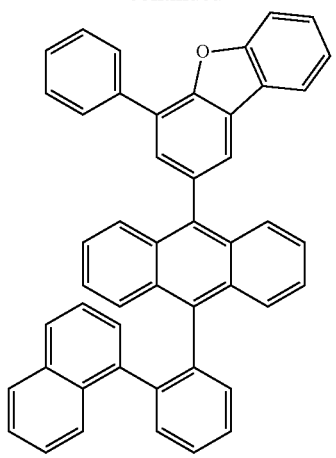
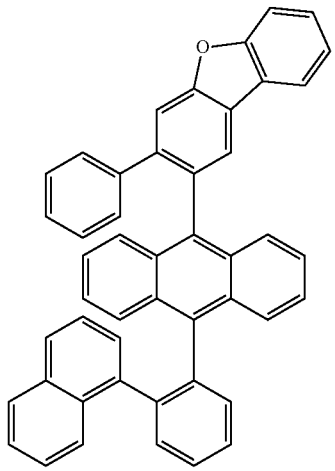
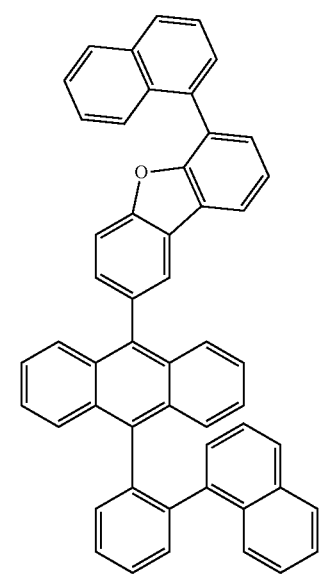

797
-continued
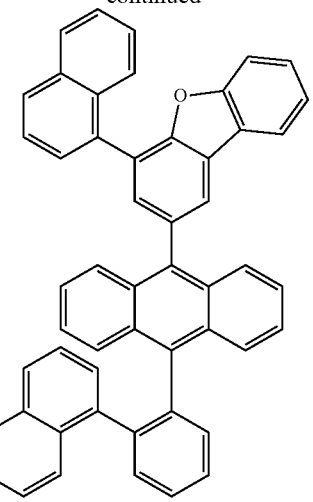
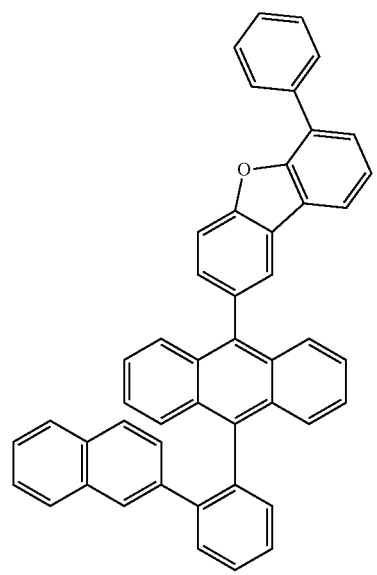
798
-continued
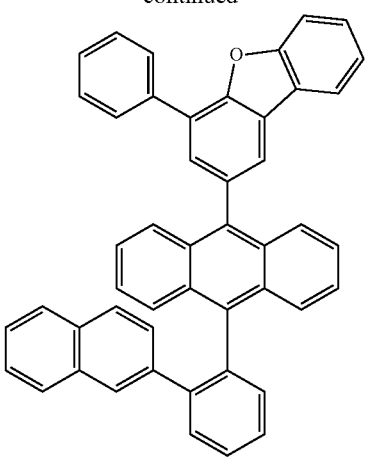
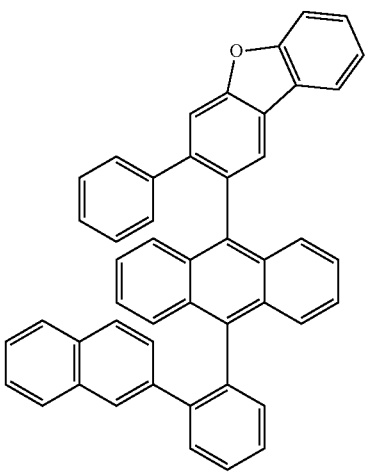
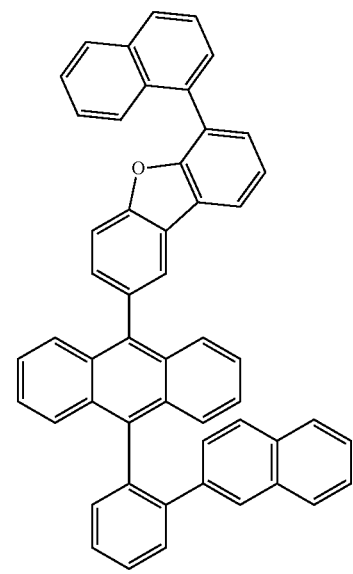

799
-continued
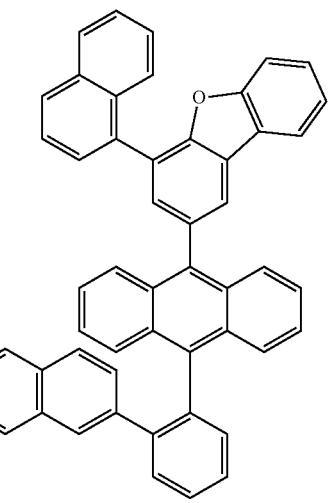
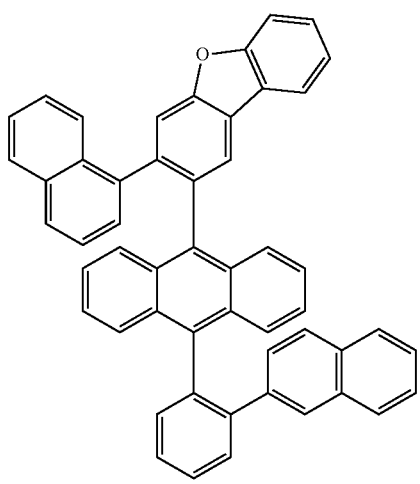
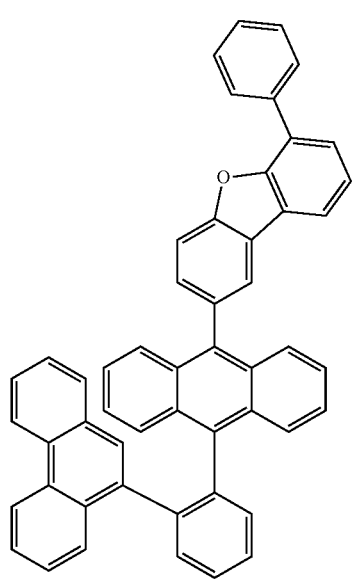
800
-continued
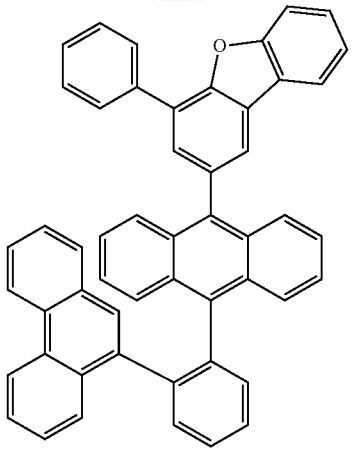
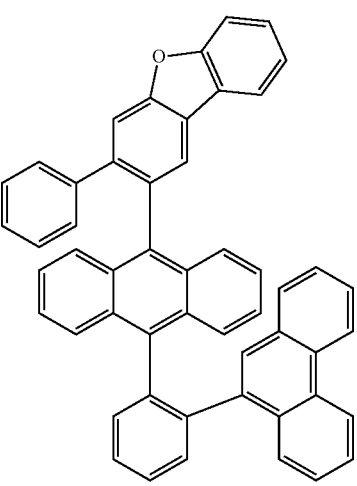

801
-continued
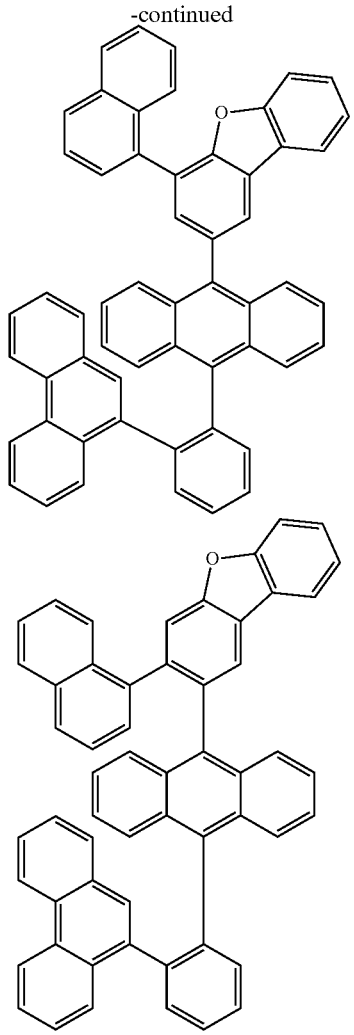
802
-continued
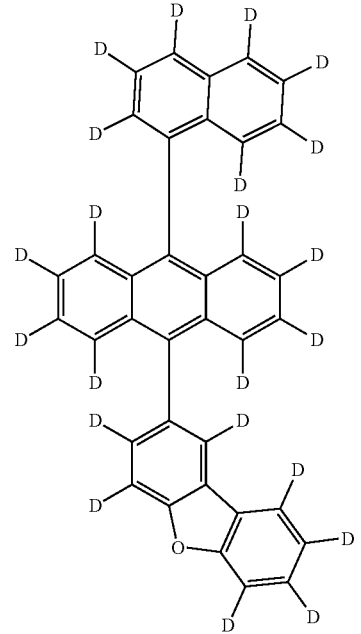
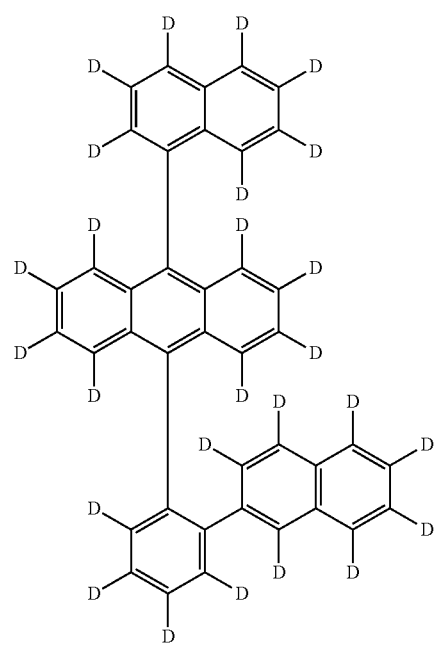

803
-continued
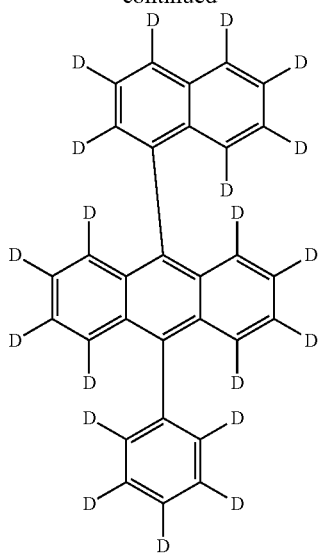
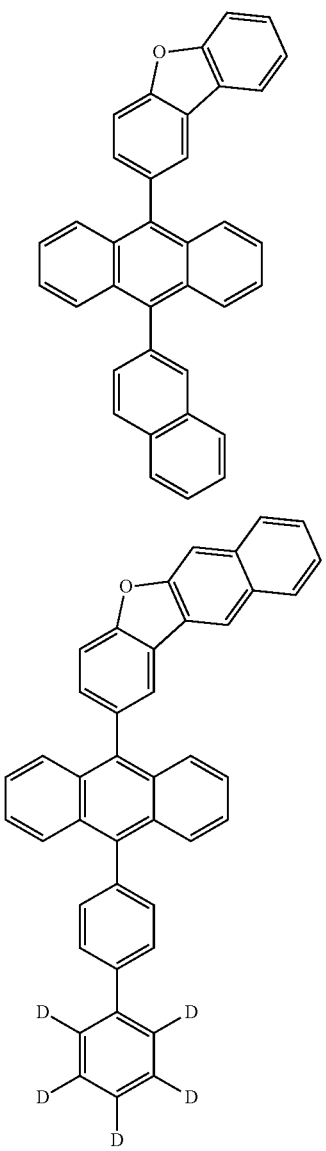
804
-continued
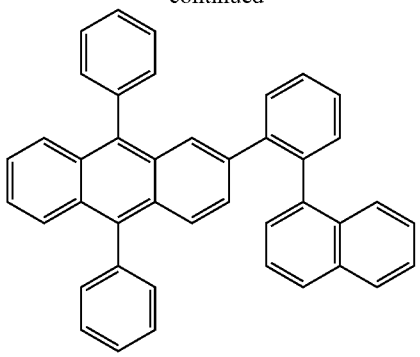
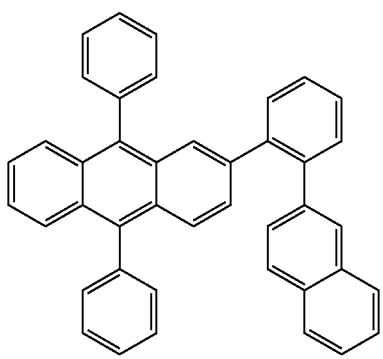
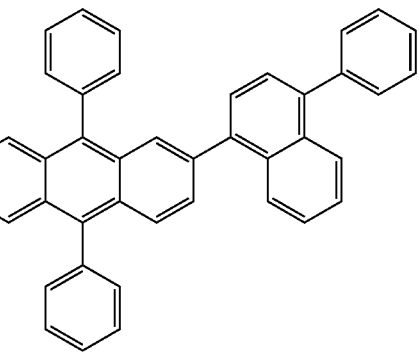

805
-continued
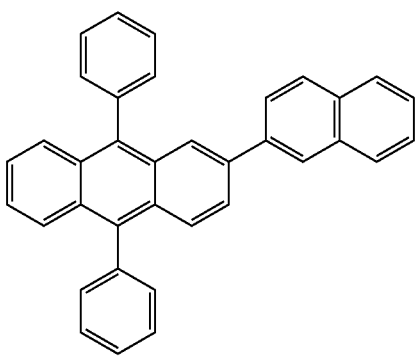
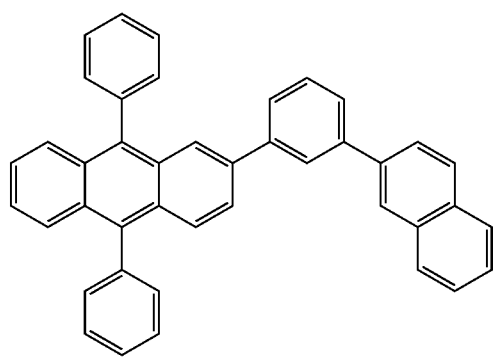
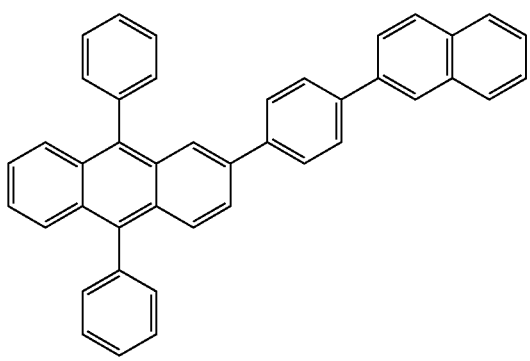
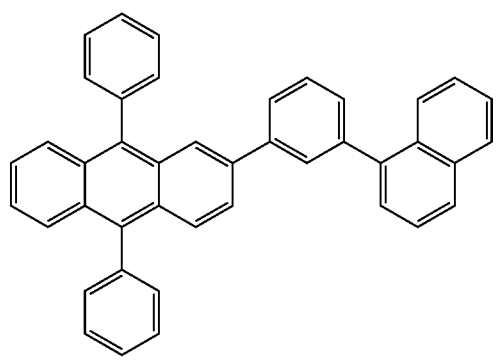
806
-continued
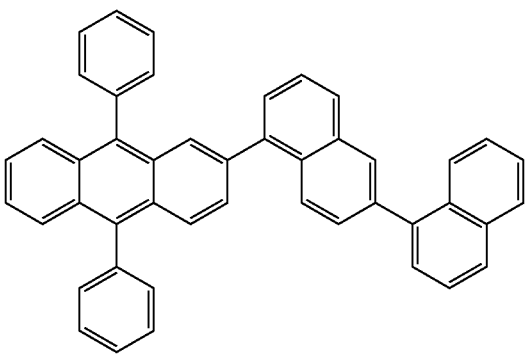
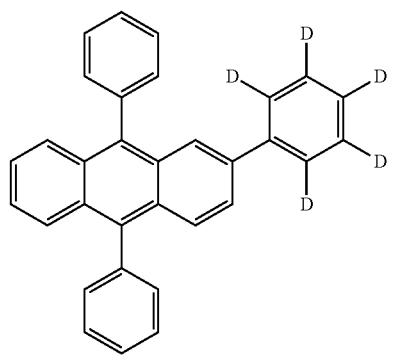
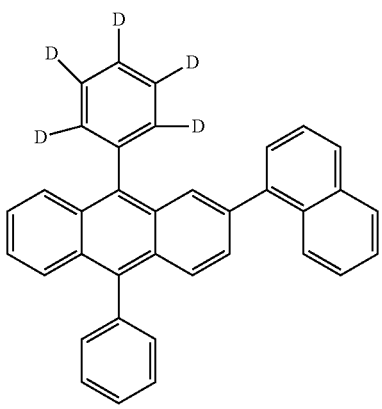
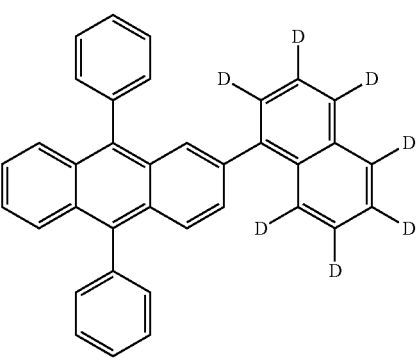

807
-continued
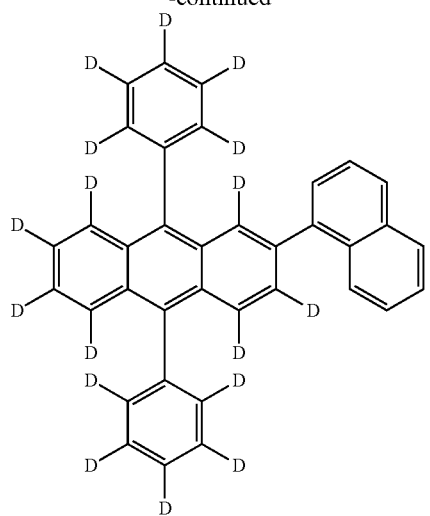
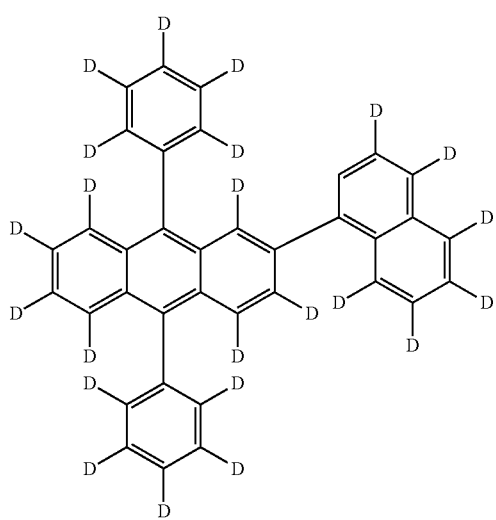
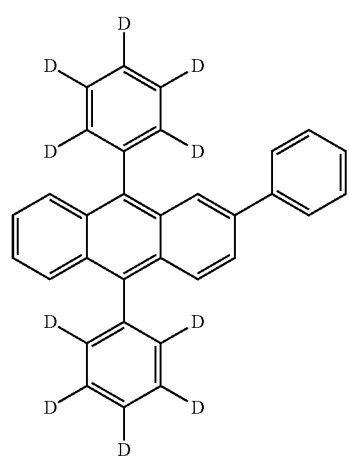
808
-continued
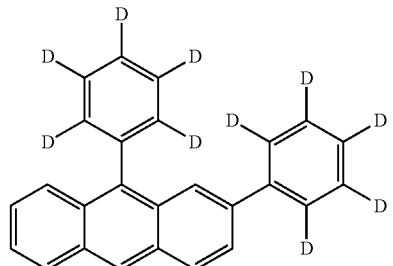
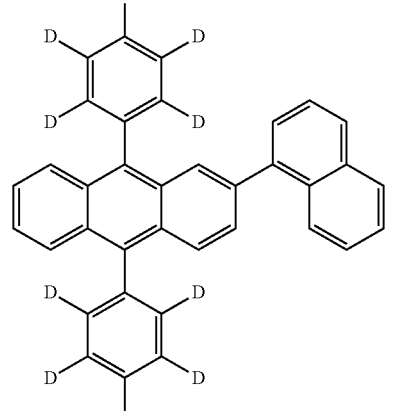
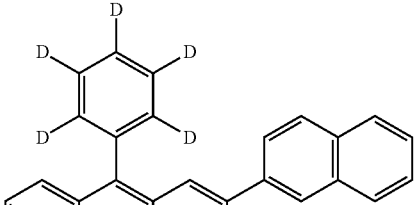
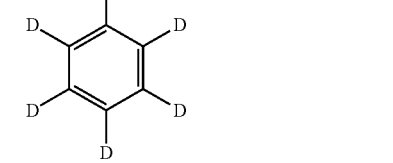
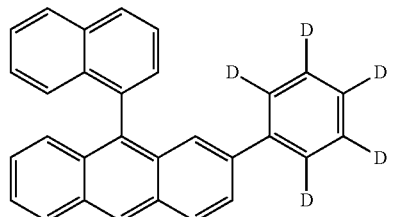
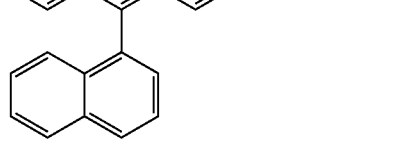

809
-continued
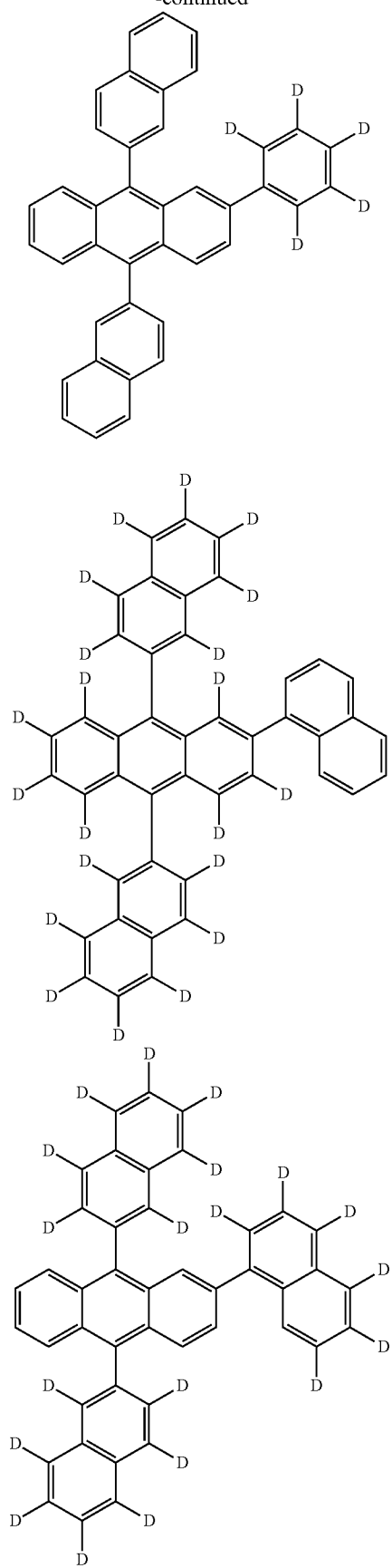
810
-continued
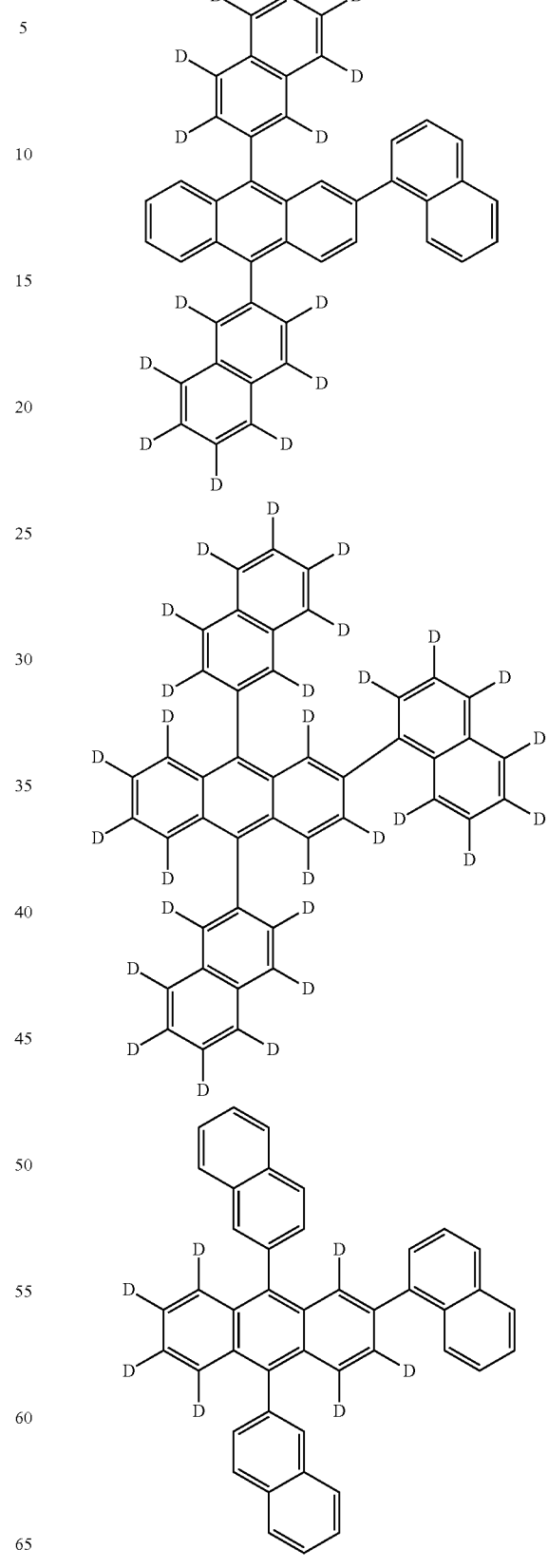

811
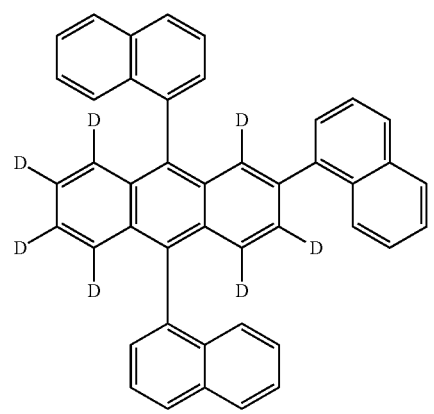
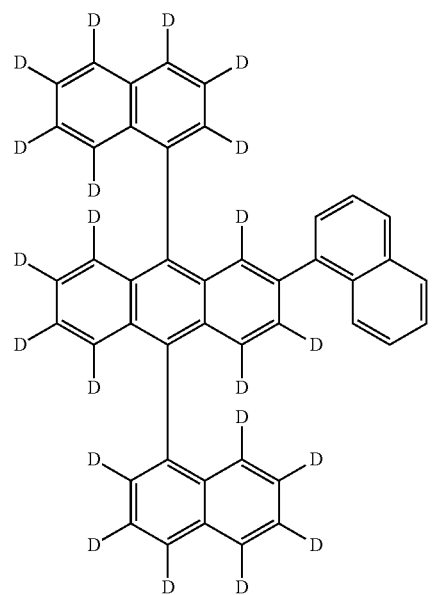
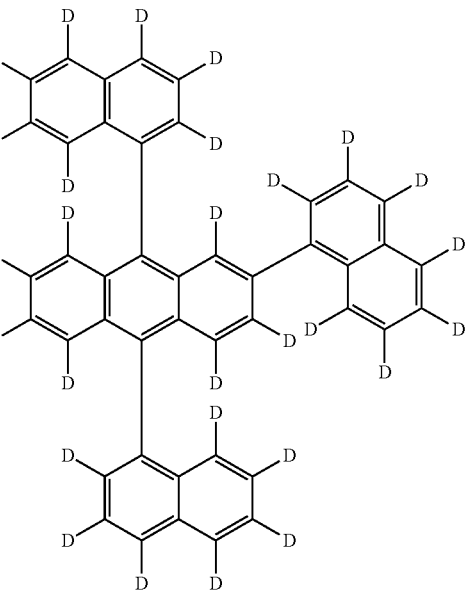
812
-continued
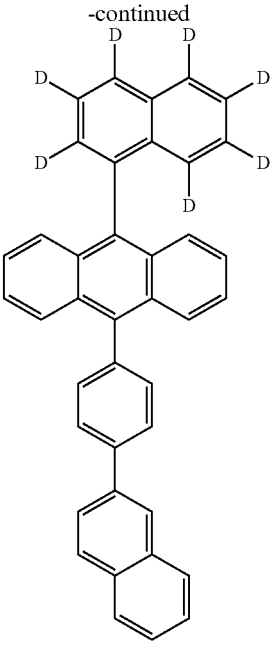
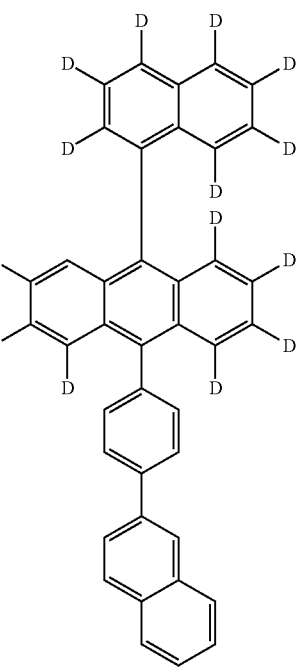

813
-continued
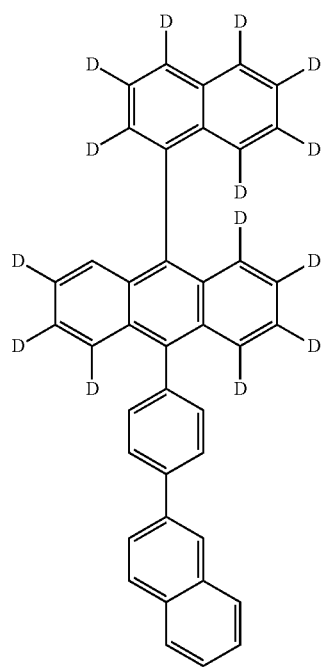
814
-continued
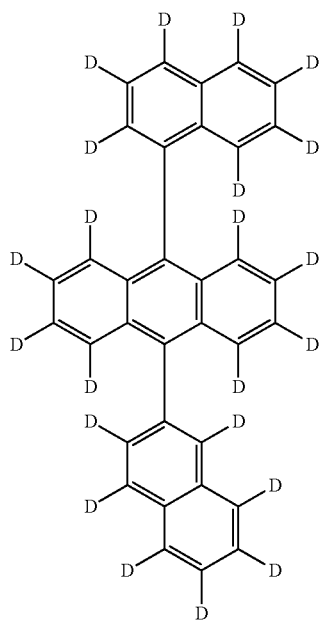
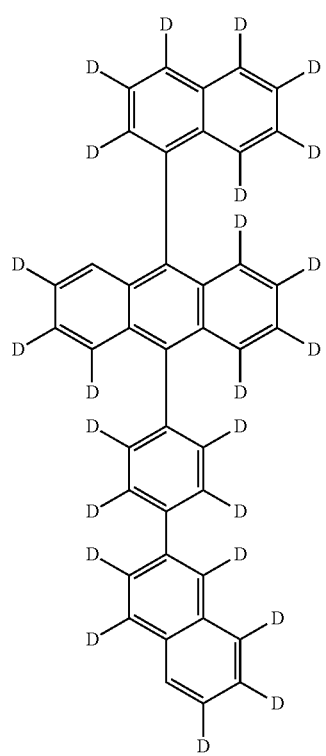
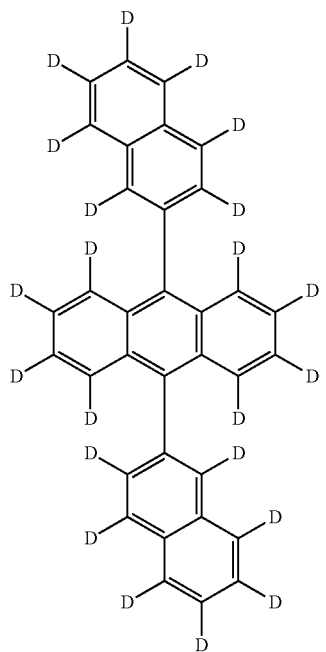

815
-continued

816
-continued

817
-continued
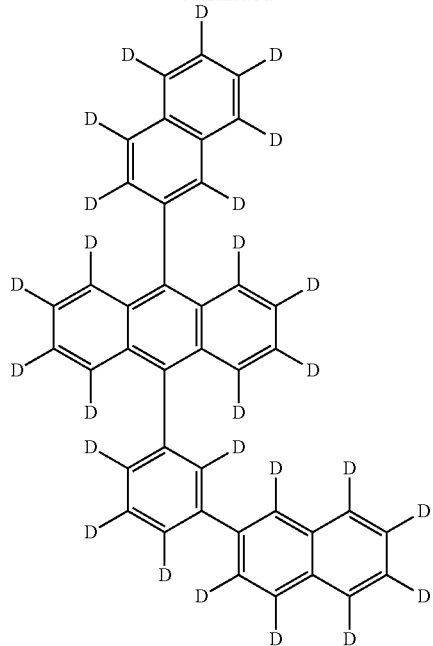
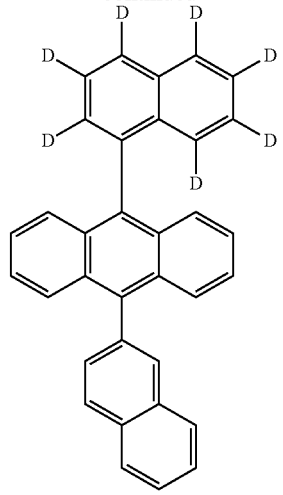
818
-continued
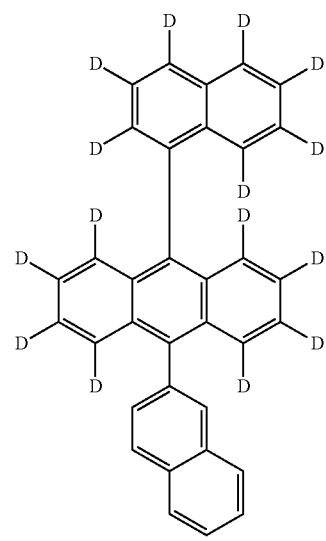
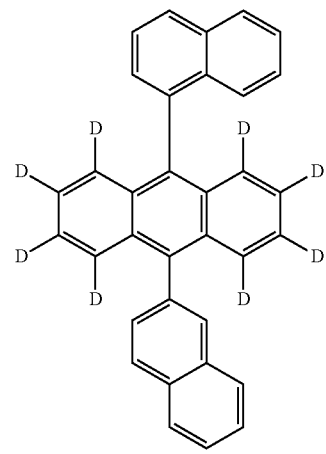

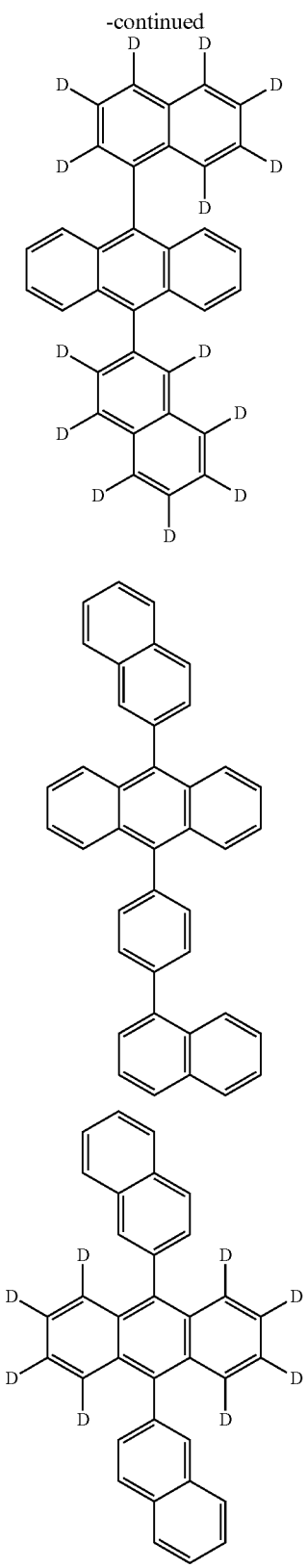

[General Formula 1]

In General Formula 1,

Ar₁ has the same definition as -L20-Ar20 of Chemical Formula H,

Ar2 has the same definition as -L21-Ar21 of Chemical Formula H, and the anthracene core of General Formula 1 may be further substituted with R20 and R21.

In one embodiment of the present specification, the compound represented by Chemical Formula 1 is used as a dopant, and the compound represented by Chemical Formula H is used as a host in the light emitting layer.

In one embodiment of the present specification, when the light emitting layer includes a host and a dopant, a content of the dopant may be selected in a range of 0.01 parts by weight to 10 parts by weight based on 100 parts by weight of the host, however, the content is not limited thereto.

The light emitting layer may further include a host material, and the host includes fused aromatic ring derivatives, heteroring-containing compounds or the like. Specifically, anthracene derivatives, pyrene derivatives, naphthalene derivatives, pentacene derivatives, phenanthrene compounds, fluoranthene compounds or the like may be included as the fused aromatic ring derivative, and carbazole derivatives, dibenzofuran derivatives, ladder-type furan compounds, pyrimidine derivatives, triazine derivatives or the like may be included as the heteroring-containing compound, and mixtures of two or more thereof may be included, however, the host material is not limited thereto.

According to one embodiment of the present specification, the organic material layer includes a light emitting layer, and the light emitting layer includes two or more mixed dopants and a host.

According to one embodiment of the present specification, one or more of the two or more mixed dopants include Chemical Formula 1, and the host includes the compound represented by Chemical Formula H. One or more of the two or more mixed dopants include Chemical Formula 1, and as According to one embodiment of the present specification, the compound represented by Chemical Formula H may be prepared using the following General Formula 1, however, the method is not limited thereto.

the rest, dopant materials known in the art may be used, however, the dopant is not limited thereto.

According to one embodiment of the present specification, one or more of the two or more mixed dopants include Chemical Formula 1, and as the rest, one or more of boron-based compounds, pyrene-based compounds and delayed fluorescence-based compounds different from Chemical Formula 1 may be used, however, the dopant is not limited thereto.

According to one embodiment of the present specification, the organic material layer includes a light emitting layer, and the light emitting layer includes one or more hosts.

According to one embodiment of the present specification, the organic material layer includes a light emitting layer, and the light emitting layer includes two or more mixed hosts.

According to one embodiment of the present specification, one or more of the two or more mixed hosts are the compound represented by Chemical Formula H.

According to one embodiment of the present specification, the two or more mixed hosts are different from each other, and each independently the compound represented by Chemical Formula H.

According to one embodiment of the present specification, the organic material layer includes a light emitting layer, and the light emitting layer includes two mixed hosts.

According to one embodiment of the present specification, the organic material layer includes a light emitting layer, the light emitting layer includes two mixed hosts, the two mixed hosts are different from each other, and the two hosts are the compound represented by Chemical Formula H.

According to one embodiment of the present specification, the organic material layer includes a light emitting layer, the light emitting layer includes a first host represented by Chemical Formula H; and a second host represented by Chemical Formula H, and the first host and the second host are different from each other.

According to one embodiment of the present specification, the first host:the second host are included in a weight ratio of 95:5 to 5:95, and preferably in a weight ratio of 70:30 to 30:70.

According to one embodiment of the present specification, the organic material layer includes a light emitting layer, and the light emitting layer includes one or more hosts and a dopant.

According to one embodiment of the present specification, the organic material layer includes a light emitting layer, the light emitting layer includes one or more hosts and a dopant, the hosts include the compound represented by Chemical Formula H, and the dopant includes the compound represented by Chemical Formula 1.

According to one embodiment of the present specification, the organic material layer includes a light emitting layer, and the light emitting layer includes two or more mixed hosts and a dopant.

According to one embodiment of the present specification, one or more of the two or more mixed hosts include the compound represented by Chemical Formula H, and the dopant includes the compound represented by Chemical Formula 1.

In the present specification, the two or more mixed hosts are different from each other.

According to one embodiment of the present specification, the organic material layer includes a light emitting layer, and the light emitting layer includes two mixed hosts and a dopant.

According to one embodiment of the present specification, the two mixed hosts are different from each other, and each independently include the compound represented by Chemical Formula H, and the dopant includes the compound represented by Chemical Formula 1.

According to one embodiment of the present specification, the organic material layer includes a light emitting layer, the light emitting layer includes a first host represented by Chemical Formula H; a second host represented by Chemical Formula H; and a dopant represented by Chemical Formula 1, and the first host and the second host are different from each other.

According to one embodiment of the present specification, the organic material layer uses one or more hosts and one or more dopants, the one or more hosts include the compound represented by Chemical Formula H, and the one or more dopants include the compound represented by Chemical Formula 1.

According to one embodiment of the present specification, the organic material layer uses two or more mixed hosts and two or more mixed dopants, the two or more mixed hosts may use the same materials as described above, and the two or more mixed dopants may use the same materials as described above.

In one embodiment of the present specification, the organic light emitting device includes a first electrode; a second electrode; a light emitting layer provided between the first electrode and the second electrode; and two or more layers of an organic material layer provided between the light emitting layer and the first electrode, or between the light emitting layer and the second electrode, wherein at least one of the two or more layers of an organic material layer includes the compound represented by Chemical Formula 1.

In one embodiment of the present specification, as the two or more layers of an organic material layer, two or more may be selected from the group consisting of a light emitting layer, a hole transfer layer, a hole injection layer, a layer carrying hole transfer and hole injection at the same time, and an electron blocking layer.

In one embodiment of the present specification, the organic material layer includes two or more electron transfer layers, and at least one of the two or more electron transfer layers includes the compound represented by Chemical Formula 1. Specifically, in one embodiment of the present specification, the compound represented by Chemical Formula 1 may be included in one of the two or more electron transfer layers, or may be included in each of the two or more electron transfer layers.

In addition, when the compound is included in each of the two or more electron transfer layers in one embodiment of the present specification, materials other than the compound represented by Chemical Formula 1 may be the same as or different from each other.

When the organic material layer including the compound represented by Chemical Formula 1 is an electron transfer layer, the electron transfer layer may further include an n-type dopant. As the n-type dopant, those known in the art may be used, and for example, metals or metal complexes may be used. For example, the electron transfer layer including the compound represented by Chemical Formula 1 may further include lithium quinolate (LiQ).

In one embodiment of the present specification, the organic material layer includes two or more hole transfer layers, and at least one of the two or more hole transfer layers includes the compound represented by Chemical Formula 1. Specifically, in one embodiment of the present specification, the compound represented by Chemical Formula 1 may be included in one of the two or more hole transfer layers, or may be included in each of the two or more hole transfer layers.

In addition, when the compound represented by Chemical Formula 1 is included in each of the two or more hole transfer layers in one embodiment of the present specification, materials other than the compound represented by Chemical Formula 1 may be the same as or different from each other.

In one embodiment of the present specification, the organic material layer may further include, in addition to the organic material layer including the compound represented by Chemical Formula 1, a hole injection layer or a hole transfer layer including a compound including an arylamine group, a carbazolyl group or a benzocarbazolyl group.

In one embodiment of the present specification, the first electrode is an anode or a cathode.

In one embodiment of the present specification, the second electrode is a cathode or an anode.

In one embodiment of the present specification, the organic light emitting device may be an organic light emitting device having a structure in which an anode, an organic material layer including one or more layers and a cathode are consecutively laminated on a substrate (normal type).

In one embodiment of the present specification, the organic light emitting device may be an organic light emitting device having a structure in a reverse direction in which a cathode, an organic material layer including one or more layers and an anode are consecutively laminated on a substrate (inverted type).

Figure 2:
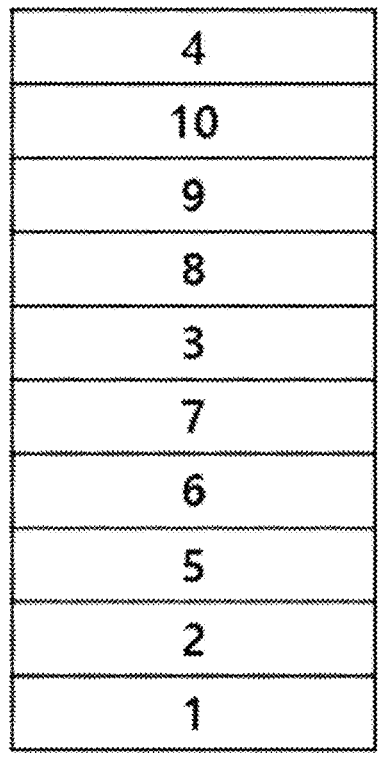

For example, structures of the organic light emitting device according to one embodiment of the present specification are illustrated in FIG. 1 and FIG. 2. FIG. 1 and FIG. 2 illustrate the organic light emitting device, and the organic light emitting device is not limited thereto.

FIG. 1 illustrates a structure of the organic light emitting device in which a substrate (1), a first electrode (2), a light emitting layer (3) and a second electrode (4) are consecutively laminated. In such a structure, the compound may be included in the light emitting layer (3).

FIG. 2 illustrates a structure of the organic light emitting device in which a substrate (1), a first electrode (2), a hole injection layer (5), a hole transfer layer (6), an electron blocking layer (7), a light emitting layer (3), a first electron transfer layer (8), a second electron transfer layer (9), an electron injection layer (10) and a second electrode (4) are consecutively laminated. In such a structure, the compound may be included in the light emitting layer (3).

The organic light emitting device of the present specification may be manufactured using materials and methods known in the art, except that one or more layers of the organic material layer include the compound, that is, the compound represented by Chemical Formula 1.

When the organic light emitting device includes a plurality of layers of the organic material layer, the plurality of layers may be formed with the same materials or different materials.

For example, the organic light emitting device of the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material usable as a cathode thereon. In addition to such a method, the organic light emitting device may also be manufactured by consecutively depositing a cathode material, an organic material layer and an anode material on a substrate.

In addition, the compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may also be manufactured by consecutively laminating a cathode material, an organic material layer and an anode material on a substrate (International Patent Application Laid Open Publication No. 2003/012890). However, the manufacturing method is not limited thereto.

As the first electrode material, materials having large work function are normally preferred so that hole injection to an organic material layer is smooth. Examples thereof include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the second electrode material, materials having small work function are normally preferred so that electron injection to an organic material layer is smooth. Examples thereof include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, however, the material is not limited thereto.

The dopant material includes, when including an additional compound in addition to the compound represented by Chemical Formula 1, aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, perylanthene and the like. In addition, the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

In the present specification, when the compound represented by Chemical Formula 1 is included in an organic material layer other than the light emitting layer, or an additional light emitting layer is provided, a light emitting material of the light emitting layer is, as a material capable of emitting light in a visible region by receiving holes and electrons from a hole transfer layer and an electron transfer layer, respectively, and binding the holes and the electrons, preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene; rubrene, and the like, but are not limited thereto.

The hole injection layer is a layer injecting holes from an electrode. The hole injection material preferably has, by having an ability to transfer holes, a hole injection effect in a first electrode and an excellent hole injection effect for a light emitting layer or a light emitting material. In addition, the hole injection material is preferably a material having an excellent ability to prevent excitons generated in the light emitting layer from moving to an electron injection layer or an electron injection material. In addition, a material having an excellent thin film forming ability is preferred. In addition, the highest occupied molecular orbital (HOMO) of the hole injection material is preferably in between the work function of a first electrode material and the HOMO of surrounding organic material layers. Specific examples of the hole injection material include metal porphyrins, oligothiophene, arylamine-based organic materials; carbazole-based organic materials; nitrile-based organic materials; hexanitrile hexaazatriphenylene-based organic materials; quinacridone-based organic materials; perylene-based organic materials; polythiophene-based conductive polymers such as anthraquinone or polyaniline, mixtures of two or more of the examples, and the like, but are not limited thereto.

The hole transfer layer is a layer receiving holes from a hole injection layer and transferring the holes to a light emitting layer. As the hole transfer material, materials having, as a material capable of receiving holes from a first electrode or a hole injection layer and moving the holes to a light emitting layer, high mobility for the holes are preferred. Specific examples thereof include arylamine-based organic materials, carbazole-based organic materials, conductive polymers, block copolymers having conjugated parts and non-conjugated parts together, and the like, but are not limited thereto.

The electron transfer layer is a layer receiving electrons from an electron injection layer and transferring the electrons to a light emitting layer. As the electron transfer material, materials capable of favorably receiving electrons from a second electrode, moving the electrons to a light emitting layer, and having high mobility for the electrons are preferred. Specific examples thereof include Al complexes of 8-hydroxyquinoline; complexes including $Alq_3$; organic radical compounds; hydroxyflavon-metal complexes; triazine derivatives; LiQ and the like, but are not limited thereto. The electron transfer layer may be used together with any desired first electrode material as used in the art. Particularly, the suitable first electrode material is a common material having low work function and having an aluminum layer or a silver layer following. Specifically, cesium, barium, calcium, ytterbium, samarium and the like are included, and in each case, an aluminum layer or a silver layer follows.

The electron injection layer is a layer injecting electrons from an electrode. As the electron injection material, materials having an excellent electron transferring ability, having an electron injection effect from a second electrode, and having an excellent electron injection effect for a light emitting layer or light emitting material are preferred. In addition, materials preventing excitons generated in the light emitting layer from moving to a hole injection layer, and having an excellent thin film forming ability are preferred. Specific examples thereof include fluorenone, anthraquinodimethane, diphenoquinone, thiopyran dioxide, oxazole, oxadiazole, triazole, triazine, midazole, perylene tetracarboxylic acid, fluorenylidene methane, anthrone or the like, and derivatives thereof, metal complex compounds, nitrogen-containing 5-membered ring derivatives, mixtures of two or more of the examples, and the like, but are not limited thereto.

The metal complex compound includes 8-hydroxyquinolinato lithium, bis(8-hydroxyquinolinato)zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium and the like, but is not limited thereto.

The electron blocking layer is a layer capable of enhancing lifetime and efficiency of a device by preventing electrons injected from an electron injection layer from passing through a light emitting layer and entering a hole injection layer. Known material may be used without limit, and the electron blocking layer may be formed between the light emitting layer and the hole injection layer, or between the light emitting layer and a layer carrying out hole injection and hole transfer at the same time.

The hole blocking layer is a layer blocking holes from passing a light emitting layer and reaching a cathode, and may be generally formed under the same condition as the electron injection layer. Specific examples thereof may include oxadiazole derivatives, triazole derivatives, phenanthroline derivatives, aluminum complexes, pyridine, pyrimidine or triazine derivatives and the like, but are not limited thereto.

The organic light emitting device according to the present specification may be a top-emission type, a bottom-emission type or a dual-emission type depending on the materials used.

In one embodiment of the present specification, the compound represented by Chemical Formula 1 may be included in, in addition to the organic light emitting device, an organic solar cell or an organic transistor.

The compound according to the present specification may also be used in an organic light emitting device including an organic phosphorescent device, an organic solar cell, an organic photo conductor, an organic transistor and the like under a similar principle used in the organic light emitting device. For example, the organic solar cell may have a structure including a cathode, an anode, and a photoactive layer provided between the cathode and the anode, and the photoactive layer may include the compound.

The organic light emitting device of the present specification may be manufactured using common organic light emitting device manufacturing methods and materials except that one or more layers of the organic material layer are formed using the compound described above.

EXAMPLES

Hereinafter, the present specification will be described in detail with reference to examples, comparative examples and the like. However, the examples and the comparative examples according to the present specification may be modified to various other forms, and the scope of the present specification is not to be construed as being limited to the examples and the comparative examples described below. Examples and comparative examples of the present specification are provided in order to more fully describe the present specification to those having average knowledge in the art.

Preparation Example 1: Synthesis of Compound A-1

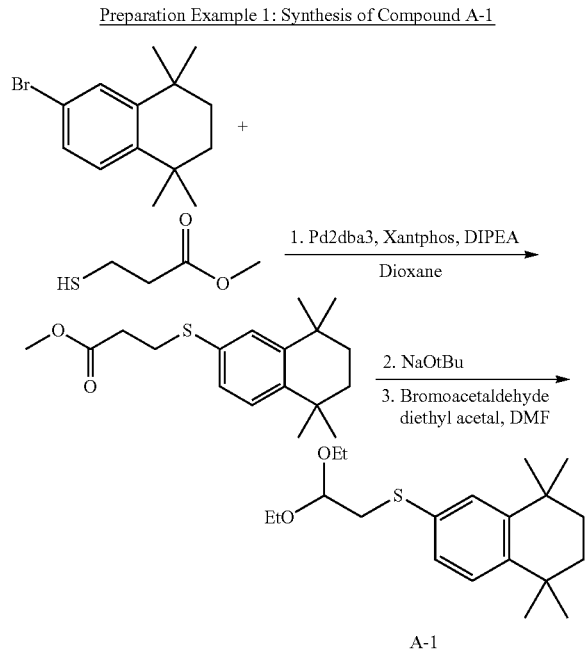

After dissolving 6-bromo-1,1,4,4-tetramethyl-1,2,3,4-tetrahydronaphthalene (40.5 g, 151.566 mmol), methyl 3-mercaptopropionate (16.6 ml, 150 mmol), $Pd_2dba_3$ (2.06 g, 2.24 mmol), Xantphos (4,5-bis(diphenylphosphino)-9,9-dimethylxanthene) (2.6 g, 4.49 mmol) and DIPEA (52 ml, 298.54 mmol) in dioxane (1000 ml), the mixture was stirred under reflux. When the reaction was finished, the result was cooled to room temperature, and stirred after adding NaOtBu (43 g, 450 mmol) thereto. When the reaction was finished, bromoacetaldehyde diethyl acetal (45.1 ml, 299 mmol) and dimethylformamide (DMF) (500 ml) were introduced thereto, and the result was stirred. When the reaction was finished, the result was cooled to room temperature, and the reaction material was transferred to a separatory funnel and then extracted. The result was dried with $MgSO_4$, filtered, concentrated, and purified using column chromatography to obtain Compound A-1 (40.9 g, yield 83%).

MS: $[M+H]^+=337$

Preparation Example 2: Synthesis of Compound A-2

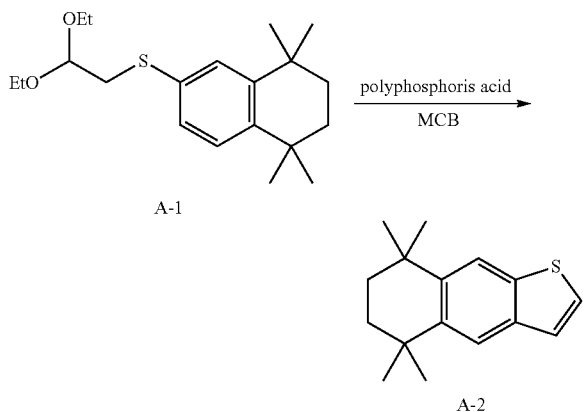

After dissolving Compound A-1 (50.5 g, 150.1 mmol) and polyphosphoric acid (105 ml) in monochlorobenzene (MCB) (750 ml), the mixture was stirred under reflux. When the reaction was finished, the result was cooled to room temperature, and the reaction material was transferred to a separatory funnel and then extracted. The result was dried with $MgSO_4$, filtered, concentrated, and purified using column chromatography to obtain Compound A-2 (33.01 g, yield 90%).

MS: $[M+H]^+=245$

Preparation Example 3: Synthesis of Compound A

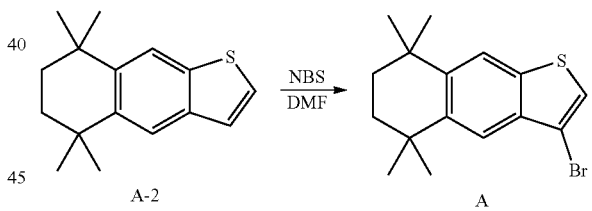

Compound A-2 (4.8 g, 19.6 mmol) and N-bromosuccinimide (NBS) (3.6 g, 20.2 mmol) were dissolved in dimethylformamide (DMF), and the temperature was maintained at −20° C. When the reaction was finished, the reaction material was transferred to a separatory funnel at room temperature and then extracted. The result was dried with $MgSO_4$, filtered, concentrated, and purified using column chromatography to obtain Compound A (4 g, yield 63%).

MS: $[M+H]^+=324$

Preparation Example 4: Synthesis of Compound B-1

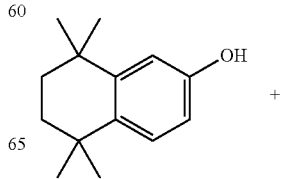

829

-continued

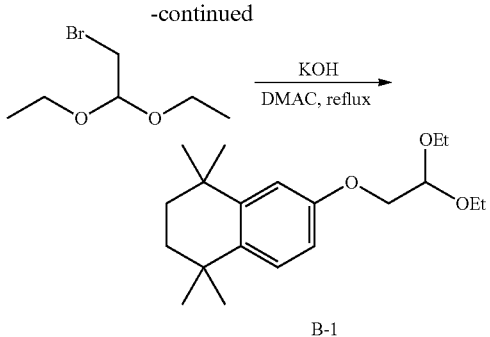

B-1

After dissolving 5,5,8,8-tetramethyl-5,6,7,8-tetrahydronaphthalen-2-ol (32 g, 156.6 mmol) and KOH (17.58 g, 313.2 mmol) in dimethylacetamide (DMAC) (313 ml), 2-bromo-1,1-diethoxyethane (30.56 g, 155.1 mmol) was slowly added dropwise thereto, and the result was stirred under reflux. When the reaction was finished, the result was cooled to room temperature, and the reaction material was transferred to a separatory funnel and then extracted. The result was dried with MgSO$_4$, filtered, concentrated, and purified using column chromatography to obtain Compound B-1 (46.71 g, yield 94%).

MS: [M+H]$^+$=320.47

Preparation Example 5: Synthesis of Compound B-2

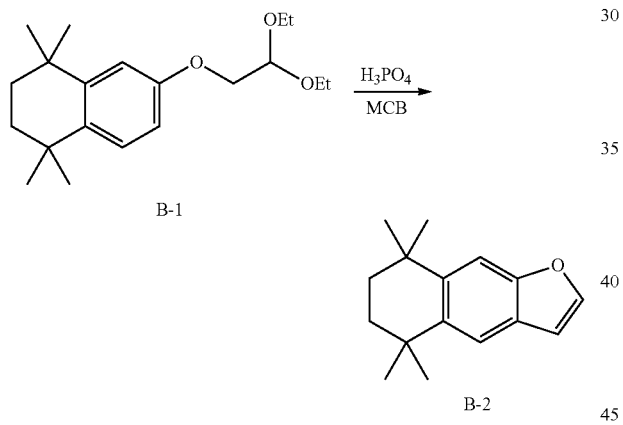

After dissolving Compound B-1 (46.71 g, 145.8 mmol) and H$_3$PO$_4$ (44 ml) in monochlorobenzene (MCB) (485 ml), the mixture was stirred under reflux. When the reaction was finished, the result was cooled to room temperature, and the reaction material was transferred to a separatory funnel and then extracted. The result was dried with MgSO$_4$, filtered, concentrated, and purified using column chromatography to obtain Compound B-2 (28.29 g, yield 85%).

MS: [M+H]$^+$=229

Preparation Example 6: Synthesis of Compound B-3

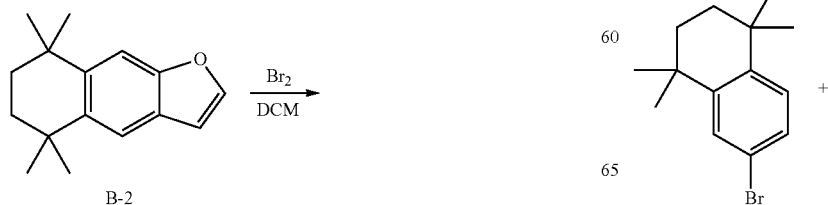

830

-continued

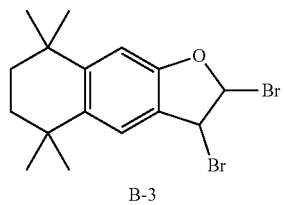

B-3

Compound B-2 (28.29 g, 123.9 mmol) was dissolved in dichloromethane (DCM) (353 ml). Br$_2$ (21.78 g, 136.3 mmol) was slowly added dropwise thereto while stirring at −10° C. When the reaction was finished, an aqueous Na$_2$SO$_3$ solution was introduced thereto at room temperature. The reaction material was transferred to a separatory funnel and then extracted. The result was dried with MgSO$_4$, filtered, concentrated, and purified using column chromatography to obtain Compound B-3 (26.45 g, yield 55%).

MS: [M+H]$^+$=389

Preparation Example 7: Synthesis of Compound B

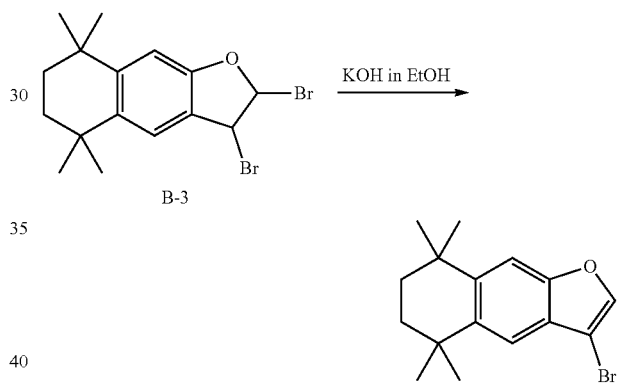

After dissolving Compound B-3 (26.45 g, 68.1 mmol) in ethanol, a KOH saturated ethanol solution was slowly added dropwise thereto at 0° C. After that, the mixture was stirred under reflux. When the reaction was finished, the result was cooled to room temperature, and the reaction material was transferred to a separatory funnel and then extracted. The result was dried with MgSO$_4$, filtered, concentrated, and purified using column chromatography to obtain Compound B (18.01 g, yield 86%).

MS: [M+H]$^+$=308

Preparation Example 8: Synthesis of Compound 1-1

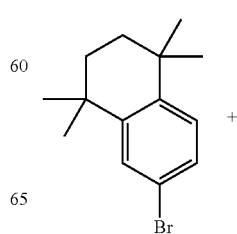

-continued

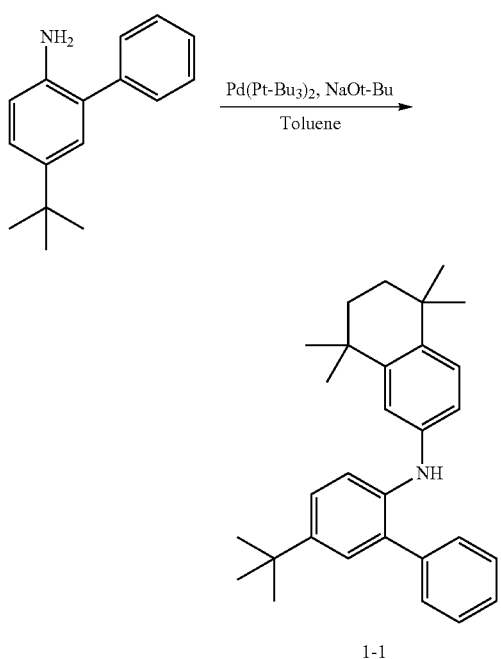

1-1

After dissolving 6-bromo-1,1,4,4-tetramethyl-1,2,3,4-tetrahydronaphthalene (25.0 g, 93.6 mmol), 5-(tert-butyl)-[1,1'-biphenyl]-2-amine (21.08 g, 93.6 mmol), Pd(Pt-Bu₃)₂ (0.96 g, 1.9 mmol) and NaOt-Bu (17.98 g, 187.1 mmol) in toluene (467 ml), the mixture was stirred under reflux. When the reaction was finished, the result was cooled to room temperature, and the reaction material was transferred to a separatory funnel and then extracted. The result was dried with MgSO₄, filtered, concentrated, and purified using column chromatography to obtain Compound 1-1 (31.19 g, yield 81%).

MS: [M+H]⁺=412

Preparation Example 9: Synthesis of Compound 1-2

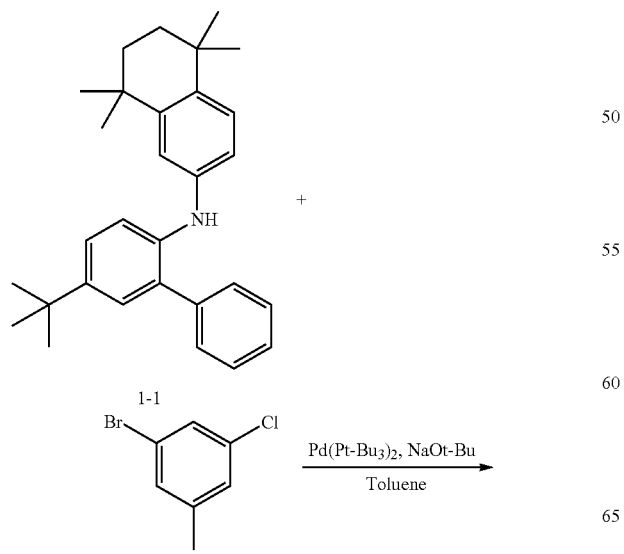

-continued

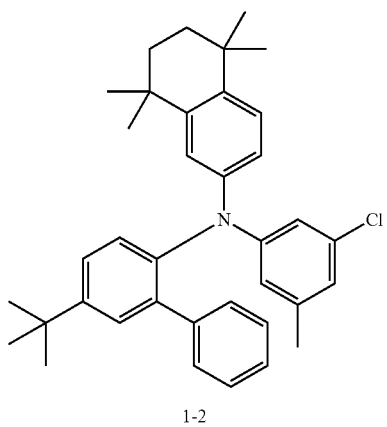

1-2

After dissolving Compound 1-1 (31.19 g, 75.8 mmol), 1-bromo-3-chloro-5-methylbenzene (15.57 g, 75.8 mmol), Pd(Pt-Bu₃)₂ (0.77 g, 1.9 mmol) and NaOt-Bu (14.56 g, 151.5 mmol) in toluene (378 ml), the mixture was stirred under reflux. When the reaction was finished, the result was cooled to room temperature, and the reaction material was transferred to a separatory funnel and then extracted. The result was dried with MgSO₄, filtered, concentrated, and purified using column chromatography to obtain Compound 1-2 (30.47 g, yield 75%).

MS: [M+H]⁺=537

Preparation Example 10: Synthesis of Compound 1-3

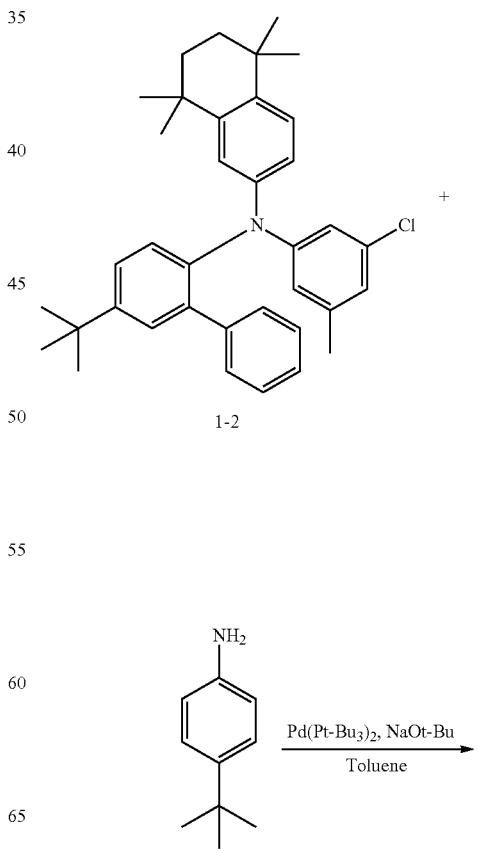

833

-continued

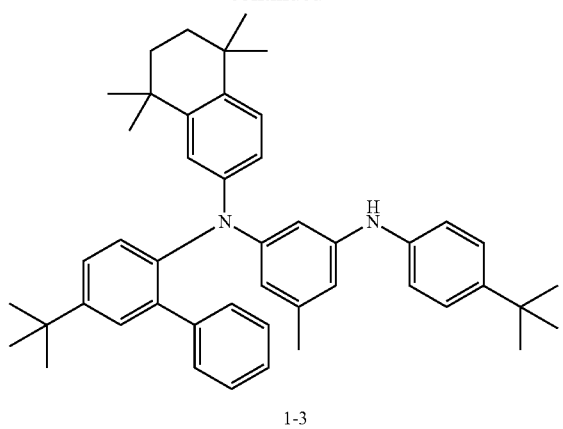

1-3

After dissolving Compound 1-2 (30.47 g, 56.8 mmol), 4-(tert-butyl)aniline (8.48 g, 56.8 mmol), Pd(Pt-Bu₃)₂ (0.58 g, 1.1 mmol) and NaOt-Bu (10.92 g, 113.7 mmol) in toluene (284 ml), the mixture was stirred under reflux. When the reaction was finished, the result was cooled to room temperature, and the reaction material was transferred to a separatory funnel and then extracted. The result was dried with MgSO₄, filtered, concentrated, and purified using column chromatography to obtain Compound 1-3 (26.55 g, yield 72%).

MS: [M+H]⁺=649

Preparation Example 11: Synthesis of Compound 1-4

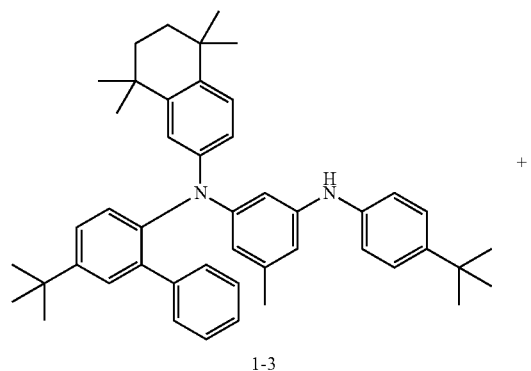

1-3

+

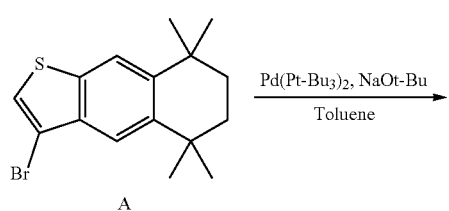

A

Pd(Pt-Bu₃)₂, NaOt-Bu
———————————→
Toluene

834

-continued

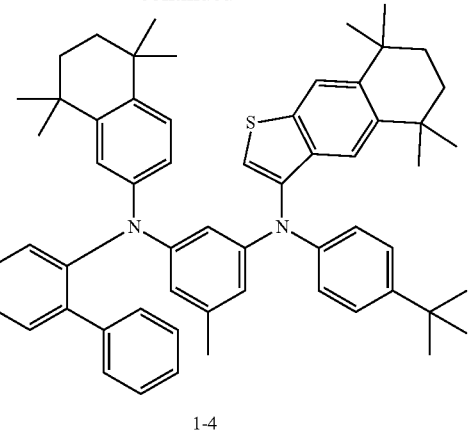

1-4

After dissolving Compound 1-3 (26.55 g, 40.9 mmol), Compound A (13.23 g, 40.9 mmol), Pd(Pt-Bu₃)₂ (0.42 g, 0.8 mmol) and NaOt-Bu (7.86 g, 81.8 mmol) in toluene (204 ml), the mixture was stirred under reflux. When the reaction was finished, the result was cooled to room temperature, and the reaction material was transferred to a separatory funnel and then extracted. The result was dried with MgSO₄, filtered, concentrated, and purified using column chromatography to obtain Compound 1-4 (30.27 g, yield 83%).

MS: [M+H]⁺=892

Preparation Example 12: Synthesis of Compound 1

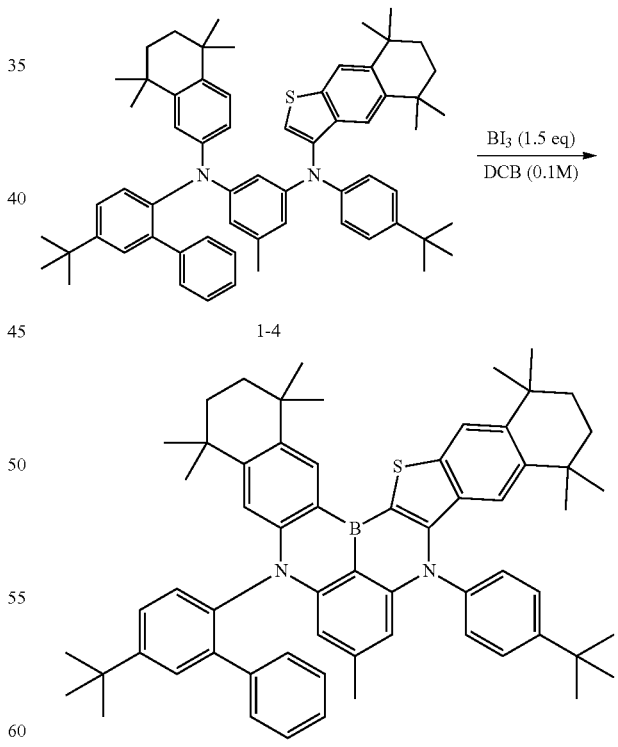

After dissolving Compound 1-4 (30.27 g, 34.0 mmol) in 1,2-dichlorobenzene (DCB) (340 ml), BI₃ (19.94 g, 50.9 mmol) was introduced thereto, and the result was stirred at 130° C. When the reaction was finished, N,N-diisopropylethylamine (DIPEA) (17.56 g, 135.8 mmol) was added thereto at 0° C. After that, the reaction material was transferred to a separatory funnel and then extracted. The result was dried with MgSO$_4$, filtered, concentrated, and purified using column chromatography to obtain Compound 1 (9.16 g, yield 30%).

MS: [M+H]$^+$=900

Preparation Example 13: Synthesis of Compound 2-1

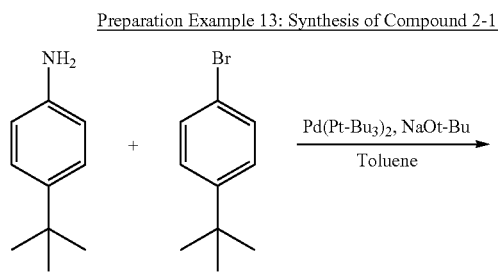

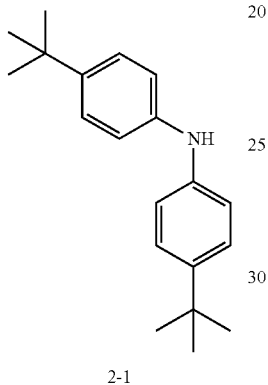

Compound 2-1 was obtained in the same manner as in Preparation of Compound 1-1 of Preparation Example 8 except that 1-bromo-4-(tert-butyl)benzene was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]$^+$=282

Preparation Example 14: Synthesis of Compound 2-2

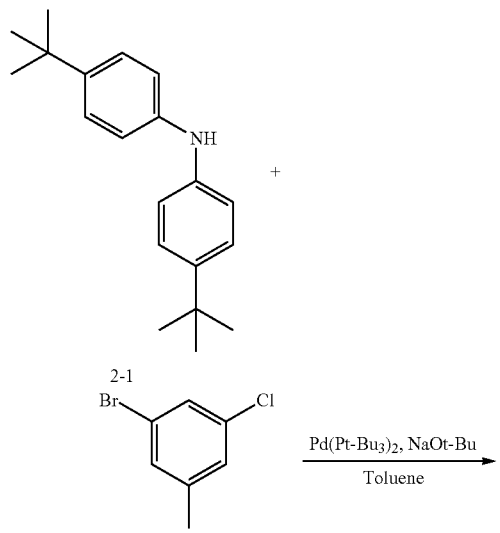

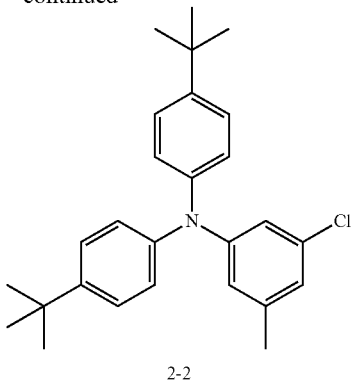

Compound 2-2 was obtained in the same manner as in Preparation of Compound 1-2 of Preparation Example 9 except that Compound 2-1 was used instead of Compound 1-1.

MS: [M+H]$^+$=407

Preparation Example 15: Synthesis of Compound 2-3

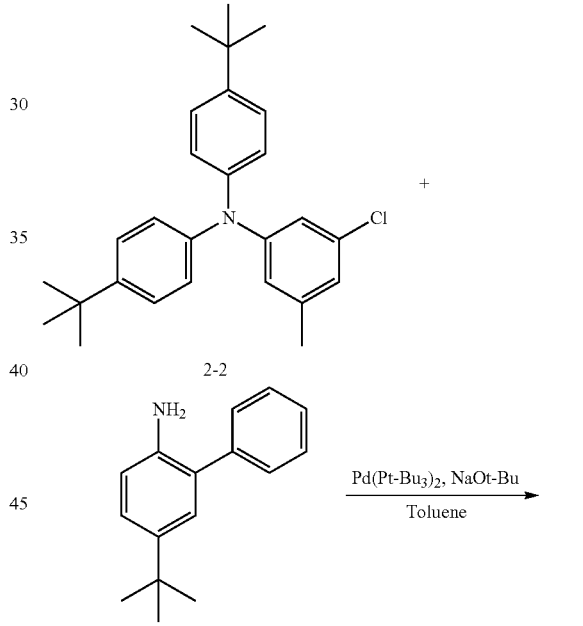

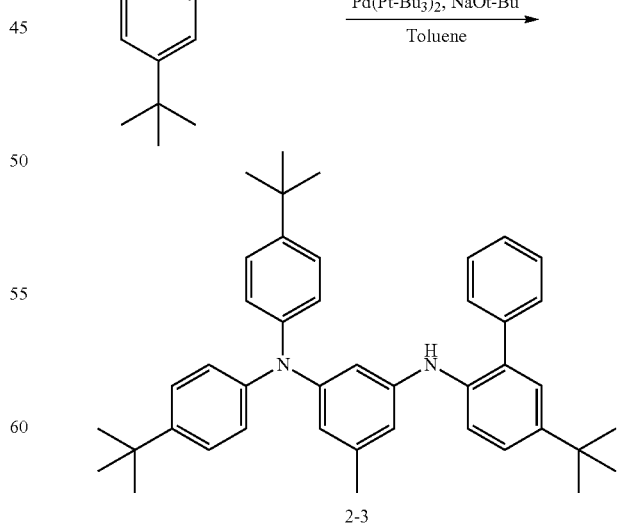

Compound 2-3 was obtained in the same manner as in Preparation of Compound 1-3 of Preparation Example 10 except that Compound 2-2 was used instead of Compound 1-2, and 5-(tert-butyl)-[1,1'-biphenyl]-2-amine was used instead of 4-(tert-butyl)aniline.

MS: [M+H]⁺=595

Preparation Example 16: Synthesis of Compound 2-4

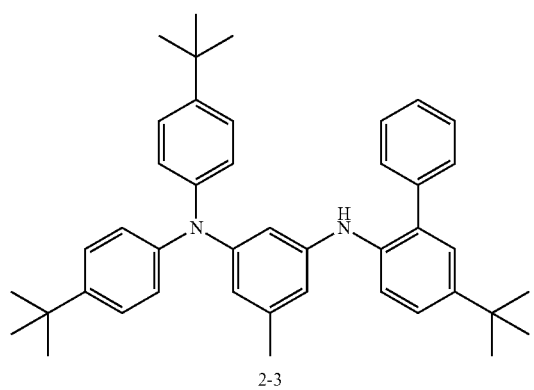

2-3

+

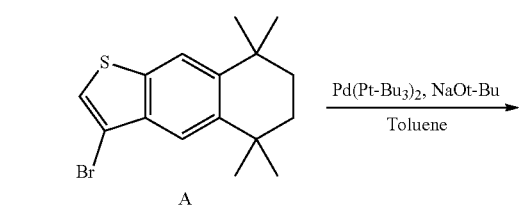

A

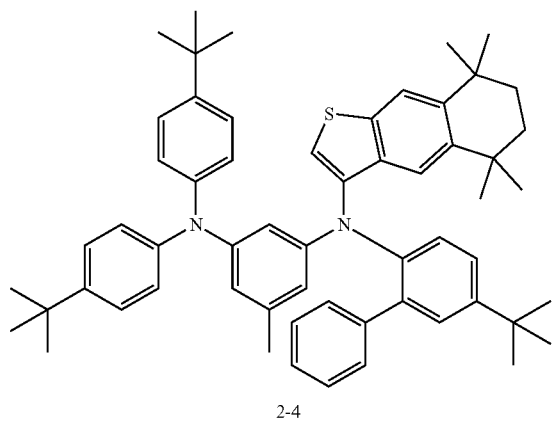

2-4

Compound 2-4 was obtained in the same manner as in Preparation of Compound 1-4 of Preparation Example 11 except that Compound 2-3 was used instead of Compound 1-3.

MS: [M+H]⁺=838

Preparation Example 17: Synthesis of Compound 2

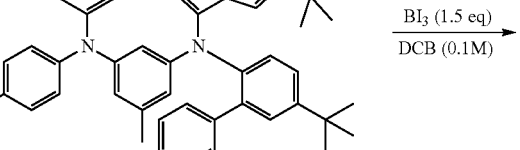

2-4

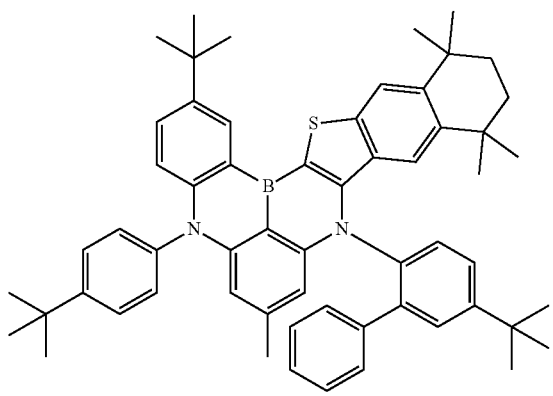

2

Compound 2 was obtained in the same manner as in Preparation of Compound 1 of Preparation Example 12 except that Compound 2-4 was used instead of Compound 1-4.

MS: [M+H]⁺=846

Preparation Example 18: Synthesis of Compound 3-1

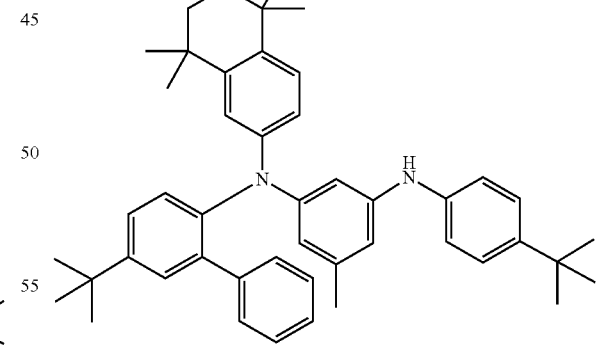

1-3

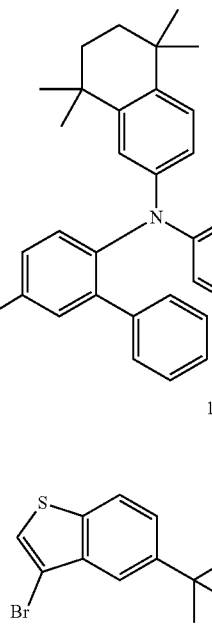

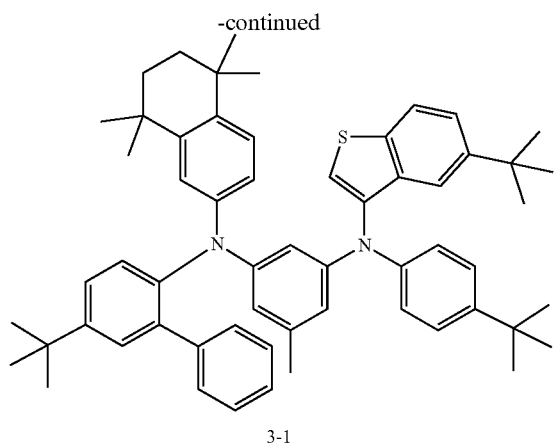

3-1

Compound 3-1 was obtained in the same manner as in Preparation of Compound 1-4 of Preparation Example 11 except that 3-bromo-5-(tert-butyl)benzo[b]thiophene was used instead of Compound A.

MS: [M+H]$^+$=838

Preparation Example 19: Synthesis of Compound 3

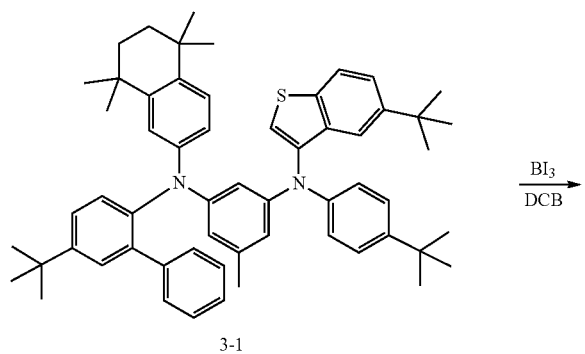

3

Compound 3 was obtained in the same manner as in Preparation of Compound 1 of Preparation Example 12 except that Compound 3-1 was used instead of Compound 1-4.

MS: [M+H]$^+$=846

Preparation Example 20: Synthesis of Compound 4-1

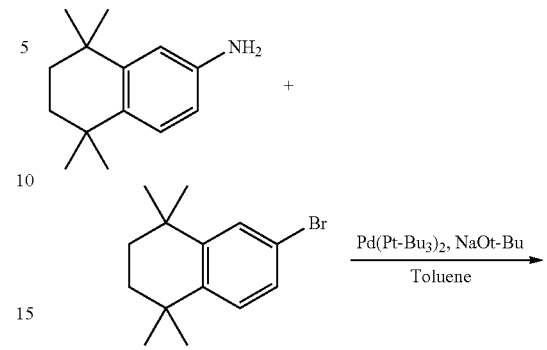

4-1

Compound 4-1 was obtained in the same manner as in Preparation of Compound 1-1 of Preparation Example 8 except that 5,5,8,8-tetramethyl-5,6,7,8-tetrahydronaphthalen-2-amine was used instead of 5-(tert-butyl)-[1,1'-biphenyl]-2-amine.

MS: [M+H]$^+$=390

Preparation Example 21: Synthesis of Compound 4-2

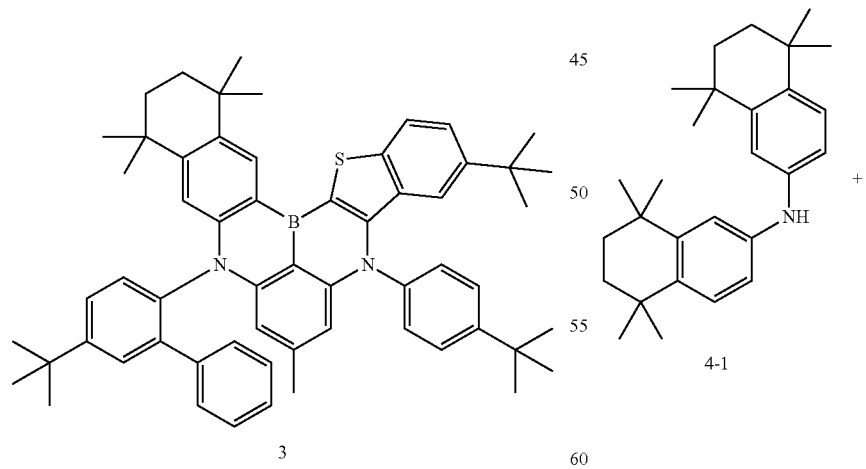

4-1

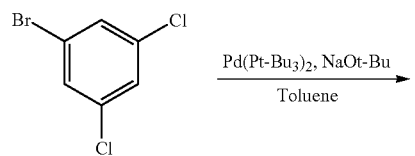

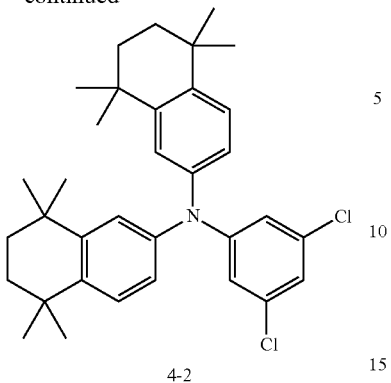

4-2

Compound 4-2 was obtained in the same manner as in Preparation of Compound 1-2 of Preparation Example 9 except that Compound 4-1 was used instead of Compound 1-1, and 1-bromo-3,5-dichlorobenzene was used instead of 1-bromo-3-chloro-5-methylbenzene.

MS: $[M+H]^+=535$

Preparation Example 22: Synthesis of Compound 4-3

Compound 4-3 was obtained in the same manner as in Preparation of Compound 1-3 of Preparation Example 10 except that Compound 4-2 was used instead of Compound 1-2, and 5-(tert-butyl)-[1,1'-biphenyl]-2-amine was used instead of 4-(tert-butyl)aniline.

MS: $[M+H]^+=724$

Preparation Example 23: Synthesis of Compound 4-4

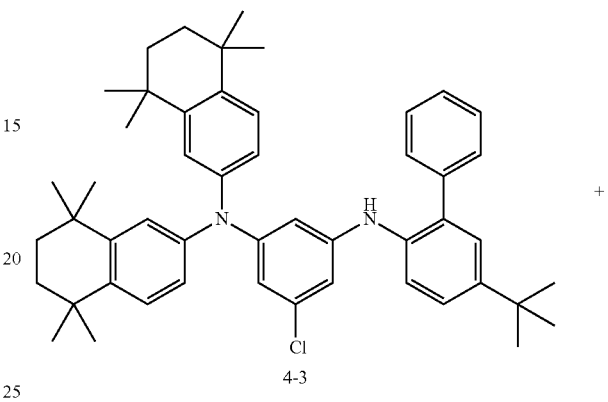

4-3

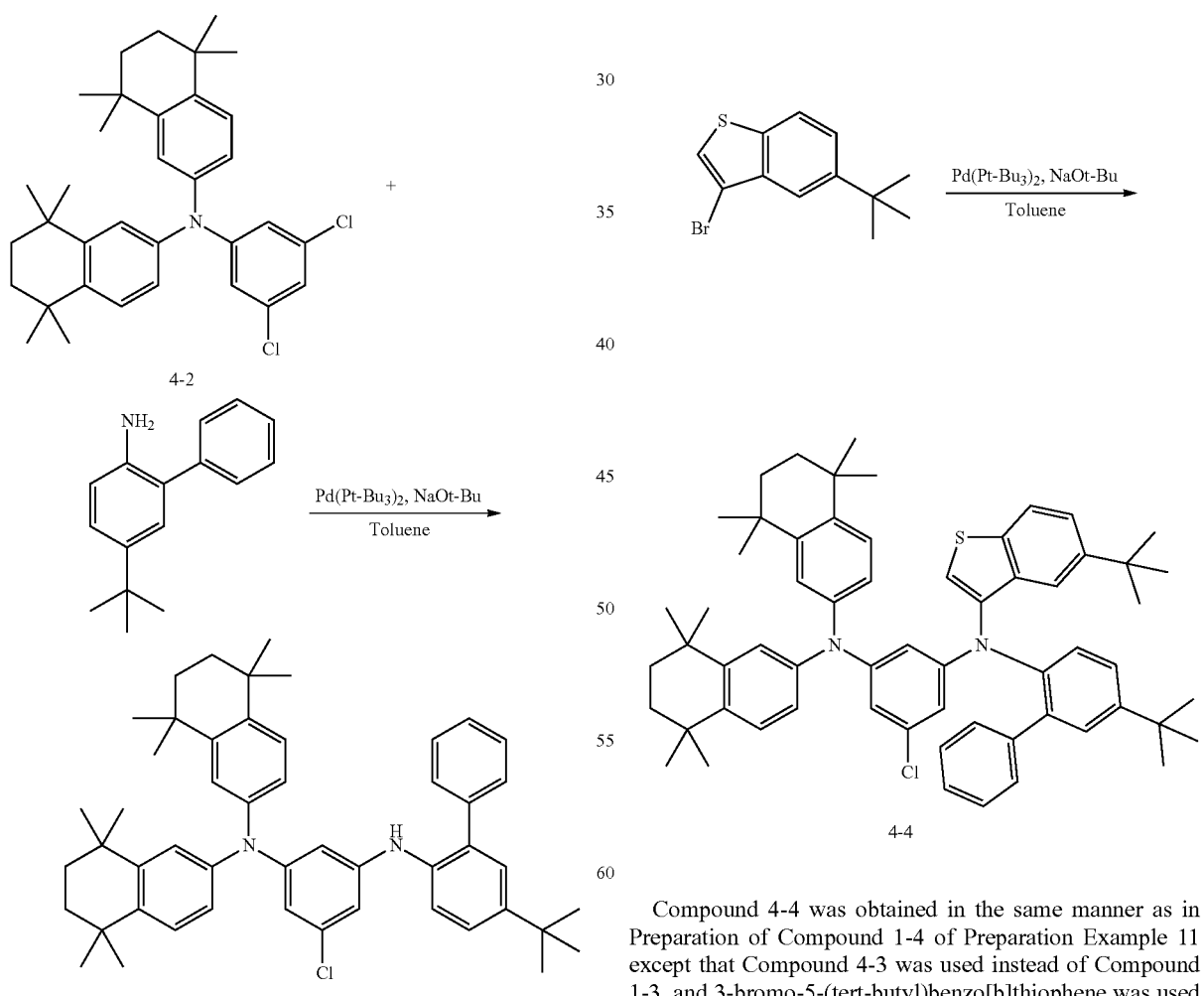

4-4

Compound 4-4 was obtained in the same manner as in Preparation of Compound 1-4 of Preparation Example 11 except that Compound 4-3 was used instead of Compound 1-3, and 3-bromo-5-(tert-butyl)benzo[b]thiophene was used instead of Compound A.

MS: $[M+H]^+=912$

Preparation Example 24: Synthesis of Compound 4-5

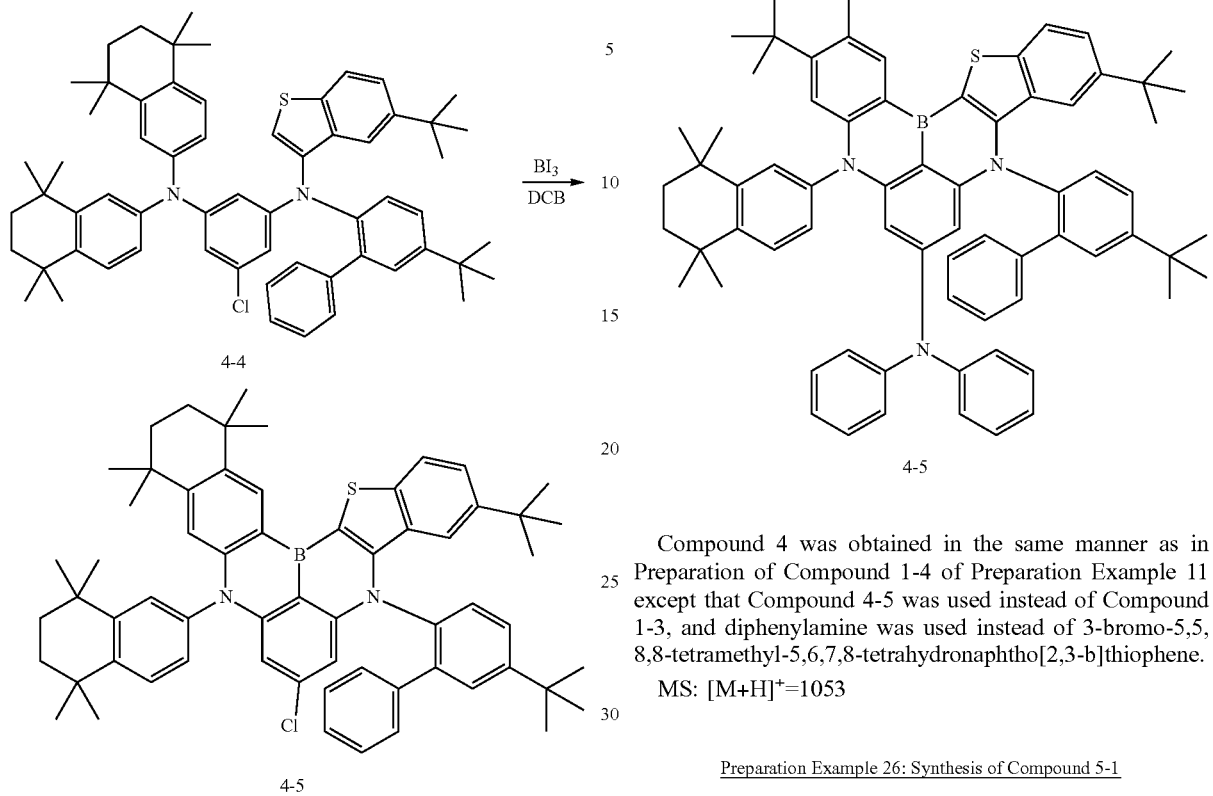

Compound 4-5 was obtained in the same manner as in Preparation of Compound 1 of Preparation Example 12 except that Compound 4-4 was used instead of Compound 1-4.

MS: [M+H]$^+$=920

Preparation Example 25: Synthesis of Compound 4

Compound 4 was obtained in the same manner as in Preparation of Compound 1-4 of Preparation Example 11 except that Compound 4-5 was used instead of Compound 1-3, and diphenylamine was used instead of 3-bromo-5,5,8,8-tetramethyl-5,6,7,8-tetrahydronaphtho[2,3-b]thiophene.

MS: [M+H]$^+$=1053

Preparation Example 26: Synthesis of Compound 5-1

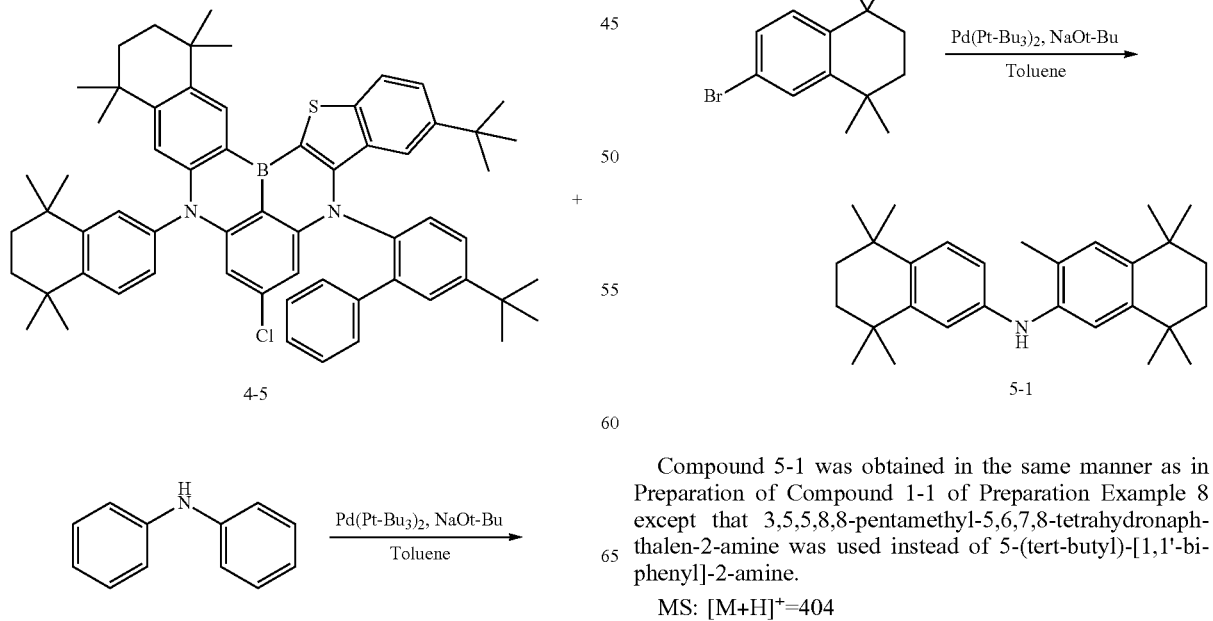

Compound 5-1 was obtained in the same manner as in Preparation of Compound 1-1 of Preparation Example 8 except that 3,5,5,8,8-pentamethyl-5,6,7,8-tetrahydronaphthalen-2-amine was used instead of 5-(tert-butyl)-[1,1'-biphenyl]-2-amine.

MS: [M+H]$^+$=404

Preparation Example 27: Synthesis of Compound 5-2

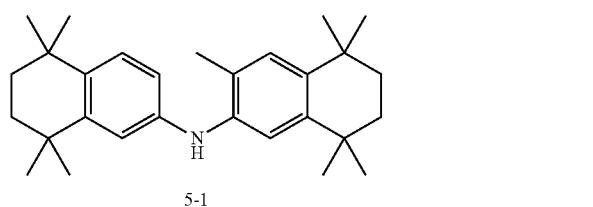

5-1

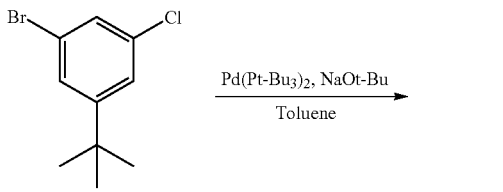

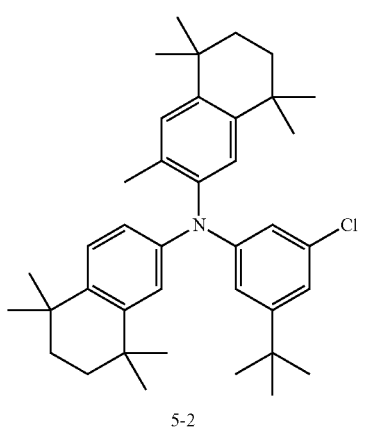

5-2

Compound 5-2 was obtained in the same manner as in Preparation of Compound 1-2 of Preparation Example 9 except that Compound 5-1 was used instead of Compound 1-1, and 1-bromo-3-(tert-butyl)-5-chlorobenzene was used instead of 1-bromo-3-chloro-5-methylbenzene.

MS: [M+H]$^+$=571

Preparation Example 28: Synthesis of Compound 5-3

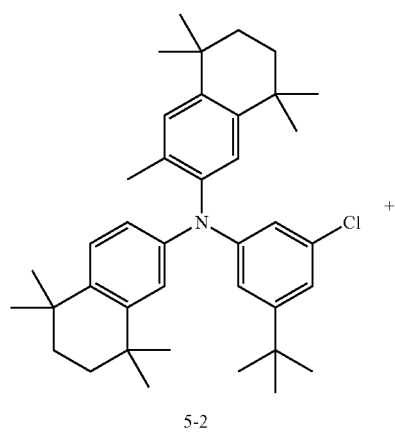

5-2

+

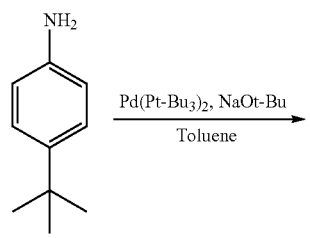

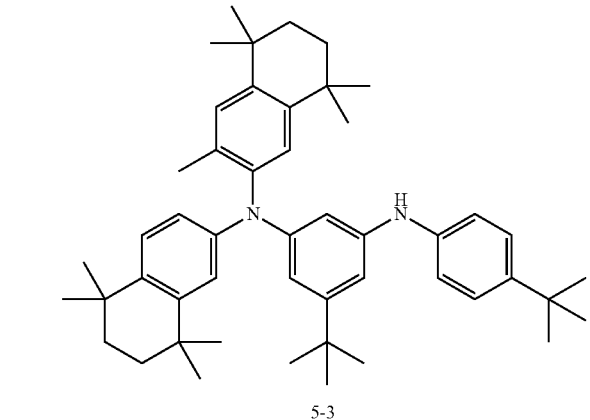

5-3

Compound 5-3 was obtained in the same manner as in Preparation of Compound 1-3 of Preparation Example 10 except that Compound 5-2 was used instead of Compound 1-2.

MS: [M+H]$^+$=684

Preparation Example 29: Synthesis of Compound 5-4

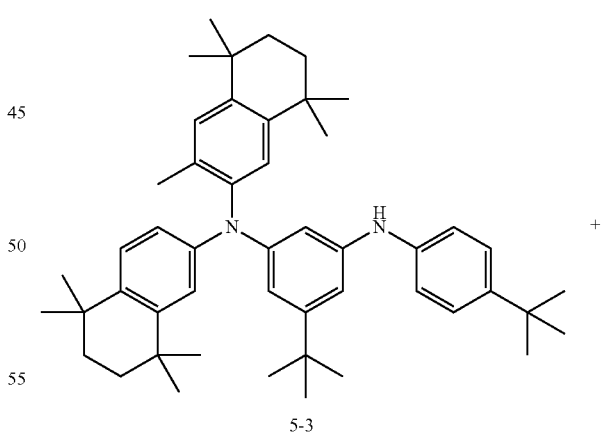

5-3

+

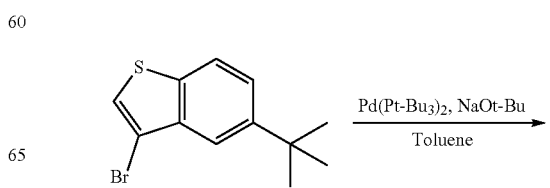

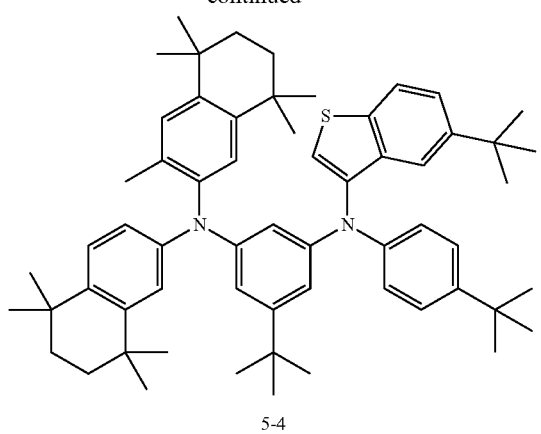

5-4

Compound 5-4 was obtained in the same manner as in Preparation of Compound 1-4 of Preparation Example 11 except that Compound 5-3 was used instead of Compound 1-3, and 3-bromo-5-(tert-butyl)benzo[b]thiophene was used instead of Compound A.

MS: [M+H]$^+$=872

Preparation Example 30: Synthesis of Compound 5

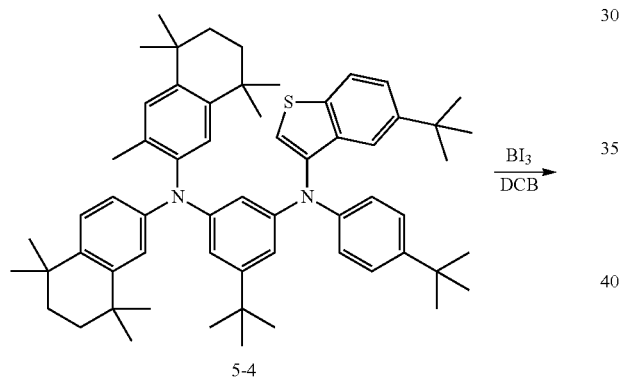

Compound 5 was obtained in the same manner as in Preparation of Compound 1 of Preparation Example 12 except that Compound 5-4 was used instead of Compound 1-4.

MS: [M+H]$^+$=880

Preparation Example 31: Synthesis of Compound 6-1

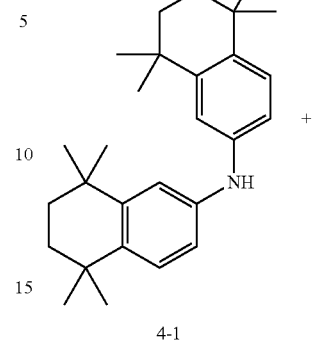

4-1

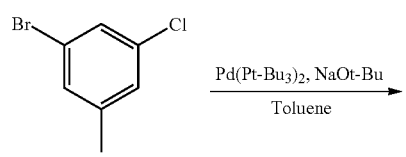

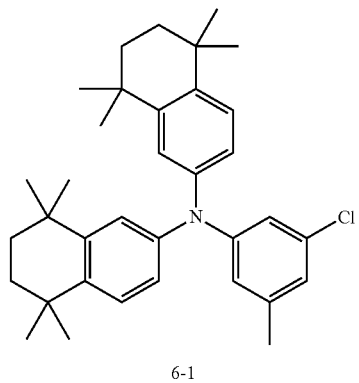

6-1

Compound 6-1 was obtained in the same manner as in Preparation of Compound 1-2 of Preparation Example 9 except that Compound 4-1 was used instead of Compound 1-1.

MS: [M+H]$^+$=515

Preparation Example 32: Synthesis of Compound 6-2

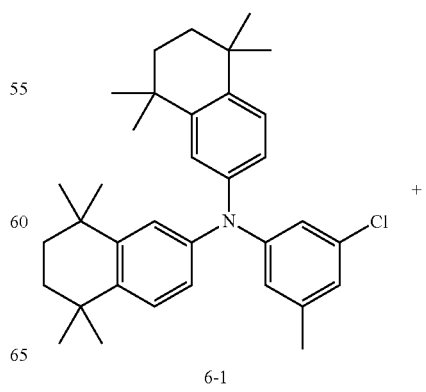

6-1

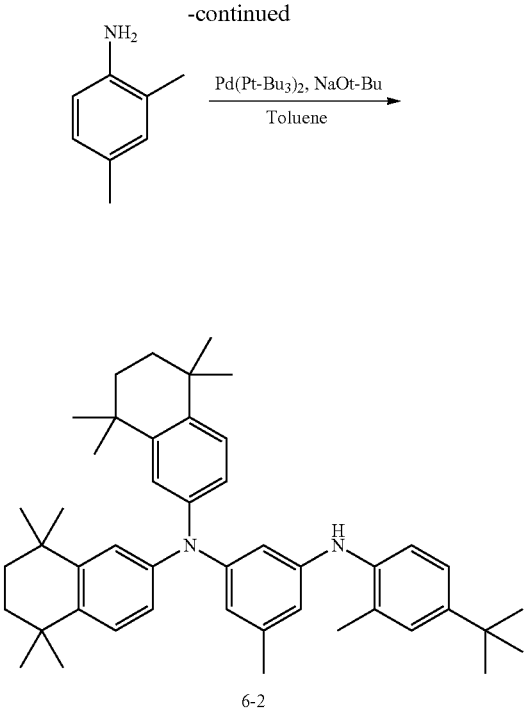

6-2

Compound 6-2 was obtained in the same manner as in Preparation of Compound 1-3 of Preparation Example 10 except that Compound 6-1 was used instead of Compound 1-2, and 2,4-dimethylaniline was used instead of 4-(tert-butyl)aniline.
MS: [M+H]⁺=642

Preparation Example 33: Synthesis of Compound 6-3

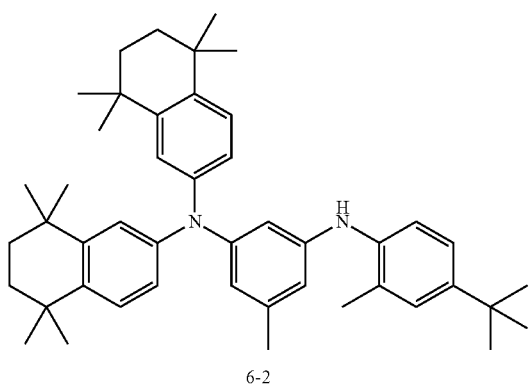

6-2

+

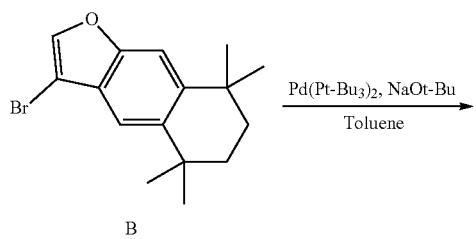

B

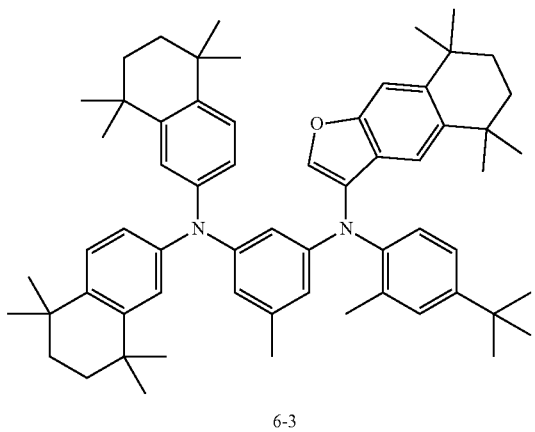

6-3

Compound 6-3 was obtained in the same manner as in Preparation of Compound 1-4 of Preparation Example 11 except that Compound 6-2 was used instead of Compound 1-3, and Compound B was used instead of Compound A.
MS: [M+H]⁺=868

Preparation Example 34: Synthesis of Compound 6

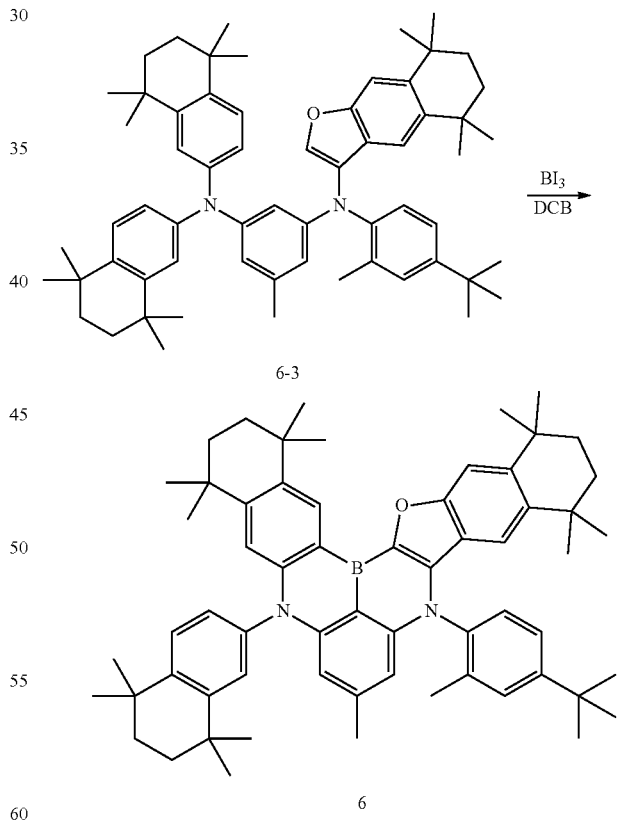

6

Compound 6 was obtained in the same manner as in Preparation of Compound 1 of Preparation Example 12 except that Compound 6-3 was used instead of Compound 1-4.
MS: [M+H]⁺=876

Preparation Example 35: Synthesis of Compound 7-1

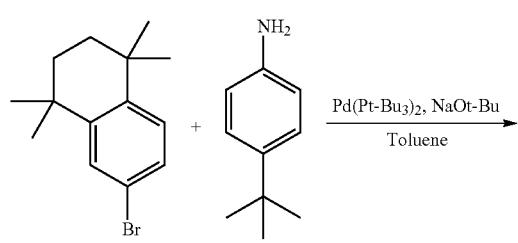

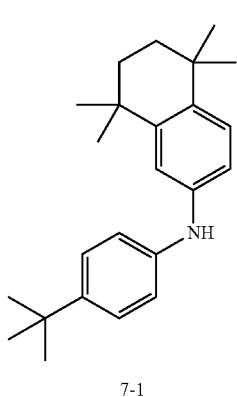

7-1

Compound 7-1 was obtained in the same manner as in Preparation of Compound 1-1 of Preparation Example 8 except that 4-(tert-butyl)aniline was used instead of 5-(tert-butyl)-[1,1'-biphenyl]-2-amine.

MS: [M+H]$^+$=336

Preparation Example 36: Synthesis of Compound 7-2

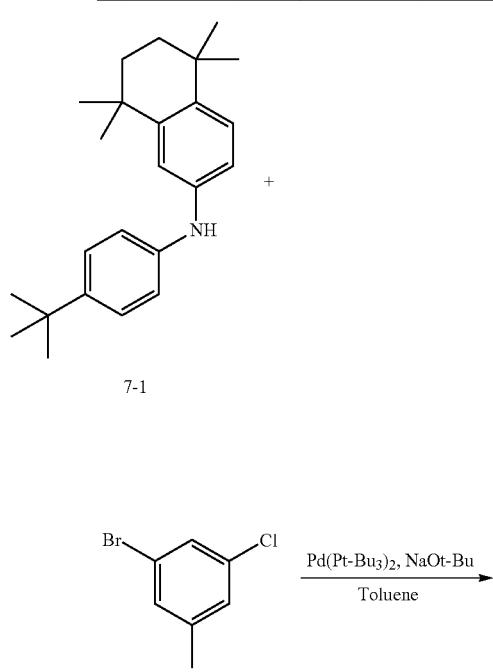

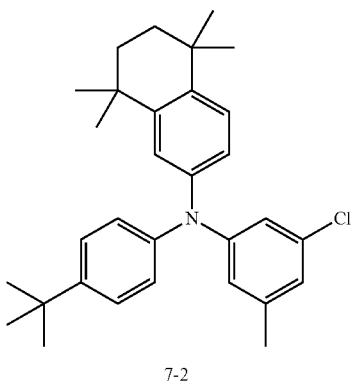

7-2

Compound 7-2 was obtained in the same manner as in Preparation of Compound 1-2 of Preparation Example 9 except that Compound 7-1 was used instead of Compound 1-1.

MS: [M+H]$^+$=461

Preparation Example 37: Synthesis of Compound 7-3

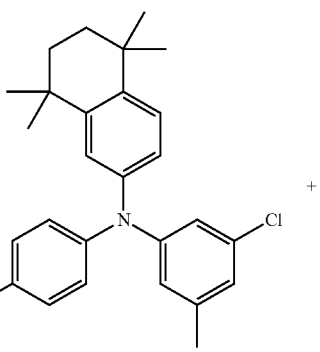

7-2

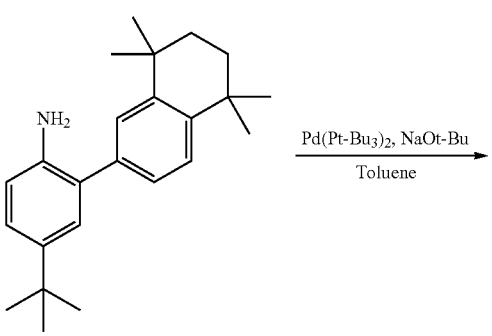

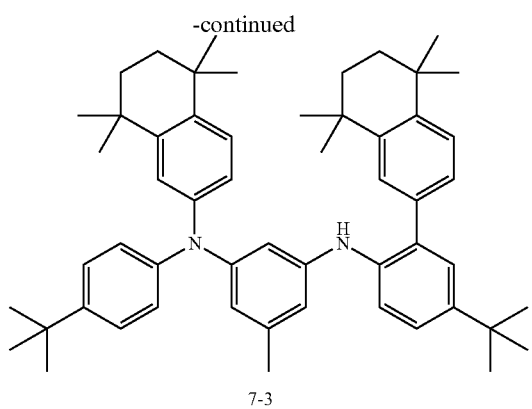

7-3

Compound 7-3 was obtained in the same manner as in Preparation of Compound 1-3 of Preparation Example 10 except that Compound 7-2 was used instead of Compound 1-2, and 4-(tert-butyl)-2-(5,5,8,8-tetramethyl-5,6,7,8-tetrahydronaphthalen-2-yl)aniline was used instead of 4-(tert-butyl)aniline.

MS: [M+H]$^+$=760

Preparation Example 38: Synthesis of Compound 7-4

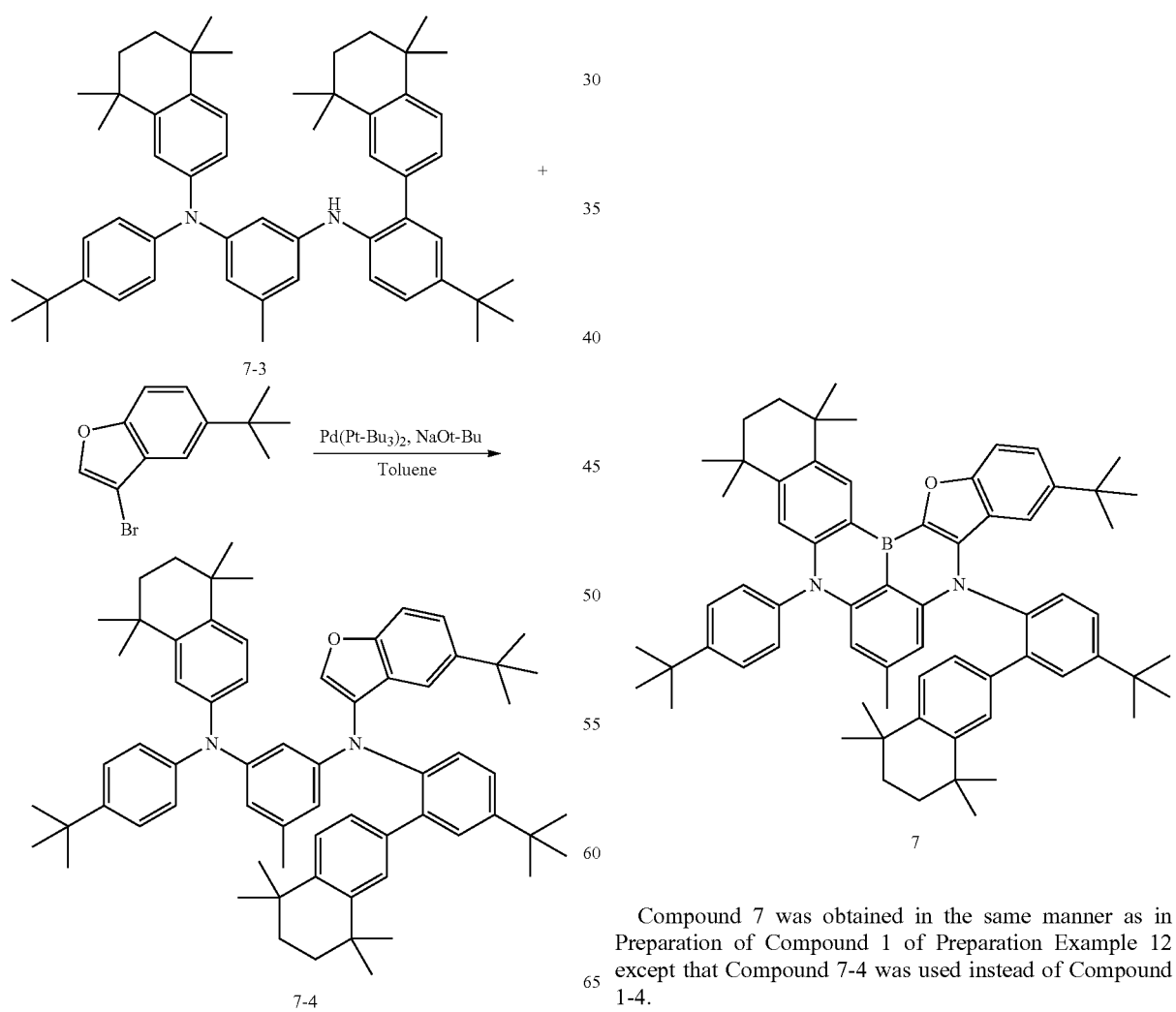

7-4

Compound 7-4 was obtained in the same manner as in Preparation of Compound 1-4 of Preparation Example 11 except that Compound 7-3 was used instead of Compound 1-3, and 3-bromo-5-(tert-butyl)benzofuran was used instead of Compound A.

MS: [M+H]$^+$=932

Preparation Example 39: Synthesis of Compound 7

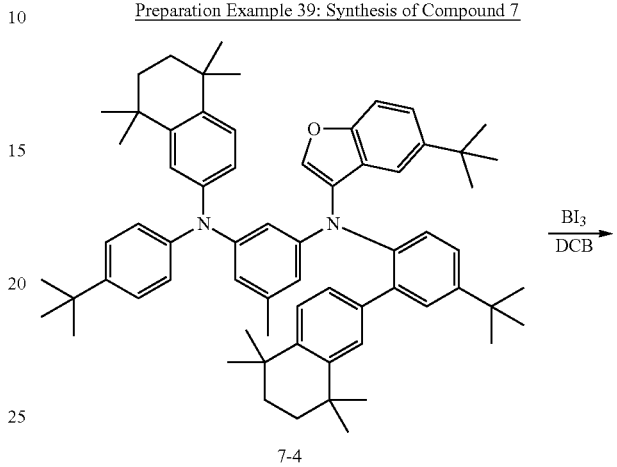

7

Compound 7 was obtained in the same manner as in Preparation of Compound 1 of Preparation Example 12 except that Compound 7-4 was used instead of Compound 1-4.

MS: [M+H]$^+$=940

Preparation Example 40: Synthesis of Compound 8-1

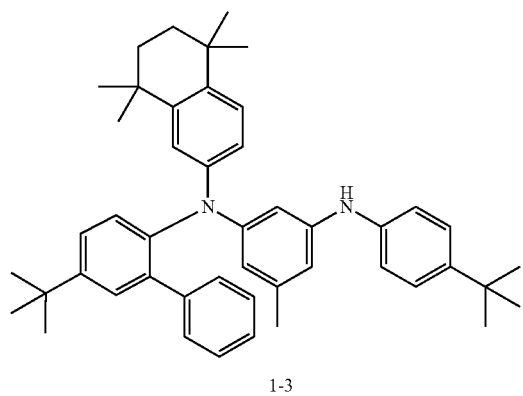

1-3

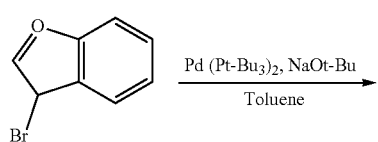

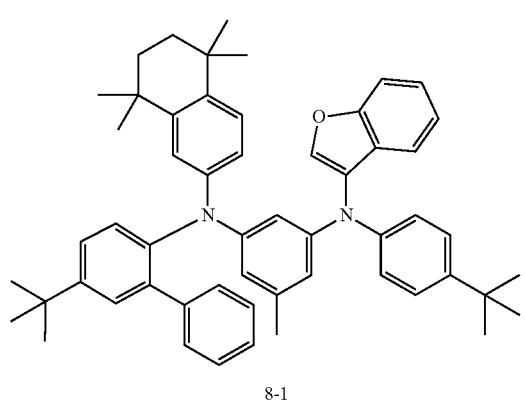

8-1

Compound 8-1 was obtained in the same manner as in Preparation of Compound 1-4 of Preparation Example 11 except that 3-bromobenzofuran was used instead of Compound A.

MS: [M+H]$^+$=766

Preparation Example 41: Synthesis of Compound 8

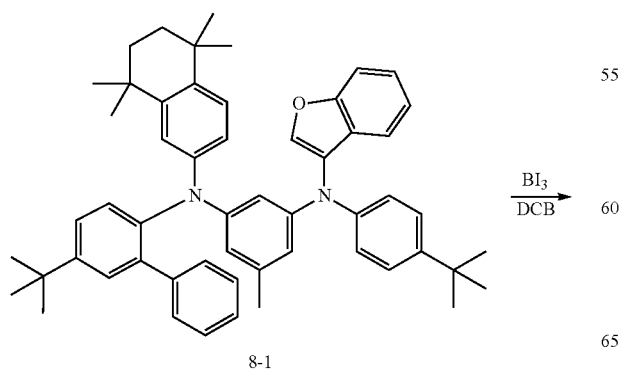

8-1

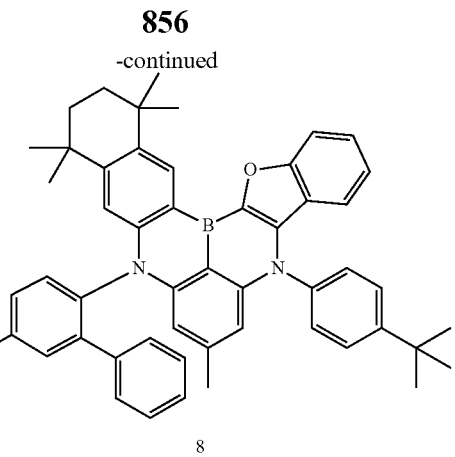

8

Compound 8 was obtained in the same manner as in Preparation of Compound 1 of Preparation Example 12 except that Compound 8-1 was used instead of Compound 1-4.

MS: [M+H]$^+$=773

Preparation Example 42: Synthesis of Compound 9-1

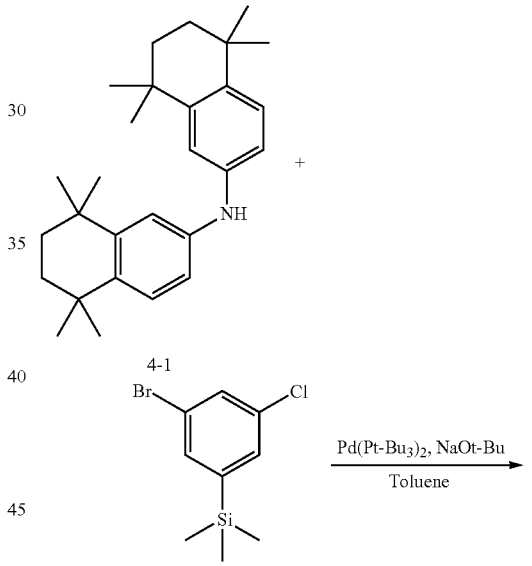

9-1

Compound 9-1 was obtained in the same manner as in Preparation of Compound 1-2 of Preparation Example 9 except that Compound 4-1 was used instead of Compound 1-1, and (3-bromo-5-chlorophenyl)trimethylsilane was used instead of 1-bromo-3-chloro-5-methylbenzene.

MS: [M+H]⁺=573

Preparation Example 43: Synthesis of Compound 9-2

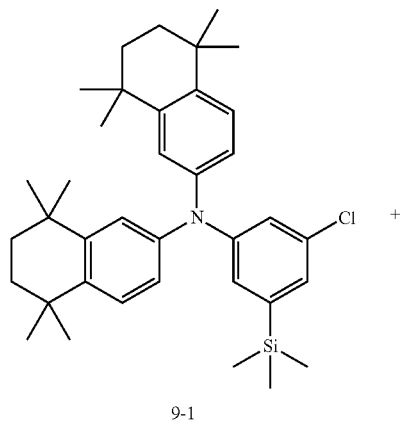

9-1

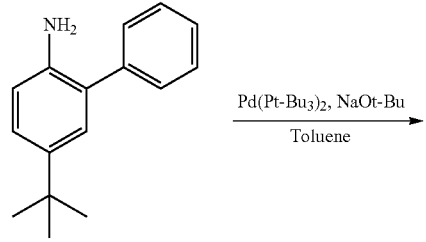

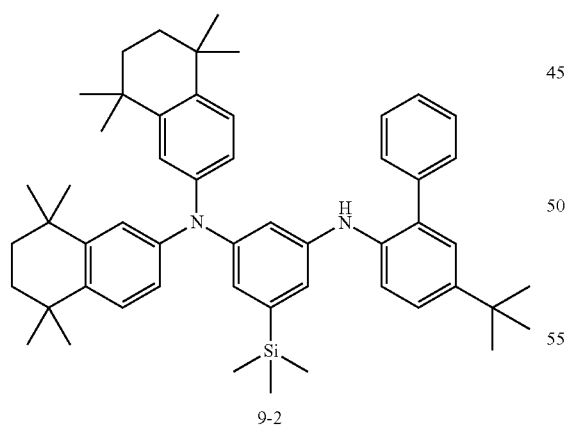

9-2

Compound 9-2 was obtained in the same manner as in Preparation of Compound 1-3 of Preparation Example 10 except that Compound 9-1 was used instead of Compound 1-2, and 5-(tert-butyl)-[1,1'-biphenyl]-2-amine was used instead of 4-(tert-butyl)aniline.

MS: [M+H]⁺=762

Preparation Example 44: Synthesis of Compound 9-3

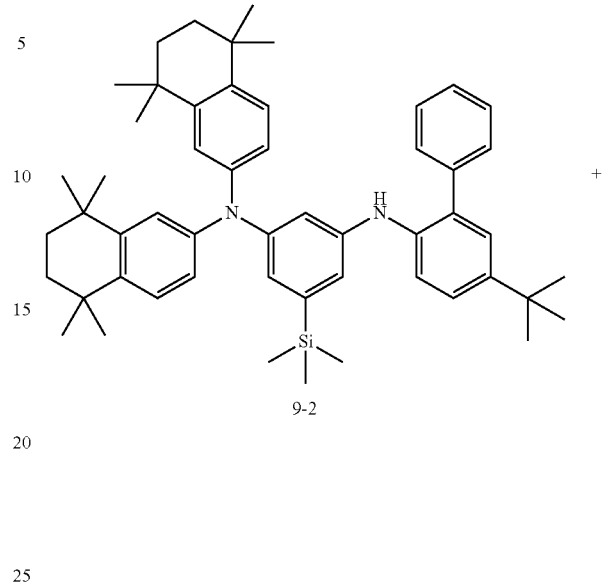

9-2


B

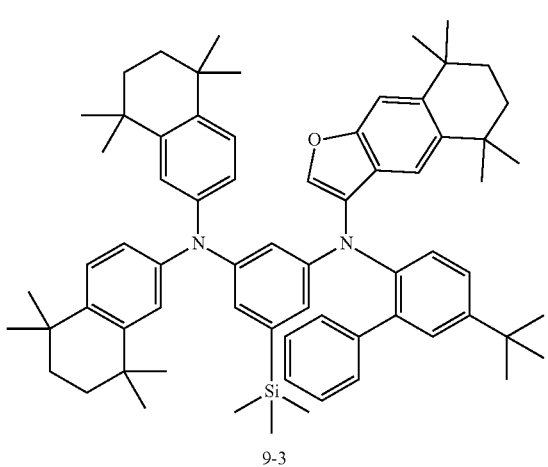

9-3

Compound 9-3 was obtained in the same manner as in Preparation of Compound 1-4 of Preparation Example 11 except that Compound 9-2 was used instead of Compound 1-3, and Compound B was used instead of Compound A.

MS: [M+H]⁺=988

Preparation Example 45: Synthesis of Compound 9

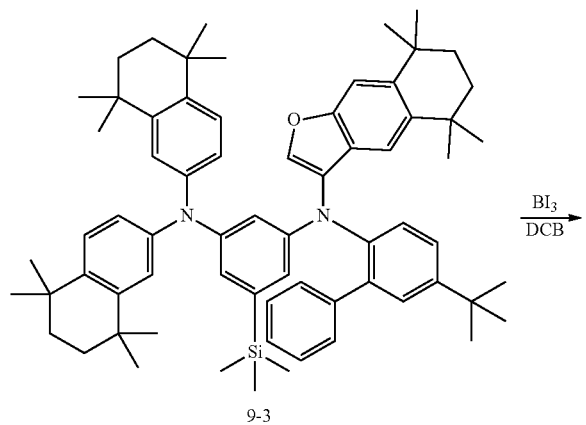

Compound 9 was obtained in the same manner as in Preparation of Compound 1 of Preparation Example 12 except that Compound 9-3 was used instead of Compound 1-4.

MS: [M+H]$^+$=996

Preparation Example 46: Synthesis of Compound 10-1

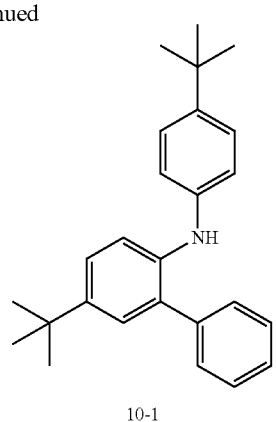

Compound 10-1 was obtained in the same manner as in Preparation of Compound 1-1 of Preparation Example 8 except that 1-bromo-4-(tert-butyl)benzene was used instead of 6-bromo-1,1,4,4-tetramethyl-1,2,3,4-tetrahydronaphthalene.

MS: [M+H]$^+$=358

Preparation Example 47: Synthesis of Compound 10-2

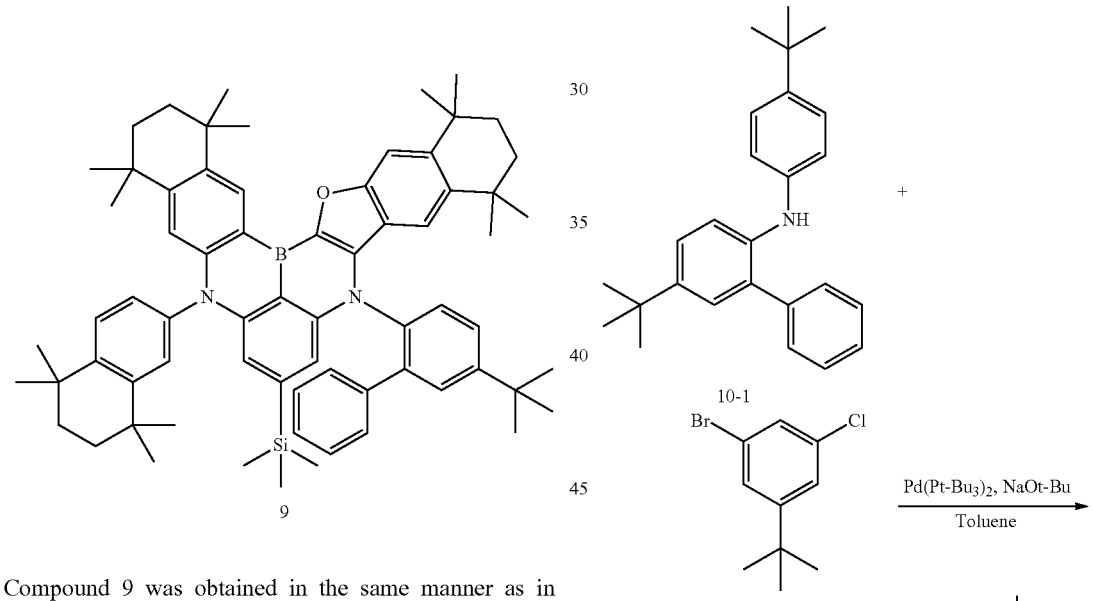

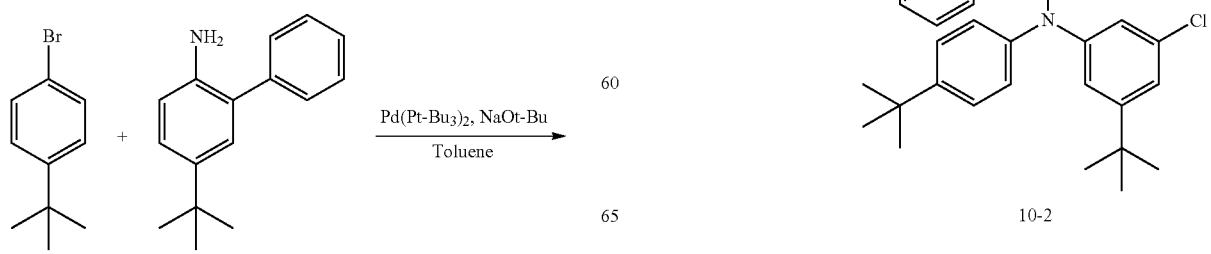

Compound 10-2 was obtained in the same manner as in Preparation of Compound 1-2 of Preparation Example 9 except that Compound 10-1 was used instead of Compound 1-1, and 1-bromo-3-(tert-butyl)-5-chlorobenzene was used instead of 1-bromo-3-chloro-5-methylbenzene.

MS: [M+H]⁺=525

Preparation Example 48: Synthesis of Compound 10-3

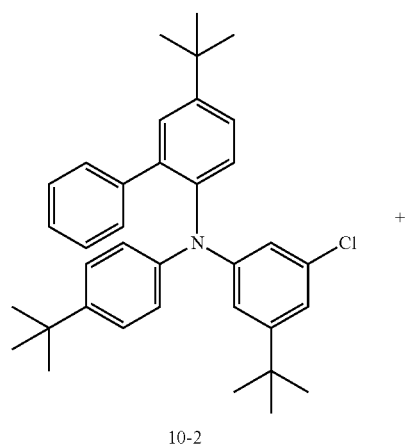

10-2

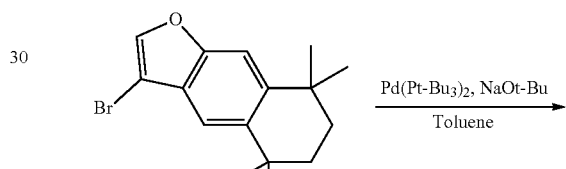

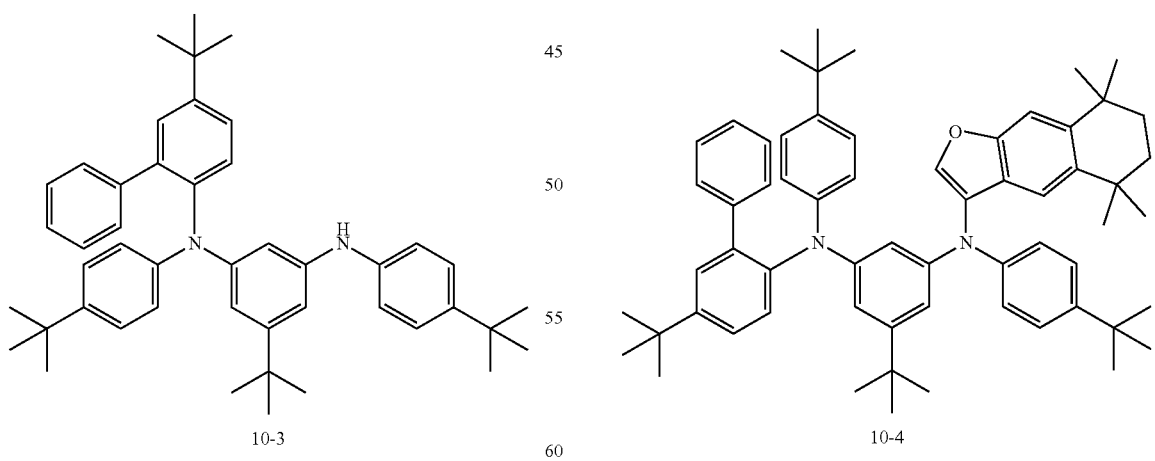

10-3

Compound 10-3 was obtained in the same manner as in Preparation of Compound 1-3 of Preparation Example 10 except that Compound 10-2 was used instead of Compound 1-2.

MS: [M+H]⁺=637

Preparation Example 49: Synthesis of Compound 10-4

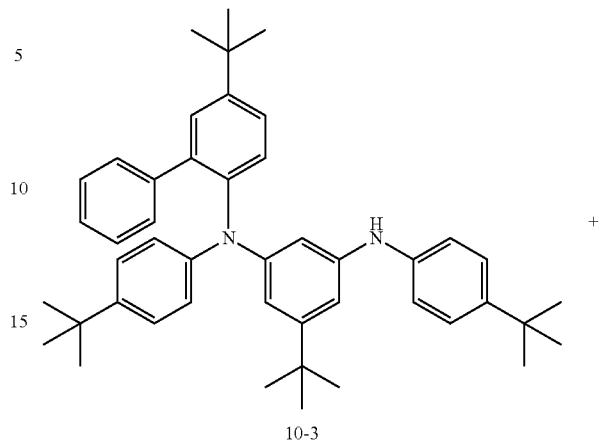

10-3

10-4

Compound 10-4 was obtained in the same manner as in Preparation of Compound 1-4 of Preparation Example 11 except that Compound 10-3 was used instead of Compound 1-3, and Compound B was used instead of Compound A.

MS: [M+H]⁺=864

Preparation Example 50: Synthesis of Compound 10

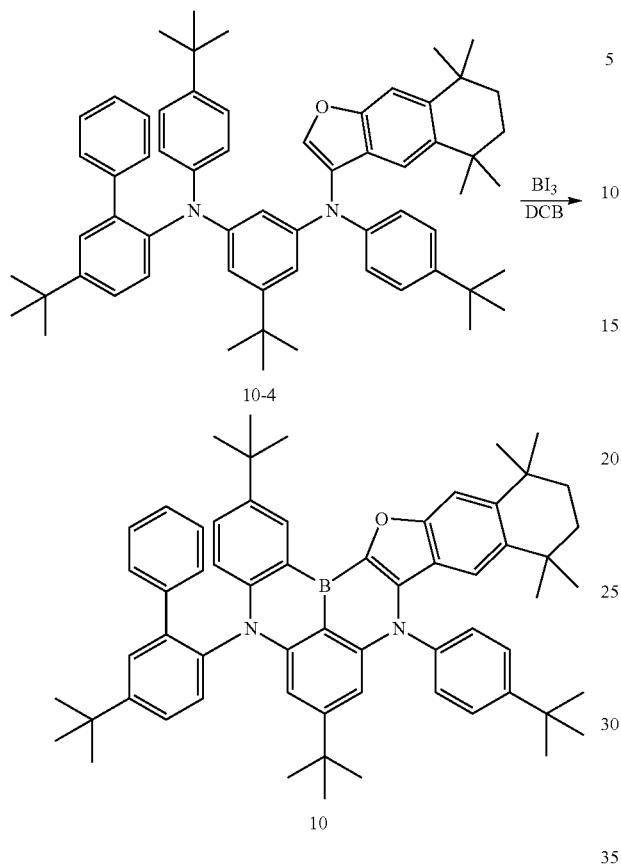

Compound 10 was obtained in the same manner as in Preparation of Compound 1 of Preparation Example 12 except that Compound 10-4 was used instead of Compound 1-4.

MS: $[M+H]^+=872$

Preparation Example 51: Synthesis of Compound C-1

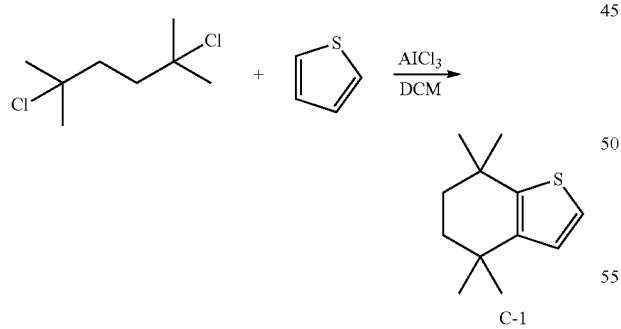

2,5-Dichloro-2,5-dimethylhexane (50 g, 273 mmol) and thiophene (22.97 g, 273 mmol) were dissolved in dichloromethane (DCM) (390 ml). AlCl$_3$ (36.41 g, 273 mmol) was slowly added thereto at 0° C., and the result was stirred at room temperature.

When the reaction was finished, the result was cooled to room temperature, and the reaction material was transferred to a separatory funnel and then extracted. The result was dried with MgSO$_4$, filtered, concentrated, and purified using column chromatography to obtain Compound C-1 (24.41 g, yield 46%).

MS: $[M+H]^+=194.34$

Preparation Example 52: Synthesis of Compound C

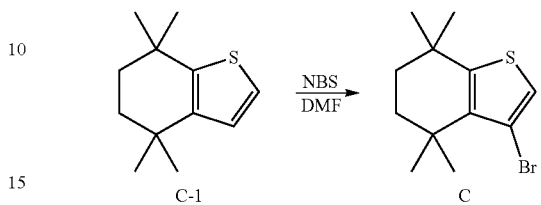

Compound C was obtained in the same manner as in Preparation of Compound A of Preparation Example 3 except that Compound C-1 was used instead of Compound A-2.

MS: $[M+H]^+=274$

Preparation Example 53: Synthesis of Compound D-1

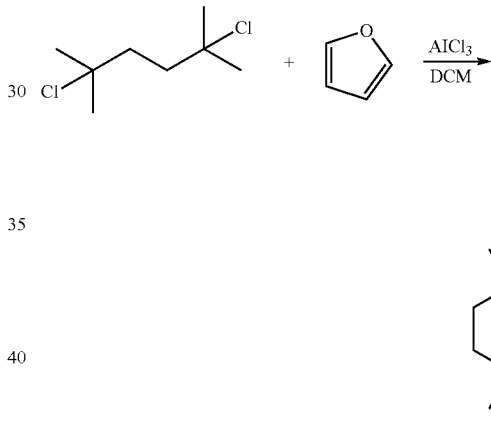

Compound D-1 was obtained in the same manner as in Preparation of Compound C-1 of Preparation Example 51 except that furan was used instead of thiophene.

MS: $[M+H]^+=179$

Preparation Example 54: Synthesis of Compound D-2

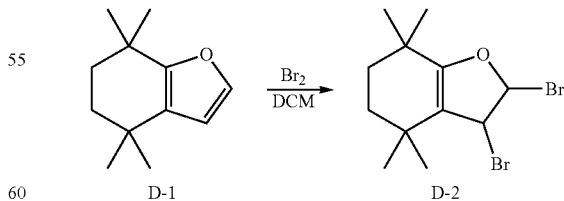

Compound D-2 was obtained in the same manner as in Preparation of Compound B-3 of Preparation Example 6 except that Compound D-1 was used instead of Compound B-2.

MS: $[M+H]^+=339$

Preparation Example 55: Synthesis of Compound D

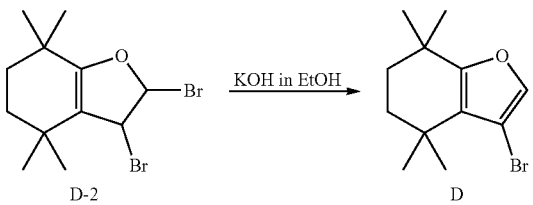

Compound D was obtained in the same manner as in Preparation of Compound B of Preparation Example 7 except that Compound D-2 was used instead of Compound B-3.

MS: [M+H]$^+$=258

Preparation Example 56: Synthesis of Compound 11-1

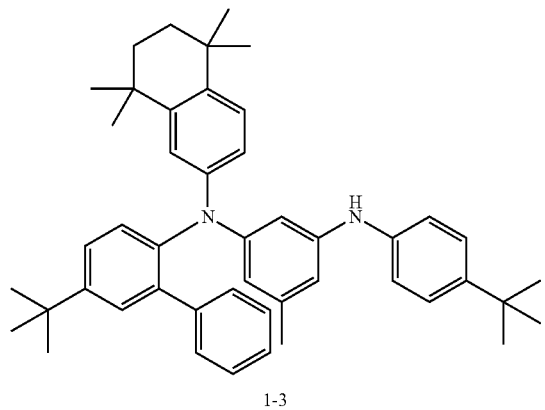

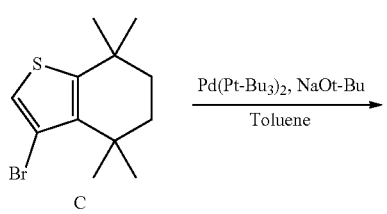

Compound 11-1 was obtained in the same manner as in Preparation of Compound 1-4 of Preparation Example 11 except that Compound C was used instead of Compound A.

MS: [M+H]$^+$=842

Preparation Example 57: Synthesis of Compound 11

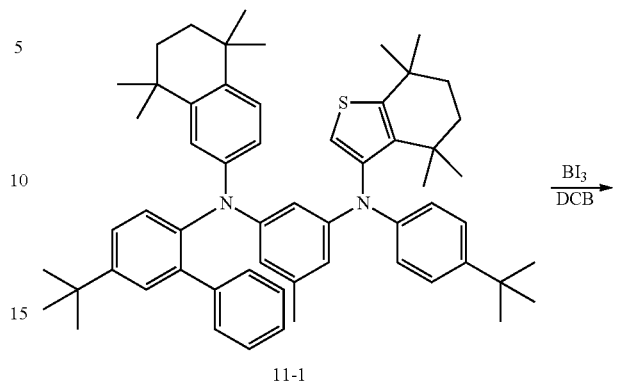

Compound 11 was obtained in the same manner as in Preparation of Compound 1 of Preparation Example 12 except that Compound 11-1 was used instead of Compound 1-4.

MS: [M+H]$^+$=850

Preparation Example 58: Synthesis of Compound 12-1

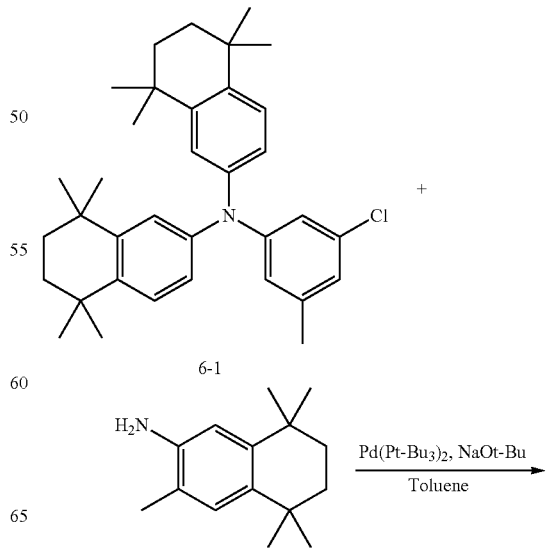

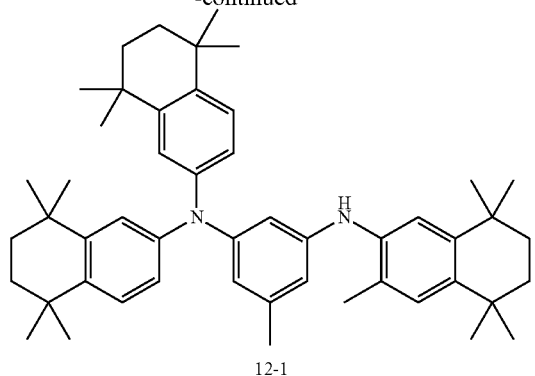

12-1

Compound 12-1 was obtained in the same manner as in Preparation of Compound 1-3 of Preparation Example 10 except that Compound 6-1 was used instead of Compound 1-2, and 3,5,5,8,8-pentamethyl-5,6,7,8-tetrahydronaphthalen-2-amine was used instead of 4-(tert-butyl)aniline.

MS: [M+H]$^+$=696

Preparation Example 59: Synthesis of Compound 12-2

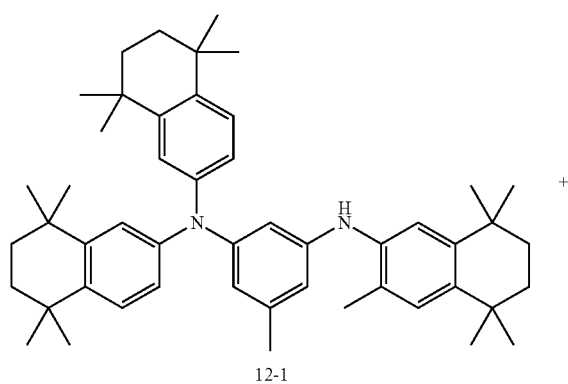

12-1

12-2

Compound 12-2 was obtained in the same manner as in Preparation of Compound 1-4 of Preparation Example 11 except that Compound 12-1 was used instead of Compound 1-3, and Compound C was used instead of Compound A.

MS: [M+H]$^+$=888

Preparation Example 60: Synthesis of Compound 12

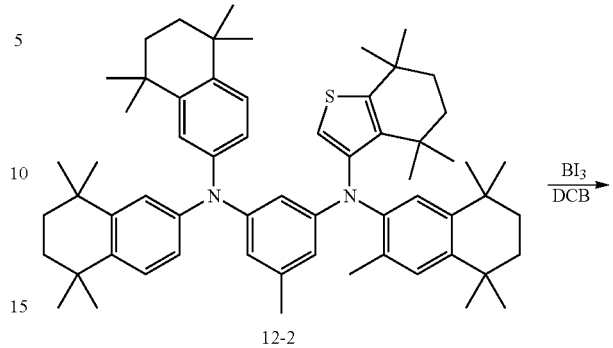

12-2

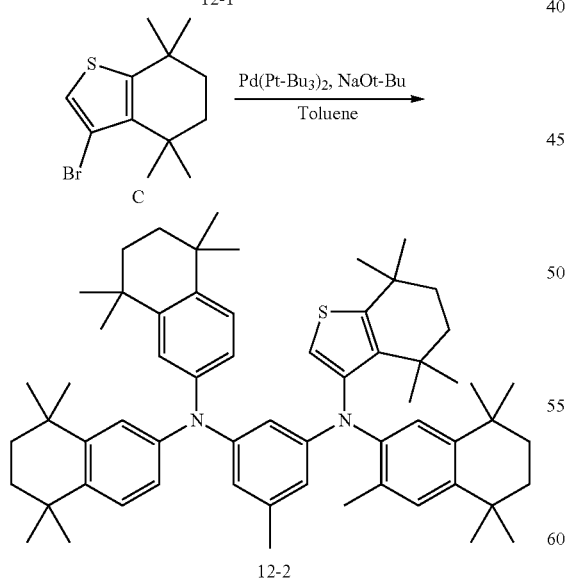

12

Compound 12 was obtained in the same manner as in Preparation of Compound 1 of Preparation Example 12 except that Compound 12-2 was used instead of Compound 1-4.

MS: [M+H]$^+$=896

Preparation Example 61: Synthesis of Compound 13-1

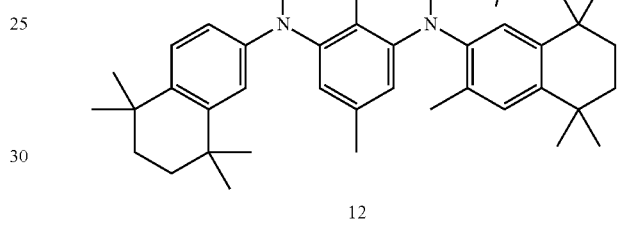

1-3

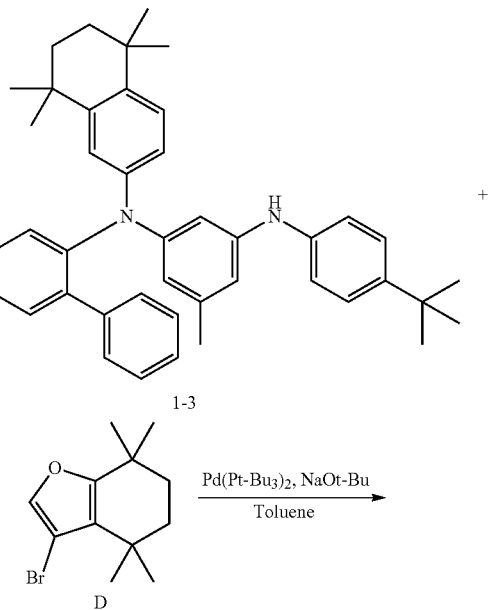

D

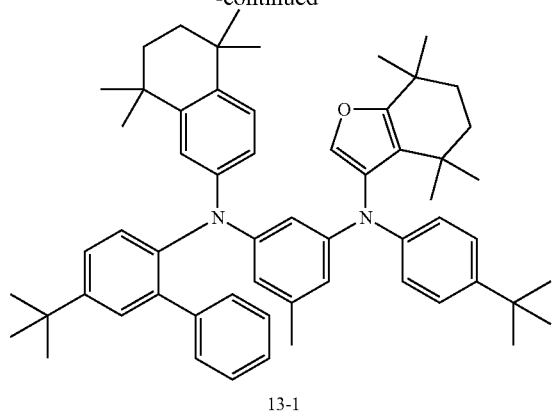

13-1

Compound 13-1 was obtained in the same manner as in Preparation of Compound 1-4 of Preparation Example 11 except that Compound D was used instead of Compound A.

MS: [M+H]$^+$=826

Preparation Example 62: Synthesis of Compound 13

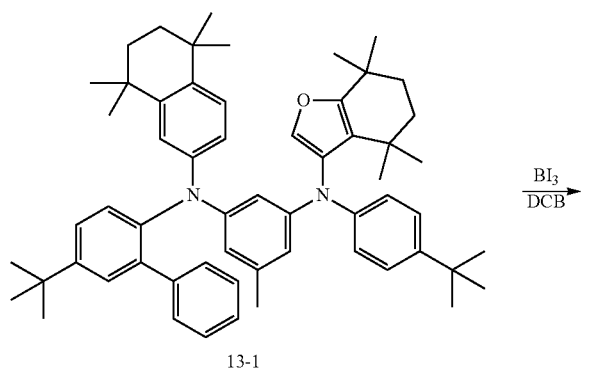

13-1

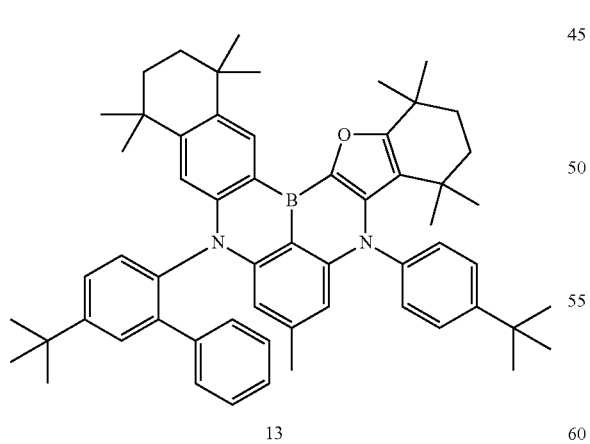

13

Compound 13 was obtained in the same manner as in Preparation of Compound 1 of Preparation Example 12 except that Compound 13-1 was used instead of Compound 1-4.

MS: [M+H]$^+$=834

Preparation Example 63: Synthesis of Compound 14-1

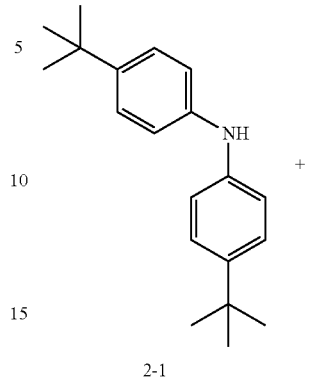

2-1

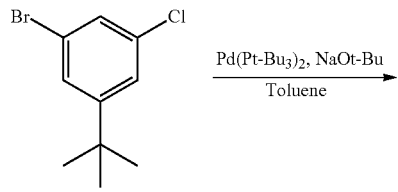

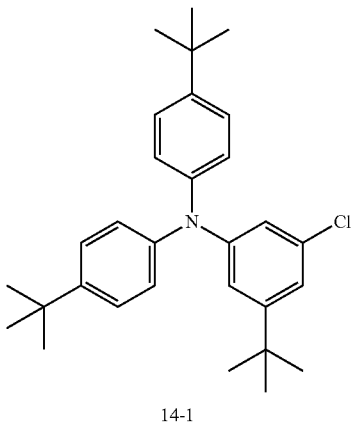

14-1

Compound 14-1 was obtained in the same manner as in Preparation of Compound 1-2 of Preparation Example 9 except that Compound 2-1 was used instead of Compound 1-1, and 1-bromo-3-(tert-butyl)-5-chlorobenzene was used instead of 1-bromo-3-chloro-5-methylbenzene.

MS: [M+H]$^+$=449

Preparation Example 64: Synthesis of Compound 14-2

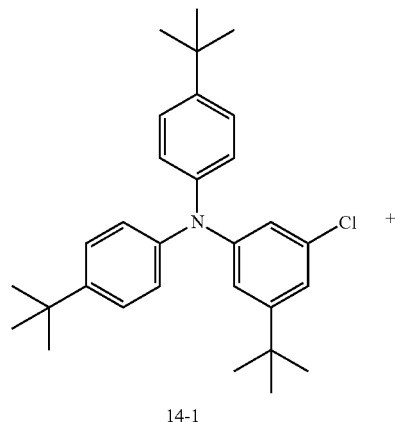

14-1

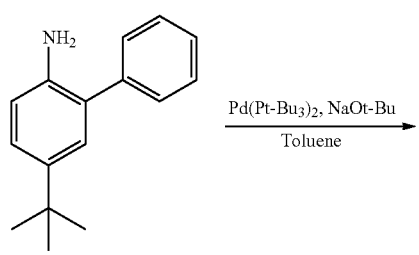

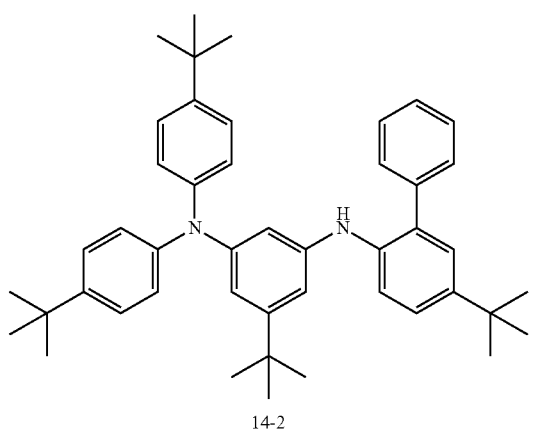

14-2

Compound 14-2 was obtained in the same manner as in Preparation of Compound 1-3 of Preparation Example 10 except that Compound 14-1 was used instead of Compound 1-2, and 5-(tert-butyl)-[1,1'-biphenyl]-2-amine was used instead of 4-(tert-butyl)aniline.

MS: [M+H]$^+$=637

Preparation Example 65: Synthesis of Compound 14-3

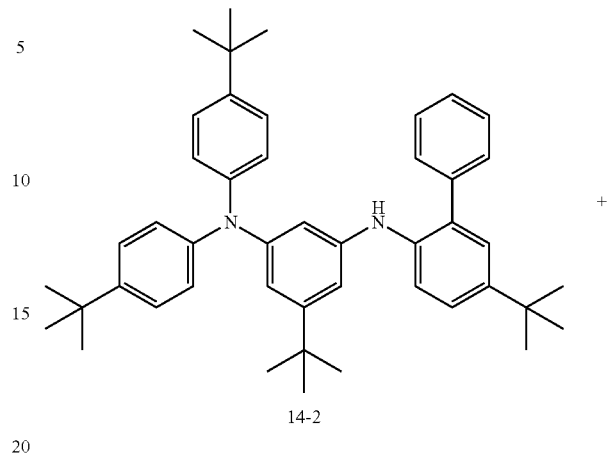

14-2

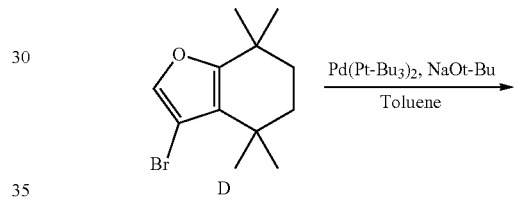

D

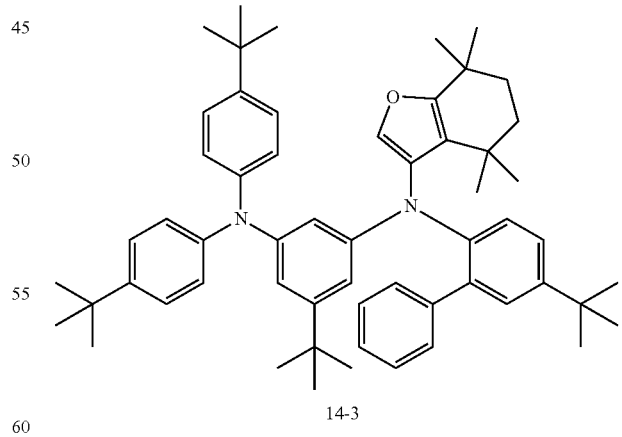

14-3

Compound 14-3 was obtained in the same manner as in Preparation of Compound 1-4 of Preparation Example 11 except that Compound 14-2 was used instead of Compound 1-3, and Compound D was used instead of Compound A.

MS: [M+H]$^+$=814

Preparation Example 66: Synthesis of Compound 14

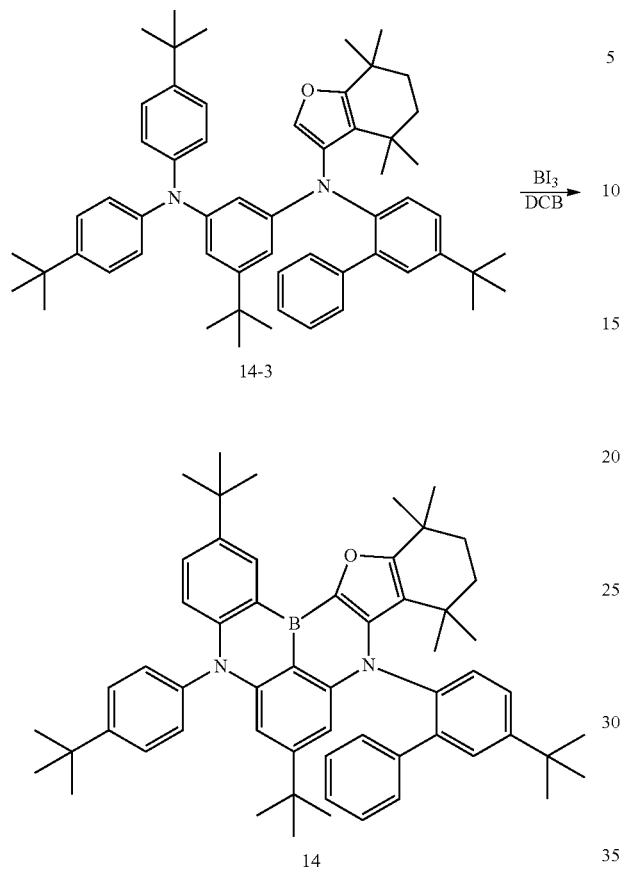

Compound 14 was obtained in the same manner as in Preparation of Compound 1 of Preparation Example 12 except that Compound 14-3 was used instead of Compound 1-4.

MS: [M+H]⁺=822

Preparation Example 67: Synthesis of Compound 15-1

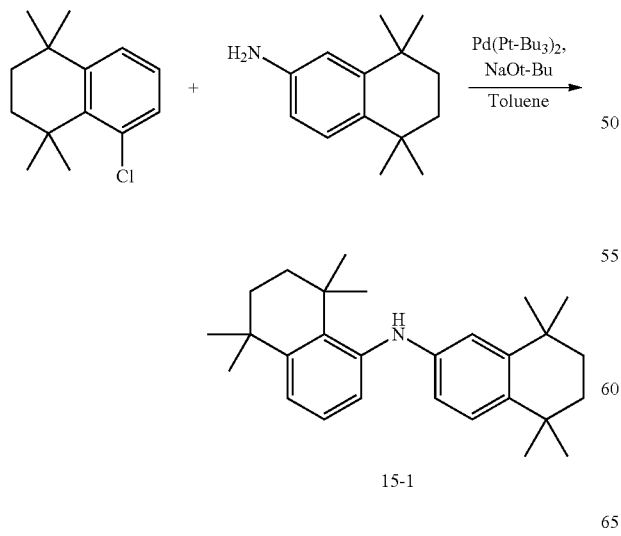

Compound 15-1 was obtained in the same manner as in Preparation of Compound 1-1 of Preparation Example 8 except that 5-chloro-1,1,4,4-tetramethyl-1,2,3,4-tetrahydronaphthalene was used instead of 6-bromo-1,1,4,4-tetramethyl-1,2,3,4-tetrahydronaphthalene, and 5,5,8,8-tetramethyl-5,6,7,8-tetrahydronaphthalen-2-amine was used instead of 5-(tert-butyl)-[1,1'-biphenyl]-2-amine.

MS: [M+H]⁺=390

Preparation Example 68: Synthesis of Compound 15-2

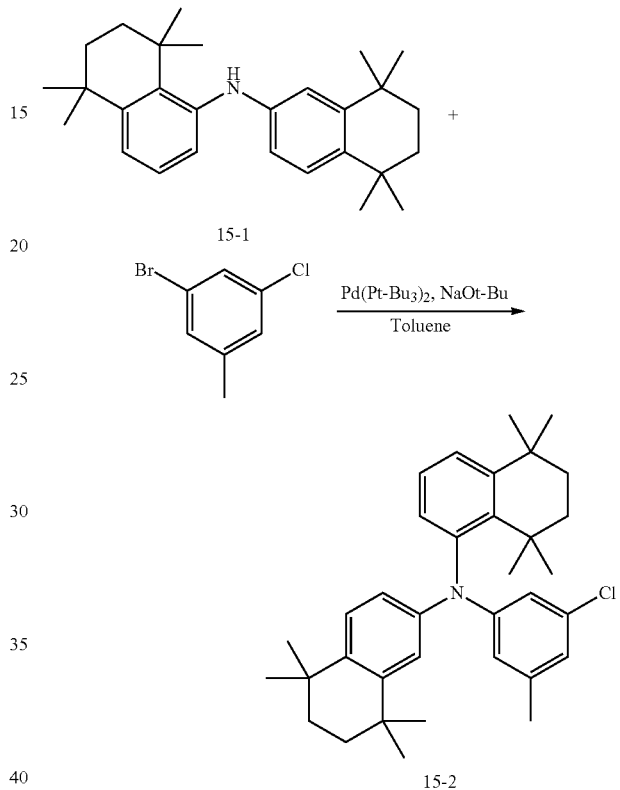

Compound 15-2 was obtained in the same manner as in Preparation of Compound 1-2 of Preparation Example 9 except that Compound 15-1 was used instead of Compound 1-1.

MS: [M+H]⁺=515

Preparation Example 69: Synthesis of Compound 15-3

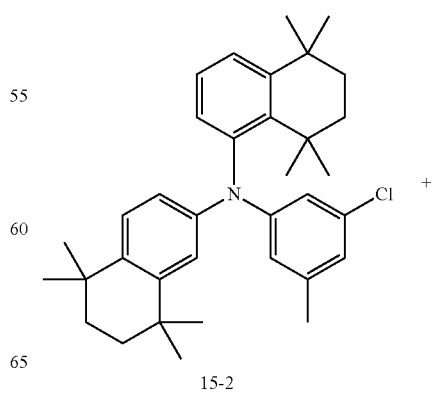

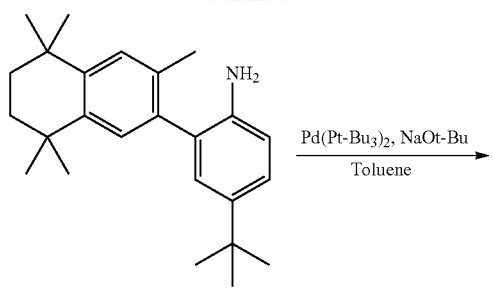
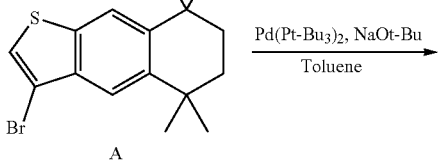

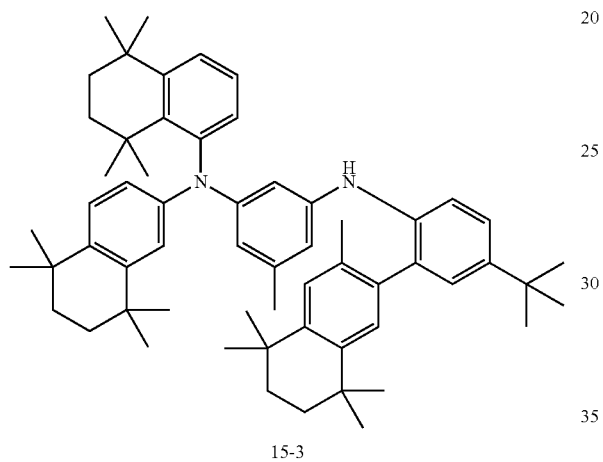

15-3

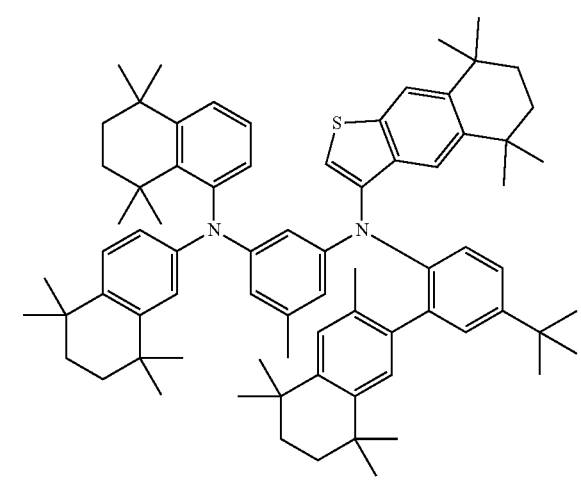

15-4

Compound 15-3 was obtained in the same manner as in Preparation of Compound 1-3 of Preparation Example 10 except that Compound 15-2 was used instead of Compound 1-2, and 4-(tert-butyl)-2-(3,5,5,8,8-pentamethyl-5,6,7,8-tetrahydronaphthalen-2-yl)aniline was used instead of 4-(tert-butyl)aniline.

MS: [M+H]$^+$=828

Compound 15-4 was obtained in the same manner as in Preparation of Compound 1-4 of Preparation Example 11 except that Compound 15-3 was used instead of Compound 1-3.

MS: [M+H]$^+$=1070

Preparation Example 70: Synthesis of Compound 15-4

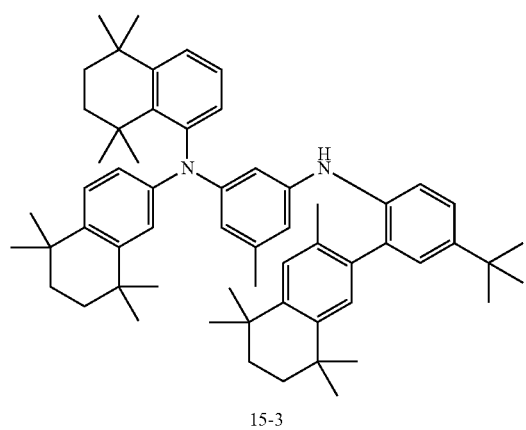

15-3

Preparation Example 71: Synthesis of Compound 15

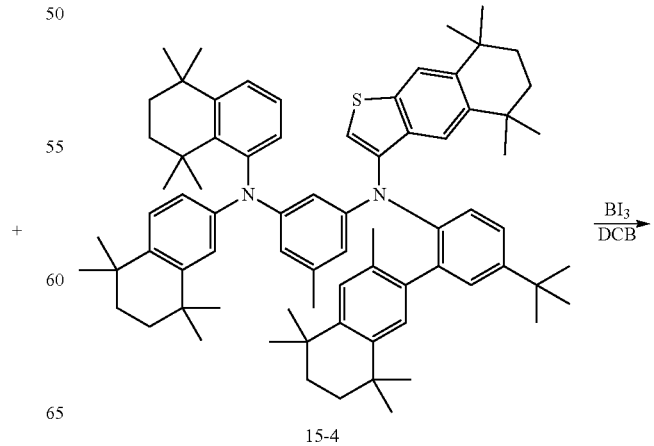

15-4

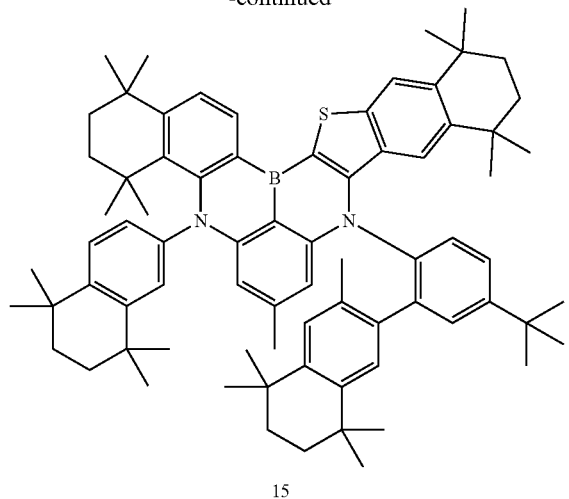

Compound 15 was obtained in the same manner as in Preparation of Compound 1 of Preparation Example 12 except that Compound 15-4 was used instead of Compound 1-4.

MS: [M+H]$^+$=1078

Preparation Example 72: Synthesis of Compound 16-1

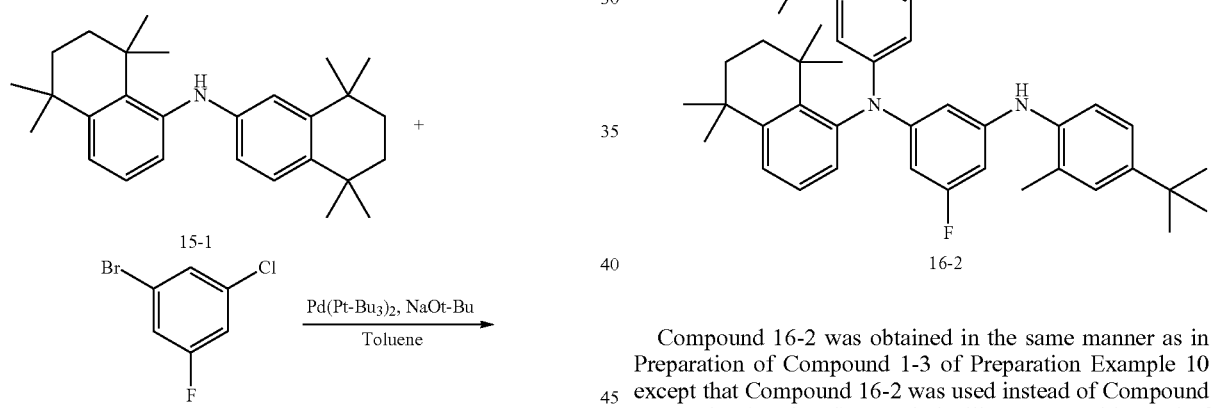

Compound 16-1 was obtained in the same manner as in Preparation of Compound 1-2 of Preparation Example 9 except that Compound 15-1 was used instead of Compound 1-1, and 1-bromo-3-chloro-5-fluorobenzene was used instead of 1-bromo-3-chloro-5-methylbenzene.

MS: [M+H]$^+$=519

Preparation Example 73: Synthesis of Compound 16-2

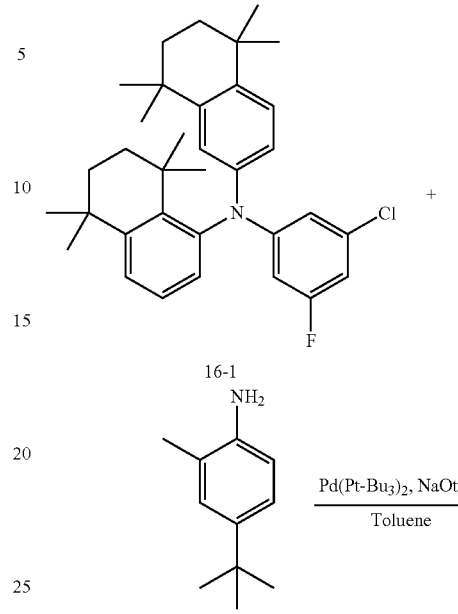

Compound 16-2 was obtained in the same manner as in Preparation of Compound 1-3 of Preparation Example 10 except that Compound 16-2 was used instead of Compound 1-2, and 4-(tert-butyl)-2-methylaniline was used instead of 4-(tert-butyl)aniline.

MS: [M+H]$^+$=645

Preparation Example 74: Synthesis of Compound 16-3

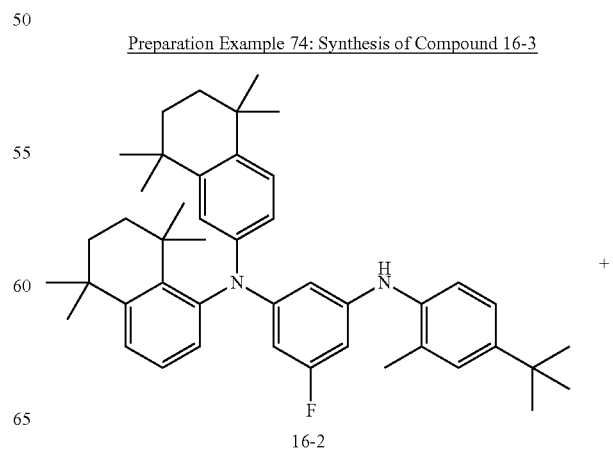

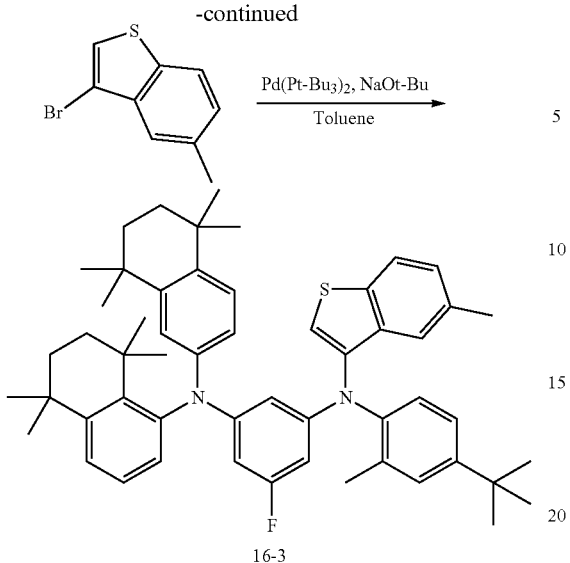

16-3

Compound 16-3 was obtained in the same manner as in Preparation of Compound 1-4 of Preparation Example 11 except that Compound 16-2 was used instead of Compound 1-3, and 3-bromo-5-methylbenzo[b]thiophene was used instead of Compound A.

MS: $[M+H]^+=792$

Preparation Example 75: Synthesis of Compound 16

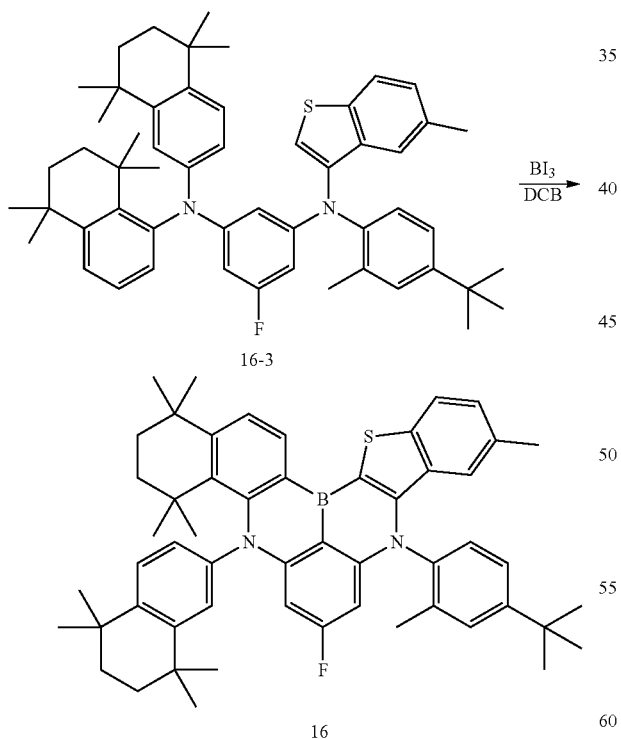

Compound 16 was obtained in the same manner as in Preparation of Compound 1 of Preparation Example 12 except that Compound 16-3 was used instead of Compound 1-4.

MS: $[M+H]^+=799$

Preparation Example 76: Synthesis of Compound 17-1

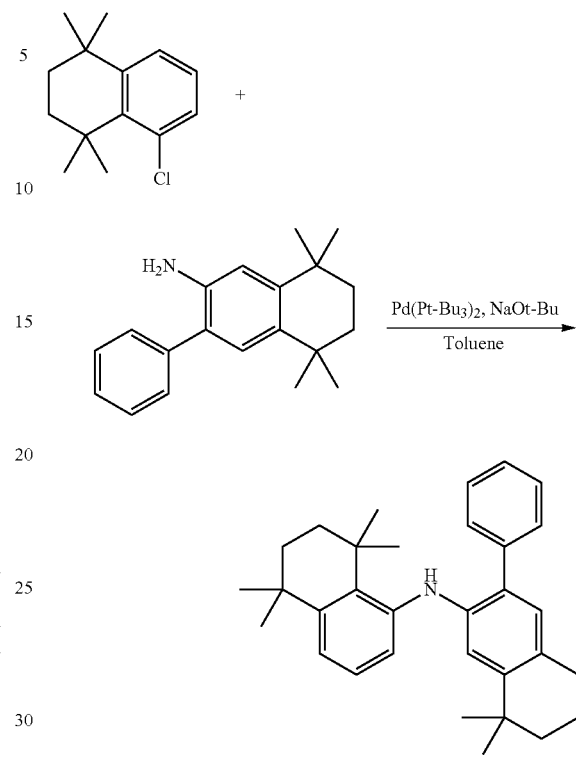

17-1

Compound 17-1 was obtained in the same manner as in Preparation of Compound 1-1 of Preparation Example 8 except that 5-chloro-1,1,4,4-tetramethyl-1,2,3,4-tetrahydronaphthalene was used instead of 6-bromo-1,1,4,4-tetramethyl-1,2,3,4-tetrahydronaphthalene, and 5,5,8,8-tetramethyl-3-phenyl-5,6,7,8-tetrahydronaphthalen-2-amine was used instead of 5-(tert-butyl)-[1,1'-biphenyl]-2-amine.

MS: $[M+H]^+=466$

Preparation Example 77: Synthesis of Compound 17-2

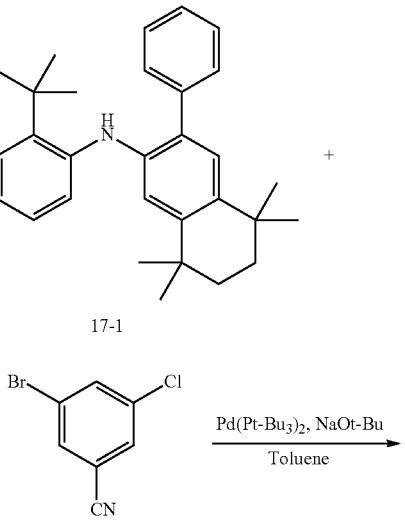

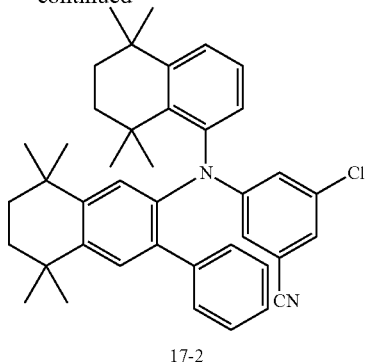

17-2

Compound 17-2 was obtained in the same manner as in Preparation of Compound 1-2 of Preparation Example 9 except that Compound 17-1 was used instead of Compound 1-1, and 3-bromo-5-chlorobenzonitrile was used instead of 1-bromo-3-chloro-5-methylbenzene.

MS: [M+H]$^+$=602

Preparation Example 78: Synthesis of Compound 17-3

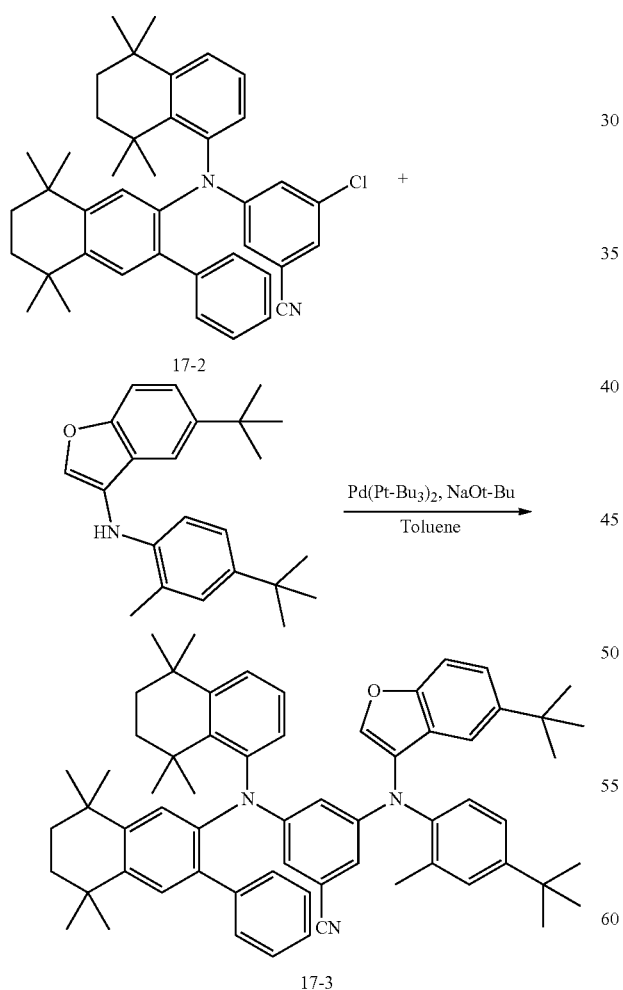

Compound 17-3 was obtained in the same manner as in Preparation of Compound 1-3 of Preparation Example 10 except that Compound 17-2 was used instead of Compound 1-2, and 5-(tert-butyl)-N-(4-(tert-butyl)-2-methylphenyl)benzofuran-3-amine was used instead of 4-(tert-butyl)aniline.

MS: [M+H]$^+$=901

Preparation Example 79: Synthesis of Compound 17

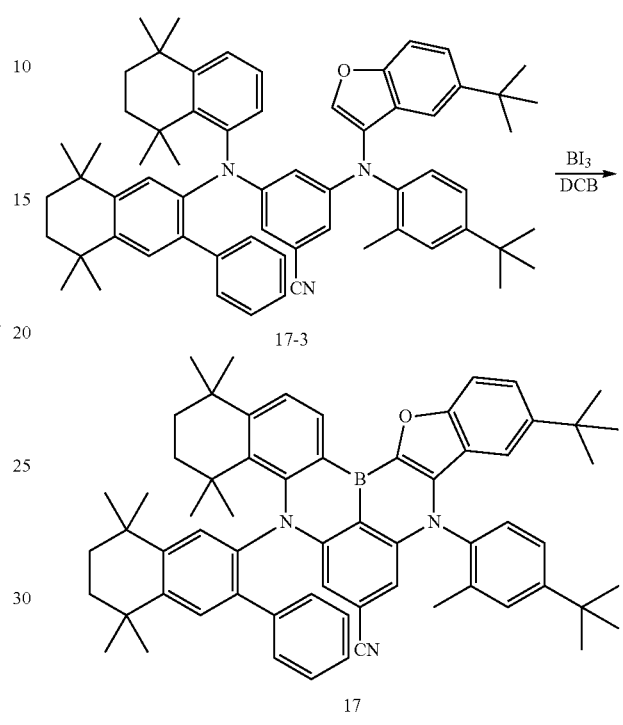

Compound 17 was obtained in the same manner as in Preparation of Compound 1 of Preparation Example 12 except that Compound 17-3 was used instead of Compound 1-4.

MS: [M+H]$^+$=909

Preparation Example 80: Synthesis of Compound E

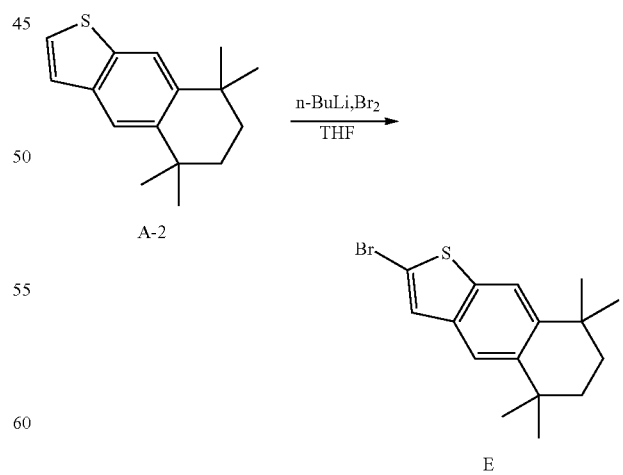

Compound A-2 (32.5 g, 133.0 mmol) was dissolved in tetrahydrofuran (THF) (660 ml). After that, n-BuLi in hexane 2.5 M (63.83 ml, 159.6 mmol) was slowly added dropwise thereto at −78° C. After 2 hours, Br$_2$ (25.5 g, 159.6 mmol) was slowly added dropwise thereto, and the temperature was raised to room temperature. When the reaction was finished, the reaction material was transferred to a separatory funnel and then extracted. The result was dried with MgSO$_4$, filtered, concentrated, and purified using column chromatography to obtain Compound E (24.5 g, yield 57%).

MS: [M+H]$^+$=324

Preparation Example 80-1: Synthesis of Compound F

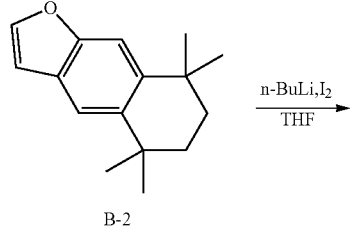

Compound F was obtained in the same manner as in Preparation of Compound E of Preparation Example 80 except that Compound B-2 was used instead of Compound A-2, and I2 was used instead of Br$_2$.

MS: [M+H]$^+$=308

Preparation Example 81: Synthesis of Compound 18-1

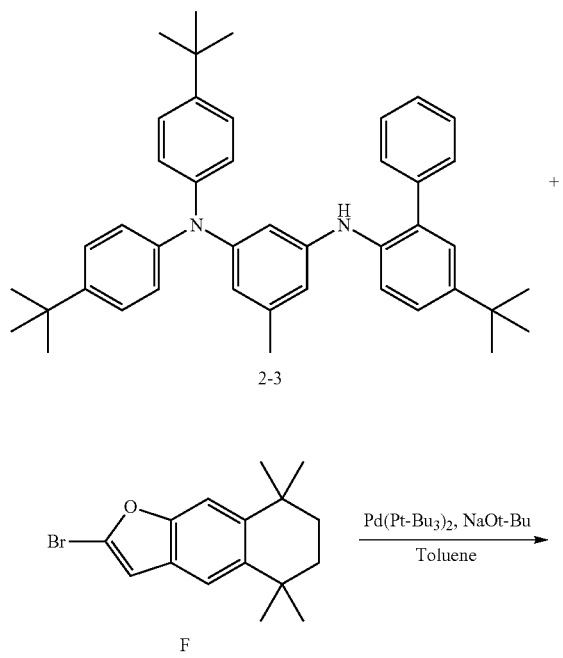

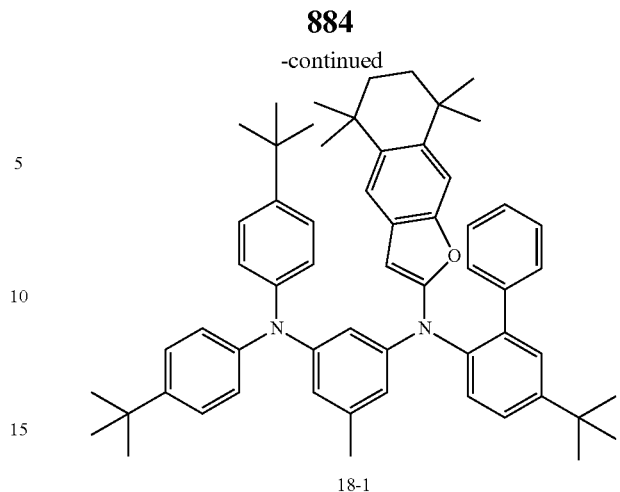

Compound 18-1 was obtained in the same manner as in Preparation of Compound 1-4 of Preparation Example 11 except that Compound 2-3 was used instead of Compound 1-3, and Compound F was used instead of Compound A.

MS: [M+H]$^+$=822

Preparation Example 82: Synthesis of Compound 18

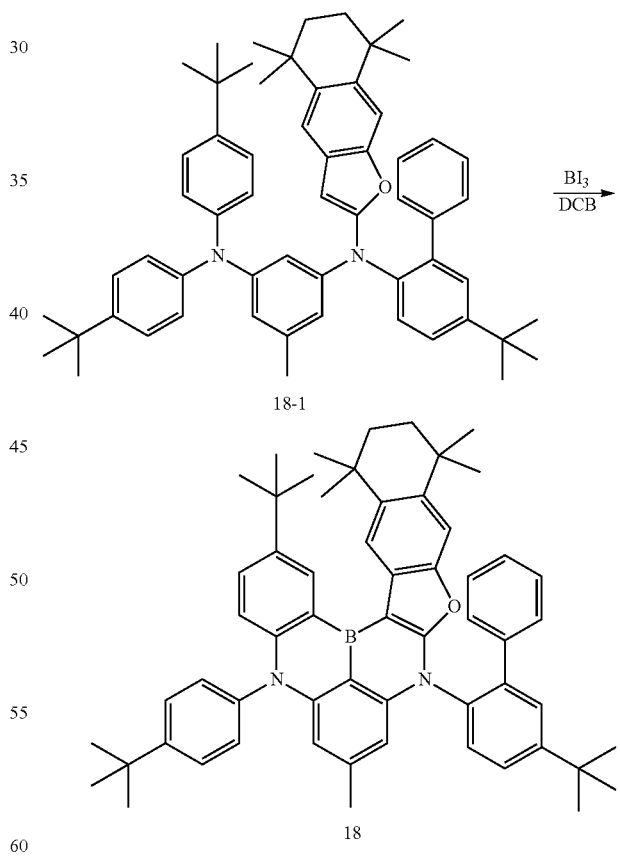

Compound 18 was obtained in the same manner as in Preparation of Compound 1 of Preparation Example 12 except that Compound 18-1 was used instead of Compound 1-4.

MS: [M+H]$^+$=829

Preparation Example 83: Synthesis of Compound 19-1

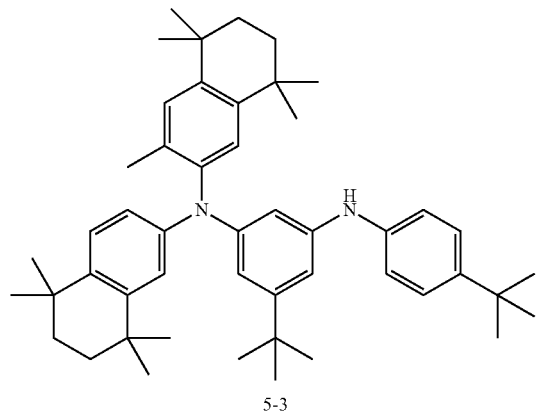

5-3

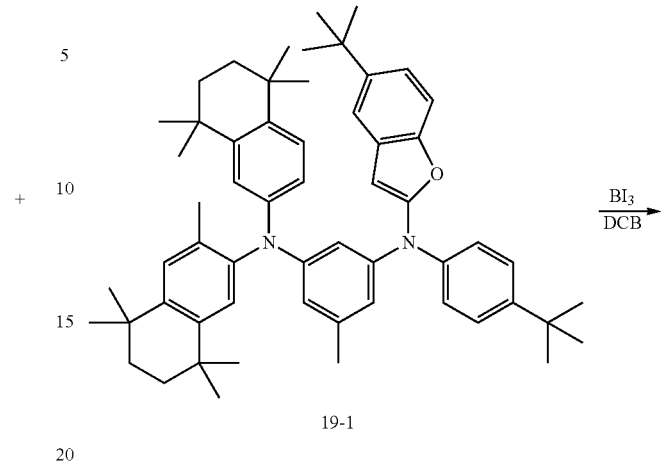

19-1

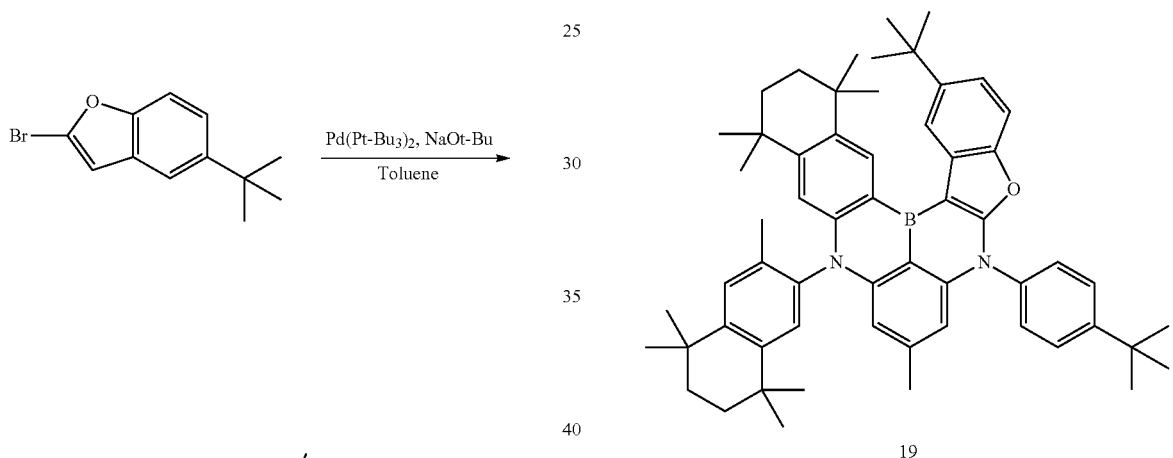

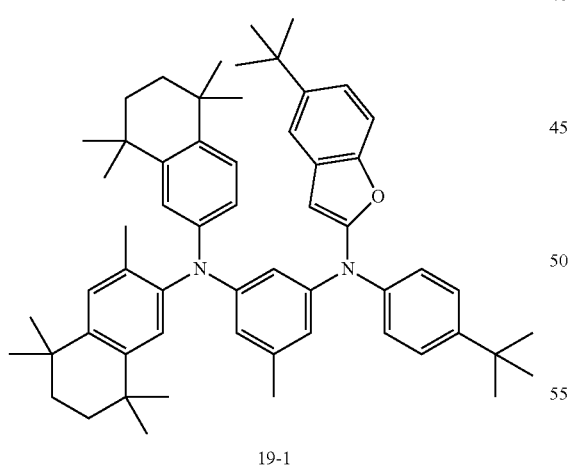

19-1

Compound 19-1 was obtained in the same manner as in Preparation of Compound 1-4 of Preparation Example 11 except that Compound 5-3 was used instead of Compound 1-3, and 2-bromo-5-(tert-butyl)benzofuran was used instead of Compound A.

MS: [M+H]$^+$=814

Preparation Example 84: Synthesis of Compound 19

Compound 19 was obtained in the same manner as in Preparation of Compound 1 of Preparation Example 12 except that Compound 19-1 was used instead of Compound 1-4.

MS: [M+H]$^+$=822

Preparation Example 85: Synthesis of Compound 20-1

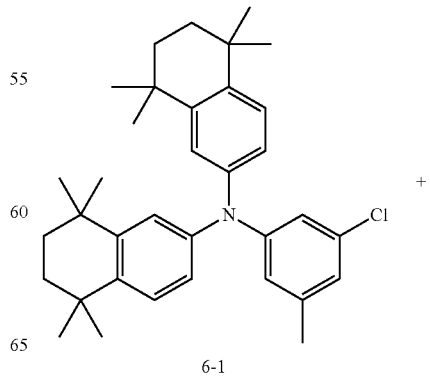

6-1

-continued

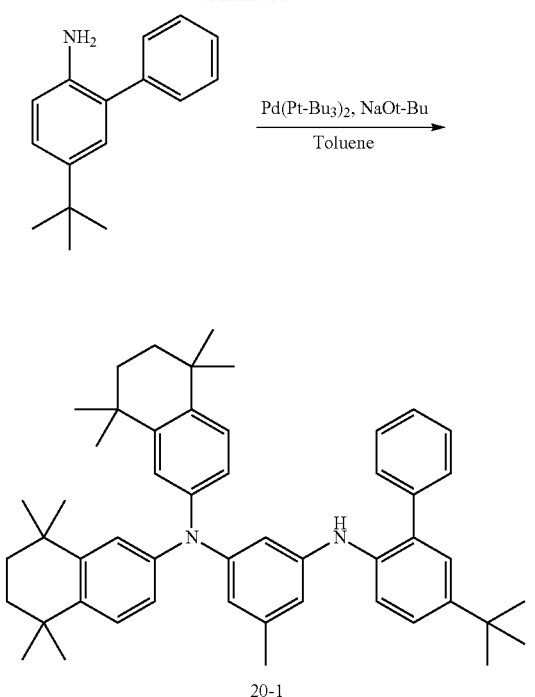

20-1

Compound 20-1 was obtained in the same manner as in Preparation of Compound 1-3 of Preparation Example 10 except that Compound 6-2 was used instead of Compound 1-2 and 5-tert-butylbiphenyl-2-amine was used instead of 4-(tert-butyl)aniline.

MS: [M+H]⁺=901

Preparation Example 86: Synthesis of Compound 20-2

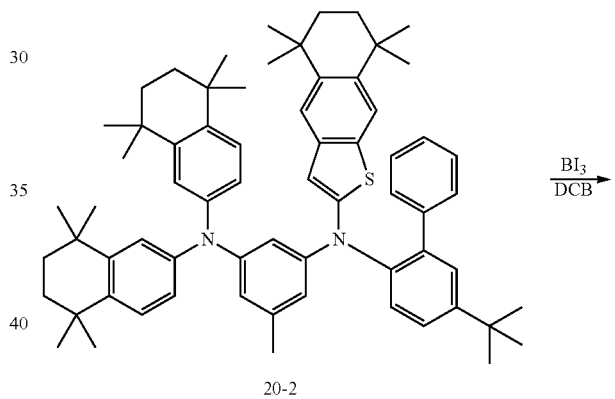

-continued

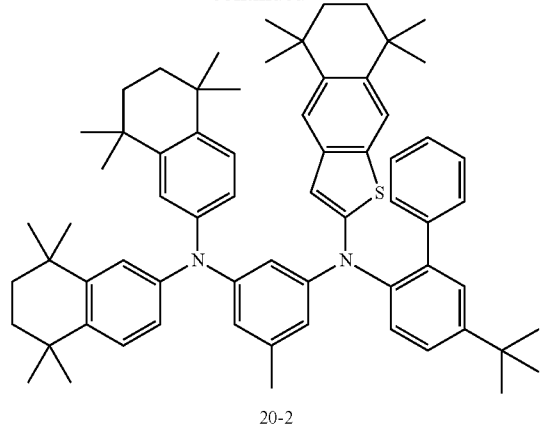

20-2

Compound 20-2 was obtained in the same manner as in Preparation of Compound 1-4 of Preparation Example 11 except that Compound 20-1 was used instead of Compound 1-3, and Compound E was used instead of Compound A.

MS: [M+H]⁺=946

Preparation Example 87: Synthesis of Compound 20

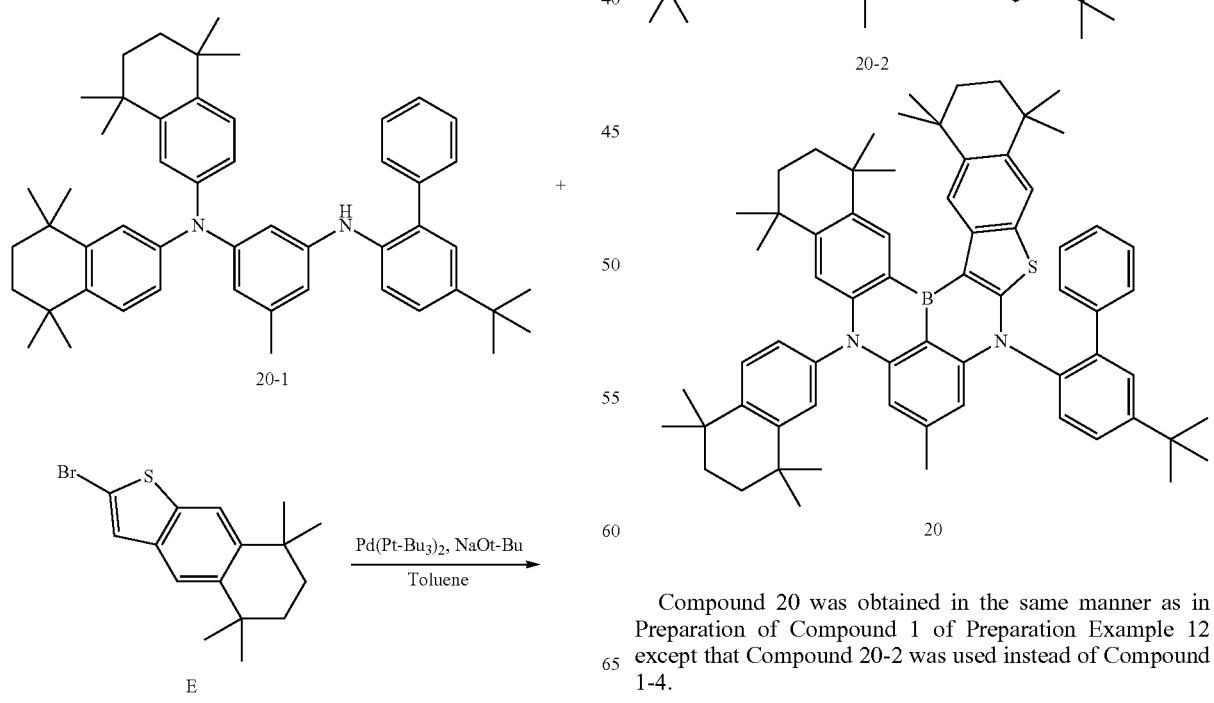

20

Compound 20 was obtained in the same manner as in Preparation of Compound 1 of Preparation Example 12 except that Compound 20-2 was used instead of Compound 1-4.

MS: [M+H]⁺=954

Preparation Example 88: Synthesis of Compound 21-1

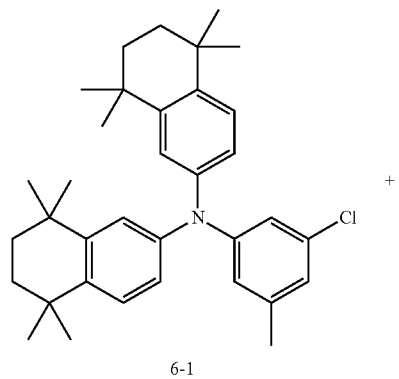

6-1

+

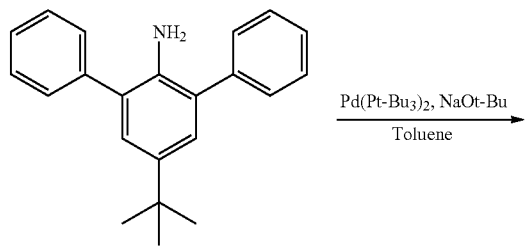

Pd(Pt-Bu₃)₂, NaOt-Bu
Toluene
→

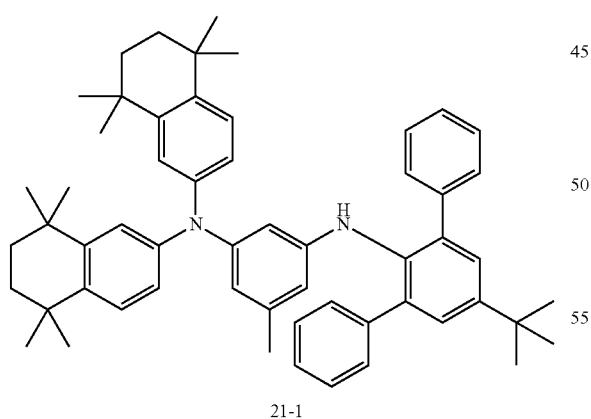

21-1

Compound 21-1 was obtained in the same manner as in Preparation of Compound 1-3 of Preparation Example 10 except that Compound 6-1 was used instead of Compound 1-2, and 5'-(tert-butyl)-[1,1':3',1''-terphenyl]-2'-amine was used instead of 4-(tert-butyl) aniline.

MS: [M+H]⁺=780

Preparation Example 89: Synthesis of Compound 21-2

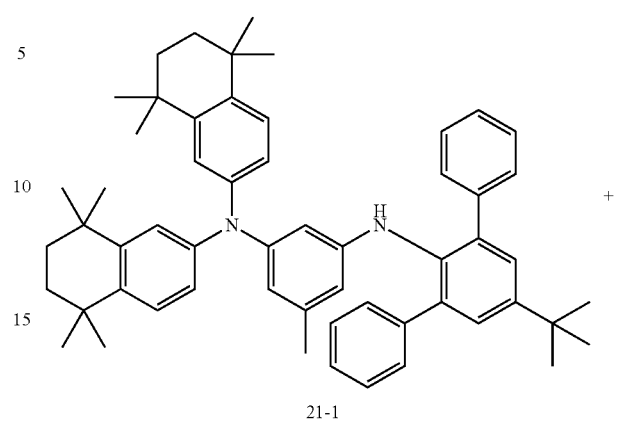

21-1

+

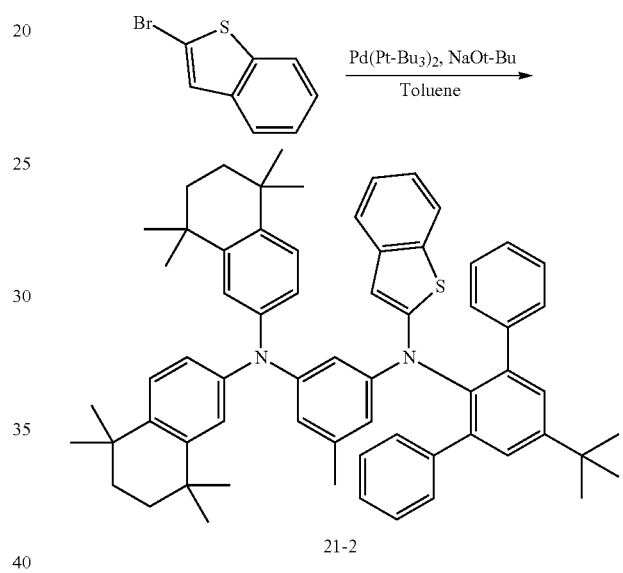

Pd(Pt-Bu₃)₂, NaOt-Bu
Toluene
→

21-2

Compound 21-2 was obtained in the same manner as in Preparation of Compound 1-4 of Preparation Example 11 except that Compound 21-1 was used instead of Compound 1-3, and 2-bromobenzo[b]thiophene was used instead of Compound A.

MS: [M+H]⁺=912

Preparation Example 90: Synthesis of Compound 21

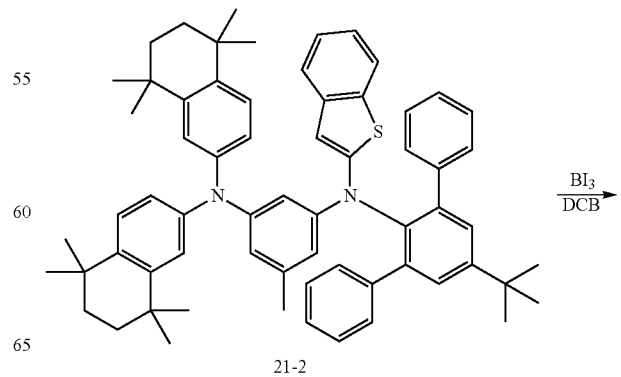

21-2

$\xrightarrow{\text{BI}_3/\text{DCB}}$

891
-continued

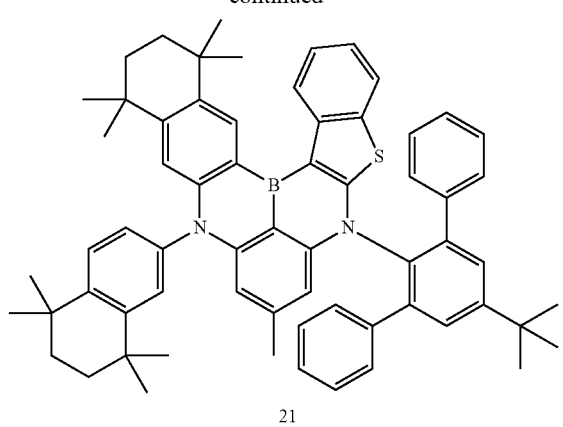

21

Compound 21 was obtained in the same manner as in Preparation of Compound 1 of Preparation Example 12 except that Compound 21-2 was used instead of Compound 1-4.

MS: [M+H]$^+$=920

Preparation Example 91: Synthesis of Compound 22-1

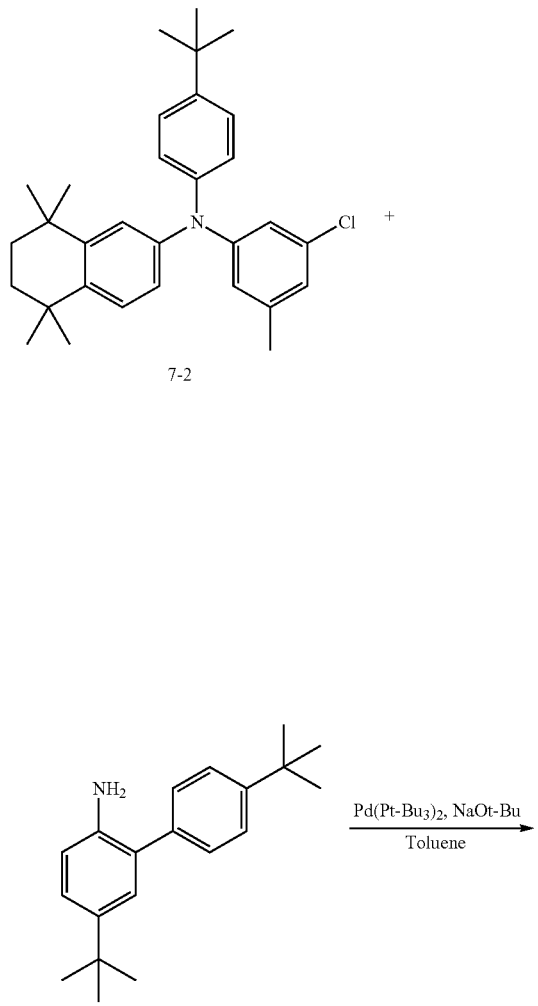

892
-continued

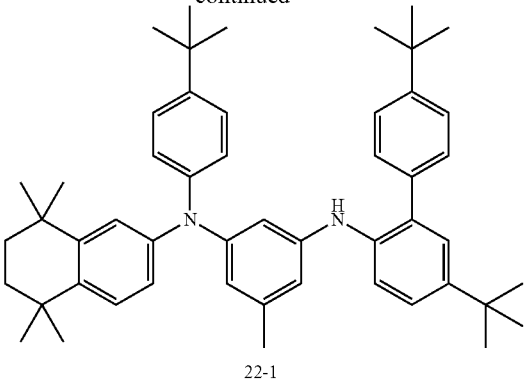

22-1

Compound 22-1 was obtained in the same manner as in Preparation of Compound 1-3 of Preparation Example 10 except that Compound 7-2 was used instead of Compound 1-2, and 4',5-di-tert-butyl-[1,1'-biphenyl]-2-amine was used instead of 4-(tert-butyl)aniline.

MS: [M+H]$^+$=706

Preparation Example 92: Synthesis of Compound 22-2

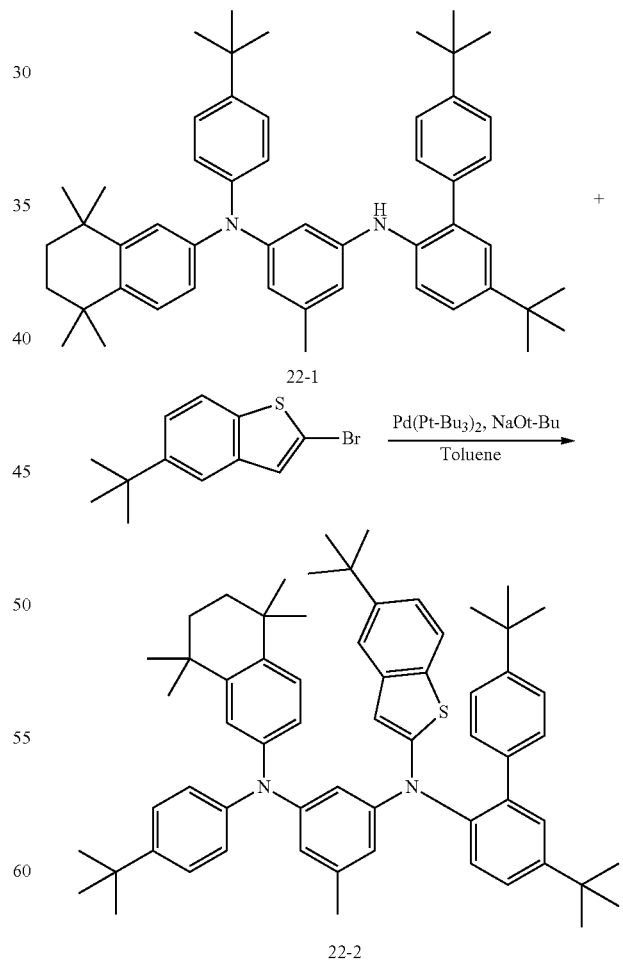

22-2

Compound 22-2 was obtained in the same manner as in Preparation of Compound 1-4 of Preparation Example 11 except that Compound 22-1 was used instead of Compound 1-3, and 2-bromo-5-(tert-butyl)benzo[b]thiophene was used instead of Compound A.

MS: [M+H]$^+$=894

Preparation Example 92-1: Synthesis of Compound 22

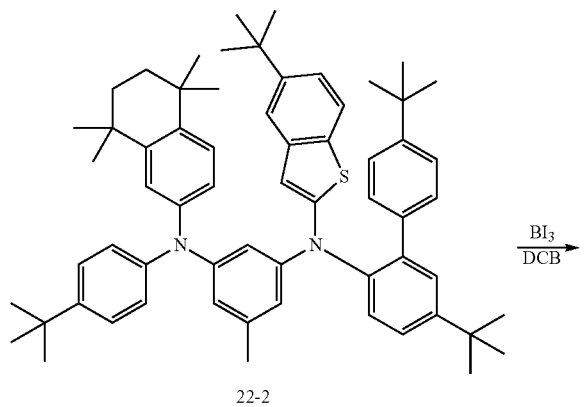

22-2

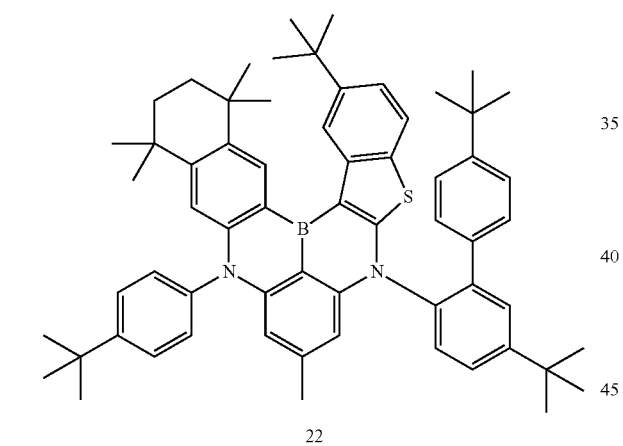

22

Compound 22 was obtained in the same manner as in Preparation of Compound 1 of Preparation Example 12 except that Compound 22-2 was used instead of Compound 1-4.

MS: [M+H]$^+$=902

Preparation Example 93: Synthesis of Compound 23-1

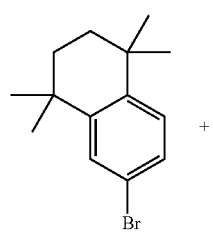

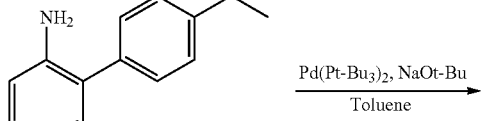

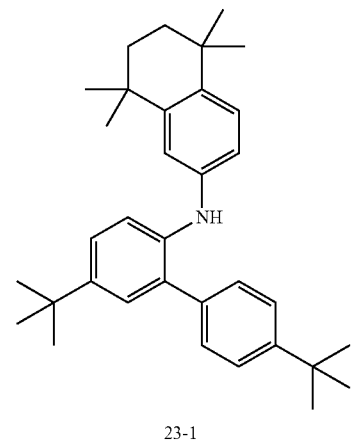

23-1

Compound 23-1 was obtained in the same manner as in Preparation of Compound 1-1 of Preparation Example 8 except that 4',5-di-tert-butyl-[1,1'-biphenyl]-2-amine was used instead of 5-(tert-butyl)-[1,1'-biphenyl]-2-amine.

MS: [M+H]$^+$=468

Preparation Example 94: Synthesis of Compound 23-2

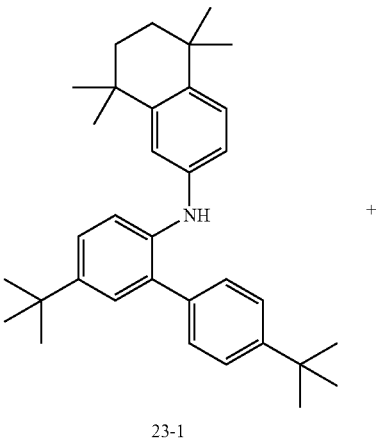

23-1

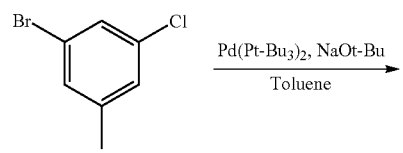

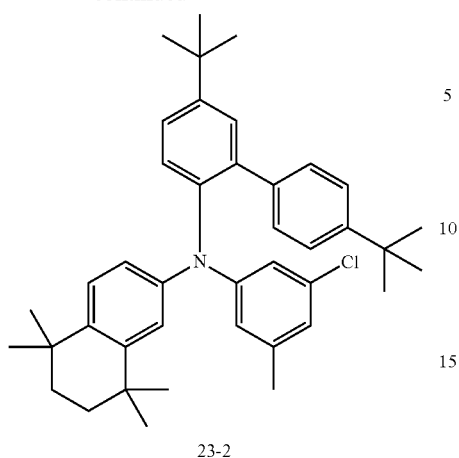

23-2

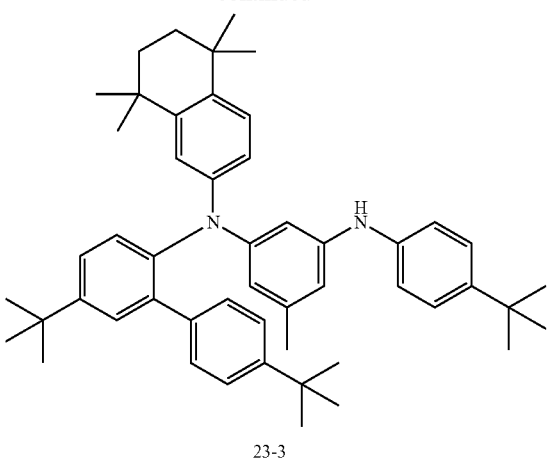

23-3

Compound 23-2 was obtained in the same manner as in Preparation of Compound 1-2 of Preparation Example 9 except that Compound 23-1 was used instead of Compound 1-1.

MS: [M+H]$^+$=593

Compound 23-3 was obtained in the same manner as in Preparation of Compound 1-3 of Preparation Example 10 except that Compound 23-2 was used instead of Compound 1-2.

MS: [M+H]$^+$=706

Preparation Example 95: Synthesis of Compound 23-3

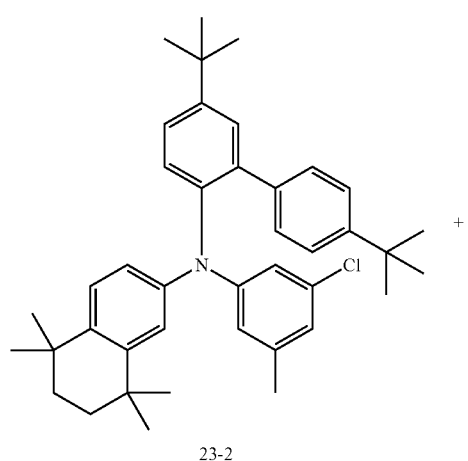

23-2

Preparation Example 96: Synthesis of Compound 23-4

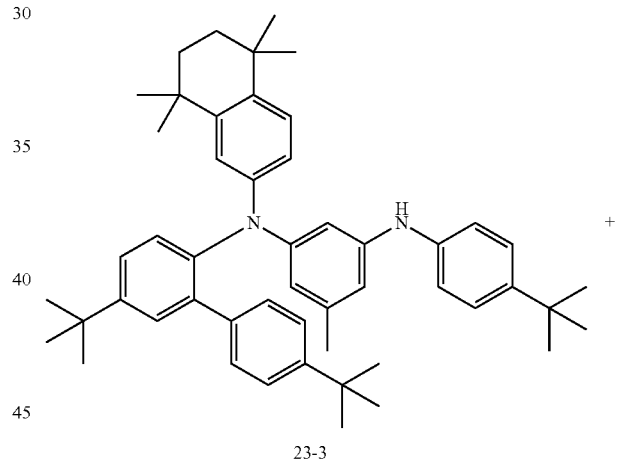

23-3

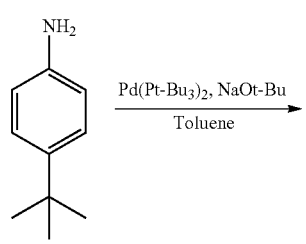

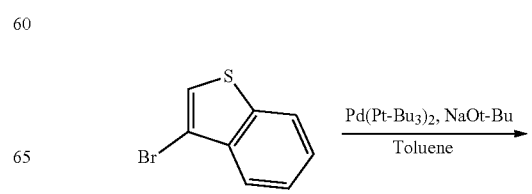

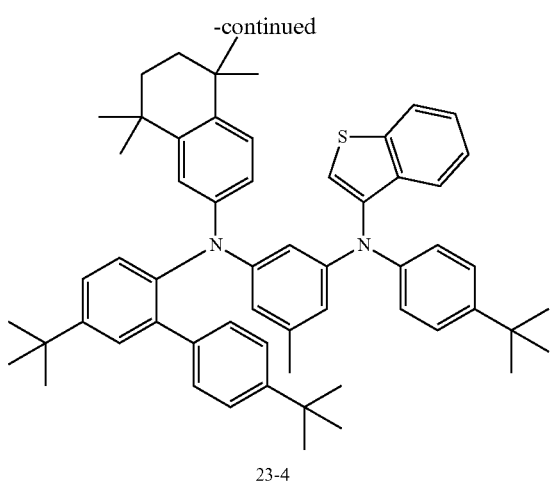

23-4

Compound 23-4 was obtained in the same manner as in Preparation of Compound 1-4 of Preparation Example 11 except that Compound 23-3 was used instead of Compound 1-3, and 3-bromobenzo[b]thiophene was used instead of Compound A.

MS: [M+H]⁺=838

Preparation Example 97: Synthesis of Compound 23

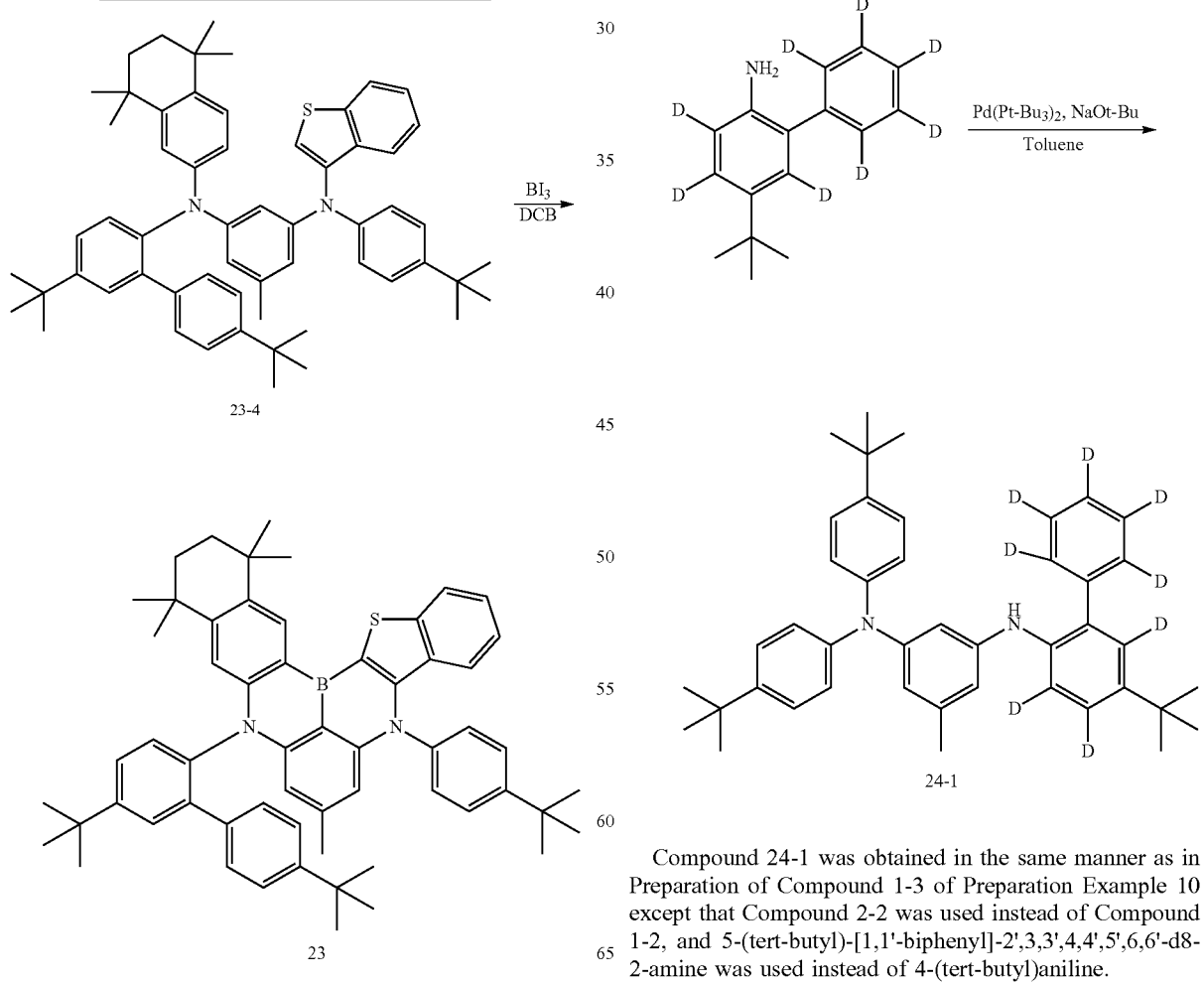

23

Compound 23 was obtained in the same manner as in Preparation of Compound 1 of Preparation Example 12 except that Compound 23-4 was used instead of Compound 1-4.

MS: [M+H]⁺=846

Preparation Example 98: Synthesis of Compound 24-1

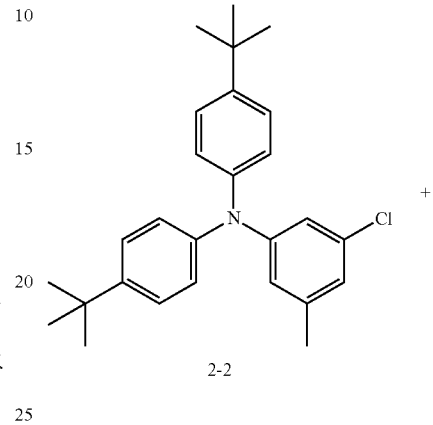

2-2

24-1

Compound 24-1 was obtained in the same manner as in Preparation of Compound 1-3 of Preparation Example 10 except that Compound 2-2 was used instead of Compound 1-2, and 5-(tert-butyl)-[1,1'-biphenyl]-2',3,3',4,4',5',6,6'-d8-2-amine was used instead of 4-(tert-butyl)aniline.

MS: [M+H]⁺=603

Preparation Example 99: Synthesis of Compound 24-2

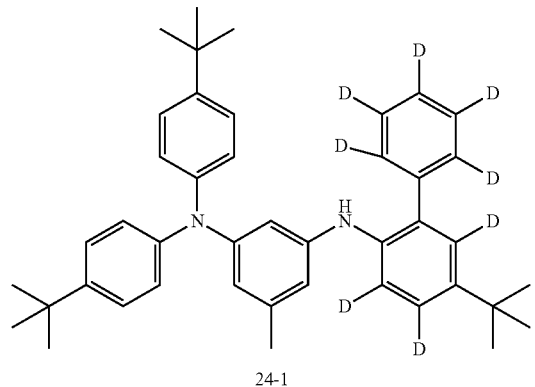

24-1

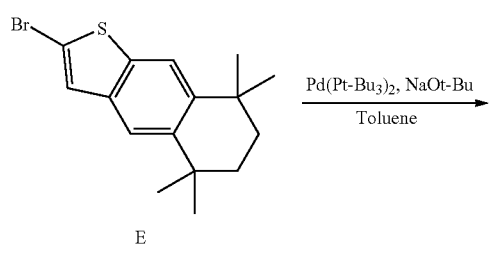

E

Pd(Pt-Bu₃)₂, NaOt-Bu / Toluene →

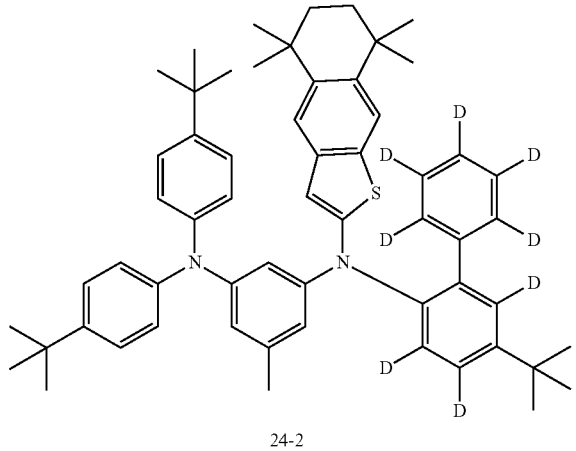

24-2

Compound 24-2 was obtained in the same manner as in Preparation of Compound 1-4 of Preparation Example 11 except that Compound 24-1 was used instead of Compound 1-3, and Compound E was used instead of Compound A.

MS: [M+H]⁺=846

Preparation Example 100: Synthesis of Compound 24

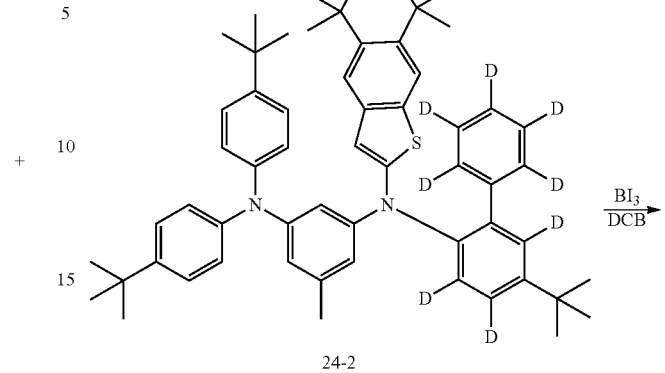

24-2

BI₃ / DCB →

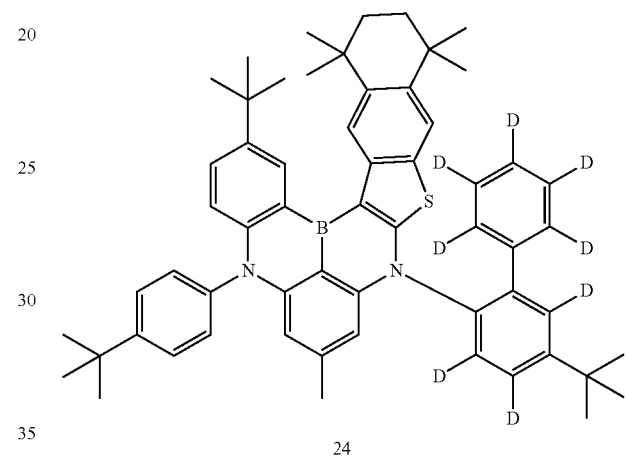

24

Compound 24 was obtained in the same manner as in Preparation of Compound 1 of Preparation Example 12 except that Compound 24-2 was used instead of Compound 1-4.

MS: [M+H]⁺=854

Preparation Example 101: Synthesis of Compound 25-1

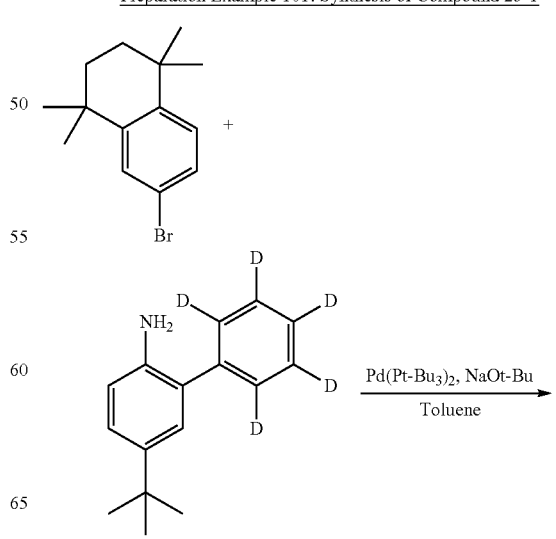

Pd(Pt-Bu₃)₂, NaOt-Bu / Toluene →

-continued

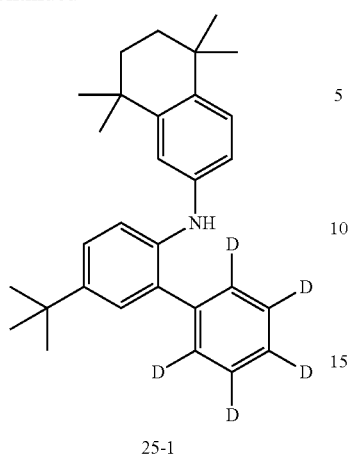

25-1

Compound 25-1 was obtained in the same manner as in Preparation of Compound 1-1 of Preparation Example 8 except that 5-(tert-butyl)-[1,1'-biphenyl]-2',3',4',5',6'-d5-2-amine was used instead of 5-(tert-butyl)-[1,1'-biphenyl]-2-amine.

MS: [M+H]$^+$=417

Preparation Example 102: Synthesis of Compound 25-2

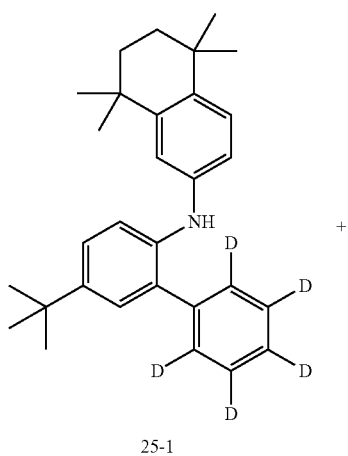

25-1

+

-continued

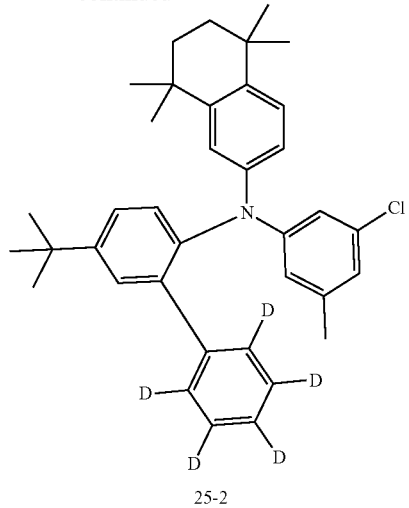

25-2

Compound 25-2 was obtained in the same manner as in Preparation of Compound 1-2 of Preparation Example 9 except that Compound 25-1 was used instead of Compound 1-1.

MS: [M+H]$^+$=542

Preparation Example 103: Synthesis of Compound 25-3

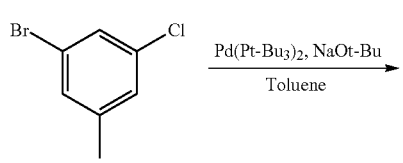

25-2

+

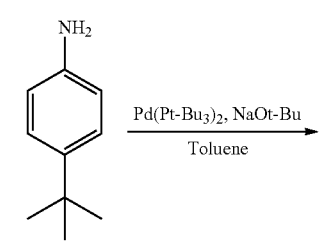

-continued

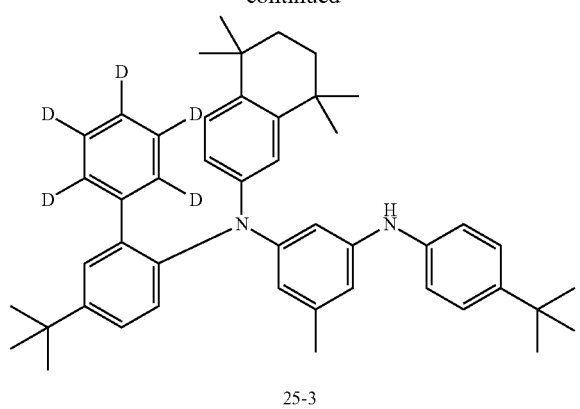

25-3

Compound 25-3 was obtained in the same manner as in Preparation of Compound 1-3 of Preparation Example 10 except that Compound 25-2 was used instead of Compound 1-2.

MS: [M+H]⁺=655

Preparation Example 104: Synthesis of Compound 25-4

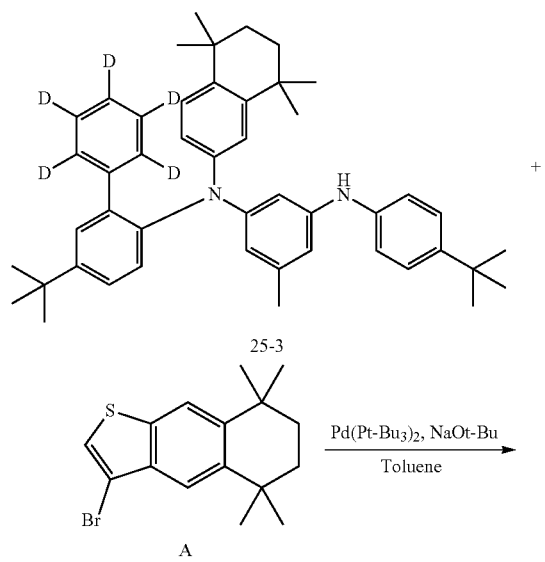

Compound 25-4 was obtained in the same manner as in Preparation of Compound 1-4 of Preparation Example 11 except that Compound 25-3 was used instead of Compound 1-3.

MS: [M+H]⁺=897

Preparation Example 104-1: Synthesis of Compound 25

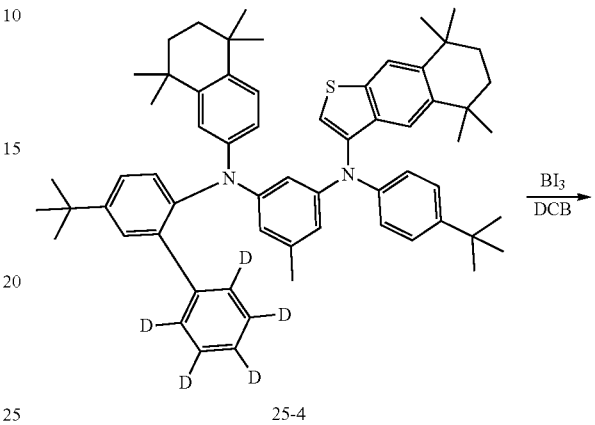

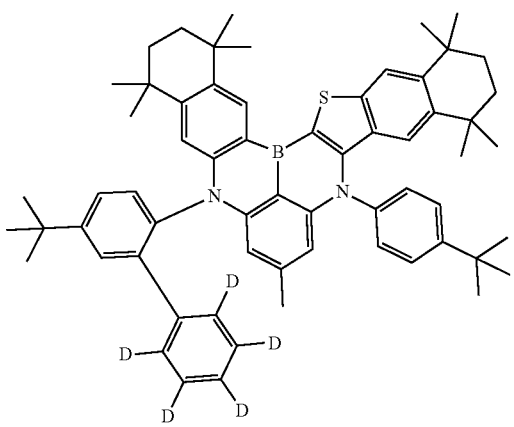

25

Compound 25 was obtained in the same manner as in Preparation of Compound 1 of Preparation Example 12 except that Compound 25-4 was used instead of Compound 1-4.

MS: [M+H]⁺=905

Preparation Example 105: Synthesis of Compound 26-1

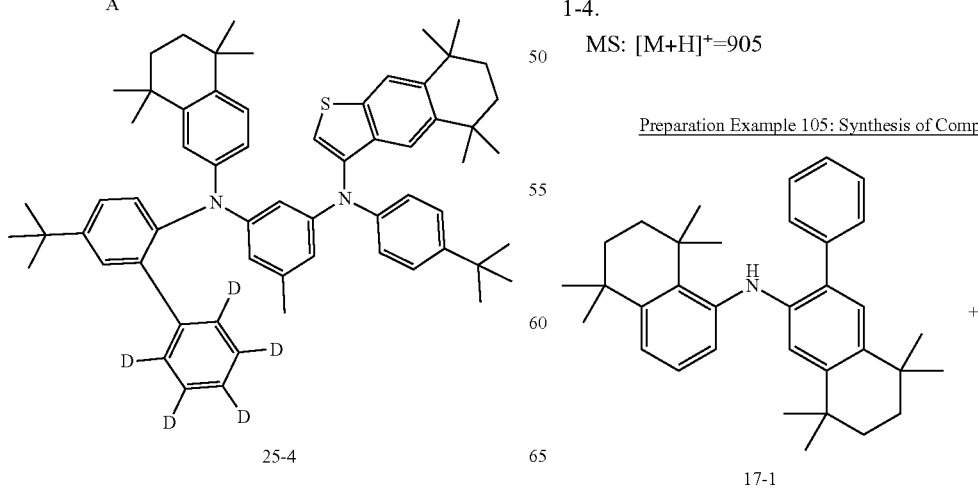

17-1

-continued

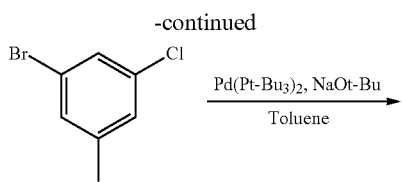

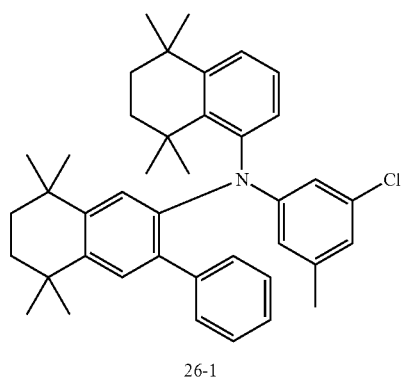

26-1

Compound 26-1 was obtained in the same manner as in Preparation of Compound 1-2 of Preparation Example 9 except that Compound 17-1 was used instead of Compound 1-1.

MS: [M+H]⁺=591

Preparation Example 106: Synthesis of Compound 26-2

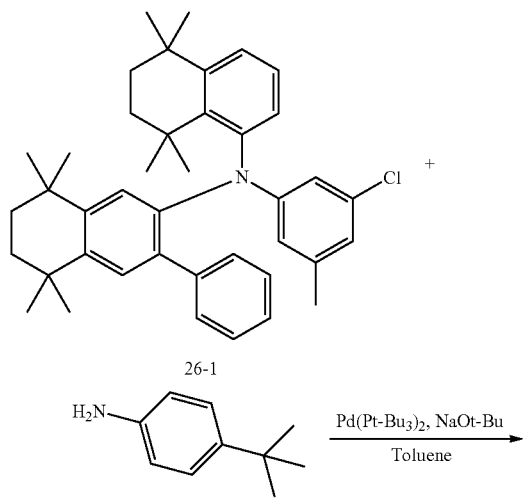

26-1

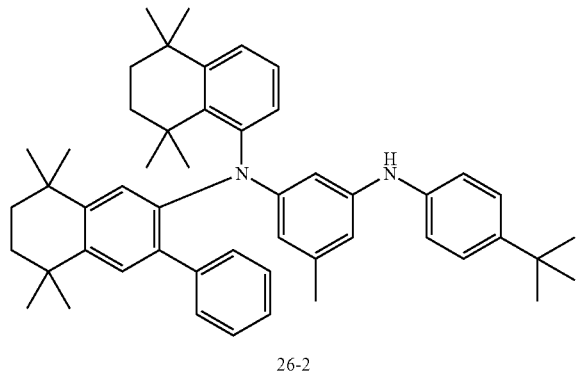

26-2

Compound 26-2 was obtained in the same manner as in Preparation of Compound 1-3 of Preparation Example 10 except that Compound 26-1 was used instead of Compound 1-2.

MS: [M+H]⁺=704

Preparation Example 107: Synthesis of Compound 26-3

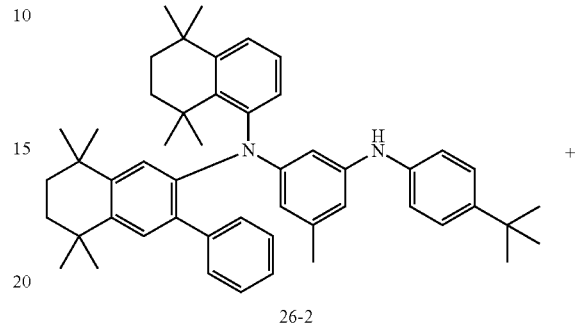

26-2

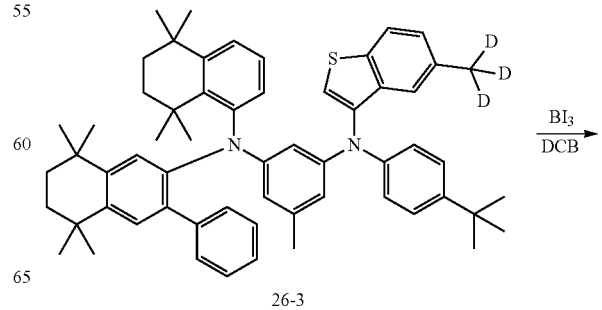

26-3

Compound 26-3 was obtained in the same manner as in Preparation of Compound 1-4 of Preparation Example 11 except that Compound 26-2 was used instead of Compound 1-3, and 3-bromo-5-(methyl-d3)benzo[b]thiophene was used instead of Compound A.

MS: [M+H]⁺=853

Preparation Example 107-1: Synthesis of Compound 26

26-3

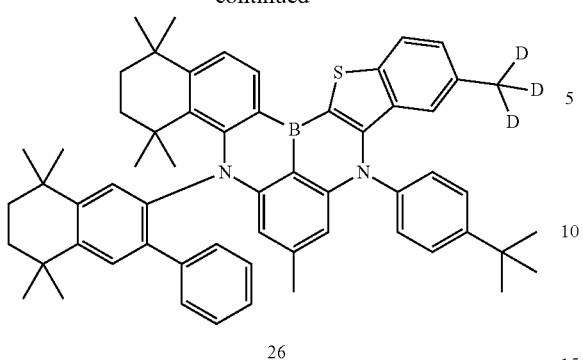

26

Compound 26 was obtained in the same manner as in Preparation of Compound 1 of Preparation Example 12 except that Compound 26-3 was used instead of Compound 1-4.

MS: [M+H]⁺=861

Preparation Example 108: Synthesis of Compound 27-1

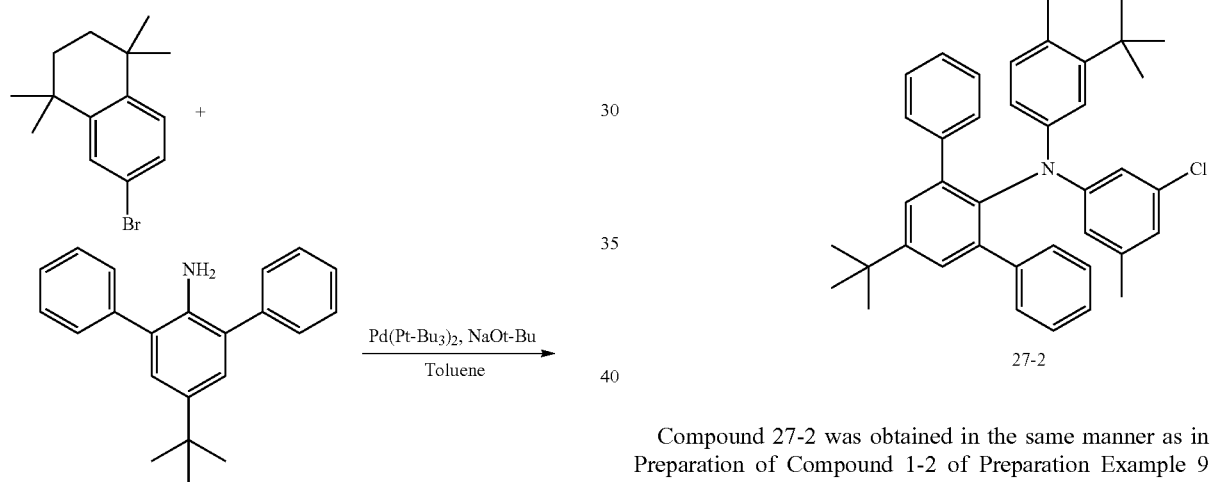

27-1

Compound 27-1 was obtained in the same manner as in Preparation of Compound 1-1 of Preparation Example 8 except that 5'-(tert-butyl)-[1,1':3',1''-terphenyl]-2'-amine was used instead of 5-(tert-butyl)-[1,1'-biphenyl]-2-amine.

MS: [M+H]⁺=488

Preparation Example 109: Synthesis of Compound 27-2

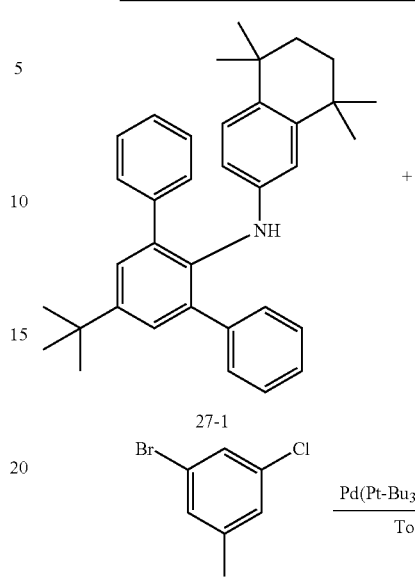

27-2

Compound 27-2 was obtained in the same manner as in Preparation of Compound 1-2 of Preparation Example 9 except that Compound 27-1 was used instead of Compound 1-1.

MS: [M+H]⁺=613

Preparation Example 110: Synthesis of Compound 27-3

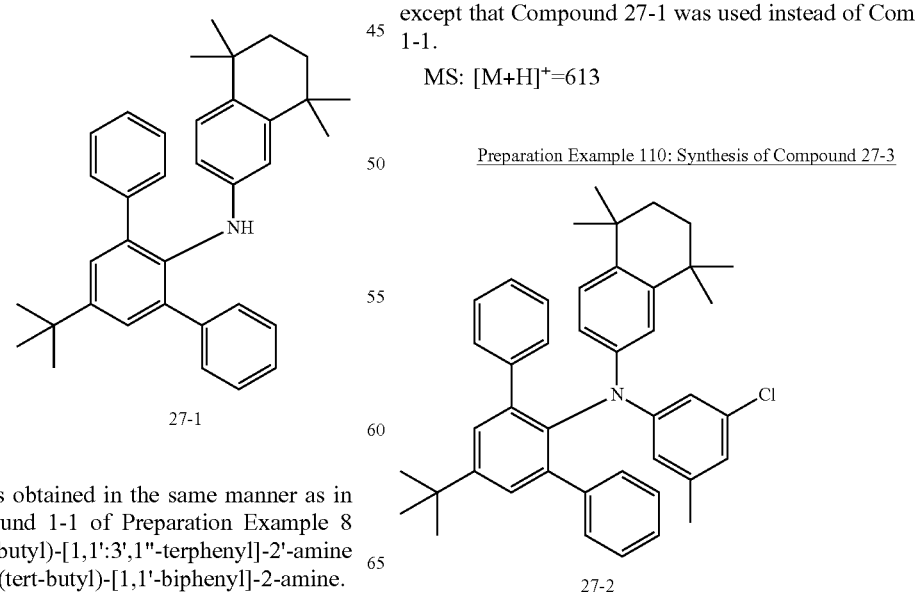

27-2

-continued

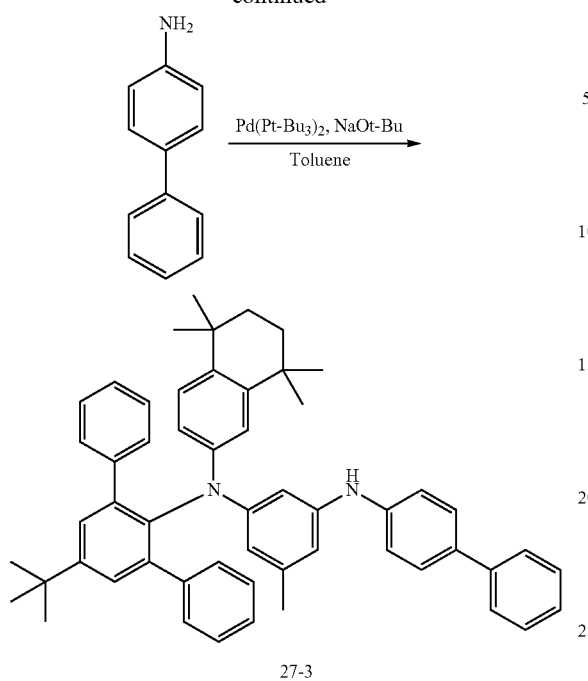

27-3

Compound 27-3 was obtained in the same manner as in Preparation of Compound 1-3 of Preparation Example 10 except that Compound 27-2 was used instead of Compound 1-2, and [1,1'-biphenyl]-4-amine was used instead of 4-(tert-butyl)aniline.

MS: [M+H]$^+$=746

Preparation Example 111: Synthesis of Compound 27-4

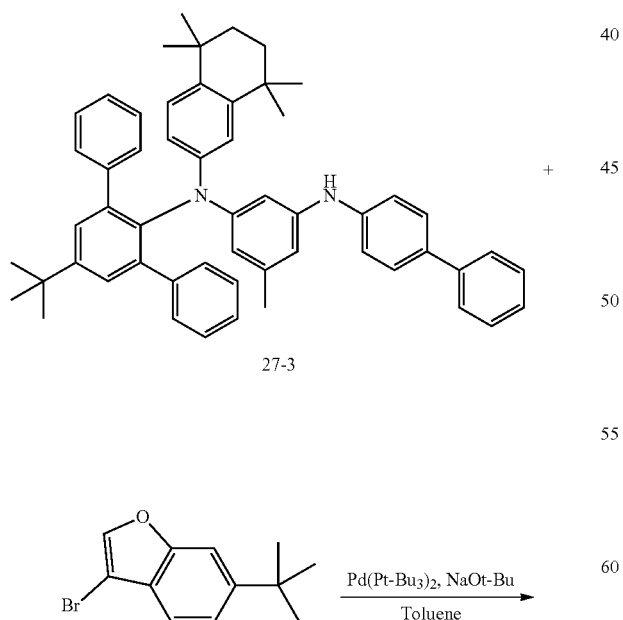

-continued

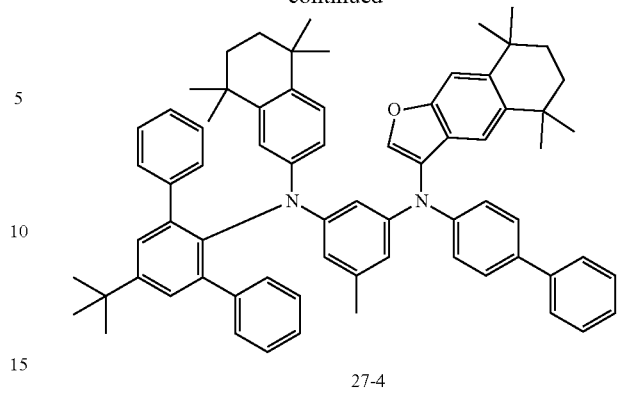

27-4

Compound 27-4 was obtained in the same manner as in Preparation of Compound 1-4 of Preparation Example 11 except that Compound 27-3 was used instead of Compound 1-3, and Compound B was used instead of Compound A.

MS: [M+H]$^+$=972

Preparation Example 112: Synthesis of Compound 27

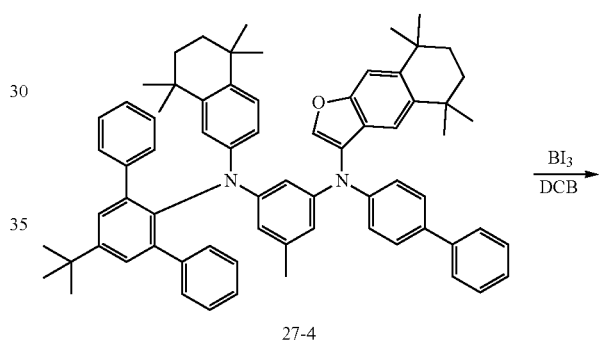

27

Compound 27 was obtained in the same manner as in Preparation of Compound 1 of Preparation Example 12 except that Compound 27-4 was used instead of Compound 1-4.

MS: [M+H]$^+$=980

Preparation Example 113: Synthesis of Compound 28-1

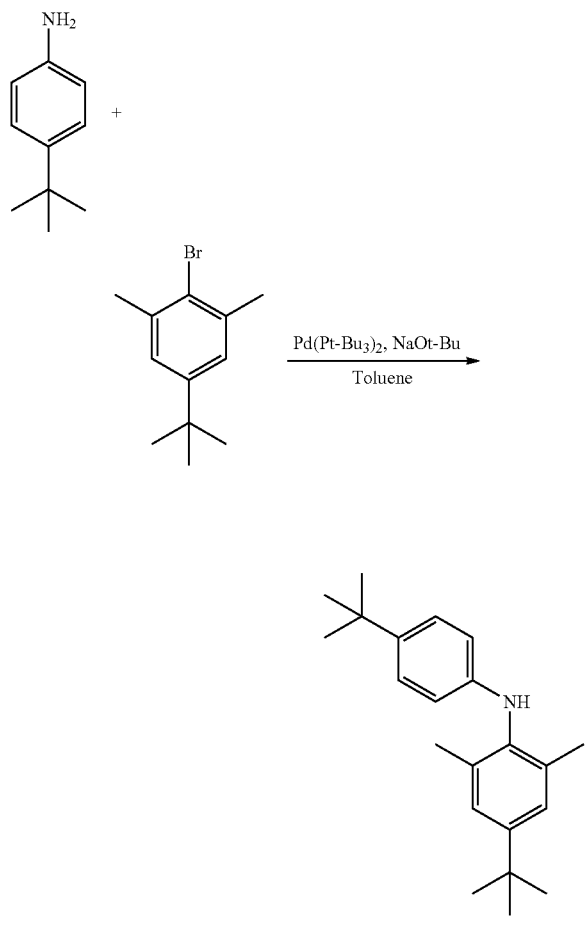

28-1

Compound 28-1 was obtained in the same manner as in Preparation of Compound 1-1 of Preparation Example 8 except that 2-bromo-5-(tert-butyl)-1,3-dimethylbenzene was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]$^+$=310

Preparation Example 114: Synthesis of Compound 28-2

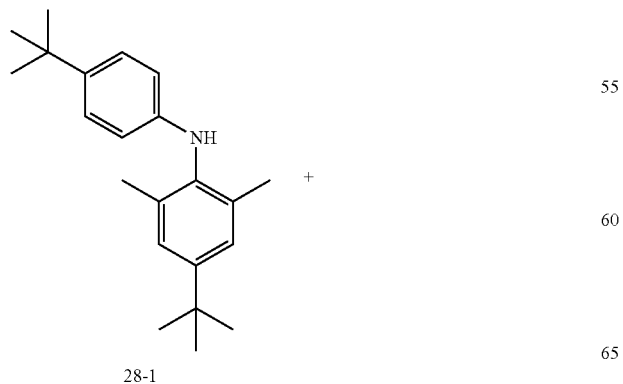

28-1

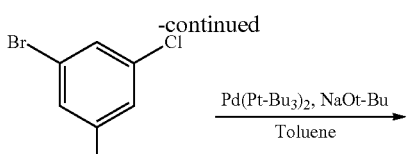

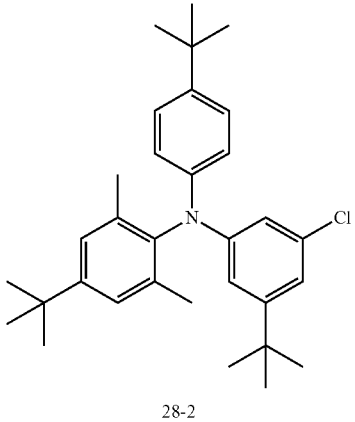

28-2

Compound 28-2 was obtained in the same manner as in Preparation of Compound 1-2 of Preparation Example 9 except that Compound 28-1 was used instead of Compound 1-1, and 1-bromo-3-(tert-butyl)-5-chlorobenzene was used instead of 1-bromo-3-chloro-5-methylbenzene.

MS: [M+H]$^+$=477

Preparation Example 115: Synthesis of Compound 28-3

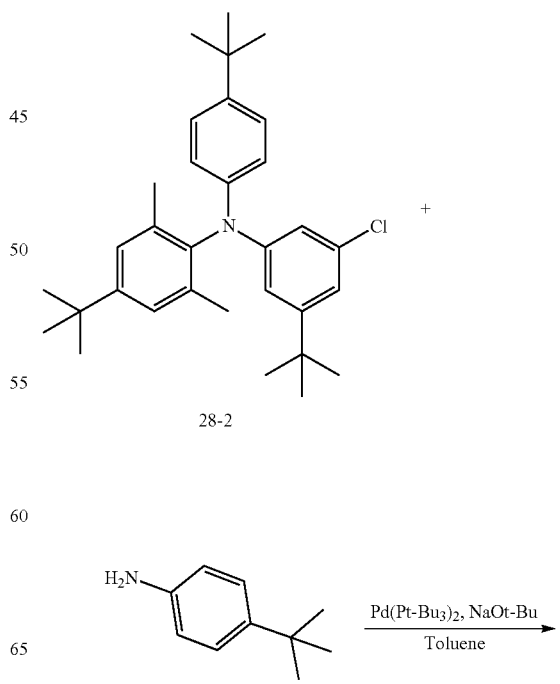

913
-continued

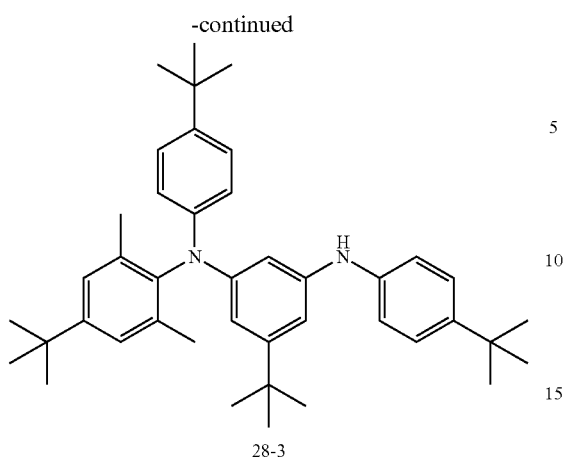

28-3

Compound 28-3 was obtained in the same manner as in Preparation of Compound 1-3 of Preparation Example 10 except that Compound 28-2 was used instead of Compound 1-2.

MS: [M+H]$^+$=589

Preparation Example 116: Synthesis of Compound 28-4

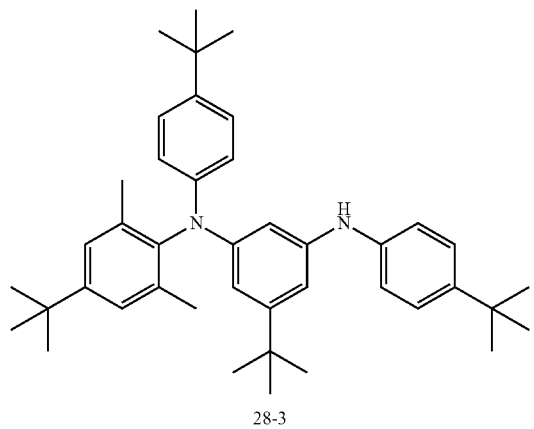

28-3

+

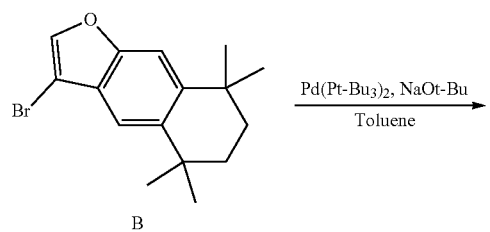

B

Pd(Pt-Bu$_3$)$_2$, NaOt-Bu
Toluene →

914
-continued

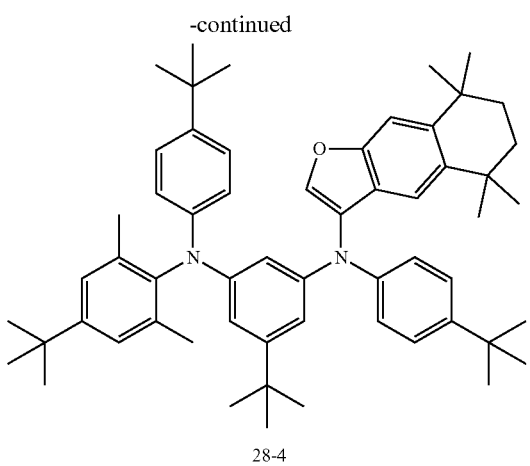

28-4

Compound 28-4 was obtained in the same manner as in Preparation of Compound 1-4 of Preparation Example 11 except that Compound 28-3 was used instead of Compound 1-3, and Compound B was used instead of Compound A.

MS: [M+H]$^+$=816

Preparation Example 117: Synthesis of Compound 28

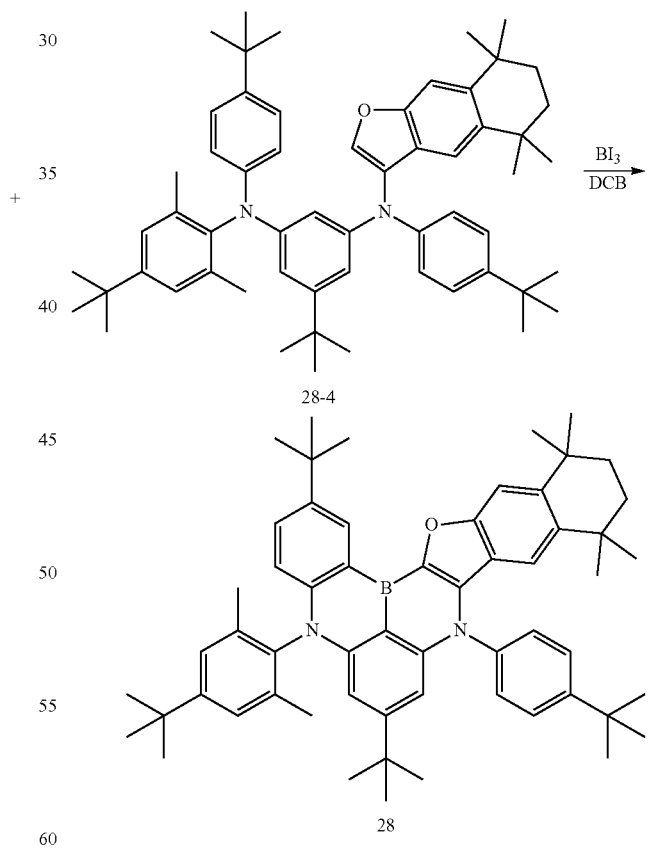

Compound 28 was obtained in the same manner as in Preparation of Compound 1 of Preparation Example 12 except that Compound 28-4 was used instead of Compound 1-4.

MS: [M+H]$^+$=824

Preparation Example 118: Synthesis of Compound G

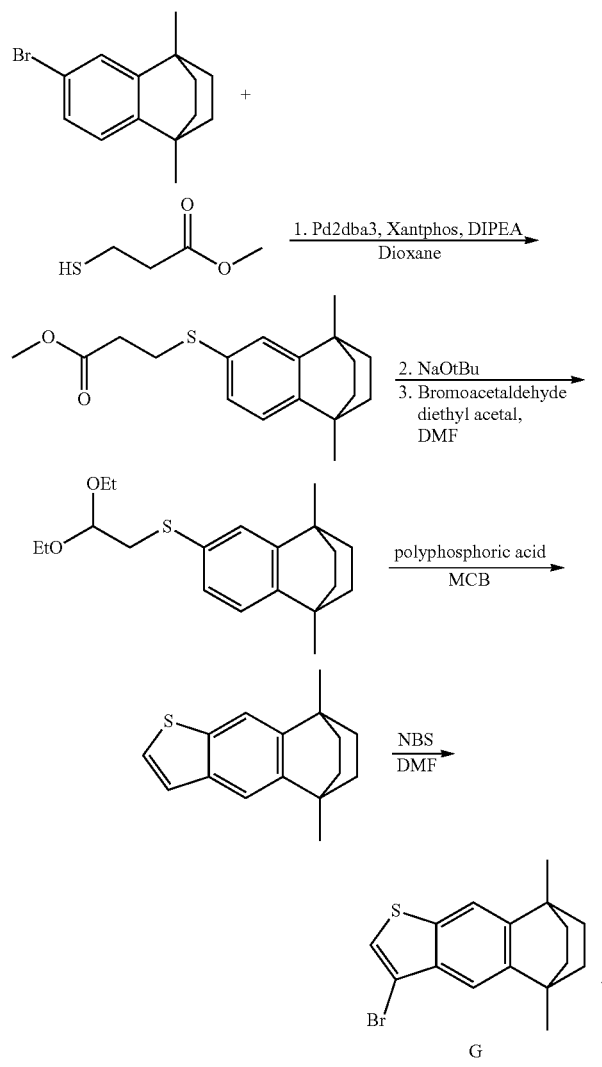

Compound G was obtained in the same manner as in Preparation of Compound A of Preparation Examples 1 to 3 except that 6-bromo-1,4-dimethyl-1,2,3,4-tetrahydro-1,4-ethanonaphthalene was used instead of 6-bromo-1,1,4,4-tetramethyl-1,2,3,4-tetrahydronaphthalene.

MS: $[M+H]^+$=322

Preparation Example 119: Synthesis of Compound H

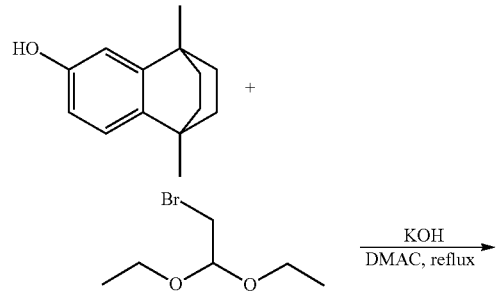

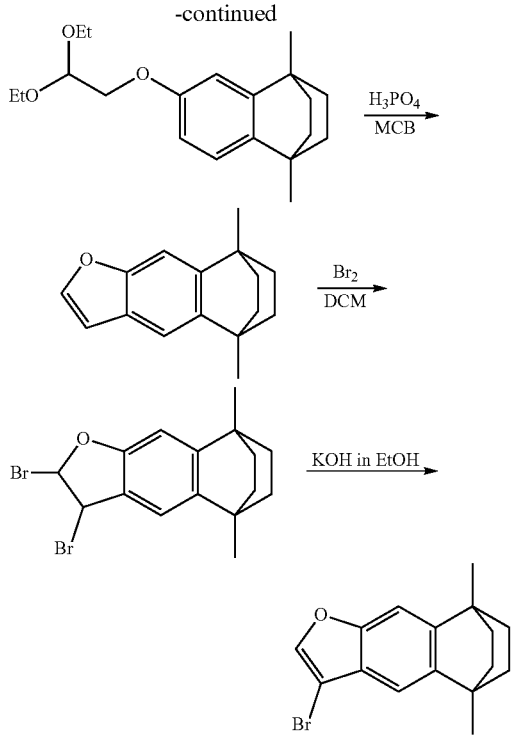

Compound H was obtained in the same manner as in Preparation of Compound B of Preparation Examples 4,5,6 and 7 except that 1,4-dimethyl-1,2,3,4-tetrahydro-1,4-ethanonaphthalen-6-ol was used instead of 5,5,8,8-tetramethyl-5,6,7,8-tetrahydronaphthalen-2-ol.

MS: $[M+H]^+$=306

Preparation Example 120: Synthesis of Compound 29-1

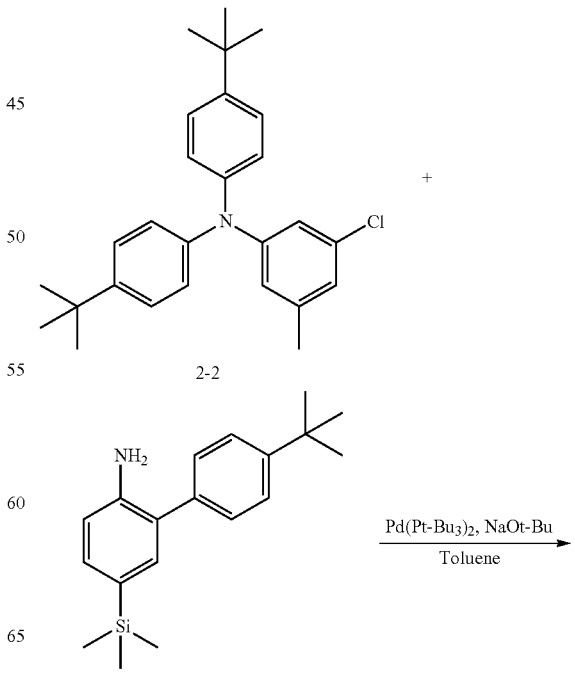

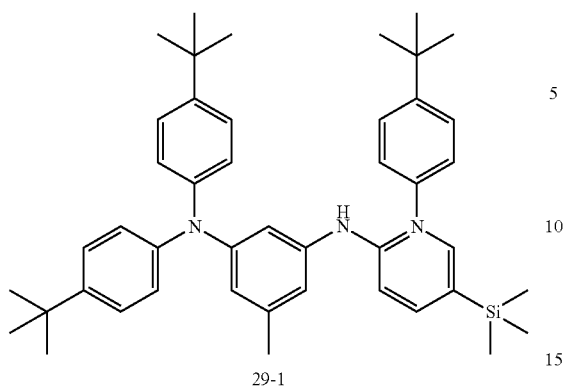

29-1

Compound 29-1 was obtained in the same manner as in Preparation of Compound 1-3 of Preparation Example 10 except that Compound 2-2 was used instead of Compound 1-2, and 4'-(tert-butyl)-5-(trimethylsilyl)-[1,1'-biphenyl]-2-amine was used instead of 4-(tert-butyl)aniline.

MS: [M+H]⁺=668

Preparation Example 121: Synthesis of Compound 29-2

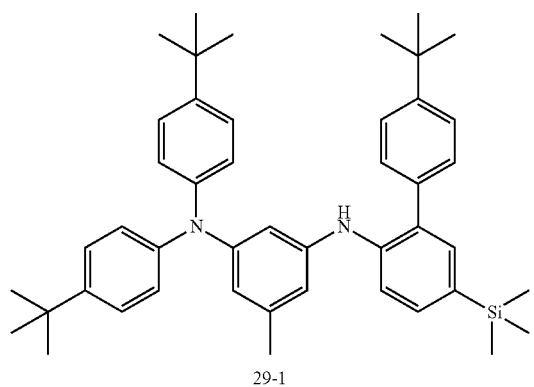

29-1

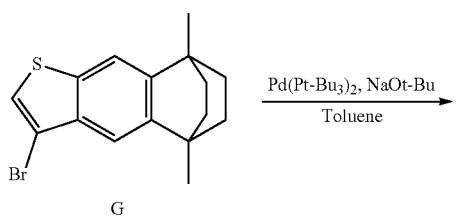

G

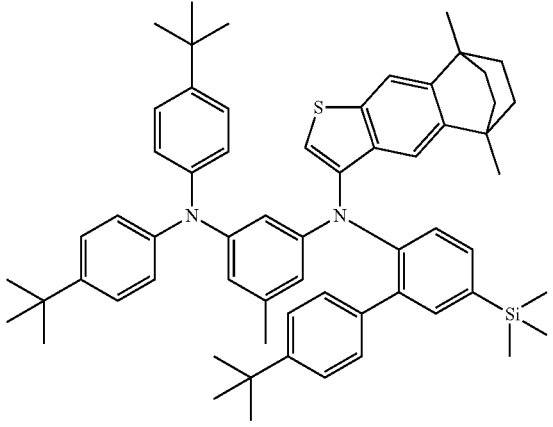

29-2

Compound 29-2 was obtained in the same manner as in Preparation of Compound 1-4 of Preparation Example 11 except that Compound 29-1 was used instead of Compound 1-3, and Compound G was used instead of Compound A.

MS: [M+H]⁺=908

Preparation Example 122: Synthesis of Compound 29

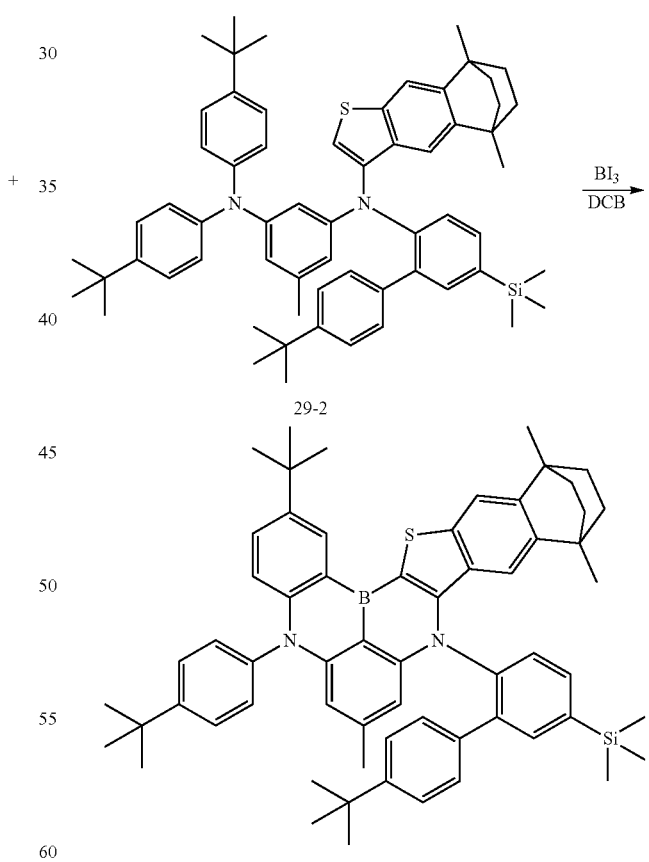

29

Compound 29 was obtained in the same manner as in Preparation of Compound 1 of Preparation Example 12 except that Compound 29-2 was used instead of Compound 1-4.

MS: [M+H]⁺=916

Preparation Example 123: Synthesis of Compound 30-1

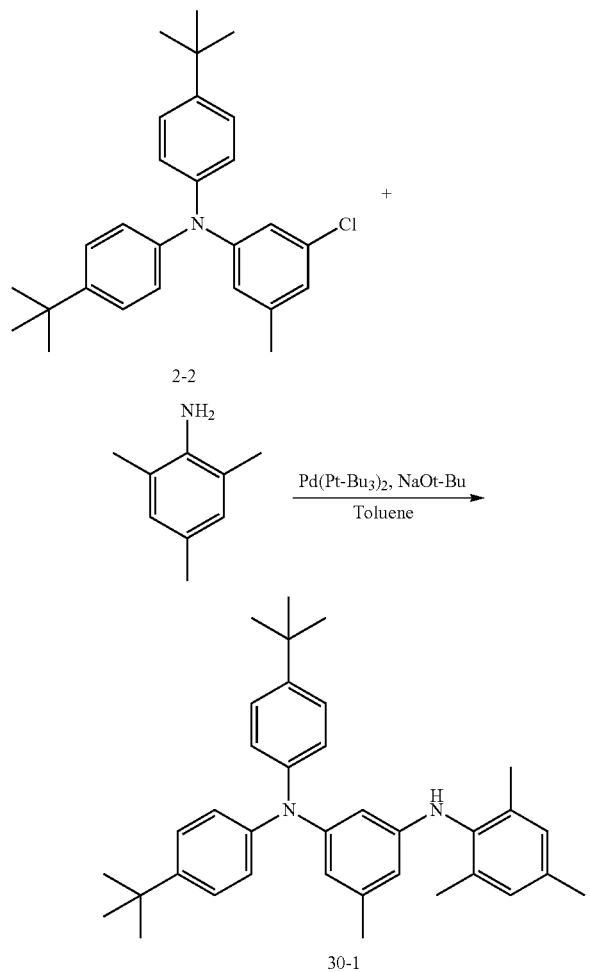

Compound 30-1 was obtained in the same manner as in Preparation of Compound 1-3 of Preparation Example 10 except that Compound 2-2 was used instead of Compound 1-2, and 2,4,6-trimethylaniline was used instead of 4-(tert-butyl)aniline.

MS: [M+H]⁺=505

Preparation Example 124: Synthesis of Compound 30-2

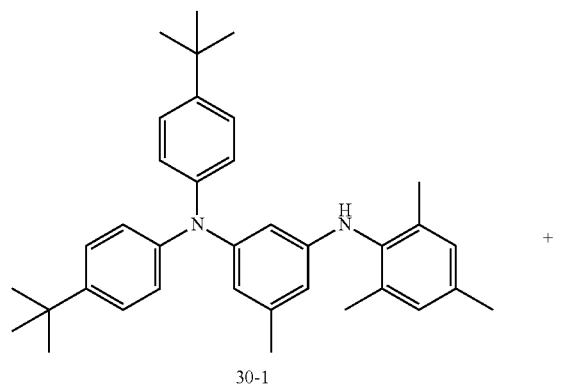

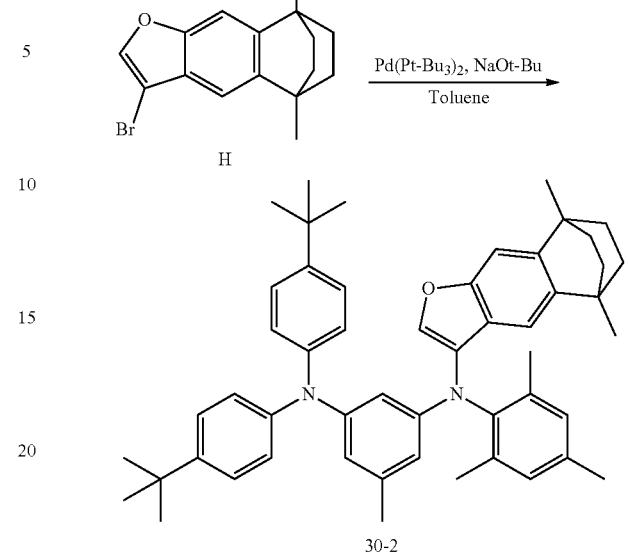

Compound 30-2 was obtained in the same manner as in Preparation of Compound 1-4 of Preparation Example 11 except that Compound 30-1 was used instead of Compound 1-3, and Compound H was used instead of Compound A.

MS: [M+H]⁺=730

Preparation Example 125: Synthesis of Compound 30

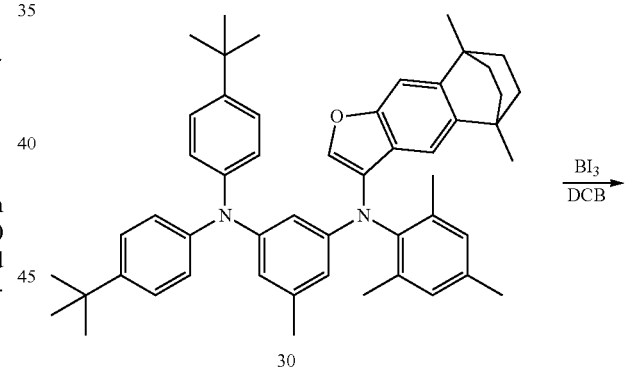

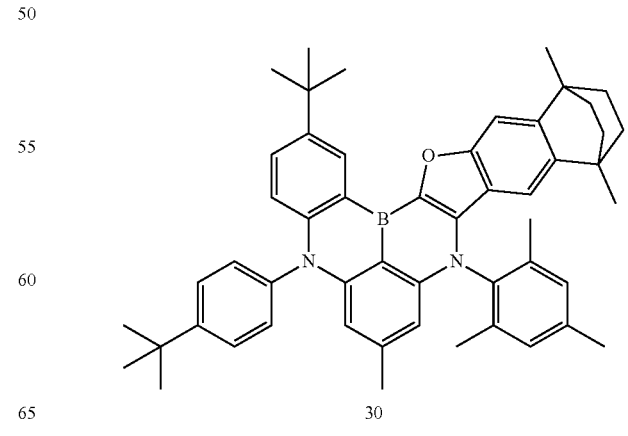

Compound 30 was obtained in the same manner as in Preparation of Compound 1 of Preparation Example 12 except that Compound 30-2 was used instead of Compound 1-4.

MS: [M+H]$^+$=737

Preparation Example 126: Synthesis of Compound 31-1

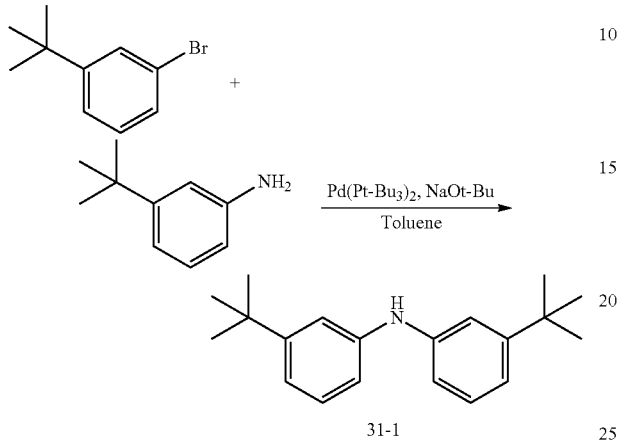

Compound 31-1 was obtained in the same manner as in Preparation of Compound 1-1 of Preparation Example 8 except that 1-bromo-3-(tert-butyl)benzene was used instead of 6-bromo-1,1,4,4-tetramethyl-1,2,3,4-tetrahydronaphthalene, and 3-(tert-butyl)aniline was used instead of 5-(tert-butyl)-[1,1'-biphenyl]-2-amine.

MS: [M+H]$^+$=282

Preparation Example 127: Synthesis of Compound 31-2

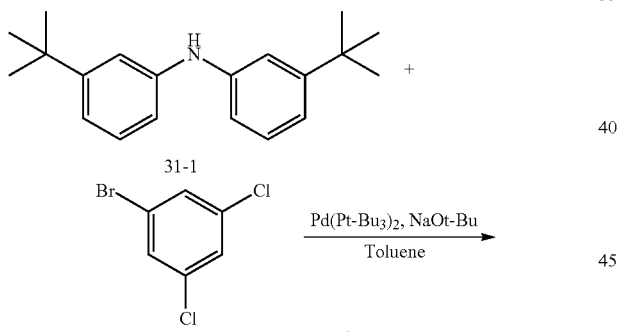

Compound 31-2 was obtained in the same manner as in Preparation of Compound 1-2 of Preparation Example 9 except that Compound 31-1 was used instead of Compound 1-1, and 1-bromo-3,5-dichlorobenzene was used instead of 1-bromo-3-chloro-5-methylbenzene.

MS: [M+H]$^+$=427

Preparation Example 128: Synthesis of Compound 31-3

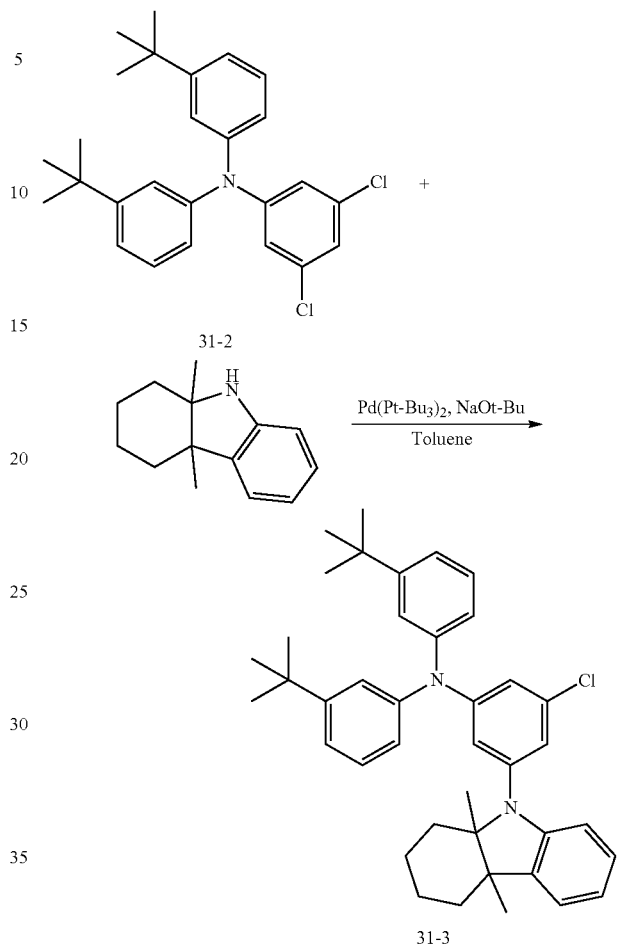

Compound 31-3 was obtained in the same manner as in Preparation of Compound 1-3 of Preparation Example 10 except that Compound 31-2 was used instead of Compound 1-2, and 4a,9a-dimethyl-2,3,4,4a, 9,9a-hexahydro-1H-carbazole was used instead of 4-(tert-butyl)aniline.

MS: [M+H]$^+$=592

Preparation Example 129: Synthesis of Compound 31-4

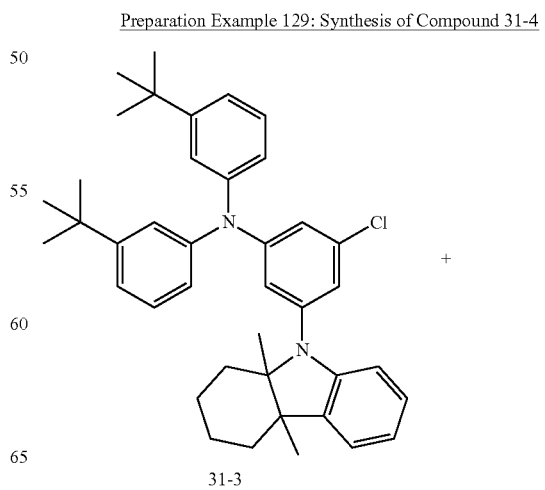

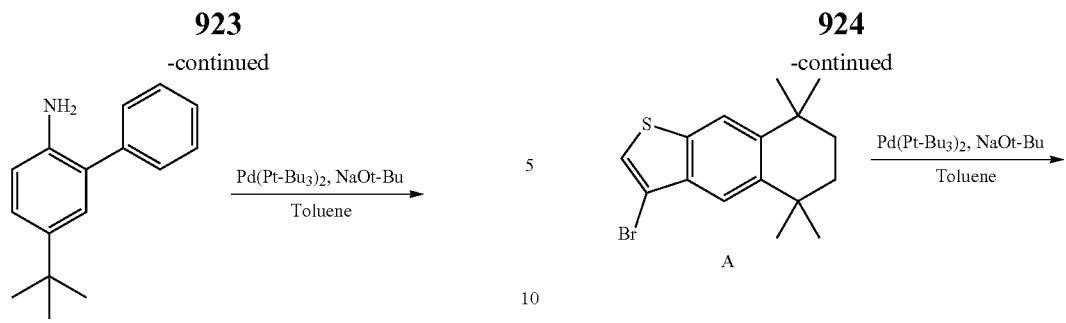

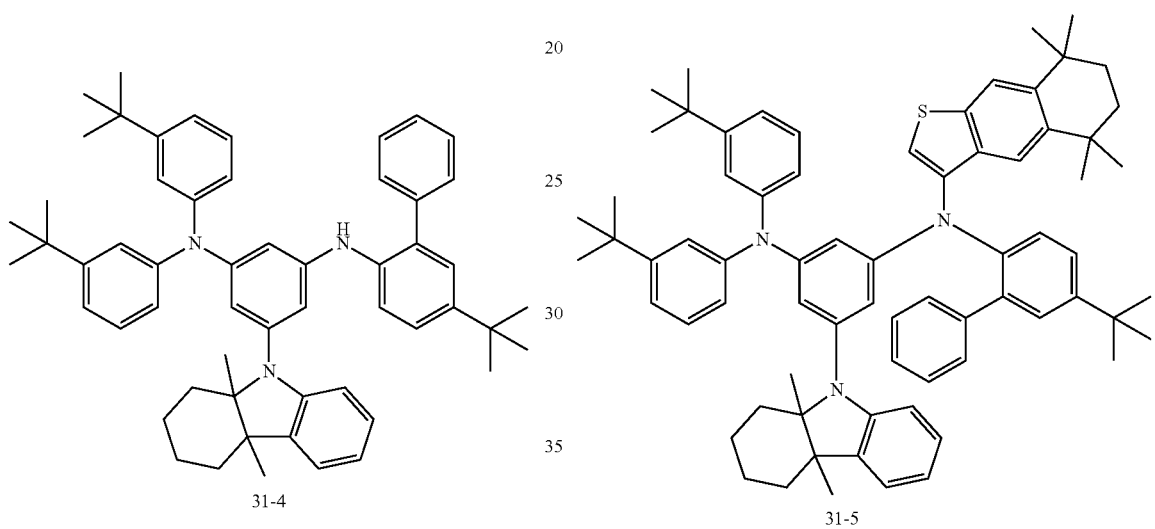

Compound 31-4 was obtained in the same manner as in Preparation of Compound 1-3 of Preparation Example 10 except that Compound 31-3 was used instead of Compound 1-2, and 5-(tert-butyl)-[1,1'-biphenyl]-2-amine was used instead of 4-(tert-butyl)aniline.

MS: [M+H]$^+$=781

Compound 31-5 was obtained in the same manner as in Preparation of Compound 1-4 of Preparation Example 11 except that Compound 31-4 was used instead of Compound 1-3.

MS: [M+H]$^+$=1023

Preparation Example 130: Synthesis of Compound 31-5

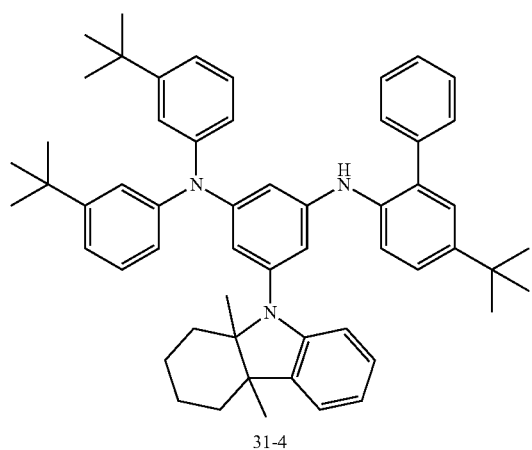

Preparation Example 130-1: Synthesis of Compound 31

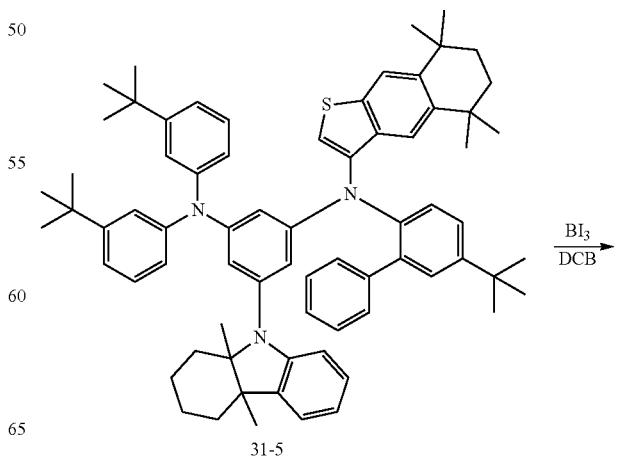

-continued

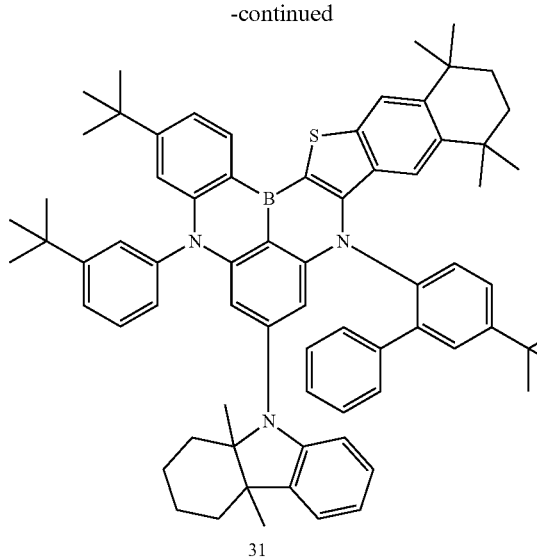

31

Compound 31 was obtained in the same manner as in Preparation of Compound 1 of Preparation Example 12 except that Compound 31-5 was used instead of Compound 1-4.

MS: [M+H]$^+$=1031

Preparation Example 131: Synthesis of Compound 32-1

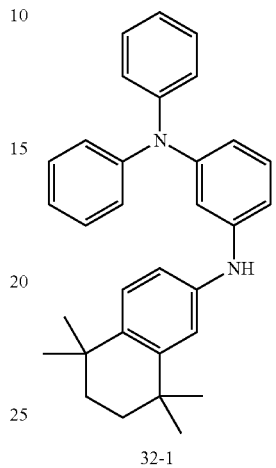

32-1

Compound 32-1 was obtained in the same manner as in Preparation of Compound 1-1 of Preparation Example 8 except that N1,N1-diphenylbenzene-1,3-diamine was used instead of 5-(tert-butyl)-[1,1'-biphenyl]-2-amine.

MS: [M+H]$^+$=447

Preparation Example 132: Synthesis of Compound 32-2

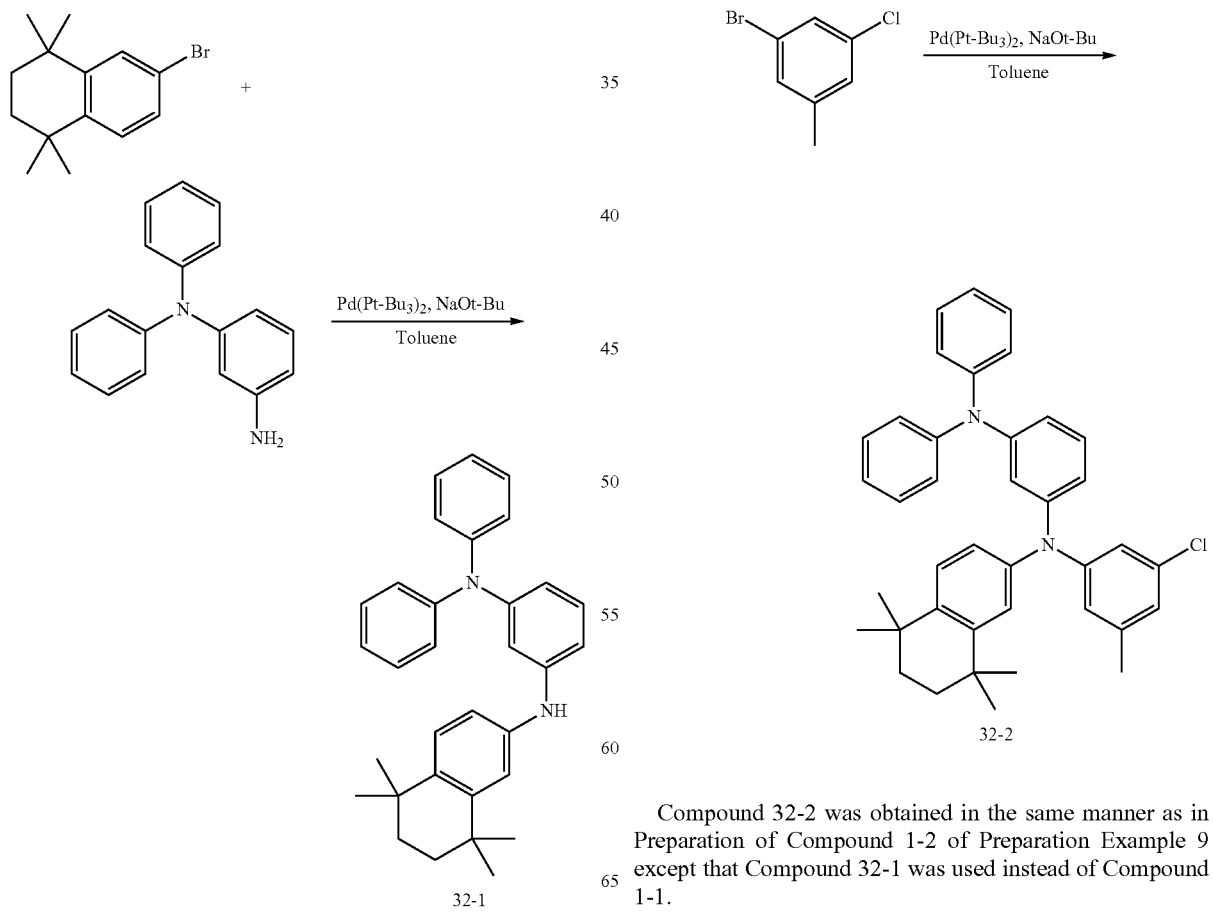

32-2

Compound 32-2 was obtained in the same manner as in Preparation of Compound 1-2 of Preparation Example 9 except that Compound 32-1 was used instead of Compound 1-1.

MS: [M+H]$^+$=572

Preparation Example 133: Synthesis of Compound 32-3

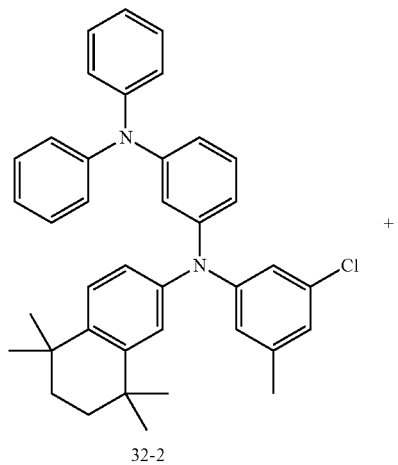

Preparation Example 134: Synthesis of Compound 32-4

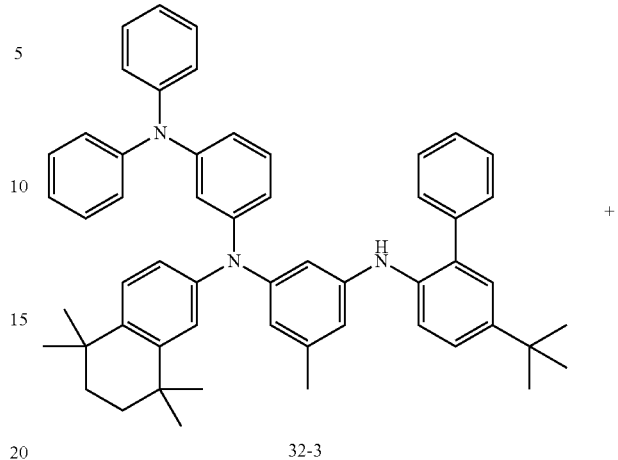

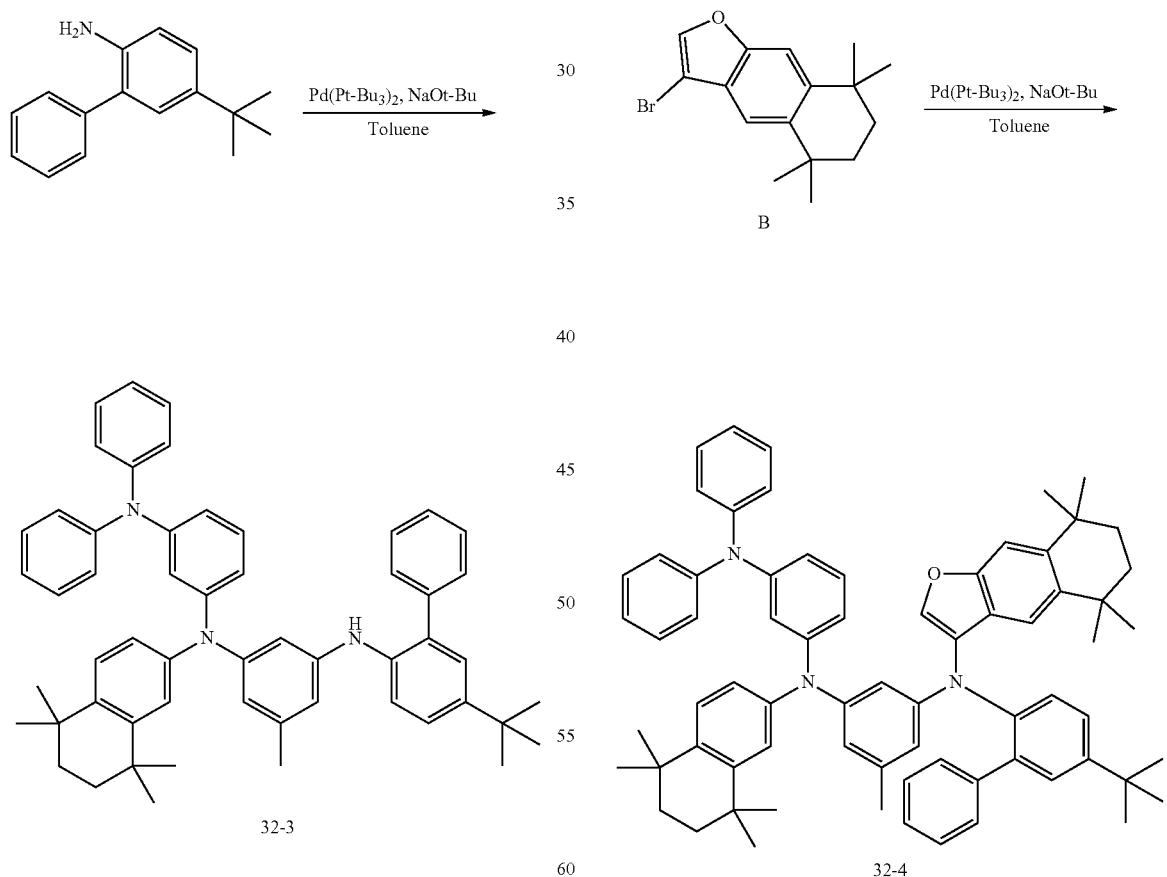

Compound 32-3 was obtained in the same manner as in Preparation of Compound 1-3 of Preparation Example 10 except that Compound 32-2 was used instead of Compound 1-2, and 5-(tert-butyl)-[1,1'-biphenyl]-2-amine was used instead of 4-(tert-butyl)aniline.

MS: [M+H]$^+$=761

Compound 32-4 was obtained in the same manner as in Preparation of Compound 1-4 of Preparation Example 11 except that Compound 32-3 was used instead of Compound 1-3, and Compound B was used instead of Compound A.

MS: [M+H]$^+$=987

Preparation Example 135: Synthesis of Compound 32

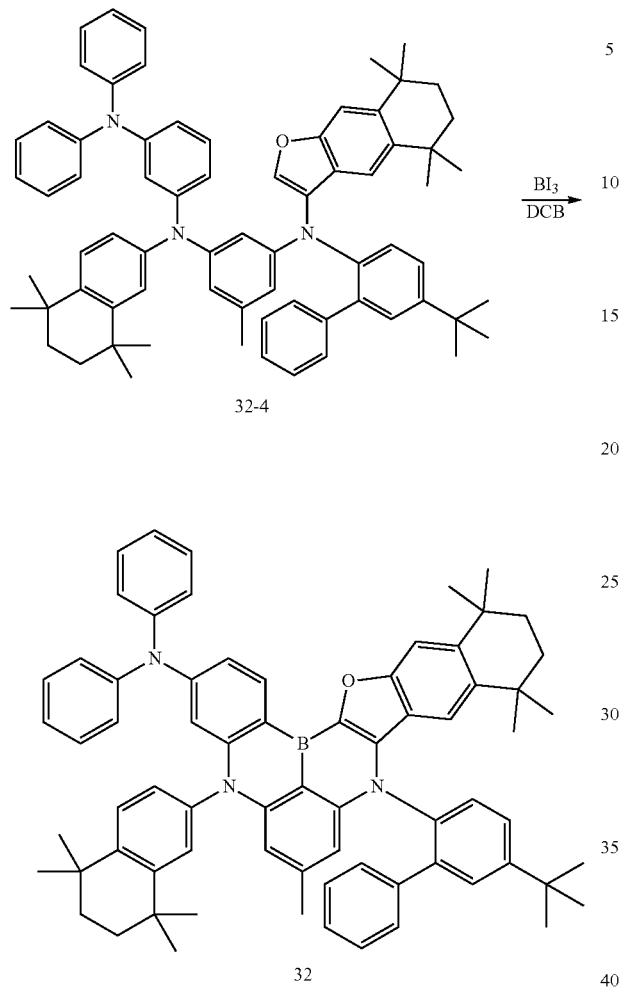

Compound 32 was obtained in the same manner as in Preparation of Compound 1 of Preparation Example 12 except that Compound 32-4 was used instead of Compound 1-4.

MS: [M+H]⁺=995

Preparation Example 136: Synthesis of Compound 33-1

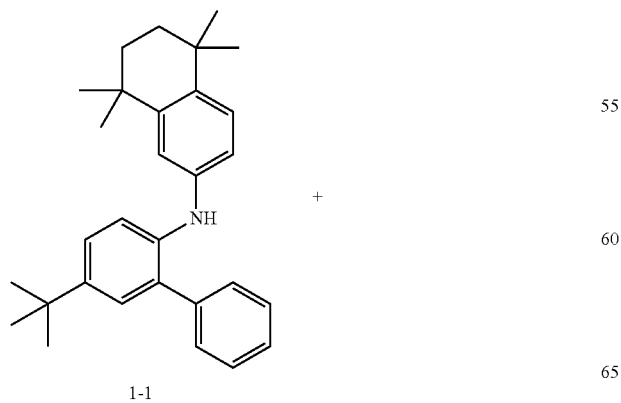

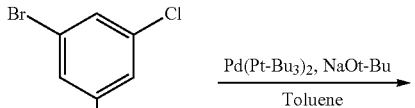

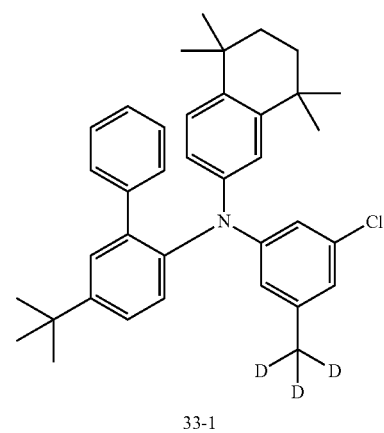

Compound 33-1 was obtained in the same manner as in Preparation of Compound 1-2 of Preparation Example 9 except that 1-bromo-3-chloro-5-(methyl-d3)benzene was used instead of 1-bromo-3-chloro-5-methylbenzene.

MS: [M+H]⁺=540

Preparation Example 137: Synthesis of Compound 33-2

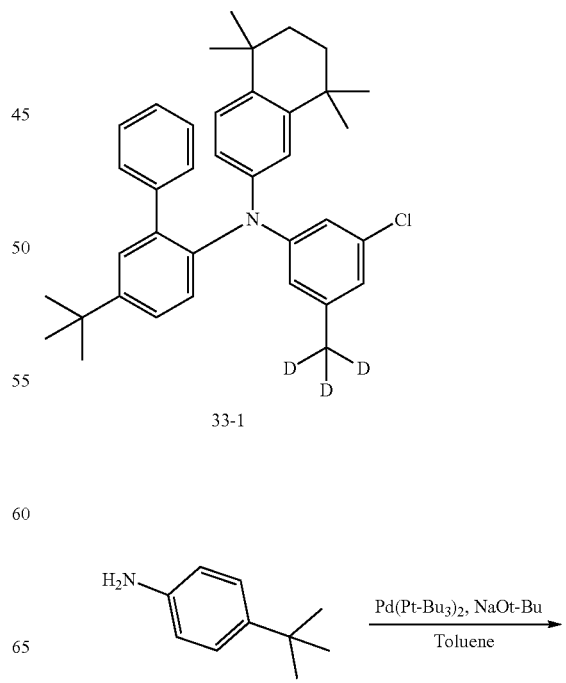

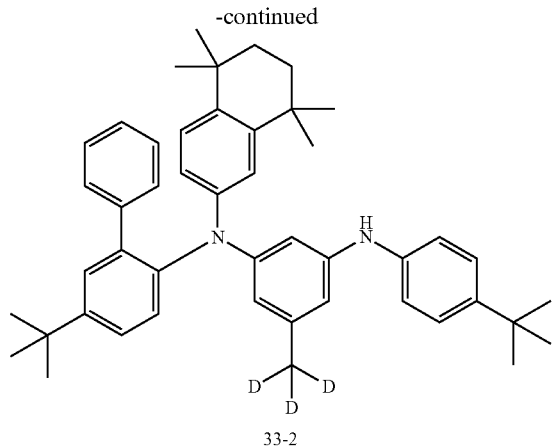

33-2

Compound 33-2 was obtained in the same manner as in Preparation of Compound 1-3 of Preparation Example 10 except that Compound 33-1 was used instead of Compound 1-2.

MS: [M+H]⁺=653

Preparation Example 138: Synthesis of Compound 33-3

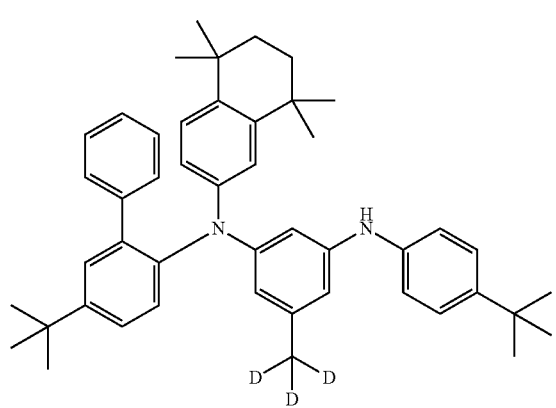

Compound 33-3 was obtained in the same manner as in Preparation of Compound 1-4 of Preparation Example 11 except that Compound 33-2 was used instead of Compound 1-3, and 3-bromo-5-(tert-butyl)benzo[b]thiophene was used instead of Compound A.

MS: [M+H]⁺=841

Preparation Example 139: Synthesis of Compound 33

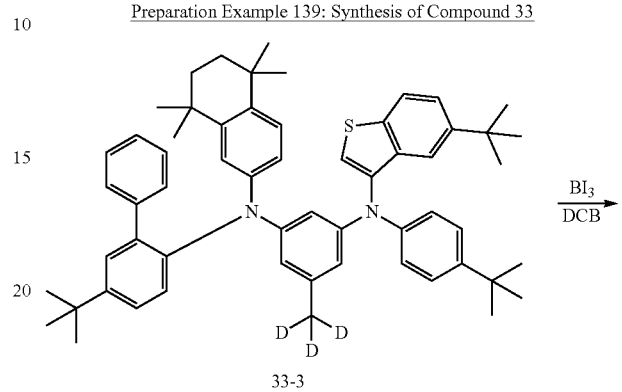

Compound 33 was obtained in the same manner as in Preparation of Compound 1 of Preparation Example 12 except that Compound 33-3 was used instead of Compound 1-4.

MS: [M+H]⁺=848

Preparation Example 140: Synthesis of Compound 34-1

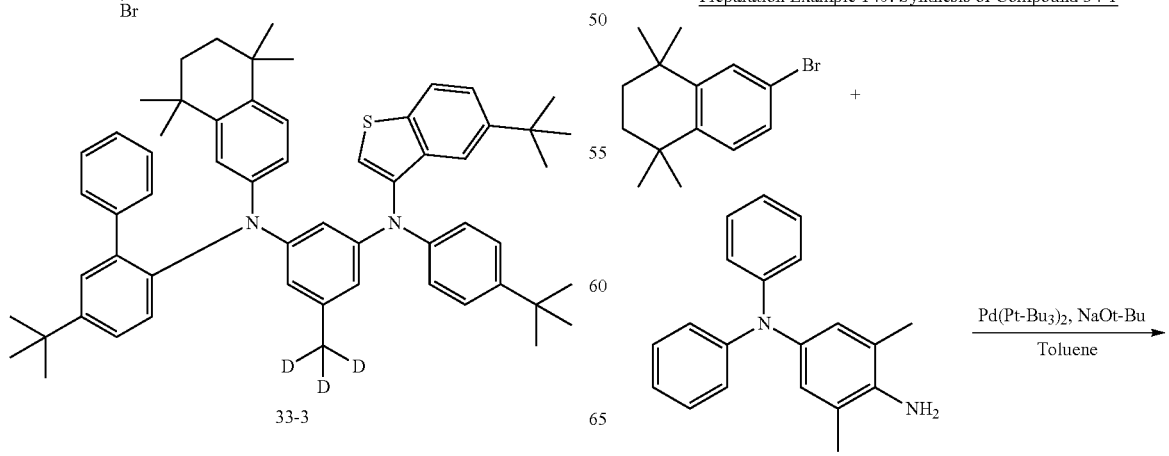

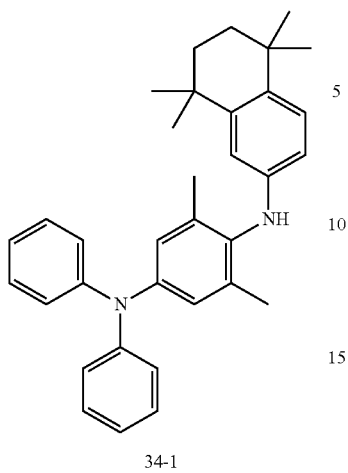

34-1

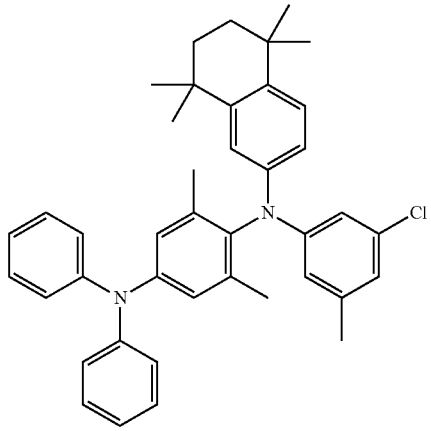

34-2

Compound 34-1 was obtained in the same manner as in Preparation of Compound 1-1 of Preparation Example 8 except that 2,6-dimethyl-N4,N4-diphenyl-N1-(5,5,8,8-tetramethyl-5,6,7,8-tetrahydronaphthalen-2-yl)benzene-1,4-diamine was used instead of 5-(tert-butyl)-[1,1'-biphenyl]-2-amine.

MS: [M+H]$^+$=475

Compound 34-2 was obtained in the same manner as in Preparation of Compound 1-2 of Preparation Example 9 except that Compound 34-1 was used instead of Compound 1-1.

MS: [M+H]$^+$=600

Preparation Example 141: Synthesis of Compound 34-2

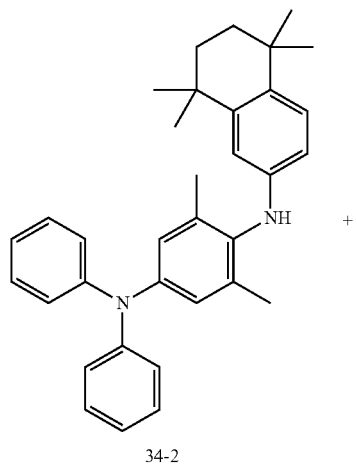

34-2

Preparation Example 142: Synthesis of Compound 34-3

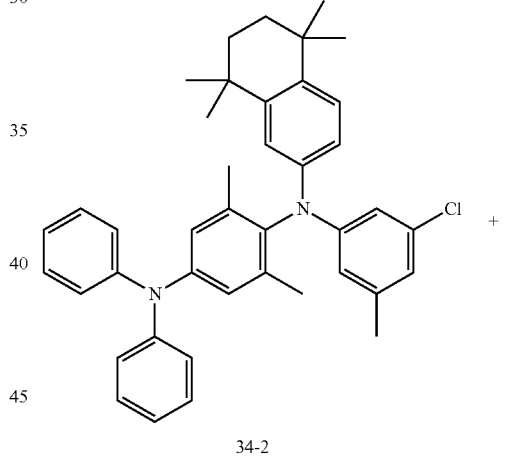

34-2

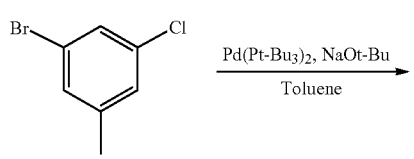

Pd(Pt-Bu$_3$)$_2$, NaOt-Bu
Toluene
$\longrightarrow$

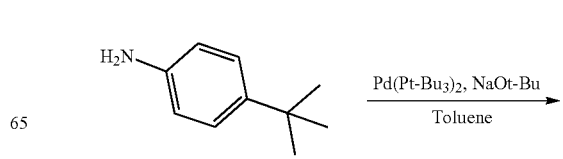

Pd(Pt-Bu$_3$)$_2$, NaOt-Bu
Toluene
$\longrightarrow$

-continued

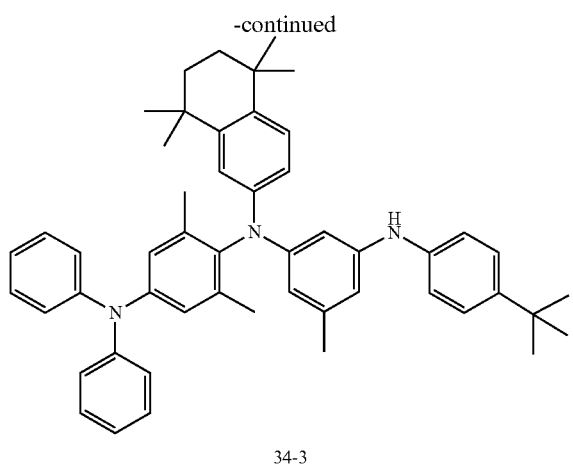

34-3

Compound 34-3 was obtained in the same manner as in Preparation of Compound 1-3 of Preparation Example 10 except that Compound 34-2 was used instead of Compound 1-2.

MS: $[M+H]^+=713$

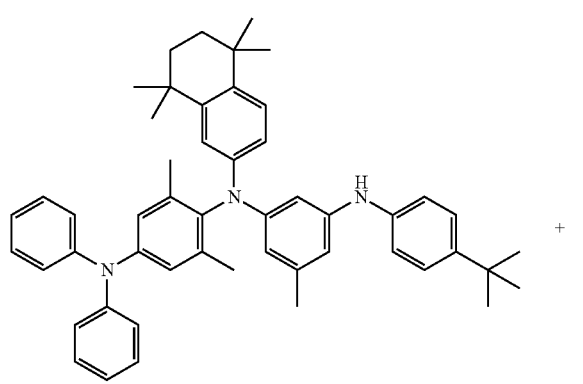

34-4

Compound 34-4 was obtained in the same manner as in Preparation of Compound 1-4 of Preparation Example 11 except that Compound 34-3 was used instead of Compound 1-3, and 3-bromo-5-(tert-butyl)benzo[b]thiophene was used instead of Compound A.

MS: $[M+H]^+=901$

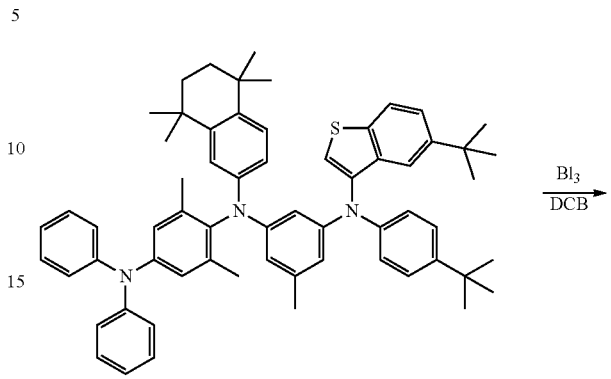

34-4

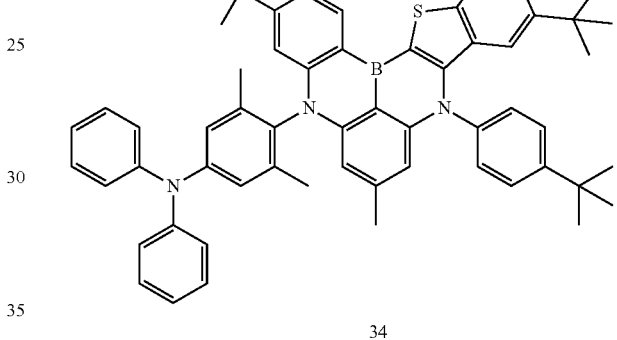

34

Compound 34 was obtained in the same manner as in Preparation of Compound 1 of Preparation Example 12 except that Compound 34-4 was used instead of Compound 1-4.

MS: $[M+H]^+=909$

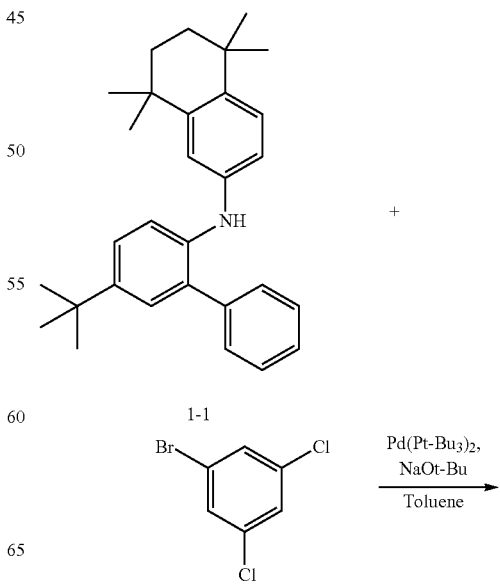

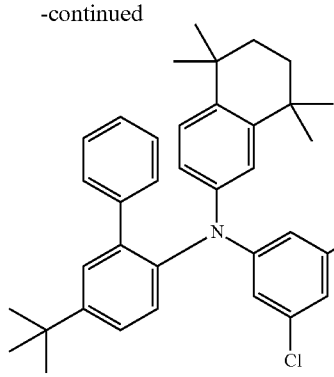

35-1

Compound 35-1 was obtained in the same manner as in Preparation of Compound 1-2 of Preparation Example 9 except that 1-bromo-3,5-dichlorobenzene was used instead of 1-bromo-3-chloro-5-methylbenzene.

MS: [M+H]⁺=557

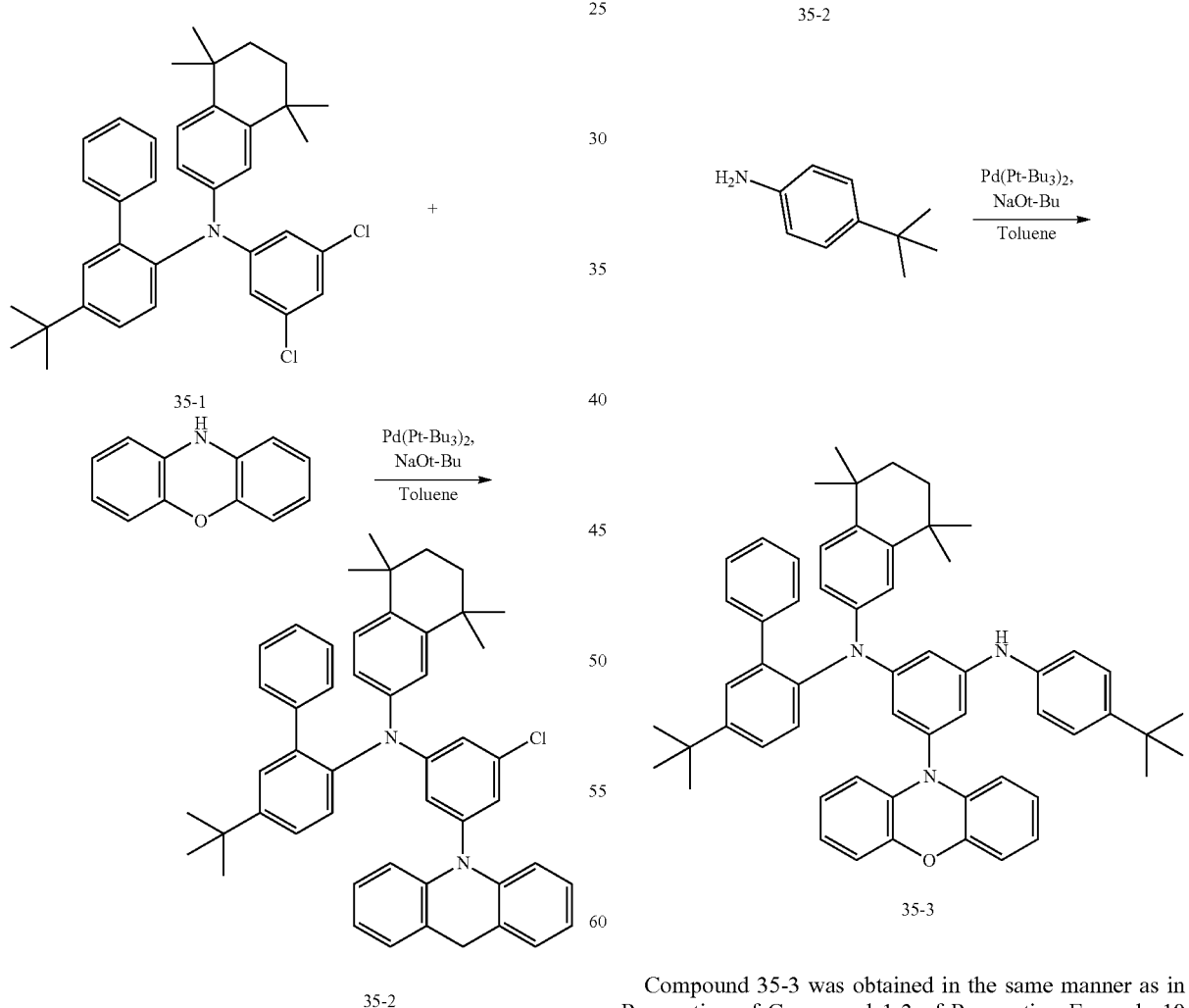

35-2

Compound 35-2 was obtained in the same manner as in Preparation of Compound 1-3 of Preparation Example 10 except that Compound 35-1 was used instead of Compound 1-2, and 10H-phenoxazine was used instead of 4-(tert-butyl)aniline.

MS: [M+H]⁺=704

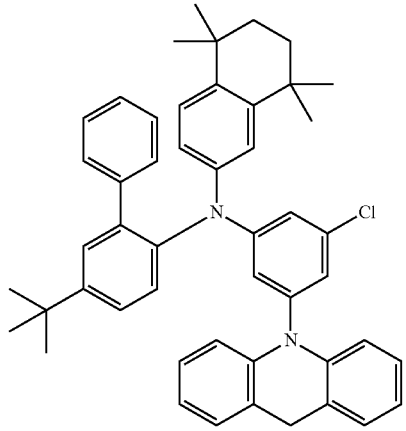

35-3

Compound 35-3 was obtained in the same manner as in Preparation of Compound 1-3 of Preparation Example 10 except that Compound 35-2 was used instead of Compound 1-2.

MS: [M+H]⁺=817

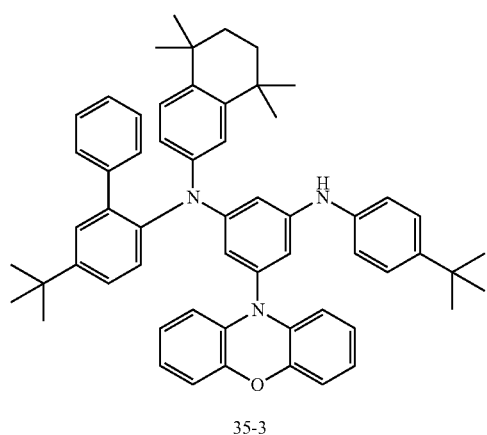

35-3

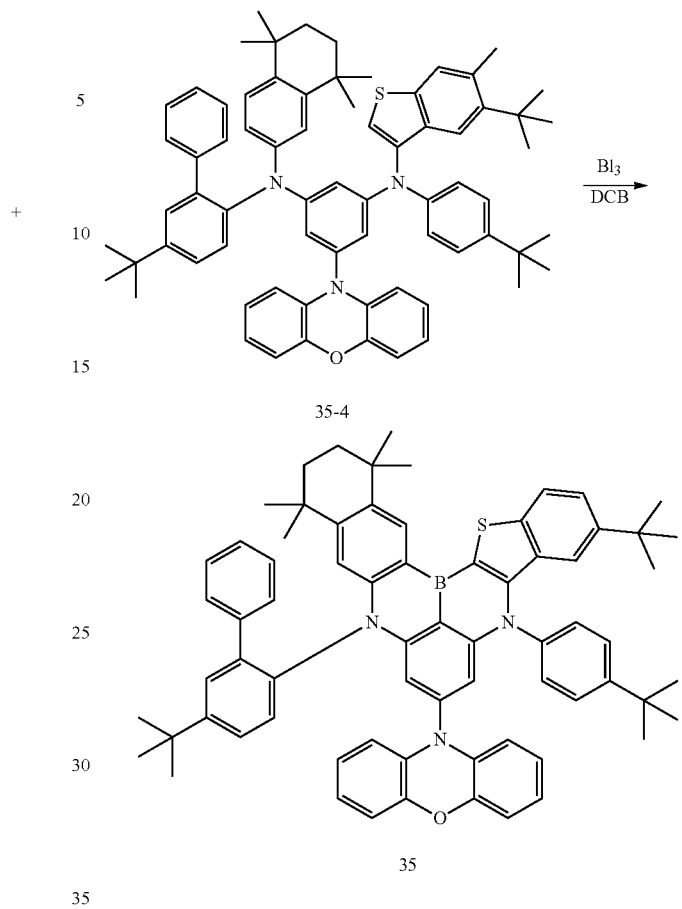

35-4

Compound 35 was obtained in the same manner as in Preparation of Compound 1 of Preparation Example 12 except that Compound 35-4 was used instead of Compound 1-4.

MS: [M+H]⁺=1013

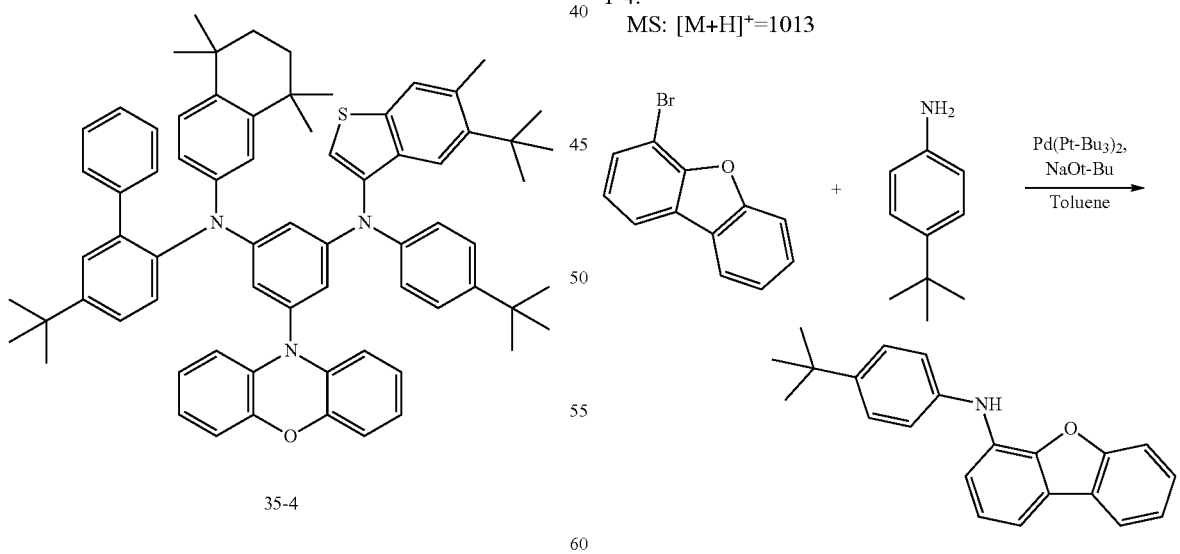

35-4

Compound 35-4 was obtained in the same manner as in Preparation of Compound 1-4 of Preparation Example 11 except that Compound 35-3 was used instead of Compound 1-3, and 3-bromo-5-(tert-butyl)benzo[b]thiophene was used instead of Compound A.

MS: [M+H]⁺=1005

36-1

Compound 36-1 was obtained in the same manner as in Preparation of Compound 1-1 of Preparation Example 8 except that 4-bromodibenzo[b,d]furan was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]$^+$=316

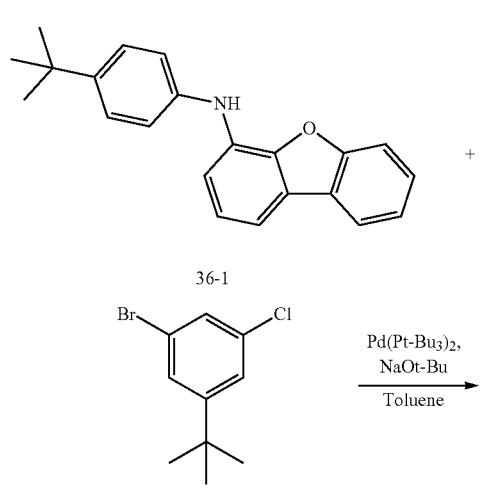

36-1

Compound 36-2 was obtained in the same manner as in Preparation of Compound 1-2 of Preparation Example 9 except that Compound 36-1 was used instead of Compound 1-1, and 1-bromo-3-(tert-butyl)-5-chlorobenzene was used instead of 1-bromo-3-chloro-5-methylbenzene.

MS: [M+H]$^+$=483

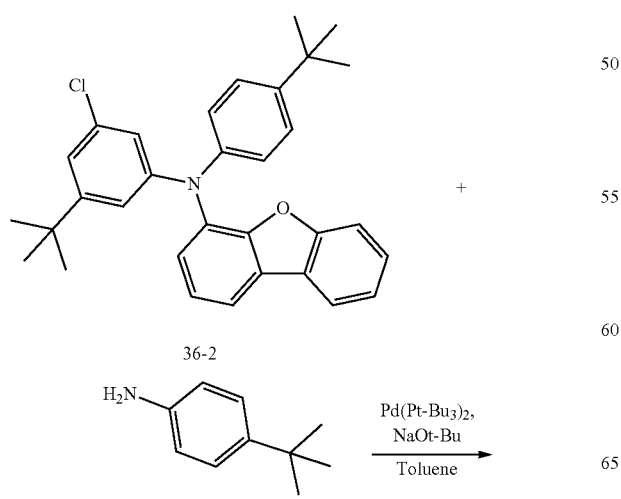

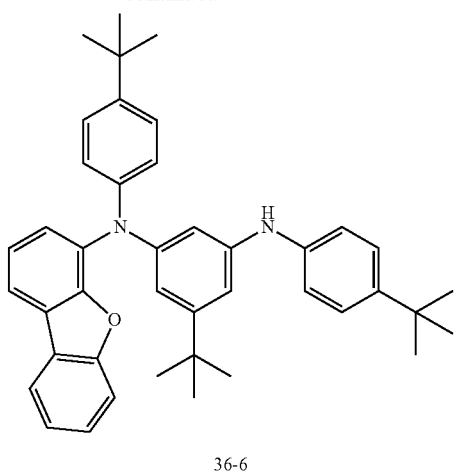

36-6

Compound 36-3 was obtained in the same manner as in Preparation of Compound 1-3 of Preparation Example 10 except that Compound 36-2 was used instead of Compound 1-2.

MS: [M+H]$^+$=595

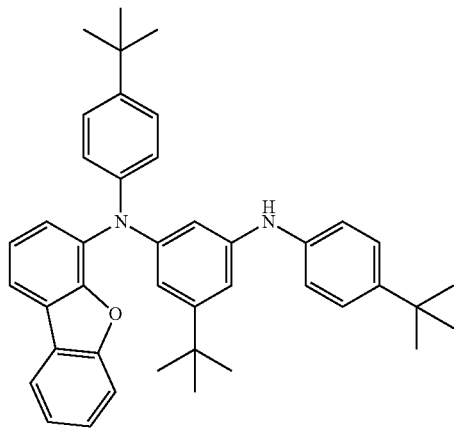

36-6

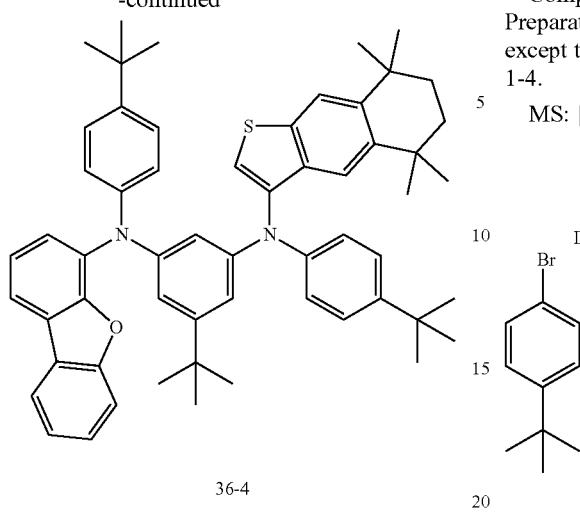

36-4

Compound 36-4 was obtained in the same manner as in Preparation of Compound 1-4 of Preparation Example 11 except that Compound 36-3 was used instead of Compound 1-3.

MS: [M+H]⁺=838

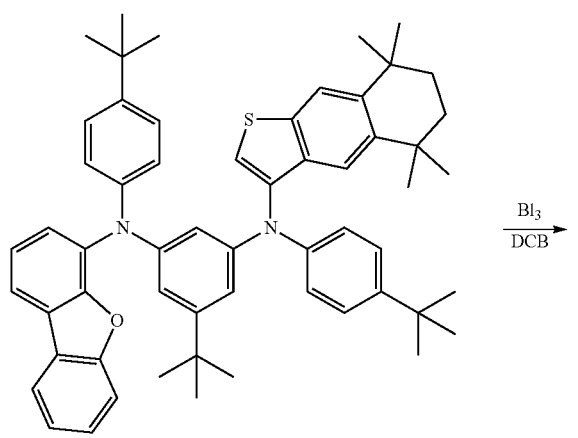

36

Compound 36 was obtained in the same manner as in Preparation of Compound 1 of Preparation Example 12 except that Compound 36-4 was used instead of Compound 1-4.

MS: [M+H]⁺=846

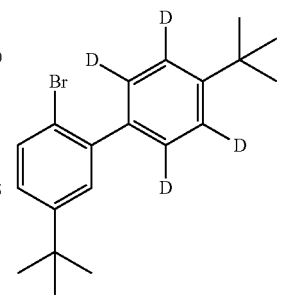

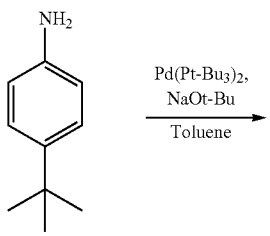

37-1

Compound 37-1 was obtained in the same manner as in Preparation of Compound 1-1 of Preparation Example 8 except that 2-bromo-4',5-di-tert-butyl-1,1'-biphenyl-2',3',5',6'-d4 was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]⁺=418

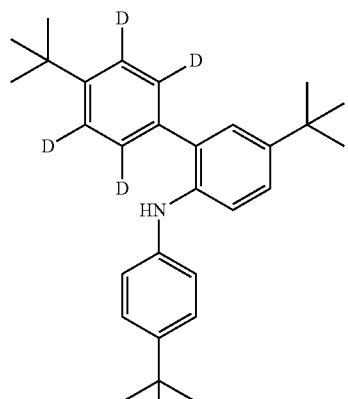

37-1

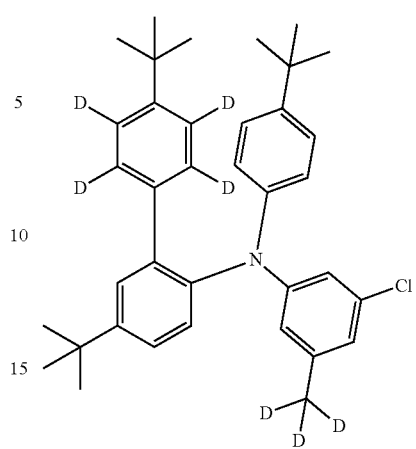

37-2

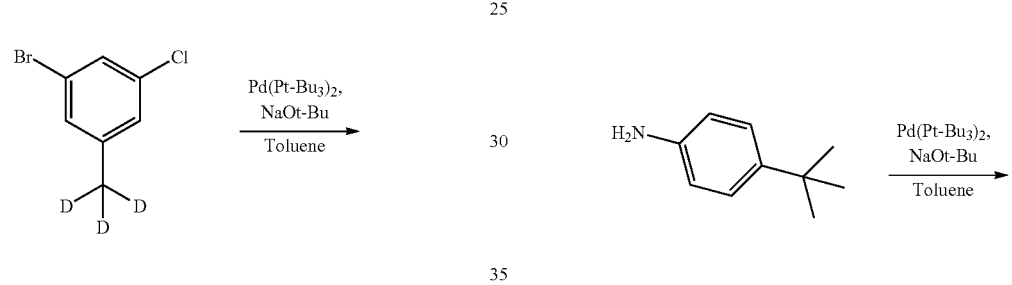

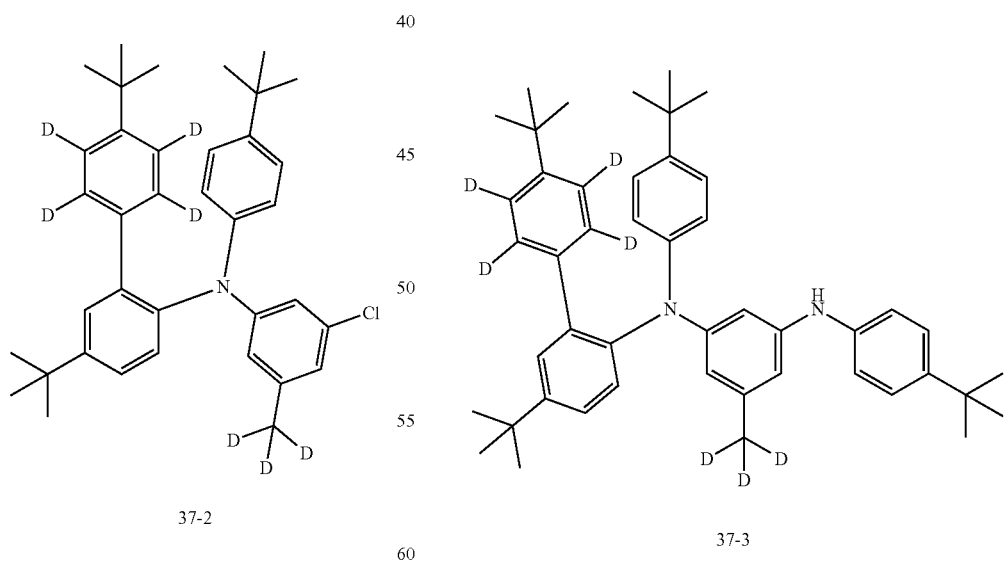

37-2

37-3

Compound 37-2 was obtained in the same manner as in Preparation of Compound 1-2 of Preparation Example 9 except that Compound 37-1 was used instead of Compound 1-1, and 1-bromo-3-chloro-5-(methyl-d3)benzene was used instead of 1-bromo-3-chloro-5-methylbenzene.

MS: [M+H]$^+$=546

Compound 37-3 was obtained in the same manner as in Preparation of Compound 1-3 of Preparation Example 10 except that Compound 37-2 was used instead of Compound 1-2.

MS: [M+H]$^+$=659

Preparation Example 158: Synthesis of Compound 37-4

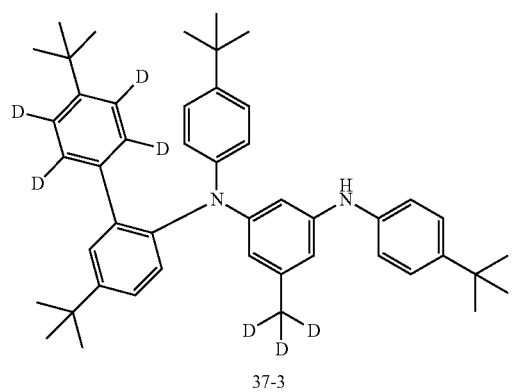

37-3

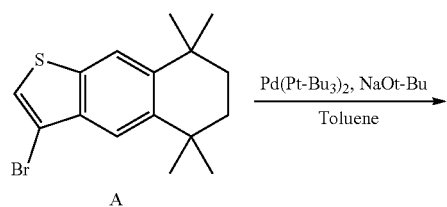

A

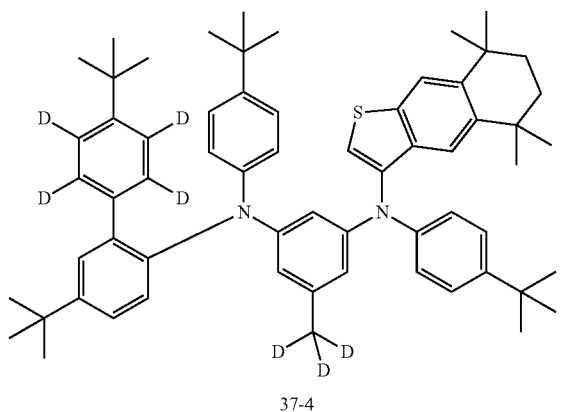

37-4

Compound 37-4 was obtained in the same manner as in Preparation of Compound 1-4 of Preparation Example 11 except that Compound 37-3 was used instead of Compound 1-3.

MS: [M+H]$^+$=901

Preparation Example 159: Synthesis of Compound 37

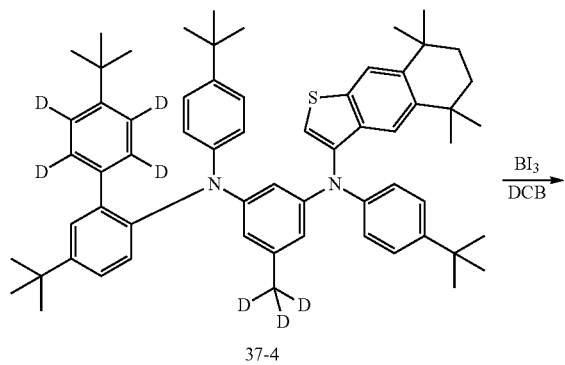

37-4

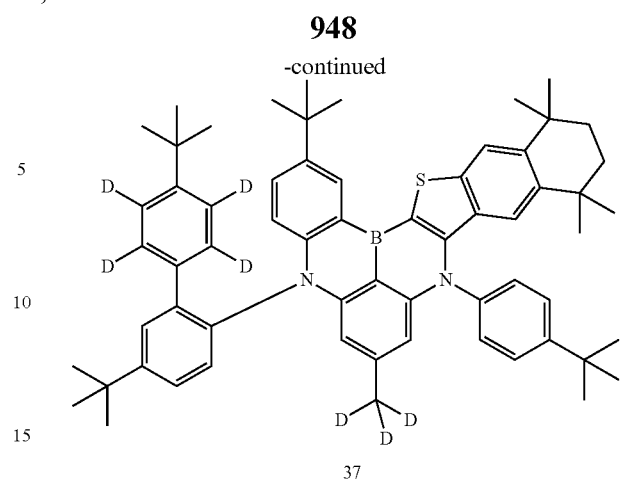

37

Compound 37 was obtained in the same manner as in Preparation of Compound 1 of Preparation Example 12 except that Compound 37-4 was used instead of Compound 1-4.

MS: [M+H]$^+$=909

Preparation Example 160: Synthesis of Compound 38-1

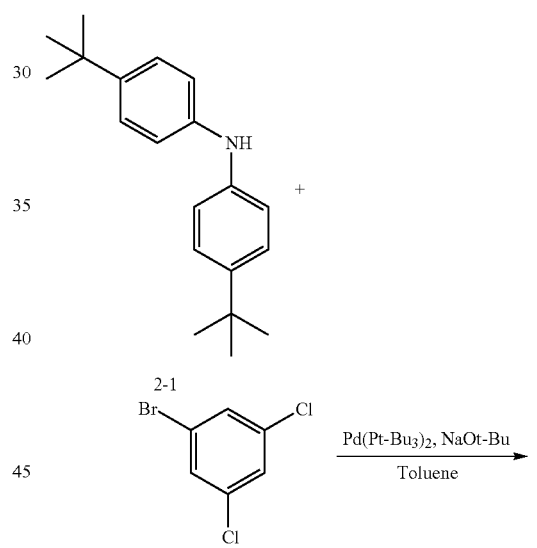

2-1

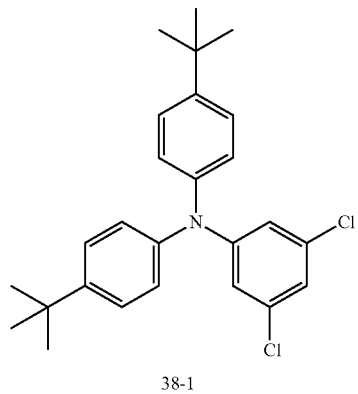

38-1

Compound 38-1 was obtained in the same manner as in Preparation of Compound 1-2 of Preparation Example 9 except that Compound 2-1 was used instead of Compound 1-1, and 1-bromo-3,5-dichlorobenzene was used instead of 1-bromo-3-chloro-5-methylbenzene.

MS: [M+H]$^+$=427

Preparation Example 161: Synthesis of Compound 38-2

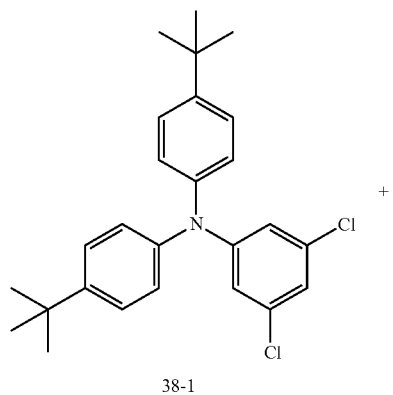

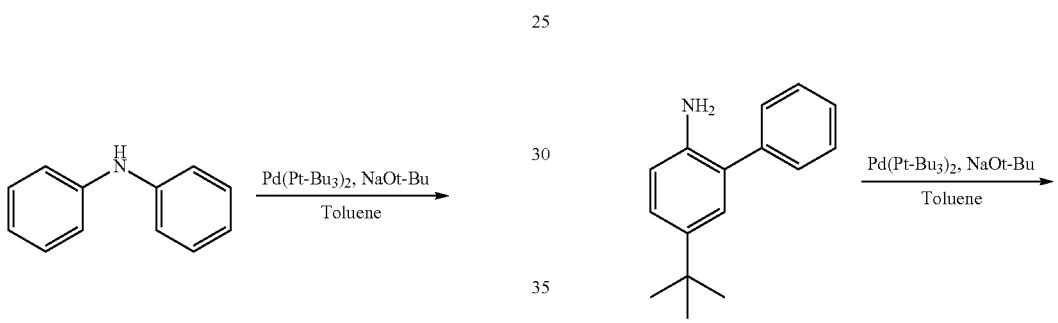

Compound 38-2 was obtained in the same manner as in Preparation of Compound 1-3 of Preparation Example 10 except that Compound 38-1 was used instead of Compound 1-2, and diphenylamine was used instead of 4-(tert-butyl)aniline.

MS: [M+H]$^+$=560

Preparation Example 162: Synthesis of Compound 38-3

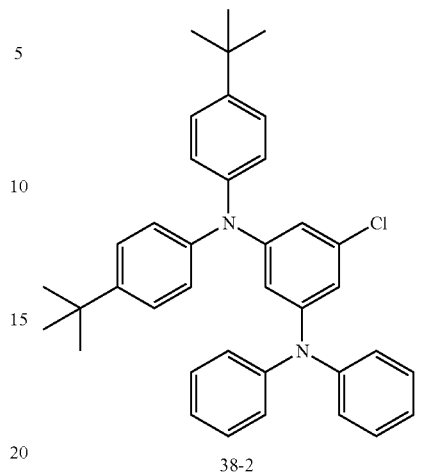

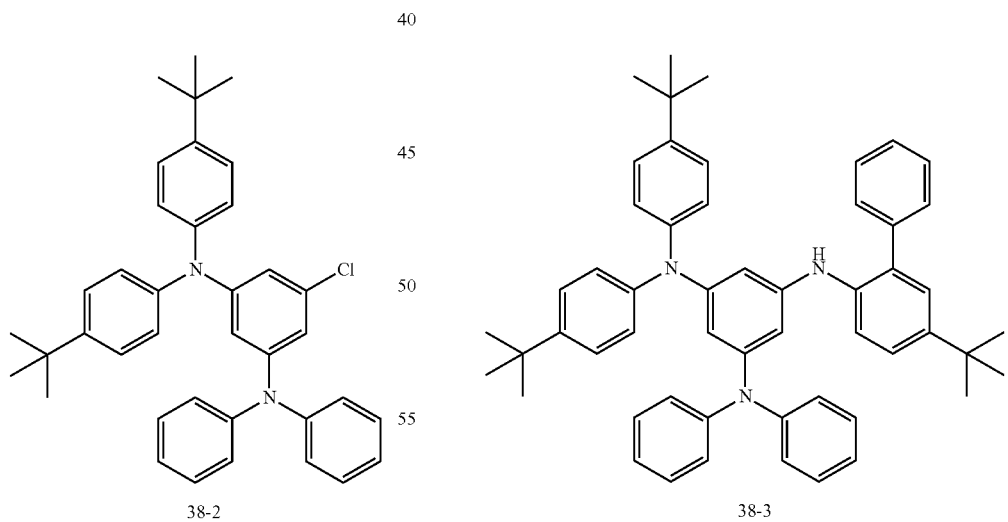

Compound 38-3 was obtained in the same manner as in Preparation of Compound 1-3 of Preparation Example 10 except that Compound 38-2 was used instead of Compound 1-2, and 5-(tert-butyl)-[1,1'-biphenyl]-2-amine was used instead of 4-(tert-butyl)aniline.

MS: [M+H]$^+$=749

Preparation Example 163: Synthesis of Compound 38-4

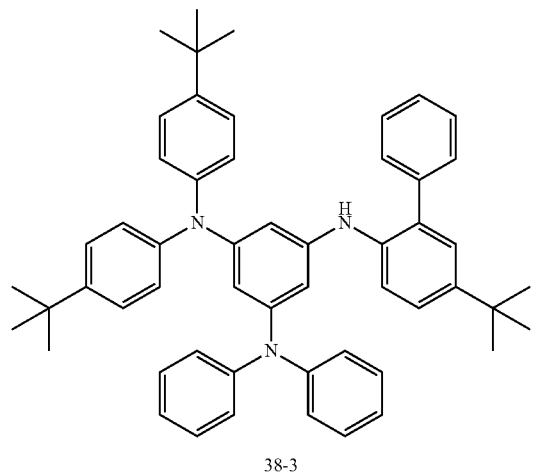

38-3

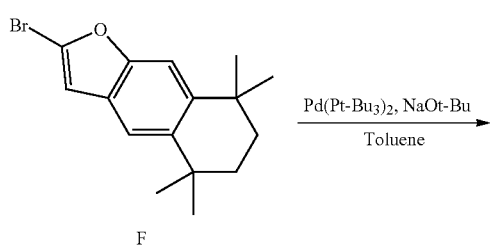

Compound 38-4 was obtained in the same manner as in Preparation of Compound 1-4 of Preparation Example 11 except that Compound 38-3 was used instead of Compound 1-3, and Compound F was used instead of Compound A.

MS: [M+H]$^+$=975

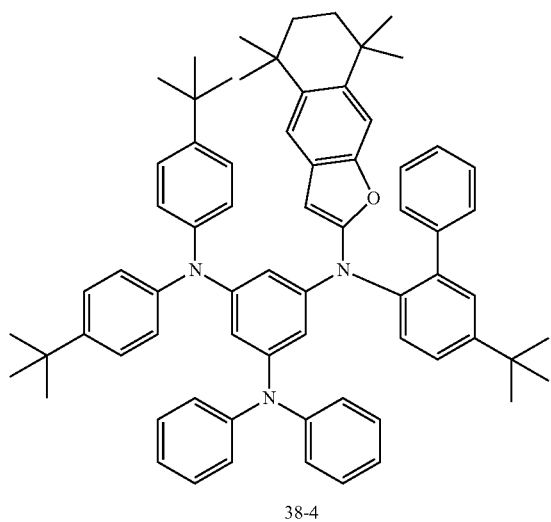

38-4

Preparation Example 163-1: Synthesis of Compound 38

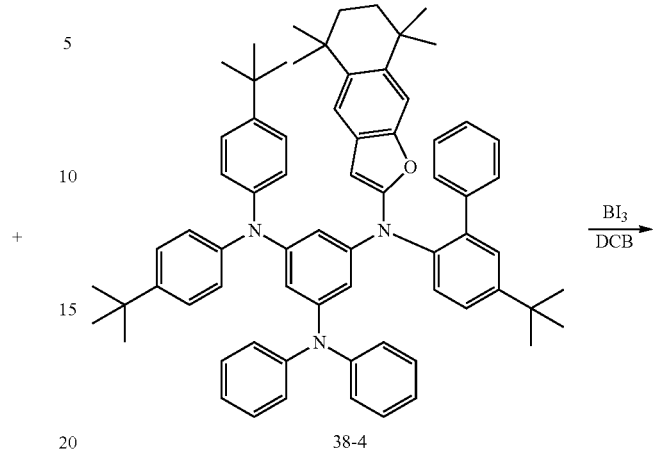

38-4

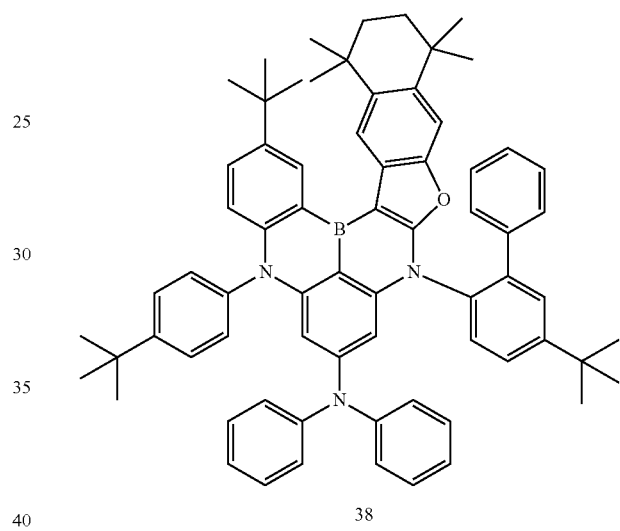

38

Compound 38 was obtained in the same manner as in Preparation of Compound 1 of Preparation Example 12 except that Compound 38-4 was used instead of Compound 1-4.

MS: [M+H]$^+$=909

Preparation Example 164: Synthesis of Compound 39-1

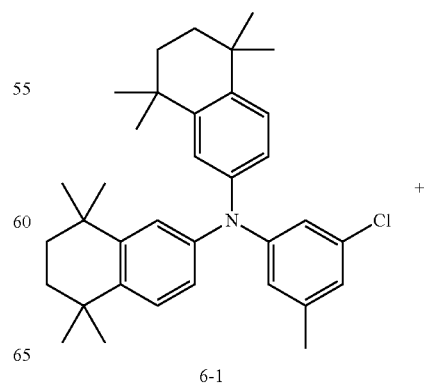

6-1

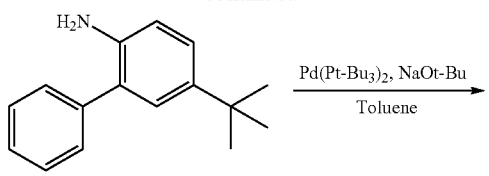

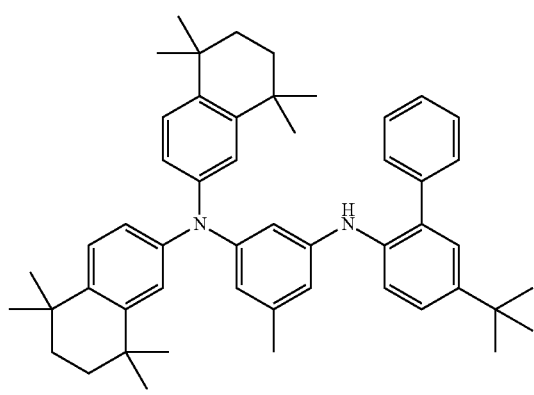

39-1

Compound 39-1 was obtained in the same manner as in Preparation of Compound 1-3 of Preparation Example 10 except that Compound 6-1 was used instead of Compound 1-2, and 5-(tert-butyl)-[1,1'-biphenyl]-2-amine was used instead of 4-(tert-butyl)aniline.

MS: [M+H]$^+$=704

Preparation Example 165: Synthesis of Compound 39-2

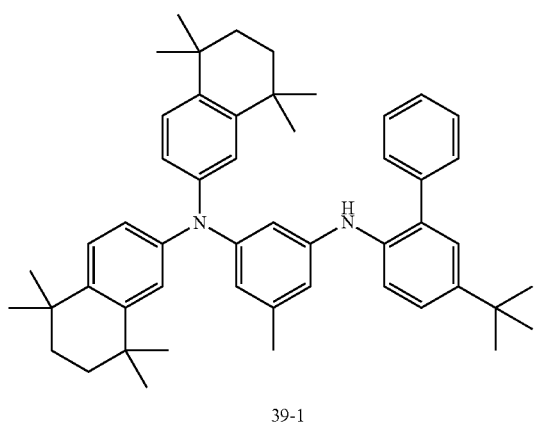

39-1

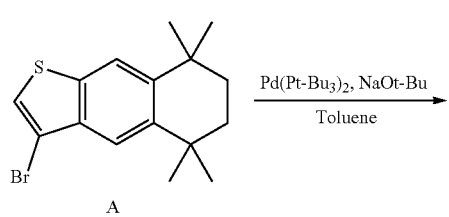

A

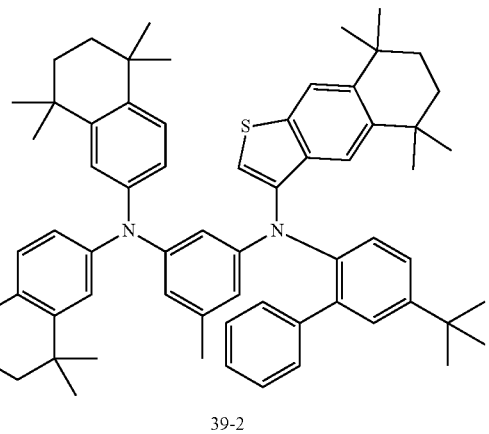

39-2

Compound 39-2 was obtained in the same manner as in Preparation of Compound 1-4 of Preparation Example 11 except that Compound 39-1 was used instead of Compound 1-3.

MS: [M+H]$^+$=946

Preparation Example 166: Synthesis of Compound 39

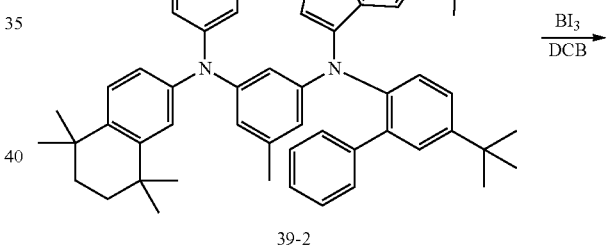

39

Compound 39 was obtained in the same manner as in Preparation of Compound 1 of Preparation Example 12 except that Compound 39-2 was used instead of Compound 1-4.

MS: [M+H]$^+$=954

Preparation Example 167: Synthesis of Compound 40-1

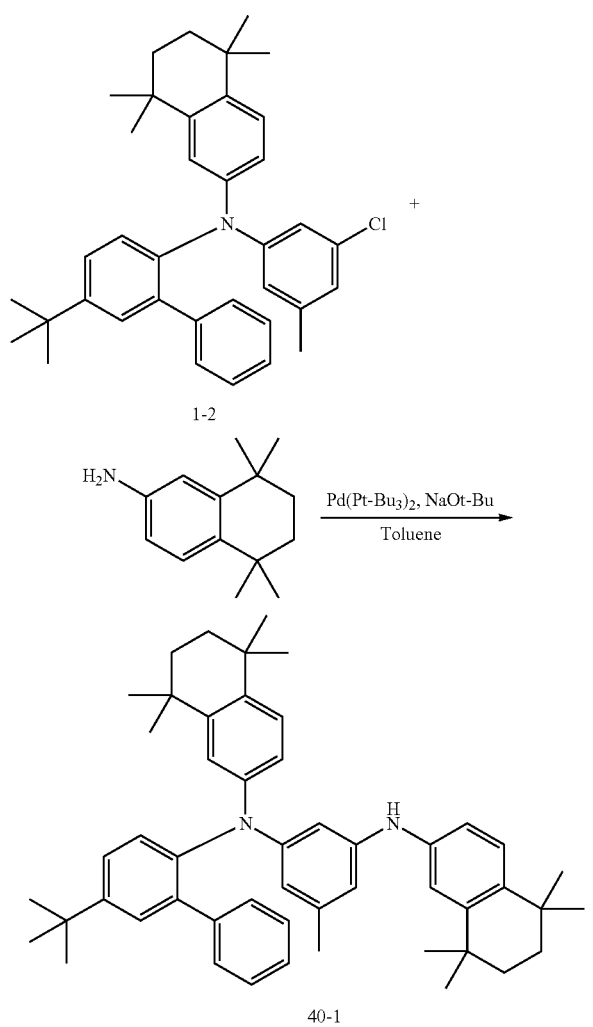

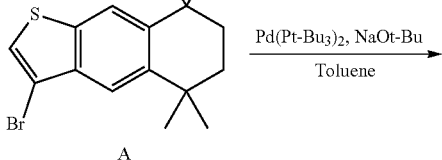

Compound 40-1 was obtained in the same manner as in Preparation of Compound 1-3 of Preparation Example 10 except that 5,5,8,8-tetramethyl-5,6,7,8-tetrahydronaphthalen-2-amine was used instead of 4-(tert-butyl)aniline.

MS: [M+H]⁺=704

Preparation Example 168: Synthesis of Compound 40-2

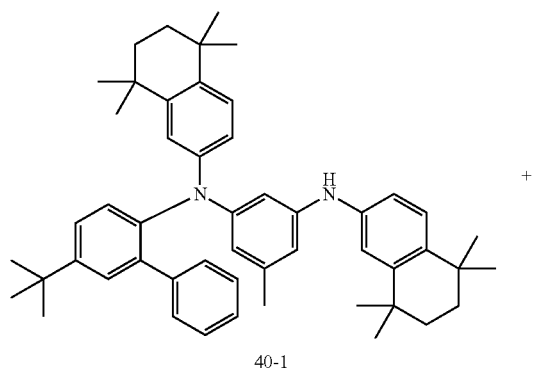

Compound 40-2 was obtained in the same manner as in Preparation of Compound 1-4 of Preparation Example 11 except that Compound 40-1 was used instead of Compound 1-3.

MS: [M+H]⁺=946

Preparation Example 168-1: Synthesis of Compound 40

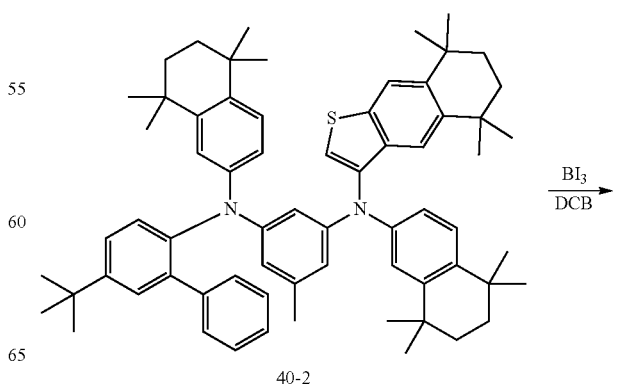

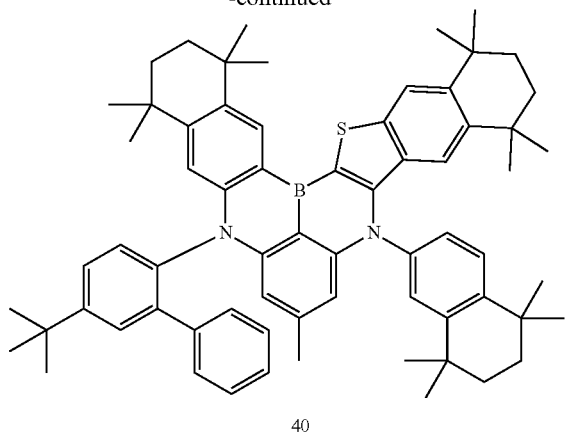

40

Compound 40 was obtained in the same manner as in Preparation of Compound 1 of Preparation Example 12 except that Compound 40-2 was used instead of Compound 1-4.

MS: [M+H]$^+$=954

Preparation Example 169: Synthesis of Compound 41-1

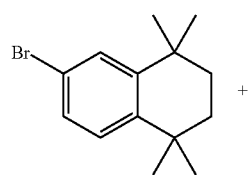

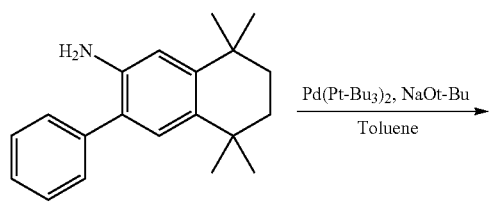

41-1

Compound 41-1 was obtained in the same manner as in Preparation of Compound 1-1 of Preparation Example 8 except that 5,5,8,8-tetramethyl-3-phenyl-5,6,7,8-tetrahydronaphthalen-2-amine was used instead of 5-(tert-butyl)-[1,1'-biphenyl]-2-amine.

MS: [M+H]$^+$=466

Preparation Example 170: Synthesis of Compound 41-2

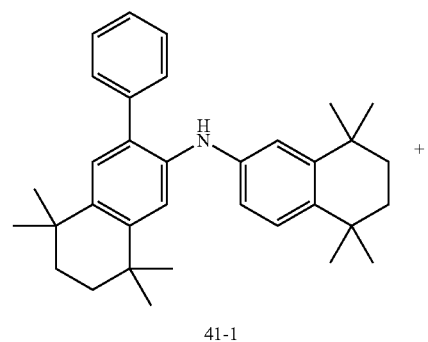

41-1

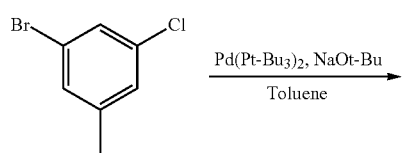

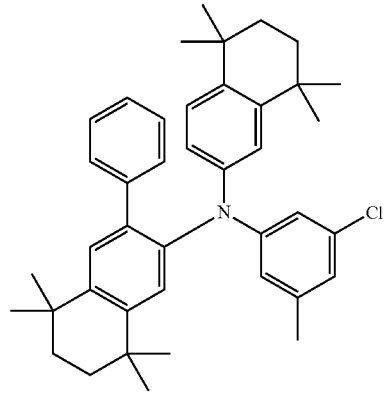

41-2

Compound 41-2 was obtained in the same manner as in Preparation of Compound 1-2 of Preparation Example 9 except that Compound 41-1 was used instead of Compound 1-1.

MS: [M+H]$^+$=591

Preparation Example 171: Synthesis of Compound 41-3

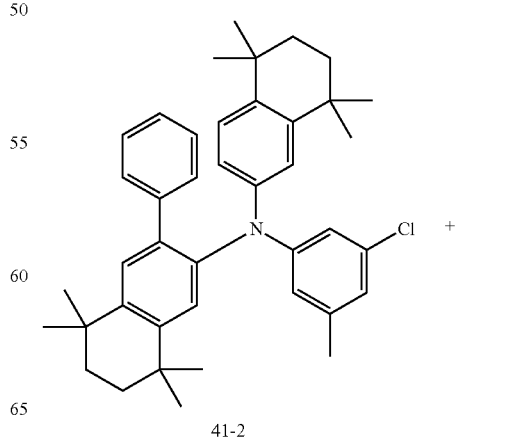

41-2

-continued

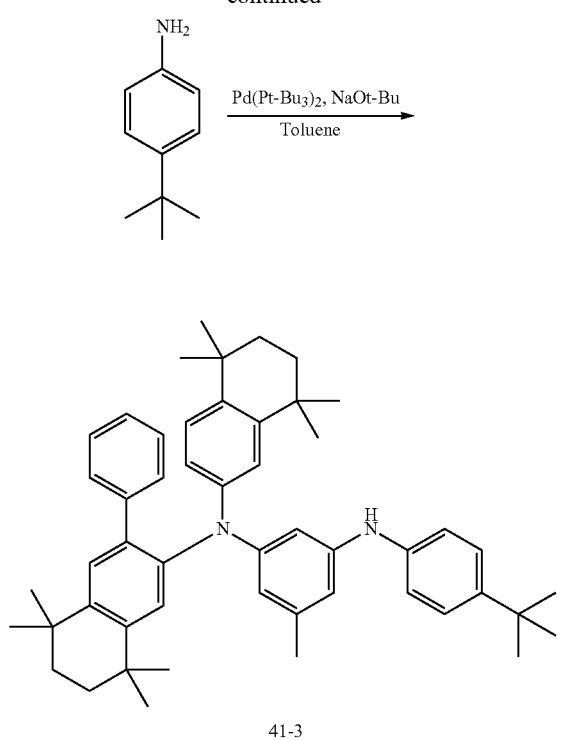

41-3

Compound 41-3 was obtained in the same manner as in Preparation of Compound 1-3 of Preparation Example 10 except that Compound 41-2 was used instead of Compound 1-2.

MS: [M+H]⁺=704

Preparation Example 172: Synthesis of Compound 41-4

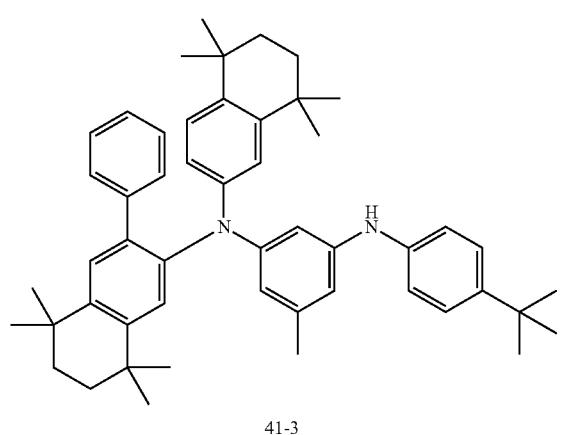

41-3

+

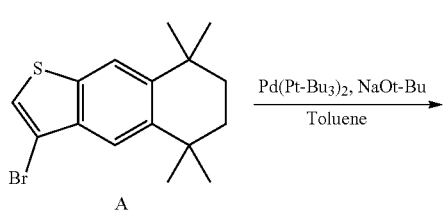

-continued

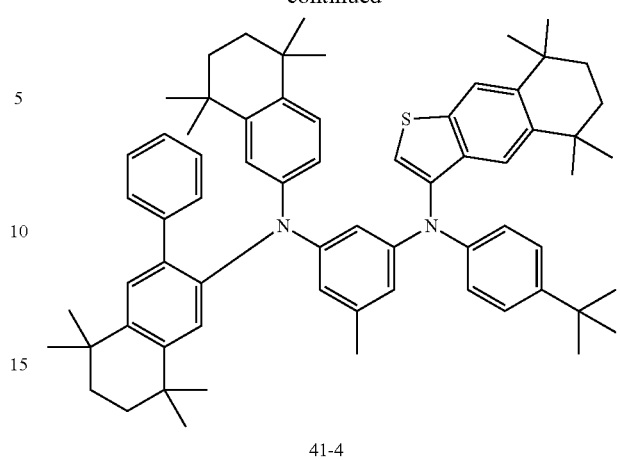

41-4

Compound 41-4 was obtained in the same manner as in Preparation of Compound 1-4 of Preparation Example 11 except that Compound 41-3 was used instead of Compound 1-3.

MS: [M+H]⁺=946

Preparation Example 173: Synthesis of Compound 41

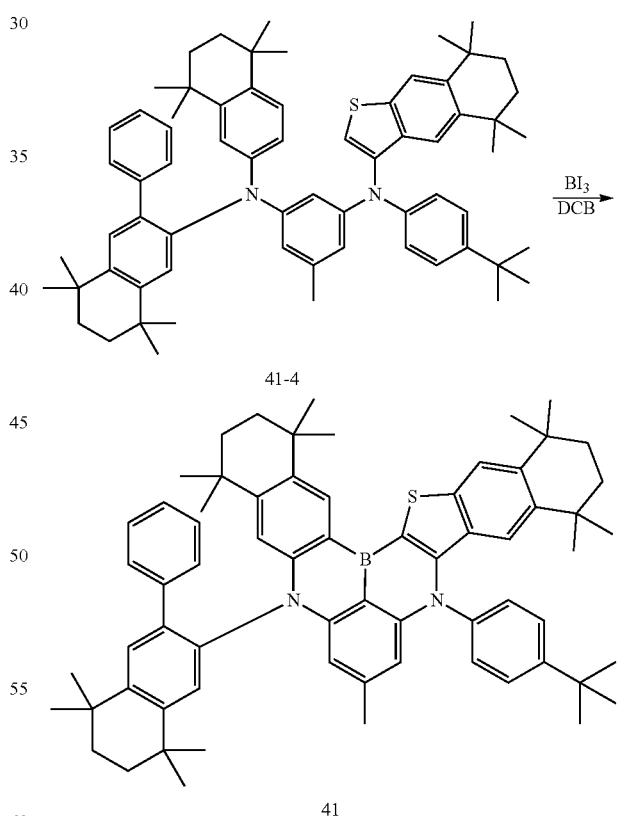

Compound 41 was obtained in the same manner as in Preparation of Compound 1 of Preparation Example 12 except that Compound 41-4 was used instead of Compound 1-4.

MS: [M+H]⁺=954

Preparation Example 174: Synthesis of Compound 42-1

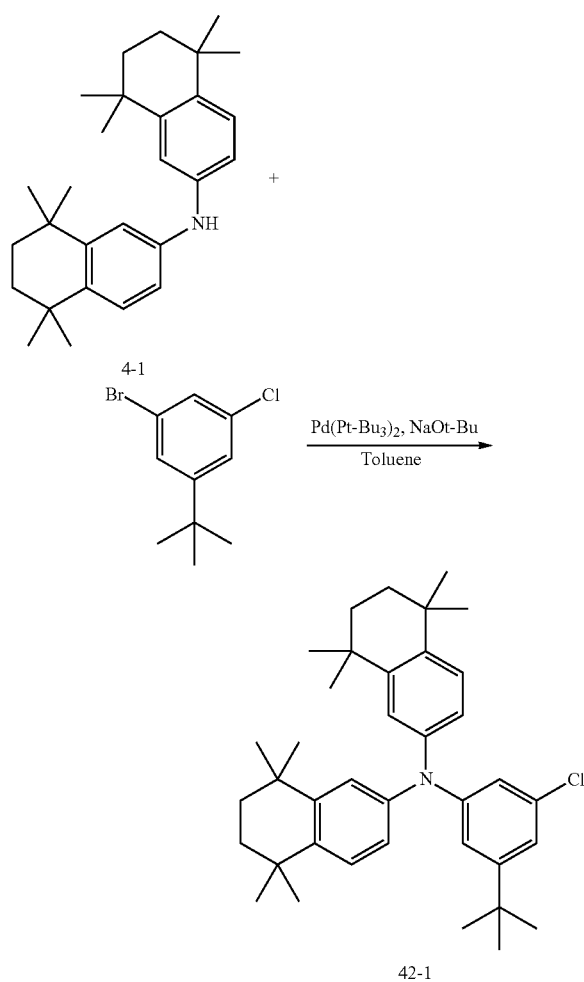

Compound 42-1 was obtained in the same manner as in Preparation of Compound 1-2 of Preparation Example 9 except that Compound 4-1 was used instead of Compound 1-1, and 1-bromo-3-(tert-butyl)-5-chlorobenzene was used instead of 1-bromo-3-chloro-5-methylbenzene.
MS: $[M+H]^+$=557

Preparation Example 175: Synthesis of Compound 42-2

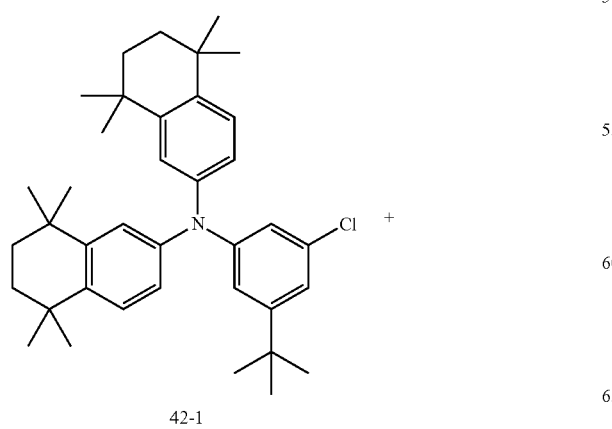

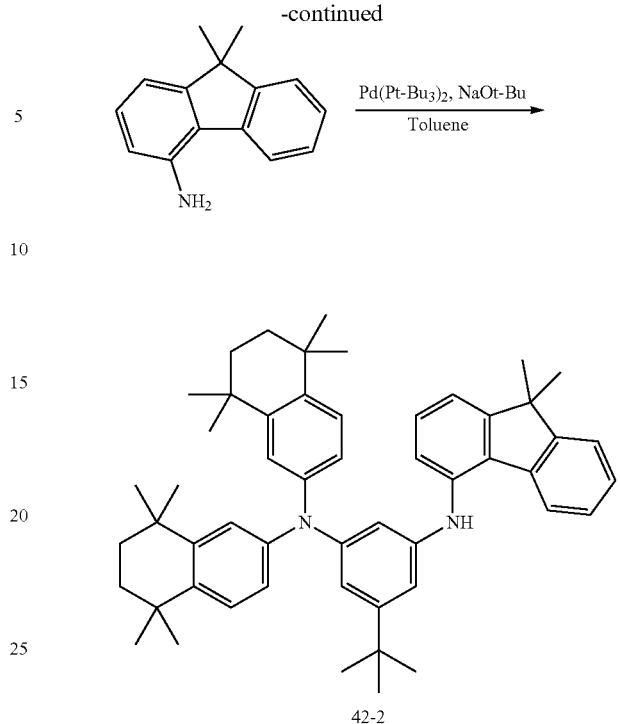

Compound 42-2 was obtained in the same manner as in Preparation of Compound 1-3 of Preparation Example 10 except that Compound 42-1 was used instead of Compound 1-2, and 9,9-dimethyl-9H-fluoren-4-amine was used instead of 4-(tert-butyl)aniline.
MS: $[M+H]^+$=730

Preparation Example 175-1: Synthesis of Compound 42-3

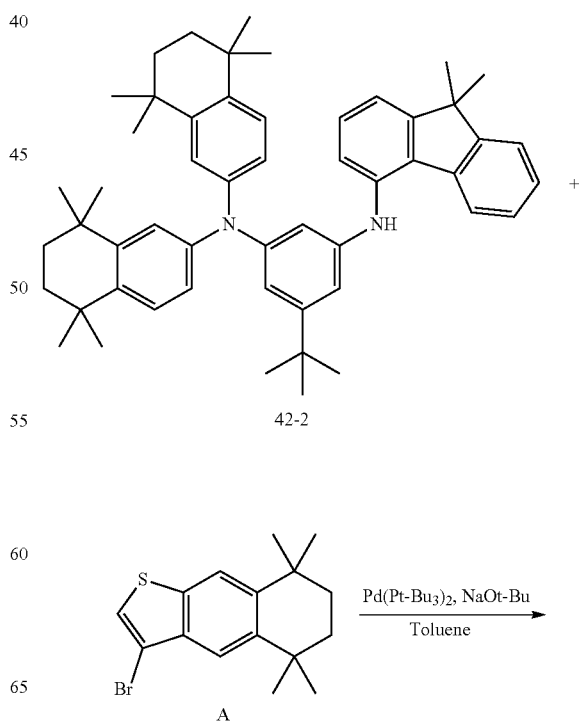

-continued

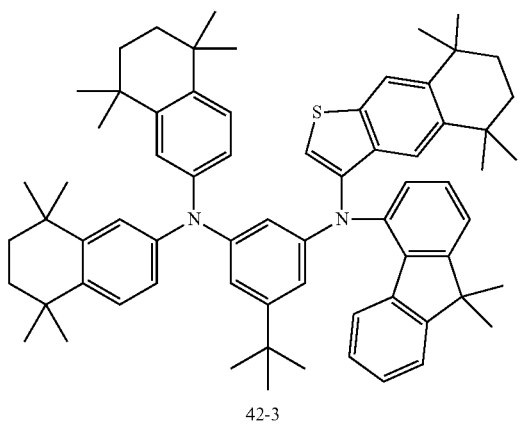
42-3

Compound 42-3 was obtained in the same manner as in Preparation of Compound 1-4 of Preparation Example 11 except that Compound 42-2 was used instead of Compound 1-3.

MS: [M+H]$^+$=972

Preparation Example 175-2: Synthesis of Compound 42

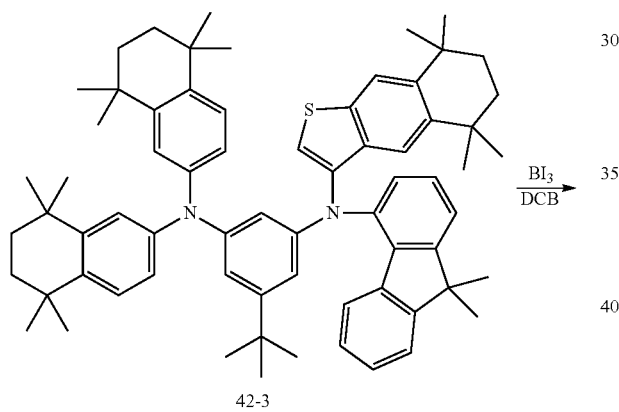
42-3

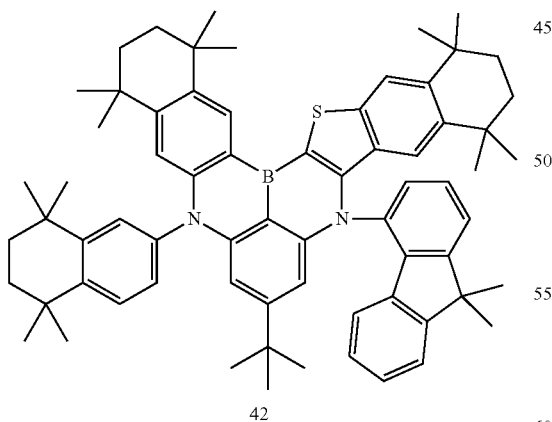
42

Compound 42 was obtained in the same manner as in Preparation of Compound 1 of Preparation Example 12 except that Compound 42-3 was used instead of Compound 1-4.

MS: [M+H]$^+$=980

Preparation Example 176: Synthesis of Compound 43-1

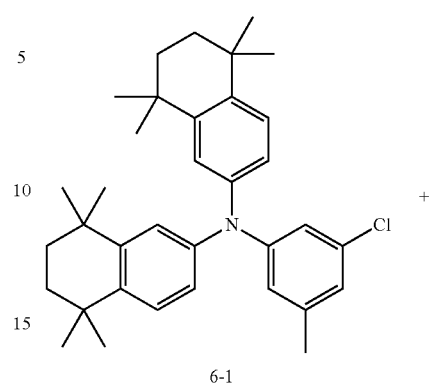
6-1

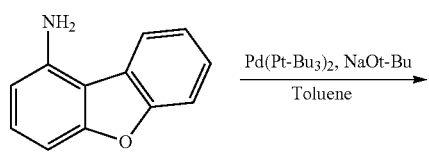

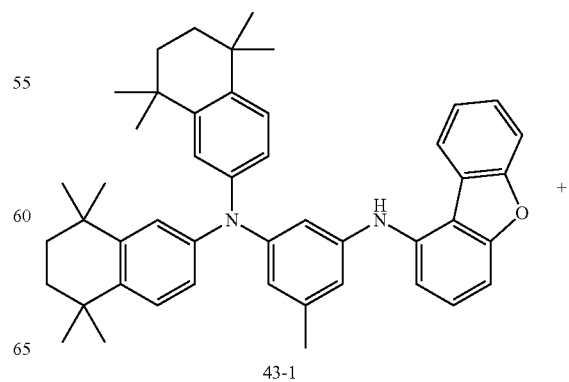
43-1

Compound 43-1 was obtained in the same manner as in Preparation of Compound 1-3 of Preparation Example 10 except that Compound 6-1 was used instead of Compound 1-2, and dibenzo[b,d]furan-1-amine was used instead of 4-(tert-butyl)aniline.

MS: [M+H]$^+$=661

Preparation Example 177: Synthesis of Compound 43-2

43-1

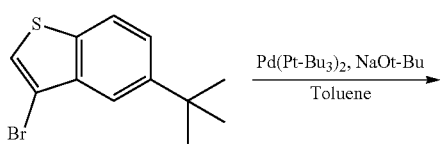

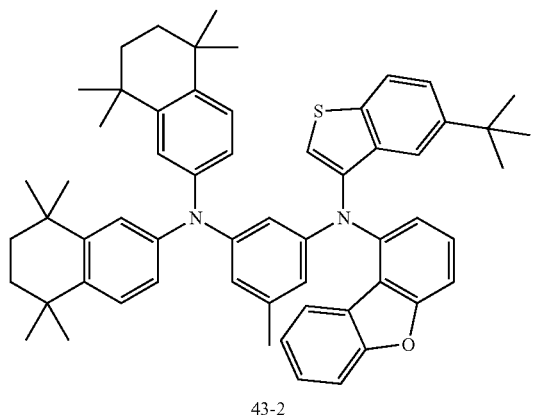

43-2

Compound 43-2 was obtained in the same manner as in Preparation of Compound 1-4 of Preparation Example 11 except that Compound 43-1 was used instead of Compound 1-3, and 3-bromo-5-(tert-butyl)benzo[b]thiophene was used instead of Compound A.

MS: [M+H]⁺=850

Preparation Example 178: Synthesis of Compound 43

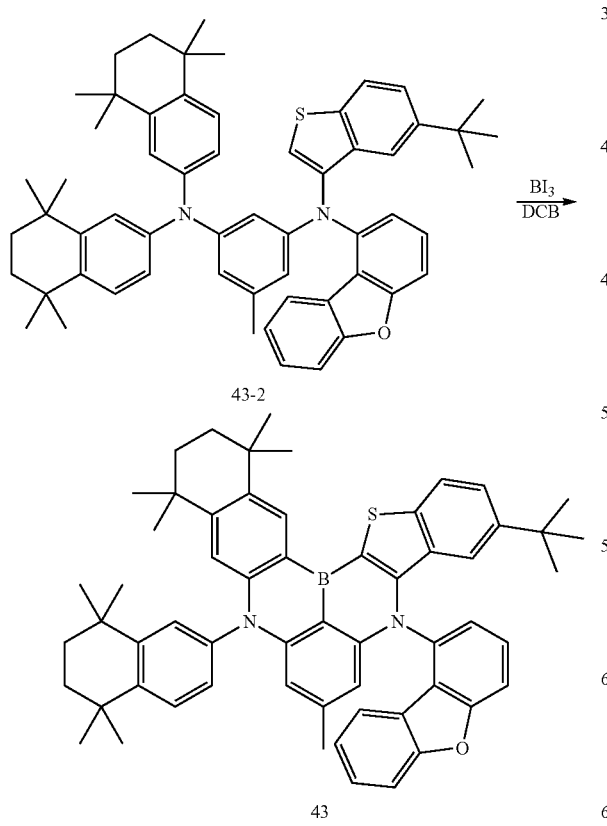

43

Compound 43 was obtained in the same manner as in Preparation of Compound 1 of Preparation Example 12 except that Compound 43-2 was used instead of Compound 1-4.

MS: [M+H]⁺=858

Preparation Example 179: Synthesis of Compound 44-1

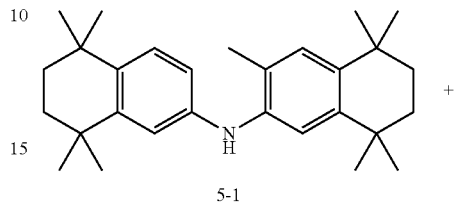

5-1

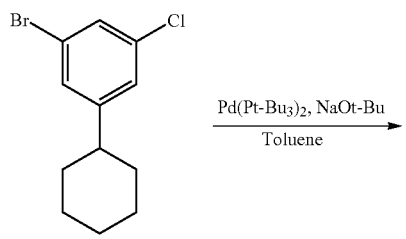

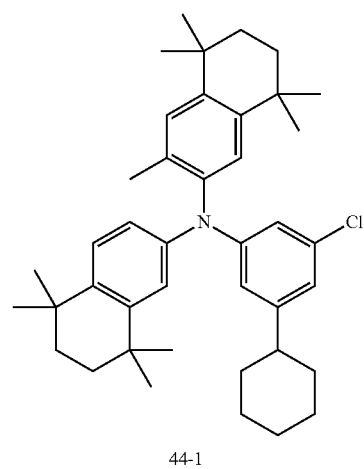

44-1

Compound 44-1 was obtained in the same manner as in Preparation of Compound 1-2 of Preparation Example 9 except that Compound 5-1 was used instead of Compound 1-1, and 1-bromo-3-chloro-5-cyclohexylbenzene was used instead of 1-bromo-3-chloro-5-methylbenzene.

MS: [M+H]⁺=597

Preparation Example 180: Synthesis of Compound 44-2

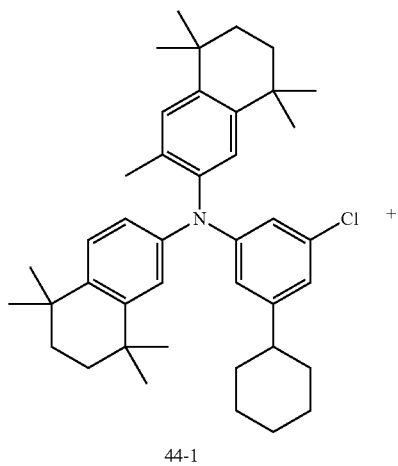

44-1

Preparation Example 181: Synthesis of Compound 44-3

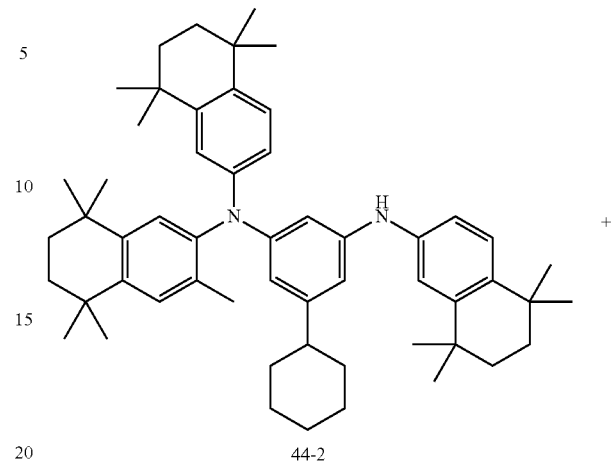

44-2

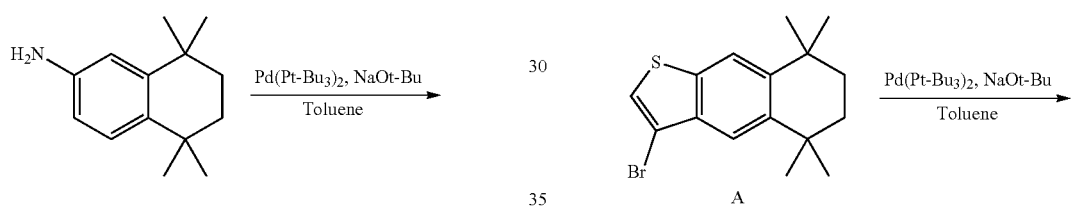

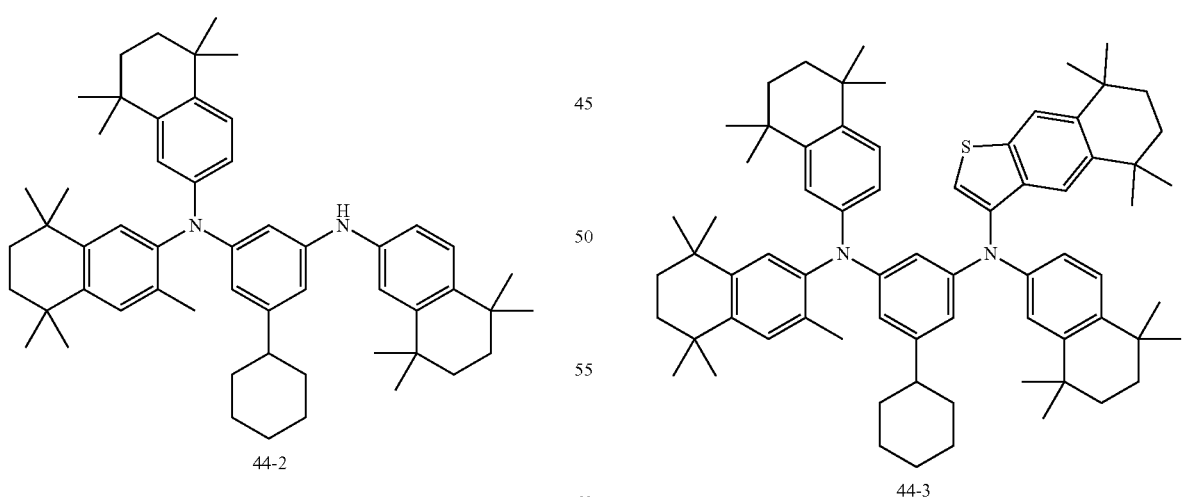

44-2

44-3

Compound 44-2 was obtained in the same manner as in Preparation of Compound 1-3 of Preparation Example 10 except that Compound 44-1 was used instead of Compound 1-2, and 5,5,8,8-tetramethyl-5,6,7,8-tetrahydronaphthalen-2-amine was used instead of 4-(tert-butyl)aniline.

MS: $[M+H]^+=764$

Compound 44-3 was obtained in the same manner as in Preparation of Compound 1-4 of Preparation Example 11 except that Compound 44-2 was used instead of Compound 1-3.

MS: $[M+H]^+=1006$

Preparation Example 181-1: Synthesis of Compound 44

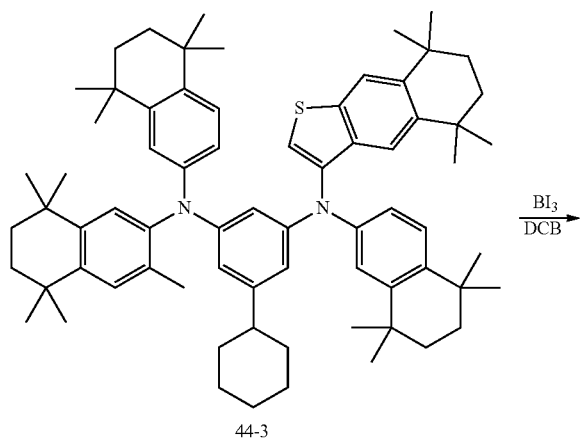

44-3

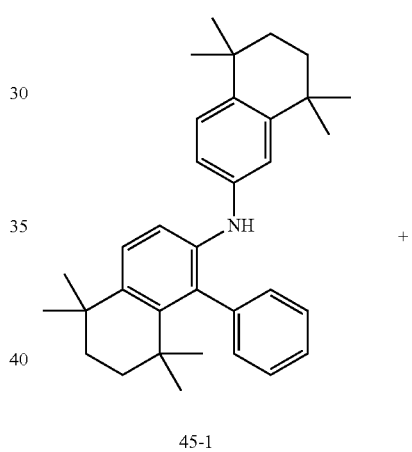

44

Compound 44 was obtained in the same manner as in Preparation of Compound 1 of Preparation Example 12 except that Compound 44-3 was used instead of Compound 1-4.

MS: [M+H]$^+$=1014

Preparation Example 182: Synthesis of Compound 45-1

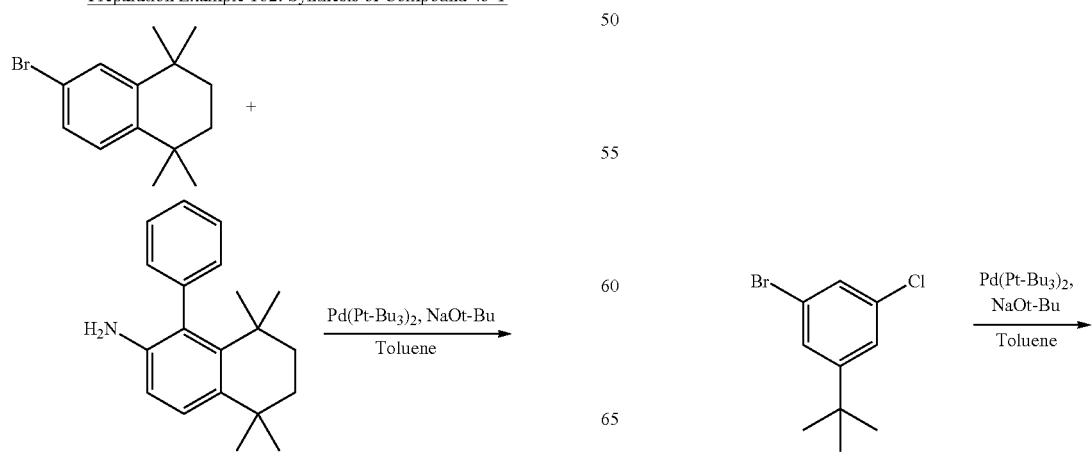

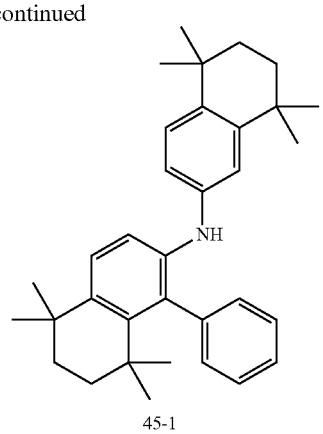

45-1

Compound 45-1 was obtained in the same manner as in Preparation of Compound 1-1 of Preparation Example 8 except that 5,5,8,8-tetramethyl-1-phenyl-5,6,7,8-tetrahydronaphthalen-2-amine was used instead of 5-(tert-butyl)-[1,1'-biphenyl]-2-amine.

MS: [M+H]$^+$=466

971

-continued

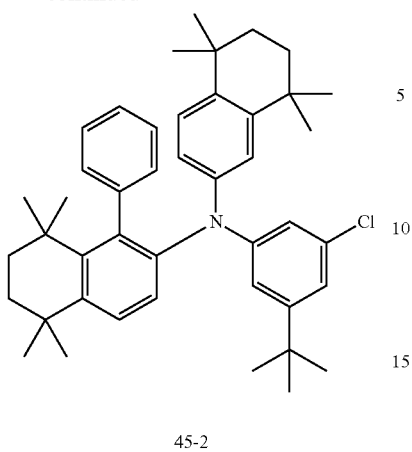

45-2

Compound 45-2 was obtained in the same manner as in Preparation of Compound 1-2 of Preparation Example 9 except that Compound 45-1 was used instead of Compound 1-1, and 1-bromo-3-(tert-butyl)-5-chlorobenzene was used instead of 1-bromo-3-chloro-5-methylbenzene.

MS: [M+H]$^+$=597

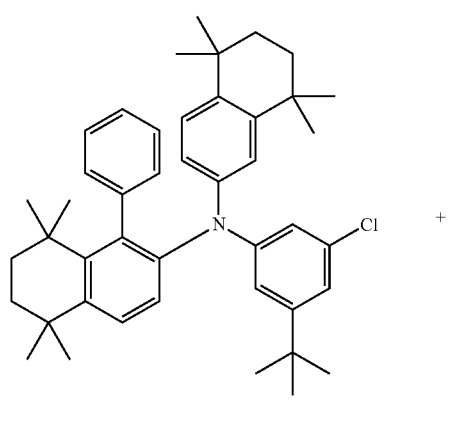

45-2

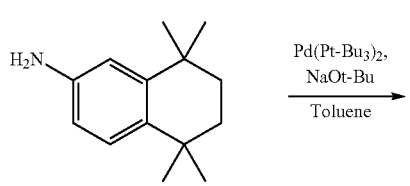

972

-continued

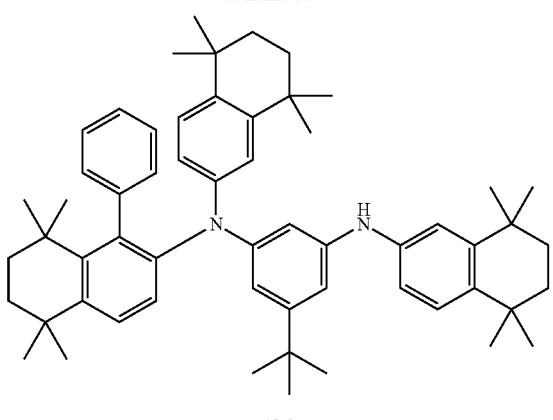

45-3

Compound 45-3 was obtained in the same manner as in Preparation of Compound 1-3 of Preparation Example 10 except that Compound 45-2 was used instead of Compound 1-2, and 5,5,8,8-tetramethyl-5,6,7,8-tetrahydronaphthalen-2-amine was used instead of 4-(tert-butyl)aniline.

MS: [M+H]$^+$=800

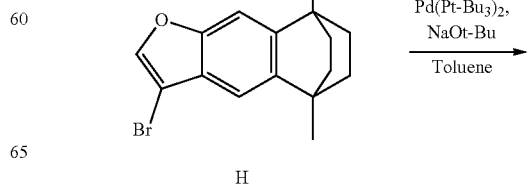

-continued

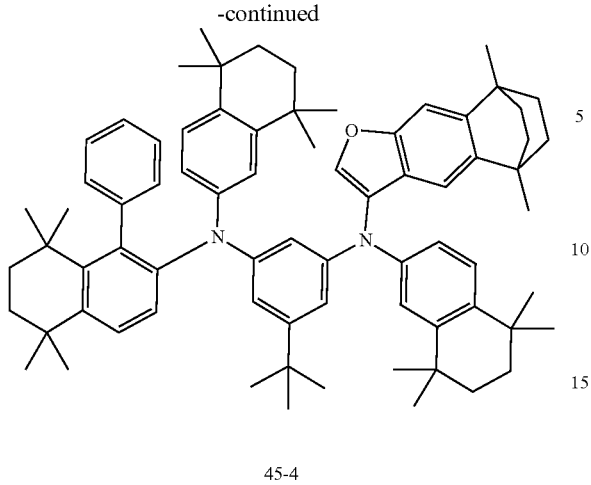

45-4

Compound 45-4 was obtained in the same manner as in Preparation of Compound 1-4 of Preparation Example 11 except that Compound 45-3 was used instead of Compound 1-3, and Compound H was used instead of Compound A.

MS: [M+H]$^+$=1024

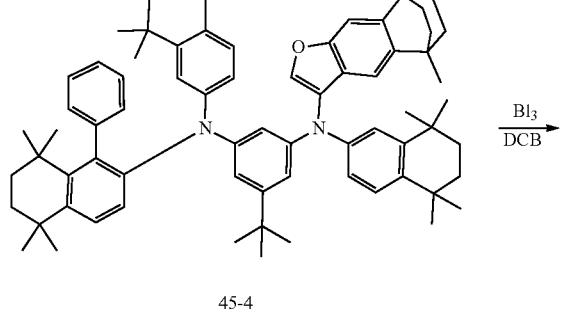

45-4

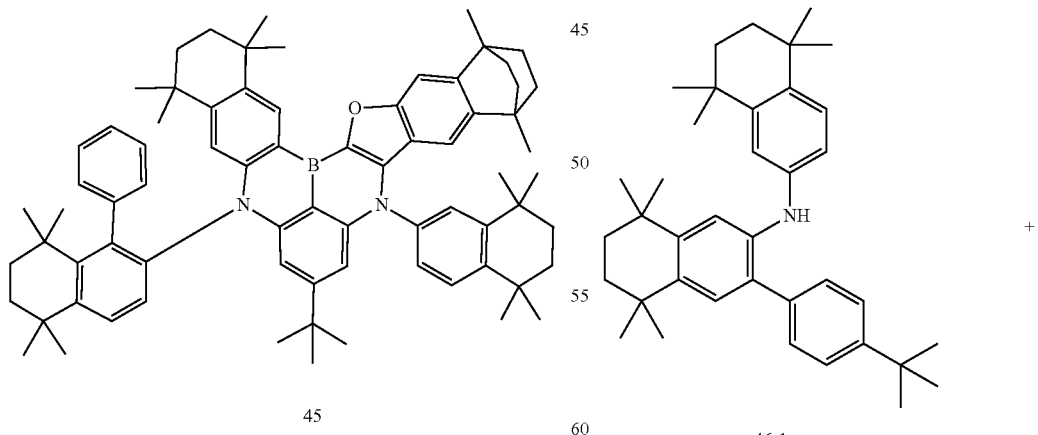

45

Compound 45 was obtained in the same manner as in Preparation of Compound 1 of Preparation Example 12 except that Compound 45-4 was used instead of Compound 1-4.

MS: [M+H]$^+$=1032

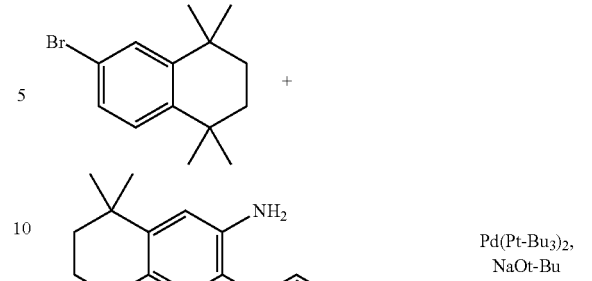

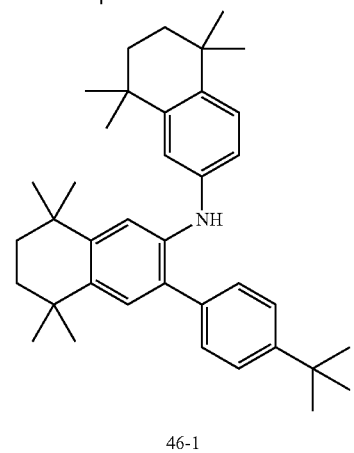

46-1

Compound 46-1 was obtained in the same manner as in Preparation of Compound 1-1 of Preparation Example 8 except that 3-(4-(tert-butyl)phenyl)-5,5,8,8-tetramethyl-5,6,7,8-tetrahydronaphthalen-2-amine was used instead of 5-(tert-butyl)-[1,1'-biphenyl]-2-amine.

MS: [M+H]$^+$=522

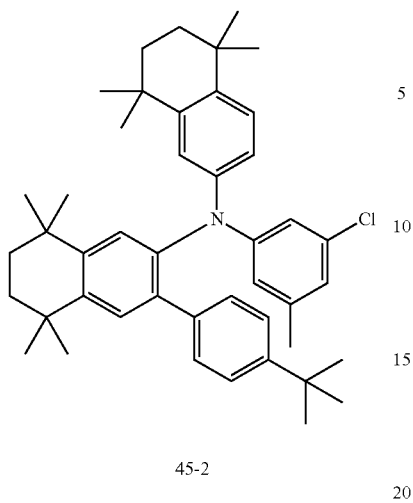

45-2

Compound 46-2 was obtained in the same manner as in Preparation of Compound 1-2 of Preparation Example 9 except that Compound 46-1 was used instead of Compound 1-1.

MS: [M+H]⁺=647

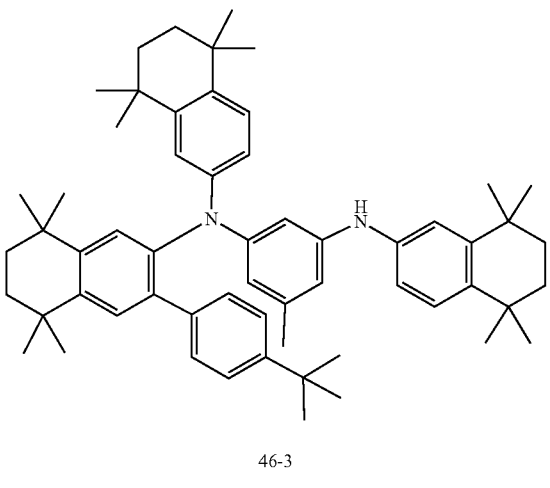

46-3

Compound 46-3 was obtained in the same manner as in Preparation of Compound 1-3 of Preparation Example 10 except that Compound 46-2 was used instead of Compound 1-2, and 5,5,8,8-tetramethyl-5,6,7,8-tetrahydronaphthalen-2-amine was used instead of 4-(tert-butyl)aniline.

MS: [M+H]⁺=814

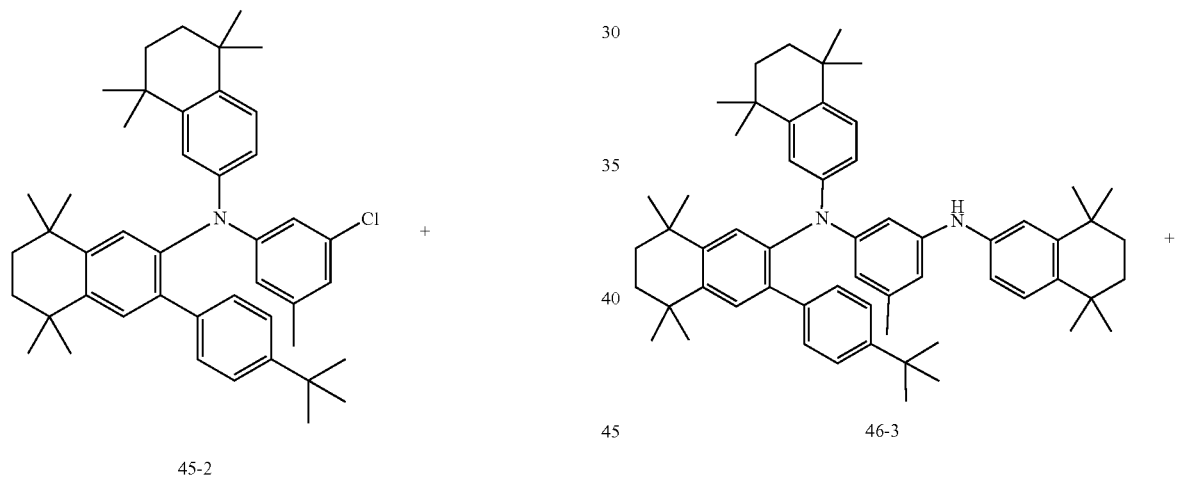

45-2

46-3

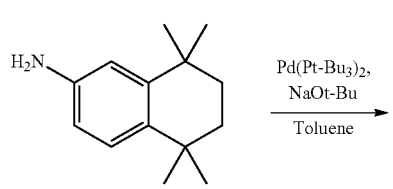

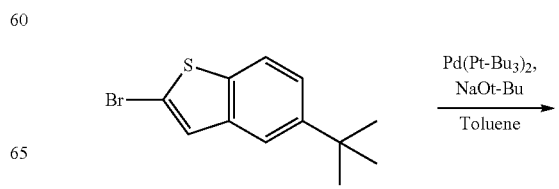

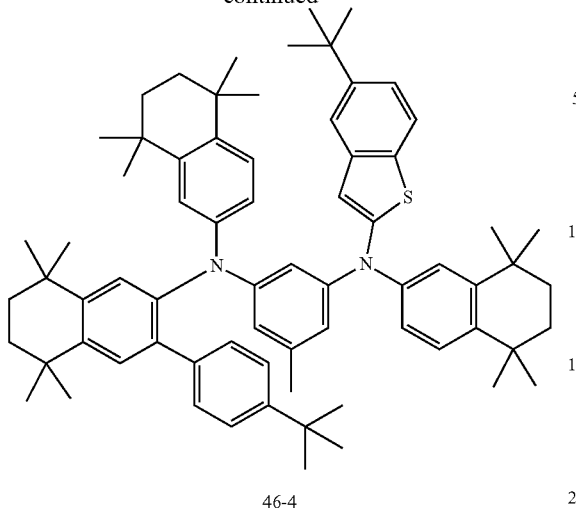

46-4

Compound 46-4 was obtained in the same manner as in Preparation of Compound 1-4 of Preparation Example 11 except that Compound 46-3 was used instead of Compound 1-3, and 2-bromo-5-(tert-butyl)benzo[b]thiophene was used instead of Compound A.

MS: [M+H]$^+$=1002

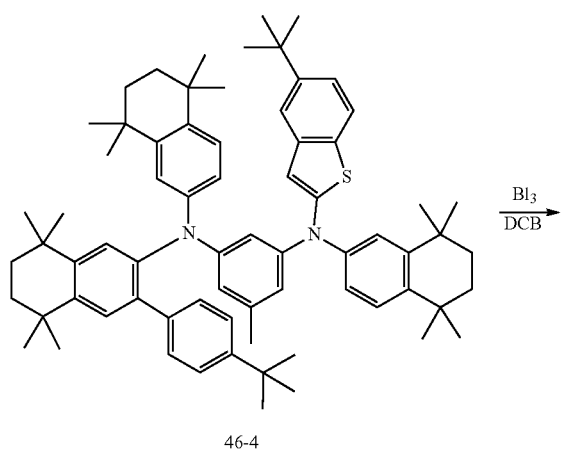

46-4

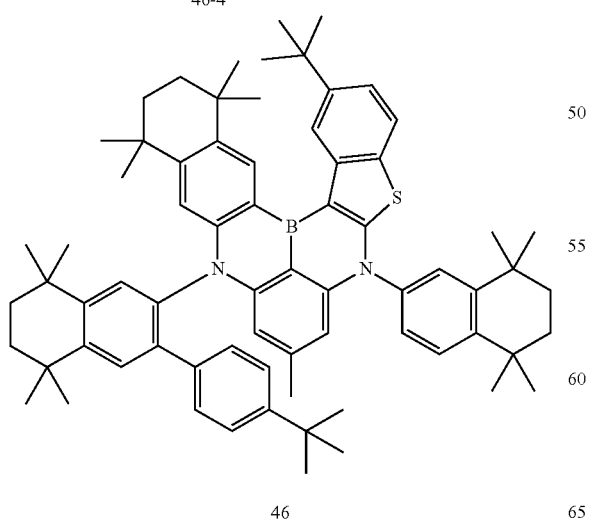

46

Compound 46 was obtained in the same manner as in Preparation of Compound 1 of Preparation Example 12 except that Compound 46-4 was used instead of Compound 1-4.

MS: [M+H]$^+$=1010

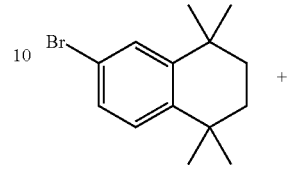

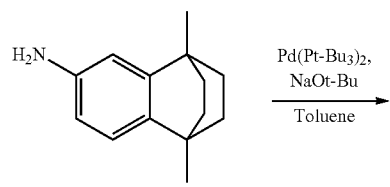

47-1

Compound 47-1 was obtained in the same manner as in Preparation of Compound 1-1 of Preparation Example 8 except that 1,4-dimethyl-1,2,3,4-tetrahydro-1,4-ethanonaphthalen-6-amine was used instead of 5-(tert-butyl)-[1,1'-biphenyl]-2-amine.

MS: [M+H]$^+$=513

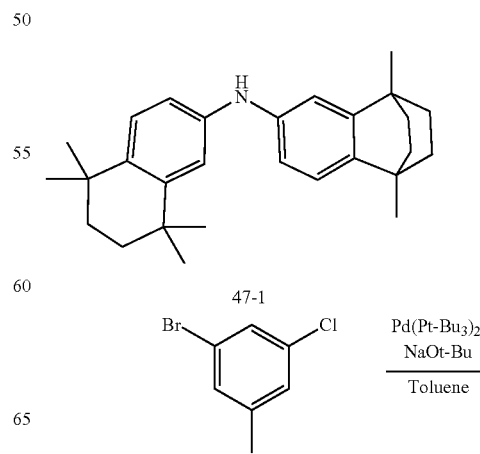

47-1

-continued

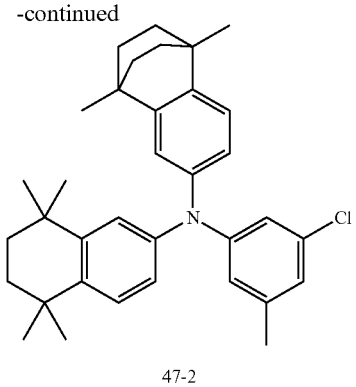

47-2

Compound 47-2 was obtained in the same manner as in Preparation of Compound 1-2 of Preparation Example 9 except that Compound 47-1 was used instead of Compound 1-1.

MS: [M+H]$^+$=513

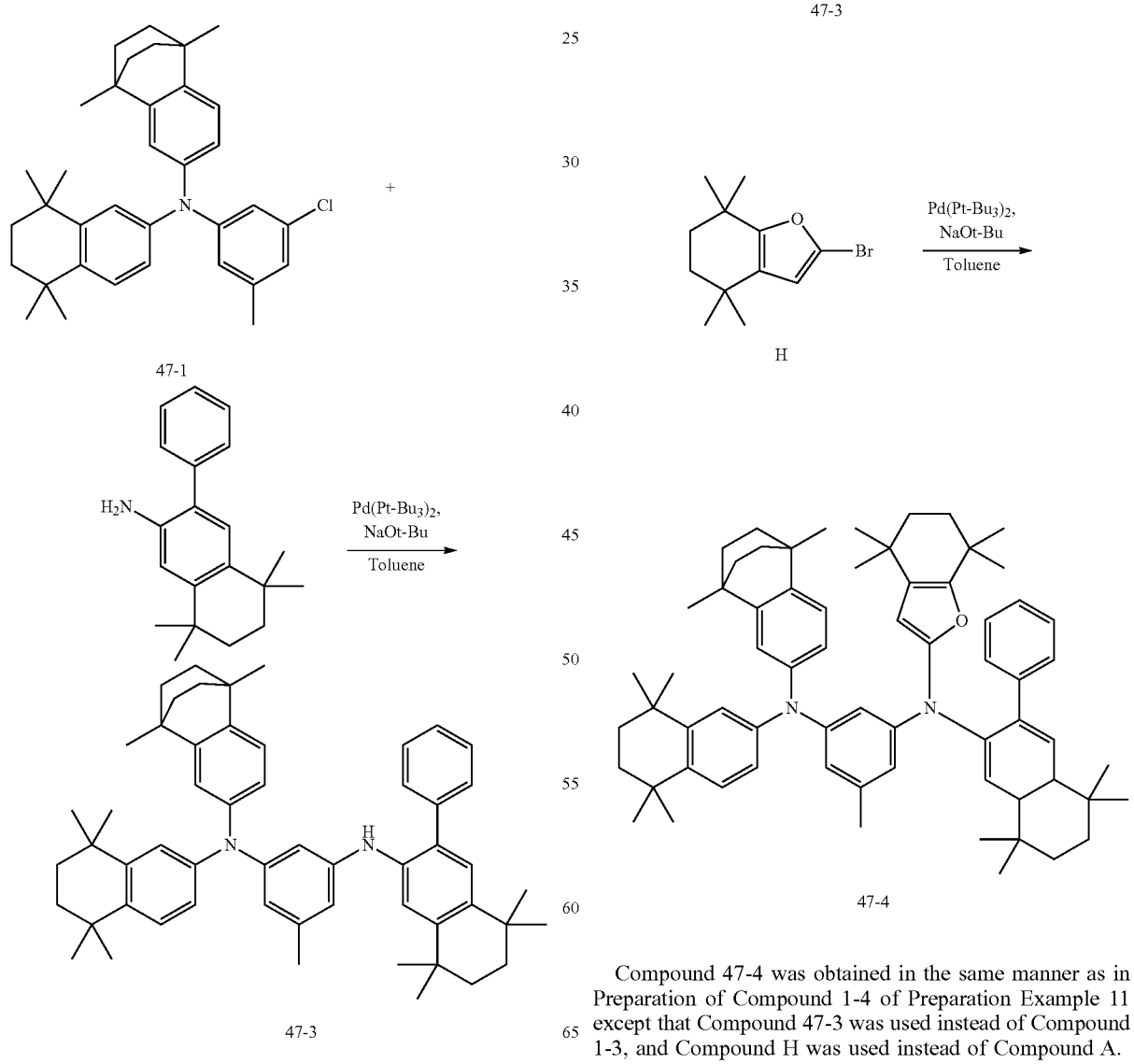

47-1

47-3

Compound 47-3 was obtained in the same manner as in Preparation of Compound 1-3 of Preparation Example 10 except that Compound 47-2 was used instead of Compound 1-2, and 5,5,8,8-tetramethyl-3-phenyl-5,6,7,8-tetrahydronaphthalen-2-amine was used instead of 4-(tert-butyl)aniline.

MS: [M+H]$^+$=756

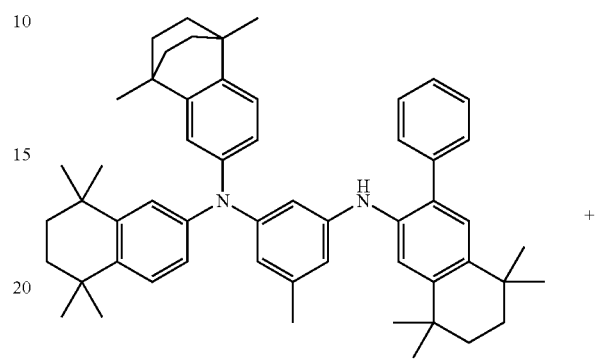

47-3

47-4

Compound 47-4 was obtained in the same manner as in Preparation of Compound 1-4 of Preparation Example 11 except that Compound 47-3 was used instead of Compound 1-3, and Compound H was used instead of Compound A.

MS: [M+H]$^+$=932

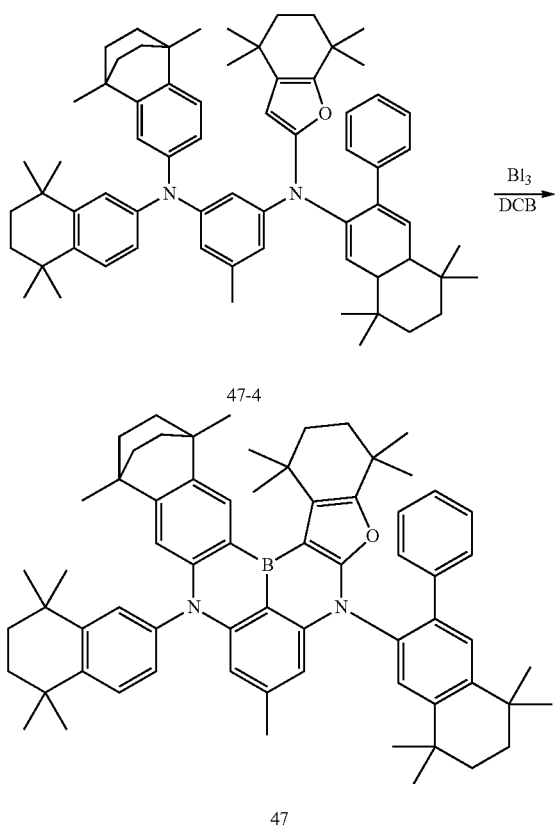

Compound 47 was obtained in the same manner as in Preparation of Compound 1 of Preparation Example 12 except that Compound 47-4 was used instead of Compound 1-4.

MS: [M+H]⁺=940

Compound 48-1 was obtained in the same manner as in Preparation of Compound 1-1 of Preparation Example 8 except that 2-bromo-5-(tert-butyl)-1,3-dimethylbenzene was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]⁺=310

Preparation Example 197: Synthesis of Compound 48-2

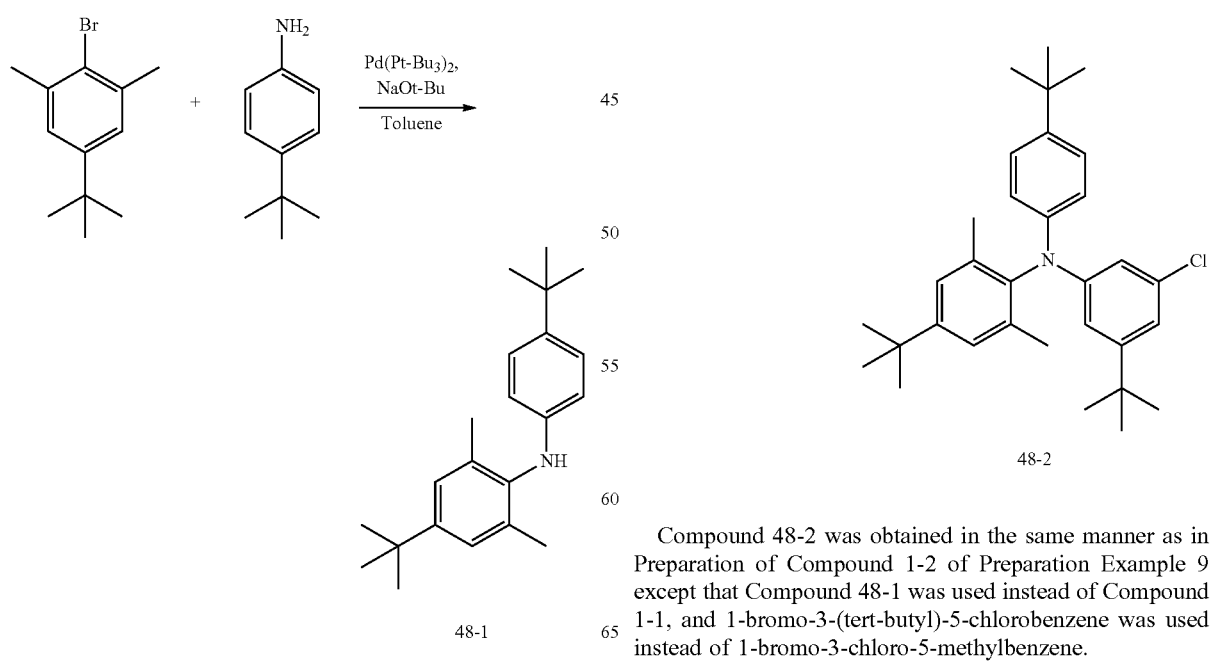

Compound 48-2 was obtained in the same manner as in Preparation of Compound 1-2 of Preparation Example 9 except that Compound 48-1 was used instead of Compound 1-1, and 1-bromo-3-(tert-butyl)-5-chlorobenzene was used instead of 1-bromo-3-chloro-5-methylbenzene.

MS: [M+H]⁺=477

Preparation Example 198: Synthesis of Compound 48-3

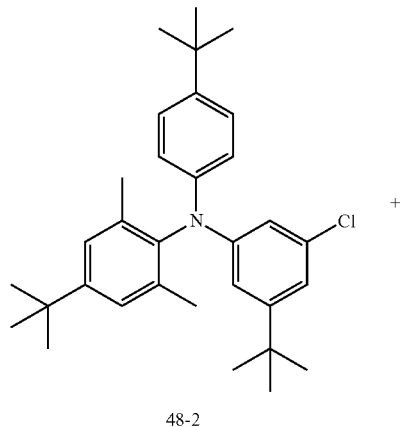

48-2

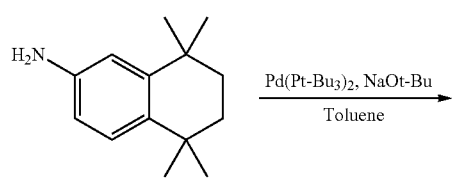

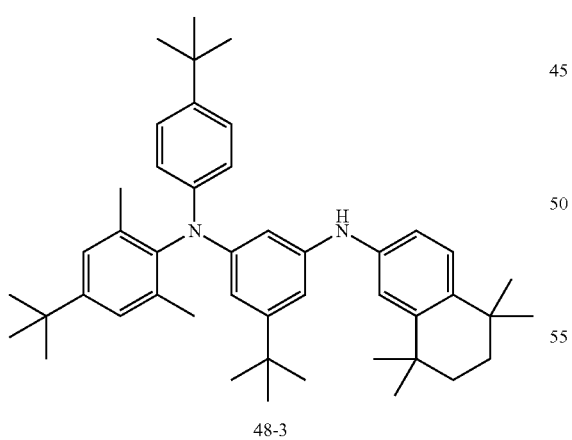

48-3

Compound 48-3 was obtained in the same manner as in Preparation of Compound 1-3 of Preparation Example 10 except that Compound 48-2 was used instead of Compound 1-2, and 5,5,8,8-tetramethyl-5,6,7,8-tetrahydronaphthalen-2-amine was used instead of 4-(tert-butyl)aniline.

MS: [M+H]$^+$=644

Preparation Example 199: Synthesis of Compound 48-4

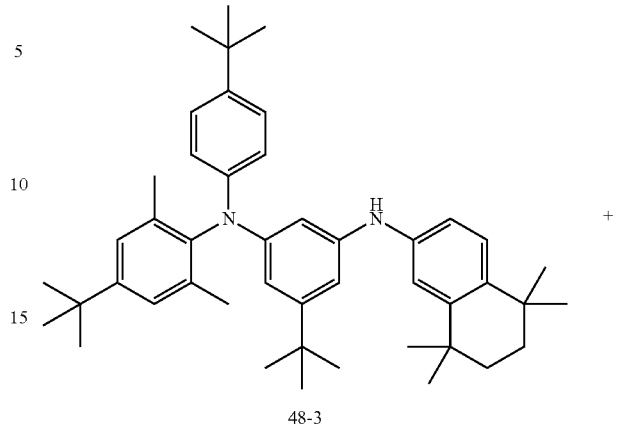

48-3

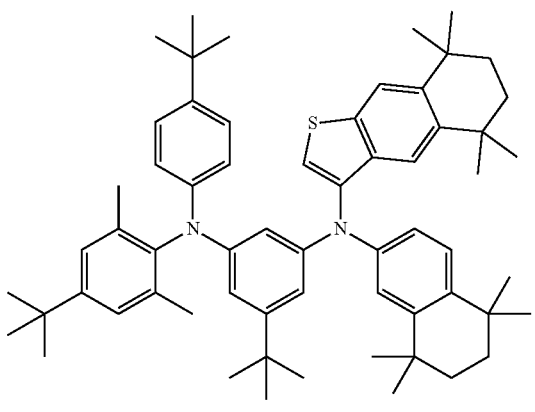

48-4

Compound 48-4 was obtained in the same manner as in Preparation of Compound 1-4 of Preparation Example 11 except that Compound 48-3 was used instead of Compound 1-3.

MS: [M+H]$^+$=886

Preparation Example 200: Synthesis of Compound 48

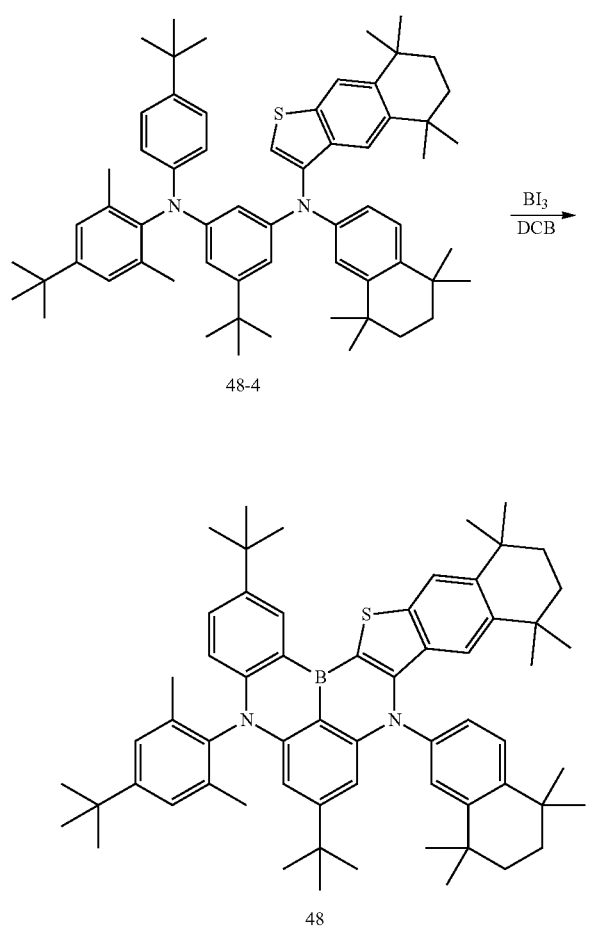

Compound 48 was obtained in the same manner as in Preparation of Compound 1 of Preparation Example 12 except that Compound 48-4 was used instead of Compound 1-4.

MS: [M+H]⁺=894

Preparation Example 201: Synthesis of Compound 49-1

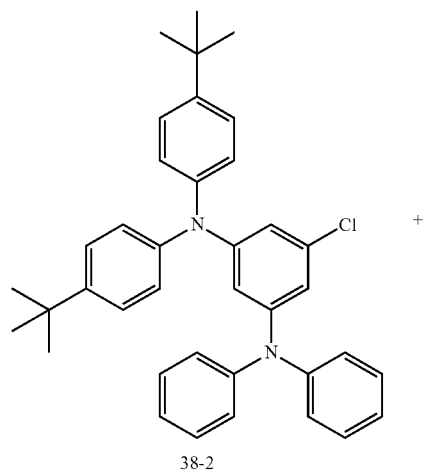

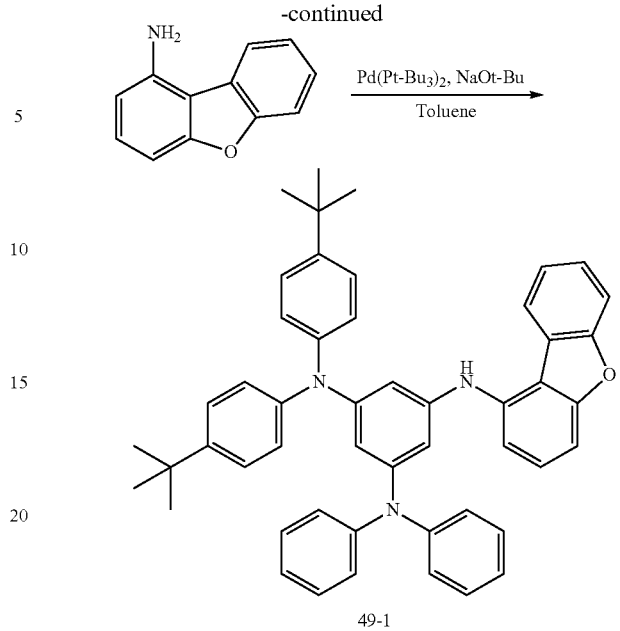

Compound 49-1 was obtained in the same manner as in Preparation of Compound 1-3 of Preparation Example 10 except that Compound 38-2 was used instead of Compound 1-2, and dibenzo[b,d]furan-1-amine was used instead of 4-(tert-butyl)aniline.

MS: [M+H]⁺=706

Preparation Example 202: Synthesis of Compound 49-2

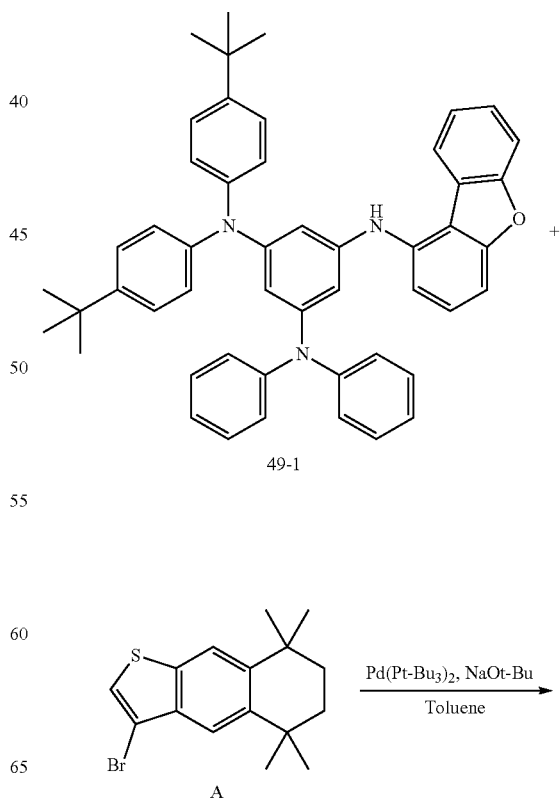

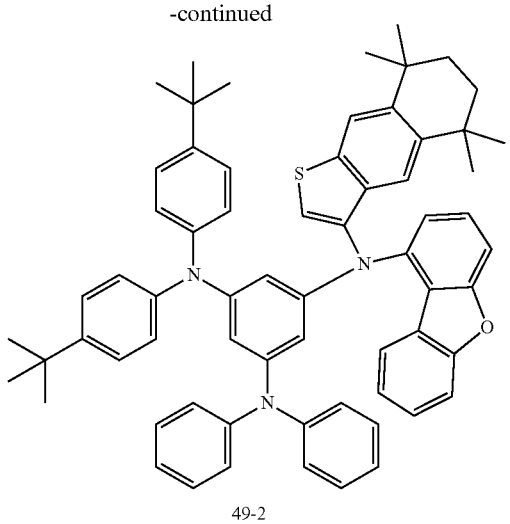

49-2

Compound 49-2 was obtained in the same manner as in Preparation of Compound 1-4 of Preparation Example 11 except that Compound 49-1 was used instead of Compound 1-3.

MS: [M+H]⁺=949

Preparation Example 202-1: Synthesis of Compound 49

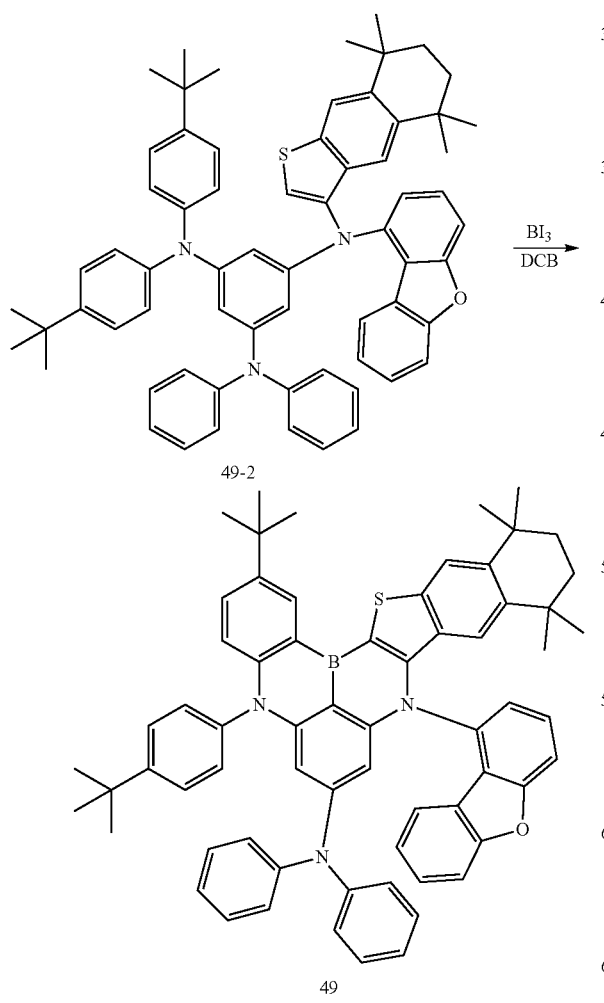

49

Compound 49 was obtained in the same manner as in Preparation of Compound 1 of Preparation Example 12 except that Compound 49-2 was used instead of Compound 1-4.

MS: [M+H]⁺=957

Preparation Example 203: Synthesis of Compound 50-1

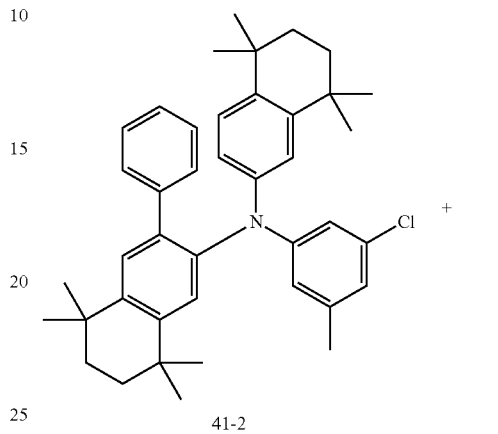

41-2

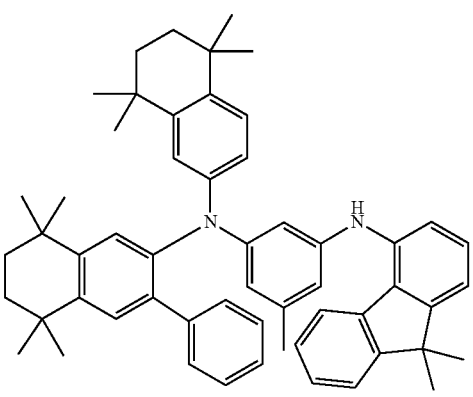

50-1

Compound 50-1 was obtained in the same manner as in Preparation of Compound 1-3 of Preparation Example 10 except that Compound 41-2 was used instead of Compound 1-2, and 9,9-dimethyl-9H-fluoren-4-amine was used instead of 4-(tert-butyl)aniline.

MS: [M+H]⁺=764

Preparation Example 204: Synthesis of Compound 50-2

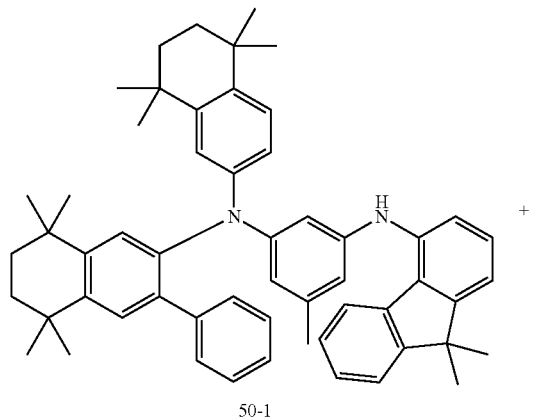

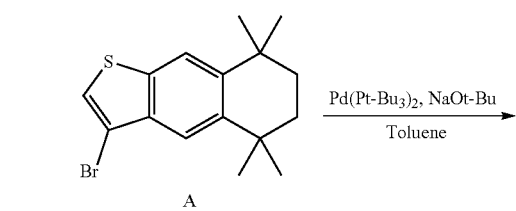

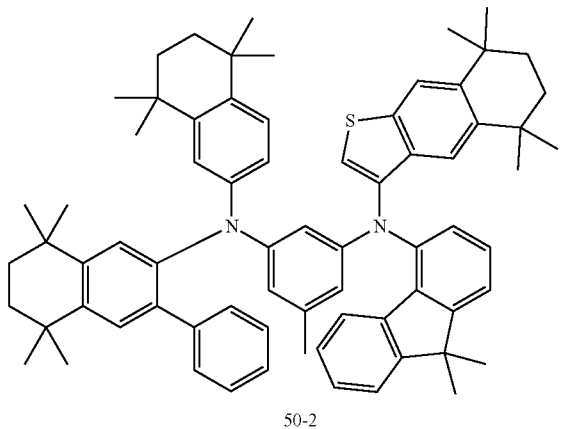

Compound 50-2 was obtained in the same manner as in Preparation of Compound 1-4 of Preparation Example 11 except that Compound 50-1 was used instead of Compound 1-3.

MS: [M+H]$^+$=1006

Preparation Example 205: Synthesis of Compound 50

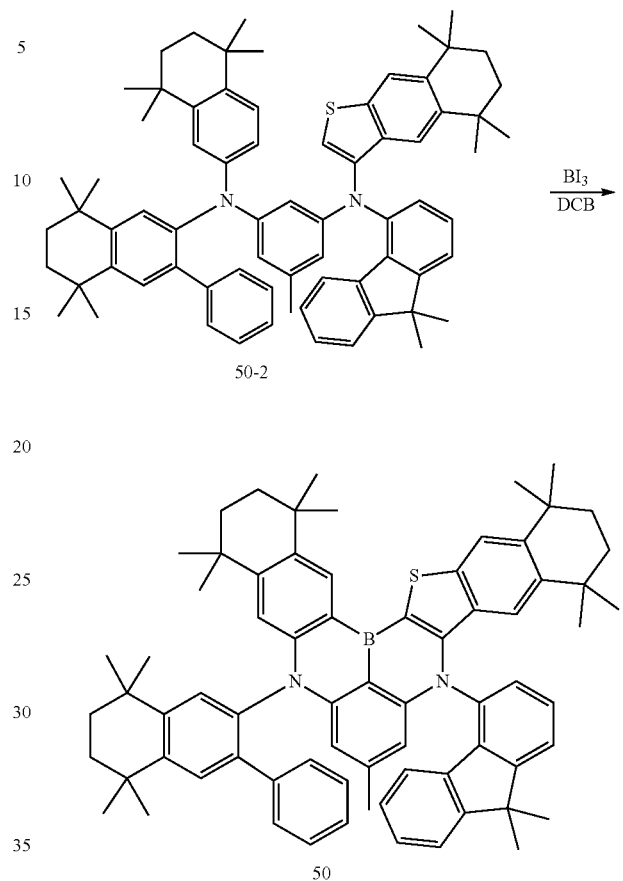

Compound 50 was obtained in the same manner as in Preparation of Compound 1 of Preparation Example 12 except that Compound 50-2 was used instead of Compound 1-4.

MS: [M+H]$^+$=1014

Preparation Example 206: Synthesis of Compound 51-1

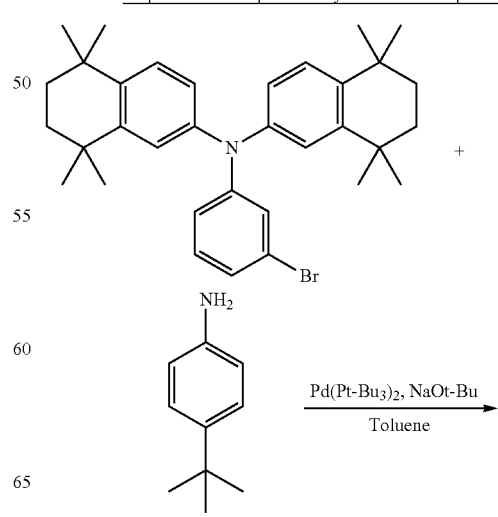

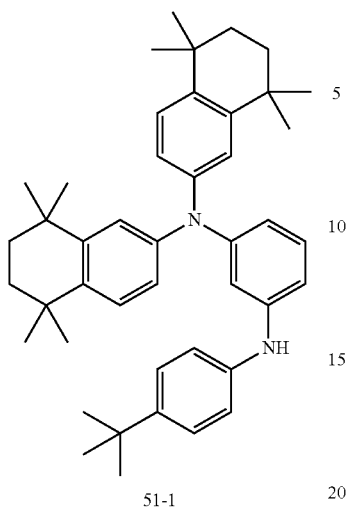

51-1

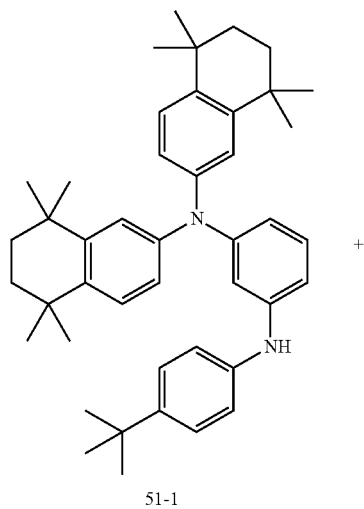

51-1

Compound 51-1 was obtained in the same manner as in Preparation of Compound 1-1 of Preparation Example 8 except that N-(3-bromophenyl)-5,5,8,8-tetramethyl-N-(5,5,8,8-tetramethyl-5,6,7,8-tetrahydronaphthalen-2-yl)-5,6,7,8-tetrahydronaphthalen-2-amine was used instead of 6-bromo-1,1,4,4-tetramethyl-1,2,3,4-tetrahydronaphthalene, and 4-(tert-butyl)aniline was used instead of 5-(tert-butyl)-[1,1'-biphenyl]-2-amine.

MS: [M+H]$^+$=613

Preparation Example 207: Synthesis of Compound 51-2

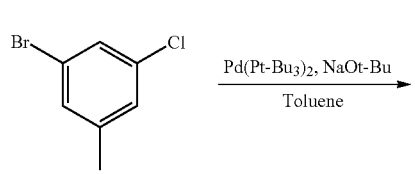

51-2

Compound 51-2 was obtained in the same manner as in Preparation of Compound 1-2 of Preparation Example 9 except that Compound 51-1 was used instead of Compound 1-1.

MS: [M+H]$^+$=738

Preparation Example 208: Synthesis of Compound 51-3

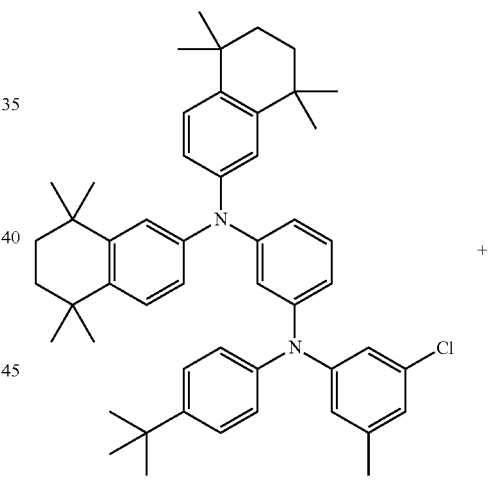

51-2

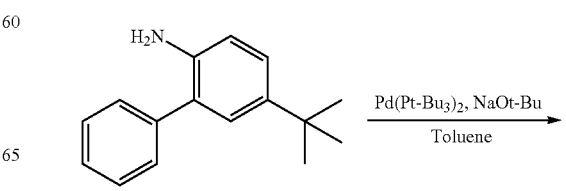

993
-continued

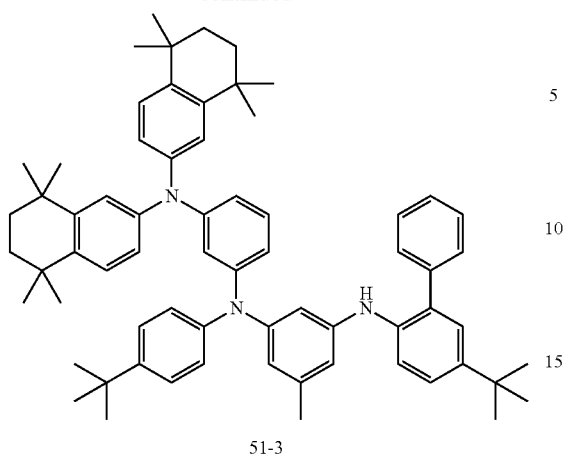

51-3

Compound 51-3 was obtained in the same manner as in Preparation of Compound 1-3 of Preparation Example 10 except that Compound 51-2 was used instead of Compound 1-2, and 5-(tert-butyl)-[1,1'-biphenyl]-2-amine was used instead of 4-(tert-butyl)aniline.

MS: [M+H]$^+$=749

Preparation Example 209: Synthesis of Compound 51-4

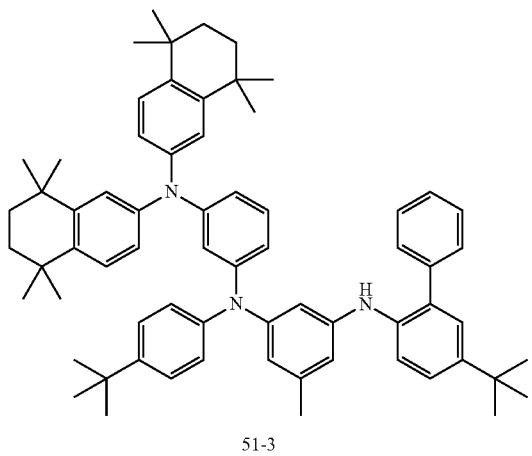

51-3

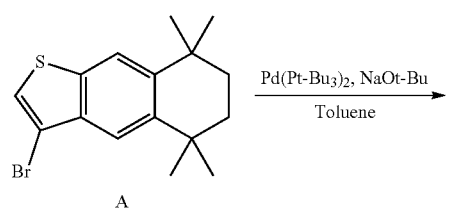

A

Pd(Pt-Bu$_3$)$_2$, NaOt-Bu
Toluene

994
-continued

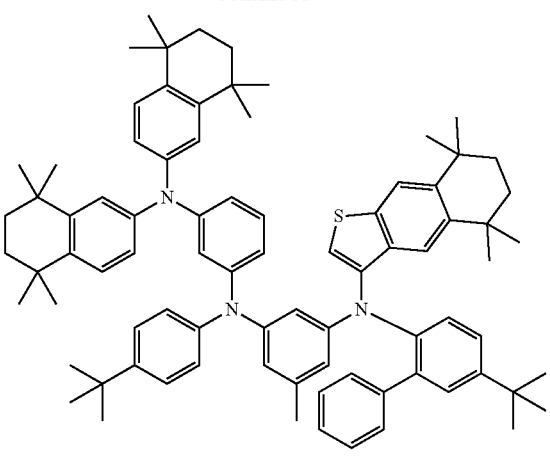

51-4

Compound 51-4 was obtained in the same manner as in Preparation of Compound 1-4 of Preparation Example 11 except that Compound 51-3 was used instead of Compound 1-3.

MS: [M+H]$^+$=1169

Preparation Example 210: Synthesis of Compound 51

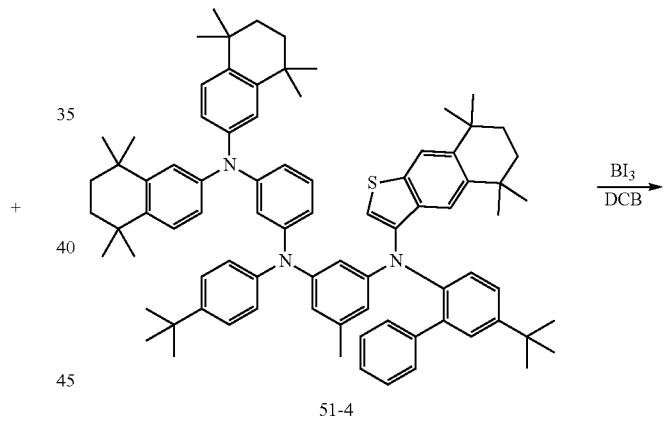

51-4

BI$_3$
DCB

51

Compound 51 was obtained in the same manner as in Preparation of Compound 1 of Preparation Example 12 except that Compound 51-4 was used instead of Compound 1-4.

MS: [M+H]⁺=1177

Preparation Example 211: Synthesis of Compound 52-1

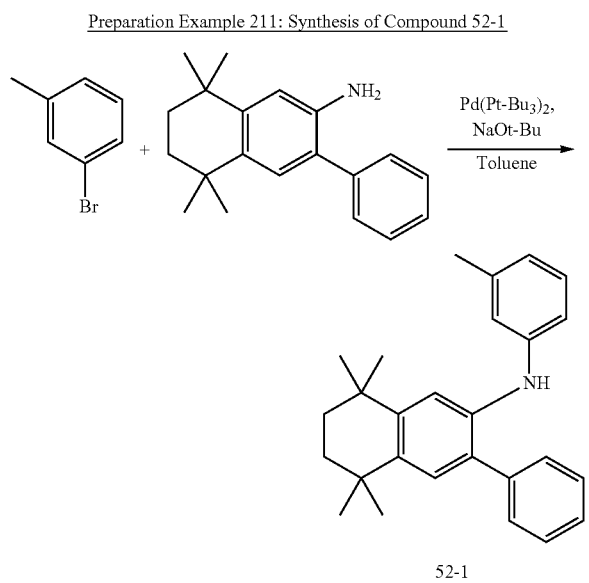

Compound 52-1 was obtained in the same manner as in Preparation of Compound 1-1 of Preparation Example 8 except that 5,5,8,8-tetramethyl-3-phenyl-5,6,7,8-tetrahydronaphthalen-2-amine was used instead of 5-(tert-butyl)-[1,1'-biphenyl]-2-amine, and 1-bromo-3-methylbenzene was used instead of 6-bromo-1,1,4,4-tetramethyl-1,2,3,4-tetrahydronaphthalene.

MS: [M+H]⁺=370

Preparation Example 212: Synthesis of Compound 52-2

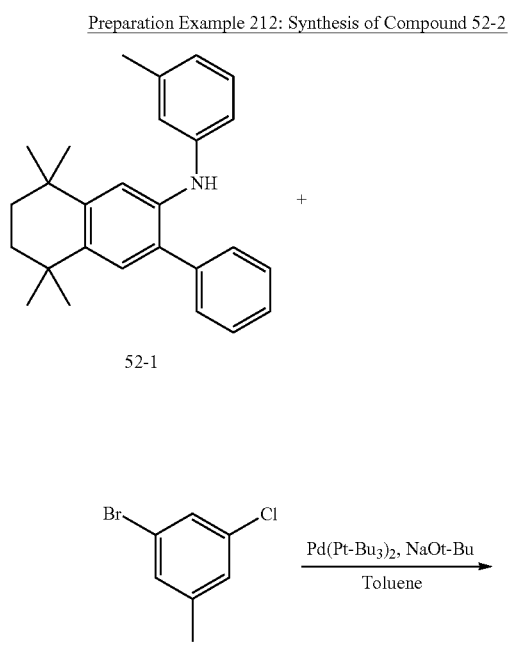

-continued

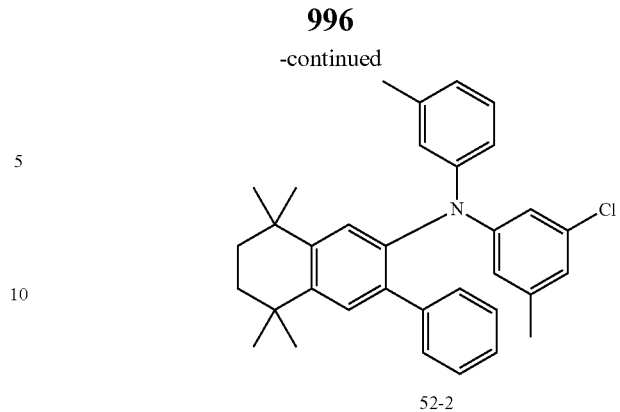

Compound 52-2 was obtained in the same manner as in Preparation of Compound 1-2 of Preparation Example 9 except that Compound 52-1 was used instead of Compound 1-1.

MS: [M+H]⁺=495

Preparation Example 213: Synthesis of Compound 52-3

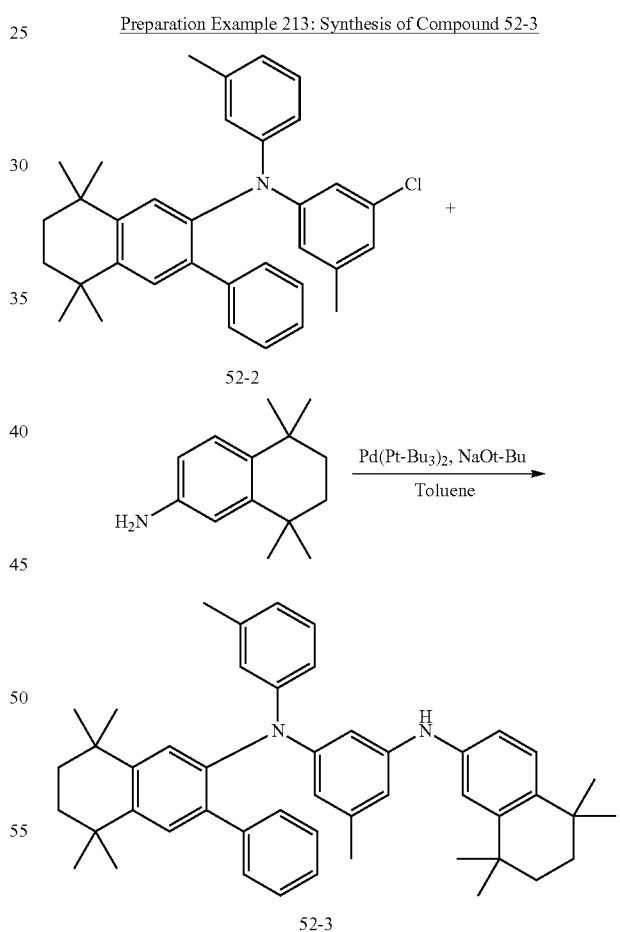

Compound 52-3 was obtained in the same manner as in Preparation of Compound 1-3 of Preparation Example 10 except that Compound 52-2 was used instead of Compound 1-2, and 5,5,8,8-tetramethyl-5,6,7,8-tetrahydronaphthalen-2-amine was used instead of 4-(tert-butyl)aniline.

MS: [M+H]⁺=661

Preparation Example 214: Synthesis of Compound 52-4

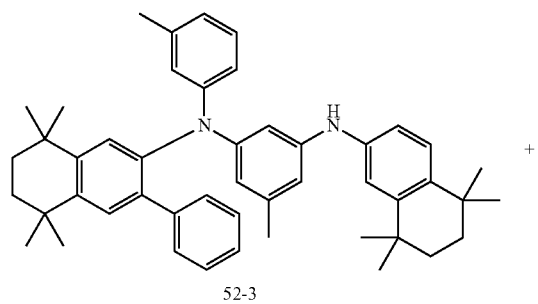

52-3

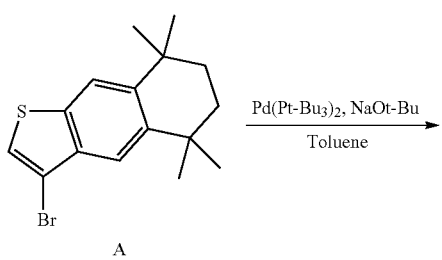

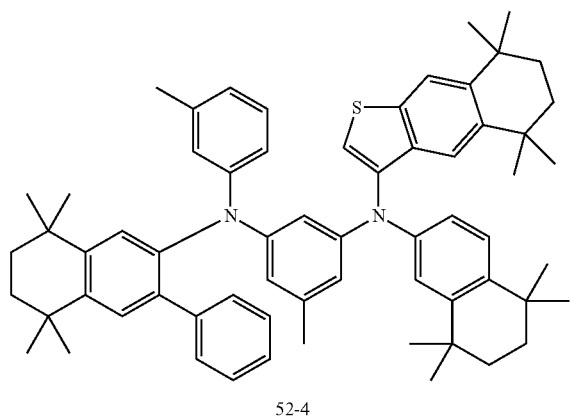

52-4

Compound 52-4 was obtained in the same manner as in Preparation of Compound 1-4 of Preparation Example 11 except that Compound 52-3 was used instead of Compound 1-3.

MS: [M+H]$^+$=904

Preparation Example 215: Synthesis of Compound 52

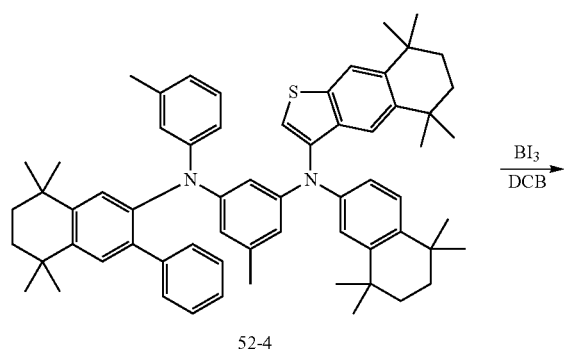

52-4

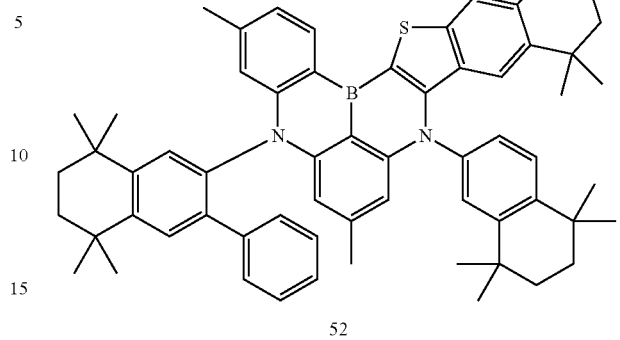

52

Compound 52 was obtained in the same manner as in Preparation of Compound 1 of Preparation Example 12 except that Compound 52-4 was used instead of Compound 1-4.

MS: [M+H]$^+$=912

Preparation Example 216: Synthesis of Compound 53-1

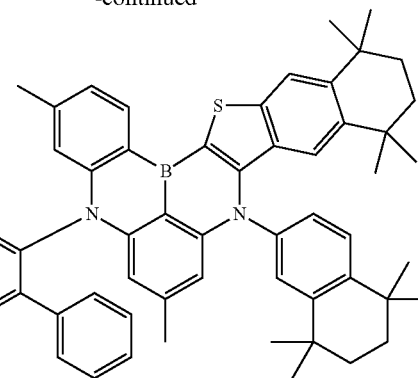

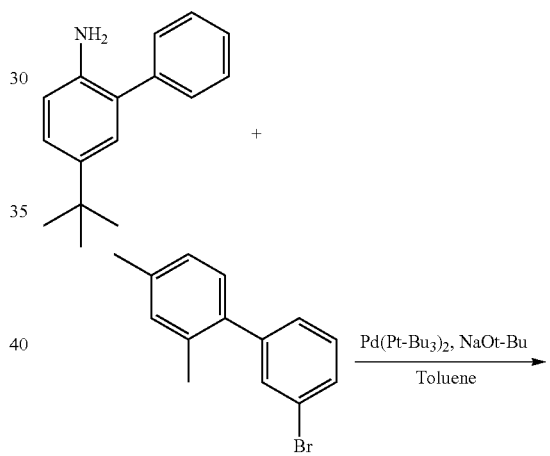

53.1

Compound 53-1 was obtained in the same manner as in Preparation of Compound 1-1 of Preparation Example 8 except that 3'-bromo-2,4-dimethyl-1,1'-biphenyl was used instead of 6-bromo-1,1,4,4-tetramethyl-1,2,3,4-tetrahydronaphthalene.

MS: [M+H]$^+$=406

Preparation Example 217: Synthesis of Compound 53-2

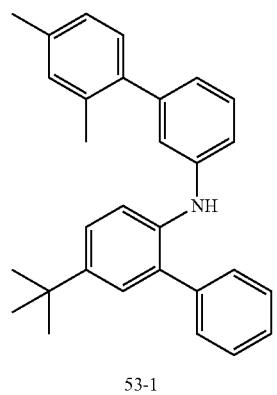

53-1

+

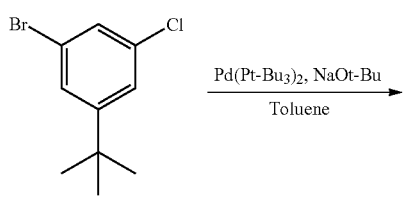

Pd(Pt-Bu₃)₂, NaOt-Bu / Toluene →

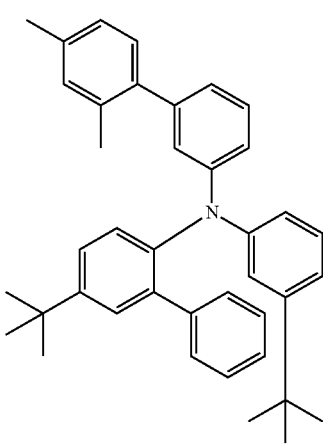

53-2

Compound 53-2 was obtained in the same manner as in Preparation of Compound 1-2 of Preparation Example 9 except that Compound 53-1 was used instead of Compound 1-1.

MS: [M+H]⁺=573

Preparation Example 218: Synthesis of Compound 53-3

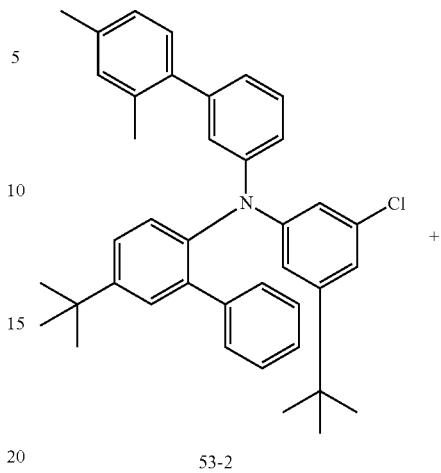

53-2

+

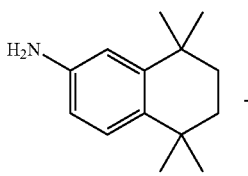

Pd(Pt-Bu₃)₂, NaOt-Bu / Toluene →

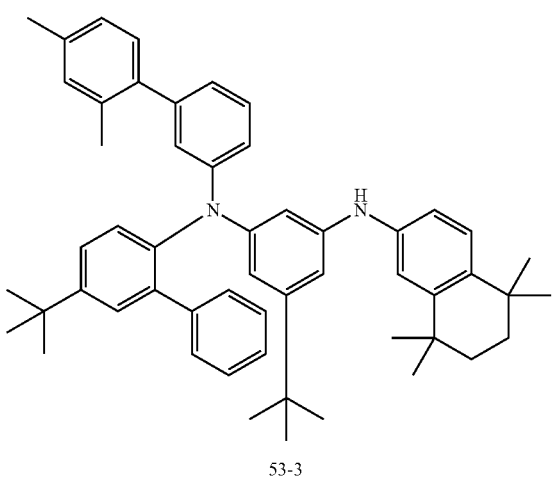

53-3

Compound 53-3 was obtained in the same manner as in Preparation of Compound 1-3 of Preparation Example 10 except that Compound 53-2 was used instead of Compound 1-2, and 5,5,8,8-tetramethyl-5,6,7,8-tetrahydronaphthalen-2-amine was used instead of 4-(tert-butyl)aniline.

MS: [M+H]⁺=740

Preparation Example 219: Synthesis of Compound 53-4

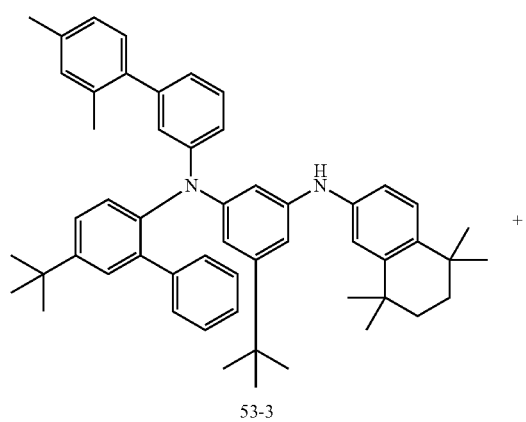

53-3

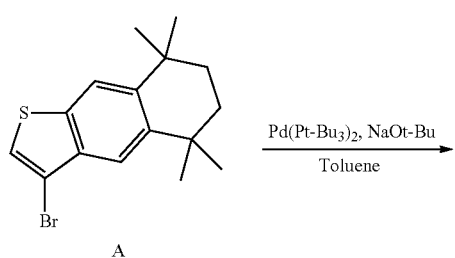

A

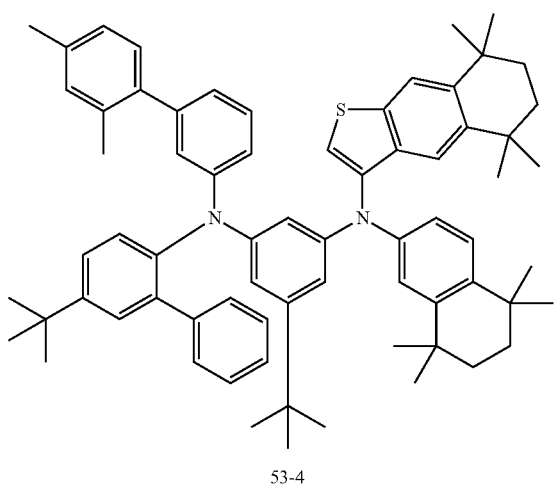

53-4

Compound 53-4 was obtained in the same manner as in Preparation of Compound 1-4 of Preparation Example 11 except that Compound 53-3 was used instead of Compound 1-3.

MS: [M+H]$^+$=982

Preparation Example 220: Synthesis of Compound 53

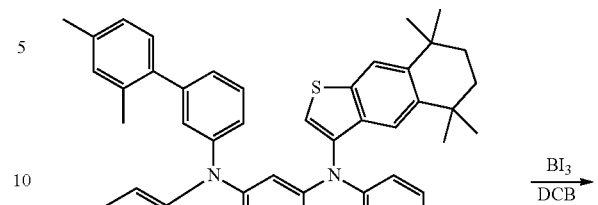

53-4

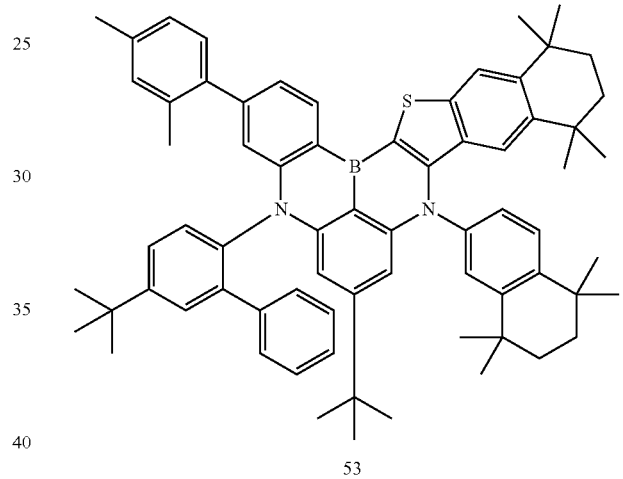

53

Compound 53 was obtained in the same manner as in Preparation of Compound 1 of Preparation Example 12 except that Compound 53-4 was used instead of Compound 1-4.

MS: [M+H]$^+$=990

Preparation Example 221: Synthesis of Compound 54-1

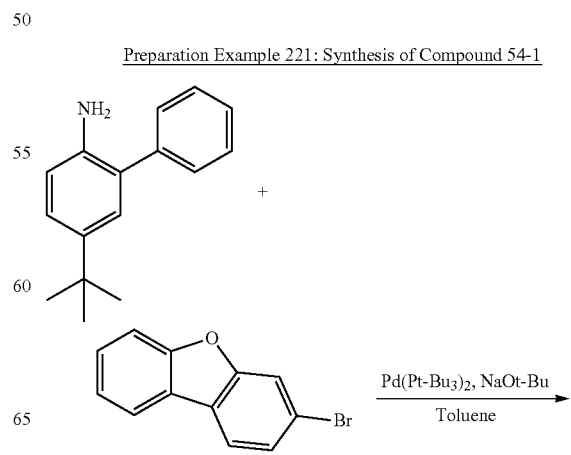

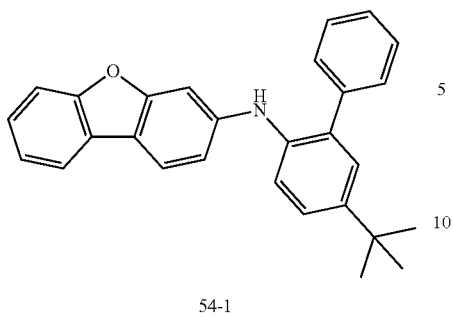

54-1

Compound 54-1 was obtained in the same manner as in Preparation of Compound 1-1 of Preparation Example 8 except that 3-bromodibenzo[b,d]furan was used instead of 6-bromo-1,1,4,4-tetramethyl-1,2,3,4-tetrahydronaphthalene.

MS: [M+H]⁺=392

Preparation Example 222: Synthesis of Compound 54-2

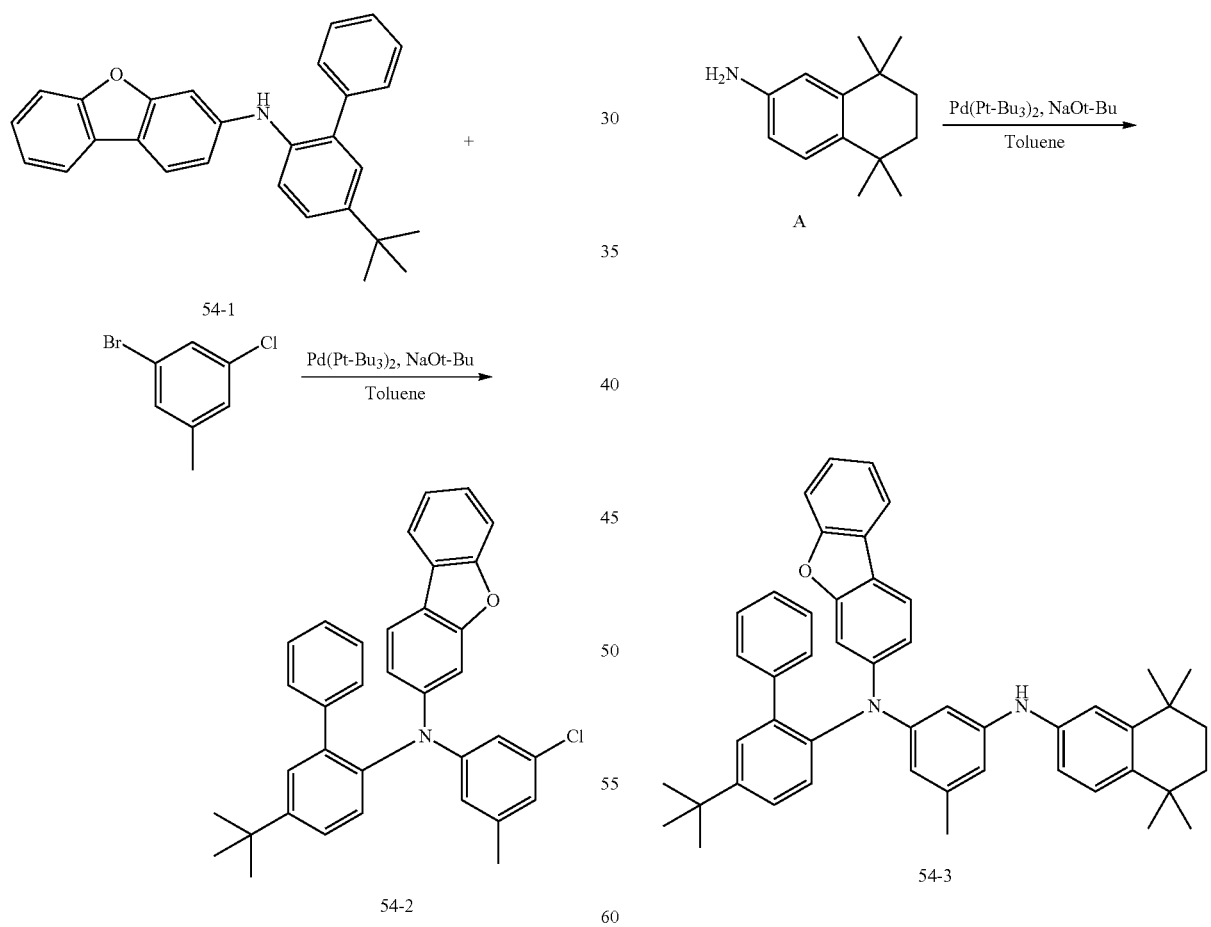

54-2

Compound 54-2 was obtained in the same manner as in Preparation of Compound 1-2 of Preparation Example 9 except that Compound 54-1 was used instead of Compound 1-1.

MS: [M+H]⁺=517

Preparation Example 223: Synthesis of Compound 54-3

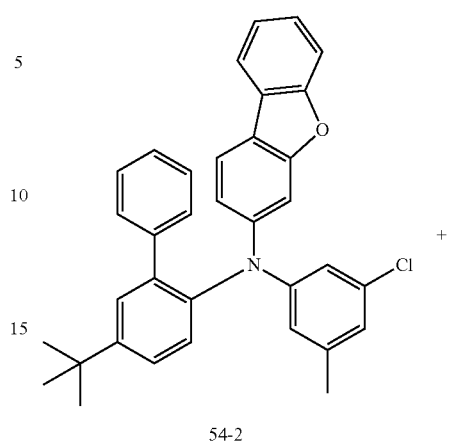

54-3

Compound 54-3 was obtained in the same manner as in Preparation of Compound 1-3 of Preparation Example 10 except that Compound 54-2 was used instead of Compound 1-2, and 5,5,8,8-tetramethyl-5,6,7,8-tetrahydronaphthalen-2-amine was used instead of 4-(tert-butyl)aniline.

MS: [M+H]⁺=683

Preparation Example 224: Synthesis of Compound 54-4

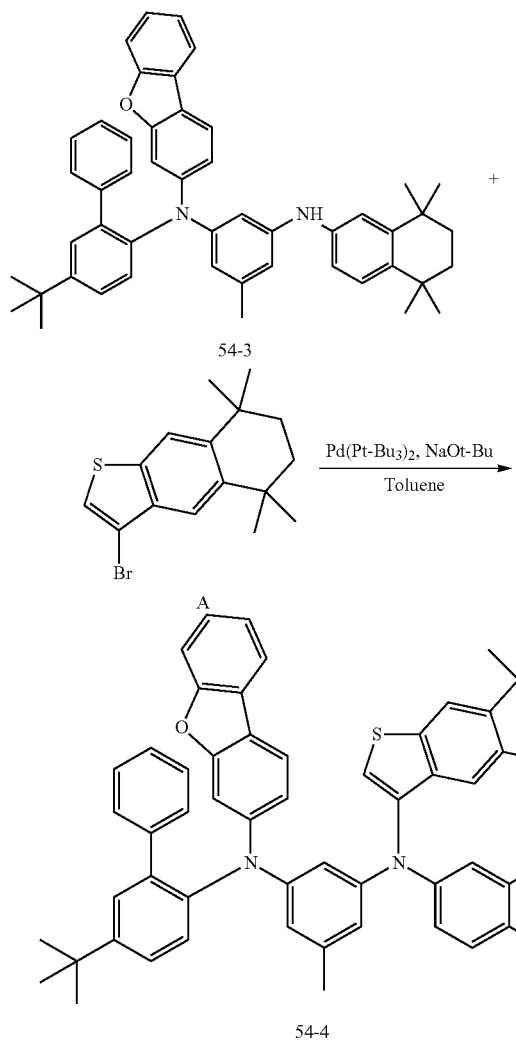

Compound 54-4 was obtained in the same manner as in Preparation of Compound 1-4 of Preparation Example 11 except that Compound 54-3 was used instead of Compound 1-3.
MS: [M+H]⁺=926

Preparation Example 225: Synthesis of Compound 54

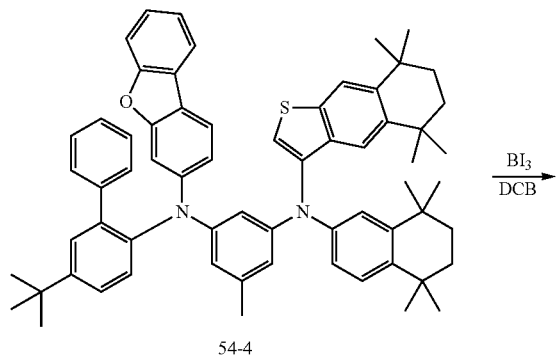

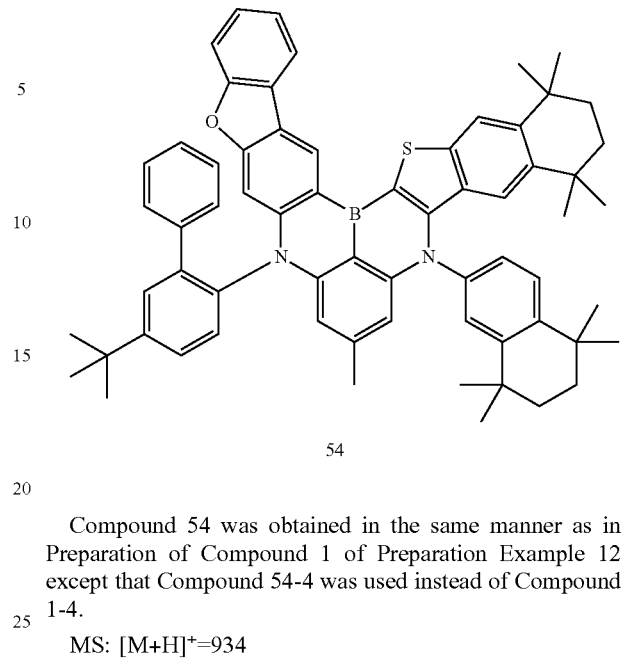

Compound 54 was obtained in the same manner as in Preparation of Compound 1 of Preparation Example 12 except that Compound 54-4 was used instead of Compound 1-4.
MS: [M+H]⁺=934

Experimental Example 1: Simulation

Example 1-1

Figure 5:
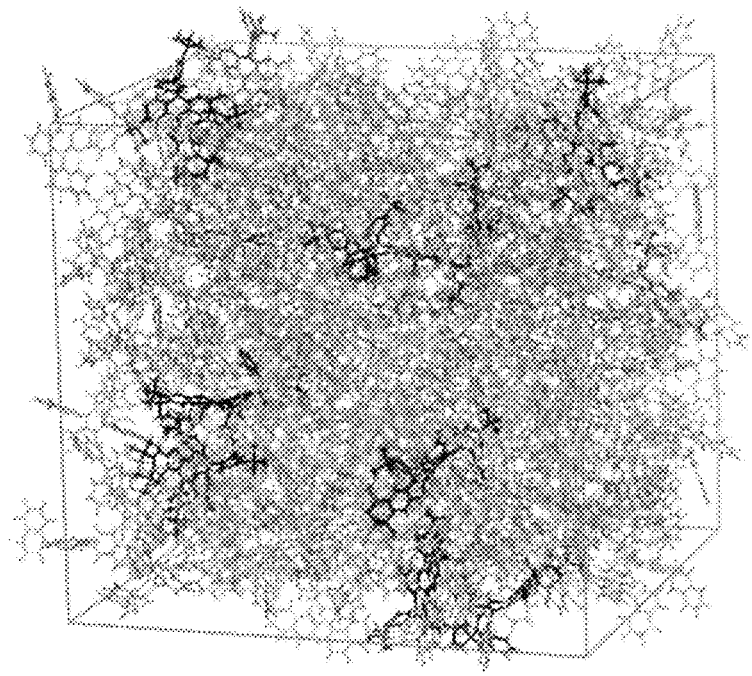

A system in which Compounds BD-1 and BH-1 are included in a weight ratio of 5:95 was prepared. Specifically, using an OPLS3e force field, an environment of a doped device was computational chemically obtained through NVT and NPT calculations employing 300 molecules (BH-1 95%, A-1 5% ratio), a temperature of 300 K and a simulation time of 30 ns, and the obtained molecular model is shown in FIG. 5.

Volume and density of the whole molecule, and an average distance between different molecules herein were obtained by calculation. The results are as shown in the following Table 1.

X-1

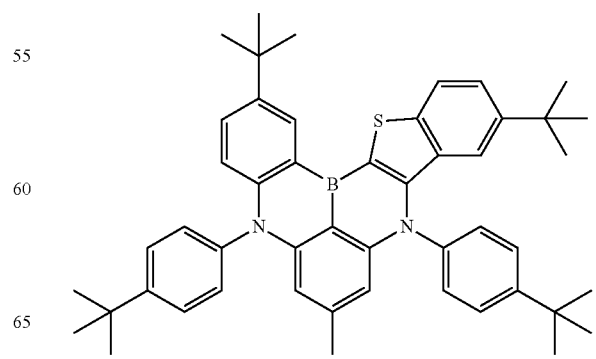

X-2

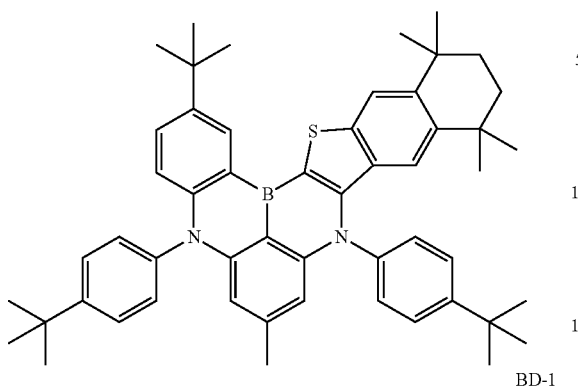

BD-1

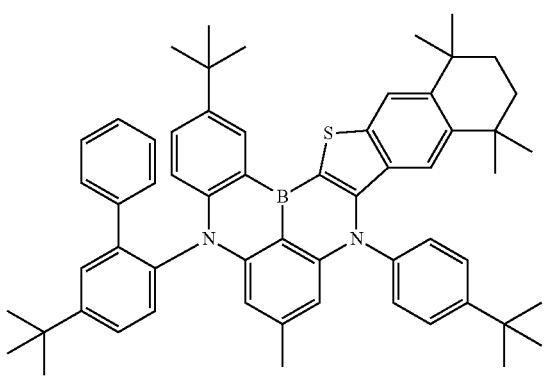

BD-2

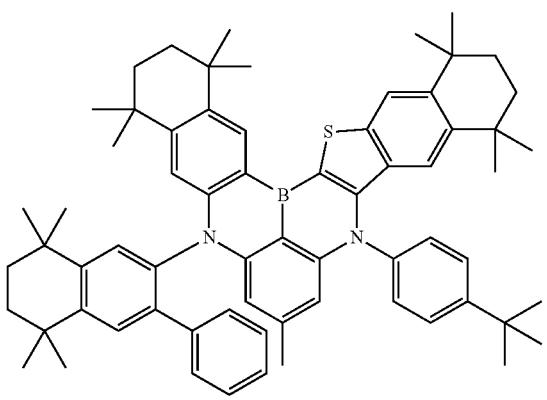

BH-1

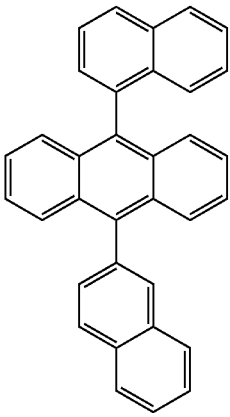

A molecular system calculation was performed in the same manner as in Example 1 except that a dopant described in the following Table 1 was used instead of Compound BD-1.

Comparative Examples 1-1 and 1-2

Molecular system calculations were performed in the same manner as in Example 1 except that dopants described in the following Table 1 were used instead of Compound BD-1.

Specifically, molecular models obtained by Examples 1-1 and 1-2 and Comparative Examples 1-1 and 1-2 are shown in FIG. 3 to FIG. 6.

Figure 3:
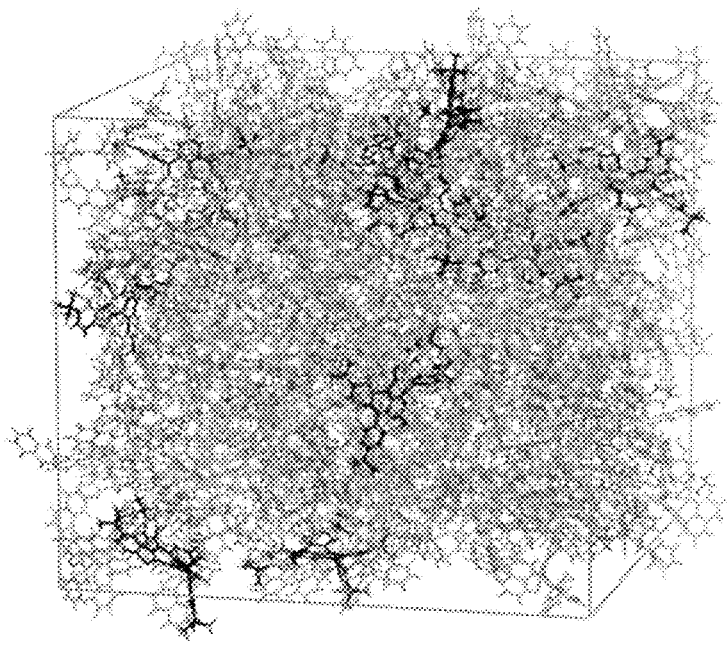
FIG. 3 to FIG. 6 are diagrams showing molecular models obtained through simulations of Experimental Example 1 of the present specification.

Specifically, FIG. 3 is a diagram showing a molecular model obtained through a simulation of the system of X-1 and BH-1 of Comparative Example 1-1.

Figure 4:
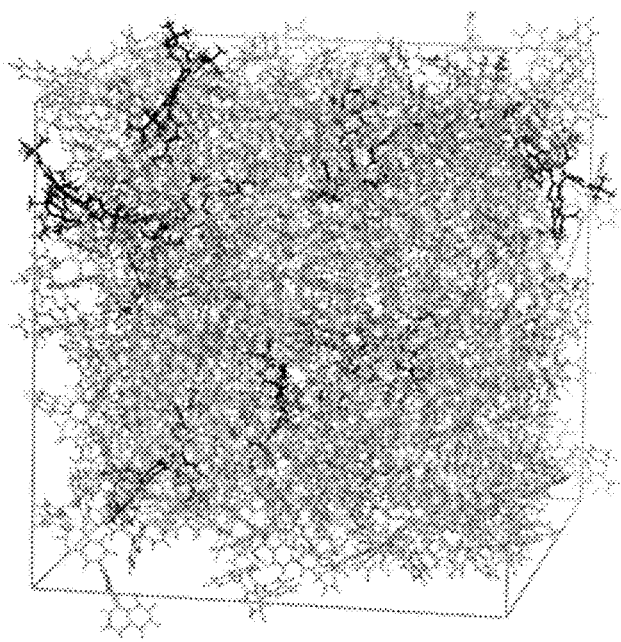

FIG. 4 is a diagram showing a molecular model obtained through a simulation of the system of X-2 and BH-1 of Comparative Example 1-2.

FIG. 5 is a diagram showing a molecular model obtained through a simulation of the system of BD-1 and BH-1 of Example 1-1.

Figure 6:
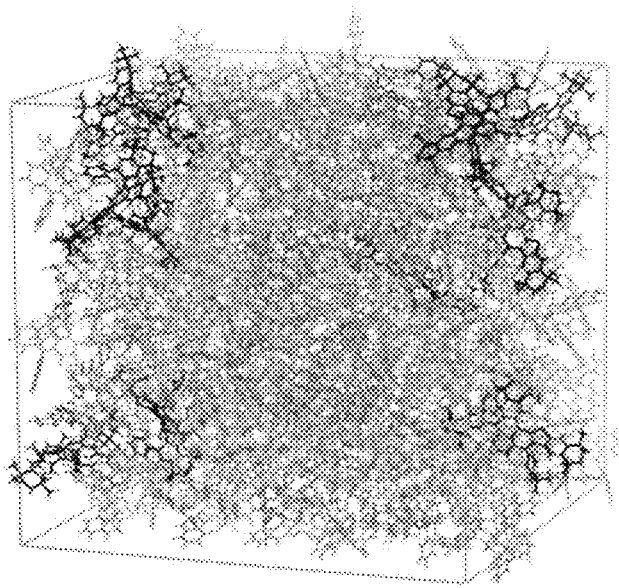

FIG. 6 is a diagram showing a molecular model obtained through a simulation of the system of BD-2 and BH-1 of Example 1-2.

TABLE 1

| Entry | System | Total Volume ($cm^3$) | Total Density ($g/cm^3$) | Intermolecular Distance (Å) |
|---|---|---|---|---|
| Comparative Example 1-1 | System of X-1 and BH-1 | $202.66 \times 10^{-27}$ | 1.093 | 15.10 |
| Comparative Example 1-2 | System of X-2 and BH-1 | $203.84 \times 10^{-27}$ | 1.094 | 15.19 |
| Example 1-1 | System of BD-1 and BH-1 | $206.36 \times 10^{-27}$ | 1.089 | 15.38 |
| Example 1-2 | System of BD-2 and BH-1 | $208.49 \times 10^{-27}$ | 1.091 | 15.56 |

From Table 1 and FIG. 3 to FIG. 6, it was identified that the distance between the host and the dopant increased in the system employing, as a dopant, each of Compounds BD-1 and BD-2 including one or more substituted or unsubstituted fused aliphatic hydrocarbon rings and including Y1 and Y2, that is, substituents at an ortho position, which is the compound of Chemical Formula 1 of the present specification, and BH-1 as a host compared to in the system of each of Compounds X-1 and X-2, and BH-1. Accordingly, it may be expected that device efficiency increases when manufacturing an organic light emitting device by introducing the compound including one or more substituted or unsubstituted fused aliphatic hydrocarbon rings and including Y1 and Y2, that is, substituents at an ortho position, which is the compound of Chemical Formula 1 of the present specification, as a dopant of a light emitting layer since a dexter energy transfer with triplet energy of the host occurs less.

Experimental Example 2: Experiment of Spectroscopic Analysis

Examples 2-1 and 2-2 and Comparative Examples 2-1 and 2-2

Figure 7:
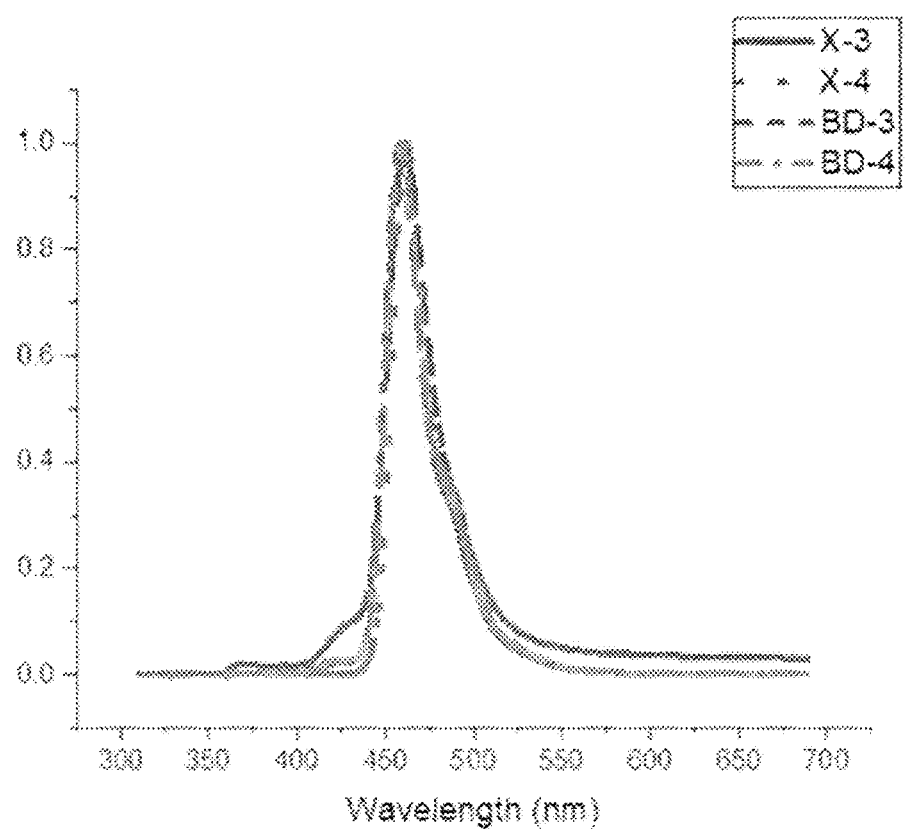
FIG. 7 and FIG. 8 are graphs showing photoluminescence analysis according to Experimental Example 2 of the present specification.
Figure 8:
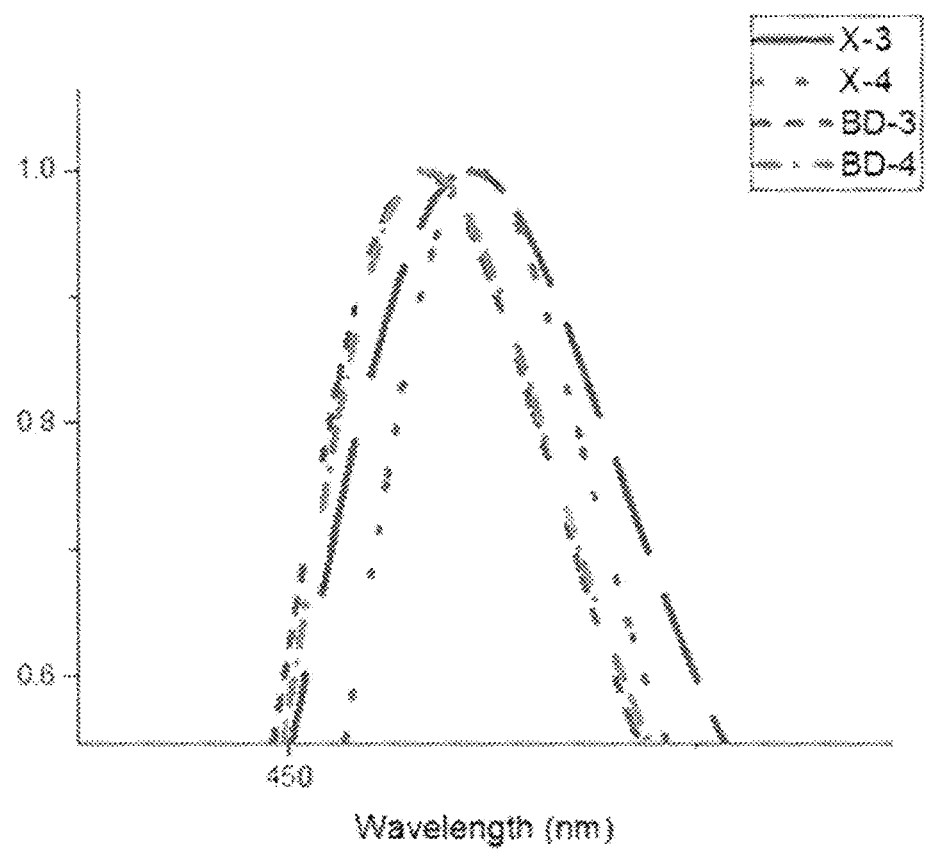

A maximum emission wavelength of each of compounds of the following Table 2 was measured and described in the following Table 2, and the maximum emission wavelength in a film state of each of the compounds of the following Table 2 was obtained as follows. On a glass substrate, a host Compound BH-1 and a dopant compound of the following Table 2 were vacuum deposited in a weight ratio of 97:3 to prepare a light emitting layer film having a thickness of 1000 Å. In the above-mentioned process, the deposition rate of the organic material was maintained at 0.1 nm/sec. For each of the prepared films, a fluorescence spectrum was measured at room temperature (300 K) using the measurement device. Herein, a wavelength value (nm) of the maximum emission peak was obtained, and the measurement graphs are shown in FIG. 7 and FIG. 8.

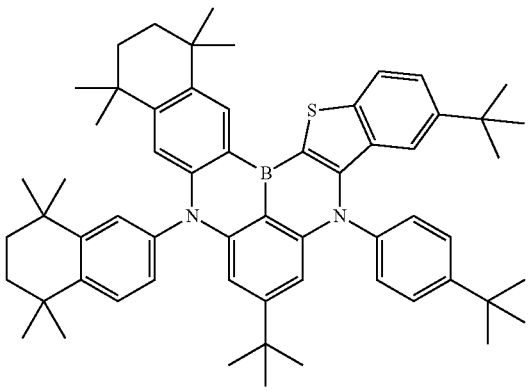

X-4

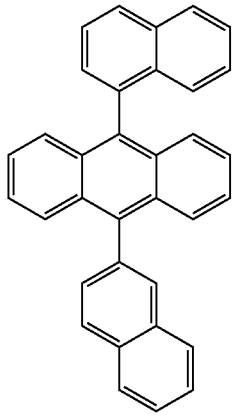

BH-1

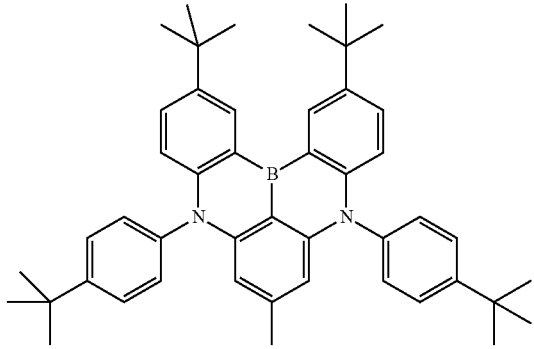

X-3

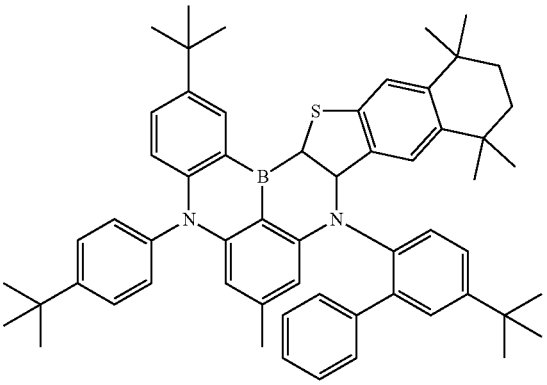

BD-3

BD-4

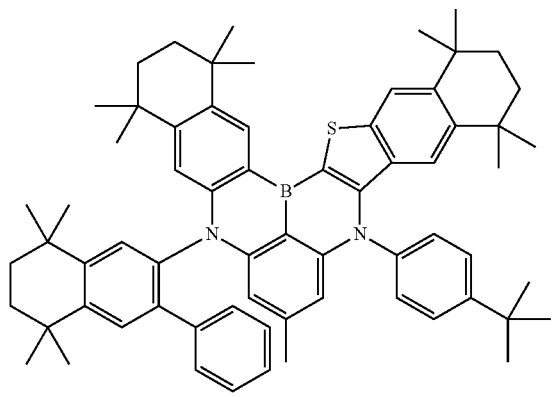

TABLE 2

|  | Dopant Compound | Maximum Emission Wavelength (nm) |
| --- | --- | --- |
| Comparative Example 2-1 | X-3 | 461 |
| Comparative Example 2-2 | X-4 | 463 |
| Example 2-1 | BD-3 | 458 |
| Example 2-2 | BD-4 | 459 |

When comparing the maximum emission wavelength values in Table 2, FIG. 7 and FIG. 8, a shorter wavelength was observed in Compounds BD-3 and BD-4 including one or more substituted or unsubstituted fused aliphatic hydrocarbon rings and including Y1 and Y2, that is, substituents at an ortho position, which is the compound of Chemical Formula 1 of the present specification, compared to in Compounds X-3 and X-4. This is due to the fact that intermolecular interaction is minimized between the host and the dopant as shown in the experimental results of the simulation of Experimental Example 1. Therefore, an organic light emitting device with high efficiency is obtained using the compound represented by Chemical Formula 1.

Experimental Example 3: Device Example

Example 3-1

A glass substrate on which indium tin oxide (ITO) was coated as a thin film to a thickness of 1,400 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum deposition apparatus.

On the transparent ITO electrode prepared as above, the following HI-A and LG-101 were thermal vacuum deposited to thicknesses of 650 Å and 50 Å, respectively, to form a hole injection layer. On the hole injection layer, a hole transfer layer was formed by vacuum depositing the following HT-A to a thickness of 600 Å. The following HT-B was vacuum deposited to a thickness of 50 Å on the hole transfer layer to form an electron blocking layer. Subsequently, on the electron blocking layer, a light emitting layer was formed to a thickness of 200 Å by vacuum depositing the following Compound 1 as a blue light emitting dopant in 4 parts by weight based on 100 parts by weight of the light emitting layer, and the following BH-A as a host. Then, on the light emitting layer, the following Compound ET-A was vacuum deposited to 50 Å as a first electron transfer layer, and subsequently, the following ET-B and LiQ were vacuum deposited in a weight ratio of 1:1 to a thickness of 360 Å to form a second electron transfer layer. An electron injection layer was formed on the second electron transfer layer by vacuum depositing LiQ to a thickness of 5 Å. On the electron injection layer, a cathode was formed by depositing aluminum and silver in a weight ratio of 10:1 to a thickness of 220 Å, and then depositing aluminum thereon to a thickness of 1000 Å.

In the above-described process, the deposition rates of the organic materials were maintained at 0.4 Å/sec to 0.9 Å/sec, the deposition rate of the aluminum of the cathode was maintained at 2 Å/sec, and the degree of vacuum during the deposition was maintained at $5 \times 10^{-8}$ torr to $1 \times 10^{-7}$ torr, and as a result, an organic light emitting device was manufactured.

HI-A

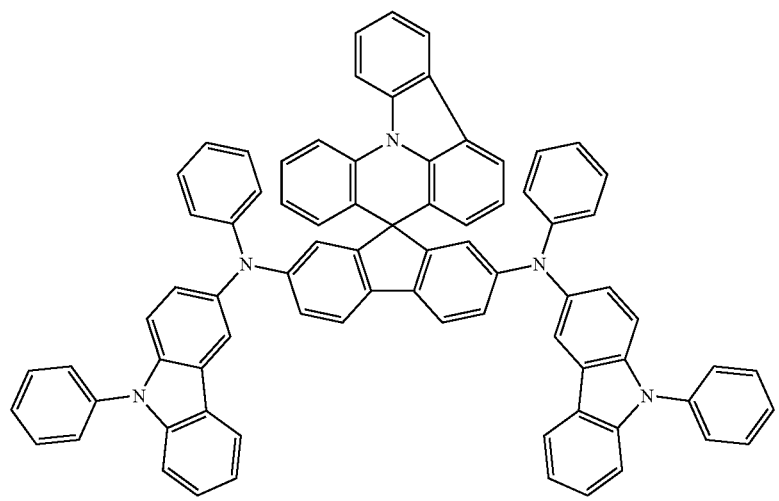

-continued
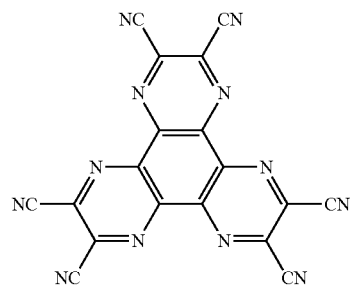
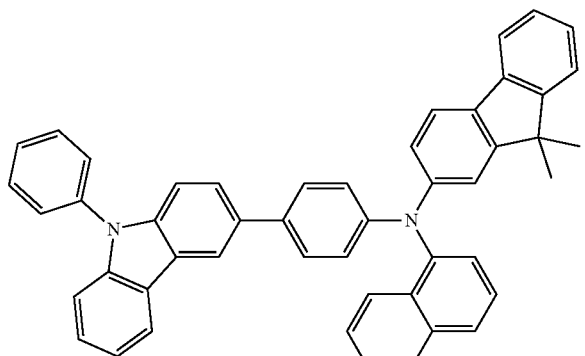
HT-B
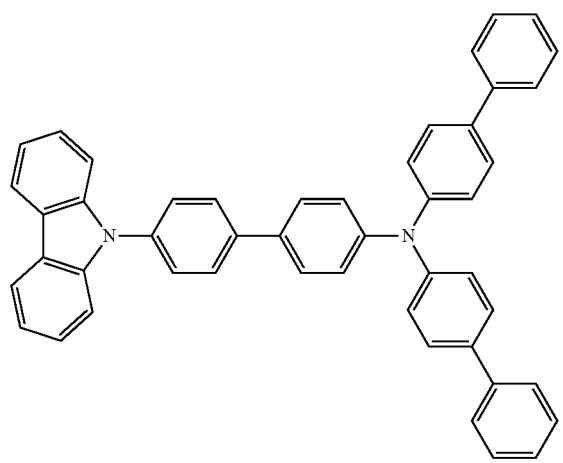
BH-A
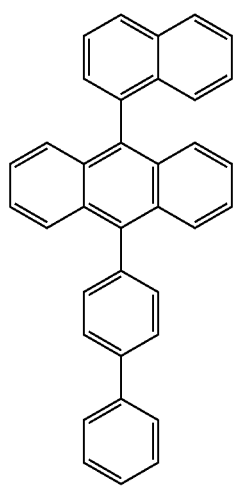

-continued

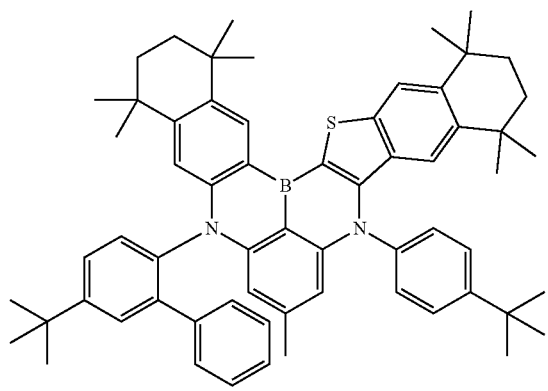
ET-A

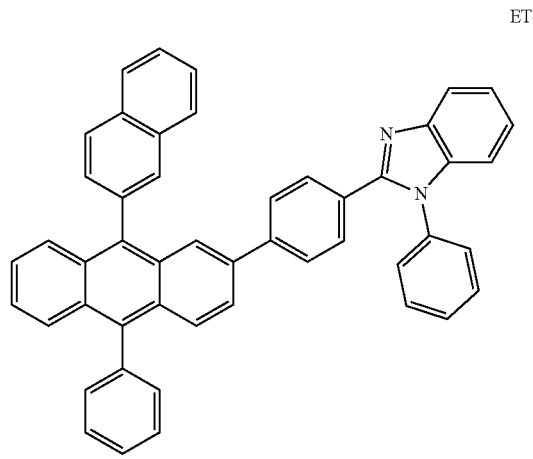
ET-B

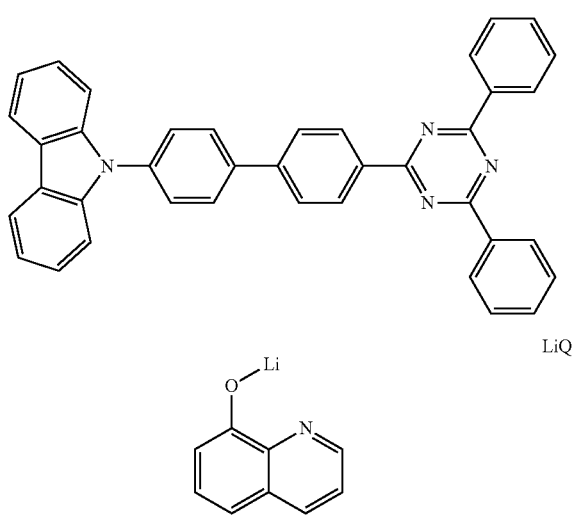
LiQ

Examples 3-2 to 3-40 and Comparative Examples 3-1 to 3-6

Organic light emitting devices of Examples 3-2 to 3-40 and Comparative Examples 3-1 to 3-6 were each manufactured in the same manner as in Example 3-1 except that compounds described in the following Table 3 were each used as the dopant of the light emitting layer instead of Compound 1, and compounds described in the following Table 3 were each used as the host material instead of BH-A.

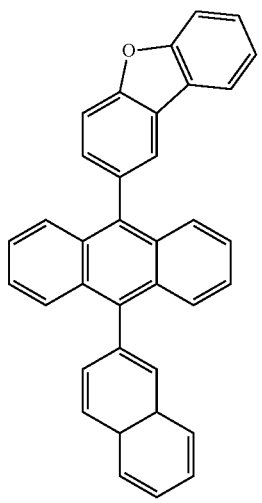

BH-B

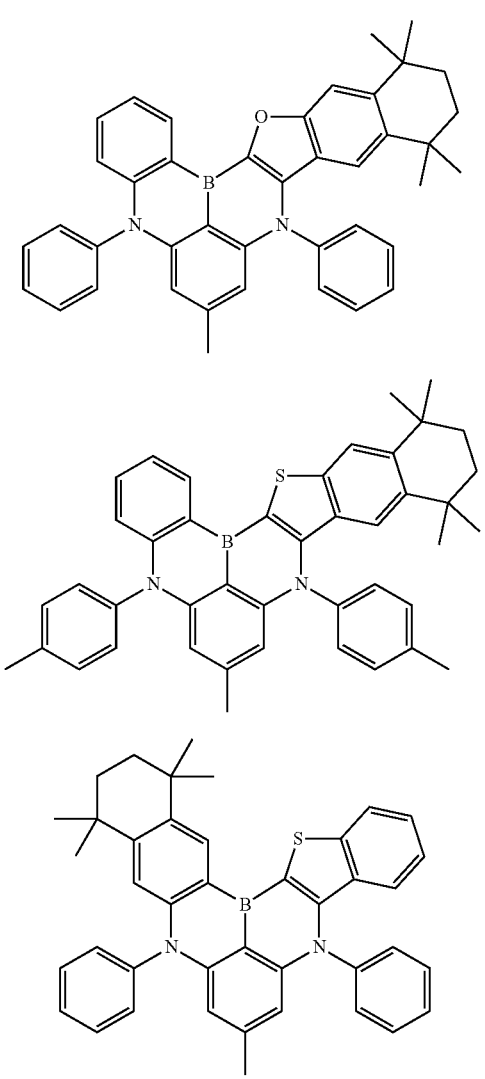

BD-A

BD-B

BD-C

For each of the organic light emitting devices of Examples 3-1 to 3-40 and Comparative Examples 3-1 to 3-6, voltage, efficiency and color coordinate when applying current density of 10 mA/cm² and a lifetime ($T_9$ s) when applying current density of 20 mA/cm² were measured, and the results are shown in the following Table 3. Herein, $T_9$ s means time taken for luminance to decrease to 95% when employing initial luminance at current density of 20 mA/cm² as 100%, and the percentage is shown based on (100%) the results of Comparative Examples 3-2 and 3-5 including Compound BD-B.

TABLE 3

| | Light Emitting Layer | | 10 mA/cm² | | | 20 mA/cm² |
|---|---|---|---|---|---|---|
| | | | Voltage | Quantum Efficiency | Color Coordinate | LT95 |
| Entry | Host | Dopant | (V) | (QE) | CIEy | (%) |
| Example 3-1 | BH-A | Compound 1 | 3.82 | 8.05 | 0.0891 | 117 |
| Example 3-2 | | Compound 2 | 3.86 | 7.95 | 0.1067 | 130 |
| Example 3-3 | | Compound 4 | 3.74 | 8.25 | 0.0913 | 124 |
| Example 3-4 | | Compound 6 | 3.85 | 8.12 | 0.0901 | 123 |
| Example 3-5 | | Compound 11 | 3.78 | 8.52 | 0.0891 | 120 |
| Example 3-6 | | Compound 24 | 3.88 | 8.06 | 0.0888 | 131 |
| Example 3-7 | | Compound 28 | 3.86 | 8.23 | 0.0809 | 123 |
| Example 3-8 | BH-A | Compound 29 | 3.89 | 8.31 | 0.1022 | 126 |
| Example 3-9 | | Compound 30 | 3.75 | 8.44 | 0.1042 | 118 |
| Example 3-10 | | Compound 31 | 3.81 | 8.32 | 0.0962 | 113 |
| Example 3-11 | | Compound 39 | 3.79 | 8.73 | 0.0941 | 130 |
| Example 3-12 | | Compound 40 | 3.95 | 7.99 | 0.1020 | 125 |
| Example 3-13 | | Compound 41 | 3.83 | 8.51 | 0.0918 | 120 |
| Example 3-14 | | Compound 48 | 3.76 | 8.65 | 0.0804 | 115 |
| Example 3-15 | | Compound 49 | 3.77 | 8.59 | 0.1025 | 123 |
| Example 3-16 | | Compound 50 | 3.74 | 8.44 | 0.0791 | 111 |
| Example 3-17 | | Compound 51 | 3.77 | 8.80 | 0.1086 | 120 |
| Example 3-18 | | Compound 52 | 3.70 | 8.91 | 0.1011 | 125 |
| Example 3-19 | | Compound 53 | 3.71 | 8.83 | 0.0994 | 132 |
| Example 3-20 | | Compound 54 | 3.81 | 8.35 | 0.0961 | 121 |
| Example 3-21 | BH-B | Compound 1 | 3.75 | 8.10 | 0.0893 | 125 |
| Example 3-22 | | Compound 2 | 3.80 | 8.08 | 0.1064 | 122 |
| Example 3-23 | | Compound 4 | 3.71 | 8.35 | 0.0910 | 135 |
| Example 3-24 | | Compound 6 | 3.76 | 8.17 | 0.0904 | 123 |
| Example 3-25 | | Compound 11 | 3.73 | 8.57 | 0.0894 | 122 |
| Example 3-26 | | Compound 24 | 3.80 | 8.16 | 0.0893 | 125 |
| Example 3-27 | | Compound 28 | 3.79 | 8.28 | 0.0813 | 126 |
| Example 3-28 | | Compound 29 | 3.70 | 8.36 | 0.1017 | 115 |
| Example 3-29 | | Compound 30 | 3.77 | 8.49 | 0.1038 | 123 |
| Example 3-30 | | Compound 31 | 3.78 | 8.37 | 0.0965 | 111 |
| Example 3-31 | | Compound 39 | 3.72 | 8.75 | 0.0943 | 123 |
| Example 3-32 | | Compound 40 | 3.89 | 8.03 | 0.1021 | 124 |
| Example 3-33 | | Compound 41 | 3.76 | 8.61 | 0.0921 | 125 |
| Example 3-34 | | Compound 48 | 3.72 | 8.70 | 0.0806 | 124 |
| Example 3-35 | | Compound 49 | 3.74 | 8.64 | 0.1027 | 128 |
| Example 3-36 | | Compound 50 | 3.70 | 8.49 | 0.0801 | 115 |
| Example 3-37 | | Compound 51 | 3.71 | 8.85 | 0.1089 | 124 |
| Example 3-38 | | Compound 52 | 3.72 | 8.72 | 0.0993 | 124 |
| Example 3-39 | | Compound 53 | 3.76 | 8.66 | 0.1106 | 121 |
| Example 3-40 | | Compound 54 | 3.80 | 8.21 | 0.1001 | 132 |
| Comparative Example 3-1 | BH-A | BD-A | 3.83 | 7.62 | 0.0871 | 99 |
| Comparative Example 3-2 | | BD-B | 3.91 | 7.53 | 0.0942 | 100 |
| Comparative Example 3-3 | | BD-C | 3.95 | 7.72 | 0.1324 | 92 |
| Comparative Example 3-4 | BH-B | BD-A | 3.77 | 7.64 | 0.0873 | 98 |
| Comparative Example 3-5 | | BD-B | 3.85 | 7.56 | 0.0931 | 100 |
| Comparative Example 3-6 | | BD-C | 3.91 | 7.74 | 0.1312 | 93 |

As seen from the device results of Table 3, the compound including one or more substituted or unsubstituted fused aliphatic hydrocarbon rings and including Y1 and Y2, that is, substituents at an ortho position, which is the compound of Chemical Formula 1 of the present specification, was superior in both device efficiency and lifetime compared to the compound that does not include the compound of Chemical Formula 1 of the present specification. When compared with BD-A, BD-B or BD-C, a dopant introducing only a fused aliphatic hydrocarbon ring substituted with an alkyl group, it was seen that the compound including one or more substituted or unsubstituted fused aliphatic hydrocarbon rings and including Y1 and Y2, that is, substituents at an ortho position, which is the compound of Chemical Formula 1 of the present specification, had superior efficiency and lifetime. This is consistent with the experimental results of the simulation of Experimental Example 1.

Through Experimental Examples 1 to 3, it was identified that the compound of Chemical Formula 1 of the present specification had superior performance of high efficiency and long lifetime.

Experimental Example 4: Thermos Gravimetric Analysis

Figure 9:
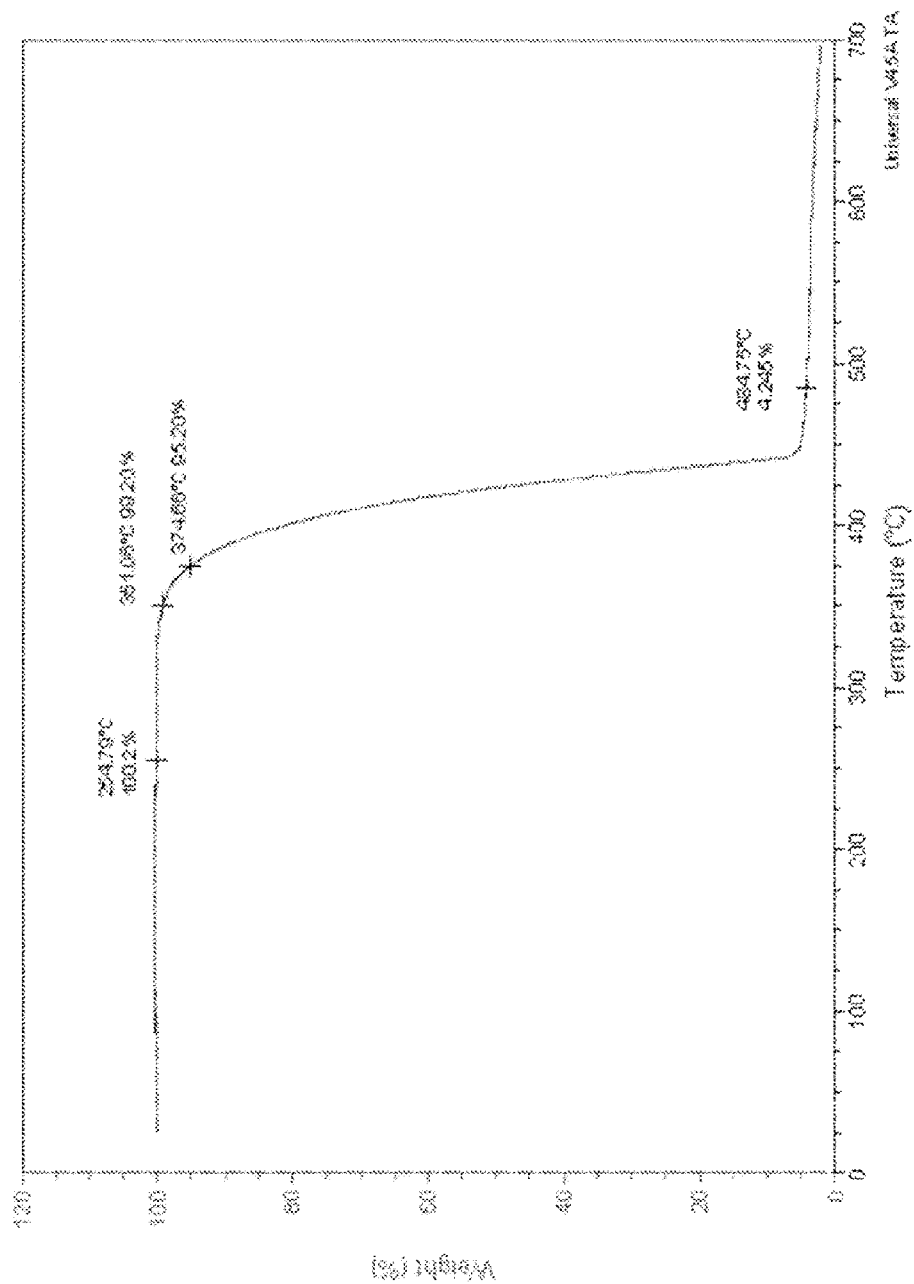
FIG. 9 is a graph showing a thermos gravimetric analysis of Example 4-1 of the present specification.
Figure 10:
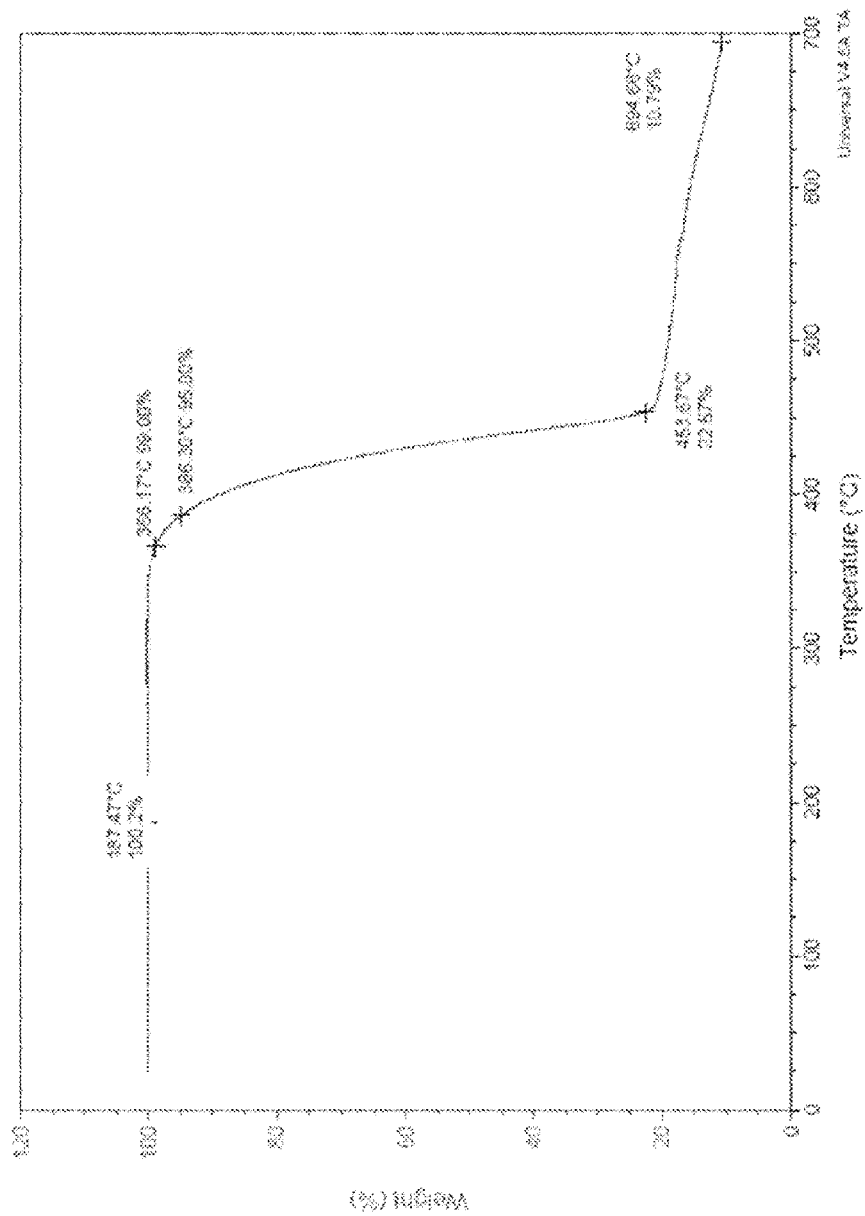
FIG. 10 is a graph showing a thermos gravimetric analysis of Comparative Example 4-1 of the present specification.

A thermos gravimetric analyzer (TGA) is a device measuring, after applying a temperature to a sample, changes in the mass of the sample as a function of time or temperature. A mass loss of a material is caused by evaporation or a chemical reaction producing gaseous products. Using Q-500, 3 mg or more and less than 5 mg of compounds of the following Table 4 completed with sublimation purification were each put on a Pt pan, and heated from room temperature to 700° C. at a rate of 10° C./min. Herein, a temperature at which the mass of each of the compounds was reduced by 5% with respect to the total weight (=Td-5% loss) and the amount (percent) of the residue remaining on the pan after heating to 700° C. were measured. The thermos gravimetric analysis graph of Compound BD-3 of Example 4-1 is shown in FIG. 9, and the thermos gravimetric analysis graph of Compound X-1 of Comparative Example 4-1 is shown in FIG. 10.

TABLE 4

| Entry | Comparative Example 4-1 | Comparative Example 4-2 | Example 4-1 | Example 4-2 |
| --- | --- | --- | --- | --- |
| Compound | X-1 | X-4 | BD-3 | BD-4 |
| Molecular Weight | 714.86 | 823.05 | 845.05 | 1007.33 |
| Td-5% loss (° C.) | 386 | 390 | 375 | 397 |
| Residue (%) | 22.7 | 0.6 | 4.2 | 2.2 |

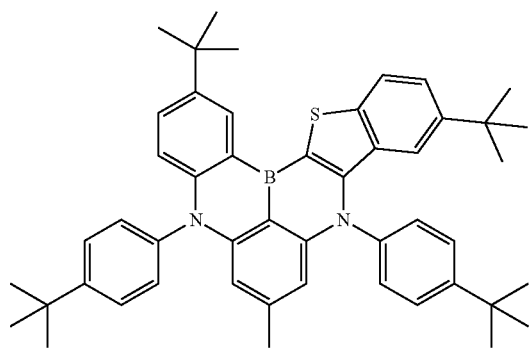

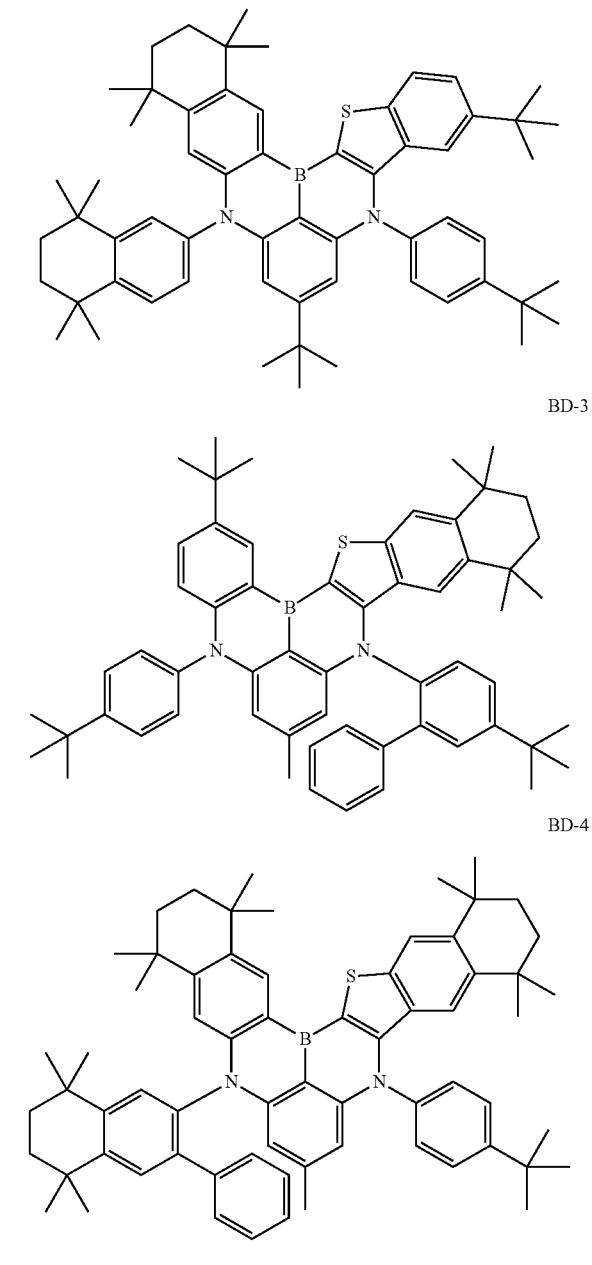

In Table 4, and FIG. 9 and FIG. 10, the Td-5% loss value was measured to be very high of 386° C. from the experimental result of the thermos gravimetric analysis on Compound X-1 of Comparative Example 4-1. On the other hand, it was identified through the experiment that Compound BD-3, the compound of Chemical Formula 1 of the present specification, of Example 4-1 had a lower Td 5% loss value of 375° C. even with a higher molecular weight. In addition, it was identified that BD-3 had 4.2% of the compound remaining on the pan after the analysis compared to X-1 having 22.7% of the compound remaining on the pan after the analysis. It was identified that Compound BD-4, the compound of Chemical Formula 1 of the present specification, of Example 4-2 had a similar Td 5% loss value with a higher molecular weight compared to Compound X-4 of Comparative Example 4-2. Through the experiment, it was identified that the compound of Chemical Formula 1 of the present specification was superior in terms of thermal stability by having a low a Td-5% loss value compared to compounds with similar molecular weights and thereby having a low sublimation temperature, and was an organic material suited for a deposition device as well.

The invention claimed is:

1. A compound represented by the following Chemical Formula 1:

[Chemical Formula 1]

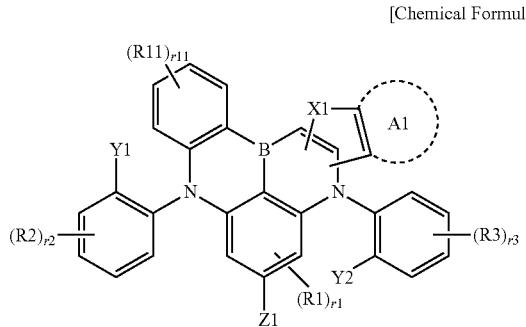

wherein in Chemical Formula 1,

X1 is O or S,

A1 is a substituted or unsubstituted aromatic hydrocarbon ring; a substituted or unsubstituted aliphatic hydrocarbon ring; or a substituted or unsubstituted fused ring of aromatic hydrocarbon ring and aliphatic hydrocarbon ring, at least one of Y1 and Y2 is deuterium; a cyano group; a halogen group; a substituted or unsubstituted alkyl group; a substituted or unsubstituted silyl group; a substituted or unsubstituted alkenyl group; a substituted or unsubstituted aryl group; or a substituted or unsubstituted heterocyclic group, or bonds to adjacent groups to form an aromatic hydrocarbon ring; a fused ring of aromatic hydrocarbon ring and aliphatic hydrocarbon ring; or a heteroring, and the remainder is hydrogen, with the proviso that when the at least one of Y1 and Y2 is a phenyl group, the at least one of Y1 and Y2 is a phenyl group substituted with one or more selected from the group consisting of deuterium; F; a cyano group; a trideuteriummethyl group; a cumyl group; a cumyl group substituted with deuterium; a trifluoromethyl group ($CF_3$); a trimethylsilyl group; and combinations thereof, Z1 is hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, R1 to R3 and R11 are the same as or different from each other, and each independently hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, or adjacent groups among R1 to R3 and R11 bond to each other to form a substituted or unsubstituted hydrocarbon ring, r1 is 1 or 2, when r1 is 2, the two R1s in the parentheses are the same as or different from each other, r2, r3 and r11 are each an integer of 1 to 4, when r2 is 2 or greater, the two or more R2s in the parentheses are the same as or different from each other, when r3 is 2 or greater, the two or more R3s in the parentheses are the same as or different from each other, when r11 is 2 or greater, the two or more R11s in the parentheses are the same as or different from each other, and the compound of Chemical Formula 1 includes at least one fused aliphatic hydrocarbon ring having 6 to 30 carbon atoms substituted with a substituted or unsubstituted linear or branched alkyl group having 1 to 30 carbon atoms.

2. The compound of claim 1, wherein the compound of Chemical Formula 1 is represented by the following Chemical Formula 1-1 or 1-2:

[Chemical Formula 1-1]

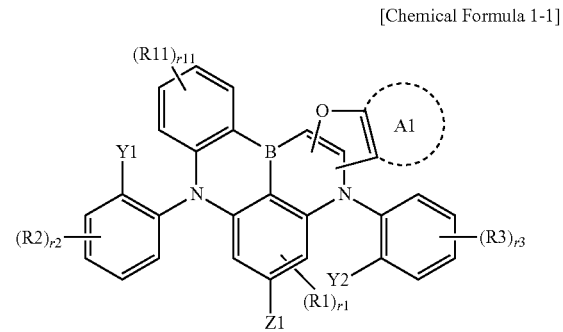

[Chemical Formula 1-2]

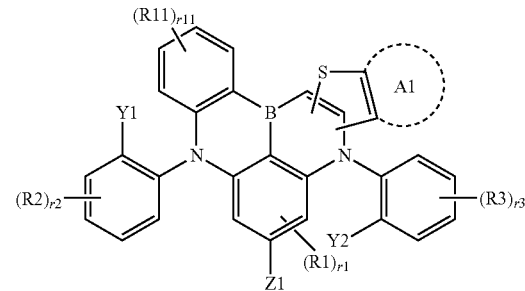

wherein in Chemical Formulae 1-1 and 1-2,

A1, Y1, Y2, Z1, R1 to R3, R11, r1 to r3 and r11 are the same as defined in Chemical Formula 1.

3. The compound of claim 1, wherein the compound of Chemical Formula 1 is represented by any one of the following Chemical Formulae 1-3 to 1-5:

[Chemical Formula 1-3]

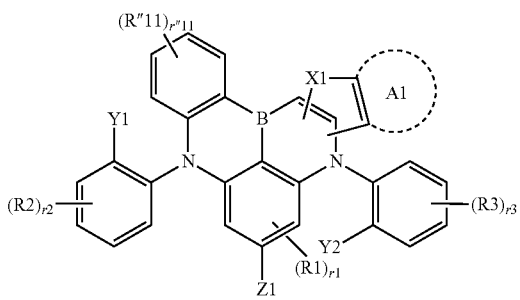

[Chemical Formula 1-4]

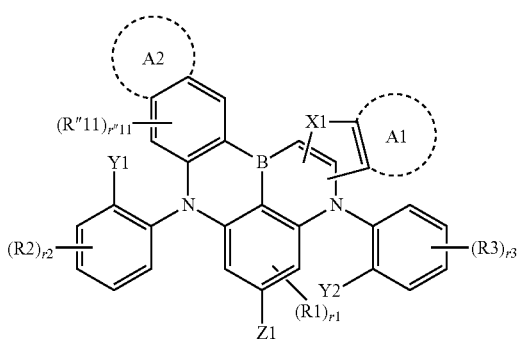

[Chemical Formula 1-5]

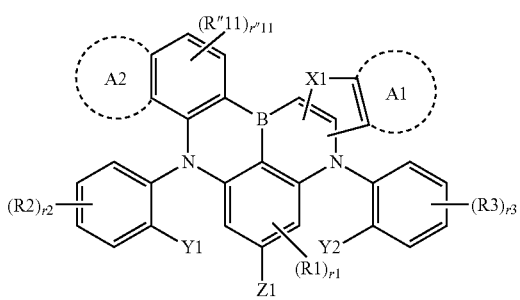

wherein in Chemical Formulae 1-3 to 1-5,

X1, A1, Y1, Y2, Z1, R1 to R3, and r1 to r3 are the same as defined in Chemical Formula 1, A2 is a substituted or unsubstituted aliphatic hydrocarbon ring, R'11 and R"11 are the same as or different from each other, and each independently hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, r'11 is an integer of 1 to 4, and when r'11 is 2 or greater, the two or more R'11 s in the parentheses are the same as or different from each other, and r"11 is 1 or 2, and when r"11 is 2, the two R"11 s in the parentheses are the same as or different from each other.

4. The compound of claim 1, wherein the compound of Chemical Formula 1 includes at least one monocyclic fused aliphatic hydrocarbon ring having 3 to 10 carbon atoms substituted with a linear or branched alkyl group having 1 to 30 carbon atoms unsubstituted or substituted with deuterium.

5. The compound of claim 1, wherein A1 is a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms, R11 is hydrogen; a substituted or unsubstituted linear or branched alkyl group having 1 to 30 carbon atoms; a substituted or unsubstituted amine group; or a substituted or unsubstituted monocyclic or polycyclic heterocyclic group having 2 to 30 carbon atoms, or adjacent groups of R11 bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic having 2 to 30 carbon atoms, at least one of Y1 and Y2 is deuterium; a cyano group; a halogen group; a substituted or unsubstituted linear or branched alkyl group having 1 to 30 carbon atoms; a substituted or unsubstituted linear or branched alkylsilyl group having 1 to 30 carbon atoms; a substituted or unsubstituted linear or branched alkenyl group having 2 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms, or bonds to adjacent groups to form a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heterocyclic having 2 to 30 carbon atoms, and the remainder is hydrogen, with the proviso that when the at least one of Y1 and Y2 is a phenyl group, the at least one of Y1 and Y2 is a phenyl group substituted with one or more selected from the group consisting of deuterium; F; a cyano group; a trideuteriummethyl group; a cumyl group substituted with deuterium; a trifluoromethyl group (CF3); a trimethylsilyl group; and combinations thereof, Z1 is hydrogen; deuterium; a halogen group; a cyano group; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted linear or branched alkylsilyl group having 1 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms, and R2 and R3 are the same as or different from each other, and each independently hydrogen; deuterium; a halogen group; a cyano group; a substituted or unsubstituted linear or branched alkyl group having 1 to 30 carbon atoms; a substituted or unsubstituted linear or branched alkylsilyl group having 1 to 30 carbon atoms; a substituted or unsubstituted monocyclic or polycyclic arylsilyl group having 6 to 30 carbon atoms; a substituted or unsubstituted amine group; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic aryl group having 6 to 30 carbon atoms, or adjacent groups bond to each other to form a substituted or unsubstituted monocyclic or polycyclic aliphatic hydrocarbon ring having 3 to 30 carbon atoms; a substituted or unsubstituted monocyclic or polycyclic aromatic hydrocarbon ring having 6 to 30 carbon atoms; a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroring having 2 to 30 carbon atoms.

6. A compound selected from the following compounds:

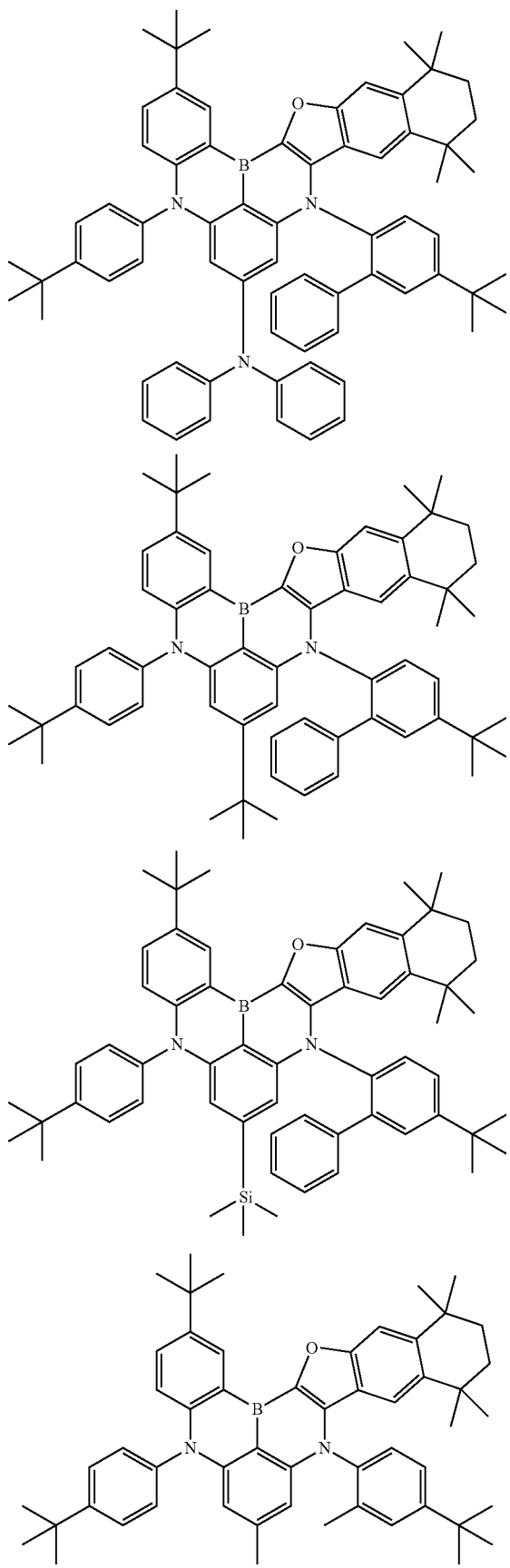

1027
-continued
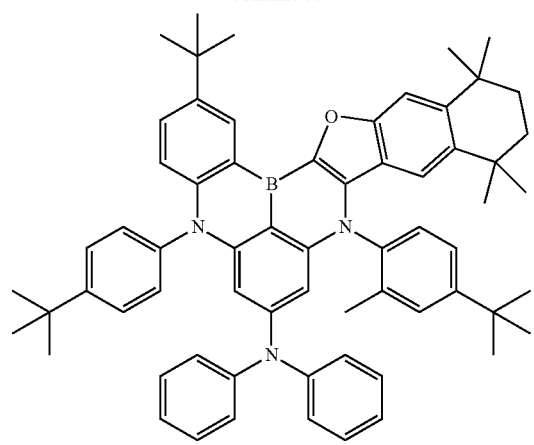
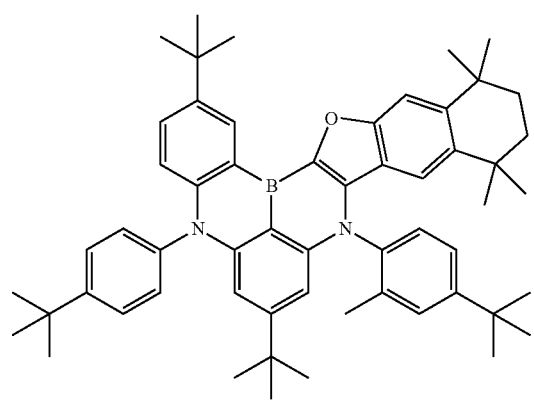
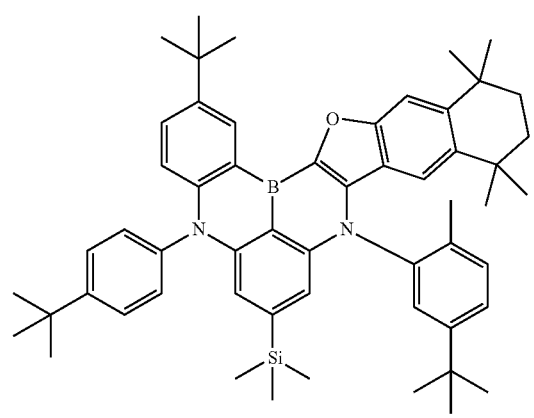
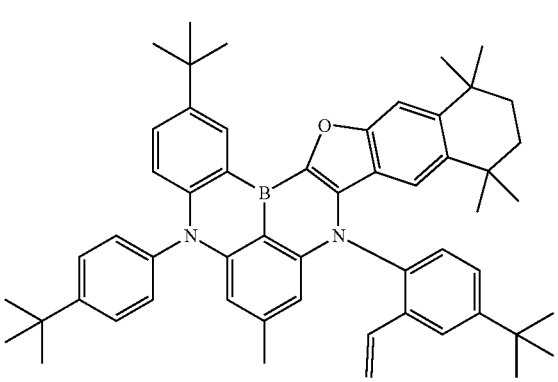
1028
-continued
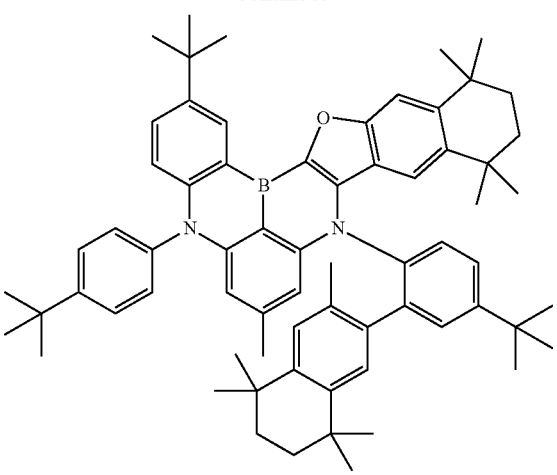

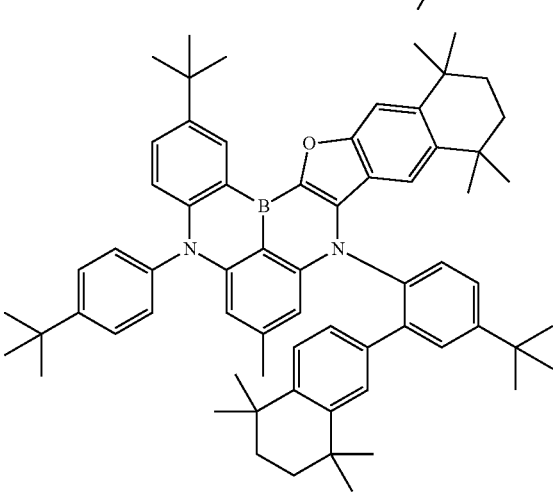

| 1029 -continued | 1030 -continued |
|---|---|
| 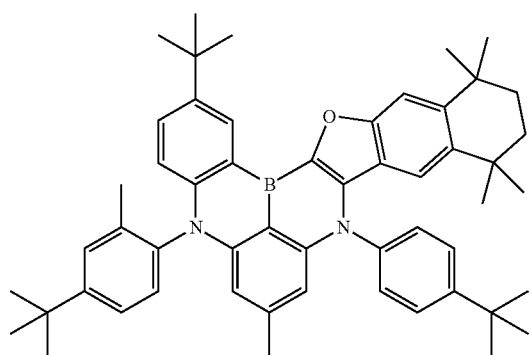 | 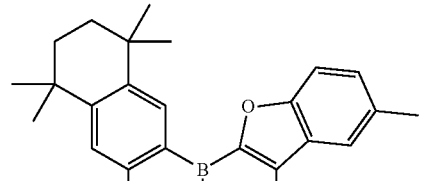 |
| 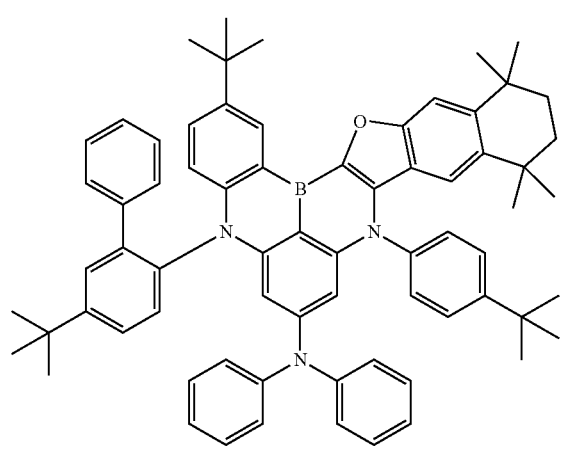 | 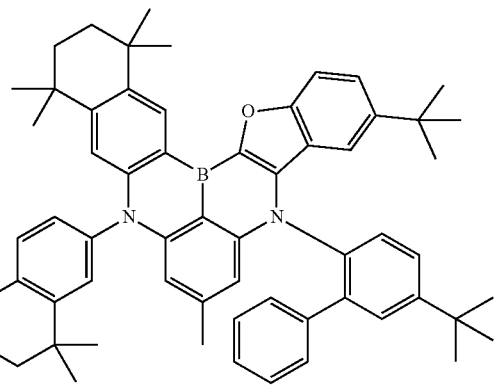 |
| 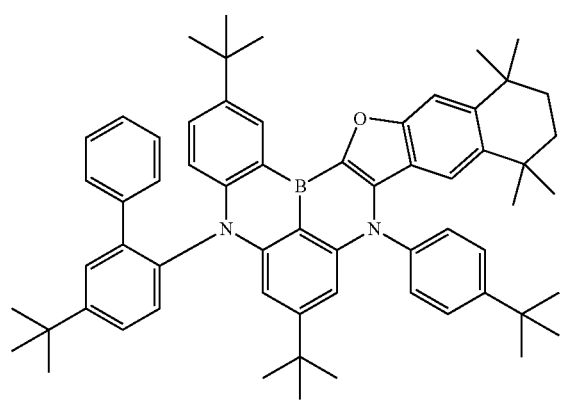 | 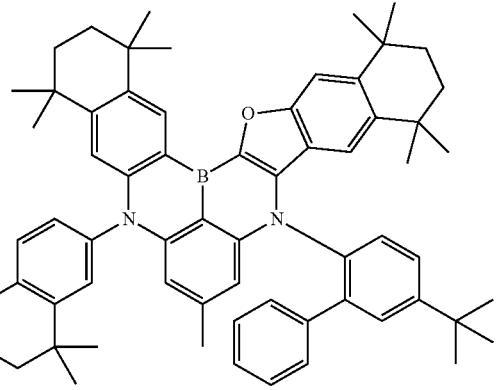 |
| 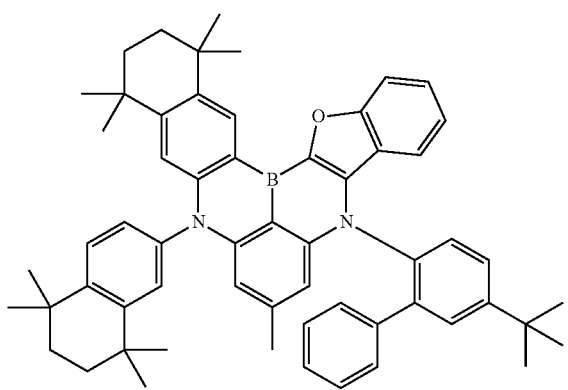 | 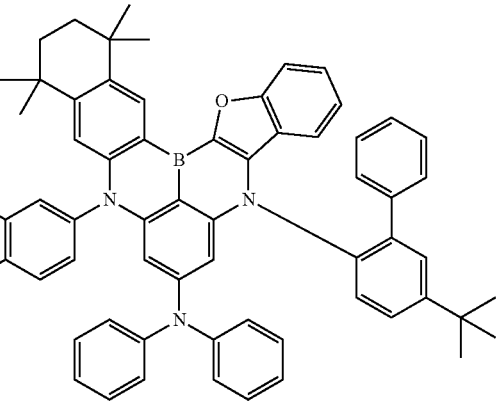 |

| 1031 -continued | 1032 -continued |
|---|---|
| 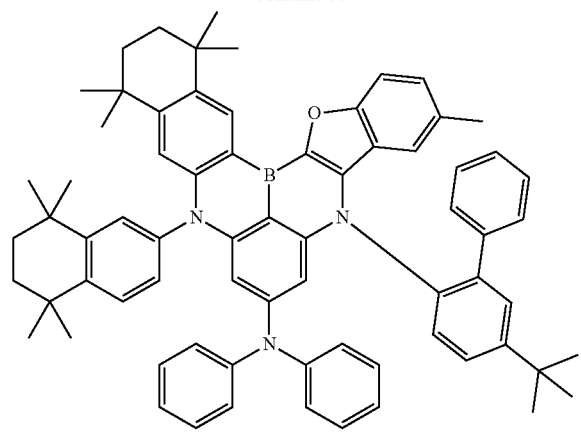 | 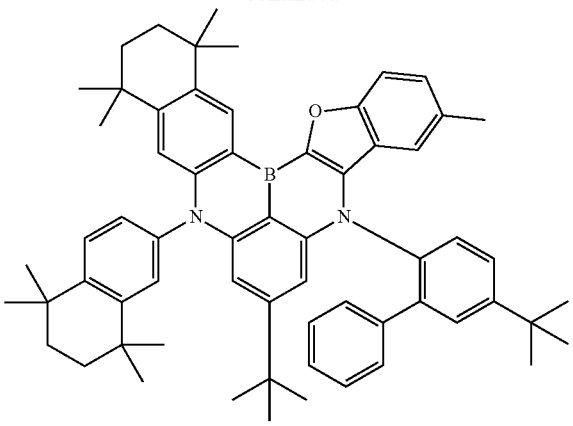 |
| 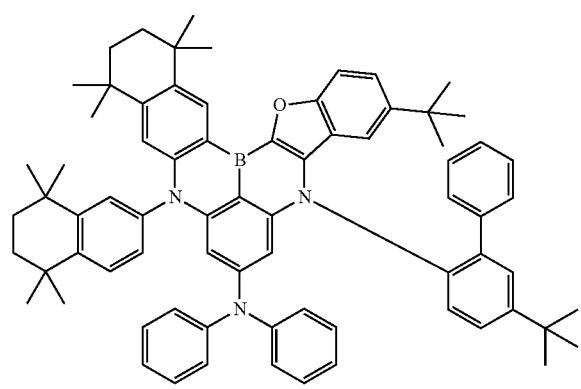 | 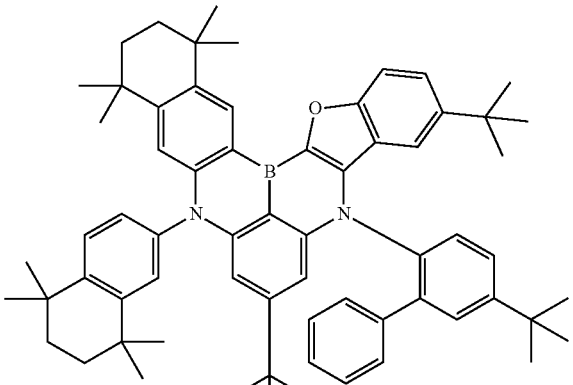 |
| 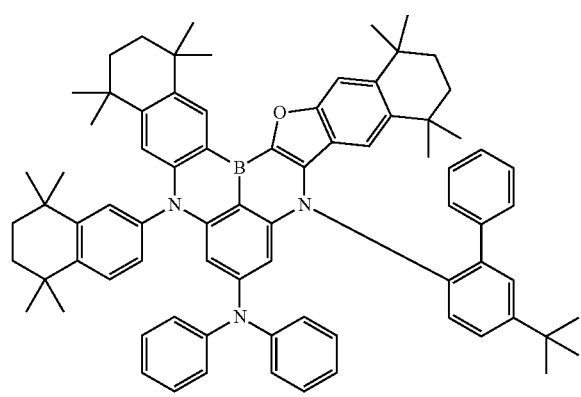 | 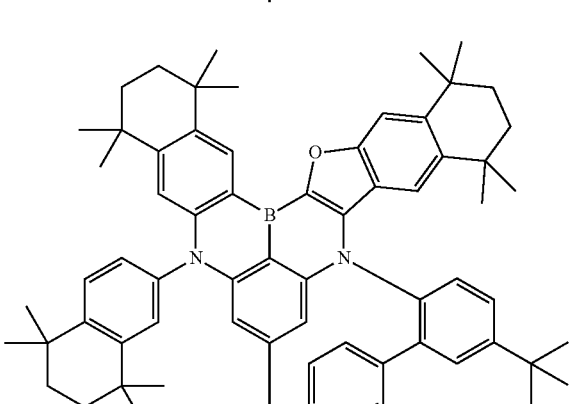 |
| 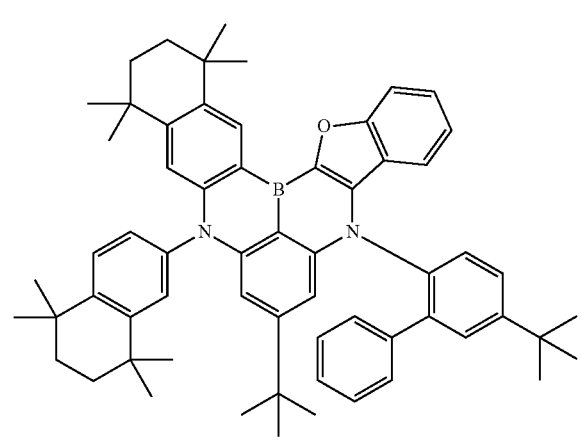 | 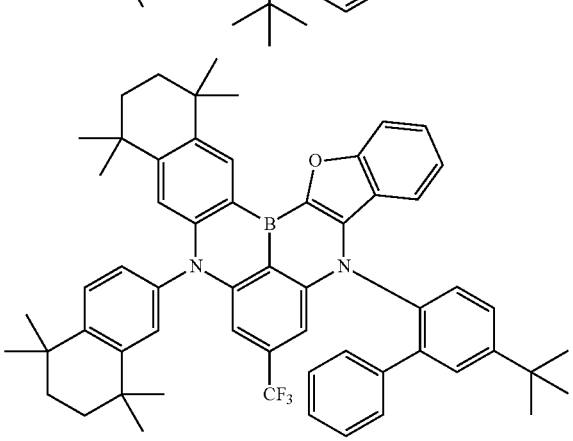 |

| 1033 -continued | 1034 -continued |
|---|---|
| 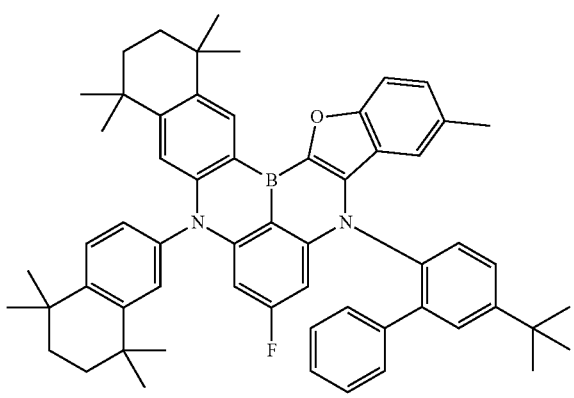 | 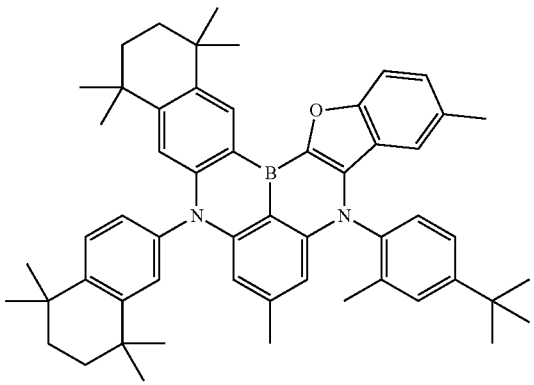 |
| 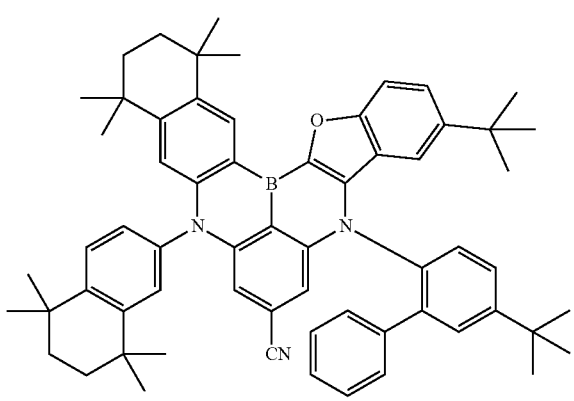 | 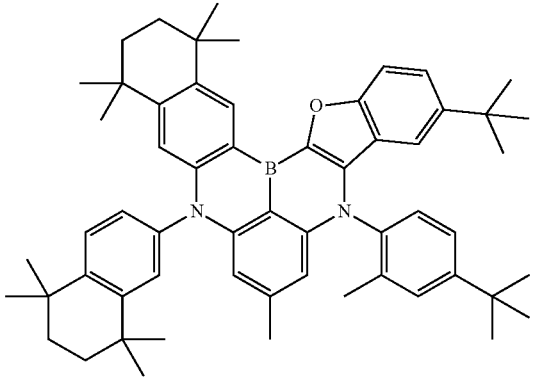 |
| 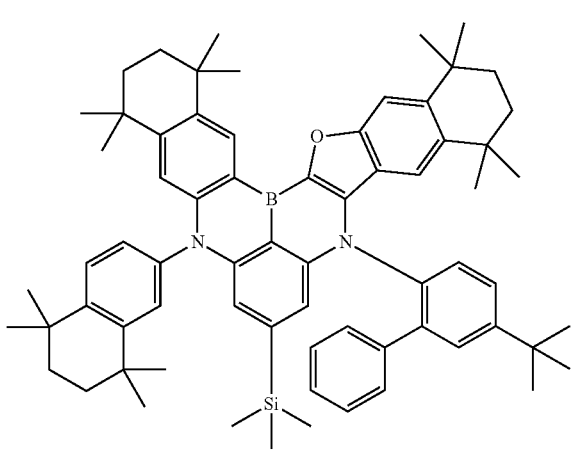 | 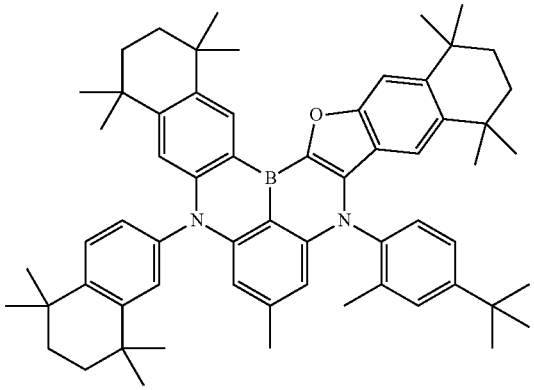 |
| 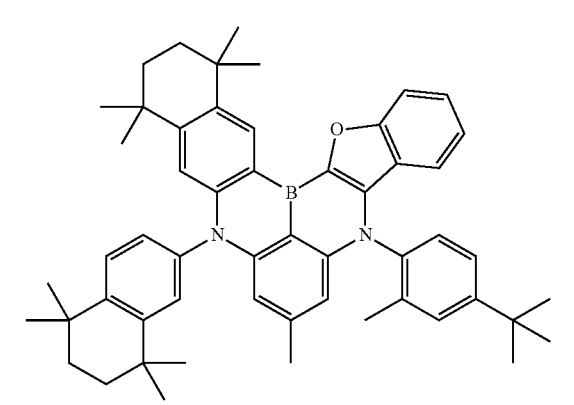 | 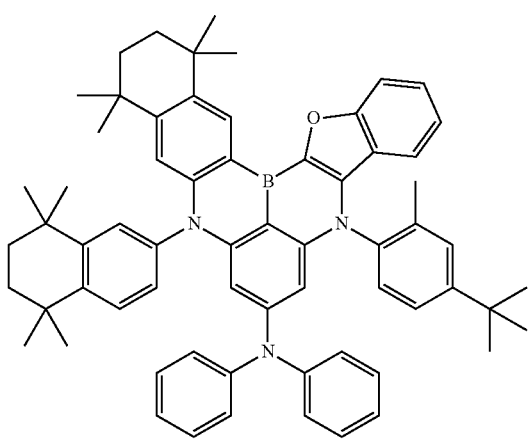 |

1035
-continued

1036
-continued

1037
-continued
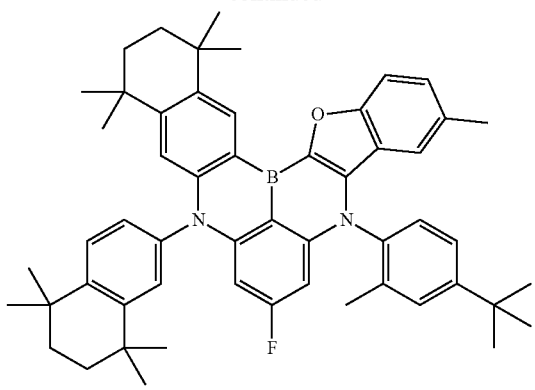
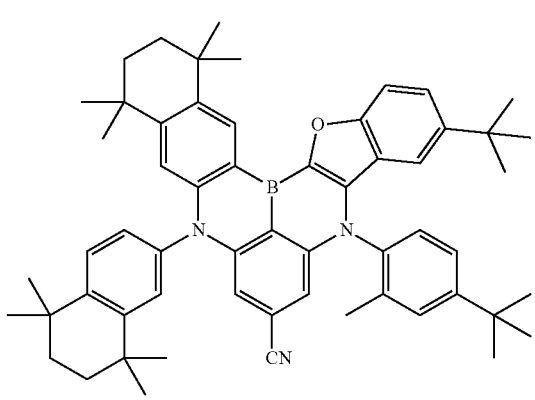
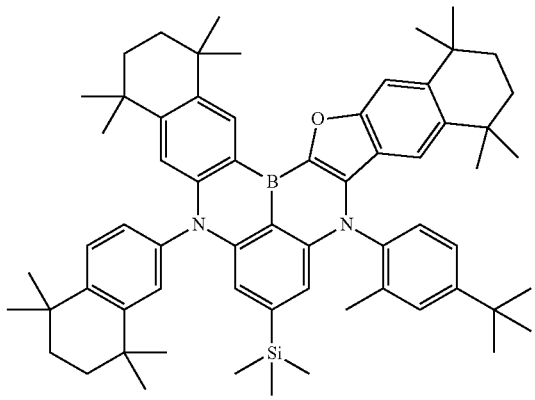
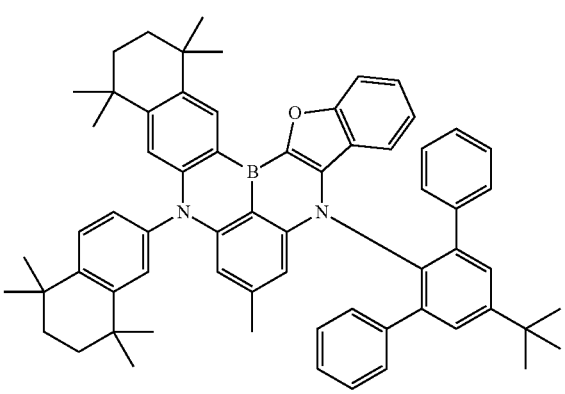
1038
-continued
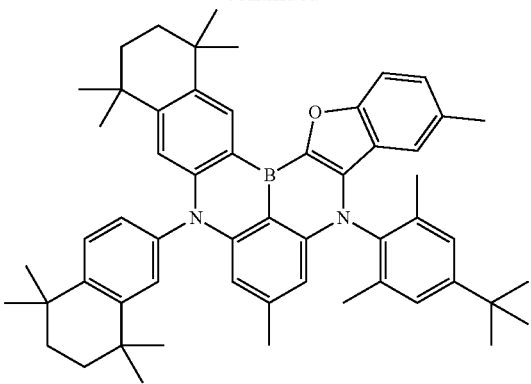
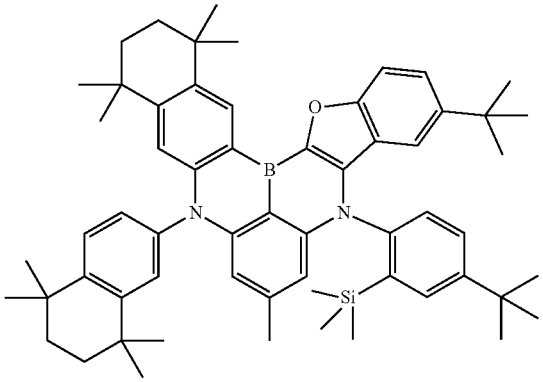
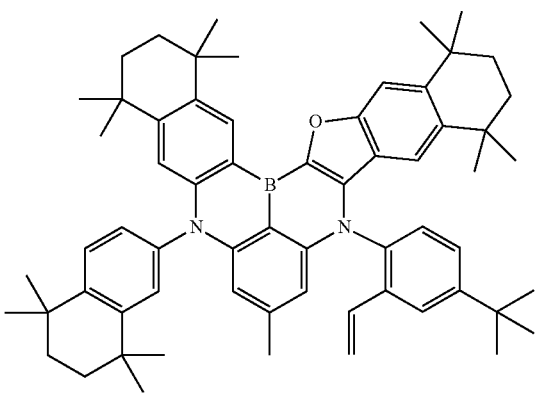
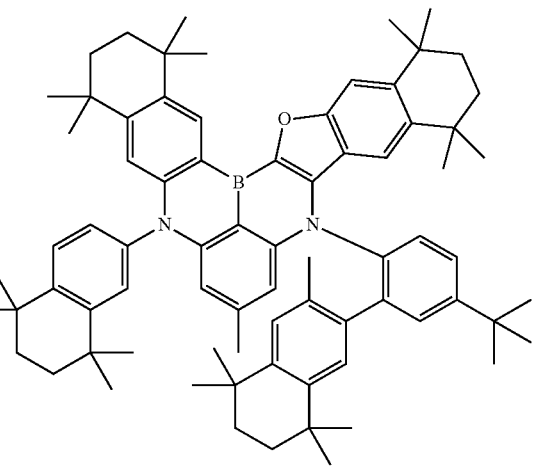

| 1039 -continued | 1040 -continued |
|---|---|
| 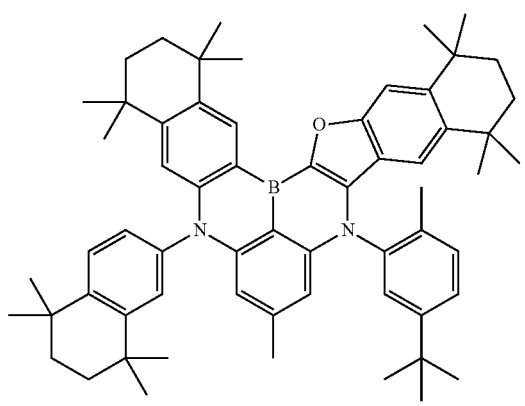 | 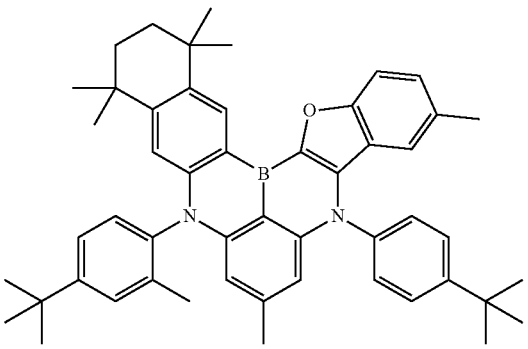 |
| 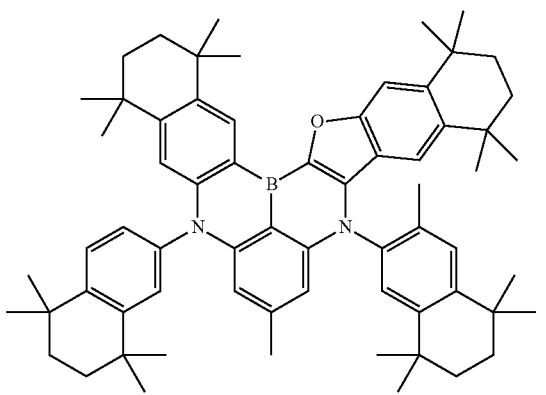 | 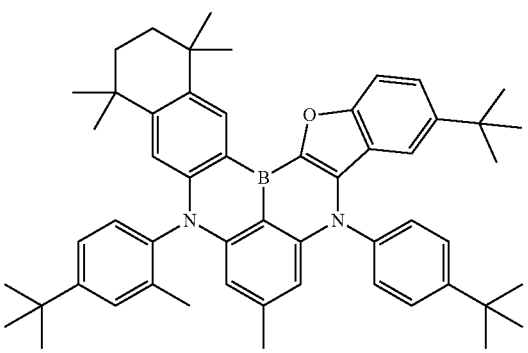 |
| 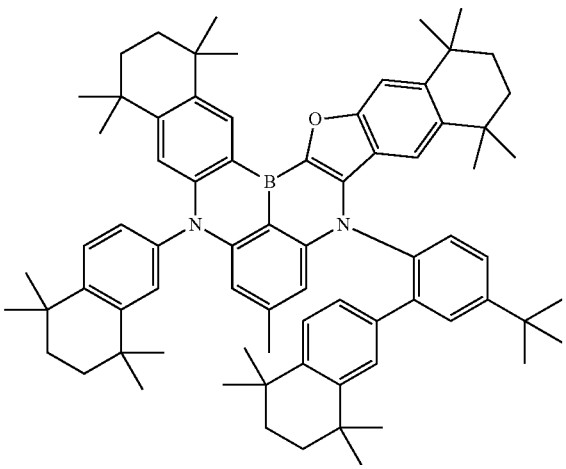 | 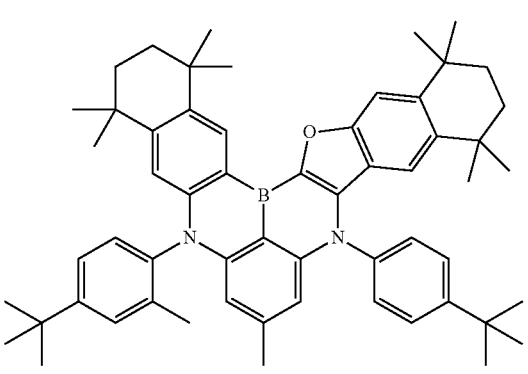 |
| 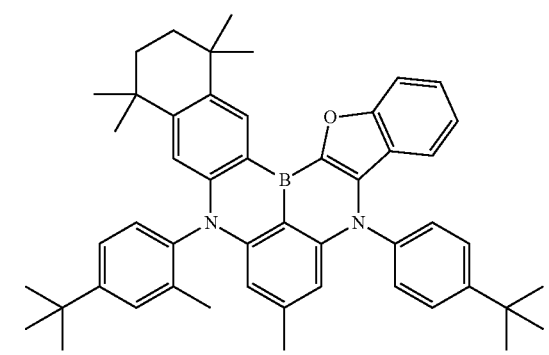 | 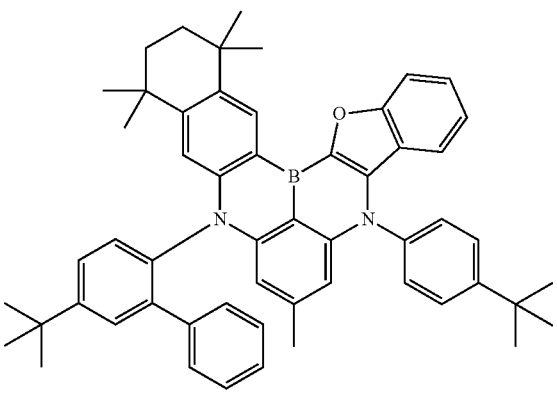 |

1041
-continued
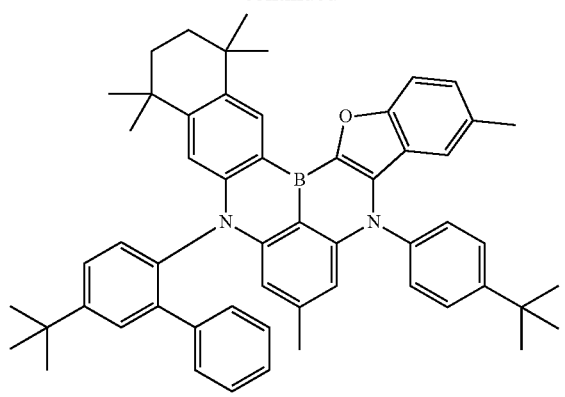
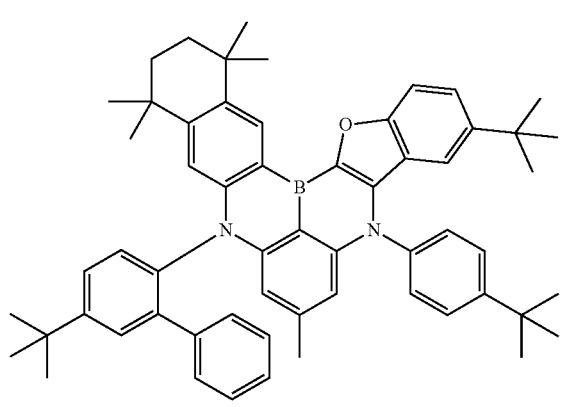
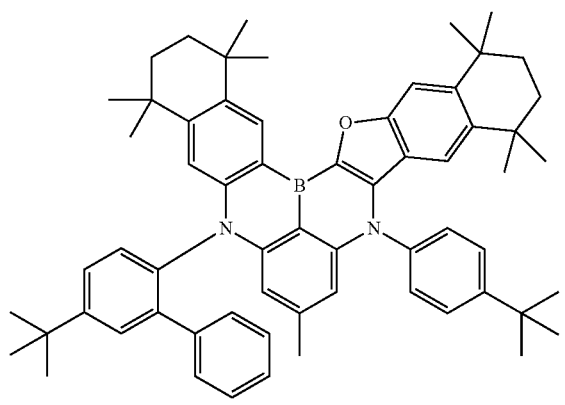
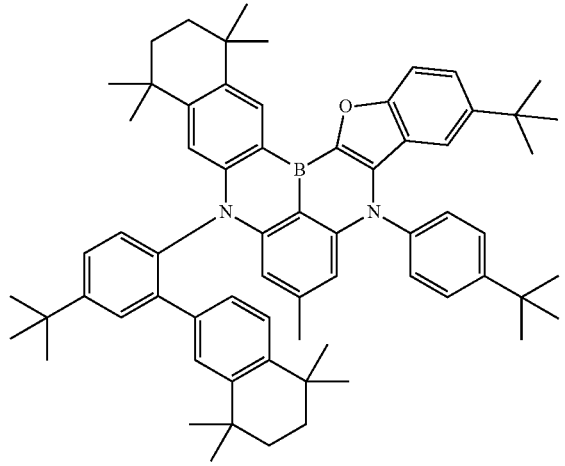
1042
-continued
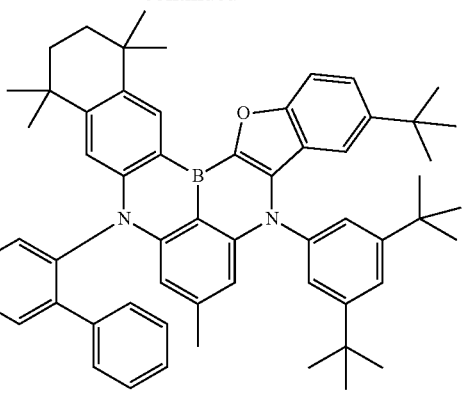
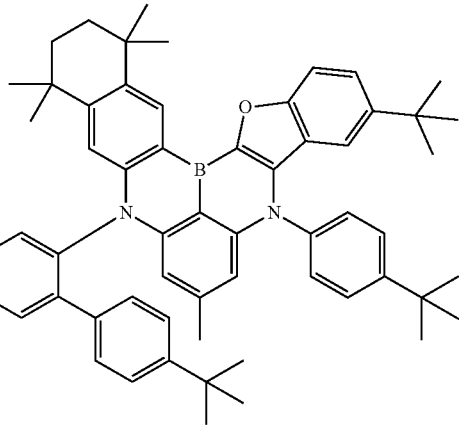
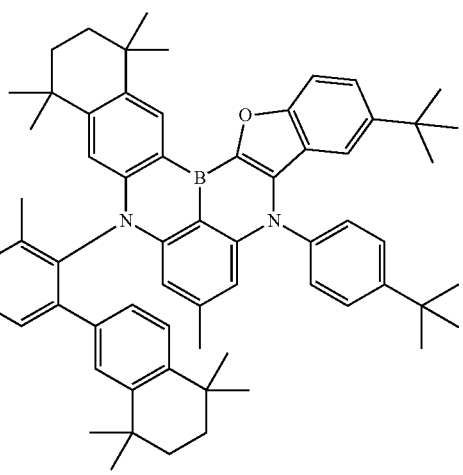
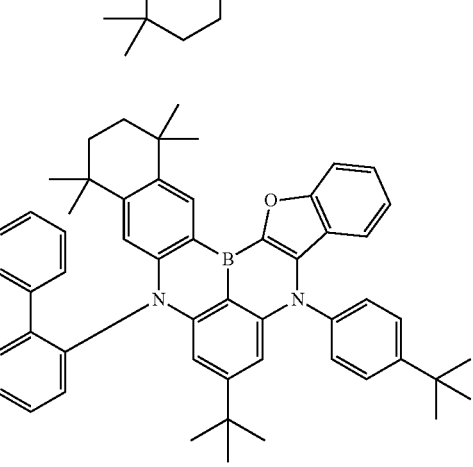

1043
-continued
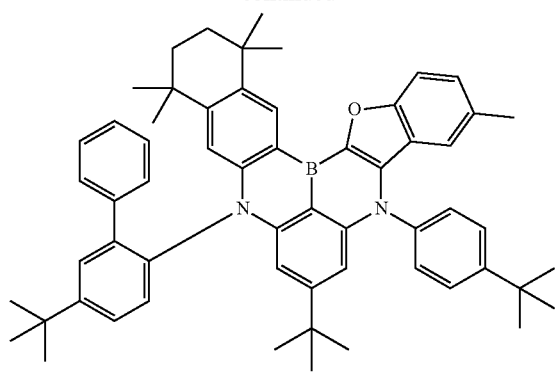
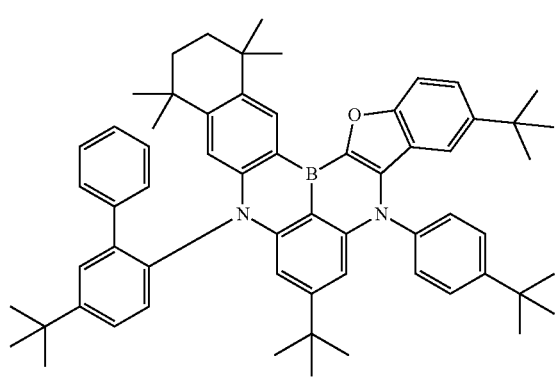
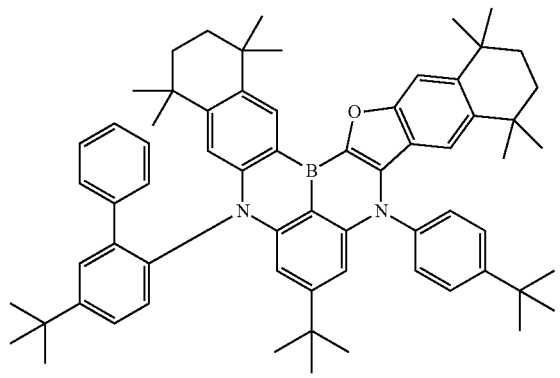
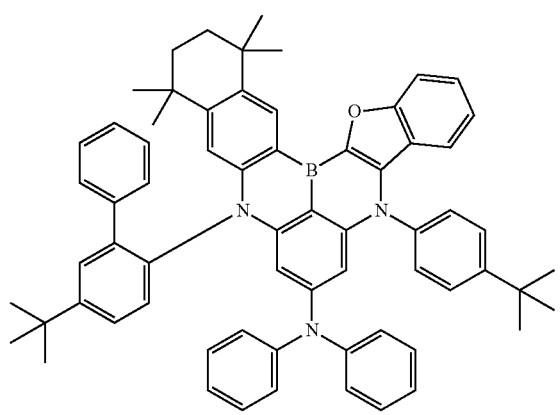
1044
-continued
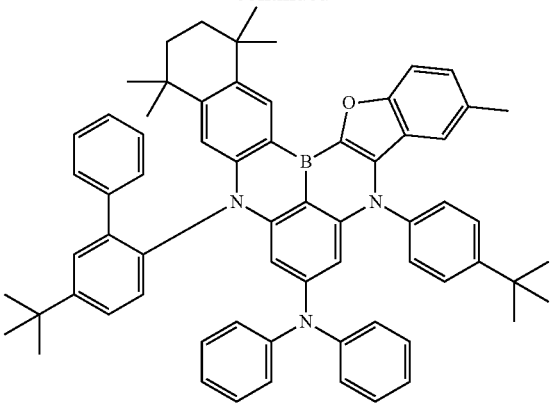
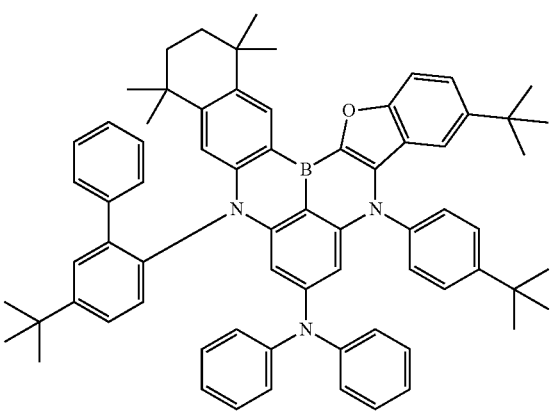
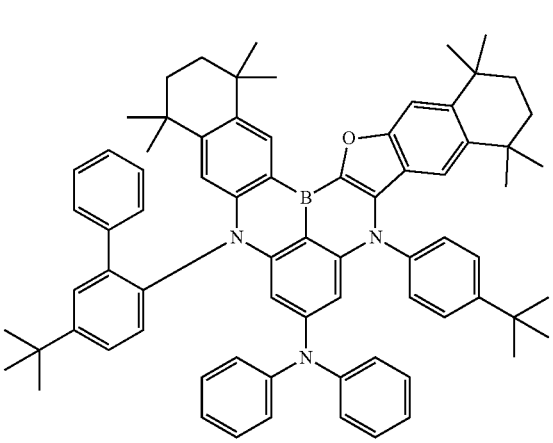
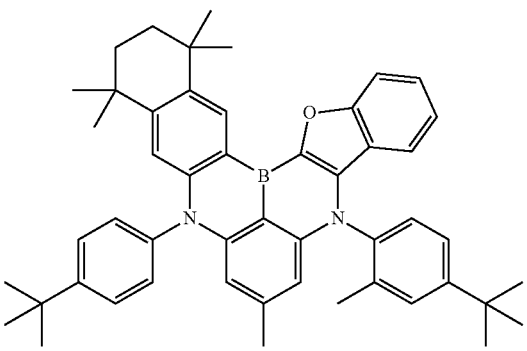

1045
-continued
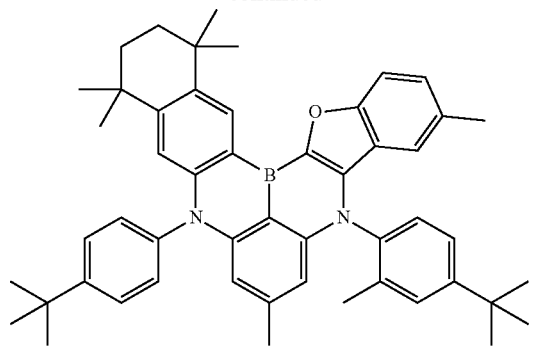
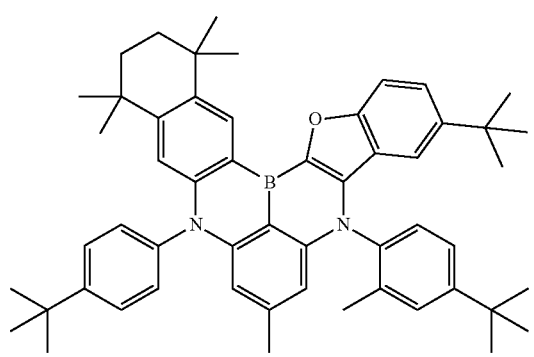
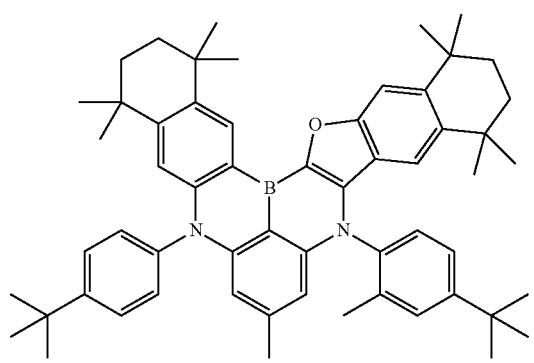
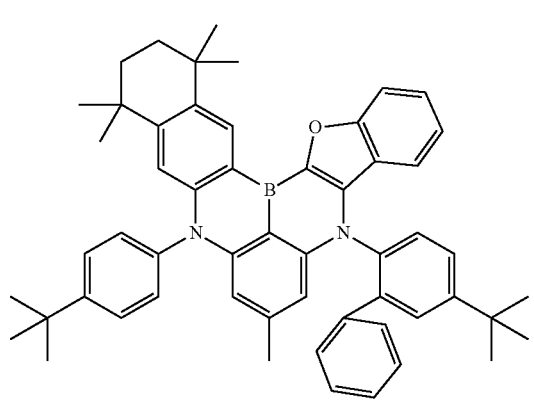
1046
-continued
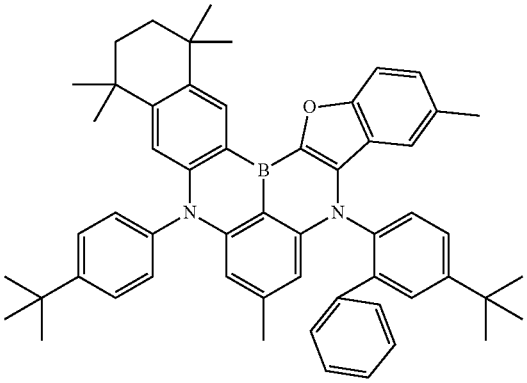
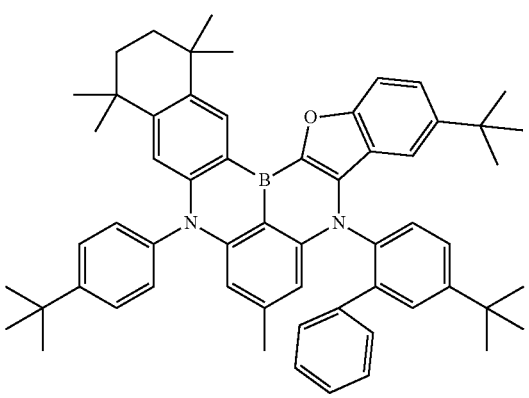
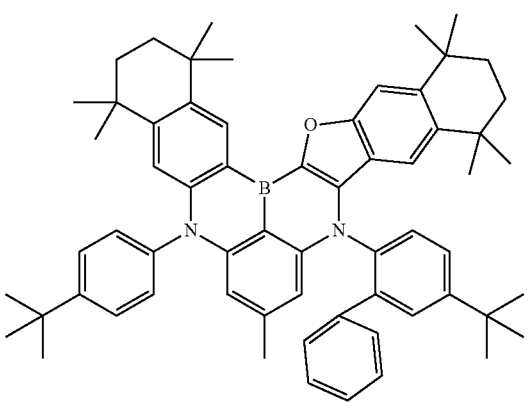
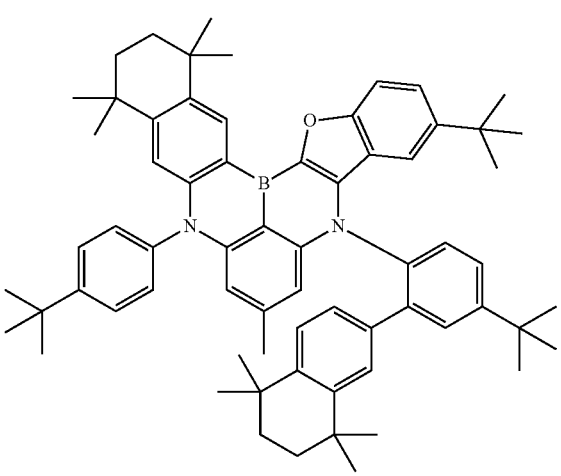

1047
-continued
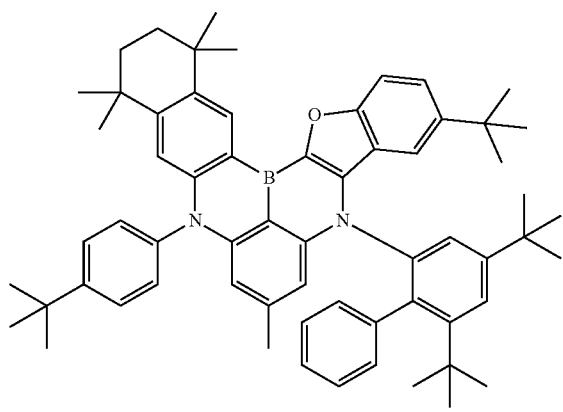
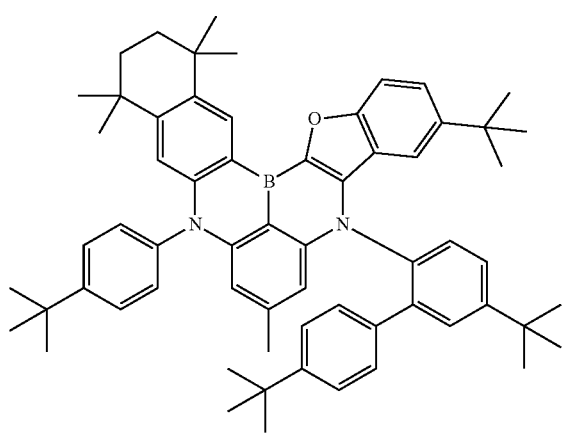
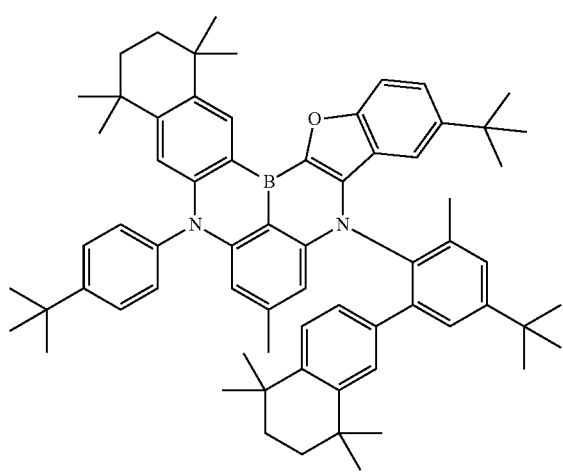
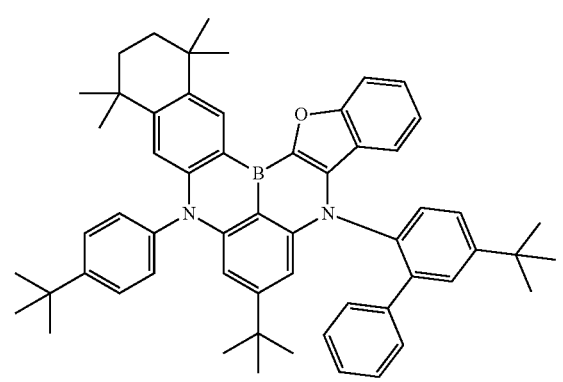
1048
-continued
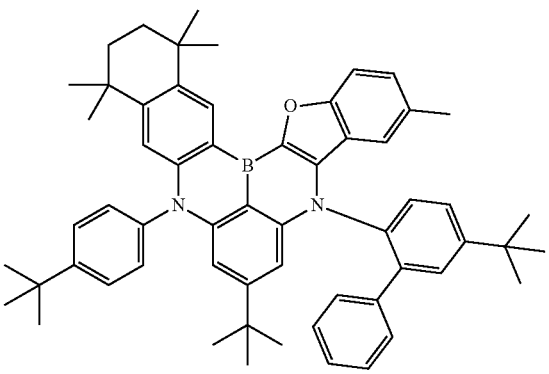
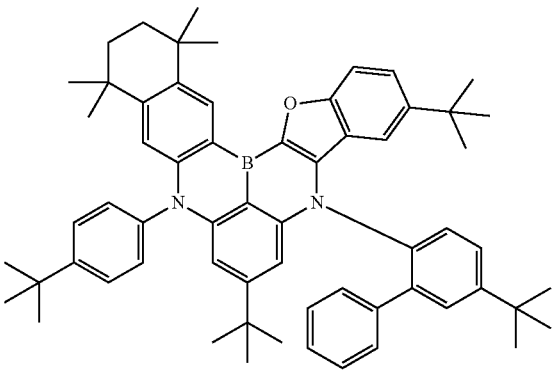
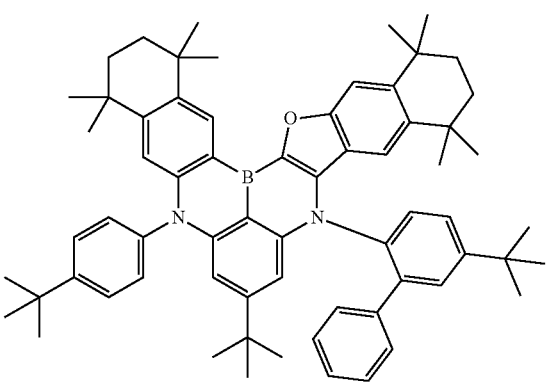
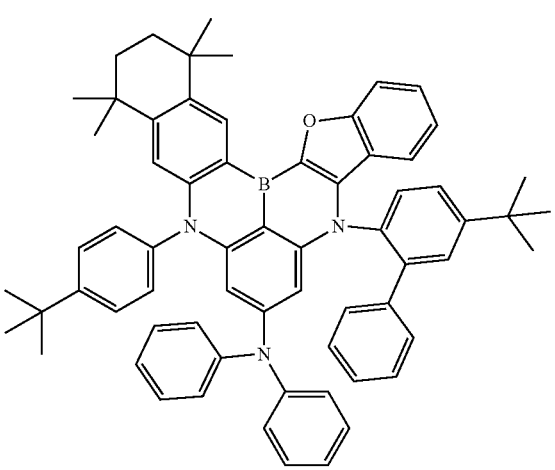

1049
-continued
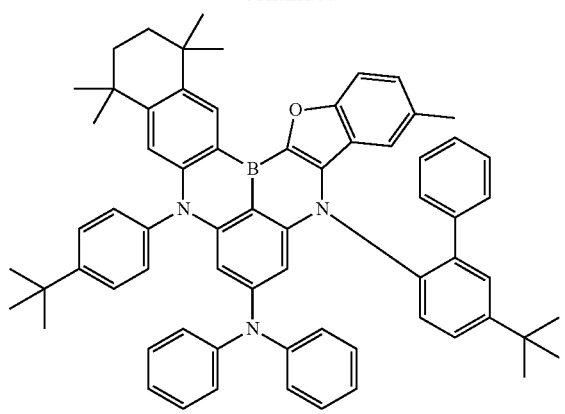
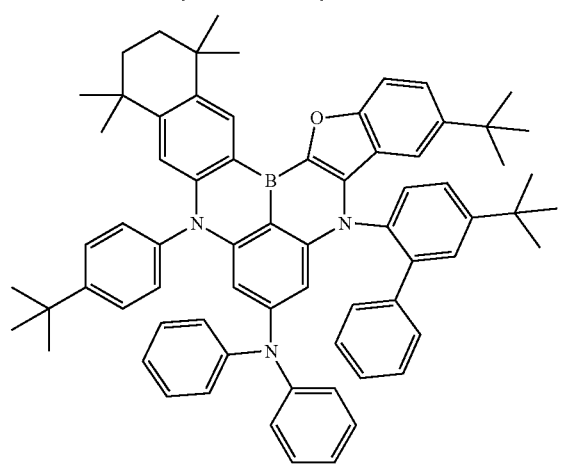
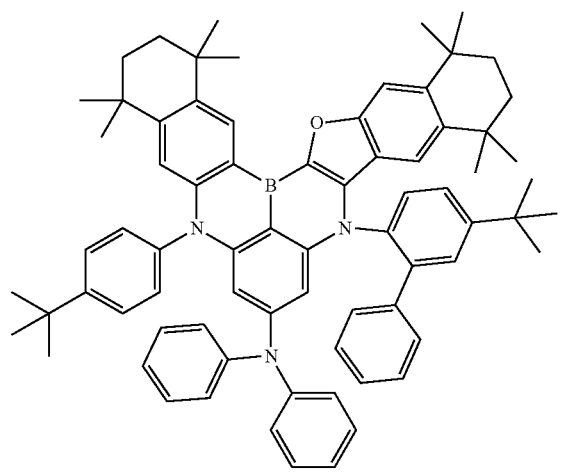
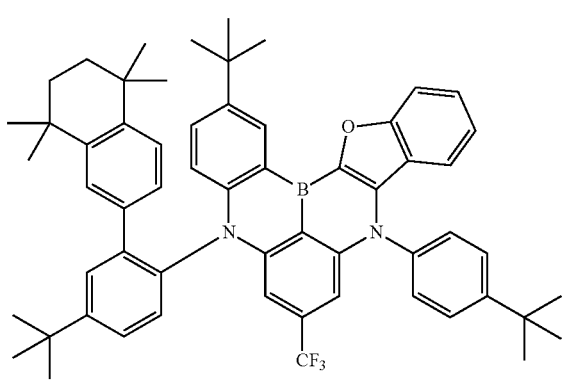
1050
-continued
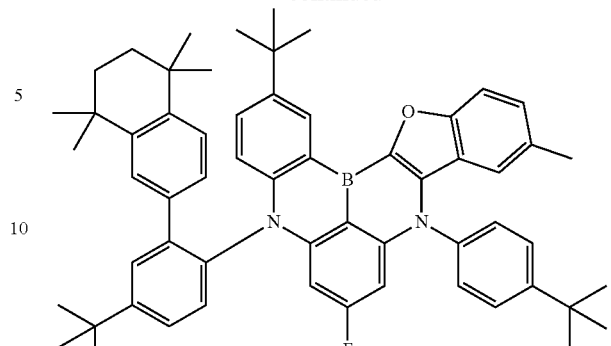
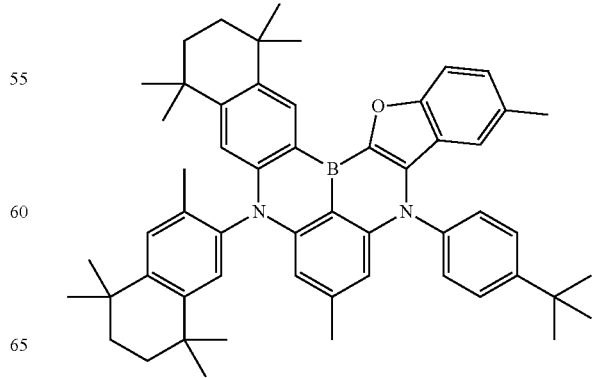

1051
-continued

1052
-continued

1053
-continued
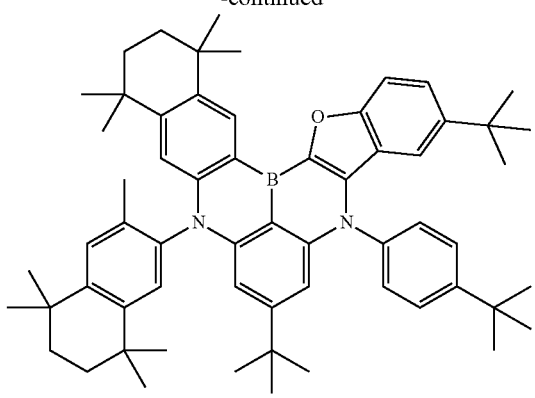
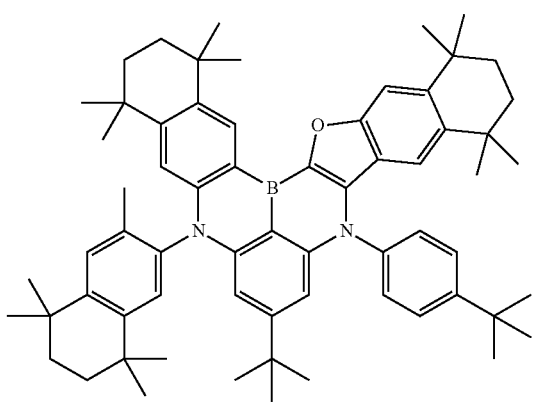
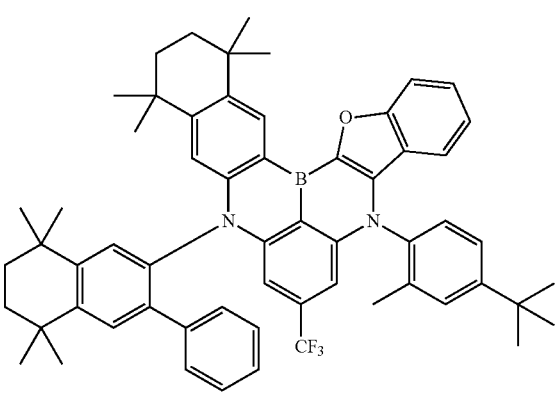
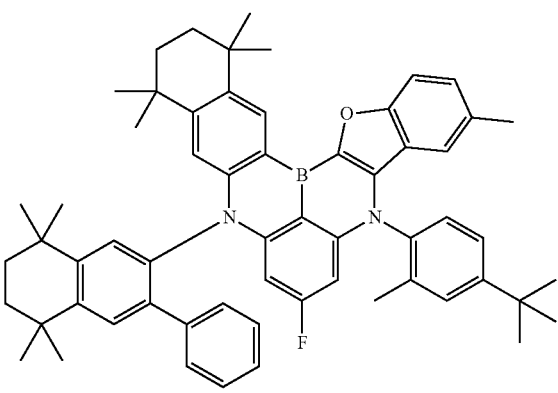
1054
-continued
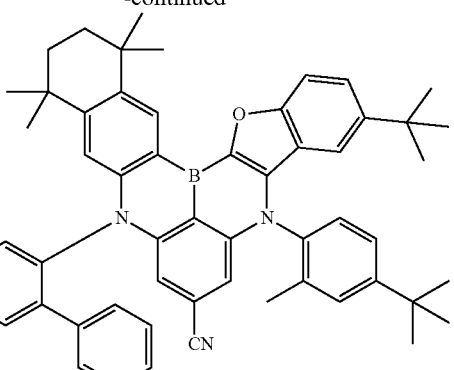
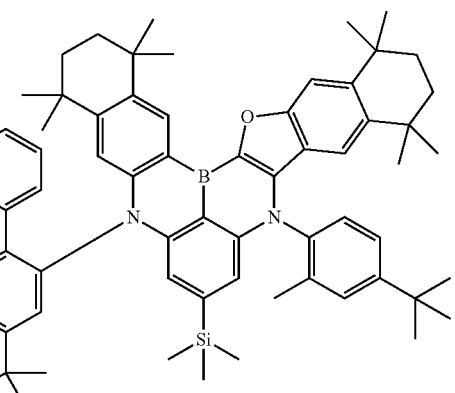
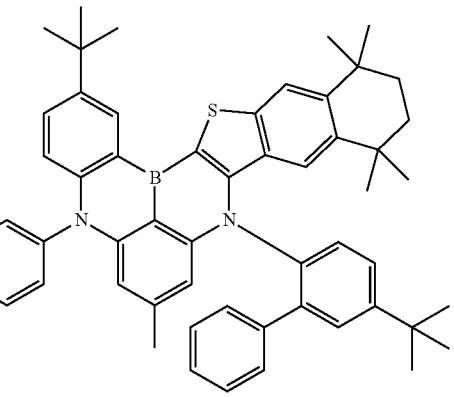
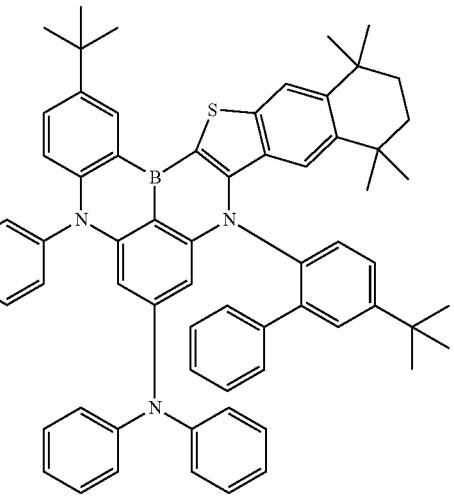

1055
-continued
1056
-continued
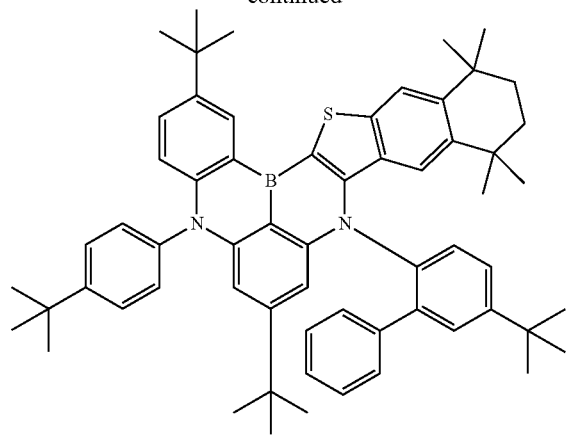
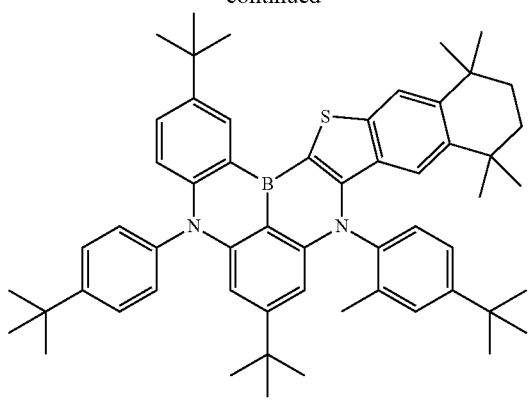
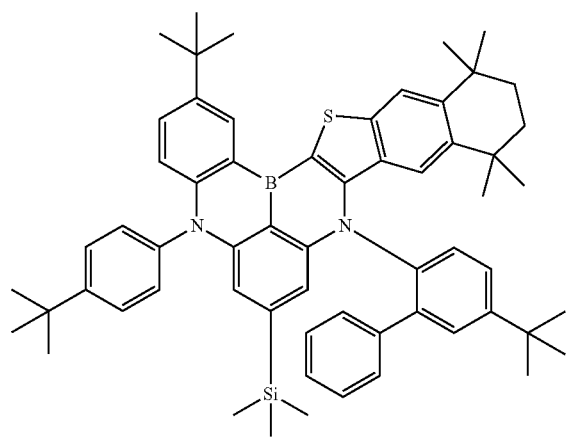
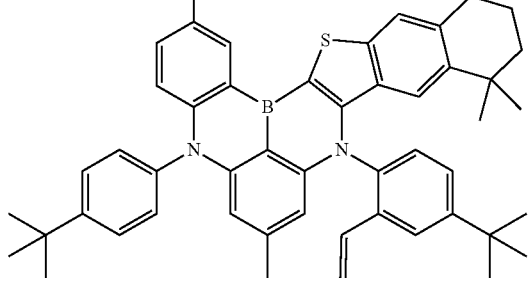
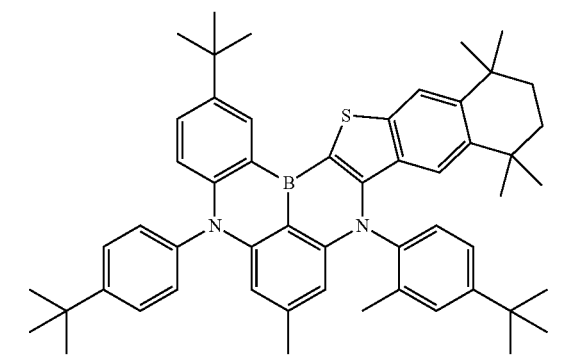
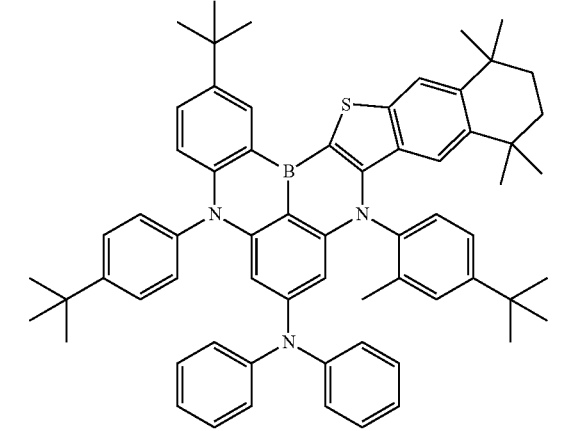
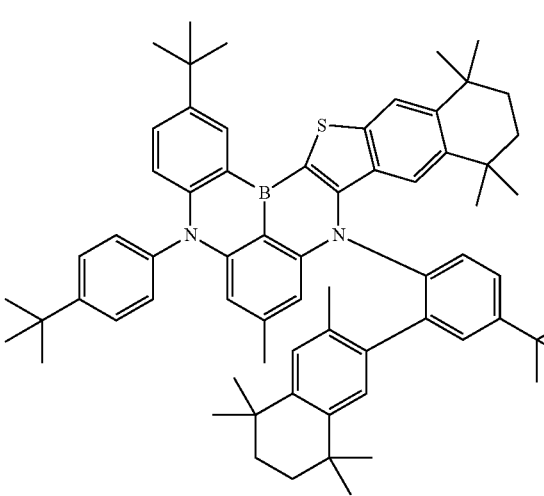

1057
-continued
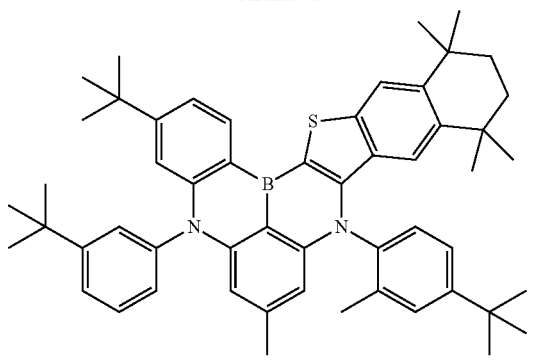
1058
-continued
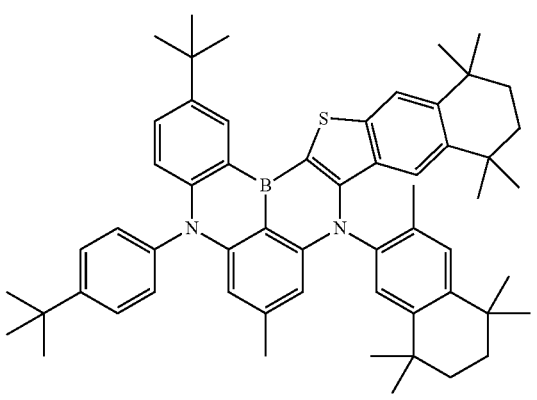
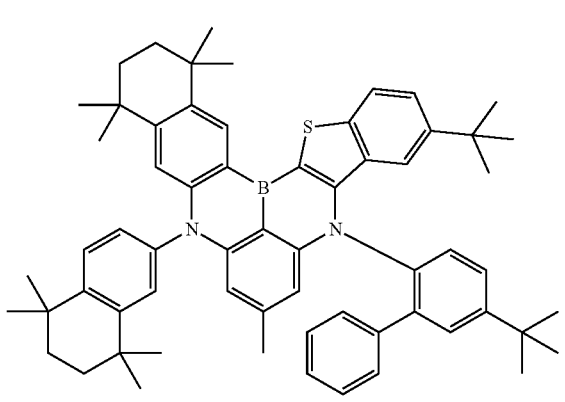
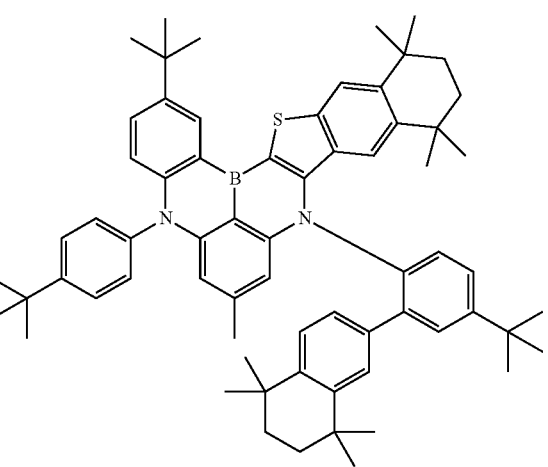
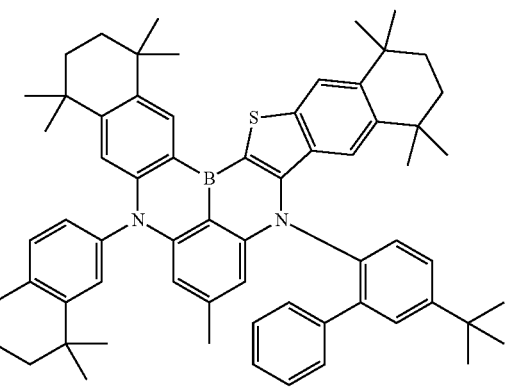
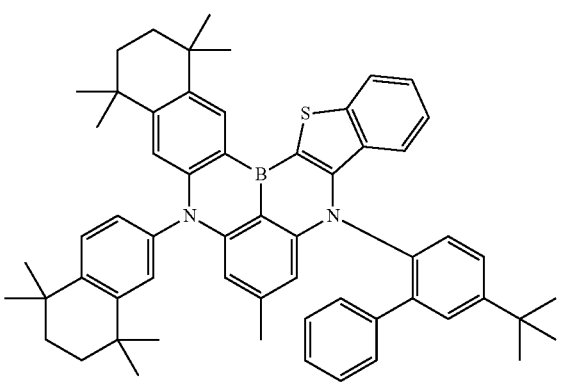
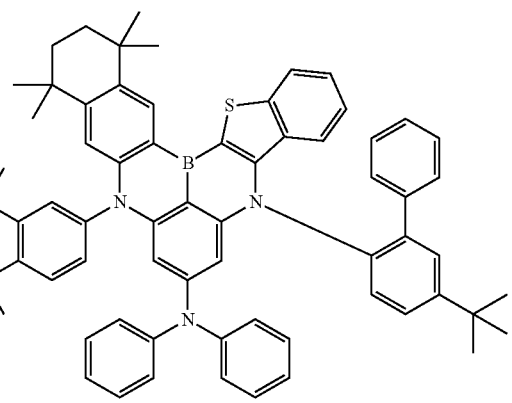

| 1059 -continued | 1060 -continued |
|---|---|
| 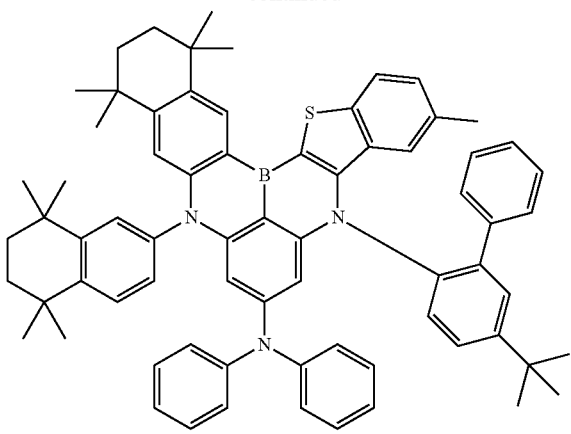 | 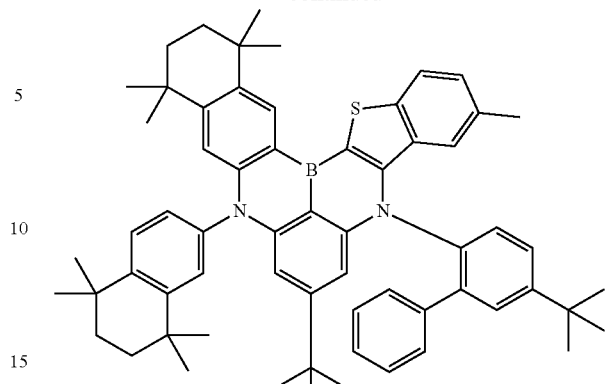 |
| 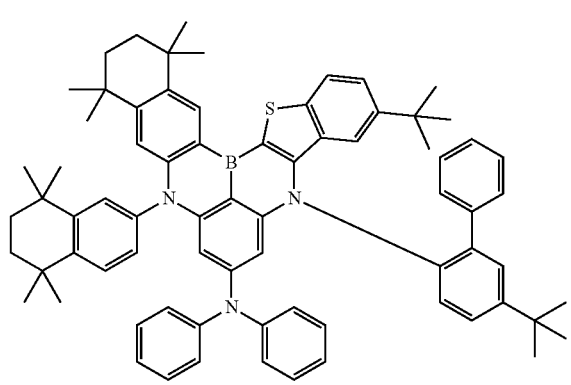 | 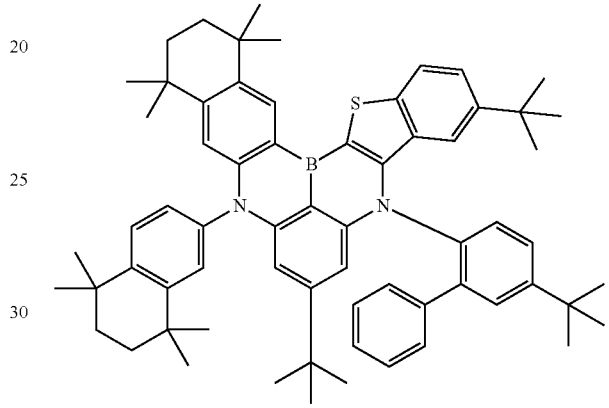 |
| 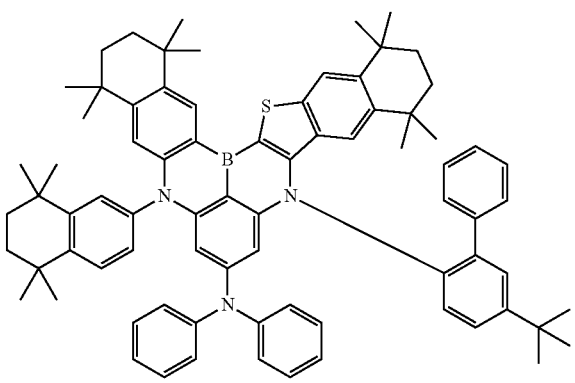 | 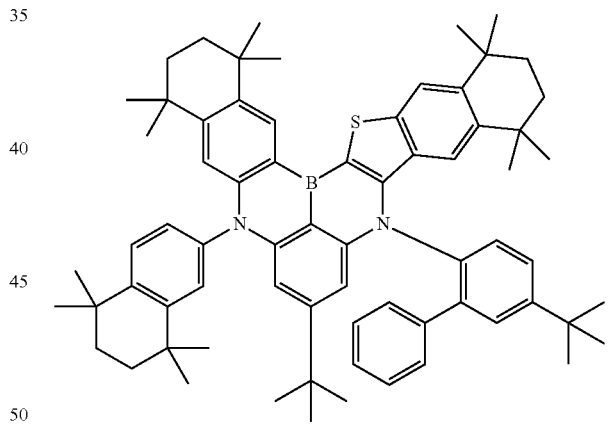 |
| 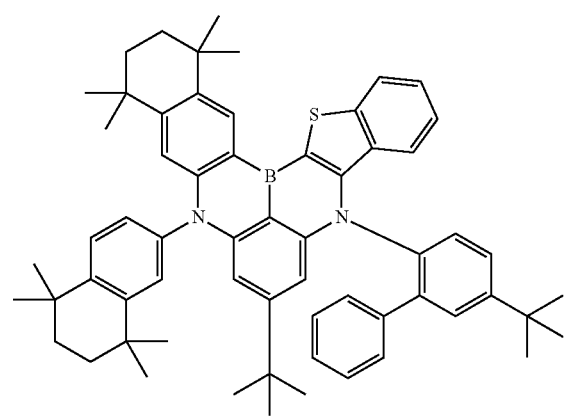 | 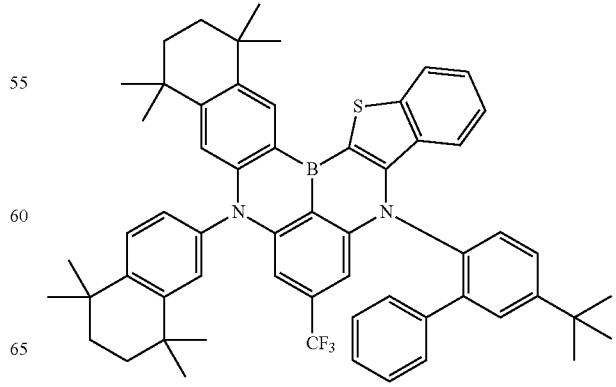 |

| 1061 -continued | 1062 -continued |
|---|---|
| 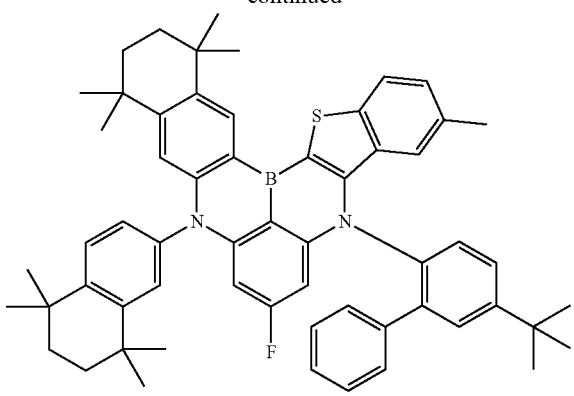 | 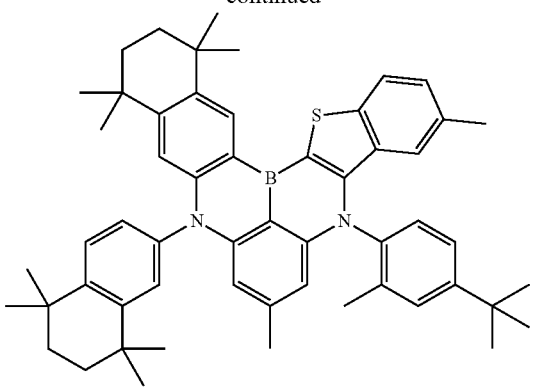 |
| 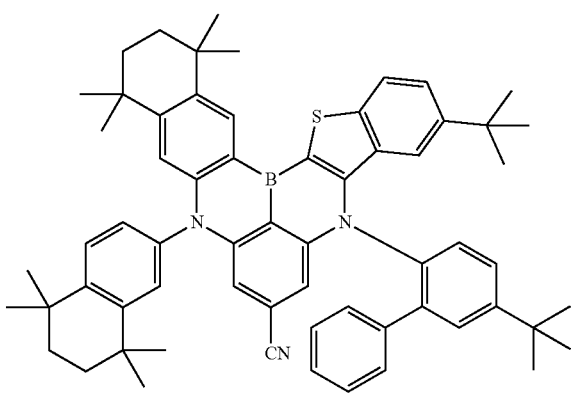 | 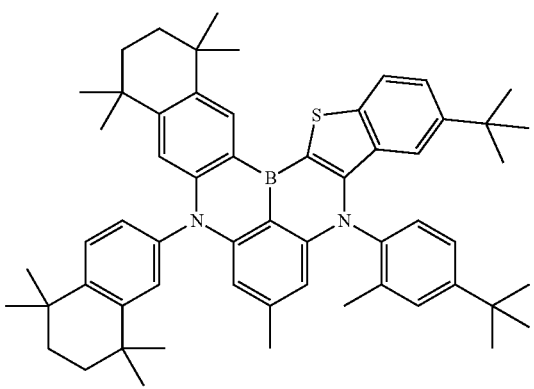 |
| 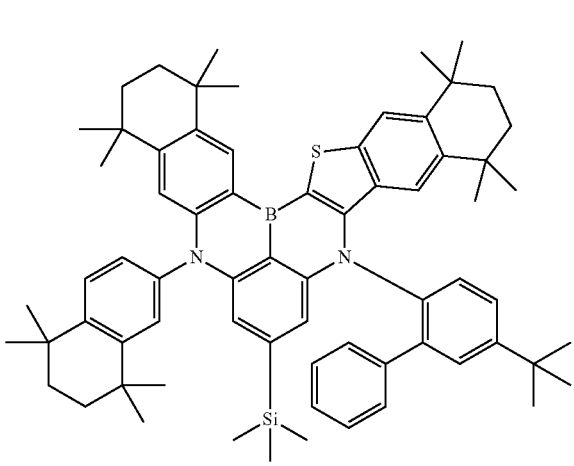 | 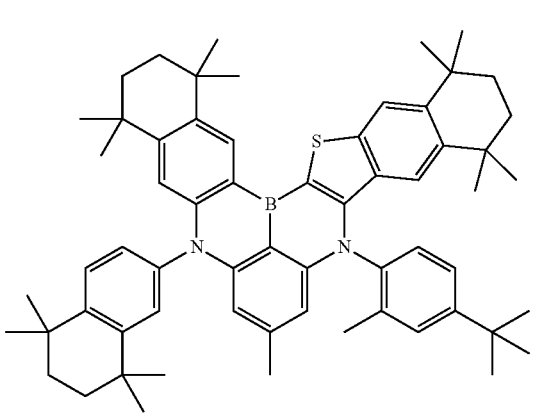 |
|  | 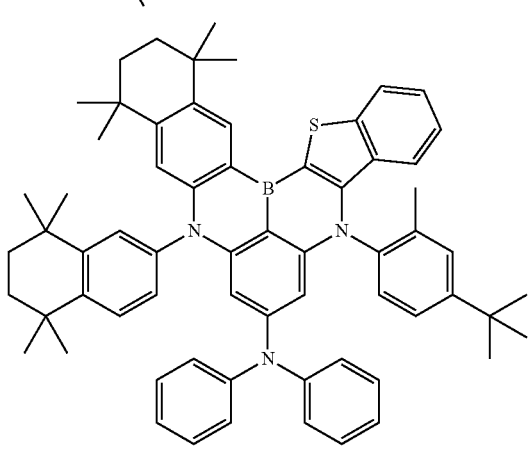 |

| 1063 -continued | 1064 -continued |
|---|---|
| 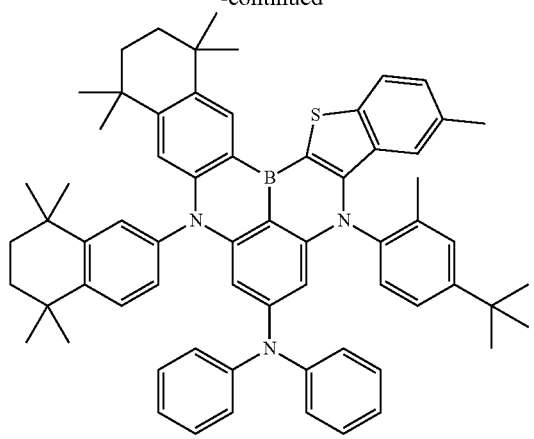 | 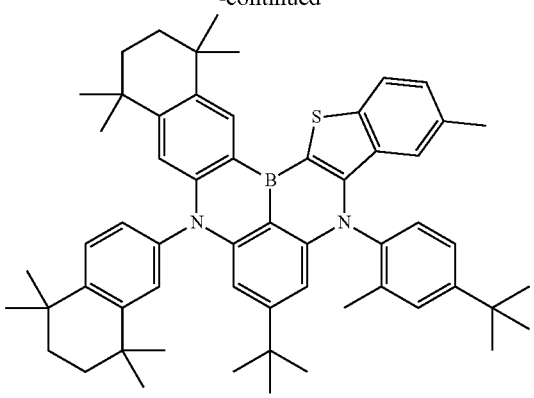 |
| 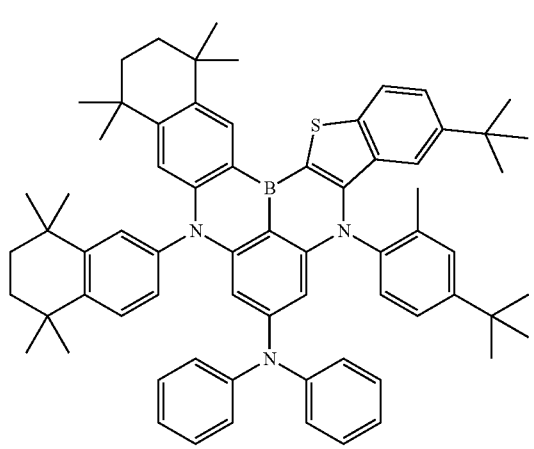 | 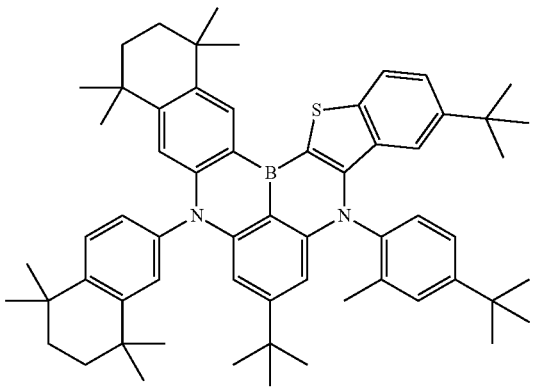 |
| 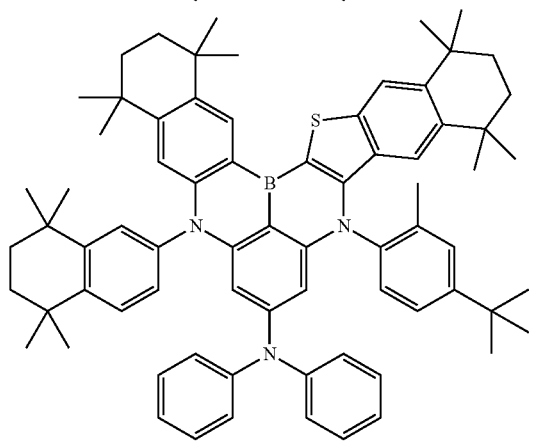 | 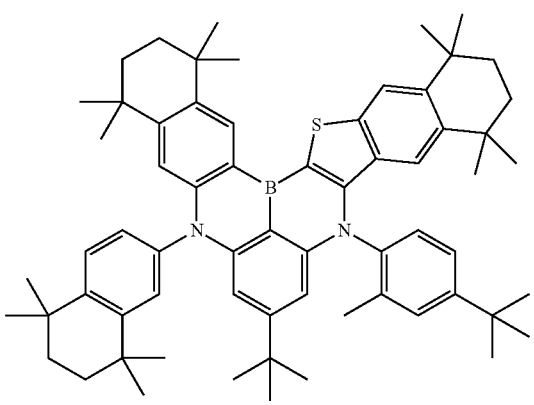 |
| 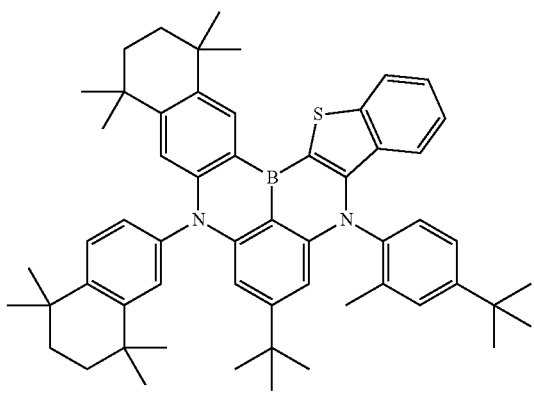 | 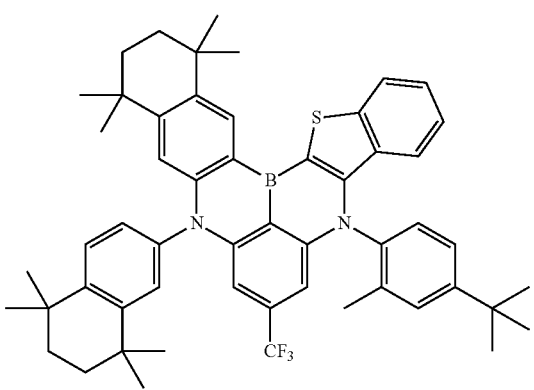 |

1065
-continued
1066
-continued
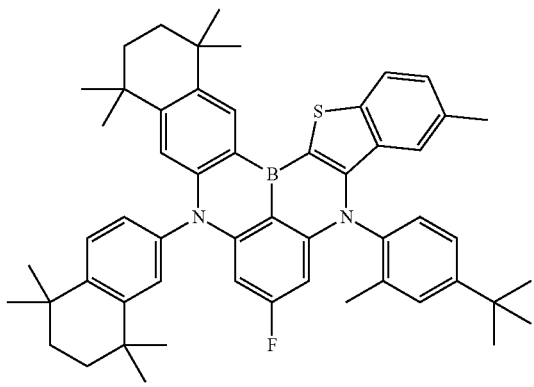
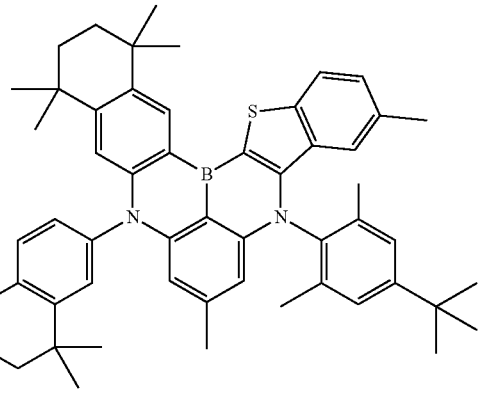

1067
-continued
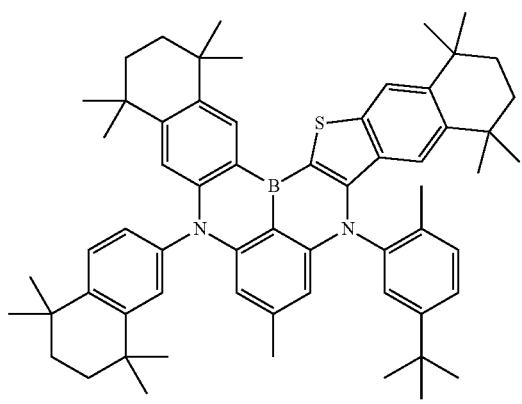
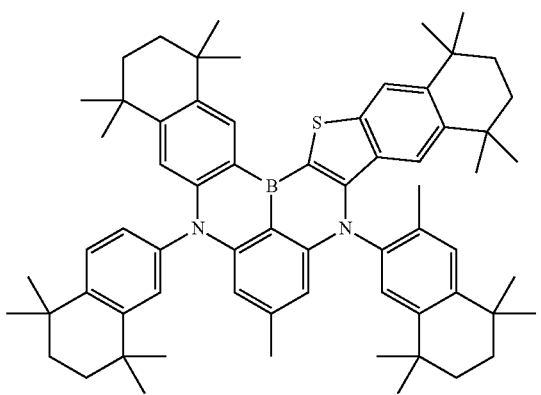
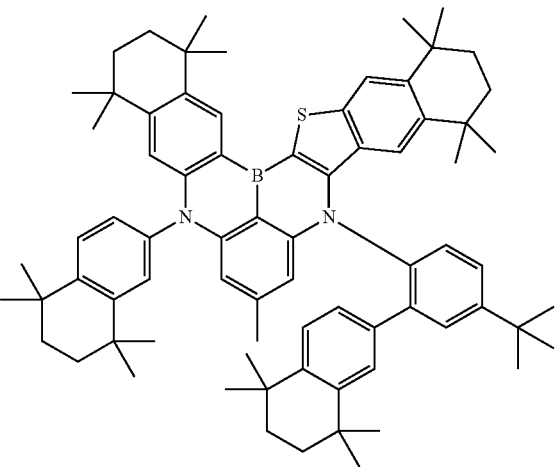
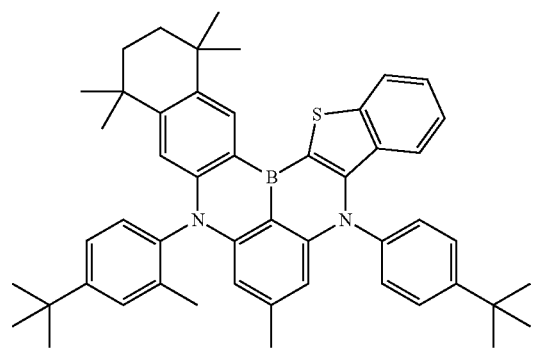
1068
-continued
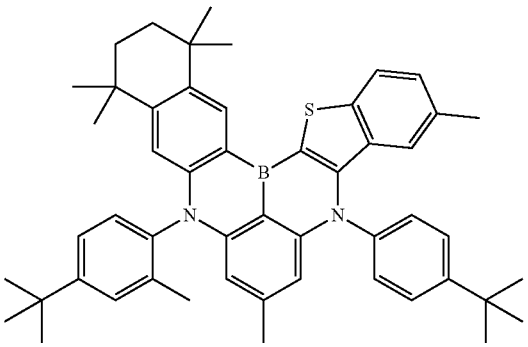
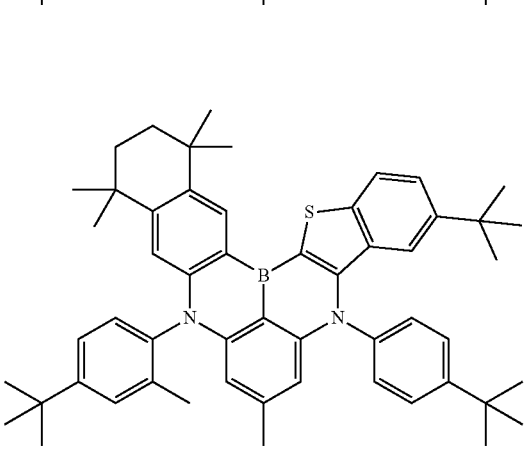
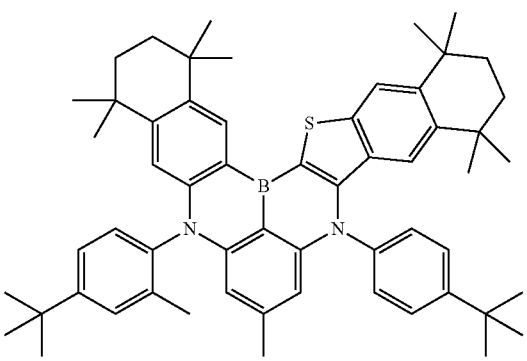
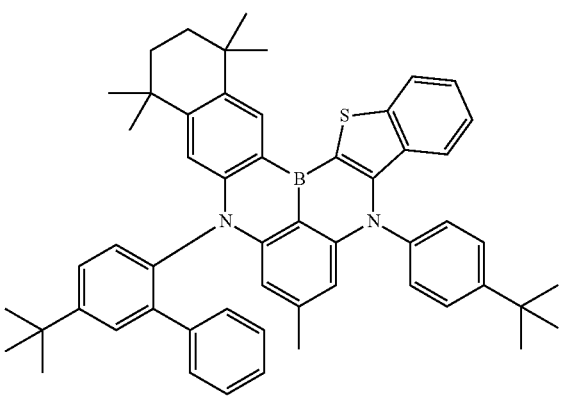

| 1069 -continued | 1070 -continued |
|---|---|
| 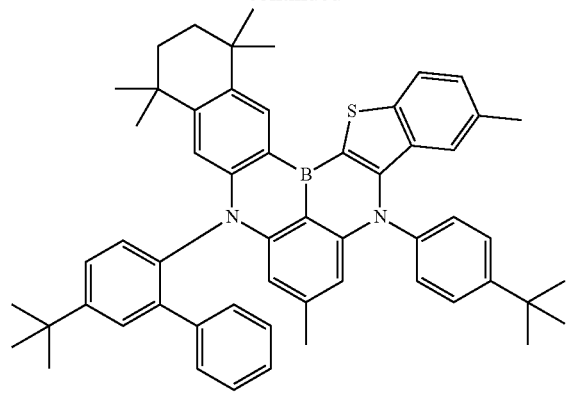 | 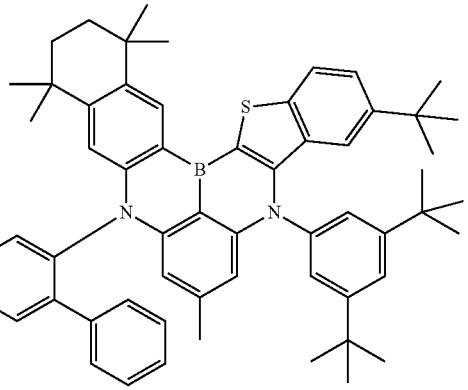 |
| 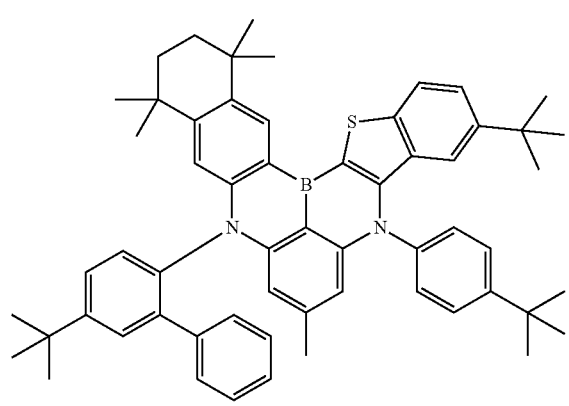 | 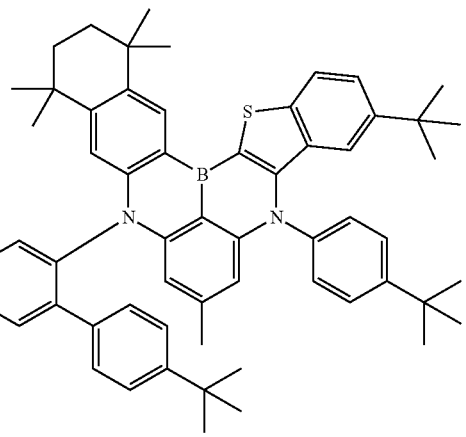 |
| 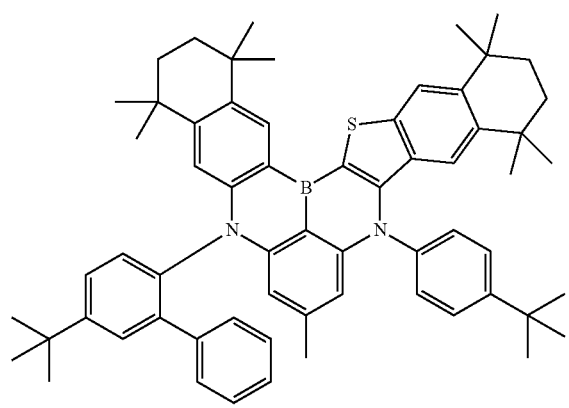 | 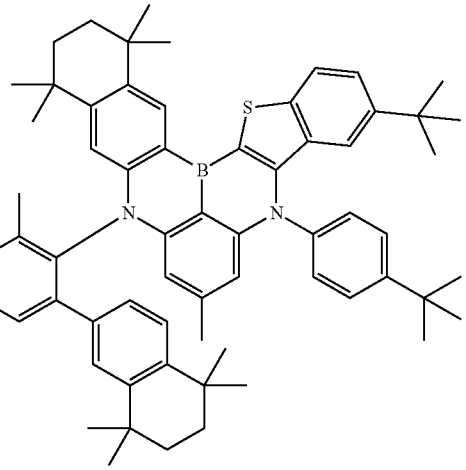 |
| 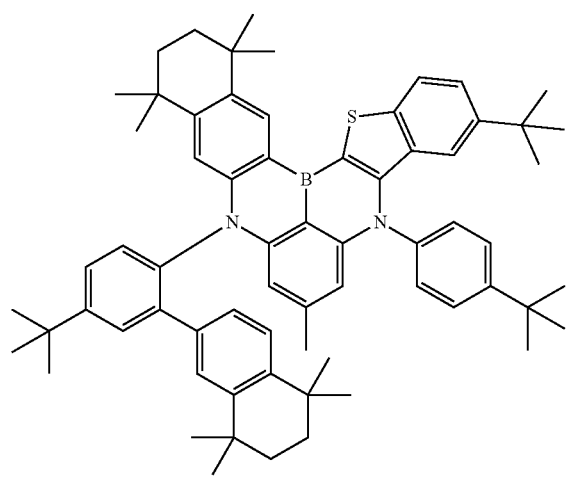 | 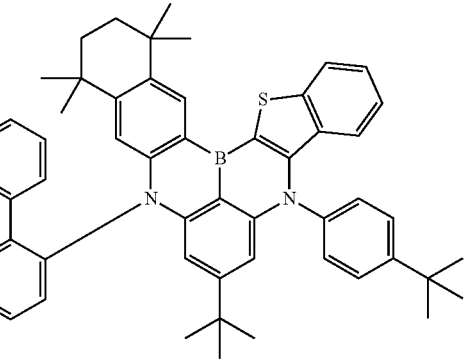 |

1071
-continued

1072
-continued

1073
-continued
1074
-continued
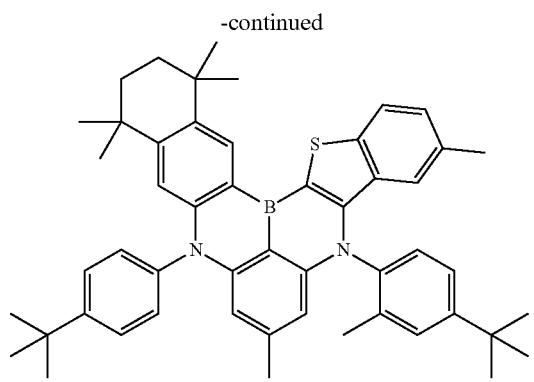
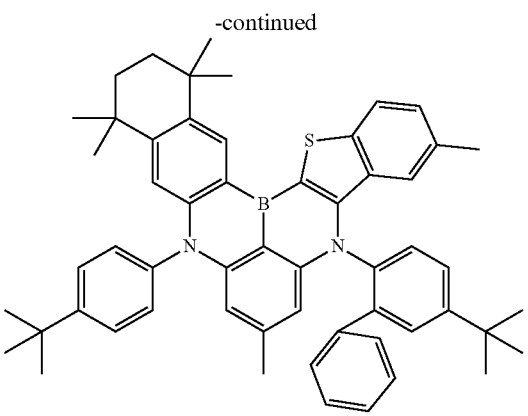

| 1075 -continued | 1076 -continued |
|---|---|
| 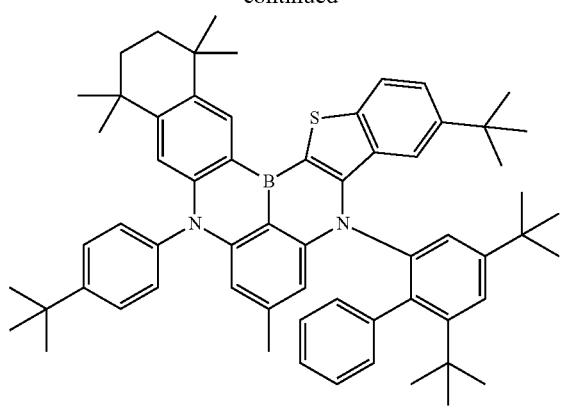 | 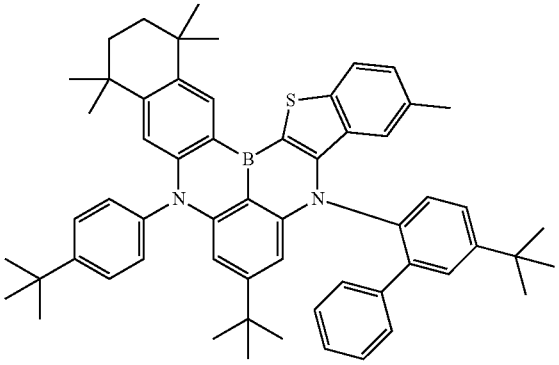 |
| 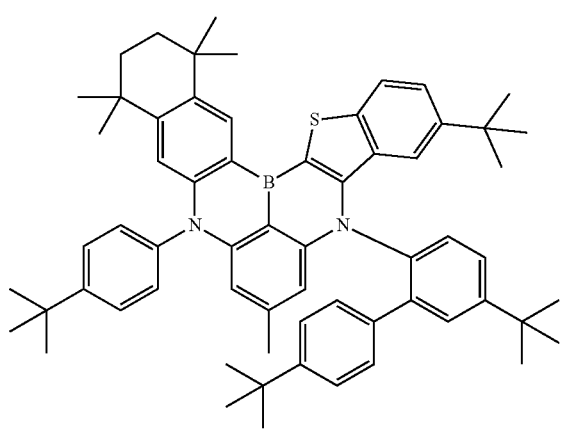 | 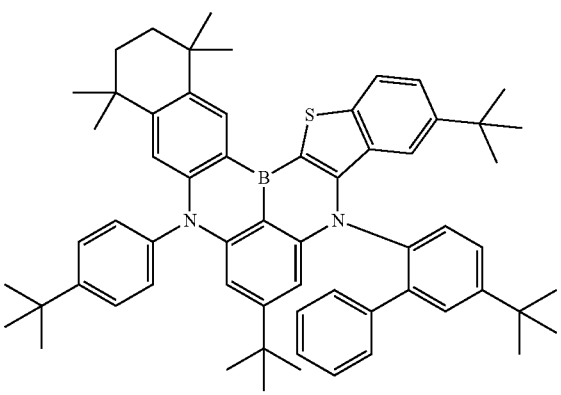 |
| 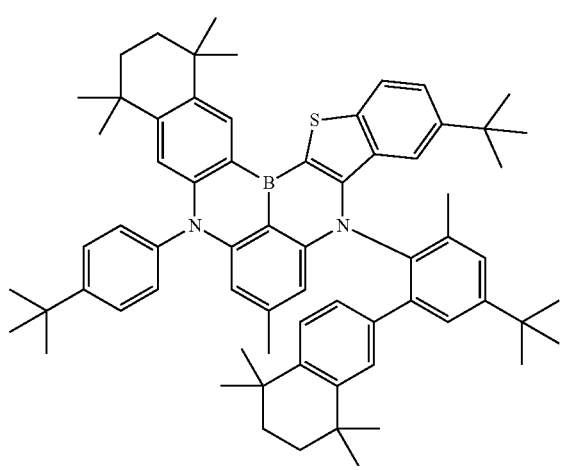 | 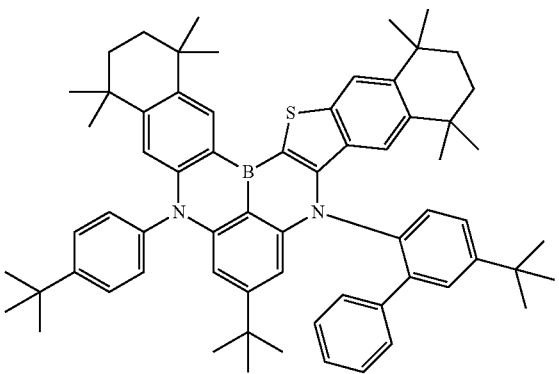 |
| 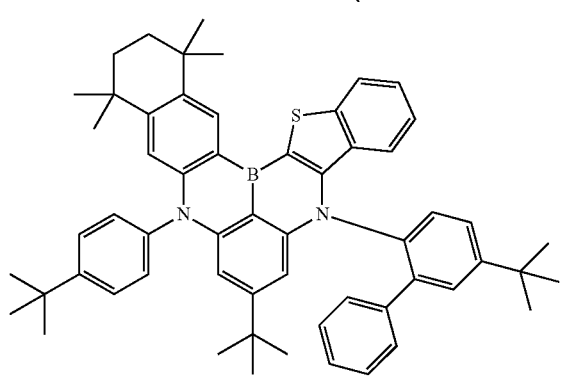 | 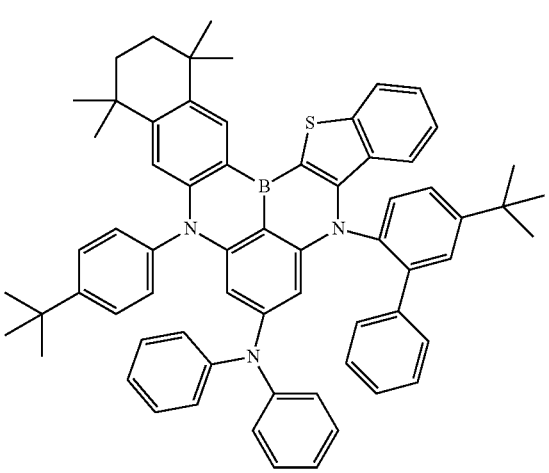 |

1077
-continued
1078
-continued
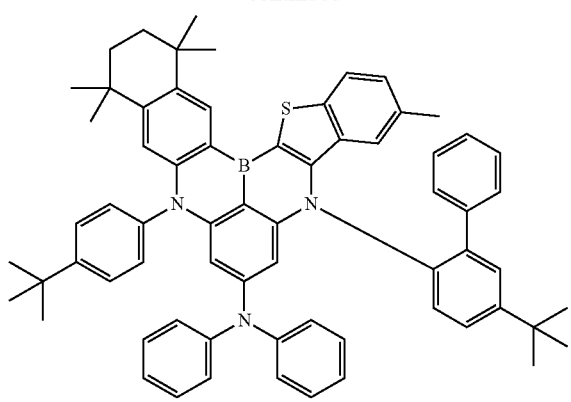
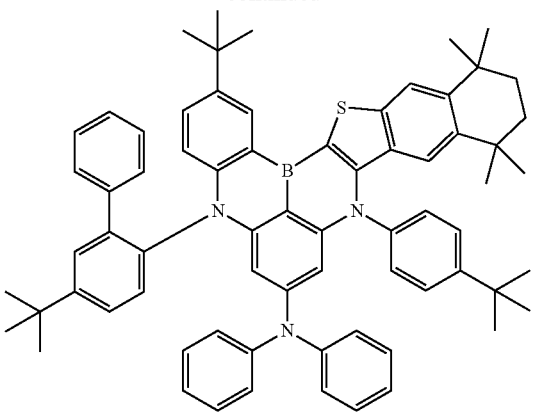
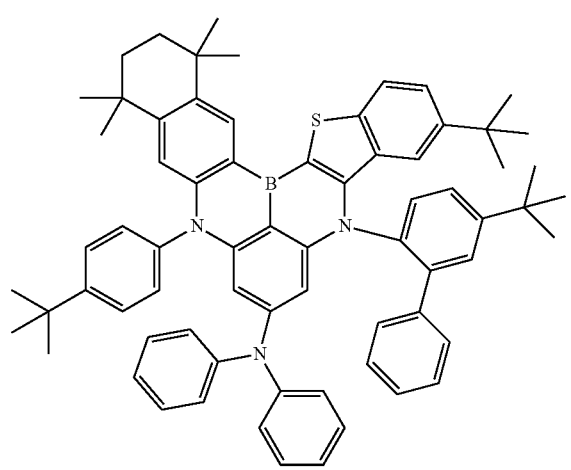
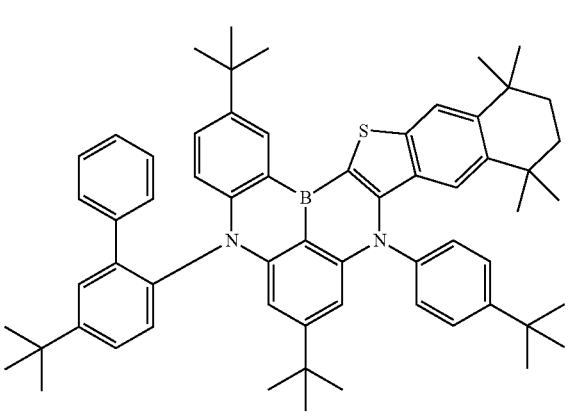
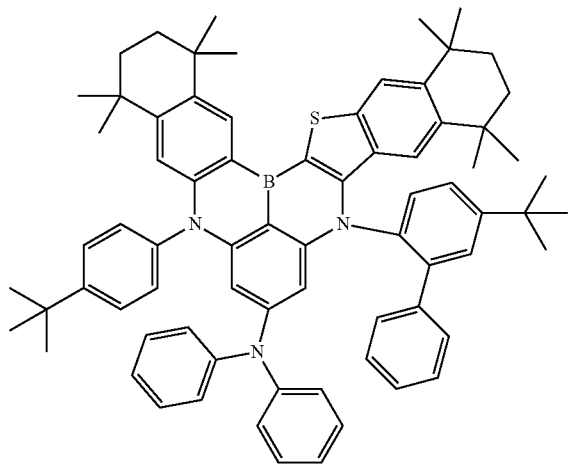
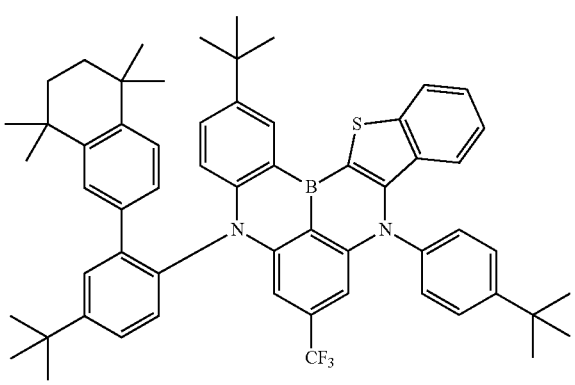
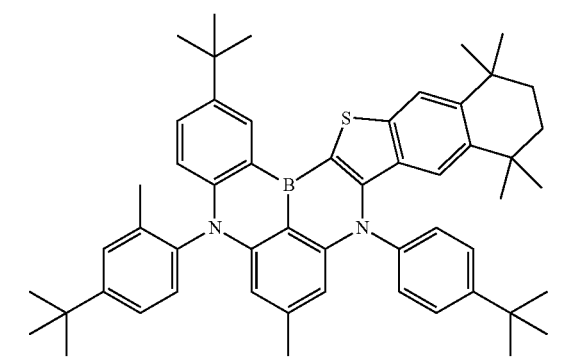
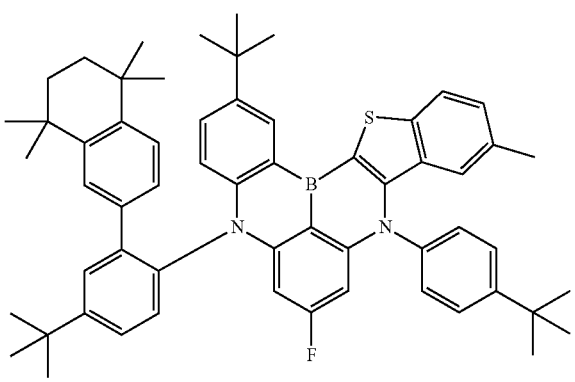

| 1079 -continued | 1080 -continued |
|---|---|
| 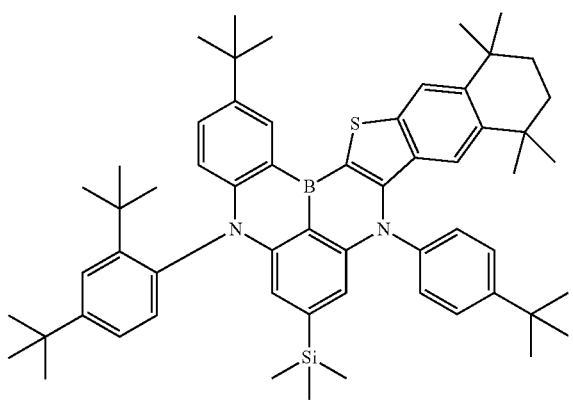 | 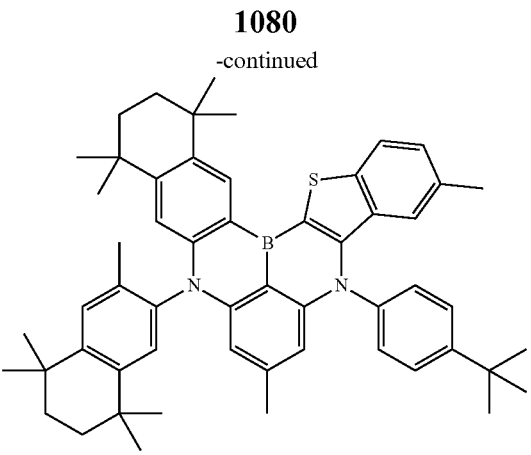 |
| 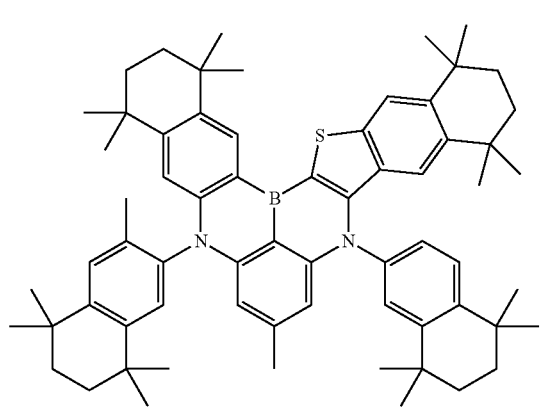 | 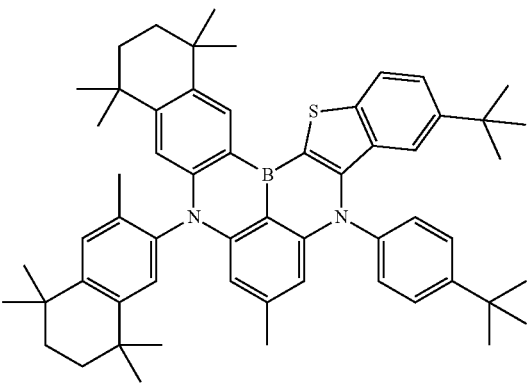 |
| 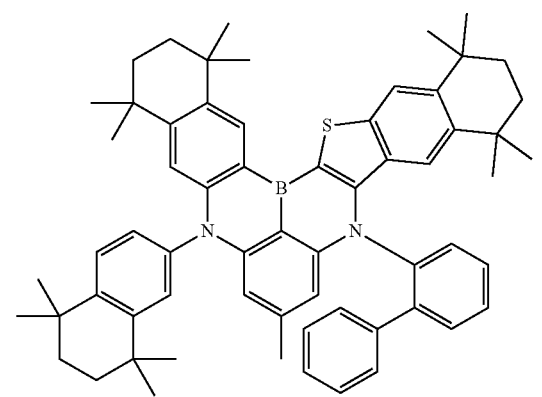 | 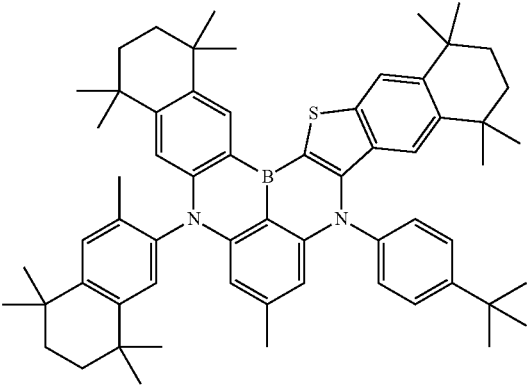 |
| 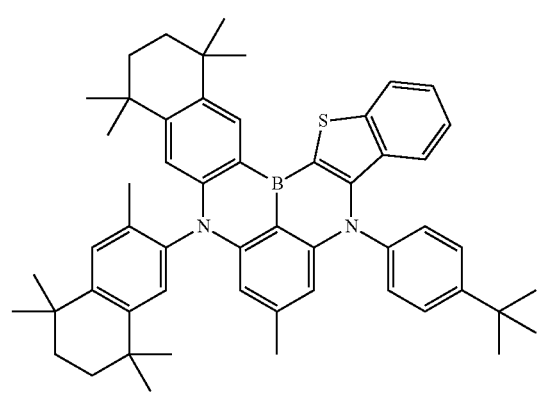 | 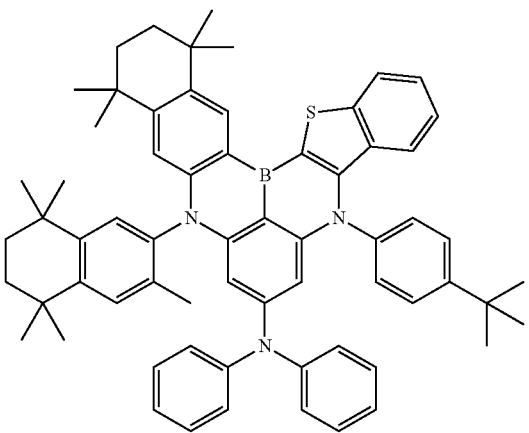 |

1081
-continued
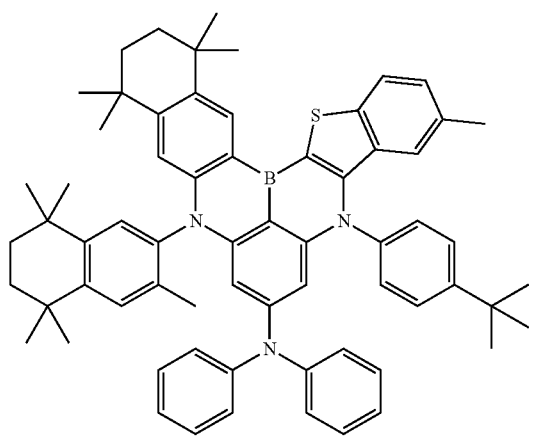
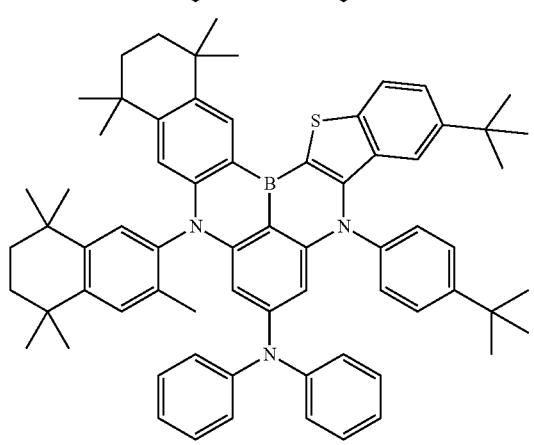
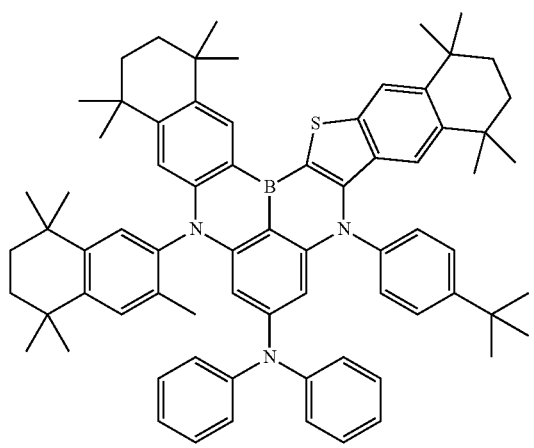
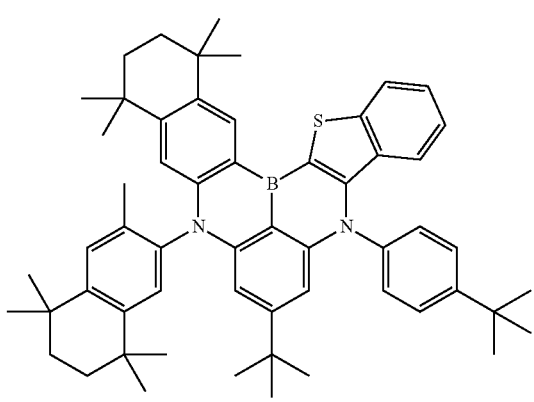
1082
-continued
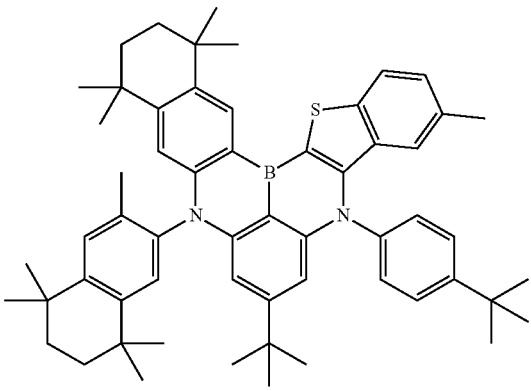
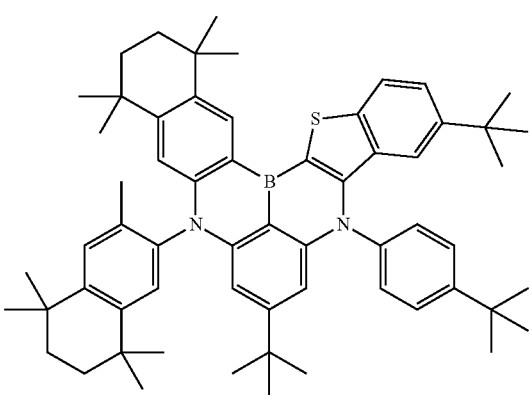
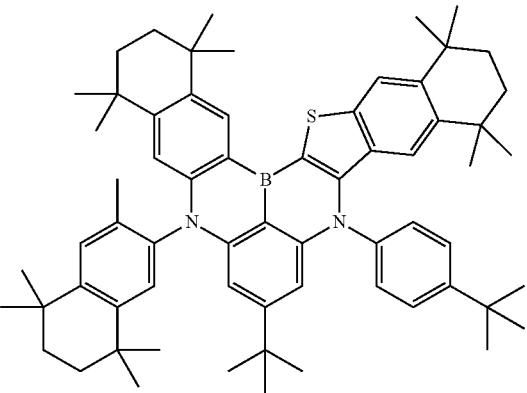
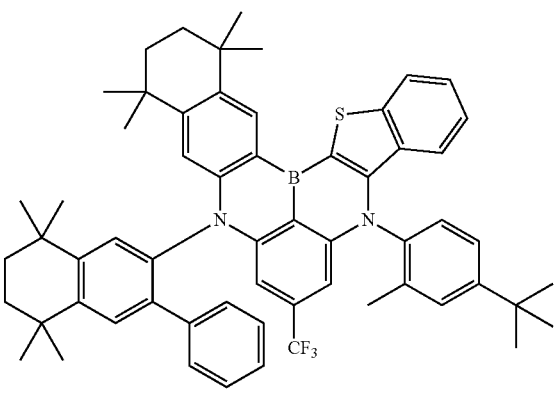

1083
-continued
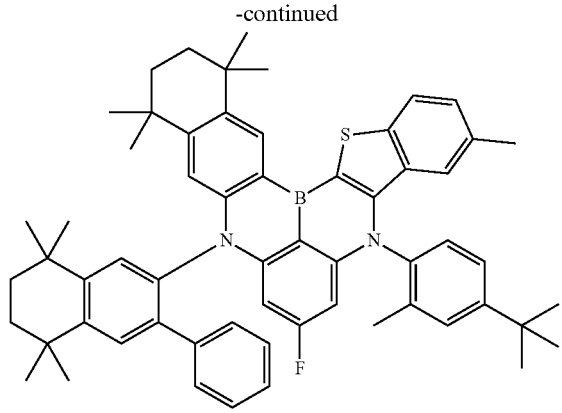
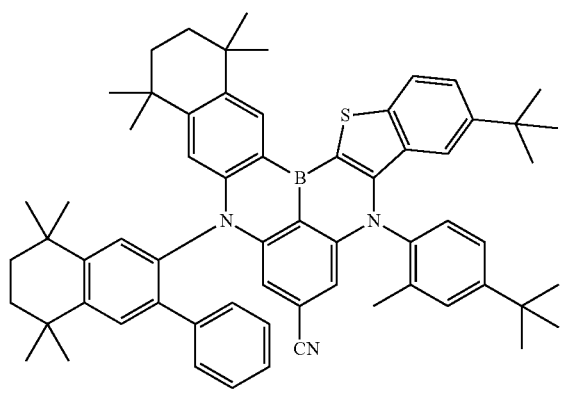

1084
-continued
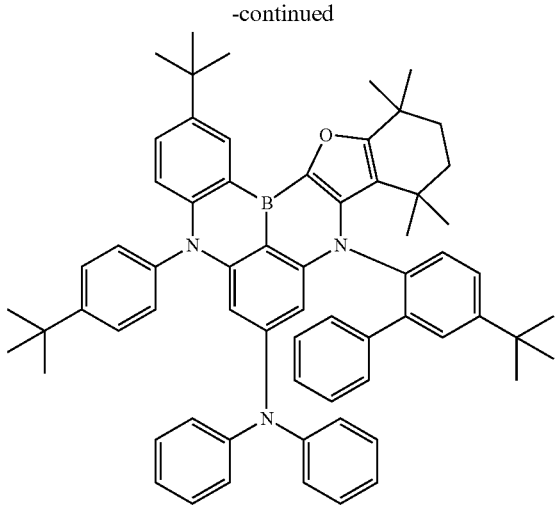
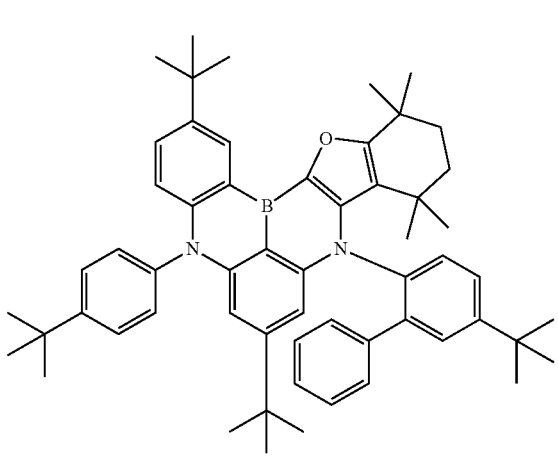
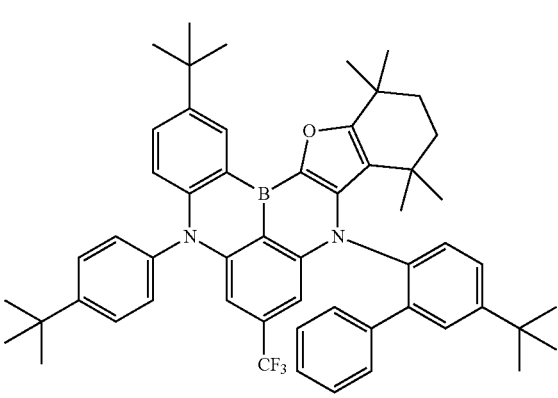
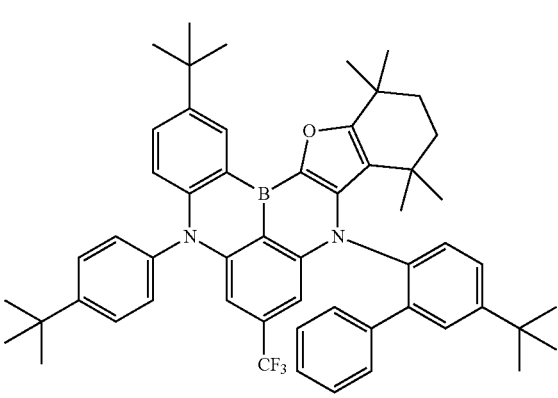

1085
-continued
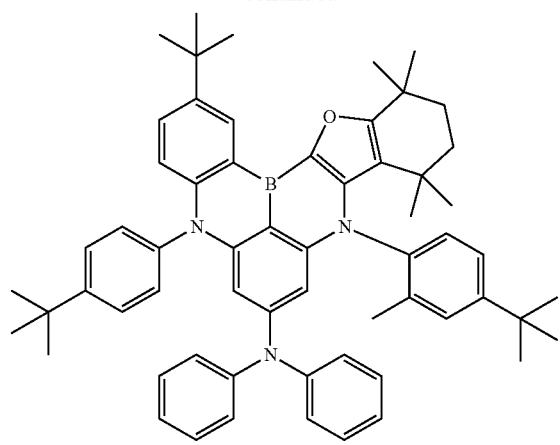
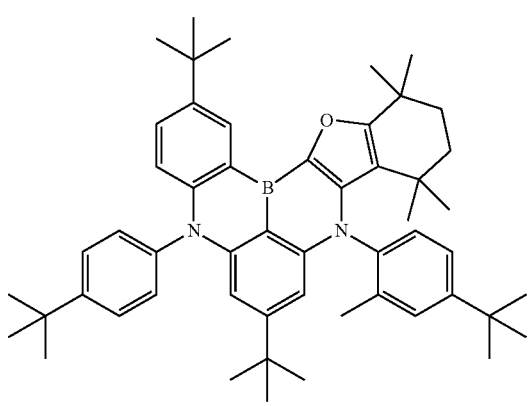
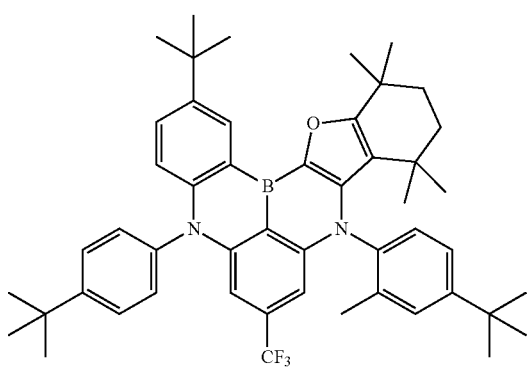
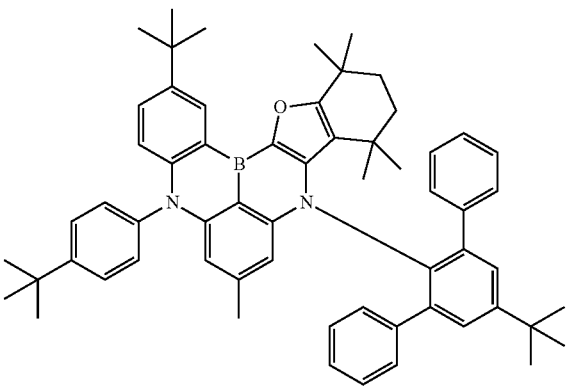
1086
-continued
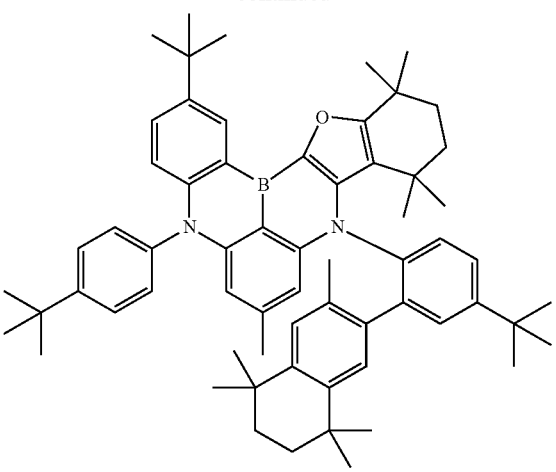
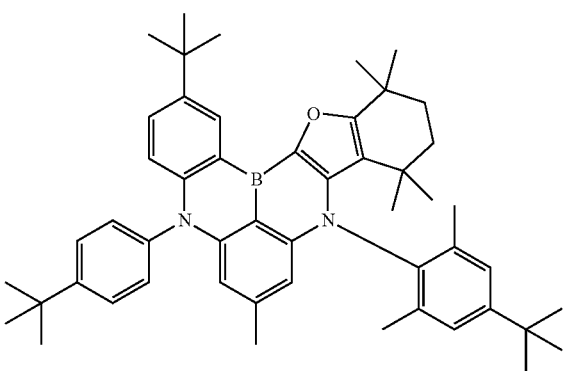
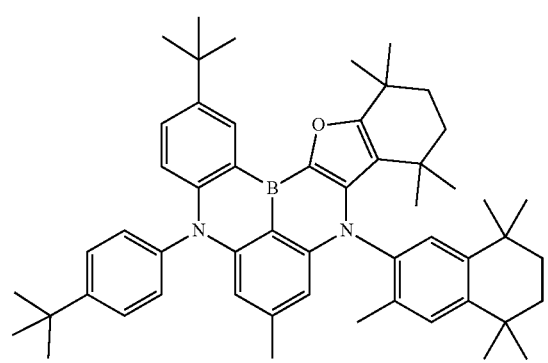
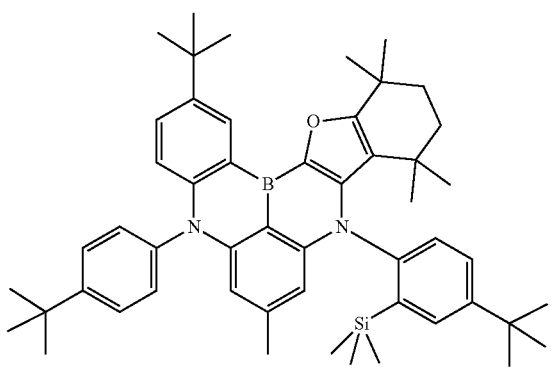

1087
-continued
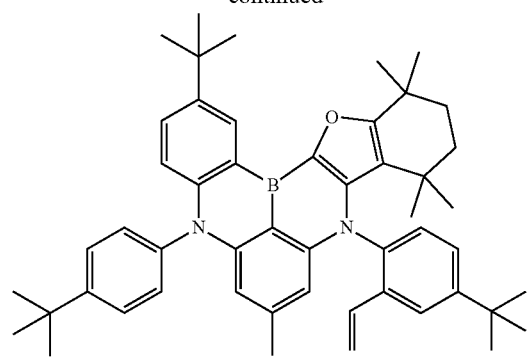
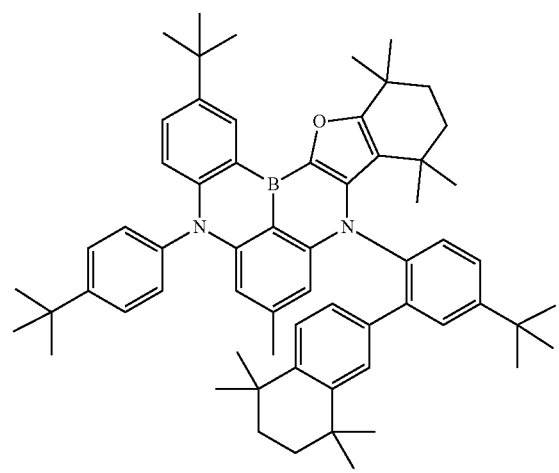
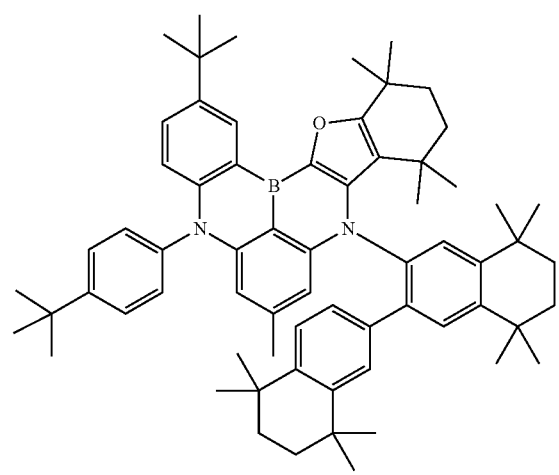
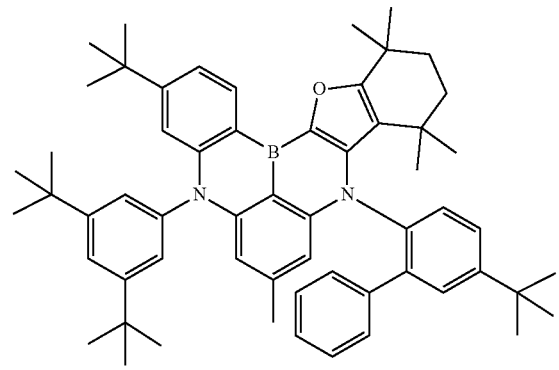
1088
-continued
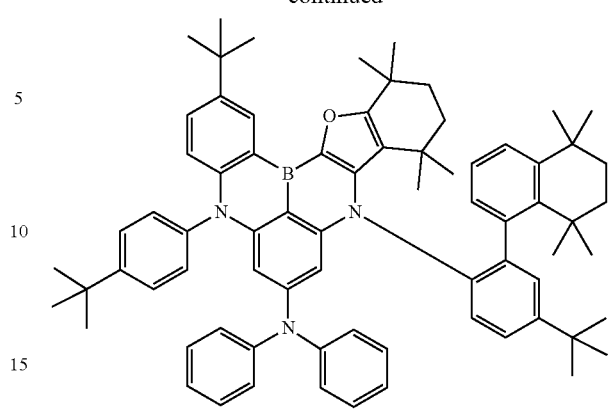
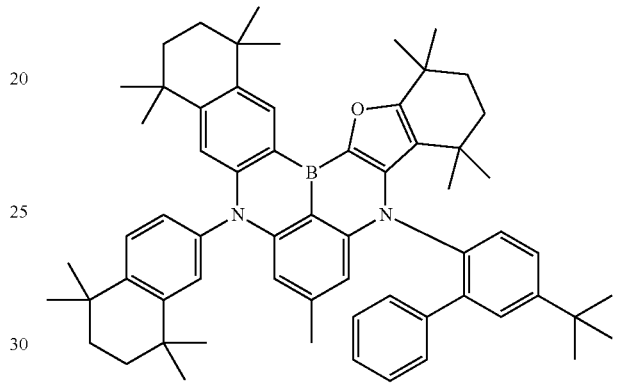
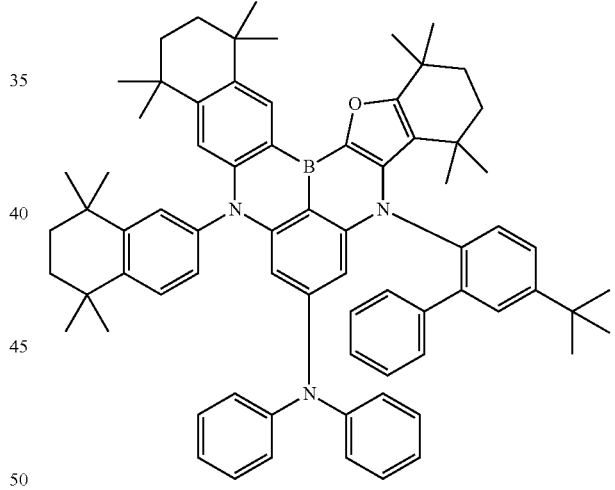
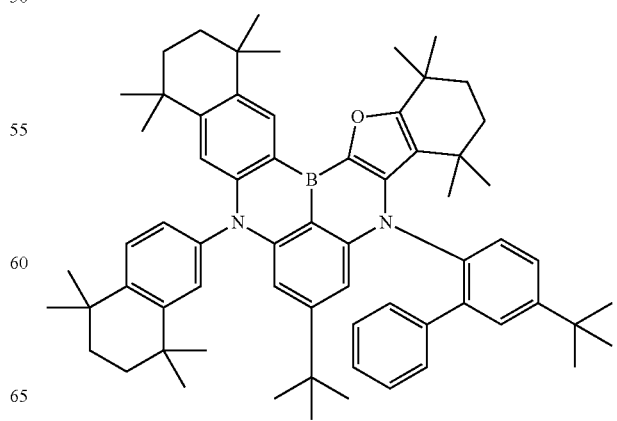

1089
-continued
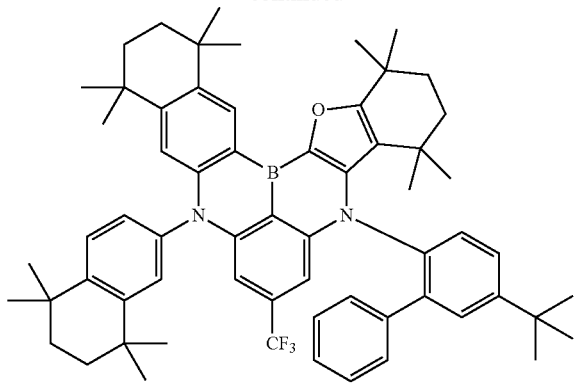
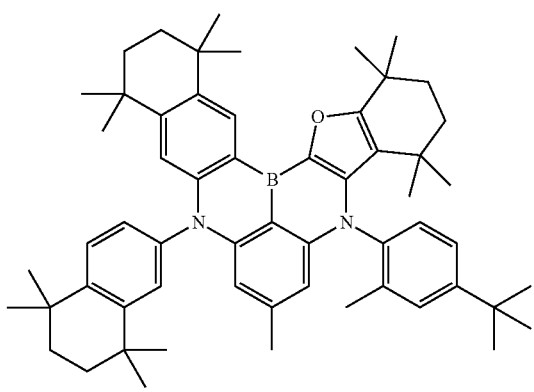
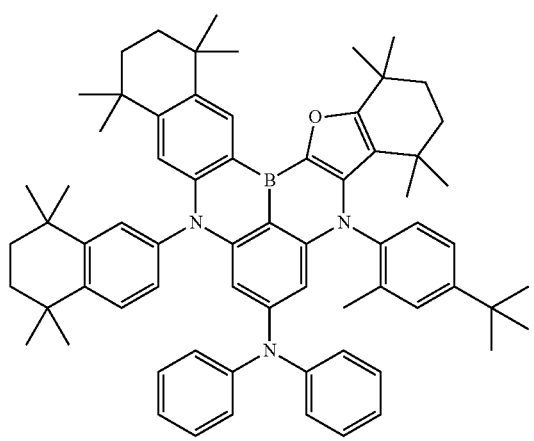
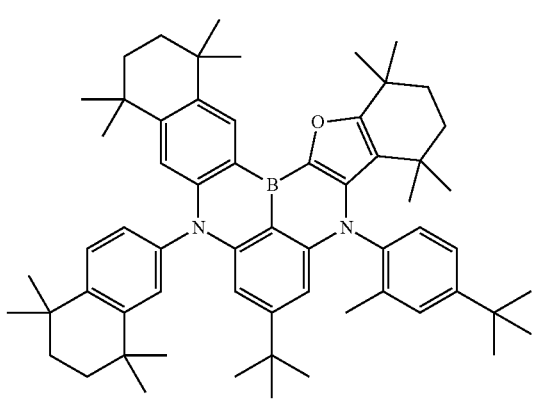
1090
-continued
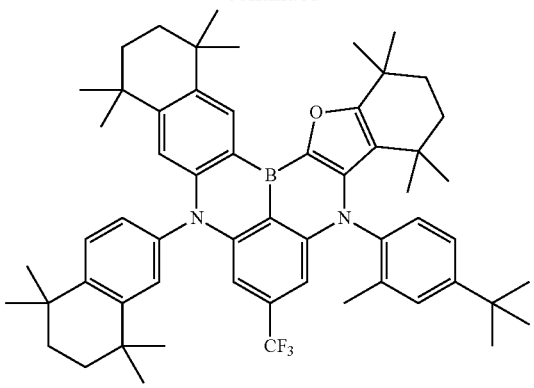
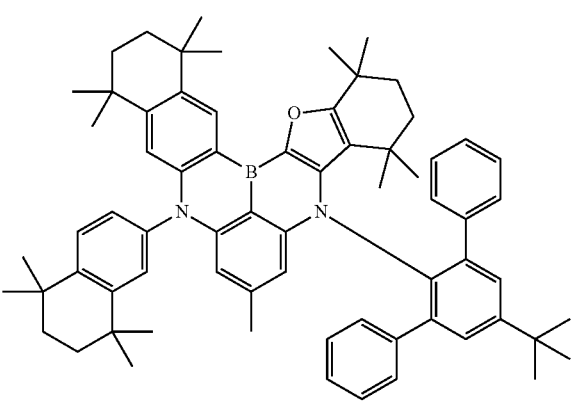
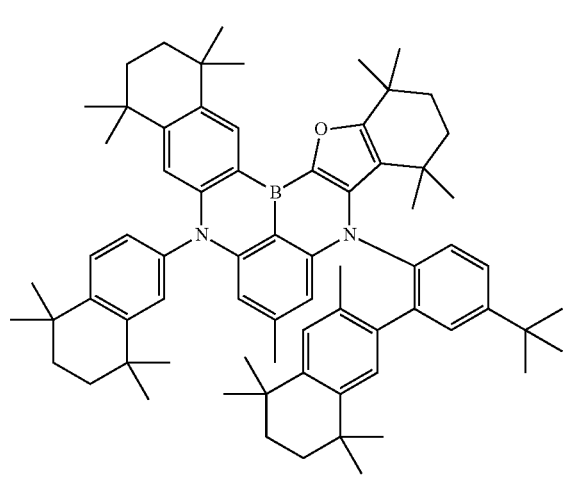
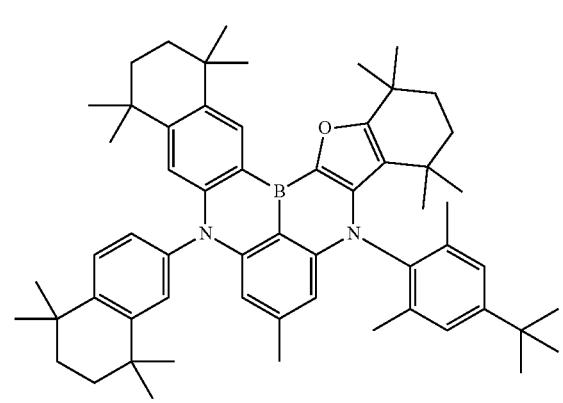

1091
-continued
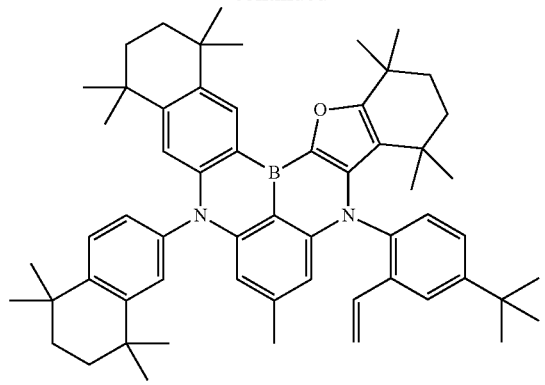
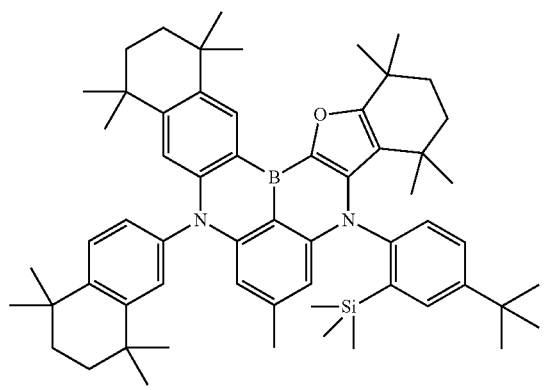
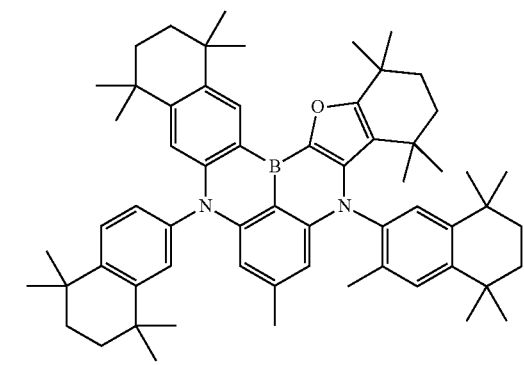
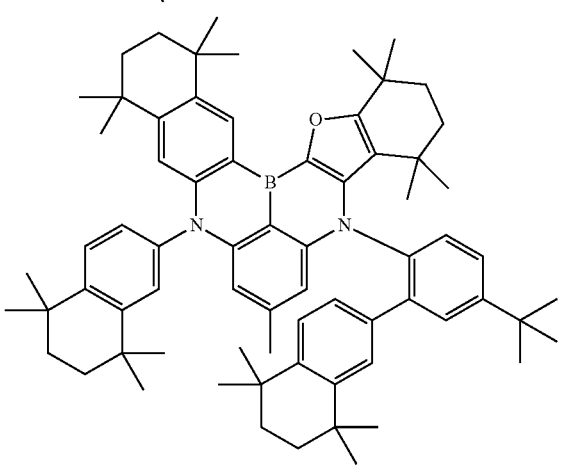
1092
-continued
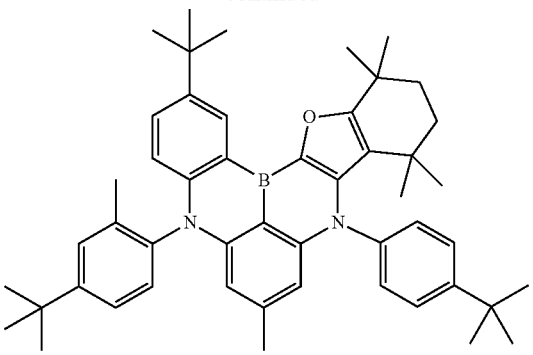
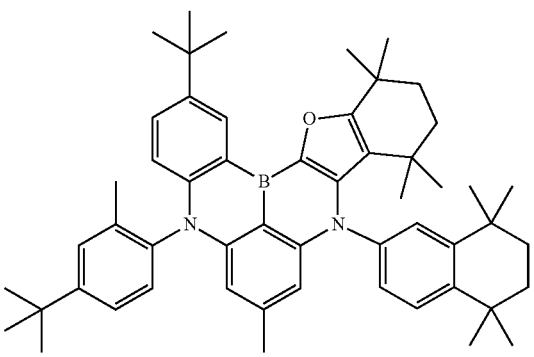
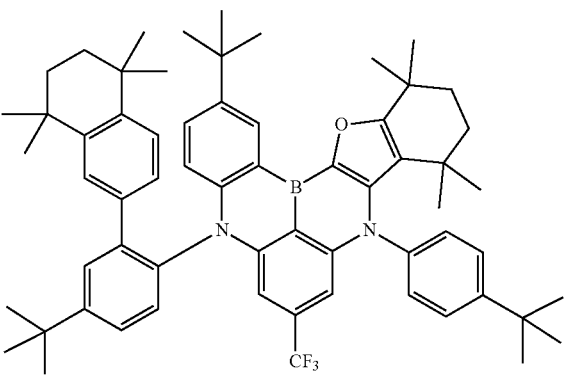
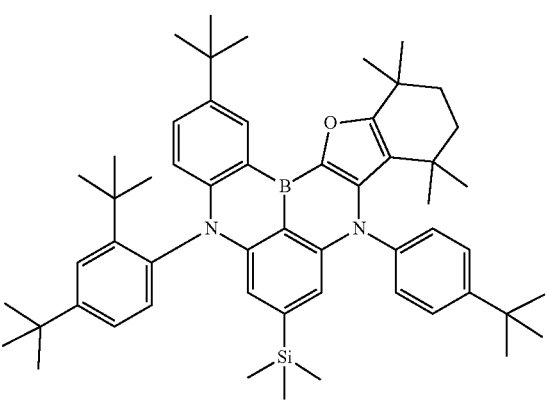

1093
-continued
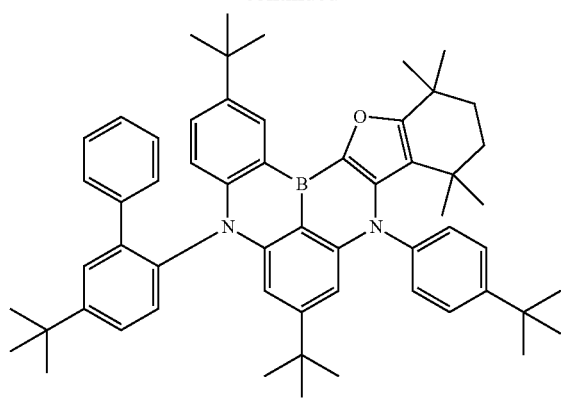
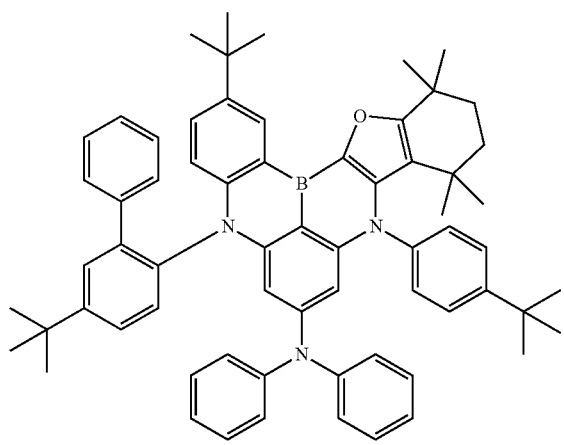
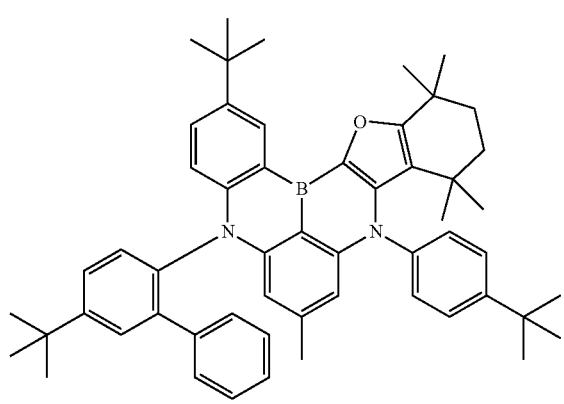
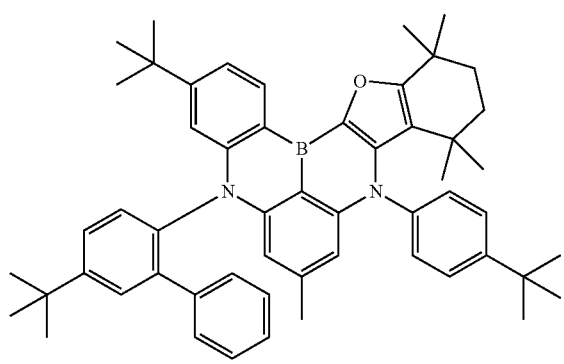
1094
-continued
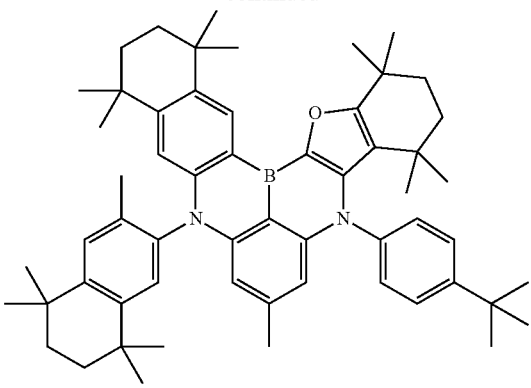
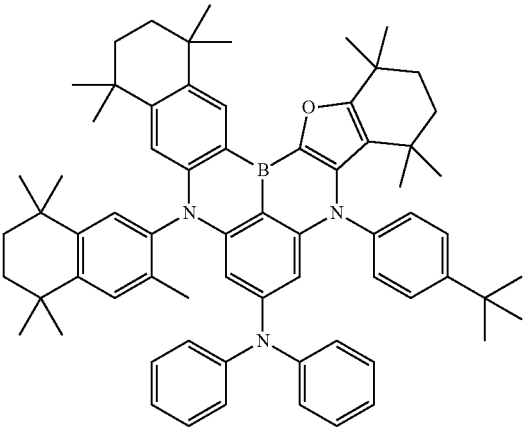
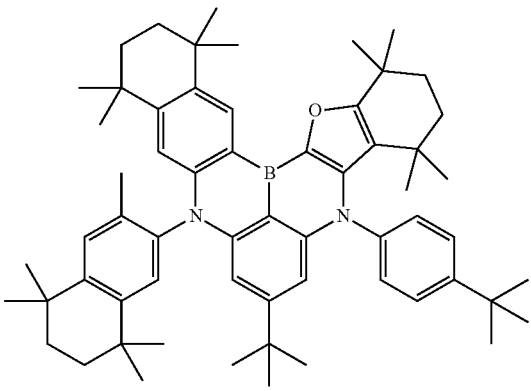
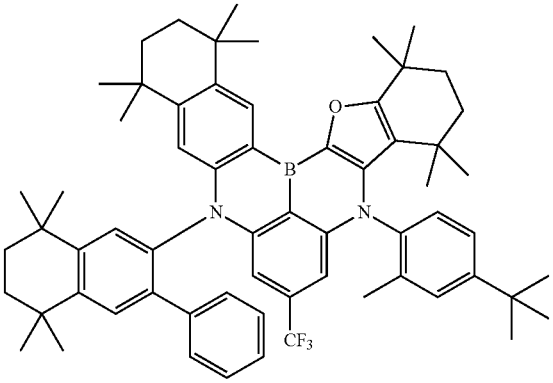

1095
-continued
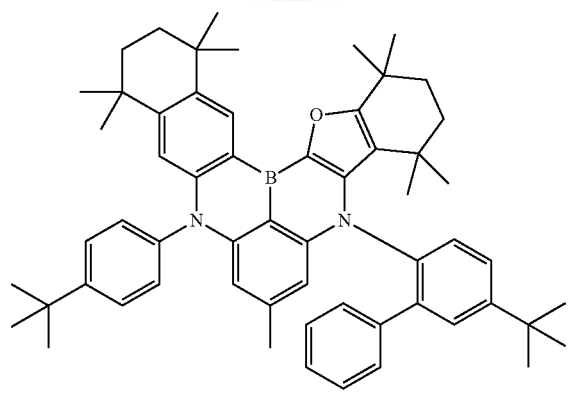
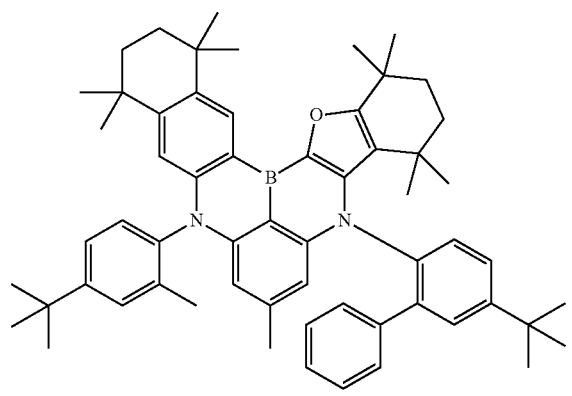
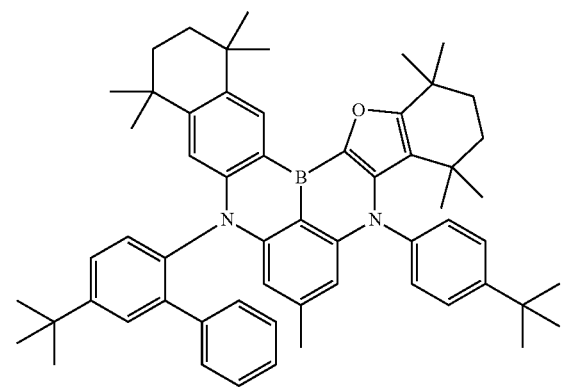
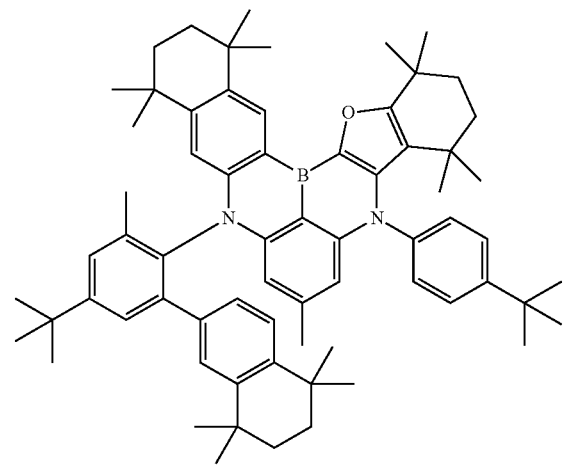
1096
-continued
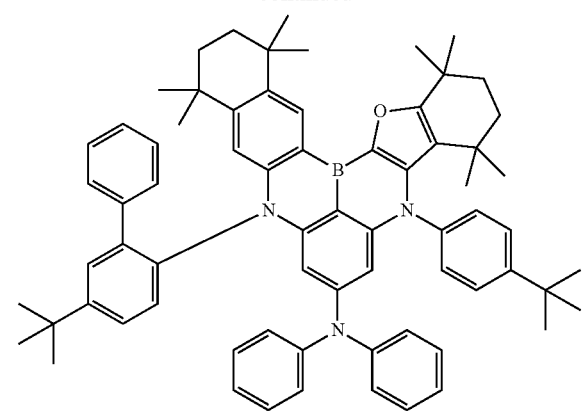
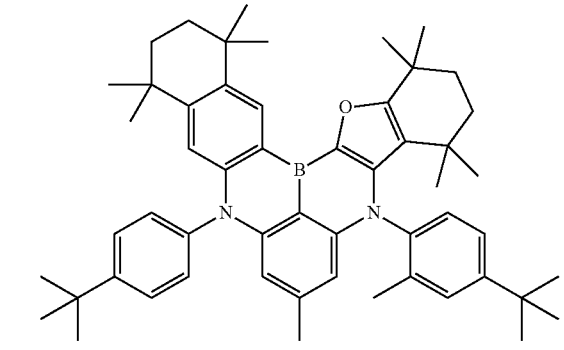
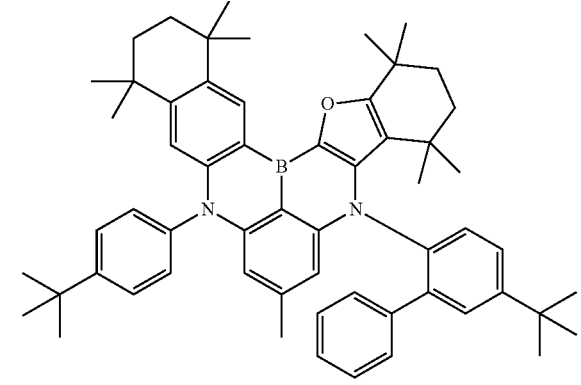
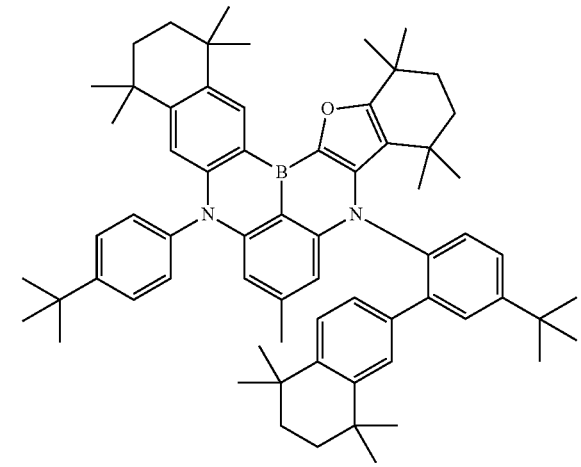

1097
-continued
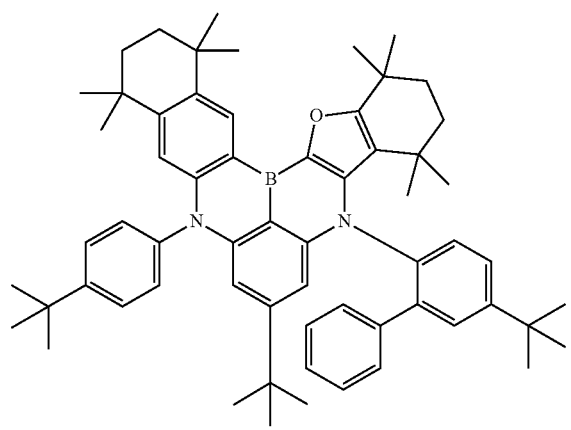
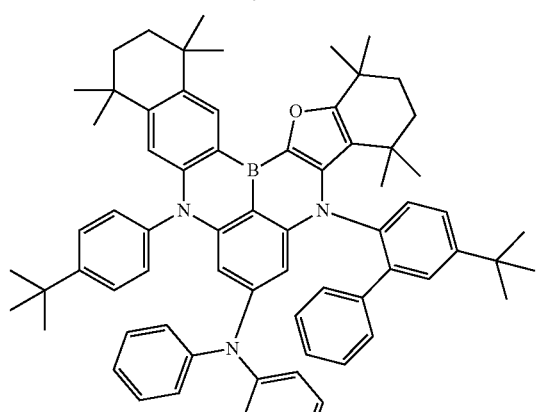
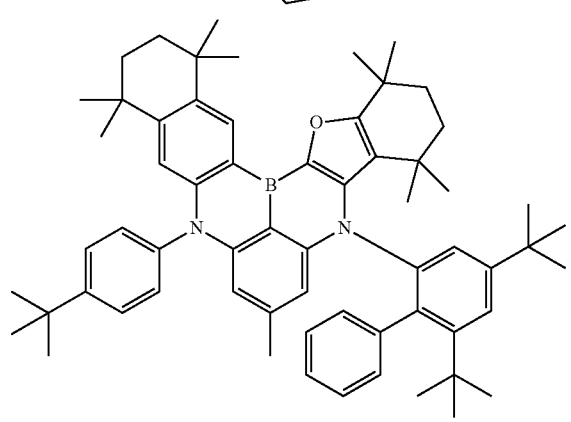
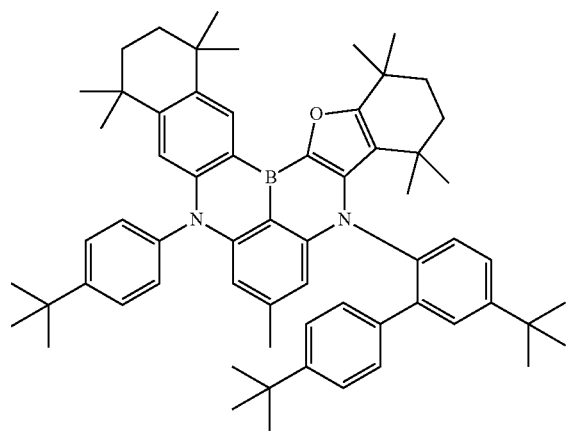
1098
-continued
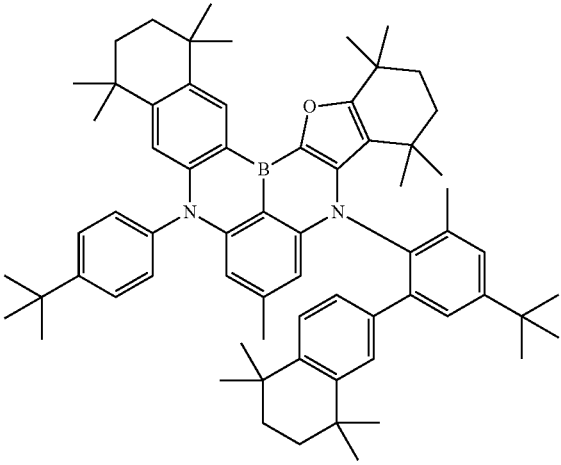 [SMILES: Cc1cc2c3c(c1)N(c1c(C)cc(C(C)(C)C)cc1-c1ccc4c(c1)C(C)(C)CCC4(C)C)c1c(oc4c1C(C)(C)CCC4(C)C)B3c1cc3c(cc1N2c1ccc(C(C)(C)C)cc1)C(C)(C)CCC3(C)C]
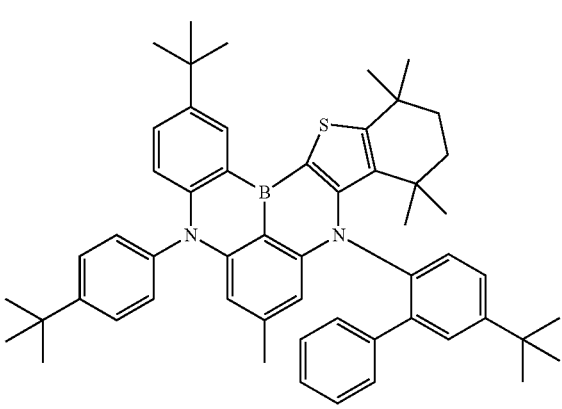
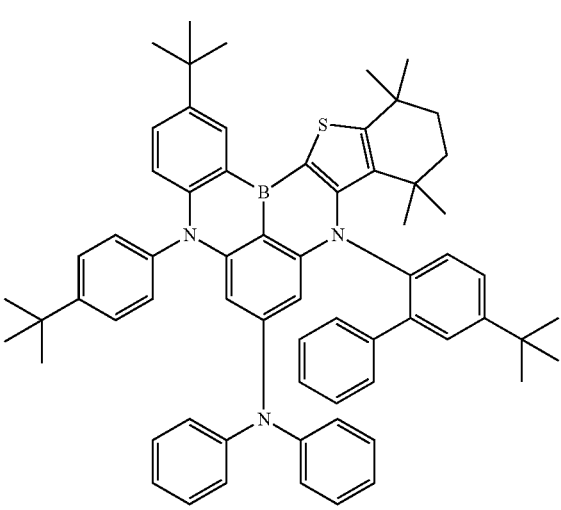

1099
-continued
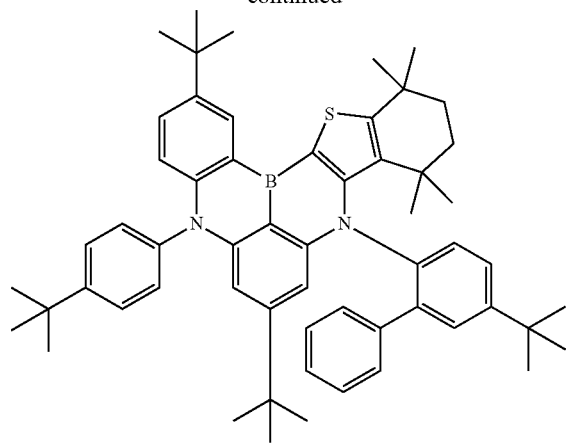
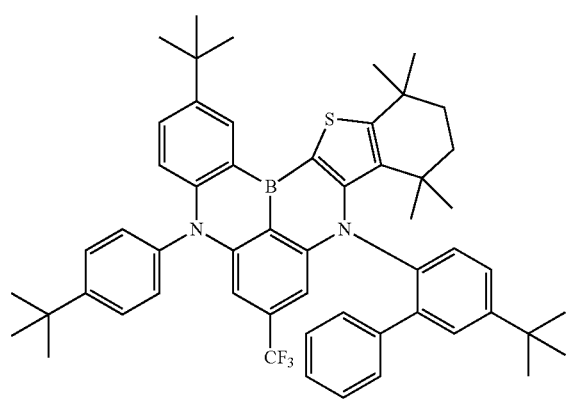
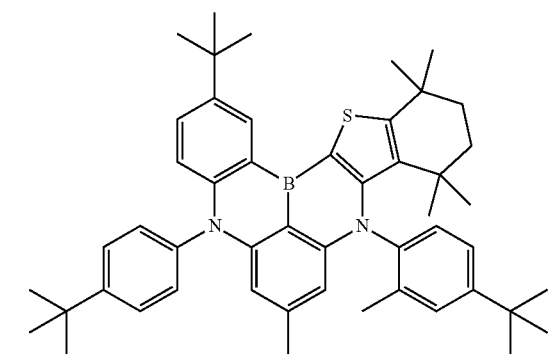
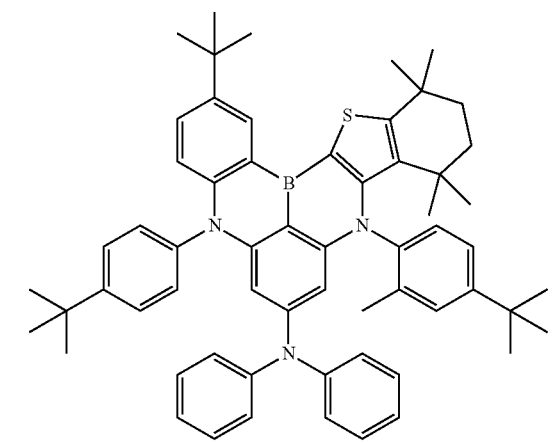
1100
-continued
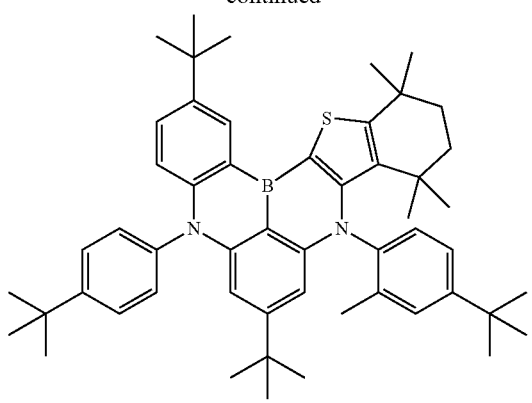
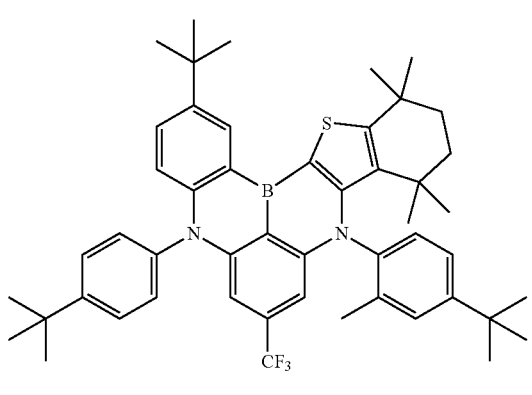
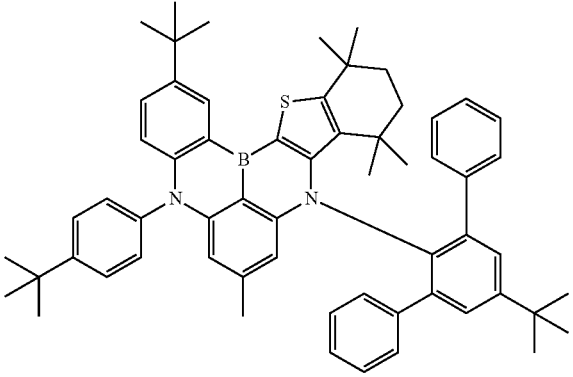
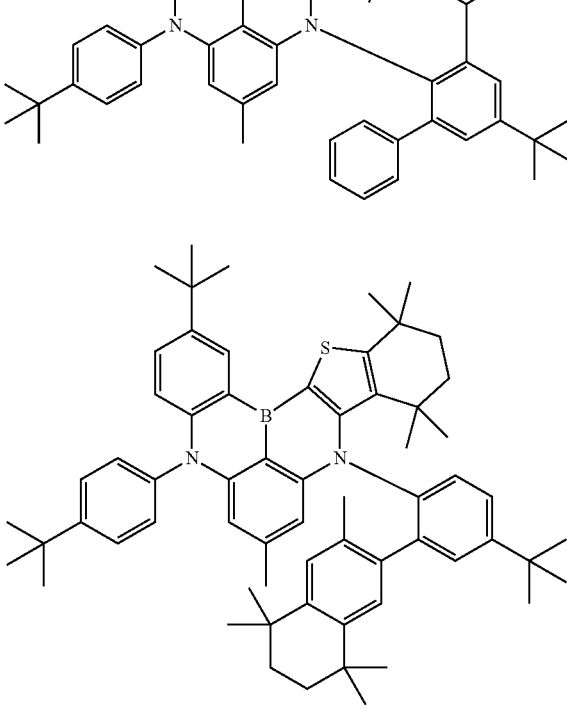

1101
-continued
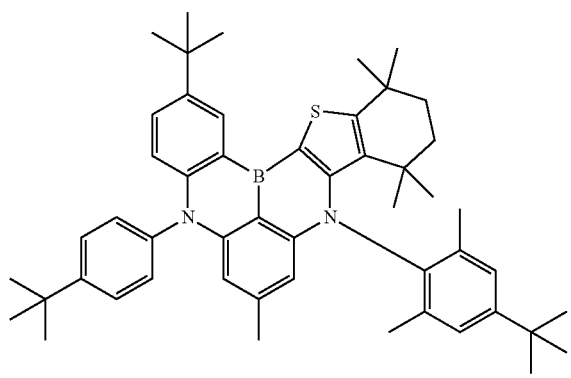
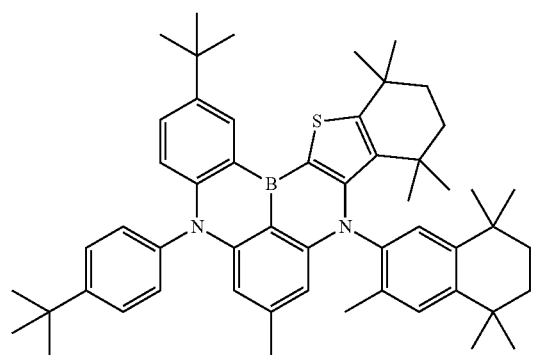
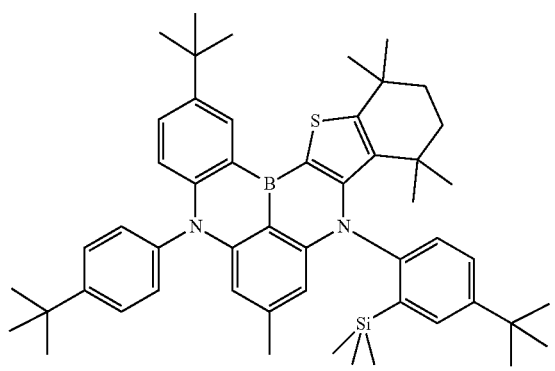
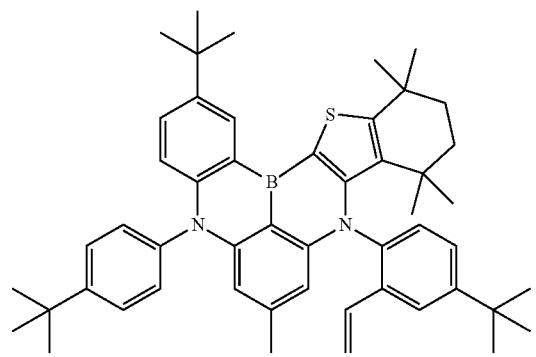
1102
-continued
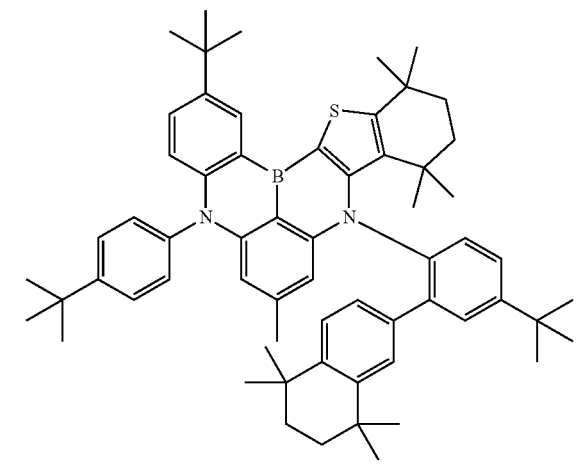
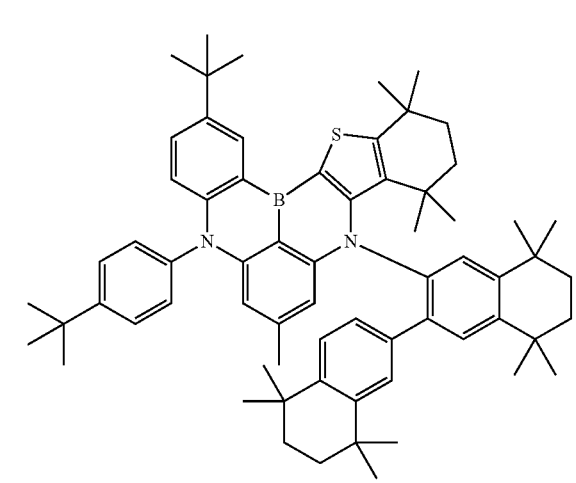
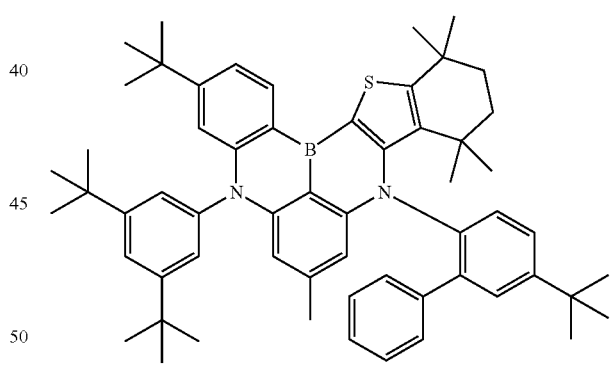
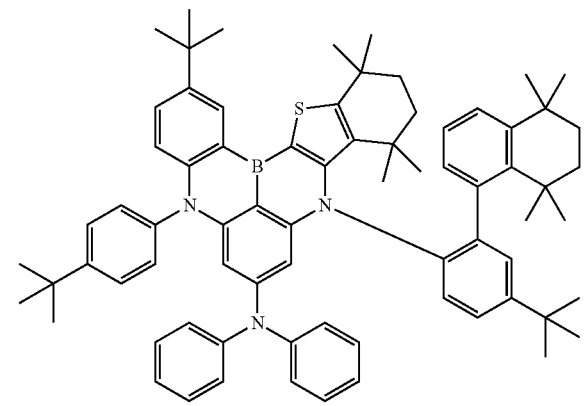

| 1103 -continued | 1104 -continued |
|---|---|
| 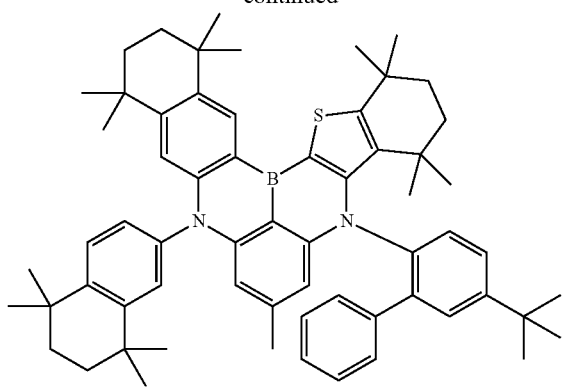 | 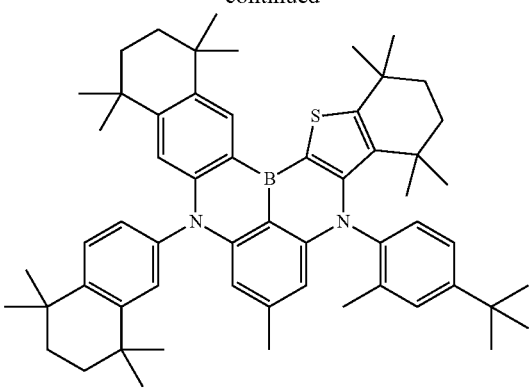 |
| 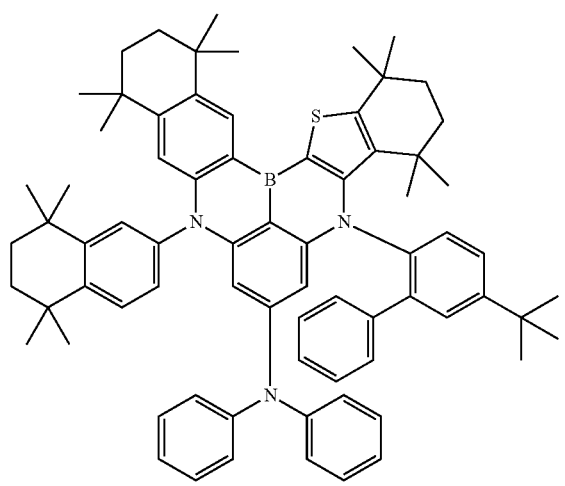 | 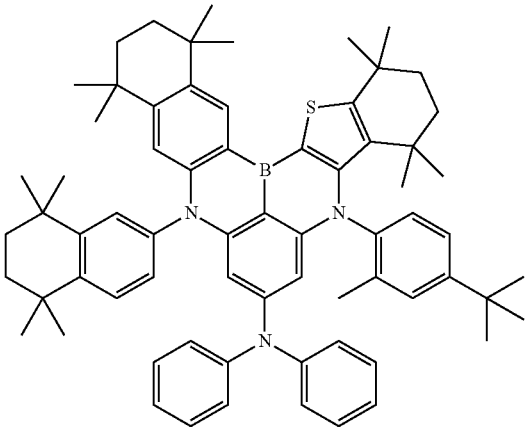 |
| 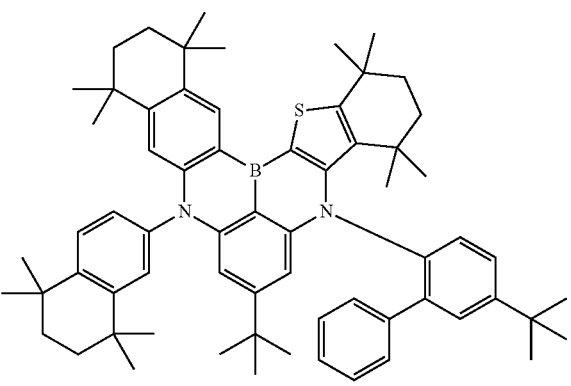 | 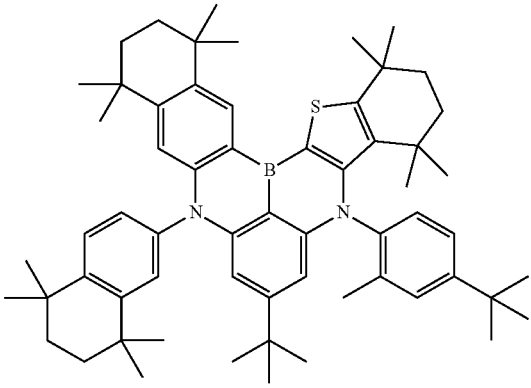 |
| 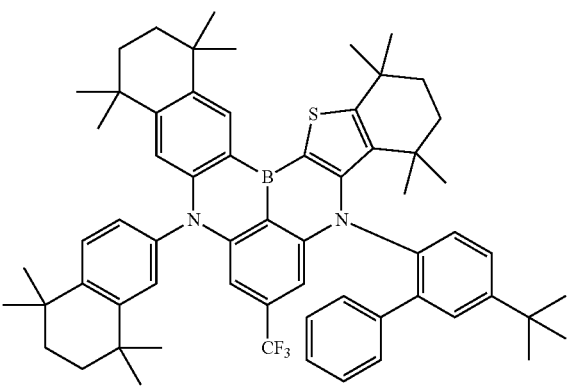 | 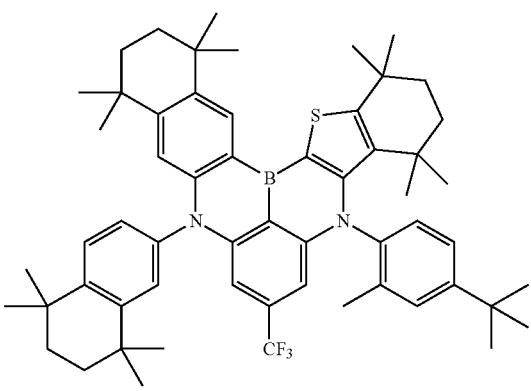 |

1105
-continued
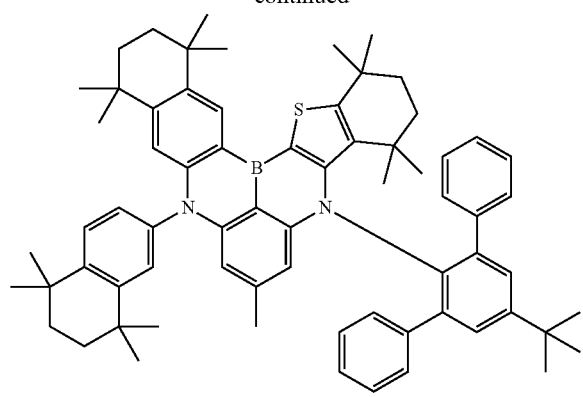
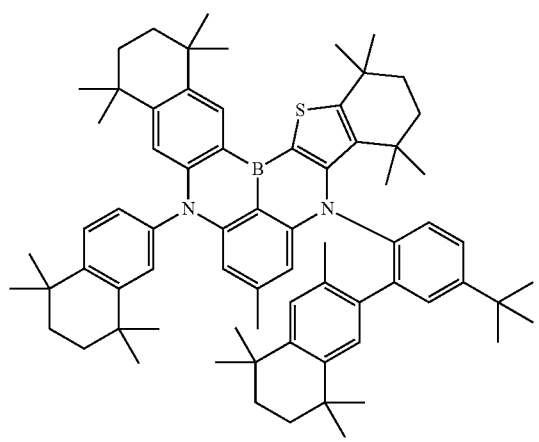
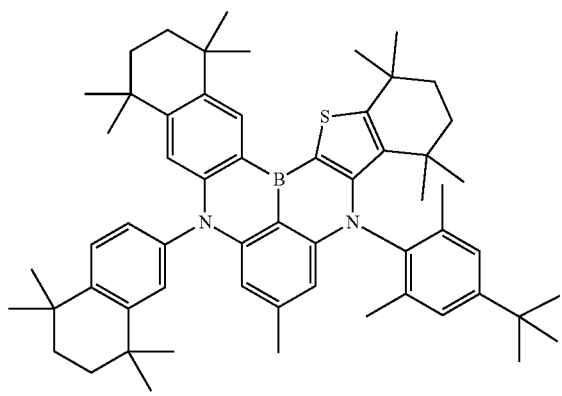
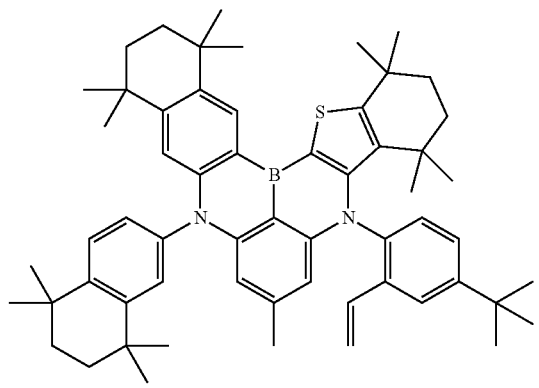
1106
-continued
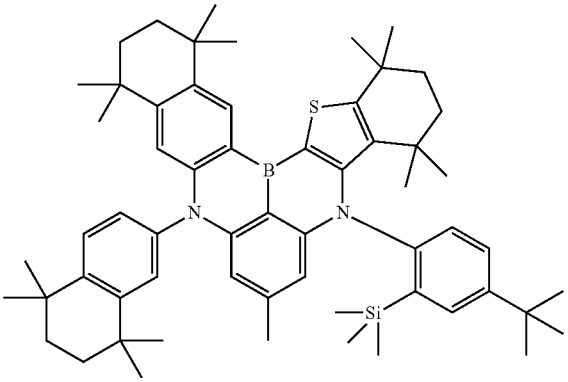
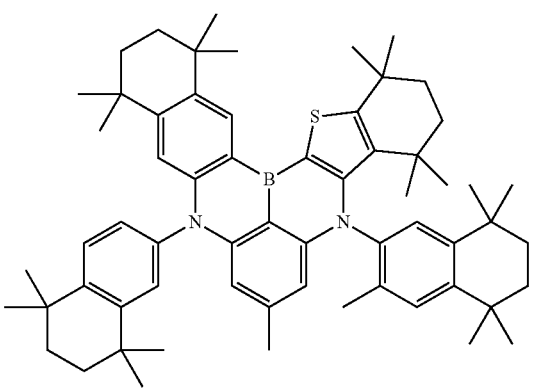
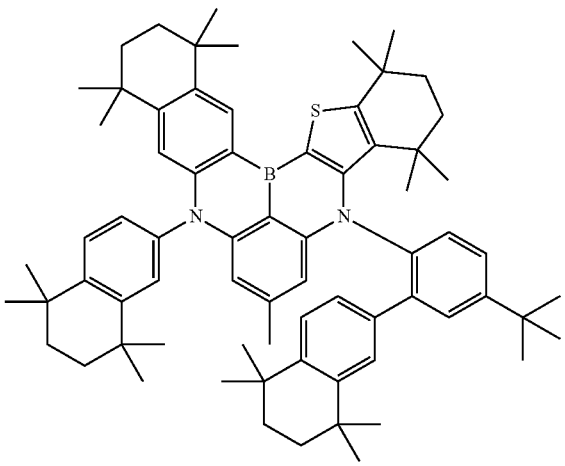
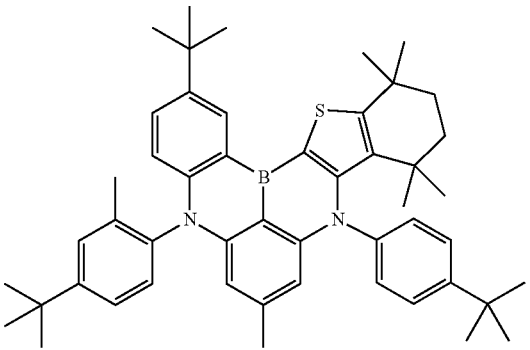

1107
-continued
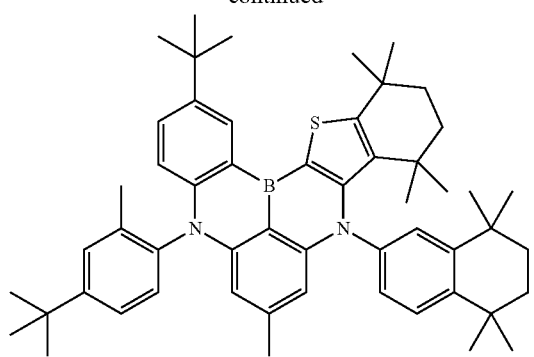
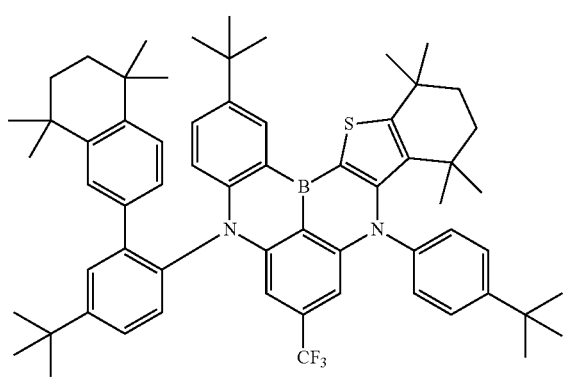
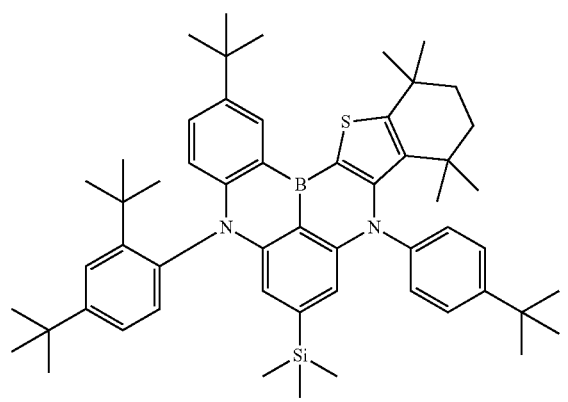
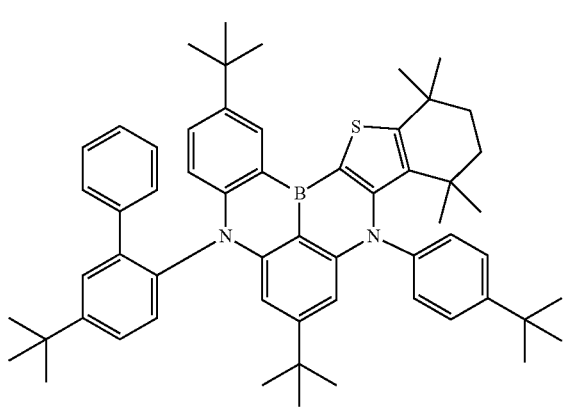
1108
-continued
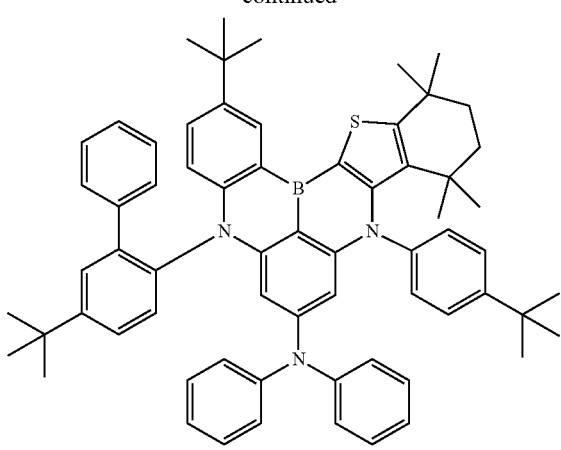
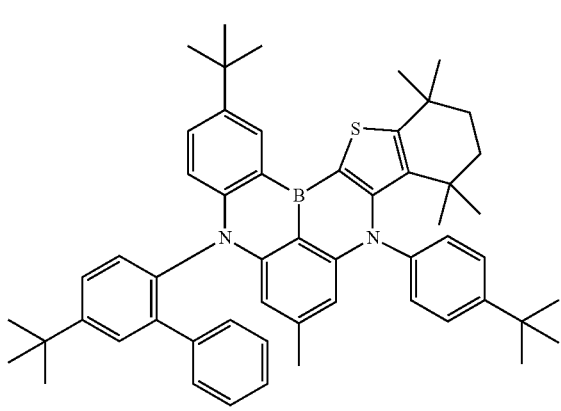
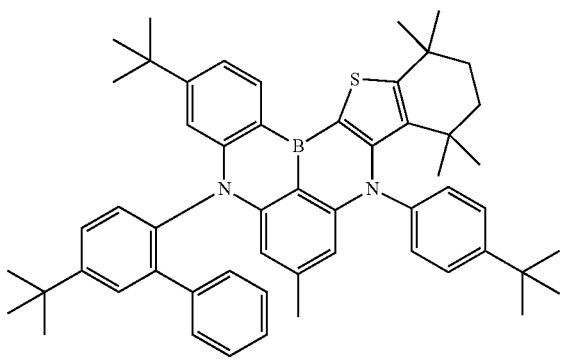
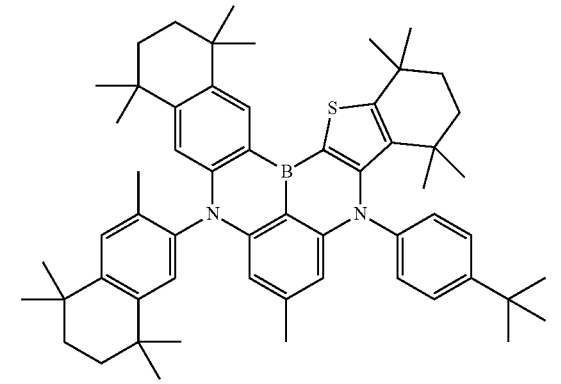

1109
-continued
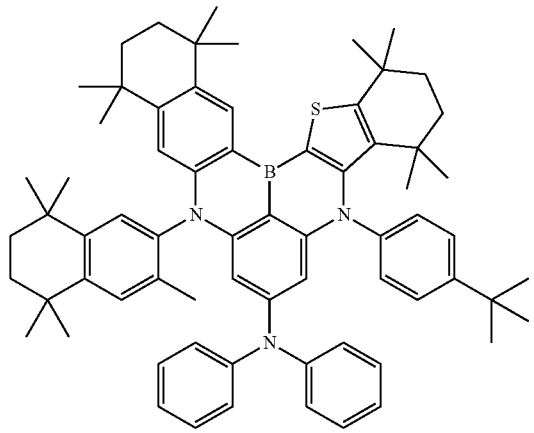
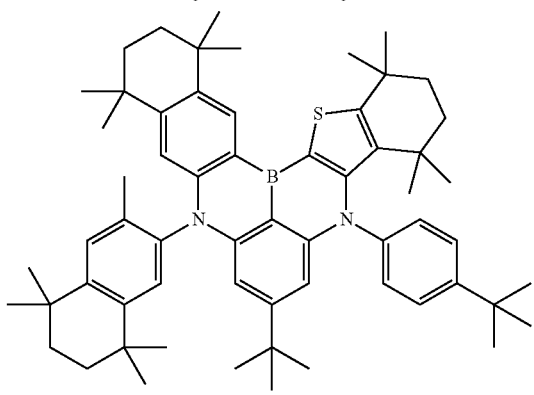
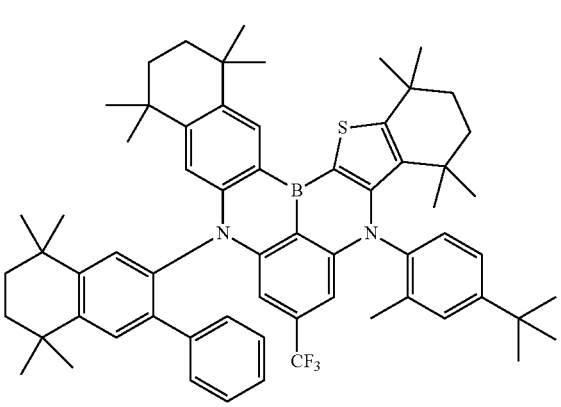
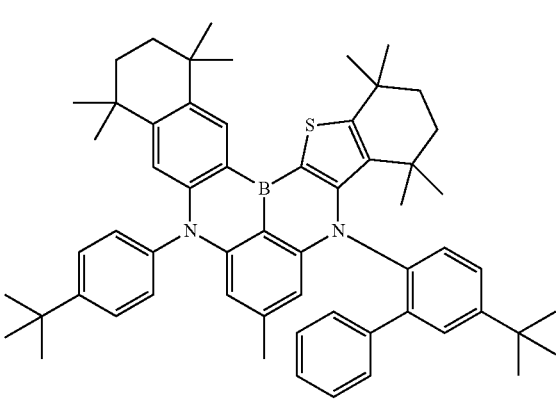
1110
-continued
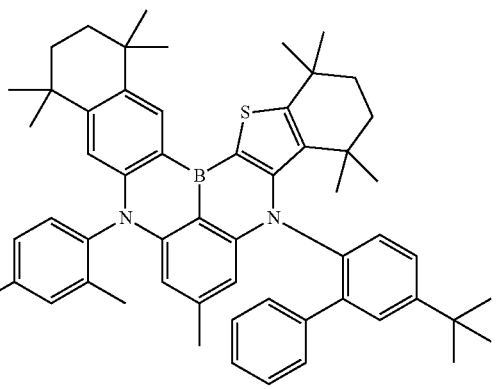
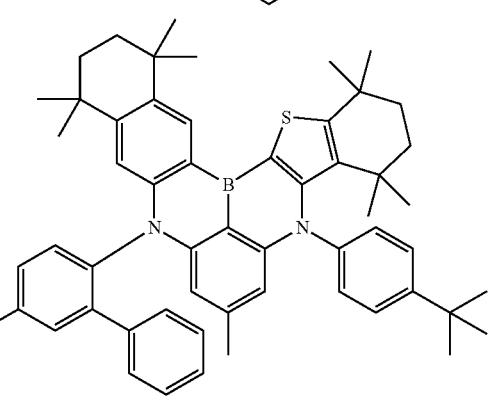
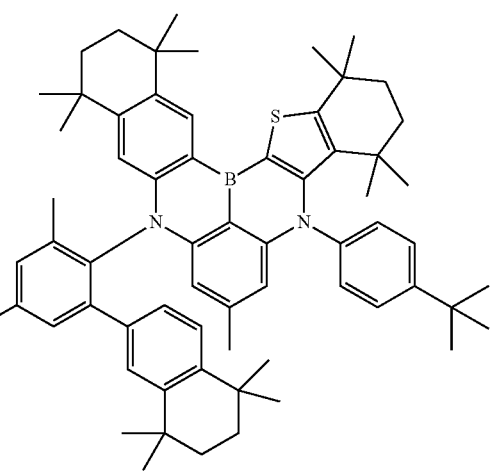
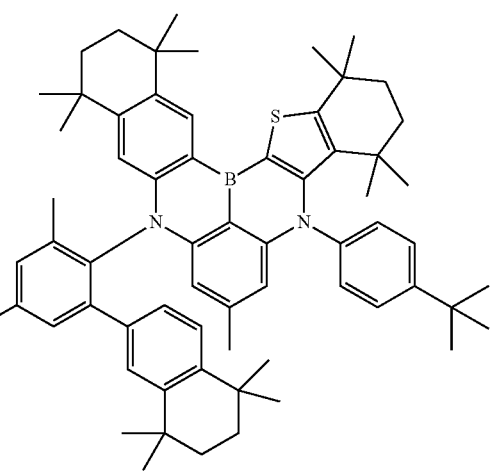

1111
-continued

1112
-continued

| 1113 -continued | 1114 -continued |
|---|---|
| 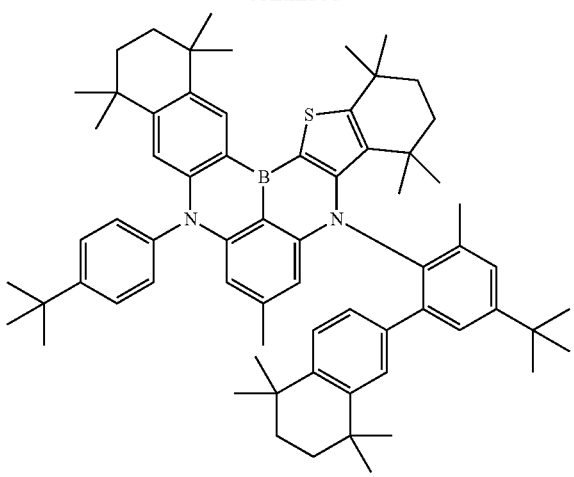 [SMILES: Cc1cc2c3c(c1)N(c1c(C)cc(C(C)(C)C)cc1-c1ccc4c(c1)C(C)(C)CCC4(C)C)c1c(sc4c1C(C)(C)CCC4(C)C)B3c1cc3c(cc1N2c1ccc(C(C)(C)C)cc1)C(C)(C)CCC3(C)C] | 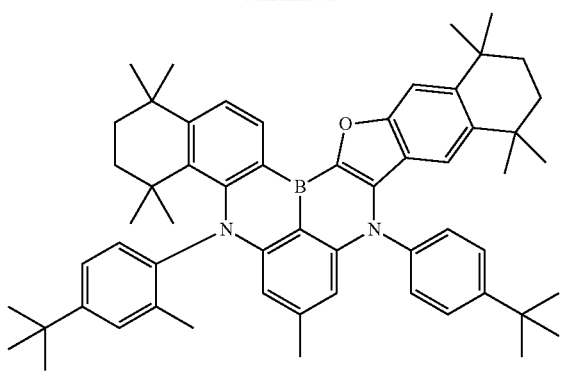 |
| 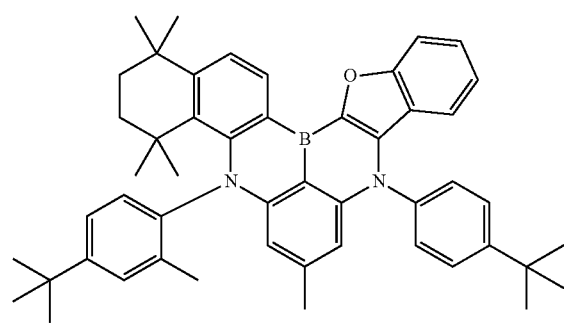 | 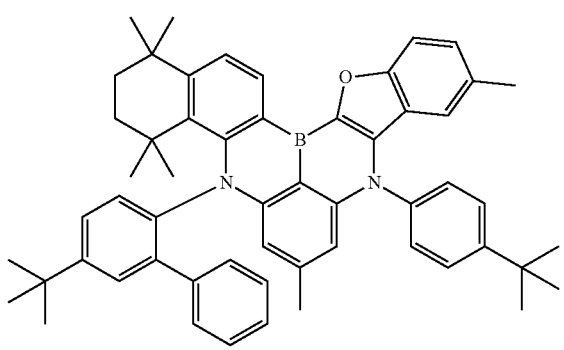 |
| 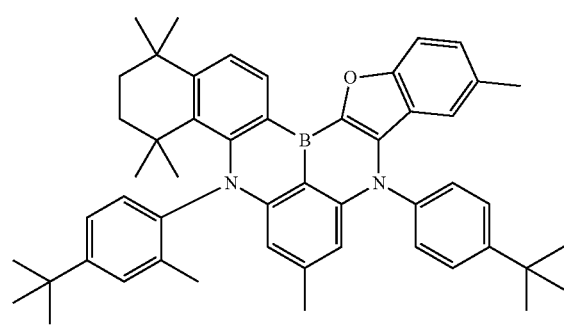 | 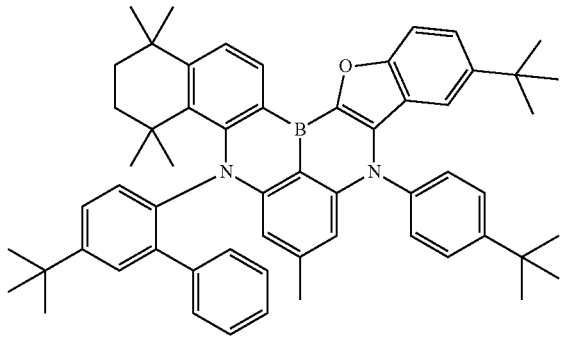 |
| 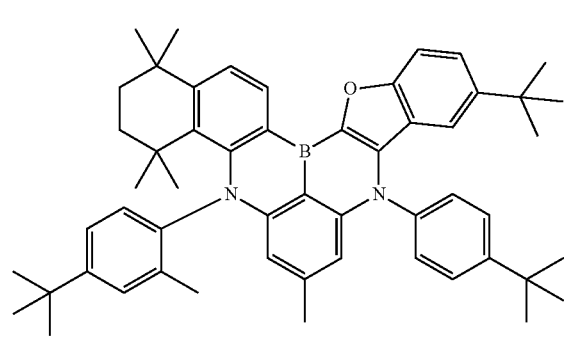 | |

| 1115 -continued | 1116 -continued |
|---|---|
| 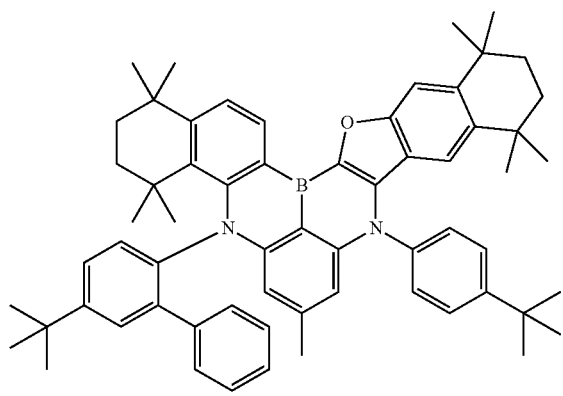 | 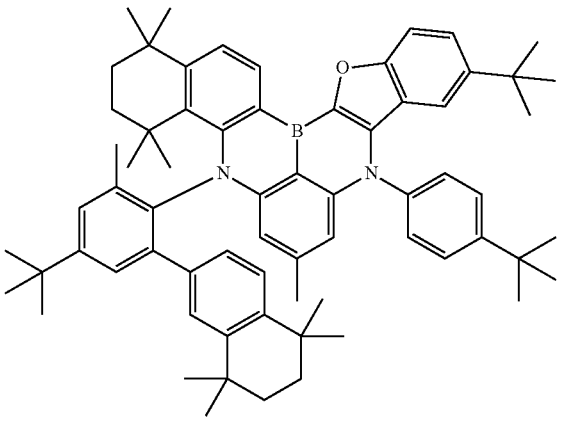 |
| 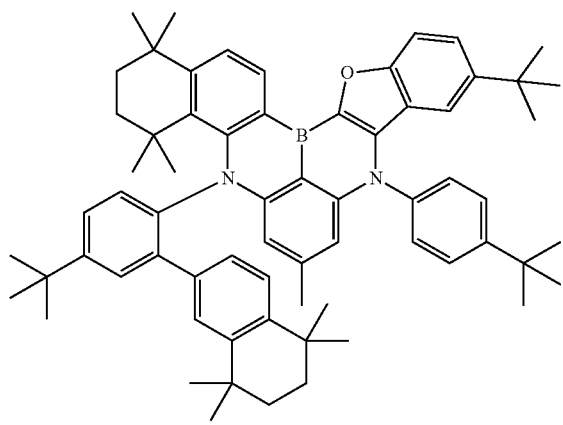 | 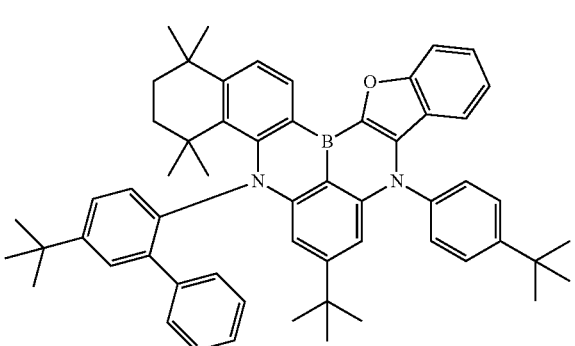 |
| 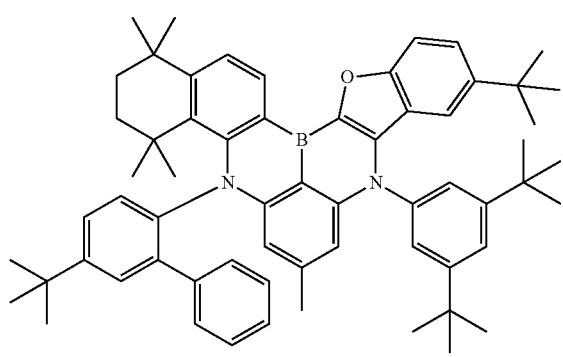 | 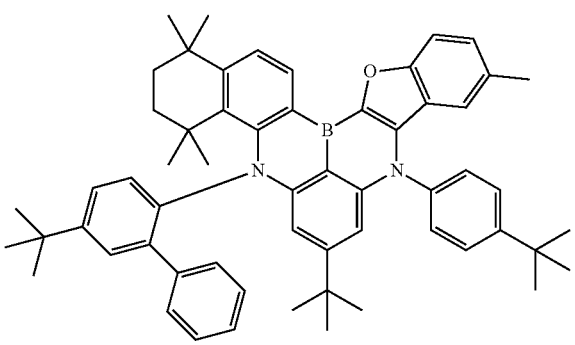 |
| 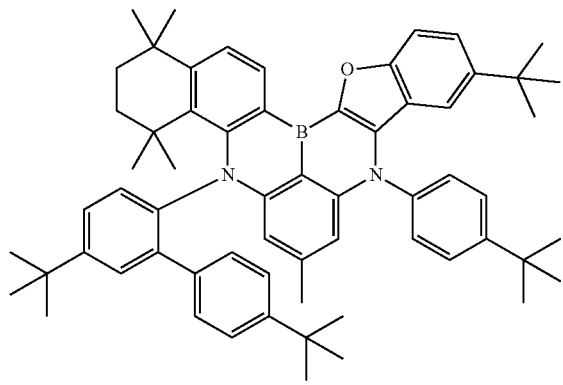 | 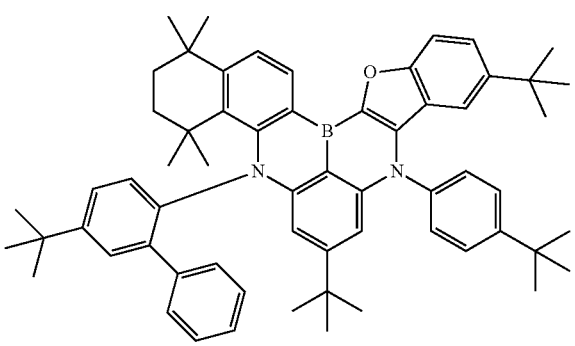 |

1117
-continued
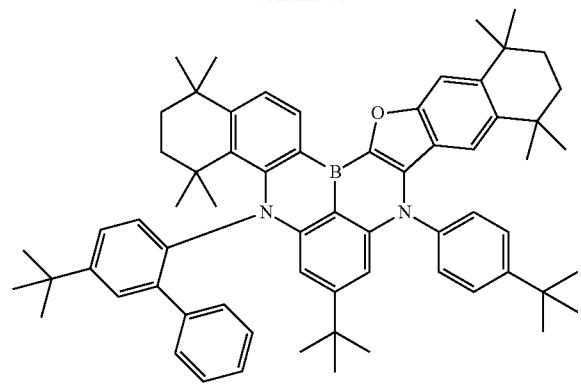
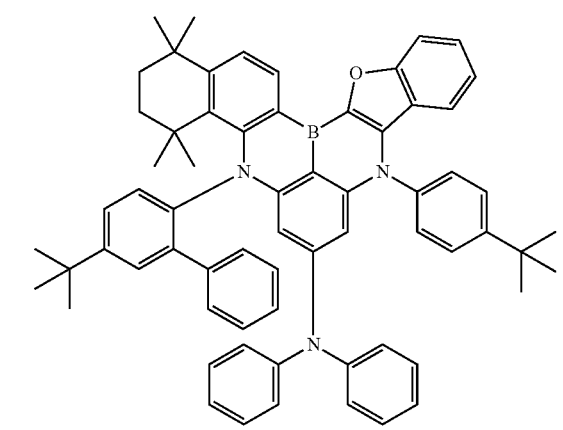
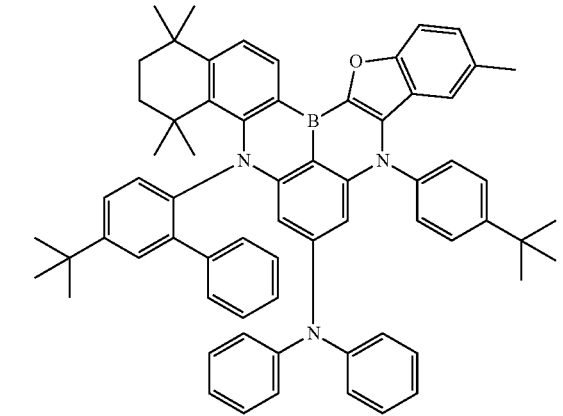
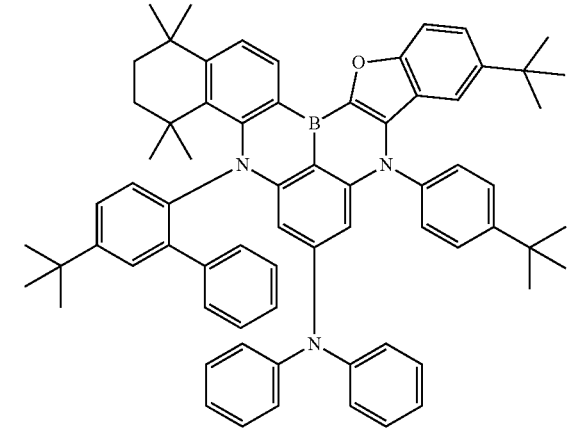
1118
-continued
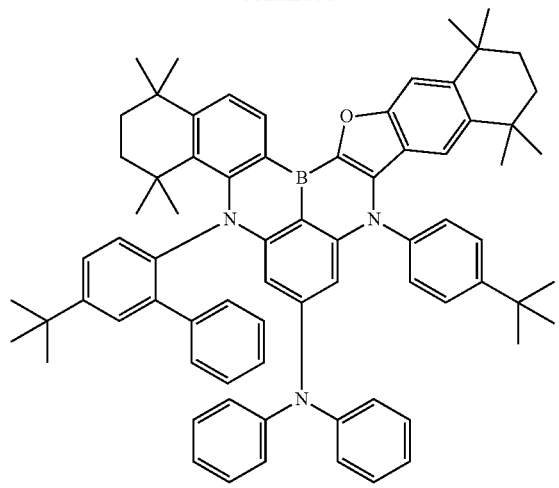
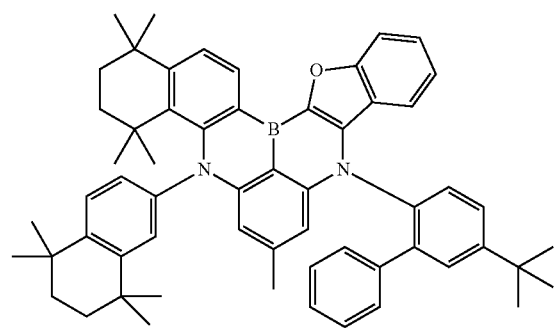
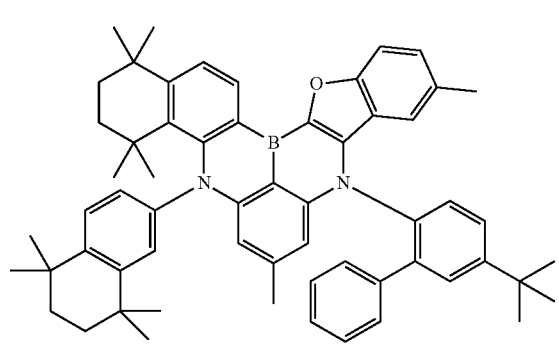
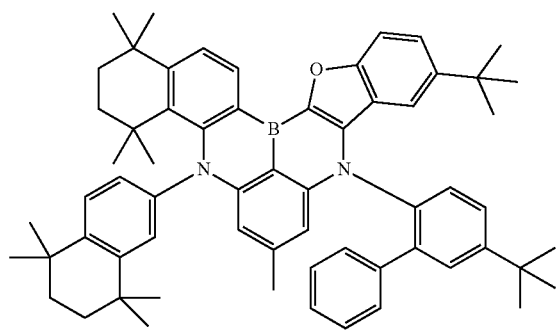

1119 -continued
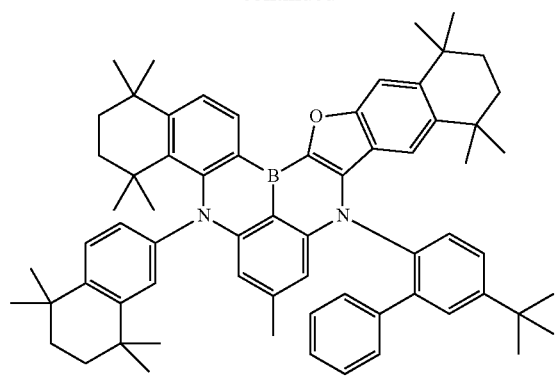
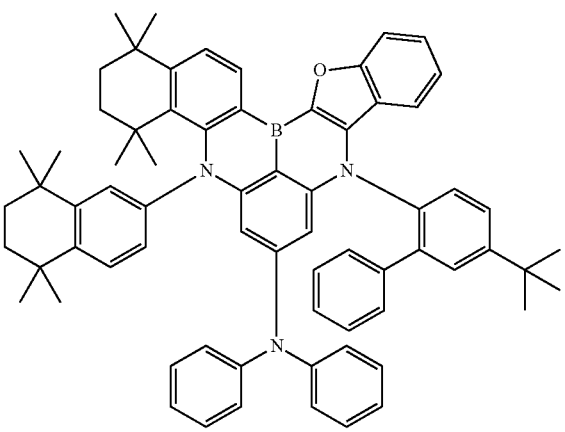
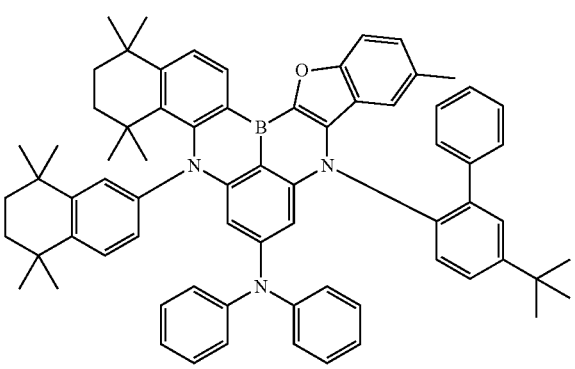
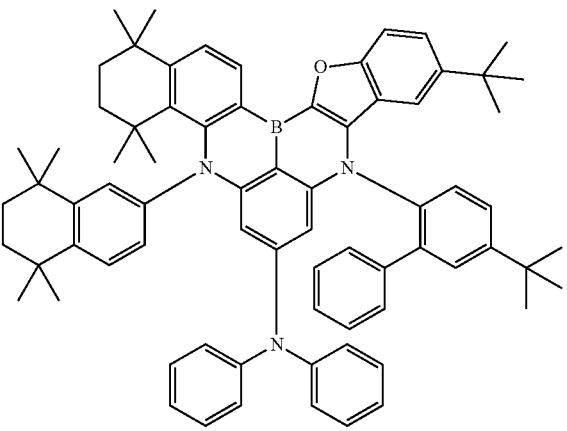
1120 -continued
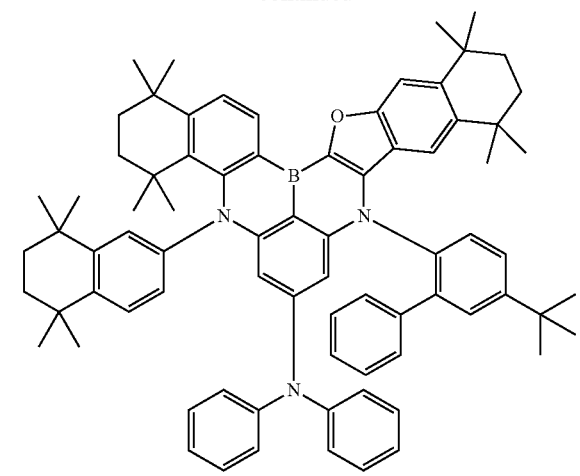
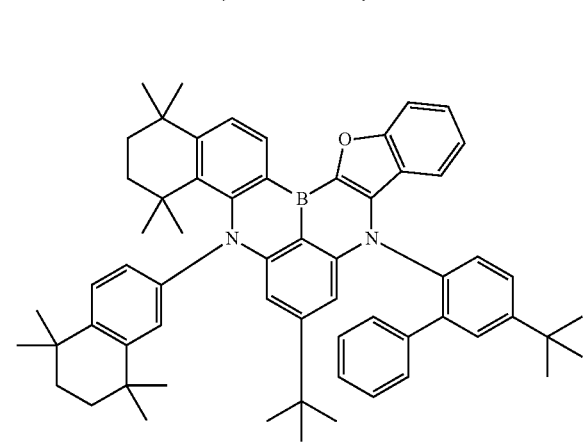
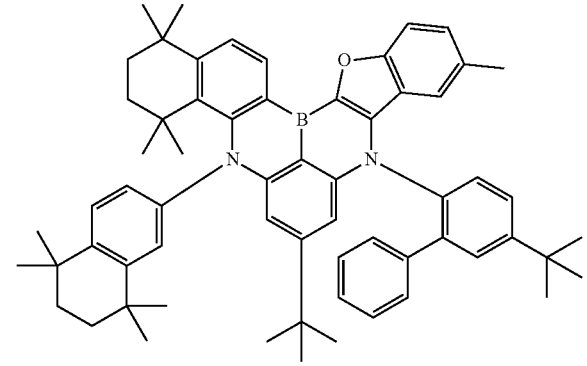
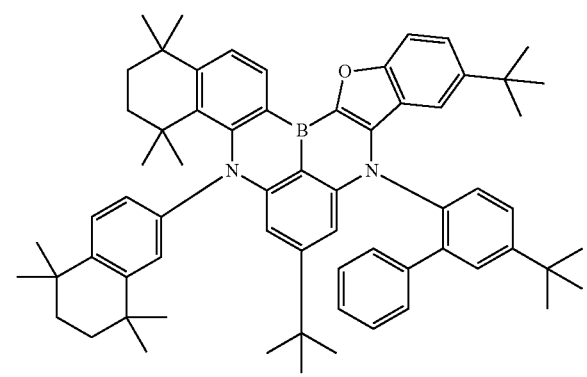

1121
-continued
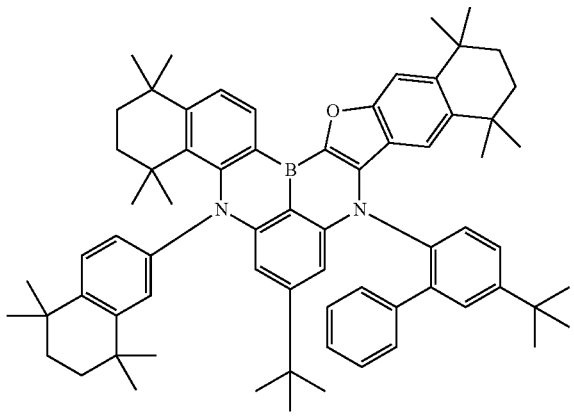
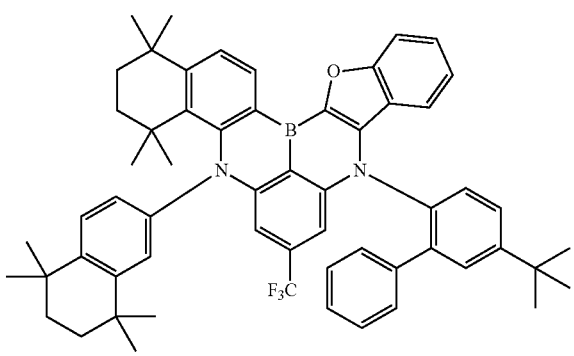
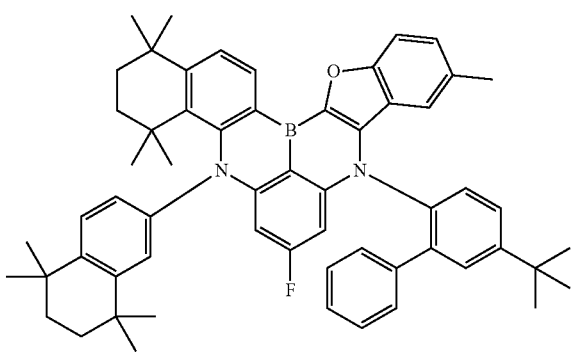
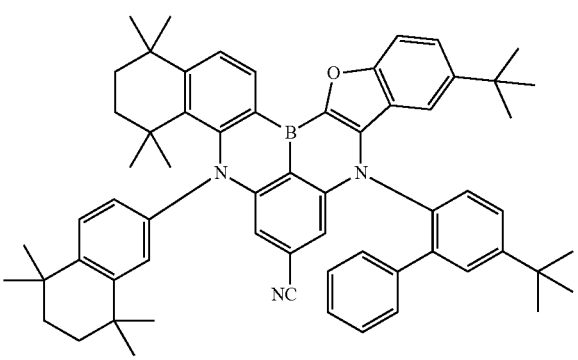
1122
-continued
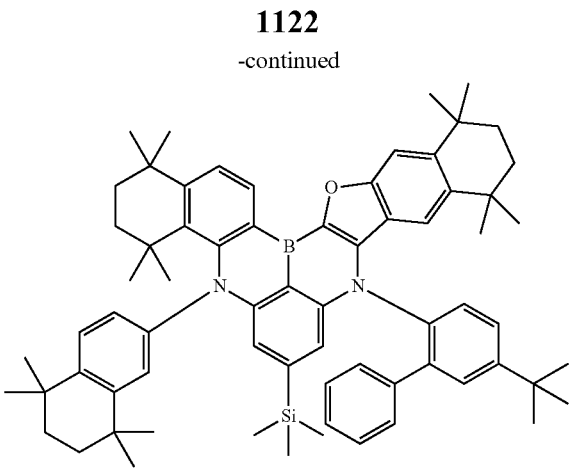
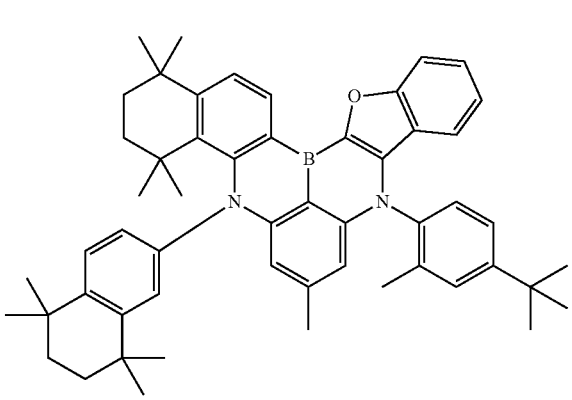
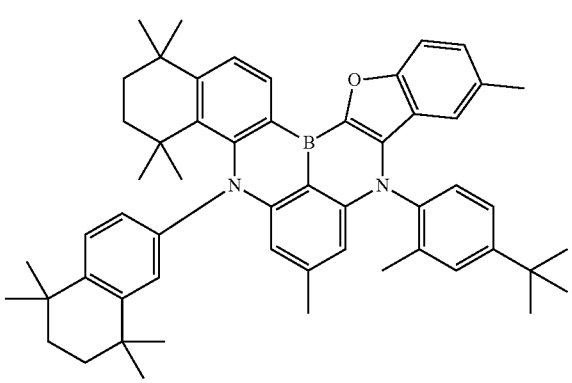
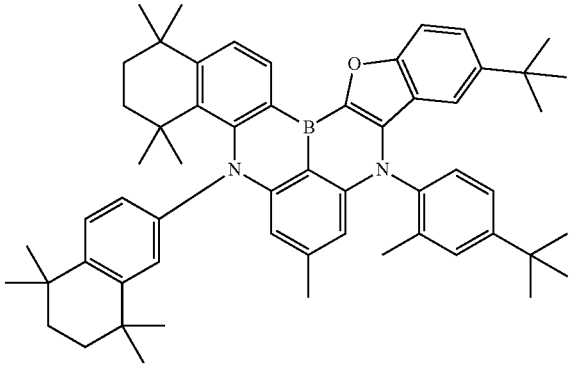

1123
-continued
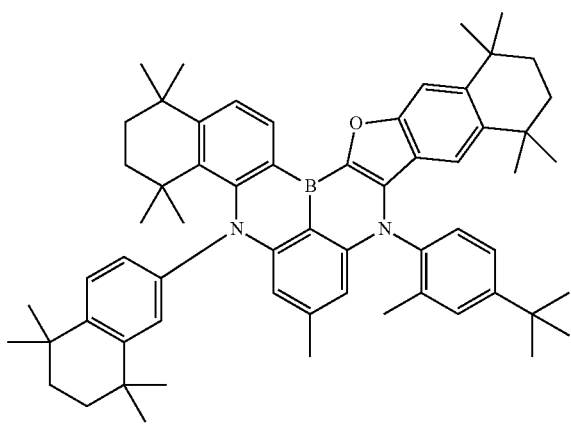

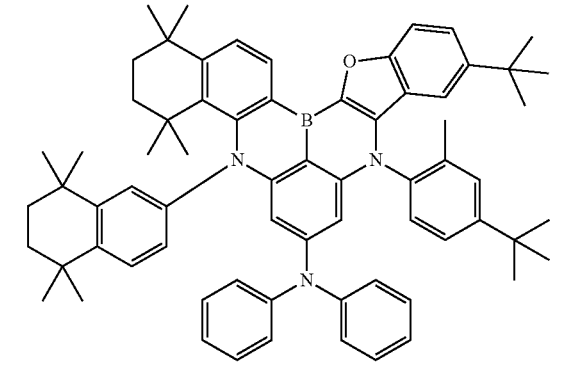
1124
-continued
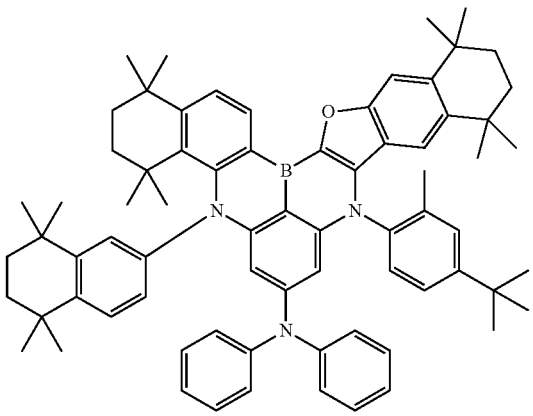
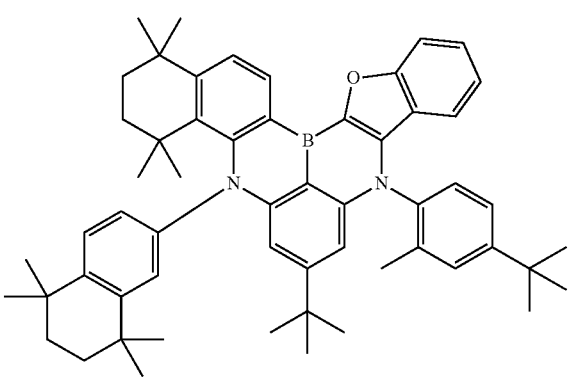
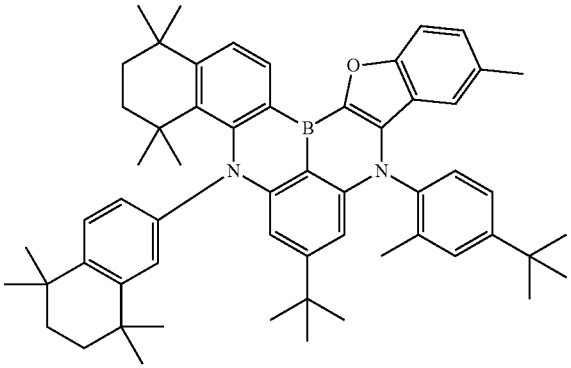
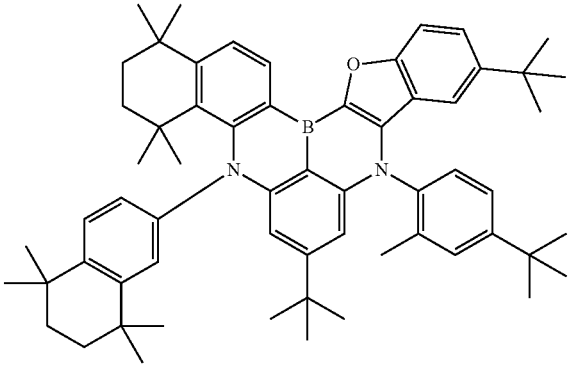

1125
-continued
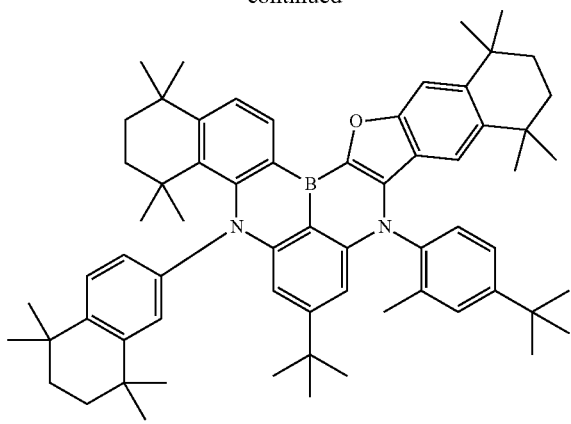
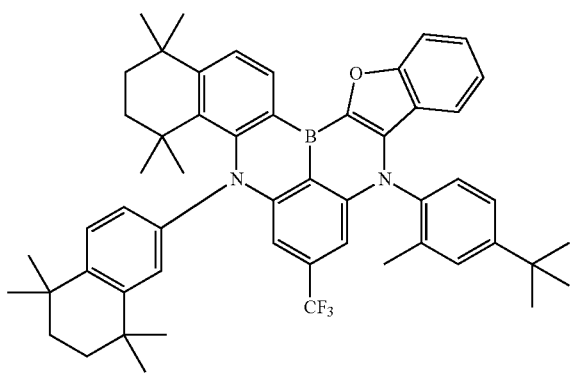
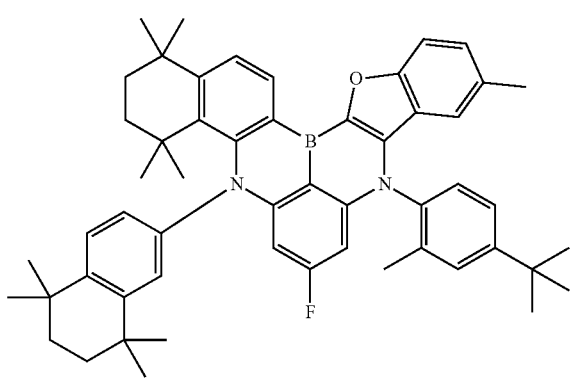
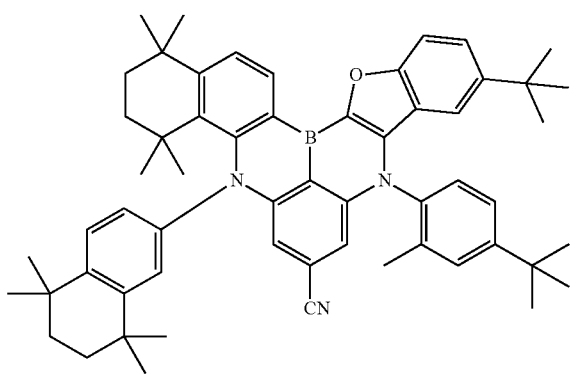
1126
-continued
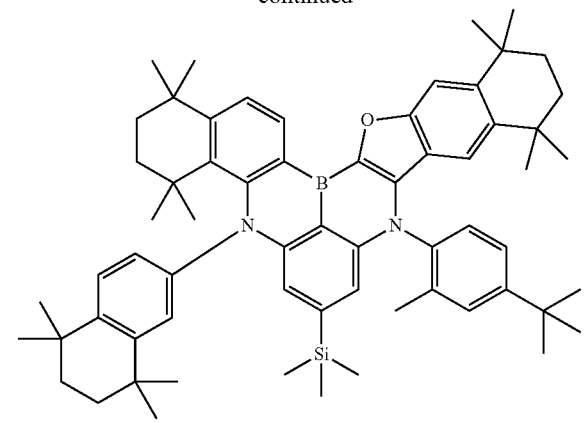
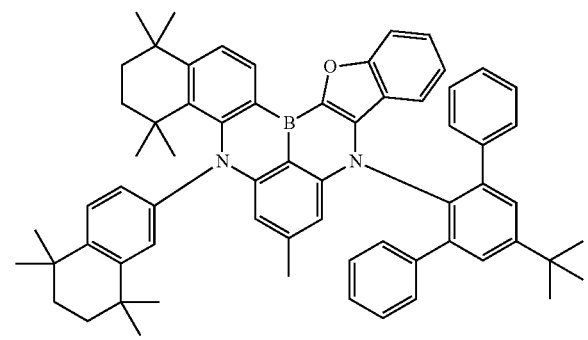
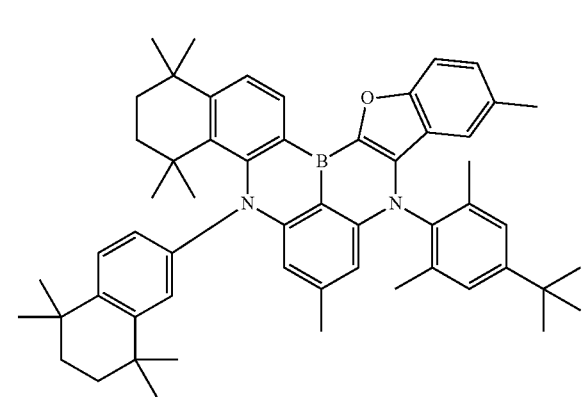
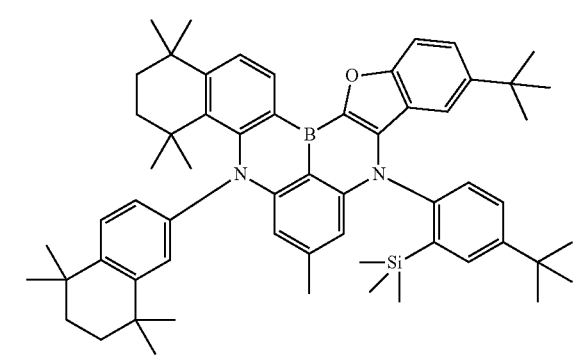

1127
-continued
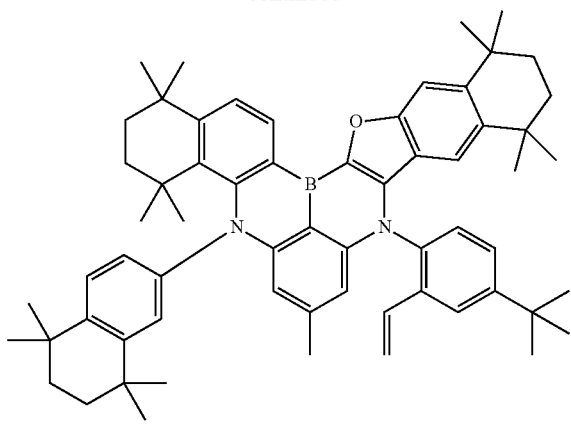
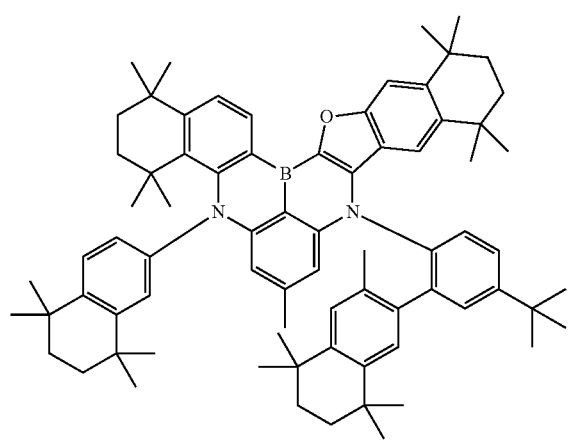
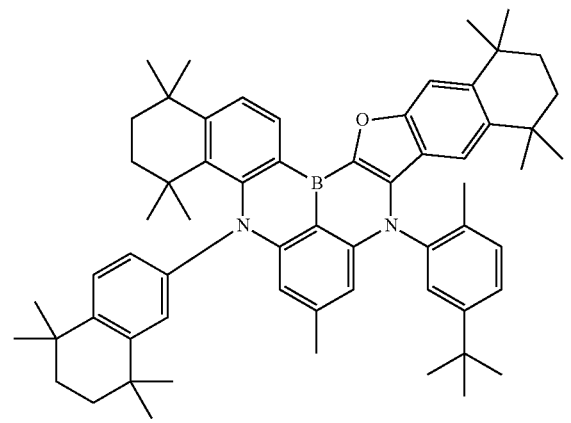
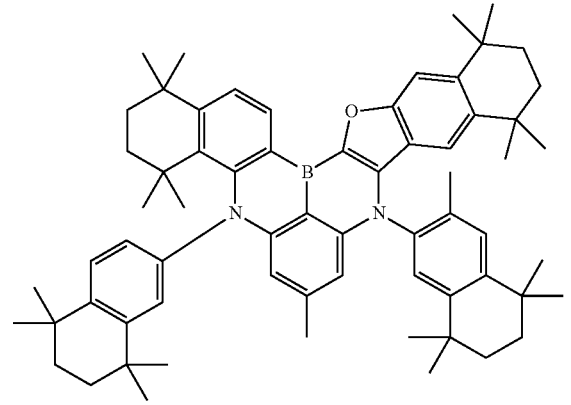
1128
-continued
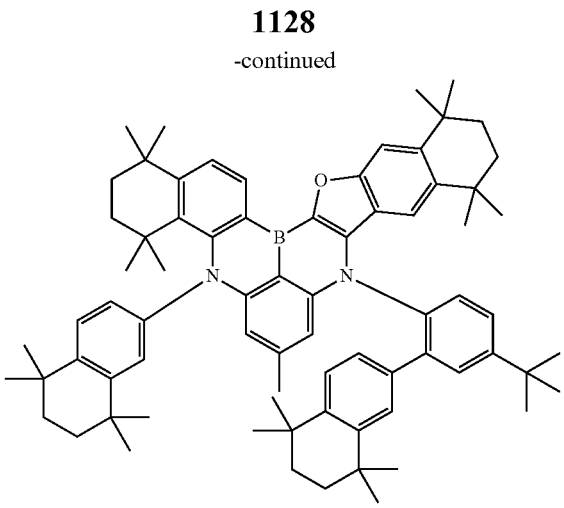
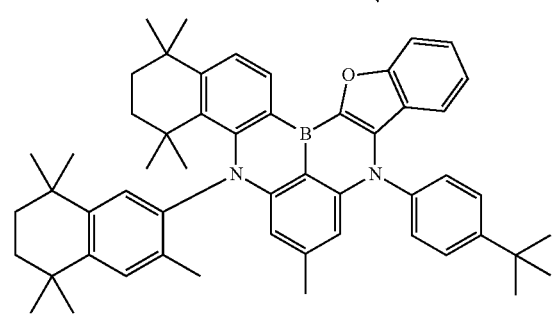
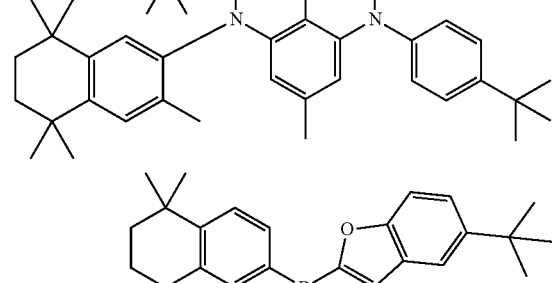
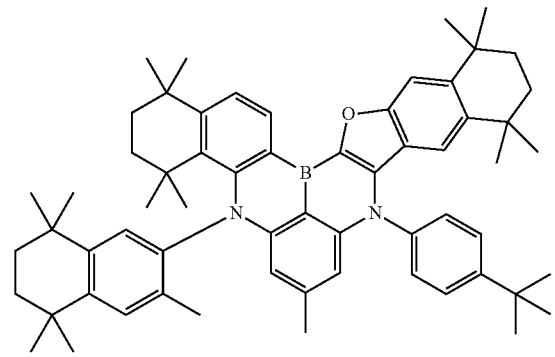

1129
-continued
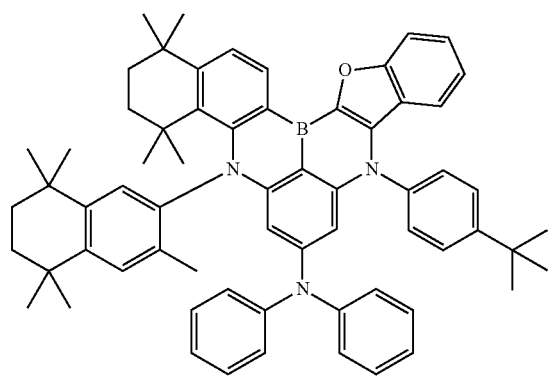
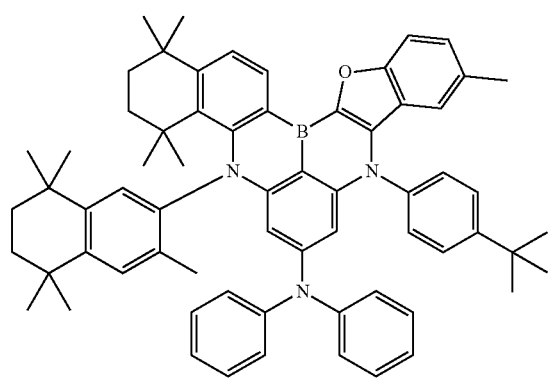
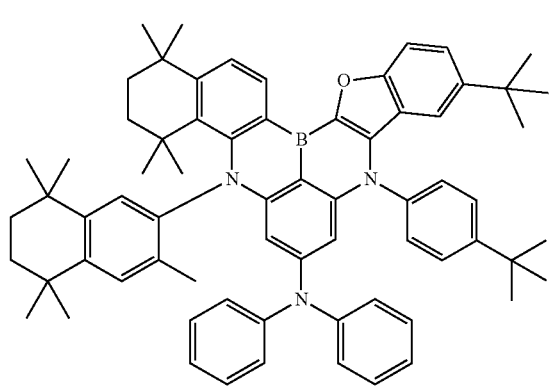
1130
-continued
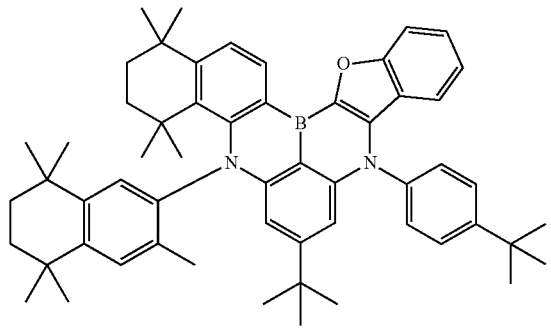
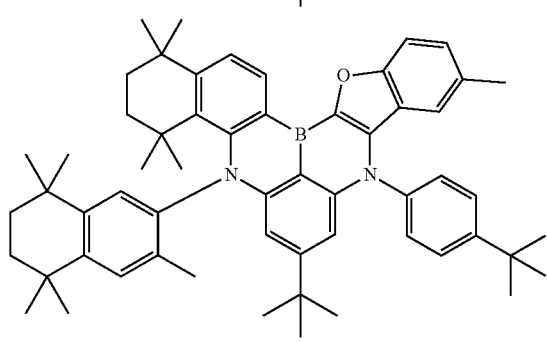
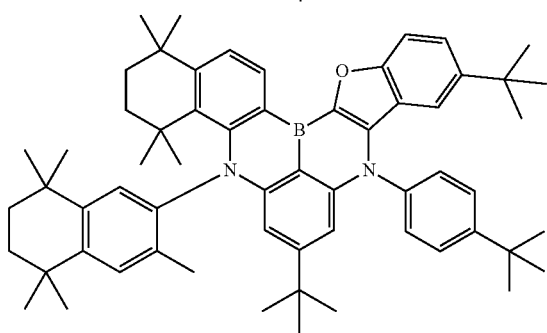
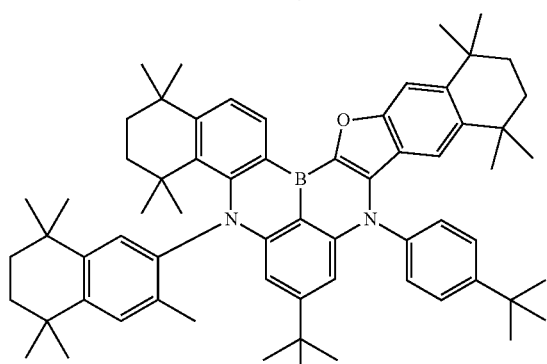
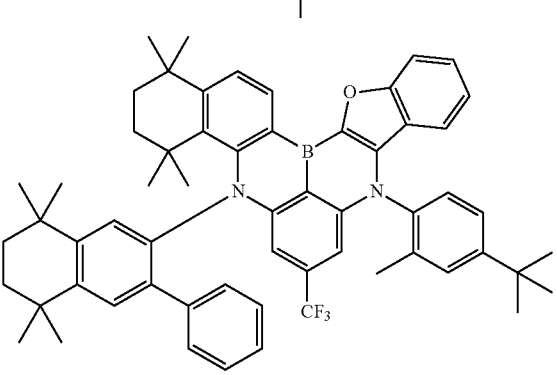

1131
-continued
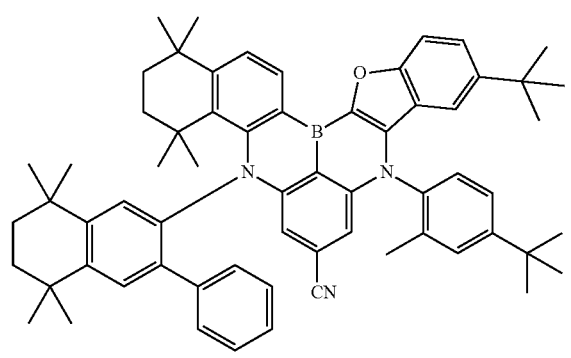
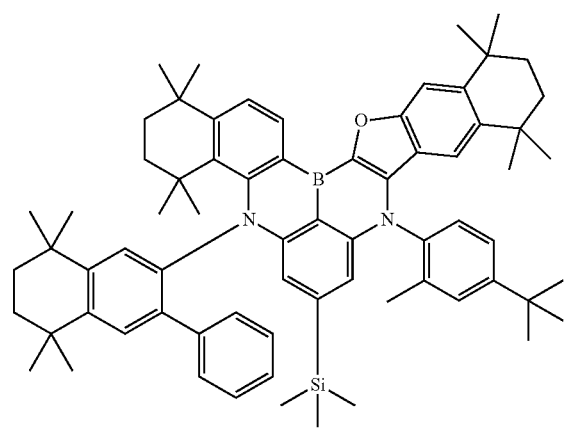
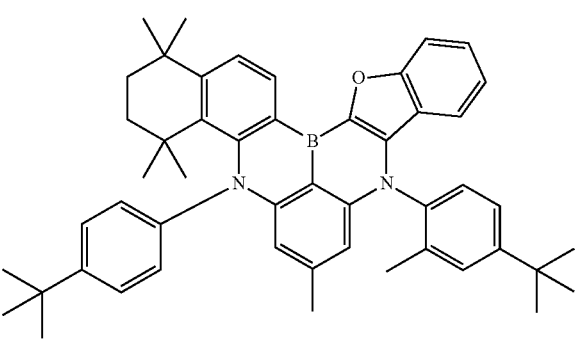
1132
-continued
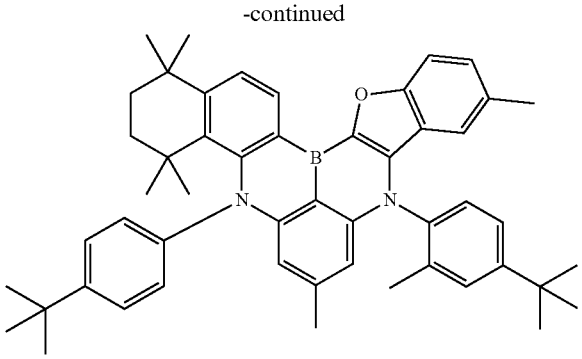
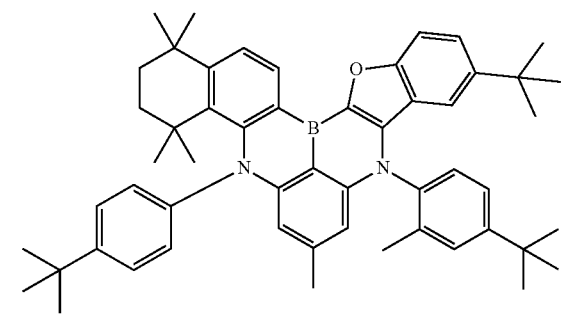
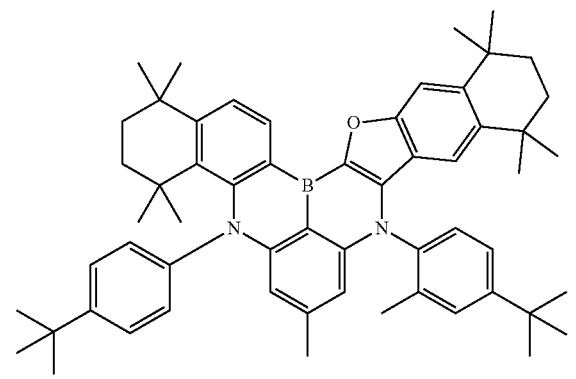
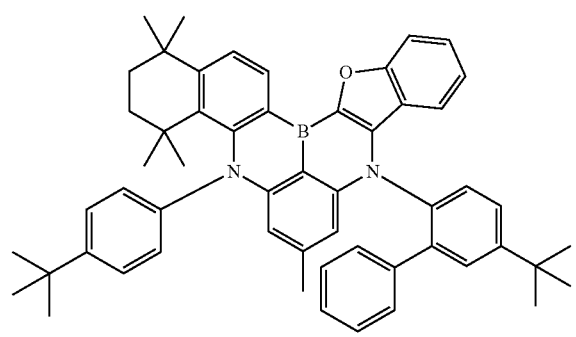
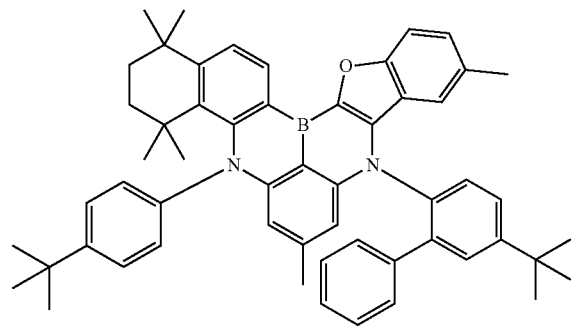

1133
-continued
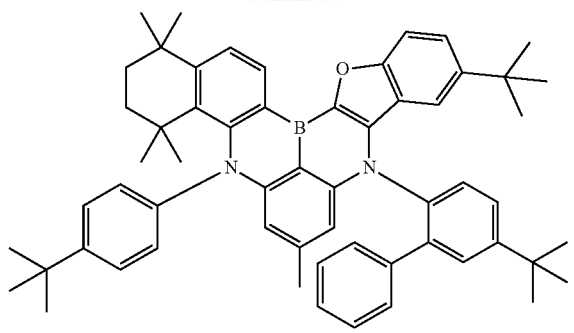
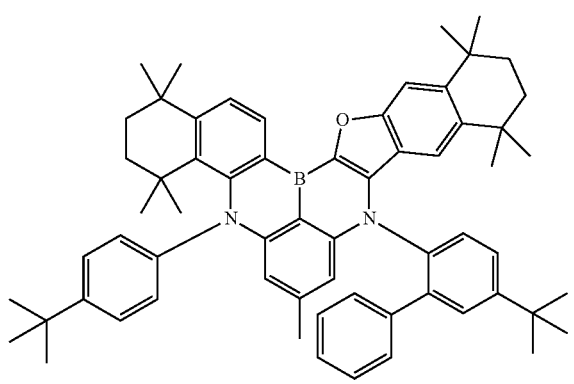
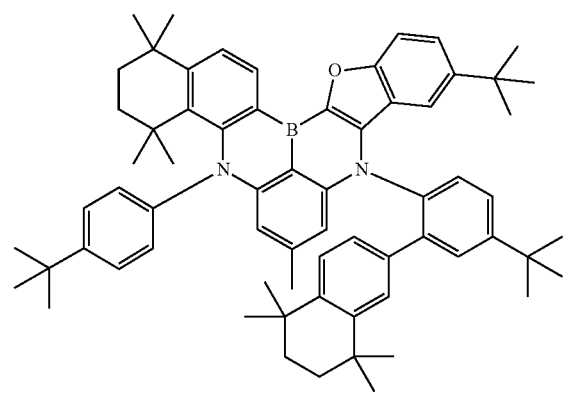
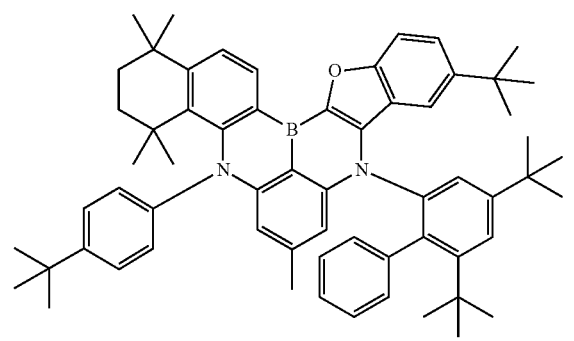
1134
-continued
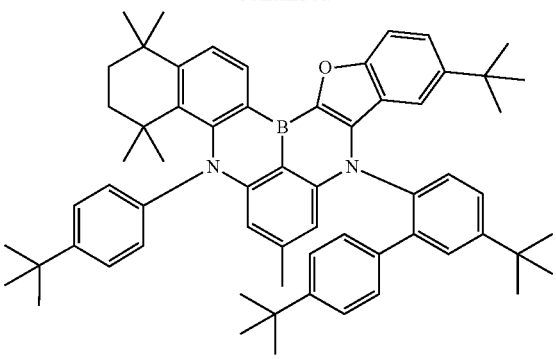
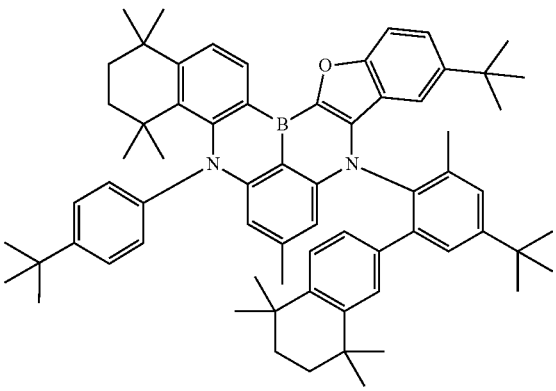
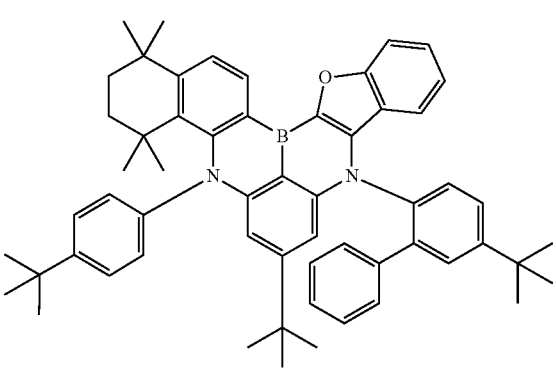
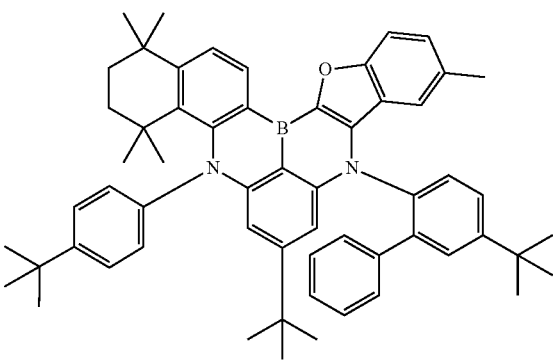

1135
-continued
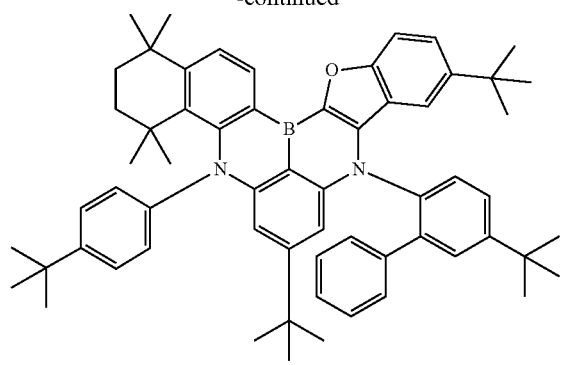
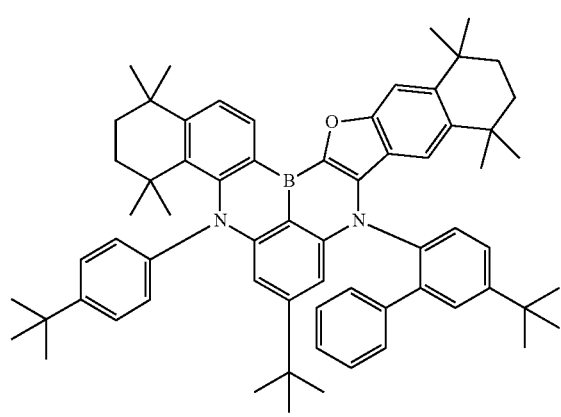
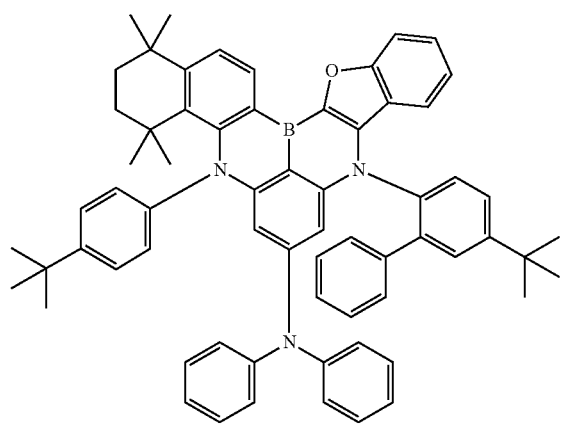
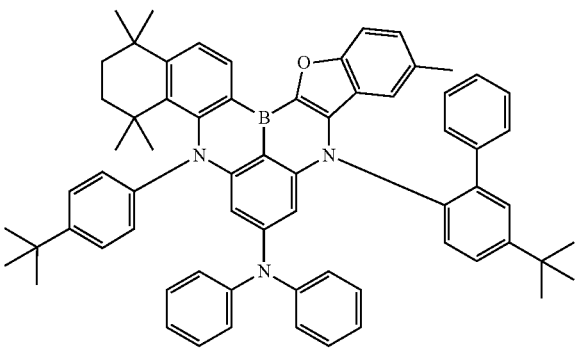
1136
-continued
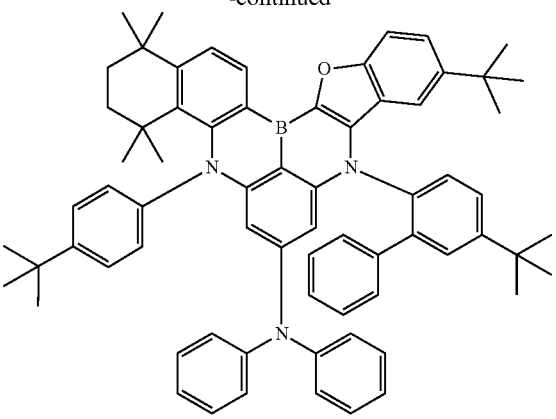
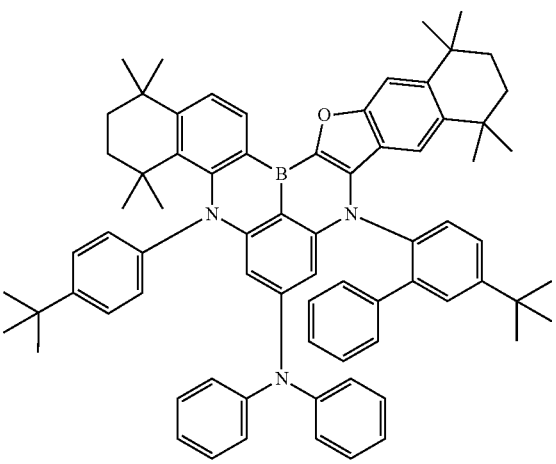
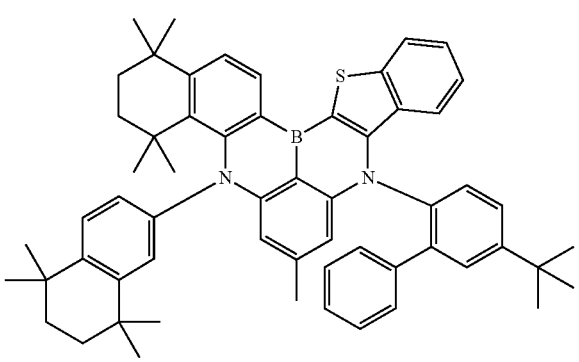
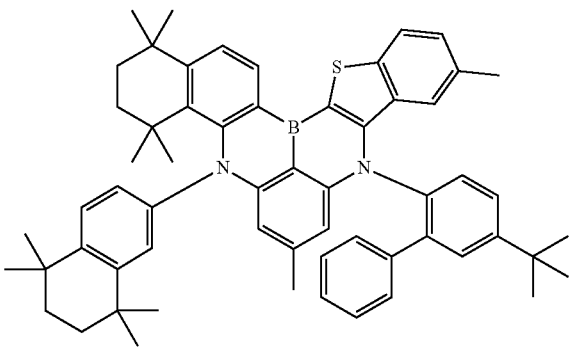

1137
-continued
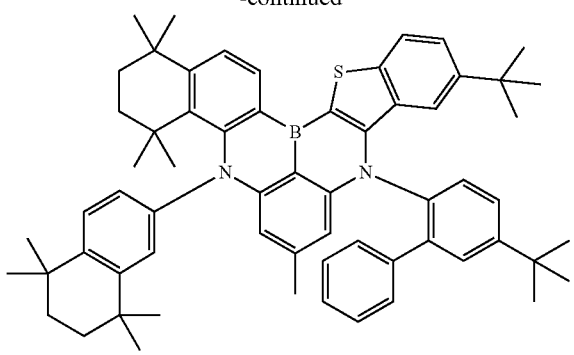
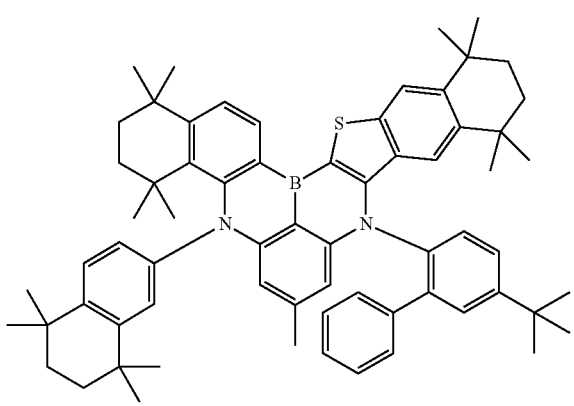
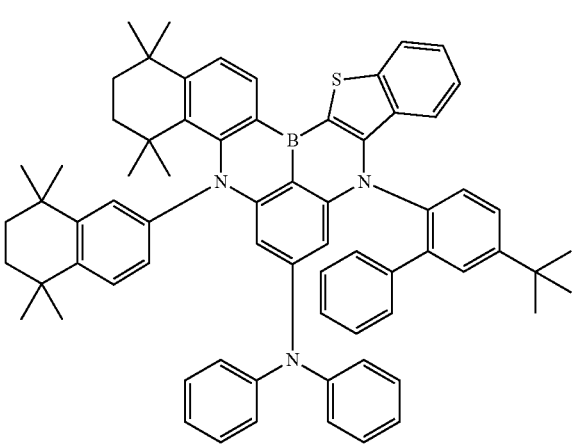
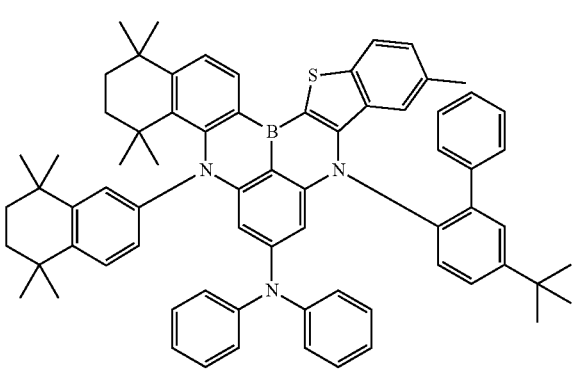
1138
-continued
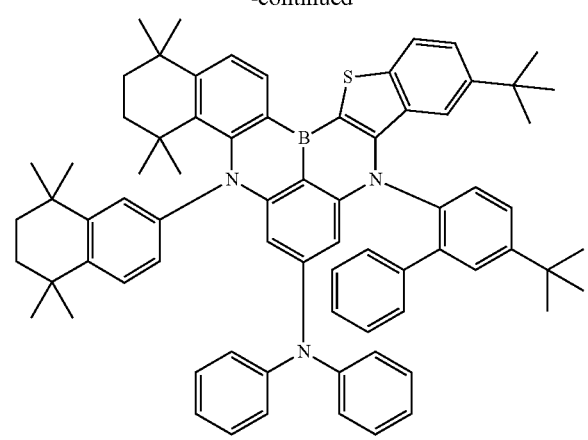
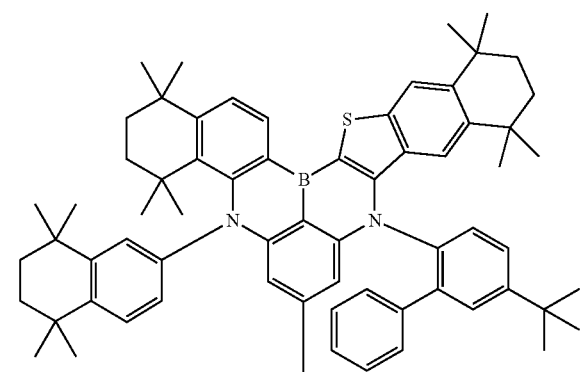
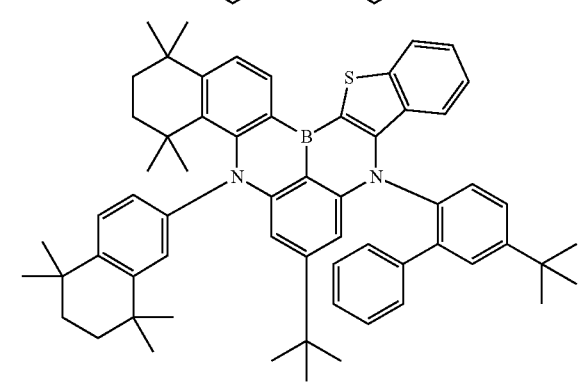
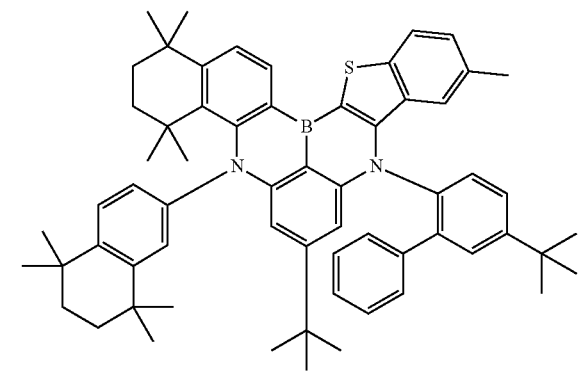

| 1139 -continued | 1140 -continued |
|---|---|
| 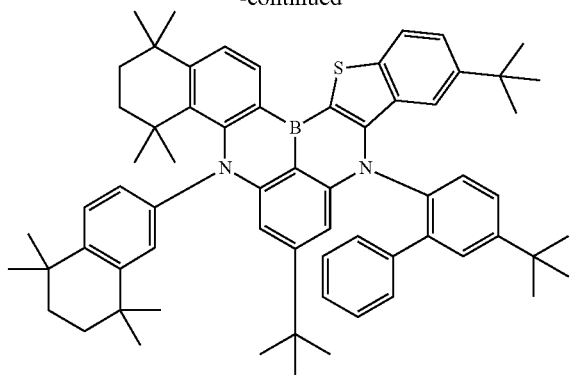 | 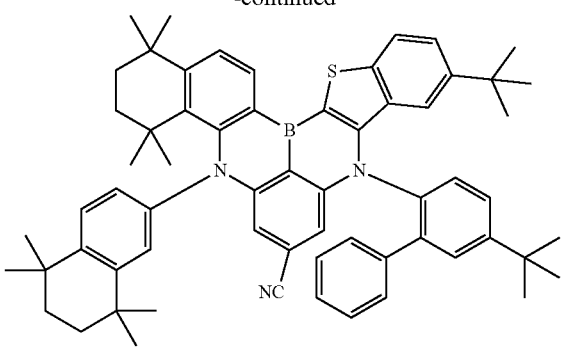 |
| 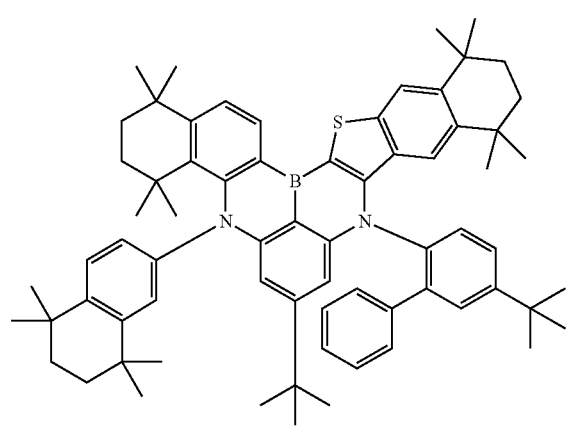 | 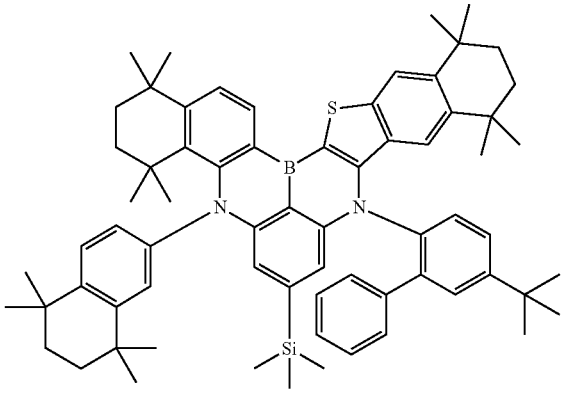 |
| 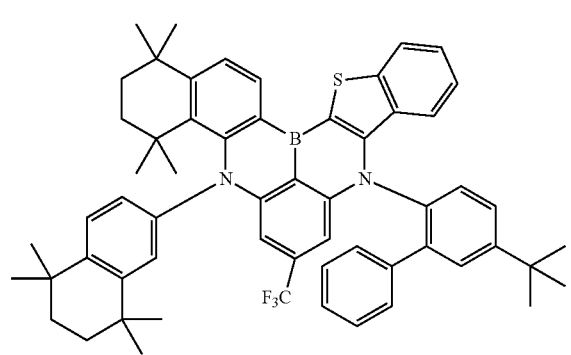 | 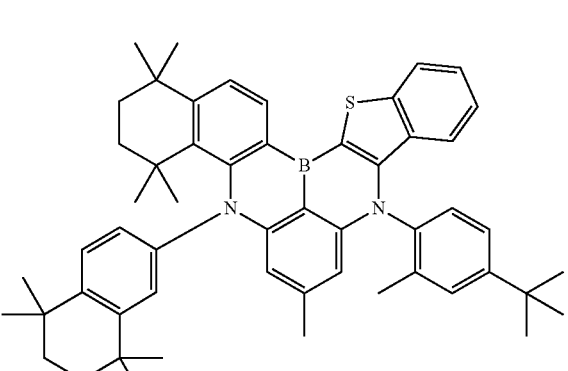 |
| 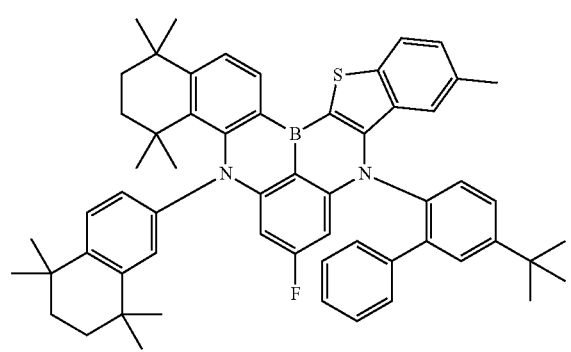 | 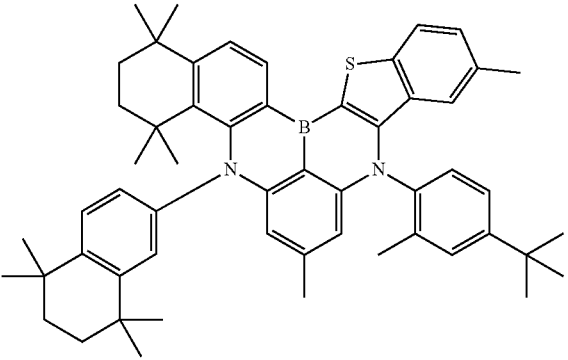 |

1141
-continued
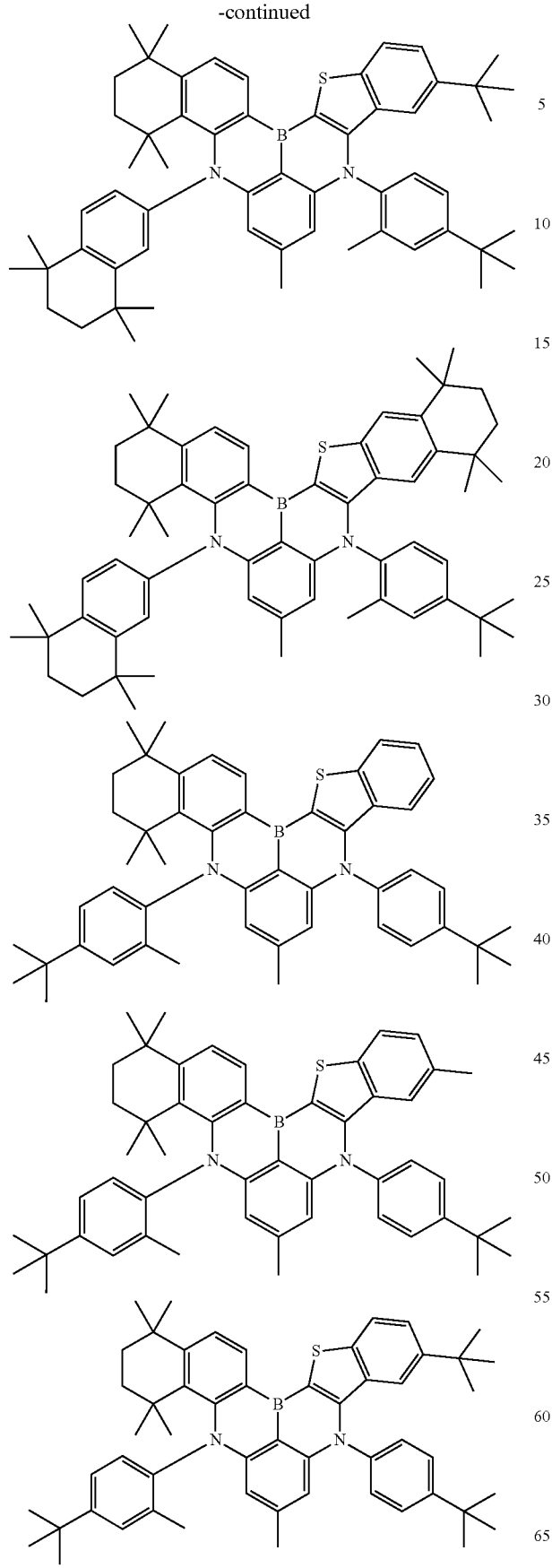
1142
-continued
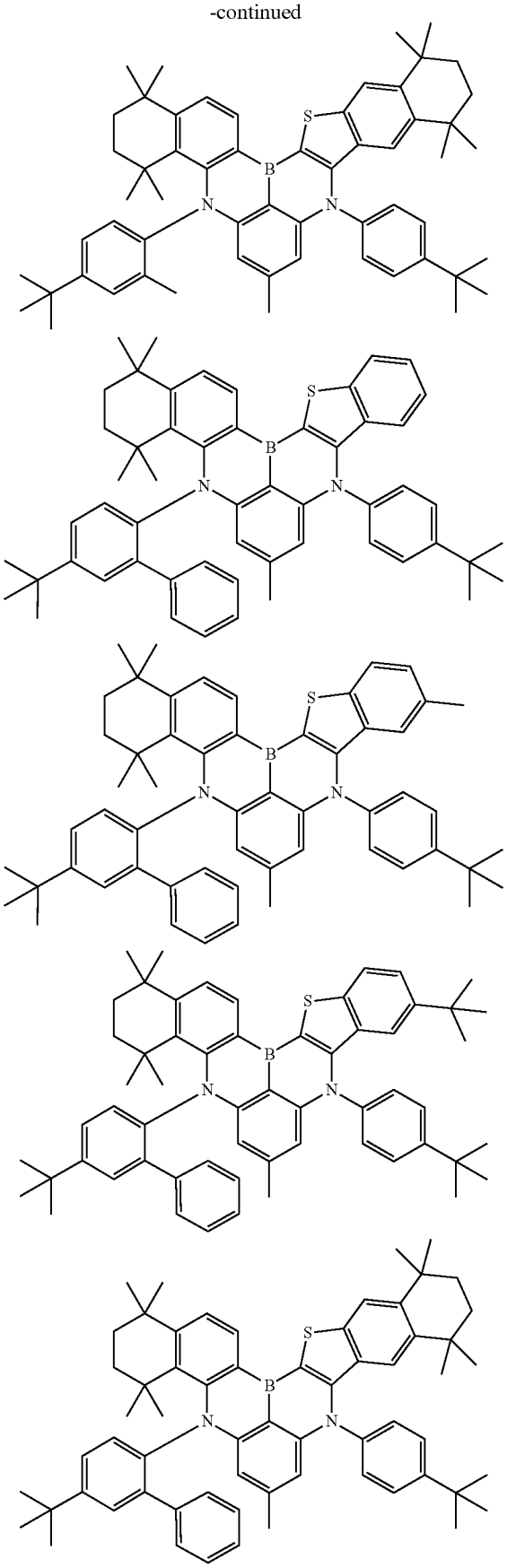

1143
-continued
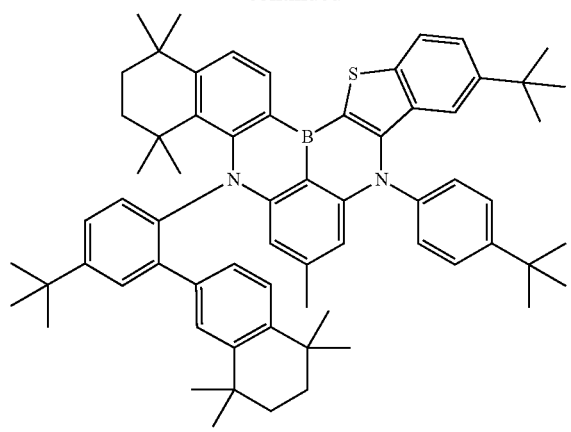
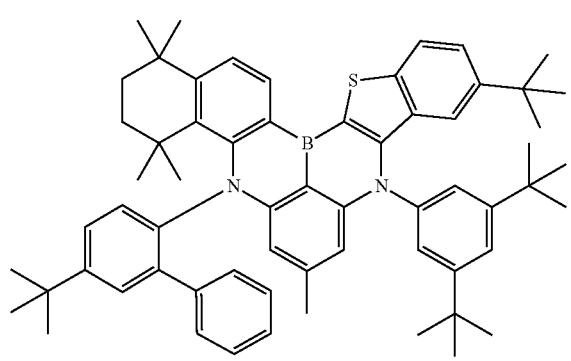
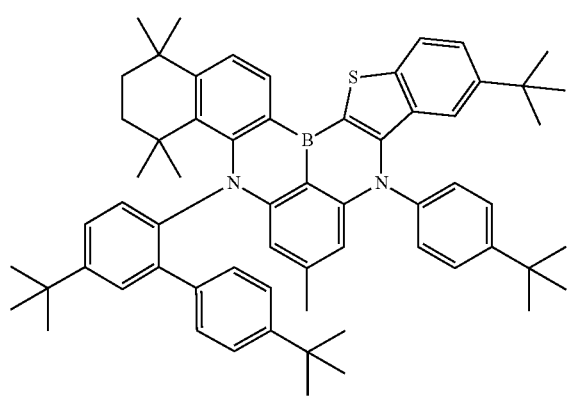
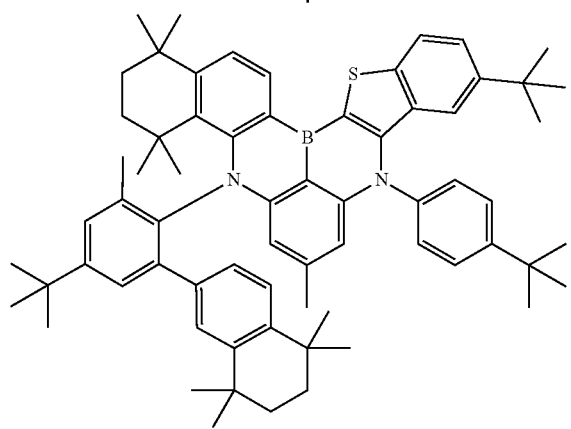
1144
-continued
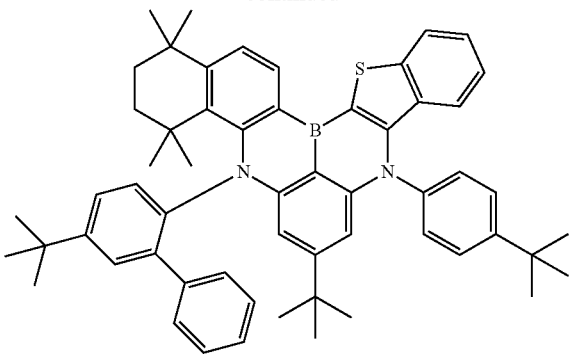
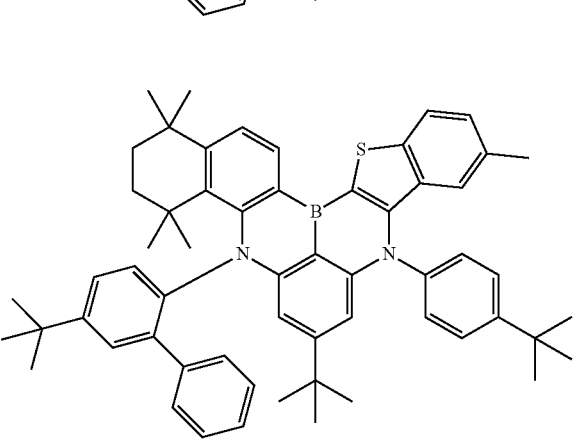
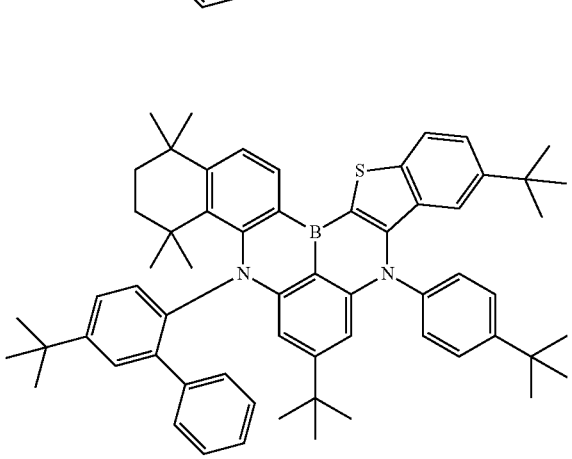
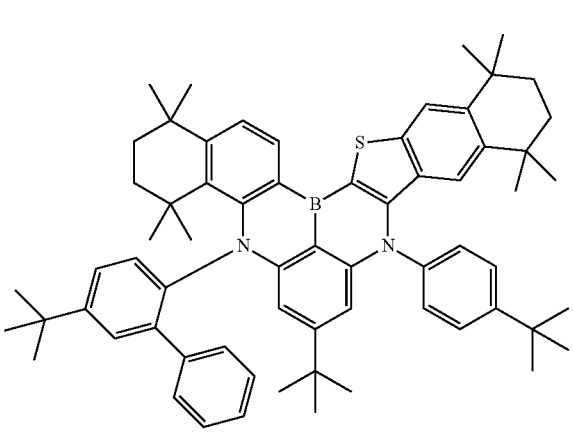

1145
-continued
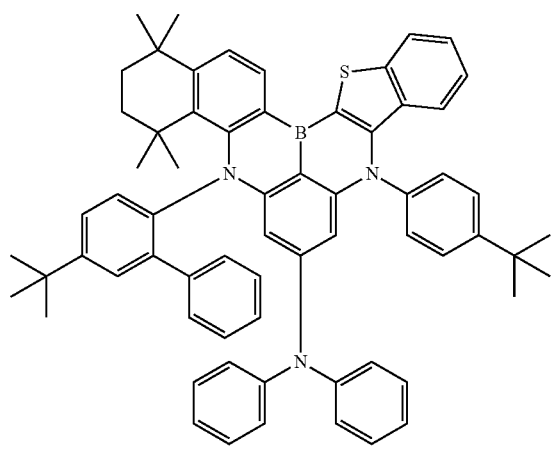
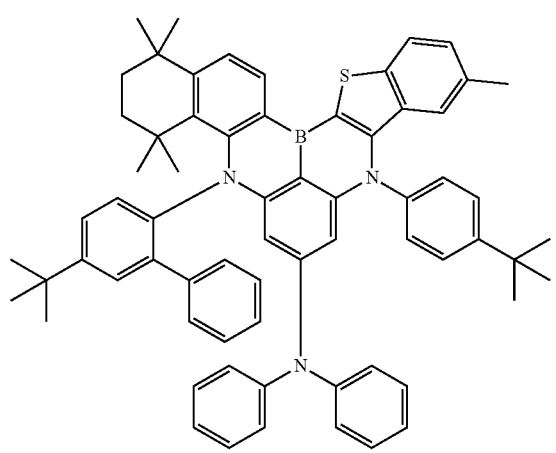
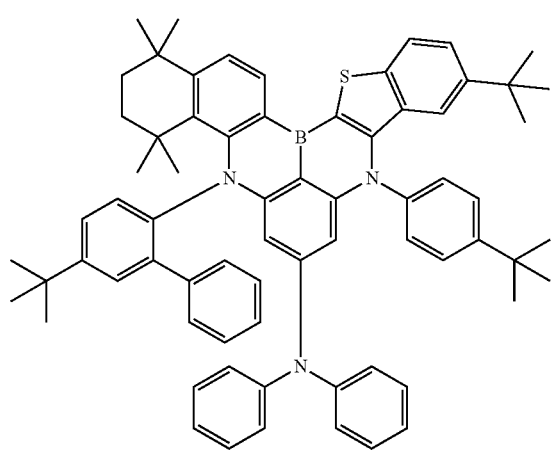
1146
-continued
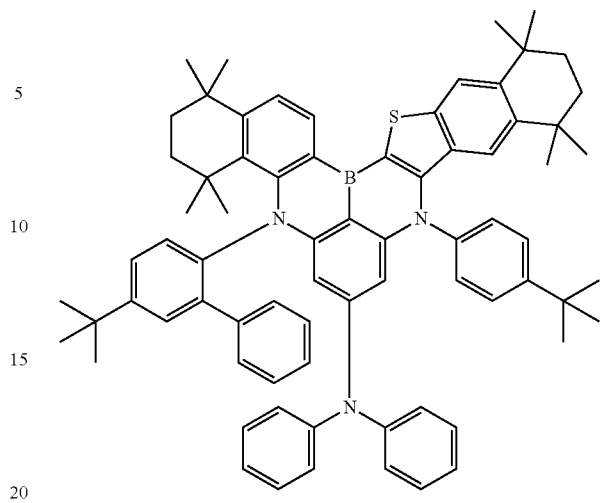
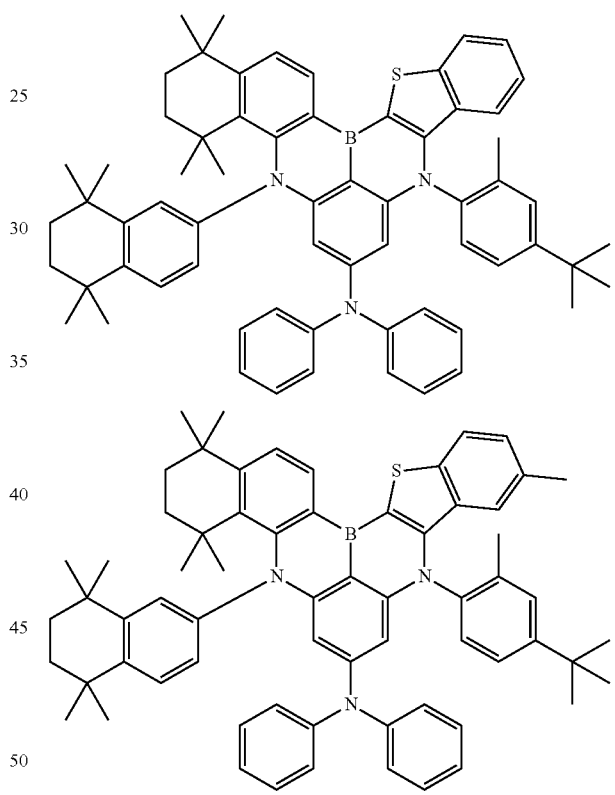
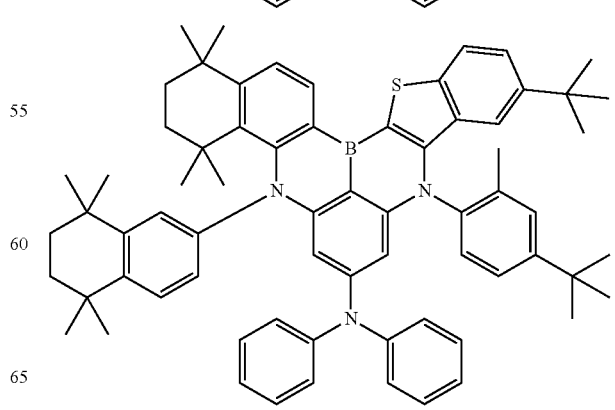

1147
-continued
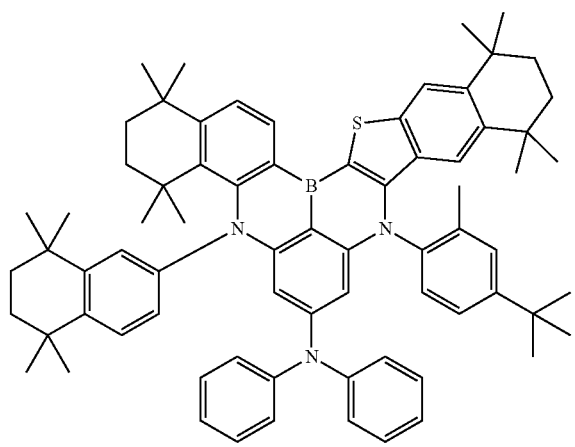
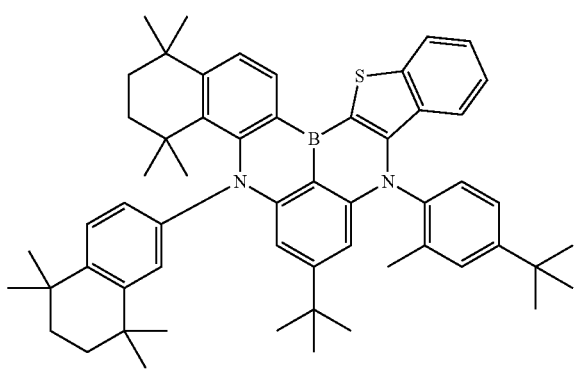
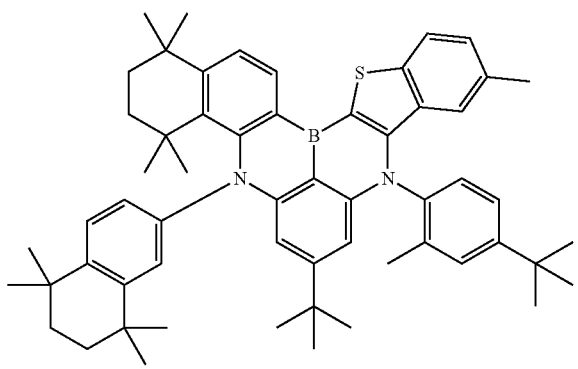
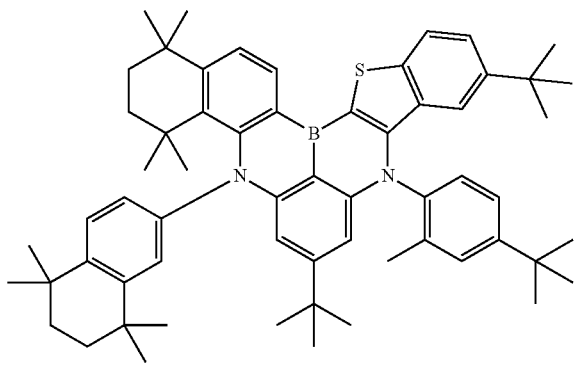
1148
-continued
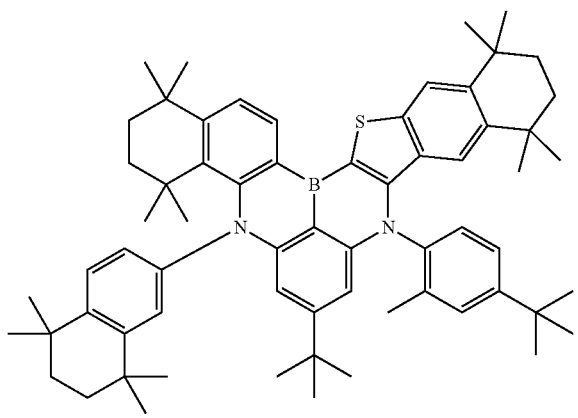
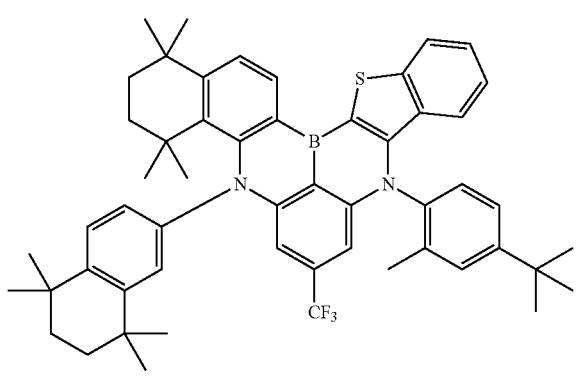
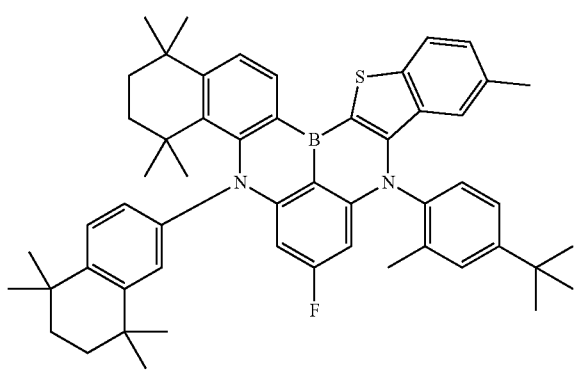
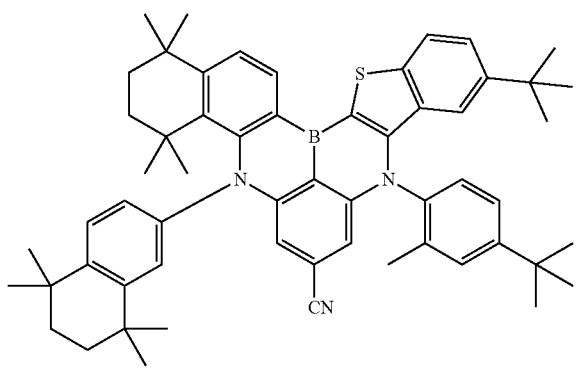

1149
-continued
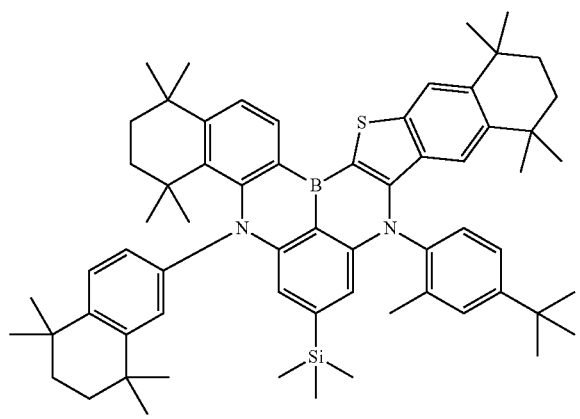
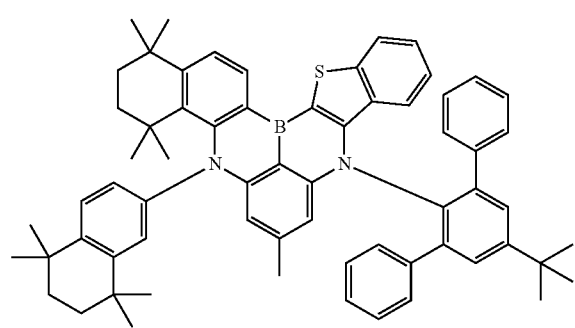
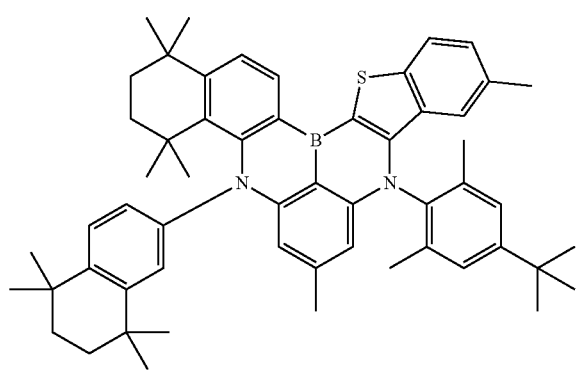
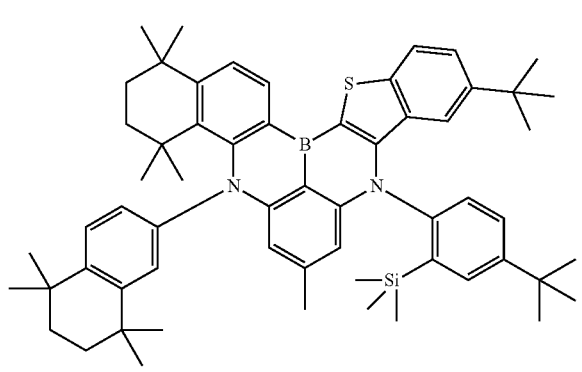
1150
-continued
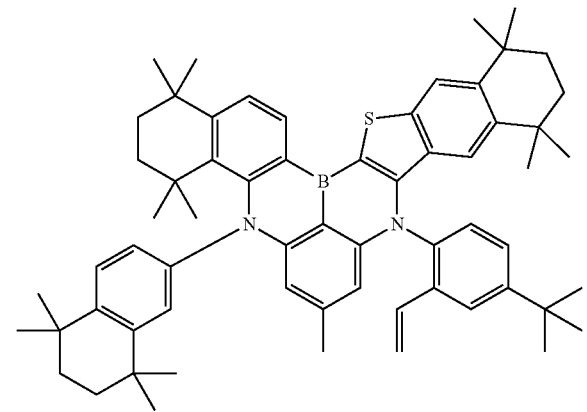
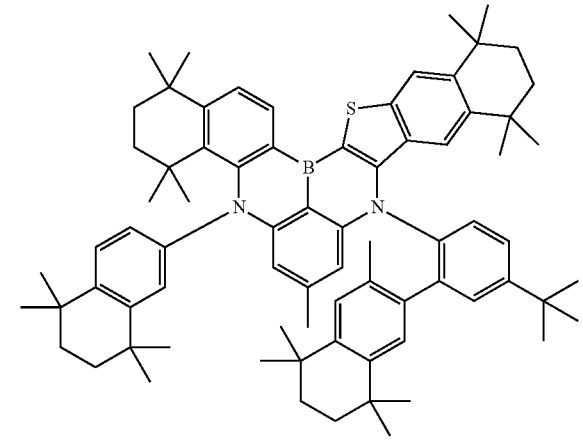
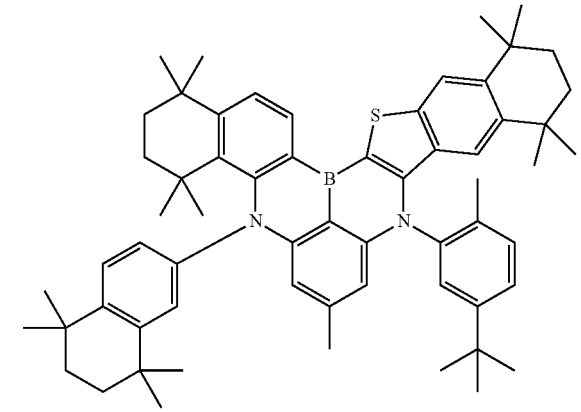
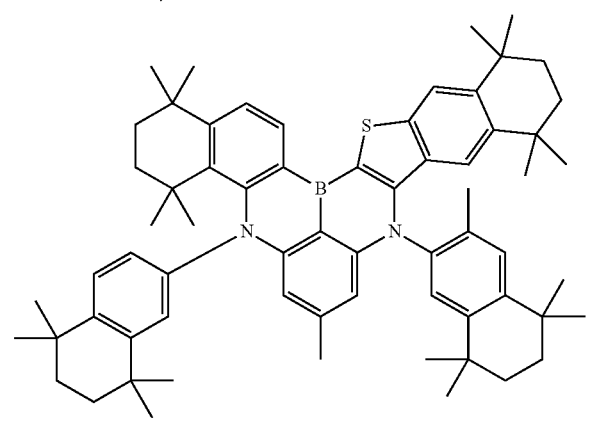

US 11,780,856 B2
| 1151 | 1152 |
|---|---|
| -continued | -continued |
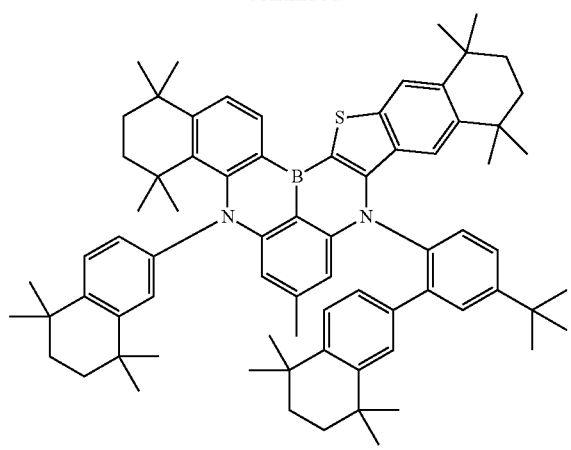
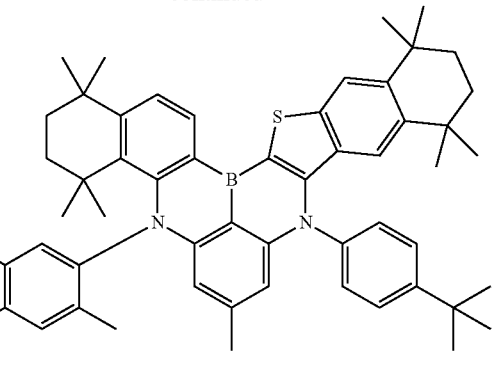
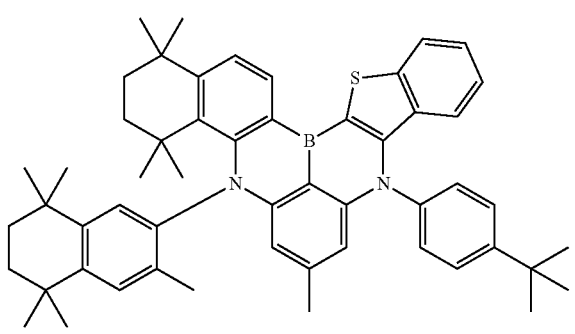
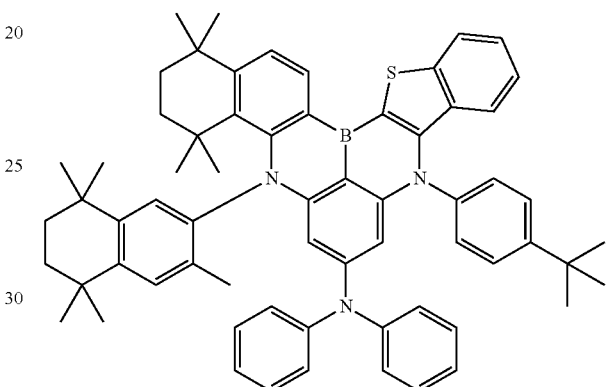
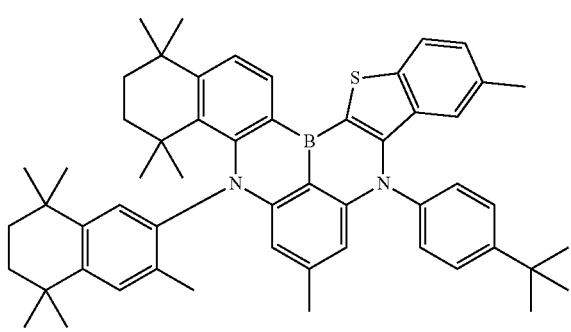
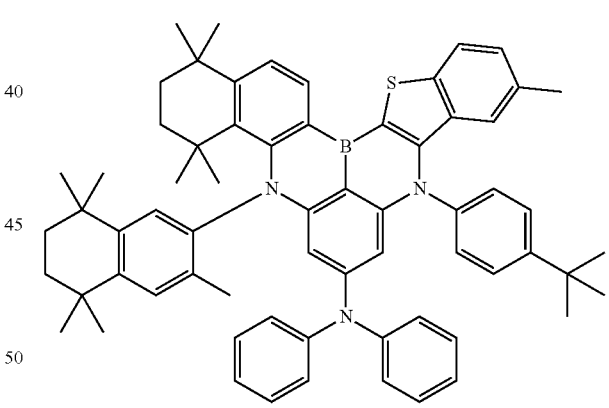
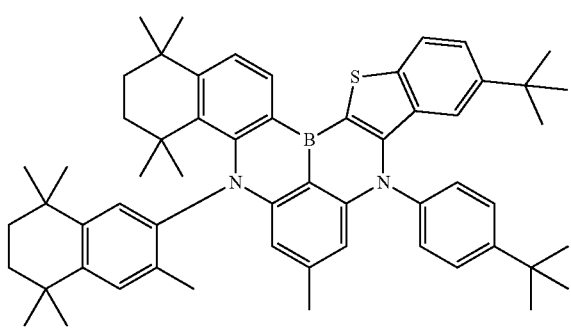
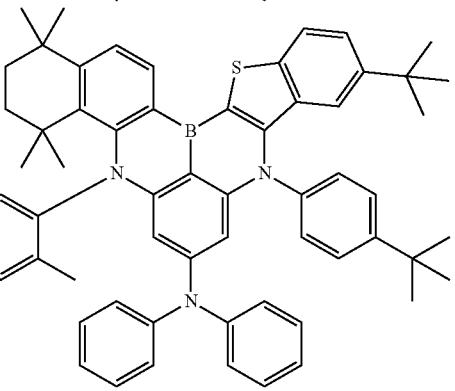

1153
-continued
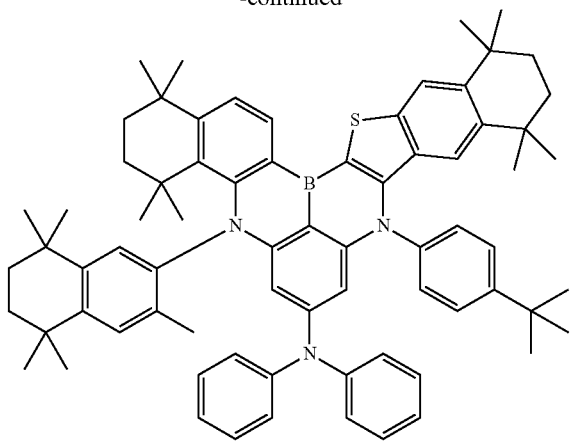
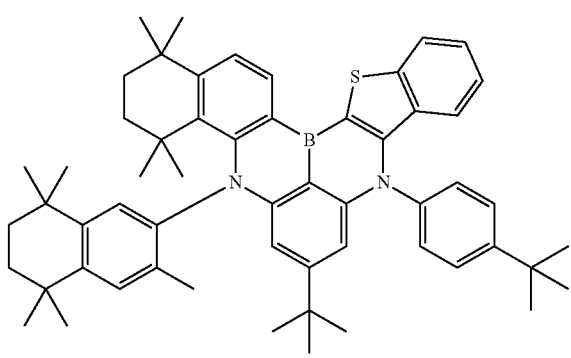
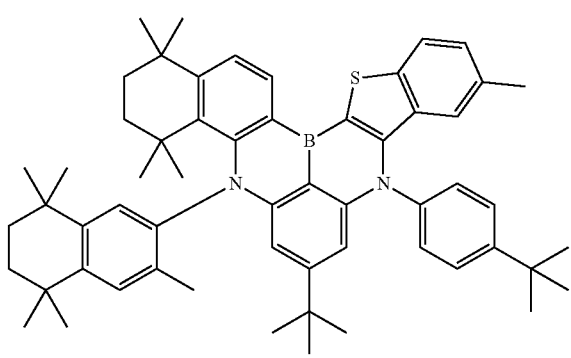
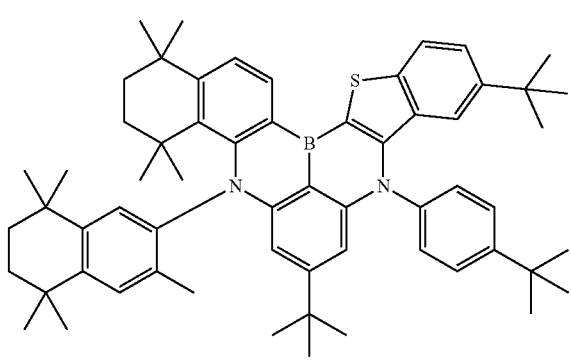
1154
-continued
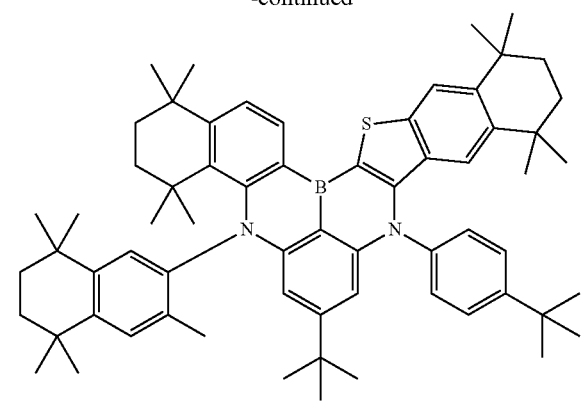
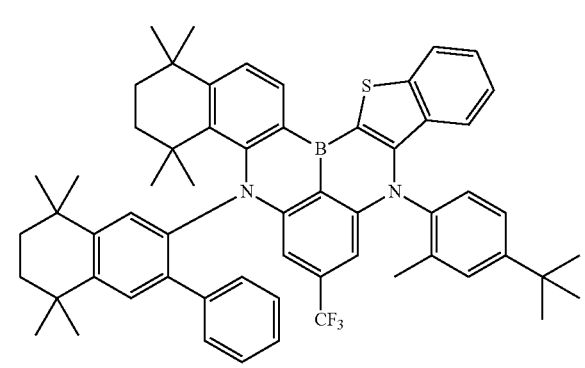
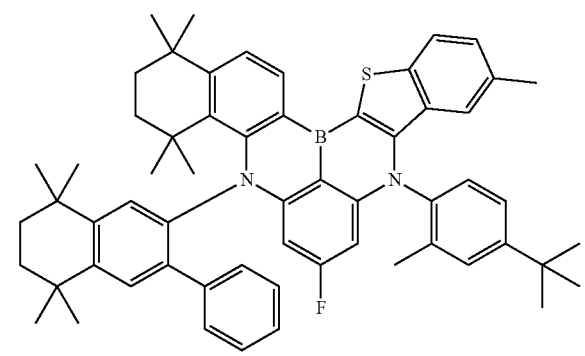
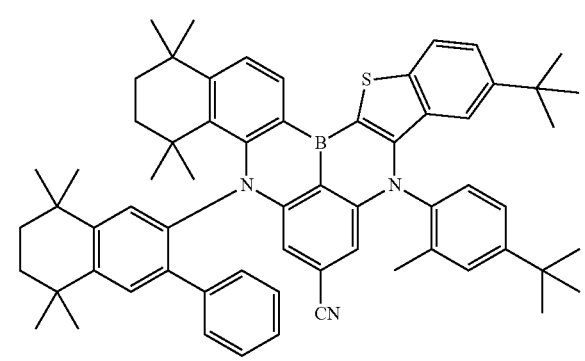

1155
-continued
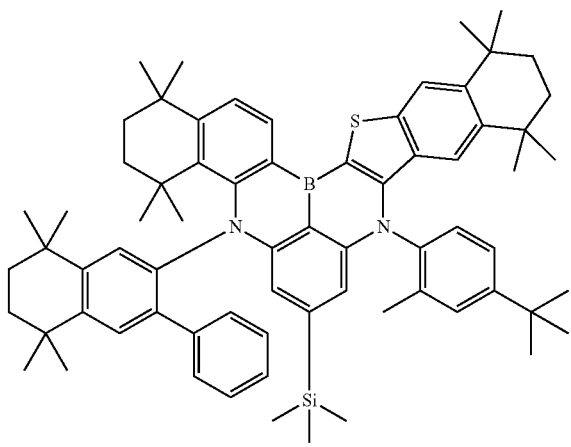
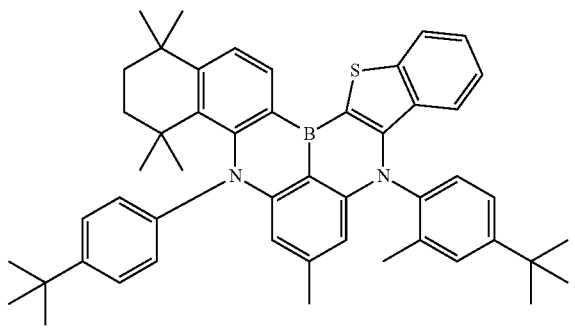
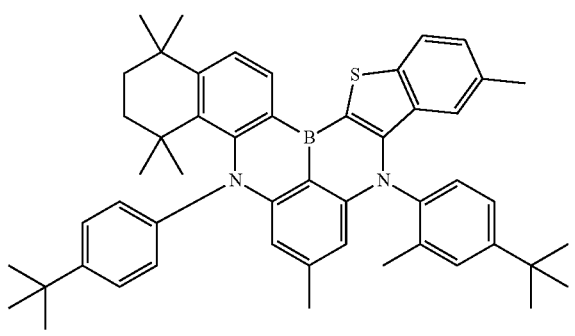
1156
-continued
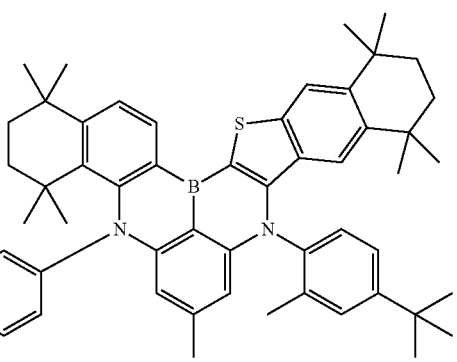
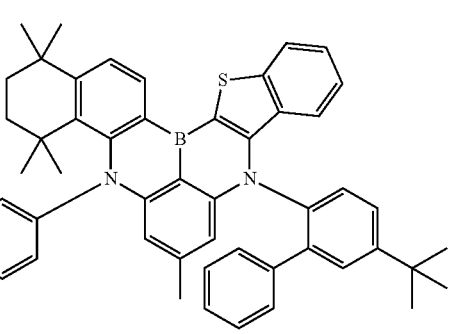
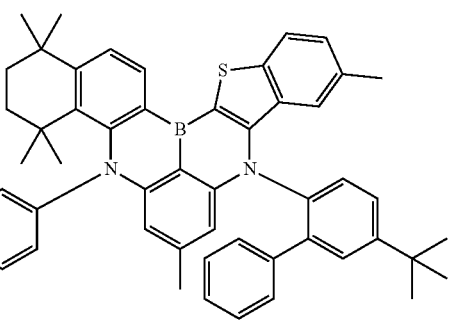
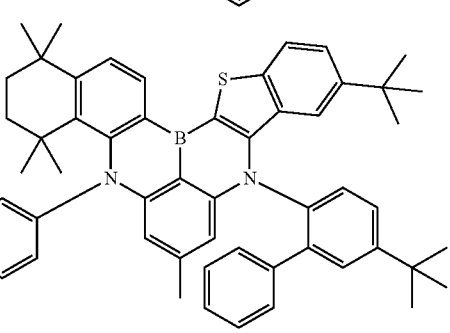
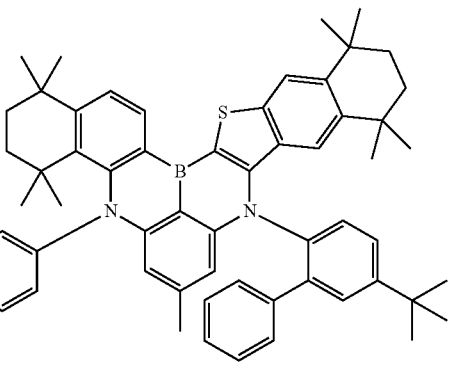

| 1157 -continued | 1158 -continued |
|---|---|
| 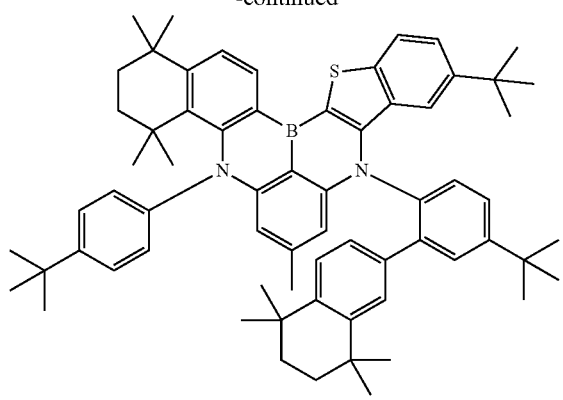 | 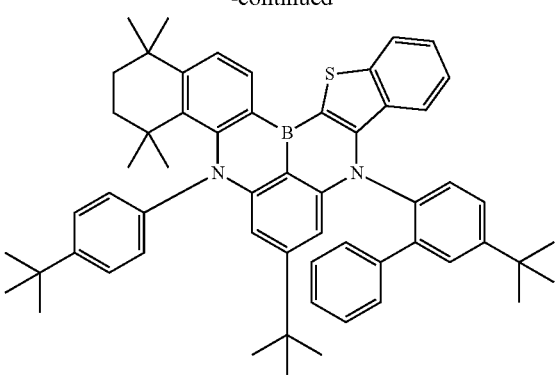 |
| 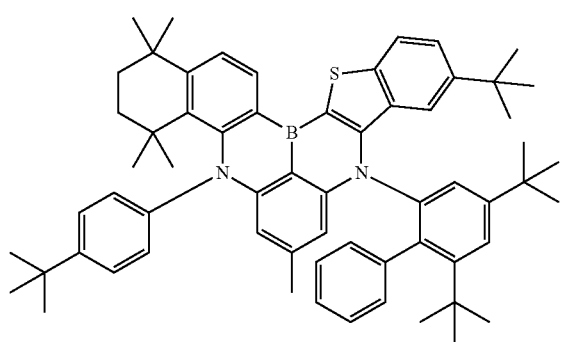 | 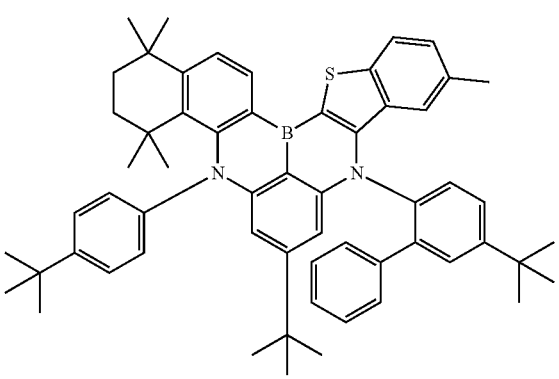 |
| 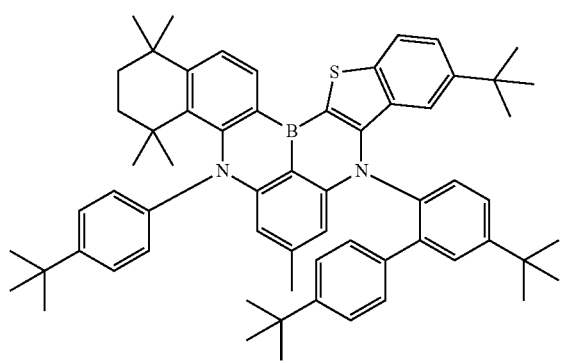 | 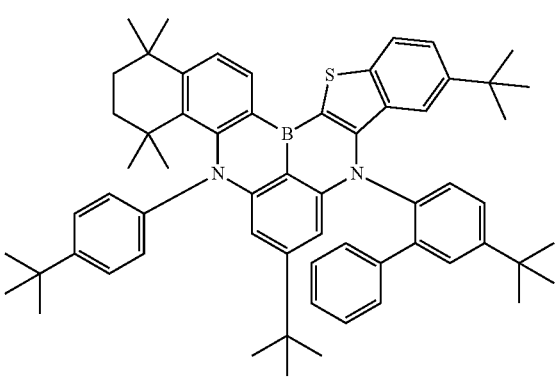 |
| 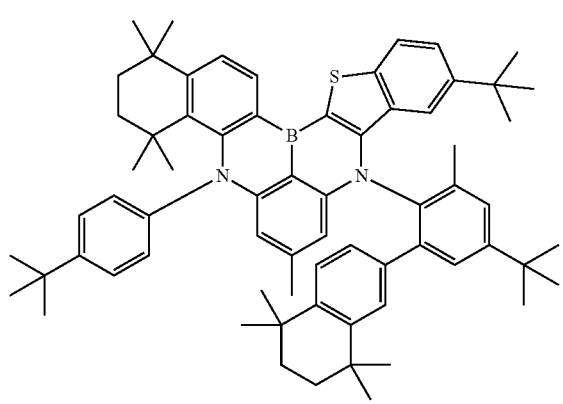 | 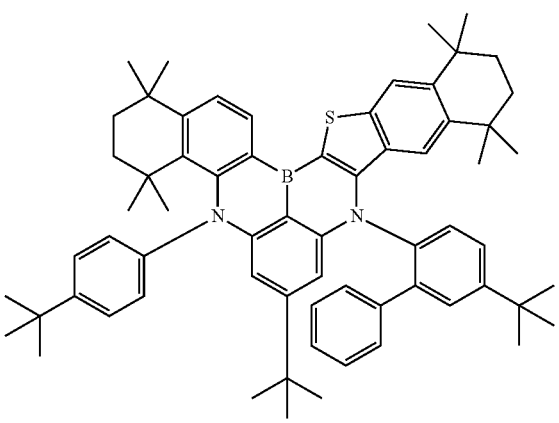 |

| 1159 -continued | 1160 -continued |
|---|---|
| 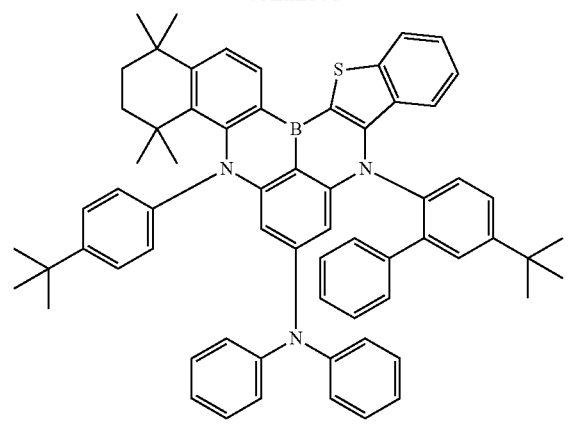 | 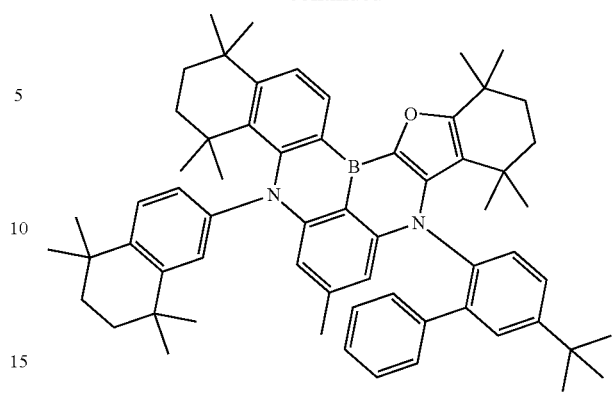 |
| 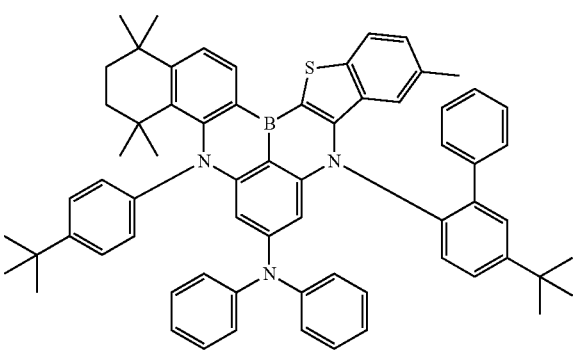 | 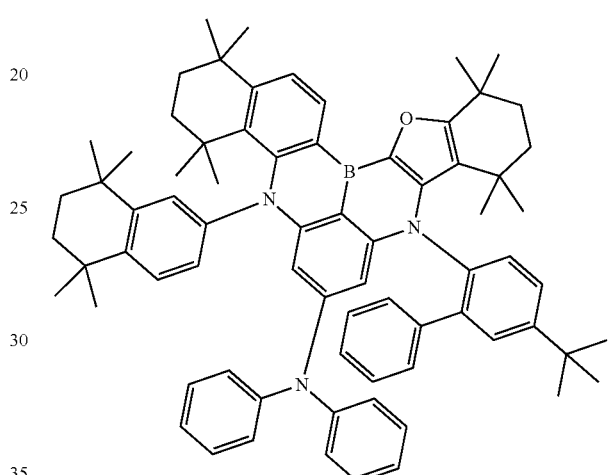 |
| 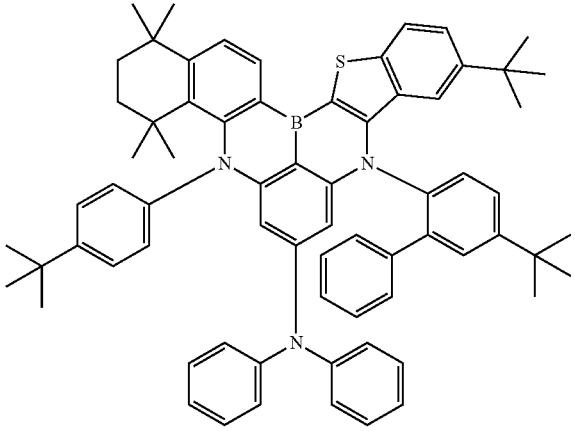 | 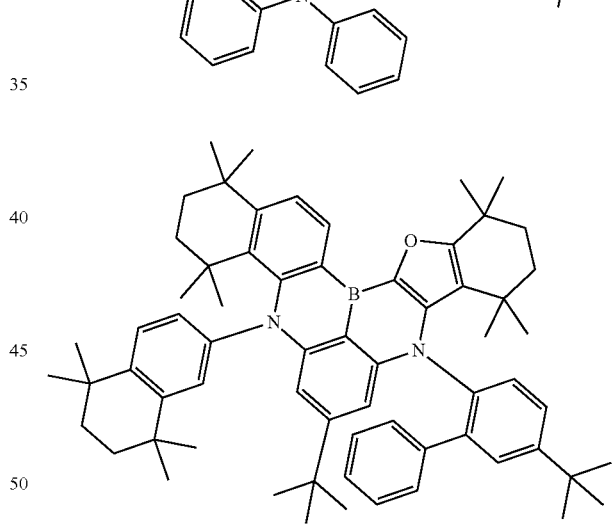 |
| 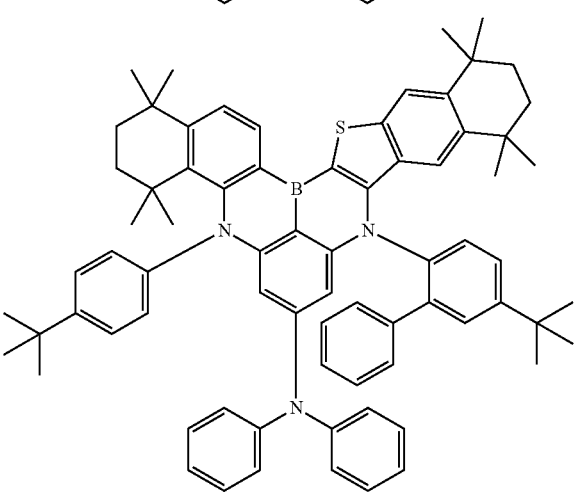 | 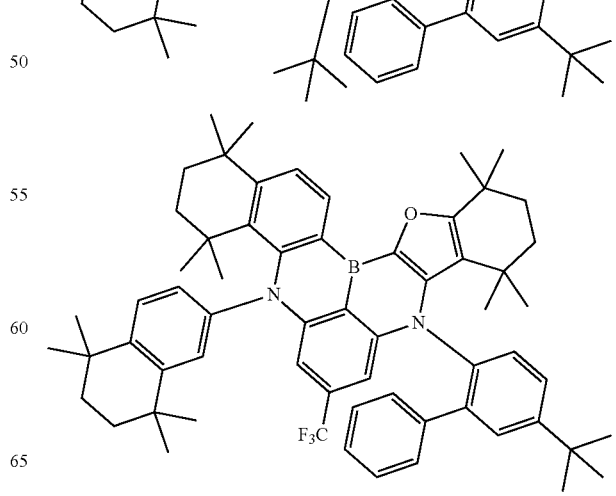 |

1161
-continued
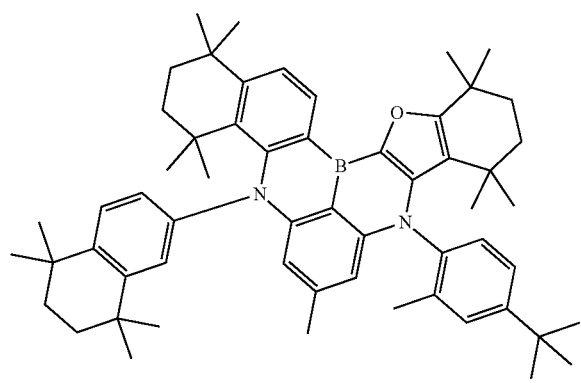
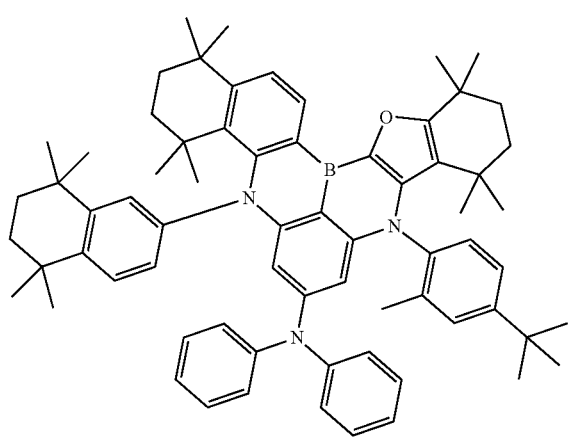
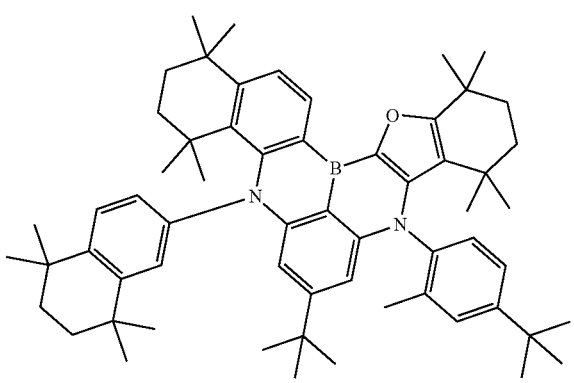
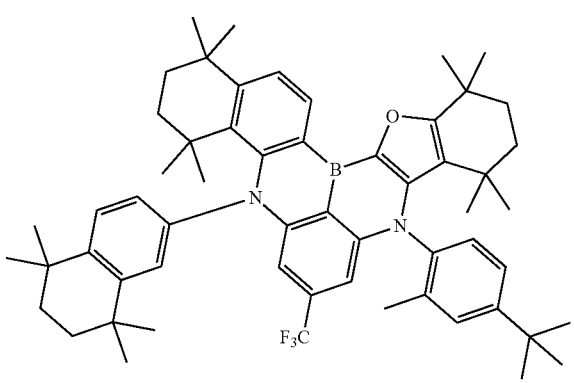
1162
-continued
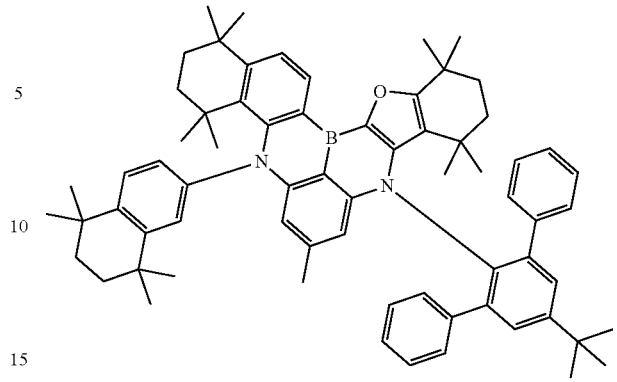
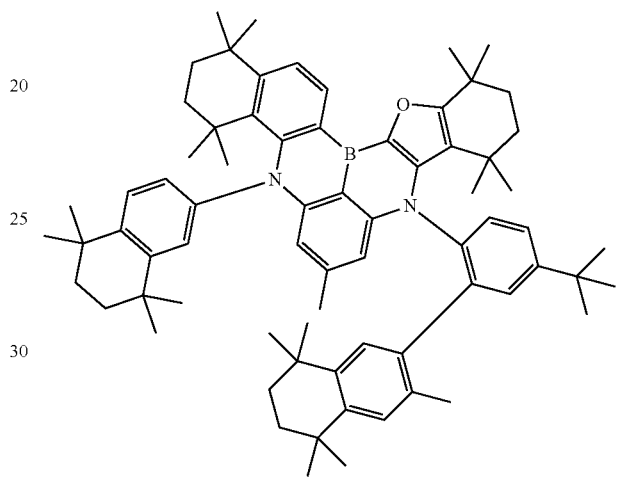
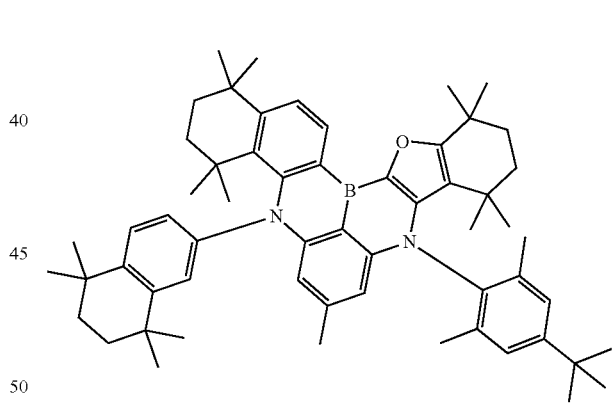
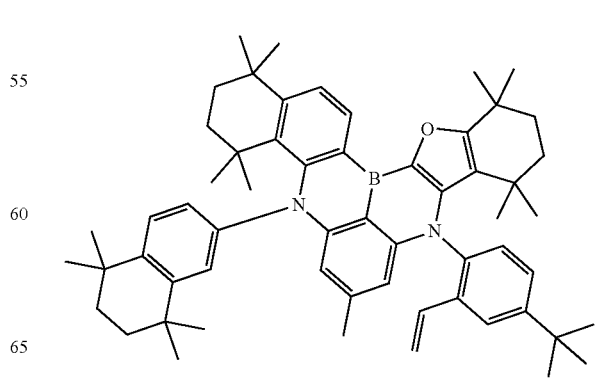

1163
-continued
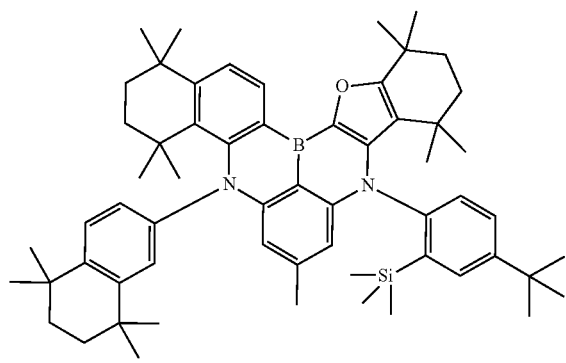
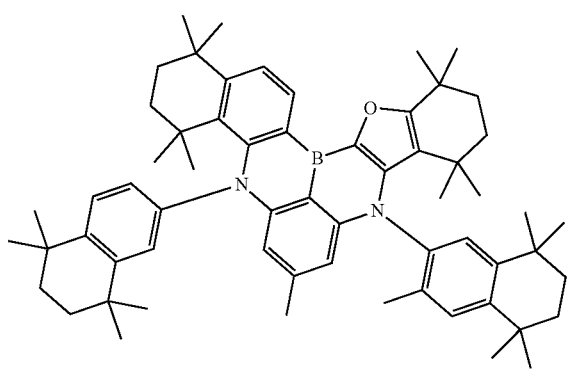
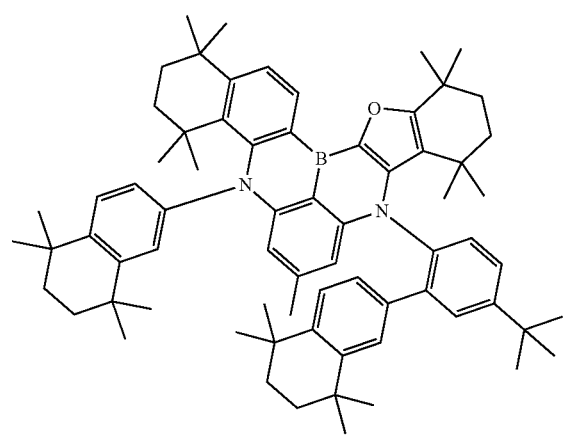
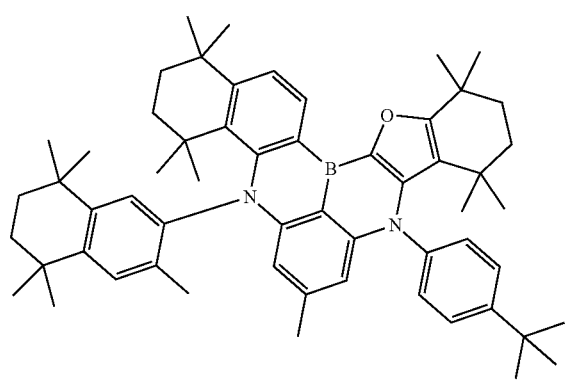
1164
-continued
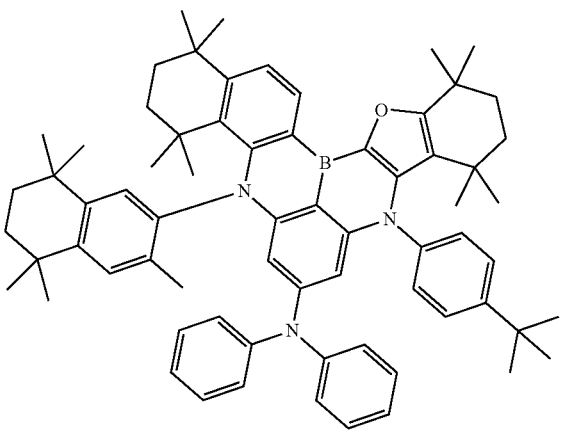
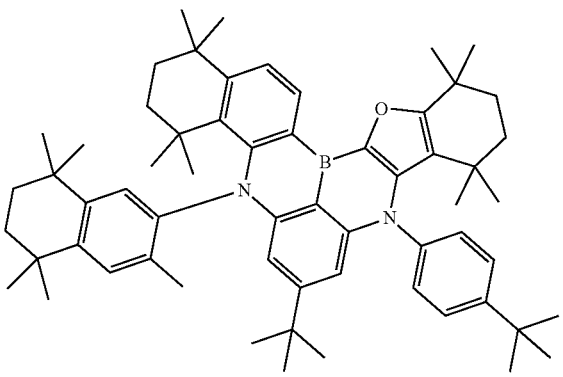
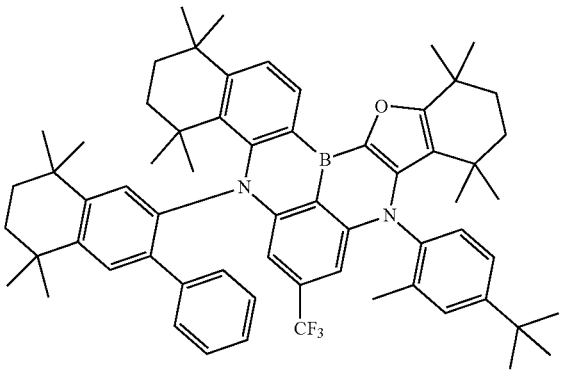
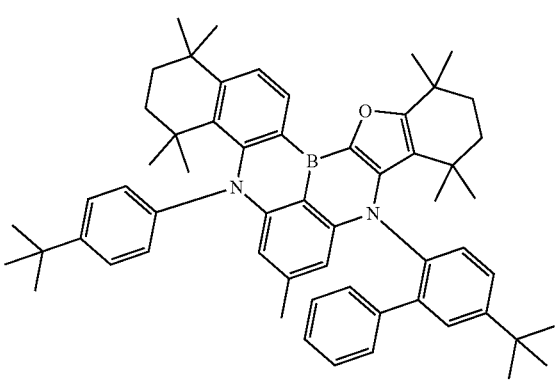

1165
-continued
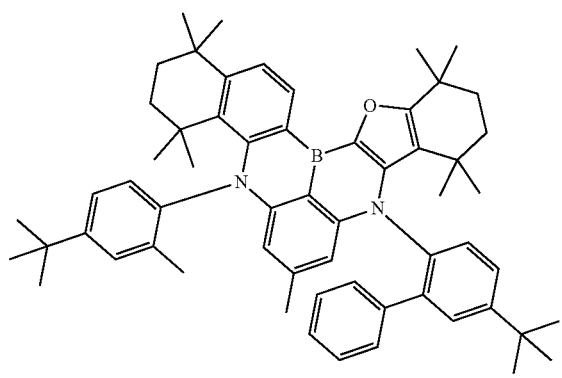
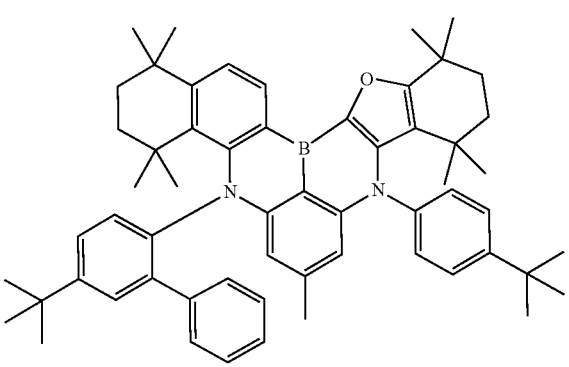
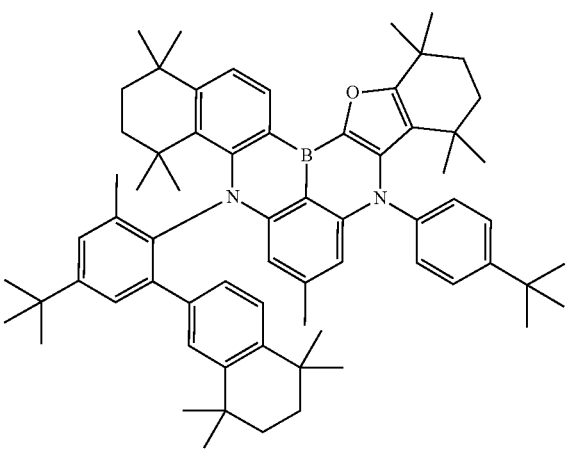
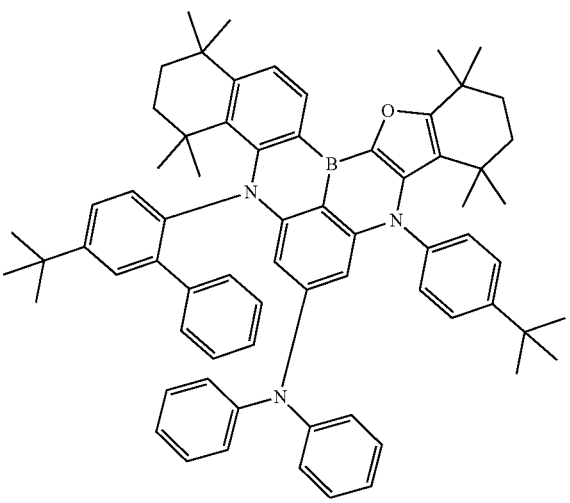
1166
-continued
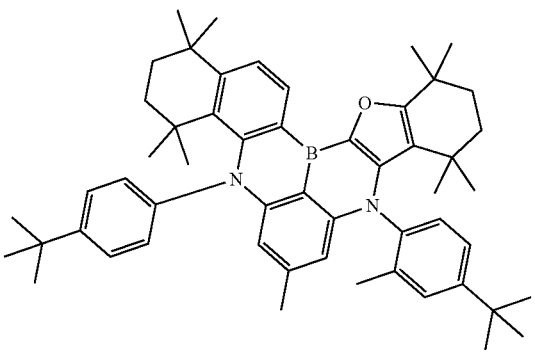
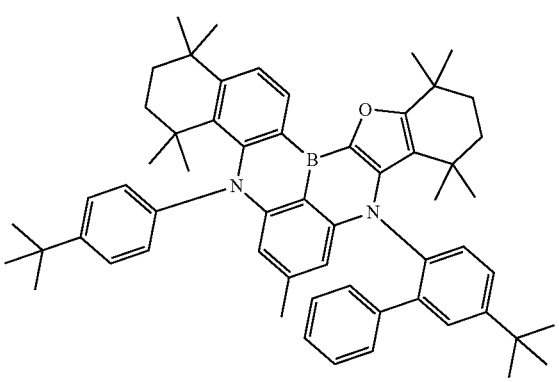
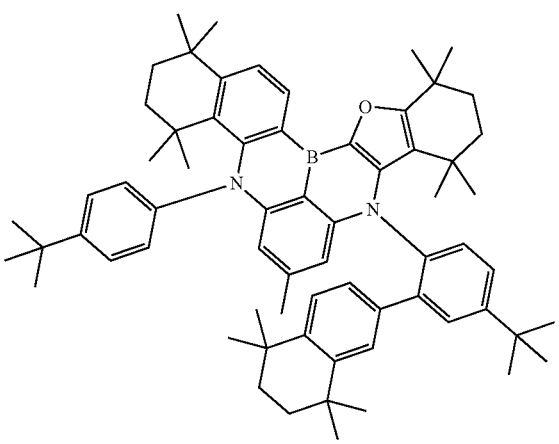
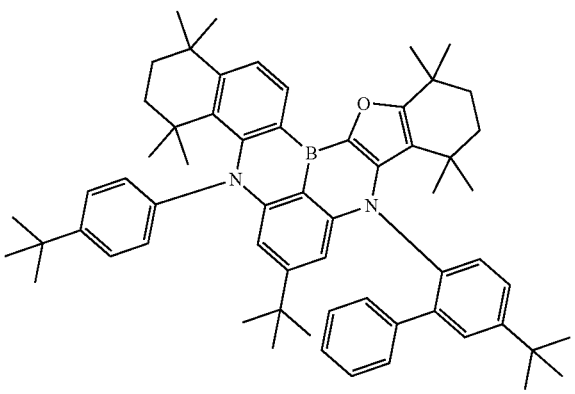

1167
-continued
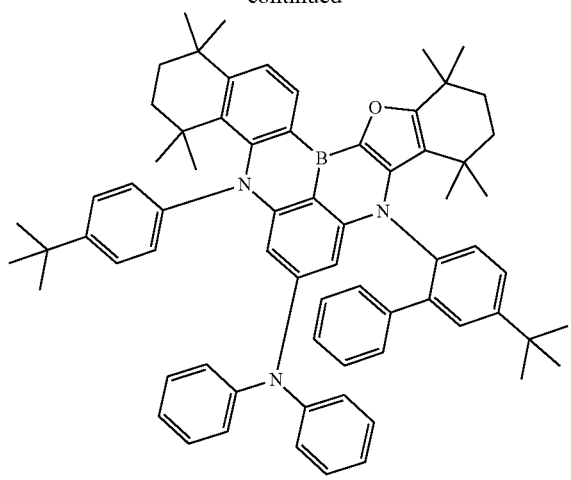
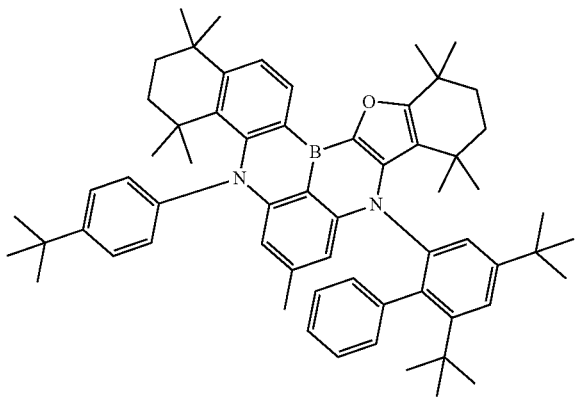
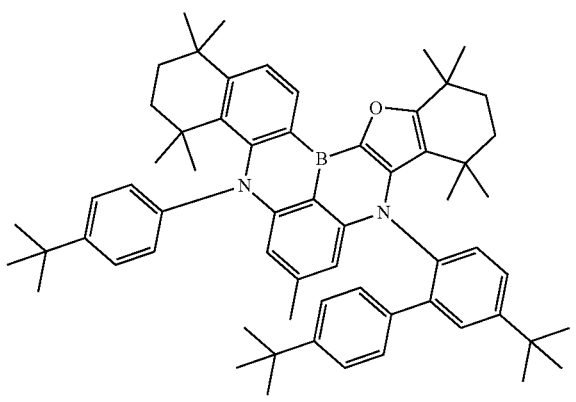
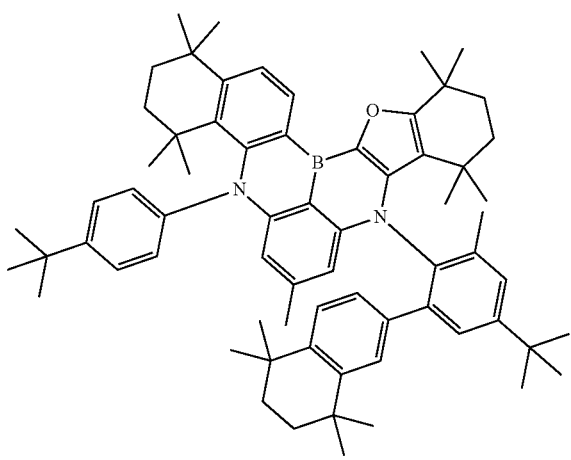 [SMILES: Cc1cc2c3c(c1)N(c1c(C)cc(C(C)(C)C)cc1-c1ccc4c(c1)C(C)(C)CCC4(C)C)c1c(oc4c1C(C)(C)CCC4(C)C)B3c1ccc3c(c1N2c1ccc(C(C)(C)C)cc1)C(C)(C)CCC3(C)C]
1168
-continued
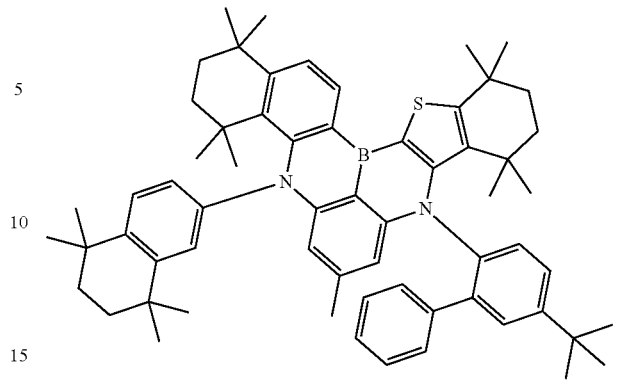
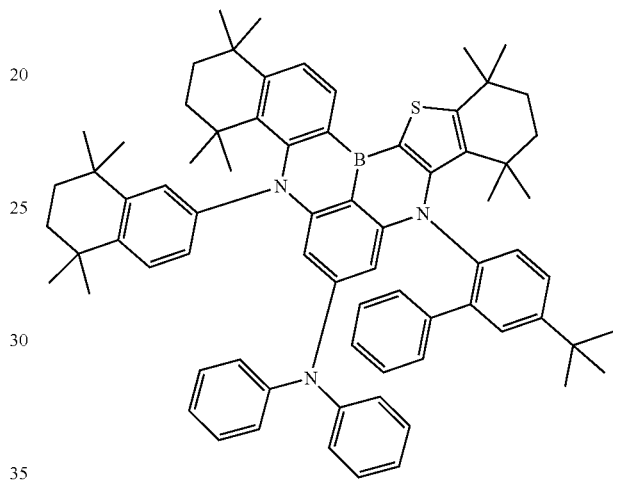
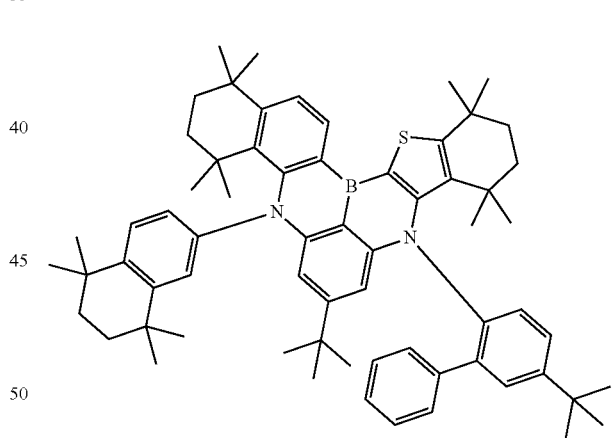
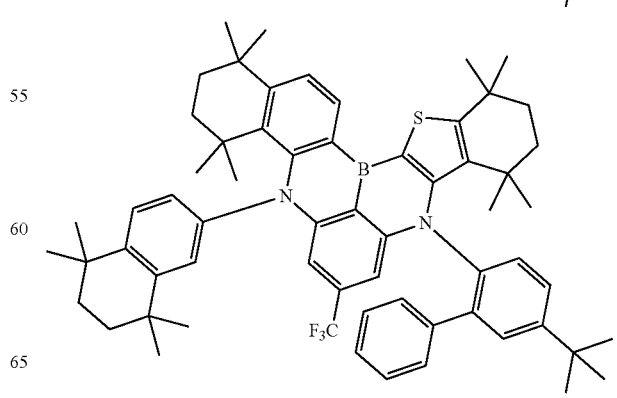

1169
-continued
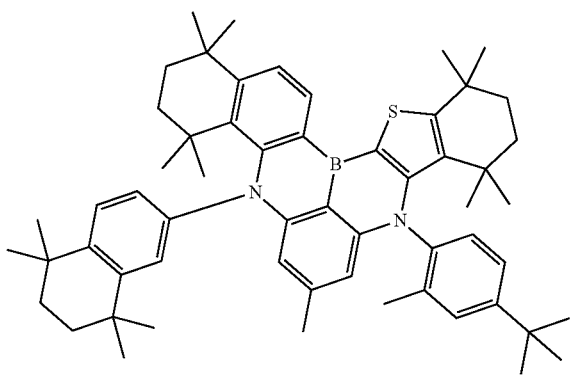
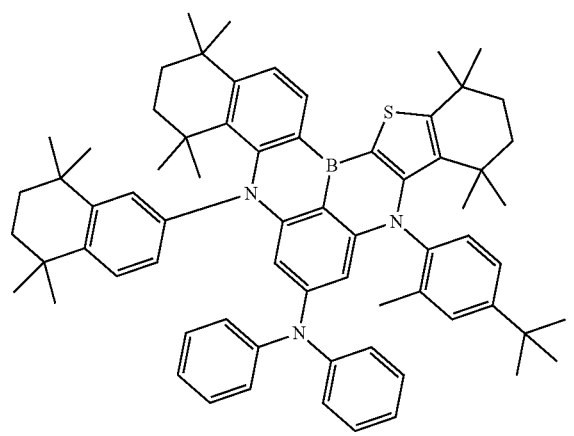
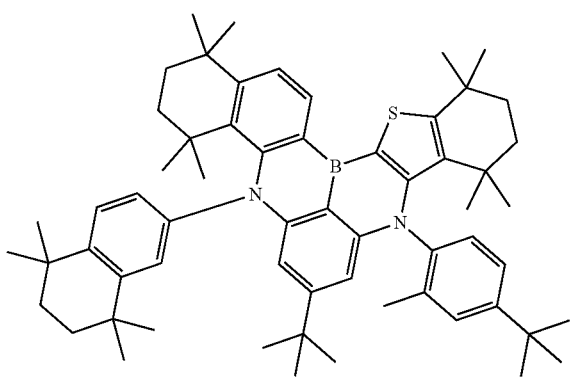
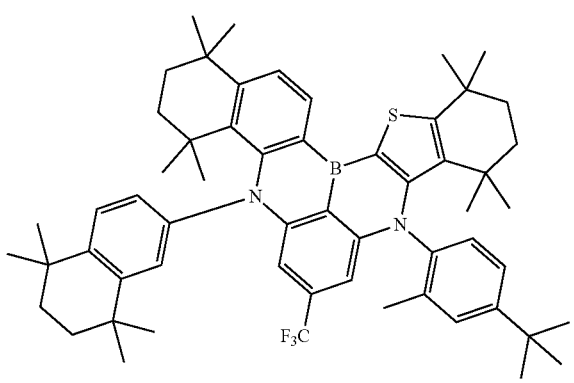
1170
-continued
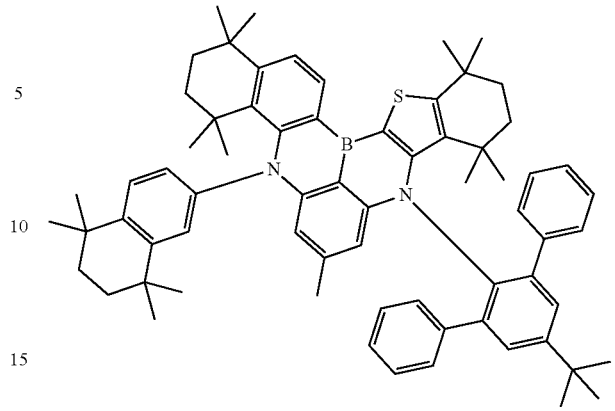

1171
-continued
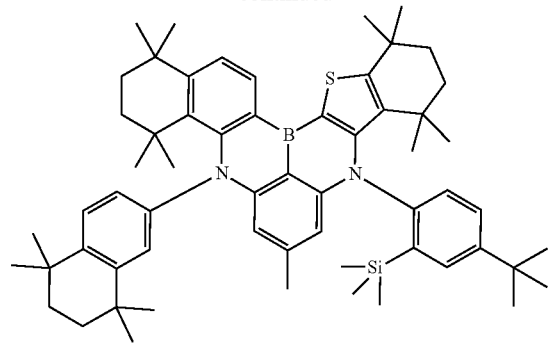
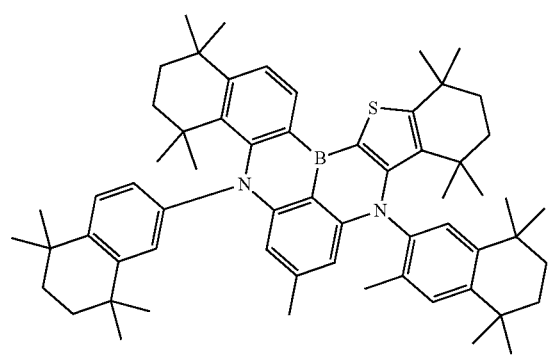
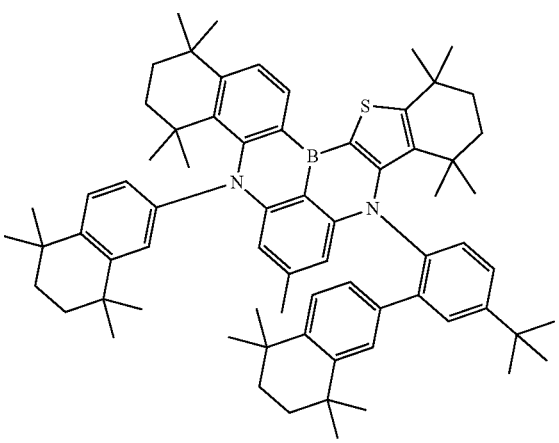
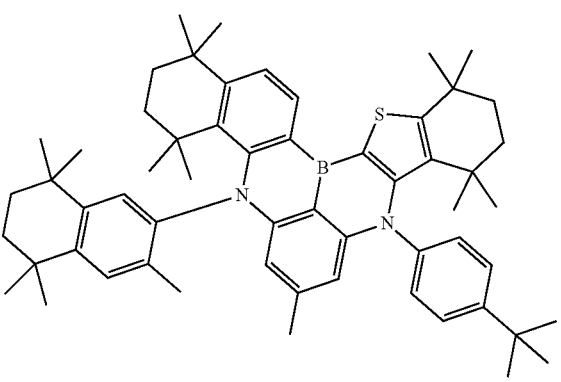
1172
-continued
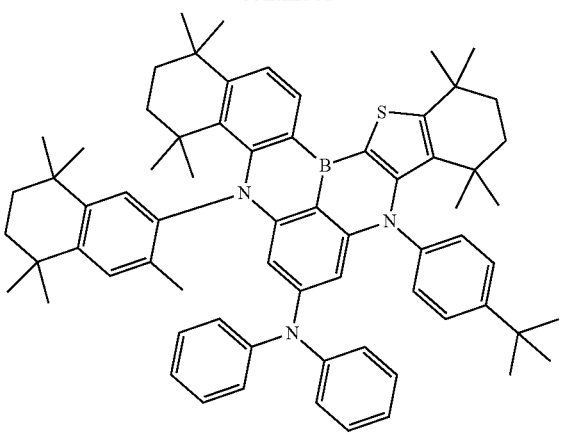
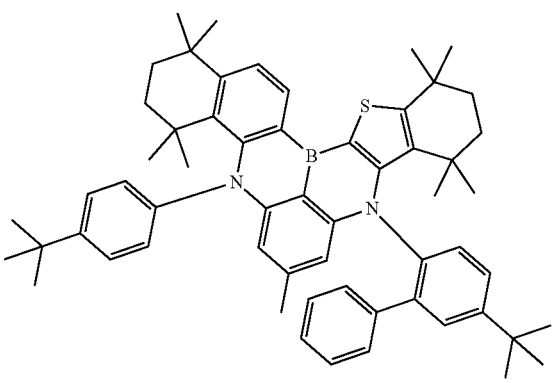

1173
-continued
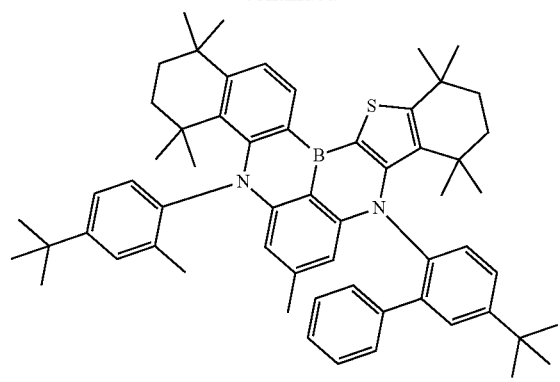
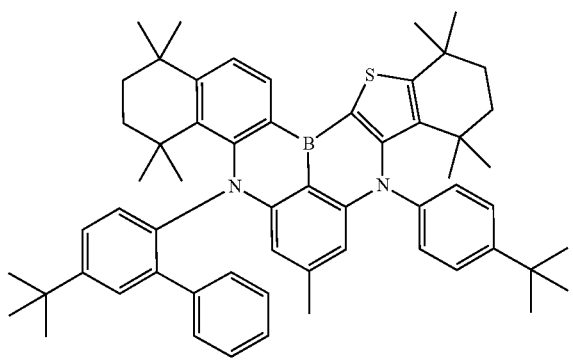
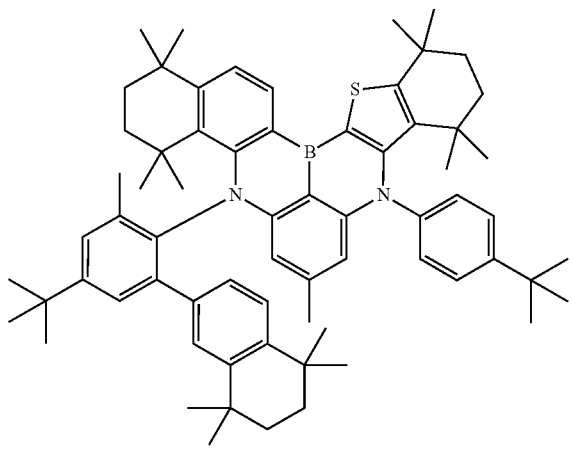
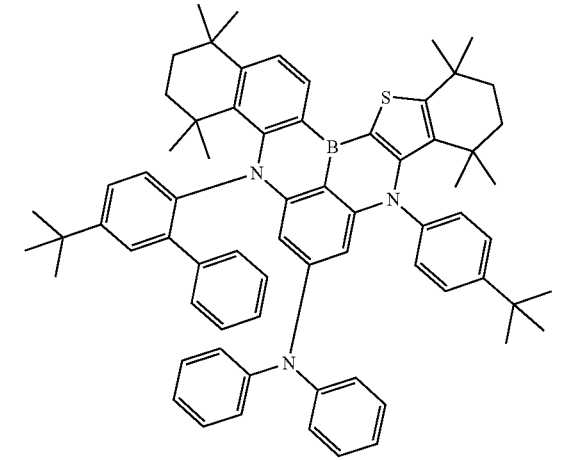
1174
-continued
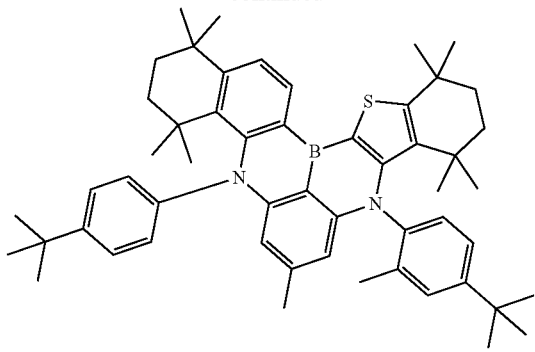
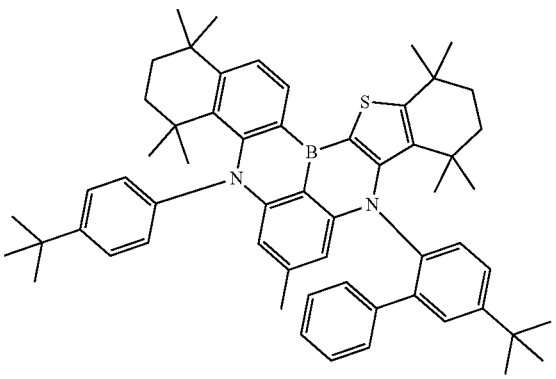
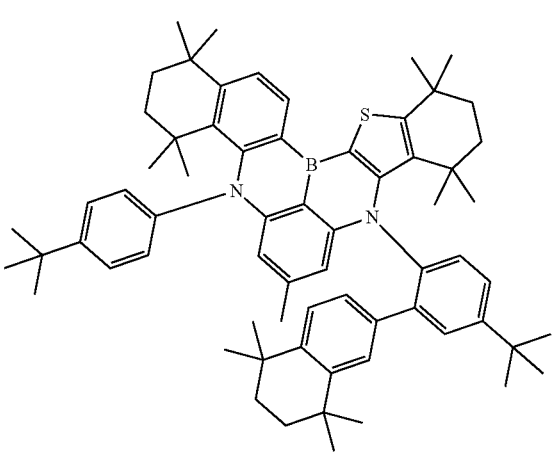
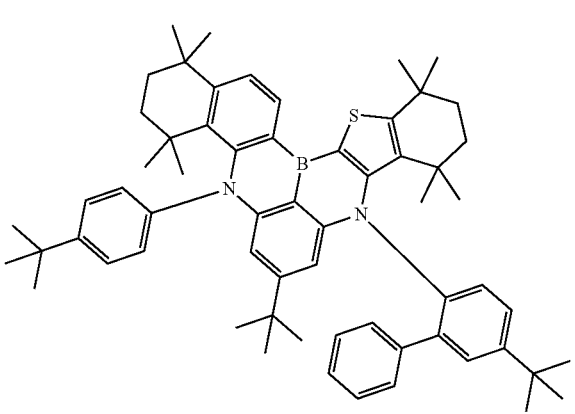

1175
-continued
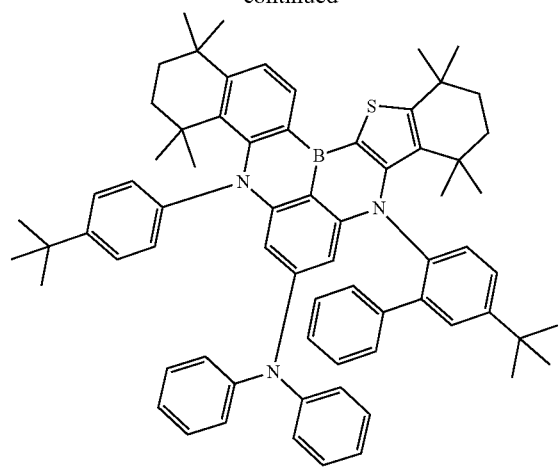
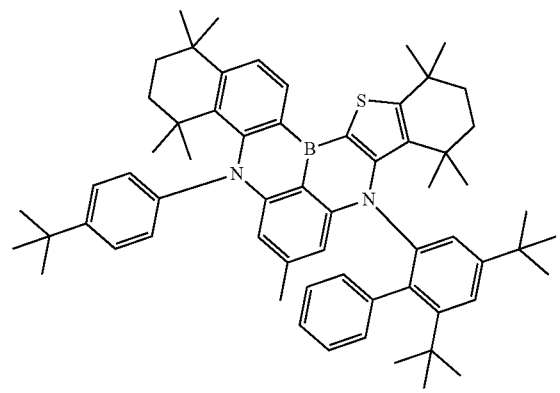
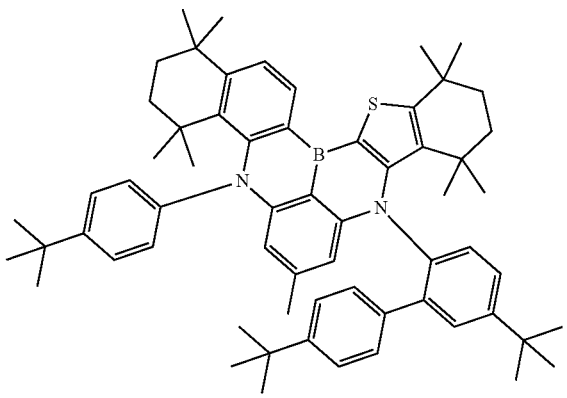
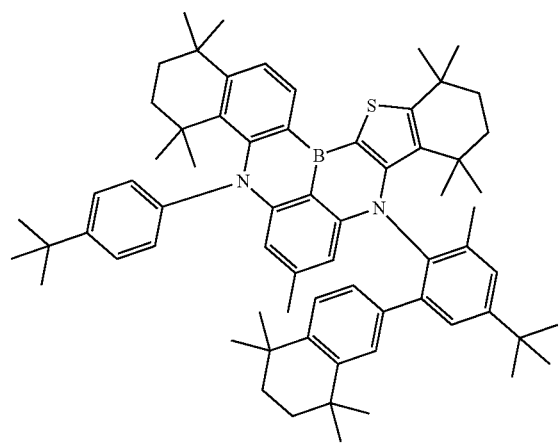 [SMILES: Cc1cc2c3c(c1)N(c1c(C)cc(C(C)(C)C)cc1-c1ccc4c(c1)C(C)(C)CCC4(C)C)c1c(sc4c1C(C)(C)CCC4(C)C)B3c1ccc3c(c1N2c1ccc(C(C)(C)C)cc1)C(C)(C)CCC3(C)C]
1176
-continued
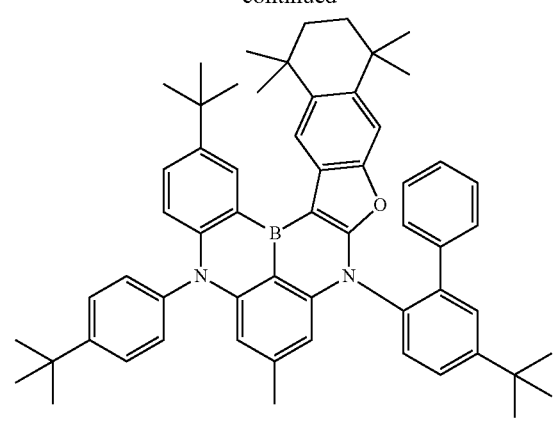
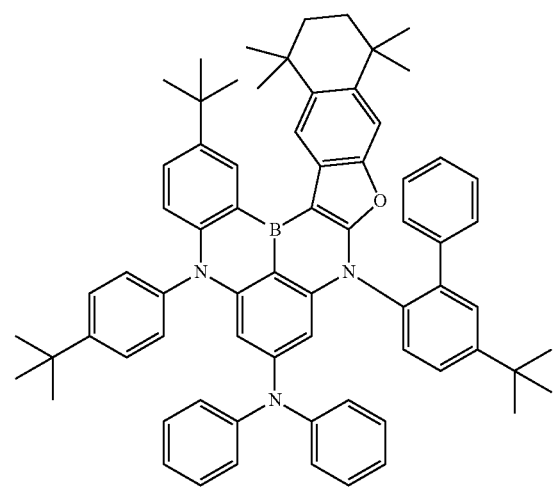
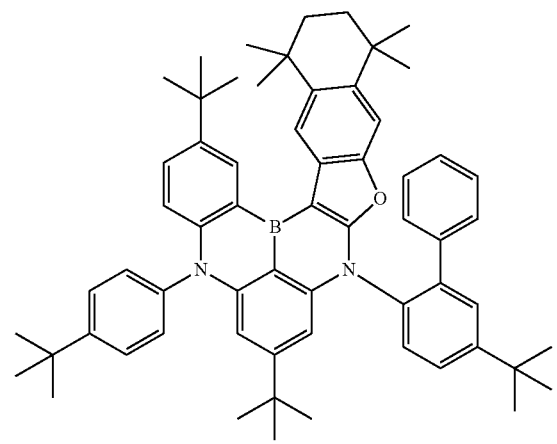

1177
-continued
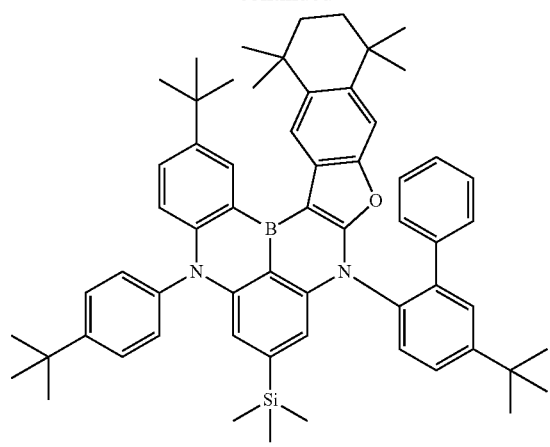
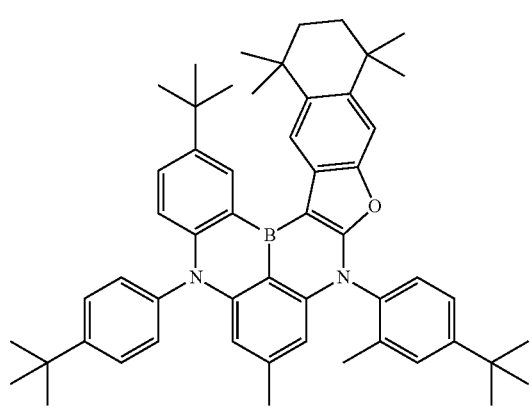
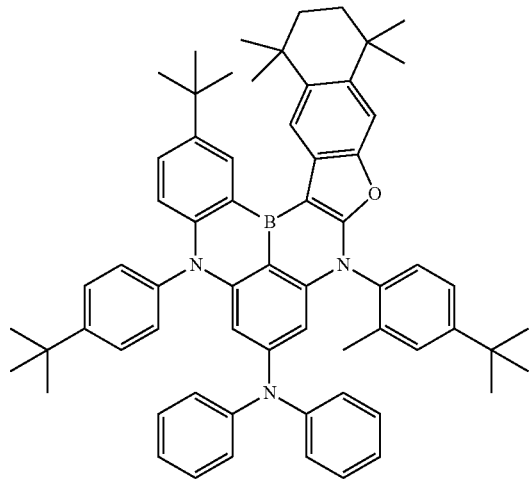
1178
-continued
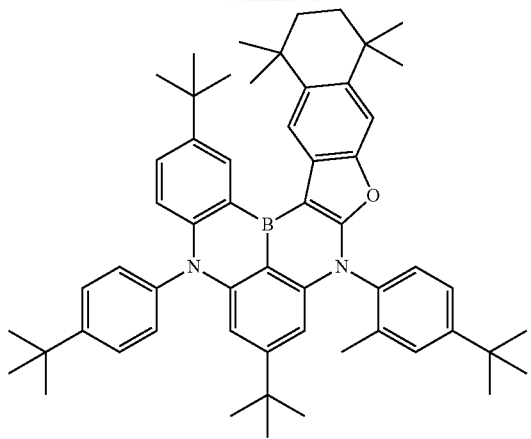
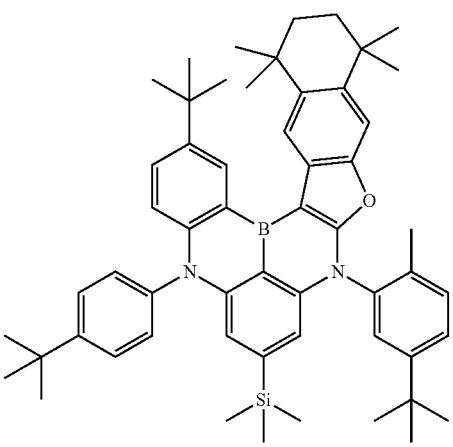
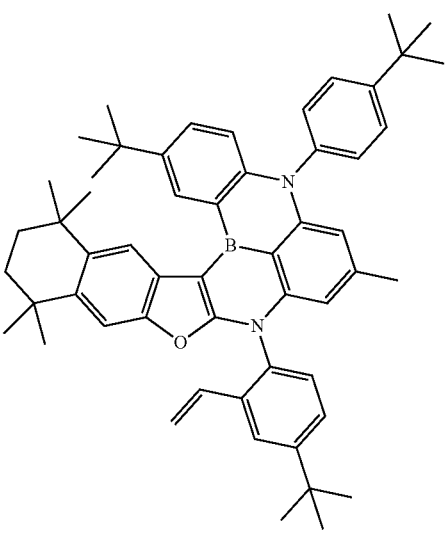

1179
-continued
1180
-continued
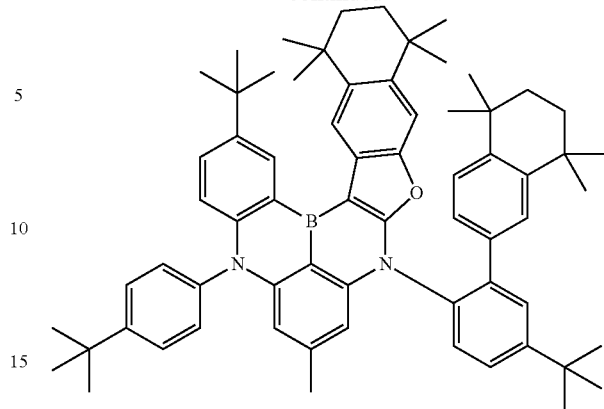
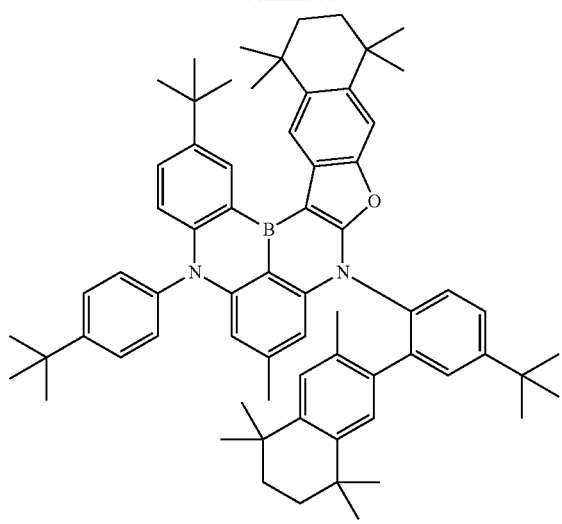
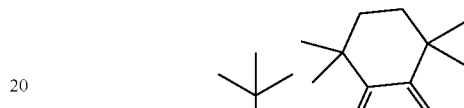
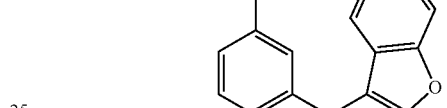
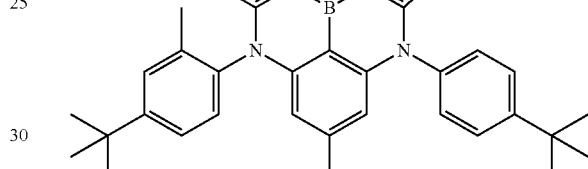
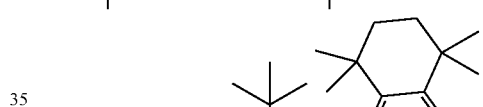
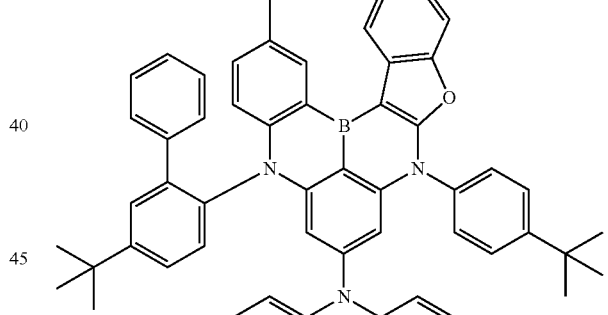
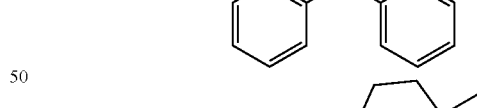
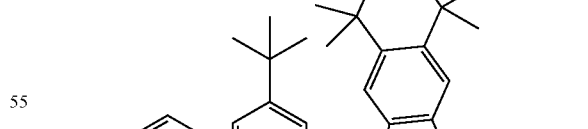
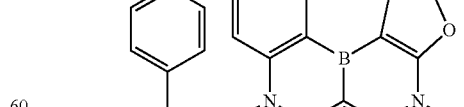
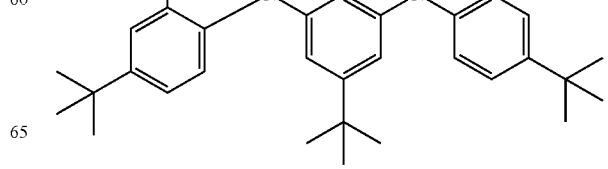

1181
-continued
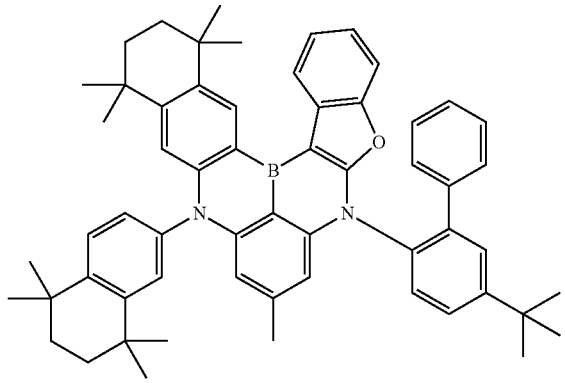
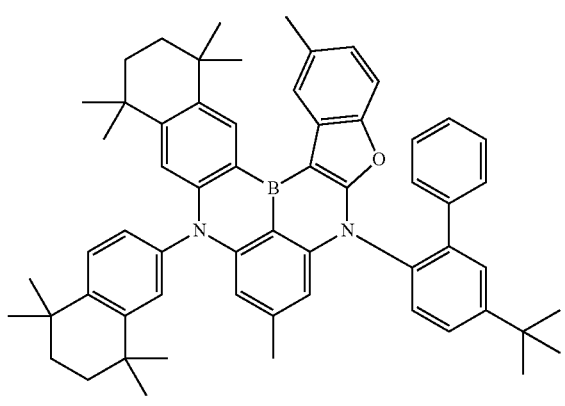
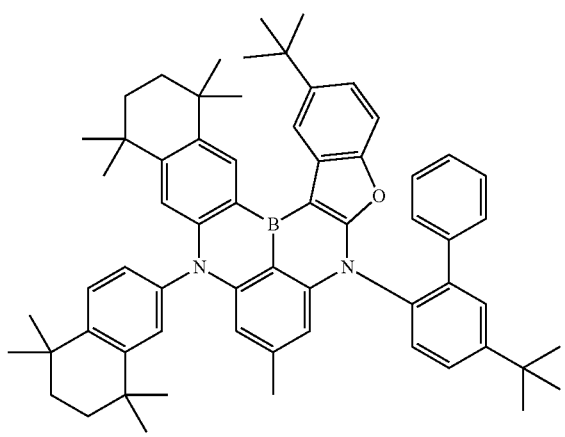
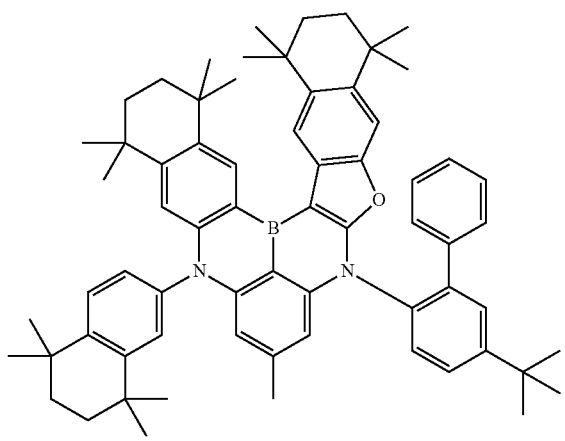
1182
-continued
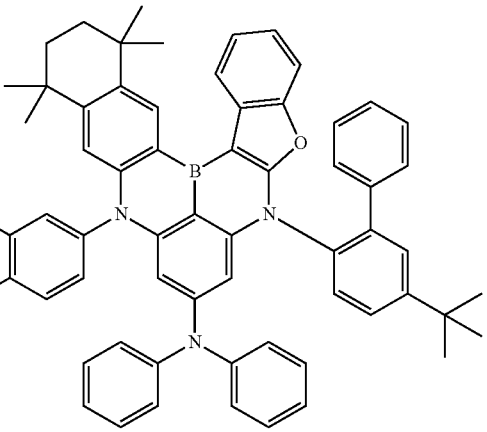
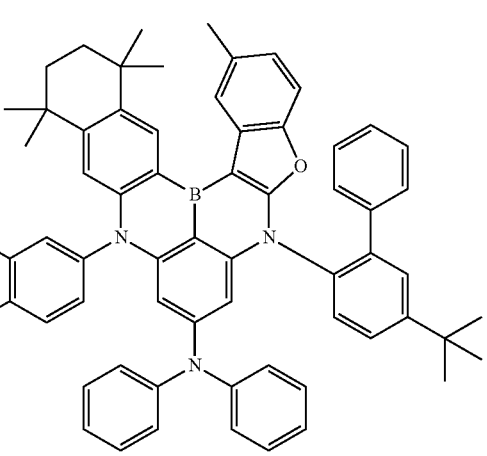
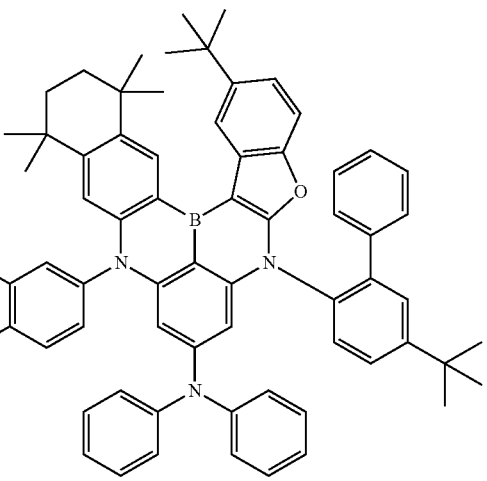

1183
-continued
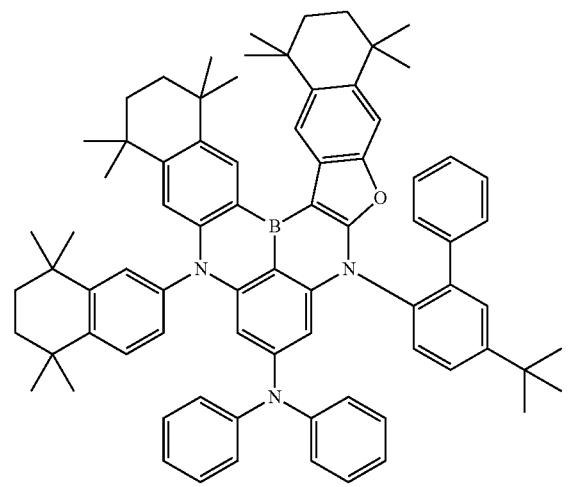
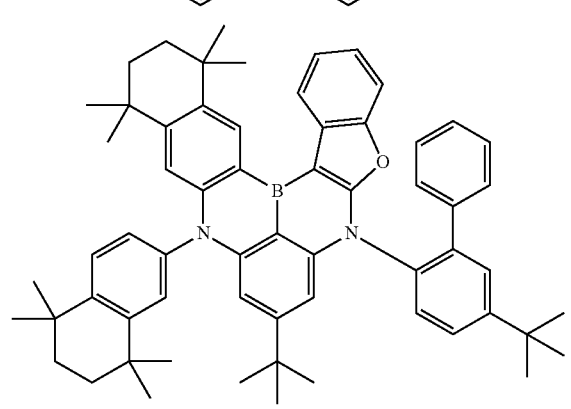
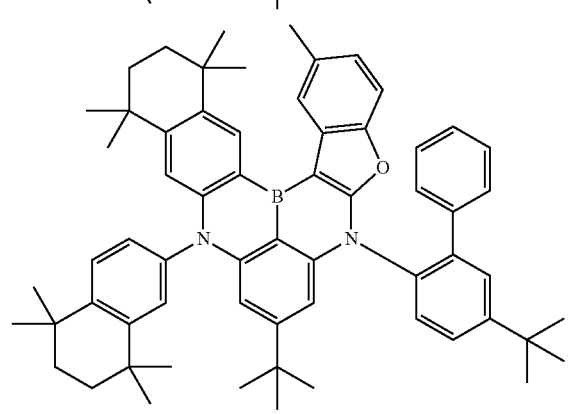
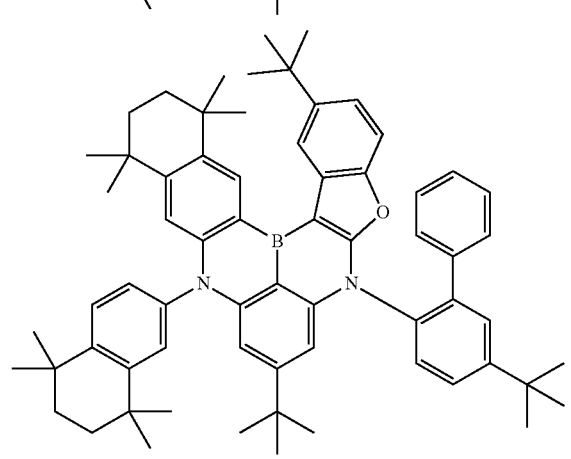
1184
-continued
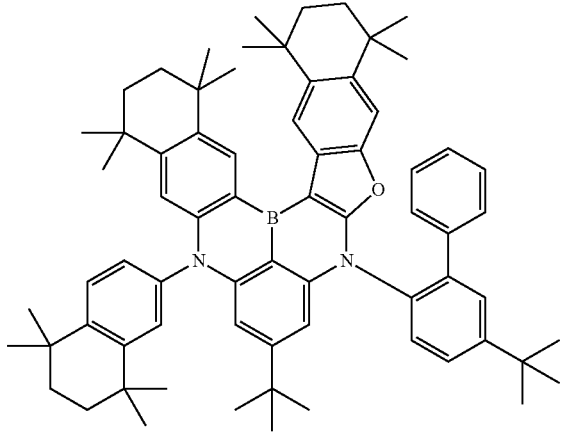
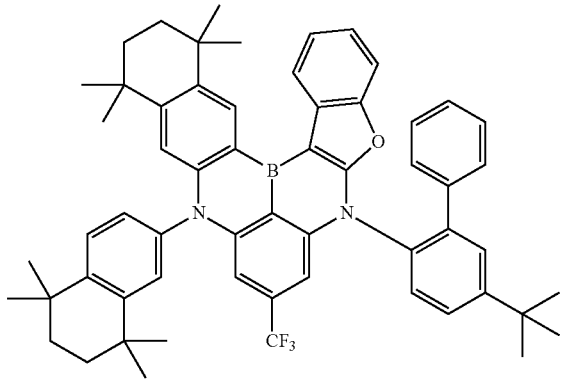
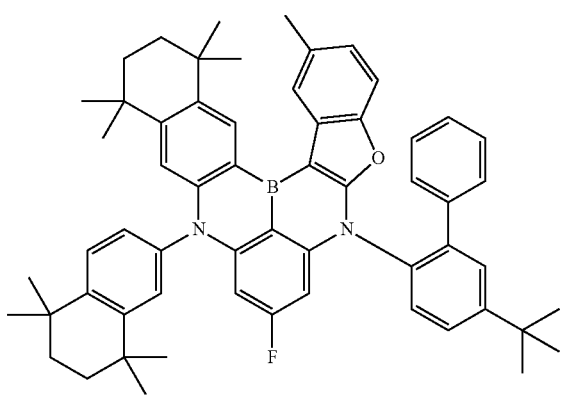
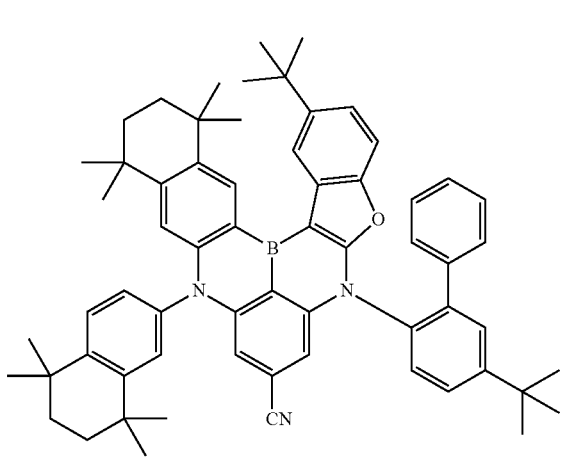

1185
-continued
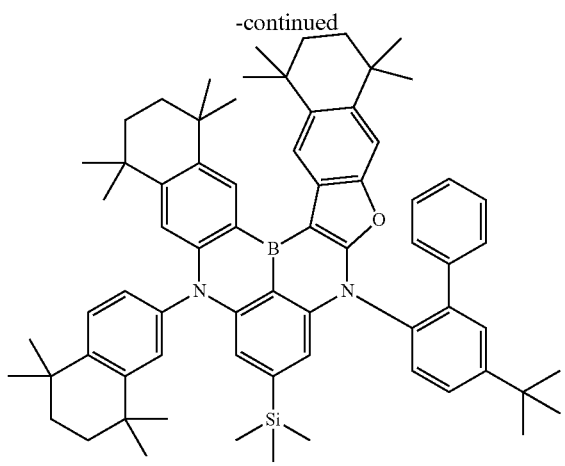
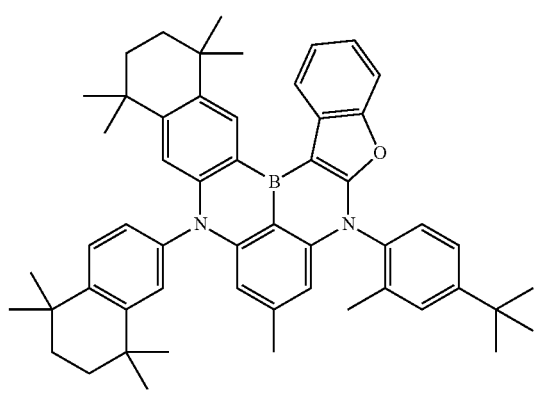
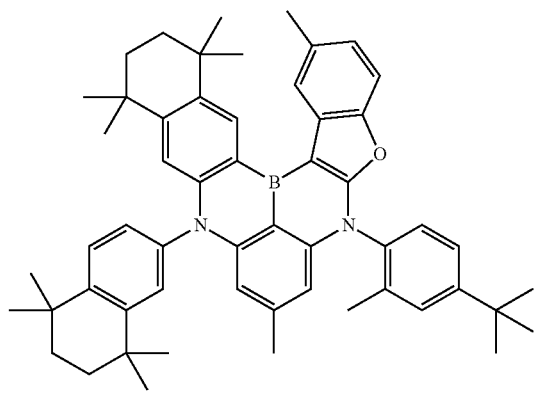
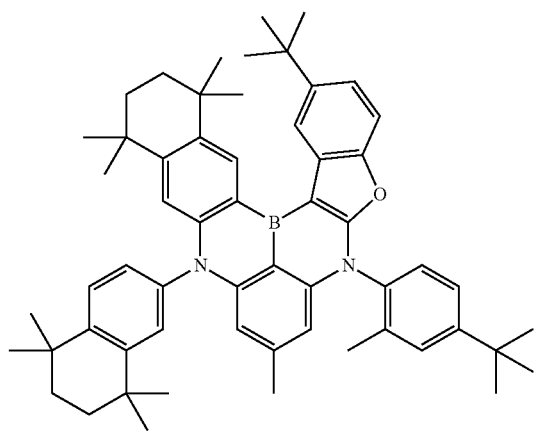
1186
-continued
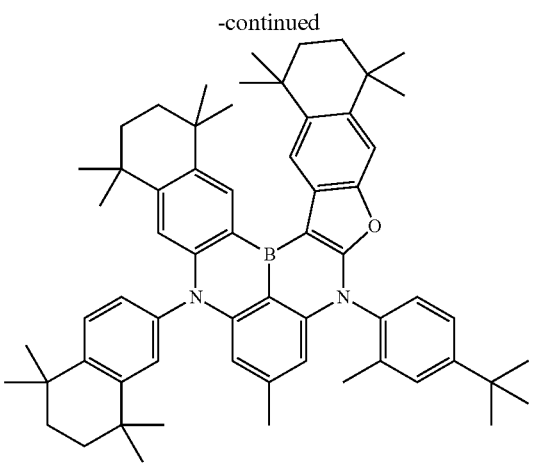
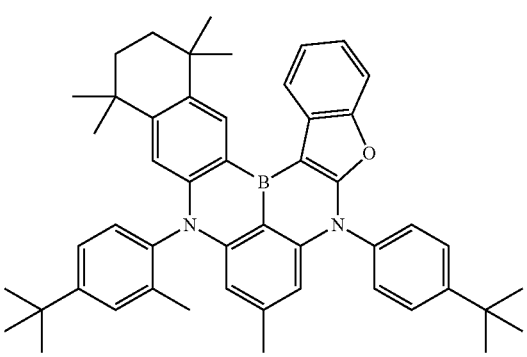
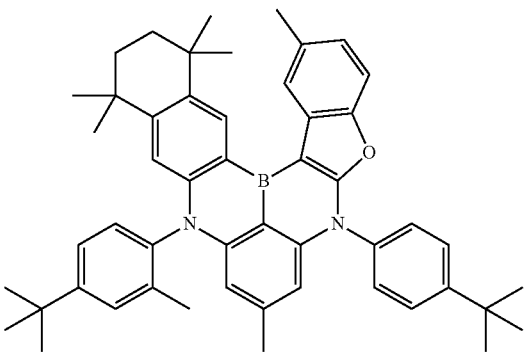
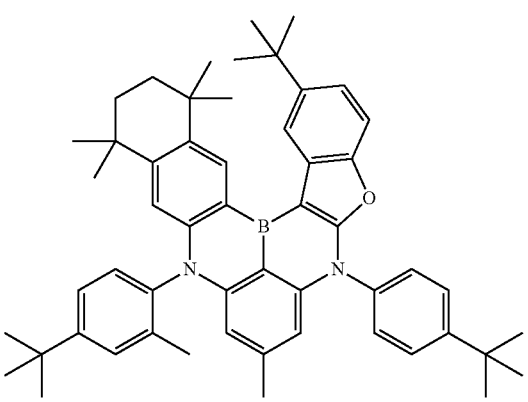

1187
-continued
1188
-continued
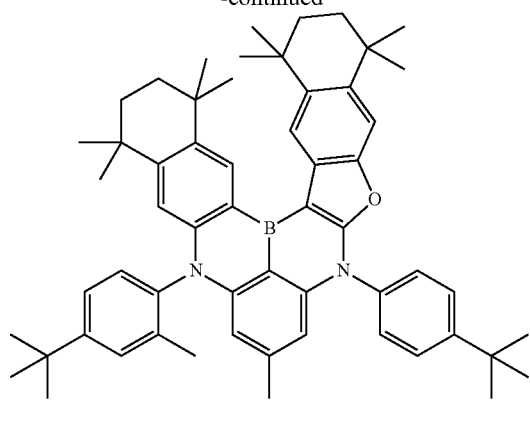
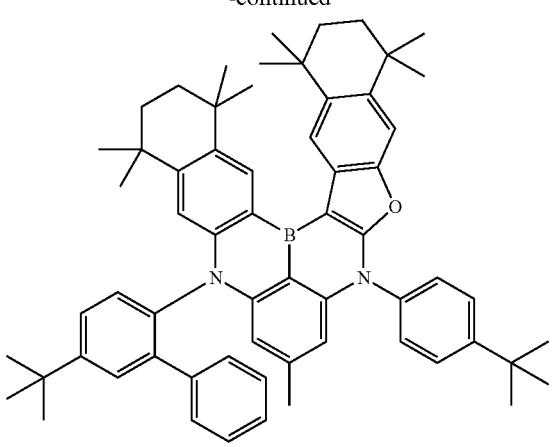
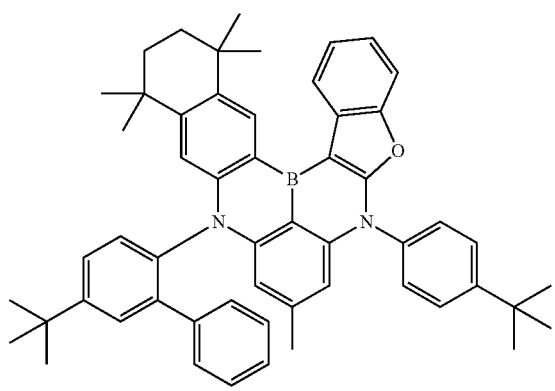
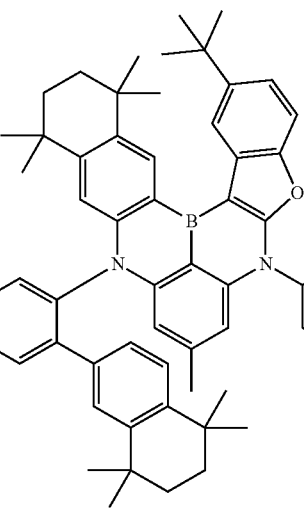
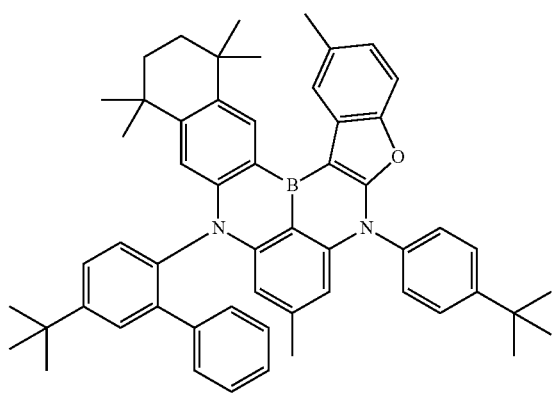
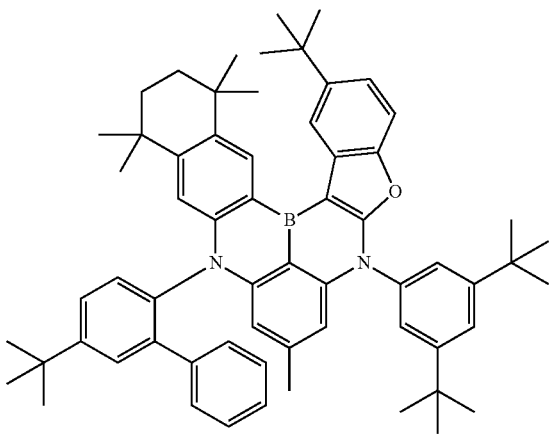

1189
-continued
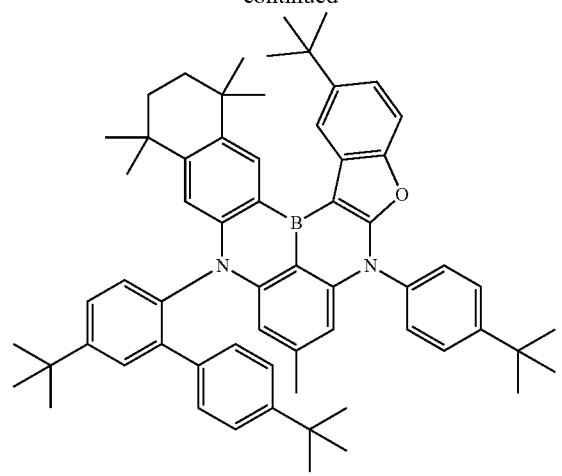
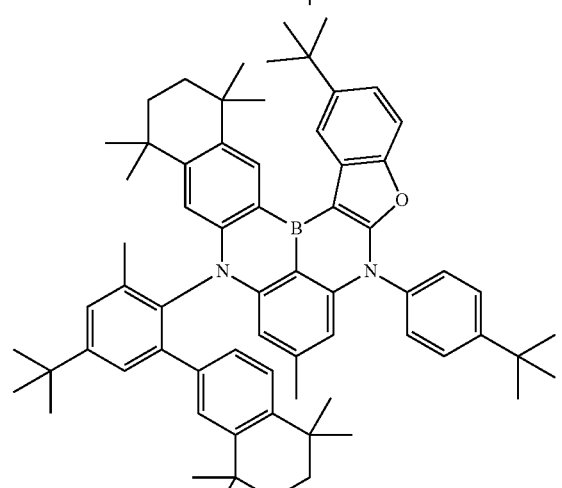
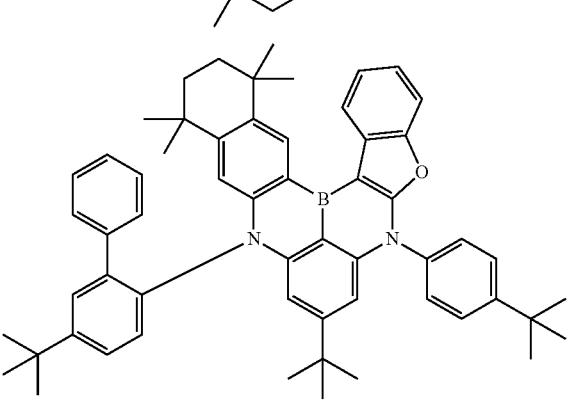
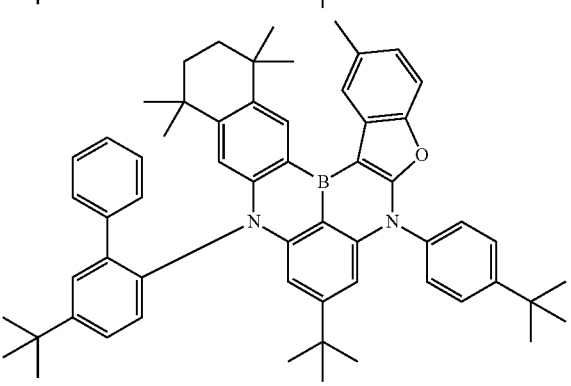
1190
-continued
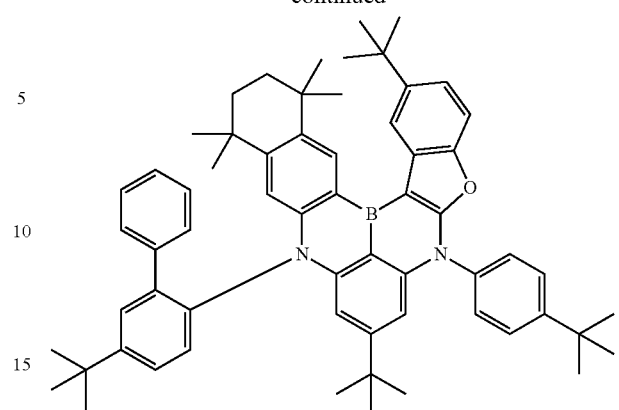
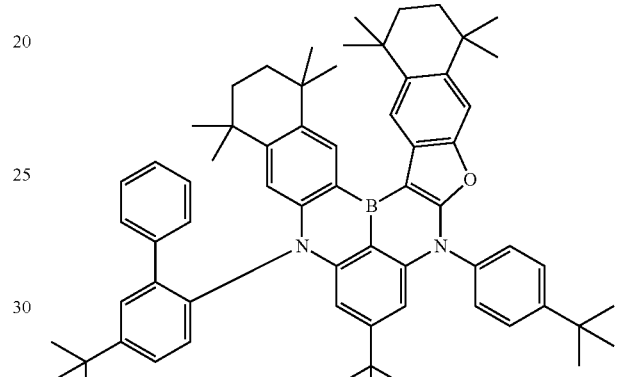
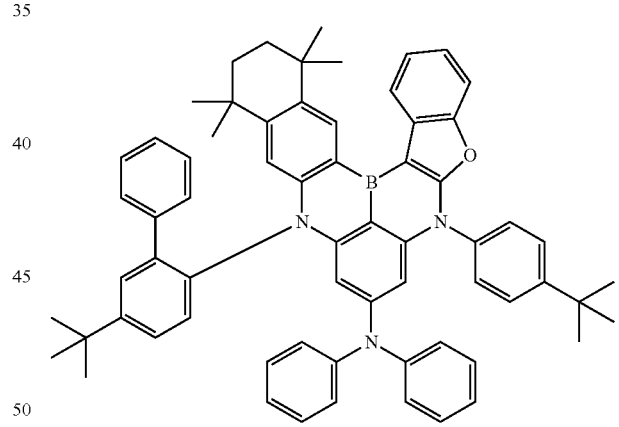
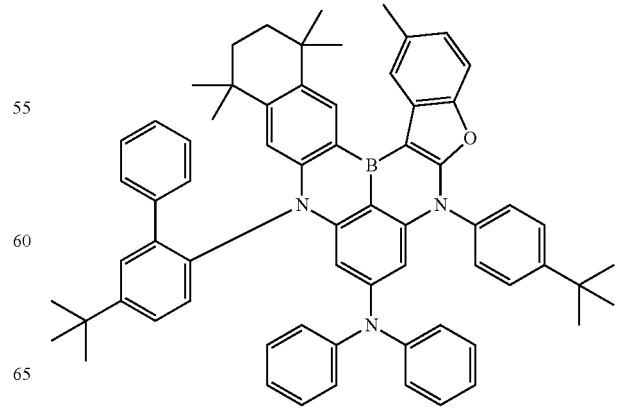

1191
-continued
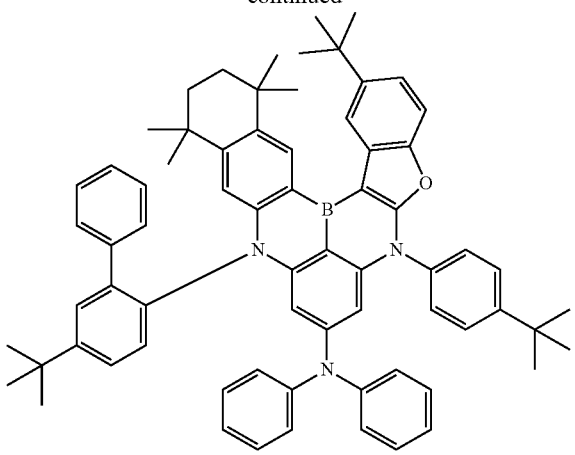
1192
-continued
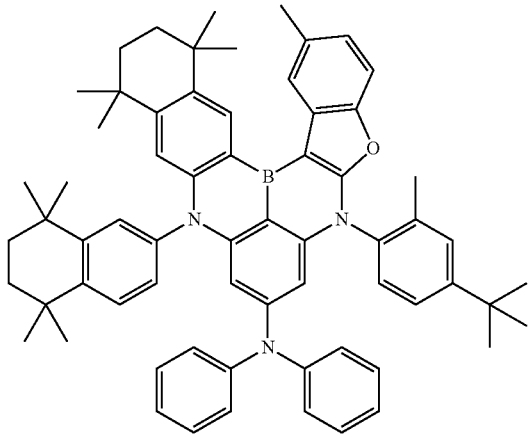
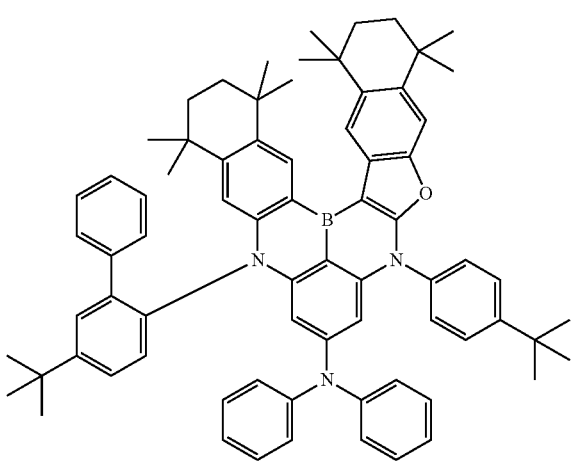
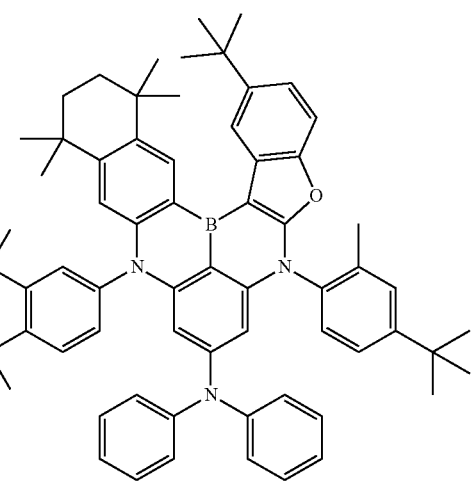
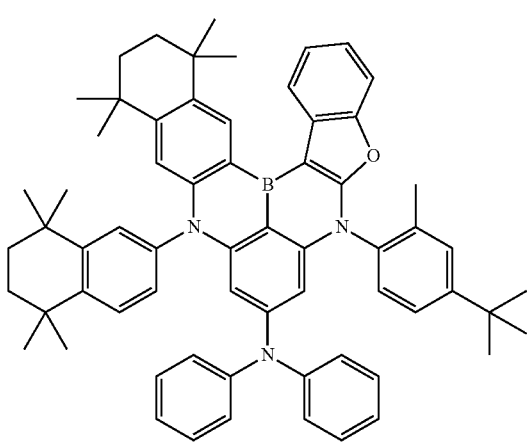
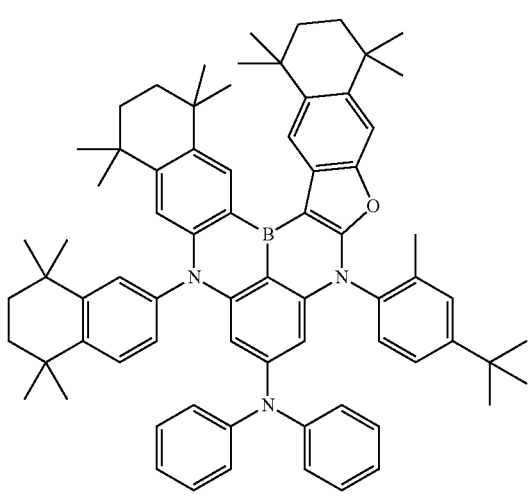

1193
-continued
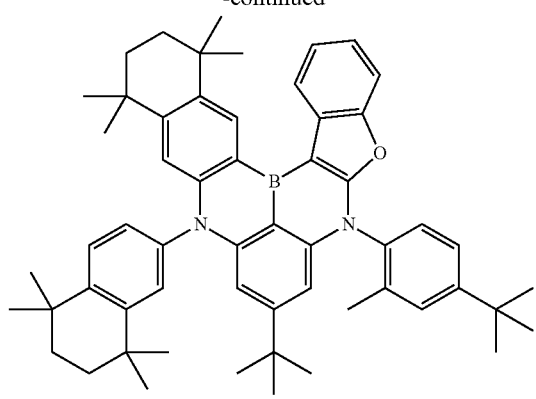
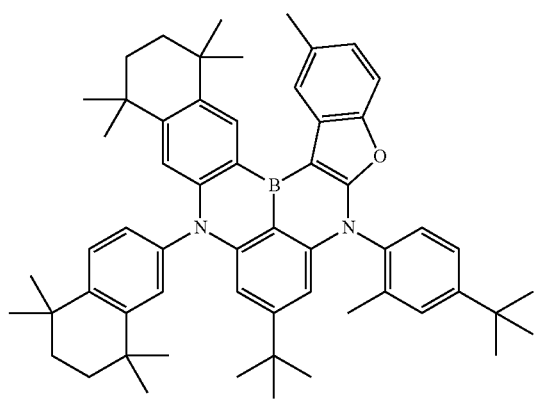
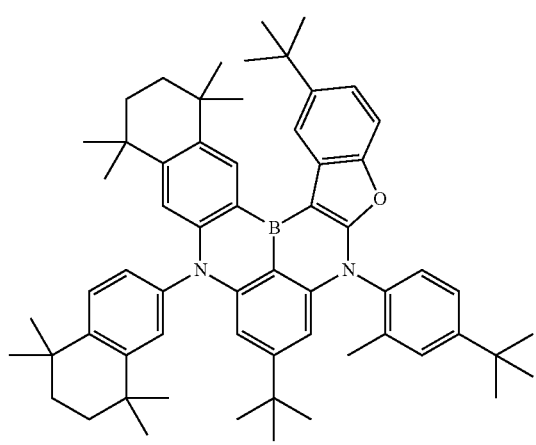
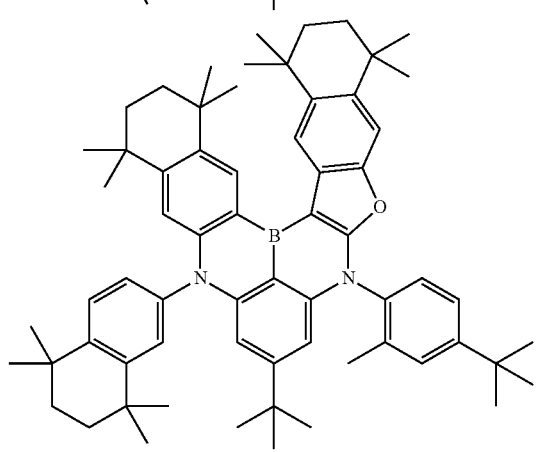
1194
-continued
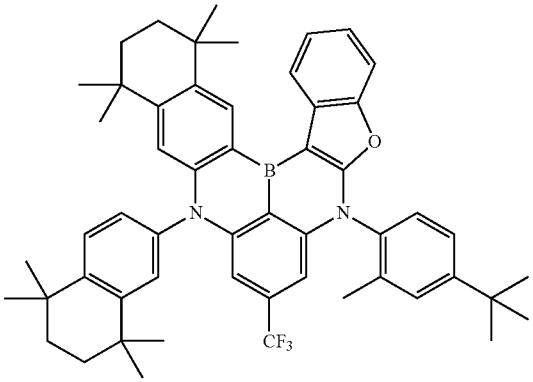
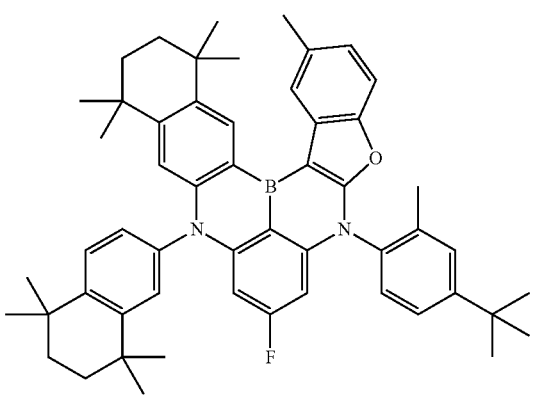
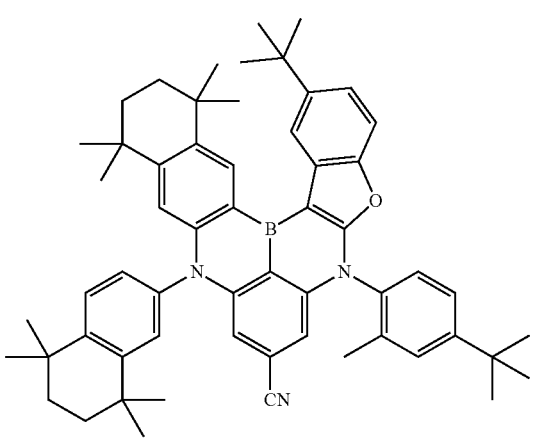
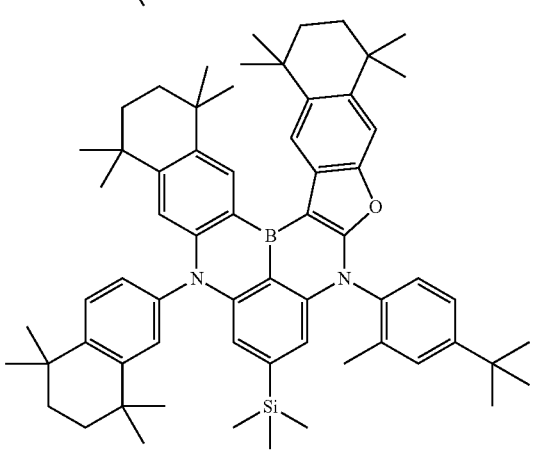

1195
-continued
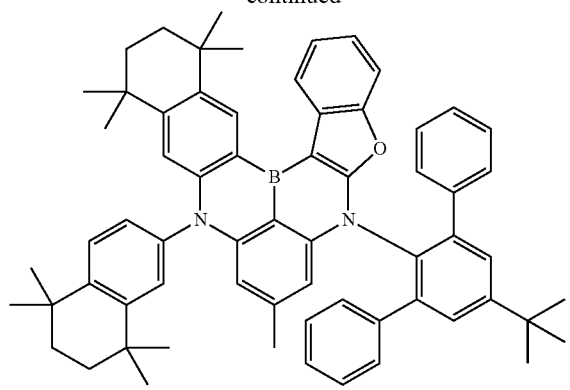
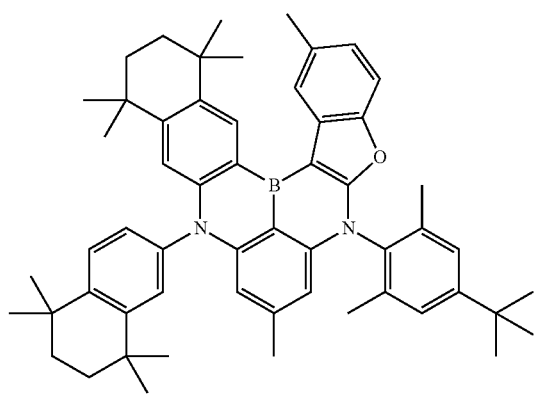
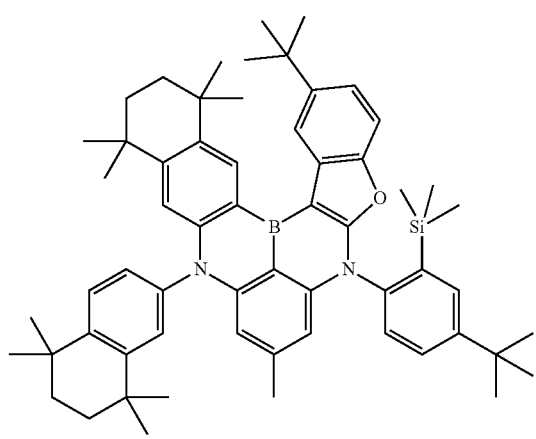
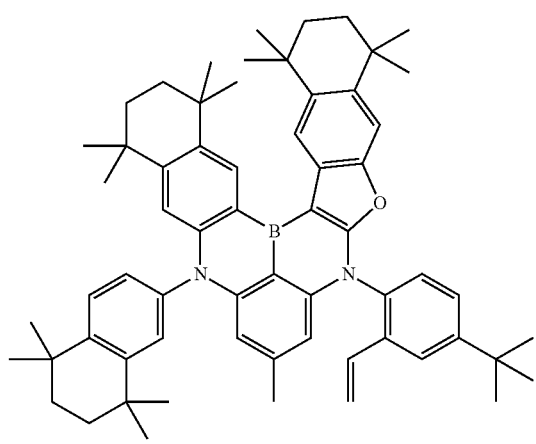
1196
-continued
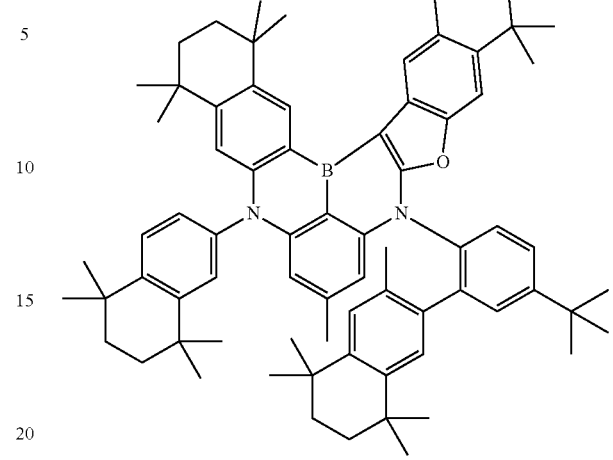
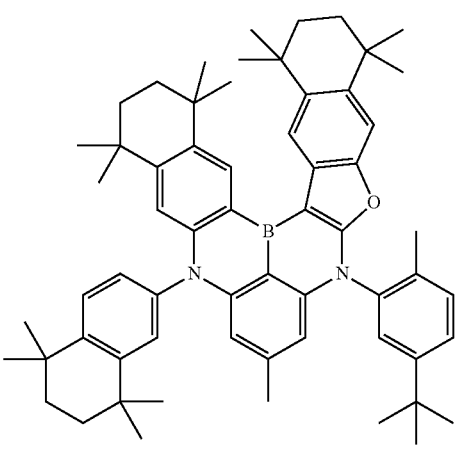

1197
-continued
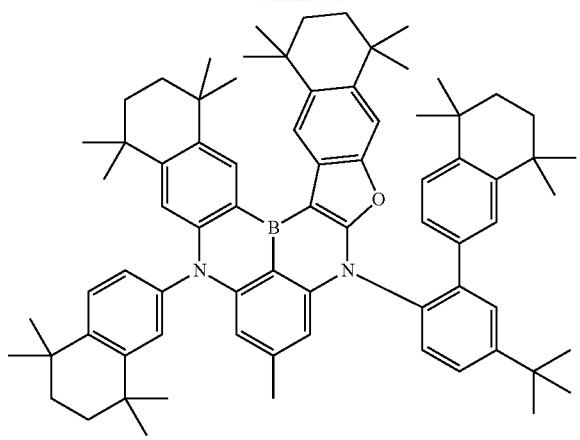
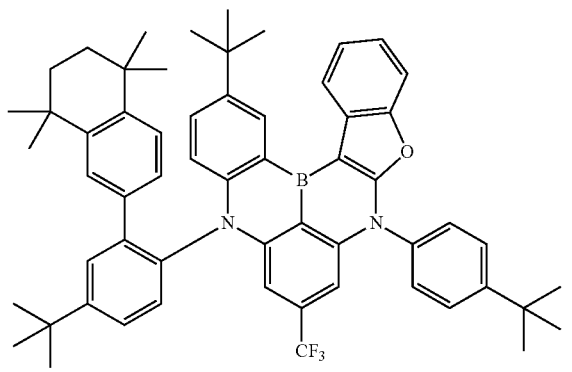
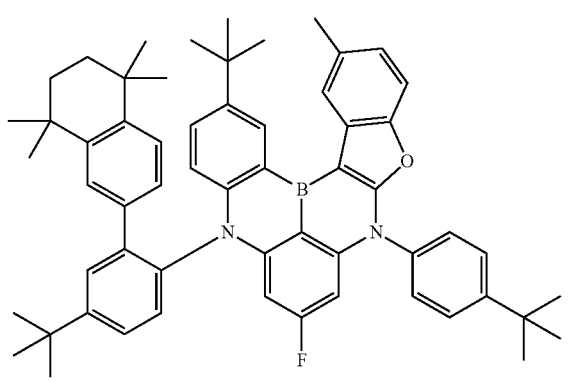
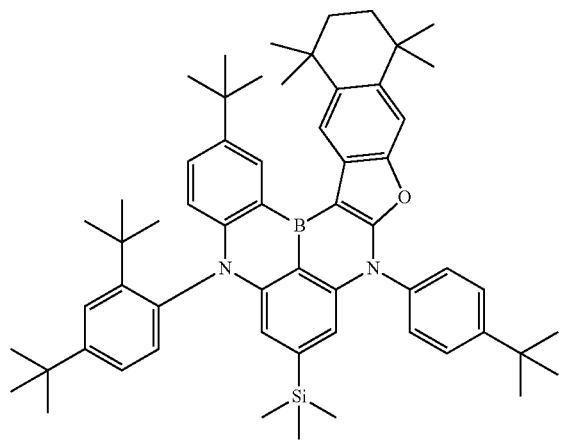 [SMILES: CC(C)(C)c1ccc(N2c3cc(C(C)(C)C)cc4c3B(c3cc(C(C)(C)C)ccc3N4c3ccc(C(C)(C)C)cc3-c3ccccc3)c3c2oc2cc4c(cc32)C(C)(C)CCC4(C)C)cc1]
1198
-continued
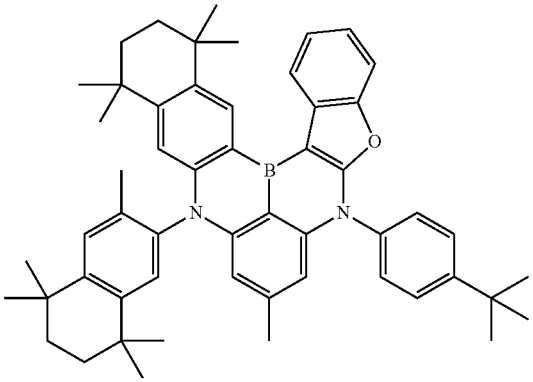
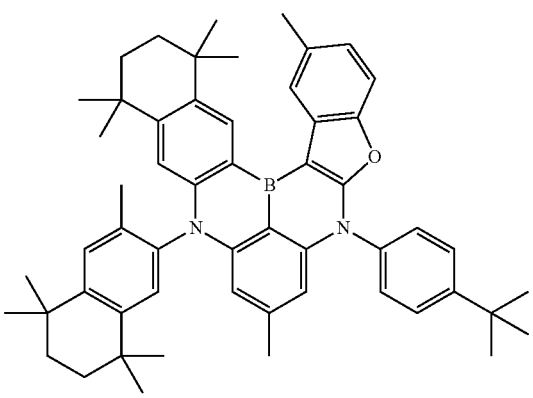
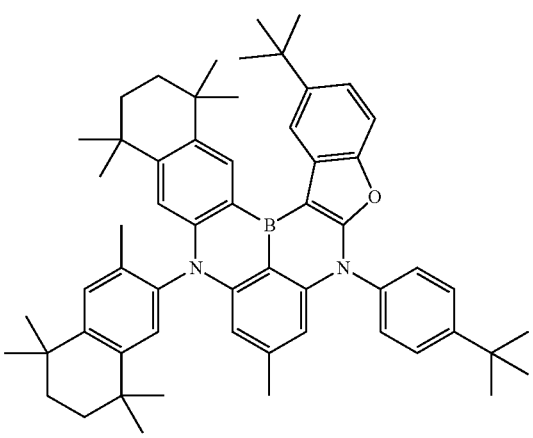
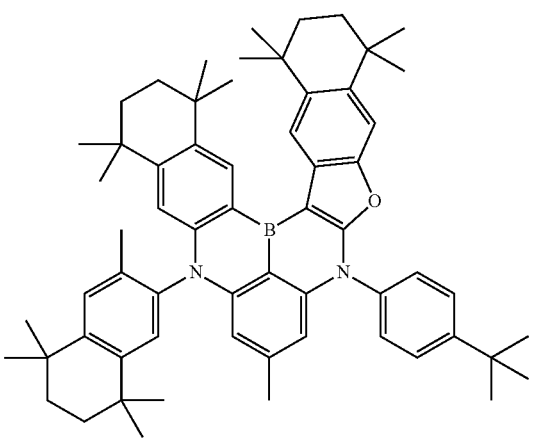

| 1199 | 1200 |
|---|---|
| 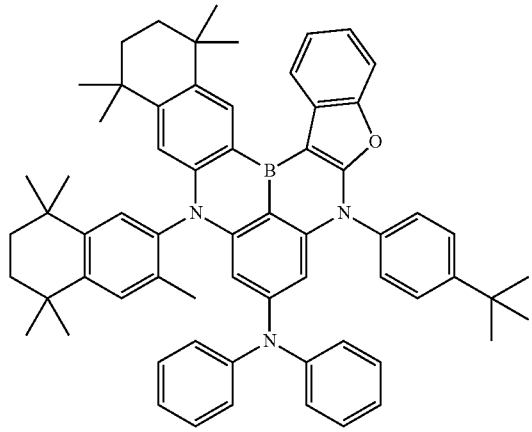 | 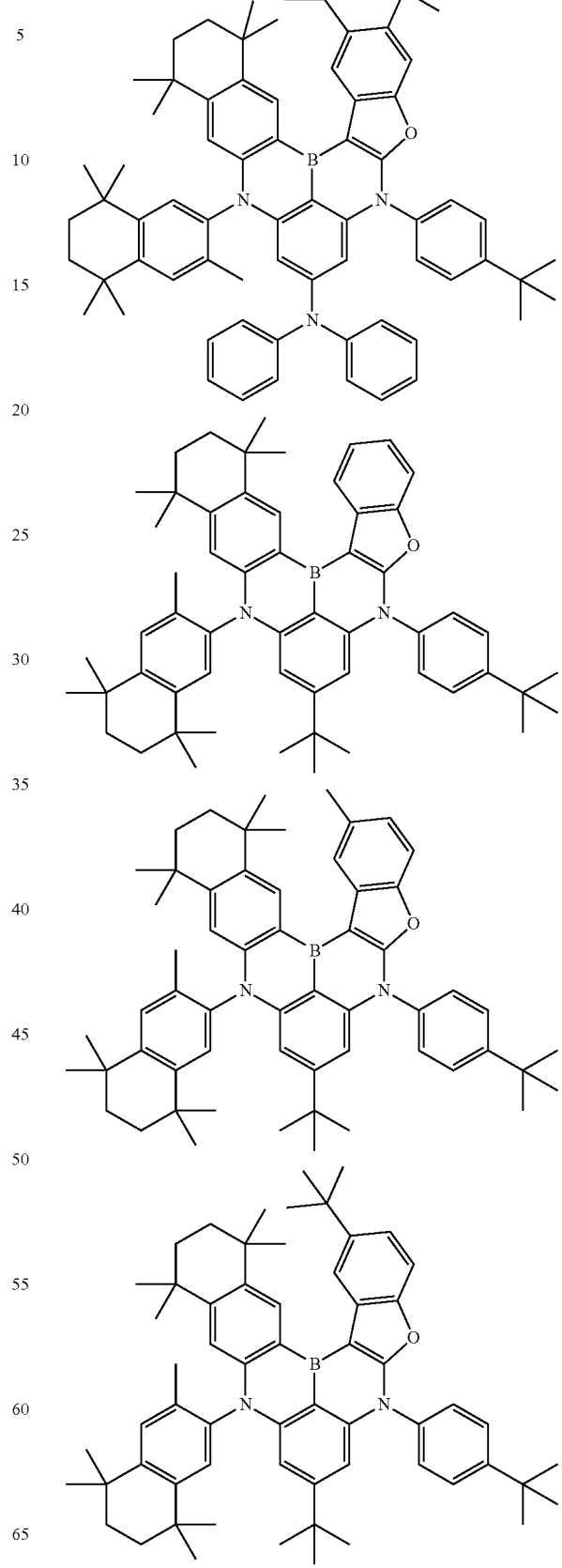 |

1201
-continued
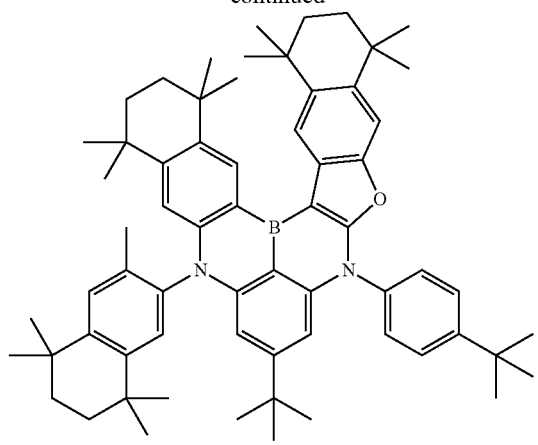
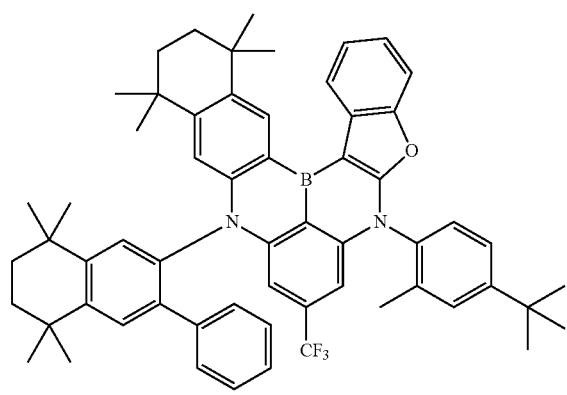
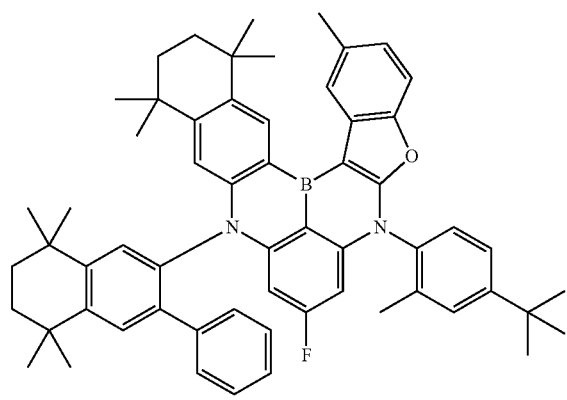
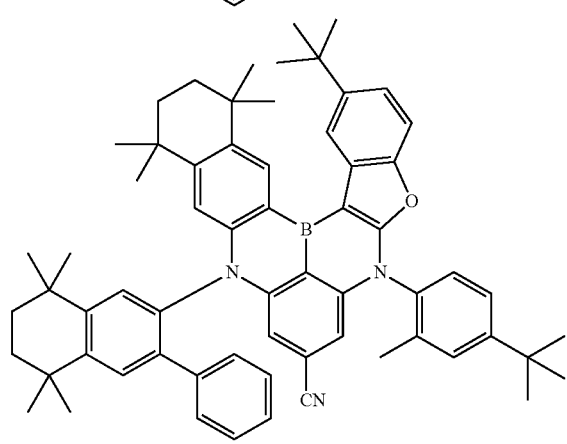
1202
-continued
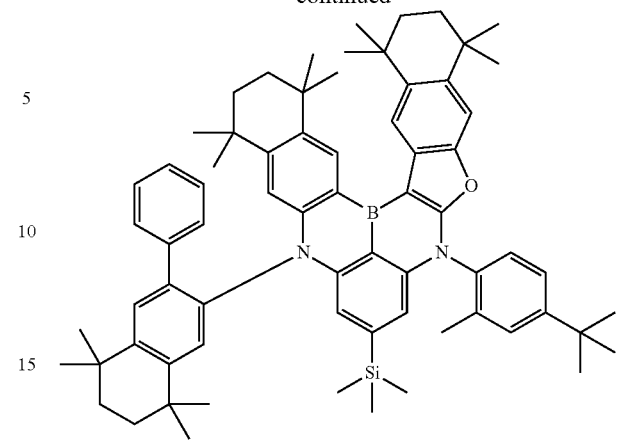
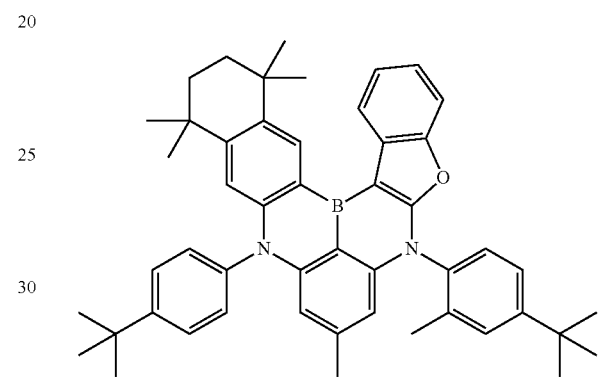
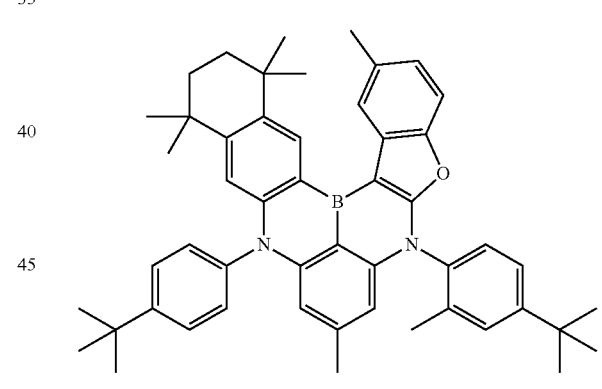
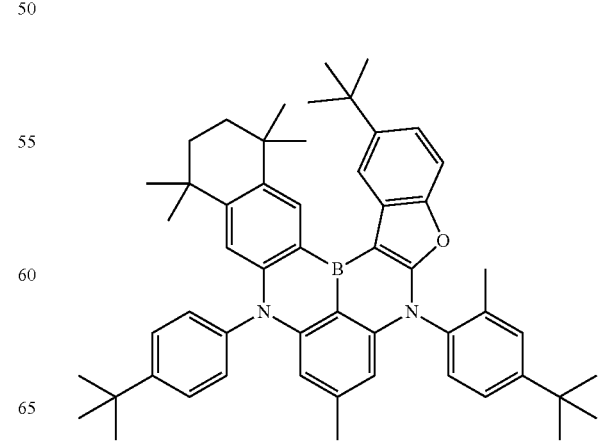

1203
-continued
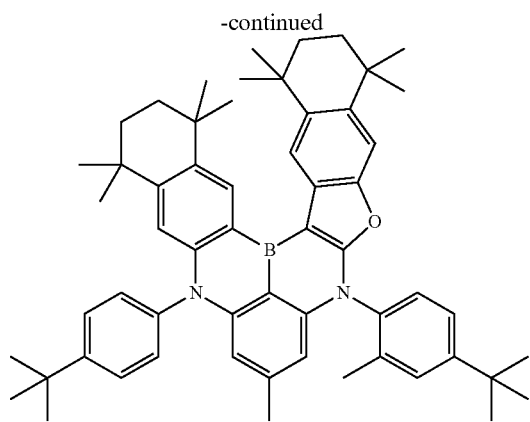
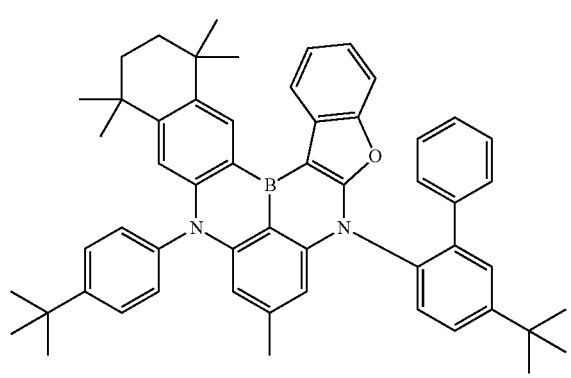
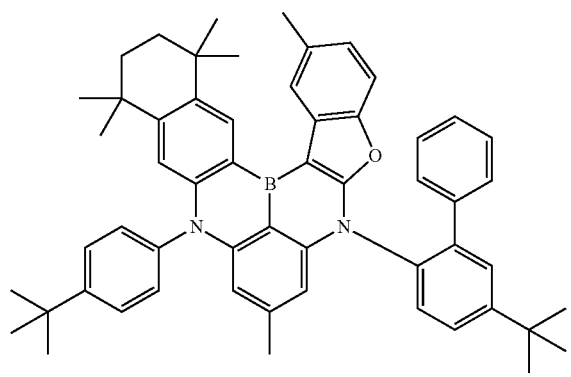
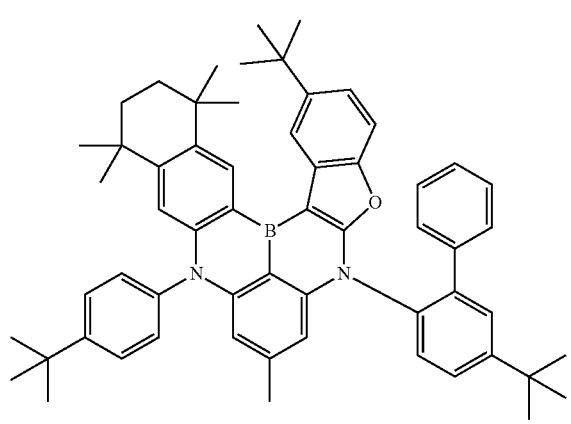
1204
-continued
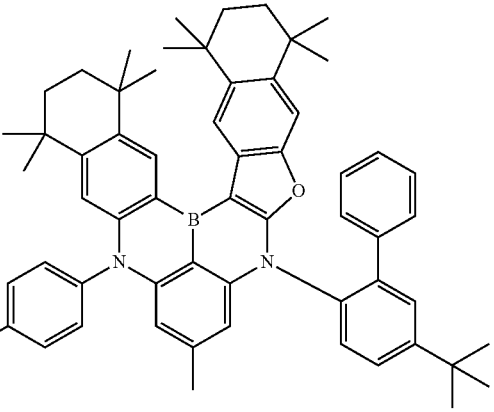
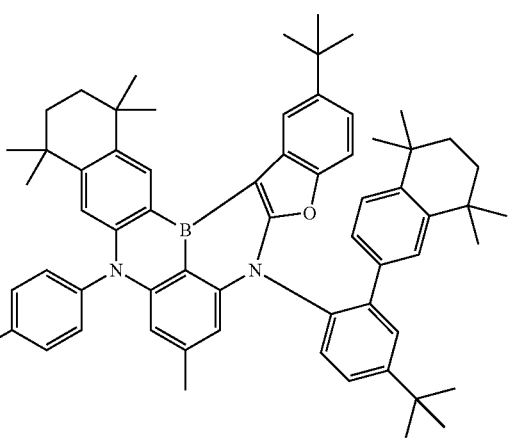
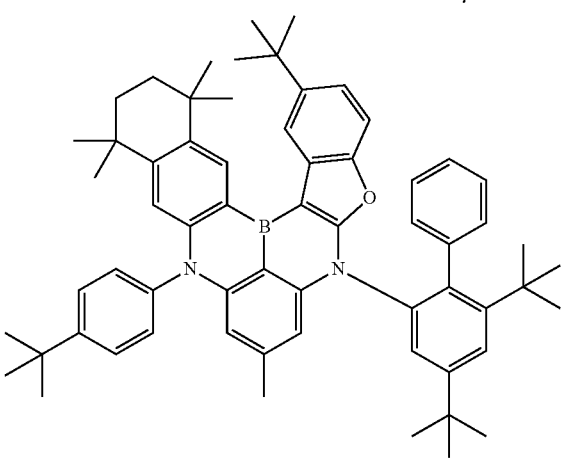
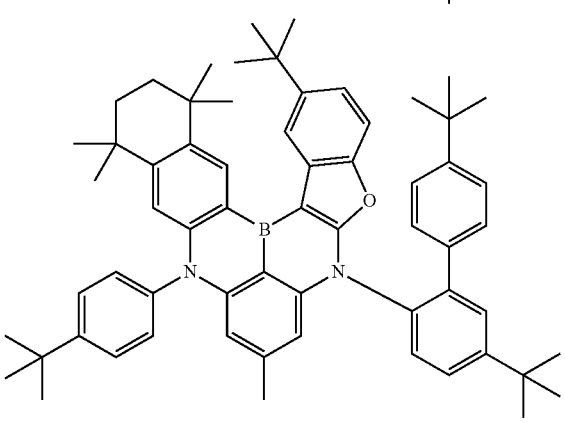

1205
-continued
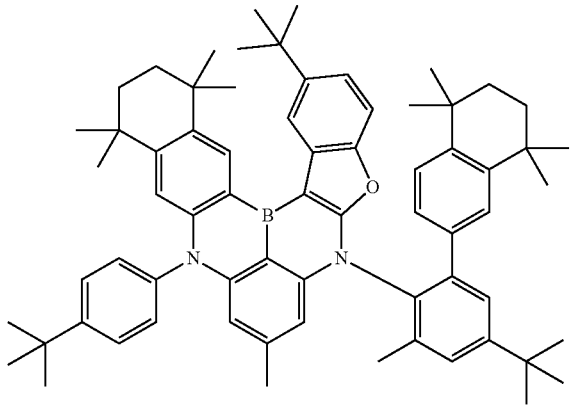

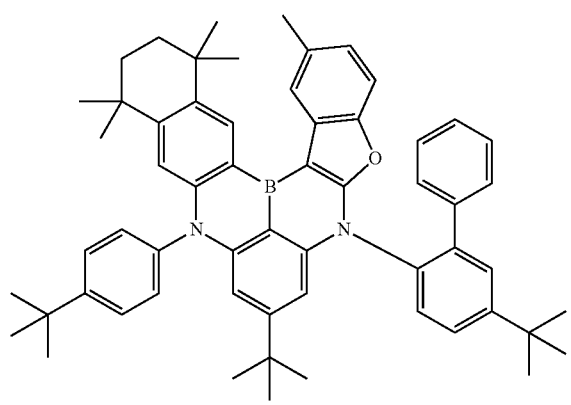
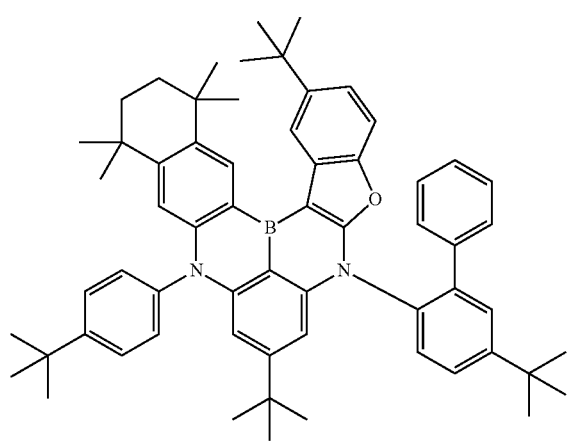
1206
-continued
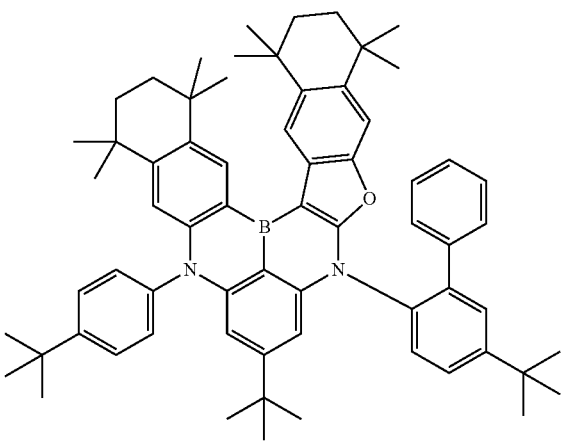
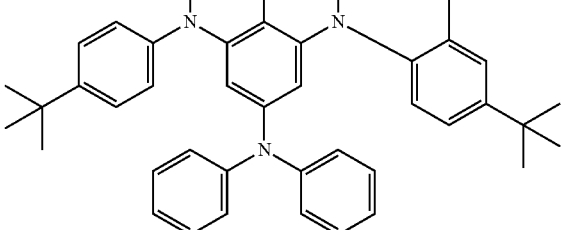
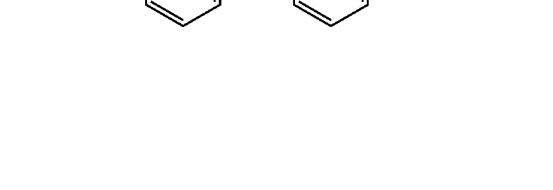
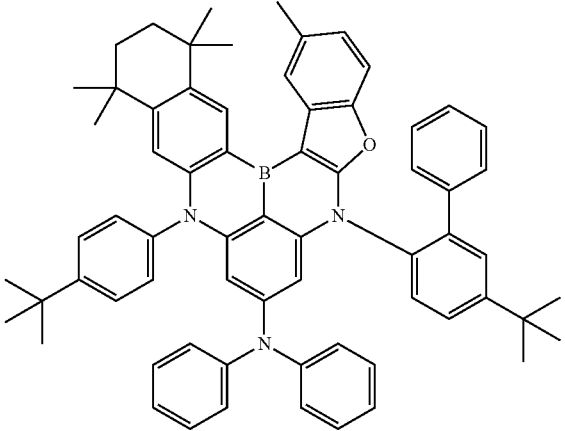

1207
-continued
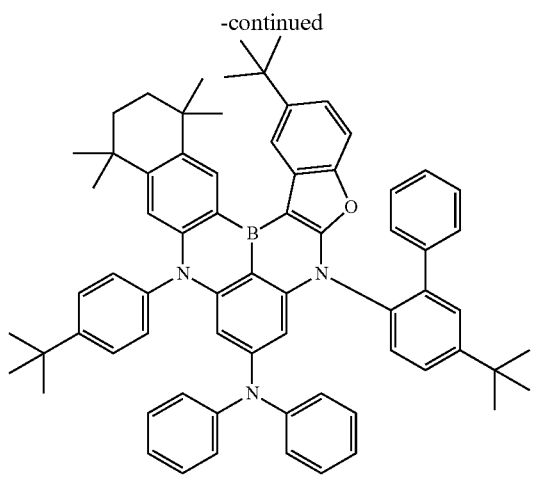
1208
-continued
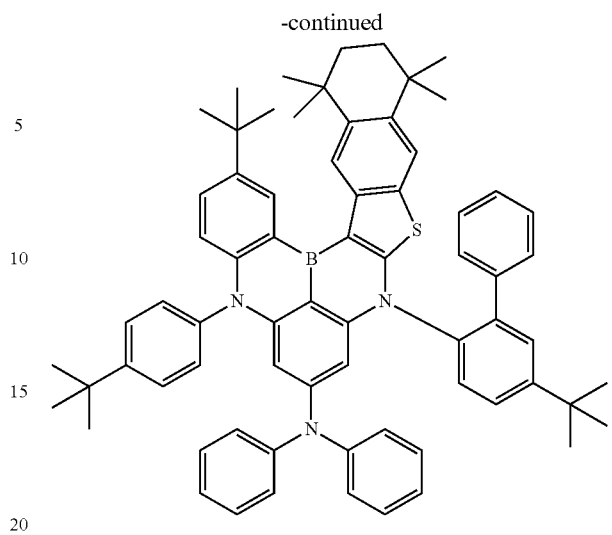
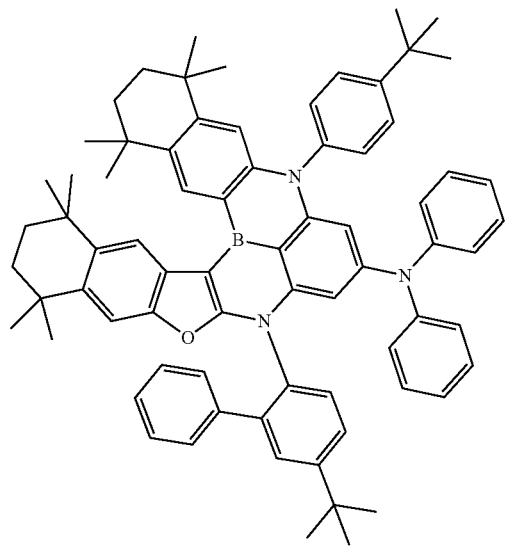
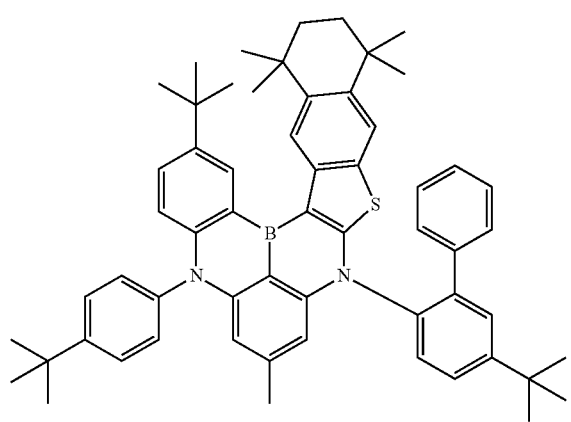
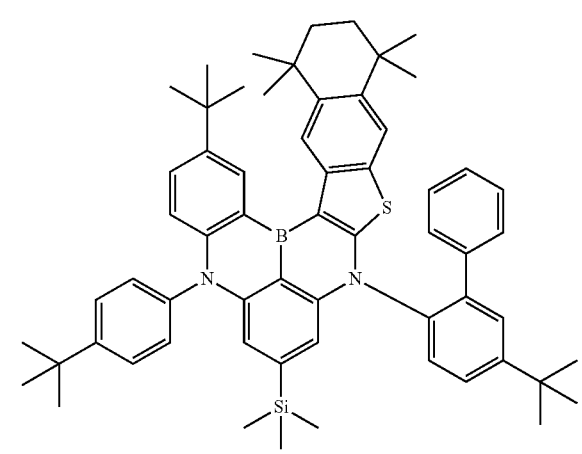

1209
-continued
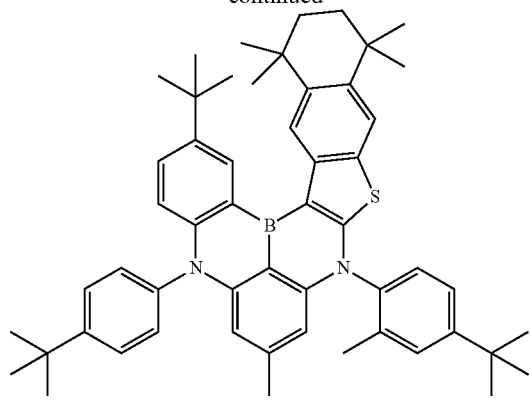
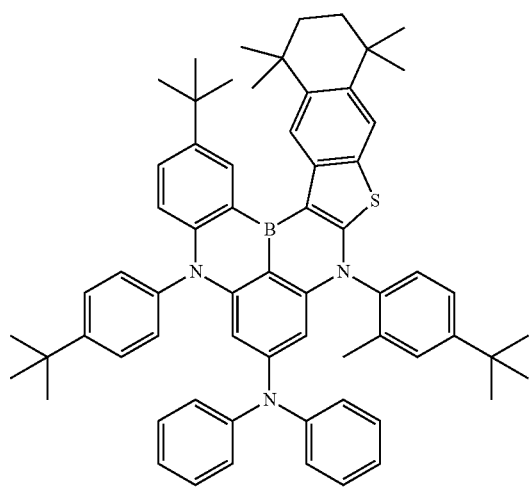
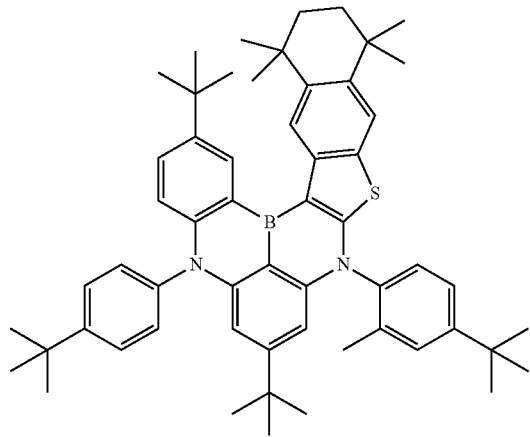
1210
-continued
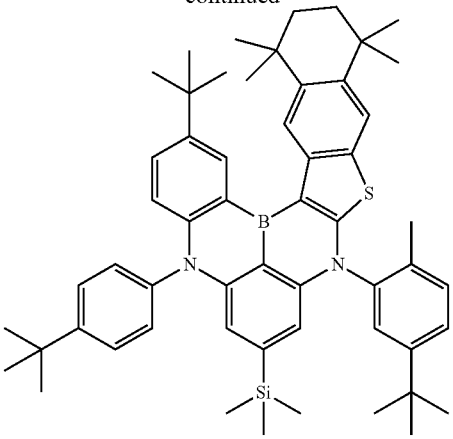
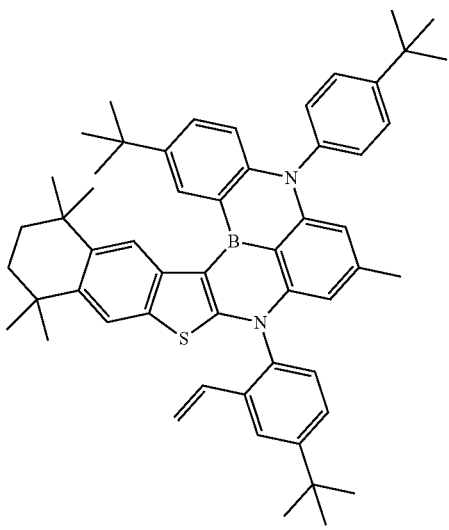
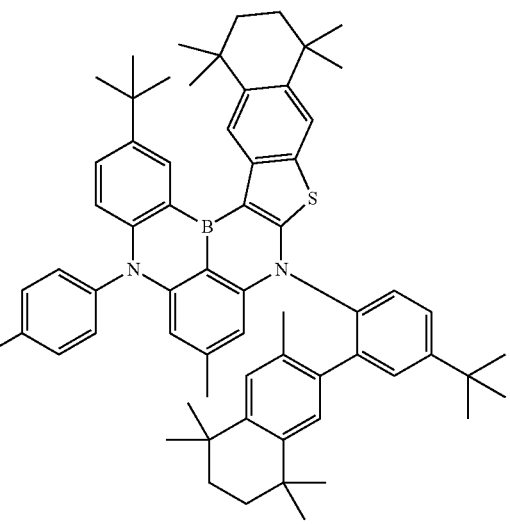

1211
-continued
1212
-continued
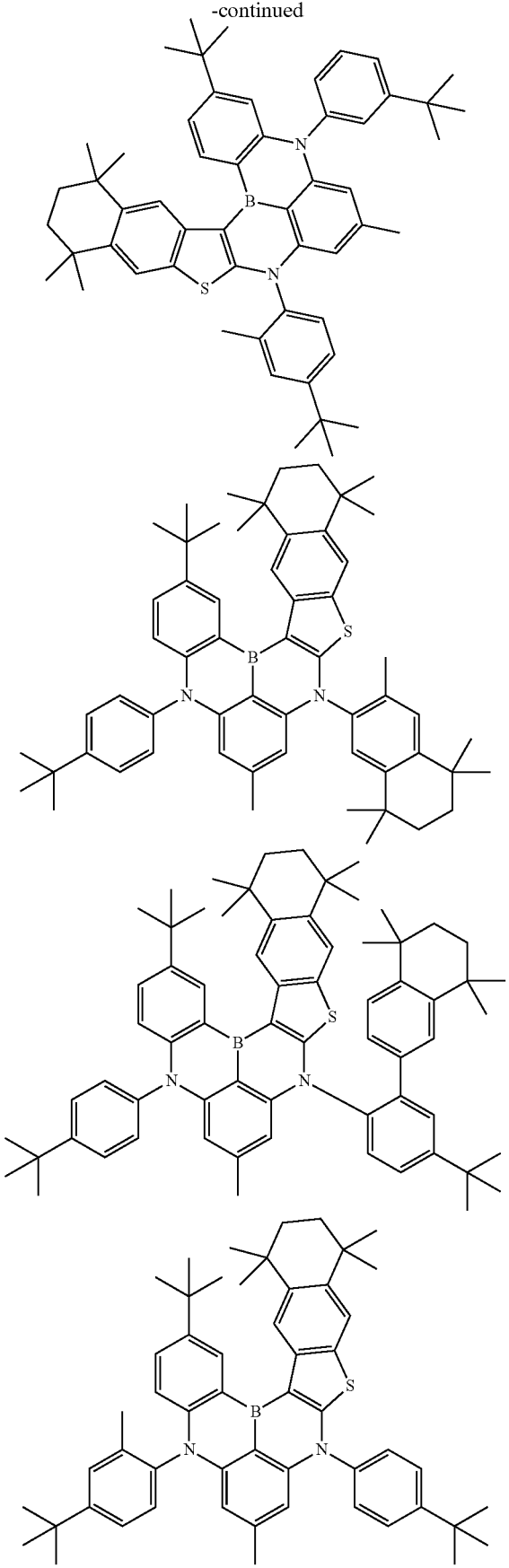
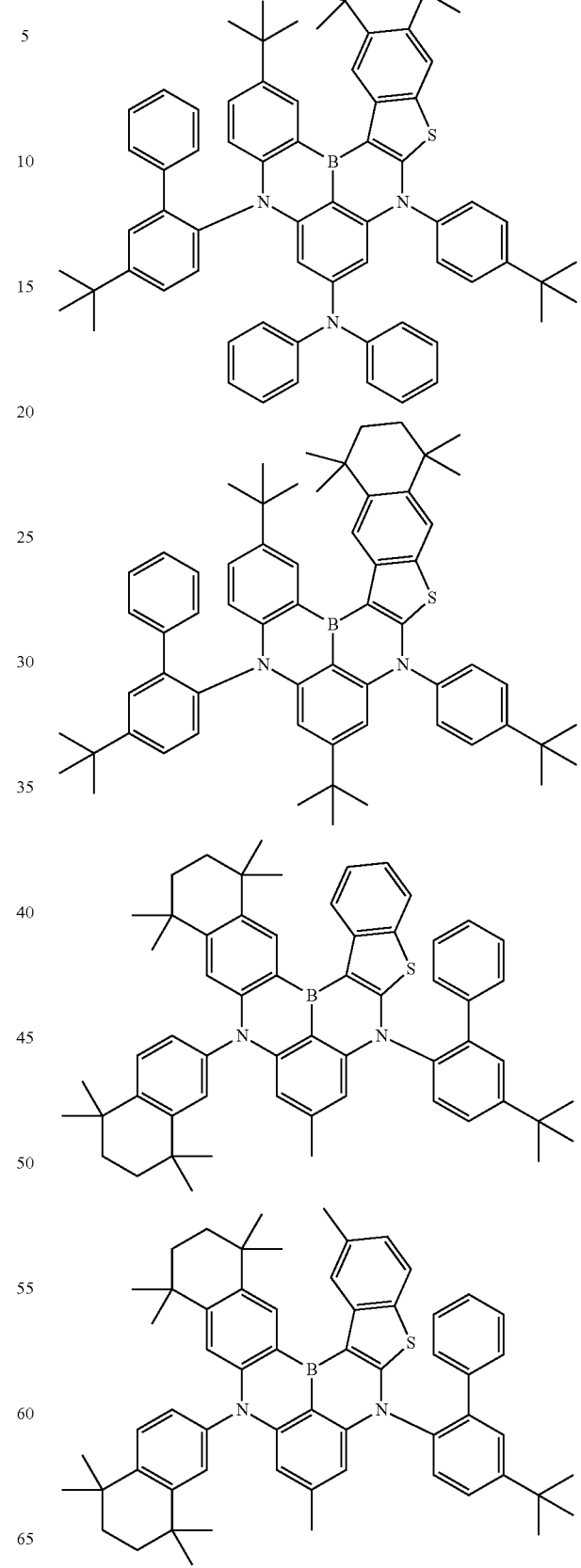

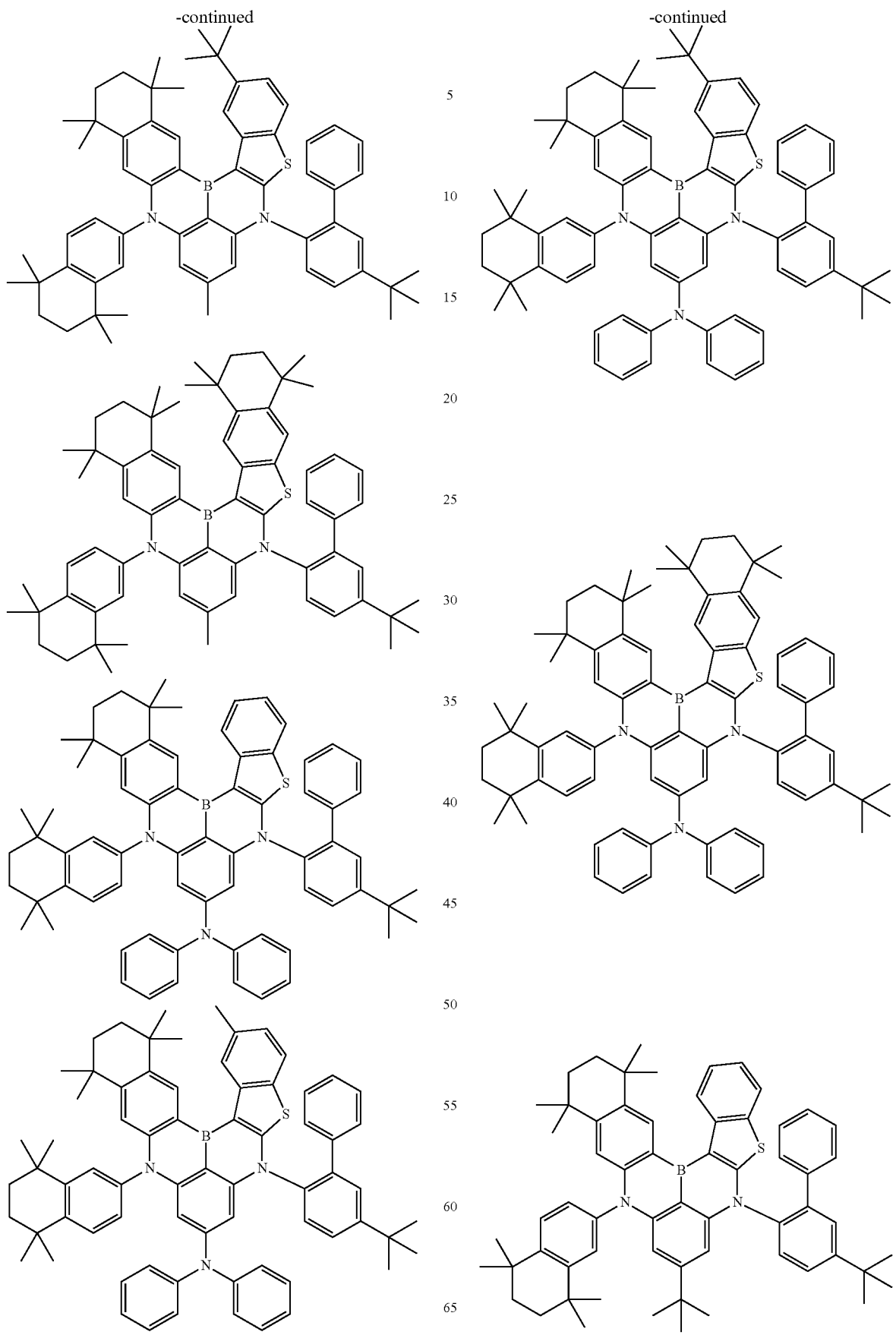

| 1215 -continued | 1216 -continued |
|---|---|
| 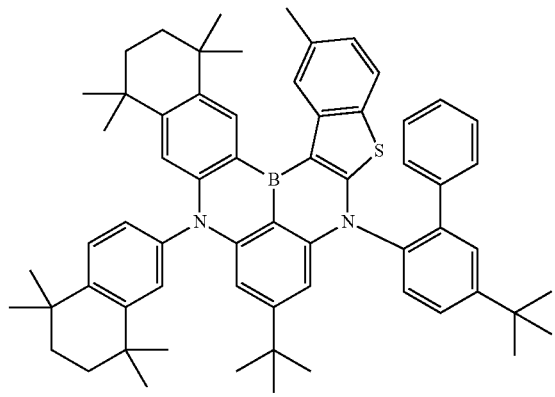 | 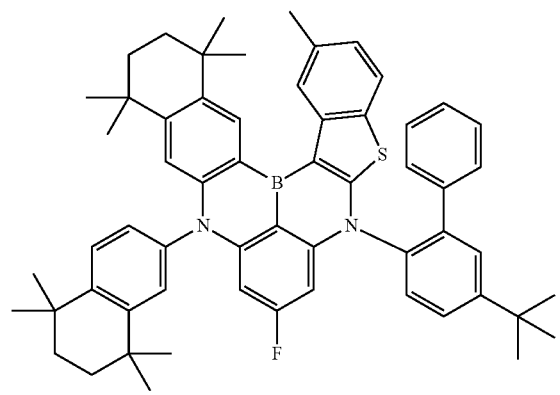 |
| 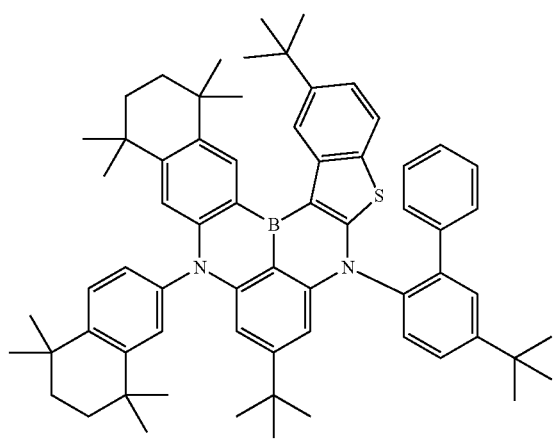 | 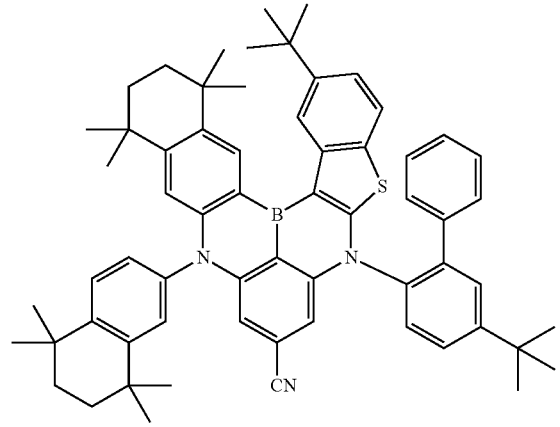 |
| 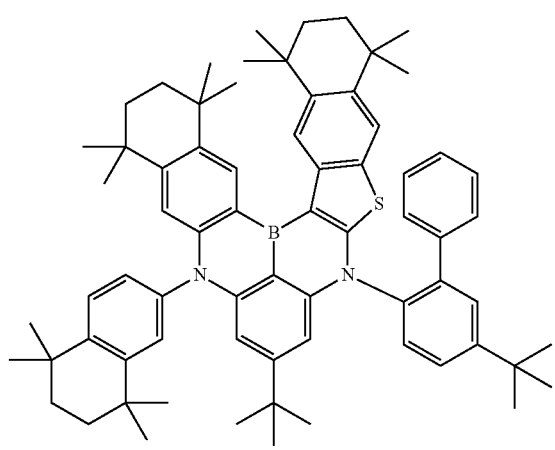 | 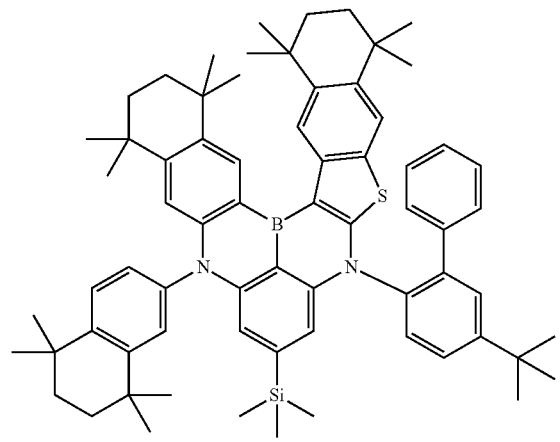 |
| 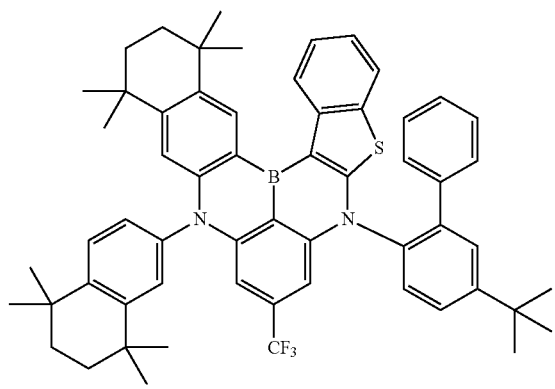 | 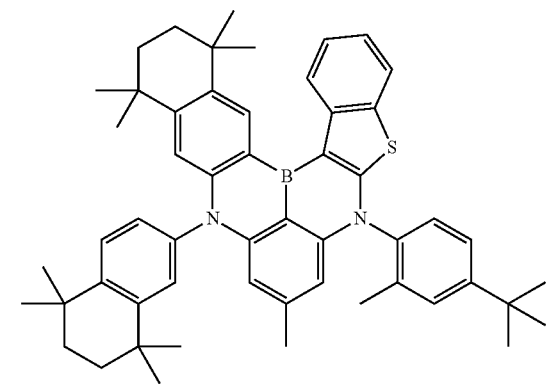 |

1217
-continued
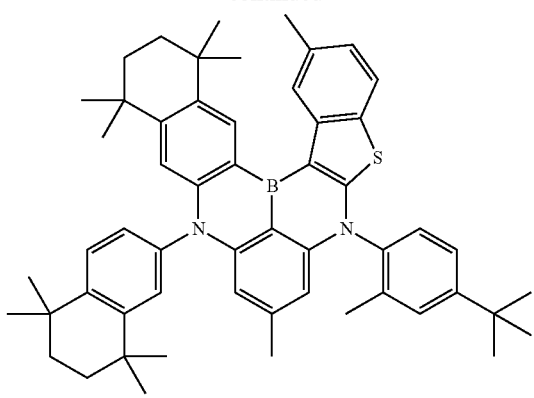
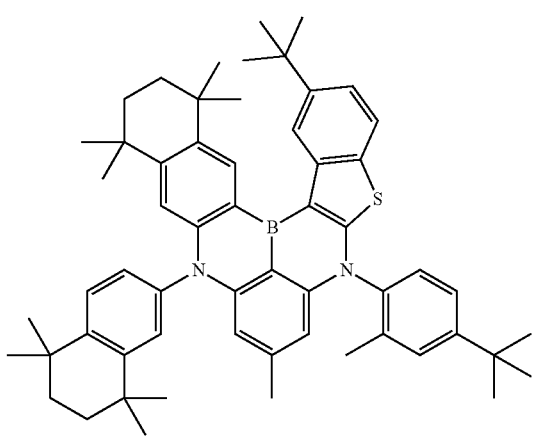
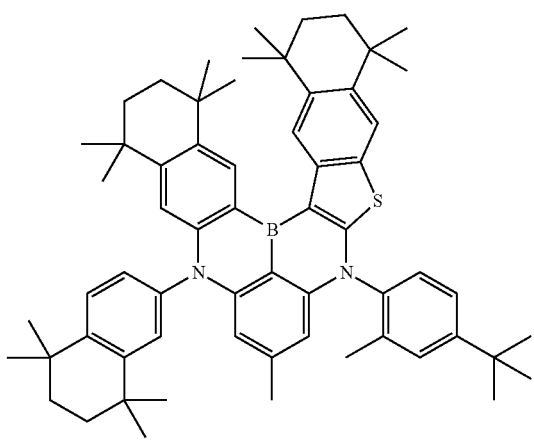
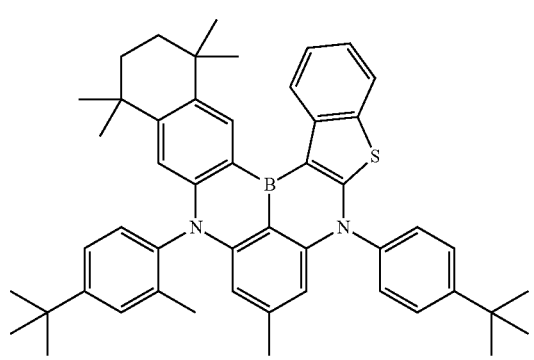
1218
-continued
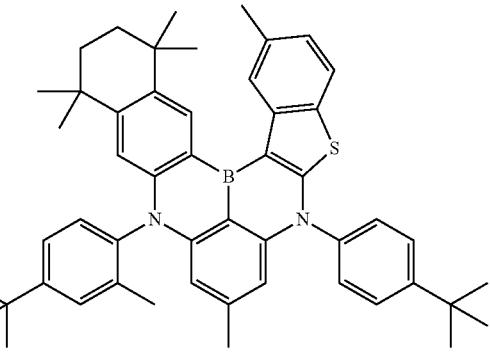
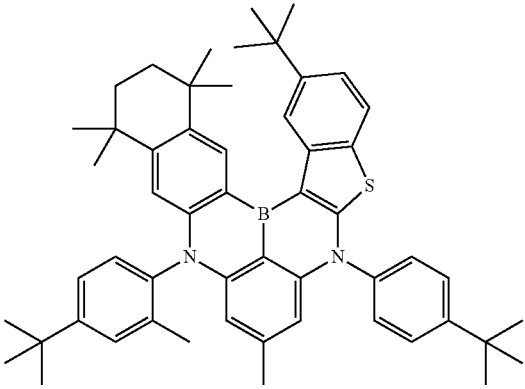
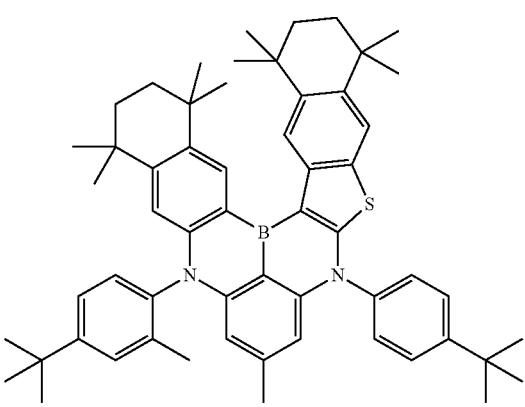
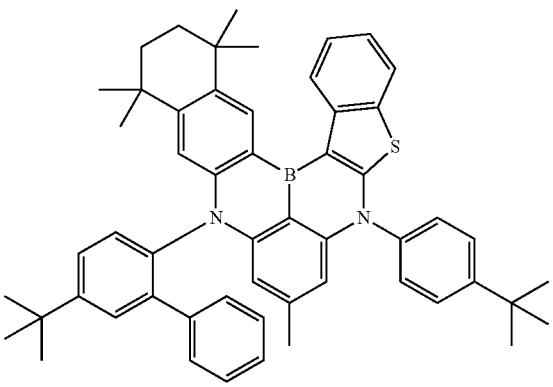

1219
-continued
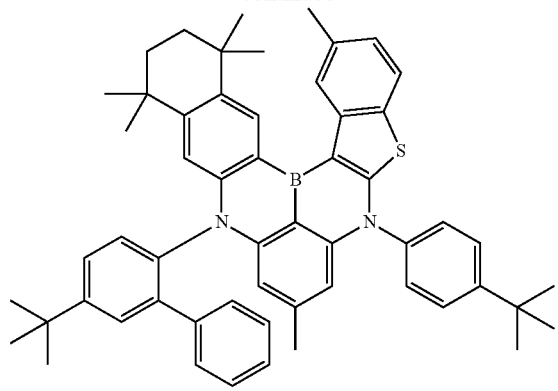
1220
-continued
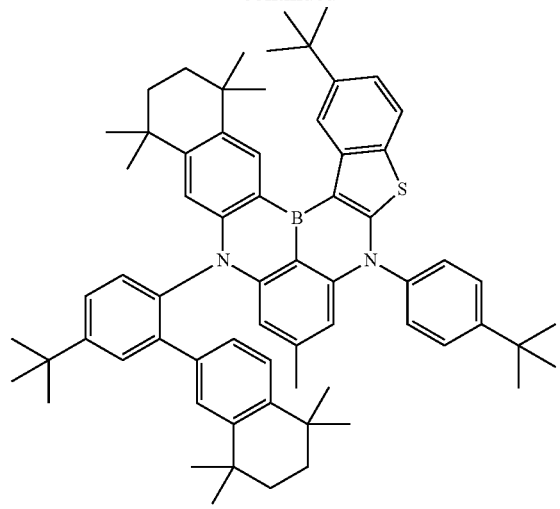
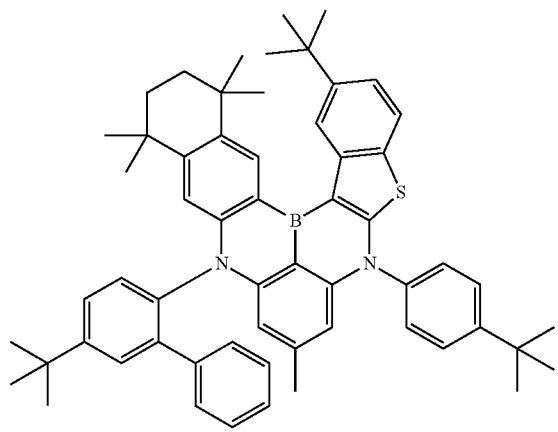
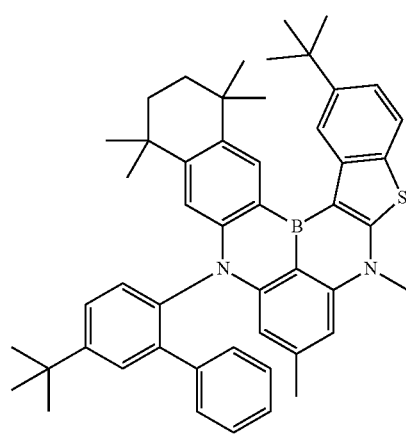
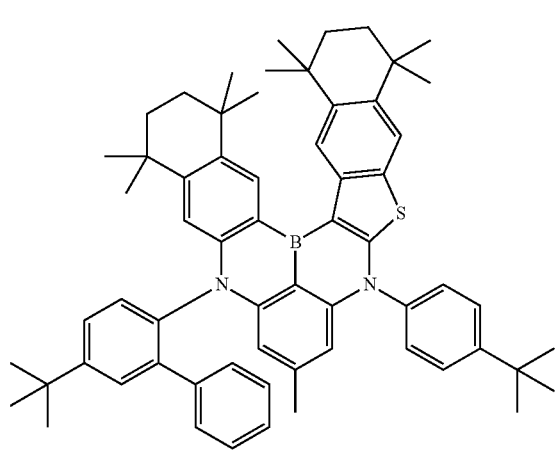
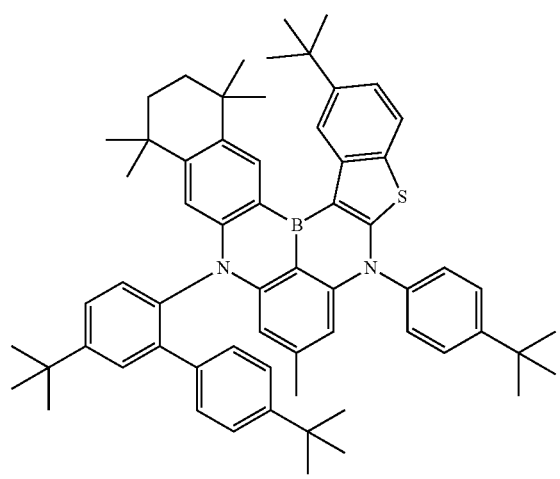

1221
-continued
1222
-continued
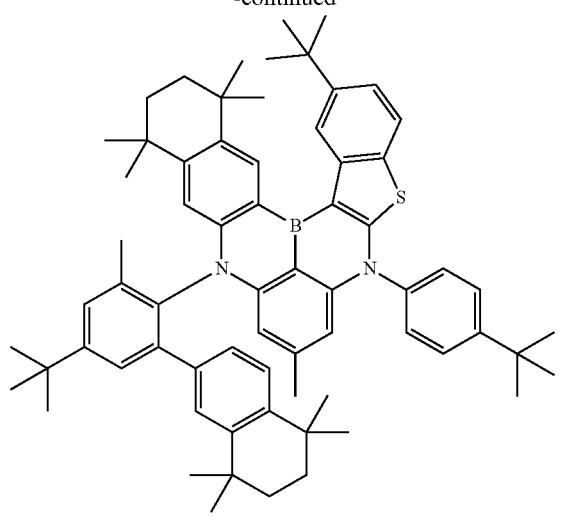
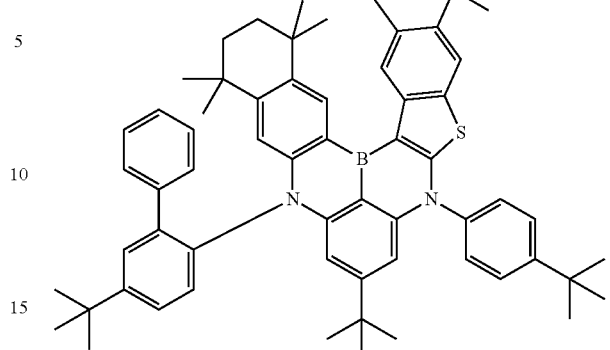
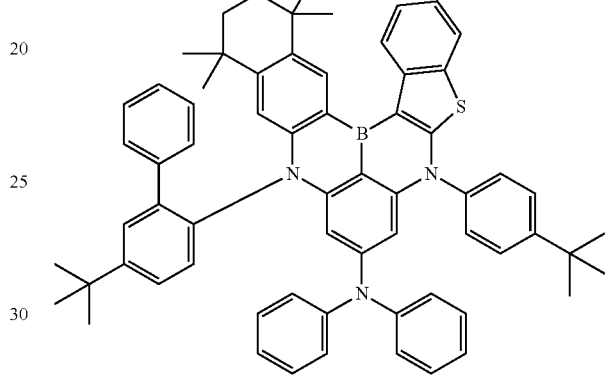
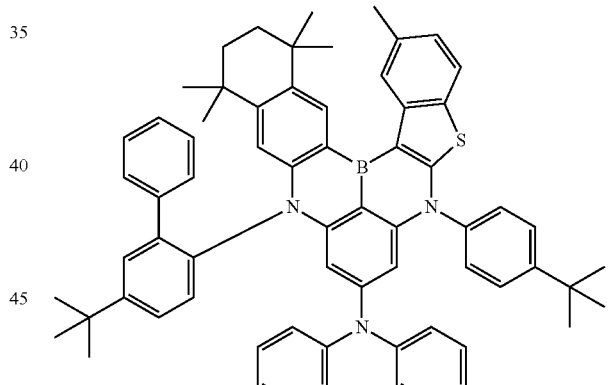
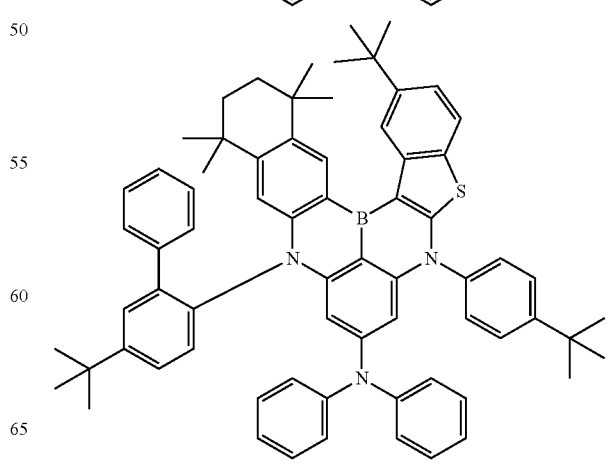

1223
-continued
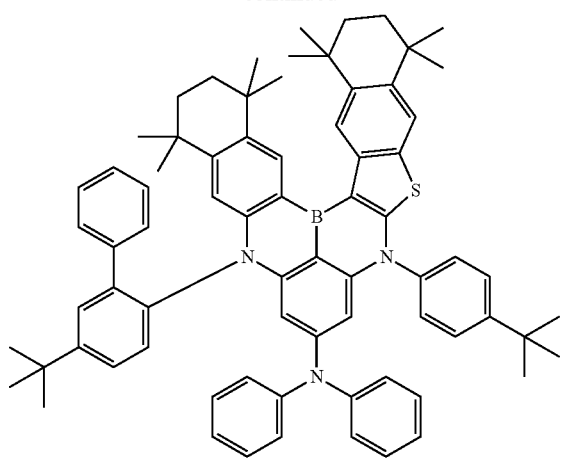
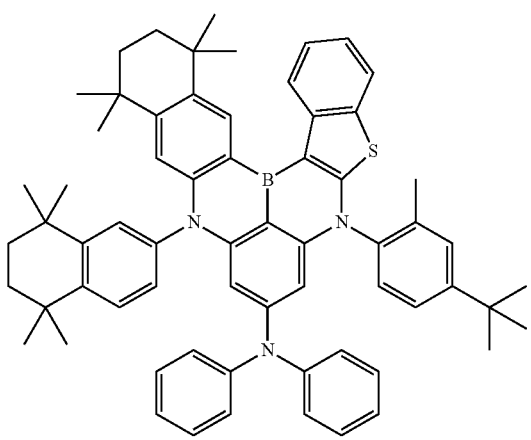
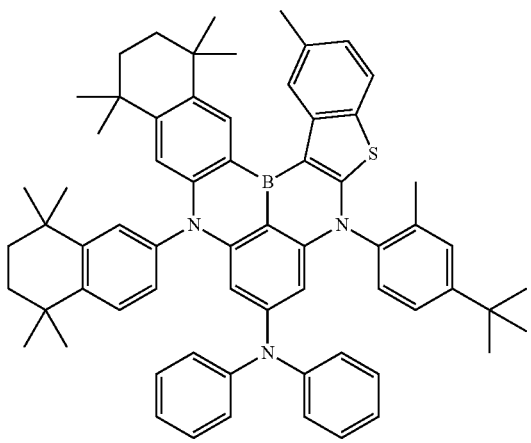
1224
-continued
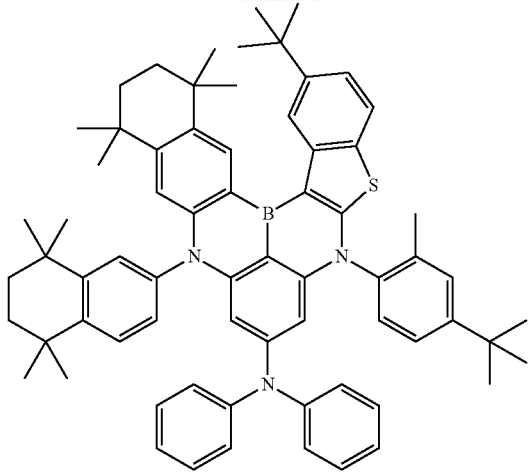
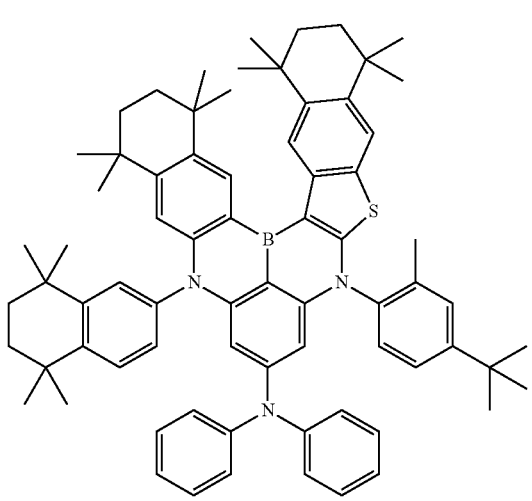
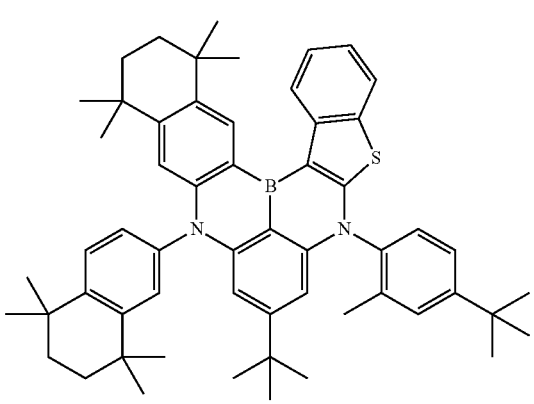

| 1225 -continued | 1226 -continued |
|---|---|
| 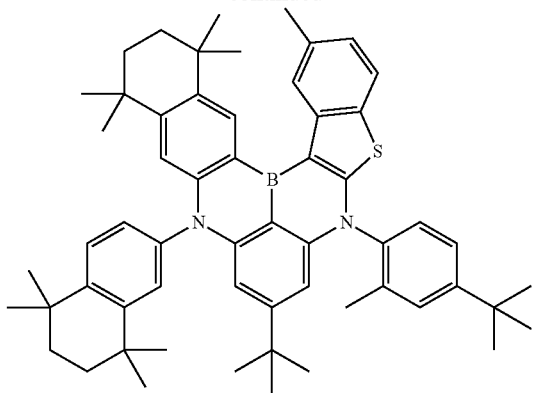 | 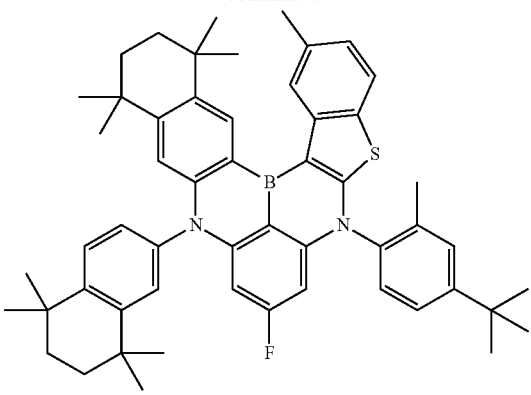 |
| 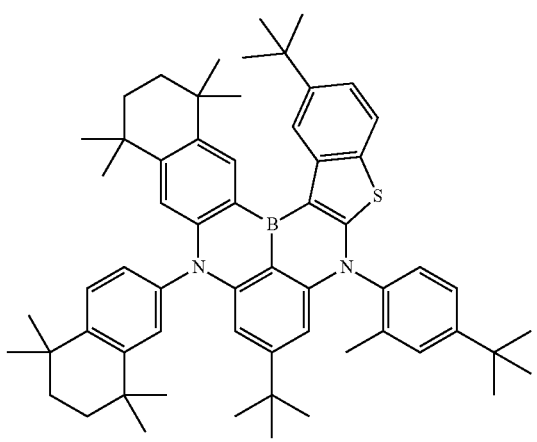 | 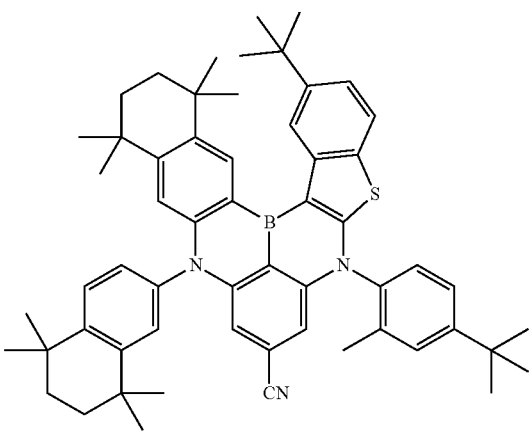 |
| 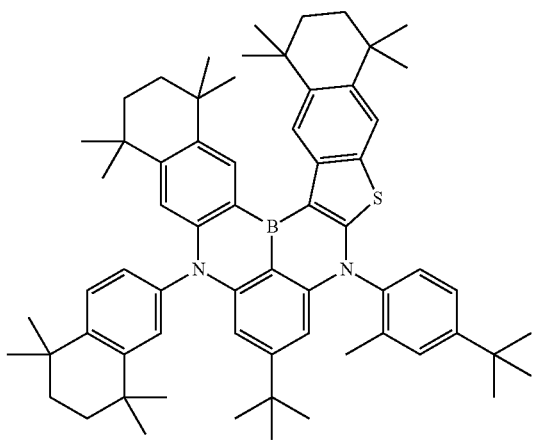 | 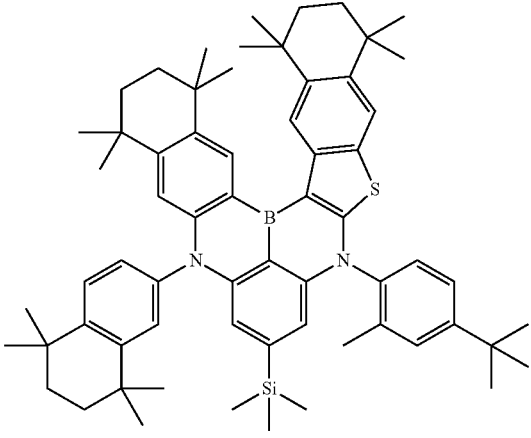 |
| 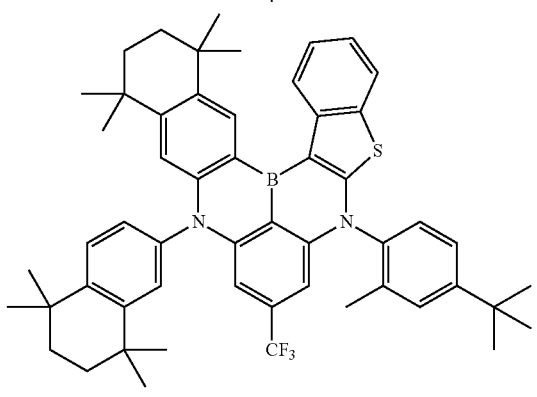 | 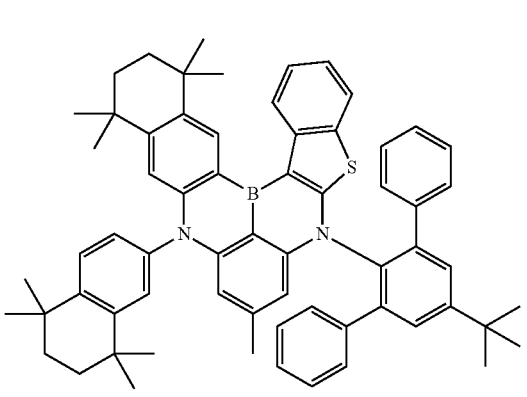 |

1227
-continued
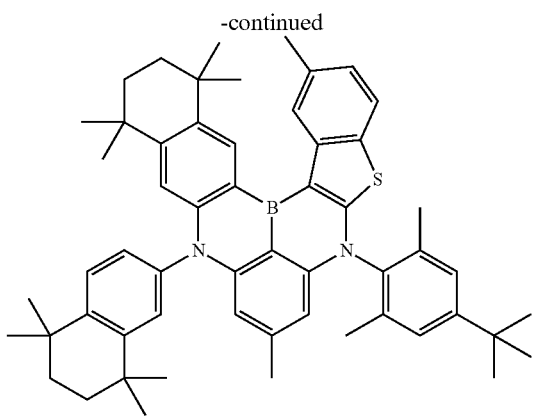
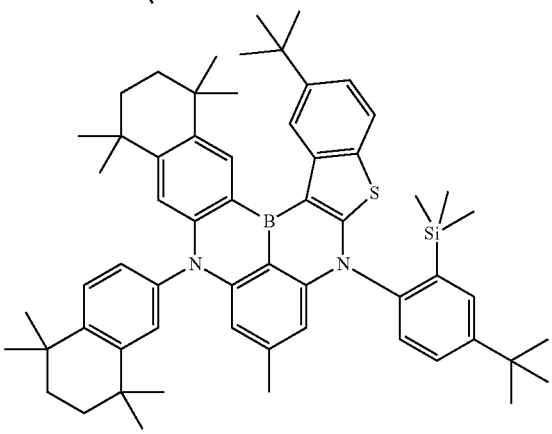
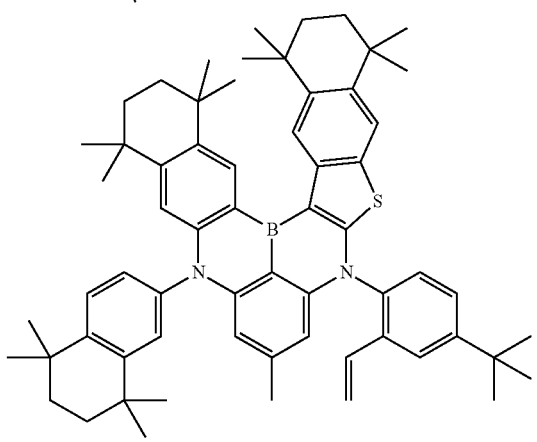
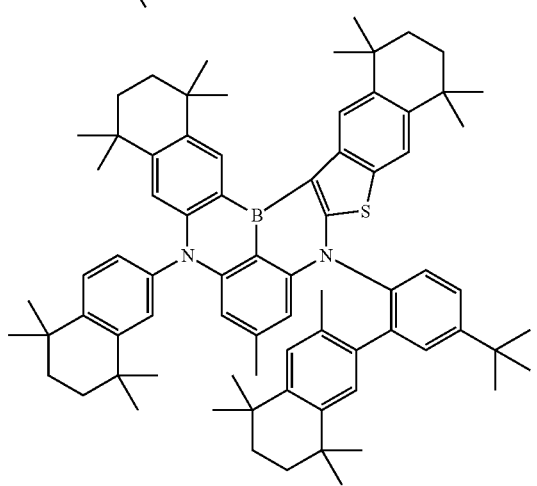
1228
-continued
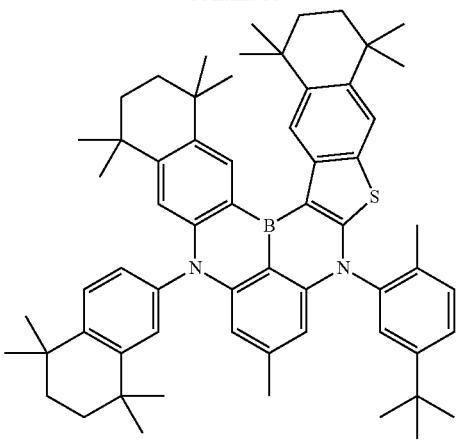
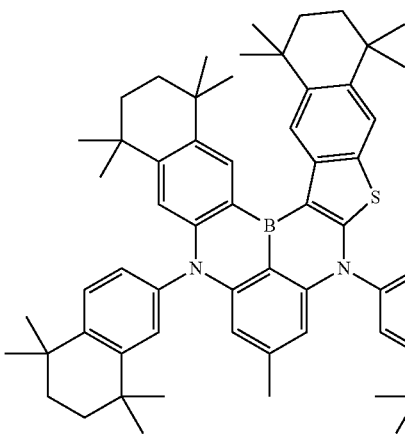
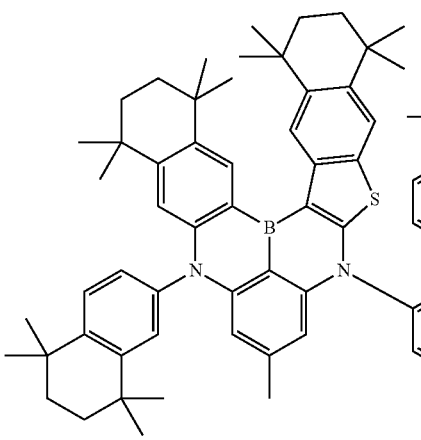
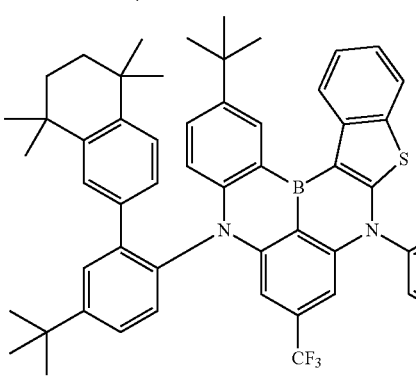

1229
-continued
1230
-continued
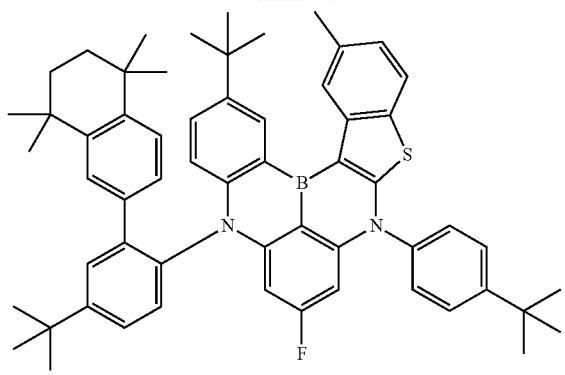
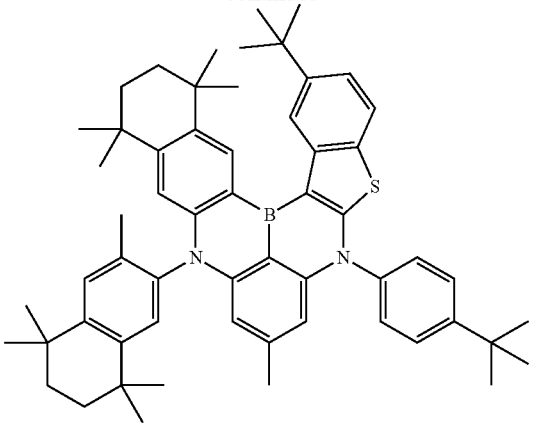
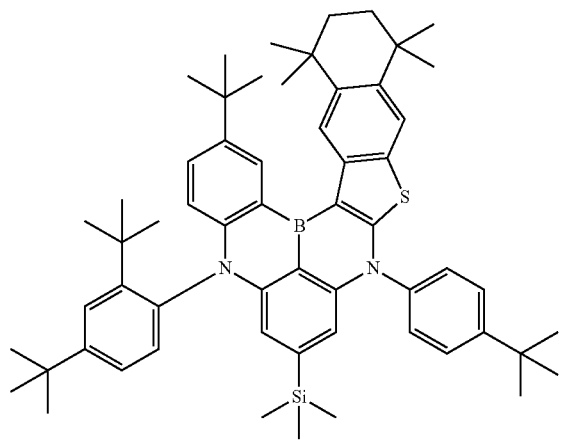
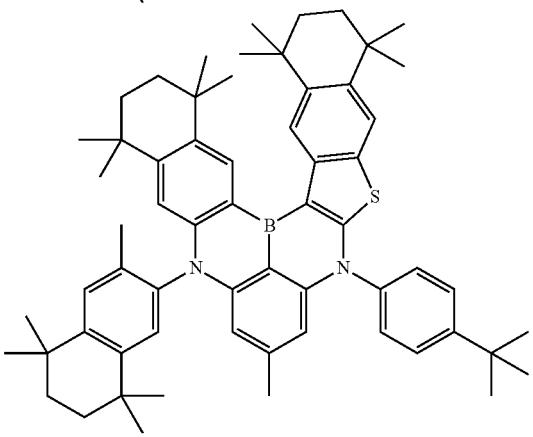
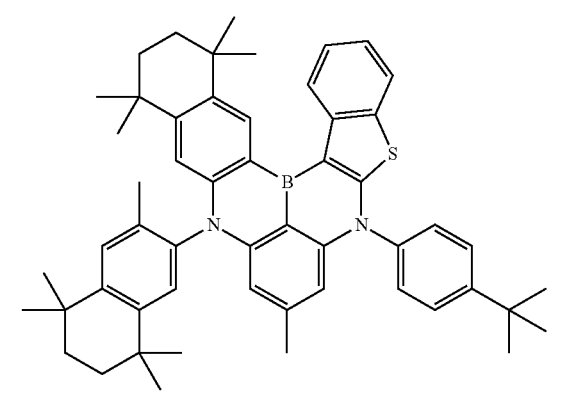
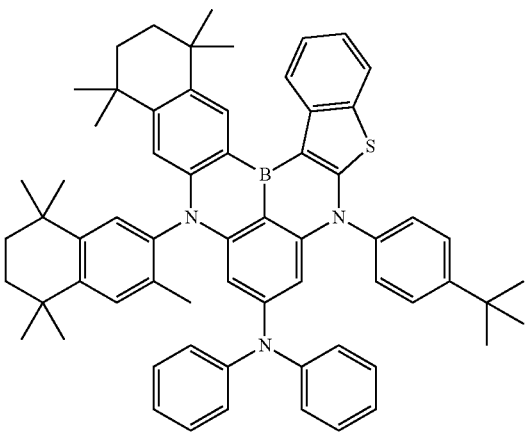
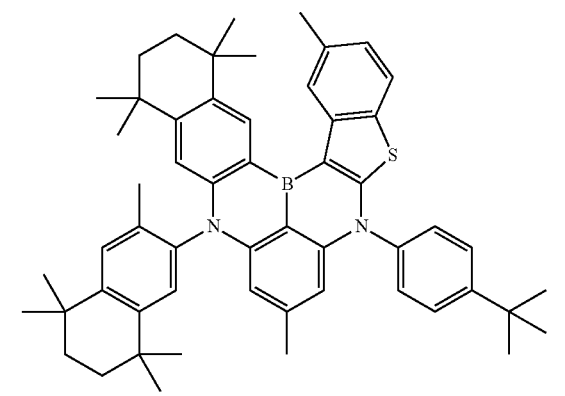
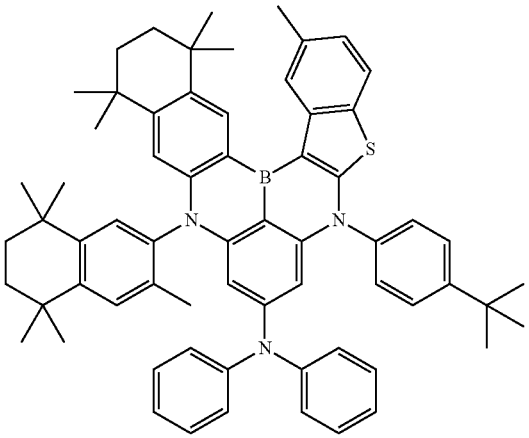

1231
-continued
1232
-continued
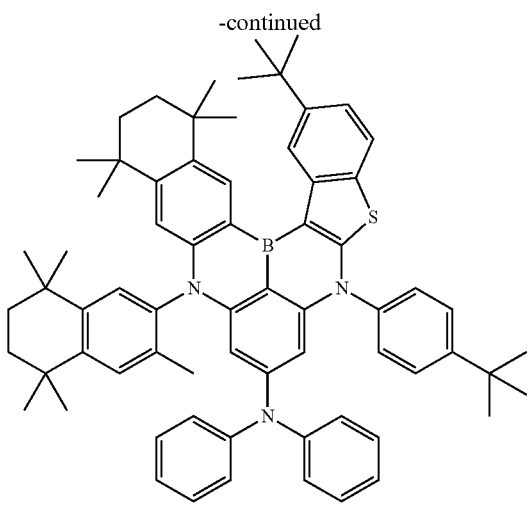
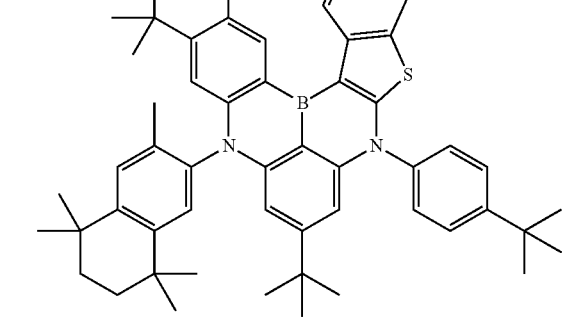
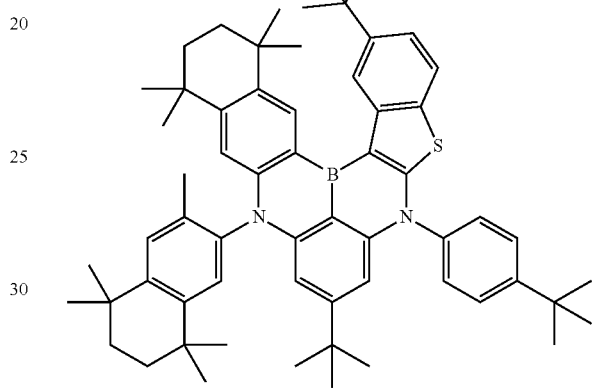
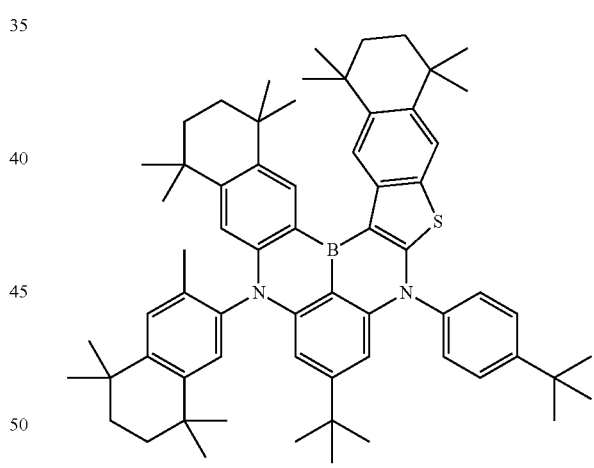
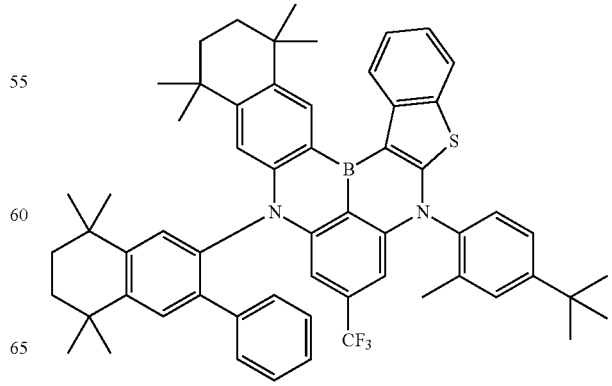

1233
-continued
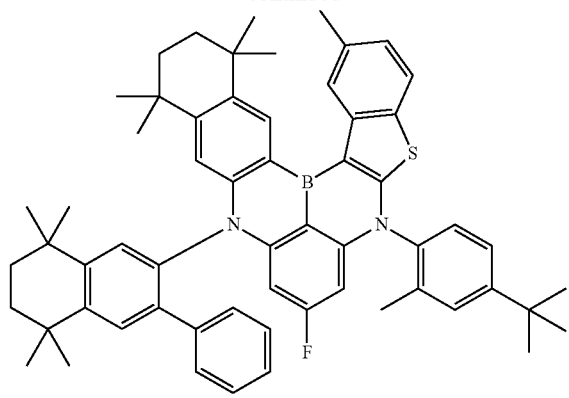
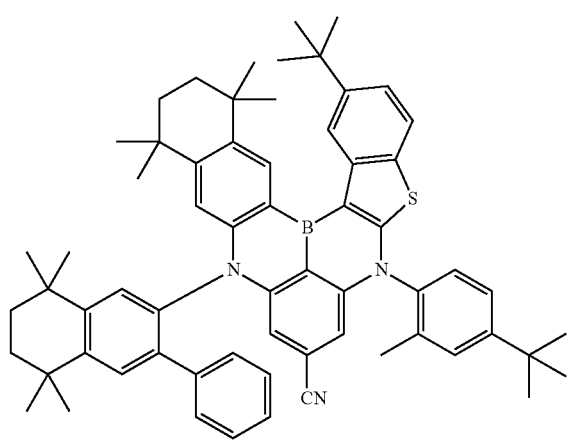
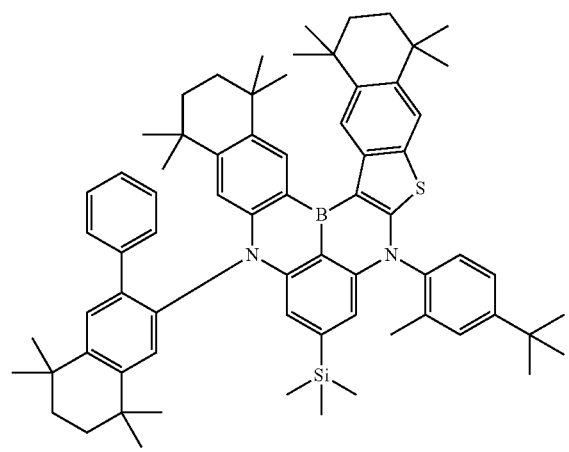
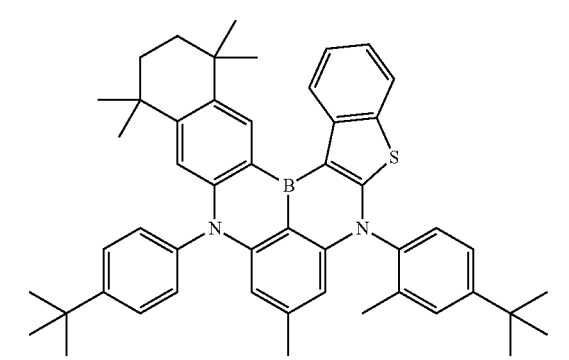
1234
-continued
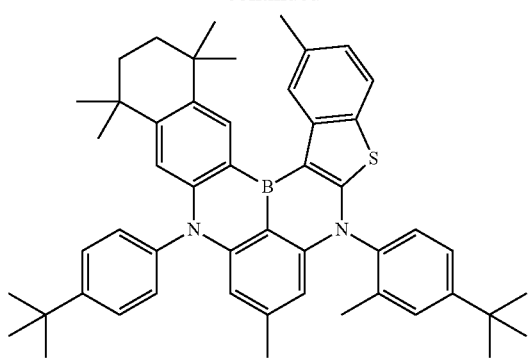
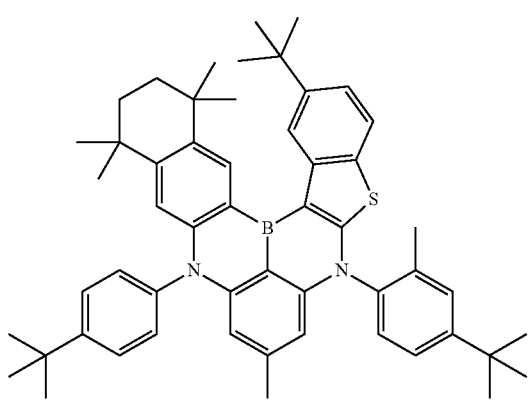
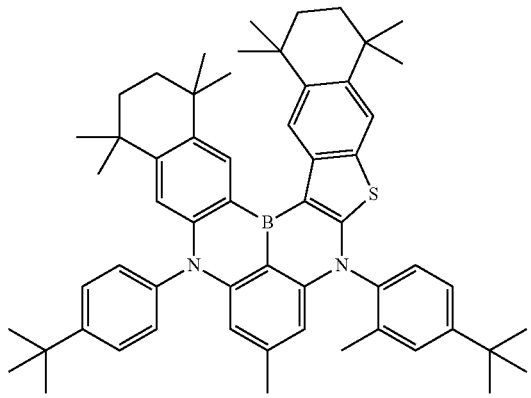
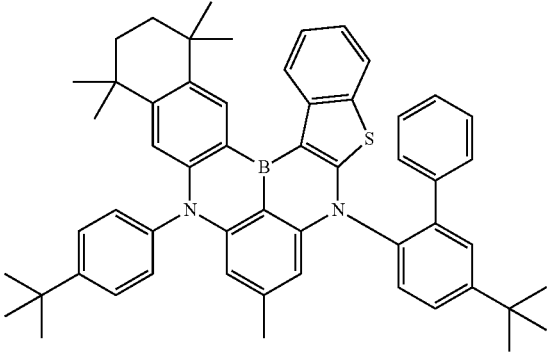

1235
-continued
1236
-continued
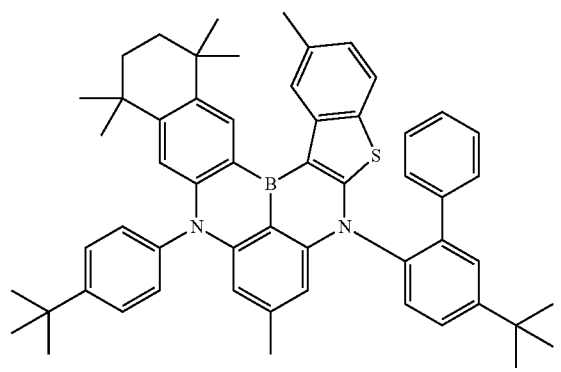
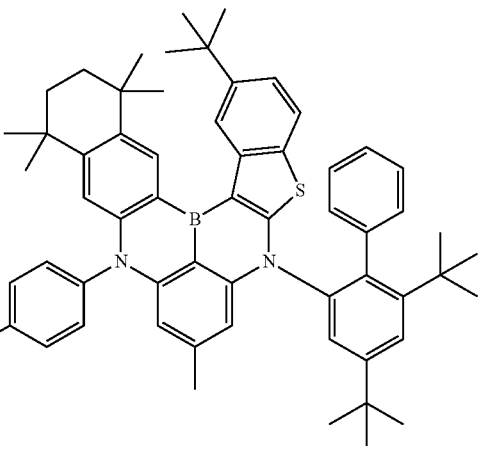
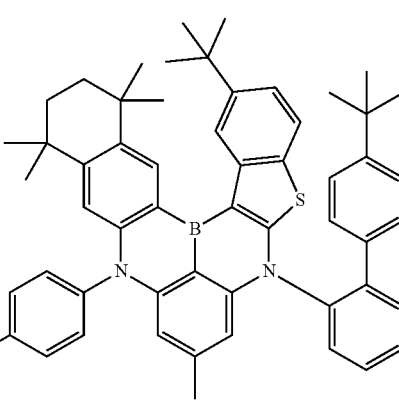
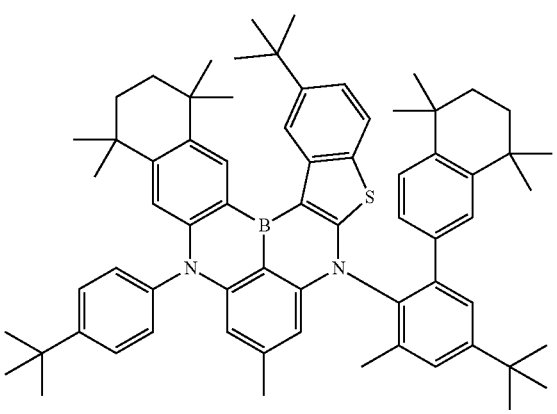
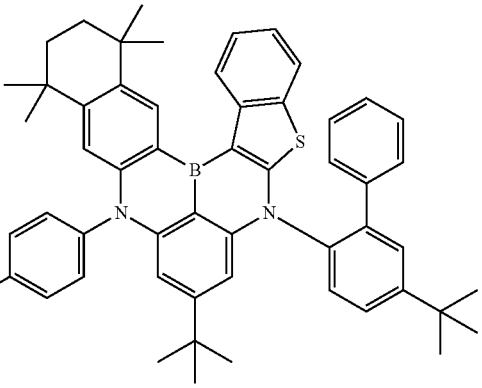

1237
-continued
1238
-continued
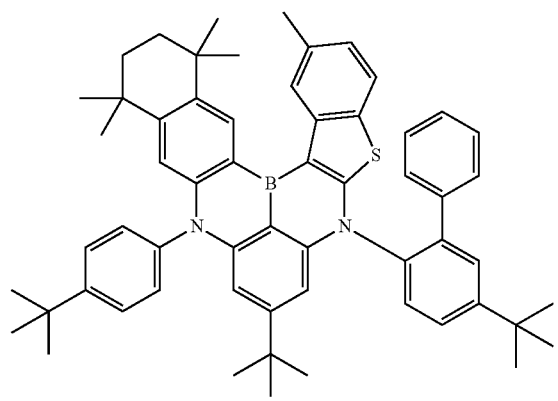
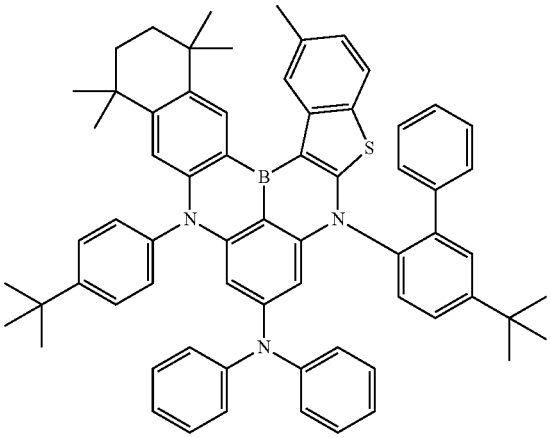
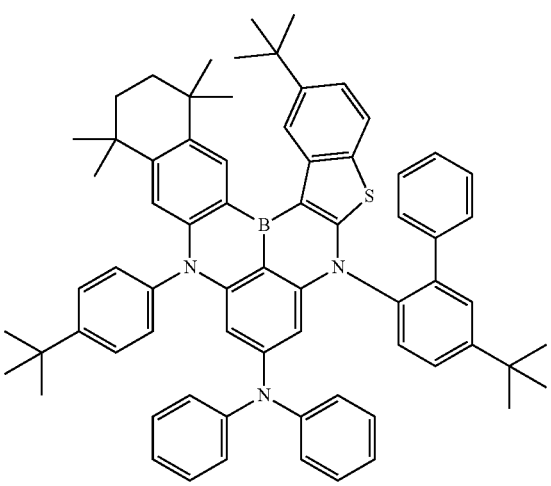
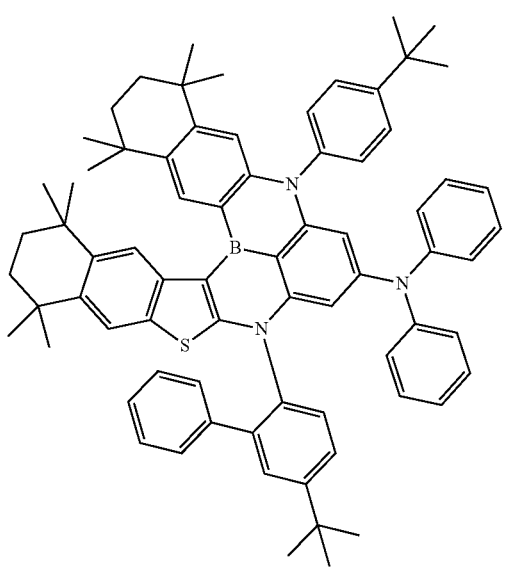

1239 -continued
1240 -continued
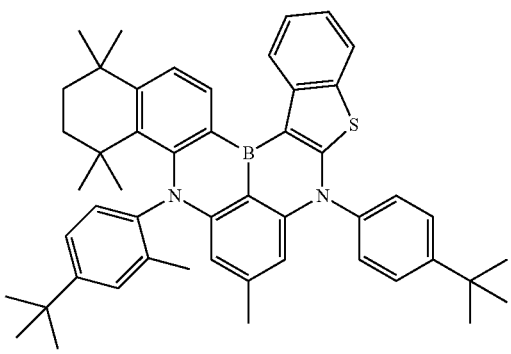
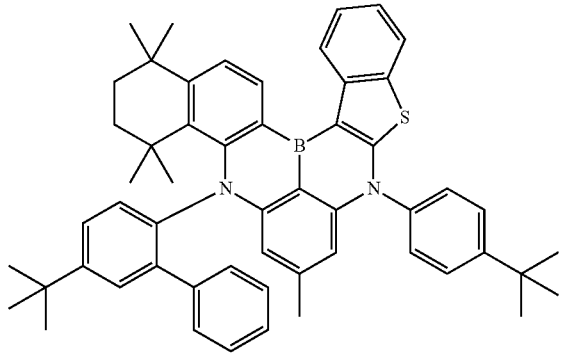
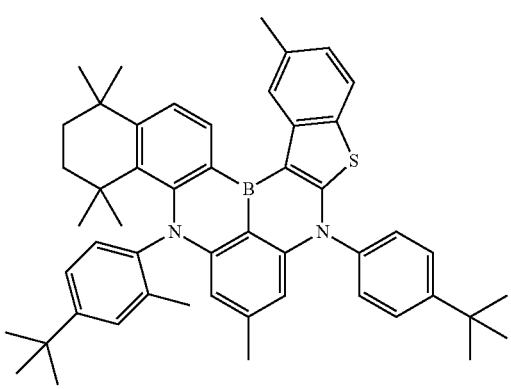
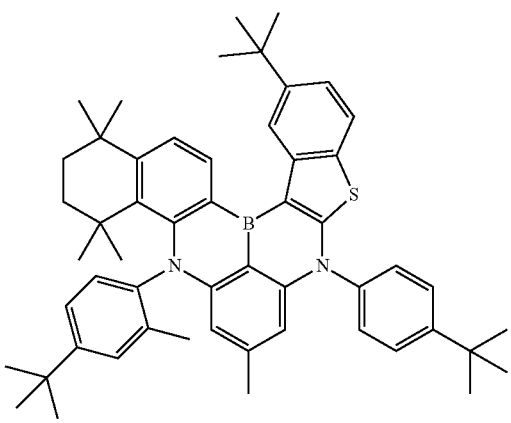
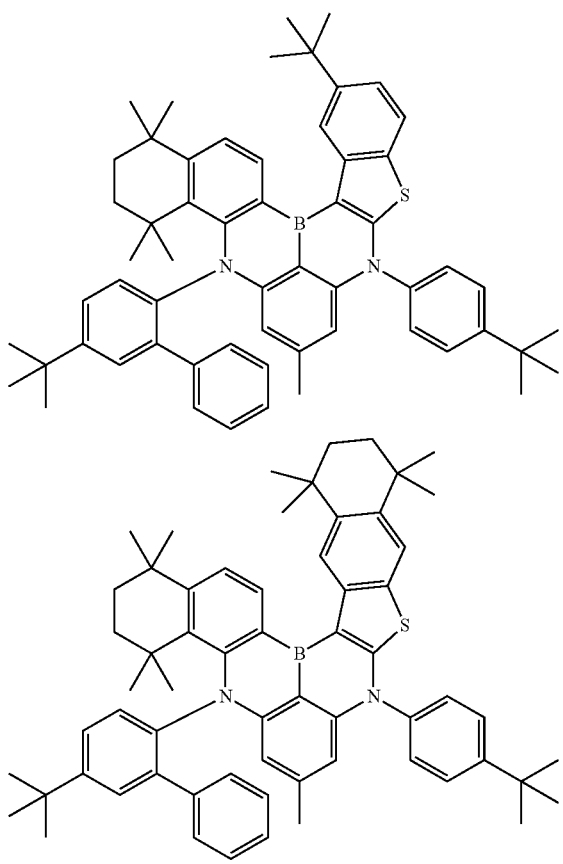

1241
-continued
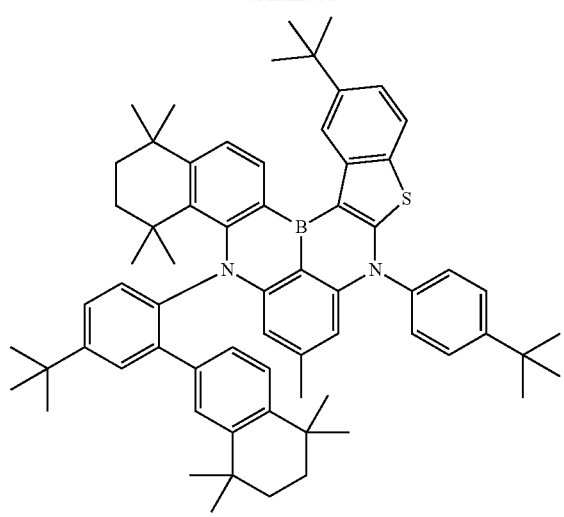
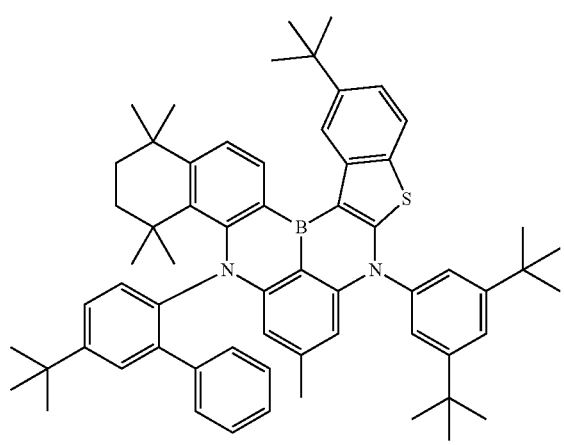
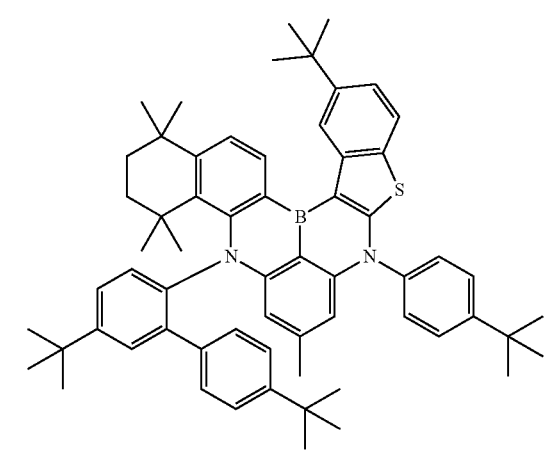
1242
-continued
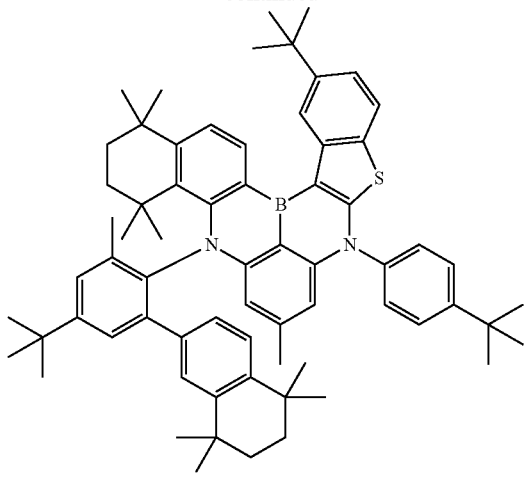
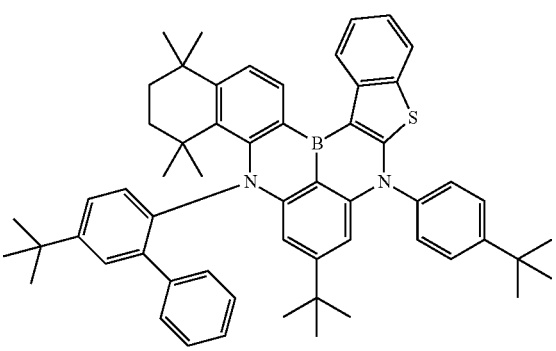
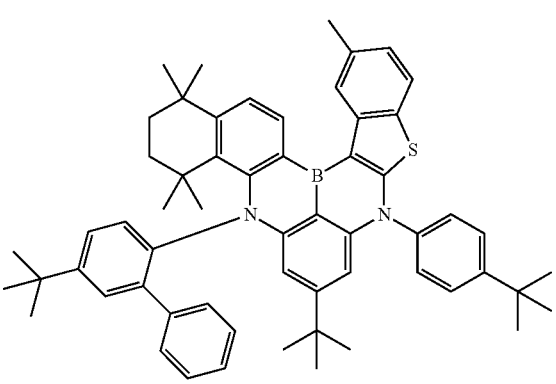
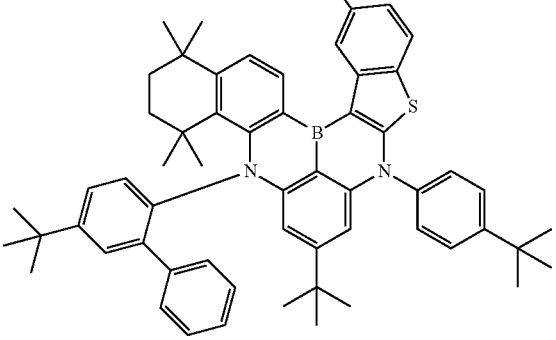

1243
-continued
1244
-continued
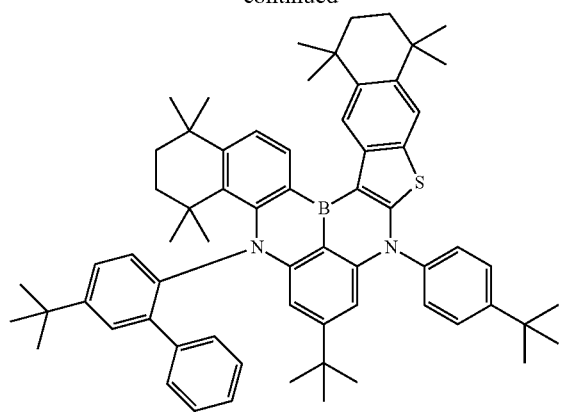
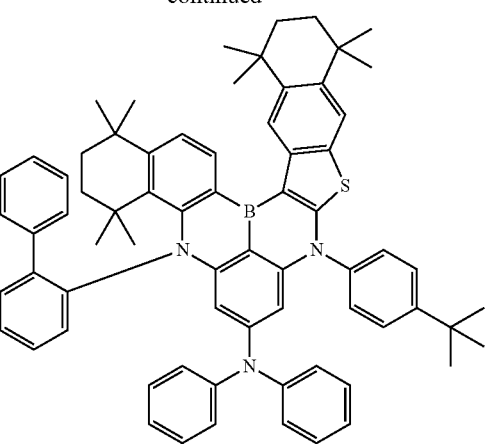

1245
-continued
1246
-continued
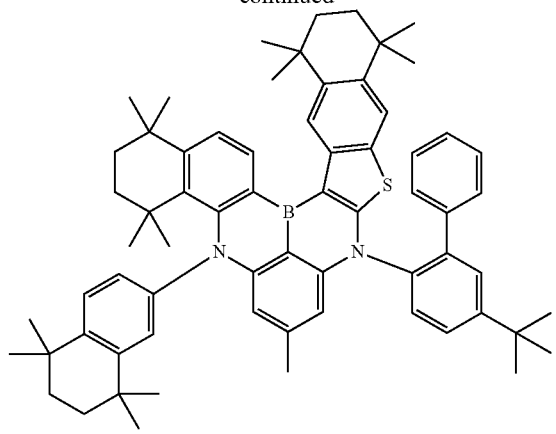
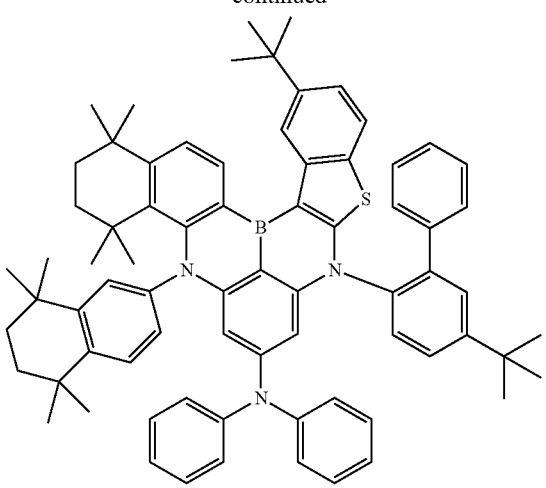
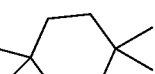
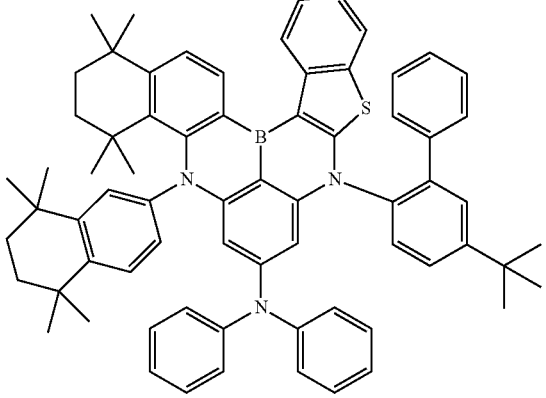
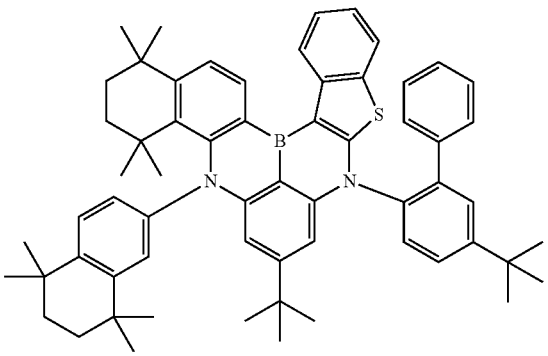
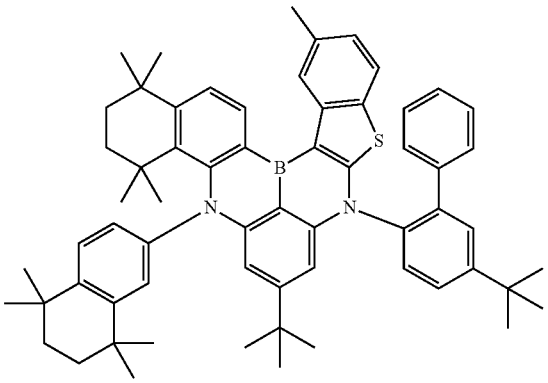

1247
-continued
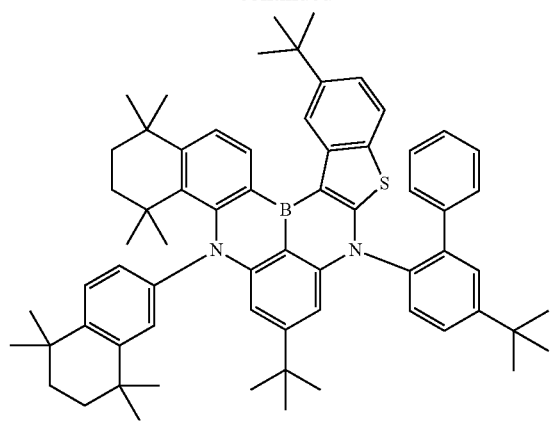
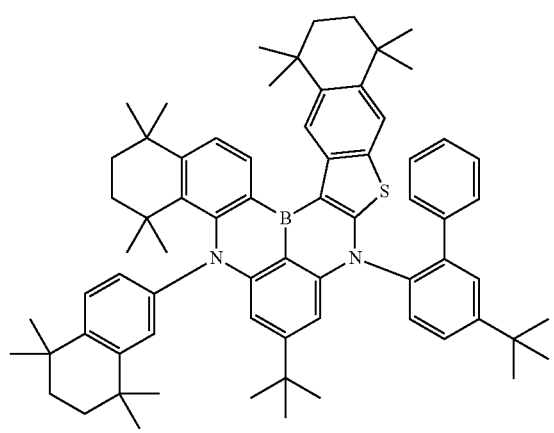
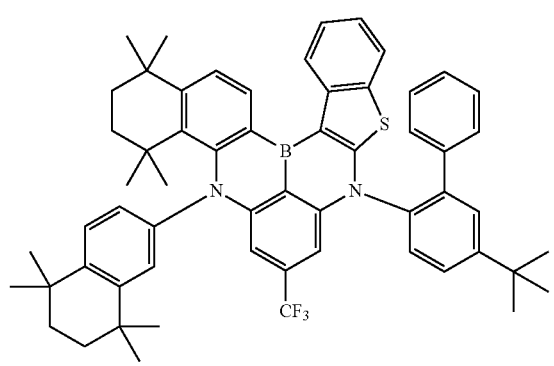
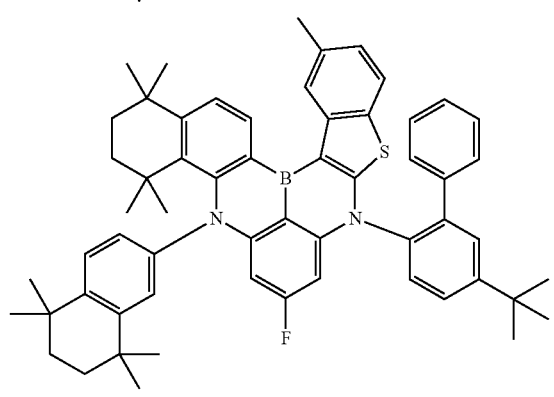
1248
-continued
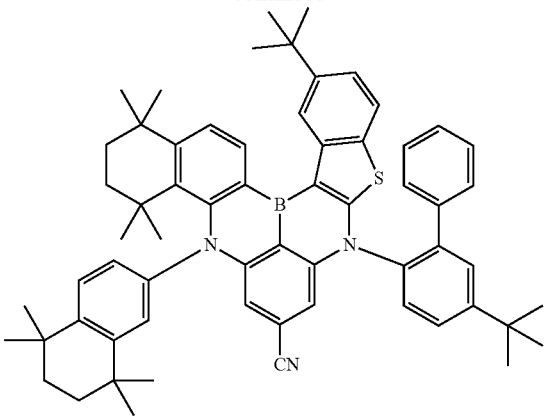
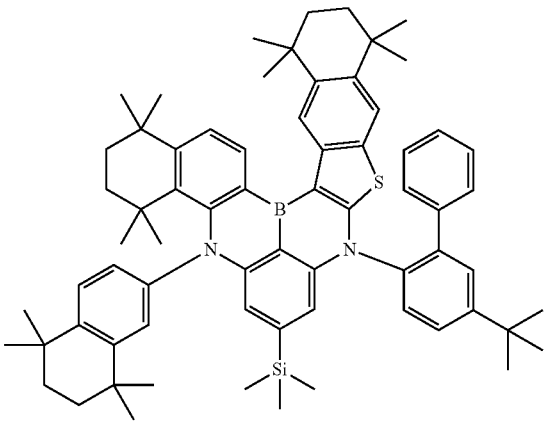
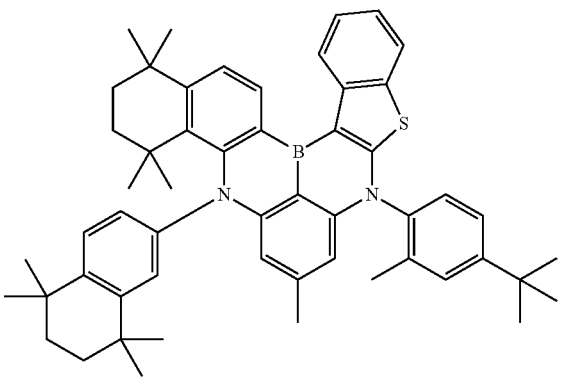
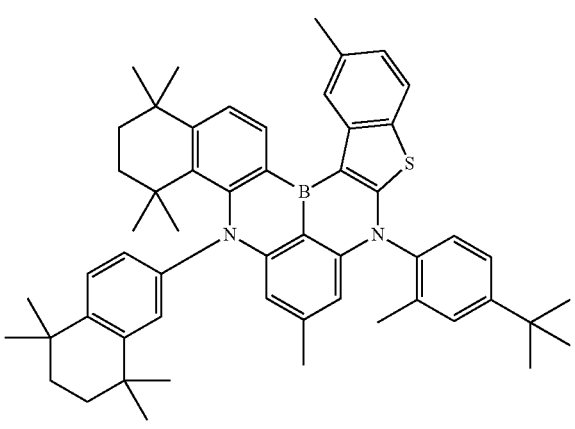

1249
-continued
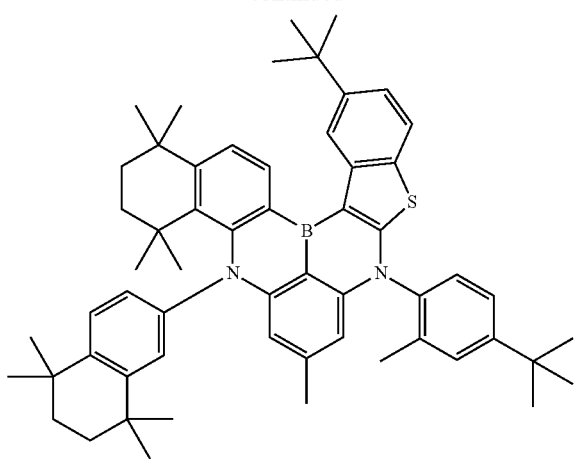
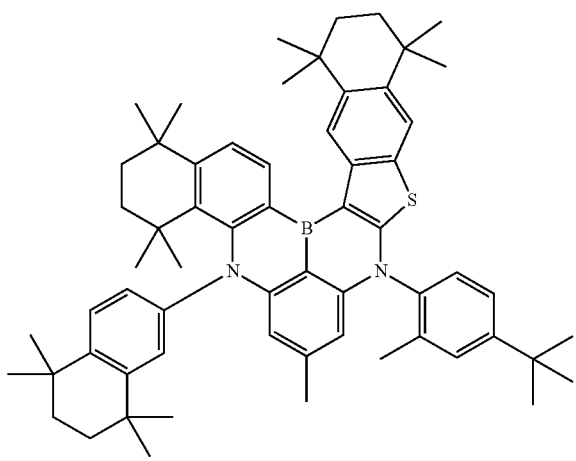
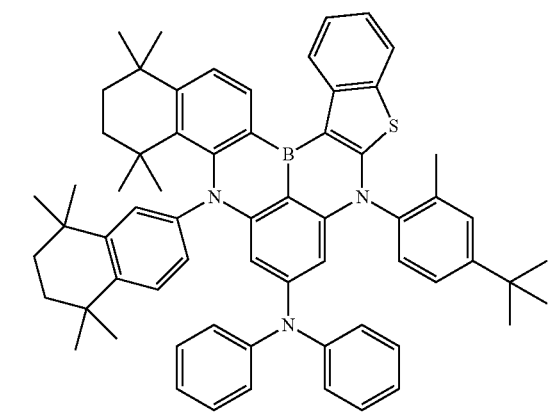
1250
-continued
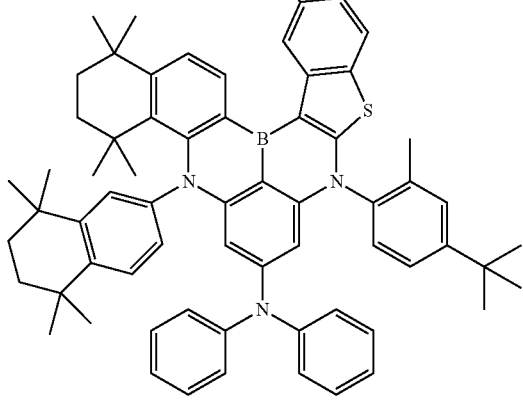
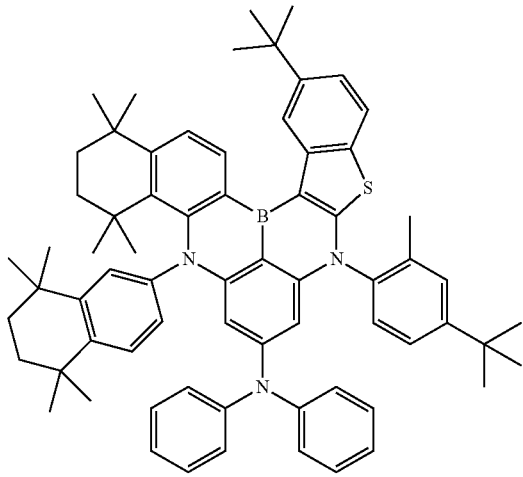
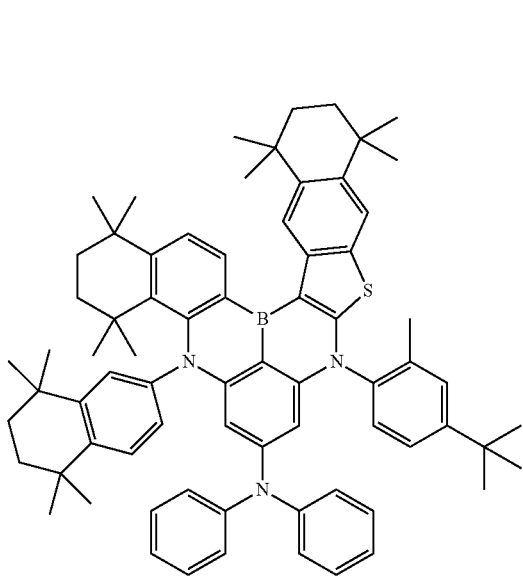

1251
-continued
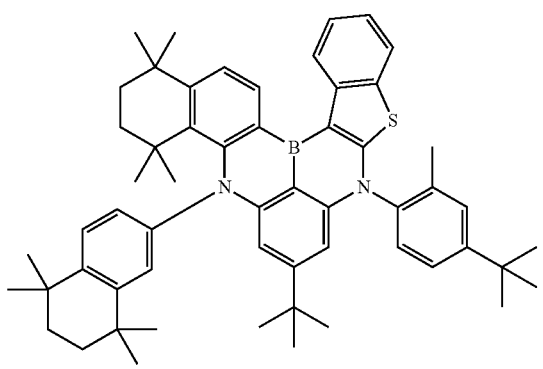
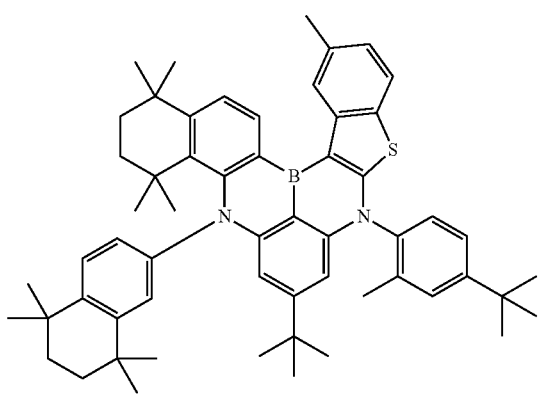
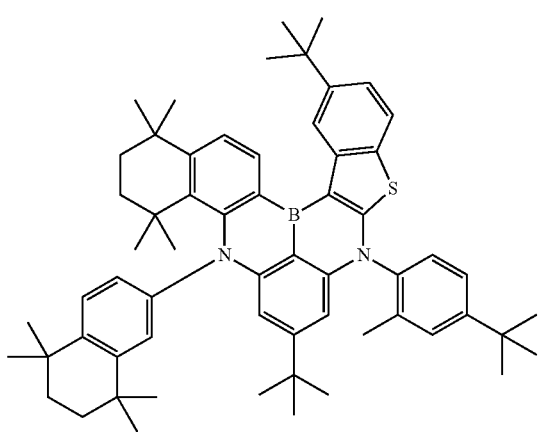
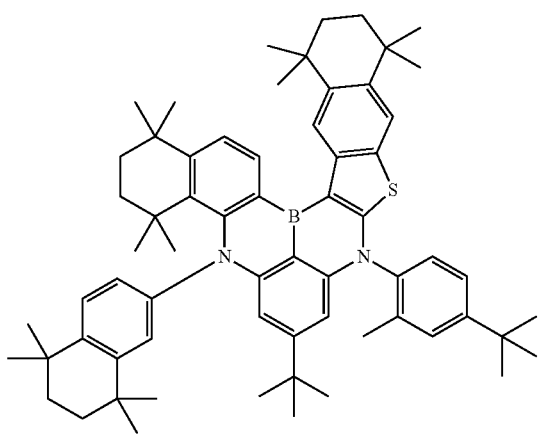
1252
-continued
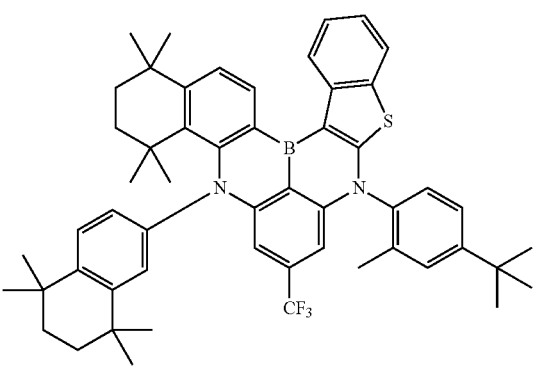
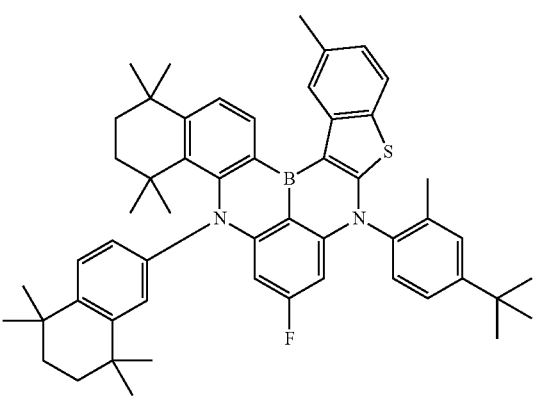
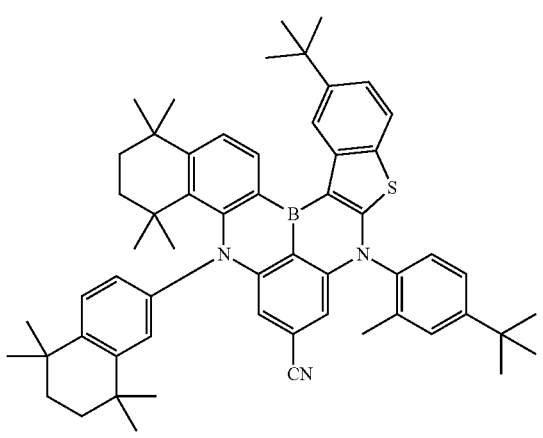
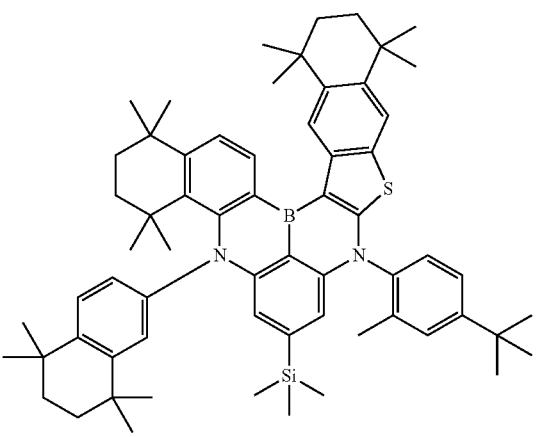

1253
-continued
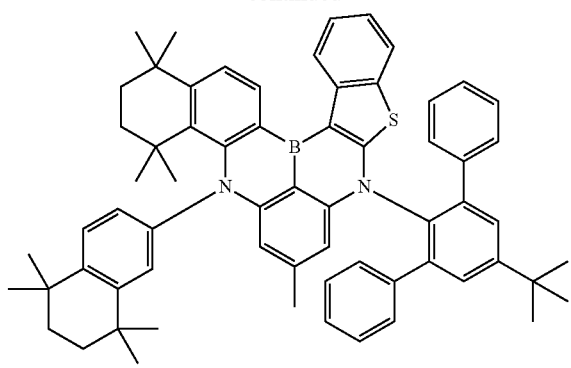
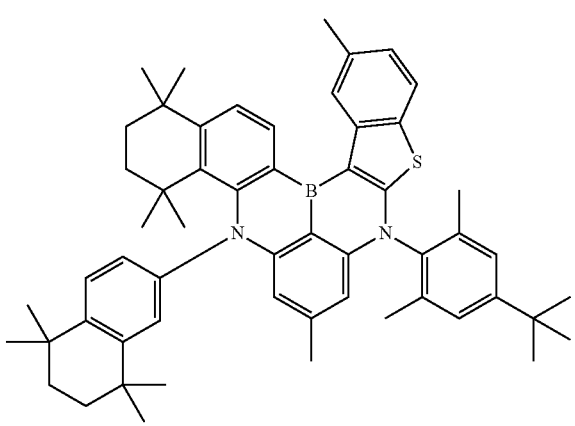
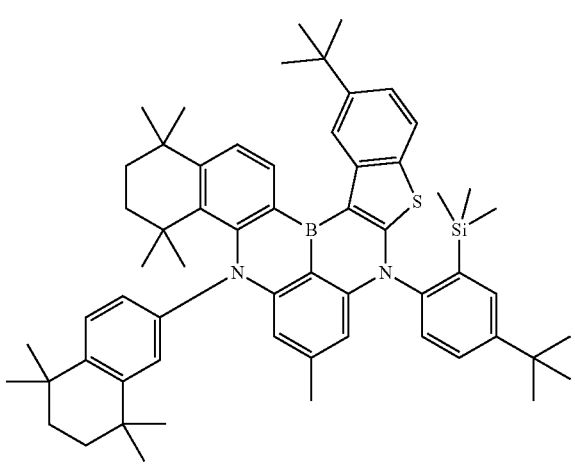
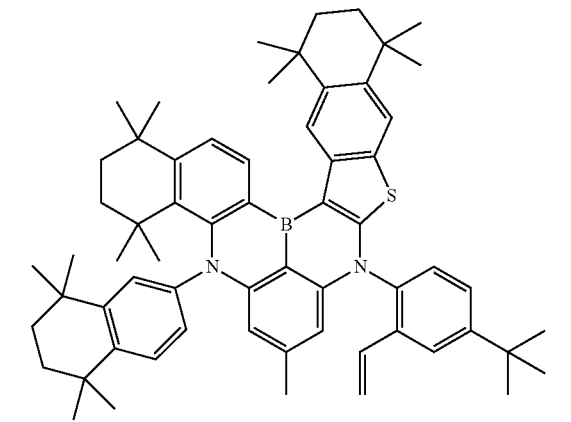
1254
-continued
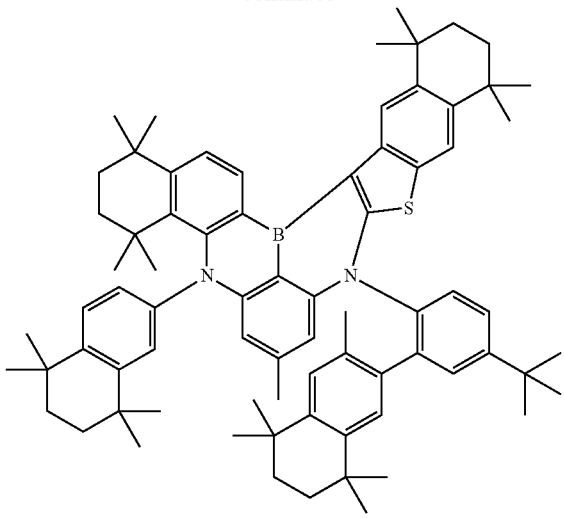
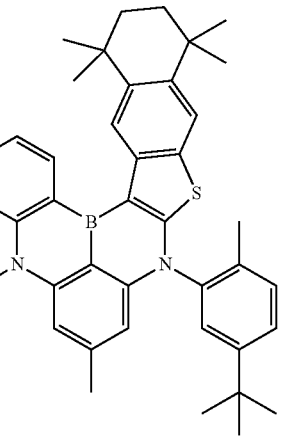
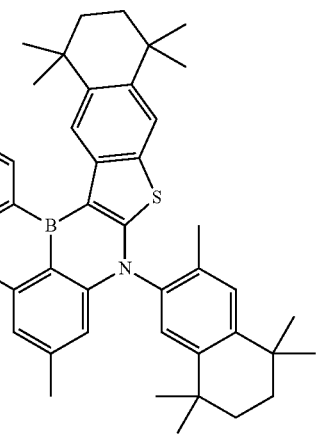

1255
-continued
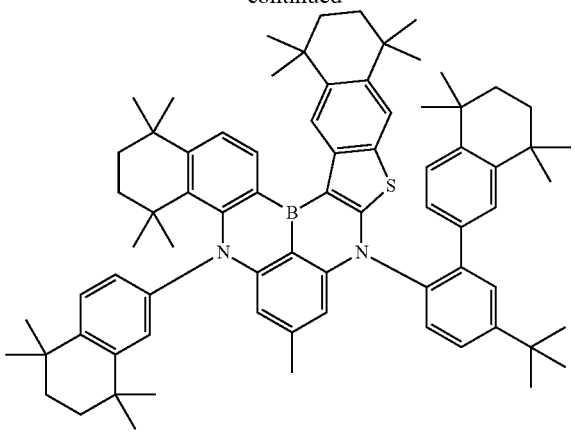
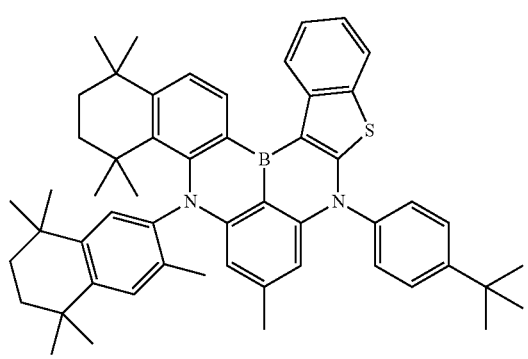
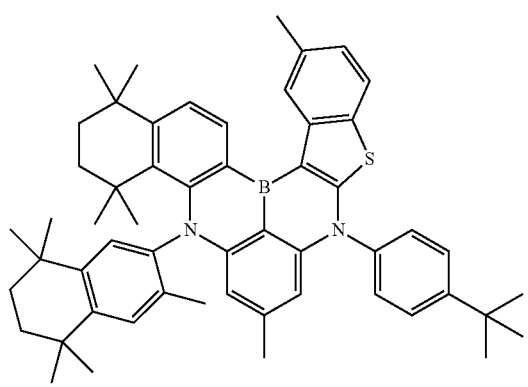
1256
-continued
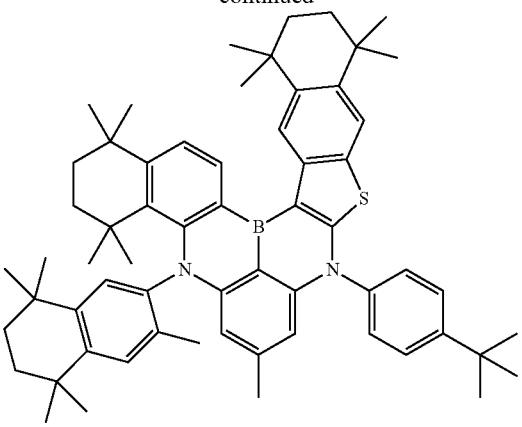
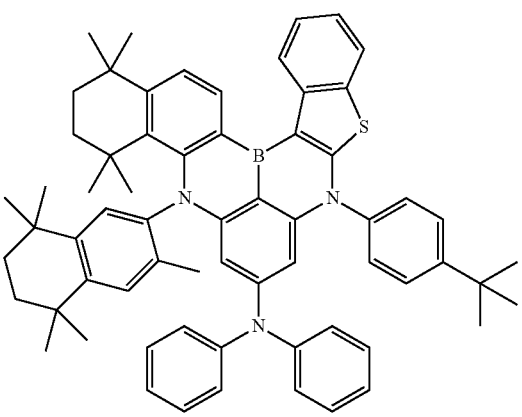
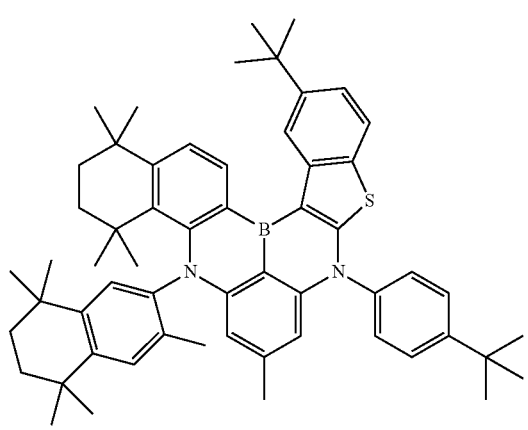
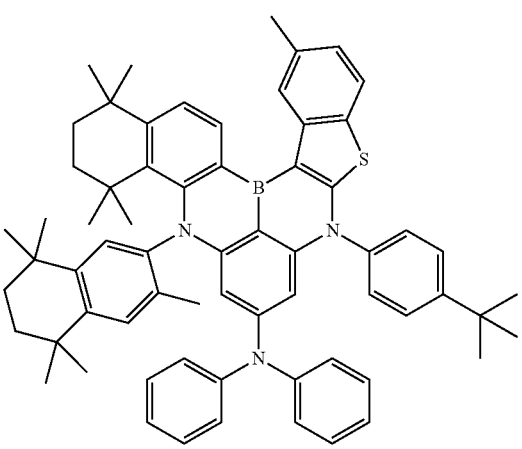

1257
-continued

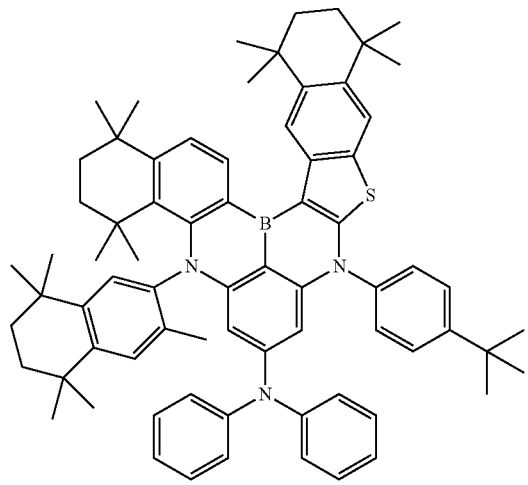
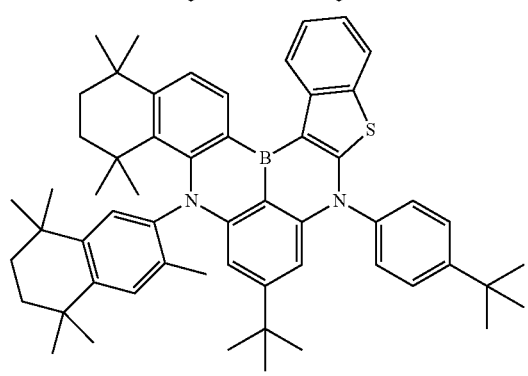
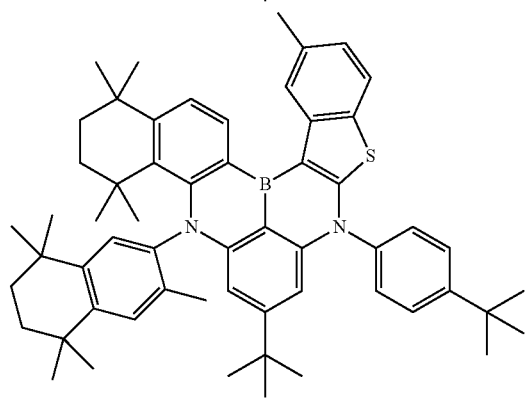
1258
-continued
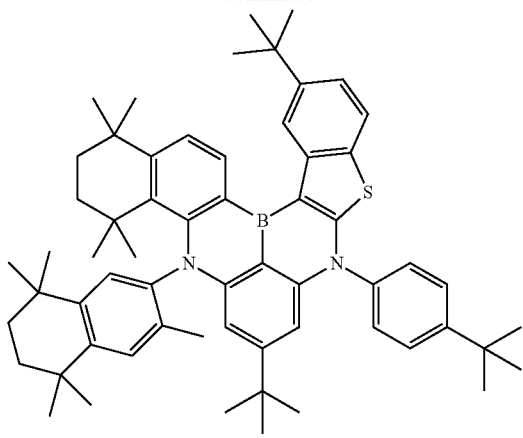
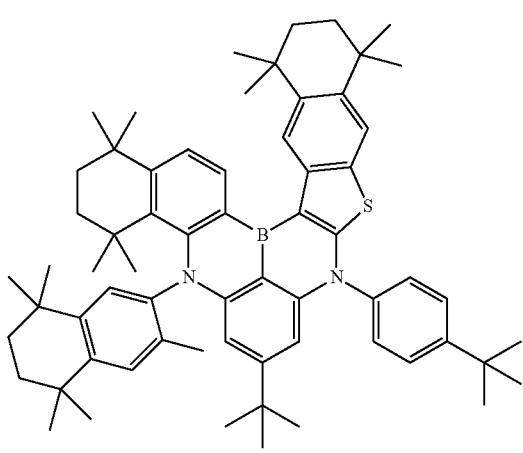
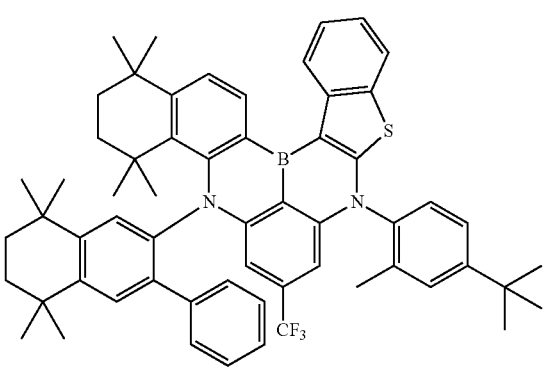
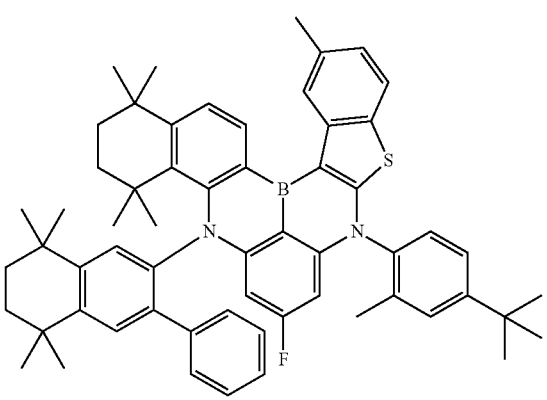

1259
-continued
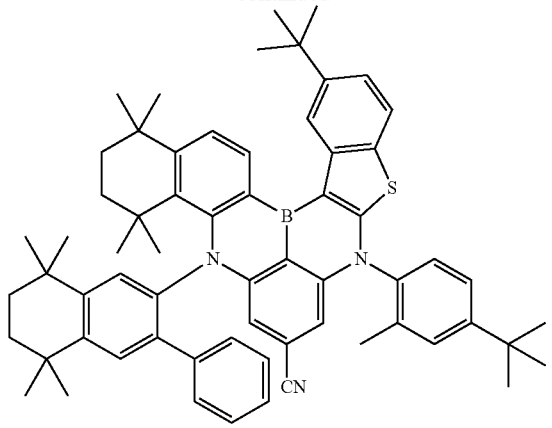
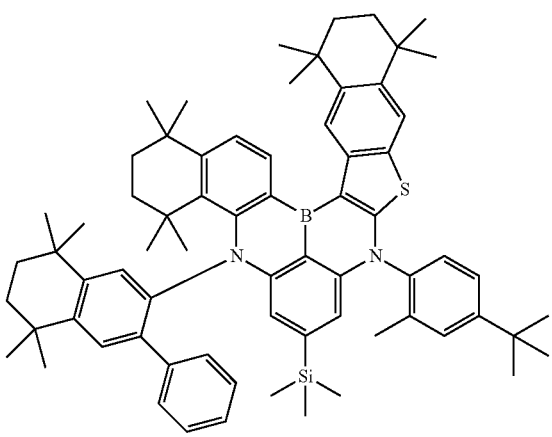
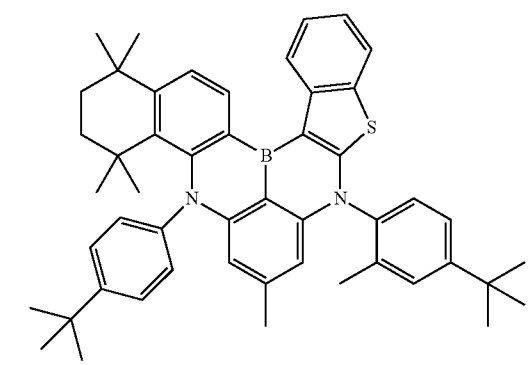
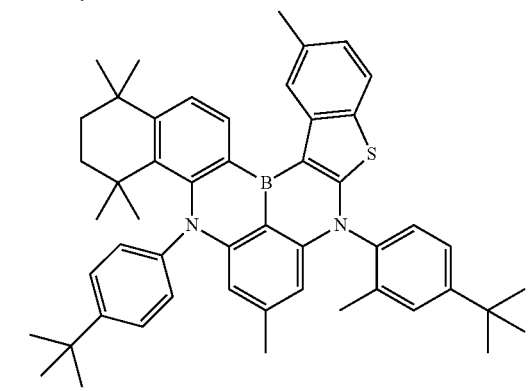
1260
-continued
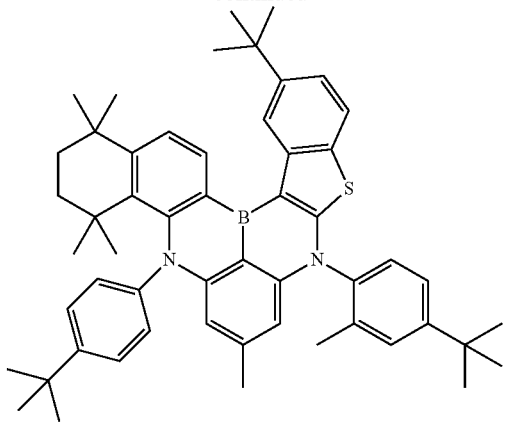
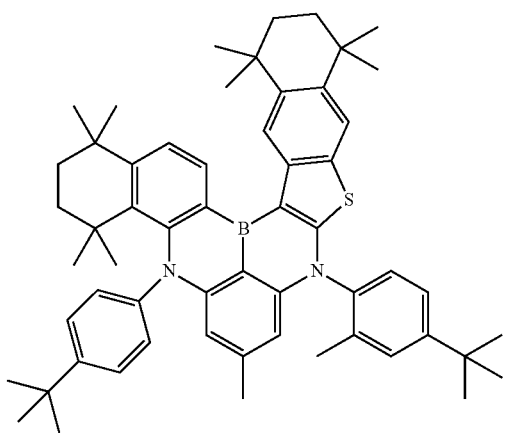
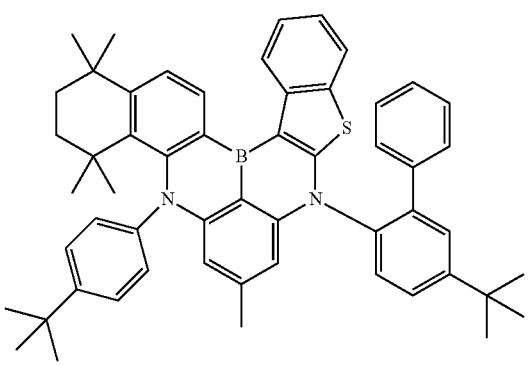
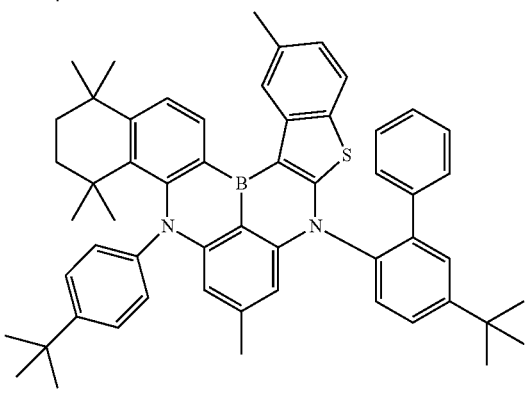

1261
-continued
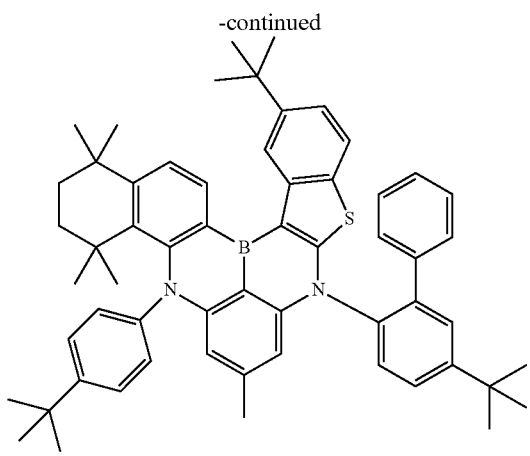
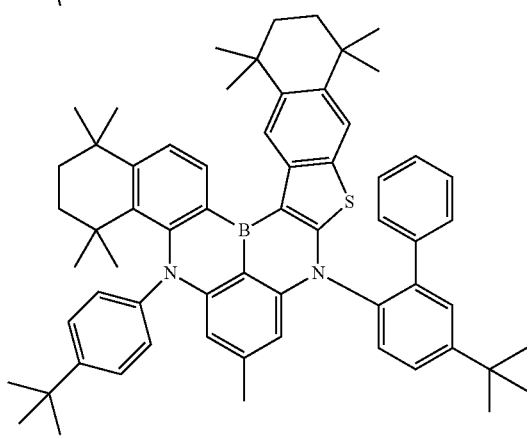
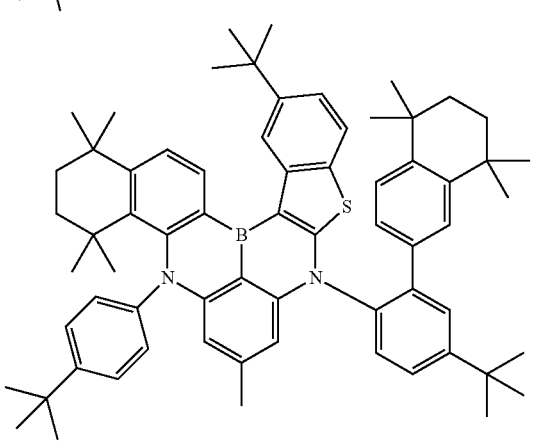
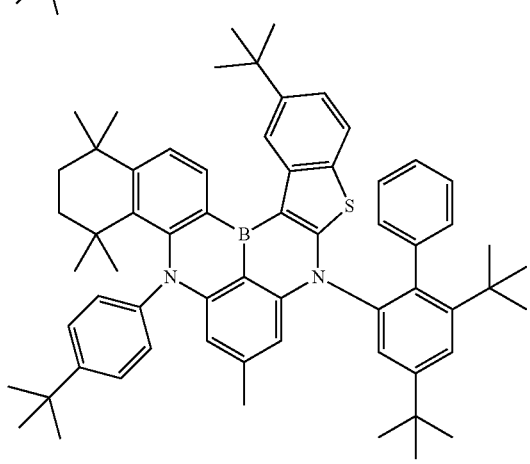
1262
-continued
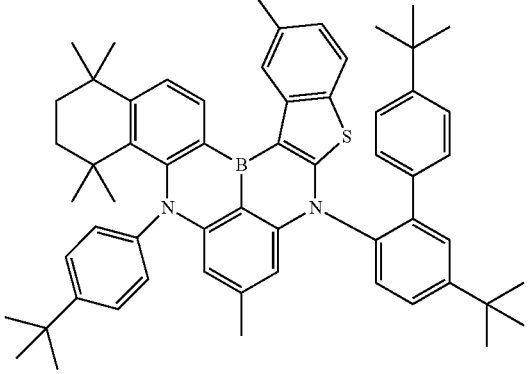
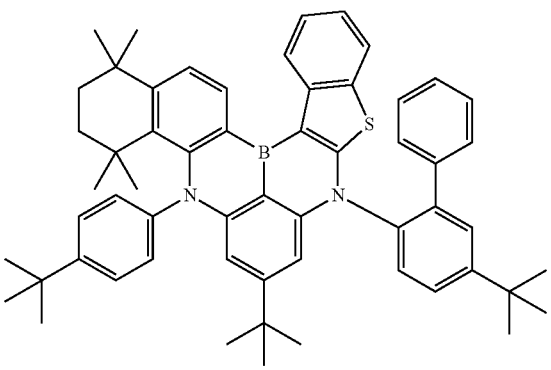
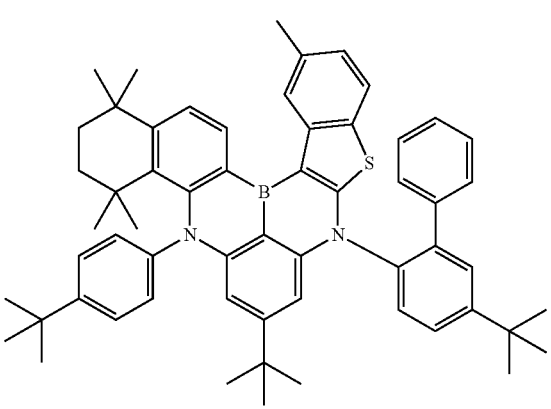

1263
-continued
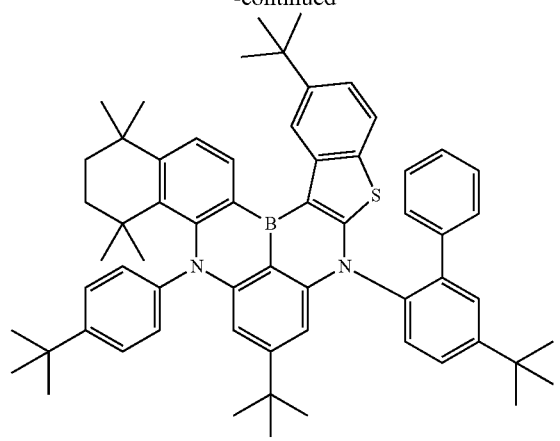
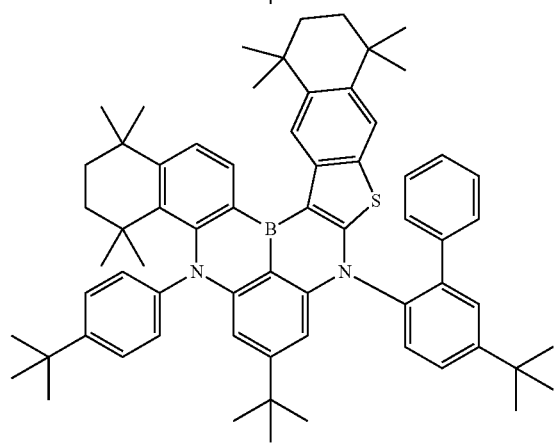
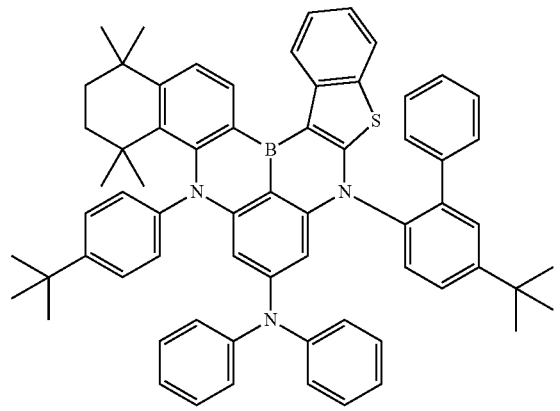
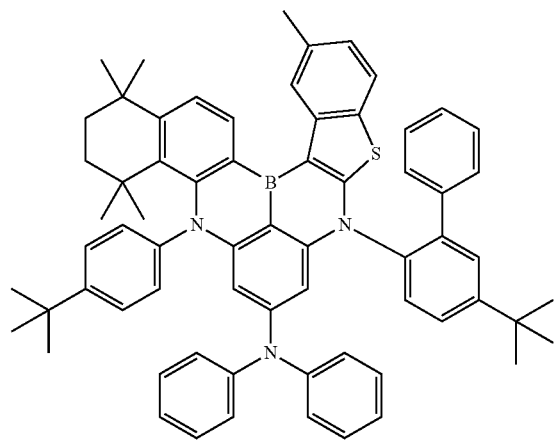
1264
-continued
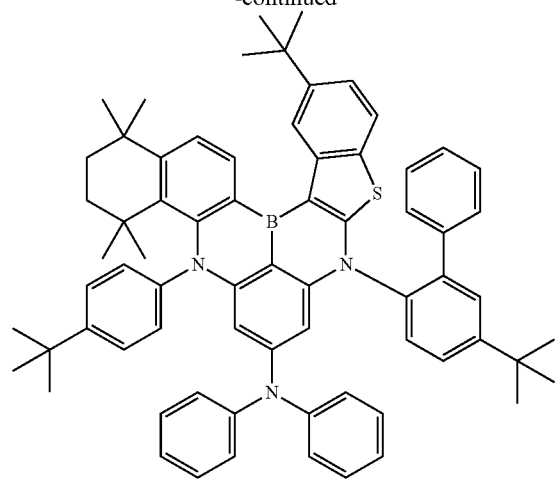
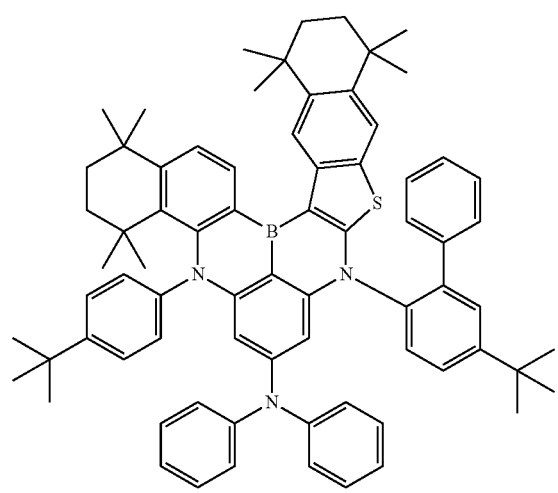
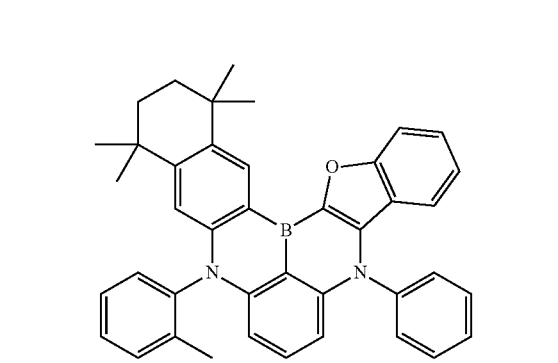
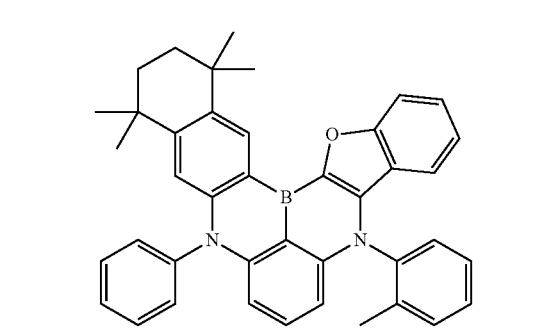

| 1265 -continued | 1266 -continued |
|---|---|
| 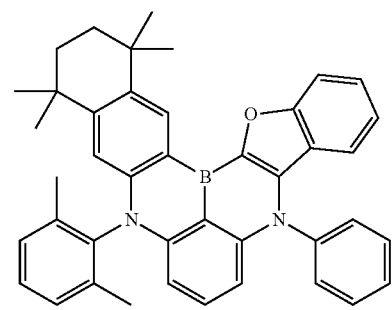 | 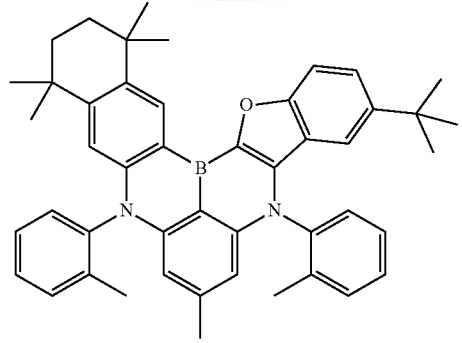 |
| 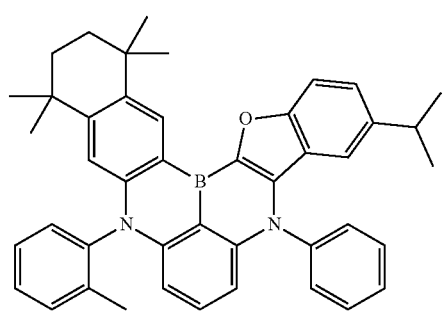 | 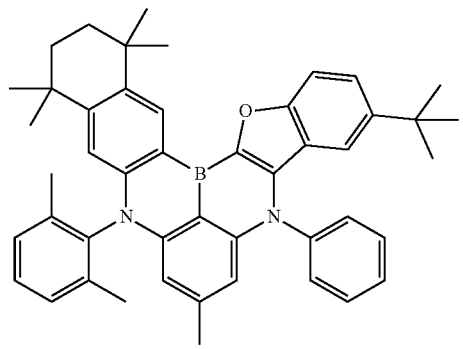 |
| 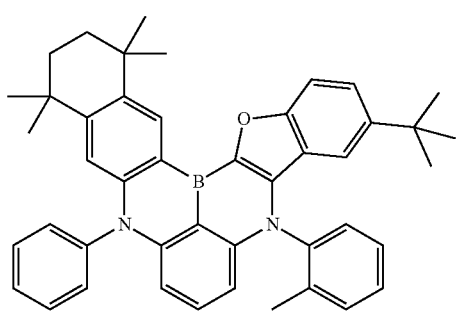 | 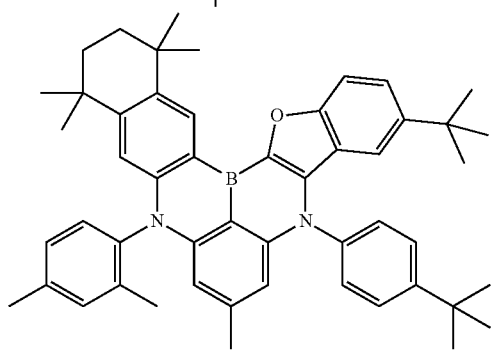 |
| 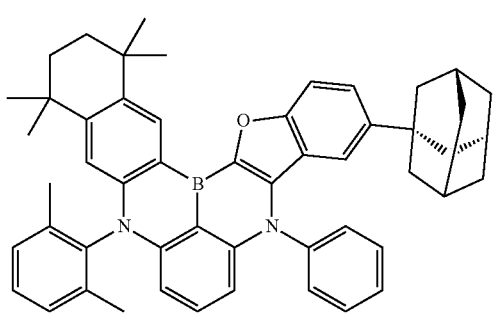 | 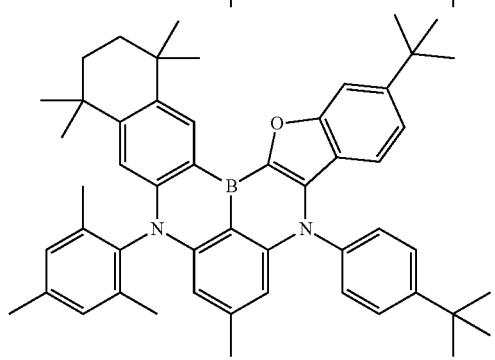 |
| 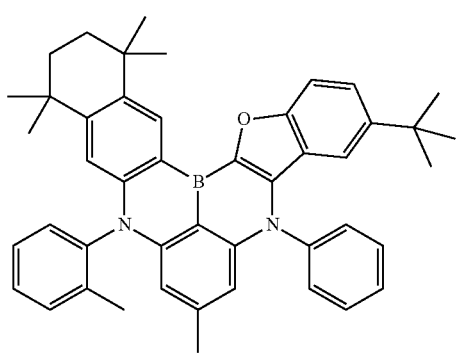 | 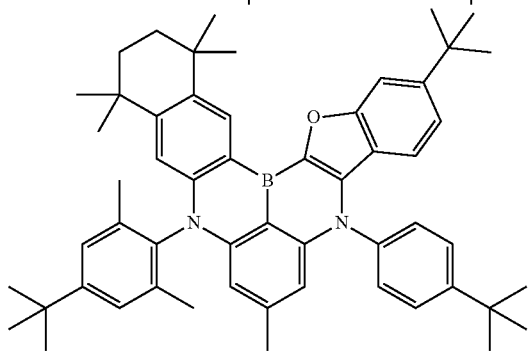 |

1267
-continued

1268
-continued

1269
-continued
1270
-continued
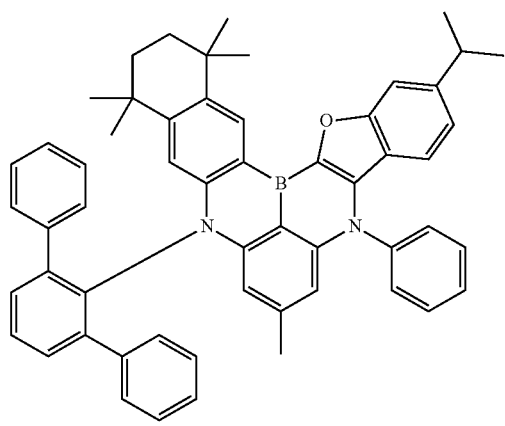
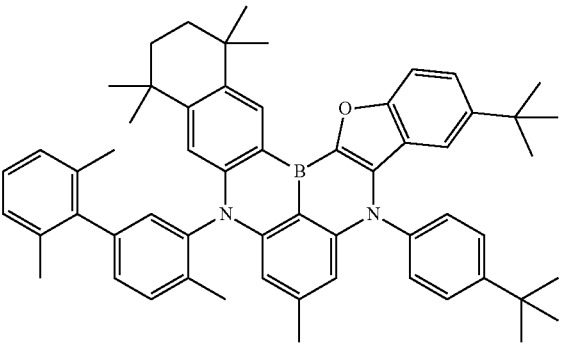

1271
-continued
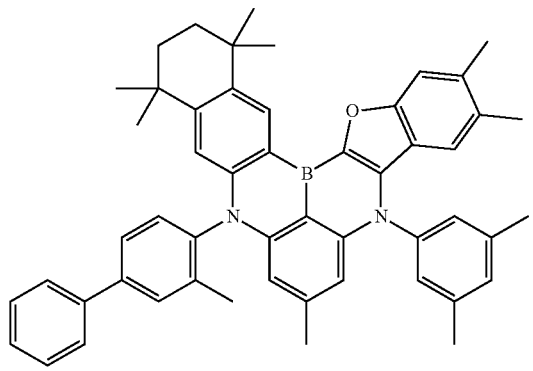
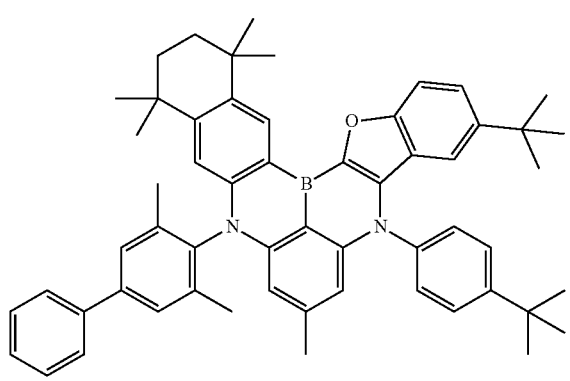
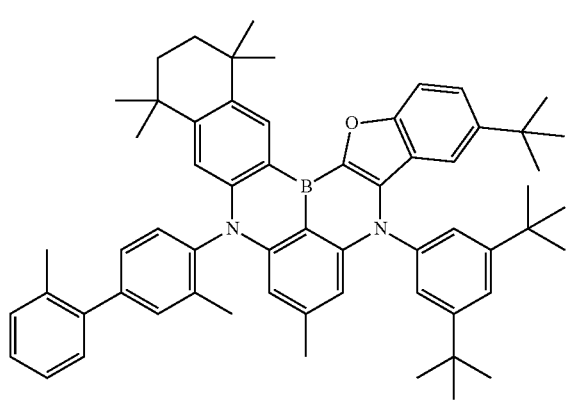
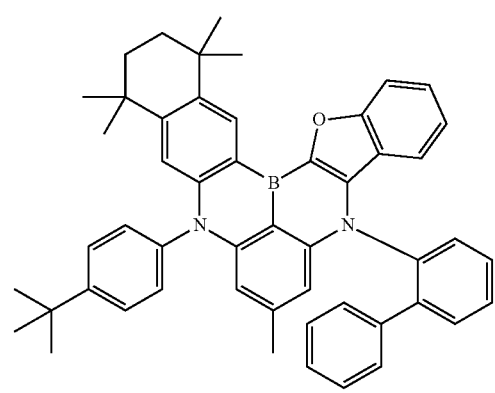
1272
-continued
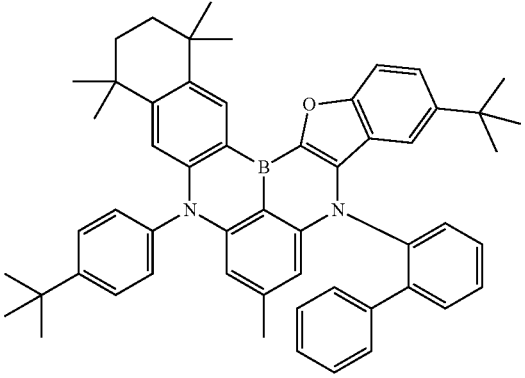
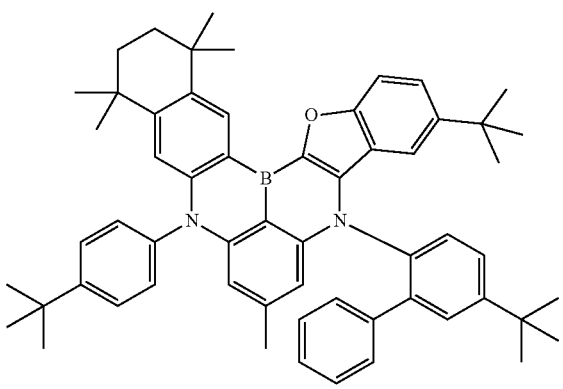
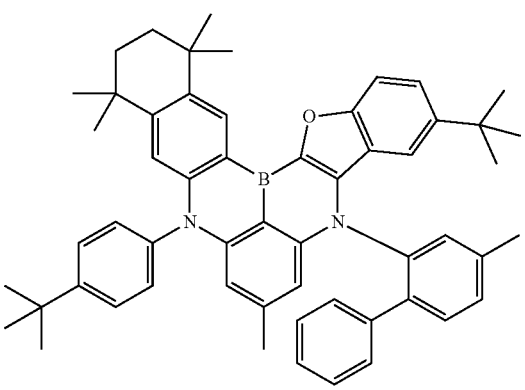
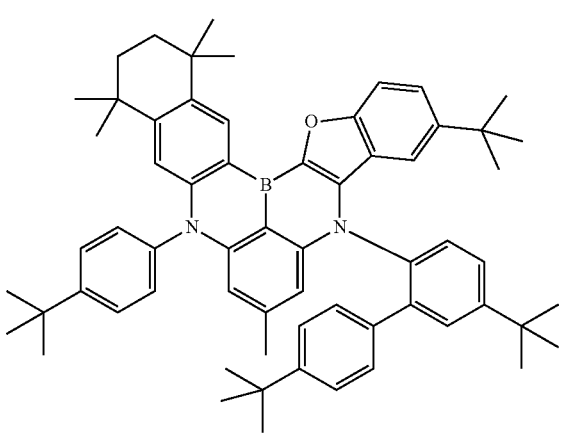

| 1273 -continued | 1274 -continued |
|---|---|
| 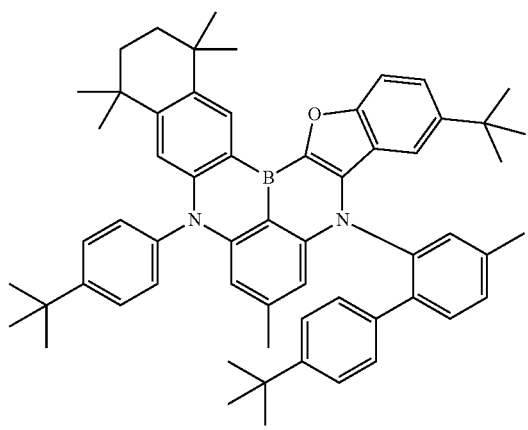 | 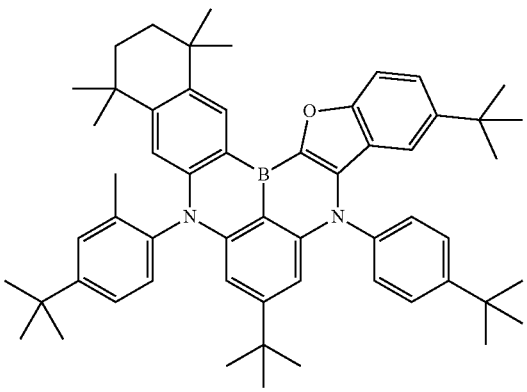 |
| 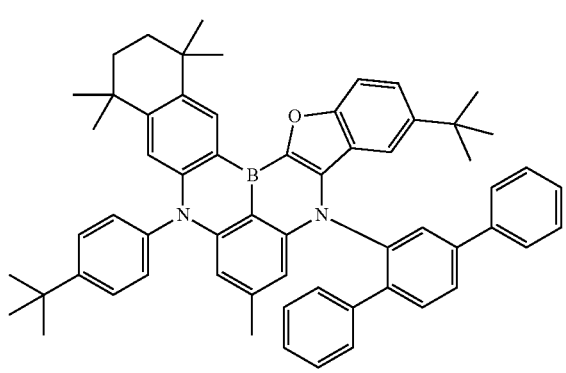 | 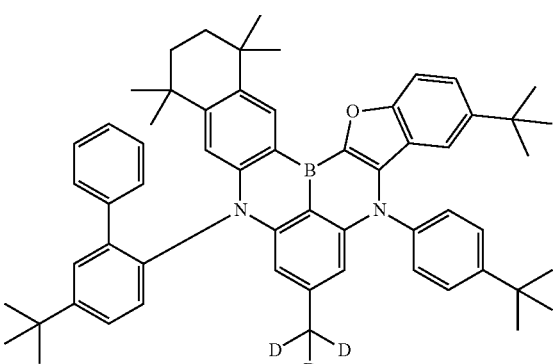 |
| 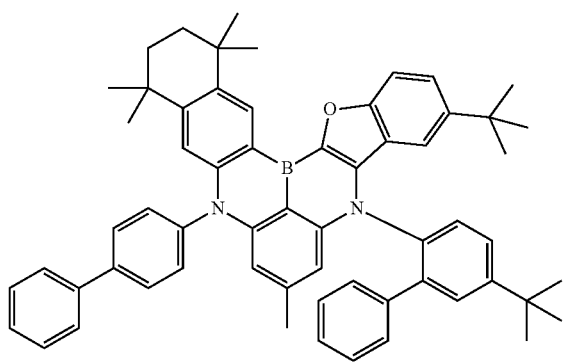 | 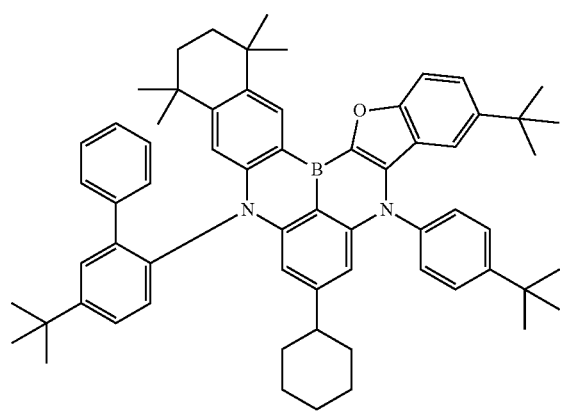 |
| 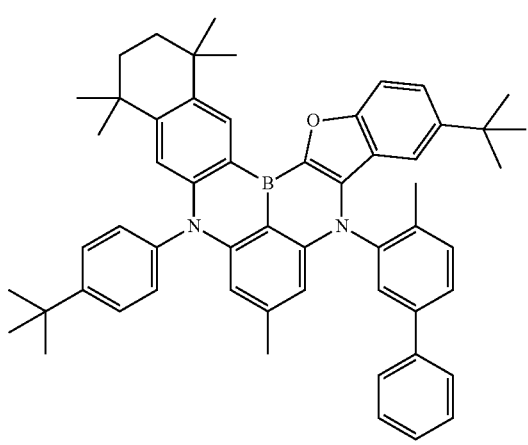 | 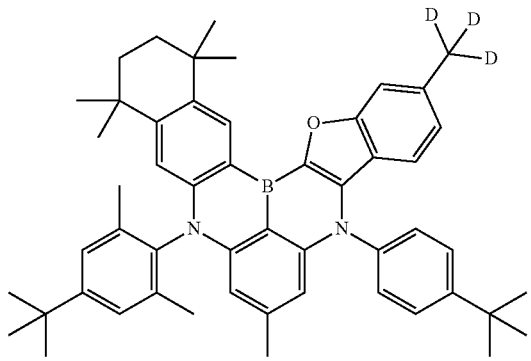 |

1275
-continued
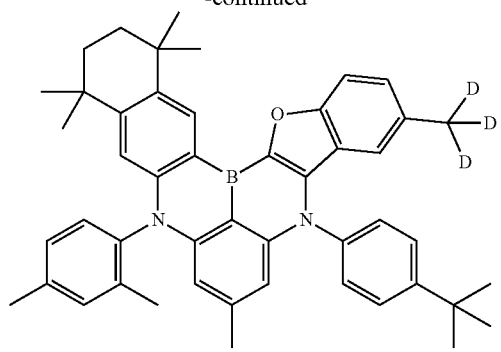
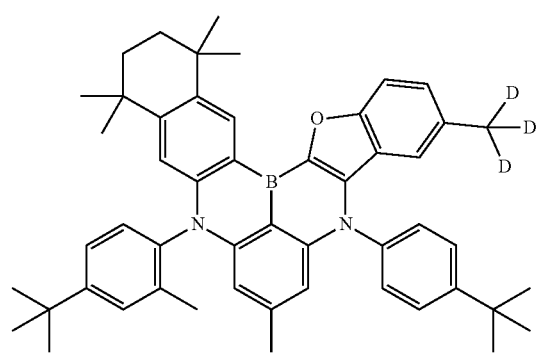
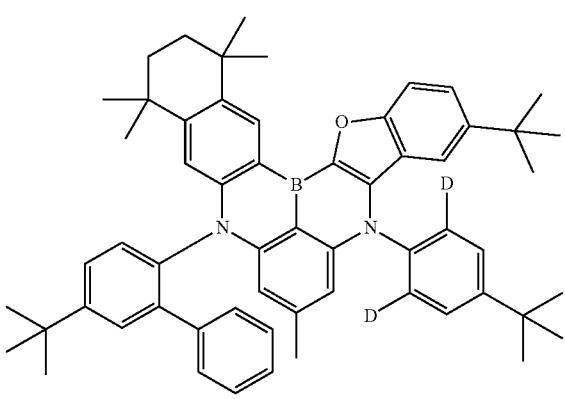
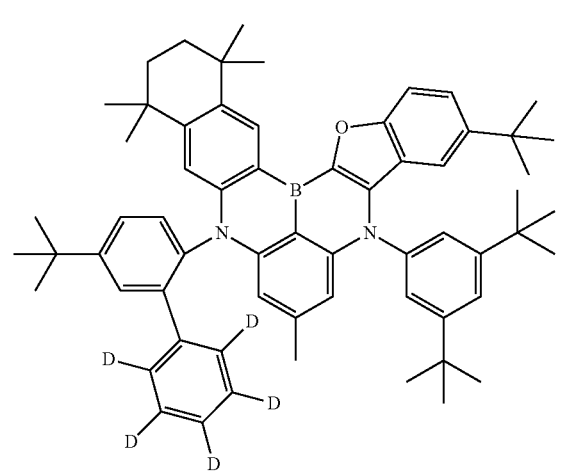
1276
-continued
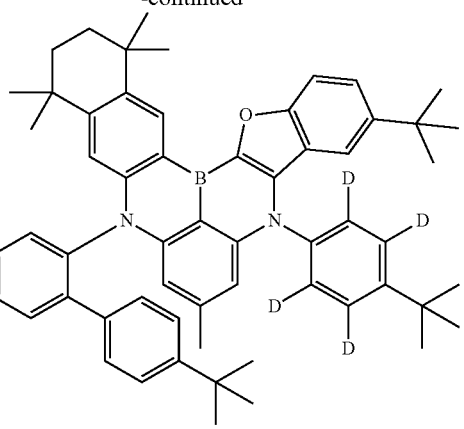
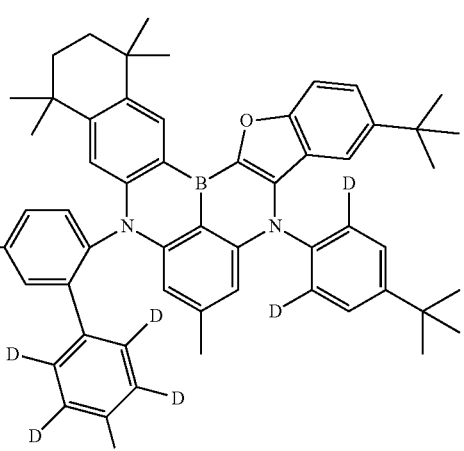
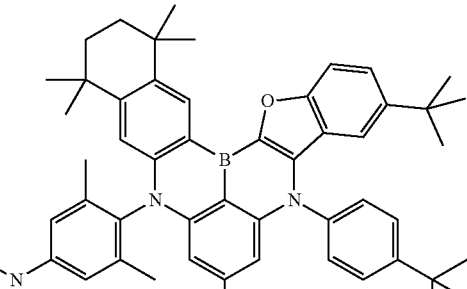
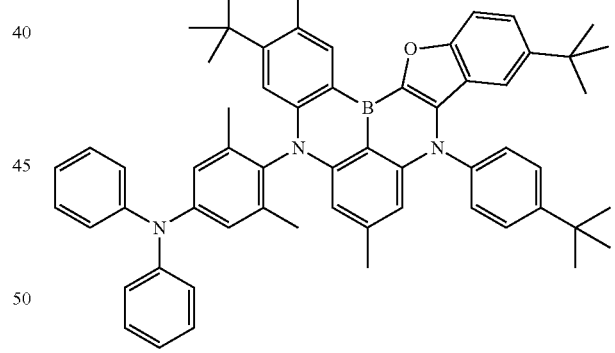
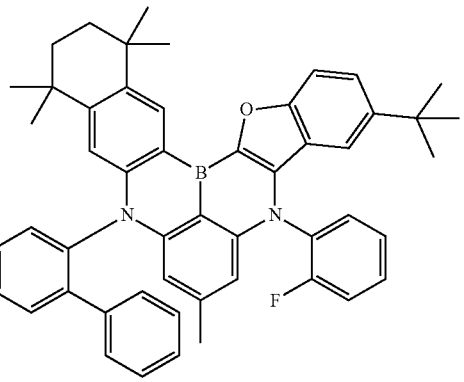
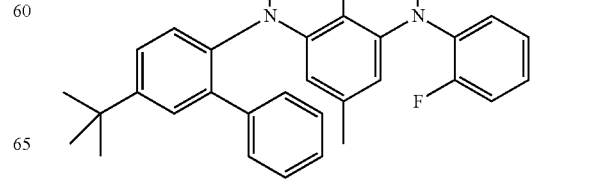

1277
-continued
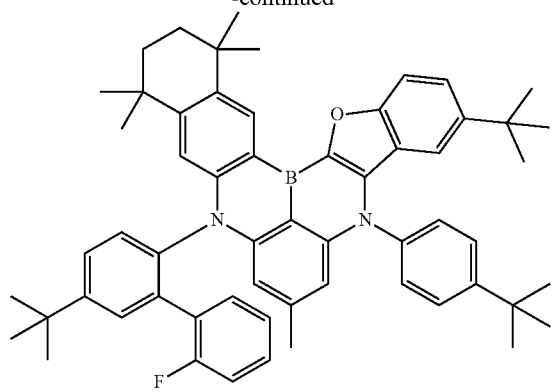
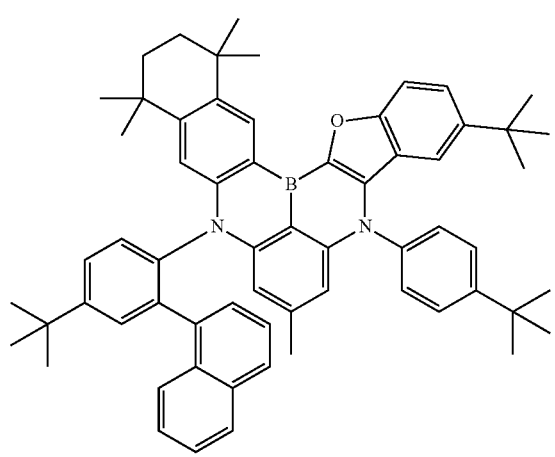

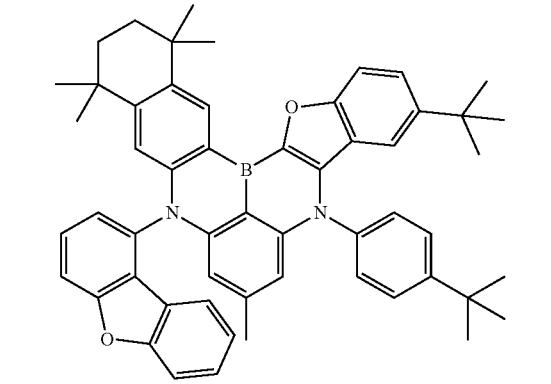
1278
-continued
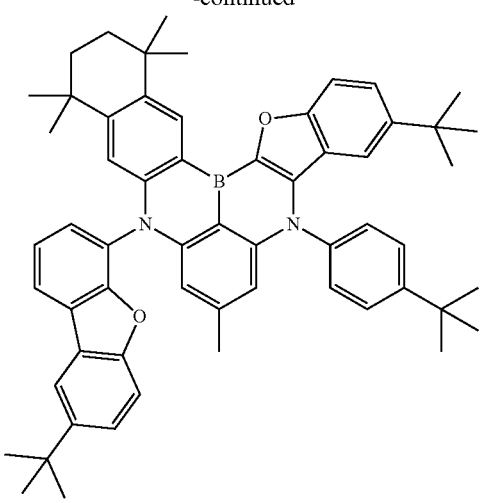
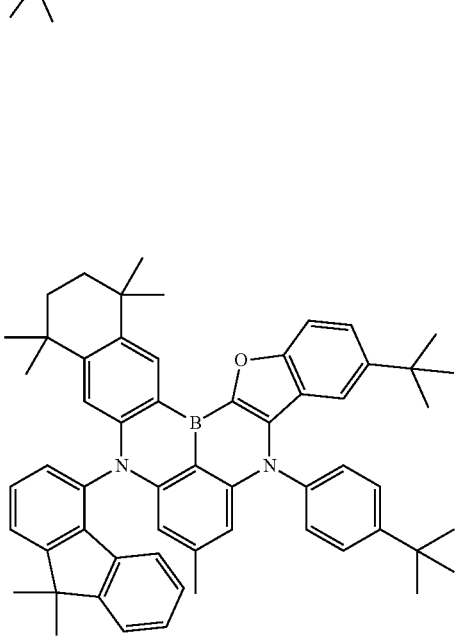
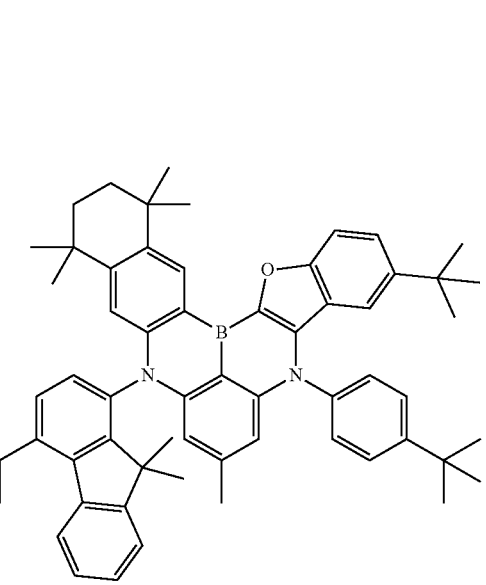

| 1279 -continued | 1280 -continued |
|---|---|
| 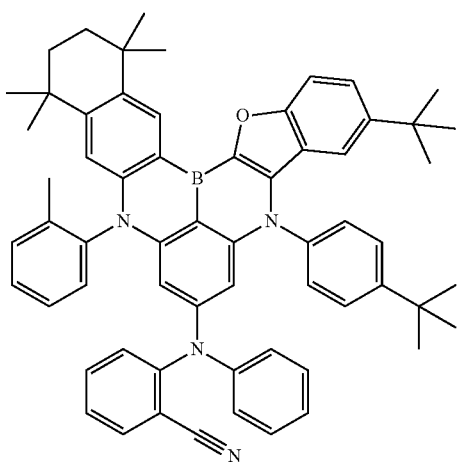 | 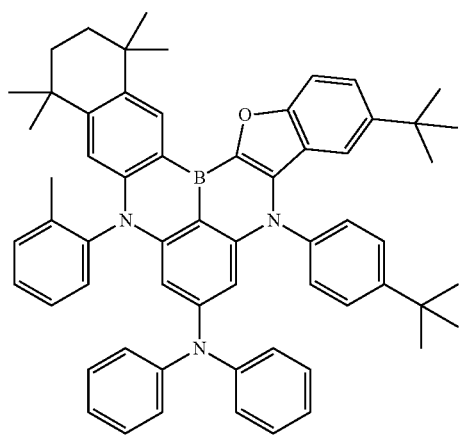 |
| 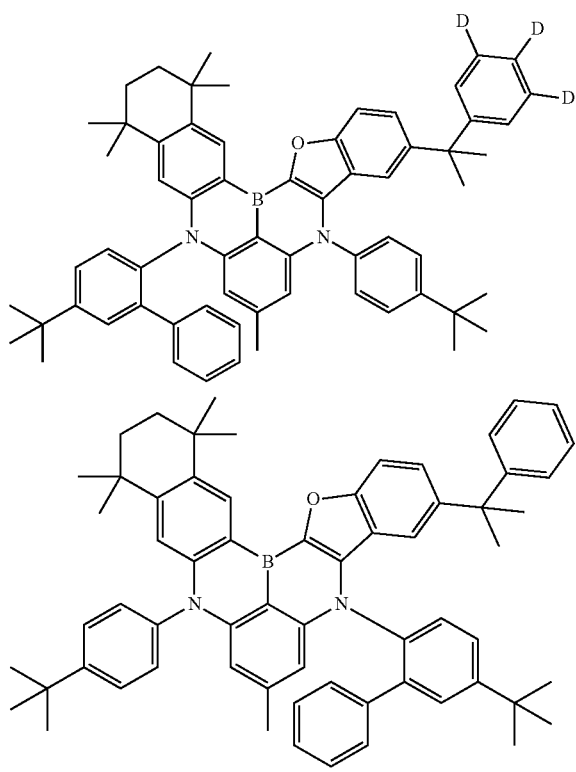 | 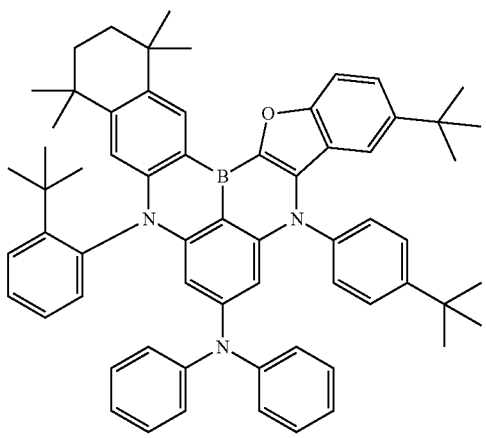 |
| 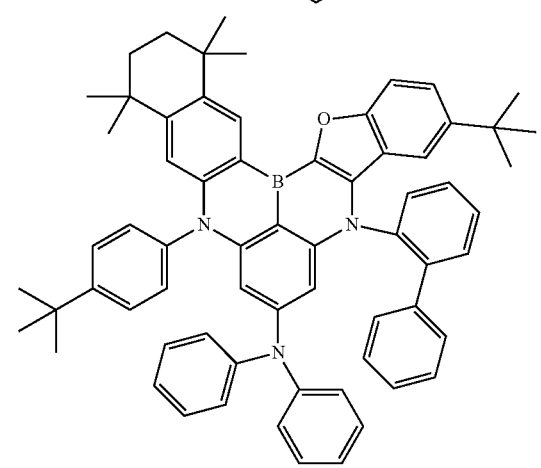 | 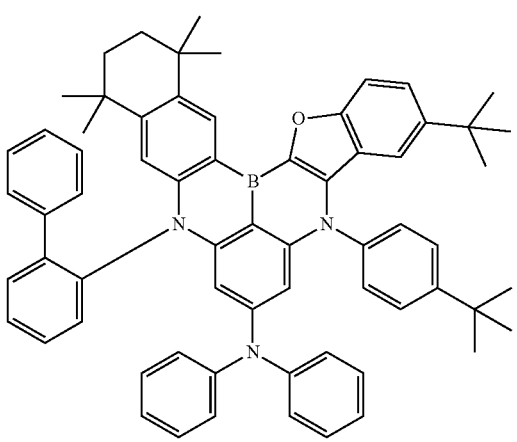 |

1281
-continued
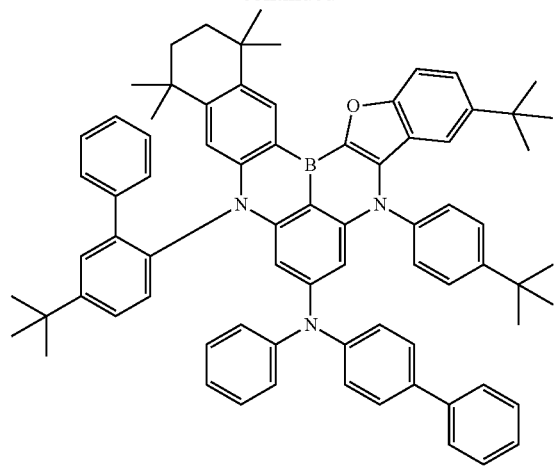
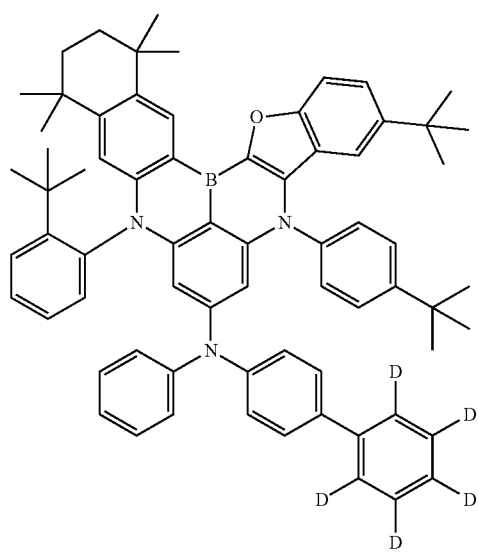
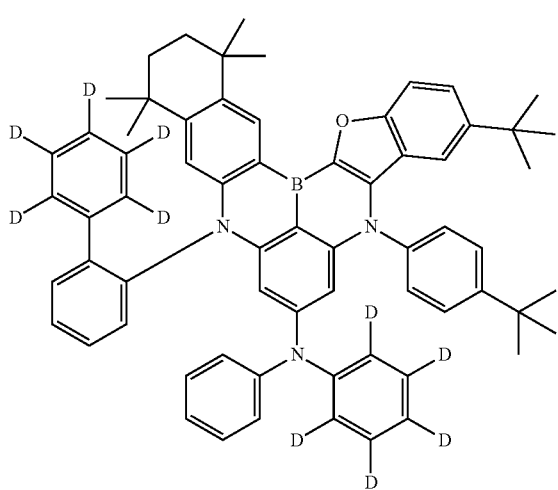
1282
-continued
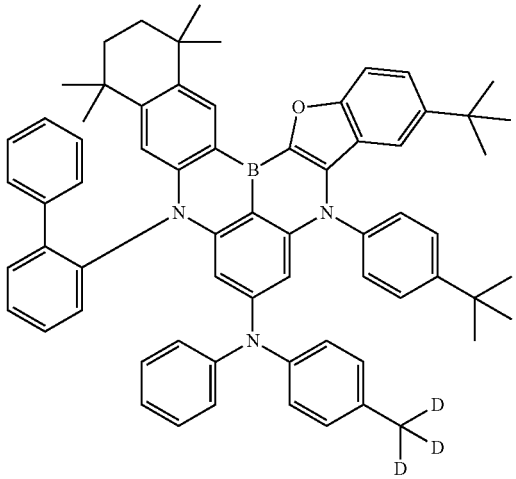
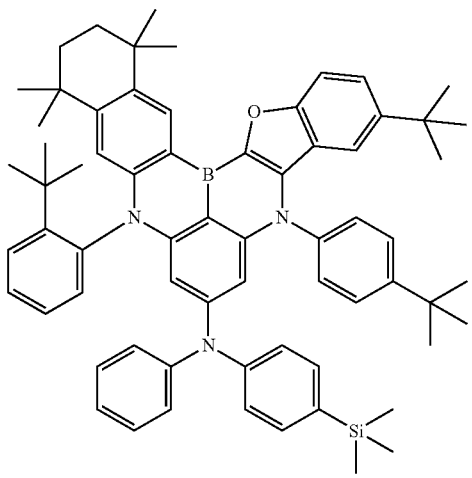
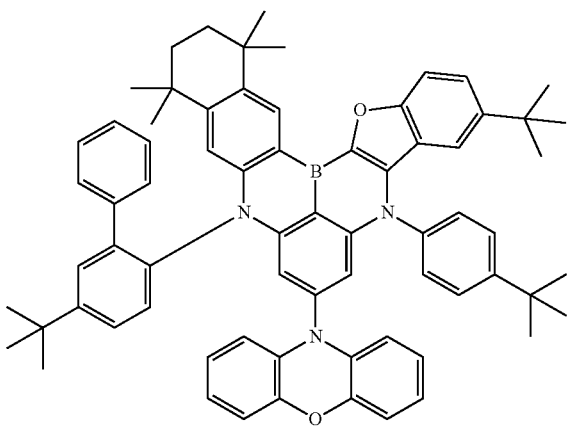

1283
-continued
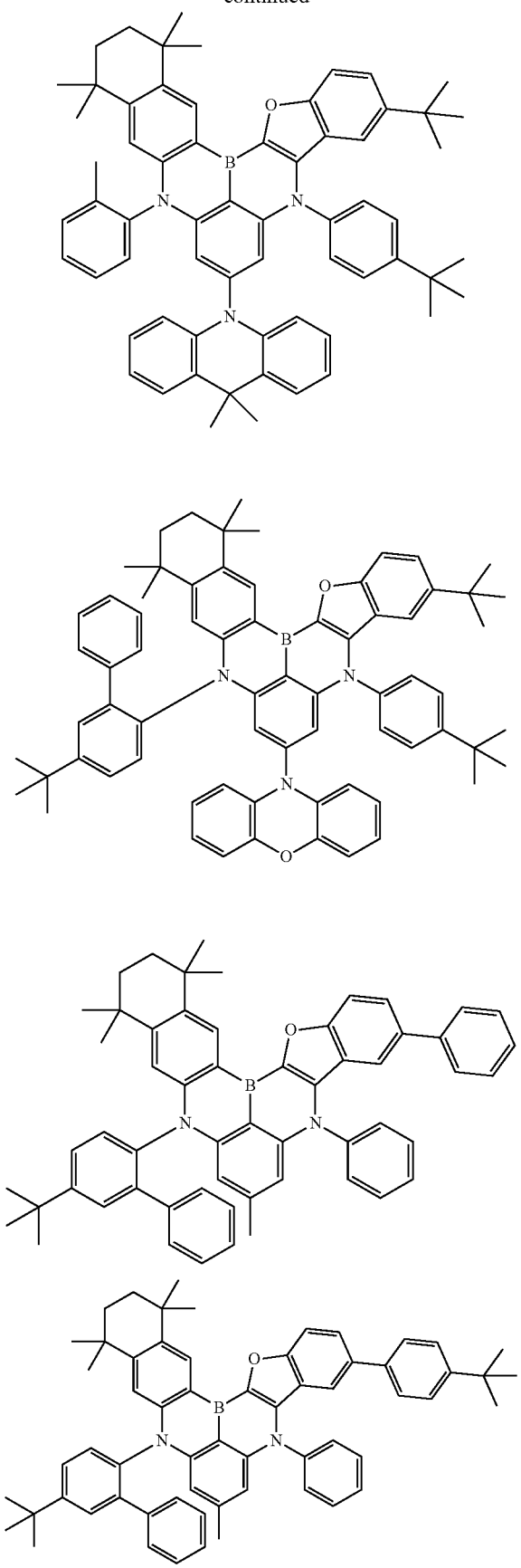
1284
-continued
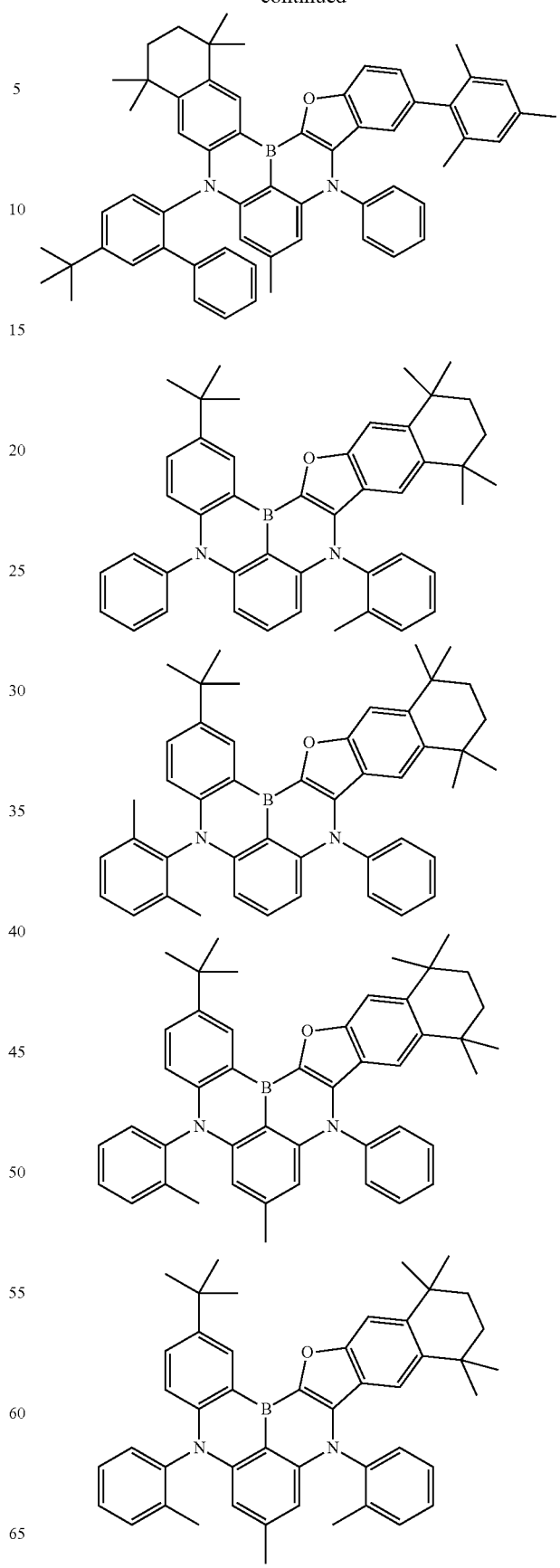

1285
-continued
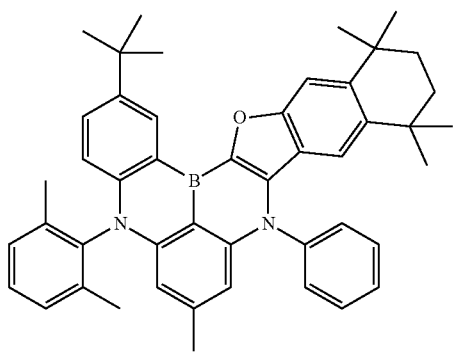
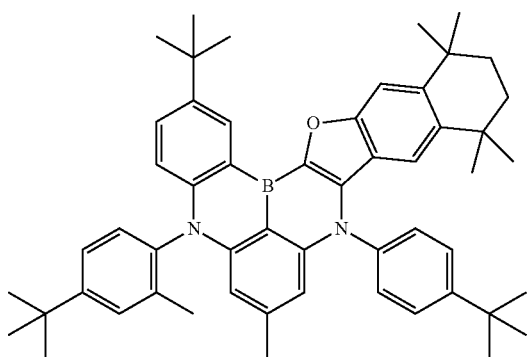
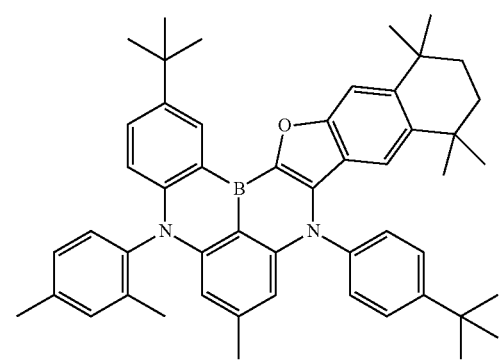
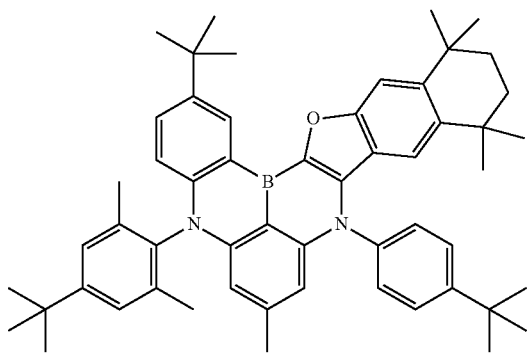
1286
-continued
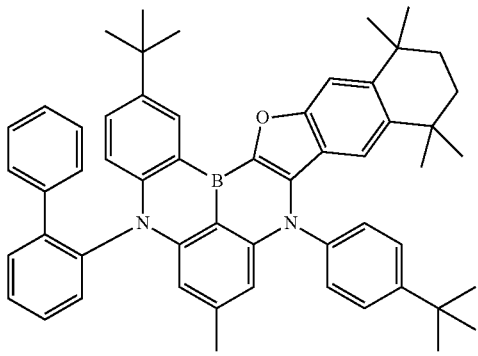
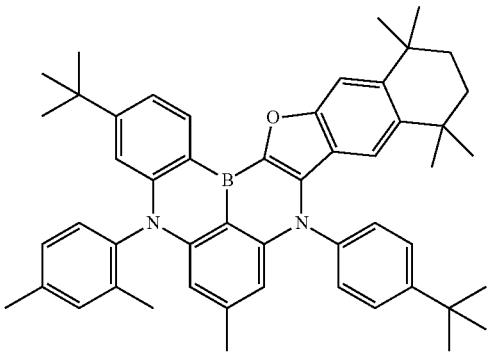
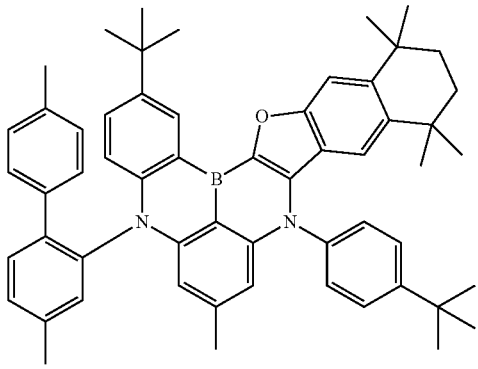
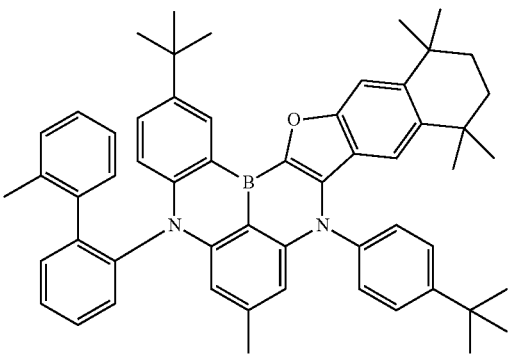

| 1287 -continued | 1288 -continued |
|---|---|
| 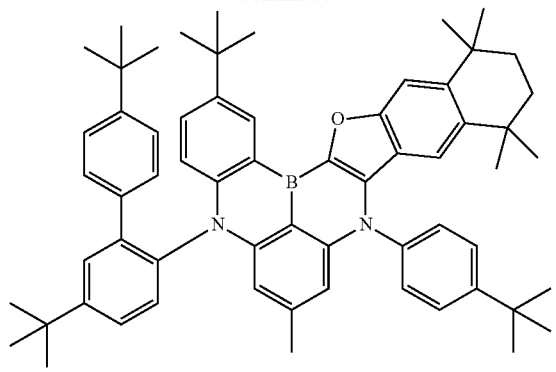 | 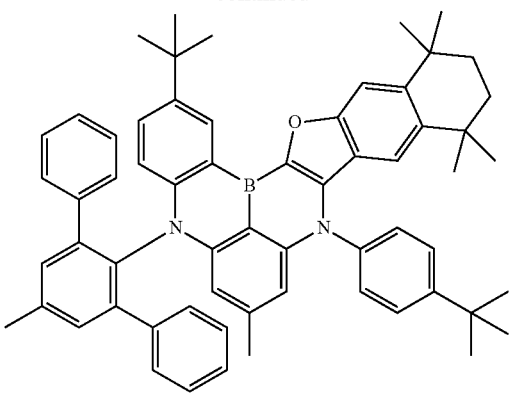 |
| 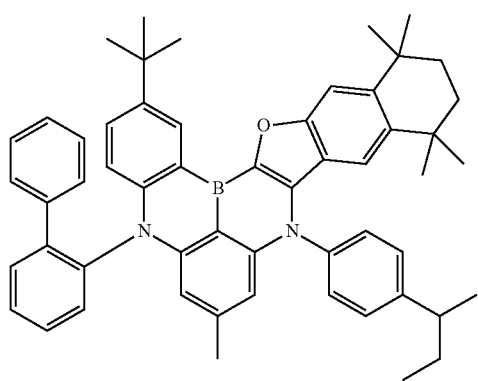 | 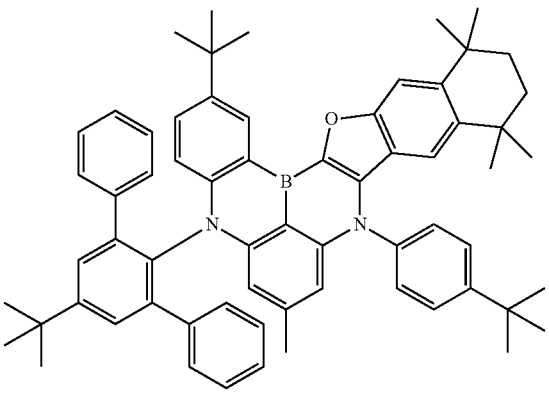 |
| 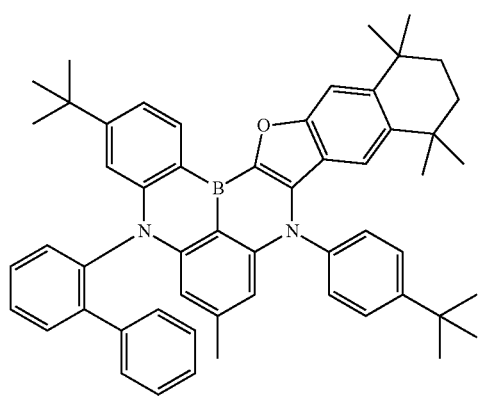 | 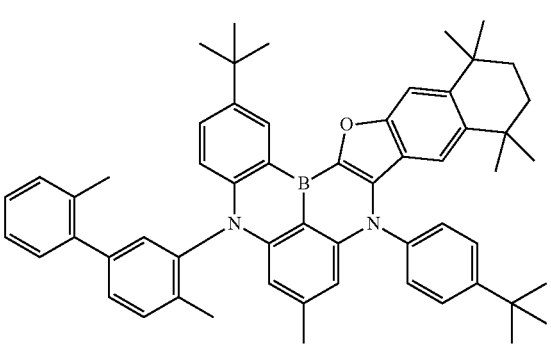 |
| 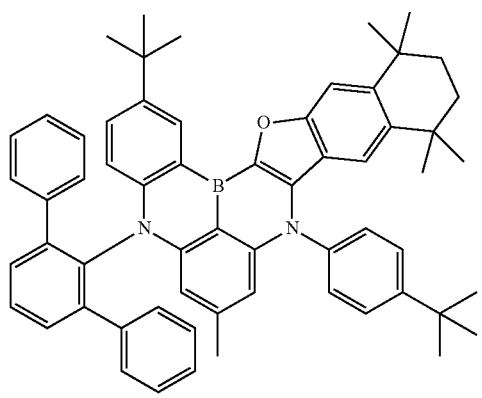 | 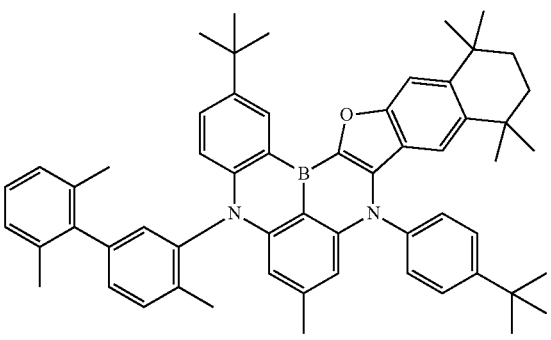 |

1289
-continued
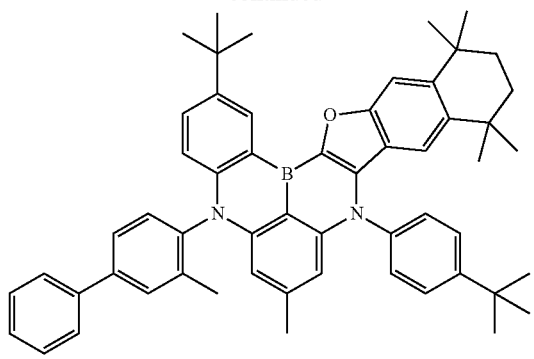
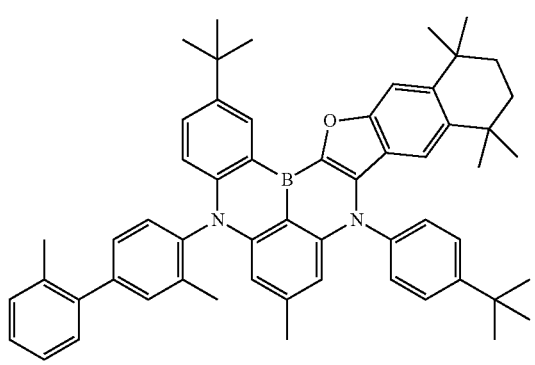
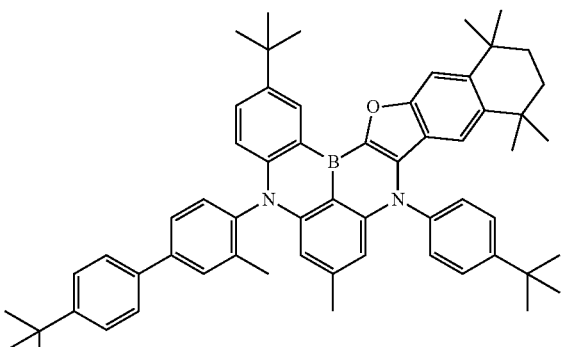
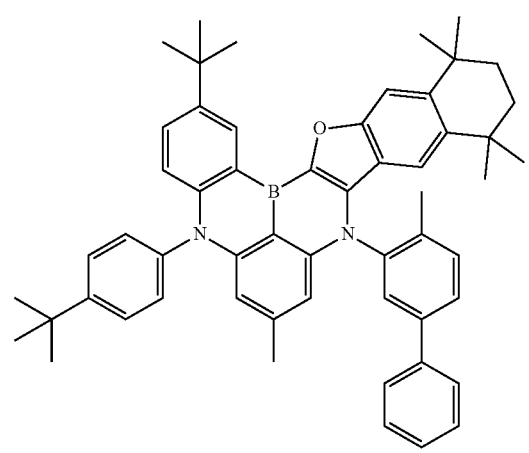
1290
-continued
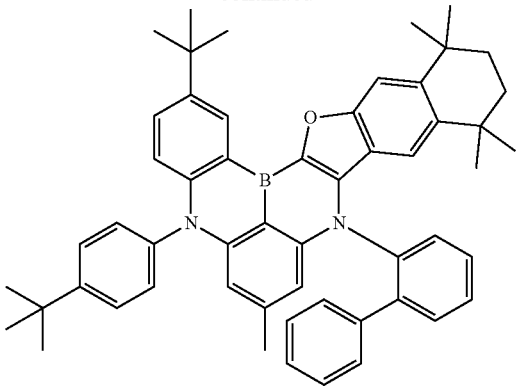
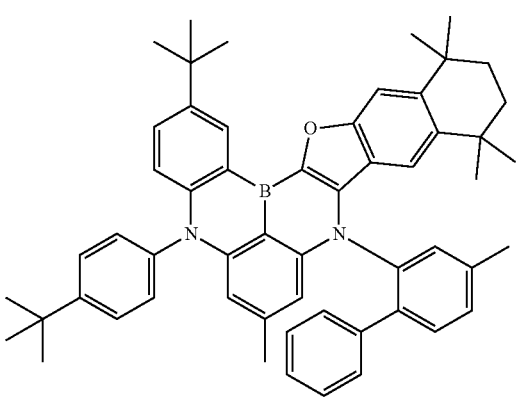
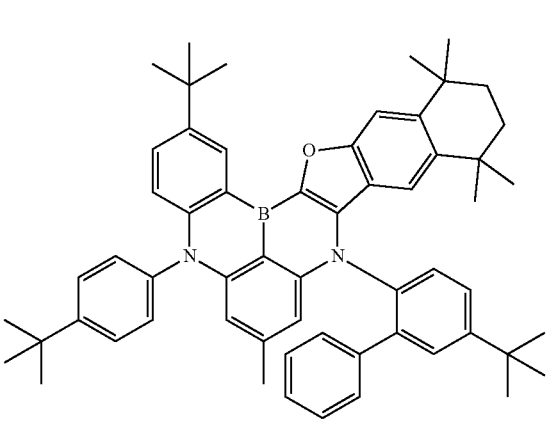
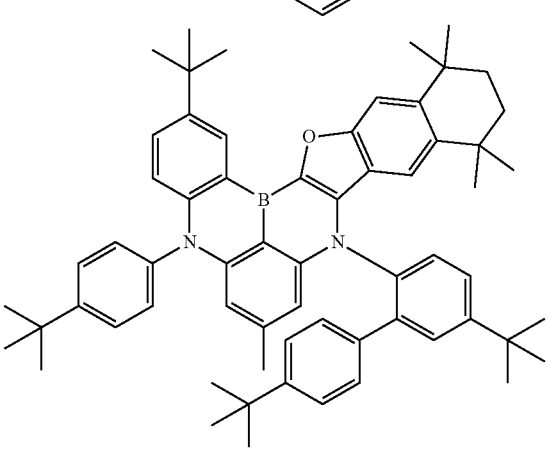

1291
-continued
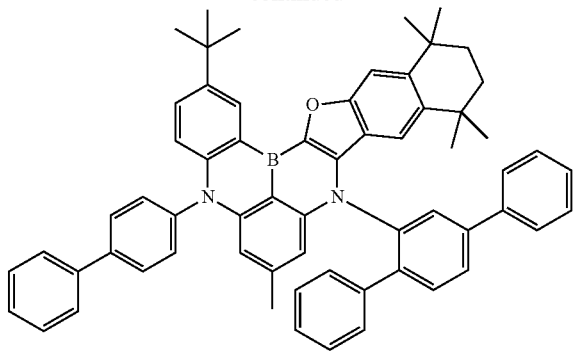
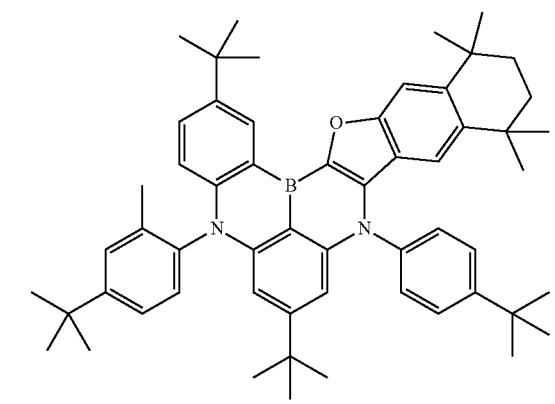
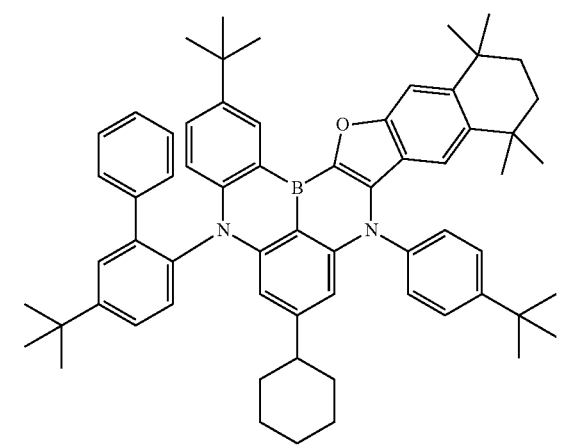
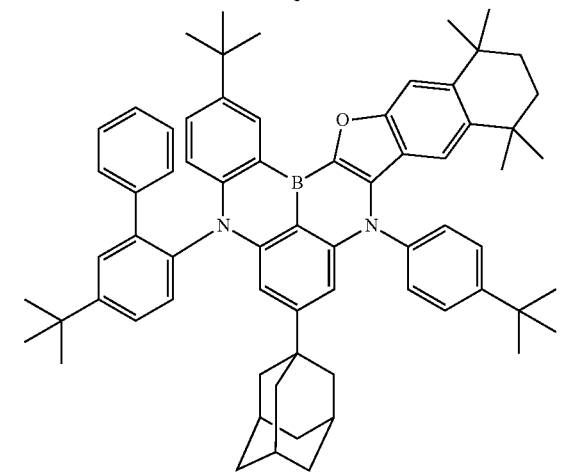
1292
-continued
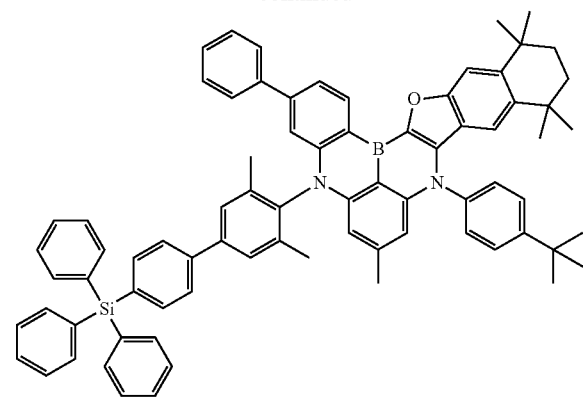
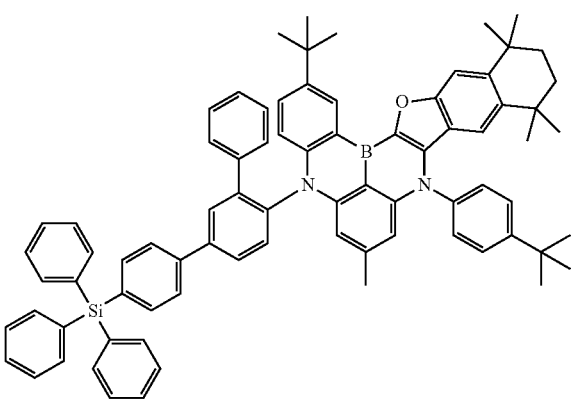
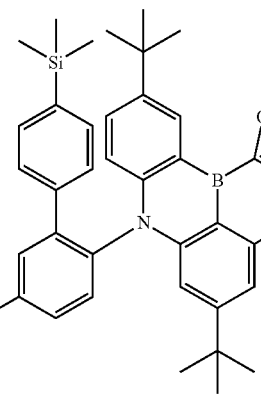
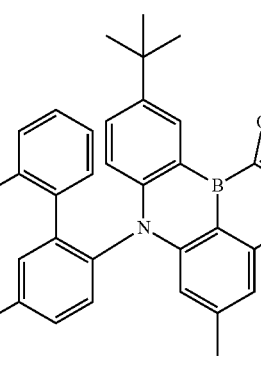

1293
-continued
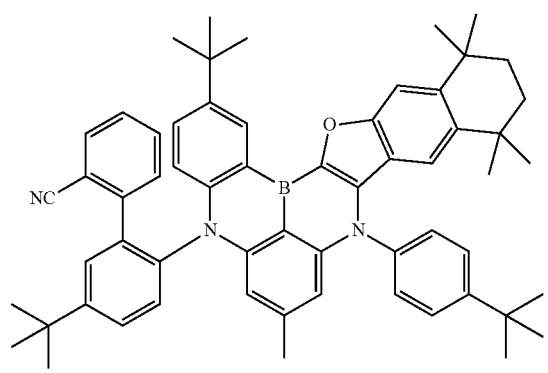
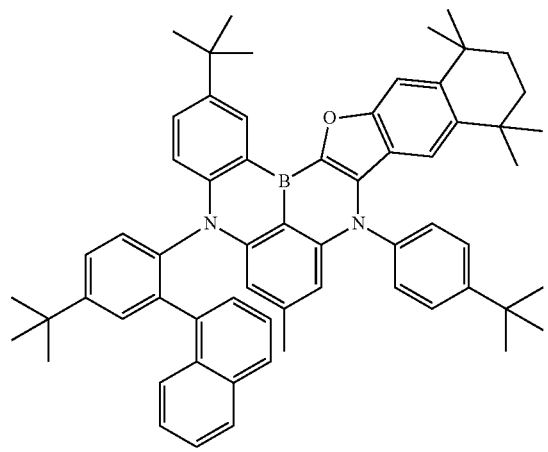
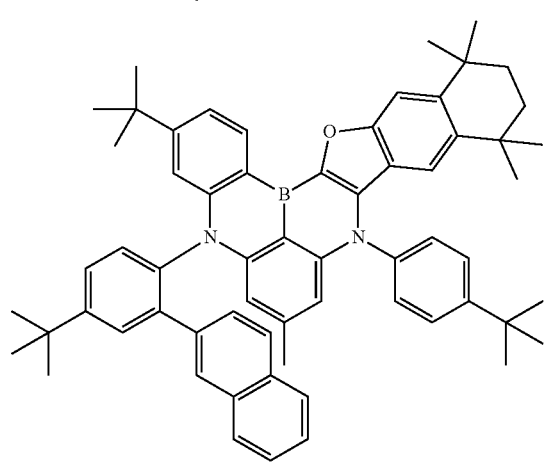
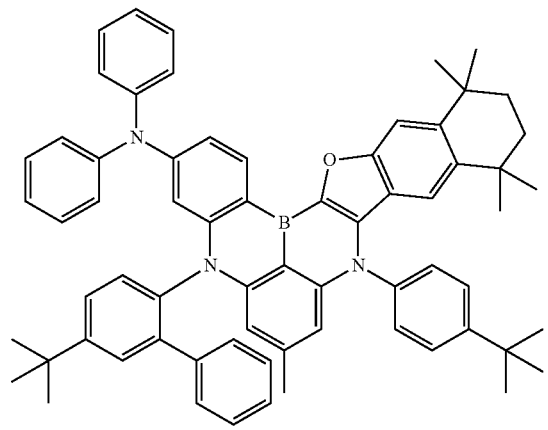
1294
-continued
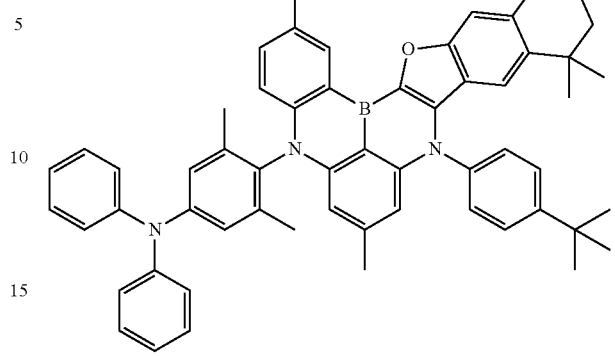
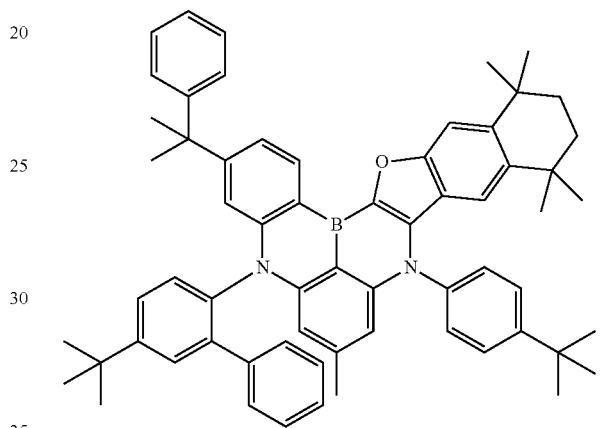
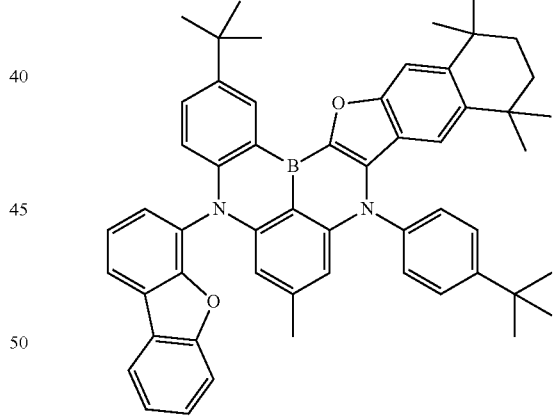
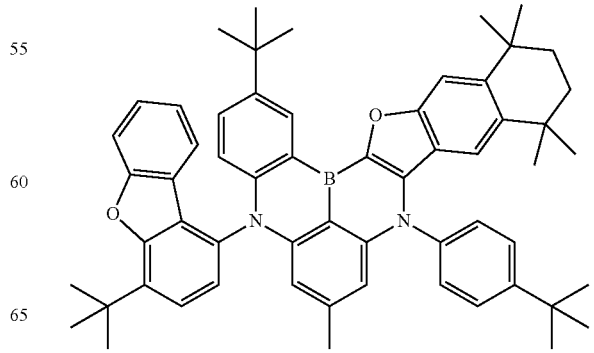

1295
-continued
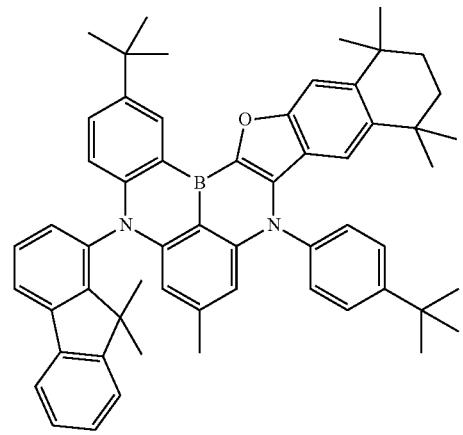
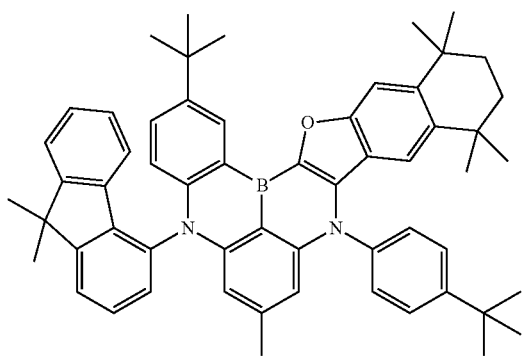
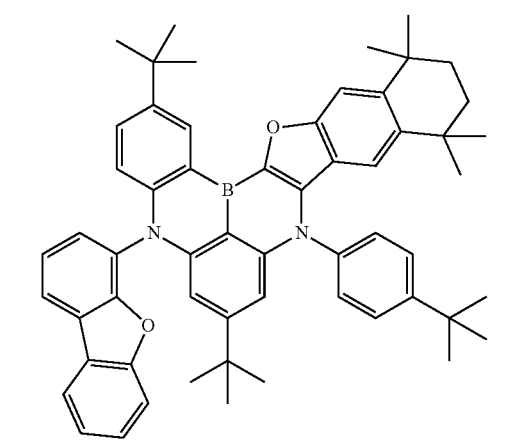
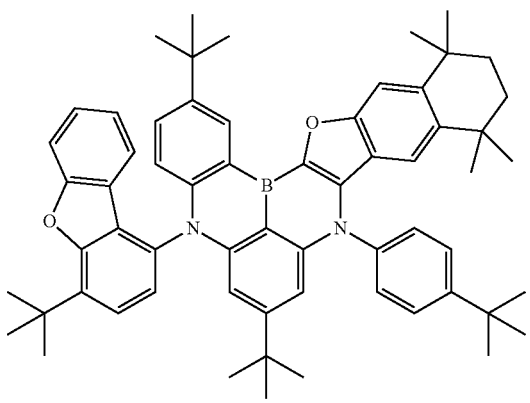
1296
-continued
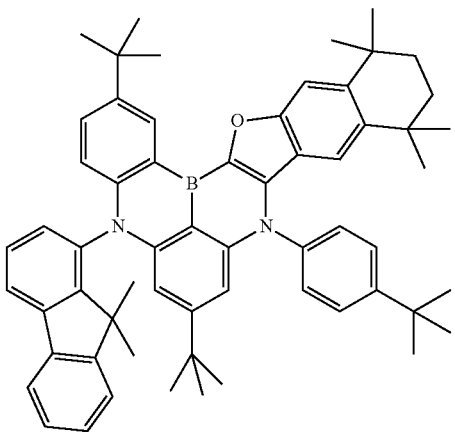
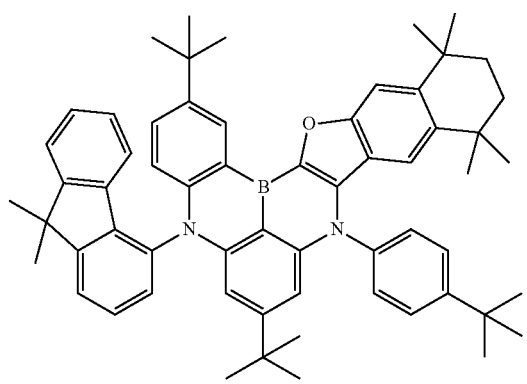
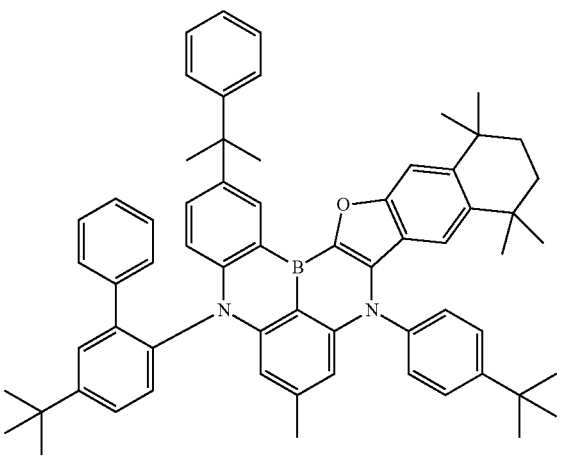

1297
-continued
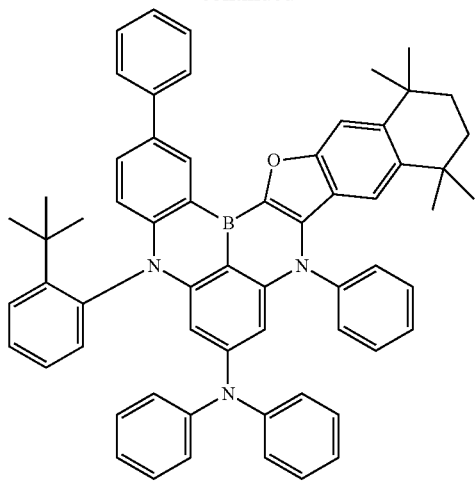
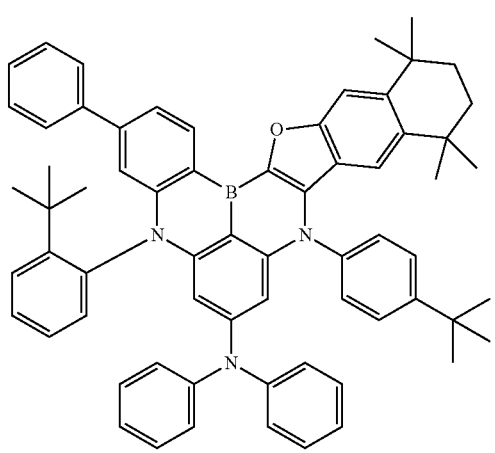
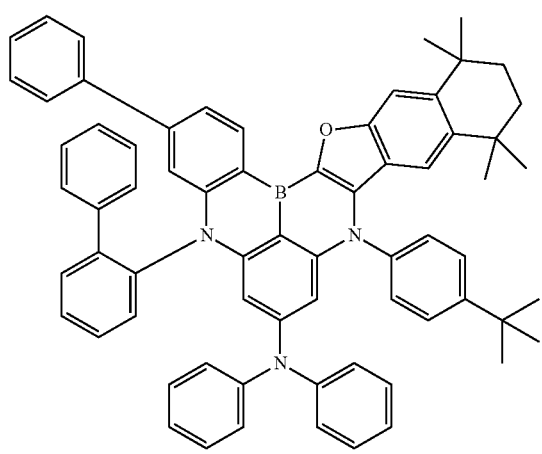
1298
-continued
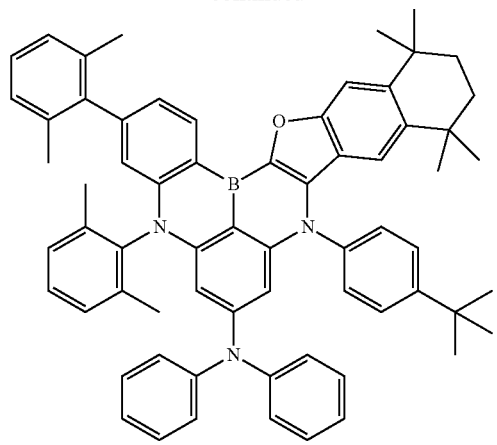
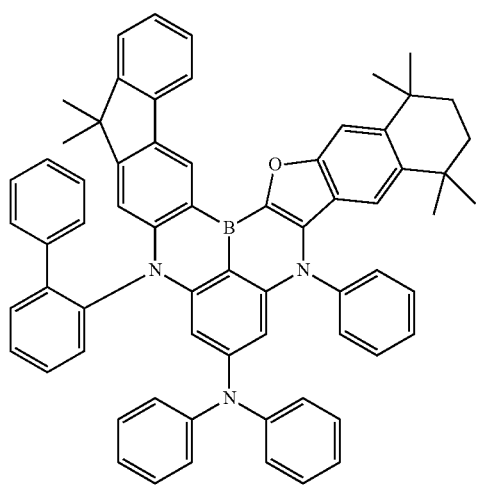
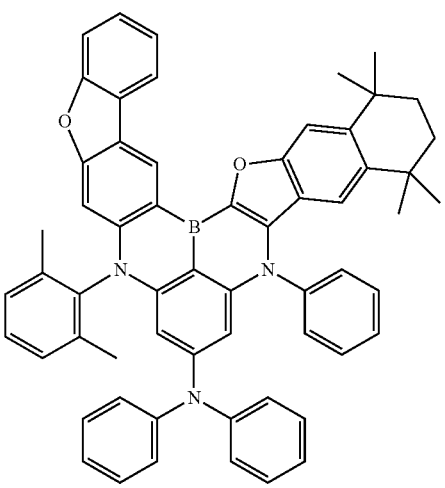

1299
-continued
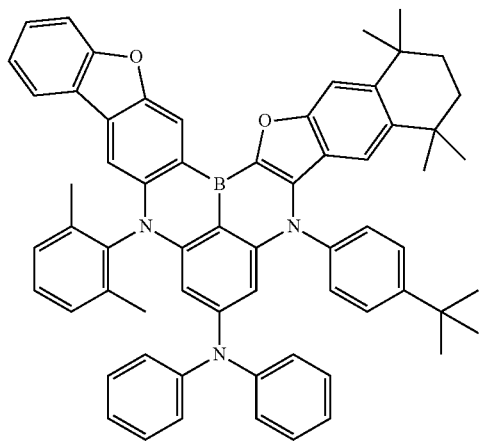
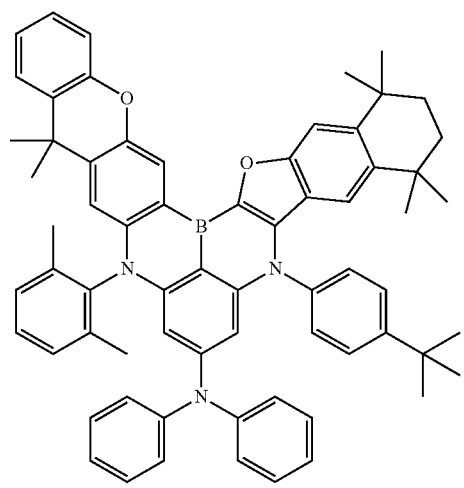
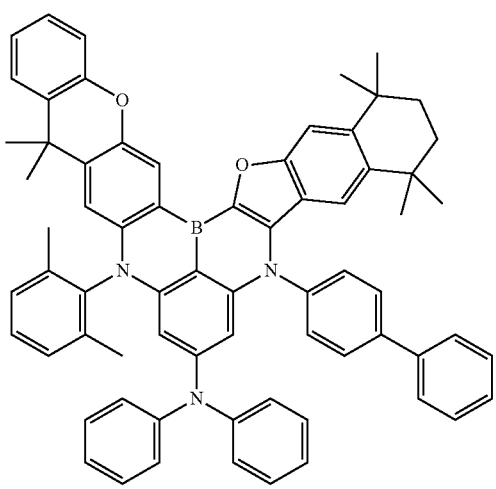
1300
-continued
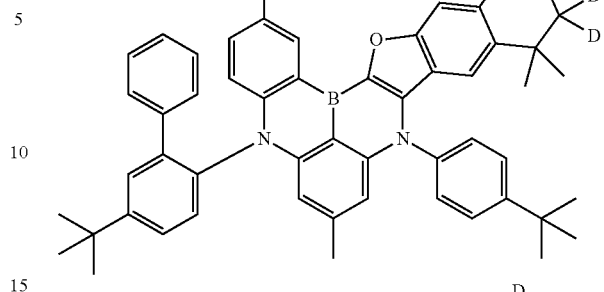
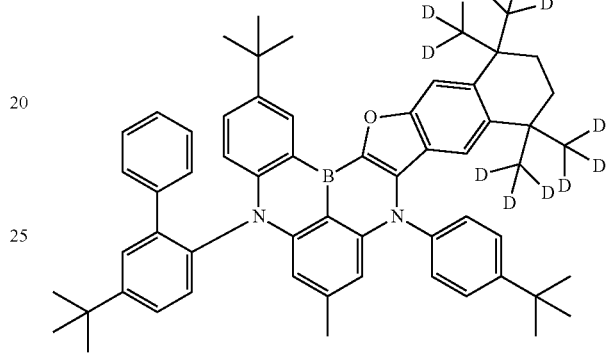
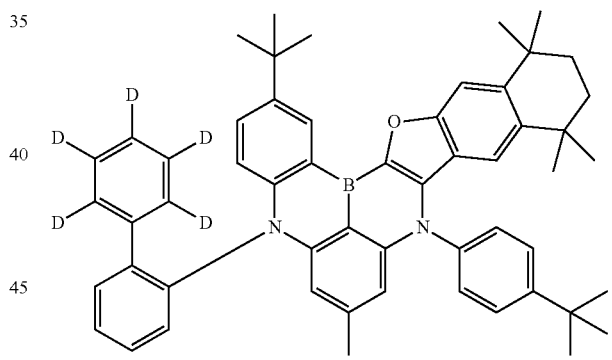
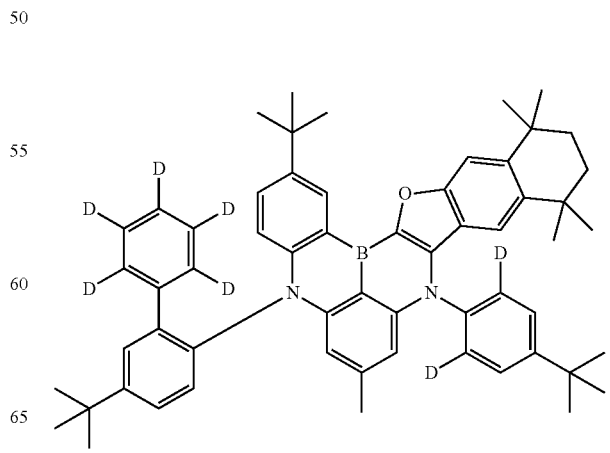

1301
-continued
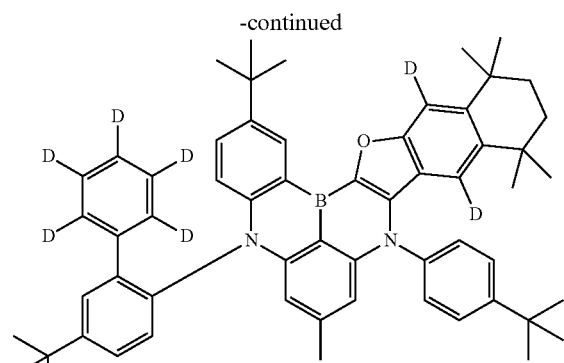
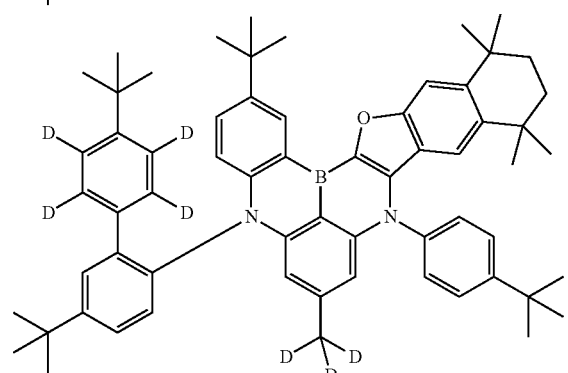
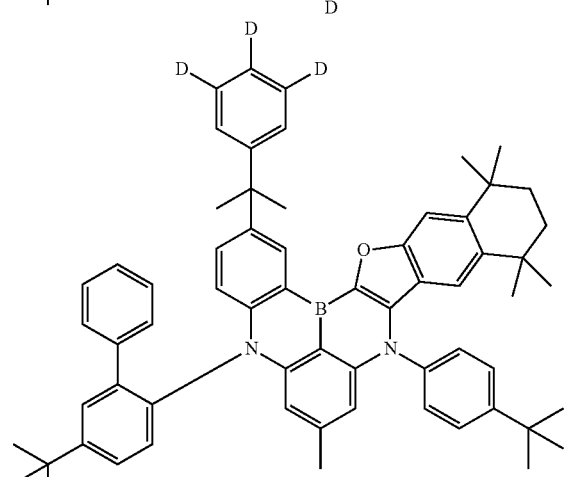
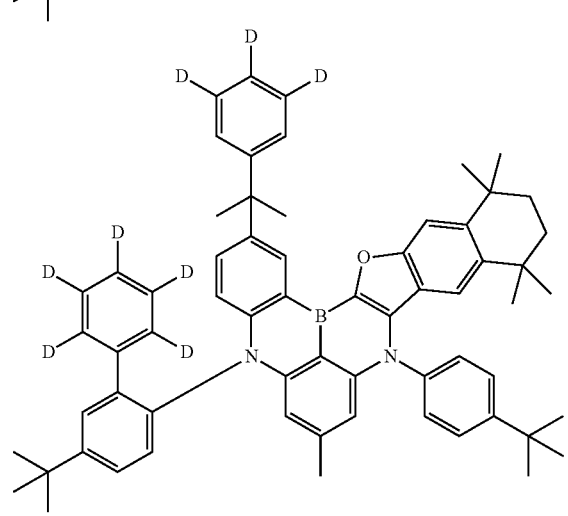
1302
-continued
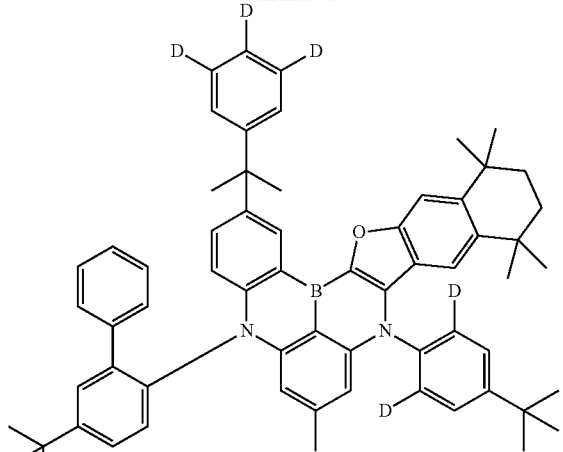
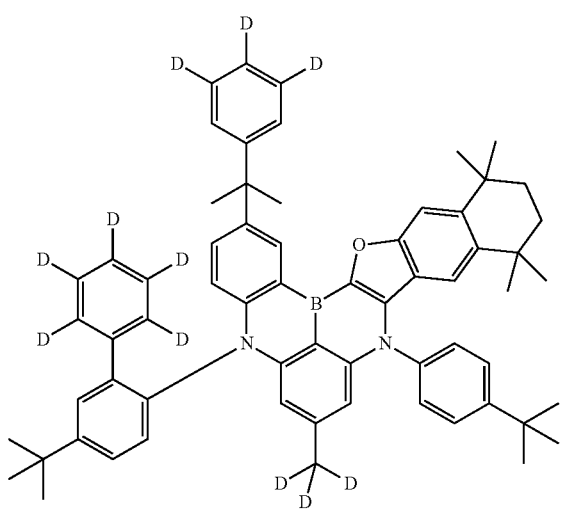
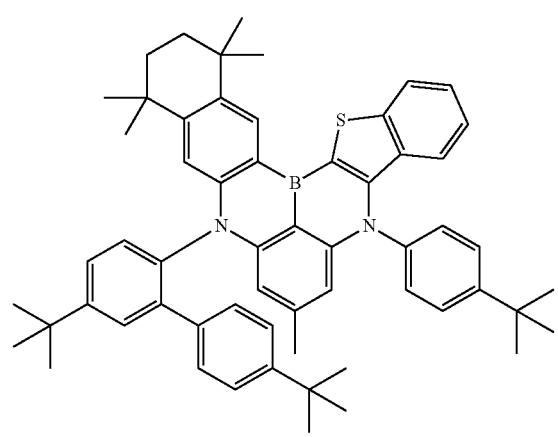

1303
-continued
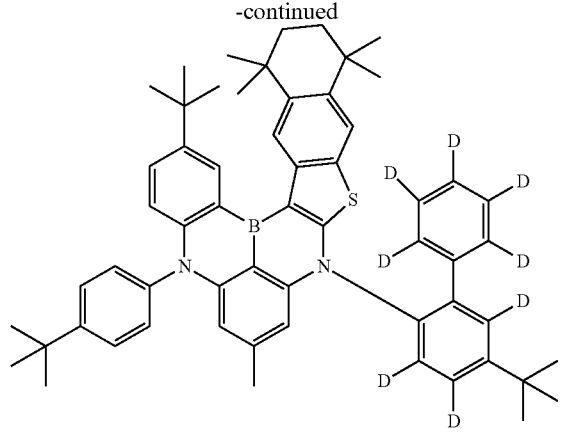
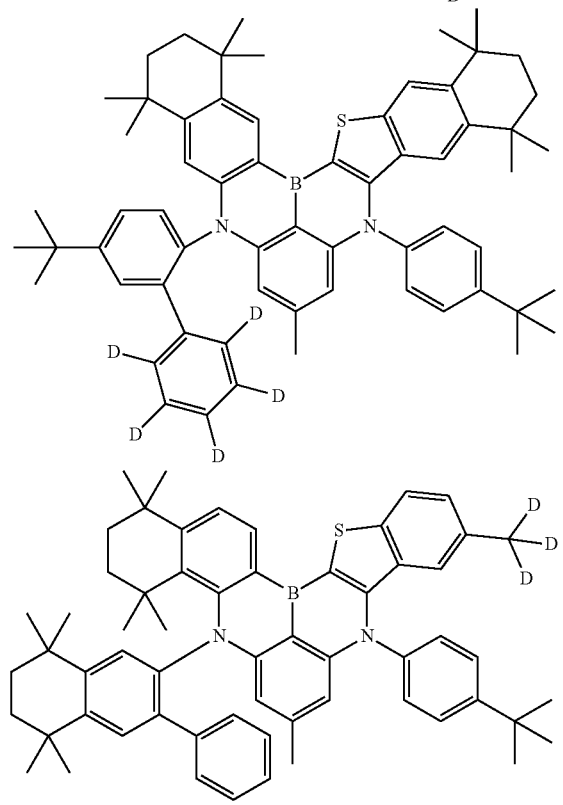
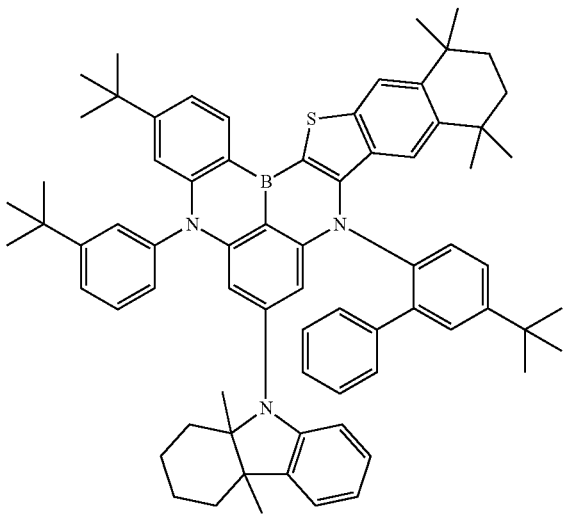
1304
-continued
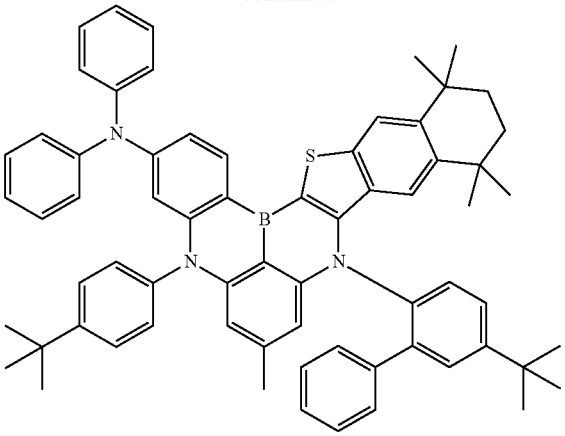
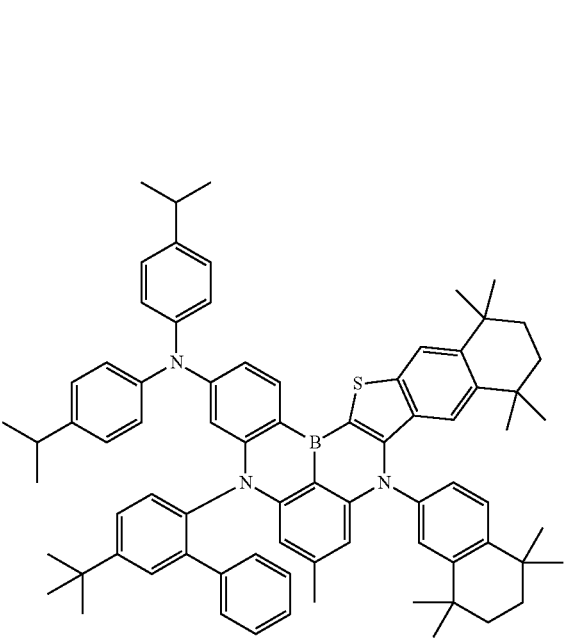
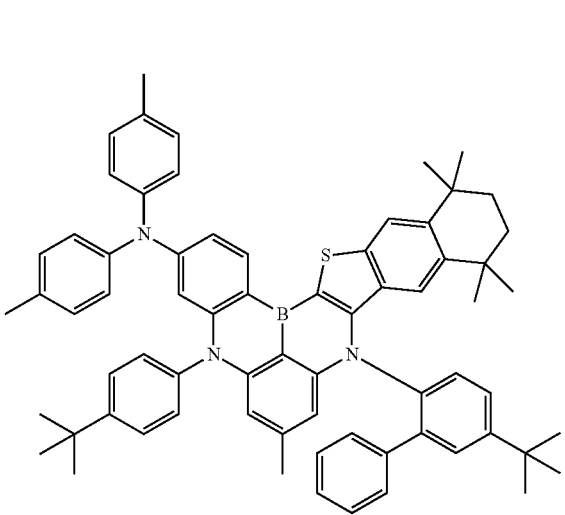

| 1305 -continued | 1306 -continued |
|---|---|
| 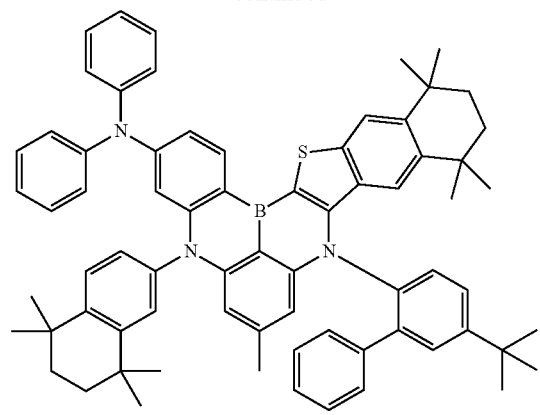 |  |
| 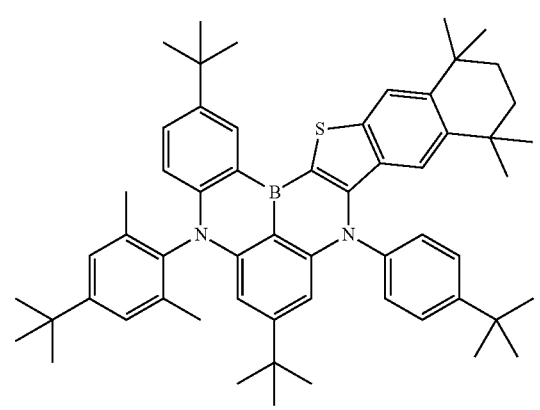 | 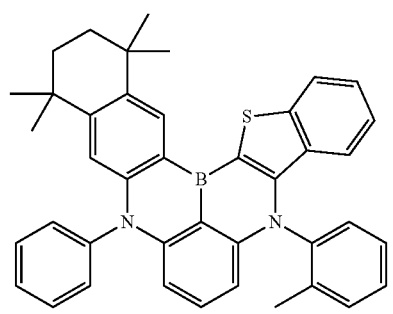 |
| 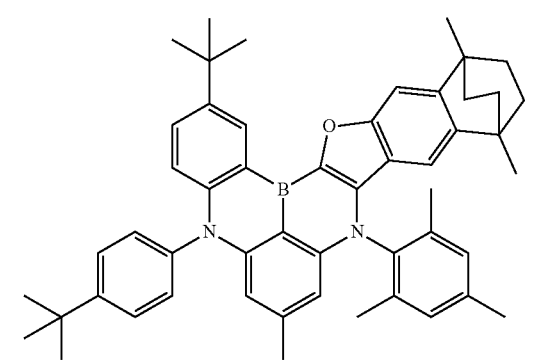 | 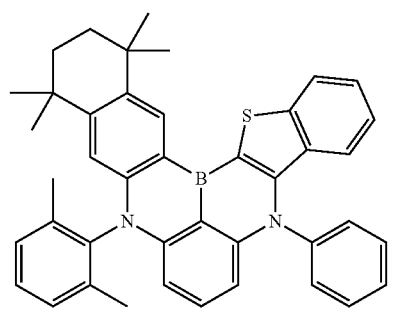 |
| 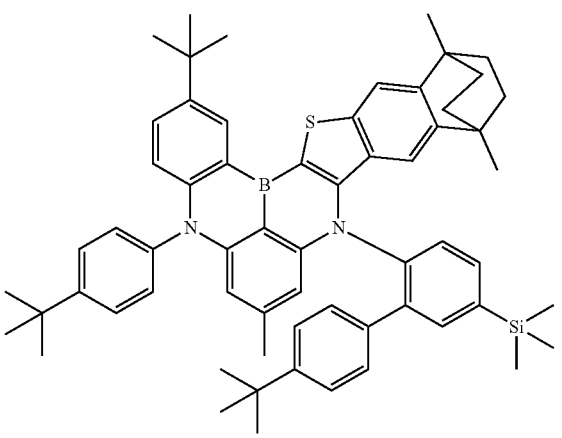 | 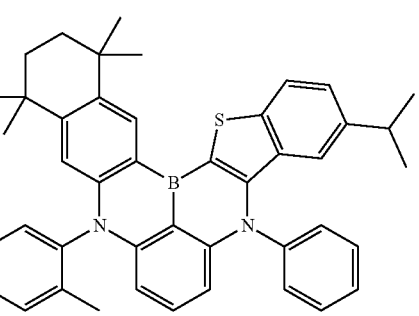 |
| | 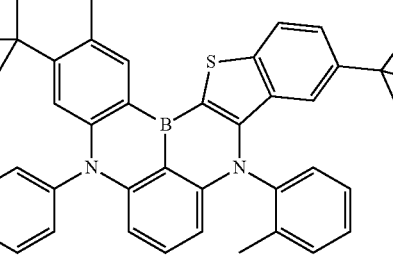 |

1307
-continued
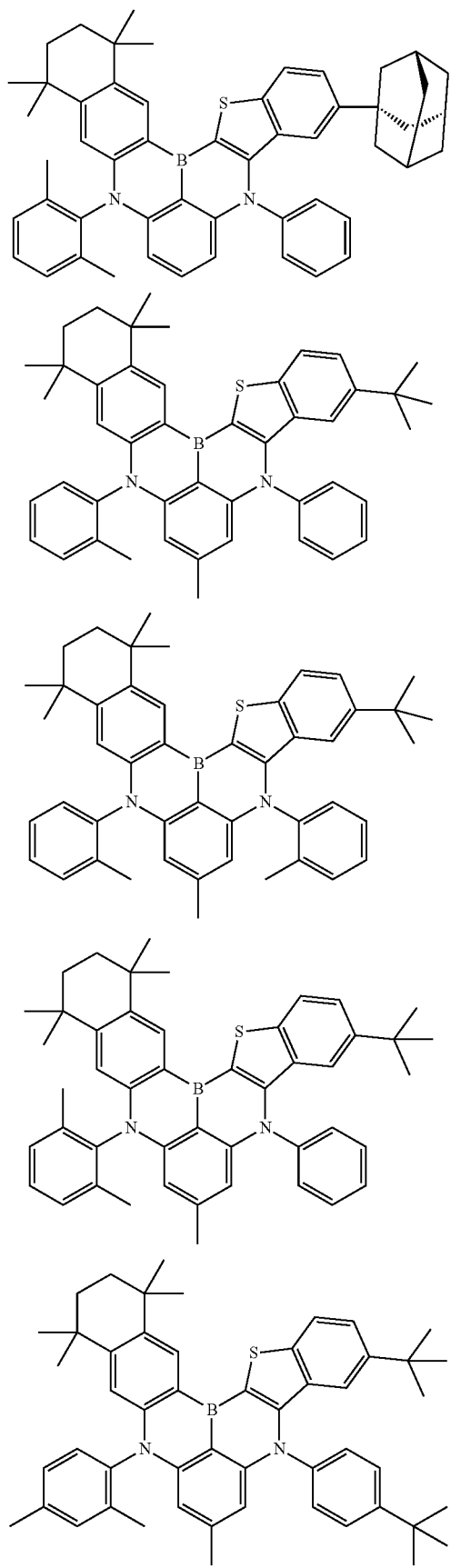
1308
-continued
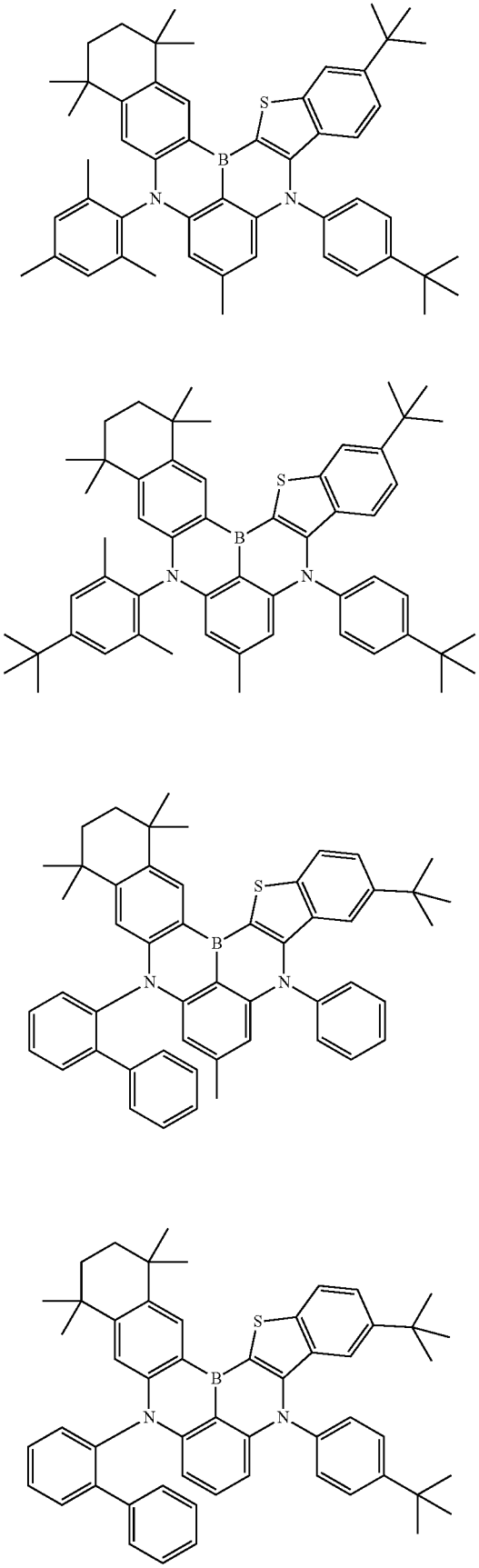

| 1309 -continued | 1310 -continued |
|---|---|
|  | 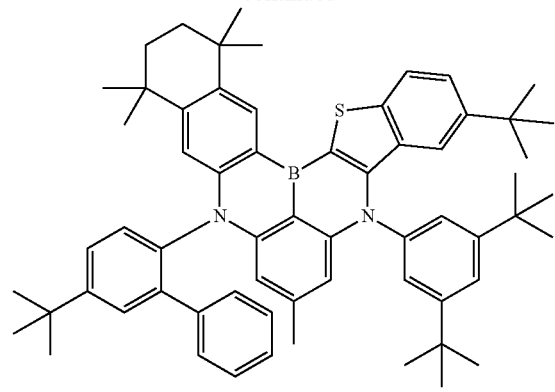 |
| 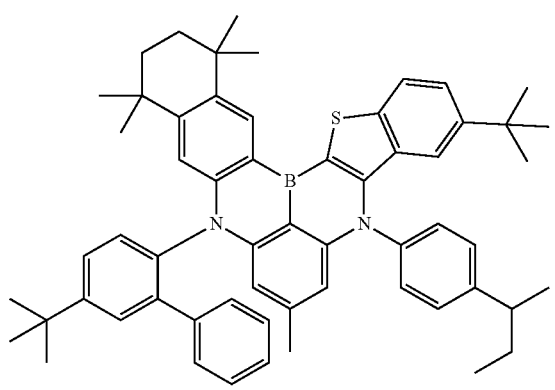 | 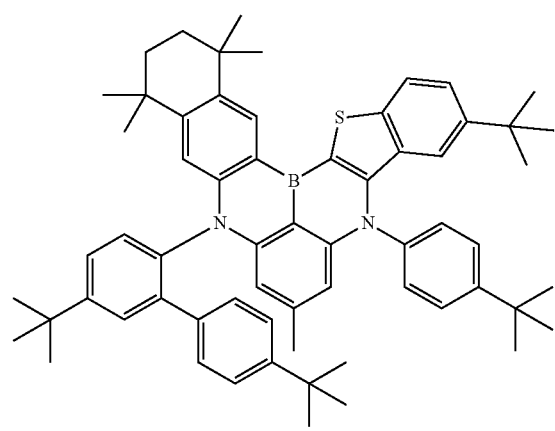 |
| 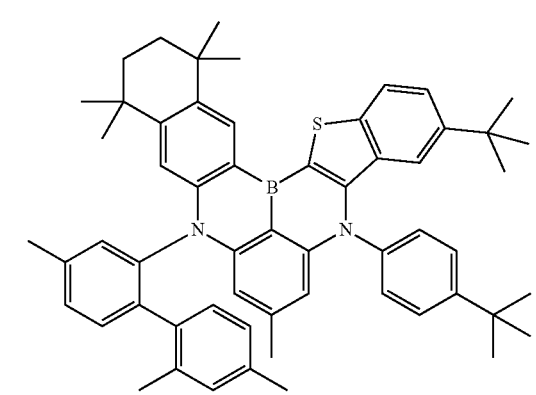 | 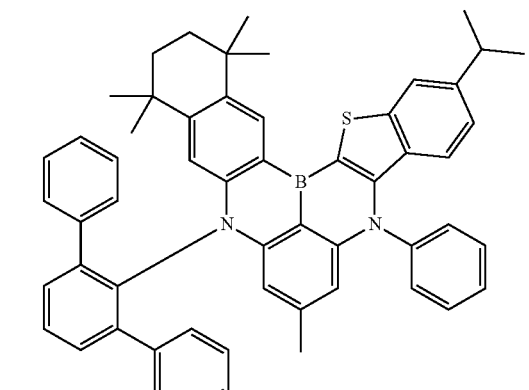 |
| 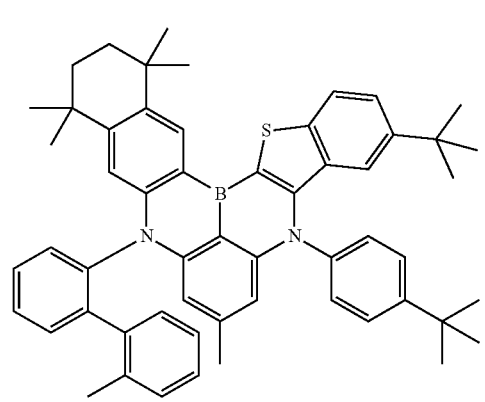 | 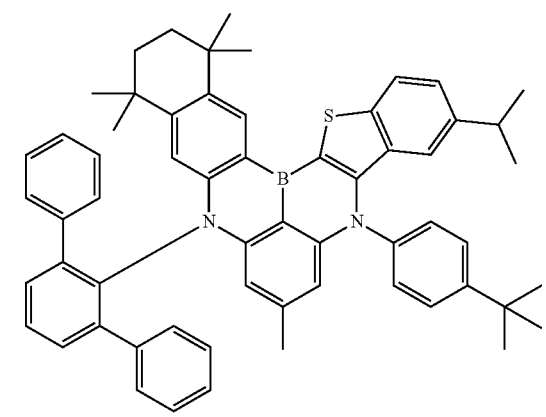 |

1311
-continued
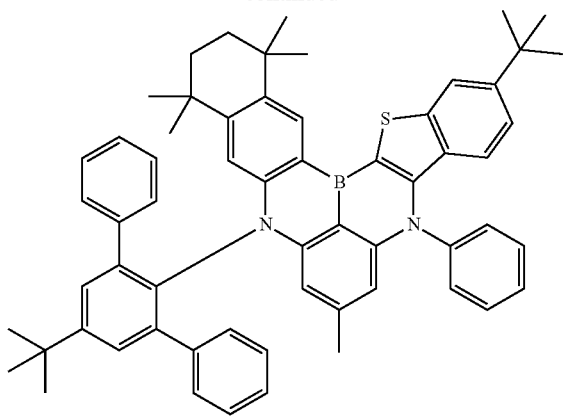
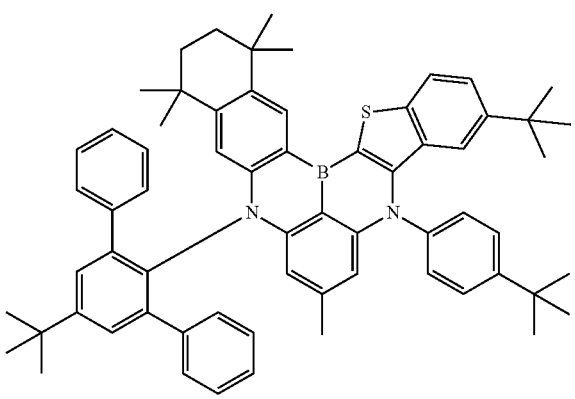
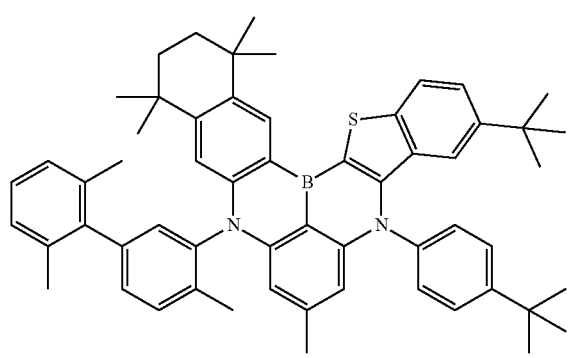
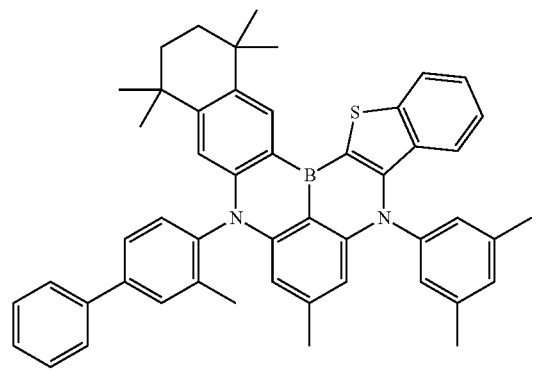
1312
-continued
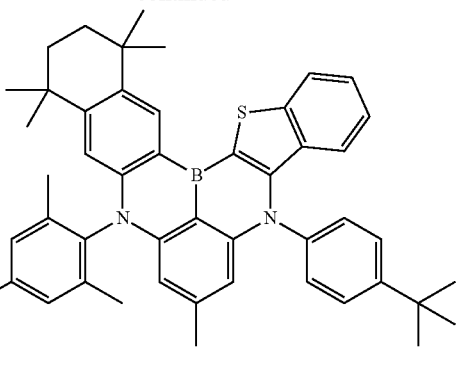
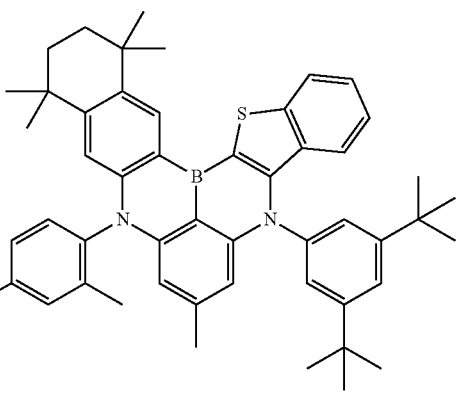
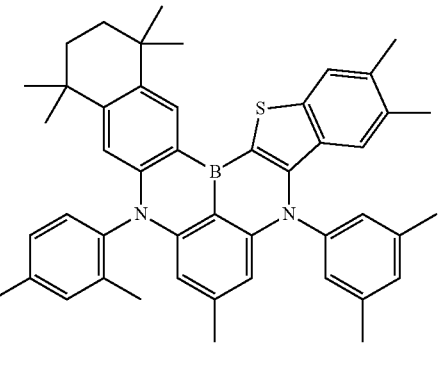
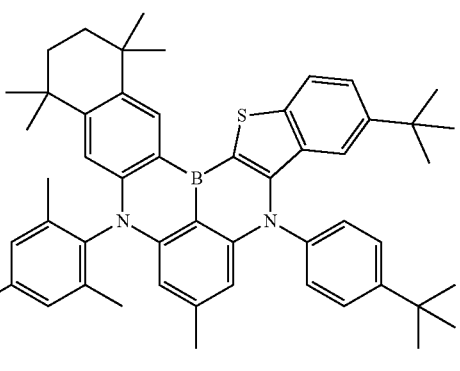

1313
-continued
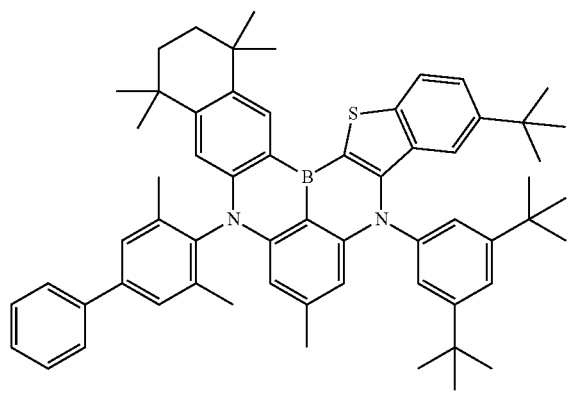
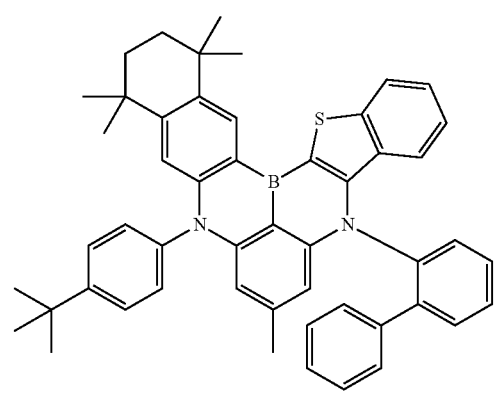
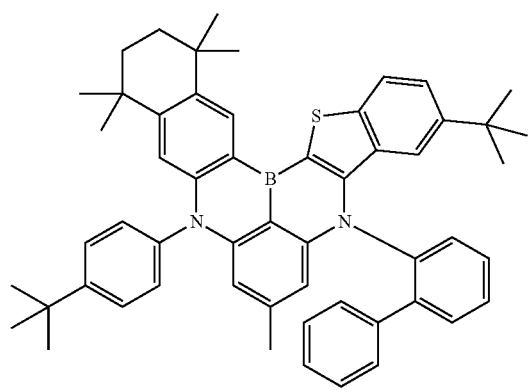
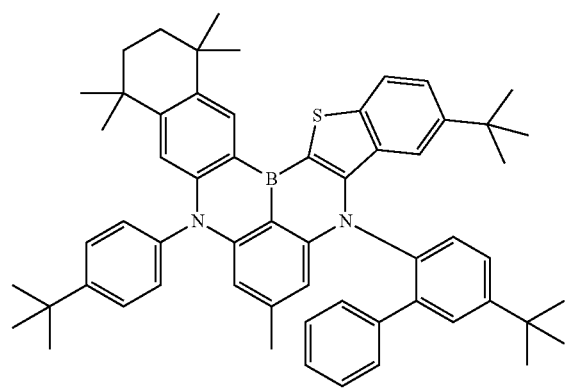
1314
-continued
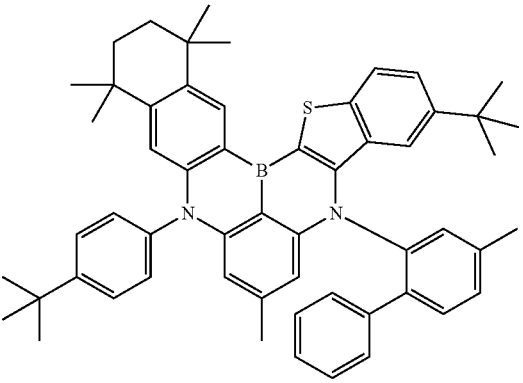
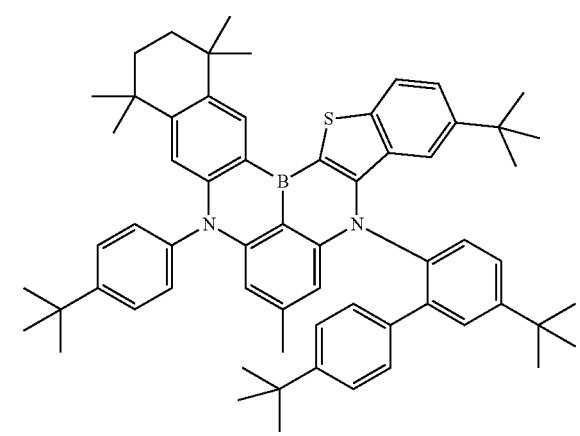
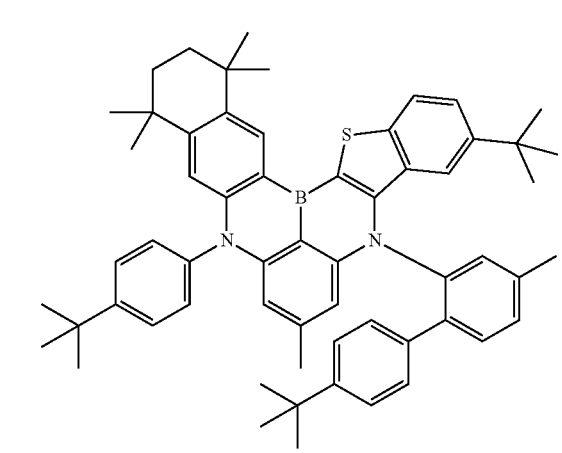
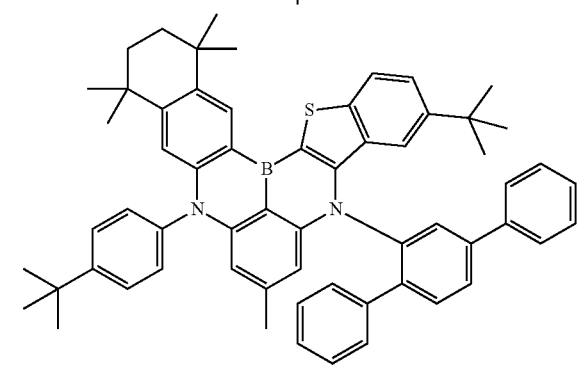

1315
-continued
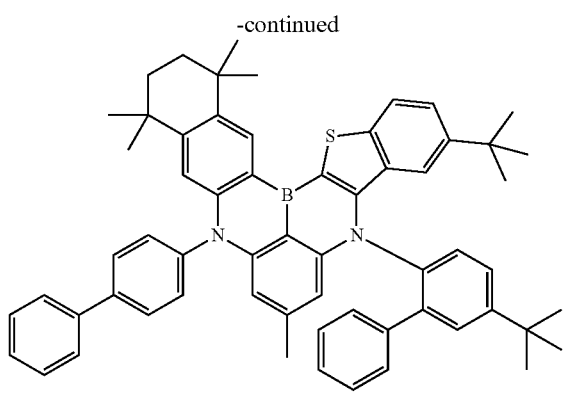
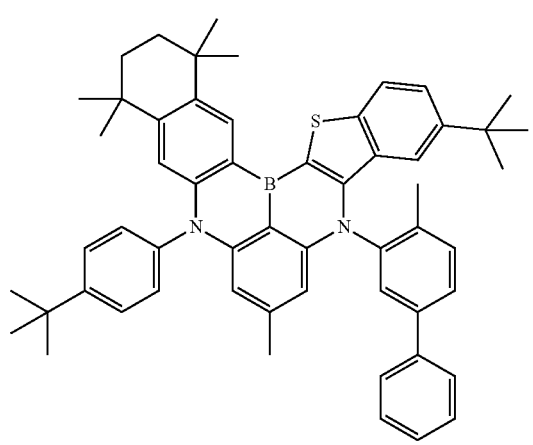
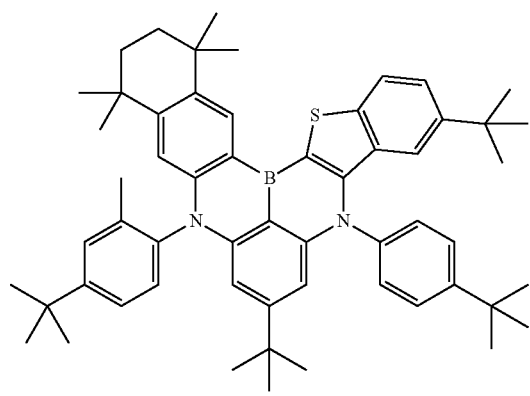
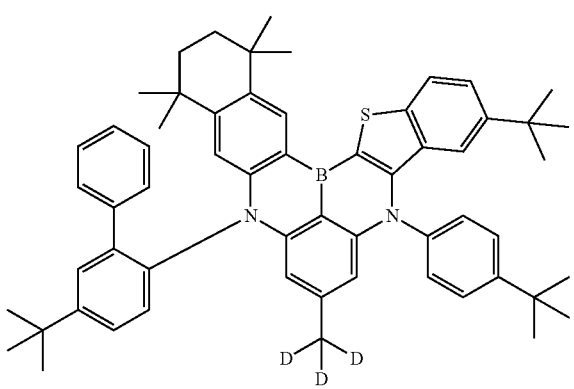
1316
-continued
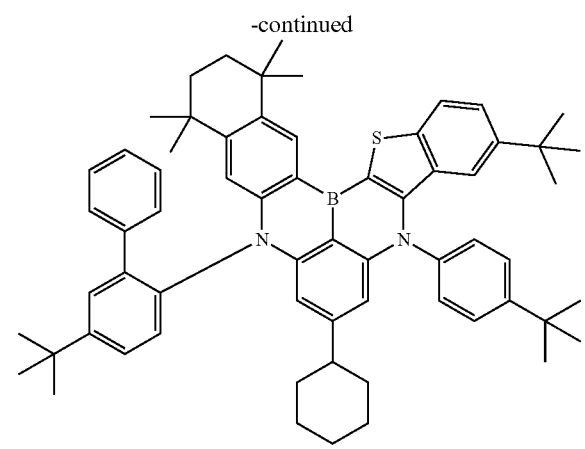
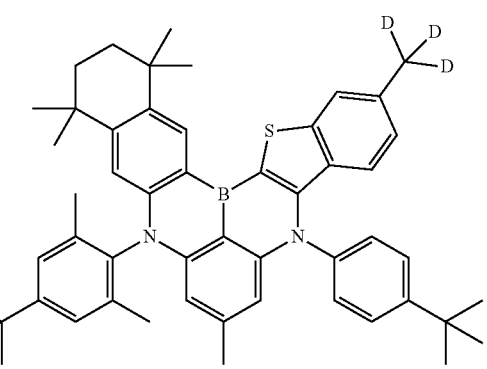
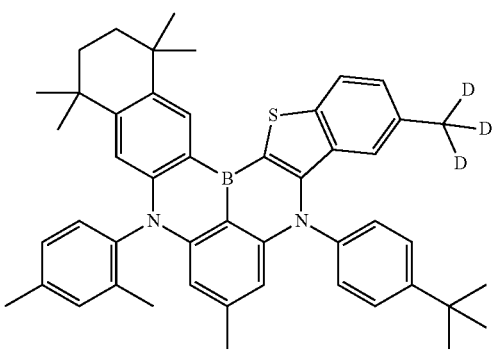
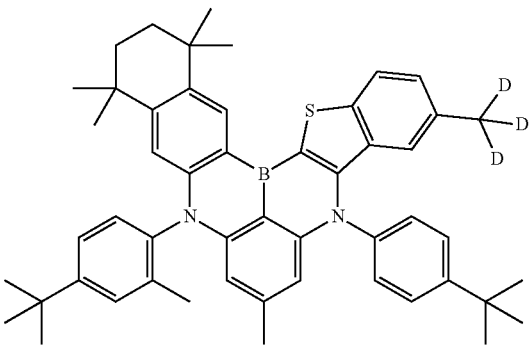

1317
-continued
1318
-continued
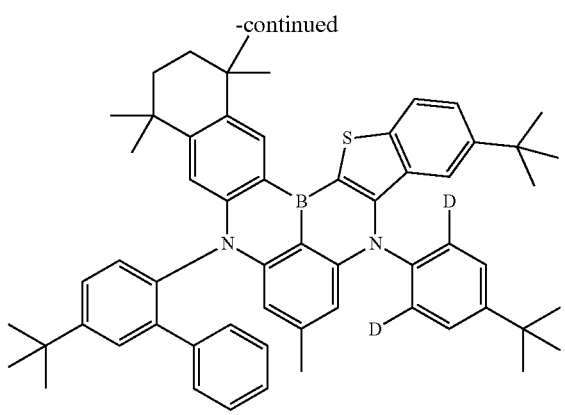
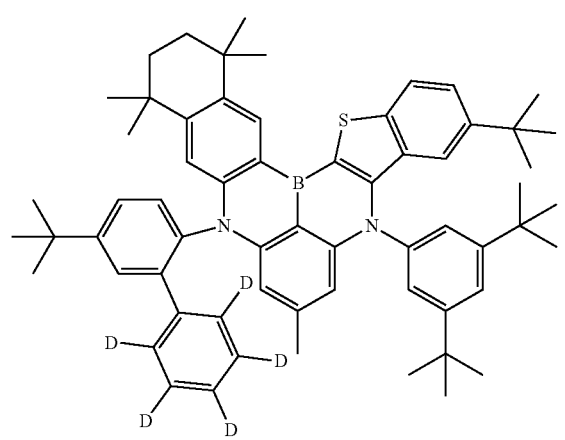
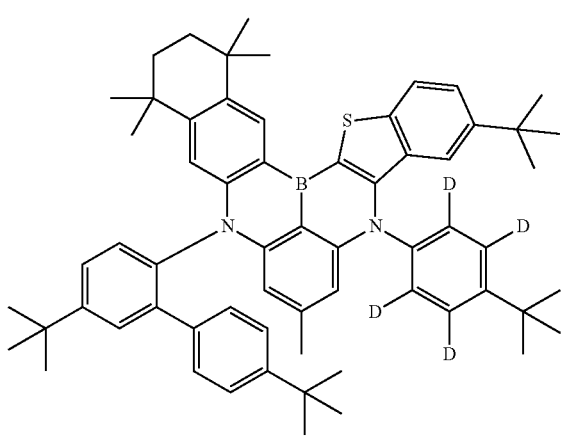
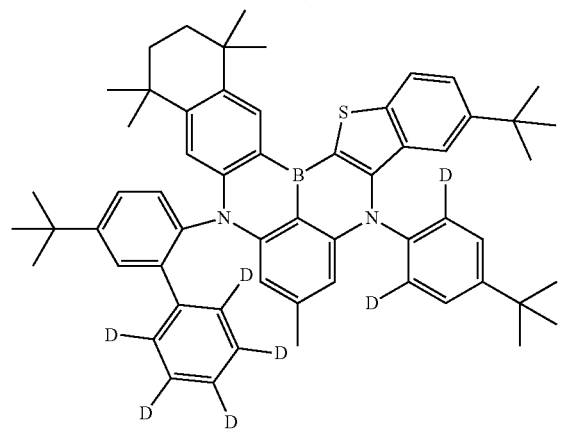

| 1319 -continued | 1320 -continued |
|---|---|
| 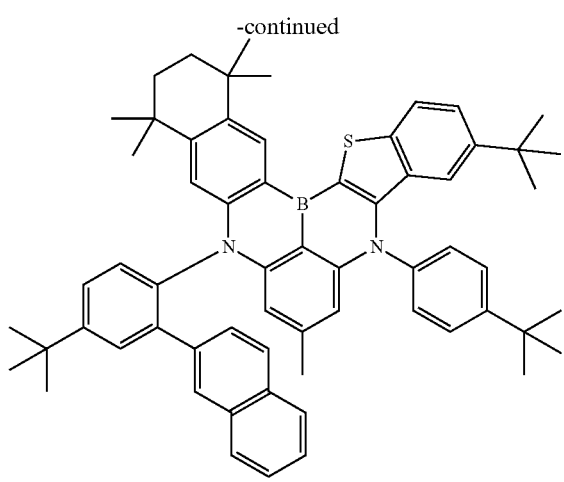 | 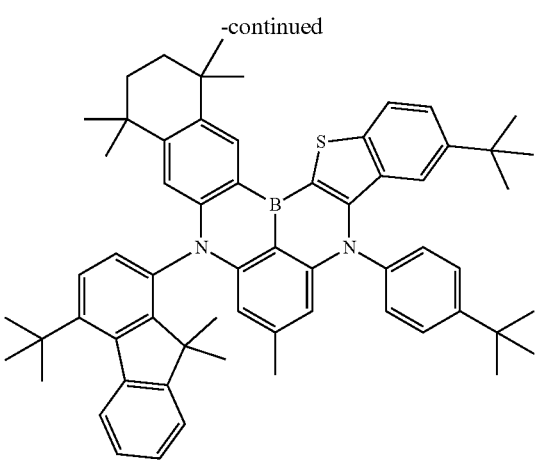 |
| 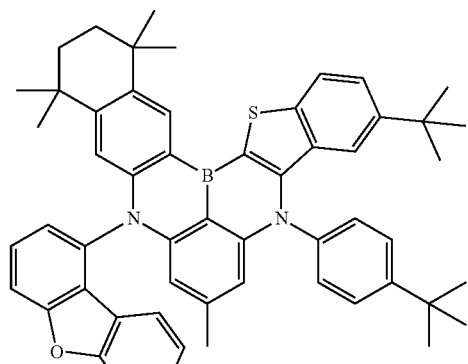 | 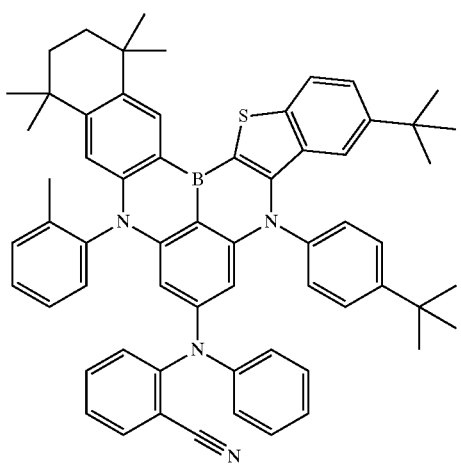 |
| 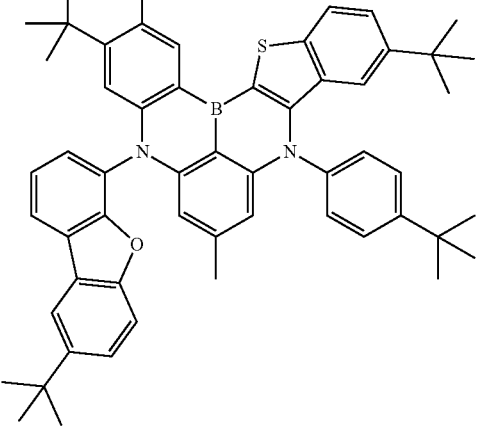 | 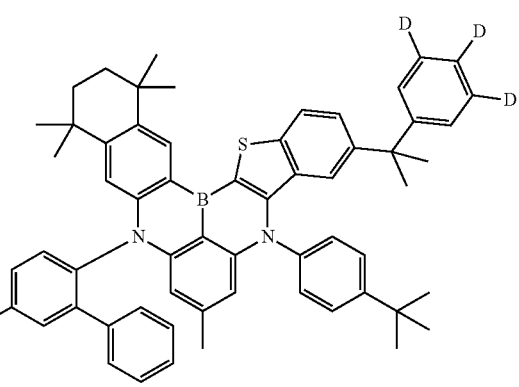 |
| 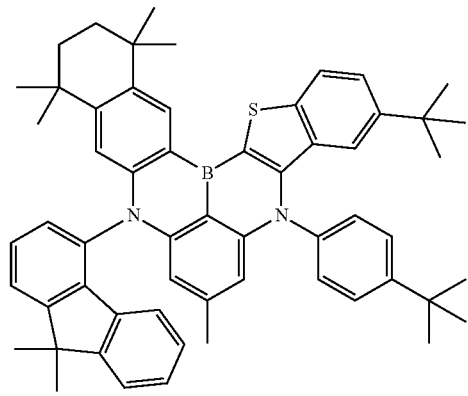 | 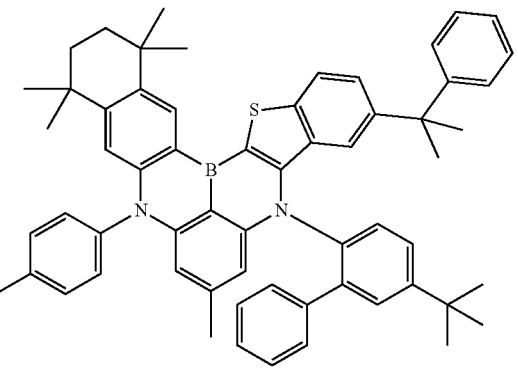 |

1321
-continued
1322
-continued
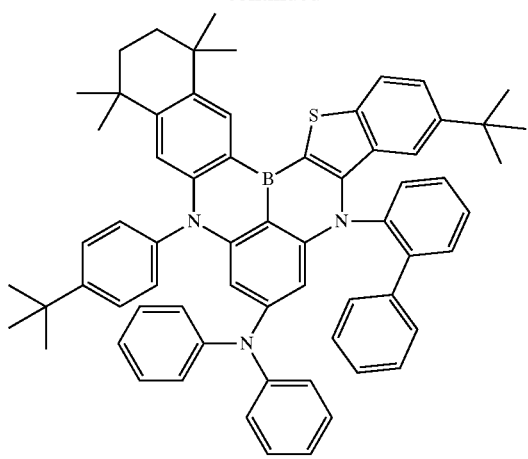
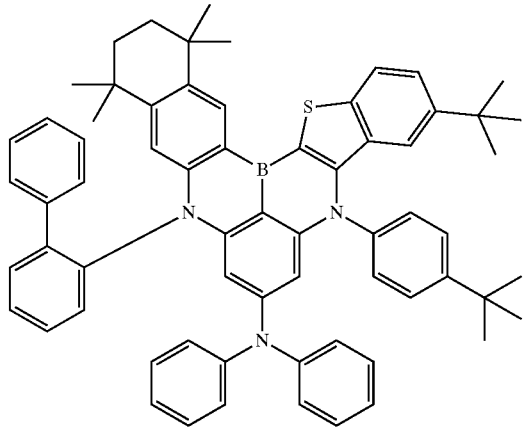
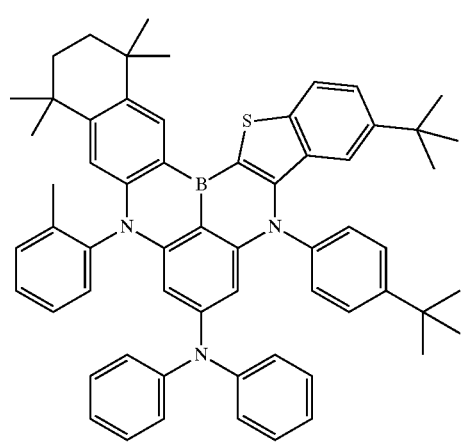
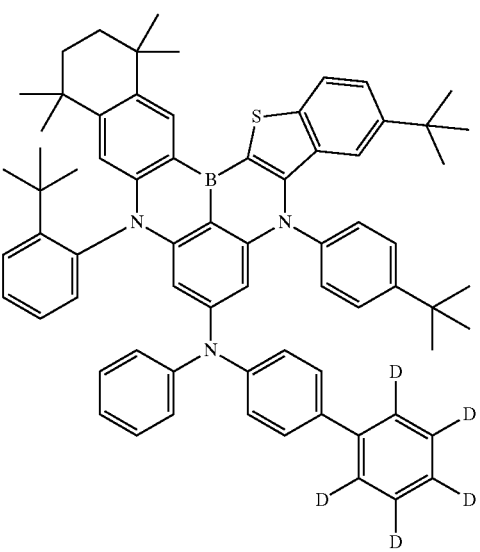
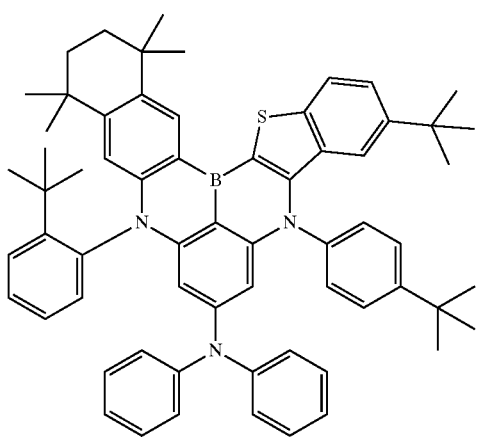

1323
-continued
1324
-continued
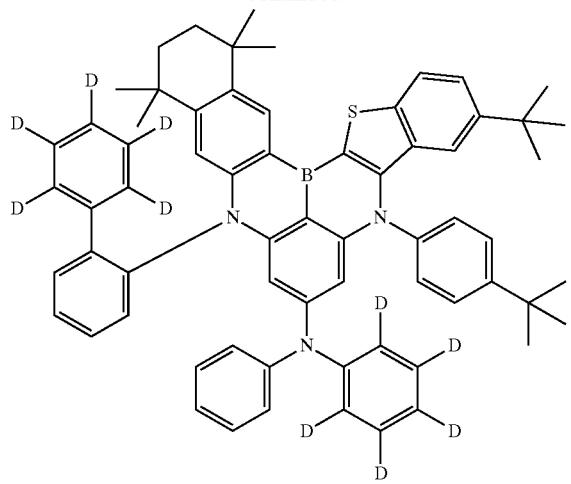
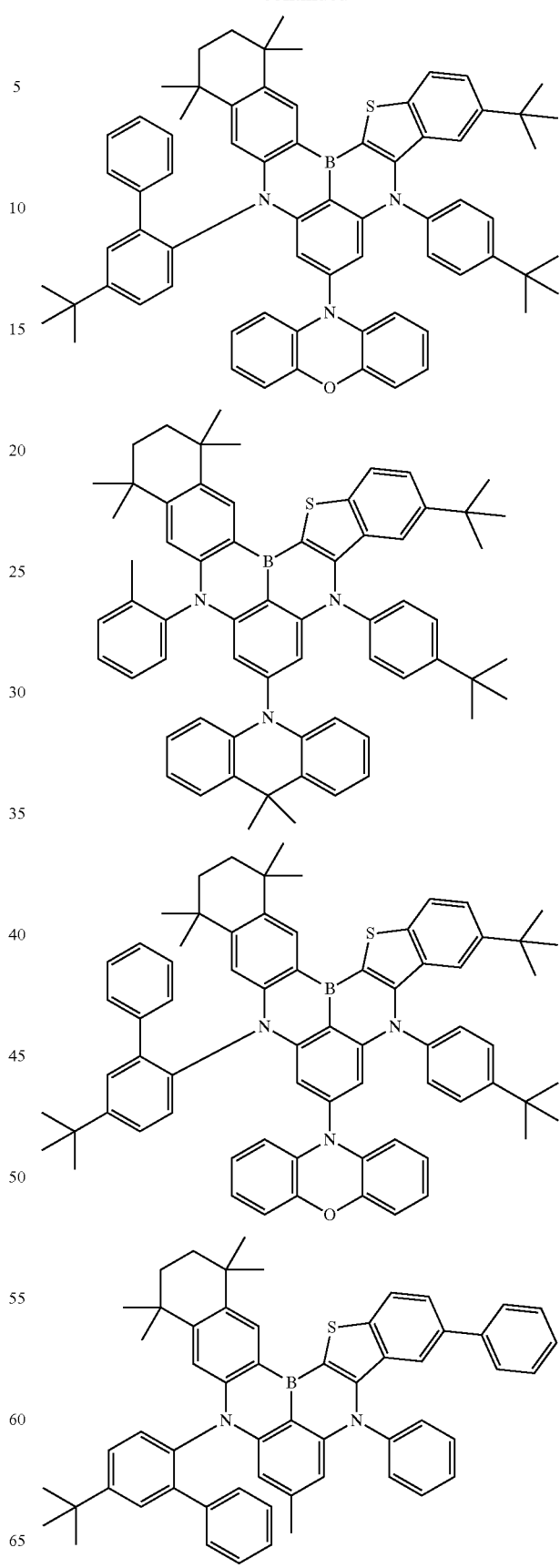

1325
-continued
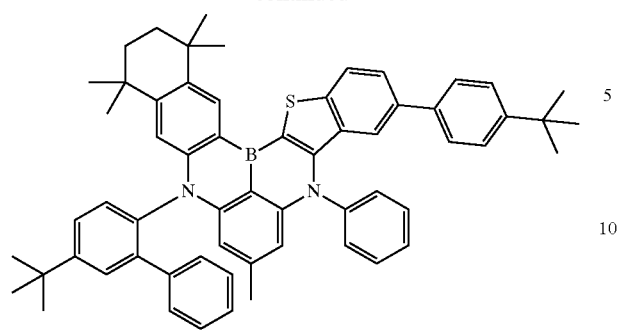

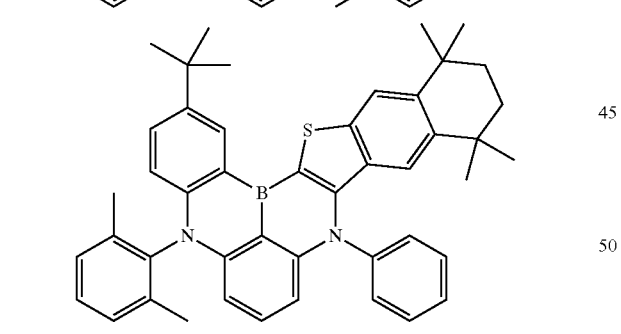
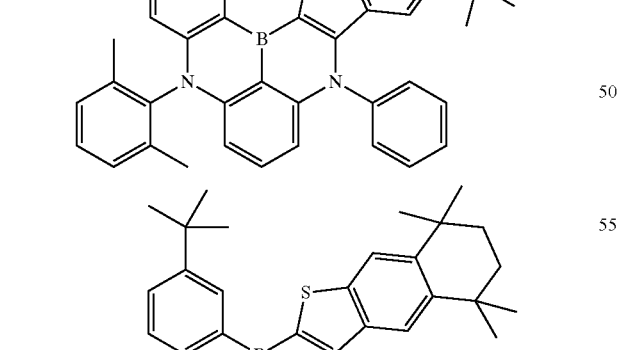
1326
-continued
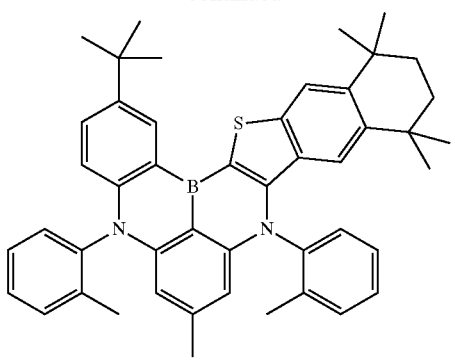
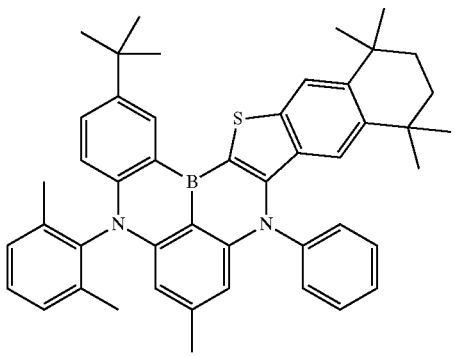
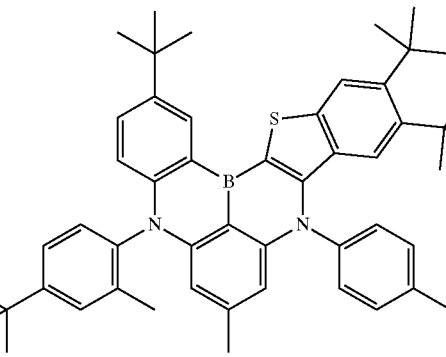
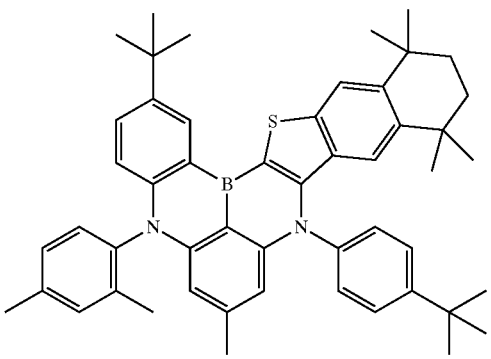

1327
-continued
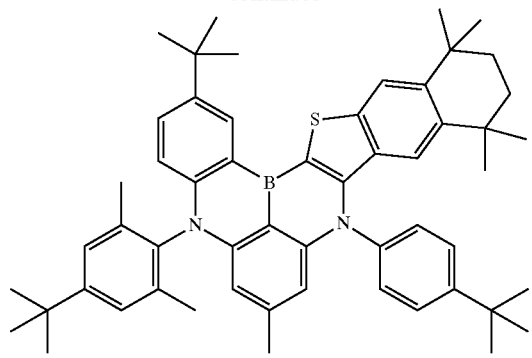
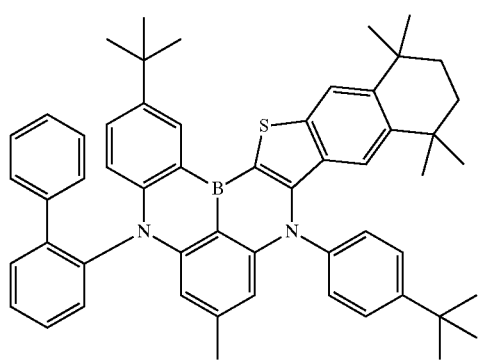
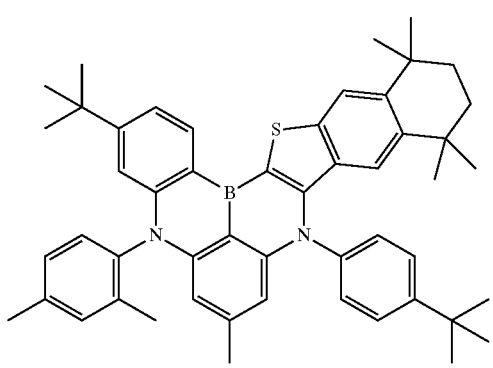
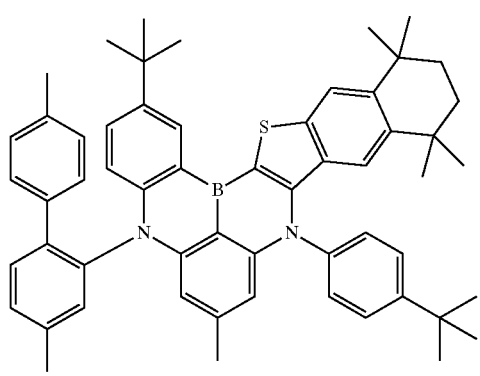
1328
-continued
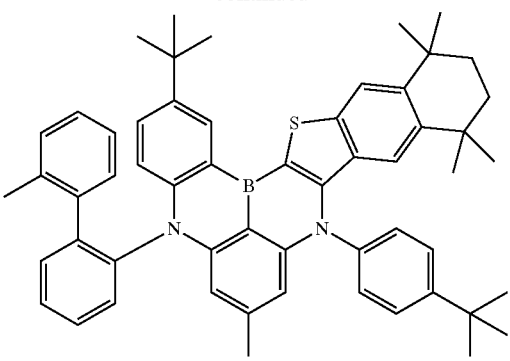
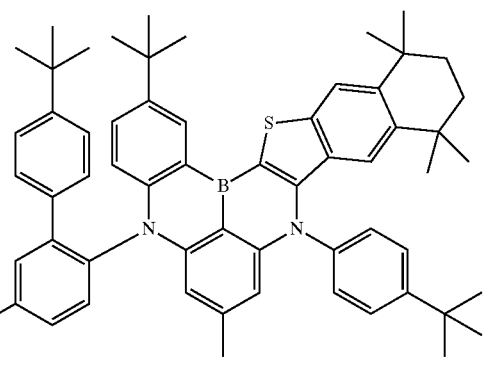
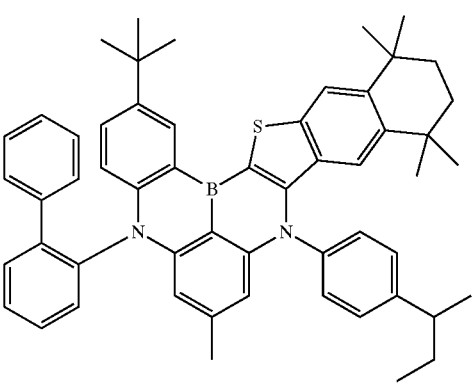
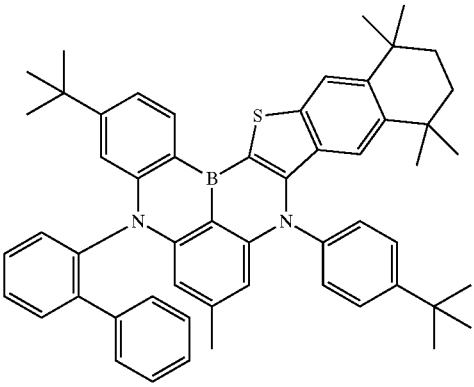

1329
-continued
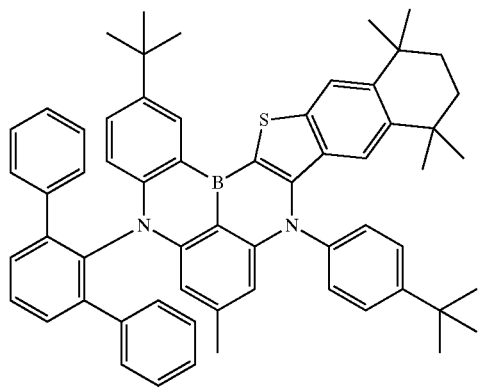
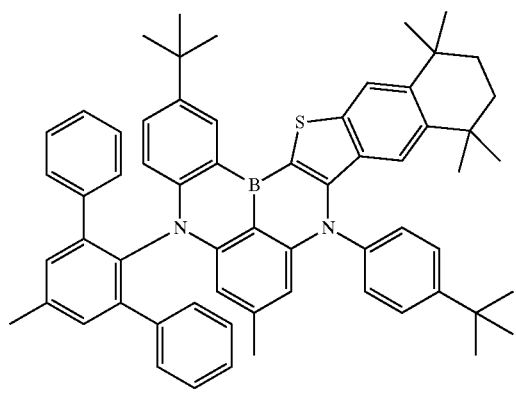
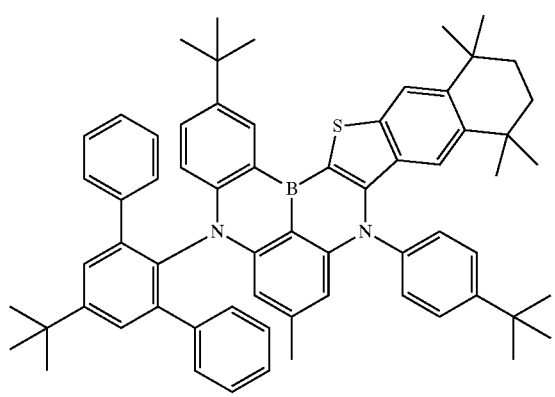
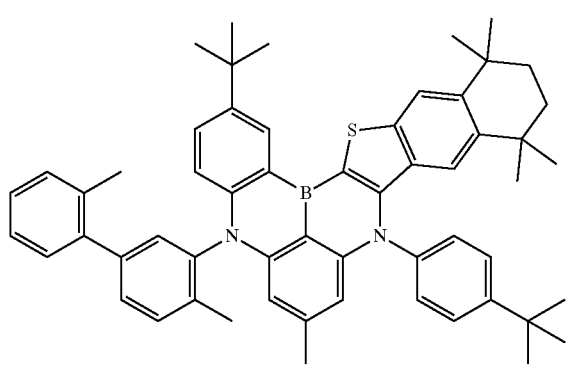
1330
-continued
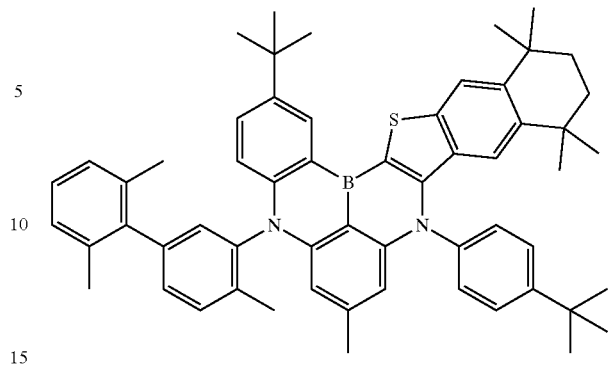
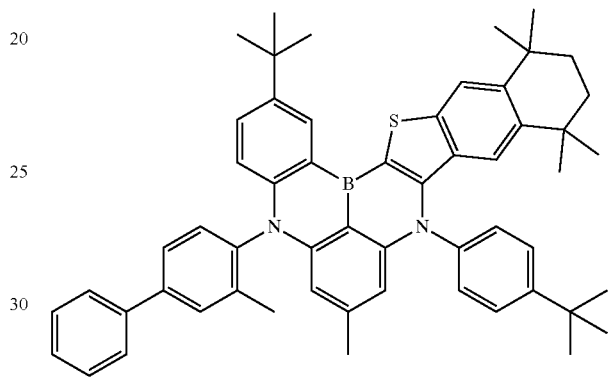
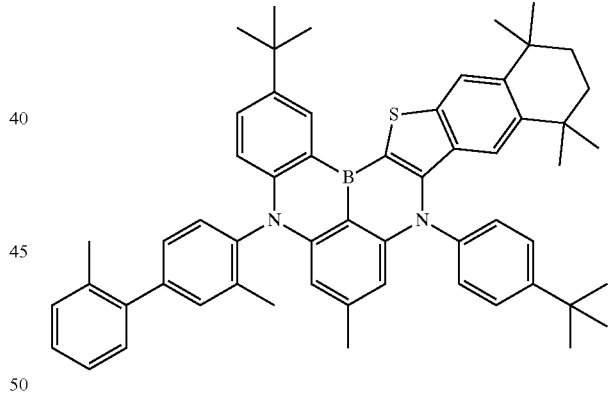
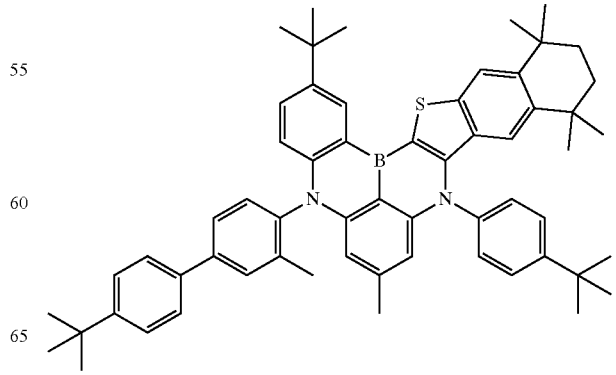

1331
-continued
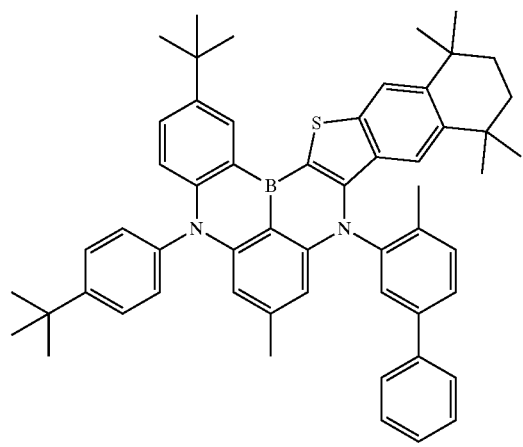
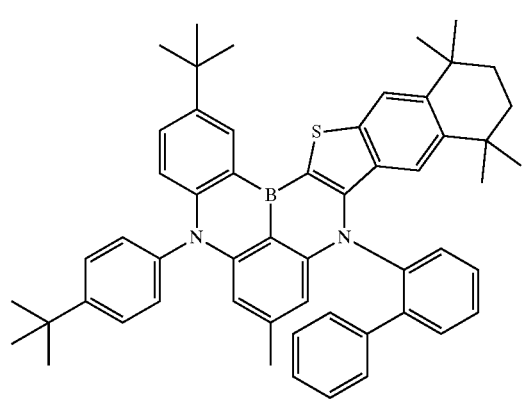
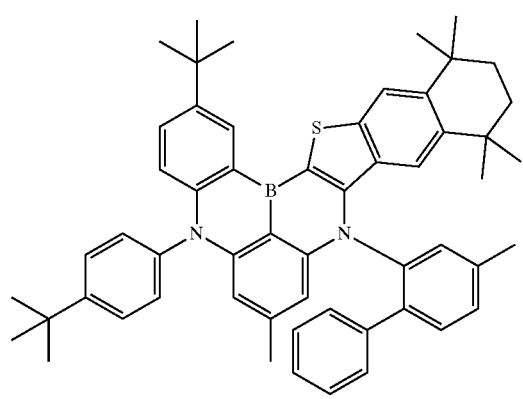
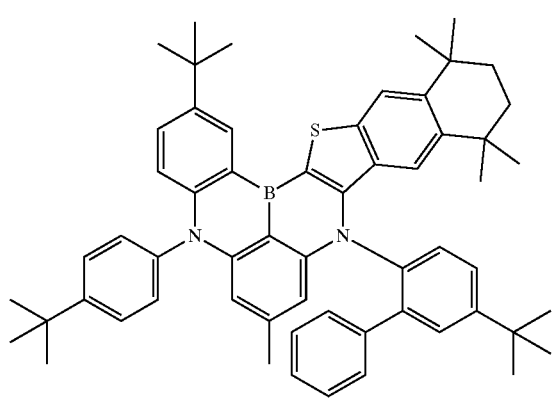
1332
-continued
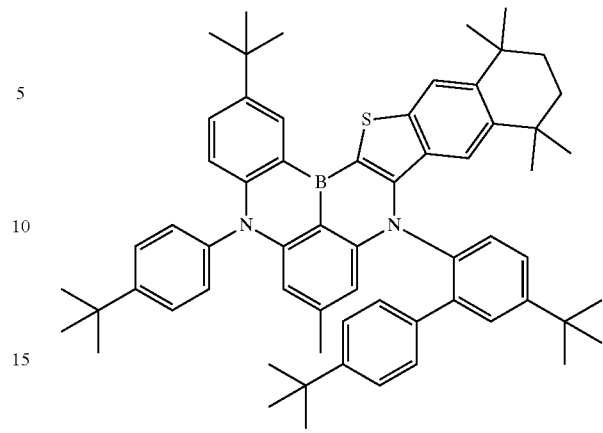
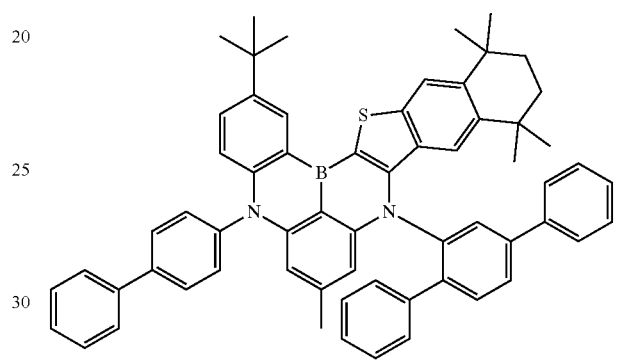
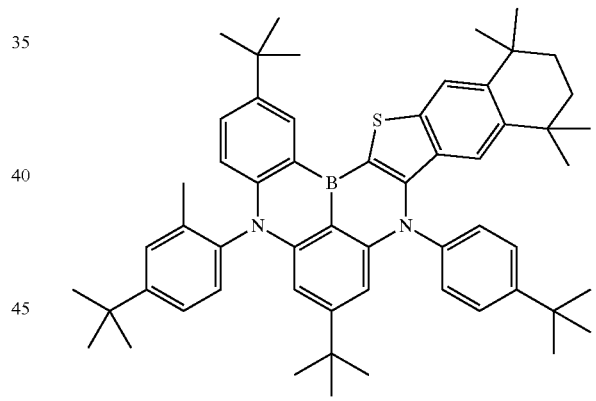
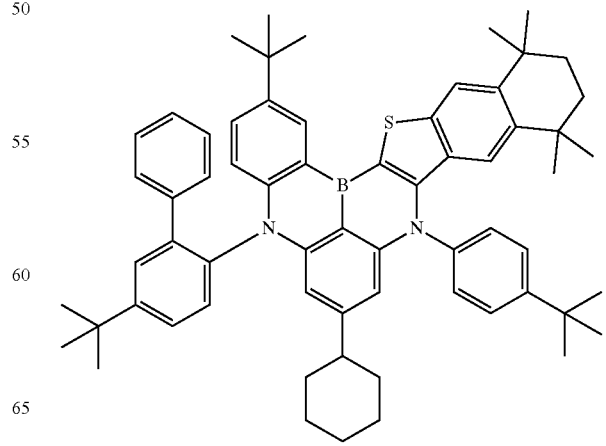

1333
-continued
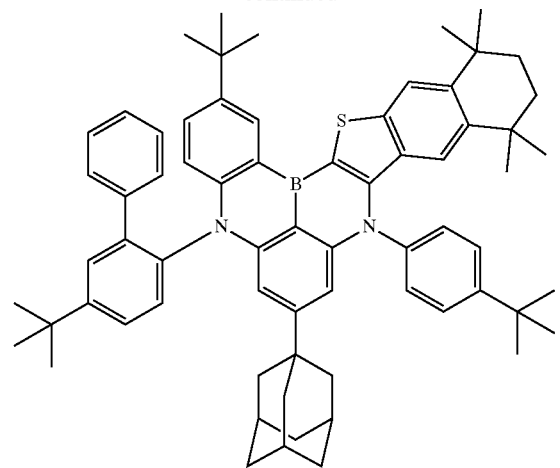
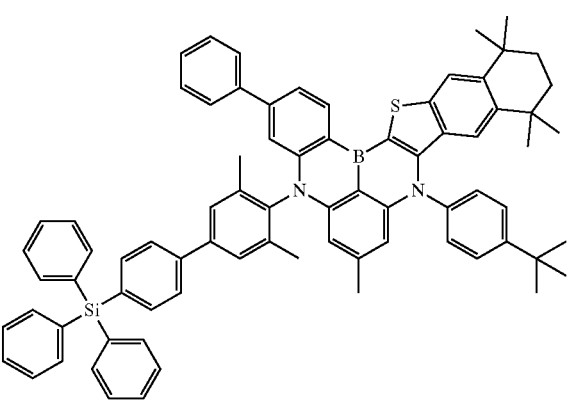
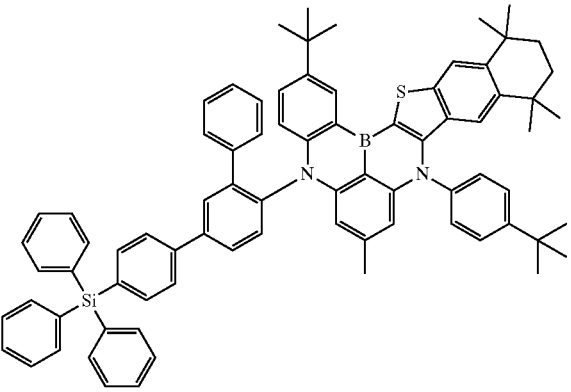
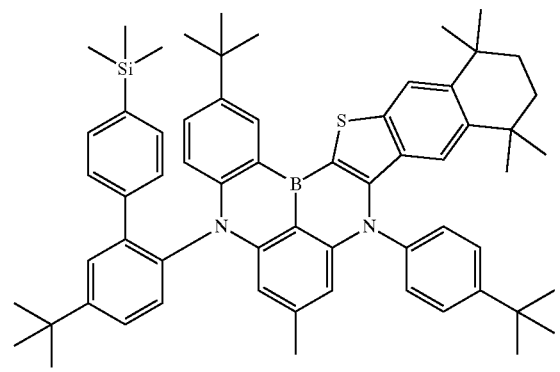
1334
-continued
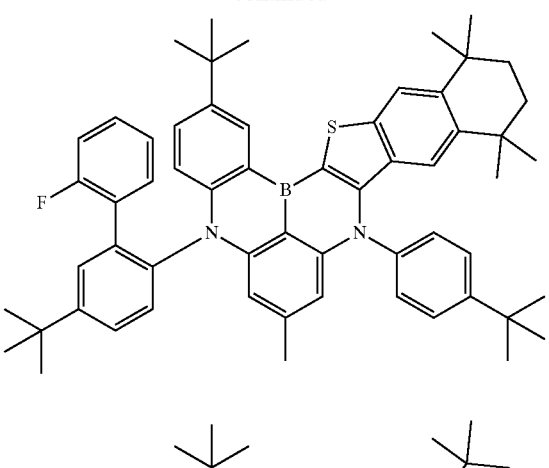

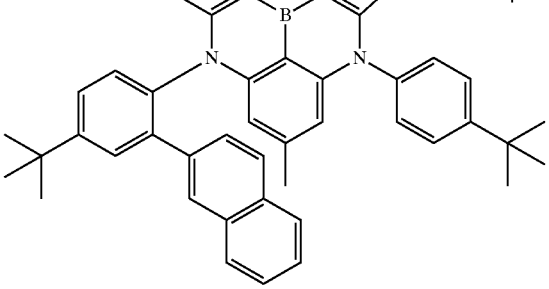
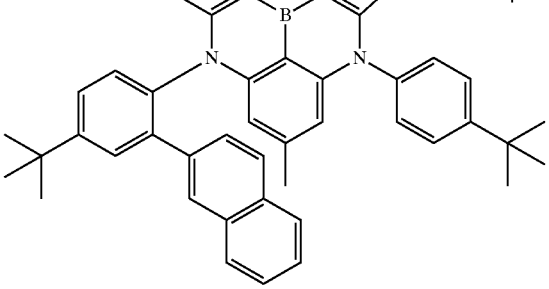

1335
-continued
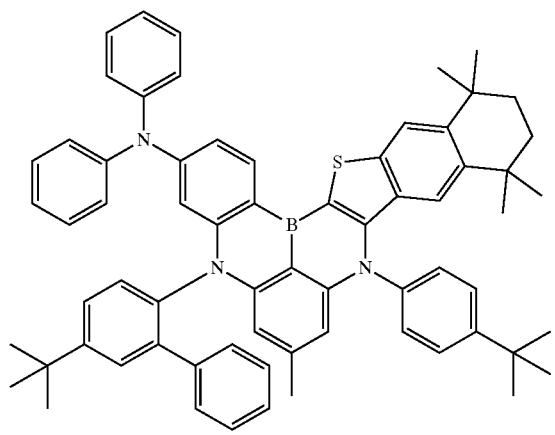
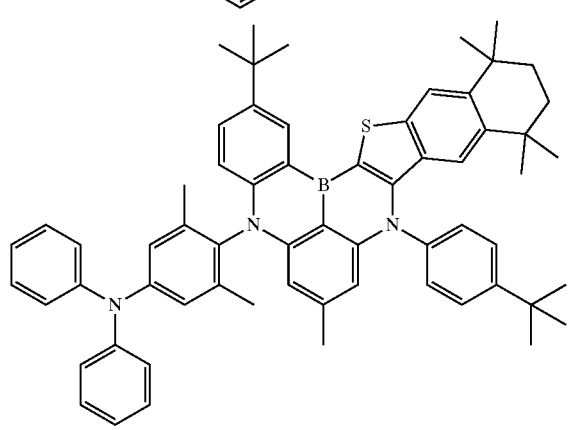
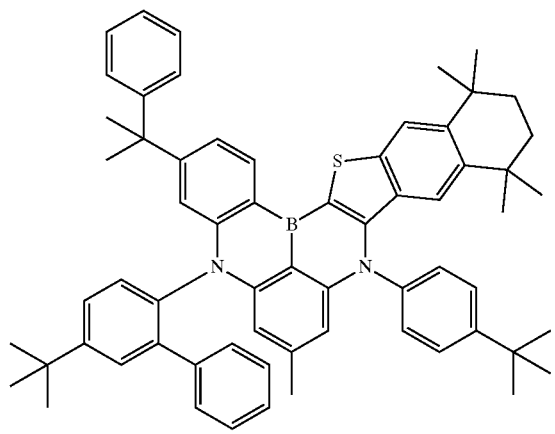
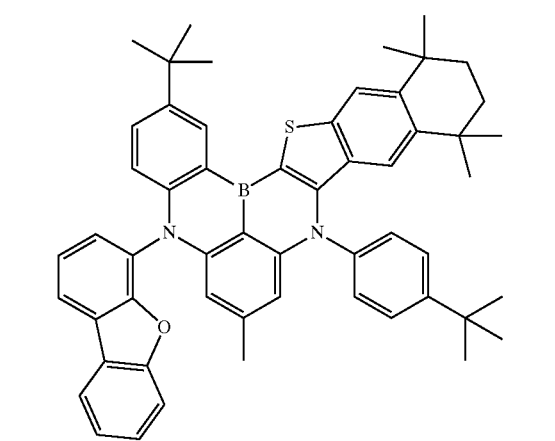
1336
-continued
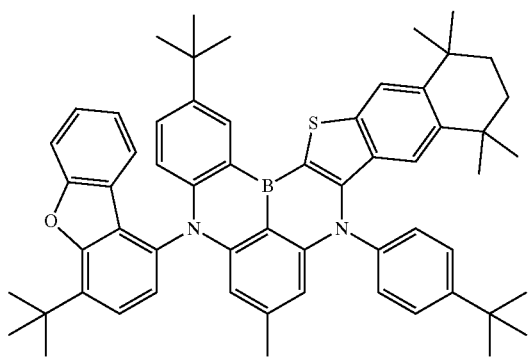
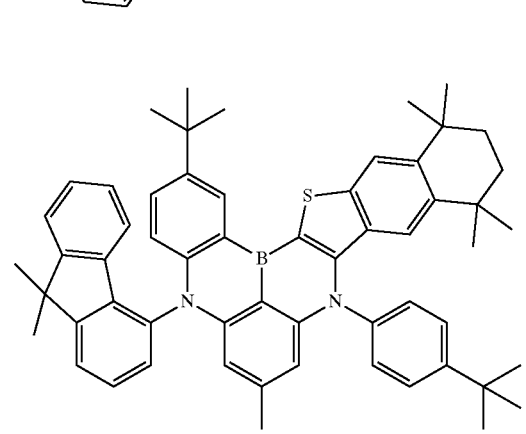
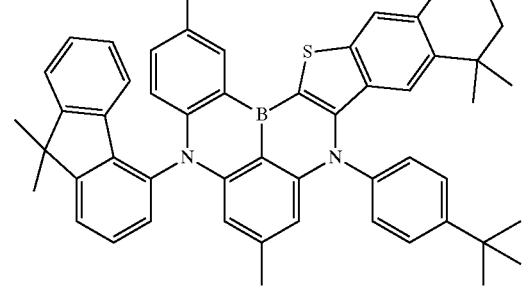
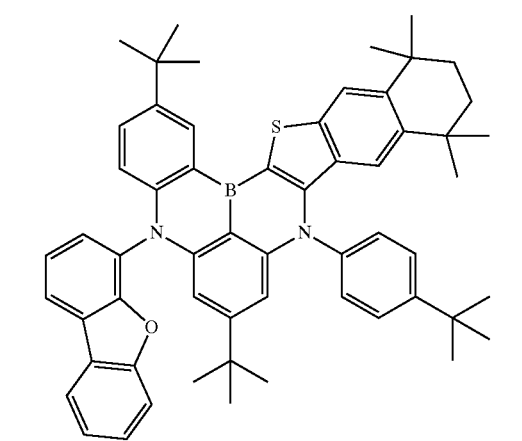

| 1337 -continued | 1338 -continued |
|---|---|
| 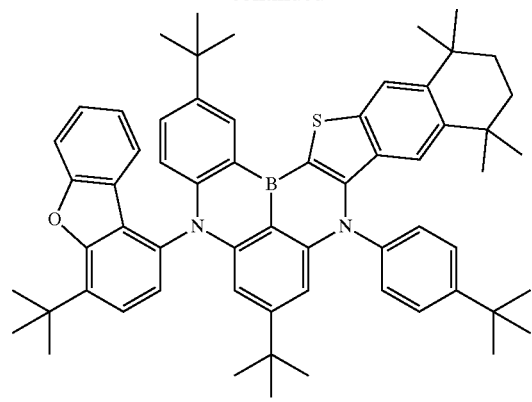 | 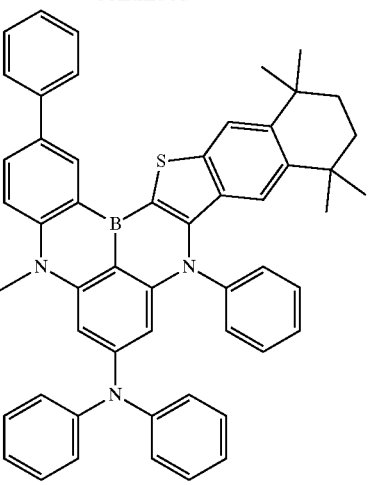 |
| 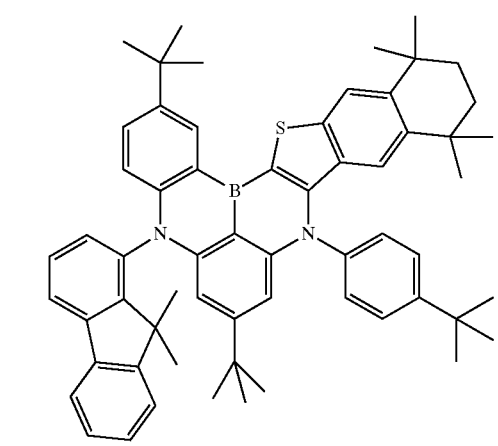 | 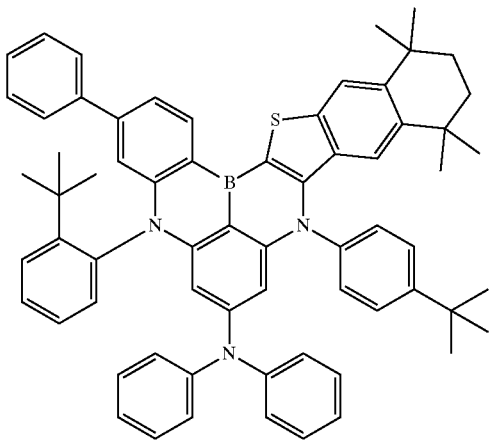 |
| 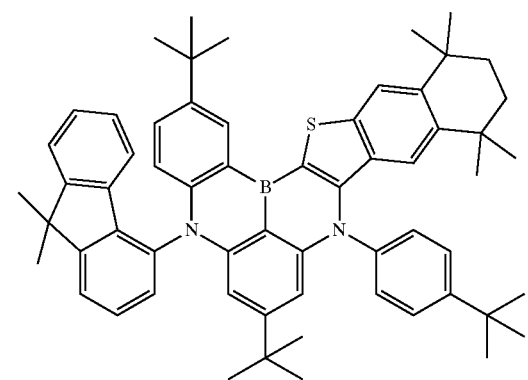 | |
| 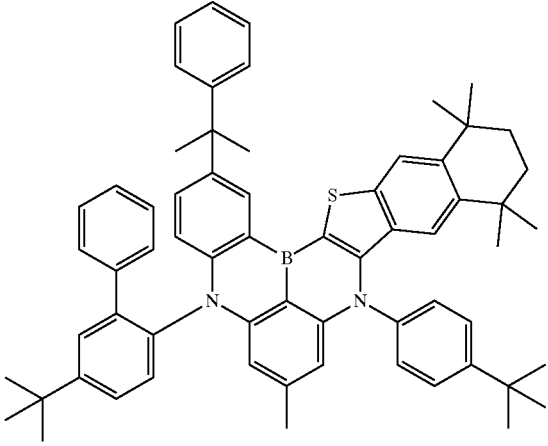 | 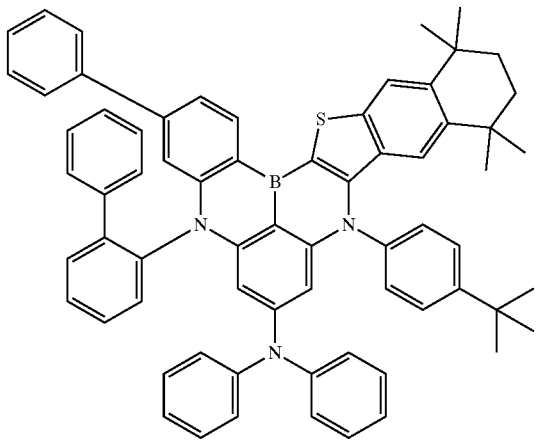 |

1339
-continued
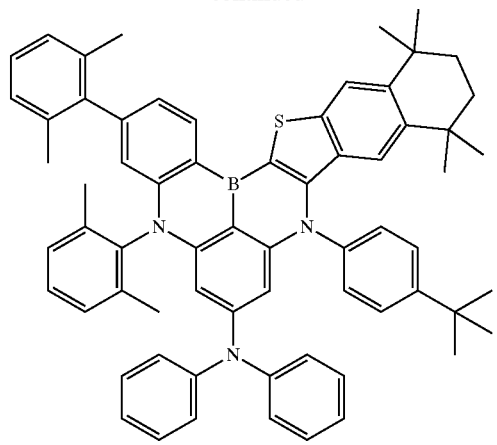
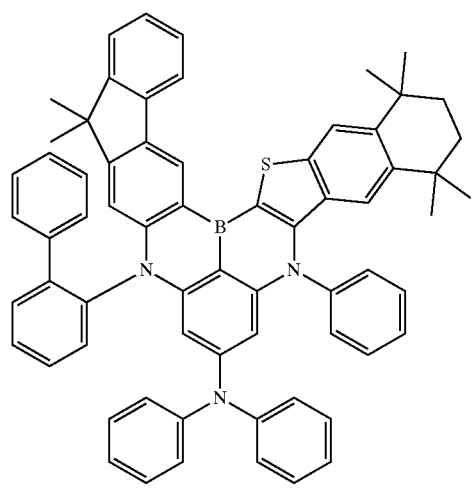
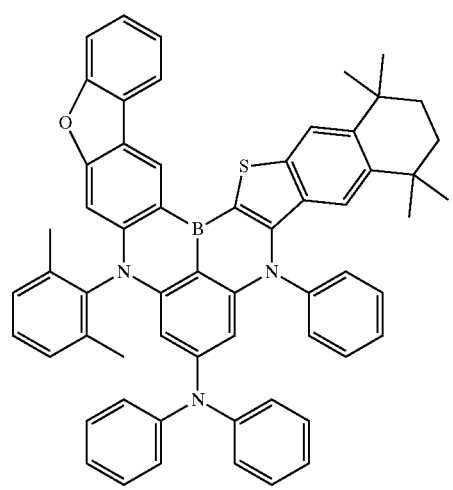
1340
-continued
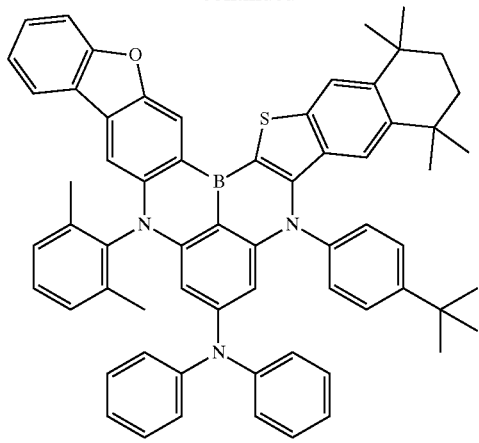
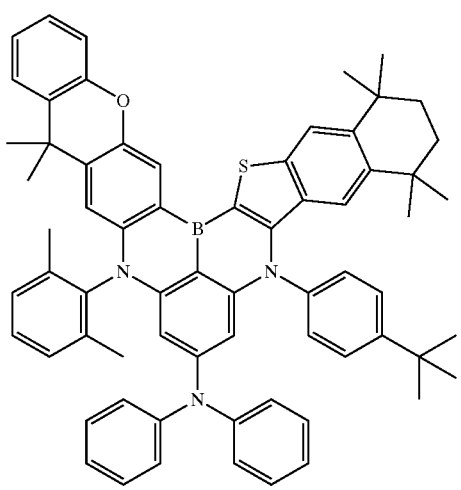
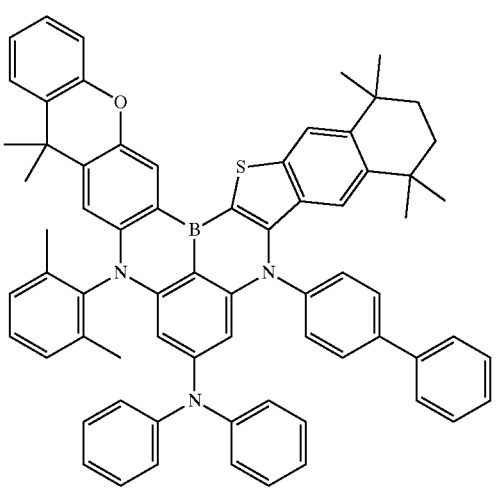

1341
-continued
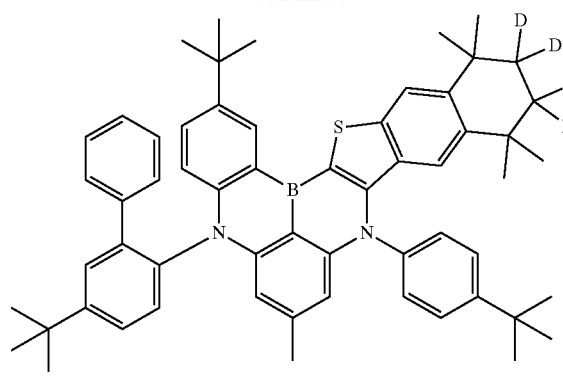
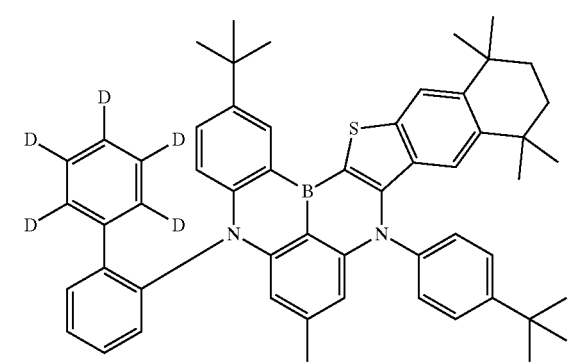
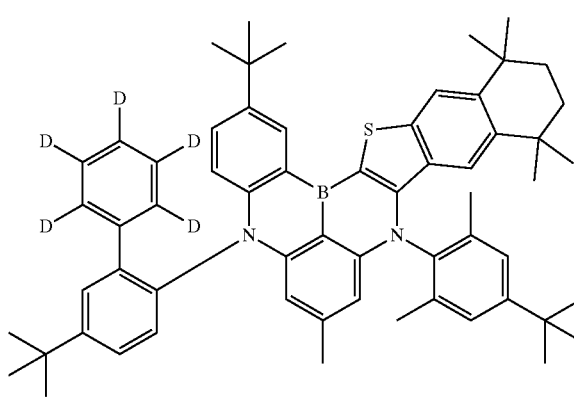
1342
-continued
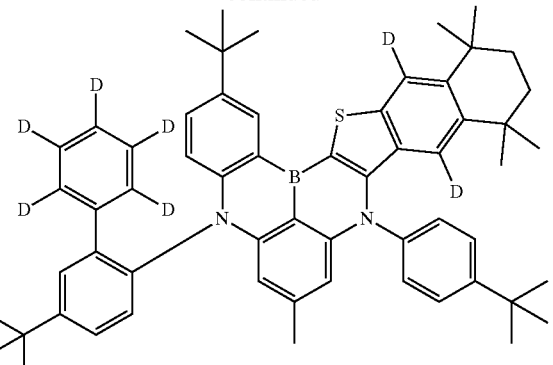
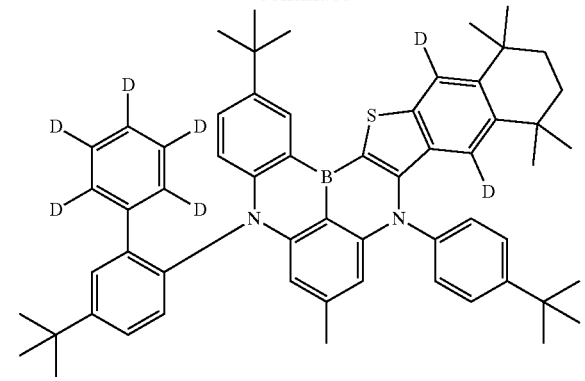
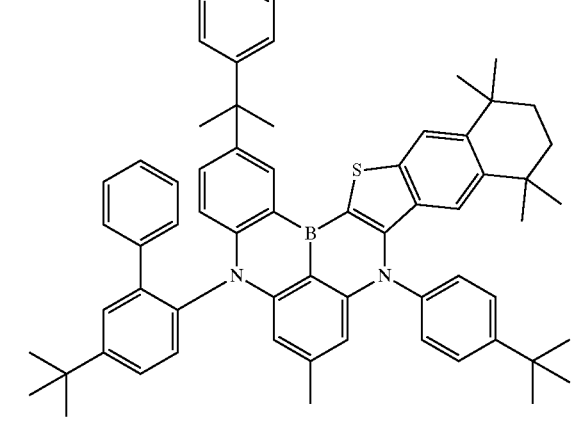

1343
-continued
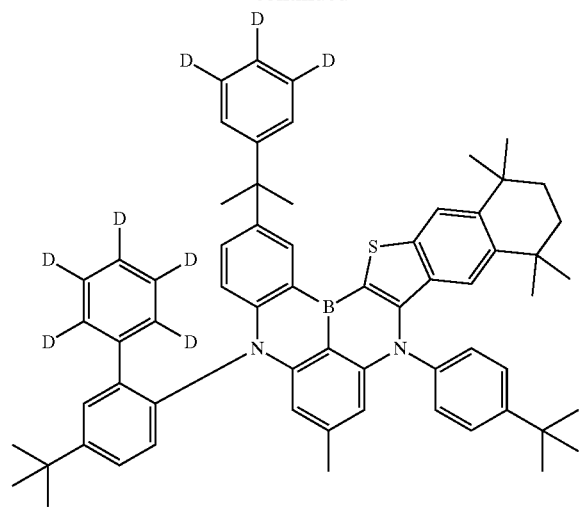
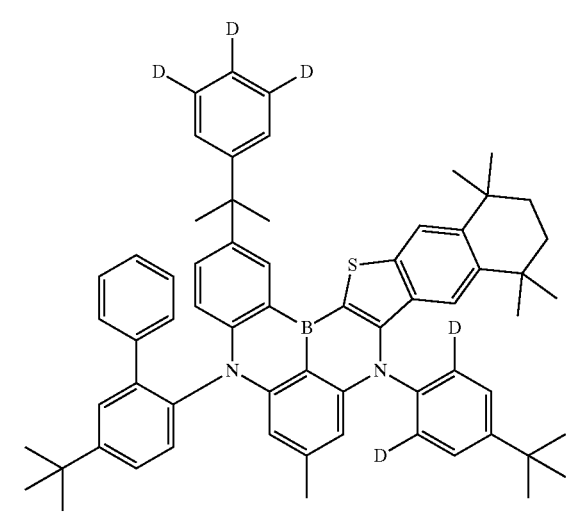
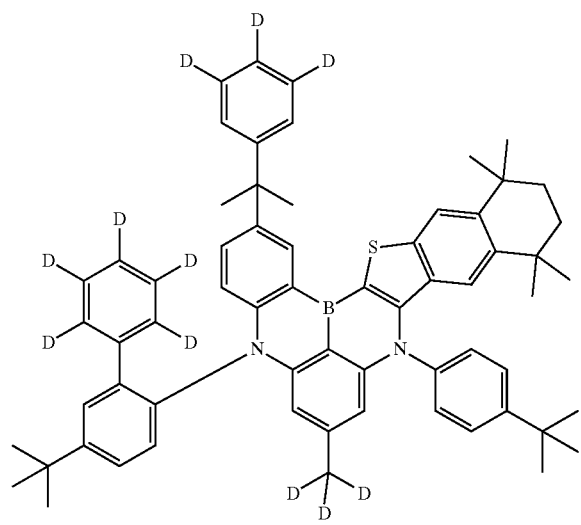 [SMILES: [2H]c1cc(C(C)(C)c2ccc3c(c2)B2c4sc5cc6c(cc5c4N(c4ccc(C(C)(C)C)cc4)c4cc(C([2H])([2H])[2H])cc(c42)N3c2ccc(C(C)(C)C)cc2-c2c([2H])c([2H])c([2H])c([2H])c2[2H])C(C)(C)CCC6(C)C)cc([2H])c1[2H]]
1344
-continued
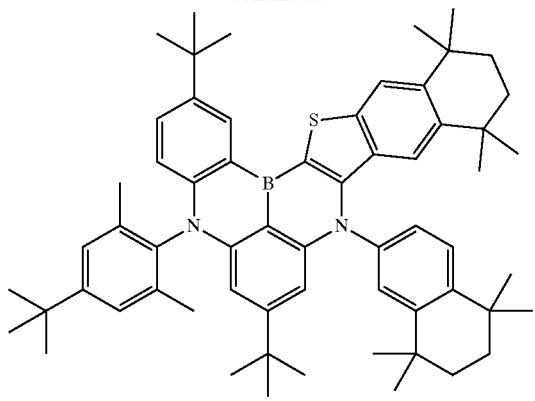
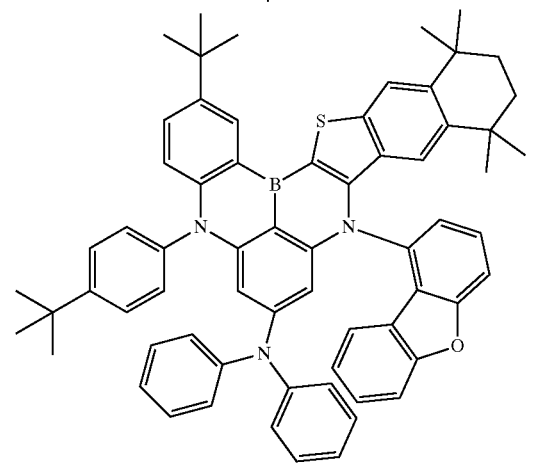
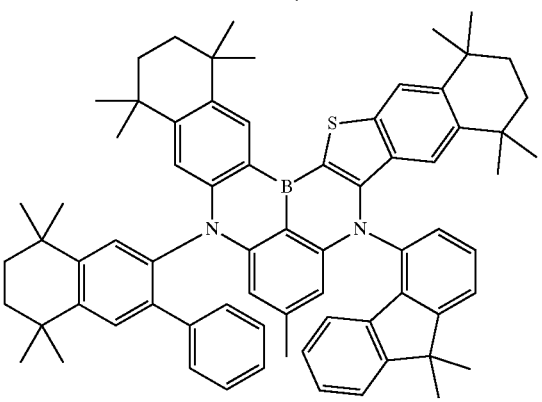
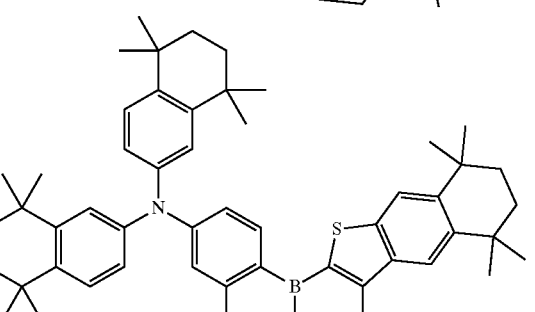
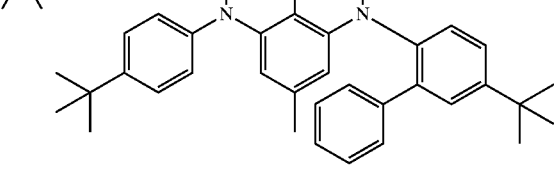

1345
-continued
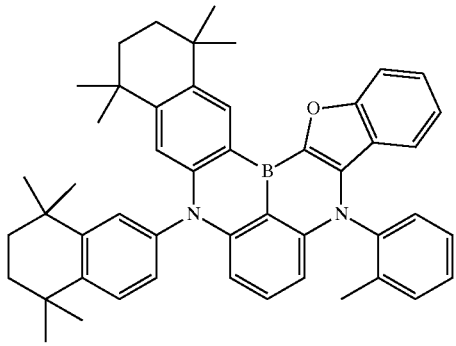
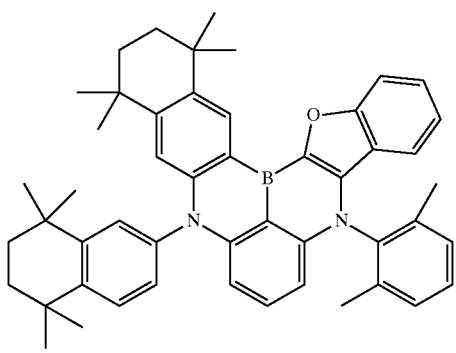
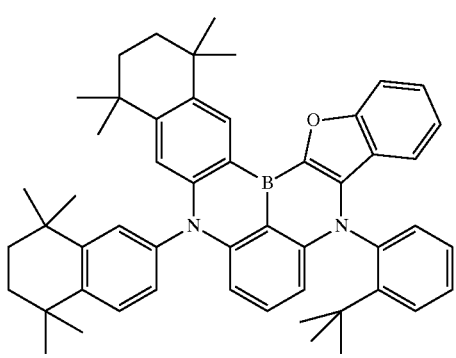
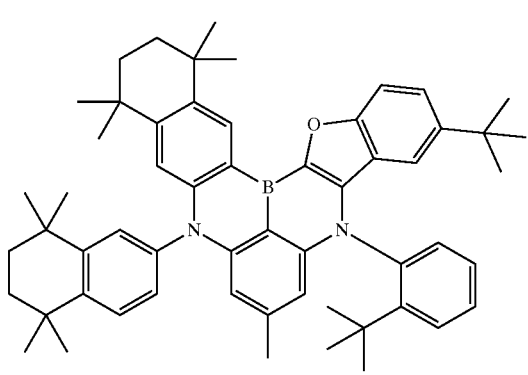
1346
-continued
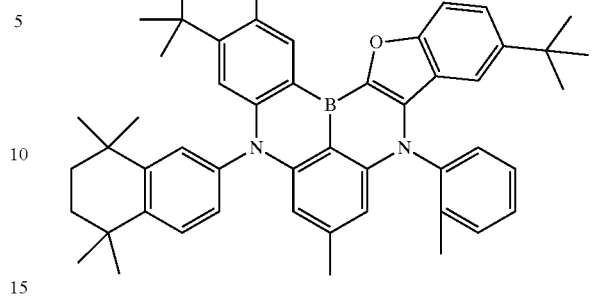
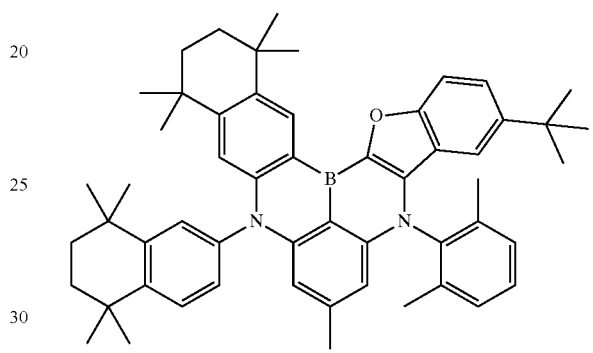
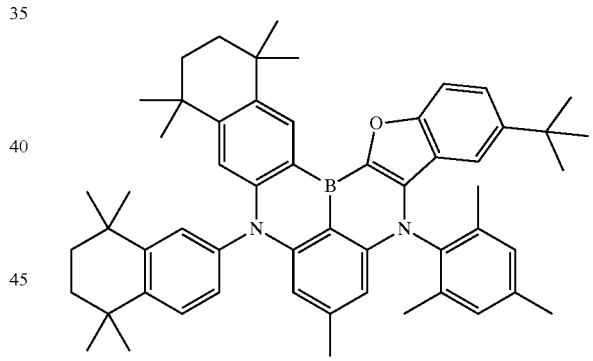
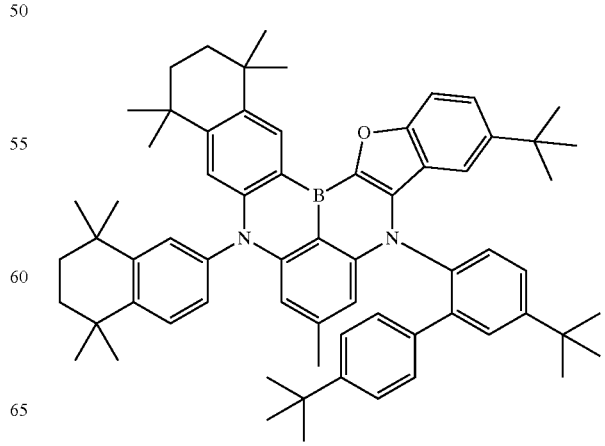

1347
-continued
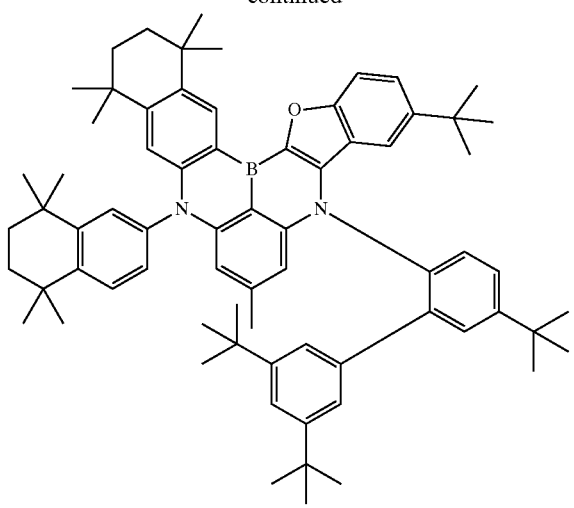
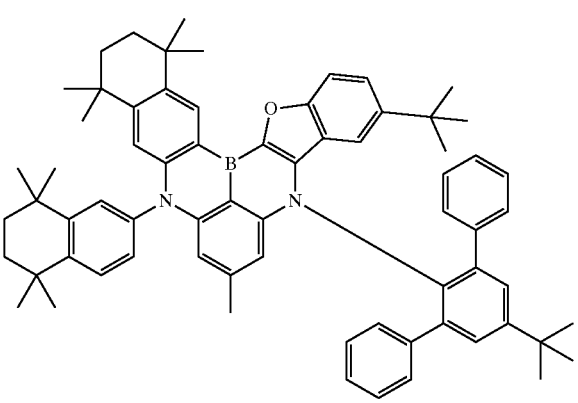
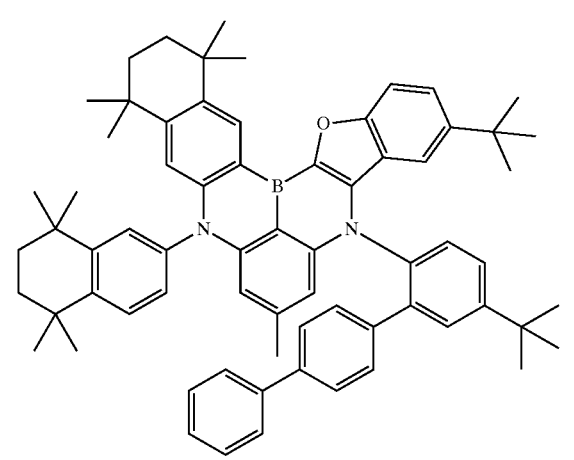
1348
-continued
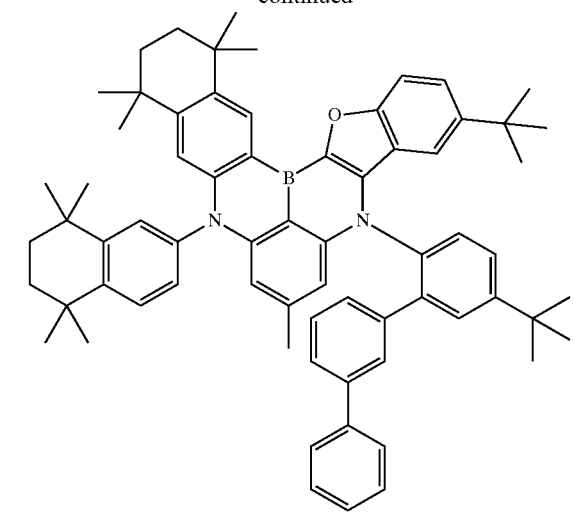
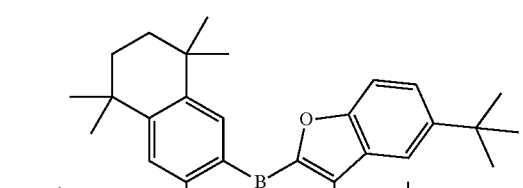
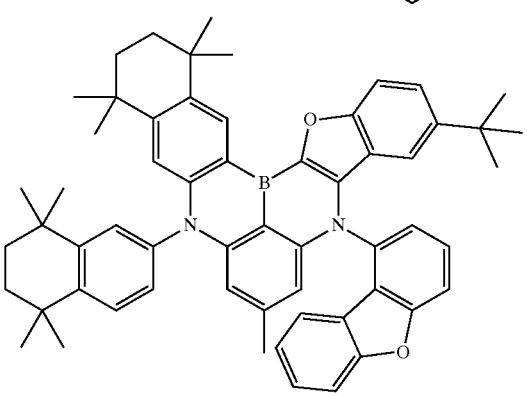
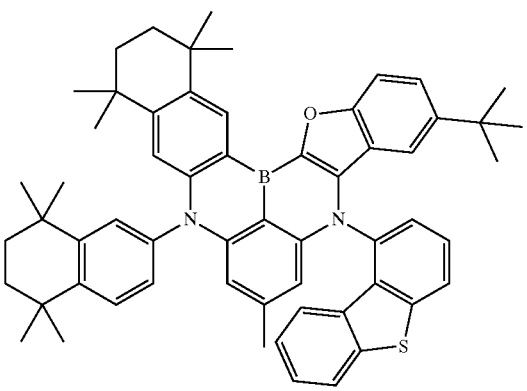

1349
-continued
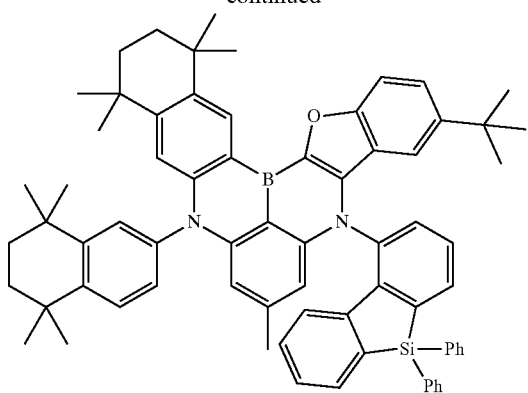
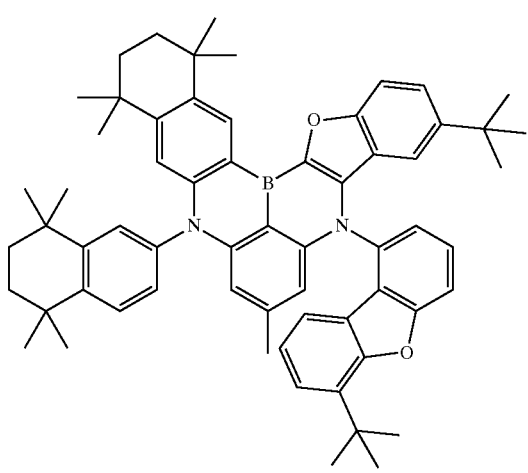
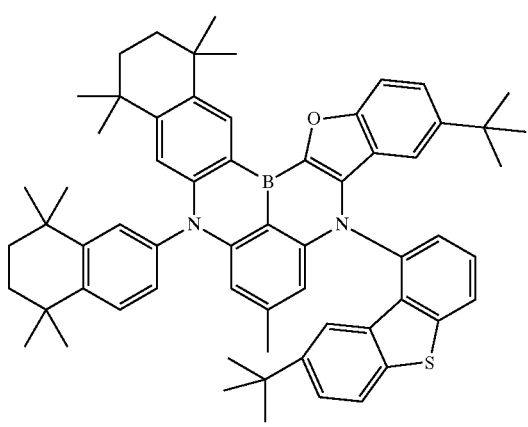
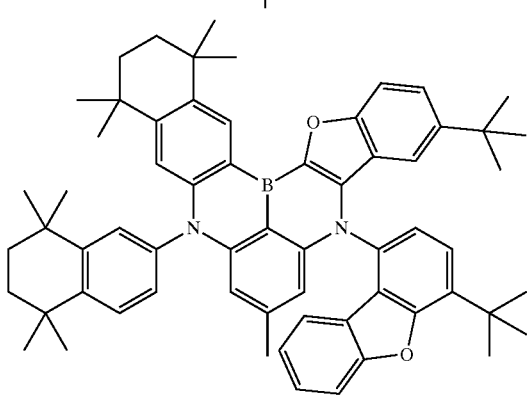
1350
-continued
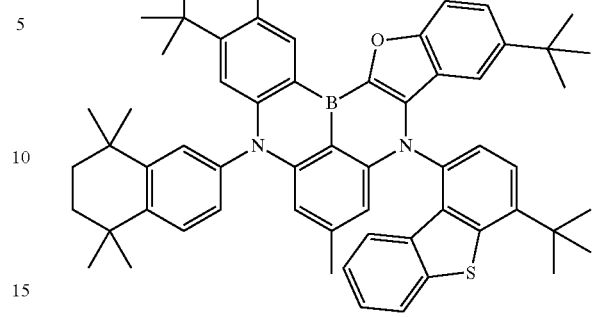
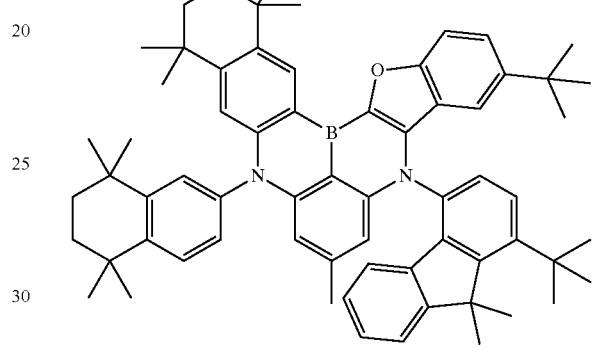
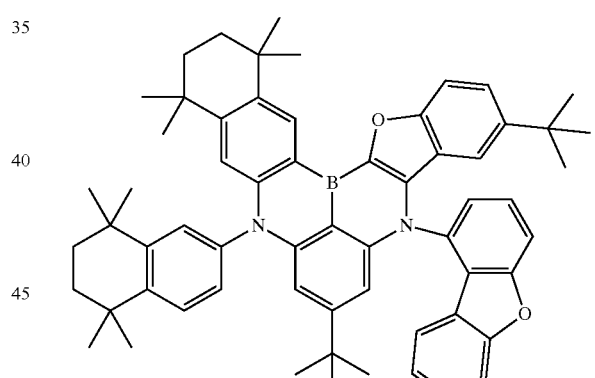
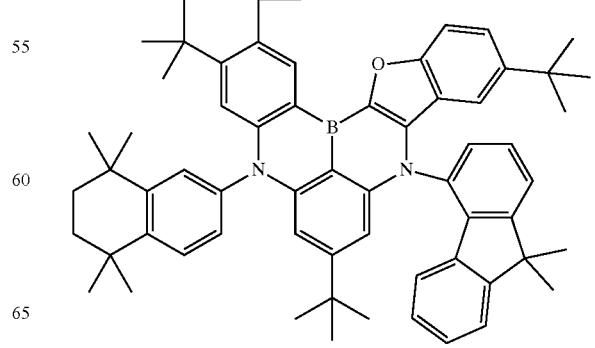

1351
-continued
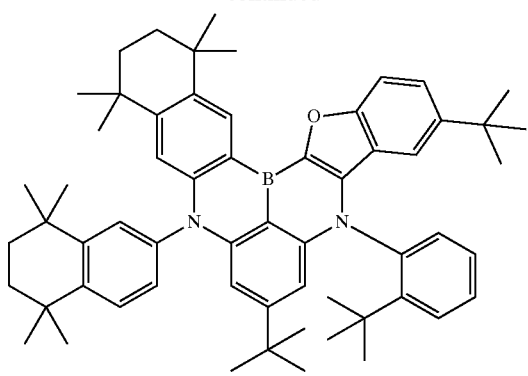
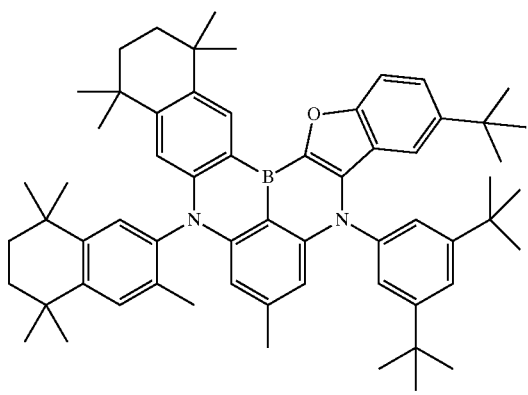
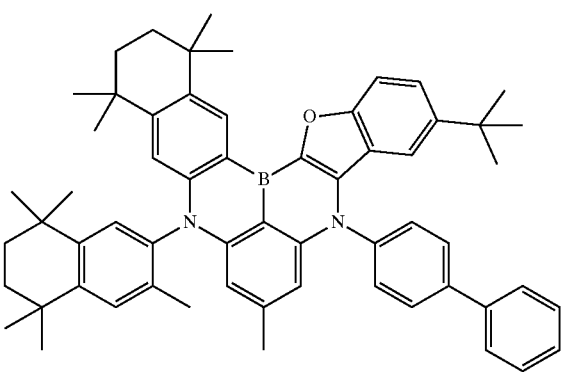
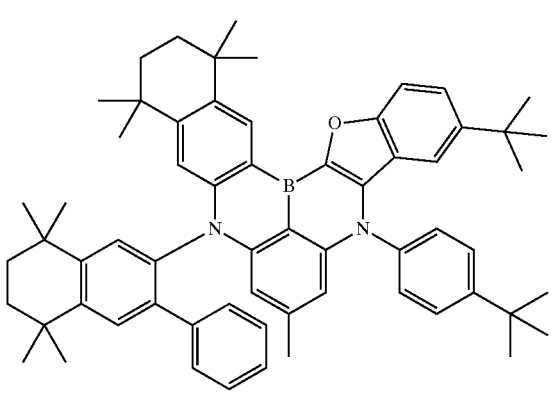
1352
-continued
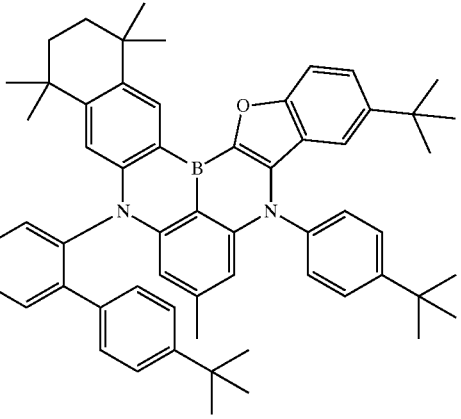
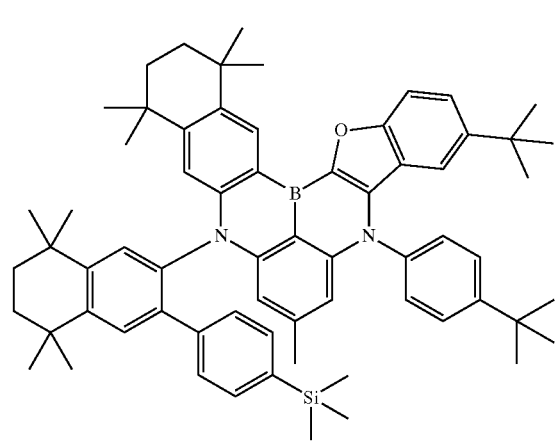

1353
-continued
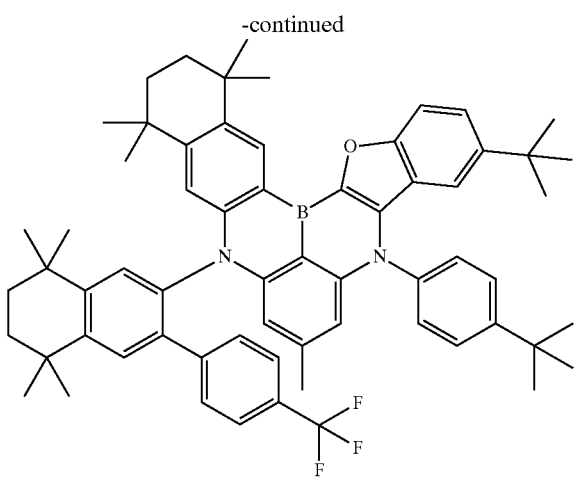
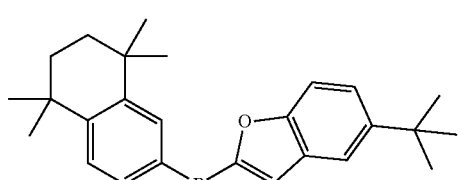
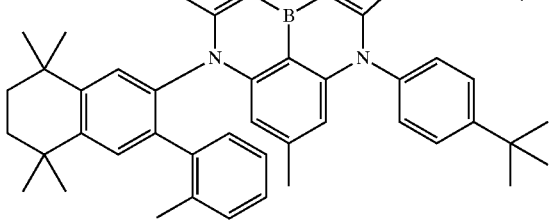
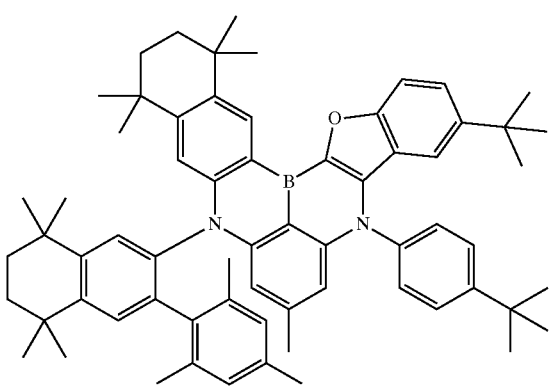
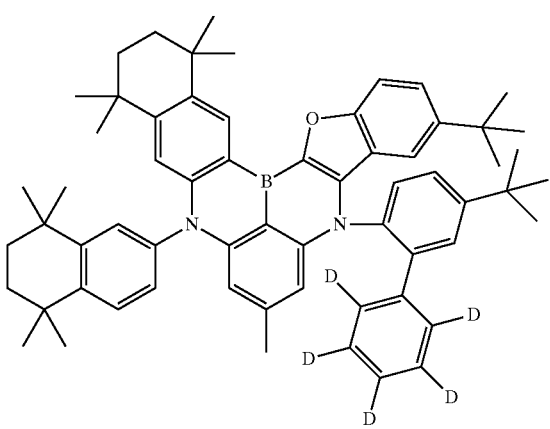
1354
-continued
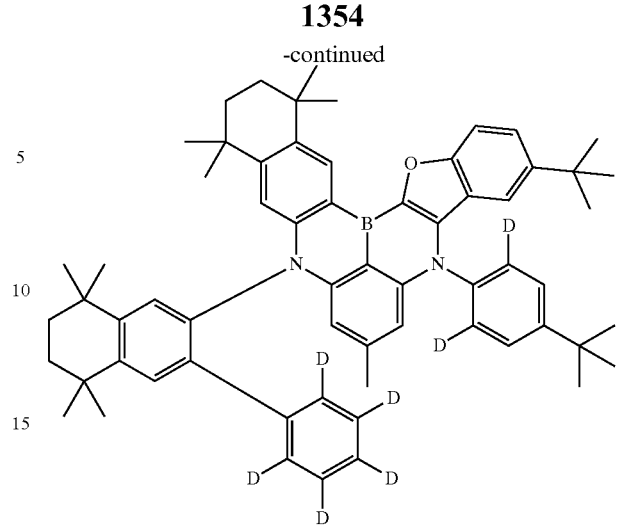
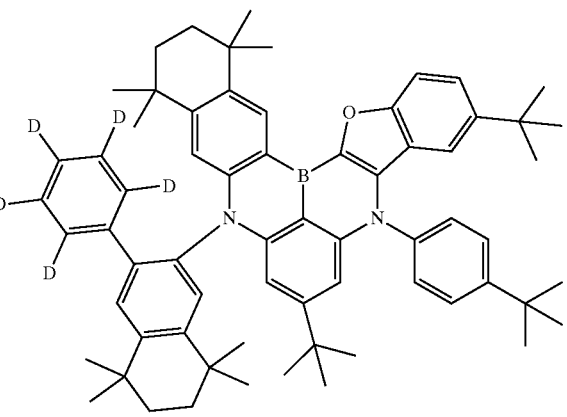
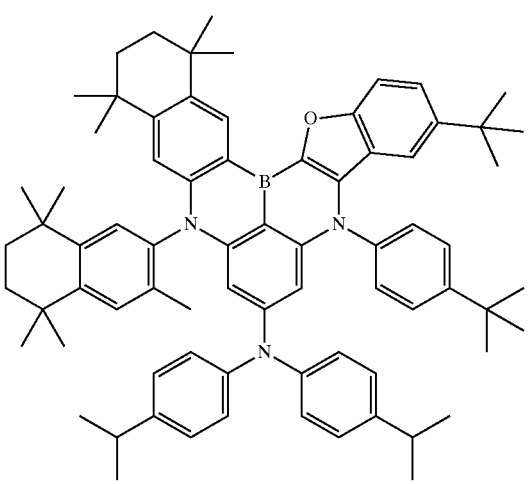

1355
-continued
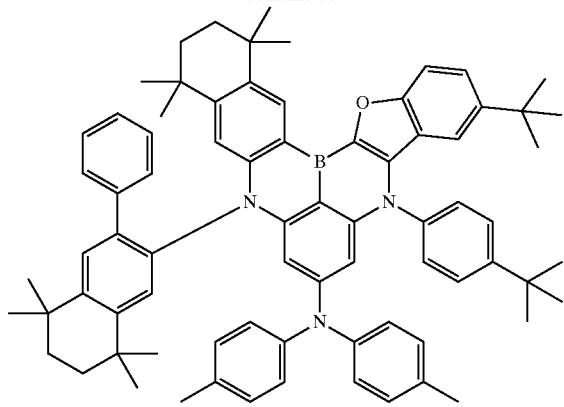
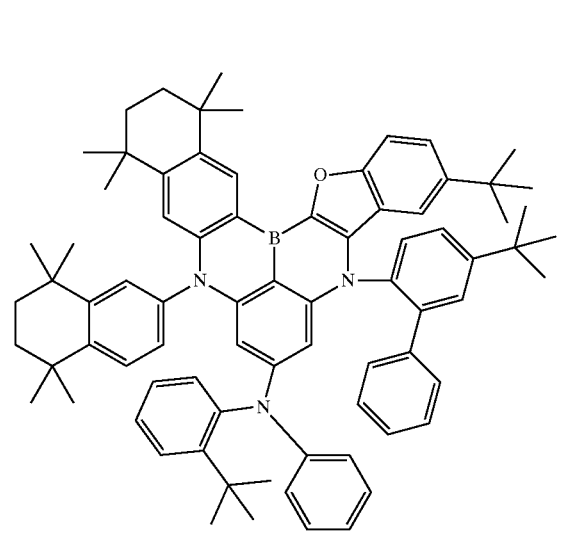
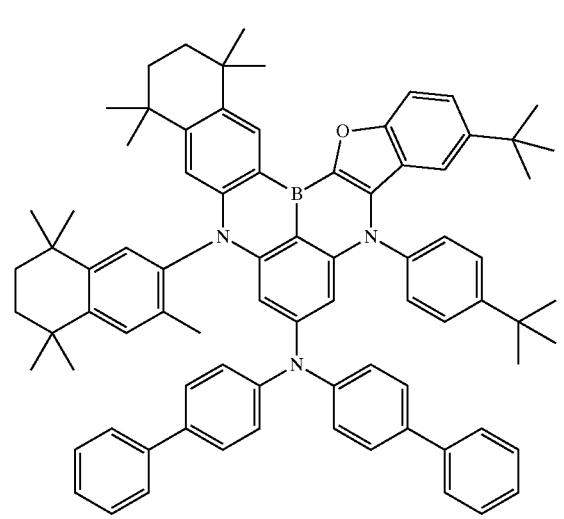
1356
-continued
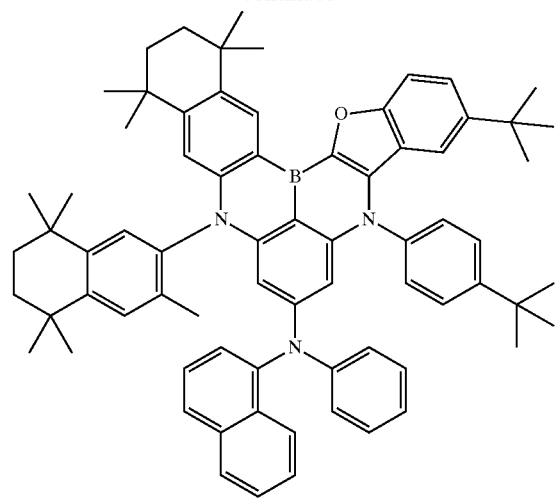
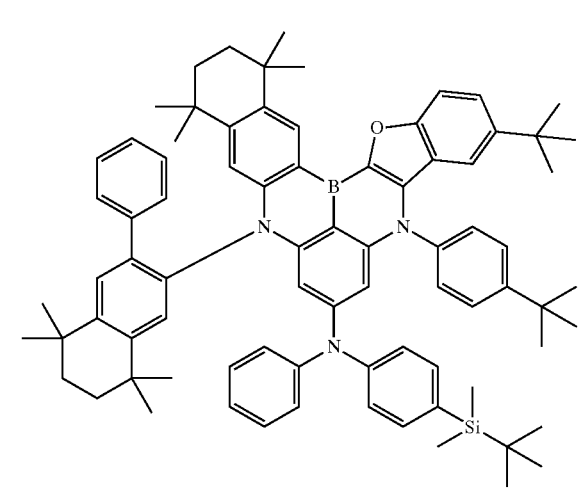
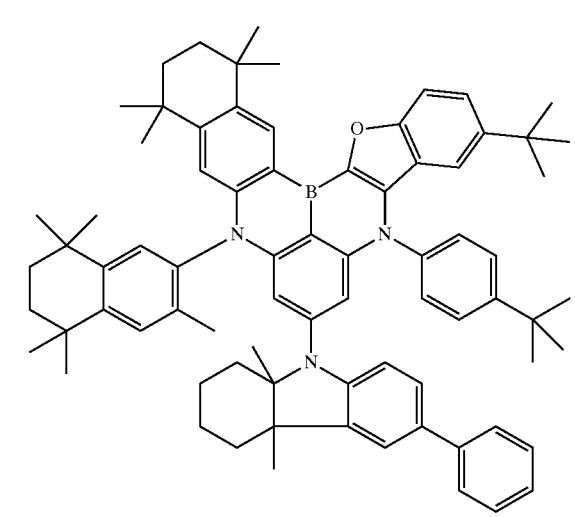

1357
-continued
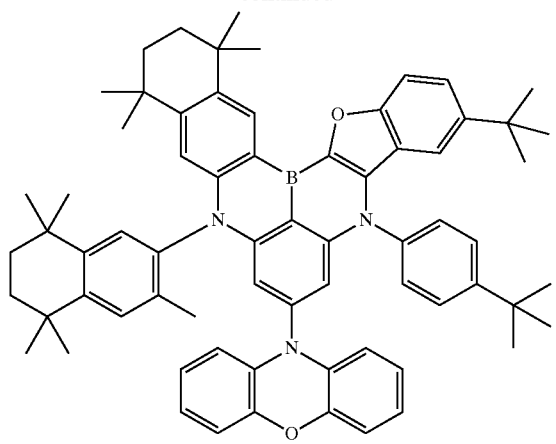
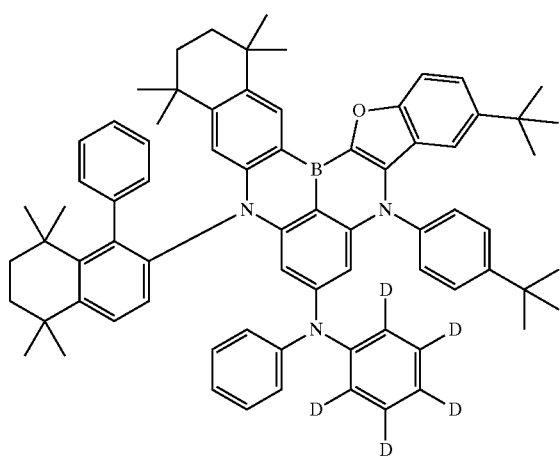
1358
-continued
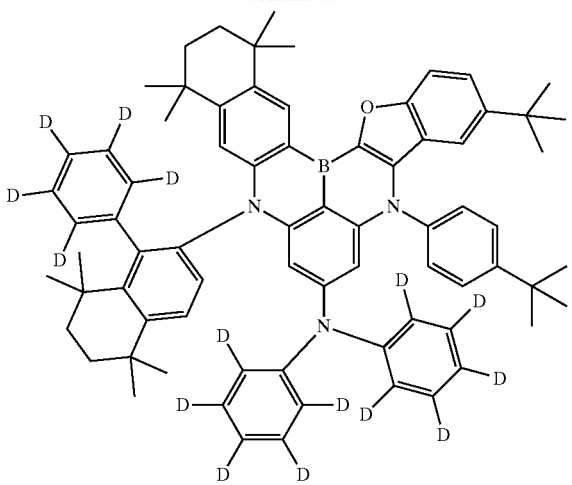
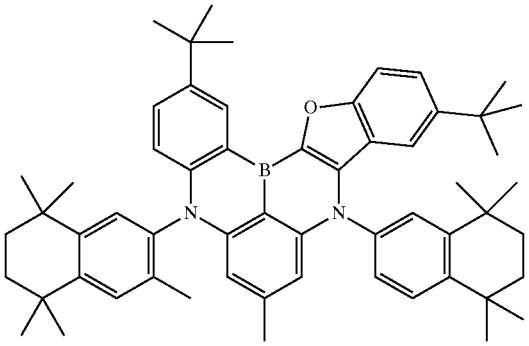
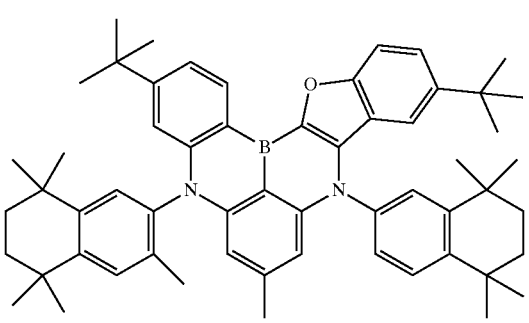
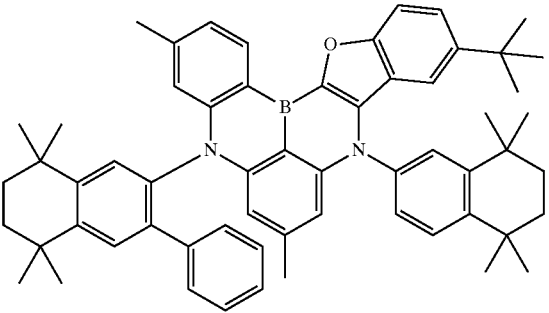

1359
-continued
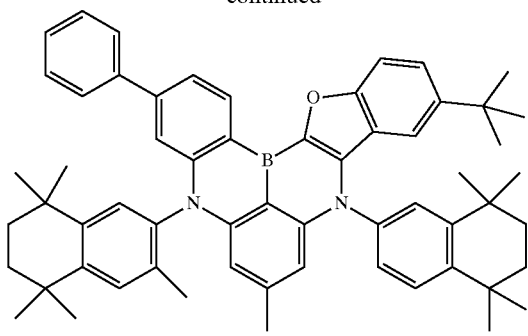
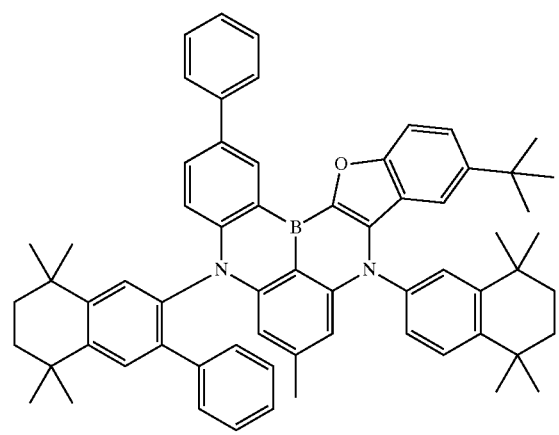
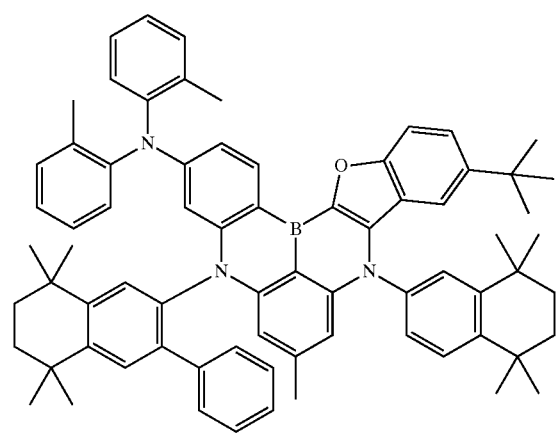
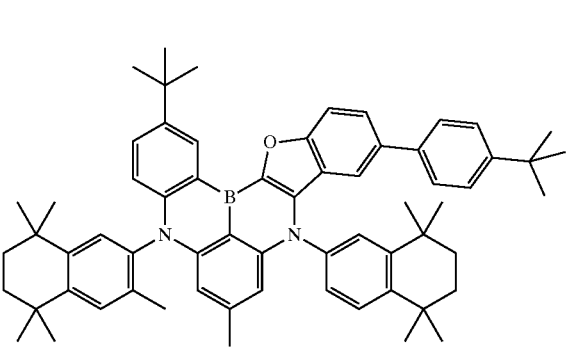
1360
-continued
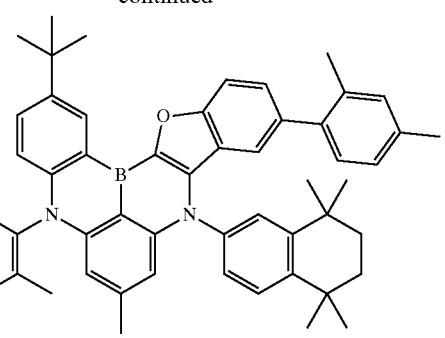
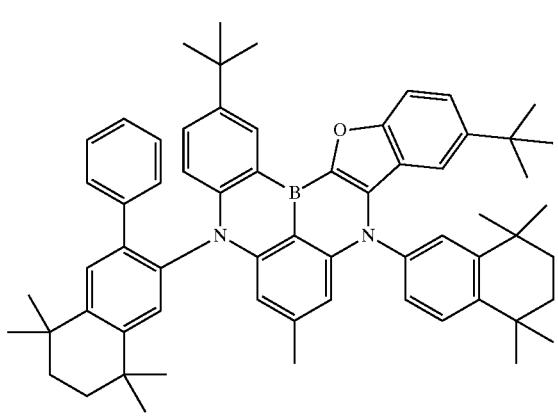
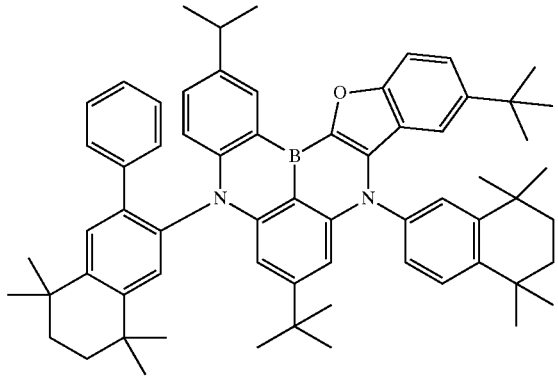
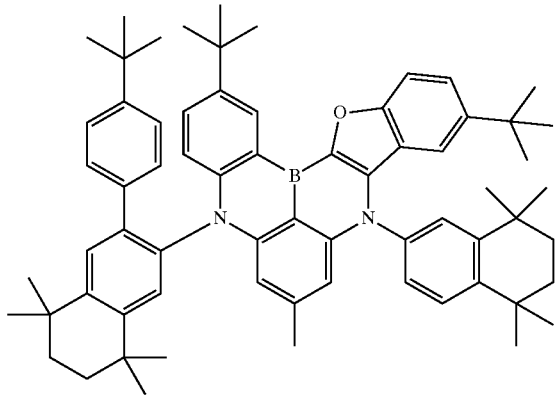

| 1361 -continued | 1362 -continued |
|---|---|
| 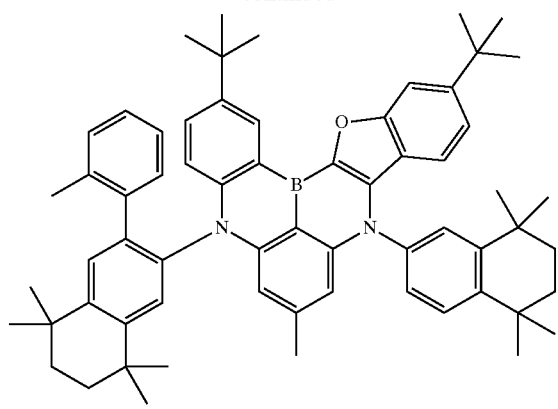 | 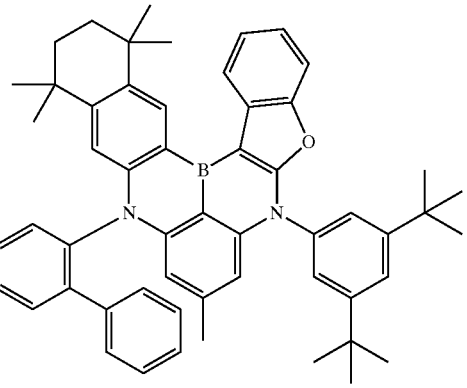 |
| 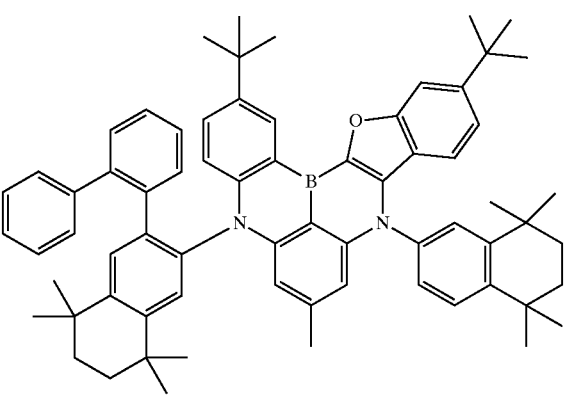 | 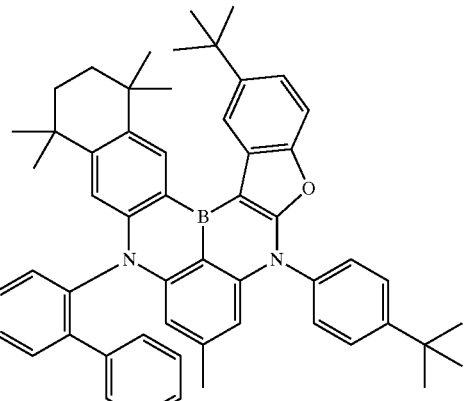 |
| 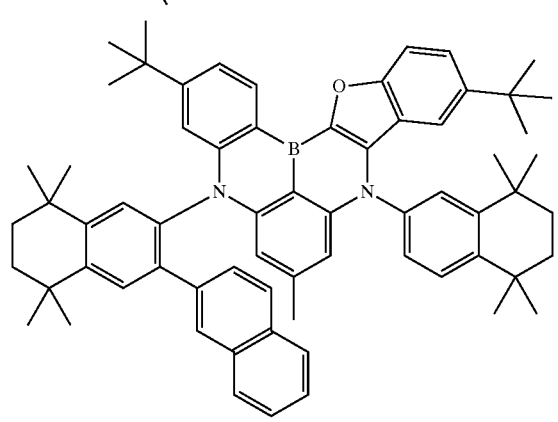 | 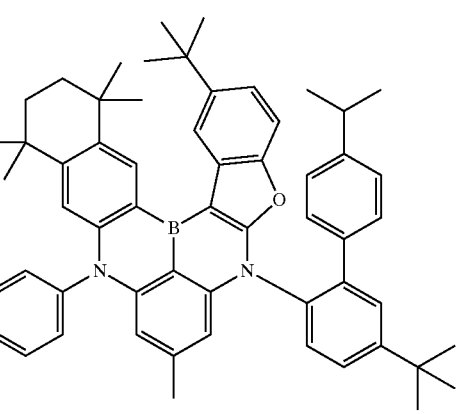 |
| 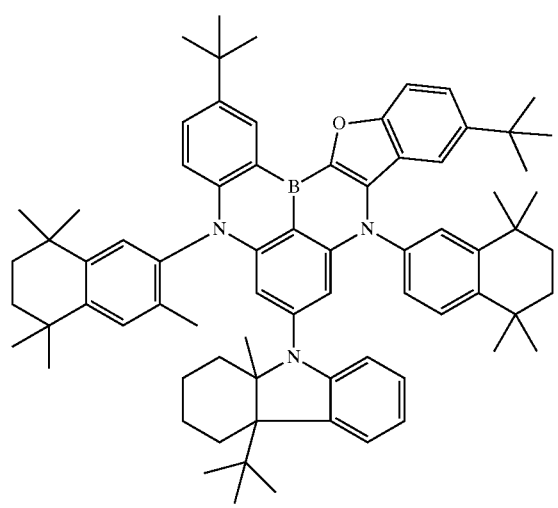 | 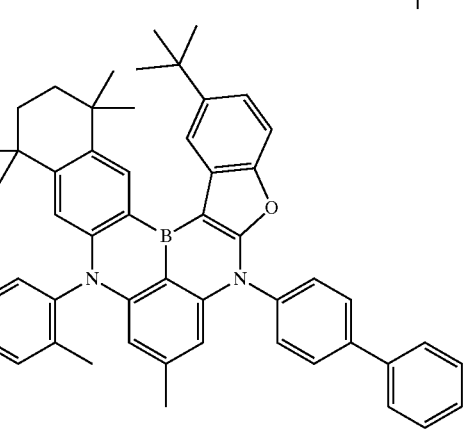 |

1363
-continued
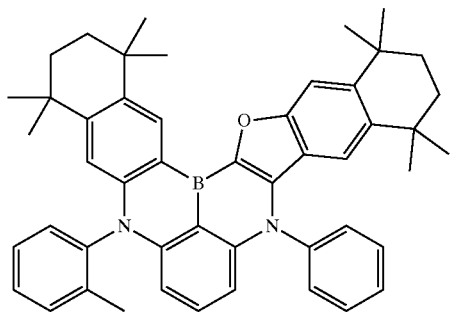
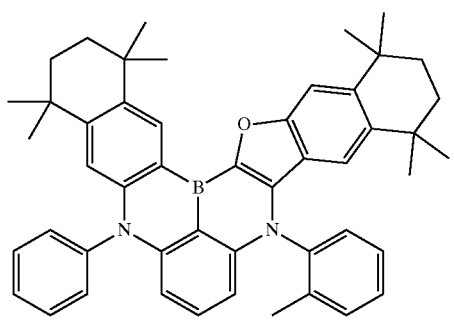
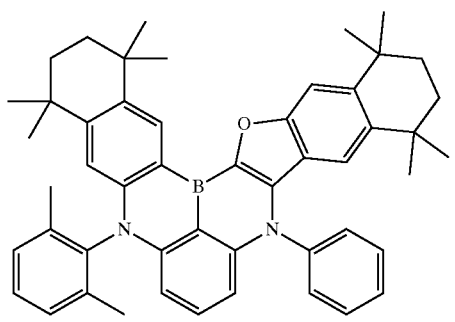
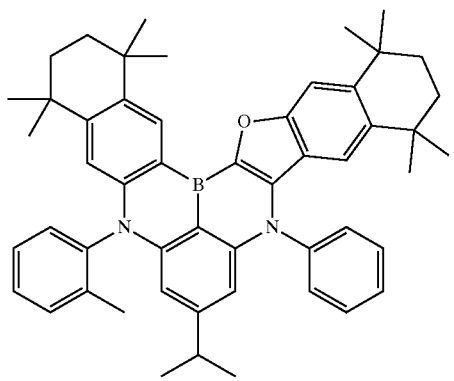
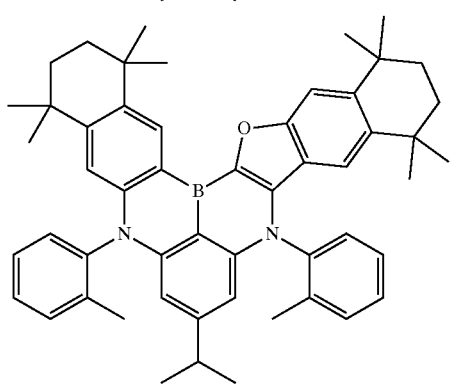
1364
-continued
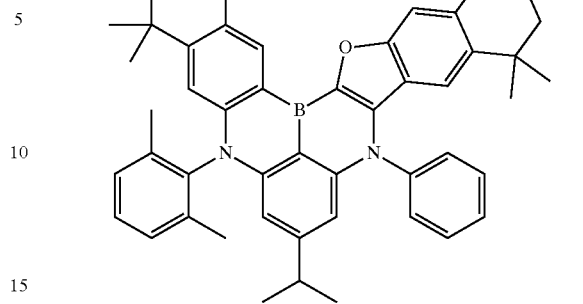
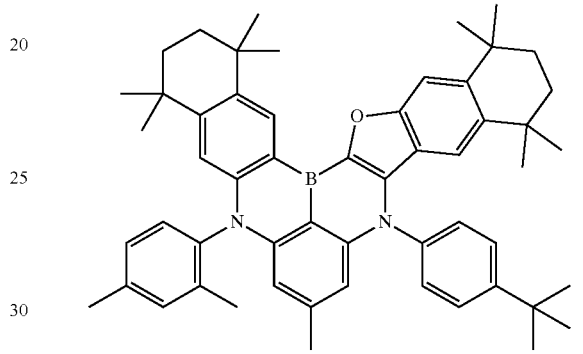
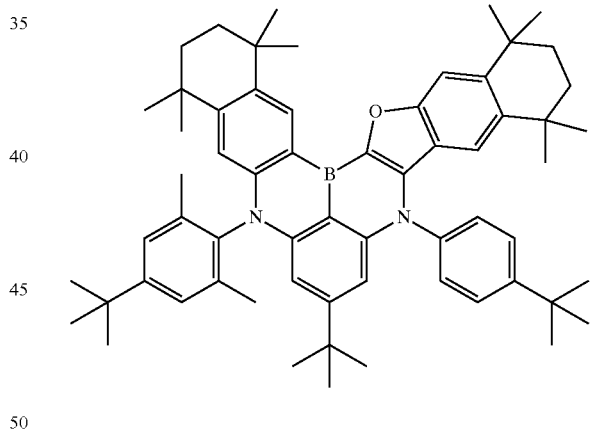
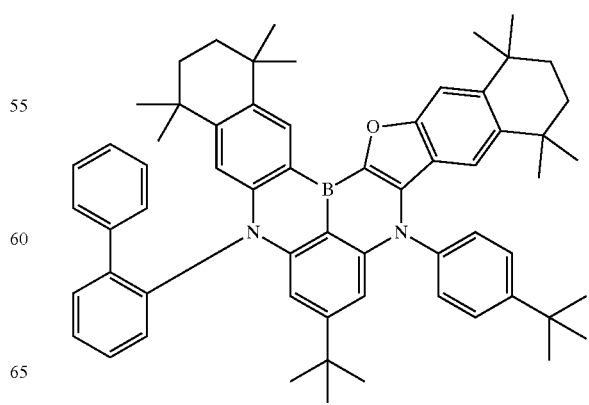

1365
-continued
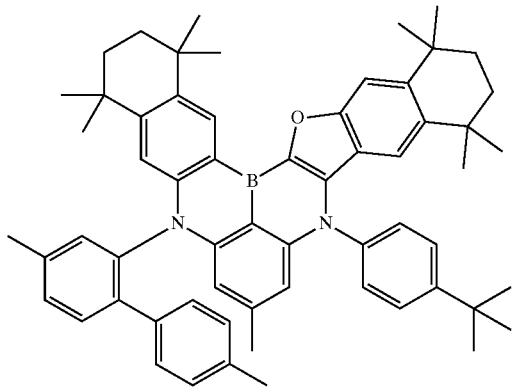
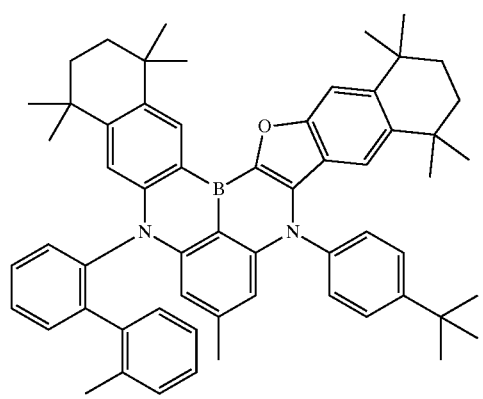
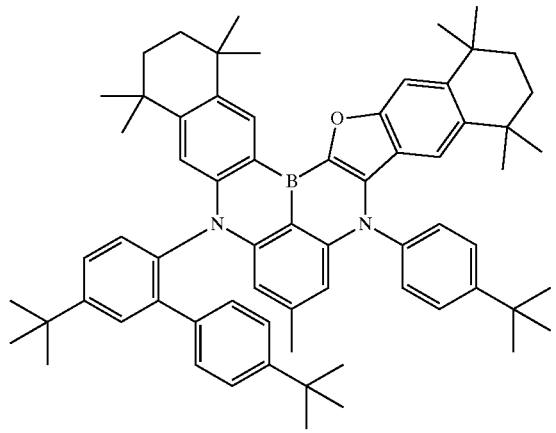
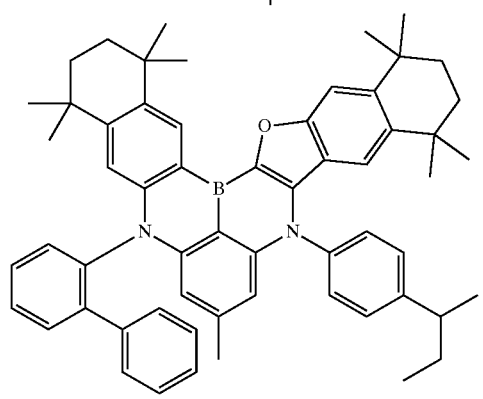
1366
-continued
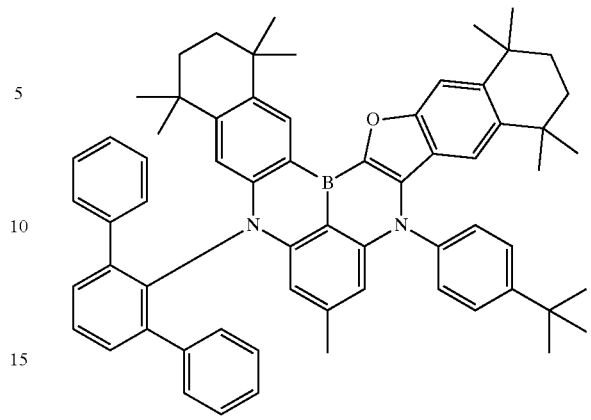
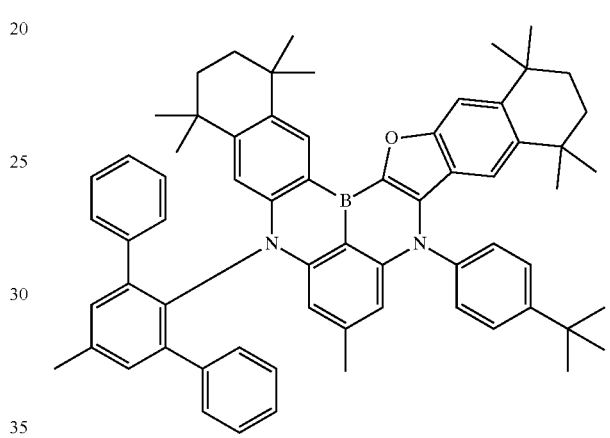
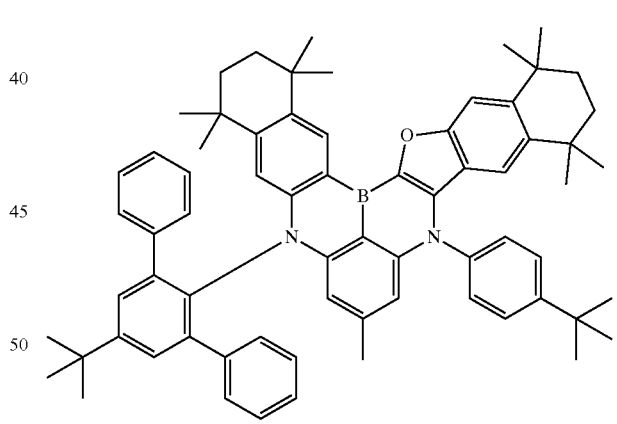
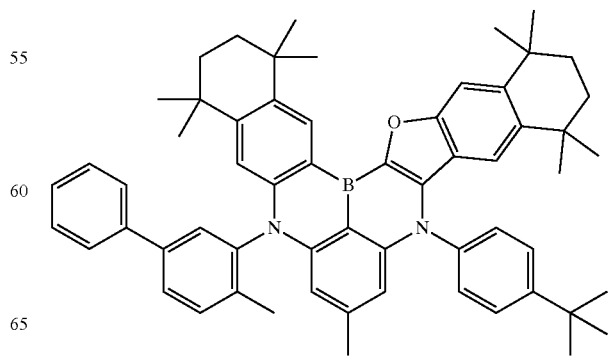

1367
-continued
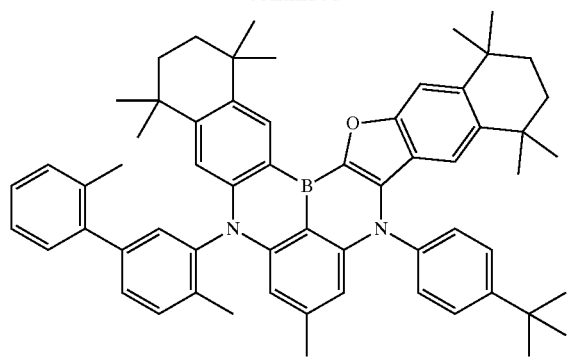
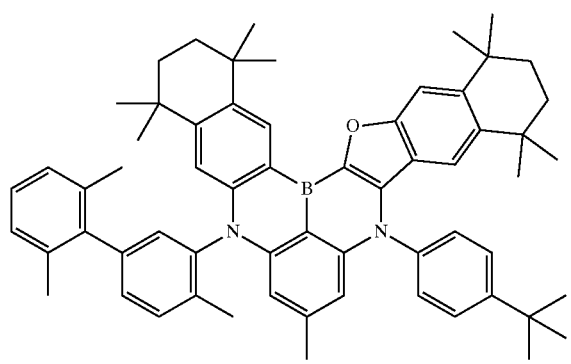
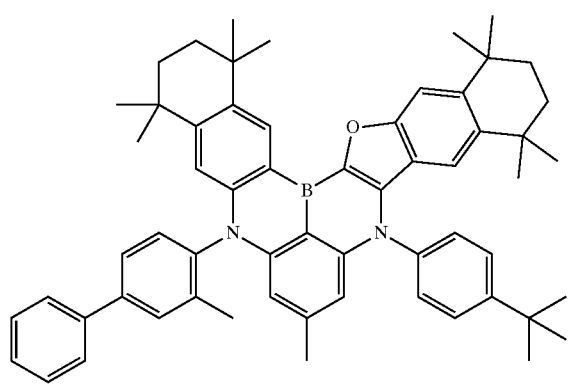
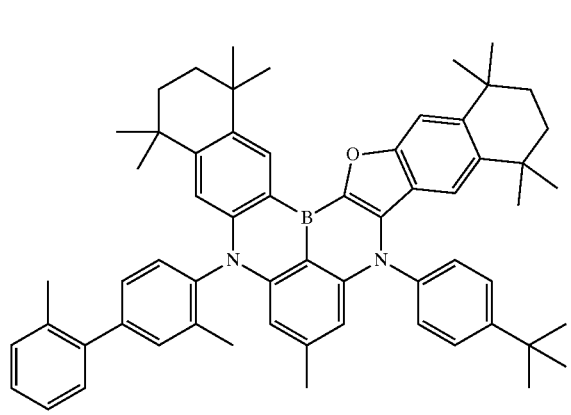
1368
-continued
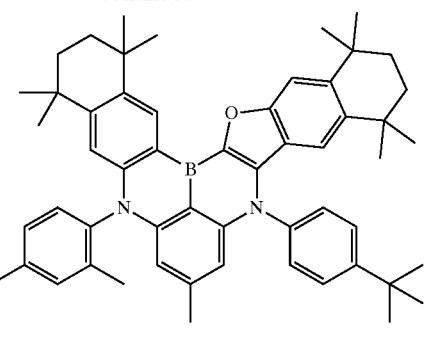
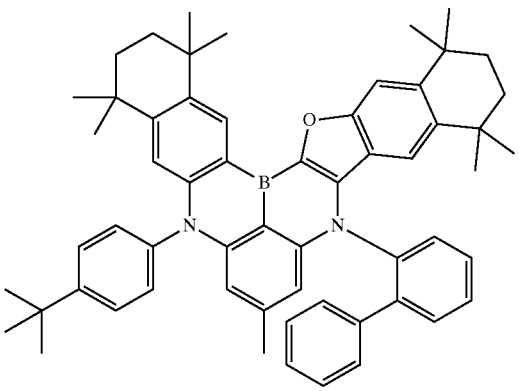
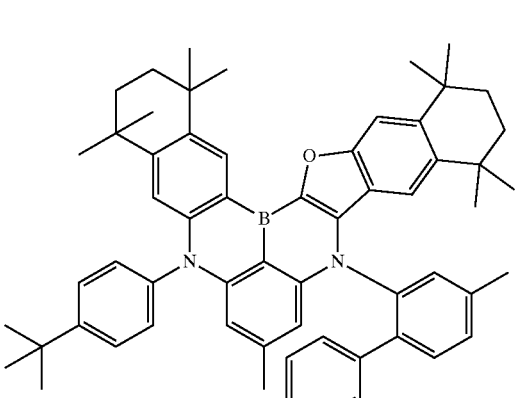
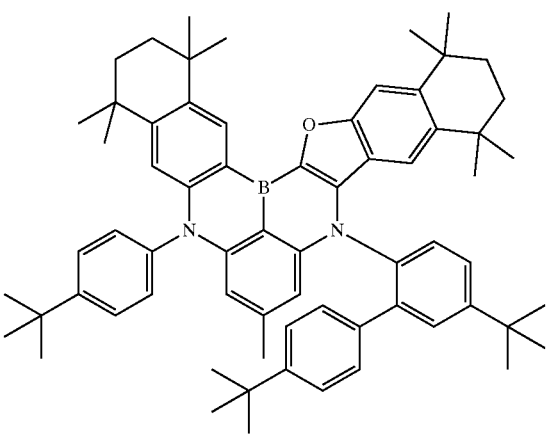

1369
-continued
1370
-continued
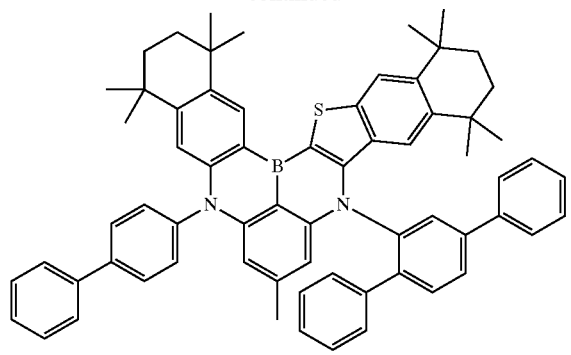
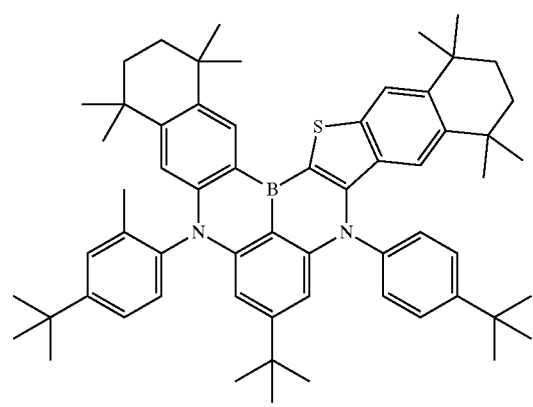
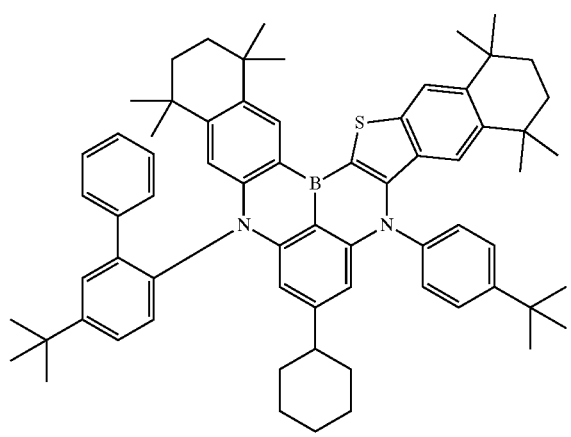
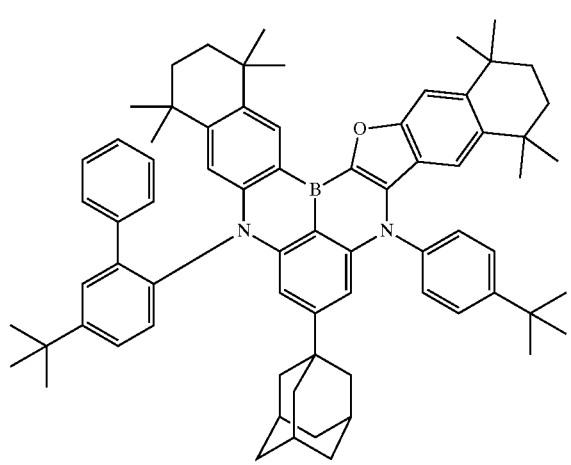
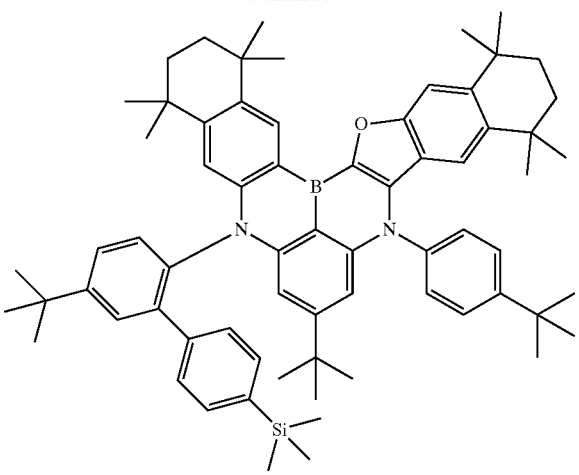
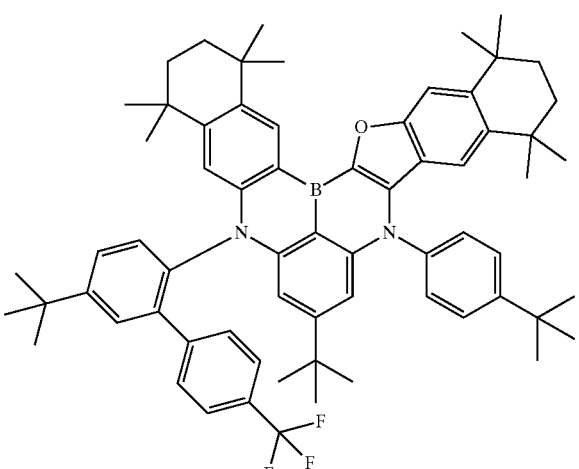
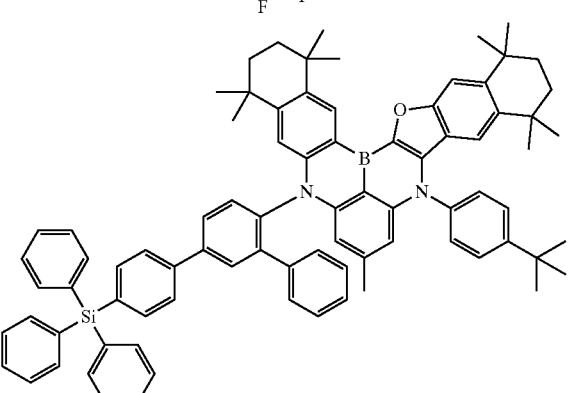
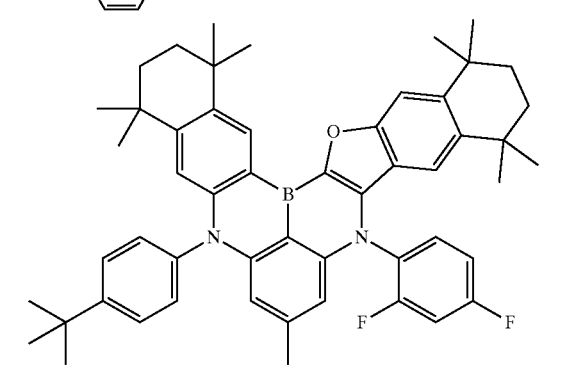

1371
-continued
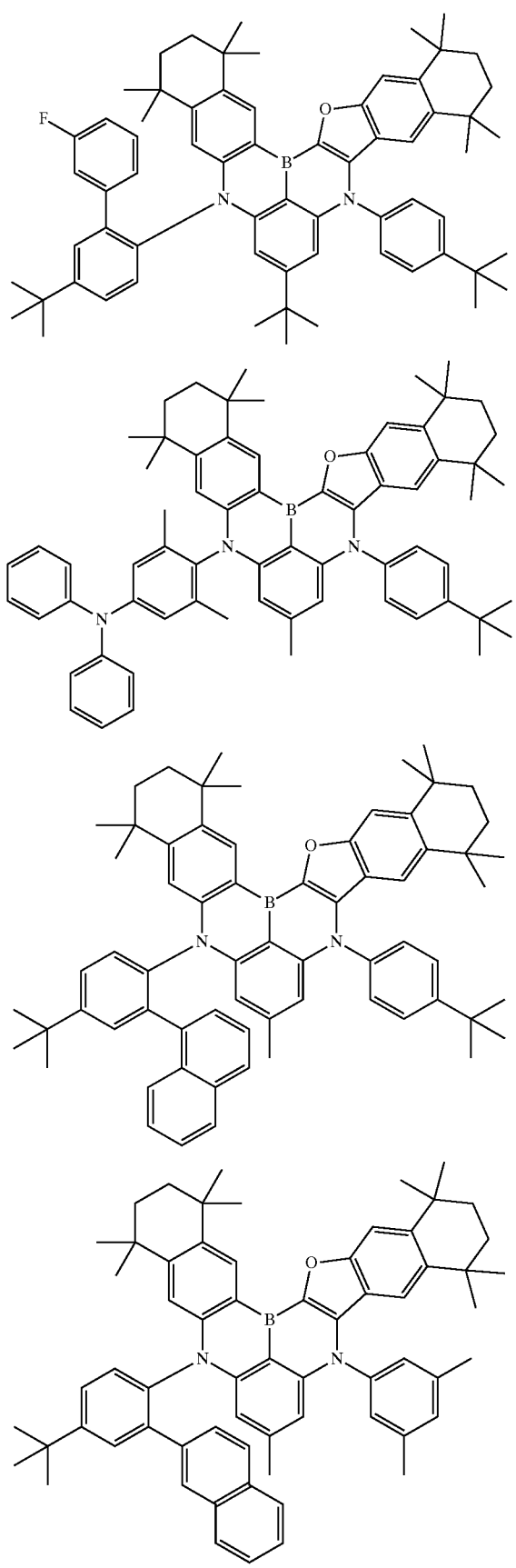
1372
-continued
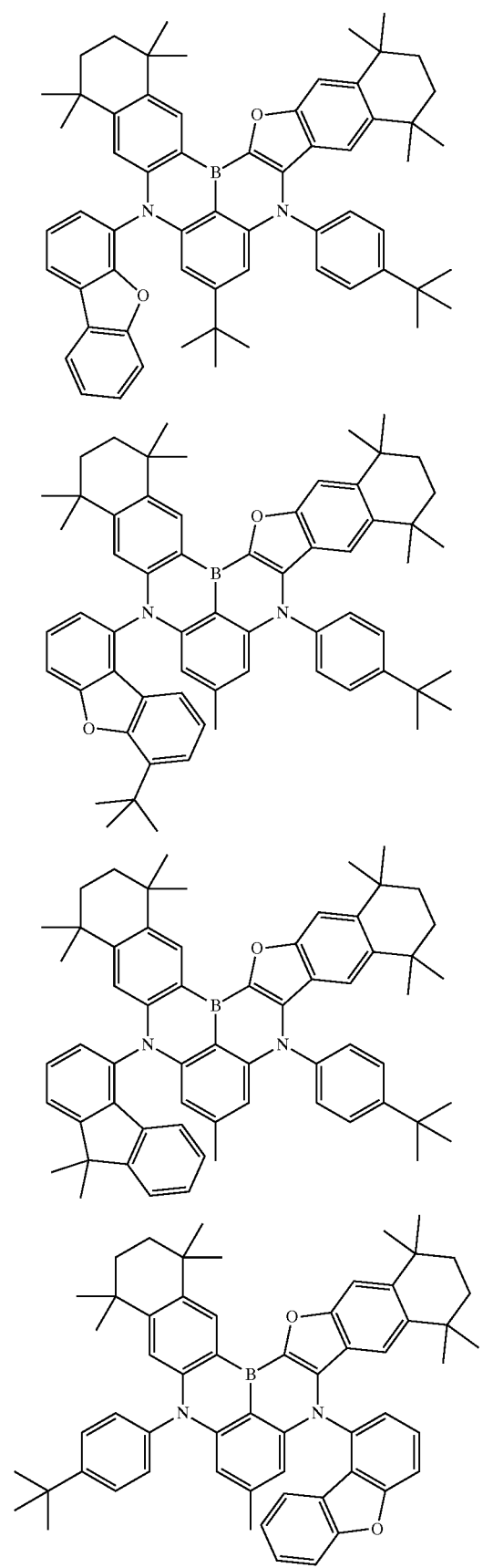

1373
-continued
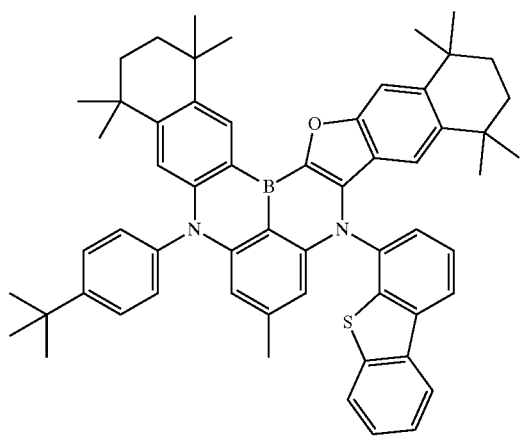
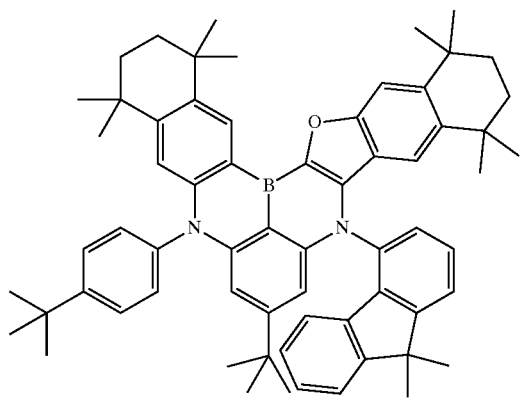
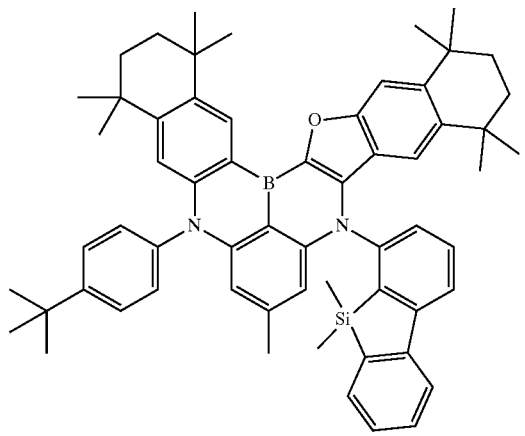
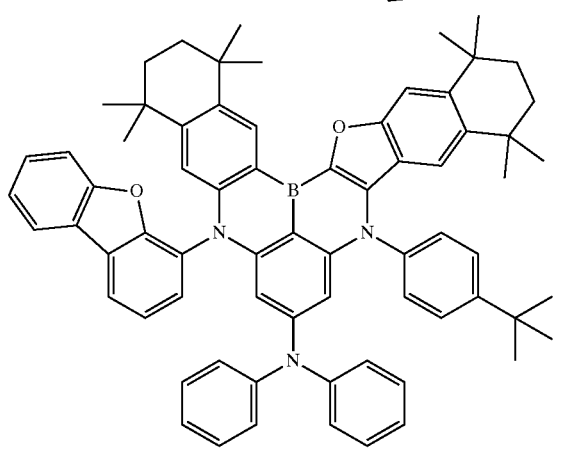
1374
-continued
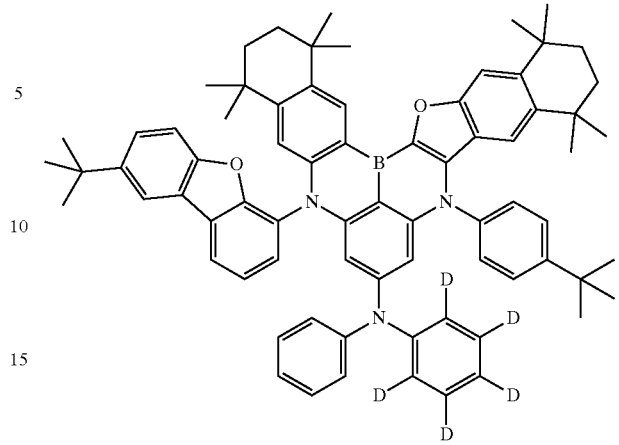
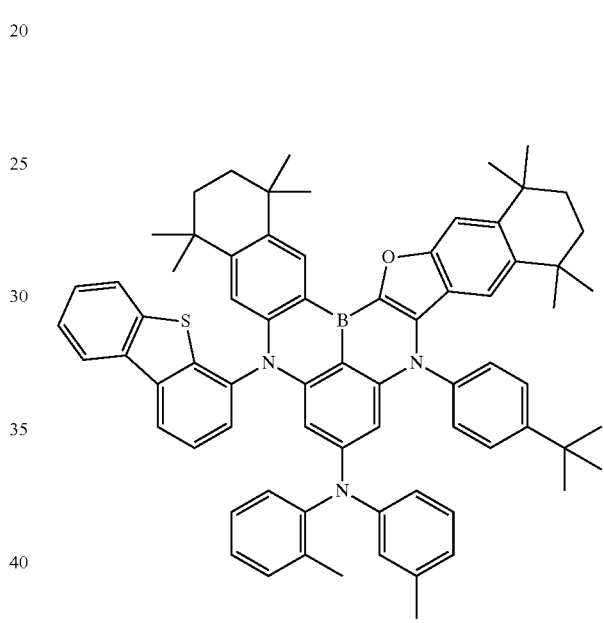
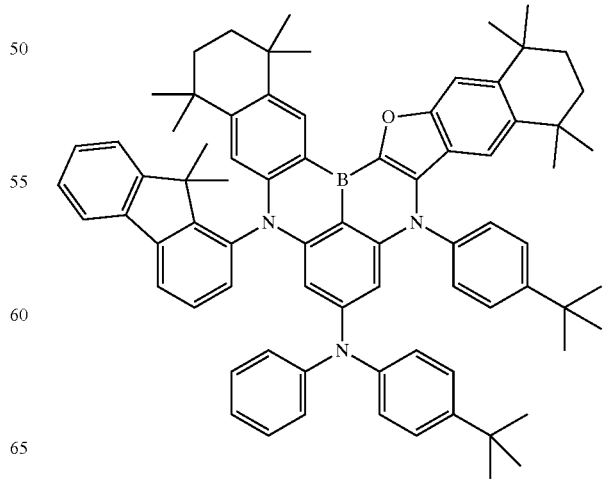

1375
-continued
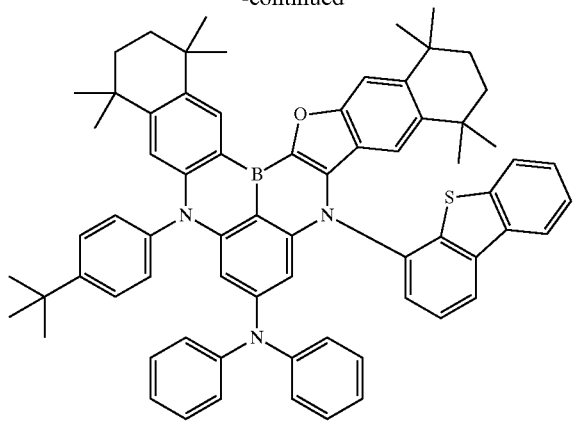
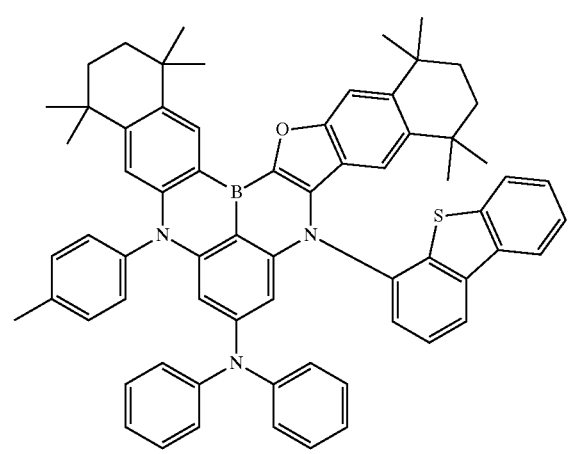
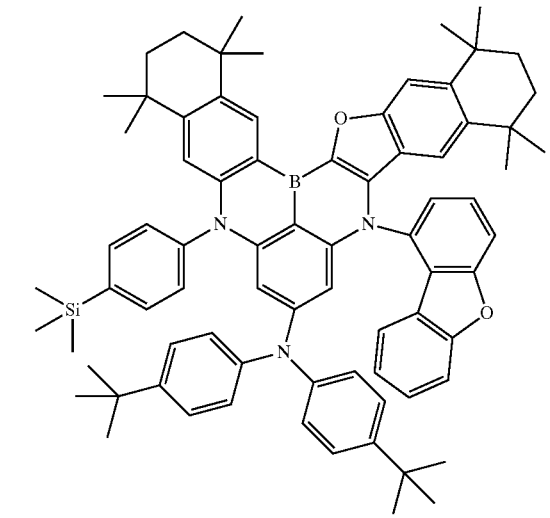
1376
-continued
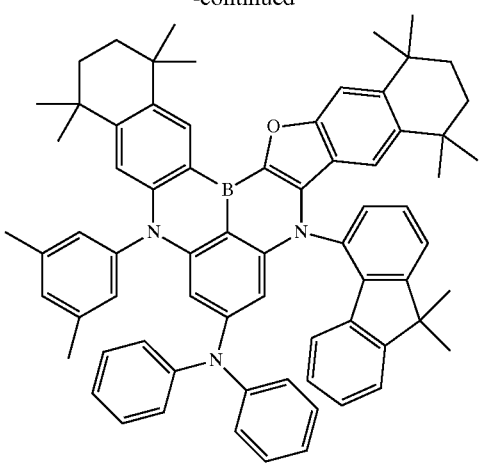
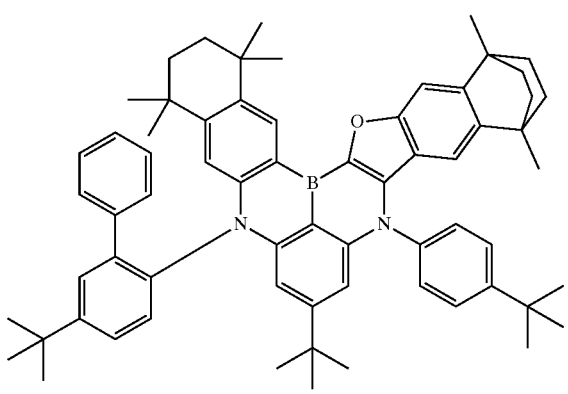
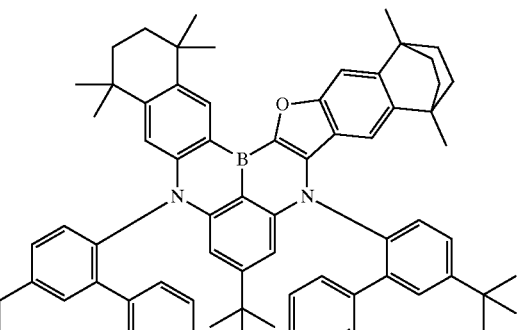
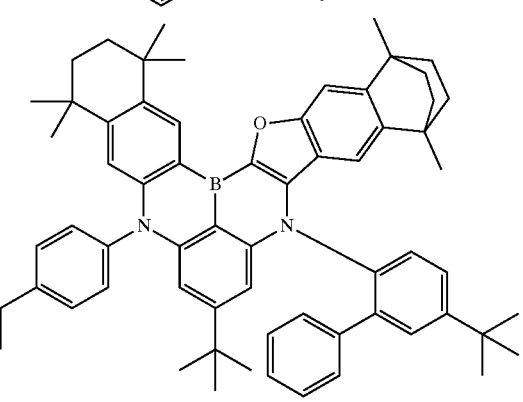

1377
-continued
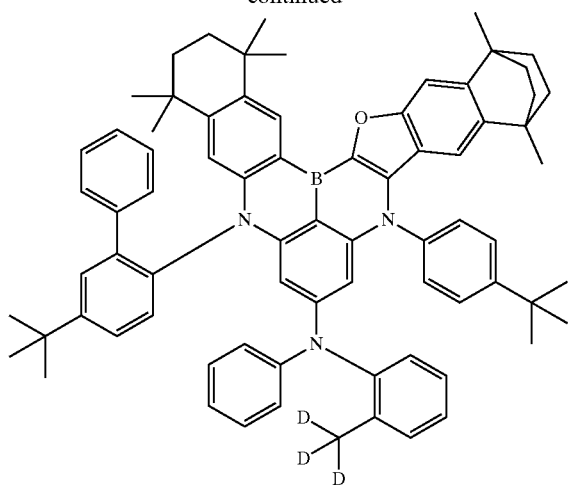
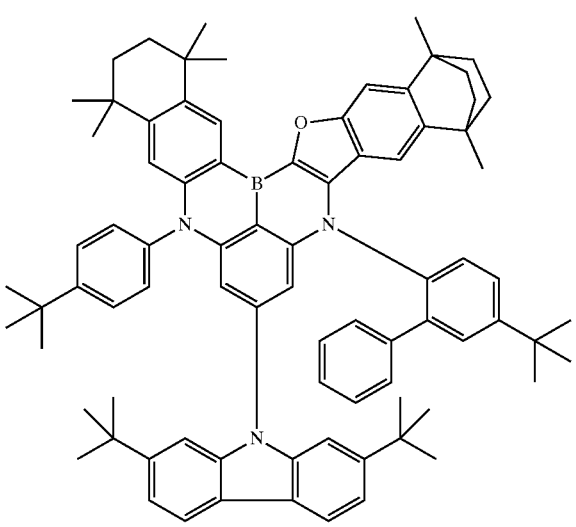
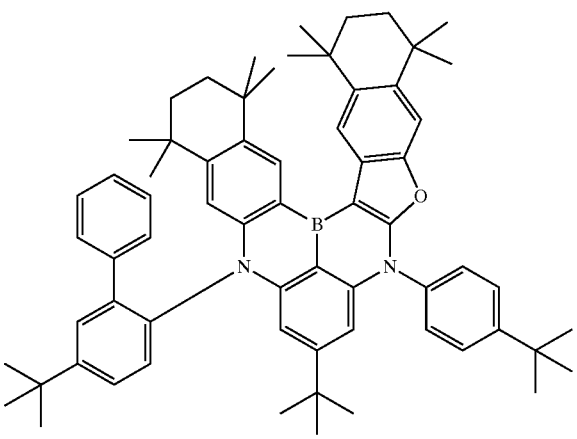
1378
-continued
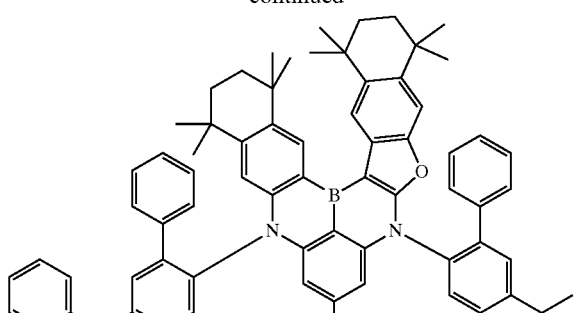
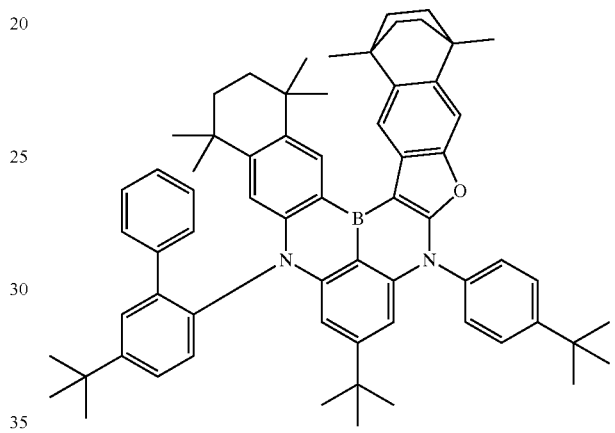
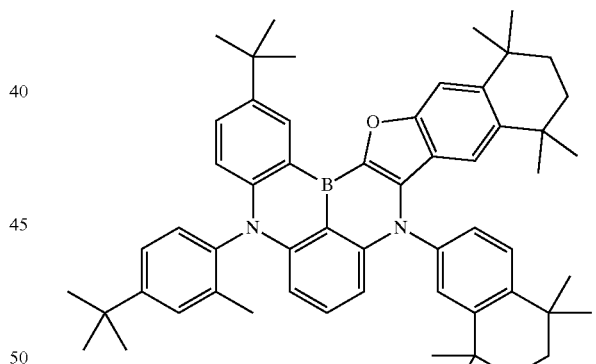
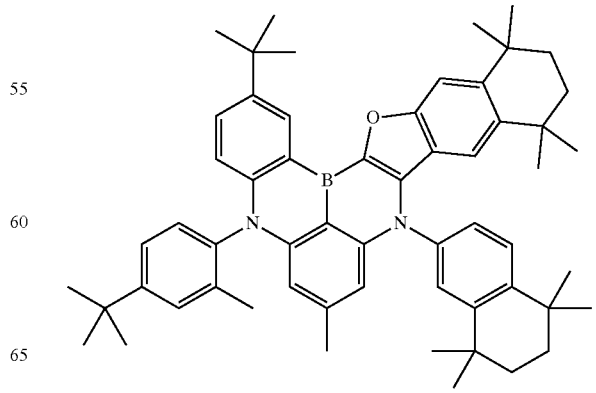

1379
-continued
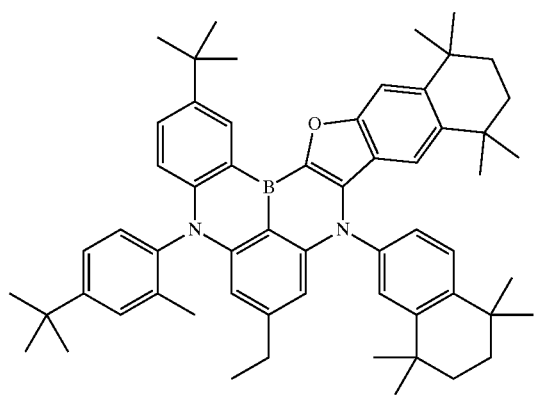
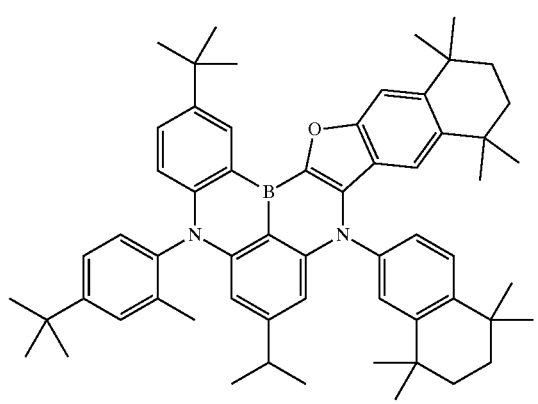
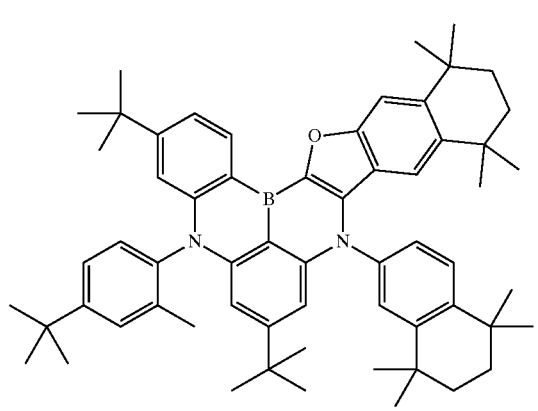
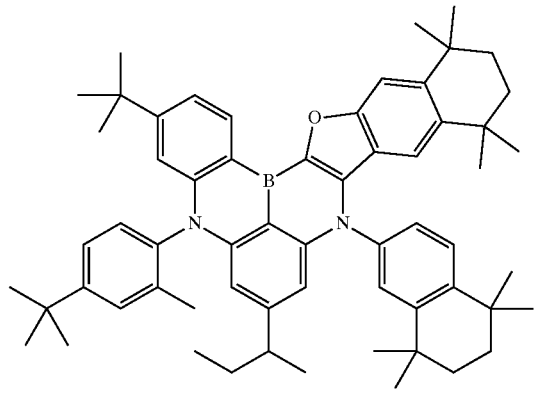
1380
-continued
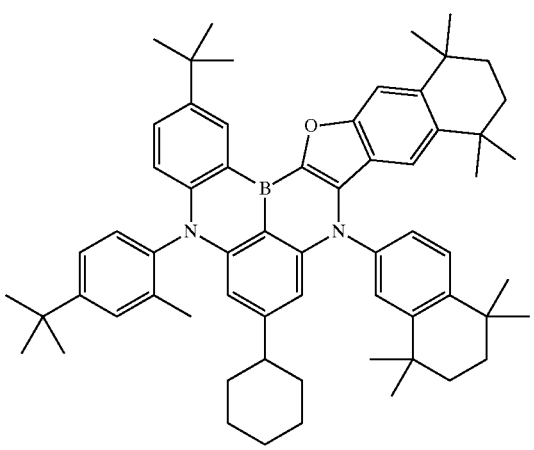
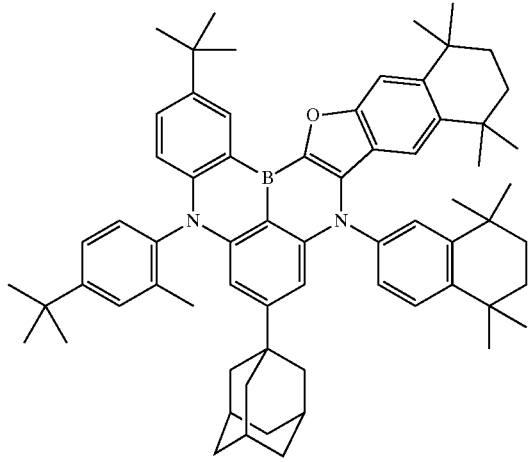
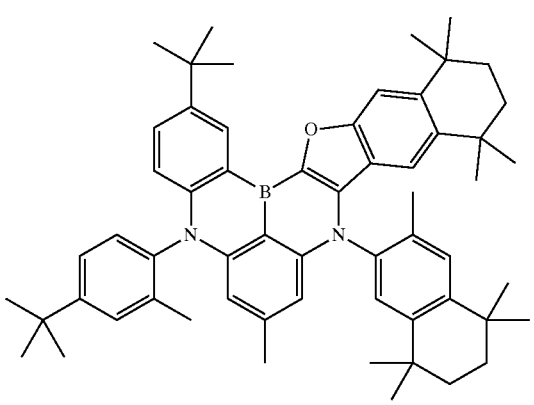
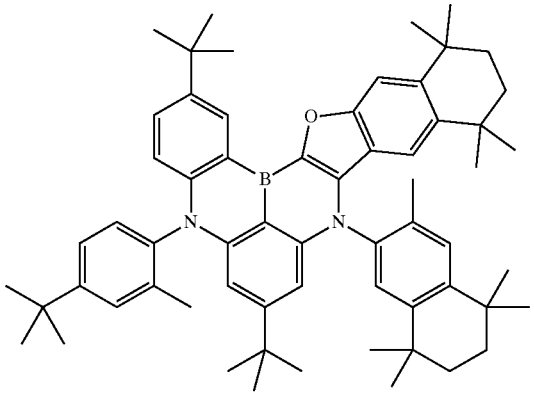

US 11,780,856 B2
1381
-continued
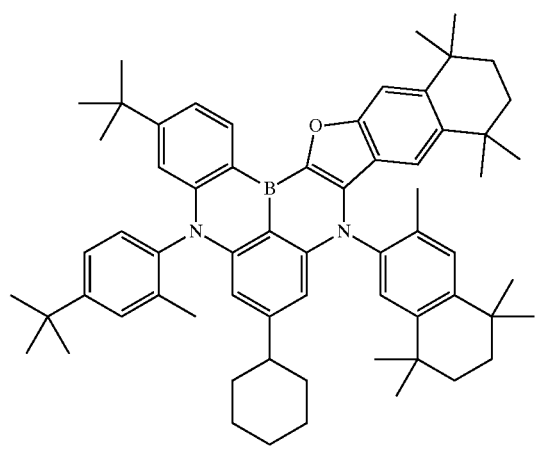
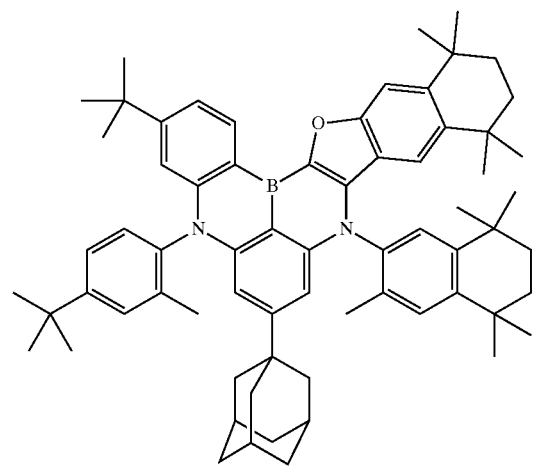
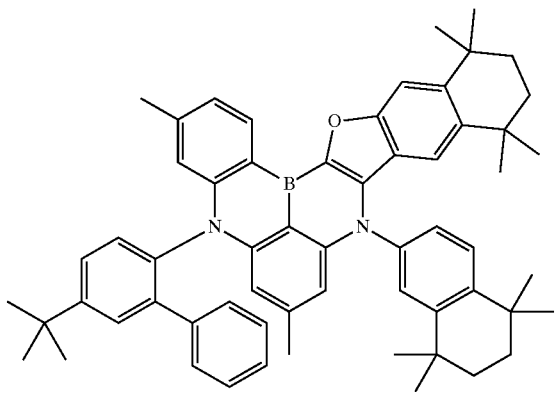
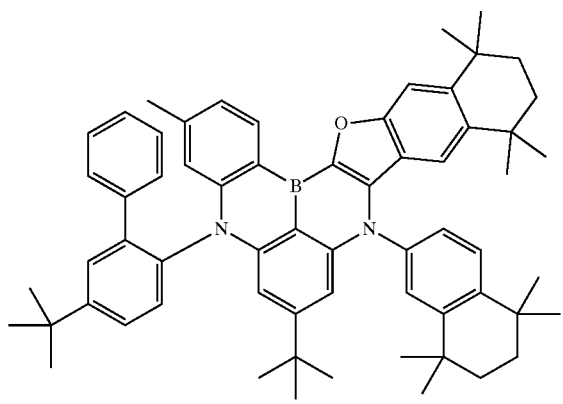
1382
-continued
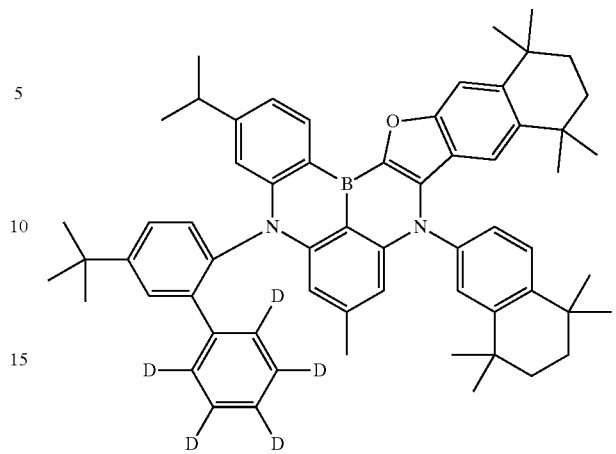
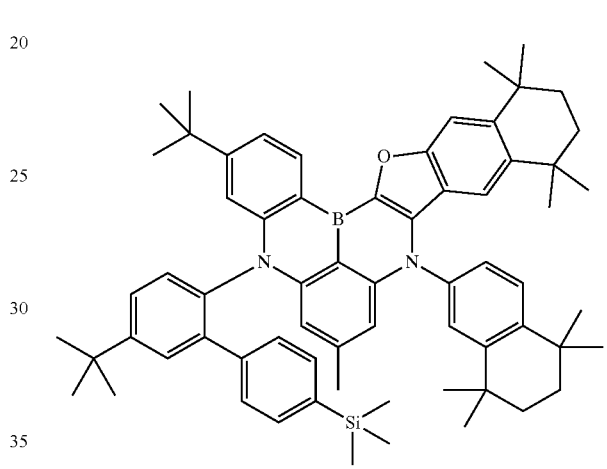
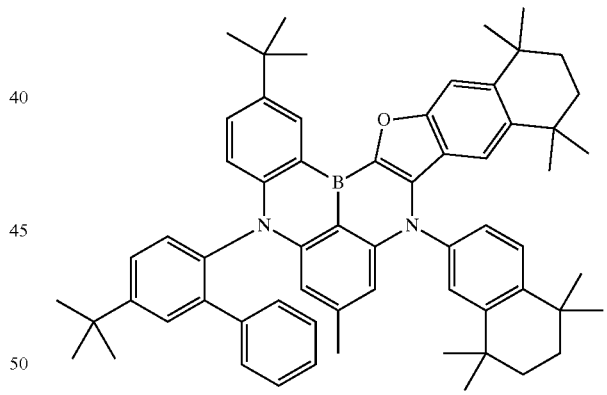
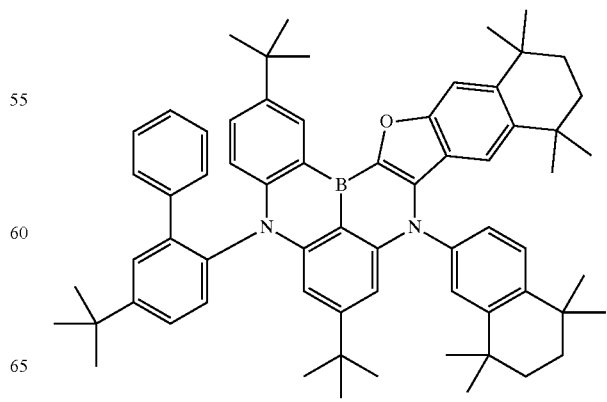

1383
-continued
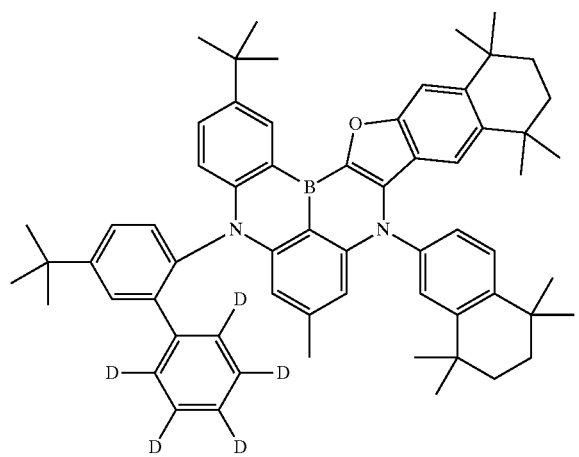
1384
-continued
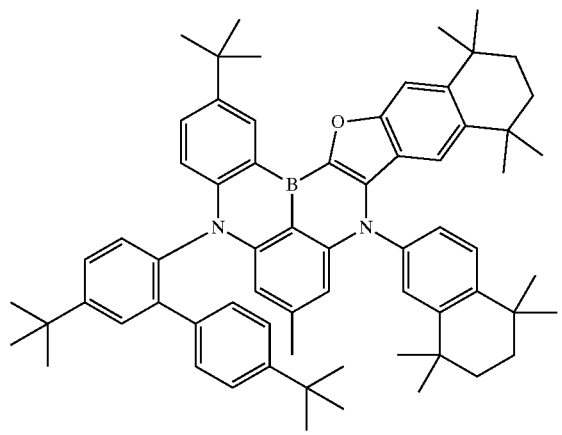
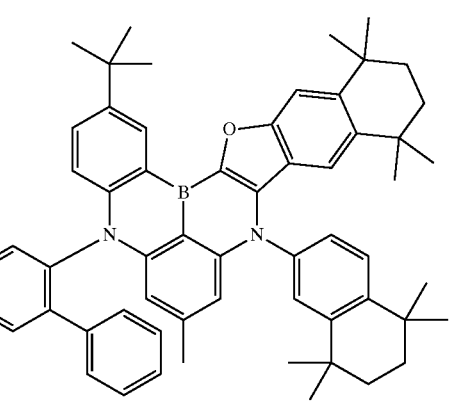
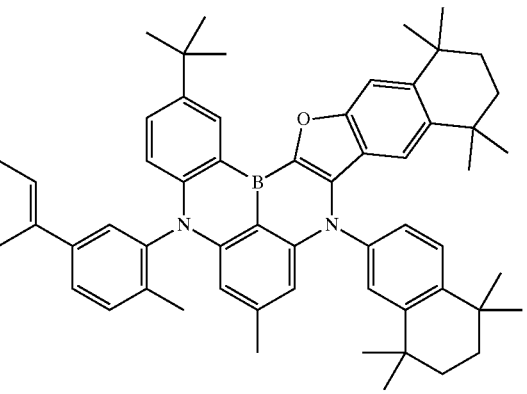
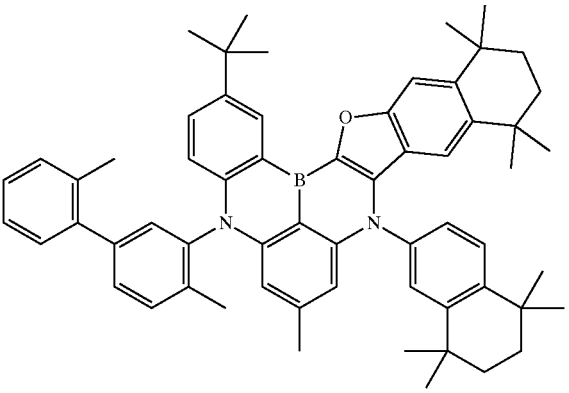

| 1385 | 1386 |
|---|---|
| -continued | -continued |
| 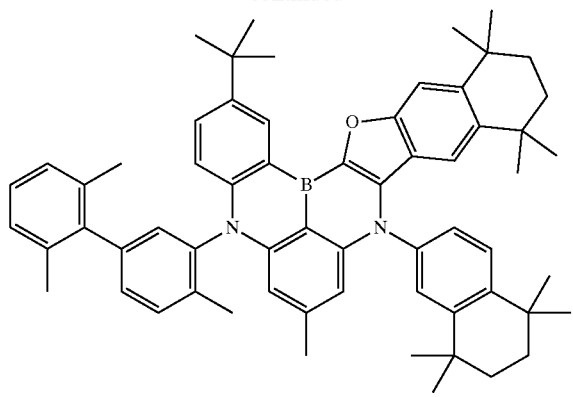 | 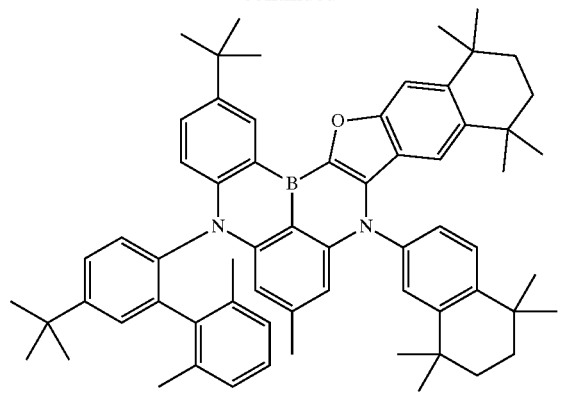 |
| 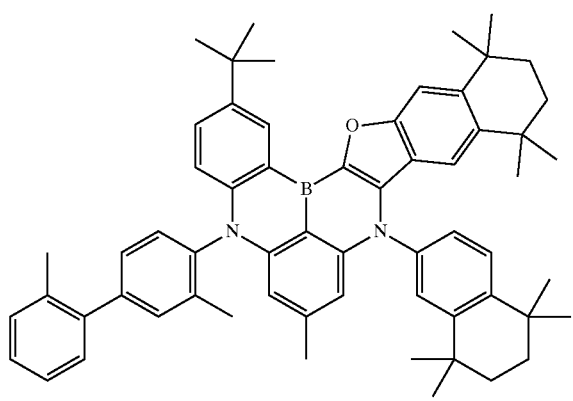 | 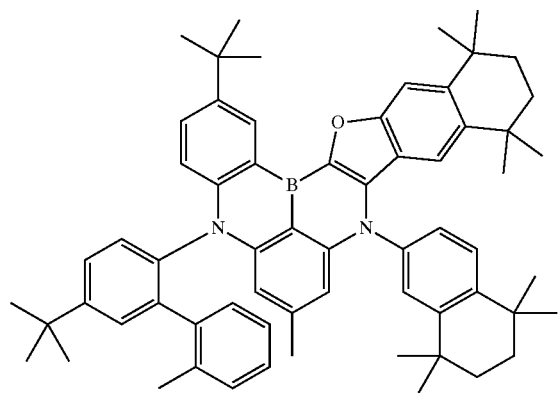 |
| 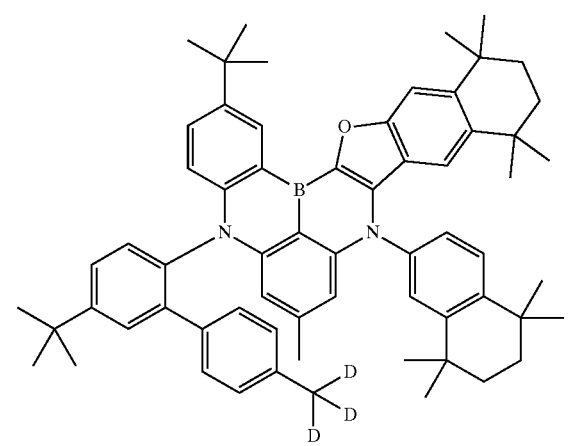 | 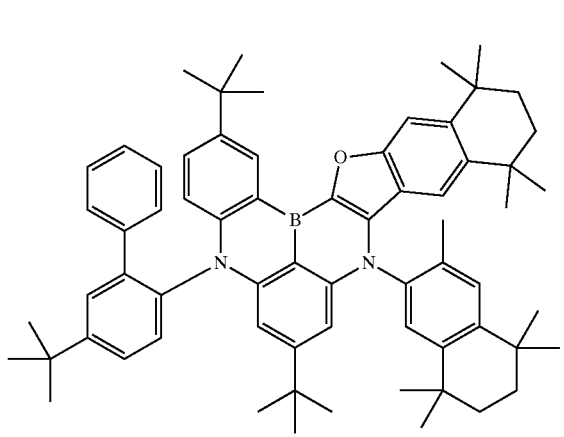 |
| 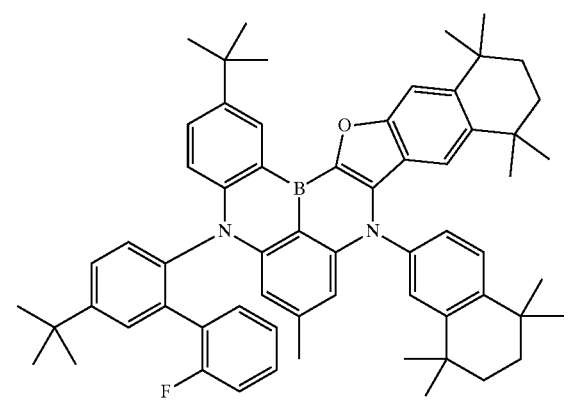 | 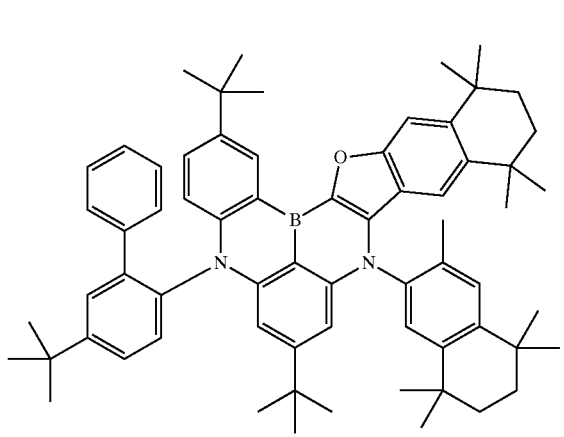 |

1387
-continued
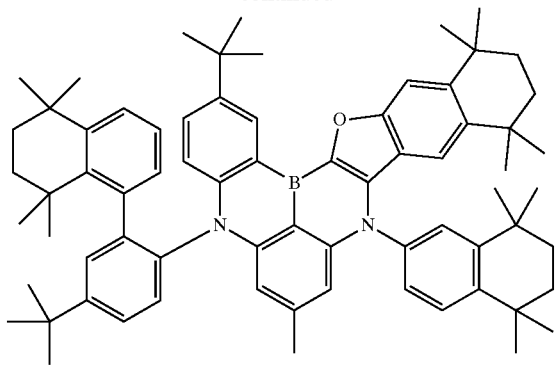
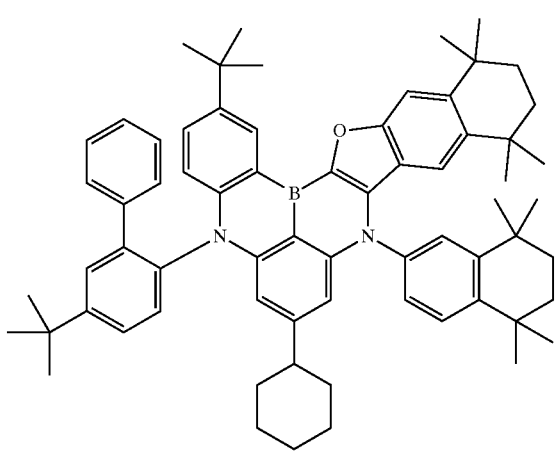
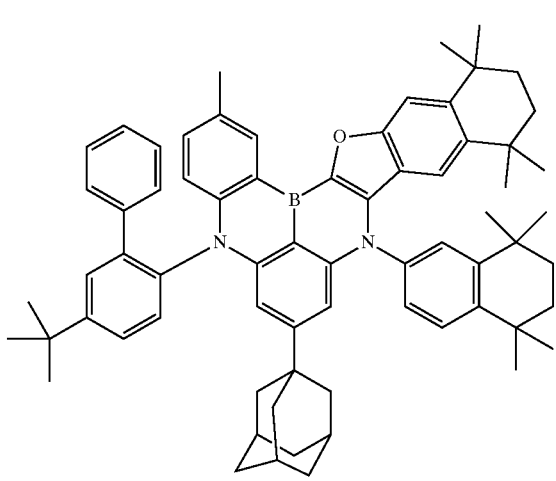
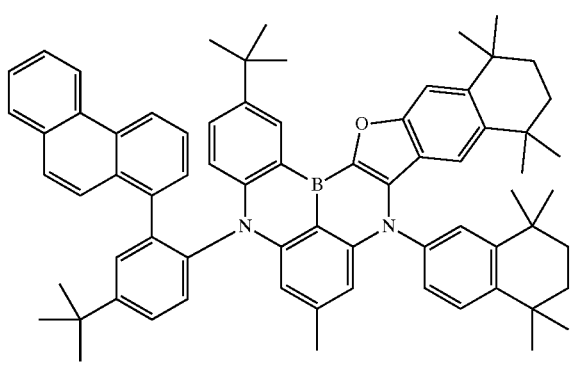
1388
-continued
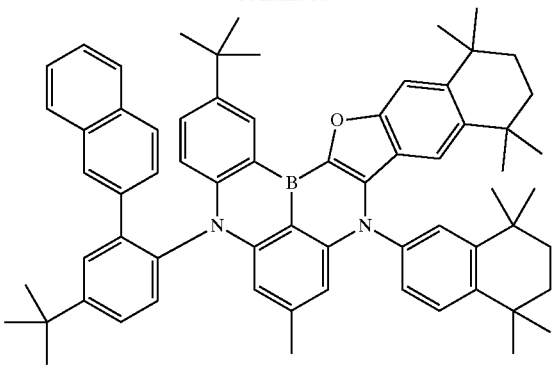
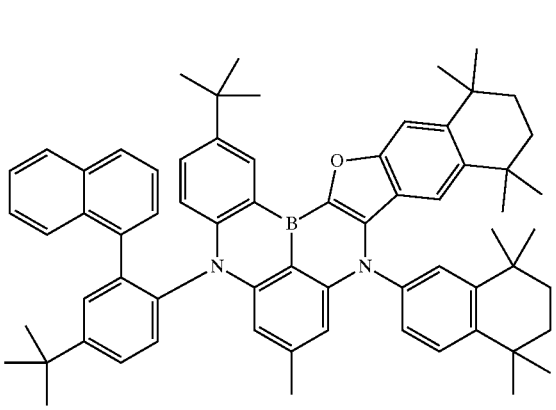
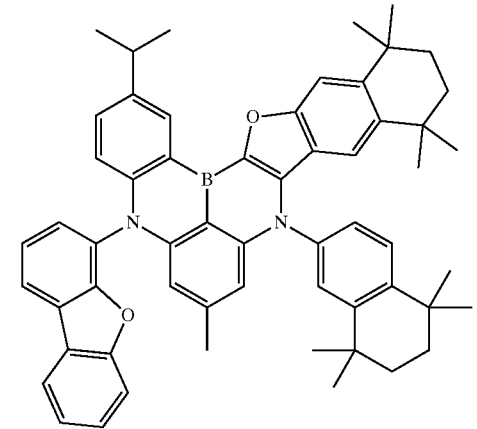
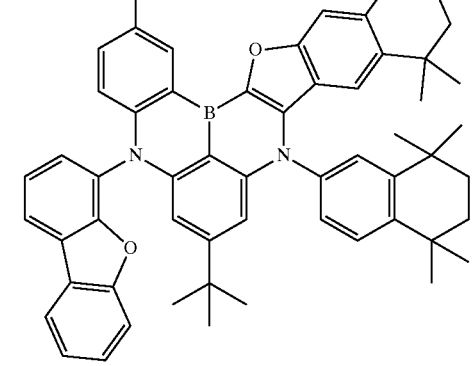

1389
-continued
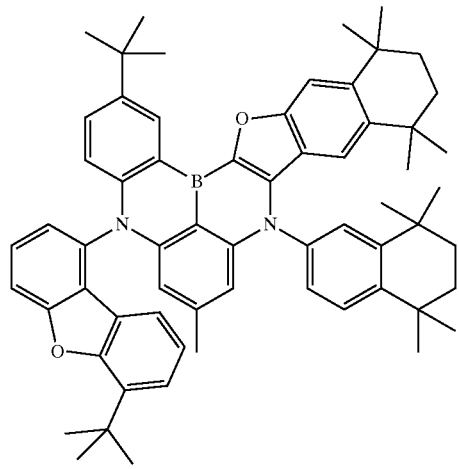
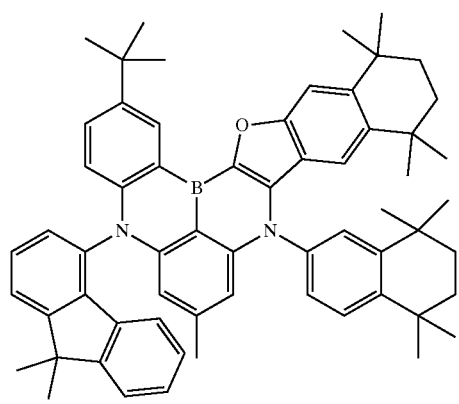
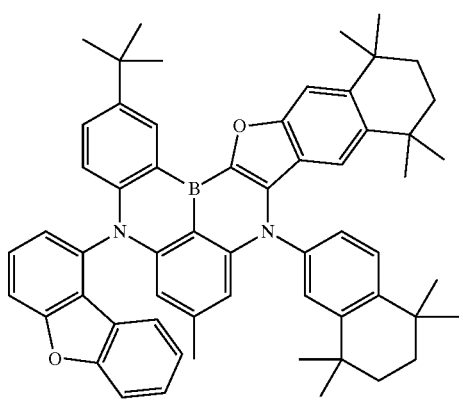
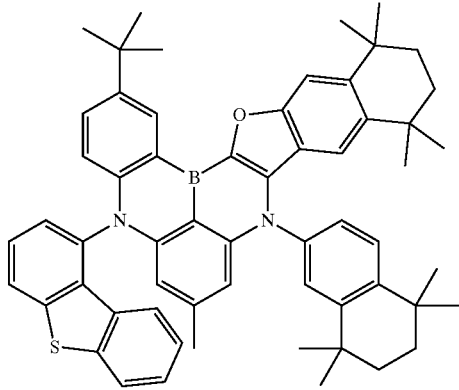
1390
-continued
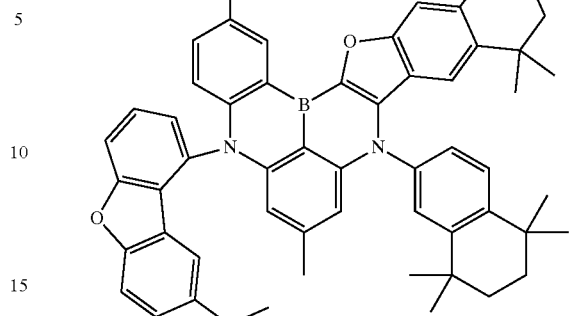
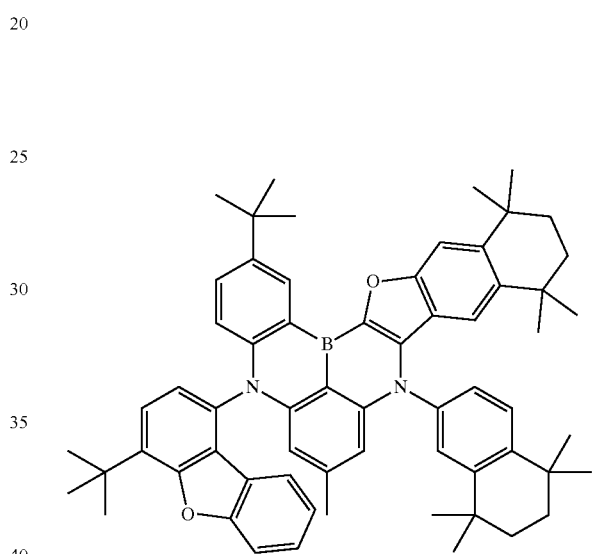
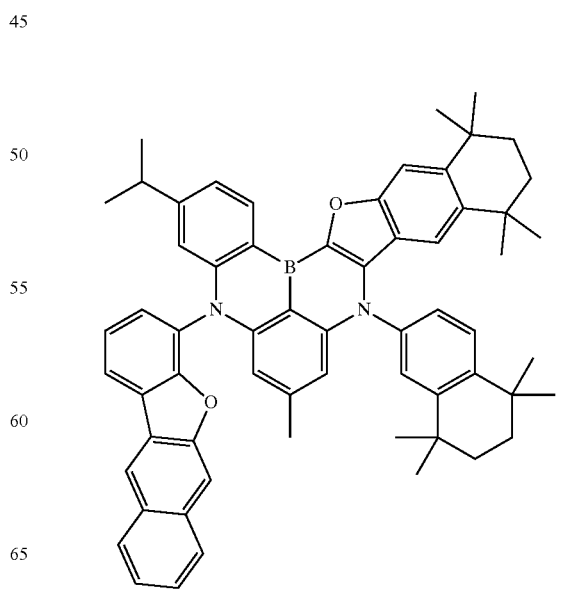

1391
-continued
1392
-continued
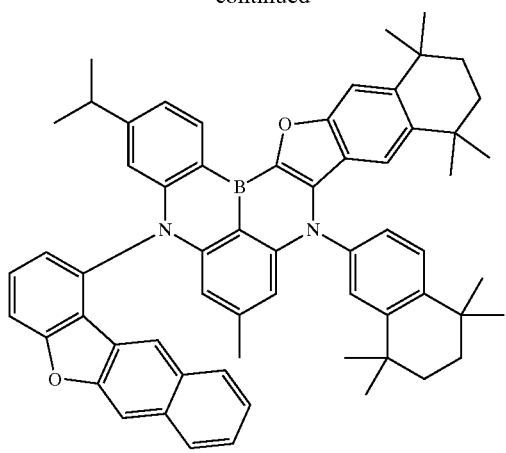
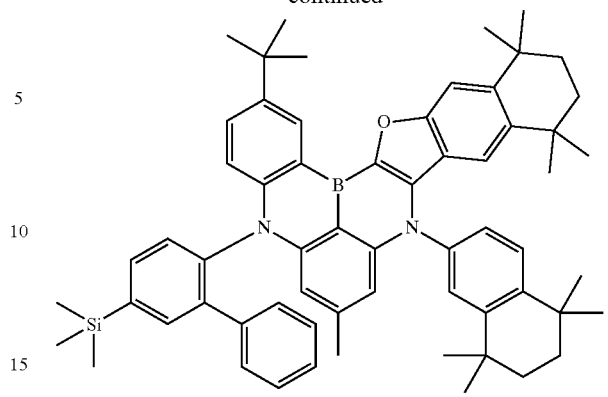
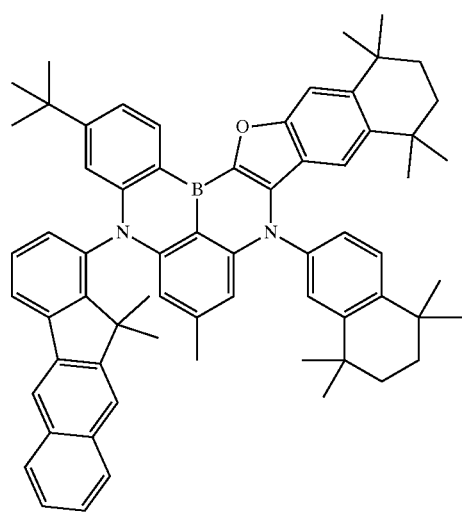
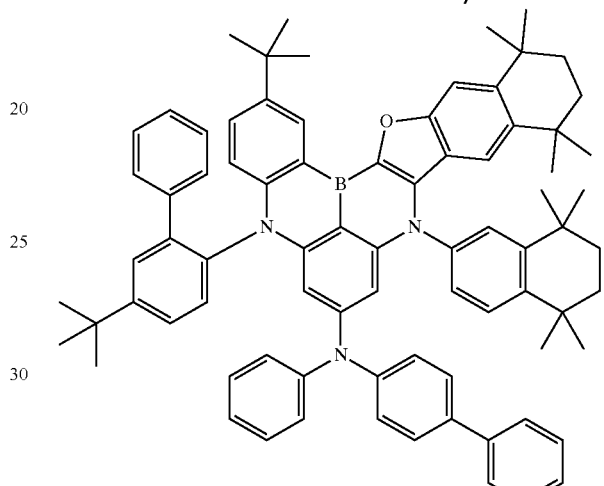
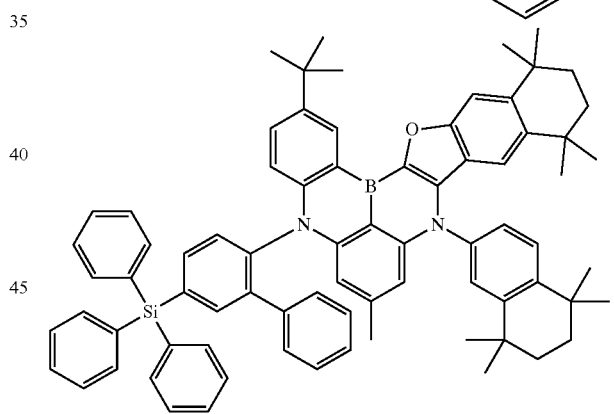
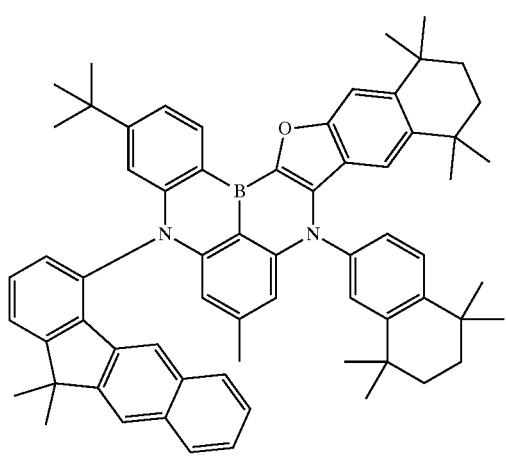
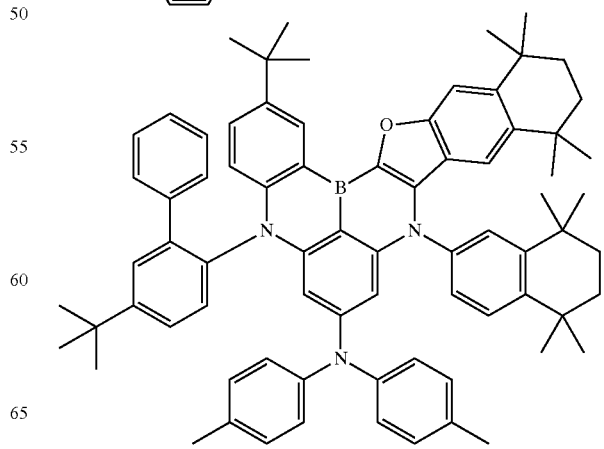

1393
-continued
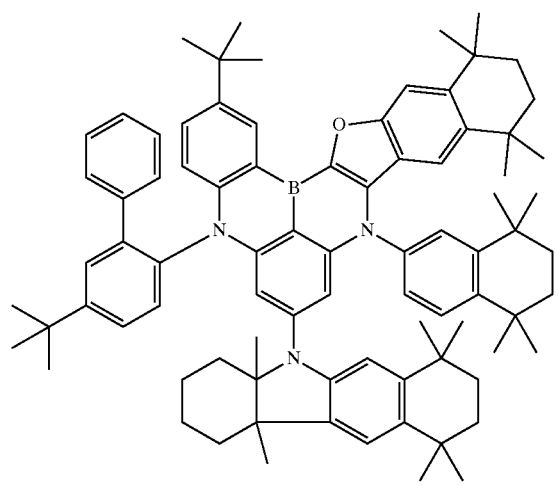
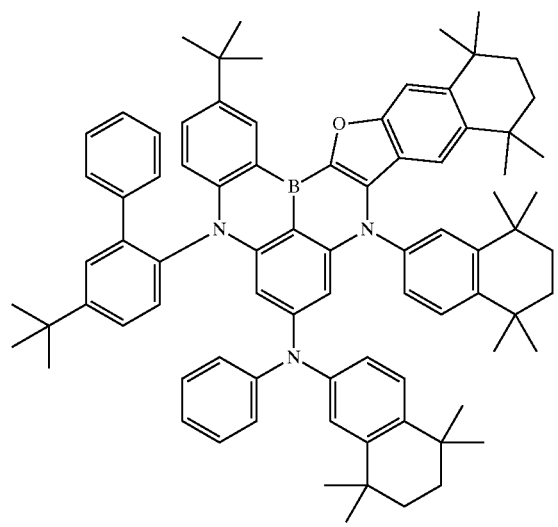
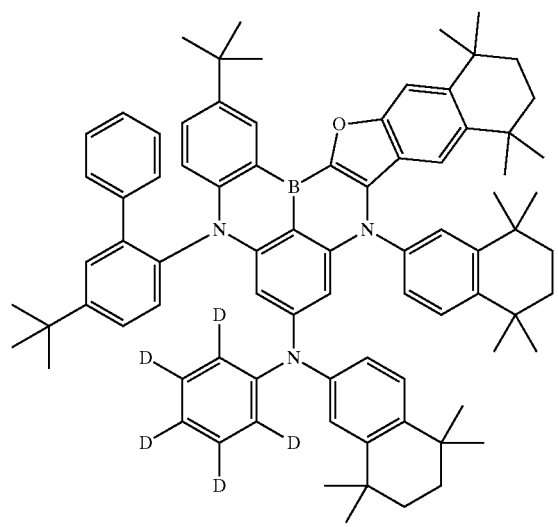
1394
-continued
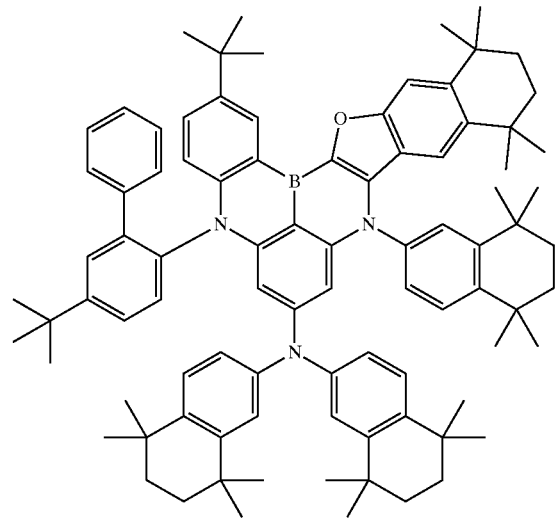 [SMILES: CC(C)(C)c1ccc2c(c1)B1c3oc4cc5c(cc4c3N(c3ccc4c(c3)C(C)(C)CCC4(C)C)c3cc(N(c4ccc6c(c4)C(C)(C)CCC6(C)C)c4ccc6c(c4)C(C)(C)CCC6(C)C)cc(c31)N2c1ccc(C(C)(C)C)cc1-c1ccccc1)C(C)(C)CCC5(C)C]
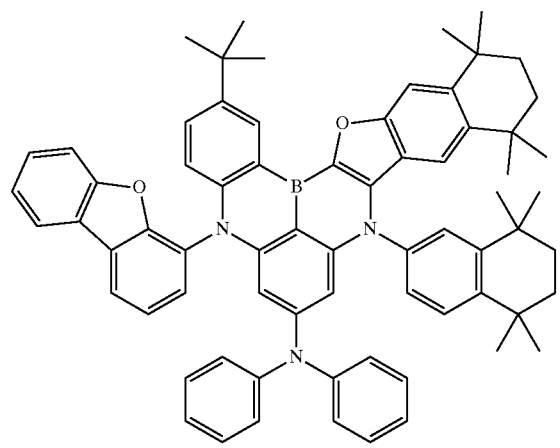
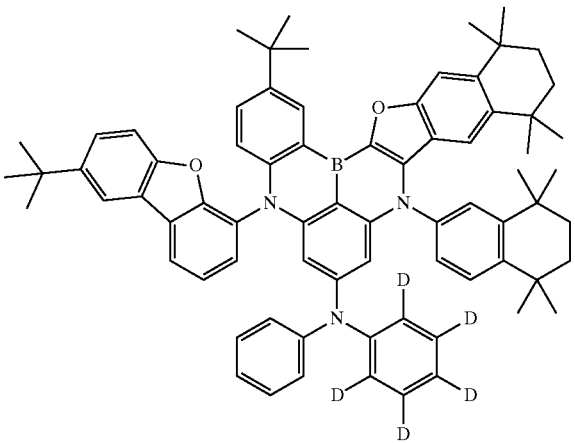

1395
-continued
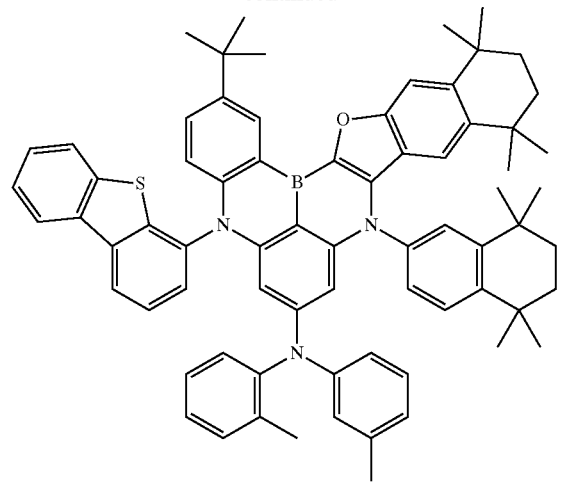
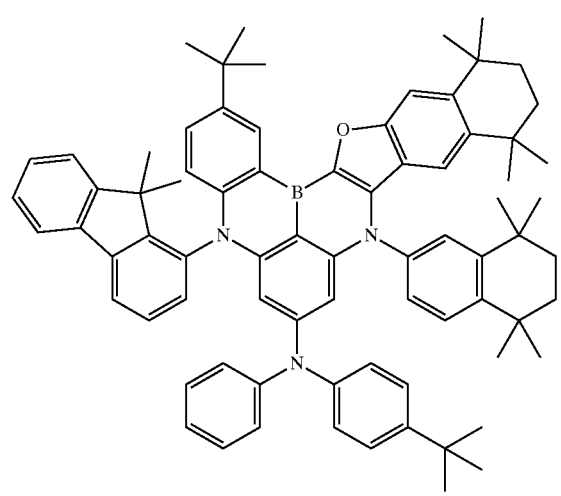
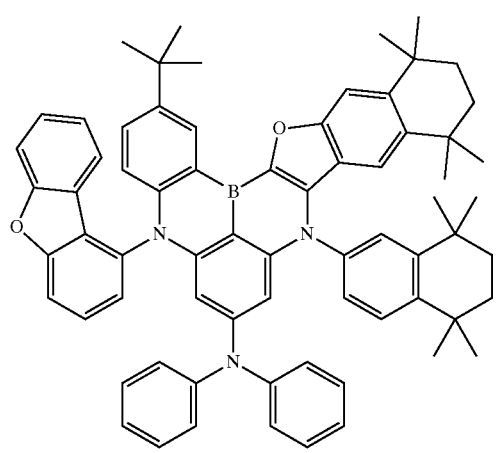
1396
-continued
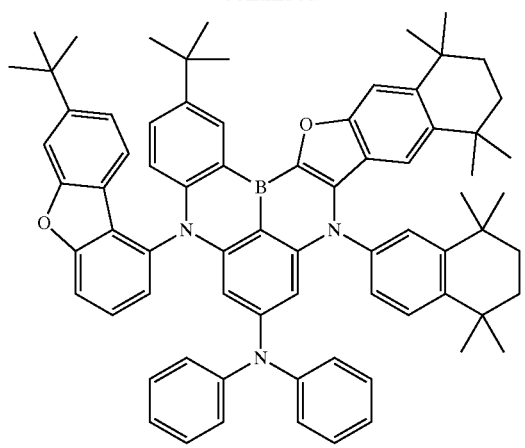
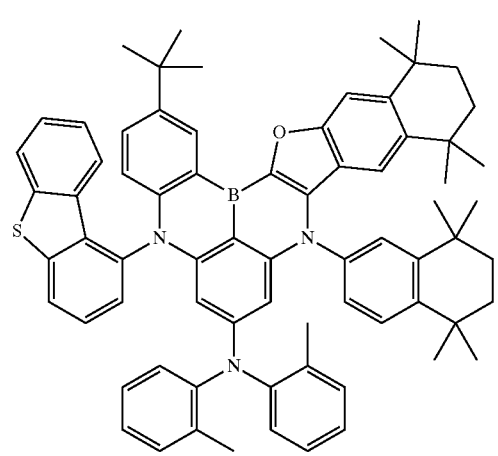
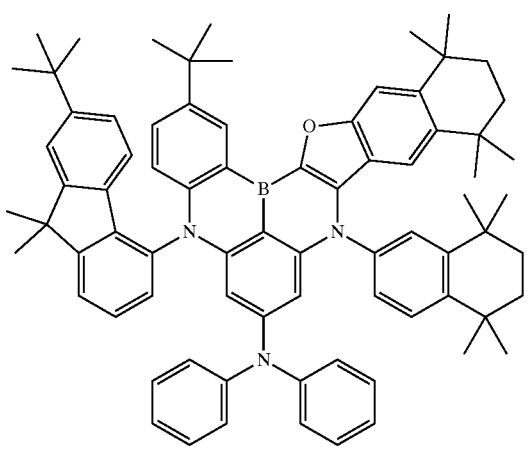

1397
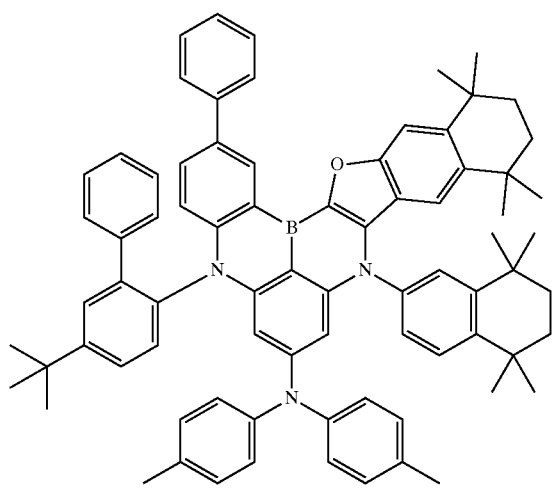
1398
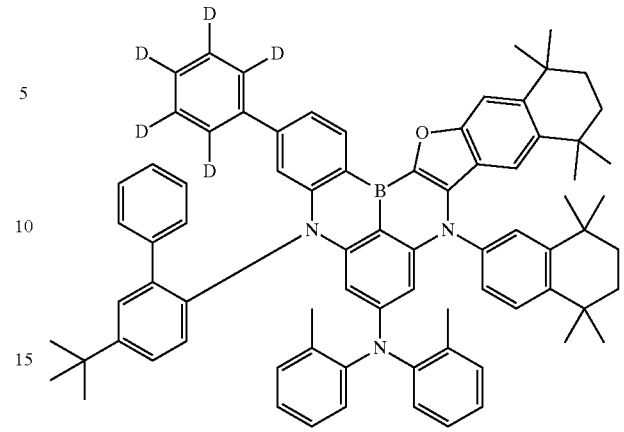
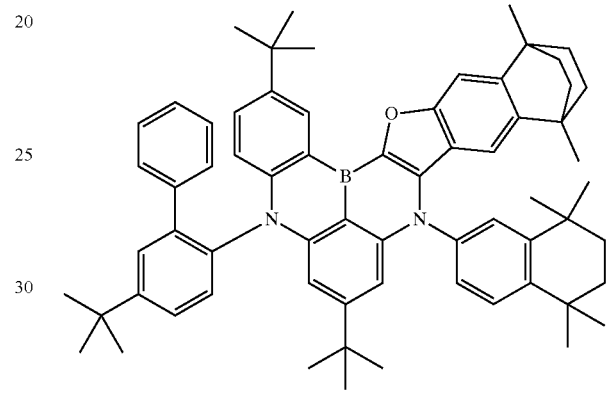
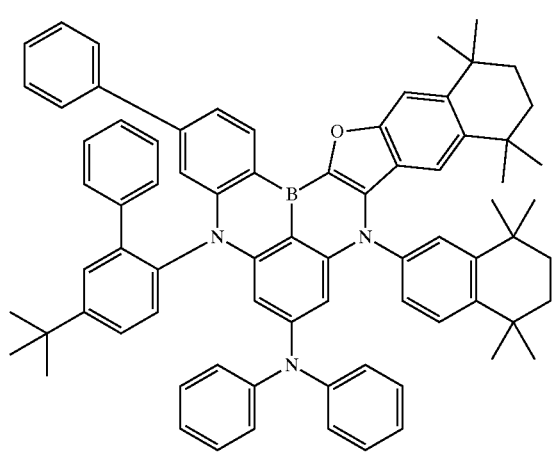
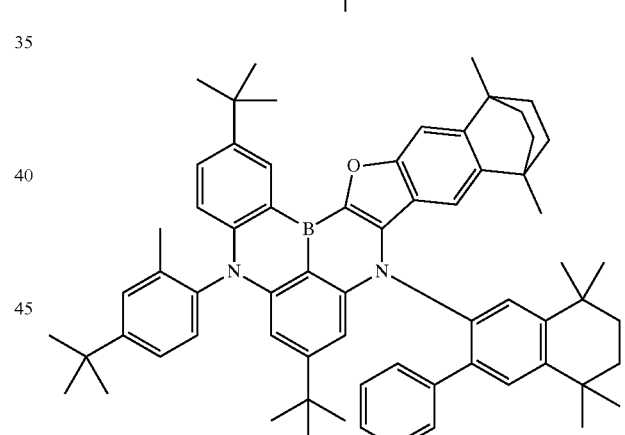

1399
-continued
1400
-continued
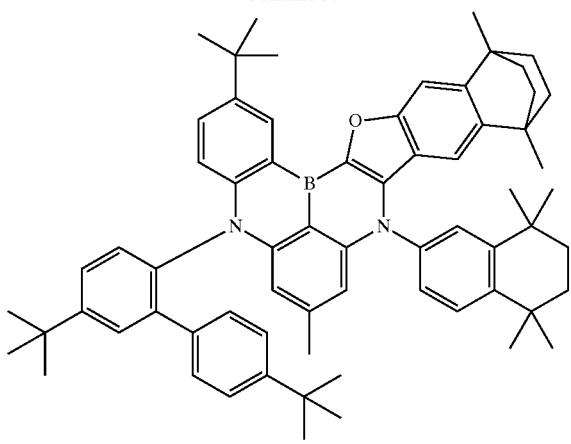
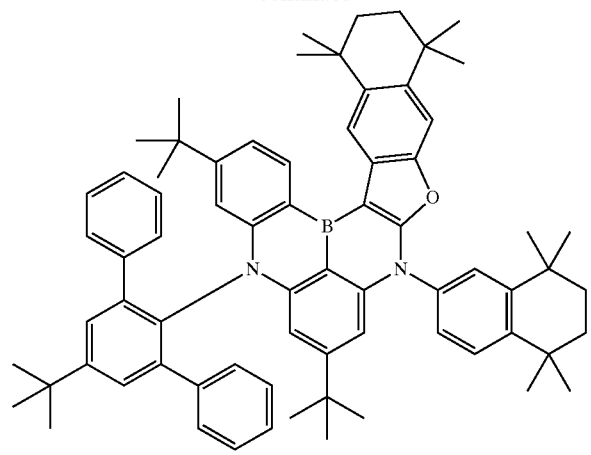

1401
-continued
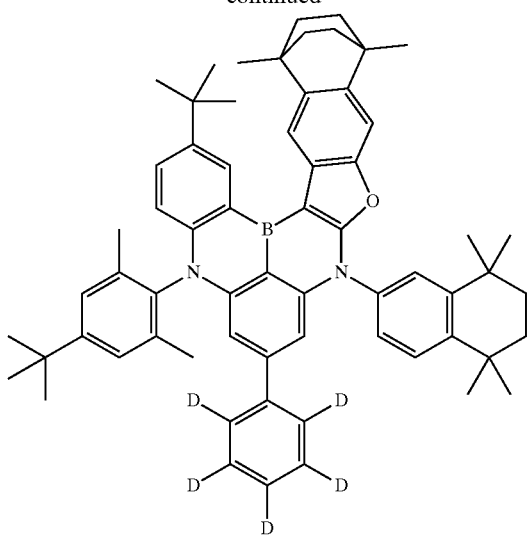
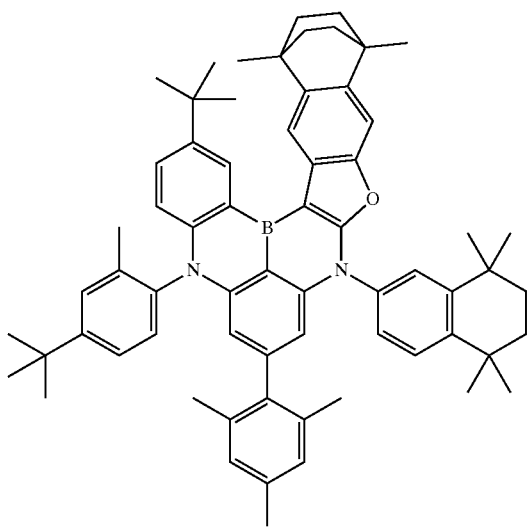
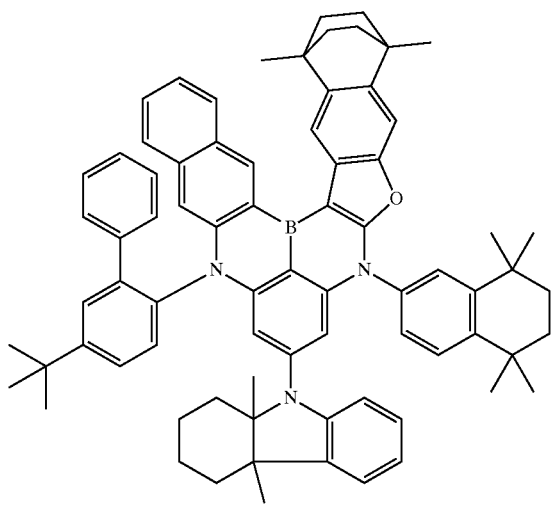
1402
-continued
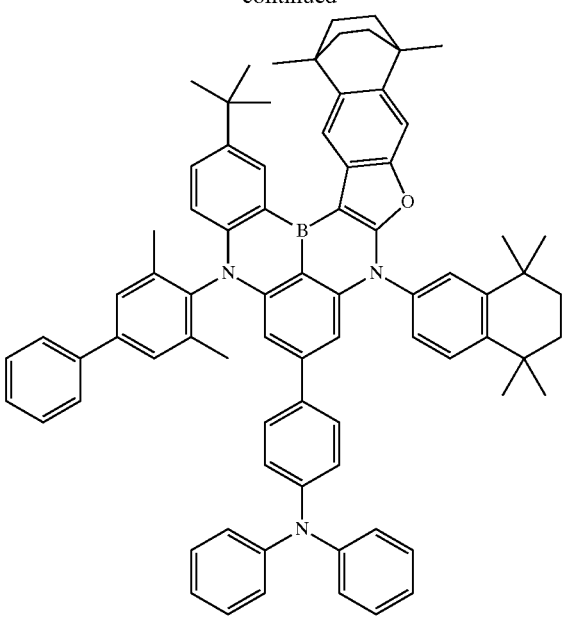
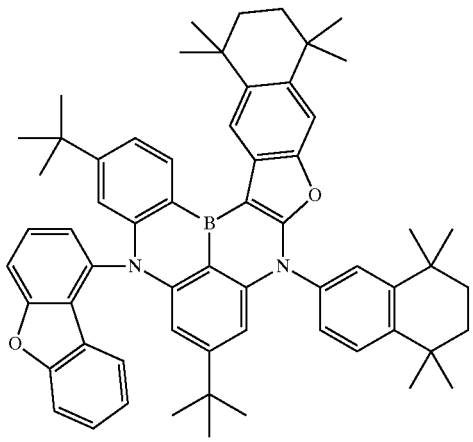
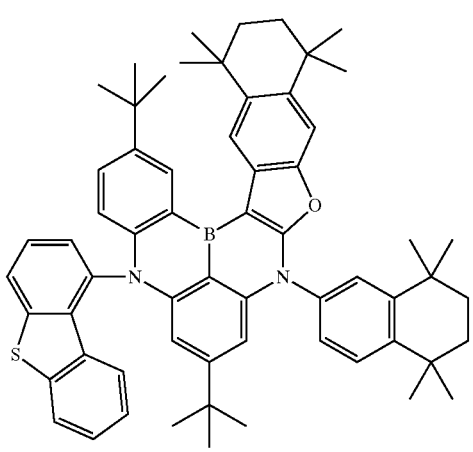 [SMILES: CC(C)(C)c1ccc2c(c1)B1c3c(cc(C(C)(C)C)cc3N2c2cccc3sc4ccccc4c23)N(c2ccc3c(c2)C(C)(C)CCC3(C)C)c2oc3cc4c(cc3c21)C(C)(C)CCC4(C)C]

1403
-continued
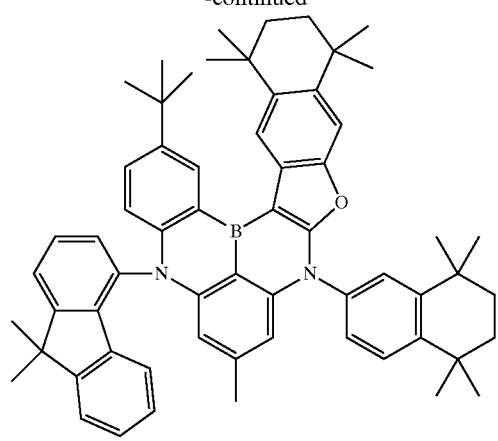
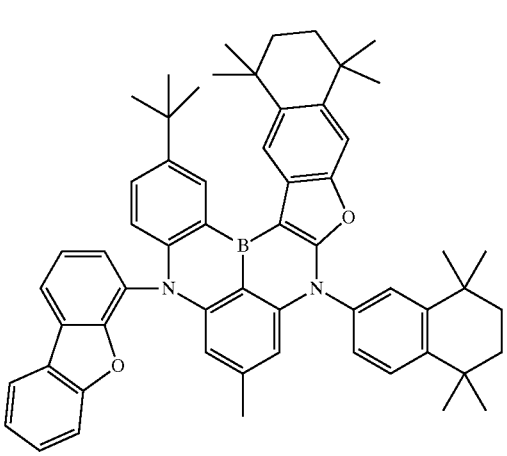
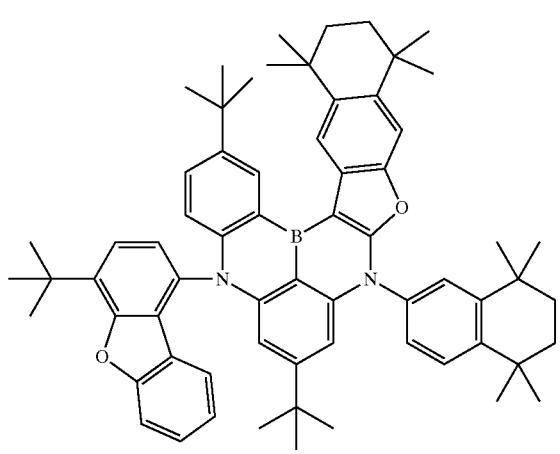
1404
-continued
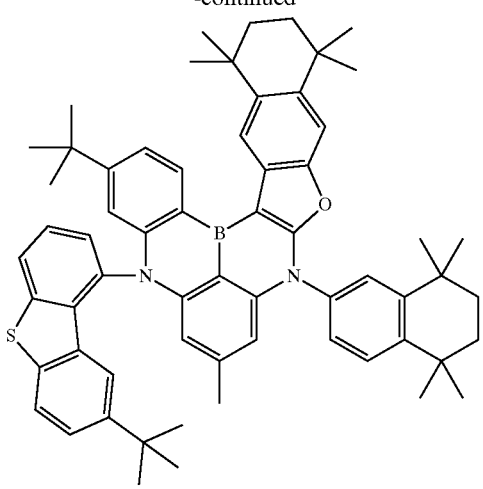
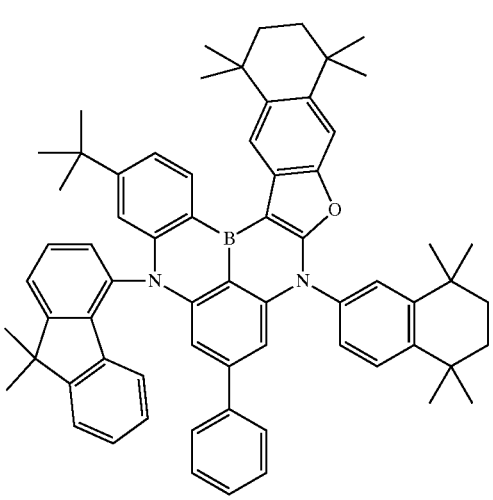
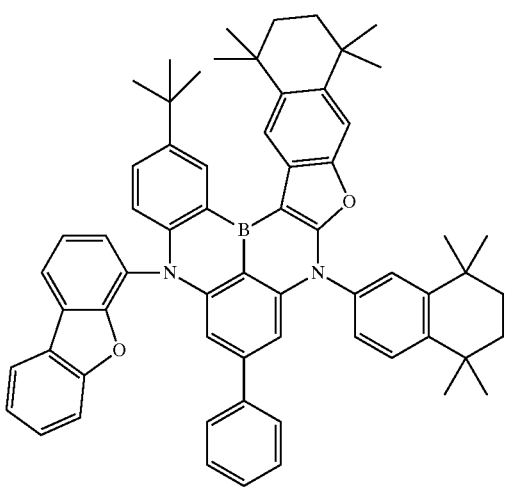

US 11,780,856 B2
1405
-continued
1406
-continued
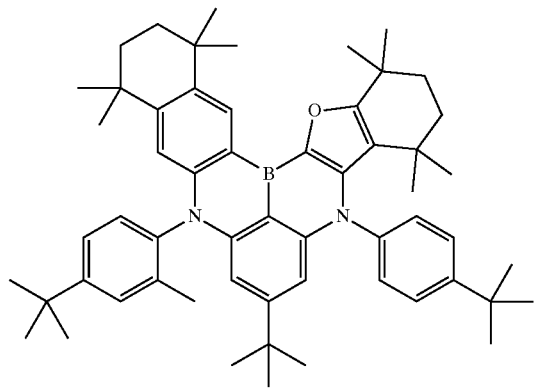
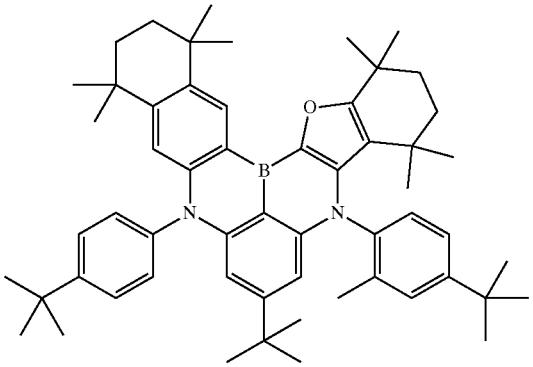
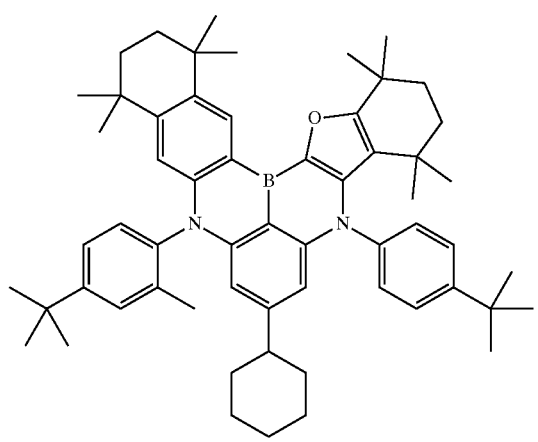
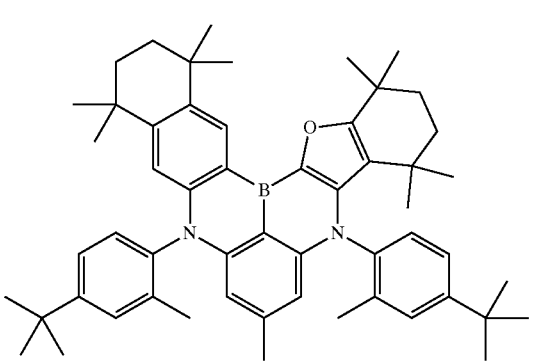
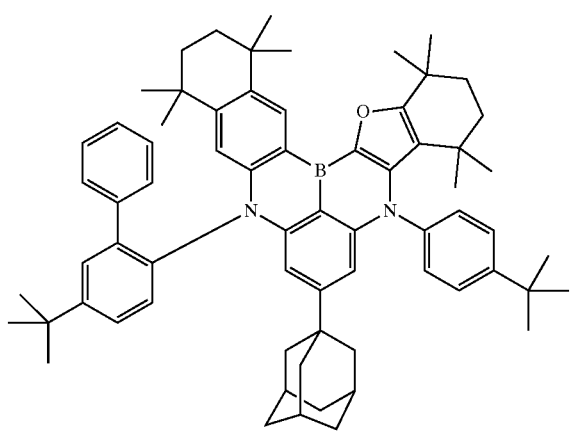
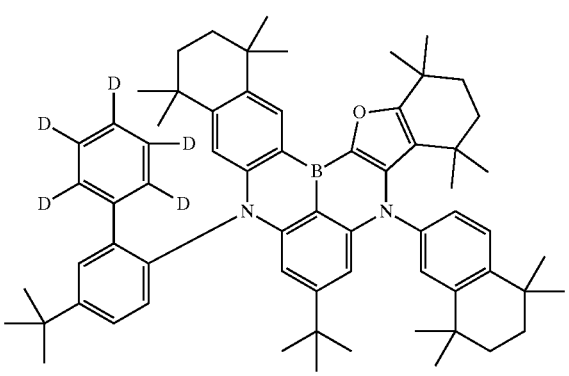
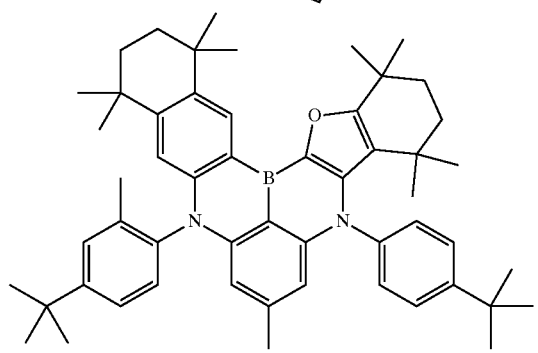
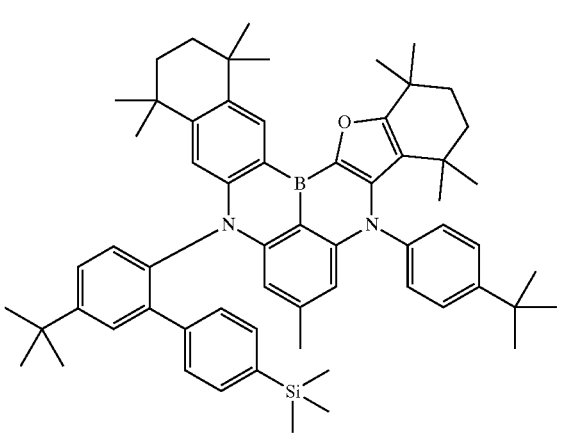

1407
-continued
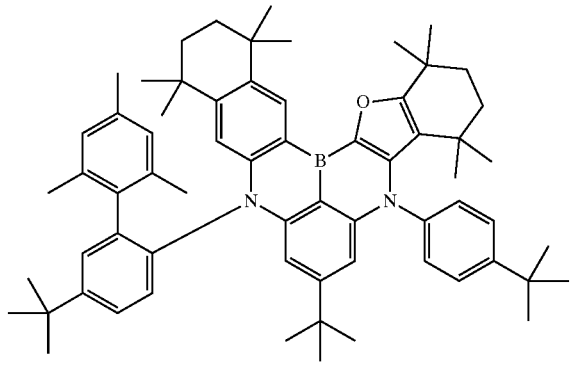
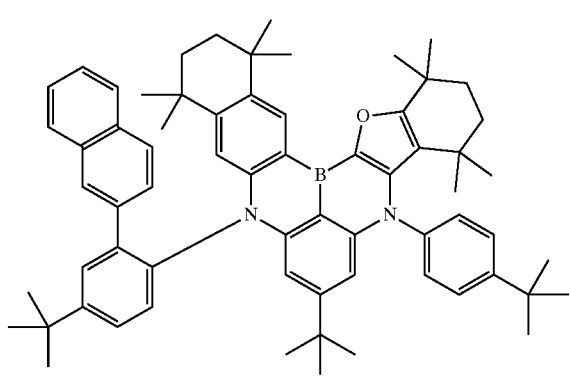
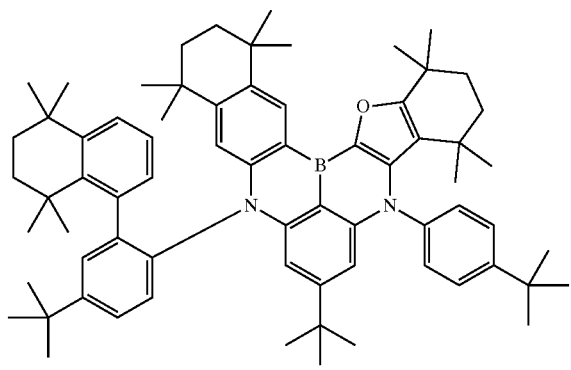
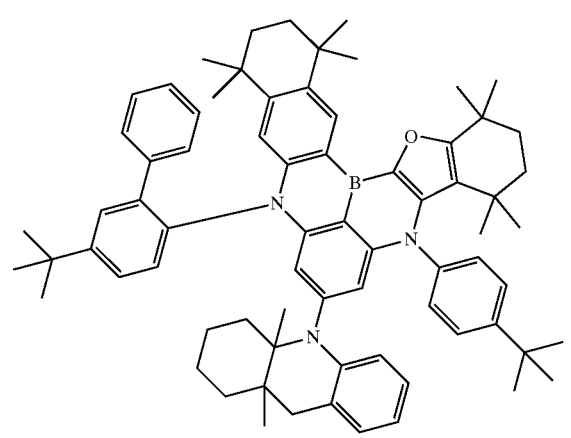
1408
-continued
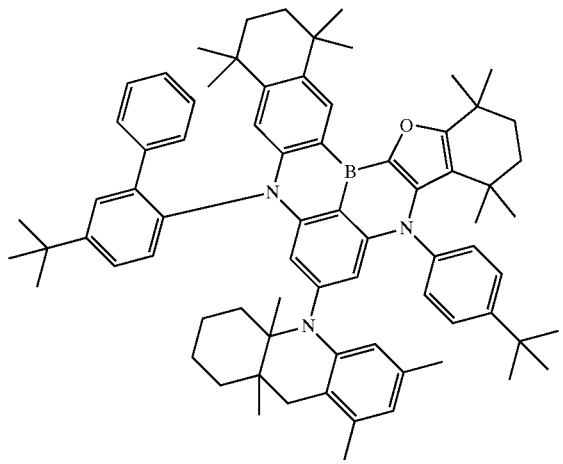
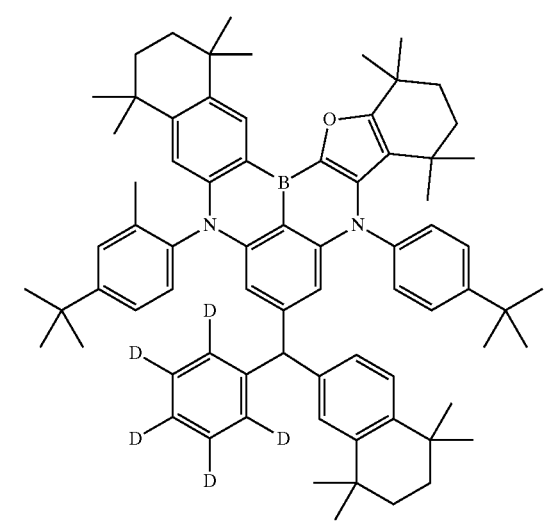
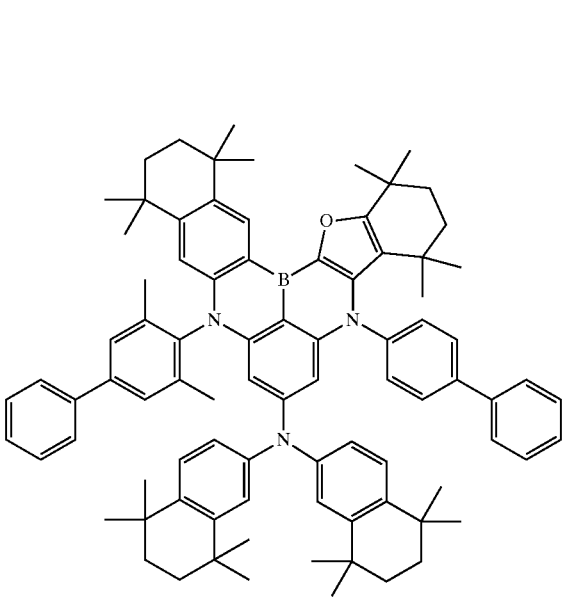

1409
-continued
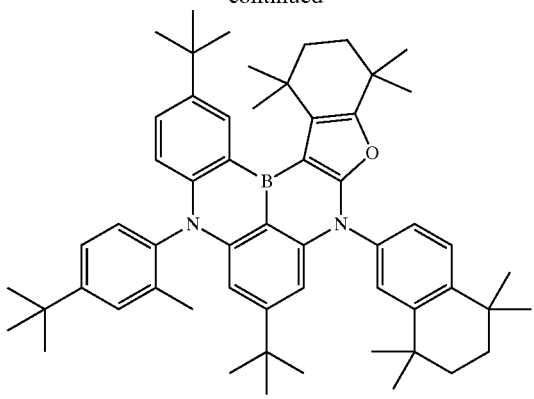
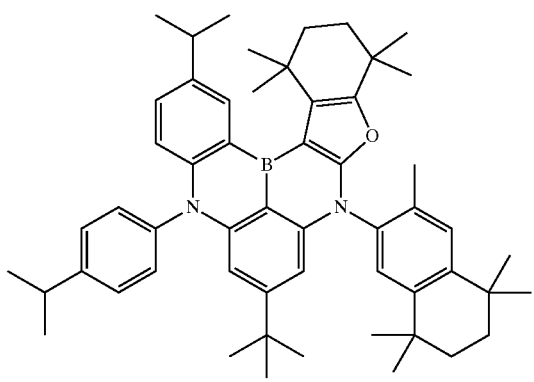
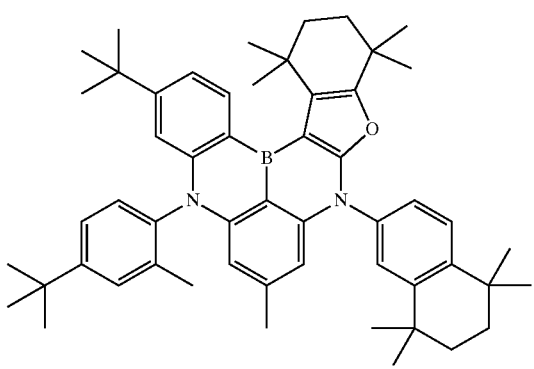
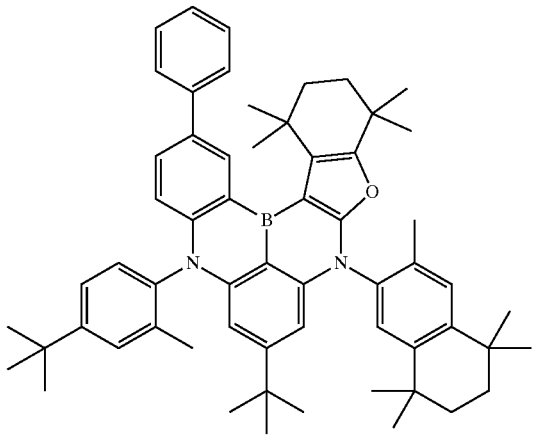
1410
-continued
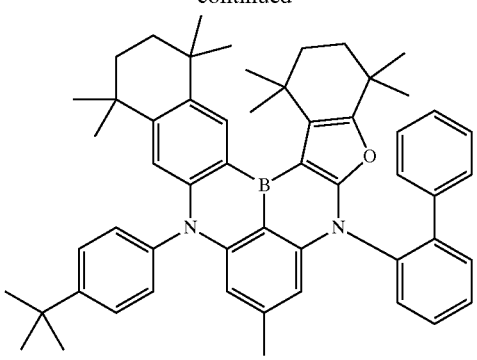
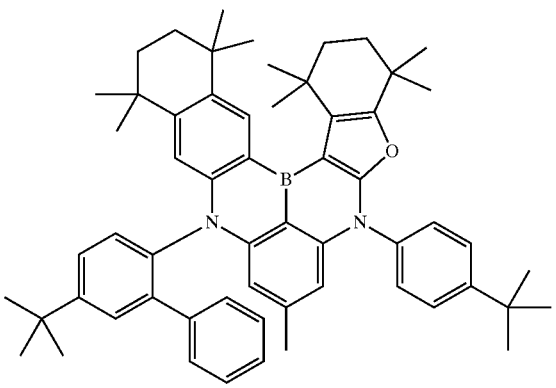
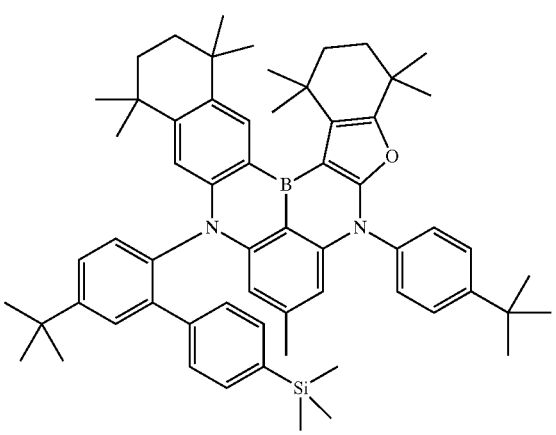
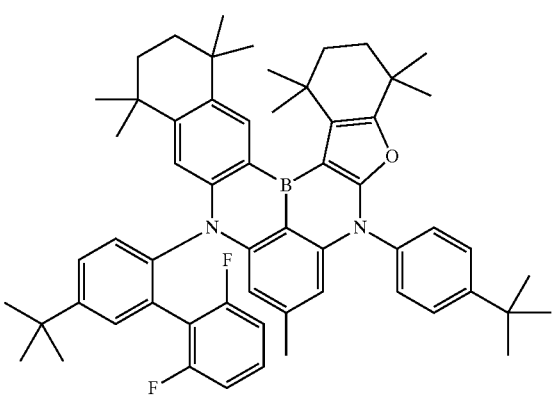

| 1411 -continued | 1412 -continued |
|---|---|
| 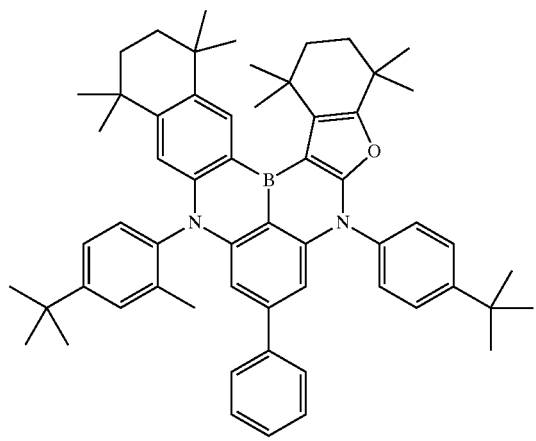 | 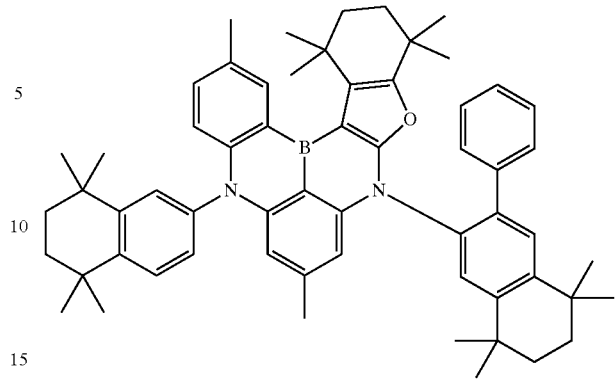 |
| 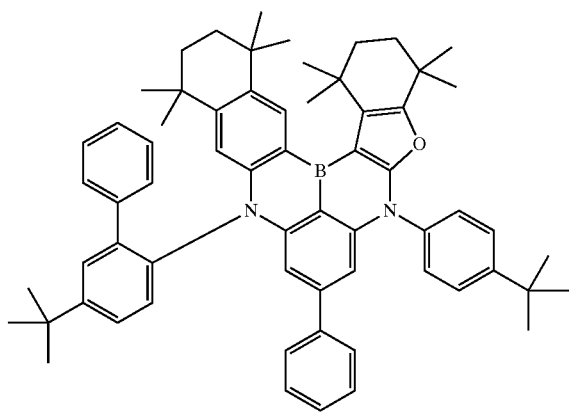 | 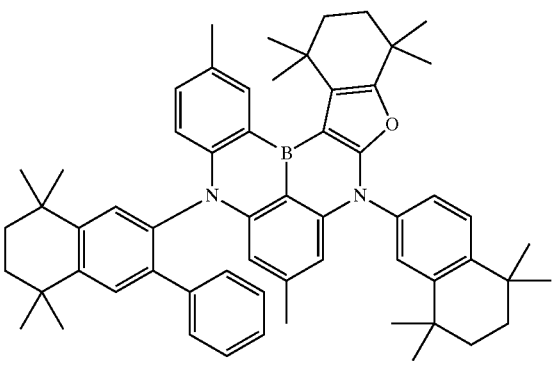 |
| 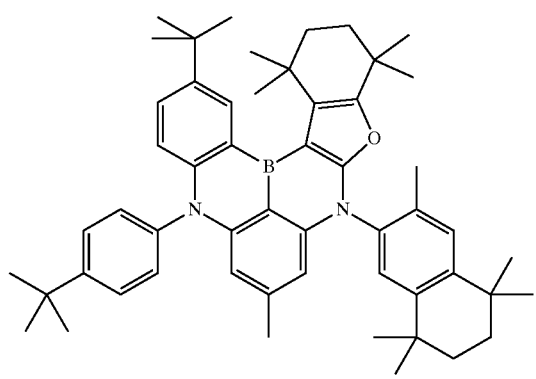 | 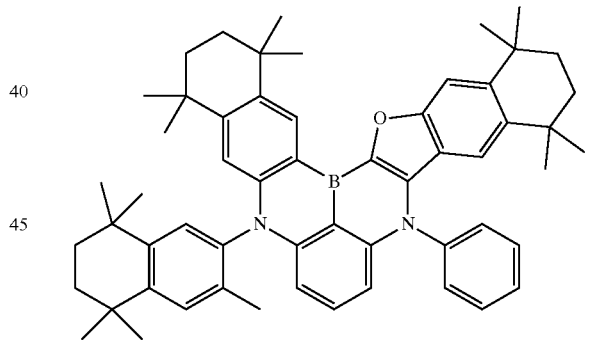 |
| 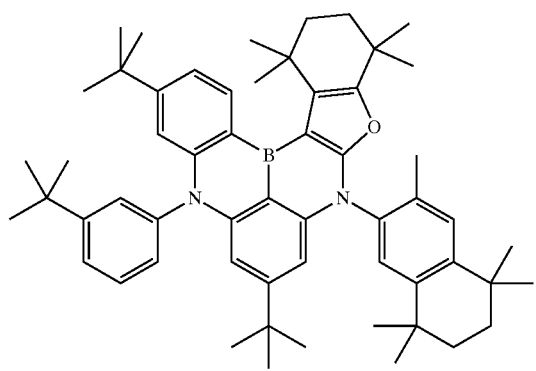 | 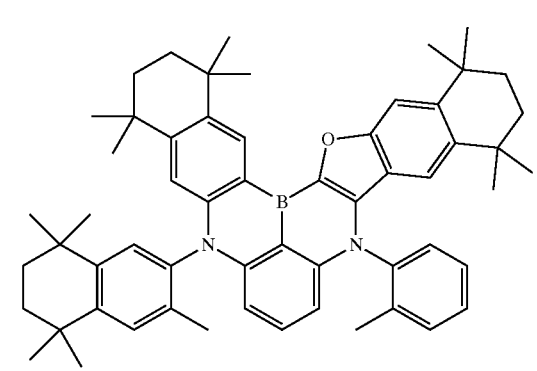 |

1413
-continued
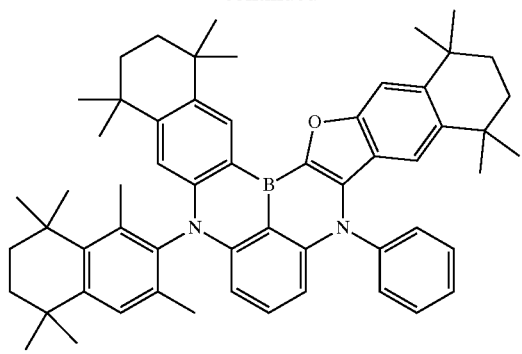
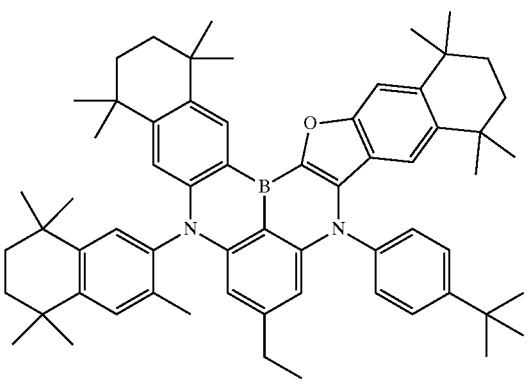
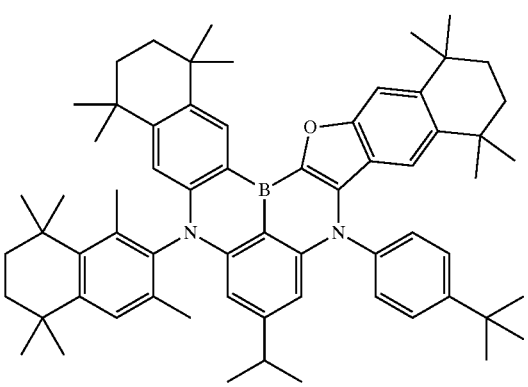
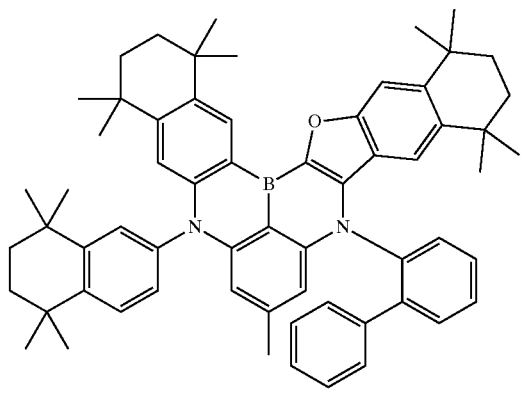
1414
-continued
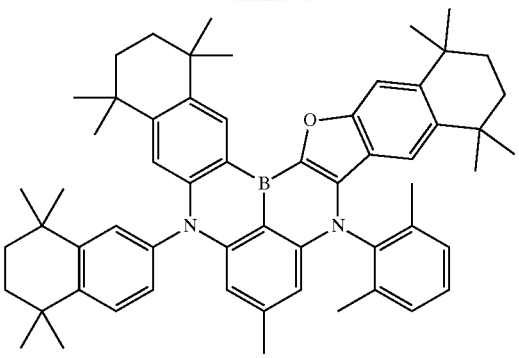
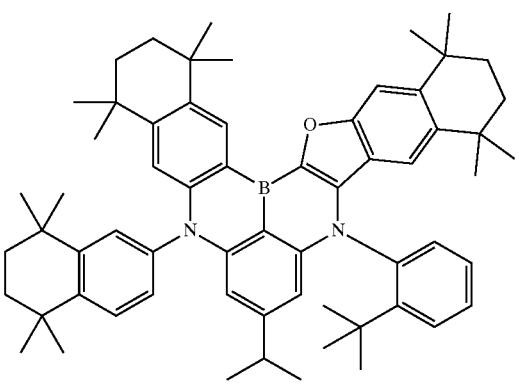
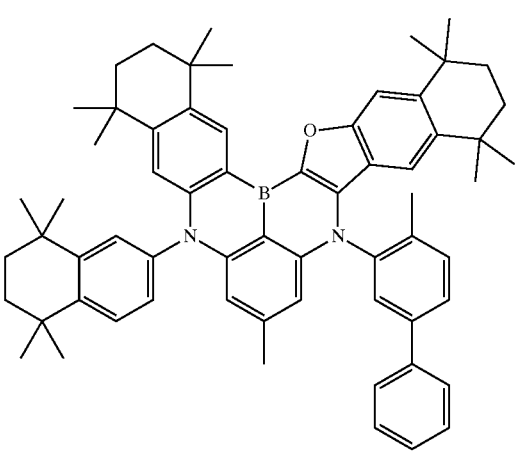
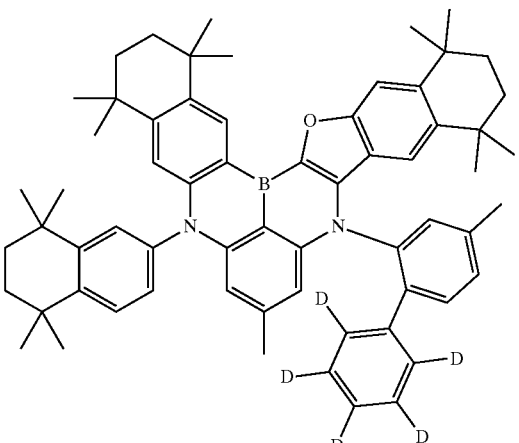

1415
-continued
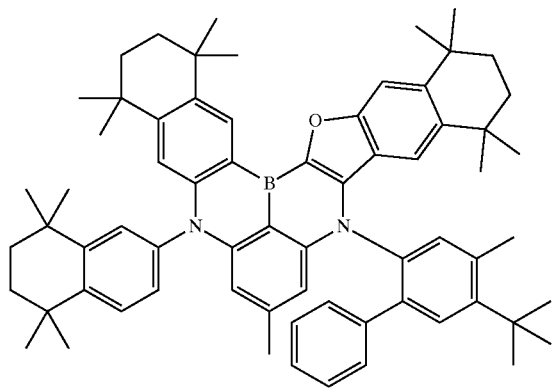
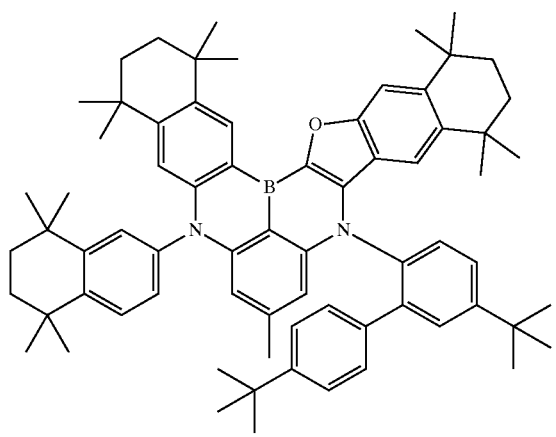
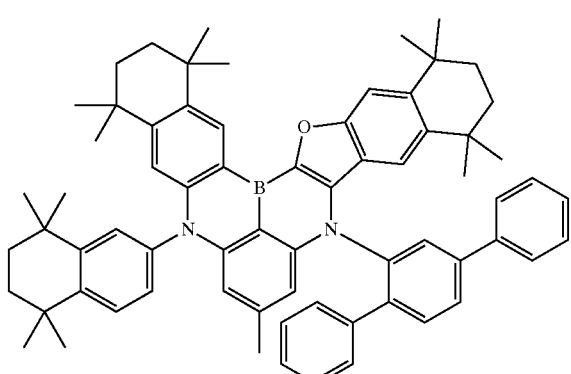
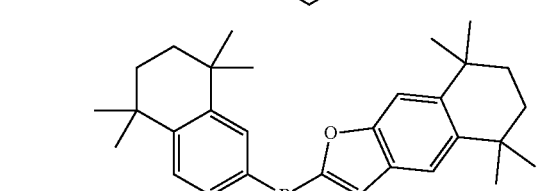
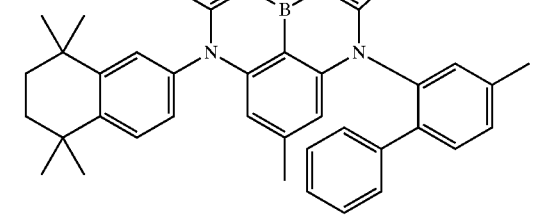
1416
-continued
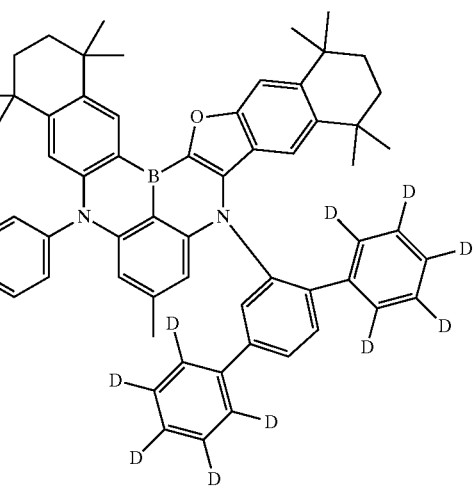
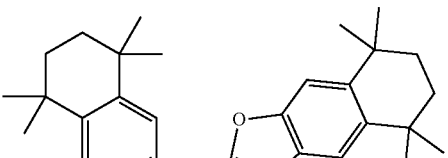
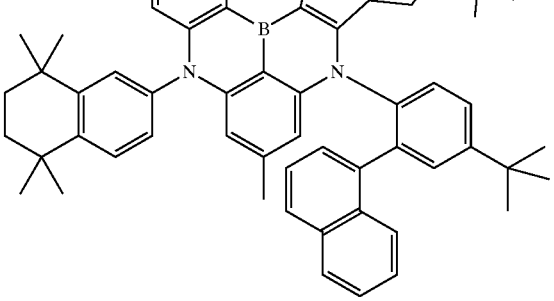
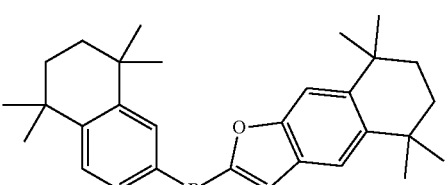
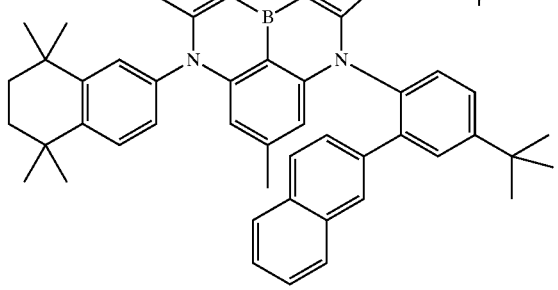

1417
-continued
1418
-continued
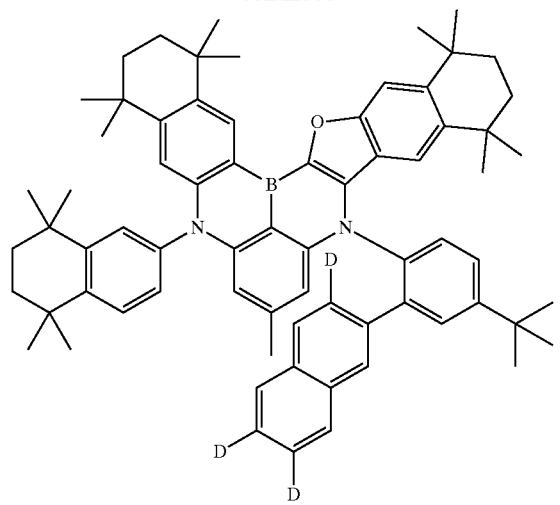
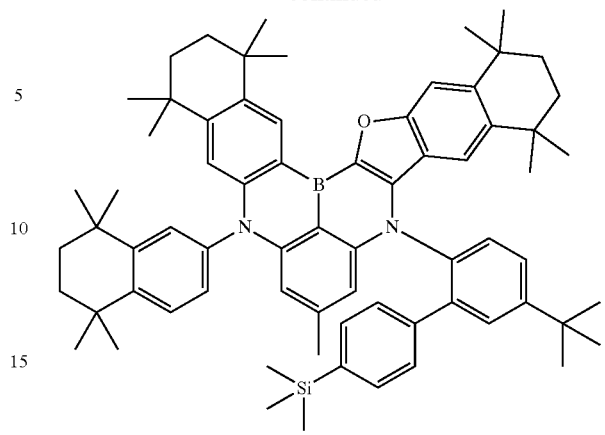
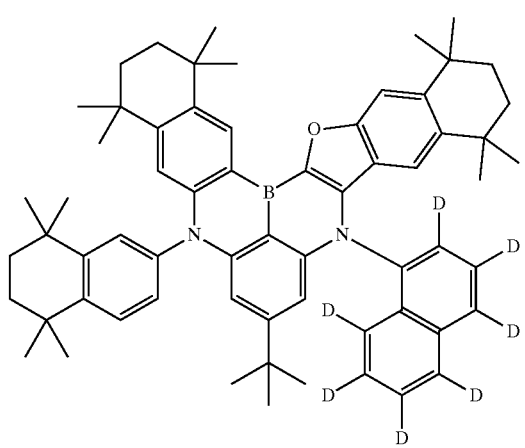
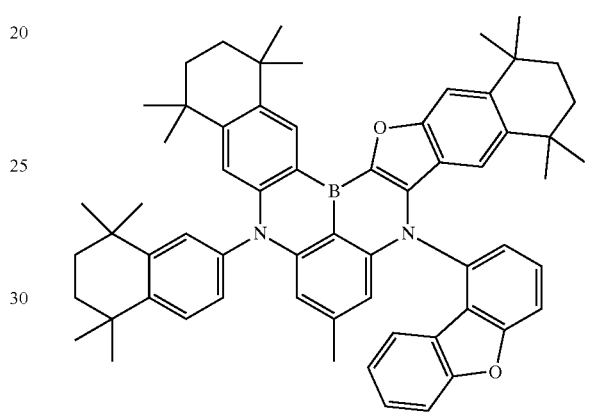
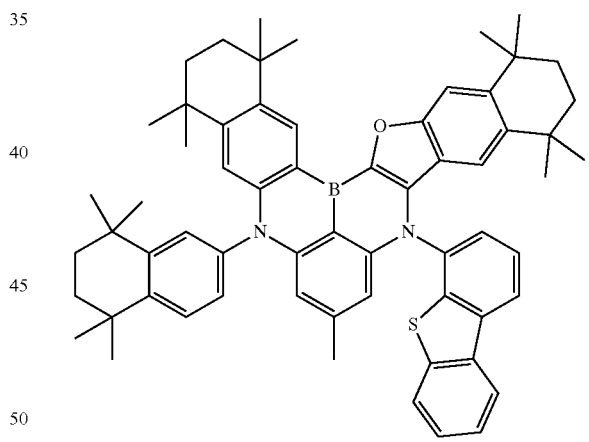
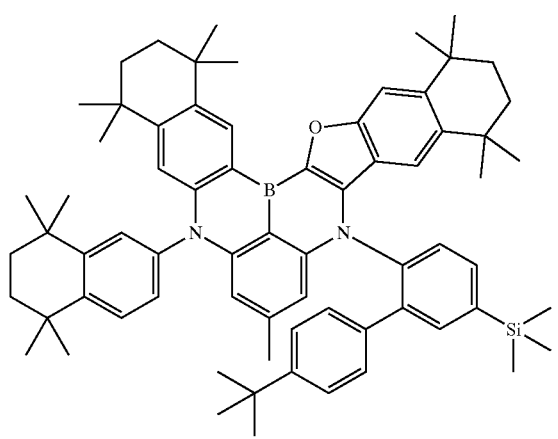
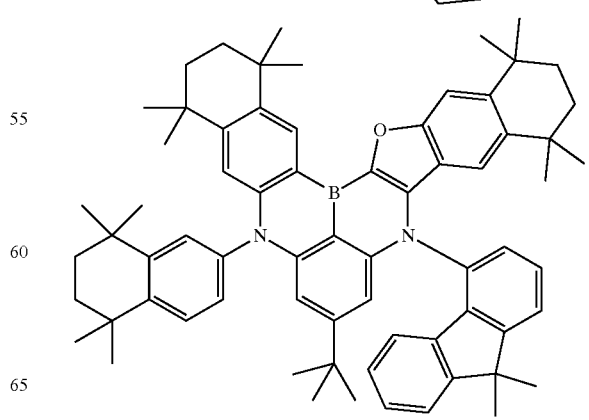

1419
-continued
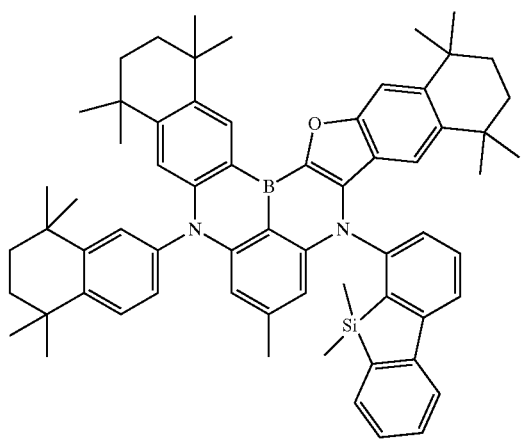
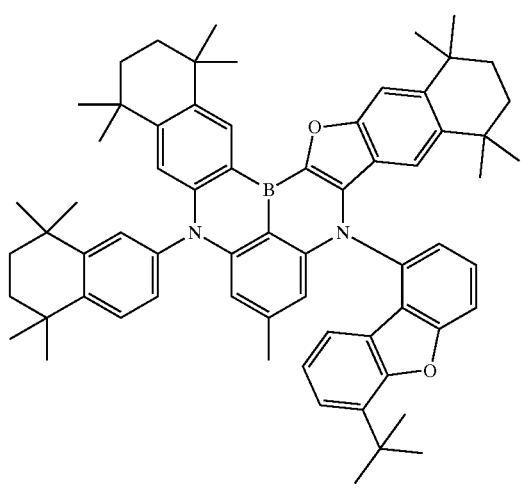
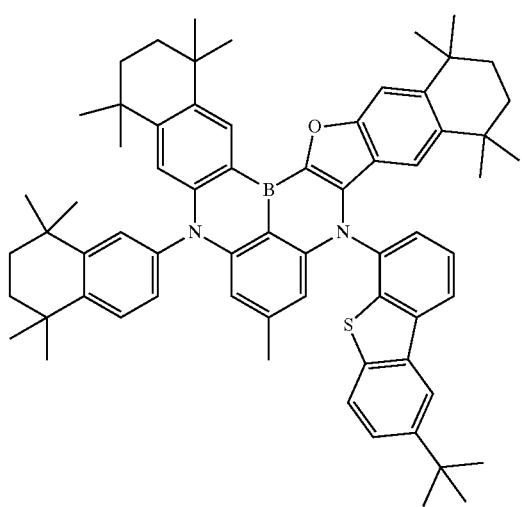
1420
-continued
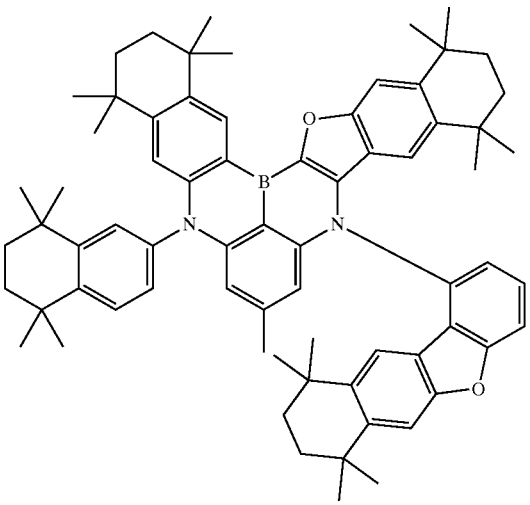
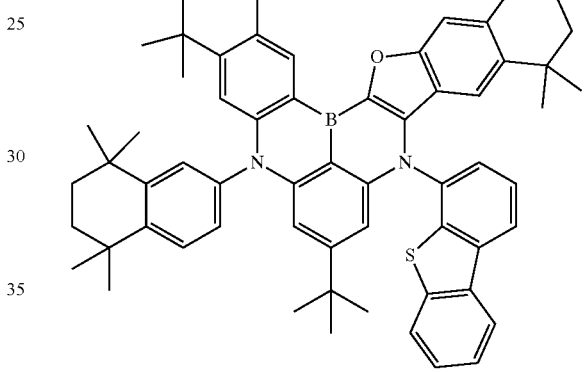
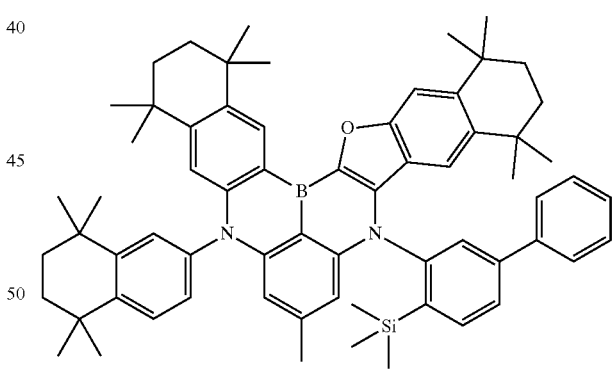
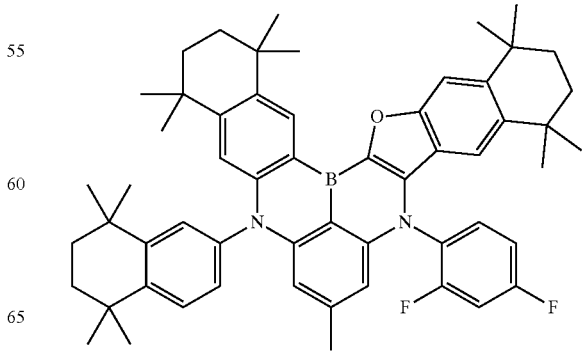

1421
-continued
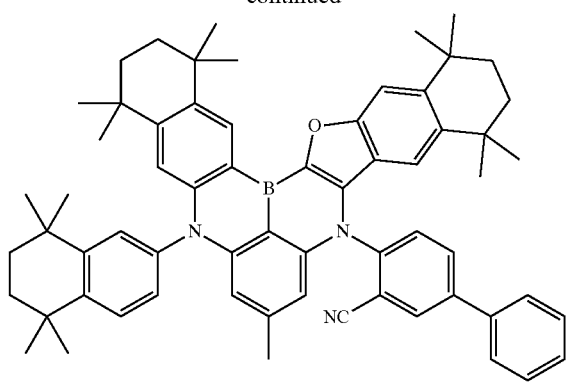
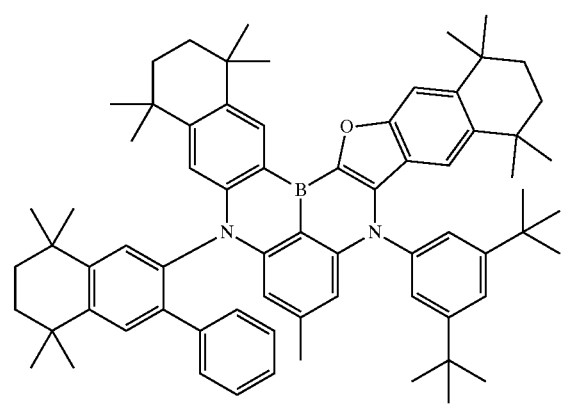
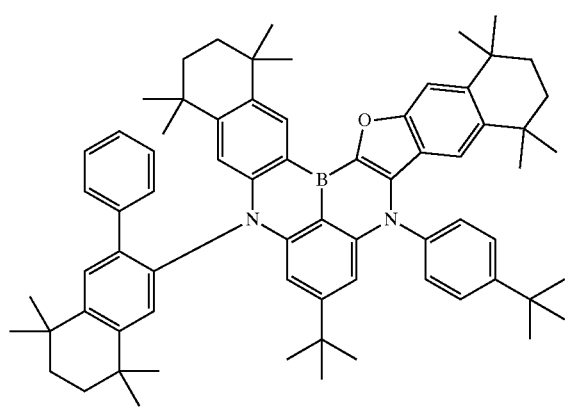
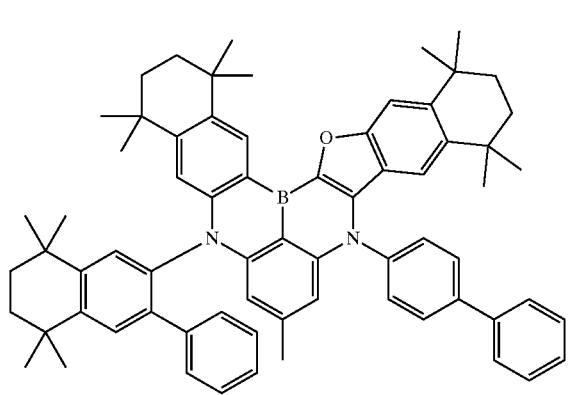
1422
-continued
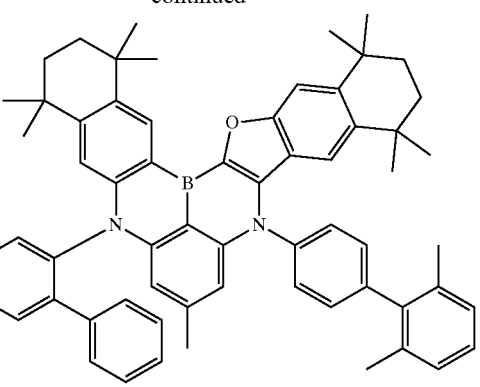
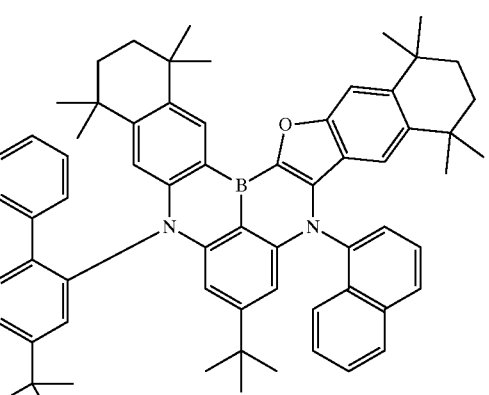
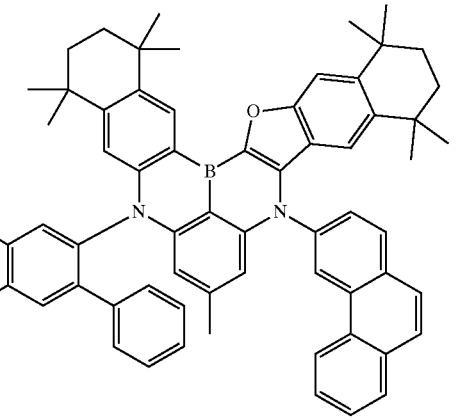
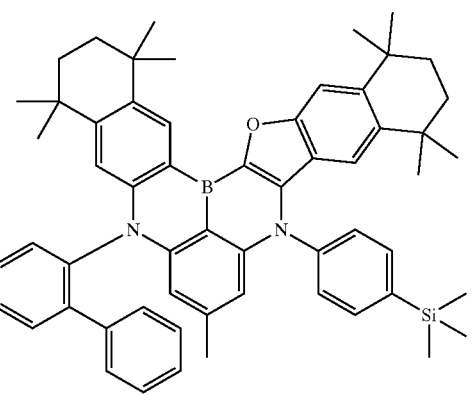

| 1423 -continued | 1424 -continued |
|---|---|
| 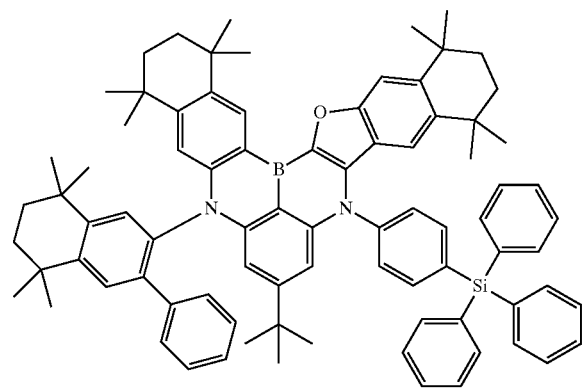 | 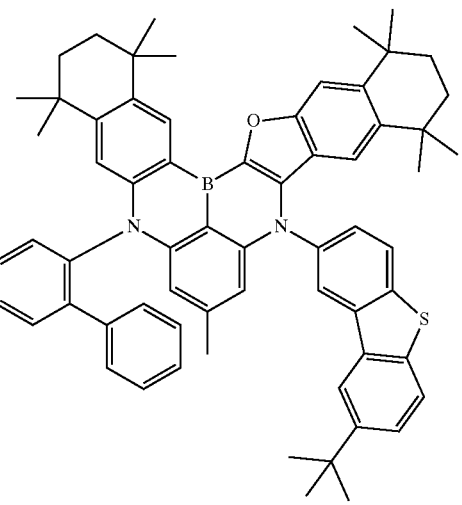 |
| 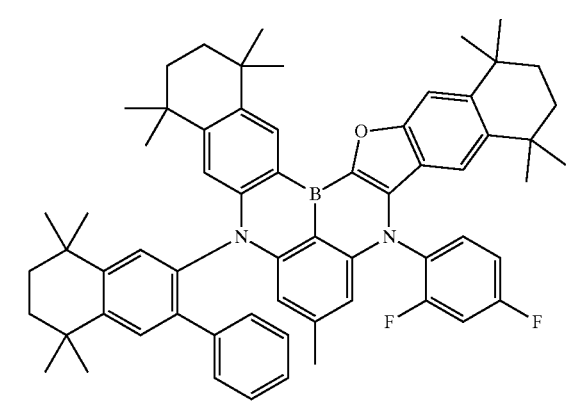 | 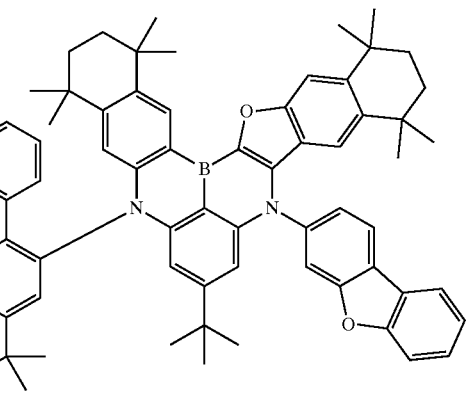 |
| 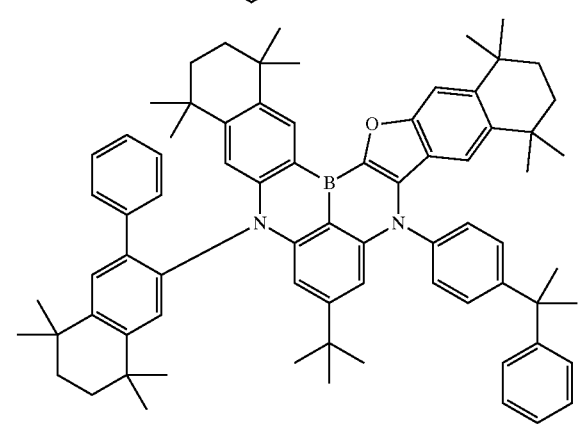 | 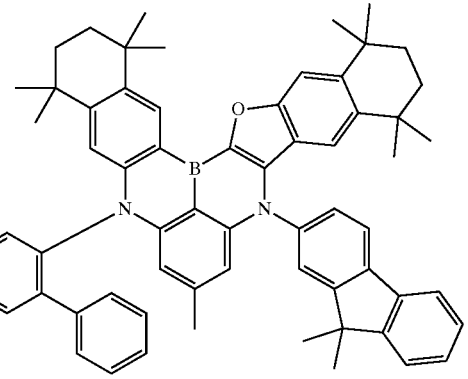 |
| 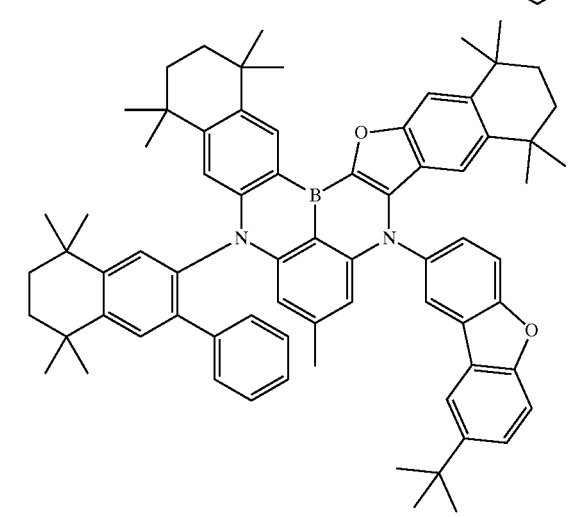 | 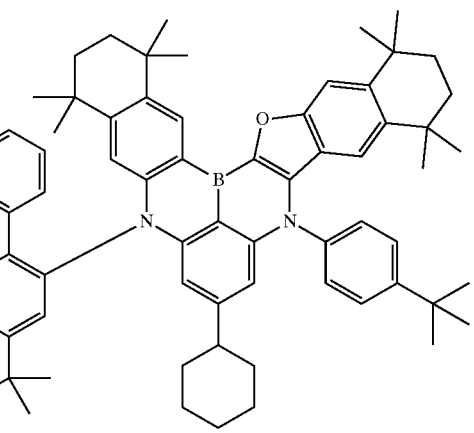 |

1425
-continued
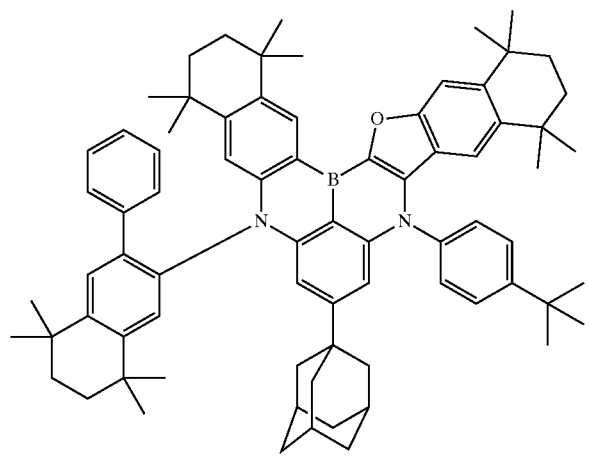
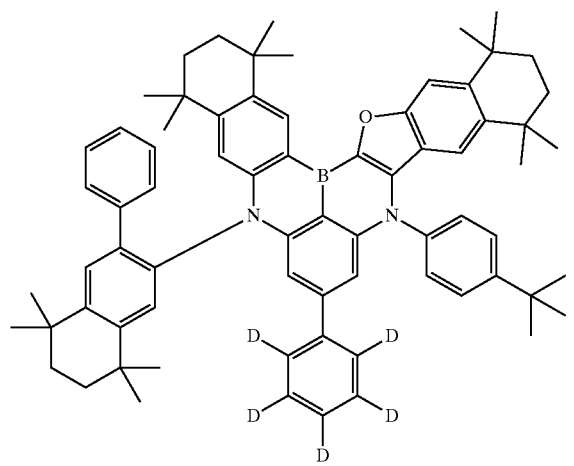
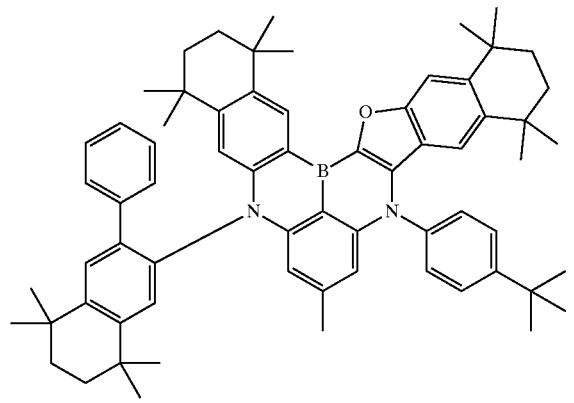
1426
-continued
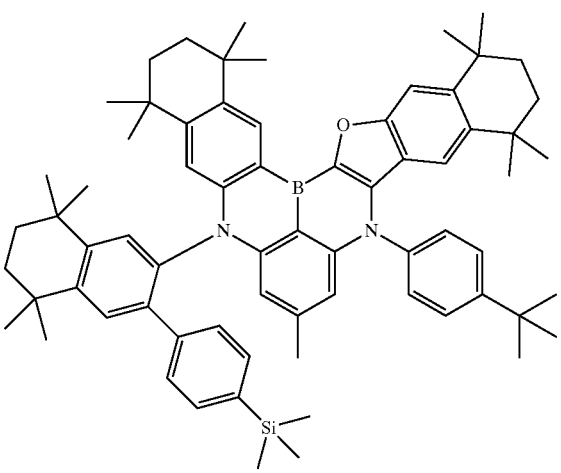
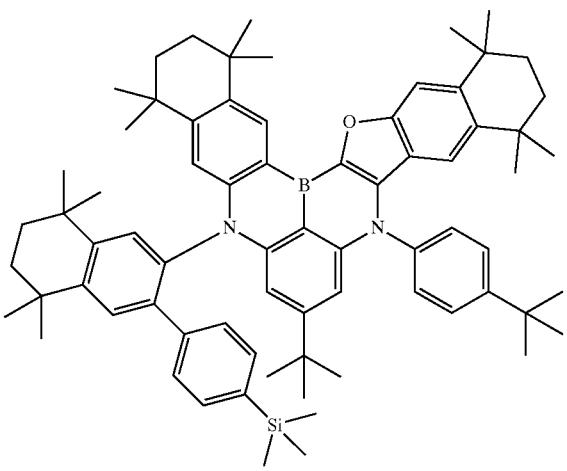
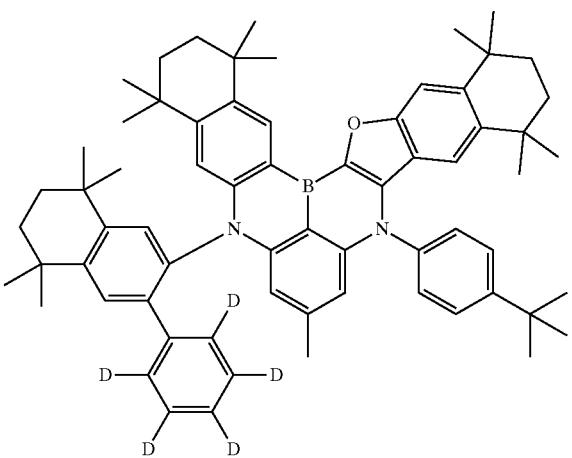

1427
-continued
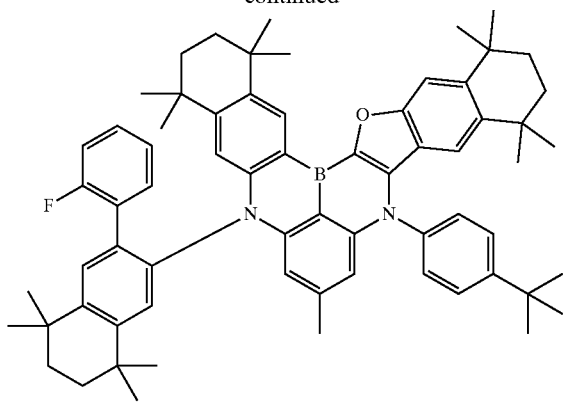
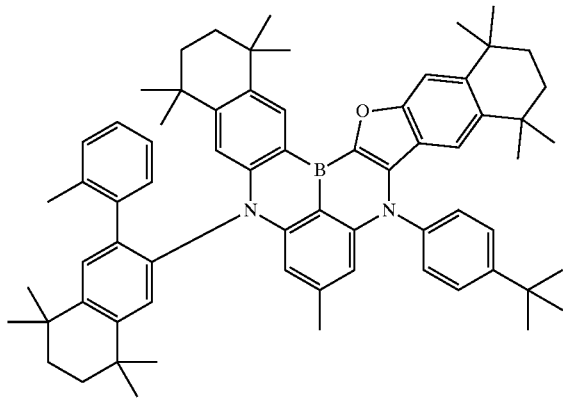
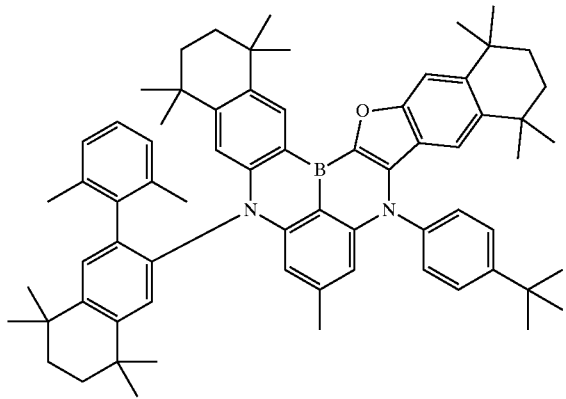
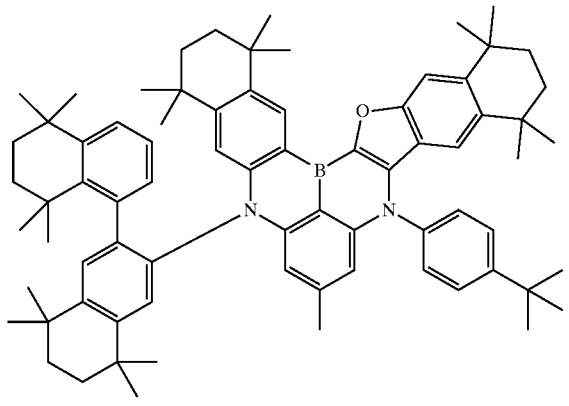
1428
-continued
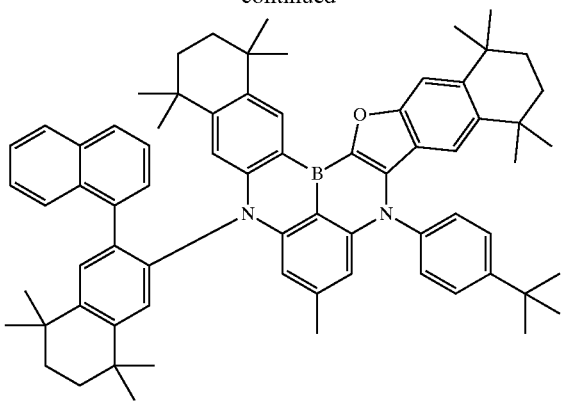
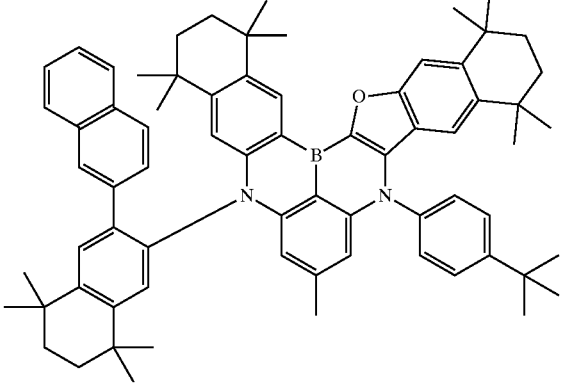
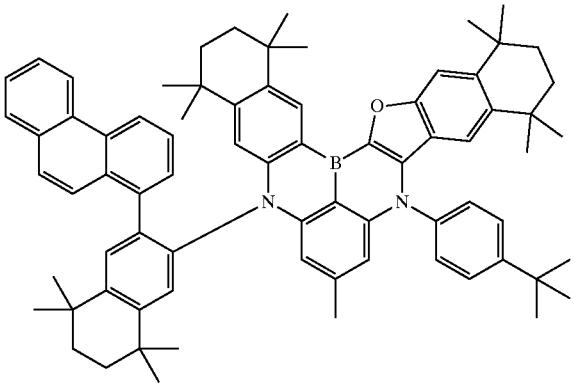
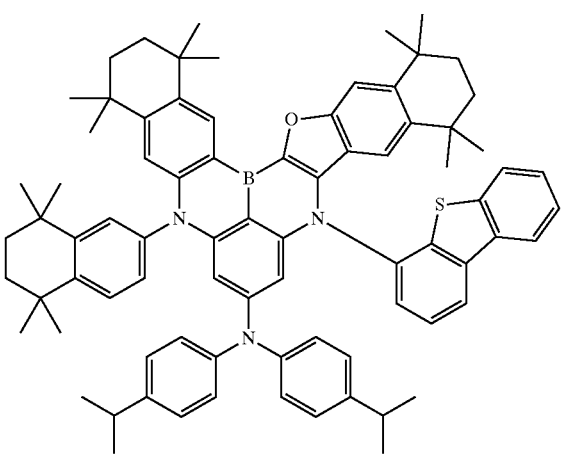

1429
-continued
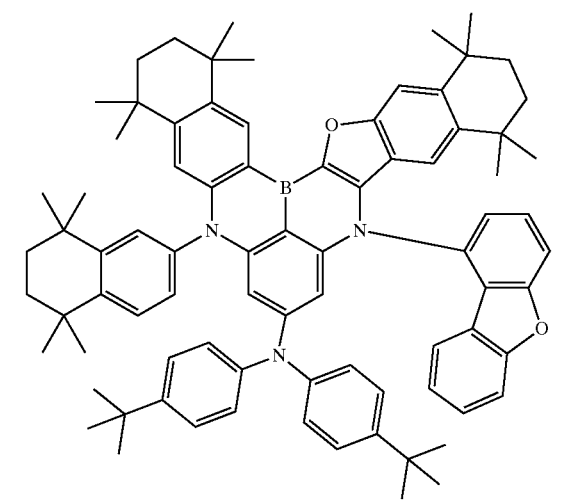
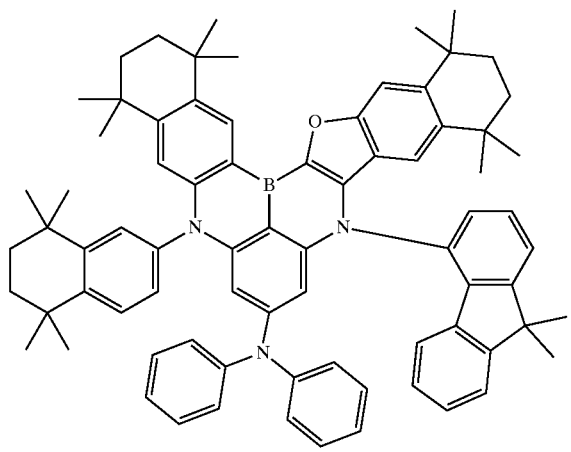
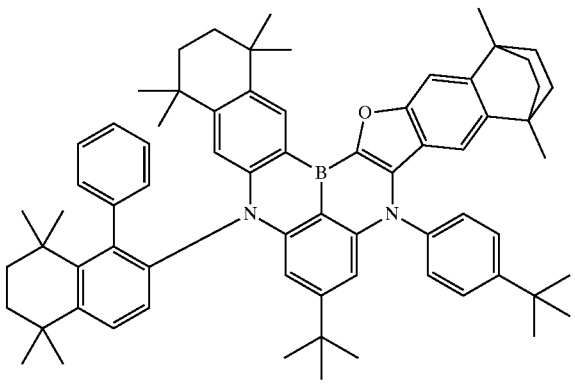
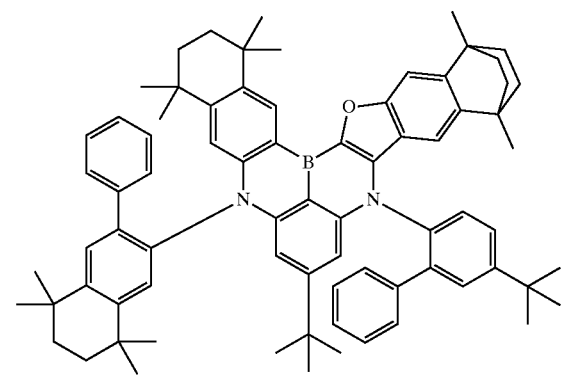
1430
-continued
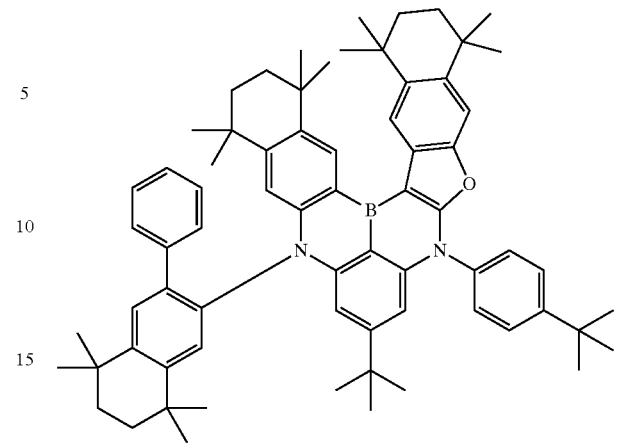
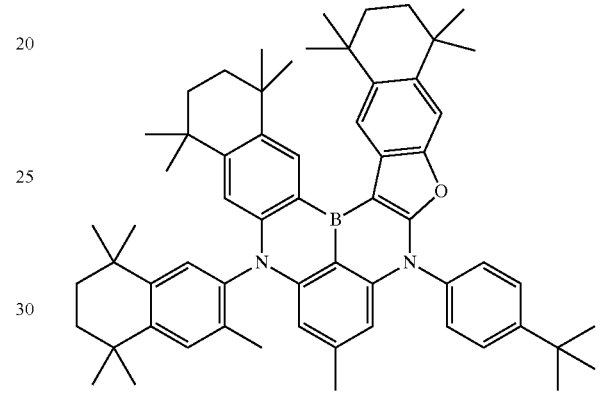
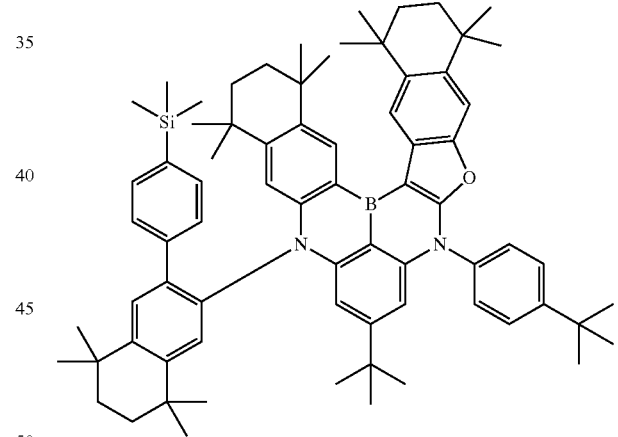
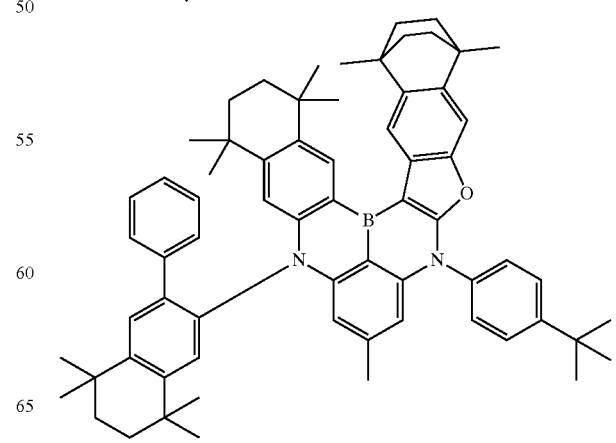

1431
-continued

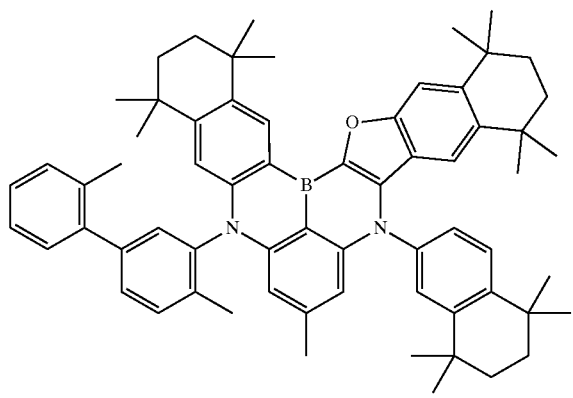
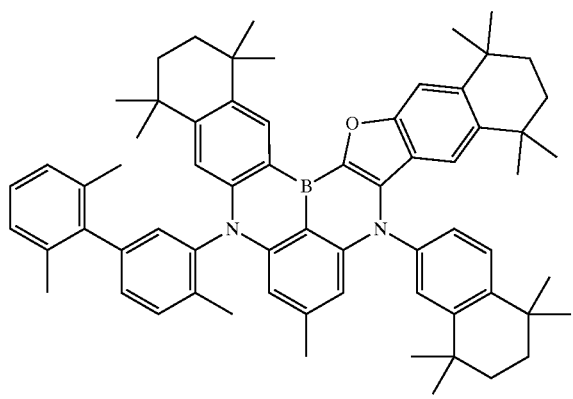
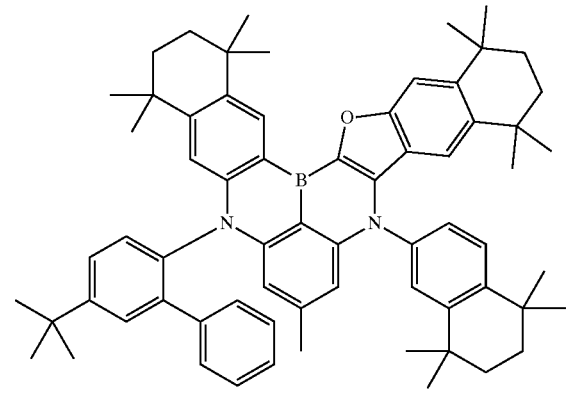
1432
-continued
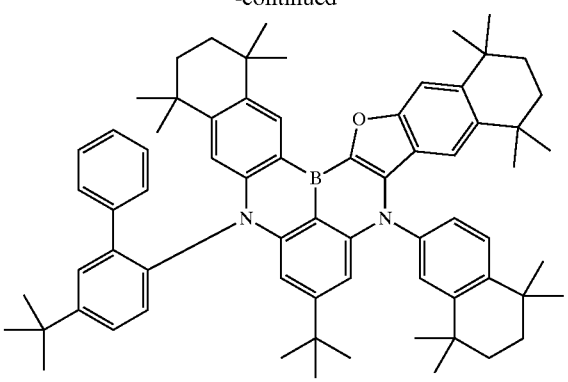
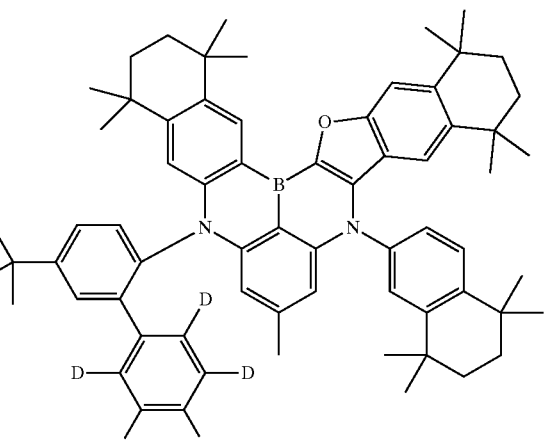
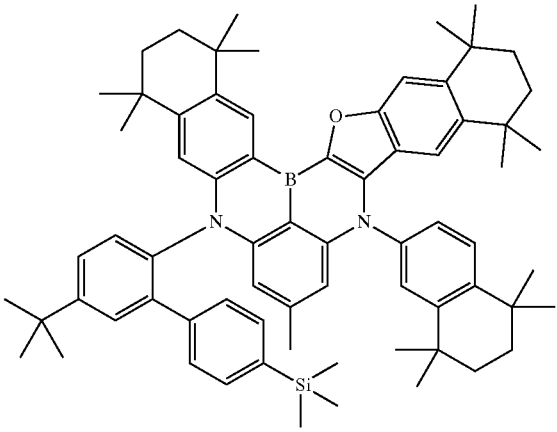
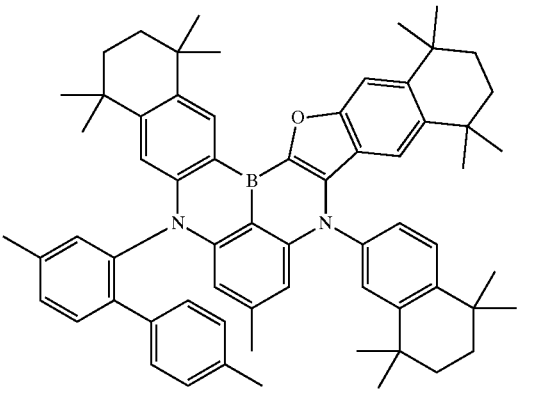

1433
-continued
1434
-continued
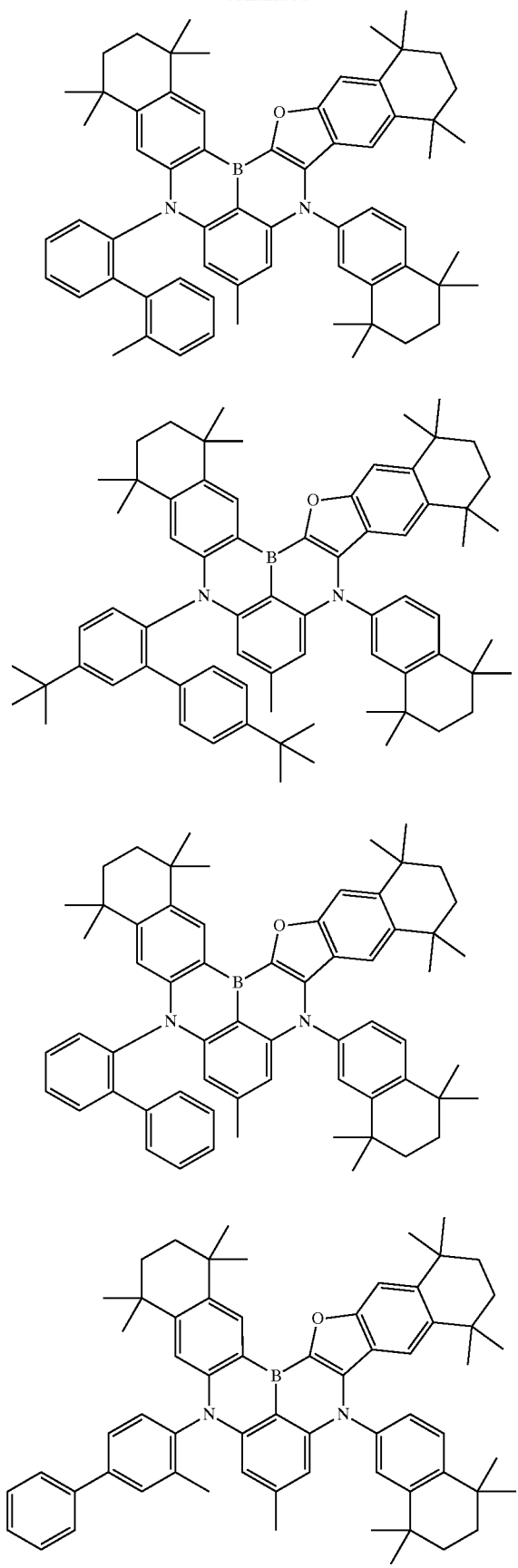
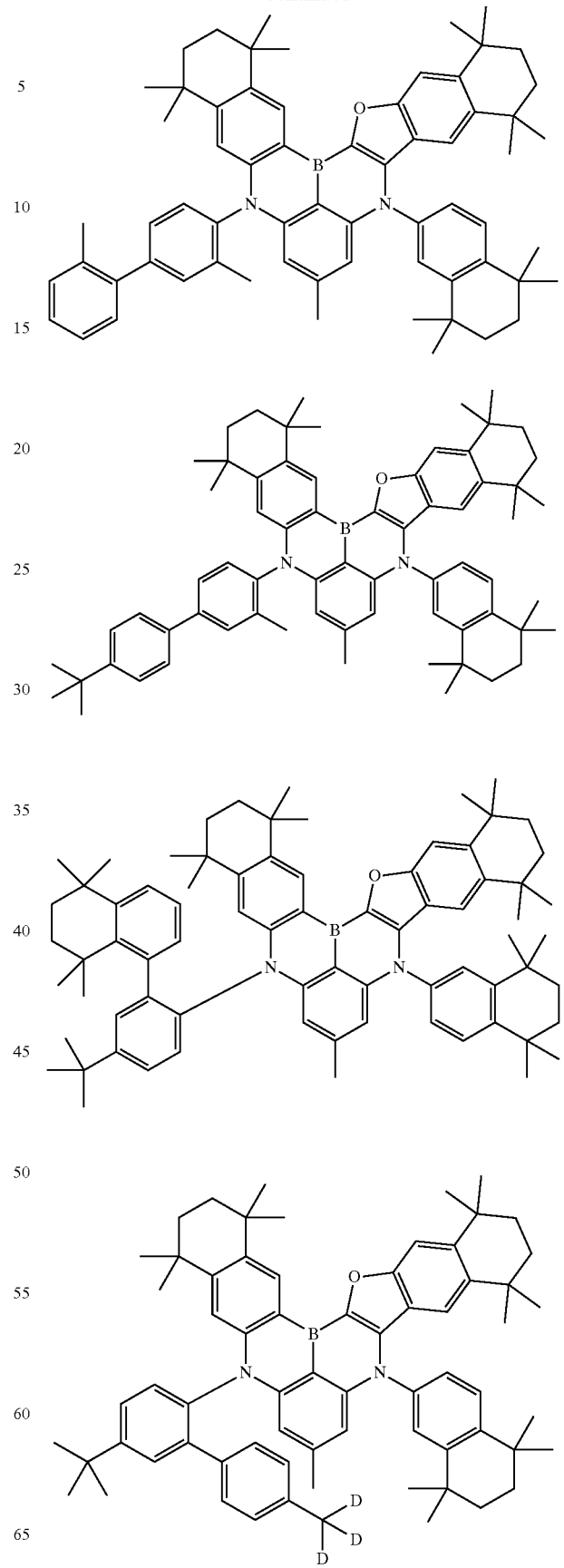

1435
-continued
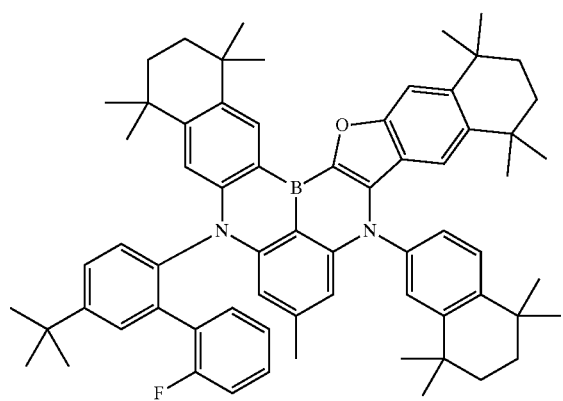
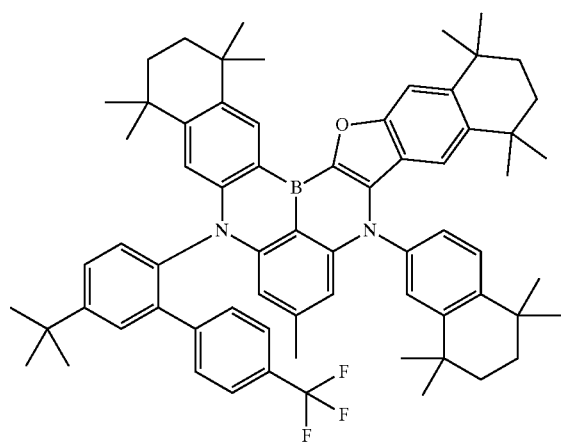
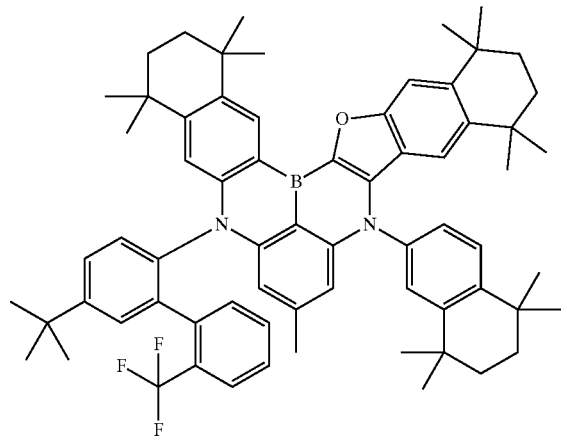
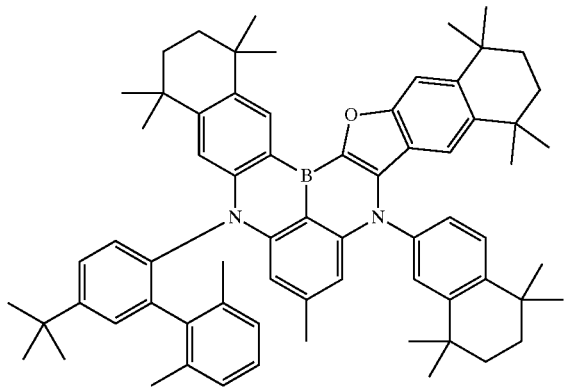
1436
-continued
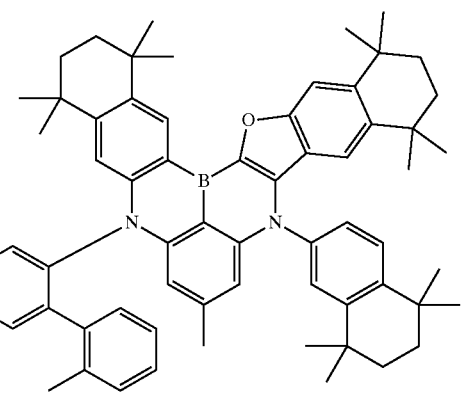
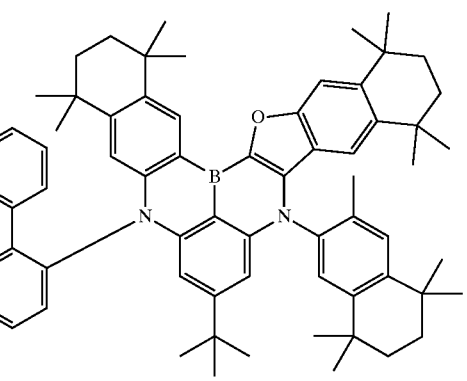
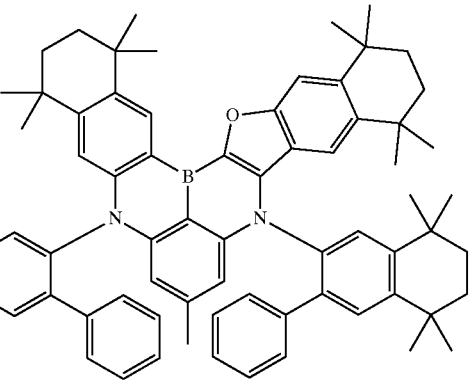
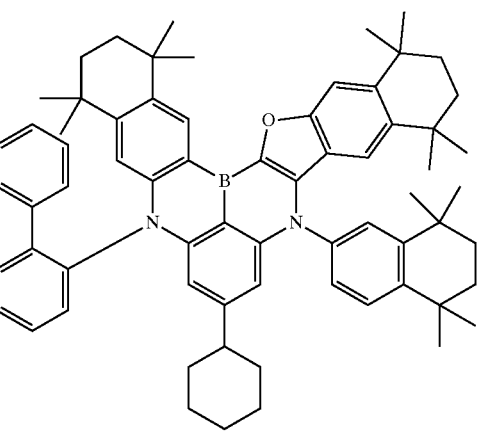

1437
-continued
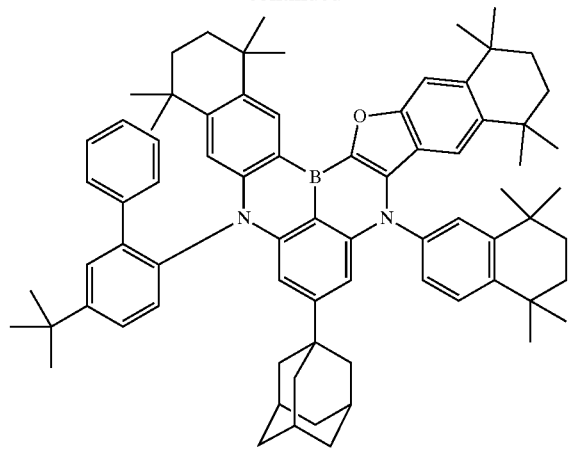
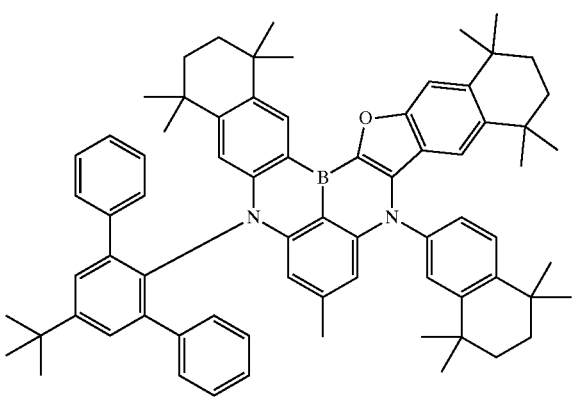
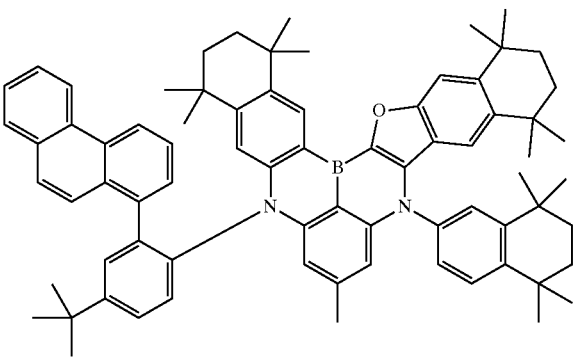
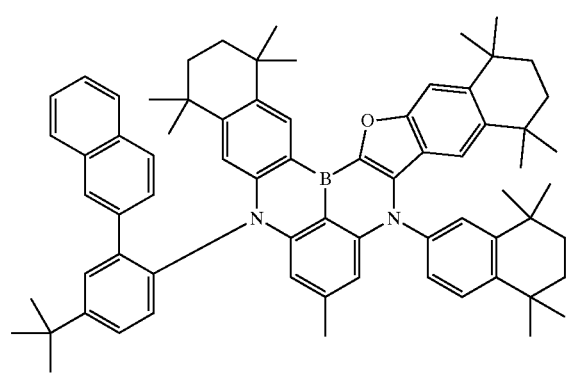
1438
-continued
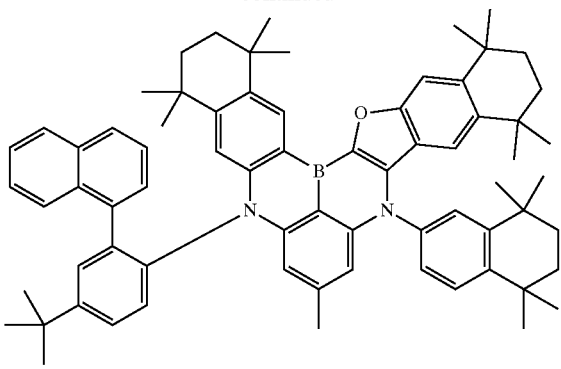
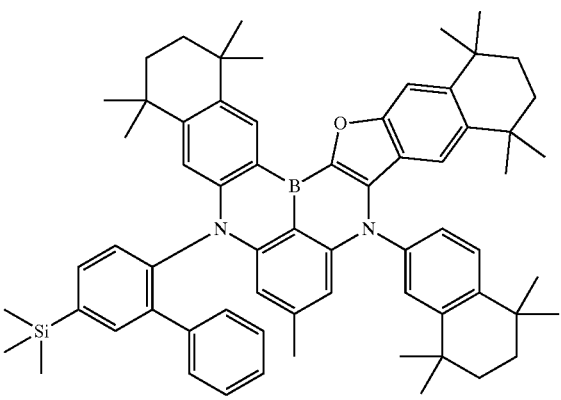
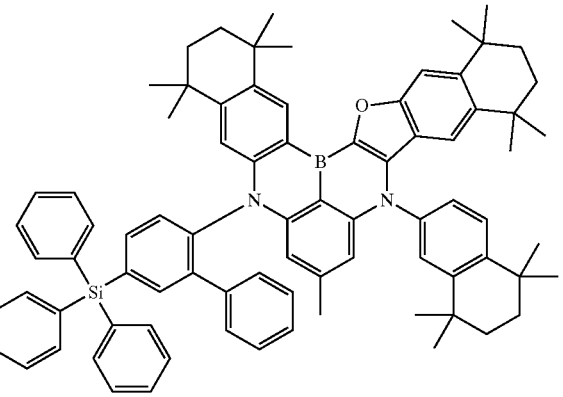
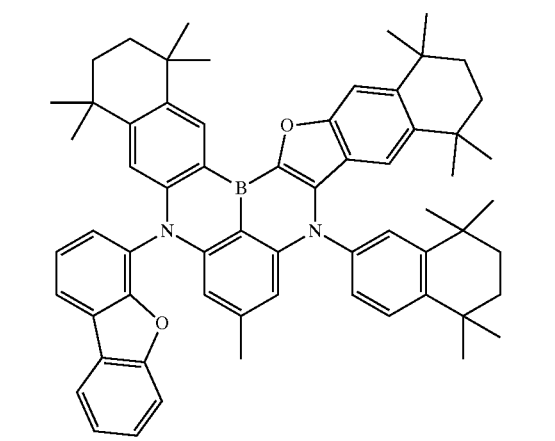

1439 -continued

1440 -continued

1441
-continued
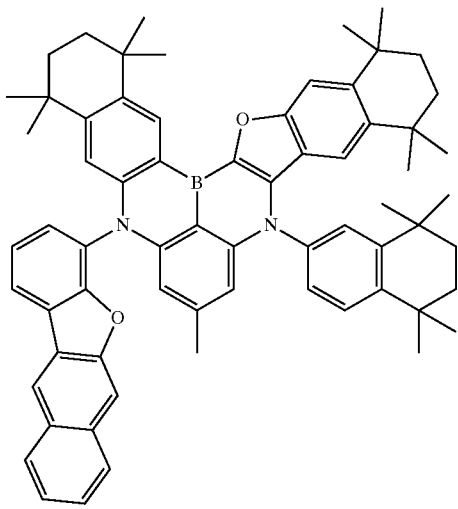
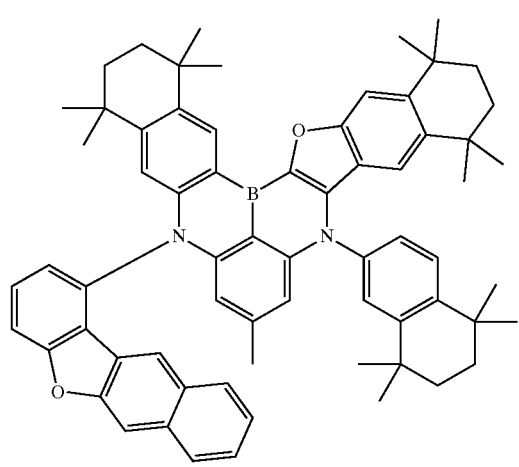
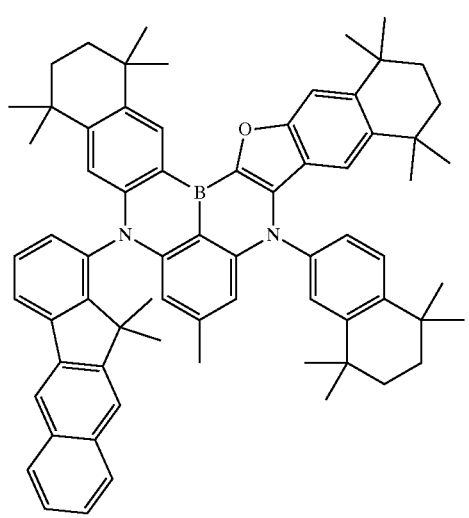
1442
-continued
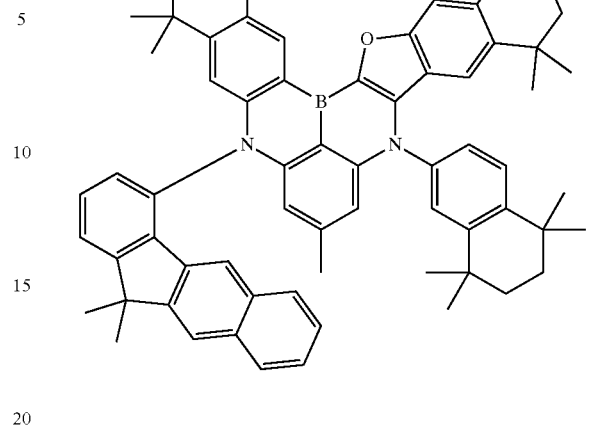
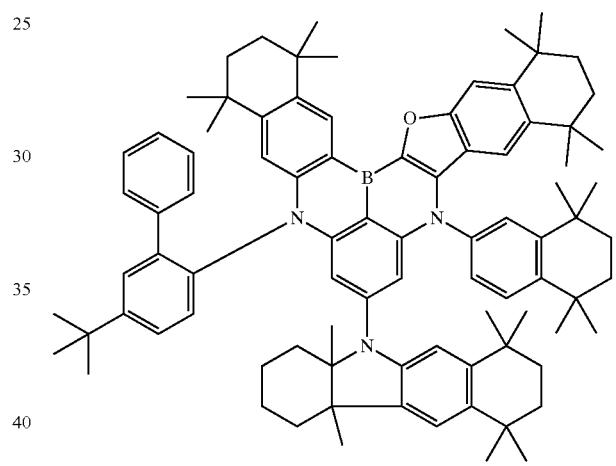
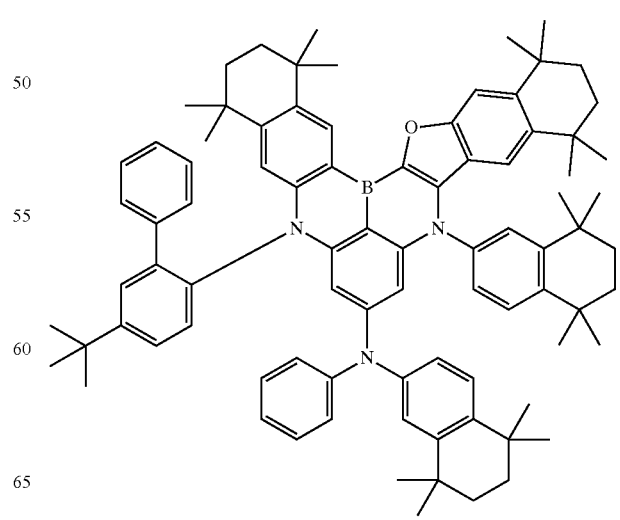

1443
-continued
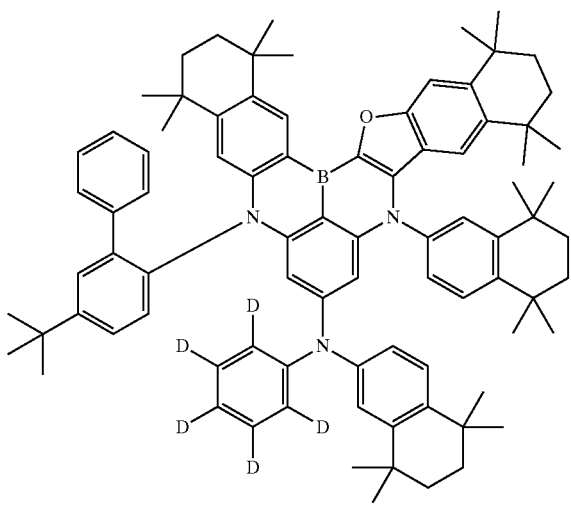
1444
-continued
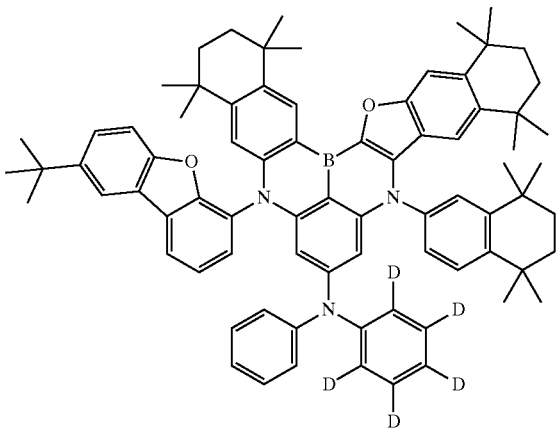
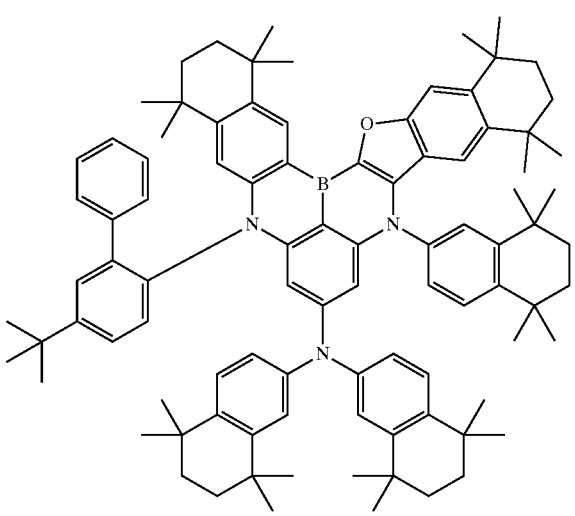
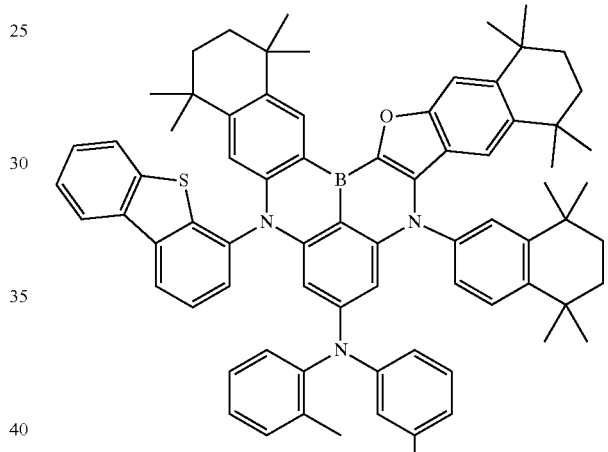
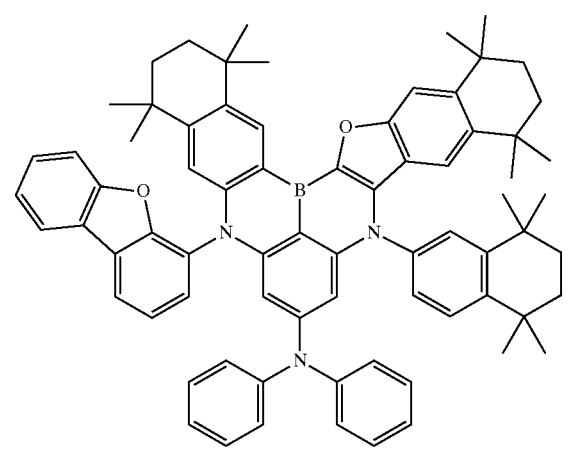
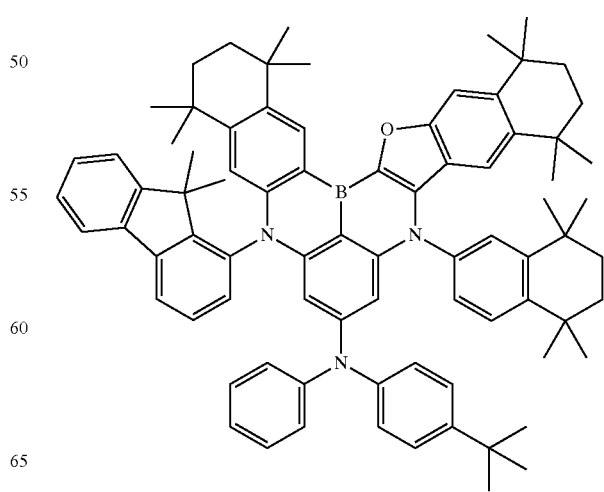

1445
-continued
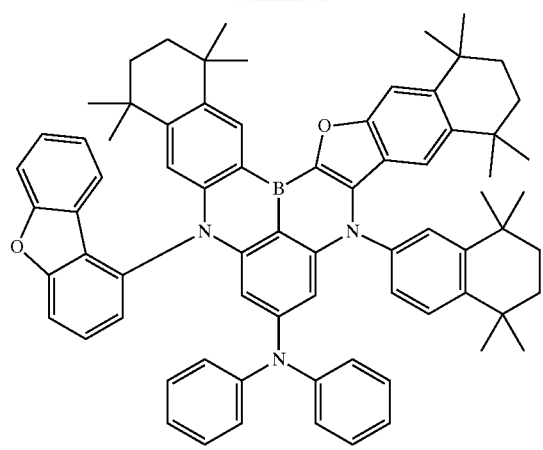
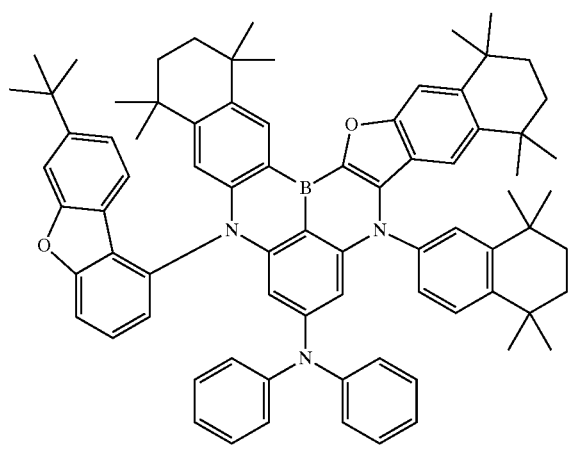
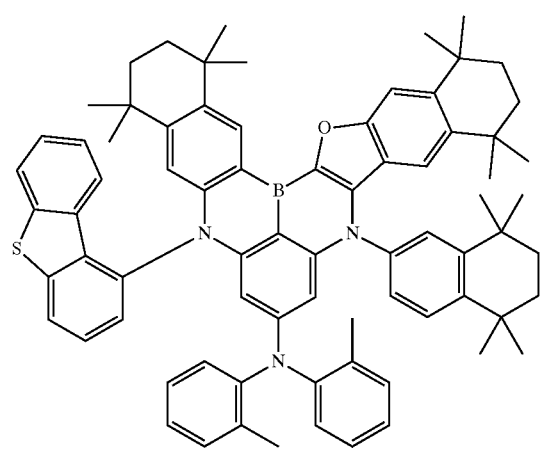
1446
-continued
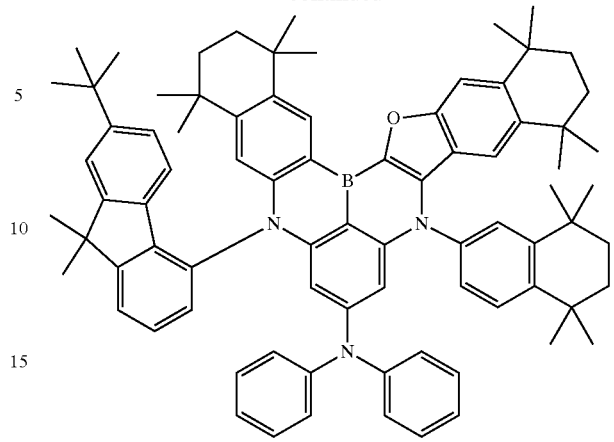
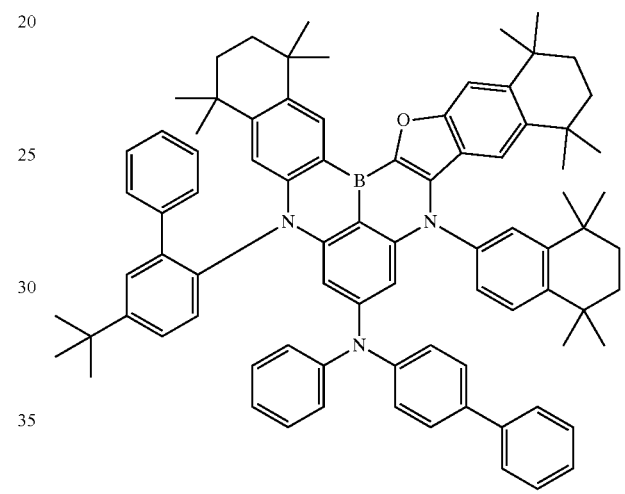
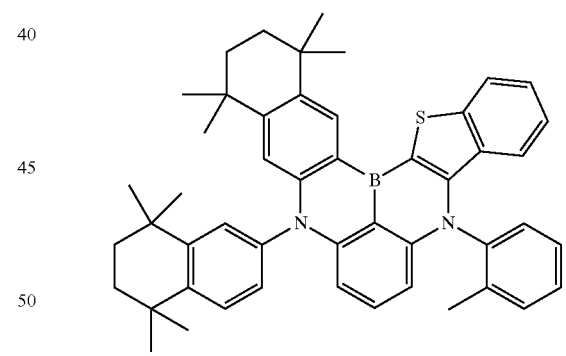
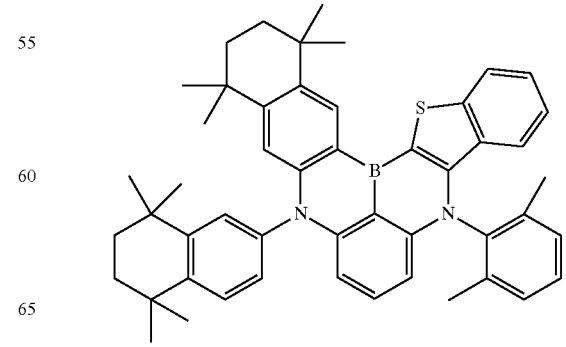

1447
-continued
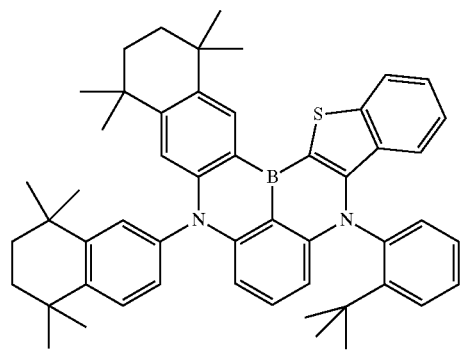
1448
-continued
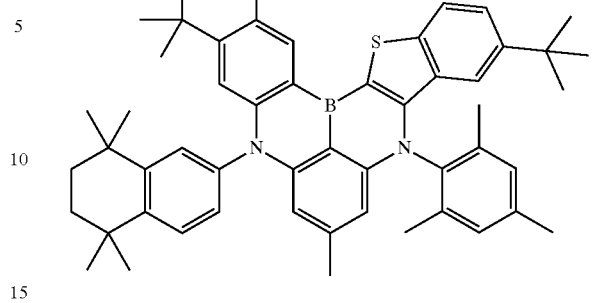
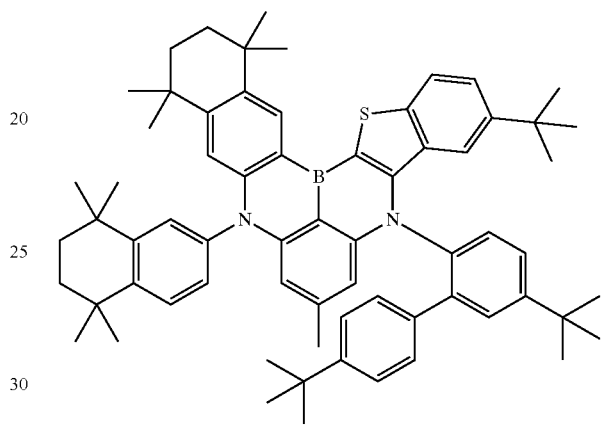
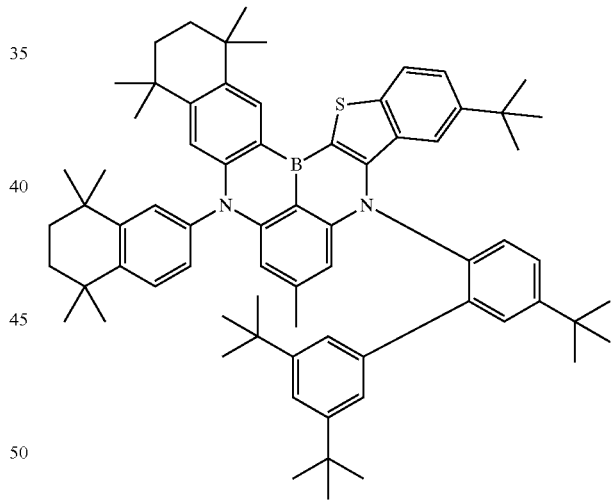
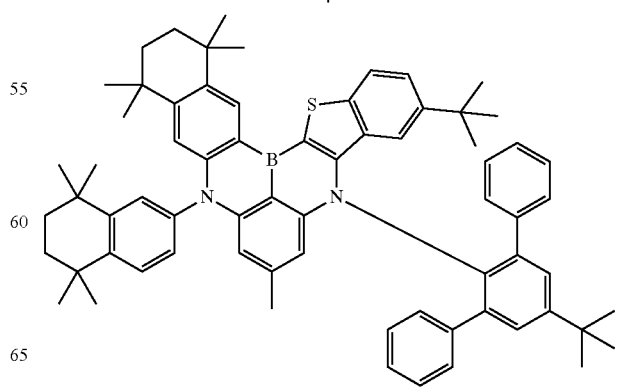

1449
-continued
1450
-continued
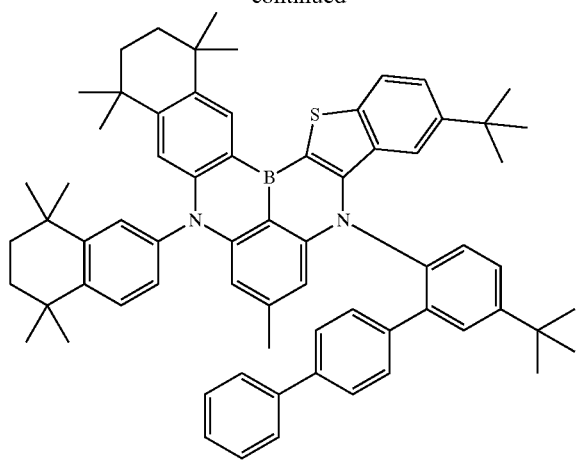
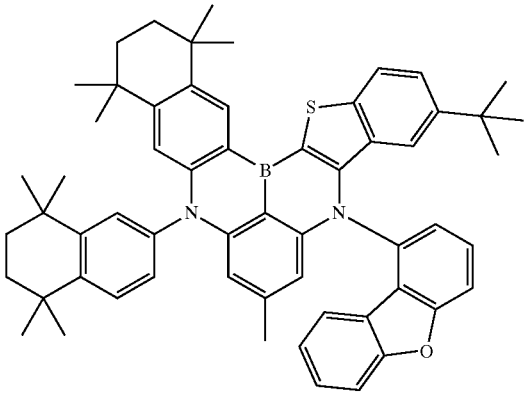
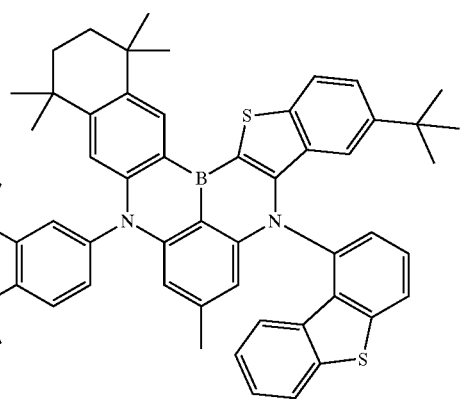
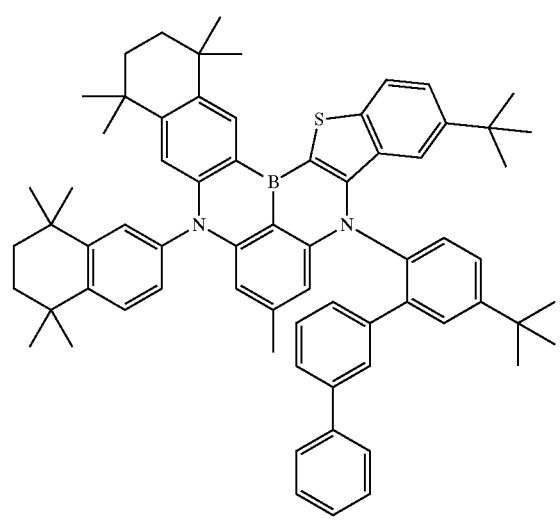
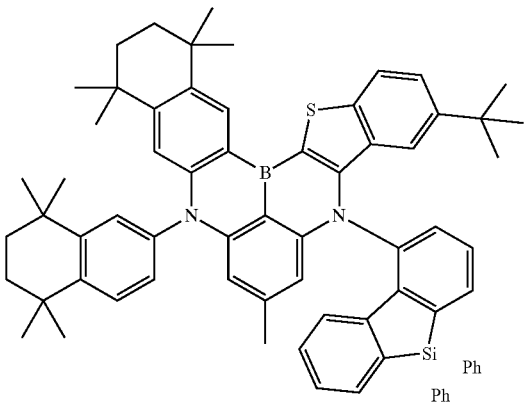
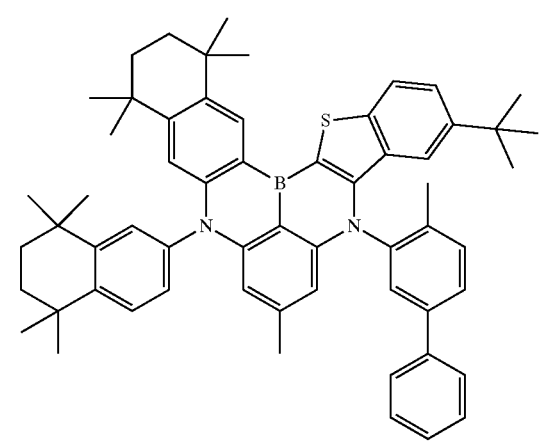
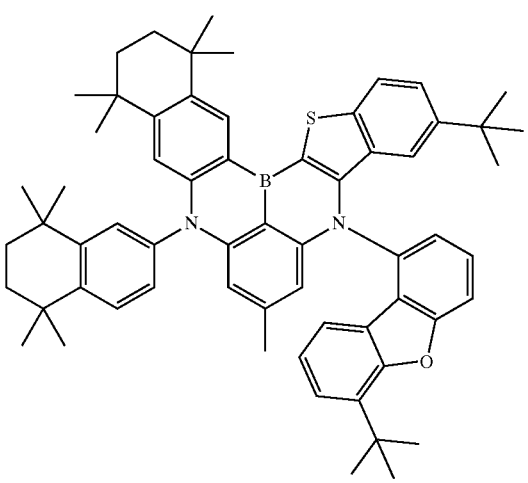

| 1451 -continued | 1452 -continued |
|---|---|
| 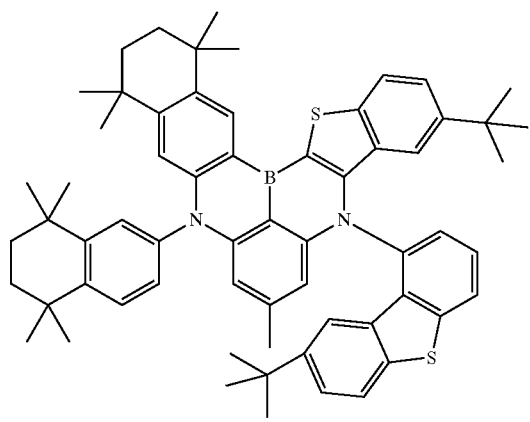 | 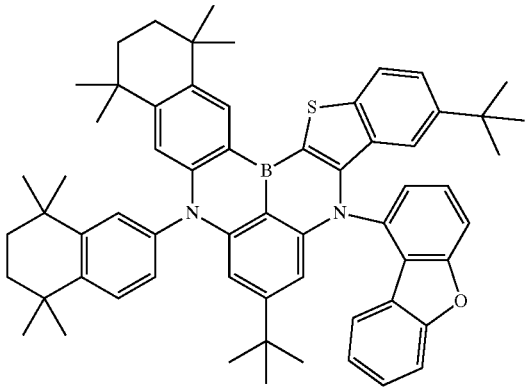 |
| 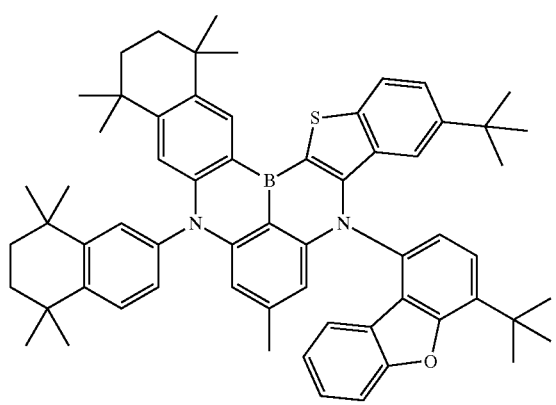 | 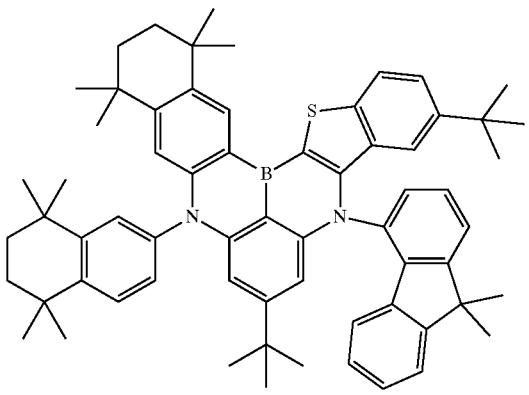 |
| 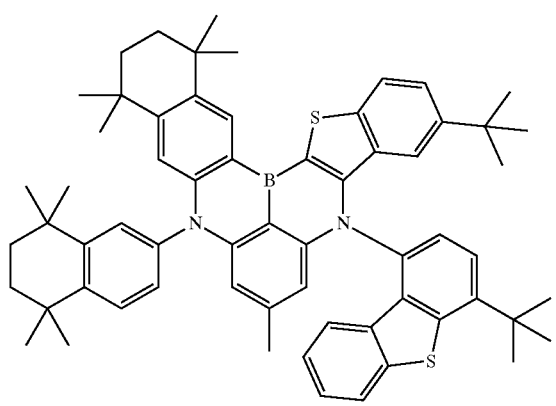 | 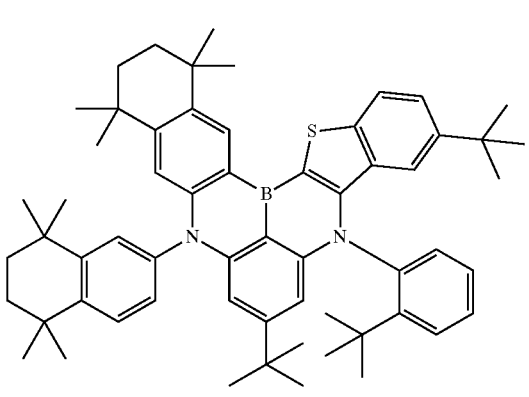 |
| 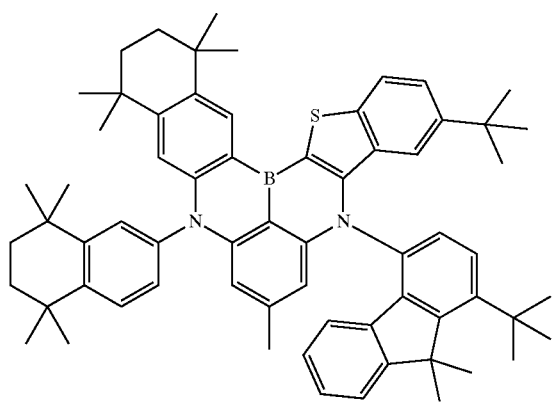 | 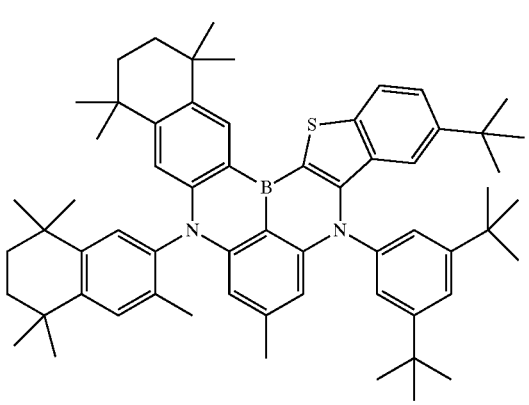 |

1453
-continued
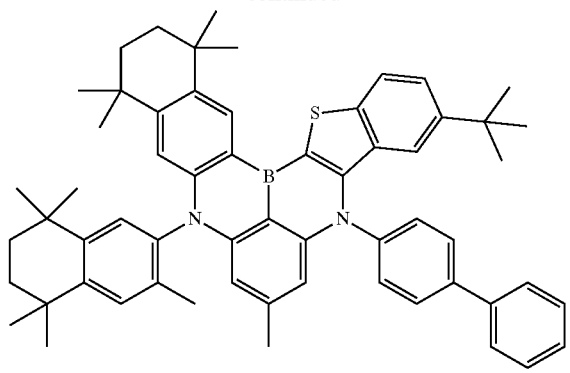
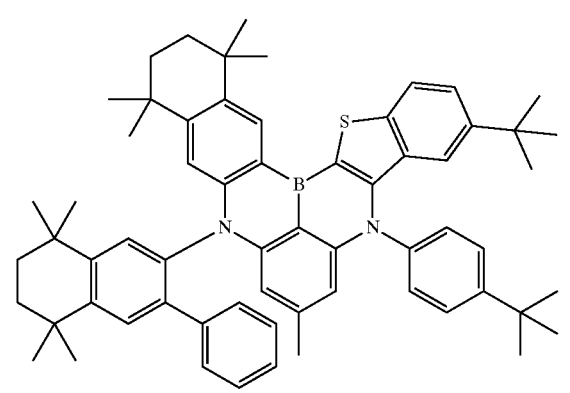
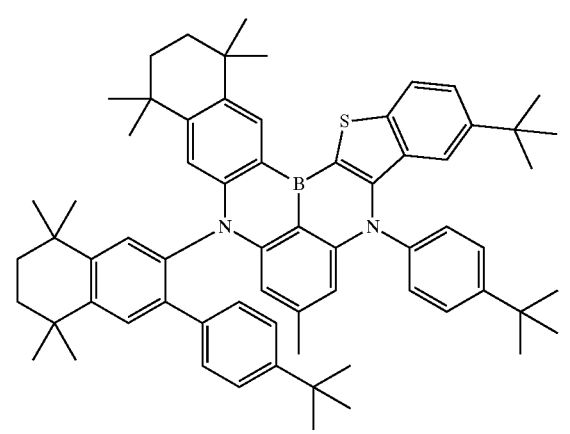
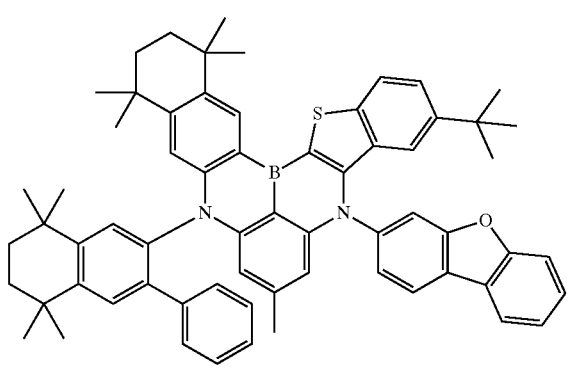
1454
-continued
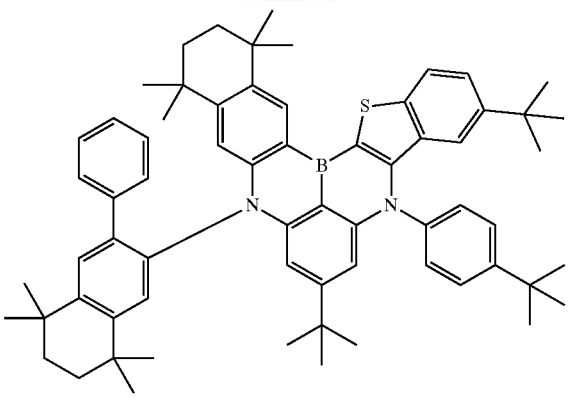
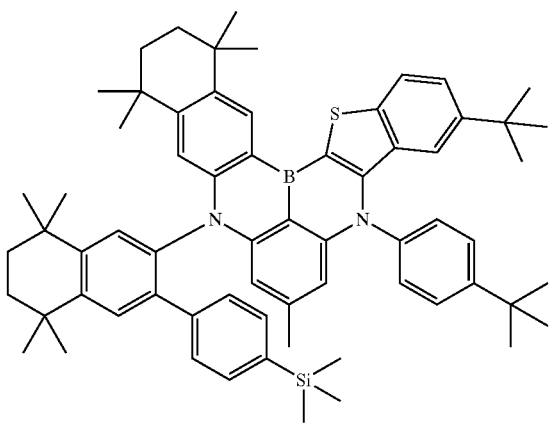
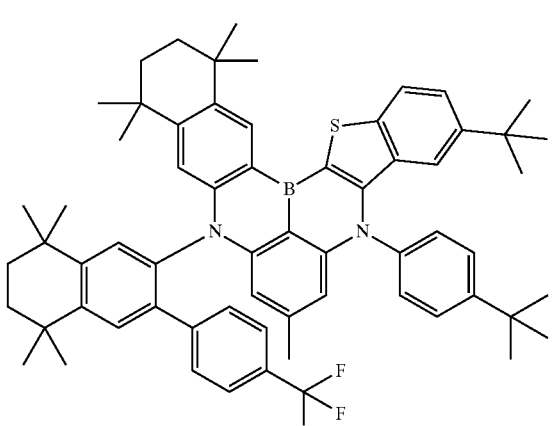
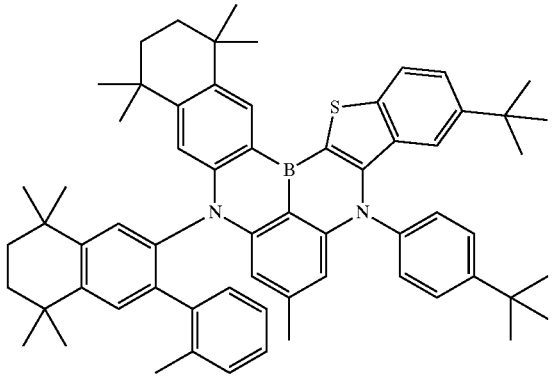

| 1455 | 1456 |
|---|---|
| -continued | -continued |
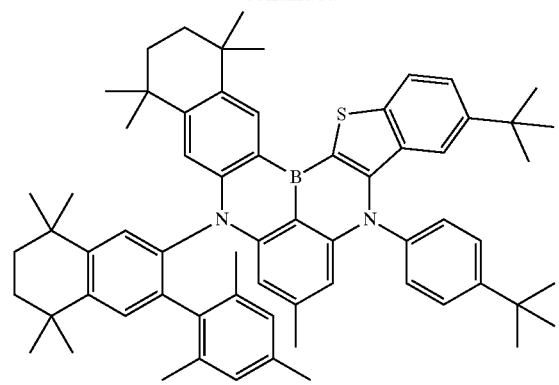
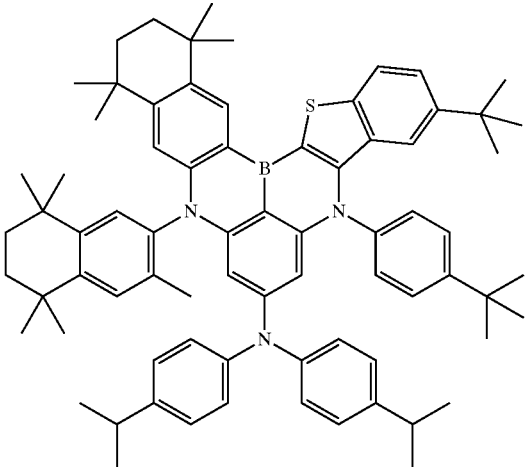
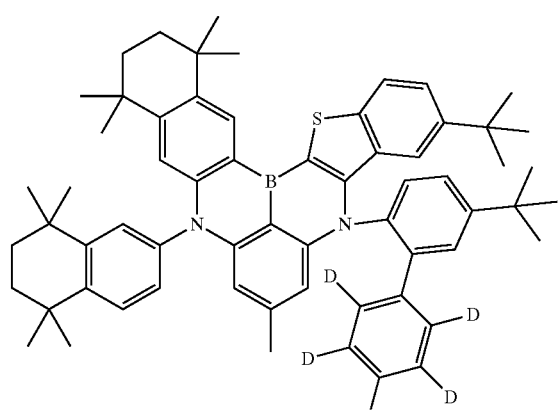
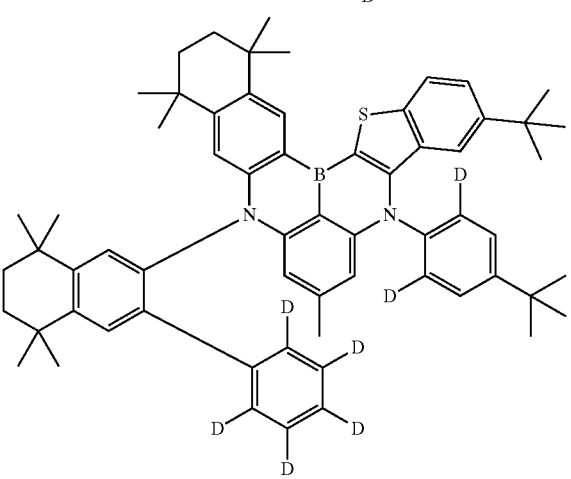
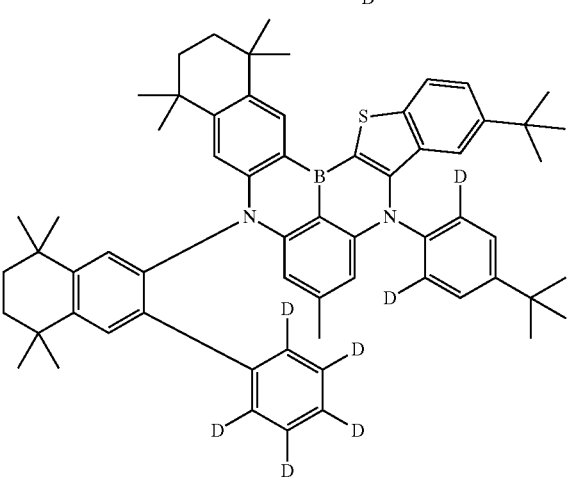
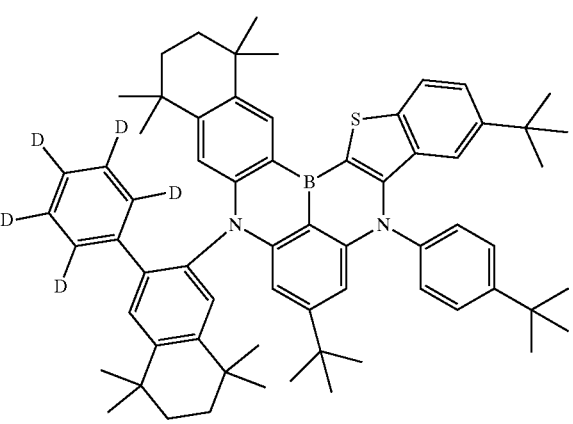

1457
-continued
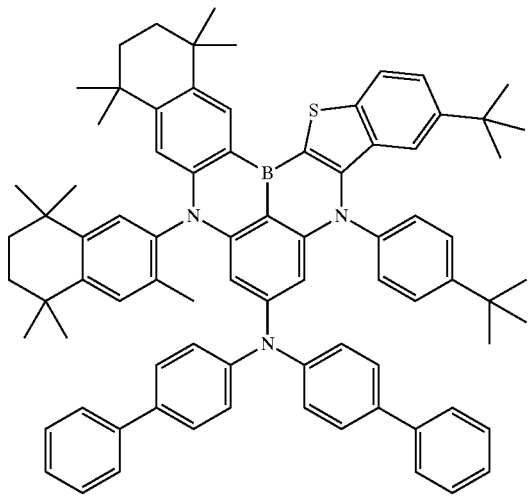
1458
-continued
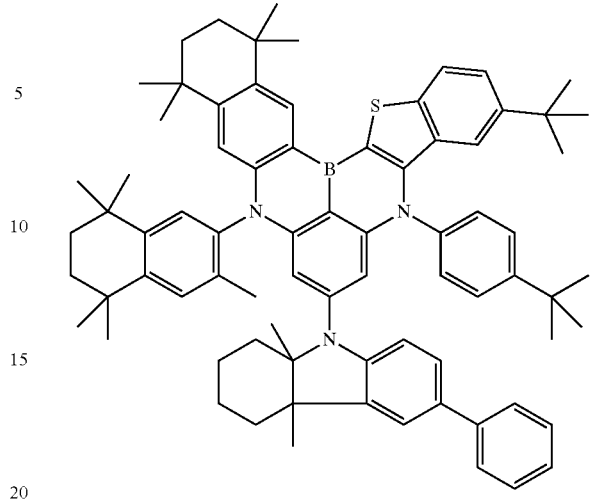
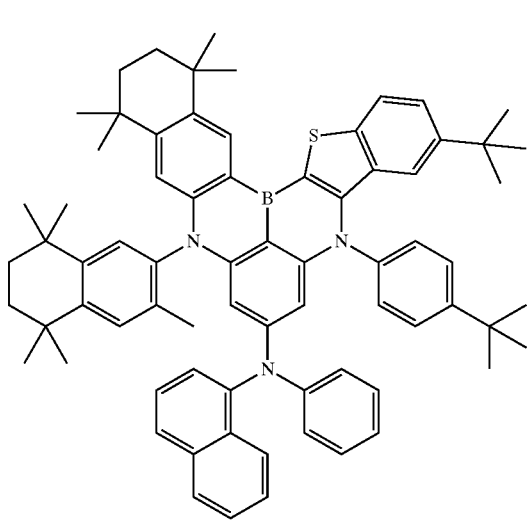
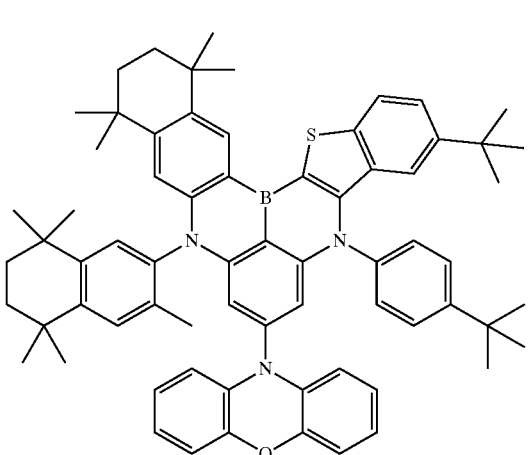
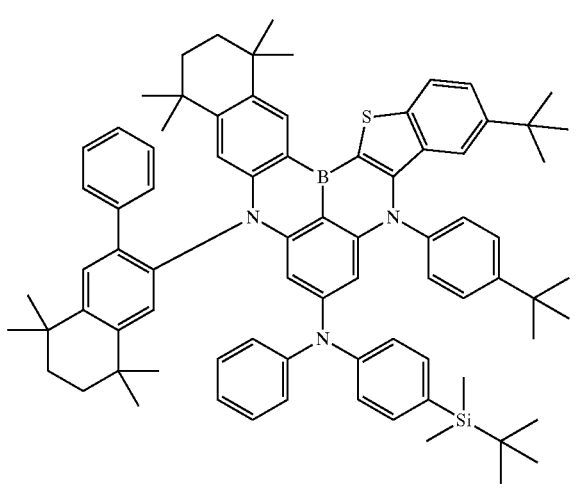
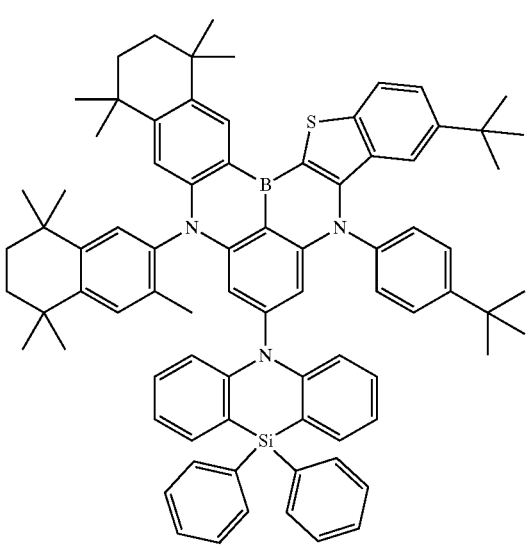

| 1459 -continued | 1460 -continued |
|---|---|
| 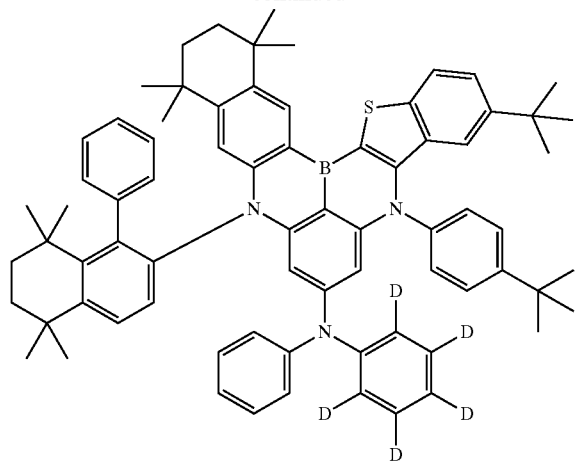 | 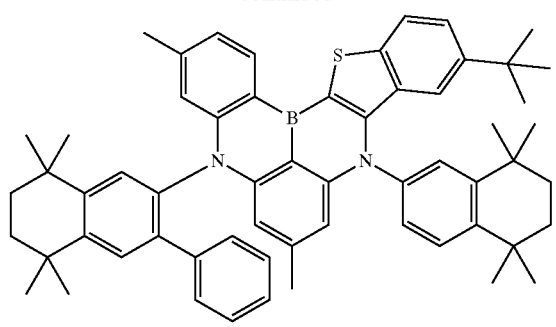 |
| 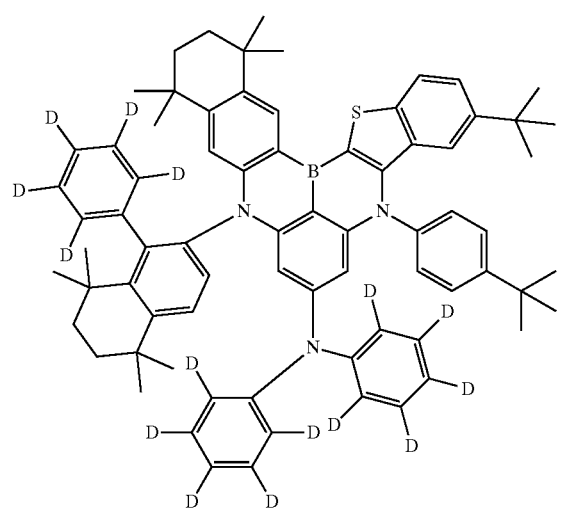 | 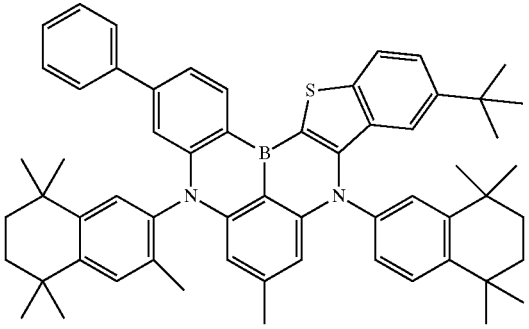 |
| 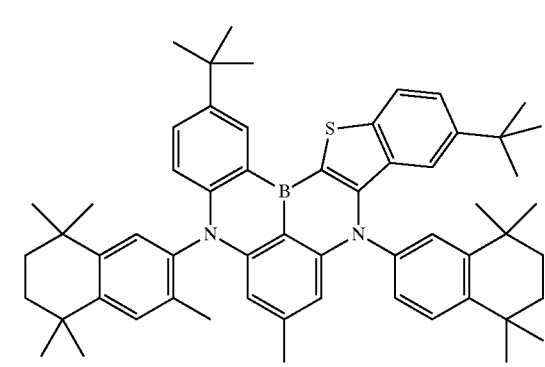 | 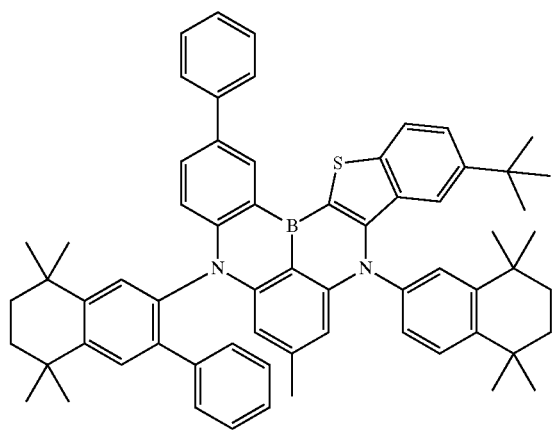 |
| 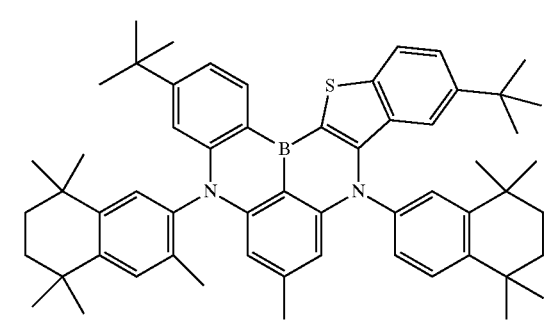 | 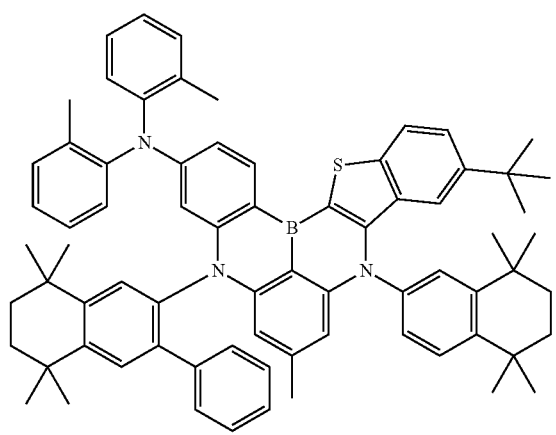 |

| 1461 | 1462 |
|---|---|
| -continued | -continued |
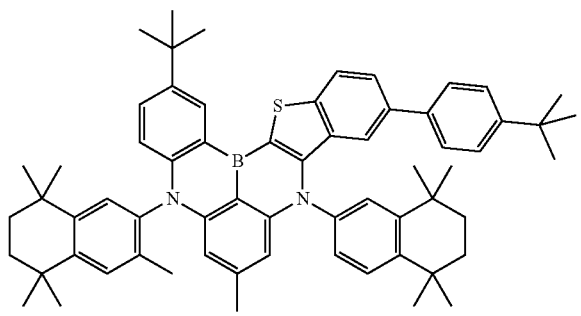
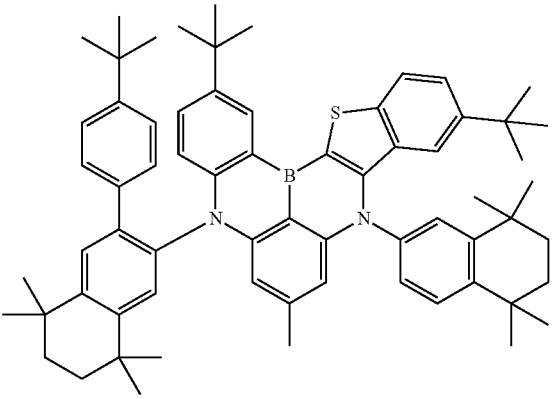
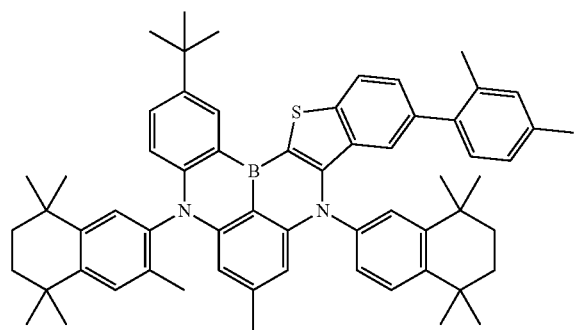
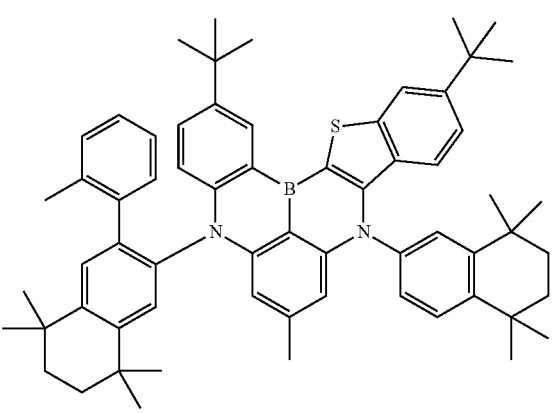
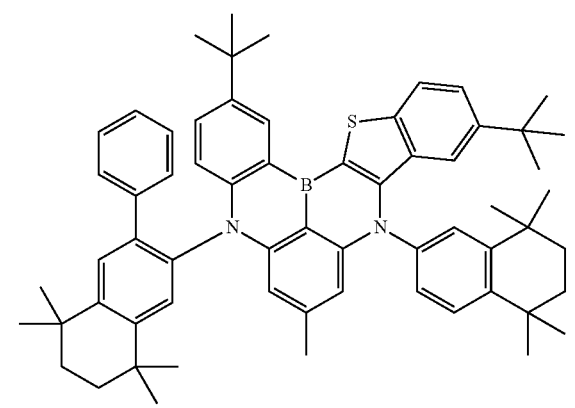
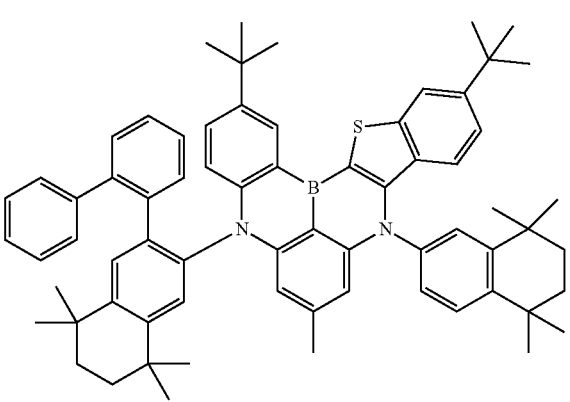
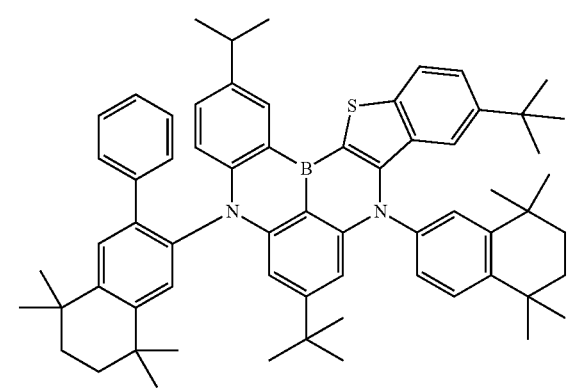
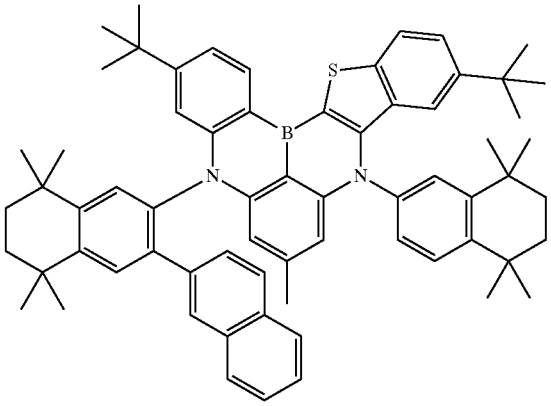

1463
-continued
1464
-continued
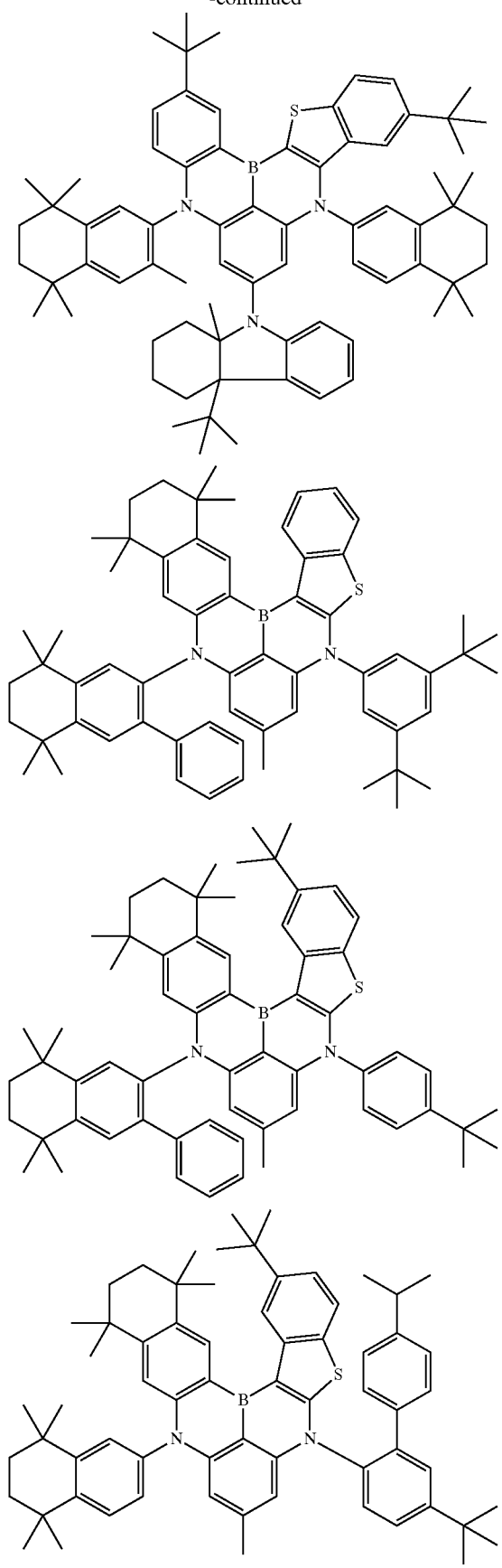
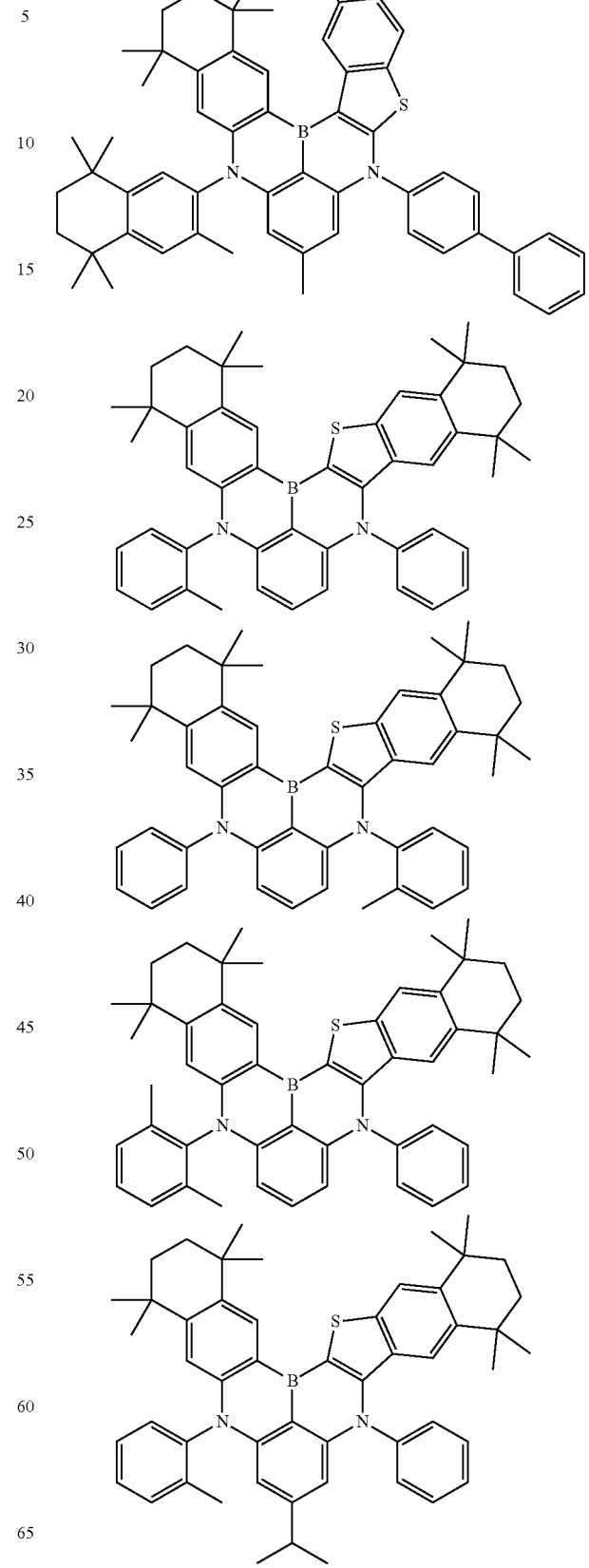

1465
-continued
1466
-continued
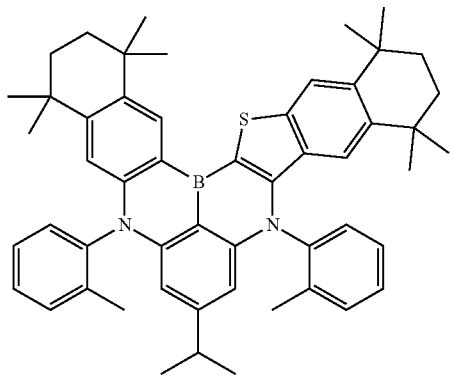
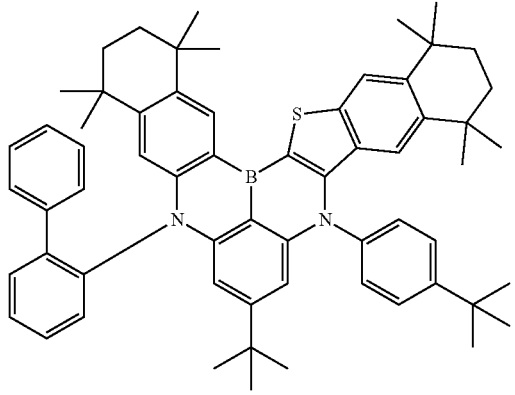
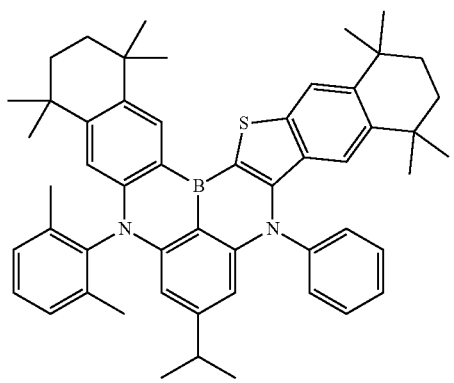
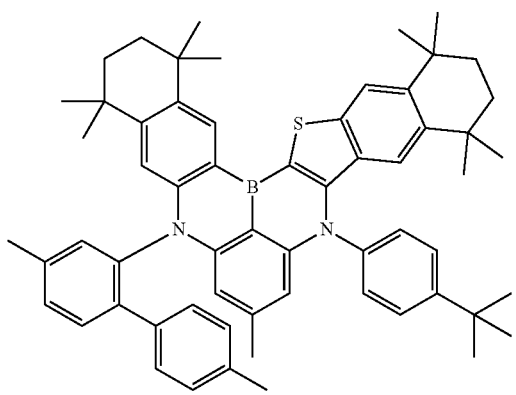
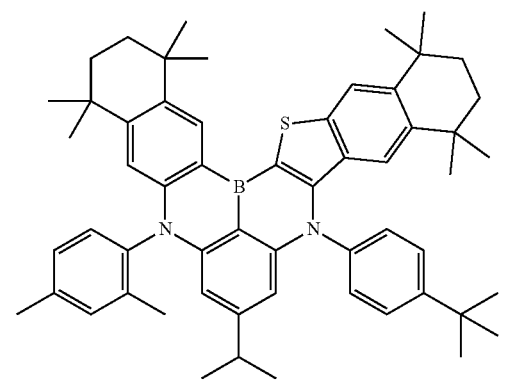
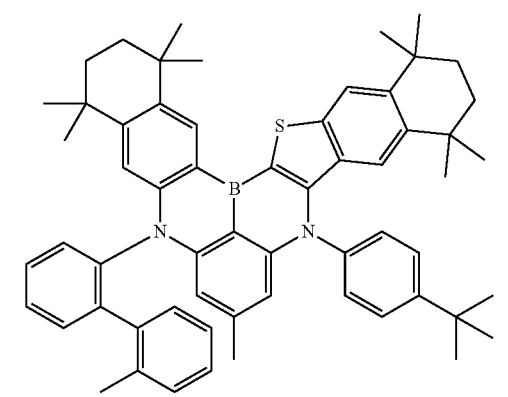
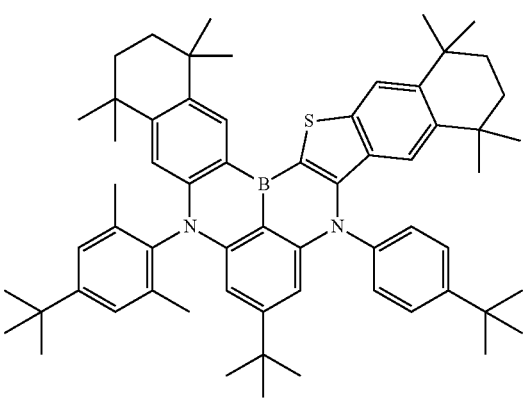
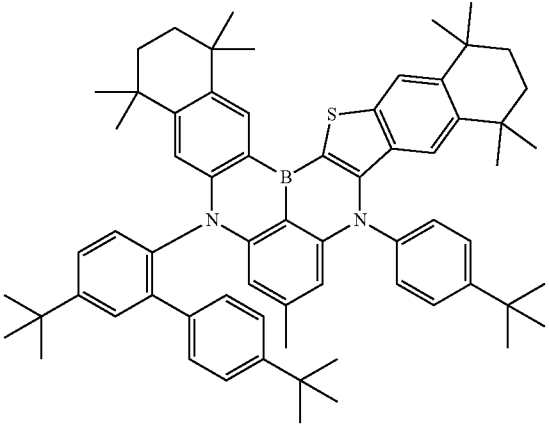

| 1467 | 1468 |
|---|---|
| -continued | -continued |
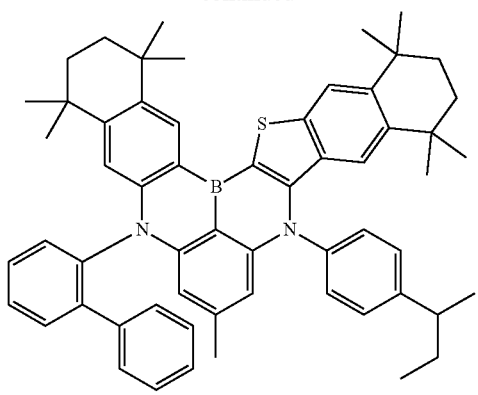
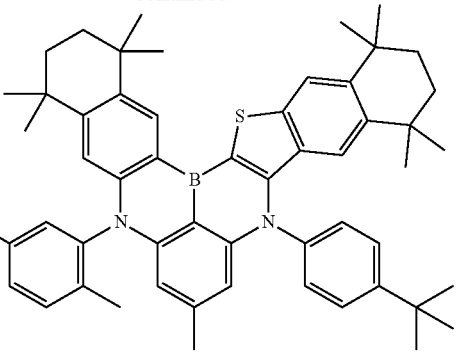
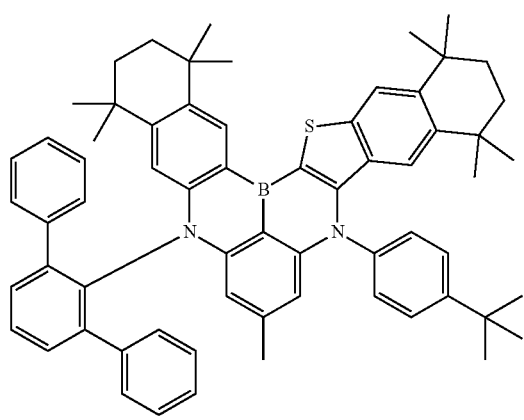
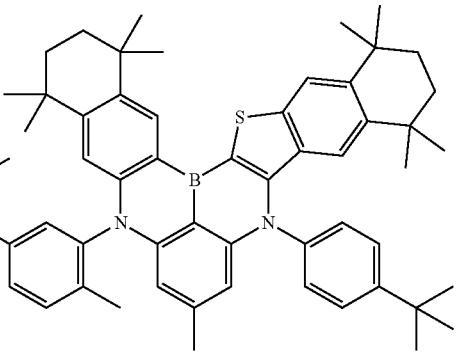
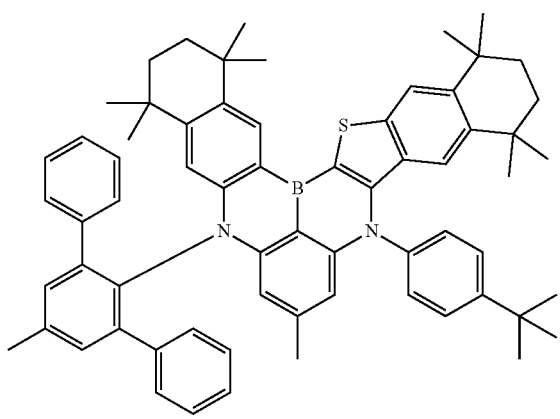
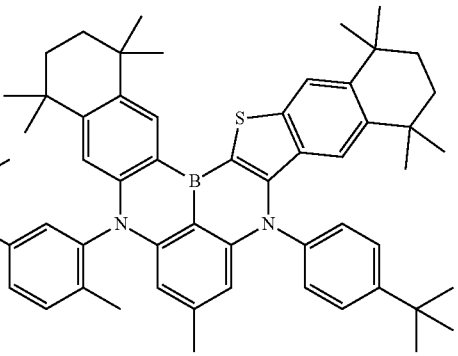
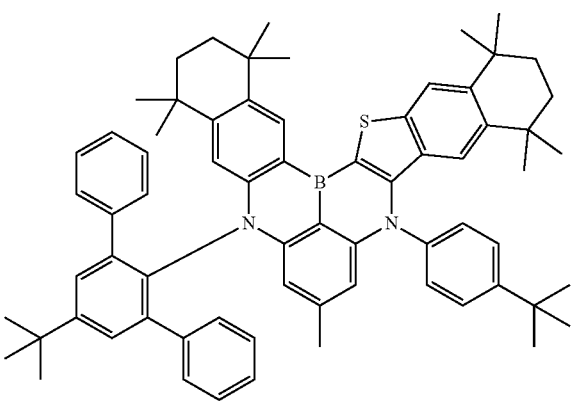
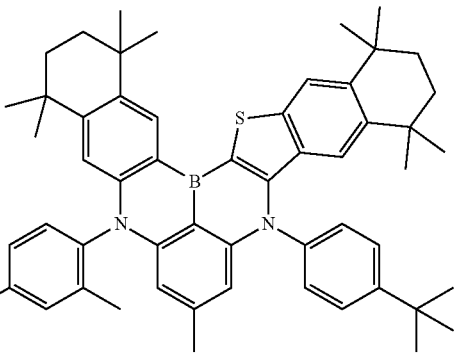

| 1469 | 1470 |
|---|---|
| -continued | -continued |
| 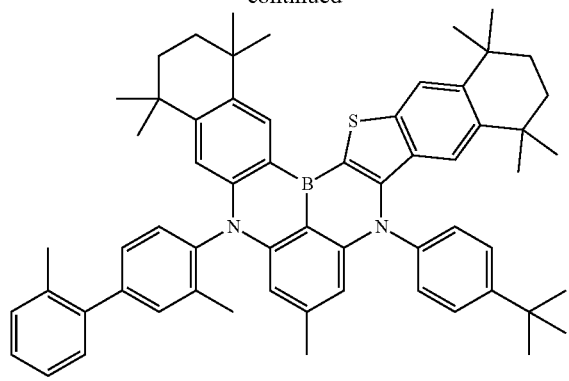 | 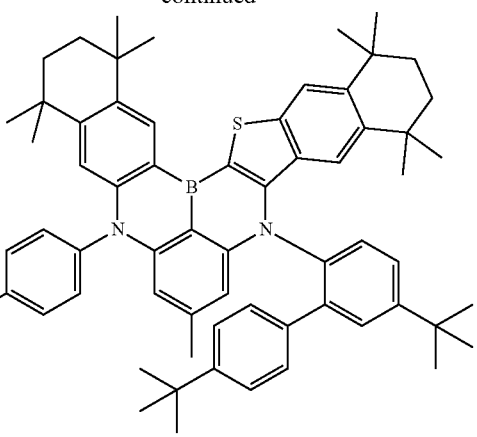 |
| 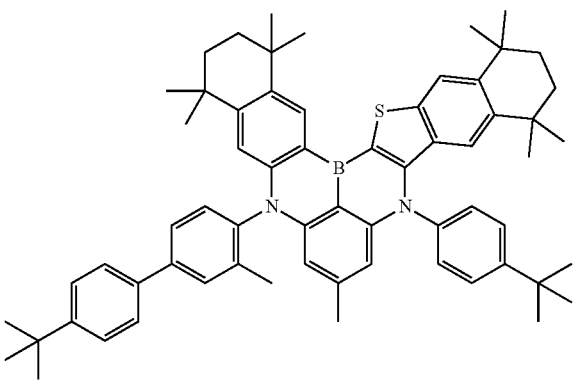 | 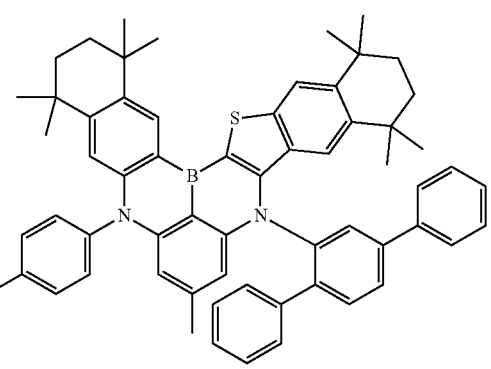 |
| 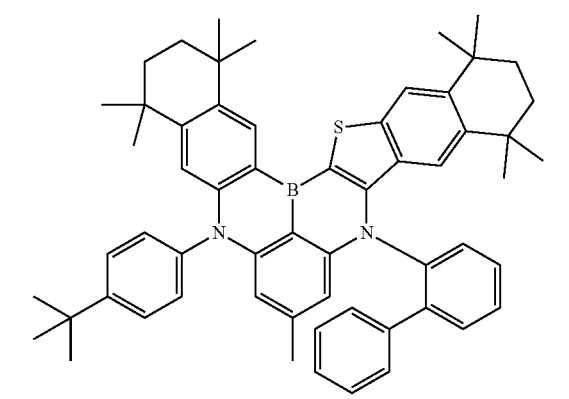 | 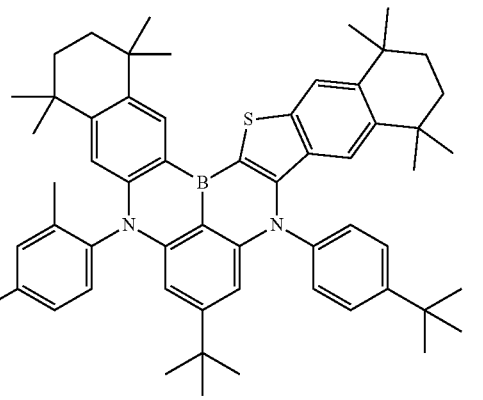 |
| 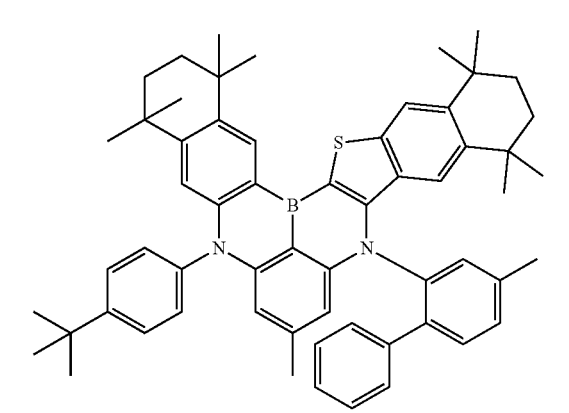 | 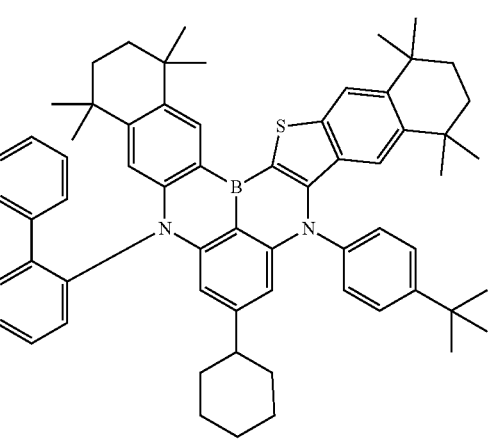 |

1471
-continued
1472
-continued
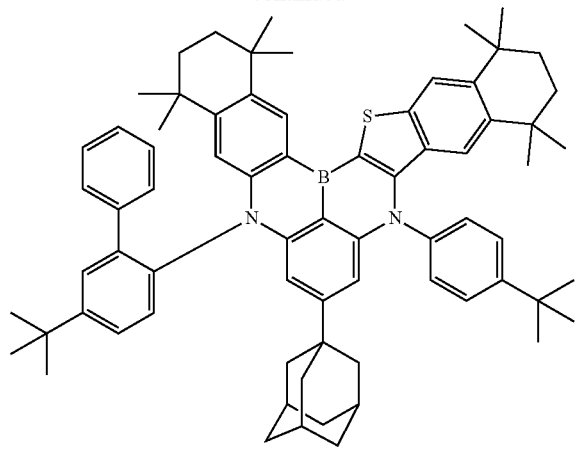
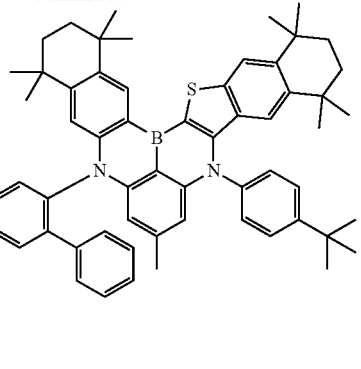
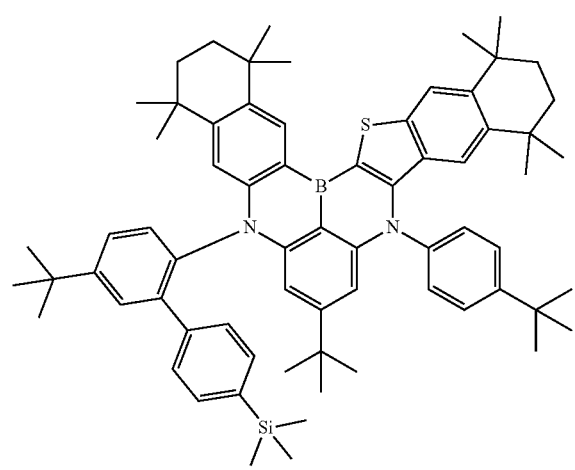
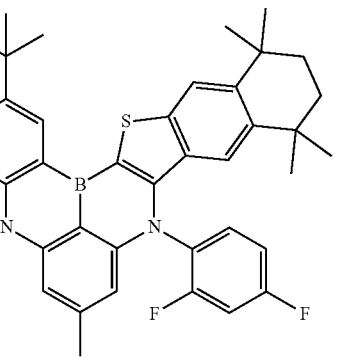
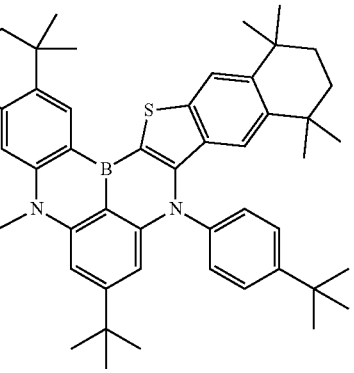
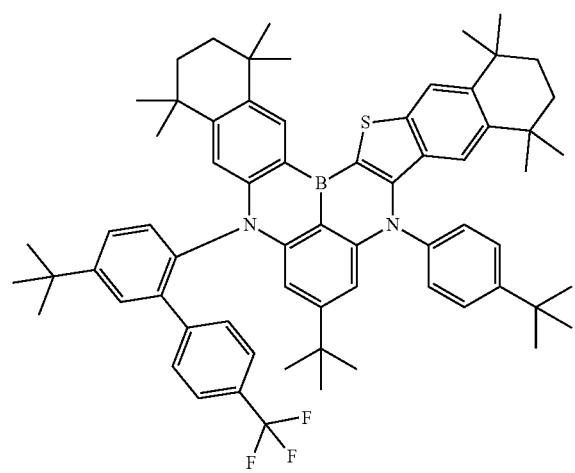
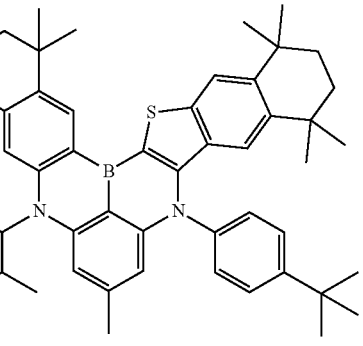

1473
-continued
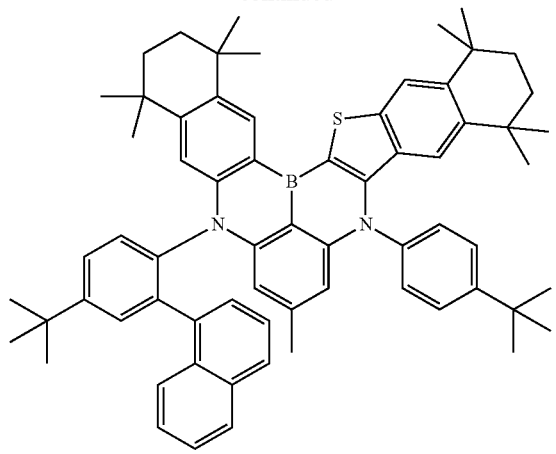
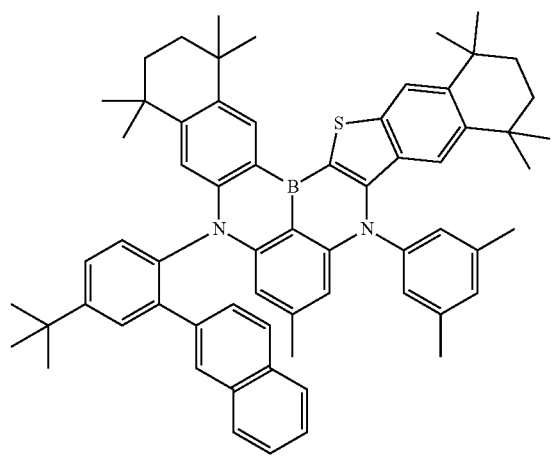
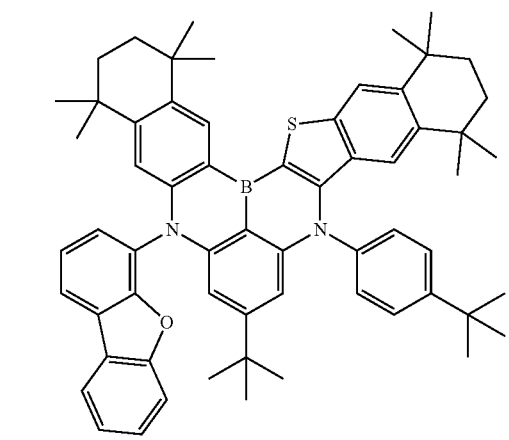
1474
-continued
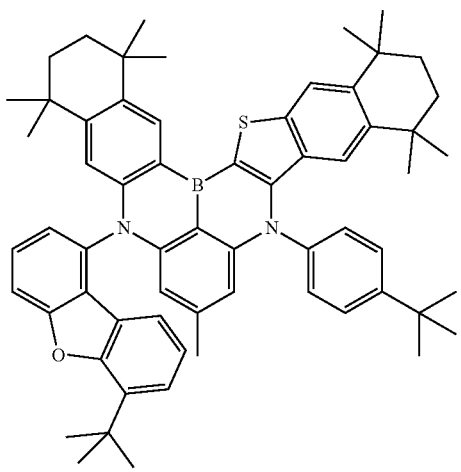
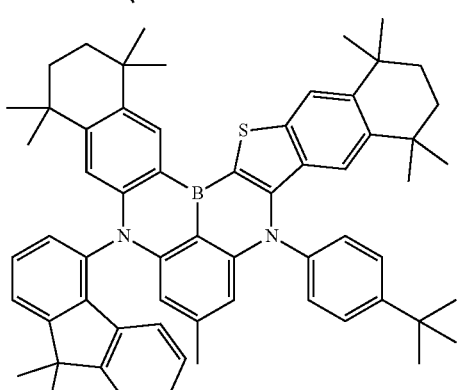
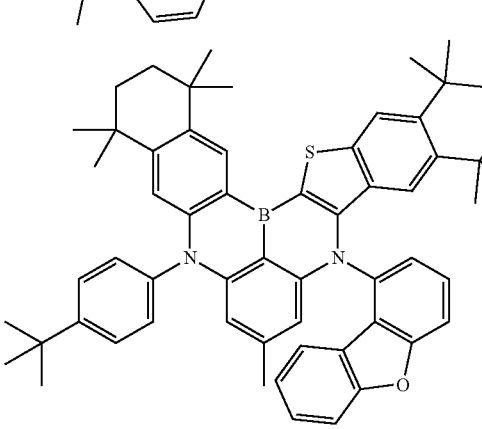

1475
-continued
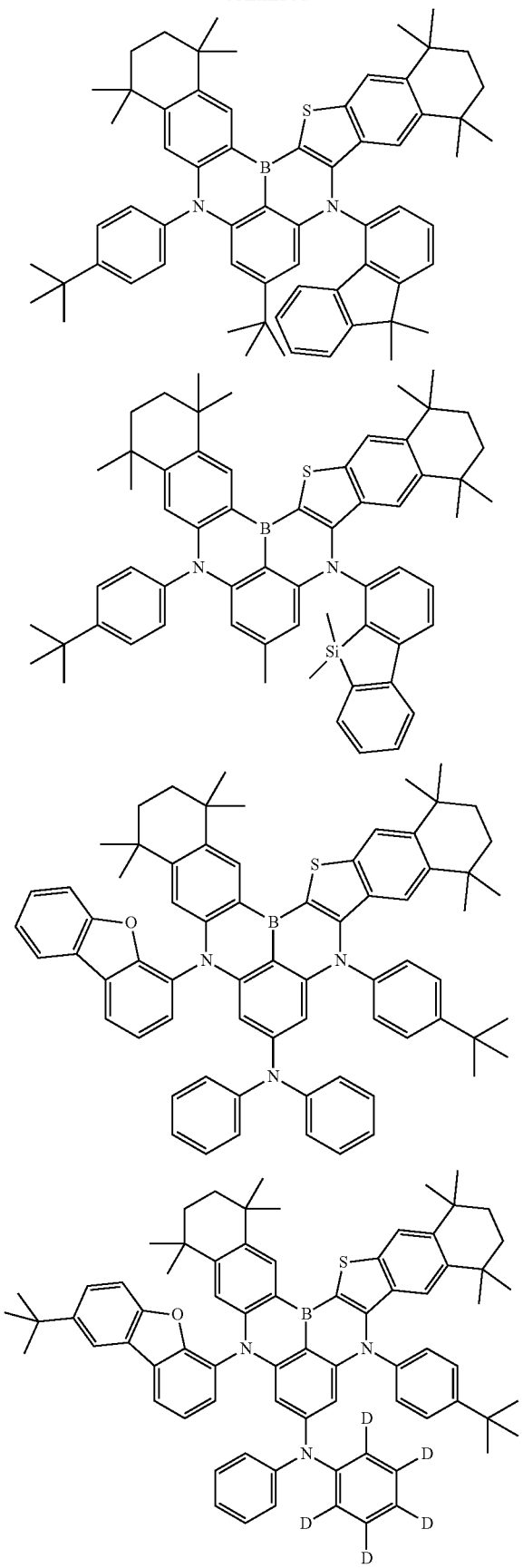
1476
-continued
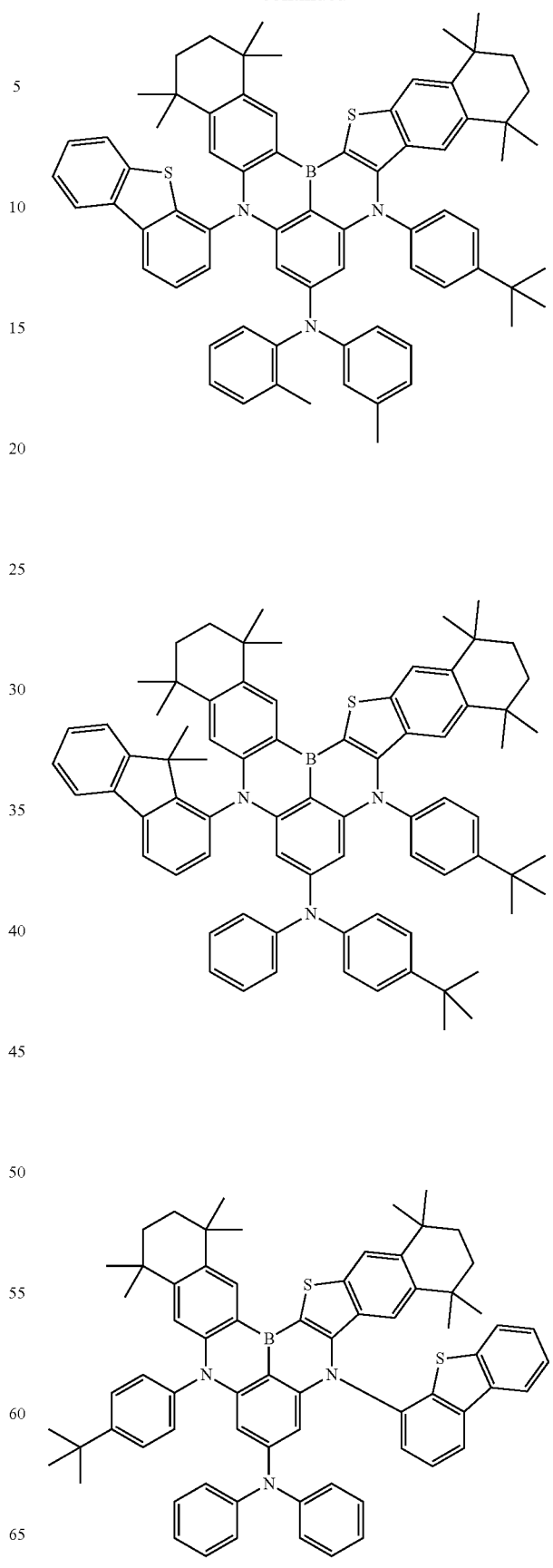

1477
-continued
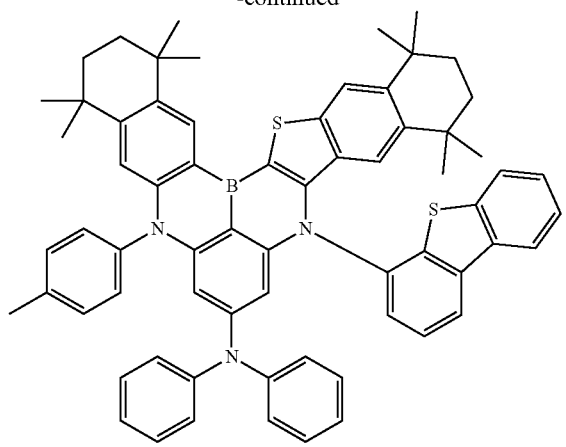
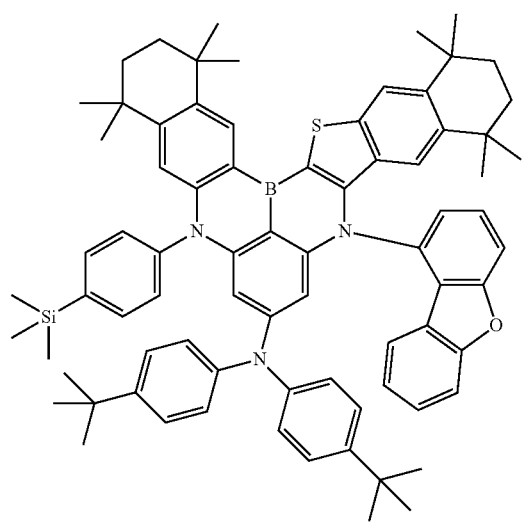
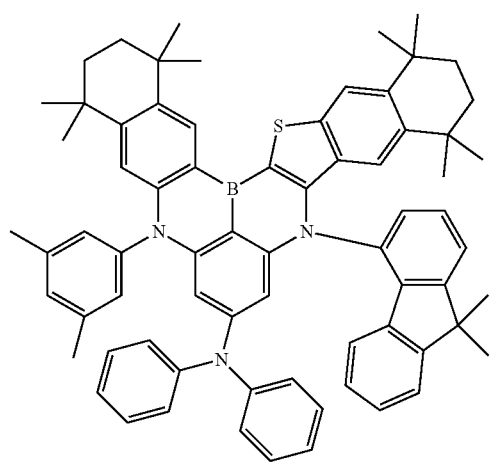
1478
-continued
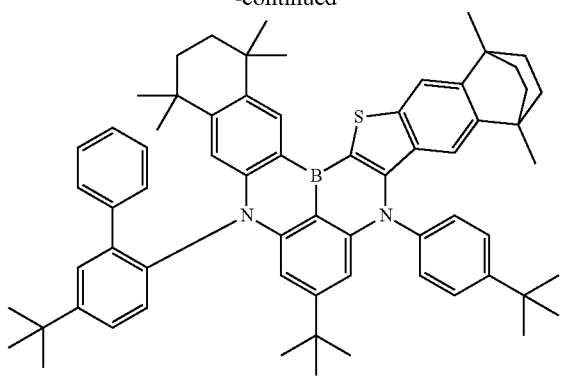
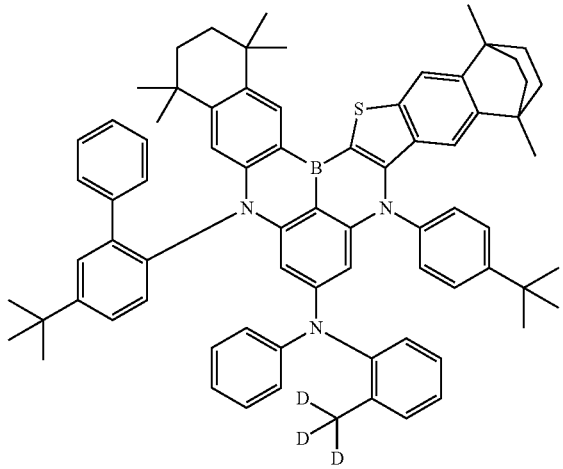

1479
-continued
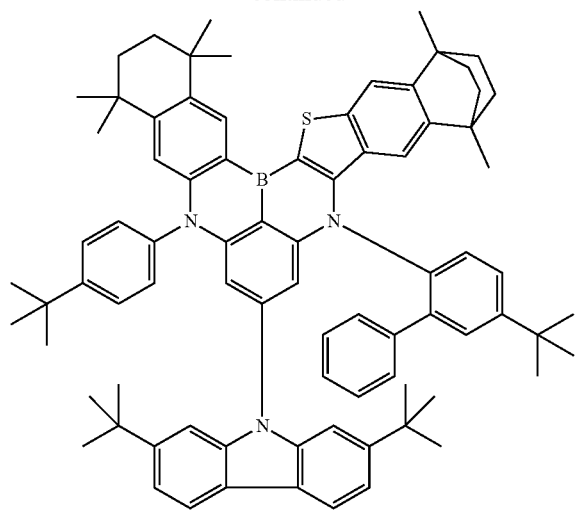
1480
-continued
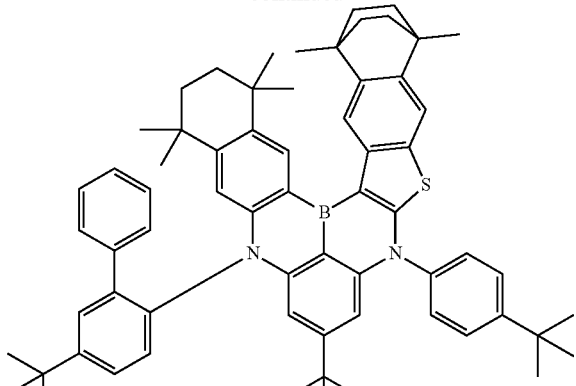
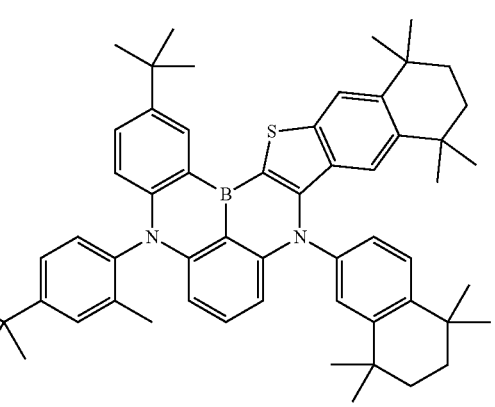
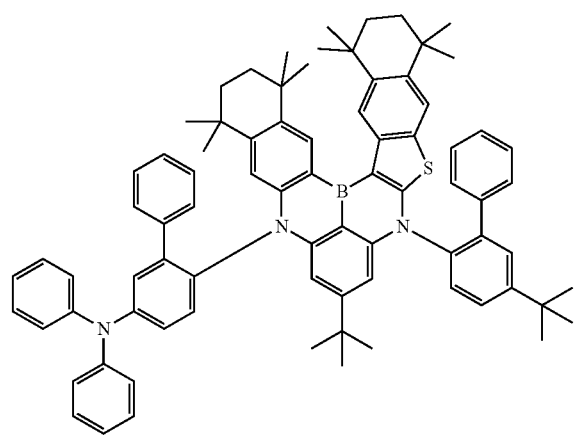
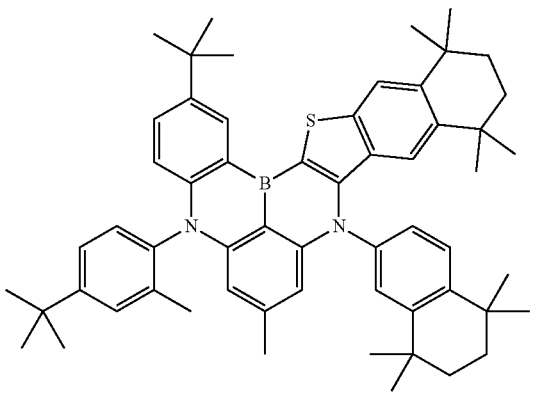
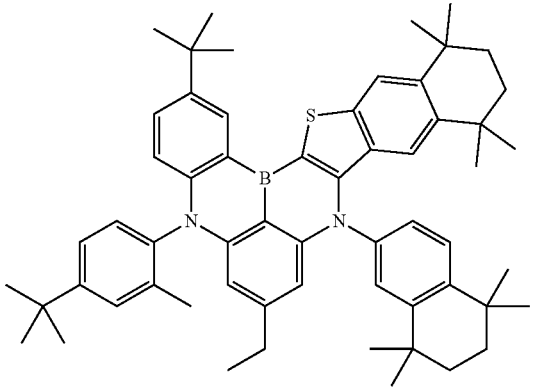

1481
-continued
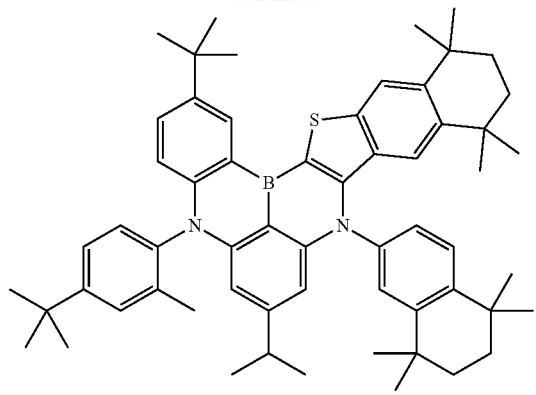
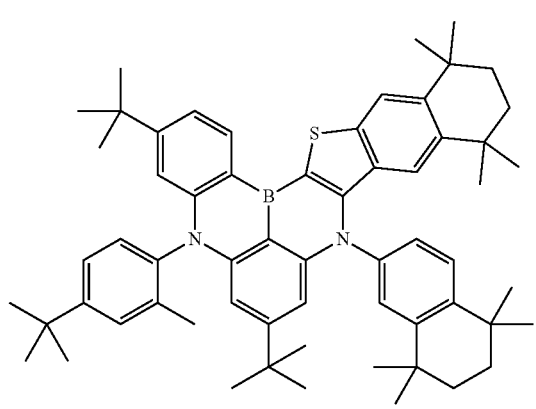
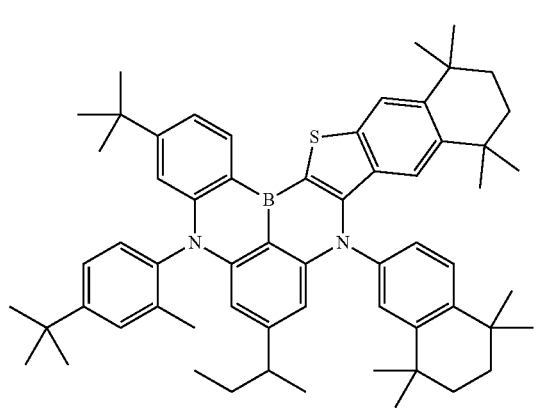
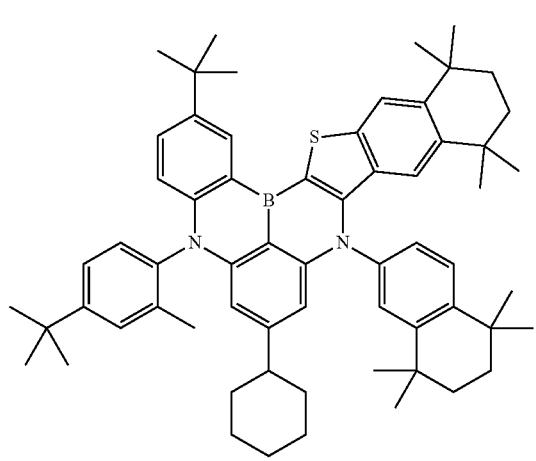
1482
-continued
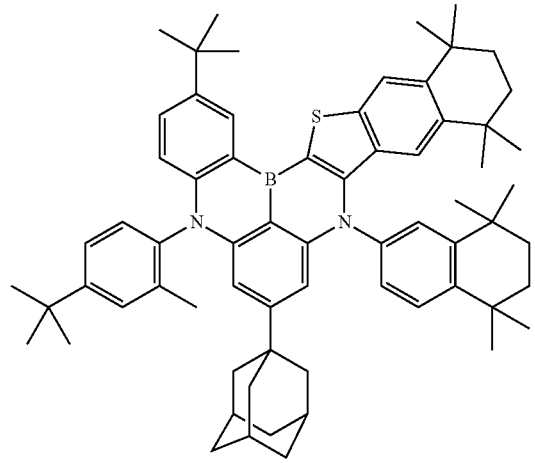
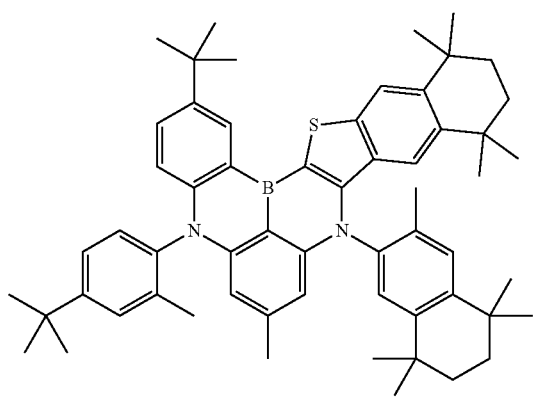
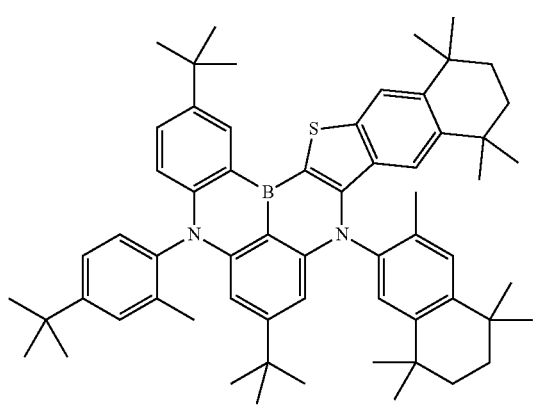
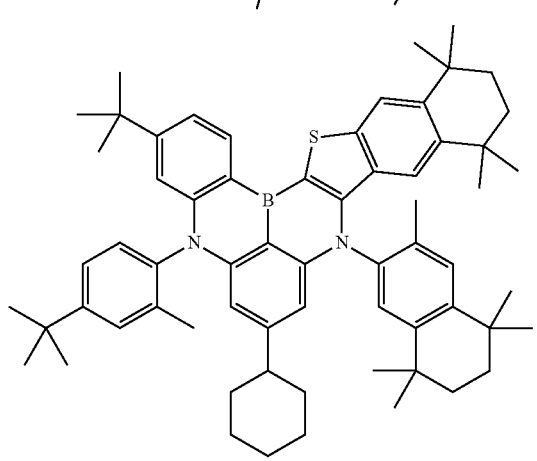

1483
-continued
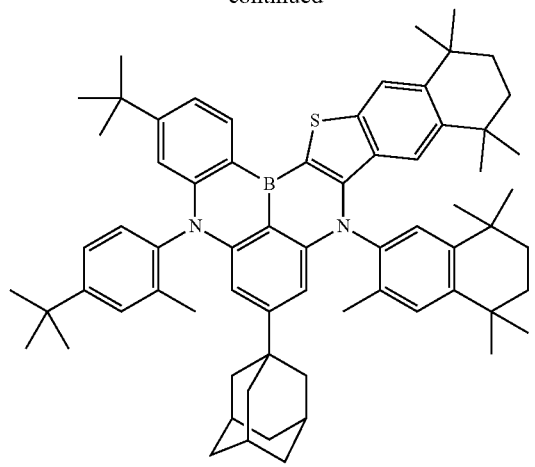
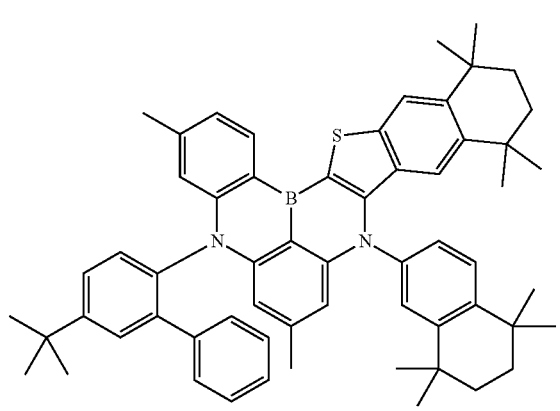
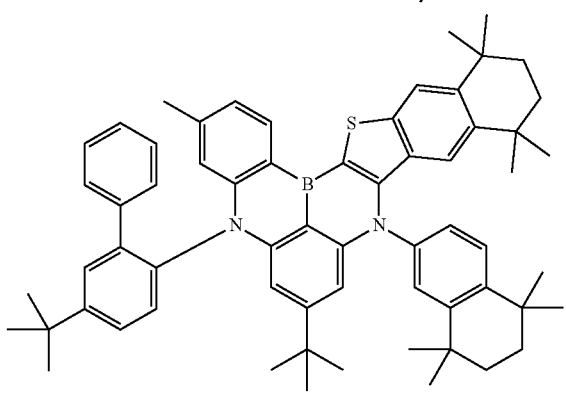
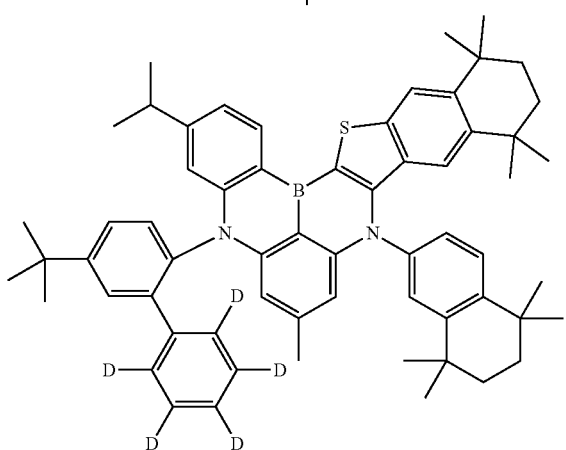
1484
-continued
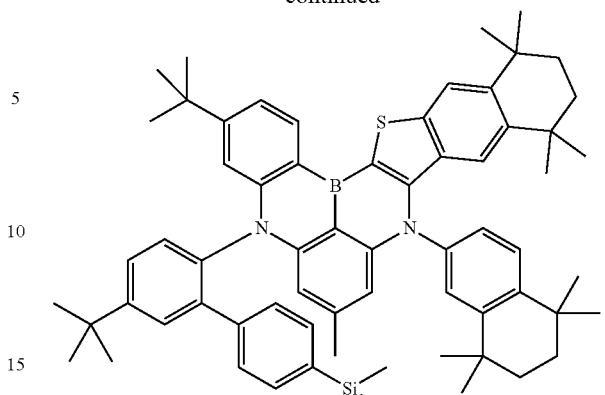
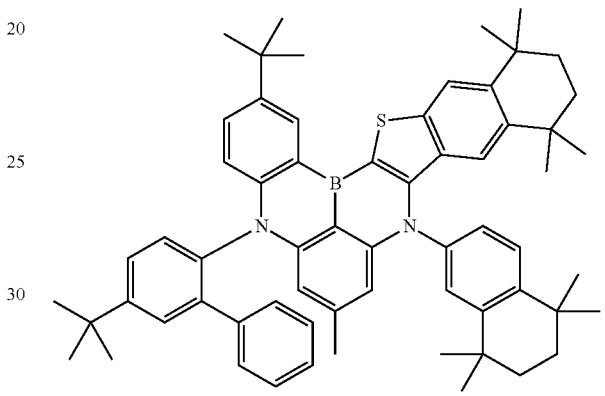
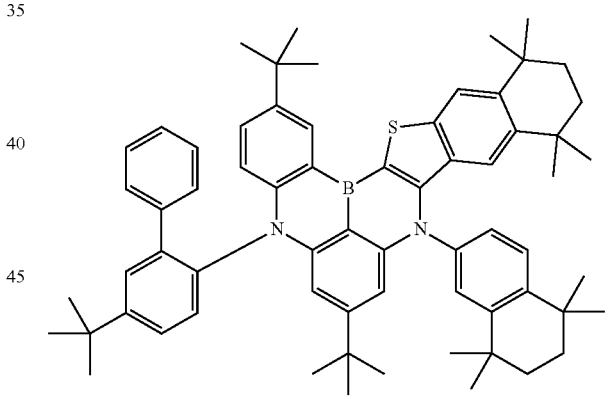
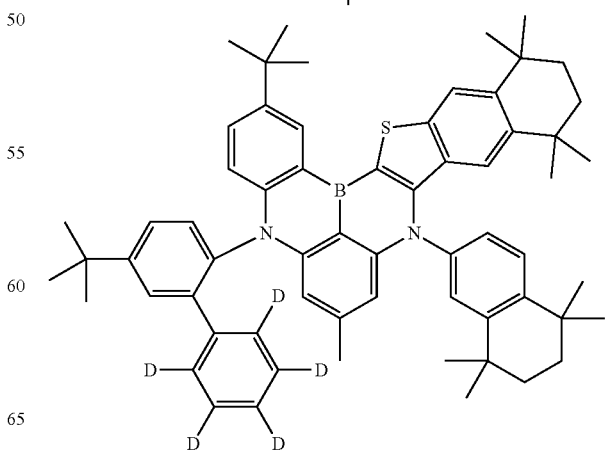

1485
-continued
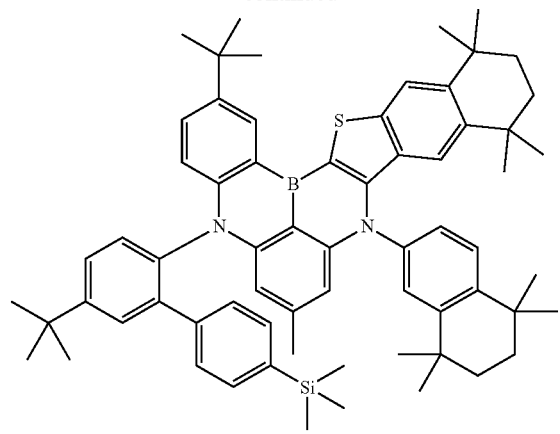
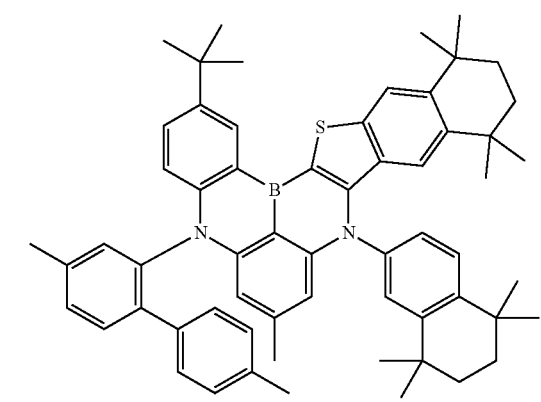
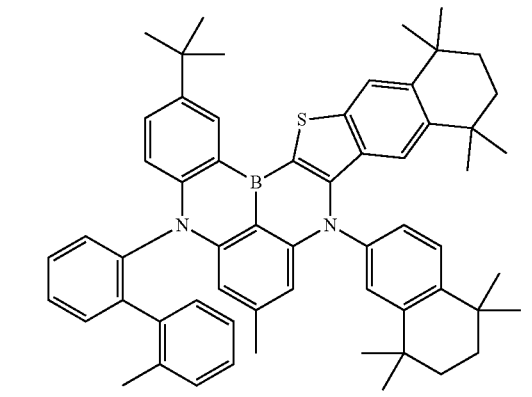
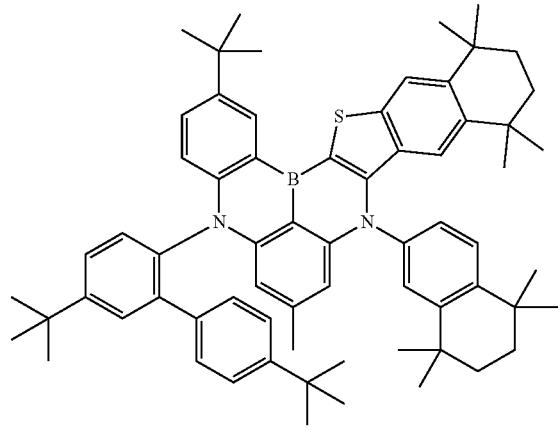
1486
-continued
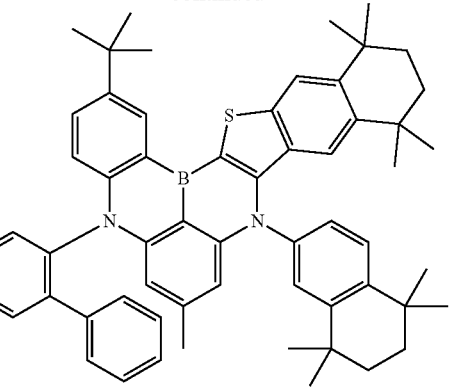
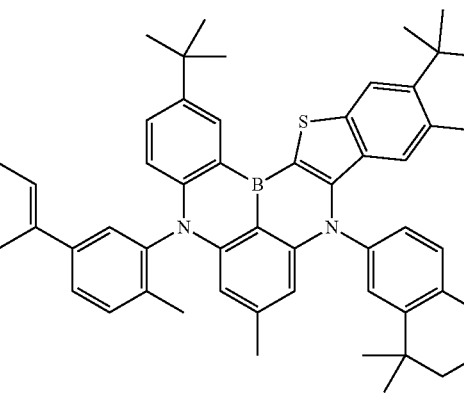
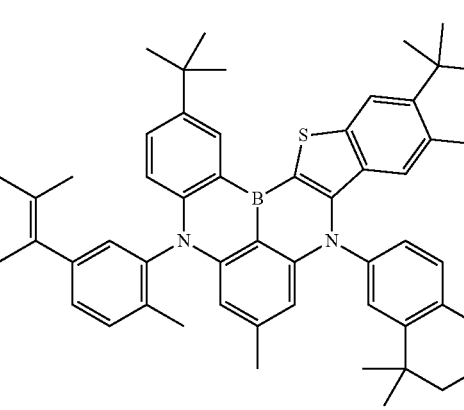
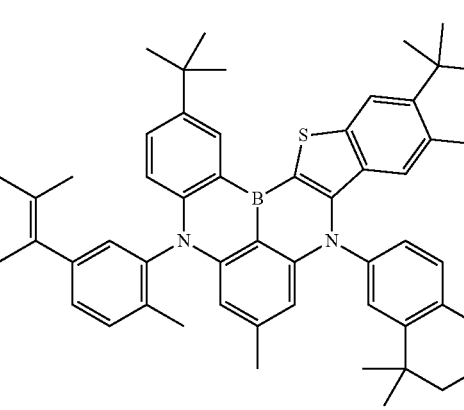

1487
-continued
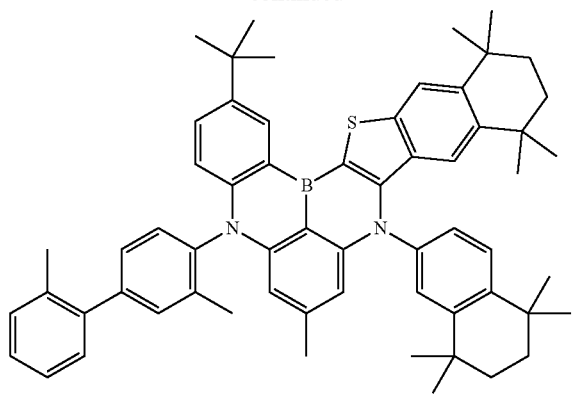
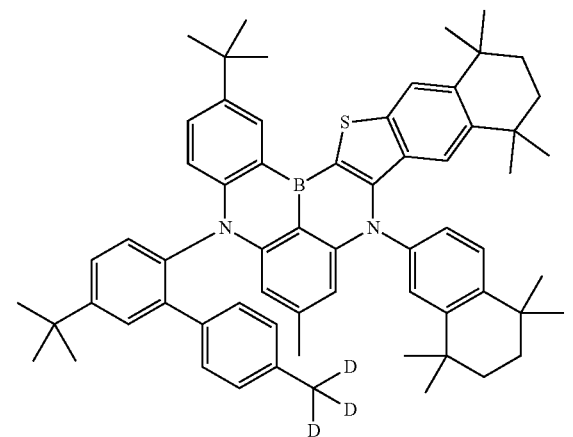
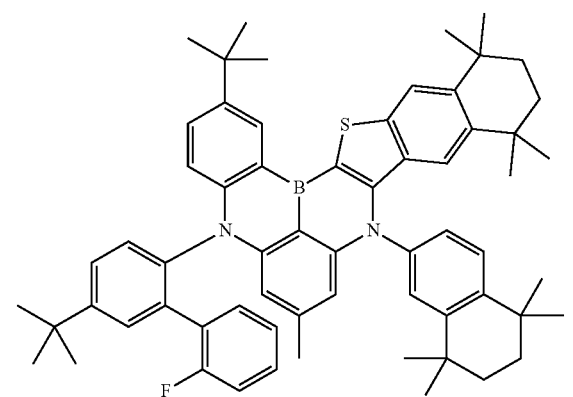
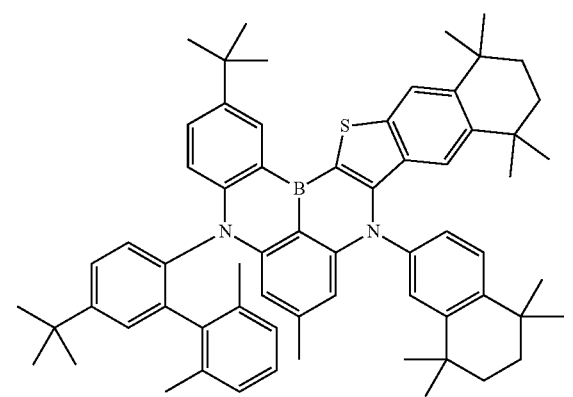
1488
-continued
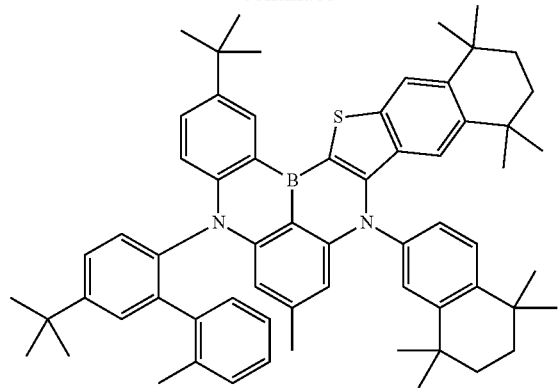
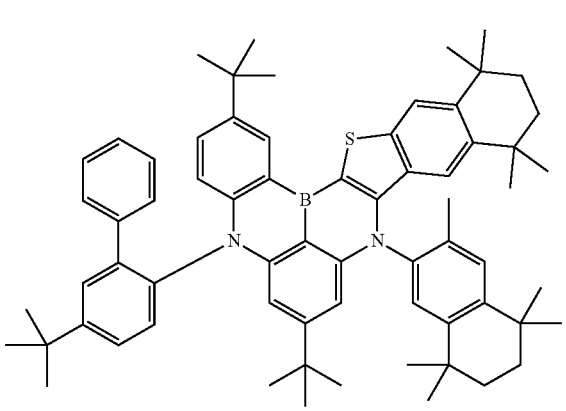
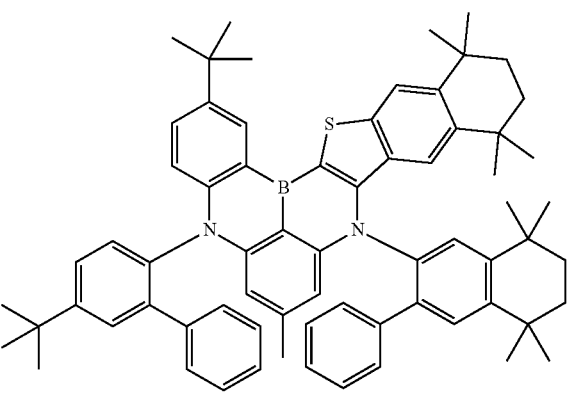

1489
-continued
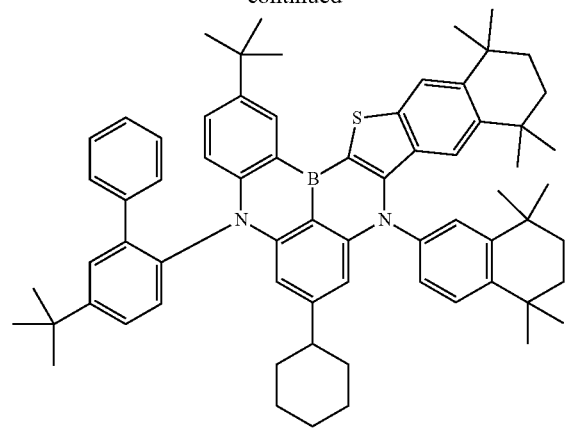
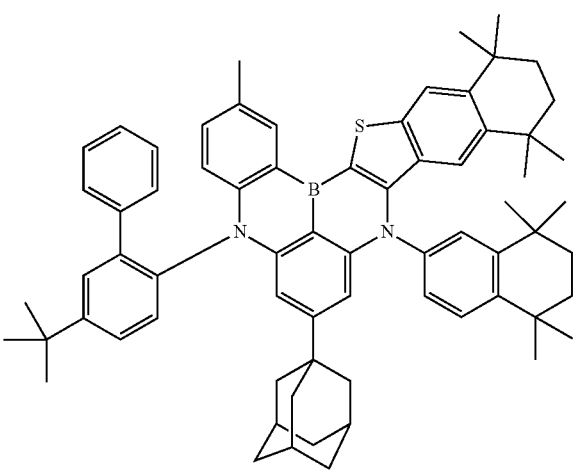
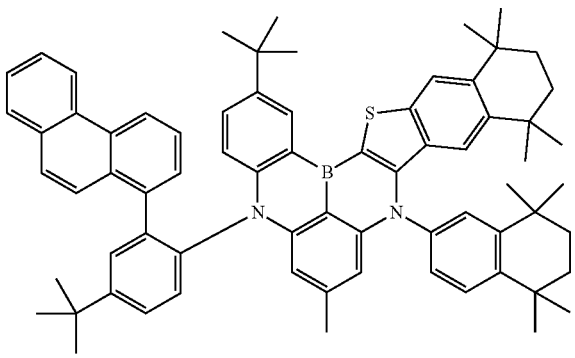
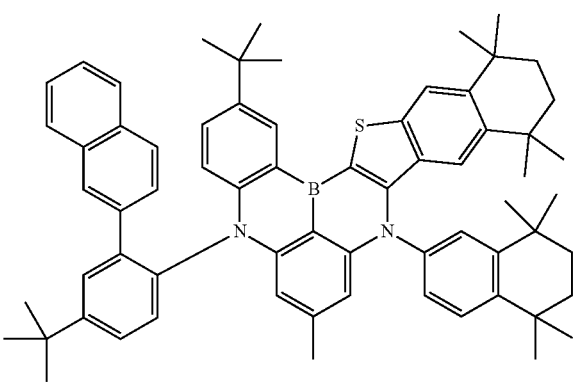
1490
-continued
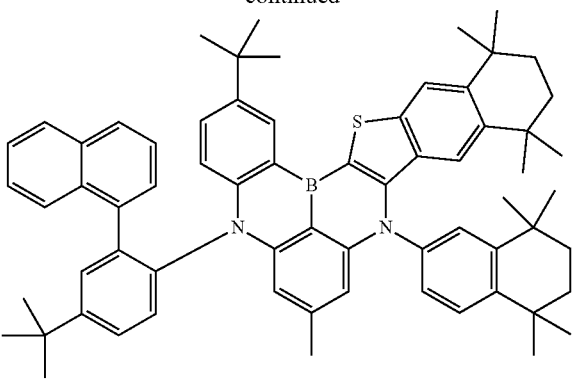
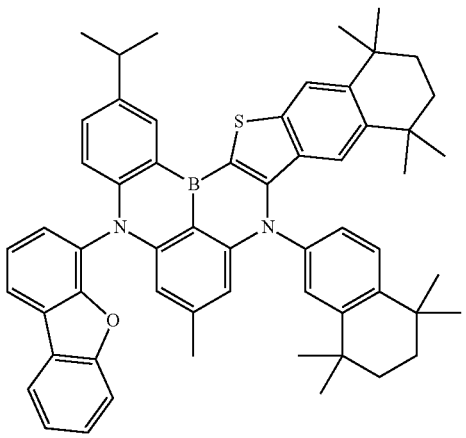
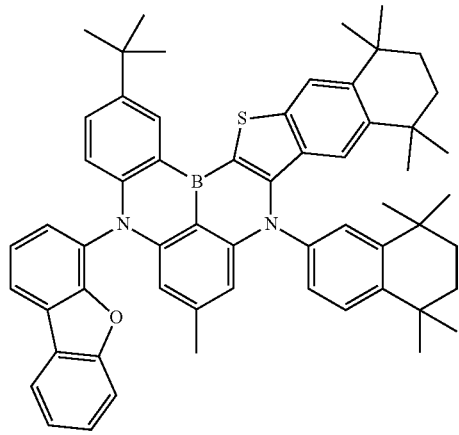
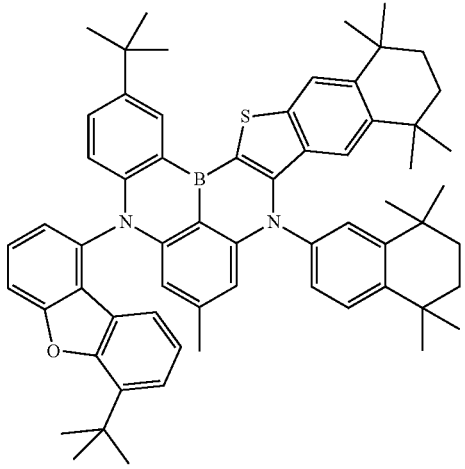

1491
-continued
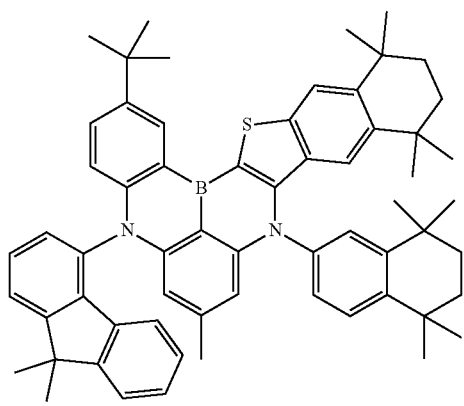
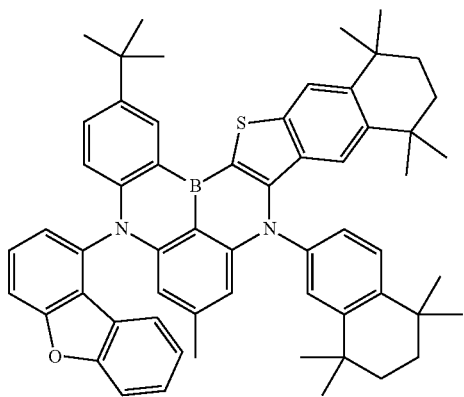
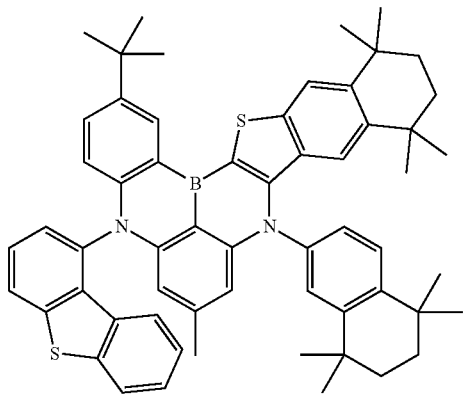
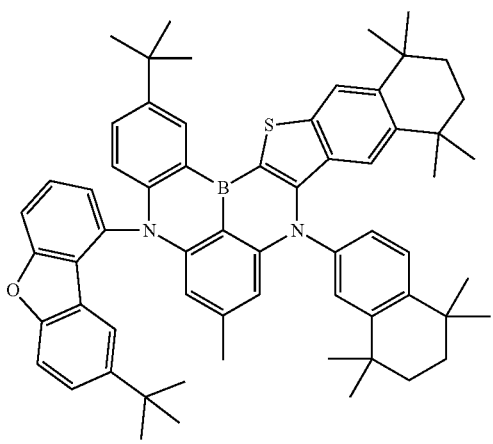
1492
-continued
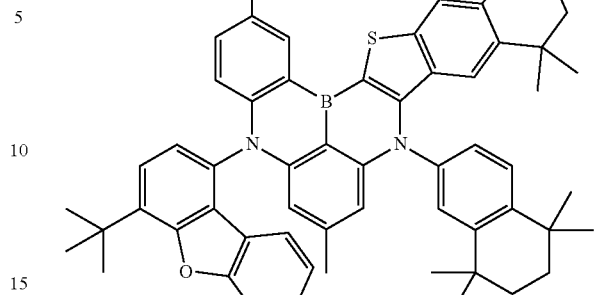
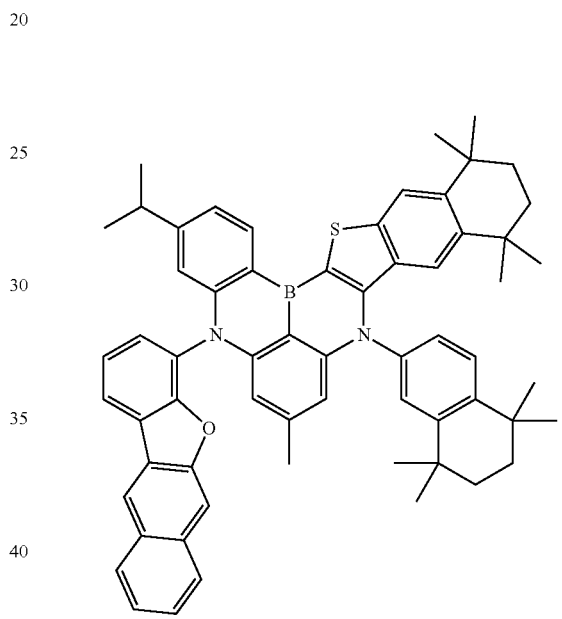
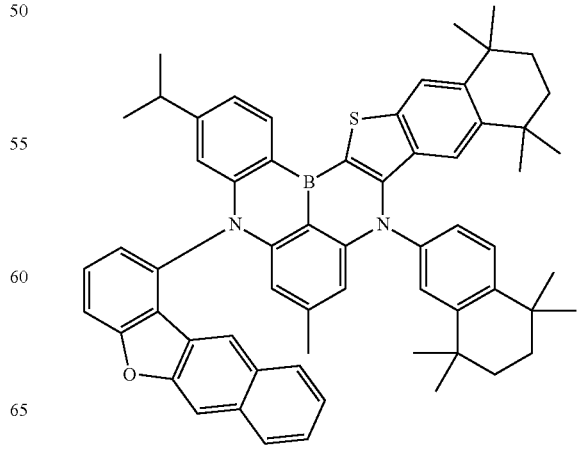

1493
-continued
1494
-continued
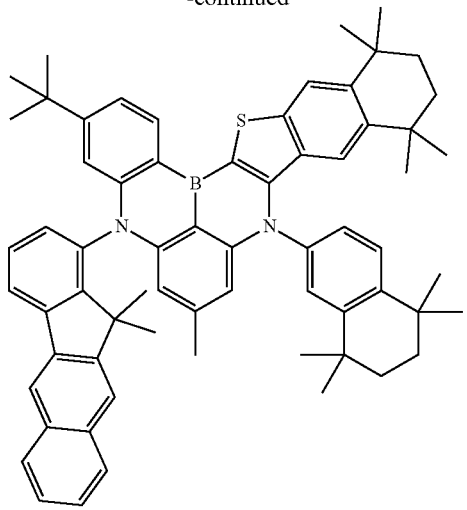
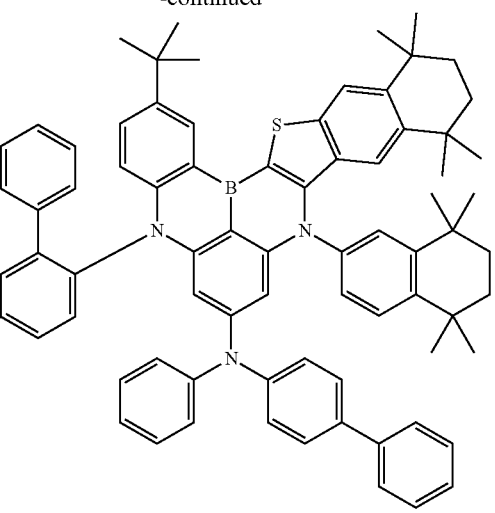
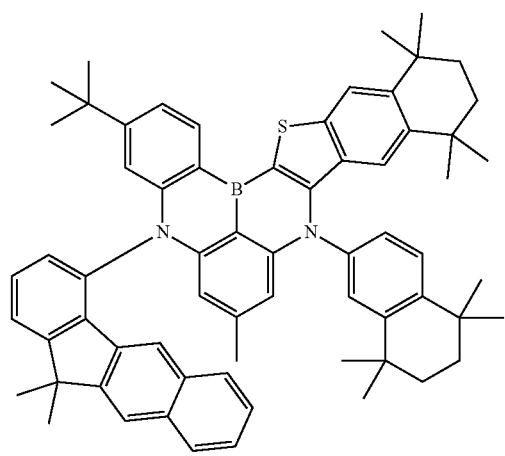
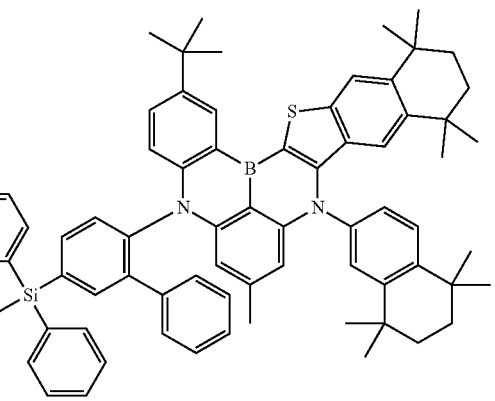
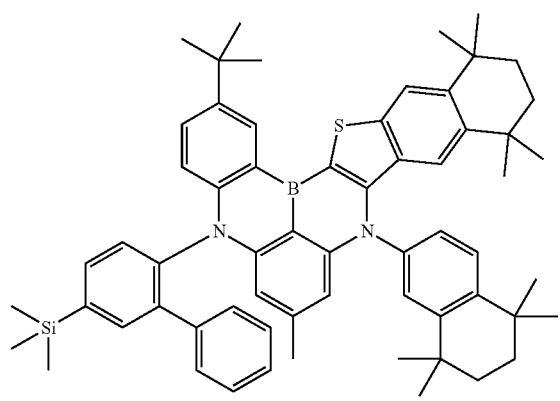
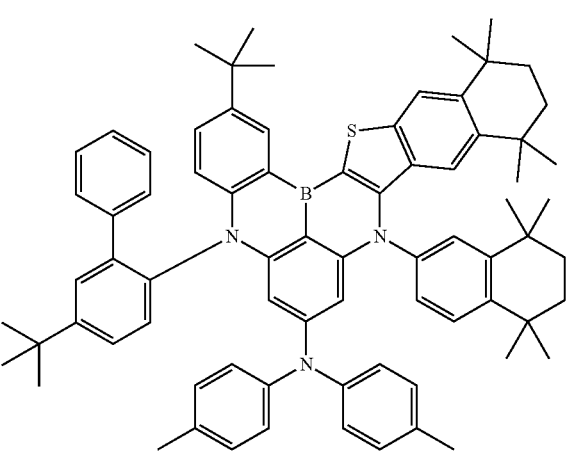

1495
-continued
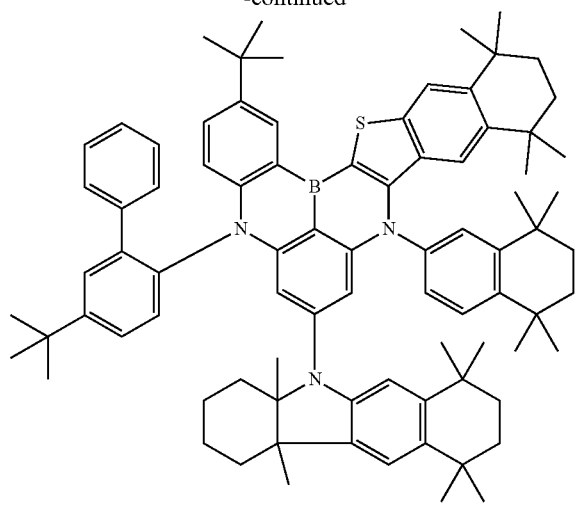
1496
-continued
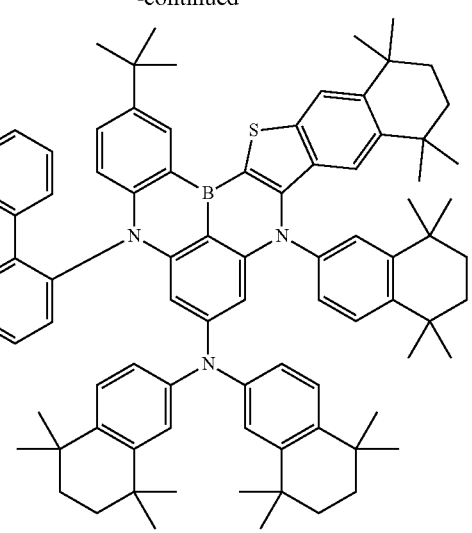
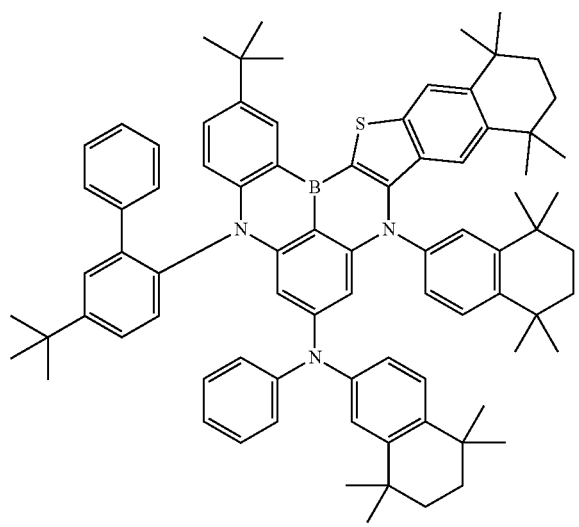 [SMILES: CC(C)(C)c1ccc2c(c1)B1c3sc4cc5c(cc4c3N(c3ccc4c(c3)C(C)(C)CCC4(C)C)c3cc(N(c4ccc6c(c4)C(C)(C)CCC6(C)C)c4ccc6c(c4)C(C)(C)CCC6(C)C)cc(c31)N2c1ccc(C(C)(C)C)cc1-c1ccccc1)C(C)(C)CCC5(C)C]
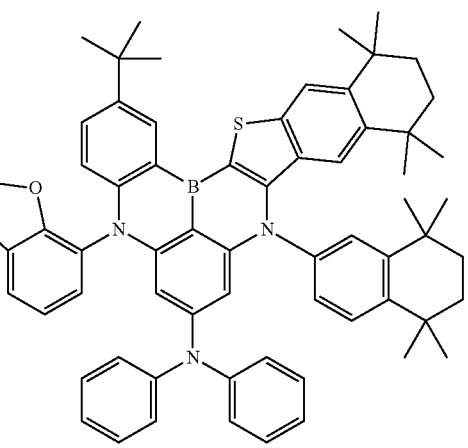
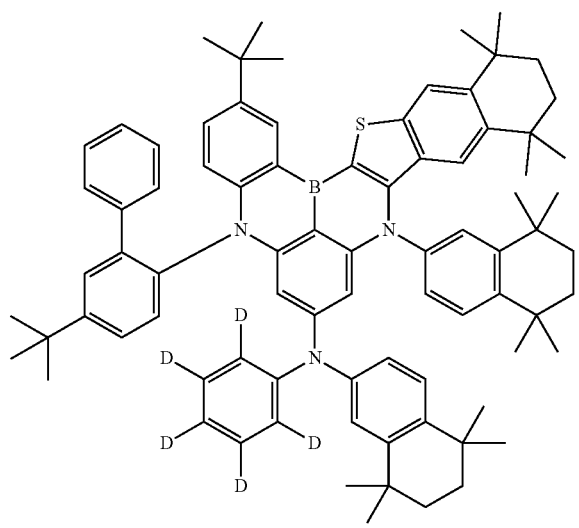
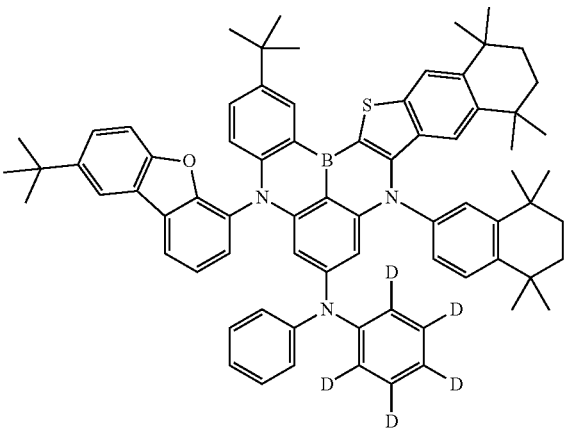

1497
-continued
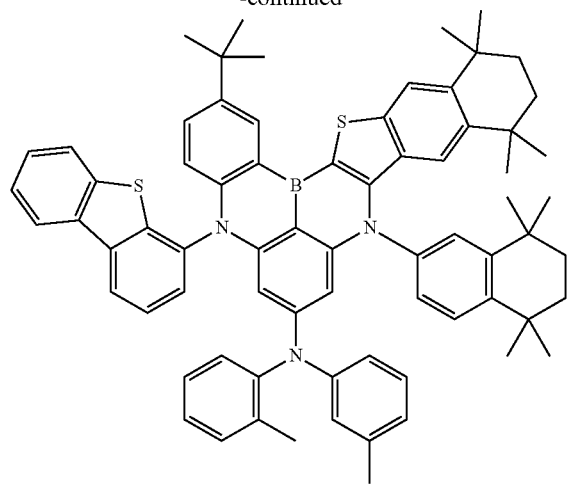
1498
-continued
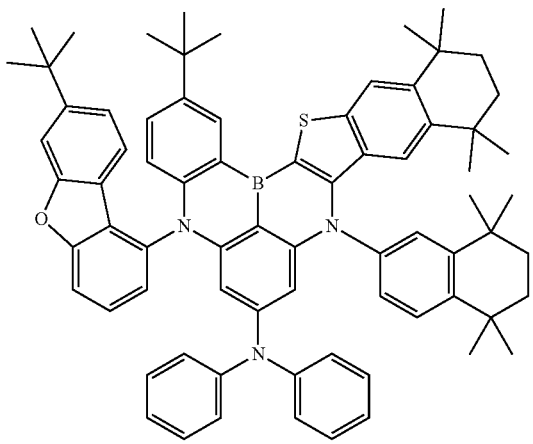
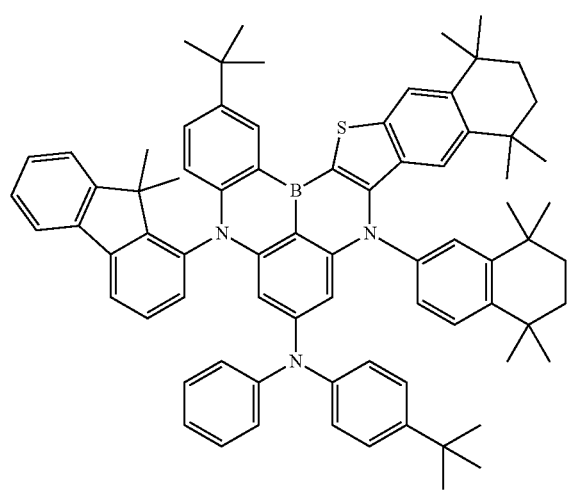
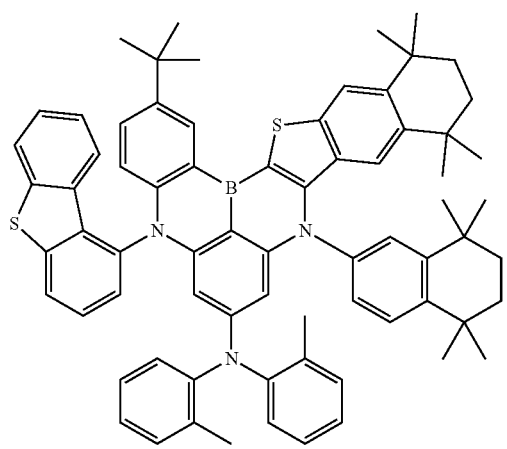
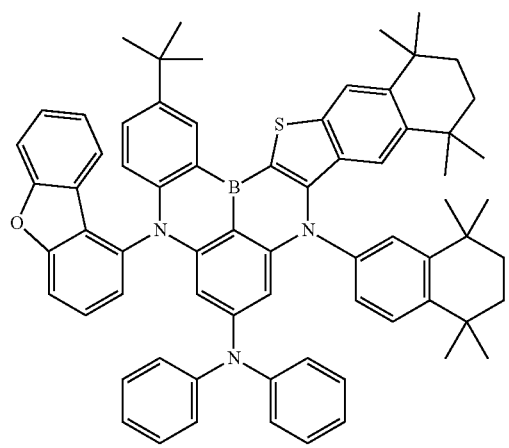
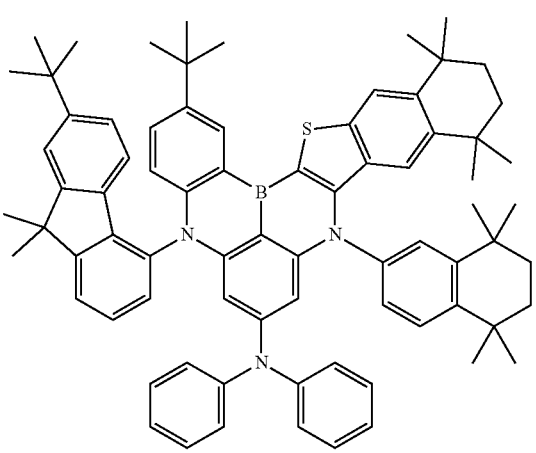

1499
-continued
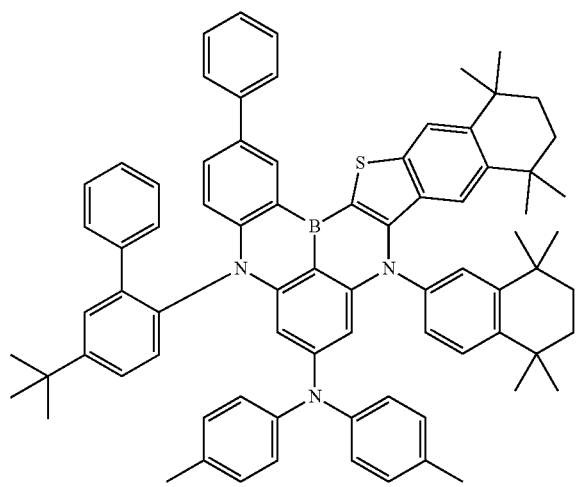
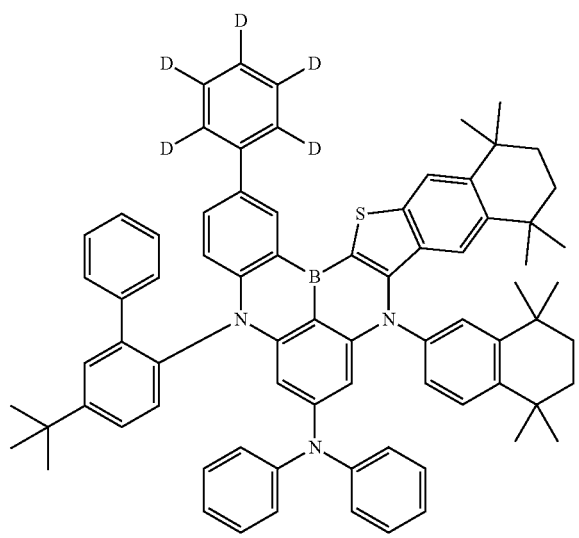
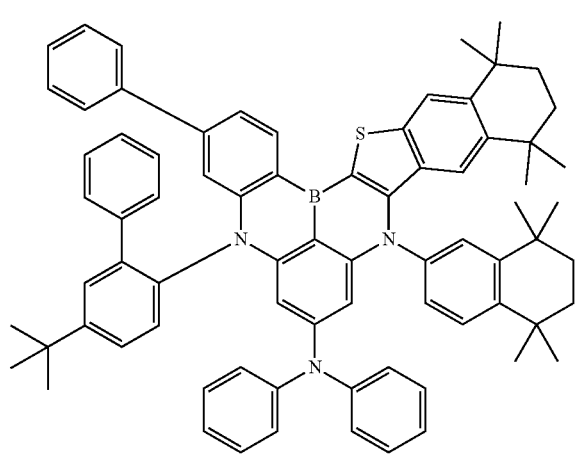
1500
-continued
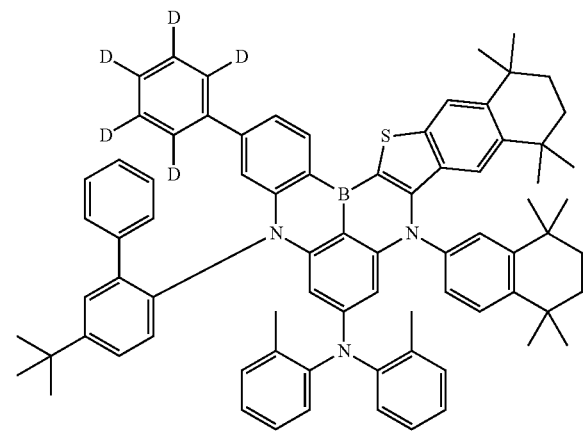

1501
-continued
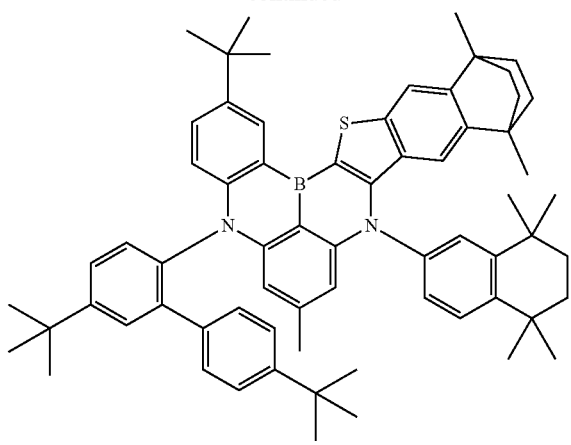
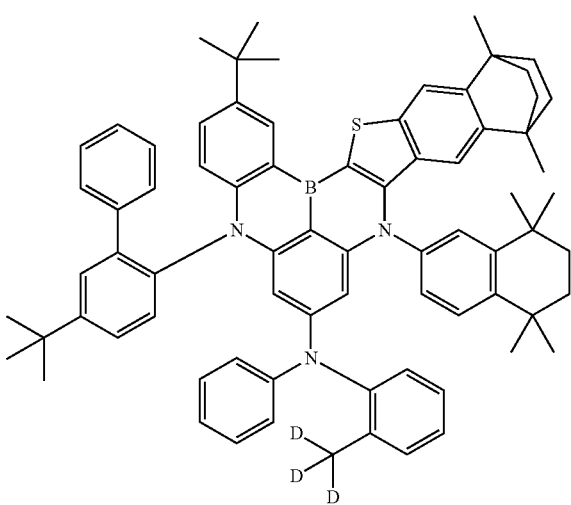
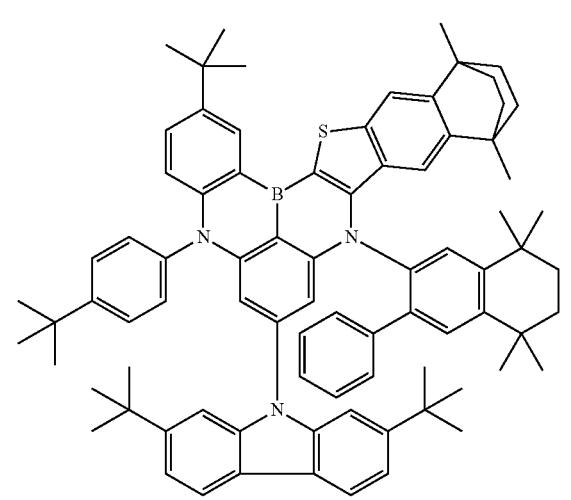
1502
-continued
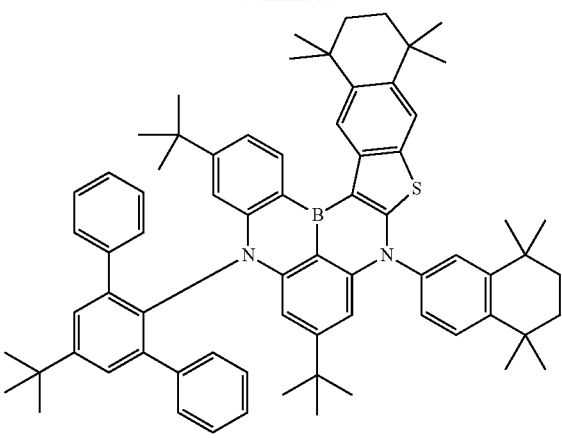
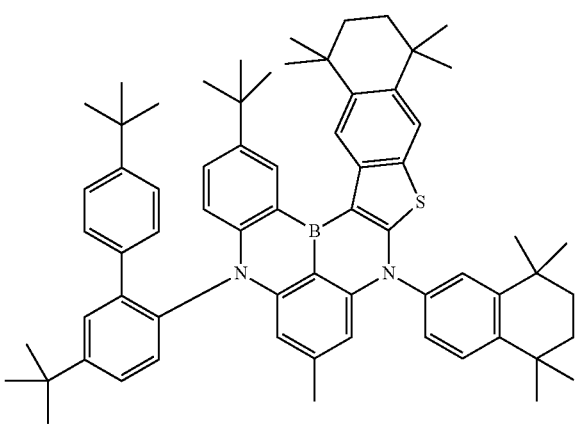
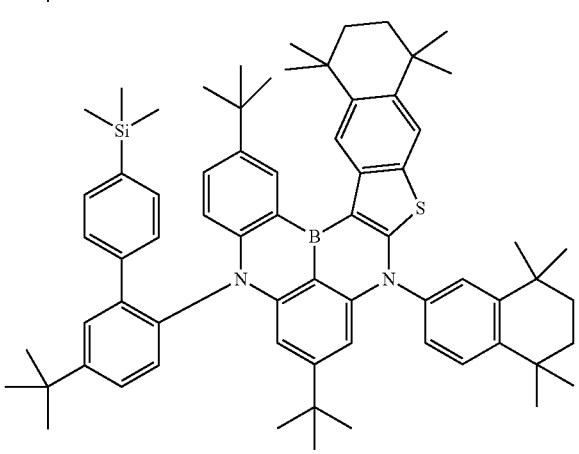
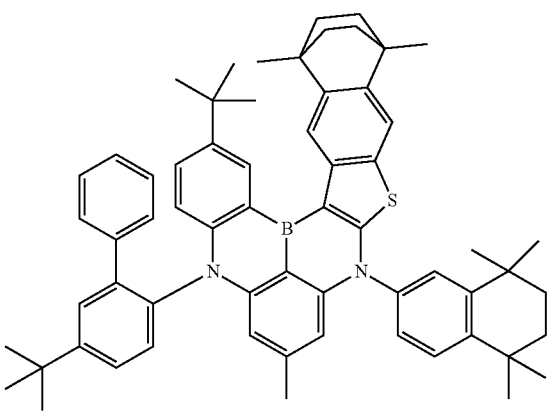

1503
-continued
1504
-continued
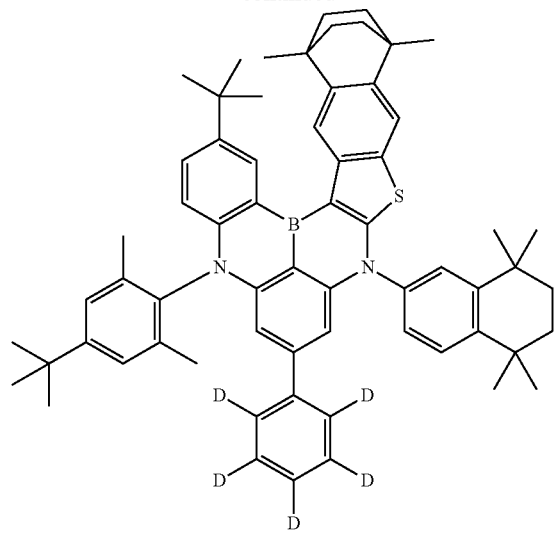
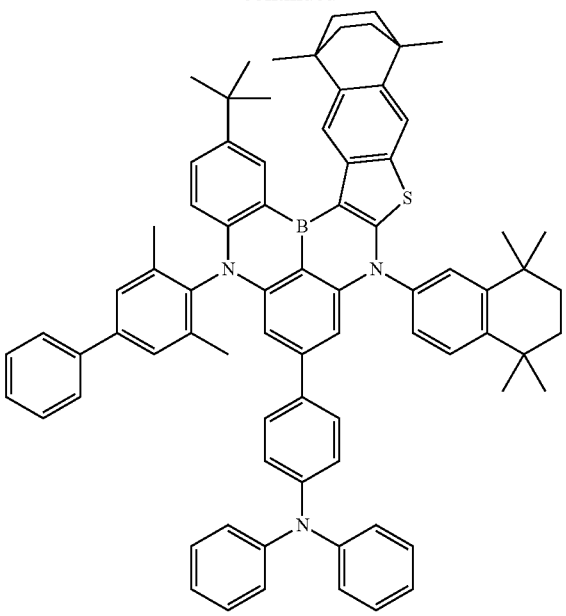
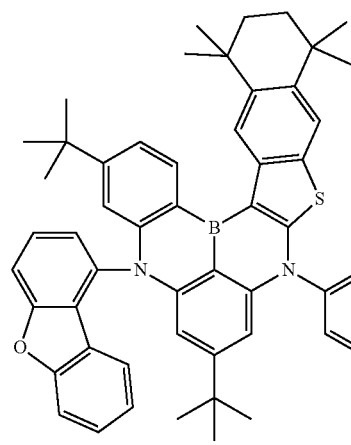
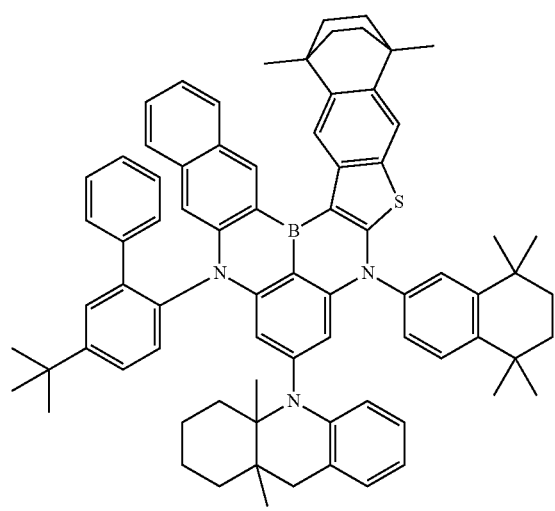
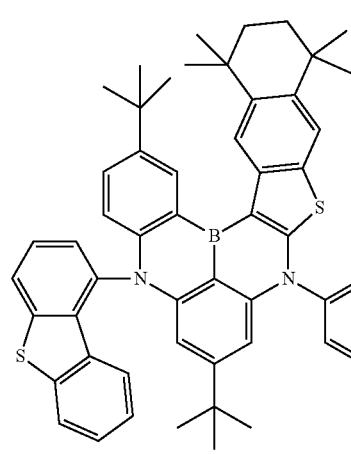

1505
-continued
1506
-continued
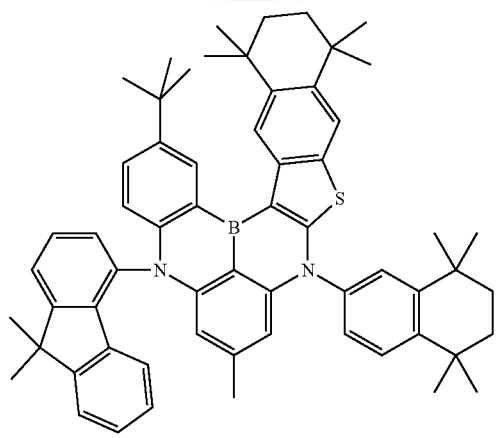
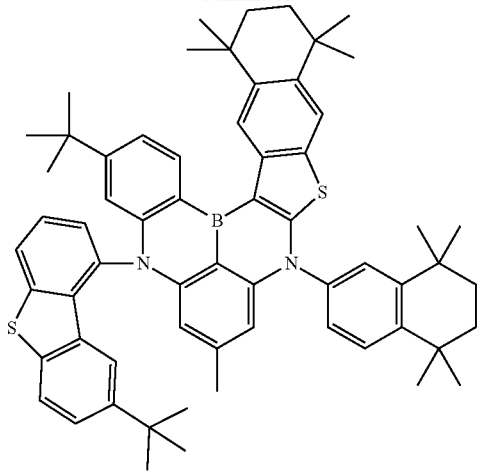
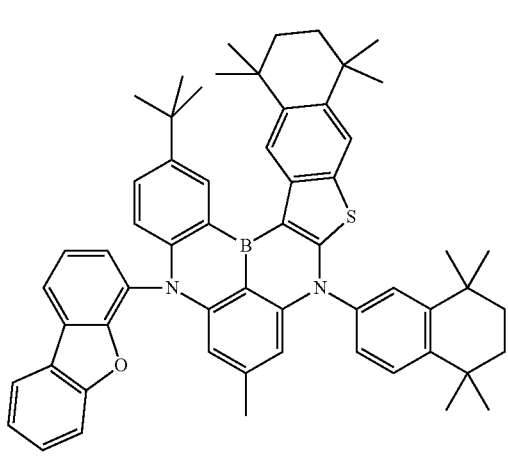
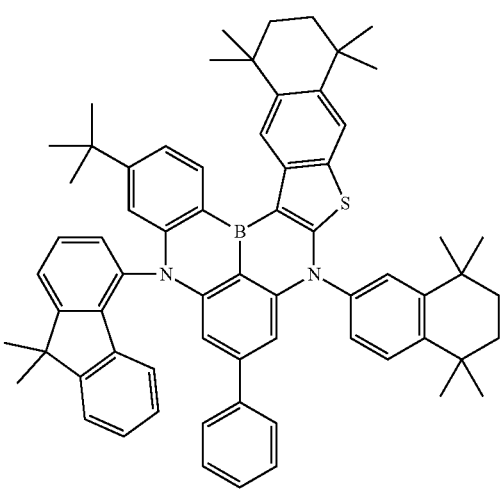
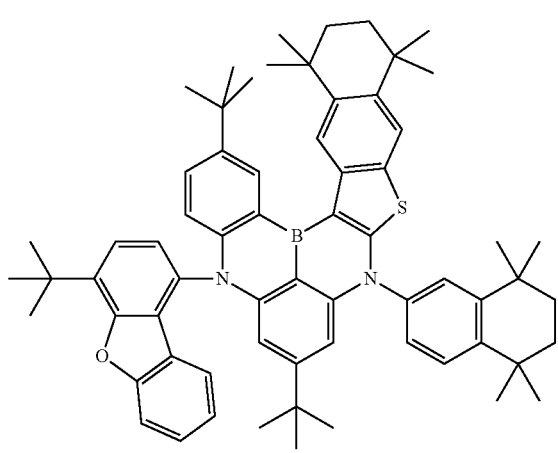
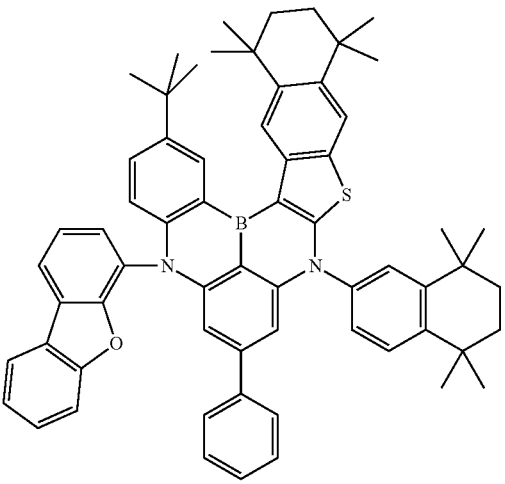

1507
-continued
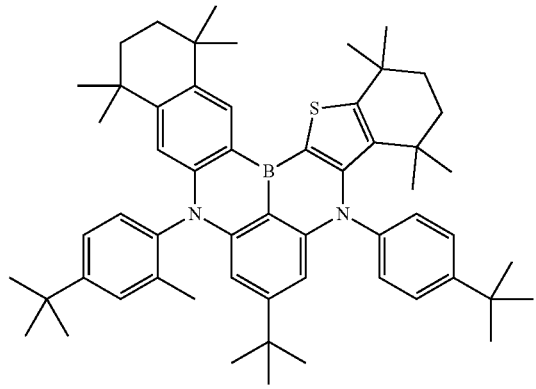
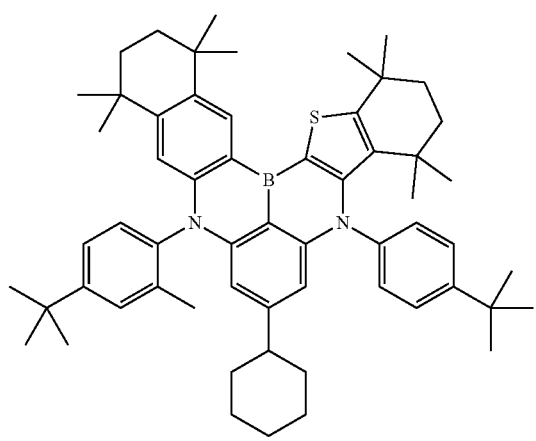
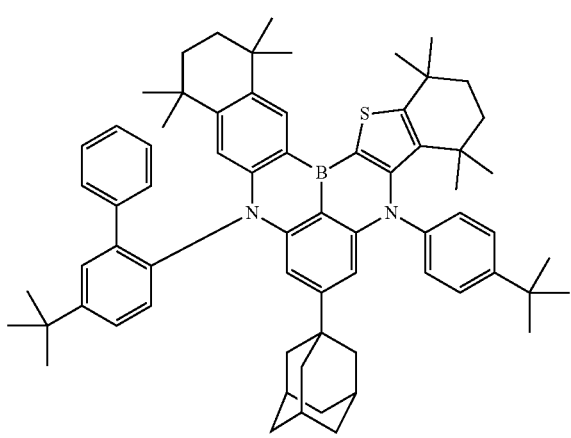
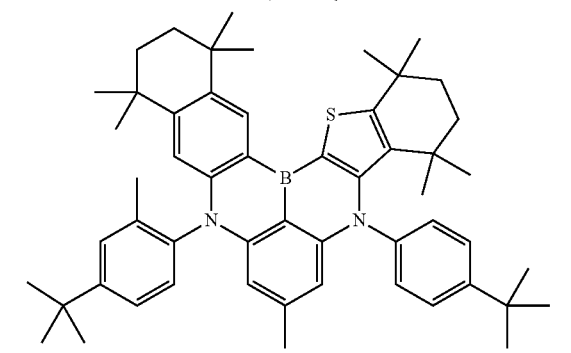
1508
-continued
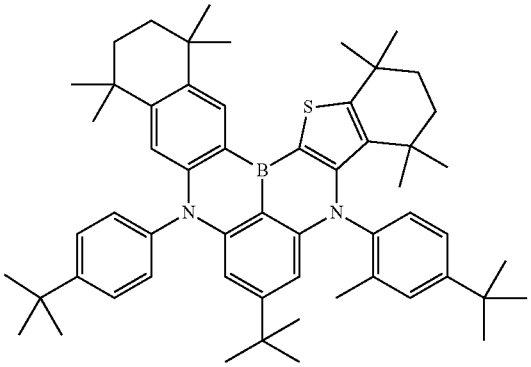
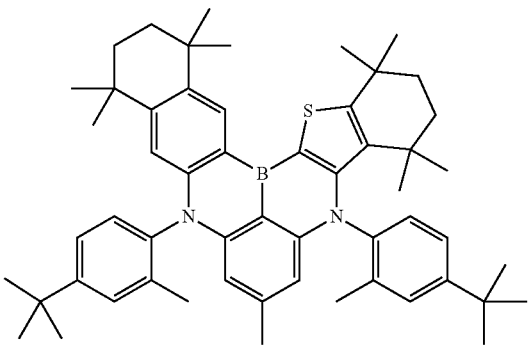
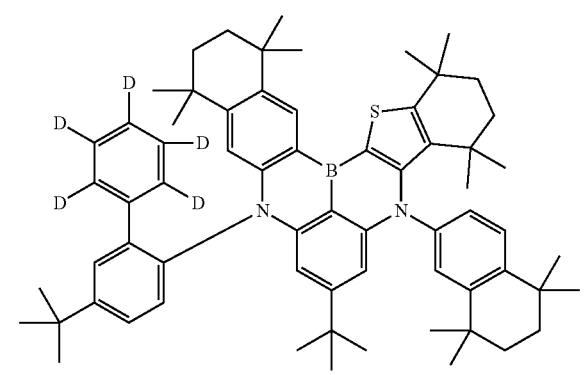
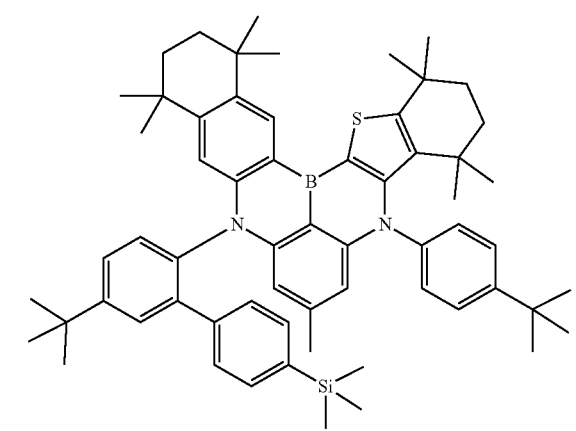

1509
-continued
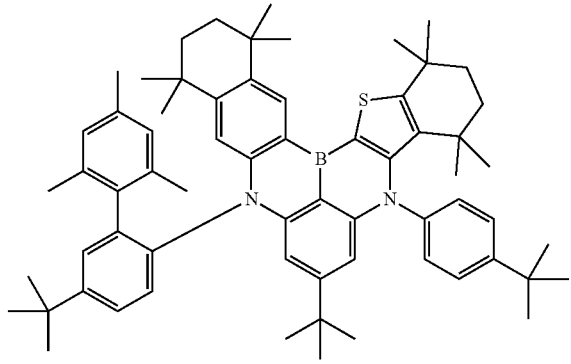
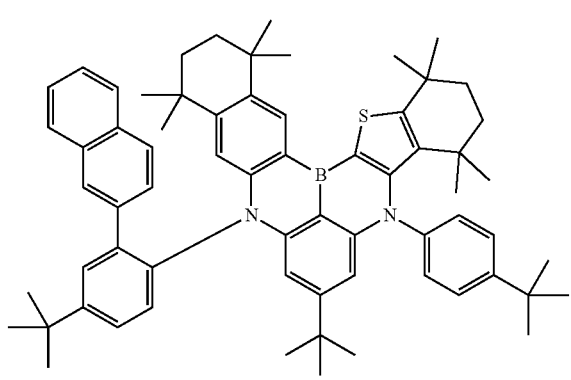
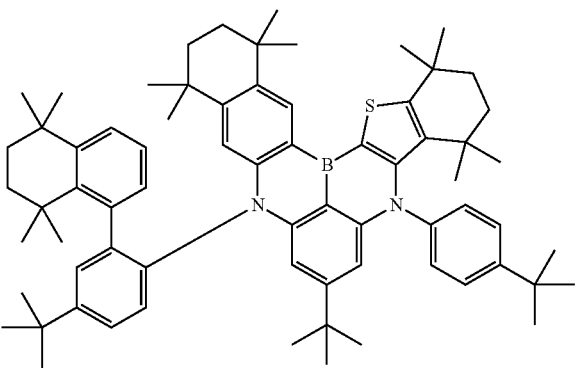
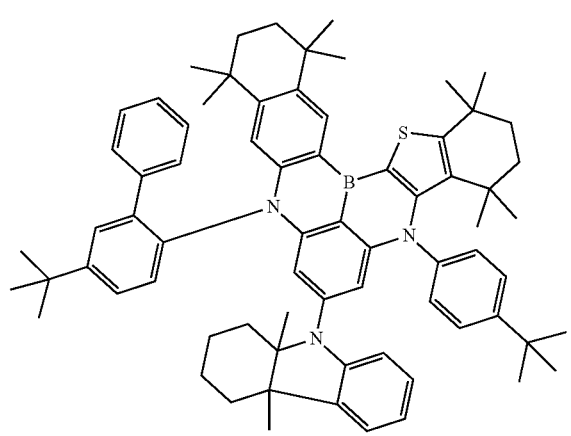
1510
-continued
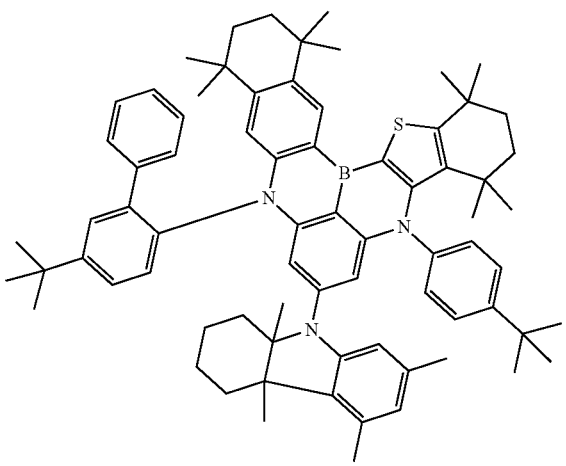
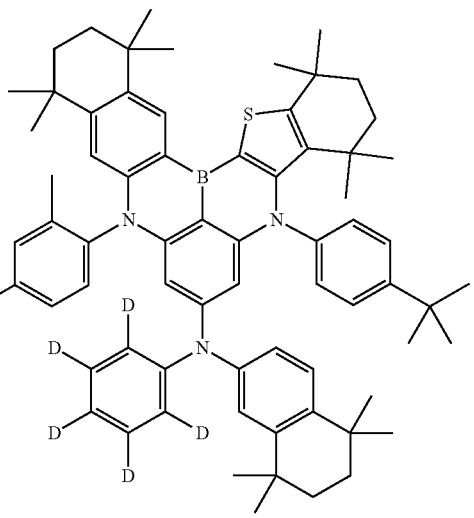
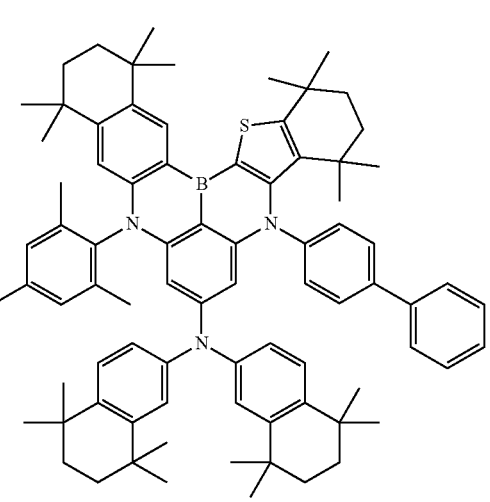

| 1511 -continued | 1512 -continued |
|---|---|
| 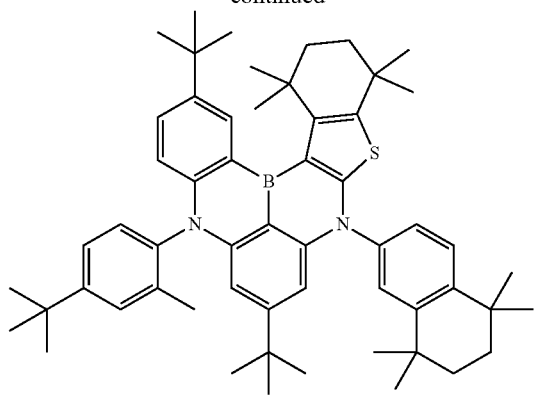 | 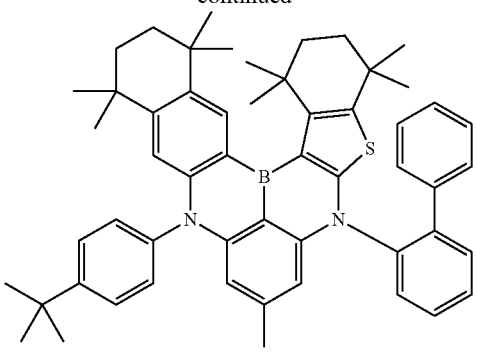 |
| 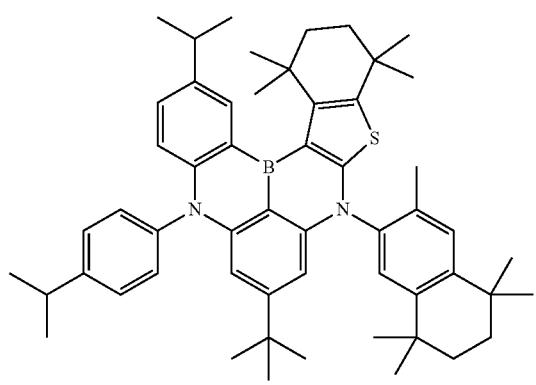 | 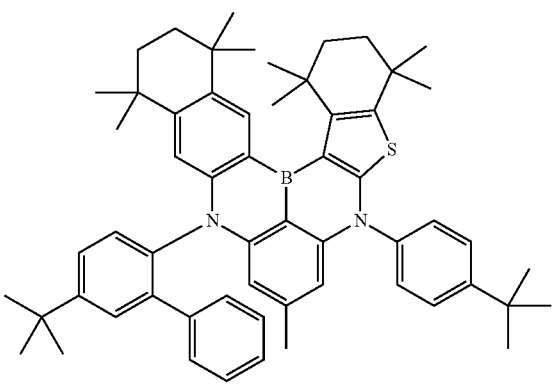 |
| 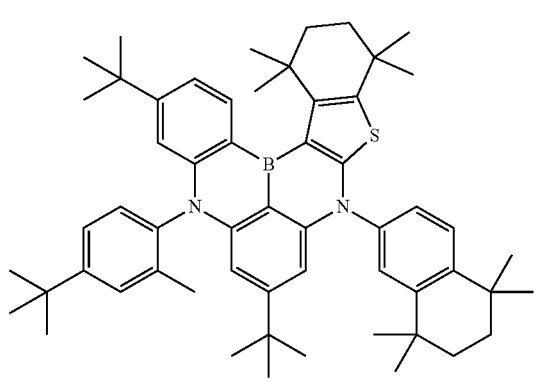 | 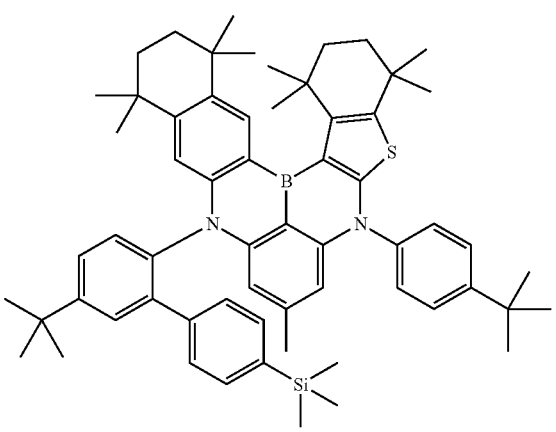 |
| 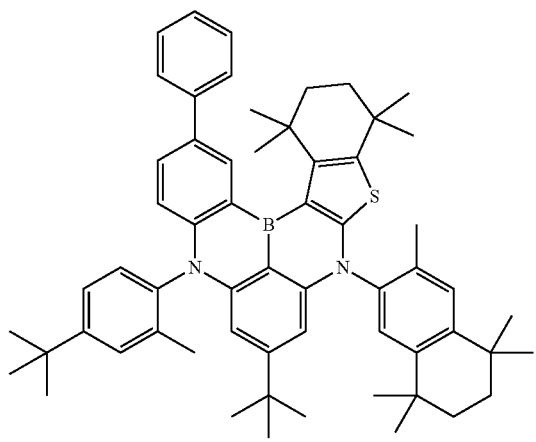 | 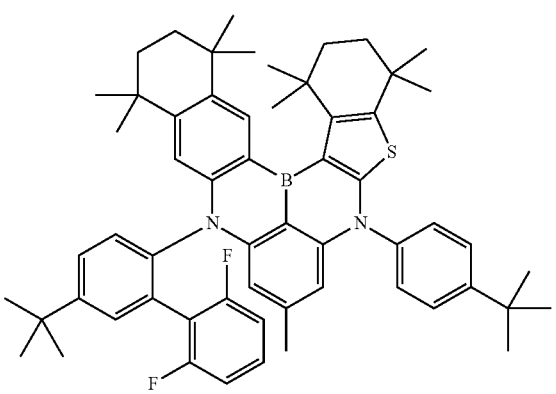 |

1513
-continued
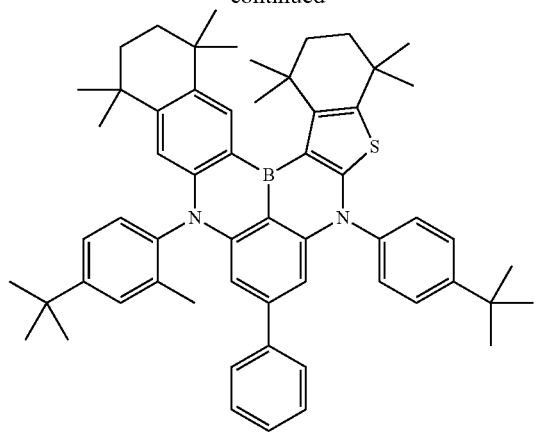
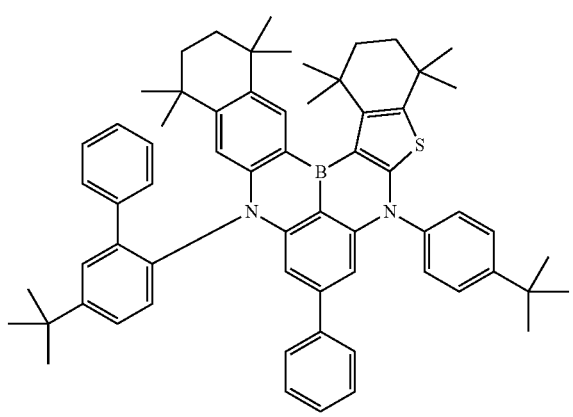
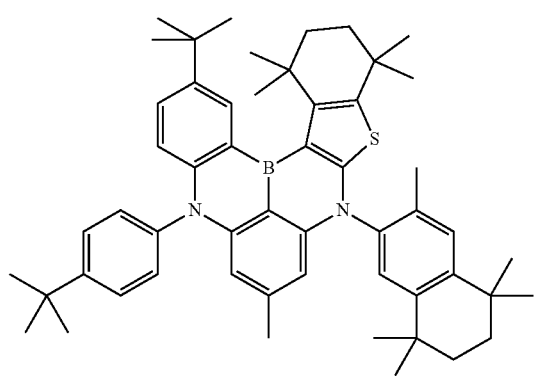
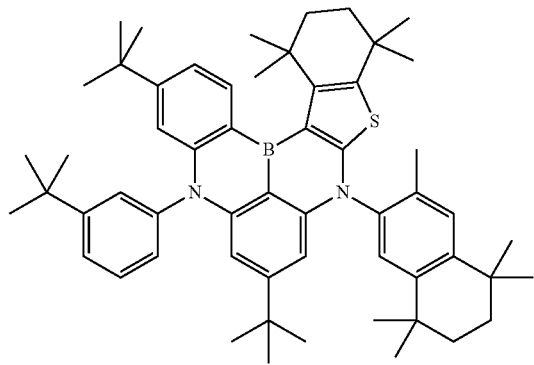
1514
-continued
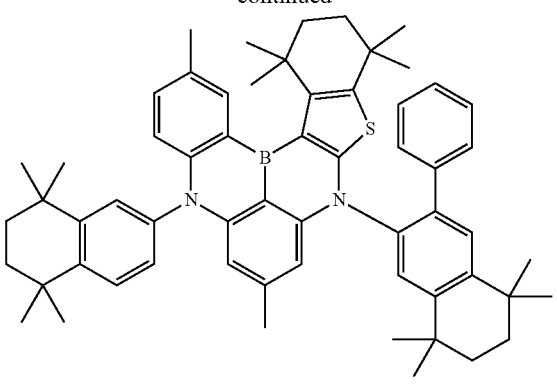
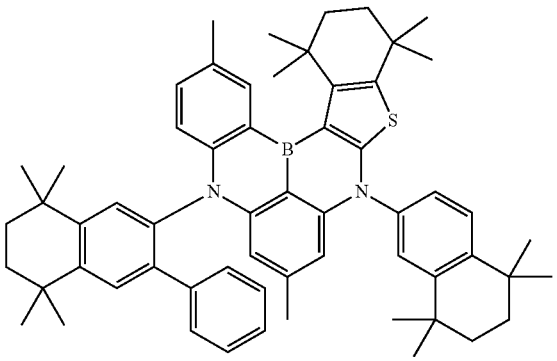
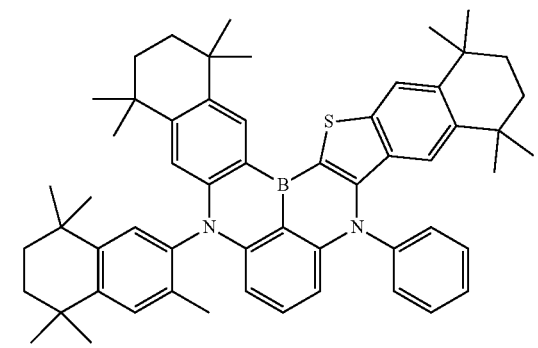
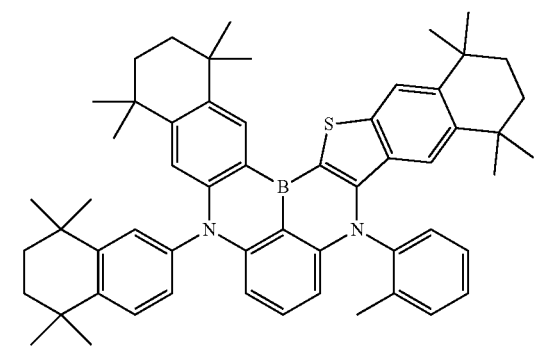

1515
-continued
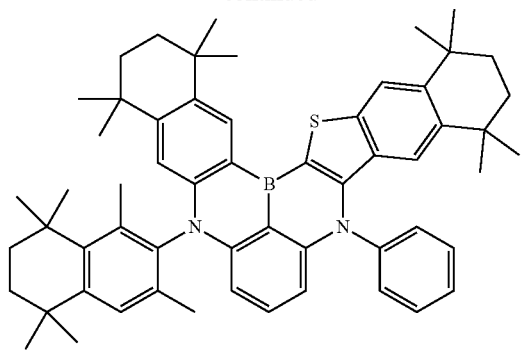
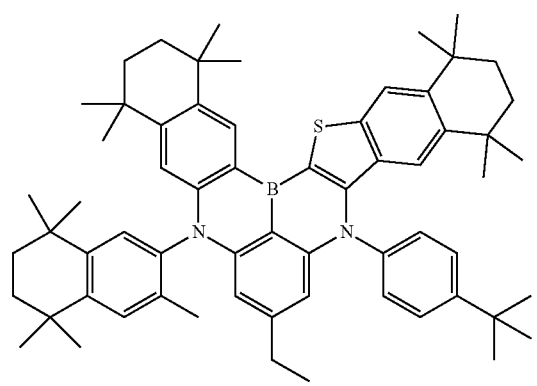
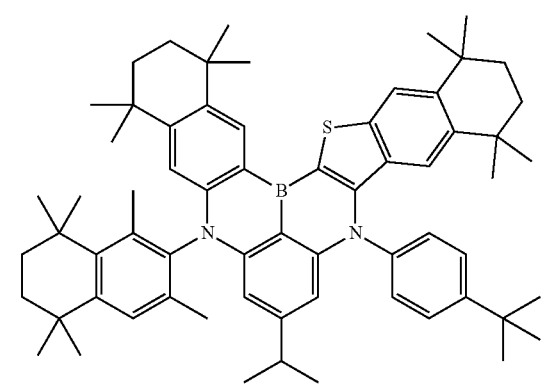
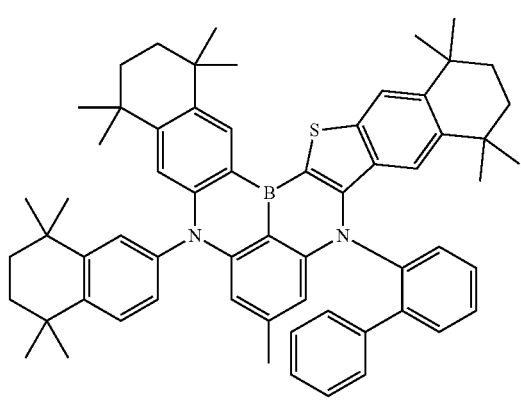
1516
-continued
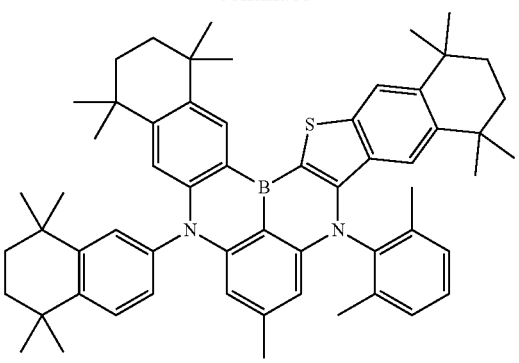
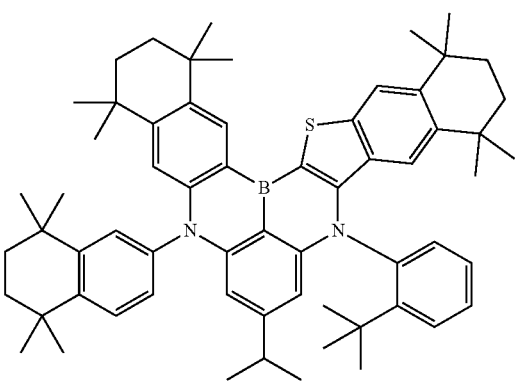
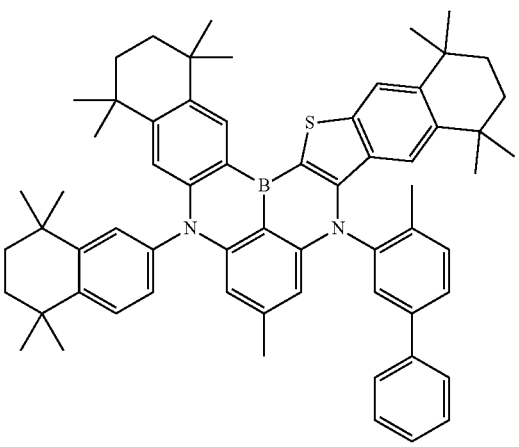
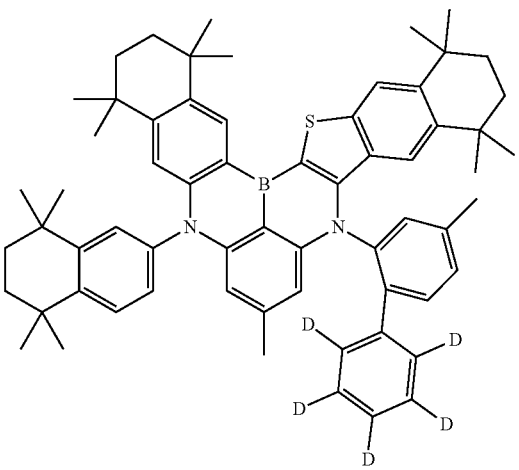

1517
-continued
1518
-continued
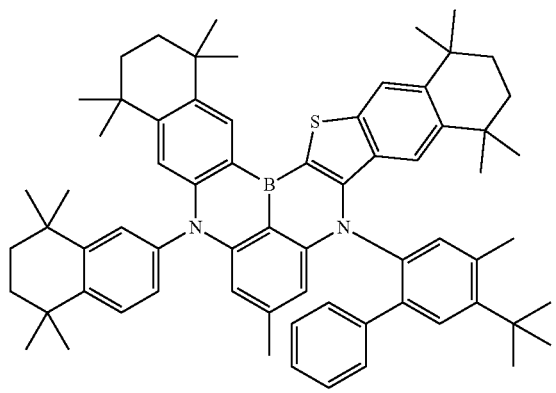
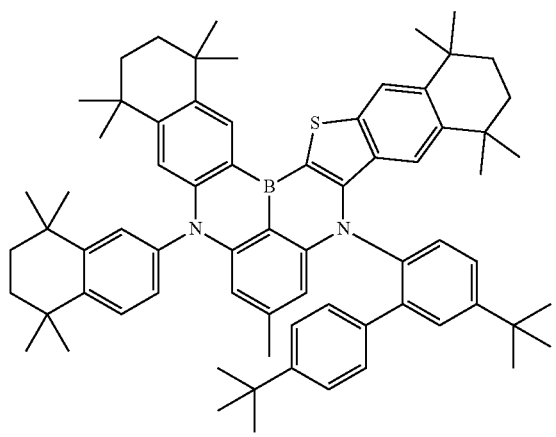
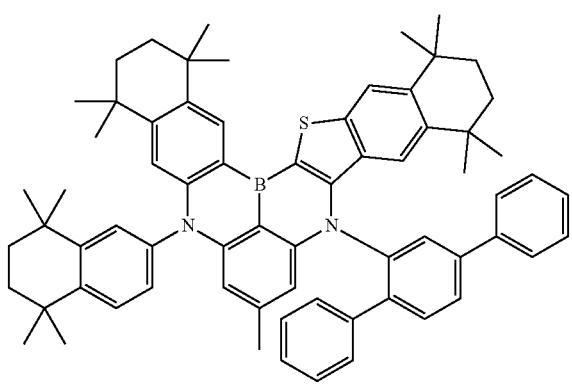
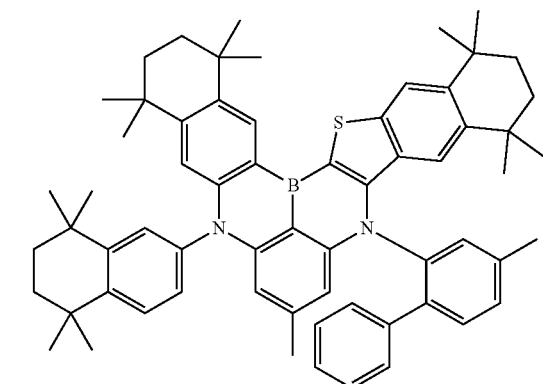
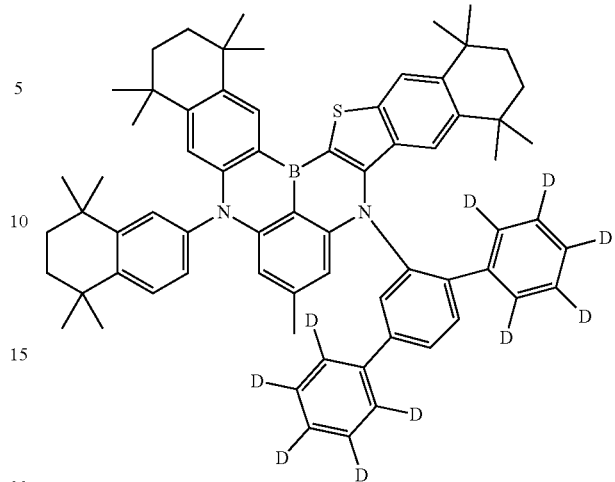
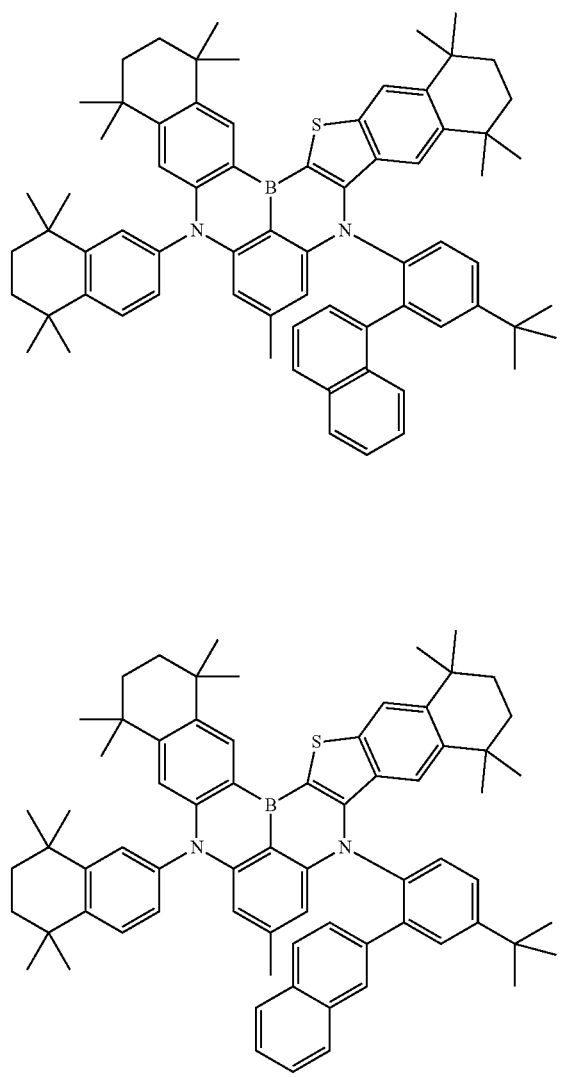

1519
-continued
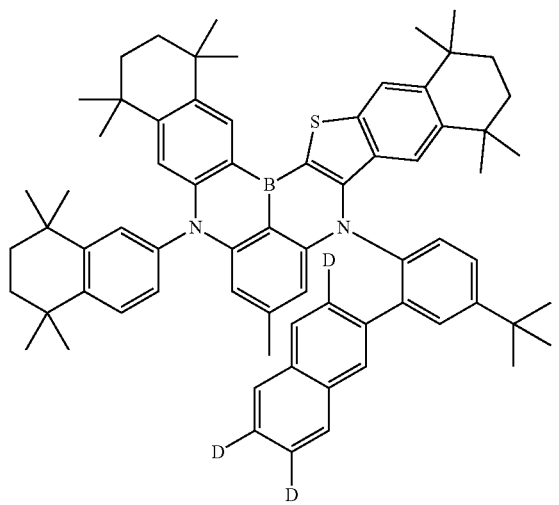
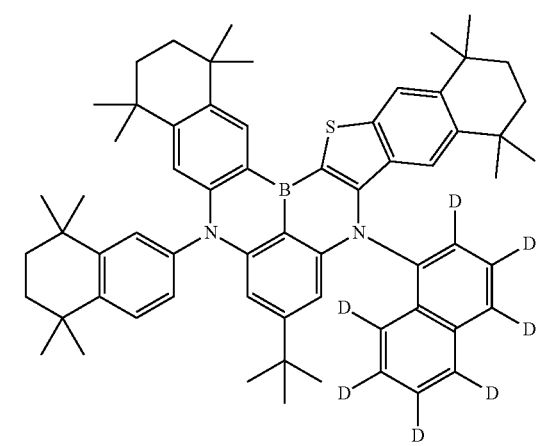
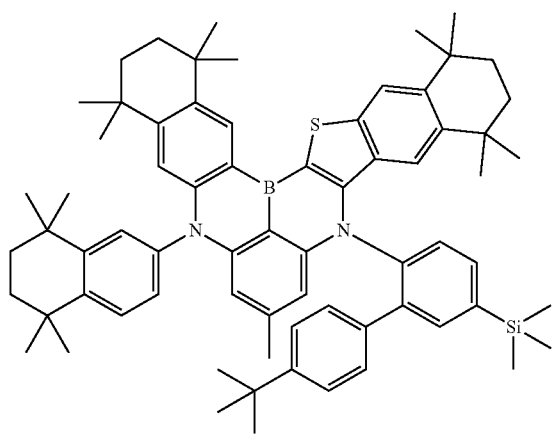
1520
-continued
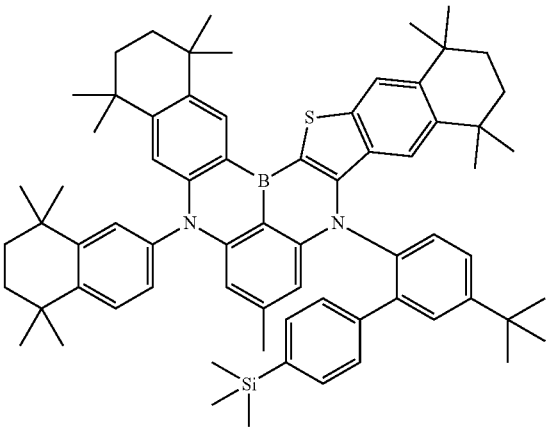
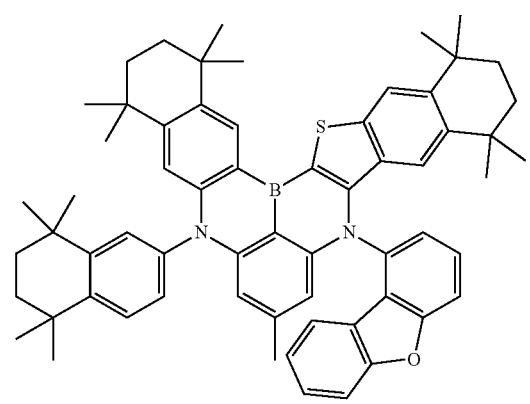
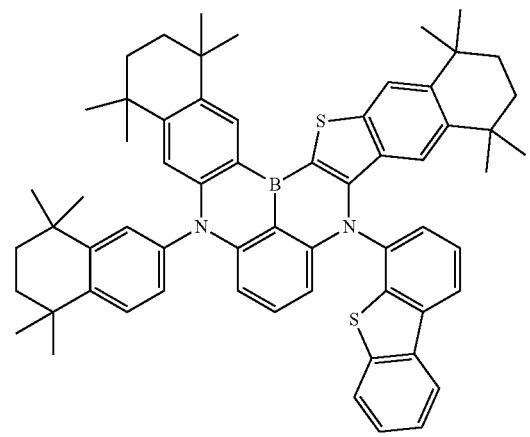
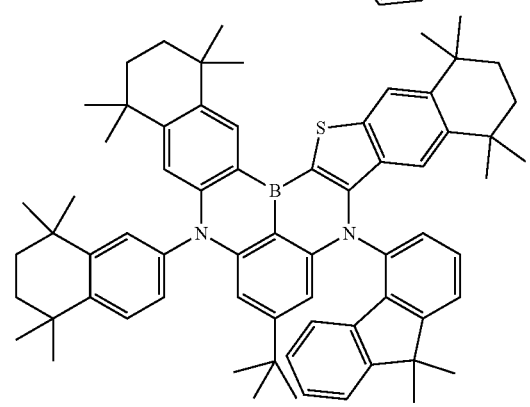

1521
-continued
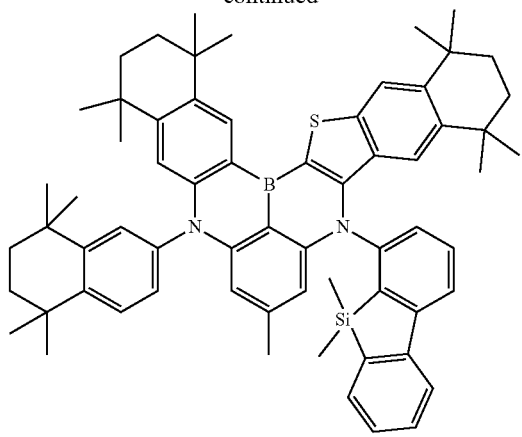
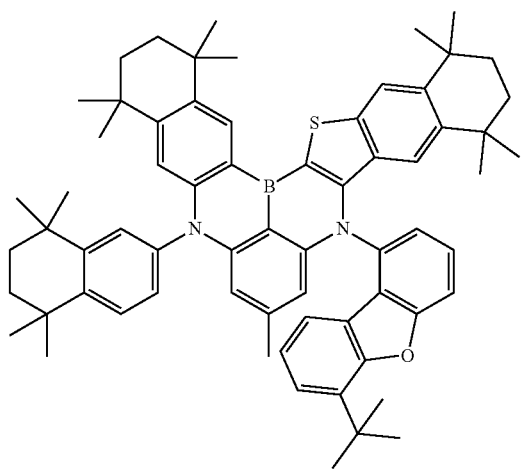
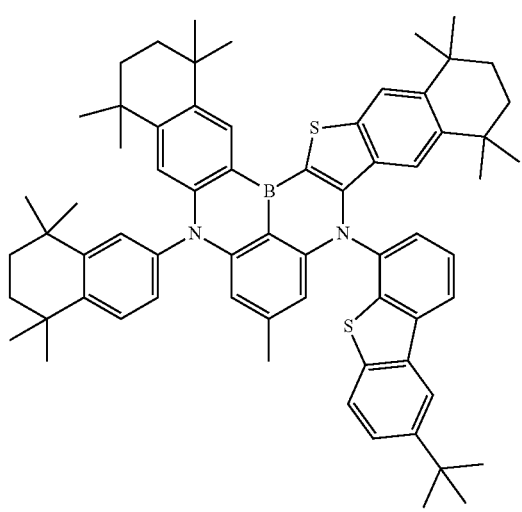
1522
-continued
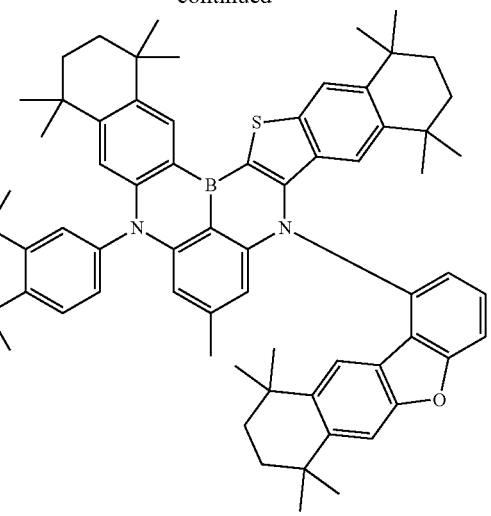
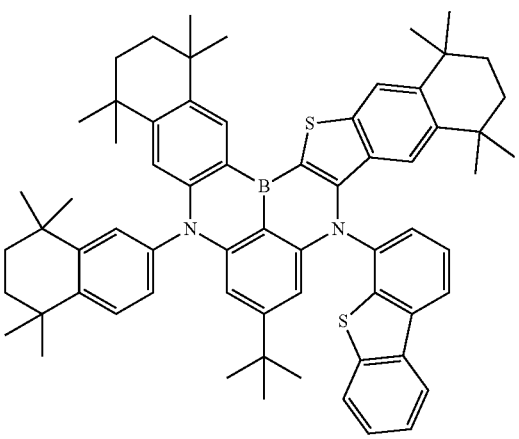
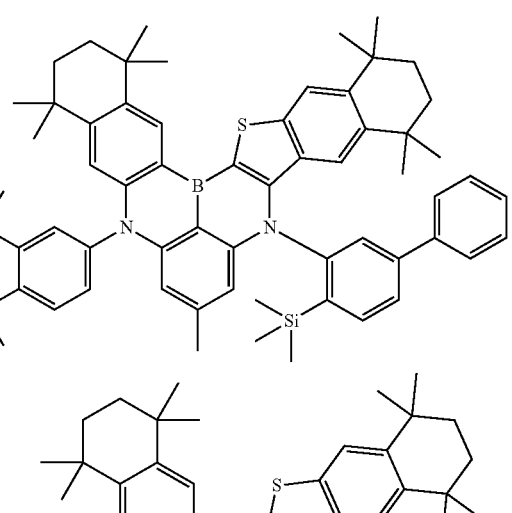
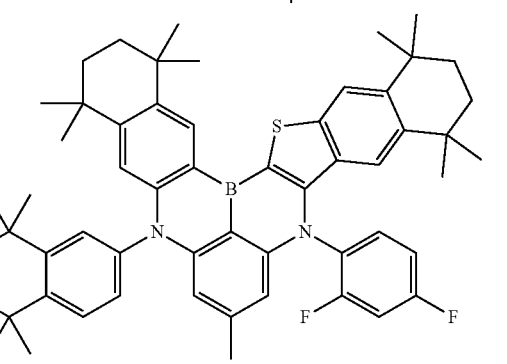

1523
-continued
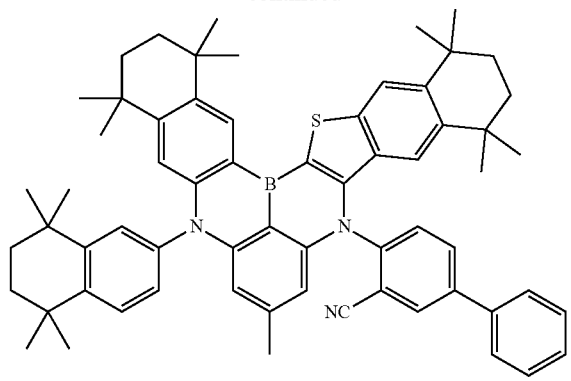
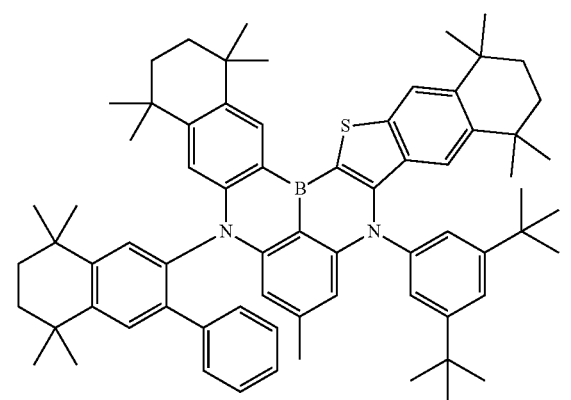
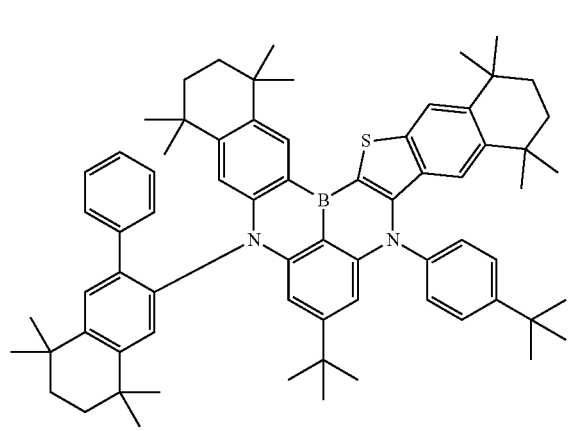
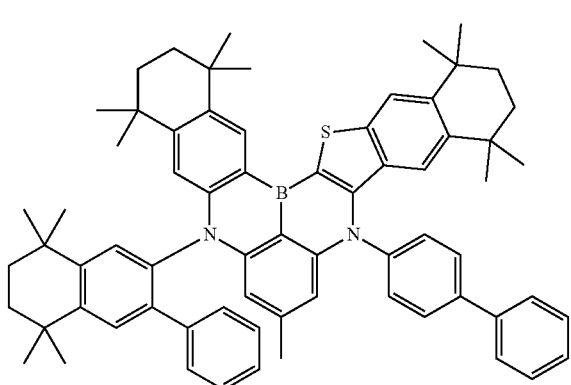
1524
-continued
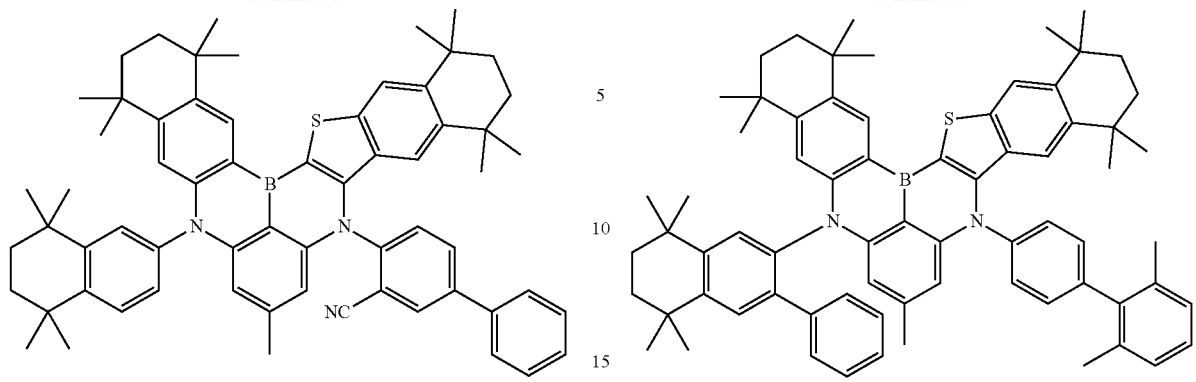
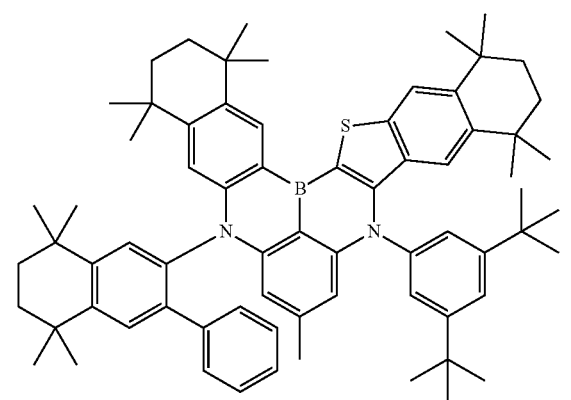
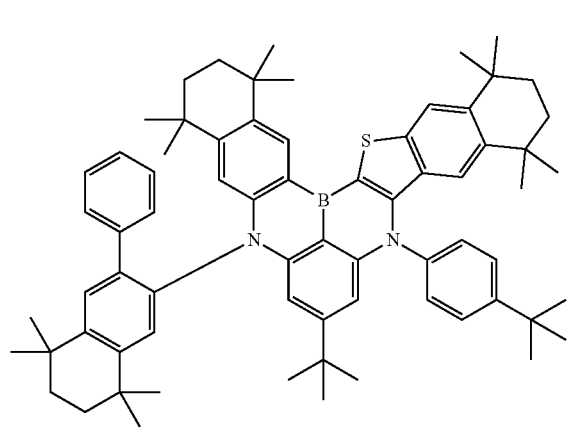
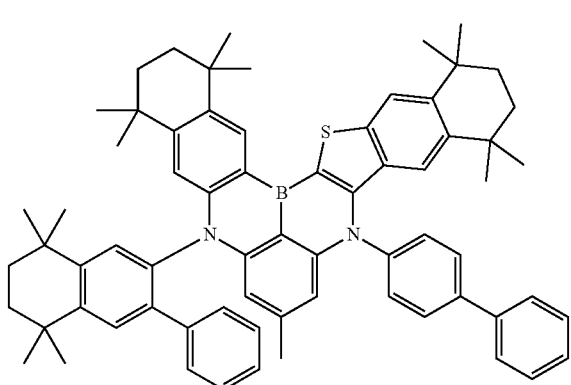

1525
-continued
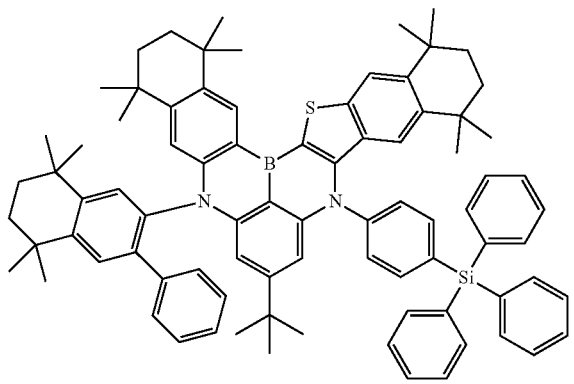
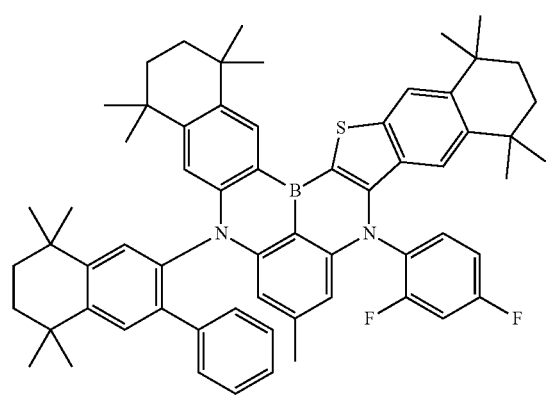
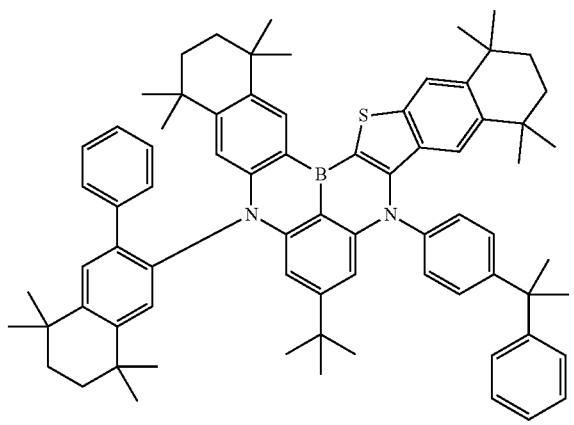
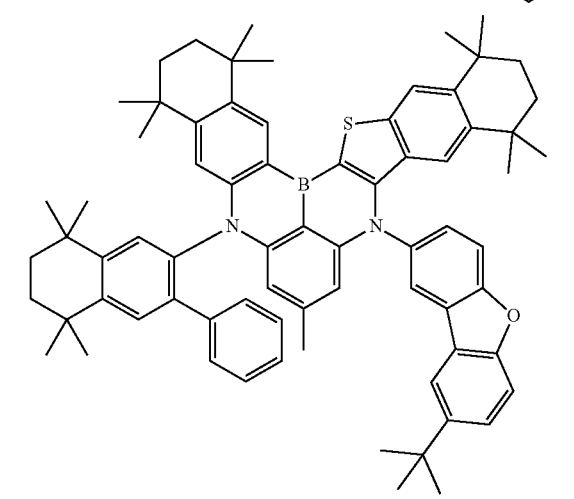
1526
-continued
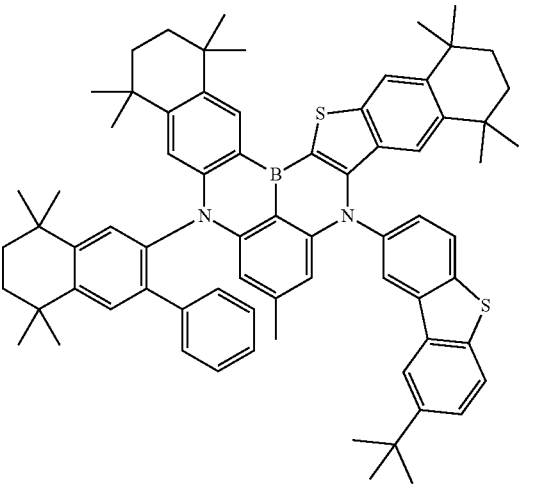
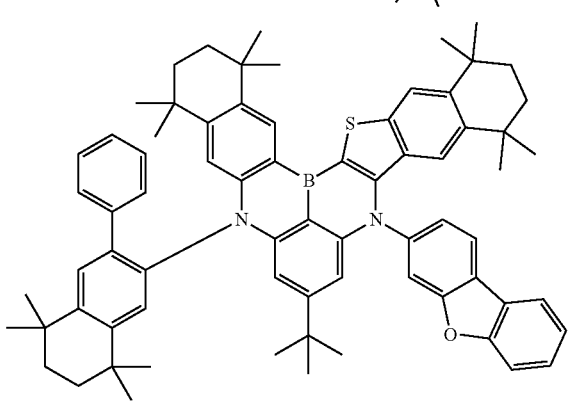
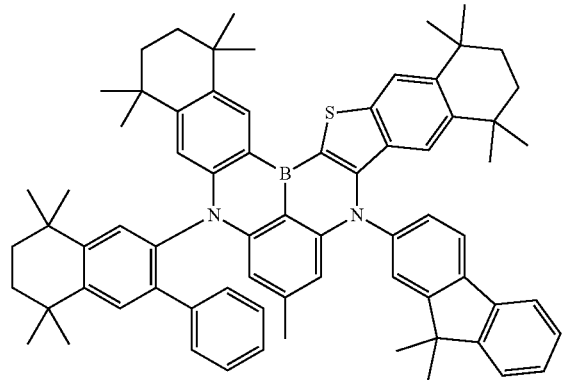
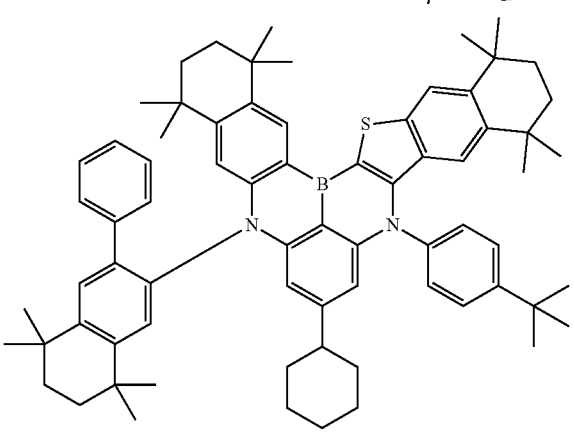

1527
-continued
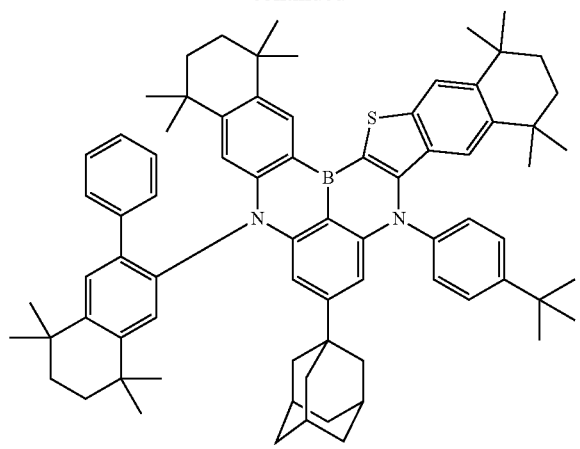
1528
-continued
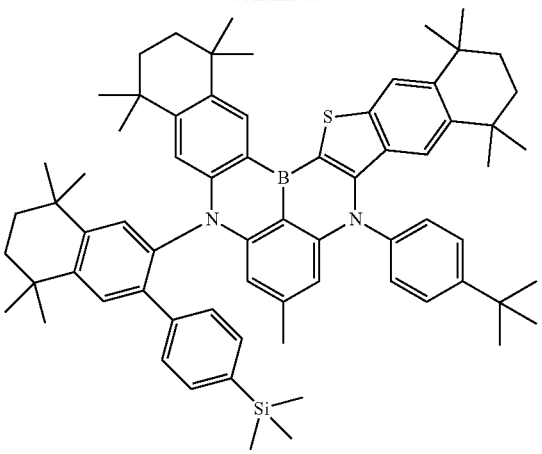
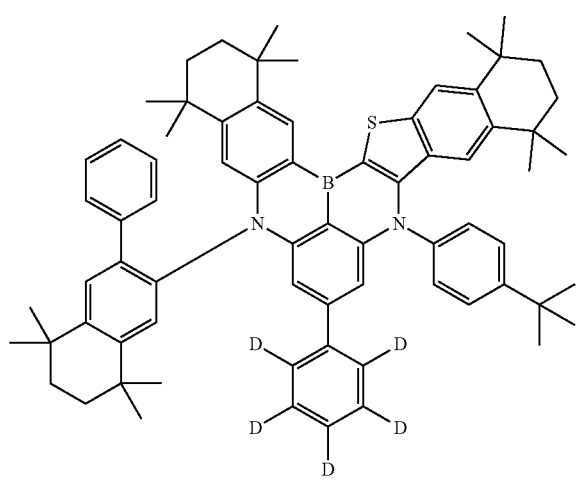
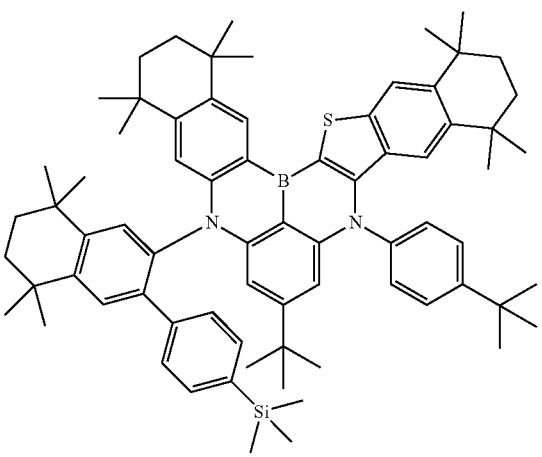
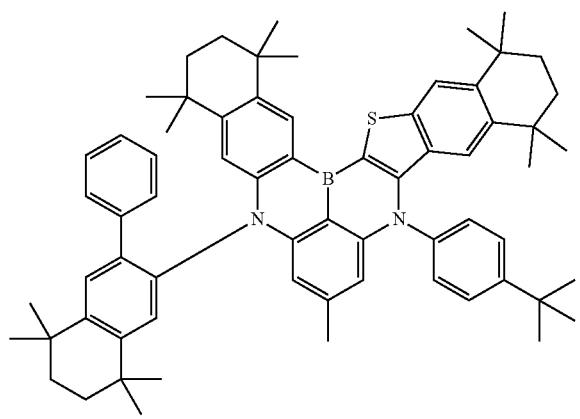
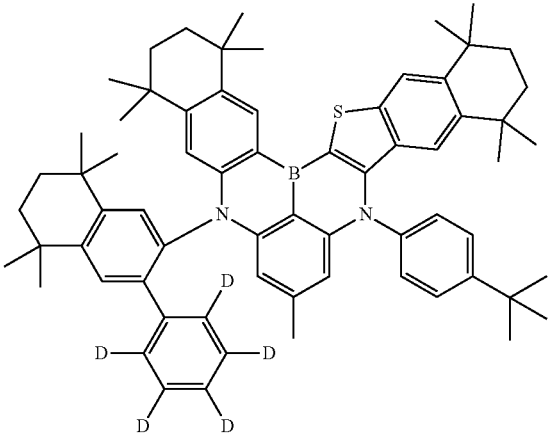

1529
-continued
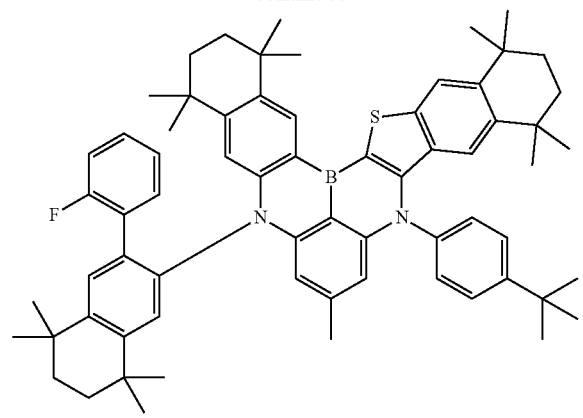
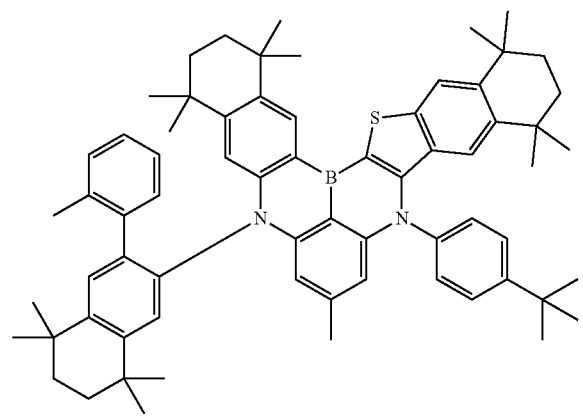
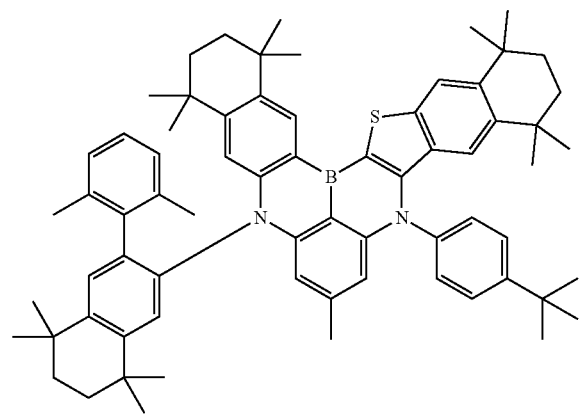
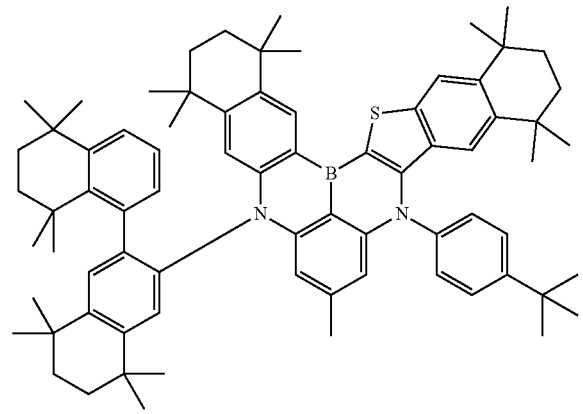
1530
-continued
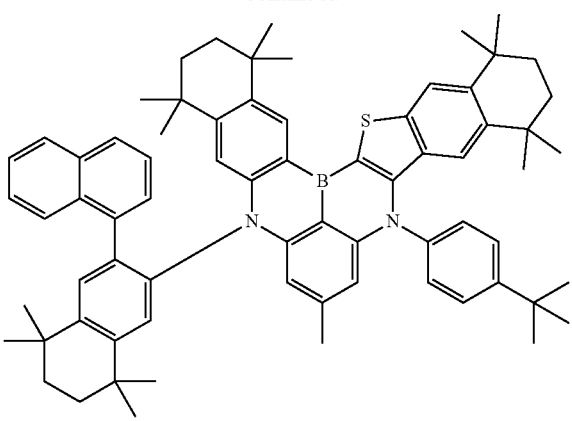
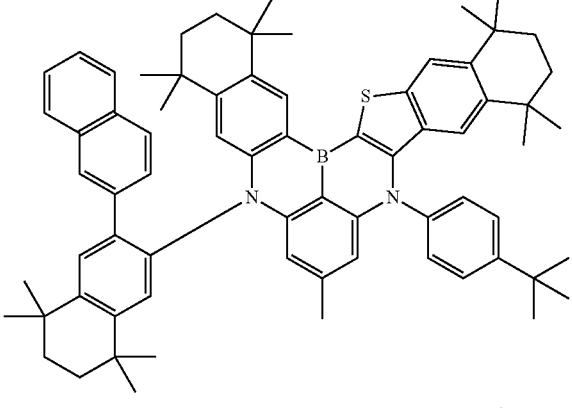
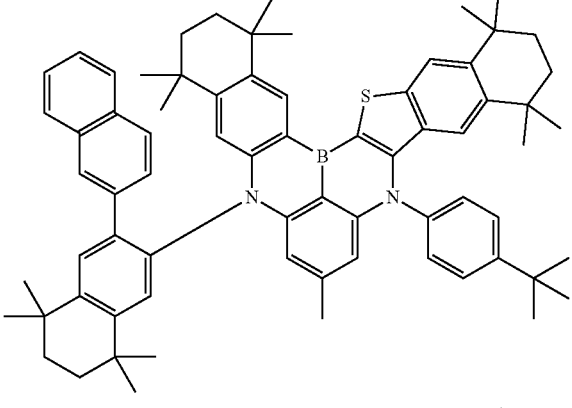
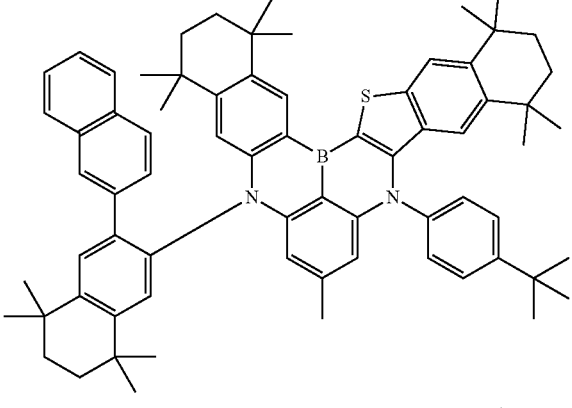

1531
-continued
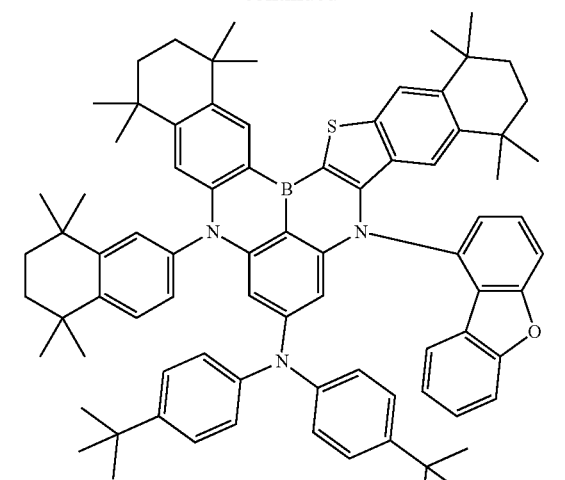
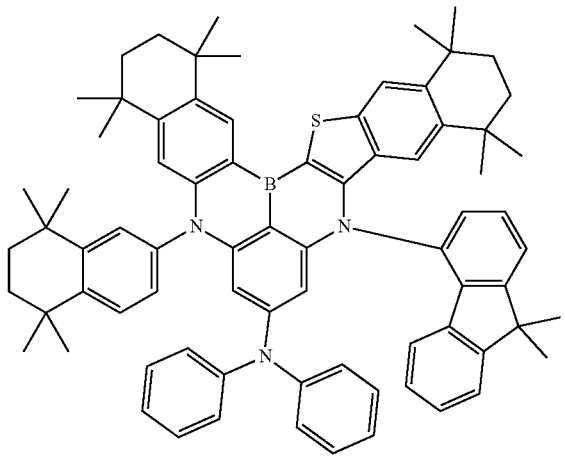
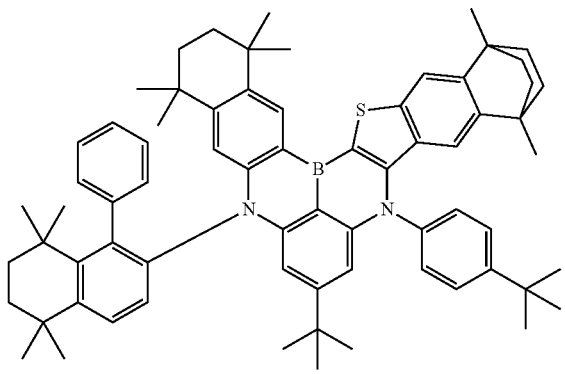
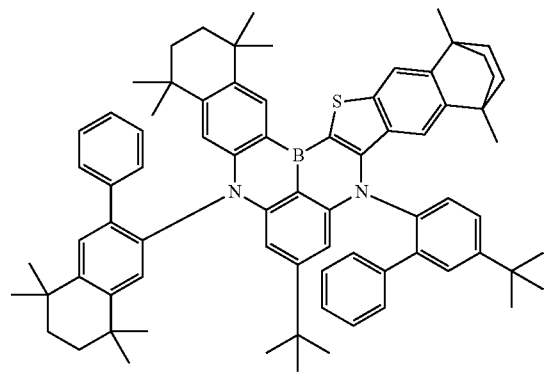
1532
-continued
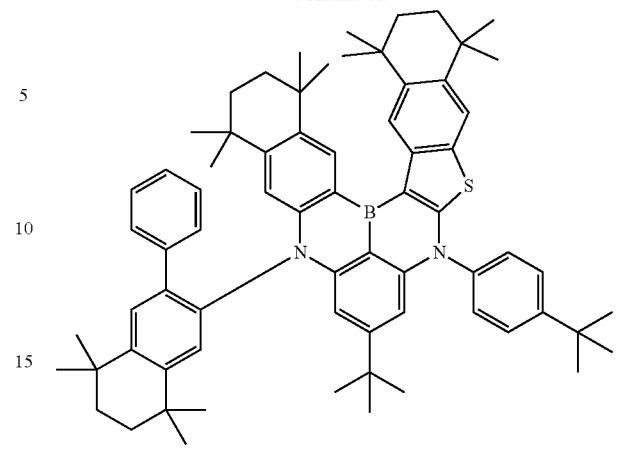
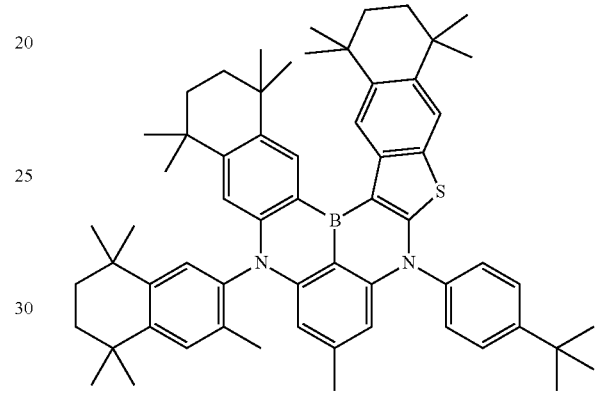
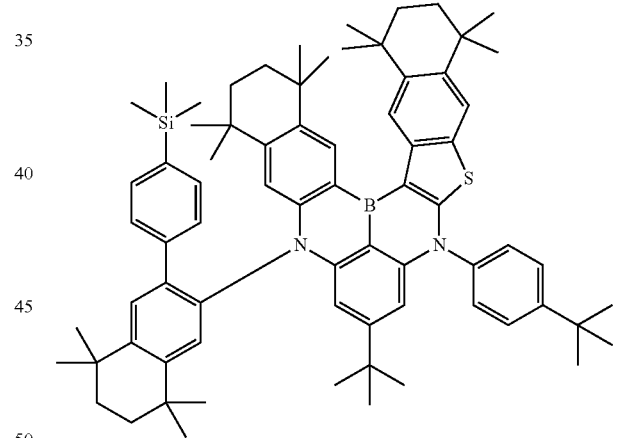
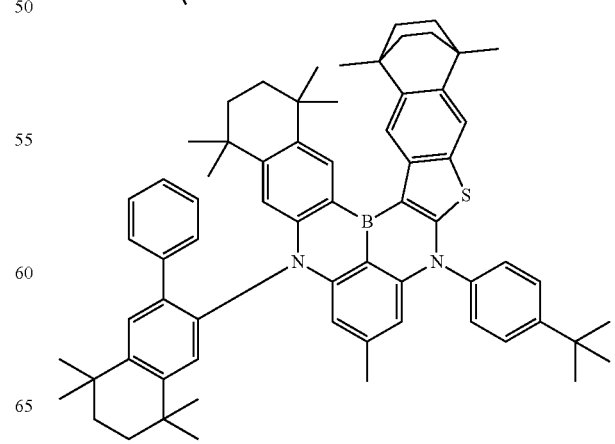

1533
-continued
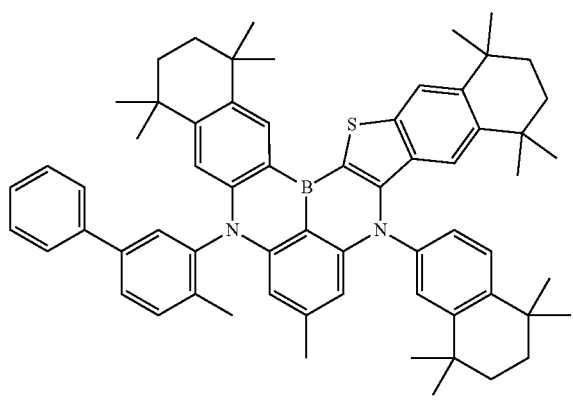
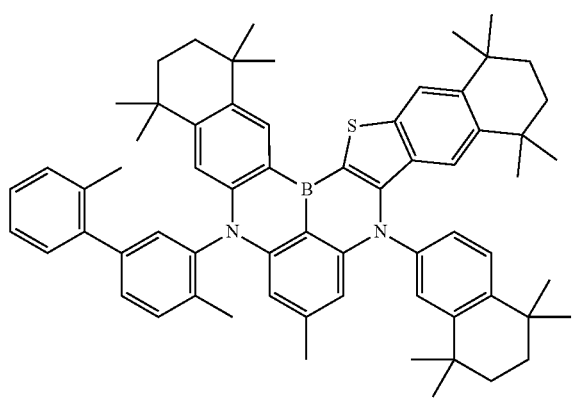
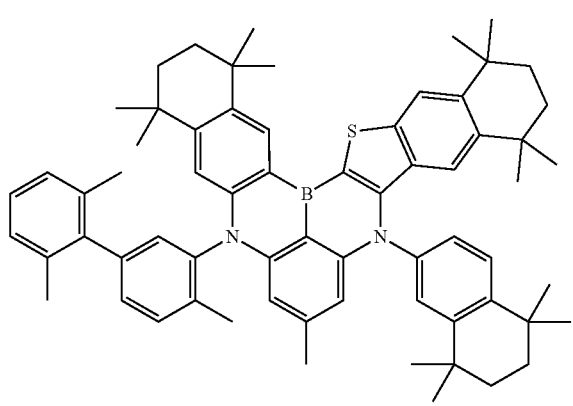
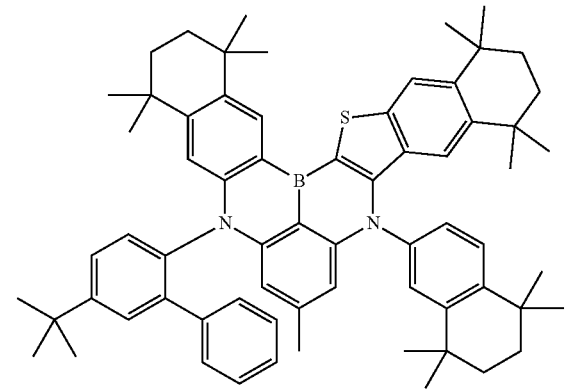
1534
-continued
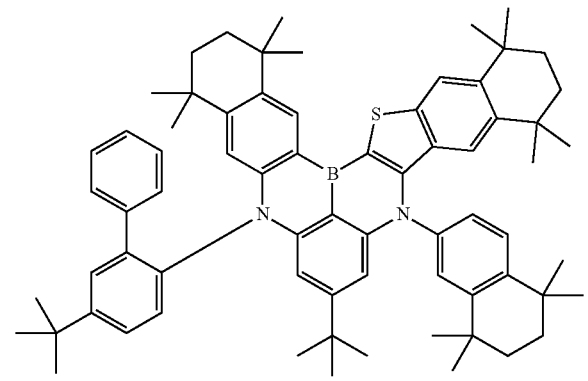
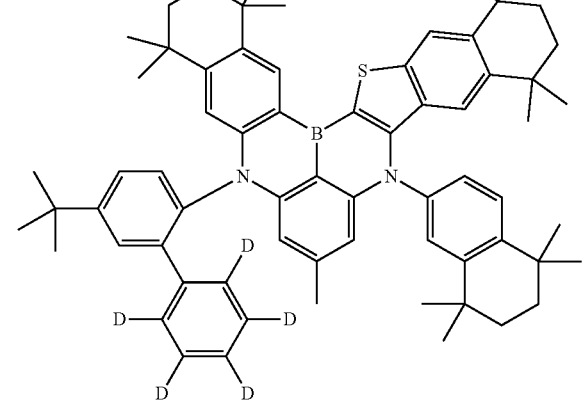
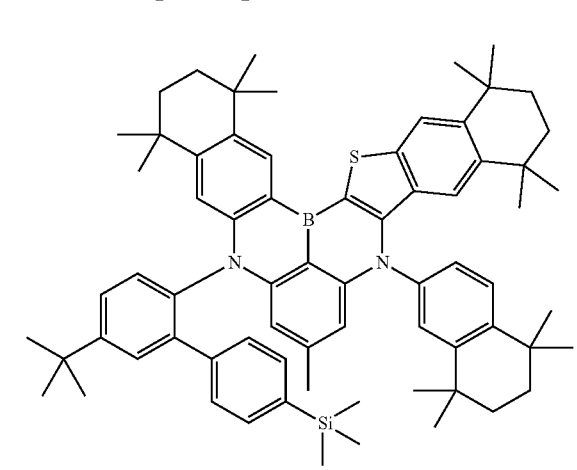
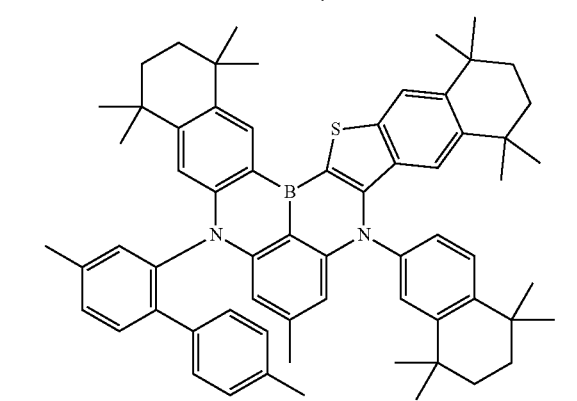

1535
-continued
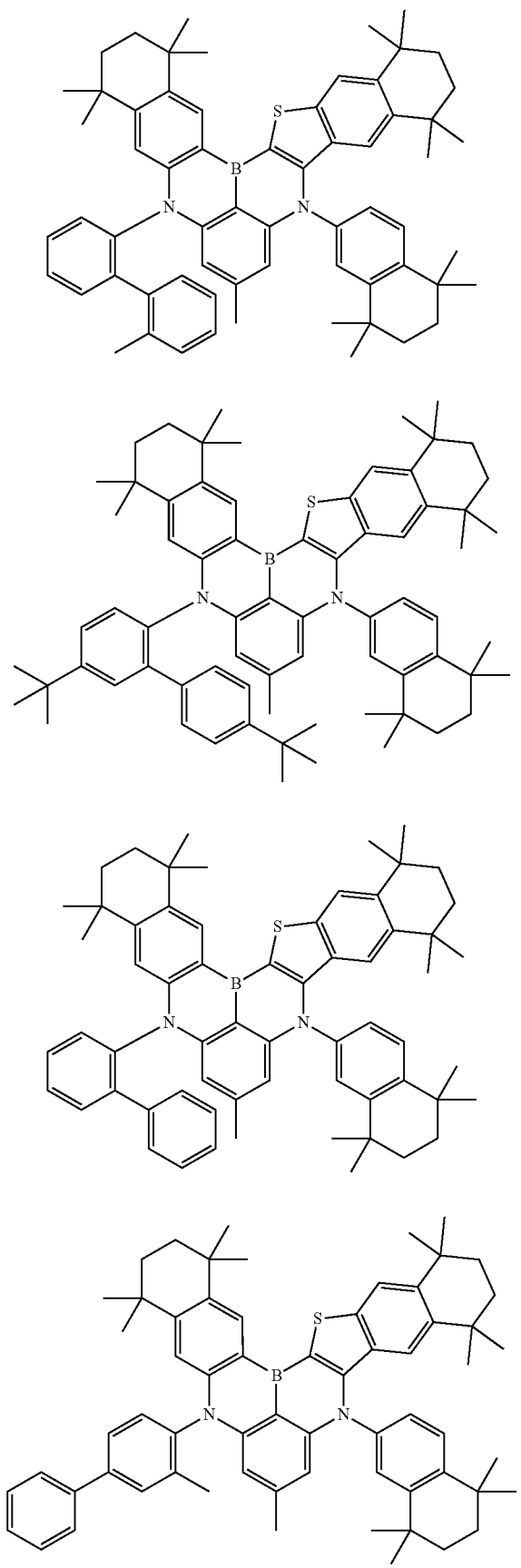
1536
-continued
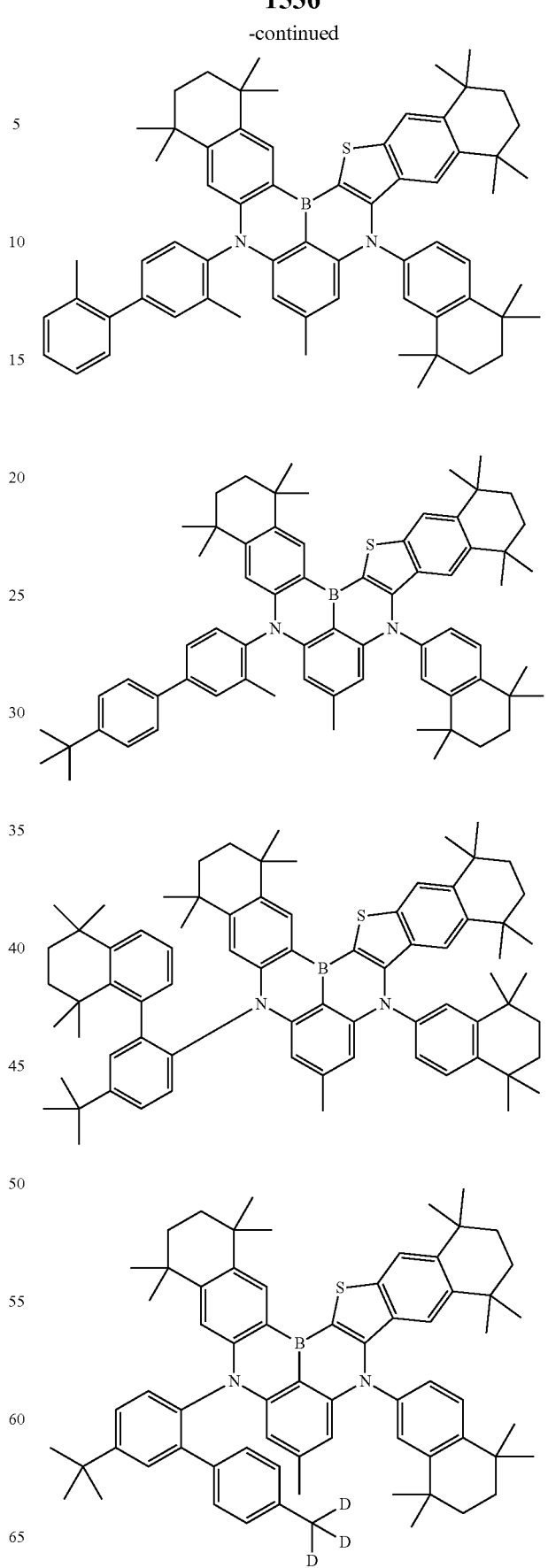

1537
-continued
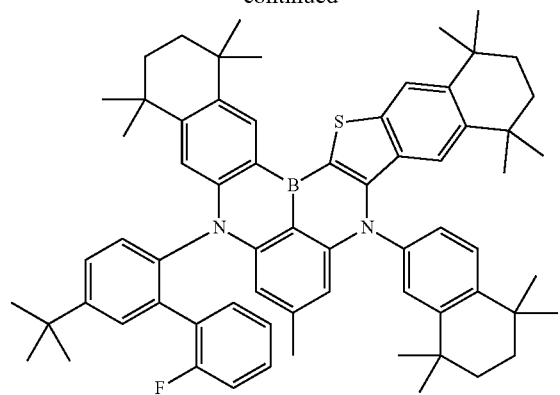
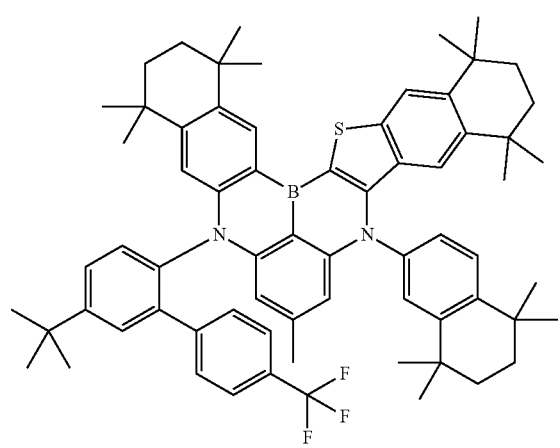
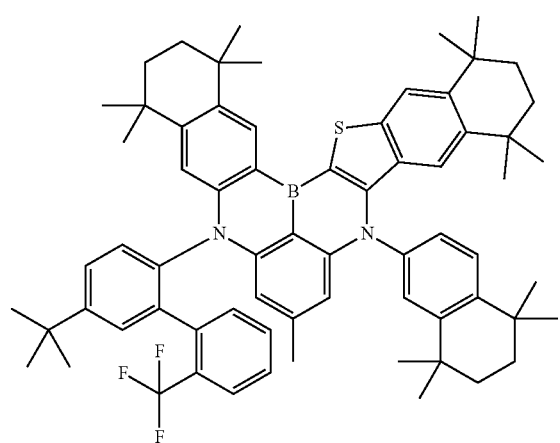
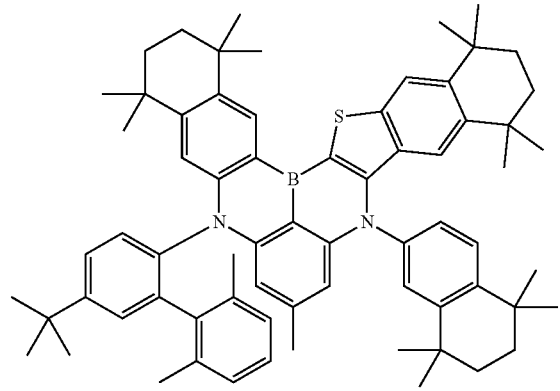
1538
-continued
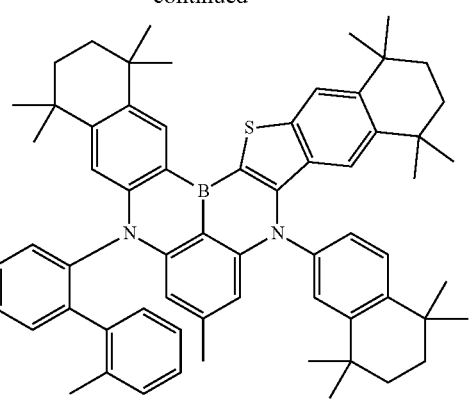
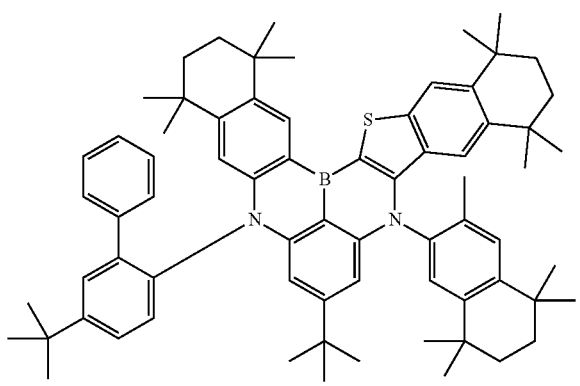
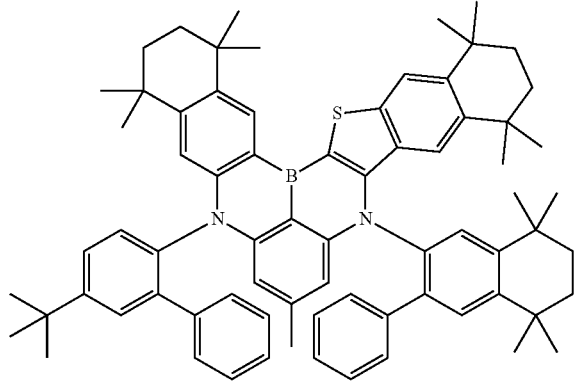
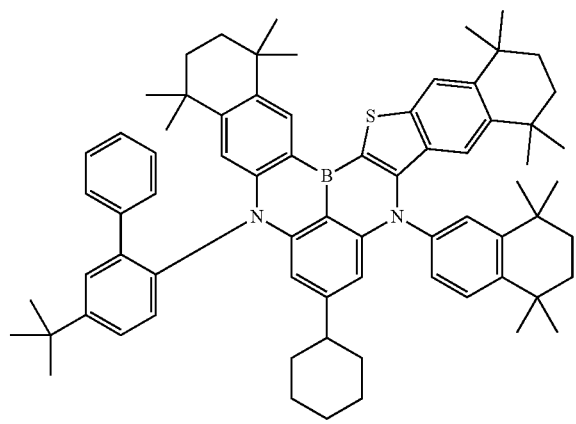

1539
-continued
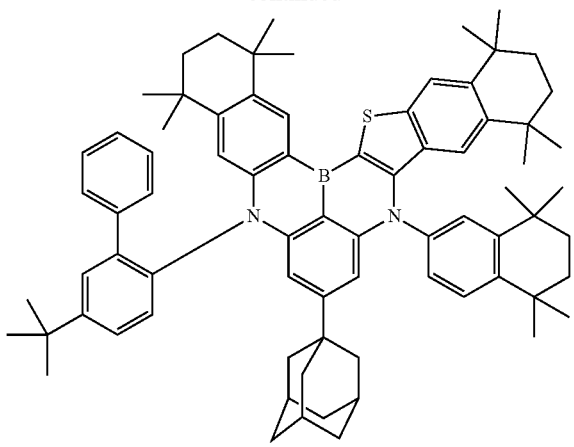
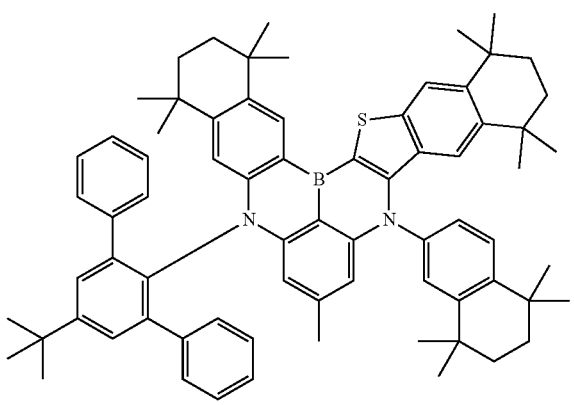
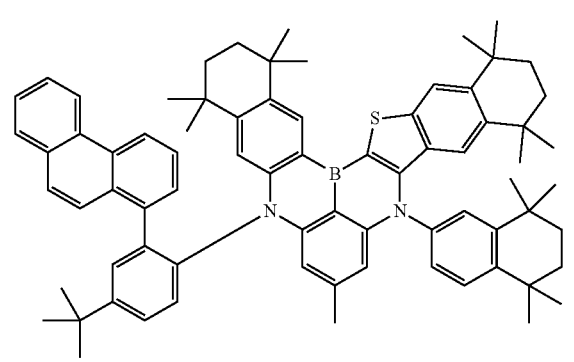
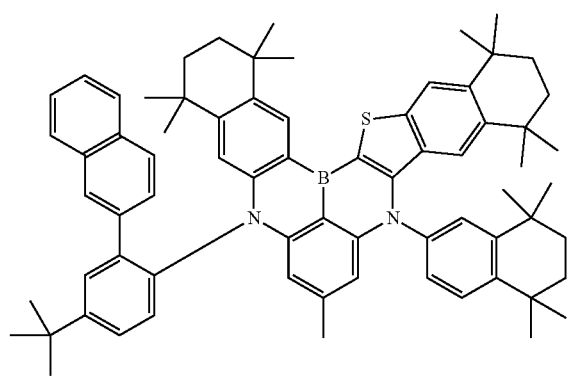
1540
-continued
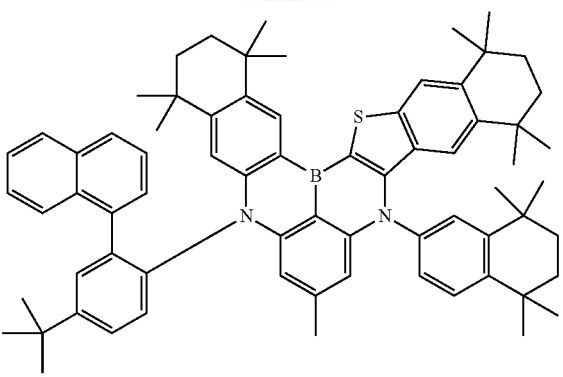
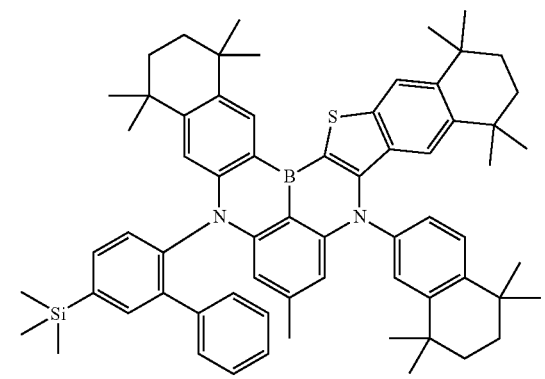
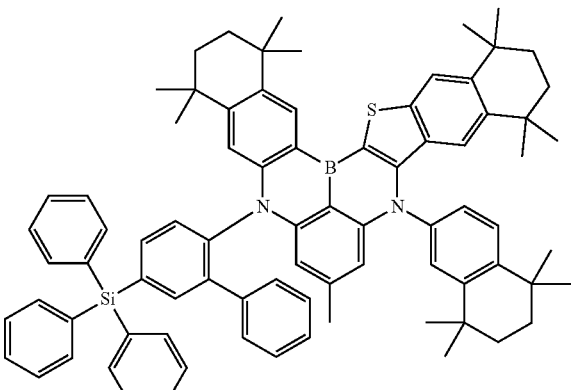
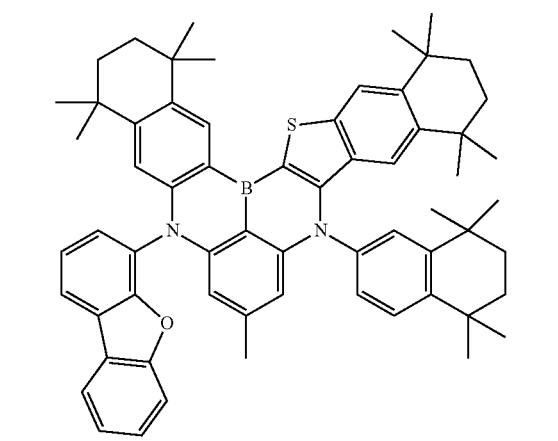

1541
-continued
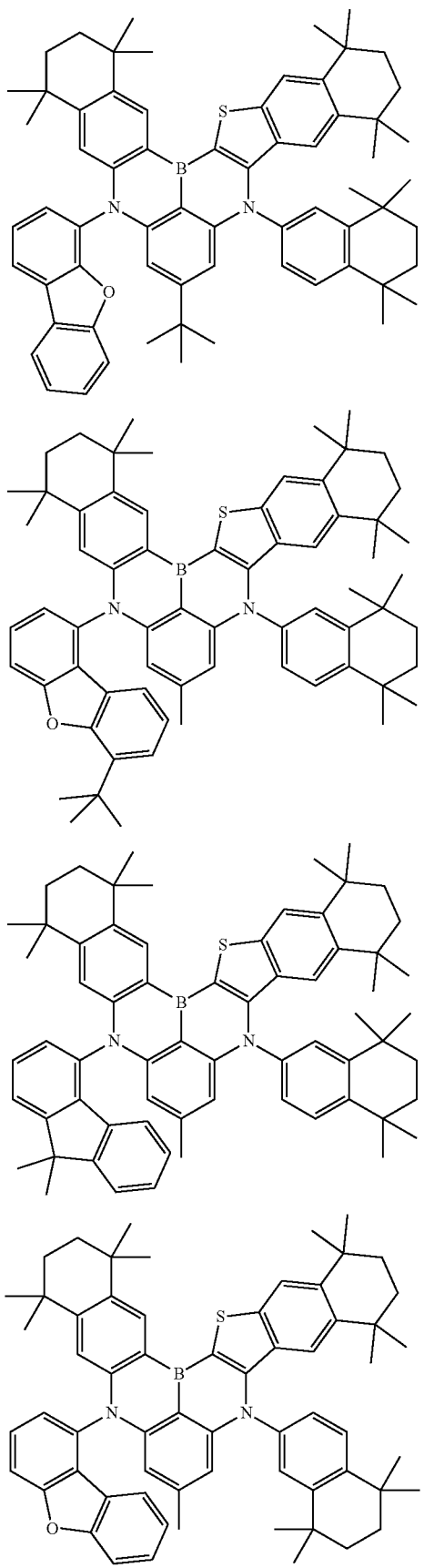
1542
-continued
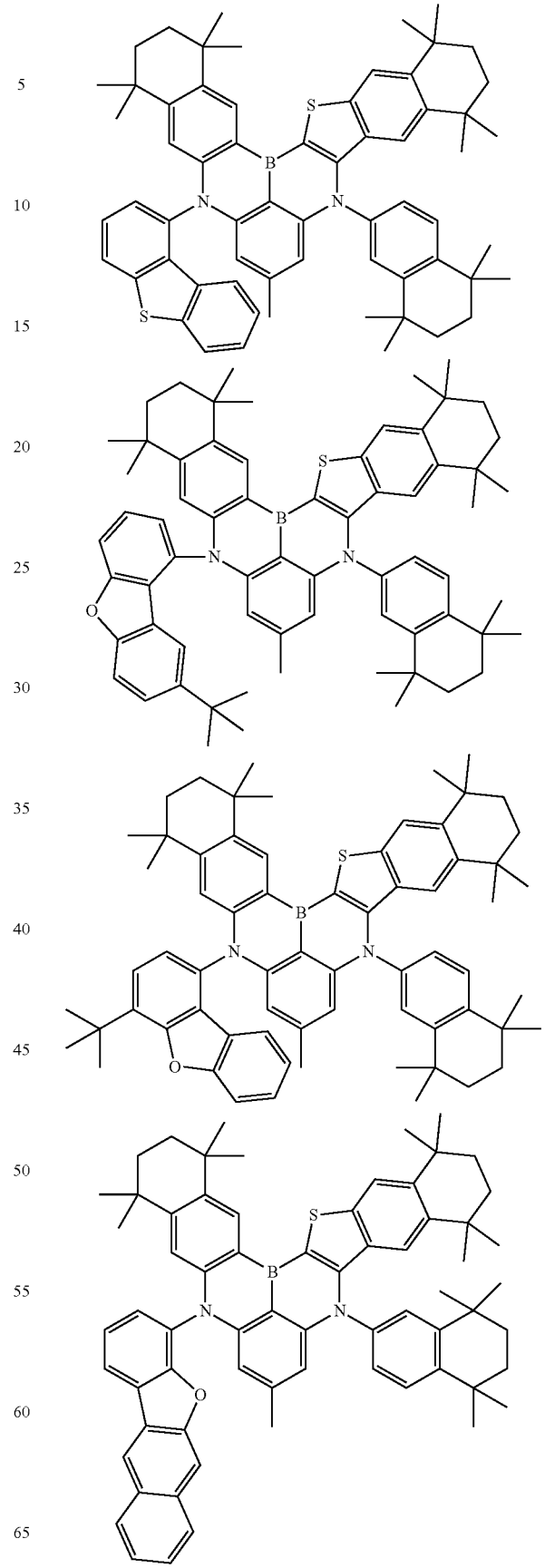

1543
-continued
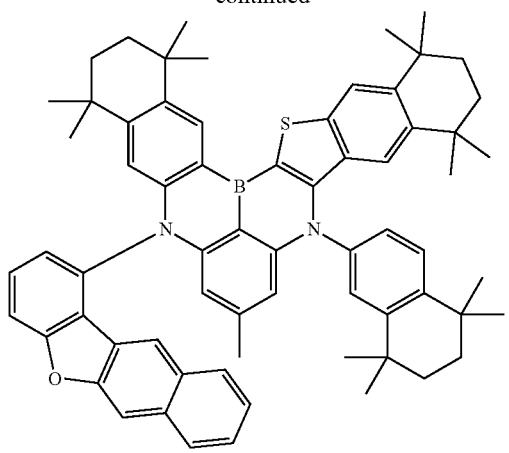
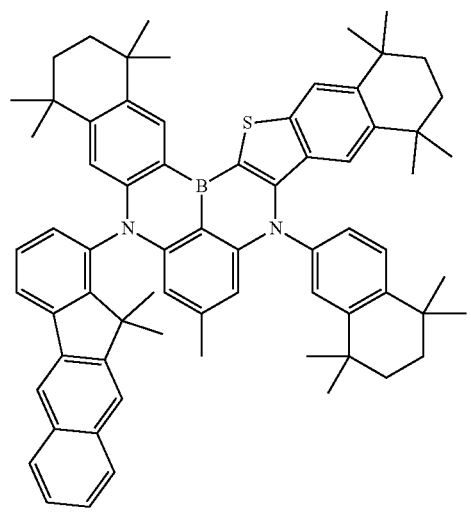
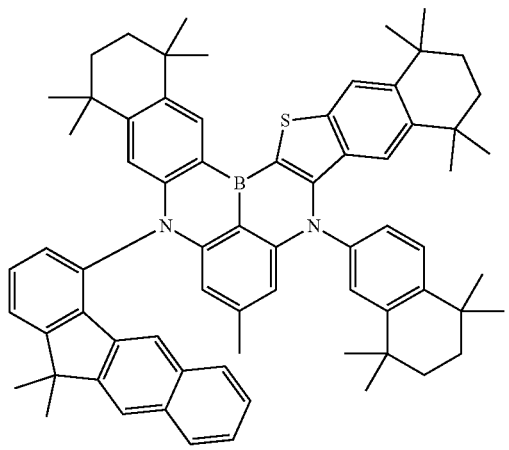
1544
-continued
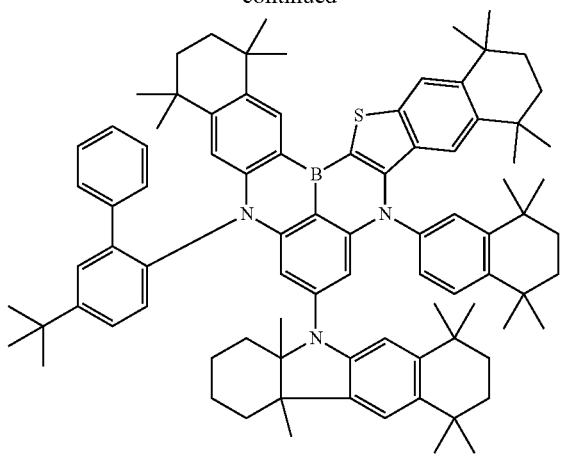
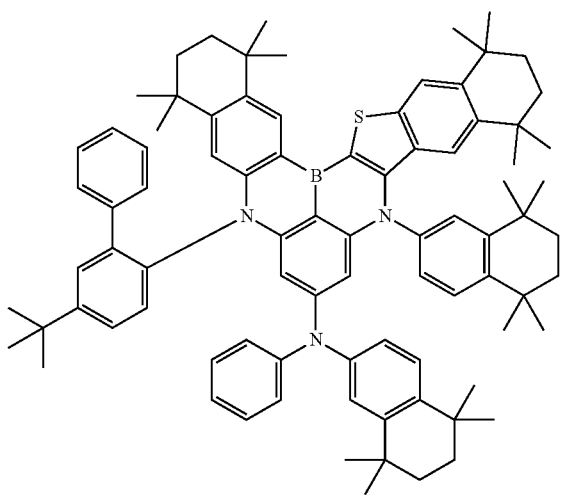
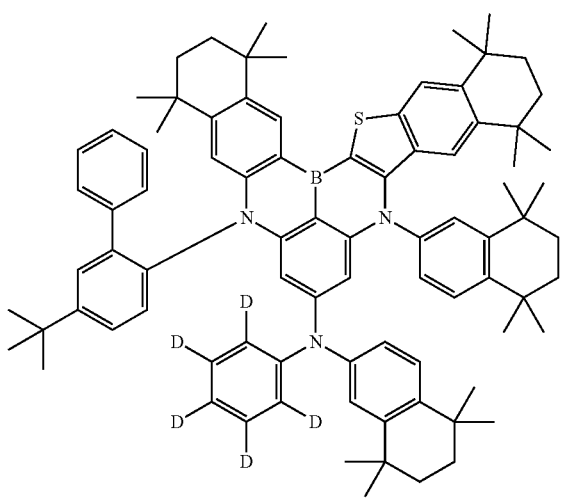

1545
-continued
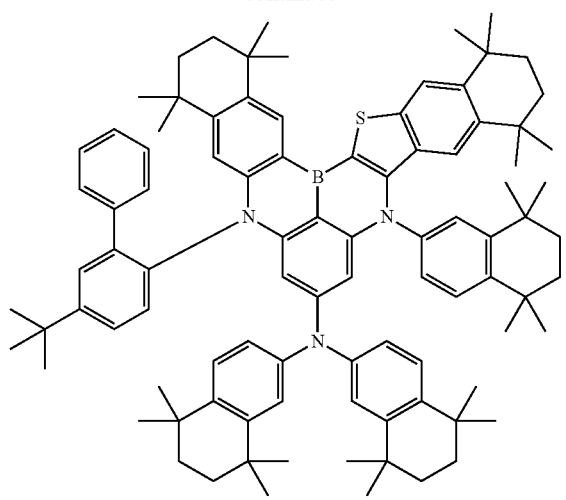
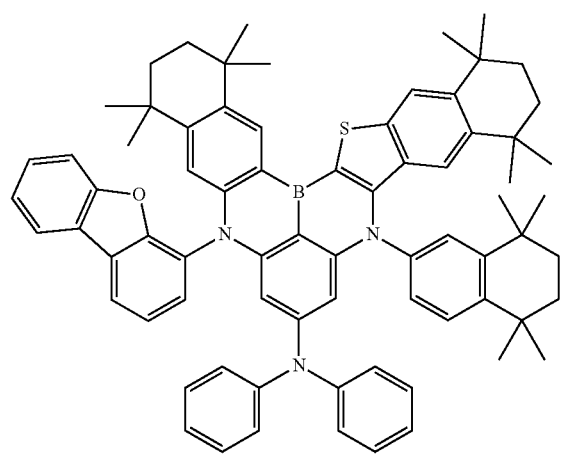
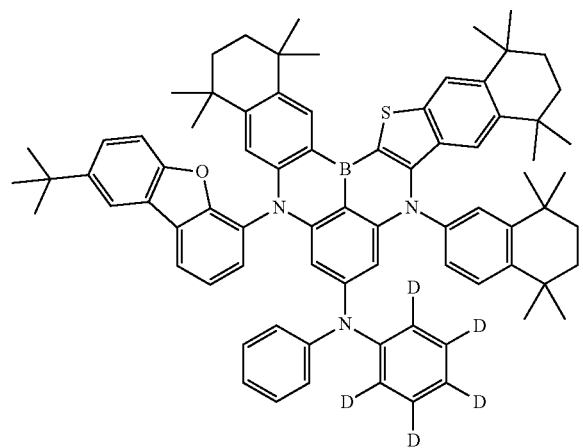
1546
-continued
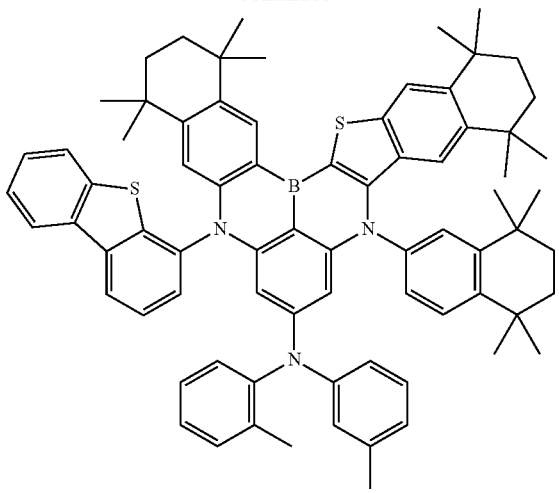
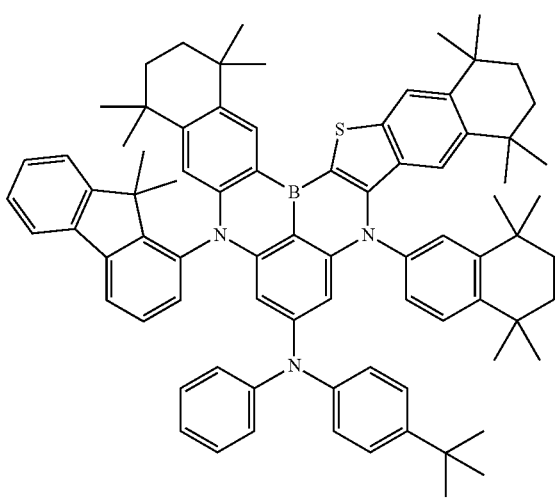
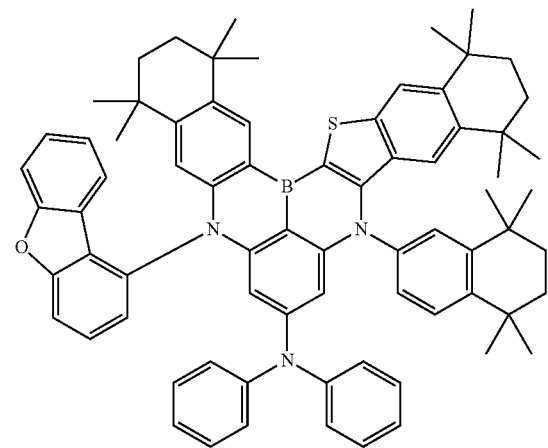

1547
-continued
1548
-continued
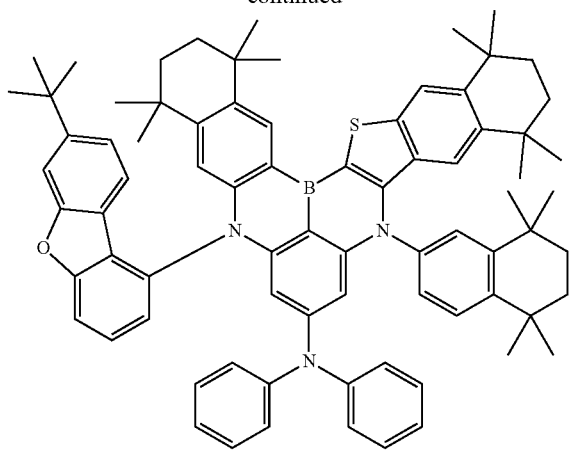
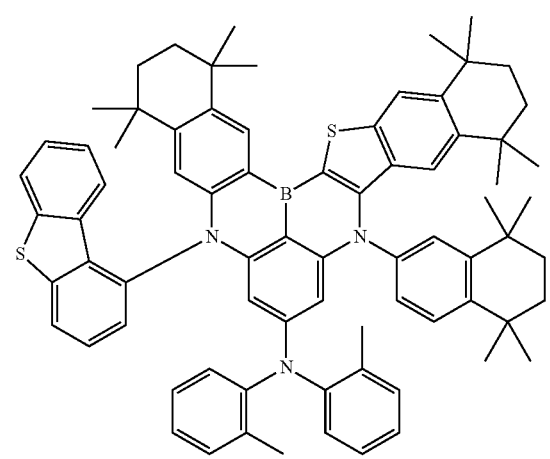
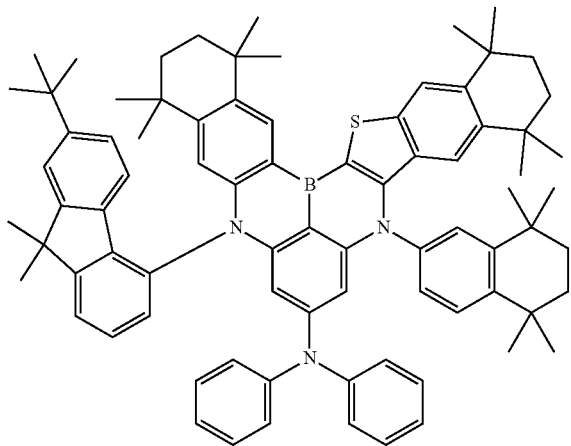
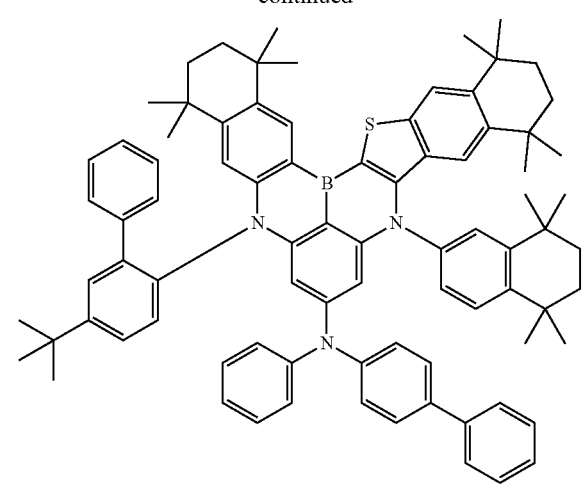
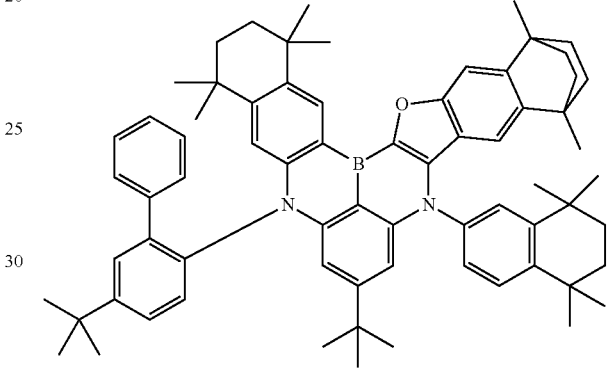
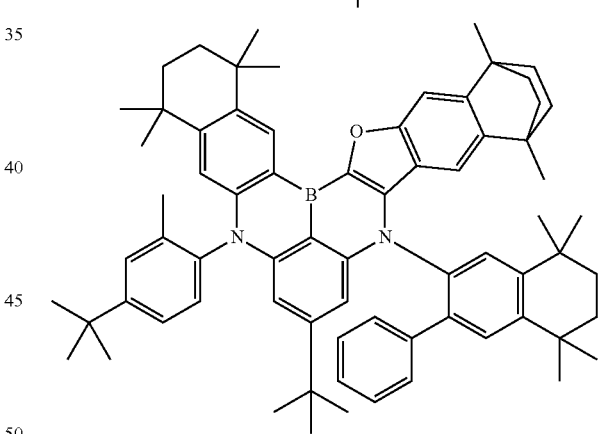
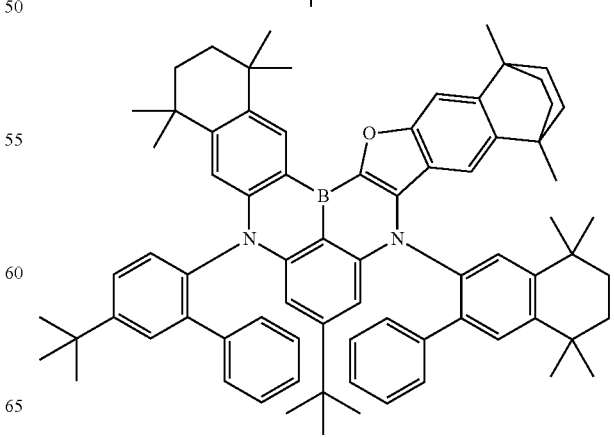

1549
-continued
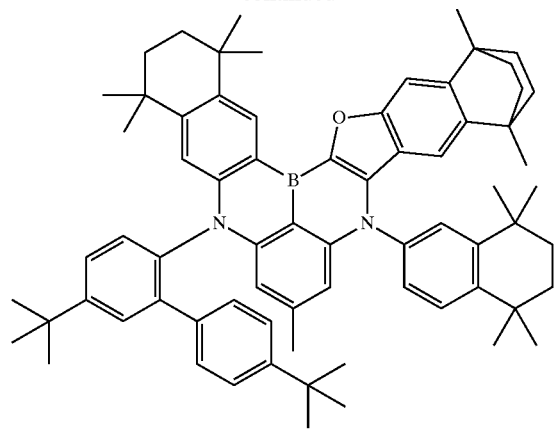
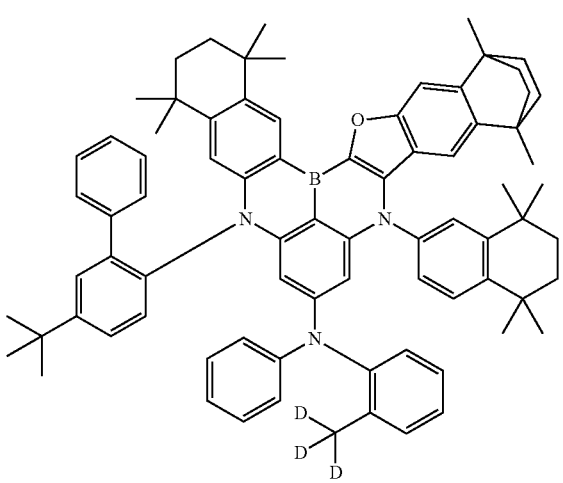
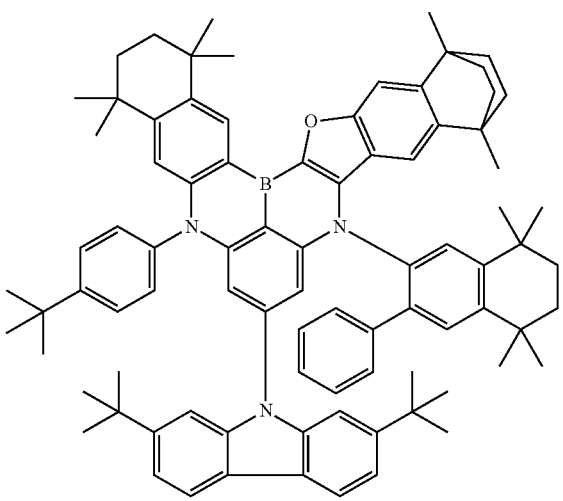
1550
-continued
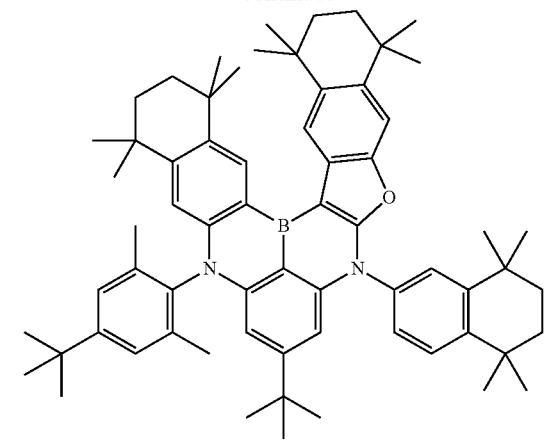
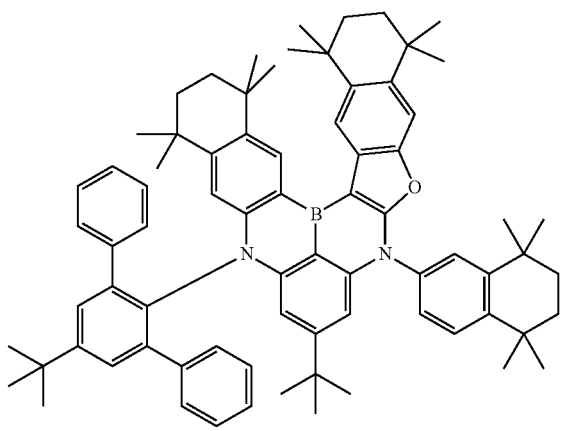
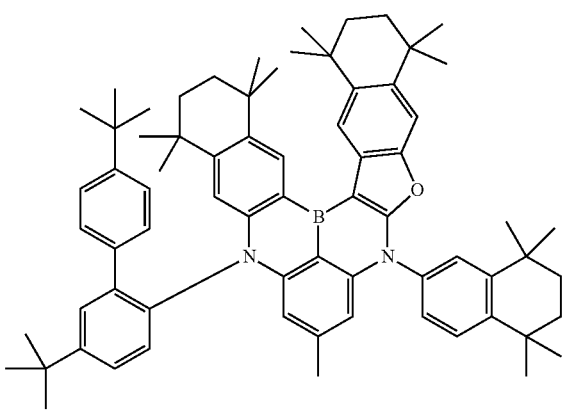
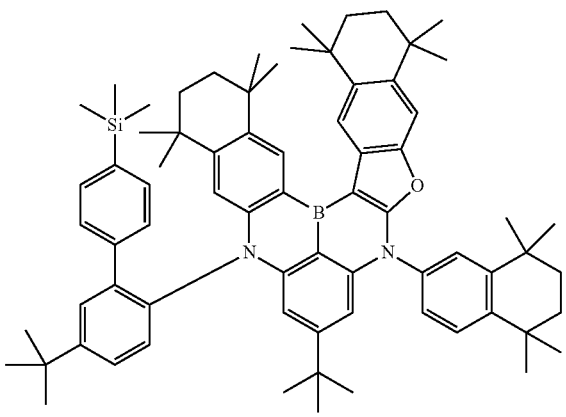

1551
-continued
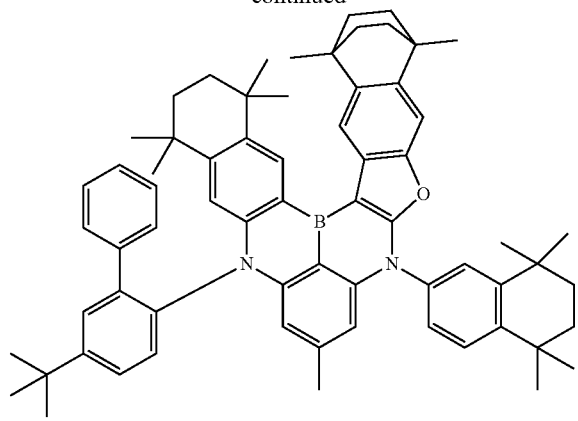
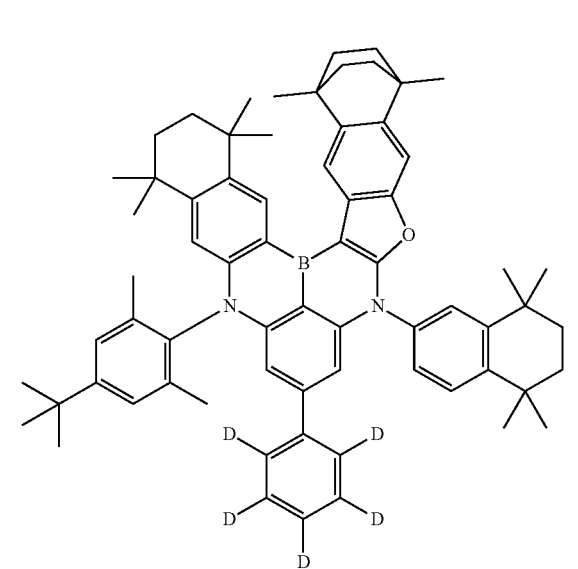
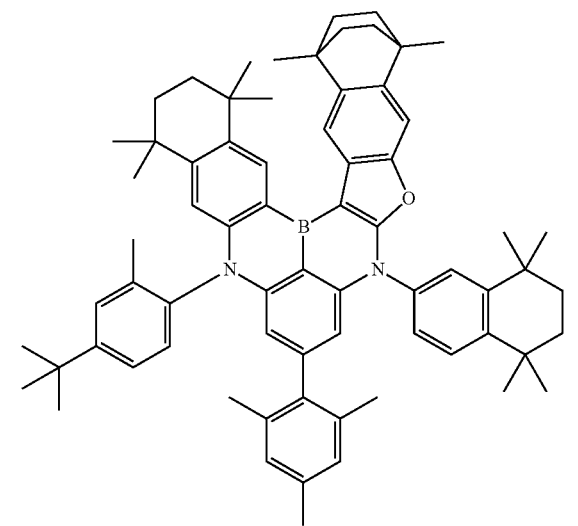
1552
-continued
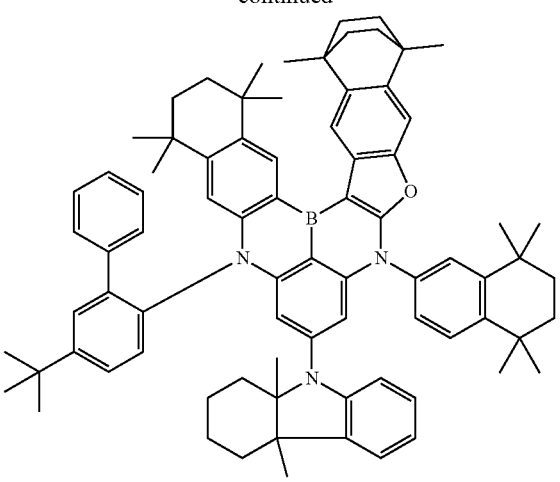
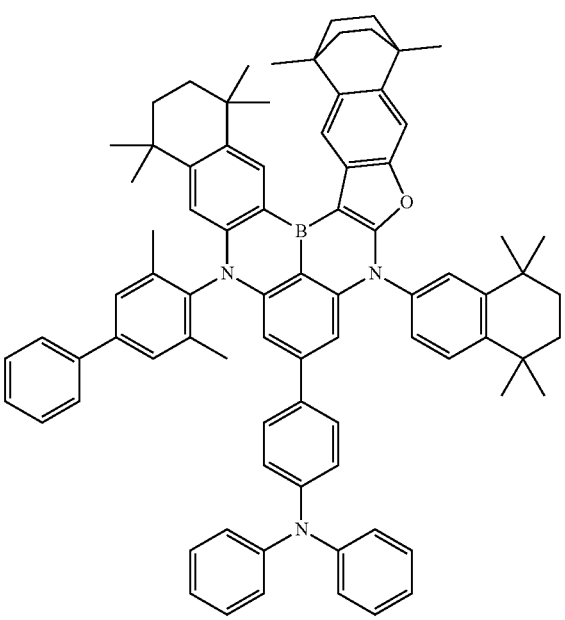
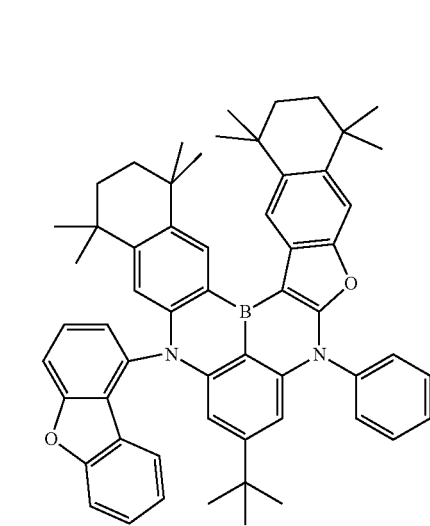

1553
-continued
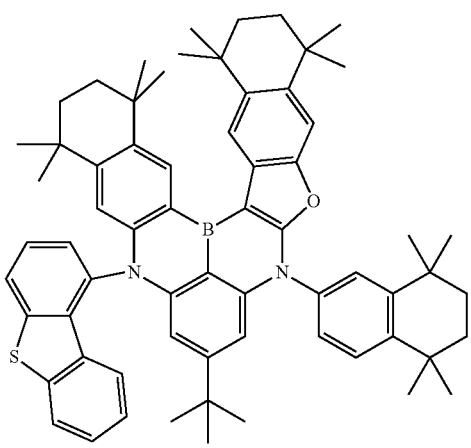
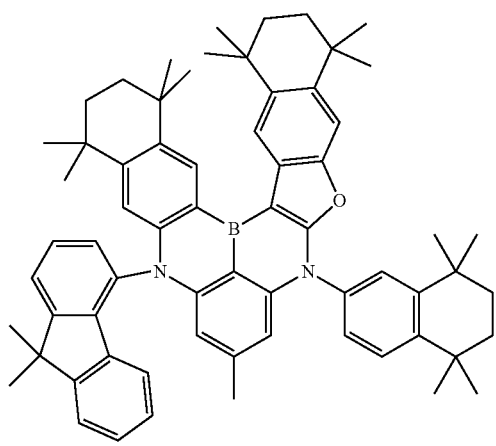
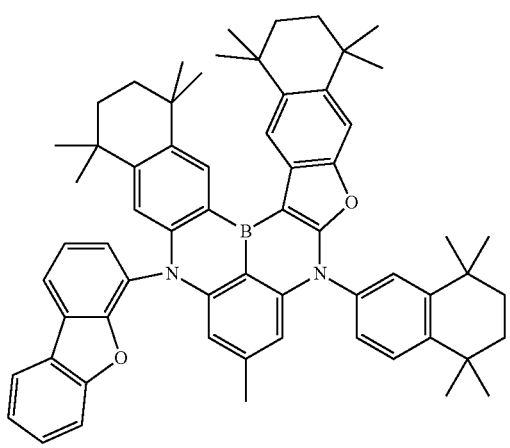
1554
-continued
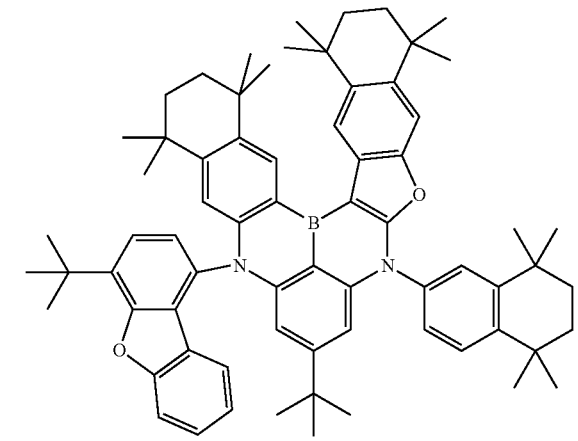
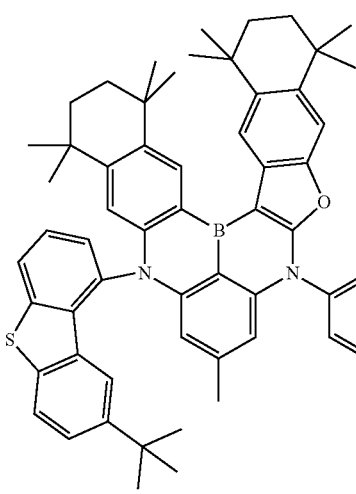
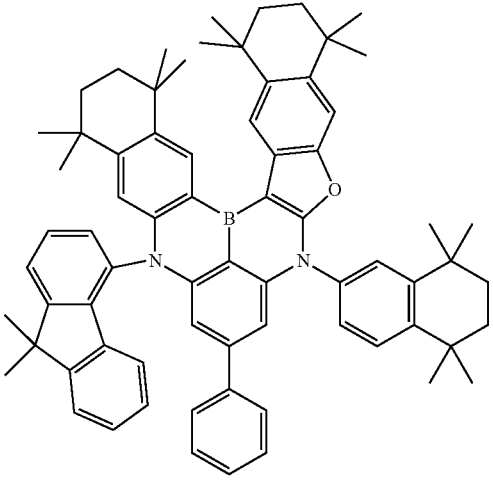

1555
-continued
1556
-continued
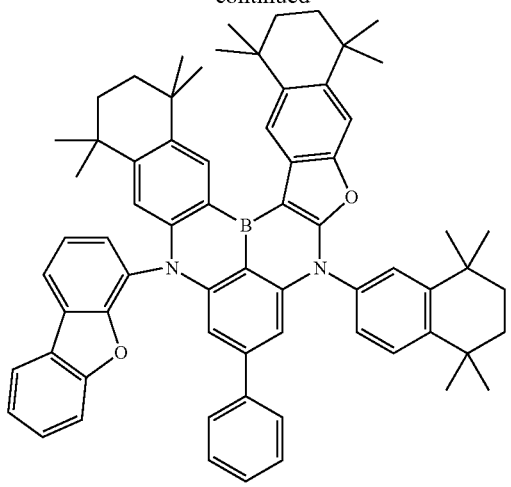
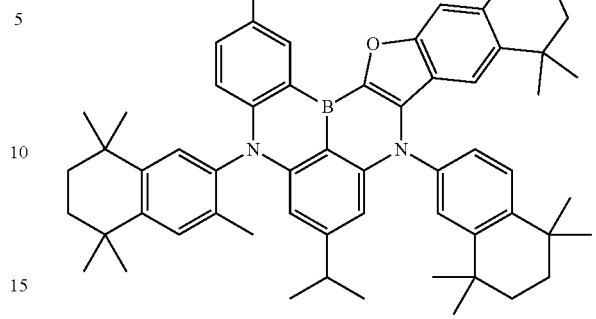
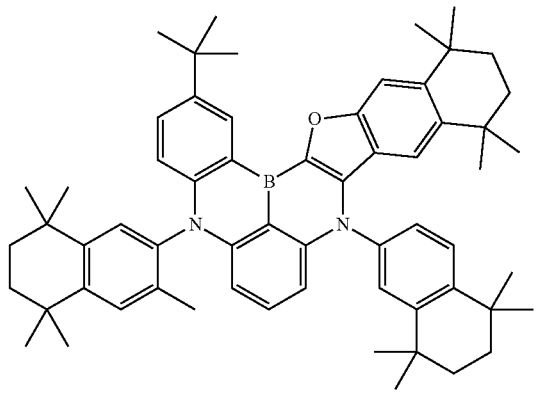
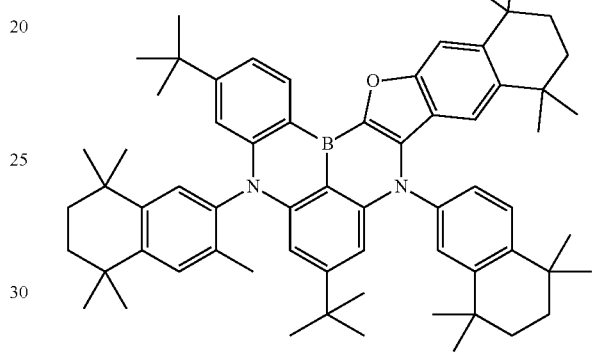
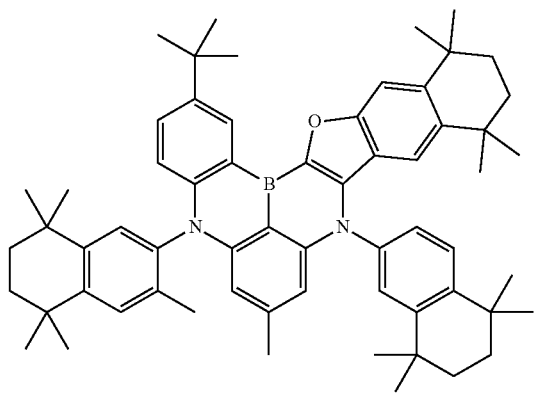
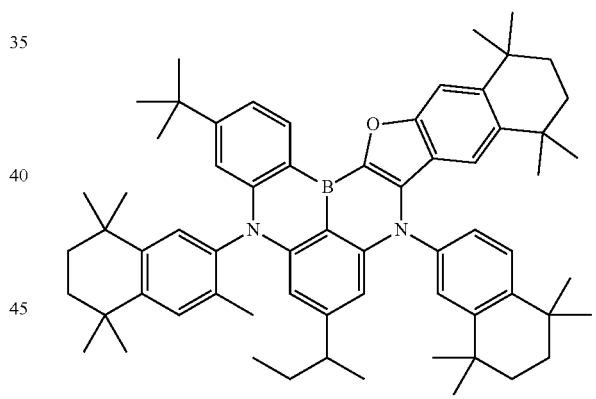
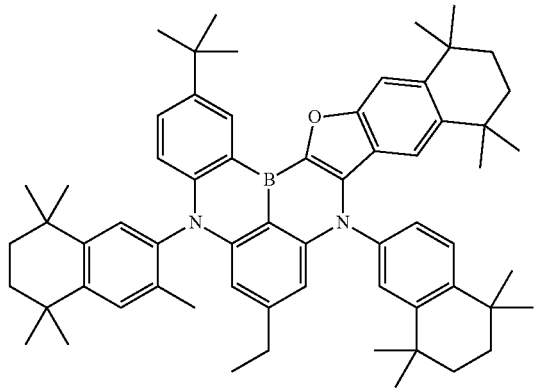
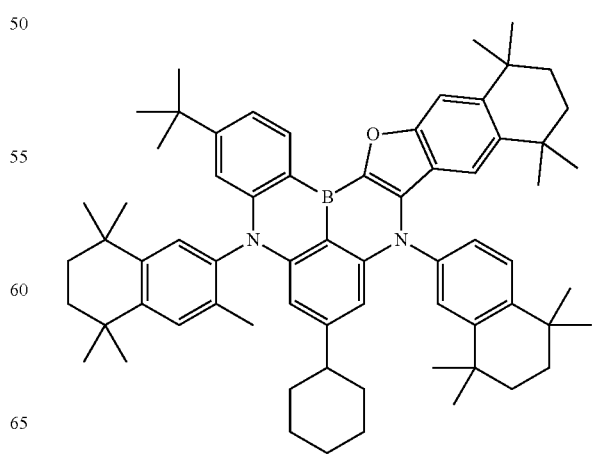

1557
-continued
1558
-continued
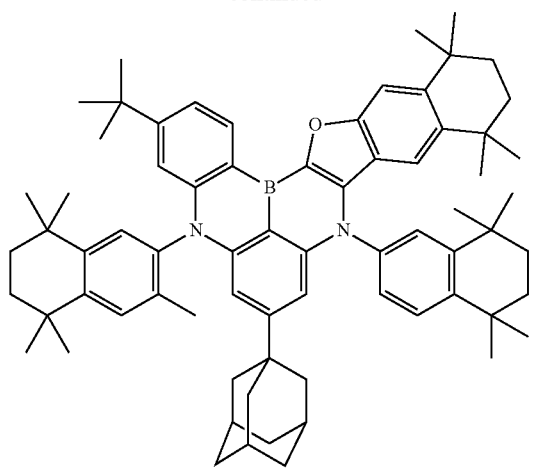
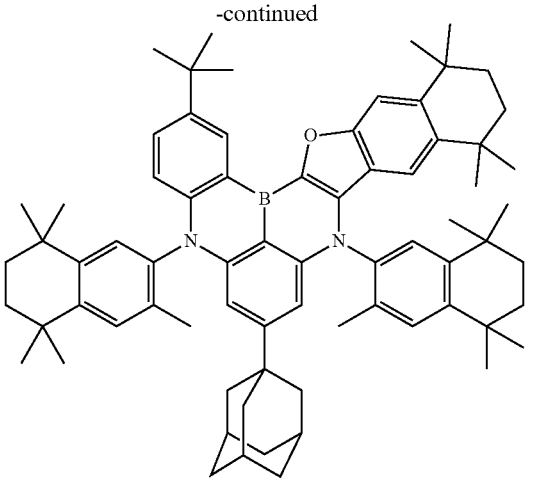
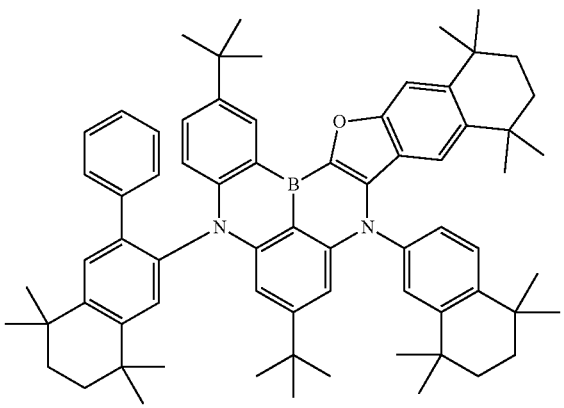
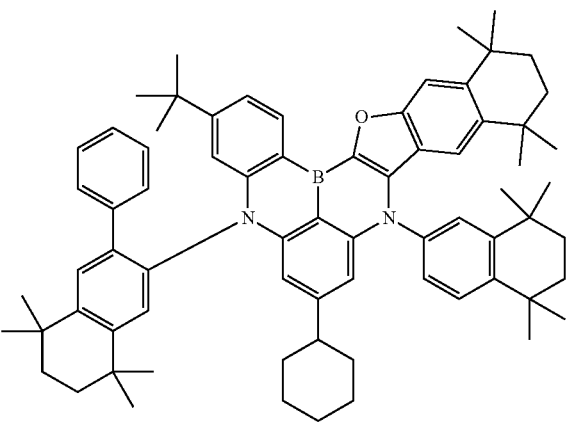

| 1559 -continued | 1560 -continued |
|---|---|
| 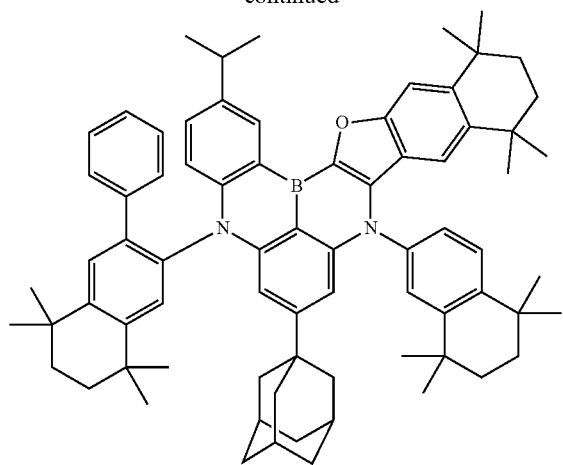 | 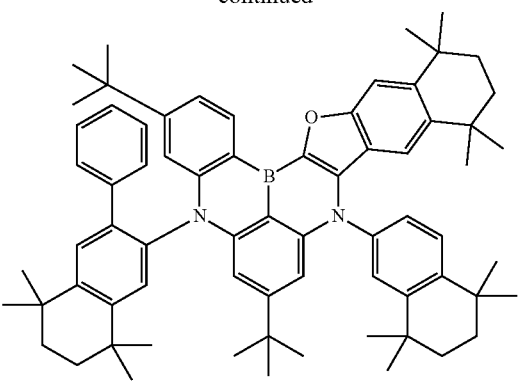 |
| 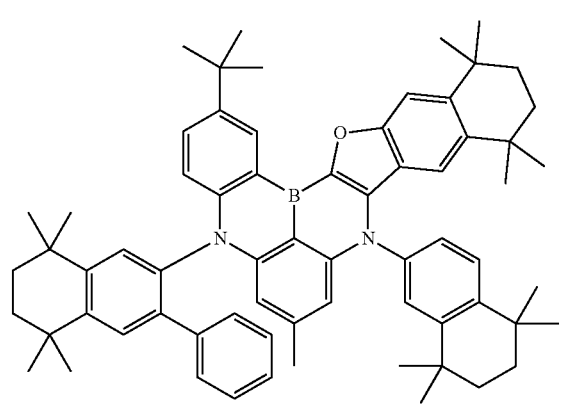 | 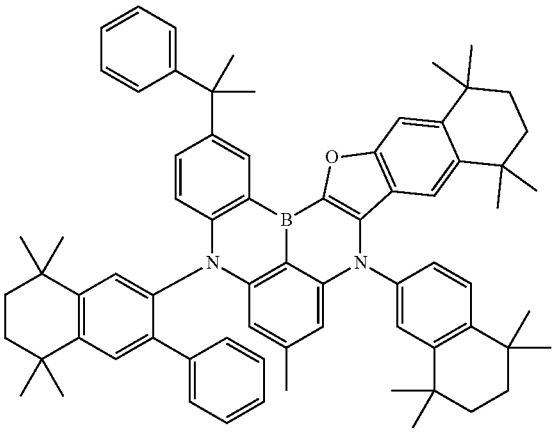 |
| 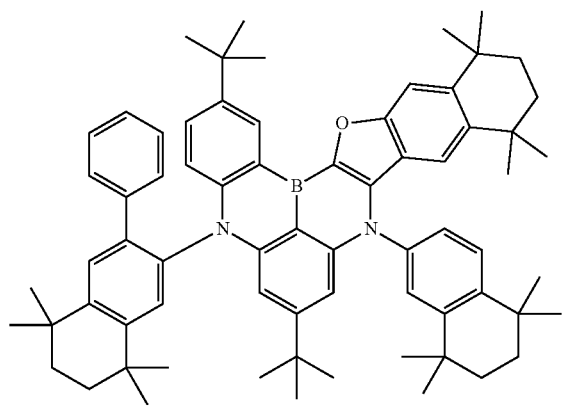 | 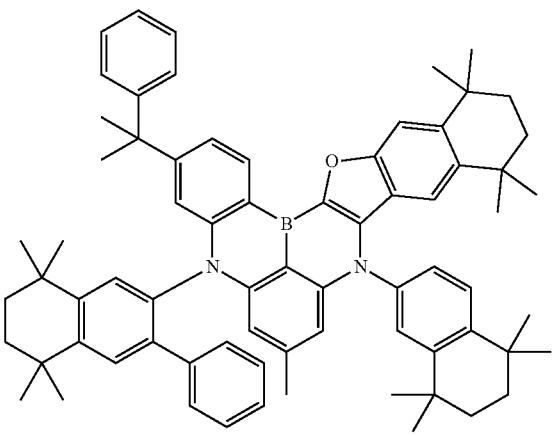 |
| 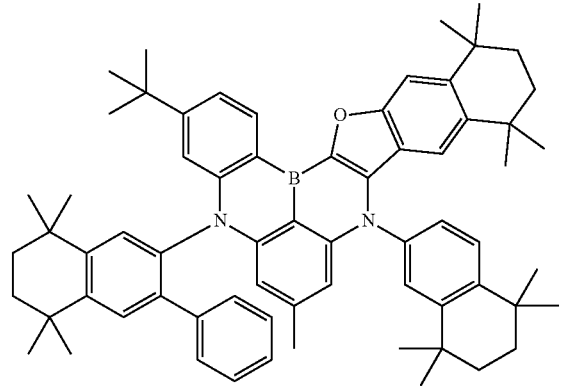 | 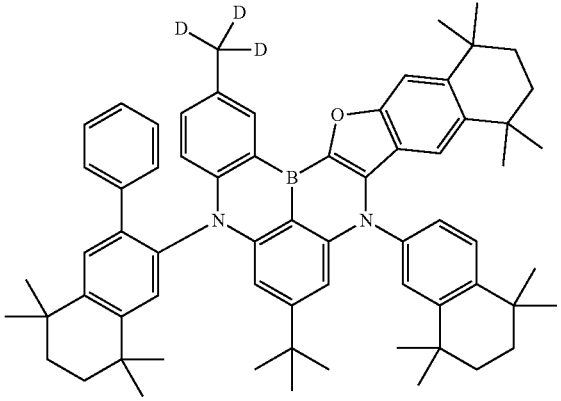 |

| 1561 -continued | 1562 -continued |
|---|---|
| 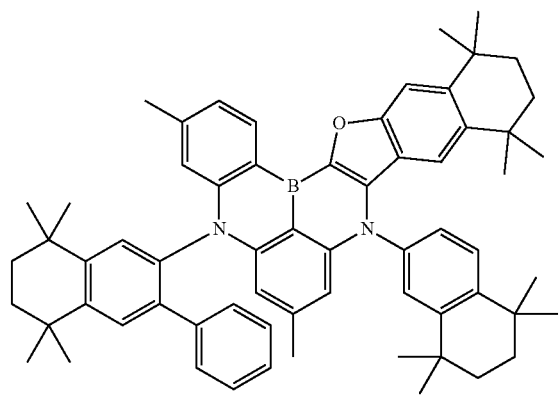 | 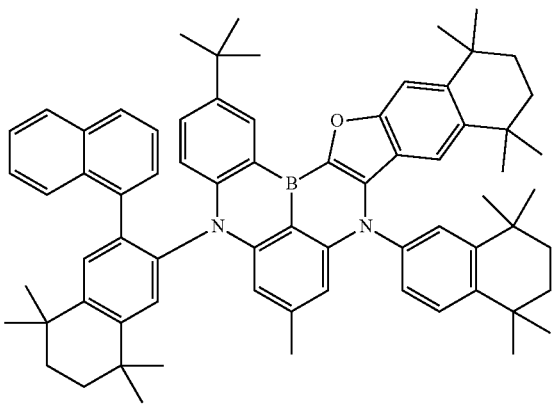 |
| 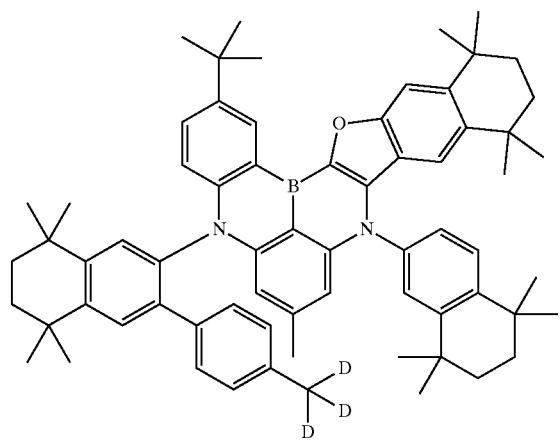 | |
| 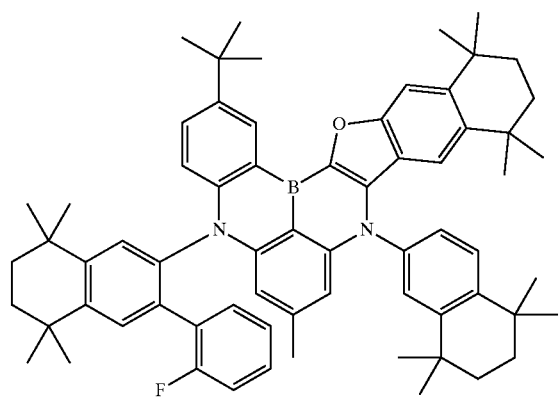 | |
| 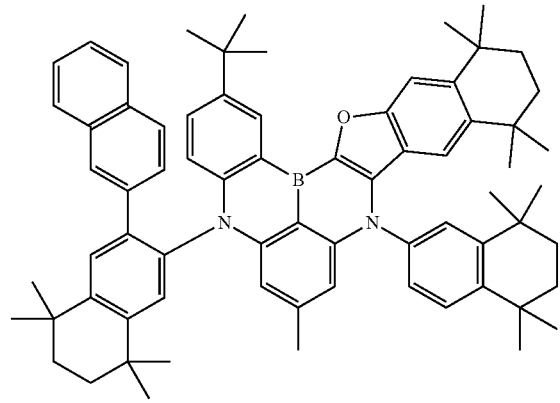 | |

1563
-continued
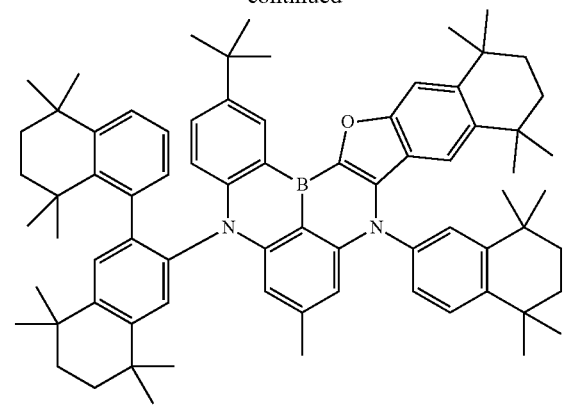
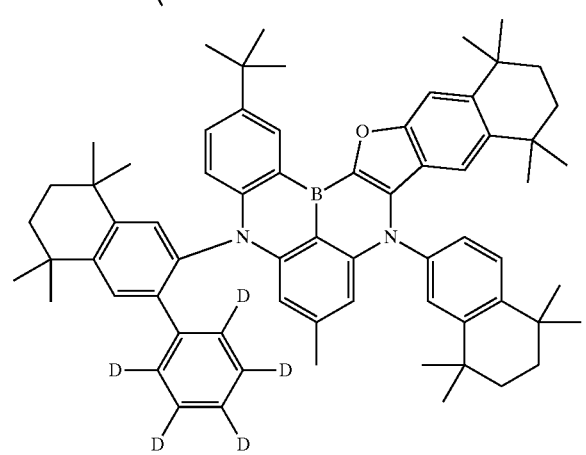
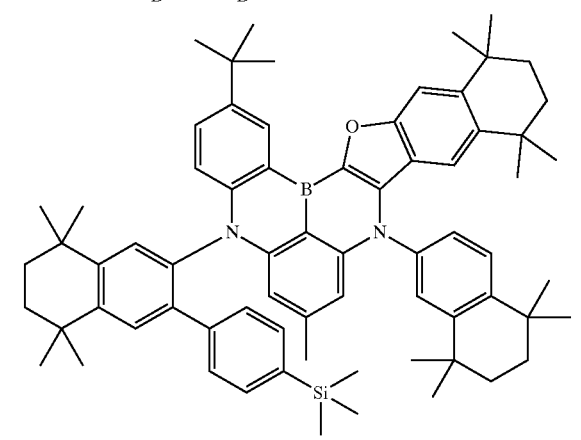
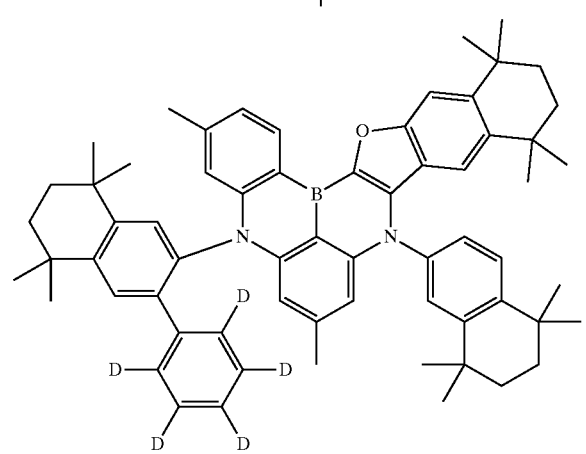
1564
-continued
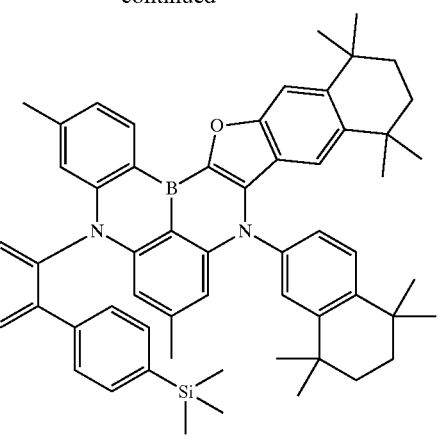
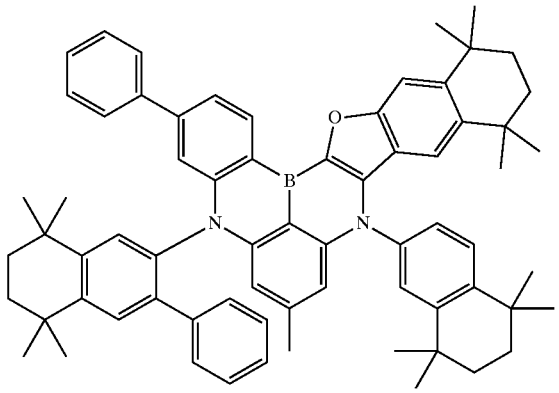
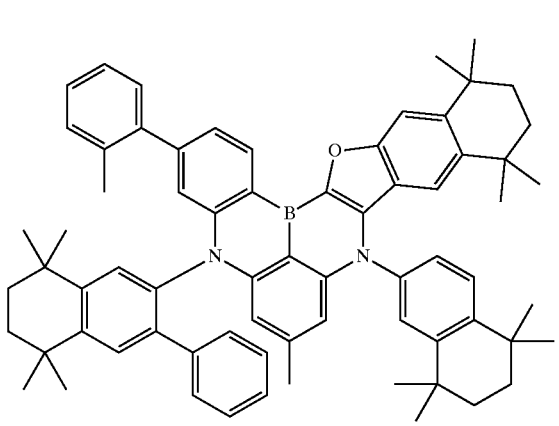
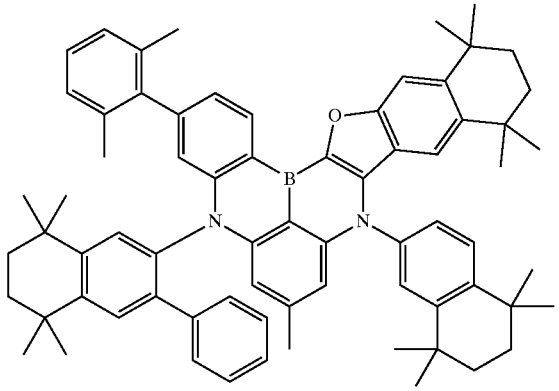

1565
-continued
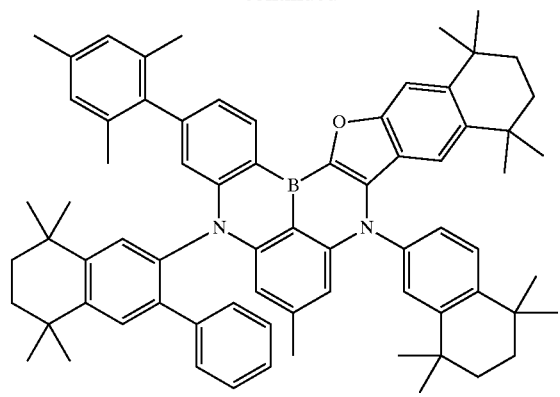
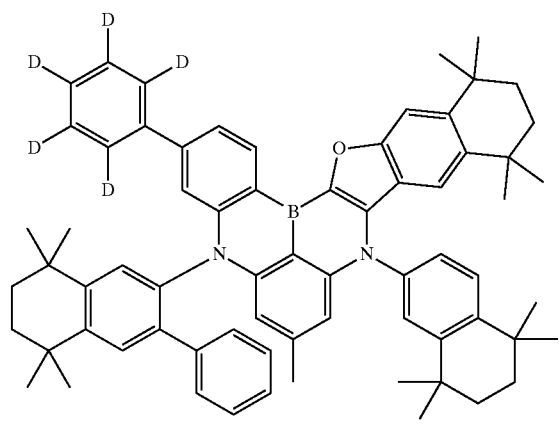
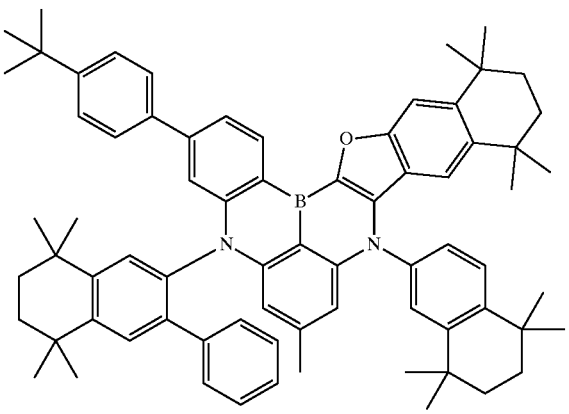
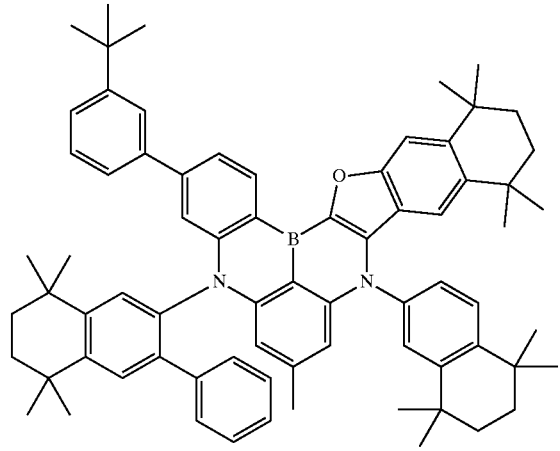
1566
-continued
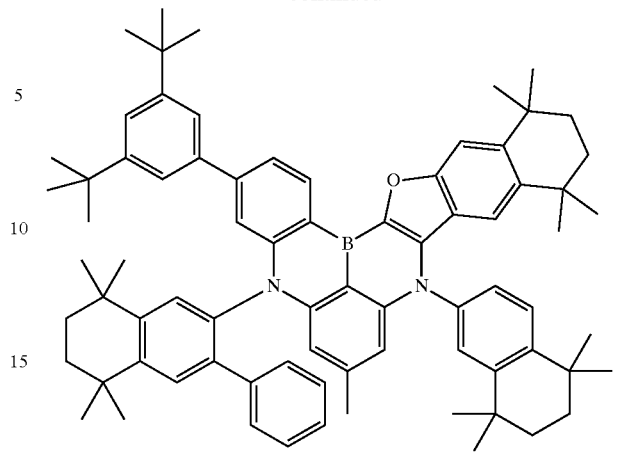
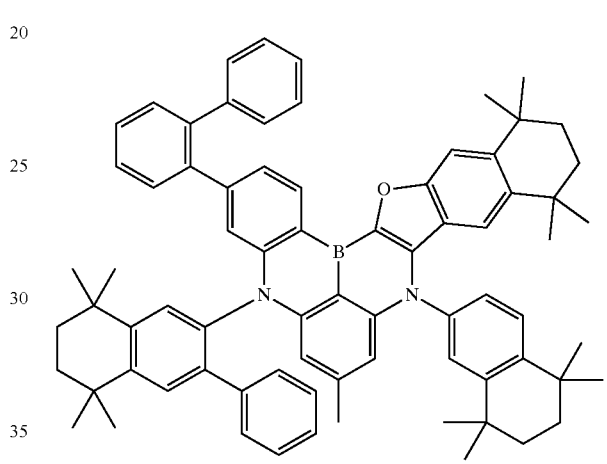
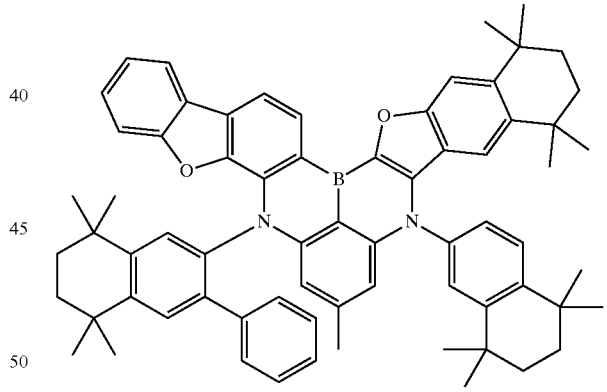
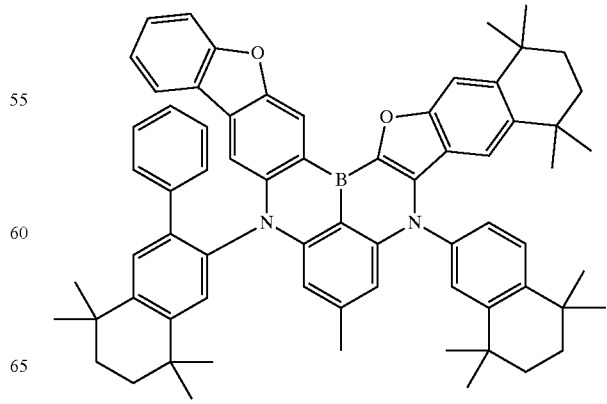

| 1567 -continued | 1568 -continued |
|---|---|
| 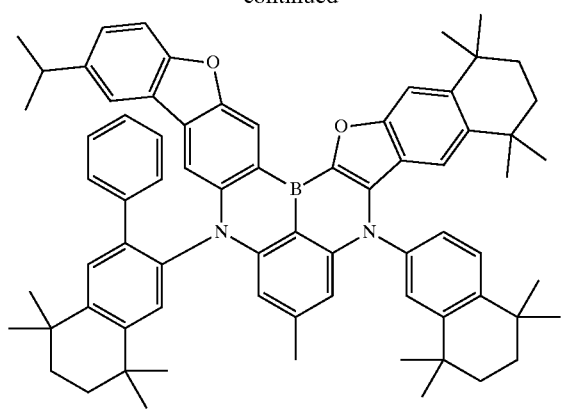 | 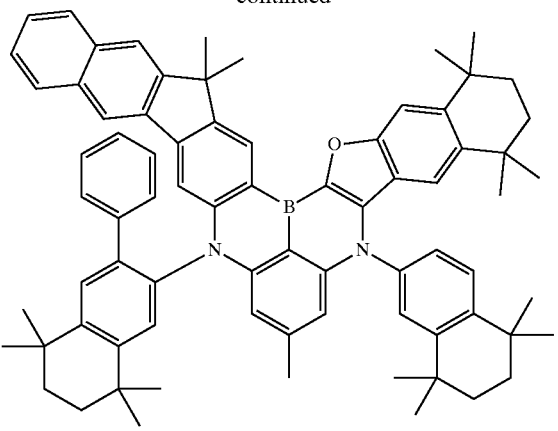 |
| 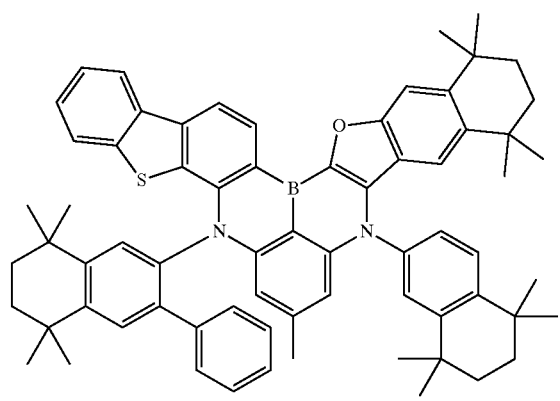 | 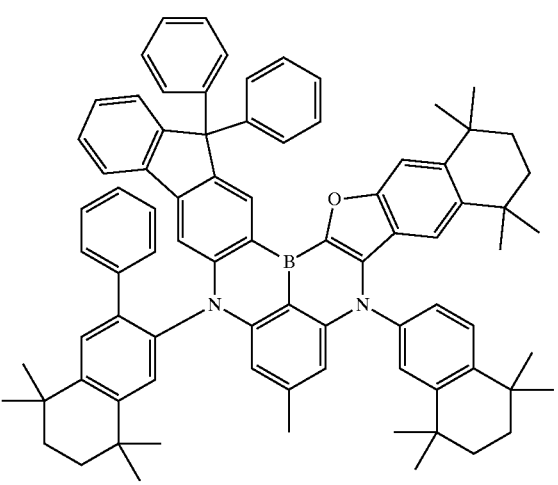 |
| 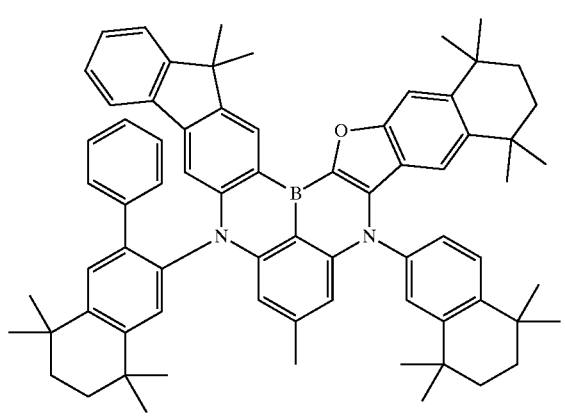 | |
| 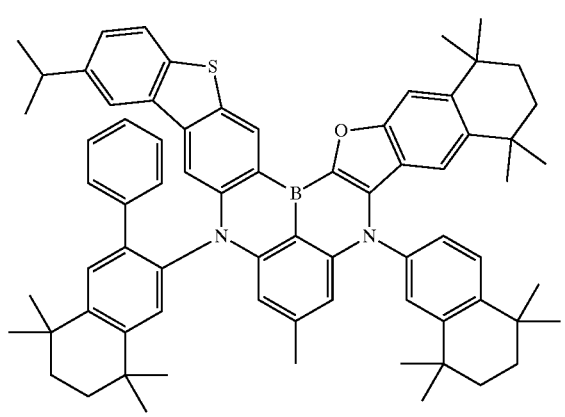 | 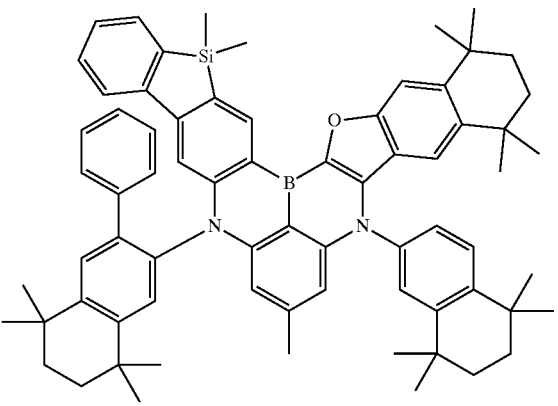 |

1569
-continued
1570
-continued
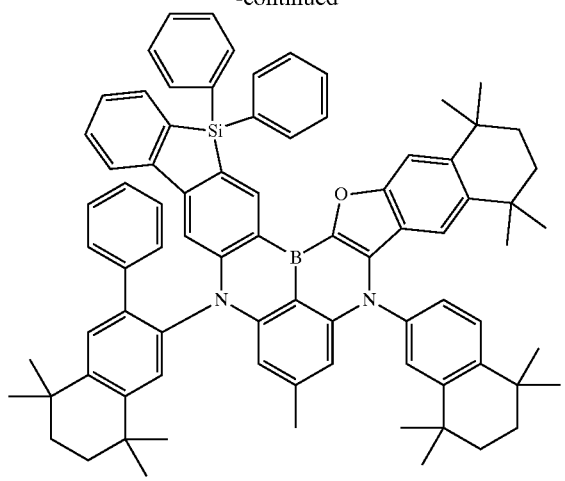
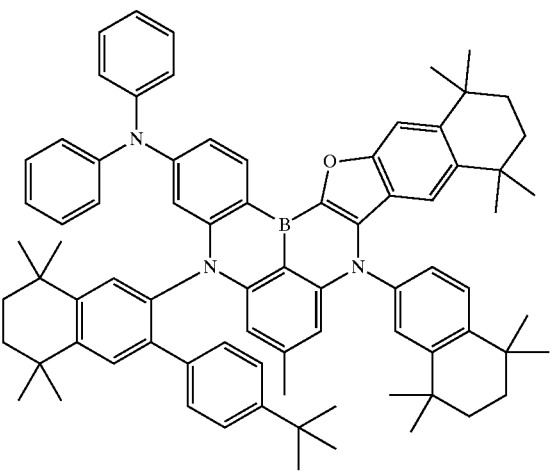
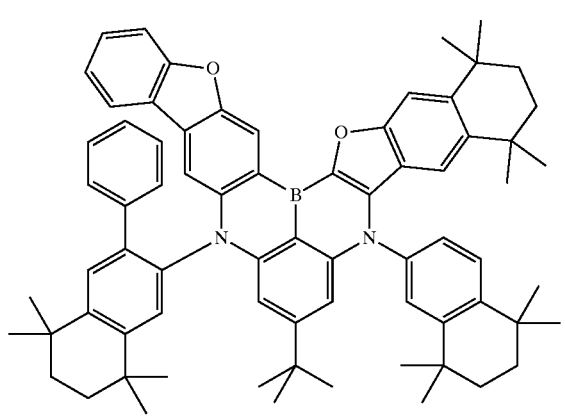
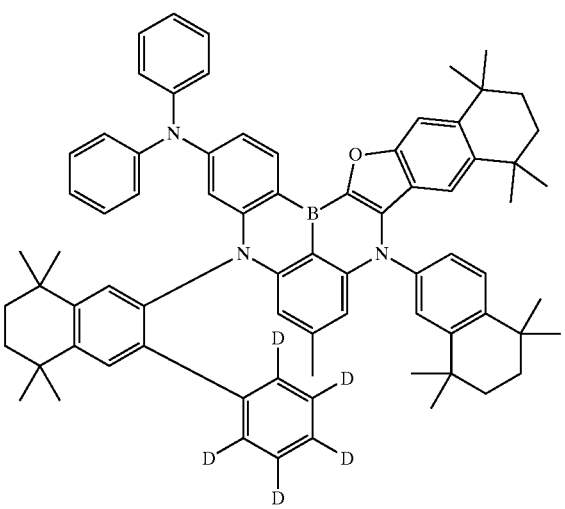
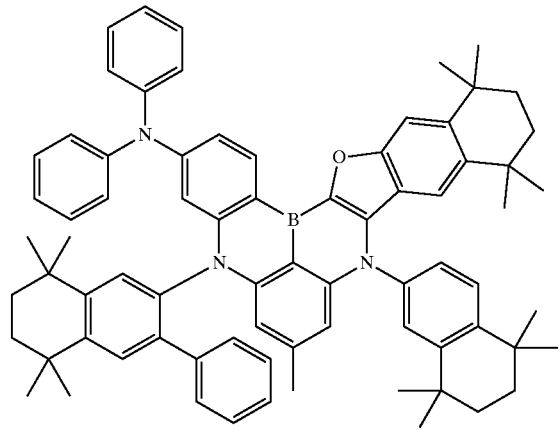
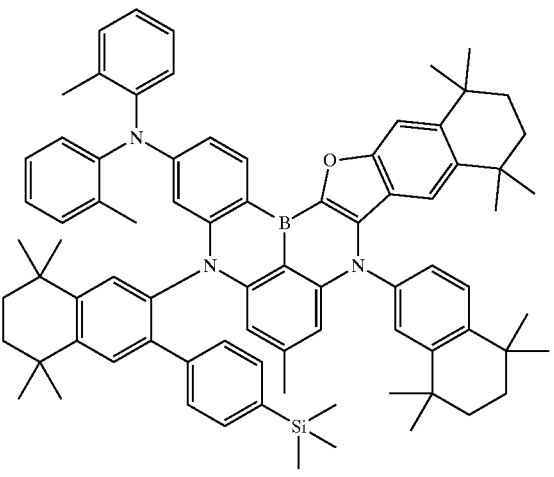

1571
-continued
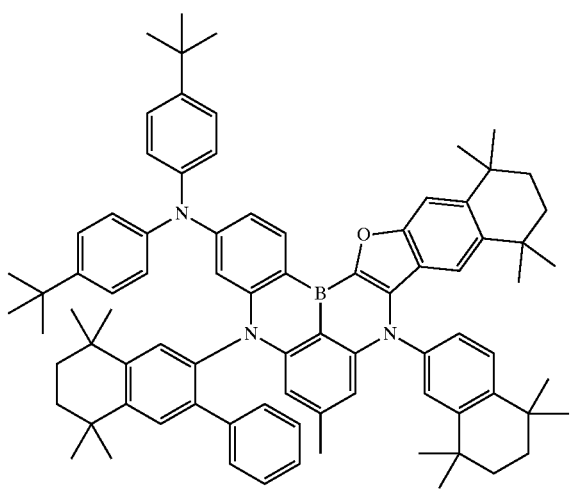
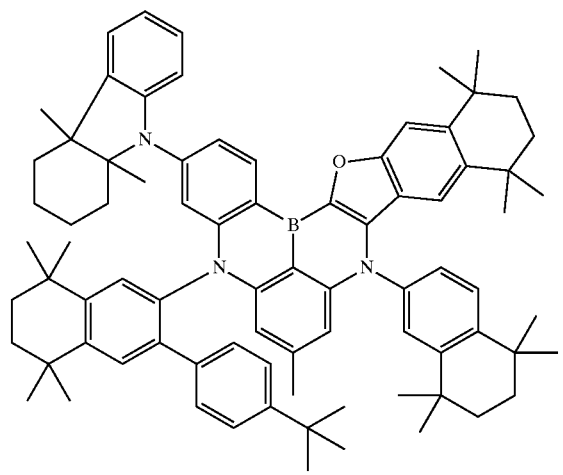
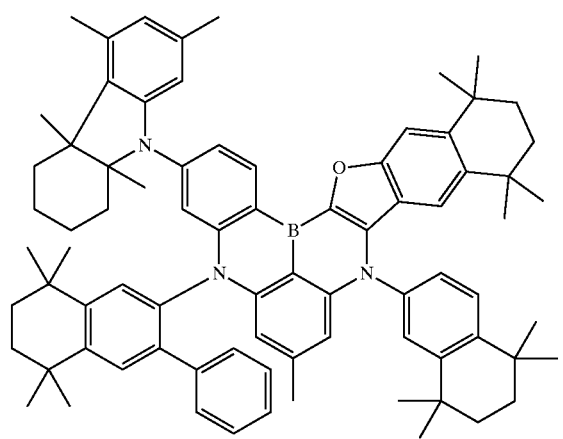
1572
-continued
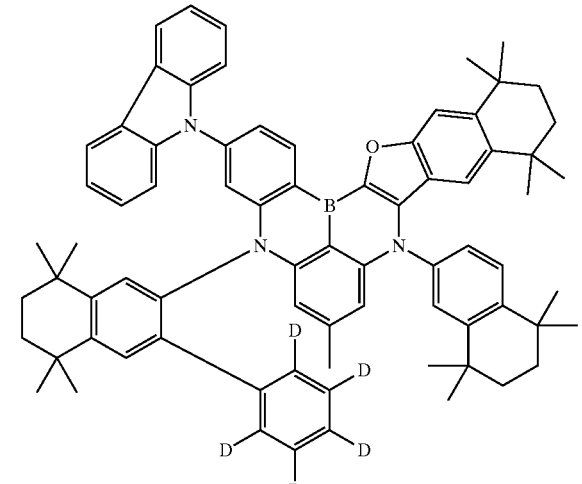
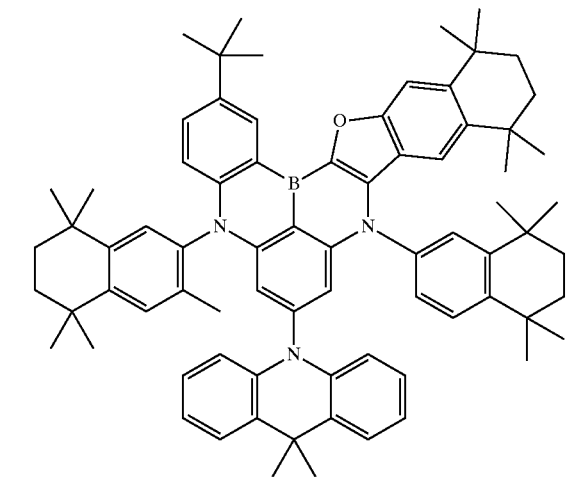
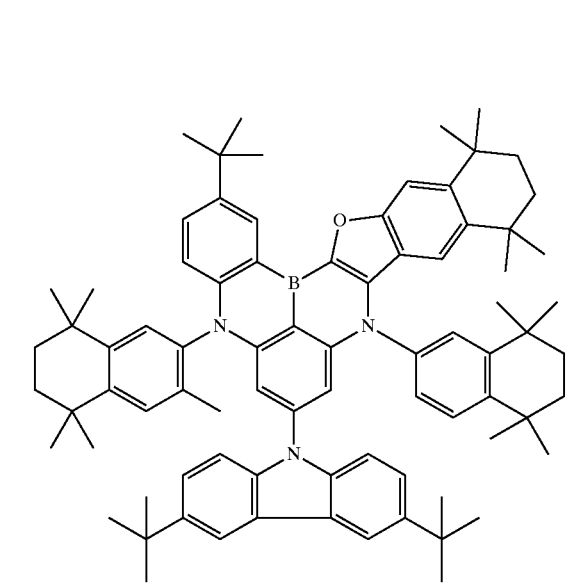

1573
-continued
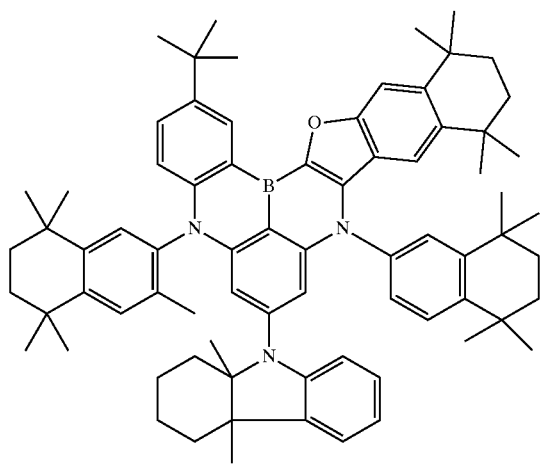
1574
-continued
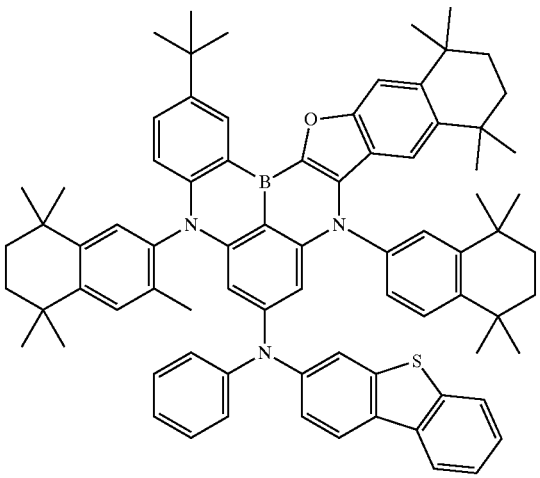
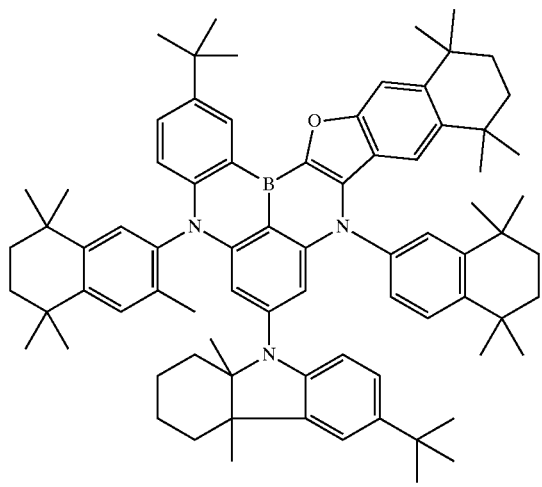
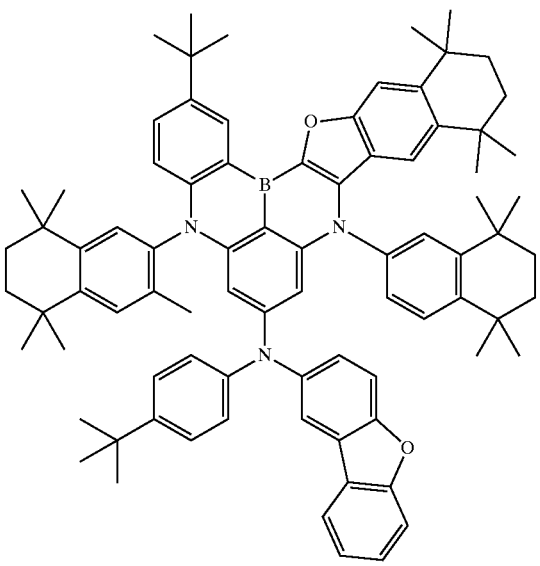
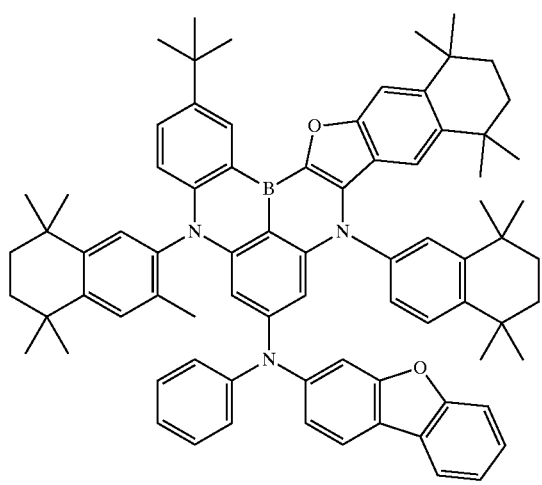
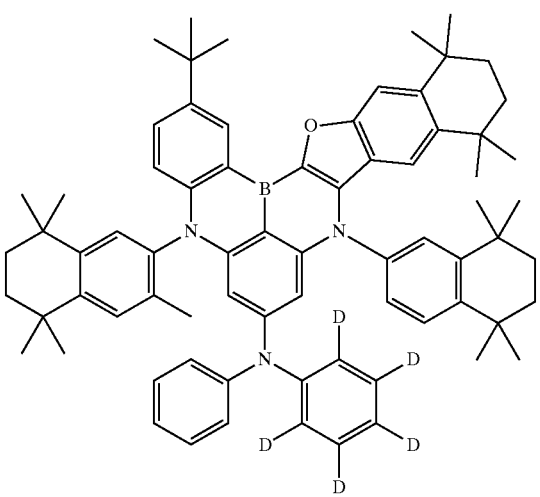

1575
-continued
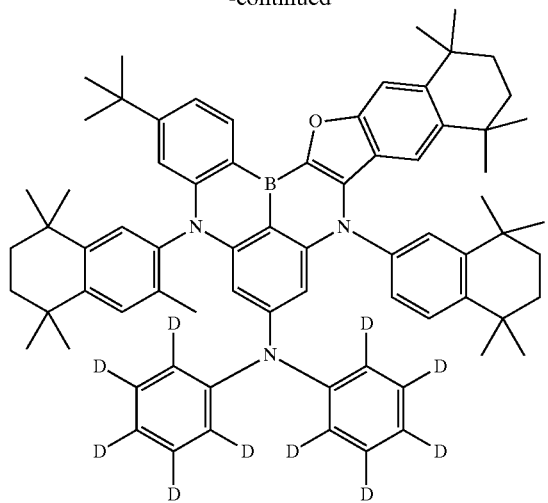
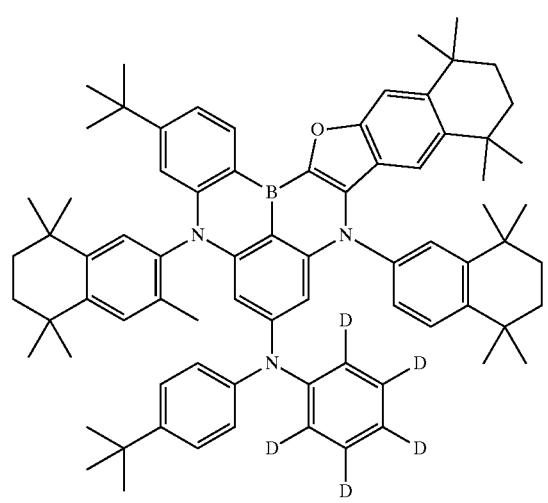
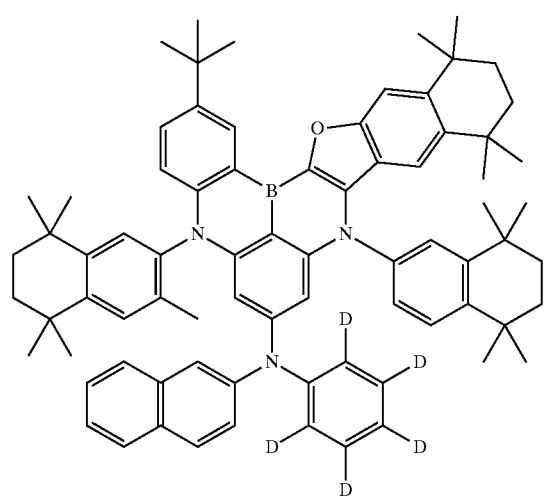
1576
-continued
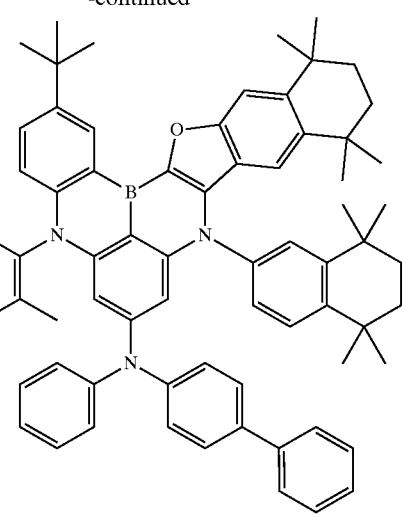
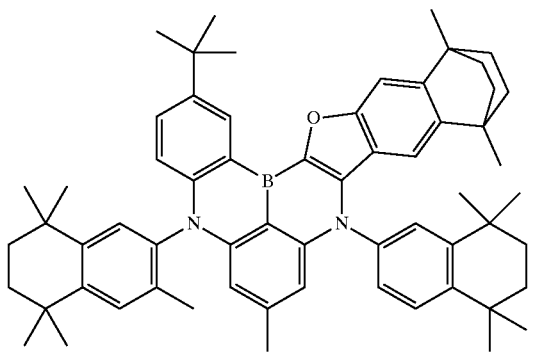
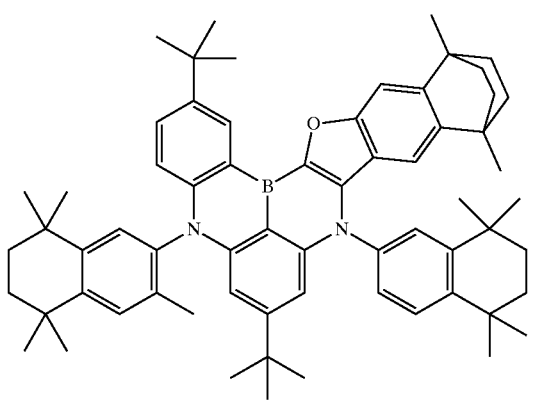
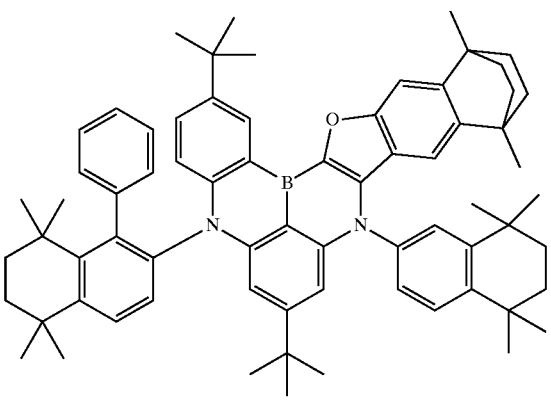

1577
-continued
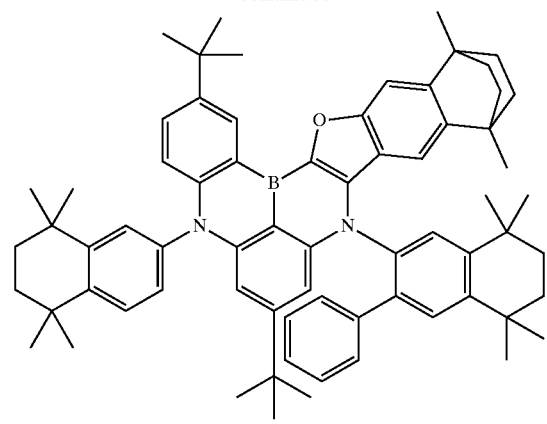
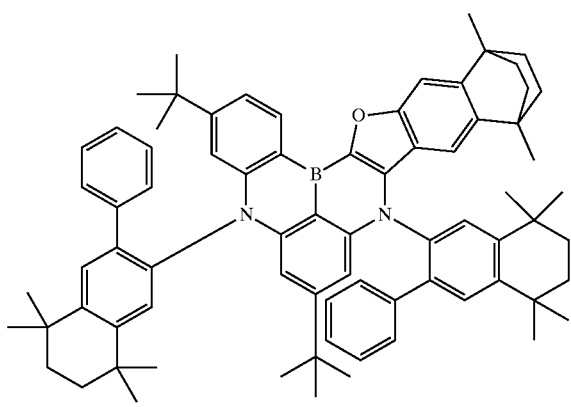
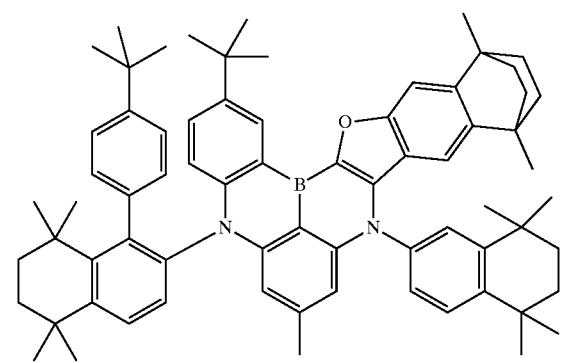
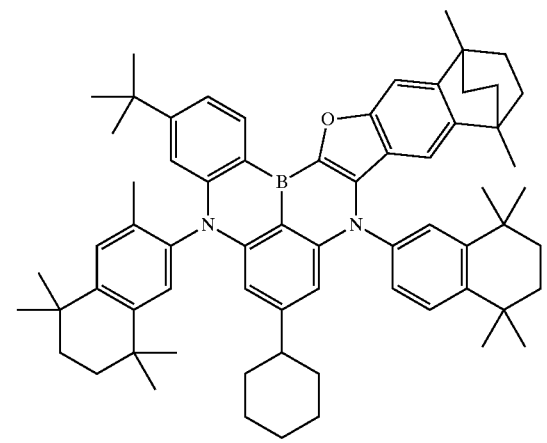
1578
-continued
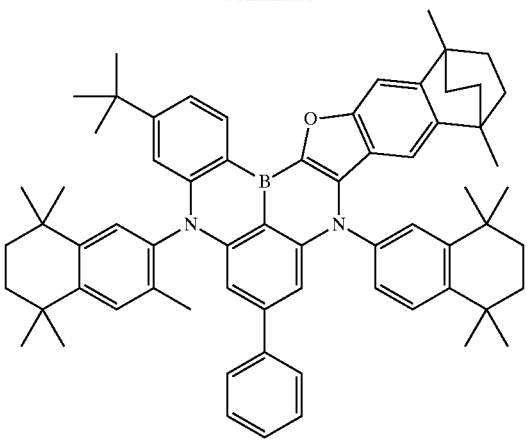
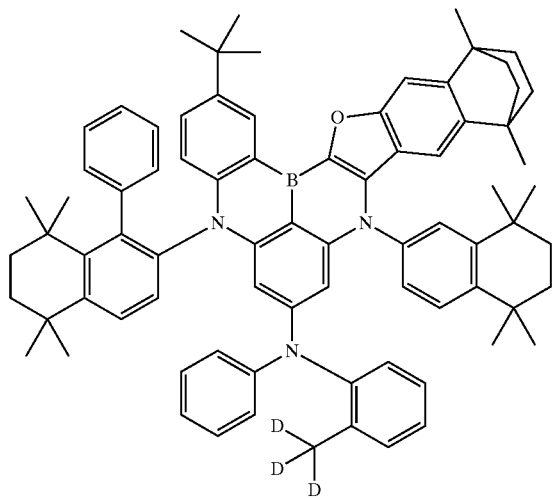
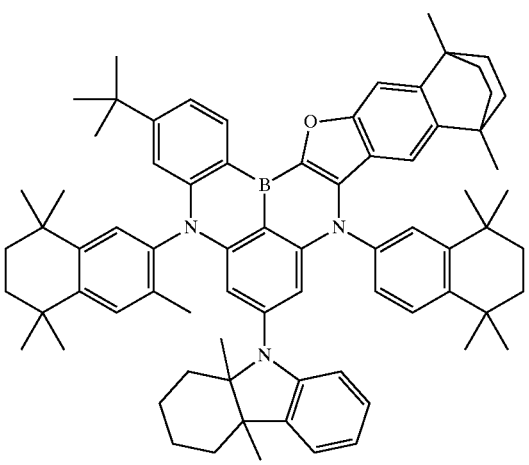

1579
-continued
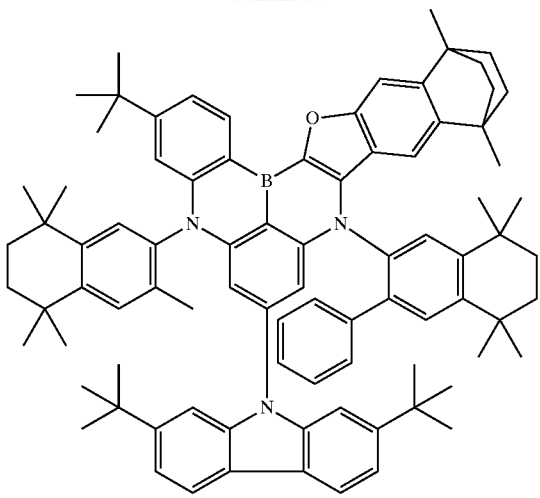
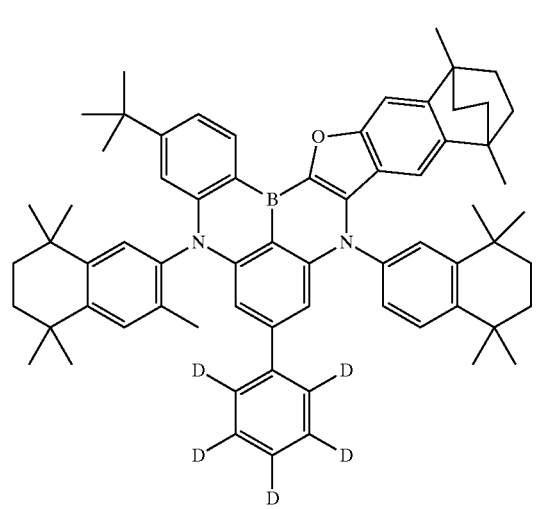
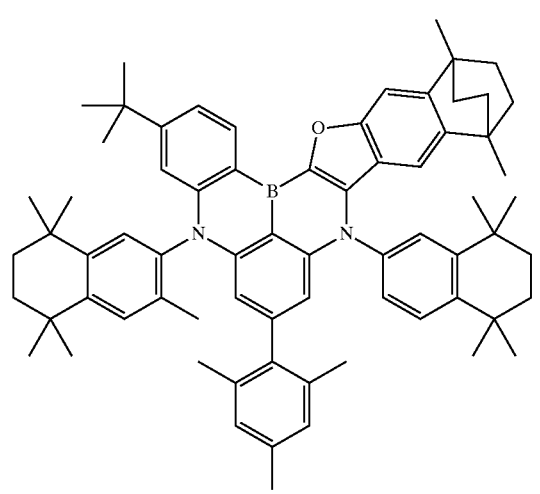
1580
-continued
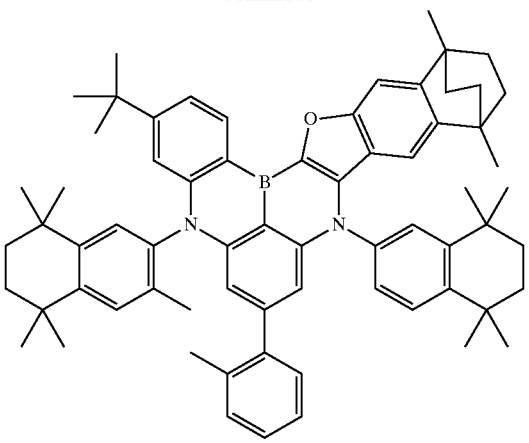
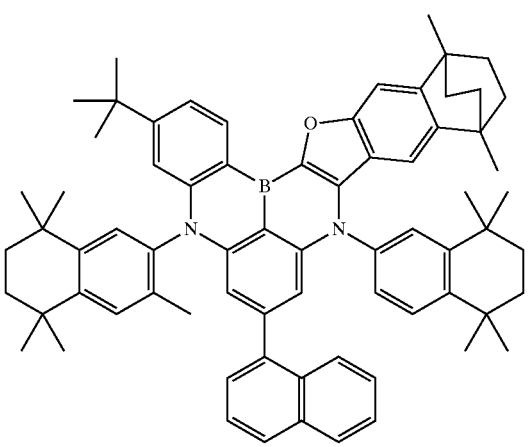
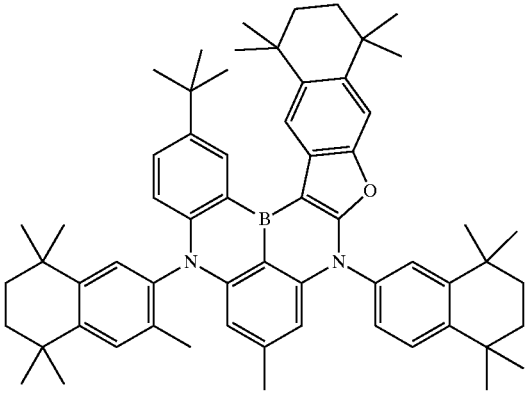

1581
-continued
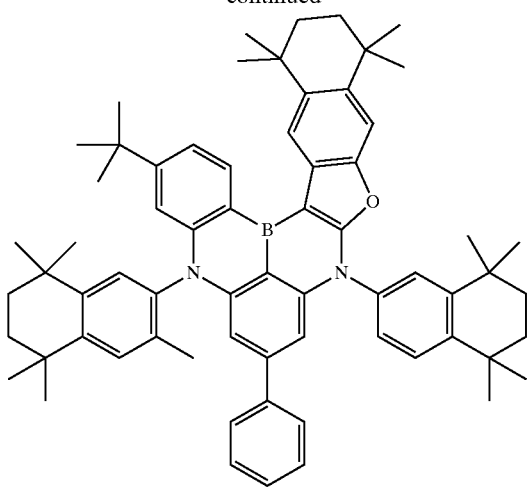
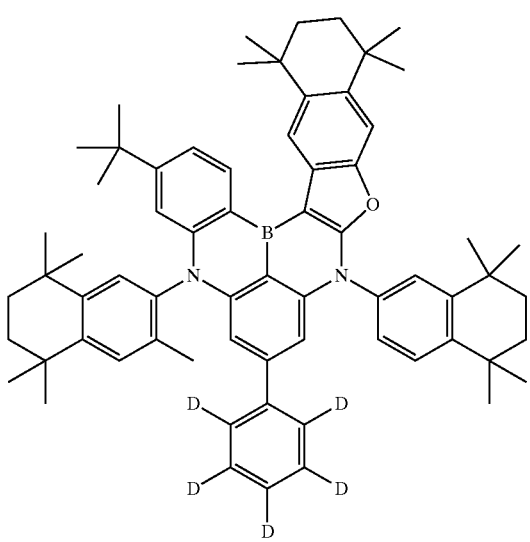
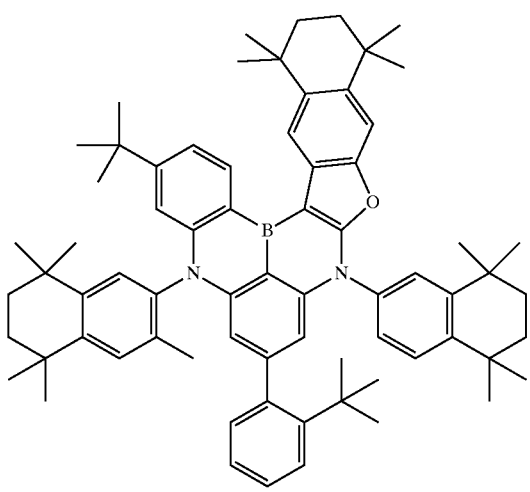
1582
-continued
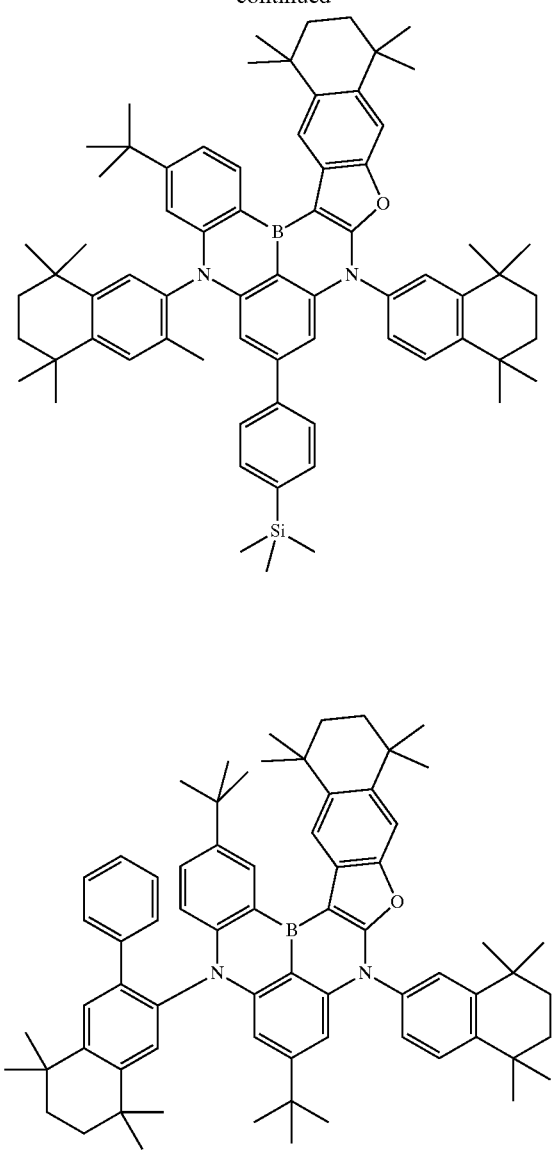

1583
-continued
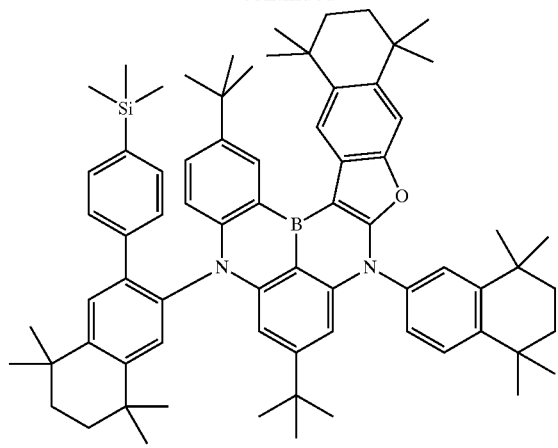
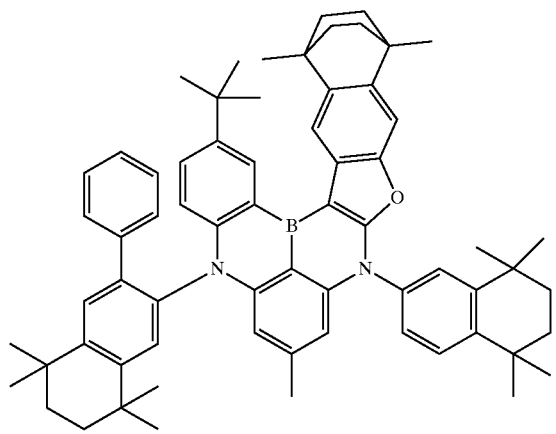
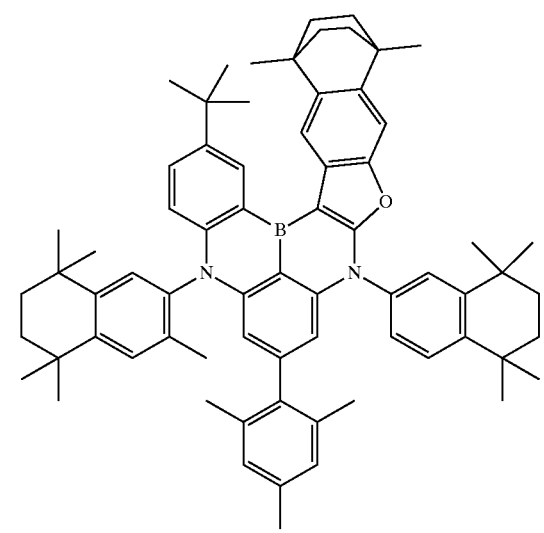
1584
-continued
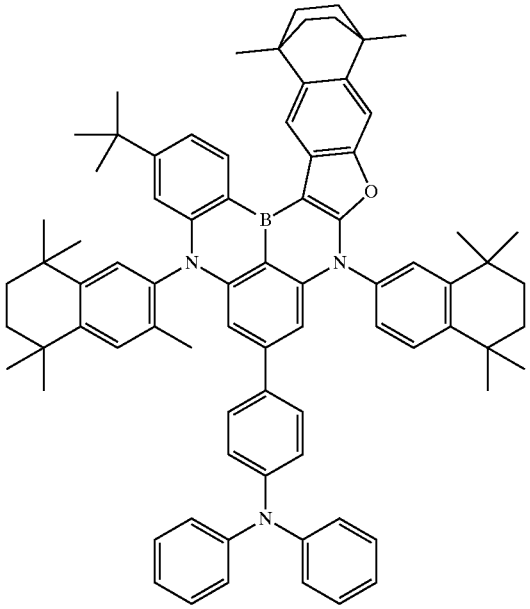
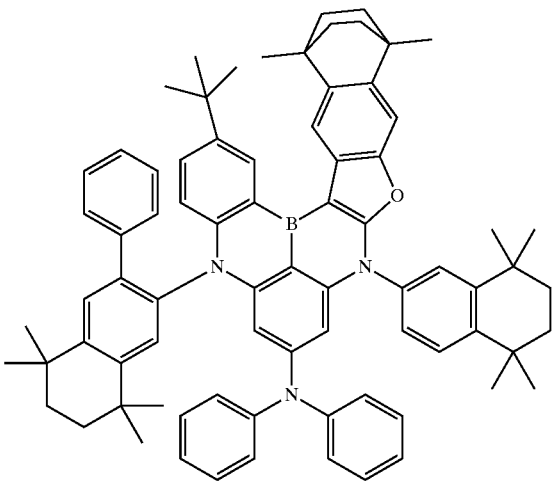
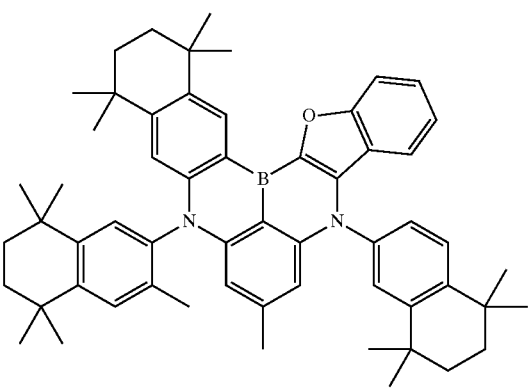

1585
-continued
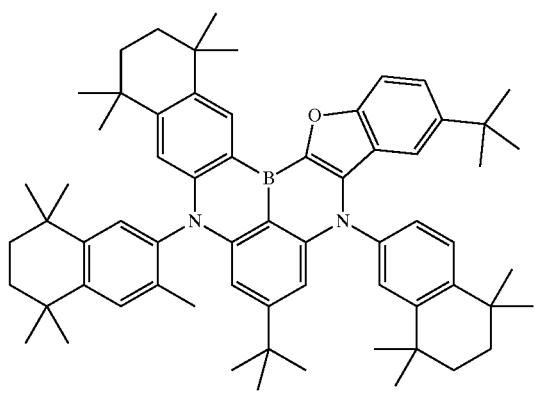
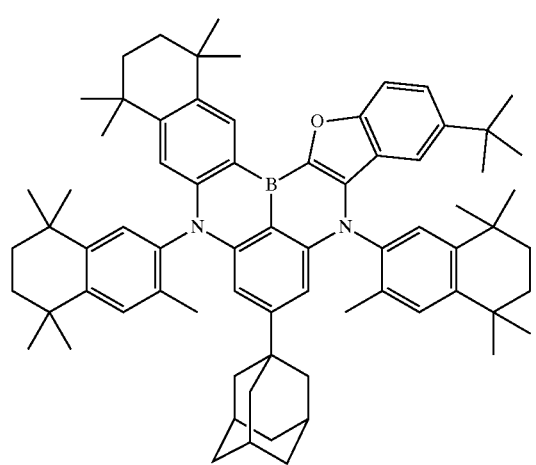
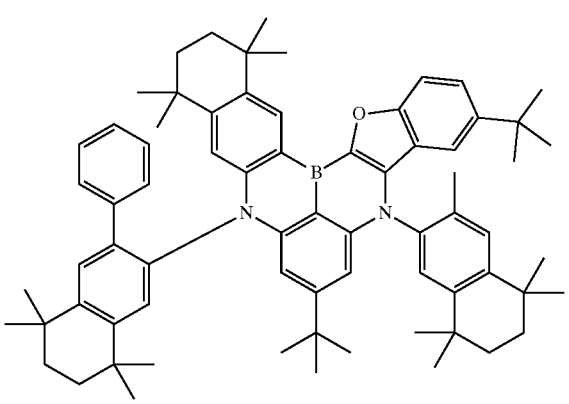
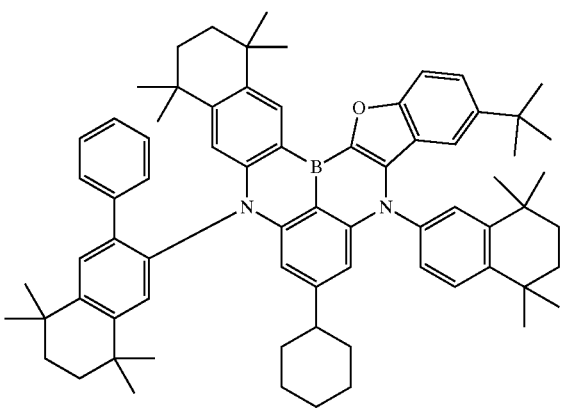
1586
-continued
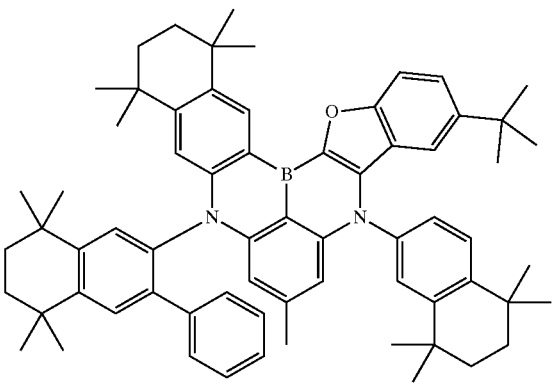
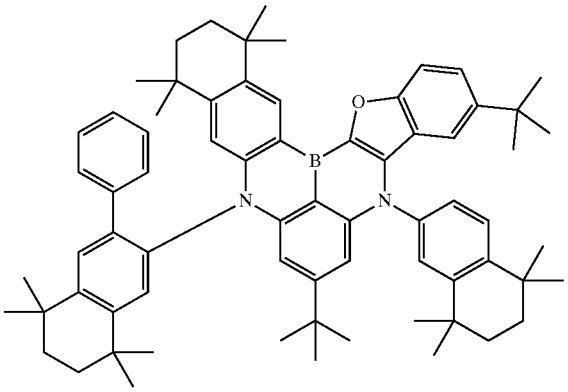
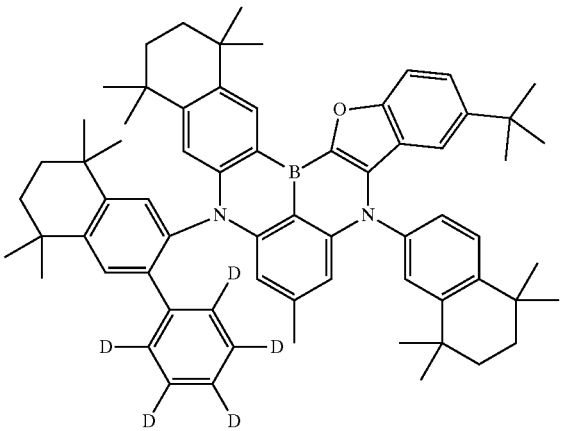
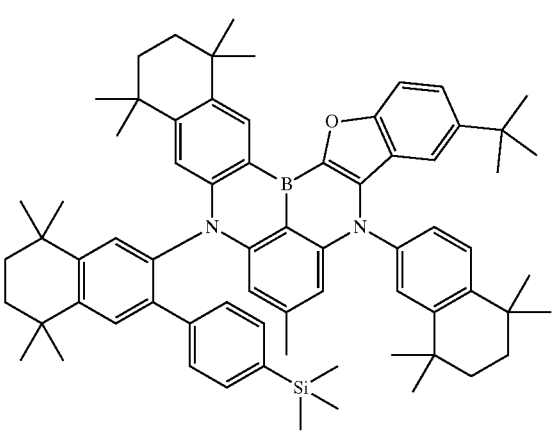

1587
-continued
1588
-continued
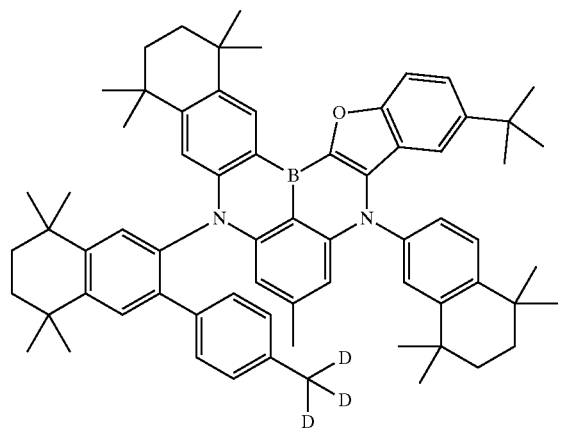
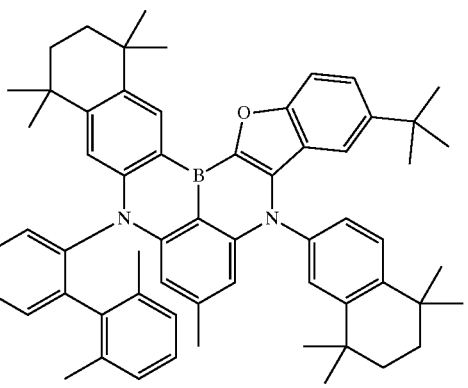
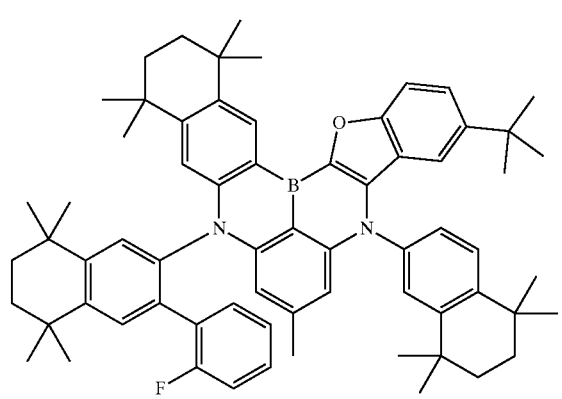
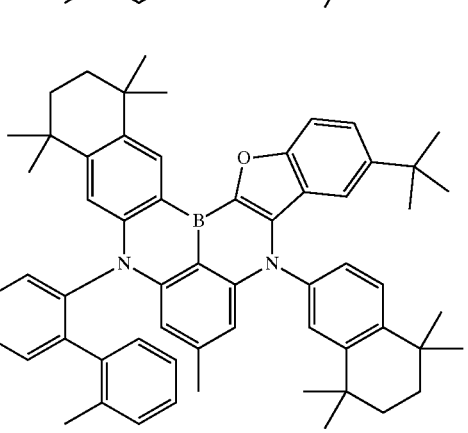
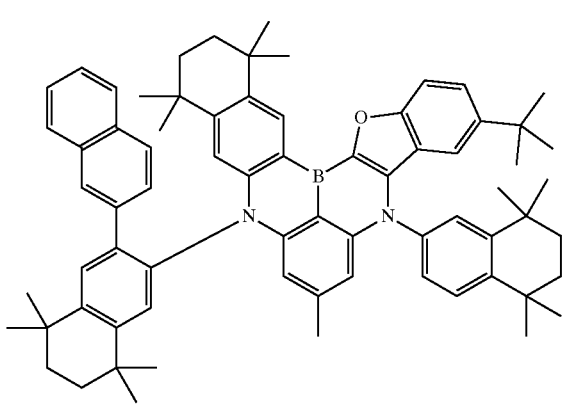
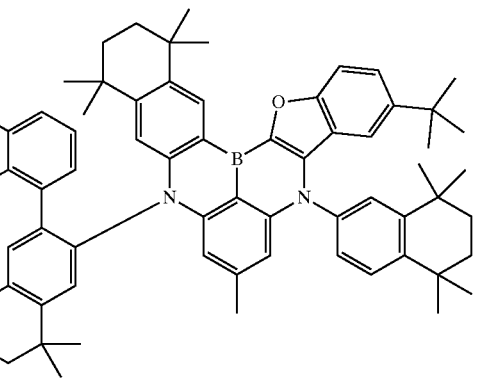
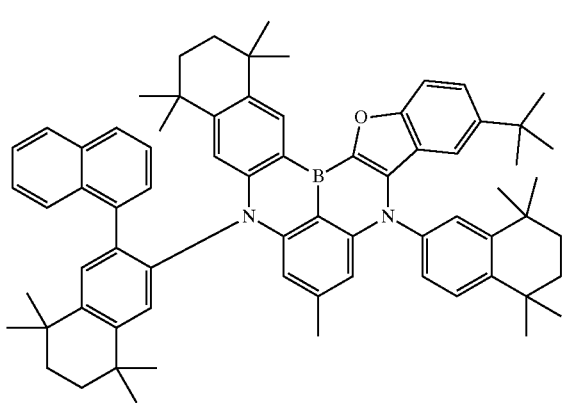
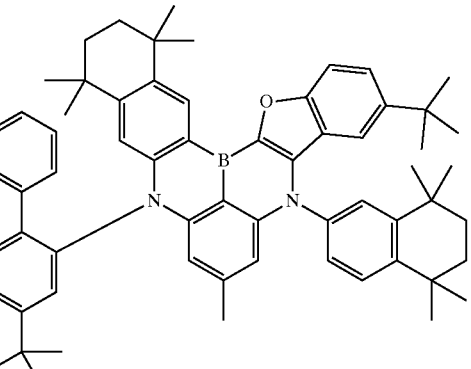

| 1589 -continued | 1590 -continued |
|---|---|
| 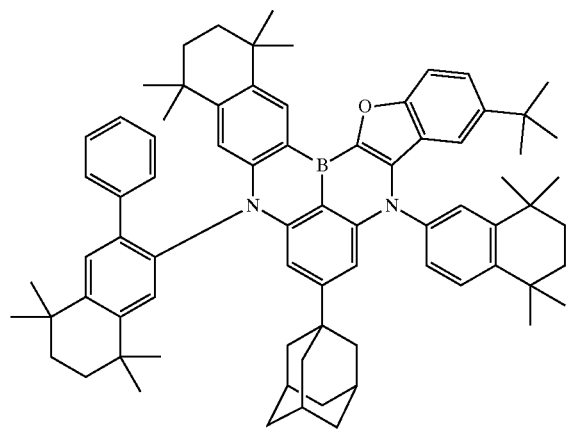 | 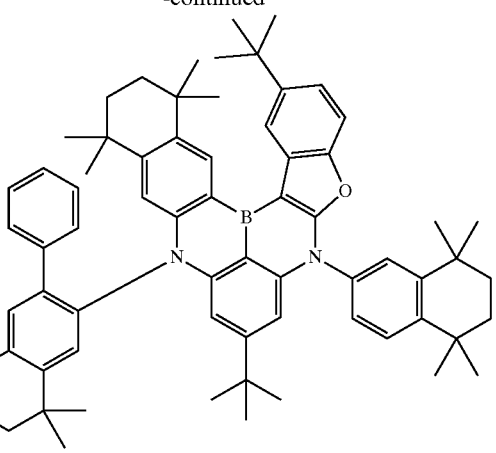 |
| 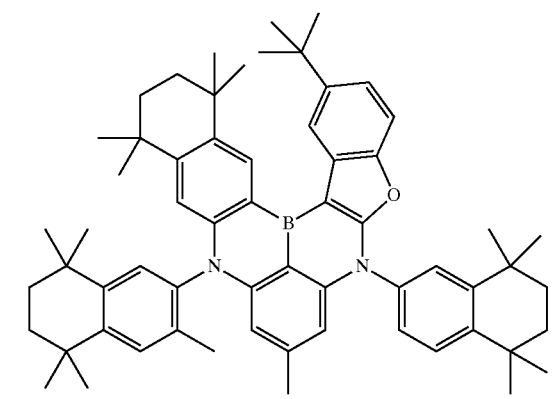 | 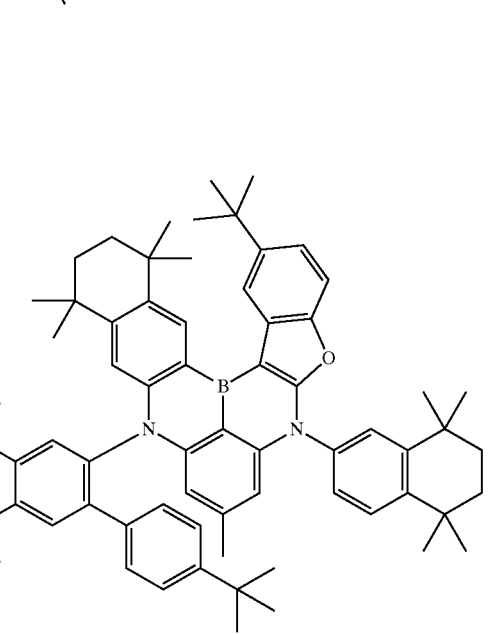 |
| 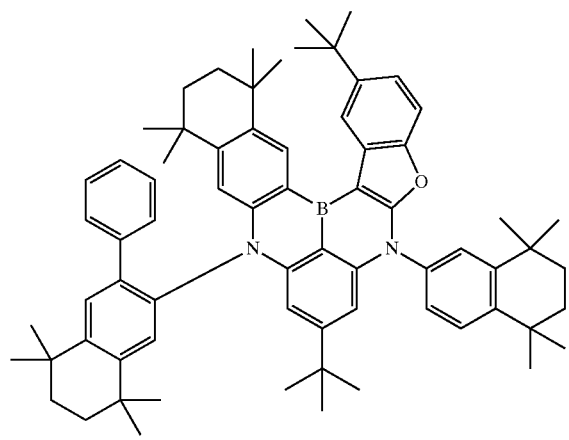 | 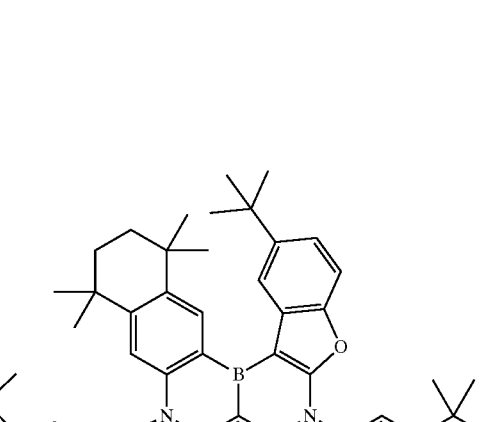 |
| 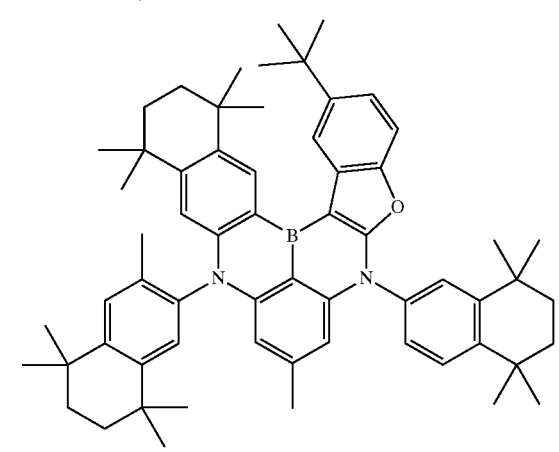 | 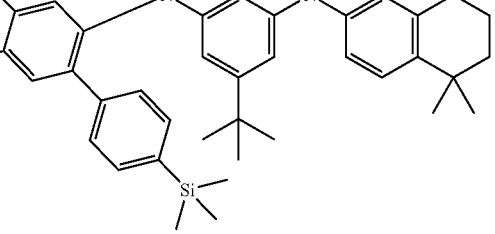 |

| 1591 | 1592 |
|---|---|
| -continued | -continued |
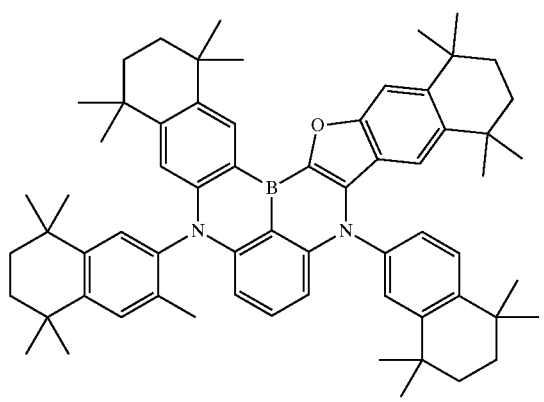
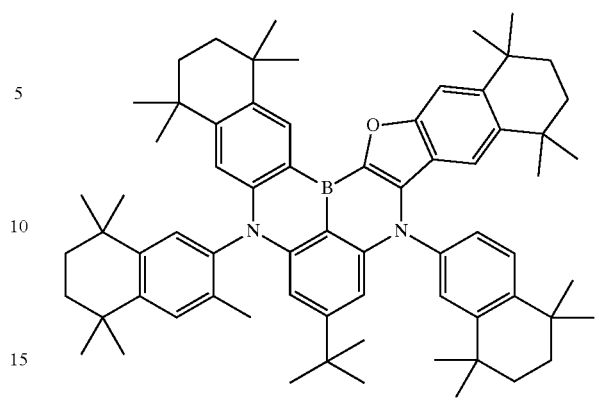
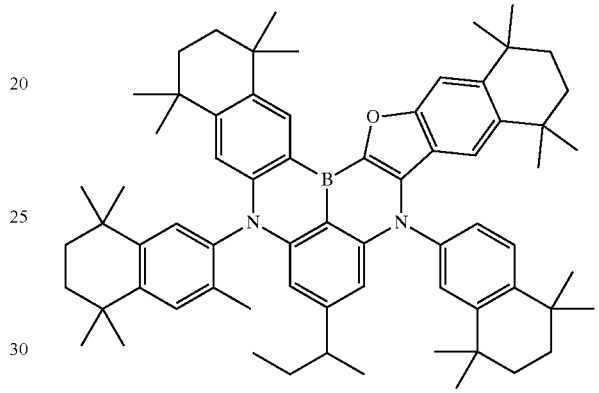
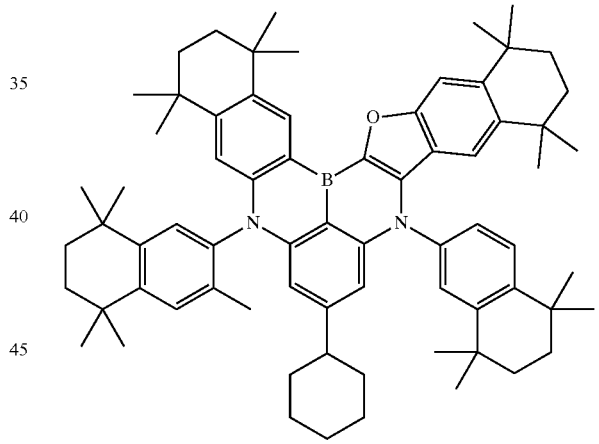
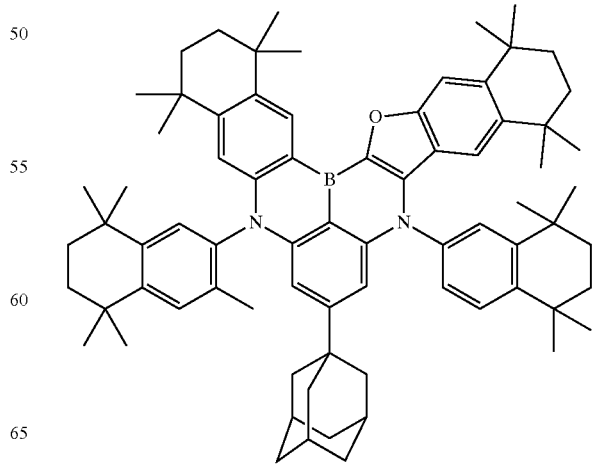

1593
-continued
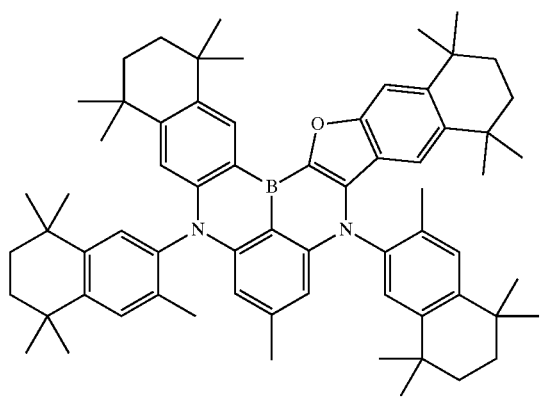
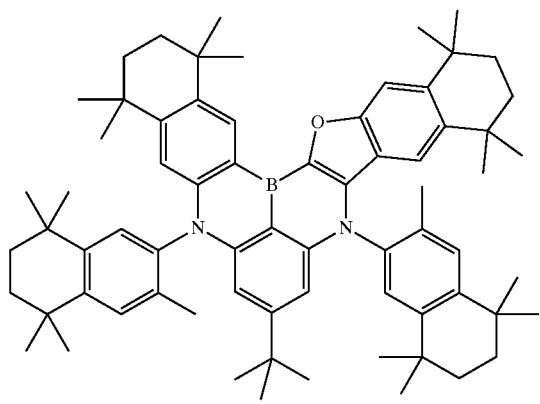
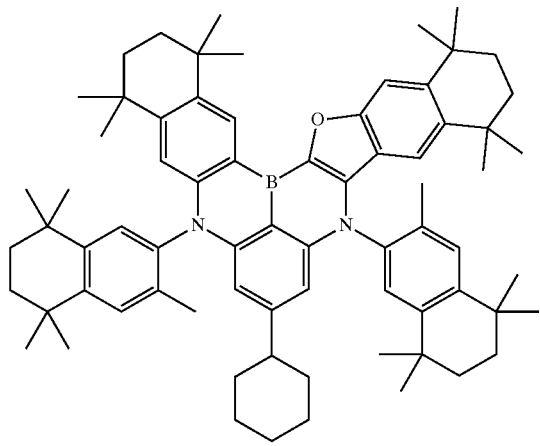
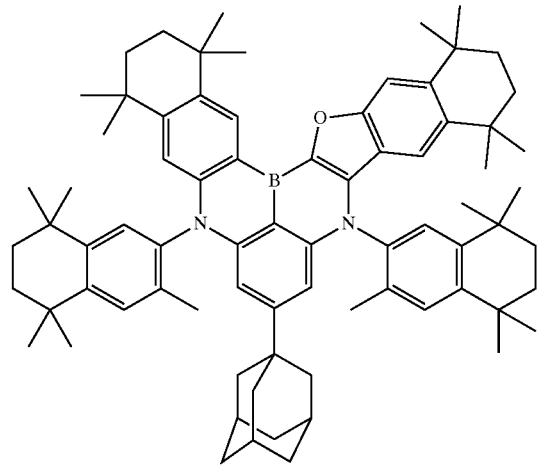
1594
-continued
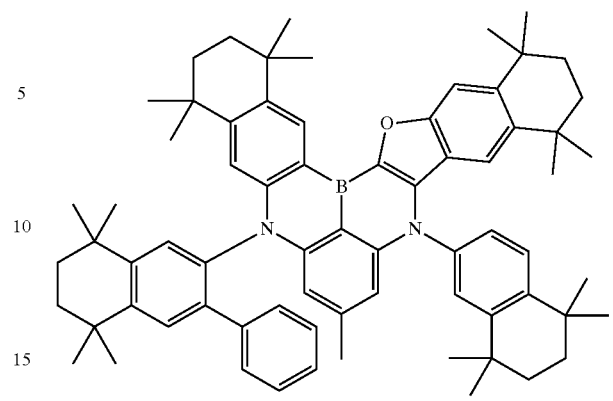
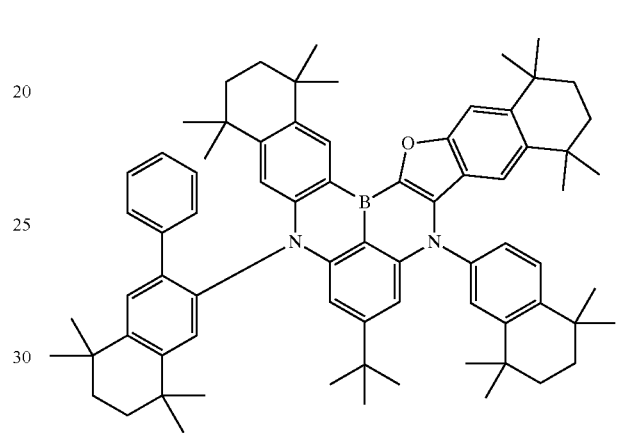
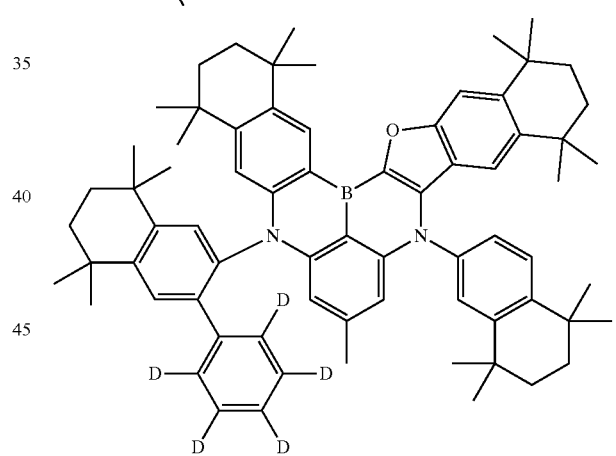
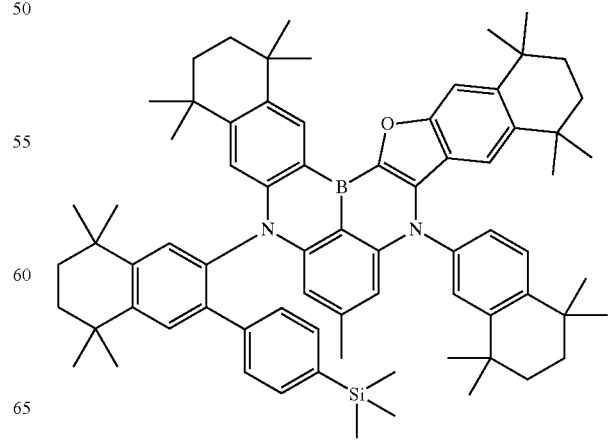

1595
-continued
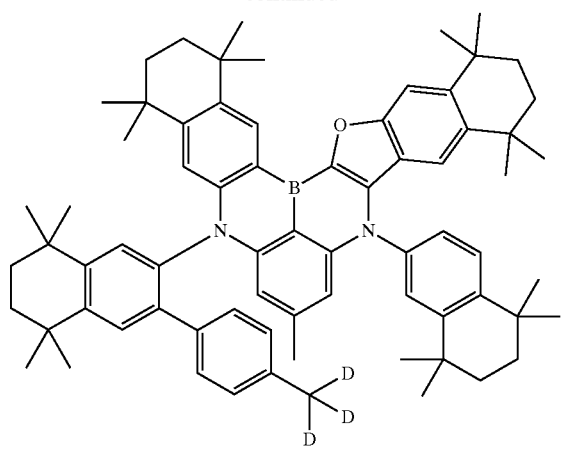
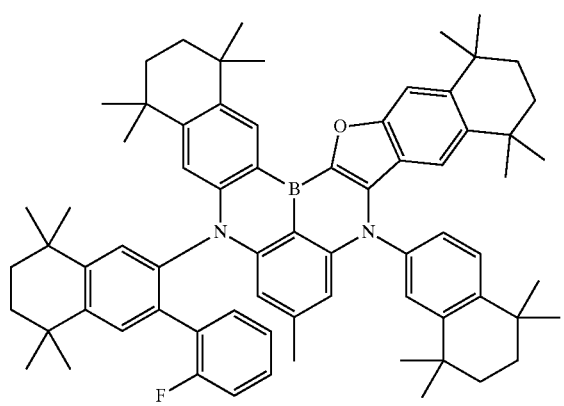
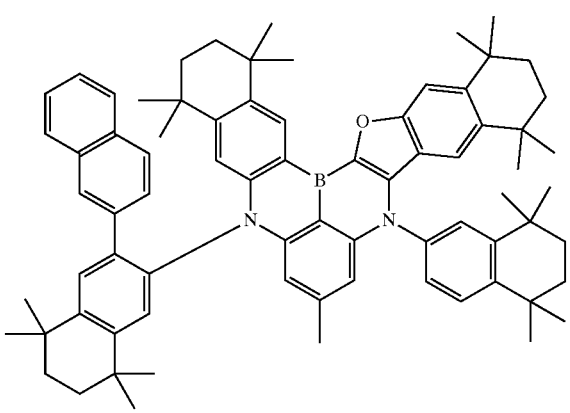
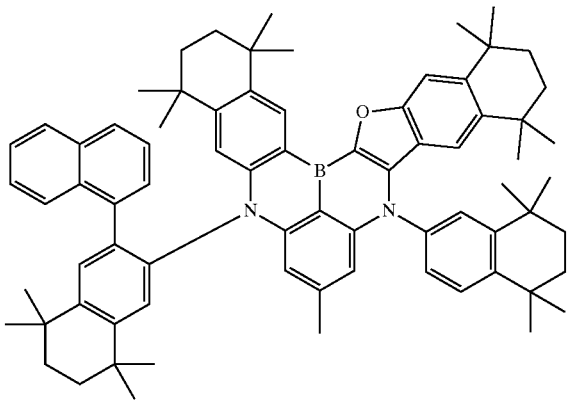
1596
-continued
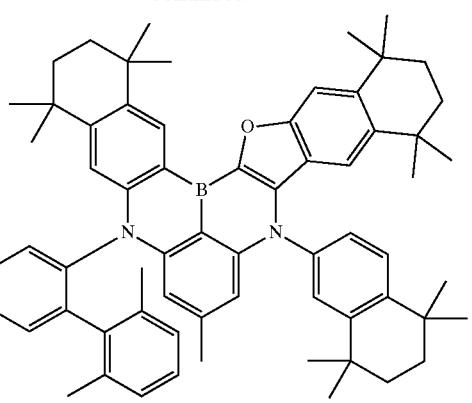
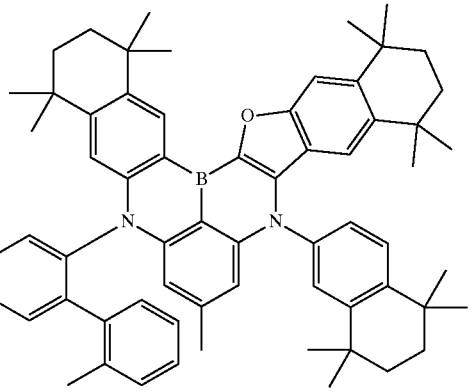
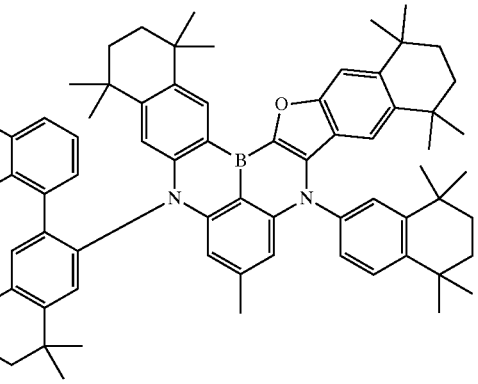
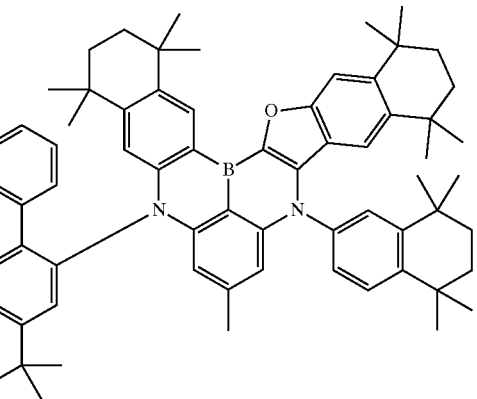

1597
-continued
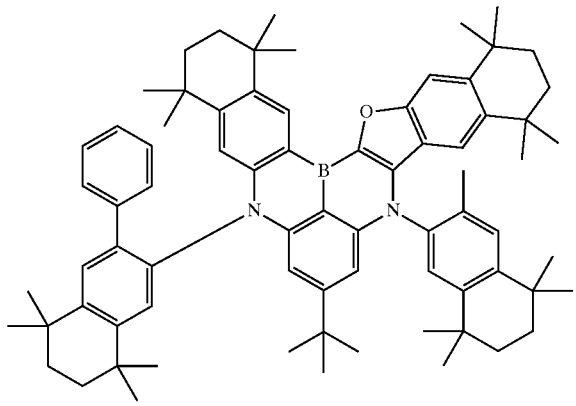
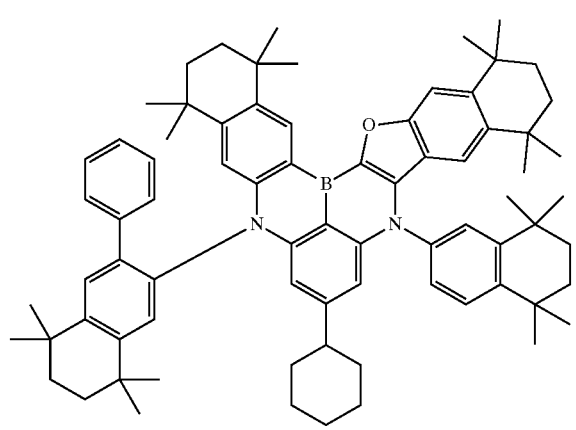
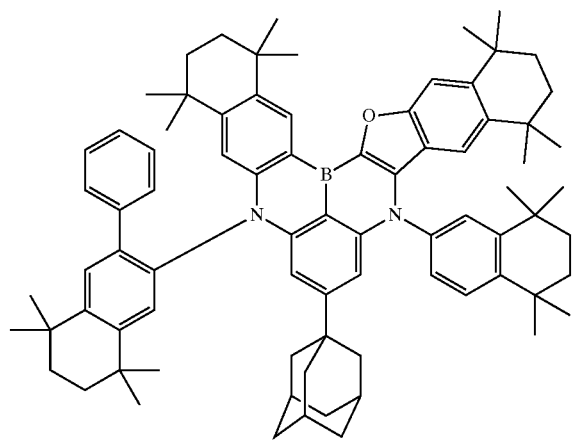
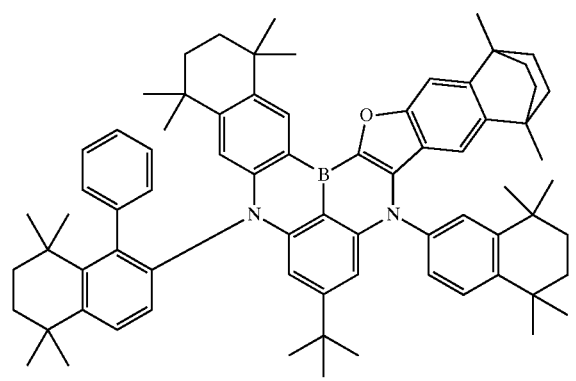
1598
-continued
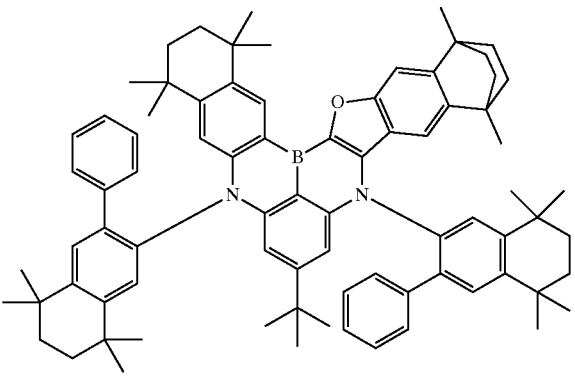
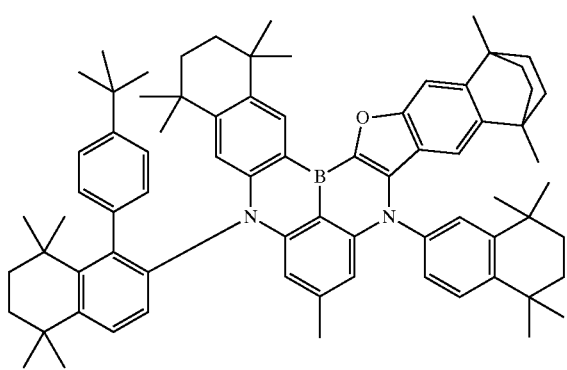
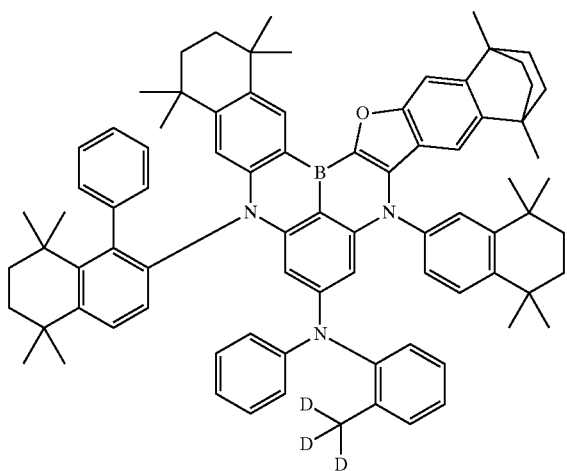
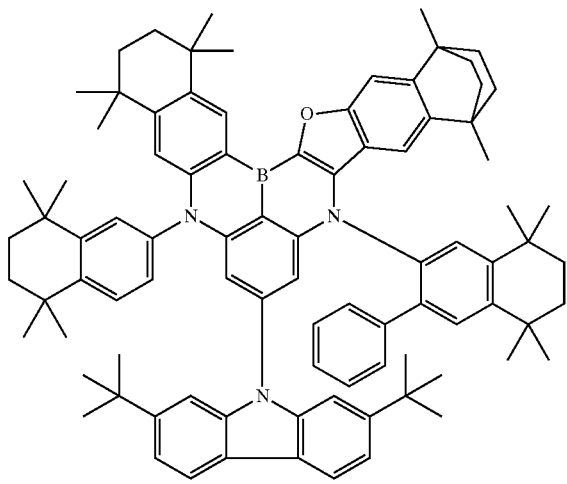

1599
-continued
1600
-continued
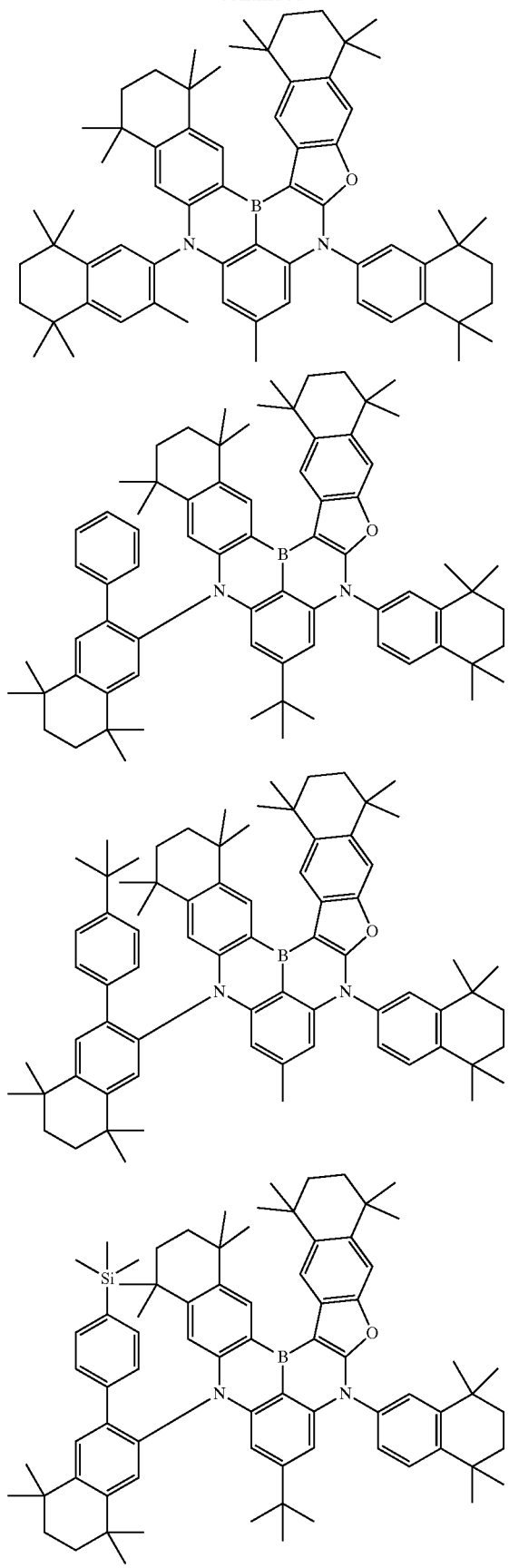
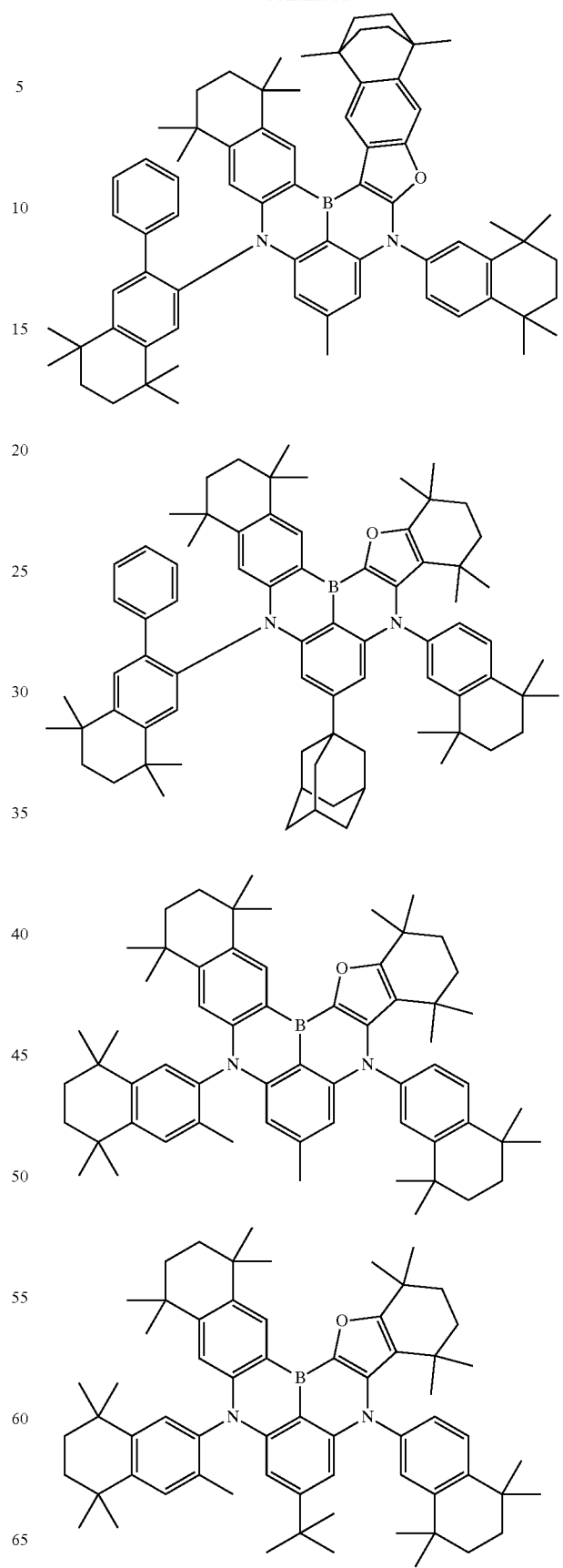

1601
-continued
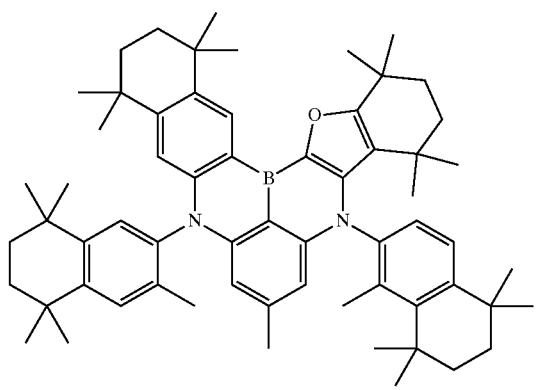
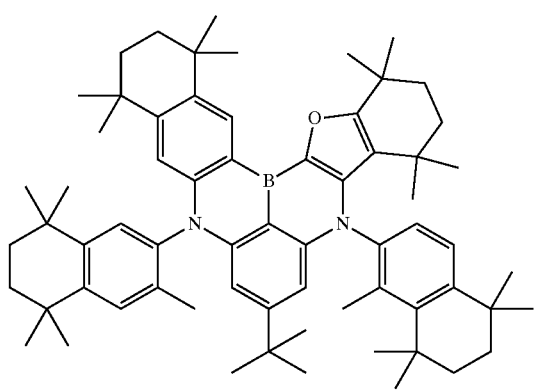
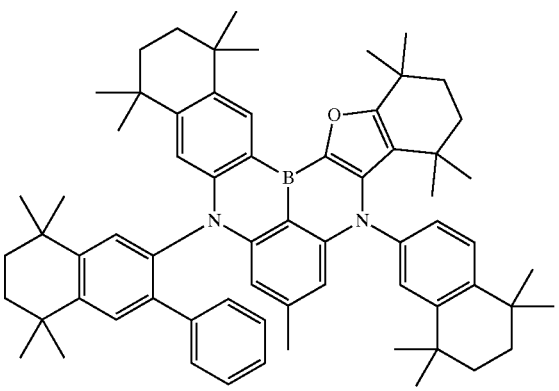
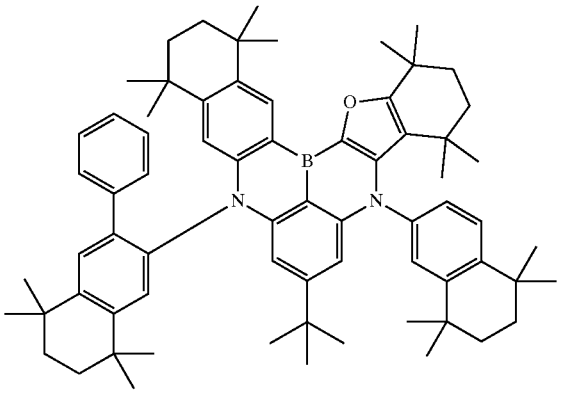
1602
-continued
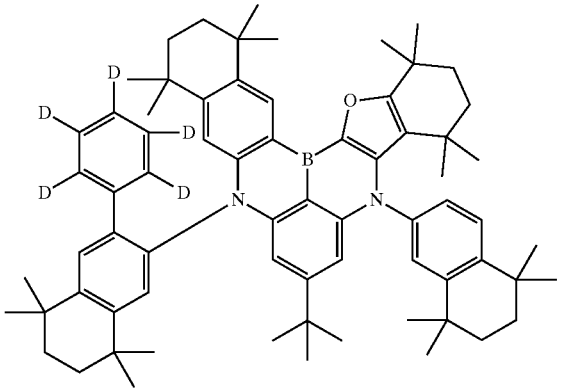
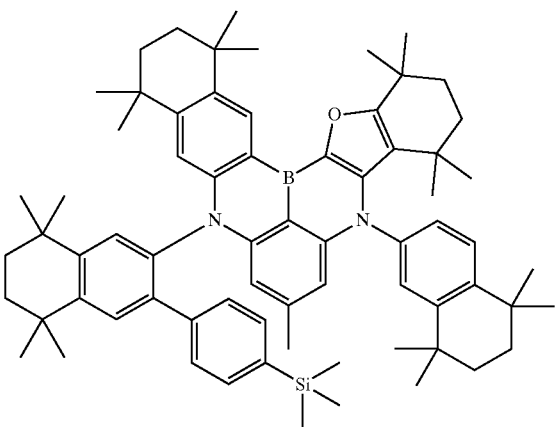
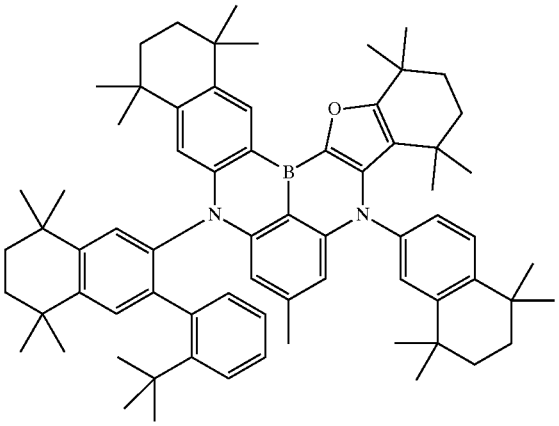
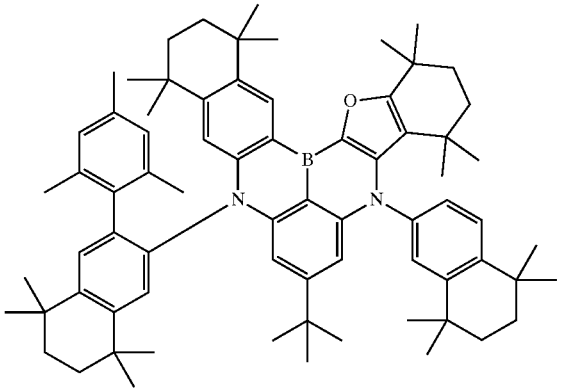

1603
-continued
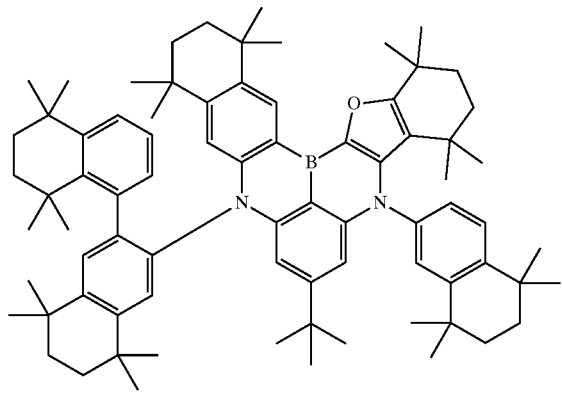
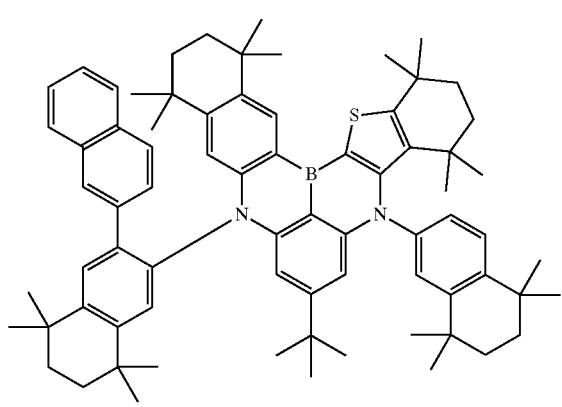
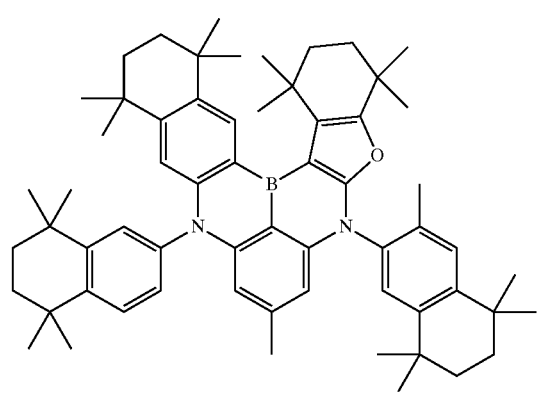
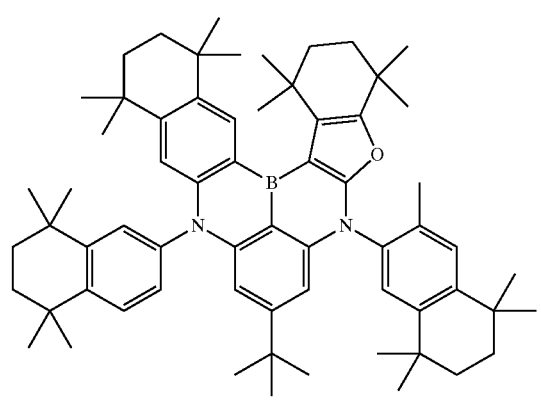
1604
-continued
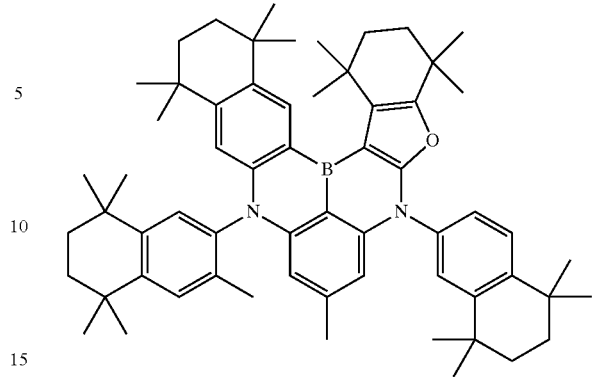
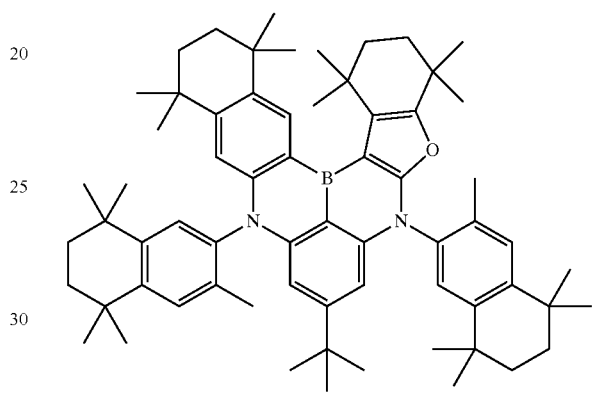
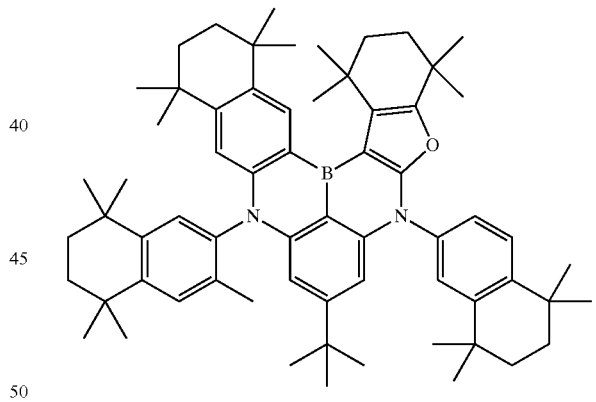
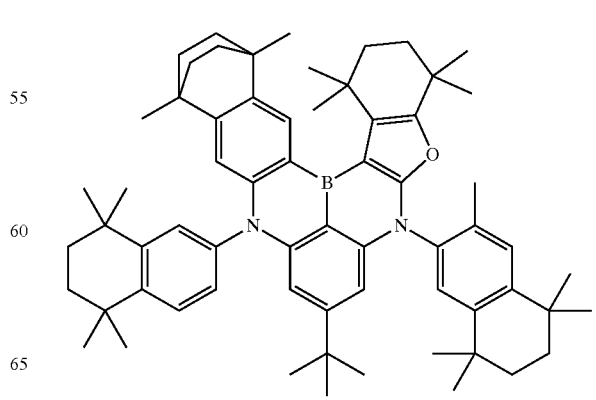

1605
-continued
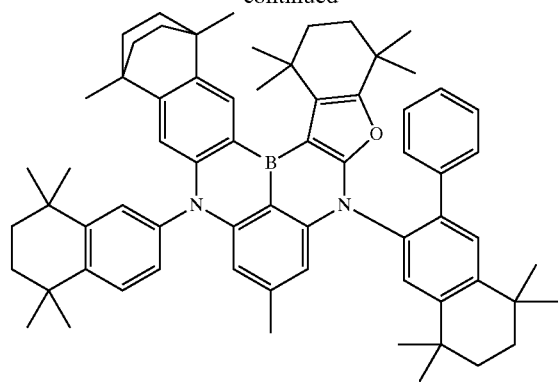
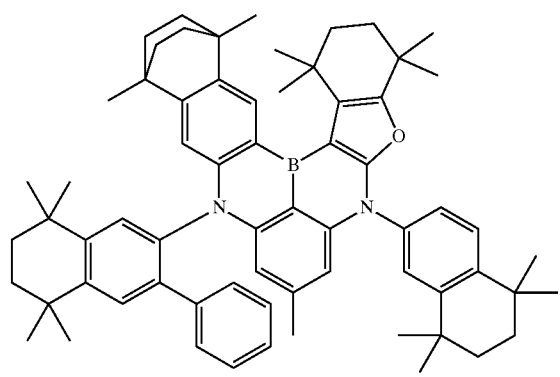
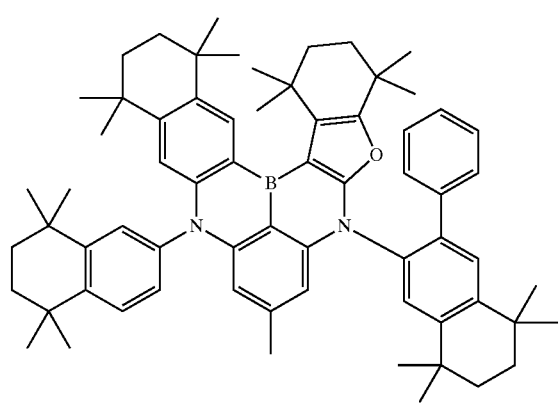
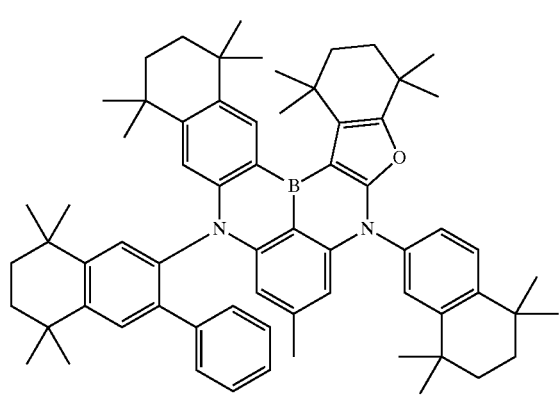
1606
-continued
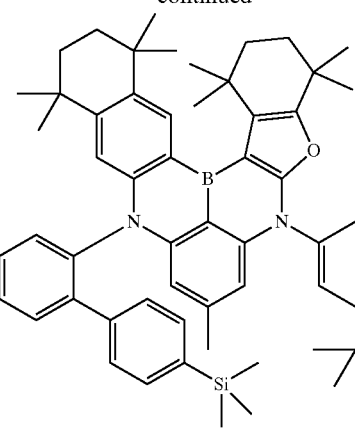
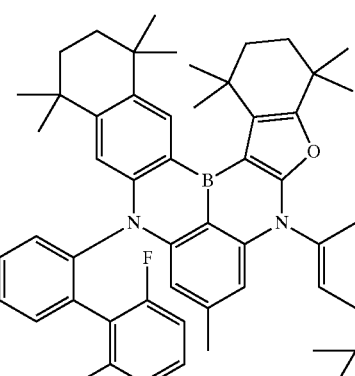
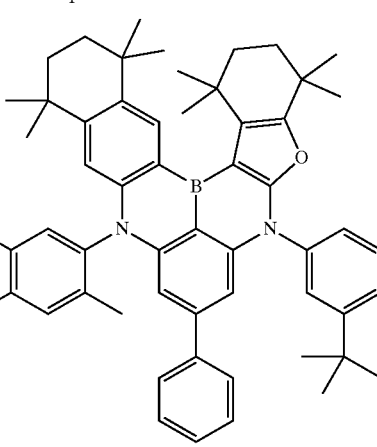
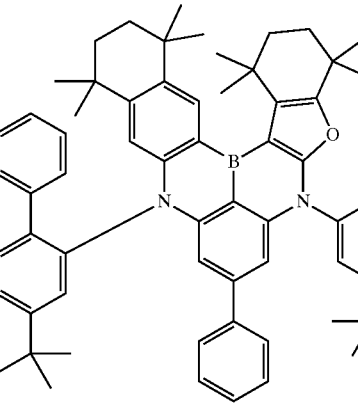

1607
-continued
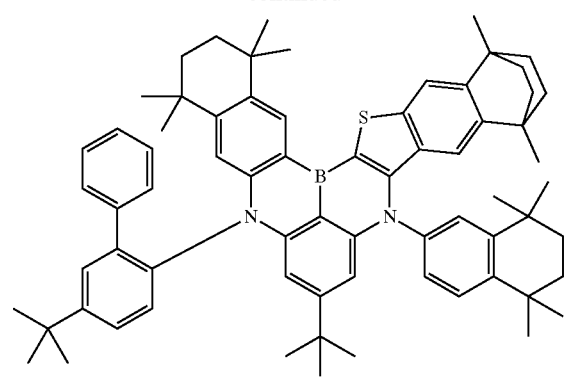
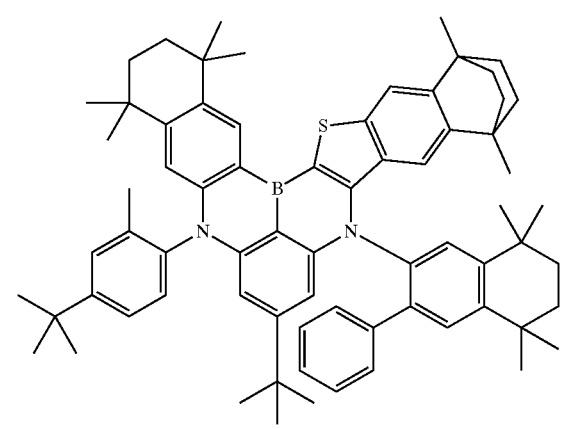
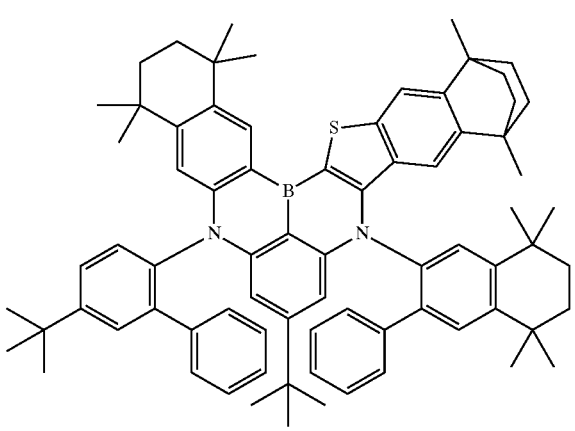
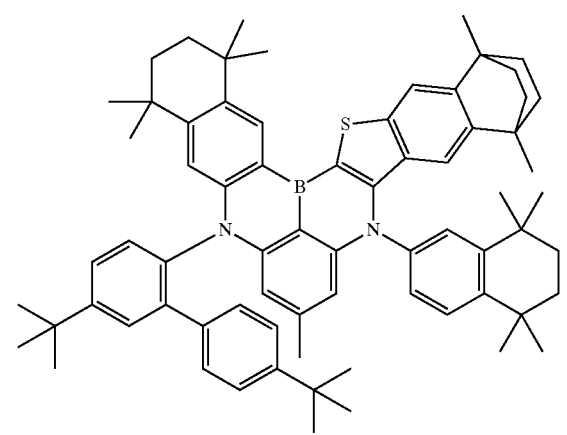
1608
-continued
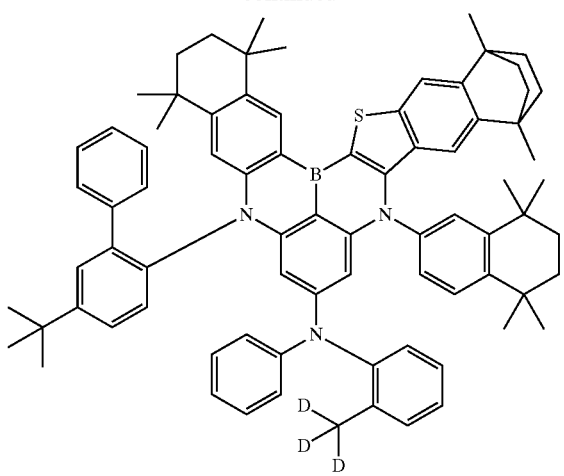
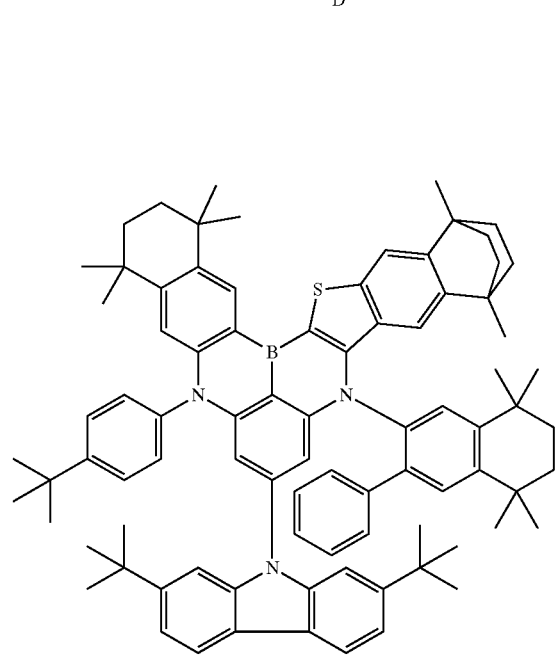
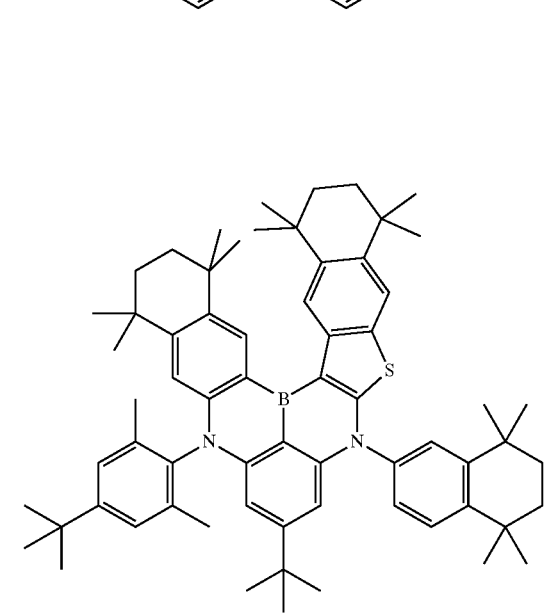

1609
-continued
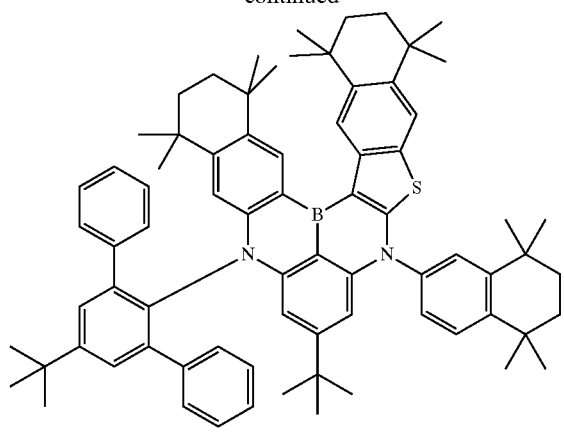
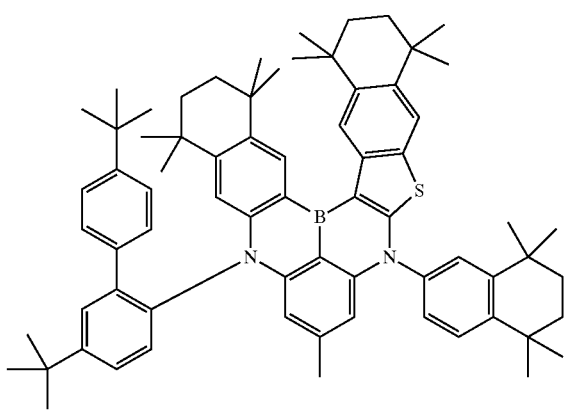
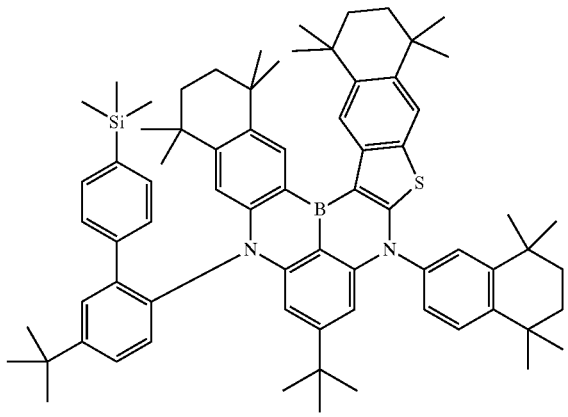
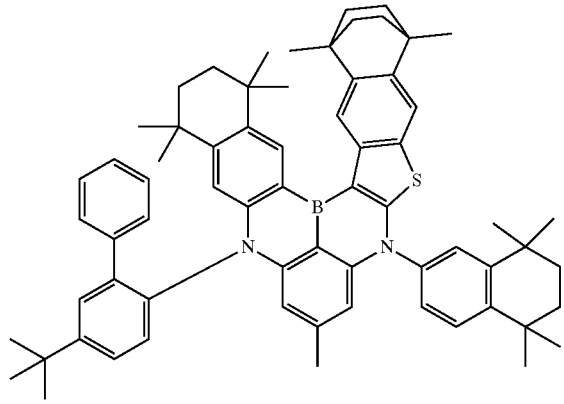
1610
-continued
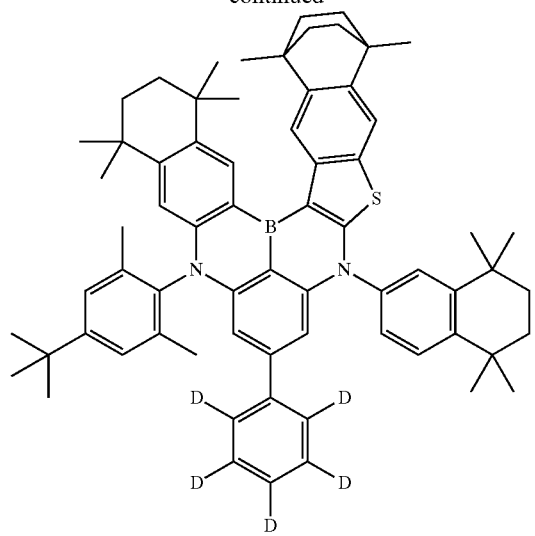
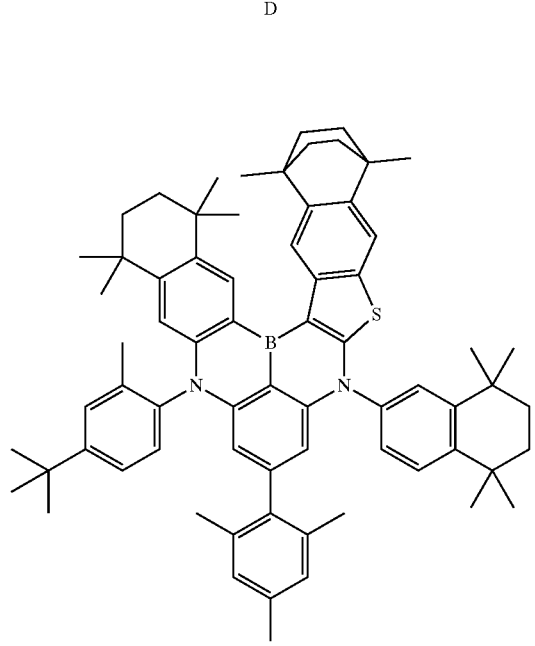
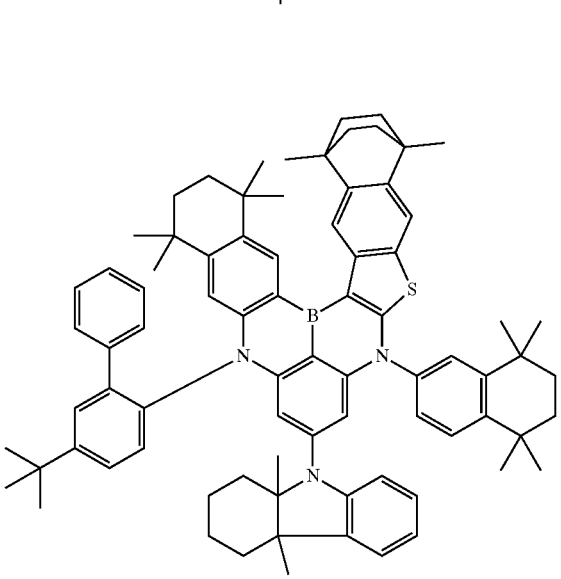

1611
-continued
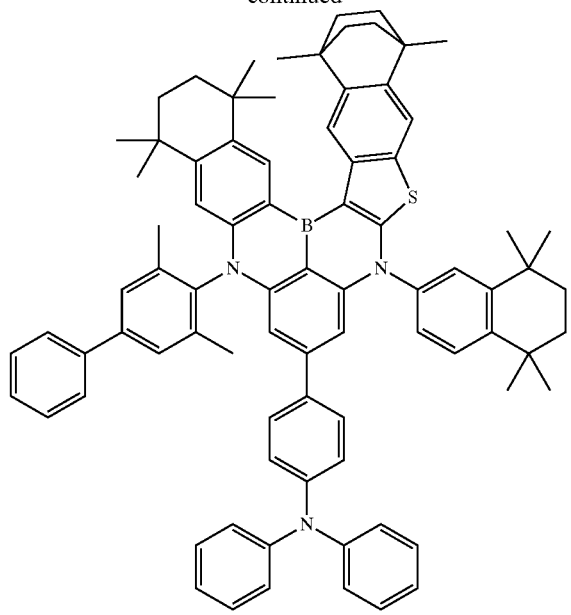
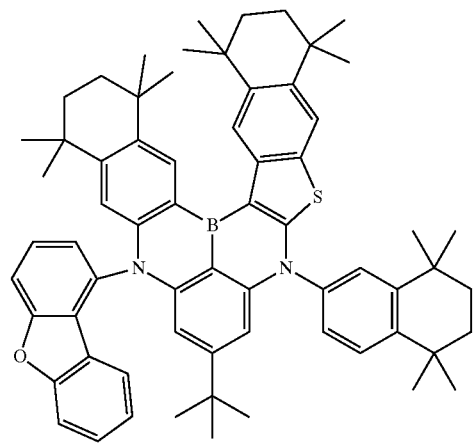
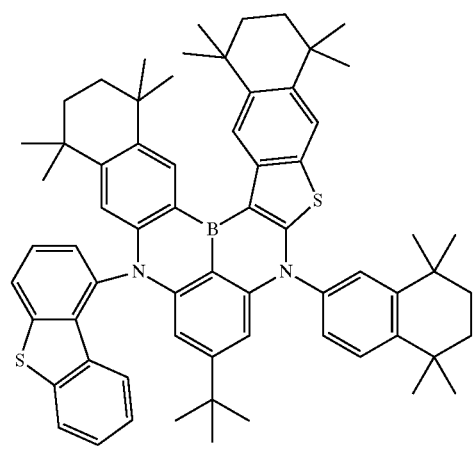
1612
-continued
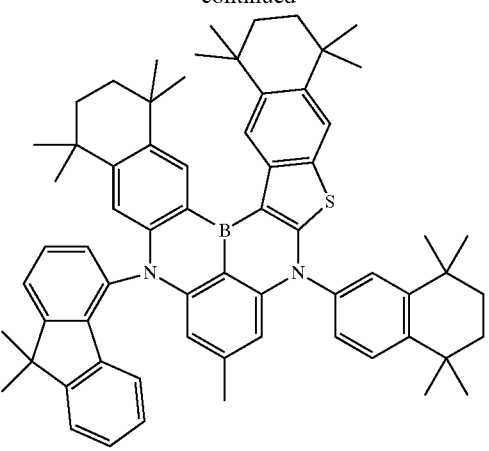
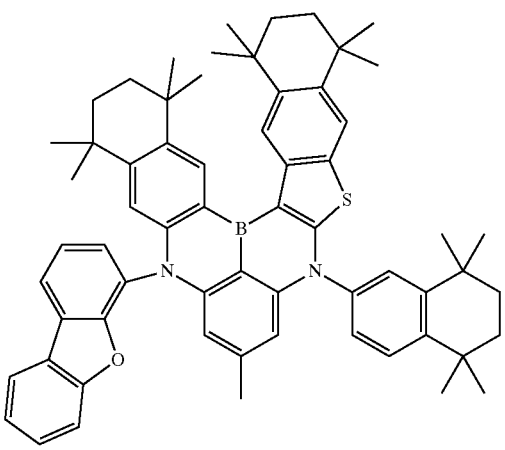
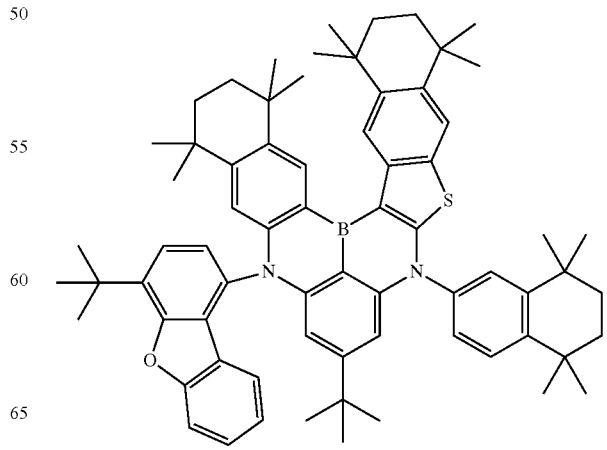

1613
-continued
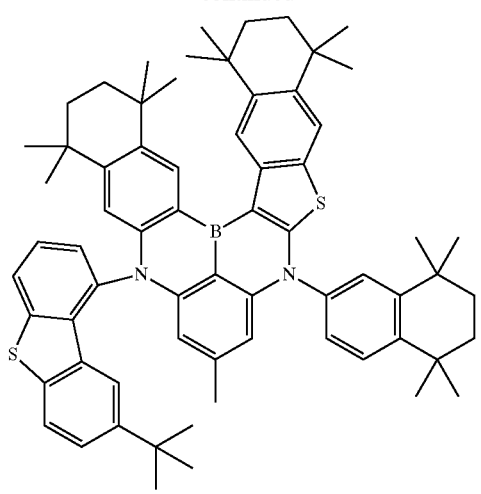
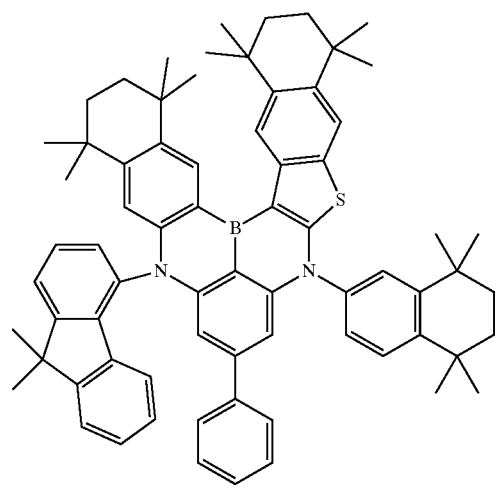
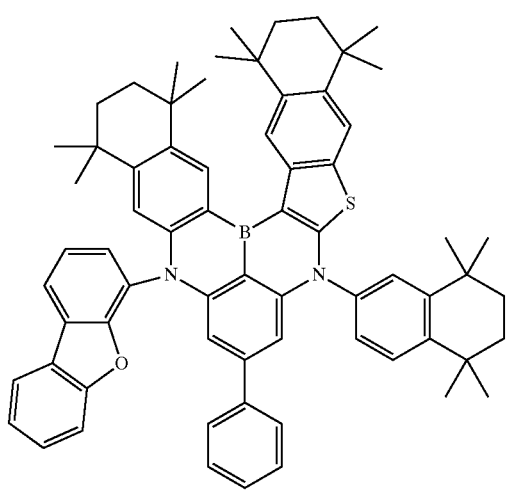
1614
-continued
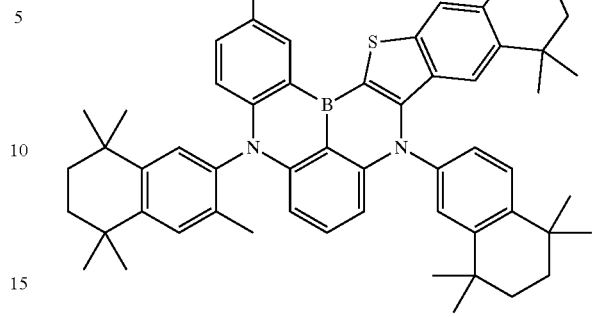
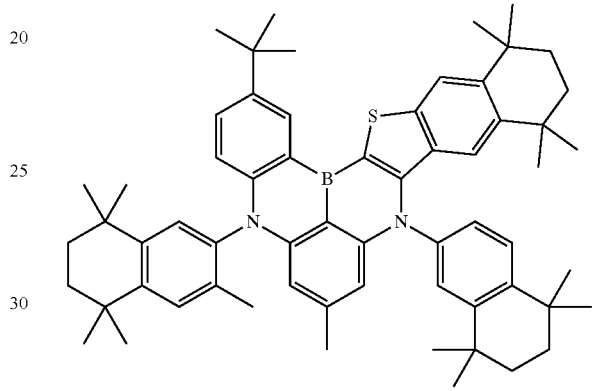
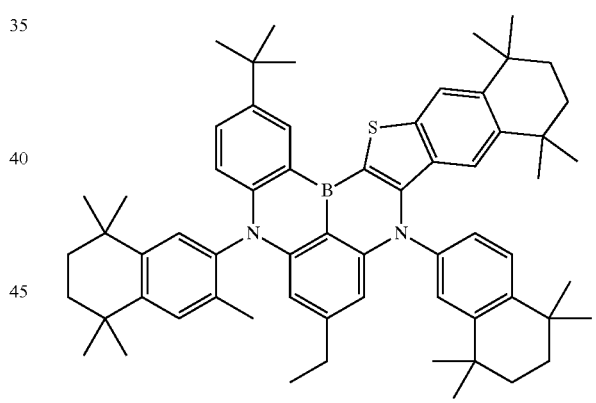
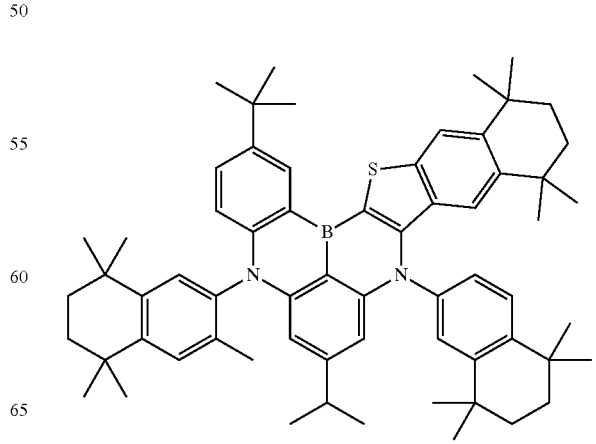

| 1615 -continued | 1616 -continued |
|---|---|
| 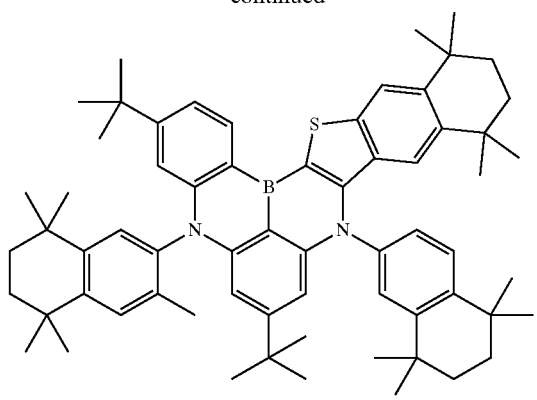 | 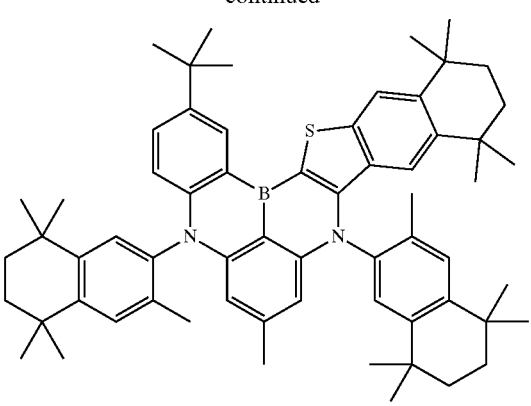 |
| 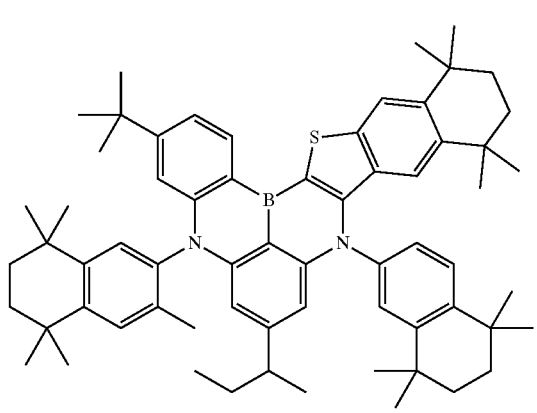 | 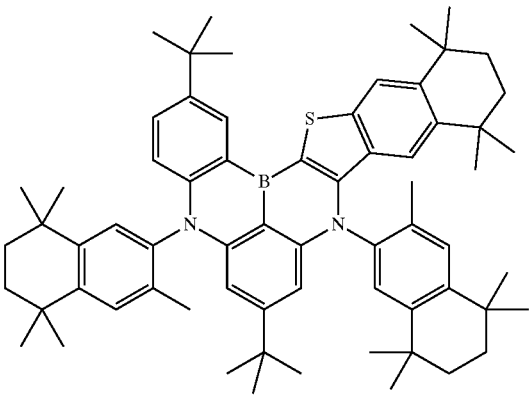 |
| 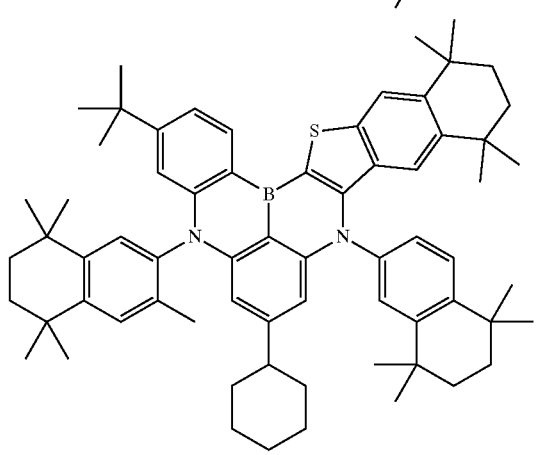 | 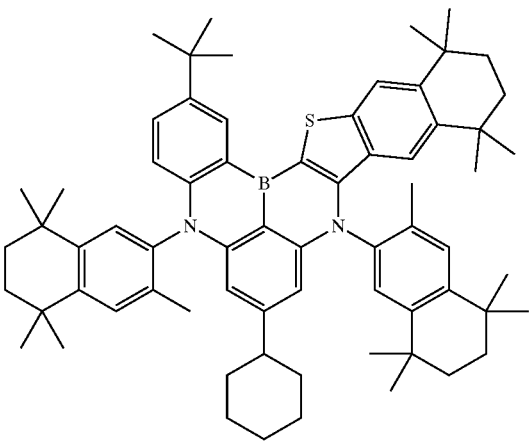 |
| 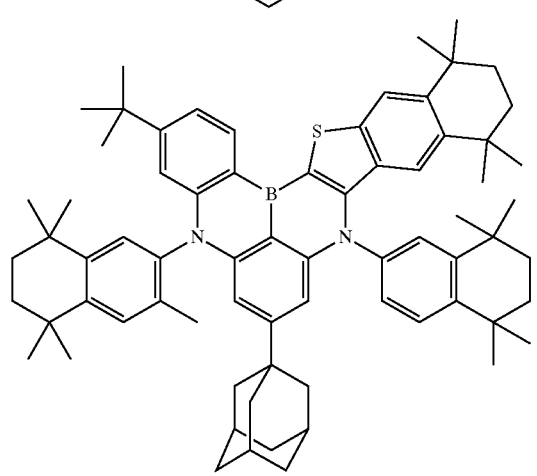 | 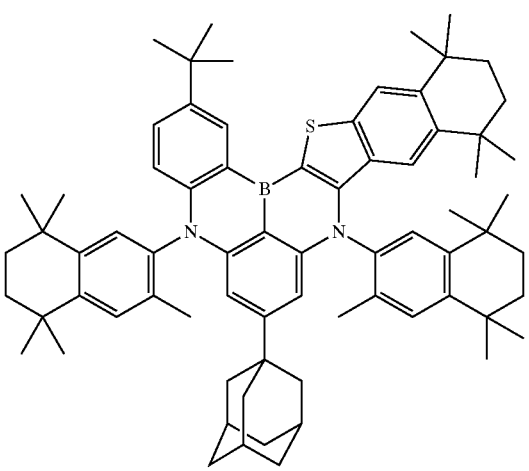 |

1617 -continued

1618 -continued

1619
-continued
1620
-continued
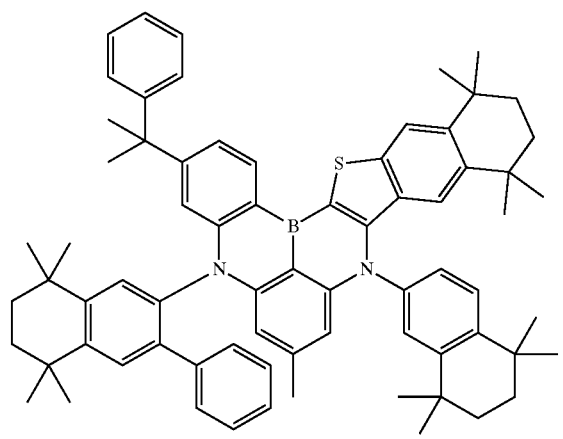
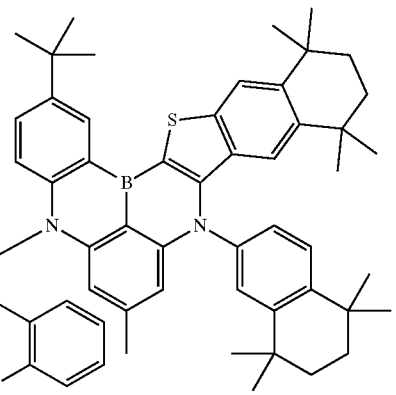
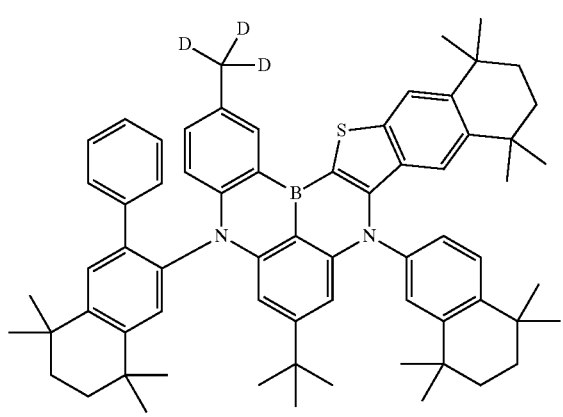
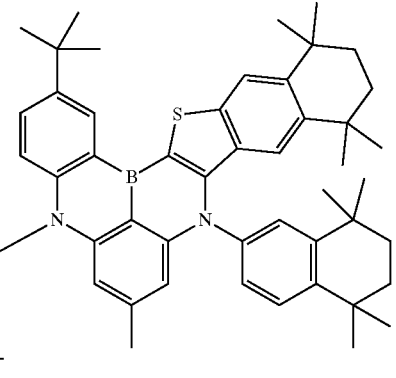
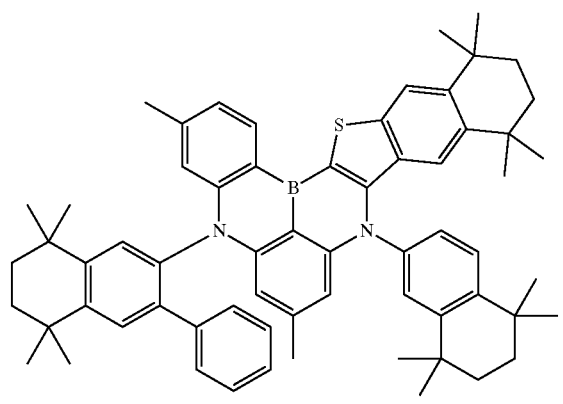
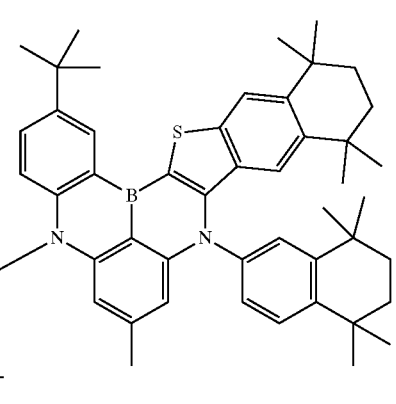
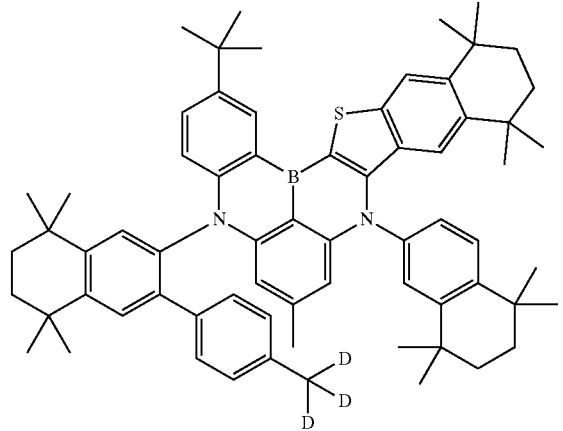
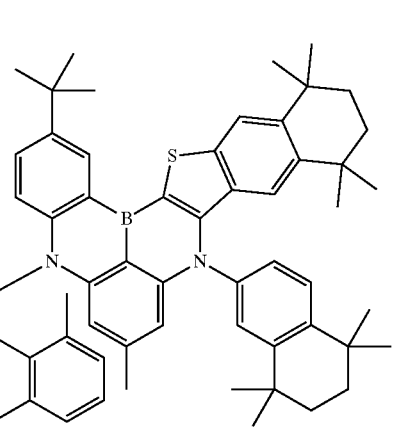

1621
-continued
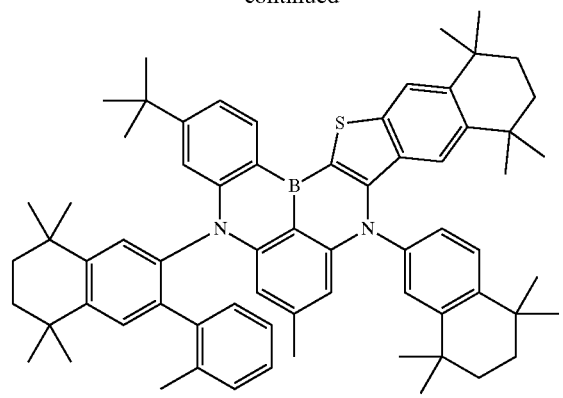
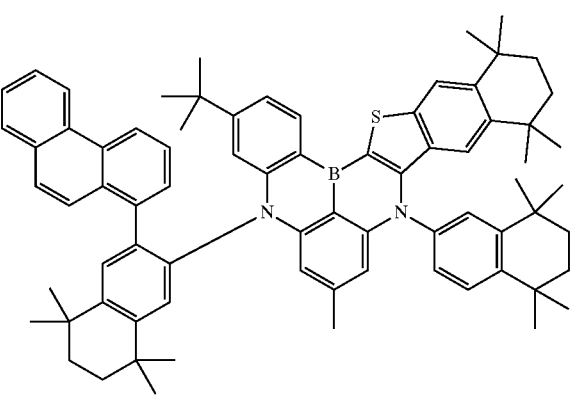
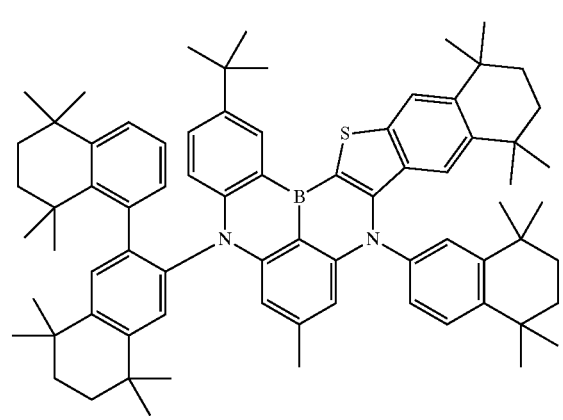
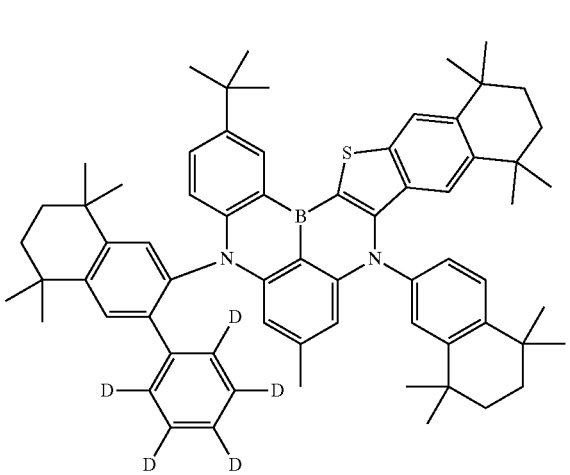
1622
-continued
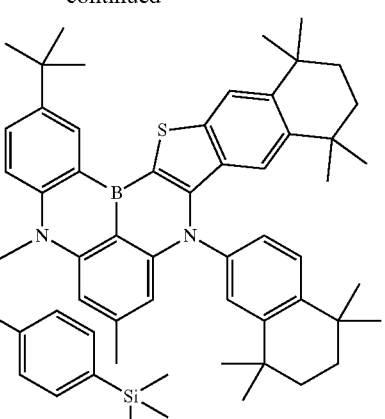
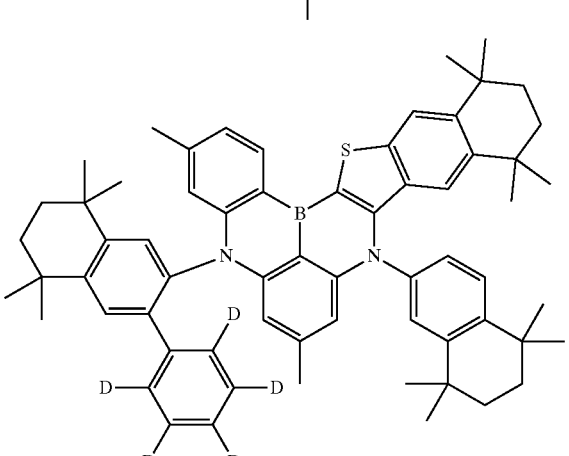
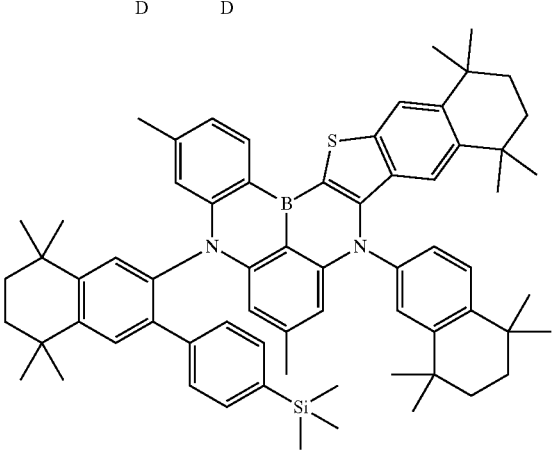
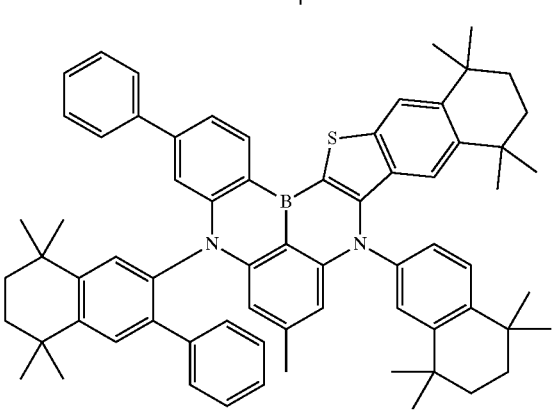

1623
-continued
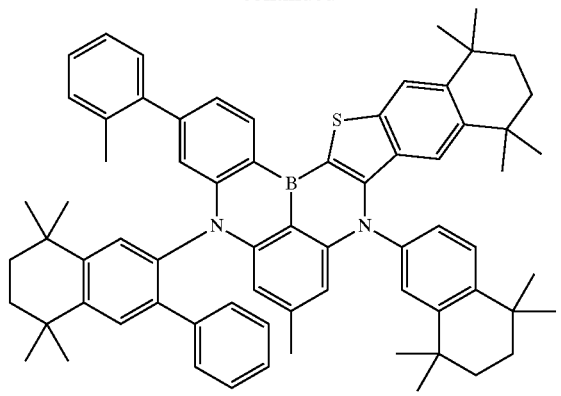
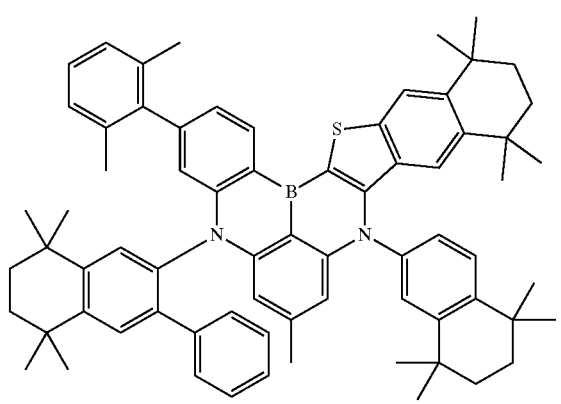
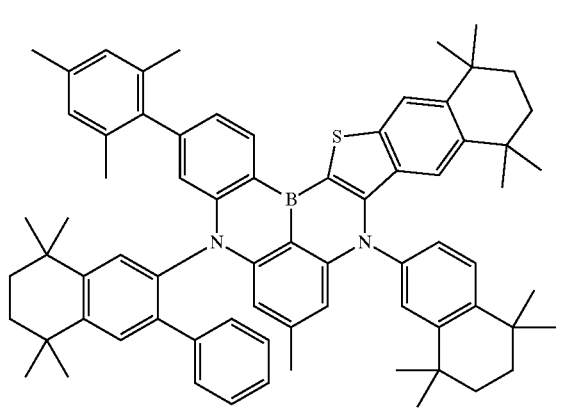
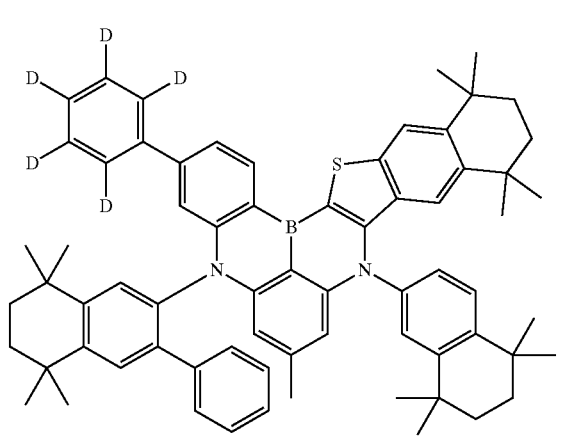
1624
-continued
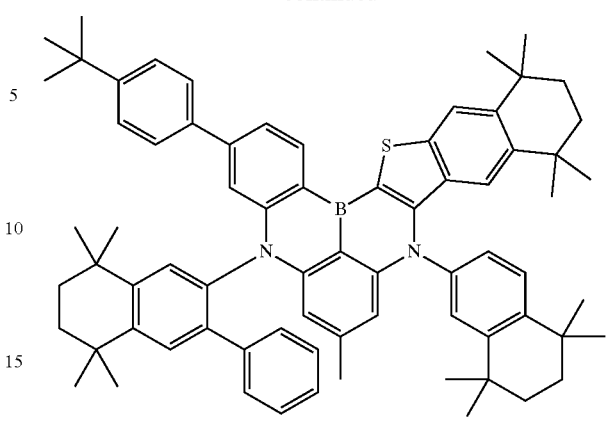
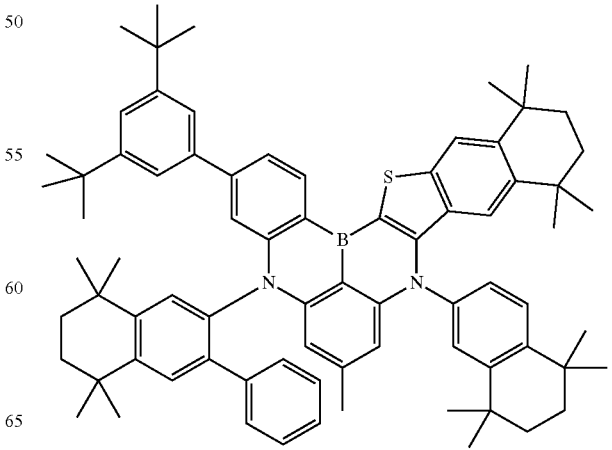
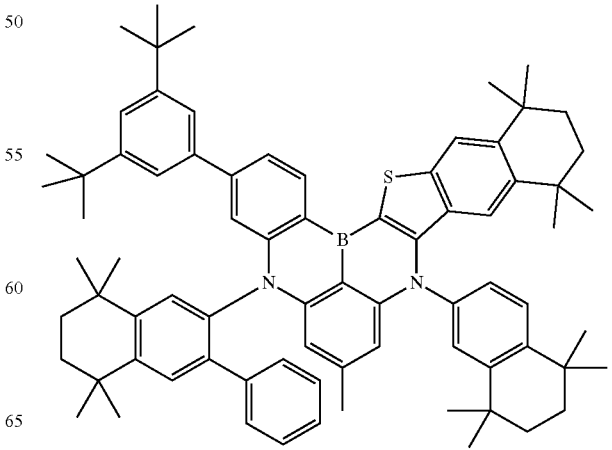

1625
-continued
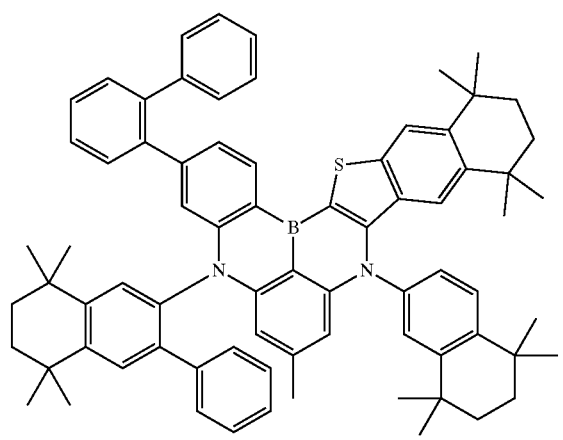
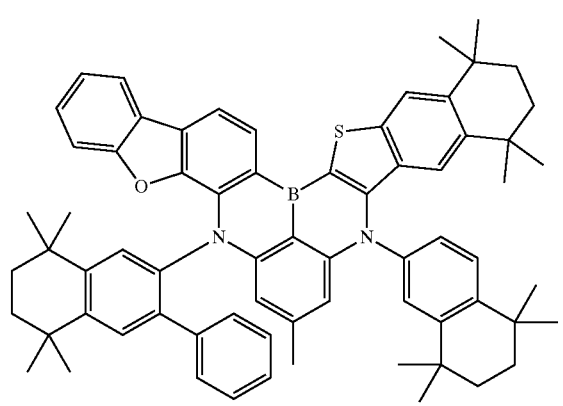
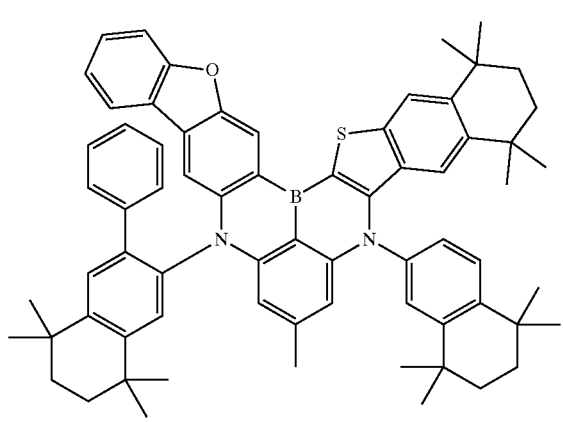
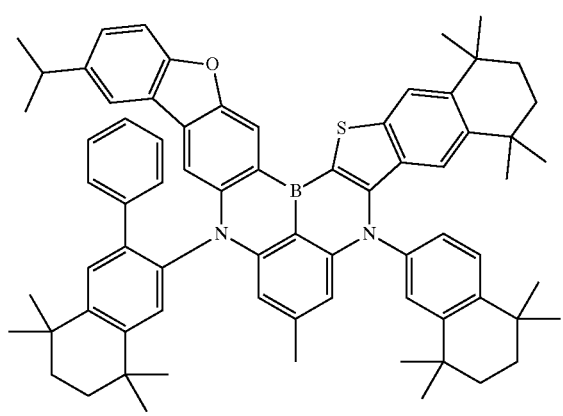
1626
-continued
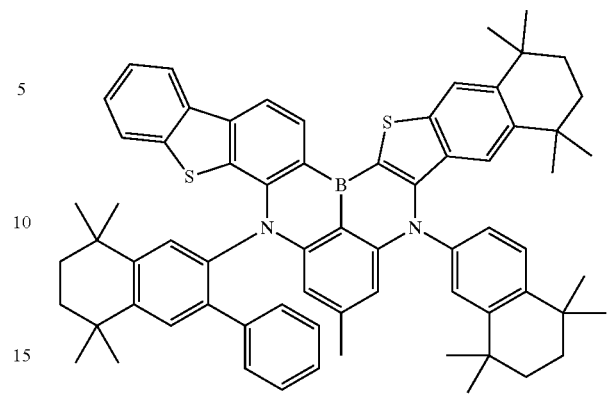
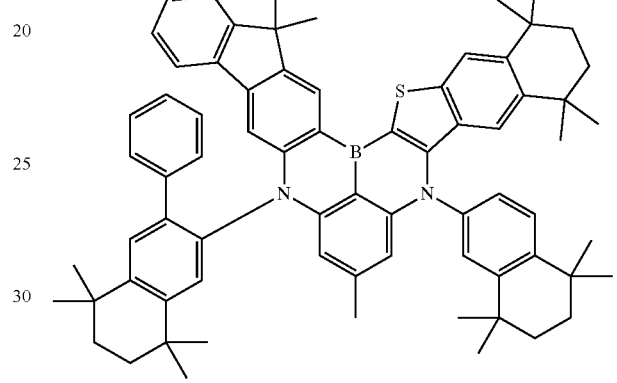
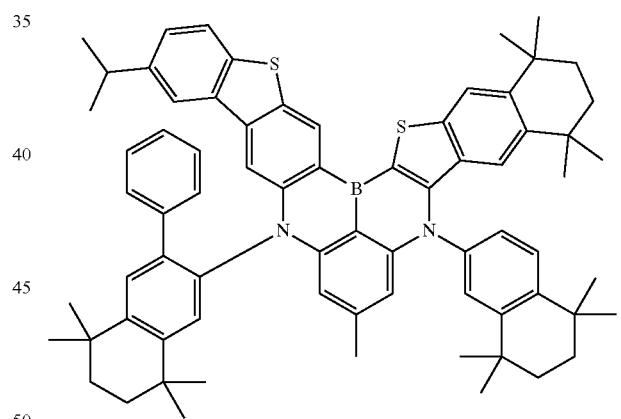
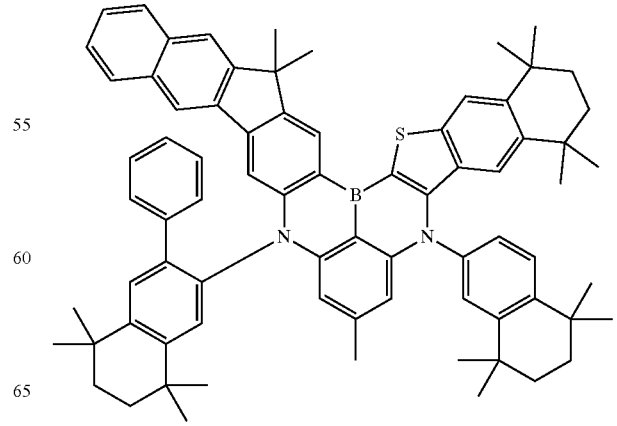

1627
-continued
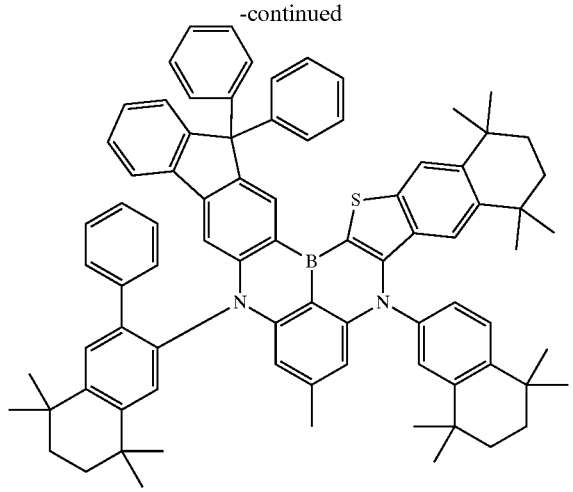
1628
-continued
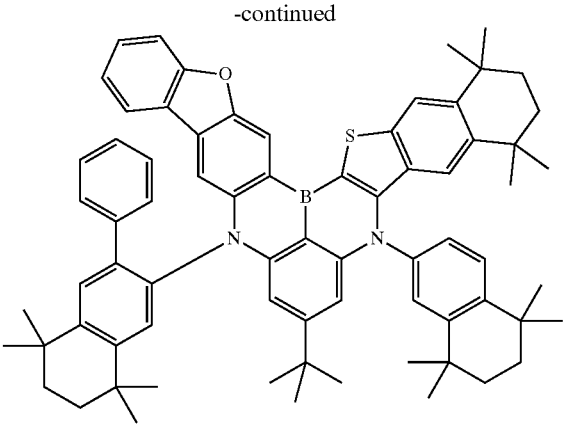
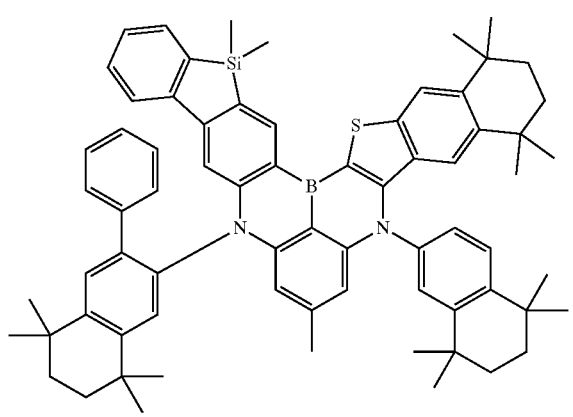
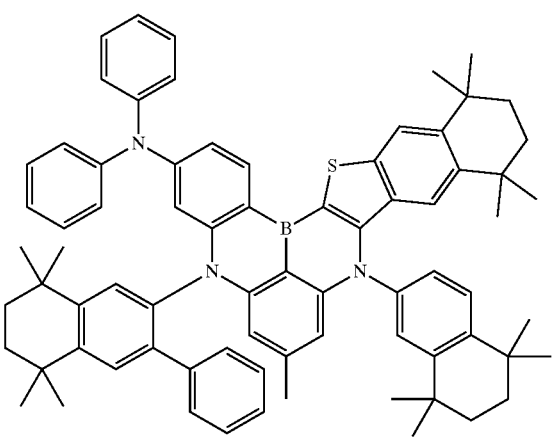
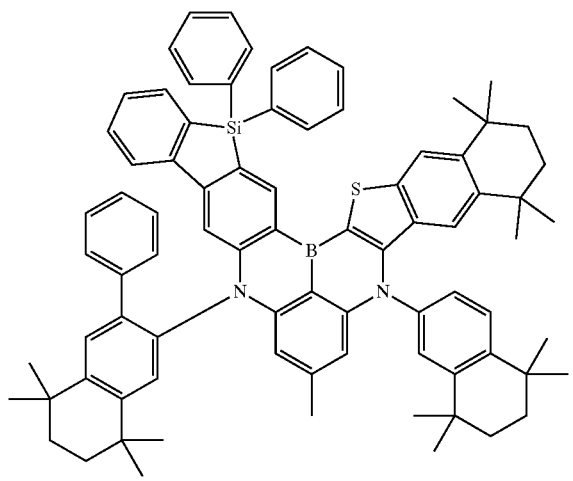
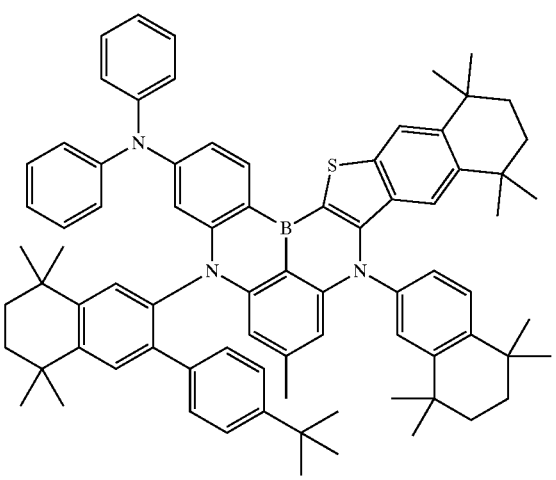

1629
-continued
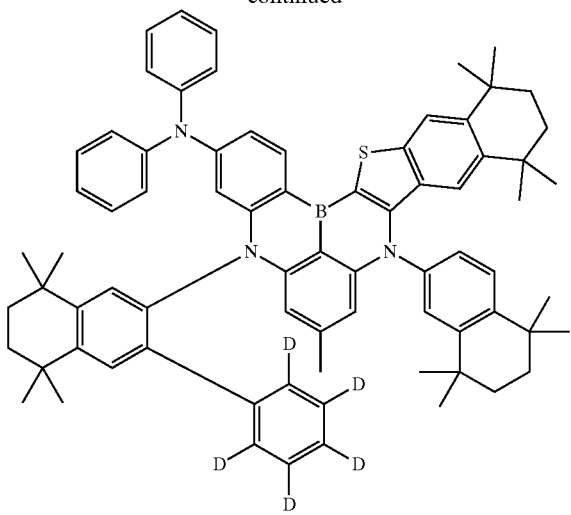
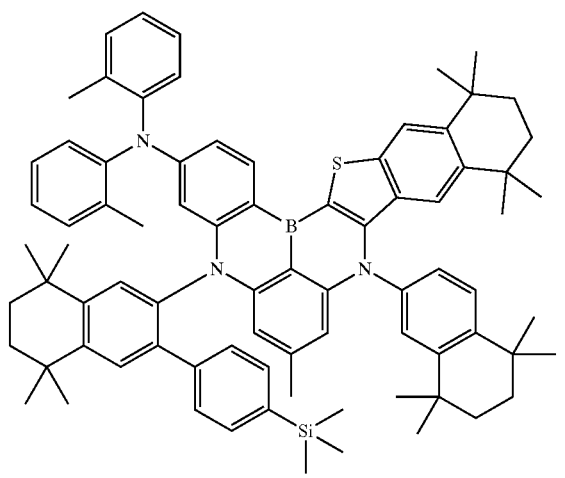
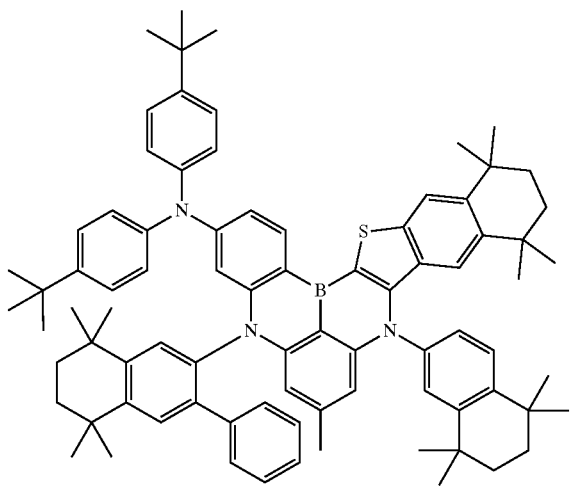
1630
-continued
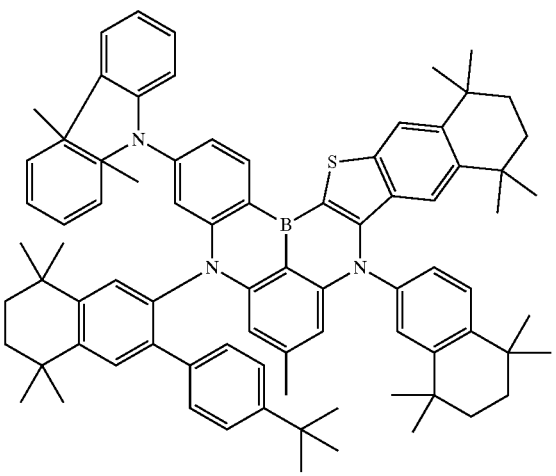
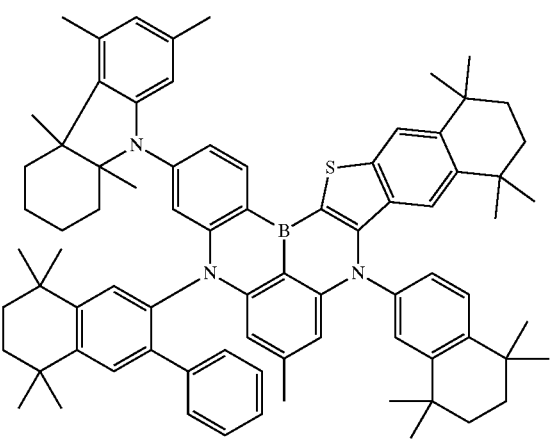
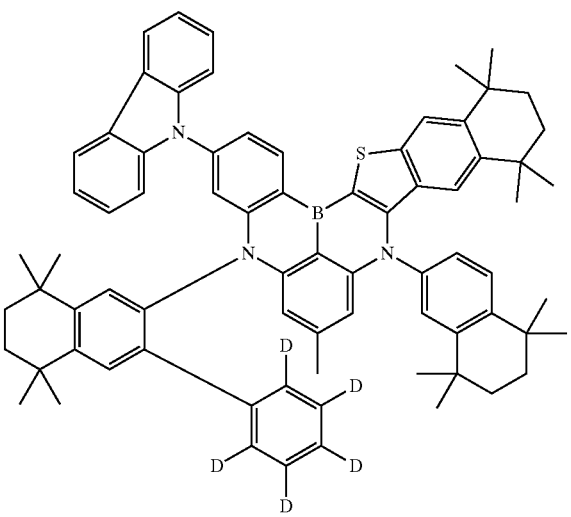

1631
-continued
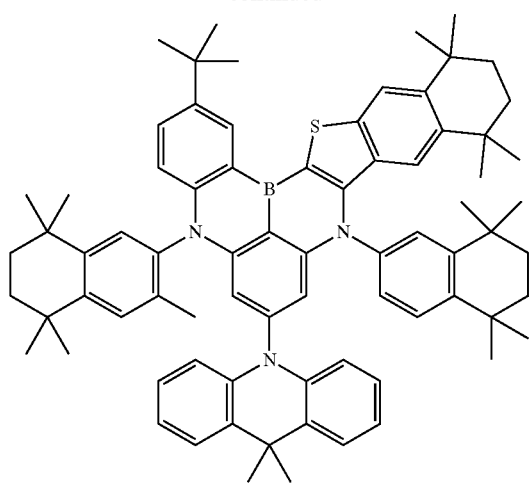
1632
-continued
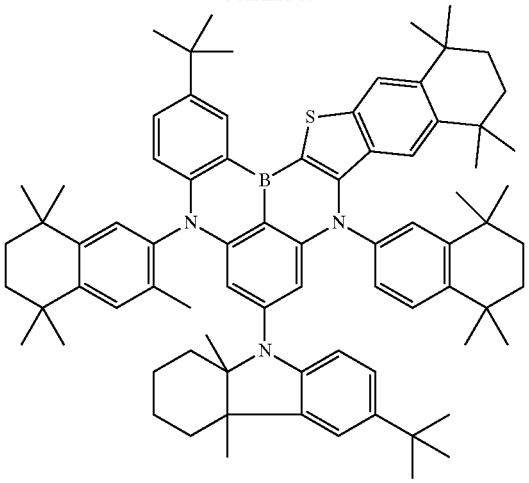
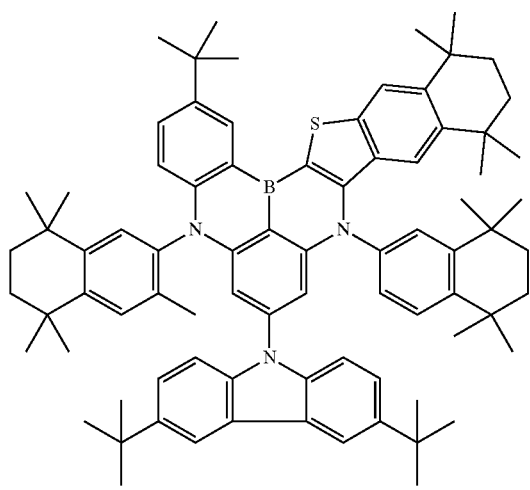
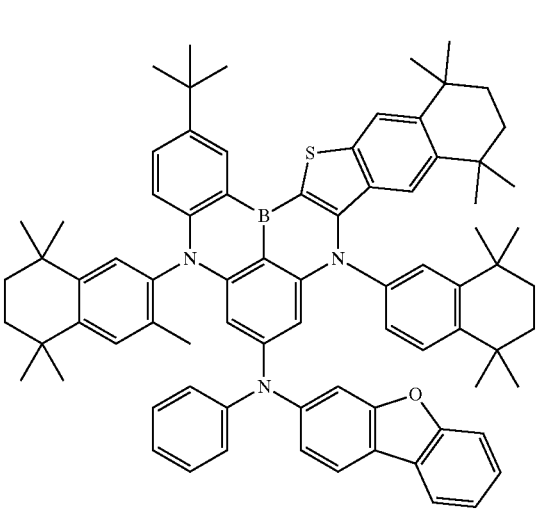
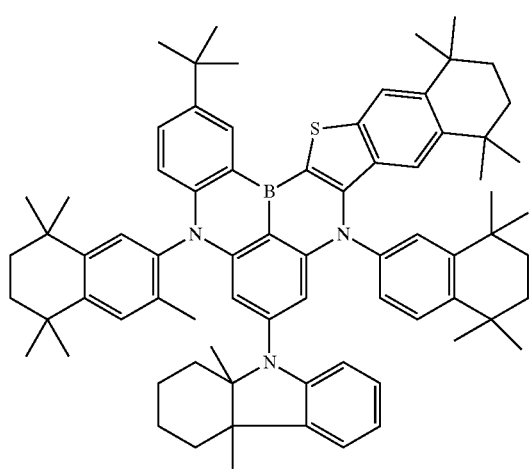
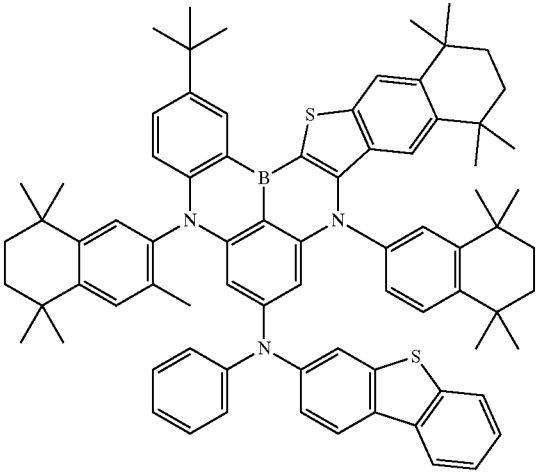

1633
-continued
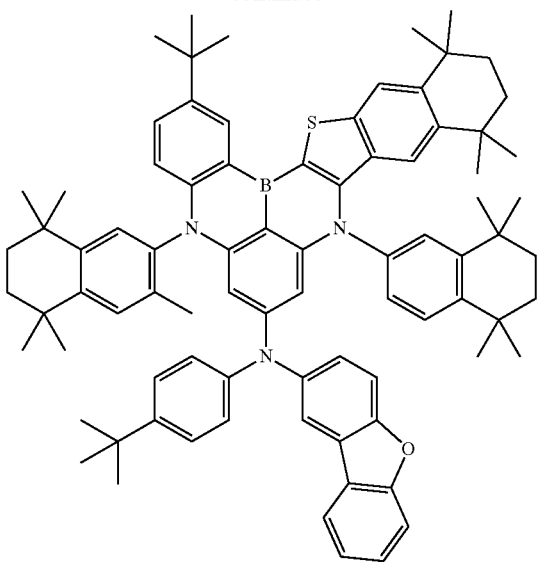
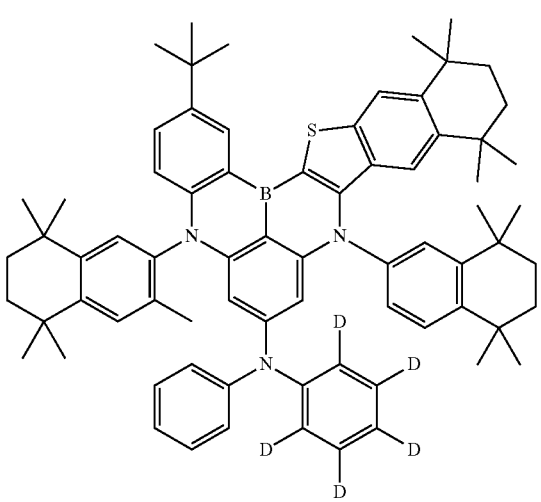 [SMILES: [2H]c1c([2H])c([2H])c(N(c2ccccc2)c2cc3c4c(c2)N(c2ccc5c(c2)C(C)(C)CCC5(C)C)c2c(sc5cc6c(cc25)C(C)(C)CCC6(C)C)B4c2cc(C(C)(C)C)ccc2N3c2cc3c(cc2C)C(C)(C)CCC3(C)C)c([2H])c1[2H]]
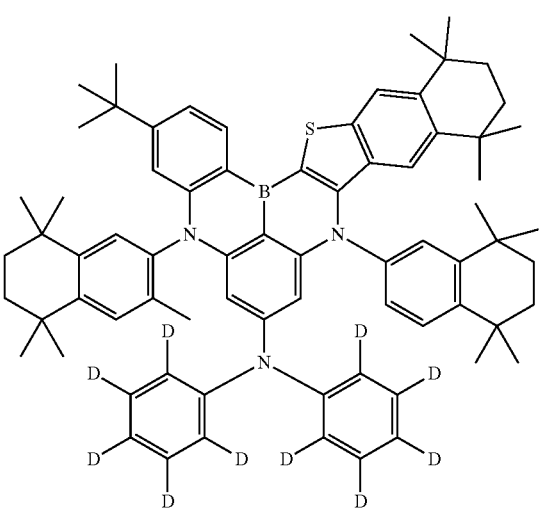
1634
-continued
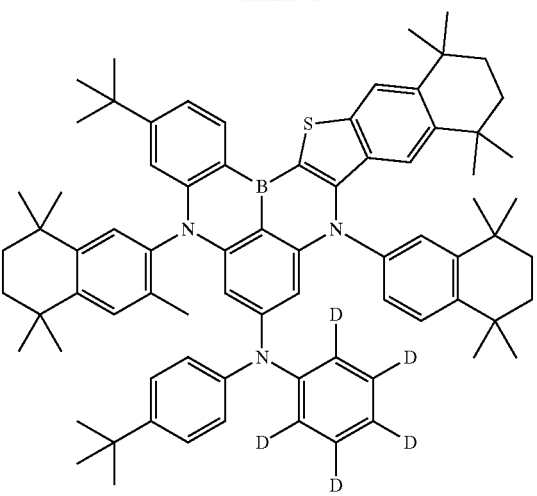
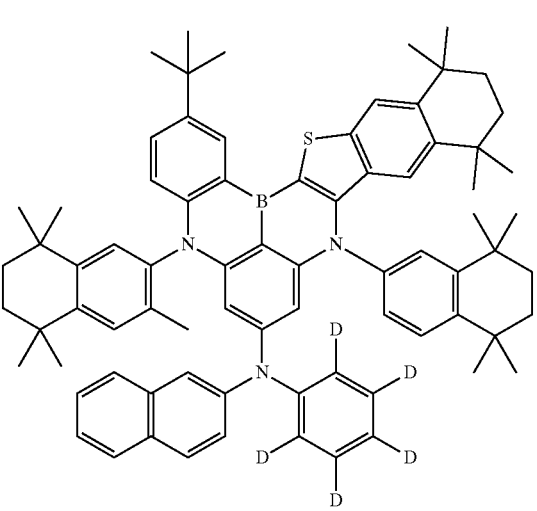
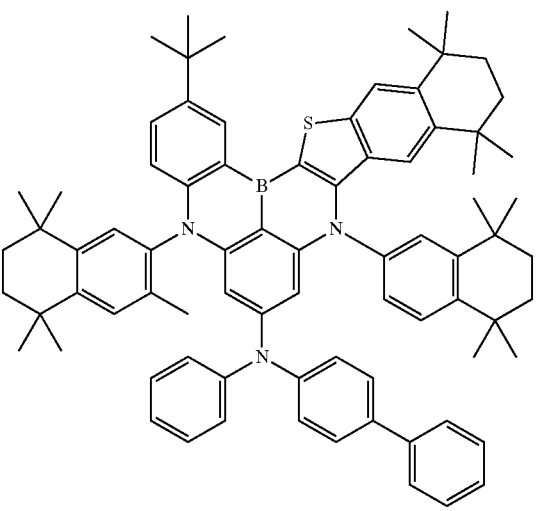 [SMILES: Cc1cc2c(cc1N1c3ccc(C(C)(C)C)cc3B3c4sc5cc6c(cc5c4N(c4ccc5c(c4)C(C)(C)CCC5(C)C)c4cc(N(c5ccccc5)c5ccc(-c7ccccc7)cc5)cc1c43)C(C)(C)CCC6(C)C)C(C)(C)CCC2(C)C]

1635
-continued
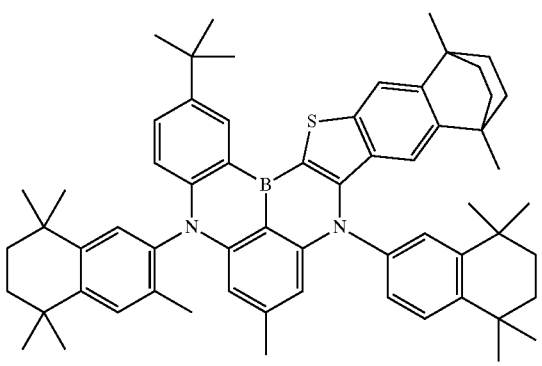
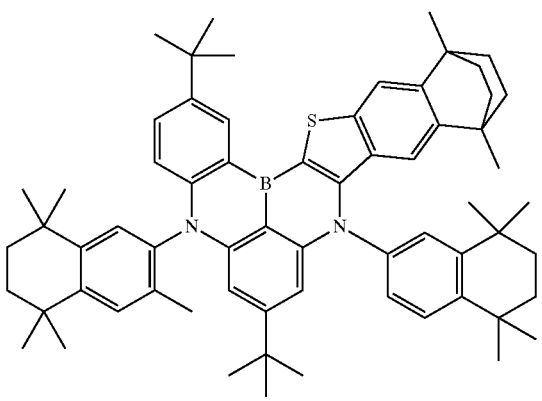
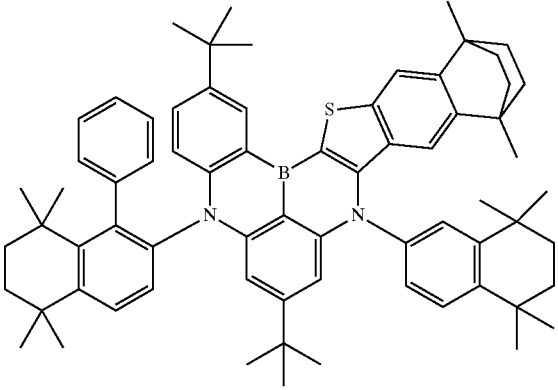
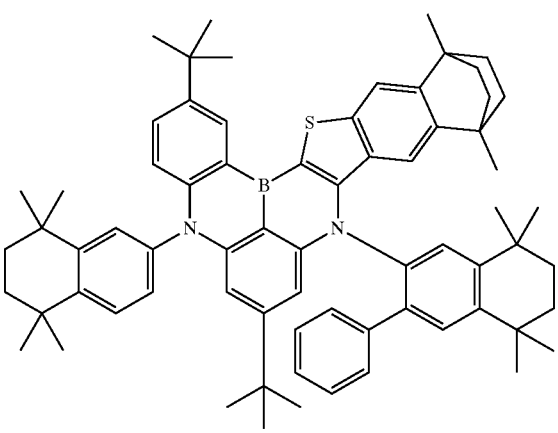
1636
-continued
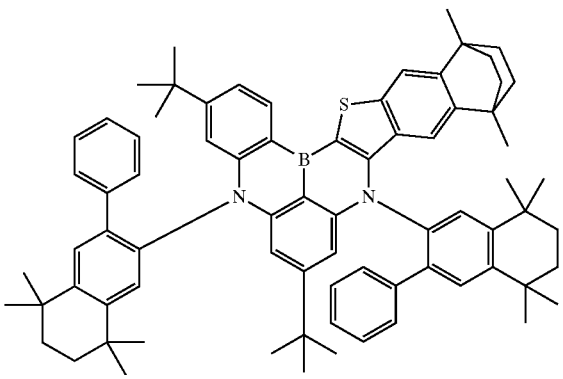
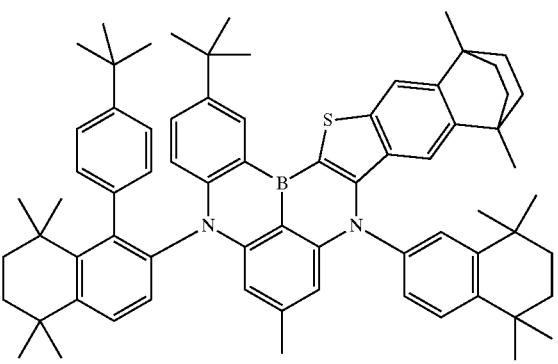
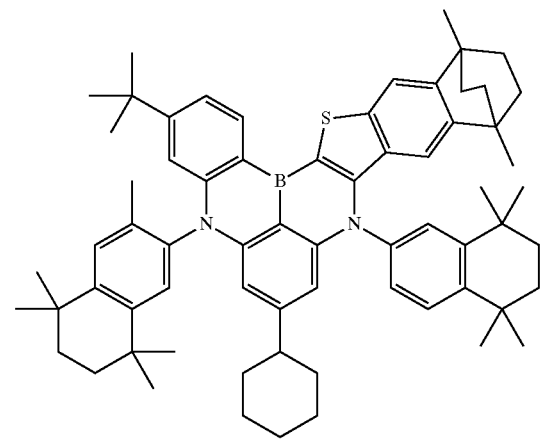
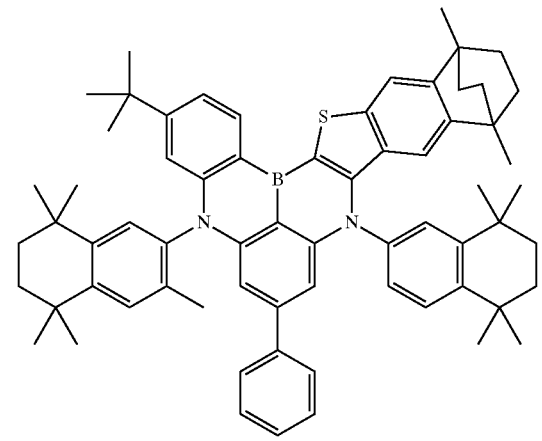

1637
-continued
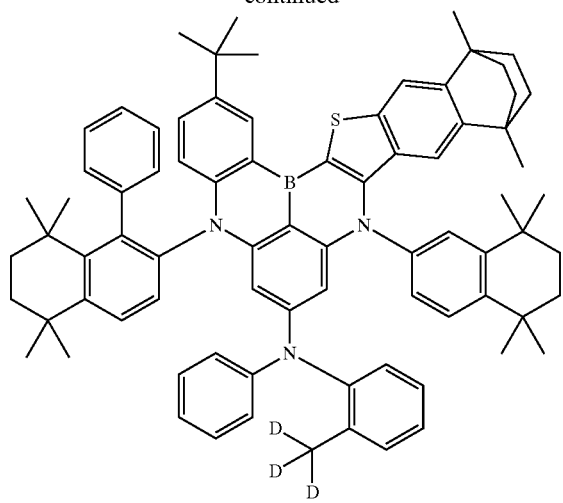
1638
-continued
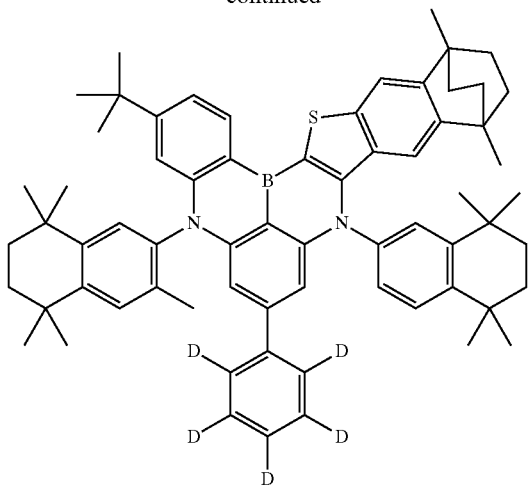
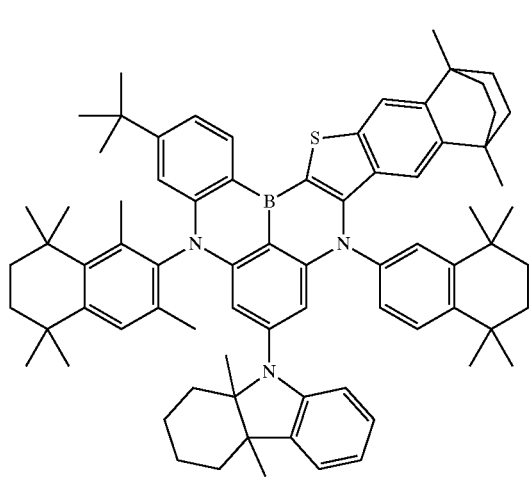
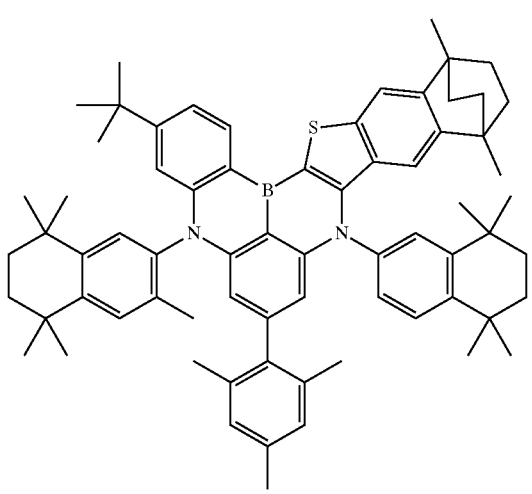
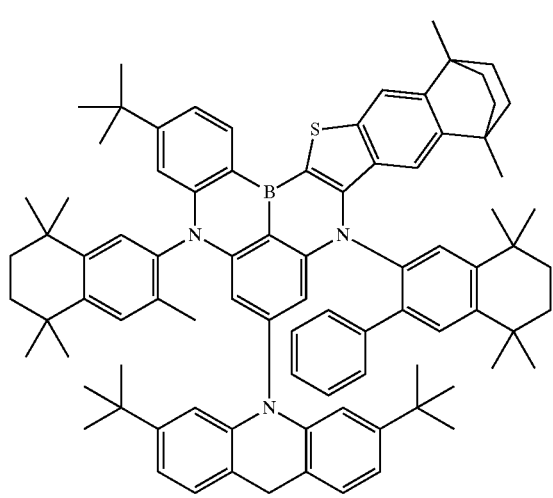
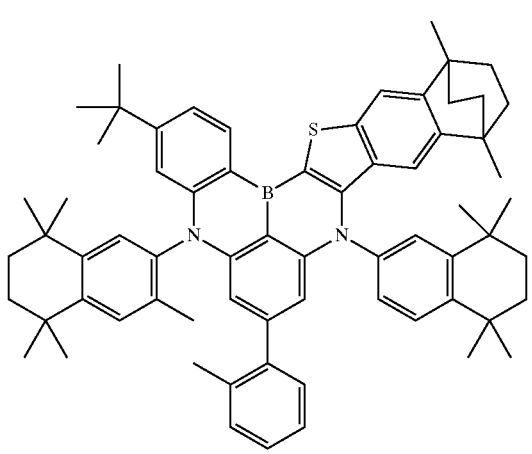

1639
-continued
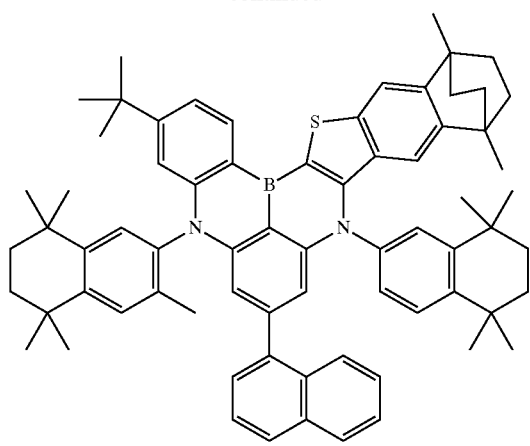
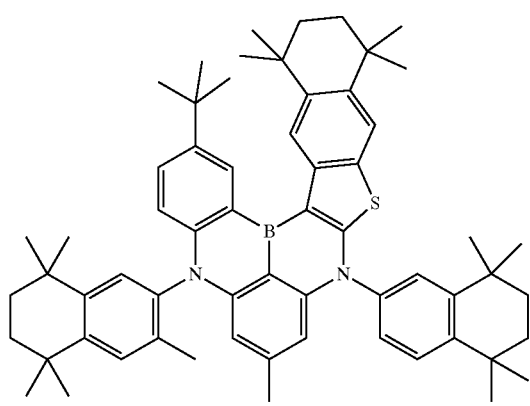
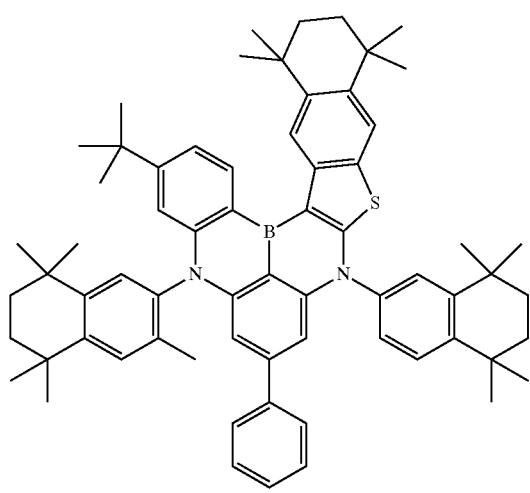
1640
-continued
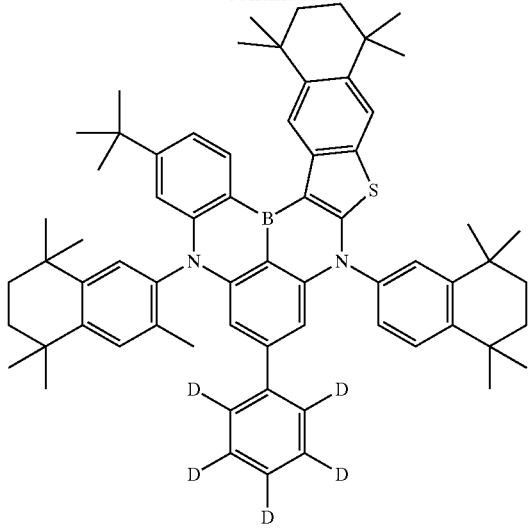
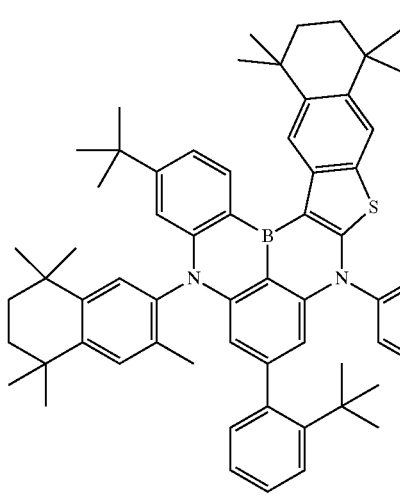
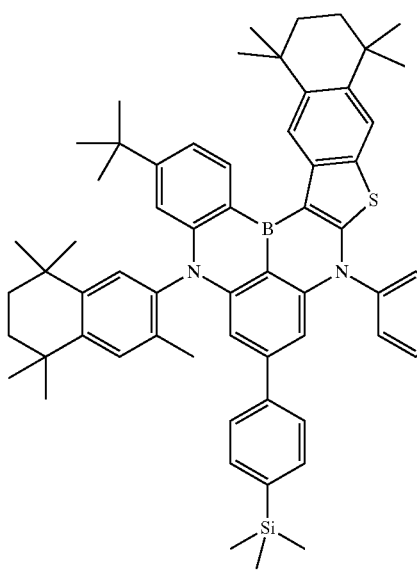

1641
-continued
1642
-continued
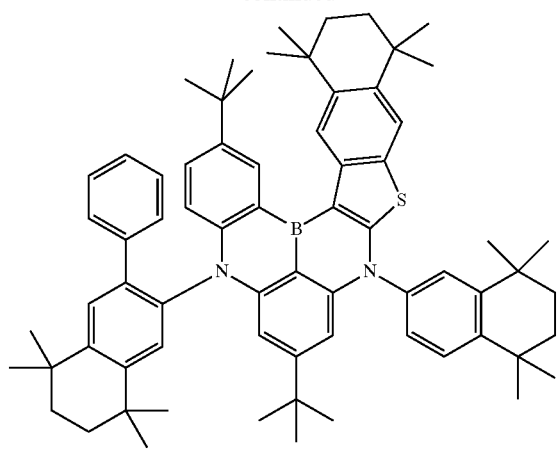
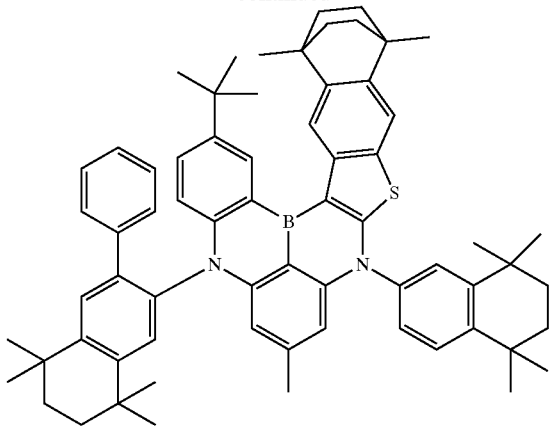
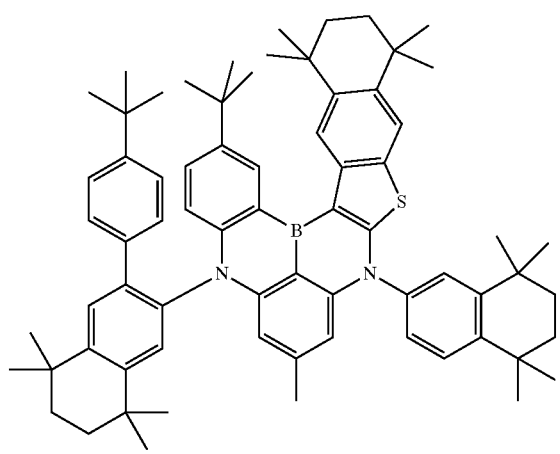
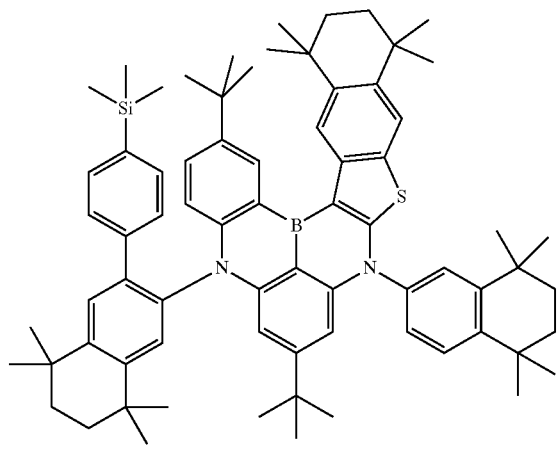
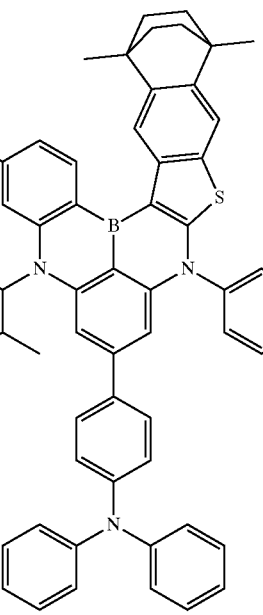

1643
-continued
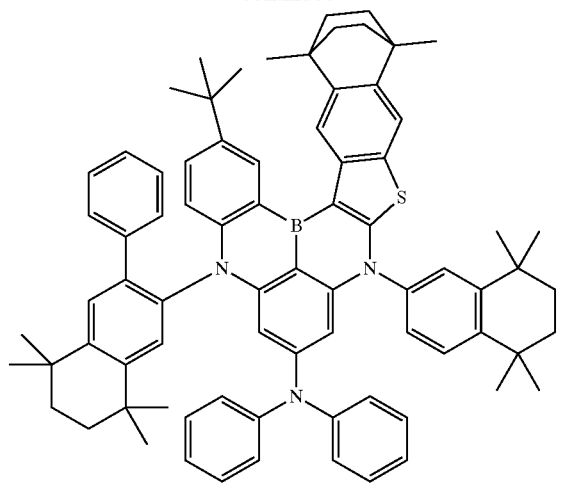
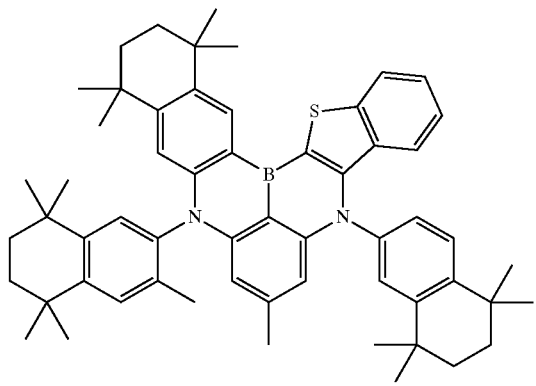 [SMILES: Cc1cc2c3c(c1)N(c1ccc4c(c1)C(C)(C)CCC4(C)C)c1c(sc4ccccc14)B3c1cc3c(cc1N2c1cc2c(cc1C)C(C)(C)CCC2(C)C)C(C)(C)CCC3(C)C]
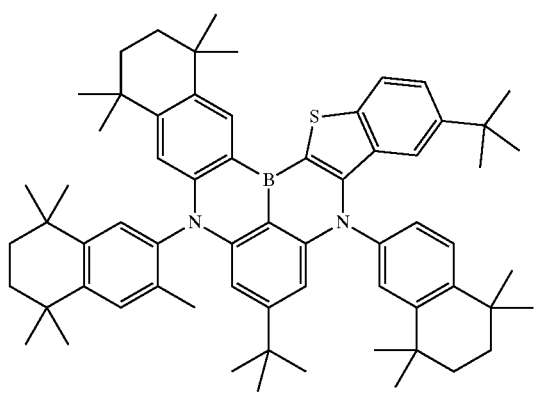
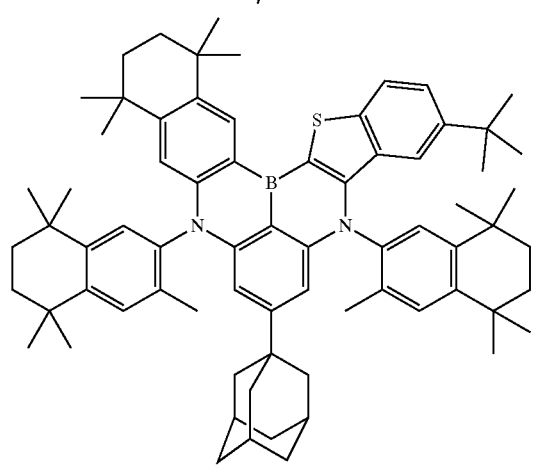
1644
-continued
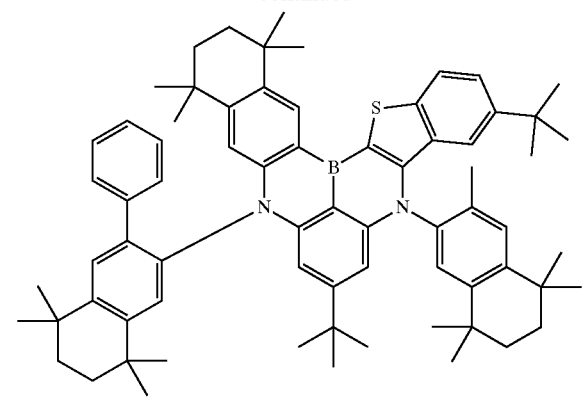
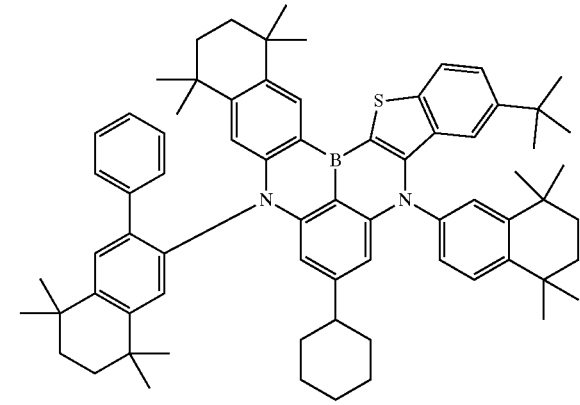
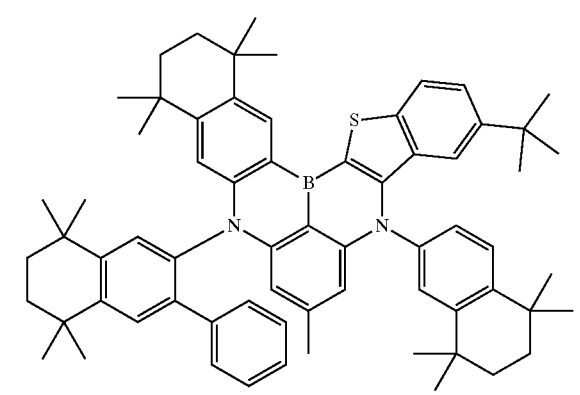
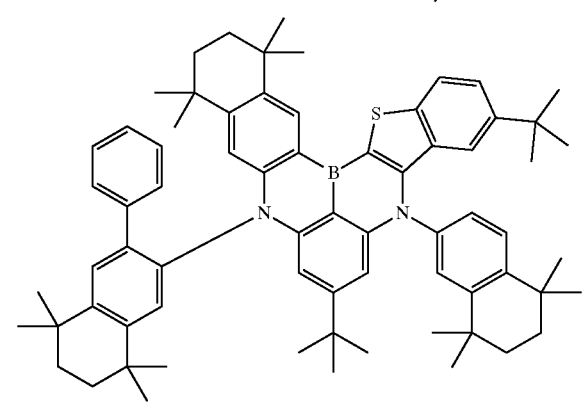

1645
-continued
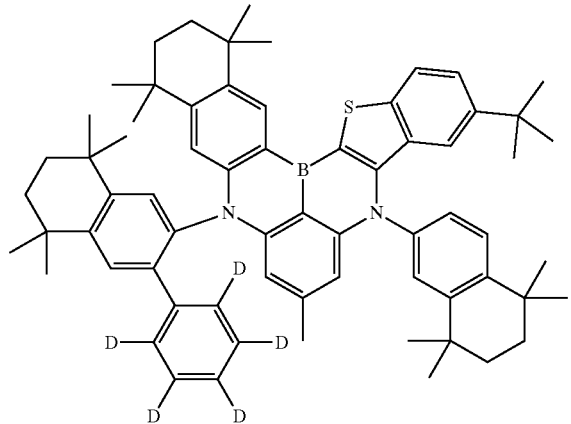
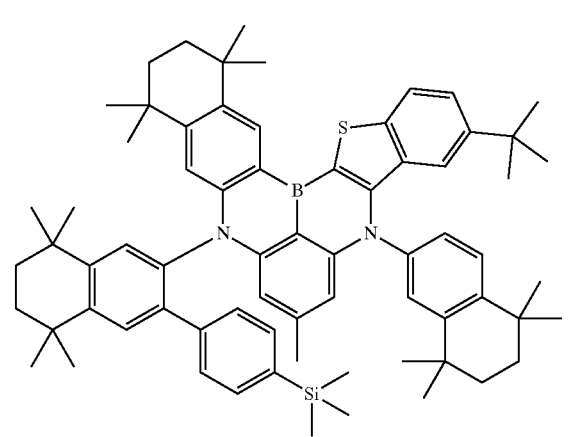
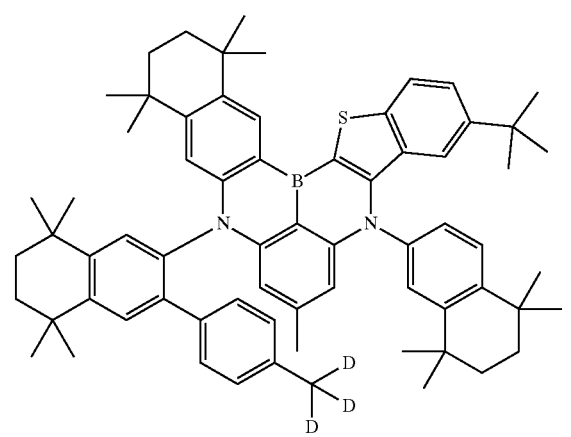
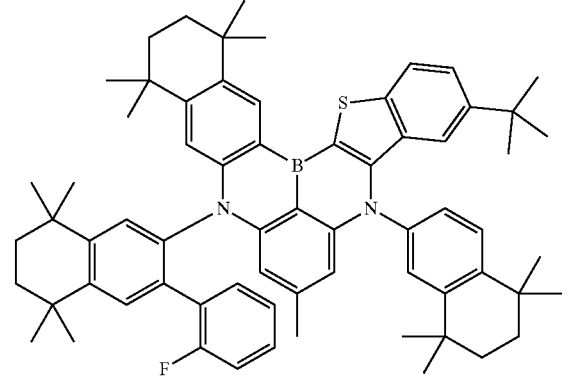
1646
-continued
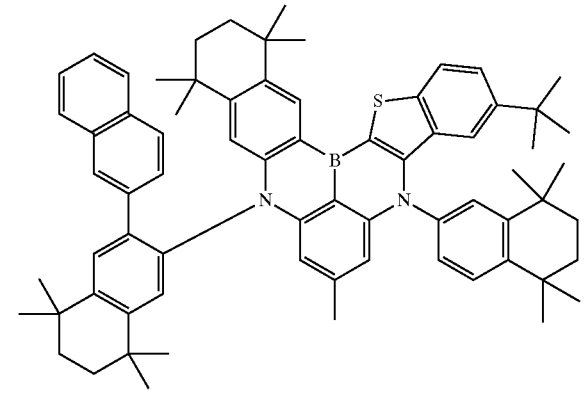
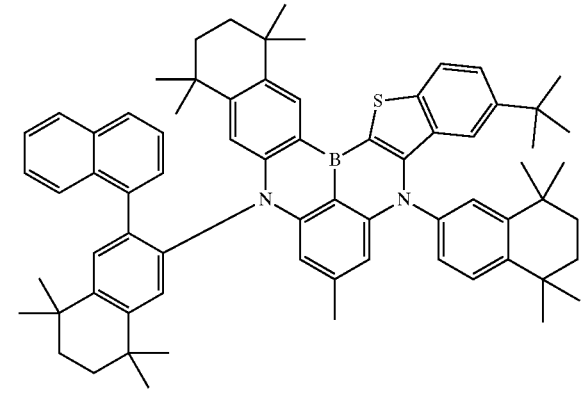
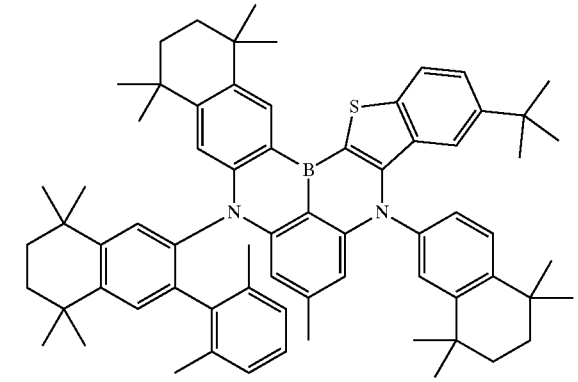
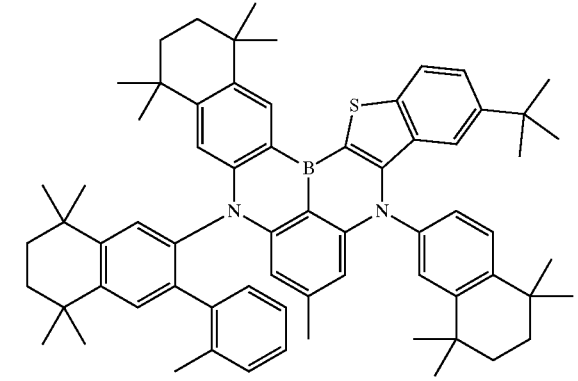

1647
-continued
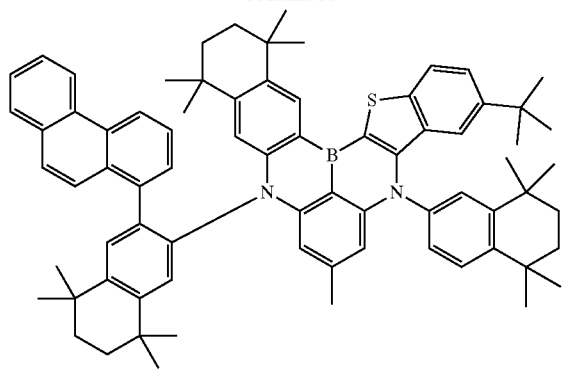
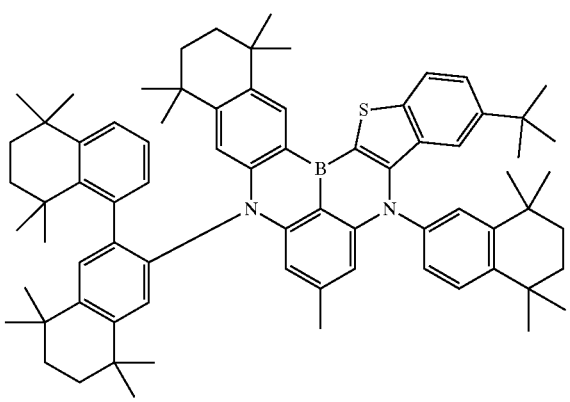
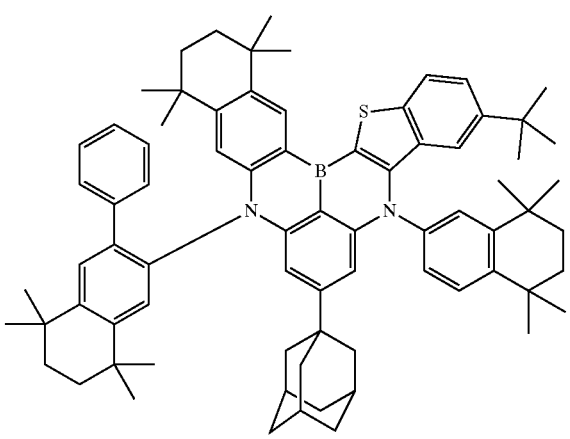
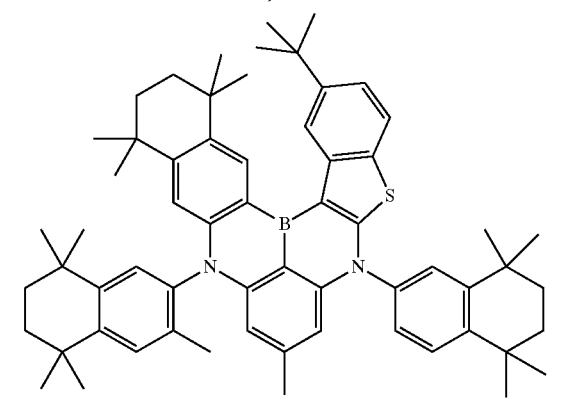
1648
-continued
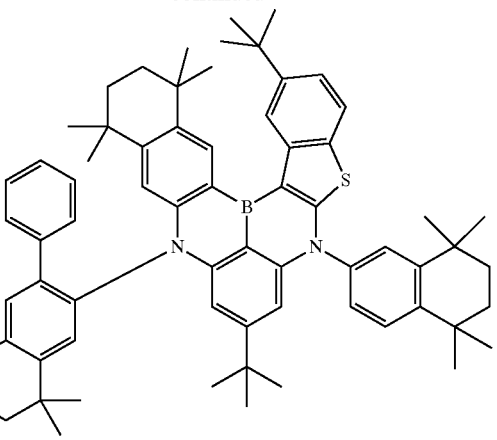
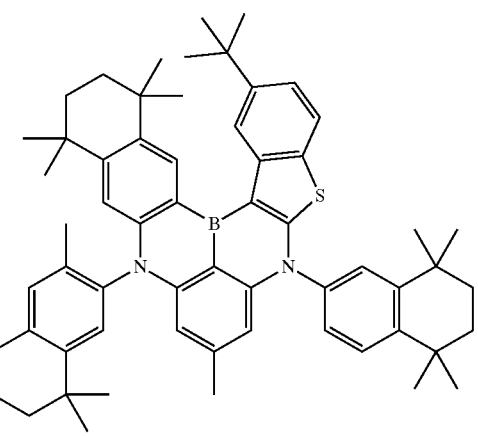
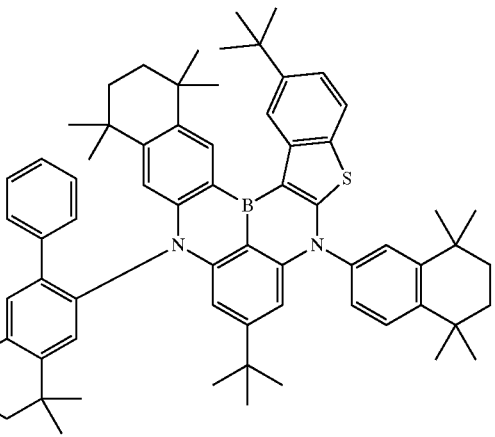

1649
-continued
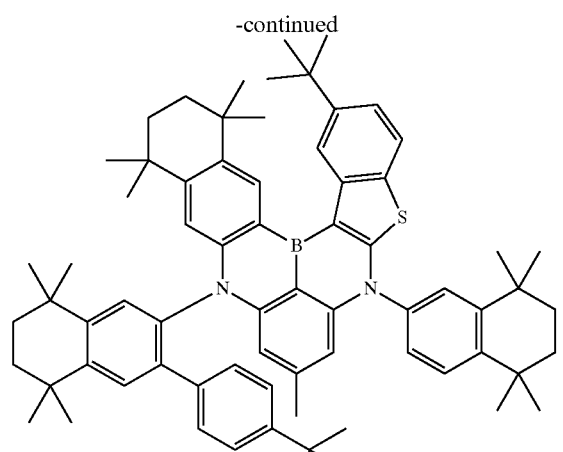
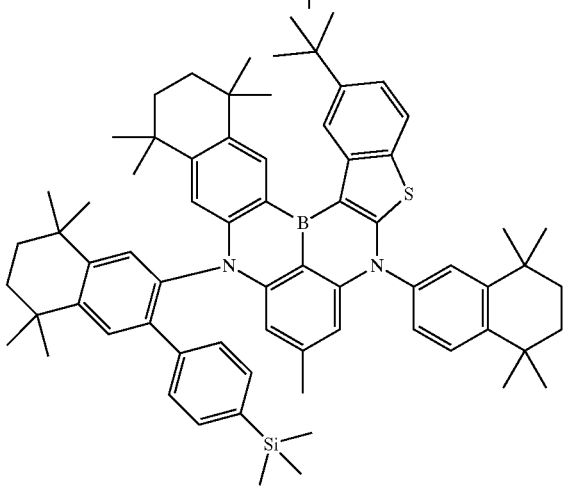
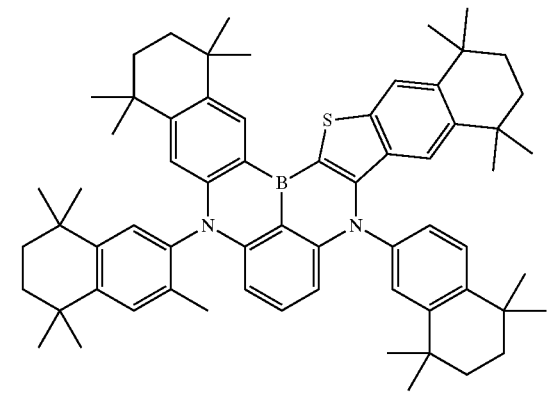
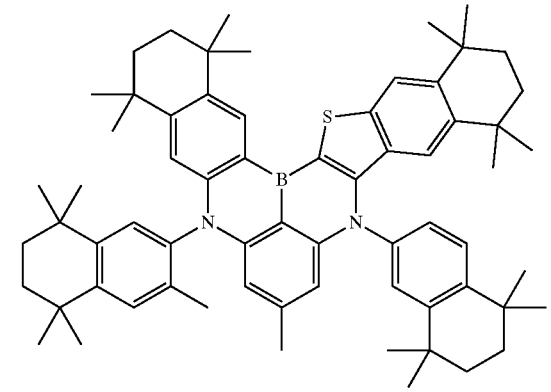
1650
-continued
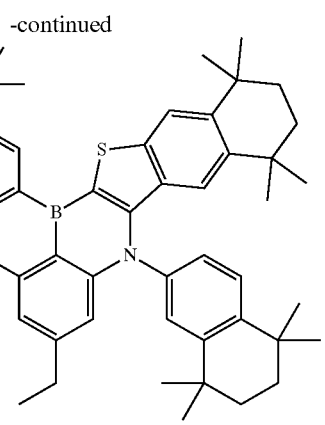
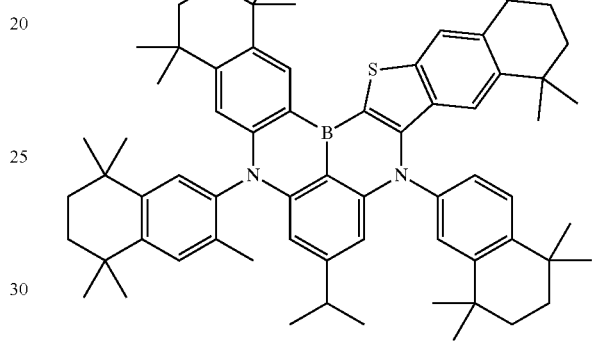
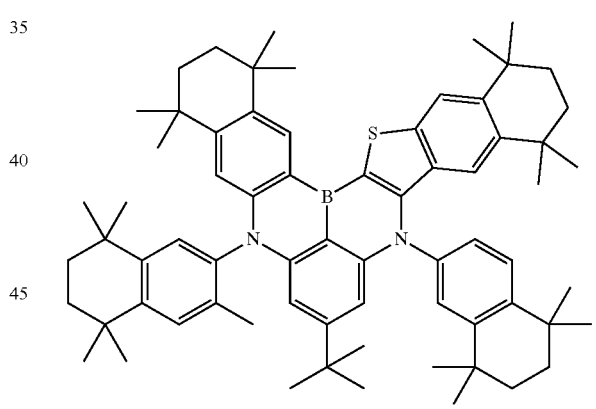
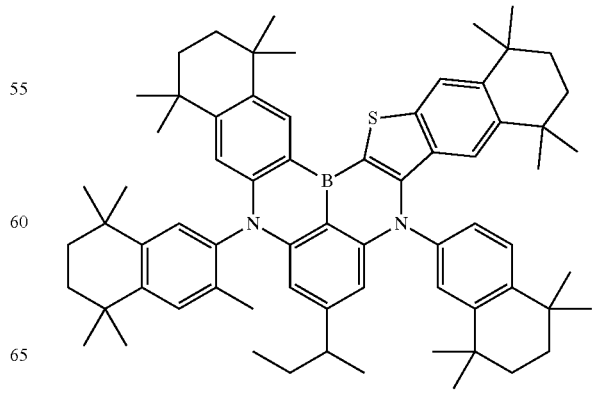

| 1651 | 1652 |
|---|---|
| -continued | -continued |
| 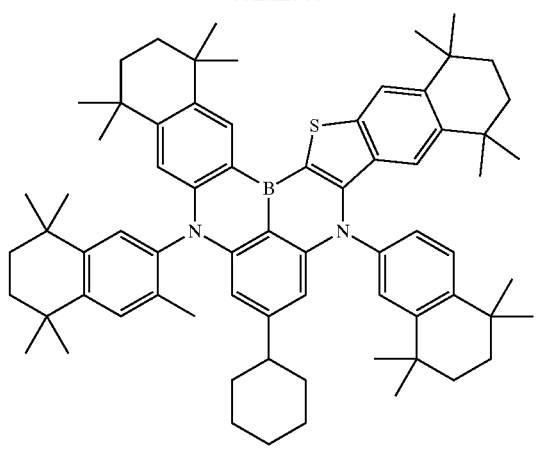 | 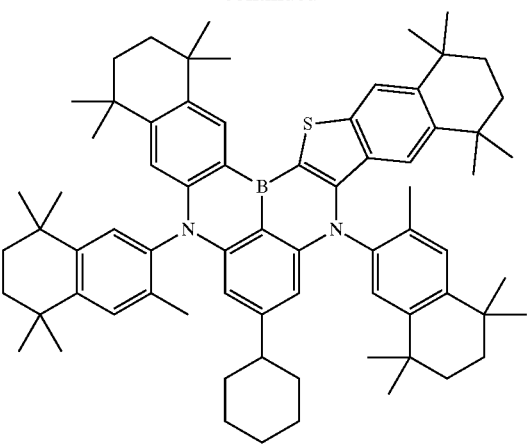 |
| 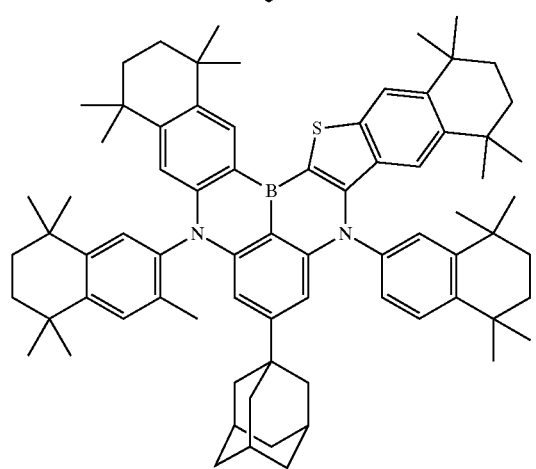 | 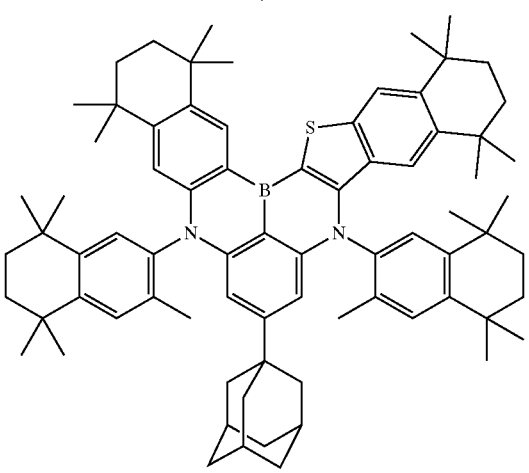 |
| 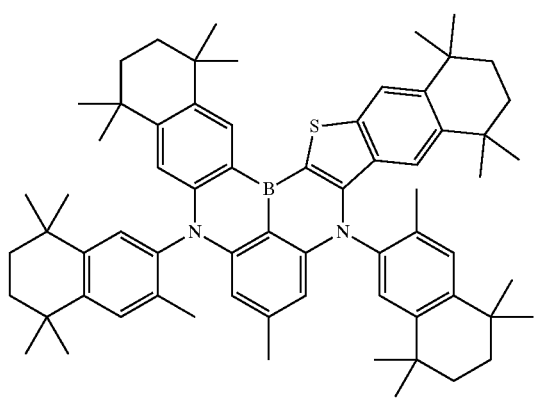 | 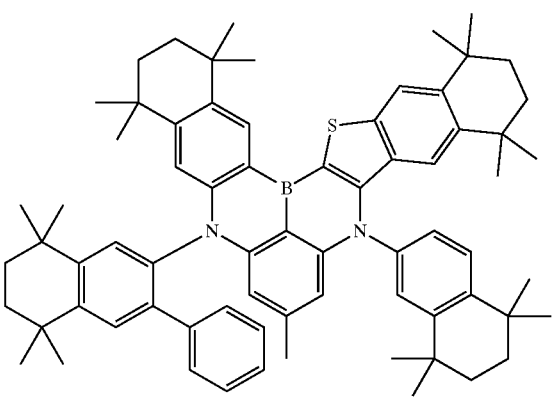 |
| 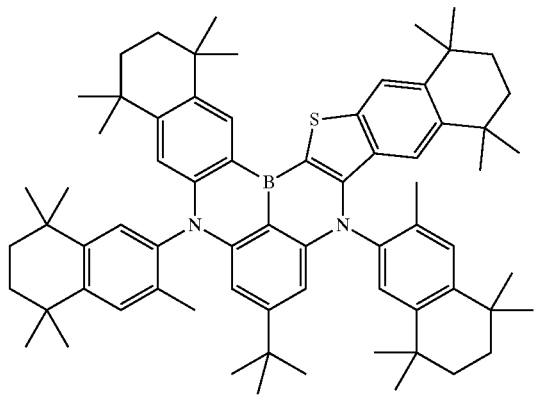 | 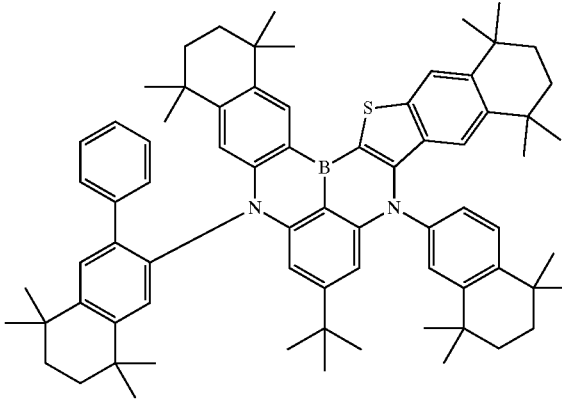 |

1653
-continued
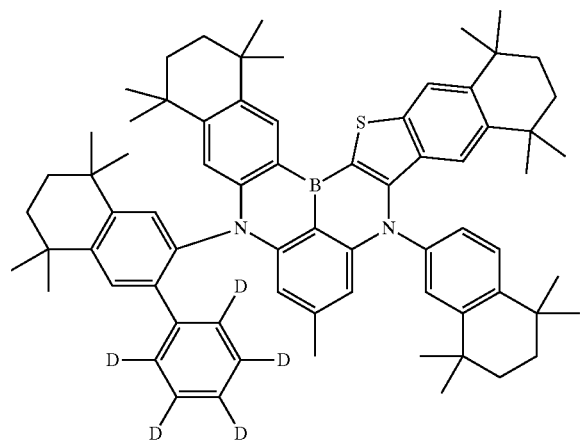
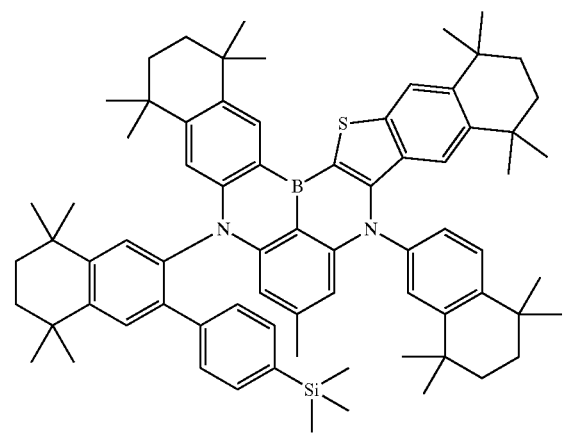
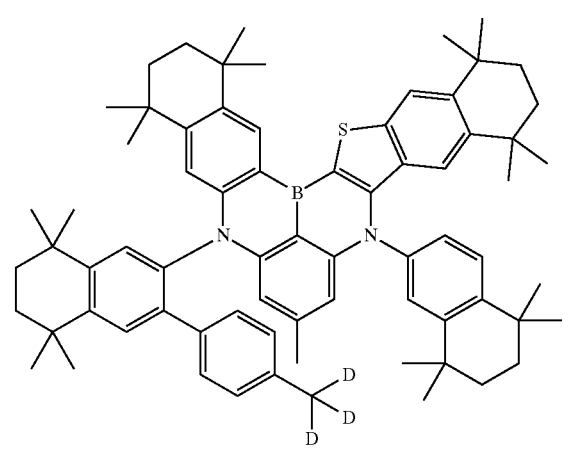
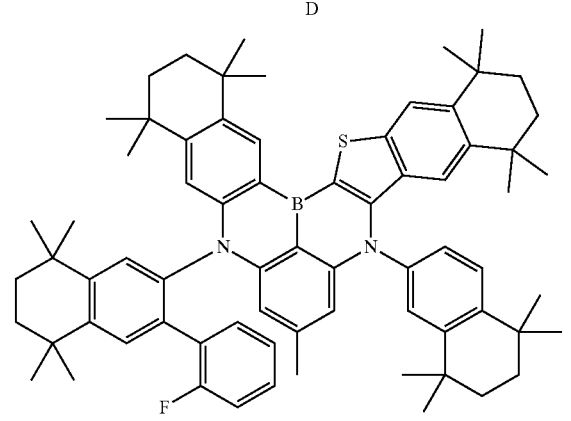
1654
-continued
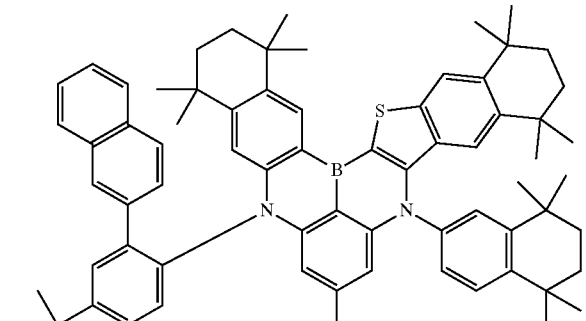
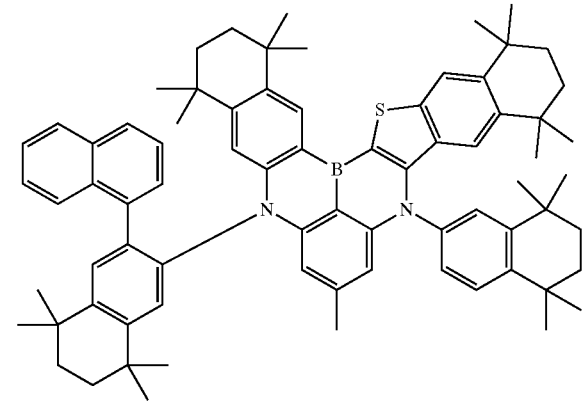
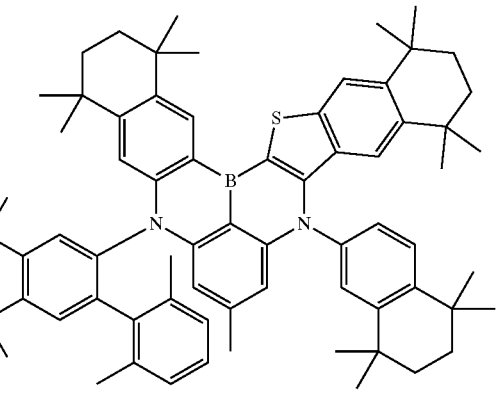
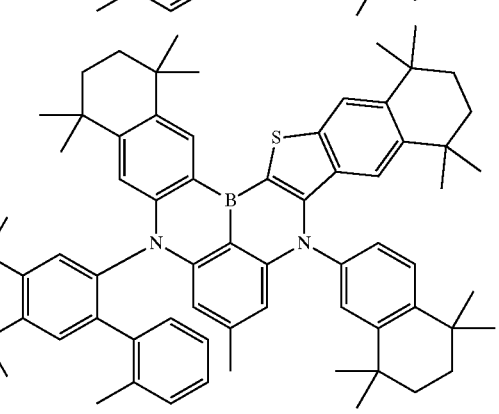

| 1655 -continued | 1656 -continued |
|---|---|
| 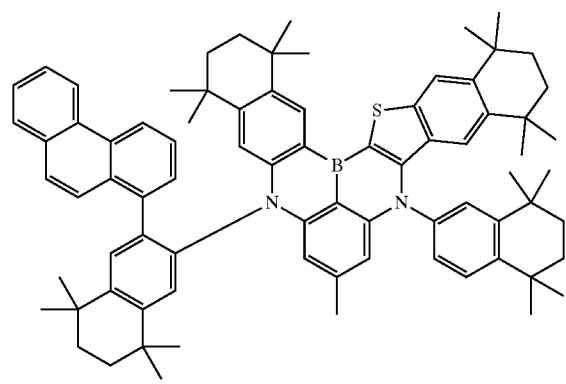 | 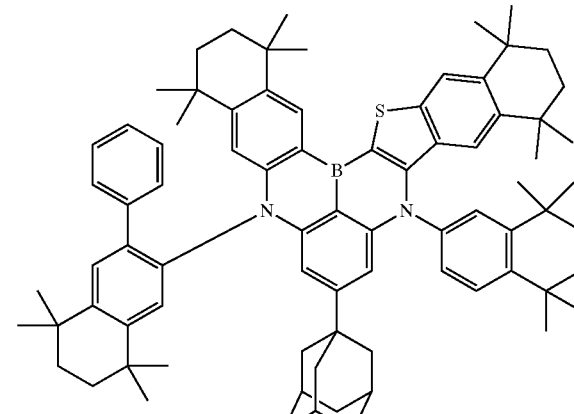 |
| 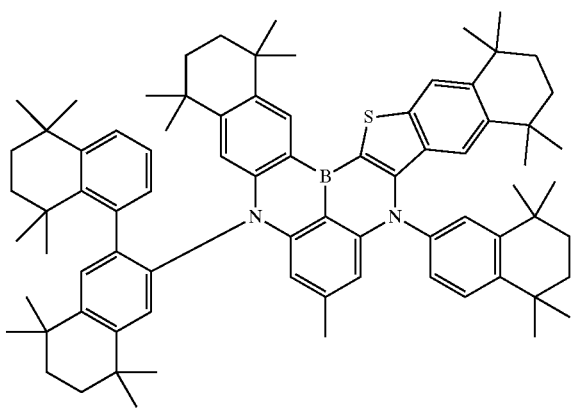 | 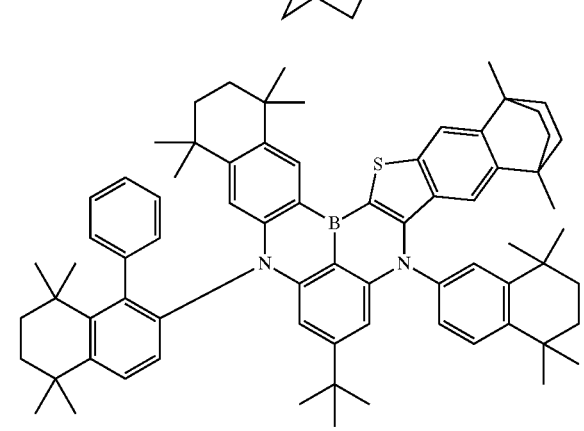 |
| 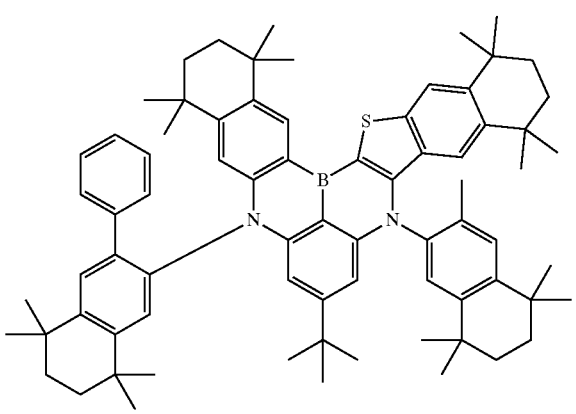 | 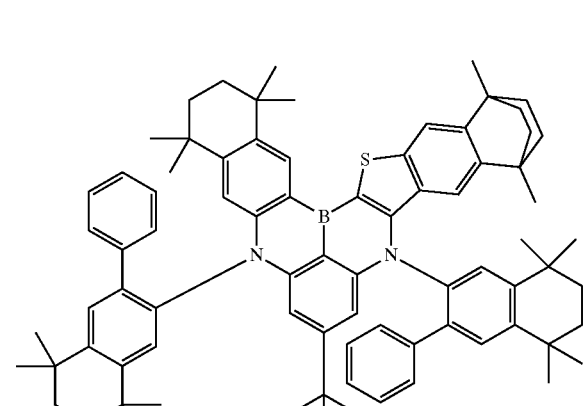 |
| 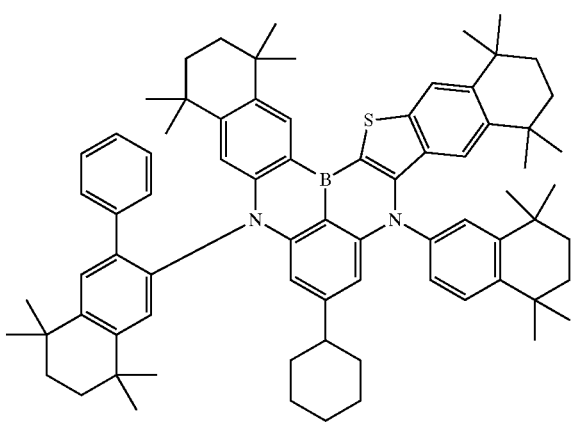 | 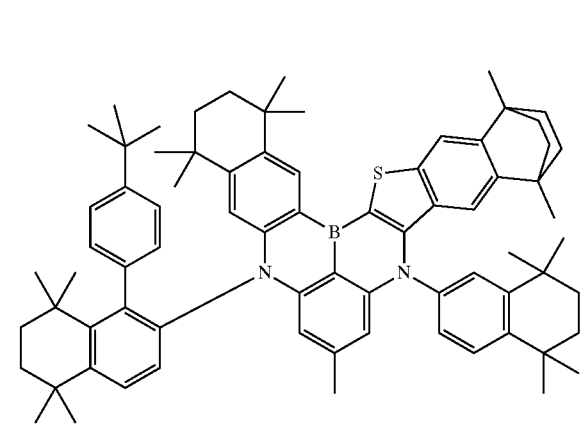 |

1657
-continued
1658
-continued
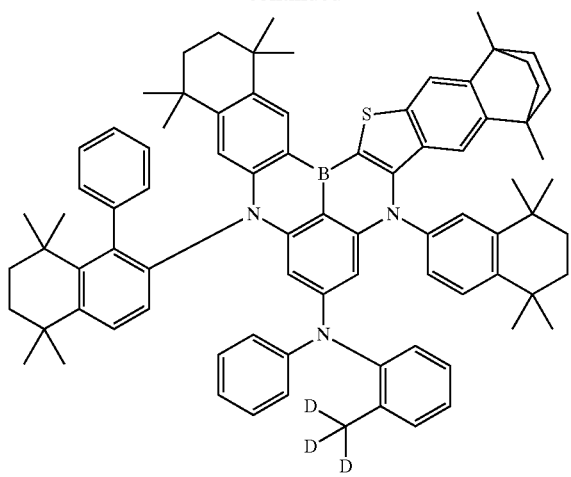
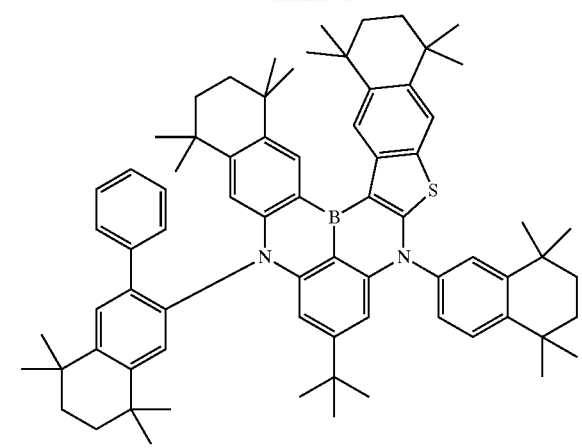
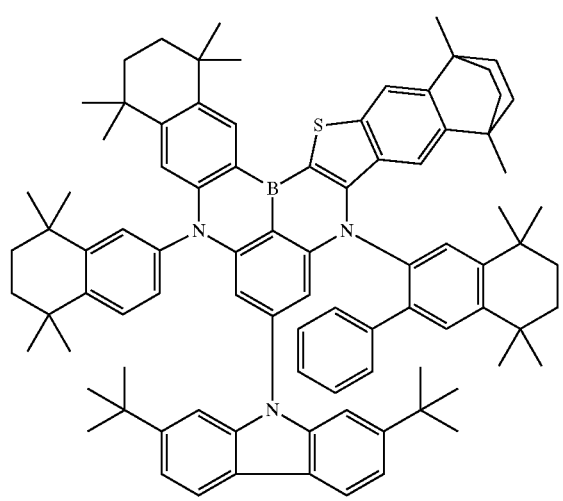
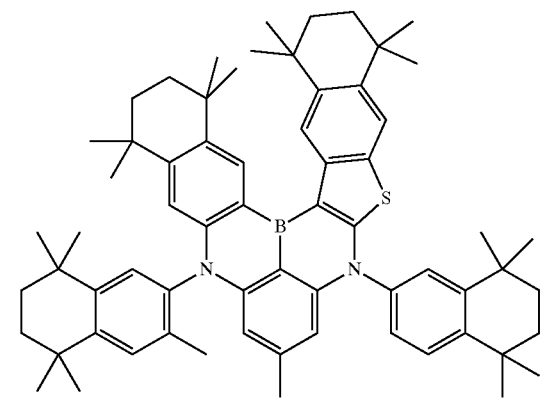
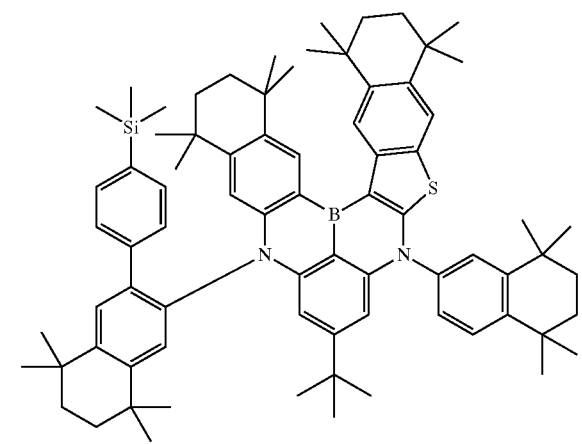

1659
-continued
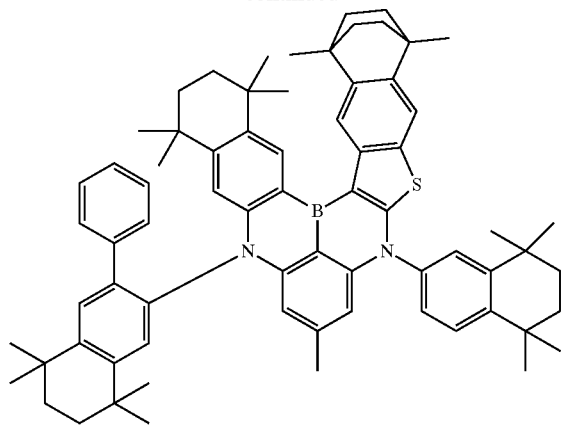
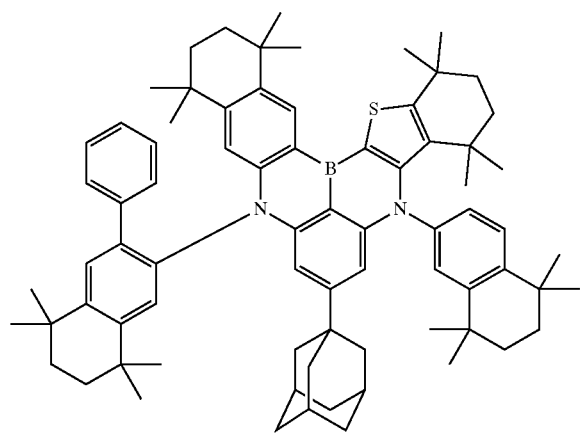
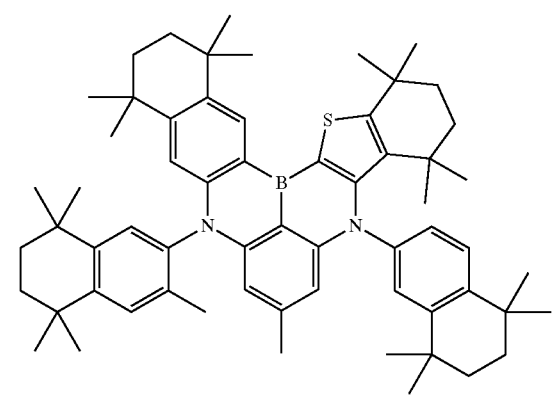
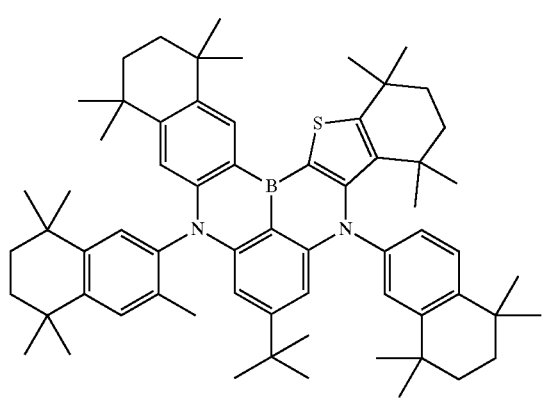
1660
-continued
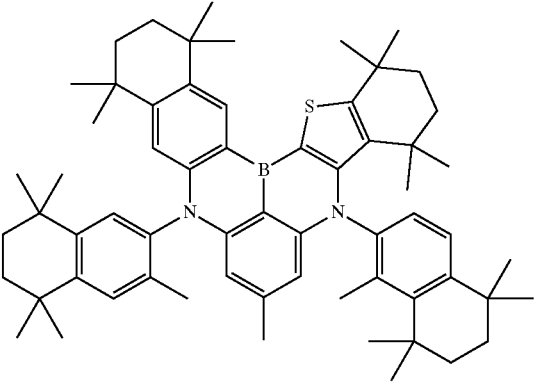
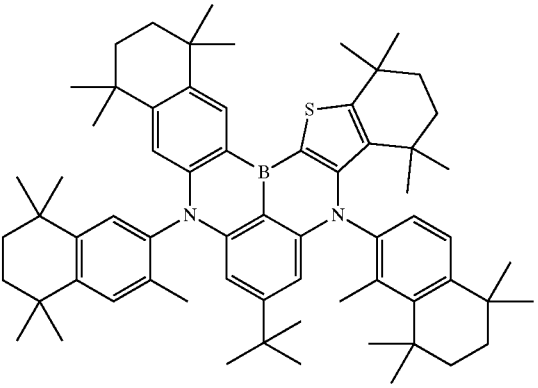
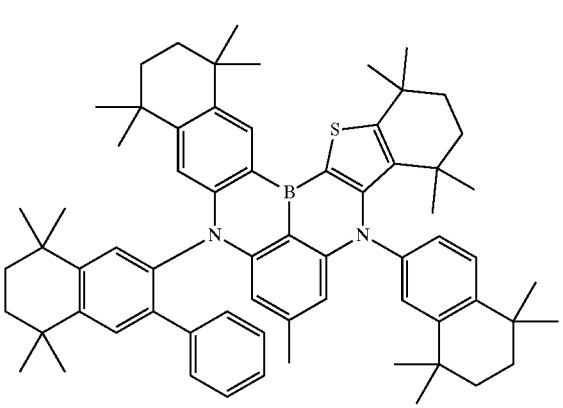
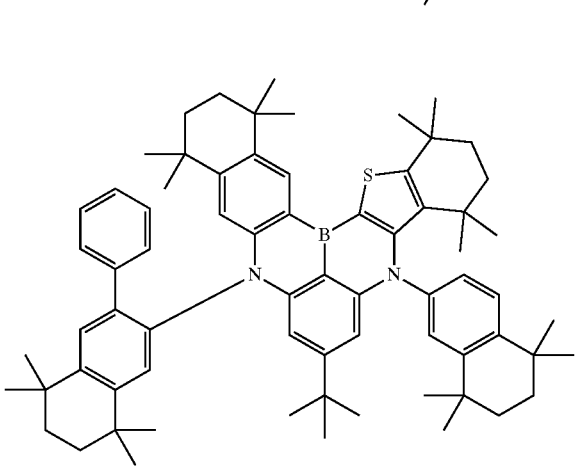

1661
-continued
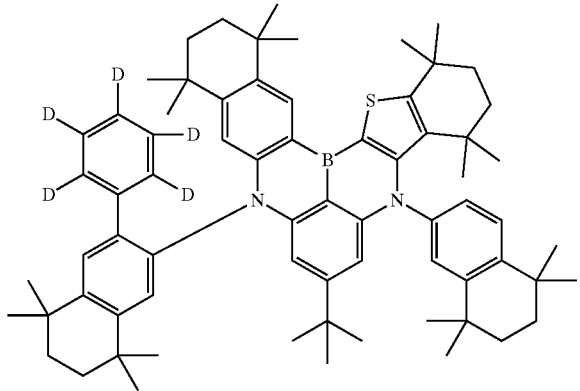
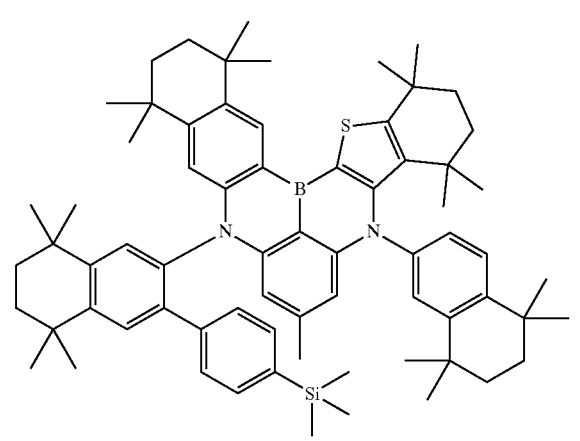
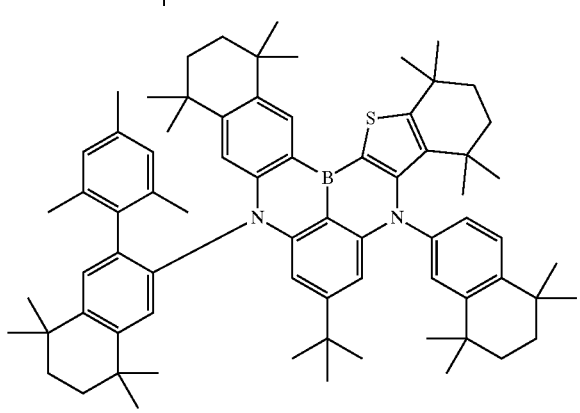
1662
-continued
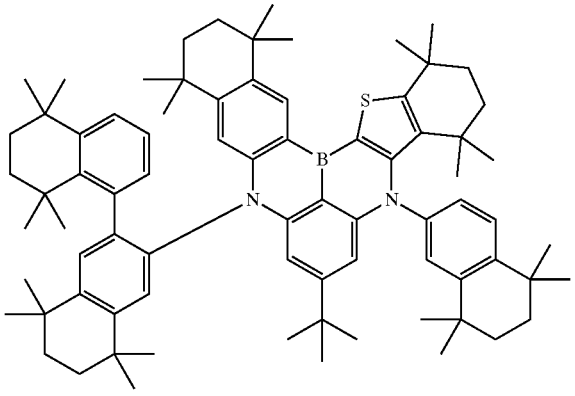
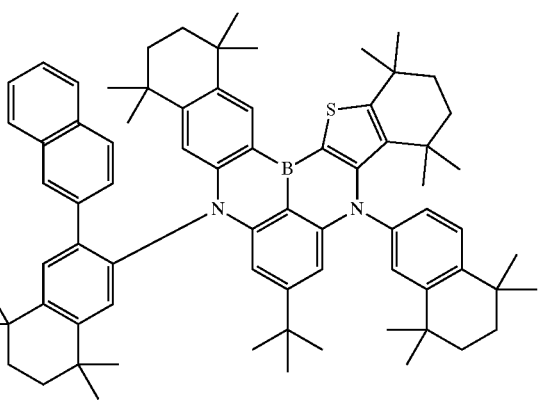
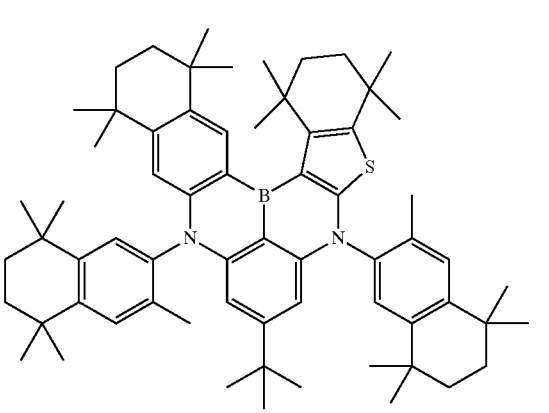

1663
-continued
1664
-continued
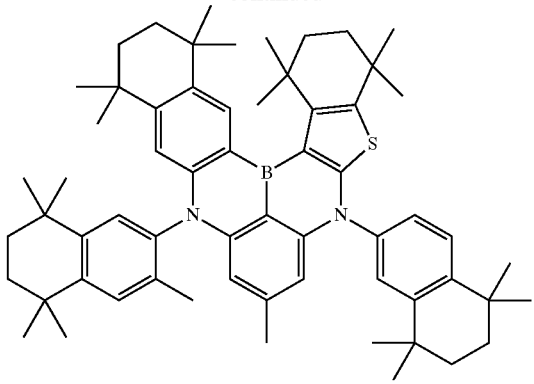 [SMILES: Cc1cc2c3c(c1)N(c1cc4c(cc1C)C(C)(C)CCC4(C)C)c1sc4c(c1B3c1cc3c(cc1N2c1cc2c(cc1C)C(C)(C)CCC2(C)C)C(C)(C)CCC3(C)C)C(C)(C)CCC4(C)C]
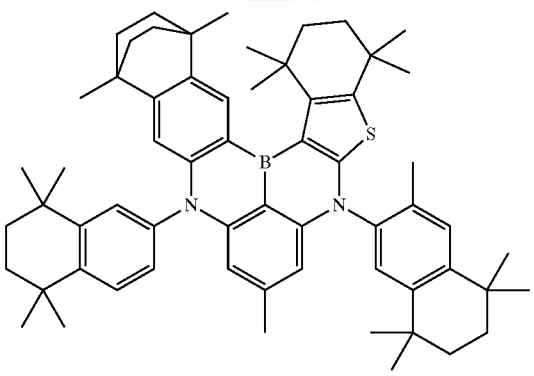

1665
-continued

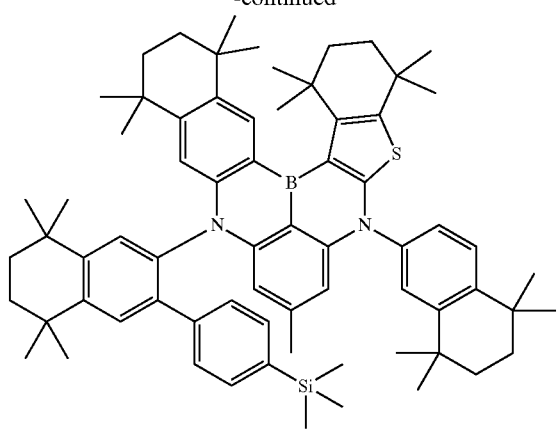

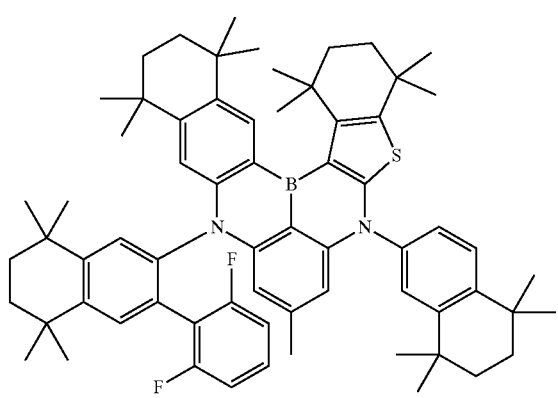

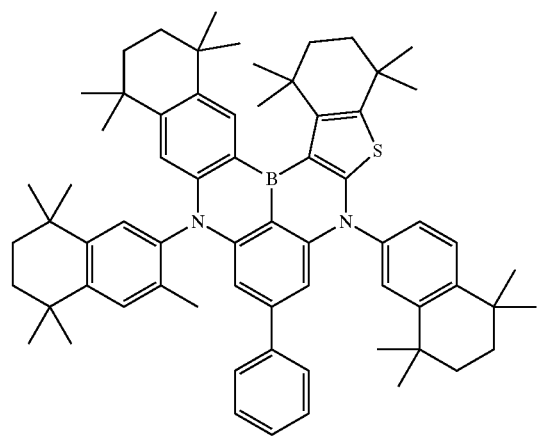

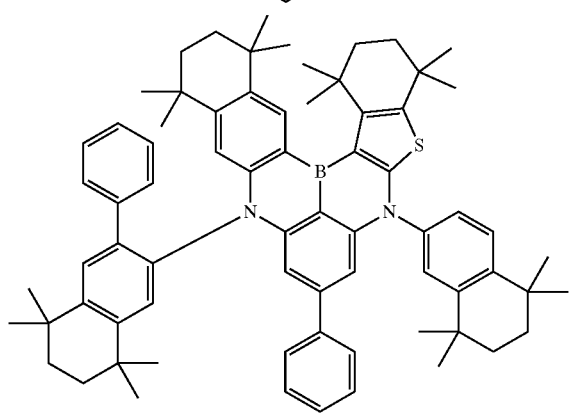

1666
-continued

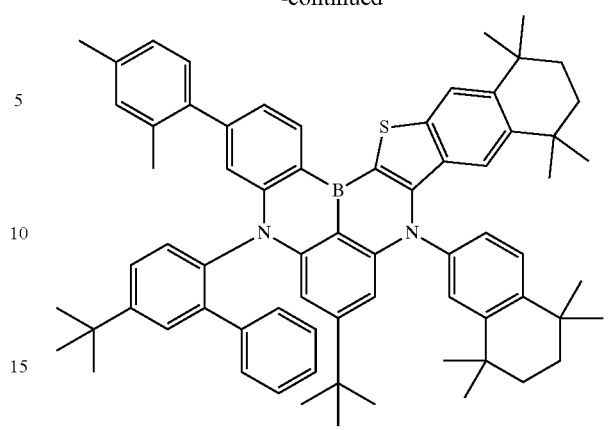

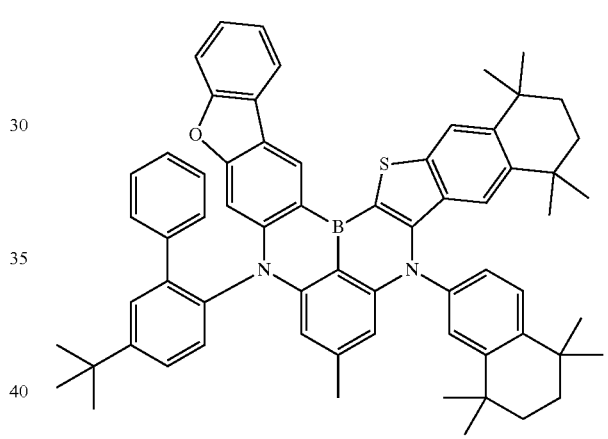

wherein in the compounds, Ph is a phenyl group, and D is deuterium.

7. An organic light emitting device comprising:
   a first electrode;
   a second electrode; and
   an organic material layer including one or more layers provided between the first electrode and the second electrode,
   wherein one or more layers of the organic material layer include the compound of claim 1.

8. The organic light emitting device of claim 7, wherein the organic material layer includes a light emitting layer, and the light emitting layer includes the compound.

9. The organic light emitting device of claim 7, wherein the organic material layer includes a light emitting layer, the light emitting layer includes a dopant material, and the dopant material includes the compound.

10. The organic light emitting device of claim 7, wherein the organic material layer includes a light emitting layer, and the light emitting layer further includes a compound represented by the following Chemical Formula H:

[Chemical Formula H]

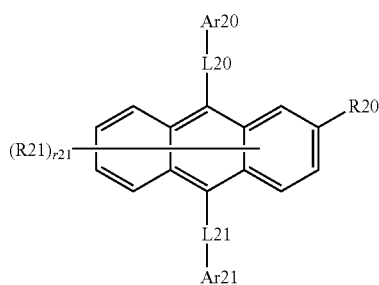

wherein in Chemical Formula H,

L20 and L21 are the same as or different from each other, and each independently a direct bond; a substituted or unsubstituted arylene group; or a substituted or unsubstituted heteroarylene group, Ar20 and Ar21 are the same as or different from each other, and each independently hydrogen; deuterium; a substituted or unsubstituted aryl group; or a substituted or unsubstituted heterocyclic group, R20 and R21 are the same as or different from each other, and each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group, and r21 is an integer of 1 to 7, and when r21 is 2 or greater, the two or more R21 s in the parentheses are the same as or different from each other.

11. The organic light emitting device of claim 10, wherein Ar20 is a substituted or unsubstituted heterocyclic group, and Ar21 is a substituted or unsubstituted aryl group.

12. The organic light emitting device of claim 7, wherein the organic material layer includes a light emitting layer, the light emitting layer further includes a host compound, and in the host compound, at least one hydrogen at a substitutable position is substituted with deuterium.

13. The organic light emitting device of claim 7, wherein the organic material layer includes a light emitting layer, and the light emitting layer includes one or more dopants and a host.

14. The organic light emitting device of claim 7, wherein the organic material layer includes a light emitting layer, and the light emitting layer includes two or more mixed dopants and a host.

15. The organic light emitting device of claim 7, wherein the organic material layer includes a light emitting layer, and the light emitting layer includes one or more hosts and a dopant.

16. The organic light emitting device of claim 7, wherein the organic material layer includes a light emitting layer, and the light emitting layer includes two or more mixed hosts and a dopant.

\* \* \* \* \*